US012091425B2

United States Patent
Bedke et al.

(10) Patent No.: US 12,091,425 B2
(45) Date of Patent: *Sep. 17, 2024

(54) COMPOUNDS THAT INHIBIT MCL-1 PROTEIN

(71) Applicant: AMGEN INC., Thousand Oaks, CA (US)

(72) Inventors: David Karl Bedke, North Attleboro, MA (US); Michael W. Gribble, Jr., Somerville, MA (US); Michael G. Johnson, San Francisco, CA (US); Todd J. Kohn, Thousand Oaks, CA (US); Kexue Li, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 149 days.

This patent is subject to a terminal disclaimer.

(21) Appl. No.: 17/501,075

(22) Filed: Oct. 14, 2021

(65) Prior Publication Data

US 2023/0052348 A1 Feb. 16, 2023

Related U.S. Application Data

(63) Continuation of application No. 16/078,152, filed as application No. PCT/US2017/019336 on Feb. 24, 2017, now Pat. No. 11,306,107.

(60) Provisional application No. 62/300,013, filed on Feb. 25, 2016.

(51) Int. Cl.
*C07D 513/10* (2006.01)
*C07D 513/20* (2006.01)
*C07D 515/10* (2006.01)

(52) U.S. Cl.
CPC ......... *C07D 513/10* (2013.01); *C07D 513/20* (2013.01); *C07D 515/10* (2013.01)

(58) Field of Classification Search
CPC .................................................. C07D 513/10
See application file for complete search history.

(56) References Cited

U.S. PATENT DOCUMENTS

| | | | |
|---|---|---|---|
| 4,522,811 A | 6/1985 | Eppstein et al. | |
| 6,468,798 B1 | 10/2002 | Deb et al. | |
| 6,471,996 B1 | 10/2002 | Sokoll et al. | |
| 6,472,375 B1 | 10/2002 | Hoon et al. | |
| 9,562,061 B2 | 2/2017 | Brown et al. | |
| 11,306,107 B2* | 4/2022 | Brown ................ | C07D 513/10 |
| 2009/0054402 A1 | 2/2009 | Wang et al. | |
| 2010/0298369 A1 | 11/2010 | Horne et al. | |
| 2014/0051683 A1 | 2/2014 | Wang et al. | |
| 2015/0045357 A1 | 2/2015 | Nikolovska-Coleska et al. | |
| 2015/0284328 A1 | 10/2015 | Wang et al. | |
| 2017/0088560 A1 | 3/2017 | Brown et al. | |
| 2021/0230189 A1 | 7/2021 | Brown et al. | |

FOREIGN PATENT DOCUMENTS

| | | |
|---|---|---|
| WO | 2008/131000 A2 | 10/2008 |
| WO | 2011/094708 A2 | 8/2011 |
| WO | 2013/052943 A2 | 4/2013 |
| WO | 2013/149124 A1 | 10/2013 |
| WO | 2015/148854 A1 | 10/2015 |
| WO | 2016/033486 A1 | 3/2016 |

OTHER PUBLICATIONS

Beroukhim,R., et al., "The landscape of somatic copy-number alteration across human cancers," Nature 463, 899-905 (2010).
Lessene, G., et al., "BCL-2 family antagonists for cancer therapy," Nat. Rev. Drug. Discov., vol. 7, 989-1000 (2008).
Akgul, C., "MCL-1 is a potential therapeutic target in multiple types of cancer," Cell. Mol. Life Sci. vol. 66 1326-1336 (2009).
Mandelin II, A. M. et al., "Myeloid cell leukemia-1 as a therapeutic target," Expert Opin. Ther. Targets, 11(3):363-373 (2007).
Rowe, R. C., et al., Handbook of Pharmaceutical Excipients, 5th Edition (2005).
Berge, S. M. et al. "Pharmaceutical Salts", J. Pharm. Sci. 66: 1-19 (1977).
Hamajima, K. et al., "Intranasal Administration of HIV-DNA Vaccine Formulated with a Polymer, Carboxymethylcellulose, Augments Mucosal Antibody Production and Cell-Mediated Immune Response," Clin. Immunol. Immunopathol., 88(2), 205-210 (1998).
Higuchi, T. et al., "Pro-drugs as Novel Delivery Systems," vol. 14 of the A.C.S. Symposium Series (1975).
Roche, E.B., "Bioreversible Carriers in Drug Design", ed. Edward B. Roche, American Pharmaceutical Association and Pergamon Press, (1987).

(Continued)

*Primary Examiner* — Paul V Ward
(74) *Attorney, Agent, or Firm* — Kimberly L. Berkowski

(57) ABSTRACT

Provided herein are myeloid cell leukemia 1 protein (Mcl-1) inhibitors, methods of their preparation, related pharmaceutical compositions, and methods of using the same. For example, provided herein are compounds of Formula I,

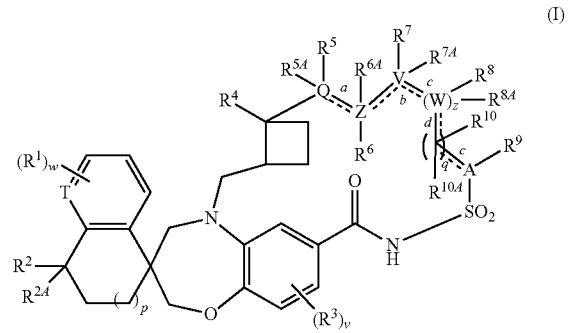

and pharmaceutically acceptable salts thereof and pharmaceutical compositions containing the compounds. The compounds and compositions provided herein may be used, for example, in the treatment of diseases or conditions, such as cancer.

7 Claims, No Drawings

(56) References Cited

OTHER PUBLICATIONS

Brubaker, J. D., et al., "A Practical, Enantioselective Synthetic Route to a Key Precursor to the Tetracycline Antibiotics," Org. Lett., 9, 3523-3525 (2007).
Krasovskiy, A et al., "Convenient Titration Method for Organometallic Zinc, Magnesium, and Lanthanide Reagents," Synthesis, 890-891 (2006).
Sigman, M. S. et al., "Palladium-Catalyzed Allylic Cross-Coupling Reactions of Primary and Secondary Homoallylic Electrophiles," J. Am. Chem. Soc., 134(28), 11408-11411 (2012).
International Search Report and Written Opinion of analogous PCT application PCT/US2017/019336 dated Jun. 12, 2018.
Farrell, R. P. "Breaking Symmetry Towards Development and Scale Up of a Complex Drug Candidate," American Chemical Society Meeting Presentation, Philadelphia, PA, Aug. 22, 2016.
Brown, B. "Interdiction at a Protein-Protein Interface: Structure-Based Design of Mcl-1 Inhibitors," American Chemical Society Meeting Presentation, Philadelphia, PA, Aug. 22, 2016.
Brown, S. "Interdiction at a Protein-Protein Interface: Structure-Based Design of Mcl-1 Inhibitors," Presentation at Caltech, Pasadena, CA, Jun. 1, 2016.

\* cited by examiner

COMPOUNDS THAT INHIBIT MCL-1 PROTEIN

This application is a continuation of and claim priority to U.S. patent application Ser. No. 16/078,152, filed on Aug. 21, 2018, pending, which is a 371 National Phase application of PCT Application No. PCT/US2017/019336, filed on Feb. 24, 2017, which claims the benefit of U.S. Provisional Application No. 62/300,013, filed on Feb. 25, 2016, each of which is hereby incorporated by reference in its entirety for all purposes as if specifically set forth herein.

FIELD OF THE INVENTION

The present invention relates to compounds that inhibit myeloid cell leukemia 1 protein (Mcl-1, also abbreviated as MCL-1 or MCL1); methods of treating diseases or conditions, such as cancer, using the compounds; and pharmaceutical compositions containing the compounds.

BACKGROUND OF THE INVENTION

One common characteristic of human cancer is overexpression of Mcl-1. Mcl-1 overexpression prevents cancer cells from undergoing programmed cell death (apoptosis), allowing the cells to survive despite widespread genetic damage.

Mcl-1 is a member of the Bcl-2 family of proteins. The Bcl-2 family includes pro-apoptotic members (such as BAX and BAK) which, upon activation, form a homo-oligomer in the outer mitochondrial membrane that leads to pore formation and the escape of mitochondrial contents, a step in triggering apoptosis. Antiapoptotic members of the Bcl-2 family (such as Bcl-2, Bcl-XL, and Mcl-1) block the activity of BAX and BAK. Other proteins (such as BID, BIM, BIK, and BAD) exhibit additional regulatory functions.

Research has shown that Mcl-1 inhibitors can be useful for the treatment of cancers. MCl-1 is overexpressed in numerous cancers. See Beroukhim et al. (2010) Nature 463, 899-90. Cancer cells containing amplifications surrounding the Mcl-1 and Bcl-2-1-1 anti-apoptotic genes depend on the expression of these genes for survival. Beroukhim et al. Mcl-1 is a relevant target for the re-initiation of apoptosis in numerous cancer cells. See G. Lessene, P. Czabotar and P. Colman, Nat. Rev. Drug. Discov., 2008, 7, 989-1000; C. Akgul Cell. Mol. Life Sci. Vol. 66, 2009; and Arthur M. Mandelin II, Richard M. Pope, Expert Opin. Ther. Targets (2007) 11(3):363-373.

New compositions and methods for preparing and formulating Mcl-1 inhibitors would be useful.

SUMMARY OF THE INVENTION

In one embodiment, the present invention provides compounds of Formula I,

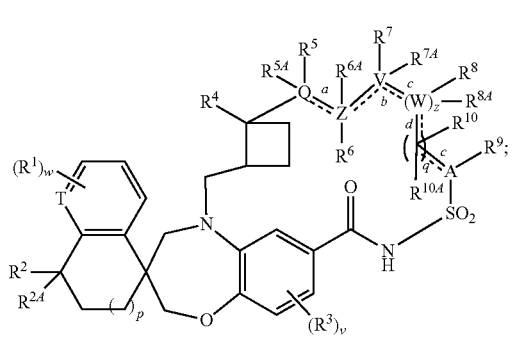

or a pharmaceutically acceptable salt thereof, wherein:

a, b, and c, each represented by the symbol ======, is a single or double chemical bond which may be cis or trans, wherein one of a, b, c, d and e is a double bond, or each of a, b, c, d and e is a single bond, or a and c are double bonds and b, d, and e are single bonds;

A is $CR^{9A}$ or N; wherein when A is $CR^{9A}$, $R^9$ and $R^{9A}$ together may form $=CH_2$;

Q is selected from C or S; wherein $R^5$ and $R^{5A}$ may both be absent if Q is S; or $R^5$ and $R^{5A}$ together may form $=O$ when Q is C or S; or $R^5$ and $R^{5A}$ together may form $=CH_2$ or $=N$ when Q is C;

T is CH, CR' or N;

V is selected from C, O, or N; wherein if V is O, then $R^7$ and $R^{7A}$ are absent; further wherein if V is N, then $R^{7A}$ is absent; and further wherein if V is C, then $R^7$ and $R^{7A}$ together may form a $=O$;

W is selected from C, O, or N; wherein if W is O, then $R^8$ and $R^{8A}$ are absent; and further wherein if W is N, then $R^{8A}$ is absent;

Z is selected from C, O, or N; wherein if Z is O, then $R^6$ and $R^{6A}$ are absent; and further wherein if Z is N, then $R^{6A}$ is absent;

a and b are single bonds if Z is O or N;

a is a single bond if Q is S;

$R^5$ and $R^{6A}$ are absent when a is a double bond;

$R^{6A}$ and $R^{7A}$ are absent when b is a double bond;

$R^{7A}$ and $R^{8A}$ are absent when c is a double bond;

$R^{8A}$ and $R^{10A}$ are absent when d is a double bond;

$R^{10A}$ and $R^{9A}$ are absent when e is a double bond;

$R^5$ is H, $C_{1-6}$alkyl, $C_{1-6}$alkenyl, $C_{1-6}$alkynyl, or $-Y-R^{11}$;

Y is independently O, or $NR^{14}$;

$R^{5A}$ is H;

p is 0 or 1;

q is 0, 1, or 2; wherein if q is 0, then d and e represent the same bond;

v is 0, 1, or 2;

w is 0, 1, or 2;

z is 0 or 1; wherein z is 0 only if q is 0; wherein if z is 0 and q is 0, then c and e represent the same bond;

each of $R^1$ and $R^3$ is independently selected from halo, $-C_{1-6}$alkylhalo, $-C_{1-6}$alkenylene, $-(CH_2CH_2O)_nR^a$, $-SO_2R^a$, $-C(=O)R^a$, $-C(=O)OR^a$, or $-C(=O)NR^aR^b$;

each of $R^2$, $R^4$, $R^6$, $R^7$, $R^8$, $R^9$, and $R^{10}$ is independently selected from H, halo, $-C_{1-6}$haloalkyl, $-C_{1-6}$alkenyl, $-C_{1-6}$alkenylene, $-C_{1-6}$alkyl-O-$C_{1-6}$alkyl, $-(CH_2CH_2O)_nR^a$, $-SO_2R^a$, $-CN$, $-C(=O)R^a$, $-C(=O)OR^a$, $-OC(=O)R^a$, $-C(=O)NR^aR^b$, a 5- to 10-membered aryl or heteroaryl, a 5- to 10-membered spirocycloalkyl or spiroheterocycloalkyl, or a 3- to 10-membered cycloalkenyl, monocyclic or bicyclic cycloalkyl, or monocyclic or bicyclic heterocycloalkyl group, where the heteroaryl, spiroheterocycloalkyl or heterocycloalkyl group can have from 1 to 4 heteroatoms independently selected from O, N or S, and the cycloalkyl, spirocycloalkyl, spiroheterocycloalkyl, or heterocycloalkyl group may include a —C=O group, and the spiroheterocycloalkyl, or heterocycloalkyl may include a —S=O or —SO$_2$;

$R^{11}$ is independently selected from H, $C_{1-6}$haloalkyl, —$C_{1-6}$alkyl, —$C_{1-6}$alkenylene, —(CH$_2$CH$_2$O)$_n$R$^a$, —SO$_2$R$^a$, —C(=O)R$^a$, —C(=O)OR$^a$, —C(=O)NR$^a$R$^b$, —$C_{1-6}$alkyl-O—$C_{1-6}$alkyl, a 5- to 10-membered aryl or heteroaryl, a 5- to 10-membered spirocycloalkyl or spiroheterocycloalkyl, or a 3- to 10-membered cycloalkenyl, monocyclic or bicyclic cycloalkyl, or monocyclic or bicyclic heterocycloalkyl group, where the heteroaryl, spiroheterocycloalkyl or heterocycloalkyl group can have from 1 to 4 heteroatoms independently selected from O, N or S, and the cycloalkyl, spirocycloalkyl, spiroheterocycloalkyl, or heterocycloalkyl group may include a —C=O group, and the spiroheterocycloalkyl, or heterocycloalkyl may include a —S=O or SO$_2$;

each of $R^{2A}$, $R^{5A}$, $R^{6A}$, $R^{7A}$, $R^{8A}$, $R^{9A}$ and $R^{10A}$ is independently H, OH, halo, —$C_{1-6}$alkyl;

alternatively $R^6$ and $R^7$ together may form a 3- to 8-membered ring, optionally containing a heteroatom selected from N, O or S atom, which may contain a double bond;

alternatively $R^6$ and $R^9$ together may form a 5- to 8-membered ring, optionally containing a heteroatom selected from N, O or S atom, which may contain a double bond;

alternatively $R^6$ and $R^{10}$ together may form a 5- to 8-membered ring, optionally containing a heteroatom selected from N, O or S atom, which may contain a double bond;

alternatively $R^8$ and $R^9$ together may form a 4- to 8-membered ring, optionally containing a heteroatom selected from N, O or S atom, which may contain a double bond;

alternatively $R^8$ and $R^{10}$ together may form a 3- to 8-membered ring, optionally containing a heteroatom selected from N, O or S atom, which may contain a double bond;

alternatively $R^9$ and $R^{10}$ together may form a 3- to 8-membered ring, optionally containing a heteroatom selected from N, O or S atom, which may contain a double bond; and the ring optionally may be substituted by $R^{14}$;

wherein the —$C_{1-6}$alkyl of any of the $R^1$, $R^2$, $R^3$, $R^4$, $R^6$, $R^7$, $R^8$, $R^9$, $R^{10}$, $R^{11}$, $R^{2A}$, $R^{6A}$, $R^{7A}$, $R^{8A}$, $R^{9A}$ and $R^{10A}$ substituents is substituted by 0, 1, 2 or 3 $R^{12}$ substituents independently selected from OH, —OC$_{1-6}$alkyl, —C$_{1-6}$alkyl-O—C$_{1-6}$alkyl, halo, —O-haloC$_{1-6}$alkyl, —CN, —NR$^a$R$^b$, —(NR$^a$R$^b$R$^c$)$^{+1}$, —SO$_2$R$^a$, —(CH$_2$CH$_2$O)$_n$CH$_3$, —C(=O)R$^a$, —OC(=O)R$^a$, —C(=O)OR$^a$, —C(=O)NR$^a$R$^b$, —O-(3- to 10-membered heterocycloalkyl), a 5- to 10-membered aryl or heteroaryl, a 5- to 10-membered spirocycloalkyl or spiroheterocycloalkyl, or a 3- to 10-membered cycloalkenyl, monocyclic or bicyclic cycloalkyl, monocyclic or bicyclic heterocycloalkyl group, where the heteroaryl, spiroheterocycloalkyl or heterocycloalkyl group can have from 1 to 4 heteroatoms independently selected from O, N or S, and the cycloalkyl, spirocycloalkyl, spiroheterocycloalkyl, or heterocycloalkyl group may include a —C=O group, and the spiroheterocycloalkyl, or heterocycloalkyl may include a —S=O or SO$_2$;

wherein the aryl, heteroaryl, cycloalkyl, heterocycloalkyl, spirocycloalkyl or spiroheterocycloalkyl group of any of the $R^1$, $R^2$, $R^3$, $R^4$, $R^6$, $R^7$, $R^8$, $R^9$, $R^{10}$, $R^{11}$, and $R^{12}$ substituents can be unsubstituted or substituted with from 1 to 4 $R^{13}$ substituents independently selected from OH, halo, —NR$^c$R$^d$, —C$_{1-6}$alkyl, —OC$_{1-6}$alkyl, —C$_{1-6}$alkyl-OH, —C$_{1-6}$alkyl-O—C$_{1-6}$alkyl, —C$_{1-6}$haloalkyl, —O-haloC$_{1-6}$alkyl, —SO$_2$R$^c$, —CN, —C(=O)NR$^c$R$^d$, —C(=O)R$^c$, —OC(=O)R$^a$, —C(=O)OR$^c$, a 5- to 10-membered aryl or heteroaryl, a 5- to 10-membered spirocycloalkyl or spiroheterocycloalkyl, or a 3- to 10-membered cycloalkenyl, monocyclic or bicyclic cycloalkyl, or monocyclic or bicyclic heterocycloalkyl group, wherein the heteroaryl, spiroheterocycloalkyl, or heterocycloalkyl group can have from 1 to 4 heteroatoms independently selected from O, N or S, and the cycloalkyl, spirocycloalkyl, spiroheterocycloalkyl, or heterocycloalkyl group may include a —C=O group, and the spiroheterocycloalkyl, or heterocycloalkyl may include a —S=O or —SO$_2$;

wherein each R$^a$, R$^b$, R$^c$, and R$^d$ is independently hydrogen, OH, —C$_{1-6}$alkyl, —C$_{1-6}$alkyl-NR$^{14}$R$^{14}$, NR$^{14}$R$^{14}$, —SO$_2$R$^{14}$, —(CH$_2$CH$_2$O)$_n$CH$_3$, —C(=O)R$^{14}$, —CN, —OC(=O)R$^{14}$, —C(=O)OR$^{14}$, —C(=O)NR$^{14}$R$^{14}$, —C$_{1-6}$haloalkyl, —O-haloC$_{1-6}$alkyl, —C$_{1-6}$alkyl-O—C$_{1-6}$alkyl, benzyl, phenyl, a —C$_{1-6}$alkylheterocycloalkyl, a 5- to 10-membered aryl or heteroaryl, a 5- to 10-membered spirocycloalkyl or spiroheterocycloalkyl, or a 3- to 10-membered cycloalkenyl, monocyclic or bicyclic cycloalkyl, or monocyclic or bicyclic heterocycloalkyl group, where the heteroaryl, spiroheterocycloalkyl, heterocycloalkyl group of the —C$_{1-6}$alkyl heterocycloalkyl group can have from 1 to 4 heteroatoms independently selected from O, N or S, and the cycloalkyl, spirocycloalkyl, spiroheterocycloalkyl, heterocycloalkyl, or the heterocycloalkyl group of the —C$_{1-6}$alkylheterocycloalkyl group may include a —C=O group, and the spiroheterocycloalkyl, or heterocycloalkyl may include a —S=O or SO$_2$; and the aryl, heteroaryl, spirocycloalkyl, spiroheterocycloalkyl, cycloalkyl, heterocycloalkyl or the heterocycloalkyl group of the —C$_{1-6}$alkylheterocycloalkyl group of R$^a$, R$^b$, R$^c$, and R$^d$ can be unsubstituted or substituted with from 1 to 4 R$^{14}$ substituents independently selected from H, OH, halo, —C$_{1-6}$alkyl, —OC$_{1-6}$alkyl, —C$_{1-6}$haloalkyl, —CN, —O-haloC$_{1-6}$alkyl, phenyl, tolyl, —C(O)C$_{1-6}$alkyl, —C(O)OCH$_3$ and —SO$_2$—N(CH$_3$)$_2$;

wherein n is independently in each instance an integer from 1 to 4; and wherein at least one of the following is true:

a) A is N; or
b) Z is O or N; or
c) Q is S; or
d) V is O or N; or
e) W is O or N; or
f) at least one of $R^2$ and $R^{2A}$ is independently OH, halo, —C$_{1-6}$ alkyl; or
g) v is 1 or 2; or
h) w is 0; or
i) w is 2; or
j) w is 1 and $R^3$ is —C$_{1-6}$haloalkyl, —C$_{1-6}$alkyl, —C$_{1-6}$alkenylene, —(CH$_2$CH$_2$O)$_n$R$^a$, —SO$_2$R$^a$, —C(=O)R$^a$, —C(=O)OR$^a$, or —C(=O)NR$^a$R$^b$; or
k) $R^4$ is C$_{1-6}$alkyl; or
l) $R^8$ is independently selected from halo, —C$_{1-6}$haloalkyl, —C$_{1-6}$alkyl, —C$_{1-6}$alkenylene, —(CH$_2$CH$_2$O)$_n$R$^a$, —SO$_2$R$^a$, —C(=O)R$^a$, —C(=O)OR$^a$, —C(=O)NR$^a$R$^b$, a 5- to 10-membered aryl or heteroaryl, a 5- to 10-membered spirocycloalkyl or spiroheterocycloalkyl, or a 3- to 10-membered cycloalkenyl, monocyclic or bicyclic cycloalkyl, or monocyclic or bicyclic heterocycloalkyl group, where the heteroaryl, spiroheterocycloalkyl or heterocycloalkyl group can have from 1 to 4 heteroatoms independently selected from O, N or S, and the cycloalkyl, spirocycloalkyl, spiroheterocycloalkyl, or heterocycloalkyl group may include a —C=O group, and the spiroheterocycloalkyl, or heterocycloalkyl may include a —S=O or $SO_2$; or m) $R^{8A}$ is independently selected from OH or halo; or n) z is 0; or o) q is 0; or p) q is 2; or q) when q is 1, $R^{10}$ is independently selected from halo, —$C_{1-6}$alkyl-OH, —$C_{1-6}$haloalkyl, —$C_{1-6}$alkenylene, —$(CH_2CH_2O)_nR^a$, —$SO_2R^a$, —$C(=O)R^a$, —$C(=O)OR^a$, —$C(=O)NR^aR^b$, a 5- to 10-membered aryl or heteroaryl, a 5- to 10-membered spirocycloalkyl or spiroheterocycloalkyl, or a 3- to 10-membered cycloalkenyl, monocyclic or bicyclic cycloalkyl, or monocyclic or bicyclic heterocycloalkyl group, where the heteroaryl, spiroheterocycloalkyl or heterocycloalkyl group can have from 1 to 4 heteroatoms independently selected from O, N or S, and the spirocycloalkyl, spiroheterocycloalkyl, or heterocycloalkyl group may include a —C=O group, and the spiroheterocycloalkyl, or heterocycloalkyl may include a —S=O or $SO_2$; or r) when q is 1, $R^{10A}$ is independently selected from OH or halo; or s) when A is C, $R^{9A}$ is independently selected from OH or halo; or t) $R^9$ is independently selected from halo, —$C_{1-6}$alkyl-OH, —$C_{1-6}$haloalkyl, —$C_{1-6}$alkenylene, —$(CH_2CH_2O)_nR^a$, —$SO_2R^a$, —$C(=O)R^a$, —$C(=O)OR^a$, —$C(=O)NR^aR^b$, a 5- to 10-membered aryl or heteroaryl, a 5- to 10-membered spirocycloalkyl or spiroheterocycloalkyl, or a 3- to 10-cycloalkenyl, monocyclic or bicyclic cycloalkyl, or monocyclic or bicyclic heterocycloalkyl group, where the heteroaryl, spiroheterocycloalkyl or heterocycloalkyl group can have from 1 to 4 heteroatoms independently selected from O, N or S, and the spirocycloalkyl, spiroheterocycloalkyl, or heterocycloalkyl group may include a —C=O group, and the spiroheterocycloalkyl, or heterocycloalkyl may include a —S=O or $SO_2$; or u) a is a double bond; or v) c is a double bond; or w) d is a double bond; or x) e is a double bond; or y) a and c are each double bonds; or z) $R^7$ and $R^{7A}$ together represent =O; or aa) when Y is 0, then $R^{11}$ is not H, $C_{1-6}$alkyl, or —$(CH_2CH_2O)_nCH_3$; or bb) Q is S; or cc) when A is $CR^{9A}$, $R^9$ and $R^{9A}$ together form =$CH_2$ or $R^7$ and $R^{7A}$ together form a =O; or dd) each $R^5$ and $R^{5A}$ is H; or ee) when is H, unsubstituted $C_{1-6}$alkyl, or —$(CH_2CH_2O)_nCH_3$, at least one of $R^8$, $R^9$, $R^{10}$, $R^2$, $R^{2A}$, $R^{6A}$, $R^{7A}$, $R^{8A}$, $R^{9A}$ and $R^{10A}$ is not H, $C_{1-6}$alkyl, 3-6-membered cycloalkyl, or $(CH_2)_n$-3-6-membered cycloalkyl.

In another embodiment, the present invention provides compounds having the Formula II:

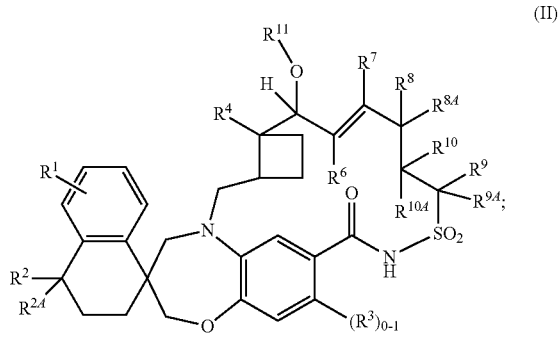

(II)

or a pharmaceutically acceptable salt thereof; wherein $R^1$, $R^2$, $R^3$, $R^4$, $R^6$, $R^7$, $R^8$, $R^9$, $R^{10}$, $R^{11}$, $R^{2A}$, $R^{8A}$, $R^{9A}$ and $R^{10A}$ are defined above.

In another embodiment, the present invention provides compounds having the Formula IIa:

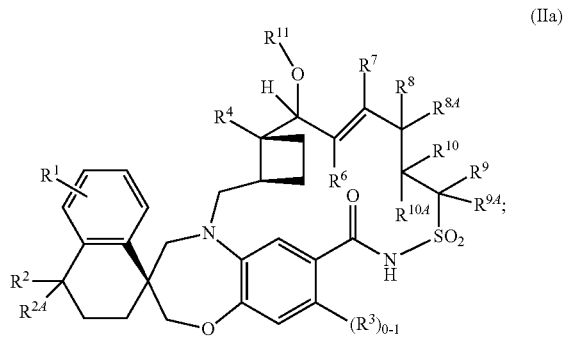

(IIa)

or a pharmaceutically acceptable salt thereof; wherein $R^1$, $R^2$, $R^3$, $R^4$, $R^6$, $R^7$, $R^8$, $R^9$, $R^{10}$, $R^{11}$, $R^{2A}$, $R^{8A}$, $R^{9A}$ and $R^{10A}$ are defined above.

In another embodiment, the present invention provides compounds having the Formula III:

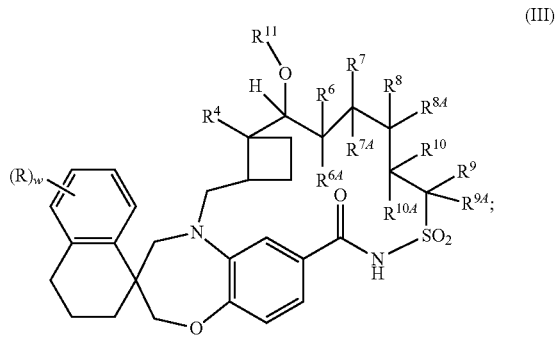

(III)

or a pharmaceutically acceptable salt thereof; wherein $R^1$, $R^2$, $R^3$, $R^4$, $R^6$, $R^7$, $R^8$, $R^9$, $R^{10}$, $R^{11}$, $R^{2A}$, $R^{6A}$, $R^{7A}$, $R^{8A}$, $R^{9A}$ and $R^{10A}$ are defined above.

In another embodiment, the present invention provides compounds having the Formula IIIa:

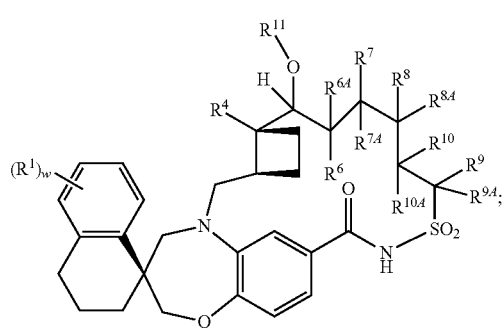

(IIIa)

or a pharmaceutically acceptable salt thereof; wherein $R^1$, $R^2$, $R^3$, $R^4$, $R^6$, $R^7$, $R^8$, $R^9$, $R^{10}$, $R^{11}$, $R^{2A}$, $R^{6A}$, $R^{7A}$, $R^{8A}$, $R^{9A}$ and $R^{10A}$ are defined above.

In another embodiment, the present invention provides compounds having the Formula IV:

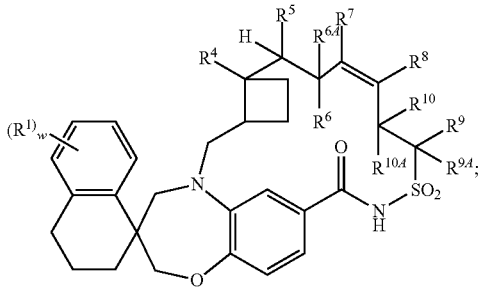

(IV)

or a pharmaceutically acceptable salt thereof; wherein $R^1$, $R^4$, $R^5$, $R^6$, $R^7$, $R^8$, $R^9$, $R^{10}$, $R^{6A}$, $R^{9A}$ and $R^{10A}$ are defined above.

In another embodiment, the present invention provides compounds having the Formula IVa:

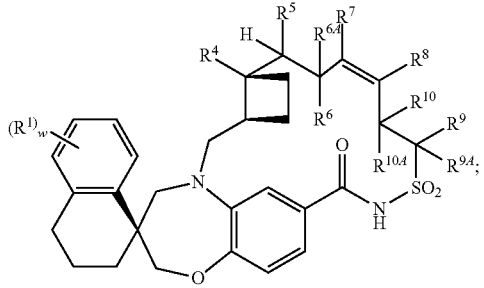

(IVa)

or a pharmaceutically acceptable salt thereof; wherein $R^1$, $R^4$, $R^5$, $R^6$, $R^7$, $R^8$, $R^9$, $R^{10}$, $R^{6A}$, $R^{9A}$ and $R^{10A}$ are defined above.

In another embodiment, the present invention provides compounds having the Formula V:

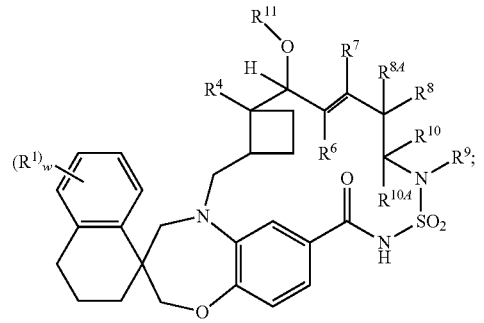

(V)

or a pharmaceutically acceptable salt thereof; wherein $R^1$, $R^4$, $R^6$, $R^7$, $R^8$, $R^9$, $R^{10}$, $R^{11}$, $R^{8A}$, and $R^{10A}$ are defined above.

In another embodiment, the present invention provides compounds having the Formula V(a):

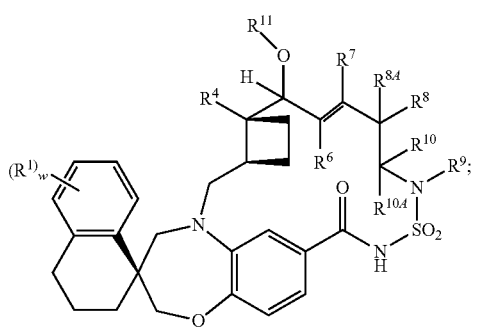

(Va)

or a pharmaceutically acceptable salt thereof; wherein $R^1$, $R^4$, $R^6$, $R^7$, $R^8$, $R^9$, $R^{10}$, $R^{11}$, $R^{8A}$, and $R^{10A}$ are defined above.

In another embodiment, the present invention provides compounds other than a compound of Formula I, wherein the compounds have the Formula VI:

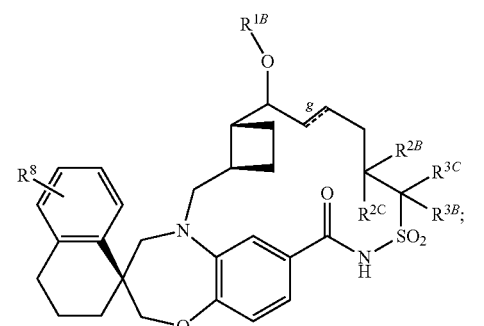

(VI)

or a pharmaceutically acceptable salt thereof;
wherein g, represented by the symbol ------ is a single or double chemical bond which may be cis or trans;
$R^B$ is a halo;
$R^{1B}$ is H, $C_{1-6}$ alkyl, or —(CH$_2$CH$_2$O)jCH3, wherein j is an integer from 1 to 4;

$R^{2B}$ is H or $C_{1-6}$alkyl;
$R^{2C}$ is H or $C_{1-6}$alkyl;
$R^{3B}$ is H or $C_{1-6}$alkyl; and
$R^{3C}$ is H, $C_{1-6}$alkyl, $C_{3-6}$ cycloalkyl, or $(CH_2)_k$—$C_{3-6}$ cycloalkyl, wherein k is an integer from 1 to 4.
In another embodiment, the present invention has a structure selected from:
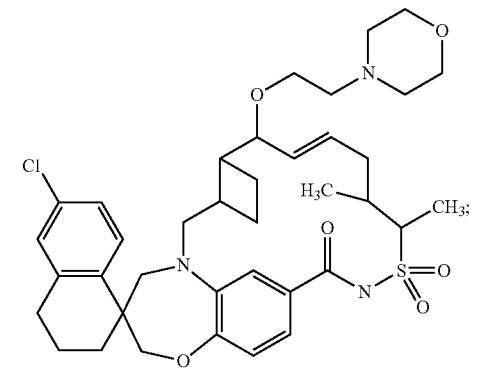
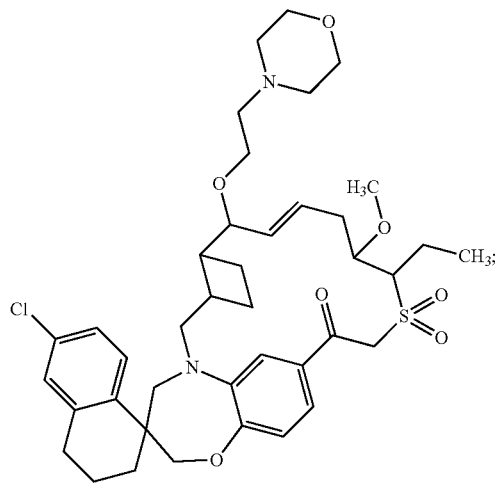
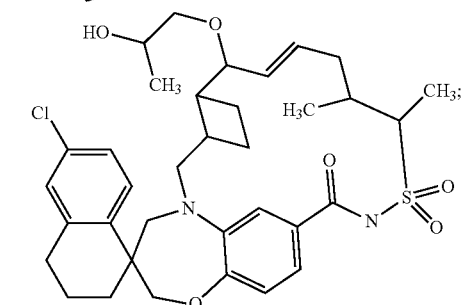
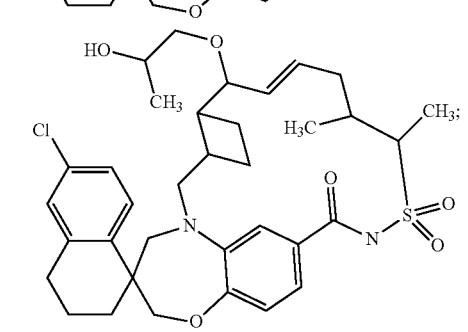
-continued
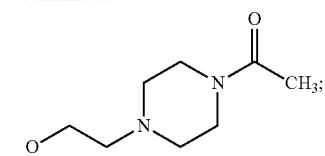
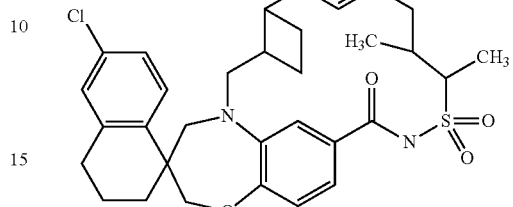
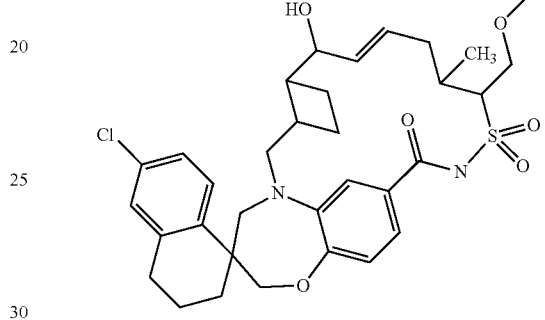
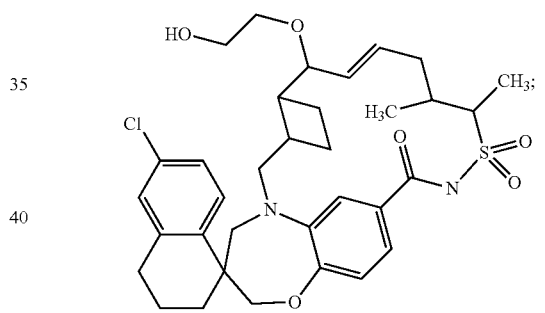
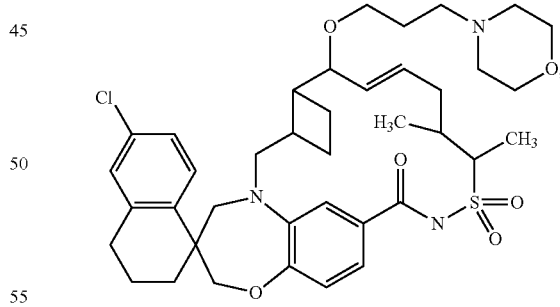
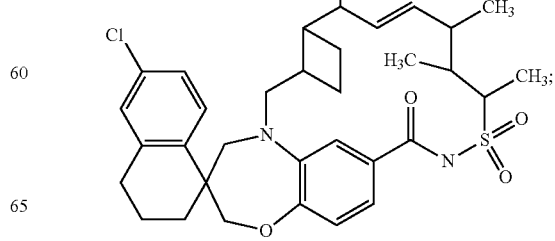

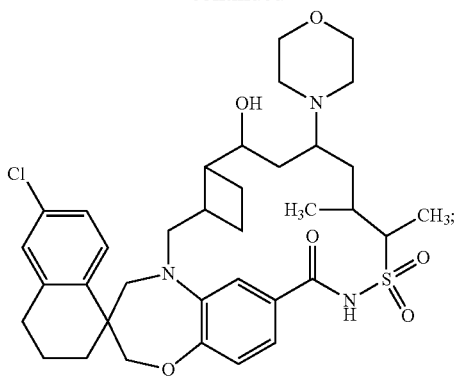
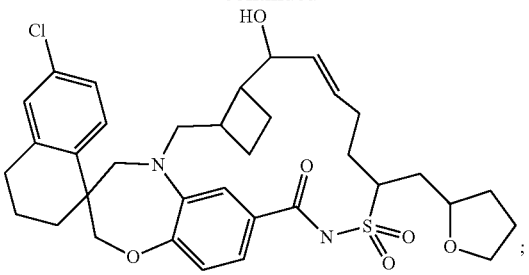
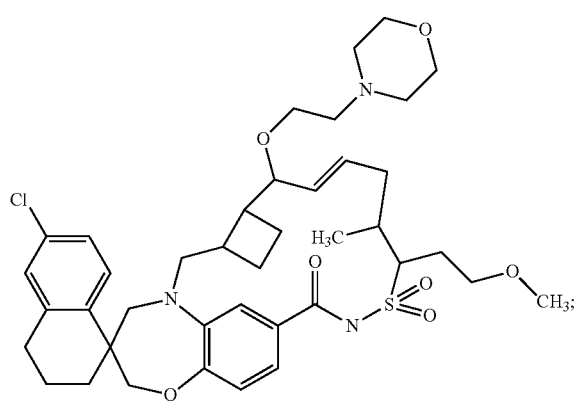
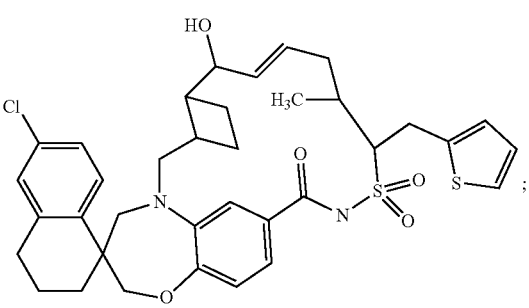
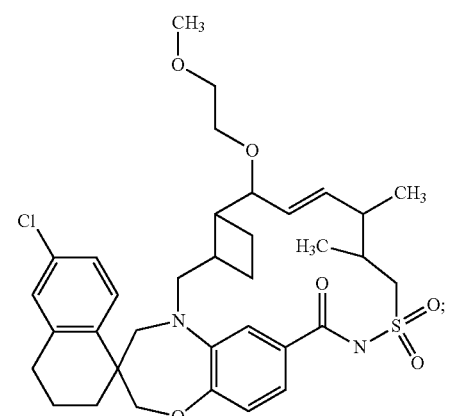
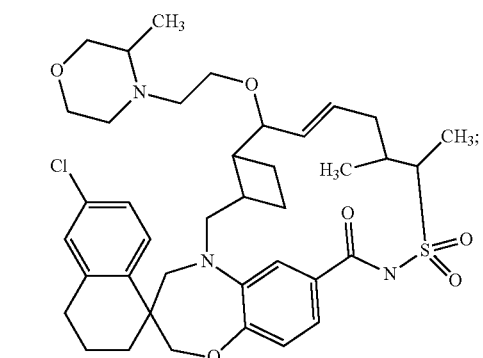
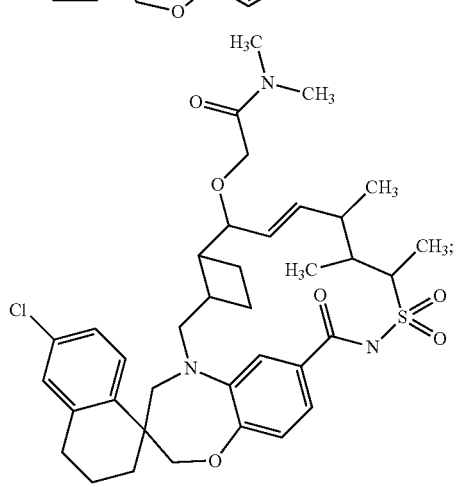
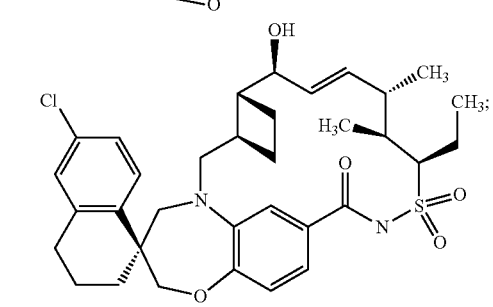

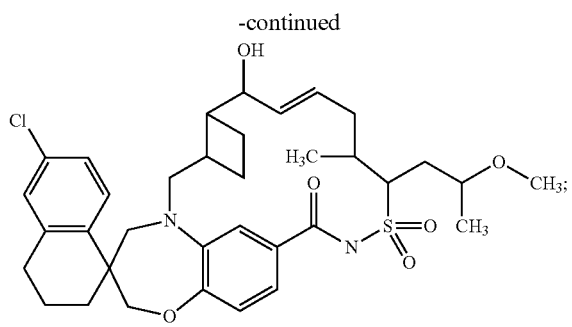
or a stereoisomer thereof; a pharmaceutically acceptable salt thereof, a pharmaceutically acceptable salt of the stereoisomer thereof and a pharmaceutically acceptable excipient.
In another embodiment, the present invention has a structure selected from:
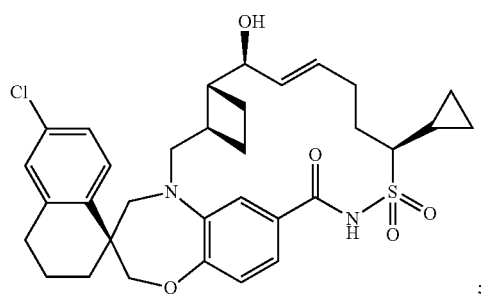
;
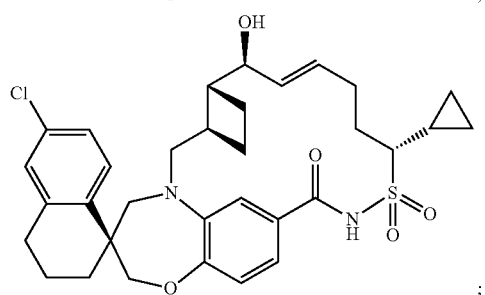
;
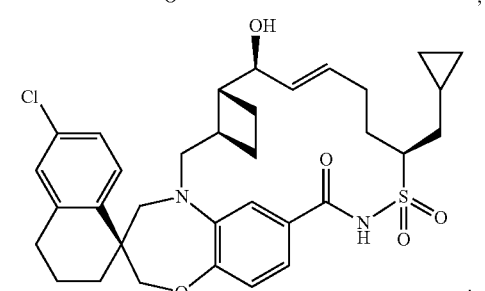
;
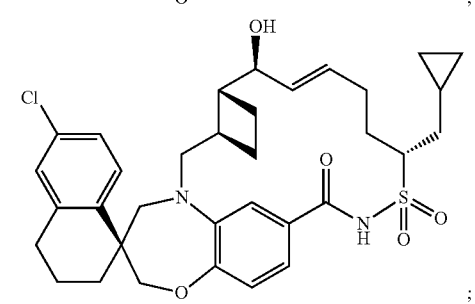
;
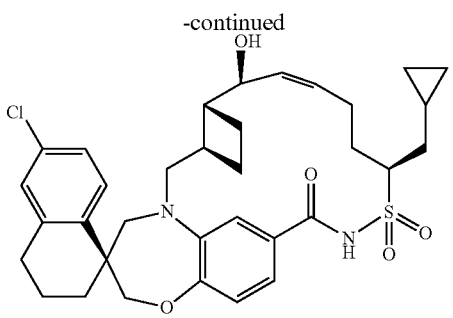
;
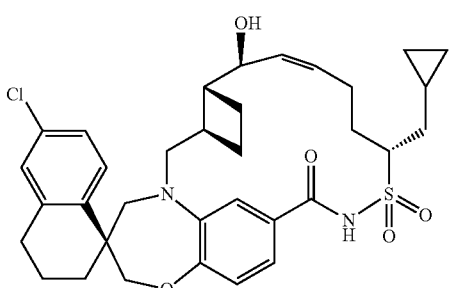
;
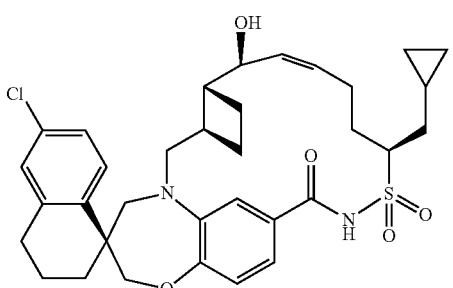
;
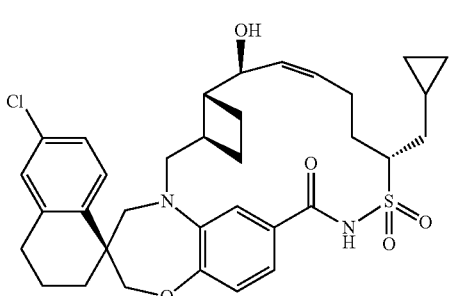
;
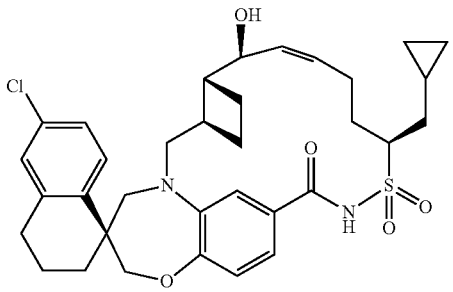
;

-continued
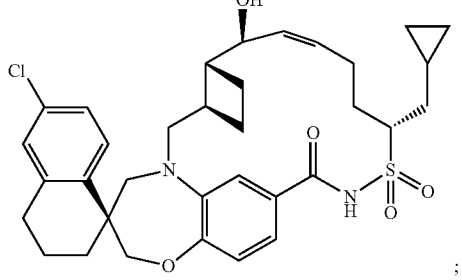
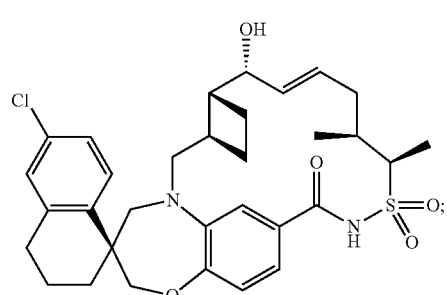
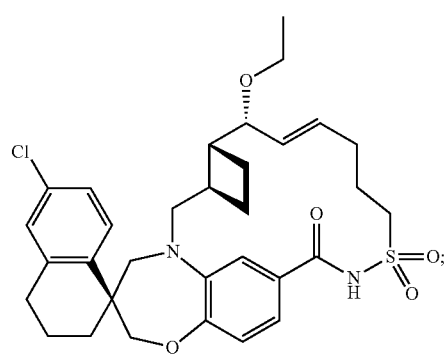
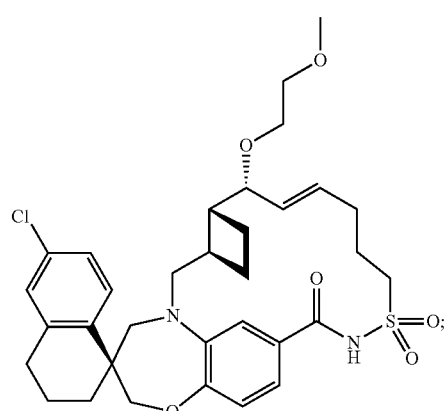
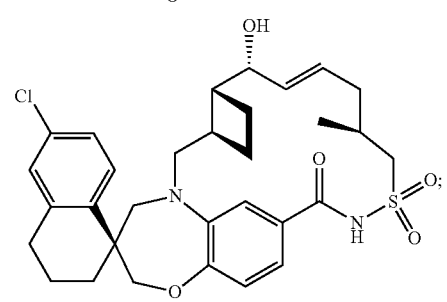
-continued
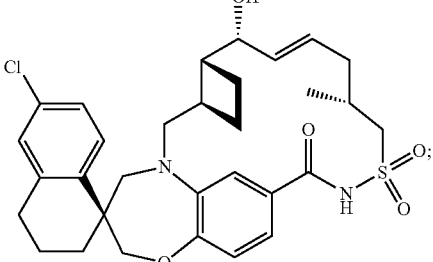
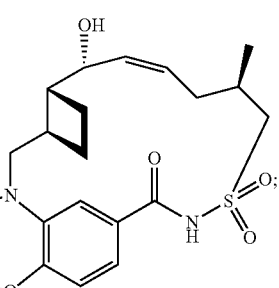
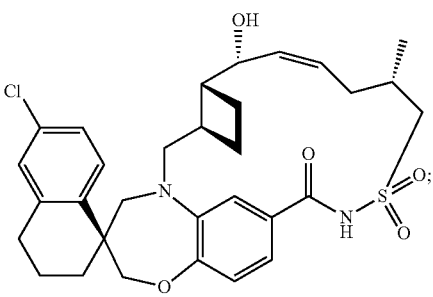
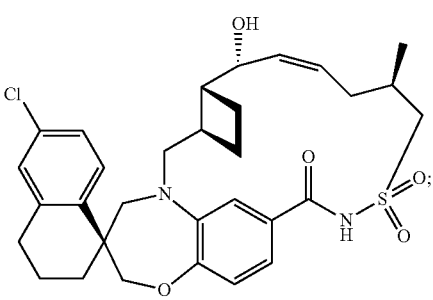
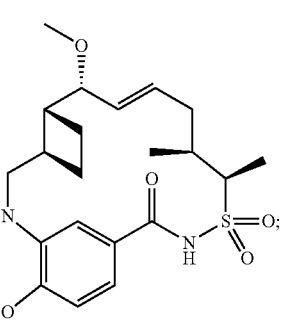

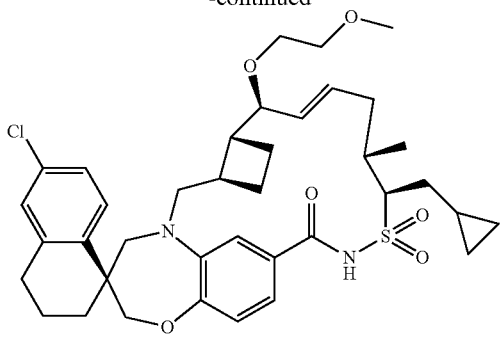
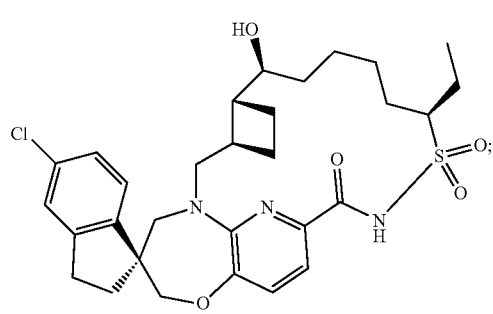
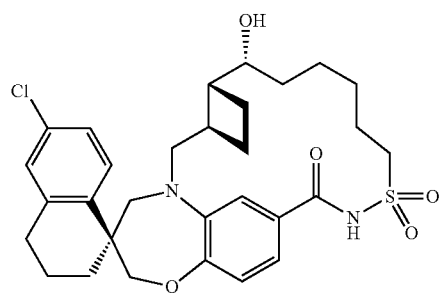
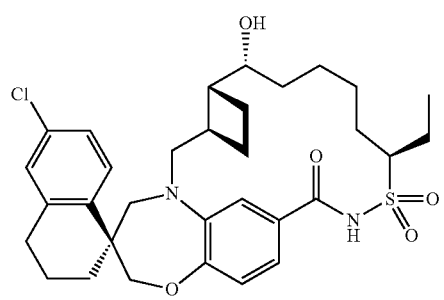
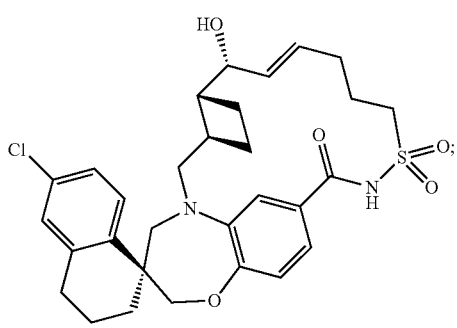
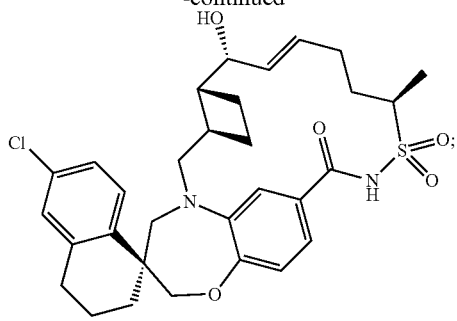
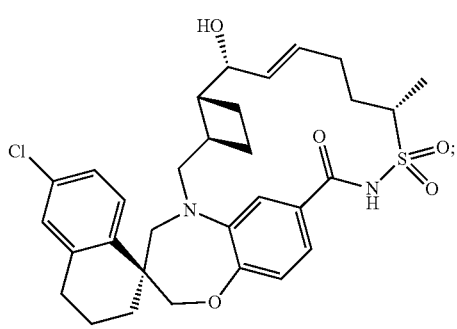
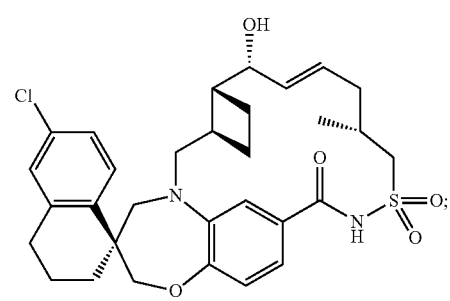
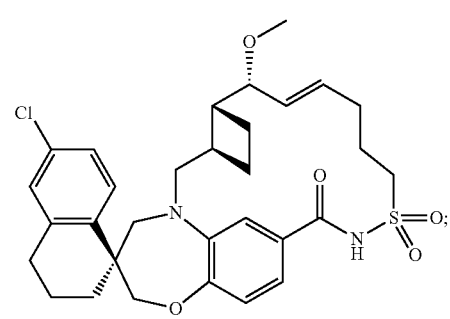
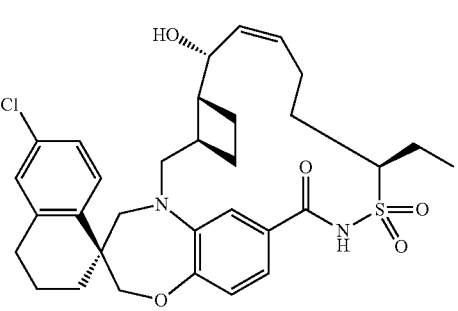

-continued
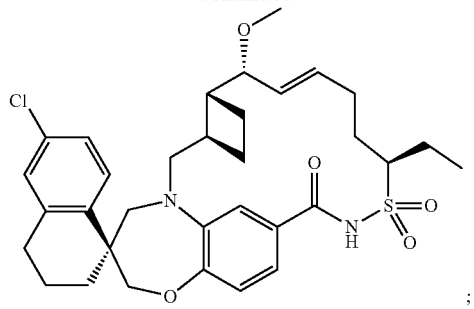
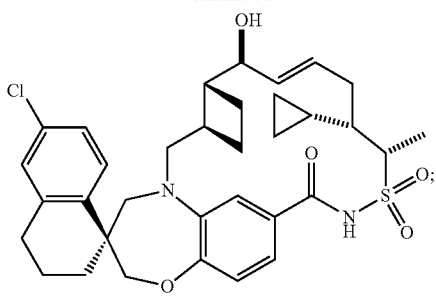
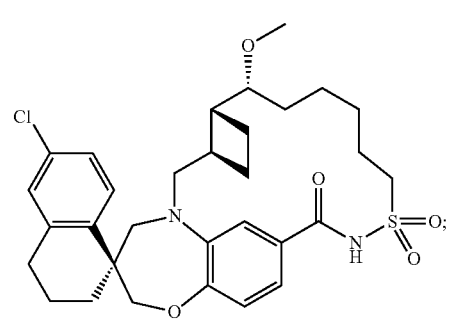
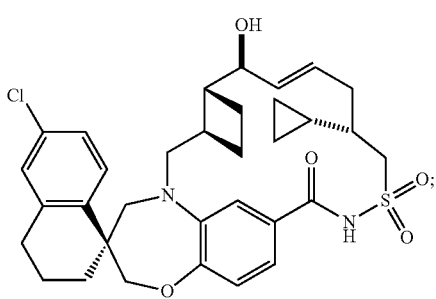
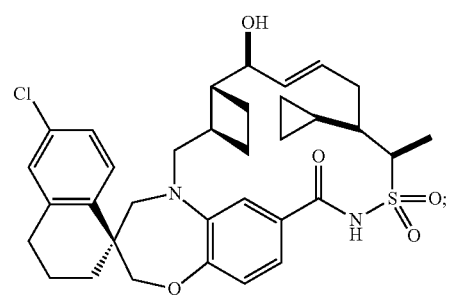
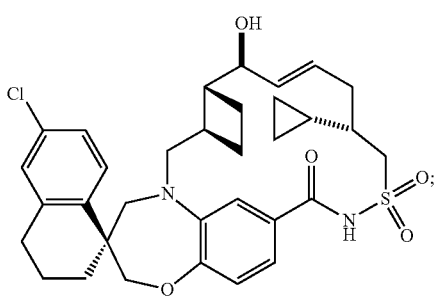
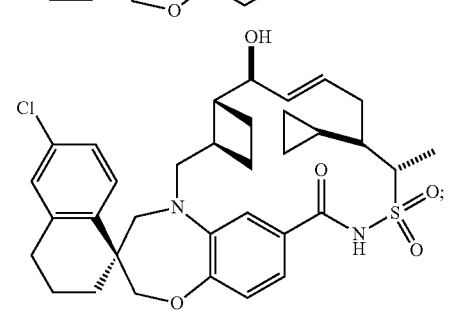
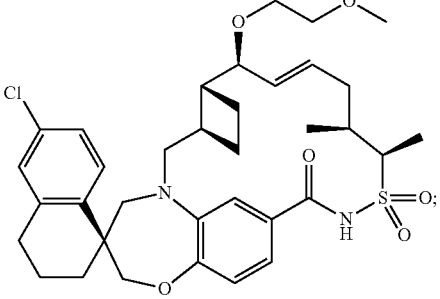

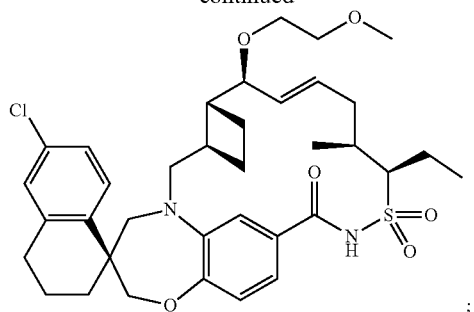
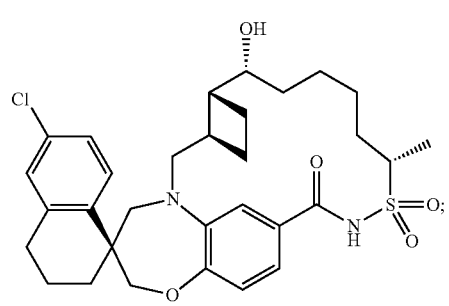
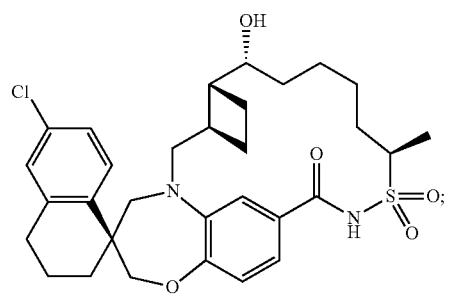
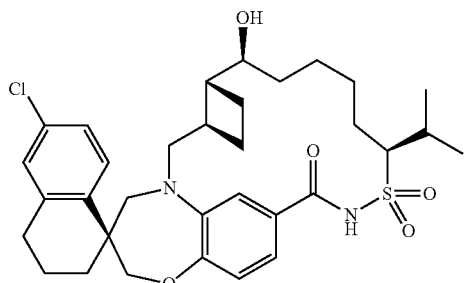
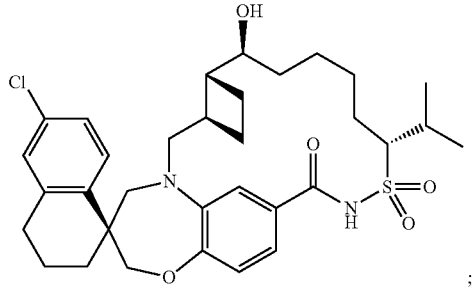
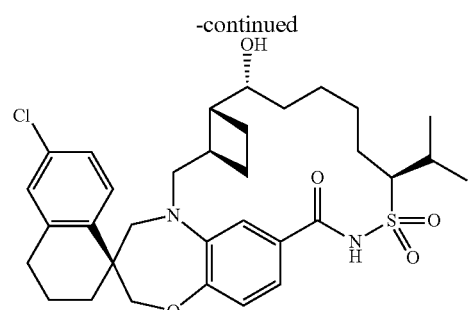
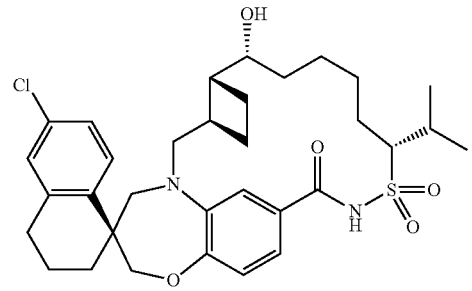
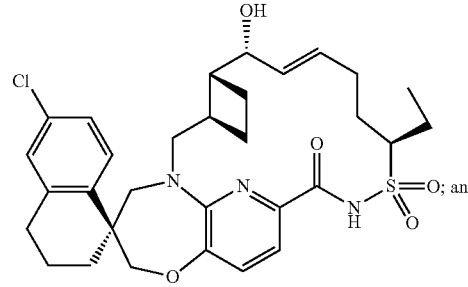

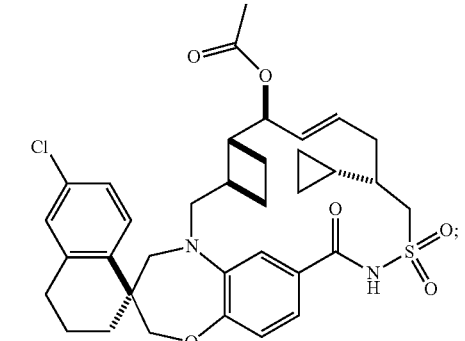
or a stereoisomer thereof; a pharmaceutically acceptable salt thereof, a pharmaceutically acceptable salt of the stereoisomer thereof.
In another embodiment, the present invention has a pharmaceutical composition comprising the compound of the present invention or a pharmaceutically acceptable stereoisomer thereof, or pharmaceutically acceptable salt thereof or stereoisomer of the salt thereof, and a pharmaceutically acceptable carrier or diluent.

In another embodiment, the present invention is a method of treating cancer, the method comprising: administering to a patient in need thereof a therapeutically effective amount of the compound of the present invention or a pharmaceutically acceptable salt thereof.

In another embodiment, the present invention is a method of treating cancer, wherein the cancer is a hematologic malignancy.

In another embodiment, the present invention is a method of treating cancer, wherein the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia.

In another embodiment, the present invention is a method of treating cancer, wherein the cancer is multiple myeloma.

In another embodiment, the present invention is a method of treating cancer, further comprising administering to the patient in need thereof a therapeutically effective amount of an additional pharmaceutically active compound.

In another embodiment, the present invention is a method of treating cancer, wherein the additional pharmaceutically active compound is carfilzomib.

In another embodiment, the present invention is a use of a compound of the present invention for treating cancer in a subject.

In another embodiment, the present invention is a use of a compound of the present invention in the preparation of a medicament for treating cancer.

In another embodiment, the present invention is a method of treating cancer, wherein the cancer is a hematologic malignancy.

In another embodiment, the present invention is a method of treating cancer, wherein the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia.

In another embodiment, the present invention is a method of treating cancer, wherein the cancer is multiple myeloma.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the claims.

DETAILED DESCRIPTION

The symbol "—" represents a covalent bond and can also be used in a radical group to indicate the point of attachment to another group. In chemical structures, the symbol is commonly used to represent a methyl group in a molecule.

As used herein, chemical structures which contain one or more stereocenters depicted with dashed and bold bonds (i.e., ⫶⫶⫶ and ▬) are meant to indicate absolute stereochemistry of the stereocenter(s) present in the chemical structure. As used herein, bonds symbolized by a simple line do not indicate a stereo-preference. Unless otherwise indicated to the contrary, chemical structures that include one or more stereocenters which are illustrated herein without indicating absolute or relative stereochemistry encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$ alkyl.

The term "compound", as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates).

The term "cycloalkyl" means a cyclic, nonaromatic hydrocarbon. Representative examples of cycloalkyl groups include cyclopropyl, cyclobutyl, cyclopentyl, cyclohexyl and cycloheptyl. A cycloalkyl group can contain one or more double bonds. Representative examples of cycloalkyl groups that contain double bonds include cyclopentenyl, cyclohexenyl, cyclohexadienyl and cyclobutadienyl. Common cycloalkyl groups are $C_{3-8}$ cycloalkyl groups.

The term "excipient", as used herein, means any pharmaceutically acceptable additive, carrier, diluent, adjuvant or other ingredient, other than the active pharmaceutical ingredient (API), which is typically included for formulation and/or administration to a patient. Handbook of Pharmaceutical Excipients, 5$^{th}$ Edition, R. C. Rowe, P. J. Sheskey, and S. C. Owen, editors, Pharmaceutical Press, 2005, Hardback, 928, 0853696187.

For the terms "for example" and "such as" and grammatical equivalences thereof, the phrase "and without limitation" is understood to follow unless explicitly stated otherwise.

The term "halogen" or "halo" means F, Cl, Br or I.

The term "oxo", when used as a substituent, means the =O group, which is typically attached to a carbon atom.

The term "patient" means subjects including animals, such as dogs, cats, cows, horses, sheep and humans. Particular patients are mammals. The term patient includes males and females.

The term "patient in need" means a patient having, or at risk of having, one or more diseases or conditions where the Mcl-1 protein is involved, such as cancers. Identifying a patient in need can be in the judgment of a subject or a health care professional and can be subjective (e.g., opinion) or objective (e.g., measurable by a test or diagnostic method).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection, and infusion.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The term "pharmaceutically acceptable" is employed herein to refer to those ligands, materials, compositions, and/or dosage forms which are, within the scope of sound medical judgment, suitable for administration to a patient, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

The term "substituted" means that a hydrogen atom on a molecule or group is replaced with a group or atom. Typical substitutents include: halogen, $C_{1-8}$alkyl, hydroxyl, $C_{1-6}$alkoxy, $NR^xR^x$, nitro, cyano, halo or perhalo$C_{1-8}$alkyl, $C_{2-8}$alkenyl, $C_{2-8}$alkynyl, $-SR^x$, $S(=O)_2R^x$, $C(=O)OR^x$, $C(=O)R^x$, wherein each $R^x$ is independently hydrogen or $C_1$-$C_8$ alkyl. It is noted that when the substituent is $-NR^xR^x$, the $R^x$ groups may be joined together with the nitrogen atom to form a ring.

A group or atom that replaces a hydrogen atom is also called a substituent.

Any particular molecule or group can have one or more substituent depending on the number of hydrogen atoms that can be replaced.

The phrases "systemic administration", "administered systemically", "peripheral administration", and "administered peripherally" as used herein mean the administration of a ligand, drug, or other material via route other than directly into the central nervous system, such that it enters the patient's system and thus, is subject to metabolism and other like processes, for example, subcutaneous administration.

The term "therapeutically effective amount" means an amount of a compound that ameliorates, attenuates or eliminates one or more symptom of a particular disease or condition, or prevents or delays the onset of one of more symptom of a particular disease or condition.

The terms "treating", "treat" or "treatment" and the like include preventative (e.g., prophylactic) and palliative treatment.

The methods provided herein include the manufacture and use of pharmaceutical compositions, which include one or more of the compounds provided herein. Also included are the pharmaceutical compositions themselves.

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxida Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A pharmaceutical composition may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

In some cases, in order to prolong the effect of one or more compounds provided herein, it is desirable to slow the absorption of the compound from subcutaneous or intramuscular injection. For example, delayed absorption of a parenterally administered compound can be accomplished by dissolving or suspending the compound in an oil vehicle.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. The dose of the compound or composition can be varied over time. All combinations, delivery methods and administration sequences are contemplated.

The compounds of the present invention and in some embodiments, other additional pharmaceutically active compounds, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent.

Formulations suitable for oral administration may be in the form of capsules (e.g., gelatin capsules), cachets, pills, tablets, lozenges (using a flavored basis, usually sucrose and acacia or tragacanth), powders, troches, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of a compound provided herein as an active ingredient. A composition may also be administered as a bolus, electuary, or paste. Oral compositions generally include an inert diluent or an edible carrier.

Pharmaceutically compatible binding agents, and/or adjuvant materials can be included as part of an oral composition. In solid dosage forms for oral administration (capsules, tablets, pills, dragees, powders, granules, and the like), the active ingredient can be mixed with one or more pharmaceutically acceptable carriers, such as sodium citrate or dicalcium phosphate, and/or any of the following: (1) fillers or extenders, such as starches, cyclodextrins, lactose, sucrose, saccharin, glucose, mannitol, and/or silicic acid; (2) binders, such as, for example, carboxymethylcellulose, microcrystalline cellulose, gum tragacanth, alginates, gelatin, polyvinyl pyrrolidone, sucrose, and/or acacia; (3) humectants, such as glycerol; (4) disintegrating agents, such as agar-agar, calcium carbonate, potato, corn, or tapioca starch, alginic acid, Primogel, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, Sterotes, solid polyethylene glycols, sodium lauryl sulfate, and mixtures thereof; (10) a glidant, such as colloidal silicon dioxide; (11) coloring agents; and (12) a flavoring agent such as peppermint, methyl salicylate, or orange flavoring. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of a powdered compound moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, microspheres, and/or nanoparticles. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions suitable for parenteral administration can include one or more compounds provided herein in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In one embodiment, the intravenous (IV) formulation consists of a composition containing hydroxypropyl beta cyclodextrin within a pH range between 8-10 as a buffered or unbuffered solution. The IV formulation can be formulated as a sterile solution ready for injection, a sterile solution ready for dilution into an IV admixture or a sterile solid for reconstitution. The API in the IV formulation may exist as a free acid/base or an in situ salt.

Examples of suitable aqueous and nonaqueous carriers which may be employed in the pharmaceutical compositions provided herein include water for injection (e.g., sterile water for injection), bacteriostatic water, ethanol, polyols (such as glycerol, propylene glycol, polyethylene glycol such as liquid polyethylene glycol, and the like), sterile buffer (such as citrate buffer), and suitable mixtures thereof, vegetable oils, such as olive oil, injectable organic esters, such as ethyl oleate, and Cremophor EL™ (BASF, Parsippany, NJ). In all cases, the composition must be sterile and should be fluid to the extent that easy syringability exists. Proper fluidity can be maintained, for example, by the use of coating materials, such as lecithin, by the maintenance of the required particle size in the case of dispersions, and by the use of surfactants.

The composition should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the methods of preparation are freeze-drying (lyophilization), which yields a powder of the active ingredient plus any additional desired ingredient from a previously sterile-filtered solution thereof.

Injectable depot forms can be made by forming microencapsule or nanoencapsule matrices of a compound provided herein in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes, microemulsions or nanoemulsions, which are compatible with body tissue.

For administration by inhalation, the compounds can be delivered in the form of an aerosol spray from a pressured container or dispenser that contains a suitable propellant (e.g., a gas such as carbon dioxide) or a nebulizer. Such methods include those described in U.S. Pat. No. 6,468,798. Additionally, intranasal delivery can be accomplished, as described in, inter alia, Hamajima et al., *Clin. Immunol. Immunopathol.*, 88(2), 205-10 (1998). Liposomes (e.g., as described in U.S. Pat. No. 6,472,375, which is incorporated herein by reference in its entirety), microencapsulation and nanoencapsulation can also be used. Biodegradable targetable microparticle delivery systems or biodegradable targetable nanoparticle delivery systems can also be used (e.g., as described in U.S. Pat. No. 6,471,996, which is incorporated herein by reference in its entirety).

Systemic administration of a therapeutic compound as described herein can also be by transmucosal or transdermal means. Dosage forms for the topical or transdermal administration of a compound provided herein include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The ointments, pastes, creams, and gels may contain, in addition to one or more compounds provided herein, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound provided herein, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A compound provided herein can be administered by aerosol. This is accomplished by preparing an aqueous aerosol, liposomal preparation, or solid particles containing a compound or composition provided herein. A nonaqueous (e.g., fluorocarbon propellant) suspension could be used. In some embodiments, sonic nebulizers are used because they minimize exposing the agent to shear, which can result in degradation of the compound.

Ordinarily, an aqueous aerosol can be made by formulating an aqueous solution or suspension of the agent together with conventional pharmaceutically acceptable carriers and stabilizers. The carriers and stabilizers vary with the requirements of the particular composition, but typically include nonionic surfactants (TWEEN® (polysorbates), PLURONIC® (poloxamers), sorbitan esters, lecithin, CREMOPHOR® (polyethoxylates)), pharmaceutically acceptable co-solvents such as polyethylene glycol, innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of a compound provided herein to the body. Such dosage forms can be made by dissolving or dispersing the agent in the proper medium. Absorption enhancers can also be used to increase the flux of the compound across the skin. The rate of such flux can be controlled by either providing a rate controlling membrane or dispersing the compound in a polymer matrix or gel.

The pharmaceutical compositions can also be prepared in the form of suppositories or retention enemas for rectal and/or vaginal delivery. Formulations presented as a suppository can be prepared by mixing one or more compounds provided herein with one or more suitable nonirritating excipients or carriers comprising, for example, cocoa butter, glycerides, polyethylene glycol, a suppository wax or a salicylate, which is solid at room temperature, but liquid at body temperature and, therefore, will melt in the rectum or vaginal cavity and release the active agent. Formulations which are suitable for vaginal administration also include pessaries, tampons, creams, gels, pastes, foams, or spray formulations containing such carriers as are known in the art to be appropriate.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially (e.g., from Alza Corporation and Nova Pharmaceuticals, Inc.). Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811, which is incorporated herein by reference in its entirety for all purposes.

The compounds of the present invention are used in the treatment of diseases, disorders or symptoms mediated by Mcl-1 inhibition. Examples of diseases, disorders or symptoms mediated by Mcl-1 inhibition include, but are not limited to, cancers. Non-limiting examples of cancers include breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia.

The cancers can include carcinomas (originating in the outer layer of cells of the skin and internal membranes, e.g., breasts, kidneys, lungs, skin); sarcomas (arising from connective tissue such as bone, muscle, cartilage, and blood vessels), and hematologic malignancies (e.g., lymphomas and leukemias, which arise in the blood or blood-forming organs such as the spleen, lymph nodes, and bone marrow). Cancer cells can include, for example, tumor cells, neoplastic cells, malignant cells, metastatic cells, and hyperplastic cells.

In an embodiment, the disease, disorder or symptom is a hyperproliferative disorder, e.g., a lymphoma, leukemia, carcinoma (e.g., renal, breast, lung, skin), multiple myeloma, or a sarcoma. In one embodiment, the leukemia is acute myeloid leukemia. In one embodiment, the hyperproliferative disorder is a relapsed or refractory cancer.

Actual dosage levels of the active ingredients in the pharmaceutical compositions provided herein may be varied so as to obtain an amount of the active ingredient which is effective to achieve the desired therapeutic response for a particular patient, composition, and mode of administration, without being toxic to the patient.

The specific dosage and dosage range depends on a number of factors, including the requirements of the patient, the severity of the condition or disease being treated, the pharmacokinetic characteristics of the compound(s) employed, and the route of administration. In some embodiments, the compositions provided herein can be provided in an aqueous solution containing about 0.1-10% w/v of a compound disclosed herein, among other substances, for parenteral administration. Typical dose ranges can include from about 0.01 to about 50 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Dosage forms or compositions containing a compound as described herein in the range of 0.005% to 100% with the balance made up from non-toxic carrier may be prepared. Methods for preparation of these compositions are known to those skilled in the art. The contemplated compositions may contain about 0.001%-100% active ingredient, in one embodiment from about 0.1 to about 95%, in another embodiment from about 75 to about 85%. Although the dosage will vary depending on the symptoms, age and body weight of the patient, the nature and severity of the disorder to be treated or prevented, the route of administration and the form of the drug, in general, a daily dosage of from about 0.01 to about 3,000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing The compounds of the present invention can be administered alone, in combination with other compounds of the present invention, or with other pharmaceutically active compounds or agents. The other pharmaceutically active compounds/agents can be intended to treat the same disease or condition as the compounds of the present invention or a different disease or condition. If the patient is to receive or is receiving multiple pharmaceutically active compounds or agents, the compounds can be administered simultaneously, or sequentially.

The compounds of the present invention, or pharmaceutically acceptable salts thereof, may be used in combination with one or more additional pharmaceutically active compounds/agents.

One or more additional pharmaceutically active compounds or agents may be administered separately, as part of a multiple dose regimen, from the compound of Formula I (e.g., sequentially, e.g., on different overlapping schedules with the administration of one or more compounds of Formula I (including any subgenera or specific compounds thereof). In other embodiments, the one or more additional compounds/agents may be part of a single dosage form, mixed together with the compound of Formula I in a single composition. In still another embodiment, the one or more additional compounds/agents can be given as a separate dose that is administered at about the same time that one or more compounds of Formula I are administered (e.g., simultaneously with the administration of one or more compounds of Formula I (including any subgenera or specific compounds thereof). Both the compound of Formula I and the one or more additional compounds/agents can be present at dosage levels of between about 1 to 100%, and more preferably between about 5 to 95% of the dosage normally administered in a monotherapy regimen.

In a particular embodiment, the additional pharmaceutically active compound/agent is a compound or agent that can be used to treat a cancer. For example, the additional pharmaceutically active compound/agent can be selected from antineoplastic agents, anti-angiogenic agents, chemotherapeutic agents, and peptidal cancer therapy agents. In another embodiment, the antineoplastic agents are selected from antibiotic-type agents, alkylating agents, antimetabolite agents, hormonal agents, immunological agents, interferon-type agents, kinase inhibitors, proteasome inhibitors, and combinations thereof. It is noted that the additional pharmaceutically active compound/agent may be a traditional small organic chemical molecule or can be a macromolecule such as a protein, antibody, peptibody, DNA, RNA or a fragment of such macromolecules.

Examples of additional pharmaceutically active compounds/agents that can be used in the treatment of cancers and that can be used in combination with one or more compounds of the present invention include: acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflornithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracil/oteracil/tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon afla-N1; interferon alfa-n3; interferon alfacon-1; interferon alpha natural; interferon beta; interferon beta-1a; interferon beta-1b; interferon gamma natural; interferon gamma-1a; interferon gamma-1b; interleukin-1 beta; iobenguane; irsogladine; lanreotide; LC 9018 (Yakult); leflunomide; lenograstim; lentinan sulfate; letrozole; leukocyte alpha interferon; leuprorelin; levamisole+fluorouracil; liarozole; lobaplatin; lonidamine; lovastatin; masoprocol; melarsoprol; metoclopramide; mifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; pentosan polysulfate sodium; pentostatin; picibanil; pirarubicin; rabbit antithymocyte polyclonal antibody; polyethylene glycol interferon alfa-2a; porfimer sodium; raltitrexed; rasburicase; rhenium Re 186 etidronate; RII retinamide; romurtide; samarium (153 Sm) lexidronam; sargramostim; sizofuran; sobuzoxane; sonermin; strontium-89 chloride; suramin; tasonermin; tazarotene; tegafur; temoporfin; teniposide; tetrachlorodecaoxide; thymalfasin; thyrotropin alfa; toremifene; tositumomab-iodine 131; treosulfan; tretinoin; trilostane; trimetrexate; triptorelin; tumor necrosis factor alpha natural; ubenimex; bladder cancer vaccine; Maruyama vaccine; melanoma lysate vaccine; valrubicin; verteporfin; virulizin; zinostatin stimalamer; abarelix; AE 941 (Aeterna); ambamustine; antisense oligonucleotide; bcl-2 (Genta); APC 8015 (Dendreon); dexaminoglutethimide; diaziquone; EL 532 (Elan); EM 800 (Endorecherche); eniluracil; etanidazole; fenretinide; galocitabine; gastrin 17 immunogen; HLA-B7 gene therapy (Vical); granulocyte macrophage colony stimulating factor; histamine dihydrochloride; ibritumomab tiuxetan; ilomastat; IM 862 (Cytran); interleukin-2; iproxifene; LDI 200 (Milkhaus); leridistim; lintuzumab; CA 125 monoclonal antibody (MAb) (Biomira); cancer MAb (Japan Pharmaceutical Development); HER-2 and Fc MAb (Medarex); idiotypic 105AD7 MAb (CRC Technology); idiotypic CEA MAb (Trilex); LYM-1-iodine 131 MAb (Techniclone); polymorphic epithelial mucin-yttrium 90 MAb (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (SUGEN); TA 077 (Tanabe); tetrathiomolybdate; thaliblastine; thrombopoietin; tin ethyl etiopurpurin; tirapazamine; cancer vaccine (Biomira); melanoma vaccine; melanoma oncolysate vaccine; viral melanoma cell lysates vaccine; valspodarl; fluorouracil; 5-fluorouracil; pacitaxel; imatinib; altretamine; cladibrine; cyclophosphamine; decarazine; irinotecan; mitosmycin; mitoxane; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; carfilzomib (published in WO2006017842); oprozomib (WO2007056464); vorinostat; capecitabine; zoledronic acid; anastrozole; sunitinib; aprepitant and nelarabine, or a pharmaceutically acceptable salt thereof.

Additional pharmaceutically active compounds/agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

In certain embodiments, a composition provided herein is conjointly administered with a chemotherapeutic agent. Suitable chemotherapeutic agents may include, natural products such as vinca alkaloids (e.g., vinblastine, vincristine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TGO2 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163 L), aurora kinase inhibitors (e.g., MLN8237), cell surface monoclonal antibodies (e.g., anti-CD38 (HUMAX-CD38), anti-CS1 (e.g., elotuzumab), HSP90 inhibitors (e.g., 17 AAG and KOS 953), P13K/Akt inhibitors (e.g., perifosine), Akt inhibitor (e.g., GSK-2141795), PKC inhibitors (e.g., enzastaurin), FTIs (e.g., Zarnestra™), anti-CD138 (e.g., BT062), Torcl/2 specific kinase inhibitor (e.g., INK128), kinase inhibitor (e.g., GS-1101), ER/UPR targeting agent (e.g., MKC-3946), cFMS inhibitor (e.g., ARRY-382), JAK1/2 inhibitor (e.g., CYT387), PARP inhibitor (e.g., olaparib and veliparib (ABT-888)), BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

The compounds of the present invention may also be used in combination with radiation therapy, hormone therapy, surgery and immunotherapy, which therapies are well known to those skilled in the art.

In certain embodiments, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chlorprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof. In a particular embodiment, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$-$C_{12}$) alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as (3-dimethylaminoethyl), carbamoyl-($C_1$-$C_2$)alkyl, N,N-di ($C_1$—$C_2$)alkylcarbamoyl-($C_1$-$C_2$)alkyl and piperidino-, pyrrolidino- or morpholino(C2-3)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers.

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The compounds of the present invention may exist in various solid states including crystalline states and as an amorphous state. The different crystalline states, also called polymorphs, and the amorphous states of the present compounds are contemplated as part of this invention.

EXAMPLES

The examples presented below illustrate specific embodiments of the present invention. These examples are meant to be representative and are not intended to limit the scope of the claims in any manner.

The following abbreviations may be used herein:

| | |
|---|---|
| ~ | about |
| Ac$_2$O | acetic anhydride |
| AcOH | acetic acid |
| Al$_2$O$_3$ | aluminum oxide |
| Bz | benzyl |

| Calcd | Calculated |
|---|---|
| CO₂ | carbon dioxide |
| CSA | 10-camphorsulfonic acid |
| DBU | 1,8-diazabicyclo[5.4.0]undec-7-ene |
| DCE | Dichloroethane |
| DCM | Dichloromethane |
| DEA | Diethylamine |
| Dess-Martin periodinane; | 1,1,1-triacetoxy-1,1-dihydro-1,2-benziodoxol-3-(1H)-one |
| DIEA or DIPEA | Diisopropylethylamine |
| DMAP | 4-dimethylaminopyridine |
| DMF | N,N-dimethylformamide |
| DMSO | dimethyl sulfoxide |
| EDC | N-ethyl-N'-(3-dimethylaminopropyl)carbodiimide |
| ee or e.e. | enantiomeric excess |
| eq | Equivalent |
| ESI or ES | electrospray ionization |
| Et | Ethyl |
| Et₂O | diethyl ether |
| EtOAc | ethyl acetate |
| Et₃N | triethylamine |
| EtOH | ethyl alcohol |
| g | gram(s) |
| GC | gas chromatography |
| h | hour(s) |
| ¹H NMR | proton nuclear magnetic resonance spectroscopy |
| H₂ | hydrogen gas |
| H₂O | Water |
| H₂SO₄ | sulfuric acid |
| HATU | 1-[Bis(dimethylamino)methylene]-1H-1,2,3-triazolo[4,5-b]pyridinium 3-oxid hexafluorophosphate |
| HCl | hydrochloric acid |
| Hex | hexane(s) |
| HPLC | high performance liquid chromatography |
| IP | intraperitoneal |
| IPA | isopropyl alcohol |
| IPAc | isopropyl acetate |
| K₂CO₃ | potassium carbonate |
| K₃PO₄ | potassium phosphate |
| KF | Karl Fischer titration |
| KHMDS | potassium hexamethyldisilazide |
| KOAc | potassium acetate |
| KOH | potassium hydroxide |
| L | liter(s) |
| LAH | lithium aluminium hydride |
| LCMS, LC-MS or LC/MS | liquid chromatography mass spectrometry |
| LiHMDS | lithium hexamethyldisilazide |
| LiOH | lithium hydroxide |
| M | molar (mol L⁻¹) |
| Me | methyl |
| MeCN | acetonitrile |
| MeI | iodomethane |
| MeOH | methyl alcohol |
| MeTHF | methyltetrahydrofuran |
| mg | milligram(s) |
| MgSO₄ | magnesium sulphate |
| min | minute(s) |
| mL | milliliter(s) |
| MS | mass spectrometry |
| MSA | methanesulfonic acid |
| MsCl | methanesulfonyl chloride |
| MTBE | methyl tert-butyl ether |
| m/z | mass-to-charge ratio |
| N | Normality (Eq/L) |
| N₂ | nitrogen gas |
| NaCl | sodium chloride |
| Na₂CO₃ | sodium carbonate |
| NaHCO₃ | sodium bicarbonate |
| NaH₂PO₄ | sodium dihydrogen phosphate |
| NaNO₂ | sodium nitrite |
| NaOH | sodium hydroxide |
| NaOtBu | sodium tert-butoxide |
| Na₂SO₄ | sodium sulfate |
| Na₂S₂O₃ | sodium thiosulfate |
| NH₃ | ammonia, azane |
| NH₄Cl | ammonium chloride |
| NH₄OH | ammonium hydroxide |
| NMP | 1-methyl-2-pyrrolidinone |
| NMR | nuclear magnetic resonance spectroscopy |
| PO | per oral |
| POCl₃ | phosphoryl chloride |
| PhMe | toluene |
| ppm | parts per million |
| QD | once daily |
| QNMR | quantitative NMR |
| RBF | round-bottomed flask |
| RT or rt or r.t. | room temperature |
| sat. or sat'd or satd | Saturated |
| SFC | supercritical fluid chromatography |
| SiO₂ | silicon dioxide, silica |
| SOCl₂ | thionyl chloride |
| tBu | tert butyl |
| TEMPO | (2,2,6,6-tetramethylpiperidin-1-yl)oxidanyl |
| TFA | triflouroacetic acid |
| THF | Tetrahydrofuran |
| TLC | thin layer chromatography |
| TsOH | toluene sulfonic acid |
| v/v | volume per volume |

It is noted that when a percent (%) is used with regard to a liquid, it is a percent by volume with respect to the solution. When used with a solid, it is the percent with regard to the solid composition.

The following synthetic schemes show generally how to make intermediates and compounds of the present invention.

General Synthetic Schemes

Synthetic Schemes

Compounds of the present invention generally can be prepared combining and further elaborating common advanced synthetic intermediates generated from commercially available starting materials, using synthetic techniques known to those of skill in the art. The syntheses of these common advanced intermediates are outlined below and further exemplification is found in the specific examples provided.

Common Advanced Intermediates

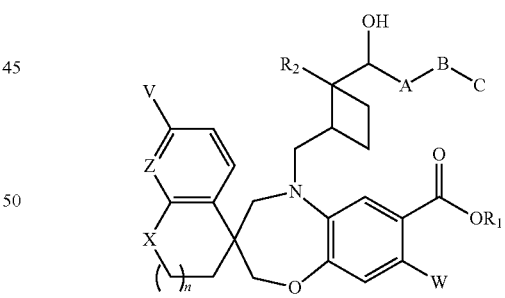

Intermediate AA

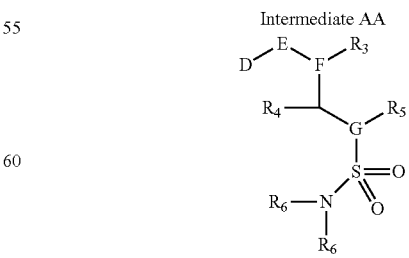

Intermediate EE

Intermediate AA11A (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic Acid

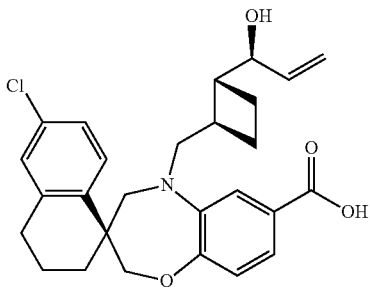 [SMILES: C=C[C@H](O)[C@@H]1CC[C@H]1CN1C[C@@]2(CCCc3cc(Cl)ccc32)COc2ccc(C(=O)O)cc21]

Step 1: 6-chloro-3,4-dihydronaphthalen-1(2H)-one

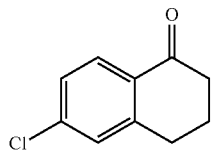 [SMILES: O=C1CCCc2cc(Cl)ccc21]

A 1 L beaker was charged with 6-amino-3,4-dihydro-1(2H)-naphthalenone (47.5 g, 1 eq), H$_2$O (250 mL), and concentrated HCl (57 mL). The mixture was stirred with a plastic straw until dissolution and cooled to <0° C. NaNO2 (22.4 g) solution in H$_2$O (45 mL) was added dropwise to the 6-aminotetralone HCl solution, while manually stirred, maintaining the temperature below 0° C. to give a dark red solution, which was used directly for chlorination.

To a 2 L 4-necked round bottom flask with open necks was added cuprous chloride (99 g, 1002 mmol) and concentrated HCl (393 mL, 4715 mmol) to give a dark solution which was cooled to 0° C. The diazotized solution (starting with 6-aminotetralone 95 g) was added portion-wise into the CuCl/HCl solution, maintaining the temp below 10° C. The resulting dark reaction mixture was allowed to warm to ambient temperature, stirred for 1 h and poured into a separatory funnel with DCM (150 mL). After partition, the aqueous layer was extracted with DCM (100 mL). The combined organic layers were washed with H$_2$O (75 mL). To the DCM stream was added saturated NaHCO$_3$ (100 mL) and Darco (15 g), the mixture was stirred for 15 min and then filtered through a celite pad. The layers were separated and the aqueous was washed with DCM (30 mL). The organic layers were combined and concentrated to give a brown oil, which could be used directly in the next step. The batch could be further purified by filtration through a plug of silica gel (~100 g) rinsing with 10-50% EtOAc/heptane followed by concentration to give the product as a brown oil (87.5 g, 82% yield).

Step 2: (R)-6-chloro-3,4-dihydro-2H-spiro[naphthalene-1,2'-oxirane] and (R)-6-chloro-3,4-dihydro-2H-spiro[naphthalene-1,2'-oxirane]

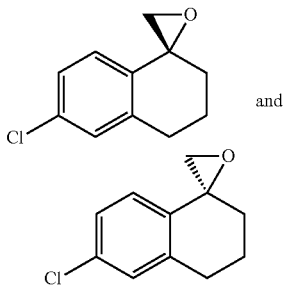

A 2 L 4-necked RBF was charged 6-chloro-3,4-dihydro-1(2H)-naphthalenone (123 g, 681 mmol), trimethylsulfonium iodide (143 g, 701 mmol) and DMSO (1100 mL, 8.94 mL/g). Potassium hydroxide (76 g, 1362 mmol) (pellets) was added. The suspension was stirred at ambient temperature for 2 days after which time crude $^1$H NMR showed no remaining starting material. The solution was poured into 800 g of crushed ice, rinsed with MTBE (200 mL) and an additional portion of MTBE (700 mL) was added. The resulting mixture was stirred for 5 min. and after partition the bottom aqueous layer was extracted with MTBE twice (500 mL, 300 mL) and combined with the main MTBE extract. The combined organic stream was washed with brine (2×600 mL) and 330 g of Al$_2$O$_3$ (neutral) was added. The resulting suspension was stirred for 5 min. at 22° C., filtered and washed with MTBE (400 mL). The filtrate was concentrated to give the title compound as a red viscous oil (125 g, 94%).

Step 3: (S)-6-chloro-1,2,3,4-tetrahydronaphthalene-1-carbaldehyde and (R)-6-chloro-1,2,3,4-tetrahydronaphthalene-1-carbaldehyde

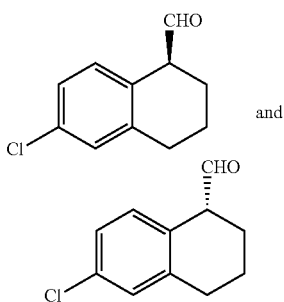

A 3 L 3-necked RBF was charged with racemic 6-chloro-3,4-dihydro-2H-spiro[naphthalene-1,2'-oxirane](160 g, 822 mmol) and THF (1760 mL, 11 mL/g). After the batch was cooled to −8° C. with a dry ice/IPA bath, boron trifluoride diethyl etherate (5.07 mL, 41.1 mmol) was added over 3 min. An exotherm raised the batch temp to 10° C. instantly. The batch was stirred at −5 to 0° C. for 5 min, and LC analysis of a sample (quenched into cold NaHCO$_3$ solution) showed complete conversion. The reaction was quenched by the addition of saturated NaHCO$_3$ (300 mL) at −5° C. followed by MTBE (400 mL, 2.5 mL/g) and the mixture was transferred to a separatory funnel and rinsed with MTBE (240 mL, 1.5 mL/g). After partition, the aqueous layer was discarded along with some white solid (likely boric acid or borax). The organic layer was washed with brine (350 mL) and concentrated under reduced pressure to give a red oil. The crude material was used directly in the next step.

Step 4: (6-chloro-1,2,3,4-tetrahydronaphthalene-1,1-diyl)dimethanol

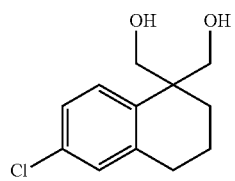

Racemic 6-chloro-1,2,3,4-tetrahydro-1-naphthalenecarbaldehyde was charged onto a 3 L 3-necked RBF and rinsed with diethylene glycol (1000 mL, 5.88 mL/g). Formaldehyde 37% solution (652 mL, 8757 mmol) was added and the resulting biphasic emulsion was cooled to 5° C. with a dry ice/IPA bath. Potassium hydroxide (45% aqueous solution, 652 mL, 11.9 mol) was added over ~30 min, maintaining the temperature below 20° C. After complete addition, the batch (20° C.) was slowly heated to 45° C. (Caution: Exothermic reaction) and aged for 1 h. HPLC showed complete conversion. Note: Some viscous insoluble tar was formed and it was removed prior to aqueous workup. To the batch was added brine (500 mL) and the mixture was extracted with DCM until the product content in the aqueous phase was less than 5%. The combined DCM extract was concentrated to 750 mL as a red oil, washed with $H_2O$ (500 mL), and the product started to crystallize out. Separated the suspension+DCM and discarded the clear top aqueous layer. The bottom layer was stirred in ice/$H_2O$ bath for 30 min, filtered and washed with DCM (~100 mL) and $H_2O$ (100 mL). The product was dried under dry air/vacuum to give a first crop (113 g, 498 mmol, 57% yield). The DCM layer from the resulting mother liquor was separated and concentrated to 200-300 g (KF=0.5%), seeded, and stirred in ice/H2O bath for 30 min. The product was filtered, washed with DCM (~50 mL), and dried in dry air/vacuum to give a second crop (14.3 g, 63.1 mmol, 7% yield) for a combined total yield of 6-chloro-1,2,3,4-tetrahydronaphthalene-1,1-diyl)dimethanol of 127 g (64%).

Step 5: (S)-(6-chloro-1-(hydroxymethyl)-1,2,3,4-tetrahydronaphthalen-1-yl)methyl 4-bromobenzoate

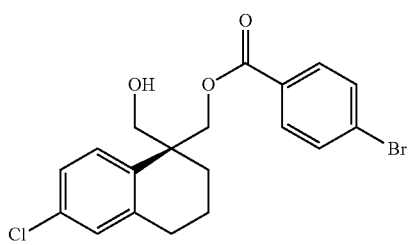

To a solution of 2,6-bis((R)-5,5-dibutyl-4-phenyl-4,5-dihydrooxazol-2-yl)pyridine (R,R-Kang Catalyst) (1.57 g, 2.64 mmol) in dry DCM (450 mL), copper(II) chloride (0.355 g, 2.64 mmol) was added and the resulting green colored solution was stirred at room temperature for 1 h. This solution was added via cannula to solution of (6-chloro-1,2,3,4-tetrahydronaphthalene-1,1-diyl)dimethanol (30 g, 132.73 mmol) in dry DCM (800 mL). The resulting mixture was cooled to −78° C. and a light green colored precipitation was observed in the reaction after some time. A solution of 4-bromobenzoyl chloride (34.77 g, 158.79 mmol) in DCM (500 mL) was then added slowly followed by the dropwise addition of N-ethyl-N-isopropylpropan-2-amine (20 g, 154 mmol). The resulting reaction mixture was stirred at −78° C. for 3 h then it was quenched with pH 3 phosphate buffer (1 L) and warmed to ambient temperature with vigorous stirring. The mixture was then diluted with DCM (2 L) and the layers were separated. The organic phase was washed with pH 3 buffer (1 L), sat. $NaHCO_3$ (1 L), and brine (2 L) then it was dried over sodium sulfate, filtered and concentrated. The crude material thus obtained was purified by column chromatography over silica gel (100-200 mesh, 80% DCM in hexane) afforded pure (S)-(6-chloro-1-(hydroxymethyl)-1,2,3,4-tetrahydronaphthalen-1-yl)methyl 4-bromobenzoate (45 g, 84%; e.r=91.4:8.6 ChiralCel OD-H (250 mm×4.6 mm); Mobile Phase: n-Hexane:IPA: 90:10; Run Time: 20 min; flow rate: 1 ml/min; sample preparation: IPA. Retention time (major peak)-9.32 min; Retention time (minor peak)-11.46 min). RE 0.6 in 100% DCM.

Step 6: (R)-(6-chloro-1-formyl-1,2,3,4-tetrahydronaphthalen-1-yl)methyl 4-bromobenzoate

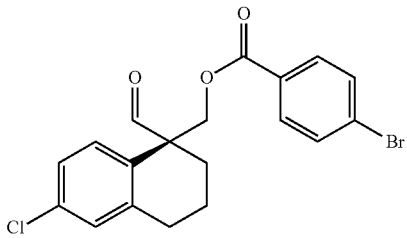 [SMILES: O=C[C@]1(COC(=O)c2ccc(Br)cc2)CCCc2cc(Cl)ccc21]

To a stirred solution of (S)-(6-chloro-1-(hydroxymethyl)-1,2,3,4-tetrahydronaphthalen-1-yl)methyl 4-bromobenzoate (100 g, 244.5 mmol) in DCM (2.5 L), Dess-Martin periodinane (121.4 g, 293.3 mmol) was added at 10° C. The cooling bath was removed after addition and the reaction mixture was stirred for 30 min at ambient temperature. Water (9 mL) was then added and the resulting biphasic mixture was stirred further at ambient temperature for 30 min. The reaction mixture was then cooled to 0° C. and quenched with 2 L of a 1:1 mixture of 10% $Na_2S_2O_3$/Saturated $NaHCO_3$ solution. The reaction mixture was stirred further at ambient temperature for 10 min then the layers were separated and the aqueous layer was extracted with ethyl acetate (2×1.5 L). The combined organic layer was washed with 1 L of 10% $Na_2S_2O_3$/Saturated $NaHCO_3$ solution and 1 L of brine then it was dried over sodium sulfate, filtered, and concentrated. Purification of the residue by column chromatography over silica gel (100-200 mesh, 5% ethyl acetate/hexane) afforded (R)-(6-chloro-1-formyl-1,2,3,4-tetrahydronaphthalen-1-yl)methyl 4-bromobenzoate (80 g, 81%). $R_f$: 0.7 in 10% ethyl acetate in hexane.

The enantiomeric purity of the title compound could be improved by the following procedure: (R)-(6-chloro-1- formyl-1,2,3,4-tetrahydronaphthalen-1-yl)methyl4-bromobenzoate (190 g) was added in toluene (950 mL) and heated to 50° C. to complete dissolution. The homogeneous solution was cooled to ambient temperature and seeded with racemic compound. The solution was cooled to −25° C. and aged overnight. The mother liquor was then decanted and concentrated to afford 160 g of enantiomerically enriched (R)-(6-chloro-1-formyl-1,2,3,4-tetrahydronaphthalen-1-yl) methyl 4-bromobenzoate (94% ee as determined by chiral HPLC).

Chiral HPLC conditions: Column: ChiralCel OD-H (250 mm×4.6 mm); Mobile Phase: n-Hexane:IPA: 90:10. Run Time: 20 min. Flow rate: 1 ml/min. Sample preparation: ethanol. Retention time (major peak)-8.488 min. (96.97%); Retention time (minor peak)-9.592 min. (3.03%).

Step 7: (R)-(6-chloro-1-(dimethoxymethyl)-1,2,3,4-tetrahydronaphthalen-1-yl)methanol

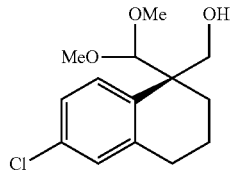 [SMILES: COC(OC)[C@]1(CO)CCCc2cc(Cl)ccc21]

To a solution of (R)-(6-chloro-1-formyl-1,2,3,4-tetrahydronaphthalen-1-yl)methyl 4-bromobenzoate (75 g, 183.8 mmol) in anhydrous MeOH (1 L), p-toluene sulfonic acid (1 g, 9.2 mmol) and trimethyl orthoformate (58.4 mL, 551 mmol) were added and the reaction mixture was refluxed until the starting material was completely consumed (~4 h). The reaction mass was concentrated to 50% volume and diluted with THF (1 L) and 1N NaOH (1 L, 1 mol). The resulting reaction mixture was stirred at 40° C. overnight then it was concentrated under reduced pressure and the residue was diluted with ethyl acetate (1.5 L). The aqueous layer was separated and extracted with ethyl acetate (2×500 mL) and the combined organic layers were washed with 1N NaOH (1 L) and brine (1 L), dried over sodium sulfate and concentrated under reduced pressure. The crude material was purified by column chromatography over 100-200 mesh size silica gel (10% ethyl acetate/hexane) affording pure (R)-(6-chloro-1-(dimethoxymethyl)-1,2,3,4-tetrahydronaphthalen-1-yl)methanol as a light brown thick oil (44 g, 89%). $R_f$: 0.5 in 30% ethyl acetate in hexane.

Step 8: tert-butyl-4-fluoro-3-nitrobenzoate

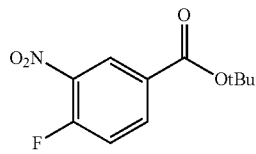 [SMILES: CC(C)(C)OC(=O)c1ccc(F)c([N+](=O)[O-])c1]

To a solution of 4-fluoro-3-nitrobenzoic acid (100 g, 540.2 mmol) in t-butanol (2.5 L), DMAP (13.18 g, 108.04 mmol) and di tert-butyl dicarbonate (248 mL, 1080.4 mmol) were added and the reaction mixture was heated at 40° C. overnight. On completion, the reaction mixture was diluted with water and the aqueous phase was extracted with ethyl acetate (3×1.5 L). The combined organic layer was washed further with water (1×1 L), brine (1×1 L) and dried over sodium sulfate. The solvent was removed under reduced pressure and the crude material thus obtained was purified by column chromatography (100-200 mesh size silica gel, eluting with a gradient of 100% hexanes to 5% Ethyl acetate in hexanes) affording pure tert-butyl-4-fluoro-3-nitrobenzoate (70 g, 54%) as light yellow solid. $R_f$: 0.5 in 5% ethyl acetate in hexane.

Step 9: (R)-tert-butyl 4-((6-chloro-1-(dimethoxymethyl)-1,2,3,4-tetrahydronaphthalen-1-yl)methoxy)-3-nitrobenzoate

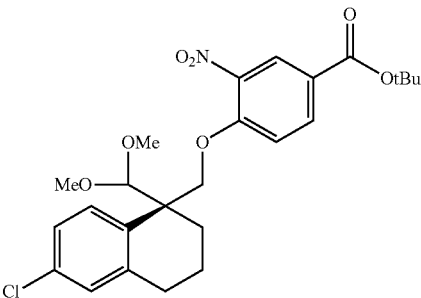 [SMILES: COC(OC)[C@]1(COc2ccc(C(=O)OC(C)(C)C)cc2[N+](=O)[O-])CCCc2cc(Cl)ccc21]

A solution of (R)-(6-chloro-1-(dimethoxymethyl)-1,2,3,4-tetrahydronaphthalen-1-yl)methanol (70 g, 259.2 mmol) in dry THF (3.5 L) was cooled to 0° C. and LiHMDS (1 M in THF) (363 mL, 363 mmol) was added dropwise. After 5 min, a solution of tert-butyl 4-fluoro-3-nitrobenzoate (74.9 g, 311 mmol) in THF (500 mL) was added dropwise via dropping funnel and the resulting mixture was warmed to ambient temperature. Upon completion (~1 h), the mixture was cooled to 0° C., quenched with saturated NH$_4$Cl solution (1 L) and extracted with ethyl acetate (3×1 L). The combined organic layers were washed with NH$_4$Cl (1 L) and brine (1 L), dried over sodium sulfate and concentrated under reduced pressure. The crude material thus obtained was purified by column chromatography using 100-200 mesh size silica gel (5% ethyl acetate/hexane) to afford (R)-tert-butyl 4-((6-chloro-1-(dimethoxymethyl)-1,2,3,4-tetrahydronaphthalen-1-yl)methoxy)-3-nitrobenzoate as yellow thick oil (110 g, 87% yield). $R_f$: 0.6 in 10% ethyl acetate in hexane Step 10a: (R)-4-((6-chloro-1-formyl-1,2,3,4-tetrahydronaphthalen-1-yl)methoxy)-3-nitrobenzoic Acid

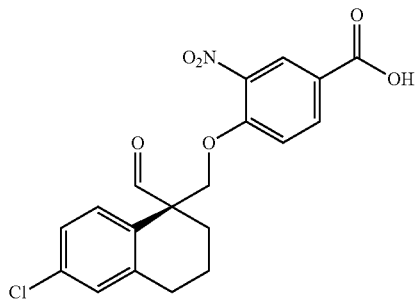 [SMILES: O=C[C@]1(COc2ccc(C(=O)O)cc2[N+](=O)[O-])CCCc2cc(Cl)ccc21]

To a solution of (R)-tert-butyl 4-((6-chloro-1-(dimethoxymethyl)-1,2,3,4-tetrahydronaphthalen-1-yl)methoxy)-3-nitrobenzoate (35 g, 71.25 mmol) in acetonitrile (1 L) erbium triflate (4.3 g, 7.1 mmol) and water (13 mL) were added. The resulting mixture was heated to 80° C. overnight. The solvent was then removed under reduced pressure and the residue was dissolved in diethyl ether (1.5 L) and washed with 1N HCl (500 mL) and brine (500 mL). The organic layer was dried over $Na_2SO_4$, filtered, and concentrated to afford (R)-4-((6-chloro-1-formyl-1,2,3,4-tetrahydronaphthalen-1-yl)methoxy)-3-nitrobenzoic acid (30 g) which was used without further purification. $R_f$: 0.15 in 30% ethyl acetate in hexane.

Alternatively, (R)-4-((6-chloro-1-formyl-1,2,3,4-tetrahydronaphthalen-1-yl)methoxy)-3-nitrobenzoic acid could be prepared from (6-chloro-1,2,3,4-tetrahydronaphthalene-1,1-diyl)dimethanol (Step 4) as follows:

A 250 mL 3-necked-round bottom flask was charged with copper (II) chloride (0.095 g, 0.02 equiv), 2,6-bis((R)-5,5-dibutyl-4-phenyl-4,5-dihydrooxazol-2-yl)pyridine (0.42 g, 0.02 equiv) and THF (28.5 g, 4V). After inertion with $N_2$, the batch was stirred at 20° C. for 0.5 h. To the homogenous green solution was added (6-chloro-1,2,3,4-tetrahydronaphthalene-1,1-diyl)dimethanol (8.0 g, 1.00 equiv) followed by THF (14.2 g, 2V) and 4-methylmorpholine (3.75 g, 1.05 equiv). The reaction mixture was cooled to −20° C., and a solution of 1-napthoyl chloride (7.06 g, 1.05 equiv) in THF (21.3 g, 3 V) was added to the batch over 0.5 h maintaining the temperature below −15° C. After aging at −20° C. for 20 h, an aliquot of the reaction slurry was sampled and assayed by HPLC (result in the table). The slurry was directly filtered through a glass-fritted funnel while maintaining the temperature at −20° C. The filter cake was washed with two portions of cold (<−10° C.) THF (2×14.2 g, 2V) rinsed through the reaction vessel. The filter cake (4-methylmorpholine·HCl) was transferred to an appropriately labeled container. The mother liquor and washes were concentrated to a minimum volume and distillative solvent swap by charging toluene until the batch volume is 6V and toluene/THF ratio is >98:2 (v/v) as measured by qNMR. To the batch at 20° C. was added heptane (11 g, 2V) and the slurry was heated to 85° C. (dissolution observed). The solution was cooled to 75° C. and charged with seed (0.27 g, 0.02 equiv). The slurry was cooled to 20° C. over 3 h and aged for >1 h. The batch was filtered through a glass-fritted filter and the cake was washed with toluene/heptane (3:1 v/v) (11 g, 2V) then toluene/heptane (1:1 v/v) (11 g, 2V). The cake was dried under $N_2$ for 12 h at ambient temperature and the cake was assayed dry by QNMR (<1 wt % toluene and heptane). The product was obtained as an off-white solid (8.75 g, 63% after wt adjustment).

A 60 L jacketed reactor vented with a bleach scrubber was charged with (S)-(6-chloro-1-(hydroxymethyl)-1,2,3,4-tetrahydronaphthalen-1-yl)methyl 1-naphthoate (2.693 Kg, 88.6 wt %, 6.3 mol) followed by DCM (17.9 Kg, 5 vol) and $EtNiPr_2$ (2.84 Kg, 3.5 equiv). After $N_2$ inertion, the batch was agitated and cooled to 0° C. To the alcohol slurry mixture in the reactor was added a solution of freshly prepared $SO_3$·pyridine (2.10 Kg, 2.5 equiv of $SO_3$·pyridine in 7.43 Kg, 3 vol. DMSO) over 30 min while maintaining the batch temperature below 15° C. After addition, HPLC assay showed >99% conversion. The batch was quenched by the addition of water (14 L, 5 vol) over 20 min. maintaining the batch temperature below 15° C. and then toluene (16.8 L, 6 vol) was added. After partition, the organic layer was treated with water (14 L, 5 vol) and toluene (16.8 L, 6 vol). The top organic layer was washed with 2 N HCl twice (14 L each, 5 vol) and brine (14 L, 5 vol). The organic layer was drained to a clean container, assayed by HPLC and then transferred back to the clean 60 L reactor through an inline filter. The batch was concentrated to a minimal volume and solvent switched to MeOH until the batch volume was 28 L (10 vol) and MeOH/toluene ratio was 3:1 (v/v) as measured by QNMR. The batch was then transferred to a 30 L jacketed reactor through an inline filter. After adjustment of the batch temperature to 30° C., the batch was seeded with the aldehyde (51 g, 0.02 equiv) as a slurry in MeOH (400 mL). After the slurry was aged for 30 min at 30° C., the batch was solvent switched by distillation with MeOH until the batch volume is 11 L (4 vol) and MeOH/toluene ratio is >99:1 (v/v). The batch was then cooled to 5° C. and $MeOH/H_2O$ mixture (3.70 Kg MeOH+1.34 Kg water) was added over 1.5 h to bring the total solvent volume to approximately 5.5 vol and final $MeOH/H_2O$ to 90/10 (v/v). The batch was heated to 65° C. over 30 min, and cooled to 20° C. over 2 h and aged for ~2 h. The batch was filtered through an Aurora filter fitted with ≤25 μm filter cloth. The cake was washed with MeOH/water (10:1) (1×2 vol), then MeOH/water (2:1) (1×2 vol). The cake was dried under $N_2$ at ambient temperature for ≥4 h until dry to give the product as an off-white solid (1.99 Kg, 72% after wt % adjustment).

A 3-necked 250 mL RBF was charged with (R)-(6-chloro-1-formyl-1,2,3,4-tetrahydronaphthalen-1-yl)methyl 1-naphthoate (10 g, 94.4 wt %, 95.3% LCAP, >99% ee), methanol (100 mL), trimethyl orthoformate (7 mL), and TsOH monohydrate (0.24 g). The RBF was inerted with $N_2$, and started agitation. The batch was heated to 60° C. and aged for 2 h and HPLC assay showed ≥98% conversion.

The batch was concentrated under vacuum (~150-190 torr, external temp ~40° C.) to minimal volume using a rotoevaporator. The batch was turned over to THF by charging THF three times (50 mL each time) and distilling under vacuum (~165 torr, external temp ~40° C.). After each of the first two THF charges, the batch was concentrated down to a minimal volume, and after the last THF charge and distillation QNMR analysis of a sample showed the target ratio of >20/1 THF/MeOH (v/v). LiOH monohydrate (10.46 g, 10 eq) and water (50 mL) were charged to the 3-necked 250 mL RBF. The reaction mixture was heated to 65° C. and aged for 18 h. HPLC assay showed >99% conversion. The batch was cooled to 20° C. and transferred to a 500-mL separatory funnel. MTBE (106 mL) was charged to the separatory funnel and shaken well. After settling for 5 min, the bottom aqueous layer was drained. The top organic layer was washed with 20% $K_2CO_3$ twice (32 mL and 11 mL). The batch was transferred to a 250 mL RBF. Assay by HPLC showed <2% naphthanoic acid byproduct. The batch was concentrated to a minimal volume at reduced pressure on the rotoevaporator (300 mbar, external temp ~40° C.). The batch was turned over to THF using a rotoevaporator (~250 mbar, external temp ~40° C.) by adding and distilling of THF (~50 mL, ~50 mL). After each THF charge, the batch was distilled down to a minimal volume. THF (50 mL) was charged to the 250 mL RBF. KF of a sample showed 0% water (≤0.1% acceptable). The batch was polish filtered (60 mL medium-frit funnel) into a clean and dry 3-necked 250 mL RBF using THF (50 mL) for rinsing and volume adjusting. To the batch was added 4-fluoro-3-nitrobenzoic acid (4.61 g, 1.0 eq), the mixture was cooled to −20° C. and 20% potassium tert-butoxide THF solution (40 mL) was added over 1.5 h maintaining the batch temperature at 20±10° C. (exothermic). After complete addition, the batch was aged at −20° C. and an aliquot assayed by HPLC after 1.5 h showed 98% conversion. To the batch in the flask was added saturated NH₄Cl solution (10 mL) maintaining the temperature at −20±10° C. followed by addition of water (20 mL) and MeTHF (34 mL) at −20±20° C. The mixture was warmed to 20° C. and agitated for 13 h. The batch was transferred to a separatory funnel, allowed to settle for ~5 min, and the bottom aqueous layer was removed keeping the rag with the organic stream. The top organic stream was washed with saturated NH₄Cl solution (10 mL) and water (20 mL) at 20° C. After 5 min of settling, the aqueous layer was separated. To the total crude organic stream (KF=14%) was added MSA (4 mL) in a 250 mL 3-necked RBF. The batch was heated to reflux (65° C.) for 25 h and LC assay showed full conversion (≥97%).

The batch was cooled to <20° C. and K₃PO₄+H₂O (4.5 g) and water (7 mL) were added. The batch was transferred to a separatory funnel and the bottom aqueous layer was drained to give the aldehyde product crude solution. The combined organic crude stream was concentrated to minimum volume using a rotary evaporator. To the batch in a 500 mL RBF was charged AcOH (~50 mL, ~50 mL) and distilled using a rotary evaporator at reduced pressure (30 mbar, external temp ~40° C.). The THF level was measured by qNMR and none was observed. The mixture was transferred to a 250 mL 3-necked RBF and HOAc was added to adjust the total volume to 40 mL, when crystallization occurred. To the batch was added H₂O (12 mL) over ~1 h. After aging for >1 h, LC assay of supernatant concentration was 9 mg/mL. If concentration is >10 mg/mL then a small portion of water (0.2 vol) can be added; after checking by LC, repeat if necessary. The batch was filtered, washed with 20% H₂O/AcOH (23 mL) and dried under N₂/vacuum for 3.25 h to give the title compound (8.22 g) as an off-white solid (82% yield corrected for purity).

Step 10b: (R)-tert butyl 4-((6-chloro-1-formyl-1,2,3,4-tetrahydronaphthalen-1-yl)methoxy)-3-nitrobenzoate

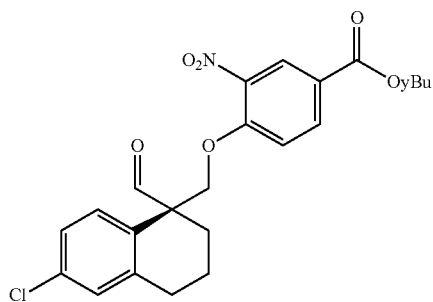

To a solution of (R)-tert-butyl 4-((6-chloro-1-(dimethoxymethyl)-1,2,3,4-tetrahydronaphthalen-1-yl)methoxy)-3-nitrobenzoate (1 g, 2.033 mmol) in anhydrous acetone (41 mL) was added amberlyst-15 (1 g, 2.033 mmol; prewashed with 2×10 mL dry acetone). The mixture was heated to 50° C. for 3.5 h, then it was filtered and rinsed with DCM. The filtrate was concentrated and dried under high vacuum overnight (it turned a dark red color). LC/MS and NMR analysis suggested 10% of corresponding carboxylic acid was present as well as 0.5 eq mesityl oxide. The mixture was advanced to the next step without further purification.

Step 11: (S)-6'-chloro-3',4,4',5-tetrahydro-2H,2'H-spiro[benzo[b][1,4]oxazepine-3,1'-naphthalene]-7-carboxylic Acid

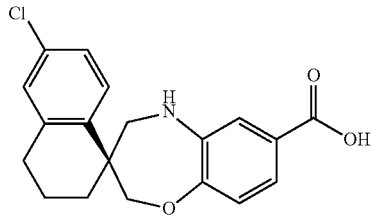

A solution of crude (R)-4-((6-chloro-1-formyl-1,2,3,4-tetrahydronaphthalen-1-yl)methoxy)-3-nitrobenzoic acid (30 g, 77.10 mmol) in acetic acid (1 L) was heated to 70° C. and iron powder (28 g, 500 mmol) was added. The resulting mixture was heated for 4 h at 70° C. Acetic acid was then removed under reduced pressure and the residue was dissolved in DCE (1 L). Sodium triacetoxy borohydride (46.5 g, 740 mmol) was added portion-wise and the reaction mixture was stirred at ambient temperature for 1 h. The reaction was then quenched with water followed by 10% aqueous citric acid (500 mL). The aqueous phase was extracted with DCM (2×1 L) and the combined organic layer was washed with brine (500 mL), dried over sodium sulfate and concentrated under reduced pressure. The residue was purified by column chromatography using 100-200 mesh size silica gel (40% ethyl acetate/hexane) to afford pure (S)-6'-chloro-3',4,4',5-tetrahydro-2H,2'H-spiro[benzo[b][1,4]oxazepine-3,1'-naphthalene]-7-carboxylic acid as white solid (24 g, 99% after two steps). R_f: 0.3 in 40% ethyl acetate in hexane.

Alternatively, (S)-6'-chloro-3',4,4',5-tetrahydro-2H,2'H-spiro[benzo[b][1,4]oxazepine-3,1'-naphthalene]-7-carboxyc acid with ((1S,4R)-7,7-dimethyl-2-oxobicyclo[2.2.1]heptan-1-yl)methanesulfonic acid (1:1) could be prepared as follows:

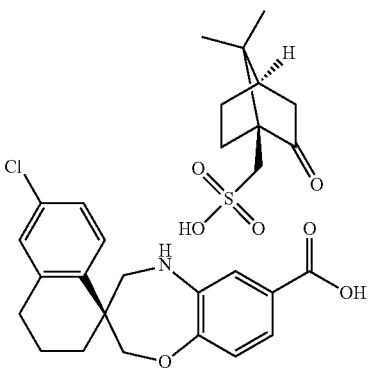

A pressure reactor was charged with (R)-4-((6-chloro-1-formyl-1,2,3,4-tetrahydronaphthalen-1-yl)methoxy)-3-nitrobenzoic acid (20 g, 94 wt %), 5% Pt/S/C wet (2.2 g), THF (400 mL) and Ti(OiPr)₄ (0.5 mL). The reactor was then sealed, purged with inert gas (3 cycles, at least once with stirring) and then it was purged with H₂ (1 cycle). The reactor was then pressurized with H₂ to 70 psig, stirring (950 rpm) was initiated and the temperature was increased to 90° C. maintaining the H₂ pressure in the reactor (70 psig at 22-30° C., 80 psig at 50-60° C. and 90 psig at 88-91° C.). After 16 h the reactor was cooled to ambient temperature and purged with inert gas (3 cycles). HPLC analysis of the reaction confirmed >98% conversion.

The reaction mixture was filtered through a Celite pad (2 inch) using additional THF for rinses, and the filtrate was concentrated under reduced pressure at 40° C. To the residue was added IPA (60 mL) and 2-4% aqueous MeOH (10 mL), the mixture was stirred for 10 minutes and then it was filtered through a pad of Celite (2 inch). MeOH was evaporated under reduced pressure at 40° C. and to the concentrated IPA solution cooled to ambient temperature was added a solution of (+)-camphor-10-sulfonic acid (CSA, 56.0 g) in IPA (200 mL) dropwise over 2 h. After 10% of the CSA solution has been added, the mixture was seeded with crystals of C1 (10-15 mg) followed by the addition of the remaining CSA solution. After stirring at ambient temperature overnight the mixture was filtered, the filter cake was washed with 100 mL of IPA and dried under vacuum/$N_2$ at ambient temperature. The product is isolated as a white solid: (S)-6'-chloro-3',4,4',5-tetrahydro-2H,2'H-spiro[benzo[b][1,4]oxazepine-3,1'-naphthalene]-7-carboxylic acid with ((1S,4R)-7,7-dimethyl-2-oxobicyclo[2.2.1]heptan-1-yl)methanesulfonic acid (1:1) (85-88% yield, 99-100 LCAP, >99.5% ee).

Step 12a: (S)-methyl 6'-chloro-3',4,4',5-tetrahydro-2H,2'H-spiro[benzo[b][1,4]oxazepine-3,1'-naphthalene]-7-carboxylate

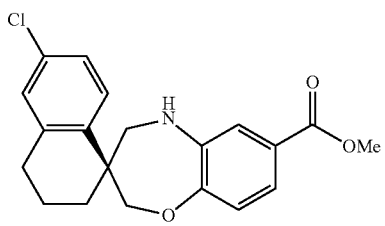 [SMILES: COC(=O)c1ccc2c(c1)NC[C@@]1(CCCc3cc(Cl)ccc31)CO2]

To a solution of (S)-6'-chloro-3',4,4',5-tetrahydro-2H,2'H-spiro[benzo[b][1,4]oxazepine-3,1'-naphthalene]-7-carboxylic acid (130 g, 379 mmol) in methanol (6 L) was added amberlyst-15 (130 g, pre-washed with anhydrous methanol) and heated to reflux for 10 h. Amberlyst was then removed by filtration and rinsed with methanol (3×300 mL). The combined filtrate was concentrated and the residue was purified by column chromatography affording pure (S)-methyl 6'-chloro-3',4,4',5-tetrahydro-2H,2'H-spiro[benzo[b][1,4]oxazepine-3,1'-naphthalene]-7-carboxylate as a white solid (105 g, 77%). $R_f$: 0.7 in 10% ethyl acetate in hexane. Chiral HPLC conditions: Column: ChiralCel OD-H (250 mm×4.6 mm, 5 μm); Mobile Phase: n-Hexane:EtOH: 95:05. Run Time: 25 min. Flow rate: 1 ml/min. Retention time (minor peak)-10.162 min. (1.98%); Retention time (major peak)-12.292 min. (98.02%).

Step 12b: (S)-tertbutyl 6'-chloro-3',4,4',5-tetrahydro-2H,2'H-spiro[benzo[b][1,4]oxazepine-3,1'-naphthalene]-7-carboxylate

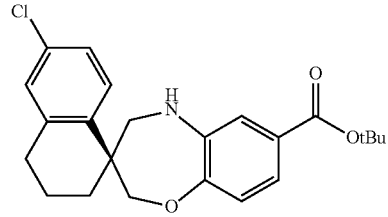

To a solution of (R)-tert-butyl 4-((6-chloro-1-formyl-1,2,3,4-tetrahydronaphthalen-1-yl)methoxy)-3-nitrobenzoate (0.9 g, 2.018 mmol) in acetic acid (20.22 ml, 353 mmol) at 70° C. was added iron (0.676 g, 12.11 mmol). The mixture was stirred vigorously for 4 h, then it was concentrated and the residue was diluted with 20 mL 1,2 DCE. Sodium triacetoxyhydroborate (1.711 g, 8.07 mmol) was added and the mixture was stirred at ambient temperature for 20 min. Upon quenching by addition of 20 mL water a very thick slurry formed. 20 mL 10% citric acid solution was added and the mixture became much lighter in color. The layers were separated and the aqueous layer was extracted with 2×20 mL dichloromethane. The combined organics were washed with 10 mL 10% citric acid and 10 mL brine, dried over $MgSO_4$, filtered, and concentrated. The residue was deposited on 3 g silica gel and purified using 5-10% ethyl acetate in hexanes to elute (S)-tert-butyl 6'-chloro-3',4,4',5-tetrahydro-2H,2'H-spiro[benzo[b][1,4]oxazepine-3,1'-naphthalene]-7-carboxylate (557 mg, 1.393 mmol, 69.0% yield). Further elution with 30% ethyl acetate in hexanes provided (S)-6'-chloro-3',4,4',5-tetrahydro-2H,2'H-spiro[benzo[b][1,4]oxazepine-3,1'-naphthalene]-7-carboxylic acid (132 mg, 0.384 mmol, 19.02% yield)

Step 13: (1R,2S)-1,2-cyclobutanediyldimethanol

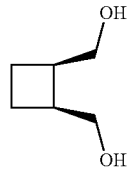

To a rapidly stirred solution of lithium aluminum hydride (1.0 m solution in THF, 1000 mL, 1000 mmol) at ambient temperature in a 3000 mL 3-necked flask under a stream of Argon was added gradually over 2 hours solid (1R,5S)-3-oxabicyclo[3.2.0]heptane-2,4-dione (40 g, 317 mmol), maintaining the internal temperature of the reaction mixture below 50° C. Upon completed addition of the anhydride the reaction was stirred overnight at ambient temperature under argon. After 16 hours the reaction mixture was cooled by an ice bath to 10° C. internal temperature and, under a fast stream of argon, a solution of 36 mL water was added drop wise by addition funnel at a rate that maintained the internal temperature between 12-15° C., approximately 1 ml/min, with vigorous stirring (500 rpm). Upon completed addition the mixture was vigorously stirred (500 rpm) in the ice-bath for 1 hour then removed from the bath and stirred to room temperature for 1 hour before cooling again with an ice bath to 5-10° C. internal temperature. To the mixture was added 36 mL of a 15% sodium hydroxide aqueous solution over a period of 45 minutes, maintaining the internal temperature between 10-20° C. To the thick mixture was added 108 mL water drop wise by addition funnel, maintaining the internal temperature between 10-20° C., over approximately 1 hour. Upon completed addition of the water the flask was removed from the ice bath, equilibrated to room temperature and left to stir vigorously under argon overnight. After stirring for 16 hours the mixture was filtered and the filtrate concentrated under reduced pressure to afford a colorless, slightly opaque oil. The oil was taken up in diethyl ether and stirred over anhydrous magnesium sulfate, filtered through a pad of Celite and the filtrate concentrated under reduced pressure to afford 32.8 g of a colorless oil, which was used in the next step without further purification (89% yield).

Step 14: (1R,2S)-cyclobutane-1,2-diylbis(methylene)diacetate

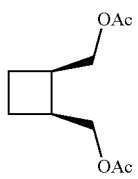 [SMILES: CC(=O)OC[C@H]1CC[C@H]1COC(C)=O]

Acetic anhydride (2.59 mL; 3.0 equiv.) was added to the (1R,2R)-1,2-cyclobutanediyldimethanol (1.06 g, 9.15 mmol) and the resulting solution heated to 50° C. After stirring overnight, the mixture was assayed by GC and showed complete conversion. The mixture was then diluted with 15 mL of heptane and concentrated under vacuum to give a clear oil. The oil was dissolved in 15 mL heptane and concentrated back down to an oil (azeotropic removal of acetic anhydride) to give the title compound as an oil 1.827 g; 88.3% purity by quantitative NMR using benzyl benzoate as an internal standard. (88% yield).

Step 15: ((1R,2S)-2-(hydroxymethyl)cyclobutyl)methyl acetate

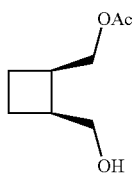 [SMILES: CC(=O)OC[C@@H]1CC[C@@H]1CO]

A 12 L 3-neck RBF equipped with mechanical stirrer was charged with a 1M sodium citrate solution (prepared by mixing sodium citrate tribasic dihydrate (682 g, 2320 mmol) and water to reach total volume ~2.3 L) and 3.48 L water (Tinternal was ~25° C.). The mixture was briefly cooled with ice/water bath to Tinternal ~20.2° C. pH~8.46 (measured with pH probe). Amano Lipase from *Pseudomonas fluorescens* (41.8 g, 1547 mmol) was then added in one charge (pH ~8.12) and the mixture was vigorously stirred at ambient temperature for 5 min. (1R,2S)-cyclobutane-1,2-diylbis(methylene)diacetate (348 g, 1547 mmol) was then added in one charge and the resulting mixture was stirred vigorously at ambient temperature monitoring Tinternal and pH. After stirring the mixture overnight (Tinternal ~20.9° C. and pH~5.45) an aliquot was collected, extracted with IPAc, diluted with ACN and analyzed by GC and the reaction was deemed complete (1.21% SM leftover, 0.17% of enantiomer, 1.8% of diol). Celite (70 g) added to the reaction mixture and the slurry was filtered through a pad of celite on a medium porosity glass filter (fast filtration, ~15-20 min), rinsing with 2.5 L IPAc. The biphasic mixture was transferred into a 12 L-extractor and stirred for ~1 min. The aqueous layer was separated and extracted with IPAc (1×4 L), and the combined organic extract was concentrated in vacuo obtaining 337.28 g (99.6% ee; ~50-60 mol % of residual IPAc by 1H-NMR; qNMR: 37.63 mg+benzyl benzoate (Aldrich catalog #B6630, lot #MKBG9990V, 61.27 mg; Result: 65 wt %; corrected yield 89%). The crude product was used as such for the next step.

Step 16: ((1R,2R)-2-formylcyclobutyl)methyl Acetate

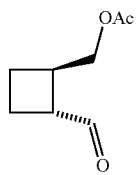 [SMILES: CC(=O)OC[C@@H]1CC[C@H]1C=O]

A 2-L Atlas reactor was charged with ((1R,2S)-2-(hydroxymethyl)cyclobutyl)methyl acetate (126.39 g, 79.6 wt % by QNMR; 636 mmol) and 1 L of DCM and the jacket temperature was set to 20° C. Iodobenzene diacetate (225 g, 700 mmol) was then added as a solid (endothermic addition: the temperature decreased to 15° C.). TEMPO (3.97 g, 25.4 mmol) was then added as a solid in one portion resulting in a cloudy orange solution which became clear over the course of 20 min. After stirring at 20° C. overnight an aliquot was collected, diluted with MeOH and analyzed by GC and the reaction was deemed complete. NOTE: An Additional kicker charge of iodobenzene diacetate and TEMPO can be used to push the reaction to completion if necessary. The reaction mixture was then cooled to Tinternal=1.8° C. (ice/dry ice/water bath) and diisopropylethylamine (194 mL; 1113 mol) was added drop-wise via addition funnel over 65 min keeping Tinternal <5° C. The cooling bath was removed and the mixture was allowed to warm to ambient temperature with stirring. After 48 h an aliquot was collected, diluted with methanol and analyzed by GC showing a 12:1 ratio of trans:cis isomers. The reaction mixture was then cooled to Tinternal <5° C. (ice/water bath) and water (230 mL) was added over 10 min (Tinternal reached 14° C.). The organic layer was separated, washed with water (125 mL) and 1M aqueous $NaH_2PO_4$ (90 mL) and concentrated in vacuo to afford 273.4 g of ((1R,2R)-2-formylcyclobutyl)methyl acetate (qNMR: 68.85 mg+benzyl benzoate (Aldrich catalog #B6630, Lot #MKBG9990V, 72.36 mg). Result: 32 wt %-contains iodobenzene as major contaminant; corrected yield 88.6%). The crude product was used as such for next step.

Step 17: ((1R,2R)-2-((R)-(1H-benzo[d][1,2,3]tri-azol-1-yl)(hydroxy)methyl)cyclobutyl)methyl Acetate

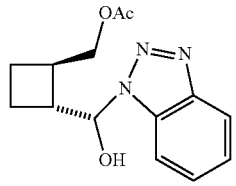 [SMILES: CC(=O)OC[C@@H]1CC[C@H]1C(O)n1nnc2ccccc21]

To a solution of crude ((1R,2R)-2-formylcyclobutyl)methyl acetate (5 g, 10.27 mmol; 32.07 wt %-contains iodobenzene) in 8 mL MTBE was added benzotriazole (1.296 g, 10.00 mmol) as a solid (slightly exothermic). The clear solution became increasingly cloudy and a precipitate formed. The mixture was allowed to equilibrate overnight at ambient temperature then heptane was added (6 mL). After aging for 6 h the mixture was filtered at ambient temperature and washed with 10 mL of 1:1 MTBE/heptane. The white solid was air dried on the frit under vacuum obtaining 2.48 g of ((1R,2R)-2-((R)-(1H-benzo[d][1,2,3]triazol-1-yl)(hydroxy)methyl)cyclobutyl)methyl acetate; 89% yield (uncorrected)

Step 18: (S)-methyl 5-(((1S,2R)-2-acetoxycyclobutyl)methyl)-6'-chloro-3',4,4',5-tetrahydro-2H,2'H-spiro[benzo[b][1,4]oxazepine-3,1'-naphthalene]-7-carboxylate

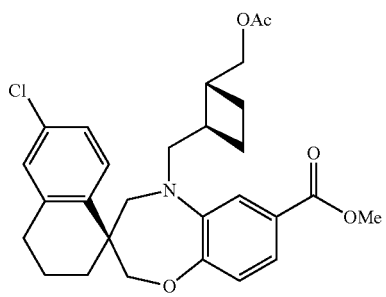 [SMILES: COC(=O)c1ccc2c(c1)N(C[C@@H]1CC[C@H]1COC(C)=O)C[C@@]1(CCCc3cc(Cl)ccc31)CO2]

((1R,2R)-2-Formylcyclobutyl)methyl acetate (4.36 g, 27.9 mmol) (steps 16) was added to a solution of (S)-methyl 6'-chloro-3',4,4',5-tetrahydro-2H,2'H-spiro[benzo[b][1,4]oxazepine-3,1'-naphthalene]-7-carboxylate (5.0 g, 13.97 mmol) (step 12) in DCM (78 mL) and AcOH (38.8 mL). The solution was stirred at ambient temperature for 10 minutes, then it was cooled to 0° C. and sodium cyanoborohydride (1.463 mL, 27.9 mmol) was added slowly portion by portion over 1 hour. After complete addition the mixture was stirred at 0° C. for 10 minutes then it was poured slowly into cold NaOH solution and extracted with EtOAc (120 ml). The organic phase was washed with brine, dried over anhydrous sodium sulfate and concentrated. The residue was loaded to a 220 g ISCO Gold column and eluted with 0% to 10% EtOAc/hexane, to provide the title compound, 6.0 g, as a white solid. m/z (ESI+ve ion) 498.1 (M+H)$^+$.

Step 19a: (S)-methyl 6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate

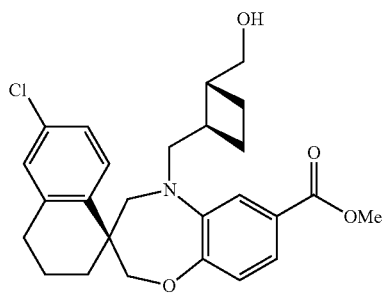 [SMILES: COC(=O)c1ccc2c(c1)N(C[C@@H]1CC[C@H]1CO)C[C@@]1(CCCc3cc(Cl)ccc31)CO2]

Potassium hydroxide (0.278 ml, 10.14 mmol) was added to a solution of (S)-methyl 5-(((1R,2S)-2-(acetoxymethyl)cyclobutyl)methyl)-6'-chloro-3',4,4',5-tetrahydro-2H,2'H-spiro[benzo[b][1,4]oxazepine-3,1'-naphthalene]-7-carboxylate (1.530 g, 3.07 mmol) in MeOH (99 ml). The mixture was stirred at ambient temperature for 4 h, then it was neutralized with 1N HCl to pH=7 and concentrated under reduced pressure. The aqueous residue was then extracted with EtOAc (400 ml) and the organic extract was washed with brine, dried over anhydrous sodium sulfate and filtered through a short plug of silica gel to afford the title compound as a white solid, 1.354 g, was obtained. m/z (ESI, +ve ion) 456.2 (M+H)$^+$.

Alternatively, (S)-methyl 6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate could be prepared as follows:

To a slurry of (S)-6'-chloro-3',4,4',5-tetrahydro-2H,2'H-spiro[benzo[b][1,4]oxazepine-3,1'-naphthalene]-7-carboxylic acid with ((1S,4R)-7,7-dimethyl-2-oxobicyclo[2.2.1]heptan-1-yl)methanesulfonic acid (1:1) (step 11) (32.22 g, 52.5 mmol) and ((1R,2R)-2-((R)-(1H-benzo[d][1,2,3]triazol-1-yl)(hydroxy)methyl)cyclobutyl)methyl acetate (step 17) (15.89 g, 57.7 mmol) in CH$_2$Cl$_2$ (226 mL, 7 mL/g) was added sodium triacetoxylborohydride (13.90 g, 65.6 mmol) in 4 portions over 30 min. Additional ((1R,2R)-2-((R)-(1H-benzo[d][1,2,3]triazol-1-yl)(hydroxy)methyl)cyclobutyl) methyl acetate (2.89 g, 10.50 mmol) and sodium triacetoxyborohydride (2.78 g, 13.12 mmol) were added to drive the reaction to completion (HPLC assay). 80 mL of water was then added and the resulting mixture was agitated for 5 min. The layers were then separated and the organic phase was washed with 60 ml water and 20 mL of brine then it was concentrated to an oil under reduced pressure. The residue was dissolved in 50 mL of MeOH and 40 mL of 5N NaOH were then added at ambient temperature (exothermic). Upon reaction completion (determined by HPLC assay) the reaction mixture was partitioned between 133 mL of MTBE and 35 mL of 1.5 M citric acid. The organic phase was transferred to a round bottom flask and the solvent was exchanged to MeCN via atmospheric distillation. This solution was seeded at 62° C. (a slurry developed) then it was allowed to reach ambient temperature and aged overnight. The slurry was then filtered at 20.5° C. through a coarse frit glass sinter funnel and the filter cake was washed using 60 mL of MeCN, then dried in a vacuum oven at 40° C. to constant weight. Final mass: 21.87 g (96.4 wt % by HPLC).

A 100 mL 3-necked-round bottom flask was charged with (S)-6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylic acid (4.53 g, 1.0 equiv), MeOH (45 mL, 10 vol), and then a prepared solution of SOCl$_2$ (11.28 mL, 1.0M in MeCN, 1.1 equiv). Under an atmosphere of N$_2$, the batch was heated to 55° C. and stirred for 18 h (or until >99% conversion as determined by HPLC). The reaction mixture was then allowed to cool to 20° C. over 2 h. To the resulting white slurry was added Hunig's base (3.94 mL, 2.2 equiv) and after aging for 0.5 h, water (9.0 mL, 2 V) was added as antisolvent over 1 h. The white slurry was aged for >2 h and the batch was filtered through a glass-fritted filter and the cake was washed with MeOH/water (5:1 v/v) (9.0 mL, 2V) then MeOH/water (2:1 v/v) (9.0 mL, 2V). The cake was dried under N$_2$ with vacuum for 12 h at ambient temperature. The product was obtained as a white solid (4.36 g, 92% yield).

Step 19b: (S)-tertbutyl 6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate

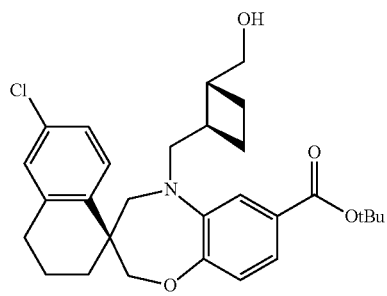 [SMILES: CC(C)(C)OC(=O)c1ccc2c(c1)N(C[C@@H]1CC[C@H]1CO)C[C@@]1(CCCc3cc(Cl)ccc31)CO2]

The title compound was synthesized from (S)-tertbutyl 6'-chloro-3',4,4',5-tetrahydro-2H,2'H-spiro[benzo[b][1,4]oxazepine-3,1'-naphthalene]-7-carboxylate (Intermediate AA11A, Step 12B) following the procedures described for Intermediate AA11A, Steps 18-19A).

Step 20a: (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate

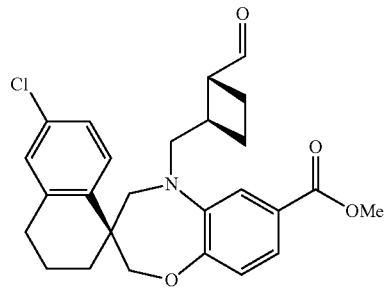

To a cooled (−70° C.) solution of DMSO (7.12 mL, 2.5 equiv) and DCM (183 mL, 10 vol) in a 1 L 3-necked-round bottom flask inerted with N$_2$ was added oxalyl chloride (26.1 mL, 1.0M in DCM, 1.3 equiv) at a rate to maintain temperature below 70° C. The batch was aged at <−70° C. for 30 min and then a prepared solution of (S)-methyl 6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate (18.3 g, 1.0 equiv) in DCM (183 mL, 10 vol) was added at a rate to maintain reaction temperature <−70° C. The batch was aged for 1.5 h and then Et$_3$N (22.4 mL, 4.0 equiv) was added at a rate to maintain batch temperature <−70° C. After aging for 1 h, the batch was allowed to warm to 20° C. and water (366 mL, 20 vol) was added. The batch was agitated at 20° C. and the phases separated. The organic layer was washed with 2×1N HCl (183 mL, 10 vol) and brine (183 mL, 10 vol). The organic layer was polish filtered and concentrated in vacuo to afford (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (19.91 g, 94% yield corrected for wt %) as a tan foam.

Step 20b: (S)-tertbutyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate

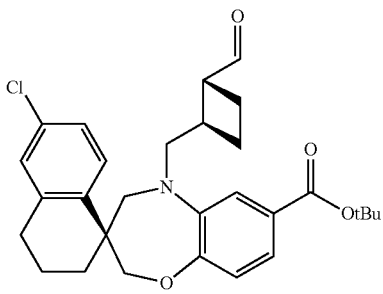 [SMILES: CC(C)(C)OC(=O)c1ccc2c(c1)N(C[C@@H]1CC[C@H]1C=O)C[C@@]1(CCCc3cc(Cl)ccc31)CO2]

The title compound was synthesized from (S)-tertbutyl 6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate (Intermediate AA 11A, Step 19B) following the procedure described for Intermediate AA11A, step 20A.

Step 21: (S)-methyl 6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylate

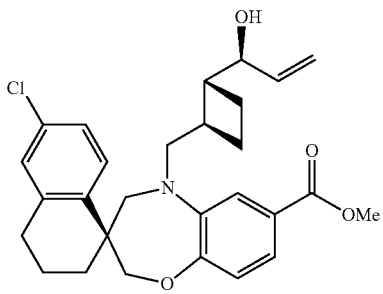 [SMILES: C=C[C@H](O)[C@@H]1CC[C@H]1CN1C[C@@]2(CCCc3cc(Cl)ccc32)COc2ccc(C(=O)OC)cc21]

An oven dried three-neck round bottom flask equipped with a pressure-equalizing addition funnel, thermocouple and magnetic stirbar was cooled to ambient temperature under a purge of argon gas. The flask was charged with (1R,2S)-2-morpholino-1-phenylpropan-1-ol (40.2 g, 182 mmol; prepared according to the literature procedure by Brubaker, J. D.; Myers, A. G. *Org. Lett.* 2007, 9, 3523-3525) against a positive pressure of argon. The addition funnel was charged with toluene (450 mL), which was dropped into the reactor. The solution was cooled in an ethyleneglycol-$CO_2$ bath (~−12° C.) and treated with butyllithium solution, 2.5 m in hexanes (72.6 mL, 182 mmol), causing a white solid to precipitate that gradually went into solution as it was stirred over 30 minutes. Divinylzinc solution, (605 mL, 182 mmol; prepared according to the literature procedure by Brubaker, J. D.; Myers, A. G. *Org. Lett.* 2007, 9, 3523-3525; The concentration of divinylzinc solution was determined by titrating against iodine (Krasovskiy, A.; Knochel, P. *Synthesis* 2006, 890-891); concentration was generally ~0.25M)) was added, and the solution was aged with stirring in the cold bath for an hour; the internal temperature was −15° C. (S)-methyl 6'-chloro-5-(((1R,2R)-2-formylcyclobutyl) methyl)-3',4,4',5-tetrahydro-2H,2'H-spiro[benzo[b][1,4] oxazepine-3,1'-naphthalene]-7-carboxylate (48.5 g, 107 mmol) (azeotroped thrice with toluene) was added as a solution in toluene (200 mL, 150 mL+2×25 mL cannula/vial rinse) via cannula (16G), over about 20 minutes. The internal temperature rose to −10° C. The mixture was stirred for 90 minutes while maintaining the internal reaction temperature below −5° C. The addition funnel was charged with 30% w/w aqueous citric acid (450 mL), then the reaction was quenched by adding the solution to the reaction mixture. The reactor was removed from the bath and permitted to stir at ambient temperature. The solution was transferred to a separatory funnel and the flask was rinsed with toluene and 30% aq citric acid (50 ml each). The layers were mixed and then separated. The organic layer was washed with water (250 mL), then brine (250 mL), and finally dried with $MgSO_4$. The solution was filtered and concentrated to yield a yellow oil, ~90 g after vacuum overnight, 20:1 dr. This was split into 3 batches and purified by column chromatography 10 to 20% EtOAc/hexanes 1.5 kg $SiO_2$, to provide (S)-methyl-6'-chloro-5-(((1R,2R)-2-((S)-1-hydroxyallyl)cyclobutyl)methyl)-3',4,4',5-tetrahydro-2H,2'H-spiro[benzo [b][1,4]oxazepine-3,1'-naphthalene]-7-carboxylate (43.3 g, 84%). The aqueous layer and washings were placed in an ice-water bath and basified to pH >13 by addition of 8N aqueous NaOH. This solution was then extracted with toluene (3×250 mL). The combined organic extracts were washed with water (250 mL) and brine (250 mL), then dried with $MgSO_4$. The solution was filtered and concentrated to recover the ligand in >95% yield. If desired the ligand could be recrystallized from heptanes.

Step 22: (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic Acid To a solution of (S)-methyl 6'-chloro-5-(((1R,2R)-2-((S)-1-hydroxyallyl)cyclobutyl)methyl)-3',4,4',5-tetrahydro-2H, 2'H-spiro[benzo[b][1,4]oxazepine-3,1'-naphthalene]-7-carboxylate (4.59 g, 9.52 mmol) in a mixture of THF (18 ml), MeOH (6.00 ml) and water (6.00 ml) was added lithium hydroxide monohydrate (0.799 g, 19.05 mmol) and the reaction was stirred at 50° C. for 4 hours. The reaction mixture was then concentrated to 15 mL, cooled to 0° C. and acidified with 2N HCl to pH=3. The resulting viscous oil was diluted with 20 mL of water and 50 mL of EtOAc and a clear two-layer mixture was obtained. More EtOAc (ca. 200 ml) was added and the organic layer was separated, washed with brine, dried with $MgSO_4$, filtered and concentrated under reduced pressure. The crude material was loaded onto a column (220 g), and purified with EtOAc in hexanes using the following gradient: 0-2.5 minutes 0% of EtOAc, 2.5 m-6 m 0-20% EtOAc, 6 m-35 m 20-60% EtOAc, 35 m-40 m 70% EtOAc to give (S)-6'-chloro-5-(((1R,2R)-2-((S)-1-hydroxy allyl)cyclobutyl)methyl)-3',4,4',5-tetrahydro-2H,2'H-spiro[benzo[b][1,4]oxazepine-3,1'-naphthalene]-7-carboxylic acid (4.22 g, 9.02 mmol, 95% yield) as a white solid.

Intermediate AA11B (S)-6'-chloro-5-(((1R,2R)-2-((R)-1-hydroxyallyl) cyclobutyl)methyl)-3',4,4',5-tetrahydro-2H,2'H-spiro [benzo[b][1,4]oxazepine-3,1'-naphthalene]-7-carboxylic Acid

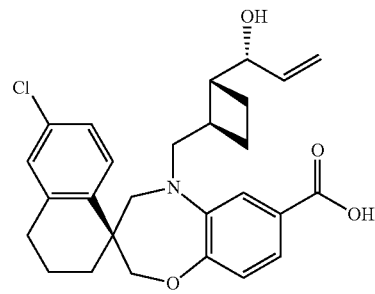 [SMILES: C=C[C@@H](O)[C@@H]1CC[C@H]1CN1C[C@@]2(CCCc3cc(Cl)ccc32)COc2ccc(C(=O)O)cc21]

Step 1: (S)-tertbutyl 6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylate and (S)-tertbutyl 6'-chloro-5-(((1R,2R)-2-((R)-1-hydroxyallyl)cyclobutyl) methyl)-3',4,4',5-tetrahydro-2H,2'H-spiro[benzo[b] [1,4]oxazepine-3,1'-naphthalene]-7-carboxylate and

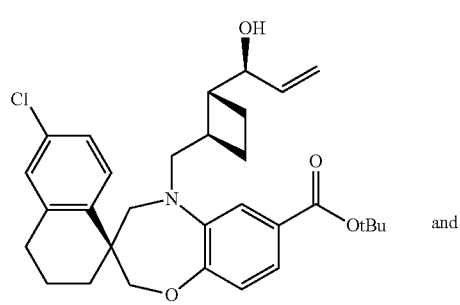

61
-continued

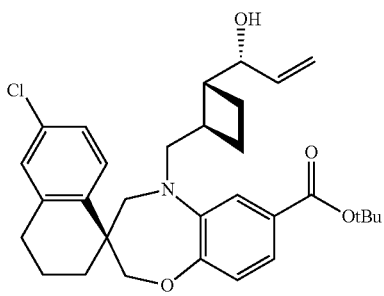

To a solution of (S)-tert-butyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20B, 0.754 g, 1.520 mmol) in THF (19.00 ml) cooled to 0° C. was added vinylmagnesium chloride solution (1.425 ml, 2.280 mmol) dropwise. The mixture was stirred at 0° C. and upon completion it was quenched with water and sat. NH$_4$Cl solution and extracted with EtOAc (200 ml). The organic phase was washed with brine, dried with anhydrous sodium sulfate and concentrated. Purification of the residue on a 220 g silica gel column eluting with 10% EtOAc in hexanes over 80 min provided (5)-tert-butyl 6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylate (312 mg). Rf 0.60 in 1:4 EtOAc in hexanes.

Further elution provided (5)-tert-butyl 6'-chloro-5-(((1R,2R)-2-((R)-1-hydroxy allyl)cyclobutyl)methyl)-3',4,4',5-tetrahydro-2H,2'H-spiro[benzo[b][1,4]oxazepine-3,1'-naphthalene]-7-carboxylate (270 mg). Rf 0.60 in 1:4 EtOAc in hexanes. (S)-tertbutyl 6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate (Intermediate AA 11A, Step 19B, 91 mg) was also isolated.

Step 2: (S)-6'-chloro-5-(((1R,2R)-2-((R)-1-hydroxyallyl)cyclobutyl)methyl)-3',4,4',5-tetrahydro-2H,2'H-spiro[benzo[b][1,4]oxazepine-3,1'-naphthalene]-7-carboxylic Acid 10 mL of a 25% TFA in DCM solution was added to (5)-tert-butyl 6'-chloro-5-(((1R,2R)-2-((R)-1-hydroxyallyl)cyclobutyl)methyl)-3',4,4',5-tetrahydro-2H,2'H-spiro[benzo[b][1,4]oxazepine-3,1'-naphthalene]-7-carboxylate (315 mg, 0.601 mmol). The reaction mixture was stirred at ambient temperature overnight then it was concentrated under reduced pressure. The residue was directly purified by on silica, eluting with 0-35% EtOAc (containing 0.3% HOAc) in hexanes to give (S)-6'-chloro-5-(((1R,2R)-2-((R)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (271 mg, 0.579 mmol, 96% yield).

62
Intermediate AA12A (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic Acid

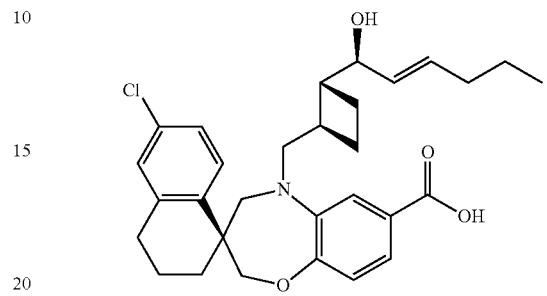

Step 1a: (S)-methyl 6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate

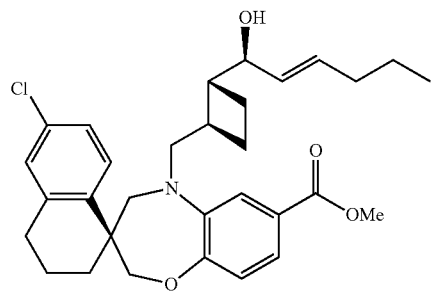 [SMILES: CCC/C=C/[C@H](O)[C@@H]1CC[C@H]1CN1C[C@@]2(CCCc3cc(Cl)ccc32)COc2ccc(C(=O)OC)cc21]

Under argon atmosphere, a dry three-neck flask charged with dry hexane (27 mL) was cooled to 0° C. To this solution was added borane-methyl sulfide complex (3.29 ml, 34.6 mmol) and cyclohexene (7.01 ml, 69.3 mmol) and the mixture was stirred at 0° C. for 2 h. To the resulting white suspension was added 1-pentyne (3.41 ml, 34.6 mmol) and the mixture was stirred at ambient temperature for 0.5 h. The mixture was then cooled to −78° C. and diethylzinc, 1.0 m solution in hexanes (32.3 ml, 32.3 mmol) was added. After addition the mixture was warmed to 0° C., stirred for 3 minutes then recooled to −78° C. This solution was named solution A. A separate flask was charged with a mixture of ((S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A, 5.24 g, 11.54 mmol) and (2s)-3-exo-(morpholino) isoborneal (0.486 g, 2.032 mmol) in n-hexane (50.9 ml) and toluene (16.97 ml). The mixture was stirred at ambient temperature until all solid was dissolved then it was cooled to 0° C. Under argon atmosphere 54 ml of solution A was added slowly via syringe during 1.6 h. After stirring for 5 min at 0° C. the mixture was quenched with saturated NH$_4$Cl solution (70 ml), diluted with water (30 ml) and extracted with EtOAc (3×270 ml), washed with brine, dried over anhydrous sodium sulfate and concentrated. The residue was loaded to a 330 g ISCO Gold column and eluted with 0% to 5% EtOAc/hexane, to provide the title compound, 3.8 gas a white solid. m/z (ESI, +ve ion) 524.1 (M+H)+.

Step 1b: (S)-tertbutyl 6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate and (S)-tertbutyl 6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate

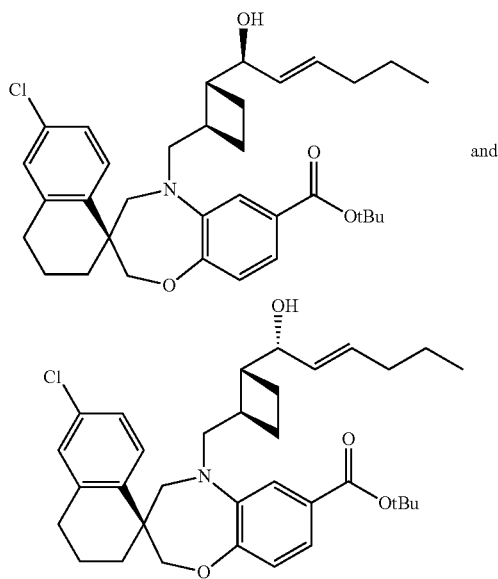

The title compound was synthesized from (5)-tert-butyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (3.19 g, Intermediate AA11A, Step 20B). The crude material was absorbed onto a plug of silica and purified on a 330 g ISCO Gold column eluting with 0 to 15% EtOAc in heptanes over 45 min to provide (S)-tertbutyl 6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (2.36 g).

Further elution provided (5)-tert-butyl 6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (0.45 g).

Step 2: (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic Acid A mixture of (S)-methyl 6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (4.6 g, 8.78 mmol) and lithium hydroxide monohydrate (3.68 g, 88 mmol) in MeOH (98 ml) and THF (98 ml) (with a few drops of water) was stirred at 50° C. overnight. The solvent was then removed and the residue was acidified with 1N HCl to pH 2-3. The mixture was extracted with EtOAc (80 ml×3) and the combined organic layer was washed with brine (10 ml), dried over anhydrous magnesium sulfate and concentrated under reduced pressure to give (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (4.25 g, 8.34 mmol, 95% yield).

Alternatively, the title compound could be synthesized as follows:

To a solid mixture of (5)-tert-butyl 6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (Intermediate AA12A, Step 1B, first eluting isomer, 4.50 g 7.95 mmol) and lithium hydroxide monohydrate (1.66 g, 39.7 mmol) was added solvent Dioxane/MeOH (1:1) (159 ml). The mixture was heated to 65° C. and stirred overnight. The mixture was then diluted with water and acidified with 1.0 N HCl to pH~4. The organic solvents were evaporated under reduced pressure and to the residue was added water. The aqueous mixture was then extracted with EtOAc thrice, and the combined organic extract was concentrated. The residue was purified on a 120 g silica gel column eluting with a gradient of 0-70% EtOAc in hexanes to provide (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (3.80 g, 7.45 mmol, 94% yield).

Intermediate AA12B (S)-6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic Acid

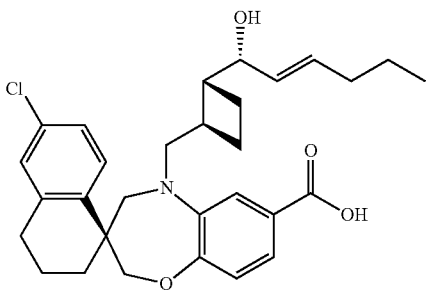

The title compound was synthesized from (S)-tertbutyl 6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (Intermediate AA12A, Step 1B, second eluting isomer) following the procedure described for Intermediate AA12A, Step 2.

Intermediate AA13A (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic Acid

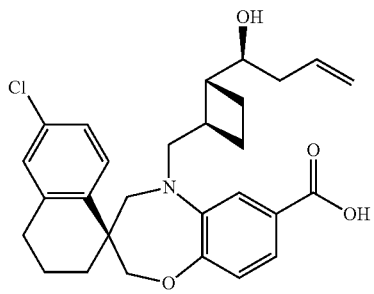 [SMILES: C=CC[C@H](O)[C@@H]1CC[C@H]1CN1C[C@@]2(CCCc3cc(Cl)ccc32)COc2ccc(C(=O)O)cc21]

Step 1a: (S)-methyl 6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate

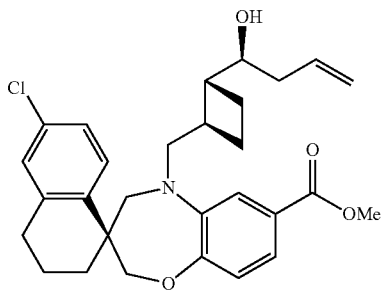 [SMILES: C=CC[C@H](O)[C@@H]1CC[C@H]1CN1C[C@@]2(CCCc3cc(Cl)ccc32)COc2ccc(C(=O)OC)cc21]

An oven-dried 200-mL flask charged with a suspension of (1R,2R)—N-methyl-1-phenyl-1-(((1S,5S,10R)-10-(trimethylsilyl)-9-borabicyclo[3.3.2]decan-9-yl)oxy)propan-2-amine (5.40 g, 14.54 mmol) in Et$_2$O (73 mL) under argon was cooled to −78° C. and treated with allylmagnesium bromide (13.22 ml, 13.22 mmol) solution, dropwise. The mixture was allowed to warm to ambient temperature and stirred for 1 h. The solution (0.17 M; solution A) was then recooled to −78° C.

A separate 200 ml flask charged with ((S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A, 2.0 g, 4.41 mmol) in Et$_2$O (22.03 ml) under argon was cooled to −78° C. To this solution was added 40 mL of the above solution A and the resulting mixture was stirred at −78° C. for 40 minutes. 4-methylmorpholine 4-oxide (3.10 g, 26.4 mmol) was then added and the mixture was allowed to warm to ambient temperature for 10 minutes. Methanol (10 ml) was then added and the volatile organics were evaporated under reduced pressure at ambient temperature. Additional methanol (100 ml) was then added and after stirring at ambient temperature for 1 h the mixture was concentrated. The residue was diluted with EtOAc (450 ml), washed with 1N HCl (15 ml), Na$_2$CO$_3$ solution (10 ml), and brine (6 ml), dried over anhydrous sodium sulfate and concentrated. The residue was loaded to a 220 g ISCO Gold column and eluted with 0% to 5% EtOAc/hexane, to provide the title compound, 1.88 g as a white solid. m/z (ESI, +ve ion) 496.0 (M+H)$^+$.

Step 1b: (S)-tertbutyl 6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate

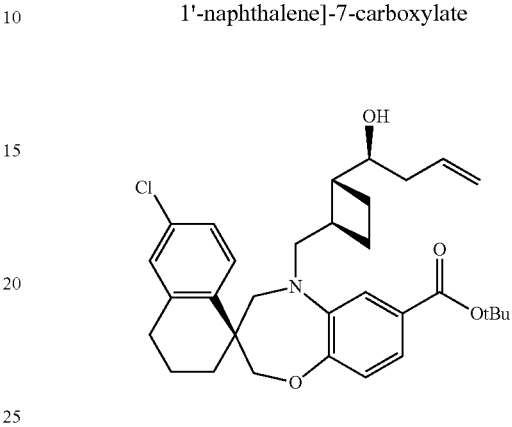

The title compound was synthesized from (5)-tert-butyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (3.0 g, Intermediate AA11A, Step 20B) following the procedure described for Intermediate AA13A, Step 1A. The crude material was purified on a 220 g silica gel column eluting with 5% EtOAc in hexanes over 60 min to provide (5)-tert-butyl 6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate (2.19 g). Rf=0.5 in 1:4 EtOAc in hexanes.

Step 2: (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic Acid A mixture of (S)-methyl 6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate (1.88 g, 3.79 mmol) and lithium hydroxide solution (1M) (34.1 ml, 34.1 mmol) in MeOH (34 ml) and THF (50 ml) was stirred at 65° C. for 50 minutes. After cooling to ambient temperature, the mixture was acidified with 1N HCl to pH 2-3, extracted with EtOAc (350 ml), dried over anhydrous sodium sulfate and concentrated to provide the title compound, 1.82 g as a white solid. m/z (ESI, +ve ion) 482.0 (M+H)$^+$.

Alternatively, the title compound could be synthesized as follows:

To a solution of (S)-tert-butyl 6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate (Intermediate AA13A, Step 1B, 250 mg, 0.465 mmol) in CH$_2$Cl$_2$ (3.717 mL) at ambient temperature, TFA (0.929 mL) was added and the reaction mixture was stirred for 4 h. The crude reaction mixture was then concentrated, the residue was taken up in EtOAc, washed once with sat. NaHCO$_3$, dried over MgSO$_4$, filtered and concentrated to give a white foam. The crude material was used as such, without further purification.

Intermediate AA13B (S)-6'-chloro-5-(((1R,2R)-2-((R)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic Acid

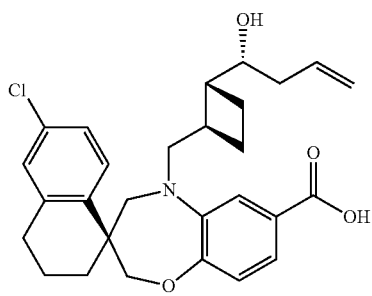 [SMILES: C=CC[C@@H](O)[C@@H]1CC[C@H]1CN1C[C@@]2(CCCc3cc(Cl)ccc32)COc2ccc(C(=O)O)cc21]

Step 1: (S)-methyl 6'-chloro-5-(((1R,2R)-2-((R)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate

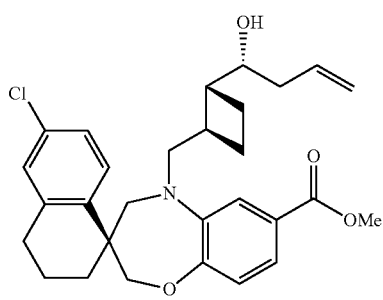 [SMILES: C=CC[C@@H](O)[C@@H]1CC[C@H]1CN1C[C@@]2(CCCc3cc(Cl)ccc32)COc2ccc(C(=O)OC)cc21]

To a mixture of allyl iodide (0.824 mL, 8.95 mmol) and (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A, 1016 mg, 2.238 mmol) in DMF (40.700 mL) was added indium powder (0.106 mL, 6.71 mmol) in one portion. The mixture was stirred at ambient temperature for 30 min then it was diluted with water (50 ml) and extracted with EtOAc (2×80 mL). The combined organics were dried over anhydrous magnesium sulfate and concentrated. The crude material was loaded onto a cartridge and purified via column chromatography (80 g ISCO gold) eluting with a gradient of 0-10-20% EtOAc/hexane over 30 min. to obtain (S)-methyl 6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate (450 mg, Intermediate AA13A, Step 1A) as the first eluting isomer.

Further elution provided (S)-methyl 6'-chloro-5-(((1R,2R)-2-((R)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate (431 mg) as the second eluting isomer.

Step 2: (S)-6'-chloro-5-(((1R,2R)-2-((R)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic Acid The title compound was synthesized from (S)-methyl 6'-chloro-5-(((1R,2R)-2-((R)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate (431 mg, 0.869 mmol) following the procedure described for Intermediate AA11A, Step 22. The crude material was used as such without further purification.

Intermediate AA16

(S)-6'-chloro-8-fluoro-5-(((1R,2R)-2-((S,E)-1-hydroxypent-2-en-1-yl)cyclobutyl)methyl)-3',4,4',5-tetrahydro-2H,2'H-spiro[benzo[b][1,4]oxazepine-3,1'-naphthalene]-7-carboxylic Acid

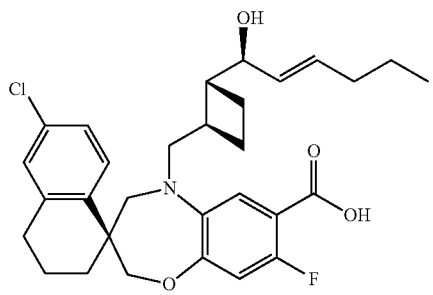

Step 1: (R)-methyl 4-((6-chloro-1-(dimethoxymethyl)-1,2,3,4-tetrahydronaphthalen-1-yl)methoxy)-2-fluoro-5-nitrobenzoate and (R)-methyl 2-((6-chloro-1-(dimethoxymethyl)-1,2,3,4-tetrahydronaphthalen-1-yl)methoxy)-4-fluoro-5-nitrobenzoate

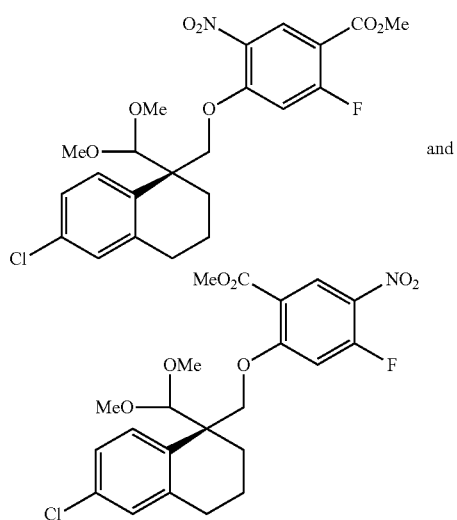

To a 0° C. solution of methyl 2,4-difluoro-5-nitrobenzoate (2406 mg, 11.08 mmol, Ace Synthesis, LLC) and (R)-(6- chloro-1-(dimethoxymethyl)-1,2,3,4-tetrahydronaphthalen-1-yl)methanol (Intermediate AA11, Step 7; 2000 mg, 7.39 mmol) in THF (37 mL) under N$_2$ atmosphere was added LiHMDS (8.86 mL, 8.86 mmol, 1.0 M solution in THF) dropwise over 5 min. The resulting solution was allowed to warm to ambient temperature and stirred for 5.0 hr. The reaction mixture was slowly poured into a saturated aqueous NH$_4$Cl solution (30 mL) and diluted with water (20 mL). The organic layer was separated and the aqueous layer was back extracted with EtOAc (2×50 mL). The organic layers were combined, washed with water (15 mL) and brine (10 mL), and dried over MgSO$_4$. After removal of organic solvents under reduced pressure, the residue was purified by flash chromatography on 40 g ISCO Gold silica gel column with 0-50% EtOAc/Hexanes to provide the title compound as a 1:1 mixture (2.78 g, 5.94 mmol, 80% yield).

Step 2: (R)-methyl 5-amino-4-((6-chloro-1-(dimethoxymethyl)-1,2,3,4-tetrahydronaphthalen-1-yl)methoxy)-2-fluorobenzoate and ((R)-methyl 5-amino-2-((6-chloro-1-(dimethoxymethyl)-1,2,3,4-tetrahydronaphthalen-1-yl)methoxy)-4-fluorobenzoate

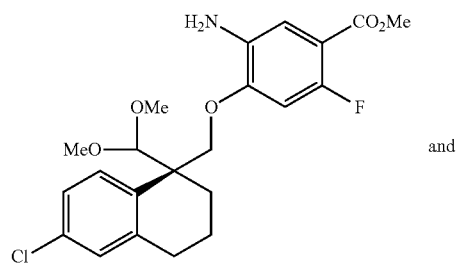

and

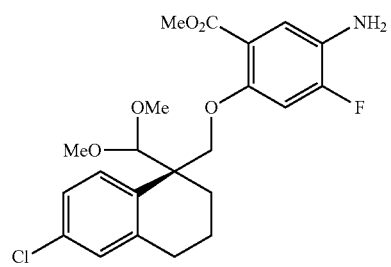

A mixture of (R)-methyl 4-((6-chloro-1-(dimethoxymethyl)-1,2,3,4-tetrahydronaphthalen-1-yl)methoxy)-2-fluoro-5-nitrobenzoate and (R)-methyl 2-((6-chloro-1-(dimethoxymethyl)-1,2,3,4-tetrahydronaphthalen-1-yl)methoxy)-4-fluoro-5-nitrobenzoate (1:1 mixture, 1.98 g), and PtO$_2$ (98 mg, Sigma-Aldrich) in EtOAc (15 mL) was left stirring under H$_2$ atmosphere at rt for 3.0 h. The resulting reaction flask was purged with N$_2$ for 5 min, and the solid was removed by filtration and washed with EtOAc. After removal of organic solvents under reduced pressure, the crude material was taken on to the next step without further purification.

Step 3: methyl 6'-chloro-8-fluoro-3',4'-dihydro-2H,2'H-spiro[benzo[b][1,4]oxazepine-3,1'-naphthalene]-7-carboxylate

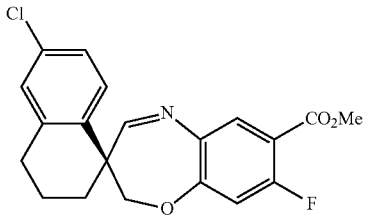 [SMILES: COC(=O)c1cc2c(cc1F)OC[C@@]1(C=N2)CCCc2cc(Cl)ccc21]

A mixture of (R)-methyl 5-amino-4-((6-chloro-1-(dimethoxymethyl)-1,2,3,4-tetrahydronaphthalen-1-yl)methoxy)-2-fluorobenzoate and ((R)-methyl 5-amino-2-((6-chloro-1-(dimethoxymethyl)-1,2,3,4-tetrahydronaphthalen-1-yl)methoxy)-4-fluorobenzoate (1:1 mixture) and HCl (4.0 N in 1,4-dioxane, Sigma Aldrich, 10.0 mL) was stirred at ambient temperature for 1.5 hr. The mixture was then slowly poured into saturated aq. NaHCO$_3$ (10 mL), diluted with water (10 mL), and extracted with DCM (2×20 mL). After removal of organic solvents under reduced pressure, the crude material was taken on to the next step without further purification Step 4: (S)-methyl 6'-chloro-8-fluoro-3',4,4',5-tetrahydro-2H,2'H-spiro[benzo[b][1,4]oxazepine-3,1'-naphthalene]-7-carboxylate

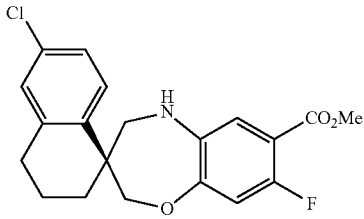 [SMILES: COC(=O)c1cc2c(cc1F)OC[C@]1(CCCc3cc(Cl)ccc31)CN2]

To a solution of (methyl 6'-chloro-8-fluoro-3',4'-dihydro-2H,2'H-spiro[benzo[b][1,4]oxazepine-3,1'-naphthalene]-7-carboxylate in DCM (12 mL) was added sodium triacetoxyborohydride (1.0 M in THF, Sigma-Aldrich; 5.0 mL, 5.0 mmol). The mixture was allowed to stir at 0° C. to rt for 4.0 h. The solution was then treated with saturated aqueous NH$_4$Cl (5 mL) and saturated aqueous citric acid solution (0.2 mL), diluted with water (15 mL), and extracted with CH$_2$Cl$_2$ (2×16 mL). The organic solutions were combined. After removal of organic solvents under reduced pressure, the residue was purified by flash chromatography on 12 g ISCO Gold silica gel column eluting with 20-70% EtOAc/Hexanes to provide the title product as a white foam (980 mg, 2.61 mmol, 61.6% yield for the three steps).

Step 5: ((S)-methyl 5-(((1R,2R)-2-(((tert-butyldim-ethylsilyl)oxy)methyl)cyclobutyl)methyl)-6'-chloro-8-fluoro-3',4,4',5-tetrahydro-2H,2'H-spiro[benzo[b][1,4]oxazepine-3,1'-naphthalene]-7-carboxylate

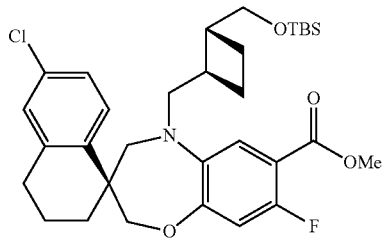 [SMILES: COC(=O)c1cc2c(cc1F)OC[C@]1(CCCc3cc(Cl)ccc31)CN2C[C@@H]1CC[C@H]1CO[Si](C)(C)C(C)(C)C]

To a mixture of (S)-methyl 6'-chloro-8-fluoro-3',4,4',5-tetrahydro-2H,2'H-spiro[benzo[b][1,4]oxazepine-3,1'-naphthalene]-7-carboxylate (900 mg, 2.395 mmol) and (1R,2R)-2-(((tert-butyldimethylsilyl)oxy)methyl)cyclobutanecarbaldehyde (Intermediate AA14, Step 7; 830 mg, 3.63 mmol) in AcOH/CH$_2$Cl$_2$ (1:4) (8 mL) in ice bath was added a solution of sodium borocyanohydride (2.395 mL, 1.0 N, 2.395 mmol, Sigma-Aldrich) in THF (2.5 mL) via syringe pump over 1.0 h. The resulting mixture was allowed to stir at ambient temperature for 10 more minutes, TLC (20% EtOAc in hexanes) of the crude reaction mixture indicated complete conversion of the starting material and clean formation of a less polar product. The mixture was quenched with saturated aq. NH$_4$Cl (8 mL), diluted with water (10 mL) and aq. citric aid solution (10 mL, 4.0 N), and extracted with EtOAc (3×15 mL). The organic layers were combined, washed with brine (5 mL) and dried over MgSO$_4$. Removal of the organic solvents under reduced pressure provided the crude title product as a brown syrup. This material was taken on to the next step without further purification.

Step 6: (S)-methyl 6'-chloro-8-fluoro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate

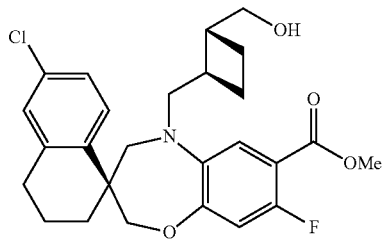 [SMILES: COC(=O)c1cc2c(cc1F)OC[C@]1(CCCc3cc(Cl)ccc31)CN2C[C@@H]1CC[C@H]1CO]

The title compound was prepared as a white solid starting from (S)-methyl 5-(((1R,2R)-2-(((tert-butyldimethylsilyl)oxy)methyl)cyclobutyl)methyl)-6'-chloro-8-fluoro-3',4,4',5-tetrahydro-2H,2'H-spiro[benzo[b][1,4]oxazepine-3,1'-naphthalene]-7-carboxylate following the procedure described for Intermediate AA14, Step 10. Purification of the crude material by flash chromatography on 40 g ISCO Gold silica gel column with 20-70% EtOAc/Hexanes provided the title products as a colorless solid (920 mg, 1.94 mmol, 81% yield for the two steps). MS m/z (ESI, +ve ion) 474.0 (M+H)$^+$.

Step 7: (S)-methyl 6'-chloro-8-fluoro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate

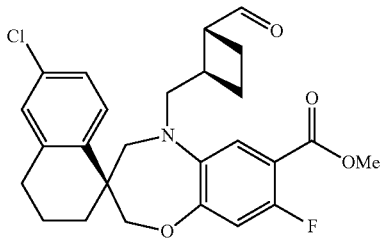 [SMILES: COC(=O)c1cc2c(cc1F)OC[C@]1(CCCc3cc(Cl)ccc31)CN2C[C@@H]1CC[C@H]1C=O]

To a solution of (S)-methyl 6'-chloro-8-fluoro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate (790 mg, 1.667 mmol) in CH$_2$Cl$_2$ (10 mL) was added Dess-Martin periodinane (Advanced Chemiblocks; 848 mg, 2.000 mmol). The mixture was left stirring at ambient temperature for 2 h then it was directly injected onto a 40 g silica gel column and purified eluting with 20-60% EtOAc/Hexanes to provide the title compound (670 mg, 1.42 mmol, 85% yield).

Step 8: (S)-methyl 6'-chloro-8-fluoro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate

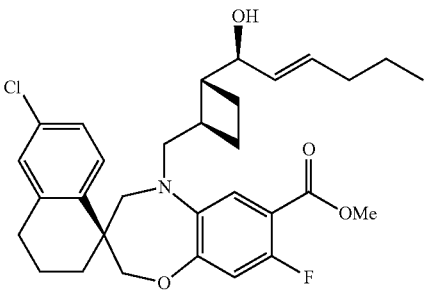 [SMILES: CCC/C=C/[C@H](O)[C@@H]1CC[C@H]1CN1C[C@@]2(CCCc3cc(Cl)ccc32)COc2cc(F)c(C(=O)OC)cc21]

The title compound was prepared as a white solid starting from (S)-methyl 6'-chloro-8-fluoro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (670 mg, 1.42 mmol) following the procedure described for Intermediate AA12, Step 1. Purification of the crude material on a 24 g column eluting with 20-60% EtOAc/Hexanes provided the title compound (670 mg, 1.23 mmol, 87% yield). MS m/z (ESI, +ve ion) 542.0 (M+H)$^+$.

Step 9: (S)-6'-chloro-8-fluoro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic Acid The title compound was prepared as a colorless solid starting from (S)-methyl 6'-chloro-8-fluoro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'- naphthalene]-7-carboxylate (670 mmol, 1.23 mmol) following the procedure described for Intermediate AA12, Step 2. Purification of the crude material on a 24 g column eluting with 40-100% EtOAc/Hexanes provided the title compound (431 mg, 0.816 mmol, 66% yield). MS m/z (ESI, +ve ion) 528.0 (M+H)$^+$.

Intermediate AA17

(S)-6'-8-dichloro-5-(((1R,2R)-2-((S,E)-1-hydroxypent-2-en-1-yl)cyclobutyl)methyl)-3',4,4',5-tetrahydro-2H,2'H-spiro[benzo[b][1,4]oxazepine-3,1'-naphthalene]-7-carboxylic Acid

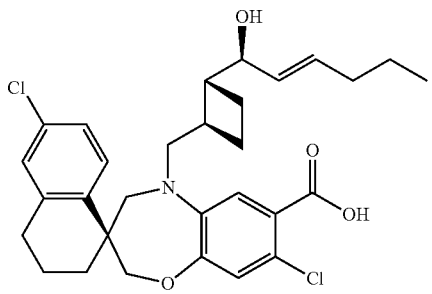 [SMILES: CCC/C=C/[C@H](O)[C@@H]1CC[C@H]1CN1C[C@@]2(CCCc3cc(Cl)ccc32)COc2cc(Cl)c(C(=O)O)cc21]

Step 1: Ethyl 2-chloro-4-fluoro-5-nitrobenzoate

A mixture of 2-chloro-4-fluoro-5-nitrobenzoic acid (14.80 ml, 114 mmol, Combi-Blocks Inc.), ferric sulfate hydrate (0.952 g, 2.277 mmol, Sigma-Aldrich Chemical Company, Inc.) and ethanol (398 ml, 6832 mmol, 200 proof, GOLD SHIELD CHEMICAL COMPANY) with 1 mL of conc. $H_2SO_4$ was reflux for 6.0 h, and then heated at 50° C. for 72 h. To the mixture was added conc. $H_2SO_4$ (2.0 mL), additional ferric sulfate hydrate (1.12 g), and water (3 mL). The mixture was refluxed for a further 12 h. After removal of organic solvents under reduced pressure, the residue was dissolved in EtOAc (700 mL), washed with water, brine, and dried over $Na_2SO_4$. After removal of organic solvents under reduced pressure, purification of the residue by flash chromatography on 24 g silica gel column with 0-50% EtOAc in hexanes provided the title compound as a pale yellow solid (14.39 g).

Step 2: (R)-ethyl 2-chloro-4-((6-chloro-1-(dimethoxymethyl)-1,2,3,4-tetrahydronaphthalen-1-yl)methoxy)-5-nitrobenzoate

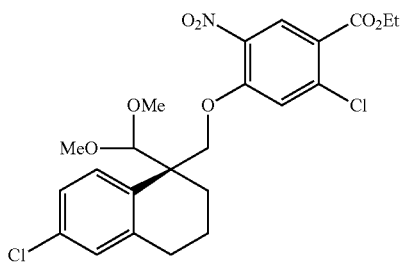 [SMILES: CCOC(=O)c1cc([N+](=O)[O-])c(OC[C@@]2(C(OC)OC)CCCc3cc(Cl)ccc32)cc1Cl]

The title compound was prepared from (R)-(6-chloro-1-(dimethoxymethyl)-1,2,3,4-tetrahydronaphthalen-1-yl)methanol (Intermediate AA11A, Step 7; 1.5 g, 5.54 mmol) and ethyl 2-chloro-4-fluoro-5-nitrobenzoate (Intermediate AA17, Step 1; 1.5 g, 6.09 mmol) following the procedure as described for the synthesis of (R)-methyl 4-((6-chloro-1-(dimethoxymethyl)-1,2,3,4-tetrahydronaphthalen-1-yl)methoxy)-2-fluoro-5-nitrobenzoate (Intermediate AA16, Step 1), except that the crude product was purified by flash chromatography on a 40 g ISCO Gold silica gel column with 0-40% EtOAc in hexanes to provide the title products (2.4 g, 4.81 mmol, 83% yield) as a single isomer.

Step 3: (R)-ethyl 5-amino-2-chloro-4-((6-chloro-1-(dimethoxymethyl)-1,2,3,4-tetrahydronaphthalen-1-yl)methoxy)benzoate

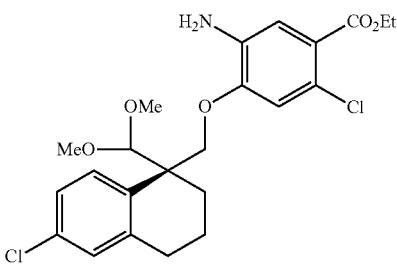

The title compound was prepared from (R)-ethyl 2-chloro-4-((6-chloro-1-(dimethoxymethyl)-1,2,3,4-tetrahydronaphthalen-1-yl)methoxy)-5-nitrobenzoate (Intermediate AA17, Step 2; 2.4 g, 4.81 mmol) following the procedure as described for the synthesis of (R)-methyl 4-((6-chloro-1-(dimethoxymethyl)-1,2,3,4-tetrahydronaphthalen-1-yl)methoxy)-2-fluoro-5-nitrobenzoate (Intermediate AA16, Step 2) and the crude product was used directly in the next step without purification.

Step 4: (S)-ethyl 6',8-dichloro-3',4'-dihydro-2H,2'H-spiro[benzo[b][1,4]oxazepine-3,1'-naphthalene]-7-carboxylate

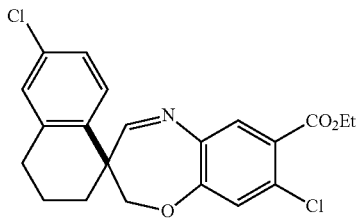 [SMILES: CCOC(=O)c1cc2c(cc1Cl)OC[C@@]1(C=N2)CCCc2cc(Cl)ccc21]

The title compound was prepared from (R)-ethyl 5-amino-2-chloro-4-(((6-chloro-1-(dimethoxymethyl)-1,2,3,4-tetrahydronaphthalen-1-yl)methoxy)benzoate (Intermediate AA17, Step 3) following the procedure as described for the synthesis of (R)-methyl4-(((6-chloro-1-(dimethoxymethyl)-1,2,3,4-tetrahydronaphthalen-1-yl)methoxy)-2-fluoro-5-nitrobenzoate (Intermediate AA16, Step 3) and the crude product was used directly in the next step without purification. MS m/z (ESI, +ve ion) 404.0 (M+H)$^+$.

Step 5: (S)-ethyl 6',8-dichloro-3',4,4',5-tetrahydro-2H,2'H-spiro[benzo[b][1,4]oxazepine-3,1'-naphthalene]-7-carboxylate

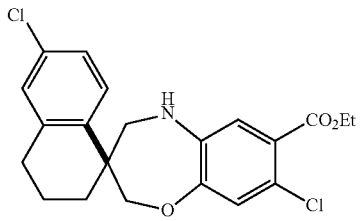 [SMILES: CCOC(=O)c1cc2c(cc1Cl)OC[C@]1(CCCc3cc(Cl)ccc31)CN2]

The title compound was prepared from (S)-ethyl 6',8-dichloro-3',4'-dihydro-2H,2'H-spiro[benzo[b][1,4]oxazepine-3,1'-naphthalene]-7-carboxylate (Intermediate AA17, Step 4) following the procedure as described for the synthesis of (R)-methyl4-(((6-chloro-1-(dimethoxymethyl)-1,2,3,4-tetrahydronaphthalen-1-yl)methoxy)-2-fluoro-5-nitrobenzoate (Intermediate AA16, Step 4), except that the crude product was purified by flash chromatography on a 40 g ISCO Gold silica gel column eluting with 20-70% EtOAc in hexanes to provide the title compound (1.35 g, 3.32 mmol, 79% for the three steps) as a white solid. MS m/z (ESI, +ve ion) 406.0 (M+H)$^+$.

Step 6: (1R,2R)-cyclobutane-1,2-diyldimethanol

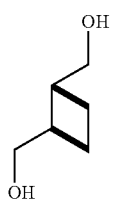

To a solution of (1R,2R)-cyclobutane-1,2-dicarboxylic acid (20.0 g, 138.8 mmol) in THF (200 mL) was added BH$_3$.DMS (29.0 mL, 305.5 mmol) dropwise at 0° C. The reaction mixture was stirred at ambient temperature for 12 h. After the completion of reaction (monitored by TLC), the reaction mixture was cooled to 0° C. and methanol (50 mL) was added dropwise. The resulting reaction mixture was stirred at ambient temperature for 30 minutes and concentrated under reduced pressure to get crude material. The crude material was again diluted with methanol (200 mL) and concentrated under reduced pressure to afford the title compound (15.0 g, 93.0%) which was carried forward to the next step without purification. R$_f$: 0.1 in 50% ethyl acetate in hexane.

Step 7: ((1R,2R)-2-(hydroxymethyl)cyclobutyl)methyl Benzoate

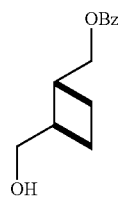

To a suspension of sodium hydride (60-65% suspension in oil, 4.9 g, 129.3 mmol) in THF (100 mL) at 0° C. was added a solution of (1R,2R)-cyclobutane-1,2-diyldimethanol (15.0 g, 129.3 mmol) in THF (50 mL) dropwise. The resulting mixture was stirred at ambient temperature for 30 min, heated at 50° C. for 2.5 h, then cooled to ambient temperature and left stirring at ambient temperature for 12 h. The reaction mixture was cooled to −50° C. and a solution of benzoyl chloride (15.0 mL, 129.3 mmol) in 50 mL THF was added to it over 30 min. The mixture was stirred at ambient temperature for 2 h. After the completion of reaction (monitored by TLC), the reaction mixture was quenched with saturated NH$_4$Cl solution (100 mL) and extracted with EtOAc (3×150 mL). The combined organic layers were dried over sodium sulphate and concentrated under reduced pressure to get crude material, which was purified by column chromatography (silica: 100-200 mesh size; elution: 0-30% ethyl acetate) to obtain the title compound (21.7 g, 76.4%). R$_f$: 0.4 in 30% ethyl acetate in hexane.

Step 8. ((1R,2R)-2-formylcyclobutyl)methyl Benzoate

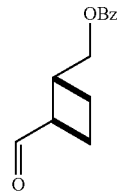

To a 500 mL 3 necked round-bottomed flask equipped with a mechanical stirrer, a nitrogen gas inlet and a temperature probe was charged ((1R,2R)-2-(hydroxymethyl) cyclobutyl)methyl benzoate (13 g, 59.0 mmol) and DCM (130 mL). The solution was cooled to 0-5° C. in an ice/water bath, and (diacetoxyiodo) benzene (Sigma Aldrich; 20.57 g, 63.9 mmol) was added followed by 2,2,6,6-tetramethylpiperidinooxy (Sigma Aldrich; 0.475 g, 3.04 mmol), and water (0.106 mL, 5.90 mmol). The reaction was stirred at 0-5° C. briefly then it was warmed up to ambient temperature slowly in 1 hour, and kept stirring at room temperature. After 4 h 0.05 eq. of 2,6,6-tetramethylpiperidinooxy (0.475 g, 3.04 mmol) was added and after 23 h 0.1 eq. of (diacetoxyiodo) benzene (1.960 g, 6.08 mmol) was added. After 46 h the reaction was quenched with 50 mL $Na_2S_2O_3$ solution and 150 mL sat. $NaHCO_3$ solution. The mixture was stirred for 30 min, extracted with DCM, concentrated and loaded on silica gel. The material was purified by column (Heptane: EtOAc=10:0 to 1.5:8.5) to afford ((1R,2R)-2-formylcyclobutyl)methyl benzoate (12.08 g, 55.3 mmol, 94% yield).

Step 9. ((1R,2R)-2-((S,E)-1-hydroxyhex-2-en-1-yl)cyclobutyl)methyl Benzoate

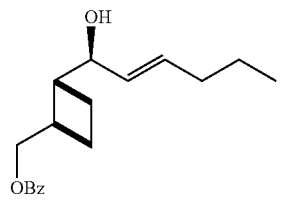

The title compound was prepared from ((1R,2R)-2-formylcyclobutyl)methyl benzoate (1.00 g), following the procedure as described for the synthesis of Intermediate AA16, Step 8, except that the crude product was purified by flash chromatography on ISCO Gold silica gel column using 0-20% EtOAc/Hexanes as eluent to provide the title compound as a white solid (845 mg, 2.93 mmol, 64% yield).

Step 10. ((1R,2R)-2-((S,E)-1-((tert-butyldimethylsilyl)oxy)hex-2-en-1-yl)cyclobutyl)methyl Benzoate

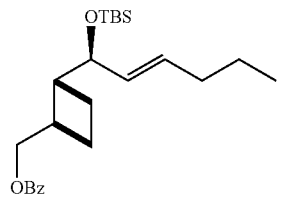

To a 0° C. solution of ((1R,2R)-2-((S,E)-1-hydroxyhex-2-en-1-yl)cyclobutyl)methyl benzoate (828 mg, 2.87 mmol), imidazole (Acros Organics 99+%, crystalline; 0.284 mL, 4.31 mmol) in $CH_2Cl_2$ (20 mL) under $N_2$ was added 2,6-dimethylpyridine (Sigma-Aldrich Chemical Company, Inc.; 1.334 mL, 11.48 mmol) followed by tert-butyldimethylsilyl trifluoromethanesulfonate (Sigma-Aldrich Chemical Company, Inc.; 1.319 mL, 5.74 mmol, The cloudy mixture was allowed to warm with the ice bath to ambient temperature and stirred for 24 h. The mixture was then quenched with saturated aqueous $NaHCO_3$ (10 mL), diluted with water (15 mL), and extracted with $CH_2Cl_2$ (3×15 mL). After removal of organic solvents under reduced pressure, purification of the residue by flash chromatography on ISCO Gold silica gel column eluting with 0-20% EtOAc/Hexanes provided the title compound as a white solid (1.155 g, 2.87 mmol, 100% yield).

Step 11. (1R,2R)-2-((S,E)-1-((tert-butyldimethylsilyl)oxy)hex-2-en-1-yl)cyclobutanecarbaldehyde

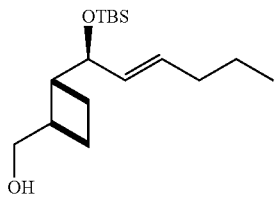

To a solution of ((1R,2R)-2-((S,E)-1-((tert-butyldimethylsilyl)oxy)hex-2-en-1-yl)cyclobutyl)methyl benzoate (1.100 g, 2.73 mmol, Step 7) in MeOH (4.55 ml) at ambient temperature was added sodium methylate (2.56 ml, 30% w/w, 13.66 mmol, Acros Organics). The solution was allowed to stir at ambient temperature for 45 min, and then treated with saturated aqeuous $NaHCO_3$ (5 mL) and water (5 mL). The resulting mixture was extracted with EtOAc (3×15 mL). The organic layers were combined and washed with water (3 mL) and brine (3 m L). Removal of organic solvents under reduced pressure provided the crude title compound as a white solid (710 mg, 2.38 mmol, 87% yield).

Step 12. (1R,2R)-2-((S,E)-1-((tert-butyldimethylsilyl)oxy)hex-2-en-1-yl)cyclobutanecarbaldehyde

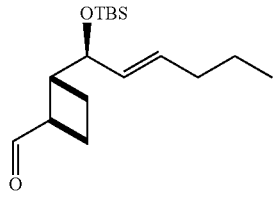

To a −78° C. solution of dimethyl sulfoxide (675 µl, 9.51 mmol, Sigma-Aldrich Chemical Company, Inc.) in $CH_2Cl_2$ (6.8 mL) under $N_2$ was added oxalyl chloride (2.38 mL, 2.0 M in $CH_2Cl_2$, 4.76 mmol) dropwise over 4 min. The mixture was allowed to stir in the cold bath for 45 min. To the solution was slowly added a solution of ((1R,2R)-2-((S,E)-1-((tert-butyldimethylsilyl)oxy)hex-2-en-1-yl)cyclobutyl) methanol (710 mg, 2.378 mmol) in $CH_2Cl_2$ (3 mL) over 2 min. The mixture was allowed to stir in the bath for 1.5 h, followed by slow addition of anhydrous triethylamine (2.0 mL, 14.27 mmol, Sigma-Aldrich Chemical Company, Inc) dropwise. The resulting mixture was removed from ice bath and left stirring at ambient temperature for 45 min. To the cloudy mixture was added saturated aqueous $NaHCO_3$ (5 mL) and water (10 m L). The resulting mixture was extracted with $CH_2Cl_2$ (2×25 mL). The organic solution was combined and washed with water (8 mL). Removal of organic solvents under reduced pressure provided crude title compound as a white solid (695 mg, 2.34 mmol, 99% yield).

Step 13: ((S)-ethyl 5-(((1R,2R)-2-((S,E)-1-((tert-butyldimethylsilyl)oxy)hex-2-en-1-yl)cyclobutyl)methyl)-6',8-dichloro-3',4,4',5-tetrahydro-2H,2'H-spiro[benzo[b][1,4]oxazepine-3,1'-naphthalene]-7-carboxylate

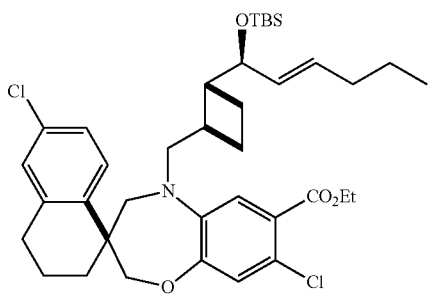

To a solution of (1R,2R)-2-((S,E)-1-((tert-butyldimethylsilyl)oxy)hex-2-en-1-yl)cyclobutanecarbaldehyde (Intermediate AA17 Step 12; 147 mg, 0.495 mmol) and (S)-ethyl 6',8-dichloro-3',4,4',5-tetrahydro-2H,2'H-spiro[benzo[b][1,4]oxazepine-3,1'-naphthalene]-7-carboxylate (Intermediate AA17 Step 5; 201 mg, 0.495 mmol) in 20% AcOH/CH$_2$Cl$_2$ (4 mL) under N$_2$ in 0° C. ice bath was added a solution of sodium borocyanohydride (2.395 mL, 1.0 N in THF, 2.395 mmol, Sigma-Aldrich Chemical Inc.) drop wise using a syringe pump over 50 min. The resulting mixture was allowed to warm to ambient temperature and left stirring for 30 min. The reaction solution was then treated with saturated aqueous NH$_4$Cl (10 mL) and water (8 mL) and the resulting mixture was extracted with EtOAc (3×12 mL). The organic layers were combined and after removal of organic solvents under reduced pressure, purification of the residue by flash chromatography on ISCO Gold silica gel column with 0-50% EtOAc/Hexanes provided the title compound as white solid (221 mg, 0.322 mmol, 65% yield).

Step 14: (S)-ethyl 6',8-dichloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate

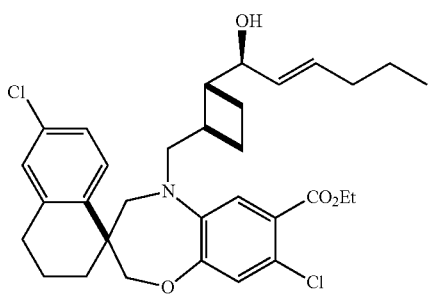 [SMILES: CCC/C=C/[C@H](O)[C@@H]1CC[C@H]1CN1C[C@@]2(CCCc3cc(Cl)ccc32)COc2cc(Cl)c(C(=O)OCC)cc21]

A solution of (S)-ethyl 5-(((1R,2R)-2-((S,E)-1-((tert-butyldimethylsilyl)oxy)hex-2-en-1-yl)cyclobutyl)methyl)-6',8-dichloro-3',4,4',5-tetrahydro-2H,2'H-spiro[benzo[b][1,4]oxazepine-3,1'-naphthalene]-7-carboxylate (220 mg, 0.320 mmol, Step 10) in THF (2 mL) was added tetrabutylammonium fluoride (0.641 mL, 1.0 M in THF, 0.641 mmol, Sigma-Aldrich Chemical Company, Inc.). The mixture was allowed to stir at ambient temperature overnight, and then treated with water (6 mL) and extracted with EtOAc (3×8 mL). The organic layers were combined and after removal of organic solvents under reduced pressure, purification of the residue by flash chromatography on ISCO Gold silica gel column with 0-50% EtOAc/Hexanes provided the title compound as white solid (114 mg, 0.199 mmol, 62% yield).

Step 15: (S)-6'-8-dichloro-5-(((1R,2R)-2-((S,E)-1-hydroxypent-2-en-1-yl)cyclobutyl)methyl)-3',4,4',5-tetrahydro-2H,2'H-spiro[benzo[b][1,4]oxazepine-3,1'-naphthalene]-7-carboxylic Acid A mixture of (S)-ethyl 6',8-dichloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (114 mg, 0.199 mmol) in THF/water (1:1) (3.98 mL) was treated with lithium hydroxide (23.84 mg, 0.996 mmol). The mixture was stirred at 50° C. for 30 min. The mixture was then quenched with HOAc (0.1 mL), diluted with water (8 mL) and extracted with EtOAc (3×12 mL). After removal of organic solvents under reduced pressure, purification of the residue by flash chromatography on 24 g silica gel column with 0-100% EtOAc in hexanes provided (S)-6'-8-dichloro-5-(((1R,2R)-2-((S,E)-1-hydroxypent-2-en-1-yl)cyclobutyl)methyl)-3',4,4',5-tetrahydro-2H,2'H-spiro[benzo[b][1,4]oxazepine-3,1'-naphthalene]-7-carboxylic acid as colorless solid. MS m/z (ESI, +ve ion) 544.0 (M+H)$^+$.

Intermediate AA18

(S)-6'-chloro-4',4'-difluoro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3, 1'-naphthalene]-7-carboxylic

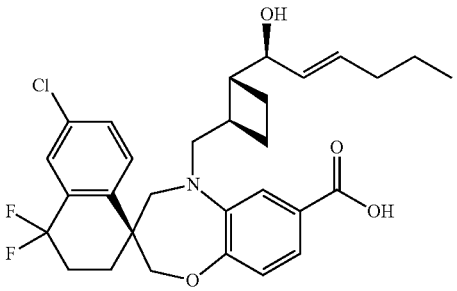 [SMILES: CCC/C=C/[C@H](O)[C@@H]1CC[C@H]1CN1C[C@@]2(CCC(F)(F)c3cc(Cl)ccc32)COc2ccc(C(=O)O)cc21]

Step 1:
5-chloro-2-fluoro-N-methoxy-N-methylbenzamide

To a stirred solution of 5-chloro-2-fluorobenzoic acid (900 g, 5.17 mol) in DCM (10 L) was added oxalyl chloride (990 g, 7.8 mol) at 0° C. After addition, DMF (3 mL) was added and the reaction mixture was stirred at ambient temperature overnight. On completion, the solvent was removed under reduced pressure, the residue was dissolved in DCM (2 L) and the solution was concentrated again to dryness. The acid chloride thus obtained (900 g, 4.66 mol) was dissolved in DCM (6 L) and N,O-dimethylhydroxylamine hydrochloride (682.27 g, 7 mmol) was added followed by a solution of triethylamine (2.7 L, 19.4 mol) in DCM (4 L) dropwise at 0° C. The reaction mixture was warmed slowly to ambient temperature, and stirred overnight. The mixture was then quenched with ice water and the layers were separated. The aqueous layer was extracted with DCM (2×3 L) and the combined organic layer was washed with 0.5 N HCl (4 L), 1N NaOH (4 L), water (5 L) and brine (5 L) then it was dried over $Na_2SO_4$ and concentrated to afford 5-chloro-2-fluoro-N-methoxy-N-methylbenzamide (900 g, 80% yield).

Step 2: diethyl 6-chloro-4-oxo-3,4-dihydronaphtha-lene-1,1(2H)-dicarboxylate

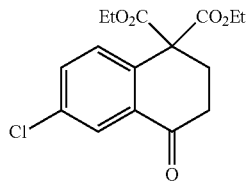 [SMILES: CCOC(=O)C1(C(=O)OCC)CCC(=O)c2cc(Cl)ccc21]

5-chloro-2-fluoro-N-methoxy-N-methylbenzamide (900 g, 4.15 mol) was dissolved in THF (10 L) and the solution was cooled to −78° C. and vinylmagnesium bromide (1.0 M solution in THF, 6.2 L, 6.2 mol) was added over 1 h. After the addition, the reaction mixture was warmed to ambient temperature slowly and allowed to stir for 2 h. The resulting suspension was cooled to −78° C. and diethyl malonate (1980 mL, 12.4 mol) was added. The mixture was then allowed to reach ambient temperature and stirred for 1 h. The reaction was then quenched with saturated $NH_4Cl$ solution (8 L) and extracted with ethyl acetate (3×8 L). The combined organic layers were washed with brine (5 L), dried over $Na_2SO_4$ and concentrated to afford a yellow oil. The above obtained oil was dissolved in DMSO (2.3 L) and potassium carbonate (288 g, 2.09 mol) was added. The mixture was heated to 70° C. overnight and upon completion, the reaction was cooled to ambient temperature and diluted with ice cold water (10 L). The aqueous layer was extracted with ethyl acetate (2×10 L) and the combined organic layer was washed with brine (3×5 L), dried over $Na_2SO_4$ and concentrated under reduced pressure. The crude material thus obtained was purified by column chromatography over silica gel (60-120 mesh, 4% ethyl acetate/ hexane) affording pure diethyl 6-chloro-4-oxo-3,4-dihydronaphthalene-1,1(2H)-dicarboxylate (900 g, 67% yield).

Step 3: diethyl 6-chloro-4,4-difluoro-3,4-dihydronaphthalene-1,1(2H)-dicarboxylate

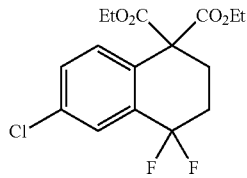 [SMILES: CCOC(=O)C1(C(=O)OCC)CCC(F)(F)c2cc(Cl)ccc21]

A solution of diethyl 6-chloro-4-oxo-3,4-dihydronaphthalene-1,1(2H)-dicarboxylate (4.5 g, 13.86 mmol) in bis(2-methoxyethyl)aminosulfur trifluoride (Deoxo-Fluor®, Sigma-Aldrich, St. Louis, MO, USA) (10.22 ml, 55.4 mmol) was treated with ethanol (0.064 g, 1.386 mmol) and heated at 60° C. for 2 d. The reaction was then cooled to room temperature and quenched by careful addition into a saturated sodium bicarbonate solution. The mixture was extracted with ethyl acetate, washed with 1N HCl, sat. $NaHCO_3$ solution, and brine. The organic phase was dried over $MgSO_4$, filtered and concentrated. Purification by normal phase silica gel column chromatography (5% ethyl acetate in hexanes) afforded diethyl 6-chloro-4,4-difluoro-3,4-dihydronaphthalene-1,1(2H)-dicarboxylate (4.0 g, 11.54 mmol, 83% yield) and recovered diethyl 6-chloro-4-oxo-3,4-dihydronaphthalene-1,1(2H)-dicarboxylate (420 mg, 1.293 mmol, 9.33% yield).

Step 4: (6-chloro-4,4-difluoro-1,2,3,4-tetrahydronaphthalene-1,1-diyl)dimethanol

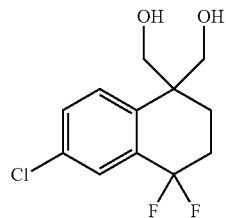 [SMILES: OCC1(CO)CCC(F)(F)c2cc(Cl)ccc21]

To a solution of diethyl 6-chloro-4,4-difluoro-3,4-dihydronaphthalene-1,1(2H)-dicarboxylate (1.05 g, 3.03 mmol) in THF (9.18 mL) at 0° C. was added lithium aluminum hydride (1.0 M in THF, 9.08 mL, 9.08 mmol). The reaction was allowed to warm to ambient temperature and stir for 1.5 h. The reaction was cooled back to 0° C. and quenched with 1 mL water followed by 20 mL 2N HCl. To the mixture was added 75 mL ethyl acetate and sufficient solid NaCl to saturate the aqueous layer. The phases were separated and the aqeuous layer was extracted with 25 mL of ethyl acetate. The combined organics were washed with brine and dried over $Na_2SO_4$, filtered, and concentrated. Purification by silica gel column chromatography using a gradient of 15-30% acetone in hexanes afforded (6-chloro-4,4-difluoro-1,2,3,4-tetrahydronaphthalene-1,1-diyl)dimethanol (600 mg, 2.284 mmol, 75% yield). Additional or alternative purification can be effected by washing or slurrying the solid product with dichloromethane.

Step 5: (S)-(6-chloro-4,4-difluoro-1-(hydroxymethyl)-1,2,3,4-tetrahydronaphthalen-1-yl)methyl 4-bromobenzoate

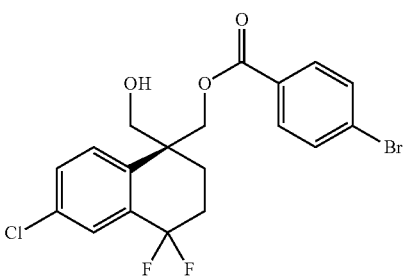 [SMILES: O=C(OC[C@@]1(CO)CCC(F)(F)c2cc(Cl)ccc21)c1ccc(Br)cc1]

Copper(II) chloride (0.134 g, 0.995 mmol) and 2,6-bis ((R)-5,5-dibutyl-4-phenyl-4,5-dihydrooxazol-2-yl)pyridine (0.612 g, 1.031 mmol, prepared according to the procedure described in Li, J. Y; You, Y. S.; Kang, S. H. *J. Am. Chem. Soc.* 2011, 133, 1772) were combined in 50 mL anhydrous DCM under argon and stirred at ambient temperature for 3 h. The catalyst solution so prepared was added to a solution of (6-chloro-4,4-difluoro-1,2,3,4-tetrahydronaphthalene-1, 1-diyl)dimethanol (4.75 g, 18.08 mmol) in 250 mL anhydrous DCM and rinsed with 25 mL anhydrous DCM. The reaction was cooled to −78° C. and treated with 4-bromobenzoyl chloride (4.76 g, 21.70 mmol) in 25 mL DCM and rinsed with 25 mL of DCM. The reaction was then treated with N-ethyl-N-isopropylpropan-2-amine (3.46 mL, 19.89 mmol) and held between −78° C. to −45° C. overnight. The reaction was then quenched with 250 mL 10% citric acid solution. The layers were separated and the organic phase was washed with 100 mL 10% citric acid solution, 200 mL sat. NaHCO$_3$ solution and 200 mL brine. The organic phase was dried over MgSO$_4$, filtered, and concentrated. Purification by silica gel column chromatography using 10-15% acetone in hexanes (330 g Redisep Gold® column, Teledyne Isco, Lincoln NE, USA) followed by repurification of mixed fractions (220 g Redisep Gold® column, Teledyne Isco, Lincoln NE, USA) afforded 6.5 g of (S)-(6-chloro-4, 4-difluoro-1-(hydroxymethyl)-1,2,3,4-tetrahydronaphthalen-1-yl)methyl 4-bromobenzoate. The enantiomeric excess was found to be 87% (15% IPA in hexanes, Chiralcel OD-H.) If desired, the enantiomeric excess may be improved by recrystallization from toluene as follows: 3.8 g of (S)-(6-chloro-4,4-difluoro-1-(hydroxymethyl)-1,2,3,4-tetrahydronaphthalen-1-yl)methyl 4-bromobenzoate (~80% ee) was heated in sufficient toluene to dissolve in a 90° C. bath. The solution is cooled to ambient temperature with stirring and seeded with racemic (6-chloro-4,4-difluoro-1-(hydroxymethyl)-1,2,3,4-tetrahydronaphthalen-1-yl)methyl 4-bromobenzoate. After 1 h at ambient temperature (crystallization occurred), the solution was cooled to 0° C. and stirred for 30 min, then warmed to ambient temperature and stirred for 1 h. The resultant solids were filtered and rinsed with 2×5 mL 0° C. toluene to afford 500 mg of racemic (6-chloro-4,4-difluoro-1-(hydroxymethyl)-1,2,3,4-tetrahydronaphthalen-1-yl)methyl 4-bromobenzoate. The mother liquor was concentrated to afford 3.3 g of 94% ee (S)-(6-chloro-4,4-difluoro-1-(hydroxymethyl)-1,2,3,4-tetrahydronaphthalen-1-yl)methyl 4-bromobenzoate.

Step 6: (R)-(6-chloro-4,4-difluoro-1-formyl-1,2,3,4-tetrahydronaphthalen-1-yl)methyl 4-bromobenzoate

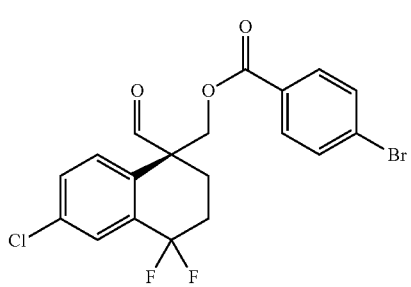 [SMILES: O=C[C@]1(COC(=O)c2ccc(Br)cc2)CCC(F)(F)c2cc(Cl)ccc21]

The title compound was synthesized from (S)-(6-chloro-4,4-difluoro-1-(hydroxymethyl)-1,2,3,4-tetrahydronaphthalen-1-yl)methyl 4-bromobenzoate following the procedure described for Intermediate AA 11, Step 6.

Step 7: (R)-(6-chloro-1-(dimethoxymethyl)-4,4-difluoro-1,2,3,4-tetrahydronaphthalen-1-yl)methanol

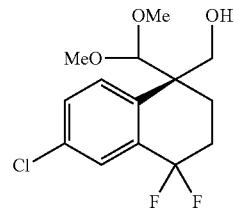 [SMILES: COC(OC)[C@]1(CO)CCC(F)(F)c2cc(Cl)ccc21]

The title compound was synthesized from (R)-(6-chloro-4,4-difluoro-1-formyl-1,2,3,4-tetrahydronaphthalen-1-yl) methyl 4-bromobenzoate following the procedure described for Intermediate AA 11, Step 7.

Step 8: (R)-tert-butyl 4-((6-chloro-1-(dimethoxymethyl)-4,4-difluoro-1,2,3,4-tetrahydronaphthalen-1-yl)methoxy)-3-nitrobenzoate

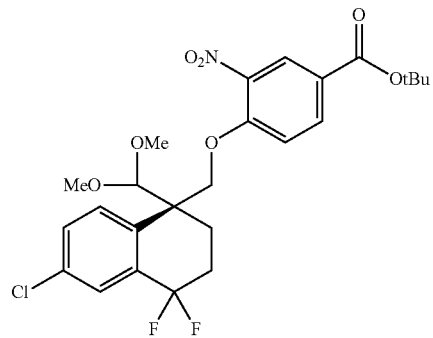 [SMILES: COC(OC)[C@]1(COc2ccc(C(=O)OC(C)(C)C)cc2[N+](=O)[O-])CCC(F)(F)c2cc(Cl)ccc21]

The title compound was synthesized from (R)-(6-chloro-1-(dimethoxymethyl)-4,4-difluoro-1,2,3,4-tetrahydronaphthalen-1-yl)methanol and tert-butyl-4-fluoro-3-nitrobenzoate (Intermediate AA 11, Step 8) following the procedure described for Intermediate AA 11, Step 9.

Step 9. (R)-tert-butyl 4-((6-chloro-4,4-difluoro-1-formyl-1,2,3,4-tetrahydronaphthalen-1-yl)methoxy)-3-nitrobenzoate

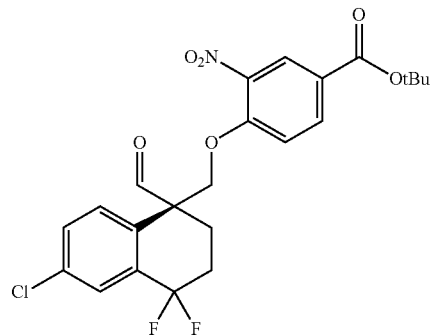 [SMILES: CC(C)(C)OC(=O)c1ccc(OC[C@@]2(C=O)CCC(F)(F)c3cc(Cl)ccc32)c([N+](=O)[O-])c1]

The title compound was synthesized from (R)-tert-butyl 4-((6-chloro-1-(dimethoxymethyl)-4,4-difluoro-1,2,3,4-tetrahydronaphthalen-1-yl)methoxy)-3-nitrobenzoate following the procedure described for Intermediate AA 11, Step 10.

Step 10: (S)-6'-chloro-4',4'-difluoro-3',4,4',5-tetrahydro-2H,2'H-spiro[benzo[b][1,4]oxazepine-3,1'-naphthalene]-7-carboxylic Acid

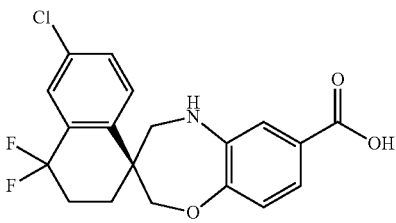 [SMILES: O=C(O)c1ccc2c(c1)NC[C@@]1(CCC(F)(F)c3cc(Cl)ccc31)CO2]

The title compound was synthesized from (R)-tert-butyl 4-((6-chloro-4,4-difluoro-1-formyl-1,2,3,4-tetrahydronaphthalen-1-yl)methoxy)-3-nitrobenzoate following the procedure described for Intermediate AA 11, Step 11.

Step 11: 1-ethoxycyclopropanol

(1-ethoxycyclopropoxy) trimethylsilane (Wonda, 500 g, 2.866 mol) was dissolved in methanol (1.4 L) and the resulting solution was stirred at ambient temperature for 2 days. The reaction was monitored by NMR and upon completion, methanol was removed in vacuo, yielding the title compound (266 g, 90.8% yield).

Step 12: Benzyl 2-cyclopropylideneacetate

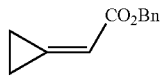

A solution of 1-ethoxycyclopropanol (266 g, 2.61 mol) and benzoic acid (63.7 g, 0.52 mol) in anhydrous chloroform (3 L), under an atmosphere of nitrogen, was refluxed for 10 min and then a solution of benzyl 2-(triphenylphosphoranylidene)acetate (Wonda, 1.07 kg, 2.61 mol) dissolved in the minimum volume of chloroform was added dropwise. The reaction was monitored by TLC and upon completion, the mixture was allowed to cool to room temperature and the solvent was removed on a rotary evaporator. The residue was directly loaded onto the column (60-120 mesh silica gel; pure hexane to 5% ethyl acetate in hexane) to afford the title compound (331 g, 67.4%). $R_f$: 0.65 in 10% ethyl acetate in hexane.

Step 13: (S)-benzyl 2-hydroxy-2-(1-hydroxycyclopropyl)acetate

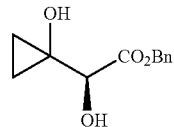

To an ice-cooled solution of benzyl 2-cyclopropylideneacetate (331 g, 1.76 mol) in a mixture of t-butanol (8.8 L) and water (8.8 L) was added AD-mix β (Aldrich, 2.45 kg). The resulting orange suspension was vigorously stirred at 0° C. Ten minutes later, methanesulfonamide (Alfa Aesar, 167 g, 1.76 mol) was added to the reaction in a single portion. The reaction mixture was stirred at 0° C. for 16 h. Upon completion, solid sodium sulfite (830 g, 6.58 mol) was added and the mixture was stirred at 0° C. for 15 minutes. The reaction mixture was diluted with ethyl acetate (10 L), the layers were separated and the aqueous layer was extracted with ethyl acetate (2×3 L). The combined organic layer was washed with brine, dried over sodium sulfate, filtered and concentrated in vacuo to yield the crude material which was purified by column chromatography (60-120 mesh silica; pure hexane to 40% ethyl acetate in hexane) affording the title compound as a translucent oil (260 g, 66.5%). $R_f$: 0.1 in 10% ethyl acetate in hexane. Chiral HPLC conditions: Column: Chiral pak IC (250 mm×4.6 mm); Mobile Phase: n-Hexane:EtOH: 90:10. Run Time: 20 min. Flow rate: 1 ml/min. Retention time (minor peak)-9.35 (5.4%); Retention time (major peak)-11.67 (94.6%).

Step 14: (R)-1-(1-hydroxycyclopropyl)ethane-1,2-diol

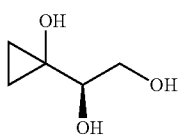

A solution of (S)-benzyl 2-hydroxy-2-(1-hydroxycyclopropyl)acetate (260 g, 1.17 mol) in THF (5 L) was cooled to 0° C. and lithium borohydride (98 g, 4.68 mol) was added portion-wise. After addition of lithium borohydride, the reaction mixture was stirred at 10° C. for 2 h. Upon completion, the reaction was cooled to 0° C. and quenched carefully with methanol (2.02 L). Ammonium acetate solution in methanol (1.5 kg in 1 L of methanol) was then added followed by the addition of acetic acid (130 mL). The reaction mixture was filtered and the filtrate was concentrated at 30° C. at rotavapor. The residue thus obtained was diluted with THF (3 L) and filtered to remove the solid. The solid cake was washed with copious amount of THF. The filtrate was concentrated by rotary evaporator (temperature of the waterbath was kept at 30° C.) to obtain the crude material (300 g) which was used as such in next step. $R_f$: 0.1 in 40% ethyl acetate in hexane.

Step 15: (R)-1-(2-((tert-butyldiphenylsilyl)oxy)-1-hydroxyethyl)cyclopropanol

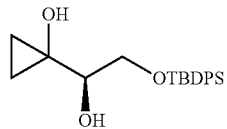

The crude material from step 4 (300 g) was dissolved in THF (5 L) and imidazole (556 g, 8.19 mol) was added. The resulting reaction mixture was cooled to 0° C. and tert-butyl diphenylsilyl chloride (1.07 L, 4.1 mol) was added dropwise over a period of 1 h. The resulting reaction mixture was stirred at rt for 4 h. Upon completion, the reaction was quenched with saturated NH₄Cl solution at 0° C. The aqueous layer was extracted with ethyl acetate (3×3 L) and the combined organic layer was washed with brine, dried over sodium sulfate and concentrated to obtain crude material which was purified by column chromatography (60-120 mesh; pure hexane to 10% ethyl acetate in hexane) affording pure title compound (240 g, 57.5% yield) as a thick oil. $R_f$: 0.45 in 30% ethyl acetate in hexane.

Step 16: (S)-2-(((tert-butyldiphenylsilyl)oxy)methyl)cyclobutanone

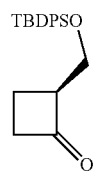

(R)-1-(2-((tert-butyldiphenylsilyl)oxy)-1-hydroxyethyl)cyclopropanol (240 g, 0.673 mol) was dissolved in anhydrous pyridine (6 L), under an atmosphere of nitrogen, and the resulting solution was cooled to 0° C. in an ice/water bath. Neat methanesulfonyl chloride (78.5 mL; 1.01 mol) was added dropwise via dropping funnel over a period of 1 h. The reaction mixture was then allowed to slowly warm to room temperature and it was stirred at room temperature for 4 h. Upon completion, the reaction mixture was quenched with ice-water and the aqueous layer was extracted with ethyl acetate (3×5 L). The combined organic layers were washed with 15% citric acid solution to removed pyridine, then with brine and finally dried over sodium sulfate. The solvent was removed under reduced pressure to obtain the crude material which was purified by column chromatography (60-120 mesh size silica; eluting with a gradient of 0-5% ethyl acetate in hexanes) affording pure title compound (163 g, 71.5% yield). $R_f$: 0.55 in 10% ethyl acetate in hexane.

Step 17: (R)-tert-butyl((2-(methoxymethylene)cyclobutyl)methoxy)-diphenyl-silane

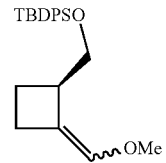

A suspension of (methoxymethyl) triphenylphosphonium chloride (dried under high vacuum for 3 h while heating at 60° C., 578 g, 1.685 mol, 3.5 equiv.) in anhydrous THF (vigorously purged with Argon for over 15 minutes immediately prior to use, 5.5 L) was cooled to −78° C. in a dry ice/acetone slurry and N-butyl lithium (2.5 M solution in hexanes, 540 mL, 1.35 mol, 2.8 equiv.) was added dropwise via cannula, giving a yellowish suspension. The dry ice slurry was immediately replaced with an ice-water bath, and the ylide suspension rapidly became dark red upon warming to zero degree. After 15 minutes, a solution of (S)-2-(((tert-butyldiphenylsilyl)oxy)methyl)cyclobutanone (163 g, 0.481 mol) in THF (1.5 L) was added to the above prepared ylide solution in a dropwise manner over a period of 30 min. After complete addition, the reaction was stirred at rt for 16 h (the color persisted). The reaction was monitored by TLC and upon completion, the mixture was cooled to 0° C. and quenched by the cautious addition of saturated ammonium chloride solution. The aqueous phase was extracted with ethyl acetate (3×3 L) and the combined organic layer was washed with brine, dried over sodium sulfate and concentrated under reduced pressure to obtain the crude material which was purified by column chromatography (60-120 mesh silica gel, pure hexane to 2% ethyl acetate in hexanes) affording the title compound (mixture of diastereomers, 105 g, 59.5%). A small amount of hydrolyzed product (described in the following step) was also observed by TLC and NMR. $R_f$: 0.6 and 0.65 (diastereomers) in 10% ethyl acetate in hexane.

Step 18: (1S,2R)-2-(((tert-butyldiphenylsilyl)oxy)methyl)cyclobutanecarbaldehyde

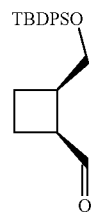

To a stirred solution of (R)-tert-butyl((2-(methoxymethylene)cyclobutyl)methoxy)-diphenyl-silane (105 g, 0.286 mol) in DCM (2.1 L), water (53 mL) was added and the resulting solution was cooled to −78° C. Then a solution of trichloroacetic acid (84 g, 0.51 mol) in DCM (500 mL) was added at −78° C. dropwise over a period of 1 h. The solution was allowed to warm to 0° C. and it was stirred at 0° C. for 15 min and then at ambient temperature for 2 h. The reaction was monitored by TLC and upon completion, the mixture was cooled to 0° C. and quenched by the addition of saturated sodium bicarbonate solution. The layers were separated and the aqueous phase was extracted with DCM (3×1 L). The combined organics were washed with brine, dried over sodium sulfate, filtered, and concentrated in vacuo to obtain the title compound (97 g, 96.2%) which had partially (~30%) epimerized to (1R,2R)-2-((tert-butyldiphenylsilyloxy)methyl)cyclobutane-carbaldehyde (described below). This mixture was used as such in the following step. R$_f$: 0.55 in 10% ethyl acetate in hexane.

Step 19: (1R,2R)-2-((tert-butyldiphenylsilyloxy) methyl)cyclobutane-carbaldehyde

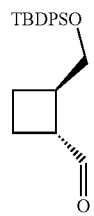

A solution of (1S,2R)-2-(((tert-butyldiphenylsilyl)oxy) methyl)cyclobutanecarbaldehyde (97.0 g, 0.275 mol) in MeOH (1.94 L) was cooled to 0° C. and potassium tert-butoxide (Aldrich, 1 M in THF, 110.0 mL, 0.110 mol) was added to it dropwise. The reaction mixture was stirred for 6 h at ambient temperature. The reaction was monitored by $^1$H NMR and upon completion, the mixture was quenched with pH 7 phosphate buffer solution (700 mL) and the aqueous phase was extracted with ethyl acetate (3×1.5 L). The combined organic layer was washed with brine (1.5 L), dried over anhydrous Na$_2$SO$_4$ and concentrated under reduced pressure affording the title compound (95.0 g, 97.9%) as yellowish thick oil. The crude compound was used in the next step without further purification. Nearly 4-5% of the other isomer ((1S,2R)-2-(((tert-butyldiphenylsilyl)oxy) methyl)cyclobutanecarbaldehyde) is also observed by NMR. R$_f$: 0.55 in 10% ethyl acetate in hexane.

The enantiomeric purity of this material could be improved as follows: To a solution of (1R,2R)-2-((tert-butyldiphenylsilyloxy)methyl)cyclobutane-carbaldehyde (95.0 g, 0.269 mol) in EtOH (950 mL) was added sodium acetate (44.2 g, 0.539 mol) and the reaction mixture was stirred at rt for 15 min. Then the reaction mixture was cooled to 0° C. and semicarbazide hydrochloride (Aldrich, 33.1 g, 0.296 mol) was added portion-wise and the reaction mixture was stirred at rt for 2 h. Upon completion, the reaction was quenched with sat. sodium bicarbonate solution (500 mL) and the aqueous layer was extracted with DCM (2×2.0 L). The combined organic layer was washed with water (1.0 L), followed by brine (1.0 L), dried over anhydrous Na$_2$SO$_4$ and concentrated under reduced pressure affording a yellowish thick gel (98.0 g, 89%). The crude semicarbazone thus obtained was dissolved in 430 mL of hot methyl tert-butyl ether (MTBE) and then 6.4 L of boiling hot n-heptane was added to the resulting solution. The mixture was allowed to stand at ambient temperature for 3 days. The crystalline product was collected and washed with a small amount of hexane (50 mL) affording 60 g of enantio-enriched material (enantiomeric excess 89%). This material was recrystallized as described above using 263 mL MTBE and 3.94 L hot n-heptane, aging at ambient temperature for 15 h delivering 55 g of enantio-enriched material (enantiomeric excess was 96%, Column: Chiral pak ADH (250 mm×4.6 mm); Mobile Phase: n-Hexane:EtOH: 97:3. Run Time: 25 min. Flow rate: 1 ml/min. Retention time (major peak)-11.65 (98.04%); Retention time (minor peak)-16.79 (1.96%). This material was dissolved in acetone (1.13 L), cooled to 0° C. and Amberlyst-15 ion exchange resin, wet (Aldrich, 55.0 g) was added. Aqueous formaldehyde (110 mL, 37% solution) was added to the reaction mixture rapidly via dropping funnel at 0° C. over a period of 10 min. The reaction mixture was stirred at ambient temperature for 3 h then it was filtered through a celite bed and concentrated under reduced pressure below 35° C. The residual turbid aqueous suspension was dilute with brine and extracted with pentane (3×1 L). The combined organic layers were washed with brine, dried over anhydrous Na$_2$SO$_4$ and concentrated under reduced pressure affording the enantio-enriched title compound (43.1 g, 91.1%) as colourless but opaque oil.

Step 20: (S)-5-(((1R,2R)-2-(((tert-butyldiphenylsilyl)oxy)methyl)cyclobutyl)methyl)-6'-chloro-4',4'-difluoro-3',4,4',5-tetrahydro-2H,2'H-spiro[benzo[b][1,4]oxazepine-3,1'-naphthalene]-7-carboxylic Acid

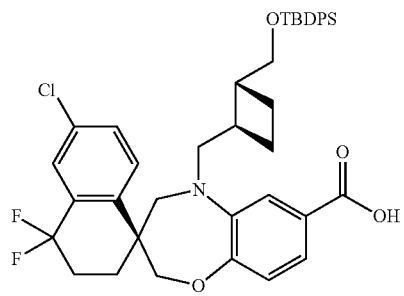

To a solution of (1R,2R)-2-(((tert-butyldiphenylsilyl)oxy) methyl)cyclobutanecarbaldehyde (Intermediate AA18, Step 19; 4.73 g, 13.43 mmol) and (S)-6'-chloro-4',4'-difluoro-3',4,4',5-tetrahydro-2H,2'H-spiro[benzo[b][1,4]oxazepine-3,1'-naphthalene]-7-carboxylic acid (step 10, 3.4 g, 8.95 mmol) in acetic acid (29.8 ml) and DCM (59.7 ml) at 0° C. (stirred for 15 minutes) was added sodium cyanoborohydride (0.281 g, 4.48 mmol) as a 1M solution in THF slowly over 2 h. The reaction appears mostly complete by TLC. The mixture was poured into ~3M NaOH (25.06 g, 627 mmol in 200 mL of water) and 300 mL of ethyl ether. The aqueous phase was extracted with ethyl ether (200 mL) and the combined organic phase was washed with 100 mL 10% Na$_2$CO$_3$/200 mL brine, followed by 1N HCl, and again brine, then it was dried over MgSO$_4$, filtered, and concentrated. The crude material was purified on a 330 g silica gel column, eluting with 15-20% ethyl acetate in hexanes. The desired product dragged and did not separate well from ((1R,2R)-2-(((tert-butyldiphenylsilyl)oxy)methyl)cyclobutyl)methanol (1.75 g, 4.94 mmol, 55.1% yield) also formed in the reaction. The mixed fractions (4 g) were collected and repurified on a 220 g silica gel column using 10-20% acetone in hexanes leading to the isolation of desired (S)-5-(((1R,2R)-2-(((tert-butyldiphenylsilyl)oxy) methyl)cyclobutyl)methyl)-6'-chloro-4',4'-difluoro-3',4,4',5-tetrahydro-2H,2'H-spiro[benzo[b][1,4]oxazepine-3,1'-naphthalene]-7-carboxylic acid (4.6 g, 6.42 mmol, 71.7% yield) and ((1R,2R)-2-(((tert-butyldiphenylsilyl)oxy)methyl)cyclobutyl)methanol (1.75 g, 4.94 mmol, 55.1% yield) The product only appeared 85% pure by NMR, but it was taken on to the next step.

Step 21: (S)-methyl 5-(((1R,2R)-2-(((tert-butyldiphenylsilyl)oxy)methyl)cyclobutyl)methyl)-6'-chloro-4',4'-difluoro-3',4,4',5-tetrahydro-2H,2'H-spiro[benzo[b][1,4]oxazepine-3,1'-naphthalene]-7-carboxylate

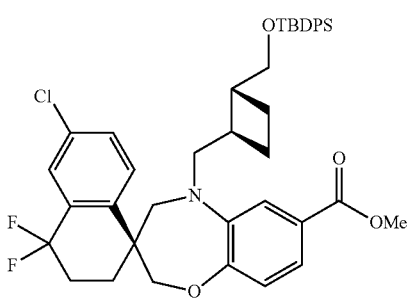

To a solution of (S)-5-(((1R,2R)-2-(((tert-butyldiphenylsilyl)oxy)methyl)cyclobutyl)methyl)-6'-chloro-4',4'-difluoro-3',4,4',5-tetrahydro-2H,2'H-spiro[benzo[b][1,4]oxazepine-3,1'-naphthalene]-7-carboxylic acid (4.6 g, 6.42 mmol) in 75 ml toluene and 25 mL methanol was added TMS-diazomethane 2M in hexane (3.85 ml, 7.71 mmol) dropwise with stirring. After stirring for 1 h LC/MS showed 80% conversion and an additional charge of 1 mL TMS-diazomethane was added. After 10 min the mixture was quenched by addition of acetic acid and concentrated under rotary evaporation (in the hood, for safety). The material thus obtained was dried under high vacuum overnight. TLC in 1% acetone in hexanes or 2% ethyl acetate in hexanes did not show separation of a significant amount of impurities, so the material was taken on crude to the next step.

Step 22: (S)-methyl 6'-chloro-4',4'-difluoro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate

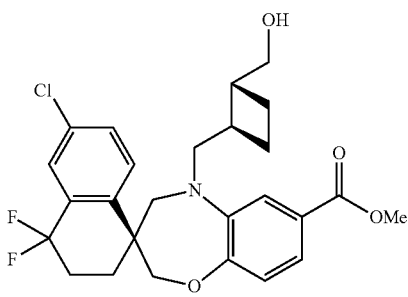 [SMILES: COC(=O)c1ccc2c(c1)N(C[C@@H]1CC[C@H]1CO)C[C@@]1(CCC(F)(F)c3cc(Cl)ccc31)CO2]

To a solution of (S)-methyl 5-(((1R,2R)-2-(((tert-butyldiphenylsilyl)oxy)methyl)cyclobutyl)methyl)-6'-chloro-4',4'-difluoro-3',4,4',5-tetrahydro-2H,2'H-spiro[benzo[b][1,4]oxazepine-3,1'-naphthalene]-7-carboxylate (4.7 g, 6.44 mmol) in THF (25.7 ml) was added TBAF (8.04 ml, 8.04 mmol) and the mixture was stirred at ambient temperature for 6 h. The mixture was then diluted with ethyl ether and washed with 2×50 mL of 50% brine, then 50 mL brine, then it was dried over MgSO₄, filtered, concentrated. The residue was deposited on silica gel (25 g) and purified on a 330 g silica gel column eluting with 20% ethyl acetate in hexanes leading to partial separation of the desired product. Note: it is necessary to remove 15% impurity that had been carried since the reductive amination—likely a diastereomeric product resulting from low ee of the cyclobutane. The mixed fractions (700 mg) were recycled through a 120 g column eluting with 20% ethyl acetate in hexanes and the purified (S)-methyl 6'-chloro-4',4'-difluoro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate (combined total yield of 2.3 g, 4.68 mmol, 72.7%) was obtained cleanly, as a white solid.

Step 23: (S)-methyl 6'-chloro-4',4'-difluoro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate

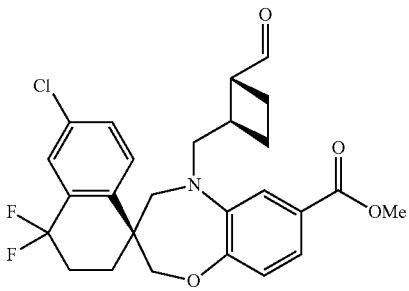 [SMILES: COC(=O)c1ccc2c(c1)N(C[C@@H]1CC[C@H]1C=O)C[C@@]1(CCC(F)(F)c3cc(Cl)ccc31)CO2]

A solution of dess-martin periodinane (1.345 g, 3.17 mmol) in 26 mL dichloromethane was filtered through a 0.45 uM membrane. To this solution was added (S)-methyl6'-chloro-4',4'-difluoro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate (1.2 g, 2.439 mmol) in 15 mL dichloromethane dropwise over 10 min. After 30 min, water (0.048 ml, 2.68 mmol) in 20 mL dichloromethane was added dropwise over 30 minutes. The mixture was then quenched with 50 mL of dess martin extractor (1:1 10% Na₂S₂O₃/sat. NaHCO₃) and stirred for 20 min. The organic layer was separated and washed with 50 ml dess martin extractor, then 25 mL sat. NaHCO₃, dried over MgSO₄, filtered, and concentrated. Crude NMR showed ~5% of dess martin byproduct. The semipure material was passed through a 40 g silica gel column eluting with 100% DCM. The desired product dragged on the column but could be efficiently isolated (1.12 g, 94% yield).

Step 24: (S)-methyl 6'-chloro-4',4'-difluoro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate

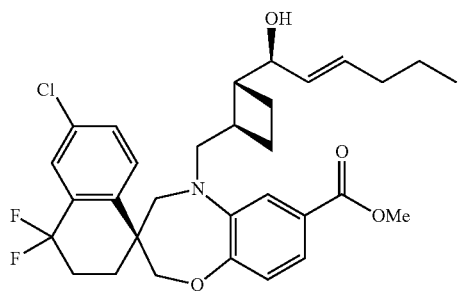

The title compound was synthesized from (S)-methyl 6'-chloro-4',4'-difluoro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate following the procedure described for Intermediate AA 12, Step 1.

Step 25: (S)-6'-chloro-4',4'-difluoro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic Acid The title compound was synthesized from (S)-methyl 6'-chloro-4',4'-difluoro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate following the procedure described for Intermediate AA 12, Step 2.

Intermediate AA19

(S)-7'-chloro-5-(((1R,2R)-2-((S)-1-hydroxyallyl)cyclobutyl)methyl)-4,5-dihydro-2H-spiro[benzo[b][1,4]oxazepine-3,4'-chroman]-7-carboxylic Acid

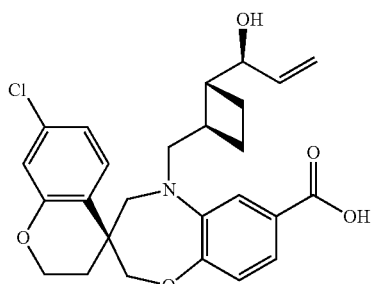

Step 1: (2-(2-bromo-5-chlorophenoxy)ethoxy)(dimethyl)(2-methyl-2-propanyl)silane

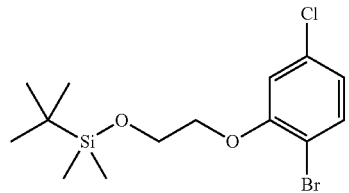 [SMILES: CC(C)(C)[Si](C)(C)OCCOc1cc(Cl)ccc1Br]

To a solution of 2-bromo-5-chlorophenol (50 g, 241 mmol) in NMP (500 mL) was added $K_2CO_3$ (66.51 g, 482 mmol), (2-bromoethoxy)-tert-butyl-dimethylsilane (56.8 mL, 265.1 mmol) and catalytic amount of KI (800 mg, 4.80 mmol), and the suspension was heated to 90° C. for 5 h. On completion, the suspension was cooled to room temperature and diluted with water (500 mL). Aqueous phase was extracted with ethyl acetate (3×250 mL). Combined organic layer was washed with water (500 mL), brine (500 mL) and dried over sodium sulphate. Solvent was removed under reduced pressure to afford crude material which was purified by column chromatography (100-200 mesh size silica gel, eluting with a gradient of 100% hexanes to 5% ethyl acetate in hexanes) affording pure (2-(2-bromo-5-chlorophenoxy)ethoxy)(dimethyl)(2-methyl-2-propanyl)silane (72 g, 83.5%) as light yellow oil. $R_f$: 0.8 in 5% Ethyl acetate in hexane.

Step 2: diethyl 2-(2-(2-((tert-butyldimethylsilyl)oxy)ethoxy)-4-chlorophenyl)malonate

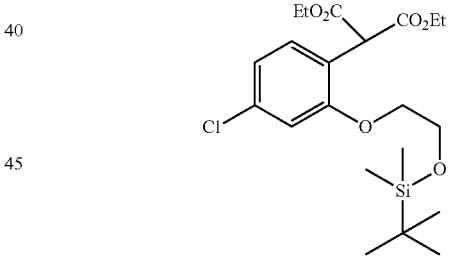

To a solution of potassium phosphate (70 g, 329.6 mmol) and $Pd(tBu_3P)_2$ (3.98 g, 7.8 mmol) (both weighed under nitrogen) in toluene (70 mL), was added 2-(2-bromo-5-chlorophenoxy)ethoxy)(dimethyl)(2-methyl-2-propanyl)silane (40 g, 109.8 mmol) dissolved in dry toluene (70 mL) (plus 2×20 mL rinses with toluene) followed by the addition of diethyl malonate (19.3 mL, 120.8 mmol). The resulting suspension was heated at 85° C. for 6 h under an atmosphere of argon. The reaction monitored by LCMS and upon completion, the suspension was cooled to room temperature and then directly loaded over silica gel and purified by column chromatography (100-200 mesh size silica gel, eluting with a gradient of 100% hexanes to 10% ethyl acetate in hexanes) to afford pure diethyl 2-(2-(2-((tert-butyldimethylsilyl)oxy)ethoxy)-4-chlorophenyl)malonate (28 g, 60%) as a clear oil. $R_f$: 0.5 in 10% ethyl acetate in hexane Step 3: diethyl 7-chlorochroman-4,4-dicarboxylate

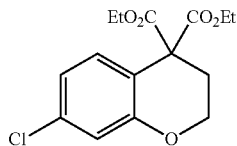 [SMILES: CCOC(=O)C1(C(=O)OCC)CCOc2cc(Cl)ccc21]

To a solution of diethyl 2-(2-(2-((tert-butyldimethylsilyl)oxy)ethoxy)-4-chlorophenyl)malonate (31 g, 69.96 mmol) and DBU (20.7 ml, 139.9 mmol) in MeCN (700 ml), under $N_2$ atmosphere, 4-nitrobenzene-1-sulfonyl fluoride (28.7 g, 139.9 mmol) was added and the resulting solution was heated to 70° C. for 24 h. The reaction was monitored by TLC and upon completion, the solution was concentrated under reduced pressure to remove the MeCN at 35° C. and the residue was diluted with water (400 mL) and aqueous phase was extracted with ethyl acetate (3×300 mL). The combined organic layer was washed with water (400 mL), 1N HCl (500 mL) followed by $NaHCO_3$ (500 mL) solution and finally with brine (500 mL). Organic layer was dried over $Na_2SO_4$, filtered, and concentrated under vacuum to get the crude material which was purified by column chromatography (100-200 mesh size silica gel, eluting with a gradient of 100% hexane to 10% ethyl acetate/hexanes). The fractions containing the product were combined and concentrated under vacuum to provide diethyl 7-chlorochroman-4,4-dicarboxylate (17 g, 78%) as colorless oil. $R_f$: 0.4 in 10% ethyl acetate in hexane.

Step 4: (7-chlorochroman-4,4-diyl)dimethanol

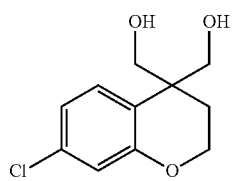 [SMILES: OCC1(CO)CCOc2cc(Cl)ccc21]

To a solution of 7-chlorochroman-4,4-dicarboxylate (15 g, 47.96 mmol) in THF (250 mL) was added DIBAL-H (1 M in THF, 480 mL, 480 mmol) dropwise at 0° C. The reaction mixture was stirred at ambient temperature for 4 h then it was quenched by the addition of saturated solution of $NH_4Cl$ (500 mL) and extracted with 700 mL of ethyl acetate. The combined organic layer was dried over sodium sulfate and concentrated. The crude material thus obtained was dissolved in THF (250 mL) and water (150 mL), and sodium borohydride (10.64 g, 287.76 mmol) was added. The reaction was stirred at ambient temperature for 3 h then it was quenched with saturated $NH_4Cl$ solution (300 mL) and extracted with ethyl acetate (2×250 mL). The combined organic layer was dried over sodium sulfate and concentrated under reduced pressure. The crude material was purified by column chromatography (100-200 mesh size silica gel, eluting with a gradient of 100% Hexane to 70% ethyl acetate/hexanes) affording pure (7-chlorochroman-4,4-diyl)dimethanol (10 g, 91%). $R_f$: 0.3 in 70% ethyl acetate in hexane.

Step 5: (S)-(7-chloro-4-(hydroxymethyl)chroman-4-yl)methyl 4-bromobenzoate

To a solution of 2,6-bis((R)-5,5-dibutyl-4-phenyl-4,5-dihydrooxazol-2-yl)pyridine (R,R-Kang Catalyst) (1.29 g, 2.186 mmol) in dry DCM (40 mL), copper(II) chloride (293.90 mg, 2.186 mmol) was added and the resulting green solution was stirred at ambient temperature for 3 h. This solution was added via cannula to a solution of (7-chlorochroman-4,4-diyl)dimethanol (10 g, 43.72 mmol) in dry DCM (1.7 L). The resulting solution was cooled to −78° C. and light green colored precipitation was observed in the reaction after some time. A solution of 4-bromobenzoyl chloride (14.3 g, 65.52 mmol) in DCM (70 mL) was then added slowly followed after 10 min by the dropwise addition of N-ethyl-N-isopropylpropan-2-amine (8.37 mL, 48.09 mmol). The resulting reaction mixture was stirred at −78° C. for 2 h then it was quenched with pH~3 phosphate buffer (500 mL) and warmed to ambient temperature with vigorous stirring. The reaction was diluted with ethyl acetate (3 L) and the layers were separated. The organic phase was washed with pH~3 buffer (1×500 mL), saturated $NaHCO_3$ (2×500 mL), and brine (1×500 mL), dried over sodium sulfate, filtered and concentrated. The crude material thus obtained was purified by column chromatography (100-200 mesh size silica gel, eluting with 100% DCM) affording pure (S)-(7-chloro-4-(hydroxymethyl)chroman-4-yl)methyl 4-bromobenzoate as a white solid (15 g, 83.4%; e.r.=92:8). This material was dissolved in 23 mL of acetone and 127 mL of hexane was added with continuous stirring. The precipitate thus obtained was filtered and washed with hexane to obtain the enantioenriched (e.r.=98.4:1.6; ChiralCel OD-H (250 mm×4.5 mm); mobile phase: n-hexane:IPA: 95:5; run time: 20 min; flow rate: 1 ml/min; sample preparation: IPA; retention time (major peak)-12.483 min.; retention time (minor peak)-15.681 min.) title compound. $R_f$: 0.5 in 100%.

Step 6: (R)-(7-chloro-4-formylchroman-4-yl)methyl 4-bromobenzoate

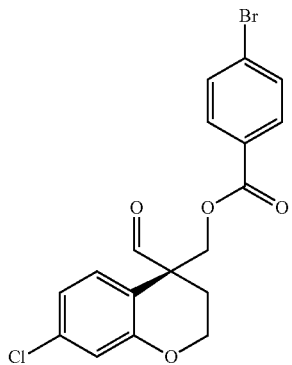 [SMILES: O=C[C@]1(COC(=O)c2ccc(Br)cc2)CCOc2cc(Cl)ccc21]

To a stirred solution of (S)-(7-chloro-4-(hydroxymethyl) chroman-4-yl)methyl 4-bromobenzoate (11 g, 26.71 mmol) in DCM (700 mL), Dess-Martin periodinane (13.59 g, 32.06 mmol) was added at 10° C. Cooling bath was removed after addition and the reaction mixture was stirred for 30 min at ambient temperature. Water (577 mg, 32.06 mmol) was then added slowly and the reaction mixture was stirred further at ambient temperature for 30 min. The reaction was then cooled to 0° C., quenched with a 1:1 mixture of 10% $Na_2S_2O_3$/saturated $NaHCO_3$ (200 mL) solution and stirred further at room temperature for 1 h. The solution was then diluted with ethyl acetate (700 mL) and the aqueous phase was separated. The organic phase was washed with 200 mL of 1:1 mixture of 10% $Na_2S_2O_3$/saturated $NaHCO_3$ solution, saturated $NaHCO_3$ solution (100 mL) and brine (100 mL), dried over sodium sulfate, filtered, and concentrated. The crude material was purified by column chromatography (100-200 mesh size silica gel, eluting with 10% ethyl acetate in hexanes) to afforded (R)-(7-chloro-4-formylchroman-4-yl)methyl 4-bromobenzoate as light yellow solid (9 g, 82%). $R_f$: 0.7 in 10% ethyl acetate in hexane.

Step 7: (R)-(6-chloro-1-(dimethoxymethyl)-1,2,3,4-tetrahydronaphthalen-1-yl)methanol

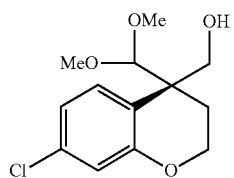 [SMILES: COC(OC)[C@]1(CO)CCOc2cc(Cl)ccc21]

To a solution of (R)-(7-chloro-4-formylchroman-4-yl) methyl 4-bromobenzoate (9 g, 21.96 mmol) in anhydrous MeOH (450 mL), p-toluene sulfonic acid (185 mg, 1.076 mmol) and trimethyl orthoformate (7.20 mL, 65.88 mmol) were added and the reaction mixture was refluxed for 4 h. The reaction mass was then concentrated to 50% volume and diluted with THF (225 mL) and 1N NaOH (225 mL, 66 mmol). The resulting mixture was stirred at room temperature overnight then it was concentrated under reduced pressure and the residue was diluted with diethyl ether (500 mL). The aqueous layer was separated and the organic layer was washed with 1N NaOH (300 mL). The combined aqueous layers were extracted with diethyl ether (200 mL) and the combined organic layers were washed again with 1N NaOH (200 mL) and brine then dried over sodium sulfate and concentrated under reduced pressure. The crude material was purified by column chromatography (100-200 mesh size silica gel, eluting with 20% ethyl acetate/hexane) to afford pure (R)-(6-chloro-1-(dimethoxymethyl)-1,2,3,4-tetrahydronaphthalen-1-yl)methanol as a colorless thick oil (5.39 g, 100%). $R_f$: 0.5 in 30% ethyl acetate in hexane.

Step 8: (R)-tert-butyl 4-((7-chloro-4-(dimethoxymethyl)chroman-4-yl)methoxy)-3-nitrobenzoate

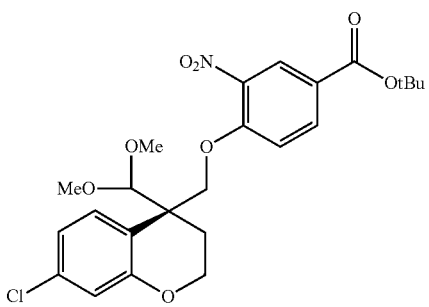 [SMILES: COC(OC)[C@]1(COc2ccc(C(=O)OC(C)(C)C)cc2[N+](=O)[O-])CCOc2cc(Cl)ccc21]

A solution of (R)-(6-chloro-1-(dimethoxymethyl)-1,2,3,4-tetrahydronaphthalen-1-yl)methanol (5.3 g, 19.43 mmol) in dry THF (150 mL) was cooled to 0° C. and LiHMDS (1 M in THF, 25.2 mL, 25.2 mmol) was added dropwise. After 5 min, a solution of tert-butyl 4-fluoro-3-nitrobenzoate (Intermediate AA11, Step 8; 5.15 g, 21.37 mmol) in THF was added dropwise via syringe and the resulting mixture was warmed to room temperature. After 1 h the reaction was cooled to 0° C., quenched with saturated $NH_4Cl$ solution (100 mL) and extracted with ethyl acetate (500 mL). The combined organic layers were washed with $NH_4Cl$ (100 mL), brine (200 mL), dried over sodium sulfate and concentrated under reduced pressure. The crude material thus obtained was purified by column chromatography (100-200 mesh size silica gel, eluting with 5% ethyl acetate/hexane) to afford (R)-tert-butyl 4-((7-chloro-4-(dimethoxymethyl) chroman-4-yl)methoxy)-3-nitrobenzoate as a yellow semi-solid (9 g, 93.8% yield). $R_f$: 0.5 in 10% ethyl acetate in hexane.

Step 9: (R)-tert-butyl 4-((7-chloro-4-formylchroman-4-yl)methoxy)-3-nitrobenzoate

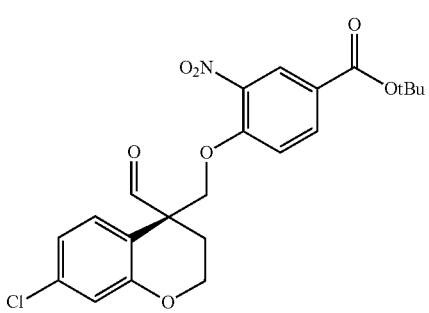 [SMILES: CC(C)(C)OC(=O)c1ccc(OC[C@@]2(C=O)CCOc3cc(Cl)ccc32)c([N+](=O)[O-])c1]

To a solution of (R)-tert-butyl 4-((7-chloro-4-(dimethoxymethyl)chroman-4-yl)methoxy)-3-nitrobenzoate (9 g, 18.22 mmol) in anhydrous acetone (100 mL) was added amberlyst-15 (9 g, 18.22 mmol) (prewashed with 2×100 mL dry acetone) and the solution was heated to 50° C. for 12 h. Upon completion, the reaction mixture was filtered and rinsed with acetone and the combined filtrate was concentrated. LCMS analysis of crude material showed 30% of the benzoic acid. The crude material was then dissolved in tert-butanol (200 mL), di tert-butyl dicarbonate (4.8 mL, 18.22 mmol) and DMAP (222 mg, 1.82 mmol) were added and the reaction mass was heated at 40° C. overnight. The mixture was then diluted with water (400 mL) and the aqueous phase was extracted with ethyl acetate (3×200 mL). The combined organic layer was dried over sodium sulfate and concentrated and the crude material was purified by column chromatography (100-200 mesh size silica gel, eluting with 5% ethyl acetate/hexane) to afford pure (R)-tert-butyl 4-((7-chloro-4-formylchroman-4-yl)methoxy)-3-nitrobenzoate as light yellow semi solid (6 g, 77.3%). R$_f$: 0.45 in 10% ethyl acetate in hexane.

Step 10: (S)-tert-butyl 7'-chloro-4,5-dihydro-2H-spiro[benzo[b][1,4]oxazepine-3,4'-chroman]-7-carboxylate

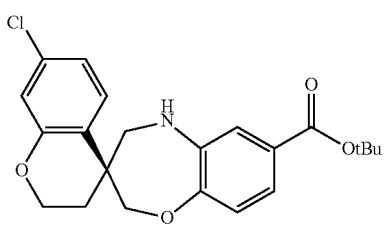 [SMILES: CC(C)(C)OC(=O)c1ccc2c(c1)NC[C@@]1(CCOc3cc(Cl)ccc31)CO2]

A solution of (R)-tert-butyl 4-((7-chloro-4-formylchroman-4-yl)methoxy)-3-nitrobenzoate (6 g, 13.41 mmol) in acetic acid (148 mL) was heated at 70° C. and iron powder (4.5 g, 80.51 mmol) was added. The resulting mixture was heated for 4 h at 70° C. Acetic acid was then removed under reduced pressure and the residue was dissolved in DCE (150 mL). Sodium triacetoxy borohydride (11.36 g, 53.64 mmol) was then added portion wise and the reaction mixture was stirred at ambient temperature for 1 h. The reaction was then quenched with water (200 mL) followed by 10% citric acid solution (400 mL). The aqueous phase was extracted with DCM (3×150 mL) and the combined organic layer was washed with brine (200 mL), dried over sodium sulfate and concentrated under reduced pressure. The residue was purified by column chromatography (100-200 mesh size silica gel, 5% ethyl acetate/hexane) to afford pure (5)-tert-butyl 7'-chloro-4,5-dihydro-2H-spiro[benzo[b][1,4]oxazepine-3,4'-chroman]-7-carboxylate as a white solid (3.5 g; e.r.=97.4: 2.6; ChiralCel OD-H (250 mm×4.5 mm); mobile phase: n-hexane:ethanol: 90:10; run time: 20 min; flow rate: 1 ml/min; Sample preparation: IPA; retention time (major peak)-10.518 min; retention time (minor peak)-8.667 min). R$_f$: 0.6 in 10% ethyl acetate in hexane.

Step 11: (S)-7'-chloro-4,5-dihydro-2H-spiro[benzo[b][1,4]oxazepine-3,4'-chroman]-7-carboxylic Acid

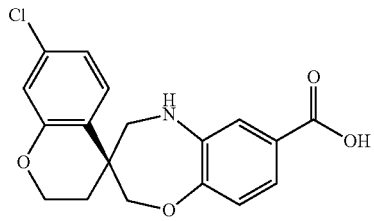 [SMILES: O=C(O)c1ccc2c(c1)NC[C@@]1(CCOc3cc(Cl)ccc31)CO2]

(R)-tert-butyl 4-((7-chloro-4-formylchroman-4-yl)methoxy)-3-nitrobenzoate (3.35 g, 7.48 mmol) was dissolved in acetic acid (64.2 ml, 1122 mmol) and to this was added iron (2.506 g, 44.9 mmol). The solution was heated at 70° C. for 4 hours. The solution was cooled to ambient temperature and then concentrated under vacuum. The residue obtained was purified on a 80 g silica gel column (dry loaded), eluting with a gradient of DCM to 2% MeOH/DCM to provide the partially purified title compound as the second eluting major component. This material was repurified on a 40 g silica gel column (dry loaded), eluting with a gradient of 100% Hexanes to 8% iPrOH/Hexanes and again on a 40 g silica gel column (dry loaded), eluting with a gradient of 0.5% MeOH/DCM to 1% MeOH/DCM to provide (S)-7'-chloro-4,5-dihydro-2H-spiro[benzo[b][1,4]oxazepine-3,4'-chroman]-7-carboxylic acid (1.12 g, 3.24 mmol, 43.3% yield) as a white solid.

Step 12: (S)-5-(((1R,2R)-2-((benzoyloxy)methyl)cyclobutyl)methyl)-7'-chloro-4,5-dihydro-2H-spiro[benzo[b][1,4]oxazepine-3,4'-chroman]-7-carboxylic Acid

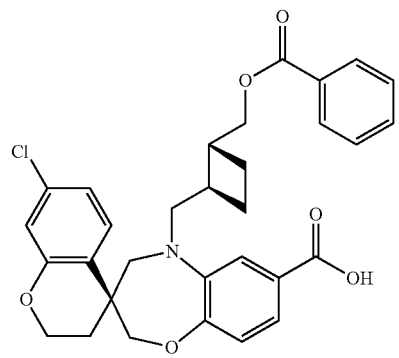 [SMILES: O=C(O)c1ccc2c(c1)N(C[C@@H]1CC[C@H]1COC(=O)c1ccccc1)C[C@@]1(CCOc3cc(Cl)ccc31)CO2]

(S)-7'-chloro-4,5-dihydro-2H-spiro[benzo[b][1,4]oxazepine-3,4'-chroman]-7-carboxylic acid (1.1 g, 3.18 mmol) was dissolved in DCM (28.3 ml) and acetic acid (3.53 ml). The solution was cooled in a ice bath under an atmosphere of N$_2$. To this was then added ((1R,2R)-2-formylcyclobutyl)methyl benzoate (Intermediate AA17, Step 8) 1M in DCM (3.50 ml, 3.50 mmol) and the solution was stirred for 10 min. Sodium cyanoborohydride 1M in THF (1.591 ml, 1.591 mmol) was then slowly added dropwise. The solution was then stirred in the ice bath for 20 minutes. To this was then slowly added an ice cold solution of NaOH (3.05 g, 76 mmol) dissolved in 40 ml of water (pH of the solution was 13). The suspension was then transferred to a separatory funnel, diluted with 6 ml of acetic acid and washed with EtOAc. The aqueous layer was washed again with EtOAc. The combined organics were dried over MgSO₄, filtered and concentrated under vacuum. The residue obtained was purified on a 40 g silica gel column (dry loaded), eluting with a gradient of 0 to 50% EtOAc in Hexanes to provide (S)-5-(((1R,2R)-2-((benzoyloxy)methyl)cyclobutyl)methyl)-7'-chloro-4,5-dihydro-2Hspiro[benzo[b][1,4]oxazepine-3,4'-chroman]-7-carboxylic acid (0.732 g, 1.336 mmol, 42.0% yield) as a white foam.

Step 13: (S)-5-(((1R,2R)-2-(hydroxymethyl)cyclobutyl)methyl)-7'-chloro-4,5-dihydro-2H-spiro[benzo[b][1,4]oxazepine-3,4'-chroman]-7-carboxylic Acid

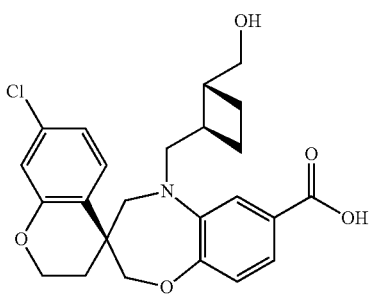 [SMILES: O=C(O)c1ccc2c(c1)N(C[C@@H]1CC[C@H]1CO)C[C@@]1(CCOc3cc(Cl)ccc31)CO2]

To a solution of (S)-5-(((1R,2R)-2-((benzoyloxy)methyl)cyclobutyl)methyl)-7'-chloro-4,5-dihydro-2H-spiro[benzo[b][1,4]oxazepine-3,4'-chroman]-7-carboxylic acid (725 mg, 1.323 mmol) in anhydrous methanol was added sodium (45.6 mg, 1.984 mmol). The mixture was allowed to stir over the weekend and it was then quenched with 3 mL 1N HCL and 10 mL water. The solvent was removed under reduced pressure and the residue was extracted with ethyl acetate, washed with brine, dried over MgSO₄, filtered, and concentrated. The crude material was purified using 20-40% acetone in hexanes to afford (S)-7'-chloro-5-(((1R,2R)-2-(hydroxymethyl)cyclobutyl)methyl)-4,5-dihydro-2H-spiro[benzo[b][1,4]oxazepine-3,4'-chroman]-7-carboxylic acid (490 mg, 1.104 mmol, 83% yield).

Step 14: (S)-methyl 5-(((1R,2R)-2-(hydroxymethyl)cyclobutyl)methyl)-7'-chloro-4,5-dihydro-2H-spiro[benzo[b][1,4]oxazepine-3,4'-chroman]-7-carboxylate

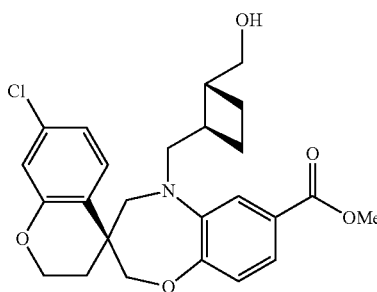

To a solution of (S)-7'-chloro-5-(((1R,2R)-2-(hydroxymethyl)cyclobutyl)methyl)-4,5-dihydro-2H-spiro[benzo[b][1,4]oxazepine-3,4'-chroman]-7-carboxylic acid (460 mg, 1.036 mmol) in 20 mL anhydrous toluene and methanol (4192 µl, 104 mmol) was added TMS-diazomethane (Aldrich, 2 M; 674 µl, 1.347 mmol). After 1 h, the mixture was concentrated to dryness and dried under high vacuum overnight. Isolated (S)-methyl 7'-chloro-5-(((1R,2R)-2-(hydroxymethyl)cyclobutyl)methyl)-4,5-dihydro-2H-spiro[benzo[b][1,4]oxazepine-3,4'-chroman]-7-carboxylate (500 mg, 1.092 mmol; contaminated by 0.33 equivalents of toluene).

Step 15: (S)-methyl 7'-chloro-5-(((1R,2R)-2-formylcyclobutyl)methyl)-4,5-dihydro-2H-spiro[benzo[b][1,4]oxazepine-3,4'-chroman]-7-carboxylate

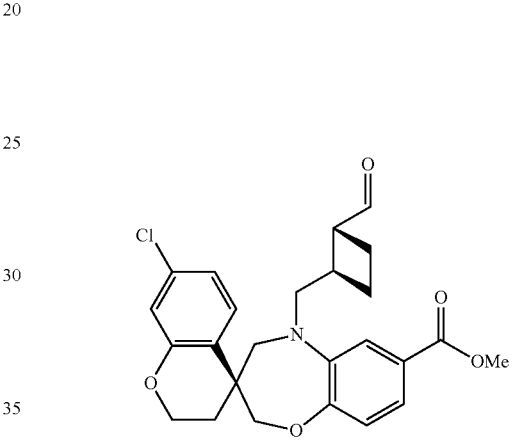

To a solution of (S)-methyl 7'-chloro-5-(((1R,2R)-2-(hydroxymethyl)cyclobutyl)methyl)-4,5-dihydro-2H-spiro[benzo[b][1,4]oxazepine-3,4'-chroman]-7-carboxylate (500 mg, 1.024 mmol) in 5 mL dichloromethane was added a solution of Dess-Martin periodinane (Chem Impex International; 500 mg, 1.178 mmol) in 5 mL dichloromethane, filtered through a 0.45 uM filter. After 30 minutes, water (18.45 µl, 1.024 mmol) in 5 mL dichloromethane was added dropwise over 30 minutes. After 1 h an additional charge of 2×100 mg dess martin periodinane was added and after 5 minutes, more water (18.45 µl, 1.024 mmol) was added. After 10 minutes the reaction was quenched by addition of 20 mL dess-martin extractor (50% sat. NaHCO₃, 50% 10% Na₂S₂O₃) and stirred for 1 h. The aqueous phase was with DCM and the combined organic phases were washed with sat. K₂CO₃ (emulsion occurred. Added water to separate layers) and brine, then dried over MgSO₄, filtered, and concentrated. The crude material was purified by column chromatography using 20-30% ethyl acetate in hexanes to afford (S)-methyl 7'-chloro-5-(((1R,2R)-2-formylcyclobutyl)methyl)-4,5-dihydro-2H-spiro[benzo[b][1,4]oxazepine-3,4'-chroman]-7-carboxylate (350 mg, 0.768 mmol, 75.0% yield).

Step 16: (S)-methyl 7'-chloro-5-(((1R,2R)-2-((S)-1-hydroxyallyl)cyclobutyl)methyl)-4,5-dihydro-2H-spiro[benzo[b][1,4]oxazepine-3,4'-chroman]-7-carboxylate

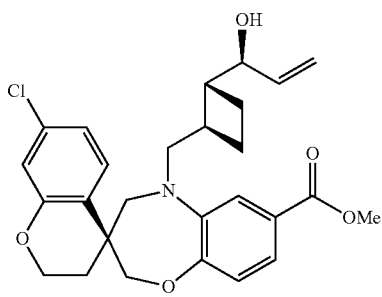

To a solution of (S)-methyl 7'-chloro-5-(((1R,2R)-2-formylcyclobutyl)methyl)-4,5-dihydro-2Hspiro[benzo[b][1,4]oxazepine-3,4'-chroman]-7-carboxylate (350 mg, 0.768 mmol) in tetrahydrofuran (7677 µl) at −10° C. under argon was added vinylmagnesium bromide (Aldrich, 1 M in THF; 998 µl, 0.998 mmol) dropwise. After 2 h the reaction was quenched by addition of sat. NH₄Cl and extracted with ethyl ether and washed with brine. The combine organics were dried over MgSO₄, filtered, and concentrated. The crude material was purified by column chromatography using 20-30% ethyl acetate in hexanes to afford (S)-methyl 7'-chloro-5-(((1R,2R)-2-((S)-1-hydroxyallyl)cyclobutyl) methyl)-4,5-dihydro-2Hspiro[benzo[b][1,4]oxazepine-3,4'-chroman]-7-carboxylate as the second eluting major isomer (150 mg, 0.310 mmol, 40.4% yield).

Step 17: (S)-7'-chloro-5-(((1R,2R)-2-((S)-1-hydroxyallyl)cyclobutyl)methyl)-4,5-dihydro-2H-spiro[benzo[b][1,4]oxazepine-3,4'-chroman]-7-carboxylic Acid The title compound was synthesized from S)-methyl 7'-chloro-5-(((1R,2R)-2-((S)-1-hydroxyallyl)cyclobutyl) methyl)-4,5-dihydro-2Hspiro[benzo[b][1,4]oxazepine-3,4'-chroman]-7-carboxylate as the second eluting major isomer (135 mg, 0.279 mmol) following the procedure described for Intermediate AA 12, Step 2. Purification by column chromatography eluting with 20 to 25% acetone in hexanes provided (S)-7'-chloro-5-(((1R,2R)-2-((S)-1-hydroxyallyl) cyclobutyl)methyl)-4,5-dihydro-2H-spiro[benzo[b][1,4] oxazepine-3,4'-chroman]-7-carboxylic acid (87 mg, 0.185 mmol, 66.4% yield).

Intermediate AA20

(S)-5'-chloro-5-(((1R,2R)-2-((S)-1-hydroxyallyl) cyclobutyl)methyl)-2',3',4,5-tetrahydro-2H-spiro [benzo[b][1,4]oxazepine-3,1'-indene]-7-carboxylic Acid

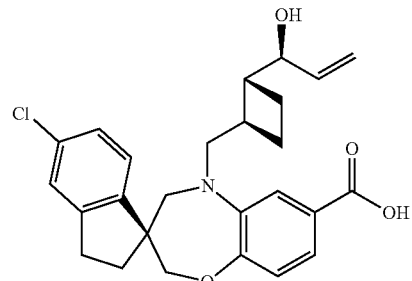

Step 1: (S)-5-chloro-2,3-dihydro-1H-inden-1-ol and (R)-5-chloro-2,3-dihydro-1H-inden-1-ol

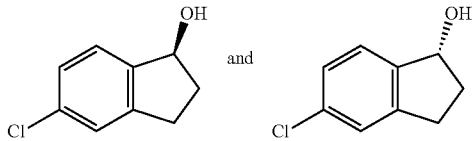 [SMILES: O[C@H]1CCc2cc(Cl)ccc21 ; O[C@@H]1CCc2cc(Cl)ccc21]

To a solution of 5-chloro-2,3-dihydro-1H-inden-1-one (50.0 g, 301.2 mmol) in THF (500 mL) was added sodium borohydride solution (23.0 g, 602.4 mmol) in water (100 mL) at 0° C. drop-wise in 1 h. The resulting reaction mixture was stirred at ambient temperature for 12 h. After completion, the reaction mixture was quenched with water (500 mL) and extracted with ethyl acetate (3×1500 mL). The organic layers were combined, dried over sodium sulfate and concentrated under reduced pressure to obtain a racemic mixture of (S)-5-chloro-2,3-dihydro-1H-inden-1-ol and (R)-5-chloro-2,3-dihydro-1H-inden-1-ol (48.0 g, 94.8% yield), which was used in next step without purification.

Step 2: (S)-1,5-dichloro-2,3-dihydro-1H-indene and (R)-1,5-dichloro-2,3-dihydro-1H-indene

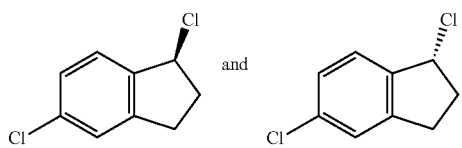 [SMILES: Clc1ccc2c(c1)CC[C@@H]2Cl ; Clc1ccc2c(c1)CC[C@H]2Cl]

To a solution of racemic 5-chloro-2,3-dihydro-1H-inden-1-ol (45.0 g, 267.8 mmol) in 1,4-dioxane (200 mL) was added thionyl chloride (45 mL) at ambient temperature dropwise in 10 minutes. The resulting reaction mixture was stirred at ambient temperature for 2 h. After completion, the reaction mixture was poured into wet ice (1 kg) and stirred for 30 minutes. The aqueous layer was extracted with ethyl acetate (3×1000 mL). The organic layer were combined, dried over sodium sulphate and concentrated under reduced pressure to obtain a racemic mixture of (S)-1,5-dichloro-2,3-dihydro-1H-indene and (R)-1,5-dichloro-2,3-dihydro-1H-indene (46.0 g, 93.8% yield), which was used in next step without purification.

Step 3: (S)-5-chloro-2,3-dihydro-1H-indene-1-carbonitrile and (R)-5-chloro-2,3-dihydro-1H-indene-1-carbonitrile

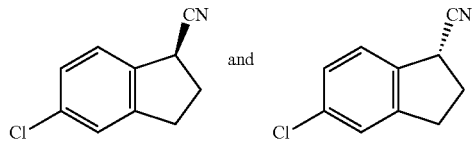 [SMILES: N#C[C@H]1CCc2cc(Cl)ccc21 ; N#C[C@@H]1CCc2cc(Cl)ccc21]

To a suspension of racemic 1,5-dichloro-2,3-dihydro-1H-indene (45.0 g, 241.9 mmol) in DMF (780 mL) was added sodium cyanide (15.4 g, 314.0 mmol) in one portion. The reaction mixture was stirred at 50° C. for 12 h. After completion, the reaction was diluted with water (1000 mL) and aqueous layer was extracted with ethyl acetate (3×1000 mL). The organic layer were combined, dried over sodium sulphate and concentrated under reduced pressure to get to get crude compound which was purified by column chromatography (silica 100-200 mesh; elution: 0-2% ethyl acetate in hexane in DCM) to obtain a racemic mixture of (S)-5-chloro-2,3-dihydro-1H-indene-1-carbonitrile and (R)-5-chloro-2,3-dihydro-1H-indene-1-carbonitrile (19.0 g, 45.2% yield).

Step 4: (S)-methyl 5-chloro-2,3-dihydro-1H-indene-1-carboxylate and (R)-methyl 5-chloro-2,3-dihydro-1H-indene-1-carboxylate

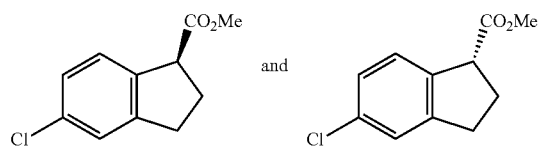 [SMILES: COC(=O)[C@H]1CCc2cc(Cl)ccc21 ; COC(=O)[C@@H]1CCc2cc(Cl)ccc21]

To a suspension of 5-chloro-2,3-dihydro-1H-indene-1-carbonitrile (19 g, 107.0 mmol) in MeOH (63 mL) and water (126 mL) was added sulfuric acid (95 mL) dropwise at 0° C. The reaction mixture was heated at 120° C. for 12 h. After completion (on TLC), the reaction mixture concentrate up to water layer and extracted with ethyl acetate (3×500 mL). The organic layer were combined, dried over sodium sulphate and concentrated under reduced pressure to get crude product, which was purified by purified by column chromatography (silica 100-200 mesh; elution: 0-2% ethyl acetate in hexane) to obtain a racemic mixture of (S)-methyl 5-chloro-2,3-dihydro-1H-indene-1-carboxylate and (R)-methyl 5-chloro-2,3-dihydro-1H-indene-1-carboxylate (12.6 g, 55.5% yield).

Step 5: (R)-1-ethyl 1-methyl 5-chloro-2,3-dihydro-1H-indene-1,1-dicarboxylate and (S)-1-ethyl 1-methyl 5-chloro-2,3-dihydro-1H-indene-1,1-dicarboxylate

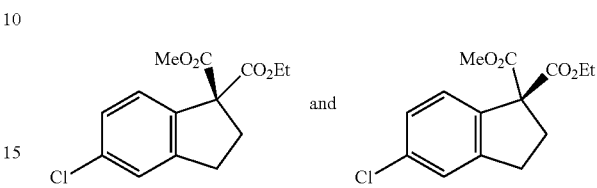

To a solution of 5-chloro-2,3-dihydro-1H-indene-1-carboxylate (12.6 g, 60.0 mmol) in THF (130 mL) was added LiHMDS 1.0M (78 mL, 72.0 mmol) dropwise at −78° C. The reaction mixture was stirred at −78° C. for 1 h. Ethyl cyanoformate (7.7 mL, 78.0 mmol) was added to reaction mixture dropwise at −78° C. in 30 minutes. After completion (on TLC), the reaction mixture was quenched with aq. NH$_4$Cl (200 mL) and extracted with ethyl acetate (3×500 mL). The organic layer was combined, dried over sodium sulfate and concentrated under reduced pressure to get crude product, which was purified by column chromatography (silica 100-200 mesh; elution: 0-2% ethyl acetate in hexane) to obtain pure 1-ethyl 1-methyl 5-chloro-2,3-dihydro-1H-indene-1,1-dicarboxylate (15.3 g, 90.5% yield).

Step 6: (5-chloro-2,3-dihydro-1H-indene-1,1-diyl)dimethanol

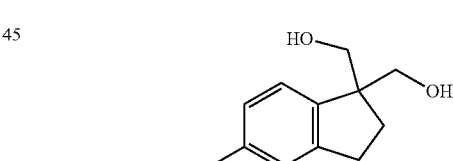

To a solution of racemic 1-ethyl 1-methyl 5-chloro-2,3-dihydro-1H-indene-1,1-dicarboxylate (60 g, 212.0 mmol) in THF (600 mL) was added LiBH$_4$ (27.8 g, 1276.5 mmol) portion wise at ambient temperature. The reaction mixture was stirred at 70° C. for 12 h. After completion (on TLC), the reaction mixture was quenched with aq. NH$_4$Cl (250 mL) and extracted with ethyl acetate (3×1000 mL). The organic layer were combined, dried over sodium sulphate and concentrated under reduced pressure to get crude product, which was purified by crystallization in DCM and hexane to obtain (5-chloro-2,3-dihydro-1H-indene-1,1-diyl)dimethanol (29.0 g, 64.4% yield).

Step 7: (S)-tert-butyl 4-((5-chloro-1-(hydroxymethyl)-2,3-dihydro-1H-inden-1-yl)methoxy)-3-nitrobenzoate and (R)-tert-butyl 4-((5-chloro-1-(hydroxymethyl)-2,3-dihydro-1H-inden-1-yl)methoxy)-3-nitrobenzoate

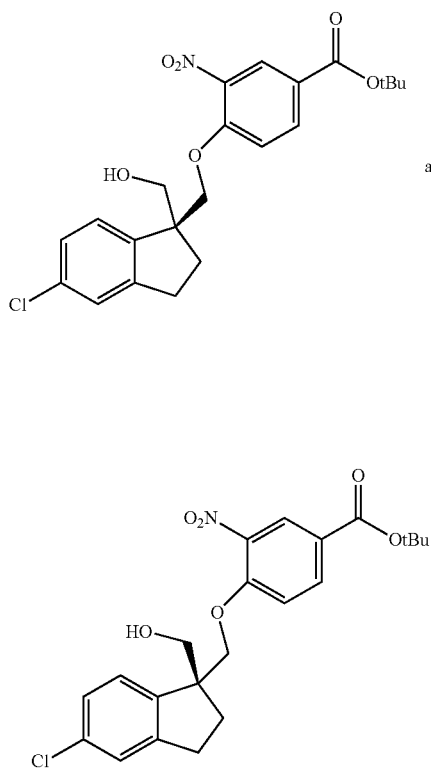

To a solution of (5-chloro-2,3-dihydro-1H-indene-1,1-diyl)dimethanol (29.0 g, 136.0 mmol) in THF (600 mL) was added LiHMDS 1.0 M (150 mL, 150.0 mmol) at 78° C. drop-wise in 20 minutes and then t-butyl 4-fluoro-3-nitrobenzoate (32.9 g, 136.0 mmol) was added. The resulting reaction mixture was stirred at −78° C. for 30 minutes and then at ambient temperature for 12 h. After completion (on TLC), the reaction mixture was quenched with aq. NH₄Cl (200 mL) and extracted with ethyl acetate (3×500 mL). The organic layer were combined, dried over sodium sulphate and concentrated under reduced pressure to get crude product, which was purified by column chromatography (silica 100-200 mesh; elution: 0-30% ethyl acetate in hexane) to obtain a racemic mixture of (S)-tert-butyl 4-((5-chloro-1-(hydroxymethyl)-2,3-dihydro-1H-inden-1-yl)methoxy)-3-nitrobenzoate and (R)-tert-butyl 4-((5-chloro-1-(hydroxymethyl)-2,3-dihydro-1H-inden-1-yl)methoxy)-3-nitrobenzoate (36.1 g, 61% yield).

Step 8: (R)-tert-butyl 4-((5-chloro-1-formyl-2,3-dihydro-1H-inden-1-yl)methoxy)-3-nitrobenzoate and (S)-tert-butyl 4-((5-chloro-1-formyl-2,3-dihydro-1H-inden-1-yl)methoxy)-3-nitrobenzoate

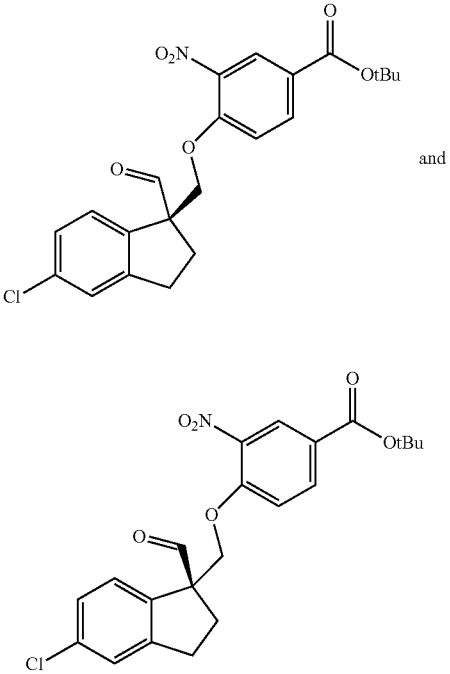

To a solution of racemic tert-butyl 4-((5-chloro-1-(hydroxymethyl)-2,3-dihydro-1H-inden-1-yl)methoxy)-3-nitrobenzoate (36.1 g, 83.37 mmol) in DCM (360 mL) was added Dess-martin periodinane (46.8 g, 110.3 mmol) at 0° C. The reaction mixture was stirred at ambient temperature for 2 h. After completion, the reaction mixture was quenched with aq. NaHCO₃ (200 mL) and extracted with ethyl acetate (3×500 mL). The organic layers were combined, dried over sodium sulfate and concentrated under reduced pressure to obtain a racemic mixture of (R)-tert-butyl 4-((5-chloro-1-formyl-2,3-dihydro-1H-inden-1-yl)methoxy)-3-nitrobenzoate and (S)-tert-butyl 4-((5-chloro-1-formyl-2,3-dihydro-1H-inden-1-yl)methoxy)-3-nitrobenzoate (50 g, 61.0%), which was carry forward for next step without purification.

Step 9: (S)-tert-butyl 5'-chloro-2',3',4,5-tetrahydro-2H-spiro[benzo[b][1,4]oxazepine-3,1'-indene]-7-carboxylate and (R)-tert-butyl 5'-chloro-2',3',4,5-tetrahydro-2H-spiro[benzo[b][1,4]oxazepine-3,1'-indene]-7-carboxylate

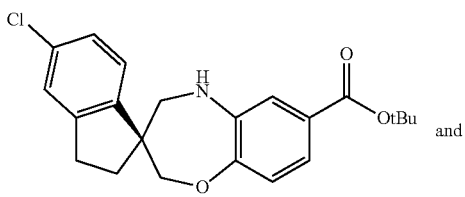

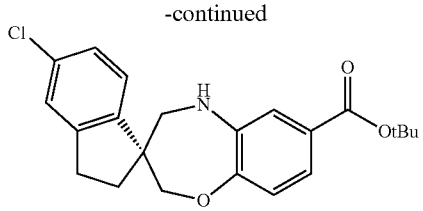

To a solution of racemic tert-butyl 4-((5-chloro-1-formyl-2,3-dihydro-1H-inden-1-yl)methoxy)-3-nitrobenzoate (50.0 g, 116.0 mmol) in THF (500 mL) and acetic acid (250 mL) was added iron powder (76.0 g, 1357 mmol) in one portion. The reaction mixture was heated at 70° C. for 3 h then it was cooled at ambient temperature and sodium cyanoborohydride (72.8 g, 1160.0 mmol) was added portion wise at ambient temperature. The reaction mixture was stirred at ambient temperature for 30 minutes then it was passed through a pad of celite and the celite pad was washed with ethyl acetate (2×100 mL). The filtrate was diluted with water (500 mL) and extracted with ethyl acetate (3×500 mL). The organic layers were combined, dried over sodium sulfate and concentrated under reduced pressure to afford the crude product, which was purified by column chromatography (silica 100-200 mesh; elution: 0-2% ethyl acetate in hexane) to obtain a racemic mixture of the title compound (18.0 g, 40.9%). The enantiomers were separated by SFC (Sample preparation: 9.5 g/500 mL (19 mg/mL) sample solution in MeOH:DCM (4:1); Column: Chiralpak OJ-H, 50×150 mm, 5 μm; Mobile Phase A: $CO_2$; Mobile Phase B: MeOH (20 mM $NH_3$) Isocratic: 48% B; Flow Rate: 250 g/min; Loading: 5.0 mL of sample solution prepared as above (~95 mg); Detection: UV @ 232 nm; Cycle Time: 7.8 min; Total Elution Time: 10 min; Instrument: Thar 350 SFC) providing (S)-tert-butyl 5'-chloro-2',3',4,5-tetrahydro-2H-spiro[benzo[b][1,4]oxazepine-3,1'-indene]-7-carboxylate as the first eluting isomer and (R)-tert-butyl 5'-chloro-2',3',4,5-tetrahydro-2H-spiro[benzo[b][1,4]oxazepine-3,1'-indene]-7-carboxylate as the second eluting isomer.

Step 10: (S)-tert-butyl 5-(((1R,2R)-2-(((tert-butyldiphenylsilyl)oxy)methyl)cyclobutyl)methyl)-5'-chloro-2',3',4,5-tetrahydro-2H-spiro[benzo[b][1,4]oxazepine-3,1'-indene]-7-carboxylate

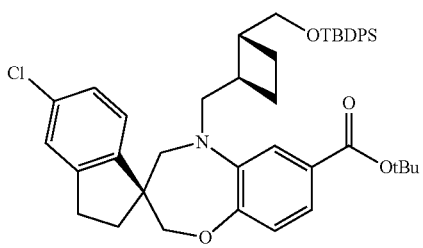

A mixture of (5)-tert-butyl 5'-chloro-2',3',4,5-tetrahydro-2H-spiro[benzo[b][1,4]oxazepine-3,1'-indene]-7-carboxylate (intermediate AA20, step 9, first eluting isomer; 0.930 g, 2.411 mmol) and (1R,2R)-2-(((tert-butyldiphenylsilyl)oxy)methyl)cyclobutanecarbaldehyde (Intermediate AA18, Step 19; 0.85 g, 2.411 mmol) in 20% AcOH/DCM (12 ml) was allowed to stir in an ice bath for 15 min. To the solution was added sodium cyanoborohydride (1.218 ml, 1.0 M in THF, 1.218 mmol, Sigma-Aldrich Chemical Company, Inc.) drop wise via syringe pump over 80 min. The resulting mixture was left stirring in the bath for 75 min. TLC (20% EtOAc/Hexanes) indicated reaction completion. The reaction solution was slowly poured into a cold aqueous NaOH solution (1.0 N, 20 mL), and the resulting mixture was allowed to stir at ambient temperature for 30 min. The organic layer was separated, and the aqueous layer was back extracted with EtOAc (3×15 mL). Organic solutions were combined. After removal of organic solvents under reduced pressure, purification of the residue by flash chromatography on ISCO Gold silica gel column with 0-25% EtOAc/Hexanes provided the title compound as a colorless syrup.

Step 11: (S)-tert-butyl 5'-chloro-5-(((1R,2R)-2-(hydroxymethyl)cyclobutyl)methyl)-2',3',4,5-tetrahydro-2H-spiro[benzo[b][1,4]oxazepine-3,1'-indene]-7-carboxylate

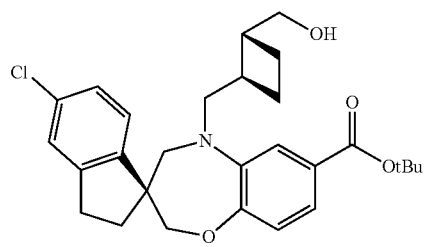 [SMILES: CC(C)(C)OC(=O)c1ccc2c(c1)N(C[C@@H]1CC[C@H]1CO)C[C@@]1(CCc3cc(Cl)ccc31)CO2]

To a flask charged with (5)-tert-butyl 5-(((1R,2R)-2-(((tert-butyldiphenylsilyl)oxy)methyl)cyclobutyl)methyl)-5'-chloro-2',3',4,5-tetrahydro-2H-spiro[benzo[b][1,4]oxazepine-3,1'-indene]-7-carboxylate (1.5 g, 2.076 mmol, Step 1) was added tetrabutylammonium fluoride (7.50 ml, 1.0 M in THF, 7.50 mmol, Sigma-Aldrich chemical Company Inc.). The solution was allowed to stir at rt for 2.0 h till TLC (20% EtOAc/Hexanes) indicated reaction completion. The resulting mixture was diluted with water (13) and extracted with EtOAc (2×15 mL). The organic layers were combined, washed with water (5 mL) and brine (5 mL), and dried over $MgSO_4$. After removal of organic solvents under reduced pressure, the residue was purified by flash chromatography on ISCO Gold silica gel column with 0-55% EtOAc/Hexanes to provide the title products as a white foam.

Step 12: (S)-tert-butyl 5'-chloro-5-(((1R,2R)-2-formylcyclobutyl)methyl)-2',3',4,5-tetrahydro-2H-spiro[benzo[b][1,4]oxazepine-3,1'-indene]-7-carboxylate

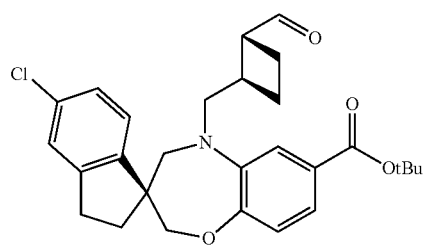 [SMILES: CC(C)(C)OC(=O)c1ccc2c(c1)N(C[C@@H]1CC[C@H]1C=O)C[C@@]1(CCc3cc(Cl)ccc31)CO2]

The title compound was prepared from ((S)-tert-butyl 5'-chloro-5-(((1R,2R)-2-(hydroxymethyl)cyclobutyl)

methyl)-2',3',4,5-tetrahydro-2H-spiro[benzo[b][1,4]
oxazepine-3,1'-indene]-7-carboxylate as a white foam, following the procedure described for the synthesis of Intermediate AA16, Step 7. m/z (ESI, +ve ion) 482.2 (M+H)+.

Step 13: (S)-tert-butyl 5'-chloro-5-(((1R,2R)-2-((S)-1-hydroxyallyl)cyclobutyl)methyl)-2',3',4,5-tetrahydro-2H-spiro[benzo[b][1,4]oxazepine-3,1'-indene]-7-carboxylate

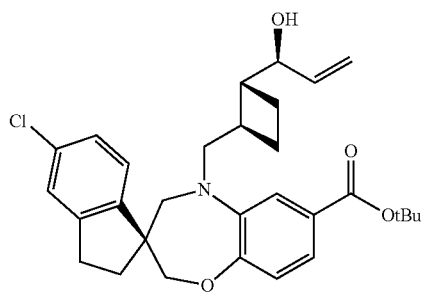 [SMILES: C=C[C@H](O)[C@@H]1CC[C@H]1CN1C[C@@]2(CCc3cc(Cl)ccc32)COc2ccc(C(=O)OC(C)(C)C)cc21]

To a −78° C. solution of (5)-tert-butyl 5'-chloro-5-(((1R,2R)-2-formylcyclobutyl)methyl)-2',3',4,5-tetrahydro-2H-spiro[benzo[b][1,4]oxazepine-3,1'-indene]-7-carboxylate (1509 mg, 3.13 mmol) in THF (16 mL) under $N_2$ was add vinylmagnesium bromide (6261 µl, 1.0 M in THF, 6.26 mmol, Sigma-Aldrich chemical Company Inc.) drop wise over 4 min. After stirring in the −78° C. bath for 2.0 hr, the reaction solution was allowed to warm with the bath to ambient temperature over 105 min. To this solution was added saturated aqueous $NH_4Cl$ (12 mL) and water (12 m) and the mixture was left at ambient temperature overnight. The organic layer was separated, and the aqueous layer was back extracted with EtOAc (3×15 mL). The organic solutions were combined, washed with brine (5 mL), and dried over $MgSO_4$. After removal of organic solvents under reduced pressure, the residue was purified by flash chromatography on ISCO Gold silica gel column with 0-30% EtOAc/Hexanes. The first eluting fraction was collected as the title product as a white foam.

Step 14: (S)-5'-chloro-5-(((1R,2R)-2-((S)-1-hydroxyallyl)cyclobutyl)methyl)-2',3',4,5-tetrahydro-2H-spiro[benzo[b][1,4]oxazepine-3,1'-indene]-7-carboxylic Acid To a solution of (S)-tert-butyl 5'-chloro-5-(((1R,2R)-2-((S)-1-hydroxyallyl)cyclobutyl)methyl)-2',3',4,5-tetrahydro-2H-spiro[benzo[b][1,4]oxazepine-3,1'-indene]-7-carboxylate (655 mg, 1.284 mmol, Step 4) in $CH_2Cl_2$ (8 mL) at ambient temperature was added trifluoroacetic acid (2 mL, Sigma-Aldrich chemical Company Inc.). The resulting mixture was allowed to stir at rt for 3.0 hr. After removal of organic solvents under reduced pressure, the residue was purified by flash chromatography on ISCO Gold silica gel column with 0-60% EtOAc/Hexanes (EtOAc contained 0.3% HOAc) to provide the title compound as a white foam.

Intermediate EE11

N,N-bis(4-methoxybenzyl)amine

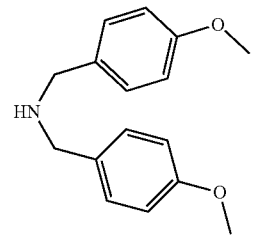 [SMILES: COc1ccc(CNCc2ccc(OC)cc2)cc1]

A solution of 4-methoxybenzaldehyde (100 g, 734.5 mmol, Spectrochem) and 4-methoxybenzyl amine (100 g, 734.5 mmol, G.L.R.) in toluene (0.8 L) was refluxed at 130° C. using a Dean Stark apparatus for 6 h. The reaction was monitored by TLC and upon completion, excess solvent was removed under reduced pressure and the residue was dissolved in methanol (0.8 L). The resulting solution was cooled to 0° C. and sodium borohydride (36.12 g, 954.8 mmol) was added in portions. After complete addition the reaction mixture was stirred for 3 h at ambient temperature. Methanol was then removed, and the residue was diluted with water (1.0 L) and ethyl acetate (2.0 L). The layers were separated and the aqueous layer was extracted with ethyl acetate (2×1.0 L). The combined organic layer was washed with water, brine and dried over sodium sulfate. Solvent was removed under reduced pressure and the crude material thus obtained was purified by column chromatography over silica gel (100-200 mesh size) eluting with a gradient of 100% hexanes to 25% ethyl acetate in hexanes affording the title compound (160 g, 84.6%) as colorless but opaque liquid. $R_f$: 0.5 in 30% Ethyl acetate in hexane.

Intermediate EE12

N,N-bis(4-methoxybenzyl)methanesulfonamide

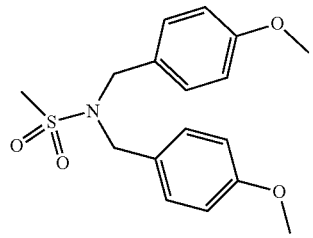 [SMILES: COc1ccc(CN(Cc2ccc(OC)cc2)S(C)(=O)=O)cc1]

A mixture of methanesulfonamide (Sigma-Aldrich, 5 g, 52.6 mmol), p-methoxybenzyl chloride (14.98 mL, 110 mmol), potassium carbonate anhydrous (36.3 g, 263 mmol) and potassium iodide (0.873 g, 5.26 mmol) in anhydrous 2-butanone (175 ml) was refluxed (75° C.) overnight. The reaction was monitored by TLC and LC/MS and upon completion, the mixture was cooled to ambient temperature, filtered, washed with diethyl ether and concentrated. The crude material (17.54 g, 52.3 mmol, 99% yield) was used with no further purification. MS (ESI, positive ion) m/z: 358.1 (M+Na).

Intermediate EE13

N,N-bis(4-methoxybenzyl)ethanesulfonamide

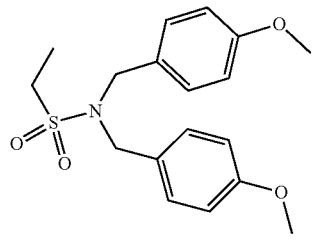 [SMILES: CCS(=O)(=O)N(Cc1ccc(OC)cc1)Cc1ccc(OC)cc1]

To a solution of N,N-bis(4-methoxybenzyl)amine (Intermediate EE11; 200 g, 775.19 mmol) in DCM (2.5 L) was added triethylamine (336.17 ml, 2325.5 mmol), and the reaction mixture was cooled to 0° C. Ethanesulfonyl chloride (95 mL, 1007.75 mmol, Aldrich) was then added in drop-wise manner followed by DMAP (19.0 g, 155.03 mmol). The resulting reaction mixture was stirred at ambient temperature for 30 min. The reaction was monitored by TLC and upon completion, the mixture was diluted with water and the layers were separated and the aqueous phase was extracted with DCM (3×1.5 L). The combined organic layer was washed with water, brine and dried over sodium sulfate. The solvent was removed under reduced pressure to afford the crude material which was purified by column chromatography over silica gel (100-200 mesh), eluting with a gradient of 0-12% ethyl acetate in hexanes affording the title compound (145 g, 53.4%) as white fluffy solid. $R_f$: 0.5 in 20% Ethyl acetate in hexane.

Intermediate EE14

N,N-bis(4-methoxybenzyl)propanesulfonamide

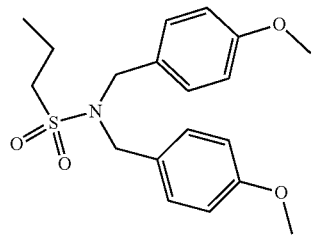 [SMILES: CCCS(=O)(=O)N(Cc1ccc(OC)cc1)Cc1ccc(OC)cc1]

To a solution of N,N-bis(4-methoxybenzyl)amine (Intermediate EE11; 405 g, 1569.7 mmol) in DCM (4.0 L) was added triethylamine (681.0 ml, 4709.3 mmol), and the reaction mixture was cooled to 0° C. Propanesulfonyl chloride (231 mL, 2040.6 mmol, Aldrich) was then added in a drop-wise manner followed by DMAP (38.3 g, 313.9 mmol). The resulting mixture was stirred at ambient temperature for 30 min. The reaction was monitored by TLC and upon completion, the mixture was diluted with 2.0 L of water, the layers were separated and the aqueous phase was extracted with DCM (3×2.0 L). The combined organic layer was washed with water, brine and dried over sodium sulfate. The solvent was removed under reduced pressure to afford the crude material which was purified by column chromatography over silica gel (100-200 mesh), eluting with a gradient of 0-12% ethyl acetate in hexanes affording the title compound (300 g, 52.44%) as white fluffy solid. $R_f$: 0.5 in 20% Ethyl acetate in hexane.

Intermediate EE15 but-3-ene-1-sulfonamide

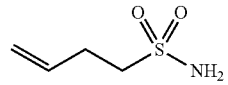

Step 1: Sodium but-3-ene-1-sulfonate

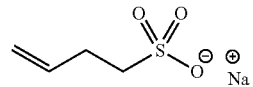

A mixture of 4-bromo-1-butene (3.01 ml, 29.6 mmol, LLBChem) and sodium sulfite (4.11 g, 32.6 mmol) in water (20 ml) was stirred at 110° C. overnight. The reaction was monitored by TLC and upon completion, water was removed under reduced pressure and the residue was triturated with acetone. The solid obtained was filtered to afford the title compound as a white solid (4.53 g) which was used as such in next step.

Step 2: but-3-ene-1-sulfonamide

A mixture of sodium but-3-ene-1-sulfonate (4.50 g, 28.5 mmol) and phosphorus oxychloride (70 mL) was stirred at 135° C. for 7 h. After this time, phosphorus oxychloride was removed under reduced pressure to obtain a dark residue containing a white solid. This residue was diluted with acetonitrile (20 ml), and then filtered to remove the precipitate. The filtrate was cooled to 0° C. and then treated with ammonia solution (30% aqueous) (30 mL) drop-wise. After complete addition, the reaction was stirred at 0° C. for 30 min. The mixture was then diluted with ethyl acetate (300 mL), washed with brine and dried over anhydrous sodium sulfate. The solvent was removed under reduced pressure and the residue was purified by column chromatography over silica gel (100-200 mesh; eluting with 1:1 EtOAc/hexane), affording the title compound as white solid, 1.55 g, (yield: 40%). $R_f$: 0.3 in 30% ethyl acetate in hexane. MS (ESI, positive ion) m/z: 117.1 (M+1).

Intermediate EE16

N,N-bis(4-methoxybenzyl)but-3-ene-1-sulfonamide

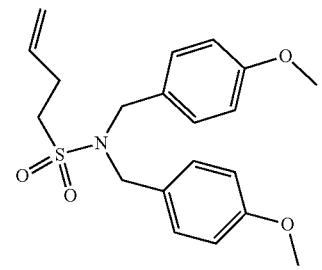 [SMILES: C=CCCS(=O)(=O)N(Cc1ccc(OC)cc1)Cc1ccc(OC)cc1]

A mixture of but-3-ene-1-sulfonamide (Intermediate EE15; 1.5 g, 11.10 mmol), p-methoxybenzyl chloride (3.76 mL, 27.7 mmol), potassium carbonate anhydrous (7.67 g, 55.5 mmol) and sodium iodide (0.166 g, 1.110 mmol) in anhydrous 2-butanone (55.5 ml) was refluxed (75° C.) overnight. The reaction was monitored by TLC and LC/MS and upon completion, the mixture was cooled to ambient temperature, filtered and concentrated. The crude material was absorbed onto a plu of silica gel and purified by chromatography through silica gel (100-200 mesh), eluting with 0 to 30% EtOAc in hexane, to provide the title compound (4.10 g, 10.92 mmol, 98% yield) as a colorless oil. $R_f$: 0.7 in 30% ethyl acetate in hexane. MS (ESI, positive ion) m/z: 376.2 (M+1).

Intermediate EE17

(R)-pent-4-ene-2-sulfonamide

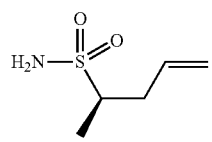

Step 1: (S)—N,N-bis(4-methoxybenzyl)pent-4-ene-2-sulfonamide and (R)—N,N-bis(4-methoxybenzyl)pent-4-ene-2-sulfonamide

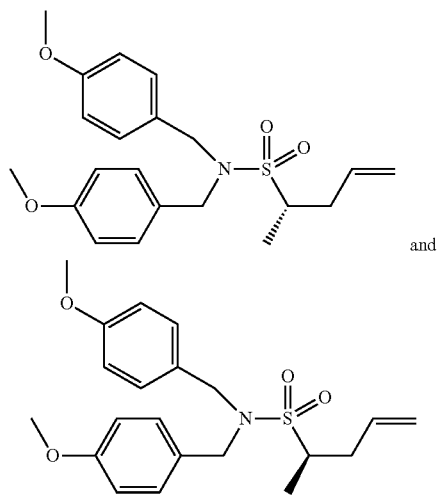

and

N,N-bis(4-methoxybenzyl)but-3-ene-1-sulfonamide (Intermediate EE16; 50.0 g, 133.2 mmol) was azeotroped with toluene and dried under vacuum for 1 h. THF (890 mL) was added and the mixture was cooled to −78° C. n-butyl lithium (2.5M in hexanes, 63.9 mL, 159.9 mmol) was then added and the reaction mixture was stirred at −78° C. for 1 h. This anion solution was added slowly to a solution of iodomethane (16.8 mL, 266.5 mmol) in THF (300 mL) cooled to −78° C. The resulting reaction mixture was stirred for another 15 min at −78° C. On completion of the reaction (monitored by TLC), the mixture was quenched with saturated NH₄Cl solution and extracted with ethyl acetate. The organic layer was dried over Na₂SO₄ and concentrated under reduced pressure to obtain crude material which was purified by column chromatography over silica gel eluting with 5-10% ethyl acetate in hexane to provide the title compound as a racemic mixture (22.0 g) of semisolid nature. Separation of the enantiomers by SFC (Column: Chiralpak AD-H, 50×250 mm, 5 μm; Mobile Phase A: CO₂; Mobile Phase B: Ethanol; Isocratic: 40% B with CO₂ recycler on; Flow Rate: 200 g/min; Loading: 2.0 mL of sample prepared as above (~100 mg); Detection: UV @ 230 nm; Cycle Time: 5 min; Total Elution Time: 10 min; Instrument: Thar 350 (Lakers)) provided (S)—N,N-bis(4-methoxybenzyl)pent-4-ene-2-sulfonamide as the first eluting isomer (retention time 2.22 min) and (R)—N,N-bis(4-methoxybenzyl)pent-4-ene-2-sulfonamide as the second eluting isomer (retention time 2.57 min).

Step 2: (R)-pent-4-ene-2-sulfonamide

To a solution of (R)—N,N-bis(4-methoxybenzyl)pent-4-ene-2-sulfonamide (Intermediate EE17, Step 1, second eluting isomer; 221 mg, 0.567 mmol) in CH₂Cl₂ (2.8 mL), was added trifluoroacetic acid (1.7 mL, 22.70 mmol) dropwise (the clear solution very rapidly turned dark). After stirring for 7 h (TLC 30% EtOAc/hexanes showed complete loss of starting material) the mixture was diluted with EtOAc, washed with sat. NaHCO₃, back extracted with EtOAc, dried over MgSO₄ and concentrated. The crude material was purified via chromatography (12 g ISCO Gold column; 0-40% EtOAc hexanes) to provide (R)-pent-4-ene-2-sulfonamide (70 mg, 0.469 mmol, 83% yield)

Intermediate EE172

(S)-pent-4-ene-2-sulfonamide

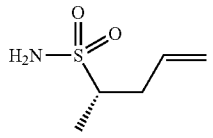

This intermediate was synthesized from (S)—N,N-bis(4-methoxybenzyl)pent-4-ene-2-sulfonamide (Intermediate EE17, Step 1, first eluting isomer) using the procedure described for Intermediate EE17, Step 2.

Intermediate EE18

(R)-hex-5-ene-3-sulfonamide

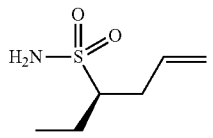

Step 1: (S)—N,N-bis(4-methoxybenzyl)hex-5-ene-3-sulfonamide and (R)—N,N-bis(4-methoxybenzyl)hex-5-ene-3-sulfonamide

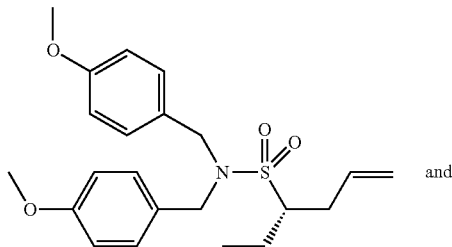

and

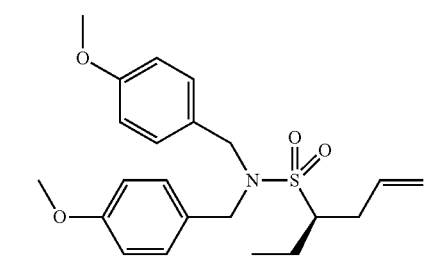

N,N-bis(4-methoxybenzyl)but-3-ene-1-sulfonamide (Intermediate EE16) (40.0 g, 106.6 mmol) was azeotroped in toluene under vacuum for 2 h. THF (700 mL) was added under argon atmosphere and the reaction mixture was cooled to −78° C. Butyl lithium (2.5M in hexanes; 71.6 mL, 127.9 mmol) was added and the reaction mixture was stirred at −78° C. for 1 h. This anion solution was added slowly to a solution of ethyl iodide (36.44 mL, 340.1 mmol) in THF (40 mL) cooled to −78° C. The resulting reaction mixture was then quenched with saturated NH₄Cl solution, allowed to reach ambient temperature and extracted with ethyl acetate. The organic layer was dried over Na₂SO₄ and concentrated under reduced pressure to obtain crude material which was purified by column chromatography over silica gel eluting with 5-10% ethyl acetate in hexane to provide the title compound as a racemic mixture (24 g) of semisolid nature. MS (ESI, positive ion) m/z; 404.03 (M+1). Separation of the enantiomers by SFC (Sample preparation: 14.4 g/200 mL (72 mg/mL) sample solution in MeOH:DCM (3:1); Column: Chiralpak AD-H, 30×250 mm, 5 μm; Mobile Phase A: CO₂; Mobile Phase B: MeOH (20 mM NH₃); Isocratic: 50% B, Flow Rate: 100 mL/min; Outlet Pressure: 100 bar; Loading: 1.0 mL of sample solution prepared as above (72 mg); Detection: UV @ 227 nm; Cycle Time: 8 min; Total Elution Time: 17 min; Instrument: Thar 350 SFC) provided (S)—N,N-bis(4-methoxybenzyl)hex-5-ene-3-sulfonamide as the first eluting isomer and (R)—N,N-bis(4-methoxybenzyl)hex-5-ene-3-sulfonamide as the second eluting isomer.

Step 2: (R)-hex-5-ene-3-sulfonamide

This intermediate was synthesized from (R)—N,N-bis(4-methoxybenzyl)hex-5-ene-3-sulfonamide (Intermediate EE18, Step 1, second eluting isomer) using the procedure described for Intermediate EE17, Step 2.

Intermediate EE182

(S)-hex-5-ene-3-sulfonamide

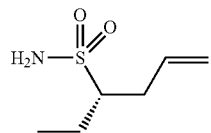

This intermediate was synthesized from (S)—N,N-bis(4-methoxybenzyl)hex-5-ene-3-sulfonamide (Intermediate EE18, Step 1, first eluting isomer) using the procedure described for Intermediate EE17, Step 2.

Intermediate EE19

N,N-bis(4-methoxybenzyl)pent-4-ene-1-sulfonamide

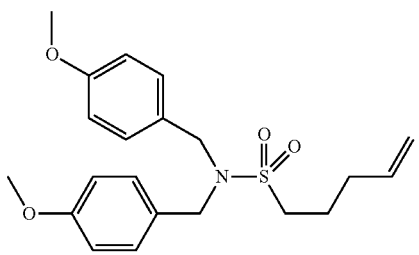 [SMILES: C=CCCCS(=O)(=O)N(Cc1ccc(OC)cc1)Cc1ccc(OC)cc1]

Step 1: Sodium pent-4-ene-1-sulfonate

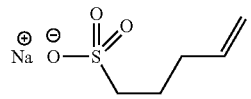

To a 3 L 3 necked round-bottomed flask equipped with a mechanical stirrer, a nitrogen gas inlet, a condenser, and a temperature probe was charged 5-bromo-1-pentene (Sigma Aldrich, 200 g, 1342 mmol), sodium sulfite (Strem Chemicals; 186 g, 1476 mmol), and water (400 mL). The mixture was heated to reflux (set at 100° C. and refluxed at 93-94° C.) 4 hours; aliquot NMR showed >95% conversion. The mixture was concentrated and azeotroped with acetone to remove water. The crude solid was washed with acetone and filtered to afford sodium pent-4-ene-1-sulfonate (350 g, 2033 mmol).

Step 2: pent-4-ene-1-sulfonamide

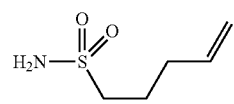

To a 3 L 3 necked round-bottomed flask equipped with a mechanical stirrer, a nitrogen gas inlet, a condenser, and a temperature probe was charged sodium pent-4-ene-1-sulfonate (100 g, 581 mmol) (~150 g of crude material from step 1) and phosphorus oxychloride (Sigma Aldrich; 532 ml, 5808 mmol). The mixture was heated to 90° C. for 18 hours after which, the reaction was filtered and the solid was washed with CH₃CN. The organic solution was concentrated and azeotroped with CH₃CN to remove POCl₃ to afford 85 g pent-4-ene-1-sulfonyl chloride intermediate. This material (solution in 300 mL CH₃CN) was charged onto a 1 L 3 necked round-bottomed flask equipped with a mechanical stirrer, a nitrogen gas inlet, a condenser, and a temperature probe. The reaction was cooled to 0-5° C. and ammonium hydroxide (Sigma Aldrich; 28% NH₃; 404 ml, 2904 mmol) was added slowly over 30 min. The reaction was stirred at 0-5° C. for 1 hour, after which EtOAc (300 mL) was added and the mixture was extracted with EtOAc and concentrated to afford pent-4-ene-1-sulfonamide (50 g, 335 mmol, 57.7% yield) as a brown oil Step 3: N,N-bis(4-methoxybenzyl)pent-4-ene-1-sulfonamide The title compound was synthesized from pent-4-ene-1-sulfonamide (4.5 g, 30.2 mmol) following the procedure described for Intermediate EE16. Purification of the crude material provided N,N-bis(4-methoxybenzyl)pent-4-ene-1-sulfonamide (11.4 g, 29.3 mmol, 97% yield) as a colorless oil.

Intermediate EE20

(R)-hex-5-ene-2-sulfonamide

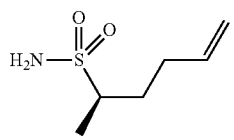

Step 1: (S)—N,N-bis(4-methoxybenzyl)hex-5-ene-2-sulfonamide and (R)—N,N-bis(4-methoxybenzyl)hex-5-ene-2-sulfonamide

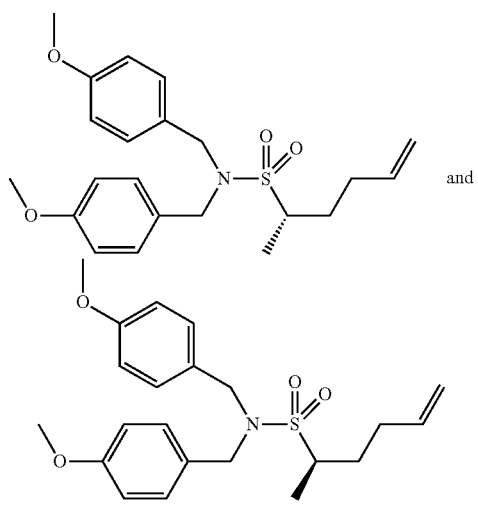

A solution of N,N-bis(4-methoxybenzyl)ethanesulfonamide (Intermediate EE13; 140.0 g, 400.64 mmol) in THF (1.4 L, THF was purged with argon for 15 min before using) was cooled to −78° C. and butyl lithium solution (2.6 M in hexanes, 200.0 ml, 520.83 mmol) was added drop-wise. The mixture turned dark pink after complete addition. The resulting solution was stirred at −78° C. for 10 min, and 4-bromo-1-butene (73.2 ml, 721.15 mmol) was added over 2 min. The solution turned colorless or light brown upon addition of 4-bromo-1-butene. After 5 min, the reaction was allowed to reach ambient temperature and stir for 1 h. The reaction was monitored by TLC and upon completion, the mixture was quenched with saturated NH₄Cl solution (400 mL) and the resulting aqueous layer was extracted with ethyl acetate (2×1.0 L). The combined organic layer was washed with brine and dried over sodium sulfate. The solvent was removed under reduced pressure to afford the crude material which was purified by column chromatography (silica gel 100-200 mesh) eluting with a gradient of 0-4% acetone in hexanes affording the title compound (racemic mixture, 80.0 g, 49.5%) as a colorless thick oil. R$_f$: 0.5 in 10% Acetone in hexane. MS (ESI, positive ion) m/z: 404.25 (M+1). Separation of the enantiomers by SFC (Sample preparation: 75 g/1.5 L (50 mg/mL) sample solution in MeOH; Column: Chiralpak IF, 21×250 mm, 5 µm; Mobile Phase A: CO₂; Mobile Phase B: MeOH (0.2% DEA); Isocratic: 40% B; Flow Rate: 80 mL/min; Outlet Pressure: 100 bar; Loading: 3.0 mL of sample solution prepared as above (150 mg); Detection: UV @ 225 nm; Cycle Time: 3.9 min; Total Elution Time: 6 min; Instrument: Thar 80 SFC) provided (S)—N,N-bis(4-methoxybenzyl)hex-5-ene-2-sulfonamide as the first eluting isomer and (R)—N,N-bis(4-methoxybenzyl)hex-5-ene-2-sulfonamide as the second eluting isomer.

Step 2: (R)-hex-5-ene-2-sulfonamide

The title compound was synthesized from (R)—N,N-bis(4-methoxybenzyl)hex-5-ene-2-sulfonamide (Intermediate EE20, Step 1, second eluting isomer) using the procedure described for Intermediate EE17, Step 2.

Intermediate EE202

(S)-hex-5-ene-2-sulfonamide

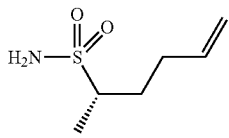

The title compound was synthesized from (S)—N,N-bis(4-methoxybenzyl)hex-5-ene-2-sulfonamide (Intermediate EE20, Step 1, first eluting isomer) using the procedure described for Intermediate EE17, Step 2.

Intermediate EE21

(R)-hept-6-ene-3-sulfonamide

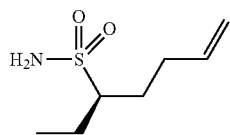

Step 1: (S)—N,N-bis(4-methoxybenzyl)hept-6-ene-3-sulfonamide and (R)—N,N-bis(4-methoxybenzyl)hept-6-ene-3-sulfonamide

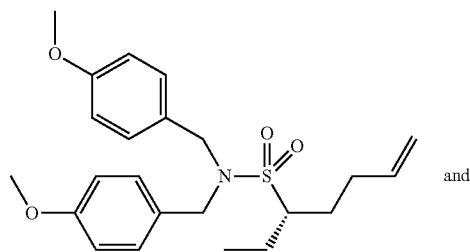

and

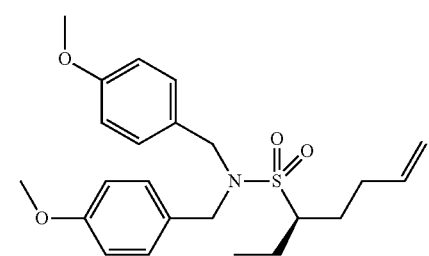

The title compound was synthesized from N,N-bis(4-methoxybenzyl)propanesulfonamide (Intermediate EE14) using the procedure described for Intermediate AA20, Step 1. $R_f$: 0.5 in 10% acetone in hexane. Separation of the enantiomers by SFC (Sample preparation: 40.55 g/170 mL (238.5 mg/mL) sample solution in MeOH; Column: Chiralpak AD-H, 50×150 mm, 5 μm; Mobile Phase A: $CO_2$; Mobile Phase B: MeOH (20 mM $NH_3$); Isocratic: 50% B; Flow Rate: 190 mL/min; Outlet Pressure: 100 bar; Loading: 1.5 mL of sample solution prepared as above (357.8 mg); Detection: UV @ 227 nm; Cycle Time: 17.5 min; Total Elution Time: 21 min; Instrument: Thar 350 SFC) provided (S)—N,N-bis(4-methoxybenzyl)hept-6-ene-3-sulfonamide as the first eluting isomer and (R)—N,N-bis(4-methoxybenzyl)hept-6-ene-3-sulfonamide as the second eluting isomer.

Step 2: (R)-hept-6-ene-3-sulfonamide

The title compound was synthesized from (R)—N,N-bis(4-methoxybenzyl)hept-6-ene-3-sulfonamide (Intermediate EE21, Step 1, second eluting isomer) using the procedure described for Intermediate EE17, Step 2.

Intermediate EE212

(S)-hept-6-ene-3-sulfonamide

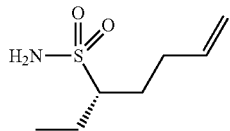

The title compound was synthesized from (S)—N,N-bis(4-methoxybenzyl)hept-6-ene-3-sulfonamide (Intermediate EE21, Step 1, first eluting isomer) using the procedure described for Intermediate EE17, Step 2.

Intermediate EE22

(2R,3S)-3-methylhex-5-ene-2-sulfonamide

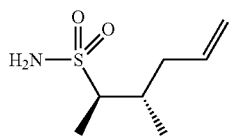

Step 1: (4S,5S)-4,5-dimethyl-1,3,2-dioxathiolane 2,2-dioxide

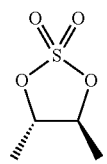

To a 500-mL, 3-necked round-bottomed flask (equipped with a water-cooled reflux condenser and an HCl trap) was added (2s,3s)-(+)-2,3-butanediol (Aldrich, Milwaukee Wisconsin)(15.00 ml, 166 mmol) and $CCl_4$ (120 ml). Thionyl chloride, reagentplus (14.57 ml, 200 mmol) was then added drop wise via a syringe over a period of 20 minutes and the resulting mixture was heated to 98° C. for 45 minutes, then it was allowed to cool to room temperature. Rf of intermediate=0.42 eluting with 50% EtOAc in heptanes; use $KMnO_4$ to visualize compound. The reaction mixture was then cooled in an ice-water bath, MeCN (120 mL) and water (150 mL) were added followed by ruthenium(III) chloride (0.035 g, 0.166 mmol). Sodium periodate (53.4 g, 250 mmol) was then added slowly portion wise over 30 minutes. The resulting biphasic brown mixture was stirred vigorously while allowed to reach room temperature for a period of 1.5 hour (internal temperature never increased above room temperature). TLC (50% EtOAc in heptanes) showed complete conversion. The crude mixture was then poured into ice water and extracted twice with 300 ml of diethyl ether. The combined organic layers were washed once with 200 ml of saturated sodium bicarbonate, washed once with 200 ml of brine, dried over sodium sulfate and concentrated by rotary evaporation to give (4S,5S)-4,5-dimethyl-1,3,2-dioxathiolane 2,2-dioxide (21.2 g, 139 mmol) as a red oil.

Step 2: (2S,3S)-3-methylhex-5-en-2-ol

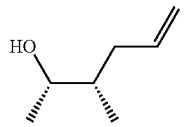

To a 500 ml flask was added (4S,5S)-4,5-dimethyl-1,3,2-dioxathiolane 2,2-dioxide (from Intermediate EE22, Step 1; 21.2 g, 139 mmol) and THF (220 mL) at which time the solution was cooled to −78° C. and was subjected to 3 cycles of evacuation/back-filling with argon. To the solution was then added dilithium tetrachlorocuprate(ii), 0.1 m solution in tetrahydrofuran (69.7 mL, 6.97 mmol). The resulting mixture was stirred at −78° C. for 30 minutes and then allylmagnesium bromide, 1.0 m solution in diethyl ether (397 mL, 397 mmol) was added slowly via cannula over 80 minutes. The resulting mixture was stirred at 0° C. for 4 hours. The mixture was then quenched carefully with 200 mL water and allowed to reach room temperature at which time the volatiles were removed by rotary evaporation. To the aqueous residue was then added 50% $H_2SO_4$ (150 mL), the mixture was stirred for 5 minutes, $Et_2O$ was then added (400 mL) and the mixture was stirred vigorously at room temperature overnight. The layers were then separated, the aqueous layer was extracted with 300 ml $Et_2O$ and the combined organic layers were washed with 300 ml of saturated sodium bicarbonate, dried over sodium sulfate, filtered and concentrated by rotary evaporation to give (2S,3S)-3-methylhex-5-en-2-ol (6.7 g, 58.7 mmol) as a clear oil. Rf=0.60 eluting with 50% EtOAc in heptanes.

Step 3: 2-(((2R,3S)-3-methylhex-5-en-2-yl)thio)pyrimidine

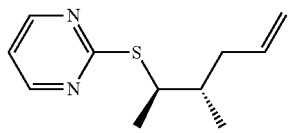

To a 2000 ml dry round bottom flask containing a stirring solution of tributylphosphine (57.7 ml, 231 mmol) in 1000 mL degassed THF (sparged with argon for 30 minutes plus 5 cycles of pump/add argon) at 0° C. was added diethyl azodicarboxylate, 40 wt. % solution in toluene (103 ml, 262 mmol) drop wise under an atmosphere of argon. Note: the orange color of DEAD was quenched almost immediately. Then a solution of (2S,3S)-3-methylhex-5-en-2-ol (from Intermediate EE22, Step 2; 17.6 g, 154 mmol; dried over sodium sulfate) was added drop wise as a solution in 50 ml of THF to the solution of phosphine/DEAD complex, via syringe-filter (0.45 um). The resulting ROH/DEAD/$Bu_3P$ mixture was aged at zero degrees for 15 minutes (solution turned light orange), at which time pyrimidine-2-thiol (49.3 g, 439 mmol) was added gradually to the top of the reaction vessel (as a solid) under positive argon pressure. The reaction was stirred at 0° C. for 1 hour then at room temperature 15 hours (Reaction not done at 12 hours by LCMS). Note: The reaction cannot be monitored by the disappearance of starting material. Use toluene as an internal standard. The crude reaction was then filtered to remove excess pyrimidine-2-thiol, diluted with 1000 ml of EtOAc, extracted twice with 500 ml of 1 N $K_2CO_3$ and once with 500 ml of brine. The aqueous layer was back extracted with 300 ml of EtOAc and the combined organic layers were dried over sodium sulfate. The organic solution was then filtered, the solvent removed by rotary evaporation and the crude filtered to remove the (E)-diethyl diazene-1,2-dicarboxylate generated in the reaction. The filtrate (125 g) was passed through a silica plug (500 g silica, eluting with 2 L of DCM) to give 75 g of crude product after solvent removal. The crude product was purified again on a Combiflash (125 g gold silica column), eluting with 10% EtOAc in heptanes to give 2-(((2R,3S)-3-methylhex-5-en-2-yl)thio)pyrimidine (20.37 g, 98 mmol) as a light yellow oil.

Step 4: 2-(((2R,3S)-3-methylhex-5-en-2-yl)sulfonyl)pyrimidine

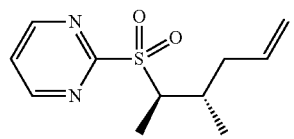 [SMILES: C=CC[C@H](C)[C@@H](C)S(=O)(=O)c1ncccn1]

To a 500 ml three neck flask with a reflux condenser was added phenylphosphonic acid (3.95 g, 24.96 mmol), sodium tungstate oxide dihydrate (8.23 g, 24.96 mmol), tetrabutylammonium sulfate, 50 wt. % solution in water (28.7 ml, 24.96 mmol), a catalytic amount of hydrogen peroxide 30% in water (12.75 ml, 125 mmol), toluene (200 ml) and 2-(((2R,3S)-3-methylhex-5-en-2-yl)thio)pyrimidine (from Intermediate EE22, Step 3; 52 g, 250 mmol). The reaction was stirred at 45° C. for 5 minutes at which time hydrogen peroxide 30% in water (58.6 ml, 574 mmol) was added portion wise (10 ml at a time). Five minutes after the first portion of hydrogen peroxide was added, an exotherm was observed (65° C.), the reaction was taken out of oil bath, the addition was stopped and the flask placed in a water bath until temperature stabilizes. The flask was taken out of the water bath and the portion wise addition of hydrogen peroxide was continued at a rate in which the internal temperature stayed between 45° C. and 55° C. (about 40 minutes). Note: an ice bath was utilized if the temperature went above 60° C. and an oil bath was used if the temperature fell below 45° C. The reaction was then stirred at 45° C. for one hour. The reaction was diluted with 1400 ml of EtOAc and extracted two times with 500 ml of water and once with 500 ml of brine. The organic layer was dried over sodium sulfate, filtered, concentrated and the crude purified on a Combiflash (330 g gold silica column per 30 grams of crude), eluting with 0%-50% EtOAc in heptanes to give 2-(((2R,3S)-3-methylhex-5-en-2-yl)sulfonyl)pyrimidine (55.7 g, 232 mmol) as a light yellow oil.

Step 5: Sodium (2R,3S)-3-methylhex-5-ene-2-sulfinate

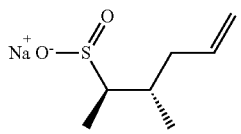

To a solution of 2-(((2R,3S)-3-methylhex-5-en-2-yl)sulfonyl)pyrimidine (from Intermediate EE22, Step 4; 52 g, 216 mmol) in MeOH (400 mL) at room temperature was added sodium methoxide solution (51.0 mL, 223 mmol) over 70 minutes. Note: sodium methoxide was added portion wise, the internal temperature was monitored and the addition was slowed or the reaction was cooled in a water bath, never letting the internal temperature exceeded 30° C. The mixture was then concentrated by rotary evaporation and the waxy solid was triturated with MTBE (add 200 ml MTBE, stir for 1 hour using a spatula to break up clumps), filtered (use a stream of nitrogen over filter cake) and washed with 100 ml of cold MTBE to obtain sodium (2R,3S)-3-methylhex-5-ene-2-sulfinate (46 g, 250 mmol) as a an off white solid.

Step 6: (2R,3S)-3-methylhex-5-ene-2-sulfonamide

To a 1000 ml three neck flask was added sodium (2R,3S)-3-methylhex-5-ene-2-sulfinate (from Intermediate EE22, Step 5; 46 g, 225 mmol), 500 ml of water and potassium acetate (44.1 g, 449 mmol) at room temperature. The pH was checked (should be around pH=8.5) at which time the flask was place in a 45° C. oil bath and hydroxylamine-o-sulfonic acid (21.09 g, 187 mmol) was added portion wise over 90 minutes. The internal temperature of the reaction was monitored and the reaction was removed from the oil bath (if needed) to control exotherm (Tmax=55° C.). Note: the reaction was monitored by LCMS every 10 minutes and was done after 0.83 eq. of hydroxylamine-o-sulfonic acid was added. The mixture was then cooled to room temperature and was extracted with 1000 ml of EtOAc. The organic phase was extracted three times with 500 ml of 1 N HCl, two times with 300 ml of saturated sodium bicarbonate, once with 200 ml of brine, dried over sodium sulfate, filtered and concentrated by rotary evaporation to provide (2R,3S)-3-methylhex-5-ene-2-sulfonamide (32 g, 181 mmol) as a white solid.

Example 1. (1S,3'R,6'R,7'S,8'E,11'R,12'R)-6-chloro-11'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

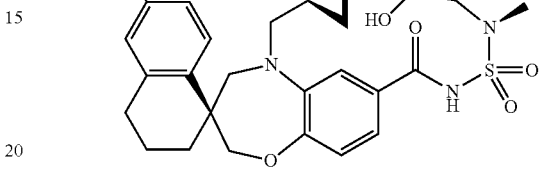

Step 1: (S)-ethyl 2-((S)-1-hydroxyethyl)pent-4-enoate

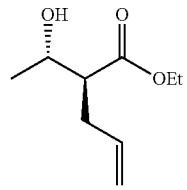

The following procedure was adapted from: Frater, G.; Müller, U.; Gunther, W. *Tetrahedron* 1984, 40, 1269-1277.

A 2 L 3-neck flask and addition funnel were dried overnight in an oven. The joints were greased, then assembled hot, and cooled under a flush of argon. The center neck was equipped with a pressure equalizing addition funnel, one side was fitted with a septa and an argon inlet line, while the other side was equipped with an adaptor connected to an oil bubbler to monitor flow of argon through the reaction system. Once cooled, lithium bis(trimethylsilyl)amide, 1.0 M solution in tetrahydrofuran (830 mL, 830 mmol) was charged to the addition funnel, and then to the reactor. The reaction flask was cooled in an acetone/CO$_2$ bath, and then a solution of (S)-(+)-3-hydroxy-N-butyric acid ethyl ester (49.4 mL, 378 mmol) in THF (50 mL) was added via cannula to the cooled reactor. This mixture stirred for 30 minutes, then was treated with allyl bromide (36.0 mL, 416 mmol). 10 minutes after the addition was complete, the reactor was removed from the bath and permitted to equilibrate to ambient temperature over 3 hours, when it was quenched by addition of saturated aqueous NH$_4$Cl (300 mL). The solution was transferred to a separatory funnel. Water was added to dissolve the precipitated solids. The layers were mixed and then separated. The aqueous phase was extracted with EtOAc (2×250 mL). The combined extracts were washed with water (300 mL) and then brine (300 mL). The solution was dried over MgSO$_4$, filtered and concentrated. $^1$H NMR analysis of the crude mixture showed that a considerable amount of HMDS was present. The concentrate was taken up in EtOAc (500 mL) then washed with 1N HCl (2×250 mL), water, and brine. The solution was dried with MgSO$_4$, filtered and concentrated to afford a yellow oil. The oil was distilled at reduced pressure (4 mmHg, 60-70° C.) to yield a clear liquid, (S)-ethyl 2-((S)-1-hydroxyethyl)pent-4-enoate (55 g, 319 mmol, 84% yield). $^1$H NMR (400 MHz, CDCl$_3$) δ 5.83-5.69 (m, 1H), 5.14-5.07 (m, 1H), 5.07-5.02 (m, 1H), 4.19 (q, J=7.1 Hz, 2H), 3.99-3.89 (m, 1H), 2.59 (d, J=7.4 Hz, 1H), 2.51-2.36 (m, 3H), 1.28 (t, J=7.1 Hz, 3H), 1.25 (d, J=6.5 Hz, 3H).

Step 2: (2R,3S)-2-allylbutane-1,3-diol

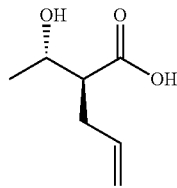

Lithium aluminum hydride, 1.0 M solution in THF (300 mL, 300 mmol) was cannulated to an oven dried 1 L Schlenk flask equipped with a nitrogen inlet through the side-arm. The flask was cooled in an ice-water bath. A solution of (S)-ethyl 2-((S)-1-hydroxyethyl)pent-4-enoate (25.9 g, 150 mmol) in THF (30 mL) was added dropwise via cannula to the stirring cold solution, over 15 minutes. The cannula and solution flask were rinsed with 15 mL of THF. The solution was stirred and the reaction progress was monitored by TLC. Upon completion, the cold solution was slowly quenched with water (11.5 mL), 15% w/v aqueous NaOH (11.5 mL) and then more water (34 mL). Once the solution had warmed to RT, the solution was treated with Na$_2$SO$_4$, and was then filtered. The solids were washed twice with hot EtOAc (2×100 mL). Concentration of the solution yielded a clear oil, characterized as (2R,3S)-2-allylbutane-1,3-diol by $^1$H NMR, of about 90% purity. The material was not purified further. $^1$H NMR (400 MHz, CDCl$_3$) δ 5.80 (tdd, J=17.2, 10.0, 7.1 Hz, 1H), 5.12-5.00 (m, 2H), 3.96-3.86 (m, 2H), 3.67 (dd, J=11.2, 6.3 Hz, 1H), 2.80 (br. s., 2H), 2.29-2.18 (m, 1H), 2.16-2.05 (m, 1H), 1.61-1.51 (m, 1H), 1.28 (dd, J=6.3, 1.0 Hz, 3H).

Step 3: (2S,3R)-3-(((tert-butyldimethylsilyl)oxy) methyl)hex-5-en-2-ol

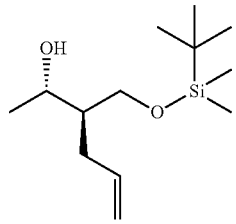 [SMILES: C=CC[C@H](CO[Si](C)(C)C(C)(C)C)[C@H](C)O]

A solution of (2R,3S)-2-allylbutane-1,3-diol (3.11 g, 23.89 mmol) in DCM (50 ml) was treated with imidazole (2.00 ml, 30.4 mmol) and then tert-butyldimethylsilyl chloride (3.988 g, 26.5 mmol) causing the clear homogenous solution to become opaque white. The solution was stirred at ambient temperature (ca. 2 h) then quenched with water (50 mL). The layers were separated, and the aqueous layer was extracted with DCM (25 mL). The combined organic layers were washed with brine, dried over Na$_2$SO$_4$, filtered and concentrated to yield clear oil. The oil was purified by column chromatography eluting with a gradient of 5 to 20% EtOAc/hexanes, on a 80 g SiO$_2$ column, to yield (2S,3R)-3-(((tert-butyldimethylsilyl)oxy)methyl)hex-5-en-2-ol (4.47 g, 18.29 mmol, 77% yield). $^1$H NMR (400 MHz, CDCl$_3$) δ 5.78 (dddd, J=16.8, 10.0, 7.8, 6.3 Hz, 1H), 5.10-5.01 (m, 2H), 3.93 (dd, J=10.2, 3.7 Hz, 1H), 3.85 (qdd, J=6.3, 6.1, 5.1 Hz, 1H), 3.65 (dd, J=10.2. 6.1 Hz, 1H), 3.58 (d, J=5.1 Hz, 1H), 2.28-2.20 (m, 1H), 2.14-2.05 (m, 1H), 1.59-1.50 (m, 1H), 1.25 (d, J=6.3 Hz, 3H), 0.91 (s, 9H), 0.09 (s, 6H).

Step 4: 2-(((2R,3R)-3-(((tert-butyldimethylsilyl)oxy) methyl)hex-5-en-2-yl)thio)pyrimidine

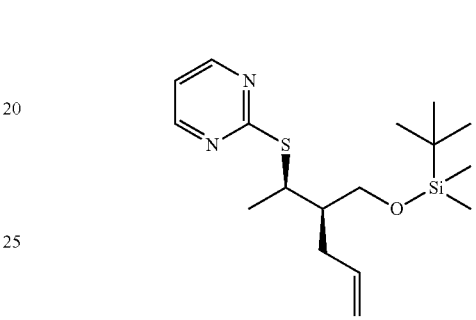

A cold (0° C.) stirred solution of (2S,3R)-3-(((tert-butyldimethylsilyl)oxy)methyl)hex-5-en-2-ol (4.77 g, 19.51 mmol) and triethylamine (3.5 ml, 25.2 mmol) in DCM (40 mL) was treated with methanesulfonyl chloride (2.0 mL, 25.8 mmol), added dropwise via syringe, which yielded an opaque mixture by the end of the addition. The solution was removed from the bath after 1 hour and stirred while equilibrating to ambient temperature. Water was added to the reaction mixture, and the layers were separated. The aqueous layer was extracted with DCM (2×) then the combined organic layers were washed with 1N HCl (2×25 mL) and then saturated aqueous NaHCO$_3$ (25 mL), which caused the formation of an emulsion that could not be broken by addition of brine, additional NaCl, water, or hexane. Finally, the mixture was diluted with 300 mL EtOAc, and separation was observed. The layers were separated, and then the organic layer was washed with brine (50 mL), dried over MgSO$_4$, filtered and concentrated to give a clear oil.

The oil was taken up in DMF (65 mL) and treated with 2-mercapto-pyrimidine (2.22 g, 19.79 mmol) and potassium carbonate (2.73 g, 19.75 mmol) then the reaction mixture was stirred at ambient temperature for 18 hours. $^1$H NMR analysis of an aliquot revealed minimal conversion. The reaction mixture was heated to 60° C.; within 5 hours the reaction failed to reach completion. More K$_2$CO$_3$ (300 mg) and 2-mercapto-pyrimidine (200 mg) were added and the solution stirred overnight (16 h). After cooling to room temperature, the reaction mixture was partitioned between water and EtOAc. The layers were separated, and the aqueous layer was extracted once with EtOAc. The combined organic extracts were washed thrice with brine, then dried over MgSO$_4$, filtered and concentrated to yield an oily yellow residue. The residue was purified by column chromatography eluting with a gradient of 10 to 30% EtOAc/hexanes on a 80 g SiO$_2$ column to afford 2-(((2R,3R)-3-(((tert-butyldimethylsilyl)oxy)methyl)hex-5-en-2-yl)thio)pyrimidine (4.76 g, 14.06 mmol, 9:1 mixture of thioether to mesylate). $^1$H NMR (400 MHz, CDCl$_3$) δ 8.50 (d, J=4.9 Hz, 2H), 6.92 (t, J=4.8 Hz, 1H), 5.84 (ddt, J=17.1, 10.1, 7.0 Hz, 1H), 5.12-5.02 (m, 2H), 4.22 (qd, J=7.1, 4.2 Hz, 1H), 3.75-3.66 (m, 2H), 2.34-2.17 (m, 2H), 2.02-1.93 (m, 1H), 1.45 (d, J=7.0 Hz, 3H), 0.88 (s, 9H), 0.03 (s, 3H), 0.00 (s, 3H); MS (ESI) m/z=339.3 [M+H]$^+$.

Step 5: 2-(((2R,3R)-3-(((tert-butyldimethylsilyl)oxy)methyl)hex-5-en-2-yl)sulfonyl)pyrimidine

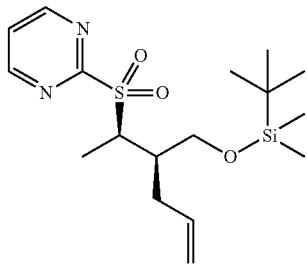 [SMILES: C=CC[C@H](CO[Si](C)(C)C(C)(C)C)[C@@H](C)S(=O)(=O)c1ncccn1]

A solution of 2-(((2R,3R)-3-(((tert-butyldimethylsilyl)oxy)methyl)hex-5-en-2-yl)thio)pyrimidine (4.76 g, 14.1 mmol) in DCM (75 mL) was cooled in an ice bath, then treated with 3-chlorobenzoperoxoic acid (6.62 g, 29.5 mmol) in a single portion. DMF (3 mL) was added causing the heterogeneous cloudy mixture to become clear. The solution was stirred in the ice-water bath and equilibrated to ambient temperature while stirring overnight. The mixture was quenched with saturated aqueous NaHCO$_3$. The layers were separated, and the aqueous layer was extracted with DCM (2×). The combined extracts were washed twice with brine and then dried over MgSO$_4$, filtered and concentrated, yielding a yellow oil. The oil was purified by column chromatography on a 80 g SiO$_2$ column, eluting with a gradient of 0 to 100% EtOAc/hexanes to yield 2-(((2R,3R)-3-(((tert-butyldimethylsilyl)oxy)methyl)hex-5-en-2-yl)sulfonyl)pyrimidine (3.8 g, 10.3 mmol, 73% yield). $^1$H NMR (400 MHz, CDCl$_3$) δ 8.91 (d, J=4.7 Hz, 2H), 7.50 (t, J=4.9 Hz, 1H), 5.67 (dddd, J=16.6, 10.4, 7.6, 6.8 Hz, 1H), 4.98-5.07 (m, 2H), 3.98 (qd, J=7.2, 3.3 Hz, 1H), 3.89 (dd, J=10.4, 4.3 Hz, 1H), 3.75 (dd, J=10.4, 5.7 Hz, 1H), 2.44-2.53 (m, 1H), 2.26-2.35 (m, 1H), 2.10-2.19 (m, 1H), 1.30 (d, J=7.2 Hz, 3H), 0.83 (s, 9H), 0.01 (s, 3H), 0.00 (s, 3H); MS (ESI) m/z=371.2 [M+H]$^+$.

Step 6: (2R,3R)-3-(((tert-butyldimethylsilyl)oxy)methyl)hex-5-ene-2-sulfonamide

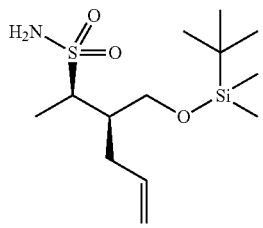 [SMILES: C=CC[C@H](CO[Si](C)(C)C(C)(C)C)[C@@H](C)S(N)(=O)=O]

2-(((2R,3R)-3-(((tert-butyldimethylsilyl)oxy)methyl)hex-5-en-2-yl)sulfonyl)pyrimidine (3.8 g, 10.25 mmol) was dissolved in MeOH (103 mL). The solution was treated with 25 wt % MeONa/MeOH (7.03 mL, 30.8 mmol). After stirring for 45 minutes, the reaction mixture was concentrated to yield a yellow foam. The foam was dissolved in water (100 mL) and treated with sodium acetate (1.73 g, 21.09 mmol) and hydroxylamine-o-sulfonic acid (1.160 g, 10.25 mmol). The solution was stirred at 50° C. for 5 hours, and was then cooled to ambient temperature. EtOAc (100 mL) was added and the layers were vigorously mixed. The organic layer was separated, and the aqueous layer was extracted twice more. The combined extracts were dried with MgSO$_4$, filtered and concentrated yielding a pale yellow residue. The residue was purified by column chromatography eluting with a gradient of 10 to 40% EtOAc/hexanes to yield (2R,3R)-3-(((tert-butyldimethylsilyl)oxy)methyl)hex-5-ene-2-sulfonamide (2.6 g, 8.45 mmol, 82% yield) as a white solid. $^1$H NMR (400 MHz, CDCl$_3$) δ 5.76 (dddd, J=16.8, 10.6, 7.4, 6.7 Hz, 1H), 5.06-5.14 (m, 2H), 4.88 (broad s, 2H), 3.80 (dd, J=10.9, 7.1 Hz, 1H), 3.65 (dd, J=10.9, 4.4 Hz, 1H), 3.25 (qd, J=7.2, 2.5 Hz, 1H), 2.48 (qdd, J=7.3, 4.5, 2.5 Hz, 1H), 2.27 (dt, J=14.0, 6.8 Hz, 1H), 1.98-2.09 (m, 1H), 1.41 (d, J=7.2 Hz, 3H), 0.91 (s, 10H), 0.09 (s, 3H), 0.09 (s, 3H).

Step 7: (S)-5-(((1R,2R)-2-((1S,5R,6R,E)-5-(((tert-butyldimethylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic Acid

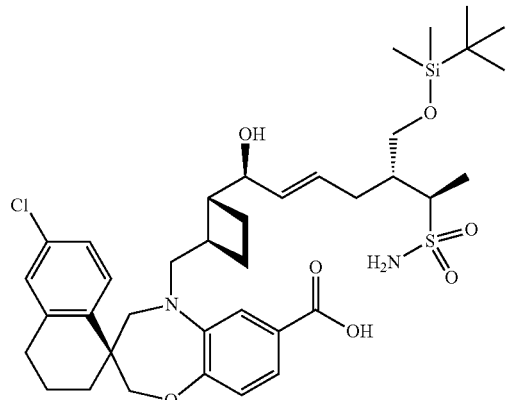

A 3-neck flask containing a solution of Intermediate AA11A (1 g, 2.137 mmol) and (2R,3R)-3-(((ter t-butyldimethylsilyl)oxy)methyl)hex-5-ene-2-sulfonamide (2.02 g, 6.57 mmol) in 1,2-dichloroethane (20 mL) was evacuated and backfilled with argon three times. Hoveyda-Grubbs 2$^{nd}$ generation catalyst (0.140 g, 0.223 mmol) was then added as a solution in 1,2-dichloroethane (1.0 mL). The dark green solution was stirred at ambient temperature, during which time it became dark brown. Within 30 minutes, starting materials, olefin homodimers and desired heterodimer product were observed by LC/MS analysis of the reaction mixture. After 4.5 hours, more catalyst (140 mg, 0.223 mmol) was added. An hour later, the reaction mixture was quenched by sparging air through the solution. The reaction solution was then concentrated and the residue was purified by column chromatography eluting with a gradient of 10% to 40% to 70% acetone/DCM, on a 80 g SiO$_2$ column to give a dark brown film (610 mg). MS (ESI): m/z=746.8 [M+H]$^+$.

Step 8: (1S,3'R,6'R,7'S,8'E,11'R,12'R)-6-chloro-11'-(((tert-butyldimethylsilyl)oxy)methyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

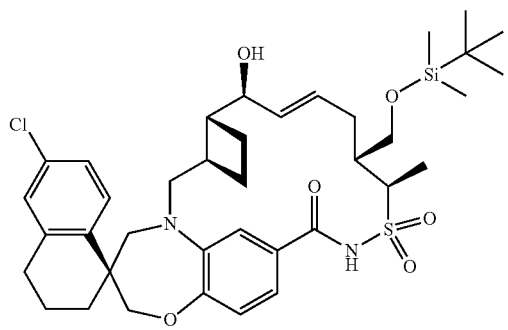

The brown residue from Step 7 (610 mg) in DCM (16 mL) was treated with 4-dimethylaminopyridine (170 mg, 1.392 mmol) and then 1-(3-dimethylaminopropyl)-3-ethylcarbodiimide HCl (313 mg, 1.632 mmol), which was added in portions over 3 minutes. The brown solution was stirred at ambient temperature for 17 hours. The solution was diluted with DCM then washed successively with 1 M HCl, saturated aqueous NaHCO$_3$ and brine. The dark brown solution was dried over MgSO$_4$, filtered and concentrated. The residue was purified by column chromatography eluting with a gradient of 30 to 60% EtOAc/hexanes on a 40 g SiO$_2$ column and a tan solid was obtained (250 mg). MS (ESI) m/z=728.8 [M+1-1]$^+$.

Step 9: (1S,3'R,6'R,7'S,8'E,11'R,12'R)-6-chloro-11'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide The tan solid from Step 8 (208 mg) was azeotroped twice with toluene, then dissolved in THF (2.9 mL). Sodium hydride, 60% dispersion in mineral oil (48 mg, 1.200 mmol) was added to the solution, which was stirred for 30 minutes. The resulting mixture was treated with methyl iodide (0.040 mL, 0.644 mmol) then stirred for 1 hour. The reaction was quenched with saturated aqueous NH$_4$Cl, and the solution was diluted with EtOAc; a small amount of water was added to dissolve the precipitated solids. The layers were separated, and the organic layer was washed with brine then dried with MgSO$_4$, filtered and concentrated to yield a light brown film (213 mg). The residue was taken up in 1M TBAF/THF solution (3.0 mL) and stirred at 50° C. for 3.5 hours. The reaction was diluted with EtOAc then washed successively with water and brine. The solution was dried with MgSO$_4$, filtered and concentrated giving an orange foam residue, which was purified by column chromatography (30 to 70% (0.02% v/v AcOH/EtOAc)/hexanes, 12 g SiO$_2$), to yield the title compound (157 mg, 0.250 mmol) as a white powder. $^1$H NMR (400 MHz, CDCl$_3$) δ 8.85 (1H, br s), 7.71 (1H, d, J=8.6 Hz), 7.19 (1H, dd, J=8.4, 2.4 Hz), 7.09 (1H, d, J=2.4 Hz), 6.97 (1H, dd, J=8.2, 2.0 Hz), 6.93 (1H, apparent d, J=8.0 Hz), 6.89 (1H, J=1.6 Hz), 5.86 (1H, ddd, J=15.1, 9.8, 2.5 Hz), 5.59 (1H, dd, J=15.1, 9.2 Hz), 4.41 (1H, q, 7.2 Hz), 4.09 (2H, apparent singlet), 3.99 (1H, dd, J=11.3, 6.0 Hz), 3.82 (1H, d, J=14.9 Hz), 3.70 (1H, d, J=14.5 Hz), 3.66 (1H, dd, J=9.4, 3.5 Hz), 3.42 (1H, dd, J=11.2, 6.2 Hz), 3.23 (3H, s), 3.01 (1H, dd, J=15.3, 10.2 Hz), 2.82-2.71 (2H, m), 2.50-2.30 (3H, m), 2.16-1.95 (6H, m), 1.87-1.80 (3H, m), 1.70-1.60 (2H, m), 1.56 (3H, d, J=8.0 Hz), 1.43-1.37 (1H, m); MS (ESI) m/z=628.9 [M+H]$^+$.

Example 2. (1S,3'R,6'R,7'R,8'E,11'R,12'R)-6-chloro-7'-methoxy-11'-(methoxymethyl)-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

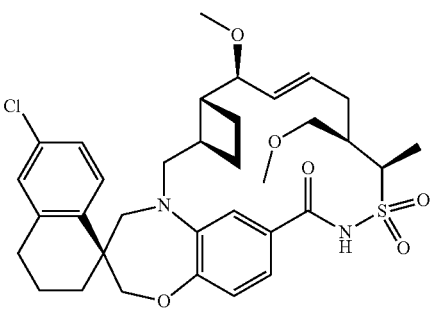

(1S,3'R,6'R,7'R,8'E,11'R,12'R)-6-chloro-11'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (7.1 mg, 0.011 mmol, Example 1) was dissolved in THF (0.5 mL). Sodium hydride, 60% dispersion in mineral oil (2.6 mg, 0.063 mmol) was added and the mixture was stirred for 30 minutes, then it was treated with iodomethane (2.1 μL, 0.034 mmol). As little reaction was initially observed, excess sodium hydride and iodomethane were added, resulting in complete conversion to the desired product by LC/MS analysis of the reaction mixture. The reaction was quenched with MeOH, and concentrated under reduced pressure. The residue was absorbed onto a plug of SiO$_2$, and then purified by column chromatography eluting with 40% (0.2% AcOH/EtOAc)/hexanes, to yield the bismethyleter product. $^1$H NMR analysis revealed the compound was contaminated with "grease." The solution was concentrated, and the residue was partitioned between MeCN and hexanes. The layers were separated, and the hexane layer extracted twice with MeCN. The combined MeCN layers were washed again with hexanes. The MeCN layer was concentrated to yield a white film, (4.8 mg, 7.46 μmol). $^1$H NMR (400 MHz, CDCl$_3$) δ 8.11 (1H, br s), 7.73 (1H, d, J=8.4 Hz), 7.21 (1H, dd, J=8.4, 2.0 Hz), 7.10 (1H, d, J=2.2 Hz), 6.91 (2H, m), 6.84 (1H, s), 5.84 (1H, ddd, J=15.0, 10.0, 2.9 Hz), 5.60 (1H, dd, J=15.0, 9.7 Hz), 4.37 (1H, q, J=4.1 Hz), 4.08 (2H, s), 3.82 (1H, dd, J=8.8, 2.9 Hz), 3.81 (1H, d, J=15.3 Hz), 3.69 (1H, d, J=14.3 Hz), 3.64 (1H, dd, J=9.0, 3.1 Hz), 3.33 (3H, s), 3.24 (1H, d, J=13.7 Hz), 3.23 (3H, s), 3.17 (1H, t, J=9.0 Hz), 2.99 (1H, dd, J=15.5, 10.0 Hz), 2.83-2.71 (2H, m), 2.61 (1H, dd, J=14.0, 10.0 Hz), 2.44 (1H, dq, J=9.5 (×3), 3.0 Hz), 2.36-2.27 (1H, m), 2.19-2.12 (1H, m), 2.05-1.94 (3H, m), 1.86-1.78 (3H, m), 1.68-1.61 (3H, m), 1.51 (3H, d, J=7.4 Hz), 1.43-1.36 (1H, m); MS (ESI) m/z=642.8 [M+H]$^+$.

Example 3. (1S,3'R,6'R,7'S,8'E,11'R,12'R)-6-chloro-11'-((1R)-1-hydroxyethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-11'-((1S)-1-hydroxyethyl)-7'-methoxy-12'-methyl-3,4-dihydro-2H,15'H-spiro[naphthalene-[20]oxa[13]thia[1,14]diazatetracyclo[14.7.2.0$^{3,6}$.0$^{19,24}$]pentacosa [8,16,18,24]tetraen]-15'-one 13',13'-dioxide

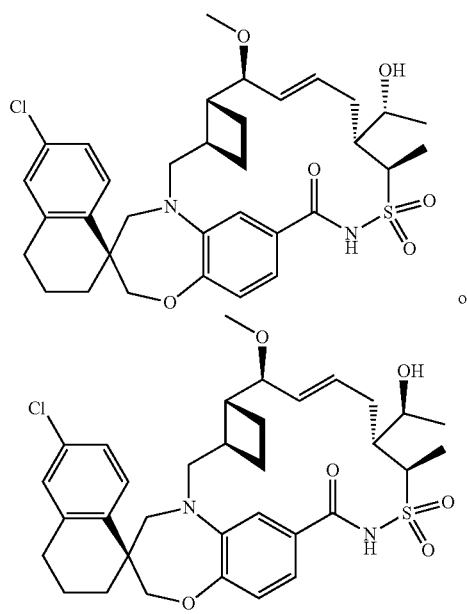

or

A mixture of (1S,3'R,6'R,7'R,8'E,11'R,12'R)-6-chloro-11'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (9.3 mg, 0.015 mmol, Example 1) and triethylamine (10 μL, 0.072 mmol) in DMSO (500 μL) was treated with pyridine sulfur trioxide (7.4 mg, 0.046 mmol). The reaction mixture was stirred at ambient temperature for 1 hour, and then was diluted with EtOAc. The resulting solution was washed with water and then brine (2×), dried over MgSO$_4$, filtered and concentrated to give a white film (10 mg). The residue was taken up in THF (0.5 mL), cooled in an ice bath and treated with MeMgBr (1.4 M in THF/PhMe, 1:3, 50 μL, 0.07 mmol). After 30 minutes, the reaction mixture was quenched by addition of saturated aqueous NH$_4$Cl. The mixture was partitioned between water and EtOAc. The layers were separated, and the aqueous layer was further extracted with EtOAc (3×). The combined extracts were dried over MgSO$_4$, filtered and concentrated to yield a white film. The film was purified by column chromatography eluting with 8:1 DCM:acetone on a 4 g SiO$_2$ column to provide one of the title compounds as the first eluting diastereomer (1.16 mg). $^1$H NMR (400 MHz, CD$_2$Cl$_2$) δ 8.31 (broad s, 1H), 7.75 (d, J=8.41 Hz, 1H), 7.21 (dd, J=8.5, 2.5 Hz, 1H), 7.13 (s, 1H), 6.90-7.04 (m, 3H), 5.80-5.91 (m, 1H), 5.59 (dd, J=16.7, 8.1 Hz, 1H), 4.33 (q, J=7.30 Hz, 1H), 4.17-4.09 (m, 2H), 4.09-4.00 (m, 1H), 3.85 (d, J=15.85 Hz, 1H), 3.73 (d, J=13.9 Hz, 1H), 3.67 (dd, J=8.7, 3.2 Hz, 1H), 3.29 (d, J=14.5 Hz, 1H), 3.22 (s, 3H), 3.08 (dd, J=10.07, 15.36 Hz, 1H), 2.88-2.72 (m, 2H), 2.52-2.32 (m, 2H), 2.15-1.79 (m, 4H), 1.76-1.66 (m, 1H), 1.62 (d, J=7.4 Hz, 3H), 1.57 (br. s., 6H), 1.50-1.39 (m, 1H), 1.20 (d, J=6.1 Hz, 3H); MS (ESI) m/z=642.8 [M+H]$^+$.

Example 4. (1S,3'R,6'R,7'S,8'E,11'R,12'R)-6-chloro-11'-((1R)-1-hydroxyethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-11'-((1S)-1-hydroxyethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

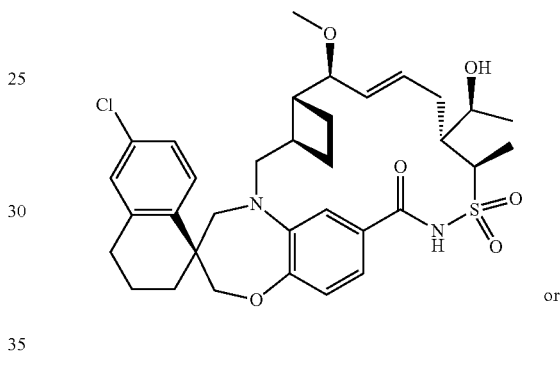

or

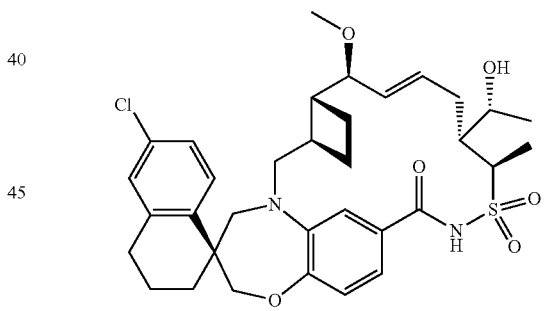

The title compound was synthesized as described for Example 3 and was isolated as the second eluting (slower) diastereomer (1.46 mg) in Example 3. $^1$H NMR (400 MHz, CD$_2$Cl$_2$) δ 8.07 (br. s., 1H), 7.71 (d, J=8.6 Hz, 1H), 7.17 (dd, J=8.4, 2.3 Hz, 1H), 7.09 (d, J=2.3 Hz, 1H), 6.94-6.87 (m, 2H), 6.84 (s, 1H), 5.90-5.79 (m, 1H), 5.62-5.52 (m, 1H), 4.50-4.42 (m, 1H), 4.34-4.27 (m, 1H), 4.13-4.04 (m, 2H), 3.82 (d, J=15.1 Hz, 1H), 3.70 (d, J=14.1 Hz, 1H), 3.62 (dd, J=9.2, 3.1 Hz, 1H), 3.25 (d, J=14.3 Hz, 1H), 3.18 (s, 3H), 3.03 (dd, J=15.4, 9.9 Hz, 1H), 2.84-2.69 (m, 2H), 2.49-2.23 (m, 4H), 2.09-2.01 (m, 1H), 2.00-1.90 (m, 2H), 1.88-1.68 (m, 2H), 1.64 (d, J=7.4 Hz, 3H), 1.30-1.24 (m, 5H), 1.19 (d, J=6.7 Hz, 3H); MS (ESI) m/z=642.8 [M+H]$^+$.

Example 5. (1S,3'R,6'R,7'S,8'E,11'R,12'R)-6-chloro-11'-(fluoromethyl)-7'-methoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

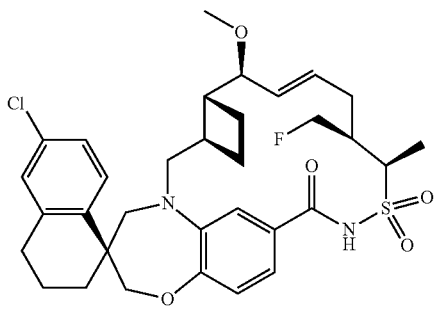

A solution of (1S,3'R,6'R,7'R,8'E,11'R,12'R)-6-chloro-11'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (9.7 mg, 0.015 mmol, Example 1) in 1,2-dichloroethane (500 μL) was treated with (diethylamino)sulfur trifluoride (5.09 μL, 0.039 mmol) at 0° C., which caused the colorless solution to become yellow. The solution was stirred for 15 minutes. The reaction solution was absorbed onto a plug of Sift and purified by column chromatography (10 to 100% EtOAc/hexanes with 0.02% AcOH, 4 g Sift) to give the title product (3.7 mg). ¹H NMR (400 MHz, CDCl₃) δ 8.18 (s, 1H), 7.70 (d, J=8.6 Hz, 1H), 7.19 (dd, J=2.2, 8.5 Hz, 1H), 7.10 (d, J=2.3 Hz, 1H), 6.96-6.89 (m, 2H), 6.86 (s, 1H), 5.85 (ddd, J=3.1, 10.1, 15.1 Hz, 1H), 5.62 (ddd, J=1.2, 9.4, 15.3 Hz, 1H), 4.73 (ddd, J=4.5, 9.4, 46.4 Hz, 1H), 4.53 (ddd, J=6.8, 9.4, 47.0 Hz, 1H), 4.44-4.38 (m, 1H), 4.15-4.06 (m, 2H), 3.82 (d, J=15.1 Hz, 1H), 3.70 (d, J=14.5 Hz, 1H), 3.65 (dd, J=3.1, 9.2 Hz, 1H), 3.23 (s, 3H), 3.01 (dd, J=10.3, 15.2 Hz, 1H), 2.86-2.70 (m, 2H), 2.60-2.41 (m, 2H), 2.39-2.26 (m, 2H), 2.25-2.20 (m, 1H), 2.21-2.08 (m, 1H), 2.07-1.91 (m, 2H), 1.90-1.77 (m, 2H), 1.72-1.52 (m, 7H), 1.40 (t, J=12.9 Hz, 1H); MS (ESI) m/z=631.2 [M+H]⁺.

Example 8. (1S,3'R,6'R,7'S,8'E,12'R)-6-chloro-4,4-difluoro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

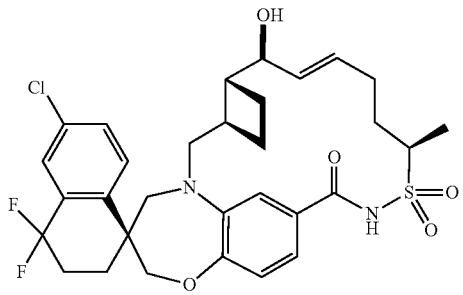

Step 1: (S)-6'-chloro-4',4'-difluoro-N—((R)-hex-5-en-2-ylsulfonyl)-5-(((1R,2R)-2-((S,E)-1-hydroxyhex-2-en-1-yl)cyclobutyl)methyl)-3',4',4',5-tetrahydro-2H,2'H-spiro[benzo[b][1,4]oxazepine-3,1'-naphthalene]-7-carboxamide

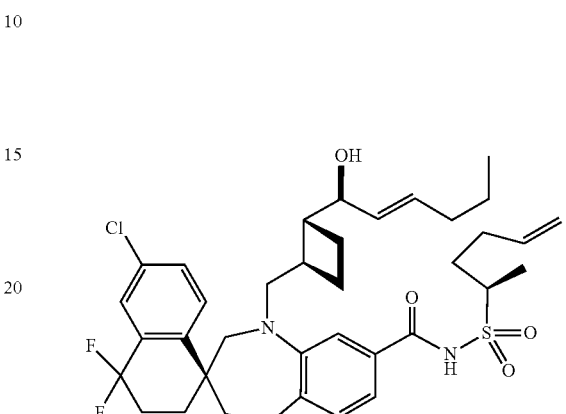

The title compound was prepared from Intermediate AA18 and Intermediate EE17 using a procedure similar to that of Example 6 Step 1.

Step 2: (1S,3'R,6'R,7'S,8'E,12'R)-6-chloro-4,4-difluoro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide To a stirred solution of (S)-6'-chloro-4',4'-difluoro-N—((R)-hex-5-en-2-ylsulfonyl)-5-(((1R,2R)-2-((S,E)-1-hydroxyhex-2-en-1-yl)cyclobutyl)methyl)-3',4',4',5-tetrahydro-2H,2'H-spiro[benzo[b][1,4]oxazepine-3,1'-naphthalene]-7-carboxamide (150 mg, 0.217 mmol, Step 1) in AcOH (5 mL) sealed and sparged with argon was added (1,3-dimesitylimidazolidin-2-ylidene)(2-isopropoxybenzylidene)ruthenium(VI) chloride (13.60 mg, 0.022 mmol). The reaction was pulled under vacuum and then again sparged with argon and set to stir for 3 h, after which the reaction was stripped of solvent and purified over silica with 20% acetone in hexanes to yield the title compound as a white solid (60 mg, 0.088 mmol, 40%). ¹H NMR (400 MHz, CD₂Cl₂) δ 7.80 (d, J=8.61 Hz, 1H), 7.62-7.72 (m, 1H), 7.47 (s, 1H), 6.91-7.05 (m, 3H), 5.77-5.94 (m, 1H), 5.61-5.77 (m, 1H), 4.23 (dd, J=4.11, 7.43 Hz, 1H), 4.12-4.19 (m, 2H), 4.02-4.10 (m, 1H), 3.87 (d, J=13.89 Hz, 1H), 3.73 (d, J=14.48 Hz, 1H), 3.21 (d, J=14.28 Hz, 1H), 2.98 (dd, J=9.39, 15.45 Hz, 1H), 2.27-2.54 (m, 5H), 2.11-2.23 (m, 2H), 2.10 (s, 2H), 2.00 (q, J=8.09 Hz, 1H),1.72-1.92 (m, 5H), 1.66 (q, J=9.32 Hz, 1H), 1.55 (d, J=7.04 Hz, 3H).

Example 9. (1S,3'R,6'R,7'S,8'E,11'S,12'R)-6-chloro-7'-(2-(3,3-difluoro-1-azetidinyl)ethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide Example 10. (1S,3'R,6'R,7'S,8'E,11'S,12'R)-6-chloro-7'-(2-(4,4-difluoro-1-piperidinyl)ethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one-13',13'-dioxide

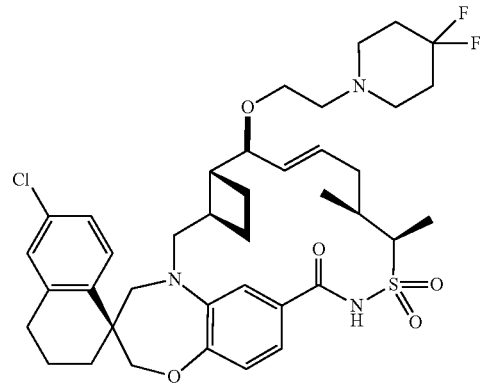

The title compound was prepared from (1S,3'R,6'R,7'S,8'E,11'S,12'R)-7'-(2-bromoethoxy)-6-chloro-11',12'-dimethyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (17 mg, 0.024 mmol, Example 14) using a procedure similar to that of Example 9. $^1$H NMR (400 MHz, CDCl$_3$) δ 7.69 (d, J=8.41 Hz, 1H), 7.19 (dd, J=2.25, 8.31 Hz, 1H), 7.10 (d, J=2.35 Hz, 1H), 6.88-6.97 (m, 2H), 6.82 (d, J=1.37 Hz, 1H), 5.82-5.96 (m, 1H), 5.82-5.95 (m, 1H), 5.52 (dd, J=9.39, 14.87 Hz, 1H), 4.30 (q, J=7.17 Hz, 1H), 4.09 (s, 2H), 3.74-3.87 (m, 3H), 3.70 (d, J=13.89 Hz, 1H), 3.52-3.63 (m, 1H), 3.17-3.29 (m, 3H), 3.01 (dd, J=10.07, 14.97 Hz, 1H), 2.72-2.84 (m, 2H), 2.28-2.50 (m, 1H), 2.09-2.24 (m, 1H), 1.93-2.06 (m, 2H), 1.74-1.88 (m, 1H), 1.67 (t, J=9.00 Hz, 1H), 1.50 (d, J=7.24 Hz, 3H), 1.32-1.46 (m, 1H), 1.06 (d, J=6.85 Hz, 3H).

Example 11. (1S,3'R,6'R,7'S,8'E,11'S,12'R)-6-chloro-11',12'-dimethyl-7'-(2-(phenylamino)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

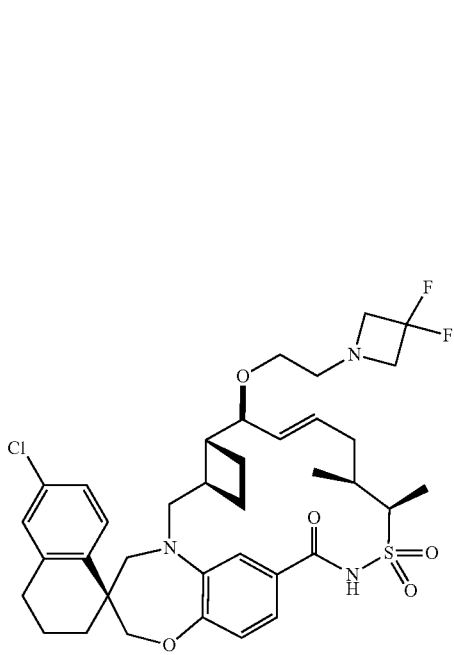

To a stirred solution of (1S,3'R,6'R,7'S,8'E,11'S,12'R)-7'-(2-bromoethoxy)-6-chloro-11',12'-dimethyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (17 mg, 0.024 mmol, Example 14) and 4,4-difluoroazetidine hydrochloride (37.9 mg, 0.241 mmol) in 250 μL DMSO was added triethylamine (50.3 μL, 0.361 mmol) and the reaction stirred at 50° C. overnight. The reaction was then cooled to rt, filtered and purified by prep HPLC to provide the title compound (1.5 mg, 2.01 μmol, 8.35% yield) as a white solid. $^1$H NMR (400 MHz, CD$_2$Cl$_2$) δ 8.07-8.37 (m, 1H), 7.70 (d, J=8.61 Hz, 1H), 7.17 (dd, J=2.35, 8.41 Hz, 1H), 7.09 (d, J=2.15 Hz, 1H), 6.92 (s, 2H), 6.81 (s, 1H), 5.76-5.95 (m, 1H), 5.51 (dd, J=9.59, 15.45 Hz, 1H), 4.25 (d, J=7.04 Hz, 1H), 4.08 (s, 2H), 3.78 (s, 3H), 3.69 (d, J=14.28 Hz, 1H), 3.51-3.61 (m, 1H), 3.42 (d, J=3.13 Hz, 2H), 3.24 (d, J=14.28 Hz, 1H), 2.97-3.08 (m, 1H), 2.72-2.85 (m, 2H), 2.70 (s, 1H), 2.38-2.50 (m, 1H), 2.28-2.38 (m, 1H), 1.92-2.23 (m, 6H), 1.64-1.88 (m, 4H), 1.44 (d, J=7.24 Hz, 3H), 1.34-1.41 (m, 1H), 1.02 (d, J=6.85 Hz, 3H).

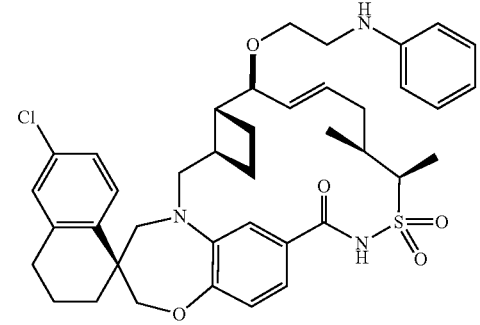

The title compound was prepared from (1S,3'R,6'R,7'S,8'E,11'S,12'R)-7'-(2-bromoethoxy)-6-chloro-11',12'-dimethyl-3,4-dihydro-2h,15'h-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 14) and aniline using a procedure similar to that of Example 9. ¹H NMR (500 MHz, CDCl₃) δ 7.70 (d, J=8.56 Hz, 1H), 7.16-7.23 (m, 3H), 7.10 (d, J=2.20 Hz, 1H), 6.89-6.98 (m, 2H), 6.86 (d, J=1.71 Hz, 1H), 6.72 (t, J=7.34 Hz, 1H), 6.64 (d, J=7.58 Hz, 2H), 5.71-5.88 (m, 1H), 5.53 (dd, J=9.29, 15.16 Hz, 1H), 4.30 (d, J=7.34 Hz, 1H), 4.11-4.18 (m, 4H), 4.09 (s, 2H), 3.79 (s, 1H), 3.76-3.79 (m, 1H), 3.70 (d, J=14.43 Hz, 1H), 3.62 (td, J=5.20, 10.15 Hz, 1H), 3.45-3.52 (m, 1H), 3.20-3.29 (m, 3H), 2.99 (dd, J=10.15, 15.28 Hz, 1H), 2.71-2.80 (m, 2H), 2.40-2.51 (m, 1H), 2.31-2.36 (m, 1H), 1.86-1.90 (m, 2H), 1.80-1.86 (m, 3H), 1.69-1.78 (m, 6H), 1.54-1.54 (m, 1H), 1.48 (d, J=7.09 Hz, 3H), 1.05 (s, 3H).

Example 12. (1S,3'R,6'R,7'S,8'E,11'S,12'R)-6-chloro-11',12'-dimethyl-7'-(2-(2-pyridinylamino)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

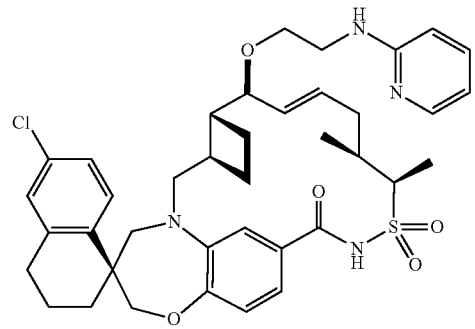

The title compound was prepared from (1S,3'R,6'R,7'S,8'E,11'S,12'R)-7'-(2-bromoethoxy)-6-chloro-11',12'-dimethyl-3,4-dihydro-2h,15'h-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 14) and pyridin-2-amine using a procedure similar to that of Example 9. ¹H NMR (500 MHz, CDCl₃) δ 8.36-8.39 (m, 1H), 8.05 (br. s., 1H), 7.77 (d, J=7.09 Hz, 2H), 7.69 (d, J=8.56 Hz, 1H), 7.26 (br. s., 1H), 7.14-7.20 (m, 1H), 7.09 (d, J=1.47 Hz, 1H), 6.86-6.95 (m, 3H), 6.85 (s, 1H), 6.72 (t, J=6.24 Hz, 1H), 5.73-5.92 (m, 1H), 5.50 (dd, J=8.80, 14.92 Hz, 1H), 4.29 (d, J=7.09 Hz, 1H), 4.08 (s, 2H), 3.76-3.91 (m, 3H), 3.61-3.74 (m, 2H), 3.48 (d, J=18.34 Hz, 4H), 3.22 (d, J=14.43 Hz, 1H), 3.00 (dd, J=10.03, 15.16 Hz, 1H), 2.78 (br. s., 3H), 2.43-2.56 (m, 2H), 2.23-2.34 (m, 3H), 1.77-1.86 (m, 2H), 1.73 (d, J=6.85 Hz, 2H), 1.56-1.69 (m, 2H), 1.49 (d, J=7.09 Hz, 4H), 1.27-1.42 (m, 2H), 1.05 (d, J=6.85 Hz, 3H).

Example 13. (1S,3'R,6'R,7'S,8'E,11'S,12'R)-6-chloro-11',12'-dimethyl-7'-(2-(methyl(2-pyridinyl)amino)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

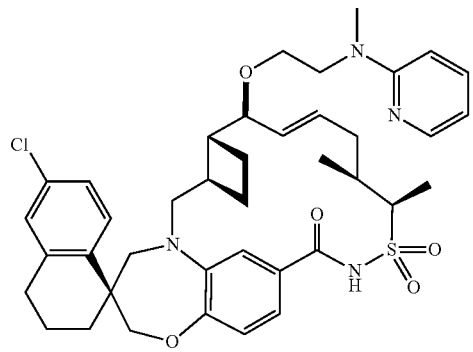

The title compound was prepared from (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 14) and N-methylpyridin-2-amine using a procedure similar to that of Example 9. ¹H NMR (500 MHz, CDCl₃) δ 8.12 (d, J=4.65 Hz, 1H), 7.55-7.76 (m, 2H), 7.10 (dd, J=2.20, 8.56 Hz, 1H), 7.02 (s, 1H), 6.89 (d, J=9.29 Hz, 1H), 6.79-6.85 (m, 2H), 6.67-6.79 (m, 2H), 5.71-5.87 (m, 1H), 5.33-5.48 (m, 1H), 4.17-4.27 (m, 1H), 3.98-4.05 (m, 2H), 3.53-3.79 (m, 6H), 3.48-3.48 (m, 1H), 3.37-3.47 (m, 1H), 3.20-3.34 (m, 3H), 3.09-3.19 (m, 2H), 2.86-2.87 (m, 1H), 2.86-3.00 (m, 2H), 2.15-2.41 (m, 4H), 1.86-2.12 (m, 7H), 1.72 (dd, J=2.20, 6.11 Hz, 2H), 1.48-1.68 (m, 3H), 1.37-1.45 (m, 3H), 0.92-1.04 (m, 3H).

Example 14. (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

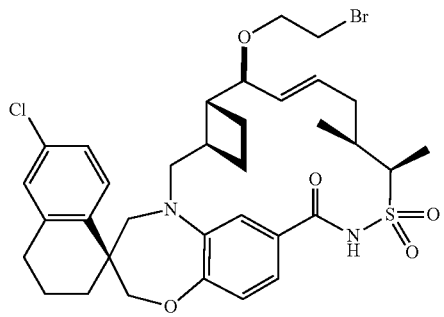

Step 1: 2-bromoethyl Trifluoromethanesulfonate

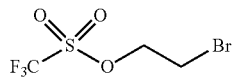

To a stirred solution of pyridine (0.712 mL, 8.80 mmol) in 80 mL at −20° C. in an ethylene glycol-dry ice bath was added trifluoromethanesulfonic anhydride (1.344 mL, 8.00 mmol) dropwise. The reaction was stirred for 10 min, followed by slow addition 2-bromoethanol (0.567 ml, 8.00 mmol), and the reaction was again left to stir, warming to RT for 10 minutes. The resulting suspension was filtered, concentrated (using a rotary evaporator, keeping the water bath temp below 20° C.) and petroleum ether (3 mL) was added. The mixture was filtered and concentrated again under reduced pressure to give the title product 2-bromoethyl trifluoromethanesulfonate (1.6 g, 6.23 mmol, 78%) as a clear colorless oil, which was stored cold in a freezer to prevent decomposition.

Step 2: (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide To a stirred solution 2-bromoethyl trifluoromethanesulfonate (844 mg, 3.28 mmol) and (1S,3'R,6'R,7'S,8'E,11'S,12'R)-6-chloro-7'-hydroxy-11',12'-dimethyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (246 mg, 0.411 mmol; Example 719, Step 2) in DCM was added 2,6-di-tert-butylpyridine (1386 μL, 6.16 mmol), sealed with a pressure release fitted cap and heated to 40° C. Over three hours, an additional five equivalents of 2-bromoethyl trifluoromethanesulfonate was added portionwise and was again heated to 60° C. After an additional hour of heating, the reaction was allowed to cool to RT, stripped of solvent and purified over silica using 20% acetone in hexanes to yield the title compound as a brown solid (210 mg, 0.297 mmol, 72.4%). $^1$H NMR (400 MHz, CDCl$_3$) δ 8.19 (br. s., 1H), 7.70 (d, J=8.61 Hz, 1H), 7.18 (dd, J=2.35, 8.41 Hz, 1H), 7.08-7.13 (m, 1H), 7.07 (s, 1H), 7.06-7.11 (m, 1H), 6.94 (d, J=0.78 Hz, 2H), 6.85-6.90 (m, 1H), 5.85 (ddd, J=3.33, 9.49, 15.16 Hz, 1H), 5.56 (dd, J=9.10, 15.16 Hz, 1H), 4.33 (q, J=7.11 Hz, 1H), 4.13 (q, J=7.24 Hz, 1H), 4.09 (s, 2H), 3.66-3.88 (m, 4H), 3.54-3.65 (m, 1H), 3.49 (q, J=6.91 Hz, 1H), 3.38-3.44 (m, 2H), 3.38-3.44 (m, 2H), 3.23 (d, J=14.28 Hz, 1H), 3.01 (dd, J=10.17, 15.26 Hz, 1H), 2.69-2.85 (m, 2H), 2.43-2.54 (m, 1H), 2.41-2.57 (m, 1H), 2.25-2.39 (m, 1H), 2.11 (d, J=9.39 Hz, 1H), 2.01 (s, 2H), 1.94-2.00 (m, 2H), 1.79-1.91 (m, 3H), 1.59-1.69 (m, 3H), 1.50 (d, J=7.24 Hz, 3H), 1.05 (d, J=6.85 Hz, 3H).

Example 15. 2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)ethanesulfonamide

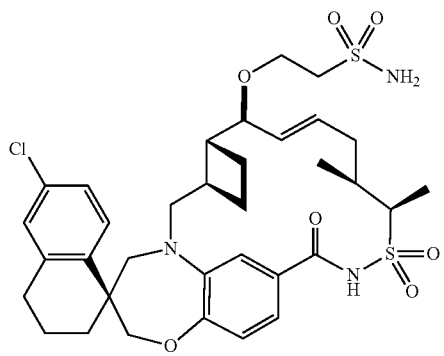

The title compound (5 mg, 7.08 μmol, 13%) was prepared from (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 14) using procedures similar to those described for Example 18, Steps 6-8 with the exception that the leaving group in Example 14 was the bromide rather than the mesylate. $^1$H NMR (500 MHz, CDCl$_3$) δ 7.88-7.98 (m, 1H), 7.69 (d, J=8.56 Hz, 1H), 7.16-7.21 (m, 1H), 7.19 (dd, J=2.20, 8.56 Hz, 1H), 7.10 (d, J=2.20 Hz, 1H), 6.89-6.96 (m, 2H), 6.84 (d, J=1.71 Hz, 1H), 5.91 (ddd, J=3.18, 9.84, 15.10 Hz, 1H), 5.55 (dd, J=9.29, 15.16 Hz, 1H), 4.32 (q, J=7.25 Hz, 1H), 4.08-4.13 (m, 2H), 3.82-3.96 (m, 3H), 3.65-3.78 (m, 2H), 3.34 (dt, J=4.40, 7.09 Hz, 2H), 3.23 (d, J=14.18 Hz, 1H), 3.02 (dd, J=10.15, 15.28 Hz, 1H), 2.72-2.86 (m, 2H), 2.41-2.51 (m, 1H), 2.35 (quin, J=9.17 Hz, 1H), 2.03-2.24 (m, 4H), 1.88 (d, J=7.34 Hz, 3H), 1.72-1.76 (m, 3H), 1.61-1.63 (m, 3H), 1.50-1.51 (m, 3H), 1.07 (s, 3H).

Example 16. (1S,3'R,6'R,7'S,9'E,11'S,12'R)-6-chloro-11',12'-dimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide

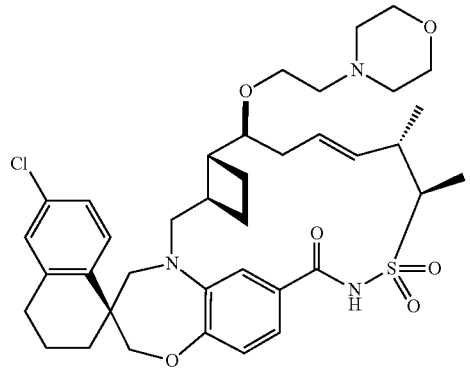

Step 1: (1S,3'R,6'R,7'S,9'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide Example 17. (1S,3'R,6'R,7'S,9'E,11'S,12'R)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide

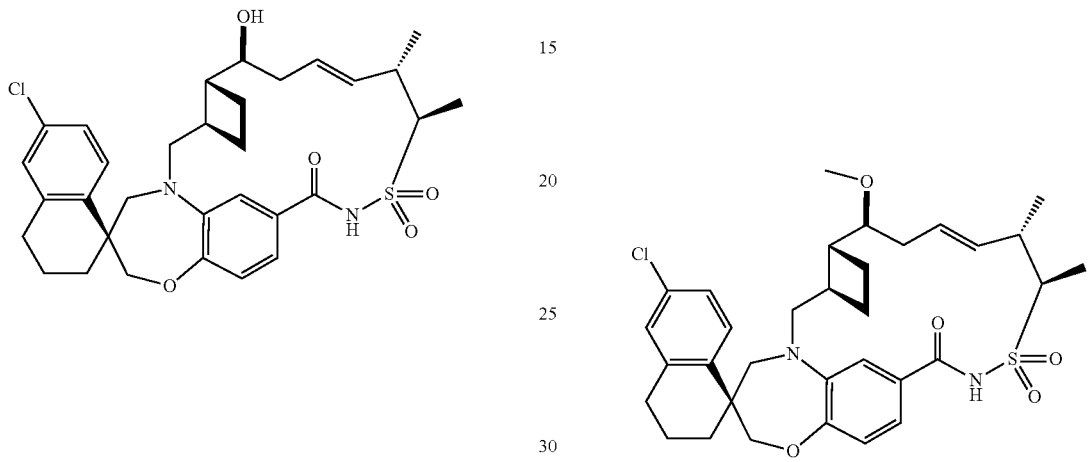

The title compound was prepared from Intermediate AA13A and (2S,3R)—N,N-bis(4-methoxybenzyl)-3-methylhex-5-ene-2-sulfonamide using procedures similar to those described for Example 556, Steps 1-4.

Step 2: (1S,3'R,6'R,7'S,9'E,11'S,12'R)-6-chloro-11',12'-dimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide To a stirred solution (1S,3'R,6'R,7'S,9'E,11'S 12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (15 mg, 0.025 mmol, Example 16, Step 1) in 350 μL DMF was added 4-(2-bromoethyl)morpholine hydrobromide (34.4 mg, 0.125 mmol), followed by sodium hydride (10.01 mg, 0.250 mmol). The reaction was stirred overnight at rt. The reaction mixture was then diluted with a few drops of water, followed by 1.5 mL DMSO, and purified directly by preparative HPLC using a 75% isocratic method over 25 min. $^1$H NMR (400 MHz, CDCl$_3$) δ 7.69 (d, J=8.41 Hz, 1H), 7.19 (dd, J=2.25, 8.31 Hz, 1H), 7.10 (d, J=2.35 Hz, 1H), 6.88-6.97 (m, 2H), 6.82 (d, J=1.37 Hz, 1H), 5.82-5.96 (m, 1H), 5.82-5.95 (m, 1H), 5.52 (dd, J=9.39, 14.87 Hz, 1H), 4.30 (q, J=7.17 Hz, 1H), 4.09 (s, 2H), 3.74-3.87 (m, 3H), 3.70 (d, J=13.89 Hz, 1H), 3.52-3.63 (m, 1H), 3.17-3.29 (m, 3H), 3.01 (dd, J=10.07, 14.97 Hz, 1H), 2.72-2.84 (m, 2H), 2.28-2.50 (m, 1H), 2.09-2.24 (m, 1H), 1.93-2.06 (m, 2H), 1.74-1.88 (m, 1H), 1.67 (t, J=9.00 Hz, 1H), 1.50 (d, J=7.24 Hz, 3H), 1.32-1.46 (m, 1H), 1.06 (d, J=6.85 Hz, 3H).

To a small vial equipped with a stirbar containing a solution of (1S,3'R,6'R,7'S,9'E,11'S,12'R)-6-chloro-7'-hydroxy-11',12'-dimethyl-3,4-dihydro-2H,15'H-SPIRO[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (15 mg, 0.025 mmol, Example 16, Step 1) in 200 μL DCE was added methyl trifluoromethanesulfonate (4.11 μL, 0.038 mmol) and 2,6-di-tert-butylpyridine (11.97 mg, 0.063 mmol). The vial was sealed and the mixture stirred at rt overnight, after which the mixture was diluted with 1.5 mL of DMSO and purified by preparative HPLC to yield the title compound as a white solid (3 mg, 4.89 mmol, 19% yield). $^1$H NMR (400 MHz, CDCl$_3$) δ 9.92-10.29 (m, 1H), 7.71 (d, J=8.61 Hz, 1H), 7.46 (dd, J=1.96, 8.22 Hz, 1H), 7.18 (dd, J=2.35, 8.61 Hz, 1H), 7.10 (d, J=2.35 Hz, 1H), 6.96-7.03 (m, 2H), 5.47-5.67 (m, 1H), 5.31-5.38 (m, 1H), 4.13-4.15 (m, 2H), 4.14 (s, 2H), 3.64-3.71 (m, 2H), 3.63 (s, 3H), 3.53-3.60 (m, 1H), 3.44-3.51 (m, 1H), 3.28-3.37 (m, 1H), 2.73-2.82 (m, 2H), 2.55 (d, J=6.85 Hz, 1H), 2.39 (br. s., 1H), 2.06-2.15 (m, 2H), 1.80-1.98 (m, 4H), 1.65-1.72 (m, 1H), 1.59 (d, J=7.04 Hz, 3H), 1.08 (d, J=6.65 Hz, 3H).

Example 18. (1S,3'R,6'R,7'R,11'S)-6-chloro-7'-methoxy-3,4-dihydro-2H,15'H-spiro[naphthalene-1,22'-[20]oxa[13]thia[1,14]diazapentacyclo[14.7.2.2$^{8,11}$.0$^{3,6}$.0$^{19,24}$]heptacosa[8,16,18,24]tetraen]-15'-one 13,13' dioxide or (1S,3'R,6'R,7'R,11'R)-6-chloro-7'-methoxy-3,4-dihydro-2H,15'H-spiro[naphthalene-1,22'-[20]oxa[13]thia[1,14]diazapentacyclo[14.7.2.2$^{8,11}$.0$^{3,6}$.0$^{19,24}$]heptacosa[8,16,18,24]tetraen]-15'-one 13,13' dioxide or (1S,3'R,6'R,7'S,11'S)-6-chloro-7'-methoxy-3,4-dihydro-2H,15'H-spiro[naphthalene-1,22'-[20]oxa[13]thia[1,14]diazapentacyclo[14.7.2.2$^{8,11}$.0$^{3,6}$.0$^{19,24}$]heptacosa[8,16,18,24]tetraen]-15'-one 13,13' dioxide or (1S,3'R,6'R,7'S,11'R)-6-chloro-7'-methoxy-3,4-dihydro-2H,15'H-spiro[naphthalene-1,22'-[20]oxa[13]thia[1,14]diazapentacyclo[14.7.2.2$^{8,11}$.0$^{3,6}$.0$^{19,24}$]heptacosa[8,16,18,24]tetraen]-15'-one 13,13' dioxide

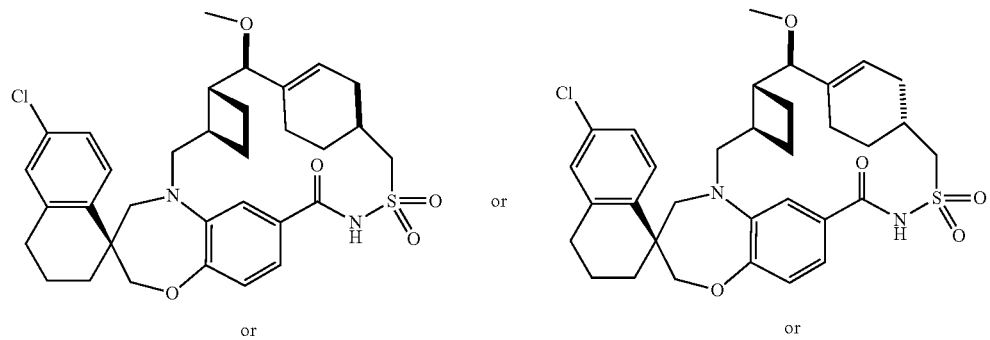

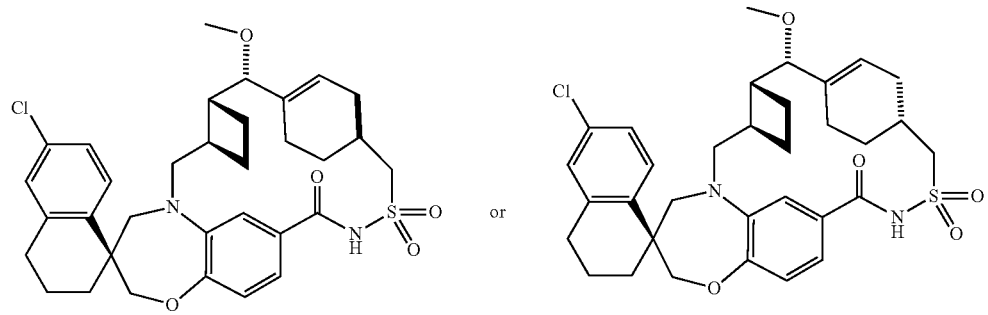

Step 1: (S)-ethyl 4-(((trifluoromethyl)sulfonyl)oxy)cyclohex-3-enecarboxylate and (R)-ethyl 4-(((trifluoromethyl)sulfonyl)oxy)cyclohex-3-enecarboxylate

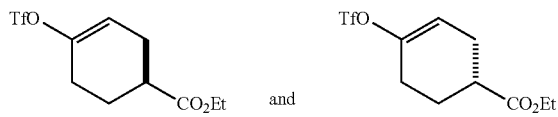 [SMILES: CCOC(=O)[C@@H]1CC=C(OS(=O)(=O)C(F)(F)F)CC1 ; CCOC(=O)[C@H]1CC=C(OS(=O)(=O)C(F)(F)F)CC1]

A stirred solution of ethyl 4-oxocyclohexanecarboxylate (10.6 g, 62.3 mmol) and 2,6-di-tert-butyl-4-methylpyridine (15.35 g, 74.7 mmol) under argon was cooled to −78° C. in a dry ice bath, followed by addition of trifluoromethanesulfonic anhydride (11.87 mL, 62.3 mmol). The reaction was stirred, warming to rt, for 40 hours. The mixture was then poured into ice water, diluted with saturated aqueous sodium bicarbonate solution, extracted with EtOAc (3×), washed with water and brine, dried with sodium sulfate, filtered and then concentrated. The residue was purified via column chromatography over a 220 g isco column eluting with 10% ethyl acetate/hexanes to yield a mixture of (S)-ethyl 4-(((trifluoromethyl)sulfonyl)oxy)cyclohex-3-enecarboxylate and (R)-ethyl 4-(((trifluoromethyl)sulfonyl)oxy)cyclohex-3-enecarboxylate (9 g, 29.8 mmol, 47.8% yield) as a brown oil.

Step 2: (S)-methyl 6'-chloro-5-(((1R,2R)-2-((R)—((S)-4-(ethoxycarbonyl)cyclohex-1-en-1-yl)(hydroxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)—((R)-4-(ethoxycarbonyl)cyclohex-1-en-1-yl)(hydroxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)—((S)-4-(ethoxycarbonyl)cyclohex-1-en-1-yl)(hydroxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)—((R)-4-(ethoxycarbonyl)cyclohex-1-en-1-yl)(hydroxy)methyl)cyclobutyl)methyl)-3',4,4',5-tetrahydro-2H,2'H-spiro[benzo[b][1,4]oxazepine-3,1'-naphthalene]-7-carboxylate

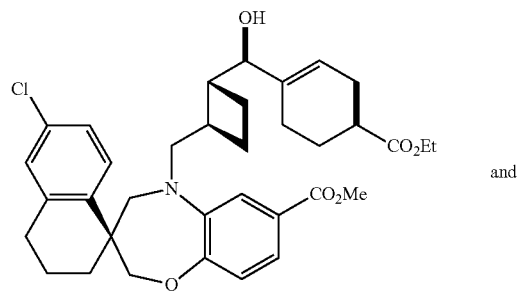
and
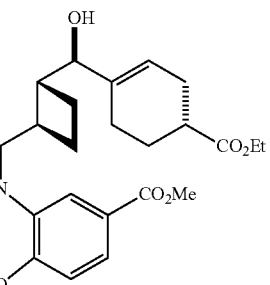
and
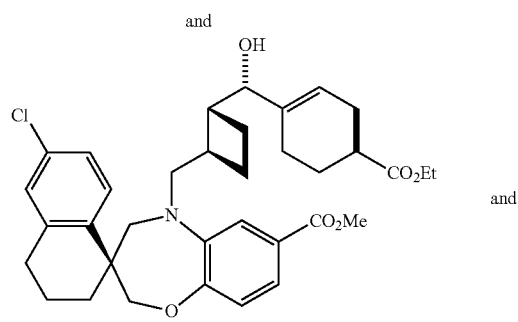
and
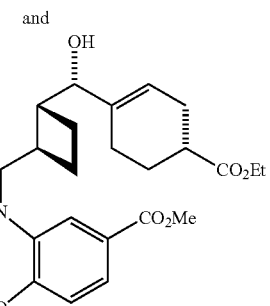

Nickel(II) chloride (0.285 g, 2.203 mmol) and chromium (II) chloride (16.24 g, 132 mmol) were added to a heat-gun dried 250 ml round bottom flask with heat dried stirbar, and the flask was immediated sealed and flushed with argon. The flask containing the dry reagents was place in an ice bath, and 45 mL fresh dry DMF was added, with stirring. The solvent was sparged with argon, and the flask removed from the bath. The solids were stirred, and then sonicated, until completely dissolved.

A mixture of (S)-ethyl 4-(((trifluoromethyl)sulfonyl)oxy)cyclohex-3-enecarboxylate and (R)-ethyl 4-(((trifluoromethyl)sulfonyl)oxy)cyclohex-3-enecarboxylate (from Step 1) and (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (2 g, 4.41 mmol, Intermediate AA11A, Step 20A) were added to a separate heat dried 250 mL flask with stir bar, and sealed, and again flushed with argon. Once the solids in the chromium nickel solution were completely dissolved, the solution was transferred to the second flask by cannula, and the reaction was stirred with an argon sparge for 1 hour. The mixture was poured into 500 mL 0.1 N aqueous EDTA solution, and the resulting purple mixture was stirred 0.5 hour, and then extracted with $Et_2O$ (3×). The ethereal layers were washed with water (2×) and brine (2×), dried over sodium sulfate, filtered and concentrated. The residue was purified via column chromatography eluting with 10% EA:Hex (containing 0.5% AcOH), to recover (S)-methyl 6'-chloro-5-(((1R,2R)-2-((R)—((S)-4-(ethoxy carbonyl)cyclohex-1-en-1-yl)(hydroxy)methyl)cyclobutyl)methyl)-3',4,4',5-tetrahydro-2h,2'h-spiro[benzo[b][1,4]oxazepine-3,1'-naphthalene]-7-carboxylate and (S)-methyl 6'-chloro-5-(((1R,2R)-2-((R)—((R)-4-(ethoxycarbonyl)cyclohex-1-en-1-yl)(hydroxy)methyl)cyclobutyl)methyl)-3',4,4',5-tetrahydro-2h,2'h-spiro[benzo[b][1,4]oxazepine-3,1'-naphthalene]-7-carboxylate and (S)-methyl 6'-chloro-5-(((1R,2R)-2-((S)—((S)-4-(ethoxycarbonyl)cyclohex-1-en-1-yl)(hydroxy)methyl)cyclobutyl)methyl)-3',4,4',5-tetrahydro-2h,2'h-spiro[benzo[b][1,4]oxazepine-3,1'-naphthalene]-7-carboxylate and (S)-methyl 6'-chloro-5-(((1R,2R)-2-((S)—((R)-4-(ethoxycarbonyl)cyclohex-1-en-1-yl)(hydroxy)methyl)cyclobutyl)methyl)-3',4,4',5-tetrahydro-2h,2'h-spiro[benzo[b][1,4]oxazepine-3,1'-naphthalene]-7-carboxylate as yellow oil (2.68 g, 4.41 mmol).

Step 3: (S)-methyl 6'-chloro-5-(((1R,2R)-2-((R)—((S)-4-(ethoxycarbonyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)—(R)-4-(ethoxycarbonyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and: (S)-methyl 6'-chloro-5-(((1R,2R)-2-((S)—((S)-4-(ethoxycarbonyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and: (S)-methyl 6'-chloro-5-(((1R,2R)-2-((S)—((R)-4-(ethoxycarbonyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate

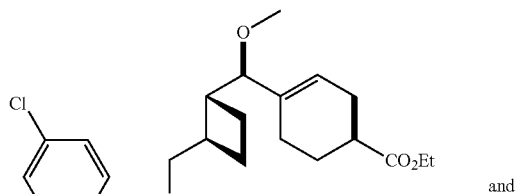

and

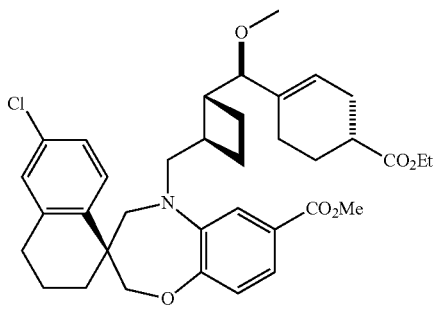

and

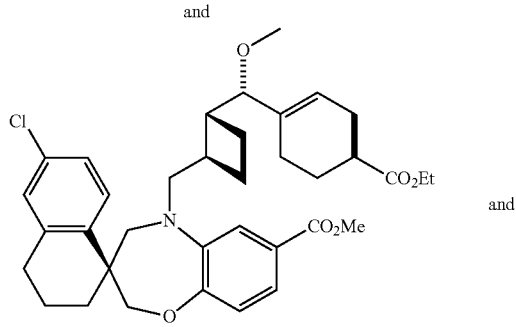

and

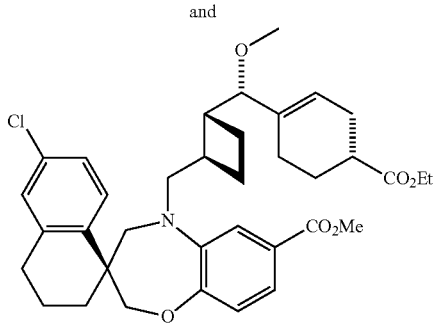

To a stirred solution mixture (S)-methyl 6'-chloro-5-(((1R,2R)-2-((R)-((S)-4-(ethoxycarbonyl)cyclohex-1-en-1-yl)(hydroxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)—((R)-4-(ethoxycarbonyl)cyclohex-1-en-1-yl)(hydroxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)—((S)-4-(ethoxycarbonyl)cyclohex-1-en-1-yl)(hydroxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)—((R)-4-(ethoxycarbonyl)cyclohex-1-en-1-yl)(hydroxy)methyl)cyclobutyl)methyl)-3',4,4',5-tetrahydro-2h,2'h-spiro[benzo[b][1,4]oxazepine-3,1'-naphthalene]-7-carboxylate (2.68 g, 4.41 mmol) and 2,6-di-tert-butylpyridine (0.706 mL, 5.29 mmol) in DCM was added methyl trifluoromethanesulfonate (0.579 mL, 5.29 mmol) and the reaction was heated to 40° C. Over the course of 3 hours an additional two equivalents of methyl trifluoromethanesulfonate and two equivalents of 2,6-di-tert-butylpyridine were added to drive the reaction to completion. The reaction was allowed to cool to RT, and two equivalents of triethylamine was added to quench any residual methyl trifluoromethanesulfonate. The mixture was loaded onto silica and purified over a 40 g isco column eluting with a gradient of 5-50% ethyl acetate/hexane (containing 0.5% AcOH) to yield (S)-methyl 6'-chloro-5-(((1R,2R)-2-((R)—((S)-4-(ethoxycarbonyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)—((R)-4-(ethoxycarbonyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)—((S)-4-(ethoxycarbonyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7- carboxylate and (S)-methyl 6'-chloro-5-((((1r,2r)-2-((s)-((r)-4-(ethoxycarbonyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate (2.2 g, 3.54 mmol).

Step 4: (S)-methyl 6'-chloro-5-((((1R,2R)-2-((R)—((S)-4-(hydroxymethyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-((((1R,2R)-2-((R)—(R)-4-(hydroxymethyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-((((1R,2R)-2-((S)—((S)-4-(hydroxymethyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-((((1R,2R)-2-((S)—(R)-4-(hydroxymethyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate

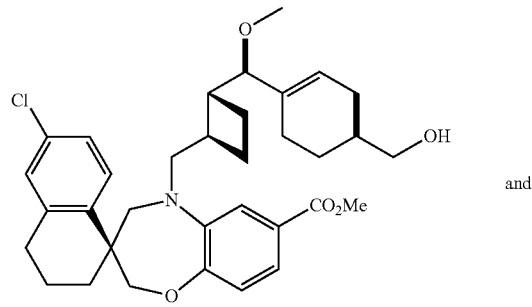

and

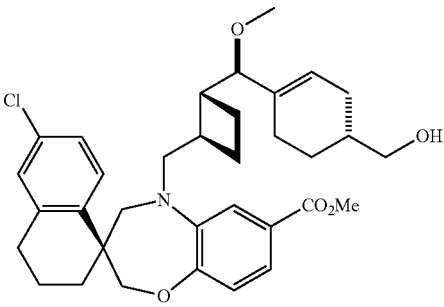

and

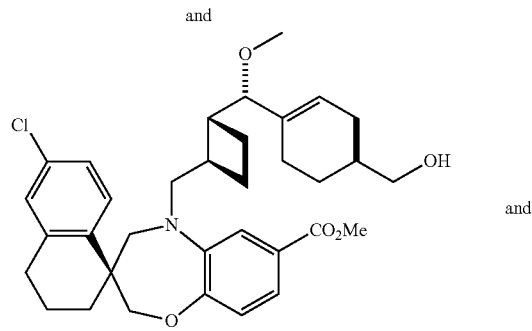

and

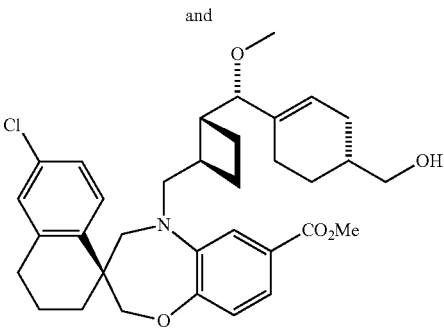

To a stirred solution (S)-methyl 6'-chloro-5-((((1R,2R)-2-((R)—((S)-4-(ethoxycarbonyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-((((1R,2R)-2-((R)—((R)-4-(ethoxy carbonyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-((((1R,2R)-2-((S)—((S)-4-(ethoxycarbonyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-((((1R,2R)-2-((S)—((R)-4-(ethoxycarbonyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate (2.2 g, 3.54 mmol) in THF at 0° C. with one equivalent MeOH was added a freshly made aqueous solution of lithium borohydride (0.039 g, 1.768 mmol) (0.1 g/mL such that LiBH$_4$ solids fully dissolved in THF), and the reaction was stirred, warming to RT for 15 minutes, and then heating to 50° C. for 15 minutes.

This procedure was repeated for several iterations, eventually adding a total of 10 equivalents of lithium borohydride. After stirring for 1 additional hour at 50° C., the reaction was cooled to 0° C. in an ice bath, and carefully quenched with 10 ml 10% acetic acid in THF, followed by water. The mixture was stirred for 0.5 hr, warming to RT, and was then extracted with EtOAc (3x), washed with water and brine, dried over sodium sulfate and purified over a 40 g isco column eluting with 25% ethyl acetate/hexane to yield (S)-methyl 6'-chloro-5-((((1R,2R)-2-((R)—(S)-4-(hydroxymethyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)—(R)-4-(hydroxymethyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)—(S)-4-(hydroxymethyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)—(R)-4-(hydroxymethyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate (635 mg, 1.095 mmol).

Step 5: (S)-methyl 6'-chloro-5-((((1R,2R)-2-((R)-methoxy((S)-4-(((methylsulfonyl)oxy)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy((R)-4-(((methylsulfonyl)oxy)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((S)-4-(((methylsulfonyl)oxy)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((R)-4-(((methylsulfonyl)oxy)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate

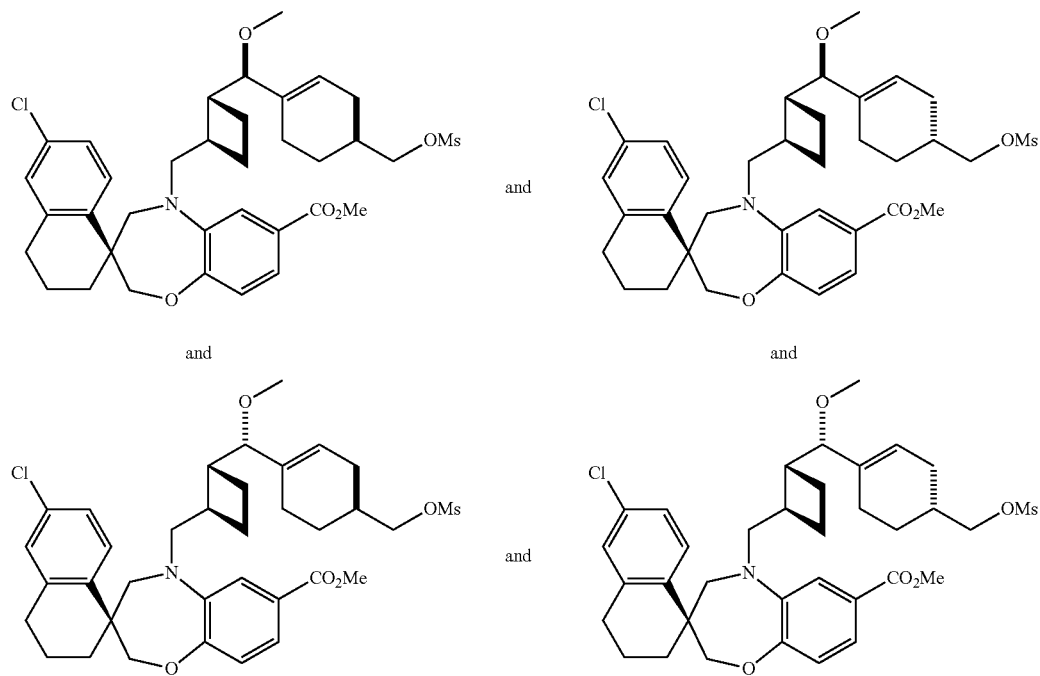

To a stirring solution of (S)-methyl 6'-chloro-5-(((1R,2R)-2-((R)—((S)-4-(hydroxymethyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)—((R)-4-(hydroxymethyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)—((S)-4-(hydroxymethyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)—((R)-4-(hydroxymethyl)cyclohex-1-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate (635 mg, 1.095 mmol) in 5 mL DCM cooled to 0° C. in an ice bath was added triethylamine (305 µL, 2.189 mmol), followed by dropwise addition methanesulfonyl chloride (128 µL, 1.642 mmol). The reaction was warmed to rt for 1 hr, diluted with saturated aqueous sodium bicarbonate solution, extracted into DCM, washed with water and 2'H-spiro[benzo[b][1,4]oxazepine-3,1'-naphthalene]-7-carboxylate (720 mg, 1.094 mmol).

Step 6: (S)-methyl 6'-chloro-5-(((1R,2R)-2-((R)-methoxy((S)-4-((pyrimidin-2-ylthio)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy((R)-4-((pyrimidin-2-ylthio)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((S)-4-((pyrimidin-2-ylthio)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((R)-4-((pyrimidin-2-ylthio)methyl)cyclohex-1-en-1-yl)methyl)cyclobutyl)methyl)-3',4,4',5-tetrahydro-2H,2'H-carboxylate

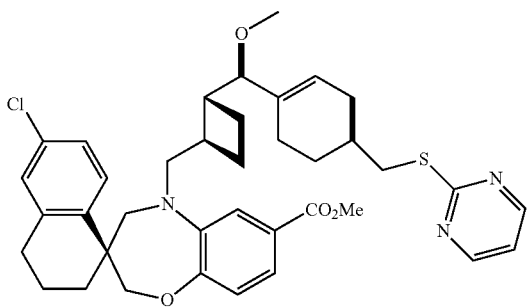

and

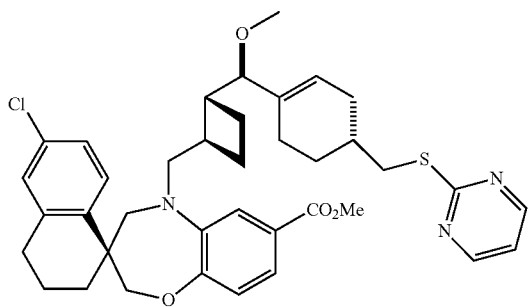

and

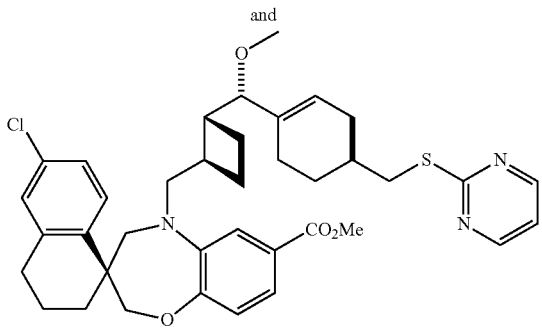

and

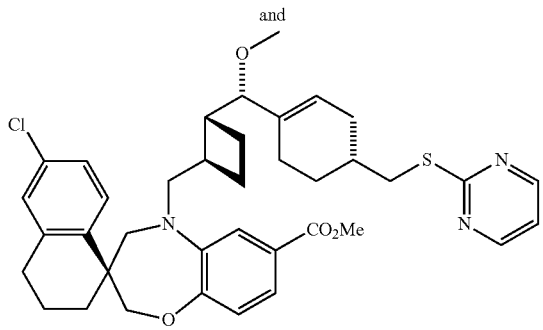

brine, dried over sodium sulfate, filtered and then concentrated to yield (S)-methyl 6'-chloro-5-(((1R,2R)-2-((R)-methoxy((S)-4-(((methylsulfonyl)oxy)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy ((R)-4-(((methylsulfonyl)oxy)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((S)-4-(((methylsulfonyl)oxy)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy ((R)-4-(((methylsulfonyl)oxy)methyl)cyclohex-1-en-1-yl)methyl)cyclobutyl)methyl)-3',4,4',5-tetrahydro-2H, To a stirred solution of (S)-methyl 6'-chloro-5-(((1R,2R)-2-((R)-methoxy ((S)-4-(((methyl sulfonyl)oxy)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy ((R)-4-(((methyl sulfonyl)oxy)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((S)-4-(((methyl sulfonyl)oxy)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((R)-4-(((methyl sulfonyl)oxy)methyl)cyclohex-1-en-1-yl)methyl)cyclobutyl)methyl)-3',4,4',5-tetrahydro-2H,2'H-spiro[benzo[b][1,4]oxazepine-3,1'- naphthalene]-7-carboxylate (720 mg, 1.094 mmol) in 2 mL dry DMF was added potassium carbonate (227 mg, 1.641 mmol), followed by pyrimidine-2-thiol (129 mg, 1.149 mmol) and the reaction was stirred at rt for 40 hrs. The reaction was then diluted with water, extracted with Et₂O (2×), washed with water (2×) and brine (2×), dried over sodium sulfate and filtered to yield (S)-methyl 6'-chloro-5-(((1R,2R)-2-((R)-methoxy ((S)-4-((pyrimidin-2-ylthio)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy ((R)-4-((pyrimidin-2-ylthio)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy ((S)-4-((pyrimidin-2-ylthio)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy ((R)-4-((pyrimidin-2-ylthio)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate (675 mg, 1.001 mmol, 92% yield) as a yellow solid.

Step 7: (S)-methyl 6'-chloro-5-(((1R,2R)-2-((R)-methoxy((S)-4-((pyrimidin-2-ylsulfonyl)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy((R)-4-((pyrimidin-2-ylsulfonyl)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((S)-4-((pyrimidin-2-ylsulfonyl)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((R)-4-((pyrimidin-2-ylsulfonyl)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate

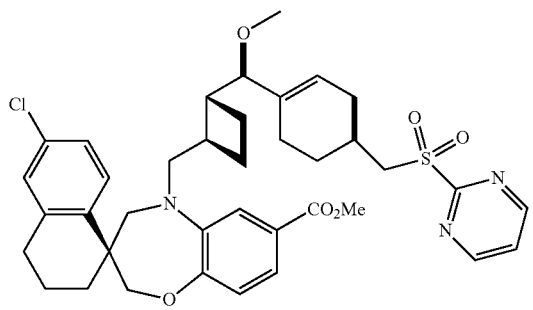

and

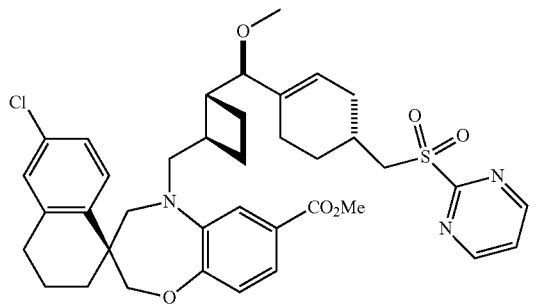

and

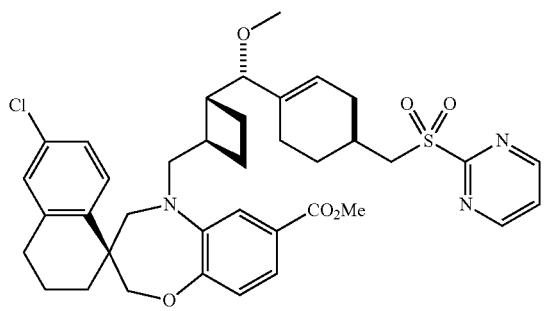

and

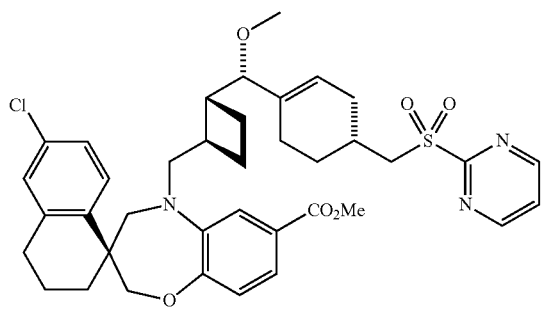

To a stirred solution of ((S)-methyl 6'-chloro-5-(((1R,2R)-2-((R)-methoxy((S)-4-((pyrimidin-2-ylthio)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy ((R)-4-((pyrimidin-2-ylthio)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy ((S)-4-((pyrimidin-2-ylthio)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy ((R)-4-((pyrimidin-2-ylthio)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate (375 mg, 0.556 mmol) in 2.25 mL dry DCM at 0° C. in an ice bath was added mCPBA (249 mg, 1.112 mmol), and the reaction was stirred for 0.5 h. The reaction was then removed from the bath and warmed to RT over 0.5 h. The reaction was again cooled to 0° C., one additional equivalent of mCPBA was added, and the reaction was stirred, warming to RT over 1 hour. The reaction was then concentrated and purified over silica eluting with 20% acetone in hexane to yield (S)-methyl 6'-chloro-5-(((1R,2R)-2-((R)-methoxy((S)-4-((pyrimidin-2-ylsulfonyl)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy((R)-4-((pyrimidin-2-ylsulfonyl)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((S)-4-((pyrimidin-2-ylsulfonyl)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((R)-4-((pyrimidin-2-ylsulfonyl)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate (160 mg, 0.227 mmol).

Step 8: (S)-methyl 6'-chloro-5-(((1R,2R)-2-((R)-methoxy((S)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy((R)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((S)-4-(sulfamoylmethyl)cyclohex-1-en-1-yl)methyl)cyclobutyl)methyl)-3',4,4',5-tetrahydro-2H,2'H-carboxylate and (S)-methyl 6'-chloro-5-(((1R,2R)-2-((S)-methoxy((R)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate

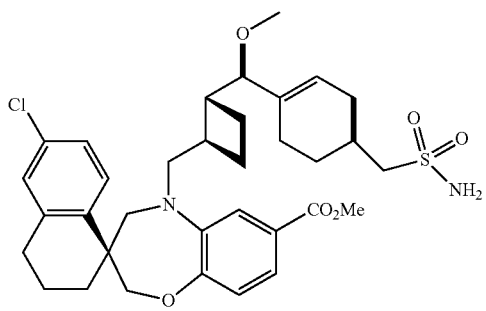

and

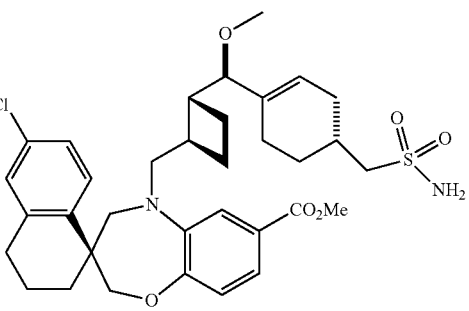

and

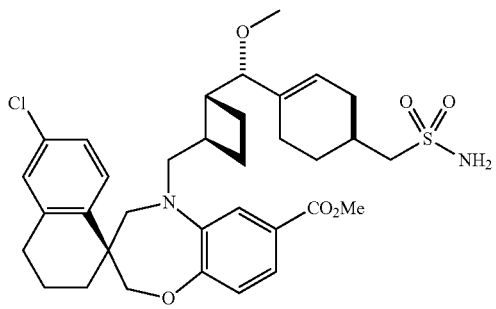

and

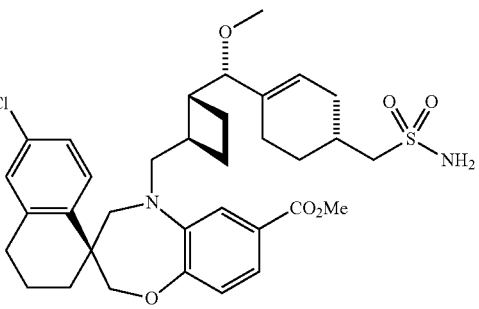

To a stirred solution of (S)-methyl 6'-chloro-5-(((1R,2R)-2-((R)-methoxy((S)-4-((pyrimidin-2-ylsulfonyl)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy((R)-4-((pyrimidin-2-ylsulfonyl)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((S)-4-((pyrimidin-2-ylsulfonyl)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy ((R)-4-((pyrimidin-2-ylsulfonyl)methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate (157 mg, 1.133 mmol) in MeOH with $K_2CO_3$, (Aminooxy)sulfonic acid (128 mg, 1.133 mmol) was added and the reaction was stirred overnight. The reaction was stripped of solvent, diluted with EtOAc and water, extracted into EtOAc, washed with water and brine, dried over sodium sulfate and then concentrated to yield (S)-methyl 6'-chloro-5-(((1R,2R)-2-((R)-methoxy((S)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy ((R)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((S)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy ((R)-4-(sulfamoyl methyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate (146 mg, 0.227 mmol, 100%) as a yellow solid.

Step 9: (S)-6'-chloro-5-(((1R,2R)-2-((R)-methoxy ((S)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((R)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-(S)-methoxy((S)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((S)-methoxy((R)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylic Acid

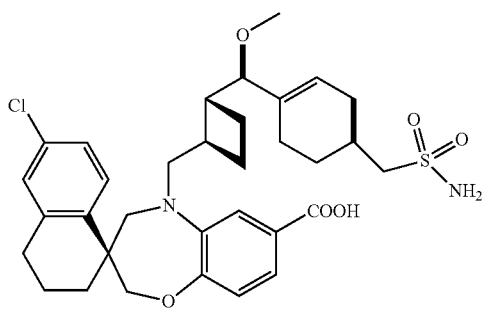

and

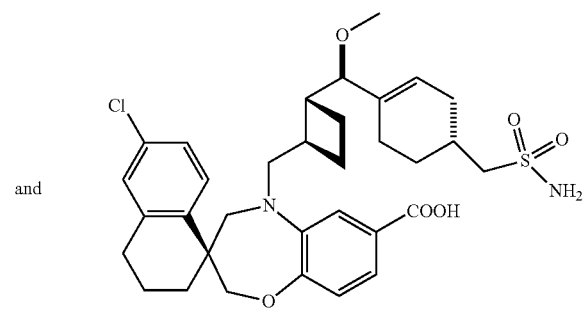

and

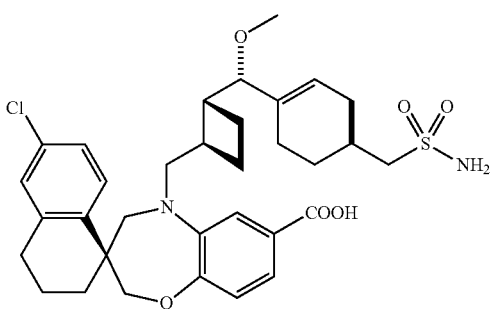
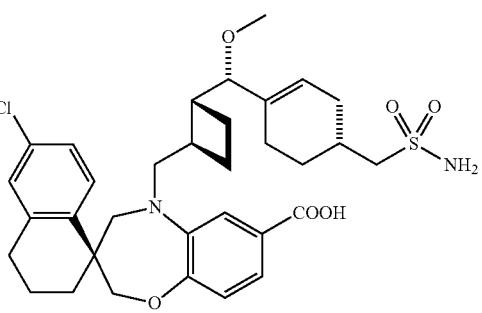

and (S)-methyl 6'-chloro-5-(((1R,2R)-2-((R)-methoxy ((S)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy((R)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((S)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((R)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylate (146 mg, 0.227 mmol) was hydrolyzed in 5 mL 4:1 THF:MeOH with 1N aqueous LiOH (2270 μL, 2.270 mmol) solution at 60° C. overnight. The mixture was then neutralized with 1N HCl, extracted into EtOAc, washed with water and brine, dried over sodium sulfate, filtered and concentrated to yield (S)-6'-chloro-5-(((1R,2R)-2-((R)-methoxy((S)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((R)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S)-methoxy((S)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S)-methoxy((R)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid (110 mg, 0.175 mmol, 77% yield) as a yellow solid.

Step 10: (1S,3'R,6'R,7'R,11'S)-6-chloro-7'-methoxy-3,4-dihydro-2H,15'H-spiro[naphthalene-1,22'-[20]oxa[13]thia[1,14]diazapentacyclo[14.7.2.2$^{8,11}$.0$^{3,6}$.0$^{19,24}$]heptacosa[8,16,18,24]tetraen]-15'-one 13,13' dioxide or (1S,3'R,6'R,7'R,11'R)-6-chloro-7'-methoxy-3,4-dihydro-2H,15'H-spiro[naphthalene-1,22'-[20]oxa[13]thia[1,14]diazapentacyclo[14.7.2.2$^{8,11}$.0$^{3,6}$.0$^{19,24}$]heptacosa[8,16,18,24]tetraen]-15'-one 13,13' dioxide or (1S,3'R,6'R,7'S,11'S)-6-chloro-7'-methoxy-3,4-dihydro-2H,15'H-spiro[naphthalene-1,22'-[20]oxa[13]thia[1,14]diazapentacyclo[14.7.2.2$^{8,11}$.0$^{3,6}$.0$^{19,24}$]heptacosa[8,16,18,24]tetraen]-15'-one 13,13' dioxide or (1S,3'R,6'R,7'S,11'R)-6-chloro-7'-methoxy-3,4-dihydro-2H,15'H-spiro[naphthalene-1,22'-[20]oxa[13]thia[1,14]diazapentacyclo[14.7.2.2$^{8,11}$.0$^{3,6}$.0$^{19,24}$]heptacosa[8,16,18,24]tetraen]-15'-one 13,13' dioxide To a stirred solution (S)-6'-chloro-5-(((1R,2R)-2-((R)-methoxy((S)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((R)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S)-methoxy((S)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S)-methoxy((R)-4-(sulfamoylmethyl)cyclohex-1-en-1-yl)methyl)cyclobutyl)methyl)-3',4,4',5-tetrahydro-2H,2'H-spiro[benzo[b][1,4]oxazepine-3,1'-naphthalene]-7-carboxylic acid (85 mg, 0.135 mmol) in 1.5 mL DCM was added 4-(pyrrolidin-1-yl)pyridine (40.0 mg, 0.270 mmol). The mixture was cooled to 0° C. in an ice bath, followed by addition of 3-(((ethylimino)methylene)amino)-N,N,N-trimethylpropan-1-aminium iodide (92 mg, 0.311 mmol) in 3 portions. The reaction mixture was allowed to warm to RT and then heated to 40° C. overnight. The reaction was allowed to cool to RT, and then stripped of solvent and purified by preparative HPLC to yield one of the title compounds as a single diastereomer. $^1$H NMR (500 MHz, ACETONITRILE-d$_3$) δ 8.96-9.39 (m, 1H), 7.74 (d, J=8.31 Hz, 1H), 7.54 (d, J=1.96 Hz, 1H), 7.22 (dd, J=2.32, 8.44 Hz, 1H), 7.14 (d, J=2.45 Hz, 1H), 7.04 (dd, J=2.08, 8.19 Hz, 1H), 6.89 (d, J=8.07 Hz, 1H), 4.62 (d, J=4.65 Hz, 1H), 4.02-4.11 (m, 3H), 3.96 (dd, J=11.86, 15.77 Hz, 1H), 3.79-3.90 (m, 1H), 3.60 (d, J=14.43 Hz, 1H), 3.33 (d, J=14.43 Hz, 1H), 3.11 (dd, J=5.14, 15.89 Hz, 1H), 2.96-3.02 (m, 1H), 2.94 (s, 3H), 2.69-2.83 (m, 2H), 2.36-2.55 (m, 4H), 1.76-1.89 (m, 4H), 1.61-1.70 (m, 5H).

Example 19. (1S,3'R,6'R,7'S,8'E)-6-chloro-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13' dioxide

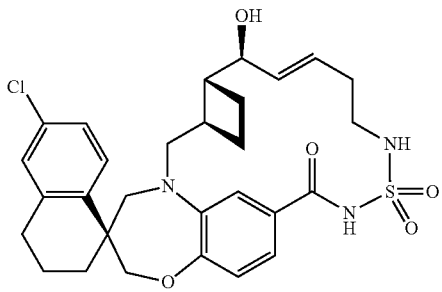

Step 1: tert-butyl N-(but-3-en-1-yl)sulfamoylcarbamate

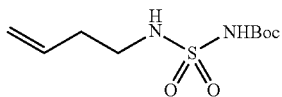

To a solution of chloro-sulfonyl isocyanate (1.062 g, 653 µL, 7.5 mmol, Sigma-Aldrich Co. St. Louis, MO) in dichloromethane (30 mL) was added t-BuOH (717 µL, 7.6 mmol) dropwise. The solution was then stirred for 30 min to allow for complete formation of tert-butoxycarbonylsulfamoyl chloride intermediate. The solution was then added via cannula to a solution of 3-buten-1-amine (367 mg, 5.0 mmol) and N,N-diisopropylethylamine (2.61 mL, 15.0 mmol) in dichloromethane (15 mL) at 0° C. The reaction mixture was allowed to stir at ambient temperature overnight. The solvent was then removed under vacuum and the crude product was purified by flash chromatography on silica gel (120 gram HP silica column, Teledyne Isco) eluting with 0% to 50% ethyl acetate in hexanes to provide tert-butyl N-(but-3-en-1-yl)sulfamoylcarbamate as a white solid (1.05 g, 84% yield).

Step 2: N-3-buten-1-ylsulfamide

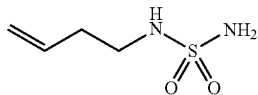

Tert-Butyl N-(but-3-en-1-yl)sulfamoylcarbamate (1.05 g, 4.19 mmol) was treated with 4 N HCl solution in 1,4-dioxane (10.5 mL) at room temperature overnight. The reaction was monitored by TLC using iodine stain. The reaction mixture was concentrated under reduced pressure and the residue was purified by flash chromatography on silica gel (80 gram flash column, Teledyne Isco) eluting with 25% to 100% ethyl acetate in hexane to provide N-3-buten-1-ylsulfamide as a colorless ceramic (630 mg, 100% yield).

Step 3: (S)—N—(N-(but-3-en-1-yl)sulfamoyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide

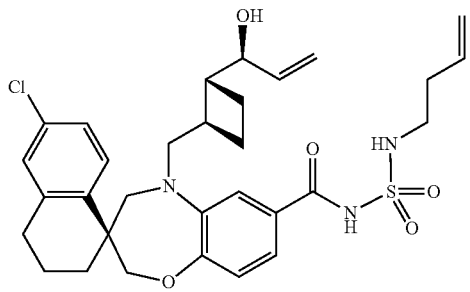 [SMILES: C=CCCNS(=O)(=O)NC(=O)c1ccc2c(c1)N(C[C@@H]1CC[C@H]1[C@@H](O)C=C)C[C@@]1(CCCc3cc(Cl)ccc31)CO2]

To a solution of (1'S)-6'-chloro-5-(((1R,2R)-2-(1-hydroxyallyl)cyclobutyl)methyl)-3',4,4',5-tetrahydro-2H,2'H-spiro[benzo[b][1,4]oxazepine-3,1'-naphthalene]-7-carboxylic acid (1.31 g, 2.8 mmol, Intermediate AA11A), N-3-buten-1-sulfamide (630 mg, 4.19 mmol), N,N-dimethylpyridin-4-amine (513 mg, 4.2 mmol), and N,N-diisopropylethylamine (1.46 mL, 8.40 mmol) in dichloromethane (28 mL) was added N$_1$-((ethylimino)methylene)-N3,N3-dimethylpropane-1,3-diamine hydrochloride (1074 mg, 5.46 mmol, Chem-Impex International, Wood Dale, IL) slowly in portions at 0° C. The reaction mixture thus obtained was stirred at room temperature overnight. The reaction mixture was concentrated under reduced pressure and the residue was purified by flash chromatography on silica gel (120 gram HP silica column, Teledyne Isco) eluting with 5% to 25% ethyl acetate (containing 1% acetic acid) in hexanes to provide (S)—N—(N-(but-3-en-1-yl)sulfamoyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide as a white solid (1.15 g, 68% yield).

Step 4: (1S,3'R,6'R,7'S,8'E)-6-chloro-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide A solution of (S)—N—(N-(but-3-en-1-yl)sulfamoyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide (1.15 g, 1.92 mmol) in 1,1-dichloroethane (1280 mL) was evacuated and purged with argon (3 cycles), then Hoveyda-Grubbs catalyst 2$^{nd}$ generation (132 mg, 0.211 mmol, Sigma-Aldrich Co. St. Louis, MO) was added to the solution under argon atmosphere. The reaction mixture thus obtained was stirred at 50° C. for 24 h and the reaction was monitored by HPLC-MS. At 24 h reaction time point, ethyl-vinylether (210 µL, 2.1 mmol) was added and the reaction mixture was stirred for an additional 10 min. The reaction mixture was concentrated under reduced pressure and the residue was purified by flash chromatography on silica gel (120 gram HP silica column, Teledyne Isco) eluting with 25% to 100% ethyl acetate (containing 1% acetic acid) in hexanes to provide (1S,3'R,6'R,7'S,8'E)-6-chloro-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide as an off-white solid (670 mg, 61% yield). $^1$H NMR (500 MHz, DMSO-d$_6$) δ ppm 11.72 (s, 1H), 8.06 (m, 1H), 7.65 (d, J=8.6 Hz, 1H), 7.25 (dd, J=8.6, 2.0 Hz, 1H), 7.17 (s, 1H), 6.93 (dd, J=9.0, 2.0 Hz, 1H), 6.87 (d, J=9.0 Hz, 1H), 6.75 (s, 1H), 5.89 (m, 1H), 5.50 (dd, J=15.4, 8.6 Hz, 1H), 4.57 (d, J=4.2 Hz, 1H), 4.01-4.05 (m, 1H), 3.94-3.98 (m, 2H), 3.71 (m, 1H), 3.57 (d, J=14.2 Hz, 1H), 3.06-3.26 (m, 2H), 2.88-3.02 (m, 2H), 2.62-2.86 (m, 2H), 2.21-2.40 (m, 2H), 2.03-2.21 (m, 2H), 1.96 (m, 1H), 1.75-1.87 (m, 3H), 1.61-1.67 (m, 3H), 1.38 (m, 1H); MS m/z (ESI, +ve ion) 572.2 (M+H)$^+$.

Example 20. (1S,3'R,6'R,7'S,8'E)-6-chloro-12'-(cyclopropylmethyl)-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide

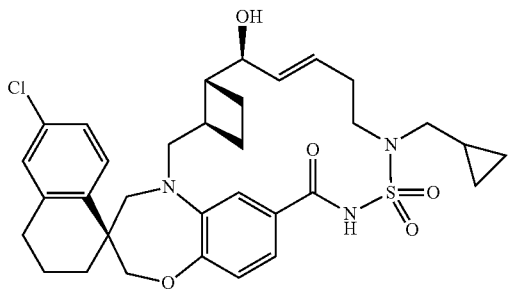 [SMILES: O=C1NS(=O)(=O)N(CC2CC2)CC/C=C/[C@H](O)[C@@H]2CC[C@H]2CN2C[C@@]3(CCCc4cc(Cl)ccc43)COc3ccc1cc32]

Step 1: (1S,3'R,6'R,7'S,8'E)-6-chloro-7'-((dimethyl(2-methyl-2-propanyl)silyl)oxy)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide

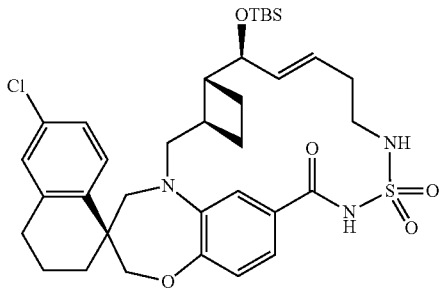 [SMILES: CC(C)(C)[Si](C)(C)O[C@H]1/C=C/CCNS(=O)(=O)NC(=O)c2ccc3c(c2)N(C[C@@H]2CC[C@H]21)C[C@@]1(CCCc2cc(Cl)ccc21)CO3]

To a solution of (1S,3'R,6'R,7'S,8'E)-6-chloro-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide (485 mg, 0.848 mmol, Example 19) in DMF (2.4 mL) were added imidazole (115 mg, 1.7 mmol) and t-butylchlorodimethylsilane (192 mg, 1.27 mmol). The solution thus obtained was stirred at room temperature for 8 h and HPLC-MS analysis indicated completion of the reaction. The reaction mixture was diluted with ethyl acetate and washed with 10% citric acid, water and brine, then dried. The solvent was evaporated and the residue was purified by chromatography on silica gel (80 g flash column, Teledyne Isco) eluting with 0% to 45% ethyl acetate in hexane to provide (1S,3'R,6'R,7'S,8'E)-6-chloro-7'-((dimethyl(2-methyl-2-propanyl)silyl)oxy)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide as a white solid (495 mg, 85% yield).

Step 2: (1S,3'R,6'R,7'S,8'E)-6-chloro-12'-(cyclopropylmethyl)-7'-((dimethyl(2-methyl-2-propanyl)silyl)oxy)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide

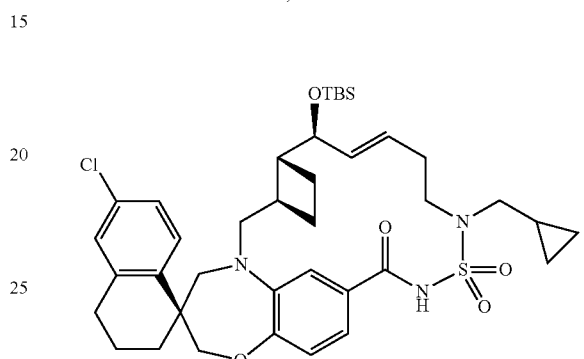

To a solution of (1S,3'R,6'R,7'S,8'E)-6-chloro-7'-((dimethyl(2-methyl-2-propanyl)silyl)oxy)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide (30 mg, 0.044 mmol) in THF (0.5 mL) wad added 1.0 M solution of lithium bis(trimethylsilyl)amide in THF (219 μL, 0.219 mmol) and the mixture was stirred at room temperature for 30 min, then (bromomethyl)cyclopropane (212 μL, 2.185 mmol) was added. The mixture thus obtained was heated at 140° C. for 3 h under microwave irradiation. HPLC-MS analysis indicated completion of the reaction. The reaction mixture was concentrated under reduced pressure and the residue was purified by flash column chromatography on silica gel (12 g HP silica, Teledyne Isco) eluting 0% to 25% ethyl acetate in hexanes to provide (1S,3'R,6'R,7'S,8'E)-6-chloro-12'-(cyclopropylmethyl)-7'-((dimethyl(2-methyl-2-propanyl)silyl)oxy)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide as a white solid (11 mg, 34% yield).

Step 3: (1S,3'R,6'R,7'S,8'E)-6-chloro-12'-(cyclopropylmethyl)-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide To a solution of (1S,3'R,6'R,7'S,8'E)-6-chloro-12'-(cyclopropylmethyl)-7'-((dimethyl(2-methyl-2-propanyl)silyl)oxy)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide (10 mg, 0.014 mmol) in THF (0.5 mL) was added 1M tetrabutylammonium fluoride in THF (27 μL, 0.027 mmol) and the mixture was heated at 50° C. overnight and HPLC-MS analysis indicated completion of the reaction. The reaction mixture was diluted with ethyl acetate and washed with water and brine, dried, then concentrated under vacuum. The residue was purified by flash chromatography on silica gel (12 gram HP silica, Teledyne Isco) eluting with 15% to 75% ethyl acetate in hexane to provide (1S,3'R,6'R,7'S,8'E)-6-Chloro-12'-(cyclopropylmethyl)-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide as a white solid (8 mg, 95%). $^1$H NMR (500 MHz, CDCl$_3$) δ ppm 8.64 (s, 1H), 7.70 (d, J=8.6 Hz, 1H), 7.17 (dd, J=8.6, 2.4 Hz, 1H), 7.09 (d, J=2.0 Hz, 1H), 6.95 (dd, J=9.0, 2.0 Hz, 1H), 6.91 (d, J=9.0 Hz, 1H), 6.87 (br. s., 1H), 5.90 (m, 1H), 5.70 (dd, J=15.0, 9.0 Hz, 1H), 4.19 (m, 1H), 4.05-4.12 (m, 2H), 3.77-3.83 (m, 2H), 3.65-3.70 (m, 2H), 3.42-3.47 (m, 1H), 3.25-3.34 (m, 2H), 3.08-3.15 (m, 1H), 2.70-2.83 (m, 2H), 2.42-2.52 (m, 1H), 2.33-2.42 (m, 2H), 2.27-2.31 (m, 1H), 1.90-2.02 (m, 3H), 1.76-1.84 (m, 2H), 1.62-1.74 (m, 3H), 1.45 (m, 1H), 1.08 (m, 1H), 0.53-0.63 (m, 2H), 0.30-0.39 (m, 2H); MS m/z (ESI, +ve ion) 626.2 (M+H)$^+$.

Example 21. (1S,3'R,6'R,7'S,8'E)-6-chloro-7'-hydroxy-12'-((2R)-tetrahydro-2-furanylmethyl)-3,4-dihydro-2H,15'H-spiro[naphthalene-1,22'-[20]oxa[13]thia]1,12,14]triazatetracyclo[14.7.2.0$^{3,6}$.0$^{19,24}$]pentacosa[8,16,18,24]tetraen]-15'-one 13,13'-dioxide and (1S,3'R,6'R,7'S,8'E)-6-chloro-7'-hydroxy-12'-((2S)-tetrahydro-2-furanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide

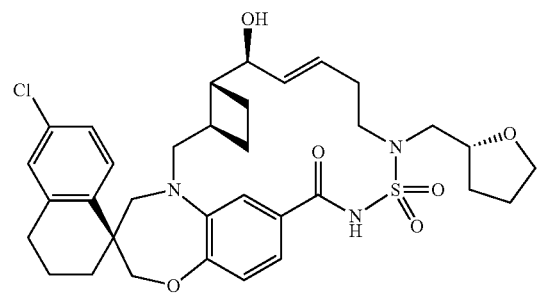

and

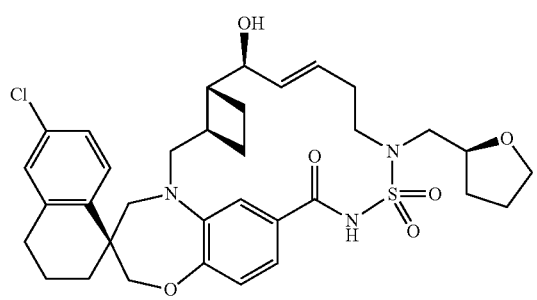

Step 1: (1S,3'R,6'R,7'S,8'E)-6-chloro-7'-((dimethyl(2-methyl-2-propanyl)silyl)oxy)-12'-((2R)-tetrahydro-2-furanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide and (1S,3'R,6'R,7'S,8'E)-6-chloro-7'-((dimethyl(2-methyl-2-propanyl)silyl)oxy)-12'-((2S)-tetrahydro-2-furanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide

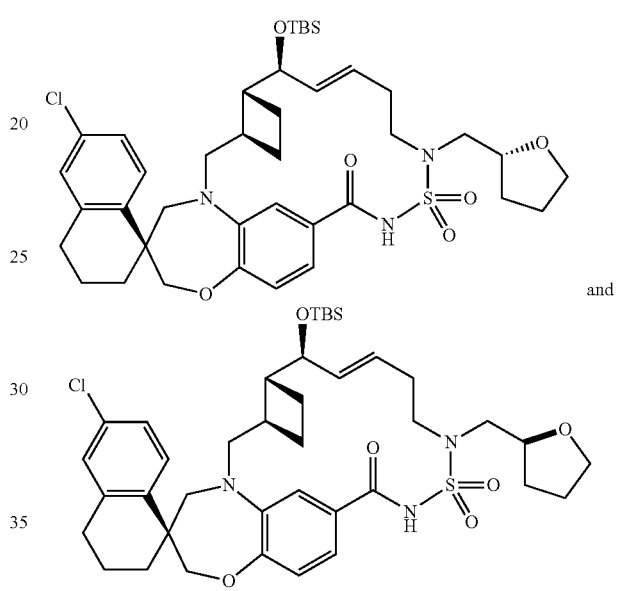

To a solution of (1S,3'R,6'R,7'S,8'E)-6-chloro-7'-((dimethyl(2-methyl-2-propanyl)silyl)oxy)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide (60 mg, 0.097 mmol, Example 20, Step 1) in THF (2.0 mL) wad added 1.0 M solution of lithium bis(trimethylsilyl)amide in THF (437 μL, 0.437 mmol) and the mixture was stirred at room temperature for 30 min, then 2-(bromomethyl)tetrahydrofuran (207 μL, 1.75 mmol) was added. The mixture thus obtained was heated at 140° C. for 3 h under microwave irradiation. HPLC-MS analysis indicated completion of the reaction. The reaction mixture was concentrated under reduced pressure and the residue was purified by flash column chromatography on silica gel (12 g HP silica, Teledyne Isco) eluting 0% to 30% ethyl acetate in hexanes to provide (1S,3'R,6'R,7'S,8'E)-6-chloro-7'-((dimethyl(2-methyl-2-propanyl)silyl)oxy)-12'-((2R)-tetrahydro-2-furanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide and (1S,3'R,6'R,7'S,8'E)-6-chloro-7'-((dimethyl(2-methyl-2-propanyl)silyl)oxy)-12'-((2S)-tetrahydro-2-furanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide as a white solid (30 mg, 45% yield).

Step 2: (1S,3'R,6'R,7'S,8'E)-6-chloro-7'-hydroxy-12'-((2R)-tetrahydro-2-furanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide and (1S,3'R,6'R,7'S,8'E)-6-chloro-7'-hydroxy-12'-((2S)-tetrahydro-2-furanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide To a solution of (1S,3'R,6'R,7'S,8'E)-6-chloro-7'-((dimethyl(2-methyl-2-propanyl)silyl)oxy)-12'-((2R)-tetrahydro-2-furanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide and (1S,3'R,6'R,7'S,8'E)-6-chloro-7'-((dimethyl(2-methyl-2-propanyl)silyl)oxy)-12'-((2S)-tetrahydro-2-furanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide (30 mg, 0.039 mmol) in THF (1 mL) was added 1 M tetrabutylammonium fluoride in THF (78 µL, 0.078 mmol) and the resulting mixture was heated at 50° C. for 7 h and HPLC-MS analysis indicated completion of the reaction. The reaction mixture was diluted with ethyl acetate and washed with water and brine, dried, then concentrated under vacuum. The residue was purified by flash chromatography on silica gel (12 gram HP silica, Teledyne Isco) eluting with 50% to 100% ethyl acetate in hexane to provide a mixture of (1S,3'R,6'R,7'S,8'E)-6-Chloro-7'-hydroxy-12'-((2R)-tetrahydro-2-furanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide and (1S,3'R,6'R,7'S,8'E)-6-chloro-7'-hydroxy-12'-((2S)-tetrahydro-2-furanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide as a white solid (25 mg, 95% yield). $^1$H NMR (500 MHz, CDCl$_3$) δ ppm 7.69 (m, 1H), 7.16 (m, 1H), 7.08 (m, 1H), 7.00 (m, 1H), 6.83-6.90 (m, 2H), 5.99-6.05 (m, 1H), 5.68 (dd, J=15.4, 7.6 Hz, 1H), 4.21 (m, 1H), 4.01-4.15 (m, 3H), 3.83-3.89 (m, 2H), 3.61-3.78 (m, 4H), 3.22-3.32 (m, 2H), 2.97-3.15 (m, 1H), 2.70-2.82 (m, 2H), 2.23-2.53 (m, 4H), 1.85-2.02 (m, 5H), 1.75-1.85 (m, 2H), 1.55-1.73 (m, 5H), 1.37-1.45 (m, 2H); MS m/z (ESI, +ve ion) 656.2 (M+H)$^+$.

Example 22. (1S,3'R,6'R,7'S,8'E)-6-chloro-7'-hydroxy-12'-(2-(2-methoxyethoxy)ethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide

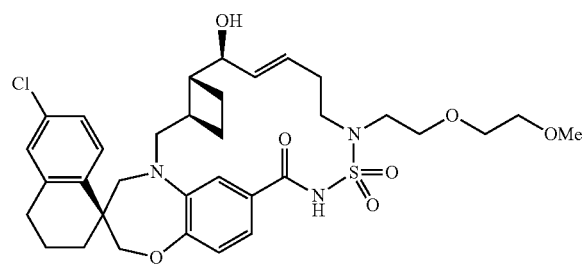 [SMILES: COCCOCCN1CC/C=C/[C@H](O)[C@@H]2CC[C@H]2CN2C[C@@]3(CCCc4cc(Cl)ccc43)COc3ccc(cc32)C(=O)NS1(=O)=O]

Step 1: (1S,3'R,6'R,7'S,8'E)-6-chloro-7'-((dimethyl(2-methyl-2-propanyl)silyl)oxy)-12'-(2-(2-methoxyethoxy)ethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide

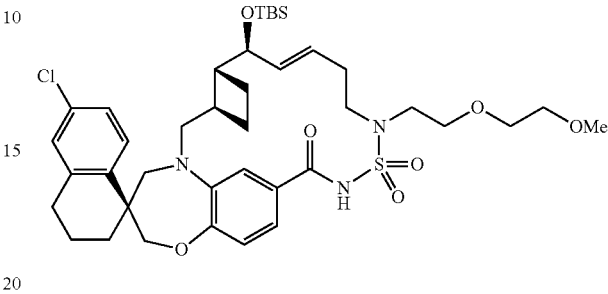

To a solution of (1S,3'R,6'R,7'S,8'E)-6-chloro-7'-((dimethyl(2-methyl-2-propanyl)silyl)oxy)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide (30 mg, 0.044 mmol, Example 20, Step 1) in THF (0.5 mL) wad added 1.0 M solution of lithium bis(trimethylsilyl)amide in THF (219 µL, 0.219 mmol) and the mixture was stirred at room temperature for 30 min, then 1-bromo-2-(2-methoxyethoxy)ethane (327 µL, 2.185 mmol, Sigma-Aldrich Co. St. Louis, MO) was added. The mixture thus obtained was heated at 140° C. for 3 h under microwave irradiation. The reaction mixture was concentrated under reduced pressure and the residue was purified by flash column chromatography on silica gel (12 g HP silica, Teledyne Isco) eluting with 0% to 25% ethyl acetate in hexanes to provide (1S,3'R,6'R,7'S,8'E)-6-Chloro-7'-((dimethyl(2-methyl-2-propanyl)silyl)oxy)-12'-(2-(2-methoxyethoxy)ethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide as a white solid (21 mg, 61% yield).

Step 2: (1S,3'R,6'R,7'S,8'E)-6-chloro-7'-hydroxy-12'-(2-(2-methoxyethoxy)ethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide To a solution of (1S,3'R,6'R,7'S,8'E)-6-chloro-7'-((dimethyl(2-methyl-2-propanyl)silyl)oxy)-12'-(2-(2-methoxyethoxy)ethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide (20 mg, 0.027 mmol) in THF (1 mL) was added 1M tetrabutylammonium fluoride in THF (53.3 µL, 0.053 mmol) and the resulting mixture was stirred at 50° C. 24 h. The reaction mixture was diluted with ethyl acetate and washed with water and brine, dried, then concentrated under vacuum. The residue was purified by flash chromatography on silica gel (12 g HP silica, Teledyne Isco) eluting with 25% to 100% ethyl acetate in hexane to provide (1S,3'R,6'R,7'S,8'E)-6-chloro-7'-hydroxy-12'-(2-(2-methoxyethoxy)ethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide as a white solid (13 mg, 72%). $^1$H NMR (500 MHz, CDCl$_3$) δ ppm 8.70 (s, 1H), 7.70 (d, J=8.6 Hz, 1H), 7.17 (dd, J=8.6, 2.4 Hz, 1H), 7.09 (d, J=2.4 Hz, 1H), 6.93 (dd, J=9.0, 2.0 Hz, 1H), 6.90 (d, J=9.0 Hz, 1H), 6.85 (br. s., 1H), 5.92 (m, 1H), 5.69 (dd, J=15.4, 8.6 Hz, 1H), 4.04-4.21 (m, 4H), 3.80-3.85 (m, 1H), 3.69-3.75 (m, 3H), 3.63-3.66 (m, 3H), 3.56-3.61 (m, 1H), 3.53-3.55 (m, 2H), 3.46-3.52 (m, 1H), 3.37 (s, 3H), 3.25 (d, J=13.9 Hz, 1H), 3.10 (br. s. 1H), 2.75-2.85 (m, 2H), 2.40-2.50 (m, 2H), 2.31-2.40 (m, 1H), 2.22-2.29 (m, 1H), 1.89-2.02 (m, 4H), 1.79-1.85 (m, 2H), 1.61-1.73 (m, 2H), 1.39-1.46 (m, 1H); MS m/z (ESI, +ve ion) 674.2 (M+H)+.

Example 23. 2-((1S,3'R,6'R,7'S,8'E)-6-chloro-7'-hydroxy-13',13'-dioxido-15'-oxo-3,4-dihydro-2H,12'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-12'-yl)-N-methylacetamide

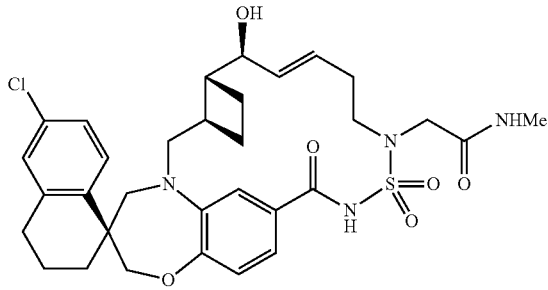 [SMILES: CNC(=O)CN1CC/C=C/[C@H](O)[C@@H]2CC[C@H]2CN2C[C@@]3(CCCc4cc(Cl)ccc43)COc3ccc(cc32)C(=O)NS1(=O)=O]

Step 1: 2-((1S,3'R,6'R,7'S,8'E)-6-chloro-7'-((dimethyl(2-methyl-2-propanyl)silyl)oxy)-13',13'-dioxido-15'-oxo-3,4-dihydro-2H,12'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-12'-yl)-N-methylacetate

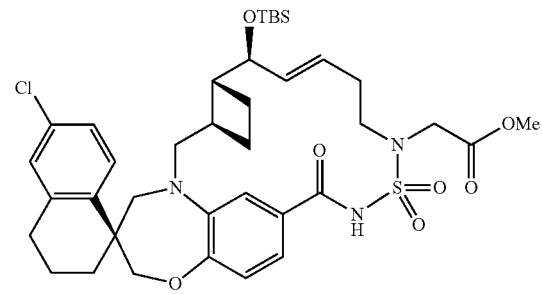

To a solution of (1S,3'R,6'R,7'S,8'E)-6-Chloro-7'-((dimethyl(2-methyl-2-propanyl)silyl)oxy)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide (45 mg, 0.066 mmol, Example 20, Step 1) in THF (1 mL) wad added 1.0 M solution of lithium bis(trimethylsilyl)amide in THF (328 µL, 0.328 mmol) and the mixture was stirred at room temperature for 30 min, then methyl 2-bromoacetate (1244, 1.311 mmol) was added. The mixture thus obtained was heated at 70° C. overnight and HPLC-MS analysis indicated completion of the reaction. The reaction mixture was concentrated under reduced pressure and the residue was purified by flash column chromatography on silica gel (12 g HP silica, Teledyne Isco) eluting with 0% to 25% ethyl acetate in hexanes to provide 2-((1S,3'R,6'R,7'S,8'E)-6-chloro-7'-((dimethyl(2-methyl-2-propanyl)silyl)oxy)-13',13'-dioxido-15'-oxo-3,4-dihydro-2H,12'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-12'-yl)-N-methylacetate as a white solid (58 mg, 82% yield).

Step 2: ((1S,3'R,6'R,7'S,8'E)-6-chloro-7'-((dimethyl(2-methyl-2-propanyl)silyl)oxy)-13',13'-dioxido-15'-oxo-3,4-dihydro-2H,12'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-12'-yl)acetic Acid

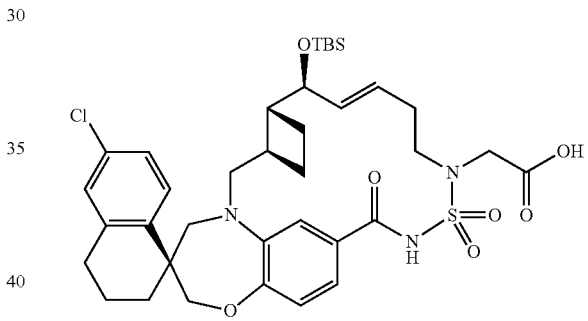

To a solution of 2-((1S,3'R,6'R,7'S,8'E)-6-chloro-7'-((dimethyl(2-methyl-2-propanyl)silyl)oxy)-13',13'-dioxido-15'-oxo-3,4-dihydro-2H,12'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-12'-yl)-N-methylacetate (58 mg, 0.076 mmol) in THF/MeOH/H$_2$O (3/1/1, 460 µL/153 µL/153 µL) was added lithium hydroxide monohydrate (6.4 mg, 0.153 mmol) and the reaction mixture was stirred at 50° C. overnight. HPLC-MS analysis indicated completion of the reaction. The reaction mixture was concentrated under reduced pressure and acidified with 2 N HCl, then extracted with ethyl acetate. The organic layers were washed with brine, dried over MgSO$_4$ and concentrated in vacuo to provide ((1S,3'R,6'R,7'S,8'E)-6-chloro-7'-((dimethyl(2-methyl-2-propanyl)silyl)oxy)-13',13'-dioxido-15'-oxo-3,4-dihydro-2H,12'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-12'-yl)acetic acid as a white solid (57 mg, 100% yield).

Step 3: 2-((1S,3'R,6'R,7'S,8'E)-6-chloro-7'-((dimethyl(2-methyl-2-propanyl)silyl)oxy)-13',13'-dioxido-15'-oxo-3,4-dihydro-2H,12'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-12'-yl)-N-methylacetamide

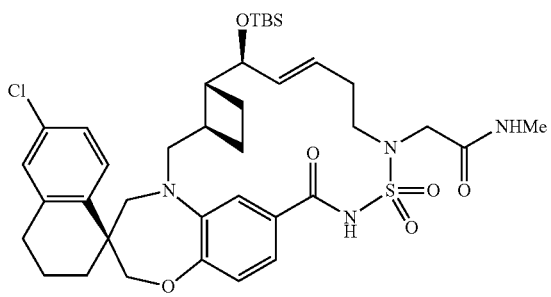

To a solution of ((1S,3'R,6'R,7'S,8'E)-6-chloro-7'-((dimethyl(2-methyl-2-propanyl)silyl)oxy)-13',13'-dioxido-15'-oxo-3,4-dihydro-2H,12'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-12'-yl)acetic acid (0.076 mmol) in dichloromethane (1 mL) were added 2 M solution of methylamine in THF (76 μL, 0.152 mmol), N₁-((ethylimino)methylene)-N3,N3-dimethylpropane-1,3-diamine hydrochloride (29 mg, 0.152 mmol, Chem-Impex International, Wood Dale, IL), 1H-benzo[d][1,2,3]triazol-1-ol (15 mg, 0.114 mmol), and N,N-diisopropylethylamine (39 μL, 0.228 mmol). The mixture thus obtained was stirred at room temperature overnight. The reaction mixture was diluted with ethyl acetate and washed with 1N HCl, water, and brine respectively. The organic layer was dried over MgSO₄ and concentrated to provide crude 2-((1S,3'R,6'R,7'S,8'E)-6-chloro-7'-((dimethyl(2-methyl-2-propanyl)silyl)oxy)-13',13'-dioxido-15'-oxo-3,4-dihydro-2H,12'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-12'-yl)-N-methylacetamide (42 mg) which was used in next de-protection step without further purification.

Step 4: 2-((1S,3'R,6'R,7'S,8'E)-6-chloro-7'-hydroxy-13',13'-dioxido-15'-oxo-3,4-dihydro-2H,12'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-12'-yl)-N-methylacetamide To a solution of 2-((1S,3'R,6'R,7'S,8'E)-6-chloro-7'-((dimethyl(2-methyl-2-propanyl)silyl)oxy)-13',13'-dioxido-15'-oxo-3,4-dihydro-2H,12'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-12'-yl)-N-methylacetamide (42 mg, 0.056 mmol) in THF (1 mL) was added 1M tetrabutylammonium fluoride in THF (112 μL, 0.112 mmol) and the resulting mixture was heated at 50° C. for 7 h and HPLC-MS analysis indicated completion of the reaction. The reaction mixture was diluted with ethyl acetate and washed with water and brine, dried, then concentrated under vacuum. The residue was purified by flash chromatography on silica gel (12 g HP silica, Teledyne Isco) eluting with 50% to 100% ethyl acetate (containing 1% AcOH) in hexane to provide 2-((1S,3'R,6'R,7'S,8'E)-6-chloro-7'-hydroxy-13',13'-dioxido-15'-oxo-3,4-dihydro-2H,12'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-12'-yl)-N-methylacetamide as an off-white solid (32 mg, 89% yield). ¹H NMR (500 MHz, CDCl₃) δ ppm 9.23 (br. s., 1H), 7.69 (d, J=8.6 Hz, 1H), 7.40 (br. s., 1H), 7.17 (dd, J=8.6, 2.4 Hz), 7.09 (d, J=2.0 Hz, 1H), 7.01 (dd, J=8.3, 2.0 Hz, 1H), 6.94 (d, J=8.3 Hz, 1H), 5.80 (m, 1H), 5.69 (dd, J=15.4, 6.8 Hz, 1H), 4.24 (d, J=19.8 Hz, 1H), 4.08-4.16 (m, 4H), 3.56-3.72 (m, 3H), 2.76-2.85 (m, 2H), 2.37-2.46 (m, 3H), 2.28-2.35 (m, 1H), 1.90-2.01 (m, 3H), 1.76-1.86 (m, 2H), 1.65-1.72 (m, 2H), 1.45-1.50 (m, 1H); MS m/z (ESI, +ve ion) 643.2 (M+H)⁺.

Example 24. 2-((1S,3'R,6'R,7'S,8'E)-6-chloro-7'-hydroxy-13',13'-dioxido-15'-oxo-3,4-dihydro-2H,12'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-12'-yl)-N,N-dimethylacetamide

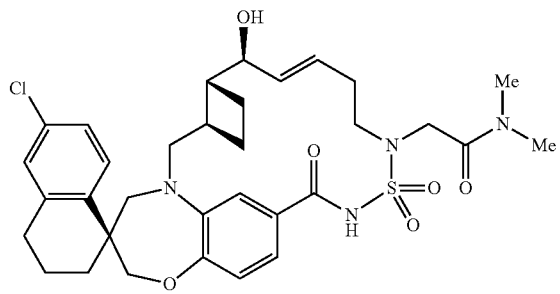 [SMILES: CN(C)C(=O)CN1CC/C=C/[C@H](O)[C@@H]2CC[C@H]2CN2C[C@@]3(CCCc4cc(Cl)ccc43)COc3ccc(cc32)C(=O)NS1(=O)=O]

Step 1: 2-((1S,3'R,6'R,7'S,8'E)-6-chloro-7'-((dimethyl(2-methyl-2-propanyl)silyl)oxy)-13',13'-dioxido-15'-oxo-3,4-dihydro-2H,12'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-12'-yl)-N,N-dimethylacetamide

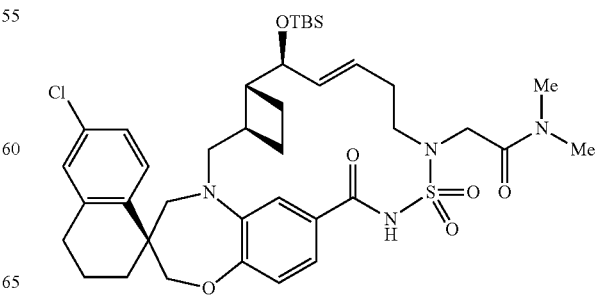

To a solution of ((1S,3'R,6'R,7'S,8'E)-6-chloro-7'-((dimethyl(2-methyl-2-propanyl)silyl)oxy)-13',13'-dioxido-15'-oxo-3,4-dihydro-2H,12'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-12'-yl)acetic acid (112 mg, 0.15 mmol, Example 23, Step 2) in DMF (2 mL) were added dimethylamine hydrochloride (24 mg, 0.30 mmol), N₁-((ethylimino)methylene)-N3,N3-dimethylpropane-1,3-diamine hydrochloride (58 mg, 0.30 mmol), 1H-benzo[d][1,2,3]triazol-1-ol (30 mg, 0.225 mmol), and N,N-diisopropylethylamine (156 µL, 0.90 mmol). The mixture thus obtained was stirred at room temperature overnight. The reaction mixture was diluted with ethyl acetate and washed with 10% citric acid, 5% NaHCO₃, water, and brine respectively. The organic layer was dried over MgSO₄ and concentrated. The residue was purified by flash chromatography on silica gel (24 g HP silica, Teledyne Isco) eluting with 25% to 75% ethyl acetate in hexanes to provide 2-((1S,3'R,6'R,7'S,8'E)-6-chloro-7'-((dimethyl(2-methyl-2-propanyl)silyl)oxy)-13',13'-dioxido-15'-oxo-3,4-dihydro-2H,12'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-12'-yl)-N,N-dimethylacetamide as a white solid (83 mg, 72%).

Step 2: 2-((1S,3'R,6'R,7'S,8'E)-6-chloro-7'-hydroxy-13',13'-dioxido-15'-oxo-3,4-dihydro-2H,12'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-12'-yl)-N,N-dimethylacetamide To a solution of 2-((1S,3'R,6'R,7'S,8'E)-6-chloro-7'-((dimethyl(2-methyl-2-propanyl)silyl)oxy)-13',13'-dioxido-15'-oxo-3,4-dihydro-2H,12'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-12'-yl)-N,N-dimethylacetamide (82 mg, 0.106 mmol) in THF (2.0 mL) was added 1M tetrabutylammonium fluoride in THF (319 µL, 0.319 mmol) and the resulting mixture was heated at 50° C. for 4 h and HPLC-MS analysis indicated completion of the reaction. The reaction mixture was diluted with ethyl acetate and washed with water and brine, dried, then concentrated under vacuum. The residue was purified by reversed phase HPLC (Eclipse Plus C18, 5 µm, 30×150 mm, Agilent) eluting with 45% to 100% acetonitrile (containing 0.1% TFA) in water (containing 0.1% TFA)] to provide 2-((1S,3'R,6'R,7'S,8'E)-6-Chloro-7'-hydroxy-13',13'-dioxido-15'-oxo-3,4-dihydro-2H,12'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-12'-yl)-N,N-dimethylacetamide as a white solid (57 mg, 82% yield). ¹H NMR (500 MHz, CDCl₃) δ ppm 9.59 (br. s., 1H), 7.71 (d, J=8.3 Hz, 1H), 7.18 (dd, J=8.3, 2.3 Hz, 1H), 7.07-7.90 (m, 2H), 6.92 (d, J=8.3 Hz, 1H), 6.88 (br. s., 1H), 5.83-5.98 (m, 1H), 5.77 (dd, J=15.4, 7.6 Hz, 1H), 4.73 (d, J=17.6 Hz, 1H), 4.04-4.18 (m, 4H), 3.65-3.82 (m, 3H), 3.52 (br. s., 1H), 3.30 (d, J=14.2 Hz, 1H), 3.15 (dd, J=15.2, 9.3 Hz, 1H), 3.04 (s, 3H), 2.98 (s, 3H), 2.65-2.83 (m, 2H), 2.54-2.62 (m, 2H), 2.43-2.53 (m, 2H), 2.36-2.41 (m, 2H), 1.90-2.05 (m, 3H), 1.75-1.85 (m, 3H), 1.70 (q, J=12.0 Hz, 1H), 1.44 (t, J=12.0 Hz, 1H); MS m/z (ESI, +ve ion) 657.2 (M+H)⁺.

Example 25. (1S,3'R,6'R,7'S,8'E,11'S)-6-chloro-7'-hydroxy-12'-(2-(2-methoxyethoxy)ethyl)-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13,13'-dioxide

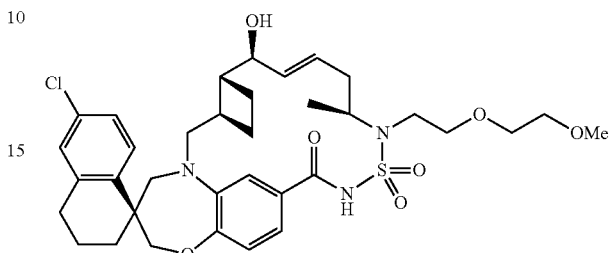

Step 1: (1S,3'R,6'R,7'S,8'E,11'S)-6-chloro-7'-((dimethyl(2-methyl-2-propanyl)silyl)oxy)-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13,13'-dioxide

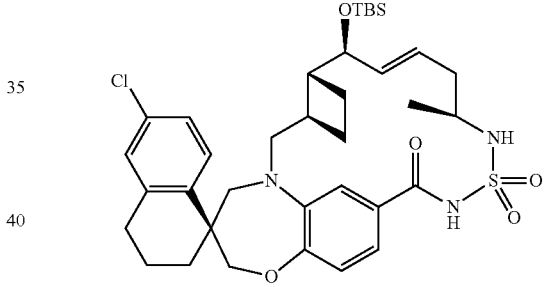

To a solution of (1S,3'R,6'R,7'S,8'E,11'S)-6-chloro-7'-hydroxy-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13,13'-dioxide (470 mg, 0.802 mmol, Example 61) in DMF (5.4 mL) were added imidazole (109 mg, 1.6 mmol) and t-butylchlorodimethylsilane (181 mg, 1.2 mmol). The solution thus obtained was stirred at room temperature for 8 h and HPLC-MS analysis indicated completion of the reaction. The reaction mixture was diluted with ethyl acetate and washed with 10% citric acid, water and brine, then dried. The solvent was evaporated and the residue was purified by chromatography on silica gel (80 g flash column, Teledyne Isco) eluting with 0% to 30% ethyl acetate in hexanes to give. (1S,3'R,6'R,7'S,8'E,11'S)-6-chloro-7'-((dimethyl(2-methyl-2-propanyl)silyl)oxy)-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13,13'-dioxide as a white solid (375 mg, 67% yield).

Step 2: (1S,3'R,6'R,7'S,8'E,11'S)-6-chloro-7'-((dimethyl(2-methyl-2-propanyl)silyl)oxy)-12'-(2-(2-methoxyethoxy)ethyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide

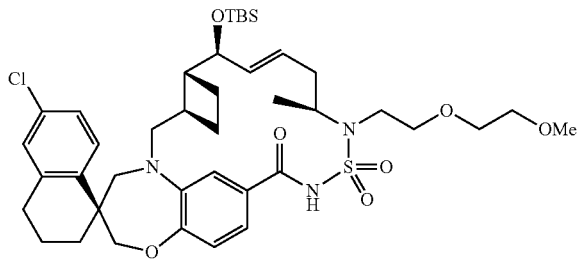 [SMILES: COCCOCCN1[C@@H](C)C/C=C/[C@H](O)[C@@H]2CC[C@H]2CN2C[C@@]3(CCCc4cc(Cl)ccc43)COc3ccc(cc32)C(=O)NS1(=O)=O]

To a solution of (1S,3'R,6'R,7'S,8'E,11'S)-6-chloro-7'-((dimethyl(2-methyl-2-propanyl)silyl)oxy)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide (70 mg, 0.10 mmol) in THF (1 mL) wad added 1.0 M solution of lithium bis(trimethylsilyl)amide in THF (500 μL, 0.50 mmol) and the mixture was stirred at room temperature for 30 min, then 1-bromo-2-(2-methoxyethoxy)ethane (538 μL, 4.0 mmol, Sigma-Aldrich Co. St. Louis, MO) was added. The mixture thus obtained was heated at 140° C. for 5 h under microwave irradiation. The reaction mixture was concentrated under reduced pressure and the residue was purified by flash column chromatography on silica gel (24 g HP silica, Teledyne Isco) eluting 0% to 35% ethyl acetate in hexanes to provide (1S,3'R,6'R,7'S,8'E,11'S)-6-Chloro-7'-((dimethyl(2-methyl-2-propanyl)silyl)oxy)-12'-(2-(2-methoxyethoxy)ethyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide as a white solid (25 mg, 31% yield).

Step 3: (1S,3'R,6'R,7'S,8'E,11'S)-6-chloro-7'-hydroxy-12'-(2-(2-methoxyethoxy)ethyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide To a solution of (1S,3'R,6'R,7'S,8'E,11'S)-6-Chloro-7'-((dimethyl(2-methyl-2-propanyl)silyl)oxy)-12'-(2-(2-methoxyethoxy)ethyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide (25 mg, 0.031 mmol) in THF (1.0 mL) was added 1M tetrabutylammonium fluoride in THF (93 μL, 0.093 mmol) and the resulting mixture was heated for 4 h at 50° C. and HPLC-MS analysis indicated completion of the reaction. The reaction mixture was diluted with ethyl acetate and washed with water and brine, dried, then concentrated under vacuum. The residue was purified by reversed phase HPLC [(Eclipse Plus C18, 5 μm, 30×150 mm, Agilent) eluting with 45% to 100% acetonitrile (containing 0.1% TFA) in water (containing 0.1% TFA)] to provide (1S,3'R,6'R,7'S,8'E,11'S)-6-chloro-7'-hydroxy-12'-(2-(2-methoxyethoxy)ethyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide as a white solid (13 mg, 61%). $^1$H NMR (500 MHz, CDCl$_3$) δ ppm 8.57 (br. s., 1H), 7.69 (d, J=8.6 Hz, 1H), 7.17 (dd, J=8.6, 2.2 Hz, 1H), 7.09 (m, 2H), 6.90 (s, 2H), 5.72-5.78 (m, 1H), 5.63 (dd, J=15.4, 7.6 Hz, 1H), 4.08-4.14 (m, 2H), 4.07 (m, 1H), 3.81-3.93 (m, 2H), 3.67-3.79 (m, 4H), 3.54-3.65 (m, 3H), 3.46-3.52 (m, 1H), 3.39 (s, 3H), 3.30 (d, J=14.2 Hz, 1H), 3.10-3.22 (m, 1H), 2.71-2.82 (m, 2H), 2.35-2.48 (m, 3H), 2.27 (dt, J=16.1, 4.8 Hz, 1H), 1.78-2.02 (m, 7H), 1.61-1.74 (m, 2H), 1.47 (t, J=12.0 Hz, 1H), 1.33 (d, J=6.6 Hz, 3H); MS m/z (ESI, +ve ion) 688.2 (M+H)$^+$.

Example 26. (1S,3'R,6'R,7'S,8'E,11'S)-6-chloro-7'-hydroxy-12'-(2-methoxyethyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide

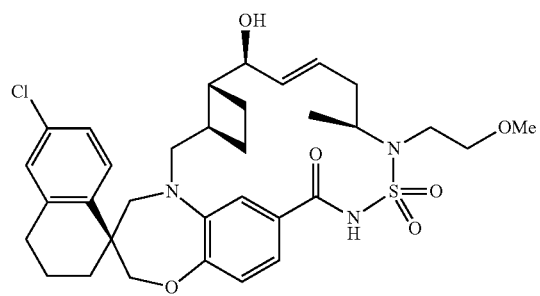 [SMILES: COCCN1[C@@H](C)C/C=C/[C@H](O)[C@@H]2CC[C@H]2CN2C[C@@]3(CCCc4cc(Cl)ccc43)COc3ccc(cc32)C(=O)NS1(=O)=O]

Step 1: (S)-tert-butyl N-(2-methoxyethyl)-N-(pent-4-en-2-yl)sulfamoylcarbamate

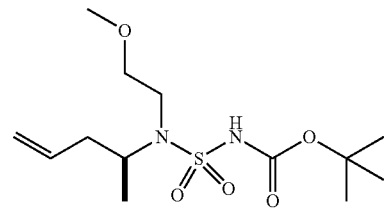 [SMILES: C=CC[C@H](C)N(CCOC)S(=O)(=O)NC(=O)OC(C)(C)C]

Part one: To a solution of (R)-pent-4-en-2-yl 4-methylbenzenesulfonate (Example 61, Step 1) in dioxane (3 mL) was added 2-methoxyethanamine (0.423 mL, 4.79 mmol) and triethylamine (1.00 mL, 7.18 mmol) in a pressure vessel equipped with a gauge. The reaction was heated at 80° C. for 18 hours and 100° C. for 5 hours to afford a product solution, which was used in the following step without workup and purification. This solution is labeled as A.

Part two: To a solution of isocyanatosulfuryl chloride (0.583 mL, 6.70 mmol) in DCM (4 mL) was added tert-butyl alcohol, anhydrous (0.732 mL, 7.65 mmol) dropwise at 0° C. under an atmosphere of N$_2$ and the reaction was stirred at this temperature for 15 minutes. To this reaction was added a solution of A and triethylamine, anhydrous (1.33 mL, 9.57 mmol) in DCM (12 mL) and the resulting mixture was stirred at room temperature for 5 days. This reaction was concentrated and purified by chromatography to afford the title compound (0.414 g, 1.28 mmol, 26.8%).

Step 2: N-(2-methoxyethyl)-N-((2S)-4-penten-2-yl) sulfuric Diamide

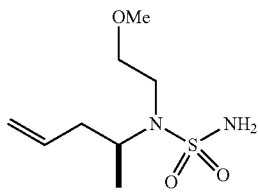

The title compound was prepared from (S)-tert-butyl-N-(2-methoxyethyl)-N-(pent-4-en-2-yl) sulfamoylcarbamate by a procedure similar to the one described in Example 29, Step 2; (0.276 g, 1.24 mmol, 97%).

Step 3: (3S)-6'-chloro-5-(((1R,2R)-2-((1S)-1-hydroxy-2-propen-1-yl)cyclobutyl)methyl)-N-((2-methoxyethyl)((2S)-4-penten-2-yl)sulfamoyl)-3',4,4',5-tetrahydro-2'H-spiro[1,5-benzoxazepine-3,1'-naphthalene]-7-carboxamide

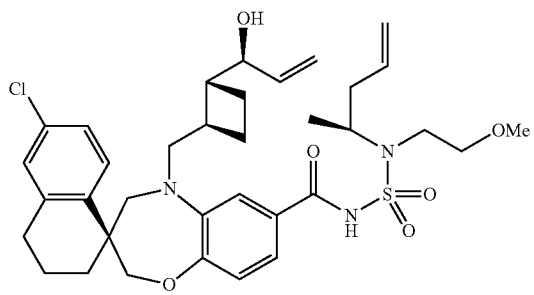 [SMILES: C=CC[C@H](C)N(CCOC)S(=O)(=O)NC(=O)c1ccc2c(c1)N(C[C@@H]1CC[C@H]1[C@@H](O)C=C)C[C@@]1(CCCc3cc(Cl)ccc31)CO2]

To a solution of (1'S)-6'-chloro-5-(((1R,2R)-2-(1-hydroxyallyl)cyclobutyl)methyl)-3',4,4',5-tetrahydro-2H,2'H-spiro[benzo[b][1,4]oxazepine-3,1'-naphthalene]-7-carboxylic acid (1.615 g, 3.45 mmol, Intermediate AA11A), N-(2-Methoxyethyl)-N-((2S)-4-penten-2-yl)sulfuric diamide (1.15 g, 5.17 mmol), N,N-dimethylpyridin-4-amine (632 mg, 5.18 mmol), and N,N-diisopropylethylamine (1.8 mL, 10.35 mmol) in dichloromethane (23 mL) was added $N_1$-((ethylimino)methylene)-N3,N3-dimethylpropane-1,3-diamine hydrochloride (1.32 g, 6.90 mmol, Chem-Impex International, Wood Dale, IL) slowly in portions at 0° C. The reaction mixture thus obtained was stirred at room temperature overnight then it was concentrated under reduced pressure. The residue was dissolved in ethyl acetate, washed with 1N HCl, water and brine then it was dried. The solvent was evaporated and the residue was purified by flash chromatography on silica gel (120 g HP silica column, Teledyne Isco) eluting with 5% to 25% ethyl acetate in hexanes to provide (3S)-6'-chloro-5-(((1R,2R)-2-((1S)-1-hydroxy-2-propen-1-yl)cyclobutyl)methyl)-N-((2-methoxyethyl)((2S)-4-penten-2-yl)sulfamoyl)-3',4,4',5-tetrahydro-2'H-spiro[1,5-benzoxazepine-3,1'-naphthalene]-7-carboxamide as a white solid (1.60 g, 69%).

Step 4: (1S,3'R,6'R,7'S,8'E,11'S)-6-chloro-7'-hydroxy-12'-(2-methoxyethyl)-11'-methyl-3,4-dihydro-2H,15'H-spiro[naphthalene-1,22'-[20]oxa[13]thia[1,12,14]triazatetracyclo[14.7.2.0~3,6~.0~19,24~]pentacosa[8,16,18,24]tetraen]-15'-one 13,13'-dioxide A solution of (S)-6'-chloro-5-(((1R,2R)-2-((S)-1-hydroxyallyl)cyclobutyl)methyl)-N—(N-(2-methoxyethyl)-N—((S)-pent-4-en-2-yl)sulfamoyl)-3',4,4',5-tetrahydro-2H,2'H-spiro[benzo[b][1,4]oxazepine-3,1'-naphthalene]-7-carboxamide (1.60 g, 2.38 mmol) in 1,2-dichloroethane (1190 mL) was evacuated and purged with argon (3 cycles), then Hoveyda-Grubbs catalyst $2^{nd}$ generation (224 mg, 0.357 mmol, Sigma-Aldrich Co. St. Louis, MO) was added to the solution under argon atmosphere. The reaction mixture thus obtained was stirred at 60° C. for 18 h and HPLC-MS analysis indicated completion of the reaction with formation of desired product as major along with other by products. Ethyl-vinylether (341 μL, 3.57 mmol) was added and the reaction mixture was stirred for an additional 10 min. The reaction mixture was concentrated under reduced pressure and the residue was purified by flash chromatography on silica gel eluting with 10% to 75% ethyl acetate (containing 0.5% acetic acid) in hexanes to provide (1S,3'R,6'R,7'S,8'E,11'S)-6-Chloro-7'-hydroxy-12'-(2-methoxy ethyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide as a white solid (600 mg, 37%). $^1$H NMR (500 MHz, CDCl$_3$) δ ppm 8.44 (s, 1H), 7.69 (d, J=8.6 Hz, 1H), 7.18 (dd, J=8.3, 2.4 Hz, 1H), 7.14 (br. s., 1H), 7.09 (d, J=2.4 Hz, 1H), 6.88-6.92 (m, 2H), 5.69-5.74 (m, 1H), 5.63 (dd, J=15.4, 7.8 Hz, 1H), 4.09-4.14 (m, 2H), 4.03 (t, J=4.8 Hz, 1H), 3.88-3.97 (m, 2H), 3.68-3.74 (m, 1H), 3.55-3.65 (m, 2H), 3.40-3.45 (m, 1H), 3.33 (s, 3H), 3.15-3.23 (m, 1H), 2.71-2.83 (m, 2H), 2.38-2.48 (m, 3H), 2.26-2.33 (m, 1H), 1.96-2.00 (m, 2H), 1.79-1.93 (m, 3H), 1.62-1.68 (m, 2H), 1.50-1.61 (m, 3H), 1.48 (t, J=12.0 Hz, 1H), 1.34 (d, J=6.6 Hz, 3H); MS m/z (ESI, +ve ion) 644.2 (M+H)$^+$.

Example 27. (1S,3'R,6'R,7'S,8'E,11'S)-6-chloro-7'-methoxy-12'-(2-methoxyethyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide

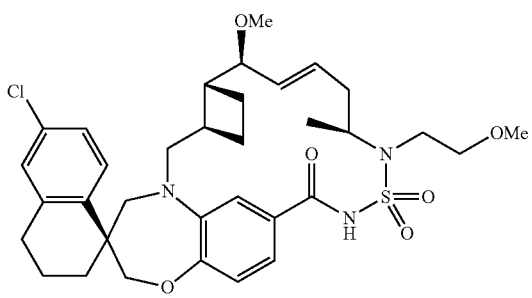 [SMILES: COCCN1[C@@H](C)C/C=C/[C@H](OC)[C@@H]2CC[C@H]2CN2C[C@@]3(CCCc4cc(Cl)ccc43)COc3ccc(cc32)C(=O)NS1(=O)=O]

To a solution of (1S,3'R,6'R,7'S,8'E,11'S)-6-chloro-7'-hydroxy-12'-(2-methoxyethyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide (64 mg, 0.10 mmol, Example 26) in THF (2 mL) was added 60% NaH in mineral oil (20 mg, 0.50 mmol) at 0° C. and the mixture was stirred for 20 min, then iodomethane (31 μL, 0.50 mmol) was added. The reaction mixture thus obtained was stirred at room temperature overnight. The reaction was quenched with sat'd NH4Cl and extracted with ethyl acetate, dried and concentrated. The residue was purified by flash column chromatography on silica gel (12 g, HP silica, Teledyne Isco) eluting with 15% to 50% ethyl acetate in hexanes to provide (1S,3'R,6'R,7'S,8'E,11'S)-6-chloro-7'-methoxy-12'-(2-methoxyethyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide as a white solid (29 mg, 44% yield). $^1$H NMR (500 MHz, CDCl$_3$) δ ppm 8.49 (br. s., 1H), 7.70 (d, J=8.6 Hz, 1H), 7.18 (dd, J=8.3, 2.4 Hz, 1H), 7.09 (d, J=2.4 Hz, 1H), 6.85-7.00 (m, 2H), 6.81 (br. s., 1H), 5.75-5.91 (m, 1H), 5.51 (dd, J=15.7, 8.8 Hz, 1H), 4.05-4.15 (m, 2H), 3.74-3.84 (m, 2H), 3.60-3.68 (m, 4H), 3.40-3.45 (m, 1H), 3.38 (s, 3H), 3.24 (s, 3H), 3.03 (dd, J=15.4, 9.5 Hz, 1H), 2.68-2.91 (m, 2H), 2.37-2.61 (m, 3H), 2.25-2.35 (m, 1H), 1.90-2.05 (m, 3H), 1.73-1.86 (m, 3H), 1.58-1.70 (m, 2H), 1.41 (t, J=12.0 Hz, 1H), 1.36 (d, J=6.8 Hz, 3H); MS m/z (ESI, +ve ion) 658.3 (M+H)$^+$.

Example 28. (1S,3'R,6'R,7'S,8'E,11'S)-6-chloro-12'-(cyclopropylmethyl)-7'-hydroxy-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide

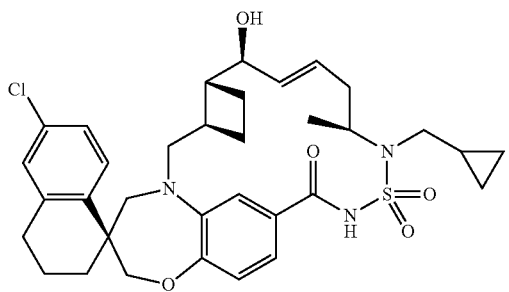 [SMILES: C[C@H]1C/C=C/[C@H](O)[C@@H]2CC[C@H]2CN2C[C@@]3(CCCc4cc(Cl)ccc43)COc3ccc(cc32)C(=O)NS(=O)(=O)N1CC1CC1]

Step 1: (R)-pent-4-en-2-yl 4-methylbenzenesulfonate

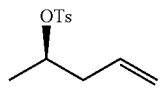

To a solution of (R)-4-penten-2-ol (10 g, 116 mmol, Sigma-Aldrich Co. St. Louis, MO), p-toluenesulfonyl chloride (26.6 g, 139 mmol), N,N-dimethylpyridin-4-amine (1.42 g, 11.61 mmol) in dichloromethane (230 mL) was added triethylamine (32.4 mL, 232 mmol) via syringe at 0° C. The reaction mixture thus obtained was stirred at room temperature for 48 h. The reaction mixture was concentrated and the residue was dissolved in ethyl acetate and washed with 1N HCl, water, and brine, then dried over MgSO$_4$. After filtration, the filtrate was concentrated under reduced pressure and the residue was purified by flash column chromatography on silica gel (330 g flash column, Teledyne Isco) eluting with 0% to 25% ethyl acetate in hexanes to provide (R)-pent-4-en-2-yl 4-methylbenzenesulfonate as a colorless oil (24.82 g, 89%).

Step 2: N-(cyclopropylmethyl)-N-((1S)-1-methyl-3-buten-1yl)sulfamide

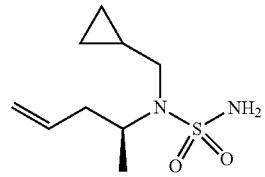

To a solution of (R)-pent-4-en-2-yl 4-methylbenzenesulfonate (2.4 g, 10 mmol) in 1,4-dioxane (20 mL) were added cyclopropylmethanamine hydrochloride (1.08 g, 10.0 mmol) and N,N-diisopropylethylamine (5.23 mL, 30.0 mmol). The mixture thus obtained was heated at 100° C. for 2 days. The reaction mixture was concentrated and the residue was dissolved in ethyl acetate and washed with 5% NaOH, then dried. The solvent was evaporated under reduced pressure to provide crude (S)—N-(cyclopropylmethyl)pent-4-en-2-amine (400 mg). The crude product was dissolved in 1,4-dioxane (5 mL) and sulfamine (1.92 g) was added. The mixture thus obtained was heated at 100° C. overnight. The solvent was evaporated under reduced pressure and the residue was subjected to flash chromatography on silica gel (120 g flash column, Teledyne Isco) eluting with 10% to 50% ethyl acetate in hexanes to provide N-(cyclopropylmethyl)-N-((1S)-1-methyl-3-buten-1yl)sulfamide as a light yellow solid (37 mg, 2% yield in two steps).

Step 3: (3S)-6'-chloro-N-((cyclopropylmethyl)((2S)-4-penten-2-yl)sulfamoyl)-5-(((1R,2R)-2-((1S)-1-hydroxy-2-propen-1-yl)cyclobutyl)methyl)-3',4,4',5-tetrahydro-2'H-spiro[1,5-benzoxazepine-3,1'-naphthalene]-7-carboxamide

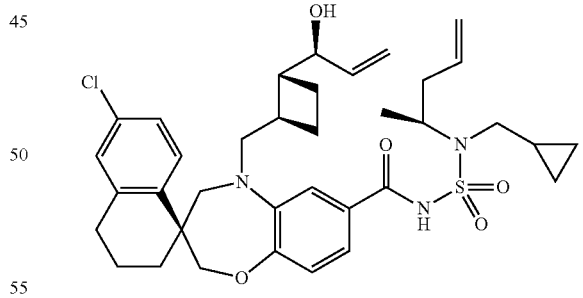

To a solution of (1'S)-6'-chloro-5-(((1R,2R)-2-(1-hydroxyallyl)cyclobutyl)methyl)-3',4,4',5-tetrahydro-2H,2'H-spiro[benzo[b][1,4]oxazepine-3,1'-naphthalene]-7-carboxylic acid (70.2 mg, 0.15 mmol, Intermediate AA11A), N-(cyclopropylmethyl)-N-((1S)-1-methyl-3-buten-1yl)sulfamide (37 mg, 0.169 mmol), N,N-dimethylpyridin-4-amine (27.5 mg, 0.225 mmol), and N,N-diisopropylethylamine (78 μL, 0.45 mmol) in dichloromethane (1.5 mL) was added N$_1$-((ethylimino)methylene)-N3,N3-dimethylpropane-1,3-diamine hydrochloride (57.5 mg, 0.30 mmol, Chem-Impex International, Wood Dale, IL) slowly in portions at 0° C. The reaction mixture thus obtained was stirred at room temperature overnight. The reaction mixture was concentrated under reduced pressure and the residue was purified by flash chromatography on silica gel (120 g HP silica column, Teledyne Isco) eluting with 5% to 25% ethyl acetate (containing 1% acetic acid) in hexanes to provide (3S)-6'-chloro-N-((cyclopropylmethyl)((2S)-4-penten-2-yl)sulfamoyl)-5-(((1R,2R)-2-((1S)-1-hydroxy-2-propen-1-yl)cyclobutyl)methyl)-3',4,4',5-tetrahydro-2'H-spiro[1,5-benzoxazepine-3,1'-naphthalene]-7-carboxamide as a white solid (56 mg, 56%).

Step 4: (1S,3'R,6'R,7'S,8'E,11'S)-6-chloro-12'-(cyclopropylmethyl)-7'-hydroxy-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide A solution of (S)-6'-chloro-N—(N-(cyclopropylmethyl)-N—((S)-pent-4-en-2-yl)sulfamoyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide (58 mg, 0.087 mmol) in 1,2-dichloroethane (58 mL) was evacuated and purged with argon (3 cycles), then Hoveyda-Grubbs catalyst 2$^{nd}$ generation (8.2 mg, 0.013 mmol, Sigma-Aldrich Co. St. Louis, MO) was added to the solution under argon atmosphere. The reaction mixture thus obtained was stirred at 50° C. for 24 h. Ethyl-vinylether (12 µL, 0.13 mmol) was added and the reaction mixture was stirred for an additional 10 min. The reaction mixture was concentrated under reduced pressure and the residue was purified by flash chromatography on silica gel (40 g HP silica column, Teledyne Isco) eluting with 10% to 75% ethyl acetate (containing 0.5% acetic acid) in hexanes to provide (1S,3'R,6'R,7'S,8'E,11'S)-6-chloro-12'-(cyclopropylmethyl)-7'-hydroxy-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13,13'-dioxide as a white solid (25 mg, 45% yield). $^1$H NMR (500 MHz, CDCl$_3$) δ ppm 8.50 (br. s., 1H), 7.69 (d, J=8.3 Hz, 1H), 7.17-7.18 (m, 2H), 7.08 (d, J=2.4 Hz, 1H), 6.86-6.92 (m, 2H), 5.62-5.72 (m, 2H), 4.08-4.14 (m, 2H), 4.01 (m, 1H), 3.89-3.95 (m, 1H), 3.62-3.76 (m, 3H), 3.30 (d, J=15.0 Hz, 1H), 3.16 (dd, J=15.8, 6.5 Hz, 1H), 2.70-2.85 (m, 2H), 2.28-2.51 (m, 4H), 1.76-2.00 (m, 6H), 1.61-1.70 (m, 2H), 1.44-1.48 (m, 1H), 1.43 (d, J=10.0 Hz, 3H), 1.06-1.11 (m, 1H), 0.54-0.62 (m, 2H), 0.42-0.46 (m, 1H), 0.29-0.33 (m, 1H); MS m/z (ESI, +ve ion) 640.3 (M+H)$^+$.

Example 29. (1S,3'R,6'R,7'S,8'E)-6-chloro-12'-ethyl-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

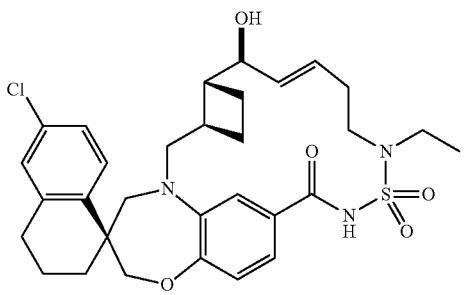 [SMILES: CCN1CC/C=C/[C@H](O)[C@@H]2CC[C@H]2CN2C[C@@]3(CCCc4cc(Cl)ccc43)COc3ccc(cc32)C(=O)NS1(=O)=O]

Step 1: tert-butyl N-(but-3-en-1-yl)-N-ethylsulfamoylcarbamate

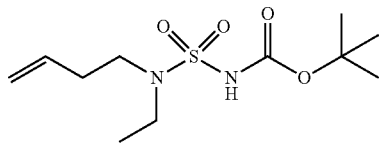 [SMILES: C=CCCN(CC)S(=O)(=O)NC(=O)OC(C)(C)C]

To a solution of isocyanatosulfuryl chloride (2.63 mL, 30.2 mmol) in DCM (5 mL) was added anhydrous tert-butyl alcohol (3.13 mL, 32.8 mmol) dropwise at 0° C. under N$_2$ atmosphere and the reaction was stirred at 0° C. for 15 minutes followed by an addition of a solution of N-ethylbut-3-en-1-amine (2.50 g, 25.2 mmol) and anhydrous triethylamine (10.5 mL, 76 mmol) in DCM (40 mL). The resulting mixture was stirred at ambient temperature overnight. The reaction was then concentrated and the residue was purified by column chromatography to afford the title compound (1.10 g, 3.95 mmol, 15.7% yield).

Step 2: N-(but-3-en-1-yl)-N-ethyl Sulfuric Diamide

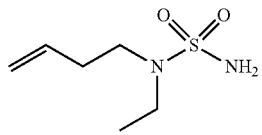

To a solution of tert-butyl N-(but-3-en-1-yl)-N-ethylsulfamoylcarbamate (1.10 g, 3.95 mmol) in dioxane (4 mL) was added 4 M hydrochloric acid solution in 1,4-dioxane (6 mL, 23.6 mmol) and the reaction was stirred at ambient temperature for 28 hours. The reaction was concentrated and the residue was dried on vacuum to afford the title compound (0.745 g, 4.18 mmol, 106% crude yield).

Step 3: (S)—N—(N-(but-3-en-1-yl)-N-ethylsulfamoyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide

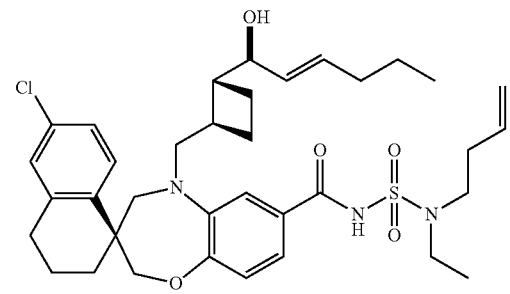 [SMILES: C=CCCN(CC)S(=O)(=O)NC(=O)c1ccc2c(c1)N(C[C@@H]1CC[C@H]1[C@@H](O)/C=C/CCC)C[C@@]1(CCCc3cc(Cl)ccc31)CO2]

To a solution of N,N-dimethylpyridin-4-amine (329 mg, 2.70 mmol), Intermediate AA12A (550 mg, 1.08 mmol), triethylamine (0.600 mL, 4.31 mmol) and N-(but-3-en-1-yl)-N-ethyl sulfuric diamide (692 mg, 3.88 mmol) in DCM (25 mL) at 0° C. was added N-(3-dimethylaminopropyl)-

N'-ethylcarbodiimide hydrochloride (517 mg, 2.70 mmol) in portions over 40 minutes. The reaction was stirred at ambient temperature overnight under N$_2$ atmosphere. The reaction was concentrated and the residue was dissolved in DCM and purified by silica gel chromatography using Redi-Sep pre-packed Gold silica gel column eluting with 0-20% of ethyl acetate (containing 0.3% acetic acid) in hexane to afford the title compound as a solid (373 mg, 0.556 mmol, 51.6% yield).

Step 4: (1S,3'R,6'R,7'S,8'E)-6-chloro-12'-ethyl-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide A 500 mL round-bottom flask was charged with (S)—N—(N-(but-3-en-1-yl)-N-ethylsulfamoyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide (0.373 g, 0.556 mmol), Hoveyda-Grubbs II catalyst (0.070 g, 0.111 mmol) and acetic acid (192 mL). The solution was purged with N$_2$ for 15 minutes and then stirred at ambient temperature under slightly reduced pressure for 17 hours. The reaction was concentrated and the residue was dissolved in methanol and purified by reversed phase preparatory HPLC (Gemini™ Prep C$_{18}$ 5 µm column; Phenomenex, Torrance, CA) to afford the title compound as the first eluting isomer (0.074 g, 0.123 mmol, 22.2% yield). $^1$H NMR (400 MHz, CDCl$_3$) δ 8.50 (br. s, 1H), 7.72 (d, J=8.41 Hz, 1H), 7.20 (dd, J=2.25, 8.51 Hz, 1H), 7.11 (d, J=2.15 Hz, 1H), 6.99-6.89 (m, 3H), 5.91 (ddd, J=4.89, 9.49, 14.8 Hz, 1H), 5.72 (dd, J=7.83, 15.1 Hz, 1H), 4.2-4.19 (m, 1H), 4.14-4.07 (m, 3H), 3.81-3.59 (m, 3H), 3.43-3.34 (m, 1H), 3.30-3.323 (m, 2H), 3.17 (m, 1H), 2.80-2.74 (m, 2H), 2.48-2.25 (m, 5H), 2.03-1.93 (m, 3H), 1.86-1.82 (m, 2H), 1.75-1.66 (m, 2H), 1.48 (t, J=12.7 Hz, 1H), 1.27 (t, J=7.04 Hz, 3H). m/z (ESI, +ve ion) 601.2 (M+H)$^+$.

Example 30. (1S,3'R,6'R,7'S,8'Z)-6-chloro-12'-ethyl-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

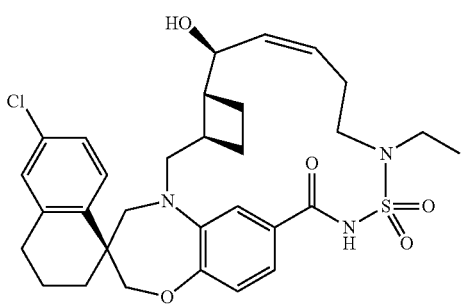 [SMILES: CCN1CC/C=C\[C@H](O)[C@@H]2CC[C@H]2CN2C[C@@]3(CCCc4cc(Cl)ccc43)COc3ccc(cc32)C(=O)NS1(=O)=O]

The title compound was isolated as the second eluting isomer (0.025 g, 0.042 mmol, 7.49% yield) from the reversed phase preparatory HPLC separation in Example 29, Step 4. $^1$H NMR (400 MHz, CDCl$_3$) δ 9.66 (br. s, 1H), 7.74 (d, J=8.61 Hz, 1H), 7.39 (dd, J=1.86, 8.31 Hz, 1H), 7.20 (dd, J=2.3, 8.4 Hz, 1H), 7.11 (d, J=3.28 Hz, 2H), 6.99 (d, J=7.89 Hz, 1H), 5.76-5.63 (m, 2H), 4.52 (t, J=6.36 Hz, 1H), 4.17-4.06 (m, 2H), 3.95-3.81 (m, 2H), 3.67 (d, J=14.28 Hz, 1H), 3.61-3.39 (m, 3H), 3.32-3.10 (m, 2H), 2.84-2.58 (m, 3H), 2.44-2.28 (m, 4H), 2.13-1.94 (m, 3H), 1.87-1.84 (m, 2H), 1.78-1.64 (m, 1H), 1.62-1.38 (m, 2H), 1.28 (t, J=7.14 Hz, 3H). m/z (ESI, +ve ion) 601.2 (M+H)$^+$.

Example 31. (1S,3'R,6'R,7'S,8'E)-6-chloro-7'-hydroxy-12'-(2-methoxyethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

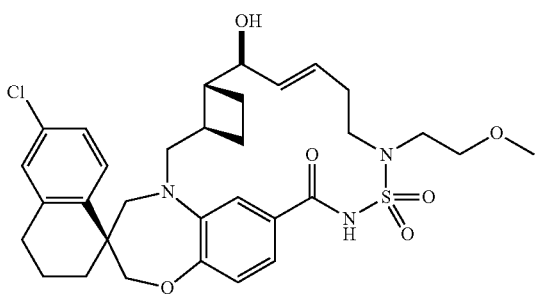 [SMILES: COCCN1CC/C=C/[C@H](O)[C@@H]2CC[C@H]2CN2C[C@@]3(CCCc4cc(Cl)ccc43)COc3ccc(cc32)C(=O)NS1(=O)=O]

Step 1: (1S,3'R,6'R,7'S,8'E)-6-chloro-7'-[(tert-butyldiphenylsilyl)oxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

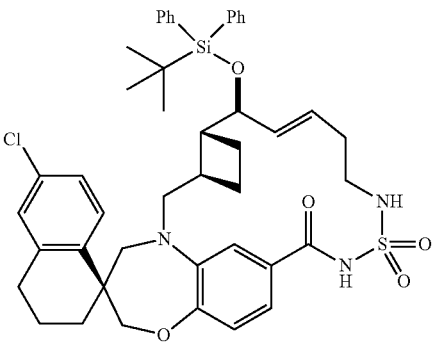 [SMILES: CC(C)(C)[Si](O[C@H]1/C=C/CCNS(=O)(=O)NC(=O)c2ccc3c(c2)N(C[C@@H]2CC[C@H]21)C[C@@]1(CCCc2cc(Cl)ccc21)CO3)(c1ccccc1)c1ccccc1]

To a solution of Example 19 (31 mg, 0.054 mmol) in DMF (0.5 mL) was added 1H-imidazole (9.59 mg, 0.141 mmol) and tert-butylchlorodiphenylsilane (0.018 mL, 0.070 mmol) under N$_2$ atmosphere and the reaction was stirred at ambient temperature for 36 hours. LCMS showed that the reaction was not completed. More tert-butylchlorodiphenylsilane (0.009 mL, 0.035 mmol) and 1H-imidazole (4.80 mg, 0.071 mmol) were added and the reaction was stirred at ambient temperature for another 6 hours. The reaction was quenched with saturated NH$_4$Cl and extracted with EtOAc. The organic extract was dried with MgSO$_4$, filtered and concentrated to give a residue which was purified by silica gel chromatography using Redi-Sep pre-packed Gold silica gel column eluting with 0-20% of ethyl acetate in hexane to afford the title compound (26 mg, 0.032 mmol, 59.2% yield).

Step 2: (1S,3'R,6'R,7'S,8'E)-6-chloro-7'-hydroxy-12'-(2-methoxyethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide To a solution of (1S,3'R,6'R,7'S,8'E)-6-chloro-7'-[(tert-butyldiphenylsilyl)oxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide (10 mg, 0.012 mmol) in DMF (0.25 mL) at 0° C. was added sodium hydride, 60% dispersion in mineral oil (1.48 mg, 0.037 mmol). After the reaction was stirred at room temperature for 30 minutes, 1-bromo-2-methoxyethane (1.49 µL, 0.015 mmol) was added. The reaction was stirred at ambient temperature for about 2 hours. Additional 1-bromo-2-methoxyethane (4.47 µl, 0.045 mmol) and sodium hydride, 60% dispersion in mineral oil (1.48 mg, 0.037 mmol) were added to facilitate the reaction and the resulting mixture was stirred at ambient temperature for another 35 hours. The reaction was quenched with saturated NH$_4$Cl and extracted with EtOAc. The organic phase was washed with brine and dried using MgSO$_4$. After filtration and concentration the crude material was purified by reversed phase preparatory HPLC (Gemini™ Prep C$_{18}$ 5 µm column; Phenomenex, Torrance, CA; gradient elution of 60% to 75% MeCN in water, where both solvents contain 0.1% TFA, 30 min method) to afford the title compound as a solid (1.14 mg, 1.81 µmol, 14.7% yield). $^1$H NMR (400 MHz, CDCl$_3$) δ 8.55 (br. s, 1H), 7.72 (d, J=8.41 Hz, 1H), 7.20 (dd, J=2.25, 8.51 Hz, 1H), 7.11 (d, J=2.15 Hz, 1H), 6.98-6.89 (m, 3H), 5.97-5.87 (m, 1H), 5.72 (dd, J=7.73, 15.5 Hz, 1H), 4.26-4.06 (m, 4H), 3.89-3.83 (dt, J=4.57, 14.9 Hz, 1H), 3.75-3.60 (m, 4H), 3.58-3.40 (m, 2H), 3.39 (s, 3H), 3.28 (d, J=14.28 Hz, 1H), 3.15 (dd, J=7.63, 14.1 Hz, 1H), 2.85-2.72 (m, 2H), 2.53-2.35 (m, 3H), 2.34-2.20 (m, 1H), 2.05-1.89 (m, 3H), 1.85 (br. S, 2H), 1.80-1.61 (m, 3H), 1.47 (t, J=11.8 Hz, 1H). m/z (ESI, +ve ion) 631.2 (M+H)$^+$.

Example 32. methyl((1S,3'R,6'R,7'S,8'E)-6-chloro-7'-hydroxy-13',13'-dioxido-15'-oxo-3,4-dihydro-2H,12'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-12'-yl)acetate

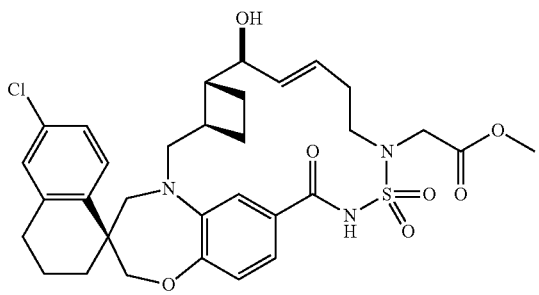 [SMILES: COC(=O)CN1CC/C=C/[C@H](O)[C@@H]2CC[C@H]2CN2C[C@@]3(CCCc4cc(Cl)ccc43)COc3ccc(cc32)C(=O)NS1(=O)=O]

Step 1: (1S,3'R,6'R,7'S,8'E)-6-chloro-7'-[(tert-butyldimethylsilyl)oxy]-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

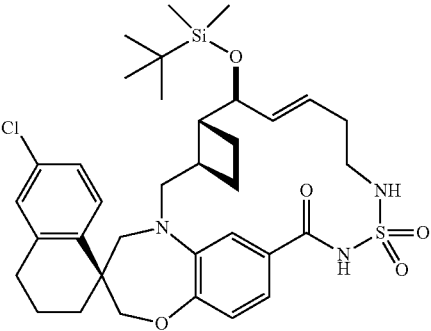

To a solution of Example 19 (141 mg, 0.246 mmol) in DCM (6 mL) at 0° C. was added N,N-diisopropylethylamine (0.107 mL, 0.616 mmol) followed by addition of tert-butyldimethylsilyl trifluoromethanesulfonate (0.074 mL, 0.320 mmol). The reaction was stirred at 0° C. for 1 hour and at ambient temperature for 3.5 hours. Trace amount of desired product was detected by LCMS from the reaction. More N,N-diisopropylethylamine (0.107 mL, 0.616 mmol) and tert-butyldimethylsilyl trifluoromethanesulfonate (0.148 mL, 0.640 mmol) were added and the reaction was stirred at ambient temperature for 40 minutes. The reaction was quenched with saturated aqueous NaHCO$_3$ and extracted with EtOAc. The organic extract was washed with brine, dried with MgSO$_4$, filtered and concentrated to give a residue which was purified by silica gel chromatography using Redi-Sep pre-packed Gold silica gel column (40 g) eluting with 0-30% of ethyl acetate in hexane to afford the title compound as a solid (114 mg, 0.166 mmol, 67.4% yield).

Step 2: methyl((1S,3'R,6'R,7'S,8'E)-6-chloro-7'-[(tert-butyldimethylsilyl)oxy]-13',13'-dioxido-15'-oxo-3,4-dihydro-2H,12'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-12'-yl)acetate

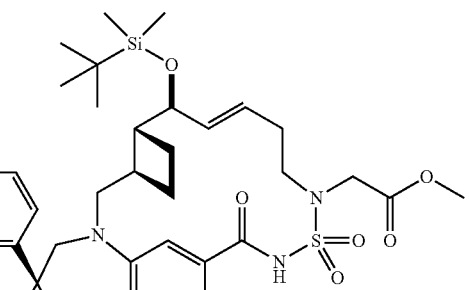

To a solution of (1S,3'R,6'R,7'S,8'E)-6-chloro-7'-[(tert-butyldimethylsilyl)oxy]-3,4-dihydro-2H,15'H-spiro[naphthalene-1,22'-[20]oxa[13]thia[1,12,14]triazatetracyclo

[14.7.2.0³,⁶.0¹⁹,²⁴]pentacosa[8,16,18,24]tetraen]-15'-one 13',13'-dioxide (61 mg, 0.089 mmol) in THF (1 mL) was added lithium bis(trimethylsilyl) amide, 1.0 M solution in tetrahydrofuran (0.355 mL, 0.355 mmol) and the reaction was stirred at ambient temperature for 10 minutes followed by addition of methyl 2-bromoacetate (0.033 mL, 0.355 mmol). The reaction was transferred to a microwave tube and irradiated at 80° C. for 11 hours and then at 100° C. for another 1.5 hours. The reaction was quenched with saturated NH₄Cl and extracted with EtOAc. The organic extract was washed with H₂O, brine and dried with MgSO₄ and filtered. After concentration the crude material was purified by silica gel chromatography using Redi-Sep pre-packed Gold silica gel column (40 g) eluting with 0-30% ethyl acetate in hexane to afford the title compound (32 mg, 0.042 mmol, 47.5% yield).

Step 3: methyl((1S,3'R,6'R,7'S,8'E)-6-chloro-7'-hydroxy-13',13'-dioxido-15'-oxo-3,4-dihydro-2H, 12'H-spiro[naphthalene-1,22'-[20]oxa[13]thia[1,12, 14]triazatetracyclo[14.7.2.0³,⁶.0¹⁹,²⁴]pentacosa[8,16, 18,24]tetraen]-12'-yl)acetate Methyl ((1S,3'R,6'R,7'S,8'E)-6-chloro-7'-[(tert-butyldimethylsilyl)oxy]-13',13'-dioxido-15'-oxo-3,4-dihydro-2H, 12'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-12'-yl)acetate (32 mg, 0.042 mmol) was treated with 1M TBAF solution in THF (0.5 mL) and a small amount of molecular sieves at 50° C. for 2 hours. The reaction was concentrated to give a crude material which was purified by reversed phase preparatory HPLC (Gemini™ Prep C₁₈ 5 µm column; Phenomenex, Torrance, CA; gradient elution of 45% to 75% MeCN in water, where both solvents contain 0.1% TFA, 30 min method) to afford the title compound (10 mg, 0.016 mmol, 36.8% yield). ¹H NMR (400 MHz, CDCl₃) δ 8.92 (br. s., 1H), 7.72 (d, J=8.41 Hz, 1H), 7.20 (dd, J=2.35, 8.41 Hz, 1H), 7.11 (d, J=1.96 Hz, 1H), 7.00-6.91 (m, 3H), 5.90-5.71 (m, 2H), 4.77 (d, J=18.78 Hz, 1H), 4.24-4.06 (m, 4H), 4.00-3.87 (m, 1H), 3.81 (s, 3H), 3.77-3.62 (m, 2H), 3.36-3.23 (m, 2H), 3.18 (br. s, 1H), 2.85-2.72 (m, 2H), 2.51-2.37 (m, 3H), 2.31 (dd, J=6.06, 9.00 Hz, 1H), 2.14 (br. s, 1H), 2.02-1.96 (m, 3H), 1.99 (m, 2H), 1.70 (m, 2H), 1.48 (t, J=12.23 Hz, 1H). m/z (ESI, +ve ion) 645.2 (M+H)⁺.

Example 33. 3-((1S,3'R,6'R,7'S,8'E)-6-chloro-7'-hydroxy-13',13'-dioxido-15'-oxo-3,4-dihydro-2H, 12'H-spiro[naphthalene-1,22'-[20]oxa[13]thia[1,12, 14]triazatetracyclo[14.7.2.0³,⁶.0¹⁹,²⁴]pentacosa[8,16, 18,24]tetraen]-12'-yl)propanoic Acid

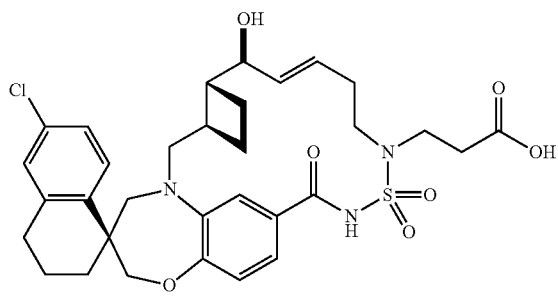

Step 1: methyl 3-((1S,3'R,6'R,7'S,8'E)-6-chloro-7'-[(tert-butyldimethylsilyl)oxy]-13',13'-dioxido-15'-oxo-3,4-dihydro-2H,12'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-12'-yl) propanoate

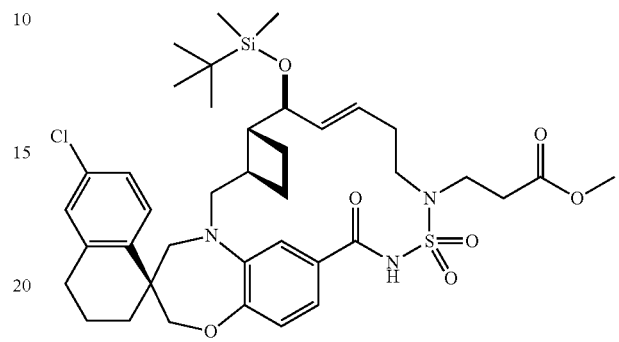

To a solution of (1S,3'R,6'R,7'S,8'E)-6-chloro-7'-[(tert-butyldimethylsilyl)oxy]-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide (14 mg, 0.020 mmol, Example 32, Step 1 in DMF (0.3 mL) was added sodium hydride (8.16 mg, 0.204 mmol) and the reaction was stirred at ambient temperature for 25 minutes followed by an addition of methyl acrylate (0.012 mL, 0.122 mmol). The resulting mixture was stirred at ambient temperature for 18 hours and 60° C. for another 4 hours. Since no improvement was obtained by LCMS, more methyl acrylate (0.0092 mL, 0.092 mmol) was added and the resulting mixture was stirred at 60° C. for 19 hours. The reaction was quenched with saturated NH₄Cl and extracted with EtOAc. The organic extract was dried using MgSO₄, filtered and concentrated to give a residue which was purified by reversed phase preparatory HPLC (Gemini™ Prep C18 5 µm column; Phenomenex, Torrance, CA; gradient elution of 50% to 85% MeCN in water, where both solvents contain 0.1% TFA, 30 min method) to afford the title compound.

Step 2: 3-((1S,3'R,6'R,7'S,8'E)-6-chloro-7'-hydroxy-13',13'-dioxido-15'-oxo-3,4-dihydro-2H,12'H-spiro [naphthalene-1,22'-[20]oxa[13]thia[1,12,14]triazatetracyclo[14.7.2.0³,⁶.0¹⁹,²⁴]pentacosa[8,16,18,24] tetraen]-12'-yl) propanoic Acid Methyl 3-((1S,3'R,6'R,7'S,8'E)-6-chloro-7'-[(tert-butyldimethylsilyl)oxy]-13',13'-dioxido-15'-oxo-3,4-dihydro-2H, 12'H-spiro[naphthalene-1,22'-[20]oxa[13]thia[1,12,14]triazatetracyclo[14.7.2.0³,⁶.0¹⁹,²⁴]pentacosa[8,16,18,24] tetraen]-12'-yl) propanoate (1.4 mg, 1.81 µmol) was treated with 1M TBAF solution in THF (0.5 mL) and a small amount of molecular sieves at 60° C. for 1.5 hours. The reaction was concentrated to give a residue, which was purified by reversed phase preparatory HPLC (Gemini™ Prep C₁₈ 5 µm column; Phenomenex, Torrance, CA) to afford the title compound as a solid. ¹H NMR (400 MHz, CDCl₃) δ 8.83 (br. s, 1H), 7.70 (d, J=8.41 Hz, 1H), 7.19 (dd, J=6.24 Hz, 1H), 7.10 (d, J=4.04 Hz, 1H), 6.97-6.83 (m, 3H), 5.92 (d, J=4.69 Hz, 1H), 5.77-5.67 (m, 1H), 4.36-4.21 (m, 2H), 4.15-4.02 (m, 2H), 3.76-3.62 (m, 3H), 3.42-3.31 (m, 1H), 3.26 (d, J=14.1 Hz, 1H), 3.11 (br. s, 1H), 2.80 (br. s, 2H), 2.45-2.39 (m, 3H), 2.32 (m, 1H), 2.15 (br. s, 5H), 2.03-1.93 (m, 3H), 1.84-1.82 (m, 2H), 1.74-1.64 (m, 2H), 1.44 (t, J=12.2 Hz, 1H). m/z (ESI, +ve ion) 643.0 (M+H)+.

Example 34. (1S,3'R,6'R,7'S,8'E)-6-chloro-7'-hydroxy-12'-(2-(methylsulfonyl)ethyl)-3,4-dihydro-2H, 15'H-spiro[naphthalene-1,22'-[20]oxa[13]thia[1,12, 14]triazatetracyclo[14.7.2.0$^{3,6}$.0$^{19,24}$]pentacosa[8,16, 18,24]tetraen]-15'-one 13',13'-dioxide

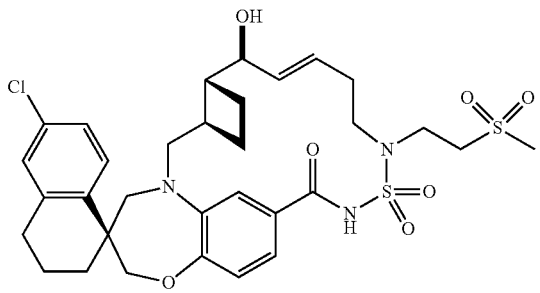

To a solution of (1S,3'R,6'R,7'S,8'E)-6-chloro-7'-[(tert-butyldimethylsilyl)oxy]-12'-(2-(methylsulfonyl)ethyl)-3,4-dihydro-2H,15'H-spiro[naphthalene-1,22'-[20]oxa[13]thia [1,12,14]triazatetracyclo[14.7.2.0$^{3,6}$.0$^{19,24}$]pentacosa[8,16, 18,24]tetraen]-15'-one 13',13'-dioxide (7.2 mg, 10.49 µmol, Example 32, Step 1) in DMF (0.2 mL) was added sodium hydride (60% dispersion in mineral oil, 4.20 mg, 0.105 mmol) and the reaction was stirred at ambient temperature for 20 minutes followed by addition of (methylsulfonyl) ethene (5.52 µL, 0.063 mmol) and the resulting mixture was stirred at ambient temperature for 80 minutes. The reaction was quenched with saturated aqueous NH$_4$Cl and extracted with EtOAc. The organic extract was washed with brine, dried with MgSO$_4$, filtered and concentrated to give a crude Michael addition product. This crude product was treated with tetrabutylammonium fluoride, 1.0 M in tetrahydrofuran (0.505 mL, 0.505 mmol) and molecular sieves at 60° C. for 1.5 hours. The reaction was concentrated and re-dissolved in MeOH and filtered. The crude material was purified by reversed phase preparatory HPLC (Gemini™ Prep C$_{18}$ 5 µm column; Phenomenex, Torrance, CA; gradient elution of 30% to 70% MeCN in water, where both solvents contain 0.1% TFA, 30 min method) to afford the title compound as a white solid (3.9 mg, 5.75 µmol, 56% yield). $^1$H NMR (400 MHz, CDCl$_3$) δ 8.86 (br. s, 1H), 7.71 (d, J=8.61 Hz, 1H), 7.20 (dd, J=2.25, 8.51 Hz, 1H), 7.11 (d, J=2.15 Hz, 1H), 7.02-6.87 (m, 3H), 5.93-5.82 (m, 1H), 5.71-5.81 (m, 1H), 4.60-4.49 (m, 1H), 4.26-4.23 (m, 1H), 4.19-4.04 (m, 2H), 3.93-3.77 (m, 2H), 3.77-3.63 (m, 2H), 3.58-3.33 (m, 3H), 3.33-3.20 (m, 1H), 3.17 (m, 1H), 3.06 (s, 3H), 2.87-2.72 (m, 2H), 2.54-2.26 (m, 4H), 2.11-1.93 (m, 4H), 1.86-1.77 (m, 2H), 1.75-1.64 (m, 2H), 1.48 (t, J=12.0 Hz, 1H). m/z (ESI, +ve ion) 679.2 (M+H)+.

Example 35. 2-((1S,3'R,6'R,7'S,8'E)-6-chloro-7'-hydroxy-13',13'-dioxido-15'-oxo-3,4-dihydro-2H, 12'H-spiro[naphthalene-1,22'-[20]oxa[13]thia[1,12, 14]triazatetracyclo[14.7.2.0$^{3,6}$.0$^{19,24}$]pentacosa[8,16, 18,24]tetraen]-12'-yl)-N,N-diethylethanesulfonamide

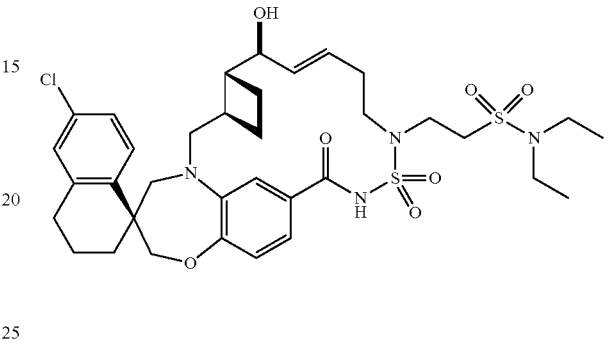

The title compound was prepared from (1S,3'R,6'R,7'S, 8'E)-6-chloro-7'-[(tert-butyldimethylsilyl)oxy]-3,4-dihydro-2H,15'H-spiro[naphthalene-1,22'-[20]oxa[13]thia[1,12,14] triazatetracyclo[14.7.2.0$^{3,6}$.0$^{19,24}$]pentacosa[8,16,18,24] tetraen]-15'-one 13',13'-dioxide (Example 32, Step 1) by a procedure similar to the one described in Example 34, and it was obtained as a white solid (1.5 mg, 2.04 µmol, 12.7% yield). $^1$H NMR (400 MHz, CDCl$_3$) δ 8.62 (s, 1H), 7.69 (d, J=8.61 Hz, 1H), 7.18 (dd, J=2.25, 8.51 Hz, 1H), 7.09 (d, J=2.15 Hz, 1H), 6.96-6.87 (m, 3H), 5.90-5.80 (m, 1H), 5.78-5.69 (m, 1H), 4.52-4.42 (m, 1H), 4.20 (dd, J=4.79, 7.14 Hz, 1H), 4.16-4.03 (m, 2H), 3.86-3.62 (m, 4H), 3.40-3.24 (m, 8H), 3.21-3.05 (m, 1H), 2.83-2.70 (m, 2H), 2.52-2.24 (m, 4H), 2.03-1.87 (m, 3H), 1.83 (br. s, 2H), 1.79-1.58 (m, 3H), 1.53-1.34 (m, 1H), 1.30-1.19 (m, 6H). m/z (ESI, +ve ion) 736.2 (M+H)+.

Example 36. (1S,3'R,6'R,7'S,8'Z)-6-chloro-7'-hydroxy-3,4-dihydro-2H,15'H-spiro[naphthalene-1,22'-[20]oxa[13]thia[1,12,14]triazatetracyclo[14.7.2.0$^{3,6}$. 0$^{19,24}$]pentacosa[8,16,18,24]tetraen]-15'-one 13',13'-dioxide

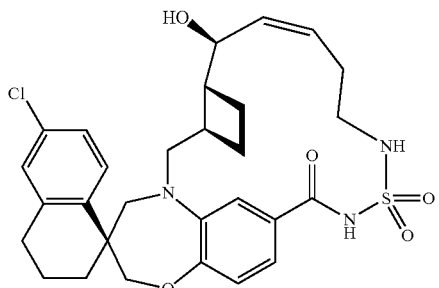

Step 1: tert-butyl N-(but-3-en-1-yl)sulfamoylcarbamate

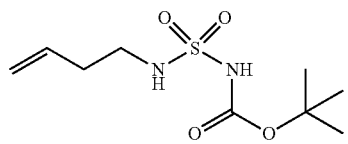 [SMILES: C=CCCNS(=O)(=O)NC(=O)OC(C)(C)C]

The title compound was prepared from but-3-en-1-amine by a procedure similar to the one described in Example 29, Step 1.

Step 2: N-(but-3-en-1-yl)sulfuric Diamide

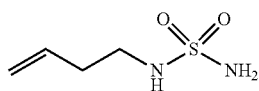

The title compound was prepared from tert-butyl N-(but-3-en-1-yl)sulfamoylcarbamate by a procedure similar to the one described in Example 29, Step 2.

Step 3: (S)—N—(N-(but-3-en-1-yl)sulfamoyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-Carboxamide

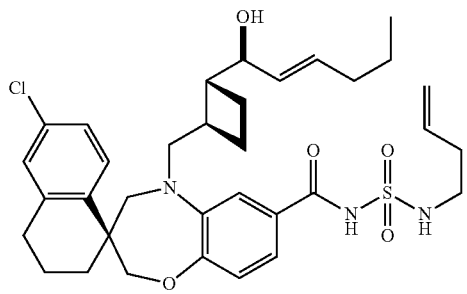

The title compound was prepared from Intermediate AA12A and N-(but-3-en-1-yl)sulfuric diamide by a procedure similar to the one described in Example 29, Step 3.

Step 4: (1S,3'R,6'R,7'S,8'Z)-6-chloro-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide The title compound was prepared from (S)—N—(N-(but-3-en-1-yl)sulfamoyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide by a procedure similar to the one described in Example 29, Step 4. $^1$H NMR (400 MHz, CDCl$_3$) δ 11.12 (br. s, 1H), 7.66 (d, J=8.61 Hz, 1H), 7.37 (d, J=7.63 Hz, 1H), 7.15 (m, 2H), 7.08 (s, 1H), 6.82 (d, J=8.41 Hz, 1H), 6.02 (br. s, 1H), 5.79-5.59 (m, 2H), 4.29 (t, J=8.41 Hz, 1H), 4.05-3.93 (m, 2H), 3.80 (d, J=5.48 Hz, 1H), 3.69 (d, J=15.6 Hz, 1H), 3.52 (d, J=14.3 Hz, 1H), 3.19 (br. s, 1H), 3.15-2.96 (m, 2H), 2.82-2.63 (m, 3H), 2.35-2.18 (m, 1H), 2.17-1.91 (m, 5H), 1.90-1.75 (m, 3H), 1.66 (dt, J=9.39, 18.4 Hz, 1H), 1.52-1.34 (m, 2H). m/z (ESI, +ve ion) 573.2 (M+H)$^+$.

Example 37. (1S,3'R,6'R,7'S,8'Z)-6-chloro-7'-hydroxy-12'-(2-(methylsulfonyl)ethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

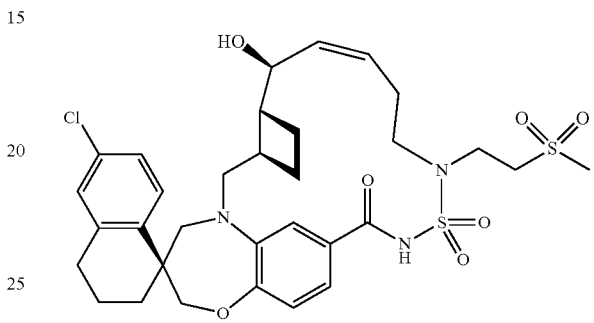

Step 1: (1S,3'R,6'R,7'S,8'Z)-6-chloro-7'-[(tert-butyldimethylsilyl)oxy]-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

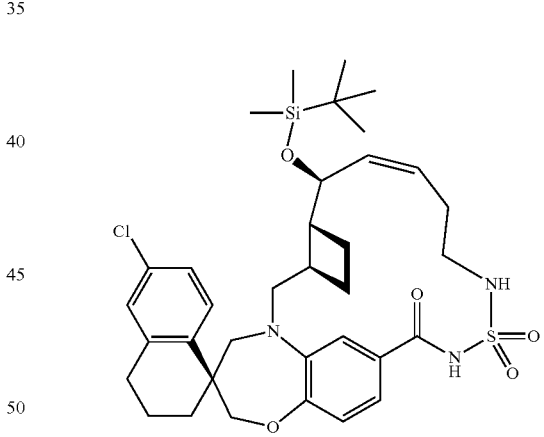

The title compound was prepared from Example 36 by a procedure similar to the one described in Example 32, Step 1.

Step 2: (1S,3'R,6'R,7'S,8'Z)-6-chloro-7'-hydroxy-12'-(2-(methylsulfonyl)ethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide The title compound was prepared from (1S,3'R,6'R,7'S,8'Z)-6-chloro-7'-[(tert-butyldimethylsilyl)oxy]-3,4-dihydro-2h,15'h-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide by a procedure similar to the one described in example 34. $^1$H NMR (400 MHz, CDCl$_3$) δ 10.1 (br. s, 1H), 7.74-7.67 (m, J=8.4 Hz, 1H), 7.36 (br. s, 1H), 7.17 (dd, J=2.0, 8.6 Hz, 1H), 7.09 (s, 2H), 7.03-6.92 (m, 1H), 5.68 (br. s, 2H), 4.50 (br. s, 1H), 4.24 (br. s, 1H), 4.19-3.99 (m, 2H), 3.84 (br. s, 1H), 3.70-3.53 (m, 3H), 3.53-3.35 (m, 1H), 3.21 (d, J=14.3 Hz, 2H), 3.05 (s, 3H), 2.84-2.61 (m, 3H), 2.34 (br. s, 4H), 2.07-1.88 (m, 4H), 1.83 (br. s, 2H), 1.79-1.62 (m, 2H), 1.56 (br. s, 1H), 1.46 (br. s, 1H). m/z (ESI, +ve ion) 679.2 (M+H)$^+$.

Example 38. (1S,3'R,6'R,7'S,8'E)-6-chloro-7'-hydroxy-12'-((2S)-2-oxetanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide or (1S,3'R,6'R,7'S,8'E)-6-chloro-7'-hydroxy-12'-((2R)-2-oxetanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

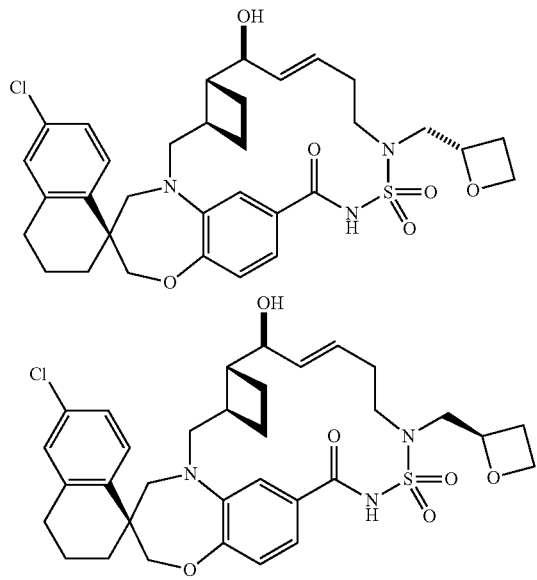

Step 1: (S)-oxetan-2-ylmethyl 4-methylbenzenesulfonate and (R)-oxetan-2-ylmethyl 4-methylbenzenesulfonate

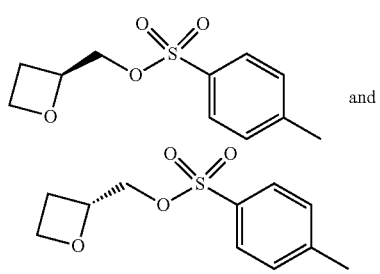

To a solution of 4-methylbenzene-1-sulfonyl chloride (3.28 g, 17.2 mmol) and 4-(dimethylamino) pyridine (0.191 g, 1.57 mmol) in DCM (40 mL) was added triethylamine, (reagentplus 99.5%, 4.36 mL, 31.3 mmol) followed by an addition of a solution of 2-hydroxymethyloxetane (1.28 mL, 15.7 mmol) in DCM (12 mL) over 10 minutes. The resulting mixture was stirred at ambient temperature for 60 hours. The reaction mixture was filtered to remove the precipitate produced in the reaction, concentrated and purified by column chromatography to afford the title compound (3.5 g, 14.4 mmol, 92% yield).

Step 2: (1S,3'R,6'R,7'S,8'E)-6-chloro-7'-[(tert-butyldimethylsilyl)oxy]-12'-((2S)-2-oxetanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide and (1S,3'R,6'R,7'S,8'E)-6-chloro-7'-[(tert-butyldimethylsilyl)oxy]-12'-((2R)-2-oxetanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

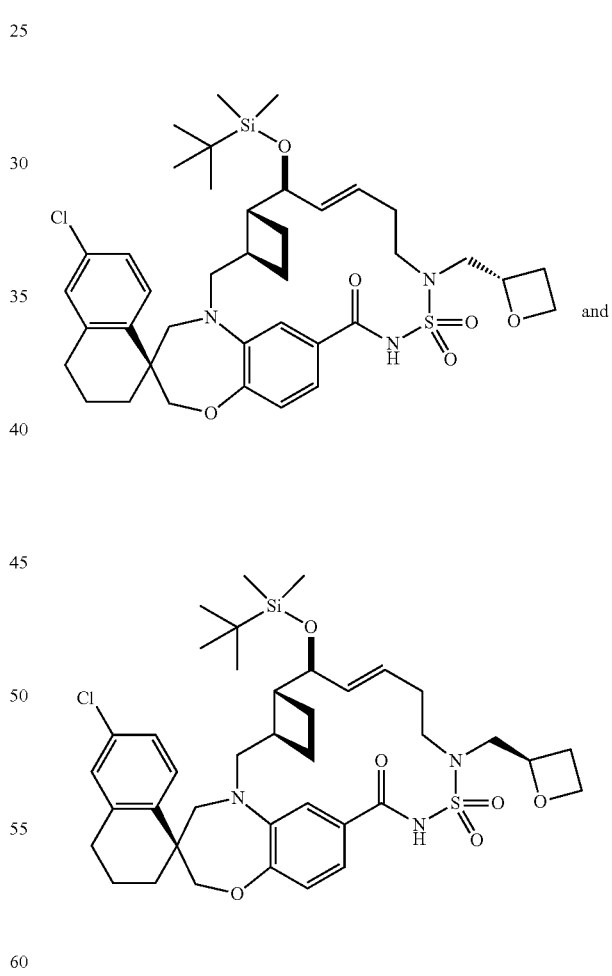

To a solution of (1S,3'R,6'R,7'S,8'E)-6-chloro-7'-[(tert-butyldimethylsilyl)oxy]-12'-((2S)-2-oxetanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16, 18,24]tetraen]-15'-one 13',13'-dioxide (60 mg, 0.087 mmol, Example 32, Step 1) in THF (1 mL) was added lithium bis(trimethylsilyl)amide, 1.0 M solution in THF (0.350 mL, 0.350 mmol) and the reaction was stirred at ice-bath for 10 minutes followed by an addition of (S)-oxetan-2-ylmethyl 4-methylbenzenesulfonate and (R)-oxetan-2-ylmethyl 4-methylbenzenesulfonate (74.1 mg, 0.306 mmol) in THF (0.4 mL). The reaction mixture was then transferred to a microwave tube under $N_2$ and heated at 100° C. for 3 hours. LCMS showed 50% of conversion to product. The reaction was quenched with saturated $NH_4Cl$ and extracted with EtOAc. The organic extract was washed with water and brine, dried using $MgSO_4$, filtered and concentrated. The crude material was purified by chromatography using Redi-Sep pre-packed Gold silica gel column (40 g) eluting with ethyl acetate in hexane to afford the title compound (16 mg, 0.021 mmol, 24.2% yield, with impurities).

Step 3: (1S,3'R,6'R,7'S,8'E)-6-chloro-7'-hydroxy-12'-((2S)-2-oxetanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide or (1S,3'R,6'R,7'S,8'E)-6-chloro-7'-hydroxy-12'-((2R)-2-oxetanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide (1S,3'R,6'R,7'S,8'E)-6-chloro-7'-[(tert-butyldimethylsilyl)oxy]-12'-((2S)-2-oxetanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide and (1S,3'R,6'R,7'S,8'E)-6-chloro-7'-[(tert-butyldimethylsilyl)oxy]-12'-((2R)-2-oxetanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide (16 mg, 0.021 mmol) was treated with tetrabutylammonium fluoride (1.0 M in tetrahydrofuran, 0.952 mL, 0.952 mmol) and a small amount of molecular sieves at 55° C. for 4 hours. The reaction was concentrated and the crude material was purified by reversed phase preparatory HPLC (Gemini™ Prep $C_{18}$ 5 µm column; Phenomenex, Torrance, CA; gradient elution of 45% to 85% MeCN in water, where both solvents contain 0.1% TFA, 30 min method) to give a mixture of two isomers with a ratio of 14/86. (6.6 mg, 5.14 µmol, 24.3% yield). The mixture was separated by SFC using a chiral column of Chromega Chiral CC4, 3.0×25 cm with the following conditions: mobile phase, 55% methanol (20 mM $NH_3$)/45% $CO_2$; flow rate, 80 mL/min; SFC outlet pressure, 100 bar; mobile phase temperature, 33° C.; wavelength, 242 nm to afford the title compound as the second eluting isomer. $^1$H NMR (400 MHz, CDCl$_3$) δ 8.72 (s, 1H), 7.72 (d, J=8.41 Hz, 1H), 7.20 (dd, J=2.25, 8.51 Hz, 1H), 7.11 (d, J=2.15 Hz, 1H), 7.02-6.92 (m, 2H), 6.88 (br. s, 1H), 6.00-5.90 (m, 1H), 5.73 (dd, J=7.63, 15.3 Hz, 1H), 5.13-5.07 (m, 1H), 4.73-4.66 (m, 1H), 4.56 (dt, J=6.21, 8.71 Hz, 1H), 4.24-4.06 (m, 4H), 3.93-3.83 (m, 1H), 3.81-3.66 (m, 4H), 3.29 (d, J=14.5 Hz, 1H), 3.15 (d, J=7.63 Hz, 1H), 2.85-2.67 (m, 4H), 2.57-2.47 (m, 1H), 2.47-2.29 (m, 3H), 2.08-1.98 (m, 4H), 1.85 (br. s, 1H), 1.79-1.61 (m, 3H), 1.47 (t, J=12.1 Hz, 1H). m/z (ESI, +ve ion) 643.2 (M+H)$^+$.

Example 39. (1S,3'R,6'R,7'S,8'E)-6-chloro-7'-hydroxy-12'-((2R)-2-oxetanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide or (1S,3'R,6'R,7'S,8'E)-6-chloro-7'-hydroxy-12'-((2S)-2-oxetanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

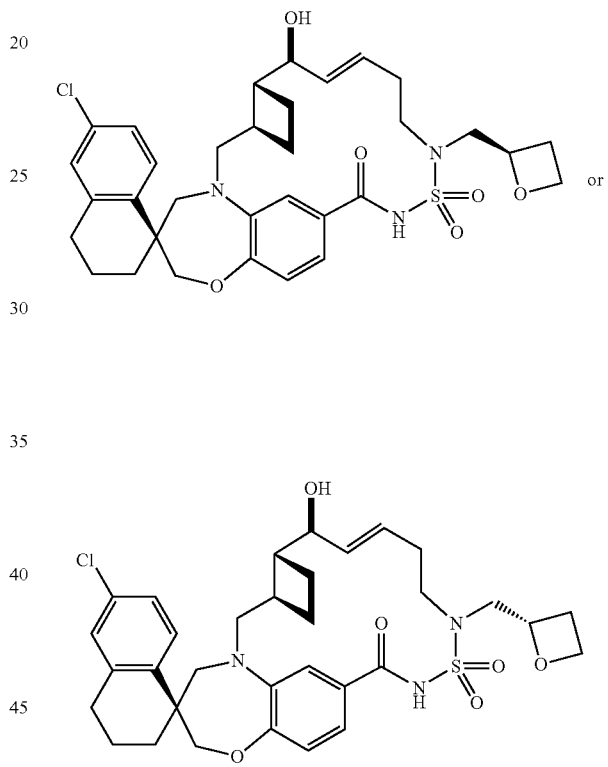

The title compound was isolated as the first eluting isomer from the SFC separation in the reaction described in Example 38, Step 3. $^1$H NMR (400 MHz, CDCl$_3$) δ 8.63 (s, 1H), 7.73 (d, J=8.61 Hz, 1H), 7.20 (dd, J=2.35, 8.61 Hz, 1H), 7.11 (d, J=2.35 Hz, 1H), 7.00-6.93 (m, 2H), 6.89 (br. s, 1H), 5.99-5.91 (m, 1H), 5.75 (dd, J=7.53, 15.4 Hz, 1H), 5.12 (qd, J=2.84, 7.60 Hz, 1H), 4.71 (td, J=6.06, 8.02 Hz, 1H), 4.56 (dt, J=5.97, 9.19 Hz, 1H), 4.27-4.20 (m, 2H), 4.16-4.07 (m, 2H), 3.93-3.86 (m, 1H), 3.77-3.64 (m, 3H), 3.54-3.46 (m, 1H), 3.29 (d, J=14.1 Hz, 1H), 3.15 (d, J=6.65 Hz, 1H), 2.83-2.70 (m, 3H), 2.56-2.40 (m, 4H), 2.35-2.27 (m, 1H), 2.07-1.91 (m, 3H), 1.89-1.64 (m, 2H), 1.60 (s, 2H), 1.55-1.39 (m, 2H). m/z (ESI, +ve ion) 643.2 (M+H)$^+$.

Example 40. (1S,3'R,6'R,7'S,8'E)-6-chloro-7'-hydroxy-12'-(3-oxetanylmethyl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

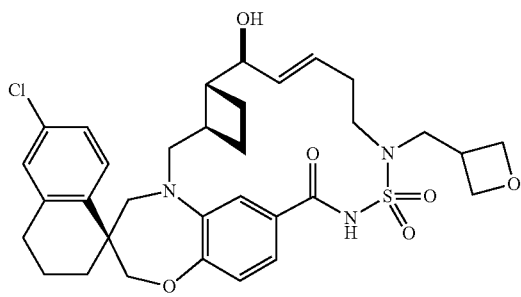

Step 1: oxetan-3-ylmethyl 4-methylbenzenesulfonate

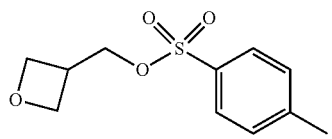 [SMILES: Cc1ccc(S(=O)(=O)OCC2COC2)cc1]

The title compound was prepared from oxetan-3-ylmethanol by a procedure similar to the one described in Example 38, Step 1 (1.80 g, 7.43 mmol, 65.5% yield).

Step 2: (1S,3'R,6'R,7'S,8'E)-6-chloro-7'-hydroxy-12'-(3-oxetanylmethyl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide To a solution of (1S,3'R,6'R,7'S,8'E)-6-chloro-7'-[(tert-butyldimethylsilyl)oxy]-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide (58 mg, 0.085 mmol, Example 32, step 1) in THF (1 mL) in an oven-dried microwave tube was added lithium bis(trimethylsilyl) amide, 1.0 M solution in THF (0.338 mL, 0.338 mmol) and the reaction was stirred at 0° C. for 10 minutes followed by the addition of a solution of oxetan-3-ylmethyl 4-methylbenzenesulfonate (71.7 mg, 0.296 mmol) in THF (0.4 mL). The resulting mixture was stirred at 100° C. in a microwave oven for 3.5 hours. The reaction was quenched with saturated NH₄Cl and extracted with EtOAc. The organic extract was washed with brine, dried with MgSO₄, filtered and concentrated to give a crude alkylation product. The crude was treated with tetrabutylammonium fluoride solution, (1.0 M in THF, 0.994 mL, 3.80 mmol) and a small amount of molecular sieve at 55° C. for 1 hour. After concentration the residue was purified by reversed phase preparatory HPLC (Gemini™ Prep C18 5 μm column; Phenomenex, Torrance, CA; gradient elution of 45% to 85% MeCN in water, where both solvents contain 0.1% TFA, 30 min method) to afford the title compound as a solid (42 mg, 0.065 μmol, 77% yield). ¹H NMR (400 MHz, CDCl₃) δ 9.16 (br. s, 1H), 7.69 (d, J=8.41 Hz, 1H), 7.19 (dd, J=2.25, 8.51 Hz, 1H), 7.11 (d, J=2.15 Hz, 1H), 6.97-6.81 (m, 2H), 6.76 (br. s, 1H), 6.11-5.97 (m, 1H), 5.72 (dd, J=7.73, 15.2 Hz, 1H), 4.92-4.82 (m, 2H), 4.66 (t, J=6.06 Hz, 1H), 4.54 (t, J=6.06 Hz, 1H), 4.45-4.28 (m, 2H), 4.17-3.95 (m, 2H), 3.85 (dd, J=6.55, 15.2 Hz, 1H), 3.69 (t, J=14.0 Hz, 3H), 3.37 (dt, J=6.82, 13.6 Hz, 1H), 3.30-3.17 (m, 2H), 3.16-2.96 (m, 2H), 2.95-2.972 (m, 2H), 2.60-2.37 (m, 2H), 2.37-2.23 (m, 2H), 2.07-1.92 (m, 3H), 1.89-1.79 (m, 2H), 1.79-1.59 (m, 2H), 1.44 (t, J=12.4 Hz, 1H). m/z (ESI, +ve ion) 643.2 (M+H)⁺.

Example 41. (1S,3'R,6'R,7'S,8'E)-6-chloro-7'-hydroxy-12'-(2-(R)-oxiranylmethyl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide and (1S,3'R,6'R,7'S,8'E)-6-chloro-7'-hydroxy-12'-(2-(S)-oxiranylmethyl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

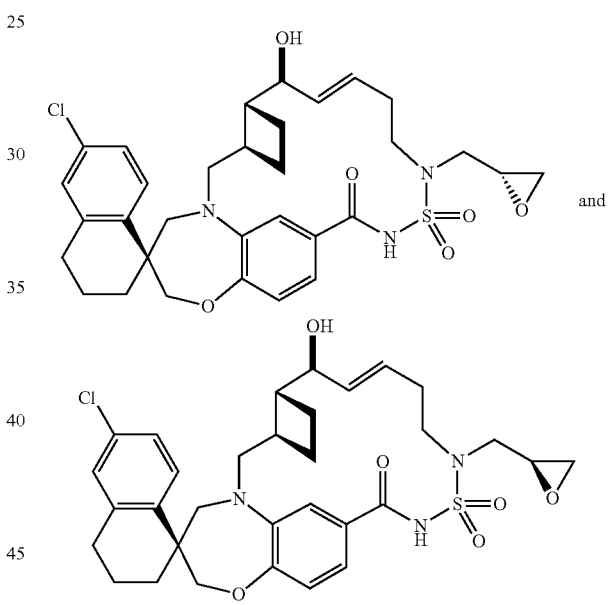

To a solution of diisopropylamine (redistilled, 99.95%, 0.069 mL, 0.490 mmol) in THF (1 mL) in an oven-dried 100 mL round-bottom flask was added butyllithium solution (1.6M in hexanes, 0.331 mL, 0.530 mmol) at 0° C. and the reaction was stirred at 0° C. for 20 minutes. To a solution of (1S,3'R,6'R,7'S,8'E)-6-chloro-7'-[(tert-butyldimethylsilyl)oxy]-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide (14 mg, 0.020 mmol; Example 32, Step 1) in THF (0.3 mL) at −78° C. was added 140 μL of the LDA solution prepared above and this mixture was stirred for 30 minutes allowing the temperature to rise from −78 degree to 0° C. followed by addition of 2-(bromomethyl) oxirane (4.22 μl, 0.051 mmol). The resulting mixture was stirred at ambient temperature for 17 hours and at 60° C. for 24 hours. No desired product was detected by LCMS. The dried reaction mixture was dissolved in 0.5 mL of 2-(bromomethyl) oxirane, transferred to an oven-dried microwave tube and stirred at 100° C. for 4 hours. The reaction was quenched with saturated NH₄Cl and extracted with EtOAc. The organic extract was washed with brine, dried with MgSO₄, filtered and concentrated. The residue was treated with tetrabutylammonium fluoride, (1.0M in THF, 1.04 mL, 1.04 mmol) and a small amount of molecular sieve at 50° C. for 1.5 hours. The reaction was concentrated to give a residue which was purified by reversed phase preparatory HPLC (Gemini™ Prep C₁₈ 5 μm column; Phenomenex, Torrance, CA; gradient elution of 30% to 70% MeCN in water, where both solvents contain 0.1% TFA, 30 min method) to afford the title compound as a mixture of two diastereoisomers with a ratio of 4/3 determined by ¹H NMR analysis. ¹H NMR (400 MHz, CDCl₃) δ 8.66 (s, 0.4H), 8.61 (s, 0.6H), 7.72 (d, J=8.4 Hz, 1H), 7.20 (dd, J=2.1, 8.5 Hz, 1H), 7.11 (d, J=2.0 Hz, 1H), 7.03-6.88 (m, 3H), 5.95-5.84 (m, 1H), 5.79-5.69 (m, 1H), 4.25-4.04 (m, 4H), 4.01-3.81 (m, 1H), 3.78-3.63 (m, 2H), 3.60-3.47 (m, 1H), 3.44-3.20 (m, 3H), 2.89-2.76 (m, 3H), 2.54-2.27 (m, 4H), 2.05-1.96 (m, 2H), 1.95-1.76 (m, 4H), 1.69 (br. s, 2H), 1.59-1.39 (m, 3H). m/z (ESI, +ve ion) 629.2 (M+H)⁺.

Example 42. (1S,3'R,6'R,7'S,8'E)-6-chloro-7'-hydroxy-12'-(2-propen-1-yl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

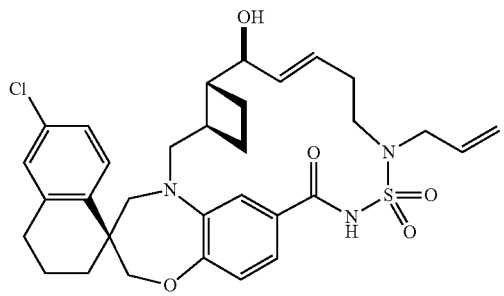

The title compound was prepared from (1S,3'R,6'R,7'S,8'E)-6-chloro-7'-[(tert-butyldimethylsilyl)oxy]-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide (Example 32, Step 1) by a procedure similar to the one described in Example 34 and it was obtained as a solid (8.0 mg, 0.013 mmol, 63.3% yield). ¹H NMR (500 MHz, CDCl₃) δ 8.53 (br. s, 1H), 7.72 (d, J=8.56 Hz, 1H), 7.20 (dd, J=2.20, 8.56 Hz, 1H), 7.10 (s, 1H), 6.99-6.90 (m, 3H), 5.94-5.84 (m, 2H), 5.73 (dd, J=15.41, 7.82, 15.4 Hz, 1H), 5.32-5.24 (m, 2H), 4.65 (d, J=13.9 Hz, 1H), 4.22 (dd, J=4.52, 7.46 Hz, 1H), 4.26-4.07 (m, 2H), 3.91 (dd, J=6.48, 16.8 Hz, 1H), 3.80-3.64 (m, 3H), 3.37-3.19 (m, 2H), 3.17 (br. s, 1H), 2.84-2.73 (m, 2H), 2.51-2.36 (m, 3H), 2.33-2.18 (m, 1H), 2.04-1.88 (m, 3H), 1.88-1.79 (m, 2H), 1.79-1.61 (m, 3H), 1.48 (t, J=12.2 Hz, 1H). m/z (ESI, +ve ion) 613.2 (M+H)⁺.

Example 43. methyl(((1S,3'R,6'R,7'S,8'E)-6-chloro-12'-ethyl-13',13'-dioxido-15'-oxo-3,4-dihydro-2H-spiro[naphthalene-1,22'-[20]oxa[13]thia[1,12,14]triazatetracyclo[14.7.2.0³,⁶.0¹⁹,²⁴]pentacosa[8,16,18,24]tetraen]-7'-yl)oxy)acetate

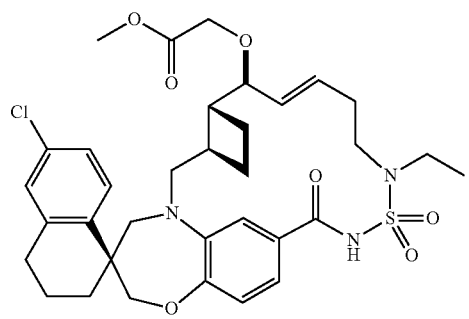

To a solution of Example 29 (16 mg, 0.027 mmol) in THF (0.53 mL) was added sodium hydride, 60% dispersion in mineral oil (5.33 mg, 0.133 mmol) and the reaction was stirred at 0° C. for 30 minutes followed by addition of methyl 2-bromoacetate (4.88 μL, 0.053 mmol). The resulting mixture was stirred at ambient temperature for 17 hours whereupon 17% of the desires product was detected by LCMS. Methyl 2-bromoacetate (4.88 μL, 0.053 mmol) and sodium hydride, 60% dispersion in mineral oil (5.33 mg, 0.133 mmol) were then added and the reaction was stirred at ambient temperature for 25 hours. The reaction was quenched with saturated NH₄Cl and extracted with EtOAc. The organic extract was washed with brine, dried with MgSO₄, filtered and concentrated to give a residue which was purified by reversed phase preparatory HPLC (Gemini™ Prep C₁₈ 5 μm column; Phenomenex, Torrance, CA; gradient elution of 50% to 85% MeCN in water, where both solvents contain 0.1% TFA, 30 min method) to afford the title compound as a solid (10.2 mg, 0.015 mmol, 56.9% yield). ¹H NMR (400 MHz, CDCl₃) δ 8.46 (s, 1H), 7.72 (d, J=8.61 Hz, 1H), 7.20 (dd, J=2.25, 8.51 Hz, 1H), 7.11 (d, J=2.15 Hz, 1H), 6.95-6.88 (m, 2H), 6.75 (s, 1H), 6.06-5.97 (m, 1H), 5.59 (dd, J=9.10, 15.6 Hz, 1H), 4.22-4.15 (m, 1H), 4.13-4.01 (m, 3H), 3.90 (dd, J=3.91, 9.00 Hz, 1H), 3.85-3.70 (m, 5H), 3.38-3.18 (m, 3H), 3.06 (dd, J=9.88, 14.8 Hz, 1H), 2.87-2.72 (m, 2H), 2.64-2.46 (m, 2H), 2.42 (br. s, 2H), 2.37-2.22 (m, 2H), 2.08-1.92 (m, 3H), 1.90-1.76 (m, 3H), 1.71-1.61 (m, 1H), 1.42 (t, J=12.2 Hz, 1H), 1.29 (t, J=7.14 Hz, 3H). m/z (ESI, +ve ion) 673.2 (M+H)⁺.

Example 44. (((1S,3'R,6'R,7'S,8'E)-6-chloro-12'-ethyl-13',13'-dioxido-15'-oxo-3,4-dihydro-2H-spiro[naphthalene-1,22'-[20]oxa[13]thia[1,12,14]triazatetracyclo[14.7.2.0³,⁶.0¹⁹,²⁴]pentacosa[8,16,18,24]tetraen]-7'-yl)oxy)acetic Acid

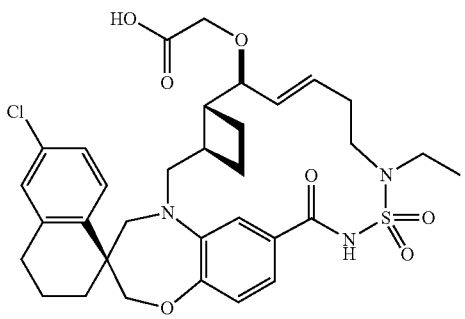

A mixture of Example 43 (8 mg, 0.012 mmol) and lithium hydroxide monohydrate (1.50 mg, 0.036 mmol) in THF (0.3 mL), water (0.10 mL) and MeOH (0.100 mL) was stirred at ambient temperature for 1 hour. The reaction was acidified with aqueous 1M HCl and concentrated to give a residue which was purified by reversed phase preparatory HPLC (Gemini™ Prep C$_{18}$ 5 μm column; Phenomenex, Torrance, CA) to afford the title compound as a solid (4 mg, 6.08 μmol, 51.1% yield). ¹H NMR (400 MHz, CDCl$_3$) δ 8.56 (s, 1H), 7.71 (d, J=8.61 Hz, 1H), 7.20 (dd, J=2.25, 8.51 Hz, 1H), 7.11 (d, J=2.35 Hz, 1H), 6.95-6.88 (m, 2H), 6.77 (br. s, 1H), 6.13-6.04 (m, 1H), 5.58 (dd, J=9.88, 15.4 Hz, 1H), 4.18-3.98 (m, 6H), 3.84-3.60 (m, 2H), 3.39 (dd, J=7.24, 14.9 Hz, 1H), 3.32-3.12 (m, 2H), 3.10 (br. s, 1H), 2.86-2.69 (m, 2H), 2.65-2.44 (m, 2H), 2.43-2.23 (m, 3H), 2.20 (br. s, 1H), 2.14-1.93 (m, 3H), 1.90-1.69 (m, 4H), 1.45 (t, J=12.4 Hz, 1H), 1.30 (t, J=7.04 Hz, 3H). m/z (ESI, +ve ion) 659.2 (M+H)⁺.

Example 45. (1S,3'R,6'R,7'S,8'E)-6-chloro-12'-ethyl-7'-hydroxy-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

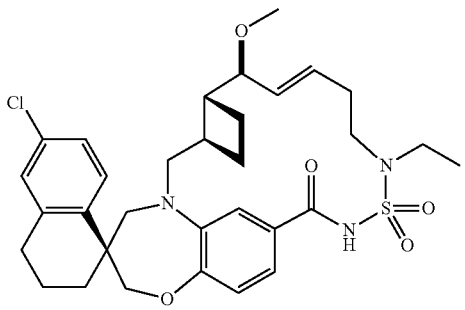

To a solution of Example 29 (2 mg, 0.035 mmol) in THF (0.5 mL) in a vial (4 mL size) at 0° C. was added sodium hydride, 60% dispersion in mineral oil (8.40 mg, 0.210 mmol) and the reaction was stirred at 0° C. for 30 minutes followed by an addition of iodomethane (6.53 μL, 0.105 mmol). The resulting mixture was stirred at ambient temperature for an additional 1 hour. LCMS showed completion of the reaction. The reaction was quenched by the dropwise addition of 1 M HCl and extracted with EtOAc. The extract was washed with water and brine, dried with MgSO$_4$, filtered and concentrated. The residue was purified by reversed phase preparatory HPLC (Gemini™ Prep C$_{18}$ 5 μm column; Phenomenex, Torrance, CA; gradient elution of 45% to 80% MeCN in water, where both solvents contain 0.1% TFA, 30 min method) to afford the title compound as a solid (6 mg, 9.77 μmol, 27.9% yield). ¹H NMR (400 MHz, CDCl$_3$) δ 8.41 (s, 1H), 7.72 (d, J=8.41 Hz, 1H), 7.20 (dd, J=2.25, 8.51 Hz, 1H), 7.11 (d, J=2.35 Hz, 1H), 6.95-6.86 (m, 2H), 6.75 (d, J=1.56 Hz, 1H), 6.06-5.97 (m, 1H), 5.61-5.53 (m, 1H), 4.24 (dd, J=7.34, 14.8 Hz, 1H), 4.14-4.04 (m, 2H), 3.88-3.68 (m, 4H), 3.38-3.18 (m, 6H), 3.01 (dd, J=9.98, 15.3 Hz, 1H), 2.86-2.72 (m, 2H), 2.61-2.39 (m, 2H), 2.35-2.19 (m, 2H), 2.19-1.93 (m, 3H), 1.89-1.63 (m, 4H), 1.42 (t, J=12.4 Hz, 1H), 1.29 (t, J=7.04 Hz, 3H). m/z (ESI, +ve ion) 615.2 (M+H)⁺.

Example 46. (1S,3'R,6'R,7'S,8'E)-6-chloro-7'-methoxy-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

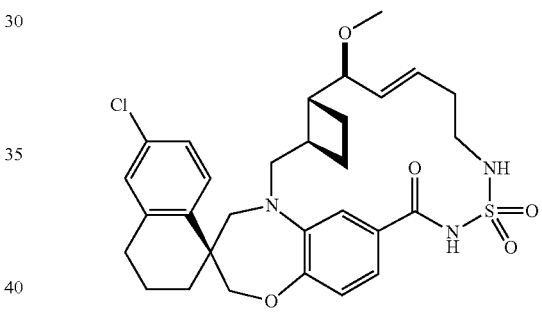

To a solution of Example 19 (11 mg, 0.019 mmol) in THF (0.25 mL) in a vial (4 mL size vial) at 0° C. was added sodium hydride, 60% dispersion in mineral oil (4.61 mg, 0.115 mmol) and the reaction was stirred at 0° C. for 20 minutes followed by the addition of iodomethane (3.59 μL, 0.058 mmol) and the reaction was stirred at ambient temperature for 4.5 hours. LCMS showed the completion of the reaction. The reaction was quenched by the dropwise addition of 1M HCl at 0° C. and then extracted with EtOAc. The EtOAc extract was washed with water and brine, dried with anhydrous MgSO$_4$, filtered and concentrated. The residue was purified by HPLC (Gemini™ Prep C$_{18}$ 5 μm column; Phenomenex, Torrance, CA; gradient elution of 45% to 80% MeCN in water, where both solvents contain 0.1% TFA, 30 min method) to afford the title compound as the first eluting compound. ¹H NMR (400 MHz, CDCl$_3$) δ 8.29 (s, 1H), 7.72 (d, J=8.41 Hz, 1H), 7.21 (dd, J=2.35, 8.61 Hz, 1H), 7.12 (d, J=2.15 Hz, 1H), 6.97-6.85 (m, 3H), 6.02-5.94 (m, 1H), 5.78 (t, J=5.97 Hz, 1H), 5.59 (dd, J=8.80, 15.3 Hz, 1H), 4.16-4.05 (m, 2H), 3.83 (d, J=14.9 Hz, 1H), 3.78-3.68 (m, 2H), 3.36-3.21 (m, 6H), 3.03 (dd, J=10.2, 15.3 Hz, 1H), 2.86-2.73 (m, 2H), 2.55-2.44 (m, 2H), 2.40-2.21 (m, 2H), 2.15-1.64 (m, 7H), 1.42 (t, J=12.5 Hz, 1H). m/z (ESI, +ve ion) 587.2 (M+H)⁺.

Example 47. (1S,3'R,6'R,7'S,8'E)-6-chloro-7'-methoxy-12'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

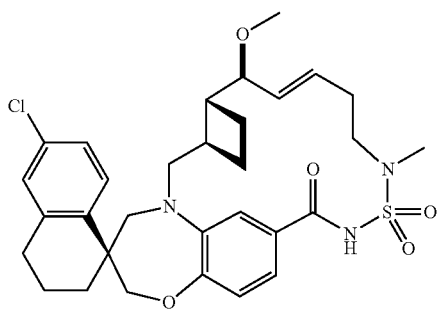

The title compound was isolated as the second eluting fraction from the reaction described in Example 46 (1.7 mg, 2.83 μmol, 14.7% yield). ¹H NMR (400 MHz, CDCl₃) δ 8.35 (s, 1H), 7.73 (d, J=8.41 Hz, 1H), 7.20 (d, J=8.84 Hz, 1H), 7.11 (d, J=2.35 Hz, 1H), 7.03-6.89 (m, 2H), 6.79 (d, J=1.57 Hz, 1H), 6.06-5.98 (m, 1H), 5.58 (dd, J=8.90, 15.6 Hz, 1H), 4.24-4.05 (m, 2H), 3.90 (dt, J=4.62, 14.8 Hz, 1H), 3.82-3.62 (m, 3H), 3.34 (s, 3H), 3.30 (s, 3H), 3.27-3.00 (m, 4H), 2.89-2.70 (m, 2H), 2.62-2.41 (m, 2H), 2.41-2.22 (m, 2H), 2.21-1.93 (m, 2H), 1.92-1.63 (m, 4H), 1.43 (t, J=12.3 Hz, 1H). m/z (ESI, +ve ion) 601.2 (M+H)⁺.

Example 48. (1S,3'R,6'R,7'S,8'E)-6-chloro-7'-(2-methoxyethoxy)-12'-(2-methoxyethyl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

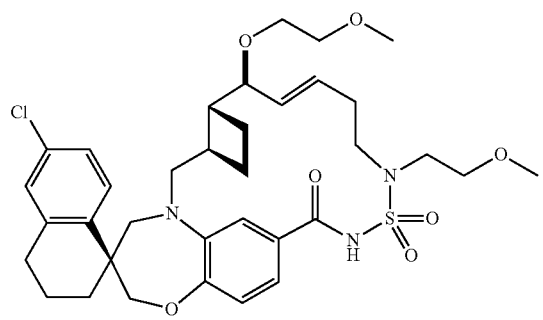

The title compound was prepared from (1S,3'R,6'R,7'S,8'E)-6-chloro-7'-[(tert-butyldiphenylsilyl)oxy]-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide (Example 31, Step 1) by a procedure similar to the one described in Example 34 (0.40 mg, 0.581 μmol, 4.71% yield). ¹H NMR (400 MHz, CDCl₃) δ 8.41 (s, 1H), 7.72 (d, J=8.6 Hz, 1H), 7.20 (dd, J=2.3, 8.4 Hz, 1H), 7.11 (d, J=2.2 Hz, 1H), 6.95-6.88 (m, 2H), 6.79 (s, 1H), 6.02-5.94 (m, 1H), 5.59 (dd, J=8.5, 15.6 Hz, 1H), 4.33 (td, J=4.3, 15.5 Hz, 1H), 4.14-4.05 (m, 2H), 3.91 (td, J=4.5, 15.0 Hz, 1H), 3.85-3.78 (m, 1H), 3.74 (br. s, 1H), 3.71-3.58 (m, 4H), 3.56-3.42 (m, 5H), 3.40 (s, 3H), 3.40 (s, 3H), 3.22 (d, J=14.3 Hz, 1H), 3.03 (dd, J=9.8, 15.3 Hz, 1H), 2.85-2.72 (m, 2H), 2.56-2.46 (m, 2H), 2.34-2.24 (m, 2H), 2.08-1.92 (m, 3H), 1.89-1.69 (m, 3H), 1.65 (s, 2H), 1.42 (t, J=12.2 Hz, 1H). m/z (ESI, +ve ion) 689.2 (M+H)⁺.

Example 49. (1S,3'R,6'R,7'S,8'E,11'S)-6-chloro-7'-hydroxy-11'-methyl-12'-((2S)-tetrahydro-2-furanylmethyl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

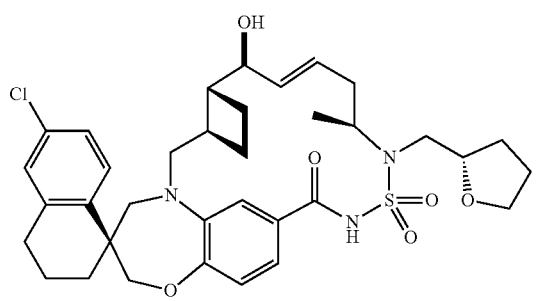

Step 1: tert-butyl N—((S)-pent-4-en-2-yl)-N—(((S)-tetrahydrofuran-2-yl)methyl)sulfamoylcarbamate

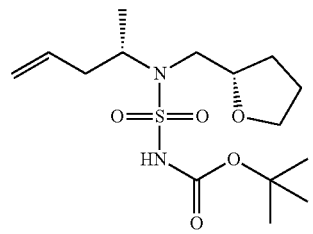 [SMILES: C=CC[C@H](C)N(C[C@@H]1CCCO1)S(=O)(=O)NC(=O)OC(C)(C)C]

The title compound was prepared from (S)—N—(((S)-tetrahydrofuran-2-yl)methyl)pent-4-en-2-amine by a procedure similar to the one described in Example 29, Step 1 (0.867 g, 2.49 mmol, 56.9% yield).

Step 2: N—((S)-pent-4-en-2-yl)-N—((S)-tetrahydrofuran-2-yl)sulfuric Diamide

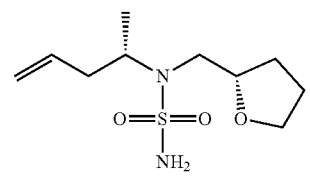 [SMILES: C=CC[C@H](C)N(C[C@@H]1CCCO1)S(N)(=O)=O]

The title compound was prepared from tert-butyl N—((S)-pent-4-en-2-yl)-N—(((S)-tetrahydrofuran-2-yl)methyl) sulfamoylcarbamate by a procedure similar to the one described in Example 29, Step 2 (0.583 g, 2.35 mmol, 94% yield).

Step 3: (S)-6'-chloro-5-(((1R,2R)-2-((S)-1-hydroxy-allyl)cyclobutyl)methyl)-N—(N—((S)-pent-4-en-2-yl)-N—((S)-tetrahydrofuran-2-yl)methyl)sulfamoyl)-3',4',4',5-tetrahydro-2H,2'H-spiro[benzo[b][1,4]oxazepine-3,1'-naphthalene]-7-carboxamide

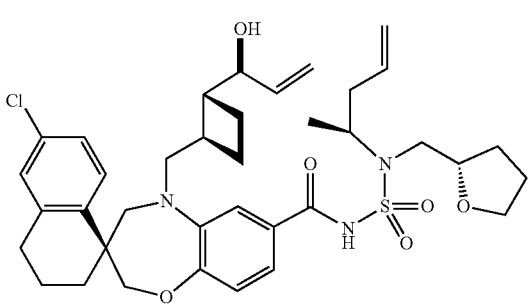

The title compound was prepared from Intermediate AA11A and N—((S)-pent-4-en-2-yl)-N—((S)-tetrahydrofuran-2-yl)sulfuric diamide by a procedure similar to the one described in Example 29, Step 3 (61 mg, 0.087 mmol, 58.4% yield).

Step 4: (1S,3'R,6'R,7'S,8'E,11'S)-6-chloro-7'-hydroxy-11'-methyl-12'-((2S)-tetrahydro-2-furanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide The title compound was prepared from (S)-6'-chloro-5-(((1R,2R)-2-((S)-1-hydroxyallyl)cyclobutyl)methyl)-N—(N—((S)-pent-4-en-2-yl)-N—(((S)-tetrahydrofuran-2-yl)methyl)sulfamoyl)-3',4',4',5-tetrahydro-2H,2'H-spiro[benzo[b][1,4]oxazepine-3,1'-naphthalene]-7-carboxamide by a procedure similar to the one described in Example 29, Step 4 and it was isolated after HPLC purification, as the first eluting isomer (2.7 mg, 4.03 μmol, 4.69% yield). $^1$H NMR (400 MHz, CDCl$_3$) δ 8.58 (s, 1H), 7.72 (d, J=8.41 Hz, 1H), 7.20 (dd, J=2.25, 8.51 Hz, 1H), 7.11 (d, J=2.15 Hz, 1H), 7.05-6.92 (m, 3H), 5.87-5.78 (m, 1H), 5.76-5.67 (m, 1H), 4.19-4.06 (m, 4H), 3.94-3.69 (m, 6H), 3.48 (dd, J=2.84, 15.9 Hz, 1H), 3.30 (d, J=14.3 Hz, 1H), 3.14 (dd, J=6.65, 15.1 Hz, 1H), 2.85-2.74 (m, 2H), 2.65 (ddd, J=5.58, 11.0, 16.3 Hz, 1H), 2.53-2.41 (m, 2H), 2.30-2.22 (m, 1H), 2.10-1.84 (m, 7H), 1.84-1.61 (m, 5H), 1.51-1.34 (m, 4H). m/z (ESI, +ve ion) 671.2 (M+H)$^+$.

Example 50. (1S,3'R,6'R,7'S,8'Z,11'S)-6-chloro-7'-hydroxy-11'-methyl-12'-((2S)-tetrahydro-2-furanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

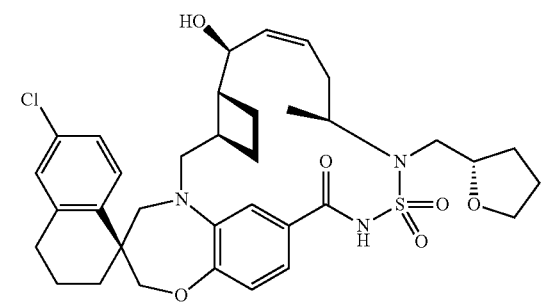

The title compound was prepared in the reaction described in Example 49, Step 4 and it was isolated after HPLC purification, as the second eluting isomer (0.8 mg, 1.19 μmol, 1.4% yield). $^1$H NMR (400 MHz, CDCl$_3$) δ 9.13 (br. s, 1H), 7.71 (d, J=8.41 Hz, 1H), 7.24 (s, 1H), 7.20-7.18 (dd, J=2.2, 8.5 Hz, 1H), 7.11 (d, J=2.15 Hz, 1H), 6.98-6.91 (m, 2H), 5.79-5.67 (m, 2H), 4.27 (br. s, 1H), 4.20-4.02 (m, 4H), 3.92-3.85 (m, 1H), 3.74-3.59 (m, 3H), 3.56 (d, J=9.19 Hz, 1H), 3.52-3.28 (m, 3H), 2.85-2.74 (m, 2H), 2.57-2.39 (m, 3H), 2.26 (dt, J=5.50, 15.4 Hz, 1H), 2.06-1.79 (m, 8H), 1.70-1.51 (m, 4H), 1.44-1.28 (m, 4H). m/z (ESI, +ve ion) 671.3 (M+H)$^+$.

Example 51. (1S,3'R,6'R,7'S,8'E,11'R)-6-chloro-7'-hydroxy-11'-methyl-12'-((2S)-tetrahydro-2-furanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

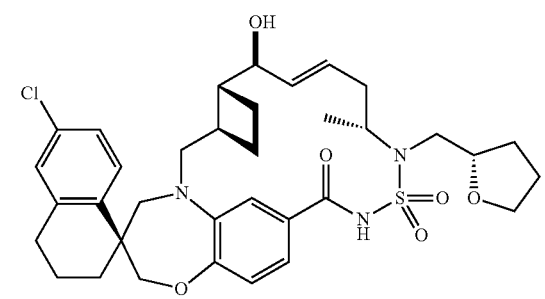

Step 1: tert-butyl N—((R)-pent-4-en-2-yl)-N—(((S)-tetrahydrofuran-2-yl)methyl)sulfamoylcarbamate

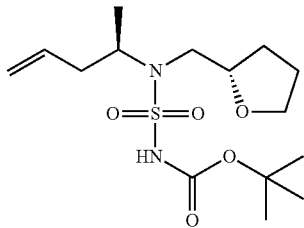 [SMILES: C=CC[C@@H](C)N(C[C@@H]1CCCO1)S(=O)(=O)NC(=O)OC(C)(C)C]

The title compound was prepared from (R)—N—(((S)-tetrahydrofuran-2-yl)methyl)pent-4-en-2-amine by a procedure similar to the one described in Example 29, Step 1 (0.88 g, 2.53 mmol, 43.9% yield).

Step 2: N—(R)-pent-4-en-2-yl, N—(S)-tetrahydrofuran-2-yl Sulfuric Diamide

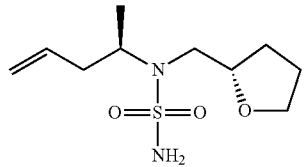 [SMILES: C=CC[C@@H](C)N(C[C@@H]1CCCO1)S(N)(=O)=O]

The title compound was prepared from tert-butyl N—((R)-pent-4-en-2-yl)-N—(((S)-tetrahydrofuran-2-yl)methyl) sulfamoylcarbamate by a procedure similar to the one described in Example 29, Step 2 (0.622 g, 2.50 mmol, 99% yield).

Step 3: (S)-6'-chloro-5-(((1R,2R)-2-((S)-1-hydroxyallyl)cyclobutyl)methyl)-N—(N—((R)-pent-4-en-2-yl)-N—(((S)-tetrahydrofuran-2-yl)methyl)sulfamoyl)-3',4,4',5-tetrahydro-2H,2'H-spiro[benzo[b][1,4]oxazepine-3,1'-naphthalene]-7-carboxamide

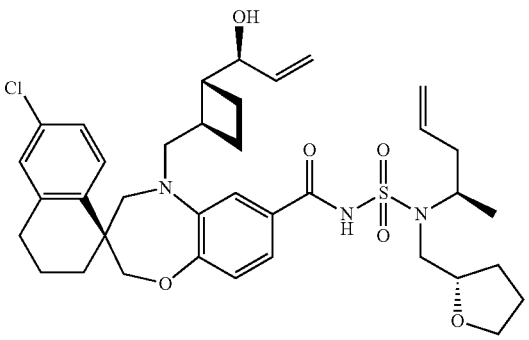

The title compound was prepared from Intermediate AA11A and N—(R)-pent-4-en-2-yl, N—(S)-tetrahydrofuran-2-yl sulfuric diamide by a procedure similar to the one described in Example 29, Step 3 (65 mg, 0.093 mmol, 62.2% yield).

Step 4: (1S,3'R,6'R,7'S,8'E,11'R)-6-chloro-7'-hydroxy-11'-methyl-12'-((2S)-tetrahydro-2-furanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide The title compound was prepared from (S)-6'-chloro-5-(((1R,2R)-2-((S)-1-hydroxyallyl)cyclobutyl)methyl)-N—(N—((R)-pent-4-en-2-yl)-N—(((S)-tetrahydrofuran-2-yl)methyl)sulfamoyl)-3',4,4',5-tetrahydro-2h,2'h-spiro[benzo[b][1,4]oxazepine-3,1'-naphthalene]-7-carboxamide by a procedure similar to the one described in Example 29, Step 4 and was isolated via preparative HPLC as the first eluting isomer (20 mg, 0.030 mmol, 32.1% yield). $^1$H NMR (400 MHz, CDCl$_3$) δ 9.15 (br. s, 1H), 7.69 (d, J=8.4 Hz, 1H), 7.22 (br. s, 1H), 7.17 (dd, J=2.1, 8.5 Hz, 1H), 7.09 (d, J=2.2 Hz, 1H), 6.97-6.87 (m, 2H), 5.70 (d, J=5.9 Hz, 2H), 4.25 (br. s, 1H), 4.18-4.06 (m, 4H), 4.03 (br. s, 1H), 3.86 (d, J=7.8 Hz, 1H), 3.72-3.57 (m, 3H), 3.57-3.44 (m, 2H), 3.40 (d, J=14.3 Hz, 2H), 2.82-2.70 (m, 2H), 2.51 (d, J=7.8 Hz, 1H), 2.42 (d, J=10.6 Hz, 2H), 2.26 (br. s, 1H), 2.06-1.78 (m, 5H), 1.75-1.47 (m, 5H), 1.41-1.21 (m, 5H). m/z (ESI, +ve ion) 671.3 (M+H)$^+$.

Example 52. (1S,3'R,6'R,7'S,8'Z,11'R)-6-chloro-7'-hydroxy-11'-methyl-12'-((2S)-tetrahydro-2-furanylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

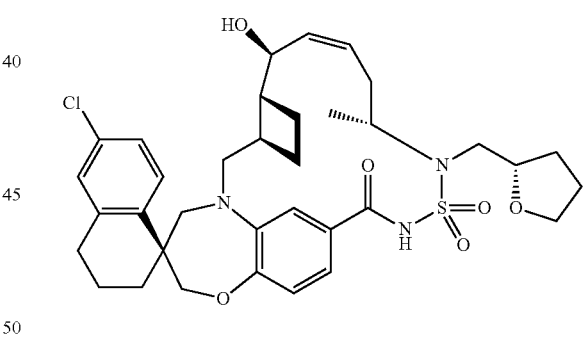

The title compound was prepared from the reaction described in Example 51, Step 4 and was isolated via preparative HPLC as the second eluting isomer (4.9 mg, 7.31 μmol, 7.85% yield). $^1$H NMR (400 MHz, CDCl$_3$) δ 10.2 (br. s, 1H), 7.74 (d, J=8.41 Hz, 1H), 7.44 (dd, J=1.86, 8.31 Hz, 1H), 7.31 (m, 1H), 7.19 (dd, J=2.35, 8.41 Hz, 1H), 7.11 (d, J=2.15 Hz, 1H), 6.98 (d, J=8.22 Hz, 1H), 5.85 (td, J=4.89, 11.0 Hz, 1H), 5.67 (dd, J=7.63, 10.6 Hz, 1H), 4.41 (t, J=7.73 Hz, 1H), 4.25-4.04 (m, 4H), 3.96-3.86 (m, 3H), 3.79 (td, J=6.06, 7.83 Hz, 1H), 3.63 (d, J=14.1 Hz, 1H), 3.22-3.02 (m, 3H), 2.90 (br. s, 1H), 2.84-2.72 (m, 2H), 2.31-2.18 (m, 2H), 2.13-1.87 (m, 7H), 1.86-1.79 (m, 2H), 1.72-1.61 (m, 2H), 1.50-1.22 (m, 6H). m/z (ESI, +ve ion) 671.4 (M+H)$^+$.

Example 53. (1S,3'R,6'R,7'S,8'E,11'S)-6-chloro-7'-hydroxy-11'-methyl-12'-((2R)-tetrahydro-2-furanylmethyl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

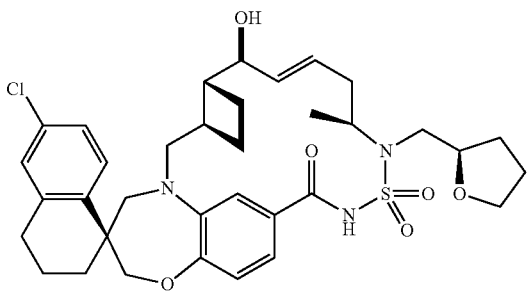

Step 1: tert-butyl N—((S)-pent-4-en-2-yl)-N—(((R)-tetrahydrofuran-2-yl)methyl)sulfamoylcarbamate

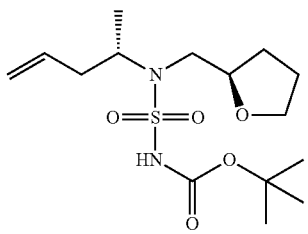 [SMILES: C=CC[C@H](C)N(C[C@H]1CCCO1)S(=O)(=O)NC(=O)OC(C)(C)C]

The title compound was prepared from (S)—N—(((R)-tetrahydrofuran-2-yl)methyl)pent-4-en-2-amine by a procedure similar to the one described in Example 29, Step 1 (0.572 g, 1.64 mmol, 37.5% yield).

Step 2: N—(S)-pent-4-en-2-yl, N—(R)-tetrahydrofuran-2-yl sulfuric Diamide

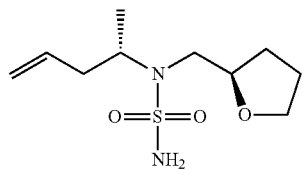

The title compound was prepared from tert-butyl N—((S)-pent-4-en-2-yl)-N—(((R)-tetrahydrofuran-2-yl)methyl) sulfamoylcarbamate by a procedure similar to the one described in Example 29, Step 2 (0.416 g, 1.68 mmol, 102% crude yield).

Step 3: (S)-6'-chloro-5-(((1R,2R)-2-((S)-1-hydroxyallyl)cyclobutyl)methyl)-N—(N—((S)-pent-4-en-2-yl)-N—(((R)-tetrahydrofuran-2-yl)methyl)sulfamoyl)-3',4,4',5-tetrahydro-2H,2'H-spiro[benzo[b][1,4]oxazepine-3,1'-naphthalene]-7-carboxamide

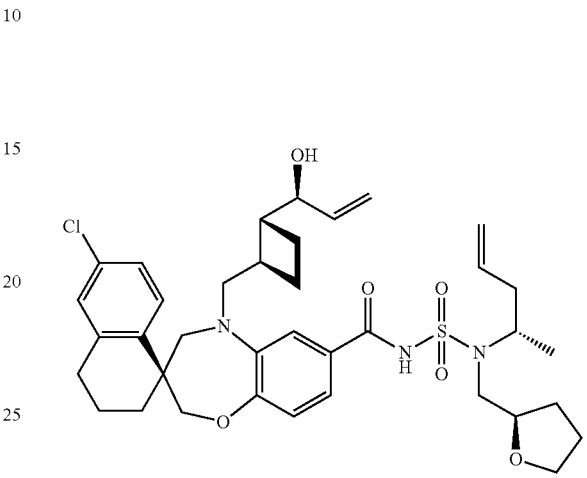

The title compound was prepared from Intermediate AA11A and N—(S)-pent-4-en-2-yl, N—(R)-tetrahydrofuran-2-yl sulfuric diamide by a procedure similar to the one described in Example 29, Step 3 (75 mg, 0.107 mmol, 71.8% yield).

Step 4: (1S,3'R,6'R,7'S,8'E,11'S)-6-chloro-7'-hydroxy-11'-methyl-12'-((2R)-tetrahydro-2-furanylmethyl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide The title compound was prepared from (S)-6'-chloro-5-(((1R,2R)-2-((S)-1-hydroxyallyl)cyclobutyl)methyl)-N—(N—((S)-pent-4-en-2-yl)-N—((R)-tetrahydrofuran-2-yl)methyl)sulfamoyl)-3',4,4',5-tetrahydro-2H,2'H-spiro[benzo[b][1,4]oxazepine-3,1'-naphthalene]-7-carboxamide by a procedure similar to the one described in Example 29, Step 4 and was isolated via preparative HPLC as the first eluting isomer (27 mg, 0.040 mmol, 37.5% yield). $^1$H NMR (400 MHz, CDCl$_3$) δ 8.87 (br. s, 1H), 7.70 (d, J=8.6 Hz, 1H), 7.25-7.16 (m, 2H), 7.11 (d, J=2.2 Hz, 1H), 7.02-6.88 (m, 2H), 5.85-5.72 (m, 1H), 5.70-5.58 (m, 1H), 4.20-4.08 (m, 2H), 4.06 (br. s, 2H), 3.94-3.71 (m, 2H), 3.71-3.53 (m, 3H), 3.50-3.24 (m, 3H), 2.86-2.74 (m, 3H), 2.71 (br. s, 3H), 2.59-2.40 (m, 3H), 2.38-2.23 (m, 1H), 2.08-1.80 (m, 6H), 1.74-1.48 (m, 4H), 1.47-1.30 (m, 3H). m/z (ESI, +ve ion) 671.2 (M+H)$^+$.

Example 54. (1S,3'R,6'R,7'S,8'Z,11'S)-6-chloro-7'-hydroxy-11'-methyl-12'-((2R)-tetrahydro-2-furanylmethyl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

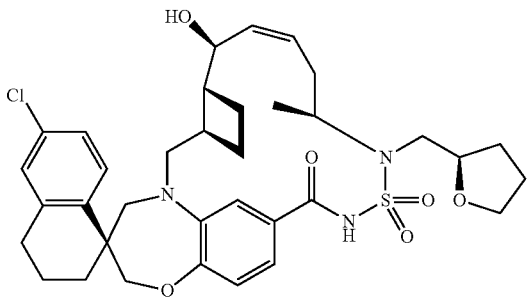

The title compound was prepared from the reaction described in Example 53, Step 4 and was isolated via preparative HPLC as the second eluting isomer (2.5 mg, 3.73 µmol, 3.47% yield). ¹H NMR (400 MHz, CDCl₃) δ 9.63 (br. s, 1H), 7.70 (d, J=8.4 Hz, 1H), 7.27-7.23 (m, 1H), 7.18 (dd, J=2.2, 8.5 Hz, 1H), 7.09 (d, J=2.2 Hz, 1H), 6.93 (d, J=8.2 Hz, 1H), 6.79 (s, 1H), 5.76-5.64 (m, 2H), 4.60-4.52 (m, 1H), 4.27-4.15 (m, 2H), 4.15-3.99 (m, 2H), 3.88-3.61 (m, 6H), 3.31 (d, J=14.3 Hz, 1H), 3.15 (dd, J=9.4, 15.1 Hz, 1H), 2.85-2.70 (m, 3H), 2.70-2.54 (m, 1H), 2.47-2.25 (m, 2H), 2.20-2.06 (m, 3H), 2.04-1.60 (m, 9H), 1.48-1.33 (m, 4H). m/z (ESI, +ve ion) 671.3 (M+H)⁺.

Example 55. (1S,3'R,6'R,7'S,8'E,11R)-6-chloro-7'-hydroxy-11'-methyl-12'-((2R)-tetrahydro-2-furanylmethyl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

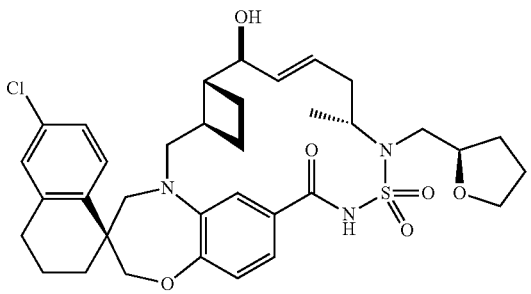

Step 1: tert-butyl N—((R)-pent-4-en-2-yl)-N—(((R)-tetrahydrofuran-2-yl)methyl)sulfamoylcarbamate

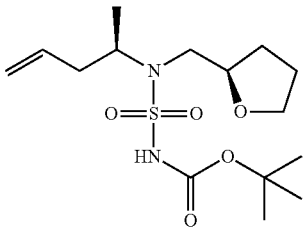 [SMILES: C=CC[C@@H](C)N(C[C@H]1CCCO1)S(=O)(=O)NC(=O)OC(C)(C)C]

The title compound was prepared from (R)—N—(((R)-tetrahydrofuran-2-yl)methyl)pent-4-en-2-amine by a procedure similar to the one described in Example 29, Step 1 (0.73 g, 2.10 mmol, 36.4% yield).

Step 2: N—(R)-pent-4-en-2-yl, N—(R)-tetrahydrofuran-2-yl Sulfuric Diamide

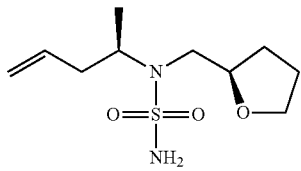 [SMILES: C=CC[C@@H](C)N(C[C@H]1CCCO1)S(N)(=O)=O]

The title compound was prepared from tert-butyl N—((R)-pent-4-en-2-yl)-N—(((R)-tetrahydrofuran-2-yl) methyl) sulfamoylcarbamate by a procedure similar to the one described in Example 29, Step 2 (0.513 g, 2.06 mmol, 99% crude yield).

Step 3: (S)-6'-chloro-5-(((1R,2R)-2-((S)-1-hydroxyallyl)cyclobutyl)methyl)-N—(N—((R)-pent-4-en-2-yl)-N—((R)-tetrahydrofuran-2-yl)methyl)sulfamoyl)-3',4,4',5-tetrahydro-2H,2'H-spiro[benzo[b][1,4]oxazepine-3,1'-naphthalene]-7-carboxamide

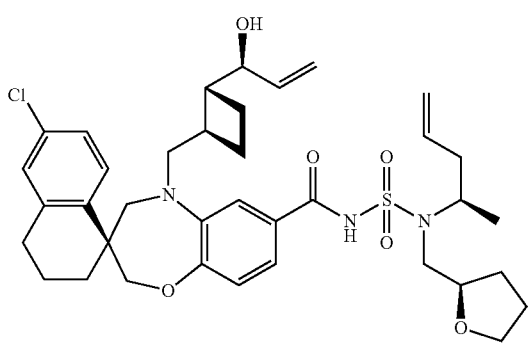

The title compound was prepared from Intermediate AA11A and N—(R)-pent-4-en-2-yl, N—(R)-tetrahydrofuran-2-yl sulfuric diamide by a procedure similar to the one described in Example 29, Step 3 (65 mg, 0.093 mmol, 62.2% yield).

Step 4: (1S,3'R,6'R,7'S,8'E,11'R)-6-chloro-7'-hydroxy-11'-methyl-12'-((2R)-tetrahydro-2-furanylmethyl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide The title compound was prepared from (S)-6'-chloro-5-(((1R,2R)-2-((S)-1-hydroxyallyl)cyclobutyl)methyl)-N—(N—((R)-pent-4-en-2-yl)-N—((R)-tetrahydrofuran-2-yl)methyl)sulfamoyl)-3',4,4',5-tetrahydro-2H,2'H-spiro[benzo[b][1,4]oxazepine-3,1'-naphthalene]-7-carboxamide by a procedure similar to the one described in Example 29, Step 4 and was isolated via preparative HPLC as the first eluting isomer (14 mg, 0.021 mmol, 22.4% yield). ¹H NMR (400 MHz, CDCl₃) δ 8.82 (br. s, 1H), 7.71 (d, J=8.6 Hz, 1H), 7.19 (d, J=7.9 Hz, 1H), 7.11 (d, J=2.3 Hz, 2H), 7.02 (d, J=8.4 Hz, 1H), 6.93 (d, J=8.0 Hz, 1H), 5.84 (br. s, 1H), 5.73 (br. s, 1H), 4.27-4.05 (m, 4H), 3.91 (q, J=7.0 Hz, 1H), 3.84-3.69 (m, 3H), 3.66-3.50 (m, 3H), 3.44 (d, J=13.7 Hz, 2H), 2.84-2.73 (m, 2H), 2.66 (t, J=10.9 Hz, 1H), 2.42 (br. s, 3H), 2.31 (br. s, 3H), 2.26-2.14 (m, 2H), 2.07 (br. s, 1H), 2.01-1.77 (m, 3H), 1.76-1.51 (m, 4H), 1.47 (d, J=6.8 Hz, 3H). m/z (ESI, +ve ion) 671.2 (M+H)⁺.

Example 56. (1S,3'R,6'R,7'S,8'Z,11'R)-6-chloro-7'-hydroxy-11'-methyl-12'-((2R)-tetrahydro-2-furanylmethyl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

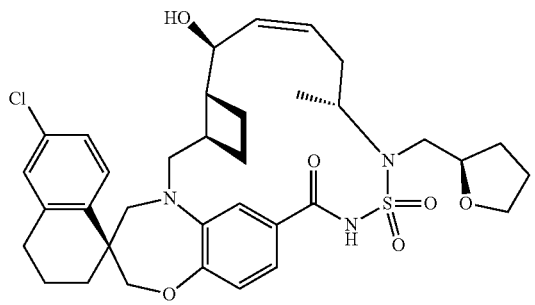

The title compound was prepared as the from the reaction described in Example 55, Step 4 and it was isolated via preparative HPLC as the second eluting isomer (4.2 mg, 6.27 μmol, 6.73% yield). ¹H NMR (400 MHz, CDCl₃) δ 10.55 (br. s, 1H), 7.76 (d, J=8.6 Hz, 1H), 7.53 (d, J=8.6 Hz, 1H), 7.30 (s, 1H), 7.20 (dd, J=2.3, 8.4 Hz, 1H), 7.11 (d, J=2.2 Hz, 1H), 6.98 (d, J=8.4 Hz, 1H), 5.84 (dt, J=4.9, 11.1 Hz, 1H), 5.68 (dd, J=7.4, 10.8 Hz, 1H), 4.43 (t, J=7.3 Hz, 1H), 4.26 (d, J=7.0 Hz, 1H), 4.20-4.04 (m, 2H), 3.98-3.84 (m, 3H), 3.77 (dt, J=6.3, 7.9 Hz, 1H), 3.66 (d, J=14.3 Hz, 1H), 3.51 (dd, J=8.7, 15.0 Hz, 1H), 3.40 (d, J=14.7 Hz, 1H), 3.21 (d, J=14.3 Hz, 1H), 3.11 (dd, J=9.0, 15.3 Hz, 2H), 2.86-2.72 (m, 2H), 2.63-2.36 (m, 1H), 2.33-2.15 (m, 3H), 2.13-1.90 (m, 6H), 1.88-1.79 (m, 2H), 1.71-1.44 (m, 7H). m/z (ESI, +ve ion) 671.3 (M+H)⁺.

Example 57. (1S,3'R,6'R,7'S,8'E,11'S)-6-chloro-12'-ethyl-7'-hydroxy-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

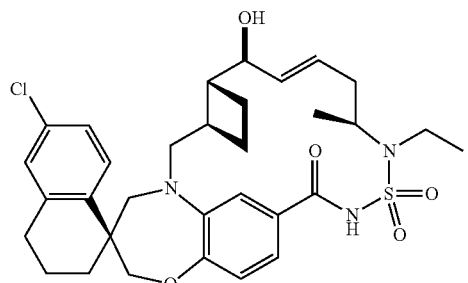

Step 1: (S)-tert-butyl N-ethyl-N-(pent-4-en-2-yl) sulfamoylcarbamate

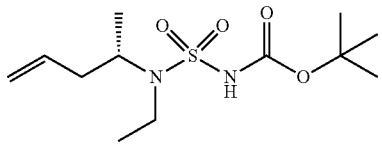 [SMILES: C=CC[C@H](C)N(CC)S(=O)(=O)NC(=O)OC(C)(C)C]

The title compound was prepared from (S)—N-ethylpent-4-en-2-amine by a procedure similar to the one described in Example 29, Step 1 (2.6 g, 8.89 mmol, 46.0% yield).

Step 2: N—(S)-pent-4-en-2-yl, N-ethyl Sulfuric Diamide

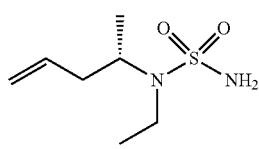

The title compound was prepared from (S)-tert-butyl N-ethyl-N-(pent-4-en-2-yl) sulfamoylcarbamate by a procedure similar to the one described in Example 29, Step 2 (1.8 g, 9.36 mmol).

Step 3: (S)-6'-chloro-N—(N-ethyl-N—((S)-pent-4-en-2-yl)sulfamoyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide

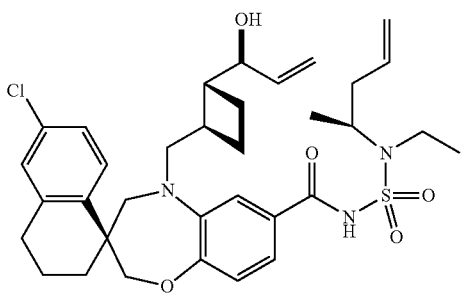

The title compound was prepared from Intermediate AA11A and N—(S)-pent-4-en-2-yl, N-ethyl sulfuric diamide by a procedure similar to the one described in Example 29, Step 3 (117 mg, 0.182 mmol, 83% yield).

Step 4: (1S,3'R,6'R,7'S,8'E,11'S)-6-chloro-12'-ethyl-7'-hydroxy-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide The title compound was prepared from (S)-6'-chloro-N—(N-ethyl-N—((S)-pent-4-en-2-yl)sulfamoyl)-5-(((1R,2R)-2-((S)-1-hydroxy allyl)cyclobutyl)methyl)-3',4,4',5-tetrahydro-2H,2'H-spiro[benzo[b][1,4]oxazepine-3,1'-naphthalene]-7-carboxamide by a procedure similar to the one described in Example 29, Step 4 and it was isolated via preparative HPLC as the first eluting isomer (48 mg, 0.078 mmol, 42.9% yield). $^1$H NMR (400 MHz, CDCl$_3$) δ 8.66 (br. s, 1H), 7.69 (d, J=8.6 Hz, 1H), 7.17 (dd, J=2.2, 8.5 Hz, 1H), 7.12-7.04 (m, 2H), 7.00-6.82 (m, 2H), 5.79-5.59 (m, 2H), 4.16-4.03 (m, 3H), 3.98-3.79 (m, 2H), 3.76-3.58 (m, 2H), 3.58-3.41 (m, 2H), 3.39-3.23 (m, 2H), 3.16 (dd, J=6.1, 14.7 Hz, 1H), 2.83-2.69 (m, 2H), 2.51-2.26 (m, 4H), 2.01-1.75 (m, 4H), 1.73-1.62 (m, 2H), 1.49-1.24 (m, 7H). m/z (ESI, +ve ion) 615.2 (M+H)$^+$.

Example 58. (1S,3'R,6'R,7'S,8'Z,11'S)-6-chloro-12'-ethyl-7'-hydroxy-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

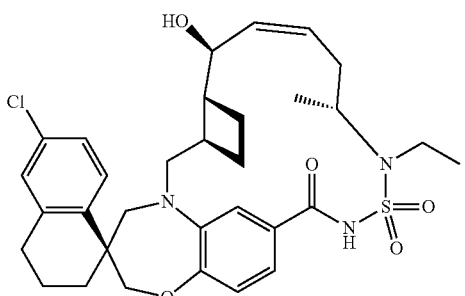

The title compound was prepared as from the reaction described in Example 57, Step 4 and it was isolated via preparative HPLC as the second eluting isomer (5 mg, 8.14 μmol, 4.47% yield). $^1$H NMR (400 MHz, CDCl$_3$) δ 8.93 (br. s, 1H), 7.69 (d, J=8.4 Hz, 1H), 7.22-7.07 (m, 3H), 6.99-6.89 (m, 1H), 6.82 (br. s, 1H), 5.78-5.63 (m, 1H), 5.58-5.50 (m, 1H), 4.58 (dd, J=4.6, 8.1 Hz, 1H), 4.23-3.96 (m, 2H), 3.93-3.77 (m, 2H), 3.76-3.50 (m, 3H), 3.40-3.14 (m, 2H), 2.86-2.72 (m, 2H), 2.63 (br. s, 2H), 2.51-2.34 (m, 1H), 2.32-2.17 (m, 1H), 2.06-1.97 (m, 2H), 1.94 (br. s, 2H), 1.90-1.66 (m, 4H), 1.52-1.29 (m, 7H). m/z (ESI, +ve ion) 615.2 (M+H)$^+$.

Example 59. (1S,3'R,6'R,7'S,8'E,11R)-6-chloro-12'-ethyl-7'-hydroxy-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

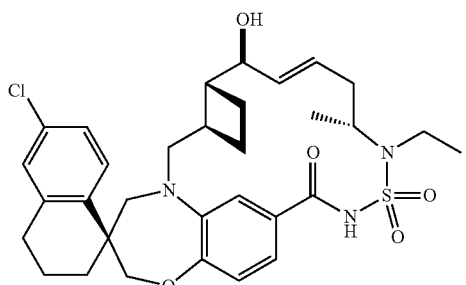

Step 1: (R)-tert-butyl N-ethyl-N-(pent-4-en-2-yl)sulfamoylcarbamate

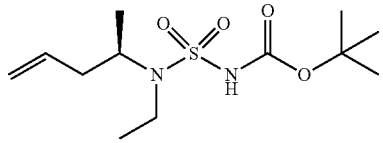 [SMILES: C=CC[C@@H](C)N(CC)S(=O)(=O)NC(=O)OC(C)(C)C]

The title compound was prepared from (R)—N-ethylpent-4-en-2-amine by a procedure similar to the one described in Example 29, Step 1 (1.25 g, 4.28 mmol, 38.4% yield).

Step 2: N—(R)-pent-4-en-2-yl, N-ethyl Sulfuric Diamide

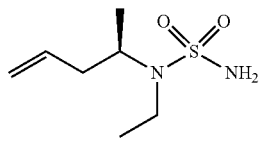

The title compound was prepared from (R)-tert-butyl N-ethyl-N-(pent-4-en-2-yl) sulfamoylcarbamate by a procedure similar to the one described in Example 29, Step 2 (0.816 g, 4.24 mmol, 99% yield).

Step 3. (S)-6'-chloro-N—(N-ethyl-N—((R)-pent-4-en-2-yl)sulfamoyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide

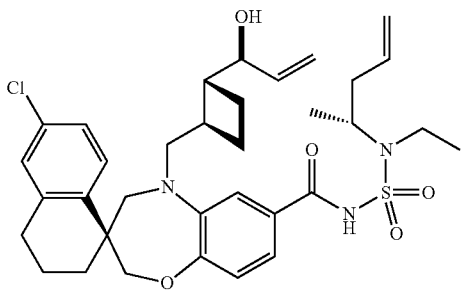

The title compound was prepared from Intermediate AA11A and N—(R)-pent-4-en-2-yl, N-ethyl sulfuric diamide by a procedure similar to the one described in Example 29, Step 3 (147 mg, 0.229 mmol, 71.4% yield).

Step 4: (1S,3'R,6'R,7'S,8'E,11R)-6-chloro-12'-ethyl-7'-hydroxy-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide The title compound was prepared from (S)-6'-chloro-N—(N-ethyl-N—((R)-pent-4-en-2-yl)sulfamoyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide by a procedure similar to the one described in Example 29, Step 4 and it was isolated via preparative HPLC as the first eluting isomer (37 mg, 0.060 mmol, 25.8% yield). ¹H NMR (400 MHz, CDCl₃) δ 8.39 (s, 1H), 7.69 (d, J=8.4 Hz, 1H), 7.30 (s, 1H), 7.19 (t, J=6.7 Hz, 1H), 7.11 (d, J=2.2 Hz, 1H), 6.99-6.86 (m, 2H), 5.78-5.59 (m, 2H), 4.26-4.02 (m, 3H), 3.90 (br. s, 1H), 3.81-3.61 (m, 1H), 3.53 (br. s, 2H), 3.50-3.27 (m, 2H), 2.79 (d, J=5.3 Hz, 2H), 2.63-2.35 (m, 6H), 2.26 (td, J=5.6, 15.3 Hz, 1H), 1.96-1.70 (m, 5H), 1.63 (br. s, 1H), 1.56 (d, J=7.0 Hz, 1H), 1.47-1.27 (m, 6H). m/z (ESI, +ve ion) 615.2 (M+H)⁺.

Example 60. (1S,3'R,6'R,7'S,8'Z,11'R)-6-chloro-12'-ethyl-7'-hydroxy-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

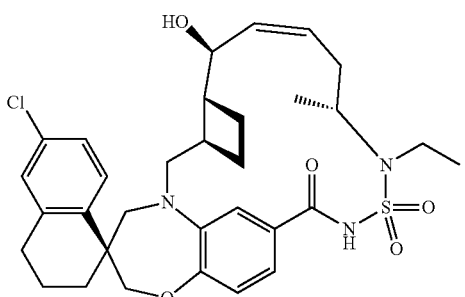

The title compound was prepared from the reaction described in Example 59, Step 4 and it was isolated via preparative HPLC as the second eluting isomer (11 mg, 0.018 mmol, 7.67% yield). ¹H NMR (400 MHz, CDCl₃) δ 10.46 (s, 1H), 7.68 (d, J=8.6 Hz, 1H), 7.54 (dd, J=2.0, 8.4 Hz, 1H), 7.24 (d, J=1.8 Hz, 1H), 7.15 (t, J=7.1 Hz, 1H), 7.08 (d, J=5.5 Hz, 1H), 6.94 (d, J=8.2 Hz, 1H), 5.82 (d, J=5.3 Hz, 1H), 5.66 (dd, J=7.1, 10.3 Hz, 1H), 4.34 (t, J=8.1 Hz, 1H), 4.16-3.96 (m, 3H), 3.90 (d, J=11.7 Hz, 1H), 3.78 (d, J=14.9 Hz, 1H), 3.50 (d, J=14.1 Hz, 1H), 3.12 (dd, J=7.2, 15.1 Hz, 1H), 3.03-2.90 (m, 2H), 2.82-2.67 (m, 3H), 2.37 (br. s, 3H), 2.32-2.19 (m, 1H), 2.16-1.96 (m, 3H), 1.94-1.70 (m, 4H), 1.64 (dd, J=8.3, 10.1 Hz, 1H), 1.44-1.26 (m, 6H). m/z (ESI, +ve ion) 615.2 (M+H)⁺.

Example 61. (1S,3'R,6'R,7'S,8'E,11'S)-6-chloro-7'-hydroxy-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

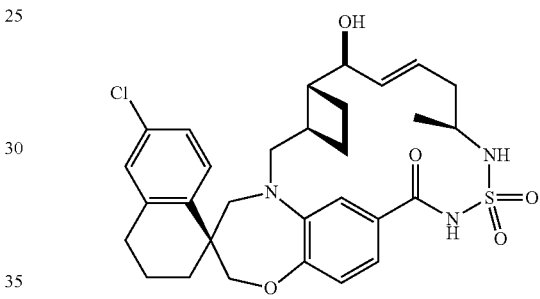

Step 1: (R)-pent-4-en-2-yl 4-methylbenzenesulfonate

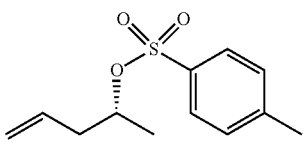 [SMILES: C=CC[C@@H](C)OS(=O)(=O)c1ccc(C)cc1]

To a solution of 4-methylbenzene-1-sulfonyl chloride (24.3 g, 128 mmol) and 4-(dimethylamino)pyridine (1.42 g, 11.6 mmol) in DCM (300 mL) was added triethylamine (reagentplus 99.5%, 32.3 mL, 232 mmol) at 0° C. followed by the addition of a solution of (R)-(−)-4-penten-2-ol (11.9 mL, 116 mmol) in DCM (60 mL) dropwise over 15 minutes using an addition funnel. The reaction was stirred at ambient temperature for 45 hours. The reaction was diluted with DCM and washed with saturated NaHCO₃, water and brine. The DCM solution was dried with MgSO₄, filtered and then concentrated to give a residue which was purified by silica gel chromatography using Redi-Sep pre-packed Gold silica gel column (300 g) to afford the title compound (23 g, 96 mmol, 82% yield) as a liquid.

Step 2: (S)—N-(4-methoxybenzyl) pent-4-en-2-amine

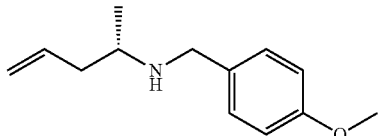

To a solution of (R)-pent-4-en-2-yl 4-methylbenzenesulfonate (5.42 g, 22.6 mmol) in dioxane (17 mL) was added 4-methoxybenzylamine (5.85 mL, 45.1 mmol) and triethylamine (3.78 mL, 27.1 mmol) in a pressure vessel equipped with a pressure gauge and the resulting mixture was purged with $N_2$ for about 20 minutes. The reaction was heated at 90° C. for 41 hours. The reaction was filtered to remove precipitate produced in the reaction and concentrated to give a residue, which was purified by silica gel chromatography using Redi-Sep pre-packed Gold silica gel column (220 g) eluting with 0-100% of EtOAc in hexane to afford the title compound (3.23 g, 15.73 mmol, 69.8% yield).

Step 3: (S)-tert-butyl n-(4-methoxybenzyl)-N-(pent-4-en-2-yl)sulfamoylcarbamate

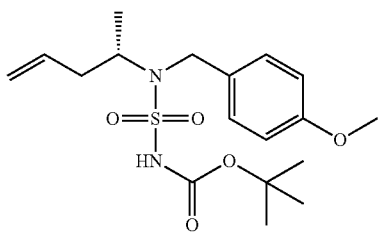 [SMILES: C=CC[C@H](C)N(Cc1ccc(OC)cc1)S(=O)(=O)NC(=O)OC(C)(C)C]

The title compound was prepared from (S)—N-(4-methoxybenzyl) pent-4-en-2-amine by a procedure similar to the one described in Example 29, Step 1 (4.65 g, 12.0 mmol, 77% yield).

Step 4: N—(S)-pent-4-en-2-yl Sulfuric Diamide

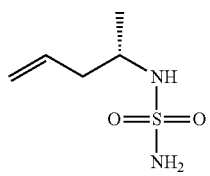

The title compound was prepared from (S)-tert-butyl N-(4-methoxybenzyl)-N-(pent-4-en-2-yl) sulfamoylcarbamate by a procedure similar to the one described in Example 29, Step 2 (1.76 g, 10.7 mmol, 92% yield).

Step 5: (S)-6'-chloro-5-(((1R,2R)-2-((S)-1-hydroxyallyl)cyclobutyl)methyl)-N—(N—((S)-pent-4-en-2-yl)sulfamoyl)-3',4,4',5-tetrahydro-2H,2'H-spiro[benzo[b][1,4]oxazepine-3,1'-naphthalene]-7-carboxamide

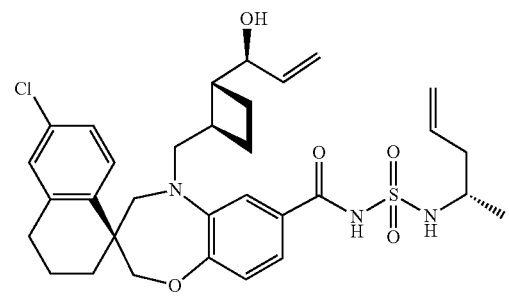

The title compound was prepared from Intermediate AA11A and N—(S)-pent-4-en-2-yl sulfuric diamide by a procedure similar to the one described in Example 29, Step 3 (1.25 g, 2.04 mmol, 87% yield).

Step 6: (1S,3'R,6'R,7'S,8'E,11'S)-6-chloro-7'-hydroxy-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide The title compound was prepared from (S)-6'-chloro-5-(((1R,2R)-2-((S)-1-hydroxyallyl)cyclobutyl)methyl)-N—(N—((S)-pent-4-en-2-yl)sulfamoyl)-3',4,4',5-tetrahydro-2H,2'H-spiro[benzo[b][1,4]oxazepine-3,1'-naphthalene]-7-carboxamide by a procedure similar to the one described in Example 29, Step 4 (641 mg, 1.09 mmol, 50.1% yield). $^1$H NMR (400 MHz, CD$_3$OD) δ 7.65 (d, J=8.6 Hz, 1H), 7.11 (dd, 8.5 Hz, 1H), 7.04 (d, J=2.2 Hz, 1H), 6.92-6.83 (m, 2H), 6.76 (d, J=1.8 Hz, 1H), 5.86-5.78 (m, 1H), 5.61 (dd, J=8.7, 15.2 Hz, 1H), 4.16 (dd, J=3.9, 8.8 Hz, 2H), 3.76 (d, J=15.1 Hz, 1H), 3.67-3.53 (m, 2H), 3.15 (d, J=14.3 Hz, 1H), 2.94 (dd, J=10.0, 15.3 Hz, 1H), 2.80-2.65 (m, 2H), 2.50-2.40 (m, 1H), 2.40-2.30 (m, 1H), 2.25-2.12 (m, 1H), 2.06-1.86 (m, 5H), 1.76 (qd, J=9.6, 19.0 Hz, 3H), 1.67-1.53 (m, 1H), 1.43-1.26 (m, 1H), 1.23-1.15 (m, 3H). m/z (ESI, +ve ion) 587.2 (M+H)$^+$.

Example 62. (1S,3'R,6'R,7'S,8'Z,11'S)-6-chloro-7'-hydroxy-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

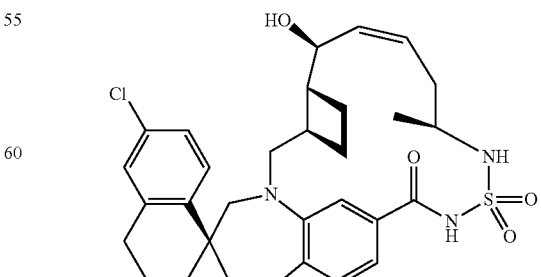

The title compound was prepared from (S)-6'-chloro-5-(((1R,2R)-2-((S)-1-hydroxyallyl)cyclobutyl)methyl)-N—(N—((S)-pent-4-en-2-yl)sulfamoyl)-3',4,4',5-tetrahydro-2H,2'H-spiro[benzo[b][1,4]oxazepine-3,1'-naphthalene]-7-carboxamide (Example 61, step 5) by a procedure similar to the one described in Example 29, Step 4 and it was isolated via preparative HPLC as the second eluting isomer (25 mg, 0.043 mmol, 2.10% yield). $^1$H NMR (400 MHz, CD$_3$OD) δ 7.72 (d, J=8.4 Hz, 1H), 7.15 (dd, J=2.2, 8.5 Hz, 1H), 7.08 (d, J=2.2 Hz, 1H), 7.03-6.98 (m, 1H), 6.96-6.87 (m, 2H), 5.69-5.59 (m, 1H), 5.57-5.51 (m, 1H), 4.47 (dd, J=4.1, 9.0 Hz, 1H), 4.15-3.98 (m, 2H), 3.93 (d, J=15.3 Hz, 1H), 3.70 (d, J=14.1 Hz, 1H), 3.58-3.40 (m, 2H), 3.18 (dd, J=9.8, 15.3 Hz, 1H), 2.86-2.70 (m, 2H), 2.58-2.35 (m, 3H), 2.21 (t, J=8.2 Hz, 1H), 2.10 (d, J=13.7 Hz, 1H), 2.03-1.82 (m, 5H), 1.80-1.70 (m, 1H), 1.45 (br. s, 1H), 1.31-1.22 (m, 3H). m/z (ESI, +ve ion) 587.2 (M+H)$^+$.

Example 63. (1S,3'R,6'R,7'S,8'Z,11'S)-6-chloro-7'-hydroxy-12'-(2-methoxyethyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

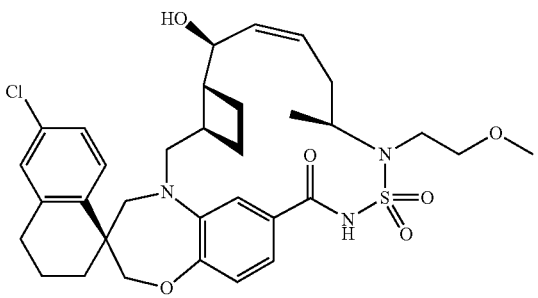

To a solution of Example 62 (24 mg, 0.043 mmol) in DMF (0.5 mL) was added sodium hydride (11.7 mg, 0.341 mmol) and the reaction was stirred at 0° C. for 15 minutes followed by the addition of 1-bromo-2-methoxyethane (0.020 mL, 0.213 mmol). The resulting mixture was stirred at ambient temperature for 2.5 days. The reaction was quenched with saturated NH$_4$Cl and extracted with EtOAc. The organic extract was washed with brine, dried with MgSO$_4$, filtered and concentrated to give a residue, which was purified by reversed phase preparative HPLC (Gemini™ Prep C$_{18}$ 5 μm column; Phenomenex, Torrance, CA; gradient elution of 60% to 85% MeCN in water, where both solvents contain 0.1% TFA, 30 min method) to afford the title compound as the first eluting isomer 1.3 mg, 2.02 μmol, 4.73% yield). $^1$H NMR (400 MHz, CDCl$_3$) δ 9.15 (s, 1H), 7.68 (d, J=8.6 Hz, 1H), 7.22-7.12 (m, 2H), 7.11-7.04 (m, 1H), 6.92 (d, J=8.2 Hz, 1H), 6.84 (s, 1H), 5.76-5.62 (m, 1H), 5.62-5.47 (m, 1H), 4.61-4.47 (m, 1H), 4.14-4.00 (m, 2H), 3.98-3.88 (m, 1H), 3.82-3.56 (m, 6H), 3.38 (s, 3H), 3.34-3.17 (m, 1H), 2.88-2.71 (m, 2H), 2.71-2.55 (m, 2H), 2.48-2.35 (m, 1H), 2.25 (quin, J=8.1 Hz, 1H), 2.11-1.81 (m, 6H), 1.79-1.63 (m, 2H), 1.52-1.33 (m, 5H). m/z (ESI, +ve ion) 645.2 (M+H)$^+$.

Example 64. (1S,3'R,6'R,7'S,8'Z,11'S)-6-chloro-7'-(2-methoxyethoxy)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

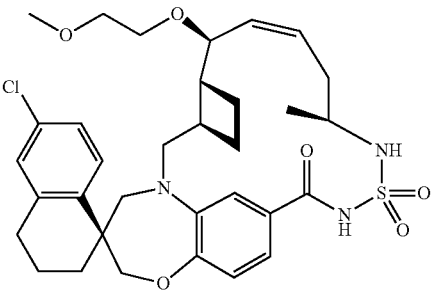

The title compound was prepared from the reaction described in Example 63 and was isolated via preparative HPLC as the second eluting isomer (3.3 mg, 5.12 μmol, 12.0% yield). $^1$H NMR (400 MHz, CDCl$_3$) δ 9.58 (br. s, 1H), 7.79-7.63 (m, 1H), 7.26-7.14 (m, 2H), 7.13-7.01 (m, 2H), 6.98-6.91 (m, 1H), 6.03 (br. s, 1H), 5.79-5.52 (m, 2H), 4.32-3.98 (m, 3H), 3.93-3.75 (m, 2H), 3.67 (d, J=4.9 Hz, 2H), 3.53 (br. s, 2H), 3.42-3.28 (m, 4H), 3.28-3.15 (m, 1H), 3.07 (br. s, 1H), 2.86-2.67 (m, 2H), 2.62-2.37 (m, 2H), 2.34-2.20 (m, 1H), 2.11 (s, 1H), 2.11-1.88 (m, 3H), 1.82 (br. s, 1H), 1.72-1.39 (m, 3H), 1.32-1.18 (m, 5H). m/z (ESI, +ve ion) 645.2 (M+H)$^+$.

Example 65. (1S,3'R,6'R,7'S,8'Z,11'S)-6-chloro-7'-(2-methoxyethoxy)-12'-(2-methoxyethyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

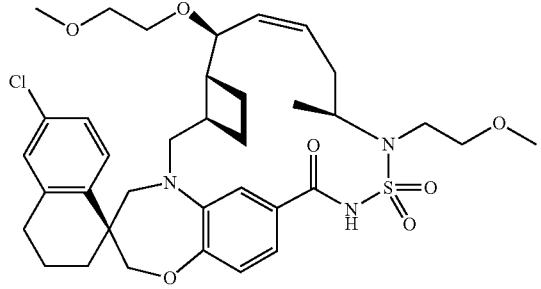

The title compound was prepared from the reaction described in Example 63 and it was isolated via preparative HPLC as the third eluting component (9.2 mg, 0.013 mmol, 30.7% yield). $^1$H NMR (400 MHz, CDCl$_3$) δ 8.95 (br. s, 1H), 7.70 (d, J=8.4 Hz, 1H), 7.18 (dd, J=2.3, 8.4 Hz, 1H), 7.13-7.01 (m, 2H), 6.98-6.86 (m, 1H), 6.74 (br. s, 1H), 5.67-5.42 (m, 2H), 4.19-3.98 (m, 3H), 3.97-3.71 (m, 4H), 3.70-3.56 (m, 4H), 3.49 (d, J=3.7 Hz, 1H), 3.43-3.28 (m, 9H), 3.24-3.23 (m, 1H), 2.88-2.64 (m, 3H), 2.63-2.47 (m, 2H), 2.24 (dt, J=3.0, 8.4 Hz, 1H), 2.11-1.74 (m, 6H), 1.73-1.59 (m, 1H), 1.51-1.32 (m, 4H). m/z (ESI, +ve ion) 703.2 (M+H)$^+$.

Example 66. (1S,3'R,6'R,7'S,8'E,11'S)-6-chloro-7'-hydroxy-11'-methyl-12'-(2-(4-morpholinyl)ethyl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

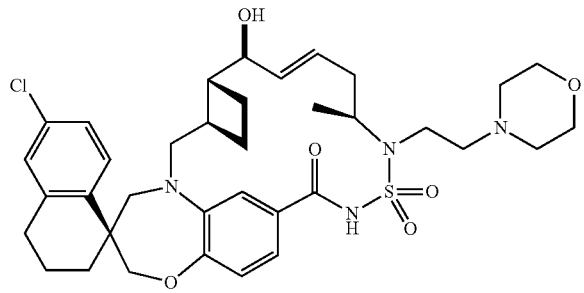

Step 1: 2-morpholinoethyl 4-methylbenzenesulfonate

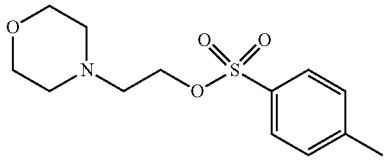 [SMILES: Cc1ccc(S(=O)(=O)OCCN2CCOCC2)cc1]

The title compound was prepared from 4-(2-hydroxyethyl) morpholine by a procedure similar to the one described in Example 61, Step 1 (0.77 g, 2.7 mmol, 35.4% yield).

Step 2: (1S,3'R,6'R,7'S,8'E,11'S)-6-chloro-7'-[(tert-butyldimethylsilyl)oxy]-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

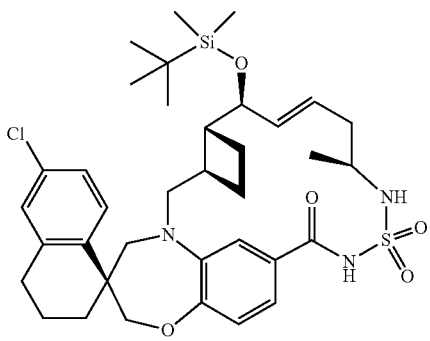

The title compound was prepared from Example 61 by a procedure similar to the one described in Example 31, Step 1 (570 mg, 0.814 mmol, 74.4% yield).

Step 3: (1S,3'R,6'R,7'S,8'E,11'S)-6-chloro-7'-hydroxy-11'-methyl-12'-(2-(4-morpholinyl)ethyl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide To a solution of (1S,3'R,6'R,7'S,8'E,11'S)-6-chloro-7'-[(tert-butyldimethylsilyl)oxy]-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide (30 mg, 0.043 mmol) in THF (0.8 mL) was added lithium bis(trimethylsilyl) amide, 1.0 M solution in THF (0.171 mL, 0.171 mmol) and the reaction was stirred at 0° C. for 10 minutes followed by addition of a solution of 2-morpholinoethyl 4-methylbenzenesulfonate (36.7 mg, 0.128 mmol) in THF (0.32 mL). The resulting mixture was then transferred to an oven-dried microwave tube under $N_2$ atmosphere. The reaction was stirred at 120° C. for 4 hours in a microwave. The reaction was diluted with THF (0.8 mL) and treated with tetrabutylammonium fluoride solution, 1.0 M in THF (0.857 mL, 0.857 mmol) and a small amount of molecular sieves at 55° C. for 1 hour in microwave. Without workup the reaction was concentrated to give a residue, which was purified by reversed phase preparative HPLC (Gemini™ Prep $C_{18}$ 5 μm column; Phenomenex, Torrance, CA) to afford the title compound (1.4 mg, 2.00 μmol, 4.67% yield). ¹H NMR (400 MHz, CD₃OD) δ 7.79-7.65 (m, 1H), 7.23-7.06 (m, 3H), 7.01-6.86 (m, 2H), 5.76-5.48 (m, 2H), 4.30-3.87 (m, 9H), 3.83-3.70 (m, 3H), 3.68-3.55 (m, 3H), 3.24-3.05 (m, 3H), 2.93-2.66 (m, 2H), 2.55-2.21 (m, 4H), 2.15-1.79 (m, 8H), 1.79-1.59 (m, 1H), 1.38-1.24 (m, 4H). m/z (ESI, +ve ion) 700.0 (M+H)⁺.

Example 67. (1S,3'R,6'R,7'S,8'E,11'S)-6-chloro-11'-methyl-7'-(2-(4-morpholinyl)ethoxy)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

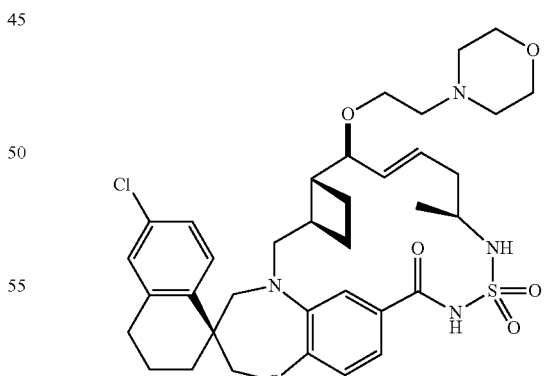

The title compound was prepared from Example 61 and 4-(2-chloroethyl)morpholine hydrochloride by a procedure similar to the one described in Example 46. ¹H NMR (400 MHz, CD₃OD) δ 7.73-7.71 (d, J=8.4 Hz, 1H), 7.27-7.07 (m, 3H), 7.03-6.88 (m, 2H), 5.72-5.49 (m, 2H), 4.29-3.95 (m, 8H), 3.86-3.69 (m, 3H), 3.67-3.53 (m, 3H), 3.49-3.47 (m, 2H), 3.19-3.12 (m, 2H), 2.88-2.65 (m, 2H), 2.53-2.19 (m, 4H), 2.14-2.00 (m, 2H), 1.97-1.78 (m, 4H), 1.76-1.62 (m, 2H), 1.55-1.17 (m, 2H), 1.05-0.78 (m, 4H). m/z (ESI, +ve ion) 700.2 (M+H)+.

Example 68. (1S,3'R,6'R,7'S,8'E,11'S)-6-chloro-7'-(2-methoxyethoxy)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

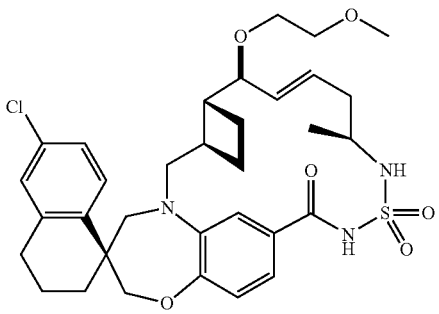

The title compound was prepared from Example 61 by a procedure similar to the one described in Example 63 and it was isolated via preparative HPLC as the second eluting isomer (5.2 mg, 8.07 µmol, 11.5% yield). $^1$H NMR (400 MHz, CD$_3$OD) δ 7.72 (d, J=8.6 Hz, 1H), 7.16 (dd, 8.5 Hz, 1H), 7.09 (d, J=2.2 Hz, 1H), 6.95-6.87 (m, 2H), 6.82 (d, J=1.6 Hz, 1H), 6.02-5.94 (m, 1H), 5.55 (dd, J=9.5, 15.4 Hz, 1H), 4.09-4.00 (m, 2H), 3.92-3.77 (m, 2H), 3.71-3.43 (m, 6H), 3.36 (s, 3H), 3.23 (d, J=14.3 Hz, 1H), 3.04 (dd, J=10.3, 15.2 Hz, 1H), 2.85-2.70 (m, 2H), 2.61 (d, J=13.7 Hz, 1H), 2.54-2.45 (m, 1H), 2.25 (t, J=9.0 Hz, 1H), 2.16-2.03 (m, 2H), 1.96-1.76 (m, 5H), 1.74-1.67 (m, 1H), 1.47-1.31 (m, 1H), 1.20 (d, J=6.8 Hz, 3H). m/z (ESI, +ve ion) 645.2 (M+H)+.

Example 69. (1S,3'R,6'R,7'S,8'E,11'S)-6-chloro-7'-(2-methoxyethoxy)-12'-(2-methoxyethyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

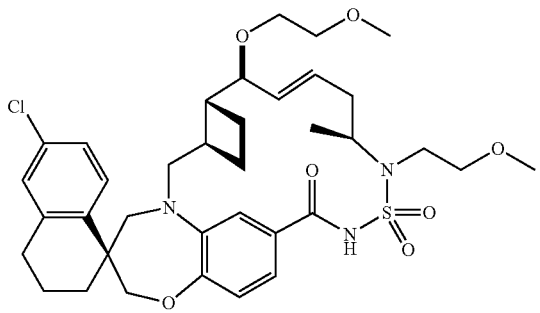

The title compound was prepared from the reaction described in Example 68 and it was isolated via preparative HPLC as the third eluting component (9.2 mg, 0.013 mmol, 18.7% yield). $^1$H NMR (400 MHz, CD$_3$OD) δ 7.71 (d, J=8.6 Hz, 1H), 7.14 (d, J=8.1 Hz, 1H), 7.08 (s, 1H), 6.97 (m, 1H), 6.91-6.85 (m, 2H), 5.79 (td, J=6.4, 15.5 Hz, 1H), 5.54 (dd, J=8.5, 15.6 Hz, 1H), 4.10 (br. s., 2H), 4.02-3.95 (m, 1H), 3.89-3.70 (m, 3H), 3.66-3.54 (m, 4H), 3.51-3.38 (m, 4H), 3.37 (s, 3H), 3.35 (s, 3H), 3.27-3.24 (d, J=14.3 Hz, 1H), 3.10 (dd, J=9.4, 15.5 Hz, 1H), 2.84-2.70 (m, 2H), 2.51-2.29 (m, 4H), 2.07 (d, J=13.7 Hz, 1H), 1.98-1.76 (m, 5H), 1.67 (q, J=9.4 Hz, 1H), 1.50-1.38 (m, 1H), 1.33 (d, J=6.7 Hz, 3H). m/z (ESI, +ve ion) 703.2 (M+H)+.

Example 70. methyl 3-(((1S,3'R,6'R,7'S,8'E,11'S)-6-chloro-11'-methyl-13',13'-dioxido-15'-oxo-3,4-dihydro-2H-spiro [naphthalene-1,22'-[20]oxa[13]thia[1,12,14]triazatetracyclo[14.7.2.0$^{3,6}$.0$^{19,24}$]pentacosa[8,16,18,24]tetraen]-7'-yl)oxy)propanoate

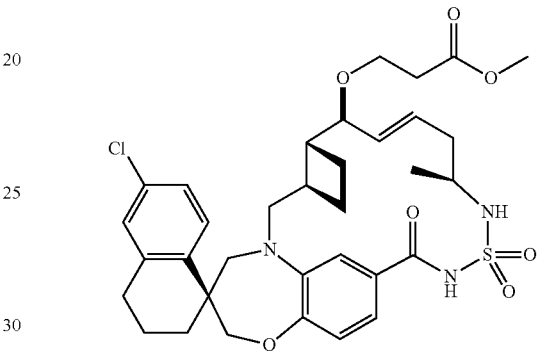

The title compound was prepared from Example 61 and methyl 3-bromopropanoate by a procedure similar to the one described in Example 63. $^1$H NMR (400 MHz, CDCl$_3$) δ 8.42 (s, 1H), 7.70 (d, J=8.4 Hz, 1H), 7.18 (dd, J=2.2, 8.5 Hz, 1H), 7.09 (d, J=2.2 Hz, 1H), 6.97-6.89 (m, 1H), 6.87-6.79 (m, 2H), 5.96-5.84 (m, 1H), 5.66 (d, J=7.6 Hz, 1H), 5.56 (dd, J=9.2, 15.3 Hz, 1H), 4.15-4.00 (m, 2H), 3.88-3.65 (m, 7H), 3.58 (td, J=6.3, 9.7 Hz, 1H), 3.19 (d, J=14.3 Hz, 1H), 2.98 (dd, J=10.1, 15.2 Hz, 1H), 2.86-2.67 (m, 2H), 2.62-2.49 (m, 3H), 2.49-2.33 (m, 1H), 2.24 (quin, J=9.2 Hz, 1H), 2.18-2.09 (m, 1H), 2.07-2.00 (m, 1H), 2.00-1.90 (m, 2H), 1.87-1.67 (m, 3H), 1.66-1.54 (m, 2H), 1.39 (t, J=13.3 Hz, 1H), 1.32-1.20 (m, 3H). m/z (ESI, +ve ion) 673.2 (M+H)+.

Example 71. (1S,3'R,6'R,7'S,8'E,11R)-6-chloro-7'-hydroxy-11'-methyl-3,4-dihydro-2H,15'H-spiro [naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

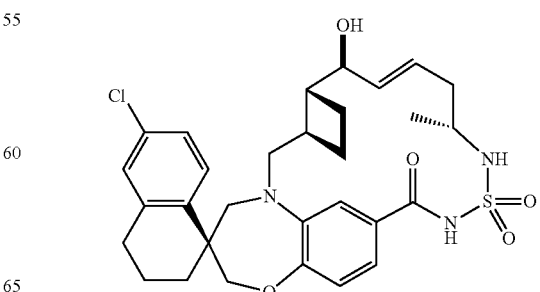

The title compound was prepared from the reaction described in Example 62 and it was isolated via preparative HPLC as the first eluting isomer (58 mg, 0.099 mmol, 4.86% yield). ¹H NMR (400 MHz, CD₃OD) δ 7.71 (d, J=8.4 Hz, 1H), 7.15 (dd, J=2.3, 8.4 Hz, 1H), 7.08 (d, J=2.2 Hz, 1H), 6.98-6.92 (m, 2H), 6.91-6.87 (m, 1H), 6.06-5.97 (m, 1H), 5.61 (dd, J=6.2, 15.4 Hz, 1H), 4.13-4.01 (m, 3H), 3.71-3.54 (m, 3H), 3.26-3.12 (m, 1H), 2.86-2.70 (m, 2H), 2.53 (t, J=9.4 Hz, 1H), 2.41-2.19 (m, 3H), 2.04 (d, J=13.7 Hz, 1H), 1.98-1.77 (m, 6H), 1.72-1.67 (m, 1H), 1.57-1.37 (m, 1H), 1.30-1.20 (m, 3H). m/z (ESI, +ve ion) 587.2 (M+H)⁺.

Example 72. (1S,3'R,6'R,7'S,8'E,11'S)-6-chloro-7'-hydroxy-12'-(3-methoxypropyl)-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

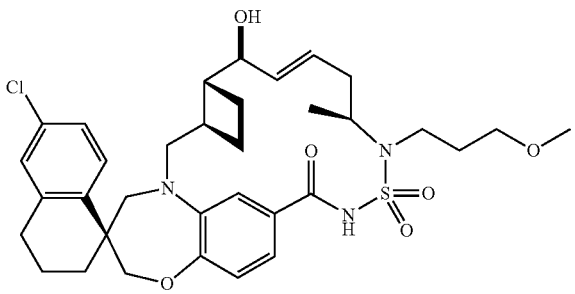

Step 1: (S)-tert-butyl N-(3-methoxypropyl)-N-(pent-4-en-2-yl)sulfamoylcarbamate

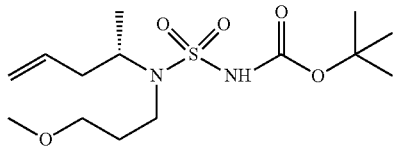 [SMILES: C=CC[C@H](C)N(CCCOC)S(=O)(=O)NC(=O)OC(C)(C)C]

The title compound was prepared from (S)—N-(3-methoxypropyl) pent-4-en-2-amine by a procedure similar to the one described in Example 29, Step 1 (2.34 g, 6.96 mmol, 56.7% yield).

Step 2: N—(S)-pent-4-en-2-yl, N-(3-methoxypropyl)sulfuric Diamide

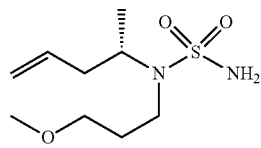

The title compound was prepared from (S)-tert-butyl N-(3-methoxypropyl)-N-(pent-4-en-2-yl) sulfamoylcarbamate by a procedure similar to the one described in Example 29, Step 2 (2.07 g, 8.76 mmol).

Step 3: (S)-6'-chloro-5-(((1R,2R)-2-((S)-1-hydroxyallyl)cyclobutyl)methyl)-N—(N-(3-methoxypropyl)-N—((S)-pent-4-en-2-yl)sulfamoyl)-3',4',4',5-tetrahydro-2H,2'H-spiro[benzo[b][1,4]oxazepine-3,1'-naphthalene]-7-carboxamide

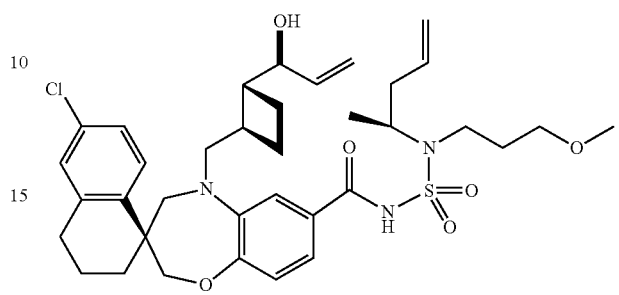

The title compound was prepared from Intermediate AA11A and N—(S)-pent-4-en-2-yl, N-(3-methoxypropyl) sulfuric diamide by a procedure similar to the one described in Example 29, Step 3 (127 mg, 0.185 mmol, 41.8% yield).

Step 4: (1S,3'R,6'R,7'S,8'E,11'S)-6-chloro-7'-hydroxy-12'-(3-methoxypropyl)-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide The title compound was prepared from (S)-6'-chloro-5-(((1R,2R)-2-((S)-1-hydroxyallyl)cyclobutyl)methyl)-N—(N-(3-methoxypropyl)-N—((S)-pent-4-en-2-yl)sulfamoyl)-3',4',4',5-tetrahydro-2H,2'H-spiro[benzo[b][1,4]oxazepine-3,1'-naphthalene]-7-carboxamide by a procedure similar to the one described in Example 29, Step 4 and was isolated via preparative HPLC as the first eluting isomer (15 mg, 0.023 mmol, 12.0% yield). ¹H NMR (400 MHz, CDCl₃) δ=8.40 (s, 1H), 7.69 (d, J=8.6 Hz, 1H), 7.18 (dd, J=2.3, 8.4 Hz, 1H), 7.08 (d, J=6.0 Hz, 2H), 6.93-6.86 (m, 2H), 5.77-5.62 (m, 2H), 4.14-4.04 (m, 3H), 3.92-3.64 (m, 4H), 3.54-3.42 (m, 2H), 3.34 (s, 5H), 3.21-3.08 (m, 1H), 2.82-2.70 (m, 2H), 2.50-2.27 (m, 4H), 2.04-1.85 (m, 6H), 1.83-1.65 (m, 4H), 1.51-1.40 (m, 1H), 1.35 (d, J=6.7 Hz, 3H). m/z (ESI, +ve ion) 659.2 (M+H)⁺.

Example 73. (1S,3'R,6'R,7'S,8'Z,11'S)-6-chloro-7'-hydroxy-12'-(3-methoxypropyl)-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

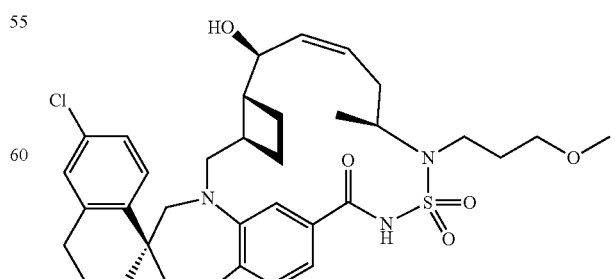

The title compound was prepared from the reaction described in Example 72, Step 4 and was isolated via preparative HPLC as the second eluting isomer (4.6 mg, 6.99 μmol, 3.69% yield). $^1$H NMR (400 MHz, CDCl$_3$) δ 9.25 (br. s, 1H), 7.66 (d, J=8.4 Hz, 1H), 7.18 (d, J=8.7 Hz, 1H), 7.12-7.06 (m, 2H), 6.89 (d, J=8.3 Hz, 1H), 6.74 (br. s, 1H), 5.74-5.63 (m, 1H), 5.55-5.47 (m, 1H), 4.61 (dd, J=4.0, 8.3 Hz, 1H), 4.06 (d, J=11.9 Hz, 1H), 3.96 (d, J=12.1 Hz, 1H), 3.83-3.59 (m, 5H), 3.49 (t, J=5.9 Hz, 2H), 3.35 (s, 3H), 3.33-3.11 (m, 2H), 2.85-2.68 (m, 3H), 2.67-2.55 (m, 1H), 2.51-2.32 (m, 1H), 2.18 (t, J=8.3 Hz, 1H), 2.13-1.91 (m, 6H), 1.91-1.69 (m, 4H), 1.48-1.43 (m, 1H), 1.41 (d, J=6.8 Hz, 3H). m/z (ESI, +ve ion) 659.3 (M+H)$^+$.

Example 74. (1S,3'R,6'R,7'S,8'E,11'S)-6-chloro-7'-(3-methoxypropoxy)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

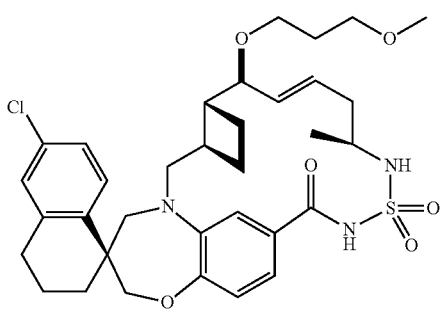

The title compound was prepared from Example 61 by a procedure similar to the one described in Example 63 and was isolated via preparative HPLC as the first eluting isomer (4.54 mg, 6.90 μmol, 11.2% yield). $^1$H NMR (400 MHz, CDCl$_3$) δ 8.44 (s, 1H), 7.70 (d, J=8.6 Hz, 1H), 7.18 (dd, J=2.2, 8.5 Hz, 1H), 7.09 (d, J=2.3 Hz, 1H), 6.94-6.89 (m, 1H), 6.88-6.80 (m, 2H), 5.92-5.83 (m, 1H), 5.65 (d, J=7.8 Hz, 1H), 5.56 (dd, J=9.1, 15.4 Hz, 1H), 4.12-4.03 (m, 2H), 3.85-3.68 (m, 4H), 3.53-3.36 (m, 3H), 3.34 (s, 3H), 3.19 (d, J=14.3 Hz, 1H), 2.98 (dd, J=10.2, 15.3 Hz, 1H), 2.84-2.70 (m, 2H), 2.58-2.38 (m, 2H), 2.25 (t, J=9.0 Hz, 1H), 2.18-1.90 (m, 5H), 1.87-1.59 (m, 6H), 1.43-1.36 (m, 1H), 1.26-1.24 (d, J=6.8 Hz, 3H). m/z (ESI, +ve ion) 659.2 (M+H)$^+$.

Example 75. (1S,3'R,6'R,7'S,8'E,11'S)-6-chloro-7'-(3-methoxypropoxy)-12'-(3-methoxypropyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

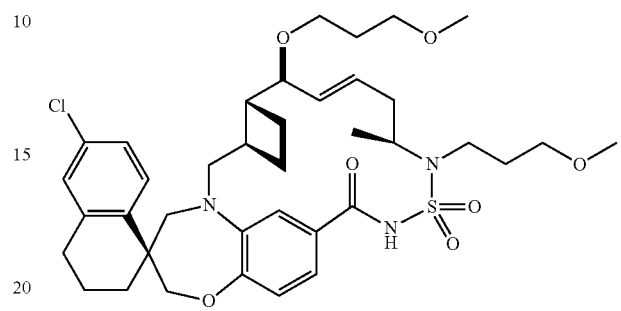

The title compound was prepared from the reaction described in Example 74 and was isolated via preparative HPLC as the third eluting isomer (10.6 mg, 0.015 mmol, 23.6% yield). $^1$H NMR (400 MHz, CDCl$_3$) δ 8.37 (s, 1H), 7.70 (d, J=8.6 Hz, 1H), 7.18 (dd, J=2.2, 8.5 Hz, 1H), 7.09 (d, J=2.2 Hz, 1H), 6.93-6.82 (m, 3H), 5.78 (td, J=6.4, 15.4 Hz, 1H), 5.52 (dd, J=8.4, 15.5 Hz, 1H), 4.09 (s, 2H), 3.99-3.82 (m, 2H), 3.79-3.63 (m, 3H), 3.53-3.36 (m, 6H), 3.34 (s, 3H), 3.33 (s, 3H), 3.21 (d, J=14.3 Hz, 1H), 3.04 (dd, J=9.0, 15.3 Hz, 1H), 2.83-2.70 (m, 2H), 2.47-2.26 (m, 4H), 2.09-1.89 (m, 5H), 1.87-1.71 (m, 6H), 1.69-1.54 (m, 1H), 1.44-1.42 (m, 1H), 1.37-1.35 (d, J=6.7 Hz, 3H). m/z (ESI, +ve ion) 731.2 (M+H)$^+$.

Example 76. (1S,3'R,6'R,7'S,8'E,11'S)-6-chloro-12'-(2-(dimethylamino)ethyl)-7'-hydroxy-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

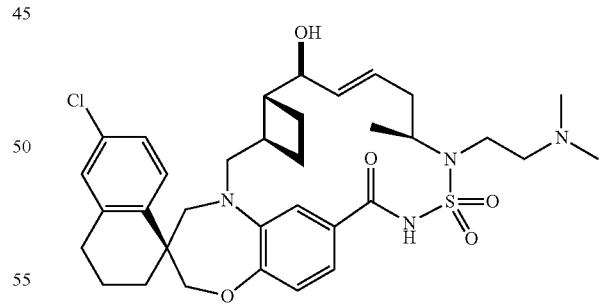

The title compound was prepared from Example 61 by a procedure similar to the one described in Example 63 (4.5 mg, 5.83 μmol, 8.34% yield). $^1$H NMR (400 MHz, CDCl$_3$) δ 7.69 (d, J=8.6 Hz, 1H), 7.27 (s, 2H), 7.17 (dd, 8.5 Hz, 1H), 7.09 (d, J=2.3 Hz, 1H), 6.97-6.85 (m, 3H), 5.75-5.64 (m, 1H), 5.64-5.51 (m, 1H), 4.33-4.15 (m, 2H), 4.10 (s, 2H), 4.02-3.88 (m, 2H), 3.80 (d, J=15.1 Hz, 1H), 3.69 (d, J=14.1 Hz, 1H), 3.43 (br. s, 2H), 3.20 (d, J=14.3 Hz, 1H), 3.09-2.93 (m, 5H), 2.90 (br. s, 3H), 2.86-2.59 (m, 4H), 2.57-2.37 (m, 4H), 2.32 (br. s, 1H), 2.23 (d, J=9.2 Hz, 3H), 2.07-1.78 (m, 6H), 1.73-1.60 (m, 2H), 1.45-1.29 (m, 4H), 1.26 (s, 1H). m/z (ESI, +ve ion) 658.2 (M+H)+.

Example 77. (1S,3'R,6'R,7'S,8'E,11'S)-6-chloro-7'-hydroxy-12'-(cis-3-methoxycyclobutyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

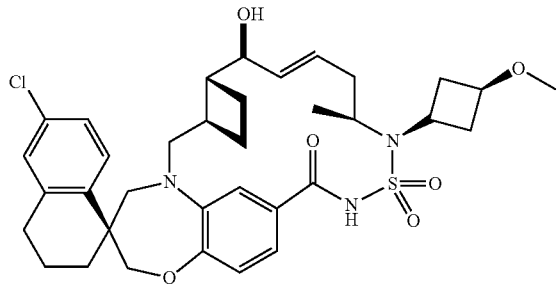

Step 1: tert-butyl N-((1S,3R)-3-methoxycyclobutyl)-N—((S)-pent-4-en-2-yl)sulfamoylcarbamate

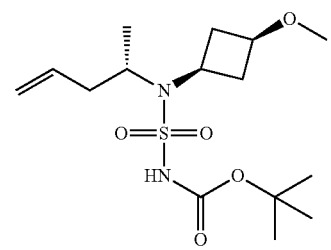 [SMILES: C=CC[C@H](C)N([C@H]1C[C@@H](OC)C1)S(=O)(=O)NC(=O)OC(C)(C)C]

The title compound was prepared from (1S,3R)-3-methoxy-N—((S)-pent-4-en-2-yl)cyclobutanamine by a procedure similar to the one described in Example 29, Step 1 (120 mg, 0.344 mmol, 8.12% yield).

Step 2: N—(S)-pent-4-en-2-yl, N-(cis-3-methoxycyclobutyl)sulfuric Diamide

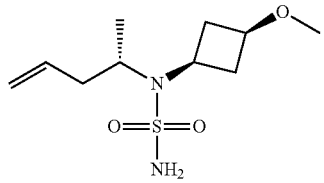 [SMILES: C=CC[C@H](C)N([C@H]1C[C@@H](OC)C1)S(N)(=O)=O]

The title compound was prepared from tert-butyl N-((1S,3R)-3-methoxycyclobutyl)-N—((S)-pent-4-en-2-yl) sulfamoylcarbamate by a procedure similar to the one described in Example 29, Step 2 (120 mg, 140% crude yield).

Step 3: (S)-6'-chloro-5-(((1R,2R)-2-((S)-1-hydroxyallyl)cyclobutyl)methyl)-N—(N-((1S,3R)-3-methoxycyclobutyl)-N—((S)-pent-4-en-2-yl)sulfamoyl)-3',4,4',5-tetrahydro-2H,2'H-spiro[benzo[b][1,4]oxazepine-3,1'-naphthalene]-7-carboxamide

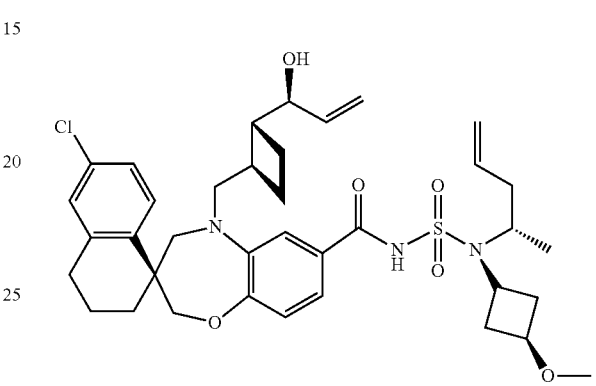

The title compound was prepared from Intermediate AA11A and N—(S)-pent-4-en-2-yl, N-(cis-3-methoxycyclobutyl)sulfuric diamide by a procedure similar to the one described in Example 29, Step 3 (53 mg, 0.076 mmol, 59.2% yield).

Step 4: (1S,3'R,6'R,7'S,8'E,11'S)-6-chloro-7'-hydroxy-12'-(cis-3-methoxycyclobutyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide The title compound was prepared from (S)-6'-chloro-5-(((1R,2R)-2-((S)-1-hydroxyallyl)cyclobutyl)methyl)-N—(N-((1S,3R)-3-methoxycyclobutyl)-N—((S)-pent-4-en-2-yl)sulfamoyl)-3',4,4',5-tetrahydro-2H,2'H-spiro[benzo[b][1,4]oxazepine-3,1'-naphthalene]-7-carboxamide by a procedure similar to the one described in Example 29, Step 4 and was isolated via preparative HPLC as the second eluting isomer (5.1 mg, 7.61 µmol, 10.0% yield). $^1$H NMR (400 MHz, CD$_3$OD) δ 7.69 (s, 1H), 7.13 (dd, J=2.2, 8.5 Hz, 1H), 7.06 (d, J=2.2 Hz, 1H), 6.99 (dd, J=1.9, 8.1 Hz, 1H), 6.88 (d, J=8.2 Hz, 1H), 6.82 (d, J=1.6 Hz, 1H), 5.92-5.84 (m, 1H), 5.64 (dd, J=7.5, 15.4 Hz, 1H), 4.14-4.01 (m, 3H), 3.92-3.69 (m, 3H), 3.67-3.57 (m, 2H), 3.24 (s, 3H), 3.07 (dd, J=9.2, 15.3 Hz, 1H), 2.79-2.73 (m, 2H), 2.70-2.50 (m, 4H), 2.47-2.30 (m, 4H), 2.07-1.89 (m, 4H), 1.89-1.76 (m, 3H), 1.64 (t, J=9.3 Hz, 1H), 1.45-1.39 (m, 1H), 1.33 (d, J=6.8 Hz, 3H). m/z (ESI, +ve ion) 671.2 (M+H)+.

Example 78. (1S,3'R,6'R,7'S,8'Z,11'S)-6-chloro-7'-hydroxy-12'-(cis-3-methoxycyclobutyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

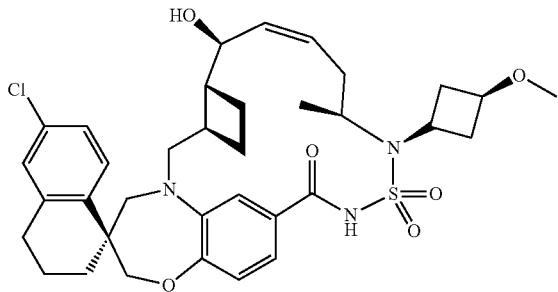

The title compound was prepared from the reaction described in Example 77, Step 4 and was isolated via preparative HPLC as the third eluting isomer (3.96 mg, 5.91 μmol, 7.78% yield). $^1$H NMR (400 MHz, CD$_3$OD) δ 7.70 (d, J=8.4 Hz, 1H), 7.14 (dd, J=2.3, 8.4 Hz, 1H), 7.10-7.04 (m, 2H), 6.90 (d, J=8.2 Hz, 1H), 6.83 (d, J=2.0 Hz, 1H), 5.64-5.50 (m, 2H), 4.65-4.50 (m, 2H), 4.09-3.98 (m, 3H), 3.76-3.67 (m, 2H), 3.61 (t, J=6.6 Hz, 1H), 3.38 (d, J=14.5 Hz, 1H), 3.24 (s, 3H), 3.21-3.09 (m, 2H), 2.87-2.74 (m, 2H), 2.73-2.59 (m, 2H), 2.44-2.36 (m, 1H), 2.29-2.18 (m, 2H), 2.12-1.84 (m, 8H), 1.81-1.71 (m, 1H), 1.46-1.34 (m, 4H). m/z (ESI, +ve ion) 671.2 (M+H)$^+$.

Example 79. (1S,3'R,6'R,7'S,8'E,11R)-6-chloro-7'-hydroxy-12'-(cis-3-methoxycyclobutyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

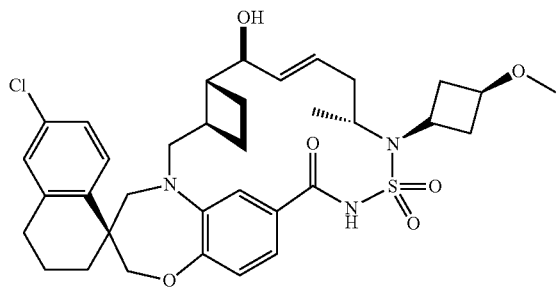

The title compound was prepared from the reaction described in Example 77, Step 4 and was isolated via preparative HPLC as the first eluting isomer (4.12 mg, 6.15 μmol, 8.10% yield). $^1$H NMR (400 MHz, CD$_3$OD) δ 7.74 (d, J=8.6 Hz, 1H), 7.19 (dd, J=2.3, 8.4 Hz, 1H), 7.12 (d, J=2.2 Hz, 1H), 6.95-6.90 (m, 2H), 6.78 (br. s, 1H), 5.84-5.76 (m, 1H), 5.68-5.60 (m, 1H), 4.33 (br. s, 1H), 4.20-3.99 (m, 4H), 3.94 (br. s, 1H), 3.80 (d, J=15.3 Hz, 1H), 3.71-3.60 (m, 2H), 3.25 (m, 3H), 3.17-3.06 (m, 1H), 2.86-2.59 (m, 5H), 2.42-2.17 (m, 4H), 2.11 (d, J=13.3 Hz, 2H), 1.94-1.85 (m, 3H), 1.81-1.64 (m, 3H), 1.52-1.38 (m, 4H). m/z (ESI, +ve ion) 671.2 (M+H)$^+$.

Example 80. (1S,3'R,6'R,7'S,8'E,11'S)-6-chloro-7'-hydroxy-12'-(4-methoxybenzyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

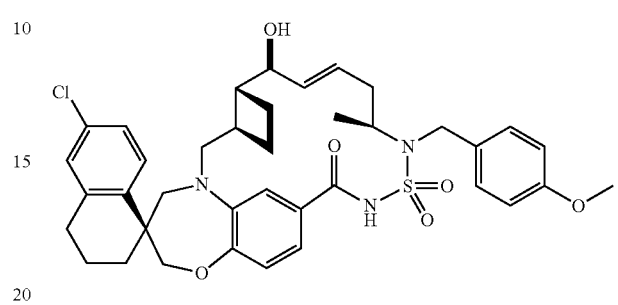

Step 1: N—(S)-pent-4-en-2-yl, N-(4-methoxybenzyl)sulfuric Diamide

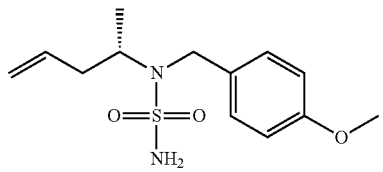

To a solution of (S)—N-(4-methoxybenzyl) pent-4-en-2-amine (1.78 g, 8.67 mmol) in dioxane (20 mL) was added sulfamide (2.92 g, 30.3 mmol) in dioxane (20 mL) and the resulting mixture was heated at 100° C. for 21 hours and at 120° C. for 1 hour. The reaction was concentrated to give a residue which was purified by silica gel chromatography using Redi-Sep pre-packed Gold silica gel column eluting with 0-70% of EtOAc in hexane to afford the title compound (2.31 g, 8.12 mmol, 94% yield).

Step 2: (S)-6'-chloro-5-(((1R,2R)-2-((S)-1-hydroxyallyl)cyclobutyl)methyl)-N—(N-(4-methoxybenzyl)-N—((S)-pent-4-en-2-yl)sulfamoyl)-3',4,4',5-tetrahydro-2H,2'H-spiro[benzo[b][1,4]oxazepine-3,1'-naphthalene]-7-carboxamide

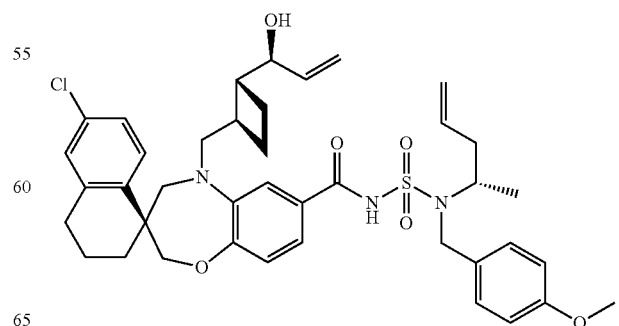

The title compound was prepared from Intermediate AA11A and N—(S)-pent-4-en-2-yl, N-(4-methoxybenzyl)sulfuric diamide by a procedure similar to the one described in Example 29, Step 3 (1.1 g, 1.50 mmol, 70.1% yield).

Step 3: (1S,3'R,6'R,7'S,8'E,11'S)-6-chloro-7'-hydroxy-12'-(4-methoxybenzyl)-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide The title compound was prepared from (S)-6'-chloro-5-(((1R,2R)-2-((S)-1-hydroxyallyl)cyclobutyl)methyl)-N—(N-(4-methoxybenzyl)-N—((S)-pent-4-en-2-yl)sulfamoyl)-3',4,4',5-tetrahydro-2H,2'H-spiro[benzo[b][1,4]oxazepine-3,1'-naphthalene]-7-carboxamide by a procedure similar to the one described in Example 29, Step 4 and was isolated via preparative HPLC as the first eluting isomer (0.48 g, 0.680 mmol, 45.4% yield). $^1$H NMR (400 MHz, CDCl$_3$) δ 8.04 (br. s, 1H), 7.68 (d, J=8.6 Hz, 1H), 7.31 (d, J=8.4 Hz, 3H), 7.17 (dd, J=2.2, 8.5 Hz, 1H), 7.09 (d, J=2.2 Hz, 1H), 6.92-6.79 (m, 1H), 6.74 (d, J=8.0 Hz, 2H), 6.66 (br. s, 1H), 5.89-5.76 (m, 1H), 5.66 (dd, J=5.0, 15.6 Hz, 1H), 4.88 (br. s, 1H), 4.26-4.04 (m, 5H), 3.80-3.75 (m, 3H), 3.58 (d, J=13.3 Hz, 2H), 3.41 (d, J=13.7 Hz, 2H), 2.83-2.70 (m, 2H), 2.59-2.39 (m, 4H), 2.39-2.24 (m, 1H), 2.02-1.52 (m, 8H), 1.11 (d, J=6.7 Hz, 3H). m/z (ESI, +ve ion) 707.2 (M+H)$^+$.

Example 81. (1S,3'R,6'R,7'S,8'Z,11'S)-6-chloro-7'-hydroxy-12'-(4-methoxybenzyl)-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

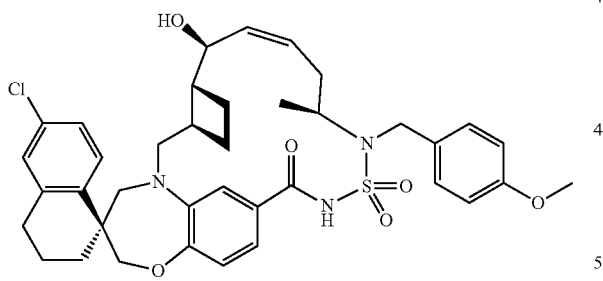

The title compound was prepared from the reaction described in Example 80, Step 3 and was isolated via preparative HPLC as the second eluting isomer (0.041 g, 0.058 mmol, 3.88% yield). $^1$H NMR (400 MHz, CDCl$_3$) δ 10.36 (br. s, 1H), 7.70 (d, J=8.6 Hz, 1H), 7.51 (dd, J=1.7, 8.3 Hz, 1H), 7.41-7.32 (m, J=8.6 Hz, 2H), 7.26 (m, 1H), 7.16 (dd, J=2.2, 8.5 Hz, 1H), 7.08 (d, J=2.2 Hz, 1H), 6.96 (d, J=8.4 Hz, 1H), 6.89-6.84 (m, J=8.8 Hz, 2H), 5.78 (dt, J=5.6, 10.8 Hz, 1H), 5.67 (dd, J=7.2, 10.4 Hz, 1H), 5.33 (d, J=16.0 Hz, 1H), 4.41 (t, J=7.2 Hz, 1H), 4.21-4.05 (m, 3H), 3.97 (d, J=11.9 Hz, 1H), 3.86 (m, 1H), 3.81 (s, 3H), 3.55 (d, J=14.1 Hz, 1H), 3.07-2.96 (m, 2H), 2.88 (t, J=11.2 Hz, 1H), 2.81-2.60 (m, 2H), 2.32-2.18 (m, 2H), 2.18-1.98 (m, 3H), 1.93-1.72 (m, 4H), 1.68-1.62 (m, 1H), 1.48-1.34 (m, 2H), 1.03 (d, J=6.8 Hz, 3H). m/z (ESI, +ve ion) 707.2 (M+H)$^+$.

Example 82. (1S,3'R,6'R,7'S,8'E,11'S)-6-chloro-12'-(4-methoxybenzyl)-7'-(2-methoxyethoxy)-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

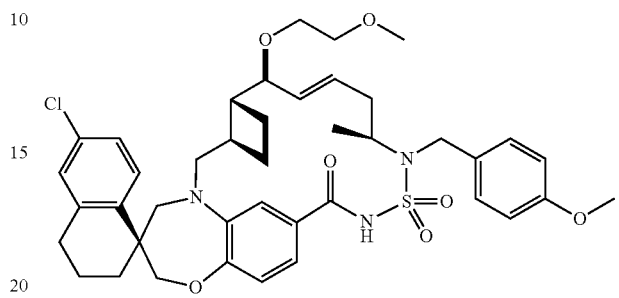

The title compound was prepared from Example 80 by a procedure similar to the one described in Example 43 (11 mg, 0.014 mmol, 24.8% yield). $^1$H NMR (400 MHz, CDCl$_3$) δ 8.42 (s, 1H), 7.71 (d, J=8.4 Hz, 1H), 7.37 (d, J=7.9 Hz, 2H), 7.18 (dd, J=2.2, 8.4 Hz, 1H), 7.09 (d, J=2.2 Hz, 1H), 6.93-6.86 (m, 5H), 5.86 (td, J=6.3, 15.4 Hz, 1H), 5.56 (dd, J=8.3, 15.6 Hz, 1H), 5.24 (d, J=16.6 Hz, 1H), 4.36 (d, J=16.8 Hz, 1H), 4.10 (s, 2H), 3.95 (q, J=6.7 Hz, 1H), 3.81 (s, 3H), 3.80-3.74 (m, 2H), 3.68 (d, J=14.3 Hz, 1H), 3.59-3.50 (m, 1H), 3.49-3.44 (m, 2H), 3.43-3.35 (m, 4H), 3.22 (d, J=14.3 Hz, 1H), 3.03 (dd, J=9.0, 15.5 Hz, 1H), 2.83-2.71 (m, 2H), 2.53-2.39 (m, 3H), 2.30 (t, J=8.5 Hz, 1H), 2.07-1.90 (m, 3H), 1.88-1.70 (m, 3H), 1.66-1.56 (m, 1H), 1.50-1.33 (m, 1H), 1.06 (d, J=6.8 Hz, 3H). m/z (ESI, +ve ion) 765.2 (M+H)$^+$.

Example 83. (1S,3'R,6'R,7'S,8'E,11'S)-6-chloro-7'-hydroxy-11',12'-dimethyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

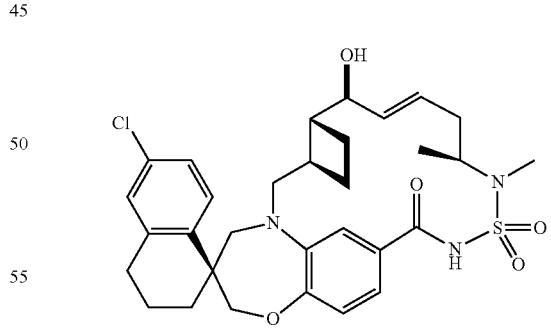

To a solution of (1S,3'R,6'R,7'S,8'E,11'S)-6-chloro-7'-[(tert-butyldimethylsilyl)oxy]-11'-methyl-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide (47 mg, 0.067 mmol, Example 66, Step 2) in THF (1 mL) was added sodium hydride, 60% dispersion in mineral oil (5.65 µL, 0.268 mmol) and the reaction was stirred at ambient temperature for 10 minutes followed by the addition of iodomethane (0.013 mL, 0.201 mmol). The resulting mixture was stirred at ambient temperature for 21 hours. The reaction was quenched with saturated NH$_4$Cl and extracted with EtOAc. The organic extract was washed with water and brine, dried with MgSO$_4$, filtered and concentrated to give a residue which was treated with tetrabutylammonium fluoride solution, 1.0 M in THF (1.34 mL, 1.34 mmol) and a small amount of molecule sieves at 55° C. for 1 hour. The reaction was concentrated to give a residue, which was purified by reversed phase preparatory HPLC (Gemini™ Prep C$_{18}$ 5 μm column; Phenomenex, Torrance, CA) to afford the title compound (2.4 mg, 4.0 μmol, 5.96% yield). $^1$H NMR (400 MHz, CDCl$_3$) δ 8.50 (s, 1H), 7.71 (d, J=8.6 Hz, 1H), 7.26 (s, 1H), 7.20 (dd, 8.5 Hz, 1H), 7.11 (d, J=2.2 Hz, 1H), 6.93 (s, 2H), 5.72-5.60 (m, 2H), 4.19-3.97 (m, 4H), 3.78-3.63 (m, 2H), 3.35 (d, J=14.3 Hz, 1H), 3.26 (d, J=14.3 Hz, 1H), 3.01 (s, 3H), 2.84-2.72 (m, 2H), 2.56-2.41 (m, 2H), 2.34-2.23 (m, 2H), 2.02-1.80 (m, 4H), 1.71 (m, 2H), 1.71-1.62 (m, 2H), 1.52 (t, J=11.7 Hz, 1H), 1.30 (d, J=6.7 Hz, 3H). m/z (ESI, +ve ion) 601.0 (M+H)$^+$.

Example 84. (1S,3'R,6'R,7'S,11R)-6-chloro-12'-ethyl-7'-hydroxy-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[16,18,24]trien]-15'-one 13',13'-dioxide

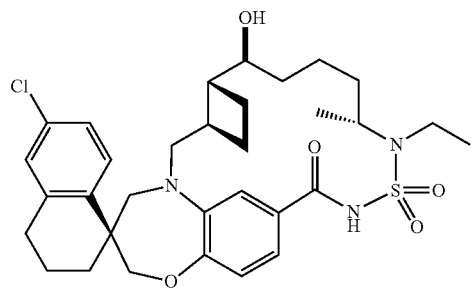

A mixture of Example 59 (13 mg, 0.021 mmol) and platinum (iv) oxide (0.961 mg, 4.23 μmol) in EtOAc (6 mL) was stirred under a H$_2$ balloon at ambient temperature for 1 hour. The reaction was filtered and concentrated to give a residue which was purified by reversed phase preparative HPLC (Gemini™ Prep C$_{18}$ 5 μm column; Phenomenex, Torrance, CA; gradient elution of 40% to 85% MeCN in water, where both solvents contain 0.1% TFA, 30 min method) to afford the title compound (6.0 mg, 9.74 μmol, 46.0% yield). $^1$H NMR (400 MHz, CDCl$_3$) δ 8.67 (s, 1H), 7.72 (d, J=8.4 Hz, 1H), 7.49 (d, J=1.8 Hz, 1H), 7.19 (dd, J=2.3, 8.6 Hz, 1H), 7.11 (d, J=2.3 Hz, 1H), 7.03-6.93 (m, 2H), 4.28 (br. s, 1H), 4.16 (s, 2H), 3.89 (d, J=14.7 Hz, 1H), 3.71 (t, J=7.0 Hz, 1H), 3.61 (d, J=14.1 Hz, 1H), 3.48 (dd, J=7.2, 14.9 Hz, 1H), 3.35-3.16 (m, 3H), 2.83-2.72 (m, 2H), 2.22 (br. s, 2H), 2.11 (s, 1H), 2.05-1.87 (m, 3H), 1.87-1.76 (m, 2H), 1.72-1.59 (m, 1H), 1.59-1.39 (m, 7H), 1.36-1.29 (m, 7H). m/z (ESI, +ve ion) 617.2 (M+H)$^+$.

Example 85. (1S,3'R,6'R,7'S,11'S)-6-chloro-12'-ethyl-7'-hydroxy-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[16,18,24]trien]-15'-one 13',13'-dioxide

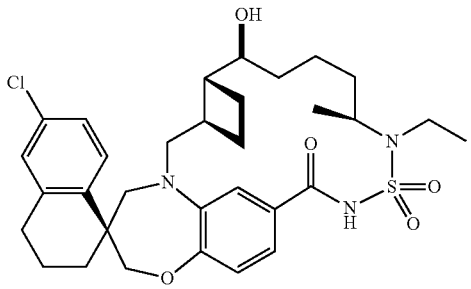

The title compound was prepared from Example 57 by a procedure similar to the one described in Example 84 (11 mg, 0.018 mmol, 68.5% yield). $^1$H NMR (400 MHz, CDCl$_3$) δ 8.87 (br. s, 1H), 7.70 (d, J=8.4 Hz, 1H), 7.41 (s, 1H), 7.19 (d, J=8.6 Hz, 1H), 7.09 (d, J=2.2 Hz, 1H), 7.00-6.86 (m, 2H), 4.15-4.03 (m, 3H), 3.88-3.68 (m, 3H), 3.65-3.56 (m, 1H), 3.33-3.21 (m, 2H), 3.12 (d, J=15.7 Hz, 1H), 2.83-2.71 (m, 2H), 2.64 (t, J=8.6 Hz, 1H), 2.48-2.38 (m, 1H), 2.12-1.79 (m, 6H), 1.71-1.57 (m, 2H), 1.50-1.25 (m, 12H), 1.16-0.93 (m, 1H). m/z (ESI, +ve ion) 617.2 (M+H)$^+$ Example 86. (1S,3'R,6'R,7'S)-6-chloro-12'-ethyl-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[16,18,24]trien]-15'-one 13',13'-dioxide

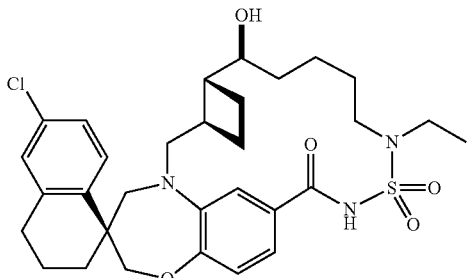

The title compound was prepared from Example 30 by a procedure similar to the one described in Example 84 (5.6 mg, 9.30 μma 55.8% yield). $^1$H NMR (400 MHz, CDCl$_3$) δ 9.22 (br. s, 1H), 7.69 (d, J=8.4 Hz, 1H), 7.21-7.09 (m, 4H), 6.94 (d, J=8.0 Hz, 1H), 4.16-4.05 (m, 2H), 3.88 (dd, J=7.2, 14.7 Hz, 1H), 3.82-3.74 (m, 1H), 3.72-3.46 (m, 4H), 3.42-3.17 (m, 3H), 2.84-2.72 (m, 2H), 2.45-2.32 (m, 1H), 2.26 (br. s, 2H), 2.02-1.78 (m, 5H), 1.75-1.63 (m, 3H), 1.62-1.41 (m, 6H), 1.27 (t, J=7.0 Hz, 3H). m/z (ESI, +ve ion) 603.2 (M+H)$^+$.

Example 87. (1S,3'R,6'R,7'S)-6-chloro-7'-hydroxy-12'-(2-propen-1-yl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[16,18,24]trien]-15'-one 13',13'-dioxide

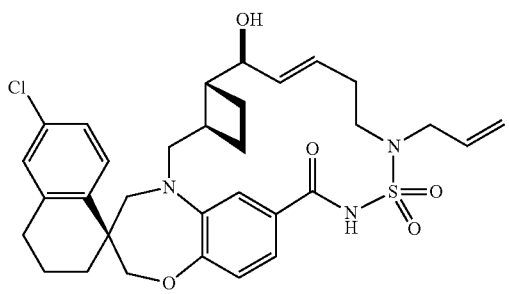

Step 1: (1S,3'R,6'R,7'S)-6-chloro-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[16,18,24]trien]-15'-one 13',13'-dioxide

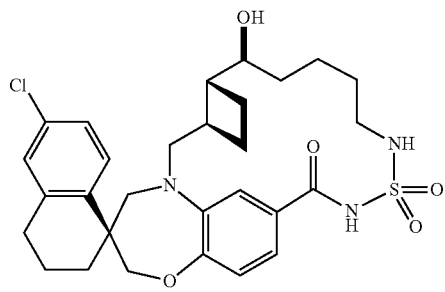

The title compound was prepared from Example 36 by a procedure similar to the one described in Example 84 (98 mg, 0.171 mmol, 80% yield).

Step 2: (1S,3'R,6'R,7'S)-6-chloro-7'-[(tert-butyldimethylsilyl)oxy]-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[16,18,24]trien]-15'-one 13',13'-dioxide

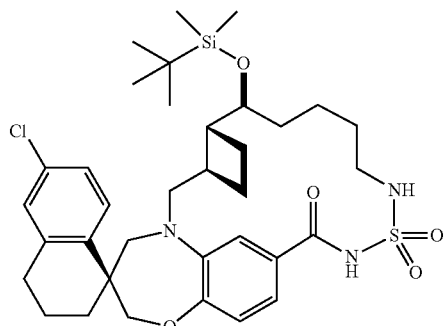

The title compound was prepared from (1S,3'R,6'R,7'S)-6-chloro-7'-hydroxy-3,4-dihydro-2h,15'h-spiro[naphthalene-1,22'-[20]oxa[13]thia[1,12,14]triazatetracyclo[14.7.2.0$^{3,6}$.0$^{19,24}$]pentacosa[16,18,24]trien]-15'-one 13',13'-dioxide by a procedure similar to the one described in Example 32, Step 1 (20 mg, 0.029 mmol, 17.0% yield).

Step 3: (1S,3'R,6'R,7'S)-6-chloro-7'-hydroxy-12'-(2-propen-1-yl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[16,18,24]trien]-15'-one 13',13'-dioxide The title compound was prepared from (1S,3'R,6'R,7'S)-6-chloro-7'-[(tert-butyldimethylsilyl)oxy]-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[16,18,24]trien 1-15'-one 13',13'-dioxide by a procedure similar to the one described in Example 34 (11 mg, 0.018 mmol, 87% yield).
$^1$H NMR (500 MHz, CDCl$_3$) δ 9.18 (br. s, 1H), 7.69 (d, J=8.4 Hz, 1H), 7.25 (br. s, 1H), 7.21-7.13 (m, 2H), 7.12-7.05 (m, 1H), 6.96 (d, J=8.1 Hz, 1H), 5.93-5.85 (m, 1H), 5.32-5.25 (m, 2H), 4.49 (d, J=14.7 Hz, 1H), 4.19-4.11 (m, 2H), 3.97 (dd, J=6.2, 16.0 Hz, 1H), 3.78 (br. s, 1H), 3.67-3.60 (m, 3H), 3.38 (d, J=12.0 Hz, 1H), 3.34-3.25 (m, 2H), 2.83-2.73 (m, 2H), 2.45-2.26 (m, 2H), 2.04-1.87 (m, 4H), 1.86-1.65 (m, 5H), 1.60-1.39 (m, 7H). m/z (ESI, +ve ion) 615.2 (M+H)$^+$.

Example 88. (1S,3'R,6'R,7'S,8'E)-6-chloro-12'-ethyl-7'-(1,3-thiazol-4-ylmethoxy)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

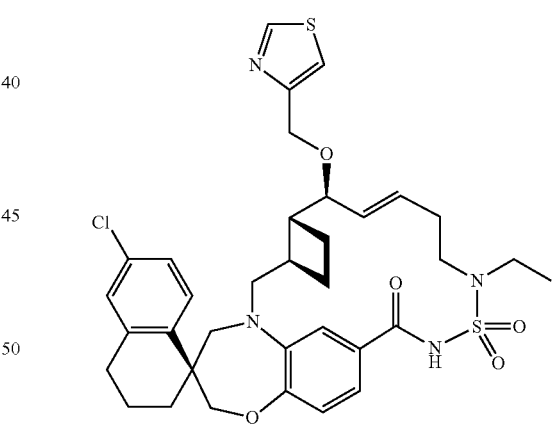

The title compound was prepared from Example 29 by a procedure similar to the one described in Example 43. $^1$H NMR (400 MHz, CDCl$_3$) δ 8.89 (d, J=11.1 Hz, 1H), 8.32 (br. s, 1H), 7.70 (d, J=8.5 Hz, 1H), 7.32 (s, 1H), 7.19-7.17 (dd, J=2.2, 8.5 Hz, 1H), 7.09 (d, J=2.3 Hz, 1H), 6.94-6.85 (m, 2H), 6.75 (s, 1H), 6.06-5.98 (m, 1H), 5.63 (dd, J=8.1, 15.6 Hz, 1H), 4.73 (d, J=12.5 Hz, 1H), 4.57 (d, J=12.9 Hz, 1H), 4.18-4.02 (m, 3H), 3.96 (dd, J=3.9, 8.8 Hz, 1H), 3.82-3.66 (m, 3H), 3.39-3.17 (m, 3H), 3.01 (dd, J=9.5, 15.6 Hz, 1H), 2.83-2.70 (m, 2H), 2.56-2.47 (m, 1H), 2.37-2.24 (m, 2H), 2.12-1.87 (m, 4H), 1.80 (br. s, 3H), 1.64 (dd, J=9.4, 19.2 Hz, 1H), 1.40 (t, J=12.1 Hz, 1H), 1.33-1.21 (m, 3H). m/z (ESI, +ve ion) 698.2 (M+H)$^+$.

245

Example 89. (1S,3'R,6'R,7'S,8'E)-6-chloro-12'-ethyl-7'-(2-oxo-2-(1-pyrrolidinyl)ethoxy)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

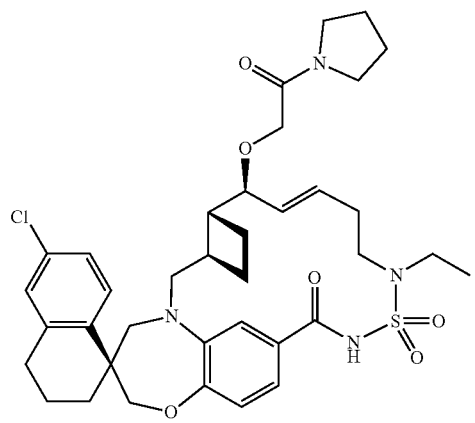

A mixture of Example 44 (4 mg, 6.08 μmol), hydroxlamine hydrochloride (2.11 mg, 0.030 mmol), N-ethyl-N-isopropylpropan-2-amine (3.49 μL, 0.020 mmol) and 41H-benzo[d][1,2,3]triazol-1-yl)oxy)tri(pyrrolidin-1-yl)phosphonium hexafluorophosphate(V) (6.32 mg, 0.012 mmol) in THF (0.25 mL) and DCM (0.25 mL) was stirred at ambient temperature for 1 hour. The reaction was quenched with H$_2$O and extracted with EtOAc. The organic extract was washed with H$_2$O, brine, dried with MgSO$_4$ and filtered. After concentration the residue was purified by reversed phase preparatory HPLC (Gemini™ Prep C$_{18}$ 5 μm column; Phenomenex, Torrance, CA; gradient elution of 40% to 85% MeCN in water, where both solvents contain 0.1% TFA, 30 min method) to afford the title compound (0.66 mg, 0.928 mmol, 15.3% yield). $^1$H NMR (400 MHz, CDCl$_3$) δ 8.67 (br. s, 1H), 7.72 (d, J=8.6 Hz, 1H), 7.20 (dd, J=2.3, 8.4 Hz, 1H), 7.11 (d, J=2.3 Hz, 1H), 6.98-6.90 (m, 2H), 6.84 (br. s, 1H), 6.11-6.03 (m, 1H), 5.61 (dd, J=8.6, 15.7 Hz, 1H), 4.21-3.99 (m, 5H), 3.89 (dd, J=4.0, 8.5 Hz, 1H), 3.81-3.64 (m, 3H), 3.60-3.50 (m, 2H), 3.48-3.23 (m, 5H), 3.12 (br. s, 1H), 2.84-2.72 (m, 2H), 2.61-2.44 (m, 2H), 2.39-2.24 (m, 3H), 2.09-1.81 (m, 6H), 1.78-1.58 (m, 4H), 1.49-1.42 (m, 1H), 1.28 (t, J=7.0 Hz, 3H). m/z (ESI, +ve ion) 712.3 (M+H)$^+$.

246

Example 90. (1S,3'R,6'R,7'S,8'E,11R,14'S)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{11,14}$.0$^{21,26}$]heptacosa[8,18,20,26]tetraen]-17'-one 15',15'-dioxide

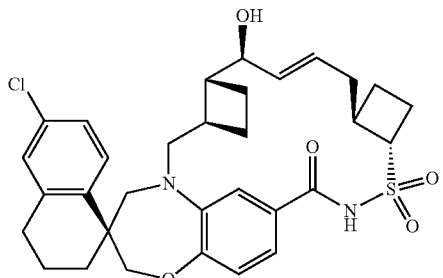

Step 1: 2-cyclobutylidene-1,1-dimethylhydrazine

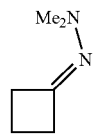

To a stirred solution of cyclobutanone (25 g, 36 mmol) in benzene (149 mL) was added 1,1-dimethylhydrazine (21.44 g, 357 mmol) and 2,2,2-trifluoroacetic acid (0.407 g, 3.57 mmol). The stirred reaction mixture was heated at reflux for five hours using a Dean-Stark trap, after which time ca. 8 mL water had condensed. The reaction mixture was then cooled to rt and partitioned between diethyl ether and water, back-extracting the aqueous phase with ether. The combined organic extracts were dried over MgSO$_4$, filtered and concentrated in vacuo. Distillation was carried out using a short-path apparatus, and the fraction boiling at 75-95° C. at ca. 20 mm of Hg was collected to provide 2-cyclobutylidene-1,1-dimethylhydrazine (18.0 g, 160 mmol, 45.0% yield).

Step 2: (S)-2-allylcyclobutanone and (R)-2-allylcyclobutanone

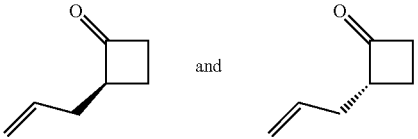

To a stirred, ca. −10° C. solution of 2-cyclobutylidene-1,1-dimethylhydrazine (12.0 g, 107 mmol) in diethyl ether (206 mL) under a nitrogen atmosphere was added n-butyllithium (nominally 2.5 M solution in hexanes; 42.8 mL, 107 mmol) dropwise via syringe over 20 minutes. The reaction mixture was stirred at −10° C. for one hour. After this time, allyl bromide (9.26 mL, 107 mmol) was added, and the mixture was allowed to warm to room temperature overnight. After this time, the mixture was acidified with aqueous HCl (1 M, 215 mL) and stirred at rt for 40 minutes. The separated aqueous layer was then extracted with diethyl ether, and the combined organic extracts were washed with brine, dried over MgSO$_4$, filtered and concentrated in vacuo (pressure: 100 mm of Hg) to give 2-allylcyclobutanone (10.55 g, 96.0 mmol, 90% yield).

Step 3: (1R,2R)-2-allylcyclobutanol and (1S,2S)-2-allylcyclobutanol

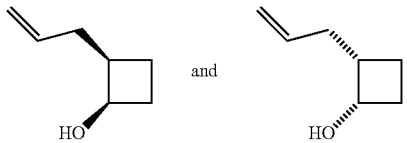

To a stirred solution of 2-allylcyclobutanone (10.5 g, 95.0 mmol) in THF (191 mL) at −78° C. under a nitrogen atmosphere was added dropwise via an addition funnel l-selectride (1 M in THF; 105 ml, 105 mmol). The reaction mixture was stirred at −78° C. for two hours and then it was allowed to warm to rt over 20 minutes. After this time, the reaction was quenched by addition of NH$_4$Cl (saturated aqueous solution) and diluted with EtOAc. The separated aqueous layer was extracted with EtOAc, and the combined organic extracts were dried over MgSO$_4$, filtered and concentrated in vacuo. Column chromatography (120 g silica gel; Hexanes:EtOAc, 1:0 to 4:1 solvent gradient) gave the title compound (5.60 g, 49.9 mmol, 52% yield) as a colorless liquid.

Step 4: (1R,2R)-2-allylcyclobutanol Methanesulfonate and (1S,2S)-2-allylcyclobutanol Methanesulfonate

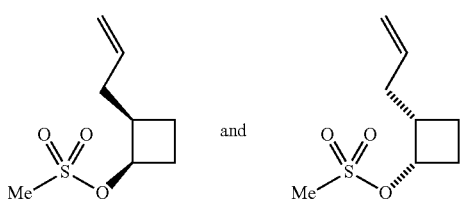

To a stirred solution of racemic cis-2-allylcyclobutanol (5.60 g, 49.9 mmol) in DCM (250 ml) at 0° C. was added triethylamine (13.9 mL, 100 mmol) followed by methanesulfonyl chloride (5.84 mL, 74.9 mmol). The reaction mixture was allowed to warm to rt overnight. After this time, the mixture was partitioned between DCM and 1M HCl (aq.). The separated aqueous layer was extracted with DCM and the combined organic extracts were washed with brine, dried over MgSO$_4$, filtered and concentrated in vacuo. Column chromatography (120 g silica gel; isocratic DCM) gave racemic cis-2-allylcyclobutanol methanesulfonate (6.63 g, 34.8 mmol, 70% yield).

Step 5: 2-(((1S,2R)-2-allylcyclobutyl)thio)pyrimidine and 2-(((1R,2S)-2-allylcyclobutyl)thio)pyrimidine

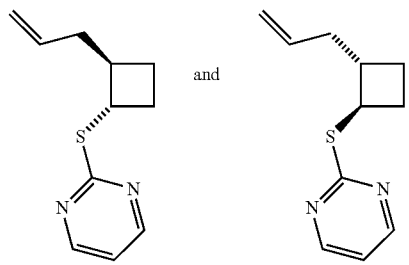

To a stirred solution of racemic cis-2-allylcyclobutanol methanesulfonate (6.60 g, 34.7 mmol) in DMF (69.4 mL) was added 2-mercaptopyrimidine (3.89 g, 34.7 mmol) and potassium carbonate (4.79 g, 34.7 mmol). The reaction mixture was heated at 70° C. for 90 minutes. After this time, the mixture had solidified. More DMF (30 mL) was added, and heating at 100° C. was continued for 90 minutes. Additional portions of 2-mercaptopyrimidine (1.9 g) and potassium carbonate (2.4 g) were then added, and the mixture was heated at 100° C. for two hours. Upon cooling to room temperature, the mixture was partitioned between EtOAc and water. The separated aqueous layer was extracted with EtOAc and the combined organic extracts were dried over MgSO$_4$, filtered and concentrated in vacuo. Column chromatography (120 g silica gel; hexanes:EtOAc, 1:0 to 4:1 solvent gradient) gave racemic trans-2-((2-allylcyclobutyl)thio)pyrimidine (4.60 g, 22.3 mmol, 64% yield).

Step 6: 2-(((1S,2R)-2-allylcyclobutyl)sulfonyl)pyrimidine and 2-(((1R,2S)-2-allylcyclobutyl)sulfonyl) pyrimidine

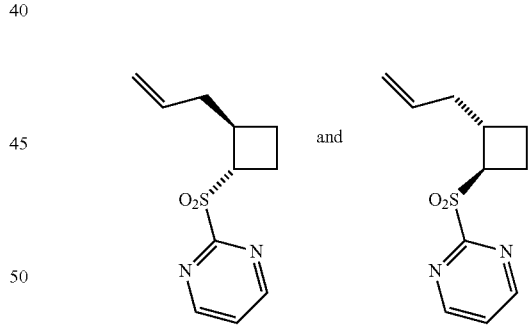

To a vigorously stirred mixture of sodium tungstate dihydrate (0.320 g, 0.969 mmol), phenylphosphonic acid (0.153 g, 0.969 mmol) and tetrabutylammonium sulfate (50 weight % solution in water; 1.126 mL, 0.969 mmol) in water (8.81 mL) was added hydrogen peroxide (30 weight % solution in water; 4.95 mL, 48.5 mmol). After two minutes, a solution of racemic trans-2-((2-allylcyclobutyl)thio)pyrimidine (4.00 g, 19.4 mmol) in toluene (88 mL) was added dropwise and the reaction mixture was stirred at 54° C. overnight. Upon cooling to rt, the mixture was between EtOAc and water. The organic layer was washed with saturated aqueous sodium sulfite, dried over MgSO$_4$, filtered and concentrated in vacuo. Column chromatography (40 g silica gel; hexanes:EtOAc, 1:0 to 3:1 solvent gradient) gave racemic trans-2-((-2-allylcyclobutyl)sulfonyl)pyrimidine (3.80 g, 15.9 mmol, 82% yield) as a colorless oil.

Step 7: (1S,2R)-2-allylcyclobutane-1-sulfonamide and (1R,2S)-2-allylcyclobutane-1-sulfonamide

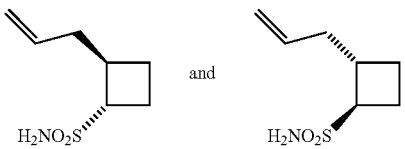

To a stirred solution of racemic trans-2-((-2-allylcyclobutyl)sulfonyl)pyrimidine (2 g, 8.39 mmol) in MeOH (84 mL) was added solid potassium carbonate (3.48 g, 25.2 mmol). The reaction mixture was stirred at rt for 30 minutes. Amidoperoxymonosulfuric acid (4.75 g, 42.0 mmol) was then added in one portion followed by 100 mL of water, causing a mild exotherm. The reaction was stirred at rt for 10 minutes, heated at 90° C. for five minutes, and finally allowed to cool to rt over one hour. The mixture was then concentrated in vacuo to ca. ⅓ of its initial volume and then it was basified by addition of 1N NaOH (aq.). The aqueous layer was back-extracted with EtOAc (2×) and the combined organics were washed with brine, dried over MgSO₄, filtered and concentrated in vacuo. The crude product was purified by column chromatography (120 g silica gel; hexanes: EtOAc, 1:0 to 3:1 solvent gradient) to give trans-2-allylcyclobutane-1-sulfonamide (0.95 g, 5.4 mmol, 65% yield).

Step 8: (S)-6'-chloro-5-(((1R,2R)-2-((S,E)-1-hydroxy-4-((1S,2R)-2-sulfamoylcyclobutyl)but-2-en-1-yl)cyclobutyl)methyl)-3',4',4',5-tetrahydro-2H,2'H-spiro[benzo[b][1,4]oxazepine-3,1'-naphthalene]-7-carboxylic Acid and (S)-6'-chloro-5-(((1R,2R)-2-((S,E)-1-hydroxy-4-((1R,2S)-2-sulfamoylcyclobutyl)but-2-EN-1-yl)cyclobutyl)methyl)-3',4',4',5-tetrahydro-2H,2'H-spiro[benzo[b][1,4]oxazepine-3,1'-naphthalene]-7-carboxylic Acid

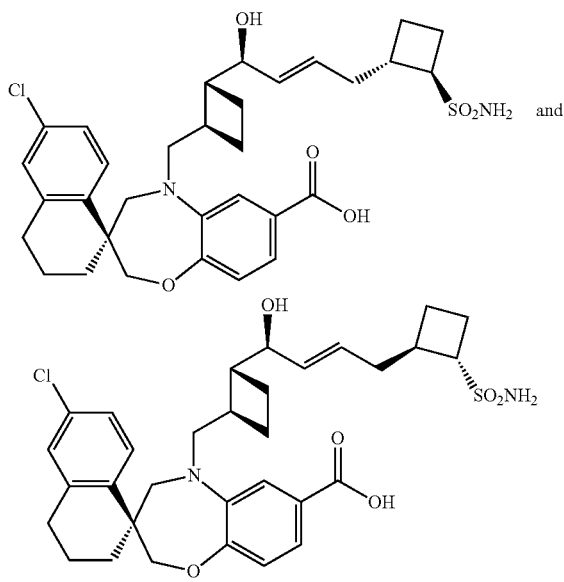

A stirred solution of Intermediate AA12A (234 mg, 0.459 mmol) in 1,2-dichloroethane (6.55 mL) was sparged with argon for five minutes. After this time, a solution of (1,3-dimesitylimidazolidin-2-ylidene)(2-isopropoxybenzylidene)ruthenium(VI) chloride (28.7 mg, 0.046 mmol) was added dropwise via syringe while sparging argon through the mixture. The reaction was stirred at rt under argon for 90 minutes. The catalyst was then deactivated by sparging air through the reaction mixture. The mixture was concentrated in vacuo, and the remaining solids were triturated with DCE (ca 2 mL) and filtered, washing the filter cake with DCE (ca 2 mL). The combined organics were concentrated in vacuo and purified by column chromatography (12 g silica gel; hexanes: (99:1 EtOAc:AcOH), 1:0 to 3:1 solvent gradient) to give a mixture of (S)-6'-chloro-5-(((1R,2R)-2-((S,E)-1-hydroxy-4-((1S,2R)-2-sulfamoylcyclobutyl)but-2-en-1-yl)cyclobutyl)methyl)-3',4',4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((1R,2S)-2-sulfamoylcyclobutyl)but-2-en-1-yl)cyclobutyl)methyl)-3',4',4',5-tetrahydro-2H,2'H-spiro[benzo[b][1,4]oxazepine-3,1'-naphthalene]-7-carboxylic acid (140 mg, 0.228 mmol, 50% combined yield).

Step 9: (1S,3'R,6'R,7'S,8'E,11'R,14'S)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{11,14}$.0$^{21,26}$]heptacosa[8,18,20,26]tetraen]-17'-one 15',15'-dioxide To a stirred, rt solution of (S)-6'-chloro-5-(((1R,2R)-2-((S,E)-1-hydroxy-4-((1S,2R)-2-sulfamoylcyclobutyl)but-2-en-1-yl)cyclobutyl)methyl)-3',4',4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((1R,2S)-2-sulfamoylcyclobutyl)but-2-en-1-yl)cyclobutyl)methyl)-3',4',4',5-tetrahydro-2H,2'H-spiro[benzo[b][1,4]oxazepine-3,1'-naphthalene]-7-carboxylic acid (i.e., the diastereomer mixture prepared in Step 8; 140 mg, 0.228 mmol total) in DCM (1.14 E+05 µL) was added DMAP (47.3 mg, 0.387 mmol). The resulting reaction mixture was cooled to 0° C. and treated with EDC (87 mg, 0.45 mmol) portionwise over five minutes. The mixture was stirred at rt overnight, and then partitioned between DCM and 1M HCl (aq.). The aqueous layer was extracted with DCM and the combined organics were washed with brine, dried over MgSO₄, filtered and concentrated in vacuo. Column chromatography (24 g silica gel, hexanes: (99:1 EtOAc:AcOH), 1:0 to 3:1 solvent gradient) gave an early-eluting diastereomer identified as (1S,3'R,6'R,7'S,8'E,11'R,14'S)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{11,14}$.0$^{21,26}$]heptacosa[8,18,20,26]tetraen]-17'-one 15',15'-dioxide (i.e., the title compound; 24 mg, 18% yield) as a white film. ¹H NMR (400 MHz, CD₃OD) δ ppm 7.72 (d, J=8.6 Hz, 1H), 7.17 (dd, J=8.4, 2.3 Hz, 1H), 7.10 (d, J=2.2 Hz, 1H), 7.05 (dd, J=8.2, 2.2 Hz, 1H), 6.95 (d, J=2.0 Hz, 1H), 6.91 (d, J=8.2 Hz, 1H), 5.84-5.95 (m, 1H), 5.58 (dd, J=15.5, 6.3 Hz, 1H), 4.28 (q, J=9.1 Hz, 1H), 4.07-4.12 (m, 1H), 4.06 (s, 2H), 3.63-3.74 (m, 2H), 3.39 (d, J=14.5 Hz, 1H), 3.17 (dd, J=15.3, 10.4 Hz, 1H), 2.83-2.92 (m, 1H), 2.71-2.82 (m, 2H), 2.48-2.61 (m, 1H), 2.22-2.44 (m, 6H), 2.00-2.11 (m, 2H), 1.85-1.99 (m, 2H), 1.67-1.84 (m, 1H), 1.55-1.65 (m, 1H), 1.43-1.53 (m, 1H). m/z (ESI, +ve ion) 597.1 (M+H)⁺. The absolute stereochemistry of the title compound (and hence also the absolute stereochemistries of all compounds stereospecifically derived from it) was established by X-ray crystallography of a co-crystal obtained upon complexation with Mcl-1. A late-eluting diastereomer having opposite chiral sense at both sulfamoylcyclobutyl stereocenters, (1S,3'R,6'R,7'S,8'E,11'S,14'R)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{11,14}$.0$^{21,26}$]heptacosa[8,18,20,26]tetraen]-17'-one 15',15'-dioxide (25 mg, 18% yield), was also obtained from the chromatography experiment.

Example 91. (1S,3'R,6'R,7'S,11'R,14'R)-6-chloro-7'-hydroxy-3,4-dihydro-2H,17'H-spiro[naphthalene-1, 24'-[22]oxa[15]thia[1,16]diazapentacyclo[16.7.2.0$^{3,6}$.0$^{11,14}$.0$^{21,26}$]heptacosa[18,20,26]trien]-17'-one 15',15'-dioxide

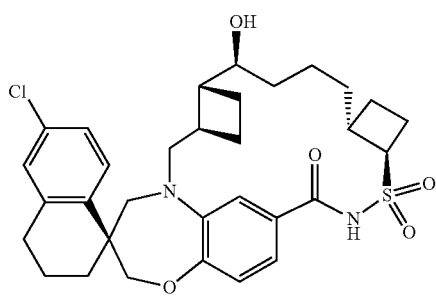 [SMILES: O=C1NS(=O)(=O)[C@@H]2CC[C@H]2CCC[C@H](O)[C@@H]2CC[C@H]2CN2C[C@@]3(CCCc4cc(Cl)ccc43)COc3ccc1cc32]

To a stirred solution of (1S,3'R,6'R,7'S,8'E,11'S,14'R)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{11,14}$.0$^{21,26}$]heptacosa[8,18,20,26]tetraen]-17'-one 15',15'-dioxide (i.e., the late diastereomer from Step 9 of Example 90; 10 mg, 0.017 mmol) in EtOAc (3349 μL) was added platinum(IV) oxide (3.8 mg, 0.017 mmol), and the reaction mixture was placed under an atmosphere of hydrogen and stirred at room temperature for 30 minutes. After this time, the reaction mixture was filtered through celite, washing the filter cake with EtOAc. The filtrate was concentrated in vacuo and purified by column chromatography (4 g silica gel; hexanes: (99:1 EtOAc:AcOH), 1:0 to 4:1 solvent gradient) to give the title compound (5.2 mg, 8.7 μmol, 52% yield) as a white solid. $^1$H NMR (400 MHz, CD$_2$Cl$_2$) δ ppm 10.38 (br. s, 1H), 7.66 (d, J=8.4 Hz, 1H), 7.49 (br. s., 1H), 7.41 (d, J=8.2 Hz, 1H), 7.15 (dd, J=8.4, 2.3 Hz, 1H), 7.09 (d, J=2.3 Hz, 1H), 6.96 (d, J=8.2 Hz, 1H), 4.18-4.25 (m, 1H), 4.12-4.17 (m, 1H), 4.05 (q, J=9.0 Hz, 1H), 3.81 (br. s., 1H), 3.44 (q, J=7.0 Hz, 1H), 3.48 (br. s., 3H), 2.92-3.07 (m, 1H), 2.71-2.80 (m, 2H), 2.41-2.57 (m, 1H), 2.23-2.35 (m, 3H), 2.01-2.10 (m, 2H), 1.89 (d, J=6.5 Hz, 1H), 1.68-1.85 (m, 4H), 1.61 (dt, J=19.5, 9.8 Hz, 4H), 1.48 (br. s., 2H), 1.32-1.44 (m, 3H). m/z (ESI, +ve ion) 599.2 (M+H)$^+$.

Example 92. (1S,3'R,6'R,7'S,11'S,14'S)-6-chloro-7'-hydroxy-3,4-dihydro-2H,17'H-spiro[naphthalene-1, 24'-[22]oxa[15]thia[1,16]diazapentacyclo[16.7.2.0$^{3,6}$.0$^{11,14}$.0$^{21,26}$]heptacosa[18,20,26]trien]-17'-one 15',15'-dioxide

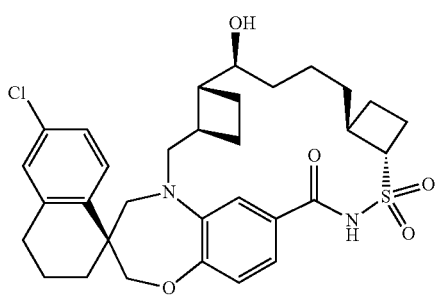 [SMILES: O=C1NS(=O)(=O)[C@H]2CC[C@@H]2CCC[C@H](O)[C@@H]2CC[C@H]2CN2C[C@@]3(CCCc4cc(Cl)ccc43)COc3ccc1cc32]

To a stirred solution of (1S,3'R,6'R,7'S,8'E,11'R,14'S)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{11,14}$.0$^{21,26}$]heptacosa[8,18,20,26]tetraen]-17'-one 15',15'-dioxide (i.e., the early-eluting diastereomer from Step 9 of Example 90; 17 mg, 0.028 mmol) in EtOAc (5.69 mL) was added platinum(IV) oxide (6.46 mg, 0.028 mmol), and the reaction mixture was placed under an atmosphere of hydrogen and stirred at room temperature for 30 minutes. After this time, the reaction mixture was filtered through celite, washing the filter cake with EtOAc. The filtrate was concentrated in vacuo and purified by column chromatography (4 g silica gel; hexanes: (99:1 EtOAc:AcOH), 1:0 to 4:1 solvent gradient) to give the title compound (6.6 mg, 0.011 mmol, 39% yield) as a white solid. $^1$H NMR (400 MHz, CD$_2$Cl$_2$) δ ppm 9.48 (br. s., 1H), 7.71 (d, J=8.4 Hz, 1H), 7.29 (dd, J=8.2, 2.0 Hz, 1H), 7.18 (d, J=2.3 Hz, 1H), 7.16 (d, J=2.2 Hz, 1H), 7.09 (d, J=2.3 Hz, 1H), 6.97 (d, J=8.4 Hz, 1H), 4.14 (s, 2H), 3.74 (q, J=9.1 Hz, 1H), 3.48-3.67 (m, 3H), 3.22-3.45 (m, 2H), 2.95 (quind, J=9.3, 9.3, 9.3, 9.3, 3.7 Hz, 1H), 2.68-2.85 (m, 4H), 2.22-2.34 (m, 1H), 2.09-2.20 (m, 1H), 2.00 (m, 3H), 1.50 (m, 14H). m/z (ESI, +ve ion) 599.2 (M+H)$^+$.

Example 93. (1S,3'R,6'R,7'S,8'E,11'S,14'R)-6-chloro-7'-(2-methoxyethoxy)-3,4-dihydro-2H,17'H-spiro[naphthalene-1,24'-[22]oxa[15]thia[1,16]diazapentacyclo[16.7.2.0$^{3,6}$.0$^{11,14}$.0$^{21,26}$]heptacosa[8,18,20,26]tetraen]-17'-one 15',15'-dioxide

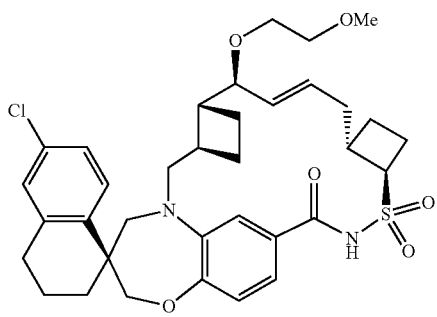 [SMILES: COCCO[C@H]1/C=C/C[C@@H]2CC[C@H]2S(=O)(=O)NC(=O)c2ccc3c(c2)N(C[C@@H]2CC[C@H]21)C[C@@]1(CCCc2cc(Cl)ccc21)CO3]

To a stirred solution of (1S,3'R,6'R,7'S,8'E,11'S,14'R)-6-chloro-7'-hydroxy-3,4-dihydro-2H,17'H-spiro[naphthalene- 1,24'-[22]oxa[15]thia[1,16]diazapentacyclo[16.7.2.0$^{3,6}$.0$^{11,14}$.0$^{21,26}$]heptacosa[8,18,20,26]tetraen]-17'-one 15',15'-dioxide (i.e., the late diastereomer from Step 9 of Example 90; 10 mg, 0.017 mmol) in DMF (335 μL) at 0° C. was added sodium hydride (60% dispersion in mineral oil; 6.7 mg, 0.17 mmol). The reaction mixture was stirred at this temperature for 15 minutes. After this time, 2-bromoethyl methyl ether (7.9 μL, 0.084 mmol) was added, and the reaction mixture was stirred at rt over the weekend. The reaction mixture was then partitioned between EtOAc and water. The separated organic layer was dried over MgSO$_4$, filtered and concentrated in vacuo. Column chromatography (4 g silica gel; DCM:acetone, 1:0 to 9:1 eluent gradient) gave the title compound (4.0 mg, 6.1 μmol, 36% yield) as a white solid. $^1$H NMR (400 MHz, CD$_2$Cl$_2$) δ ppm 8.56 (br. s, 1H), 7.70 (d, J=8.4 Hz, 1H), 7.16 (dd, J=8.6, 2.3 Hz, 1H), 7.09 (d, J=2.2 Hz, 1H), 6.94-7.04 (br. s., 2H), 6.88-6.93 (m, 1H), 5.71-5.84 (m, 1H), 5.60 (dd, J=15.6, 7.6 Hz, 1H), 4.56 (d, J=8.4 Hz, 1H), 4.10 (s, 2H), 3.83 (dd, 5.5 Hz, 1H), 3.59-3.74 (m, 3H), 3.44-3.53 (m, 3H), 3.33 (s, 3H), 3.12-3.32 (m, 2H), 2.86-2.98 (m, 1H), 2.69-2.81 (m, 2H), 2.52 (dd, J=9.1, 5.6 Hz, 1H), 2.43 (dt, J=20.0, 9.8 Hz, 1H), 2.13-2.35 (m, 4H), 2.00 (s, 2H), 1.60-1.94 (m, 7H), 1.40-1.52 (m, 1H). m/z (ESI, +ve ion) 655.3 (M+H)$^+$.

Example 94. (1S,3'R,6'R,7'S,8'E,11'R,14'S)-6-chloro-7'-((1-methyl-1H-1,2,4-triazol-3-yl)methoxy)-3,4-dihydro-2H,17'H-spiro[naphthalene-1,24'-[22]oxa[15]thia[1,16]diazapentacyclo[16.7.2.0$^{3,6}$.0$^{11,14}$.0$^{21,26}$]heptacosa[8,18,20,26]tetraen]-17'-one 15',15'-dioxide

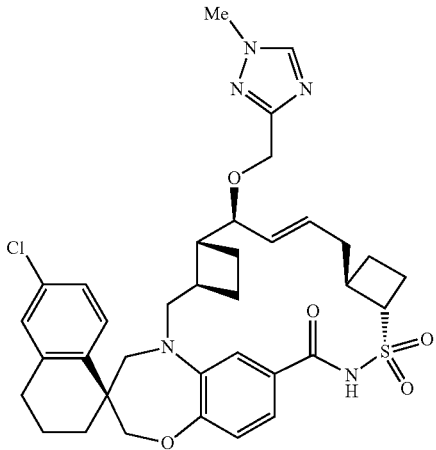

To a stirred solution of (1S,3'R,6'R,7'S,8'E,11'R,14'S)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{11,14}$.0$^{21,26}$]heptacosa[8,18,20,26]tetraen]-17'-one 15',15'-dioxide (i.e., the early diastereomer from Step 9 of Example 90; 7.0 mg, 0.012 mmol) in THF (234 μL) under an atmosphere of nitrogen was added sodium hydride (60% dispersion in mineral oil; 4.7 mg, 0.12 mmol). The reaction was stirred at rt for 15 minutes and then it was treated with a solution of 3-(chloromethyl)-1-methyl-1H-1,2,4-triazole hydrochloride (9.8 mg, 0.059 mmol) in DMF (234 μL) dropwise over one minute. The resulting mixture was stirred at rt for three hours. After this time, additional portions of sodium hydride (4.7 mg, 0.12 mmol) and 3-(chloromethyl)-1-methyl-1H-1,2,4-triazole hydrochloride (9.9 mg, 0.059 mmol) were added and the reaction was stirred at rt over the weekend. The reaction mixture was then partitioned between EtOAc and brine. The separated organic layer was dried over MgSO$_4$, filtered and concentrated in vacuo. Column chromatography (1 g silica gel; hexanes: (99:1 EtOAc:AcOH), 1:0 to 1:2 eluent gradient) gave the title compound (3.5 mg, 5.1 μmol, 43% yield) as a white solid. $^1$H NMR (500 MHz, CD$_2$Cl$_2$) δ ppm 8.01 (s, 1H), 7.69 (d, J=8.6 Hz, 1H), 7.16 (dd, J=8.4, 2.3 Hz, 1H), 7.08 (d, J=2.2 Hz, 1H), 6.89-6.99 (m, 2H), 6.87 (d, J=8.1 Hz, 1H), 5.79-5.88 (m, 1H), 5.61 (dd, J=15.5, 7.9 Hz, 1H), 4.60-4.67 (m, 1H), 4.57 (d, J=11.7 Hz, 1H), 4.41 (d, J=12.0 Hz, 1H), 4.04-4.11 (m, 2H), 3.91 (s, 3H), 3.88 (s, 1H), 3.60-3.71 (m, 2H), 3.25 (d, J=14.2 Hz, 1H), 3.12 (br. s, 1H), 2.85-2.94 (m, 1H), 2.69-2.81 (m, 2H), 2.47-2.55 (m, 1H), 2.39-2.46 (m, 1H), 2.27-2.34 (m, 1H), 2.16-2.27 (m, 3H), 1.95-2.03 (m, 2H), 1.86-1.95 (m, 2H), 1.61-1.86 (m, 6H), 1.39-1.48 (m, 1H). m/z (ESI, +ve ion) 692.2 (M+H)$^+$.

Example 95. (1S,3'R,6'R,7'S,8'E,11'R,14'S)-6-chloro-7'-methoxy-3,4-dihydro-2H,17'H-spiro[naphthalene-1,24'-[22]oxa[15]thia[1,16]diazapentacyclo[16.7.2.0$^{3,6}$.0$^{11,14}$.0$^{21,26}$]heptacosa[8,18,20,26]tetraen]-17'-one 15',15'-dioxide

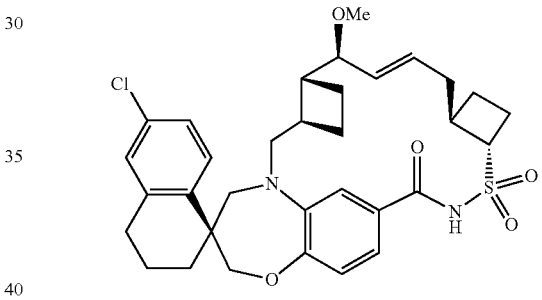

To a stirred solution of (1S,3'R,6'R,7'S,8'E,11'R,14'S)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{11,14}$.0$^{21,26}$]heptacosa[8,18,20,26]tetraen]-17'-one 15',15'-dioxide (i.e., the early diastereomer from Step 9 of Example 90; 4.0 mg, 6.7 μmop in THF (0.67 mL) under a nitrogen atmosphere was added sodium hydride (60% dispersion in mineral oil; 1.3 mg, 0.033 mmol) in one portion. After 10 minutes, iodomethane (1.3 μL, 0.020 mmol) was added and the resulting mixture was stirred at rt for four hours. Additional portions of sodium hydride (4.0 mg, 0.099 mmol) and MeI (5 μL, 0.077 mmol) were than added, and the reaction mixture was stirred at rt overnight. On the following day, the reaction mixture was partitioned between EtOAc and water. The separated organic layer was dried over MgSO$_4$, filtered and concentrated in vacuo. Column chromatography (ca. 1 g silica gel; hexanes: (99:1 EtOAc:AcOH), 1:0 to 4:1 eluent gradient) gave the title compound (1.4 mg, 2.3 μma 34% yield) as a white solid. $^1$H NMR (400 MHz, CD$_2$Cl$_2$) δ ppm 8.40 (br. s., 1H), 7.70 (d, J=8.4 Hz, 1H), 7.16 (dd, J=8.6, 2.3 Hz, 1H), 7.09 (d, J=2.2 Hz, 1H), 6.86-7.01 (m, 3H), 5.73-5.84 (m, 1H), 5.52-5.62 (m, 1H), 4.57-4.68 (m, 1H), 4.04-4.14 (m, 2H), 3.71 (dd, J=8.2, 4.9 Hz, 1H), 3.66 (d, J=14.7 Hz, 1H), 3.31 (s, 2H), 3.27 (d, J=14.7 Hz, 1H), 3.15 (br. s., 1H), 2.87-2.99 (m, 1H), 2.69-2.83 (m, 2H), 2.38-2.56 (m, 2H), 2.12-2.33 (m, 4H), 2.04 (br. s., 1H), 1.77-2.00 (m, 4H), 1.61-1.76 (m, 4H), 1.39-1.50 (m, 2H), 1.31 (br. s., 1H). m/z (ESI, +ve ion) 611.2 (M+H)+.

Example 96. (1S,3'R,6'R)-6-chloro-8'-(4-methoxy-benzyl)-3,4-dihydro-2H,7'H,15'H-spiro[naphthalene-1,22'-[20]oxa[13]thia[1,8,14]triazatetracyclo[14.7.2.0³,⁶.0¹⁹,²⁴]pentacosa[16,18,24]trien]-7',15'-dione 13',13'-dioxide

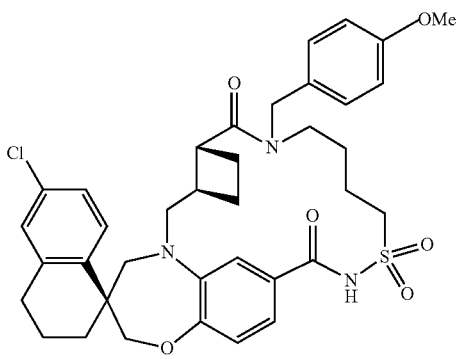 [SMILES: Cc1ccc(CN2CCCCS(=O)(=O)NC(=O)c3ccc4c(c3)N(C[C@@H]3CC[C@H]3C2=O)C[C@@]2(CCCc3cc(Cl)ccc32)CO4)cc1]

Step 1: prop-2-ene-1-sulfonamide

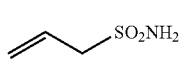

To a 250-mL round-bottom flask was added prop-2-ene-1-sulfonyl chloride (Matrix Scientific; 2.00 g, 14.2 mmol) in 10 mL of 1,4-dioxane. Ammonia (0.5 M solution in methanol; 71.1 mL, 35.6 mmol) was added to the solution at rt over one hour, causing formation of a white precipitate. The reaction mixture was stirred at rt overnight and then diluted with water (20 mL). The resulting mixture was extracted with 3:1 chloroform:isopropanol (4×30 mL). The organics were concentrated in vacuo and the resulting crude material was further purified by column chromatography (40 g silica gel; 40 to 100% eluent gradient of EtOAc in hexanes) to provide prop-2-ene-1-sulfonamide (0.72 g, 5.9 mmol, 42% yield).

Step 2: (1R,2R)-2-(((S)-7-(tert-butyoxycarbonyl)-6'-chloro-3',4'-dihydro-2H,2'H-spiro[benzo[b][1,4]oxazepine-3,1'-naphthalen]-5(4H)-yl)methyl)cyclobutanecarboxylic Acid

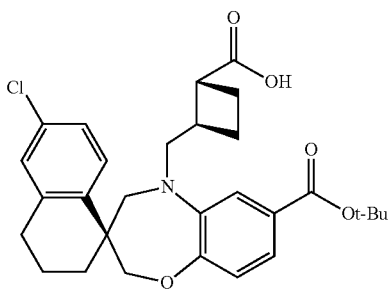 [SMILES: CC(C)(C)OC(=O)c1ccc2c(c1)N(C[C@@H]1CC[C@H]1C(=O)O)C[C@@]1(CCCc3cc(Cl)ccc31)CO2]

To a stirred solution of (S)-tert-butyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (440 mg, 0.887 mmol, Intermediate AA11A, step 20B) in t-BuOH (1.8 mL) and 2-methyl-2-butene (1.8 mL) was added a solution of sodium chlorite (168 mg, 1.86 mmol) and dihydrogen sodium phosphate (112 µL, 1.86 mmol) in water (1.5 mL). The reaction mixture was stirred at rt for five hours. After this time, the reaction mixture was partitioned between EtOAc and 1 M HCl. The separated organic layer was dried over MgSO₄, filtered and concentrated in vacuo. Column chromatography (12 g silica gel; hexanes: (99:1 EtOAc:AcOH), 1:0 to 2:1 eluent gradient) gave (1R,2R)-2-(((S)-7-(tert-butoxycarbonyl)-6'-chloro-3',4'-dihydro-2H,2'H-spiro[benzo[b][1,4]oxazepine-3,1'-naphthalen]-5(4H)-yl)methyl)cyclobutanecarboxylic acid (300 mg, 0.586 mmol, 66% yield).

Step 3: (S)-tert-butyl 5-(((1R,2R)-2-(allyl(4-methoxybenzyl)carbamoyl)cyclobutyl)methyl)-6'-chloro-3',4,4',5-tetrahydro-2H,2'H-carboxylate

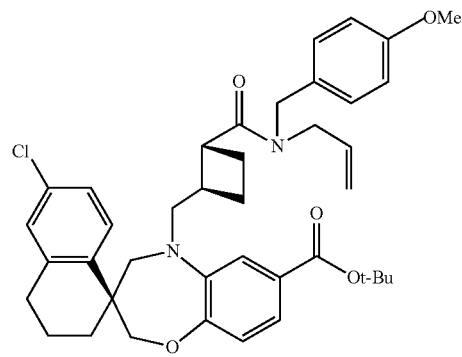 [SMILES: C=CCN(Cc1ccc(C)cc1)C(=O)[C@@H]1CC[C@H]1CN1C[C@@]2(CCCc3cc(Cl)ccc32)COc2ccc(C(=O)OC(C)(C)C)cc21]

To a stirred solution of (1R,2R)-2-(((S)-7-(tert-butoxycarbonyl)-6'-chloro-3',4'-dihydro-2H,2'H-spiro[benzo[b][1,4]oxazepine-3,1'-naphthalen]-5(4H)-yl)methyl)cyclobutanecarboxylic acid (300 mg, 0.586 mmol) and N-(4-methoxybenzyl)prop-2-en-1-amine (208 mg, 1.17 mmol) in DCM (2929 µL) was added EDC (146 mg, 0.762 mmol) and HOBT (117 mg, 0.762 mmol). The reaction mixture was stirred at rt overnight and then partitioned between DCM and saturated sodium bicarbonate (aq.). The separated organic layer was dried over MgSO₄, filtered and concentrated in vacuo. Column chromatography (12 g silica gel; hexanes: (99:1 EtOAc:AcOH), 1:0 to 4:1 eluent gradient) gave (S)-tert-butyl 5-(((1R,2R)-2-(allyl(4-methoxybenzyl)carbamoyl)cyclobutyl)methyl)-6'-chloro-3',4,4',5-tetrahydro-2H,2'H-spiro[benzo[b][1,4]oxazepine-3,1'-naphthalene]-7-carboxylate (300 mg, 0.447 mmol, 76% yield).

Step 4: (S)-5-(((1R,2R)-2-(allyl(4-methoxybenzyl)carbamoyl)cyclobutyl)methyl)-6'-chloro-3',4,4',5-tetrahydro-2H,2'H-spiro[benzo[b][1,4]oxazepine-3,1'-naphthalene]-7-carboxylic Acid

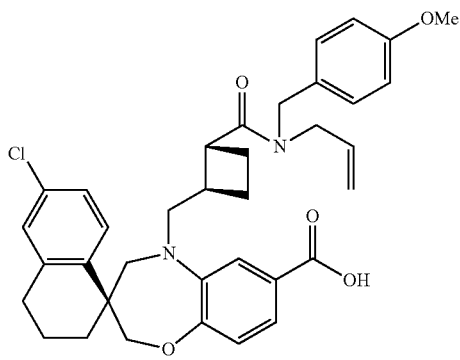 [SMILES: C=CCN(Cc1ccc(OC)cc1)C(=O)[C@@H]1CC[C@H]1CN1C[C@@]2(CCCc3cc(Cl)ccc32)COc2ccc(C(=O)O)cc21]

A solution of (S)-tert-butyl 5-(((1R,2R)-2-(allyl(4-methoxybenzyl)carbamoyl)cyclobutyl)methyl)-6'-chloro-3',4,4',5-tetrahydro-2H,2'H-spiro[benzo[b][1,4]oxazepine-3,1'-naphthalene]-7-carboxylate (300 mg, 0.447 mmol) in CH$_2$Cl$_2$ (3352 µL) and TFA (1117 µL) was stirred at rt overnight. After this time, the reaction mixture was concentrated in vacuo and partitioned between DCM and saturated sodium bicarbonate. The separated organic layer was dried over MgSO$_4$, filtered and concentrated in vacuo to give crude (S)-5-(((1R,2R)-2-(allyl(4-methoxybenzyl)carbamoyl)cyclobutyl)methyl)-6'-chloro-3',4,4',5-tetrahydro-2H,2'H-spiro[benzo[b][1,4]oxazepine-3,1'-naphthalene]-7-carboxylic acid (230 mg, 0.374 mmol, 84% yield), which was used in the subsequent step without further purification.

Step 5: (S)-5-(((1R,2R)-2-(allyl(4-methoxybenzyl)carbamoyl)cyclobutyl)methyl)-N-(allylsulfonyl)-6'-chloro-3',4,4',5-tetrahydro-2H,2'H-spiro[benzo[b][1,4]oxazepine-3,1'-naphthalene]-7-carboxamide

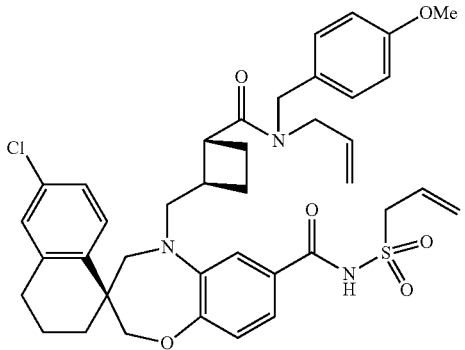 [SMILES: C=CCN(Cc1ccc(OC)cc1)C(=O)[C@@H]1CC[C@H]1CN1C[C@@]2(CCCc3cc(Cl)ccc32)COc2ccc(C(=O)NS(=O)(=O)CC=C)cc21]

To a stirred solution of (S)-5-(((1R,2R)-2-(allyl(4-methoxybenzyl)carbamoyl)cyclobutyl)methyl)-6'-chloro-3',4,4',5-tetrahydro-2H,2'H-spiro[benzo[b][1,4]oxazepine-3,1'-naphthalene]-7-carboxylic acid (50 mg, 0.081 mmol) in DCM (1626 µL) was added prop-2-ene-1-sulfonamide (29.5 mg, 0.244 mmol, Example 96, step 1), EDC (46.7 mg, 0.244 mmol) and DMAP (29.8 mg, 0.244 mmol). The reaction was stirred at rt for three hours and was then partitioned between DCM and saturated sodium bicarbonate (aq.). The separated organic layer was dried over MgSO$_4$, filtered and concentrated in vacuo. Column chromatography (12 g silica gel, hexanes: (99:1 EtOAc:AcOH), 1:0 to 3:1 eluent gradient) gave (S)-5-(((1R,2R)-2-(allyl(4-methoxybenzyl)carbamoyl)cyclobutyl)methyl)-N-(allylsulfonyl)-6'-chloro-3',4,4',5-tetrahydro-2H,2'H-spiro[benzo[b][1,4]oxazepine-3,1'-naphthalene]-7-carboxamide (42 mg, 0.058 mmol, 72% yield).

Step 6: (1S,3'R,6'R,10'E)-6-chloro-8'-(4-methoxybenzyl)-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[10,16,18,24]tetraen]-7',15'-dione 13',13'-dioxide or (1S,3'R,6'R,10'Z)-6-chloro-8'-(4-methoxybenzyl)-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[10,16,18,24]tetraen]-7',15'-dione 13',13'-dioxide

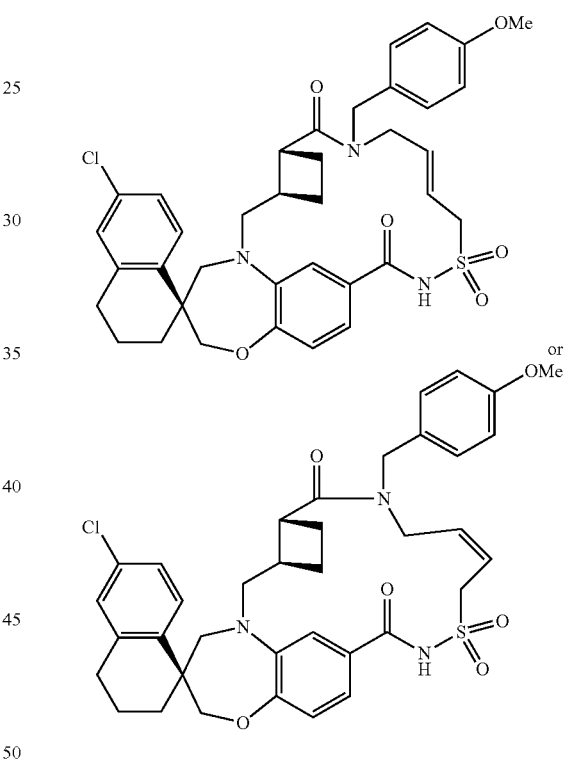

A stirred solution of (S)-5-(((1R,2R)-2-(allyl(4-methoxybenzyl)carbamoyl)cyclobutyl)methyl)-N-(allylsulfonyl)-6'-chloro-3',4,4',5-tetrahydro-2H,2'H-spiro[benzo[b][1,4]oxazepine-3,1'-naphthalene]-7-carboxamide (41 mg, 0.057 mmol) in toluene (57 mL) was sparged with argon for 20 minutes. After this time, Hoveyda-Grubbs, 2$^{nd}$ generation catalyst (7.1 mg, 0.011 mmol) was added and the reaction mixture was heated at 110° C. for 90 minutes. Upon cooling to rt, air was sparged through the mixture for five minutes to deactivate the catalyst. The solvent was then evaporated in vacuo and the resulting residue was purified by column chromatography (4 g silica gel; hexanes: (99:1 EtOAc:AcOH), 1:0 to 4:1 eluent gradient) to give the title compound (20 mg, 0.029 mmol, 51% yield). Stereochemical configuration of the olefin at the 10' position was not rigorously determined.

Step 7: (1S,3'R,6'R)-6-chloro-8'-(4-methoxybenzyl)-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[16,18,24]trien]-7',15'-dione 13',13'-dioxide To a stirred solution of either (1S,3'R,6'R,10'E)-6-chloro-8'-(4-methoxybenzyl)-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[10,16,18,24]tetraen]-7',15'-dione 13',13'-dioxide or (1S,3'R,6'R,10'Z)-6-chloro-8'-(4-methoxybenzyl)-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[10,16,18,24]tetraen]-7',15'-dione 13',13'-dioxide (85 mg, 0.123 mmol) in ethyl acetate (15 mL) was added platinum(IV) oxide (28.0 mg, 0.123 mmol). The flask was evacuated and filled with hydrogen gas (three times) and the reaction mixture stirred at rt for one hour under a hydrogen atmosphere. After this time, an additional portion of platinum (IV) oxide (15 mg, 0.066 mmol) was added and the flask was charged with hydrogen again as described above. The reaction mixture was stirred at rt for five more hours, and was then filtered through celite, washing the filter cake with ethyl acetate. The filtrate was concentrated in vacuo and the resulting crude material was purified by column chromatography (4 g silica gel; hexanes:(99:1 EtOAc:AcOH), 1:0 to 3:1 eluent gradient) to give (1S,3'R,6'R)-6-chloro-8'-(4-methoxybenzyl)-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[16,18,24]trien]-7',15'-dione 13',13'-dioxide (20 mg, 0.029 mmol, 23% yield) as a white solid. $^1$H NMR (400 MHz, CDCl$_3$) δ ppm 10.17 (s, 1H), 9.89 (br. s., 1H), 7.73 (d, J=8.6 Hz, 1H), 7.51 (dd, J=8.3, 2.1 Hz, 1H), 7.43 (d, J=2.0 Hz, 1H), 7.18 (dd, J=8.5, 2.2 Hz, 1H), 7.09 (d, J=2.3 Hz, 1H), 7.01-7.05 (m, 2H), 6.99 (d, J=8.4 Hz, 1H), 6.85-6.93 (m, 2H), 4.33-4.54 (m, 2H), 4.07-4.19 (m, 2H), 3.82 (s, 3H), 3.63-3.75 (m, 3H), 3.52-3.63 (m, 1H), 3.39-3.51 (m, 1H), 3.29-3.38 (m, 1H), 3.10-3.28 (m, 3H), 2.87-2.99 (m, 1H), 2.71-2.83 (m, 2H), 2.08 (d, J=3.9 Hz, 1H), 1.85-2.04 (m, 5H), 1.66-1.85 (m, 2H), 1.45-1.62 (m, 3H). m/z (ESI, +ve ion) 692.2 (M+H)$^+$.

Example 97. (1S,3'R,6'R,10'E)-6-chloro-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[10,16,18,24]tetraen]-7',15'-dione 13',13'-dioxide or (1S,3'R,6'R,10'Z)-6-chloro-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[10,16,18,24]tetraen]-7',15'-dione 13',13'-dioxide

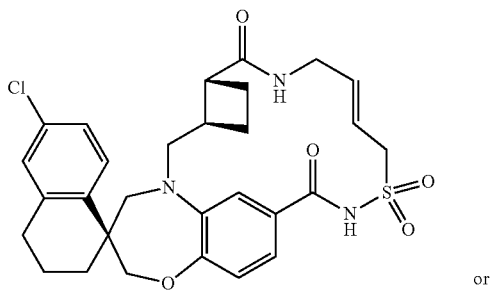

or

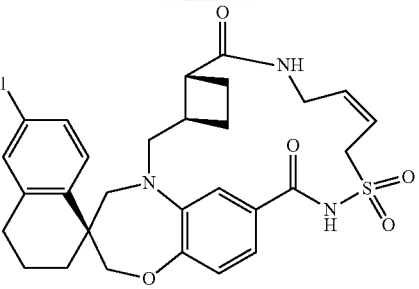

A stirred solution of either (1S,3'R,6'R,1 O'E)-6-chloro-8'-(4-methoxybenzyl)-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[10,16,18,24]tetraen]-7',15'-dione 13',13'-dioxide or (1S,3'R,6'R,10'Z)-6-chloro-8'-(4-methoxybenzyl)-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[10,16,18,24]tetraen]-7',15'-dione 13',13'-dioxide (20 mg, 0.029 mmol; Example 96, Step 7) in trifluoroacetic acid (2232 µL, 29.0 mmol) was heated at 65° C. for five hours, cooled to room temperature, and concentrated in vacuo. The resulting residue was partitioned between DCM and saturated sodium bicarbonate (aq.). The organic layer was dried over MgSO$_4$, filtered and concentrated in vacuo. Column chromatography (4 g silica gel; hexanes: (99:1 EtOAc:AcOH), 1:0 to 3:1 eluent gradient) gave the title compound (2.8 mg, 4.91 µmol, 16.95% yield) as a white solid. $^1$H NMR (400 MHz, CDCl$_3$) δ ppm 9.68 (s, 1H), 7.67 (d, J=8.4 Hz, 1H), 7.26-7.30 (m, 1H), 7.18 (dd, J=8.5, 2.2 Hz, 1H), 7.09 (d, J=2.2 Hz, 1H), 6.97 (d, J=8.2 Hz, 1H), 6.89 (d, J=2.0 Hz, 1H), 5.94 (t, J=5.4 Hz, 1H), 5.87 (dt, J=15.6, 7.5 Hz, 1H), 5.67-5.77 (m, 1H), 4.22 (dd, J=14.3, 8.0 Hz, 1H), 4.09 (s, 2H), 4.03 (dd, J=14.1, 7.0 Hz, 1H), 3.74-3.91 (m, 3H), 3.67 (d, J=13.9 Hz, 1H), 3.23-3.36 (m, 2H), 2.71-2.82 (m, 4H), 1.99-2.08 (m, 2H), 1.88-1.97 (m, 2H), 1.74-1.88 (m, 2H), 1.52 (t, J=11.5 Hz, 1H). m/z (ESI, +ve ion) 570.2 (M+H)$^+$.

Example 98. (1S,3'R,6'R)-6-chloro-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[16,18,24]triene]-7',15'-dione 13',13'-dioxide

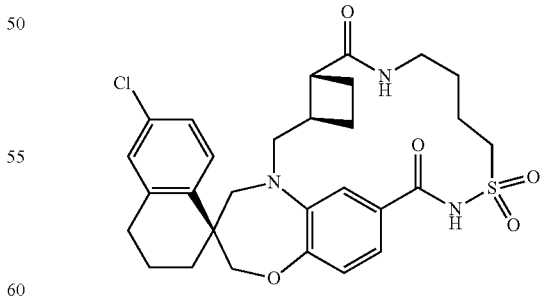

A stirred solution of (1S,3'R,6'R)-6-chloro-8'-(4-methoxybenzyl)-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[16,18,24]trien]-7',15'-dione 13',13'-dioxide (15 mg, 0.022 mmol, Example 96, step 7) in trifluoroacetic acid (835 µL, 10.8 mmol) was heated at 65°

C. for three hours. After this time, the reaction mixture was cooled to rt and concentrated in vacuo. The resulting residue was partitioned between DCM and saturated sodium bicarbonate (aq.). The aqueous layer was extracted with DCM (2×) and the combined organics were dried over MgSO$_4$, filtered and concentrated in vacuo. Column chromatography (4 g silica gel; hexanes: (99:1 EtOAc:AcOH), 1:0 to 2:1 eluent gradient) gave (1S,3'R,6'R)-6-chloro-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[16,18,24]triene]-7',15'-dione 13',13'-dioxide (4.9 mg, 8.6 μmol, 39% yield) as a white solid. $^1$H NMR (400 MHz, CDCl$_3$) δ ppm 9.86-10.23 (m, 1H), 7.71 (d, J=8.6 Hz, 1H), 7.39 (dd, J=8.2, 2.0 Hz, 1H), 7.23 (d, J=2.0 Hz, 1H), 7.18 (dd, J=8.6, 2.3 Hz, 1H), 7.09 (d, J=2.2 Hz, 1H), 6.96 (d, J=8.4 Hz, 1H), 5.95 (t, J=6.3 Hz, 1H), 4.03-4.12 (m, 2H), 3.96 (d, J=15.1 Hz, 1H), 3.70-3.82 (m, 1H), 3.63-3.70 (m, 2H), 3.41-3.50 (m, 1H), 3.07-3.24 (m, 3H), 2.74-2.84 (m, 4H), 2.04-2.15 (m, 1H), 1.86-2.03 (m, 6H), 1.69-1.83 (m, 4H), 1.44 (t, J=11.9 Hz, 1H). m/z (ESI, +ve ion) 572.2 (M+H)$^+$.

Example 99. (1S,3'R,6'R)-6-chloro-8'-methyl-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[16,18,24]trien]-7',15'-dione 13',13'-dioxide

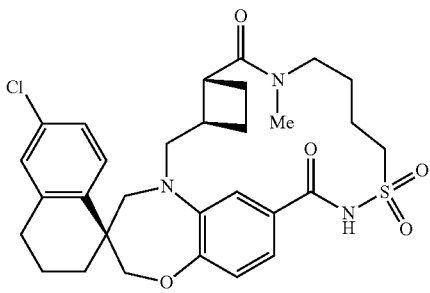 [SMILES: CN1CCCCS(=O)(=O)NC(=O)c2ccc3c(c2)N(C[C@@H]2CC[C@H]2C1=O)C[C@@]1(CCCc2cc(Cl)ccc21)CO3]

Step 1: (S)-tert-butyl 5-(((1R,2R)-2-(allyl(methyl)carbamoyl)cyclobutyl)methyl)-6'-chloro-3',4,4',5-tetrahydro-2H,2'H-spiro[benzo[b][1,4]oxazepine-3,1'-naphthalene]-7-carboxylate

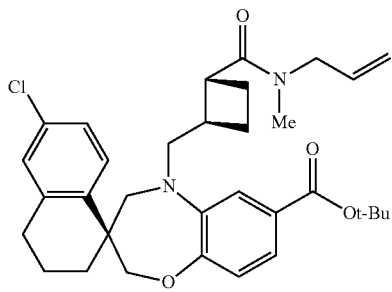 [SMILES: C=CCN(C)C(=O)[C@@H]1CC[C@H]1CN1C[C@@]2(CCCc3cc(Cl)ccc32)COc2ccc(C(=O)OC(C)(C)C)cc21]

To a stirred solution of (1R,2R)-2-(((S)-7-(tert-butoxycarbonyl)-6'-chloro-3',4'-dihydro-2H,2'H-spiro[benzo[b][1,4]oxazepine-3,1'-naphthalen]-5(4H)-yl)methyl)cyclobutanecarboxylic acid (125 mg, 0.244 mmol; Example 96, step 2) in DCM (1221 μL) was added EDC (56.2 mg, 0.293 mmol), HOBT (44.9 mg, 0.293 mmol) and N-methylallylamine (34.7 μL, 0.488 mmol). The resulting reaction mixture was stirred at rt for four hours and then partitioned between DCM and saturated sodium bicarbonate (aq.). The organics were dried over MgSO$_4$, filtered and concentrated in vacuo. The resulting residue by column chromatography (12 g silica gel; hexanes: (99:1 EtOAc:AcOH), 1:0 to 85:5 eluent gradient) to give (S)-tert-butyl 5-(((1R,2R)-2-(allyl(methyl)carbamoyl)cyclobutyl)methyl)-6'-chloro-3',4,4',5-tetrahydro-2H,2'H-spiro[benzo[b][1,4]oxazepine-3,1'-naphthalene]-7-carboxylate (120 mg, 0.212 mmol, 87% yield).

Step 2: (S)-5-(((1R,2R)-2-(allyl(methyl)carbamoyl)cyclobutyl)methyl)-6'-chloro-3',4,4',5-tetrahydro-2H,2'H-spiro[benzo[b][1,4]oxazepine-3,1'-naphthalene]-7-carboxylic Acid

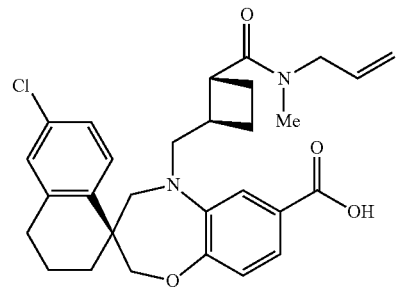 [SMILES: C=CCN(C)C(=O)[C@@H]1CC[C@H]1CN1C[C@@]2(CCCc3cc(Cl)ccc32)COc2ccc(C(=O)O)cc21]

A solution of (S)-tert-butyl 5-(((1R,2R)-2-(allyl(methyl)carbamoyl)cyclobutyl)methyl)-6'-chloro-3',4,4',5-tetrahydro-2H,2'H-spiro[benzo[b][1,4]oxazepine-3,1'-naphthalene]-7-carboxylate (120 mg, 0.212 mmol) in DCM (1593 μL) and TFA (531 μL) was stirred at rt for six hours and then concentrated in vacuo. The residue was partitioned between DCM and saturated sodium bicarbonate (aq.). The organics were dried over MgSO$_4$, filtered and concentrated in vacuo to give crude (S)-5-(((1R,2R)-2-(allyl(methyl)carbamoyl)cyclobutyl)methyl)-6'-chloro-3',4,4',5-tetrahydro-2H,2'H-spiro[benzo[b][1,4]oxazepine-3,1'-naphthalene]-7-carboxylic acid (90 mg, 0.18 mmol, 83% yield) as a white solid.

Step 3: (S)-5-(((1R,2R)-2-(allyl(methyl)carbamoyl)cyclobutyl)methyl)-N-(allylsulfonyl)-6'-chloro-3',4,4',5-tetrahydro-2H,2'H-spiro[benzo[b][1,4]oxazepine-3,1'-naphthalene]-7-carboxamide

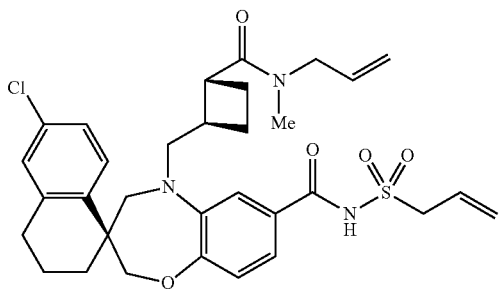 [SMILES: C=CCN(C)C(=O)[C@@H]1CC[C@H]1CN1C[C@@]2(CCCc3cc(Cl)ccc32)COc2ccc(C(=O)NS(=O)(=O)CC=C)cc21]

To a stirred solution of (S)-5-(((1R,2R)-2-(allyl(methyl)carbamoyl)cyclobutyl)methyl)-6'-chloro-3',4,4',5-tetrahydro-2H,2'H-spiro[benzo[b][1,4]oxazepine-3,1'-naphthalene]-7-carboxylic acid (70 mg, 0.138 mmol) in DCM (1375 µL) under a nitrogen atmosphere was added prop-2-ene-1-sulfonamide (33.3 mg, 0.275 mmol; Example 96, step 1) and DMAP (33.6 mg, 0.275 mmol). The reaction mixture was cooled at 0° C. and treated with EDC (52.7 mg, 0.275 mmol) portionwise over one minute. The reaction was allowed to warm to rt overnight. After this time, the reaction mixture was partitioned between DCM and saturated sodium bicarbonate (aq.). The organic layer was dried over MgSO$_4$, filtered and concentrated in vacuo. The residue was purified by column chromatography (12 g silica gel; hexanes: (99:1 EtOAc:AcOH), 1:0 to 4:1 eluent gradient) to give (S)-5-(((1R,2R)-2-(allyl(methyl)carbamoyl)cyclobutyl)methyl)-N-(allylsulfonyl)-6'-chloro-3',4,4',5-tetrahydro-2H,2'H-spiro[benzo[b][1,4]oxazepine-3,1'-naphthalene]-7-carboxamide (65 mg, 0.106 mmol, 77% yield).

Step 4: (1S,3'R,6'R,10'E)-6-chloro-8'-methyl-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[10,16,18,24]tetraen]-7',15'-dione 13',13'-dioxide or (1S,3'R,6'R,10'Z)-6-chloro-8'-methyl-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[10,16,18,24]tetraen]-7',15'-dione 13',13'-dioxide

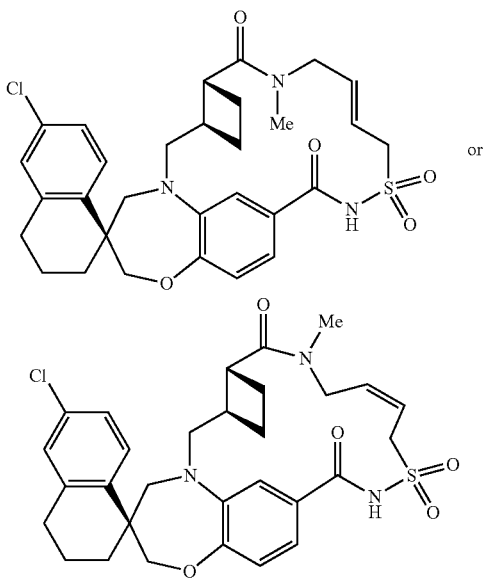

A stirred solution of (S)-5-(((1R,2R)-2-(allyl(methyl)carbamoyl)cyclobutyl)methyl)-N-(allylsulfonyl)-6'-chloro-3',4,4',5-tetrahydro-2H,2'H-spiro[benzo[b][1,4]oxazepine-3,1'-naphthalene]-7-carboxamide (0.065 g, 0.106 mmol) in toluene (106 mL) was sparged with argon for 20 minutes. Hoveyda-grubbs 2$^{nd}$ generation catalyst (0.013 g, 0.021 mmol) was added and the reaction mixture was heated at reflux for 90 minutes. After this time, the reaction mixture was cooled to rt and air was bubbled through it for 10 minutes to deactivate the catalyst. Solvents were evaporated in vacuo and the product was purified by column chromatography (12 g silica gel, hexanes: (99:1 EtOAc:AcOH), 1:0 to 85:15 eluent gradient) to give the title compound (0.030 g, 0.051 mmol, 48% yield). The stereochemical configuration of the olefin at the 10' position was not rigorously determined.

Step 5: (1S,3'R,6'R)-6-chloro-8'-methyl-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[16,18,24]trien]-7',15'-dione 13',13'-dioxide To a solution of either (1S,3'R,6'R,10'E)-6-chloro-8'-methyl-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[10,16,18,24]tetraen]-7',15'-dione 13',13'-dioxide or (1S,3'R,6'R,10'Z)-6-chloro-8'-methyl-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[10,16,18,24]tetraen]-7',15'-dione 13',13'-dioxide (15 mg, 0.026 mmol) in ethyl acetate (2568 µL) was added platinum (IV) oxide (5.83 mg, 0.026 mmol), and the reaction mixture was placed under a hydrogen atmosphere and stirred at rt for two hours. After this time, an additional portion of Pt (IV) oxide (5.0 mg, 0.022 mmol) was added and stirring under hydrogen was continued for two more hours. The reaction mixture was then filtered through celite, washing the filter cake with EtOAc. The solvent was evaporated in vacuo and the product was purified by column chromatography (4 g silica gel; hexanes: (99:1 EtOAc:AcOH), 1:0 to 85:15) to give (1S,3'R,6'R)-6-chloro-8'-methyl-3,4-dihydro-2H,7'H,15'H-spiro[naphthalene-1,22'-[20]oxa[13]thia[1,8,14]triazatetracyclo[14.7.2.0$^{3,6}$.0$^{19,24}$]pentacosa[16,18,24]trien]-7',15'-dione 13',13'-dioxide (6.0 mg, 10 µmol, 40% yield) as a white solid. $^1$H NMR (400 MHz, CDCl$_3$) δ ppm 10.17 (s, 1H), 7.74 (d, J=8.4 Hz, 1H), 7.50 (dd, J=8.3, 2.1 Hz, 1H), 7.37 (d, J=2.0 Hz, 1H), 7.19 (dd, J=8.6, 2.3 Hz, 1H), 7.09 (d, J=2.2 Hz, 1H), 6.97 (d, J=8.4 Hz, 1H), 4.06-4.20 (m, 2H), 3.60-3.78 (m, 3H), 3.34-3.45 (m, 1H), 3.23-3.32 (m, 2H), 3.05-3.22 (m, 2H), 2.97 (s, 2H), 2.91 (q, J=9.4 Hz, 1H), 2.74-2.81 (m, 2H), 2.23-2.32 (m, 1H), 2.09-2.17 (m, 4H), 1.40-2.03 (m, 12H). m/z (ESI, +ve ion) 586.2 (M+H)$^+$.

Example 100. (1S,3'R,6'R,7'S,8'E,10'S,12'R)-6-chloro-7'-hydroxy-3,4-dihydro-2H,15'H-spiro[naphthalene-1,22'-[20]oxa[13]thia[1,14]diazapentacyclo[14.7.2.1$^{10,12}$.0$^{3,6}$.0$^{19,24}$]hexacosa[8,16,18,24]tetraen]-15'-one 13',13'-dioxide

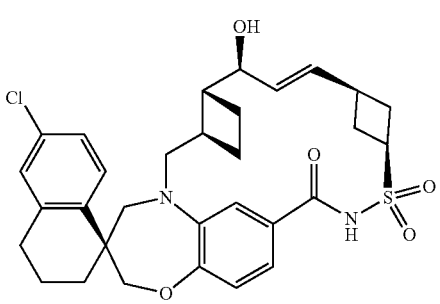 [SMILES: O=C1NS(=O)(=O)[C@H]2C[C@@H](/C=C/[C@H](O)[C@@H]3CC[C@H]3CN3C[C@@]4(CCCc5cc(Cl)ccc54)COc4ccc1cc43)C2]

Step 1: methyl 3,3-dimethoxycyclobutanecarboxylate

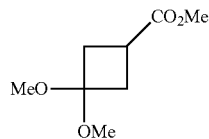

A solution of 3-oxocyclobutanecarboxylic acid (10.5 g, 92.0 mmol) and p-toluenesulfonic acid monohydrate (0.700 g, 3.68 mmol) in MeOH (300 mL) was heated at reflux overnight. After this time, the reaction mixture was cooled to rt, concentrated to a small volume in vacuo, and diluted with water. The resulting mixture was extracted with DCM (2×). The organic layer was dried over $MgSO_4$, filtered and concentrated in vacuo to give methyl 3,3-dimethoxycyclobutanecarboxylate (14 g, 80 mmol, 87% yield).

Step 2: (3,3-dimethoxycyclobutyl)methanol

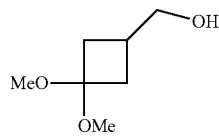

To a stirred solution of methyl 3,3-dimethoxycyclobutanecarboxylate (14 g, 80 mmol) in THF (161 ml) at 0° C. under a nitrogen atmosphere was added lithium aluminum hydride (2M in THF, 44.2 ml, 88 mmol) dropwise over five minutes. When the addition was complete, the ice bath was removed and the reaction was stirred at rt for one hour. The reaction was then carefully quenched by addition of water (6 mL), 20 g of celite were added, and the mixture was stirred vigorously. The resulting slurry was filtered, washing the filter cake with ethyl acetate. Concentration of the filtrate in vacuo gave (3,3-dimethoxycyclobutyl)methanol (9.0 g, 62 mmol, 77% yield).

Step 3: tert-butyl((3,3-dimethoxycyclobutyl)methoxy)diphenylsilane

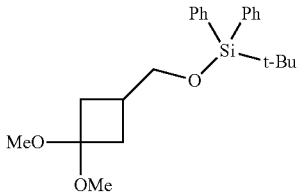 [SMILES: COC1(OC)CC(CO[Si](c2ccccc2)(c2ccccc2)C(C)(C)C)C1]

To a stirred solution of (3,3-dimethoxycyclobutyl)methanol (8.0 g, 55 mmol) in DCM (219 mL) was added triethylamine (11.4 mL, 82.0 mmol), DMAP (0.669 g, 5.47 mmol) and tert-butyldiphenylsilyl chloride (15.5 mL, 60.2 mmol). The reaction mixture was stirred at rt overnight. The reaction mixture was then partitioned between DCM and $NaHCO_3$ (sat. aq. solution). The organic layer was washed with brine, dried over $MgSO_4$, filtered and concentrated in vacuo. The resulting oil was adsorbed onto a 40 g silica gel cartridge, and purified by column chromatography (220 g silica gel; hexanes:EtOAc, 1:0 to 20:80 eluent gradient) to give tert-butyl((3,3-dimethoxycyclobutyl)methoxy)diphenylsilane (14 g, 36 mmol, 66% yield) as a colorless oil.

Step 4: 3-(((tert-butyldiphenylsilyl)oxy)methyl)cyclobutanone

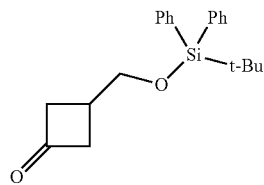 [SMILES: CC(C)(C)[Si](OCC1CC(=O)C1)(c1ccccc1)c1ccccc1]

To a stirred solution of tert-butyl((3,3-dimethoxycyclobutyl)methoxy)diphenylsilane (13 g, 39 mmol) in acetone (75 mL) and water (37.6 mL) was added p-toluenesulfonic acid monohydrate (0.643 g, 3.38 mmol). The reaction mixture was heated at 55° C. for four hours, and was then cooled to rt and partitioned between EtOAc and saturated $NaHCO_3$ (aq.). The organic layer was dried over $MgSO_4$, filtered and concentrated in vacuo to give 3-(((tert-butyldiphenylsilyl)oxy)methyl)cyclobutanone (9.06 g, 26.8 mmol, 79% yield) as a white solid.

Step 5: (1S,3S)-3-(((tert-butyldiphenylsilyl)oxy)methyl)cyclobutanol and (1R,3S)-3-(((tert-butyldiphenylsilyl)oxy)methyl)cyclobutanol

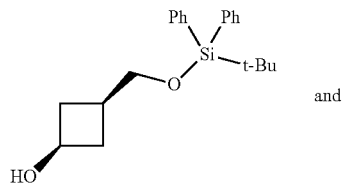

and

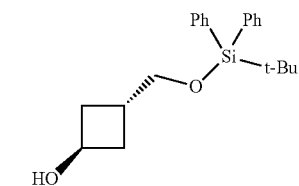

To a stirred solution of 3-(((tert-butyldiphenylsilyl)oxy)methyl)cyclobutanone (5.00 g, 14.8 mmol) in THF (46.9 mL) was added sodium borohydride (0.559 g, 14.8 mmol) followed by MeOH (2.345 mL). The resulting reaction mixture was stirred at rt for two hours. After this time, the reaction mixture was partitioned between EtOAc and water. The organic layer was washed with brine, dried over $MgSO_4$, filtered and concentrated in vacuo to give 3-(((tert-butyldiphenylsilyl)oxy)methyl)cyclobutanol (mixture of cis and trans isomers, predominantly cis; 5.00 g, 14.7 mmol, 99% yield).

Step 6: trans-3-(((tert-butyldiphenylsilyl)oxy) methyl)cyclobutanol

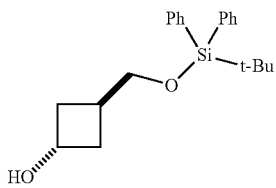

To a stirred solution of 3-(((tert-butyldiphenylsilyl)oxy) methyl)cyclobutanol (diastereomer mixture favoring the cis isomer prepared in Step 5 above; 3.80 g, 11.2 mmol) in THF (112 mL) was added benzoic acid (2.044 g, 16.74 mmol) and triphenylphosphine (4.39 g, 16.7 mmol). The reaction was cooled to 0° C. for 10 minutes and then (E)-diisopropyl diazene-1,2-dicarboxylate (3.25 mL, 16.7 mmol) was added dropwise via syringe over 10 minutes. After this time, the reaction was stirred at 0° C. for 30 minutes and was then stirred overnight at room temperature. The reaction mixture was then partitioned between EtOAc and brine. The organic layer was dried over $MgSO_4$, filtered and concentrated in vacuo. The crude product was adsorbed onto a 40 g silica gel cartridge and purified by column chromatography (80 g silica column; hexanes:EtOAc, 1:0 to 95:5 eluent gradient) to give the intermediate trans-3-(((tert-butyldiphenylsilyl) oxy)methyl)cyclobutyl benzoate (3.7 g) containing minor impurities.

To a stirred solution of trans-3-(((tert-butyldiphenylsilyl) oxy)methyl)cyclobutyl benzoate (3.7 g, 8.3 mmol) in THF (41.6 mL) was added a solution of sodium hydroxide (0.333 g, 8.32 mmol) in water (6 mL) followed by MeOH (6 mL). The reaction mixture was stirred at rt for one hour and then partitioned between EtOAc and water. The organic layer was dried over $MgSO_4$, filtered and concentrated in vacuo. The crude product was purified by column chromatography (80 g silica gel, hexanes:EtOAc, 1:0 to 4:1 solvent gradient) to give trans-3-(((tert-butyldiphenylsilyl)oxy)methyl)cyclobutanol (2.3 g, 6.7 mmol, 61% overall yield from the diastereomer mixture prepared in Step 5).

Step 7: trans-3-(((tert-butyldiphenylsilyl)oxy) methyl)cyclobutyl Methanesulfonate

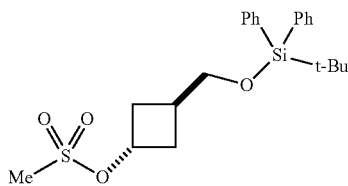 [SMILES: CC(C)(C)[Si](OC[C@H]1C[C@H](OS(C)(=O)=O)C1)(c1ccccc1)c1ccccc1]

To a stirred solution of trans-3-(((tert-butyldiphenylsilyl) oxy)methyl)cyclobutanol (2.3 g, 6.7 mmol) in DCM (33.8 ml) was added triethylamine (1.883 mL, 13.51 mmol) followed by methanesulfonyl chloride (0.892 mL, 11.4 mmol). The reaction mixture was stirred at rt for two hours and then partitioned between DCM and 1M HCl (aq.). The organic layer was dried over $MgSO_4$, filtered and concentrated in vacuo to give crude trans-3-(((tert-butyl diphenylsilyl)oxy) methyl)cyclobutyl methanesulfonate (2.43 g, 5.80 mmol, 86% yield), which was used in the subsequent step without further purification.

Step 8: cis-3-(((tert-butyldiphenylsilyl)oxy)methyl) cyclobutyl)thio)pyrimidine

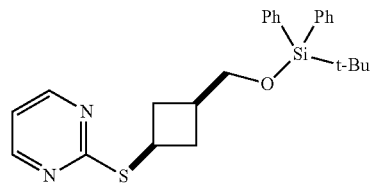 [SMILES: CC(C)(C)[Si](OC[C@H]1C[C@@H](Sc2ncccn2)C1)(c1ccccc1)c1ccccc1]

To a stirred solution of trans-3-(((tert-butyldiphenylsilyl) oxy)methyl)cyclobutyl methanesulfonate (2.43 g, 5.80 mmol) in DMF (23.22 mL) was added potassium carbonate (1.203 g, 8.71 mmol) and 2-mercaptopyrimidine (0.781 g, 6.97 mmol). The resulting reaction mixture was heated at 70° C. for two hours. After this time, additional portions of 2-mercaptopyrimidine (0.3 g, 2.7 mmol) and $K_2CO_3$ (0.5 g, 3.6 mmol) were added and the reaction mixture was stirred at 70° C. for four more hours. Upon cooling the rt, the reaction mixture was partitioned between EtOAc and water. The aqueous layer was extracted with EtOAc, and the combined organic extracts were washed with brine (2×), dried over $MgSO_4$, filtered and concentrated in vacuo. The crude product was adsorbed onto a 24 g silica cartridge and purified by flash chromatography (80 g silica; hexanes: EtOAc, 1:0 to 4:1 solvent gradient) to provide cis-2-((3-(((tert-butyldiphenylsilyl)oxy)methyl)cyclobutyl)thio)pyrimidine (2.1 g, 4.8 mmol, 83% yield).

Step 9: cis-3-(pyrimidin-2-ylthio)cyclobutyl)methanol

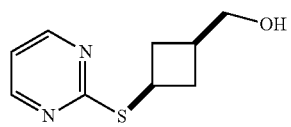 [SMILES: OC[C@H]1C[C@@H](Sc2ncccn2)C1]

To a stirred solution of cis-2-((-3-(((tert-butyldiphenylsilyl)oxy)methyl)cyclobutyl)thio)pyrimidine (2.1 g, 4.8 mmol) in THF (48.3 mL) was added tetrabutylammonium fluoride (1 M in THF; 5.31 mL, 5.31 mmol). The resulting reaction mixture was stirred at rt for two hours and then partitioned between EtOAc and brine. The organic layer was dried over $MgSO_4$, filtered and concentrated in vacuo. Column chromatography (24 g silica gel; hexanes:EtOAc, 1:0 to 3:1 solvent gradient) gave cis-(3-(pyrimidin-2-ylthio) cyclobutyl)methanol (0.70 g, 3.6 mmol, 74% yield).

Step 10: cis-3-(pyrimidin-2-ylthio)cyclobutanecarbaldehdye

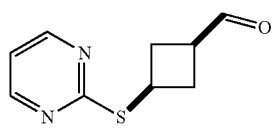 [SMILES: O=C[C@H]1C[C@@H](Sc2ncccn2)C1]

To a stirred solution of cis-(3-(pyrimidin-2-ylthio)cyclobutyl)methanol (0.70 g, 3.6 mmol) in DCM (17.83 mL) was added Dess-Martin periodinane (1.513 g, 3.57 mmol), and the resulting reaction mixture was stirred at rt for 30 minutes. After this time, the reaction mixture was diluted with diethyl ether, saturated aqueous sodium thiosulfate (sat aq. solution) was added, and the resulting mixture was stirred at rt for 20 minutes. The organic layer was separated, washed with sodium thiosulfate (sat. aq. solution), NaHCO₃ (sat. aq. solution), dried over MgSO₄, filtered and concentrated in vacuo to give cis-3-(pyrimidin-2-ylthio)cyclobutanecarbaldehyde (0.57 g, 2.9 mmol, 82% yield).

Step 11: 2-((cis-3-vinylcyclobutyl)thio)pyrimidine

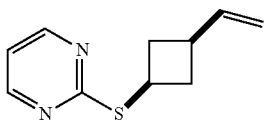

To a stirred solution of methyltriphenylphosphonium bromide (5.24 g, 14.7 mmol) in THF (29.3 mL) was added potassium tert-butoxide (0.988 g, 8.80 mmol), and the resulting reaction mixture was stirred at rt for 30 minutes. After this time, the reaction mixture was cooled to 0° C. and treated with a solution of cis-3-(pyrimidin-2-ylthio)cyclobutanecarbaldehyde (0.57 g, 2.93 mmol) in THF (3 mL) dropwise over five minutes. The resulting mixture was stirred at 0° C. for 30 minutes and at rt overnight. On the following day, the reaction mixture was partitioned between EtOAc and water. The organic layer was dried over MgSO₄, filtered and concentrated in vacuo. The crude residue was purified by column chromatography (12 g silica gel; hexanes:EtOAc, 1:0 to 2:1 solvent gradient) gave cis-2-((3-vinylcyclobutyl)thio)pyrimidine (0.28 g, 1.456 mmol, 49.6% yield).

Step 12: 2-((cis-3-vinylcyclobutyl)sulfonyl)pyrimidine

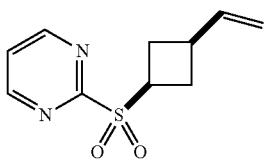

To a stirred solution of cis-2-((-3-vinylcyclobutyl)thio)pyrimidine (280 mg, 1.46 mmol) in DCM (7281 µL) was added meta-chloroperoxybenzoic acid (ca. 77%, balance meta-chlorobenzoic acid and water; 718 mg, 3.20 mmol). The reaction mixture was stirred at rt for two hours and partitioned between DCM and NaHCO₃. The organic layer was dried over MgSO₄, filtered and concentrated in vacuo. Column chromatography (12 g silica gel; hexanes:EtOAc, 1:0 to 2:1 solvent gradient) gave cis-2-((3-vinylcyclobutyl)sulfonyl)pyrimidine (140 mg, 0.624 mmol, 43% yield).

Step 13: cis-3-vinylcyclobutane-1-sulfonamide

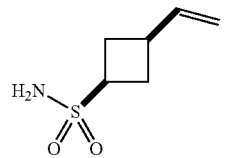

To a stirred solution of cis-2-((3-vinylcyclobutyl)sulfonyl)pyrimidine (0.14 g, 0.624 mmol) in MeOH (6.24 mL) was added sodium methoxide (0.143 mL, 0.624 mmol), and the resulting reaction mixture was stirred at rt for 45 minutes. After this time, the solvent was evaporated in vacuo. Diethyl ether was added to the mixture, and the solid was filtered, washed with diethyl ether and dried under vacuum to give crude sodium cis-3-vinylcyclobutane-1-sulfinate (0.1 g, 0.595 mmol, 95% yield).

To a stirred solution of sodium cis-3-vinylcyclobutane-1-sulfinate (0.1 g, 0.595 mmol) in water (5.95 mL) was added sodium acetate (0.098 g, 1.189 mmol) and hydroxylamine-O-sulfonic acid (0.101 g, 0.892 mmol), and the reaction mixture was heated at 50° C. for one hour. After this time, the reaction was cooled to rt and basified with 1M aqueous NaOH. The aqueous layer was extracted with EtOAc (2×), DCM (2×), and the combined organics were dried over MgSO₄, filtered and concentrated in vacuo to give 35 mg of cis-3-vinylcyclobutane-1-sulfonamide. The aqueous layer was concentrated in vacuo and dried under high vacuum overnight. The resulting white solid was triturated with DCM, filtered and dried under high vacuum and additional 30 mg of desired product. Both product fractions were combined to give cis-3-vinylcyclobutane-1-sulfonamide (0.062 g, 0.39 mmol, 65% yield).

Step 14: (S)-6'-chloro-5-(((1R,2R)-2-((S,E)-1-hydroxy-3-((1S,3R)-3-sulfamoylcyclobutyl)allyl)cyclobutyl)methyl)-3',4,4',5-tetrahydro-2H,2'H-spiro[benzo[b][1,4]oxazepine-3,1'-naphthalene]-7-carboxylic Acid

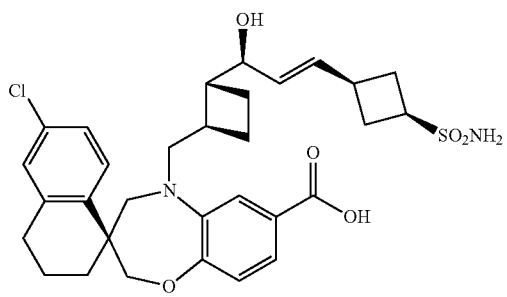 [SMILES: NS(=O)(=O)[C@H]1C[C@@H](/C=C/[C@H](O)[C@@H]2CC[C@H]2CN2C[C@@]3(CCCc4cc(Cl)ccc43)COc3ccc(C(=O)O)cc32)C1]

A solution of Intermediate AA12A (62 mg, 0.12 mmol) and cis-3-vinylcyclobutane-1-sulfonamide (58.8 mg, 0.365 mmol) in 1,2-dichloroethane (1736 µL) was sparged with argon for 10 minutes. The reaction mixture was then charged with (1,3-dimesitylimidazolidin-2-ylidene)(2-isopropoxybenzylidene)ruthenium(VI) chloride (7.6 mg, 0.012 mmol) and stirred at rt for three hours, after which time the catalyst was then deactivated by sparging air through the mixture for five minutes. Solvents were removed in vacuo and the residue was purified by column chromatography (4 g silica gel; hexanes: (99:1 EtOAc:AcOH), 1:0 to 6:4 solvent gradient) to give (S)-6'-chloro-5-(((1R,2R)-2-((S,E)-1-hydroxy-3-((1S,3R)-3-sulfamoylcyclobutyl)allyl)cyclobutyl)methyl)-3',4,4',5-tetrahydro-2H,2'H-spiro[benzo[b][1,4]oxazepine-3,1'-naphthalene]-7-carboxylic acid (40 mg, 0.067 mmol, 54.7% yield).

Step 15: (1S,3'R,6'R,7'S,8'E,10'S,12'R)-6-chloro-7'-hydroxy-3,4-dihydro-2H,15'H-spiro[naphthalene-1,22'-[20]oxa[13]thia[1,14]diazapentacyclo[14.7.2.1$^{10,12}$.0$^{3,6}$.0$^{19,24}$]hexacosa[8,16,18,24]tetraen]-15'-one 13',13'-dioxide To a stirred, 0° C. solution of (S)-6'-chloro-5-(((1R,2R)-2-((S,E)-1-hydroxy-3-((1S,3R)-3-sulfamoylcyclobutyl)allyl)cyclobutyl)methyl)-3',4,4',5-tetrahydro-2H,2'H-spiro[benzo[b][1,4]oxazepine-3,1'-naphthalene]-7-carboxylic acid (40 mg, 0.067 mmol) in DCM (3.33 E+04 µL) was added DMAP (13.8 mg, 0.113 mmol) followed by EDC (25.5 mg, 0.133 mmol). The resulting reaction mixture was stirred at rt over the weekend and then washed with 1M aqueous citric acid. The organic layer was dried over MgSO$_4$, filtered and concentrated in vacuo. The resulting crude residue was purified by column chromatography (4 g silica gel, DCM:acetone, 1:0 to 9:1 solvent gradient) to give (1S,3'R,6'R,7'S,8'E,10'S,12'R)-6-chloro-7'-hydroxy-3,4-dihydro-2H,15'H-spiro[naphthalene-1,22'-[20]oxa[13]thia[1,14]diazapentacyclo[14.7.2.1$^{10,12}$0$^{3,6}$.0$^{19,24}$]hexacosa[8,16,18,24]tetraen]-15'-one 13',13'-dioxide (8.5 mg, 22% yield) as a white solid. $^1$H NMR (400 MHz, CD$_2$Cl$_2$) δ ppm 8.05 (br. s., 1H), 7.71 (d, J=8.6 Hz, 1H), 7.17 (dd, J=8.4, 2.3 Hz, 1H), 7.10 (d, J=2.2 Hz, 1H), 6.91-7.01 (m, 3H), 5.97 (dd, J=15.7, 6.6 Hz, 1H), 5.52 (dd, J=15.3, 7.0 Hz, 1H), 4.02-4.17 (m, 4H), 3.71-3.85 (m, 2H), 3.34 (d, J=14.3 Hz, 1H), 3.14 (dd, J=15.2, 10.1 Hz, 1H), 2.93-3.08 (m, 2H), 2.82-2.93 (m, 1H), 2.68-2.81 (m, 3H), 2.51 (br. s., 1H), 2.29-2.41 (m, 1H), 2.15-2.25 (m, 1H), 2.04 (d, J=10.8 Hz, 1H), 1.78-1.99 (m, 4H), 1.58-1.72 (m, 2H), 1.40-1.51 (m, 2H). m/z (ESI, +ve ion) 585.2 (M+H)$^+$.

Example 101. (1S,3'R,6'R,7'S,10'S,12'S)-6-chloro-7'-hydroxy-3,4-dihydro-2H,15'H-spiro[naphthalene-1,22'-[20]oxa[13]thia[1,14]diazapentacyclo[14.7.2.1$^{10,12}$0$^{3,6}$.0$^{19,24}$]hexacosa[16,18,24]trien]-15'-one 13',13'-dioxide

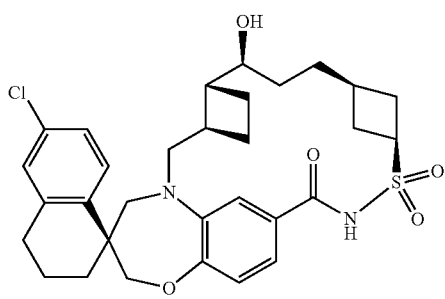 [SMILES: O=C1NS(=O)(=O)[C@H]2C[C@@H](CC[C@H](O)[C@@H]3CC[C@H]3CN3C[C@@]4(CCCc5cc(Cl)ccc54)COc4ccc1cc43)C2]

To a stirred solution of (1S,3'R,6'R,7'S,8'E,10'S,12'R)-6-chloro-7'-hydroxy-3,4-dihydro-2H,15'H-spiro[naphthalene-1,22'-[20]oxa[13]thia[1,14]diazapentacyclo[14.7.2.1$^{10,12}$.0$^{3,6}$.0$^{19,24}$]hexacosa[8,16,18,24]tetraen]-15'-one 13',13'-dioxide (5.0 mg, 8.6 µmol, Example 100, step 15) in EtOAc (1715 µl) was added platinum(IV) oxide (1.95 mg, 8.6 µmol). The flask was evacuated and placed under a hydrogen atmosphere and the reaction mixture was stirred at rt for 90 minutes. The reaction mixture was then filtered through celite, washing the filter cake with EtOAc. Evaporation of solvents gave (1S,3'R,6'R,7'S,10'S,12'S)-6-chloro-7'-hydroxy-3,4-dihydro-2H,15'H-spiro[naphthalene-1,22'-[20]oxa[13]thia[1,14]diazapentacyclo[14.7.2.1$^{10,12}$.0$^{3,6}$.0$^{19,24}$]hexacosa[16,18,24]trien]-15'-one 13',13'-dioxide (2.1 mg, 3.6 µmol, 42% yield) as an off-white solid. $^1$H NMR (500 MHz, CD$_2$Cl$_2$) δ ppm 8.15 (br. s., 1H), 7.72 (d, J=8.6 Hz, 1H), 7.17 (dd, J=8.4, 2.3 Hz, 1H), 7.09 (d, J=2.4 Hz, 1H), 6.91-7.04 (m, 3H), 4.06-4.17 (m, 2H), 4.01 (quin, J=8.7 Hz, 1H), 3.76 (d, J=14.7 Hz, 1H), 3.71 (d, J=14.4 Hz, 1H), 3.52-3.61 (m, 1H), 3.36 (d, J=14.2 Hz, 1H), 3.30 (dd, J=15.3, 8.4 Hz, 1H), 2.70-2.84 (m, 2H), 2.61-2.69 (m, 1H), 2.48-2.59 (m, 2H), 2.38-2.48 (m, 2H), 2.18-2.30 (m, 2H), 2.04 (d, J=9.8 Hz, 2H), 1.80-1.96 (m, 3H), 1.64-1.79 (m, 3H), 1.42-1.63 (m, 5H). m/z (ESI, +ve ion) 585.3 (M+H)$^+$.

Example 102. (1S,3'R,6'R,7'S,8'E,10'R,12'S)-6-chloro-7'-hydroxy-3,4-dihydro-2H,15'H-spiro[naphthalene-1,22'-[20]oxa[13]thia[1,14]diazapentacyclo[14.7.2.1$^{1'',2}$.0$^{3,6}$.0$^{19,24}$]hexacosa[8,16,18,24]tetraen]-15'-one 13',13'-dioxide

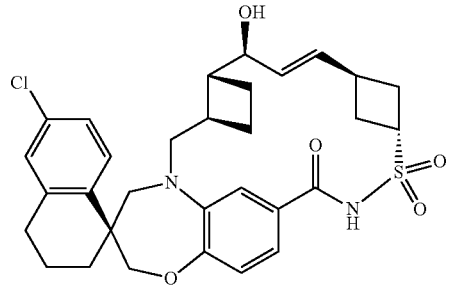 [SMILES: O=C1NS(=O)(=O)[C@H]2C[C@H](/C=C/[C@H](O)[C@@H]3CC[C@H]3CN3C[C@@]4(CCCc5cc(Cl)ccc54)COc4ccc1cc43)C2]

Step 1: (1S,3S)-3-(((tert-butyldiphenylsilyl)oxy)methyl)cyclobutyl methanesulfonate and (1R,3S)-3-(((tert-butyldiphenylsilyl)oxy)methyl)cyclobutyl Methanesulfonate

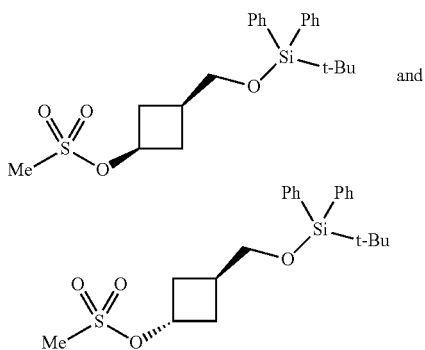

To a stirred solution of 3-(((tert-butyldiphenylsilyl)oxy)methyl)cyclobutanol (cis and trans mixture; 5.00 g, 14.7 mmol; Example 100, Step 5) in DCM (73.4 mL) was added triethylamine (4.09 ml, 29.4 mmol) followed by methanesulfonyl chloride (1.72 mL, 22.0 mmol). The reaction mixture was stirred at rt overnight and then partitioned between DCM and 1M HCl (aq.). The organic layer was washed with brine, dried over MgSO₄, filtered and concentrated in vacuo to give crude 3-(((tert-butyldiphenylsilyl)oxy)methyl)cyclobutyl methanesulfonate (cis and trans mixture; 6.00 g, 14.3 mmol, 98% yield), which was used in the subsequent step without further purification.

Step 2: 2-(((1R,3R)-3-(((tert-butyldiphenylsilyl)oxy)methyl)cyclobutyl)thio)pyrimidine and 2-(((1S,3R)-3-(((tert-butyldiphenylsilyl)oxy)methyl)cyclobutyl)thio)pyrimidine

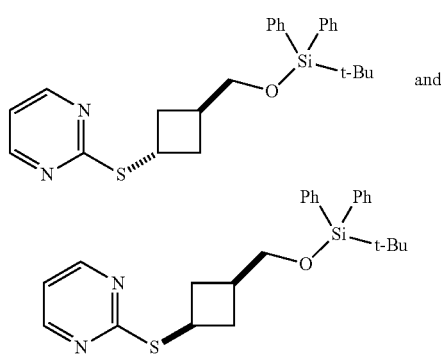

To a stirred solution of 3-(((tert-butyldiphenylsilyl)oxy)methyl)cyclobutyl methanesulfonate (cis and trans mixture; 6.00 g, 14.3 mmol; Example 102, Step 1) in DMF (57.3 mL) were added 2-mercaptopyrimidine (1.929 g, 17.20 mmol) and potassium carbonate (2.97 g, 21.50 mmol). The reaction mixture was stirred at rt over the weekend and then partitioned between EtOAc and water. The organic layer was washed with brine, dried over MgSO₄, filtered and concentrated in vacuo. The resulting crude residue was purified by column chromatography (80 g silica gel; hexanes:EtOAc, 1:0 to 4:1 solvent gradient) to give 2-((3-(((tert-butyldiphenylsilyl)oxy)methyl)cyclobutyl)thio)pyrimidine (mixture of cis and trans isomers; 5.00 g, 11.50 mmol, 80% yield)

Step 3: ((1R,3R)-3-(pyrimidin-2-ylthio)cyclobutyl)methanol and ((1S,3R)-3-(pyrimidin-2-ylthio)cyclobutyl)methanol

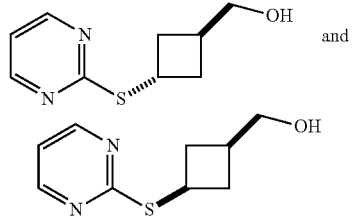

To a stirred solution of 2-((3-(((tert-butyldiphenylsilyl)oxy)methyl)cyclobutyl)thio)pyrimidine (cis and trans mixture; 5.00 g, 11.5 mmol; Example 102, Step 2) in THF (115 mL) was added TBAF (1 M in THF; 12.65 mL, 12.65 mmol), and the resulting reaction mixture was stirred at rt overnight. On the following day, the reaction mixture was partitioned between EtOAc and water. The organic layer was dried over MgSO₄, filtered and concentrated in vacuo to give a crude residue that was further purified by column chromatography (40 g silica gel; hexanes:EtOAc, 1:0 to 1:4 solvent gradient) to provide (3-(pyrimidin-2-ylthio)cyclobutyl)methanol (cis and trans mixture; 1.86 g, 9.48 mmol total, 82% yield).

Step 4: (1R,3R)-3-(pyrimidin-2-ylthio)cyclobutanecarbaldehyde and (1S,3R)-3-(pyrimidin-2-ylthio)cyclobutanecarbaldehyde

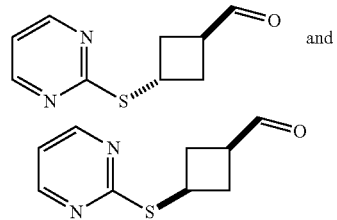

To a stirred solution of (3-(pyrimidin-2-ylthio)cyclobutyl)methanol (mixture of cis and trans isomers; 1.75 g, 8.92 mmol; Example 102, Step 3) in DCM (44.6 ml) was added Dess-Martin periodinane (4.54 g, 10.7 mmol), and the resulting reaction mixture was stirred at rt for 20 minutes. An additional portion of Dess-Martin periodinane (1.5 g, 7.6 mmol) was added, and stirring was continued for 30 minutes, after which time a third portion of Dess-Martin periodinane was added (1.5 g, 7.6 mmol). The reaction mixture was stirred at rt for 40 minutes, diluted in diethyl ether, and treated with saturated aqeuous sodium thiosulfate, giving a biphasic mixture that was vigorously stirred for 20 minutes. The organic layer was separated, washed sequentially with saturated aqueous sodium thiosulfate and saturated sodium bicarbonate, and dried over MgSO₄. Filtration and evaporated of solvents in vacuo gave a crude residue that was further purified by column chromatography (24 g silica gel; hexanes:diethyl ether, 1:0 to 3:1 solvent gradient) to provide 3-(pyrimidin-2-ylthio)cyclobutanecarbaldehyde (mixture of cis and trans isomers; 0.76 g, 3.9 mmol total, 44% yield).

Step 5: 2-(((1R,3R)-3-vinylcyclobutyl)thio)pyrimidine and 2-(((1S,3R)-3-vinylcyclobutyl)thio)pyrimidine

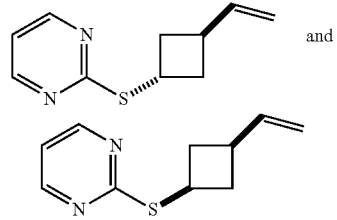

To a stirred suspension of methyltriphenylphosphonium bromide (6.90 g, 19.30 mmol) in THF (38.6 mL) was added potassium tert-butoxide (1.300 g, 11.58 mmol). The reaction was stirred at rt for 30 minutes, cooled to 0° C., and treated with a solution of 3-(pyrimidin-2-ylthio)cyclobutanecarbaldehyde (cis and trans mixture; 0.75 g, 3.9 mmol; Example 102, Step 4) in THF (4 mL) dropwise over one minute. Five minutes later, the cooling bath was removed, and the reaction mixture was stirred at ambient temperature for four hours, after which it was partitioned between EtOAc and water. The separated organic layer was washed with brine, dried over MgSO₄, filtered and concentrated in vacuo. Flash chromatographic purification (12 g silica gel; hexanes:diethyl ether, 1:0 to 4:1 solvent gradient) of the crude residue gave 2-((3-vinylcyclobutyl)thio)pyrimidine (cis and trans isomer mixture; 0.51 g, 2.6 mmol, 69% yield) as a colorless liquid.

Step 6: 2-(((1R,3R)-3-vinylcyclobutyl)sulfonyl)pyrimidine and 2-(((1S,3R)-3-vinylcyclobutyl)sulfonyl)pyrimidine

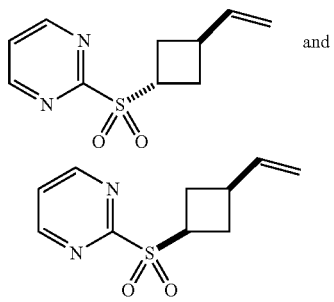

To a vigorously stirred mixture of sodium tungstate dihydrate (0.044 g, 0.133 mmol), phenylphosphonic acid (0.021 g, 0.133 mmol) and tetrabutylammonium sulfate (50 weight % solution in water; 0.154 mL, 0.133 mmol) in water (2.411 mL) was added hydrogen peroxide (30 weight % solution in water; 0.677 mL, 6.63 mmol). After two minutes, a solution of 2-((3-vinylcyclobutyl)thio)pyrimidine (cis and trans mixture; 0.51 g, 2.6 mmol; Example 102, Step 5) in toluene (24.11 mL) was added, and the resulting reaction mixture was stirred at 50° C. overnight. On the following day, the reaction mixture was cooled to rt and partitioned between EtOAc and water. The aqueous layer was extracted with EtOAc, and the combined organic extracts were washed with brine, dried over MgSO₄, filtered and concentrated in vacuo to give crude 2-((3-vinylcyclobutyl)sulfonyl)pyrimidine (diastereomer mixture, cis:trans=ca. 1:5; 0.43 g, 1.9 mmol total, 72% yield), which was used in the subsequent step without further purification.

Step 7: (1R,3R)-3-vinylcyclobutane-1-sulfonamide and (1S,3R)-3-vinylcyclobutane-1-sulfonamide

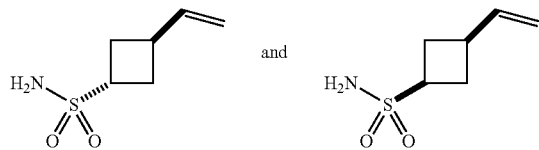

To a solution of 2-((3-vinylcyclobutyl)sulfonyl)pyrimidine (cis and trans mixture; 0.43 g, 1.9 mmol; Example 102, Step 6) in MeOH (19.17 mL) was added sodium methoxide (25% solution in methanol; 0.438 mL, 1.92 mmol) and the resulting reaction mixture was stirred at rt for 90 minutes. Solvents were evaporated in vacuo and the resulting solid was triturated with Et₂O and dried under high vacuum for 10 minutes to give crude sodium 3-vinylcyclobutane-1-sulfinate (0.30 g, 1.7 mmol, 93% yield).

To a stirred solution of predominantly trans sodium 3-vinylcyclobutane-1-sulfinate (0.30 g, 1.7 mmol) in water (17.84 mL) were added sodium acetate (0.293 g, 3.57 mmol) and hydroxylamine-O-sulfonic acid (0.242 g, 2.140 mmol), and the resulting reaction mixture was heated at 55° C. for two hours. Upon cooling, the mixture was basified with 1M aqueous NaOH. The aqueous layer was extracted with EtOAc (2×) and DCM (1×), and the combined organic extracts were dried over MgSO₄, filtered and concentrated in vacuo to give 3-vinylcyclobutane-1-sulfonamide (cis:trans=ca. 1:7 by NMR; 0.18 g, 1.1 mmol; 37% yield) as a white solid.

Step 8: (S)-6'-chloro-5-(((1R,2R)-2-((S,E)-1-hydroxy-3-((1R,3S)-3-sulfamoylcyclobutyl)allyl)cyclobutyl)methyl)-3',4,4',5-tetrahydro-2H,2'H-spiro[benzo[b][1,4]oxazepine-3,1'-naphthalene]-7-carboxylic Acid

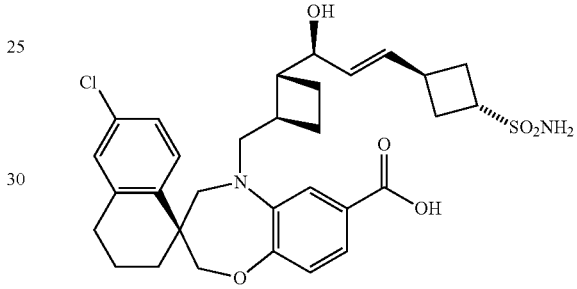

A stirred solution of Intermediate AA12A (80.0 mg, 0.157 mmol) and predominantly trans-3-vinylcyclobutane-1-sulfonamide (cis:trans=ca. 1:7; 25.3 mg, 0.157 mmol) in 1,2-dichloroethane (3137 µL) was sparged with argon for 10 minutes and then charged with a solution of (1,3-dimesitylimidazolidin-2-ylidene)(2-isopropoxybenzylidene)ruthenium(VI) chloride (9.83 mg, 0.016 mmol) in DCM (1 mL). The resulting reaction mixture was stirred at rt for three hours, after which the catalyst was deactivated by bubbling air through the reaction mixture. Silica gel (ca. 2 g) was added to the mixture and solvents were removed in vacuo. The silica-adsorbed product was transferred to a solid loading cartridge and purified by column chromatography (12 g silica column; hexanes: (99:1 EtOAc:AcOH), 1:0 to 6:4 solvent gradient) to give (S)-6'-chloro-5-(((1R,2R)-2-((S,E)-1-hydroxy-3-((1R,3S)-3-sulfamoylcyclobutyl)allyl)cyclobutyl)methyl)-3',4,4',5-tetrahydro-2H,2'H-spiro[benzo[b][1,4]oxazepine-3,1'-naphthalene]-7-carboxylic acid (82 mg, 0.14 mmol, 87% yield).

Step 9: (1S,3'R,6'R,7'S,8'E,10'R,12'S)-6-chloro-7'-hydroxy-3,4-dihydro-2H,15'H-spiro[naphthalene-1,22'-[20]oxa[13]thia[1,14]diazapentacyclo[14.7.2.1$^{10,12}$.0$^{3,6}$.0$^{19,24}$]hexacosa[8,16,18,24]tetraen]-15'-one 13',13'-dioxide To a stirred solution of (S)-6'-chloro-5-(((1R,2R)-2-((S,E)-1-hydroxy-3-((1R,3S)-3-sulfamoylcyclobutyl)allyl)cyclobutyl)methyl)-3',4,4',5-tetrahydro-2H,2'H-spiro[benzo[b][1,4]oxazepine-3,1'-naphthalene]-7-carboxylic acid (0.041 g, 0.068 mmol) in DCM (34.1 mL) was added DMAP (0.014 g, 0.12 mmol), and the resulting solution was cooled to 0° C. and charged with EDC (0.026 g, 0.14 mmol) portionwise over five minutes. After five minutes at 0° C., the cooling bath was removed and the reaction mixture was stirred at rt over the weekend. After this time, the reaction mixture was partitioned between DCM and 1M HCl (aq.). The organic layer was dried over MgSO$_4$, filtered and concentrated in vacuo. Flash chromatographic purification (4 g silica gel; hexanes: (99:1 EtOAc:AcOH), 1:0 to 3:1 solvent gradient) gave the desired product (8 mg), albeit in impure form. This material was further purified by a second round of column chromatography (ca. 1 g silica gel; DCM: acetone, 1:0 to 9:1 solvent gradient) to give (1S,3'R,6'R,7'S, 8'E,10'R,12'S)-6-chloro-7'-hydroxy-3,4-dihydro-2H,15'H-spiro[naphthalene-1,22'-[20]oxa[13]thia[1,14] diazapentacyclo[14.7.2.1$^{10,12}$.0$^{3,6}$.0$^{19,24}$]hexacosa[8,16,18, 24]tetraen]-15'-one 13',13'-dioxide (1.3 mg, 2.2 µmol, 3.3% yield) as an off-white solid. $^1$H NMR (400 MHz, CD$_2$Cl$_2$) δ ppm 7.64-7.83 (m, 2H), 7.19 (dd, J=8.6, 2.3 Hz, 1H), 7.12 (d, J=2.2 Hz, 1H), 6.91-7.02 (m, 2H), 6.86 (d, J=1.8 Hz, 1H), 5.83-5.92 (m, 1H), 5.69-5.80 (m, 1H), 4.24-4.41 (m, 3H), 4.05 (d, J=11.9 Hz, 1H), 3.50-3.62 (m, 2H), 3.30 (d, J=14.3 Hz, 1H), 3.16 (dd, J=14.3, 8.8 Hz, 1H), 2.90 (d, J=4.7 Hz, 1H), 2.75-2.84 (m, 2H), 2.60-2.73 (m, 2H), 2.54 (td, J=8.3, 4.4 Hz, 1H), 2.35-2.46 (m, 1H), 2.01-2.06 (m, 1H), 1.93-2.00 (m, 1H), 1.69-1.92 (m, 5H), 1.46-1.69 (m, 4H). m/z (ESI, +ve ion) 583.2 (M+H)$^+$.

Example 103. (1S,3'R,6'R,7'S,10'R,12'R)-6-chloro-7'-hydroxy-3,4-dihydro-2H,15'H-spiro[naphthalene-1,22'-[20]oxa[13]thia[1,14]diazapentacyclo [14.7.2.1$^{10,12}$0$^{3,6}$.0$^{19,24}$]hexacosa[16,18,24]trien]-15'-one 13',13'-dioxide

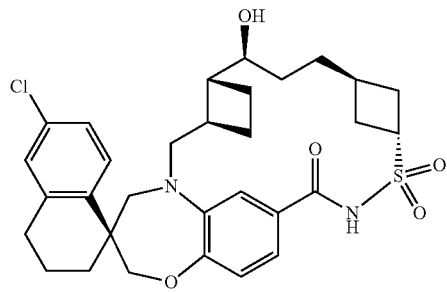 [SMILES: O=C1NS(=O)(=O)[C@H]2C[C@H](CC[C@H](O)[C@@H]3CC[C@H]3CN3C[C@@]4(CCCc5cc(Cl)ccc54)COc4ccc1cc43)C2]

To a stirred solution of (1S,3'R,6'R,7'S,8'E,10'R,12'S)-6-chloro-7'-hydroxy-3,4-dihydro-2H,15'H-spiro[naphthalene-1,22'-[20]oxa[13]thia[1,14]diazapentacyclo[14.7.2.1$^{10,12}$. 0$^{3,6}$.0$^{19,24}$]hexacosa[8,16,18,24]tetraen]-15'-one 13',13'-dioxide (7.0 mg, 0.012 mmol; Example 102) in EtOAc (2401 µL) was added platinum(IV) oxide (3.00 mg, 0.013 mmol). The flask was evacuated and placed under a hydrogen atmosphere, and the reaction mixture was stirred for one hour, filtered through celite and concentrated in vacuo. Flash chromatographic purification (1 g silica gel; hexanes: (99:1 EtOAc:AcOH), 1:0 to 1:2 solvent gradient) gave (1S,3'R, 6'R,7'S,10'R,12'R)-6-chloro-7'-hydroxy-3,4-dihydro-2H, 15'H-spiro[naphthalene-1,22'-[20]oxa[13]thia[1,14]diazapentacyclo[14.7.2.1$^{10,12}$.0$^{3,6}$.0$^{19,24}$]hexacosa[16,18,24]tri en]-15'-one 13',13'-dioxide (1.3 mg, 2.2 µmol, 19% yield) as a white solid. $^1$H NMR (400 MHz, CD$_2$Cl$_2$) δ ppm 8.18 (br. s., 1H), 7.72 (d, J=8.4 Hz, 1H), 7.18 (d, J=8.4 Hz, 1H), 7.09 (s, 1H), 6.95 (br. s., 2H), 6.88 (br. s., 1H), 4.02-4.17 (m, 2H), 3.94 (br. s., 1H), 3.80 (d, J=15.5 Hz, 1H), 3.73 (d, J=14.1 Hz, 1H), 3.54-3.60 (m, 1H), 3.28 (d, J=14.1 Hz, 1H), 3.11-3.20 (m, 1H), 2.91 (br. s., 1H), 2.72-2.82 (m, 2H), 2.57-2.70 (m, 2H), 2.13-2.44 (m, 4H), 1.97-2.04 (m, 1H), 1.74-1.96 (m, 4H), 1.37-1.74 (m, 8H). m/z (ESI, +ve ion) 585.1 (M+H)$^+$.

Example 104. (1S,3'R,6'R,7'S,8'E,10'S,14'S)-6-chloro-7'-hydroxy-3,4-dihydro-2H,17'H-spiro[naphthalene-1,24'-[22]oxa[15]thia[1,16]diazapentacyclo [16.7.2.1$^{10,14}$.0$^{3,6}$.0$^{21,26}$]octacosa[8,18,20,26] tetraen]-17'-one 15',15'-dioxide or (1S,3'R,6'R,7'S, 8'E,10'R,14'R)-6-chloro-7'-hydroxy-3,4-dihydro-2H, 17'H-spiro[naphthalene-1,24'-[22]oxa[15]thia[1,16] diazapentacyclo[16.7.2.1$^{10,14}$.0$^{3,6}$.0$^{21,26}$]octacosa[8, 18,20,26]tetraen]-17'-one 15',15'-dioxide

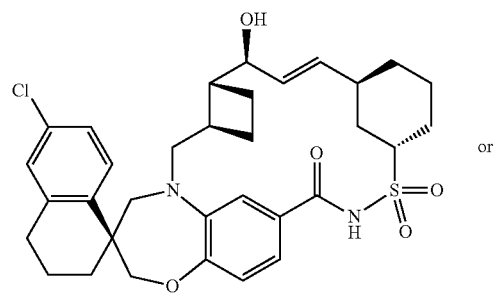

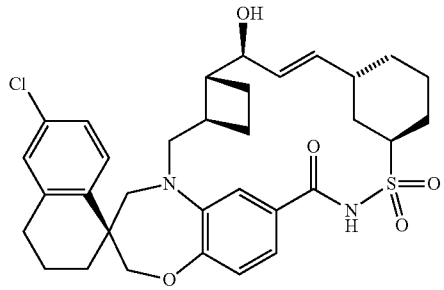

Step 1: (S)-3-vinylcyclohexanone and (R)-3-vinylcyclohexanone

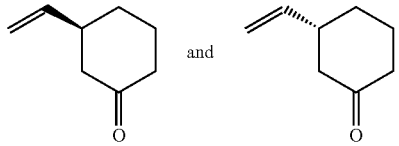

The title compound was prepared according to the procedure described by Kerdesky, et al., *Journal of Medicinal Chemistry*, 1987, 30, 1177-1186.

Step 2: (1R,3S)-3-vinylcyclohexanol and (1S,3R)-3-vinylcyclohexanol

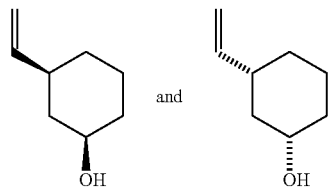

To a stirred, 0° C. solution of 3-vinylcyclohexanone (3.30 g, 26.6 mmol) in THF (100 mL) under a nitrogen atmosphere was added sodium borohydride (1.11 g, 29.2 mmol) portionwise over three minutes. After five minutes the cooling bath was removed and the reaction was warmed to rt for one hour. The reaction was then quenched by addition of water (5 mL) and the resulting mixture was stirred at rt for 20 minutes and subsequently partitioned between EtOAc and water. The organic layer was dried over MgSO$_4$, filtered and concentrated in vacuo. Column chromatography (80 g silica gel; hexanes:EtOAc, 1:0 to 3:1 solvent gradient) gave racemic cis-3-vinylcyclohexanol (2.00 g, 15.9 mmol, 60% yield).

Step 3: (1R,3S)-3-vinylcyclohexyl Methanesulfonate and (1S,3R)-3-vinylcyclohexyl Methanesulfonate

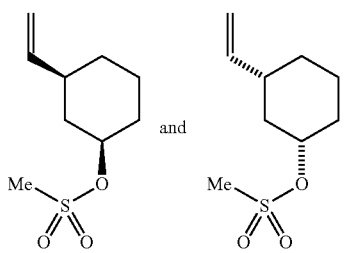

To a stirred, 0° C. solution of racemic cis-3-vinylcyclohexanol (2.00 g, 15.9 mmol) in DCM (79 mL) under a nitrogen atmosphere was added triethylamine (4.42 mL, 31.7 mmol) followed by methanesulfonyl chloride (1.85 mL, 23.8 mmol). After five minutes, the cooling bath was removed and the reaction was stirred at rt overnight. On the following day, the reaction mixture was partitioned between DCM and 1M HCl (aq.). The organic layer was washed with brine, dried over MgSO$_4$, filtered and concentrated in vacuo. Column chromatography (80 g silica gel; isocratic DCM eluent) gave racemic cis-3-vinylcyclohexyl methanesulfonate (2.40 g, 11.7 mmol, 74% yield) as a light yellow liquid.

Step 4: 2-(((1S,3S)-3-vinylcyclohexyl)thio)pyrimidine and 2-(((1R,3R)-3-vinylcyclohexyl)thio)pyrimidine

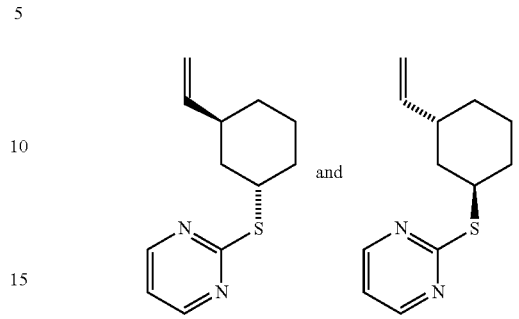

To a stirred solution of racemic cis-3-vinylcyclohexyl methanesulfonate (2.30 g, 11.3 mmol) in DMF (37.5 mL) were added 2-mercaptopyrimidine (1.263 g, 11.26 mmol) and potassium carbonate (1.556 g, 11.26 mmol). The reaction mixture was stirred at 80° C. for three hours. Upon cooling to room temperature, the mixture was partitioned between EtOAc and water. The aqueous layer was extracted with EtOAc, and the combined organic extracts were washed with brine, dried over MgSO$_4$, filtered and concentrated in vacuo. Column chromatography (40 g silica gel; hexanes:EtOAc, 1:0 to 4:1 solvent gradient) gave racemic trans-2-((3-vinylcyclohexyl)thio)pyrimidine (1.32 g, 5.99 mmol, 53% yield).

Step 5: 2-(((1S,3S)-3-vinylcyclohexyl)sulfonyl)pyrimidine and 2-(((1R,3R)-3-vinylcyclohexyl)sulfonyl)pyrimidine

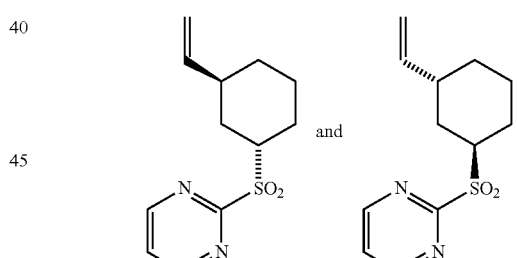

To a vigorously stirred mixture of sodium tungstate dihydrate (0.099 g, 0.300 mmol), phenylphosphonic acid (0.047 g, 0.300 mmol) and tetrabutylammonium sulfate (50 weight % solution in water; 0.348 mL, 0.300 mmol) in water (5.45 mL) was added hydrogen peroxide (30 weight % solution in water; 1.530 mL, 14.98 mmol). After two minutes, a solution of racemic trans-2-((3-vinylcyclohexyl)thio)pyrimidine (1.32 g, 5.99 mmol) in toluene (54.5 mL) was added, and the reaction mixture was heated at 50° C. overnight. Upon cooling to rt, the mixture was partitioned between EtOAc and water. The organic layer was dried over MgSO$_4$, filtered and concentrated in vacuo. Purification of the crude residue by column chromatography (24 g silica gel; hexanes:EtOAc, 1:0 to 3:1 solvent gradient) gave racemic trans-2-((3-vinylcyclohexyl)sulfonyl)pyrimidine (1.00 g, 3.96 mmol, 66% yield).

Step 6: (1S,3S)-3-vinylcyclohexane-1-sulfonamide and (1R,3R)-3-vinylcyclohexane-1-sulfonamide

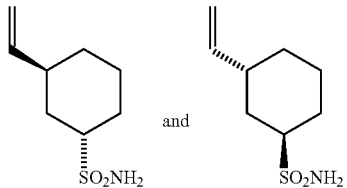

To a stirred solution of racemic trans-2-((3-vinylcyclohexyl)sulfonyl)pyrimidine (1.00 g, 3.96 mmol) in MeOH (39.6 mL) was added sodium methoxide (25 weight % solution in MeOH; 0.906 ml, 3.96 mmol), and the resulting reaction mixture was stirred at rt for 45 minutes. After this time, solvents were removed in vacuo and the residue was triturated with diethyl ether. The resulting solids were filtered, washed with diethyl ether and dried under high vacuum to give crude racemic sodium trans-3-vinylcyclohexane-1-sulfinate (0.778 g, 3.96 mmol, 100% crude yield for the pyrimidine cleavage step), which was used without further purification.

To a solution of crude racemic sodium trans-3-vinylcyclohexane-1-sulfinate (0.78 g, 4.0 mmol) in water (39.7 mL) were added sodium acetate (0.652 g, 7.95 mmol) and hydroxylamine-O-sulfonic acid (0.450 g, 3.97 mmol), and the resulting reaction mixture was heated at 50° C. for 30 minutes. After this time, the reaction was cooled to 0° C. for 10 minutes and basified to pH=ca. 12 with NaOH (up to pH 12). The resulting mixture was extracted with EtOAc, and the combined organic extracts were dried over MgSO$_4$, filtered and concentrated in vacuo to give racemic trans-3-vinylcyclohexane-1-sulfonamide (0.64 g, 3.4 mmol, 85% yield for the nucleophilic sulfonamidation; 85% overall yield from the sulfonyl pyrimidine).

Step 7: (S)-6'-chloro-5-(((1R,2R)-2-((S,E)-1-hydroxy-3-((1R,3R)-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((S,E)-1-hydroxy-3-((1S,3S)-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic Acid

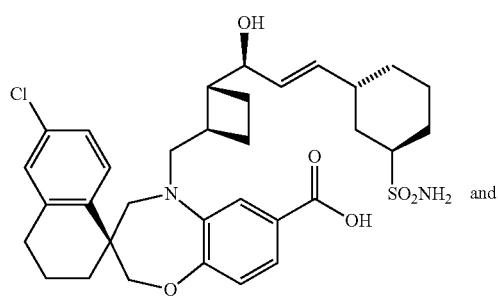

-continued

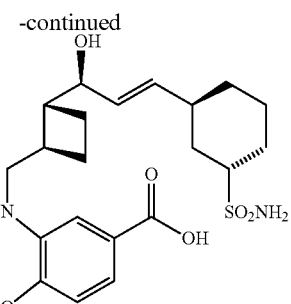

A solution of Intermediate AA12A (130 mg, 0.255 mmol) in 1,2-dichloroethane (3641 μL) was sparged with argon for 10 minutes and charged with (1,3-dimesitylimidazolidin-2-ylidene)(2-isopropoxybenzylidene)ruthenium(VI) chloride (16.0 mg, 0.0250 mmol), and the resulting mixture was stirred at rt overnight. On the following day, the catalyst was deactivated by sparging air through the mixture for five minutes. Solvents were removed in vacuo, and the crude residue obtained was purified by column chromatography (4 g silica gel; hexanes: (99:1 EtOAc:AcOH), 1:0 to 6:4 solvent gradient) to give a mixture of (S)-6'-chloro-5-(((1R,2R)-2-((S,E)-1-hydroxy-3-((1R,3R)-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-3-((1S,3S)-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic acid (95 mg, 0.15 mmol total, 59% combined yield).

Step 8: (1S,3'R,6'R,7'S,8'E,10'S,14'S)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide or (1S,3'R,6'R,7'S,8'E,10'R,14'R)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide To a stirred solution containing a mixture of (S)-6'-chloro-5-(((1R,2R)-2-((S,E)-1-hydroxy-3-((1R,3R)-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-3-((1S,3S)-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic acid (95 mg, 0.15 mmol total) in DCM (7.55 E+04 μL) at 0° C. under a nitrogen atmosphere was added DMAP (31.4 mg, 0.257 mmol). After five minutes, the reaction mixture was charged with EDC (57.9 mg, 0.302 mmol) portionwise over five minutes and stirred at rt over the weekend. After this time, the reaction mixture was partitioned between DCM and 1 M HCl (aq.). The organic layer was dried over MgSO$_4$, filtered and concentrated in vacuo. Purification of the resulting crude residue by column chromatography (12 g silica gel; hexanes: (99:1 EtOAc:AcOH), 1:0 to 4:1 solvent gradient) gave one of the title compounds as the first eluting isomer (18 mg, 0.029 mmol, 20% yield) as a white solid. $^1$H NMR (400 MHz, CD$_3$OD) δ ppm 7.72 (d, J=8.4 Hz, 1H), 7.17 (dd, J=8.5, 2.2 Hz, 1H), 7.10 (d, J=2.2 Hz, 1H), 6.83-6.98 (m, 3H), 5.91 (dd, J=15.6, 6.6 Hz, 1H), 5.62 (dd, J=15.2, 4.8 Hz, 1H), 4.06-4.14 (m, 2H), 3.96-4.05 (m, 3H), 3.68 (d, J=14.7 Hz, 1H), 3.43-3.57 (m, 2H), 2.69-2.92 (m, 4H), 2.17-2.30 (m, 2H), 1.97-2.08 (m, 3H), 1.73-1.96 (m, 6H), 1.64 (br. s., 4H), 1.45-1.56 (m, 1H), 1.24 (t, J=7.1 Hz, 1H). m/z (ESI, +ve ion) 611.2 (M+H)+.

Example 105. (1S,3'R,6'R,7'S,8'E,10'R,14'R)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide or (1S,3'R,6'R,7'S,8'E,10'S,14'S)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide

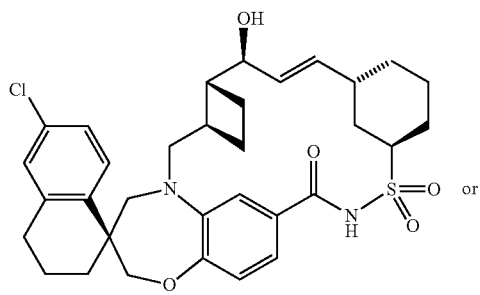

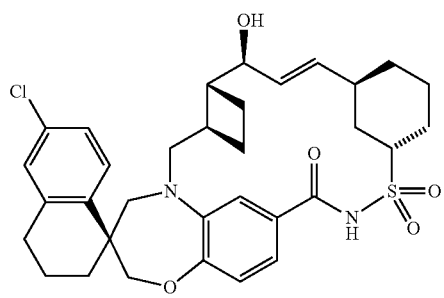

The title compound was prepared as described in Example 104, step 8 and was isolated as the second eluting isomer (16 mg, 0.026 mmol, 17% yield) as an off-white solid. $^1$H NMR (400 MHz, CD$_2$Cl$_2$) δ ppm 7.71 (d, J=8.4 Hz, 1H), 7.17 (dd, J=8.6, 2.3 Hz, 1H), 7.09 (d, J=2.2 Hz, 1H), 6.93 (d, J=0.8 Hz, 2H), 6.88 (s, 1H), 5.76-5.85 (m, 1H), 5.61-5.71 (m, 1H), 4.46 (t, J=4.8 Hz, 1H), 4.12-4.22 (m, 1H), 4.07-4.11 (m, 2H), 3.87 (d, J=14.9 Hz, 1H), 3.69 (d, J=14.3 Hz, 1H), 3.22 (d, J=14.3 Hz, 1H), 3.01 (dd, J=15.4, 9.9 Hz, 1H), 2.69-2.84 (m, 3H), 2.40-2.50 (m, 1H), 2.27-2.40 (m, 2H), 2.03 (br. s., 1H), 1.92 (d, J=7.4 Hz, 5H), 1.68-1.76 (m, 3H), 1.60-1.68 (m, 2H), 1.49-1.60 (m, 3H), 1.36-1.47 (m, 1H). m/z (ESI, +ve ion) 611.2 (M+H)+.

Example 106. (1S,3'R,6'R,7'S,10'R,14'S)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[18,20,26]trien]-17'-one 15',15'-dioxide or (1S,3'R,6'R,7'S,10'S,14'R)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[18,20,26]trien]-17'-one 15',15'-dioxide

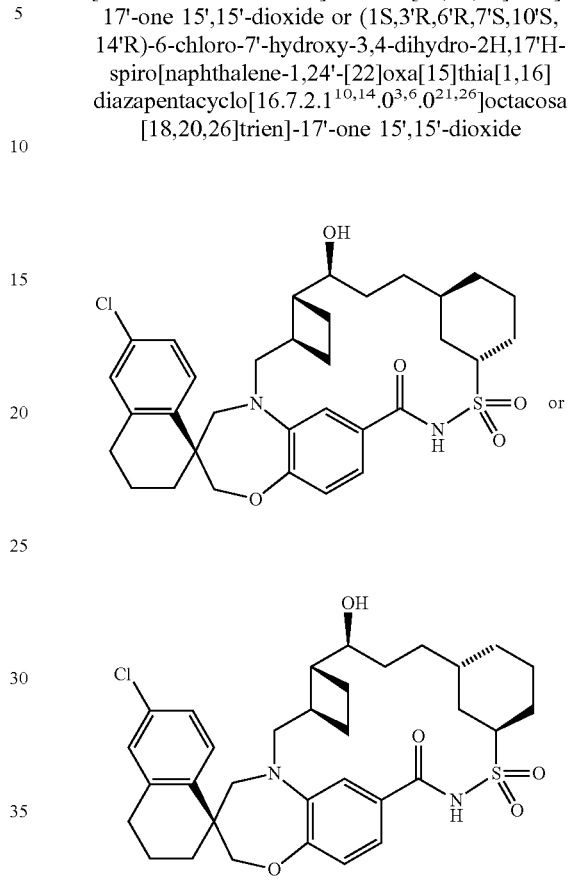

To a stirred solution of either (1S,3'R,6'R,7'S,8'E,10'S,14'S)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide or (1S,3'R,6'R,7'S,8'E,10'R,14'R)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide (Example 104; 10 mg, 0.016 mmol) in EtOAc (3272 μL) was added platinum(IV) oxide (3.7 mg, 0.016 mmol), and the reaction vessel was evacuated and filled with hydrogen (3×). The reaction mixture was stirred at rt for 45 minutes and filtered through celite, washing the filter cake with EtOAc. Removal of solvents in vacuo and purification of the resulting residue by column chromatography (4 g silica gel; hexanes: (99:1 EtOAc:AcOH), 1:0 to 80:20 solvent gradient) gave the title compound (4.7 mg, 7.7 μmol, 47% yield) as a white solid. $^1$H NMR (500 MHz, CD$_3$OD) δ ppm 7.73 (d, J=8.6 Hz, 1H), 7.17 (dd, J=8.6, 2.2 Hz, 1H), 7.10 (d, J=2.2 Hz, 1H), 7.07 (br. s., 1H), 7.03 (dd, J=8.1, 2.0 Hz, 1H), 6.93 (d, J=8.1 Hz, 1H), 4.01-4.10 (m, 2H), 3.77-3.90 (m, 2H), 3.70 (d, J=14.4 Hz, 1H), 3.55 (dd, J=11.0, 2.7 Hz, 1H), 3.40 (d, J=14.2 Hz, 1H), 3.19-3.28 (m, 1H), 2.70-2.87 (m, 2H), 2.58 (quin, J=8.3 Hz, 1H), 2.18-2.26 (m, 1H), 2.02-2.12 (m, 6H), 1.85-1.98 (m, 4H), 1.72-1.84 (m, 2H), 1.61-1.72 (m, 3H), 1.39-1.60 (m, 5H), 1.27-1.34 (m, 1H). m/z (ESI, +ve ion) 613.3 (M+H)+.

Example 107. (1S,3'R,6'R,7'S,10'S,14'R)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[18,20,26]trien]-17'-one 15',15'-dioxide or (1S,3'R,6'R,7'S,10'R,14'S)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[18,20,26]trien]-17'-one 15',15'-dioxide Example 108. (1S,3'R,6'R,7'S,8'E,10'R,14'R)-6-chloro-7'-methoxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide or (1S,3'R,6'R,7'S,8'E,10'S,14'S)-6-chloro-7'-methoxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide

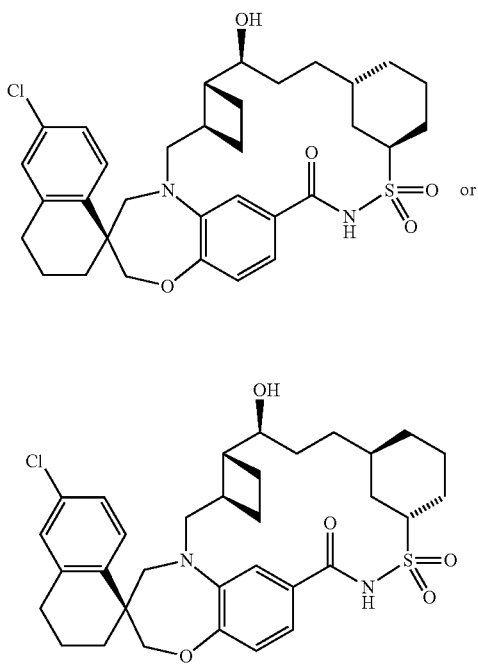

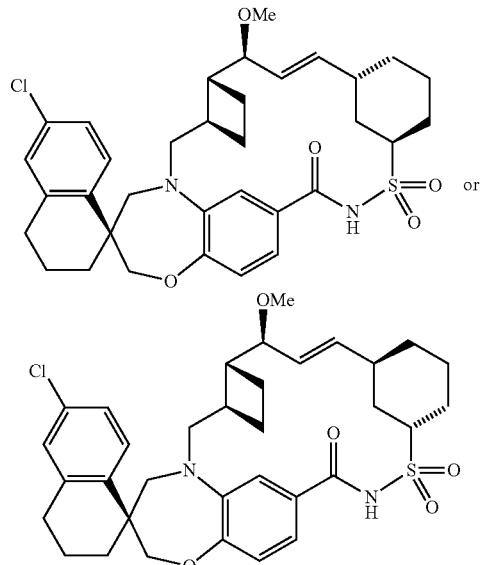

To a stirred solution of either (1S,3'R,6'R,7'S,8'E,10'R,14'R)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide or (1S,3'R,6'R,7'S,8'E,10'S,14'S)-6-chloro-7'-hydroxy-3,4-dihydro-2H,17'H-spiro[naphthalene-1,24'-[22]oxa[15]thia[1,16]diazapentacyclo[16.7.2.1$^{10,14}$ 0$^{3,6}$.0$^{21,26}$]octacosa[8,18,20,26]tetraen]-17'-one 15',15'-dioxide (Example 105; 8.0 mg, 0.013 mmol) in EtOAc (2618 μL) was added platinum(IV) oxide (3.0 mg, 0.013 mmol), and the reaction vessel was evacuated and filled with hydrogen (3×). The reaction mixture was stirred for 45 minutes at ambient temperature and then filtered through celite, washing the filter cake with EtOAc. Removal of solvent in vacuo and purification of the resulting crude residue by column chromatography (4 g silica gel; hexanes: (99:1 EtOAc:AcOH), 1:0 to 75:25 solvent gradient) gave the title compound (2.1 mg, 3.4 μmol, 26% yield) as a white solid. $^1$H NMR (400 MHz, CD$_2$Cl$_2$) δ ppm 7.76 (d, J=8.6 Hz, 1H), 7.22 (dd, J=8.4, 2.3 Hz, 1H), 7.14 (d, J=2.3 Hz, 1H), 7.01-7.06 (m, 1H), 6.93-7.00 (m, 2H), 4.08-4.25 (m, 3H), 3.78-3.91 (m, 2H), 3.74 (d, J=14.1 Hz, 1H), 3.25 (d, J=14.3 Hz, 1H), 3.07 (dd, J=15.4, 9.3 Hz, 1H), 2.73-2.90 (m, 2H), 2.23-2.54 (m, 3H), 2.05-2.10 (br. s., 1H), 1.93-2.03 (m, 3H), 1.39-1.91 (m, 17H). m/z (ESI, +ve ion) 613.2 (M+H)$^+$.

To a stirred solution of either (1S,3'R,6'R,7'S,8'E,10'R,14'R)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide or (1S,3'R,6'R,7'S,8'E,10'S,14'S)-6-chloro-7'-hydroxy-3,4-dihydro-2H,17'H-spiro[naphthalene-1,24'-[22]oxa[15]thia[1,16]diazapentacyclo[16.7.2.1$^{10,14}$ 0$^{3,6}$.0$^{21,26}$]octacosa[8,18,20,26]tetraen]-17'-one 15',15'-dioxide (Example 105; 4.0 mg, 6.5 μmol) in THF (654 μL) under a nitrogen atmosphere was added sodium hydride (60% dispersion in mineral oil; 1.3 mg, 0.033 mmol). The resulting mixture was stirred at rt for 20 minutes, charged with iodomethane (2.05 μL, 0.033 mmol and stirred at rt over the weekend. Subsequently, the reaction mixture was partitioned between EtOAc and 1 M HCl (aq.). The organic layer was dried over MgSO$_4$, filtered and concentrated in vacuo. Purification of the crude residue by column chromatography (1 g silica gel; hexanes: (99:1 EtOAc:AcOH), 1:0 to 4:1 solvent gradient) gave the title compound (1.5 mg, 2.4 μmol, 37% yield) as a white solid. $^1$H NMR (400 MHz, CD$_2$Cl$_2$) δ ppm 8.03 (br. s., 1H), 7.71 (d, J=8.4 Hz, 1H), 7.17 (dd, J=8.4, 2.3 Hz, 1H), 7.09 (d, J=2.3 Hz, 1H), 6.90-6.94 (m, 1H), 6.86-6.89 (m, 1H), 6.84 (d, J=1.8 Hz, 1H), 5.81 (dd, J=15.7, 6.7 Hz, 1H), 5.47 (ddd, J=15.6, 6.7, 1.4 Hz, 1H), 4.25 (t, J=12.0 Hz, 1H), 4.04-4.12 (m, 2H), 3.85 (d, J=15.5 Hz, 1H), 3.79-3.83 (m, 1H), 3.71 (d, J=13.7 Hz, 1H), 3.25 (s, 2H), 3.24 (d, J=14.1 Hz, 1H), 3.01 (dd, J=15.3, 10.4 Hz, 1H), 2.75-2.81 (m, 2H), 2.44-2.55 (m, 1H), 2.29-2.39 (m, 2H), 2.02-2.08 (m, 1H), 1.78-1.98 (m, 6H), 1.46-1.76 (m, 10H), 1.35-1.45 (m, 2H). m/z (ESI, +ve ion) 625.2 (M+H)$^+$.

Example 109. (1S,3'R,6'R,7'S,8'E,10'S,14'R)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide or (1S,3'R,6'R,7'S,8'E,10'R,14'S)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide

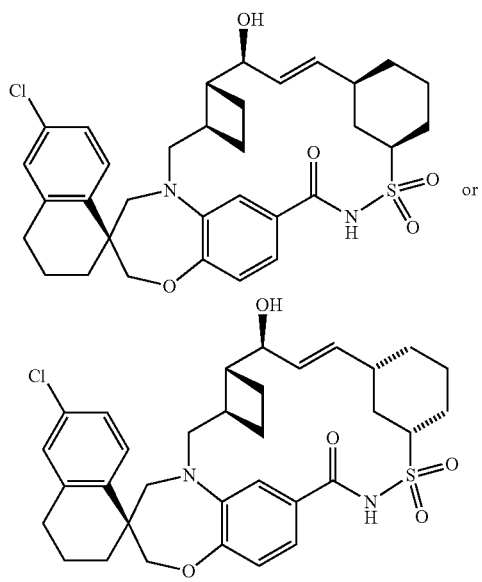

Step 1: (1S,3S)-3-vinylcyclohexanol and (1R,3R)-3-vinylcyclohexanol

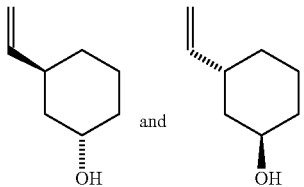

To a solution of 3-vinylcyclohexanone (Example 104, Step 1; 1.70 g, 13.7 mmol) in THF (68.4 mL) at −78° C. under a nitrogen atmosphere was added dropwise via syringe a solution of L-Selectride (1 M in THF; 16.43 ml, 16.43 mmol). The reaction mixture was stirred at this temperature for one hour and was then allowed to warm to rt over 20 minutes, after which time the reaction was quenched by addition of water (4.5 mL) and the mixture was treated with MeOH (2 mL) and 15% aqueous NaOH (18.3 mL). The resulting mixture was cooled to 0° C. in an ice/water bath, and hydrogen peroxide (30 weight % solution in water, 7.0 mL) was added dropwise via syringe over 5 minutes. Stirring at rt was continued for an additional five minutes and then the mixture was extracted twice with diethyl ether. The combined organic extracts were washed with sodium sulfite (saturated aq. solution) until it tested negative for peroxides using Quantofix indicator paper. The organic layer was dried over MgSO$_4$, filtered and concentrated in vacuo. Column chromatography (40 g silica gel; hexanes:EtOAc, 1:0 to 7:3 eluent gradient) gave racemic trans-3-vinylcyclohexanol (1.00 g, 7.92 mmol, 58% yield).

Step 2: (1S,3S)-3-vinylcyclohexyl Methanesulfonate and (1R,3R)-3-vinylcyclohexyl Methanesulfonate

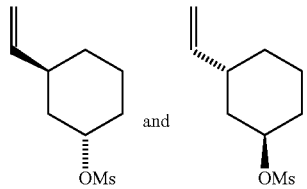

To a stirred solution of racemic trans-3-vinylcyclohexanol (1.00 g, 7.92 mmol) in DCM (39.6 mL) at 0° C. under a nitrogen atmosphere was added dropwise via syringe methanesulfonyl chloride (0.926 mL, 11.9 mmol). The reaction mixture was allowed to warm to rt overnight and was subsequently partitioned between DCM and 1 M HCl (aq.). The organic layer was dried over MgSO$_4$, filtered and concentrated in vacuo. Column chromatography (40 g silica gel, isocratic DCM eluent) gave racemic trans-3-vinylcyclohexyl methanesulfonate (1.35 g, 6.61 mmol, 83% yield).

Step 3: 2-(((1R,3S)-3-vinylcyclohexyl)thio)pyrimidine and 2-(((1S,3R)-3-vinylcyclohexyl)thio)pyrimidine

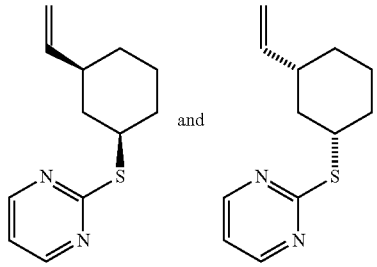

To a stirred solution of racemic trans-3-vinylcyclohexyl methanesulfonate (1.35 g, 6.61 mmol) in DMF (13.22 mL) were added 2-mercaptopyrimidine (0.815 g, 7.27 mmol) and potassium carbonate (1.00 g, 7.27 mmol). The reaction mixture was stirred at 60° C. for three hours, after which time additional portions of 2-mercaptopyrimidine (0.40 g, 3.6 mmol) and potassium carbonate (0.50 g, 3.6 mmol) were added to it. The reaction mixture was then heated at 95° C. for two hours. Upon cooling to rt, the mixture was partitioned between EtOAc and water, and the organic layer was washed with brine (2×), dried over MgSO$_4$, filtered and concentrated in vacuo. Purification of the crude residue by column chromatography (40 g silica gel; hexanes:EtOAc, 1:0 to 3:1 solvent gradient) gave racemic cis-2-((3-vinylcyclohexyl)thio)pyrimidine (0.64 g, 2.9 mmol, 44% yield).

Step 4: 2-(((1R,3S)-3-vinylcyclohexyl)sulfonyl)
pyrimidine and 2-(((1S,3R)-3-vinylcyclohexyl)
sulfonyl)pyrimidine

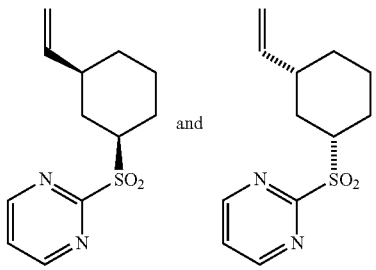 [SMILES: C=C[C@H]1CCC[C@@H](S(=O)(=O)c2ncccn2)C1 ; C=C[C@@H]1CCC[C@H](S(=O)(=O)c2ncccn2)C1]

To a vigorously stirred mixture of sodium tungstate dihydrate (0.048 g, 0.145 mmol), phenylphosphonic acid (0.023 g, 0.145 mmol) and tetrabutylammonium sulfate (50 weight % solution in water (0.169 mL, 0.145 mmol) in water (2.64 mL) was added hydrogen peroxide (30 weight % solution in water; 0.742 mL, 7.26 mmol). After two minutes, a solution of cis-2-((3-vinylcyclohexyl)thio)pyrimidine (0.64 g, 2.90 mmol) in toluene (26.4 mL) was added dropwise via syringe and the reaction was stirred at 54° C. overnight. On the following day, the mixture was treated with additional portions of sodium tungstate dihydrate (0.048 g, 0.145 mmol), tetrabutylammonium sulfate (50% in water; 0.169 mL, 0.145 mmol), phenylphosphonic acid (0.023 g, 0.145 mmol) and hydrogen peroxide (30% in water; 0.742 mL, 7.26 mmol) and the reaction was heated at 75° C. for three more hours. After this time, the mixture was cooled to rt and partitioned between EtOAc and water. The aqueous layer was extracted with EtOAc, and the combined organic extracts were dried over MgSO$_4$, filtered and concentrated in vacuo. Purification of the crude residue by column chromatography (12 g silica gel; hexanes:EtOAc, 1:0 to 6:4 solvent gradient) gave racemic cis-2-((3-vinycyclohexyl)sulfonyl)pyrimidine (0.320 g, 1.27 mmol, 44% yield).

Step 5: (1R,3S)-3-vinylcyclohexane-1-sulfonamide
and (1S,3R)-3-vinylcyclohexane-1-sulfonamide

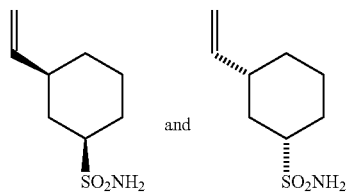

To a stirred solution of racemic cis-2-((3-vinylcyclohexyl)sulfonyl)pyrimidine (0.320 g, 1.27 mmol) in MeOH (12.68 mL) was added sodium methoxide (25 weight % solution in methanol; 0.290 ml, 1.268 mmol), and the resulting reaction mixture was stirred at rt for 75 minutes, after which time solvents were removed in vacuo to give a white solid that was triturated with diethyl ether and dried under high vacuum to provide the intermediate, crude sodium trans-3-vinylcyclohexane-1-sulfinate (0.24 g, 1.223 mmol, 96% crude yield for the pyrimidine cleavage step).

A stirred solution of crude sodium trans-3-vinylcyclohexane-1-sulfinate (0.24 g, 1.223 mmol) in water (12.23 mL) was charged with sodium acetate (0.201 g, 2.446 mmol) and hydroxylamine-O-sulfonic acid (0.277 g, 2.446 mmol), and the resulting reaction mixture was heated at 50° C. for 30 minutes. Subsequently, the mixture was cooled to 0° C. for 10 minutes and basified to pH=ca. 12 by addition of sodium hydroxide. The crude product was extracted into EtOAc, and the organics were dried over MgSO$_4$, filtered and concentrated in vacuo to give racemic cis-3-vinylcyclohexane-1-sulfonamide (0.17 g, 0.90 mmol, 73% yield for the sulfinate amidation step, 70% overall yield from the sulfonyl pyrimidine).

Step 6: (S)-6'-chloro-5-(((1R,2R)-2-((S,E)-1-hydroxy-3-((1S,3R)-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((S,E)-1-hydroxy-3-((1R,3S)-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic Acid

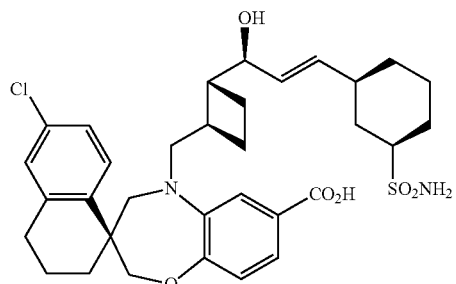

and

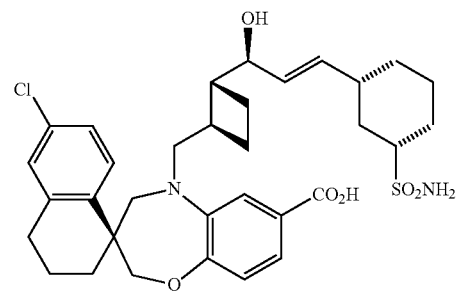

To a stirred solution of Intermediate AA12A (143 mg, 0.280 mmol) in 1,2-dichloroethene (40054) was added racemic cis-3-vinylcyclohexane-1-sulfonamide (159 mg, 0.841 mmol). The reaction mixture was sparged with argon for five minutes and charged with a solution of (1,3-dimesitylimidazolidin-2-ylidene)(2-isopropoxybenzylidene)ruthenium (VI) chloride (17.6 mg, 0.028 mmol) in DCE (1 mL). The resulting mixture was stirred at ambient temperature for two hours, after which time the catalyst was deactivated by bubbling air through the reaction mixture for 10 minutes. The mixture was partially concentrated in vacuo and purified as such by column chromatography (12 g silica gel; hexanes: (99:1 EtOAc:AcOH), 1:0 to 70:30 solvent gradient) to give (S)-6'-chloro-5-(((1R,2R)-2-((S,E)-1-hydroxy-3-((1S,3R)-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-3-((1R,3S)-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic acid (110 mg, 0.175 mmol total, 62% combined yield) as an inseparable mixture of diastereomers.

Step 7: (1S,3'R,6'R,7'S,8'E,10'S,14'R)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide or (1S,3'R,6'R,7'S,8'E,10'R,14'S)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide To a stirred solution containing a mixture of (S)-6'-chloro-5-(((1R,2R)-2-((S,E)-1-hydroxy-3-((1S,3R)-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-3-((1R,3S)-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic acid (110 mg, 0.175 mmol total) in DCM (8.74 E+04 µL) was added DMAP (36.3 mg, 0.297 mmol) under a nitrogen atmosphere. This solution was cooled at 0° C. and charged with EDC (67.0 mg, 0.350 mmol) portionwise over four minutes, and the resulting reaction mixture was allowed to warm to rt overnight. On the following day, the reaction mixture was partitioned between 1M HCl (aq.) and DCM, and the aqueous layer was back-extracted with DCM. The combined organic extracts were dried over MgSO$_4$, filtered and concentrated in vacuo. Purification of the crude residue by column chromatography (24 g silica gel; hexanes: (99:1 EtOAc:AcOH), 1:0 to 7:3 solvent gradient) gave on of the title compounds (10 mg) as the first eluting isomer. This material was further purified by reverse-phase preparative HPLC (15 to 70% (99.9:0.1 ACN:TFA) in (99.9:0.1 water:TFA) eluent gradient, 30 minutes) to provide the title compound as a white film (1.6 mg, 4.7% yield based on the mixture of acyclic precursors used in Step 6 of Example 109). $^1$H NMR (400 MHz, CD$_2$Cl$_2$) δ ppm 8.00 (br. s., 1H), 7.73 (d, J=8.4 Hz, 1H), 7.18 (dd, J=8.6, 2.3 Hz, 1H), 7.10 (d, J=2.2 Hz, 1H), 6.98-7.02 (m, 2H), 6.93-6.97 (m, 1H), 6.87 (s, 1H), 5.66-5.75 (m, 1H), 5.52-5.61 (m, 1H), 4.19-4.26 (m, 2H), 3.97 (d, J=12.1 Hz, 1H), 3.70 (dd, J=14.2, 3.4 Hz, 1H), 3.63 (d, J=14.7 Hz, 1H), 3.43 (tt, J=12.1, 3.4 Hz, 1H), 3.31 (d, J=14.3 Hz, 1H), 2.97 (dd, J=14.2, 11.1 Hz, 1H), 2.76-2.81 (m, 1H), 2.52 (d, J=7.8 Hz, 1H), 2.21-2.34 (m, 2H), 2.08-2.17 (m, 2H), 1.95-2.03 (m, 1H), 1.79-1.94 (m, 3H), 1.59-1.72 (m, 5H), 1.46-1.57 (m, 4H), 1.35-1.42 (m, 1H), 0.99-1.12 (m, 1H). m/z (ESI, +ve ion) 611.2 (M+H)$^+$.

Example 110. (1S,3'R,6'R,7'S,8'E,10'R,14'S)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide or (1S,3'R,6'R,7'S,8'E,10'S,14'R)-6-chloro-7'-hydroxy-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide

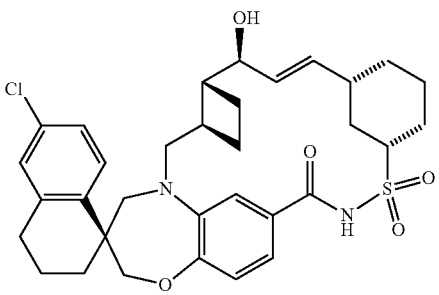

or

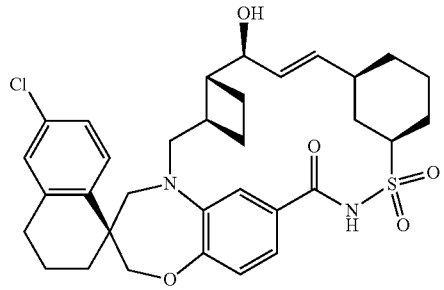

The title compound was prepared as described in Example 109, Step 7 and was isolated as the second eluting isomer (10 mg). This material was further purified by reverse-phase preparative HPLC (15 to 70% (99.9:0.1 ACN:TFA) in (99.9:0.1 water:TFA) eluent gradient, 30 minutes) to give the title compound as an off-white solid (5.0 mg, 1.5% yield based on the mixture of acyclic precursors used in Step 6 of Example 109). $^1$H NMR (400 MHz, CD$_2$Cl$_2$) δ ppm 8.32 (br. s., 1H), 7.72 (d, J=8.6 Hz, 1H), 7.17 (dd, J=8.5, 2.2 Hz, 1H), 7.10 (d, J=2.3 Hz, 1H), 6.90-7.00 (m, 2H), 6.84 (s, 1H), 5.92 (dd, J=15.6, 5.2 Hz, 1H), 5.62 (dd, J=15.8, 4.7 Hz, 1H), 4.26 (t, J=4.1 Hz, 1H), 4.16 (d, J=11.9 Hz, 1H), 4.01 (d, J=12.1 Hz, 1H), 3.70-3.79 (m, 2H), 3.62-3.70 (m, 1H), 3.23-3.59 (m, 3H), 3.16 (dd, J=14.6, 10.9 Hz, 1H), 2.73-2.83 (m, 2H), 2.65 (t, J=7.8 Hz, 1H), 2.18-2.35 (m, 3H), 2.14 (d, J=11.3 Hz, 1H), 2.03 (d, J=3.5 Hz, 1H), 1.73-1.96 (m, 7H), 1.62-1.70 (m, 1H), 1.41-1.60 (m, 3H). m/z (ESI, +ve ion) 611.2 (M+H)$^+$.

Example 111. (1S,3'R,6'R,7'S,8'E,10'R,14'S,28'S)-6-chloro-7'-hydroxy-28'-methyl-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide

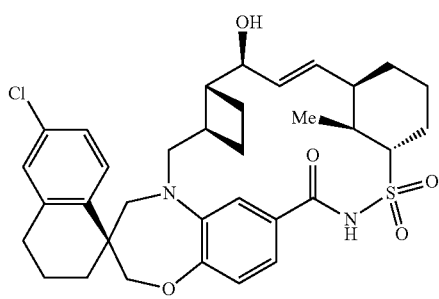 [SMILES: C[C@H]1[C@H]2/C=C/[C@H](O)[C@@H]3CC[C@H]3CN3C[C@@]4(CCCc5cc(Cl)ccc54)COc4ccc(cc43)C(=O)NS(=O)(=O)[C@H]1CCC2]

Step 1: (S)-2-bromo-2-methylcyclohexanone and (R)-2-bromo-2-methylcyclohexanone

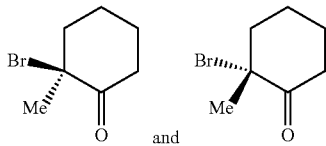 [SMILES: C[C@]1(Br)CCCCC1=O ; C[C@@]1(Br)CCCCC1=O]

A suspension of 2-methylcyclohexanone (14.1 mL, 116 mmol) and N-bromosuccinimide (20.63 g, 116 mmol) in CCl4 (290 mL) was heated at reflux for 90 minutes. The reaction mixture was subsequently cooled to 0° C., and the white solids were removed by filtration. The filtrate was concentrated in vacuo to give crude 2-bromo-2-methylcyclohexanone (21 g, 110 mmol, 95% yield) as a brown liquid.

Step 2: 2-methylcyclohex-2-enone

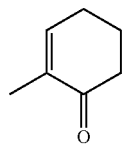

To a stirred solution of 2-bromo-2-methylcyclohexanone (21 g, 110 mmol) in DMF (220 mL) was added portionwise lithium carbonate (17.87 g, 242 mmol). The resulting mixture was heated at 145° C. overnight, cooled to rt and partitioned between Et$_2$O and brine. The aqueous layer was extracted with Et$_2$O (2×), and the combined organic extracts were washed with brine (2×), dried over MgSO$_4$, filtered and concentrated in vacuo. The resulting crude residue was purified by distillation through a short-path apparatus at a pressure of ca. 20 mm Hg, collecting the fraction boiling at 90-115° C. to provide 2-methylcyclohex-2-enone (8.7 g, 79 mmol, 71.9% yield) as a colorless liquid.

Step 3: (2S,3S)-2-methyl-3-vinylcyclohexanone and (2R,3R)-2-methyl-3-vinylcyclohexanone and (2S,3R)-2-methyl-3-vinylcyclohexanone and (2R,3S)-2-methyl-3-vinylcyclohexanone

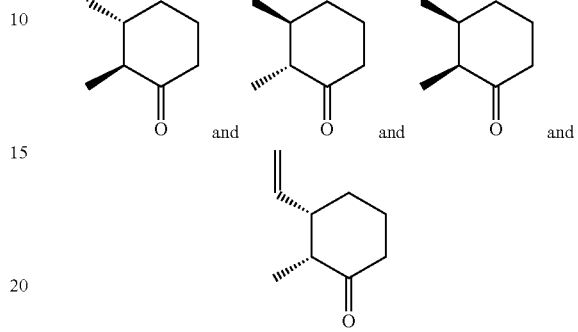

Copper(I) iodide (2.204 g, 11.57 mmol) was added to a stirred, 0° C. solution of vinylmagnesium bromide (1 M in THF; 136 mL, 136 mmol) under a nitrogen atmosphere and the resulting solution was stirred for 15 min at this temperature. A solution of 2-methylcyclohex-2-enone (7.5 g, 68.1 mmol) in THF (76 mL) was then added dropwise via addition funnel over five minutes. Five minutes later, the cooling bath was removed and stirring was continued at ambient temperature for one hour, after which time the reaction was quenched by careful addition of saturated ammonium chloride (aq) and the resulting mixture was partitioned between Et$_2$O and water. The organic layer was washed with brine, dried over MgSO$_4$, filtered and concentrated in vacuo. Column chromatography (120 g silica gel; hexanes:EtOAc, 1:0 to 4:1 solvent) gave the title compounds (3.0 g, 32% combined yield) as a mixture of diastereomers.

Step 4: (1R,2R,3R)-2-methyl-3-vinylcyclohexanol and (1R,2S,3R)-2-methyl-3-vinylcyclohexanol and (1R,2R,3S)-2-methyl-3-vinylcyclohexanol and (1R,2S,3S)-2-methyl-3-vinylcyclohexanol and (1S,2S,3S)-2-methyl-3-vinylcyclohexanol and (1S,2R,3S)-2-methyl-3-vinylcyclohexanol and (1S,2S,3R)-2-methyl-3-vinylcyclohexanol and (1S,2R,3R)-2-methyl-3-vinylcyclohexanol

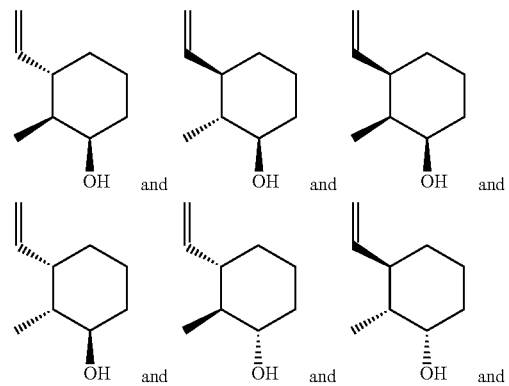

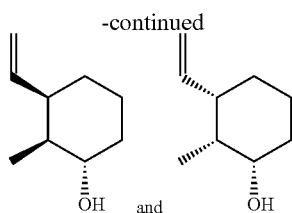

To a stirred solution of 2-methyl-3-vinylcyclohexanone (diastereomer mixture obtained in Step 3; 3.0 g, 21.71 mmol) in THF (109 mL) was added sodium borohydride (0.821 g, 21.7 mmol). The reaction mixture was stirred at rt for one hour and subsequently quenched by addition of MeOH (5 mL). This mixture was stirred at rt for one more hour and then partitioned between EtOAc and water. The aqueous layer was extracted with EtOAc, and the combined organic extracts were washed with brine, dried over MgSO$_4$, filtered and concentrated in vacuo to give the desired product (3.0 g, 99% combined yield) as a 1:1:1:1 mixture of four diastereomers, each of which was present as the racemate (8 total stereoisomers).

Step 5: (1R,2R,3R)-2-methyl-3-vinylcyclohexyl methanesulfonate and (1R,2S,3R)-2-methyl-3-vinylcyclohexyl Methanesulfonate and (1R,2R,3S)-2-methyl-3-vinylcyclohexyl Methanesulfonate and (1R,2S,3S)-2-methyl-3-vinylcyclohexyl Methanesulfonate and (1S,2S,3S)-2-methyl-3-vinylcyclohexyl Methanesulfonate and (1S,2R,3S)-2-methyl-3-vinylcyclohexyl Methanesulfonate and (1S,2S,3R)-2-methyl-3-vinylcyclohexyl Methanesulfonate and (1S,2R,3R)-2-methyl-3-vinylcyclohexyl Methanesulfonate

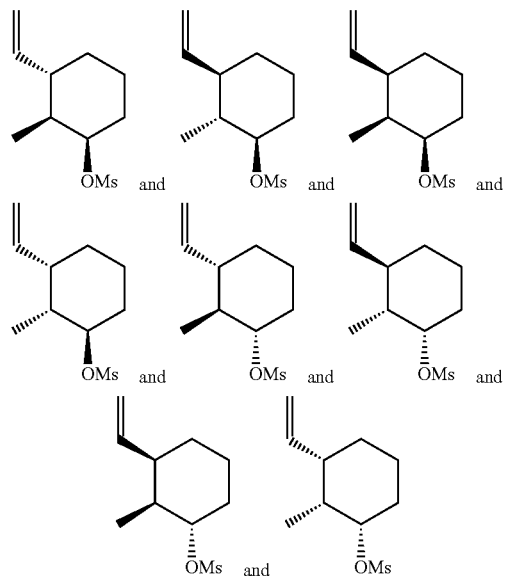

A stirred solution of 2-methyl-3-vinylcyclohexanol (racemic diastereomer mixture prepared in Step 4; 3.0 g, 5.3 mmol) in DCM (26.7 mL) was cooled to 0° C. and charged with triethylamine (1.491 mL, 10.70 mmol) and methanesulfonyl chloride (0.625 mL, 8.02 mmol). The reaction mixture was stirred at 0° C. for 10 minutes and then allowed to warm to rt for one hour. After this time, the reaction mixture was partitioned between DCM and 1M HCl (aq). The organic layer was washed with saturated NaHCO$_3$ (aq.), dried over MgSO$_4$, filtered and concentrated in vacuo. The crude residue was purified by column chromatography (120 g silica gel, isocratic DCM eluent) to give 2-methyl-3-vinylcyclohexyl methanesulfonate compound as a 1:1:1:1 mixture of diastereomers, each of which was present as the racemate (3.2 g, 3.7 mmol total, 69% combined yield).

Step 6: 2-(((1R,2S,3S)-2-methyl-3-vinylcyclohexyl)sulfonyl)pyrimidine and 2-(((1S,2R,3R)-2-methyl-3-vinylcyclohexyl)sulfonyl)pyrimidine

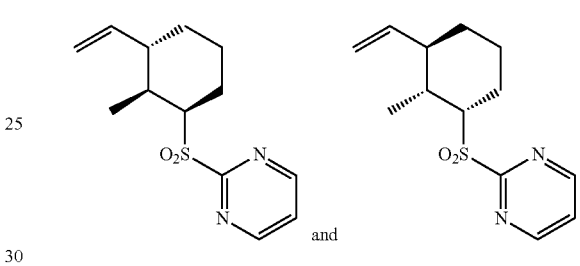

To a stirred solution of 2-methyl-3-vinylcyclohexyl methanesulfonate (racemic diastereomer mixture obtained in Step 5; 3.2 g, 3.7 mmol) in DMF (12.21 mL) were added potassium carbonate (0.760 g, 5.50 mmol) and 2-mercaptopyrimidine (0.493 g, 4.40 mmol), and the resulting reaction mixture was stirred at 70° C. overnight. After this time, additional portions of K$_2$CO$_3$ (1.5 g, 11 mmol) and 2-mercaptopyrimidine (1.0 g, 8.9 mmol) were added, and the reaction mixture was stirred at 100° C. for three hours, after which time it was cooled to rt and partitioned between EtOAc and brine. The organic layer was washed with brine, dried over MgSO$_4$, filtered and concentrated in vacuo. The crude residue was purified by column chromatography (80 g silica gel; hexanes:EtOAc, 1:0 to 3:1 solvent gradient) to give a racemic mixture of 2-(((1R,2S,3S)-2-methyl-3-vinylcyclohexyl)thio)pyrimidine and 2-(((1S,2R,3R)-2-methyl-3-vinylcyclohexyl)thio)pyrimidine (1.2 g, 35% material recovery) as the only isolated product.

This material was redissolved in DCM (25.6 mL) and the resulting solution was charged with meta-chloroperoxybenzoic acid (ca. 77%, balance=meta-chlorobenzoic acid and water; 2.98 g, 13.31 mmol) and stirred at rt for three hours. After this time, the reaction mixture was partitioned between DCM and saturated aqueous sodium bicarbonate. The organic layer was dried over MgSO$_4$, filtered and concentrated in vacuo. Purification of the crude residue by column chromatography (24 g silica gel; hexanes:EtOAc, 1:0 to 2:1 solvent gradient) gave a racemic mixture of 2-(((1R,2S,3S)-2-methyl-3-vinylcyclohexyl)sulfonyl)pyrimidine and 2-(((1S,2R,3R)-2-methyl-3-vinylcyclohexyl)sulfonyl)pyrimidine (0.40 g, 1.5 mmol, 10% overall yield).

297

Step 7: (1R,2S,3S)-2-methyl-3-vinylcyclohexane-1-sulfonamide and (1S,2R,3R)-2-methyl-3-vinylcyclohexane-1-sulfonamide

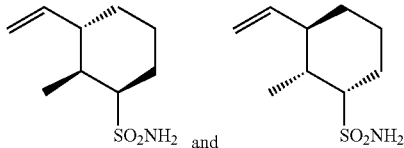

To a stirred solution containing a racemic mixture of 2-(((1R,2S,3S)-2-methyl-3-vinylcyclohexyl)sulfonyl)pyrimidine and 2-(((1S,2R,3R)-2-methyl-3-vinylcyclohexyl)sulfonyl)pyrimidine (400 mg, 1.50 mmol) in MeOH (15 mL) was added sodium methoxide (25 weight % solution in methanol; 343 µL, 1.50 mmol), and the resulting reaction mixture was stirred at rt for one hour. The solvent was evaporated in vacuo and diethyl ether was added to the mixture. The solids were filtered under vacuum, washed with diethyl ether and dried under high vacuum to give a racemic mixture of sodium (1R,2R,3S)-2-methyl-3-vinylcyclohexane-1-sulfinate and sodium (1S,2S,3R)-2-methyl-3-vinylcyclohexane-1-sulfinate (0.310 g, 1.47 mmol, 98% yield).

A solution of a racemic mixture of sodium (1R,2R,3S)-2-methyl-3-vinylcyclohexane-1-sulfinate and sodium (1S,2S,3R)-2-methyl-3-vinylcyclohexane-1-sulfinate (0.31 g, 1.474 mmol) in water (14.74 mL) was charged with sodium acetate (0.242 g, 2.95 mmol) and hydroxylamine-O-sulfonic acid (0.250 g, 2.211 mmol), and the reaction mixture was heated at 50° C. for one hour. After this time, the reaction mixture was cooled to rt, basified with NaOH to pH=ca. 12 and extracted with EtOAc. The aqueous layer was extracted with EtOAc followed by DCM, and the combined organic extracts were dried over $MgSO_4$, filtered and concentrated in vacuo to give a racemic mixture of (1R,2S,3S)-2-methyl-3-vinylcyclohexane-1-sulfonamide and (1S,2R,3R)-2-methyl-3-vinylcyclohexane-1-sulfonamide (0.20 g, 0.98 mmol, 67% yield for the sulfinate amidation, 66% overall yield).

Step 8: (S)-6'-chloro-5-(((1R,2R)-2-((S,E)-1-hydroxy-3-((1R,2R,3S)-2-methyl-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((S,E)-1-hydroxy-3-((1S,2S,3R)-2-methyl-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic Acid

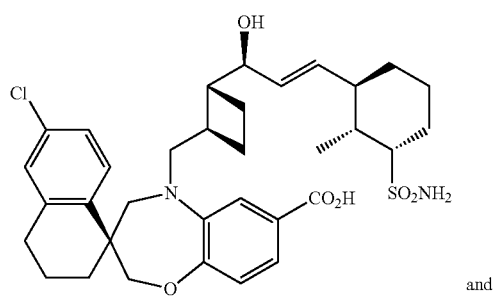

and

298

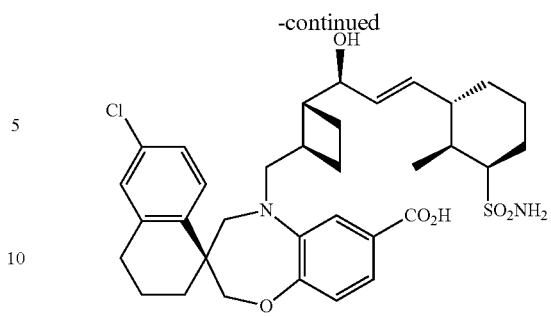

A solution of Intermediate AA12A (80.0 mg, 0.157 mmol) and a racemic mixture of (1R,2S,3S)-2-methyl-3-vinylcyclohexane-1-sulfonamide and (1S,2R,3R)-2-methyl-3-vinylcyclohexane-1-sulfonamide (96.0 mg, 0.471 mmol) in 1,2-dichloroethane (1568 µL) was sparged with argon for 10 minutes and then charged with (1,3-dimesitylimidazolidin-2-ylidene)(2-isopropoxybenzylidene)ruthenium(VI) chloride (9.83 mg, 0.016 mmol). The resulting mixture was stirred at rt for two hours. After this time, titanium tetra (isopropoxide) (3 drops) and an additional portion of (1,3-dimesitylimidazolidin-2-ylidene)(2-isopropoxybenzylidene)ruthenium(VI) chloride (9.83 mg, 0.016 mmol) were added. Stirring at room temperature was continued overnight. On the following day, the catalyst was deactivated by sparging air through the mixture for five minutes. Solvents were removed in vacuo, and the residue was purified by column chromatography (4 g silica gel; hexanes:(99:1 EtOAc:AcOH), 1:0 to 6:4 solvent gradient) to give a mixture (S)-6'-chloro-5-(((1R,2R)-2-((S,E)-1-hydroxy-3-((1R,2R,3S)-2-methyl-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-3-((1S,2S,3R)-2-methyl-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic acid (40 mg, 0.062 mmol total, 40% combined yield).

Step 9: (1S,3'R,6'R,7'S,8'E,10'R,14'S,28'R)-6-chloro-7'-hydroxy-28'-methyl-3,4-dihydro-2H,17'H-spiro[naphthalene-1,24'-[22]oxa[15]thia[1,16]diazapentacyclo[$16.7.2.1^{10,14}.0^{3,6}.0^{21,26}$]octacosa[8,18,20,26]tetraen]-17'-one 15',15'-dioxide To a stirred solution of (S)-6'-chloro-5-(((1R,2R)-2-((S,E)-1-hydroxy-3-((1R,2R,3S)-2-methyl-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-3-((1S,2S,3R)-2-methyl-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic acid (40 mg, 0.062 mmol) in DCM (3.11 E+04 µL) at 0° C. was added DMAP (12.9 mg, 0.106 mmol) followed by EDC (23.84 mg, 0.124 mmol). The reaction mixture was stirred at rt for two days and then partitioned between DCM and aqueous citric acid. The organic layer was dried over $MgSO_4$, filtered and concentrated in vacuo. Purification of the crude residue by column chromatography (4 g silica gel; DCM:acetone, 1:0 to 9:1 solvent gradient) gave the title compound, (1S,3'R,6'R,7'S,8'E,10'R,14'S,28'R)-6-chloro-7'-hydroxy-28'-methyl-3,4-dihydro-2H,17'H-spiro[naphthalene-1,24'-[22]oxa[15]thia[1,16]diazapentacyclo[$16.7.2.1^{10,}$ $_{14}.0^{3,6}.0^{21,26}$]octacosa[8,18,20,26]tetraen]-17'-one 15',15'-dioxide (4.5 mg, 11.6% yield) as the second eluting isomer. $^1$H NMR (400 MHz, CD$_3$OD) δ ppm 7.72 (d, J=8.4 Hz, 1H), 7.68 (d, J=8.6 Hz, 0.2H), 7.51-7.53 (m, 0.2H), 7.36-7.41 (m, 0.3H), 7.17 (dd, J=8.4, 2.3 Hz, 1H), 7.10 (s, 1H), 6.85-6.97 (m, 2H), 6.06-6.18 (m, 1H), 5.67 (d, J=12.1 Hz, 1H), 5.59-5.63 (m, 0.4H), 4.15-4.27 (m, 1H), 3.98-4.07 (m, 2H), 3.66 (d, J=14.5 Hz, 1H), 3.42-3.52 (m, 2H), 2.70-2.97 (m, 3H), 2.63 (s, 1H), 2.38 (br. s., 1H), 2.22-2.31 (m, 1H), 2.17-2.19 (m, 1H), 2.16 (s, 3H), 2.02-2.13 (m, 3H), 1.60-1.97 (m, 10H), 1.39-1.56 (m, 3H), 1.14-1.36 (m, 9H). m/z (ESI, +ve ion) 624.8 (M+H)$^+$.

Example 112. (1S,3'R,6'R,7'S,8'E,10'S,14'R,28'S)-6-chloro-7'-hydroxy-28'-methyl-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide

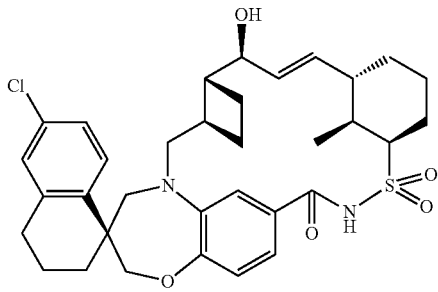 [SMILES: C[C@H]1[C@@H]2/C=C/[C@H](O)[C@@H]3CC[C@H]3CN3C[C@@]4(CCCc5cc(Cl)ccc54)COc4ccc(cc43)C(=O)NS(=O)(=O)[C@@H]1CCC2]

Step 1: (S)-methyl 5-(((1R,2R)-2-acryloylcyclobutyl)methyl)-6'-chloro-3',4,4',5-tetrahydro-2H,2'H-spiro[benzo[b][1,4]oxazepine-3,1'-naphthalene]-7-carboxylate

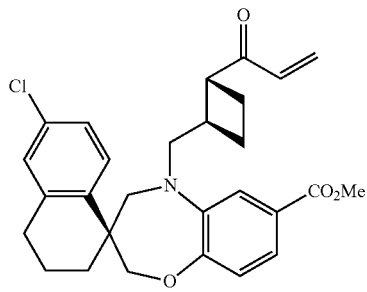 [SMILES: C=CC(=O)[C@@H]1CC[C@H]1CN1C[C@@]2(CCCc3cc(Cl)ccc32)COc2ccc(C(=O)OC)cc21]

To a stirred solution of Intermediate AA11A (1.78 g, 3.69 mmol) in DCM (36.9 mL) was added Dess-Martin periodinane (1.88 g, 4.43 mmol), and the resulting reaction mixture was stirred at rt for 45 minutes. After this time, the mixture was diluted with diethyl ether and saturated sodium thiosulfate (aq.) was added to it. This mixture was stirred at rt for 10 minutes, and then the layers were separated. The organic layer was washed with saturated sodium thiosulfate (aq.), saturated sodium bicarbonate (aq.), dried over MgSO$_4$, filtered and concentrated in vacuo. Purification of the crude residue by column chromatography (40 g silica gel; hexanes: EtOAc, 1:0 to 3:1 solvent gradient) gave (S)-methyl 5-(((1R, 2R)-2-acryloylcyclobutyl)methyl)-6'-chloro-3',4,4',5-tetrahydro-2H,2'H-spiro[benzo[b][1,4]oxazepine-3,1'-naphthalene]-7-carboxylate (1.2 g, 2.5 mmol, 68% yield).

Step 2: (S)-methyl 6'-chloro-5-(((1R,2R)-2-((E)-3-((1S,2S,3R)-2-methyl-3-(pyrimidin-2-ylthio)cyclohexyl)acryloyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((E)-3-((1R,2R,3S)-2-methyl-3-(pyrimidin-2-ylthio)cyclohexyl)acryloyl)cyclobutyl)methyl)-3',4,4',5-tetrahydro-2H,2'H-spiro[benzo[b][1,4]oxazepine-3,1'-naphthalene]-7-carboxylate

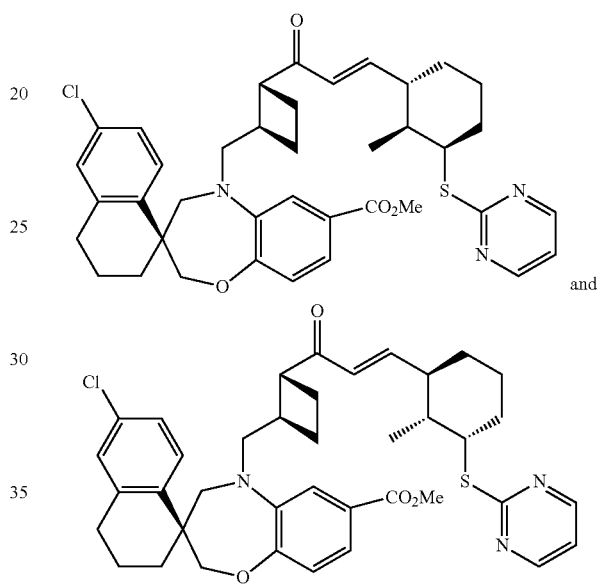

A solution of (S)-methyl 5-(((1R,2R)-2-acryloylcyclobutyl)methyl)-6'-chloro-3',4,4',5-tetrahydro-2H,2'H-spiro[benzo[b][1,4]oxazepine-3,1'-naphthalene]-7-carboxylate (0.430 g, 0.896 mmol) and a racemic mixture of a racemic mixture of 2-(((1R,2S,3S)-2-methyl-3-vinylcyclohexyl)thio)pyrimidine and 2-(((1S,2R,3R)-2-methyl-3-vinylcyclohexyl)thio)pyrimidine (prepared as in the first part of Step 6 in Example 111; 0.231 g, 0.985 mmol) in 4.6 mL DCE was sparged with argon for 10 minutes and then charged with a solution of (1,3-dimesitylimidazolidin-2-ylidene)(2-isopropoxybenzylidene)ruthenium(VI) chloride (0.070 g, 0.11 mmol) in DCE (2 mL) by dropwise addition over one minute. The resulting reaction mixture was heated at reflux overnight. On the following day, the catalyst was deactivated by sparging air through the reaction mixture for five minutes. Purification of the crude products by column chromatography (24 g silica gel; hexanes:EtOAc, 1:0 to 3:1) gave a mixture of (S)-methyl 6'-chloro-5-(((1R,2R)-2-((E)-3-((1S,2S,3R)-2-methyl-3-(pyrimidin-2-ylthio)cyclohexyl) acryloyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((E)-3-((1R,2R,3S)-2-methyl-3-(pyrimidin-2-ylthio)cyclohexyl) acryloyl)cyclobutyl)methyl)-3',4,4',5-tetrahydro-2H,2'H-spiro[benzo[b][1,4]oxazepine-3,1'-naphthalene]-7-carboxylate (0.400 g, 0.583 mmol total, 65% combined yield).

Step 3: (S)-methyl 6'-chloro-5-(((1R,2R)-2-((E)-3-((1S,2S,3R)-2-methyl-3-(pyrimidin-2-ylsulfonyl)cyclohexyl)acryloyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((E)-3-((1R,2R,3S)-2-methyl-3-(pyrimidin-2-ylsulfonyl)cyclohexyl)acryloyl)cyclobutyl)methyl)-3',4,4',5-tetrahydro-2H,2'H-spiro[benzo[b][1,4]oxazepine-3,1'-naphthalene]-7-carboxylate

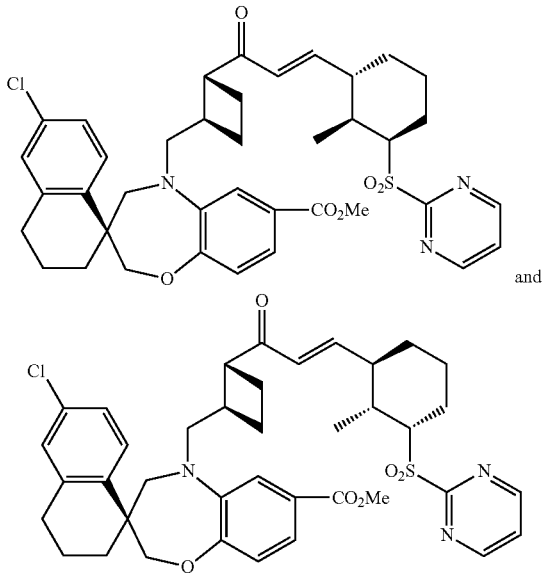

To a stirred solution of (S)-methyl 6'-chloro-5-(((1R,2R)-2-((E)-3-((1S,2S,3R)-2-methyl-3-(pyrimidin-2-ylthio)cyclohexyl)acryloyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((E)-3-((1R,2R,3S)-2-methyl-3-(pyrimidin-2-ylthio)cyclohexyl)acryloyl)cyclobutyl)methyl)-3',4,4',5-tetrahydro-2H,2'H-spiro[benzo[b][1,4]oxazepine-3,1'-naphthalene]-7-carboxylate (diastereomer mixture obtained in Step 2; 0.900 g, 1.31 mmol) in toluene (2.384 mL) and water (0.238 mL) were added sodium tungstate dihydrate (0.043 g, 0.13 mmol), phenylphosphonic acid (0.015 mL, 0.13 mmol) and tetrabutylammonium sulfate (50 weight % solution in water; 0.152 mL, 0.131 mmol). After two minutes, hydrogen peroxide (30 weight % solution in water; 0.335 mL, 3.28 mmol) was added in one portion, and the reaction mixture was heated at 55° C. After one hour, additional portions of phenylphosphonic acid (0.015 mL, 0.131 mmol), tetrabutylammonium sulfate (50% solution; 0.152 mL, 0.131 mmol), sodium tungstate dihydrate (0.043 g, 0.131 mmol) and hydrogen peroxide (30% solution; 0.30 mL, 2.9 mmol) were added, and the reaction was subsequently heated at 95° C. for one hour. Further additions of sodium tungstate dihydrate (0.043 g, 0.131 mmol) and hydrogen peroxide (30% solution; 0.50 mL, 4.8 mmol) were performed at this time, and heating at 95° C. was continued for two more hours. The reaction mixture was then cooled to rt and partitioned between EtOAc and saturated aqueous sodium sulfite. The aqueous layer was extracted with EtOAc, and the combined organic extracts were washed sequentially with saturated aqueous sodium thiosulfate and brine, dried over MgSO₄, filtered and concentrated in vacuo. Purification of the crude residue by column chromatography (24 g silica gel; hexanes:EtOAc, 1:0 to 3:1 solvent gradient) gave a mixture of (S)-methyl 6'-chloro-5-(((1R,2R)-2-((E)-3-((1S,2S,3R)-2-methyl-3-(pyrimidin-2-ylsulfonyl)cyclohexyl)acryloyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((E)-3-((1R,2R,3S)-2-methyl-3-(pyrimidin-2-ylsulfonyl)cyclohexyl)acryloyl)cyclobutyl)methyl)-3',4,4',5-tetrahydro-2H,2'H-spiro[benzo[b][1,4]oxazepine-3,1'-naphthalene]-7-carboxylate (0.36 g, 0.50 mmol total, 38% combined yield).

Step 4: (S)-methyl 6'-chloro-5-(((1R,2R)-2-((S,E)-1-hydroxy-3-((1S,2S,3R)-2-methyl-3-(pyrimidin-2-ylsulfonyl)cyclohexyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S,E)-1-hydroxy-3-((1R,2R,3S)-2-methyl-3-(pyrimidin-2-ylsulfonyl)cyclohexyl)allyl)cyclobutyl)methyl)-3',4,4',5-tetrahydro-2H,2'H-spiro[benzo[b][1,4]oxazepine-3,1'-naphthalene]-7-carboxylate

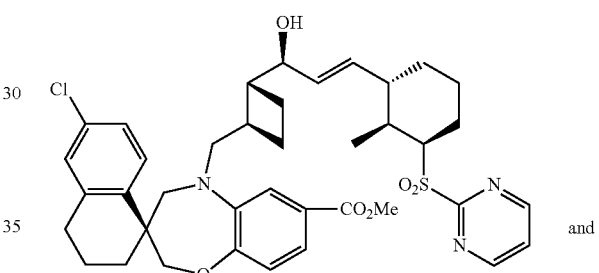

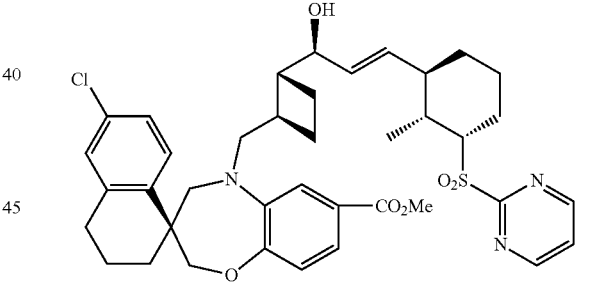

To a stirred, 0° C. solution of (S)-methyl 6'-chloro-5-(((1R,2R)-2-((E)-3-((1S,2S,3R)-2-methyl-3-(pyrimidin-2-ylsulfonyl)cyclohexyl)acryloyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((E)-3-((1R,2R,3S)-2-methyl-3-(pyrimidin-2-ylsulfonyl)cyclohexyl)acryloyl)cyclobutyl)methyl)-3',4,4',5-tetrahydro-2H,2'H-spiro[benzo[b][1,4]oxazepine-3,1'-naphthalene]-7-carboxylate (diastereomer mixture obtained in Step 3; 0.35 g, 0.487 mmol) in THF (8.66 mL) and MeOH (1.083 mL) were added cerium(III) chloride (0.132 g, 0.536 mmol) and sodium borohydride (0.041 g, 1.072 mmol), and the reaction mixture was stirred at 0° C. for one hour. After this time, 1M aqueous citric acid was added, and the mixture was extracted with EtOAc. The aqueous layer was extracted with EtOAc, and the combined organic extracts were dried over MgSO₄, filtered and concentrated in vacuo. Purification of the crude residue by column chromatography gave in order of elution: (S)-methyl 6'-chloro-5-(((1R,2R)-2-((S,E)-1-hydroxy-3-((1S,2S,3R)-2-methyl-3-(pyrimidin-2-ylsulfonyl)cyclohexyl)allyl)cyclobutyl)methyl)-3',4,4',5-tetrahydro-2H,2'H-spiro[benzo[b][1,4]oxazepine-3,1'-naphthalene]-7-carboxylate (0.130 g, 37% yield), and (S)-methyl 6'-chloro-5-(((1R,2R)-2-((S,E)-1-hydroxy-3-((1R,2R,3S)-2-methyl-3-(pyrimidin-2-ylsulfonyl)cyclohexyl)allyl)cyclobutyl)methyl)-3',4,4',5-tetrahydro-2H,2'H-spiro[benzo[b][1,4]oxazepine-3,1'-naphthalene]-7-carboxylate (135 mg, 38% yield). Comparison of the final product (Step 7 of this example) to the early-eluting diastereomer obtained in Step 9 of Example 111) established the absolute stereochemistries of these compounds.

Step 5: (S)-methyl 6'-chloro-5-(((1R,2R)-2-((E)-3-((1S,2S,3R)-2-methyl-3-sulfamoylcyclohexyl)acryloyl)cyclobutyl)methyl)-3',4,4',5-tetrahydro-2H,2'H-spiro[benzo[b][1,4]oxazepine-3,1'-naphthalene]-7-carboxylate

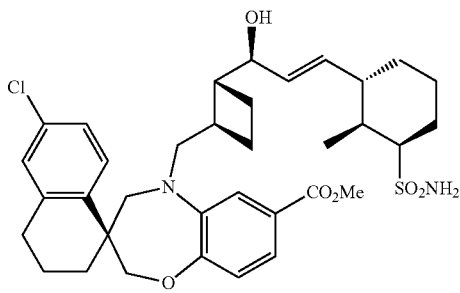 [SMILES: COC(=O)c1ccc2c(c1)N(C[C@@H]1CC[C@H]1[C@@H](O)/C=C/[C@@H]1CCC[C@@H](S(N)(=O)=O)[C@H]1C)C[C@@]1(CCCc3cc(Cl)ccc31)CO2]

To a stirred solution of (S)-methyl 6'-chloro-5-(((1R,2R)-2-((S,E)-1-hydroxy-3-((1S,2S,3R)-2-methyl-3-(pyrimidin-2-ylsulfonyl)cyclohexyl)allyl)cyclobutyl)methyl)-3',4,4',5-tetrahydro-2H,2'H-spiro[benzo[b][1,4]oxazepine-3,1'-naphthalene]-7-carboxylate (the early-eluting diastereomer obtained in Step 4; 136 mg, 0.189 mmol) in MeOH (3776 µL) was added potassium carbonate (130 mg, 0.944 mmol), and the resulting mixture was stirred at rt for one hour and subsequently charged with a solution of hydroxylamine-O-sulfonic acid (27.8 mg, 0.245 mmol) in water (3 mL). The resulting mixture was heated at 50° C. for 90 minutes, cooled to room temperature, and partitioned between EtOAc and 1M HCl (aq.). The aqueous layer was extracted with DCM, and the combined organic extracts were dried over MgSO₄, filtered and concentrated in vacuo. Purification of the crude residue by column chromatography (24 g silica gel; hexanes:EtOAc, 1:0 to 3:1 solvent gradient) gave (S)-methyl 6'-chloro-5-(((1R,2R)-2-((E)-3-((1S,2S,3R)-2-methyl-3-sulfamoylcyclohexyl)acryloyl)cyclobutyl)methyl)-3',4,4',5-tetrahydro-2H,2'H-spiro[benzo[b][1,4]oxazepine-3,1'-naphthalene]-7-carboxylate (62 mg, 0.094 mmol, 50.0% yield).

Step 6: (S)-6'-chloro-5-(((1R,2R)-2-((S,E)-1-hydroxy-3-((1S,2S,3R)-2-methyl-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic Acid

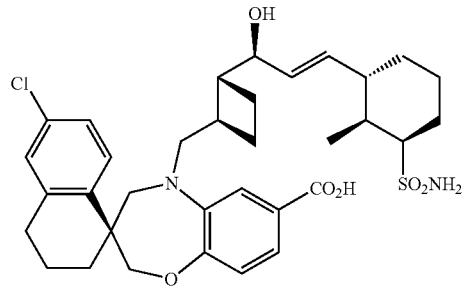 [SMILES: C[C@H]1[C@H](/C=C/[C@H](O)[C@@H]2CC[C@H]2CN2C[C@@]3(CCCc4cc(Cl)ccc43)COc3ccc(C(=O)O)cc32)CCC[C@H]1S(N)(=O)=O]

To a stirred solution of (S)-methyl 6'-chloro-5-(((1R,2R)-2-((E)-3-((1S,2S,3R)-2-methyl-3-sulfamoylcyclohexyl)acryloyl)cyclobutyl)methyl)-3',4,4',5-tetrahydro-2H,2'H-spiro[benzo[b][1,4]oxazepine-3,1'-naphthalene]-7-carboxylate (62 mg, 0.094 mmol) in THF (629 µL) and MeOH (629 µL) was added a solution of sodium hydroxide (18.9 mg, 0.472 mmol) in water (629 µL). The reaction mixture was stirred at 60° C. for three hours, cooled to rt and partitioned between DCM and 1M HCl (aq.). The aqueous layer was extracted with DCM, and the combined organic extracts were washed with brine, dried over MgSO₄, filtered and concentrated in vacuo to give (S)-6'-chloro-5-(((1R,2R)-2-((S,E)-1-hydroxy-3-((1S,2S,3R)-2-methyl-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic acid (40 mg, 0.062 mmol, 66% yield).

Step 7: (1S,3'R,6'R,7'S,8'E,10'S,14'R,28'S)-6-chloro-7'-hydroxy-28'-methyl-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide To a stirred solution of (S)-6'-chloro-5-(((1R,2R)-2-((S,E)-1-hydroxy-3-((1S,2S,3R)-2-methyl-3-sulfamoylcyclohexyl)allyl)cyclobutyl)methyl)-3',4,4',5-tetrahydro-2H,2'H-spiro[benzo[b][1,4]oxazepine-3,1'-naphthalene]-7-carboxylic acid (40 mg, 0.062 mmol) in DCM (3.11 E+04 µL) under a nitrogen atmosphere was added DMAP (12.9 mg, 0.106 mmol). The resulting solution was cooled to 0° C. and treated with EDC (23.84 mg, 0.124 mmol) portionwise over one minute. When the addition was complete, the cooling bath was removed and the reaction was stirred at rt overnight. On the following day, the reaction mixture was partitioned between DCM and 1M HCl (aq.), and the organic layer was washed with brine, dried over MgSO₄, filtered and concentrated in vacuo. Purification of the crude residue by column chromatography (4 g silica gel; DCM:Acetone, 1:0 to 9:1 solvent gradient) gave the desired compound (14 mg) along with ca. 5% of the (10'R,14'S,28'R) diastereomer. A second round of chromatography (4 g silica gel; DCM:Acetone, 1:0 to 9:1 gradient) furnished diastereopure (1S,3'R,6'R,7'S,8'E,10'S,14'R,28'S)-6-chloro-7'-hydroxy-28'-methyl-3,4-dihydro-2H,17'H-spiro[naphthalene-1,24'-[22]oxa[15]thia[1,16]diazapentacyclo[16.7.2.1$^{10,14}$.0$^{3,6}$.0$^{21,26}$]octacosa[8,18,20,26]tetraen]-17'-one 15',15'-dioxide (8.2 mg, 0.013 mmol, 21% yield) as a white solid. $^1$H NMR (500 MHz, CD$_2$Cl$_2$) δ ppm 8.14 (s, 1H), 7.71 (d, J=8.6 Hz, 1H), 7.17 (dd, J=8.4, 2.3 Hz, 1H), 7.09 (d, J=2.4 Hz, 1H), 6.88-6.96 (m, 3H), 5.94-6.02 (m, 1H), 5.77 (ddd, J=15.4, 6.8, 1.0 Hz, 1H), 4.38 (br. s., 1H), 4.30 (dt, J=12.9, 2.8 Hz, 1H), 4.09 (s, 2H), 3.85 (d, J=15.2 Hz, 1H), 3.70 (d, J=14.2 Hz, 1H), 3.25 (d, J=14.2 Hz, 1H), 3.04 (dd, J=15.4, 10.0 Hz, 1H), 2.70-2.84 (m, 2H), 2.41-2.50 (m, 1H), 2.29-2.40 (m, 2H), 2.10-2.19 (m, 1H), 1.90-2.07 (m, 5H), 1.65-1.90 (m, 8H), 1.54-1.63 (m, 1H), 1.37-1.52 (m, 3H), 1.20 (d, J=7.1 Hz, 3H). m/z (ESI, +ve ion) 624.8 (M+H)$^+$.

Example 113. (1S,3'R,6'S,7'E,9'R,11'S,12'R)-6-chloro-9'-(2-hydroxyethyl)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide

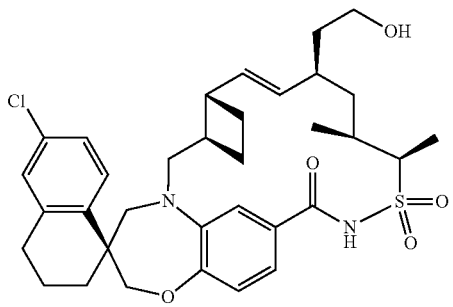 [SMILES: C[C@@H]1[C@@H](C)C[C@H](CCO)/C=C/[C@@H]2CC[C@H]2CN2C[C@@]3(CCCc4cc(Cl)ccc43)COc3ccc(cc32)C(=O)NS1(=O)=O]

N,N-diisopropylethylamine (21.2 μL, 0.122 mmol) was added to a stirred suspension of the macrocycle starting material (Example 192; 78.0 mg, 0.122 mmol) and BOP (53.8 mg, 0.122 mmol) in THF (2433 μL). The mixture was stirred at rt for 10 minutes, and then sodium borohydride (4.60 mg, 0.122 mmol) was added in one portion at rt. After 30 min, an additional portion of sodium borohydride (15 mg, 0.40 mmol) was added, and stirring at rt was continued for 30 minutes. A third portion of sodium borohydride (10 mg, 0.27 mmol) was then added, and, after a final 30 minutes of stirring, the mixture was partitioned between EtOAc and 1M HCl (aq.). The organic layer was sequentially washed with saturated sodium bicarbonate (aq.) and brine, dried over MgSO$_4$, filtered and concentrated in vacuo. Purification of the crude residue by column chromatography (4 g silica gel; DCM:Acetone, 1:0 to 4:1 solvent gradient) gave (1S,3'R,6'S,7'E,9'R,11'S,12'R)-6-chloro-9'-(2-hydroxyethyl)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide (76 mg, 0.121 mmol, 100% yield) as a white solid. $^1$H NMR (400 MHz, CD$_2$Cl$_2$) δ ppm 8.35 (br. s., 1H), 7.71 (d, J=8.6 Hz, 1H), 7.16 (dd, J=8.5, 2.2 Hz, 1H), 7.10 (d, J=2.2 Hz, 1H), 6.82-7.03 (m, 3H), 5.79 (d, J=12.5 Hz, 1H), 5.13 (dd, J=15.5, 7.8 Hz, 1H), 4.10-4.20 (m, 2H), 3.52-3.83 (m, 4H), 3.03-3.29 (m, 2H), 2.71-2.84 (m, 2H), 2.55 (br. s., 1H), 2.14-2.27 (m, 2H), 1.95-2.09 (m, 1H), 1.74-1.94 (m, 4H), 1.36-1.71 (m, 11H), 1.22-1.34 (m, 1H), 0.97 (d, J=6.8 Hz, 3H). m/z (ESI, +ve ion) 626.8 (M+H)$^+$.

Example 114. (1S,3'R,6'S,7'E,9'R,11'S,12'R)-6-chloro-9'-(2-methoxyethyl)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide

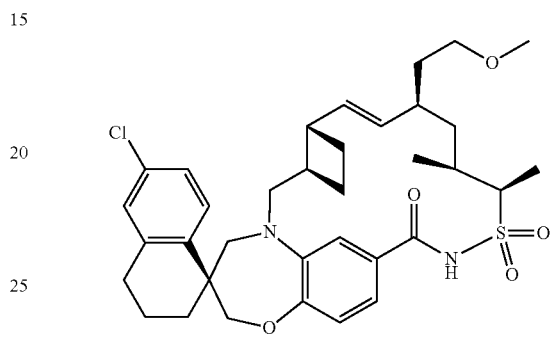

To a stirred solution of (1S,3'R,6'S,7'E,9'R,11'S,12'R)-6-chloro-9'-(2-hydroxyethyl)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide (Example 113; 16 mg, 0.026 mmol) in THF (1020 μL) under a nitrogen atmosphere was added sodium hydride (60% dispersion in mineral oil; 5.10 mg, 0.128 mmol). The reaction mixture was stirred at rt for 10 minutes, charged with iodomethane (7.98 μL, 0.128 mmol) and stirred at rt over the weekend. The reaction mixture was then partitioned between EtOAc and water, and the organic layer was dried over MgSO$_4$, filtered and concentrated in vacuo. Purification of the crude residue by column chromatography (4 g silica gel; DCM:Acetone, 1:0 to 3:1 solvent gradient) gave (1S,3'R,6'S,7'E,9'R,11'S,12'R)-6-chloro-9'-(2-methoxyethyl)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide (5.7 mg, 8.9 μmol, 35% yield) as a white solid. $^1$H NMR (400 MHz, CD$_2$Cl$_2$) δ ppm 8.07 (br. s., 1H), 7.72 (d, J=8.6 Hz, 1H), 7.17 (dd, J=8.5, 2.2 Hz, 1H), 7.09 (d, J=2.2 Hz, 1H), 6.95-7.04 (m, 2H), 6.89-6.94 (m, 1H), 5.81 (dd, J=15.4, 4.8 Hz, 1H), 5.16 (dd, J=15.7, 7.3 Hz, 1H), 4.09-4.17 (m, 2H), 3.83 (d, J=15.1 Hz, 1H), 3.63 (d, J=14.1 Hz, 1H), 3.32 (td, J=6.7, 1.6 Hz, 2H), 3.28 (s, 3H), 3.20 (d, J=14.1 Hz, 1H), 3.07 (dd, J=15.5, 8.2 Hz, 1H), 2.69-2.83 (m, 2H), 2.51-2.62 (m, 1H), 2.13-2.24 (m, 2H), 1.94-2.07 (m, 1H), 1.72-1.94 (m, 4H), 1.37-1.70 (m, 11H), 1.30 (br. s., 1H), 0.96 (d, J=6.8 Hz, 3H). m/z (ESI, +ve ion) 640.8 (M+H)$^+$.

Example 115. (1S,3'R,6'S,7'E,9'R,11'S,12'R)-6-chloro-11',12'-dimethyl-9'-(2-(4-morpholinyl)ethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide

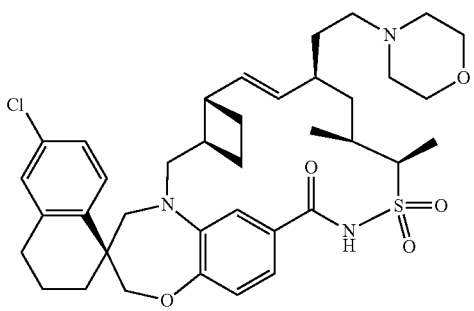 [SMILES: C[C@@H]1[C@@H](C)C[C@H](CCN2CCOCC2)/C=C/[C@@H]2CC[C@H]2CN2C[C@@]3(CCCc4cc(Cl)ccc43)COc3ccc(cc32)C(=O)NS1(=O)=O]

Step 1: (1S,3'R,6'S,7'E,9'R,11'S,12'R)-6-chloro-9'-formylmethyl-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide

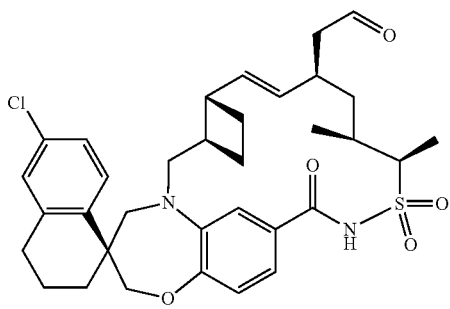 [SMILES: C[C@@H]1[C@@H](C)C[C@H](CC=O)/C=C/[C@@H]2CC[C@H]2CN2C[C@@]3(CCCc4cc(Cl)ccc43)COc3ccc(cc32)C(=O)NS1(=O)=O]

To a stirred solution of (1S,3'R,6'S,7'E,9'R,11'S,12'R)-6-chloro-9'-(2-hydroxyethyl)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide (20 mg, 0.032 mmol; Example 113) in DCM (1275 µL) was added Dess-Martin periodinane (17.6 mg, 0.041 mmol) in one portion, and the reaction mixture was stirred at rt for 40 minutes. After this time, ether and saturated sodium thiosulfate (aq.) were added and the resulting mixture was stirred at rt for 10 minutes. The layers were separated and the organic layer was washed sequentially with saturated sodium thiosulfate (aq.) and saturated sodium bicarbonate (aq.), dried over MgSO$_4$, filtered and concentrated in vacuo to give (1S,3'R,6'S,7'E,9'R,11'S,12'R)-6-chloro-9'-formylmethyl-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide (9.0 mg, 0.014 mmol, 45.1% yield).

Step 2: (1S,3'R,6'S,7'E,9'R,11'S,12'R)-6-chloro-11',12'-dimethyl-9'-(2-(4-morpholinyl)ethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide To a stirred solution of (1S,3'R,6'S,7'E,9'R,11'S,12'R)-6-chloro-9'-formylmethyl-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide (9.0 mg, 0.014 mmol) in 1,2-dichloroethane (720 µL) was added morpholine (3.8 µL, 0.043 mmol), and the resulting solution was stirred at rt for one hour. Sodium triacetoxyborohydride (9.1 mg, 0.043 mmol) was then added in one portion, and the reaction mixture was stirred at rt for two hours and subsequently partitioned between DCM and water. The organic layer was dried over MgSO$_4$, filtered and concentrated in vacuo. Purification of the crude residue by column chromatography (4 g silica gel; DCM:acetone, 1:0 to 1:1 solvent gradient) gave (1S,3'R,6'S,7'E,9'R,11'S,12'R)-6-chloro-11',12'-dimethyl-9'-(2-(4-morpholinyl)ethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide (1.45 mg, 2.08 µmol, 14% yield) as a white solid. $^1$H NMR (400 MHz, CD$_2$Cl$_2$) δ ppm 7.72 (d, J=8.4 Hz, 1H), 7.16 (dd, J=8.5, 2.4 Hz, 1H), 7.01-7.11 (m, 3H), 6.90 (d, J=8.0 Hz, 1H), 5.78 (dd, J=15.6, 5.2 Hz, 1H), 5.18 (dd, J=15.9, 8.3 Hz, 1H), 4.07-4.15 (m, 2H), 4.00 (br. s., 1H), 3.81 (d, J=15.5 Hz, 1H), 3.73 (t, J=4.6 Hz, 4H), 3.63 (d, J=14.5 Hz, 1H), 3.22 (d, J=14.3 Hz, 1H), 3.06 (dd, J=15.3, 8.4 Hz, 1H), 2.73-2.79 (m, 2H), 2.33-2.58 (m, 8H), 2.09-2.29 (m, 3H), 1.95-2.03 (m, 2H), 1.75-1.94 (m, 5H), 1.60-1.68 (m, 1H), 1.41-1.50 (m, 4H), 1.37 (d, J=7.0 Hz, 3H), 0.97 (d, J=6.8 Hz, 3H). m/z (ESI, +ve ion) 696.3 (M+H)$^+$.

Example 116. (1S,3'R,6'R,7'S,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'R,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'S,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'R,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

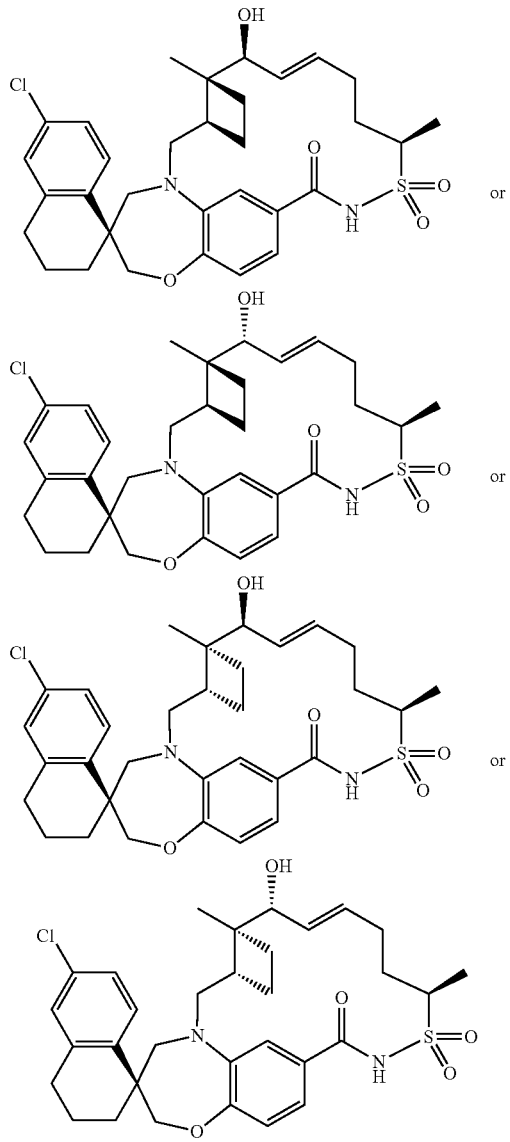

Step 1: (1R,2R)-methyl 2-((tert-butyldiphenylsilyl)methyl)-1-methylcyclobutanecarboxylate and (1S,2S)-methyl 2-((tert-butyldiphenylsilyl)methyl)-1-methylcyclobutanecarboxylate

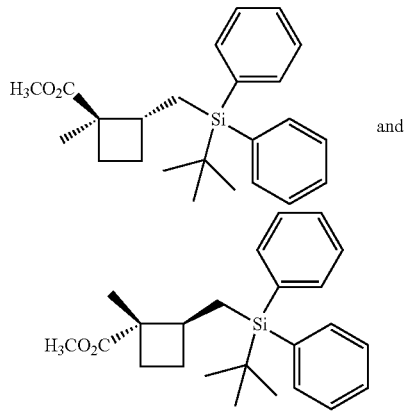

A solution of methyl methacrylate (17.66 mL, 166 mmol) in DCM (80 mL) was added to a stirred solution of titanium (IV) chloride (19.20 mL, 174 mmol) in DCM (160 mL). A solution of allyl (tert-butyl) diphenylsilane (67.4 g, 240 mmol) in DCM (80 mL) was then added and the reaction was heated at reflux for 2 days. After this time the reaction was cooled to ambient temperature and poured into NaHCO$_3$ (saturated aqueous solution) and ice. NH$_4$Cl (saturated aqueous solution) was then added, the organic layer was separated, and the aqueous layer was extracted with DCM (×2). The combined organic extracts were filtered over celite. The filtrate was dried over MgSO$_4$, filtered and evaporated in vacuo. The residue was adsorbed in a plug of Sift (65 g) and purified by column chromatography (330 g SiO$_2$, hexanes:EtOAc, 1:0 to 20:1) to provide (1R,2R)-methyl 2-((tert-butyldiphenylsilyl)methyl)-1-methylcyclobutanecarboxylate and (1S,2S)-methyl 2-((tert-butyldiphenylsilyl)methyl)-1-methylcyclobutanecarboxylate (46.9 g, 123 mmol, 74%). m/z (ESI, +ve ion) 627.1 (M+H)$^+$.

Step 2: (1R,2R)-methyl 2-((tert-butyldifluorosilyl)methyl)-1-methylcyclobutanecarboxylate and (1S,2S)-methyl 2-((tert-butyldifluorosilyl)methyl)-1-methylcyclobutanecarboxylate

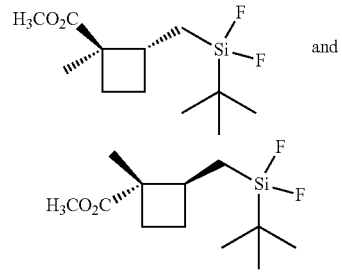

To a stirred solution of (1R,2R)-methyl 2-((tert-butyldiphenylsilyl)methyl)-1-methylcyclobutanecarboxylate and (1S,2S)-methyl 2-((tert-butyldiphenylsilyl)methyl)-1-methylcyclobutanecarboxylate (46.9 g, 123 mmol) in DCM (616 mL) was added boron trifluoride acetic acid complex (86 mL, 616 mmol). The reaction was heated at reflux overnight. After this time the reaction was cooled to ambient temperature and poured into ice/NaHCO₃. The separated organic layer was dried over MgSO₄, filtered and evaporated in vacuo to give (1R,2R)-methyl 2-((tert-butyldifluorosilyl)methyl)-1-methylcyclobutanecarboxylate and (1S,2S)-methyl 2-((tert-butyldifluorosilyl)methyl)-1-methylcyclobutanecarboxylate (29.6 g, 112 mmol, 91% yield).

Step 3: (1R,2R)-methyl 2-(hydroxymethyl)-1-methylcyclobutanecarboxylate and (1S,2S)-methyl 2-(hydroxymethyl)-1-methylcyclobutanecarboxylate

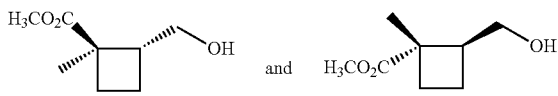

To a stirred solution of (1R,2R)-methyl 2-((tert-butyldifluorosilyl)methyl)-1-methylcyclobutanecarboxylate and (1S,2S)-methyl 2-((tert-butyldifluorosilyl)methyl)-1-methylcyclobutanecarboxylate (29.6 g, 112 mmol) in THF/MeOH (300 mL/300 mL) was added potassium fluoride (19.51 g, 336 mmol) and sodium bicarbonate (9.41 g, 112 mmol) and the reaction was cooled to 0° C. A 30% aqueous solution of hydrogen peroxide (57.2 mL, 560 mmol) was then added dropwise via addition funnel over 15 minutes. After this time the reaction was allowed to warm to ambient temperature and stirred overnight. After this time the reaction was treated with Et₂O, cooled to 0° C. and treated with a saturated aqueous solution of Na₂SO₃. The separated organic layer was washed with Na₂SO₃ (sat aq solution; until organic layer tested negative with starch paper), dried over MgSO₄, filtered and evaporated in vacuo. The resulting residue was adsorbed in a 80 g pre-pack silica cartridge and then purified by column chromatography (330 g SiO₂, hexanes:EtOAc, 1:0 to 4:1) to give (1R,2R)-methyl 2-(hydroxymethyl)-1-methylcyclobutanecarboxylate and (1S,2S)-methyl 2-(hydroxymethyl)-1-methylcyclobutanecarboxylate (7.3 g, 46.18 mmol, 41.2% yield).

Step 4: (1R,2R)-methyl 2-formyl-1-methylcyclobutanecarboxylate and (1S,2S)-methyl 2-formyl-1-methylcyclobutanecarboxylate

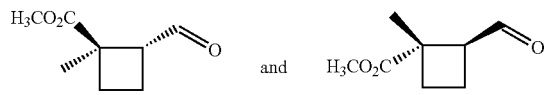

To a stirred solution of (1R,2R)-methyl 2-(hydroxymethyl)-1-methylcyclobutanecarboxylate (2.5 g, 15.80 mmol) and (1S,2S)-methyl 2-formyl-1-methylcyclobutanecarboxylate in DCM (79 mL) was added Dess-Martin periodinane (8.04 g, 18.96 mmol) in one portion. The reaction was stirred at ambient temperature for 30 minutes. After this time the reaction was diluted with Et₂O (100 mL) and treated with Na₂S₂O₃ (saturated aqueous solution). The separated organic layer was dried over MgSO₄, filtered and carefully evaporated in vacuo. Column chromatography (24 g SiO₂, Pentane:Et₂O (1:0 to 5:1) gave (1R,2R)-methyl 2-formyl-1-methylcyclobutanecarboxylate and (1S,2S)-methyl 2-formyl-1-methylcyclobutanecarboxylate (1.3 g, 8.333 mmol, 53% yield) as a colorless liquid.

Step 5: (S)-tert-butyl 6'-chloro-5-(((1R,2R)-2-(methoxycarbonyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-(methoxycarbonyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2R)-2-(methoxycarbonyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1R,2S)-2-(methoxycarbonyl)-2-methylcyclobutyl)methyl)-3',4,4',5-tetrahydro-2H,2'H-spiro[benzo[b][1,4]oxazepine-3,1'-naphthalene]-7-carboxylate

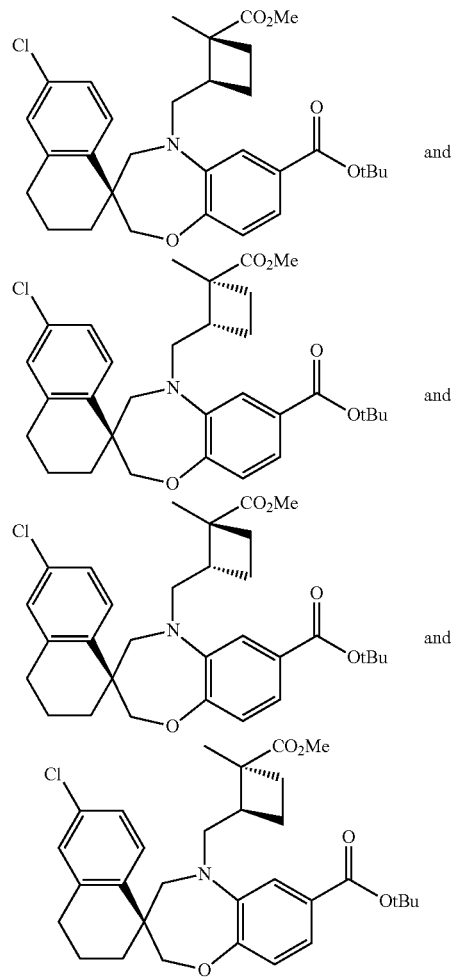

A solution of (5)-tert-butyl 6'-chloro-3',4,4',5-tetrahydro-2H,2'H-spiro[benzo[b][1,4]oxazepine-3,1'-naphthalene]-7-carboxylate (Intermediate AA11A, Step 12B; 2 g, 5.00 mmol) and (1R,2R)-methyl 2-formyl-1-methylcyclobutanecarboxylate and (1S,2S)-methyl 2-formyl-1-methylcyclobutanecarboxylate (1.172 g, 7.50 mmol) in CH₂Cl₂ (33.3 mL) and AcOH (16.67 mL) was stirred at ambient temperature for 20 minutes. After this time the reaction was cooled to 0° C. and treated with a solution of sodium cyanoborohydride (0.126 g, 2.00 mmol) in THF (3 mL) dropwise via syringe pump for 2 hours. The reaction was stirred at ambient temperature overnight. After this time the reaction was partitioned between EtOAc and aq NaOH. The separated aqueous layer was extracted with DCM and the combined organic extracts were dried over MgSO₄, filtered and evaporated in vacuo. Column chromatography (40 g SiO₂, hexanes:EtOAc (containing 1% AcOH), 1:0 to 9:1) gave (S)-tert-butyl 6'-chloro-5-(((1R,2R)-2-(methoxycarbonyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-(methoxycarbonyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2R)-2-(methoxycarbonyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1R,2S)-2-(methoxycarbonyl)-2-methylcyclobutyl)methyl)-3',4,4',5-tetrahydro-2H,2'H-spiro[benzo[b][1,4]oxazepine-3,1'-naphthalene]-7-carboxylate (2.15 g, 3.98 mmol, 80% yield) as a white solid.

Step 6: (S)-tert-butyl 6'-chloro-5-(((1R,2R)-2-(hydroxymethyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-(hydroxymethyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2R)-2-(hydroxymethyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1R,2S)-2-(hydroxymethyl)-2-methylcyclobutyl)methyl)-3',4,4',5-tetrahydro-2H,2'H-spiro[benzo[b][1,4]oxazepine-3,1'-naphthalene]-7-carboxylate

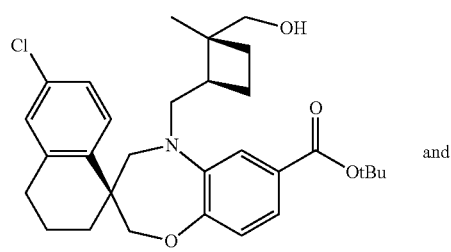 and

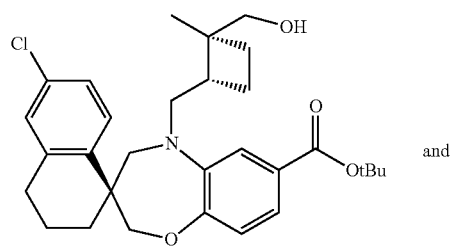 and

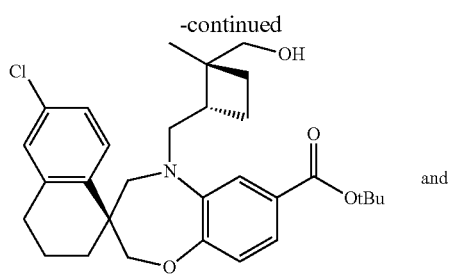 and

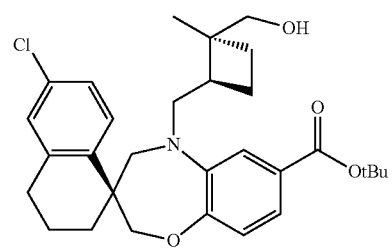

To a stirred solution of (S)-tert-butyl 6'-chloro-5-(((1R,2R)-2-(methoxycarbonyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-(methoxycarbonyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2R)-2-(methoxycarbonyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1R,2S)-2-(methoxycarbonyl)-2-methylcyclobutyl)methyl)-3',4,4',5-tetrahydro-2H,2'H-spiro[benzo[b][1,4]oxazepine-3,1'-naphthalene]-7-carboxylate (2.15 g, 3.98 mmol) in Et₂O (80 mL) was added lithium borohydride (0.087 g, 3.98 mmol). The reaction was stirred at ambient temperature for 4 hours. After this time the reaction was diluted with EtOAc and quenched by the careful addition of NH₄Cl (sat aq solution). The separated aqueous layer was extracted with EtOAc and the combined organic extracts were dried over MgSO₄, filtered and evaporated in vacuo. Column chromatography (80 g SiO₂, hexanes:EtOAc (containing 1% AcOH), 1:0 to 9:1) gave a 1:1 mixture of (S)-tert-butyl 6'-chloro-5-(((1R,2R)-2-(hydroxymethyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-(hydroxymethyl)-2-methylcyclobutyl)methyl)-3',4,4',5-tetrahydro-2H,2'H-spiro[benzo[b][1,4]oxazepine-3,1'-naphthalene]-7-carboxylate as the first eluting major component (0.95 g).

Further elution provided a 1:1 mixture of (S)-tert-butyl 6'-chloro-5-(((1S,2R)-2-(hydroxymethyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1R,2S)-2-(hydroxymethyl)-2-methylcyclobutyl)methyl)-3',4,4',5-tetrahydro-2H,2'H-spiro[benzo[b][1,4]oxazepine-3,1'-naphthalene]-7-carboxylate as the second eluting minor component (0.42 g).

Step 7: (S)-tert-butyl 6'-chloro-5-(((1R,2R)-2-formyl-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-formyl-2-methylcyclobutyl)methyl)-3',4,4',5-tetrahydro-2H,2'H-spiro[benzo[b][1,4]oxazepine-3,1'-naphthalene]-7-carboxylate Step 8: (5)-tert-butyl 6'-chloro-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate

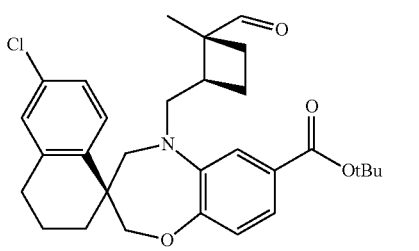

and

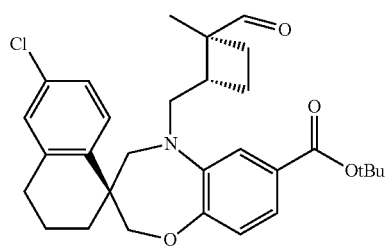

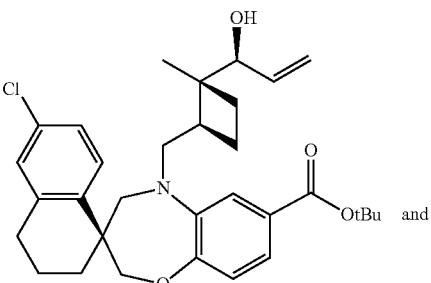

and

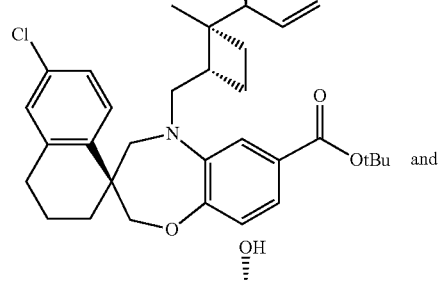

and

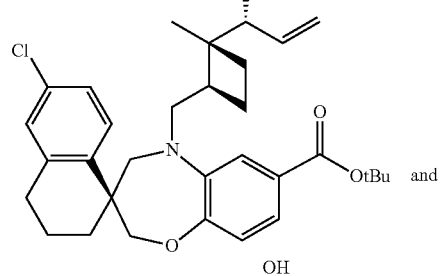

and

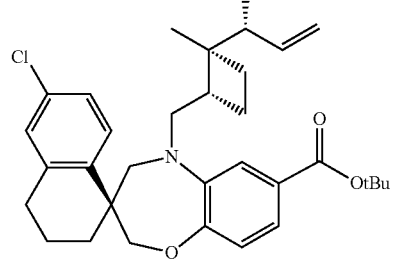

To a stirred solution of (5)-tert-butyl 6'-chloro-5-(((1R,2R)-2-(hydroxymethyl)-2-methylcyclobutyl)methyl)-3',4,4',5-tetrahydro-2H,2'H-spiro[benzo[b][1,4]oxazepine-3,1'-naphthalene]-7-carboxylate and (5)-tert-butyl 6'-chloro-5-(((1S,2S)-2-(hydroxymethyl)-2-methylcyclobutyl)methyl)-3',4,4',5-tetrahydro-2H,2'H-spiro[benzo[b][1,4]oxazepine-3,1'-naphthalene]-7-carboxylate (Step 6, first eluting major component; 0.98 g, 1.914 mmol) in CH$_2$Cl$_2$ (19.14 mL) at rt was added Dess-Martin periodinane (0.893 g, 2.105 mmol) in one portion. The reaction was stirred at ambient temperature for 30 minutes. After this time the reaction was partitioned between Et$_2$O and Na$_2$S$_2$O$_3$ (sat aq solution). The separated organic layer was dried over MgSO$_4$, filtered and evaporated in vacuo. Column chromatography (24 g SiO$_2$, hexanes:EtOAc, 1:0 to 5:1) gave (5)-tert-butyl 6'-chloro-5-(((1R,2R)-2-formyl-2-methylcyclobutyl)methyl)-3',4,4',5-tetrahydro-2H,2'H-spiro[benzo[b][1,4]oxazepine-3,1'-naphthalene]-7-carboxylate and (5)-tert-butyl 6'-chloro-5-(((1S,2S)-2-formyl-2-methylcyclobutyl)methyl)-3',4,4',5-tetrahydro-2H,2'H-spiro[benzo[b][1,4]oxazepine-3,1'-naphthalene]-7-carboxylate (0.85 g, 1.666 mmol, 87% yield) as a white solid.

To a stirred solution of (S)-tert-butyl 6'-chloro-5-(((1R,2R)-2-formyl-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-

2-formyl-2-methylcyclobutyl)methyl)-3',4,4',5-tetrahydro-2H,2'H-spiro[benzo[b][1,4]oxazepine-3,1'-naphthalene]-7-carboxylate (570 mg, 1.118 mmol) in THF (11.2 mL) at 0° C. under a N₂ atmosphere was added a 1M solution of vinylmagnesium bromide (838 µL, 1.341 mmol) in THF. The reaction was stirred at this temperature for 30 minutes and at ambient temperature for 2 hours. After this time the reaction was partitioned between EtOAc and NH₄Cl. The separated organic layer was dried over MgSO₄, filtered and evaporated in vacuo. Column chromatography (12 g SiO₂, hexanes:EtOAc (containing 1% AcOH), 1:0 to 85:15) gave (S)-tert-butyl 6'-chloro-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate or (S)-tert-butyl 6'-chloro-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate as the first eluting major component (200 mg). Further elution provided (S)-tert-butyl 6'-chloro-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate or (S)-tert-butyl 6'-chloro-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate as the second eluting minor component (80 mg).

Step 9: (S)-6'-chloro-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic Acid

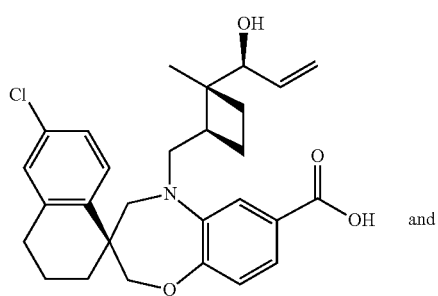

A solution of (S)-tert-butyl 6'-chloro-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate or (S)-tert-butyl 6'-chloro-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate (Example 116, Step 8, first eluting major isomer; 200 mg, 0.372 mmol) in CH₂Cl₂ (2.5 mL) and TFA (1.2 mL) was stirred at ambient temperature for 4 hours. After this time the reaction was evaporated in vacuo. The resulting residue was partitioned between DCM and NaHCO₃. The separated organic layer was dried over MgSO₄, filtered and evaporated in vacuo to give (S)-6'-chloro-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2S)-2-((R)-1-hydroxyallyl)-2-methylcyclobutyl)methyl)-3', 4,4',5-tetrahydro-2H,2'H-spiro[benzo[b][1,4]oxazepine-3,1'-naphthalene]-7-carboxylic acid (180 mg, 0.373 mmol, 100% yield).

Step 10: (S)-6'-chloro-N—((R)-hex-5-en-2-ylsulfonyl)-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-EN-2-ylsulfonyl)-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide or (S)-6'-chloro-N—((R)-hex-5-en-2-ylsulfonyl)-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-en-2-ylsulfonyl)-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide

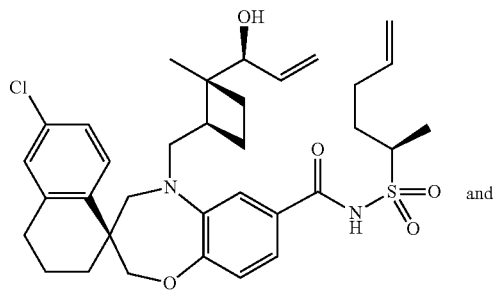

and

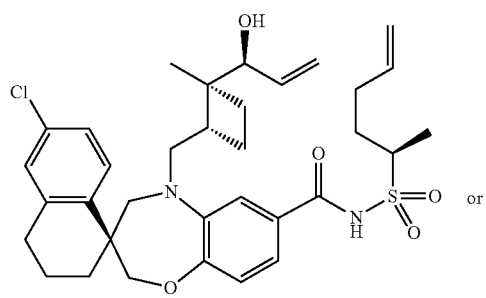

or

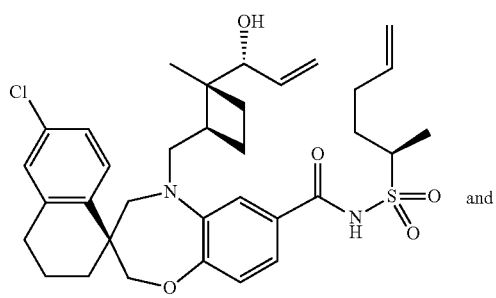

and

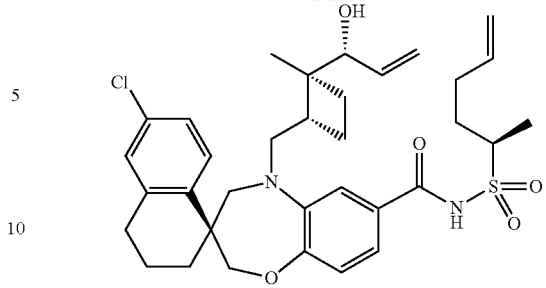

To a stirred solution of (S)-6'-chloro-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid (105 mg, 0.218 mmol), (R)-hex-5-ene-2-sulfonamide (Intermediate EE20; 107 mg, 0.654 mmol), DMAP (39.9 mg, 0.327 mmol) and triethylamine (60.7 µL, 0.436 mmol) at 0° C. under a N$_2$ atmosphere was added EDC (84 mg, 0.436 mmol) portionwise over 1 minute. The reaction was stirred at ambient temperature overnight. After this time the reaction was treated with more EDC (42 mg), DMAP (20 mg), Et$_3$N (0.03 mL) and chiral sulfonamide (50 mg) and the reaction was stirred at ambient temperature for 24 hours. After this time the reaction was partitioned between EtOAc and NaHCO$_3$. The separated organic layer was dried over MgSO$_4$, filtered and evaporated in vacuo. Column chromatography (12 g hexanes:EtOAc (containing 1% AcOH, 1:0 to 4:1) gave (S)-6'-chloro-N—((R)-hex-5-en-2-ylsulfonyl)-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-en-2-ylsulfonyl)-5-(((1S,2S)-2-((S)-1-hydroxy allyl)-2-methylcyclobutyl)methyl)-3',4,4',5-tetrahydro-2H,2'H-spiro[benzo[b][1,4]oxazepine-3,1'-naphthalene]-7-carboxamide or (S)-6'-chloro-N—((R)-hex-5-en-2-ylsulfonyl)-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-en-2-ylsulfonyl)-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide as the first eluting major component (29 mg).

Further elution provided (S)-6'-chloro-N—((R)-hex-5-en-2-ylsulfonyl)-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-en-2-ylsulfonyl)-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide or (S)-6'-chloro-N—((R)-hex-5-en-2-ylsulfonyl)-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-en-2-ylsulfonyl)-5-(((1S, 2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide as the first eluting major component (27 mg).

Step 11: (1S,3'R,6'R,7'S,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'R,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'S,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'R,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide A stirred solution of (S)-6'-chloro-N—((R)-hex-5-en-2-ylsulfonyl)-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-en-2-ylsulfonyl)-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide or (S)-6'-chloro-N—((R)-hex-5-en-2-ylsulfonyl)-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-en-2-ylsulfonyl)-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide (Example 116, Step 10, second eluting isomer; 27 mg, 0.043 mmol) in CH$_2$Cl$_2$ (21.5 mL) was degassed with Ar(g) for 10 minutes. After this time the reaction was heated at reflux for 3 hours. LC/MS after this time shows starting material and only a few traces of desired product. The reaction was then treated with 0.15 eq of a different bottle of Hoveyda Grubbs 2nd generation and stirring continued at reflux for 6 hours and at 40° C. (oil bath) overnight. After this time the reaction was cooled to ambient temperature and the catalyst was deactivated by sparging air through the mixture for 5 minutes. The reaction was evaporated in vacuo and the product was purified by column chromatography (4 g SiO$_2$, hexanes:EtOAc (containing 1% AcOH), 1:0 to 3:1) to give (1S,3'R,6'R,7'S,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'R,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'S,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'R,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (3.2 mg, 5.34 µmol, 12.41% yield). $^1$H NMR (400 MHz, MeOH-d4) δ 7.72 (d, J=8.6 Hz, 1H), 7.17 (dd, J=2.3, 8.6 Hz, 1H), 7.10 (d, J=2.2 Hz, 1H), 6.98 (dd, J=2.0, 8.4 Hz, 1H), 6.91 (d, J=8.2 Hz, 1H), 6.80 (d, J=2.0 Hz, 1H), 5.86 (td, J=6.7, 15.1 Hz, 1H), 5.76 (dd, J=7.4, 15.7 Hz, 1H), 4.21-4.12 (m, 1H), 4.10-4.02 (m, 2H), 3.91 (d, J=7.4 Hz, 1H), 3.78 (d, J=15.3 Hz, 1H), 3.66 (d, J=14.7 Hz, 1H), 3.24 (d, J=14.3 Hz, 1H), 3.11 (dd, J=10.8, 15.1 Hz, 1H), 2.87-2.70 (m, 2H), 2.50-2.41 (m, 1H), 2.41-2.32 (m, 1H), 2.22 (dd, J=6.3, 9.8 Hz, 1H), 2.09 (d, J=13.5 Hz, 1H), 1.98-1.85 (m, 5H), 1.77-1.65 (m, 1H), 1.47 (d, J=7.0 Hz, 3H), 1.46-1.42 (m, 1H), 1.41-1.32 (m, 2H), 1.31 (s, 3H). MS (ESI, +ve ion) m/z 599.2 (M+H)$^+$.

Example 117. (1S,3'R,6'R,7'S,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-1S-one 13',13'-dioxide or (1S,3'R,6'R,7'R,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'S,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'R,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

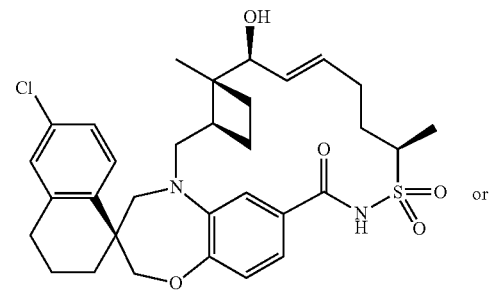

or

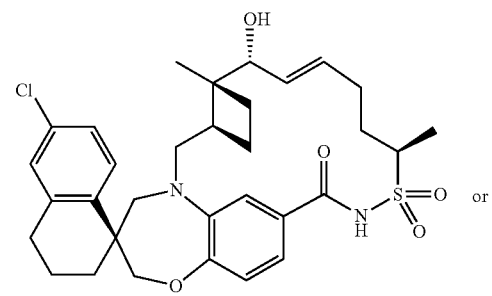

or

323

-continued

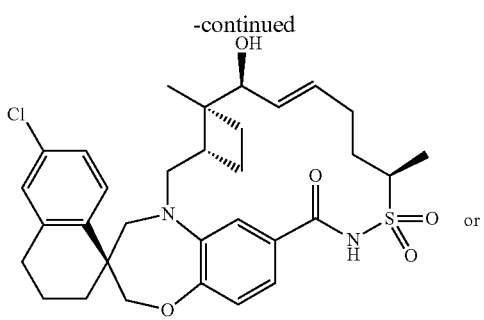

or

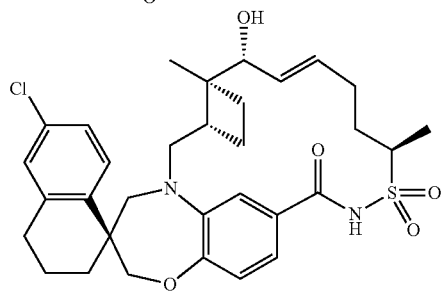

Step 1: (S)-6'-chloro-5-((((1R,2R)-2-((S)-1-hydroxy-allyl)-2-methylcyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-((((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic Acid

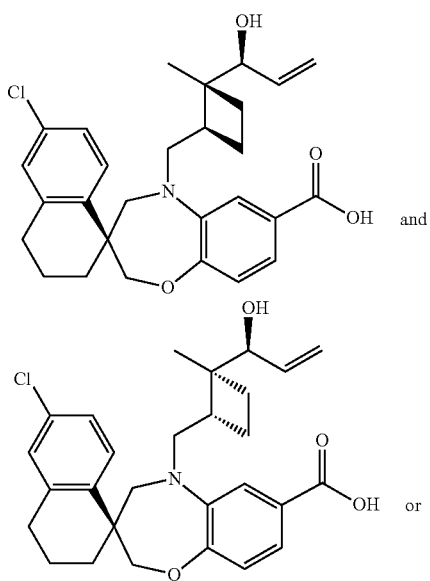

324

-continued

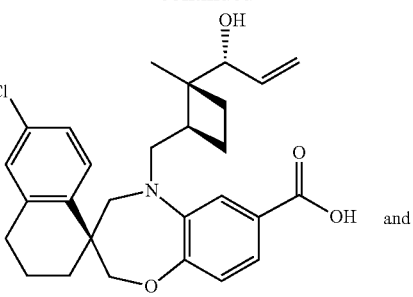

and

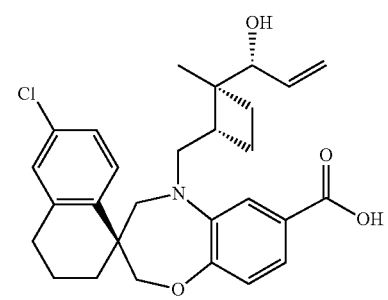

The title compounds were synthesized from (S)-tert-butyl 6'-chloro-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate or (S)-tert-butyl 6'-chloro-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylate (Example 116, Step 8, second eluting minor isomer; 80 mg, 0.149 mmol) following the procedure described for Example 116, Step 9. After aqueous workup, the isolated crude mixture of (S)-6'-chloro-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid (55 mg, 0.114 mmol, 77% yield) was taken on without further purification.

Step 2: (S)-6'-chloro-N—((R)-hex-5-en-2-ylsulfonyl)-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-S-EN-2-ylsulfonyl)-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide or (S)-6'-chloro-N—((R)-hex-5-en-2-ylsulfonyl)-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-en-2-ylsulfonyl)-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide

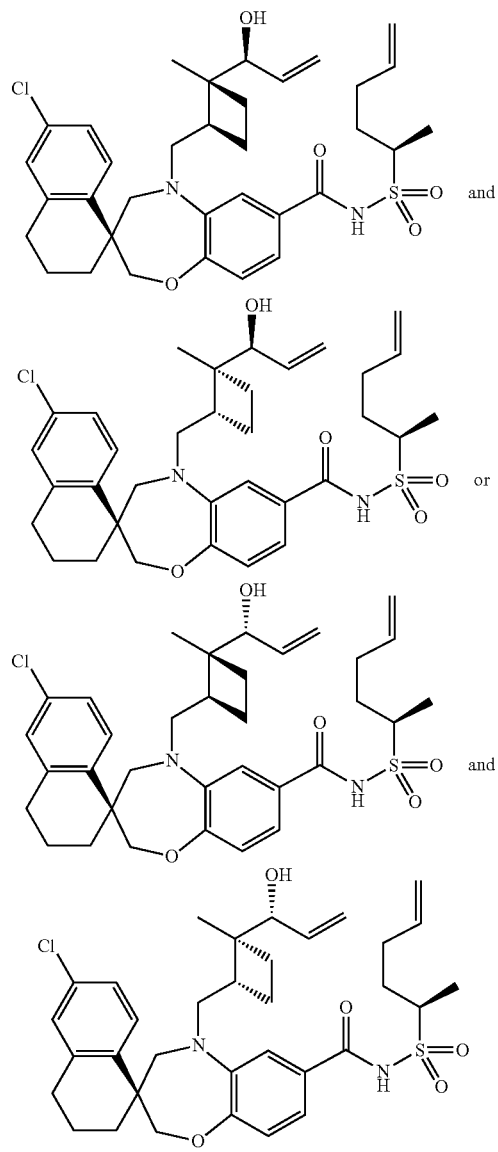

The title compounds were synthesized from (S)-6'-chloro-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid (55 mg, 0.114 mmol) and (R)-hex-5-ene-2-sulfonamide (Intermediate EE20; 56 mg, 0.342 mmol) following the procedure described for Example 116, Step 10. Column chromatography (12 g SiO$_2$, hexanes:EtOAc (containing 1% AcOH)) gave (S)-6'-chloro-N—((R)-hex-5-en-2-ylsulfonyl)-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-en-2-ylsulfonyl)-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide or (S)-6'-chloro-N—((R)-hex-5-en-2-ylsulfonyl)-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-en-2-ylsulfonyl)-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide as the first eluting major component (40 mg, 0.064 mmol, 56% yield).

Step 3: (1S,3'R,6'R,7'S,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'R,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'S,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'R,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide The title compound was synthesized from (S)-6'-chloro-N—((R)-hex-5-en-2-ylsulfonyl)-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-en-2-ylsulfonyl)-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide or (S)-6'-chloro-N—((R)-hex-5-en-2-ylsulfonyl)-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-en-2-ylsulfonyl)-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3, 1'-naphthalene]-7-carboxamide (40 mg, 0.064 mmol) following the procedure described for Example 116, Step 11. The reaction was evaporated in vacuo and the product was purified by column chromatography (4 g SiO$_2$, hexanes: EtOAc (containing 1% AcOH), 1:0 to 5:1) to give (1S,3'R, 6'R,7'S,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'R,8'E,12'R)-6-chloro-7'-hydroxy-6',12'-dimethyl-3,4-dihydro-2H, 15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'S,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'R,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as the first eluting major isomer (5.0 mg, 8.34 μmol, 13.09% yield). $^1$H NMR (400 MHz, MeOH-d4) δ 7.73 (d, J=8.4 Hz, 1H), 7.34 (d, J=2.0 Hz, 1H), 7.15 (dd, J=2.3, 8.4 Hz, 1H), 7.09 (d, J=2.2 Hz, 1H), 6.99 (dd, J=2.2, 8.2 Hz, 1H), 6.91 (d, J=7.8 Hz, 1H), 5.87 (td, J=5.1, 15.6 Hz, 1H), 5.73 (dd, J=6.3, 15.7 Hz, 1H), 4.19-4.10 (m, 1H), 4.09-4.03 (m, 2H), 3.94 (d, J=15.1 Hz, 1H), 3.75 (d, J=6.1 Hz, 1H), 3.62 (d, J=14.3 Hz, 1H), 3.20 (d, J=14.1 Hz, 1H), 3.02 (dd, J=10.7, 15.0 Hz, 1H), 2.85-2.71 (m, 2H), 2.70-2.61 (m, 1H), 2.44-2.32 (m, 1H), 2.25-2.15 (m, 1H), 2.13-2.02 (m, 2H), 1.97-1.84 (m, 3H), 1.84-1.78 (m, 1H), 1.77-1.65 (m, 3H), 1.44 (d, J=7.0 Hz, 3H), 1.47-1.38 (m, 1H), 1.30 (s, 3H). MS (ESI, +ve ion) m/z 599.2 (M+H)$^+$.

Example 118. (1S,3'R,6'R,7'S,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'R, 8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S, 7'R,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

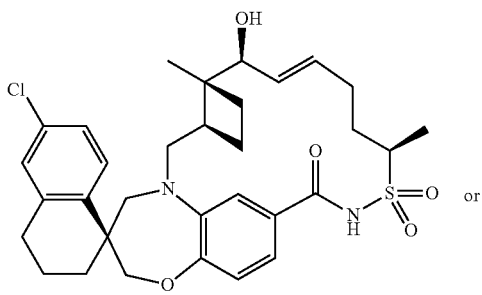

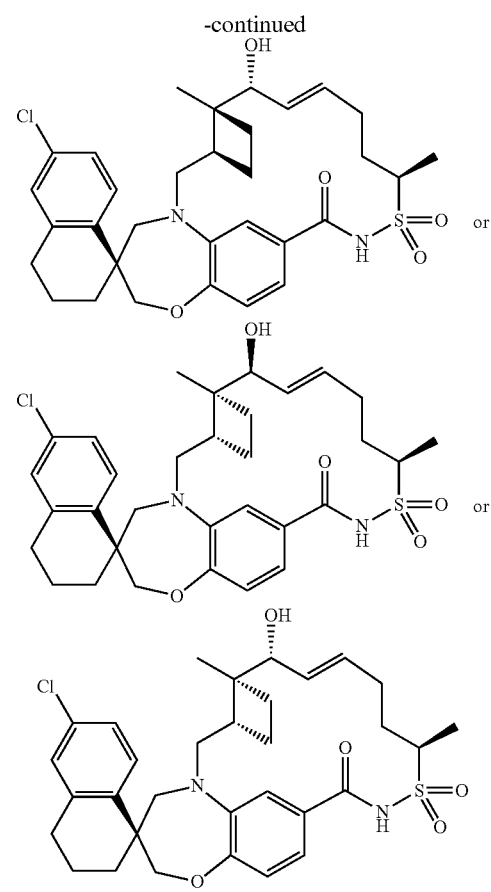

The title compound was synthesized from (S)-6'-chloro-N—((R)-hex-5-en-2-ylsulfonyl)-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-en-2-ylsulfonyl)-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide or (S)-6'-chloro-N—((R)-hex-5-en-2-ylsulfonyl)-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-en-2-ylsulfonyl)-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide (Example 117, Step 2; 40 mg, 0.064 mmol) following the procedure described for Example 116, Step 11. The reaction was evaporated in vacuo and the product was purified by column chromatography (4 g SiO$_2$, hexanes:EtOAc (containing 1% AcOH), 1:0 to 5:1) to give (1S,3'R,6'R,7'S,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S, 3'R,6'R,7'R,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'S,8'E,12'R)-6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'R,8'E,12'R)-

6-chloro-7'-hydroxy-6',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as the second eluting minor isomer (3.2 mg, 5.34 μmol, 8.37% yield). $^1$H NMR (400 MHz, MeOH-d4) δ 7.59 (d, J=8.2 Hz, 1H), 7.16-7.09 (m, 2H), 7.02 (dd, J=3.1, 8.8 Hz, 1H), 6.95 (d, J=8.2 Hz, 1H), 6.91 (s, 1H), 5.89 (td, J=6.8, 15.5 Hz, 1H), 5.69 (dd, J=7.8, 15.3 Hz, 1H), 4.15 (d, J=11.9 Hz, 1H), 4.01 (d, J=11.9 Hz, 1H), 3.94 (d, J=7.8 Hz, 1H), 3.92-3.86 (m, 1H), 3.69 (dd, J=2.6, 14.0 Hz, 1H), 3.47 (d, J=14.5 Hz, 1H), 3.35 (d, J=14.5 Hz, 1H), 2.94 (dd, J=12.0, 14.2 Hz, 1H), 2.83-2.74 (m, 2H), 2.57-2.46 (m, 1H), 2.44-2.32 (m, 1H), 2.27-2.16 (m, 1H), 2.12-2.01 (m, 3H), 1.91-1.81 (m, 3H), 1.80-1.69 (m, 3H), 1.66-1.60 (m, 1H), 1.47 (d, J=7.0 Hz, 3H), 1.11 (s, 3H). MS (ESI, +ve ion) m/z 599.2 (M+H)$^+$.

Example 119. (1S,3'R,6'R,7'S,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'R,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'S,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'R,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

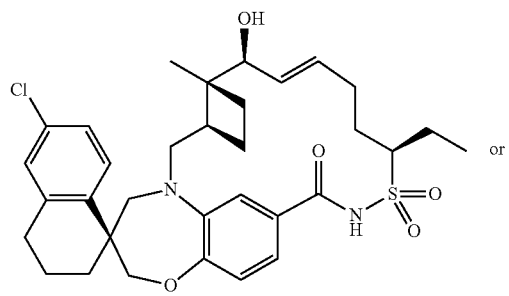

or

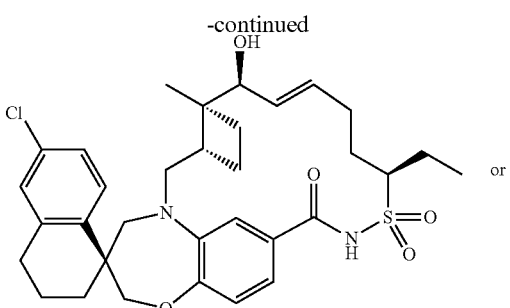

or

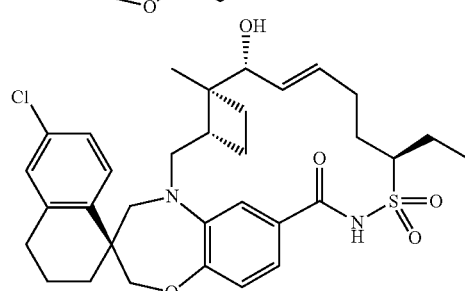

-continued

Step 1: (S)-6'-chloro-N—((R)-hept-6-en-3-ylsulfonyl)-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hept-6-EN-3-ylsulfonyl)-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide or (S)-6'-chloro-N—((R)-hept-6-en-3-ylsulfonyl)-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hept-6-en-3-ylsulfonyl)-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide

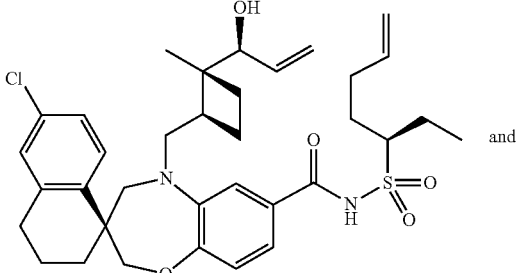

and

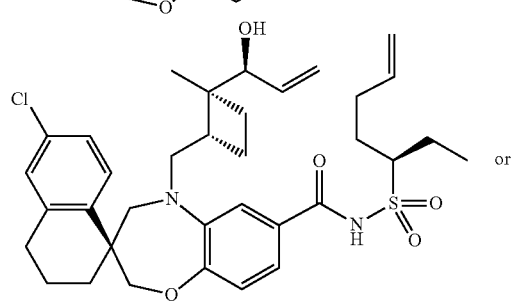

or

-continued

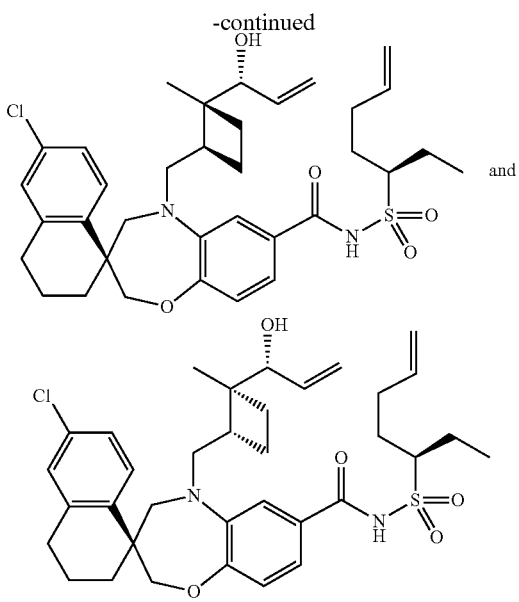

The title compounds were synthesized from (S)-6'-chloro-5-(((1R,2R)-2-((5)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxylic acid (107 mg, 0.222 mmol) and (R)-hept-6-ene-3-sulfonamide (Intermediate EE21; 118 mg, 0.666 mmol) following the procedure described for Example 116, Step 10. Column chromatography (12 g Sift, hexanes:EtOAc (containing 1% AcOH, 1:0 to 4:1)) gave (S)-6'-chloro-N—((R)-hept-6-en-3-ylsulfonyl)-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hept-6-en-3-ylsulfonyl)-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide or (S)-6'-chloro-N—((R)-hept-6-en-3-ylsulfonyl)-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hept-6-en-3-ylsulfonyl)-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide as the first eluting major component (45 mg, 0.070 mmol, 31.7% yield).

Further elution provided (S)-6'-chloro-N—((R)-hept-6-en-3-ylsulfonyl)-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hept-6-en-3-ylsulfonyl)-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide or (S)-6'-chloro-N—((R)-hept-6-en-3-ylsulfonyl)-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hept-6-en-3-ylsulfonyl)-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide as the second eluting minor component (29 mg, 0.045 mmol, 20.4% yield).

Step 2: (1S,3'R,6'R,7'S,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'R,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'S,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'R,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide The title compound was synthesized from (S)-6'-chloro-N—((R)-hept-6-en-3-ylsulfonyl)-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hept-6-en-3-ylsulfonyl)-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide or (S)-6'-chloro-N—((R)-hept-6-en-3-ylsulfonyl)-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hept-6-en-3-ylsulfonyl)-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide (Example 119, Step 1, first eluting major component; 17 mg, 0.027 mmol) following the procedure described for Example 116, Step 11. The reaction was evaporated in vacuo and the product was purified by column chromatography (4 g SiO$_2$, hexanes:EtOAc (containing 1% AcOH), 1:0 to 3:1) to give (1S,3'R,6'R,7'S,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'R,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'S,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'R,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (2.5 mg, 0.005 mmol, 15.4% yield). $^1$H NMR (400 MHz, MeOH-d4) δ 7.63 (d, J=8.2 Hz, 1H), 7.18-7.11 (m, 3H), 7.08 (br. s., 1H), 6.94 (d, J=8.2 Hz, 1H), 5.88 (td, J=5.8, 15.6 Hz, 1H), 5.68 (dd, J=7.2, 15.5 Hz, 1H), 4.18 (d, J=11.7 Hz, 1H), 4.02 (d, J=11.9 Hz, 1H), 3.82 (dd, J=2.5, 13.9 Hz, 1H), 3.69 (d, J=7.0 Hz, 1H), 3.57-3.49 (m, 1H), 3.44 (d, J=14.1 Hz, 1H), 3.36 (d, J=14.3 Hz, 1H), 2.95 (dd, J=11.6, 14.4 Hz, 1H), 2.84-2.74 (m, 2H), 2.66 (q, J=9.3 Hz, 1H), 2.53-2.38 (m, 2H), 2.25-1.70 (m, 10H), 1.42-1.34 (m, 2H), 1.14 (s, 3H), 1.13 (t, J=7.4 Hz, 3H). MS (ESI, +ve ion) m/z 613.2 (M+H)$^+$.

Example 120. (1S,3'R,6'R,7'S,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'R,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'S,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'R,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

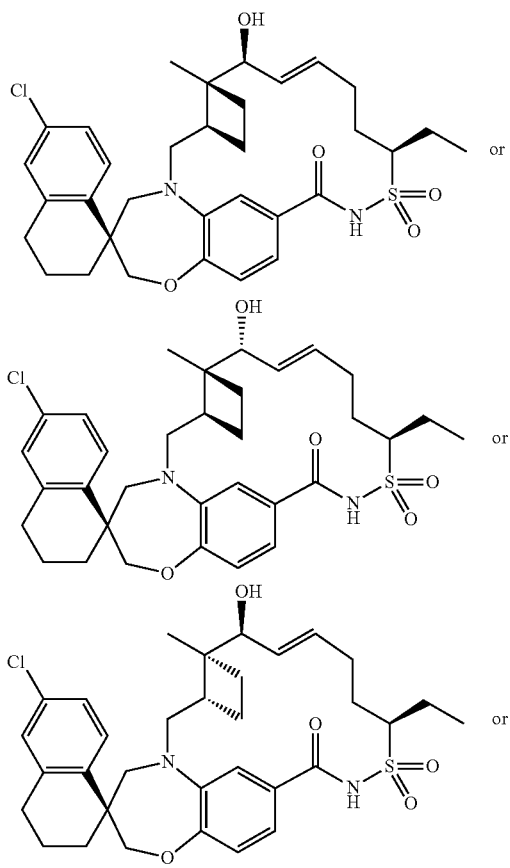

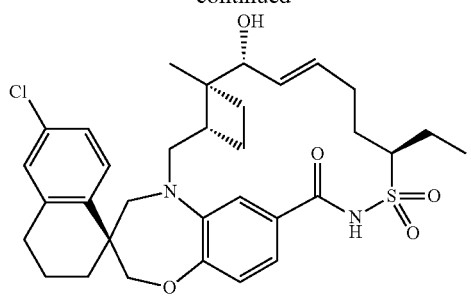

The title compound was synthesized from (S)-6'-chloro-N—((R)-hept-6-en-3-ylsulfonyl)-5-(((1R,2R)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hept-6-en-3-ylsulfonyl)-5-(((1S,2S)-2-((S)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide or (S)-6'-chloro-N—((R)-hept-6-en-3-ylsulfonyl)-5-(((1R,2R)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hept-6-en-3-ylsulfonyl)-5-(((1S,2S)-2-((R)-1-hydroxyallyl)-2-methylcyclobutyl)methyl)-3',4,4',5-tetrahydro-2H,2'H-spiro[benzo[b][1,4]oxazepine-3,1'-naphthalene]-7-carboxamide (Example 119, Step 1, second eluting minor component; 29 mg, 0.045 mmol) following the procedure described for Example 116, Step 11. The reaction was evaporated in vacuo and the product was purified by column chromatography (4 g SiO$_2$, hexanes: EtOAc (containing 1% AcOH), 1:0 to 4:1) to give (1S,3'R,6'R,7'S,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'R,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'S,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'S,6'S,7'R,8'E,12'R)-6-chloro-12'-ethyl-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (4.2 mg, 0.007 mmol, 15.2% yield). $^1$H NMR (400 MHz, CD$_3$OD) δ 7.72 (d, J=8.4 Hz, 1H), 7.16 (dd, J=2.2, 8.5 Hz, 1H), 7.10 (d, J=2.2 Hz, 1H), 6.96 (dd, J=2.5, 9.0 Hz, 1H), 6.91 (d, J=7.4 Hz, 1H), 6.78 (d, J=2.0 Hz, 1H), 5.86 (td, J=7.0, 15.3 Hz, 1H), 5.76 (dd, J=7.8, 15.3 Hz, 1H), 4.10-4.04 (m, 2H), 4.04-3.98 (m, 1H), 3.90 (d, J=7.6 Hz, 1H), 3.78 (d, J=15.1 Hz, 1H), 3.66 (d, J=14.3 Hz, 1H), 3.23 (d, J=14.3 Hz, 1H), 3.09 (dd, J=10.7, 15.2 Hz, 1H), 2.87-2.69 (m, 2H), 2.49-2.40 (m, 1H), 2.37 (dd, J=4.8, 10.3 Hz, 1H), 2.30-2.19 (m, 1H), 2.12-2.05 (m, 2H), 1.98-1.77 (m, 8H), 1.48-1.33 (m, 2H), 1.30 (s, 3H), 1.15 (t, J=7.5 Hz, 3H). MS (ESI, +ve ion) m/z 613.2 (M+H)$^+$.

Example 121. (1S,3'R,6'S,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide (1S,3'R,6'S,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'S,6'R,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'S,6'R,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide


or


or


or

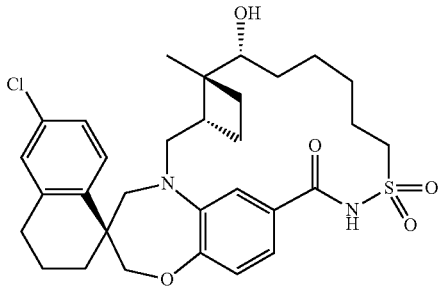

Step 1: (S)-tert-butyl 6'-chloro-5-(((1S,2R)-2-formyl-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1R,2S)-2-formyl-2-methylcyclobutyl)methyl)-3',4,4',5-tetrahydro-2H,2'H-spiro[benzo[b][1,4]oxazepine-3,1'-naphthalene]-7-carboxylate

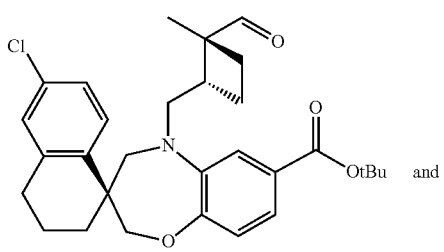 and

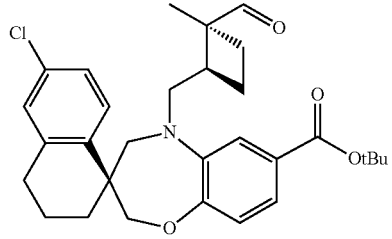

The title compounds were synthesized from (S)-tert-butyl 6'-chloro-5-(((1S,2R)-2-(hydroxymethyl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1R,2S)-2-(hydroxymethyl)-2-methylcyclobutyl)methyl)-3',4,4',5-tetrahydro-2H,2'H-spiro[benzo[b][1,4]oxazepine-3,1'-naphthalene]-7-carboxylate (Example 116, Step 6, second eluting minor component; 430 mg, 0.840 mmol) following the procedure described for Example 116, Step 7. Column chromatography (4 g SiO₂, hexanes:EtOAc, 1:0 to 9:1) gave (5)-tert-butyl 6'-chloro-5-(((1S,2R)-2-formyl-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1R,2S)-2-formyl-2-methylcyclobutyl)methyl)-3',4,4',5-tetrahydro-2H,2'H-spiro[benzo[b][1,4]oxazepine-3,1'-naphthalene]-7-carboxylate (388 mg, 0.761 mmol, 91% yield).

Step 2: (S)-tert-butyl 6'-chloro-5-((((1S,2R)-2-((S)-1-hydroxybut-3-en-1-yl)-2-methylcyclobutyl)methyl)-3',4',4',5-tetrahydro-2H,2'H-spiro[benzo[b][1,4]oxazepine-3,1'-naphthalene]-7-carboxylate and (S)-tert-butyl 6'-chloro-5-((((1S,2R)-2-((R)-1-hydroxybut-3-en-1-yl)-2-methylcyclobutyl)methyl)-3',4',4',5-tetrahydro-2H,2'H-spiro[benzo[b][1,4]oxazepine-3,1'-naphthalene]-7-carboxylate and (S)-tert-butyl 6'-chloro-5-((((1R,2S)-2-((S)-1-hydroxybut-3-en-1-yl)-2-methylcyclobutyl)methyl)-3',4',4',5-tetrahydro-2H,2'H-spiro[benzo[b][1,4]oxazepine-3,1'-naphthalene]-7-carboxylate and (S)-tert-butyl 6'-chloro-5-((((1R,2S)-2-((R)-1-hydroxybut-3-en-1-yl)-2-methylcyclobutyl)methyl)-3',4',4',5-tetrahydro-2H,2'H-spiro[benzo[b][1,4]oxazepine-3,1'-naphthalene]-7-carboxylate

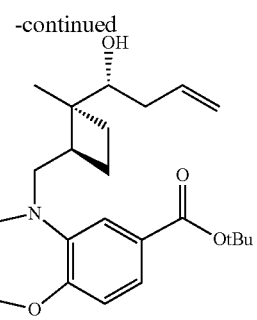

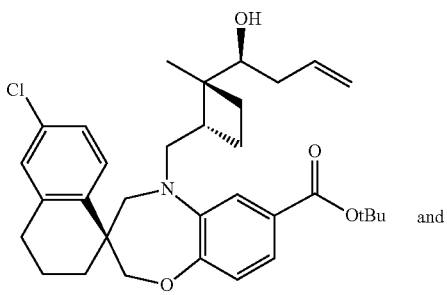 and

 and

 and

To a stirred solution of allyl iodide (280 µL, 3.04 mmol) and (S)-tert-butyl 6'-chloro-5-((((1S,2R)-2-formyl-2-methylcyclobutyl)methyl)-3',4',4',5-tetrahydro-2H,2'H-spiro[benzo[b][1,4]oxazepine-3,1'-naphthalene]-7-carboxylate and (5)-tert-butyl 6'-chloro-5-((((1R,2S)-2-formyl-2-methylcyclobutyl)methyl)-3',4',4',5-tetrahydro-2H,2'H-spiro[benzo[b][1,4]oxazepine-3,1'-naphthalene]-7-carboxylate (388 mg, 0.761 mmol) in DMF (15.2 mL) was added indium (Sigma Aldrich; 262 mg, 2.282 mmol). The reaction was stirred at ambient temperature for 30 minutes. After this time the reaction was partitioned between EtOAc and 1M LiCl. The separated organic layer was dried over MgSO₄, filtered and evaporated in vacuo. Column chromatography (40 g SiO₂, hexanes:EtOAc (containing 1% AcOH, 1:0 to 85:15) gave (5)-tert-butyl 6'-chloro-5-((((1S,2R)-2-((S)-1-hydroxybut-3-en-1-yl)-2-methylcyclobutyl)methyl)-3',4',4',5-tetrahydro-2H,2'H-spiro[benzo[b][1,4]oxazepine-3,1'-naphthalene]-7-carboxylate and (5)-tert-butyl 6'-chloro-5-((((1S,2R)-2-((R)-1-hydroxybut-3-en-1-yl)-2-methylcyclobutyl)methyl)-3',4',4',5-tetrahydro-2H,2'H-spiro[benzo[b][1,4]oxazepine-3,1'-naphthalene]-7-carboxylate or (S)-tert-butyl 6'-chloro-5-((((1R,2S)-2-((S)-1-hydroxybut-3-en-1-yl)-2-methylcyclobutyl)methyl)-3',4',4',5-tetrahydro-2H,2'H-spiro[benzo[b][1,4]oxazepine-3,1'-naphthalene]-7-carboxylate and (S)-tert-butyl 6'-chloro-5-((((1R,2S)-2-((R)-1-hydroxybut-3-en-1-yl)-2-methylcyclobutyl)methyl)-3',4',4',5-tetrahydro-2H,2'H-spiro[benzo[b][1,4]oxazepine-3,1'-naphthalene]-7-carboxylate as the first eluting major component (210 mg, 0.380 mmol, 50% yield).

Further elution provided (S)-tert-butyl 6'-chloro-5-((((1S,2R)-2-((S)-1-hydroxybut-3-en-1-yl)-2-methylcyclobutyl)methyl)-3',4',4',5-tetrahydro-2H,2'H-spiro[benzo[b][1,4]oxazepine-3,1'-naphthalene]-7-carboxylate and (S)-tert-butyl 6'-chloro-5-((((1S,2R)-2-((R)-1-hydroxybut-3-en-1-yl)-2-methylcyclobutyl)methyl)-3',4',4',5-tetrahydro-2H,2'H-spiro[benzo[b][1,4]oxazepine-3,1'-naphthalene]-7-carboxylate or (S)-tert-butyl 6'-chloro-5-((((1R,2S)-2-((S)-1-hydroxybut-3-en-1-yl)-2-methylcyclobutyl)methyl)-3',4',4',5-tetrahydro-2H,2'H-spiro[benzo[b][1,4]oxazepine-3,1'-naphthalene]-7-carboxylate and (S)-tert-butyl 6'-chloro-5-((((1R,2S)-2-((R)-1-hydroxybut-3-en-1-yl)-2-methylcyclobutyl)methyl)-3',4',4',5-tetrahydro-2H,2'H-spiro[benzo[b][1,4]oxazepine-3,1'-naphthalene]-7-carboxylate as the second eluting minor component (114 mg, 0.206 mmol, 27% yield).

Step 3: (S)-6'-chloro-5-((((1S,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-((((1S,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-((((1R,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-((((1R,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic Acid

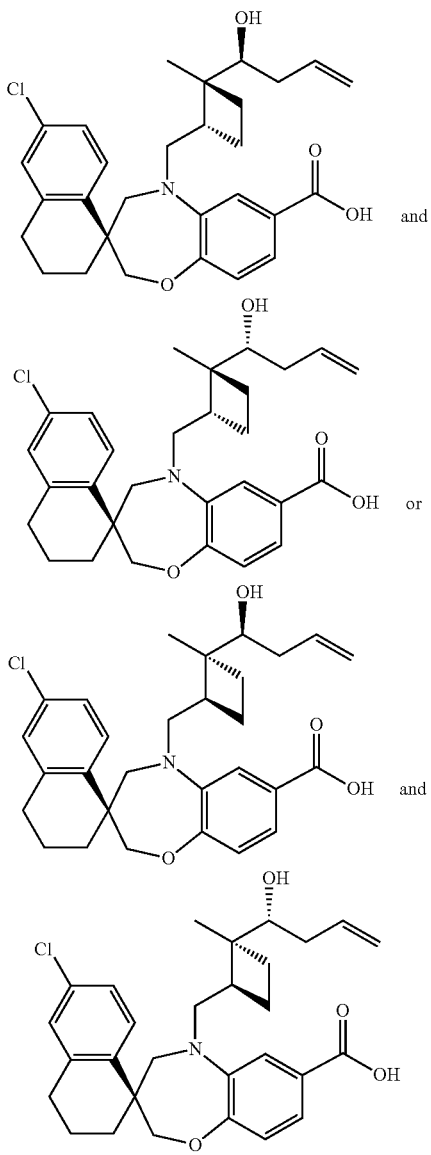

and or and

The title compounds were synthesized from (S)-tert-butyl 6'-chloro-5-((((1S,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-((((1S,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylate or (S)-tert-butyl 6'-chloro-5-((((1R,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-((((1R,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylate (Example 121, Step 2, first eluting major component; 210 mg, 0.380 mmol) following the procedure described for Example 116, Step 9. After aqueous workup, the isolated crude mixture of (S)-6'-chloro-5-((((1S,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-((((1S,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid or (S)-6'-chloro-5-((((1R,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-((((1R,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid was taken on to the next step without further purification.

Step 4: (S)—N-(but-3-en-1-yl sulfonyl)-6'-chloro-5-((((1S,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-((((1S,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide or (S)—N-(but-3-en-1-ylsulfonyl)-6'-chloro-5-((((1R,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-((((1R,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide

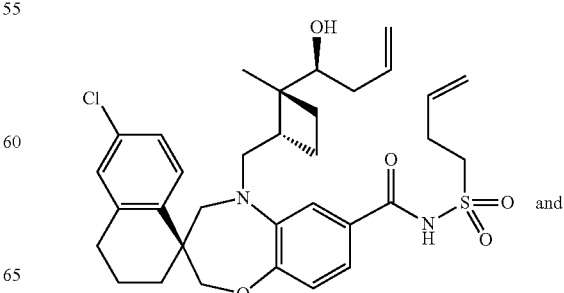

and

-continued

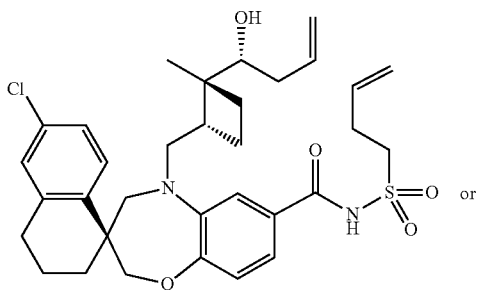

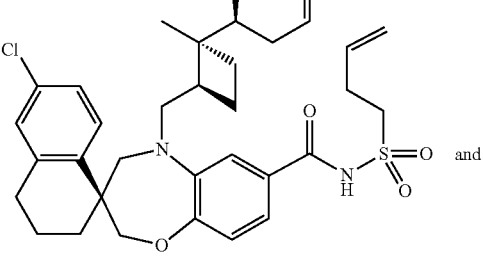
and

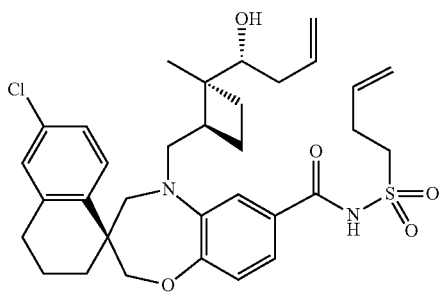

The title compounds were synthesized from (S)-6'-chloro-5-(((1S,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1R,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid (200 mg, 0.403 mmol) and but-3-ene-1-sulfonamide (Intermediate EE15; 164 mg, 1.21 mmol) following the procedure described for Example 116, Step 10. The crude material was dissolved in DCM and adsorbed in a 5 g silica gel cartridge and purified by column (4 g SiO$_2$, hexanes:EtOAc (containing 1% AcOH), gradient 1:0 to 85:15 and 85:15 isocratic) to give (S)—N-(but-3-en-1-ylsulfonyl)-6'-chloro-5-(((1S,2R)-2-((5)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1S,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide or (S)—N-(but-3-en-1-ylsulfonyl)-6'-chloro-5-(((1R,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1R,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide as the first eluting minor isomer (20 mg, 0.033 mmol, 8.1% yield).

Further elution provided (S)—N-(but-3-en-1-ylsulfonyl)-6'-chloro-5-(((1S,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1S,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide or (S)—N-(but-3-en-1-ylsulfonyl)-6'-chloro-5-(((1R,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1R,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide as the second eluting major isomer (95 mg, 0.155 mmol, 38.5% yield).

Step 5: (1S,3'R,6'S,7'S, 9'Z)-6-chloro-7'-hydroxy-6'-methyl-3,4-dihydro-2H, 15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'R,6'S,7'R, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'R,6'S,7'S, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'R,6'S,7'R, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide or (1S,3'S,6'R,7'S, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'S,6'R,7'R, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'S,6'R,7'S, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'S,6'R,7'R, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide -continued

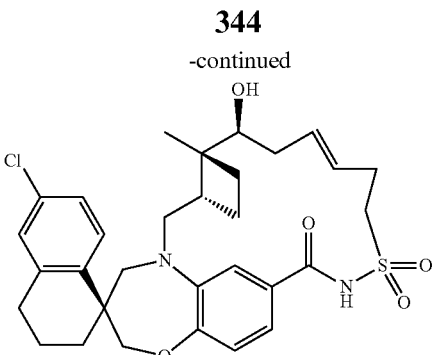

and

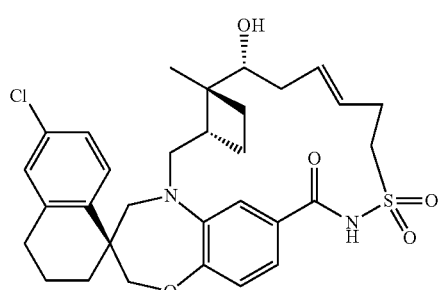

or

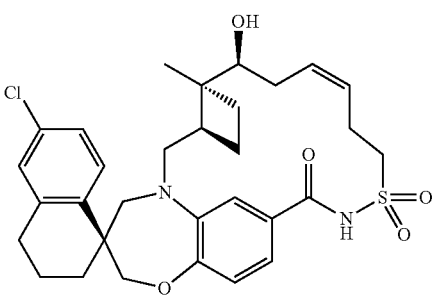

and

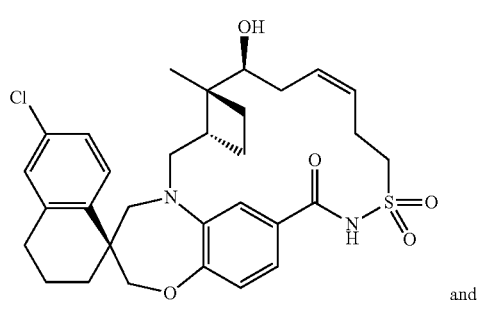

and

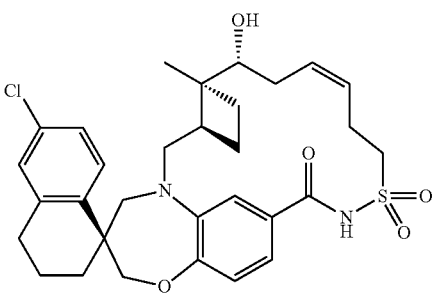

and

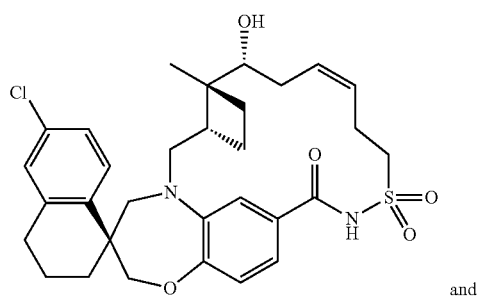

and

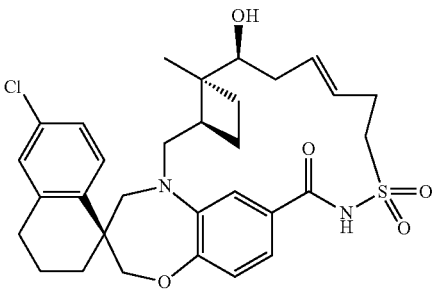

and

-continued

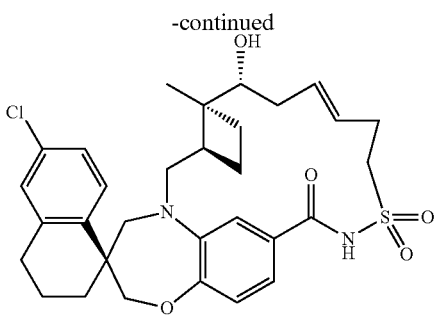

A stirred solution of (S)—N-(but-3-en-1-ylsulfonyl)-6'-chloro-5-(((1S,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1S,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide or (S)—N-(but-3-en-1-ylsulfonyl)-6'-chloro-5-(((1R,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1R,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide (Example 121, Step 4, second eluting major isomer; 95 mg, 0.155 mmol) in Toluene (155 mL) was degassed by sparging Ar(g) through for 20 minutes. After this time Hoveyda-Grubbs catalyst $2^{nd}$ generation (19.4 mg, 0.031 mmol) was added and the reaction was heated at reflux for 90 minutes. After this time the reaction was cooled to ambient temperature and the catalyst was deactivated by sparging air through. The reaction was evaporated in vacuo and the residue was adsorbed in a 5 g $SiO_2$ plug and purified by column chromatography (4 g $SiO_2$, hexanes:EtOAc (containing 1% AcOH), 1:0 to 85:15) to give (1S,3'R,6'S,7'S, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'S,7'R, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'S,7'S, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'S,7'R, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'S,6'R,7'S, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'S,6'R,7'R, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'S,6'R,7'S, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'S,6'R,7'R, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (75 mg, 0.128 mmol, 83% yield).

Step 6: (1S,3'R,6'S,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (1S,3'R,6'S,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'S,6'R,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'S,6'R,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide To a stirred solution of (1S,3'R,6'S,7'S, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (75 mg, 0.128 mmol) in ethyl acetate (25.6 mL) was added platinum(IV) oxide (Sigma Aldrich; 14.55 mg, 0.064 mmol). The system was evacuated and filled with $H_2$(g) (×3). The reaction was stirred at ambient temperature for 1 hour. After this time an additional portion of $PtO_2$ (6 mg) was added and the system was placed under $H_2$. After 1 hour an additional portion of $PtO_2$ (10 mg) and the reaction was placed under $H_2$ for 1 hour. After this time TLC and LC/MS shows desired product. The reaction was filtered over celite washing the cake with EtOAc (200 mL). The solvent was evaporated in vacuo. The resulting residue was purified by column chromatography (12 g $SiO_2$, hexanes:EtOAc (containing 1% AcOH), 1:0 to 80:20) to obtain partial separation of two single diastereomers. (1S,3'R,6'S,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'S,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'S,6'R,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'S,6'R,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide (4 mg, 0.0068 mmol, 10.6% yield) was obtained as the second eluting minor isomer. ¹H NMR (500 MHz, CD₂Cl₂) δ 9.62 (br. s., 1H), 7.73 (d, J=8.3 Hz, 1H), 7.31 (dd, J=2.2, 8.3 Hz, 1H), 7.22 (d, J=2.2 Hz, 1H), 7.17 (dd, J=2.3, 8.4 Hz, 1H), 7.09 (d, J=2.2 Hz, 1H), 6.95 (d, J=8.3 Hz, 1H), 4.12-4.08 (m, 2H), 3.87 (d, J=14.9 Hz, 1H), 3.69 (d, J=14.2 Hz, 1H), 3.61 (d, J=9.5 Hz, 1H), 3.57 (ddd, J=3.7, 6.4, 14.9 Hz, 1H), 3.39-3.31 (m, 1H), 3.13 (d, J=14.4 Hz, 1H), 3.01 (dd, J=9.7, 15.3 Hz, 1H), 2.83-2.70 (m, 2H), 2.34 (q, J=9.4 Hz, 1H), 2.06-1.97 (m, 3H), 1.95-1.88 (m, 2H), 1.88-1.82 (m, 2H), 1.72-1.63 (m, 3H), 1.59 (td, J=4.9, 14.2 Hz, 3H), 1.46-1.38 (m, 2H), 1.28-1.20 (m, 2H), 1.13 (s, 3H). MS (ESI, +ve ion) m/z 587.2 (M+H)⁺.

Example 122. (1S,3'R,6'S,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15',13'-dioxide (1S,3'R,6'S,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'S,6'R,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'S,6'R,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]tetraen]-15'-one 13',13'-dioxide

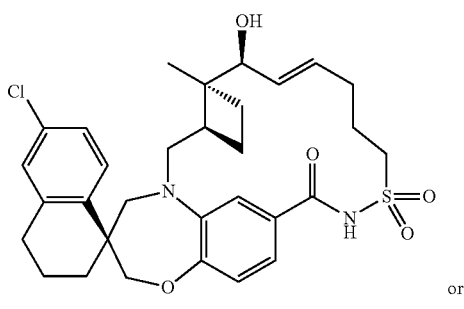

or

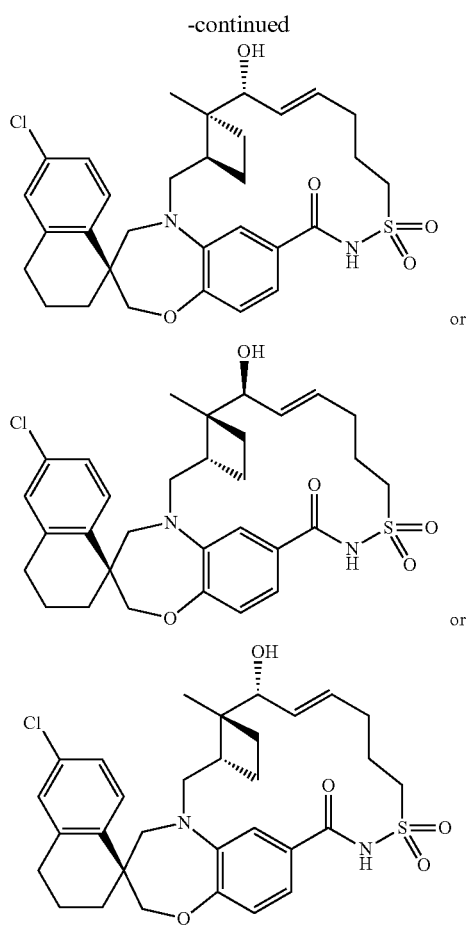

The title compound was synthesized as described for Example 121, step 6. (1S,3'R,6'S,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'S,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'S,6'R,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'S,6'R,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide (10 mg, 0.017 mmol, 26.6% yield) was obtained as the first eluting major isomer. ¹H NMR (400 MHz, CDCl₃) δ 9.95 (br. s., 1H), 7.73 (d, J=8.4 Hz, 1H), 7.43 (dd, J=2.1, 8.3 Hz, 1H), 7.22 (d, J=2.2 Hz, 1H), 7.20 (dd, J=2.3, 8.4 Hz, 1H), 7.10 (d, J=2.3 Hz, 1H), 6.93 (d, J=8.2 Hz, 1H), 4.20 (d, J=12.3 Hz, 1H), 4.08 (d, J=11.7 Hz, 1H), 3.87 (d, J=14.7 Hz, 1H), 3.67-3.60 (m, 1H), 3.60 (d, J=9.2 Hz, 1H), 3.48-3.40 (m, 1H), 3.37 (d, J=14.1 Hz, 1H), 3.25 (d, J=13.9 Hz, 1H), 2.87 (dd, J=9.9, 14.8 Hz, 1H), 2.75 (t, J=5.9 Hz, 2H), 2.33 (q, J=9.5 Hz, 1H), 2.08-1.94 (m, 3H), 1.91-1.72 (m, 7H), 1.71-1.62 (m, 3H), 1.62-1.54 (m, 1H), 1.48-1.39 (m, 1H), 1.33-1.23 (m, 2H), 1.12 (s, 3H). MS (ESI, +ve ion) m/z 587.2 (M+H)⁺.

Example 123. (1S,3'R,6'S,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (1S,3'R,6'S,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'S,6'R,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'S,6'R,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide

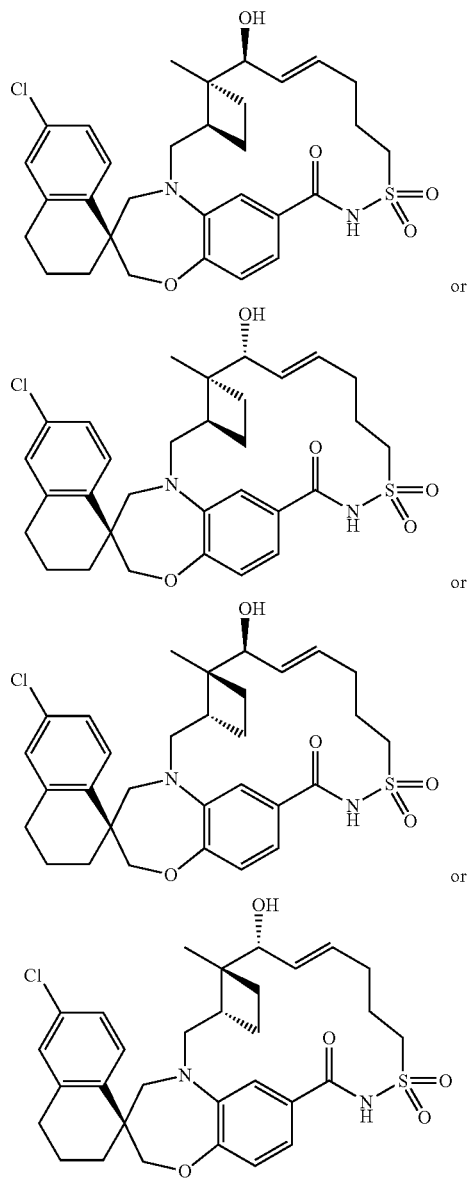

Step 1: (S)-6'-chloro-5-(((1S,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1S,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic Acid

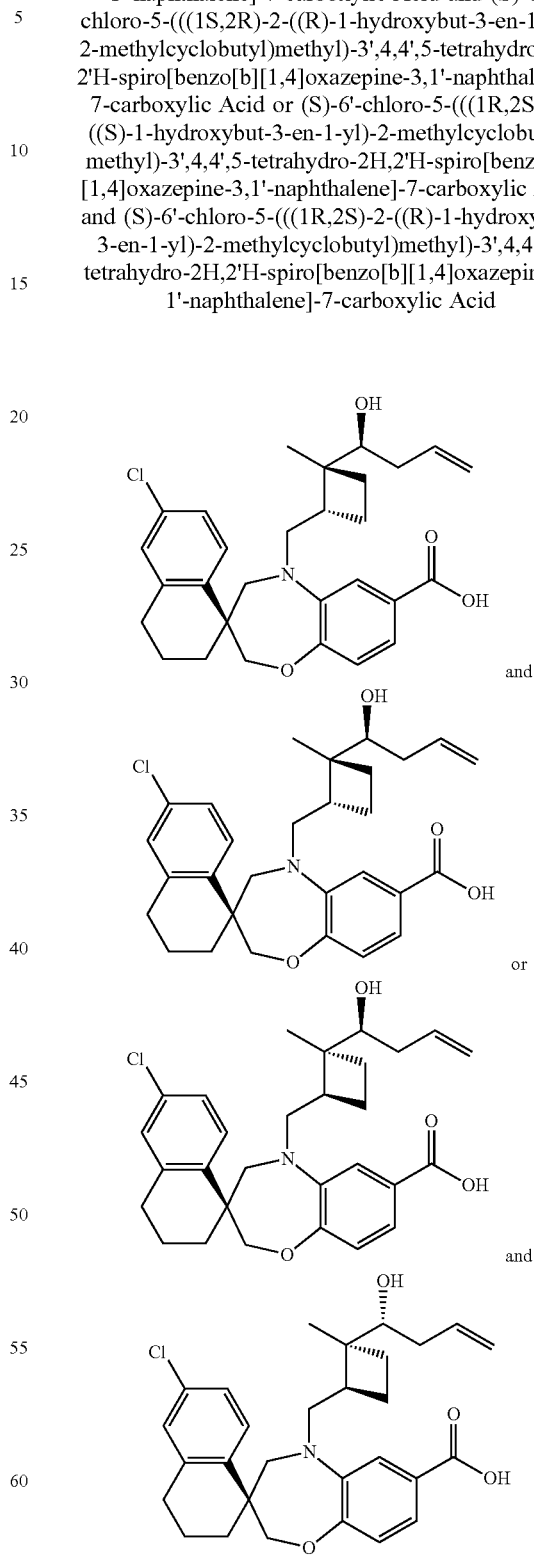

The title compounds were synthesized from (S)-tert-butyl 6'-chloro-5-(((1S,2R)-2-((S)-1-hydroxybut-3-en-1-yl)-2-methylcyclobutyl)methyl)-3',4,4',5-tetrahydro-2H,2'H-spiro

351

[benzo[b][1,4]oxazepine-3,1'-naphthalene]-7-carboxylate and (S)-tert-butyl 6'-chloro-5-(((1S,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylate or (S)-tert-butyl 6'-chloro-5-(((1R,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1R,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylate (Example 121, Step 2, second eluting minor component; 150 mg, 0.272 mmol) following the procedure described for Example 116, Step 9. After aqueous workup, the isolated crude mixture of (S)-6'-chloro-5-(((1S,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1R,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid was taken on to the next step without further purification.

Step 2: (S)—N-(but-3-en-1-ylsulfonyl)-6'-chloro-5-(((1S,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1S,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide or (S)—N-(but-3-en-1-ylsulfonyl)-6'-chloro-5-(((1R,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1R,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide

352

The title compounds were synthesized from (S)-6'-chloro-5-(((1S,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1R,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid (110 mg, 0.222 mmol) and but-3-ene-1-sulfonamide (Intermediate EE15; 90 mg, 0.665 mmol) following the procedure described for Example 116, Step 10. Purification by column chromatography (12 g SiO$_2$, hexanes:EtOAc (containing 1% AcOH), gradient 1:0 to 85:15) to give (S)—N-(but-3-en-1-ylsulfonyl)-6'-chloro-5-(((1S,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1S,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide or (S)—N-(but-3-en-1-ylsulfonyl)-6'-chloro-5-(((1R,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1R,2S)-2-((R)-1-hydroxybut-3-en-1-yl)-2- methylcyclobutyl)methyl)-3',4,4',5-tetrahydro-2H,2'H-spiro[benzo[b][1,4]oxazepine-3,1'-naphthalene]-7-carboxamide (100 mg, 0.163 mmol, 73.5% yield).

Step 3: (1S,3'R,6'S,7'S, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'R,6'S,7'R, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'R,6'S,7'S, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'R,6'S,7'R, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide or (1S,3'S,6'R,7'S, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'S,6'R,7'R, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'S,6'R,7'S, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'S,6'R, 7'R, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide

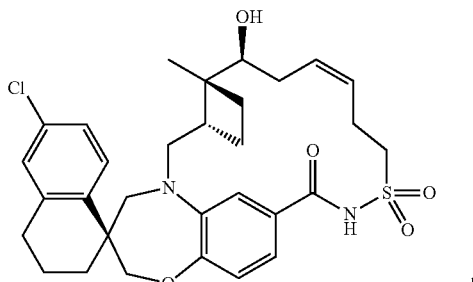

and

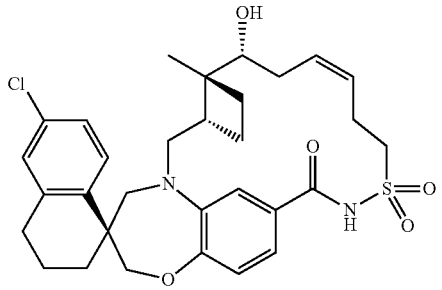

and

-continued

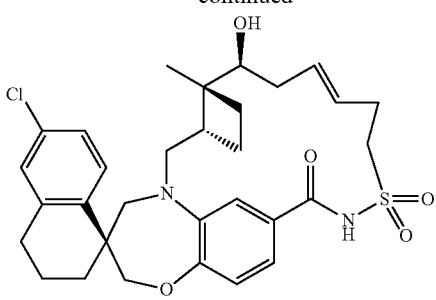

and

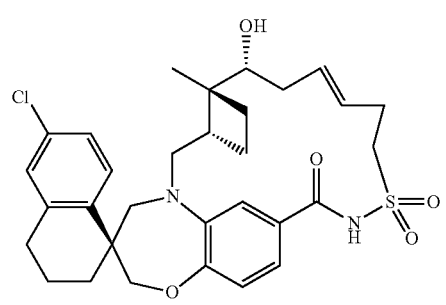

or

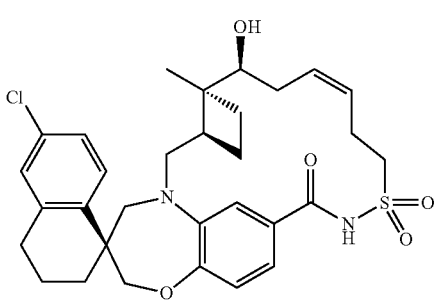

and

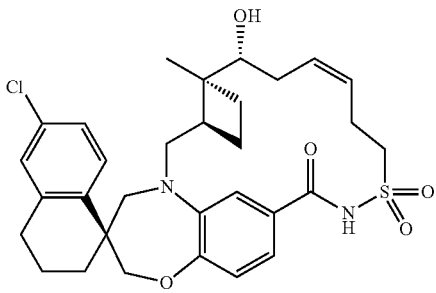

and

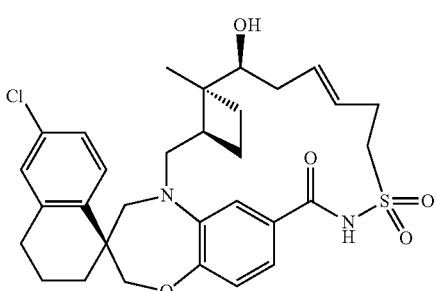

and

-continued

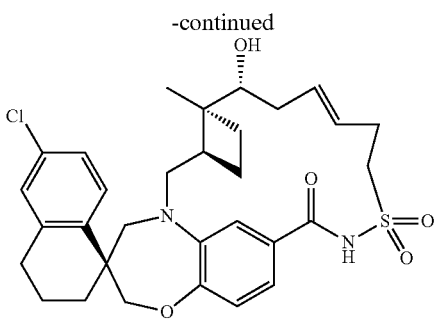

The title compounds were synthesized from (S)—N-(but-3-en-1-ylsulfonyl)-6'-chloro-5-(((1S,2R)-2-((S)-1-hydroxy-but-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1S,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide or (S)—N-(but-3-en-1-ylsulfonyl)-6'-chloro-5-(((1R,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1R,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide (100 mg, 0.163 mmol) following the procedure described for Example 121, Step 5. The reaction was evaporated in vacuo and the residue was purified by column chromatography (12 g SiO$_2$, hexanes:EtOAc (containing 1% AcOH), 1:0 to 9:1) to give (1S,3'R,6'S,7'S, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'S,7'R, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'S,7'S, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'S,7'R, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'S,7'S, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'S,6'R,7'R, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'S,6'R,7'S, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'S,6'R,7'R, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (75 mg, 0.128 mmol, 79% yield).

Step 4: (1S,3'R,6'S,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (1S,3'R,6'S,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'S,6'R,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'S,6'R,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide The title compound was synthesized from (1S,3'R,6'S,7'S, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'S,7'R, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'S,7'S, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'S,7'R, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'S,6'R,7'S, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'S,6'R,7'R, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'S,6'R,7'S, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'S,6'R,7'R, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (75 mg, 0.128 mmol) following the procedure described for Example 121, Step 6. The crude material was purified by column chromatography (12 g SiO$_2$, hexanes:EtOAc (containing 1% AcOH), 1:0 to 85:15) to give a 1:1 mixture of diastereomers. The two diastereomers (total of 38 mg) were separated by reverse-phase HPLC eluting with a gradient of 40-95% acetonitrile (containing 0.1% TFA) in water (containing 0.1% TFA). (1S,3'R,6'S,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S, 3'R,6'S,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'S,6'R,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13', 13'-dioxide or (1S,3'S,6'R,7'R)-6-chloro-7'-hydroxy-6'- methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide was obtained as a 4:1 mixture of diastereomers as the second eluting major component (20 mg, 0.034 mmol, 26.6% yield). Analytical data are provided for the major isomer. $^1$H NMR (500 MHz, CDCl$_3$) δ 9.06 (br. s., 1H), 7.72 (d, J=8.6 Hz, 1H), 7.24 (d, J=2.0 Hz, 1H), 7.19 (d, J=1.2 Hz, 1H), 7.18 (d, J=2.0 Hz, 1H), 7.09 (d, J=2.2 Hz, 1H), 6.94 (d, J=8.1 Hz, 1H), 4.09 (s, 2H), 3.91 (d, J=14.9 Hz, 1H), 3.81 (td, J=7.2, 14.6 Hz, 1H), 3.68 (d, J=14.2 Hz, 1H), 3.51-3.41 (m, 1H), 3.33 (d, J=9.5 Hz, 1H), 3.15 (d, J=14.2 Hz, 1H), 3.00 (dd, J=9.8, 15.2 Hz, 1H), 2.85-2.71 (m, 2H), 2.50 (q, J=9.0 Hz, 1H), 2.06-1.92 (m, 3H), 1.91-1.77 (m, 6H), 1.77-1.69 (m, 2H), 1.66-1.54 (m, 3H), 1.46-1.36 (m, 3H), 1.30 (s, 3H). MS (ESI, +ve ion) m/z 587.2 (M+H)$^+$.

Example 124. (1S,3'R,6'R,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'S,6'S,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'S,6'S,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]tetraen]-15'-one 13',13'-dioxide

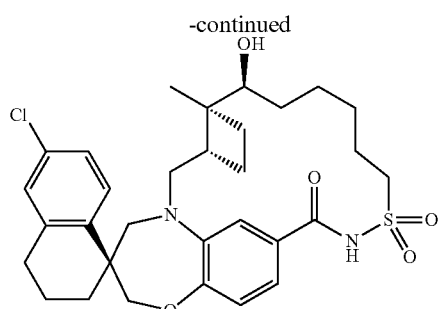

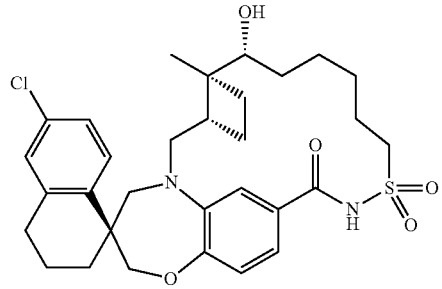

Step 1: (S)-tert-butyl 6'-chloro-5-(((1R,2R)-2-((S)-1-hydroxybut-3-en-1-yl)-2-methylcyclobutyl)methyl)-3',4',4',5-tetrahydro-2H,2'H-spiro[benzo[b][1,4]oxazepine-3,1'-naphthalene]-7-carboxylate and (S)-tert-butyl 6'-chloro-5-(((1R,2R)-2-((R)-1-hydroxybut-3-en-1-yl)-2-methylcyclobutyl)methyl)-3',4',4',5-tetrahydro-2H,2'H-spiro[benzo[b][1,4]oxazepine-3,1'-naphthalene]-7-carboxylate or (S)-tert-butyl 6'-chloro-5-(((1S,2S)-2-((S)-1-hydroxybut-3-en-1-yl)-2-methylcyclobutyl)methyl)-3',4',4',5-tetrahydro-2H,2'H-spiro[benzo[b][1,4]oxazepine-3,1'-naphthalene]-7-carboxylate and (S)-tert-butyl 6'-chloro-5-(((1S,2S)-2-((R)-1-hydroxybut-3-en-1-yl)-2-methylcyclobutyl)methyl)-3',4',4',5-tetrahydro-2H,2'H-spiro[benzo[b][1,4]oxazepine-3,1'-naphthalene]-7-carboxylate

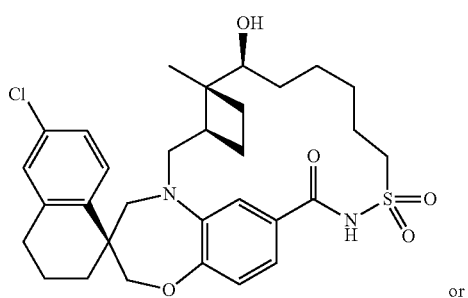

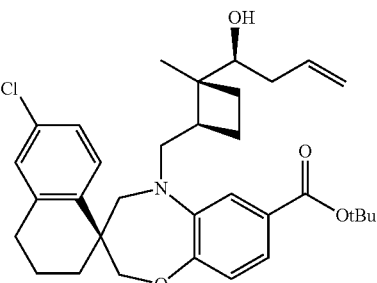

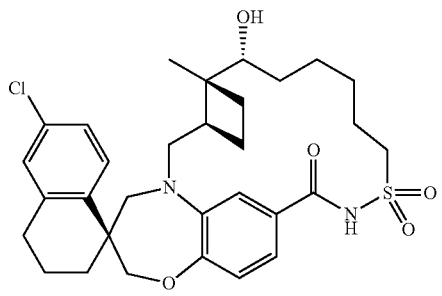

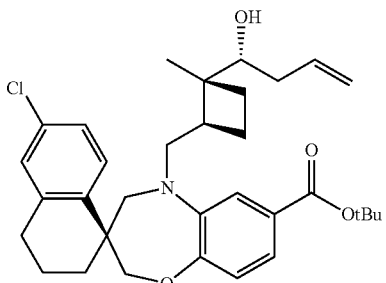

-continued

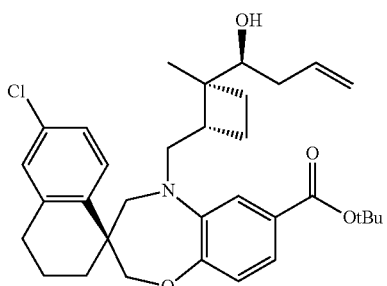

and

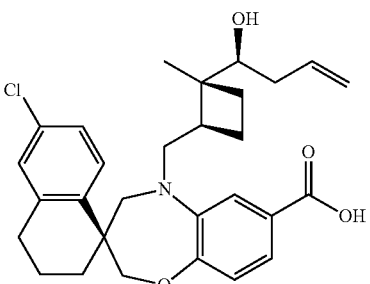

The title compounds were synthesized from (S)-tert-butyl 6'-chloro-5-(((1R,2R)-2-formyl-2-methylcyclobutyl)methyl)-3',4,4',5-tetrahydro-2H,2'H-spiro[benzo[b][1,4]oxazepine-3,1'-naphthalene]-7-carboxylate or (S)-tert-butyl 6'-chloro-5-(((1S,2S)-2-formyl-2-methylcyclobutyl)methyl)-3',4,4',5-tetrahydro-2H,2'H-spiro[benzo[b][1,4]oxazepine-3,1'-naphthalene]-7-carboxylate (Example 116, Step 7; 141 mg, 0.276 mmol) following the procedure described for Example 121, Step 2. Purification of the crude material by column chromatography provided (5)-tert-butyl 6'-chloro-5-(((1R,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylate and (5)-tert-butyl 6'-chloro-5-(((1R,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylate or (5)-tert-butyl 6'-chloro-5-(((1S,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylate and (5)-tert-butyl 6'-chloro-5-(((1S,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylate (130 mg, 0.235 mmol, 85% yield).

Step 2: (S)-6'-chloro-5-(((1R,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1S,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1S,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic Acid

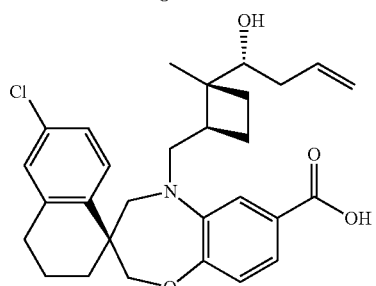

and

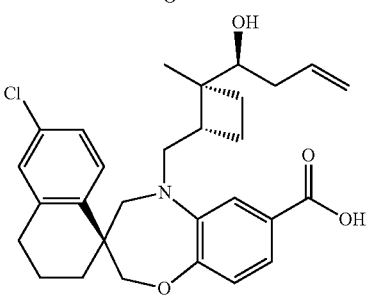

or

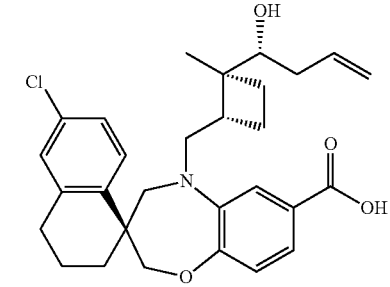

and

The title compounds were synthesized from (S)-tert-butyl 6'-chloro-5-(((1R,2R)-2-((S)-1-hydroxybut-3-en-1-yl)-2-methylcyclobutyl)methyl)-3',4,4',5-tetrahydro-2H,2'H-spiro

[benzo[b][1,4]oxazepine-3,1'-naphthalene]-7-carboxylate and (S)-tert-butyl 6'-chloro-5-(((1R,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylate or (S)-tert-butyl 6'-chloro-5-(((1S,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylate and (5)-tert-butyl 6'-chloro-5-(((1S,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylate (130 mg, 0.235 mmol) following the procedure described for Example 116, Step 9. After aqueous workup, the isolated crude mixture of (S)-6'-chloro-5-(((1R,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1S,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid was taken on to the next step without further purification.

Step 3: (S)—N-(but-3-en-1-ylsulfonyl)-6'-chloro-5-(((1R,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1R,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide or (S)—N-(but-3-en-1-ylsulfonyl)-6'-chloro-5-(((1S,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1S,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide -continued

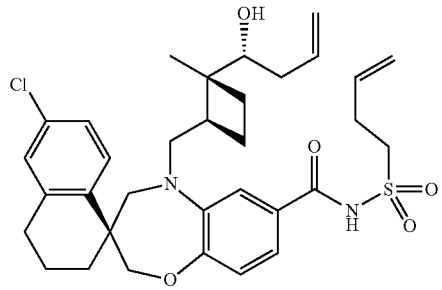

or

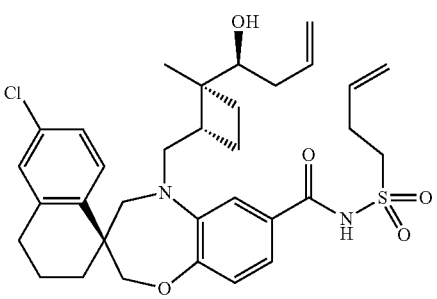

and

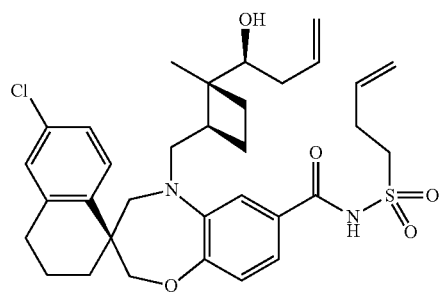

and

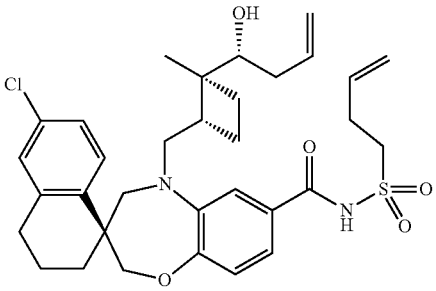

The title compounds were synthesized from (S)-6'-chloro-5-(((1R,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1S,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxylic acid (100 mg, 0.202 mmol) and but-3-ene-1-sulfonamide (Intermediate EE15; 82 mg, 0.605 mmol) following the procedure described for Example 116, Step 10. The crude material was purified by column (12 g SiO$_2$, hexanes:EtOAc (containing 1% AcOH), gradient 1:0 to 4:1) to give (S)—N-(but-3-en-1-ylsulfonyl)-6'-chloro-5-(((1R,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1R,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide or (S)—N-(but-3-en-1-ylsulfonyl)-6'-chloro-5-(((1S,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-yl sulfonyl)-6'-chloro-5-(((1S,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide as the first eluting major isomer (66 mg, 0.108 mmol, 53.2% yield).

Further elution provided (S)—N-(but-3-en-1-ylsulfonyl)-6'-chloro-5-(((1R,2R)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1R,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide or (S)—N-(but-3-en-1-ylsulfonyl)-6'-chloro-5-(((1S,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1S,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide as the second eluting minor isomer (16 mg, 0.026 mmol, 12.9% yield).

Step 4: (1S,3'R,6'R,7'S, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'R, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'R, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'S,6'S,7'S, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'S,6'S,7'R, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'S,6'S,7'S, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'S,6'S,7'R, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide

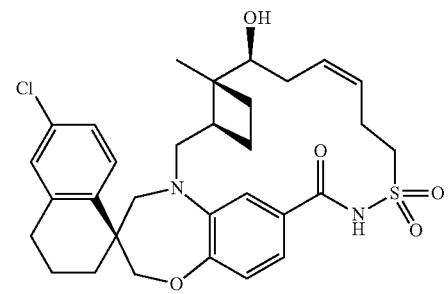

and

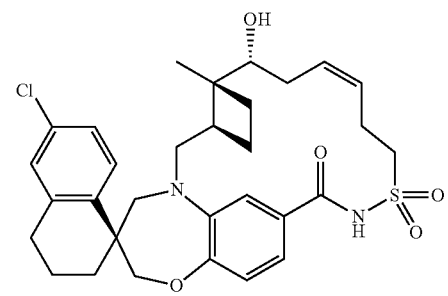

and

365
-continued

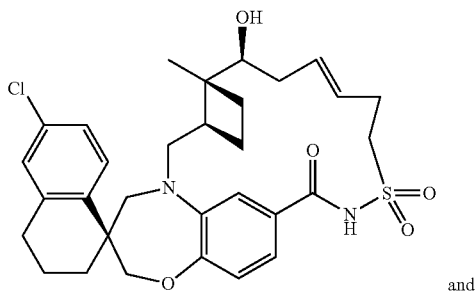

and

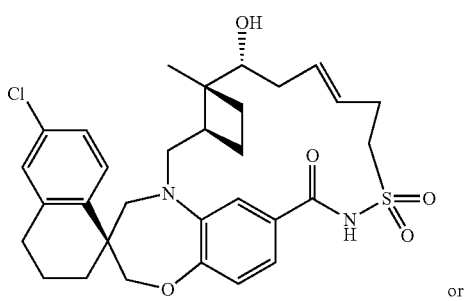

or

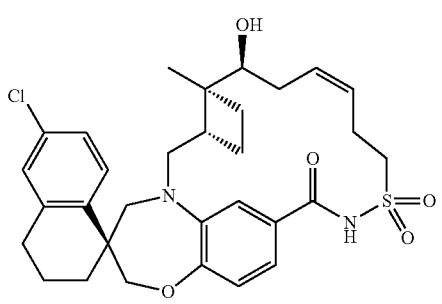

and

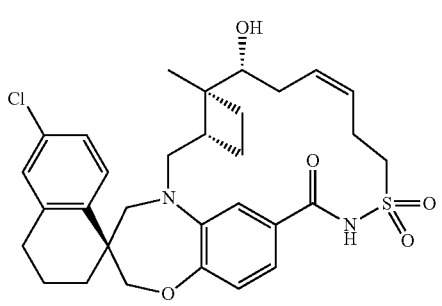

and


and

366
-continued

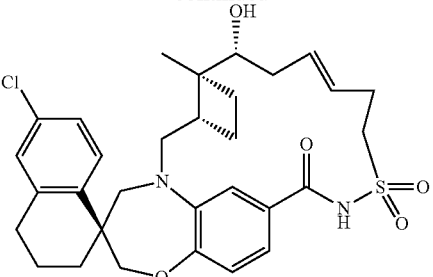

The title compounds were synthesized from (S)—N-(but-3-en-1-ylsulfonyl)-6'-chloro-5-(((1R,2R)-2-((S)-1-hydroxy-but-3-en-1-yl)-2-methylcyclobutyl)methyl)-3',4,4',5-tetra-hydro-2H,2'H-spiro[benzo[b][1,4]oxazepine-3,1'-naphthalene]-7-carboxamide and (S)—N-(but-3-en-1-ylsulfonyl)-6'-chloro-5-(((1R,2R)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide or (S)—N-(but-3-en-1-ylsulfonyl)-6'-chloro-5-(((1S,2S)-2-((S)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide and (S)—N-(but-3-en-1-ylsulfonyl)-6'-chloro-5-(((1S,2S)-2-((R)-1-hydroxybut-3-en-1-yl)-2-methylcyclobutyl)methyl)-3',4,4',5-tetrahydro-2H,2'H-spiro[benzo[b][1,4]oxazepine-3,1'-naphthalene]-7-carboxamide (Example 124, Step 3, first eluting major isomer; 66 mg, 0.108 mmol) following the procedure described for Example 121, Step 5. The reaction was evaporated in vacuo and the residue was purified by column chromatography (12 g SiO$_2$, hexanes:EtOAc (containing 1% AcOH), 1:0 to 85:15) to give (1S, 3'R,6'R,7'S, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'R, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'R, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'S,6'S,7'S, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'S,6'S,7'R, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'S,6'S,7'S, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'S,6'S,7'R, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (3 mg, 0.005 mmol, 4.76% yield).

Step 5: (1S,3'R,6'R,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'S,6'S,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'S,6'S,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide The title compound was synthesized from (1S,3'R,6'R,7'S, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'R, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'R, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'S,6'S,7'S, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'S,6'S,7'R, 9'Z)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'S,6'S,7'S, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'S,6'S,7'R, 9'E)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (3 mg, 0.005 mmol) following the procedure described for Example 121, Step 6. Purification of the crude material by column chromatography (1 g SiO$_2$, hexanes:EtOAc (containing 1% AcOH), 1:0 to 85:15) provided (1S,3'R,6'R,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'S,6'S,7'S)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'S,6'S,7'R)-6-chloro-7'-hydroxy-6'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (1.8 mg, 0.003 mmol, 59.8% yield). $^1$H NMR (400 MHz, CD$_2$Cl$_2$) δ 8.44 (br. s, 1H), 7.72 (d, J=8.6 Hz, 1H), 7.53 (s, 1H), 7.19 (dd, J=2.3, 8.6 Hz, 1H), 7.10 (d, J=2.3 Hz, 1H), 7.07 (dd, J=1.9, 8.1 Hz, 1H), 7.01 (d, J=7.4 Hz, 1H), 4.14-4.09 (m, 2H), 3.92-3.82 (m, 3H), 3.61 (dd, J=4.2, 11.1 Hz, 1H), 3.53-3.45 (m, 1H), 3.39-3.31 (m, 1H), 3.10 (d, J=14.1 Hz, 1H), 2.84-2.71 (m, 3H), 2.46-2.38 (m, 1H), 2.35-2.29 (m, 1H), 1.99-1.85 (m, 4H), 1.54 (br. s, 7H), 1.45-1.33 (m, 4H), 1.15 (s, 3H). MS (ESI, +ve ion) m/z 587.2 (M+H)$^+$.

Example 125. (1S,3'R,6'R,7'S,8'E,11'R)-6-chloro-7'-hydroxy-6',11'-dimethyl-3,4-dihydro-2H,14'H-spiro[naphthalene-1,21'-[19]oxa[12]thia[1,13]diazatetracyclo[13.7.2.0$^{3,6}$.0$^{18,23}$]pentacosa[8,15,17,23]tetraen]-14'-one 12',12'-dioxide or (1S,3'R,6'R,7'R,8'E,11'R)-6-chloro-7'-hydroxy-6',11'-dimethyl-3,4-dihydro-2H,14'H-spiro[naphthalene-1,21'-[19]oxa[12]thia[1,13]diazatetracyclo[13.7.2.0$^{3,6}$.0$^{18,23}$]pentacosa[8,15,17,23]tetraen]-14'-one 12',12'-dioxide or (1S,3'S,6'S,7'S,8'E,11'R)-6-chloro-7'-hydroxy-6',11'-dimethyl-3,4-dihydro-2H,14'H-spiro[naphthalene-1,21'-[19]oxa[12]thia[1,13]diazatetracyclo[13.7.2.0$^{3,6}$.0$^{18,23}$]pentacosa[8,15,17,23]tetraen]-14'-one 12',12'-dioxide or (1S,3'S,6'S,7'R,8'E,11'R)-6-chloro-7'-hydroxy-6',11'-dimethyl-3,4-dihydro-2H,14'H-spiro[naphthalene-1,21'-[19]oxa[12]thia[1,13]diazatetracyclo[13.7.2.0$^{3,6}$.0$^{18,23}$]pentacosa[8,15,17,23]tetraen]-14'-one 12',12'-dioxide

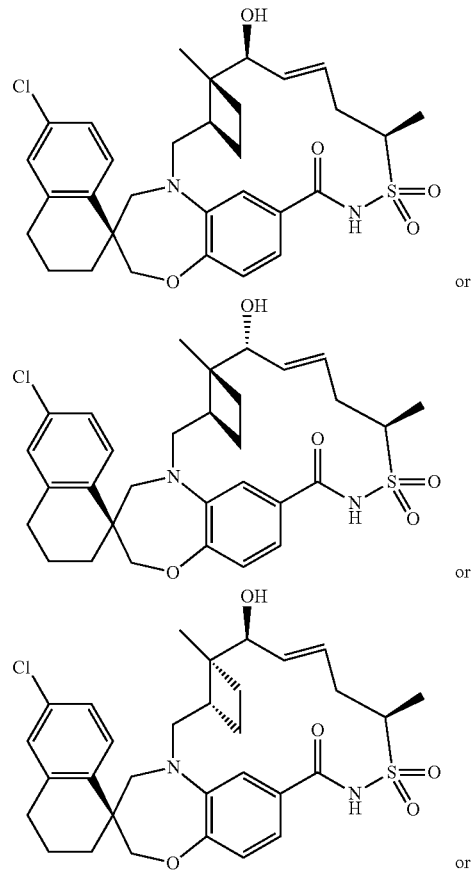

-continued

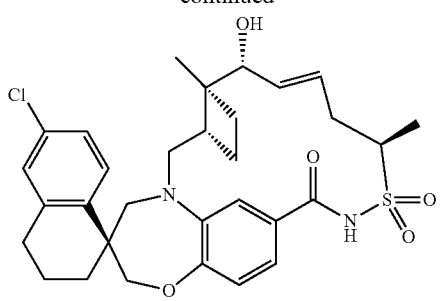

Step 1: (S)-tert-butyl 6'-chloro-5-(((1R,2R)-2-((1S, 5R,E)-1-hydroxy-5-sulfamoylhex-2-en-1-yl)-2-methylcyclobutyl)methyl)-3',4,4',5-tetrahydro-2H, 2'H-spiro[benzo[b][1,4]oxazepine-3,1'-naphthalene]-7-carboxylate and (S)-tert-butyl 6'-chloro-5-(((1R, 2R)-2-((1R,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3, 1'-naphthalene]-7-carboxylate or (S)-tert-butyl 6'-chloro-5-(((1S,2S)-2-((1S,5R,E)-1-hydroxy-5-sulfamoylhex-2-en-1-yl)-2-methylcyclobutyl) methyl)-3',4,4',5-tetrahydro-2H,2'H-spiro[benzo[b] [1,4]oxazepine-3,1'-naphthalene]-7-carboxylate and (S)-tert-butyl 6'-chloro-5-(((1S,2S)-2-((1R,5R,E)-1-hydroxy-5-sulfamoylhex-2-en-1-yl)-2-methylcyclobutyl)methyl)-3',4,4',5-tetrahydro-2H,2'H-spiro [benzo[b][1,4]oxazepine-3,1'-naphthalene]-7-carboxylate


and

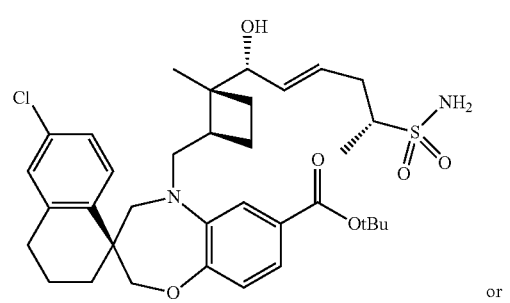

or

-continued

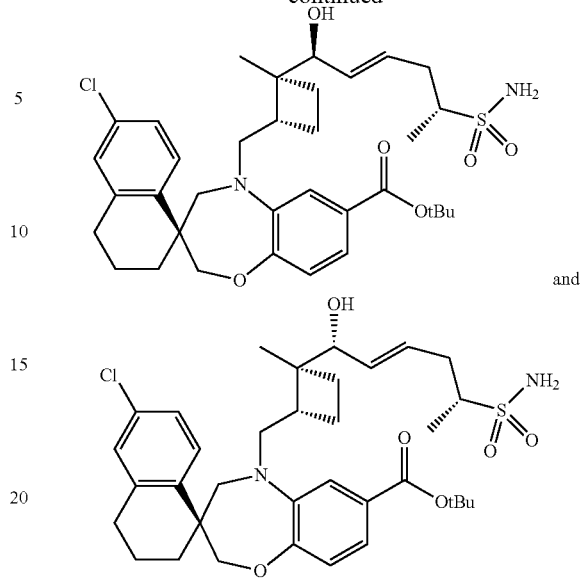

To a stirred solution of (S)-tert-butyl 6'-chloro-5-(((1R, 2R)-2-((S)-1-hydroxyallyl)-2-methylcyclobutyl)methyl)-3', 4,4',5-tetrahydro-2H,2'H-spiro[benzo[b][1,4]oxazepine-3, 1'-naphthalene]-7-carboxylate and (S)-tert-butyl 6'-chloro-5-(((1S,2S)-2-((S)-1-hydroxyallyl)-2-methylcyclobutyl) methyl)-3',4,4',5-tetrahydro-2H,2'H-spiro[benzo[b][1,4] oxazepine-3,1'-naphthalene]-7-carboxylate or (5)-tert-butyl 6'-chloro-5-(((1R,2R)-2-((R)-1-hydroxyallyl)-2-methylcyclobutyl)methyl)-3',4,4',5-tetrahydro-2H,2'H-spiro[benzo [b][1,4]oxazepine-3,1'-naphthalene]-7-carboxylate and (5)-tert-butyl 6'-chloro-5-(((1S,2S)-2-((R)-1-hydroxyallyl)-2-methylcyclobutyl)methyl)-3',4,4',5-tetrahydro-2H,2'H-spiro [benzo[b][1,4]oxazepine-3,1'-naphthalene]-7-carboxylate (Example 116, Step 8, first eluting isomer; 140 mg, 0.260 mmol) and (R)-pent-4-ene-2-sulfonamide (Intermediate EE17; 116 mg, 0.780 mmol) in Et$_2$O (2 mL) was degassed with Ar(g) for 10 minutes. After this time the reaction was treated with copper(I) iodide (1.7 mg, 9.11 μmol) and Grubbs catalyst, 2$^{nd}$ generation (6.63 mg, 7.80 μmol). The reaction was heated at reflux for 5 hours. After this time the catalyst was deactivated by sparging air through the reaction. The reaction was then evaporated in vacuo and purified by column chromatography (12 g SiO$_2$, hexanes:EtOAc (containing 1% AcOH), 1:0 to 2:1) to give (S)-tert-butyl 6'-chloro-5-(((1R,2R)-2-((1S,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1R, 2R)-2-((1R,5R,E)-1-hydroxy-5-sulfamoylhex-2-en-1-yl)-2-methylcyclobutyl)methyl)-3',4,4',5-tetrahydro-2H,2'H-spiro [benzo[b][1,4]oxazepine-3,1'-naphthalene]-7-carboxylate or (S)-tert-butyl 6'-chloro-5-(((1S,2S)-2-((1S,5R,E)-1-hydroxy-5-sulfamoylhex-2-en-1-yl)-2-methylcyclobutyl) methyl)-3',4,4',5-tetrahydro-2H,2'H-spiro[benzo[b][1,4] oxazepine-3,1'-naphthalene]-7-carboxylate and (5)-tert-butyl 6'-chloro-5-(((1S,2S)-2-((1R,5R,E)-1-hydroxy-5-sulfamoylhex-2-en-1-yl)-2-methylcyclobutyl)methyl)-3',4, 4',5-tetrahydro-2H,2'H-spiro[benzo[b][1,4]oxazepine-3,1'-naphthalene]-7-carboxylate as the first eluting major component (50 mg, 0.076 mmol, 29.0% yield).

Further elution provided (5)-tert-butyl 6'-chloro-5-(((1R, 2R)-2-((1S,5R,E)-1-hydroxy-5-sulfamoylhex-2-en-1-yl)-2- methylcyclobuty tetrahydro-2H,2'H-spiro[benzo[b][1,4] oxazepine-3,1'-naphthalene]-7-carboxylate and (5)-tert-butyl 6'-chloro-5-(((1R,2R)-2-((1R,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylate or (5)-tert-butyl 6'-chloro-5-(((1S,2S)-2-((1S,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylate and (5)-tert-butyl 6'-chloro-5-(((1S,2S)-2-((1R,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylate as the first eluting major component (15 mg, 0.023 mmol, 8.7% yield).

Step 2: (S)-6'-chloro-5-(((1R,2R)-2-((1S,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1R,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1S,2S)-2-((1S,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1S,2S)-2-((1R,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylic Acid

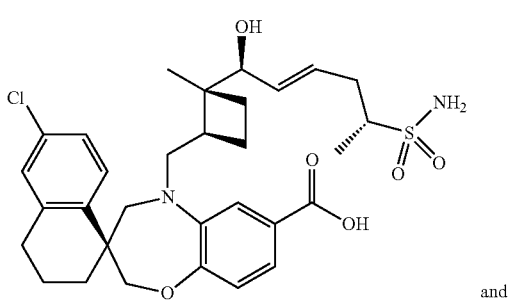

and

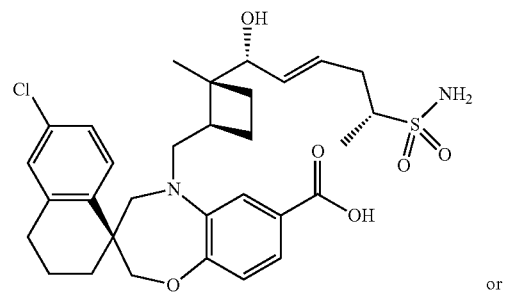

or

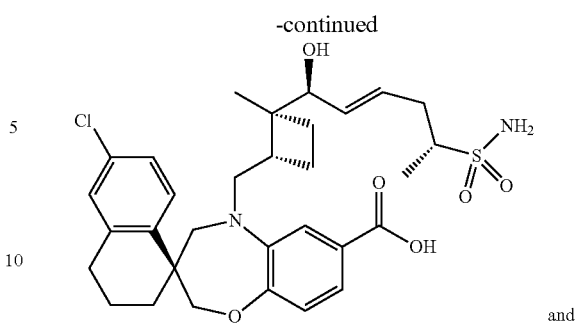

and

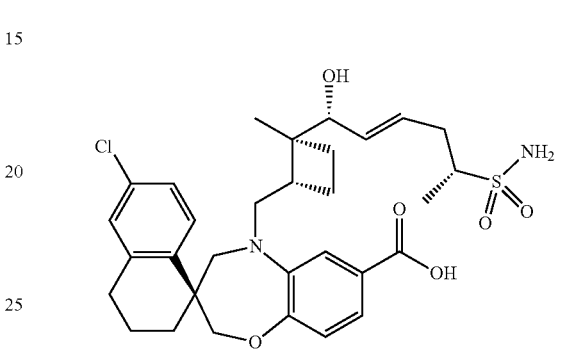

To a stirred solution (5)-tert-butyl 6'-chloro-5-(((1R,2R)-2-((1S,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylate and (5)-tert-butyl 6'-chloro-5-(((1R,2R)-2-((1R,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylate or (S)-tert-butyl 6'-chloro-5-(((1S,2S)-2-((1S,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-((1R,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylate (Example 125, Step 1 first eluting major component; 50 mg, 0.076 mmol) in DCM (1517 μL) was added trifluoroacetic acid (117 μL, 1.517 mmol). The reaction was stirred at ambient temperature for 3 hours. After this time the reaction was evaporated in vacuo. The crude material was dissolved in DCM and washed with aqueous NaHCO₃. The crude isolated mixture of (S)-6'-chloro-5-(((1R,2R)-2-((1S,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1R,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1S,2S)-2-((1S,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2S)-2-((1R,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylic acid (45 mg, 0.075 mmol, 98% yield) was used without further purification in the next step.

Step 3: (1S,3'R,6'R,7'S,8'E,11'R)-6-chloro-7'-hydroxy-6',11'-dimethyl-3,4-dihydro-2H,14'H-spiro[naphthalene-1,21'-[19]oxa[12]thia[1,13]diazatetracyclo[13.7.2.0³,⁶.0¹⁸,²³]pentacosa[8,15,17,23]tetraen]-14'-one 12',12'-dioxide or (1S,3'R,6'R,7'R,8'E,11R)-6-chloro-7'-hydroxy-6',11'-dimethyl-3,4-dihydro-2H,14'H-spiro[naphthalene-1,21'-[19]oxa[12]thia[1,13]diazatetracyclo[13.7.2.0³,⁶.0¹⁸,²³]pentacosa[8,15,17,23]tetraen]-14'-one 12',12'-dioxide or (1S,3'S,6'S,7'S,8'E,11R)-6-chloro-7'-hydroxy-6',11'-dimethyl-3,4-dihydro-2H,14'H-spiro[naphthalene-1,21'-[19]oxa[12]thia[1,13]diazatetracyclo[13.7.2.0³,⁶.0¹⁸,²³]pentacosa[8,15,17,23]tetraen]-14'-one 12',12'-dioxide or (1S,3'S,6'S,7'R,8'E,11'R)-6-chloro-7'-hydroxy-6',11'-dimethyl-3,4-dihydro-2H,14'H-spiro[naphthalene-1,21'-[19]oxa[12]thia[1,13]diazatetracyclo[13.7.2.0³,⁶.0¹⁸,²³]pentacosa[8,15,17,23]tetraen]-14'-one 12',12'-dioxide To an ice cooled solution of (S)-6'-chloro-5-(((1R,2R)-2-((1S,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1R,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1S,2S)-2-((1S,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1S,2S)-2-((1R,5R,E)-1-hydroxy-5-sulfamoylhex-2-en-1-yl)-2-methylcyclobutyl)methyl)-3',4,4',5-tetrahydro-2H,2'H-spiro[benzo[b][1,4]oxazepine-3,1'-naphthalene]-7-carboxylic acid (0.045 g, 0.075 mmol) and 4-dimethylaminopyridine (0.015 g, 0.127 mmol) in $CH_2Cl_2$ (37.3 mL) under a $N_2$ atmosphere was added EDC (0.029 g, 0.149 mmol) portionwise over 2 min. The reaction was allowed to warm to ambient temperature overnight. After this time the reaction was partitioned between EtOAc and $NaHCO_3$. The separated organic layer was dried over $MgSO_4$, filtered and evaporated in vacuo. Purification by reverse phase HPLC eluting with a gradient of 35-95% acetonitrile (containing 0.1% TFA) in water (containing 0.1% TFA) over 40 minutes provided (1S,3'R,6'R,7'S,8'E,11'R)-6-chloro-7'-hydroxy-6',11'-dimethyl-3,4-dihydro-2H,14'H-spiro[naphthalene-1,21'-[19]oxa[12]thia[1,13]diazatetracyclo[13.7.2.0³,⁶.0¹⁸,²³]pentacosa[8,15,17,23]tetraen]-14'-one 12',12'-dioxide or (1S,3'R,6'R,7'R,8'E,11'R)-6-chloro-7'-hydroxy-6',11'-dimethyl-3,4-dihydro-2H,14'H-spiro[naphthalene-1,21'-[19]oxa[12]thia[1,13]diazatetracyclo[13.7.2.0³,⁶.0¹⁸,²³]pentacosa[8,15,17,23]tetraen]-14'-one 12',12'-dioxide or (1S,3'S,6'S,7'S,8'E,11'R)-6-chloro-7'-hydroxy-6',11'-dimethyl-3,4-dihydro-2H,14'H-spiro[naphthalene-1,21'-[19]oxa[12]thia[1,13]diazatetracyclo[13.7.2.0³,⁶.0¹⁸,²³]pentacosa[8,15,17,23]tetraen]-14'-one 12',12'-dioxide or (1S,3'S,6'S,7'R,8'E,11'R)-6-chloro-7'-hydroxy-6',11'-dimethyl-3,4-dihydro-2H,14'H-spiro[naphthalene-1,21'-[19]oxa[12]thia[1,13]diazatetracyclo[13.7.2.0³,⁶.0¹⁸,²³]pentacosa[8,15,17,23]tetraen]-14'-one 12',12'-dioxide as the second eluting major isomer (3.1 mg, 5.30 µmol, 7.10% yield). ¹H NMR (500 MHz, $CD_3OD$) δ 7.73 (d, J=8.6 Hz, 1H), 7.60-7.26 (m, 1H), 7.15 (d, J=8.3 Hz, 1H), 7.10 (d, J=2.2 Hz, 1H), 7.12 (br. s., 1H), 6.87 (br. s., 1H), 6.07 (td, J=6.6, 15.4 Hz, 1H), 5.80 (dd, J=7.6, 15.4 Hz, 1H), 4.09-4.00 (m, 2H), 3.76 (br. s., 2H), 3.68 (d, J=14.4 Hz, 1H), 2.88-2.71 (m, 3H), 2.70-2.50 (m, 2H), 2.14-2.06 (m, 2H), 2.01-1.84 (m, 4H), 1.52-1.39 (m, 5H), 1.29 (s, 3H), 1.22 (s, 3H). MS (ESI, +ve ion) m/z 585.1 (M+H)⁺.

Example 126. (1S,3'R,6'R,7'S,8'E,10'R,11'R)-6-chloro-10'-(hydroxymethyl)-7'-methoxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'S,11'S)-6-chloro-10'-(hydroxymethyl)-7'-methoxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

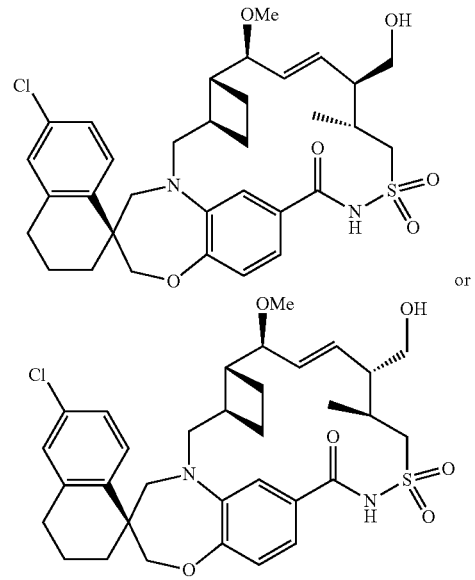

Step 1: (3S,4S)-3-methyl-4-vinyldihydrofuran-2(3H)-one and (3R,4R)-3-methyl-4-vinyldihydrofuran-2(3H)-one

A 50 mL round bottom flask fitted with a short-path distillation apparatus was charged with (E)-but-2-ene-1,4-diol (TCI; 10 g, 114 mmol), triethyl orthopropionate (Sigma Aldrich; 44.0 mL, 221 mmol) and benzohydroquinone (Acros Organics; 1.000 g, 9.08 mmol) and the mixture was heated at 140-150° C. for 12 hours (EtOH was collected in a receiving flask for the first 2 hours of the reaction). After this time the reaction was distilled under reduced pressure (ca. 20 mm of Hg) and the fraction boiling between 110-130° C. was collected to give (3S,4S)-3-methyl-4-vinyldihydrofuran-2(3H)-one and (3R,4R)-3-methyl-4-vinyldihydrofuran-2(3H)-one (8.2 g, 65.0 mmol, 57.3% yield).

Step 2: (2S,3S)-3-(hydroxymethyl)-N-methoxy-N,2-dimethylpent-4-enamide and (2R,3R)-3-(hydroxymethyl)-N-methoxy-N,2-dimethylpent-4-enamide

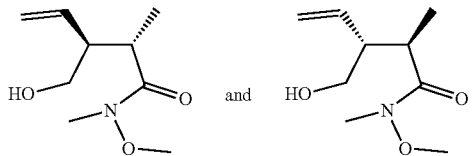

Trimethylaluminum (Sigma Aldrich, 2 M in hexanes; 9.51 mL, 19.02 mmol) was added at 0° C. to a suspension of N,O-dimethylhydroxylamine hydrochloride (Sigma Aldrich; 1.856 g, 19.02 mmol) in DCM (15.85 mL) and the resulting mixture was stirred for 2 hours at 0° C. Next a solution of (3S,4S)-3-methyl-4-vinyldihydrofuran-2(3H)-one and (3R,4R)-3-methyl-4-vinyldihydrofuran-2(3H)-one (1 g, 7.93 mmol) in DCM (15.85 mL) was added dropwise over 5 minutes and the mixture was stirred at 0° C. for 2 hours. After this time the reaction was quenched by the careful addition of HCl (1M aqueous solution). The separated aqueous layer was extracted with DCM and the combined organic extracts were washed with brine, dried over MgSO$_4$, filtered and evaporated in vacuo to give (2S,3S)-3-(hydroxymethyl)-N-methoxy-N,2-dimethylpent-4-enamide and (2R,3R)-3-(hydroxymethyl)-N-methoxy-N,2-dimethylpent-4-enamide (1.2 g, 6.41 mmol, 81% yield). Analytical Data showed desired product and starting material (ca. 3:1 ratio). This material was used without further purification in the next step.

Step 3: (2S,3S)-3-(((tert-butyldiphenylsilyl)oxy)methyl)-N-methoxy-N,2-dimethylpent-4-enamide and (2R,3R)-3-(((tert-butyldiphenylsilyl)oxy)methyl)-N-methoxy-N,2-dimethylpent-4-enamide

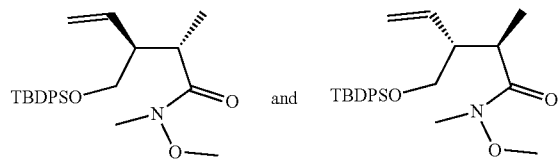

To a stirred solution of (2S,3S)-3-(hydroxymethyl)-N-methoxy-N,2-dimethylpent-4-enamide and (2R,3R)-3-(hydroxymethyl)-N-methoxy-N,2-dimethylpent-4-enamide (1.2 g, 6.41 mmol) in DMF (32.0 mL) was added imidazole (Sigma Aldrich; 0.873 g, 12.82 mmol) and tert-butyldiphenylsilyl chloride (1.811 mL, 7.05 mmol) and the reaction was stirred at ambient temperature overnight. After this time the reaction was partitioned between EtOAc and water. The separated organic layer was washed with brine, dried over MgSO$_4$, filtered and evaporated in vacuo. Column chromatography (40 g SiO$_2$, hexanes:EtOAc, 1:0 to 4:1) gave (2S,3S)-3-(((tert-butyldiphenylsilyl)oxy)methyl)-N-methoxy-N,2-dimethylpent-4-enamide and (2R,3R)-3-(((tert-butyldiphenylsilyl)oxy)methyl)-N-methoxy-N,2-dimethylpent-4-enamide (1.6 g, 3.76 mmol, 58.7% yield). Analytical Data were consistent with the desired product (contaminated with the corresponding lactone).

Step 4: (2S,3S)-3-(((tert-butyldiphenylsilyl)oxy)methyl)-2-methylpent-4-en-1-ol and (2R,3R)-3-(((tert-butyldiphenylsilyl)oxy)methyl)-2-methylpent-4-en-1-ol

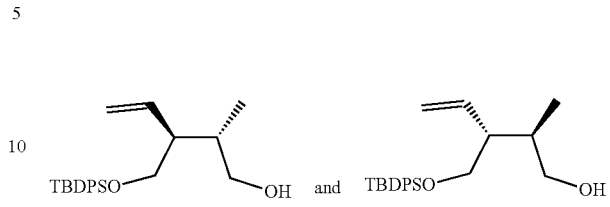

To a solution of (2S,3S)-3-(((tert-butyldiphenylsilyl)oxy)methyl)-N-methoxy-N,2-dimethylpent-4-enamide (1.5 g, 3.52 mmol) in THF (17.62 mL) was added lithium borohydride (Sigma Aldrich; 0.230 g, 10.57 mmol) followed by methanol (0.428 mL, 10.57 mmol). The reaction was stirred at ambient temperature for 3 hours. After this time an additional portion of lithium borohydride (0.230 g, 10.57 mmol) and methanol (0.428 mL, 10.57 mmol) was added and the reaction was stirred at ambient temperature over the weekend. After this time the reaction was diluted with EtOAc (70 mL) and 1M HCl. The separated aqueous layer was extracted with EtOAc and the combined organic extracts were washed with brine, dried over MgSO$_4$, filtered and evaporated in vacuo. Column chromatography (40 g Sift, hexanes:EtOAc, 1:0 to 4:1) gave (2S,3S)-3-(((tert-butyldiphenylsilyl)oxy)methyl)-2-methylpent-4-en-1-ol and (2R,3R)-3-(((tert-butyldiphenylsilyl)oxy)methyl)-2-methylpent-4-en-1-ol (0.84 g, 2.279 mmol, 64.7% yield) as a colorless oil.

Step 5: (2S,3S)-3-(((tert-butyldiphenylsilyl)oxy)methyl)-2-methylpent-4-en-1-yl methanesulfonate and (2R,3R)-3-(((tert-butyldiphenylsilyl)oxy)methyl)-2-methylpent-4-en-1-yl methanesulfonate

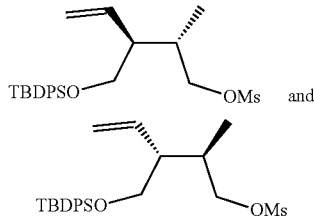

To a stirred solution of (2S,3S)-3-(((tert-butyldiphenylsilyl)oxy)methyl)-2-methylpent-4-en-1-ol (0.83 g, 2.252 mmol) in DCM (22.52 mL) was added triethylamine (Acros Organics; 0.565 mL, 4.05 mmol) and methanesulfonyl chloride (Sigma Aldrich; 0.228 mL, 2.93 mmol). The reaction was stirred at ambient temperature for 30 minutes. After this time the reaction was partitioned between DCM and NaHCO$_3$. The separated organic layer was washed with brine, dried over MgSO$_4$, filtered and evaporated in vacuo to give (2S,3S)-3-(((tert-butyldiphenylsilyl)oxy)methyl)-2-methylpent-4-en-1-yl methanesulfonate and (2R,3R)-3-(((tert-butyldiphenylsilyl)oxy)methyl)-2-methylpent-4-en-1-yl methanesulfonate (0.91 g, 2.037 mmol, 90% yield) as a light yellow oil.

Step 6: 2-(((2S,3S)-3-(((tert-butyldiphenylsilyl)oxy)methyl)-2-methylpent-4-en-1-yl)thio)pyrimidine and 2-(((2R,3R)-3-(((tert-butyldiphenylsilyl)oxy)methyl)-2-methylpent-4-en-1-yl)thio)pyrimidine

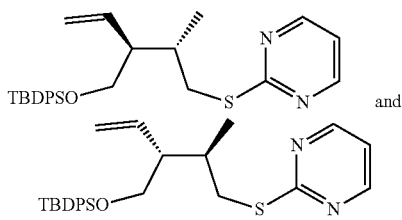

To a solution of (2S,3S)-3-(((tert-butyldiphenylsilyl)oxy)methyl)-2-methylpent-4-en-1-yl methanesulfonate and (2S,3S)-3-(((tert-butyldiphenylsilyl)oxy)methyl)-2-methylpent-4-en-1-yl methanesulfonate (0.91 g, 2.037 mmol) in DMF (6.79 mL) was added 2-mercaptopyrimidine (TCI; 0.274 g, 2.445 mmol) and potassium carbonate (0.422 g, 3.06 mmol). The reaction was stirred at ambient temperature for 20 minutes and at 50° C. for 3 hours. After this time the reaction was cooled to ambient temperature and partitioned between EtOAc and brine. The separated organic layer was washed with brine, dried over $MgSO_4$, filtered and evaporated in vacuo. Column chromatography (24 g Sift, hexanes:EtOAc, 1:0 to 4:1) gave 2-(((2S,3S)-3-(((tert-butyldiphenylsilyl)oxy)methyl)-2-methylpent-4-en-1-yl)thio)pyrimidine and 2-(((2R,3R)-3-(((tert-butyldiphenylsilyl)oxy)methyl)-2-methylpent-4-en-1-yl)thio)pyrimidine (0.63 g, 1.362 mmol, 66.8% yield).

Step 7: 2-(((2S,3S)-3-(((tert-butyldiphenylsilyl)oxy)methyl)-2-methylpent-4-en-1-yl)sulfonyl)pyrimidine and 2-(((2R,3R)-3-(((tert-butyldiphenylsilyl)oxy)methyl)-2-methylpent-4-en-1-yl)sulfonyl)pyrimidine

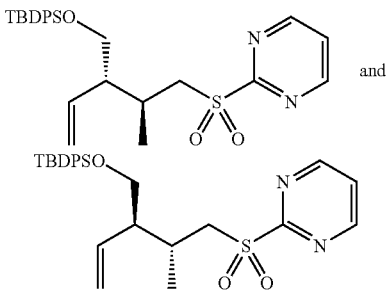

To a well stirred mixture of tetrabutylammonium sulfate, 50 wt. % solution in water (Sigma Aldrich; 78 µL, 0.067 mmol), phenylphosphonic acid (Sigma Aldrich; 7.46 µL, 0.067 mmol) and sodium tungstate dihydrate (Sigma Aldrich; 22.10 mg, 0.067 mmol) was added hydrogen peroxide (Sigma Aldrich; 342 µL, 3.35 mmol) and the reaction was stirred at ambient temperature for 5 minutes. After this time a solution of 2-(((2S,3S)-3-(((tert-butyldiphenylsilyl)oxy)methyl)-2-methylpent-4-en-1-yl)thio)pyrimidine and (2R,3R)-3-(((tert-butyldiphenylsilyl)oxy)methyl)-2-methylpent-4-en-1-yl methanesulfonate (620 mg, 1.340 mmol) in toluene (1340 µL) was added and the reaction was stirred at ambient temperature for 30 minutes and at 55° C. for 1 hour. After this time LC/MS shows desired product. The reaction was stored in the freezer overnight. Next morning the reaction was partitioned between EtOAc and water. The separated aqueous layer was extracted with EtOAc and the combined organic extracts were dried over $MgSO_4$, filtered and evaporated in vacuo. Column chromatography (12 g $SiO_2$, hexanes:EtOAc, 1:0 to 2:1) gave 2-(((2S,3S)-3-(((tert-butyldiphenylsilyl)oxy)methyl)-2-methylpent-4-en-1-yl)sulfonyl)pyrimidine and 2-(((2R,3R)-3-(((tert-butyldiphenylsilyl)oxy)methyl)-2-methylpent-4-en-1-yl)sulfonyl)pyrimidine (612 mg, 1.237 mmol, 92% yield).

Step 8: sodium (2S,3S)-3-(((tert-butyldiphenylsilyl)oxy)methyl)-2-methylpent-4-ene-1-sulfinate and sodium (2R,3R)-3-(((tert-butyldiphenylsilyl)oxy)methyl)-2-methylpent-4-ene-1-sulfinate

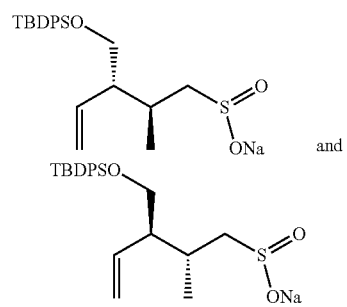

To a stirred solution of 2-(((2S,3S)-3-(((tert-butyldiphenylsilyl)oxy)methyl)-2-methylpent-4-en-1-yl)sulfonyl)pyrimidine and 2-(((2R,3R)-3-(((tert-butyldiphenylsilyl)oxy)methyl)-2-methylpent-4-en-1-yl)sulfonyl)pyrimidine (0.62 g, 1.253 mmol) in MeOH (12.53 mL) was added sodium methoxide (0.344 mL, 1.504 mmol). The reaction was stirred at ambient temperature for 45 minutes. After this time the reaction was evaporated in vacuo providing sodium (2S,3S)-3-(((tert-butyldiphenylsilyl)oxy)methyl)-2-methylpent-4-ene-1-sulfinate and sodium (2R,3R)-3-(((tert-butyldiphenylsilyl)oxy)methyl)-2-methylpent-4-ene-1-sulfinate (0.62 g). Analytical Data were consistent with desired product (contaminated with 2-methoxypyrimidine). This material was used without further purification in the next step.

Step 9: (2S,3S)-3-(((tert-butyldiphenylsilyl)oxy)methyl)-2-methylpent-4-ene-1-sulfonamide and (2R,3R)-3-(((tert-butyldiphenylsilyl)oxy)methyl)-2-methylpent-4-ene-1-sulfonamide

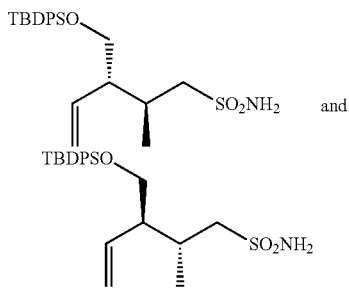

To a stirred solution of sodium (2S,3S)-3-(((tert-butyldiphenylsilyl)oxy)methyl)-2-methylpent-4-ene-1-sulfinate and (2R,3R)-3-(((tert-butyldiphenylsilyl)oxy)methyl)-2-methylpent-4-ene-1-sulfinate (0.55 g, 1.254 mmol) in water (12.54 mL) and MeOH (2 mL) was added sodium acetate (0.206 g, 2.508 mmol) followed by amidoperoxymonosulfuric acid (0.170 g, 1.505 mmol). The reaction was stirred at ambient temperature for 30 minutes and at 50° C. for 1 hour. After this time the reaction was allowed to cool to rt and evaporated in vacuo. The mixture was partitioned between EtOAc and water. The separated aqueous layer was extracted with EtOAc (×2) and the combined organic extracts were dried over MgSO$_4$, filtered and evaporated in vacuo. Column chromatography (12 g SiO$_2$, hexanes:EtOAc, 1:0 to 2:1) gave (2S,3S)-3-(((tert-butyldiphenylsilyl)oxy)methyl)-2-methylpent-4-ene-1-sulfonamide and (2R,3R)-3-(((tert-butyldiphenylsilyl)oxy)methyl)-2-methylpent-4-ene-1-sulfonamide (0.35 g, 0.811 mmol, 64.7% yield).

Step 10: (S)-5-(((1R,2R)-2-((1S,4S,5S,E)-4-(((tert-butyldiphenylsilyl)oxy)methyl)-1-hydroxy-5-methyl-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic Acid and (S)-5-(((1R,2R)-2-((1S,4R,5R,E)-4-(((tert-butyldiphenylsilyl)oxy)methyl)-1-hydroxy-5-methyl-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic Acid

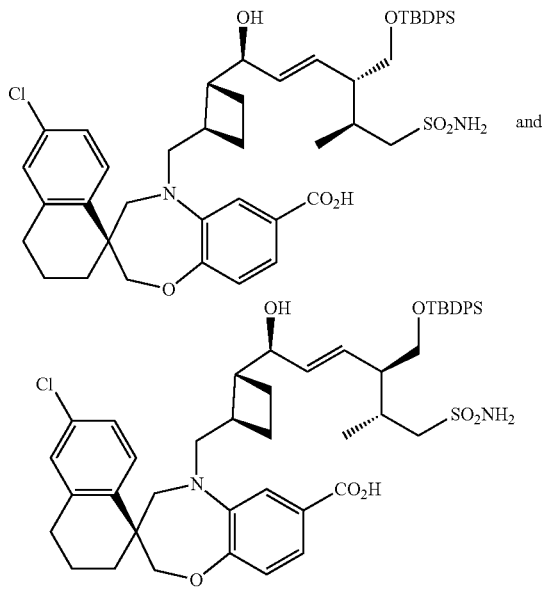

A solution of (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Intermediate AA11A; 100 mg, 0.214 mmol) and (2S,3S)-3-(((tert-butyldiphenylsilyl)oxy)methyl)-2-methylpent-4-ene-1-sulfonamide and (2R,3R)-3-(((tert-butyldiphenylsilyl)oxy)methyl)-2-methylpent-4-ene-1-sulfonamide (Example 126, Step 9; 304 mg, 0.705 mmol) in 1,2-dichloroethane (3053 μL) was degassed for 10 minutes with Ar(g). The reaction was then treated with a solution of (1,3-dimesitylimidazolidin-2-ylidene)(2-isopropoxybenzylidene)ruthenium(VI) chloride (Sigma Aldrich; 13.39 mg, 0.021 mmol) in 1,2-dichloroethane (3053 μL) and stirred at ambient temperature for 1 hour. After this time Ti(iPrO)$_4$ (3 drops) was added and the reaction was stirred at ambient temperature for 4 hours. After this time the catalyst was deactivated by sparging air through the reaction mixture for 5 minutes. SiO$_2$ (ca 1 g) was added to the reaction mixture and the solvent was evaporated in vacuo. The solid was transferred into a solid loading cartridge and purified by column chromatography (4 g SiO$_2$, hexane:acetone, 1:0 to 70:30) to give (S)-5-(((1R,2R)-2-((1S,4S,5S,E)-4-(((tert-butyldiphenylsilyl)oxy)methyl)-1-hydroxy-5-methyl-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid and (S)-5-(((1R,2R)-2-((1S,4R,5R,E)-4-(((tert-butyldiphenylsilyl)oxy)methyl)-1-hydroxy-5-methyl-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid (18 mg, 0.021 mmol, 9.66% yield).

Step 11: (1S,3'R,6'R,7'S,8'E,10'R,11R)-6-chloro-10'-(hydroxymethyl)-7'-methoxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,11'S)-6-chloro-10'-(hydroxymethyl)-7'-methoxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide To a stirred solution of (S)-5-(((1R,2R)-2-((1S,4S,5S,E)-4-(((tert-butyldiphenylsilyl)oxy)methyl)-1-hydroxy-5-methyl-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid and (S)-5-(((1R,2R)-2-((1S,4R,5R,E)-4-(((tert-butyldiphenylsilyl)oxy)methyl)-1-hydroxy-5-methyl-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid (0.018 g, 0.021 mmol) in DCM (10.33 mL) at 0° C. was added N,N-dimethylpyridin-4-amine (4.29 mg, 0.035 mmol) followed by N1-((ethylimino)methylene)-N3,N3-dimethylpropane-1,3-diamine hydrochloride (Oakwood; 7.92 mg, 0.041 mmol). The reaction was stirred at ambient temperature overnight. After this time the reaction was partitioned between DCM and NaHCO$_3$. The separated aqueous layer was extracted with DCM and the combined organic extracts were dried over MgSO$_4$, filtered and evaporated in vacuo. The crude product (15 mg) was dissolved in THF (1.5 mL) and sodium hydride (2.478 mg, 0.103 mmol) was added followed by iodomethane (6.46 μl, 0.103 mmol) and the reaction was stirred at ambient temperature for 4 hours. After this time the reaction was partitioned between EtOAc and 1M HCl. The separated organic layer was dried over MgSO$_4$, filtered and evaporated in vacuo. The crude material (14 mg) thus obtained was dissolved in THF and treated with TBAF (Sigma Aldrich, 1M solution in THF; 0.207 mL, 0.207 mmol). The reaction was stirred at ambient temperature for 3 days. After this time the reaction was partitioned between EtOAc and water. The separated organic layer was dried over MgSO$_4$, filtered and evaporated in vacuo. Column chromatography (4 g SiO$_2$, DCM:Acetone, 1:0 to 3:1) gave (1S,3'R,6'R,7'S,8'E,10'R,11'R)-6-chloro-10'-(hydroxymethyl)-7'-methoxy-11'-methyl-3,4-dihydro- 2H,15'H-spiro[naphthalene-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'S,11'S)-6-chloro-10'-(hydroxymethyl)-7'-methoxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (1.4 mg, 2.225 μmol, 10.77% yield) as a single diastereomer. ¹H NMR (400 MHz, CD₂Cl₂) δ 7.71 (d, J=8.4 Hz, 1H), 7.17 (dd, J=2.2, 8.5 Hz, 1H), 7.09 (d, J=2.3 Hz, 1H), 6.91 (d, J=0.8 Hz, 2H), 6.84 (s, 1H), 5.84 (dd, J=8.3, 15.4 Hz, 1H), 5.54 (dd, J=8.9, 15.6 Hz, 1H), 4.31 (dd, J=3.9, 15.3 Hz, 1H), 4.08 (s, 2H), 3.83 (d, J=15.7 Hz, 1H), 3.76-3.64 (m, 3H), 3.63-3.55 (m, 2H), 3.24 (d, J=14.5 Hz, 1H), 3.20 (s, 3H), 3.08 (dd, J=9.1, 15.2 Hz, 1H), 3.03 (dd, J=10.3, 15.4 Hz, 1H), 2.85-2.70 (m, 2H), 2.52-2.37 (m, 2H), 2.37-2.26 (m, 1H), 2.10-2.01 (m, 1H), 1.98-1.89 (m, 2H), 1.87-1.73 (m, 3H), 1.72-1.63 (m, 2H), 1.41-1.36 (m, 1H), 1.22 (d, J=7.0 Hz, 3H). MS (ESI, +ve ion) m/z 629.2 (M+H)⁺.

Example 127. (1S,3'R,6'R,7'S,8'E,10'S,12'S)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'S,12'R)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,12'R)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,12'S)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

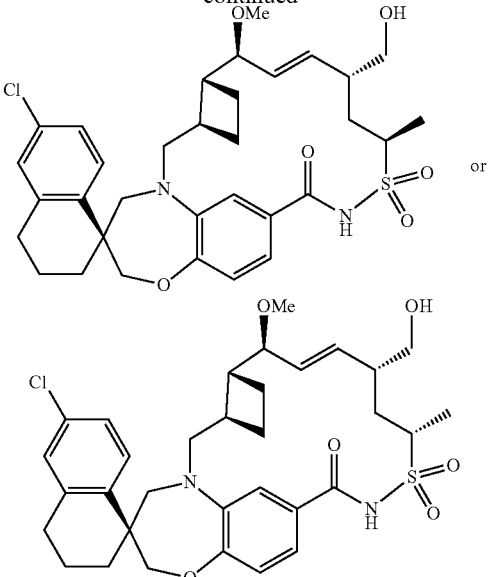

Step 1: (Z)-4-((tert-butyldiphenylsilyl)oxy)but-2-en-1-ol

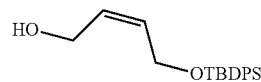

To a stirred solution of cis-2-butene-1,4-diol (10.00 mL, 114 mmol), triethylamine (15.82 mL, 114 mmol) and DMAP (0.693 g, 5.68 mmol) in DCM (100 mL) was added TBDPS-Cl (14.58 mL, 56.8 mmol) in DCM (50 mL) dropwise via an addition funnel. After the addition was complete the reaction was stirred at ambient temperature overnight. After this time water was added to the reaction. The separated organic layer was washed with 1M HCl, dried over MgSO₄, filtered and evaporated in vacuo. The crude product was loaded into a 40 g SiO₂ cartridge and purified by column (120 g redisep gold, hexanes:EtOAc, 1:0 to 4:1) to give (Z)-4-((tert-butyldiphenylsilyl)oxy)but-2-en-1-ol (13 g, 39.8 mmol, 35.1% yield).

Step 2: (S)-ethyl 3-(((tert-butyldiphenylsilyl)oxy)methyl)pent-4-enoate and (R)-ethyl 3-(((tert-butyldiphenylsilyl)oxy)methyl)pent-4-enoate

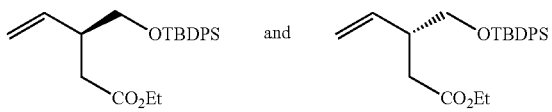

Triethyl orthoacetate (Sigma Aldrich; 37.4 mL, 203 mmol) and propionic acid (Sigma Aldrich; 0.149 mL, 1.991 mmol) were added to a solution of (Z)-4-((tert-butyldiphenylsilyl)oxy)but-2-en-1-ol (13 g, 39.8 mmol) in p-xylene (160 mL). The mixture was heated at 140° C. for 3 hours with removal of ethanol using a short pad distillation kit. After this time the reaction was allowed to cool to ambient temperature and water was added to the reaction. The separated organic layer was washed with NaHCO₃ (sat. aq. solution) and then it was dried over MgSO₄, filtered and evaporated in vacuo. Column chromatography (120 g SiO₂, hexanes:EtOAc, 1:0 to 4:1) gave (S)-ethyl 3-(((tert-butyldiphenylsilyl)oxy)methyl)pent-4-enoate and (R)-ethyl 3-(((tert-butyldiphenylsilyl)oxy)methyl)pent-4-enoate (11.9 g, 30.0 mmol, 75% yield) as a colorless oil.

Step 3: (S)-3-(((tert-butyldiphenylsilyl)oxy)methyl)pent-4-enal and (R)-3-(((tert-butyldiphenylsilyl)oxy)methyl)pent-4-enal

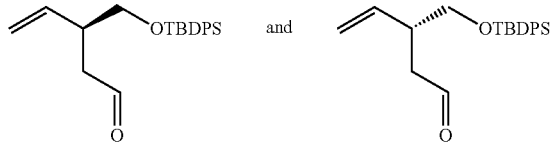

To a stirred solution of (S)-ethyl 3-(((tert-butyldiphenylsilyl)oxy)methyl)pent-4-enoate and (R)-ethyl 3-(((tert-butyldiphenylsilyl)oxy)methyl)pent-4-enoate (11.9 g, 30.0 mmol) in toluene (150 mL) at −78° C. was added dropwise via syringe a solution of DIBAl-H (Sigma Aldrich, 1M in hexanes; 33.0 mL, 33.0 mmol). The reaction was stirred at −78° C. for 1 hour. After this time the reaction was cooled to 0° C. and treated with 1.32 mL of water, 1.32 mL of 15% aq. NaOH and 3 mL of water. The reaction was stirred for 30 minutes at ambient temperature. After this time EtOAc (200 mL) was added to the reaction followed by water (50 mL) and 1M NaOH (50 mL) and the mixture was stirred for 10 minutes. The separated organic layer was dried over MgSO₄, filtered and evaporated in vacuo to give crude (S)-3-(((tert-butyldiphenylsilyl)oxy)methyl)pent-4-enal and (R)-3-(((tert-butyldiphenylsilyl)oxy)methyl)pent-4-enal (10 g, 28.4 mmol, 95% yield). This material was used without further purification in the next step.

Step 4: (2R,4S)-4-(((tert-butyldiphenylsilyl)oxy)methyl)hex-5-en-2-ol or (2S,4S)-4-(((tert-butyldiphenylsilyl)oxy)methyl)hex-5-en-2-OL or (2S,4R)-4-(((tert-butyldiphenylsilyl)oxy)methyl)hex-5-en-2-ol or (2R,4R)-4-(((tert-butyldiphenylsilyl)oxy)methyl)hex-5-en-2-OL and (2R,4S)-4-(((tert-butyldiphenylsilyl)oxy)methyl)hex-5-en-2-OL or (2S,4S)-4-(((tert-butyldiphenylsilyl)oxy)methyl)hex-5-en-2-OL or (2S,4R)-4-(((tert-butyldiphenylsilyl)oxy)methyl)hex-5-en-2-ol or (2R,4R)-4-(((tert-butyldiphenylsilyl)oxy)methyl)hex-5-en-2-ol

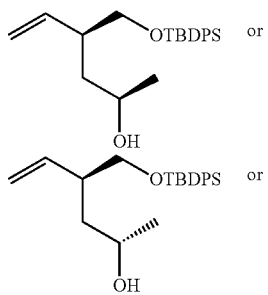

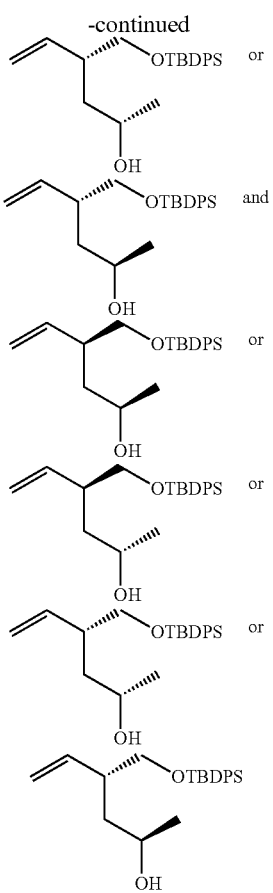

To a stirred solution of (S)-3-(((tert-butyldiphenylsilyl)oxy)methyl)pent-4-enal and (R)-3-(((tert-butyldiphenylsilyl)oxy)methyl)pent-4-enal (6.1 g, 17.30 mmol) in THF (87 mL) at 0° C. under a N₂ atmosphere was added dropwise via syringe a solution of methylmagnesium bromide (Sigma Aldrich, 1.4 M in THF/toluene; 13.60 mL, 19.03 mmol). The reaction was stirred while allowing to warm to ambient temperature for 1 hour. After this time the reaction was cooled to 0° C. and carefully treated with 1M HCl (sat. aq. solution) and EtOAc. The mixture was stirred at ambient temperature for 10 minutes. After this time the reaction was partitioned between EtOAc and water. The separated organic layer was washed with brine, dried over MgSO₄, filtered and evaporated in vacuo to give a 1:1 mixture of (2R,4S)-4-(((tert-butyldiphenylsilyl)oxy)methyl)hex-5-en-2-ol or (2S,4S)-4-(((tert-butyldiphenylsilyl)oxy)methyl)hex-5-en-2-ol or (2S,4R)-4-(((tert-butyldiphenylsilyl)oxy)methyl)hex-5-en-2-ol or (2R,4R)-4-(((tert-butyldiphenylsilyl)oxy)methyl)hex-5-en-2-ol and (2R,4S)-4-(((tert-butyldiphenylsilyl)oxy)methyl)hex-5-en-2-ol or (2S,4S)-4-(((tert-butyldiphenylsilyl)oxy)methyl)hex-5-en-2-ol or (2S,4R)-4-(((tert-butyldiphenylsilyl)oxy)methyl)hex-5-en-2-ol or (2R,4R)-4-(((tert-butyldiphenylsilyl)oxy)methyl)hex-5-en-2-ol as the first eluting major component (3.5 g, 9.496 mmol, 54.9%).

Further elution provided a 4:1 mixture of (2R,4S)-4-(((tert-butyldiphenylsilyl)oxy)methyl)hex-5-en-2-ol or (2S,4S)-4-(((tert-butyldiphenylsilyl)oxy)methyl)hex-5-en-2-ol or (2S,4R)-4-(((tert-butyldiphenylsilyl)oxy)methyl)hex-5-en-2-ol or (2R,4R)-4-(((tert-butyldiphenylsilyl)oxy)methyl)hex-5-en-2-ol and (2R,4S)-4-(((tert-butyldiphenylsilyl)oxy)methyl)hex-5-en-2-ol or (2S,4S)-4-(((tert-butyldiphenylsilyl)oxy)methyl)hex-5-en-2-ol or (2S,4R)-4-(((tert-butyldiphenylsilyl)oxy)methyl)hex-5-en-2-ol or (2R,4R)-4-(((tert-butyldiphenylsilyl)oxy)methyl)hex-5-en-2-ol as the second eluting minor component (2.0 g, 5.426 mmol, 31.3%).

Step 5: (2R,4S)-4-(((tert-butyldiphenylsilyl)oxy) methyl)hex-5-en-2-yl methanesulfonate or (2S,4S)-4-(((tert-butyldiphenyl silyl)oxy)methyl)hex-5-en-2-yl methanesulfonate or (2S,4R)-4-(((tert-butyldiphenylsilyl)oxy)methyl)hex-5-en-2-yl methanesulfonate or (2R,4R)-4-(((tert-butyldiphenyl silyl)oxy)methyl)hex-5-en-2-yl methanesulfonate and (2R,4S)-4-(((tert-butyldiphenylsilyl)oxy)methyl) hex-5-en-2-yl methanesulfonate or (2S,4S)-4-(((tert-butyldiphenylsilyl)oxy)methyl)hex-5-en-2-yl methanesulfonate or (2S,4R)-4-(((tert-butyldiphenylsilyl) oxy)methyl)hex-5-en-2-yl methanesulfonate or (2R,4R)-4-(((tert-butyldiphenylsilyl)oxy)methyl)hex-5-en-2-yl methanesulfonate

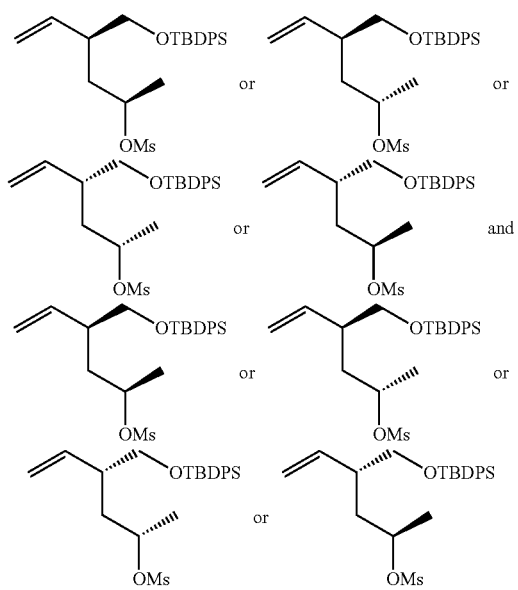

To a stirred solution of a mixture of (2R,4S)-4-(((tert-butyldiphenylsilyl)oxy)methyl)hex-5-en-2-ol or (2S,4S)-4-(((tert-butyldiphenylsilyl)oxy)methyl)hex-5-en-2-ol or (2S,4R)-4-(((tert-butyldiphenylsilyl)oxy)methyl)hex-5-en-2-ol or (2R,4R)-4-(((tert-butyldiphenylsilyl)oxy)methyl)hex-5-en-2-ol and (2R,4S)-4-(((tert-butyldiphenylsilyl)oxy) methyl)hex-5-en-2-ol or (2S,4S)-4-(((tert-butyldiphenylsilyl)oxy)methyl)hex-5-en-2-ol or (2S,4R)-4-(((tert-butyldiphenylsilyl)oxy)methyl)hex-5-en-2-ol or (2R,4R)-4-(((tert-butyldiphenylsilyl)oxy)methyl)hex-5-en-2-ol (Example 12, step 4, second eluting minor component; 2.0 g, 5.426 mmol) in DCM (27.1 mL) at 0° C. under a N₂ atmosphere was added triethylamine (1.134 mL, 8.14 mmol) followed by methanesulfonyl chloride (Sigma Aldrich; 0.465 mL, 5.97 mmol). The reaction was stirred at 0° C. for 5 minutes and then the cooling bath was removed and the reaction was stirred at ambient temperature for 30 minutes. After this time the reaction was partitioned between DCM and 1M HCl. The separated organic layer was washed with NaHCO₃ (sat. aq. solution), brine (sat. aq. solution) and then it was dried over MgSO₄, filtered and evaporated in vacuo to give (2R,4S)-4-(((tert-butyldiphenylsilyl)oxy)methyl) hex-5-en-2-yl methanesulfonate or (2S,4S)-4-(((tert-butyldiphenylsilyl)oxy)methyl)hex-5-en-2-yl methanesulfonate or (2S,4R)-4-(((tert-butyldiphenylsilyl)oxy)methyl)hex-5-en-2-yl methanesulfonate or (2R,4R)-4-(((tert-butyldiphenylsilyl)oxy)methyl)hex-5-en-2-yl methanesulfonate and (2R,4S)-4-(((tert-butyldiphenylsilyl)oxy)methyl)hex-5-en-2-yl methanesulfonate or (2S,4S)-4-(((tert-butyldiphenylsilyl)oxy)methyl)hex-5-en-2-yl methanesulfonate or (2S,4R)-4-(((tert-butyldiphenylsilyl)oxy)methyl)hex-5-en-2-yl methanesulfonate or (2R,4R)-4-(((tert-butyldiphenylsilyl) oxy)methyl)hex-5-en-2-yl methanesulfonate (2.4 g, 5.37 mmol, 99% yield).

Step 6: 2-(((2S,4S)-4-(((tert-butyldiphenylsilyl)oxy) methyl)hex-5-en-2-yl)thio)pyrimidine or 2-(((2R,4S)-4-(((tert-butyldiphenylsilyl)oxy)methyl)hex-5-en-2-yl)thio)pyrimidine or 2-(((2R,4R)-4-(((tert-butyldiphenylsilyl)oxy)methyl)hex-5-en-2-yl)thio) pyrimidine or 2-(((2S,4R)-4-(((tert-butyldiphenylsilyl)oxy)methyl)hex-5-en-2-yl)thio) pyrimidine and 2-(((2S,4S)-4-(((tert-butyldiphenylsilyl)oxy)methyl)hex-5-en-2-yl)thio) pyrimidine or 2-(((2R,4S)-4-(((tert-butyldiphenylsilyl)oxy)methyl)hex-5-en-2-yl)thio) pyrimidine or 2-(((2R,4R)-4-(((tert-butyldiphenylsilyl)oxy)methyl)hex-5-en-2-yl)thio) pyrimidine or 2-(((2S,4R)-4-(((tert-butyldiphenylsilyl)oxy)methyl)hex-5-en-2-yl)thio) pyrimidine

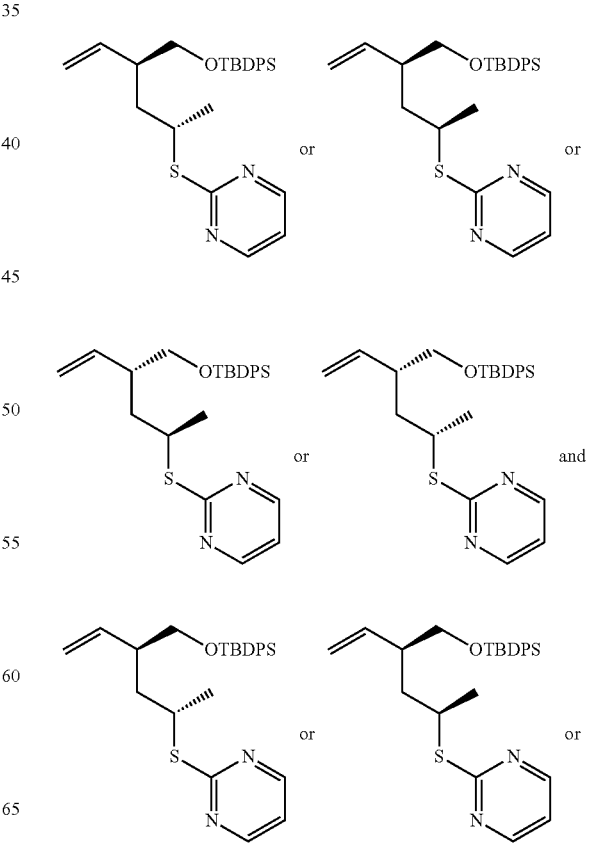

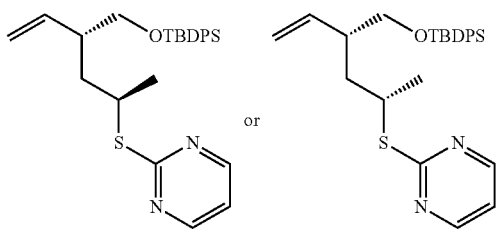

To a stirred solution of (2R,4S)-4-(((tert-butyldiphenylsilyl)oxy)methyl)hex-5-en-2-yl methanesulfonate or (2S,4S)-4-(((tert-butyldiphenylsilyl)oxy)methyl)hex-5-en-2-yl methanesulfonate or (2S,4R)-4-(((tert-butyldiphenylsilyl)oxy)methyl)hex-5-en-2-yl methanesulfonate or (2R,4R)-4-(((tert-butyldiphenylsilyl)oxy)methyl)hex-5-en-2-yl methanesulfonate and (2R,4S)-4-(((tert-butyldiphenylsilyl)oxy)methyl)hex-5-en-2-yl methanesulfonate or (2S,4S)-4-(((tert-butyldiphenylsilyl)oxy)methyl)hex-5-en-2-yl methanesulfonate or (2S,4R)-4-(((tert-butyldiphenylsilyl)oxy)methyl)hex-5-en-2-yl methanesulfonate or (2R,4R)-4-(((tert-butyldiphenylsilyl)oxy)methyl)hex-5-en-2-yl methanesulfonate (2.4 g, 5.37 mmol) in DMF (10.75 mL) was added potassium carbonate (0.965 g, 6.98 mmol) and 2-mercaptopyrimidine (0.723 g, 6.45 mmol) and the mixture was stirred at ambient temperature for 1 hour. After this time the reaction was heated at 60° C. for 90 minutes and then it was treated with more DMF (8 mL) and stirred at 45° C. overnight. After this time an additional portion of 2-mercaptopyrimidine (0.3 g) and potassium carbonate (0.4 g) was added and the reaction was stirred at 60° C. for 40 minutes and at 100° C. for 3 hours. After this time the reaction was allowed to cool to ambient temperature and partitioned between EtOAc and brine. The separated organic layer was washed with brine, dried over MgSO$_4$, filtered and evaporated in vacuo. Column chromatography (40 g SiO$_2$, hexanes:EtOAc, 1:0 to 3:1) gave 2-(((2S,4S)-4-(((tert-butyldiphenylsilyl)oxy)methyl)hex-5-en-2-yl)thio)pyrimidine or 2-(((2R,4S)-4-(((tert-butyldiphenylsilyl)oxy)methyl)hex-5-en-2-yl)thio)pyrimidine or 2-(((2R,4R)-4-(((tert-butyldiphenylsilyl)oxy)methyl)hex-5-en-2-yl)thio)pyrimidine or 2-(((2S,4R)-4-(((tert-butyldiphenylsilyl)oxy)methyl)hex-5-en-2-yl)thio)pyrimidine and 2-(((2S,4S)-4-(((tert-butyldiphenylsilyl)oxy)methyl)hex-5-en-2-yl)thio)pyrimidine or 2-(((2R,4S)-4-(((tert-butyldiphenylsilyl)oxy)methyl)hex-5-en-2-yl)thio)pyrimidine or 2-(((2R,4R)-4-(((tert-butyldiphenylsilyl)oxy)methyl)hex-5-en-2-yl)thio)pyrimidine or 2-(((2S,4R)-4-(((tert-butyldiphenylsilyl)oxy)methyl)hex-5-en-2-yl)thio)pyrimidine (1.6 g, 3.46 mmol, 64.4% yield).

Step 7: 2-(((2S,4S)-4-(((tert-butyldiphenylsilyl)oxy)methyl)hex-5-en-2-yl)sulfonyl)pyrimidine or 2-(((2R,4S)-4-(((tert-butyldiphenylsilyl)oxy)methyl)hex-5-en-2-yl)sulfonyl)pyrimidine or 2-(((2R,4R)-4-(((tert-butyldiphenylsilyl)oxy)methyl)hex-5-en-2-yl)sulfonyl)pyrimidine or 2-(((2S,4R)-4-(((tert-butyldiphenylsilyl)oxy)methyl)hex-5-en-2-yl)sulfonyl)pyrimidine and 2-(((2S,4S)-4-(((tert-butyldiphenylsilyl)oxy)methyl)hex-5-en-2-yl)sulfonyl)pyrimidine or 2-(((2R,4S)-4-(((tert-butyldiphenylsilyl)oxy)methyl)hex-5-en-2-yl)sulfonyl)pyrimidine or 2-(((2R,4R)-4-(((tert-butyldiphenylsilyl)oxy)methyl)hex-5-en-2-yl)sulfonyl)pyrimidine or 2-(((2S,4R)-4-(((tert-butyldiphenylsilyl)oxy)methyl)hex-5-en-2-yl)sulfonyl)pyrimidine

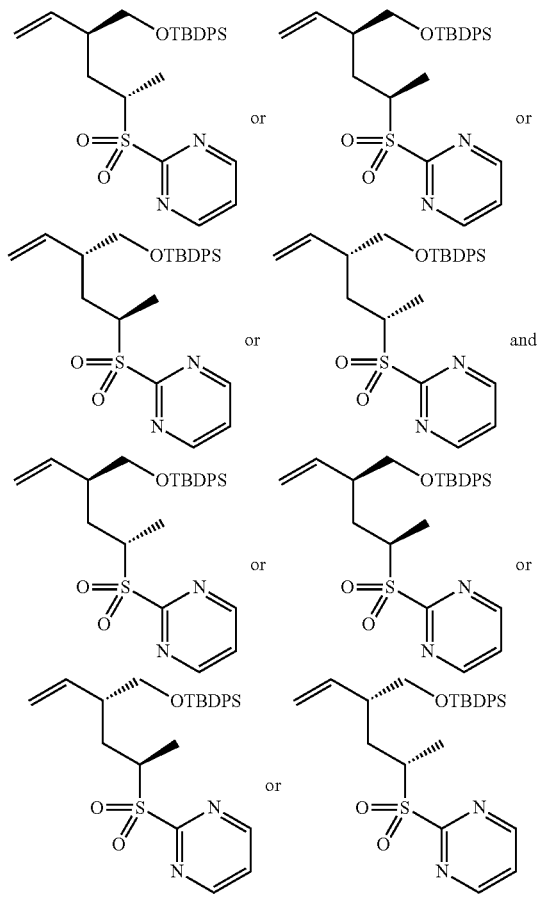

To a well stirred mixture of tetrabutylammonium sulfate, 50 wt. % solution in water (Sigma Aldrich; 0.201 mL, 0.173 mmol), phenylphosphonic acid (Sigma Aldrich; 0.027 g, 0.173 mmol) and sodium tungstate dihydrate (Sigma Aldrich; 0.057 g, 0.173 mmol) was added hydrogen peroxide (0.883 mL, 8.64 mmol) and the reaction was stirred at ambient temperature for 5 minutes. After this time a solution of 2-(((2S,4S)-4-(((tert-butyldiphenylsilyl)oxy)methyl)hex-5-en-2-yl)thio)pyrimidine or 2-(((2R,4S)-4-(((tert-butyldiphenylsilyl)oxy)methyl)hex-5-en-2-yl)thio)pyrimidine or 2-(((2R,4R)-4-(((tert-butyldiphenylsilyl)oxy)methyl)hex-5-en-2-yl)thio)pyrimidine or 2-(((2S,4R)-4-(((tert-butyldiphenylsilyl)oxy)methyl)hex-5-en-2-yl)thio)pyrimidine and 2-(((2S,4S)-4-(((tert-butyldiphenylsilyl)oxy)methyl)hex-5-en-2-yl)thio)pyrimidine or 2-(((2R,4S)-4-(((tert-butyldiphenylsilyl)oxy)methyl)hex-5-en-2-yl)thio)pyrimidine or 2-(((2R,4R)-4-(((tert-butyldiphenylsilyl)oxy)methyl)hex-5-en-2-yl)thio)pyrimidine or 2-(((2S,4R)-4-(((tert-butyldiphenylsilyl)oxy)methyl)hex-5-en-2-yl)thio)pyrimidine (1.6 g, 3.46 mmol) in toluene (3.46 mL) was added and the reaction was stirred at ambient temperature overnight. After this time the reaction was partitioned between EtOAc and water. The separated organic layer was washed with Na₂S₂O₃, NaHSO₃ and brine (at this stage organic layer tested negative for peroxides using Quantofix strips), dried over MgSO₄, filtered and evaporated in vacuo. Purification by column chromatography (24 g SiO₂, hexanes:EtOAc, 1:0 to 2:1) gave 2-(((2S,4S)-4-(((tert-butyldiphenylsilyl)oxy)methyl)hex-5-en-2-yl)sulfonyl)pyrimidine or 2-(((2R,4S)-4-(((tert-butyldiphenylsilyl)oxy)methyl)hex-5-en-2-yl)sulfonyl)pyrimidine or 2-(((2R,4R)-4-(((tert-butyldiphenylsilyl)oxy)methyl)hex-5-en-2-yl)sulfonyl)pyrimidine or 2-(((2S,4R)-4-(((tert-butyldiphenylsilyl)oxy)methyl)hex-5-en-2-yl)sulfonyl)pyrimidine and 2-(((2S,4S)-4-(((tert-butyldiphenylsilyl)oxy)methyl)hex-5-en-2-yl)sulfonyl)pyrimidine or 2-(((2R,4S)-4-(((tert-butyldiphenylsilyl)oxy)methyl)hex-5-en-2-yl)sulfonyl)pyrimidine or 2-(((2R,4R)-4-(((tert-butyldiphenylsilyl)oxy)methyl)hex-5-en-2-yl)sulfonyl)pyrimidine or 2-(((2S,4R)-4-(((tert-butyldiphenylsilyl)oxy)methyl)hex-5-en-2-yl)sulfonyl)pyrimidine (1.33 g, 2.69 mmol, 78% yield).

Step 8: sodium (2S,4S)-4-(((tert-butyldiphenylsilyl)oxy)methyl)hex-5-ene-2-sulfinate or sodium (2R,4S)-4-(((tert-butyldiphenylsilyl)oxy)methyl)hex-5-ene-2-sulfinate or sodium (2R,4R)-4-(((tert-butyldiphenylsilyl)oxy)methyl)hex-5-ene-2-sulfinate or sodium (2S,4R)-4-(((tert-butyldiphenylsilyl)oxy)methyl)hex-5-ene-2-sulfinate and sodium (2S,4S)-4-(((tert-butyldiphenylsilyl)oxy)methyl)hex-5-ene-2-sulfinate or sodium (2R,4S)-4-(((tert-butyldiphenylsilyl)oxy)methyl)hex-5-ene-2-sulfinate or sodium (2R,4R)-4-(((tert-butyldiphenylsilyl)oxy)methyl)hex-5-ene-2-sulfinate or sodium (2S,4R)-4-(((tert-butyldiphenylsilyl)oxy)methyl)hex-5-ene-2-sulfinate

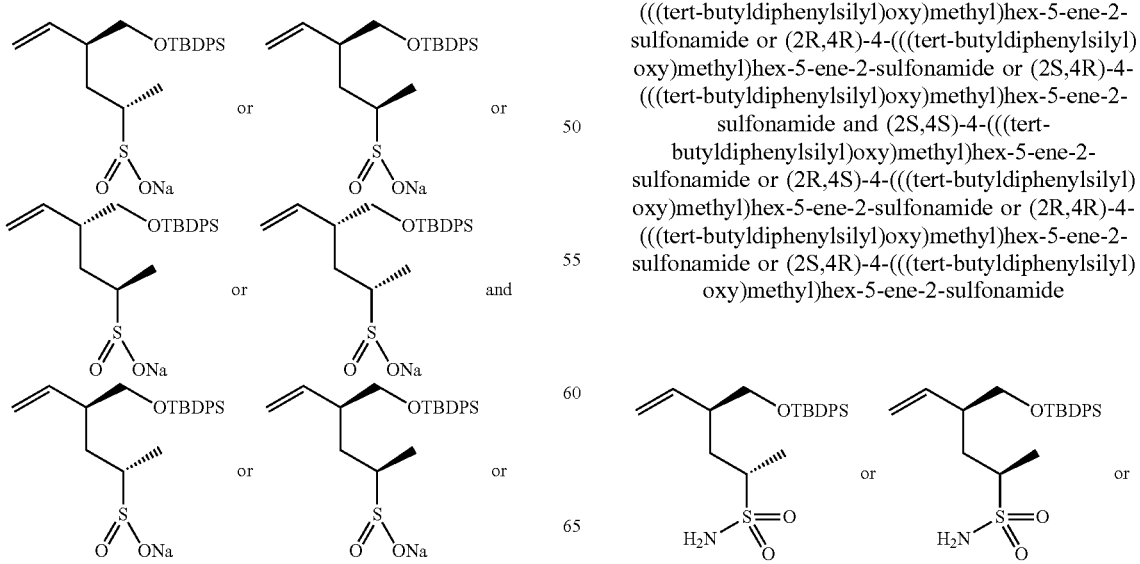

To a stirred solution of 2-(((2S,4S)-4-(((tert-butyldiphenylsilyl)oxy)methyl)hex-5-en-2-yl)sulfonyl)pyrimidine or 2-(((2R,4S)-4-(((tert-butyldiphenylsilyl)oxy)methyl)hex-5-en-2-yl)sulfonyl)pyrimidine or 2-(((2R,4R)-4-(((tert-butyldiphenylsilyl)oxy)methyl)hex-5-en-2-yl)sulfonyl)pyrimidine or 2-(((2S,4R)-4-(((tert-butyldiphenylsilyl)oxy)methyl)hex-5-en-2-yl)sulfonyl)pyrimidine and 2-(((2S,4S)-4-(((tert-butyldiphenylsilyl)oxy)methyl)hex-5-en-2-yl)sulfonyl)pyrimidine or 2-(((2R,4S)-4-(((tert-butyldiphenylsilyl)oxy)methyl)hex-5-en-2-yl)sulfonyl)pyrimidine or 2-(((2R,4R)-4-(((tert-butyldiphenylsilyl)oxy)methyl)hex-5-en-2-yl)sulfonyl)pyrimidine or 2-(((2S,4R)-4-(((tert-butyldiphenylsilyl)oxy)methyl)hex-5-en-2-yl)sulfonyl)pyrimidine (1.33 g, 2.69 mmol) in MeOH (26.9 mL) was added sodium methoxide (0.676 mL, 2.96 mmol) and the reaction was stirred at ambient temperature for 30 minutes. After this time the reaction was evaporated in vacuo to give sodium (2S,4S)-4-(((tert-butyldiphenylsilyl)oxy)methyl)hex-5-ene-2-sulfinate or sodium (2R,4S)-4-(((tert-butyldiphenylsilyl)oxy)methyl)hex-5-ene-2-sulfinate or sodium (2R,4R)-4-(((tert-butyldiphenylsilyl)oxy)methyl)hex-5-ene-2-sulfinate or sodium (2S,4R)-4-(((tert-butyldiphenylsilyl)oxy)methyl)hex-5-ene-2-sulfinate and sodium (2S,4S)-4-(((tert-butyldiphenylsilyl)oxy)methyl)hex-5-ene-2-sulfinate or sodium (2R,4S)-4-(((tert-butyldiphenylsilyl)oxy)methyl)hex-5-ene-2-sulfinate or sodium (2R,4R)-4-(((tert-butyldiphenylsilyl)oxy)methyl)hex-5-ene-2-sulfinate or sodium (2S,4R)-4-(((tert-butyldiphenylsilyl)oxy)methyl)hex-5-ene-2-sulfinate (contaminated with 2-methoxypyrimidine; 1.17 g, 2.67 mmol, 99% yield).

Step 9: (2S,4S)-4-(((tert-butyldiphenylsilyl)oxy)methyl)hex-5-ene-2-sulfonamide or (2R,4S)-4-(((tert-butyldiphenylsilyl)oxy)methyl)hex-5-ene-2-sulfonamide or (2R,4R)-4-(((tert-butyldiphenylsilyl)oxy)methyl)hex-5-ene-2-sulfonamide or (2S,4R)-4-(((tert-butyldiphenylsilyl)oxy)methyl)hex-5-ene-2-sulfonamide and (2S,4S)-4-(((tert-butyldiphenylsilyl)oxy)methyl)hex-5-ene-2-sulfonamide or (2R,4S)-4-(((tert-butyldiphenylsilyl)oxy)methyl)hex-5-ene-2-sulfonamide or (2R,4R)-4-(((tert-butyldiphenylsilyl)oxy)methyl)hex-5-ene-2-sulfonamide or (2S,4R)-4-(((tert-butyldiphenylsilyl)oxy)methyl)hex-5-ene-2-sulfonamide

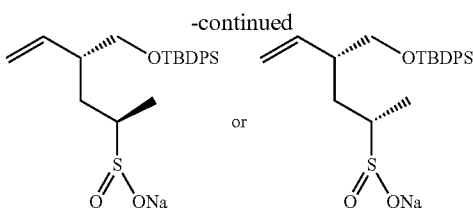

-continued

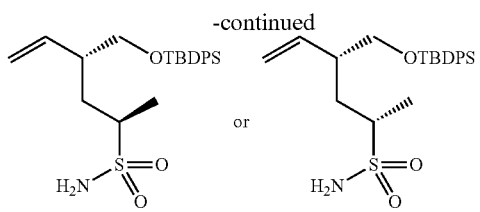

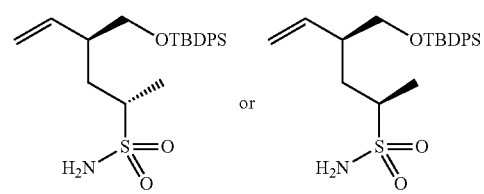

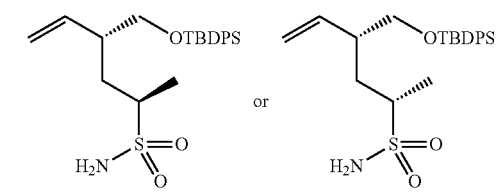

To a stirred solution of sodium (2S,4S)-4-(((tert-butyldiphenylsilyl)oxy)methyl)hex-5-ene-2-sulfinate or sodium (2R,4S)-4-(((tert-butyldiphenylsilyl)oxy)methyl)hex-5-ene-2-sulfinate or sodium (2R,4R)-4-(((tert-butyldiphenylsilyl)oxy)methyl)hex-5-ene-2-sulfinate or sodium (2S,4R)-4-(((tert-butyldiphenylsilyl)oxy)methyl)hex-5-ene-2-sulfinate and sodium (2S,4S)-4-(((tert-butyldiphenylsilyl)oxy)methyl)hex-5-ene-2-sulfinate or sodium (2R,4S)-4-(((tert-butyldiphenylsilyl)oxy)methyl)hex-5-ene-2-sulfinate or sodium (2R,4R)-4-(((tert-butyldiphenylsilyl)oxy)methyl)hex-5-ene-2-sulfinate or sodium (2S,4R)-4-(((tert-butyldiphenylsilyl)oxy)methyl)hex-5-ene-2-sulfinate (1.17 g, 2.67 mmol) in water (26.7 mL) was added sodium acetate (0.438 g, 5.33 mmol) and amidoperoxymonosulfuric acid (0.362 g, 3.20 mmol). The reaction was stirred at 50° C. for 90 minutes. After this time the reaction was cooled to ambient temperature, treated with MeOH (2 mL) and it was sonicated for 2 minutes. The reaction was placed back in the heating bath at 50° C. for 2 hours. After this time the reaction was cooled to ambient temperature and partitioned between 1M NaOH and Ethyl Acetate. The separated aqueous layer was extracted with EtOAc (×2) and the combined organic extracts were washed with brine, dried over MgSO₄, filtered and evaporated in vacuo. Column chromatography (40 g Sift, hexanes:EtOAc, 1:0 to 3:1) gave (2S,4S)-4-(((tert-butyldiphenylsilyl)oxy)methyl)hex-5-ene-2-sulfonamide or (2R,4S)-4-(((tert-butyldiphenylsilyl)oxy)methyl)hex-5-ene-2-sulfonamide or (2R,4R)-4-(((tert-butyldiphenylsilyl)oxy)methyl)hex-5-ene-2-sulfonamide or (2S,4R)-4-(((tert-butyldiphenylsilyl)oxy)methyl)hex-5-ene-2-sulfonamide and (2S,4S)-4-(((tert-butyldiphenylsilyl)oxy)methyl)hex-5-ene-2-sulfonamide or (2R,4S)-4-(((tert-butyldiphenylsilyl)oxy)methyl)hex-5-ene-2-sulfonamide or (2R,4R)-4-(((tert-butyldiphenylsilyl)oxy)methyl)hex-5-ene-2-sulfonamide or (2S,4R)-4-(((tert-butyldiphenylsilyl)oxy)methyl)hex-5-ene-2-sulfonamide (0.65 g, 1.506 mmol, 56.5% yield).

Step 10: (S)-5-(((1R,2R)-2-((1S,4S,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic Acid or (S)-5-(((1R,2R)-2-((1S,4S,6R,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic Acid or (S)-5-(((1R,2R)-2-((1S,4R,6R,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic Acid or (S)-5-(((1R,2R)-2-((1S,4R,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic Acid and (S)-5-(((1R,2R)-2-((1S,4S,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic Acid or (S)-5-(((1R,2R)-2-((1S,4S,6R,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic Acid or (S)-5-(((1R,2R)-2-((1S,4R,6R,E)-4-(((tert-butyldiphenyl silyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic Acid or (S)-5-(((1R,2R)-2-((1S,4R,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic Acid

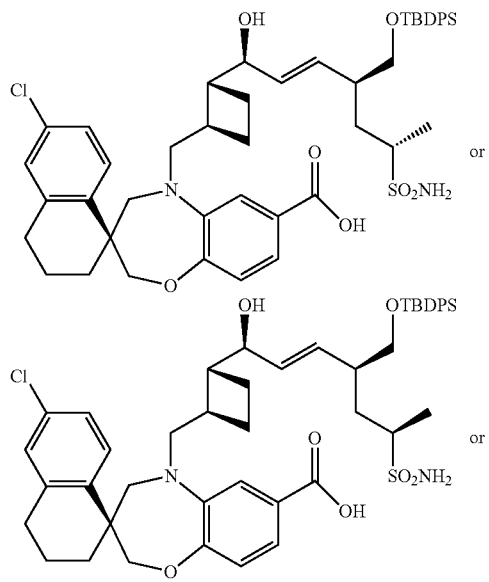

393

-continued

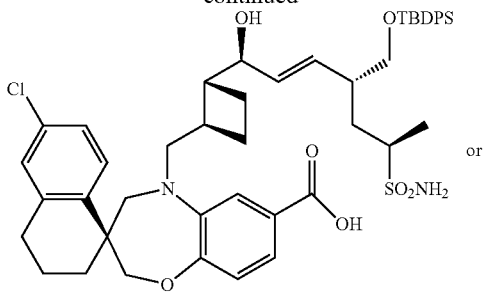

and

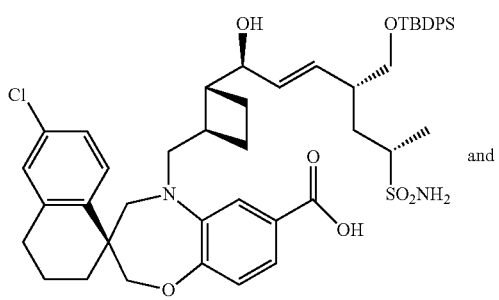

or

394

-continued

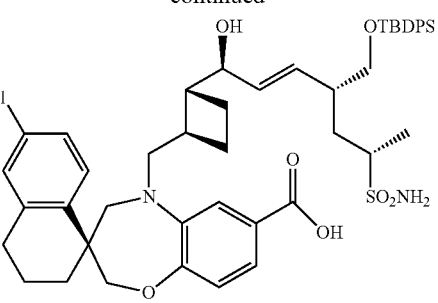

A solution of (2S,4S)-4-(((tert-butyldiphenylsilyl)oxy)methyl)hex-5-ene-2-sulfonamide or (2R,4S)-4-(((tert-butyldiphenylsilyl)oxy)methyl)hex-5-ene-2-sulfonamide or (2R,4R)-4-(((tert-butyldiphenylsilyl)oxy)methyl)hex-5-ene-2-sulfonamide or (2S,4R)-4-(((tert-butyldiphenylsilyl)oxy)methyl)hex-5-ene-2-sulfonamide and (2S,4S)-4-(((tert-butyldiphenylsilyl)oxy)methyl)hex-5-ene-2-sulfonamide or (2R,4S)-4-(((tert-butyldiphenylsilyl)oxy)methyl)hex-5-ene-2-sulfonamide or (2R,4R)-4-(((tert-butyldiphenylsilyl)oxy)methyl)hex-5-ene-2-sulfonamide or (2S,4R)-4-(((tert-butyldiphenylsilyl)oxy)methyl)hex-5-ene-2-sulfonamide (498 mg, 1.154 mmol) in 1,2-dichloroethane (3846 µL) was degassed for 10 minutes by sparging Ar(g). The reaction was then treated with a solution of Hoveyda-Grubbs catalyst $2^{nd}$ generation (24.10 mg, 0.038 mmol) in DCE (0.8 mL) and Ti(iPrO)$_4$ (3 drops) and a solution of (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Intermediate AA11A; 180 mg, 0.385 mmol) in DCE (2 mL) was added dropwise via syringe pump over 3 hours while sparging Ar(g) through the reaction (30 minutes after the addition had started, Ti(iPrO)$_4$ (3 drops was added); 1 hour after the addition had started an additional portion of Hoveyda-Grubbs catalyst $2^{nd}$ generation (24 mg) and Ti(iPrO)$_4$ (3 drops) was added). Once that the addition was completed the reaction was stirred at ambient temperature overnight. After this time the catalyst was deactivated by sparging air (g) through the reaction mixture for 5 minutes. SiO$_2$ (ca. 3 g) was added to the mixture and the solvent was evaporated in vacuo. The product was transferred to a solid loading cartridge and purified by column chromatography (12 g SiO$_2$, DCM:acetone, 1:0 to 4:1) to give (S)-5-(((1R,2R)-2-((1S,4S,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4S,6R,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4R,6R,E)-4-(((tert-butyldiphenylsilyl)

oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4R,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid and (S)-5-(((1R,2R)-2-((1S,4S,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4S,6R,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4R,6R,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4R,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid as the first eluting minor component (38 mg, 0.044 mmol, 11.3% yield).

Further elution provided (S)-5-(((1R,2R)-2-((1S,4S,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4S,6R,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4R,6R,E)-4-(((tert-butyl diphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4R,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid and (S)-5-(((1R,2R)-2-((1S,4S,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4S,6R,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4R,6R,E)-4-(((tert-butyl diphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4R,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid as the second eluting major component (58 mg, 0.067 mmol, 17.3% yield).

Step 11: (1S,3'R,6'R,7'S,8'E,10'S,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,21}$]pentacosa[8,16,18,24]tetraen]-15'-one 13',13'-dioxide or (1S,3'R,6'R,7'S,8'E,10'S,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

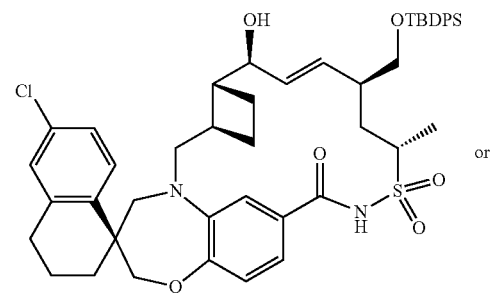

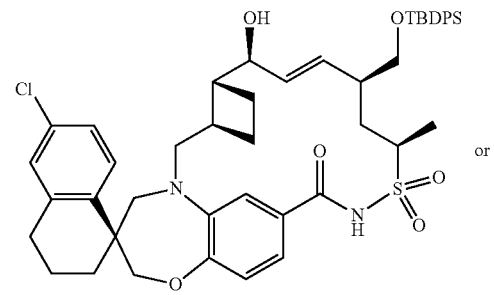

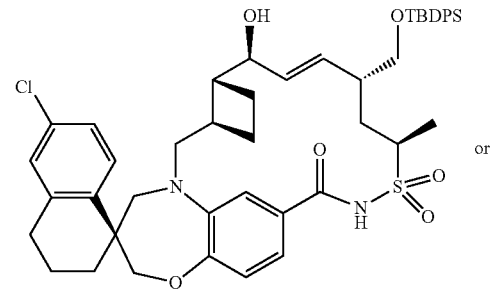

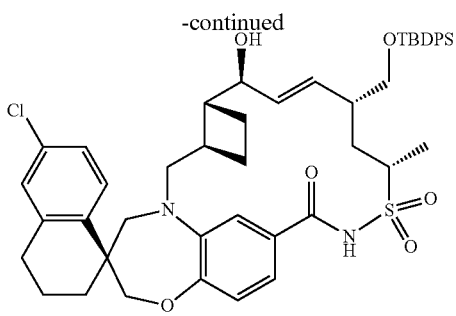

To a stirred solution of (S)-5-(((1R,2R)-2-((1S,4S,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4S,6R,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4R,6R,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4R,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid and (S)-5-(((1R,2R)-2-((1S,4S,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4S,6R,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4R,6R,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4R,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid (Example 127, Step 10, first eluting minor component; 38 mg, 0.044 mmol) in DCM (14.5 mL) at 0° C. under a N$_2$ atmosphere was added N,N-dimethylpyridin-4-amine (9.05 mg, 0.074 mmol). After 3 minutes N1-((ethylimino)methylene)-N3,N3-dimethylpropane-1,3-diamine hydrochloride (16.72 mg, 0.087 mmol) was added portionwise over 3 minutes and the reaction was allowed to stirred at ambient temperature overnight. After this time the reaction was partitioned between DCM and 1M HCl. The separated aqueous layer was back-extracted with DCM and the combined organic extracts were washed with brine, dried over MgSO$_4$, filter and evaporated in vacuo. The product was adsorbed in ca. 1 g of SiO$_2$ and purified by column chromatography (4 g SiO$_2$, DCM:acetone, 1:0 to 4:1) to provide (1S,3'R,6'R,7'S,8'E,10'S,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one or (1S,3'R,6'R,7'S,8'E,10'R,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as the first eluting major isomer (12 mg, 0.014 mmol, 32.3% yield).

Further elution provided (1S,3'R,6'R,7'S,8'E,10'S,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as the second eluting minor isomer (7 mg, 0.008 mmol, 18.8% yield).

Step 12: (1S,3'R,6'R,7'S,8'E,10'S,12'S)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-dioxide or (1S,3'R,6'R,7'S,8'E,10'R,12'R)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide To a stirred solution of (1S,3'R,6'R,7'S,8'E,10'S,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 12, Step 11, first eluting major isomer; 12 mg, 0.014 mmol) in THF (703 μL) under a N$_2$ atmosphere was added sodium hydride (5.62 mg, 0.141 mmol) and the reaction was stirred at ambient temperature for 15 minutes. After this time iodomethane (4.40 μl, 0.070 mmol) was added and the reaction was stirred at ambient temperature overnight. The reaction was then treated with EtOAc and water. The separated organic layer was washed with brine, dried over MgSO$_4$, filtered and evaporated in vacuo to give the desired methyl-ether intermediate.

The crude product was dissolved in THF (0.3 mL) and treated with TBAF (Sigma Aldrich, 1M in THF; 141 μL, 0.141 mmol). The reaction was stirred at ambient temperature overnight. After this time the reaction was partitioned between EtOAc and 1M HCl. The separated aqueous layer was extracted with EtOAc and the combined organic extracts were washed with brine, dried over MgSO$_4$, filtered and evaporated in vacuo. Column chromatography (ca. 2 g SiO$_2$, DCM:acetone, 1:0 to 9:1) gave the partially purified title compound. Further purification by column chromatography (ca. 1 g SiO$_2$, hexanes:EtOAc (containing 1% AcOH), 1:0 to 2:1) gave (1S,3'R,6'R,7'S,8'E,10'S,12'S)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (1.6 mg, 2.54 μmol, 18.09% yield). $^1$H NMR (400 MHz, CD$_2$Cl$_2$) δ 7.71 (d, J=8.6 Hz, 1H), 7.17 (dd, J=2.3, 8.4 Hz, 1H), 7.09 (d, J=2.2 Hz, 1H), 6.95 (dd, J=2.0, 8.0 Hz, 1H), 6.91 (d, J=8.0 Hz, 1H), 6.84 (s, 1H), 5.73 (dd, J=6.9, 15.7 Hz, 1H), 5.56 (dd, J=7.6, 15.8 Hz, 1H), 4.29-4.20 (m, 1H), 4.14-4.07 (m, 2H), 3.79 (d, J=15.7 Hz, 1H), 3.72-3.68 (m, 1H), 3.66 (d, J=14.7 Hz, 1H), 3.62 (dd, J=6.5, 10.6 Hz, 1H), 3.53 (dd, J=7.4, 10.2 Hz, 1H), 3.24 (s, 3H), 3.20 (d, J=14.7 Hz, 1H), 3.06 (dd, J=8.9, 15.4 Hz, 1H), 2.84-2.68 (m, 2H), 2.60-2.44 (m, 2H), 2.35-2.25 (m, 1H), 2.21 (ddd, J=3.8, 6.9, 14.9 Hz, 1H), 2.02 (br. s., 1H), 1.98-1.88 (m, 2H), 1.86-1.79 (m, 1H), 1.78-1.62 (m, 4H), 1.57 (d, J=7.0 Hz, 3H), 1.42 (t, J=11.6 Hz, 1H). MS (ESI, +ve ion) m/z 629.2 (M+H)$^+$.

Example 128. (1S,3'R,6'R,7'S,8'E,10'S,12'S)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-1S-one 13',13'-dioxide or (1S,3'R,6'R,7'S,8'E,10'S,12'R)-6-chloro-10'-(hydroxymethyl)-7'-methoxy-12'-methyl-3,4-dihydro-2H,15'H-spiro[naphthalene-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,10'S,12'S)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-10'-(hydroxymethyl)-7'-methoxy-12'-methyl-3,4-dihydro-2H,15'H-spiro[naphthalene-[20]oxa[13]thia[1,14]diazatetracyclo[14.7.2.0$^{3,6}$.0$^{19,24}$]pentacosa[8,16,18,24]tetraen]-15'-one 13',13'-dioxide

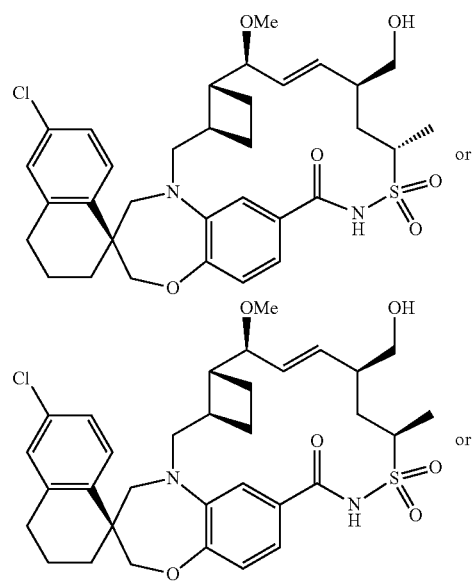

401
-continued
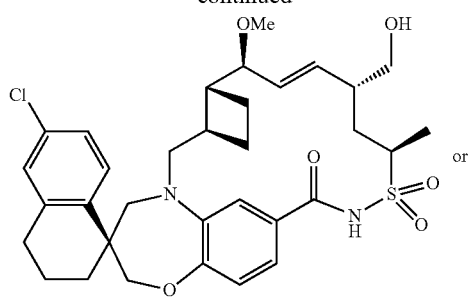
402
-continued
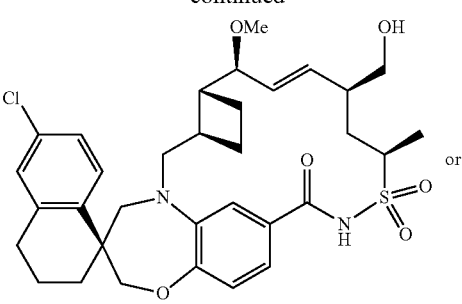
or
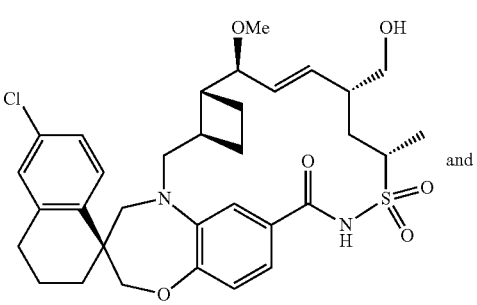
and
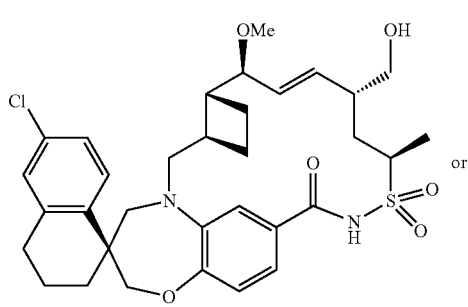
or
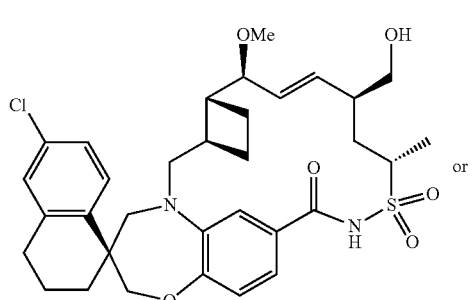
or
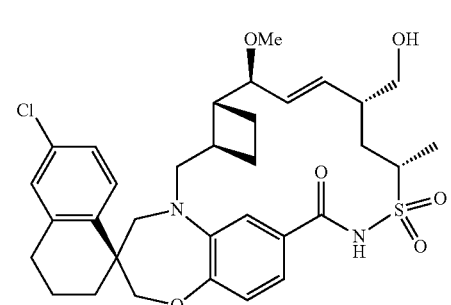

Step 1: (1S,3'R,6'R,7'S,8'E,10'S,12'S)-6-chloro-10'-(((tert-butyldiphenyl silyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'S,12'R)-6-chloro-10'-(((tert-butyldiphenyl silyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,12'R)-6-chloro-10'-(((tert-butyldiphenyl silyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide and (1S,3'R,6'R,7'S,8'E,10'S,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'S,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,1O'R,12'R)-6-chloro-10'-(((tert-butyldiphenyl silyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

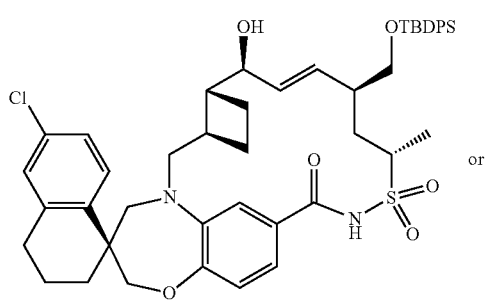 or

-continued

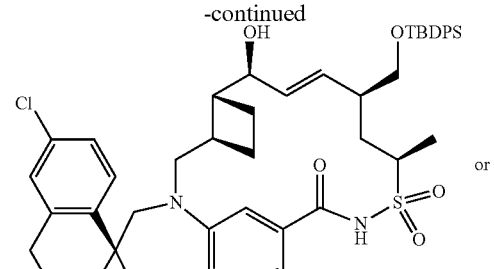 or

 or

 and

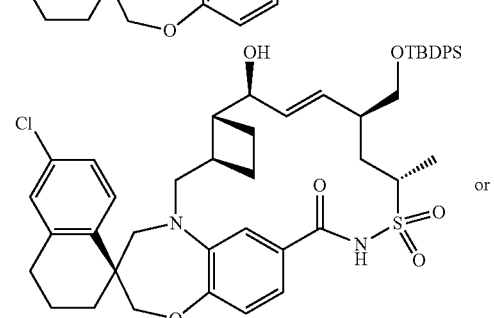 or

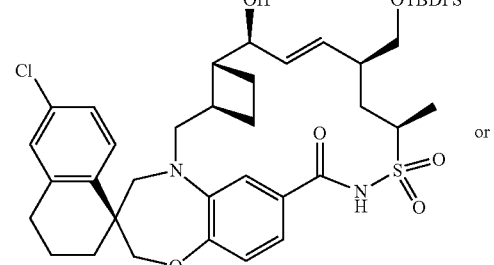 or

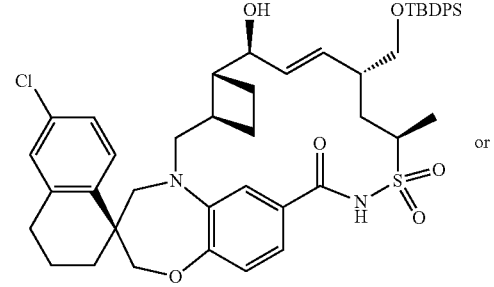 or

-continued

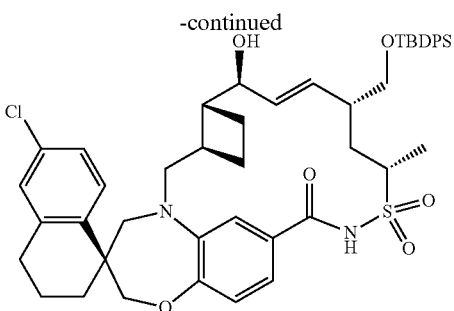

To a stirred solution of (S)-5-(((1R,2R)-2-((1S,4S,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4S,6R,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4R,6R,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4R,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid and (S)-5-(((1R,2R)-2-((1S,4S,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4S,6R,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4R,6R,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((1S,4R,6S,E)-4-(((tert-butyldiphenylsilyl)oxy)methyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid (Example 127, Step 10, second eluting major component; 58 mg, 0.067 mmol) in DCM (22.2 mL) at 0° C. under a $N_2$ atmosphere was added N,N-dimethylpyridin-4-amine (13.82 mg, 0.113 mmol). After 3 minutes N1-((ethylimino)methylene)-N3,N3-dimethylpropane-1,3-diamine hydrochloride (25.5 mg, 0.133 mmol) was added portionwise over 3 minutes and the reaction was allowed to warm to ambient temperature overnight. After this time the reaction was partitioned between DCM and 1M HCl. The separated aqueous layer was back-extracted with DCM and the combined organic extracts were washed with brine, dried over $MgSO_4$, filtered and evaporated in vacuo. The product was adsorbed in ca. 1 g of $SiO_2$ and purified by column chromatography (4 g $SiO_2$, DCM:Acetone, 1:0 to 4:1) to provide (1S,3'R,6'R,7'S,8'E,10'S,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,10'S,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as the first eluting isomer (7 mg, 0.008 mmol, 12.3% yield).

Further elution provided (1S,3'R,6'R,7'S,8'E,10'S,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,10'S,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as the second eluting isomer (7 mg, 0.008 mmol, 12.3% yield).

Step 2: (1S,3'R,6'R,7'S,8'E,10'S,12'S)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(hydroxymethyl)-7'-methoxy-12'-methyl-3,4-dihydro-2H,15'H-spiro[naphthalene-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,10'S,12'S)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-10'-(hydroxymethyl)-7'-methoxy-12'-methyl-3,4-dihydro-2H,15'H-spiro[naphthalene-[20]oxa[13]thia[1,14]diazatetracyclo[14.7.2.0$^{3,6}$.0$^{19,24}$]pentacosa[8,16,18,24]tetraen]-15'-one 13',13'-dioxide To a stirred solution of (1S,3'R,6'R,7'S,8'E,10'S,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,10'S,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 128, Step 1, first eluting isomer; 7 mg, 0.008 mmol) in THF (410 µL) under a N$_2$ atmosphere was added sodium hydride (3.28 mg, 0.082 mmol) and the reaction was stirred at ambient temperature for 15 minutes. After this time iodomethane (2.56 µL, 0.041 mmol) was added and the reaction was stirred at ambient temperature overnight. The reaction was then treated with EtOAc and water. The separated organic layer was washed with brine, dried over MgSO$_4$, filtered and evaporated in vacuo to give the desired methyl-ether intermediate. The crude product (9 mg) was dissolved in THF (0.3 mL) and treated with TBAF (Sigma Aldrich, 1 M in THF; 123 µL, 0.123 mmol). The reaction was stirred at ambient temperature overnight. After this time the reaction was partitioned between EtOAc and 1M HCl. The separated organic layer was dried over MgSO$_4$, filtered and evaporated in vacuo. Column chromatography (ca. 2 g SiO$_2$, DCM:acetone, 1:0 to 4:1) gave the title compound as a 70:30 mixture of diastereomers (1.9 mg, 3.02 µmol, 36.8% yield). Analytical data are reported for the major isomer. $^1$H NMR (400 MHz, CD$_2$Cl$_2$) δ 7.71 (d, J=8.4 Hz, 1H), 7.17 (dd, J=2.2, 8.4 Hz, 1H), 7.09 (d, J=2.3 Hz, 1H), 6.98-6.90 (m, 3H), 5.65 (dd, J=4.9, 16.2 Hz, 1H), 5.48 (ddd, J=2.0, 6.5, 16.4 Hz, 1H), 4.30-4.21 (m, 1H), 4.14-4.08 (m, 2H), 3.84 (d, J=15.5 Hz, 1H), 3.80-3.75 (m, 1H), 3.71 (dd, J=4.3, 10.4 Hz, 1H), 3.69 (d, J=13.5 Hz, 1H), 3.50 (dd, J=6.7, 10.9 Hz, 1H), 3.26 (s, 3H), 3.20 (d, J=14.7 Hz, 1H), 3.04 (dd, J=9.7, 15.6 Hz, 1H), 2.85-2.69 (m, 2H), 2.52-2.38 (m, 2H), 2.32-2.17 (m, 2H), 2.02 (br. s., 1H), 1.98-1.90 (m, 2H), 1.78-1.59 (m, 5H), 1.52 (d, J=7.0 Hz, 3H), 1.47-1.36 (m, 1H). MS (ESI, +ve ion) m/z 629.2 (M+H)$^+$.

Example 129. (1S,3'R,6'R,7'S,8'E,10'S,12'S)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'S,12'R)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,12'R)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,12'S)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide and (1S,3'R,6'R,7'S,8'E,10'S,12'S)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'S,12'R)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,12'R)-6-chloro-10'-(hydroxymethyl)-7'-methoxy-12'-methyl-3,4-dihydro-2H,15'H-spiro[naphthalene-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,12'S)-6-chloro-10'-(hydroxymethyl)-7'-methoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

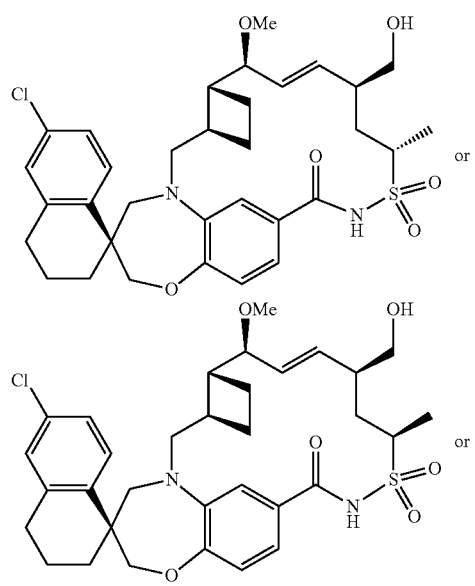

-continued

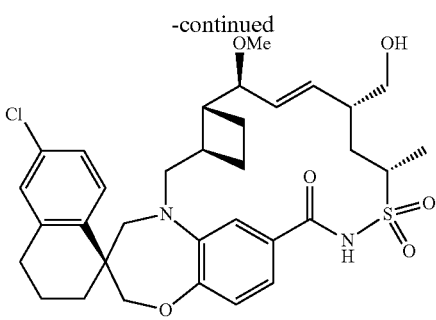

To a stirred solution of (1S,3'R,6'R,7'S,8'E,10'S,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,10'S,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-10'-(((tert-butyldiphenylsilyl)oxy)methyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 128, Step 1, second eluting isomer; 7 mg, 0.008 mmol) in THF (410 μL) under a N$_2$ atmosphere was added sodium hydride (1 mg, 0.025 mmol) and the reaction was stirred at ambient temperature for 15 minutes. After this time iodomethane (1 μL, 0.008 mmol) was added and the reaction was stirred at ambient temperature overnight. The reaction was then treated with EtOAc and water. The separated organic layer was washed with brine, dried over MgSO$_4$, filtered and evaporated in vacuo to give the desired methyl-ether intermediate. The crude product (9 mg) was dissolved in THF (0.3 mL) and treated with TBAF (Sigma Aldrich, 1 M in THF; 8 μL, 0.008 mmol). The reaction was stirred at ambient temperature overnight. After this time the reaction was partitioned between EtOAc and 1M HCl. The separated organic layer was dried over MgSO$_4$, filtered and evaporated in vacuo. Column chromatography (ca. 2 g SiO$_2$, DCM: acetone, 1:0 to 4:1) gave the title compound as a 3:1 mixture of diastereomers (1.4 mg, 2.23 μma 27.1% yield). Analytical data are reported for the major isomer. $^1$H NMR (400 MHz, CD$_2$Cl$_2$) δ 8.12 (s, 1H), 7.68 (d, J=8.4 Hz, 1H), 7.16 (dd, J=2.3, 8.4 Hz, 1H), 7.10 (d, J=2.2 Hz, 1H), 7.07-7.04 (m, 1H), 7.03 (d, J=8.0 Hz, 1H), 6.92 (d, J=8.4 Hz, 1H), 5.82 (dd, J=7.0, 15.8 Hz, 1H), 5.47 (dd, J=7.2, 15.8 Hz, 1H), 4.11 (s, 2H), 3.98 (dd, J=6.0, 12.8 Hz, 1H), 3.65 (dd, J=6.4, 10.5 Hz, 1H), 3.59-3.51 (m, 2H), 3.50-3.37 (m, 4H), 3.30 (s, 3H), 2.83-2.69 (m, 2H), 2.64-2.57 (m, 1H), 2.56-2.47 (m, 1H), 2.46-2.22 (m, 4H), 2.13 (ddd, J=3.8, 6.0, 15.2 Hz, 1H), 1.95-1.78 (m, 4H), 1.78-1.65 (m, 3H), 1.55 (d, J=7.0 Hz, 3H). MS (ESI, +ve ion) m/z 629.2 (M+H)$^+$.

Example 130. (1S,3'R,6'R,7'S,8'E,11'R,15'S)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'R)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'S)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'R,15'R)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide

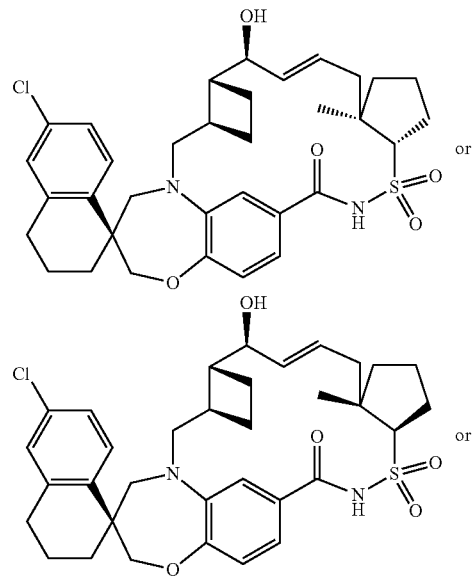

-continued

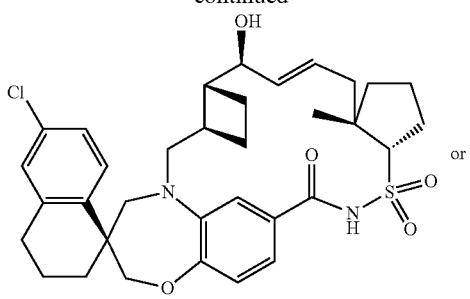

Step 1: (R)-2-allyl 1-methyl-2-oxocyclopentanecarboxylate and (R)-2-allyl 1-methyl-2-oxocyclopentanecarboxylate

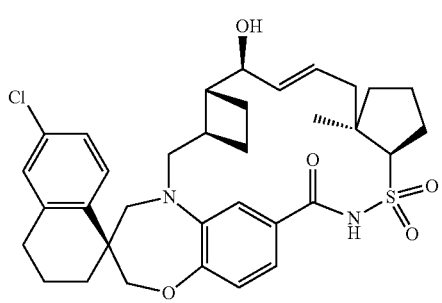

To a stirred solution of THF (110 mL) under a N₂ atmosphere was added sodium hydride (0.972 g, 24.31 mmol). Diallyl adipate (Pfaltz & Bauer, Inc.; 5.00 ml, 22.10 mmol) in THF (30 mL) was then added dropwise via syringe (reaction turns blue as starting material is added) and the reaction was stirred at ambient temperature for 1 hour. After this time the reaction was heated at reflux for 90 minutes. The reaction was then cooled to ambient temperature and iodomethane (1.796 mL, 28.7 mmol) was added dropwise via syringe over 1 minute and the reaction was then heated to reflux for 2 hours. The reaction was then cooled to ambient temperature and partitioned between EtOAc and brine. The separated organic layer was dried over MgSO₄, filtered and evaporated in vacuo. Column chromatography (80 g SiO₂, hexanes:EtOAc, 1:0 to 4:1) gave (R)-2-allyl 1-methyl-2-oxocyclopentanecarboxylate and (S)-2-allyl 1-methyl-2-oxocyclopentanecarboxylate (3.35 g, 18.38 mmol, 83% yield).

Step 2: (S)-2-allyl-2-methyl-2-cyclopentanone and (R)-2-allyl-2-methyl-2-cyclopentanone

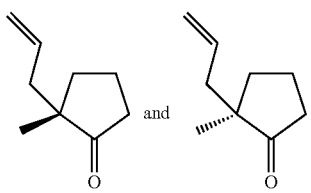

To a solution of (R)-2-allyl 1-methyl-2-oxocyclopentanecarboxylate and (S)-2-allyl 1-methyl-2-oxocyclopentanecarboxylate (3.35 g, 18.38 mmol) in THF (36.8 mL) was added palladium(II) acetate (Sigma Aldrich; 0.041 g, 0.184 mmol) and triphenylphosphine (Sigma Aldrich; 0.193 g, 0.735 mmol) and the reaction was heated at reflux under a N₂ atmosphere for 1 hour. After this time the reaction was cooled to ambient temperature and partitioned between Et₂O and brine. The separated organic layer was dried over MgSO₄, filtered and evaporated in vacuo. The resulting liquid was purified by short path distillation under house vacuum (ca. 20 mm of Hg) and the fraction boiling at 100-125° C. was collected to (S)-2-allyl-2-methyl-2-cyclopentanone and (R)-2-allyl-2-methyl-2-cyclopentanone (1.4 g, 10.13 mmol, 55.1% yield).

Step 3: (1R,2R)-2-allyl-2-methylcyclopentanol and (1S,2S)-2-allyl-2-methylcyclopentanol and (1R,2S)-2-allyl-2-methylcyclopentanol and (1S,2R)-2-allyl-2-methylcyclopentanol

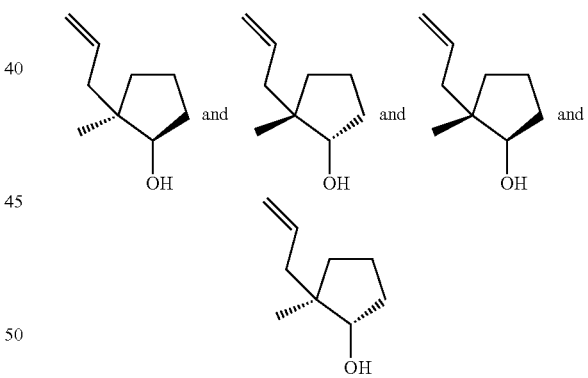

To a stirred solution of (S)-2-allyl-2-methyl-2-cyclopentanone and (R)-2-allyl-2-methyl-2-cyclopentanone (1.12 g, 8.10 mmol) in Et₂O (40.5 mL) at −78° C. under a N₂ atmosphere was added dropwise via syringe a solution of 1-selectride (Sigma Aldrich, 1M in THF; 8.91 mL, 8.91 mmol). The reaction was stirred at −78° C. for 2 hours and then it was allowed to warm to ambient temperature for 20 minutes. After this time the reaction was quenched with NH₄Cl (saturated aqueous solution) and diluted with EtOAc. The separated aqueous layer was extracted with EtOAc and the combined organic extracts were dried over MgSO₄, filtered and evaporated in vacuo. Column chromatography (24 g Sift, hexanes:EtOAc, 1:0 to 4:1) gave (1R,2R)-2-allyl-2-methylcyclopentanol and (1S,2S)-2-allyl-2-methylcyclopentanol and (1R,2S)-2-allyl-2-methylcyclopentanol and (1S,2R)-2-allyl-2-methylcyclopentanol (1 g, 7.13 mmol, 88% yield).

Step 4: (1R,2R)-2-allyl-2-methylcyclopentyl Methanesulfonate and (1S,2S)-2-allyl-2-methylcyclopentyl Methanesulfonate and (1R,2S)-2-allyl-2-methylcyclopentyl Methanesulfonate and (1S,2R)-2-allyl-2-methylcyclopentyl Methanesulfonate

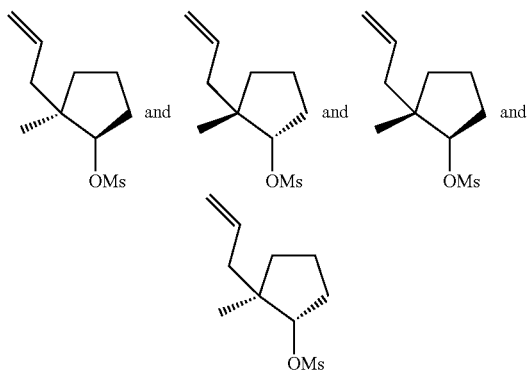

To a stirred solution of (1R,2R)-2-allyl-2-methylcyclopentanol and (1S,2S)-2-allyl-2-methylcyclopentanol and (1R,2S)-2-allyl-2-methylcyclopentanol and (1S,2R)-2-allyl-2-methylcyclopentanol (1.0 g, 7.13 mmol) in DCM (35.7 mL) at 0° C. under a $N_2$ atmosphere was added triethylamine (1.99 mL, 14.26 mmol) followed by methanesulfonyl chloride (0.72 mL, 9.27 mmol). The reaction was allowed to warm to ambient temperature for 2 hours. After this time the reaction was partitioned between DCM and $NaHCO_3$. The separated organic layer was dried over $MgSO_4$, filtered and evaporated in vacuo. Column chromatography (40 g Sift redisep gold, DCM) gave (1R,2R)-2-allyl-2-methylcyclopentyl methanesulfonate and (1S,2S)-2-allyl-2-methylcyclopentyl methanesulfonate and (1R,2S)-2-allyl-2-methylcyclopentyl methanesulfonate and (1S,2R)-2-allyl-2-methylcyclopentyl methanesulfonate (1.24 g, 5.68 mmol, 80% yield).

Step 5: 2-(((1S,2R)-2-allyl-2-methylcyclopentyl)thio)pyrimidine and 2-(((1R,2S)-2-allyl-2-methylcyclopentyl)thio)pyrimidine and 2-(((1S,2S)-2-allyl-2-methylcyclopentyl)thio)pyrimidine and 2-(((1R,2R)-2-allyl-2-methylcyclopentyl)thio)pyrimidine

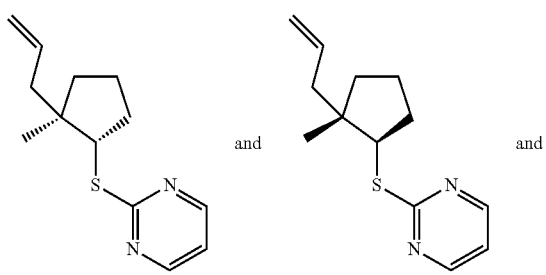

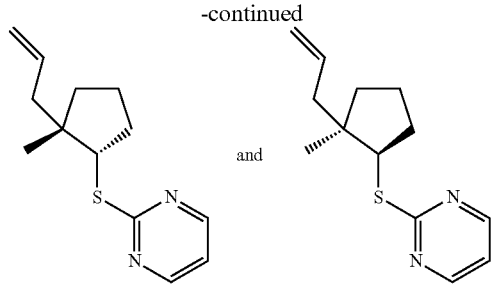

To a stirred solution of (1R,2R)-2-allyl-2-methylcyclopentyl methanesulfonate and (1S,2S)-2-allyl-2-methylcyclopentyl methanesulfonate and (1R,2S)-2-allyl-2-methylcyclopentyl methanesulfonate and (1S,2R)-2-allyl-2-methylcyclopentyl methanesulfonate (2.7 g, 12.37 mmol) in DMF (49.5 mL) was added 2-mercaptopyrimidine (TCI Co. ltd.; 1.66 g, 14.84 mmol) and cesium carbonate (2.05 g, 14.84 mmol). The reaction was heated at 60° C. overnight. After this time an additional portion of 2-mercaptopyrimidine (0.5 g) was added and the reaction was heated at 80° C. for 3 hours. After this time an additional portion of 2-mercaptopyrimidine (0.5 g) was added and the reaction was heated at 100° C. for 3 hours. After this time the reaction was cooled to ambient temperature and partitioned between EtOAc and brine. The separated organic layer was dried over $MgSO_4$, filtered and evaporated in vacuo. Column chromatography (40 g Sift, hexanes:EtOAc, 1:0 to 3:1) gave 2-(((1S,2R)-2-allyl-2-methylcyclopentyl)thio)pyrimidine and 2-(((1R,2S)-2-allyl-2-methylcyclopentyl)thio)pyrimidine and 2-(((1S,2S)-2-allyl-2-methylcyclopentyl)thio)pyrimidine and 2-(((1R,2R)-2-allyl-2-methylcyclopentyl)thio)pyrimidine (0.59 g, 2.52 mmol, 20.36% yield).

Step 6: 2-(((1S,2R)-2-allyl-2-methylcyclopentyl)sulfonyl)pyrimidine and 2-(((1R,2S)-2-allyl-2-methylcyclopentyl)sulfonyl)pyrimidine and 2-(((1S,2S)-2-allyl-2-methylcyclopentyl)sulfonyl)pyrimidine and 2-(((1R,2R)-2-allyl-2-methylcyclopentyl)sulfonyl)pyrimidine

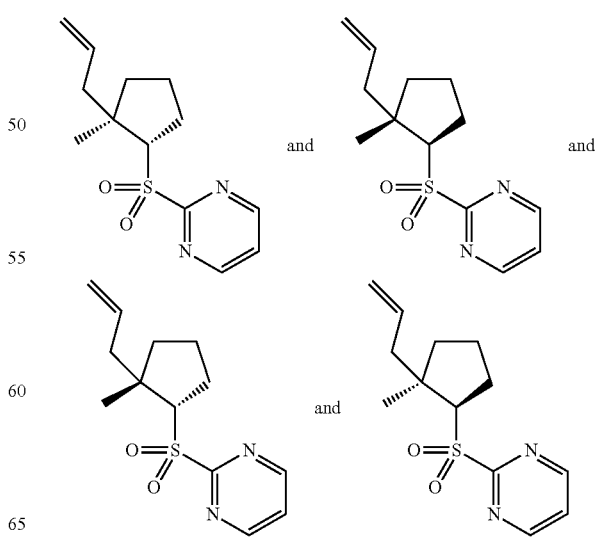

To a stirred solution of 2-(((1S,2R)-2-allyl-2-methylcyclopentyl)thio)pyrimidine and 2-(((1R,2S)-2-allyl-2-methylcyclopentyl)thio)pyrimidine and 2-(((1S,2S)-2-allyl-2-methylcyclopentyl)thio)pyrimidine and 2-(((1R,2R)-2-allyl-2-methylcyclopentyl)thio)pyrimidine (0.59 g, 2.52 mmol) in DCM (16.78 mL) was added MCPBA (Sigma Aldrich, 77% wt.; 1.185 g, 5.29 mmol). The reaction was stirred at ambient temperature for 3 hours. After this time the reaction was partitioned between DCM and NaHCO₃. The separated organic layer was dried over MgSO₄, filtered and evaporated in vacuo. Column chromatography (24 g Sift, hexanes:EtOAc, 1:0 to 3:1) gave 2-(((1S,2R)-2-allyl-2-methylcyclopentyl)sulfonyl)pyrimidine and 2-(((1R,2S)-2-allyl-2-methylcyclopentyl)sulfonyl)pyrimidine and 2-(((1S,2S)-2-allyl-2-methylcyclopentyl)sulfonyl)pyrimidine and 2-(((1R,2R)-2-allyl-2-methylcyclopentyl)sulfonyl)pyrimidine (0.19 g, 0.713 mmol, 28.3% yield).

Step 7: Sodium (1S,2R)-2-allyl-2-methylcyclopentane-1-sulfinate and Sodium (1R,2S)-2-allyl-2-methylcyclopentane-1-sulfinate and Sodium (1S,2S)-2-allyl-2-methylcyclopentane-1-sulfinate and Sodium (1R,2R)-2-allyl-2-methylcyclopentane-1-sulfinate To a stirred solution of 2-(((1S,2R)-2-allyl-2-methylcyclopentyl)sulfonyl)pyrimidine and 2-(((1R,2S)-2-allyl-2-methylcyclopentyl)sulfonyl)pyrimidine and 2-(((1S,2S)-2-allyl-2-methylcyclopentyl)sulfonyl)pyrimidine and 2-(((1R,2R)-2-allyl-2-methylcyclopentyl)sulfonyl)pyrimidine (0.19 g, 0.713 mmol) in MeOH (7.13 mL) was added sodium methoxide (Sigma Aldrich, 25% wt.; 0.179 mL, 0.785 mmol). The reaction was stirred at ambient temperature for 1 hour. After this time the reaction was evaporated in vacuo and treated with Et₂O. The white solid was triturated with Et₂O, filtered and dried under vacuum to give sodium (1S,2R)-2-allyl-2-methylcyclopentane-1-sulfinate and sodium (1R,2S)-2-allyl-2-methylcyclopentane-1-sulfinate and sodium (1S,2S)-2-allyl-2-methylcyclopentane-1-sulfinate and sodium (1R,2R)-2-allyl-2-methylcyclopentane-1-sulfinate (0.14 g, 0.666 mmol, 93% yield).

Step 8: (1S,2R)-2-allyl-2-methylcyclopentane-1-sulfonamide and (1R,2S)-2-allyl-2-methylcyclopentane-1-sulfonamide and (1S,2S)-2-allyl-2-methylcyclopentane-1-sulfonamide and (1R,2R)-2-allyl-2-methylcyclopentane-1-sulfonamide

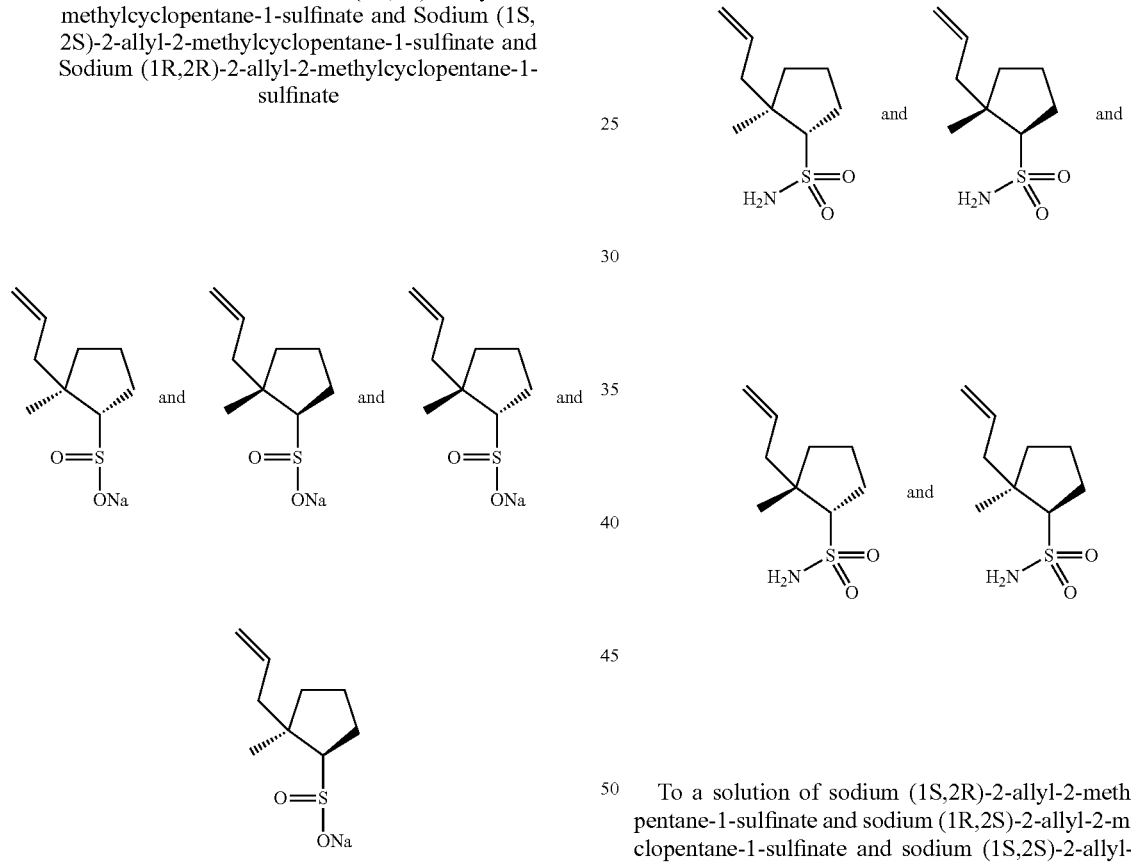

To a solution of sodium (1S,2R)-2-allyl-2-methylcyclopentane-1-sulfinate and sodium (1R,2S)-2-allyl-2-methylcyclopentane-1-sulfinate and sodium (1S,2S)-2-allyl-2-methylcyclopentane-1-sulfinate and sodium (1R,2R)-2-allyl-2-methylcyclopentane-1-sulfinate (0.14 g, 0.666 mmol) in water (6.66 mL) was added sodium acetate (0.109 g, 1.332 mmol) and (aminooxy)sulfonic acid (Sigma Aldrich; 0.113 g, 0.999 mmol) and the reaction was heated at 50° C. for 1 hour. After this time the reaction was cooled to ambient temperature and basified with NaOH. The aqueous layer was extracted with EtOAc (×2), DCM (×2), dried over MgSO₄, filtered and evaporated in vacuo to give (1S,2R)-2-allyl-2-methylcyclopentane-1-sulfonamide and (1R,2S)-2-allyl-2-methylcyclopentane-1-sulfonamide and (1S,2S)-2-allyl-2-methylcyclopentane-1-sulfonamide and (1R,2R)-2-allyl-2-methylcyclopentane-1-sulfonamide (0.079 g, 0.389 mmol, 58.4% yield).

Step 9: (S)-6'-chloro-5-(((1R,2R)-2-((S,E)-1-hydroxy-4-((1R,2S)-1-methyl-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((S,E)-1-hydroxy-4-((1S,2R)-1-methyl-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((S,E)-1-hydroxy-4-((1S,2S)-1-methyl-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((S,E)-1-hydroxy-4-((1R,2R)-1-methyl-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic Acid

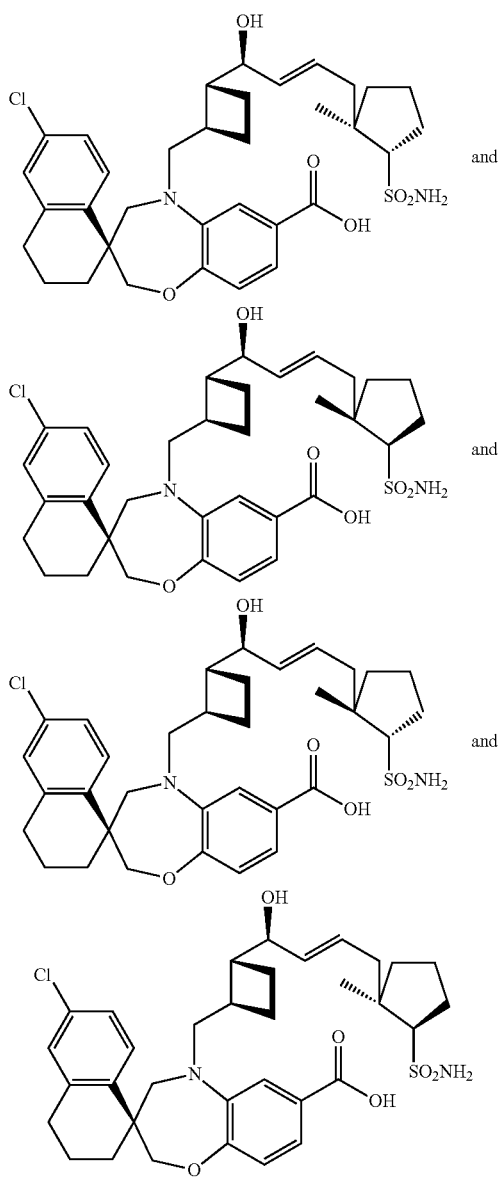

A solution of (S)-6'-chloro-5-(((1R,2R)-2-((S)-1-hydroxyallyl)cyclobutyl)methyl)-3',4,4',5-tetrahydro-2H,2'Hspiro[benzo[b][1,4]oxazepine-3,1'-naphthalene]-7-carboxylic acid (Intermediate AA1A; 100 mg, 0.214 mmol) and (1S,2R)-2-allyl-2-methylcyclopentane-1-sulfonamide and (1R,2S)-2-allyl-2-methylcyclopentane-1-sulfonamide and (1S,2S)-2-allyl-2-methylcyclopentane-1-sulfonamide and (1R,2R)-2-allyl-2-methylcyclopentane-1-sulfonamide (109 mg, 0.534 mmol) in 1,2-dichloroethane (3053 µL) was degassed for 10 minutes with Ar. After this time a solution of (1,3-dimesitylimidazolidin-2-ylidene)(2-isopropoxybenzylidene)ruthenium(VI) chloride (Sigma Aldrich; 13.39 mg, 0.021 mmol) in DCE (1 mL) was added and the reaction was stirred at ambient temperature for 1 hour. After this time 2 drops of Ti(PriO)$_4$ was added and the reaction was stirred at ambient temperature for 2 hours. After this time the catalyst was deactivated by sparging air through the reaction for 5 minutes. Sift (ca. 1 g) was added and the mixture was evaporated in vacuo. The product was loaded onto a solid loading cartridge and purified by column chromatography (4 g SiO$_2$, DCM:acetone, 1:0 to 85:15) to give (S)-6'-chloro-5-(((1R,2R)-2-((S,E)-1-hydroxy-4-((1R,2S)-1-methyl-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((1S,2R)-1-methyl-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((1S,2S)-1-methyl-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((1R,2R)-1-methyl-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid (50 mg, 0.078 mmol, 36.4% yield). The product was azeotroped from toluene (×2) before it was used in the next step.

Step 10: (1S,3'R,6'R,7'S,8'E,11R,15'S)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'R)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'S)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'R,15'R)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide To a stirred solution of (S)-6'-chloro-5-(((1R,2R)-2-((S,E)-1-hydroxy-4-((1R,2S)-1-methyl-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((1S,2R)-1-methyl-2-sulfamoylcyclopentyl)but-2-en-1-yl)cyclobutyl)methyl)-3',4,4',5-tetrahydro-2H,2'H- spiro[benzo[b][1,4]oxazepine-3,1'-naphthalene]-7-carboxylic acid and (S)-6'-chloro-5-(((1R,2R)-2-((S,E)-1-hydroxy-4-((1S,2S)-1-methyl-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((1R,2R)-1-methyl-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid (42 mg, 0.065 mmol) in DCM (32.6 mL) at 0° C. was added DMAP (Sigma Aldrich; 13.56 mg, 0.111 mmol), followed by EDC (Oakwood; 25.03 mg, 0.131 mmol; added portionwise over 2 minutes). The reaction was allowed to warm to ambient temperature overnight. After this time the reaction was washed with 1M HCl. The separated organic layer was dried over MgSO$_4$, filtered and evaporated in vacuo. The crude product was combined with the crude product of a previous run (ca. 50 mg) and purified by column chromatography (12 g Sift redisep gold, DCM: Acetone, 1:0 to 85:15) to give the partially purified title compound as the first eluting isomer (7 mg). This material was further purified by column chromatography (1 g, hexanes:EtOAc (containing 1% AcOH), 1:0 to 1:1) to give (1S,3'R,6'R,7'S,8'E,11'R,15'S)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'R)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'R)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide (1.8 mg, 0.003 mmol). $^1$H NMR (400 MHz, CD$_2$Cl$_2$) δ 7.71 (d, J=8.6 Hz, 1H), 7.17 (dd, J=2.3, 8.4 Hz, 1H), 7.09 (d, J=2.3 Hz, 1H), 6.91 (d, J=0.8 Hz, 2H), 6.81 (s, 1H), 5.86 (ddd, J=6.1, 8.2, 15.1 Hz, 1H), 5.67 (dd, J=9.1, 15.2 Hz, 1H), 4.31 (t, J=9.2 Hz, 1H), 4.24 (dd, J=4.2, 9.1 Hz, 1H), 4.07 (s, 2H), 3.82 (d, J=15.3 Hz, 1H), 3.71 (d, J=14.1 Hz, 1H), 3.20 (d, J=14.3 Hz, 1H), 3.01 (dd, J=10.0, 15.5 Hz, 1H), 2.85-2.67 (m, 2H), 2.48-2.29 (m, 3H), 2.28-2.14 (m, 3H), 1.99-1.89 (m, 3H), 1.88-1.76 (m, 3H), 1.74-1.68 (m, 2H), 1.67-1.61 (m, 2H), 1.55-1.45 (m, 1H), 1.39 (t, J=12.3 Hz, 1H), 1.12 (s, 3H). MS (ESI, +ve ion) m/z 625.3 (M+H)$^+$.

Example 131. (1S,3'R,6'R,7'S,8'E,11'R,15'S)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'R)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'S)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'R,15'R)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide

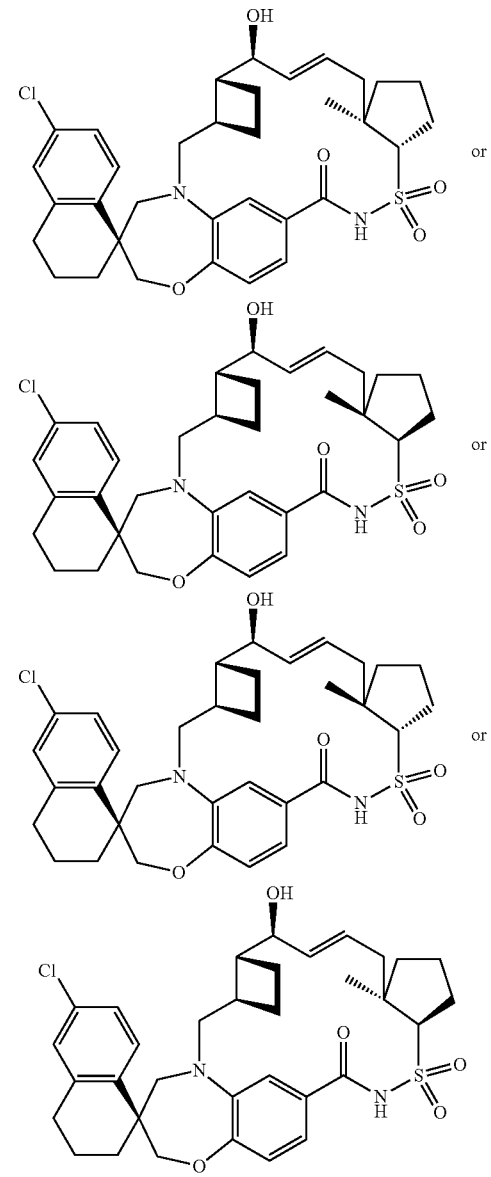

The title compound was synthesized as described in Example 120, Step 10 and was isolated as the second eluting isomer (10 mg). This material was further purified by column chromatography (1 g, hexanes:EtOAc (containing 1% AcOH), 1:0 to 1:1) to give (1S,3'R,6'R,7'S,8'E,11'R, 15'S)-6-chloro-7'-hydroxy-11'-methyl-3,4-dihydro-2H, 18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S, 15'R)-6-chloro-7'-hydroxy-11'-methyl-3,4-dihydro-2H, 18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21, 27]tetraen]-18'-one 16',16'-dioxide or (1S,3'R,6'R,7'S,8'E, 11'S,15'S)-6-chloro-7'-hydroxy-11'-methyl-3,4-dihydro-2H, 18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21, 27]tetraen]-18'-one 16',16'-dioxide or (1S,3'R,6'R,7'S,8'E, 11'R,15'R)-6-chloro-7'-hydroxy-11'-methyl-3,4-dihydro-2H,18'H-spiro[naphthalene-1,25'-[23]oxa[16]thia[1,17] diazapentacyclo[17.7.2.0$^{3,6}$.0$^{11,15}$.0$^{22,27}$]octacosa[8,19,21, 27]tetraen]-18'-one 16',16'-dioxide (4.0 mg, 0.006 mmol). $^1$H NMR (400 MHz, CD$_2$Cl$_2$) δ 7.69 (d, J=8.4 Hz, 1H), 7.22-7.12 (m, 2H), 7.09 (d, J=2.2 Hz, 1H), 6.95 (br. s., 1H), 6.93 (d, J=8.2 Hz, 1H), 6.17 (td, J=7.2, 15.0 Hz, 1H), 5.67 (dd, J=5.1, 15.5 Hz, 1H), 4.18 (t, J=4.7 Hz, 1H), 4.12 (s, 2H), 3.89-3.81 (m, 1H), 3.61 (d, J=14.5 Hz, 1H), 3.52-3.32 (m, 3H), 2.85-2.71 (m, 2H), 2.62-2.53 (m, 2H), 2.51-2.46 (m, 1H), 2.44-2.34 (m, 2H), 2.22 (dd, J=7.4, 15.5 Hz, 1H), 2.00-1.93 (m, 2H), 1.91-1.82 (m, 4H), 1.80-1.72 (m, 4H), 1.56-1.46 (m, 2H), 1.04 (s, 3H). MS (ESI, +ve ion) m/z 625.3 (M+H)$^+$.

Example 132. (1S,3'R,6'R,7'S,8'E,11R,15'S)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21, 27]tetraen]-18'-one 16',16'-dioxide or (1S,3'R,6'R, 7'S,8'E,11'S,15'R)-6-chloro-7'-hydroxy-11'-methyl-3, 4-dihydro-2H,18'H-spiro[naphthalene-1,25'-[23]oxa [16]thia[1,17]diazapentacyclo[17.7.2.0$^{3,6}$.0$^{11,15}$.0$^{22, 27}$]octacosa[8,19,21,27]tetraen]-18'-one 16',16'-dioxide or (1S,3'R,6'R,7'S,8'E,11'S,15'S)-6-chloro-7'-hydroxy-11'-methyl-3,4-dihydro-2H,18'H-spiro [naphthalene-1,25'-[23]oxa[16]thia[1,17] diazapentacyclo[17.7.2.0$^{3,6}$.0$^{11,15}$.0$^{22,27}$]octacosa[8, 19,21,27]tetraen]-18'-one 16',16'-dioxide or (1S,3'R, 6'R,7'S,8'E,11'R,15'R)-6-chloro-7'-hydroxy-11'-methyl-3,4-dihydro-2H,18'H-spiro[naphthalene-1, 25'-[23]oxa[16]thia[1,17]diazapentacyclo[17.7.2. 0$^{3,6}$.0$^{11,15}$.0$^{22,27}$]octacosa[8,19,21,27]tetraen]-18'-one 16',16'-dioxide

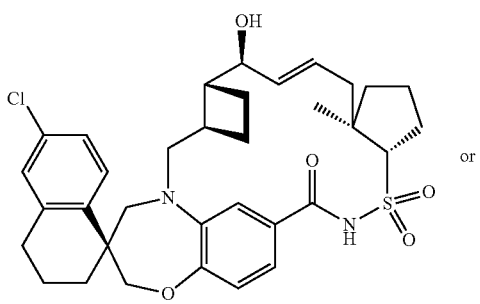

The title compound was synthesized as described in Example 120, Step 10 and was isolated as the third eluting isomer (5 mg). This material was further purified by column chromatography (1 g, hexanes:EtOAc (containing 1% AcOH), 1:0 to 1:1) to give (1S,3'R,6'R,7'S,8'E,11'R,15'S)-6-chloro-7'-hydroxy-11'-methyl-3,4-dihydro-2H,18'H-spiro [naphthalene-1,25'-[23]oxa[16]thia[1,17]diazapentacyclo [17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'R)-6-chloro-7'-hydroxy-11'-methyl-3,4-dihydro-2H,18'H-spiro [naphthalene-1,25'-[23]oxa[16]thia[1,17]diazapentacyclo [17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'S)-6-chloro-7'-hydroxy-11'-methyl-3,4-dihydro-2H,18'H-spiro [naphthalene-1,25'-[23]oxa[16]thia[1,17]diazapentacyclo [17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'R,15'R)-6-chloro-7'-hydroxy-11'-methyl-3,4-dihydro-2H,18'H-spiro [naphthalene-1,25'-[23]oxa[16]thia[1,17]diazapentacyclo [17.7.2.0$^{3,6}$.0$^{11,15}$.0$^{22,27}$]octacosa[8,19,21,27]tetraen]-18'-one 16',16'-dioxide (1.5 mg, 0.002 mmol). $^1$H NMR (400 MHz, CD$_2$Cl$_2$) δ 7.65 (d, J=8.6 Hz, 1H), 7.15 (dd, J=2.3, 8.4 Hz, 1H), 7.10 (d, J=2.3 Hz, 1H), 6.99-6.90 (m, 1H), 6.89 (s, 2H), 5.70-5.56 (m, 2H), 4.27 (t, J=8.1 Hz, 1H), 4.16 (br. s., 2H), 4.02 (br. s., 1H), 3.61 (d, J=14.1 Hz, 1H), 3.50-3.37 (m, 2H), 3.22 (br. s., 1H), 2.82-2.70 (m, 3H), 2.62-2.52 (m, 1H), 2.48-2.31 (m, 4H), 1.88-1.46 (m, 12H), 1.15 (s, 3H). MS (ESI, +ve ion) m/z 624.8 (M+H)$^+$.

Example 133. (1S,3'R,6'R,7'S,8'E,11R,15'S)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'R)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'S)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'R,15'R)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide

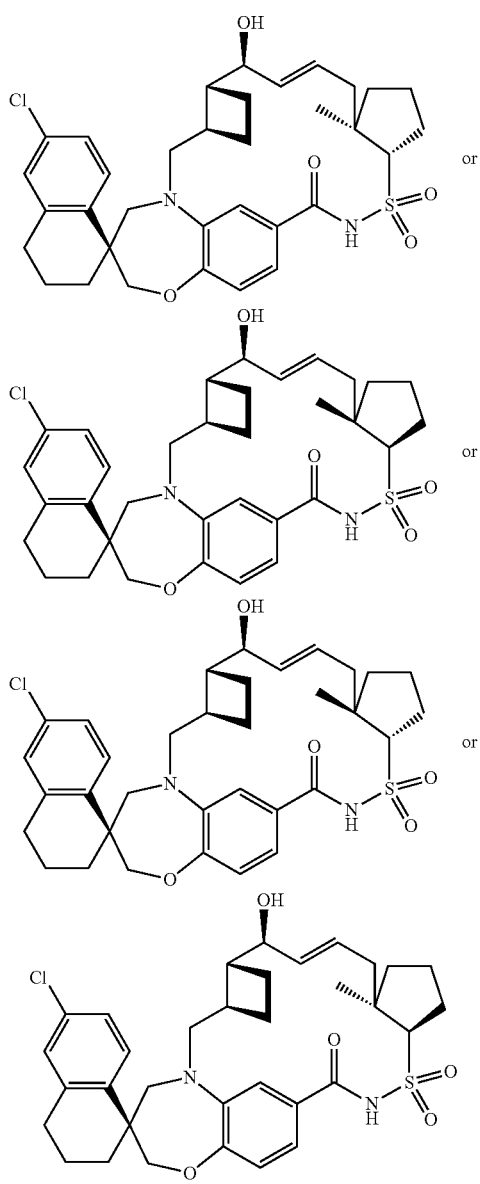

The title compound was synthesized as described in Example 120, Step 10 and was isolated as the third eluting isomer (6 mg). This material was further purified by column chromatography (1 g, hexanes:EtOAc (containing 1% AcOH), 1:0 to 1:1) to give (1S,3'R,6'R,7'S,8'E,11'R,15'S)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'R)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'S)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'R,15'R)-6-chloro-7'-hydroxy-11'-methyl-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide (2.5 mg, 0.004 mmol). $^1$H NMR (400 MHz, CD$_2$Cl$_2$) δ 7.72 (d, J=8.6 Hz, 1H), 7.28 (dd, J=2.0, 8.2 Hz, 1H), 7.17 (dd, J=2.3, 8.4 Hz, 1H), 7.09 (d, J=2.2 Hz, 1H), 6.96 (d, J=8.2 Hz, 1H), 6.74 (br. s., 1H), 6.20 (br. s., 1H), 5.67 (dd, J=7.9, 15.2 Hz, 1H), 4.18 (dd, J=3.3, 8.0 Hz, 1H), 4.09 (s, 2H), 3.85 (br. s., 1H), 3.77 (dd, J=2.2, 14.8 Hz, 1H), 3.74 (d, J=14.5 Hz, 1H), 3.37 (d, J=14.5 Hz, 1H), 3.11 (dd, J=10.9, 15.4 Hz, 1H), 2.86-2.70 (m, 3H), 2.58-2.46 (m, 1H), 2.46-2.24 (m, 4H), 1.97-1.90 (m, 2H), 1.86-1.74 (m, 5H), 1.74-1.68 (m, 2H), 1.67-1.62 (m, 2H), 1.46-1.38 (m, 1H), 1.11 (s, 3H). MS (ESI, +ve ion) m/z 624.8 (M+H)$^+$.

Example 134. (1S,3'R,6'R,7'S,8'E,10'S,13'R)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide or (1S,3'R,6'R,7'S,8'E,10'R,13'S)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide

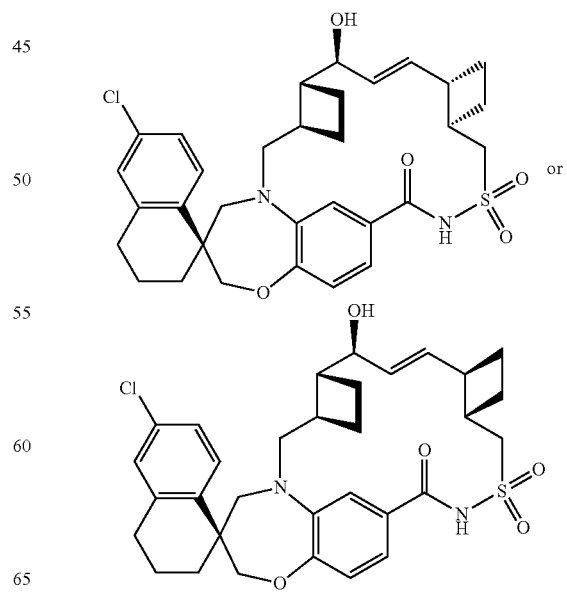

Step 1: (1R,2R)-cyclobutane-1,2-diyldimethanol and (1S,2S)-cyclobutane-1,2-diyldimethanol

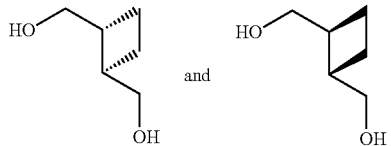 [SMILES: OC[C@@H]1CC[C@H]1CO ; OC[C@H]1CC[C@@H]1CO]

Trans-1,2-cyclobutanedicarboxylic acid (Synthon; 5 g, 34.7 mmol) in THF (34.7 mL) was transferred into a 3 neck round bottom flask fitted with an addition funnel, nitrogen inlet and thermometer and the flask was cooled to 0° C. Borane tetrahydrofuran complex (Sigma Aldrich, 1M in THF; 83 mL, 83 mmol) was then cannulated into the addition funnel. The borane tetrahydrofuran complex was then added into the stirred cooled mixture dropwise over 15 minutes (hydrogen gas evolved rapidly). After the addition was completed the reaction was allowed to warm to ambient temperature overnight under a $N_2$ atmosphere. After this time the reaction was treated with MeOH (50 mL) and then the mixture was transferred to a 500 mL flask and evaporated in vacuo. The solution was taken back up in MeOH and concentrated again. This process was repeated 3 times. The final clear grey oil was kept under vacuum for 3 hours to give (1R,2R)-cyclobutane-1,2-diyldimethanol and (1S,2S)-cyclobutane-1,2-diyldimethanol (3.5 g, 30.1 mmol, 87% yield).

Step 2: ((1R,2R)-2-(((tert-butyldimethylsilyl)oxy)methyl)cyclobutyl)methanol and ((1S,2S)-2-(((tert-butyldimethylsilyl)oxy)methyl)cyclobutyl)methanol

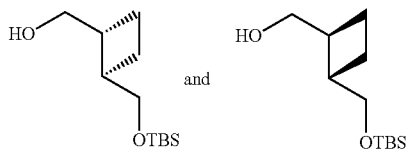 [SMILES: CC(C)(C)[Si](C)(C)OC[C@@H]1CC[C@H]1CO ; CC(C)(C)[Si](C)(C)OC[C@H]1CC[C@@H]1CO]

To a suspension of sodium hydride (0.861 g, 21.52 mmol) in THF (86 mL) at 0° C. under a $N_2$ atmosphere was added a solution of (1R,2R)-cyclobutane-1,2-diyldimethanol and (1S,2S)-cyclobutane-1,2-diyldimethanol (2.5 g, 21.52 mmol) in THF (20 mL) dropwise over 20 minutes. After this time the reaction was heated at 55° C. for 45 minutes and then it was cooled down to 0° C. and treated with a solution of TBS-Cl (Sigma Aldrich; 3.24 g, 21.52 mmol) in THF (15 mL). The reaction was stirred at ambient temperature overnight. After this time the reaction was quenched with $NH_4Cl$ (sat. aq. solution) and diluted with EtOAc. The separated aqueous layer was extracted with EtOAc, and the combined organic extracts were washed with brine, dried over $MgSO_4$, filtered and evaporated in vacuo. Column chromatography (80 g $SiO_2$, hexanes:EtOAc, 1:0 to 4:1) gave ((1R,2R)-2-(((tert-butyldimethylsilyl)oxy)methyl)cyclobutyl)methanol and ((1S,2S)-2-(((tert-butyldimethylsilyl)oxy)methyl)cyclobutyl)methanol (3.45 g, 14.97 mmol, 69.6% yield).

Step 3: ((1R,2R)-2-(((tert-butyldimethylsilyl)oxy)methyl)cyclobutyl)methyl methane sulfonate and ((1S,2S)-2-(((tert-butyldimethylsilyl)oxy)methyl)cyclobutyl)methyl methanesulfonate

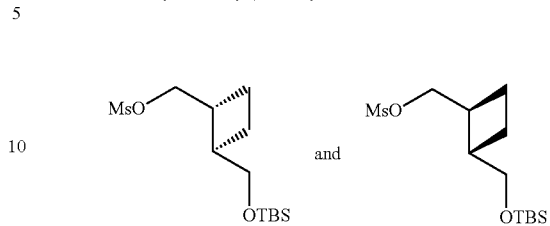

To a stirred solution of ((1R,2R)-2-(((tert-butyldimethylsilyl)oxy)methyl)cyclobutyl)methanol and ((1S,2S)-2-(((tert-butyldimethylsilyl)oxy)methyl)cyclobutyl)methanol (3.45 g, 14.97 mmol) in DCM (74.9 mL) at 0° C. was added triethylamine (3.13 mL, 22.46 mmol) followed by methanesulfonyl chloride (1.283 mL, 16.47 mmol). The reaction was stirred at ambient temperature for 2 hours. After this time the reaction was transferred to a separating funnel and successively washed with 1M HCl, $NaHCO_3$ and brine. The separated organic layer was dried over $MgSO_4$, filtered and evaporated in vacuo to give ((1R,2R)-2-(((tert-butyldimethylsilyl)oxy)methyl)cyclobutyl)methyl methane sulfonate and ((1S,2S)-2-(((tert-butyldimethylsilyl)oxy)methyl)cyclobutyl)methyl methanesulfonate (4.15 g, 13.45 mmol, 90% yield).

Step 4: ((1R,2R)-2-(((1-phenyl-1H-tetrazol-5-yl)thio)methyl)cyclobutyl)methanol and ((1S,2S)-2-(((1-phenyl-1H-tetrazol-5-yl)thio)methyl)cyclobutyl)methanol

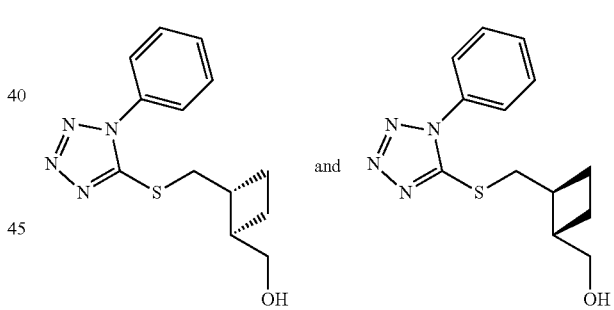

EtOH (45 mL) was degassed by sparging Ar(g) through for 30 minutes. 1-phenyl-1h-tetrazole-5-thiol (Sigma Aldrich; 4.79 g, 26.9 mmol) in the previously degassed EtOH (25 mL) under a $N_2$ atmosphere was treated with sodium ethoxide (Sigma Aldrich, 21% in EtOH; 7.53 mL, 20.18 mmol) and the mixture was stirred at ambient temperature for 30 minutes. After this time a solution of ((1R,2R)-2-(((tert-butyldimethylsilyl)oxy)methyl)cyclobutyl)methyl methane sulfonate and ((1S,2S)-2-(((tert-butyldimethylsilyl)oxy)methyl)cyclobutyl)methyl methanesulfonate (4.15 g, 13.45 mmol) in degassed EtOH (20 mL) was added dropwise via syringe and the mixture was stirred at ambient temperature over the weekend. After this time the reaction was heated at 60° C. for 3 hours. After this time the reaction was cooled to ambient temperature and the mixture was concentrated in vacuo. The residual material was partitioned between ethyl acetate and brine. The brine layer was back-extracted with ethyl acetate and the combined organics were then dried over magnesium sulfate, filtered, and evaporated in vacuo. Column chromatography (40 g SiO$_2$, hexanes:EtOAc, 1:0 to 1:1) gave ((1R,2R)-2-(((1-phenyl-1H-tetrazol-5-yl)thio)methyl)cyclobutyl)methanol and ((1S,2S)-2-(((1-phenyl-1H-tetrazol-5-yl)thio)methyl)cyclobutyl)methanol (2.0 g, 7.24 mmol, 53.8% yield).

Step 5: ((1R,2R)-2-(((1-phenyl-1H-tetrazol-5-yl)sulfonyl)methyl)cyclobutyl)methanol and ((1S,2S)-2-(((1-phenyl-1H-tetrazol-5-yl)sulfonyl)methyl)cyclobutyl)methanol

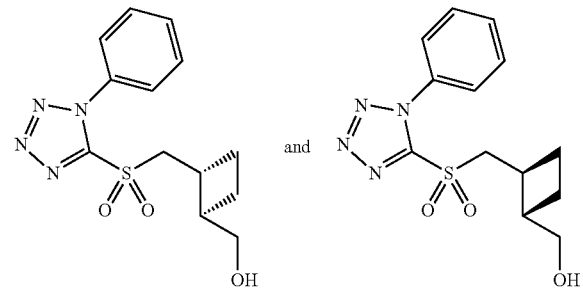 [SMILES: O=S(=O)(C[C@@H]1CC[C@H]1CO)c1nnnn1-c1ccccc1 ; O=S(=O)(C[C@H]1CC[C@@H]1CO)c1nnnn1-c1ccccc1]

To a stirred solution of ((1R,2R)-2-(((1-phenyl-1H-tetrazol-5-yl)thio)methyl)cyclobutyl)methanol and ((1S,2S)-2-(((1-phenyl-1H-tetrazol-5-yl)thio)methyl)cyclobutyl)methanol (0.5 g, 1.809 mmol) in toluene (3.29 mL) and water (0.329 mL) was added phenylphosphonic acid (Sigma Aldrich; 0.029 g, 0.181 mmol), tetrabutylammonium sulfate (Sigma Aldrich, 50 wt. % solution in water; 0.210 mL, 0.181 mmol), sodium tungstate dihydrate (Sigma Aldrich; 0.060 g, 0.181 mmol) and hydrogen peroxide (0.462 mL, 4.52 mmol). The reaction was stirred overnight at 40° C. After this time the reaction was cooled to ambient temperature and partitioned between EtOAc and Na$_2$SO$_3$. The separated aqueous layer was extracted with EtOAc and the combined organic extracts was washed with Na$_2$SO$_3$, brine, dried over MgSO$_4$, filtered and evaporated in vacuo. Column chromatography (24 g SiO$_2$, hexanes:EtOAc, 1:0 to 2:1) gave ((1R,2R)-2-(((1-phenyl-1H-tetrazol-5-yl)sulfonyl)methyl)cyclobutyl)methanol and ((1S,2S)-2-(((1-phenyl-1H-tetrazol-5-yl)sulfonyl)methyl)cyclobutyl)methanol (0.42 g, 1.362 mmol, 75% yield).

Step 6: 2-((((1R,2R)-2-(((1-phenyl-1H-tetrazol-5-yl)sulfonyl)methyl)cyclobutyl)methyl)thio)pyrimidine and 2-((((1S,2S)-2-(((1-phenyl-1H-tetrazol-5-yl)sulfonyl)methyl)cyclobutyl)methyl)thio)pyrimidine

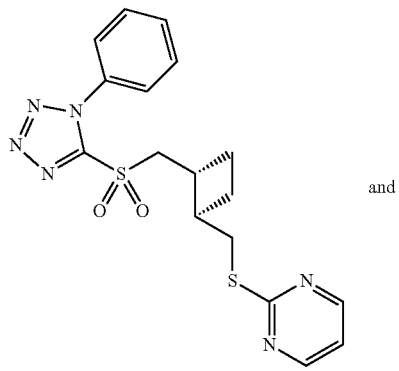

and

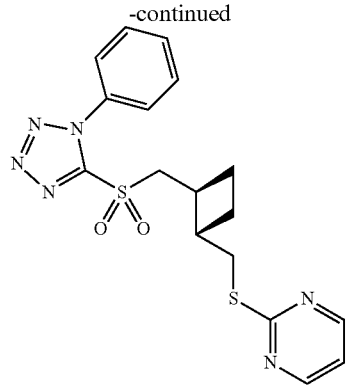

A dry flask containing a stir bar was charged with triphenylphosphine (Sigma Aldrich; 196 mg, 0.746 mmol) and the atmosphere was replaced with Ar and degassed toluene (6486 µL) was added. The solution was cooled to −5° C. in an ice/brine bath. Diethyl azodicarboxylate (Sigma Aldrich, 40 wt. % solution in toluene; 294 µL, 0.746 mmol) was then added dropwise over 1 minute and the reaction was stirred for 10 min. at −5° C. After this time ((1R,2R)-2-(((1-phenyl-1H-tetrazol-5-yl)sulfonyl)methyl)cyclobutyl)methanol and ((1S,2S)-2-(((1-phenyl-1H-tetrazol-5-yl)sulfonyl)methyl)cyclobutyl)methanol (200 mg, 0.649 mmol) in toluene (2.5 mL) was added and the reaction was stirred at −5° C. for 5 minutes. After this time 2-mercaptopyrimidine (Sigma Aldrich; 84 mg, 0.746 mmol) in THF (1.5 mL) was added over 2 minutes in 2 portions. The reaction was stirred at −5° C. for 3 hours. After this time the reaction was then quenched by addition of pH 7 buffer and the mixture was diluted with EtOAc. The separated aqueous layer was extracted with EtOAc and the combined organic extracts were washed with brine, dried over MgSO$_4$, filtered and evaporated in vacuo. Column chromatography (12 g SiO$_2$, hexanes:EtOAc, 1:0 to 4:1) gave 2-((((1R,2R)-2-(((1-phenyl-1H-tetrazol-5-yl)sulfonyl)methyl)cyclobutyl)methyl)thio)pyrimidine and 2-((((1S,2S)-2-(((1-phenyl-1H-tetrazol-5-yl)sulfonyl)methyl)cyclobutyl)methyl)thio)pyrimidine (200 mg, 0.497 mmol, 77% yield).

Step 7: (S)-methyl 5-(((1R,2R)-2-((S)-1-((tert-butyldimethylsilyl)oxy)allyl)cyclobutyl)methyl)-6'-chloro-3',4,4',5-tetrahydro-2H,2'H-spiro[benzo[b][1,4]oxazepine-3,1'-naphthalene]-7-carboxylate

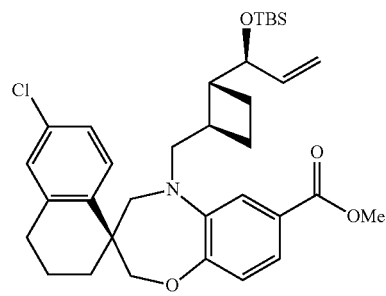 [SMILES: C=C[C@H](O[Si](C)(C)C(C)(C)C)[C@@H]1CC[C@H]1CN1C[C@@]2(CCCc3cc(Cl)ccc32)COc2ccc(C(=O)OC)cc21]

To a 250 mL flask which had been charged with an oven-dried stir bar was added (S)-methyl 6'-chloro-5-(((1R,2R)-2-((S)-1-hydroxyallyl)cyclobutyl)methyl)-3',4,4',5-tetrahydro-2H,2'Hspiro[benzo[b][1,4]oxazepine-3,1'-naphthalene]-7-carboxylate (Intermediate AA11A, Step 21; 8.77 g, 18.19 mmol). The atmosphere was replaced with nitrogen and the starting material was dissolved in anhydrous DCM (100 mL). 2,6-lutidine (5.4 mL; 46.6 mmol) was added and the solution was cooled to −5° C. Tert-butyldimethylsilyl trifluoromethanesulfonate (Aldrich; 5.0 mL, 21.77 mmol) was added dropwise over the course of seven minutes via syringe. After 1 hour the mixture was quenched by the addition of saturated sodium bicarbonate (20 mL) and the mixture was partitioned between DCM and saturated sodium bicarbonate. The aqeuous layer was back-extracted twice. The combined organics were washed with 10% citric acid, water, brine and dried over magnesium sulfate, filtered, and stripped in vacuo to give the crude product. This material was further purified by flash chromatography on a 330 g isco Gold silica column eluted with 0 to 20% EtOAc (containing 1% AcOH) in heptanes providing (S)-methyl 5-(((1R,2R)-2-((S)-1-((tertbutyldimethylsilyl)oxy)allyl)cyclobutyl)methyl)-6'-chloro-3',4,4',5-tetrahydro-2H,2'H-spiro[benzo[b][1,4]oxazepine-3,1'-naphthalene]-7-carboxylate (5 g, 8.39 mmol, 46% yield).

Step 8: (S)-methyl 5-(((1R,2R)-2-((1R,2R)-1-((tert-butyldimethylsilyl)oxy)-2,3-dihydroxypropyl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((1R,2S)-1-((tert-butyldimethylsilyl)oxy)-2,3-dihydroxypropyl)cyclobutyl)methyl)-6'-chloro-3',4,4',5-tetrahydro-2H,2'H-spiro[benzo[b][1,4]oxazepine-3,1'-naphthalene]-7-carboxylate

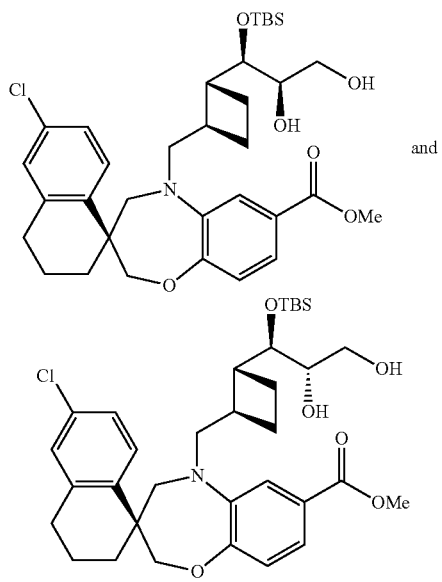

and

Osmium tetroxide (Sigma Aldrich; 0.132 ml, 0.419 mmol) was added to a stirred biphasic mixture of (S)-methyl 5-(((1R,2R)-2-((S)-1-((tert-butyldimethylsilyl)oxy)allyl)cyclobutyl)methyl)-6'-chloro-3',4,4',5-tetrahydro-2H,2'Hspiro[benzo[b][1,4]oxazepine-3,1'-naphthalene]-7-carboxylate (5 g, 8.39 mmol) and NMO (Sigma Aldrich; 3.93 g, 33.5 mmol) suspended in acetone (55.9 mL) and water (28.0 mL). The mixture was stirred at ambient temperature overnight. After this time an additional portion of NMO (0.4 g) and OsO$_4$ (0.01 g) was added followed by THF (50 mL) and tBuOH (15 mL). The mixture was stirred at ambient temperature for 3 hours. After this time the reaction was quenched by addition of solid sodium sulfite in water and the mixture was stirred at ambient temperature for 1 hour. After this time the reaction was partitioned between EtOAc and saturated sodium sulfite. The aqueous layer was back-extracted with EtOAc and the combined organics were washed with citric acid (15%), saturated sodium bicarbonate, brine, dried over magnesium sulfate, filtered, and evaporated in vacuo to give the crude product. Column chromatography (120 g Sift, hexanes:EtOAc, 1:0 to 3:1) gave (S)-methyl 5-(((1R,2R)-2-((1R,2R)-1-((tert-butyldimethylsilyl)oxy)-2,3-dihydroxypropyl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((1R,2S)-1-((tert-butyldimethylsilyl)oxy)-2,3-dihydroxypropyl)cyclobutyl)methyl)-6'-chloro-3',4,4',5-tetrahydro-2H,2'H-spiro[benzo[b][1,4]oxazepine-3,1'-naphthalene]-7-carboxylate (4.6 g, 7.30 mmol, 87% yield) as a white solid.

Step 9: (S)-methyl 5-(((1R,2R)-2-((R)-1-((tert-butyldimethylsilyl)oxy)-2-oxoethyl)cyclobutyl)methyl)-6'-chloro-3',4,4',5-tetrahydro-2H,2'Hspiro[benzo[b][1,4]oxazepine-3,1'-naphthalene]-7-carboxylate

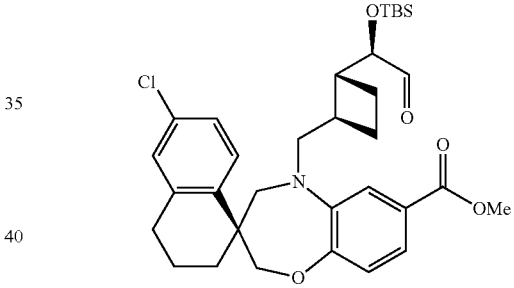

To a stirred solution of (S)-methyl 5-(((1R,2R)-2-((1R,2R)-1-((tert-butyldimethylsilyl)oxy)-2,3-dihydroxypropyl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((1R,2S)-1-((tert-butyldimethylsilyl)oxy)-2,3-dihydroxypropyl)cyclobutyl)methyl)-6'-chloro-3',4,4',5-tetrahydro-2H,2'H-spiro[benzo[b][1,4]oxazepine-3,1'-naphthalene]-7-carboxylate (600 mg, 0.952 mmol) in THF (4760 μL) and water (4760 μL) was added sodium periodate (Sigma Aldrich; 814 mg, 3.81 mmol) in one portion. The reaction was stirred at ambient temperature for 90 minutes. After this time the reaction was treated with an additional portion of sodium periodate (270 mg) and the mixture was stirred at ambient temperature for 30 minutes. After this time the reaction was partitioned between EtOAc and water. The separated aqueous layer was extracted with EtOAc and the combined organic extracts were washed with brine, dried over MgSO$_4$, filtered and evaporated in vacuo to give (S)-methyl 5-(((1R,2R)-2-((R)-1-((tert-butyldimethylsilyl)oxy)-2-oxoethyl)cyclobutyl)methyl)-6'-chloro-3',4,4',5-tetrahydro-2H,2'H-spiro[benzo[b][1,4]oxazepine-3,1'-naphthalene]-7-carboxylate (400 mg, 0.669 mmol, 70.2% yield) as a white solid.

Step 10: (S)-methyl 5-(((1R,2R)-2-((S,E)-1-((tert-butyldimethylsilyl)oxy)-3-((1S,2R)-2-((pyrimidin-2-ylthio)methyl)cyclobutyl)allyl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S,E)-1-((tert-butyldimethylsilyl)oxy)-3-((1R,2S)-2-ylthio)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S,Z)-1-((tert-butyldimethylsilyl)oxy)-3-((1S,2R)-2-((pyrimidin-2-ylthio)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S,Z)-1-((tert-butyldimethylsilyl)oxy)-3-((1R,2S)-2-((pyrimidin-2-ylthio)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate

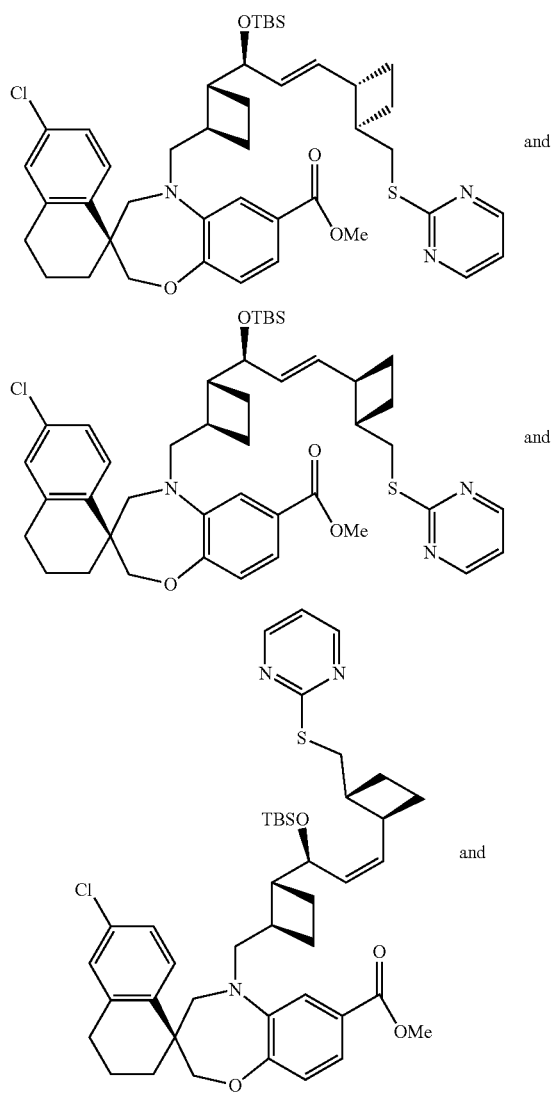

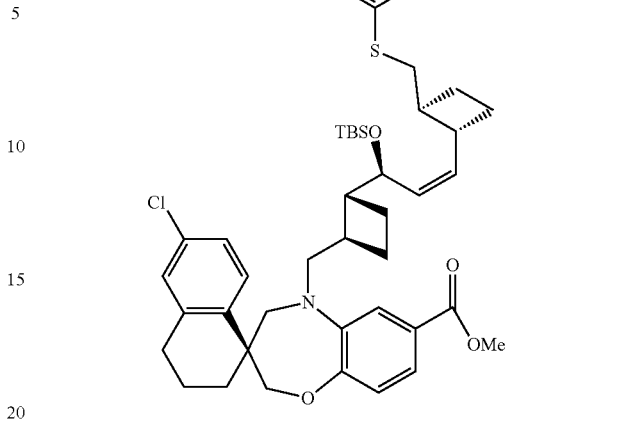

To a stirred solution of 2-(((((1R,2R)-2-(((1-phenyl-1H-tetrazol-5-yl)sulfonyl)methyl)cyclobutyl)methyl)thio)pyrimidine and 2-(((((1S,2S)-2-(((1-phenyl-1H-tetrazol-5-yl)sulfonyl)methyl)cyclobutyl)methyl)thio)pyrimidine (Example 134, step 6; 50.5 mg, 0.125 mmol) in THF (1.0 mL) was added 18-crown-6 (Sigma Aldrich; 66.3 mg, 0.251 mmol) and the mixture was cooled to −78° C. under a $N_2$ atmosphere. The mixture was then treated with KHMDS (Sigma Aldrich, 1M in THF; 125 µL, 0.125 mmol) dropwise over 2 minutes (rxn turns yellow) and the mixture was stirred at −78° C. for 35 minutes. After this time a solution of (S)-methyl 5-(((1R,2R)-2-((R)-1-((tertbutyldimethylsilyl)oxy)-2-oxoethyl)cyclobutyl)methyl)-6'-chloro-3',4,4',5-tetrahydro-2H,2'Hspiro[benzo[b][1,4]oxazepine-3,1'-naphthalene]-7-carboxylate (75 mg, 0.125 mmol) in THF (1.5 mL) was added dropwise via syringe over 2 min and the mixture was stirred at −78° C. for 90 minutes. After this time the mixture was quenched at −78° C. with $NH_4Cl$ (sat. aq. solution) and diluted with EtOAc and water and allowed to warm to ambient temperature. The separated organic layer was dried over $MgSO_4$, filtered and evaporated in vacuo. Column chromatography (12 g $SiO_2$, hexanes:EtOAc, 1:0 to 85:15) gave a ca. 5:1 mixture of (S)-methyl 6'-chloro-5-(((1R,2R)-2-((S,E)-1-((tertbutyldimethylsilyl)oxy)-3-((1S,2R)-2-((pyrimidin-2-ylthio)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S,E)-1-((tertbutyldimethylsilyl)oxy)-3-((1R,2S)-2-((pyrimidin-2-ylthio)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S,Z)-1-((tertbutyldimethylsilyl)oxy)-3-((1S,2R)-2-((pyrimidin-2-ylthio)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S,Z)-1-((tertbutyldimethylsilyl)oxy)-3-((1R,2S)-2-((pyrimidin-2-ylthio)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate (23 mg, 0.030 mmol, 23.69% yield).

Step 11: (S)-methyl 6'-chloro-5-((((1R,2R)-2-((S,E)-1-((tertbutyldimethylsilyl)oxy)-3-((1S,2R)-2-((pyrimidin-2-ylsulfonyl)methyl)cyclobutyl)allyl)cyclobutyl)methyl)-3',4,4',5-tetrahydro-2H, 2'H-spiro[benzo[b][1,4]oxazepine-3,1'-naphthalene]-7-carboxylate and (S)-methyl 6'-chloro-S-(((1R,2R)-2-((S,E)-1-((tertbutyldimethylsilyl)oxy)-3-((1R,2S)-2-((pyrimidin-2-ylsulfonyl)methyl)cyclobutyl)allyl)cyclobutyl)methyl)-3',4,4',5-tetrahydro-2H, 2'H-spiro[benzo[b][1,4]oxazepine-3,1'-naphthalene]-7-carboxylate and (S)-methyl 6'-chloro-5-(((1R,2R)-2-((S,Z)-1-((tertbutyldimethylsilyl)oxy)-3-((1S,2R)-2-((pyrimidin-2-ylsulfonyl)methyl)cyclobutyl)allyl)cyclobutyl)methyl)-3',4,4',5-tetrahydro-2H, 2'H-spiro[benzo[b][1,4]oxazepine-3,1'-naphthalene]-7-carboxylate and (S)-methyl 6'-chloro-5-(((1R,2R)-2-((S,Z)-1-((tertbutyldimethylsilyl)oxy)-3-((1R,2S)-2-((pyrimidin-2-ylsulfonyl)methyl)cyclobutyl)allyl)cyclobutyl)methyl)-3',4,4',5-tetrahydro-2H, 2'H-spiro[benzo[b][1,4]oxazepine-3,1'-naphthalene]-7-carboxylate

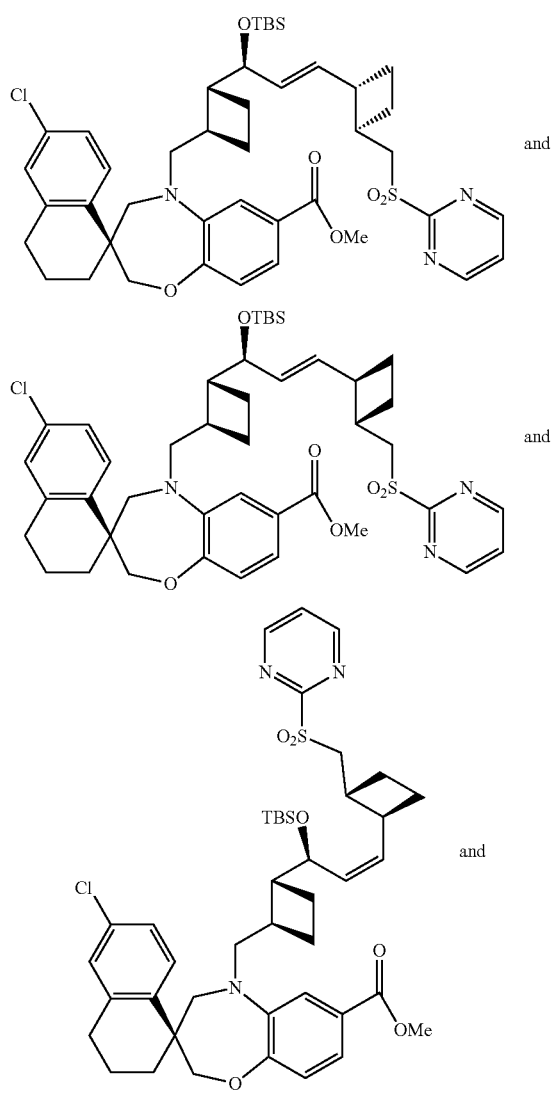

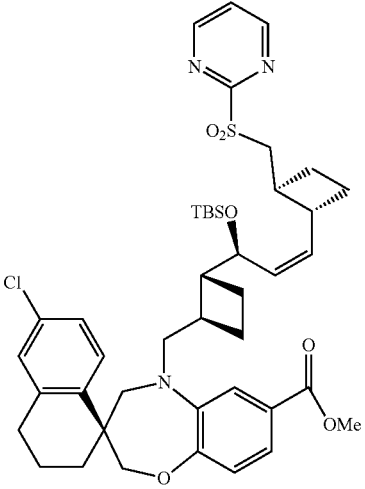

To a stirred solution of (S)-methyl 6'-chloro-5-(((1R,2R)-2-((S,E)-1-((tertbutyldimethylsilyl)oxy)-3-((1S,2R)-2-((pyrimidin-2-ylthio)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S,E)-1-((tertbutyldimethylsilyl)oxy)-3-((1R,2S)-2-((pyrimidin-2-ylthio)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S,Z)-1-((tertbutyldimethylsilyl)oxy)-3-((1S,2R)-2-((pyrimidin-2-ylthio)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S,Z)-1-((tertbutyldimethylsilyl)oxy)-3-((1R,2S)-2-((pyrimidin-2-ylthio)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate (57 mg, 0.074 mmol) in toluene (1338 μL) and water (134 μL) was added sodium tungstate dihydrate (Sigma Aldrich; 2.427 mg, 7.36 μmol), phenylphosphonic acid (Sigma Aldrich; 0.819 μL, 7.36 μmol), tetrabutylammonium sulfate (Sigma Aldrich, 50 wt. % solution in water; 8.55 μL, 7.36 μmol) followed by hydrogen peroxide (18.79 μL, 0.184 mmol). The reaction was stirred at ambient temperature for 1 hour. After this time an additional portion of phenylphosphonic acid (0.819 μL, 7.36 μmol), sodium tungstate dihydrate (2.427 mg, 7.36 μmol) and hydrogen peroxide (18.79 μL, 0.184 mmol) was added and the reaction was heated at 60° C. for 4 hours. After this time the reaction was cooled to ambient temperature and partitioned between EtOAc and sat. aq. $Na_2SO_3$. The separated aqueous layer was extracted with EtOAc and the combined organic extracts were washed with $Na_2SO_3$, dried over $MgSO_4$, filtered and evaporated in vacuo. The crude material was combined with that from a previous run and purified by column chromatography (4 g $SiO_2$, hexanes:EtOAc, 1:0 to 4:1) to give (S)-methyl 6'-chloro-5-(((1R,2R)-2-((S,E)-1-((tertbutyldimethylsilyl)oxy)-3-((1S,2R)-2-((pyrimidin-2-ylsulfonyl)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S,E)-1-((tertbutyldimethylsilyl)oxy)-3-((1R,2S)-2-((pyrimidin-2-ylsulfonyl)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-

437

((((1R,2R)-2-((S,Z)-1-((tertbutyldimethylsilyl)oxy)-3-((1S,2R)-2-((pyrimidin-2-ylsulfonyl)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-((((1R,2R)-2-((S,Z)-1-((tertbutyldimethylsilyl)oxy)-3-((1R,2S)-2-((pyrimidin-2-ylsulfonyl)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate (50 mg, 0.062 mmol).

Step 12: (S)-methyl 6'-chloro-5-((((1R,2R)-2-((S,E)-1-((tertbutyldimethylsilyl)oxy)-3-((1S,2R)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-((((1R,2R)-2-((S,E)-1-((tertbutyldimethylsilyl)oxy)-3-((1R,2S)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-((((1R,2R)-2-((S,Z)-1-((tertbutyldimethylsilyl)oxy)-3-((1S,2R)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-((((1R,2R)-2-((S,Z)-1-((tertbutyldimethylsilyl)oxy)-3-((1R,2S)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylate

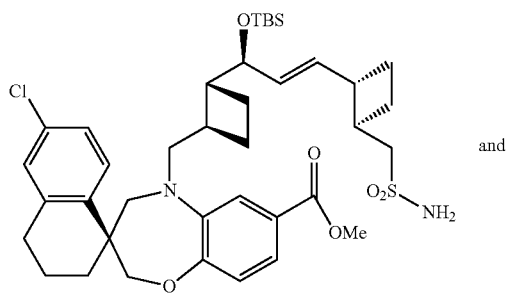

and

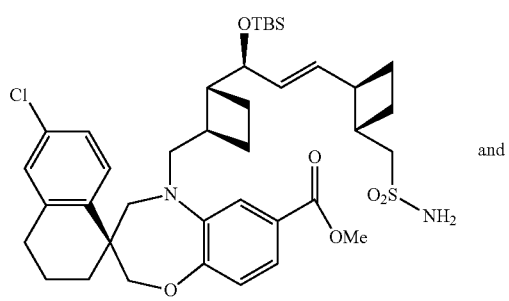

438

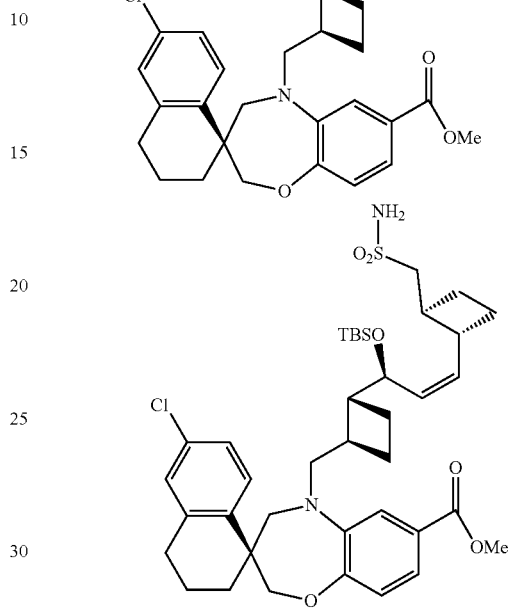

To a stirred solution of (S)-methyl 6'-chloro-5-((((1R,2R)-2-((S,E)-1-((tertbutyldimethylsilyl)oxy)-3-((1S,2R)-2-((pyrimidin-2-ylsulfonyl)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-((((1R,2R)-2-((S,E)-1-((tertbutyldimethylsilyl)oxy)-3-((1R,2S)-2-((pyrimidin-2-ylsulfonyl)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-((((1R,2R)-2-((S,Z)-1-((tertbutyldimethylsilyl)oxy)-3-((1S,2R)-2-((pyrimidin-2-ylsulfonyl)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-((((1R,2R)-2-((S,Z)-1-((tertbutyldimethylsilyl)oxy)-3-((1R,2S)-2-((pyrimidin-2-ylsulfonyl)methyl)cyclobutyl)allyl)cyclobutyl)methyl)-3',4,4',5-tetrahydro-2H,2'H-spiro[benzo[b][1,4]oxazepine-3,1'-naphthalene]-7-carboxylate (50 mg, 0.062 mmol) in MeOH (1.8 mL) was added potassium carbonate (42.8 mg, 0.310 mmol). The reaction was stirred at ambient temperature for 1 hour. After this time the reaction was treated with hydroxylaminesulfonic acid (Sigma Aldrich; 10.52 mg, 0.093 mmol) in water (1.0 mL) and the mixture was heated at 45° C. for 90 minutes. After this time the reaction was cooled to ambient temperature and partitioned between EtOAc and 1M HCl. The separated organic layer was dried over MgSO$_4$, filtered and evaporated in vacuo. Column chromatography (4 g SiO$_2$, hexanes: EtOAc, 1:0 to 4:1) gave (S)-methyl 6'-chloro-5-((((1R,2R)-2-((S,E)-1-((tertbutyldimethylsilyl)oxy)-3-((1S,2R)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-

(((1R,2R)-2-((S,E)-1-((tertbutyldimethylsilyl)oxy)-3-((1R,2S)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S,Z)-1-((tertbutyldimethylsilyl)oxy)-3-((1S,2R)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S,Z)-1-((tertbutyldimethylsilyl)oxy)-3-((1R,2S)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylate (23 mg, 0.031 mmol, 49.9% yield).

Step 13: (S)-6'-chloro-5-(((1R,2R)-2-((S,E)-1-((tert-butyldimethylsilyl)oxy)-3S,2R)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((S,E)-1-((tertbutyldimethylsilyl)oxy)-3-((1R,2S)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((S,Z)-1-((tertbutyldimethylsilyl)oxy)-3-((1S,2R)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((S,Z)-1-((tertbutyldimethylsilyl)oxy)-3-((1R,2S)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylic Acid

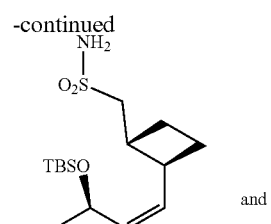

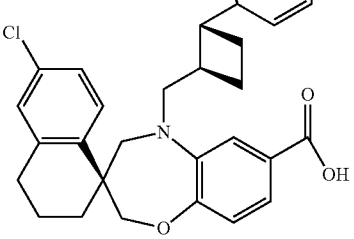

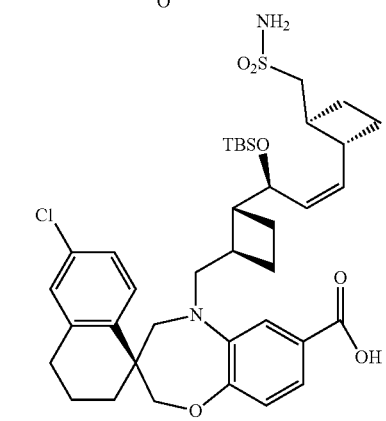


and

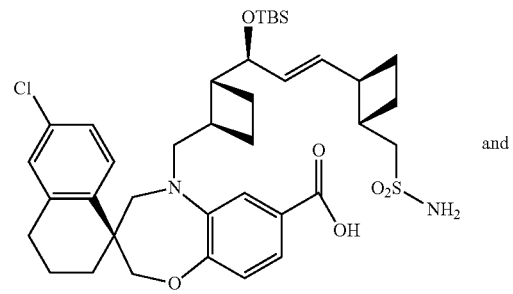

and

To a stirred solution of (S)-methyl 6'-chloro-5-(((1R,2R)-2-((S,E)-1-((tertbutyldimethylsilyl)oxy)-3,2R)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S,E)-1-((tertbutyldimethylsilyl)oxy)-3-((1R,2S)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S,Z)-1-((tertbutyldimethylsilyl)oxy)-3-((1S,2R)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S,Z)-1-((tertbutyldimethylsilyl)oxy)-3-((1R,2S)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylate (23 mg, 0.031 mmol) in THF (516 μL) and MeOH (516 μL) was added lithium hydroxide (22.23 mg, 0.928 mmol) in water (516 μL). The reaction was stirred at 60° C. for 4 hours and at ambient temperature overnight. After this time an additional portion of lithium hydroxide (22.23 mg, 0.928 mmol) in water (516 μL) was added and the reaction was stirred at 60° C. for 24 hours. After this time the reaction was cooled to ambient temperature and partitioned between EtOAc and water. The separated organic layer was dried over MgSO$_4$, filtered and evaporated in vacuo to give (S)-6'-chloro-5-(((1R,2R)-2-((S,E)-1-((tertbutyldimethylsilyl)oxy)-3-((1S,2R)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-((tertbutyldimethylsilyl)oxy)-3-((1R,2S)-2-

(sulfamoylmethyl)cyclobutyl)allyl)cyclobutyl)methyl)-3',4, 4',5-tetrahydro-2H,2'H-spiro[benzo[b][1,4]oxazepine-3,1'-naphthalene]-7-carboxylic acid and (S)-6'-chloro-5-(((1R,2R)-2-((S,Z)-1-((tertbutyldimethylsilyl)oxy)-3-((1S,2R)-2-(sulfamoylmethyl)cyclobutyl)allyl)cyclobutyl)methyl)-3',4, 4',5-tetrahydro-2H,2'H-spiro[benzo[b][1,4]oxazepine-3,1'-naphthalene]-7-carboxylic acid and (S)-6'-chloro-5-(((1R,2R)-2-((S,Z)-1-((tertbutyldimethylsilyl)oxy)-3-((1R,2S)-2-(sulfamoylmethyl)cyclobutyl)allyl)cyclobutyl)methyl)-3',4, 4',5-tetrahydro-2H,2'H-spiro[benzo[b][1,4]oxazepine-3,1'-naphthalene]-7-carboxylic acid (22.5 mg, 0.031 mmol, 100% yield).

Step 14: (1S,3'R,6'R,7'S,8'E,10'S,13'R)-6-chloro-7'-((tertbutyldimethylsilyl)oxy)-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide and (1S,3'R,6'R,7'S,8'E,10'R,13'S)-6-chloro-7'-((tertbutyldimethylsilyl)oxy)-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide and (1S,3'R,6'R,7'S,8'Z,10'S,13'R)-6-chloro-7'-((tertbutyldimethylsilyl)oxy)-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide and (1S,3'R,6'R,7'S,8'Z,10'R,13'S)-6-chloro-7'-((tertbutyldimethylsilyl)oxy)-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide

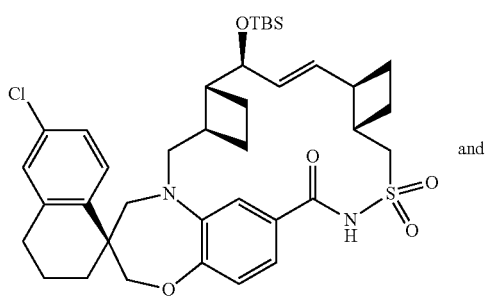

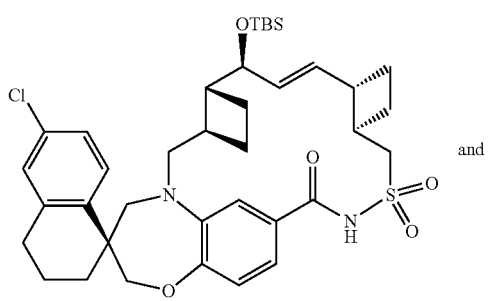

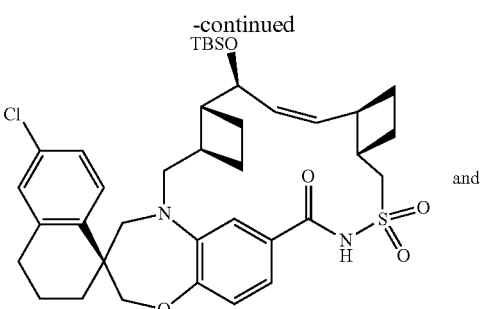

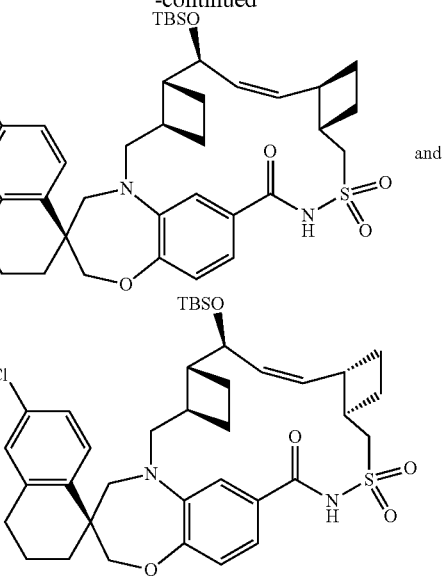

To a stirred solution of (S)-6'-chloro-5-(((1R,2R)-2-((S,E)-1-((tertbutyldimethylsilyl)oxy)-3-((1S,2R)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-((tertbutyldimethylsilyl)oxy)-3-((1R,2S)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,Z)-1-((tertbutyldimethylsilyl)oxy)-3-((1S,2R)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,Z)-1-((tertbutyldimethylsilyl)oxy)-3-((1R,2S)-2-(sulfamoylmethyl)cyclobutyl)allyl)cyclobutyl)methyl)-3',4,4',5-tetrahydro-2H,2'H-spiro[benzo[b][1,4]oxazepine-3,1'-naphthalene]-7-carboxylic acid (22 mg, 0.030 mmol) in DCM (15.1 mL) was added EDC (Sigma Aldrich; 11.56 mg, 0.060 mmol). The reaction was cooled to 0° C. and treated with DMAP (Sigma Aldrich; 6.26 mg, 0.051 mmol) portionwise over 2 minutes. After this time the cooling bath was removed and the reaction was allowed to warm to ambient temperature overnight. After this time the reaction was partitioned between 1M HCl and DCM. The separated organic layer was washed with NaHCO$_3$, dried over MgSO$_4$, filtered and evaporated in vacuo to give (1S,3'R,6'R,7'S,8'E,10'S,13'R)-6-chloro-7'-((tertbutyldimethylsilyl)oxy)-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide and (1S,3'R,6'R,7'S,8'E,10'R,13'S)-6-chloro-7'-((tertbutyldimethylsilyl)oxy)-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide and (1S,3'R,6'R,7'S,8'Z,10'S,13'R)-6-chloro-7'-((tertbutyldimethylsilyl)oxy)-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide and (1S,3'R,6'R,7'S,8'Z,10'R,13'S)-6-chloro-7'-((tertbutyldimethylsilyl)oxy)-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'- one 15',15'-dioxide (14 mg, 0.020 mmol, 65.2% yield). This material was used without further purification in the next step.

Step 15: (1S,3'R,6'R,7'S,8'E,10'S,13'R)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide or (1S,3'R,6'R,7'S,8'E,10'R,13'S)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide In a 25 mL round bottom flask containing (1S,3'R,6'R,7'S,8'E,10'S,13'R)-6-chloro-7'-((tertbutyldimethylsilyl)oxy)-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide and (1S,3'R,6'R,7'S,8'E,10'R,13'S)-6-chloro-7'-((tertbutyldimethylsilyl)oxy)-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide and (1S,3'R,6'R,7'S,8'Z,10'S,13'R)-6-chloro-7'-((tertbutyldimethylsilyl)oxy)-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide and (1S,3'R,6'R,7'S,8'Z,10'R,13'S)-6-chloro-7'-((tertbutyldimethylsilyl)oxy)-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide was added a 1M THF solution of TBAF (394 µL, 0.394 mmol). The reaction was stirred at ambient temperature for 1 hour. The desired product was not observed. An additional portion of 1M THF solution of TBAF (394 µL, 0.394 mmol) was added and the reaction was stirred at ambient temperature for 8 hours. After this time the reaction was stored in the freezer for 14 days. The reaction was treated with an additional portion of TBAF (394 µL, 0.394 mmol) and then it was stirred at ambient temperature for 3 days. After this time the reaction was partitioned between EtOAc and 1M HCl. The separated organic layer was washed with NaHCO$_3$ and the organic layer was dried over MgSO$_4$, filtered and evaporated in vacuo. Column chromatography (1 g SiO$_2$, DCM:acetone, 1:0 to 7:3) gave a mixture of the title compounds (9 mg). This material was purified by reverse phase preparative HPLC (C18 column, 10 to 90% acetonitrile:water, 30 minutes) to give (1S,3'R,6'R,7'S,8'E,10'S,13'R)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide or (1S,3'R,6'R,7'S,8'E,10'R,13'S)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide as the first eluting minor isomer (1.5 mg, 0.003 mmol, 12.8% yield). $^1$H NMR (500 MHz, CD$_2$Cl$_2$) δ 8.79 (br. s., 1H), 7.72 (d, J=8.6 Hz, 1H), 7.17 (dd, J=1.7, 8.3 Hz, 1H), 7.14 (d, J=8.6 Hz, 1H), 7.09 (d, J=1.5 Hz, 1H), 6.95 (d, J=8.1 Hz, 1H), 6.74 (s, 1H), 6.13 (dd, J=3.8, 15.5 Hz, 1H), 5.63 (dd, J=6.2, 15.3 Hz, 1H), 4.22 (br. s., 1H), 4.11-4.04 (m, 2H), 3.74 (d, J=14.2 Hz, 1H), 3.77 (br. s., 1H), 3.68 (d, J=14.4 Hz, 1H), 3.56 (dd, J=4.8, 14.8 Hz, 1H), 3.37 (d, J=14.7 Hz, 1H), 3.12 (dd, J=10.9, 14.8 Hz, 1H), 2.90-2.82 (m, 1H), 2.82-2.71 (m, 2H), 2.66-2.56 (m, 1H), 2.45 (dd, J=8.3, 14.7 Hz, 1H), 2.38-2.30 (m, 2H), 2.14-1.52 (m, 12H). MS (ESI, +ve ion) m/z 624.8 (M+H)$^+$.

Example 135. (1S,3'R,6'R,7'S,8'E,10'R,13'S)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide or (1S,3'R,6'R,7'S,8'E,10'S,13'R)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide

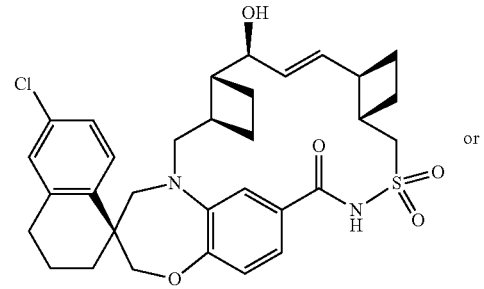

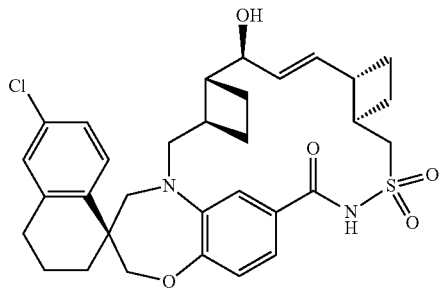

The title compound was synthesized as described in Example 134, Step 15. After purification by reverse phase preparative HPLC (C18 column, 10 to 90% acetonitrile:water, 30 minutes) (1S,3'R,6'R,7'S,8'E,10'R,13'S)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide or (1S,3'R,6'R,7'S,8'E,10'S,13'R)-6-chloro-7'-hydroxy-3,4-dihydro-2H,17'H-spiro[naphthalene-1,24'-[22]oxa[15]thia[1,16]diazapentacyclo[16.7.2.0$^{3,6}$.0$^{10,13}$.0$^{21,26}$]heptacosa[8,18,20,26]tetraen]-17'-one 15',15'-dioxide was isolated as the second eluting major isomer (2.6 mg, 0.004 mmol, 22.1% yield). $^1$H NMR (500 MHz, CD$_2$Cl$_2$) δ 9.24 (br. s., 1H), 7.71 (d, J=8.6 Hz, 1H), 7.22 (dd, J=1.5, 8.1 Hz, 1H), 7.17 (dd, J=2.2, 8.6 Hz, 1H), 7.09 (d, J=2.2 Hz, 1H), 6.95 (d, J=8.3 Hz, 1H), 6.74 (br. s., 1H), 6.16 (d, J=15.2 Hz, 1H), 5.56 (dd, J=6.1, 15.6 Hz, 1H), 4.26-4.15 (m, 1H), 4.13-4.04 (m, 2H), 3.75 (br. s., 1H), 3.71 (d, J=14.2 Hz, 1H), 3.67-3.61 (m, 1H), 3.58 (dd, J=3.2, 14.9 Hz, 1H), 3.40 (d, J=14.4 Hz, 1H), 3.23-3.13 (m, 1H), 2.88 (d, J=8.3 Hz, 1H), 2.83-2.71 (m, 2H), 2.59-2.47 (m, 2H), 2.38 (br. s., 1H), 2.16-2.07 (m, 1H), 2.06-2.01 (m, 2H), 1.96-1.85 (m, 4H), 1.78-1.67 (m, 4H), 1.60 (td, J=7.4, 14.7 Hz, 1H), 1.48-1.41 (m, 1H). MS (ESI, +ve ion) m/z 624.8 (M+H)$^+$.

Example 136. (1S,3'R,6'R,7'S,8'E,11'S,12'R)-6-chloro-7'-hydroxy-11'-methyl-12'((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11',12'S)-6-chloro-7'-hydroxy-11'-methyl-12'((2S)-tetrahydro-2-furanylmethyl)-3,4-dihydro-2H,15'H-spiro[naphthalene-1,22'420]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-11'-methyl-12'((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-7'-hydroxy-11'-methyl-12'((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'R)-6-chloro-7'-hydroxy-11'-methyl-12'((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'S)-6-chloro-7'-hydroxy-11'-methyl-12'((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'R,12'R)-6-chloro-7'-hydroxy-11'-methyl-12'((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'R,12'S)-6-chloro-7'-hydroxy-11'-methyl-12'((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-hydroxy-11'-methyl-12'((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methyl-12'((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-11'-methyl-12'((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-7'-hydroxy-11'-methyl-12'((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'R)-6-chloro-7'-hydroxy-11'-methyl-12'((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'S)-6-chloro-7'-hydroxy-11'-methyl-12'((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'R,12'R)-6-chloro-7'-hydroxy-11'-methyl-12'((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'R,12'S)-6-chloro-7'-hydroxy-11'-methyl-12'((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

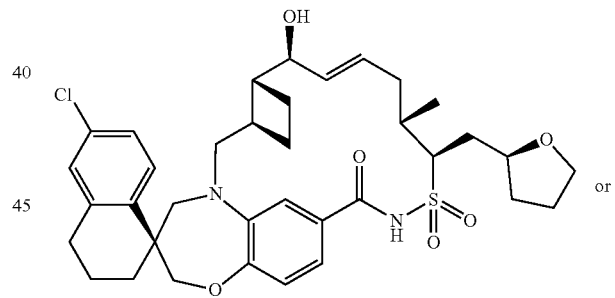

or

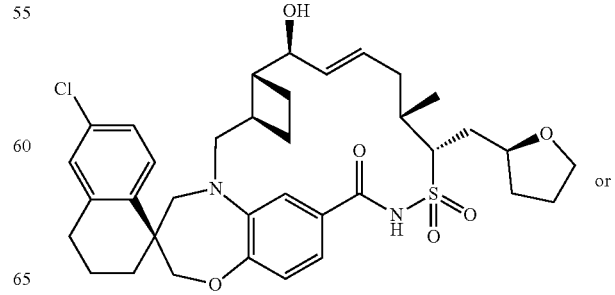

or

447
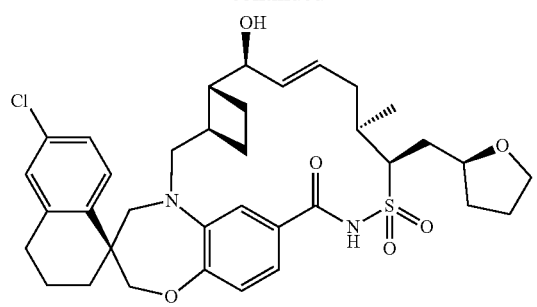
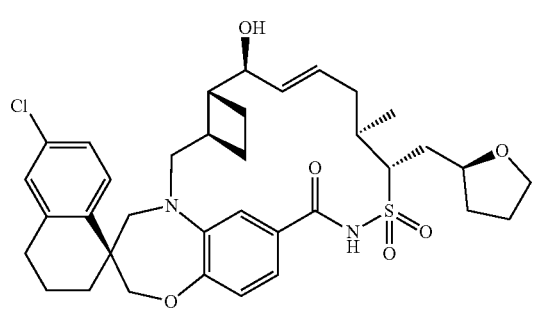
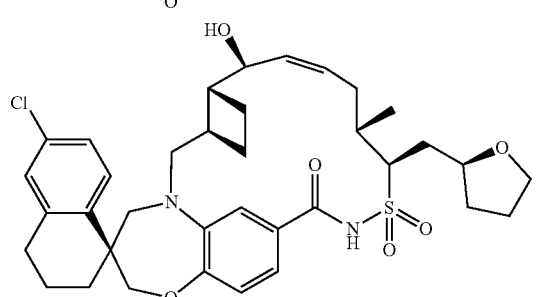
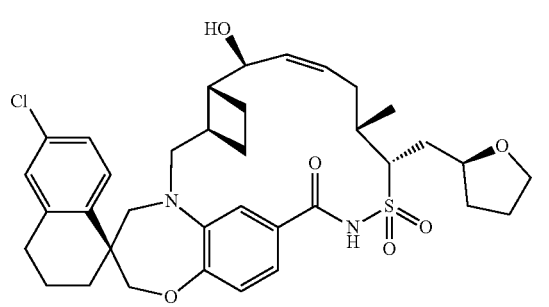
448
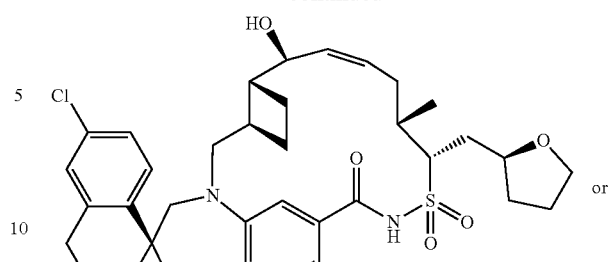
or
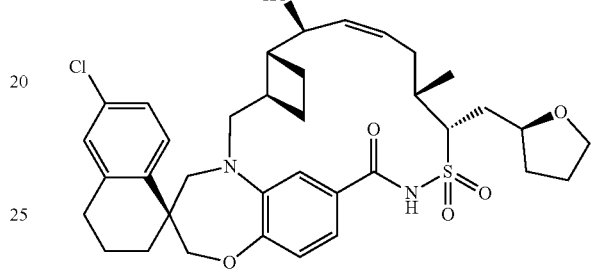
or
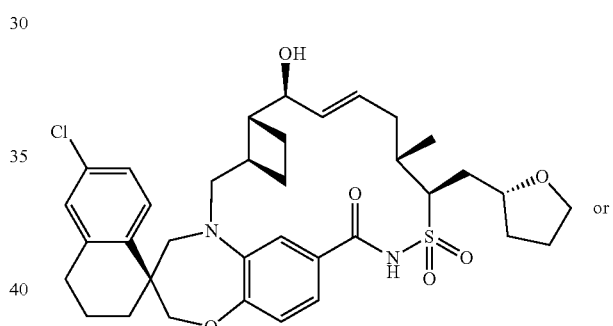
or
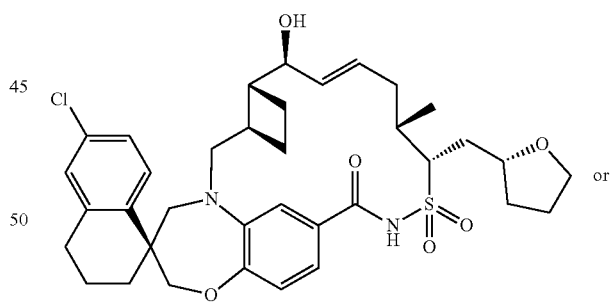
or 449
-continued

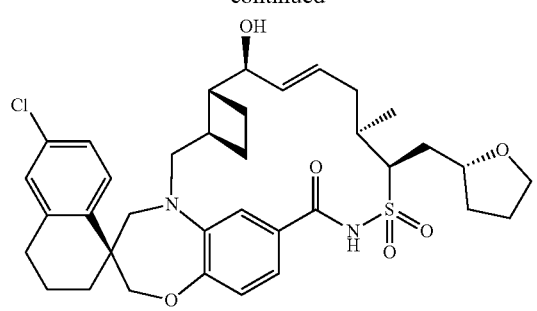

or

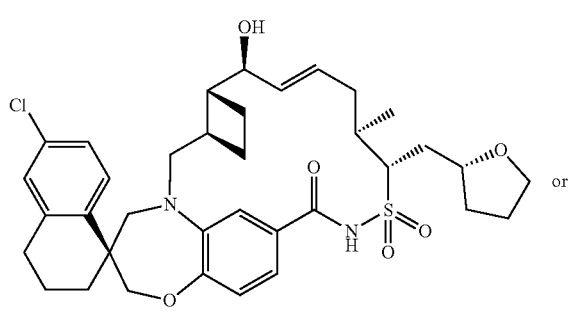

or

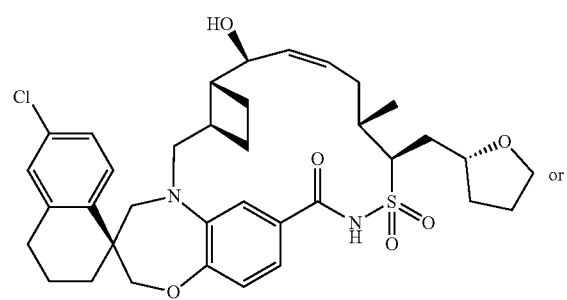

or


or

450
-continued

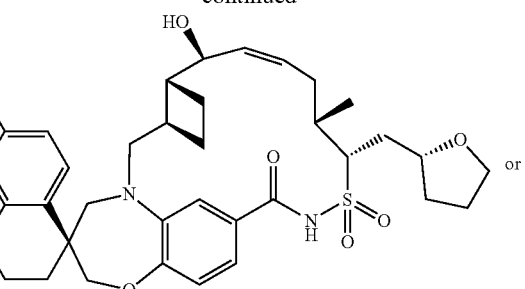

or

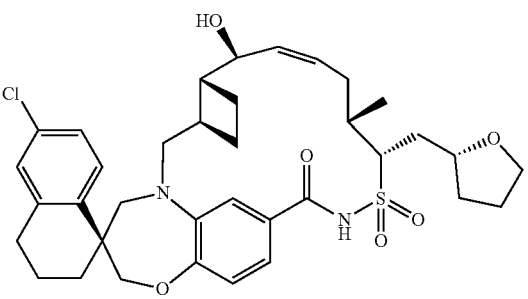 [SMILES: C[C@H]1C/C=C\[C@H](O)[C@@H]2CC[C@H]2CN2C[C@@]3(CCCc4cc(Cl)ccc43)COc3ccc(cc32)C(=O)NS(=O)(=O)[C@H]1C[C@H]1CCCO1]

Step 1: (2S,3R)—N,N-bis(4-methoxybenzyl)-3-methyl-1-(tetrahydro-2-furanyl)-5-hexene-2-sulfonamide and (2S,3S)—N,N-bis(4-methoxybenzyl)-3-methyl-1-(tetrahydro-2-furanyl)-5-hexene-2-sulfonamide and (2R,3R)—N,N-bis(4-methoxybenzyl)-3-methyl-1-(tetrahydro-2-furanyl)-5-hexene-2-sulfonamide and (2R,3S)—N,N-bis(4-methoxybenzyl)-3-methyl-1-(tetrahydro-2-furanyl)-5-hexene-2-sulfonamide and (2S,3R)—N,N-bis(4-methoxybenzyl)-3-methyl-1-((2R)-tetrahydro-2-furanyl)-5-hexene-2-sulfonamide and (2S,3S)—N,N-bis(4-methoxybenzyl)-3-methyl-1-((2R)-tetrahydro-2-furanyl)-5-hexene-2-sulfonamide and (2R,3R)—N,N-bis(4-methoxybenzyl)-3-methyl-1-((2R)-tetrahydro-2-furanyl)-5-hexene-2-sulfonamide and (2R,3S)—N,N-bis(4-methoxybenzyl)-3-methyl-1-((2R)-tetrahydro-2-furanyl)-5-hexene-2-sulfonamide

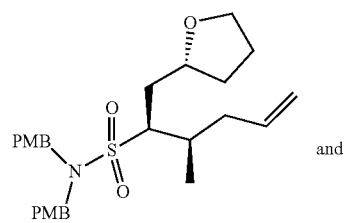

and

451
-continued
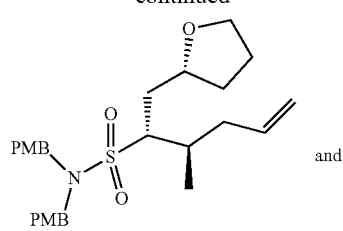
and
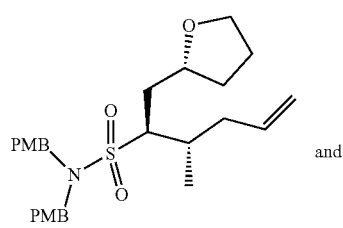
and
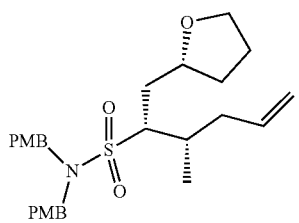
and
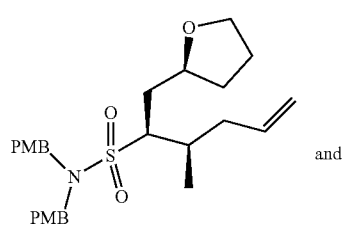
and
452
-continued
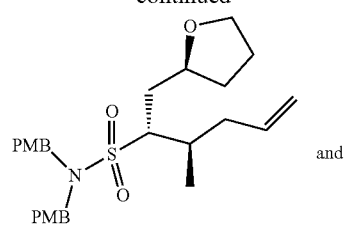
and
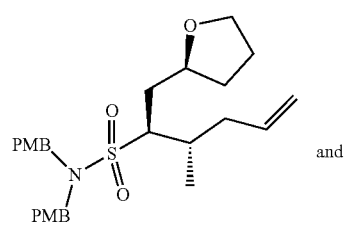
and
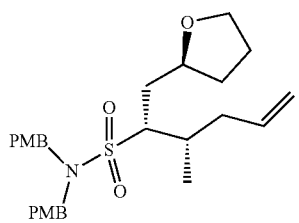
and
The title compounds were prepared from a mixture of (2S)—N,N-bis(4-methyoxybenzyl)-2-methylpent-4-ene-1-sulfonamide and (2R)—N,N-bis(4-methyoxybenzyl)-2-methylpent-4-ene-1-sulfonamide (Example 472, Step 1) using a similar procedure described in Example 380, Step 2, replacing (bromomethyl)cyclopropane with 2-(bromomethyl)tetrahydrofuran.

453

Step 2: (2S,3R)-3-methyl-1-((2R)-tetrahydro-2-furanyl)-5-hexene-2-sulfonamide and (2R,3R)-3-methyl-1-((2R)-tetrahydro-2-furanyl)-5-hexene-2-sulfonamide and (2S,3S)-3-methyl-1-((2R)-tetrahydro-2-furanyl)-5-hexene-2-sulfonamide and (2R,3S)-3-methyl-1-((2R)-tetrahydro-2-furanyl)-5-hexene-2-sulfonamide (2S,3R)-3-methyl-1-((2S)-tetrahydro-2-furanyl)-5-hexene-2-sulfonamide and (2R,3R)-3-methyl-1-((2S)-tetrahydro-2-furanyl)-5-hexene-2-sulfonamide and (2S,3S)-3-methyl-1-((2S)-tetrahydro-2-furanyl)-5-hexene-2-sulfonamide and (2R,3S)-3-methyl-1-((2S)-tetrahydro-2-furanyl)-5-hexene-2-sulfonamide

 and

 and

 and

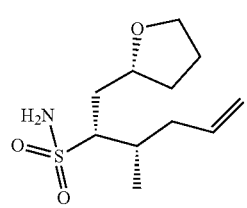 and

454

-continued

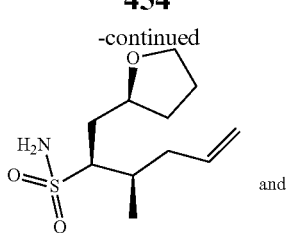 and

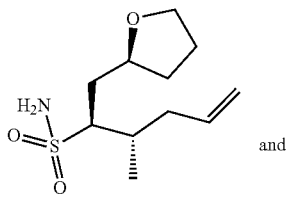 and

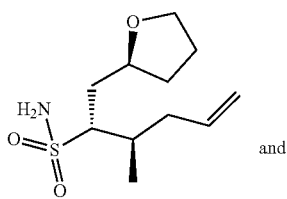 and

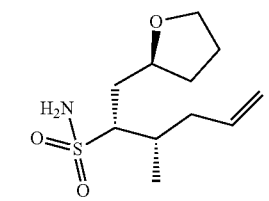

The title compounds were prepared from above mixture of (2S,3R)—N,N-bis(4-methoxybenzyl)-3-methyl-1-(tetrahydro-2-furanyl)-5-hexene-2-sulfonamide and (2S,3S)—N,N-bis(4-methoxy benzyl)-3-methyl-1-(tetrahydro-2-furanyl)-5-hexene-2-sulfonamide and (2R,3R)—N,N-bis(4-methoxybenzyl)-3-methyl-1-(tetrahydro-2-furanyl)-5-hexene-2-sulfonamide and (2R,3S)—N,N-bis(4-methoxybenzyl)-3-methyl-1-(tetrahydro-2-furanyl)-5-hexene-2-sulfonamide and (2S,3R)—N,N-bis(4-methoxybenzyl)-3-methyl-1-((2R)-tetrahydro-2-furanyl)-5-hexene-2-sulfonamide and (2S,3S)—N,N-bis(4-methoxybenzyl)-3-methyl-1-((2R)-tetrahydro-2-furanyl)-5-hexene-2-sulfonamide and (2R,3R)—N,N-bis(4-methoxybenzyl)-3-methyl-1-((20-tetrahydro-2-furanyl)-5-hexene-2-sulfonamide and (2R,3S)—N,N-bis(4-methoxybenzyl)-3-methyl-1-((2R)-tetrahydro-2-furanyl)-5-hexene-2-sulfonamide using a similar procedure described in Example 472, Step 3.

Step 3: (3S)-6'-chloro-5-(((1R,2R)-2-((1S,2E)-1-hydroxy-2-hexen-1-yl)cyclobutyl)methyl)-N-(((2R,3R)-3-methyl-1-(((2S)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3S)-3-methyl-1-(((2S)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3S)-3-methyl-1-(((2S)-tetrahydro-2-furanyl)-5-hexen-2-yl)sulfonyl)-3',4,4',5-tetrahydro-2'H-spiro[1,5-BENZ oxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3S)-3-methyl-1-(((2S)-tetrahydro-2-furanyl)-5-hexen-2-yl)sulfonyl)-3',4,4',5-tetrahydro-2'H-spiro[1,5-BENZ oxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3R)-3-methyl-1-(((2R)-tetrahydro-2-furanyl)-5-hexen-2-yl)sulfonyl)-3',4,4',5-tetrahydro-2'H-spiro[1,5-BENZ oxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3S)-3-methyl-1-(((2R)-tetrahydro-2-furanyl)-5-hexen-2-yl)sulfonyl)-3',4,4',5-tetrahydro-2'H-spiro[1,5-BENZ oxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3S)-3-methyl-1-(((2R)-tetrahydro-2-furanyl)-5-hexen-2-yl)sulfonyl)-3',4,4',5-tetrahydro-2'H-spiro[1,5-BENZ oxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3S)-3-methyl-1-(((2R)-tetrahydro-2-furanyl)-5-hexen-2-yl)sulfonyl)-3',4,4',5-tetrahydro-2'H-spiro[1,5-BENZ oxazepine-3,1'-naphthalene]-7-carboxamide -continued

and

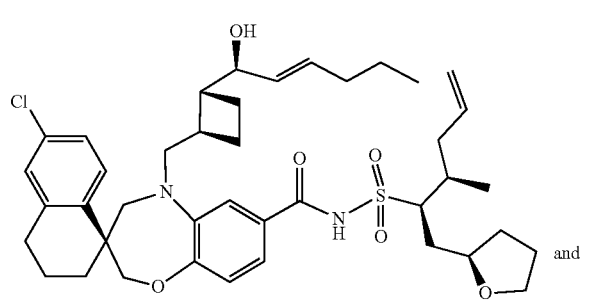

and

457

-continued

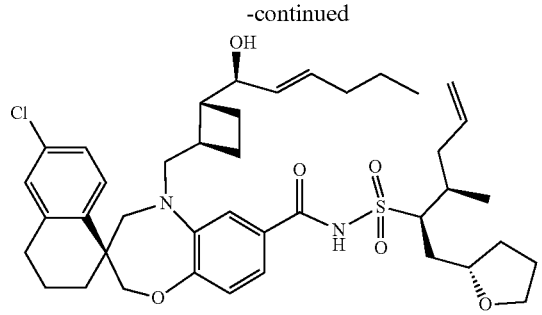

and

458

-continued

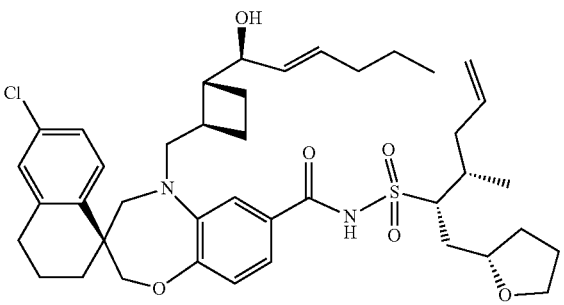

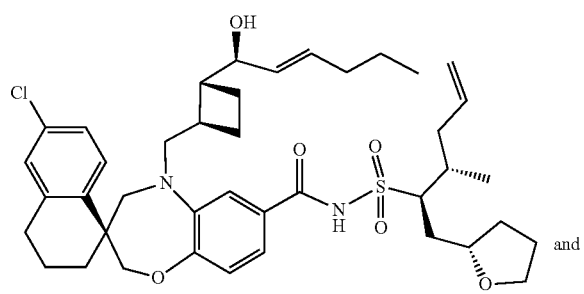

and

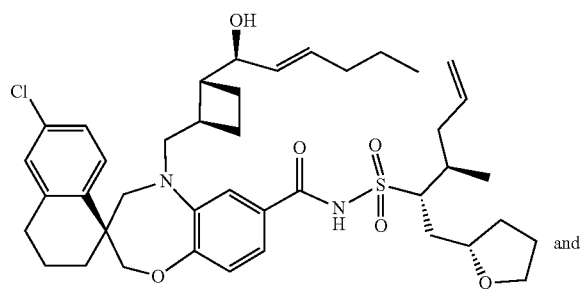

and

N,N-dimethylpyridin-4-amine (182 mg, 1.49 mmol) was added to a solution of (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A, 380 mg, 0.745 mmol), a mixture of (2S,3R)-3-methyl-1-((2R)-tetrahydro-2-furanyl)-5-hexene-2-sulfonamide and (2R,3R)-3-methyl-1-((2R)-tetrahydro-2-furanyl)-5-hexene-2-sulfonamide and (2S,3S)-3-methyl-1-((2R)-tetrahydro-2-furanyl)-5-hexene-2-sulfonamide and (2R,3S)-3-methyl-1-((2R)-tetrahydro-2-furanyl)-5-hexene-2-sulfonamide (2S,3R)-3-methyl-1-((2S)-tetrahydro-2-furanyl)-5-hexene-2-sulfonamide and (2R,3R)-3-methyl-1-((2S)-tetrahydro-2-furanyl)-5-hexene-2-sulfonamide and (2S,3S)-3-methyl-1-((2S)-tetrahydro-2-furanyl)-5-hexene-2-sulfonamide and (2R,3S)-3-methyl-1-((2S)-tetrahydro-2-furanyl)-5-hexene-2-sulfonamide (369 mg, 1.49 mmol) and triethylamine (0.326 mL, 2.352 mmol) in DCM (2 mL) at ambient temperature. Then N1-((ethylimino)methylene)-N3,N3-dimethylpropane-1,3-diamine hydrochloride (286 mg, 1.49 mmol) was then added slowly. The reaction mixture was stirred at ambient temperature for 18 h and washed with saturated sodium bicarbonate. The mixture was diluted with dichloromethane, and the organic layer was washed with water, brine, dried (MgSO$_4$), filtered and concentrated. The crude residue was chromatographed (silica gel, 5 to 100%, EtOAc+1% HOAc/hexane) to afford the title compound (430 mg, 78%). m/z (ESI, +ve ion) 739.3 (M+Na)$^+$.

Step 4: (1S,3'R,6'R,7'S,8'E,11'S,12'R)-6-chloro-7'-hydroxy-11'-methyl-12'((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methyl-12'((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-7'-hydroxy-11'-methyl-12'((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-7'-hydroxy-11'-methyl-12'((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-hydroxy-11'-methyl-12'((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methyl-12'((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-11'-methyl-12'((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-7'-hydroxy-11'-methyl-12'((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide A round bottom flask was charged with a mixture of (3S)-6'-chloro-5-(((1R,2R)-2-((1S,2E)-1-hydroxy-2-hexen-1-yl)cyclobutyl)methyl)-N-(((2R,3R)-3-methyl-1-(((2S)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3S)-3-methyl-1-(((2S)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3S)-3-methyl-1-(((2S)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3S)-3-methyl-1-(((2S)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide (3S)-6'-chloro-5-(((1R,2R)-2-((1S,2E)-1-hydroxy-2-hexen-1-yl)cyclobutyl)methyl)-N-(((2R,3R)-3-methyl-1-(((2R)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3S)-3-methyl-1-(((2R)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3S)-3-methyl-1-(((2R)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide (432 mg, 0.584 mmol) in DCE (195.0 mL). The mixture was stirred at ambient temperature and bubbled argon into the reaction flask for 30 min. To this homogeneous solution was added Hoveyda-Grubbs II (73.2 mg, 0.117 mmol) at ambient temperature and stirred under reduced pressure for 18. The reaction mixture was concentrated and the crude material was chromatographed (silica gel, 0 to 100%, EtOAc+0.5% HOAc/hexane) to afford an oil. This oil was further purified by reversed phase preparatory HPLC (Gemini™ Prep C$_{18}$ 5 µm column; Phenomenex, Torrance, CA; gradient elution of 25% to 75% MeCN in water, where both solvents contain 0.1% TFA, 30 min method) to afford the title compound as the first eluenting isomer. $^1$H NMR (400 MHz, CD$_2$Cl$_2$) δ 8.24 (br s, 1H), 7.70 (d, J=8.4 Hz, 1H), 7.16 (dd, J=2.3, 8.4 Hz, 1H), 7.09 (d, J=2.3 Hz, 1H), 7.00 (br s, 1H), 6.96-6.89 (m, 2H), 5.85-5.77 (m, 1H), 5.73-5.65 (m, 1H), 5.33-5.30 (m, 6H), 4.21-4.05 (m, 5H), 3.92-3.82 (m, 1H), 3.82-3.61 (m, 3H), 3.43 (q, J=7.0 Hz, 1H), 3.29 (d, J=14.3 Hz, 1H), 3.14 (br s, 1H), 2.82-2.69 (m, 2H), 2.44-2.27 (m, 3H), 2.16 (dd, J=3.7, 11.3 Hz, 2H), 2.10-2.02 (m, 2H), 2.00-1.88 (m, 5H), 1.85-1.76 (m, 4H), 1.72-1.67 (m, 1H), 1.62 (d, J=7.0 Hz, 1H), 1.57-1.40 (m, 6H), 1.34-1.21 (m, 5H), 1.17-1.11 (m, 2H), 1.05 (d, J=6.7 Hz, 3H), 0.92-0.81 (m, 3H). m/z (ESI, +ve ion) 669.2 (M+H)$^+$.

Example 137. (1S,3'R,6'R,7'S,8'E,11'R,12'S)-6-chloro-7'-hydroxy-11'-methyl-12'-((2R)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-11'-methyl-12'-((2R)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methyl-12'-((2R)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-hydroxy-11'-methyl-12'-((2R)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'R,12'S)-6-chloro-7'-hydroxy-11'-methyl-12'-((2R)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'R,12'R)-6-chloro-7'-hydroxy-11'-methyl-12'-((2R)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'S)-6-chloro-7'-hydroxy-11'-methyl-12'-((2R)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'R)-6-chloro-7'-hydroxy-11'-methyl-12'-((2R)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-7'-hydroxy-11'-methyl-12'-((2S)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-11'-methyl-12'-((2S)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methyl-12'-((2S)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-hydroxy-11'-methyl-12'-((2S)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'R,12'S)-6-chloro-7'-hydroxy-11'-methyl-12'-((2S)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'R,12'R)-6-chloro-7'-hydroxy-11'-methyl-12'-((2S)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'S)-6-chloro-7'-hydroxy-11'-methyl-12'-((2S)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'R)-6-chloro-7'-hydroxy-11'-methyl-12'-((2S)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

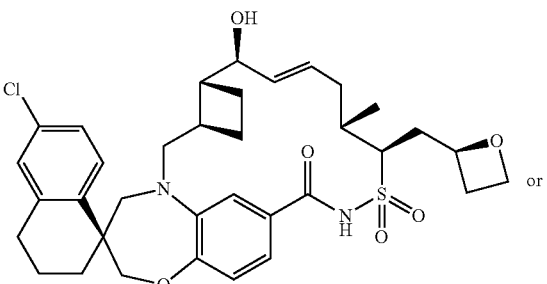

or


or

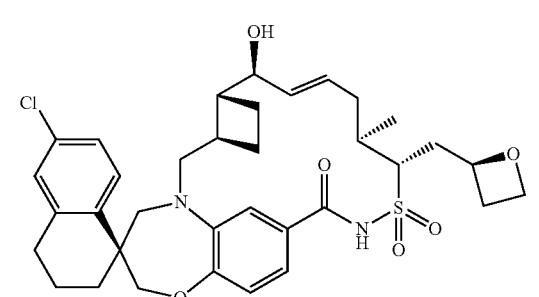

or

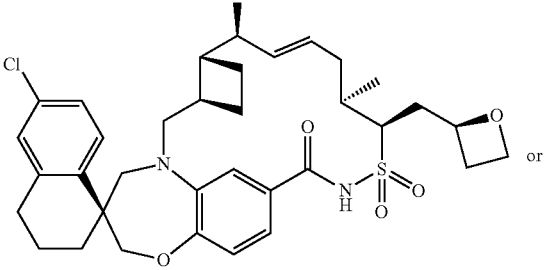

or

463
-continued
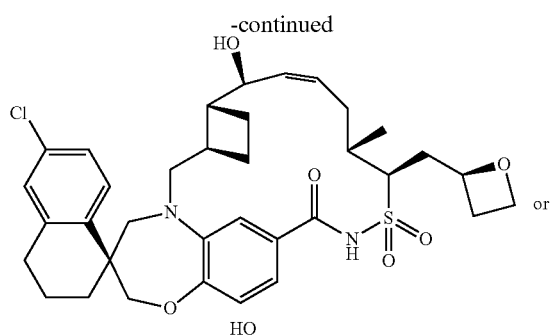
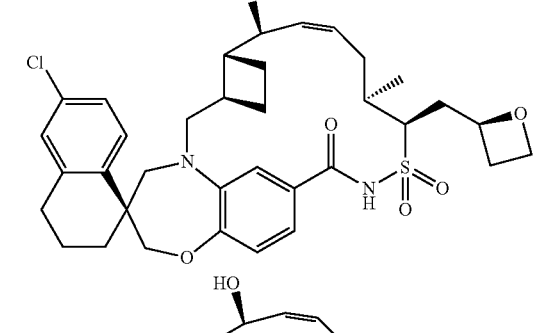
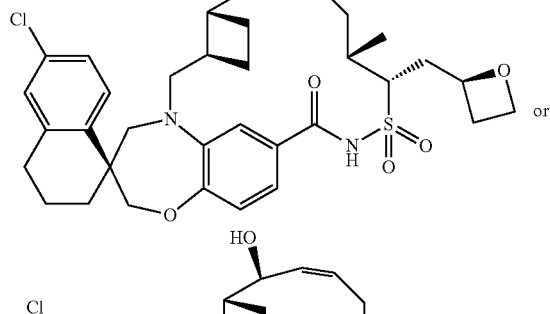

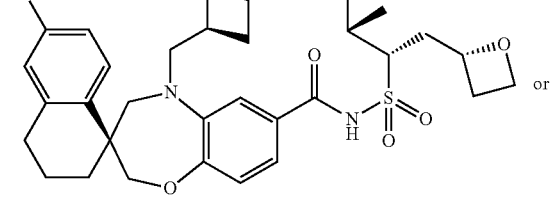
464
-continued
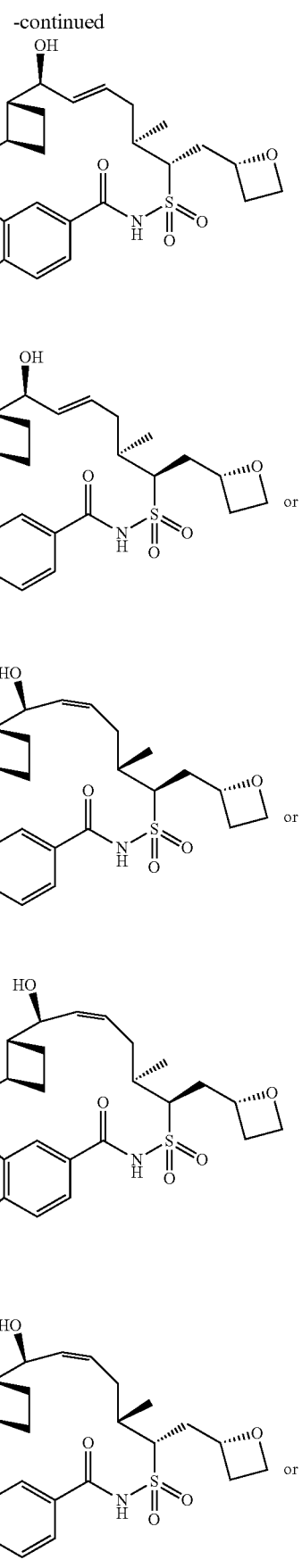

-continued

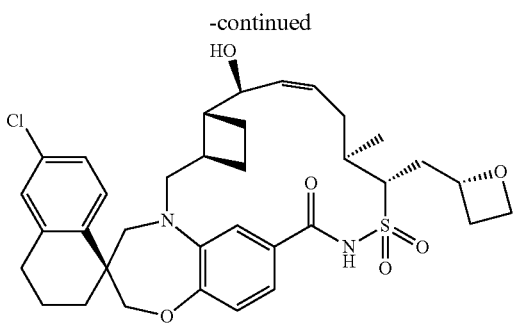

Step 1: (but-3-en-1-yloxy)(tert-butyl)diphenylsilane

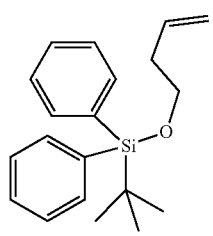 [SMILES: C=CCCO[Si](c1ccccc1)(c1ccccc1)C(C)(C)C]

To a solution of 3-buten-1-ol (5 mL, 58.5 mmol) and imidazole (7.71 mL, 117 mmol) in DMF (30 mL) was added tert-butylchlorodiphenylsilane (18.24 mL, 70.1 mmol) at ambient temperature under Ar. The reaction mixture was stirred at this temperature for 18 h. The mixture was quenched with saturated aqueous $NH_4Cl$, and extracted with DCM. The combined organic layers were washed with brine, dried ($Na_2SO_4$) and concentrated. The resulting residue was chromatographed (silica gel, 0-5%, EtOAc/hexane) to afford the title compound (17 g, 94%).

Step 2: tert-butyl(2-(OXIRAN-2-yl)ethoxy)diphenylsilane

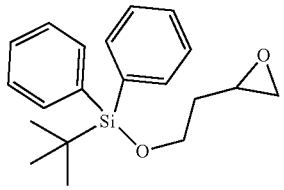 [SMILES: CC(C)(C)[Si](OCCC1CO1)(c1ccccc1)c1ccccc1]

To a solution of (but-3-en-1-yloxy)(tert-butyl)diphenylsilane (17.3 g, 55.8 mmol) in anhydrous dichloromethane (150 mL) at ambient temperature was added 3-chlorobenzoperoxoic acid (18.75 g, 84.0 mmol) portionwise. The reaction mixture was stirred at this temperature for 18 h. A white precipitate was formed. The mixture was quenched with saturated aqueous $NaHCO_3$, and extracted with DCM (3×). The organic layer was washed with saturated aqueous $NaHCO_3$ (3×), dried ($Na_2SO_4$), concentrated and chromatographed (silica gel, 0-5%, EtOAc/hexane) to afford the title compound (17.2 g, 94%) as a colorless.

Step 3: (4R,5S,7S)-7-hydroxy-N,N-bis(4-methoxybenzyl)-4-methyl-9-(((2-methyl-2-propanyl)(diphenyl)silyl)oxy)-1-nonene-5-sulfonamide and (4S,5S,7S)-7-hydroxy-N,N-bis(4-methoxybenzyl)-4-methyl-9-(((2-methyl-2-propanyl)(diphenyl)silyl)oxy)-1-nonene-5-sulfonamide and (4R,5R,7S)-7-hydroxy-N,N-bis(4-methoxybenzyl)-4-methyl-9-(((2-methyl-2-propanyl)(diphenyl)silyl)oxy)-1-nonene-5-sulfonamide and (4S,5R,7S)-7-hydroxy-N,N-bis(4-methoxybenzyl)-4-methyl-9-(((2-methyl-2-propanyl)(diphenyl)silyl)oxy)-1-nonene-5-sulfonamide and (4R,5S,7R)-7-hydroxy-N,N-bis(4-methoxybenzyl)-4-methyl-9-(((2-methyl-2-propanyl)(diphenyl)silyl)oxy)-1-nonene-5-sulfonamide and (4S,5S,7R)-7-hydroxy-N,N-bis(4-methoxybenzyl)-4-methyl-9-(((2-methyl-2-propanyl)(diphenyl)silyl)oxy)-1-nonene-5-sulfonamide and (4S,5S,7R)-7-hydroxy-N,N-bis(4-methoxybenzyl)-4-methyl-9-(((2-methyl-2-propanyl)(diphenyl)silyl)oxy)-1-nonene-5-sulfonamide and (4S,5R,7R)-7-hydroxy-N,N-bis(4-methoxybenzyl)-4-methyl-9-(((2-methyl-2-propanyl)(diphenyl)silyl)oxy)-1-nonene-5-sulfonamide

and

and

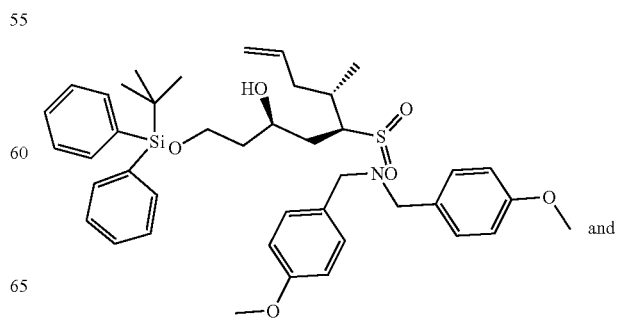
and

-continued

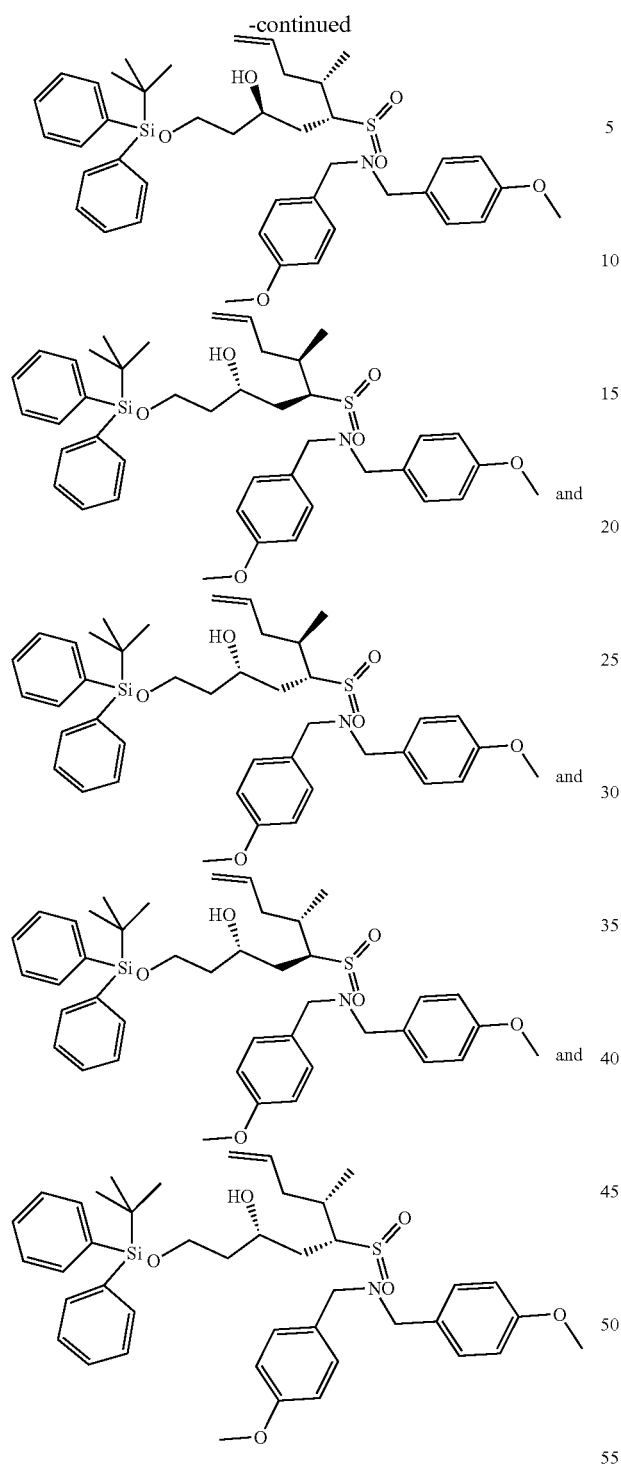

To a round bottom flask was added (2S)—N,N-bis(4-methoxybenzyl)-2-methylpent-4-ene-1-sulfonamide (1.70 g, 4.21 mmol; Example 380, Step 1) in THF (6 mL) at −78° C., butyllithium solution, 2.5 M in hexanes (2.022 mL, 5.06 mmol). The mixture was stirred for 5 min at this temperature, followed by the addition of tert-butyl-(2-(oxiran-2-yl)ethoxy)diphenylsilane (5.50 g, 16.85 mmol). The reaction mixture was then allowed to warm up to ambient temperature and stirred for 2 h. the mixture was quenched with saturated NH₄Cl, and extracted with diethyl ether (2×). The combined organic layers were washed with brine, dried (MgSO₄), filtered and concentrated. The resulting crude residue was chromatographed (silica gel, 0 to 20%, EtOAc/hexane) to afford the title compound (1.0 g, 32.5%). m/z (ESI, +ve ion) 752.2 (M+Na)⁺.

Step 4: (4R,5S,7R)-9-dihydroxy-N,N-bis(4-methoxybenzyl)-4-methyl-1-nonene-5-sulfonamide and (4R,5R,7R)-9-dihydroxy-N,N-bis(4-methoxybenzyl)-4-methyl-1-nonene-5-sulfonamide and (4S,5S,7R)-9-dihydroxy-N,N-bis(4-methoxybenzyl)-4-methyl-1-nonene-5-sulfonamide and (4S,5R,7R)-9-dihydroxy-N,N-bis(4-methoxybenzyl)-4-methyl-1-nonene-5-sulfonamide and (4R,5S,7S)-9-dihydroxy-N,N-bis(4-methoxybenzyl)-4-methyl-1-nonene-5-sulfonamide and (4R,5R,7S)-9-dihydroxy-N,N-bis(4-methoxybenzyl)-4-methyl-1-nonene-5-sulfonamide and (4S,5S,7S)-9-dihydroxy-N,N-bis(4-methoxybenzyl)-4-methyl-1-nonene-5-sulfonamide and (4S,5R,7S)-9-dihydroxy-N,N-bis(4-methoxybenzyl)-4-methyl-1-nonene-5-sulfonamide

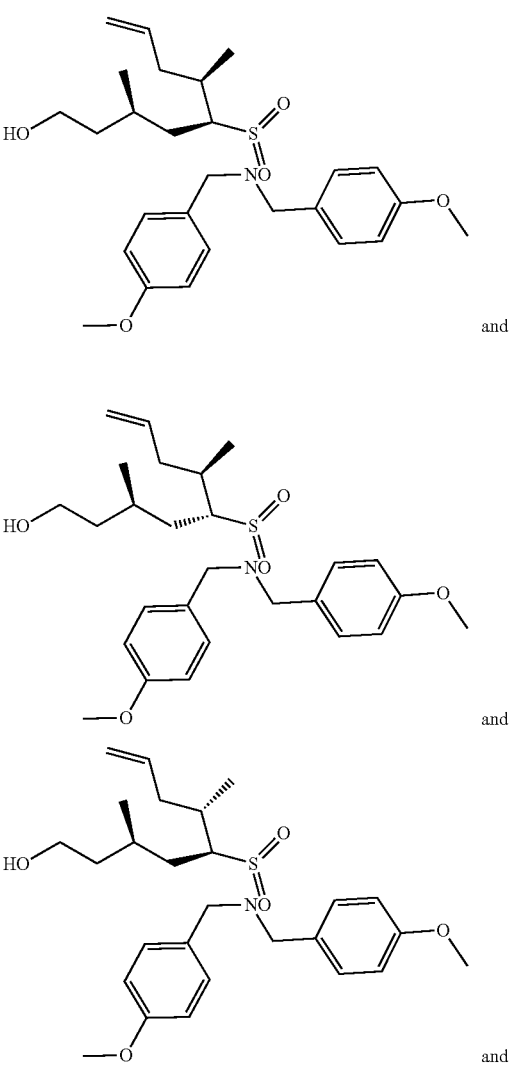

-continued

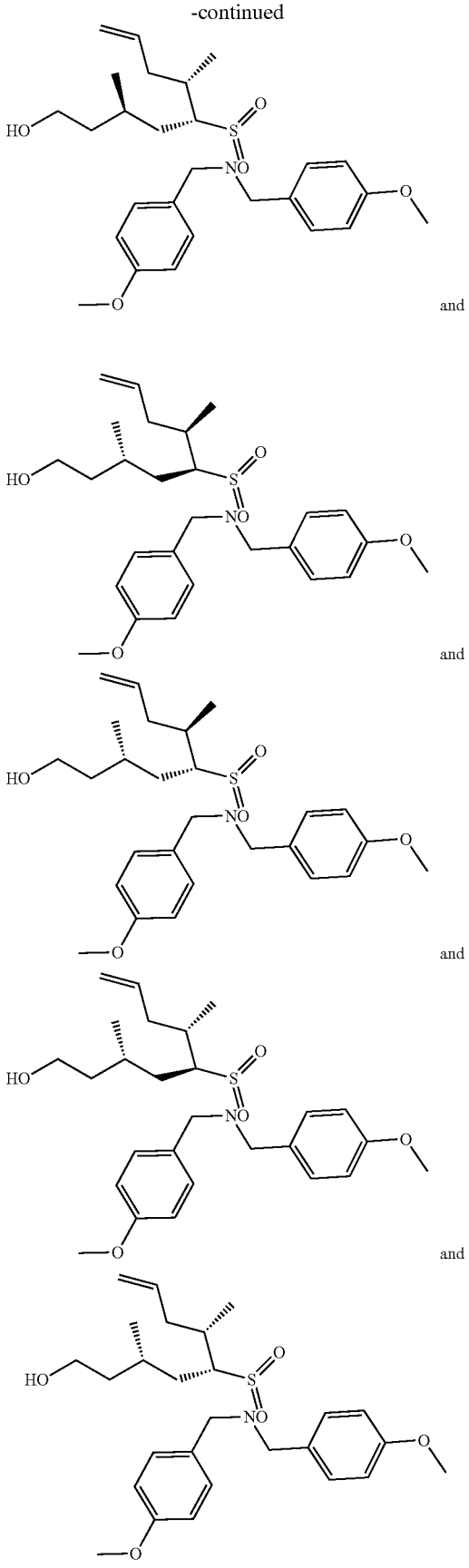

and

To a solution of (4R,5S,7S)-7-Hydroxy-N,N-bis(4-methoxybenzyl)-4-methyl-9-(((2-methyl-2-propanyl)(diphenyl)silyl)oxy)-1-nonene-5-sulfonamide and (4S,5S,7S)-7-hydroxy-N,N-bis(4-methoxybenzyl)-4-methyl-9-(((2-methyl-2-propanyl)(diphenyl)silyl)oxy)-1-nonene-5-sulfonamide and (4R,5R,7S)-7-hydroxy-N,N-bis(4-methoxybenzyl)-4-methyl-9-(((2-methyl-2-propanyl)(diphenyl)silyl)oxy)-1-nonene-5-sulfonamide and (4S,5R,7S)-7-hydroxy-N,N-bis(4-methoxybenzyl)-4-methyl-9-(((2-methyl-2-propanyl)(diphenyl)silyl)oxy)-1-nonene-5-sulfonamide and (4R,5S,7R)-7-hydroxy-N,N-bis(4-methoxybenzyl)-4-methyl-9-(((2-methyl-2-propanyl)(diphenyl)silyl)oxy)-1-nonene-5-sulfonamide and (4S,5S,7R)-7-hydroxy-N,N-bis(4-methoxybenzyl)-4-methyl-9-(((2-methyl-2-propanyl)(diphenyl)silyl)oxy)-1-nonene-5-sulfonamide and (4S,5S,7R)-7-hydroxy-N,N-bis(4-methoxybenzyl)-4-methyl-9-(((2-methyl-2-propanyl)(diphenyl)silyl)oxy)-1-nonene-5-sulfonamide and (4S,5R,7R)-7-hydroxy-N,N-bis(4-methoxybenzyl)-4-methyl-9-(((2-methyl-2-propanyl)(diphenyl)silyl)oxy)-1-nonene-5-sulfonamide (1.80 g, 2.466 mmol) in THF (15 mL) was added tetrabutylammonium fluoride solution, 1.0 M in THF (4.93 mL, 4.93 mmol) at 0° C. The reaction was allowed to warm up to ambient temperature and stirred for 18 h. The reaction was quenched with saturated aqueous NH$_4$Cl, and extracted with EtOAc. The organic layer was washed with brine, dried (Na$_2$SO$_4$), concentrated and chromatographed (silica gel, 20 to 100%, EtOAc/hexane) to afford the title compound (0.95 g, 78%).

Step 5: (2S,3S,5R)-5,7-dihydroxy-3-(2-propen-1-yl)-2-heptanesulfonamide and (2S,3R,5R)-5,7-dihydroxy-3-(2-propen-1-yl)-2-heptanesulfonamide and (2R,3S,5R)-5,7-dihydroxy-3-(2-propen-1-yl)-2-heptanesulfonamide and (2R,3R,5R)-5,7-dihydroxy-3-(2-propen-1-yl)-2-heptanesulfonamide and (2S,3S,5S)-5,7-dihydroxy-3-(2-prop EN-1-yl)-2-heptanesulfonamide and (2S,3R,5S)-5,7-dihydroxy-3-(2-prop EN-1-yl)-2-heptanesulfonamide and (2R,3S,5S)-5,7-dihydroxy-3-(2-prop EN-1-yl)-2-heptanesulfonamide and (2R,3R,5S)-5,7-dihydroxy-3-(2-propen-1-yl)-2-heptanesulfonamide

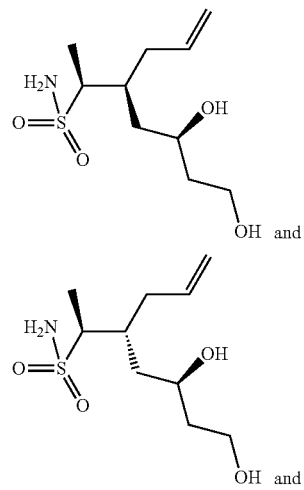

-continued

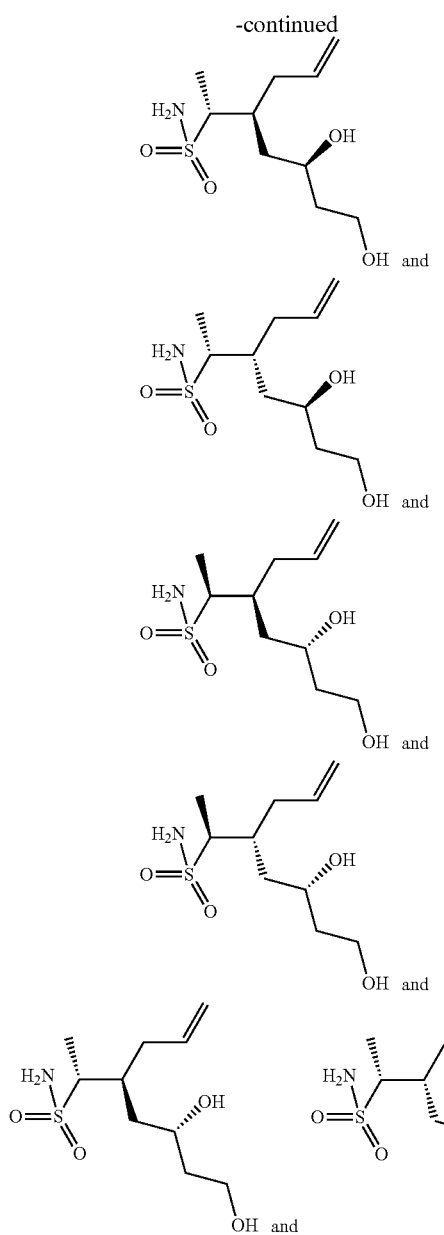

To a solution of (4R,5S,7R)-9-dihydroxy-N,N-bis(4-methoxybenzyl)-4-methyl-1-nonene-5-sulfonamide and (4R,5R,7R)-9-dihydroxy-N,N-bis(4-methoxybenzyl)-4-methyl-1-nonene-5-sulfonamide and (4S,5S,7R)-9-dihydroxy-N,N-bis(4-methoxybenzyl)-4-methyl-1-nonene-5-sulfonamide and (4S,5R,7R)-9-dihydroxy-N,N-bis(4-methoxybenzyl)-4-methyl-1-nonene-5-sulfonamide and (4r,5s,7s)-9-dihydroxy-N,N-bis(4-methoxybenzyl)-4-methyl-1-nonene-5-sulfonamide and (4R,5R,7S)-9-dihydroxy-N,N-bis(4-methoxybenzyl)-4-methyl-1-nonene-5-sulfonamide and (4S,5S,7S)-9-dihydroxy-N,N-bis(4-methoxybenzyl)-4-methyl-1-nonene-5-sulfonamide and (4S,5R,7S)-9-dihydroxy-N,N-bis(4-methoxybenzyl)-4-methyl-1-nonene-5-sulfonamide (2.00 g, 4.07 mmol) in anisole (22.11 mL, 203 mmol) was added 2,2,2-trifluoroacetic acid (15.67 mL, 203 mmol) at ambient temperature and stirred for 18 h. The excess TFA was removed under reduced pressure and the reaction mixture was chromatographed (silica gel, 0 to 20%, MeOH/0.3% AcOH+DCM) to afford the trifluoroacetate as an oil. The oil was then dissolved in a mixed solvent (THF/MeOH/H$_2$O: 8 mL/8 mL/8 mL) and was added LiOH (4 eq). The resulting mixture was stirred at ambient temperature for 1 h, concentrated, added water, and extracted with 25% iPrOH in CHCl$_3$. The organic layer was concentrated to afford the title compound (610 mg, 60%).

Step 6: (3R,5S)-3-hydroxy-5-((1S)-1-sulfamoylethyl)-7-octen-1-y and (3R,5R)-3-hydroxy-5-((1S)-1-sulfamoylethyl)-7-octen-1-y and (3R,5R)-3-hydroxy-5-((1R)-1-sulfamoylethyl)-7-octen-1-y and (3R,5S)-3-hydroxy-5-((1R)-1-sulfamoylethyl)-7-octen-1-y and (3S,5S)-3-hydroxy-5-((1S)-1-sulfamoylethyl)-7-octen-1-y and (3S,5R)-3-hydroxy-5-((1S)-1-sulfamoylethyl)-7-octen-1-y and (3S,5R)-3-hydroxy-5-((1R)-1-sulfamoylethyl)-7-octen-1-y and (3S,5S)-3-hydroxy-5-((1R)-1-sulfamoylethyl)-7-octen-1-y

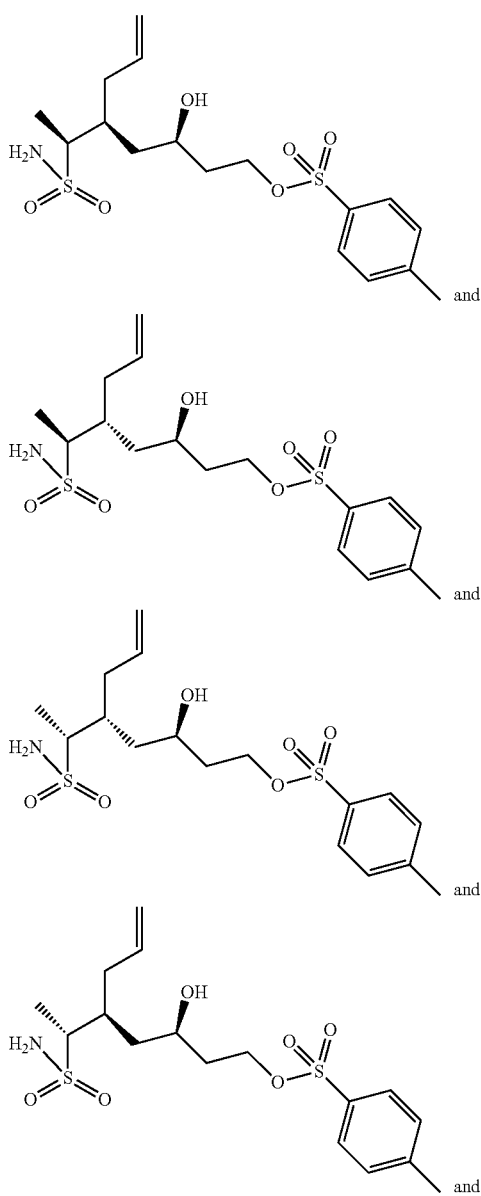

-continued

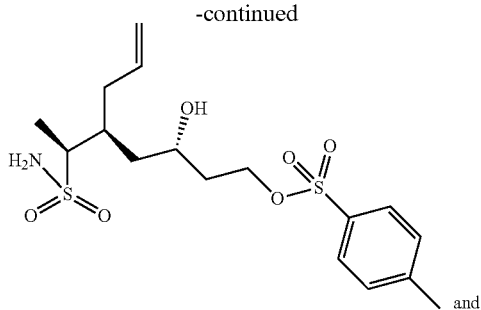

and

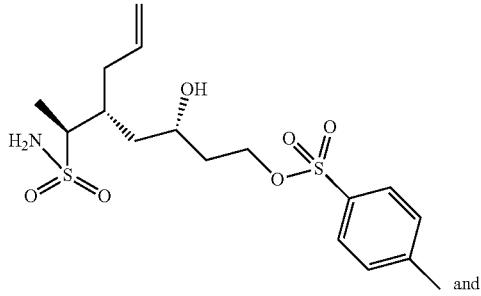

and


and

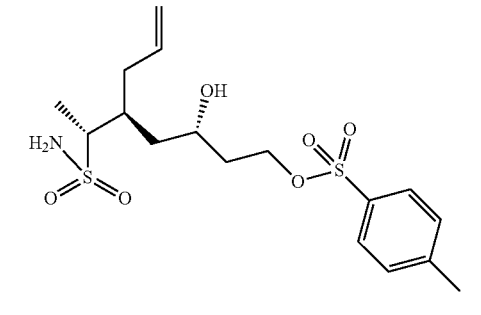

To a mixture of (2S,3S,5R)-5,7-dihydroxy-3-(2-propen-1-yl)-2-heptanesulfonamide and (2S,3R,5R)-5,7-dihydroxy-3-(2-propen-1-yl)-2-heptanesulfonamide and (2R,3S,5R)-5,7-dihydroxy-3-(2-propen-1-yl)-2-heptanesulfonamide and (2R,3R,5R)-5,7-dihydroxy-3-(2-propen-1-yl)-2-heptanesulfonamide (2S,3S,5S)-5,7-dihydroxy-3-(2-propen-1-yl)-2-heptanesulfonamide and (2S,3R,5S)-5,7-dihydroxy-3-(2-propen-1-yl)-2-heptanesulfonamide and (2R,3S,5S)-5,7-dihydroxy-3-(2-propen-1-yl)-2-heptanesulfonamide and (2R,3R,5S)-5,7-dihydroxy-3-(2-propen-1-yl)-2-heptanesulfonamide (480 mg, 1.910 mmol) in DCM (10 mL) at 0° C. was added triethylamine (1.06 mL, 7.64 mmol), and a solution of p-toluenesulfonyl chloride (728 mg, 3.82 mmol) in portions. The mixture was stirred from 0° C. to ambient temperature for 2 h and extracted with 10% MeOH in DCM. The organic layer was washed with H$_2$O, dried (MgSO$_4$), filtered and concentrated. The resulting crude orange oil was chromatographed (silica gel, 0 to 20%, MeOH/0.3% AcOH in DCM) to afford the title compound (500 mg, 64.6%).

Step 7: (2S,3R)-3-methyl-1-((2R)-2-oxetanyl)-5-hexene-2-sulfonamide and (2S,3S)-3-methyl-1-((2R)-2-oxetanyl)-5-hexene-2-sulfonamide and (2R,3R)-3-methyl-1-((2R)-2-oxetanyl)-5-hexene-2-sulfonamide and (2R,3S)-3-methyl-1-((2R)-2-oxetanyl)-5-hexene-2-sulfonamide and (2S,3R)-3-methyl-1-((2S)-2-oxetanyl)-5-hexene-2-sulfonamide and (2S,3S)-3-methyl-1-((2S)-2-oxetanyl)-5-hexene-2-sulfonamide and (2R,3R)-3-methyl-1-((2S)-2-oxetanyl)-5-hexene-2-sulfonamide and (2R,3S)-3-methyl-1-((2S)-2-oxetanyl)-5-hexene-2-sulfonamide

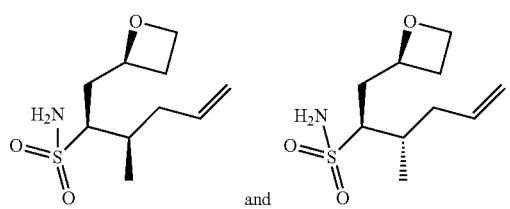

and                    and

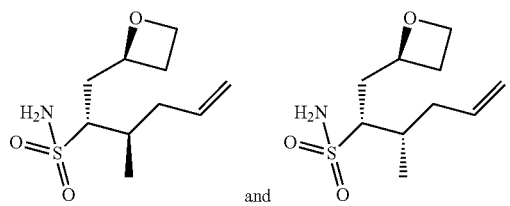

and                    and

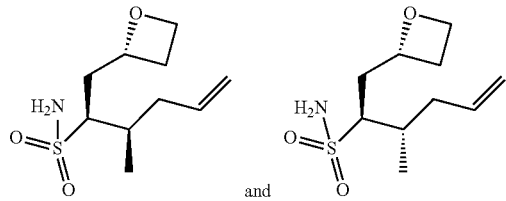

and                    and

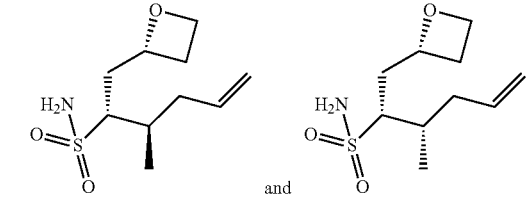

and

Potassium 2-methylpropan-2-olate (2.50 mL, 2.47 mmol) was added to a solution of 3-hydroxy-6-methyl-5-sulfamoylnon-8-en-1-yl 4-methylbenzenesulfonate (500 mg, 1.233 mmol) in THF (12 mL) at ambient temperature. The reaction mixture was stirred at for 2 h. Solvent was evaporated, the residue was extracted with 10% MeOH/DCM. The organic layer was washed with saturated NH$_4$Cl, brine, dried (Na$_2$SO$_4$) and concentrated to afford the title compound (154 mg, 53.5%).

Step 8: (3S)-6'-chloro-5-(((1R,2R)-2-((1S,2E)-1-hydroxy-2-hexen-1-yl)cyclobutyl)methyl)-N-(((2R,3S)-3-methyl-1-((2S)-2-oxetanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2S,3R)-3-methyl-1-((2S)-2-oxetanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3R)-3-methyl-1-((2S)-2-oxetanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2S,3S)-3-methyl-1-((2S)-2-oxetanyl)-5-hexen-2-yl)sulfonyl)-3',4,4',5-tetrahydro-2'H-spiro[1,5-BENZ oxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3S)-3-methyl-1-((2R)-2-oxetanyl)-5-hexen-2-yl)sulfonyl)-3',4,4',5-tetrahydro-2'H-spiro[1,5-BENZ oxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2S,3R)-3-methyl-1-((2R)-2-oxetanyl)-5-hexen-2-yl)sulfonyl)-3',4,4',5-tetrahydro-2'H-spiro[1,5-BENZ oxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3R)-3-methyl-1-((2R)-2-oxetanyl)-5-hexen-2-yl)sulfonyl)-3',4,4',5-tetrahydro-2'H-spiro[1,5-BENZ oxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2S,3S)-3-methyl-1-((2R)-2-oxetanyl)-5-hexen-2-yl)sulfonyl)-3',4,4',5-tetrahydro-2'H-spiro[1,5-BENZ oxazepine-3,1'-naphthalene]-7-carboxamide

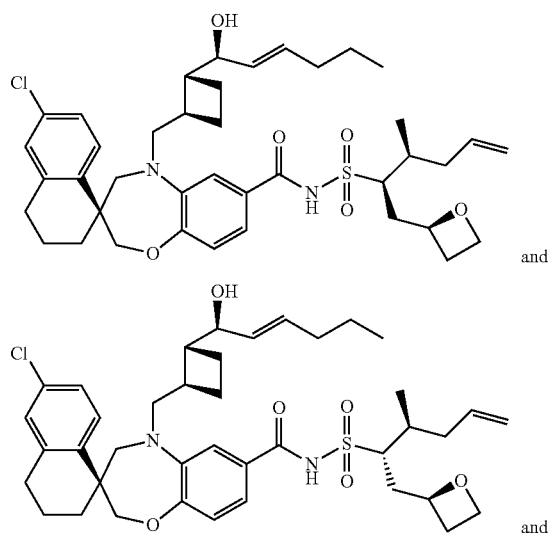

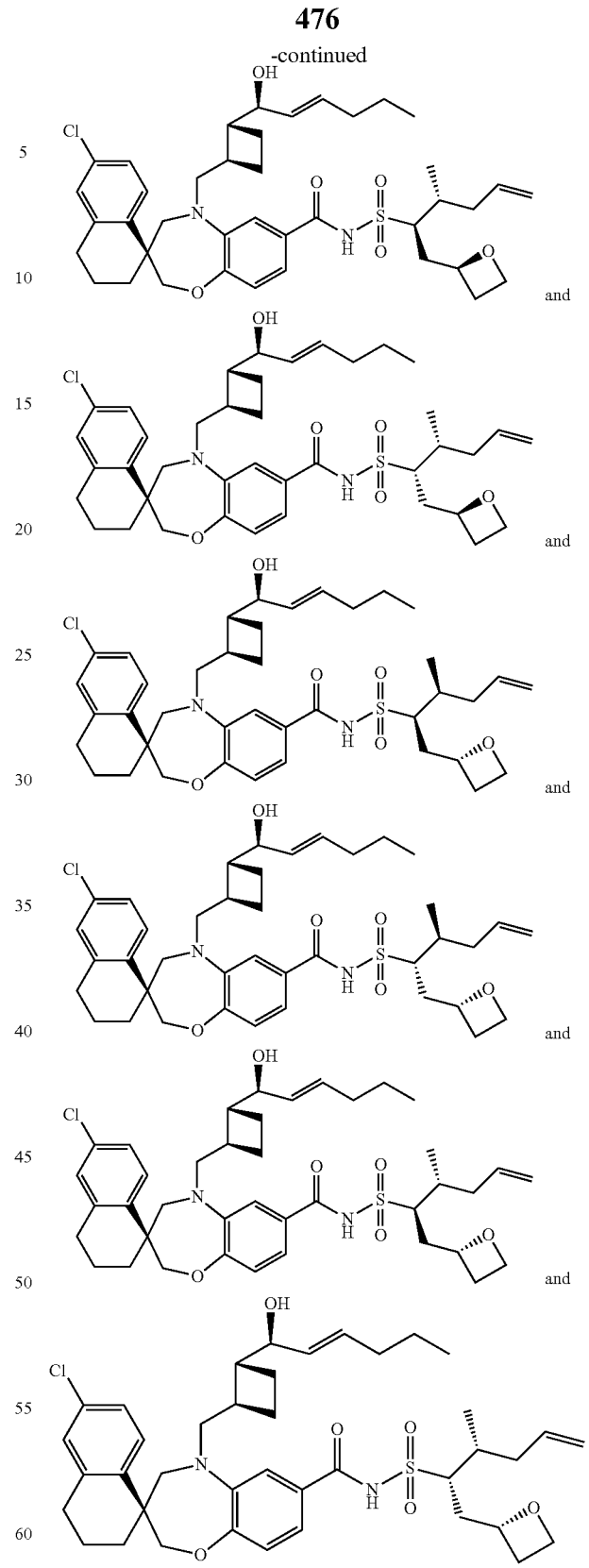

The title compounds were prepared from a mixture of (2S,3R)-3-methyl-1-((2R)-2-oxetanyl)-5-hexene-2-sulfonamide and (2S,3S)-3-methyl-1-((2R)-2-oxetanyl)-5-hexene-2-sulfonamide and (2R,3R)-3-methyl-1-((2R)-2-oxetanyl)-

5-hexene-2-sulfonamide and (2R,3S)-3-methyl-1-((2R)-2-oxetanyl)-5-hexene-2-sulfonamide (2S,3R)-3-methyl-1-((2S)-2-oxetanyl)-5-hexene-2-sulfonamide and (2S,3S)-3-methyl-1-((2S)-2-oxetanyl)-5-hexene-2-sulfonamide and (2R,3R)-3-methyl-1-((2S)-2-oxetanyl)-5-hexene-2-sulfonamide and (2R,3S)-3-methyl-1-((2S)-2-oxetanyl)-5-hexene-2-sulfonamide and (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A) by a similar procedure described in Step 3 of Example 136.

Step 9: (1S,3'R,6'R,7'S,8'E,11'R,12'S)-6-chloro-7'-hydroxy-11'-methyl-12'-((2R)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-11'-methyl-12'-((2R)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methyl-12'-((2R)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-hydroxy-11'-methyl-12'-((2R)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'R,12'S)-6-chloro-7'-hydroxy-11'-methyl-12'-((2R)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'R,12'R)-6-chloro-7'-hydroxy-11'-methyl-12'-((2R)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'S)-6-chloro-7'-hydroxy-11'-methyl-12'-((2R)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'R)-6-chloro-7'-hydroxy-11'-methyl-12'-((2R)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methyl-12'-((2S)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-11'-methyl-12'-((2S)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methyl-12'-((2S)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-hydroxy-11'-methyl-12'-((2S)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'R,12'S)-6-chloro-7'-hydroxy-11'-methyl-12'-((2S)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'R,12'R)-6-chloro-7'-hydroxy-11'-methyl-12'-((2S)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'S)-6-chloro-7'-hydroxy-11'-methyl-12'-((2S)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'R)-6-chloro-7'-hydroxy-11'-methyl-12'-((2S)-2-oxetanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide A round bottom flask was charged with a mixture of (3S)-6'-chloro-5-(((1R,2R)-2-((1S,2E)-1-hydroxy-2-hexen-1-yl)cyclobutyl)methyl)-N-(((2R,3S)-3-methyl-1-((2S)-2-oxetanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-((2S,3R)-3-methyl-1-((2s)-2-oxetanyl)-5-hexen-2-yl)sulfonyl)-3',4,4',5-tetrahydro-2'h-spiro[1,5-benzoxazepine-3,1'-naphthalene]-7-carboxamide and (3s)-6'-chloro-5-(((1R,2R)-2-((1S,2E)-1-hydroxy-2-hexen-1-yl)cyclobutyl)methyl)-N-(((2R,3R)-3-methyl-1-((2S)-2-oxetanyl)-5-hexen-2-yl)sulfonyl)-3',4,4',5-tetrahydro-2'h-spiro[1,5-benzoxazepine-3,1'-naphthalene]-7-carboxamide and (3S)-6'-chloro-5-(((1R,2R)-2-((1s,2e)-1-hydroxy-2-hexen-1-yl)cyclobutyl)methyl)-N-(((2S,3S)-3-methyl-1-((2S)-2-oxetanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3S)-3-methyl-1-((2R)-2-oxetanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2S,3R)-3-methyl-1-((2R)-2-oxetanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3R)-3-methyl-1-((2R)-2-oxetanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2S,3S)-3-methyl-1-((2R)-2-oxetanyl)-5-hexen-2-yl)sulfonyl)-3',4,4',5-tetrahydro-2'H-spiro[1,5-benzoxazepine-3,1'-naphthalene]-7-carboxamide (265 mg, 0.365 mmol) in DCE (179.0 mL). The mixture was stirred at ambient temperature and bubbled with argon into the reaction flask for 30 min. To this homogeneous solution was added Hoveyda-Grubbs II (45.8 mg, 0.073 mmol) at ambient temperature and the mixture was stirred under reduced pressure for 18 h. The reaction mixture was concentrated and the crude residue was chromatographed (silica gel column, 0 to 100%, EtOAc+0.5% HOAc/hexane) to afford a mixture of the isomers. The mixture was further purified by reversed phase preparatory HPLC (Gemini™ Prep $C_{18}$ 5 μm column; Phenomenex, Torrance, CA; gradient elution of 25% to 75% MeCN in water, where both solvents contain 0.1% TFA, 30 min method) to afford the title compound as the first eluenting isomer. $^1$H NMR (400 MHz, $CD_2Cl_2$) δ 8.12 (br s, 1H), 7.74-7.69 (m, 1H), 7.17 (dd, J=2.2, 8.5 Hz, 1H), 7.13-7.06 (m, 1H), 7.01-6.81 (m, 3H), 5.85-5.65 (m, 2H), 5.20-5.06 (m, 1H), 4.66 (br s, 1H), 4.50 (br s, 1H), 4.20-4.04 (m, 4H), 3.82 (d, J=15.3 Hz, 1H), 3.68 (d, J=13.7 Hz, 1H), 3.25 (d, J=14.3 Hz, 1H), 3.04 (dd, J=9.6, 15.3 Hz, 1H), 2.84-2.70 (m, 3H), 2.350-2.10 (m, 6H), 2.10-1.50 (m, 8H), 1.45-1.35 (m, 1H), 1.11 (br s, 1H), 1.04 (d, J=6.5 Hz, 3H). m/z (ESI, +ve ion) 677.0 (M+Na)$^+$.

Example 138. (1S,3'R,6'R,7'S,8'E,12'R)-6-chloro-7'-hydroxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-7'-hydroxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-6-chloro-7'-hydroxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-6-chloro-7'-hydroxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

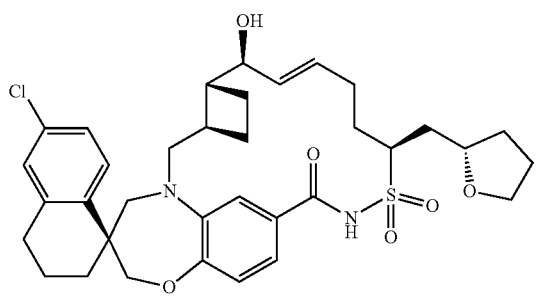

or

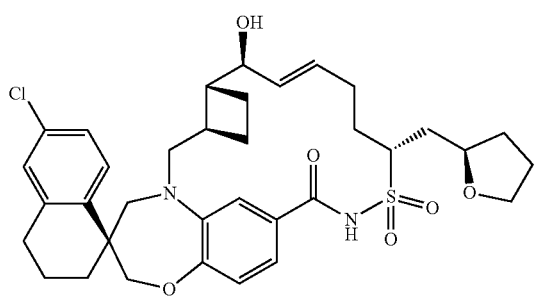

or

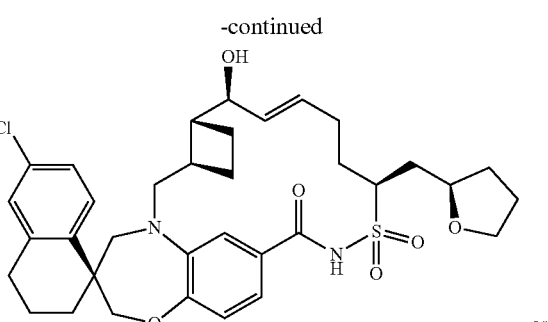

or

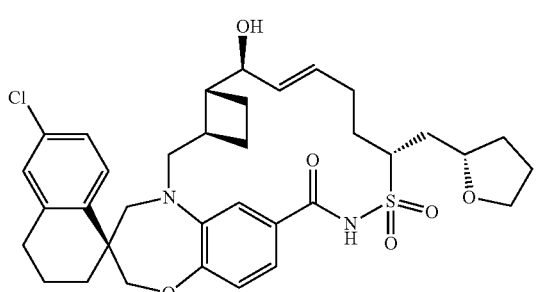

Step 1: (2R)—N,N-bis(4-methoxybenzyl)-1-((2R)-tetrahydro-2-furanyl)-5-hexene-2-sulfonamide and (2R)—N,N-bis(4-methoxybenzyl)-1-((2S)-tetrahydro-2-furanyl)-5-hexene-2-sulfonamide and (2S)—N,N-bis(4-methoxybenzyl)-1-((2S)-tetrahydro-2-furanyl)-5-hexene-2-sulfonamide and (2S)—N,N-bis(4-methoxybenzyl)-1-((2R)-tetrahydro-2-furanyl)-5-hexene-2-sulfonamide

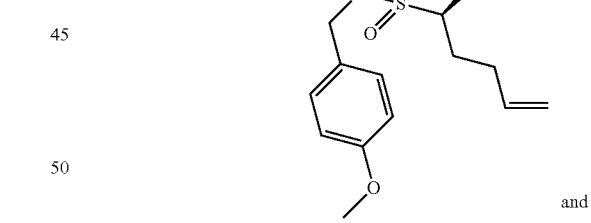

and

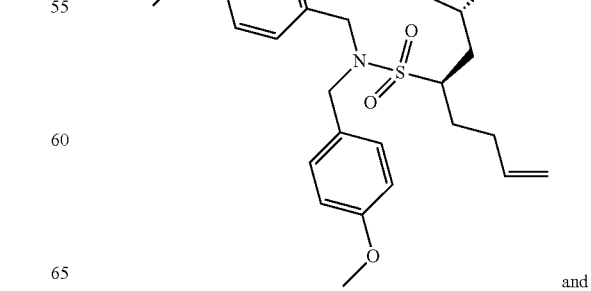

and

-continued

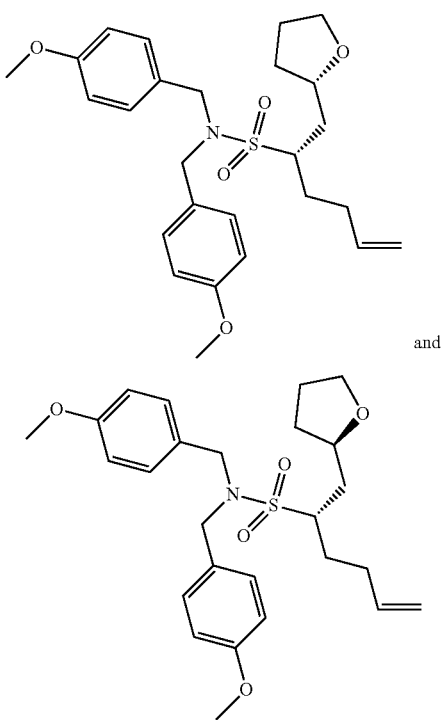

and

The title compound was prepared from N,N-bis(4-methoxybenzyl)pent-4-ene-1-sulfonamide (Intermediate EE19), using a similar procedure described in Example 373, Step 2, replacing 2-(bromomethyl)thiazole with 2-(bromomethyl)tetrahydrofuran.

Step 2: (2R)-1-((2R)-tetrahydro-2-furanyl)-5-hexene-2-sulfonamide and (2R)-1-((2S)-tetrahydro-2-furanyl)-5-hexene-2-sulfonamide and (2S)-1-((2S)-tetrahydro-2-furanyl)-5-hexene-2-sulfonamide and (2S)-1-((2R)-tetrahydro-2-furanyl)-5-hexene-2-sulfonamide

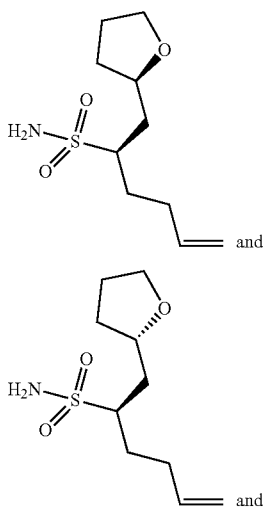

and

-continued

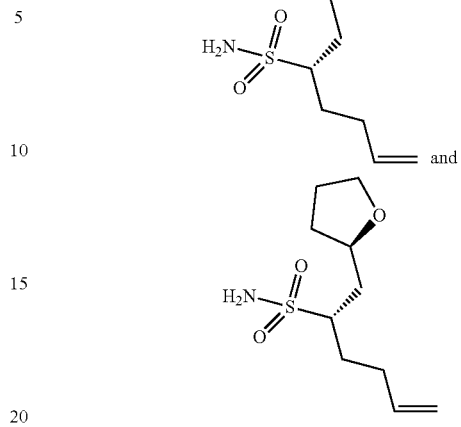

The title compound was prepared from (2R)—N,N-bis(4-methoxybenzyl)-1-((2R)-tetrahydro-2-furanyl)-5-hexene-2-sulfonamide, (2S)—N,N-bis(4-methoxybenzyl)-1-((2S)-tetrahydro-2-furanyl)-5-hexene-2-sulfonamide, (2S)—N,N-bis(4-methoxybenzyl)-1-((2R)-tetrahydro-2-furanyl)-5-hexene-2-sulfonamide and (2R)—N,N-bis(4-methoxybenzyl)-1-((2S)-tetrahydro-2-furanyl)-5-hexene-2-sulfonamide by a similar procedure described in Step 3 of Example 373.

Step 3: (3S)-6'-chloro-5-(((1R,2R)-2-((1S,2E)-1-hydroxy-2-hexen-1-yl)cyclobutyl)methyl)-N-(((2S)-1-((2S)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R)-1-((2S)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2S)-1-((2R)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R)-1-((2R)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide

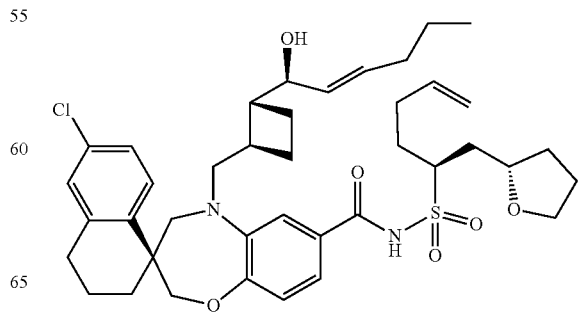

or

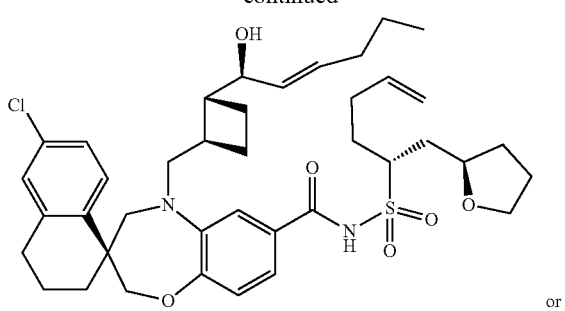

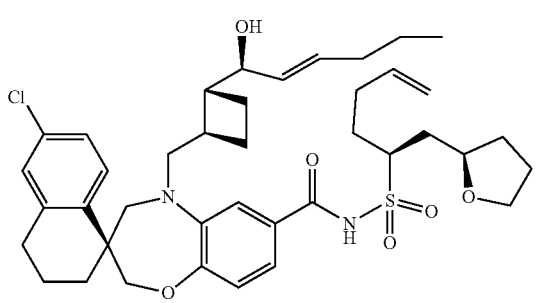

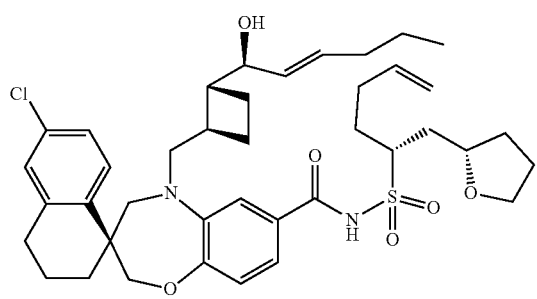

The title compounds were prepared from a mixture of (2R)-1-((2R)-tetrahydro-2-furanyl)-5-hexene-2-sulfonamide, (2R)-1-((2S)-tetrahydro-2-furanyl)-5-hexene-2-sulfonamide, (2S)-1-((2R)-tetrahydro-2-furanyl)-5-hexene-2-sulfonamide, and (2S)-1-((2S)-tetrahydro-2-furanyl)-5-hexene-2-sulfonamide, reacting with (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A) by a similar procedure described in Step 3 of Example 136.

Step 4: (1S,3'R,6'R,7'S,8'E,12'R)-6-chloro-7'-hydroxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-7'-hydroxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-6-chloro-7'-hydroxy-12'-((2R)-tetrahydro-2-furanylmethyl)-3,4-dihydro-2H,15'H-spiro[naphthalene-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-6-chloro-7'-hydroxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide A round bottom flask was charged with a mixture of (3S)-6'-chloro-5-(((1R,2R)-2-((1S,2E)-1-hydroxy-2-hexen-1-yl)cyclobutyl)methyl)-N-(((2S)-1-((2S)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide, (3S)-6'-chloro-5-(((1R,2R)-2-((1S,2E)-1-hydroxy-2-hexen-1-yl)cyclobutyl)methyl)-N-(((2S)-1-((2R)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide, (3S)-6'-chloro-5-(((1R,2R)-2-((1S,2E)-1-hydroxy-2-hexen-1-yl)cyclobutyl)methyl)-N-(((2R)-1-((2S)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide, and (3S)-6'-chloro-5-(((1R,2R)-2-((1S,2E)-1-hydroxy-2-hexen-1-yl)cyclobutyl)methyl)-N-(((2R)-1-((2R)-tetrahydro-2-furanyl)-5-hexen-2-yl)sulfonyl)-3',4,4',5-tetrahydro-2'H-spiro[1,5-benzoxazepine-3,1'-naphthalene]-7-carboxamide (180 mg, 0.248 mmol) in toluene (85 mL). The mixture was stirred and sparged with Ar into the reaction flask for 30 min at ambient temperature. To this homogeneous solution was added Hoveyda-Grubbs II (31.1 mg, 0.050 mmol). The reaction mixture was stirred at ambient temperature under reduced pressure for 18 h. Solvent was evaporated, and the crude residue was chromatographed (silica gel, 10 to 100%, EtOAc+0.5% HOAc/hexane) to afford an oil. Further purification of this oil by reversed phase preparatory HPLC (Gemini™ Prep C$_{18}$ 5 μm column; Phenomenex, Torrance, CA; gradient elution of 25% to 75% MeCN in water, where both solvents contain 0.1% TFA, 30 min method) afforded the title compound as the first eluenting isomer. $^1$H NMR (400 MHz, CD$_2$Cl$_2$) δ 7.71 (d, J=8.6 Hz, 1H), 7.17 (dd, J=2.3, 8.6 Hz, 1H), 7.09 (d, J=2.2 Hz, 1H), 6.96 (s, 1H), 6.93-6.88 (m, 3H), 5.89-5.81 (m, 1H), 5.70 (dd, J=15.3, 8.0 Hz, 1H), 4.28-4.16 (m, 3H), 4.12-4.04 (m, 2H), 3.88-3.68 (m, 4H), 3.26 (d, J=14.3 Hz, 1H), 3.04 (dd, J=9.5, 15.4 Hz, 1H), 2.83-2.70 (m, 2H), 2.45-2.20 (m, 5H), 2.12-2.01 (m, 3H), 1.97-1.46 (m, 12H). m/z (ESI, +ve ion) 656.2 (M+Na)$^+$.

Example 139. (1S,3'R,6'R,7'S,8'E,12'R)-6-chloro-7'-hydroxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,12'R)-6-chloro-7'-hydroxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,12'S)-6-chloro-7'-hydroxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,12'S)-6-chloro-7'-hydroxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

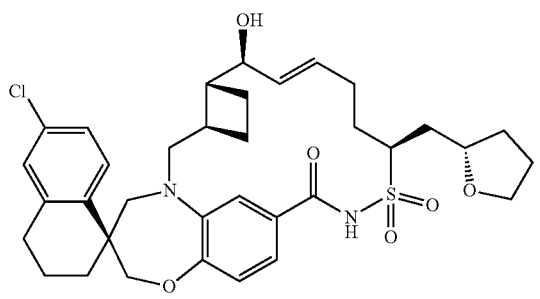

or

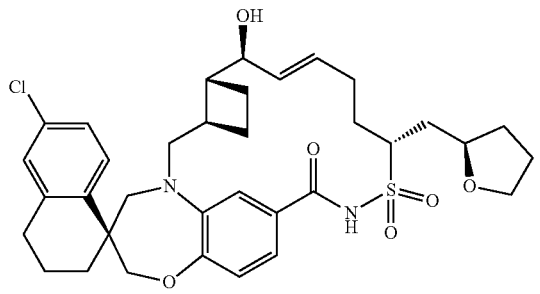

or

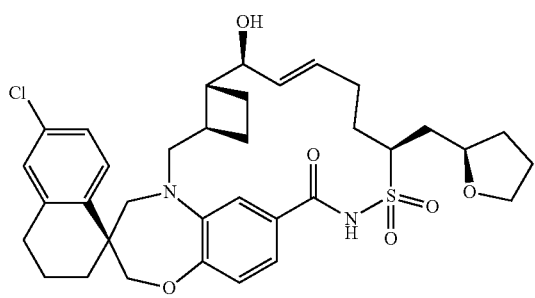

or

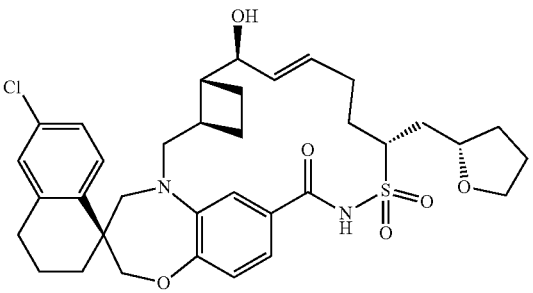

The title compound was obtained as a white solid as the second eluting isomer from the reversed phase preparative HPLC separation in Example 138. ¹H NMR (400 MHz, CD$_2$Cl$_2$) δ 7.71 (d, J=8.6 Hz, 1H), 7.16 (dd, J=2.2, 8.5 Hz, 1H), 7.09 (d, J=2.3 Hz, 1H), 6.96-6.87 (m, 3H), 5.86-5.77 (m, 1H), 5.68 (dd, J=7.4, 15.3 Hz, 1H), 4.20-4.04 (m, 5H), 3.92-3.67 (m, 4H), 3.25 (d, J=14.1 Hz, 1H), 3.04 (dd, J=9.0, 15.3 Hz, 1H), 2.83-2.69 (m, 2H), 2.45-2.22 (m, 5H), 2.11-1.46 (m, 15H). m/z (ESI, +ve ion) 656.2 (M+Na)⁺.

Example 140. (1S,3'R,6'R,7'S,8'E,12'R)-6-chloro-7'-hydroxy-12'-((2S)-tetrahydro-2-furanylmethyl)-3,4-dihydro-2H,15'H-spiro [naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,12'R)-6-chloro-7'-hydroxy-12'-((2R)-tetrahydro-2-furanylmethyl)-3,4-dihydro-2H,15'H-spiro[naphthalene-1,22'-[20]oxa[13]thia [1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,12'S)-6-chloro-7'-hydroxy-12'-((2R)-tetrahydro-2-furanylmethyl)-3,4-dihydro-2H,15'H-spiro[naphthalene-1,22'-[20]oxa[13]thia [1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,12'S)-6-chloro-7'-hydroxy-12'-((2S)-tetrahydro-2-furanylmethyl)-3,4-dihydro-2H,15'H-spiro[naphthalene-1,22'-[20]oxa[13]thia [1,14]diazatetracyclo[14.7.2.0³,⁶.0¹⁹,²⁴]pentacosa[8,16,18,24]tetraen]-15'-one 13',13'-dioxide

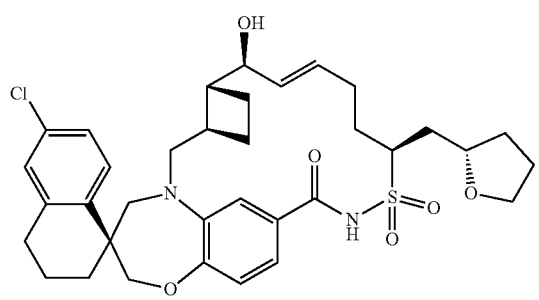

or

-continued

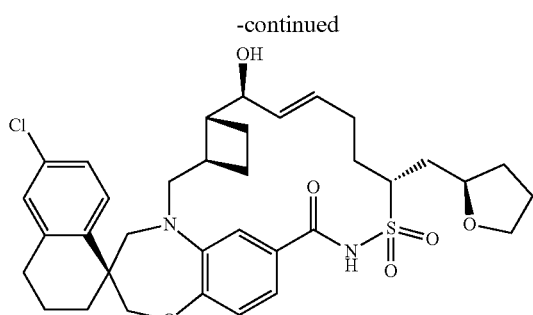

or

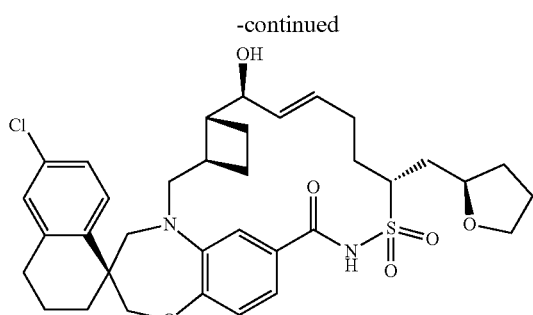

or

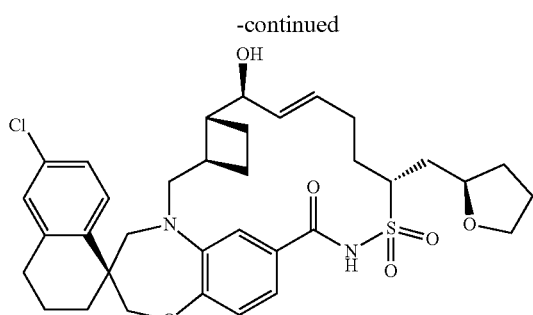

The title compound was obtained as a white solid as the third eluenting isomer from the reversed phase preparative HPLC separation in Example 138. $^1$H NMR (400 MHz, CD$_2$Cl$_2$) δ 8.20 (br s, 1H), 7.66 (d, J=8.4 Hz, 1H), 7.52 (br s, 1H), 7.15 (dd, J=2.3, 8.4 Hz, 1H), 7.10 (d, J=2.3 Hz, 1H), 6.97-6.87 (m, 2H), 5.70 (dd, J=4.1, 15.8 Hz, 1H), 5.58-5.48 (m, 1H), 4.27-4.17 (m, 3H), 4.12-4.04 (m, 1H), 3.97-3.66 (m, 5H), 3.38 (d, J=14.1 Hz, 1H), 3.19 (d, J=16.8 Hz, 1H), 2.80-2.70 (m, 3H), 2.55-2.41 (m, 2H), 2.38-1.40 (m, 15H), 1.58-1.40 (m, 1H). m/z (ESI, +ve ion) 656.2 (M+Na)$^+$.

Example 141. (1S,3'R,6'R,7'S,9'Z,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'R,7'S,9'Z,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'R,7'S,9'E,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'R,7'S,9E,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide

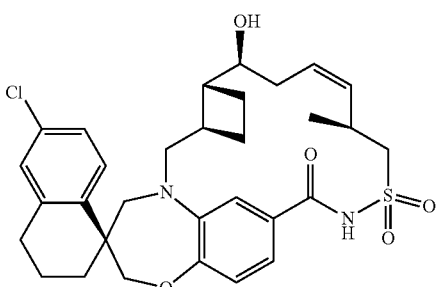

or

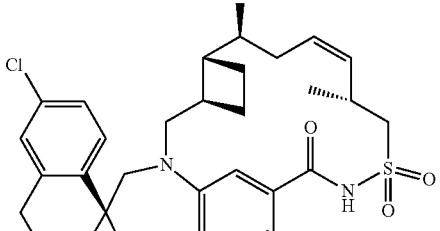

or

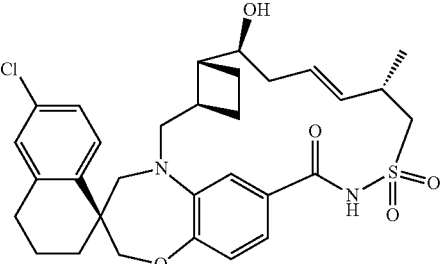

or

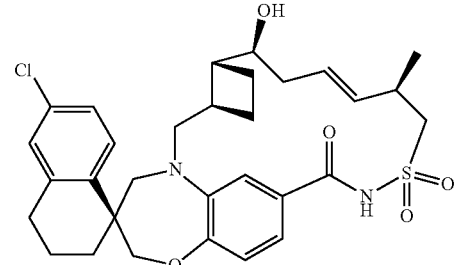

489

Step 1: (2S)-2-methyl-3-butene-1-sulfonamide and (2R)-2-methyl-3-butene-1-sulfonamide

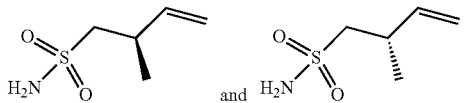

The title compound was prepared from 2-methyl-3-buten-1-ol using a similar procedure described in Intermediate E22, Step 3-6, replacing (2S,3S)-3-methylhex-5-en-2-ol in Step 3.

Step 2: (3S)-6'-chloro-5-(((1R,2R)-2-((1S)-1-hydroxy-3-buten-1-yl)cyclobutyl)methyl)-N-(((2S)-2-methyl-3-buten-1-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S)-1-hydroxy-3-buten-1-yl)cyclobutyl)methyl)-N-(((2R)-2-methyl-3-buten-1-yl)sulfonyl)-3',4,4',5-tetrahydro-2'H-spiro[1,5-benzoxazepine-3,1'-naphthalene]-7-carboxamide

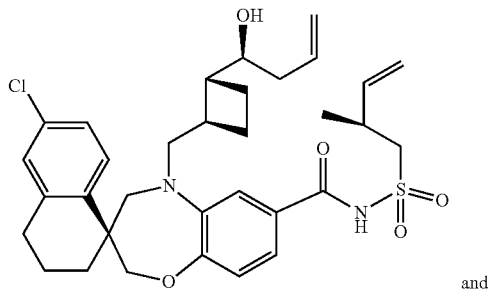

and

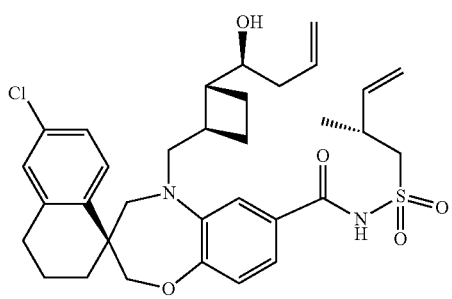

490

The title compound was prepared from (2S)-2-methyl-3-butene-1-sulfonamide and (2R)-2-methyl-3-butene-1-sulfonamide and (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA13A) using a similar procedure described in Step 4 of Example 136.

Step 3: (1S,3'R,6'R,7'S,9'Z,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'R,7'S,9'Z,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'R,7'S,9'E,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'R,7'S,9E,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide A round bottom flask was charged with (1'S)-6'-chloro-5-(((1R,2R)-2-((S)-1-hydroxybut-3-en-1-yl)cyclobutyl)methyl)-N-((2-methylbut-3-en-1-yl)sulfonyl)-3',4,4',5-tetrahydro-2H,2'H-spiro[benzo[b][1,4]oxazepine-3,1'-naphthalene]-7-carboxamide (0.200 g, 0.326 mmol) in toluene (112 mL). The mixture was stirred at ambient temperature and sparged with N2 into the reaction flask for 30 min. To this homogeneous solution was added Hoveyda-Grubbs II (0.041 g, 0.065 mmol). The mixture was stirred and heated at 100° C. for 2 h. Solvent was evaporated and the crude residue was chromatographed (silica gel, 10 to 100%, EtOAc+0.5% HOAc/hexane) to afford a mixture of the title isomers. Further purification by both reversed phase preparatory HPLC (Gemini™ Prep C$_{18}$ 5 μm column; Phenomenex, Torrance, CA; gradient elution of 25% to 75% MeCN in water, where both solvents contain 0.1% TFA, 30 min method) and then chiral separation (Column: Chiralpak OD-H, 3.0×25 cm; Mobile phase: 35% Methanol (20 mM NH3)/65% CO$_2$; Flow rate: 120 mL/min; SFC Outlet pressure: 100 bar, Temp.=23 C, Wavelength: 248 nm; Sample dissolved to 6 mg/mL in (3:1) Methanol:DCM (30 mg in 5 mL); introduced 0.4 mL of sample solution, or 2.4 mg crude sample in each preparative injection) afforded the title compound as the first eluenting isomer. $^1$H NMR (400 MHz, CD$_2$Cl$_2$) δ 7.73 (d, J=8.4 Hz, 1H), 7.48-7.38 (m, 2H), 7.17 (dd, J=2.3, 8.4 Hz, 1H), 7.09 (d, J=2.3 Hz, 1H), 6.97 (d, J=8.8 Hz, 1H), 5.15 (s, 1H), 5.09 (s, 1H), 4.32-4.17 (m, 2H), 4.16-4.07 (m, 2H), 3.70-3.59 (m, 2H), 3.23 (d, J=13.9 Hz, 1H), 3.12 (dd, J=8.7, 15.2 Hz, 1H), 2.95-2.86 (m, 2H), 2.82-2.71 (m, 2H), 2.55-2.44 (m, 1H), 2.42-2.23 (m, 2H), 2.06-1.87 (m, 6H), 1.85-1.72 (m, 2H), 1.07 (t, J=7.2 Hz, 4H). m/z (ESI, +ve ion) 685.2 (M+Na)$^+$.

Example 142. methyl 1-(((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)carbonyl)-4-piperidinecarboxylate or methyl 1-(((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)carbonyl)-4-piperidinecarboxylate or methyl 1-(((1S,3'R,6'R,7'S,8'Z,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)carbonyl)-4-piperidinecarboxylate or methyl 1-(((1S,3'R,6'R,7'S,8'Z,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)carbonyl)-4-piperidinecarboxylate

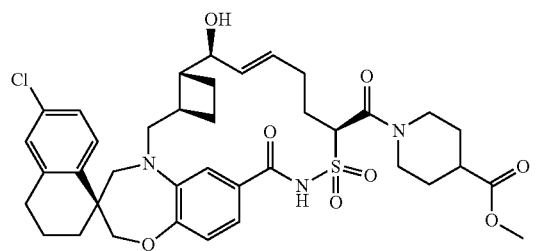

or


or


or

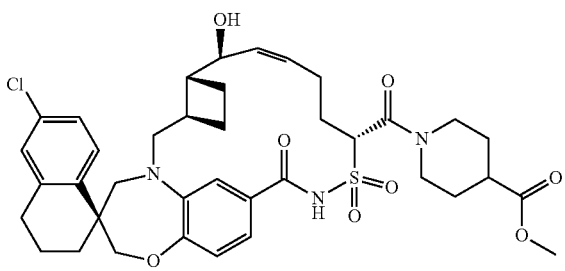

Step 1: methyl(2R)—(N,N-bis(4-methoxybenzyl)sulfamoyl)hex-5-enoate and methyl(2S)—(N,N-bis(4-methoxybenzyl)sulfamoyl)hex-5-enoate

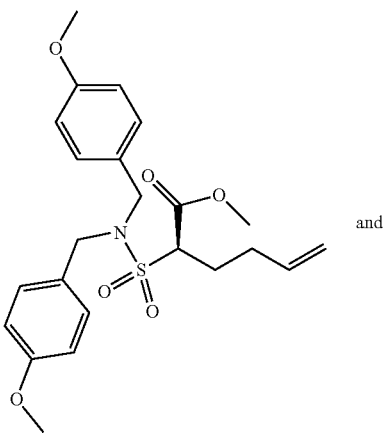

and

To a round bottom flask was added N,N-bis(4-methoxybenzyl)pent-4-ene-1-sulfonamide (Intermediate EE19, 3.40 g, 8.73 mmol) in THF (34.9 mL) at −78° C., and butyllithium solution, 2.5 M in hexanes (3.84 mL, 9.60 mmol). The mixture was stirred for 5 min and then added chlorocarbonic acid, methyl ester (1.01 mL, 13.09 mmol). The reaction mixture was stirred at this temperature for another 20 min and allowed to warm up to ambient temperature. The mixture was quenched with saturated aqueous NH$_4$Cl, and extracted with diethyl ether (2×). The combined organic layers were washed with brine, dried (MgSO$_4$), and filtered. The filtrate was concentrated to afford the title compound which was used without further purification.

Step 2: (2R)—(N,N-bis(4-methoxybenzyl)sulfamoyl)hex-5-enoic Acid and (2S)—(N,N-bis(4-methoxybenzyl)sulfamoyl)hex-5-enoic Acid

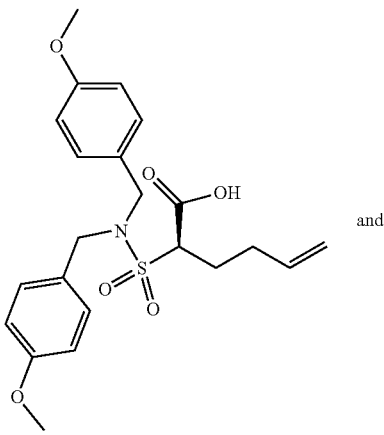

and

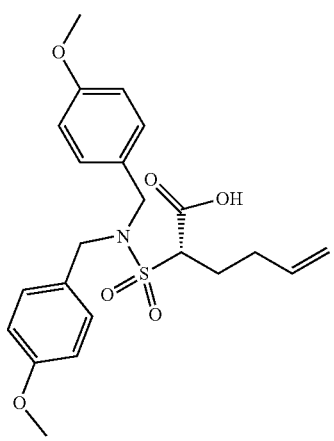

To a round bottom flask charging with a mixture of methyl(2R)—(N,N-bis(4-methoxybenzyl)sulfamoyl)hex-5-enoate (3.90 g, 8.71 mmol) and methyl(2S)—(N,N-bis(4-methoxybenzyl)sulfamoyl)hex-5-enoate (3.90 g, 8.71 mmol) in THF (36 mL) was added sodium hydroxide (1.39 g, 34.9 mmol) in water (7.3 mL). The reaction mixture was stirred at 50° C. for 18 h and then neutralized with aqueous 1.0 N HCl. The mixture was extracted with EtOAc (2×). The combined organic layers were washed with brine and dried (MgSO$_4$), and filtered. The filtrated was concentrated and the resulting residue was chromatographed (silica gel, 0 to 100%, EtOAc+0.3% HOAc/hexane) to afford the title compounds.

Step 3: methyl 1-((2R)—(N,N-bis(4-methoxybenzyl)sulfamoyl) hex-5-enoyl)piperidine-4-carboxylate and methyl 1-((2S)—(N,N-bis(4-methoxybenzyl)sulfamoyl)hex-5-enoyl) piperidine-4-carboxylate

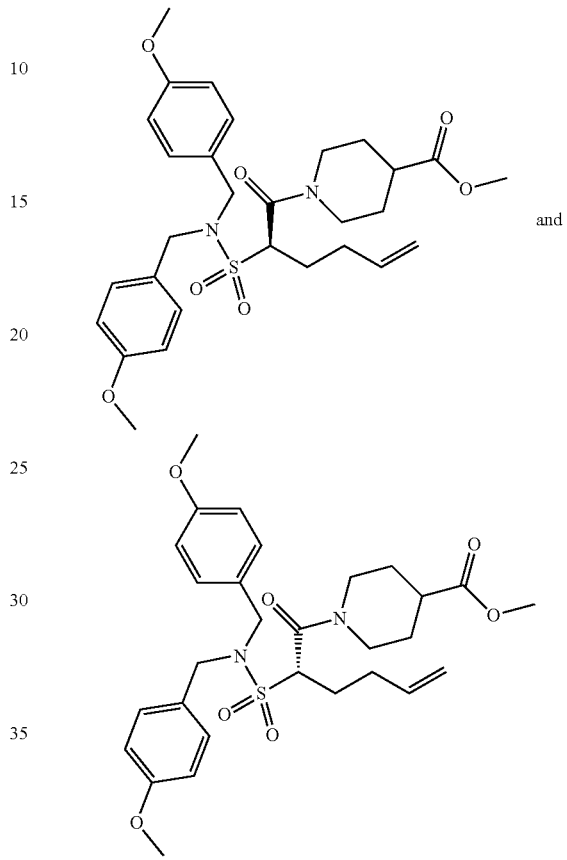

To a solution of (2S)—(N,N-bis(4-methoxybenzyl)sulfamoyl)hex-5-enoic acid and (2R)—(N,N-bis(4-methoxybenzyl)sulfamoyl)hex-5-enoic acid (2.10 g, 4.84 mmol), HATU (3.68 g, 9.69 mmol) and N,N-diisopropylethylamine (2.53 mL, 14.53 mmol) in DMF (19.4 mL) was added methyl isonipecotate (1.38 g, 9.69 mmol). The reaction mixture was stirred at 40° C. for 18 h. The mixture was added water, and extracted with EtOAc. The organic layer was concentrated and chromatographed (silica gel, 0 to 30%, acetone/DCM) to afford the title compound as a mixture of two isomers (350 mg, 12.9%). m/z (ESI, +ve ion) 581.2 (M+Na)$^+$.

Step 4: methyl 1-((2R)-sulfamoylhex-5-enoyl)piperidine-4-carboxylate and methyl 1-((2S)-sulfamoylhex-5-enoyl)piperidine-4-carboxylate

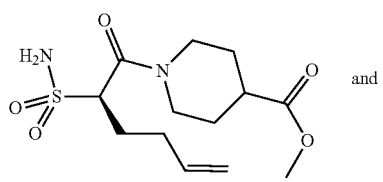

and

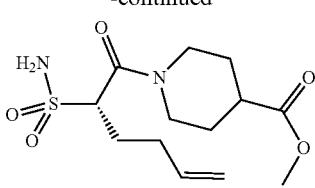

The title compounds were prepared from methyl 1-((2R)—(N,N-bis(4-methoxybenzyl)sulfamoyl) hex-5-enoyl)piperidine-4-carboxylate and methyl 1-((2S)—(N,N-bis(4-methoxybenzyl)sulfamoyl)hex-5-enoyl)piperidine-4-carboxylate using a similar procedure described in Step 2 of Example 136.

Step 5: methyl 1-((S)-2-N—((S)-6'-chloro-5-(((1R,2R)-2-((S,E)-1-hydroxyhex-2-en-1-yl)cyclobutyl)methyl)-3'4,4',5-tetrahydro-2'H-spiro[benzo[b][1,4]oxazepine-3,1'-naphthalen]-7-ylcarbonyl) sulfamoyl)hex-5-enoyl)piperidine-4-carboxylate and methyl 1-((R)-2-N—((S)-6'-chloro-5-(((1R,2R)-2-((S,E)-1-hydroxyhex-2-en-1-yl)cyclobutyl)methyl)-3'4,4',5-tetrahydro-2'H-spiro[benzo[b][1,4]oxazepine-3,1'-naphthalen]-7-ylcarbonyl)sulfamoyl)hex-5-enoyl)piperidine-4-carboxylate

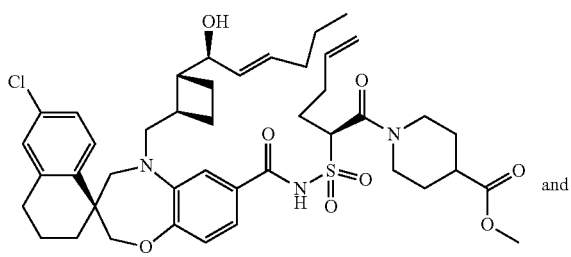

and

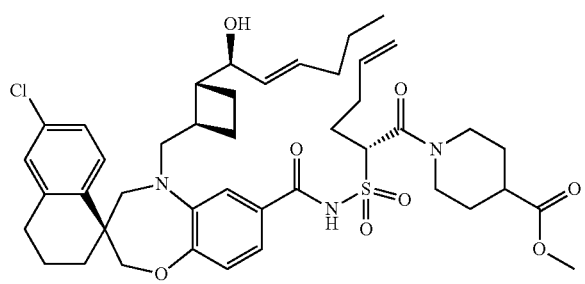

The title compounds were prepared from methyl 1-((2R)-sulfamoylhex-5-enoyl)piperidine-4-carboxylate and methyl 1-((2S)-sulfamoylhex-5-enoyl)piperidine-4-carboxylate and (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A) using a similar procedure described in Step 3 of Example 136.

Step 6: methyl 1-(((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)carbonyl)-4-piperidinecarboxylate or methyl 1-(((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)carbonyl)-4-piperidinecarboxylate or methyl 1-(((1S,3'R,6'R,7'S,8'Z,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)carbonyl)-4-piperidinecarboxylate or methyl 1-(((1S,3'R,6'R,7'S,8'Z,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)carbonyl)-4-piperidinecarboxylate A round bottom flask was charged with a mixture of methyl 1-((S)-2-N—((S)-6'-chloro-5-(((1R,2R)-2-((S,E)-1-hydroxyhex-2-en-1-yl)cyclobutyl)methyl)-3'4,4',5-tetrahydro-2'H-spiro[benzo[b][1,4]oxazepine-3,1'-naphthalen]-7-ylcarbonyl)sulfamoyl)hex-5-enoyl)piperidine-4-carboxylate and methyl 1-((R)-2-N—((S)-6'-chloro-5-(((1R,2R)-2-((S,E)-1-hydroxyhex-2-en-1-yl)cyclobutyl)methyl)-3'4,4',5-tetrahydro-2'H-spiro[benzo[b][1,4]oxazepine-3,1'-naphthalen]-7-ylcarbonyl)sulfamoyl)hex-5-enoyl)piperidine-4-carboxylate (0.125 g, 0.154 mmol) in AcOH (53.2 mL). The mixture was stirred at ambient temperature and sparged Ar into the reaction flask for 15 min. To this homogeneous solution was added Hoveyda-Grubbs II (0.019 g, 0.031 mmol). The mixture was stirred at ambient temperature under reduced pressure for 3 days after which time air was sparged into the flask for 10 min. Solvent was evaporated, and the residue was purified by reversed phase preparatory HPLC (Gemini™ Prep C$_{18}$ 5 μm column; Phenomenex, Torrance, CA; gradient elution of 25% to 75% MeCN in water, where both solvents contain 0.1% TFA, 30 min method) to afford the title compound as the first eluting isomer. $^1$H NMR (400 MHz, CD$_2$Cl$_2$) δ 7.71 (d, J=8.4 Hz, 1H), 7.16 (dd, J=2.3, 8.7 Hz, 1H), 7.09 (d, J=2.2 Hz, 1H), 6.99-6.87 (m, 3H), 5.69 (br s, 1H), 5.55-5.47 (m, 1H), 4.55-4.35 (m, 1H), 4.35-4.19 (m, 2H), 4.17-4.01 (m, 3H), 3.84 (d, J=15.5 Hz, 1H), 3.75-3.65 (m, 4H), 3.48-3.28 (m, 1H), 3.25 (d, J=14.3 Hz, 1H), 3.11-2.97 (m, 2H), 2.83-2.70 (m, 2H), 2.70-2.52 (m, 3H), 2.50-2.27 (m, 5H), 2.11-2.04 (m, 3H), 2.015-1.87 (m, 6H), 1.88-1.74 (m, 3H), 1.74-1.60 (m, 3H). m/z (ESI, +ve ion) 762.1 (M+Na)$^+$.

497

Example 143. methyl 1-(((1S,3'R,6'R,7'S,8'Z,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)carbonyl)-4-piperidinecarboxylate or methyl 1-(((1S,3'R,6'R,7'S,8'Z,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)carbonyl)-4-piperidinecarboxylate

498

Example 144. (1S,3'R,6'R,7'S,8'E,10'S,11'S)-6-chloro-7'-hydroxy-10',11'-dimethyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 13',13'-dioxide or (1S,3'R,6'R,7'S,8'E,10'S,11'R)-6-chloro-7'-hydroxy-10',11'-dimethyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 13',13'-dioxide or (1S,3'R,6'R,7'S,8'E,10'R,11R)-6-chloro-7'-hydroxy-10',11'-dimethyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 13',13'-dioxide or (1S,3'R,6'R,7'S,8'E,10'R,11'S)-6-chloro-7'-hydroxy-10',11'-dimethyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 13',13'-dioxide

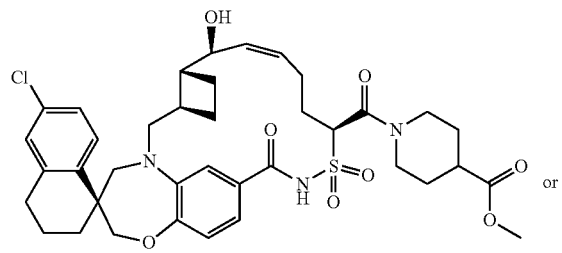

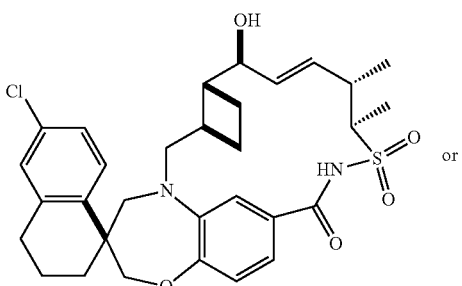

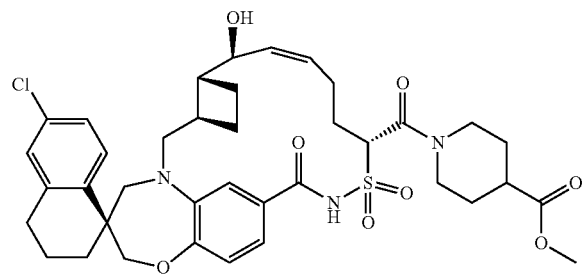

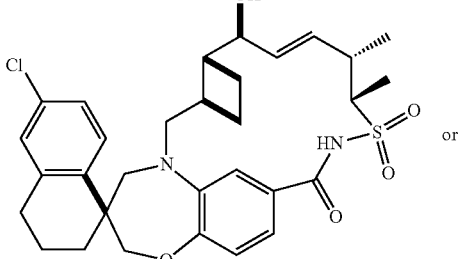

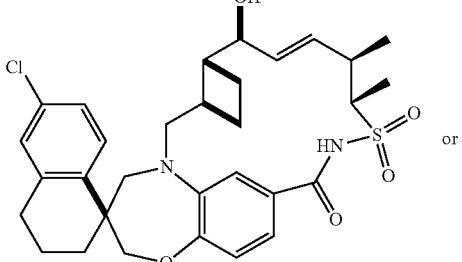

The title compound was obtained as the third eluenting isomer from the reversed phase preparatory HPLC separation in Example 142. $^1$H NMR (400 MHz, CDCl$_3$) δ 8.61 (br s, 1H), 7.73 (d, J=12.1 Hz, 1H), 7.63 (d, J=8.4 Hz, 1H), 7.21-7.13 (m, 1H), 7.11 (d, J=2.3 Hz, 1H), 7.01-6.89 (m, 3H), 5.67-5.58 (m, 1H), 5.42 (dd, J=3.1, 10.4 Hz, 1H), 4.60-4.57 (m, 1H), 4.50-4.10 (m, 6H), 3.83 (d, J=13.3 Hz, 1H), 3.75-3.70 (m, 4H), 3.57-3.47 (m, 1H), 3.41 (d, J=9.4 Hz, 1H), 3.37-3.25 (m, 1H), 3.24-3.05 (m, 1H), 2.88-2.79 (m, 2H), 2.63-2.44 (m, 3H), 2.42-2.16 (m, 5H), 2.14-1.98 (m, 3H), 1.90-1.60 (m, 9H). m/z (ESI, +ve ion) 762.1 (M+Na)$^+$.

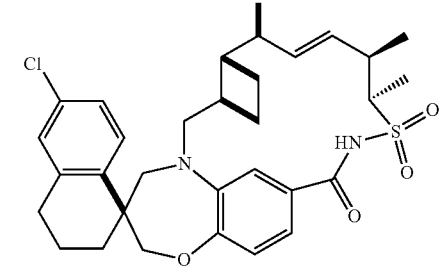

Step 1: (2S,3R)-3-methyl-4-pentene-2-sulfonamide and (2S,3S)-3-methyl-4-pentene-2-sulfonamide and (2R,3S)-3-methyl-4-pentene-2-sulfonamide and (2S,3R)-3-methyl-4-pentene-2-sulfonamide

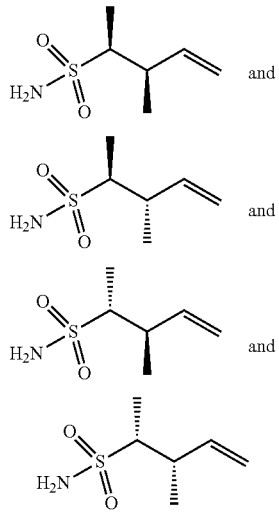

The title compounds were prepared by a similar sequence described in EE22, using but-3-en-ol with (2S,3S)-3-methylhex-5-en-2-ol as the starting alcohol in Step 3.

Step 2: (3S)-6'-chloro-5-(((1R,2R)-2-((1S,2E,4R,5S)-1-hydroxy-4-methyl-5-sulfamoyl-2-hexen-1-yl)cyclobutyl)methyl)-3',4,4',5-tetrahydro-2'H-spiro[1,5-benzoxazepine-3,1'-naphthalene]-7-carboxylic Acid and (3S)-6'-chloro-5-(((1R,2R)-2-((1S,2E,4S,5S)-1-hydroxy-4-methyl-5-sulfamoyl-2-hexen-1-yl)cyclobutyl)methyl)-3',4,4',5-tetrahydro-2'H-spiro[1,5-benzoxazepine-3,1'-naphthalene]-7-carboxylic Acid (3S)-6'-chloro-5-(((1R,2R)-2-((1S,2E,4S,5R)-1-hydroxy-4-methyl-5-sulfamoyl-2-hexen-1-yl)cyclobutyl)methyl)-3',4,4',5-tetrahydro-2'H-spiro[1,5-benzoxazepine-3,1'-naphthalene]-7-carboxylic Acid (3S)-6'-chloro-5-(((1R,2R)-2-((1S,2E,4R,5R)-1-hydroxy-4-methyl-5-sulfamoyl-2-hexen-1-yl)cyclobutyl)methyl)-3',4,4',5-tetrahydro-2'H-spiro[1,5-benzoxazepine-3,1'-naphthalene]-7-carboxylic Acid

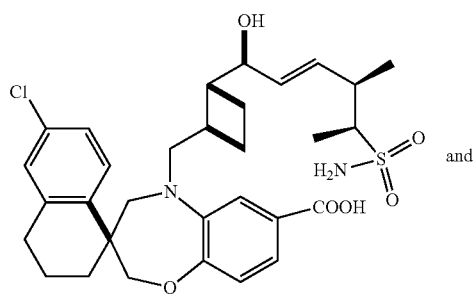

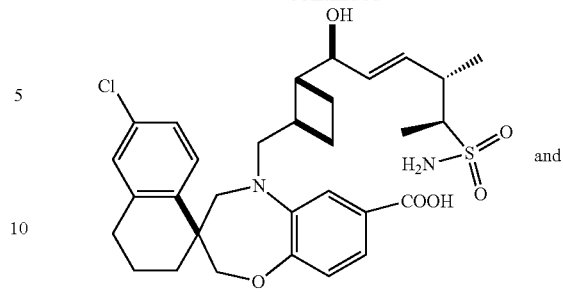

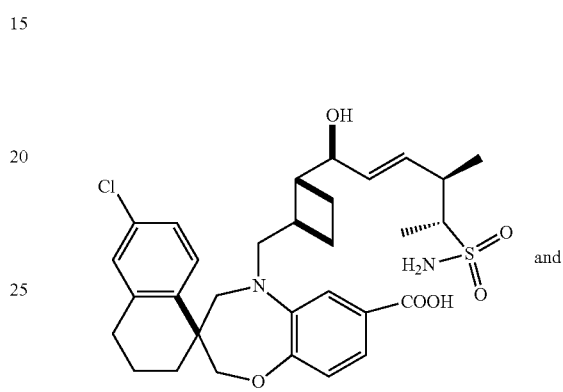

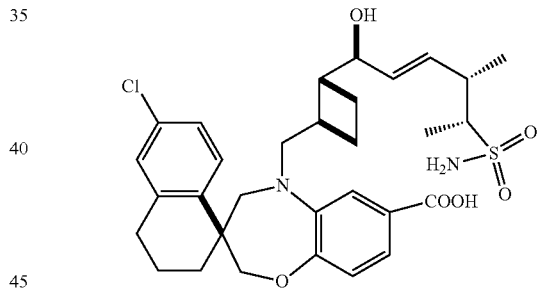

A vial was charged with (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A, 180 mg, 0.353 mmol) and a mixture of (2S,3R)-3-methyl-4-pentene-2-sulfonamide, (2S,3S)-3-methyl-4-pentene-2-sulfonamide, (2R,3S)-3-methyl-4-pentene-2-sulfonamide, (2S,3R)-3-methyl-4-pentene-2-sulfonamide (288 mg, 1.764 mmol) in DCE (5 mL). The mixture was sparged with Argon first for 10 min. To this mixture was added Hoveyda-Grubbs II (22.11 mg, 0.035 mmol) at ambient temperature. The reaction was stirred and heated at 50° C. for 3 h, then air was sparged into the flask for 15 min. The mixture was filtered, and the filtrate was directly chromatographed (silica gel, 0 to 100%, EtOAc/hexane, and then to 100% EtOAc+1% HOAc/hexane) to afford the title compounds (106 mg, 49.8%). m/z (ESI, +ve ion) 603.2 (M+Na)$^+$.

Step 3: (1S,3'R,6'R,7'S,8'E,10'S,11'S)-6-chloro-7'-hydroxy-10',11'-dimethyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 13',13'-dioxide or (1S,3'R,6'R,7'S,8'E,10'S,11'R)-6-chloro-7'-hydroxy-10',11'-dimethyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 13',13'-dioxide or (1S,3'R,6'R,7'S,8'E,10'R,11'R)-6-chloro-7'-hydroxy-10',11'-dimethyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 13',13'-dioxide or (1S,3'R,6'R,7'S,8'E,10'R,11'S)-6-chloro-7'-hydroxy-10',11'-dimethyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 13',13'-dioxide To a mixture of (3S)-6'-chloro-5-(((1R,2R)-2-((1S,2E,4R,5S)-1-hydroxy-4-methyl-5-sulfamoyl-2-hexen-1-yl)cyclobutyl)methyl)-3',4,4',5-tetrahydro-2'h-spiro[1,5-benzoxazepine-3,1'-naphthalene]-7-carboxylic acid, (3S)-6'-chloro-5-(((1R,2R)-2-((1S,2E,4S,5S)-1-hydroxy-4-methyl-5-sulfamoyl-2-hexen-1-yl)cyclobutyl)methyl)-3',4,4',5-tetrahydro-2'h-spiro[1,5-benzoxazepine-3,1'-naphthalene]-7-carboxylic acid, (3S)-6'-chloro-5-(((1R,2R)-2-((1S,2E,4S,5R)-1-hydroxy-4-methyl-5-sulfamoyl-2-hexen-1-yl)cyclobutyl)methyl)-3',4,4',5-tetrahydro-2'h-spiro[1,5-benzoxazepine-3,1'-naphthalene]-7-carboxylic acid and (3S)-6'-chloro-5-(((1R,2R)-2-((1S,2E,4R,5R)-1-hydroxy-4-methyl-5-sulfamoyl-2-hexen-1-yl)cyclobutyl)methyl)-3',4,4',5-tetrahydro-2'h-spiro[1,5-benzoxazepine-3,1'-naphthalene]-7-carboxylic acid (110 mg, 0.182 mmol) was added N,N-dimethylpyridin-4-amine (DMAP) (44.6 mg, 0.365 mmol) and triethylamine (0.076 mL, 0.547 mmol) in DCM (100 mL) at ambient temperature. N-(3-dimethylaminopropyl)-N'-ethylcarbodiimide hydrochloride (69.9 mg, 0.365 mmol) was added slowly. The mixture was stirred at ambient temperature for 18 h. The reaction was then diluted with dichloromethane, washed with saturated sodium bicarbonate, saturated ammonium chloride, and brine. The combined organic layers were dried (MgSO$_4$), filtered and the filtrate was concentrated. The crude residue was purified by reversed phase preparatory HPLC (Gemini™ Prep C$_{18}$ 5 μm column; Phenomenex, Torrance, CA; gradient elution of 25% to 75% MeCN in water, where both solvents contain 0.1% TFA, 30 min method) to afford the title compound as the second eluenting isomer. $^1$H NMR (400 MHz, C$_6$D$_6$) δ=7.98 (br s, 1H), 7.72 (d, J=8.8 Hz, 1H), 7.30 (dd, J=2.1, 8.3 Hz, 1H), 7.18 (d, J=8.7 Hz, 1H), 7.10 (d, J=2.2 Hz, 1H), 6.96 (d, J=6.9 Hz, 1H), 6.86 (s, 1H), 5.84 (dd, J=4.3, 15.5 Hz, 1H), 5.74 (dd, J=8.8, 15.8 Hz, 1H), 4.16-4.05 (m, 3H), 3.75-3.63 (m, 2H), 3.45-3.20 (m, 3H), 2.83-2.71 (m, 2H), 2.56-2.46 (m, 1H), 2.43-2.33 (m, 1H), 2.09-1.80 (m, 6H), 1.68-1.58 (m, 3H), 1.57 (d, J=7.2 Hz, 3H), 1.13 (d, J=6.8 Hz, 3H). m/z (ESI, +ve ion) 585.2 (M+Na)$^+$.

Example 145. (((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetonitrile or ((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetonitrile or ((1S,3'R,6'R,7'S,8'Z,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetonitrile or ((1S,3'R,6'R,7'S,8'Z,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetonitrile

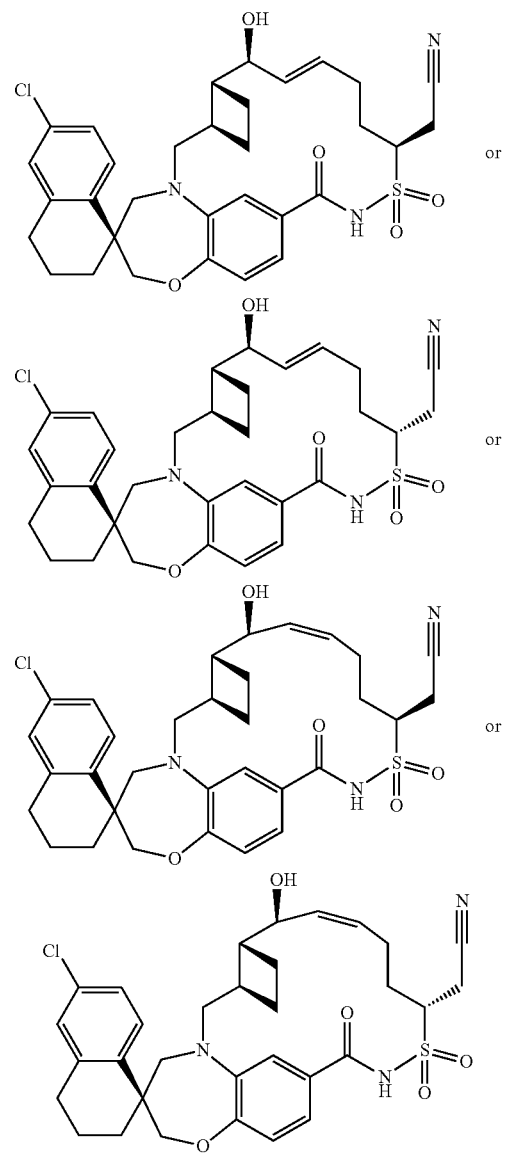

Step 1: (3S)-1-hydroxy-N,N-bis(4-methoxybenzyl)-6-heptene-3-sulfonamide and (3R)-1-hydroxy-N,N-bis(4-methoxybenzyl)-6-heptene-3-sulfonamide

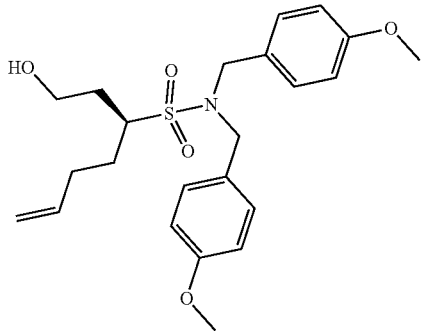

and

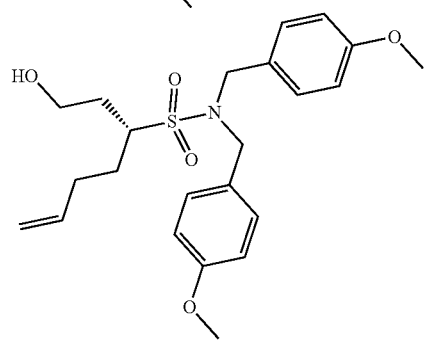

To a solution of N,N-bis(4-methoxybenzyl)pent-4-ene-1-sulfonamide (Intermediate EE19, 2.55 g, 6.55 mmol) in THF (26 mL) was added butyllithium solution, 2.5 M in hexanes (2.88 mL, 7.20 mmol) at −78° C. dropwise. The reaction mixture was stirred at −78° C. for 10 min, and then ethylene oxide gas was introduced into the reaction flask by sparging from a cylinder for 1 h at the same temperature. The reaction mixture was allowed to warm to ambient temperature. The mixture was then quenched with saturated aqueous NH₄Cl, and extracted with EtOAc (2×). The combined organic layers were washed with brine, dried (Na₂SO₄), and filtered. The filtrate was concentrated. The resulting residue was chromatographed (silica gel, 30 to 60%, EtOAc/hexane) to afford the title compounds (1.80 g, 63.4%) as a colorless oil.

Step 2: (3R)—(N,N-bis(4-methoxybenzyl)sulfamoyl)hept-6-enoic acid and (3S)—(N,N-bis(4-methoxybenzyl)sulfamoyl)hept-6-enoic acid

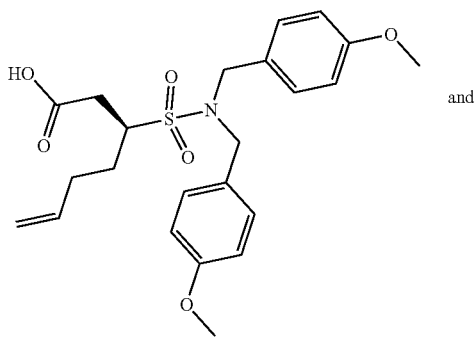

and

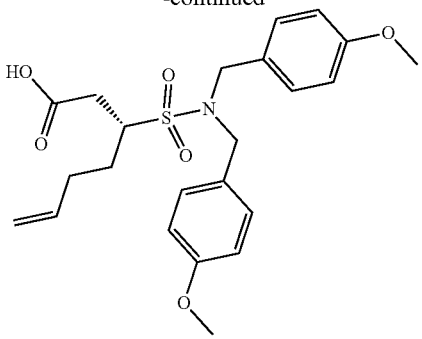

In a round bottom flask equipped with an additional funnel was added (3S)-1-hydroxy-N,N-bis(4-methoxybenzyl)-6-heptene-3-sulfonamide and (3R)-1-hydroxy-N,N-bis(4-methoxybenzyl)-6-heptene-3-sulfonamide (1.00 g, 2.31 mmol), KBr (27.4 mg, 0.231 mmol), 5% sodium bicarbonate in water (10.85 mL, 6.46 mmol), and TEMPO (396 mg, 2.54 mmol) in acetone (15 mL). To this mixture was added 6% sodium hypochlorite in water (2.07 mL, 1.67 mmol) at 0° C. through the additional funnel. The resulting reaction mixture was stirred at this temperature for 1 h. The mixture was diluted with diethyl ether, added ice cold aqueous 1.0 N HCl (30 mL) with brine (30 mL). The organic layer was washed with brine, dried (Na₂SO₄) and concentrated. The residue was chromatographed (silica gel, 0 to 100%, EtOAc+0.5% HOAc/DCM) to afford the title compounds (530 mg, 51.3%) as a pale brown syrup.

Step 3: (3R)—(N,N-bis(4-methoxybenzyl)sulfamoyl)hept-6-enamide and (3S)—(N,N-bis(4-methoxybenzyl)sulfamoyl)hept-6-enamide

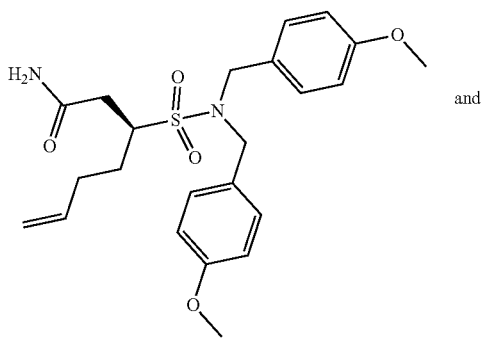

and

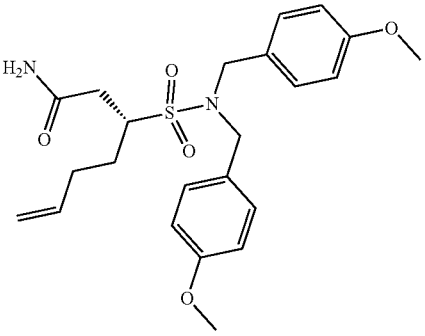

To a solution of 3-(N,N-bis(4-methoxybenzyl)sulfamoyl)hept-6-enoic acid (530 mg, 1.18 mmol), and N,N-diisopropylethylamine (0.618 mL, 3.55 mmol) in DMF (1.00 mL) was added 7.0 N ammonia solution in methanol (0.846 mL, 5.92 mmol). The reaction mixture was stirred at 50° C. for 18 h. Solvent was evaporated, and the crude residue was chromatographed (silica gel, 0 to 40%, acetone+10% MeOH/DCM) to afford the title compounds (50 mg, 9.45%).

Step 4: (2S)-1-cyano-N,N-bis(4-methoxybenzyl)-5-hexene-2-sulfonamide and (2R)-1-cyano-N,N-bis(4-methoxybenzyl)-5-hexene-2-sulfonamide

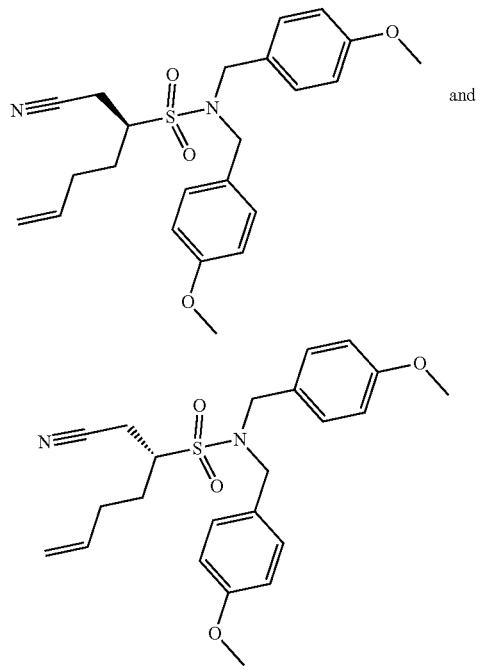

A solution of (3R)—(N,N-bis(4-methoxybenzyl)sulfamoyl)hept-6-enoic acid and (3S)—(N,N-bis(4-methoxybenzyl)sulfamoyl)hept-6-enoic acid (50 mg, 0.112 mmol) and triethylamine (0.078 mL, 0.560 mmol) in tetrahydrofuran (3 mL) was added trifluoroacetic anhydride (0.039 mL, 0.280 mmol) and stirred from 0° C. to ambient temperature for 2 h. The mixture was quenched with H₂O, and extracted with EtOAc (2×). The organic layer was washed with brine, dried (MgSO₄), and filtrated. The filtrate was concentrated. The resulting residue was chromatographed (silica gel, 0 to 50%, acetone/DCM) to afford the title compounds (45 mg, 94%).

Step 5: (2S)-1-cyano-5-hexene-2-sulfonamide and (2R)-1-cyano-5-hexene-2-sulfonamide

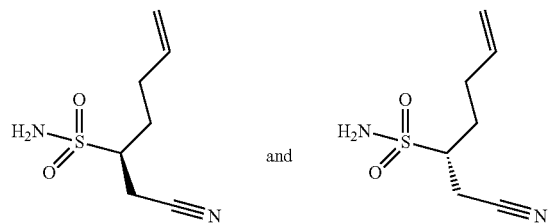

The title compounds were prepared from a mixture of (2S)-1-cyano-N,N-bis(4-methoxybenzyl)-5-hexene-2-sulfonamide and (2R)-1-cyano-N,N-bis(4-methoxybenzyl)-5-hexene-2-sulfonamide using a similar procedure described in Step 2 of Example 137.

Step 6: (3S)-6'-chloro-N-(((2S)-1-cyano-5-hexen-2-yl)sulfonyl)-5-(((1R,2R)-2-((1S,2E)-1-hydroxy-2,5-hexadien-1-yl)cyclobutyl)methyl)-3',4,4',5-tetrahydro-2'H-spiro[1,5-benzoxazepine-3,1'-naphthalene]-7-carboxamide and (3S)-6'-chloro-N-(((2R)-1-cyano-5-hexen-2-yl)sulfonyl)-5-(((1R,2R)-2-((1S,2E)-1-hydroxy-2,5-hexadien-1-yl)cyclobutyl)methyl)-3',4,4',5-tetrahydro-2'H-spiro[1,5-benzoxazepine-3,1'-naphthalene]-7-carboxamide

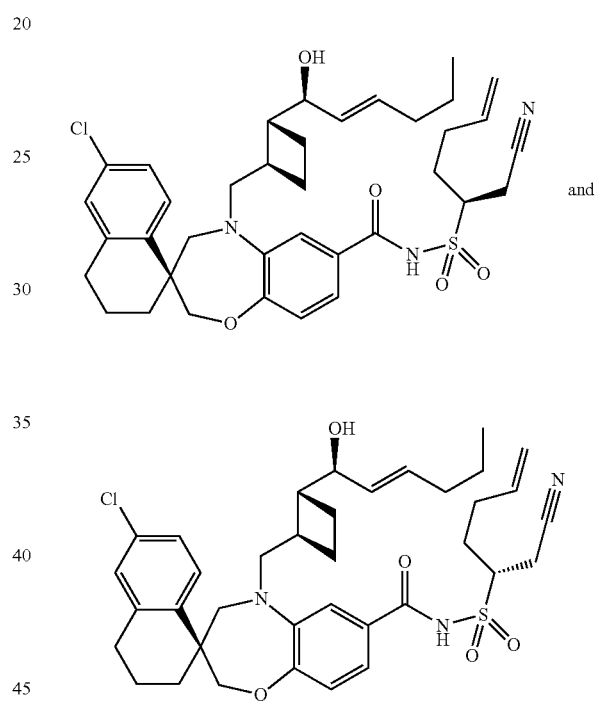

To a mixture of (2S)-1-cyano-5-hexene-2-sulfonamide and (2R)-1-cyano-5-hexene-2-sulfonamide was added N,N-Dimethylpyridin-4-amine (DMAP) (96 mg, 0.784 mmol), (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A, 200 mg, 0.392 mmol) and triethylamine (0.164 mL, 1.176 mmol) in DCM (2 mL) at ambient temperature. N-(3-dimethylaminopropyl)-n'-ethylcarbodiimide hydrochloride (150 mg, 0.784 mmol) was added slowly and the reaction mixture was stirred at ambient temperature for 18 h. The mixture was diluted with dichloromethane. The organic layer was washed with aqueous 1.0 N HCl, brine and dried (MgSO₄) and filtered. The filtrate was concentrated and the resulting residue was chromatographed (silica gel, 10 to 100%, EtOAc+1% HOAc/hexane) to afford the title compounds (230 mg, 86%). m/z (ESI, +ve ion) 702.3 (M+Na)⁺.

Step 7: ((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-12'-yl)acetonitrile or ((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-12'-yl)acetonitrile or ((1S,3'R,6'R,7'S,8'Z,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-12'-yl)acetonitrile or ((1S,3'R,6'R,7'S,8'Z,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-12'-yl)acetonitrile A round bottom flask was charged with (3S)-6'-chloro-N-(((2S)-1-cyano-5-hexen-2-yl)sulfonyl)-5-(((1R,2R)-2-((1S,2E)-1-hydroxy-2,5-hexadien-1-yl)cyclobutyl)methyl)-3',4,4',5-tetrahydro-2'h-spiro[1,5-benzoxazepine-3,1'-naphthalene]-7-carboxamide and (3S)-6'-chloro-N-(((2R)-1-cyano-5-hexen-2-yl)sulfonyl)-5-(((1R,2R)-2-((1S,2E)-1-hydroxy-2,5-hexadien-1-yl)cyclobutyl)methyl)-3',4,4',5-tetrahydro-2'h-spiro[1,5-benzoxazepine-3,1'-naphthalene]-7-carboxamide (0.260 g, 0.382 mmol) in AcOH (132 mL). The mixture was stirred at ambient temperature and argon was sparged into the reaction flask for 15 min. To this homogeneous solution was added Hoveyda-Grubbs II (0.048 g, 0.076 mmol). The mixture was stirred at ambient temperature under reduced pressure for 18 h. Air was sparged into the reaction for 10 min. Solvent was removed and the crude residue was purified by reversed phase preparatory HPLC (Gemini™ Prep C$_{18}$ 5 μm column; Phenomenex, Torrance, CA; gradient elution of 25% to 75% MeCN in water, where both solvents contain 0.1% TFA, 30 min method) to afford the title compound as the first eluenting isomer (8 mg, 3.43%). ¹H NMR (400 MHz, CD$_2$Cl$_2$) δ 7.71 (d, J=8.4 Hz, 1H), 7.17 (dd, J=1.8, 9.2 Hz, 1H), 7.10 (d, J=1.8 Hz, 1H), 7.03-6.88 (m, 3H), 5.83-5.68 (m, 2H), 4.35-4.40 (m, 1H), 4.21 (t, J=4.7 Hz, 1H), 4.15-4.02 (m, 2H), 3.81 (d, J=14.9 Hz, 1H), 3.70 (d, J=14.1 Hz, 1H), 3.26 (d, J=14.3 Hz, 1H), 3.16-2.98 (m, 3H), 2.91-2.70 (m, 2H), 2.47-2.20 (m, 6H), 2.15-1.51 (m, 6H), 1.42 (t, J=12.1 Hz, 2H). m/z (ESI, +ve ion) 585.2 (M+Na)⁺.

Example 146. (1S,3'R,6'R,7'S,8'E,12'S)-6-chloro-7'-hydroxy-12'-(4-morpholinylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,12'R)-6-chloro-7'-hydroxy-12'-(4-morpholinylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

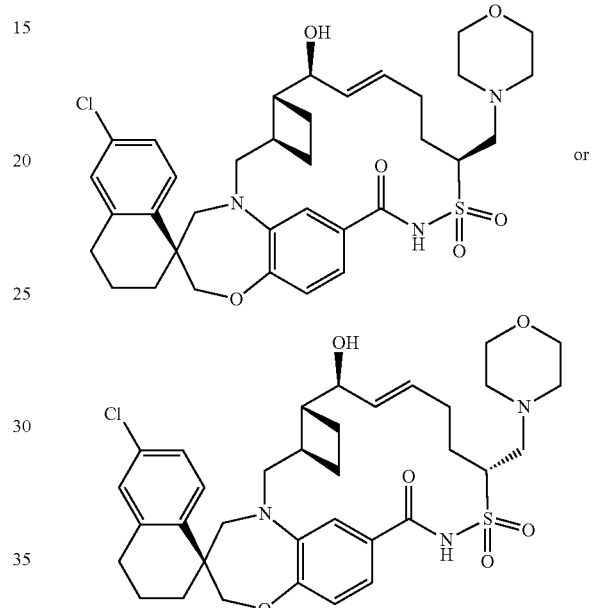

Step 1: (2R)1-hydroxy-N,N-bis(4-methoxybenzyl)hex-5-ene-2-sulfonamide and (2S)-1-hydroxy-N,N-bis(4-methoxybenzyl)-5-hexene-2-sulfonamide

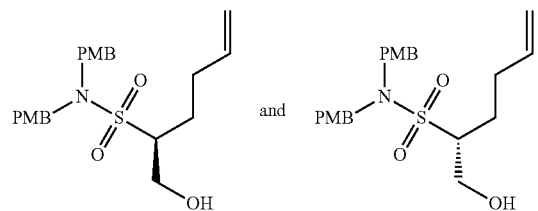

To a round bottom flask was added methyl 2-(N,N-bis(4-methoxybenzyl)sulfamoyl)hex-5-enoate (from Example 142, Step 1, 0.82 g, 1.83 mmol), lithium borohydride (0.08 g, 3.66 mmol) in THF (9.16 mL), and a few drops of water at ambient temperature. The reaction mixture was stirred for 18 h and added aqueous 1.0 N HCl (2 mL). The mixture was extracted with EtOAc (2×). The combined organic layers were washed with water, brine, dried (MgSO$_4$), and filtered. The filtrate was concentrated and the crude residue was chromatographed (silica gel, 20 to 60%, EtOAc/hexane) to afford the title compound.

Step 2: (2S)—N,N-bis(4-methoxybenzyl)-1-oxo-5-hexene-2-sulfonamide and (2R)—N,N-bis(4-methoxybenzyl)-1-oxo-5-hexene-2-sulfonamide

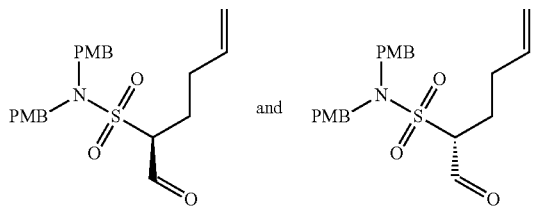

To a solution of (2R)-1-hydroxy-N,N-bis(4-methoxybenzyl)hex-5-ene-2-sulfonamide and (2S)-1-hydroxy-N,N-bis(4-methoxybenzyl)-5-hexene-2-sulfonamide (2.00 g, 4.77 mmol) in DCM (20 mL) was added Dess-Martin periodinane (4.04 g, 9.53 mmol) at ambient temperature. The reaction mixture was stirred at ambient temperature for 12 h. The mixture was then quenched with saturated aqueous Na$_2$S$_2$O$_3$ (15 mL), and extracted with Et$_2$O (2×). The combined organic layers were washed with saturated aqueous NaHCO$_3$, brine, dried (MgSO$_4$), and Filtered, the filtrate was concentrated, and the crude residue was chromatographed (silica gel, 10 to 40%, EtOAc/hexane) to afford the title compounds.

Step 3: (2R)—N,N-bis(4-methoxybenzyl)-1-(4-morpholinyl)-5-hexene-2-sulfonamide and (2S)—N,N-bis(4-methoxybenzyl)-1-(4-morpholinyl)-5-hexene-2-sulfonamide

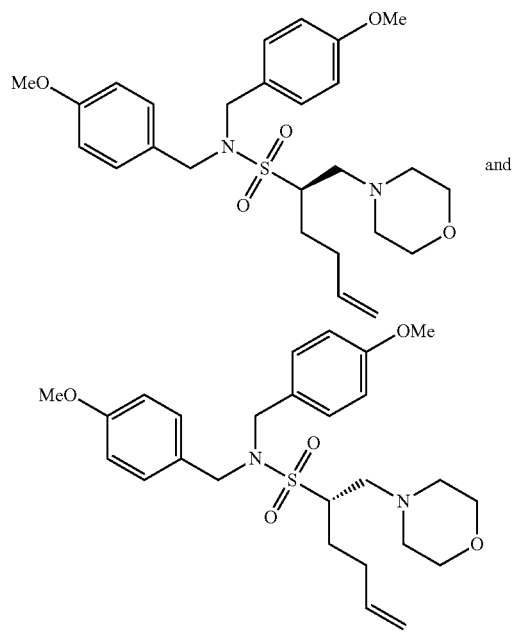

To a mixture of (2S)—N,N-bis(4-methoxybenzyl)-1-oxo-5-hexene-2-sulfonamide, (2R)—N,N-bis(4-methoxybenzyl)-1-oxo-5-hexene-2-sulfonamide (1.60 g, 3.83 mmol), morpholine (0.84 mL, 9.58 mmol), and acetic acid (5 drops) in DCE (25 mL) was added sodium triacetoxyborohydride (2.44 g, 11.50 mmol) at ambient temperature. The mixture was stirred for 12 h, and additional morpholine and sodium triacetoxyborohydride (2.44 g, 11.50 mmol) were added to reach the completion. The reaction was quenched with saturated aqueous NH$_4$Cl, and extracted with EtOAc. The organic layer was washed with brine, dried (MgSO$_4$) and concentrated. The residue was purified by the reversed phase preparatory HPLC (Gemini™ Prep C$_{18}$ 5 μm column; Phenomenex, Torrance, CA; gradient elution of 10% to 90% MeCN in water, where both solvents contain 0.1% TFA, 30 min method) to afford the title compounds (1.20 g, 64.1%).

Step 4: (2S)-1-(4-morpholinyl)-5-hexene-2-sulfonamide and (2R)-1-(4-morpholinyl)-5-hexene-2-sulfonamide

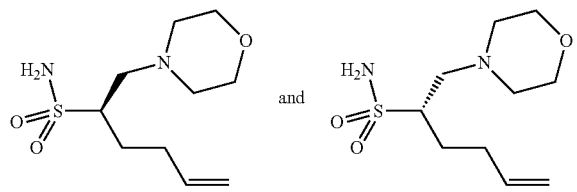 [SMILES: C=CCC[C@H](CN1CCOCC1)S(N)(=O)=O ; C=CCC[C@@H](CN1CCOCC1)S(N)(=O)=O]

The title compounds were prepared from (2R)—N,N-bis(4-methoxybenzyl)-1-(4-morpholinyl)-5-hexene-2-sulfonamide and (2S)—N,N-bis(4-methoxybenzyl)-1-(4-morpholinyl)-5-hexene-2-sulfonamide using a similar procedure in Step 2 of Example 136.

Step 5: (3S)-6'-chloro-5-(((1R,2R)-2-((1S,2E)-1-hydroxy-2-hexen-1-yl)cyclobutyl)methyl)-N-(42S)-1-(4-morpholinyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R)-1-(4-morpholinyl)-5-hexen-2-yl)sulfonyl)-3',4,4',5-tetrahydro-2'H-spiro[1,5-benzoxazepine-3,1'-naphthalene]-7-carboxamide

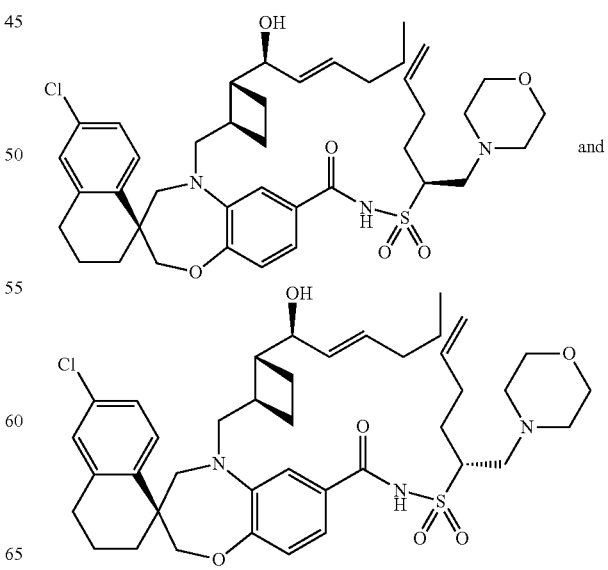

To a mixture of (2R)-1-(4-morpholinyl)-5-hexene-2-sulfonamide and (2S)-1-(4-morpholinyl)-5-hexene-2-sulfonamide was added N,N-dimethylpyridin-4-amine (DMAP) (96 mg, 0.784 mmol), a solution of (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A, 200 mg, 0.392 mmol) and triethylamine (0.164 mL, 1.176 mmol) in DCM (2 mL) at ambient temperature. N-(3-dimethylaminopropyl)-n'-ethylcarbodiimide hydrochloride (150 mg, 0.784 mmol) was then added slowly. The mixture was stirred at ambient temperature for 18 h. The mixture was added water and diluted with dichloromethane. The organic layer was washed with aqueous 1.0 N HCl, brine, dried (MgSO$_4$) and filtered. The filtrate was concentrated and the resulting residue was chromatographed (silica gel, 10 to 100%, EtOAc+1% HOAc/hexane) to afford the title compounds (230 mg, 86%).

Step 6: (1S,3'R,6'R,7'S,8'E,12'S)-6-chloro-7'-hydroxy-12'-(4-morpholinylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-hydroxy-12'-(4-morpholinylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'Z,12'S)-6-chloro-7'-hydroxy-12'-(4-morpholinylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'Z,12'R)-6-chloro-7'-hydroxy-12'-(4-morpholinylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide A round bottom flask was charged with (3S)-6'-chloro-5-(((1R,2R)-2-((1S,2E)-1-hydroxy-2-hexen-1-yl)cyclobutyl)methyl)-N-(((2S)-1-(4-morpholinyl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R)-1-(4-morpholinyl)-5-hexen-2-yl)sulfonyl)-3',4,4',5-tetrahydro-2'h-spiro[1,5-benzoxazepine-3,1'-naphthalene]-7-carboxamide (210 mg, 0.284 mmol) in DCE (142 mL). The mixture was stirred at ambient temperature and argon was sparged into the reaction flask for 30 min. To this homogeneous solution was added Hoveyda-Grubbs II (35.5 mg, 0.057 mmol) and stirred at ambient temperature under reduced pressure for 18 h. Solvent was evaporated and the crude residue was chromatographed (silica gel, 10 to 100%, EtOAc+0.5% HOAc/hexane, and then 100% 10% MeOH/DCM) to afford an oil. Further purification of this oil by reversed phase preparatory HPLC (Gemini™ Prep C$_{18}$ 5 μm column; Phenomenex, Torrance, CA; gradient elution of 25% to 75% MeCN in water, where both solvents contain 0.1% TFA, 30 min method) afforded the title compound as the first eluting isomer. $^1$H NMR (400 MHz, CD$_2$Cl$_2$) δ 7.71 (d, J=8.5 Hz, 1H), 7.16 (dd, J=2.2, 8.5 Hz, 1H), 7.09 (d, J=2.2 Hz, 1H), 7.03 (dd, J=8.1, 1.7 Hz, 1H), 6.96-6.91 (m, 2H), 5.81-5.72 (m, 1H), 5.67 (dd, J=5.7, 15.5 Hz, 1H), 5.15-4.51 (br, 2H), 4.49 (br s, 2H), 4.34-4.16 (m, 1H), 4.14-3.94 (m, 6H), 3.82-3.57 (m, 3H), 3.52-3.24 (m, 5H), 3.11 (dd, J=8.3, 15.4 Hz, 1H), 2.83-2.68 (m, 2H), 2.47-2.30 (m, 3H), 2.30-2.12 (m, 2H), 2.06-1.98 (m, 2H), 1.98-1.60 (m, 6H). m/z (ESI, +ve ion) 670.2 (M+Na)$^+$.

Example 147. (1S,3'R,6'R,7'S,8'Z,12'R)-6-chloro-7'-hydroxy-12'-(4-morpholinylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'Z,12'S)-6-chloro-7'-hydroxy-12'-(4-morpholinylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

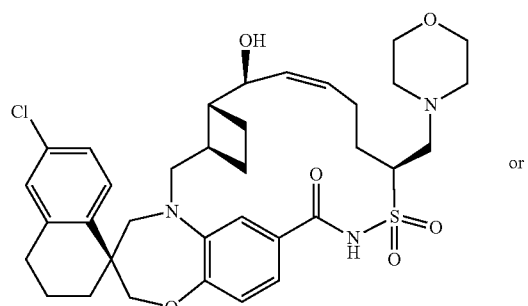

or

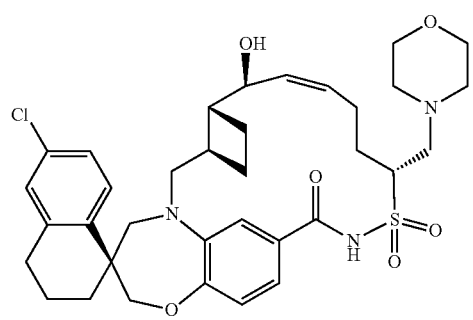

The title compound was obtained as the third eluting isomer from the reversed phase preparatory HPLC separation in Example 146. $^1$H NMR (400 MHz, CD$_2$Cl$_2$) δ 7.72 (d, J=8.4 Hz, 1H), 7.42 (dd, J=2.1, 8.3 Hz, 1H), 7.38 (d, J=3.7 Hz, 1H), 7.16 (dd, J=2.2, 8.5 Hz, 1H), 7.09 (d, J=2.2 Hz, 1H), 6.97 (d, J=8.4 Hz, 1H), 5.72-5.62 (m, 1H), 5.58 (dd, J=6.1, 11.0 Hz, 1H), 4.42 (t, J=7.2 Hz, 1H), 4.17 (d, J=6.7 Hz, 1H), 4.13 (d, J=2.9 Hz, 2H), 4.03-3.88 (m, 5H), 3.83 (d, J=15.8 Hz, 1H), 3.65 (d, J=14.1 Hz, 1H), 3.50-3.29 (br, 2H), 3.28 (d, J=4.3 Hz, 1H), 3.24 (d, J=4.5 Hz, 1H), 2.80-2.72 (m, 2H), 2.67-2.52 (m, 2H), 2.50-1.65 (m, 13H), 1.57-1.43 (m, 2H). m/z (ESI, +ve ion) 670.2 (M+Na)$^+$.

Example 148. (1S,3'R,6'R,7'S,8'E,12'S)-6-chloro-12'-cyclopropyl-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,12'S)-6-chloro-12'-cyclopropyl-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

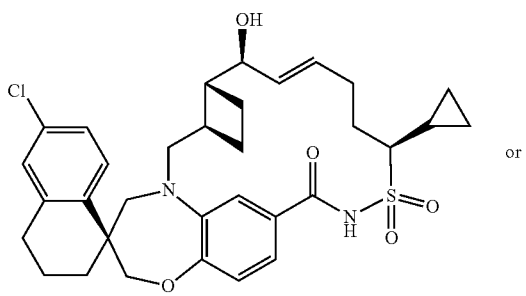

or

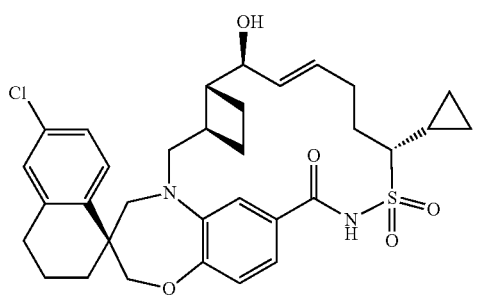

Step 1: bis(4-methoxybenzyl)amine

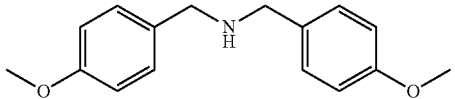

To a three neck round bottom flask was added (4-methoxyphenyl)methanamine (35.7 g, 260 mmol) and 4-methoxybenzaldehyde (31.7 mL, 260 mmmol) in EtOH (300 mL, 200 proof). The reaction mixture was stirred and the internal temperature was increased to 41° C. A precipitate was formed. After about 5 min, additional ethanol (300 mL) was added to the reaction while stirring. The reaction mixture was stirred for 1 h and NaBH₄ (5.91 g, 156 mmol) was added portionwise in 40 min. The maximum internal temperature was about 33° C. The reaction was then cooled in an ice bath, and the slurry was added concentrated HCl (42 mL) dropwise maintaining internal temperature <15° C. The reaction mixture was allowed to warm up to ambient temperature, and filtered. The solid was wash with ethanol and the resulting cake was dried under nitrogen to afford the title compound.

Step 2: 1-cyclopropyl-N,N-bis(4-methoxybenzyl) methanesulfonamide

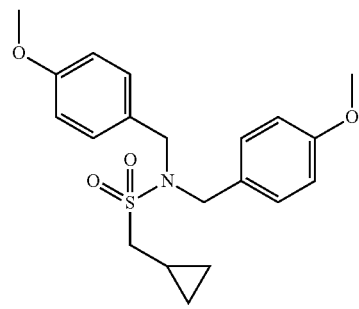 [SMILES: COc1ccc(CN(Cc2ccc(OC)cc2)S(=O)(=O)CC2CC2)cc1]

To a solution of bis(4-methoxybenzyl)amine (3.02 g, 11.74 mmol) and triethylamine (5.71 mL, 41.1 mmol) in CH₂Cl₂ (58.7 mL) at 0° C. was added cyclopropylmethanesulfonyl chloride (1.00 mL, 6.47 mmol) dropwise over 5 minutes. The cloudy mixture was stirred at 0° C. for 1 h and then diluted with CH₂Cl₂. The mixture was washed twice with brine. The aqueous layer was back extracted with EtOAc and the combined organic layers were dried (MgSO₄), and filtered. Solvent was evaporated, and the crude orange oil was chromatographed (silica gel, 0 to 60%, EtOAc/hexane) to afford the title compound (2.49 g, 56.5%). m/z (ESI, +ve ion) 398.2 (M+Na)⁺.

Step 3: 1-cyclopropyl-N,N-bis(4-methoxybenzyl) pent-4-ene-1-sulfonamide

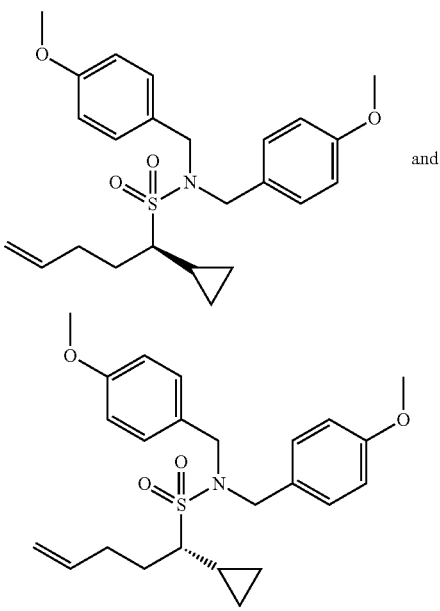

and

To a solution of 1-cyclopropyl-N,N-bis(4-methoxybenzyl)methanesulfonamide (2.10 g, 5.59 mmol) in THF (20 mL) was added butyllithium solution, 2.5 M in hexanes (2.461 mL, 6.15 mmol) at −78° C. dropwise. The reaction mixture was stirred at −78° C. for 10 min, and 4-bromo-1-butene (1.70 mL, 16.78 mmol) was added at this temperature. The reaction was stirred and then allowed to warm up to ambient temperature for 1 h. The mixture was quenched with saturated aqueous NH₄Cl, and extracted with EtOAc (2×). The organic layer was washed with brine, dried (Na₂SO₄) and filtered. The filtrate was concentrated and the resulting residue was chromatographed (SiO₂, 10 to 40%, EtOAc/hexane) to afford the title compound (2.0 g, 83%) as a colorless oil. m/z (ESI, +ve ion) 452.2 (M+Na)⁺.

Step 4: (1R)-1-cyclopropyl-4-pentene-1-sulfonamide and (1S)-1-cyclopropyl-4-pentene-1-sulfonamide

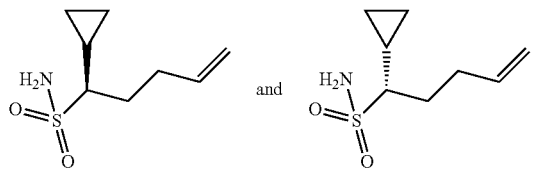

The title compounds were prepared from above mixture of (1R)-1-cyclopropyl-4-pentene-1-sulfonamide and (1S)-1-cyclopropyl-4-pentene-1-sulfonamide using a similar procedure described in Step 2 of Example 136.

Step 5: (3S)-6'-chloro-N-(((1R)-1-cyclopropyl-4-penten-1-yl)sulfonyl)-5-(((1R,2R)-2-((1S,2Z)-1-hydroxy-2-hexen-1-yl)cyclobutyl)methyl)-3',4,4',5-tetrahydro-2'H-spiro[1,5-benzoxazepine-3,1'-naphthalene]-7-carboxamide and (3S)-6'-chloro-N-(((1S)-1-cyclopropyl-4-penten-1-yl)sulfonyl)-5-(((1R,2R)-2-((1S,2Z)-1-hydroxy-2-hexen-1-yl)cyclobutyl)methyl)-3',4,4',5-tetrahydro-2'H-spiro[1,5-benzoxazepine-3,1'-naphthalene]-7-carboxamide

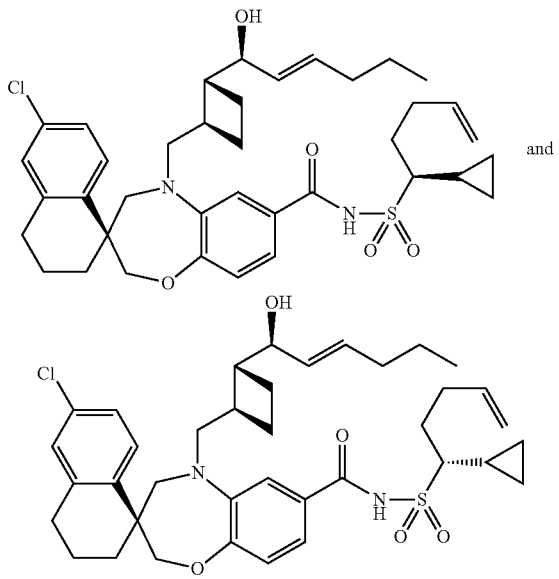

A mixture of (1R)-1-cyclopropyl-4-pentene-1-sulfonamide and (1S)-1-cyclopropyl-4-pentene-1-sulfonamide was added N,N-dimethylpyridin-4-amine (DMAP) (47.9 mg, 0.392 mmol), a solution of (S)-6'-chloro-5-(((1R,2R)-2-((S, E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A, 100 mg, 0.196 mmol) and triethylamine (0.082 mL, 0.588 mmol) in DCM (2 mL). N-(3-dimethylaminopropyl)-N'-ethylcarbodiimide hydrochloride (75 mg, 0.392 mmol) was added slowly at last. The reaction mixture was stirred at ambient temperature for 18 h and then quenched with aqueous 1.0 N HCl. The mixture was diluted with dichloromethane. The organic layer was washed with brine, dried (MgSO₄), and filtered. The filtrate was concentrated and the resulting residue was chromatographed (silica gel, 10 to 100%, EtOAc+1% HOAc/hexane) to afford the title compounds, 130 mg (97%). m/z (ESI, +ve ion) 681.3 (M+H)⁺.

Step 6: (1S,3'R,6'R,7'S,8'E,12'S)-6-chloro-12'-cyclopropyl-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,12'S)-6-chloro-12'-cyclopropyl-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide A round bottom flask was charged with a mixture of (3S)-6'-chloro-n-(((1R)-1-cyclopropyl-4-penten-1-yl)sulfonyl)-5-(((1R,2R)-2-((1S,2Z)-1-hydroxy-2-hexen-1-yl)cyclobutyl)methyl)-3',4,4',5-tetrahydro-2'H-spiro[1,5-benzoxazepine-3,1'-naphthalene]-7-carboxamide and (3S)-6'-chloro-n-(((1S)-1-cyclopropyl-4-penten-1-yl)sulfonyl)-5-(((1R,2R)-2-((1S,2Z)-1-hydroxy-2-hexen-1-yl)cyclobutyl)methyl)-3',4,4',5-tetrahydro-2'H-spiro[1,5-benzoxazepine-3,1'-naphthalene]-7-carboxamide (0.090 g, 0.132 mmol) in AcOH (46 mL). The mixture was stirred at ambient temperature and argon was sparged into the reaction flask for 30 min. To this homogeneous solution was added Hoveyda-Grubbs II (0.017 g, 0.026 mmol) and the mixture was stirred at ambient temperature under reduced pressure for 18 h. Solvent was evaporated and the residue was purified by reversed phase preparatory HPLC (Gemini™ Prep C₁₈ 5 μm column; Phenomenex, Torrance, CA; gradient elution of 25% to 75% MeCN in water, where both solvents contain 0.1% TFA, 30 min method) to afford the title compound as the first eluenting isomer. ¹H NMR (400 MHz, CD₂Cl₂) δ 8.16 (s, 1H), 7.70 (d, J=8.4 Hz, 1H), 7.17 (dd, J=2.2, 8.5 Hz, 1H), 7.09 (d, J=2.2 Hz, 1H), 6.90 (s, 2H), 6.85 (s, 1H), 5.82-5.68 (m, 2H), 4.22 (dd, J=3.9, 7.0 Hz, 1H), 4.07 (s, 2H), 3.82 (d, J=15.3 Hz, 1H), 3.70 (d, J=14.1 Hz, 1H), 3.39 (dt, J=2.7, 10.3 Hz, 1H), 3.24 (d, J=14.1 Hz, 1H), 3.02 (dd, J=9.7, 15.4 Hz, 1H), 2.82-2.69 (m, 2H), 2.53-2.27 (m, 4H), 2.06-1.90 (m, 4H), 1.88-1.60 (m, 6H), 1.39 (t, J=12.4 Hz, 1H), 1.05-0.96 (m, 1H), 0.90-0.74 (m, 3H), 0.44 (d, J=4.3 Hz, 1H). m/z (ESI, +ve ion) 611.3 (M+H)⁺.

Example 149. (1S,3'R,6'R,7'S,8'E,12'S)-6-chloro-12'-cyclopropyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'S)-6-chloro-12'-cyclopropyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide Example 150. (1S,3'R,6'R,11'S,12'S)-6-chloro-11',12'-dimethyl-3,4-dihydro-2H,9'H,15'H-spiro[naphthalene-1,22'-[20]oxa[13]thia[1,8,14]triazatetracyclo[14.7.2.0$^{3,6}$.0$^{19,24}$]pentacosa[16,18,24]triene]-9',1S-dione 13',13'-dioxide or (1S,3'R,6'R,11R,12'S)-6-chloro-11',12'-dimethyl-3,4-dihydro-2H,9'H,15'H-spiro[naphthalene-1,22'-[20]oxa[13]thia[1,8,14]triazatetracyclo [14.7.2.0$^{3,6}$.0$^{19,24}$]pentacosa[16,18,24]triene]-9',15'-dione 13',13'-dioxide or (1S,3'R,6'R,11'R,12'R)-6-chloro-11',12'-dimethyl-3,4-dihydro-2H,9'H,15'H-spiro[naphthalene-1,22'-[20]oxa[13]thia[1,8,14]triazatetracyclo [14.7.2.0$^{3,6}$.0$^{19,24}$]pentacosa[16,18,24]triene]-9',15'-dione 13',13'-dioxide or (1S,3'R,6'R,11'S,12'R)-6-chloro-11',12'-dimethyl-3,4-dihydro-2H,9'H,15'H-spiro[naphthalene-1,22'-[20]oxa[13]thia[1,8,14]triazatetracyclo [14.7.2.0$^{3,6}$.0$^{19,24}$]pentacosa[16,18,24]triene]-9',15'-dione 13',13'-dioxide

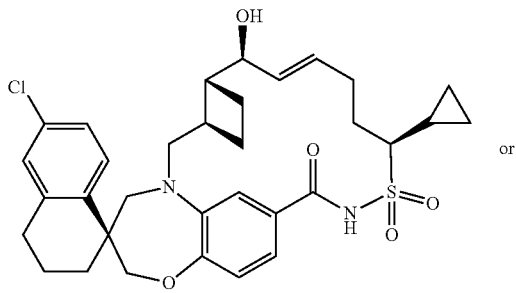

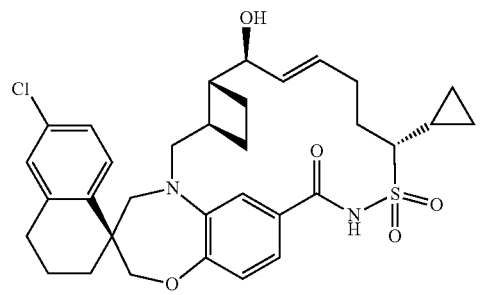

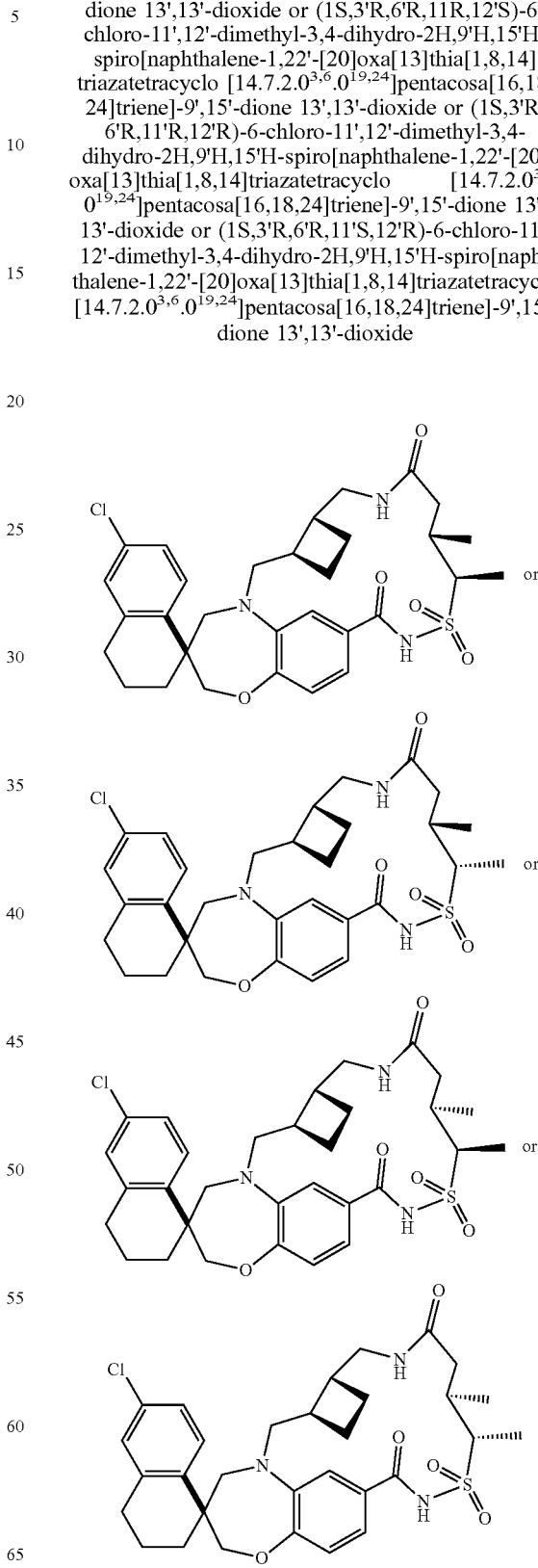

The title compound was obtained as the second eluenting isomer from the reversed phase preparatory HPLC separation in Example 148. $^1$H NMR (400 MHz, CD$_2$Cl$_2$) δ 9.33 (br s, 1H), 7.72 (d, J=8.6 Hz, 1H), 7.27 (dd, J=2.0, 8.2 Hz, 1H), 7.17 (dd, J=2.3, 8.6 Hz, 1H), 7.09 (d, J=2.3 Hz, 1H), 6.99-6.87 (m, 2H), 5.83-5.67 (m, 1H), 5.59 (dd, J=8.0, 11.0 Hz, 1H), 4.57 (dd, J=5.6, 7.3 Hz, 1H), 4.11 (s, 2H), 3.91 (d, J=15.3 Hz, 1H), 3.71 (d, J=14.3 Hz, 1H), 3.28 (d, J=14.3 Hz, 1H), 3.22-2.99 (m, 2H), 2.83-2.58 (m, 3H), 2.46-2.18 (m, 3H), 2.09-1.84 (m, 5H), 1.82-1.62 (m, 3H), 1.57-1.34 (m, 1H), 1.34-1.15 (m, 2H), 0.91-0.72 (m, 3H), 0.39-0.31 (m, 1H). m/z (ESI, +ve ion) 611.2 (M+H)$^+$.

Step 1: (2R,3R)-3-methylhex-5-en-2-ol and (2S,3S)-3-methyl-5-hexen-2-ol

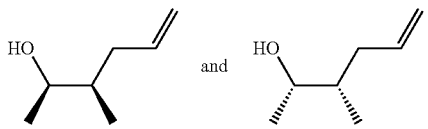

To a solution of (+/−)-trans-2,3-dimethyloxirane (8.74 mL, 97 mmol) in Et$_2$O (48.5 mL) at −30° C. was added copper (I) iodide (5.55 g, 29.1 mmol) at first and then allylmagnesium bromide, 1.0 N solution in diethyl ether (194 mL, 194 mmol) dropwise in 1 h. The reaction mixture was allowed to warm to ambient temperature and stirred for 18 h. The reaction was quenched with saturated aqueous ammonium chloride (300 mL), kept stirring for 1 h and extracted with ether (3×). The combined organic layers were dried (MgSO$_4$) and filtered. The filtrate was concentrated at 3° C. in a cold rotovap bath. The resulting residue was transferred to a smaller flask and distilled (137° C.) to afford the title compounds (10.1 g, 91%).

Step 2: 2-(((2S,3R)-3-methyl-5-hexen-2-yl)sulfanyl)pyrimidine and 2-(((2R,3S)-3-methyl-5-hexen-2-yl)sulfanyl)pyrimidine

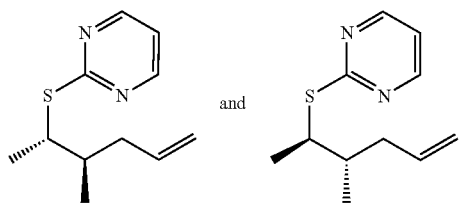

To a mixture of (2R,3R)-3-methylhex-5-en-2-ol and (2S,3S)-3-methyl-5-hexen-2-ol (10.0 g, 88 mmol) in Et$_2$O (175 mL) was added triethylamine (24.36 mL, 175 mmol) and methanesulfonyl chloride (7.45 mL, 96.0 mmol) at −78° C. The mixture was stirred and then allowed to warm up to ambient temperature. The solid was filtered off and washed with diethyl ether (×3). The filtrate was washed with 1.0 N HCl, brine, dried (MgSO$_4$), and concentrated. The resulting residue was dissolved in ethanol (60 mL) and added 21% sodium ethoxide in ethanol (36.0 mL, 96 mmol). Pyrimidine-2-thiol (10.80 g, 96 mmol) was added. The reaction mixture was stirred for 18 h at 50° C., concentrated, and then triturated in Et$_2$O. The crude residue was chromatographed (silica gel, 5 to 40%, EtOAc/hexane) to afford the title compounds (8.90 g, 48.8%) as a colorless oil. m/z (ESI, +ve ion) 209.2 (M+H)$^+$.

Step 3: 2-(((2S,3R)-3-methyl-5-hexen-2-yl)sulfonyl)pyrimidine and 2-(((2R,3S)-3-methyl-5-hexen-2-yl)sulfonyl)pyrimidine

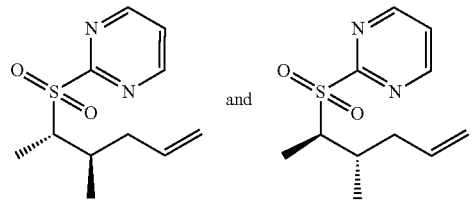 [SMILES: C=CC[C@@H](C)[C@H](C)S(=O)(=O)c1ncccn1 ; C=CC[C@H](C)[C@@H](C)S(=O)(=O)c1ncccn1]

To a flask charged with 2-(((2R,3S)-3-methylhex-5-en-2-yl)thio)pyrimidine (3.45 g, 16.56 mmol) in DCM (2 mL) was added 3-chloroperoxybenzoic acid, 77% max. (7.61 g, 33.9 mmol) at 0° C. The reaction was stirred at this temperature for 15 minutes and then was allowed to warm up to ambient temperature. The reaction was kept stirring for 18 h. The mixture was quenched with sodium bicarbonate (300 mL), and extracted with diethyl ether (3×200 mL). The combined organic layers were dried (MgSO$_4$), filtered and the filtrate was concentrated. The resulting residue was chromatographed (silica gel column, 0 to 100%, EtOAc/hexane) to afford the title compound (2.72 g, 68.3%) as an oil. m/z (ESI, +ve ion) 241.2 (M+H)$^+$.

Step 4: (3S,4R)-3-methyl-4-(pyrimidin-2-ylsulfonyl)pentanoic acid and (3S,4S)-3-methyl-4-(2-pyrimidinylsulfonyl) pentanoic acid and (3R,4S)-3-methyl-4-(2-pyrimidinylsulfonyl)pentanoic acid and (3R,4R)-3-methyl-4-(2-pyrimidinylsulfonyl) pentanoic acid

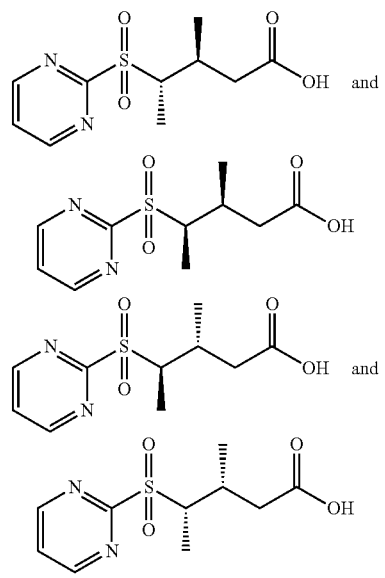

To a rapidly stirring solution of 2-(((2S,3R)-3-methyl-5-hexen-2-yl)sulfonyl)pyrimidine and 2-(((2R,3S)-3-methyl-5-hexen-2-yl)sulfonyl)pyrimidine (1.1 g, 5.28 mmol) in water (19.50 mL), acetonitrile (13.0 mL) and CCl$_4$ (13.0 mL) was added sodium periodate (13.55 g, 63.4 mmol). The reaction mixture was stirred vigorously at ambient tempera- Step 5: (S)-methyl 5-(((1R,2R)-2-(aminomethyl)cyclobutyl)methyl)-6'-chloro-3',4,4',5-tetrahydro-2H,2'H-spiro[benzo[b][1,4]oxazepine-3,1'-naphthalene]-7-carboxylate

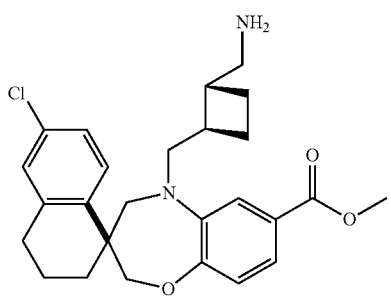 [SMILES: COC(=O)c1ccc2c(c1)N(C[C@@H]1CC[C@H]1CN)C[C@@]1(CCCc3cc(Cl)ccc31)CO2]

To a solution of ammonium acetate (0.949 mL, 13.22 mmol) and (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A, 300 mg, 0.661 mmol) in MeOH (1.322 mL) was added sodium cyanoborohydride (1.00 g, 1.00 mmol). The reaction was stirred for 18 h at 30° C. Solvent was evaporated to afford the title compound. m/z (ESI, +ve ion) 455.2 (M+H)$^+$.

Step 6: (3S)-6'-chloro-5-(((1R,2R)-2-(((((3R,4S)-3-methyl-4-(2-pyrimidinylsulfonyl)pentanoyl)amino)methyl)cyclobutyl)methyl)-3',4,4',5-tetrahydro-2'H-spiro[1,5-benzoxazepine-3,1'-naphthalene]-7-carboxylic acid and (3S)-6'-chloro-5-(((1R,2R)-2-(((((3R,4R)-3-methyl-4-(2-pyrimidinylsulfonyl)pentanoyl)amino)methyl)cyclobutyl)methyl)-3',4,4',5-tetrahydro-2'H-spiro[1,5-benzoxazepine-3,1'-naphthalene]-7-carboxylic acid and (3S)-6'-chloro-5-(((1R,2R)-2-(((((3S,4S)-3-methyl-4-(2-pyrimidinylsulfonyl)pentanoyl)amino)methyl)cyclobutyl)methyl)-3',4,4',5-tetrahydro-2'H-spiro[1,5-benzoxazepine-3,1'-naphthalene]-7-carboxylic acid and (3S)-6'-chloro-5-(((1R,2R)-2-(((((3S,4R)-3-methyl-4-(2-pyrimidinylsulfonyl)pentanoyl)amino)methyl)cyclobutyl)methyl)-3',4,4',5-tetrahydro-2'H-spiro[1,5-benzoxazepine-3,1'-naphthalene]-7-carboxylic acid

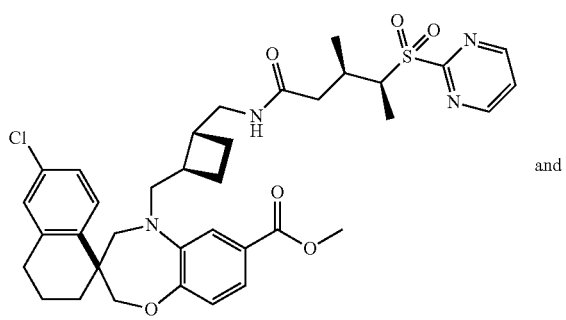
and

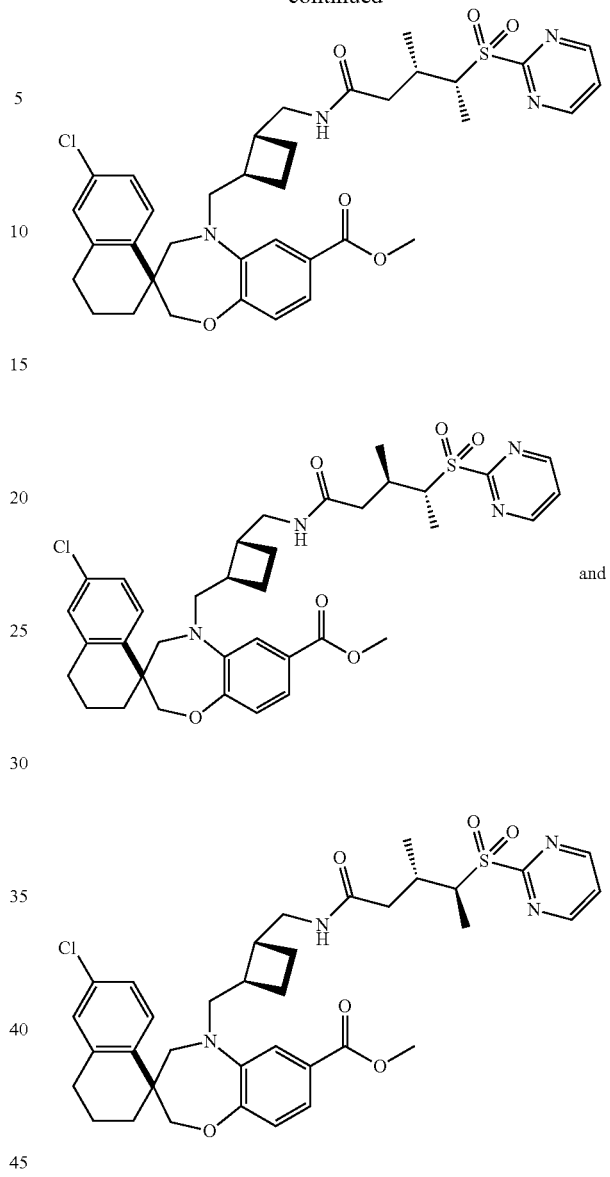
and

To a solution of (S)-methyl 5-(((1R,2R)-2-(aminomethyl)cyclobutyl)methyl)-6'-chloro-3',4,4',5-tetrahydro-2H,2'H-spiro[benzo[b][1,4]oxazepine-3,1'-naphthalene]-7-carboxylate (20 mg, 0.044 mmol) and a mixture of (3S,4R)-3-methyl-4-(pyrimidin-2-ylsulfonyl)pentanoic acid, (3S,4S)-3-methyl-4-(2-pyrimidinylsulfonyl)pentanoic acid, (3R,4S)-3-methyl-4-(2-pyrimidinylsulfonyl) pentanoic acid and (3R,4R)-3-methyl-4-(2-pyrimidinylsulfonyl)pentanoic acid (17.03 mg, 0.066 mmol) in DCM (2 mL) was added diisopropylethylamine (0.0593 mL, 0.341 mmol) and then 1-[bis(dimethylamino)methylene]-1h-benzotriazolium 3-oxide hexafluorophosphate (25.01 mg, 0.066 mmol). The reaction mixture was stirred at ambient temperature for 1 h. The mixture was diluted with DCM, washed with saturated sodium bicarbonate, dried (MgSO$_4$), and filtered. The filtrate was concentrated and the resulting residue was chromatographed (silica gel, 0 to 10%, MeOH/CH$_2$Cl$_2$) to afford the title compounds (20 mg, 65.4%) as a light-yellow oil. m/z (ESI, +ve ion) 717.2 (M+H)$^+$.

Step 7: Sodium (2S,3S)5-(((((1R,2R)-2-(((S)-6'-chloro-7-(methoxycarbonyl)-3',4'-dihydro-2H,2'H-spiro[benzo[b][1,4]oxazepine-3,1'-naphthalen]-5(4H)-yl)methyl)cyclobutyl)methyl)amino)-3-methyl-5-oxopentane-2-sulfinate and sodium (2S,3R)5-(((((1R,2R)-2-(((S)-6'-chloro-7-(methoxycarbonyl)-3',4'-dihydro-2H,2'H-spiro[benzo[b][1,4]oxazepine-3,1'-naphthalen]-5(4H)-yl)methyl)cyclobutyl)methyl)amino)-3-methyl-5-oxopentane-2-sulfinate and sodium (2R,3S)5-(((((1R,2R)-2-(((S)-6'-chloro-7-(methoxycarbonyl)-3',4'-dihydro-2H,2'H-spiro[benzo[b][1,4]oxazepine-3,1'-naphthalen]-5(4H)-yl)methyl)cyclobutyl)methyl)amino)-3-methyl-5-oxopentane-2-sulfinate and sodium (2R,3R)5-(((((1R,2R)-2-(((S)-6'-chloro-7-(methoxycarbonyl)-3',4'-dihydro-2H,2'H-spiro[benzo[b][1,4]oxazepine-3,1'-naphthalen]-5(4H)-yl)methyl)cyclobutyl)methyl)amino)-3-methyl-5-oxopentane-2-sulfinate

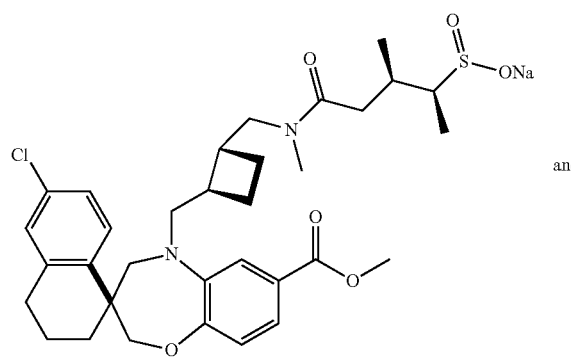

and

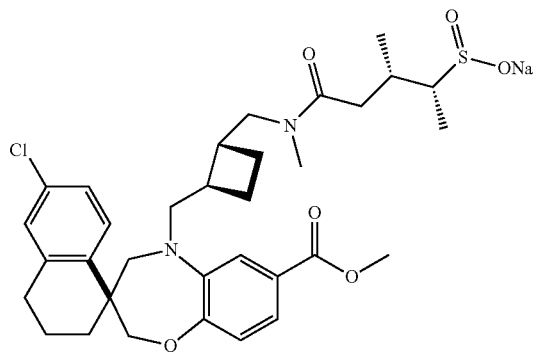

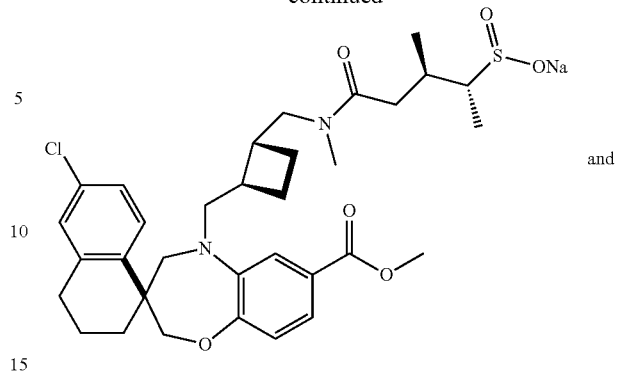

and

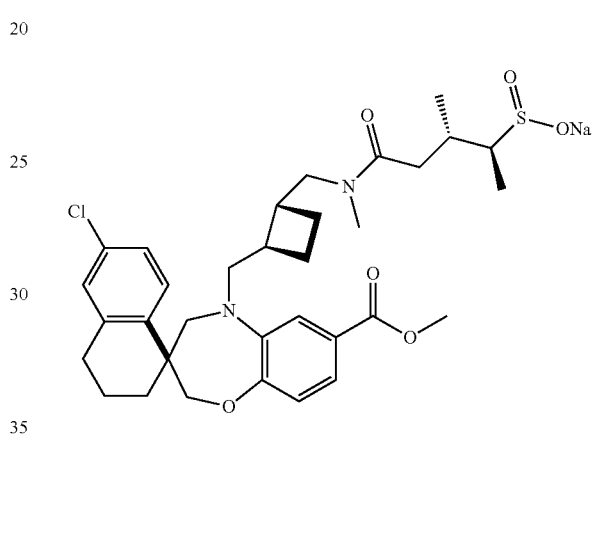

A solution of (3S)-6'-chloro-5-((((1R,2R)-2-(((((3R,4S)-3-methyl-4-(2-pyrimidinyl sulfonyl)pentanoyl)amino)methyl)cyclobutyl)methyl)-3',4,4',5-tetrahydro-2'h-spiro[1,5-benzoxazepine-3,1'-naphthalene]-7-carboxylic acid and (3S)-6'-chloro-5-((((1R,2R)-2-(((((3R,4R)-3-methyl-4-(2-pyrimidinylsulfonyl)pentanoyl)amino)methyl)cyclobutyl)methyl)-3',4,4',5-tetrahydro-2'h-spiro[1,5-benzoxazepine-3,1'-naphthalene]-7-carboxylic acid and (3S)-6'-chloro-5-((((1R,2R)-2-(((((3S,4S)-3-methyl-4-(2-pyrimidinylsulfonyl)pentanoyl)amino)methyl)cyclobutyl)methyl)-3',4,4',5-tetrahydro-2'H-spiro[1,5-benzoxazepine-3,1'-naphthalene]-7-carboxylic acid and (3S)-6'-chloro-5-((((1R,2R)-2-(((((3S,4R)-3-methyl-4-(2-pyrimidinyl sulfonyl)pentanoyl)amino)methyl)cyclobutyl)methyl)-3',4,4',5-tetrahydro-2'H-spiro[1,5-benzoxazepine-3,1'-naphthalene]-7-carboxylic acid (20 mg, 0.029 mmol) in MeOH (0.15 mL) was treated with sodium methoxide, 25 wt. % solution in methanol (0.0322 mL, 0.141 mmol). The reaction was stirred at ambient temperature for 1 h, then the solvent was evaporated and the resulting residue was taken into the next step without further purification.

Step 8: (3S)-6'-chloro-5-((((1R,2R)-2-((((3R,4R)-3-methyl-4-sulfamoylpentanoyl)amino)methyl)cyclobutyl)methyl)-3',4,4',5-tetrahydro-2'H-spiro[1,5-benzoxazepine-3,1'-naphthalene]-7-carboxylic acid and (3S)-6'-chloro-5-((((1R,2R)-2-((((3R,4S)-3-methyl-4-sulfamoylpentanoyl)amino)methyl)cyclobutyl)methyl)-3',4,4',5-tetrahydro-2'H-spiro[1,5-benzoxazepine-3,1'-naphthalene]-7-carboxylic acid and (3S)-6'-chloro-5-((((1R,2R)-2-((((3S,4S)-3-methyl-4-sulfamoylpentanoyl)amino)methyl)cyclobutyl)methyl)-3',4,4',5-tetrahydro-2'H-spiro[1,5-benzoxazepine-3,1'-naphthalene]-7-carboxylic acid and (3S)-6'-chloro-5-((((1S,2R)-2-((((3R,4S)-3-methyl-4-sulfamoylpentanoyl)amino)methyl)cyclobutyl)methyl)-3',4,4',5-tetrahydro-2'H-spiro[1,5-benzoxazepine-3,1'-naphthalene]-7-carboxylic acid

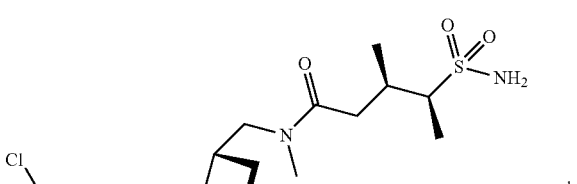

and

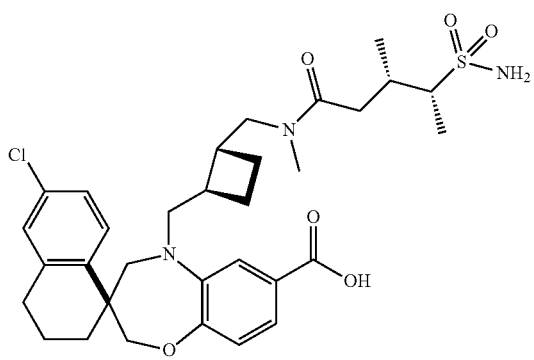

and

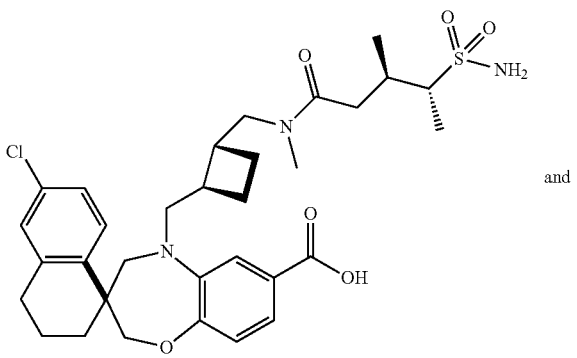

and

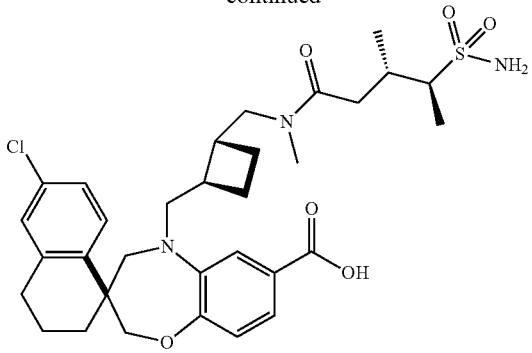

To a stirred solution of sodium (2S,3S)5-(((((1R,2R)-2-(((S)-6'-chloro-7-(methoxycarbonyl)-3',4'-dihydro-2H,2'H-spiro[benzo[b][1,4]oxazepine-3,1'-naphthalen]-5(4H)-yl)methyl)cyclobutyl)methyl)amino)-3-methyl-5-oxopentane-2-sulfinate and sodium (2S,30S-(((((1R,2R)-2-(((S)-6'-chloro-7-(methoxycarbonyl)-3',4'-dihydro-2H,2'H-spiro[benzo[b][1,4]oxazepine-3,1'-naphthalen]-5(4H)-yl)methyl)cyclobutyl)methyl)amino)-3-methyl-5-oxopentane-2-sulfinate and sodium (2R,3S)5-(((((1R,2R)-2-(((S)-6'-chloro-7-(methoxycarbonyl)-3',4'-dihydro-2H,2'H-spiro[benzo[b][1,4]oxazepine-3,1'-naphthalen]-5(4H)-yl)methyl)cyclobutyl)methyl)amino)-3-methyl-5-oxopentane-2-sulfinate and sodium (2R,3R)5-(((((1R,2R)-2-(((S)-6'-chloro-7-(methoxycarbonyl)-3',4'-dihydro-2H,2'H-spiro[benzo[b][1,4]oxazepine-3,1'-naphthalen]-5(4H)-yl)methyl)cyclobutyl)methyl)amino)-3-methyl-5-oxopentane-2-sulfinate (18 mg, 0.028 mmol) in water (0.860 mL) was added sodium acetate (4.62 mg, 0.056 mmol) and hydroxylamine-o-sulfonic acid (3.18 mg, 0.028 mmol). The reaction was stirred at ambient temperature for 18 h. The mixture was diluted with water and then extracted with diethyl ether (3×). The combined organic layers were dried (MgSO$_4$), and filtered. The filtrate was concentrated and the residual was added toluene to azeotropically remove water (×3). The resulting oil was taken to the next step without further purification.

Step 9: (1S,3'R,6'R,11'S,12'S)-6-chloro-11',12'-dimethyl-3,4-dihydro-2H,9'H,15'H-spiro[naphthalene-1,22'-[20]oxa[13]thia[1,8,14]triazatetracyclo[14.7.2.0$^{3,6}$.0$^{19,24}$]pentacosa[16,18,24]triene]-9',15'-dione 13',13'-dioxide or (1S,3'R,6'R,11'R,12'S)-6-chloro-11',12'-dimethyl-3,4-dihydro-2H,9'H,15'H-spiro[naphthalene-1,22'-[20]oxa[13]thia[1,8,14]triazatetracyclo [14.7.2.0$^{3,6}$.0$^{19,24}$]pentacosa[16,18,24]triene]-9',15'-dione 13',13'-dioxide or (1S,3'R,6'R,11R,12'R)-6-chloro-11',12'-dimethyl-3,4-dihydro-2H,9'H,15'H-spiro[naphthalene-1,22'-[20]oxa[13]thia[1,8,14]triazatetracyclo [14.7.2.0$^{3,6}$.0$^{19,24}$]pentacosa[16,18,24]triene]-9',15'-dione 13',13'-dioxide or (1S,3'R,6'R,11'S,12'R)-6-chloro-11',12'-dimethyl-3,4-dihydro-2H,9'H,15'H-spiro[naphthalene-1,22'-[20]oxa[13]thia[1,8,14]triazatetracyclo [14.7.2.0$^{3,6}$.0$^{19,24}$]pentacosa[16,18,24]triene]-9',15'-dione 13',13'-dioxide The title compound was prepared from a mixture of (3S)-6'-chloro-5-((((1R,2R)-2-((((3R,4R)-3-methyl-4-sulfamoylpentanoyl)amino)methyl)cyclobutyl)methyl)-3',4,4',5-tetrahydro-2'H-spiro[1,5-benzoxazepine-3,1'-naphthalene]-7-carboxylic acid, (3S)-6'-chloro-5-((((1R,2R)-2-((((3R,4S)-

3-methyl-4-sulfamoylpentanoyl)amino)methyl)cyclobutyl)
methyl)-3',4,4',5-tetrahydro-2'H-spiro[1,5-benzoxazepine-3,
1'-naphthalene]-7-carboxylic acid, (3S)-6'-chloro-5-(((1R,
2R)-2-((((3S,4S)-3-methyl-4-sulfamoylpentanoyl)amino)
methyl)cyclobutyl)methyl)-3',4,4',5-tetrahydro-2'H-spiro[1,
5-benzoxazepine-3,1'-naphthalene]-7-carboxylic acid and
(3S)-6'-chloro-5-(((1S,2R)-2-((((3R,4S)-3-methyl-4-sulfa-
moylpentanoyl)amino)methyl)cyclobutyl)methyl)-3',4,4',5-
tetrahydro-2'H-spiro[1,5-benzoxazepine-3,1'-naphthalene]-
7-carboxylic acid (0.011 g, 0.058 mmol) using a similar
procedure described in Step 3 of Example 144 and the
reversed phase preparatory HPLC purification (Gemini™
Prep $C_{18}$ 5 μm column; Phenomenex, Torrance, CA; gradi-
ent elution of 25% to 75% MeCN in water, where both
solvents contain 0.1% TFA, 30 min method) as the first
eluenting isomer. $^1$H NMR (400 MHz, $CD_2Cl_2$) δ 11.68 (br
s, ½ H), 10.79 (br s, ½ H), 7.73 (d, J=8.0 Hz, 1H), 7.43 (d,
J=2.0 Hz, ½ H), 7.38 (dd, J=8.4, 2.0 Hz, ½ H), 7.32-7.26 (m,
1H), 7.17 (d, J=8.4 Hz, 1H), 7.11-7.07 (m, 1H), 6.92 (t,
J=7.7 Hz, 1H), 6.04 (br s, ½ H), 5.89 (br s, ½ H), 4.13-4.06
(m, 1H), 3.99-3.87 (m, 1H), 3.82-3.68 (m, 2H), 3.65-3.57
(m, ½ H), 3.42-3.24 (m, 2H), 3.02-2.91 (m, 1H), 2.85-2.77
(m, ½ H), 2.73-2.65 (m, 2H), 2.65-2.46 (m, 2H), 2.46-2.06
(m, 2H), 2.08-1.81 (m, 5H), 1.80-1.72 (m, 3H), 1.31 (t, J=7.0
Hz, 3H), 1.30-1.21 (m, 2H), 1.09 (dd, J=4.0, 6.9 Hz, 3H).
m/z (ESI, +ve ion) 600.2 (M+H)$^+$.

Example 151. (1S,3'R,6'R,11'R,12'R)-6-chloro-11',
12'-dimethyl-3,4-dihydro-2H,9'H,15'H-spiro[naph-
thalene-1,22'-[20]oxa[13]thia[1,8,14]triazatetracyclo
[14.7.2.0$^{3,6}$.0$^{19,24}$]pentacosa[16,18,24]triene]-9',15'-
dione 13',13'-dioxide or (1S,3'R,6'R,11'R,12'S)-6-
chloro-11',12'-dimethyl-3,4-dihydro-2H,9'H,15'H-
spiro[naphthalene-1,22'-[20]oxa[13]thia[1,8,14]
triazatetracyclo [14.7.2.0$^{3,6}$.0$^{19,24}$]pentacosa[16,18,
24]triene]-9',15'-dione 13',13'-dioxide or (1S,3'R,
6'R,11'S,12'R)-6-chloro-11',12'-dimethyl-3,4-
dihydro-2H,9'H,15'H-spiro[naphthalene-1,22'-[20]
oxa[13]thia[1,8,14]triazatetracyclo [14.7.2.0$^{3,6}$.
0$^{19,24}$]pentacosa[16,18,24]triene]-9',15'-dione 13',
13'-dioxide or (1S,3'R,6'R,11'S,12'S)-6-chloro-11',
12'-dimethyl-3,4-dihydro-2H,9'H,15'H-spiro[naph-
thalene-1,22'-[20]oxa[13]thia[1,8,14]triazatetracyclo
[14.7.2.0$^{3,6}$.0$^{19,24}$]pentacosa[16,18,24]triene]-9',15'-
dione 13',13'-dioxide

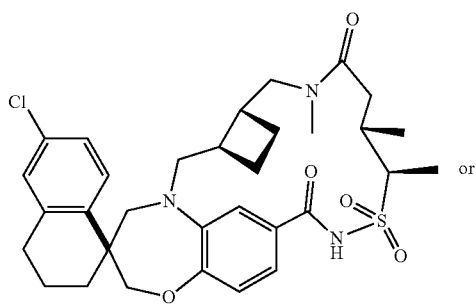 or

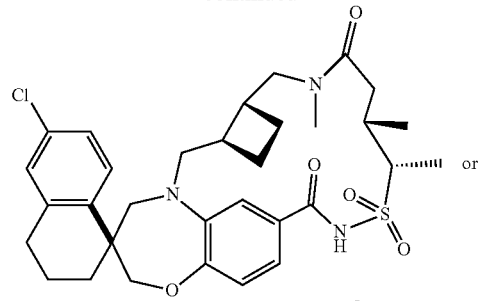 or

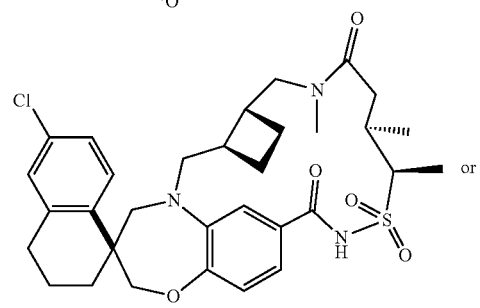 or

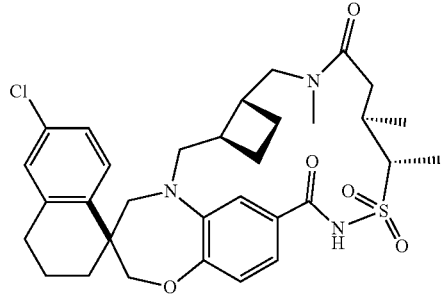

Step 1: (S)-methyl 6'-chloro-5-(((1R,2R)-2-((meth-
ylamino) methyl)cyclobutyl)methyl)-3',4,4',5-tetra-
hydro-2H,2'H-spiro[benzo[b][1,4]oxazepine-3,1'-
naphthalene]-7-carboxylate

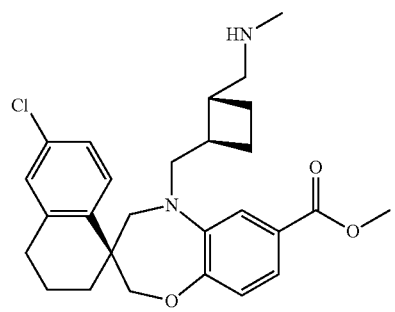 [SMILES: CNC[C@@H]1CC[C@H]1CN1C[C@@]2(CCCc3cc(Cl)ccc32)COc2ccc(C(=O)OC)cc21]

To a solution of (S)-methyl 6'-chloro-5-(((1R,2R)-2-form-
ylcyclobutyl)methyl)-3',4,4',5-tetrahydro-2H,2'H-spiro
[benzo[b][1,4]oxazepine-3,1'-naphthalene]-7-carboxylate
(Intermediate Intermediate AA11A, Step 20A, 190 mg,
0.419 mmol) in DCE (4 mL) was added 2.0 M methyl amine
solution in THF (2.51 mL, 5.02 mmol), sodium triacetoxy-
borohydride (532 mg, 2.51 mmol) and 3 drops of HOAc.
The reaction mixture was quenched with water and extracted
with diethyl ether. The organic layer was washed with brine, dried (MgSO₄) and concentrated. The residue was chromatographed (silica gel, 0 to 10%, MeOH/CH₂Cl₂) to afford the title compound.

Step 2: (S)-methyl 6'-chloro-5-(((1R,2R)-2-(43R,4S)—N,3-dimethyl-4-(pyrimidin-2ylsulfonyl)pentanamido)methyl) cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-(((3R,4R)—N,3-dimethyl-4-(pyrimidin-2ylsulfonyl)pentanamido)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-(((3S,4S)—N,3-dimethyl-4-(pyrimidin-2ylsulfonyl)pentanamido)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-(((3S,4R)—N,3-dimethyl-4-(pyrimidin-2ylsulfonyl)pentanamido)methyl)cyclobutyl)methyl)-3',4,4',5-tetrahydro-2H,2'H-spiro[benzo[b][1,4]oxazepine-3,1'-naphthalene]-7-carboxylate

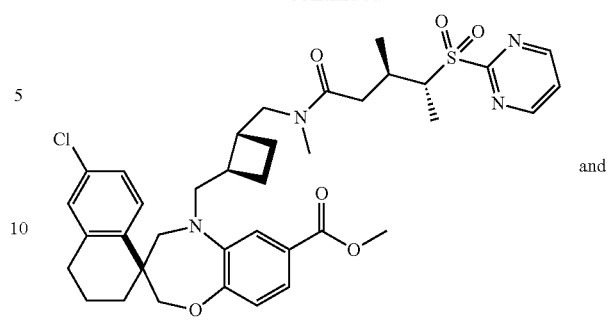

and

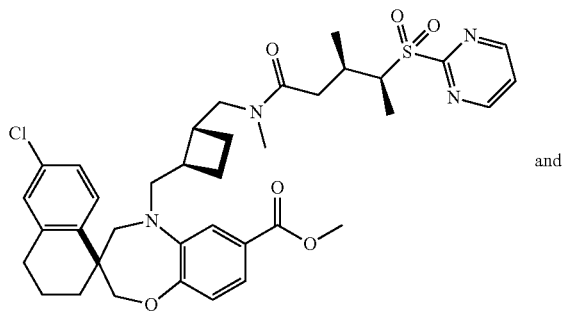

and

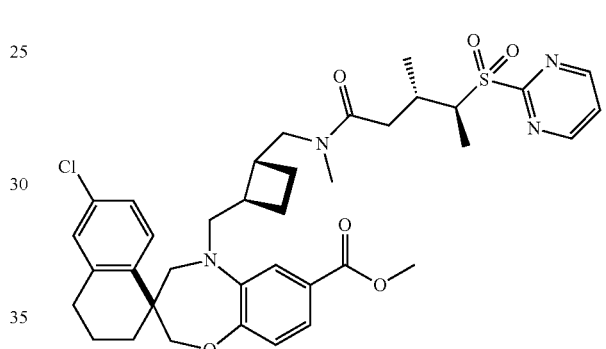

and

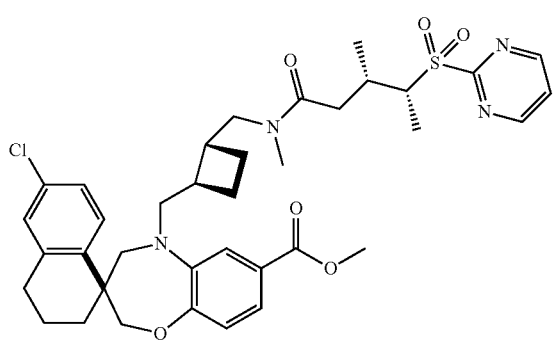

To a solution of (3S,4R)-3-methyl-4-(pyrimidin-2-ylsulfonyl)pentanoic acid and (3S,4S)-3-methyl-4-(2-pyrimidinylsulfonyl) pentanoic acid, (3R,4S)-3-methyl-4-(2-pyrimidinylsulfonyl)pentanoic acid, (3R,4R)-3-methyl-4-(2-pyrimidinylsulfonyl)pentanoic acid (From Example 140, Step 4, 66.1 mg, 0.256 mmol) and (S)-methyl 6'-chloro-5-(((1R,2R)-2-((methylamino)methyl)cyclobutyl)methyl)-3',4,4',5-tetrahydro-2H,2'H-spiro[benzo[b][1,4]oxazepine-3,1'-naphthalene]-7-carboxylate (80 mg, 0.171 mmol) in DCM (2 mL) was added diisopropyl ethylamine (0.0593 mL, 0.341 mmol) and then 1-[bis(dimethylamino)methylene]-1h-benzotriazolium 3-oxide hexafluorophosphate (97 mg, 0.256 mmol). The reaction was allowed to stir at ambient temperature for 1 h. the mixture was diluted with DCM, washed with saturated sodium bicarbonate. The organic layer was dried (MgSO₄), filtered and concentrated. The crude residue was chromatographed (silica gel, 0 to 10%, MeOH/CH₂Cl₂) to afford the title compound (100 mg, 83%) as a light yellow oil. m/z (ESI, +ve ion) 709.2 (M+H)⁺.

531

Step 3: Sodium (2S,3R)-5-((((1R,2R)-2-(((S)-6'-chloro-7-(methoxycarbonyl)-3',4'-dihydro-2H,2'H-spiro[benzo[b][1,4]oxazepine-3,1'-naphthalen]-5(4H)-yl)methyl)cyclobutyl)methyl)(methyl)amino)-3-methyl-5-oxopentane-2-sulfinate and sodium (2R,3R)-5-((((1R,2R)-2-(((S)-6'-chloro-7-(methoxycarbonyl)-3',4'-dihydro-2H,2'H-spiro[benzo[b][1,4]oxazepine-3,1'-naphthalen]-5(4H)-yl)methyl)cyclobutyl)methyl)(methyl)amino)-3-methyl-5-oxopentane-2-sulfinate and sodium (2S,3S)-5-((((1R,2R)-2-(((S)-6'-chloro-7-(methoxycarbonyl)-3',4'-dihydro-2H,2'H-spiro[benzo[b][1,4]oxazepine-3,1'-naphthalen]-5(4H)-yl)methyl)cyclobutyl)methyl)(methyl)amino)-3-methyl-5-oxopentane-2-sulfinate and sodium (2R,3S)-5-((((1R,2R)-2-(((S)-6'-chloro-7-(methoxycarbonyl)-3',4'-dihydro-2H,2'H-spiro[benzo[b][1,4]oxazepine-3,1'-naphthalen]-5(4H)-yl)methyl)cyclobutyl)methyl)(methyl)amino)-3-methyl-5-oxopentane-2-sulfinate

532

-continued

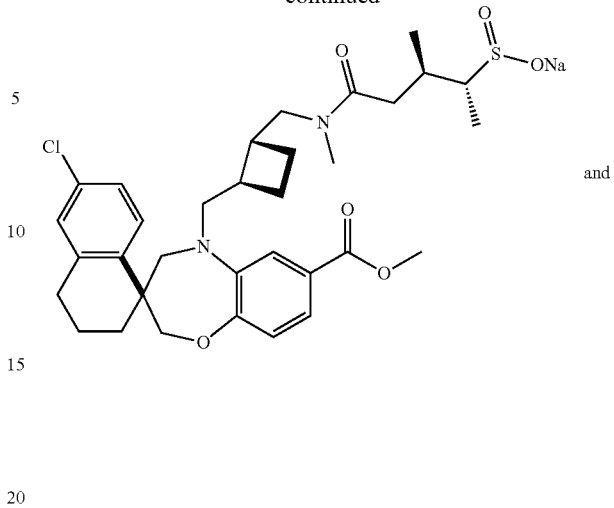

and

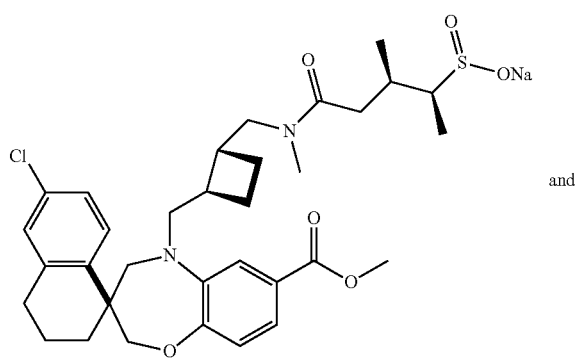

and

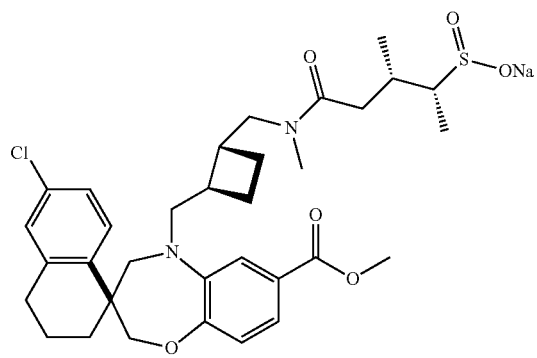

A solution of (S)-methyl 6'-chloro-5-(((1R,2R)-2-(43R,4S)—N,3-dimethyl-4-(pyrimidin-2ylsulfonyl)pentanamido)methyl)cyclobutyl)methyl)-3',4,4',5-tetrahydro-2H,2'H-spiro[benzo[b][1,4]oxazepine-3,1'-naphthalene]-7-carboxylate and (s)-methyl 6'-chloro-5-(((1R,2R)-2-(((3R,4R)—N,3-dimethyl-4-(pyrimidin-2ylsulfonyl)pentanamido)methyl)cyclobutyl)methyl)-3',4,4',5-tetrahydro-2H,2'H-spiro[benzo[b][1,4]oxazepine-3,1'-naphthalene]-7-carboxylate and (s)-methyl 6'-chloro-5-(((1R,2R)-2-(((3S,4S)—N,3-dimethyl-4-(pyrimidin-2ylsulfonyl)pentanamido)methyl)cyclobutyl)methyl)-3',4,4',5-tetrahydro-2H,2'H-spiro[benzo[b][1,4]oxazepine-3,1'-naphthalene]-7-carboxylate and (s)-methyl 6'-chloro-5-(((1R,2R)-2-(((3S,4R)—N,3-dimethyl-4-(pyrimidin-2ylsulfonyl) pentanamido)methyl)cyclobutyl)methyl)-3',4,4',5-tetrahydro-2H,2'H-spiro[benzo[b][1,4]oxazepine-3,1'-naphthalene]-7-carboxylate (100 mg, 0.141 mmol) in MeOH (1 mL) was treated with sodium methoxide, 25 wt. % solution in methanol (0.0322 mL, 0.141 mmol) and the mixture was stirred at ambient temperature for 1 h. Solvent was evaporated and the resulting residue was obtained as the title compound and was used without further purification.

Step 4: (S)-methyl 6'-chloro-5-((((1R,2R)-2-(((3R,4S)—N,3-dimethyl-4-sulfamoylpentanamido)methyl)cyclobutyl)methyl)-3',4',5-tetrahydro-2H,2'H-spiro[benzo[b][1,4]oxazepine-3,1'-naphthalene]-7-carboxylate and (S)-methyl 6'-chloro-5-((((1R,2R)-2-(((3S,4R)—N,3-dimethyl-4-sulfamoylpentanamido)methyl)cyclobutyl)methyl)-3',4',5-tetrahydro-2H,2'H-spiro[benzo[b][1,4]oxazepine-3,1'-naphthalene]-7-carboxylate and (S)-methyl 6'-chloro-5-((((1R,2R)-2-(((3R,4R)—N,3-dimethyl-4-sulfamoylpentanamido)methyl)cyclobutyl)methyl)-3',4',5-tetrahydro-2H,2'H-spiro[benzo[b][1,4]oxazepine-3,1'-naphthalene]-7-carboxylate and (S)-methyl 6'-chloro-5-((((1R,2R)-2-(((3S,4S)—N,3-dimethyl-4-sulfamoylpentanamido)methyl)cyclobutyl)methyl)-3',4',5-tetrahydro-2H,2'H-spiro[benzo[b][1,4]oxazepine-3,1'-naphthalene]-7-carboxylate

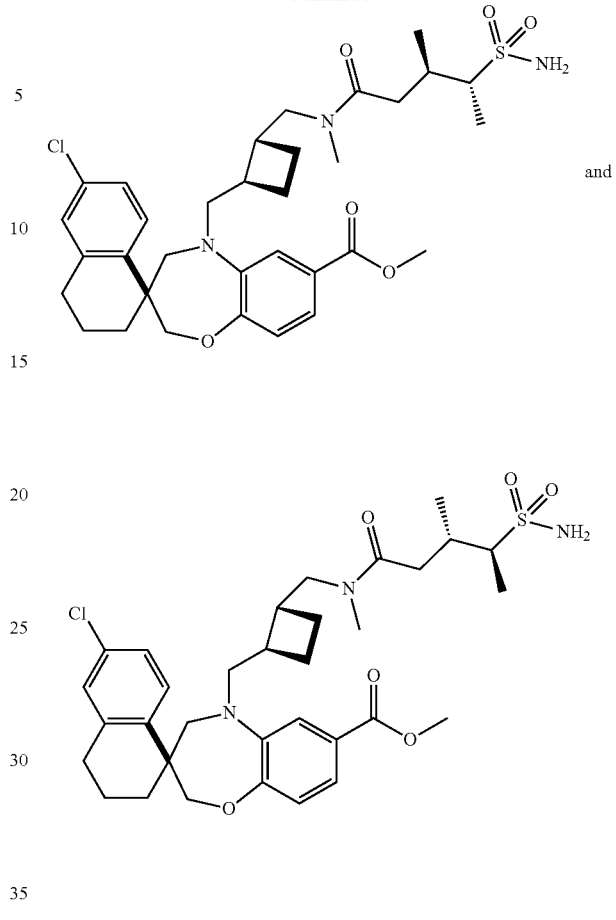

and

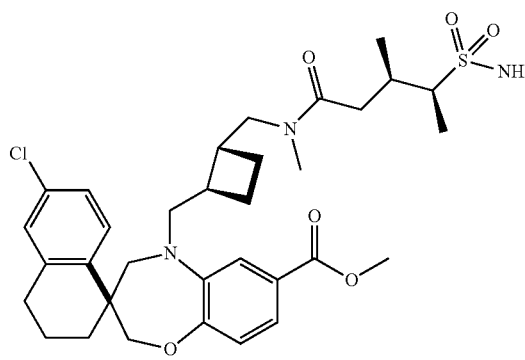

and

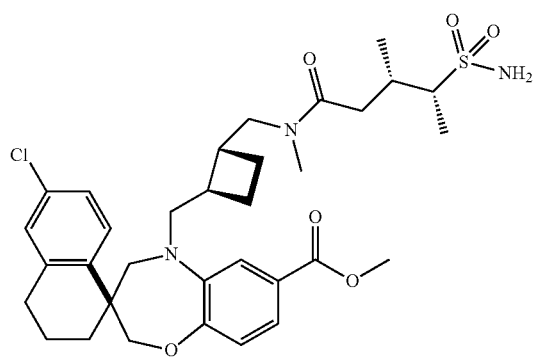

To a stirred solution of sodium (2S,3R)-5-(((((1R,2R)-2-(((S)-6'-chloro-7-(methoxycarbonyl)-3',4'-dihydro-2H,2'H-spiro[benzo[b][1,4]oxazepine-3,1'-naphthalen]-5(4H)-yl)methyl)cyclobutyl)methyl)(methyl)amino)-3-methyl-5-oxopentane-2-sulfinate and sodium (2R,3R)-5-(((((1R,2R)-2-(((S)-6'-chloro-7-(methoxycarbonyl)-3',4'-dihydro-2H,2'H-spiro[benzo[b][1,4]oxazepine-3,1'-naphthalen]-5(4H)-yl)methyl)cyclobutyl)methyl)(methyl)amino)-3-methyl-5-oxopentane-2-sulfinate and sodium (2S,3S)-5-(((((1R,2R)-2-(((S)-6'-chloro-7-(methoxycarbonyl)-3',4'-dihydro-2H,2'H-spiro[benzo[b][1,4]oxazepine-3,1'-naphthalen]-5(4H)-yl)methyl)cyclobutyl)methyl) (methyl)amino)-3-methyl-5-oxopentane-2-sulfinate and sodium (2R,3S)-5-(((((1R,2R)-2-(((S)-6'-chloro-7-(methoxycarbonyl)-3',4'-dihydro-2H,2'H-spiro[benzo[b][1,4]oxazepine-3,1'-naphthalen]-5(4H)-yl)methyl)cyclobutyl)methyl)(methyl)amino)-3-methyl-5-oxopentane-2-sulfinate (92 mg, 0.141 mmol) in water (0.860 mL) was added sodium acetate (23.11 mg, 0.282 mmol) and hydroxylamine-o-sulfonic acid (15.93 mg, 0.141 mmol). The reaction mixture was stirred at ambient temperature for 17 h. The mixture was then treated with aqueous 15% NaOH, and extracted with EtOAc (×2). The combined organic layers were dried (MgSO₄) and filtered. The filtrate was concentrated to afford the title compound (91 mg, 100%) which was used without further purification.

Step 5: (S)-6'-chloro-5-(((1R,2R)-2-(((3R,4S)—N,3-dimethyl-4-sulfamoyl pentanamido)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-(((3S,4S)—N,3-dimethyl-4-sulfamoyl pentanamido)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-(((3R,4R)—N,3-dimethyl-4-sulfamoyl pentanamido)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-(((3S,4R)—N,3-dimethyl-4-sulfamoyl pentanamido)methyl)cyclobutyl)methyl)-3',4,4',5-tetrahydro-2H,2'H-spiro[benzo[b][1,4]oxazepine-3,1'-naphthalene]-7-carboxylic acid

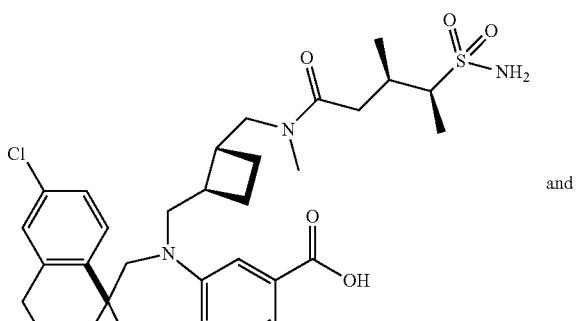

and

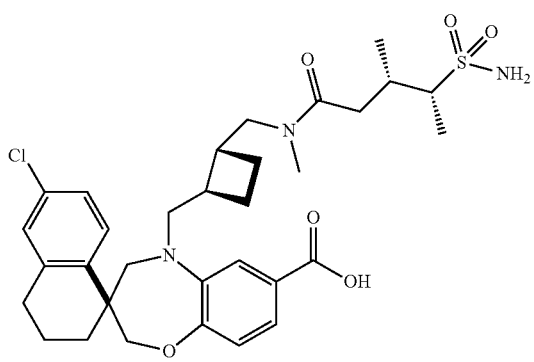

and

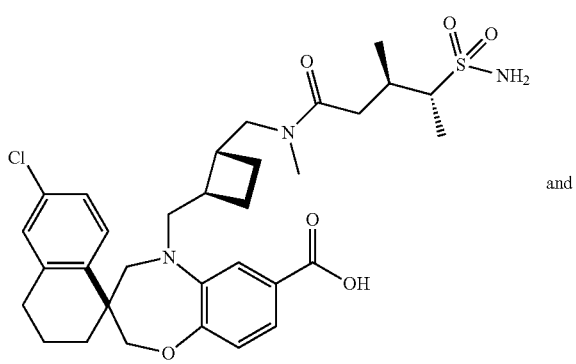

and

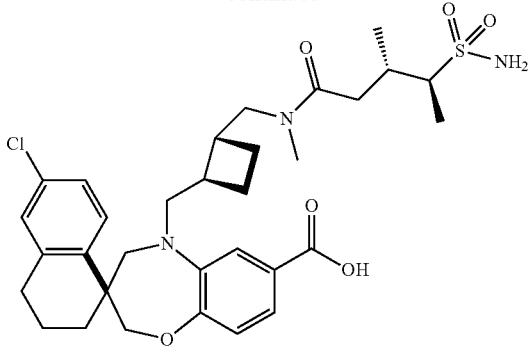

To a solution of (S)-methyl 6'-chloro-5-(((1R,2R)-2-(((3R,4S)—N,3-dimethyl-4-sulfamoylpentanamido)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-(((3S,4R)—N,3-dimethyl-4-sulfamoylpentanamido)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-(((3R,4R)—N,3-dimethyl-4-sulfamoylpentanamido)methyl) cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-(((3S,4S)—N,3-dimethyl-4-sulfamoyl pentanamido)methyl)cyclobutyl)methyl)-3',4,4',5-tetrahydro-2H,2'H-spiro[benzo[b][1,4]oxazepine-3,1'-naphthalene]-7-carboxylate and (92 mg, 0.142 mmol) in THF (1 mL) and MeOH (1 mL) was added aqueous 2.0 N LiOH (2 mL). The reaction mixture was stirred at 50° C. for 1 h. The mixture was neutralized with 1.0 N HCl, and extracted with diethyl ether. The organic layer was dried (MgSO$_4$), and filtered and the filtrate was concentrated. The crude residue was used for the next step without further purification.

Step 6: (1S,3'R,6'R,11R,12'R)-6-chloro-11',12'-dimethyl-3,4-dihydro-2H,9'H,15'H-spiro[naphthalene-1,22'-[20]oxa[13]thia[1,8,14]triazatetracyclo [14.7.2.0$^{3,6}$.0$^{19,24}$]pentacosa[16,18,24]triene]-9',15'-dione 13',13'-dioxide or (1S,3'R,6'R,11R,12'S)-6-chloro-11',12'-dimethyl-3,4-dihydro-2H,9'H,15'H-spiro[naphthalene-1,22'-[20]oxa[13]thia[1,8,14]triazatetracyclo [14.7.2.0$^{3,6}$.0$^{19,24}$]pentacosa[16,18,24]triene]-9',15'-dione 13',13'-dioxide or (1S,3'R,6'R,11S,12'R)-6-chloro-11',12'-dimethyl-3,4-dihydro-2H,9'H,15'H-spiro[naphthalene-1,22'-[20]oxa[13]thia[1,8,14]triazatetracyclo [14.7.2.0$^{3,6}$.0$^{19,24}$]pentacosa[16,18,24]triene]-9',15'-dione 13',13'-dioxide or (1S,3'R,6'R,11'S,12'S)-6-chloro-11',12'-dimethyl-3,4-dihydro-2H,9'H,15'H-spiro[naphthalene-1,22'-[20]oxa[13]thia[1,8,14]triazatetracyclo [14.7.2.0$^{3,6}$.0$^{19,24}$]pentacosa[16,18,24]triene]-9',15'-dione 13',13'-dioxide N,N-dimethylpyridin-4-amine (9.66 mg, 0.079 mmol) was added to a solution of (1'S)-6'-chloro-5-(((1R,2R)-2-((N,3-dimethyl-4-sulfamoylpentanamido)methyl)cyclobutyl)methyl)-3',4,4',5-tetrahydro-2H,2'H-spiro[benzo[b][1,4]oxazepine-3,1'-naphthalene]-7-carboxylic acid and triethylamine (0.082 mL, 0.592 mmol) in DCM (2 mL) at ambient temperature. The mixture was then added N1-((ethylimino)methylene)-N3,N3-dimethylpropane-1,3-diamine hydrochloride (0.015 g, 0.079 mmol) slowly and stirred at ambient temperature for 17 h. The reaction mixture was diluted with dichloromethane and quenched with 1.0 N HCl. The combined organic layers were washed with brine, dried (MgSO₄), filtered and concentrated. The crude residue was purified by reversed phase preparatory HPLC (Gemini™ Prep C₁₈ 5 µm column; Phenomenex, Torrance, CA; gradient elution of 25% to 75% MeCN in water, where both solvents contain 0.1% TFA, 30 min method) to afford the title compound as the first eluenting isomer. ¹H NMR (400 MHz, CD₂Cl₂) δ 11.58 (br s, 1H), 7.73 (dd, J=2.9, 8.6 HZ, Hz, 1H), 7.48 (d, J=5.2 Hz, 1H), 7.38 (dd, J=2.2, 8.2 Hz, 1H), 7.16 (dd, J=2.4, 9.8 Hz, 1H), 7.08 (d, J=5.5 Hz, 1H), 6.90 (dd, J=4.5, 8.2 Hz, 1H), 4.17-3.98 (m, 3H), 3.87 (d, J=15.8 Hz, 1H), 3.70 (d, J=14.9 Hz, 1H), 3.50 (d, J=7.4 Hz, 1H), 3.38 (d, J=14.7 Hz, 1H), 3.09 (dd, J=10.4, 15.3 Hz, 1H), 3.01-2.96 (m, 2H), 2.90-2.66 (m, 3H), 2.64-2.26 (m, 3H), 2.25-1.96 (m, 4H), 1.96 (m, 10H), 1.19-1.01 (m, 3H), 0.99-0.76 (m, 3H). m/z (ESI, +ve ion) 615.2 (M+H)⁺.

Example 152. (1S,3'R,6'R,11R,12'R)-6-chloro-11',12'-dimethyl-3,4-dihydro-2H,9'H,15'H-spiro[naphthalene-1,22'-[20]oxa[13]thia[1,8,14]triazatetracyclo[14.7.2.0³,⁶.0¹⁹,²⁴]pentacosa[16,18,24]triene]-9',15'-dione 13',13'-dioxide or (1S,3'R,6'R,11R,12'S)-6-chloro-11',12'-dimethyl-3,4-dihydro-2H,9'H,15'H-spiro[naphthalene-1,22'-[20]oxa[13]thia[1,8,14]triazatetracyclo [14.7.2.0³,⁶.0¹⁹,²⁴]pentacosa[16,18,24]triene]-9',15'-dione 13',13'-dioxide or (1S,3'R,6'R,11S,12'R)-6-chloro-11',12'-dimethyl-3,4-dihydro-2H,9'H,15'H-spiro[naphthalene-1,22'-[20]oxa[13]thia[1,8,14]triazatetracyclo [14.7.2.0³,⁶.0¹⁹,²⁴]pentacosa[16,18,24]triene]-9',15'-dione 13',13'-dioxide or (1S,3'R,6'R,11'S,12'S)-6-chloro-11',12'-dimethyl-3,4-dihydro-2H,9'H,15'H-spiro[naphthalene-1,22'-[20]oxa[13]thia[1,8,14]triazatetracyclo[14.7.2.0³,⁶.0¹⁹,²⁴]pentacosa[16,18,24]triene]-9',15'-dione 13',13'-dioxide

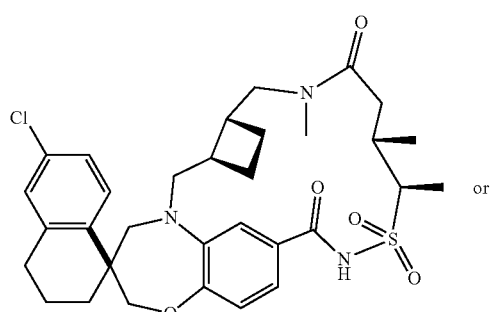 or

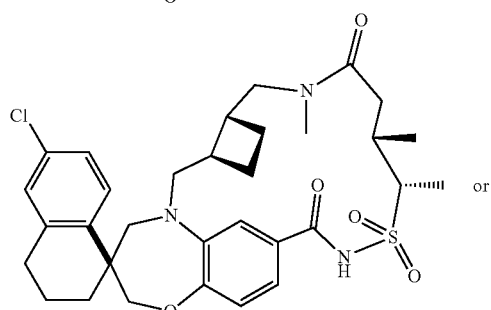 or

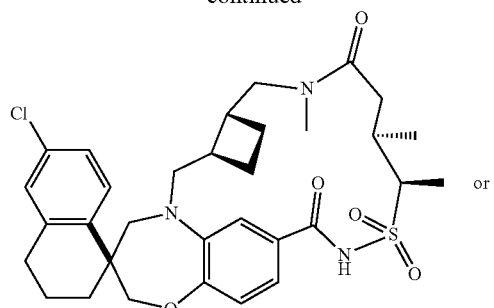 or

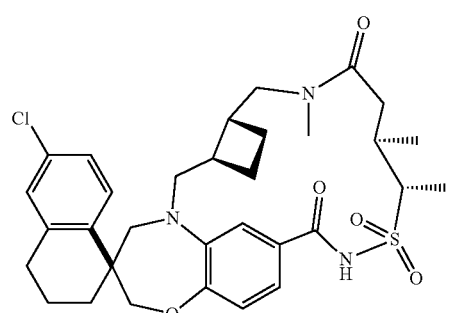

The title compound was obtained as the second eluting isomer from the reversed phase preparatory HPLC separation in Example 141. ¹H NMR (400 MHz, C₆D₆) δ=9.59 (d, J=8.6 Hz, 1H), 9.42 (d, J=5.9 Hz, 1H), 9.35 (dd, J=2.1, 8.3 Hz, 1H), 9.03 (dd, J=2.2, 8.4 Hz, 1H), 8.93 (dd, J=1.6, 6.0 Hz, 1H), 8.78 (d, J=8.2 Hz, 1H), 5.98-5.84 (m, 2H), 5.78-5.62 (m, 2H), 5.51 (d, J=15.3 Hz, 1H), 5.25-5.06 (m, 2H), 4.84-4.74 (m, 4H), 4.68-4.56 (m, 3H), 4.43 (d, J=13.9 Hz, 1H), 4.36-4.17 (m, 2H), 4.07 (t, J=7.6 Hz, 1H), 4.00-3.00 (m, 12H), 2.95 (t, J=7.0 Hz, 3H). m/z (ESI, +ve ion) 615.2 (M+H)⁺.

Example 153. (1S,3'R,6'R,7'S,8'Z,12'S)-6-chloro-7'-hydroxy-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraene]-12'-carbonitrile 13',13'-dioxide or (1S,3'R,6'R,7'S,8'Z,12'R)-6-chloro-7'-hydroxy-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraene]-12'-carbonitrile 13',13'-dioxide

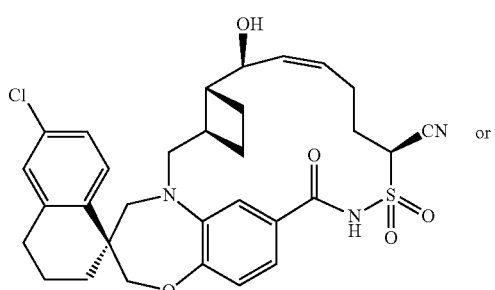 or

539

-continued

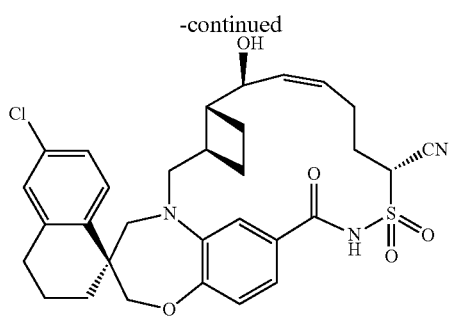

Step 1: methyl(2S)—(N,N-bis(4-methoxybenzyl)
sulfamoyl)hex-5-enoate and methyl(2R)—(N,N-bis
(4-methoxybenzyl)sulfamoyl)hex-5-enoate

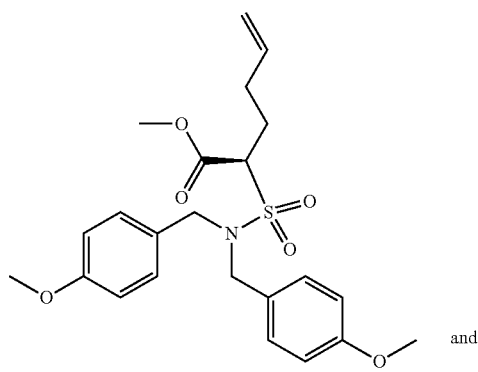

and

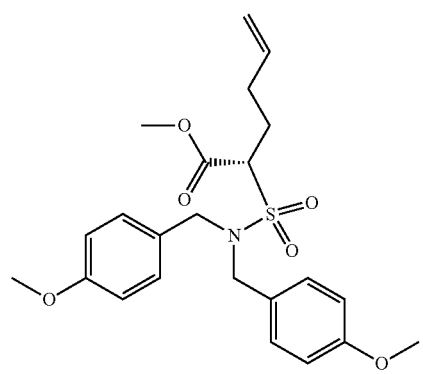

To a round bottom flask was added N,N-bis(4-methoxy-benzyl)pent-4-ene-1-sulfonamide (EE19, 3.40 g, 8.73 mmol) in THF (34.9 mL) at −78° C., butyllithium solution, 2.5 M in hexanes (3.84 mL, 9.60 mmol), and followed by the addition of chlorocarbonic acid, methyl ester (1.01 mL, 13.09 mmol) after stirring for 5 min. The reaction mixture was stirred and then allowed to warm up to ambient temperature. The mixture was quenched with saturated aqueous NH₄Cl, and extracted with diethyl ether (2×). The combined organic extracts were washed with brine, dried (MgSO₄), and filtered. The filtrate was concentrated to afford the title compound as a colorless oil without further purification.

540

Step 2: (2S)—(N,N-bis(4-methoxybenzyl)sulfa-
moyl)hex-5-enoic acid and (2R)—(N,N-bis(4-
methoxybenzyl)sulfamoyl)hex-5-enoic acid

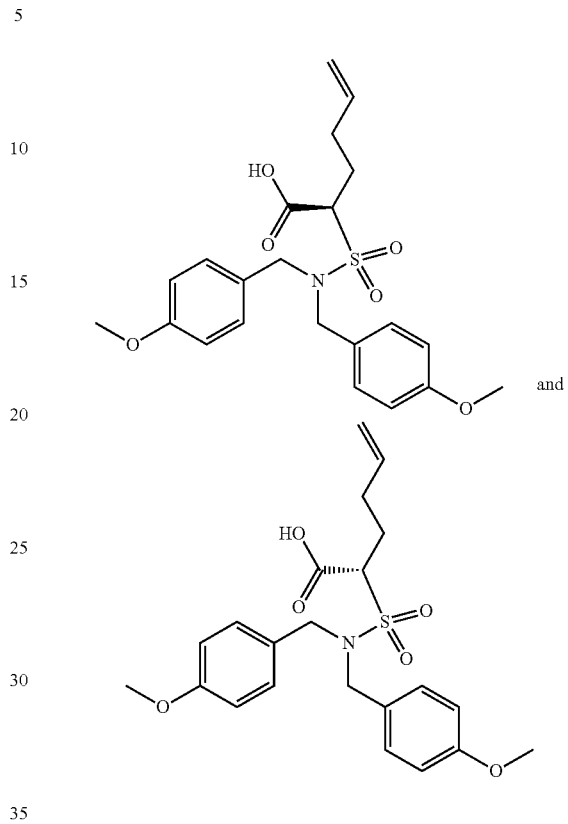

and

To a round bottom flask was added methyl 2-(N,N-bis(4-methoxybenzyl)sulfamoyl)hex-5-enoate (3.90 g, 8.71 mmol) in THF (36.3 mL), sodium hydroxide (1.39 g, 34.9 mmol) in water (7.26 mL). The reaction mixture was stirred at 50° C. for 18 h. The reaction was neutralized with 1.0 N HCl, extracted with EtOAc (2×). The organic extract was washed with brine, dried (MgSO₄), and filtered. The filtrate was concentrated and chromatographed (silica gel, 0 to 100% EtOAc+0.3% HOAc/hexane) to afford the title compound (2.60 g, 69%).

Step 3: (2S)—(N,N-bis(4-methoxybenzyl)sulfa-
moyl)hex-5-enamide and (2R)—(N,N-bis(4-
methoxybenzyl)sulfamoyl)hex-5-enamide

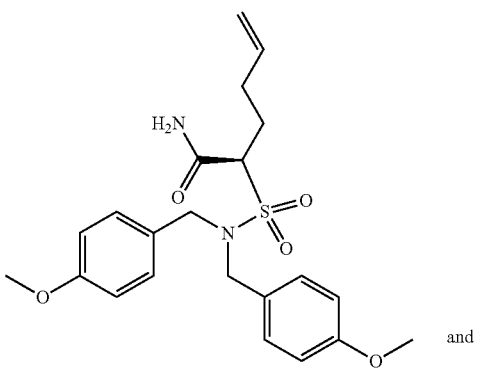

and

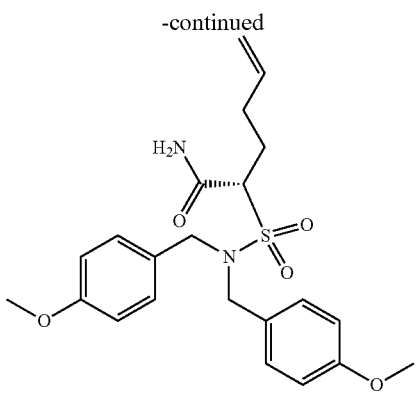

To a solution of 2-(N,N-bis(4-methoxybenzyl)sulfamoyl)hex-5-enoic acid (1.00 g, 2.31 mmol), and N,N-diisopropylethylamine (1.20 mL, 6.92 mmol) in DMF (11.5 mL) was added ammonia, 7.0 N solution in methanol (0.49 mL, 3.46 mmol). The reaction mixture was stirred at 40° C. for 18 h. The mixture was washed with water, extracted with EtOAc. The organic layer was concentrated and chromatographed (silica gel, 0 to 40%, acetone/DCM+10% MeOH) to afford the title compound (330 mg, 33.1%) as an off-white oil.

Step 4: (1S)-1-cyano-N,N-bis(4-methoxybenzyl)pent-4-ene-1-sulfonamide and (1R)-1-cyano-N,N-bis(4-methoxybenzyl)-4-pentene-1-sulfonamide

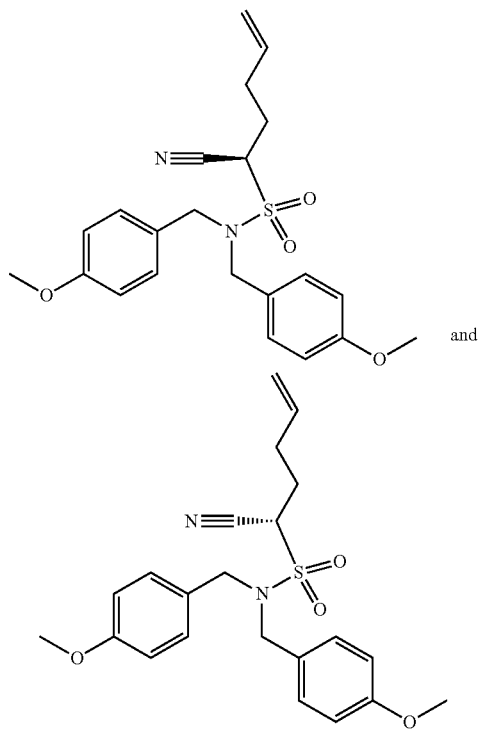

A mixture of 2-(N,N-bis(4-methoxybenzyl)sulfamoyl)hex-5-enamide (400 mg, 0.925 mmol) in phosphorus oxychloride (847 μL, 9.25 mmol) was heated at 60° C. for 2 h. The reaction mixture was cooled to ambient temperature and poured into ice water slowly. The combined organic layers were extracted with diethyl ether (3×), dried (MgSO₄), filtered and concentrated. The resulting residue was chromatographed (silica gel, 0 to 100%, acetone/DCM) to afford the title compound, (310 mg, 81%) as a colorless oil.

Step 5: (1S)-1-cyanopent-4-ene-1-sulfonamide and (1R)-1-cyanopent-4-ene-1-sulfonamide and

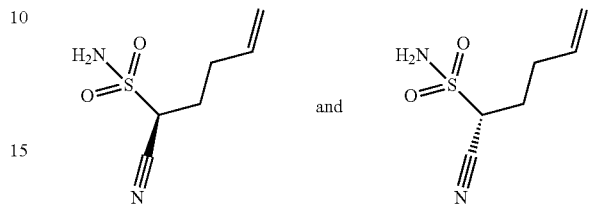

The title compounds were prepared from (1S)-cyanopent-4-ene-1-sulfonamide and (1R)-cyano-pent-4-ene-1-sulfonamide using a similar procedure described in Step 3 of Example 373.

Step 6: (3S)-6'-chloro-N-(((1S)-1-cyano-4-penten-1-yl)sulfonyl)-5-(((1R,2R)-2-((1S,2E)-1-hydroxy-2-hexen-1-yl)cyclobutyl)methyl)-3',4,4',5-tetrahydro-2'H-spiro[1,5-benzoxazepine-3,1'-naphthalene]-7-carboxamide and (3S)-6'-chloro-N-(((1R)-1-cyano-4-penten-1-yl) sulfonyl)-5-(((1R,2R)-2-((1S,2E)-1-hydroxy-2-hexen-1-yl)cyclobutyl)methyl)-3',4,4',5-tetrahydro-2'H-spiro[1,5-benzoxazepine-3,1'-naphthalene]-7-carboxamide

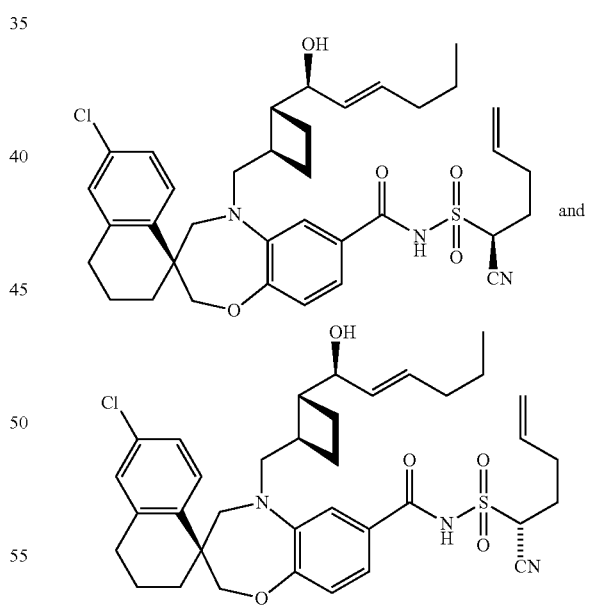

N,N-dimethylpyridin-4-amine (DMAP) (47.9 mg, 0.392 mmol) was added to a solution of (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A, 100 mg, 0.196 mmol), triethylamine (0.082 mL, 0.588 mmol) and 1-cyanopent-4-ene-1-sulfonamide (68 mg, 0.392 mmol) in DCM (2 mL) at ambient temperature. N-(3-Dimethylaminopropyl)-N-ethylcarbodiimide hydrochloride (75 mg, 0.392 mmol) was added slowly and the reaction mixture was stirred at ambient temperature for 18 h. The residue was chromatographed (silica gel, 10% to 100%, EtOAc+1.0% AcOH/hexanes) to afford the title compounds (130 mg, 100% yield).

Step 7: (1S,3'R,6'R,7'S,8'E,12'S)-6-chloro-7'-hydroxy-15'-oxo-3,4-dihydro-2H-spiro[naphthalene-1, 22'-[20]oxa[13]thia[1,14]diazatetracyclo[14.7.2.0$^{3,6}$.0$^{19,24}$]pentacosa[8,16,18,24]tetraene]-12'-carbonitrile 13',13'-dioxide or (1S,3'R,6'R,7'S,8'E,12'R)-6-chloro-7'-hydroxy-15'-oxo-3,4-dihydro-2H-spiro[naphthalene-1,22'-[20]oxa[13]thia [1,14]diazatetracyclo[14.7.2.0$^{3,6}$.0$^{19,24}$]pentacosa[8,16,18,24]tetraene]-12'-carbonitrile 13',13'-dioxide A round bottom flask was charged with (1'S)-6'-chloro-N-((1-cyanopent-4-en-1-yl)sulfonyl)-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide (0.130 g, 0.195 mmol) in AcOH (67.3 mL). To the homogeneous solution was added Hoveyda-Grubbs II (0.024 g, 0.039 mmol) at room temperature. The mixture was stirred at ambient temperature under reduced pressure overnight and then air was bubbled through for 10 min. The reaction mixture was concentrated. The crude product was purified by reversed phase preparatory HPLC (Gemini™ Prep C$_{18}$ 5 µm column; Phenomenex, Torrance, CA; gradient elution of 35% to 95% MeCN in water, where both solvents contain 0.1% TFA, 30 min method) to afford the title compound as a white solid (3 mg, 2.58%). $^1$H NMR (400 MHz, CD$_2$Cl$_2$) δ 7.76-7.68 (m, 1H), 7.22-7.15 (m, 1H), 7.12-7.06 (m, 1H), 6.99-6.86 (m, 3H), 5.76 (ddd, J=2.35, 3.91, 11.74 Hz, 2H), 5.24 (ddd, J=3.33, 10.76, 14.09 Hz, 1H), 4.32-4.19 (m, 1H), 4.13-4.08 (m, 2H), 3.83 (d, J=16.24 Hz, 1H), 3.68 (d, J=13.50 Hz, 1H), 3.26 (d, J=14.28 Hz, 1H), 3.06 (dd, J=9.39, 15.45 Hz, 1H), 2.83-2.71 (m, 2H), 2.54-2.24 (m, 6H), 2.09-1.76 (m, 8H), 1.44-1.36 (m, 2H). m/z (ESI, +ve ion) 596.2 (M+H)$^+$.

Example 154. (1S,3'R,6'R,7'S,8'E,12'R)-12'-(2-(tert-butylsulfonyl)ethyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,12'S)-12'-(2-(tert-butylsulfonyl)ethyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

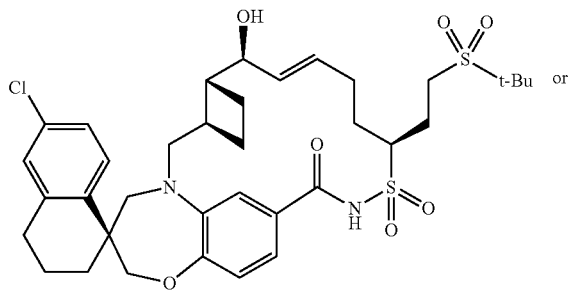

or

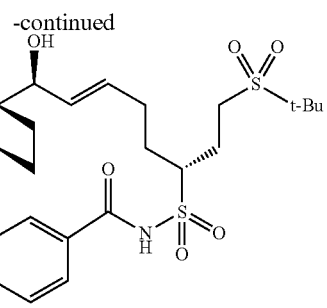

Step 1: (3R)-1-hydroxy-N,N-bis(4-methoxybenzyl)-6-heptene-3-sulfonamide and (3S)-1-hydroxy-N,N-bis(4-methoxybenzyl)-6-heptene-3-sulfonamide

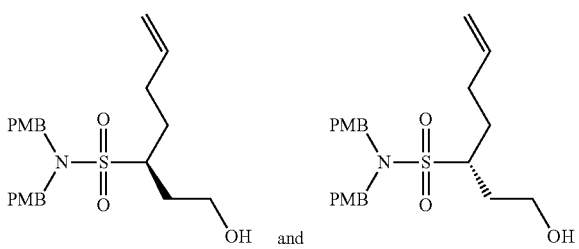

To a solution of N,N-bis(4-methoxybenzyl)pent-4-ene-1-sulfonamide (EE19, 4.85 g, 12.45 mmol) in THF (49.8 mL) was added butyllithium solution, 2.5 M in hexanes (5.98 mL, 14.94 mmol) −78° C. dropwise. After the reaction was stirred at −78° C. for 10 min, ethylene oxide gas (bp=10.7°) was sparged into the reaction flask for 30 minutes at this temperature. The reaction was allowed to warm to ambient temperature and stirred for 1 h. The reaction mixture was quenched with saturated aqueous NH$_4$Cl, and extracted with EtOAc (2×). The organic layers were washed with brine, dried (Na$_2$SO$_4$) and filtered. The filtrate was concentrated and chromatographed (silica gel, 30% to 65%, EtOAc/Hex) to afford the title compounds (4.6 g, 85%) as a colorless oil.

Step 2: (3S)—N,N-bis(4-methoxybenzyl)-1-((2-methyl-2-propanyl)sulfanyl)-6-heptene-3-sulfonamide and (3R)—N,N-bis(4-methoxybenzyl)-1-((2-methyl-2-propanyl)sulfanyl)-6-heptene-3-sulfonamide

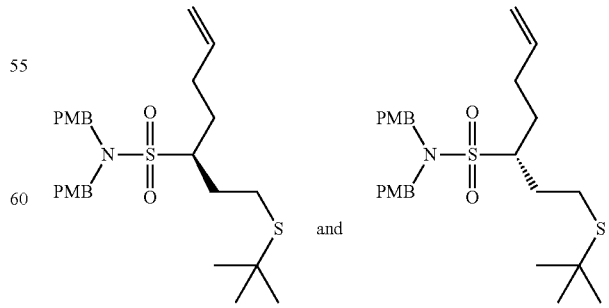

To a solution of (3R)-1-hydroxy-N,N-bis(4-methoxybenzyl)-6-heptene-3-sulfonamide and (3s)-1-hydroxy-N,N-bis (4-methoxybenzyl)-6-heptene-3-sulfonamide (500 mg, 1.15 mmol) in toluene (2.31 mL) was added cyanomethylenetri-n-butylphosphorane (0.84 mL, 3.46 mmol) and tert-butyl-thiol (0.39 mL, 3.46 mmol). The reaction mixture was sealed and stirred for 18 h at 100° C. The mixture was then cooled and concentrated. The crude material was chromatographed (silica gel, 0 to 100%, EtOAc/hexane) to afford the title compound (350 mg, 60.0%) as a light yellow oil.

Step 3: (3S)—N,N-bis(4-methoxybenzyl)-1-((2-methyl-2-propanyl)sulfonyl)-6-heptene-3-sulfona-mide and (3R)—N,N-bis(4-methoxybenzyl)-1-((2-methyl-2-propanyl)sulfonyl)-6-heptene-3-sulfonamide and (3R)—N,N-bis(4-methoxybenzyl)-1-((2-methyl-2-propanyl)sulfonyl)-6-heptene-3-sulfonamide and (3R)—N,N-bis(4-methoxybenzyl)-1-((2-methyl-2-propanyl)sulfonyl)-6-heptene-3-sulfonamide

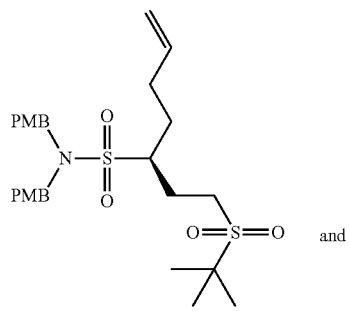

and

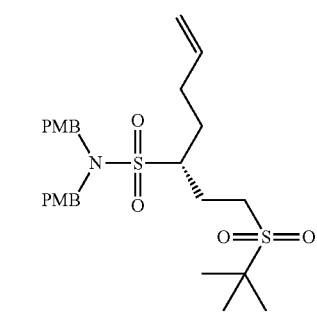

To a solution of (3S)—N,N-bis(4-methoxybenzyl)-1-((2-methyl-2-propanyl)sulfanyl)-6-heptene-3-sulfonamide and (3R)—N,N-bis(4-methoxybenzyl)-1-((2-methyl-2-propa-nyl)sulfanyl)-6-heptene-3-sulfonamide (320 mg, 0.633 mmol) in DCM (3 mL) at 0° C. was added 3-chloroperoxy-benzoic acid, 77% max. (312 mg, 1.39 mmol). The reaction was stirred at this temperature for 15 minutes. The reaction was quenched with saturated aqueous sodium bicarbonate, and extracted with DCM (3×). The combined organic layers were washed with brine, dried (MgSO$_4$), and filtered. The filtrated was concentrated and chromatographed (silica gel, 0 to 100%, EtOAc/hexane) to afford the title compound (210 mg, 61.7%) as an oil.

Step 4: (3R)-1-((2-methyl-2-propanyl)sulfonyl)-6-heptene-3-sulfonamide and (3S)-1-((2-methyl-2-propanyl)sulfonyl)-6-heptene-3-sulfonamide

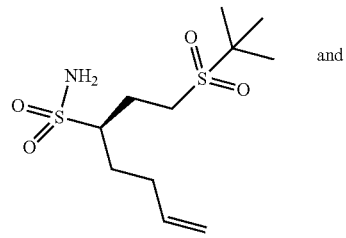

and

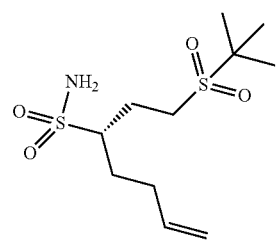

The title compounds were prepared from (3S)—N,N-bis(4-methoxybenzyl)-1-((2-methyl-2-propanyl)sulfonyl)-6-heptene-3-sulfonamide and (3R)—N,N-bis(4-methoxyben-zyl)-1-((2-methyl-2-propanyl)sulfonyl)-6-heptene-3-sulfonamide using a similar procedure described in Step 3 in Example 373.

Step 5: (3S)-6'-chloro-5-(((1R,2R)-2-((1S,2E)-1-hydroxy-2-hexen-1-yl)cyclobutyl)methyl)-N-(((3S)-1-((2-methyl-2-propanyl)sulfonyl)-6-hepten-3-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((3R)-1-((2-methyl-2-propanyl)sulfonyl)-6-hepten-3-yl)sulfo-nyl)-3',4,4',5-tetrahydro-2'H-spiro[1,5-benzoxazepine-3,1'-naphthalene]-7-carboxamide

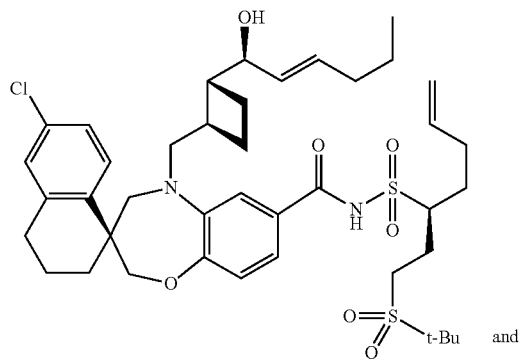

and

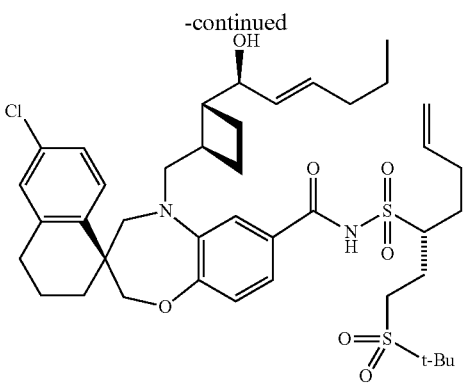

N,N-dimethylpyridin-4-amine (DMAP) (47.9 mg, 0.392 mmol) was added to a solution of (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A, 100 mg, 0.196 mmol), triethylamine (0.082 mL, 0.588 mmol) and (3R)-1-((2-methyl-2-propanyl)sulfonyl)-6-heptene-3-sulfonamide and (3S)-1-((2-methyl-2-propanyl)sulfonyl)-6-heptene-3-sulfonamide (117 mg, 0.392 mmols) in DCM (2 mL) at ambient temperature. N-(3-dimethylaminopropyl)-N-ethylcarbodiimide hydrochloride (75 mg, 0.392 mmol) was added slowly and the reaction mixture was stirred at ambient temperature for 18 h. The residue was chromatographed (silica gel, 10% to 100%, EtOAc+AcOH/hexane) to afford the title compound (130 mg, 84%).

Step 6: (1S,3'R,6'R,7'S,8'E,12'R)-12'-(2-(tert-butylsulfonyl)ethyl)-6-chloro-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,12'S)-12'-(2-(tert-butylsulfonyl)ethyl)-6-chloro-7'-hydroxy-3,4-dihydro-2H,15'H-spiro[naphthalene-1,22'-[20]oxa[13]thia [1,14]diazatetracyclo[14.7.2.0³,⁶.0¹⁹,²⁴]pentacosa[8,16,18,24]tetraen]-15'-one 13',13'-dioxide A round bottom flask was charged with (1'S)—N-41-(tert-butylsulfonyl)hept-6-en-3-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide (0.130 g, 0.165 mmol) in AcOH (56.8 mL). To this homogeneous solution was added Hoveyda-Grubbs II (0.021 g, 0.033 mmol) at ambient temperature. The mixture was stirred at ambient temperature under reduced pressure for 18 h and then air was sparged into the flask for 10 min. The reaction mixture was concentrated. The crude oil was purified by reversed phase preparatory HPLC (Gemini™ Prep $C_{18}$ 5 μm column; Phenomenex, Torrance, CA; gradient elution of 35% to 95% MeCN in water, where both solvents contain 0.1% TFA, 30 min method) to afford the title compound as the second eluting isomer as a white solid (8 mg, 6.75%). $^1$H NMR (400 MHz, CD$_2$Cl$_2$) δ 7.72 (d, J=8.61 Hz, 1H), 7.32 (dd, J=2.05, 8.31 Hz, 1H), 7.16 (d, J=2.35 Hz, 1H), 7.09 (d, J=2.35 Hz, 1H), 6.98 (d, J=8.22 Hz, 2H), 5.81-5.68 (m, 1H), 5.63-5.51 (m, 1H), 4.52 (t, J=6.85 Hz, 1H), 4.11 (s, 2H), 3.99-3.79 (m, 2H), 3.70 (d, J=14.48 Hz, 1H), 3.44-3.10 (m, 4H), 2.86-2.72 (m, 2H), 2.67-2.53 (m, 2H), 2.46-2.16 (m, 5H), 2.12-1.91 (m, 6H), 1.75-1.57 (m, 4H), 1.43 (s, 9H). m/z (ESI, +ve ion) 719.2 (M+H)⁺.

Example 155. (1S,3'R,6'R,7'S,8'E,12'R)-12'-(2-(tert-butylsulfonyl)ethyl)-6-chloro-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,12'S)-12'-(2-(tert-butylsulfonyl)ethyl)-6-chloro-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

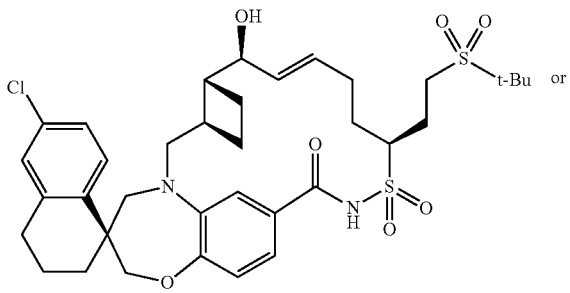

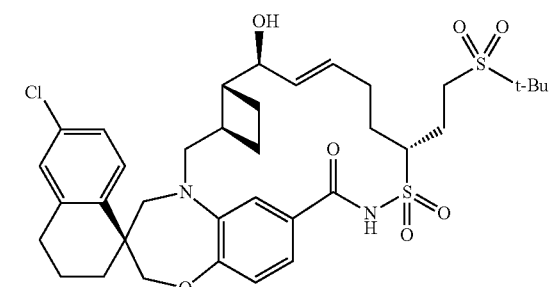

The title compound (16 mg, 13.5%) was obtained as the first eluting isomer from Example 154, Step 6. $^1$H NMR (400 MHz, CD$_2$Cl$_2$) δ 8.43-8.17 (m, 1H), 7.71 (d, J=8.61 Hz, 1H), 7.17 (dd, J=2.35, 8.41 Hz, 1H), 7.09 (d, J=2.35 Hz, 1H), 6.95-6.84 (m, 3H), 5.94-5.65 (m, 2H), 4.39-4.26 (m, 1H), 4.20 (dd, J=4.01, 7.34 Hz, 1H), 4.08 (s, 2H), 3.82 (d, J=13.89 Hz, 1H), 3.70 (d, J=14.09 Hz, 1H), 3.36 (t, J=6.85 Hz, 2H), 3.25 (d, J=14.28 Hz, 1H), 3.03 (dd, J=9.39, 15.26 Hz, 1H), 2.85-2.62 (m, 2H), 2.54-2.19 (m, 6H), 2.10-1.90 (m, 4H), 1.81 (br. s., 6H), 1.43 (s, 9H). m/z (ESI, +ve ion) 719.2 (M+H)⁺.

Example 156. (1S,3'R,6'R,7'S,8'E,12'S)-12'-(2-(tert-butylsulfonyl)ethyl)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-12'-(2-(tert-butylsulfonyl)ethyl)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

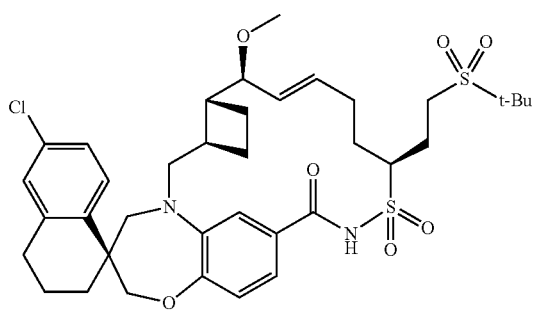

or

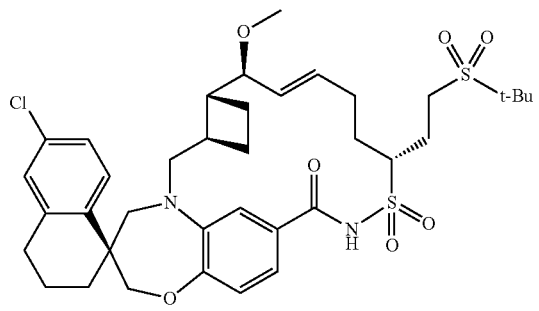

The title compound (3.4 mg, 67%) was prepared from (1S,3'R,6'R,7'S,8'E,12'R)-12'-(2-(tert-butylsulfonyl)ethyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-12'-(2-(tert-butylsulfonyl)ethyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 155) using a similar procedure described in Example 718, Step 1. $^1$H NMR (400 MHz, CD$_2$Cl$_2$) δ 7.70 (d, J=8.61 Hz, 1H), 7.17 (dd, J=2.25, 8.51 Hz, 1H), 7.09 (d, J=2.15 Hz, 1H), 6.90 (s, 2H), 6.84-6.81 (m, 1H), 5.81 (td, J=6.50, 14.97 Hz, 1H), 5.58-5.49 (m, 1H), 4.43-4.28 (m, 1H), 4.07 (s, 2H), 3.87-3.76 (m, 1H), 3.70 (d, J=14.28 Hz, 1H), 3.63 (dd, J=3.42, 8.90 Hz, 1H), 3.45-3.29 (m, 2H), 3.25 (d, J=14.28 Hz, 1H), 3.01 (dd, J=10.27, 15.36 Hz, 1H), 2.81-2.72 (m, 2H), 2.55-2.25 (m, 7H), 2.05-2.01 (m, 1H), 1.99-1.73 (m, 8H), 1.72-1.60 (m, 2H), 1.45-1.39 (m, 9H). m/z (ESI, +ve ion) 733.2 (M+H)$^+$.

Example 157. (1S,3'R,6'R,7'S,8'E,12'S)-6-chloro-12'-(cyclopropylmethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-12'-(cyclopropylmethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'S)-6-chloro-12'-(cyclopropylmethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'R)-6-chloro-12'-(cyclopropylmethyl)-7'-hydroxy-3,4-dihydro-2H,15'H-spiro[naphthalene-1,22'-[20]oxa[13]thia[1,14]diazatetracyclo[14.7.2.0$^{3,6}$.019,24]pentacosa[8,16,18,24]tetraen]-15'-one 13',13'-dioxide

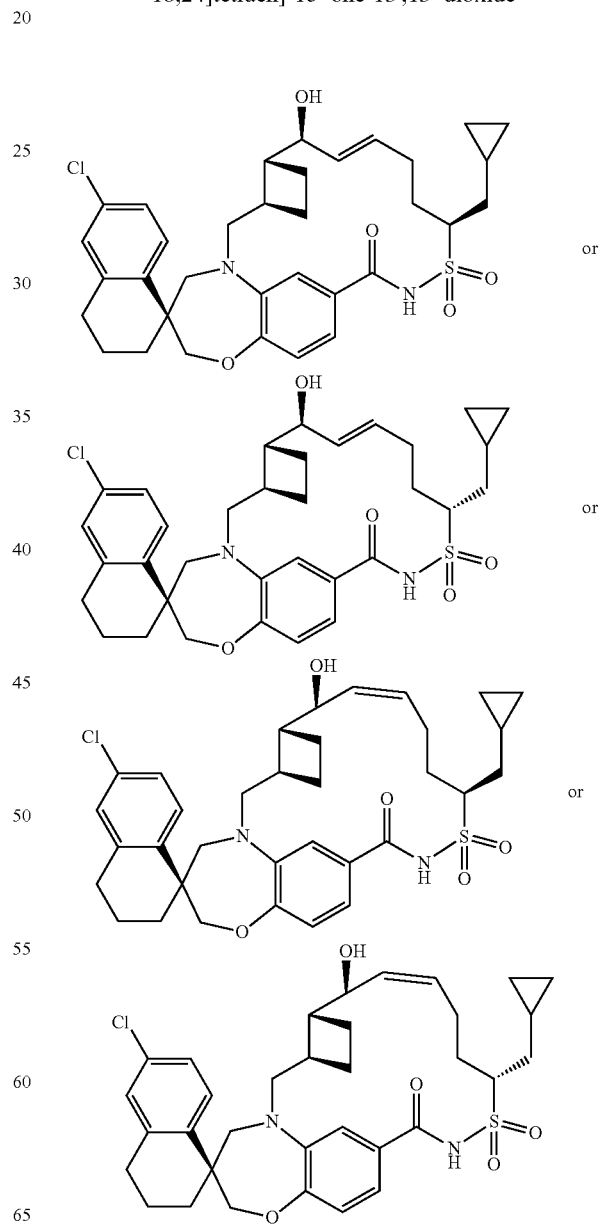

551

Step 1: (2S)-1-cyclopropyl-5-hexene-2-sulfonamide and (2R)-1-cyclopropyl-5-hexene-2-sulfonamide

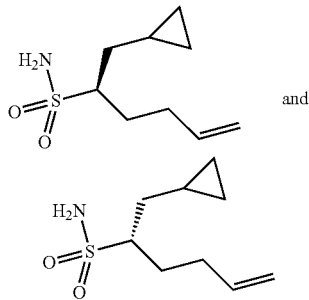

The title compounds were prepared from N,N-bis(4-methoxybenzyl)pent-4-ene-1-sulfonamide (EE19) using a similar procedure described in Step 1 and then 5 of Example 153, replacing chlorocarbonic acid methyl ester with (bromomethyl)-cyclopropane in Step 1.

Step 2: (1S,3'R,6'R,7'S,8'E,12'S)-6-chloro-12'-(cyclopropylmethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-12'-(cyclopropylmethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'S)-6-chloro-12'-(cyclopropylmethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'R)-6-chloro-12'-(cyclopropylmethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide The title compound was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12) using a similar procedure described in Example 153, Step 6 to 7, replacing 1-cyanopent-4-ene-1-sulfonamide in Step 6 with 1-cyclopropylhex-5-ene-2-sulfonamide. This crude oil of Step 7 was purified by reversed phase preparatory HPLC (Gemini™ Prep C$_{18}$ 5 μm column; Phenomenex, Torrance, CA; gradient elution of 50% to 90% MeCN in water, where both solvents contain 0.1% TFA, 30 min method) to afford the title compound as the first eluting isomer as a white foam (9 mg, 9.7%). $^1$H NMR (400 MHz, CD$_2$Cl$_2$) δ 8.00 (s, 1H), 7.53 (d, J=8.61 Hz, 1H), 6.99 (dd, J=2.35, 8.61 Hz, 1H), 6.91 (d, J=2.35 Hz, 1H), 6.76-6.68 (m, 3H), 5.73-5.60 (m, 1H), 5.53 (dd, J=7.63, 15.45 Hz, 2H), 3.90 (s, 4H), 3.65 (d, J=13.89 Hz, 1H), 3.53 (d, J=14.28 Hz, 1H), 3.07 (d, J=14.28 Hz, 1H), 2.86 (dd, J=9.29, 15.36 Hz, 1H), 2.68-2.48 (m, 2H), 2.06 (s, 4H), 1.94-1.72 (m, 6H), 1.61 (br. s., 6H), 0.92-0.79 (m, 1H), 0.41 (d, J=7.83 Hz, 2H), 0.11 to −0.09 (m, 2H). m/z (ESI, +ve ion) 625.2 (M+H)$^+$.

552

Example 158. (1S,3'R,6'R,7'S,8'E,12'S)-6-chloro-12'-(cyclopropylmethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-12'-(cyclopropylmethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'S)-6-chloro-12'-(cyclopropylmethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'R)-6-chloro-12'-(cyclopropylmethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

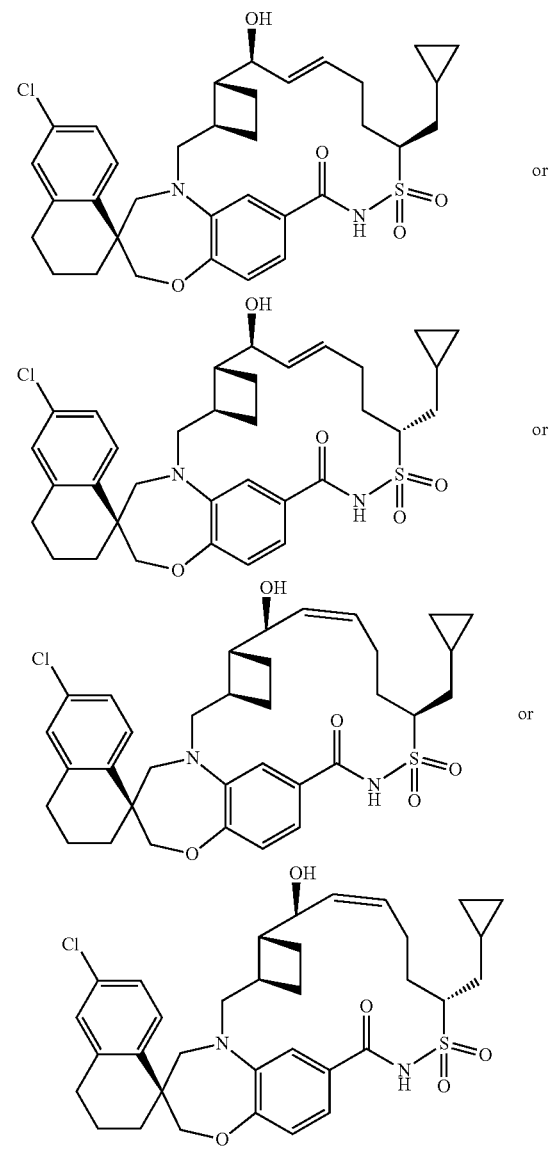

The title compound (6 mg, 6.5%) was isolated as the second eluting isomer from the reversed phase preparatory HPLC separation in Example 157. $^1$H NMR (400 MHz, CD$_2$Cl$_2$) δ 8.17 (br. s., 1H), 7.67 (d, J=8.61 Hz, 1H), 7.57-7.39 (m, 1H), 7.15 (dd, J=2.35, 8.41 Hz, 1H), 7.10 (d, J=2.35 Hz, 1H), 6.99-6.83 (m, 2H), 5.69 (dt, J=4.70, 15.45 Hz, 1H), 5.61-5.45 (m, 1H), 4.21 (s, 2H), 4.01-3.80 (m, 3H), 3.71 (d, J=13.89 Hz, 1H), 3.40 (d, J=14.08 Hz, 1H), 3.20 (d, J=15.65 Hz, 1H), 2.83-2.71 (m, 2H), 2.56-2.41 (m, 2H), 2.38-2.26 (m, 1H), 2.17-1.99 (m, 4H), 1.87-1.78 (m, 5H), 1.78-1.55 (m, 4H), 1.08-0.93 (m, 1H), 0.68-0.46 (m, 2H), 0.31-0.12 (m, 2H). m/z (ESI, +ve ion) 625.2 (M+H)$^+$.

Example 159. (1S,3'R,6'R,7'S,8'E,12'S)-6-chloro-12'-(cyclopropylmethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-12'-(cyclopropylmethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'Z,12'S)-6-chloro-12'-(cyclopropylmethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'Z,12'R)-6-chloro-12'-(cyclopropylmethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

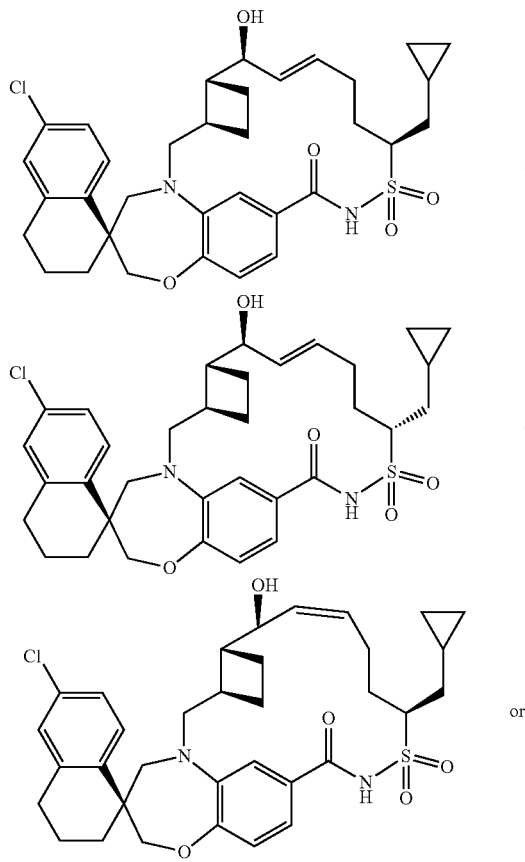

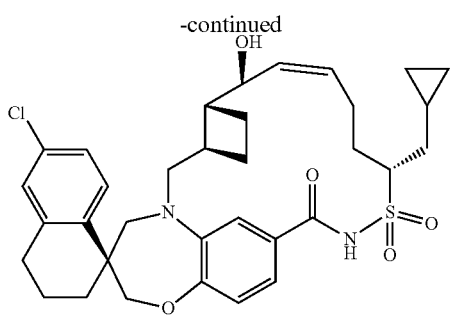

The title compound (7 mg, 7.5%) was isolated as the third eluting isomer from the reversed phase preparatory HPLC separation in Example 157. $^1$H NMR (400 MHz, CD$_2$Cl$_2$) δ 9.40-9.24 (m, 1H), 7.72 (d, J=8.41 Hz, 1H), 7.26 (dd, J=1.96, 8.22 Hz, 1H), 7.17 (dd, J=2.15, 8.41 Hz, 1H), 7.09 (s, 1H), 6.96 (d, J=8.22 Hz, 1H), 6.89 (d, J=1.96 Hz, 1H), 5.81-5.66 (m, 1H), 5.64-5.53 (m, 1H), 4.63-4.49 (m, 1H), 4.10 (s, 2H), 3.91 (d, J=15.65 Hz, 1H), 3.71 (d, J=14.48 Hz, 1H), 3.27 (d, J=14.28 Hz, 1H), 3.20-3.10 (m, 1H), 3.09-2.98 (m, 1H), 2.82-2.73 (m, 2H), 2.69-2.55 (m, 1H), 2.50-2.36 (m, 1H), 2.34-2.27 (m, 1H), 2.24-2.17 (m, 1H), 2.05 (br. s., 6H), 1.78-1.64 (m, 4H), 1.54-1.39 (m, 1H), 1.26 (s, 2H), 0.95-0.82 (m, 2H), 0.80-0.69 (m, 1H), 0.42-0.26 (m, 1H). m/z (ESI, +ve ion) 625.3 (M+H)$^+$.

Example 160. methyl(1S,3'R,6'R,7'S,8'E,12'S)-6-chloro-7'-hydroxy-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraene]-12'-carboxylate 13',13'-dioxide or methyl (1S,3'R,6'R,7'S,8'E,12'R)-6-chloro-7'-hydroxy-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraene]-12'-carboxylate 13',13'-dioxide

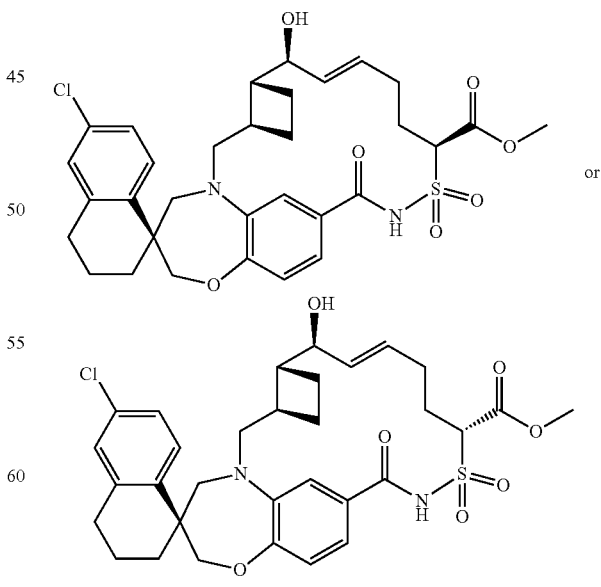

The title compound was prepared from (S)-6'-chloro-5-(((1R,2R)-2-((S,E)-1-hydroxyhex-2-en-1-yl)cyclobutyl)

methyl)-3',4,4',5-tetrahydro-2H,2'H-spiro[benzo[b][1,4]oxazepine-3,1'-naphthalene]-7-carboxylic acid (Intermediate AA12A) using a similar procedure described in Example 153, Step 6 to 7, replacing 1-cyanopent-4-ene-1-sulfonamide in Step 6 with methyl 2-sulfamoylhex-5-enoate. The crude oil of Step 7 was purified by reversed phase preparatory HPLC (Gemini™ Prep C$_{18}$ 5 μm column; Phenomenex, Torrance, CA; gradient elution of 50% to 90% MeCN in water, where both solvents contain 0.1% TFA, 30 min method) to afford the title compound the fastest eluting isomer (21 mg, 7.7%). $^1$H NMR (400 MHz, CD$_2$Cl$_2$) δ 8.27 (s, 1H), 7.70 (d, J=8.6 Hz, 1H), 7.17 (dd, J=2.3, 8.4 Hz, 1H), 7.09 (d, J=2.3 Hz, 1H), 6.96-6.87 (m, 3H), 5.73 (dd, J=9.0, 14.1 Hz, 1H), 5.05 (dd, J=3.3, 10.6 Hz, 1H), 4.20 (br. s., 1H), 4.09 (s, 2H), 3.87 (s, 3H), 3.84 (d, J=16.2 Hz, 1H), 3.70 (d, J=14.3 Hz, 1H), 3.25 (d, J=14.1 Hz, 1H), 3.04 (dd, J=9.0, 15.7 Hz, 1H), 2.81-2.72 (m, 2H), 2.49-2.27 (m, 4H), 2.04 (d, J=13.5 Hz, 2H), 1.99-1.71 (m, 9H), 1.41 (t, J=12.2 Hz, 1H). m/z (ESI, +ve ion) 629.2 (M+H)$^+$.

Example 161. methyl(((1S,3'R,6'R,7'S,8'E,12'S)-6-chloro-12'-cyclopropyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetate or methyl(((1S,3'R,6'R,7'S,8'E,12'R)-6-chloro-12'-cyclopropyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetate

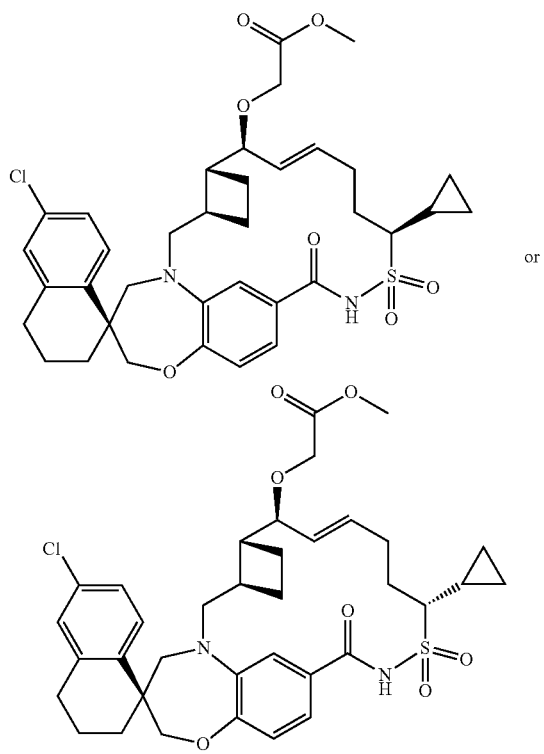

To a solution of (1S,3'R,6'R,7'S,8'E,12'S)-6-chloro-12'-cyclopropyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-6-chloro-12'-cyclopropyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 148, the first eluting isomer, 7.00 mg, 0.011 mmol) in THF (1.145 mL) was added sodium hydride, 60% dispersion in mineral oil (1.37 mg, 0.057 mmol). After 15 min, bromoacetic acid methyl ester (0.002 mL, 0.023 mmol) was added. The reaction was stirred at ambient temperature. After 30 minutes the reaction was quenched with aqueous saturated ammonium chloride, brine and was extracted with diethyl ether (3×). The combined organic layers were concentrated. The crude residue was chromatographed (silica gel, 0% to 100%, EtOAc+0.5% acetic acid/hexane) to afford the title compound (4.6 mg, 58.8%) as colorless glass. $^1$H NMR (400 MHz, CD$_2$Cl$_2$) δ 7.70 (d, J=8.41 Hz, 1H), 7.17 (dd, J=2.45, 8.51 Hz, 1H), 7.09 (d, J=2.15 Hz, 1H), 6.92-6.88 (m, 2H), 6.79 (s, 1H), 5.76 (ddd, J=3.81, 9.10, 15.26 Hz, 1H), 5.56 (dd, J=8.41, 15.06 Hz, 1H), 4.07 (d, J=2.74 Hz, 2H), 3.97 (d, J=4.11 Hz, 2H), 3.89-3.77 (m, 2H), 3.72 (s, 3H), 3.44 (dt, J=2.35, 10.27 Hz, 1H), 3.25 (d, J=14.28 Hz, 1H), 3.03 (dd, J=10.47, 15.36 Hz, 1H), 2.80-2.72 (m, 2H), 2.61-2.48 (m, 2H), 2.32 (s, 3H), 1.99-1.90 (m, 2H), 1.88-1.77 (m, 5H), 1.74-1.64 (m, 2H), 1.07-0.96-(m, 2H), 0.75-0.82 (m, 2H), 0.48-0.39 (m, 2H). m/z (ESI, +ve ion) 683.2 (M+H)$^+$.

Example 162. (1S,3'R,6'R,7'S,8'E,12'R)-12'-(2-(benzylsulfonyl)ethyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-12'-(2-(benzylsulfonyl)ethyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

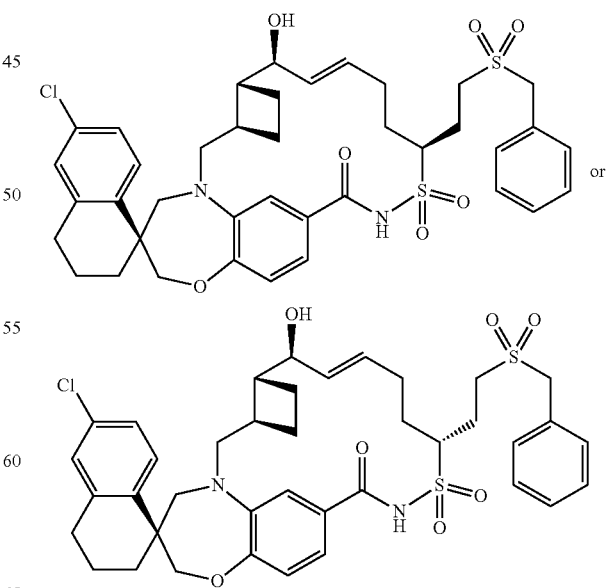

Step 1: (3R)-1-(benzylsulfanyl)-N,N-bis(4-methoxybenzyl)-6-heptene-3-sulfonamide and (3S)-1-(benzylsulfanyl)-N,N-bis(4-methoxybenzyl)-6-heptene-3-sulfonamide

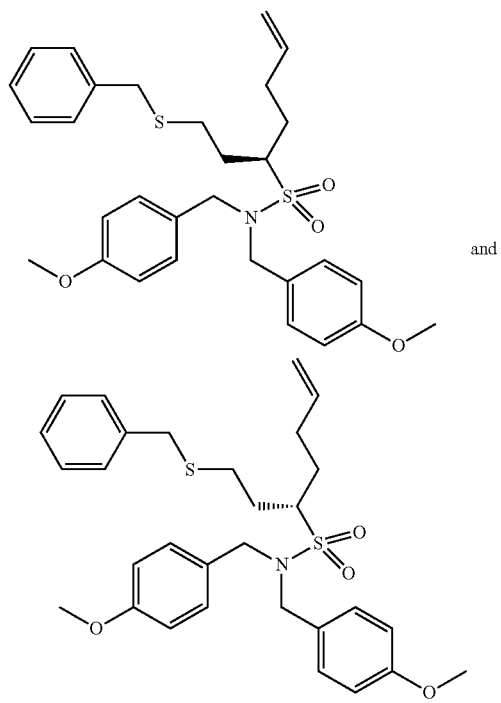

and

To a mixture of (3R)-1-hydroxy-N,N-bis(4-methoxybenzyl)-6-heptene-3-sulfonamide and (3S)-1-hydroxy-N,N-bis(4-methoxybenzyl)-6-heptene-3-sulfonamide (Example 154, 500 mg, 1.15 mmol) in toluene (2.3 mL) was added cyanomethylenetri-n-butylphosphorane (0.84 mL, 3.46 mmol) and benzyl thiol (0.41 mL, 3.46 mmol) at ambient temperature. The reaction was sealed, stirred and heated at 100° C. for 18 h. The mixture was cooled, concentrated and the crude residue was chromatographed (silica gel, 0 to 100%, EtOAc/hexane) to afford the title compound (456 mg, 73.3%) as a light-yellow oil.

Step 2: (3R)-1-(benzylsulfonyl)-N,N-bis(4-methoxybenzyl)-6-heptene-3-sulfonamide and (3S)-1-(benzylsulfonyl)-N,N-bis(4-methoxybenzyl)-6-heptene-3-sulfonamide

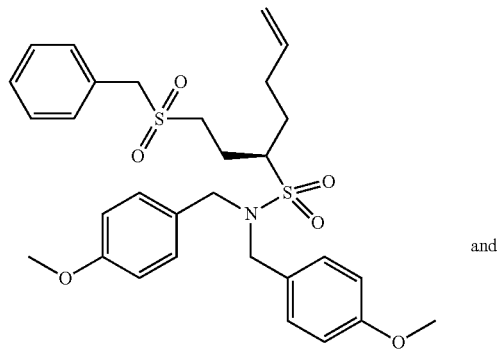

and

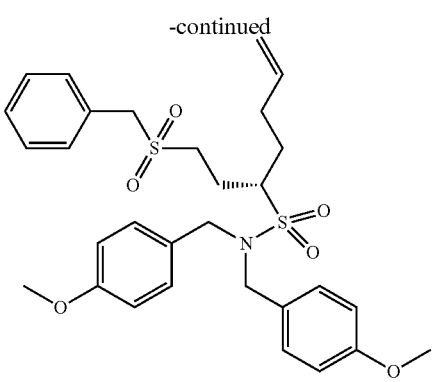

To a mixture of (3R)-1-(benzylsulfanyl)-N,N-bis(4-methoxybenzyl)-6-heptene-3-sulfonamide and (3S)-1-(benzylsulfanyl)-N,N-bis(4-methoxybenzyl)-6-heptene-3-sulfonamide (420 mg, 0.78 mmol) in DCM (3 mL) at 0° C. was added 3-chloroperoxybenzoic acid, 77% max. (384 mg, 1.71 mmol). The reaction mixture was stirred for 15 minutes at this temperature and then quenched with saturated aqueous sodium bicarbonate. The mixture was extracted with DCM (3×) and the organic layer was washed with brine, dried (MgSO$_4$), and filtered. The filtrate was concentrated and chromatographed (silica gel, 0 to 100%, EtOAc/hexane) to afford the title compound (350 mg, 79%) as an oil.

Step 3: (3S)-1-(benzylsulfonyl)-6-heptene-3-sulfonamide and (3S)-1-(benzylsulfonyl)-6-heptene-3-sulfonamide

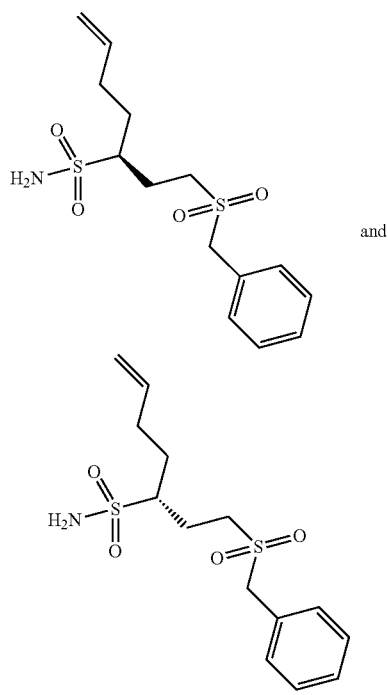

The title compound was prepared from (3R)-1-(benzylsulfonyl)-N,N-bis(4-methoxybenzyl)-6-heptene-3-sulfonamide and (3S)-1-(benzylsulfonyl)-N,N-bis(4-methoxybenzyl)-6-heptene-3-sulfonamide using a similar procedure in Step 5 of Example 153.

559

Step 4: (1S,3'R,6'R,7'S,8'E,12'R)-12'-(2-(benzylsulfonyl)ethyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-12'-(2-(benzylsulfonyl)ethyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide The title compound was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12) using a similar procedure described in Example 153, Step 6 & 7, replacing 1-cyanopent-4-ene-1-sulfonamide with (3S)-1-(benzylsulfonyl)-6-heptene-3-sulfonamide and (3S)-1-(benzylsulfonyl)-6-heptene-3-sulfonamide in Step 6, and the crude residue of Step 7 was purified by reversed phase preparatory HPLC (Gemini™ Prep C$_{18}$ 5 μm column; Phenomenex, Torrance, CA; gradient elution of 50% to 90% MeCN in water, where both solvents contain 0.1% TFA, 30 min method) to afford the title compound as the first eluting isomer (16 mg, 12.6%). $^1$H NMR (400 MHz, CD$_2$Cl$_2$) δ 8.40-8.25 (m, 1H), 7.75 (d, J=8.61 Hz, 1H), 7.55-7.43 (m, 5H), 7.21 (dd, J=2.35, 8.61 Hz, 1H), 7.14 (d, J=2.35 Hz, 1H), 6.99-6.88 (m, 3H), 5.86-5.67 (m, 2H), 4.35 (s, 2H), 4.33-4.20 (m, 2H), 4.13 (s, 2H), 3.86 (d, J=13.50 Hz, 1H), 3.74 (d, J=14.28 Hz, 1H), 3.36 (t, J=7.73 Hz, 1H), 3.29 (d, J=14.28 Hz, 1H), 3.08 (dd, J=9.29, 15.36 Hz, 1H), 2.85-2.76 (m, 2H), 2.54-2.30 (m, 6H), 2.29-2.16 (m, 1H), 2.13-2.04 (m, 1H), 2.03-1.93 (m, 2H), 1.91-1.78 (m, 6H), 1.51-1.38 (m, 1H). m/z (ESI, +ve ion) 753.2 (M+H)$^+$.

Example 163. (1S,3'R,6'R,7'S,8'E,12'R)-12'-(2-(benzylsulfonyl)ethyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-12'-(2-(benzylsulfonyl)ethyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

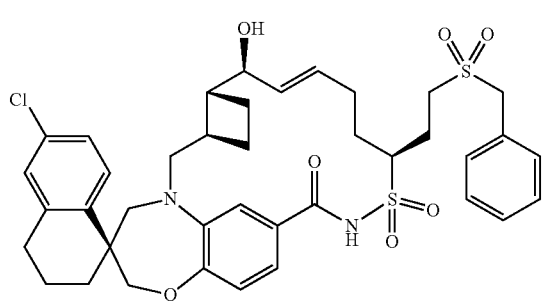

or

560

-continued

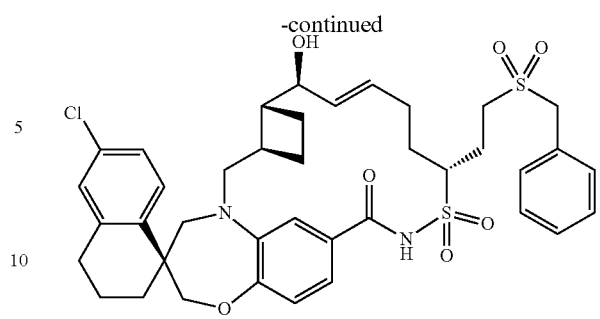

The title compound (8 mg, 6.7%) was isolated as the second eluting isomer from the reversed phase preparatory HPLC separation in Example 162. $^1$H NMR (400 MHz, CD$_2$Cl$_2$) δ 7.72 (d, J=8.41 Hz, 1H), 7.42 (br. s., 5H), 7.31 (s, 1H), 7.16 (br. s., 1H), 7.09 (s, 1H), 7.01-6.92 (m, 2H), 5.79-5.64 (m, 1H), 5.61-5.46 (m, 1H), 4.62-4.44 (m, 1H), 4.31 (s, 2H), 4.11 (s, 2H), 3.95-3.82 (m, 2H), 3.74-3.62 (m, 1H), 3.25 (d, J=14.48 Hz, 4H), 2.77 (br. s., 2H), 2.64-2.44 (m, 2H), 2.28 (d, J=6.06 Hz, 4H), 2.08-1.91 (m, 6H), 1.71 (br. s., 3H), 1.53-1.34 (m, 1H). m/z (ESI, +ve ion) 753.2 (M+H)$^+$.

Example 164. (1S,3'R,6'R,7'S,8'E,10'S)-6-chloro-7'-hydroxy-10'-methyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide or (1S,3'R,6'R,7'S,8'E,10'S)-6-chloro-7'-hydroxy-10'-methyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide

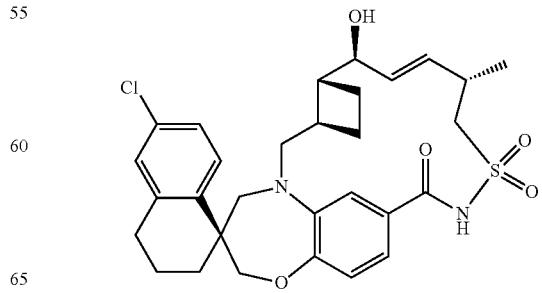

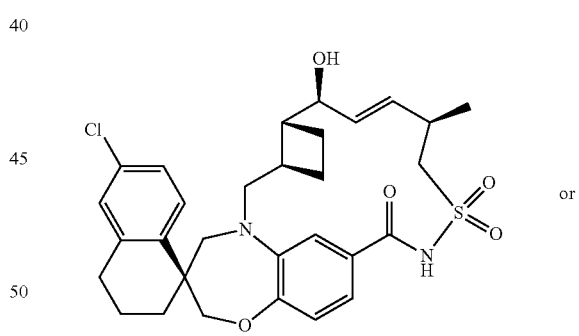

or

Step 1: 2-(((2R)-2-methyl-3-buten-1-yl)sulfanyl)pyrimidine and 2-(((2S)-2-methyl-3-buten-1-yl)sulfanyl)pyrimidine

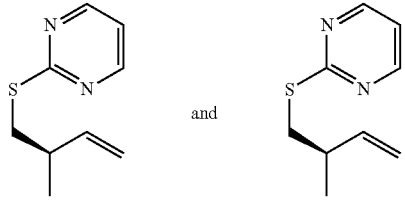

A solution of 2-methyl-3-buten-1-ol (2.395 mL, 23.22 mmol) and triethylamine (6.46 mL, 46.4 mmol) in Et₂O (46.4 mL) was cooled to −78° C. and treated with methanesulfonyl chloride (2.156 mL, 27.9 mmol). The mixture was allowed to warm to ambient temperature and then filtered. The solid was washed with ether and the filtrate was concentrated. The crude mesylate was added to a solution of sodium ethoxide (10.40 mL, 27.9 mmol) and pyrimidine-2-thiol (3.13 g, 27.9 mmol) in EtOH (44 mL). The mixture was stirred for 17 h at 50° C. and then concentrated in vacuo. The residue was triturated in Et₂O and the solid was removed. The filtrate was concentrated and the crude oil was chromatographed (silica gel, 5% to 20%, EtOAc/hexane) to afford the title compound (3.59 g, 86%) as a colorless oil.

Step 2: 2-(((2R)-2-methyl-3-buten-1-yl)sulfonyl)pyrimidine and 2-(((2R)-2-methyl-3-buten-1-yl)sulfonyl)pyrimidine

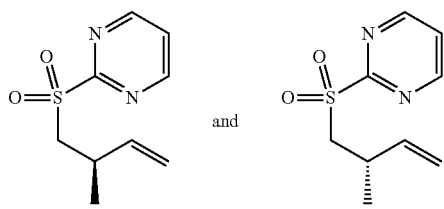

To a flask containing 2-(((2R)-2-methyl-3-buten-1-yl)sulfanyl)pyrimidine and 2-(((2S)-2-methyl-3-buten-1-yl)sulfanyl)pyrimidine (3.59 g, 19.91 mmol) in DCM (1 mL) was added 3-chloroperoxybenzoic acid, 77% max. (9.15 g, 40.8 mmol) at 0° C. The reaction was allowed to stir at this temperature for 15 minutes and then allowed to warm up to ambient temperature. The reaction was quenched with aqueous sodium bicarbonate (100 mL), and extracted with diethyl ether (3×). The organic layer was dried (MgSO₄), filtered and the filtrate was concentrated. The crude oil was chromatographed (silica gel, 0% to 100%, EtOAc/hexane) to afford the title compound (3.47 g, 82%) as light-yellow oil.

Step 3: Sodium (2R)-methylbut-3-ene-1-sulfinate and sodium (2S)-methylbut-3-ene-1-sulfinate

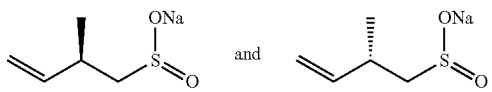

A mixture of 2-(((2R)-2-methyl-3-buten-1-yl)sulfonyl)pyrimidine and 2-(((2R)-2-methyl-3-buten-1-yl)sulfonyl)pyrimidine (3.47 g, 16.35 mmol) in MeOH was treated with sodium methoxide, 25 wt. % solution in methanol (3.74 mL, 16.35 mmol) and allowed to stir at ambient temperature for 1 h. The resulting mixture was concentrated in vacuo and the residue was triturated in Et₂O. The solid was filtered to afford the title compound which was used without further purification.

Step 4: (2S)-methylbut-3-ene-1-sulfonamide and (2R)-methylbut-3-ene-1-sulfonamide

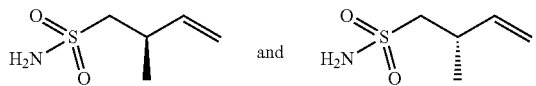

A mixture of sodium (2S)-methylbut-3-ene-1-sulfinate and sodium (2R)-methylbut-3-ene-1-sulfinate (2.55 g, 16.33 mmol) in water (163 mL) was added sodium acetate (2.68 g, 32.7 mmol) followed by hydroxylamine-o-sulfonic acid (1.85 g, 16.33 mmol). The reaction was stirred at ambient temperature for 18 h. The reaction was cooled and treated with aqueous 1.0 N NaOH. The aqueous layer was extracted with EtOAc (2×). The combined organic extracts were dried (MgSO₄), filtered and the filtrate was evaporated in vacuo to afford the title compound (2.1 g, 86%).

Step 5: (3S)-6'-chloro-5-(((1R,2R)-2-((1S,2E,4R)-1-hydroxy-4-methyl-5-sulfamoyl-2-penten-1-yl)cyclobutyl)methyl)-3',4,4',5-tetrahydro-2'H-spiro[1,5-benzoxazepine-3,1'-naphthalene]-7-carboxylic acid and (3S)-6'-chloro-5-(((1R,2R)-2-((1S,2E,4S)-1-hydroxy-4-methyl-5-sulfamoyl-2-penten-1-yl)cyclobutyl)methyl)-3',4,4',5-tetrahydro-2'H-spiro[1,5-benzoxazepine-3,1'-naphthalene]-7-carboxylic acid

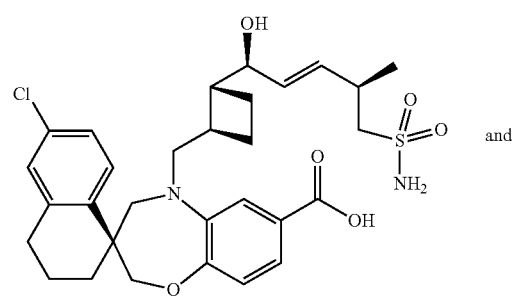

-continued

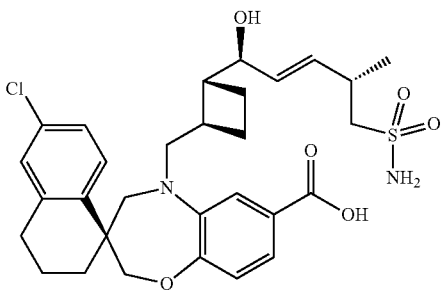

A vial was charged with (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A, 180 mg, 0.353 mmol) and (2S)-methylbut-3-ene-1-sulfonamide and (2R)-methylbut-3-ene-1-sulfonamide (263 mg, 1.764 mmol) in DCE (5.097 mL). The mixture was sparged with argon and added Hoveyda-Grubbs II (22.11 mg, 0.035 mmol) at ambient temperature. The reaction was run at 50° C. for 18 h. The reaction mixture was bubbled with air for 15 minutes and filtered. The filtrate was directly chromatographed (silica gel, 0 to 100%, EtOAc+1.0% HOAc/hexanes) to afford the title compound (106 mg, 51.0%). MS (ESI) m/z: [M+1]=589.2

Step 6: (1S,3'R,6'R,7'S,8'E,10'S)-6-chloro-7'-hydroxy-10'-methyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa [8,15,17,23]tetraen]-14'-one 12',12'-dioxide or (1S,3'R,6'R,7'S,8'E,10'S)-6-chloro-7'-hydroxy-10'-methyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide N,N-dimethylpyridin-4-amine (DMAP) (41.5 mg, 0.339 mmol) was added to a solution of (3S)-6'-chloro-5-(((1R,2R)-2-((1S,2E,4R)-1-hydroxy-4-methyl-5-sulfamoyl-2-penten-1-yl)cyclobutyl)methyl)-3',4,4',5-tetrahydro-2'h-spiro[1,5-benzoxazepine-3,1'-naphthalene]-7-carboxylic acid, (3S)-6'-chloro-5-(((1R,2R)-2-((1S,2E,4S)-1-hydroxy-4-methyl-5-sulfamoyl-2-penten-1-yl)cyclobutyl)methyl)-3',4,4',5-tetrahydro-2'h-spiro[1,5-benzoxazepine-3,1'-naphthalene]-7-carboxylic acid (100 mg, 0.170 mmol) and triethylamine (0.071 mL, 0.509 mmol) in DCM (2 mL) at ambient temperature. Then N-(3-dimethylaminopropyl)-N'-ethylcarbodiimide hydrochloride (65.1 mg, 0.339 mmol) was added slowly and it was stirred at ambient temperature for 18 h. The reaction mixture was diluted with dichloromethane (10 mL) and washed with aqueous saturated sodium bicarbonate (5 mL), aqueous saturated ammonium chloride (5 mL), and brine (5 mL) separately. The combined organic layers were dried (MgSO$_4$), filtered and concentrated. The crude oil was purified by reversed phase preparatory HPLC (Gemini™ Prep C$_{18}$ 5 µm column; Phenomenex, Torrance, CA; gradient elution of 35% to 95% MeCN in water, where both solvents contain 0.1% TFA, 30 min method) to afford the title compound as the first eluting isomer (4 mg, 3.9%). $^1$H NMR (400 MHz, CD$_2$Cl$_2$) δ 8.36 (br. s., 1H), 7.70 (d, J=8.41 Hz, 1H), 7.24-7.05 (m, 3H), 7.01-6.87 (m, 2H), 5.75 (ddd, J=5.67, 6.46, 18.39 Hz, 1H), 4.13 (s, 2H), 3.98 (t, J=6.16 Hz, 1H), 3.80-3.55 (m, 4H), 3.48-3.20 (m, 3H), 2.90-2.69 (m, 3H), 2.60 (d, J=7.24 Hz, 2H), 2.03-1.76 (m, 9H), 1.17 (d, J=6.85 Hz, 3H). m/z (ESI, +ve ion) 571.2 (M+H)$^+$.

Example 165. (1S,3'R,6'R,7'S,8'E,10'S)-6-chloro-7'-hydroxy-10'-methyl-3,4-dihydro-2H,14'H-spiro[naphthalene-1,21'-[19]oxa[12]thia [1,13]diazatetracyclo[13.7.2.0$^{3,6}$.0$^{18,23}$]tetracosa[8,15,17,23]tetraen]-14'-one 12',12'-dioxide or (1S,3'R,6'R,7'S,8'E,10'S)-6-chloro-7'-hydroxy-10'-methyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa [8,15,17,23]tetraen]-14'-one 12',12'-dioxide

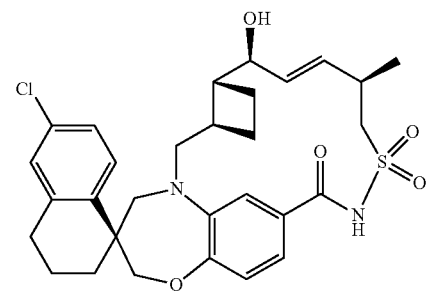

or

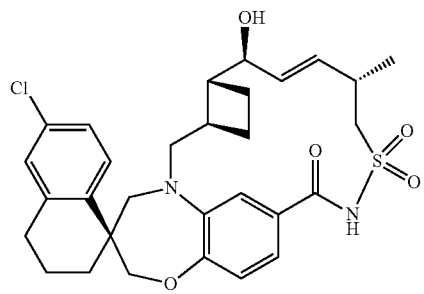

The title compound (1.9 mg, 1.8%) was obtained as the second eluting isomer from the reversed phase preparatory HPLC separation in Example 164, Step 6. $^1$H NMR (400 MHz, CD$_2$Cl$_2$) δ 7.71 (d, J=8.41 Hz, 1H), 7.23 (d, J=2.15 Hz, 1H), 7.18 (dd, J=2.35, 8.41 Hz, 1H), 7.10 (d, J=2.15 Hz, 1H), 6.96 (d, J=8.22 Hz, 1H), 6.88-6.81 (m, 1H), 5.84 (td, J=3.52, 15.26 Hz, 1H), 5.68 (td, J=8.41, 16.04 Hz, 1H), 4.12 (d, J=1.76 Hz, 3H), 3.76-3.51 (m, 3H), 3.47-3.18 (m, 3H), 2.94-2.58 (m, 4H), 2.44-2.30 (m, 1H), 2.00 (s, 9H), 1.12 (d, J=6.85 Hz, 3H). m/z (ESI, +ve ion) 571.2 (M+H)$^+$.

Example 166. (1S,3'R,6'R,7'S,8'E,10'S,11'R)-6-chloro-7'-hydroxy-10',11'-dimethyl-3,4-dihydro-2H,14'H-spiro[naphthalene-1,21'-[19]oxa[12]thia[1,13]diazatetracyclo[13.7.2.0³,⁶.0¹⁸,²³]tetracosa [8,15,17,23]tetraen]-14'-one 12',12'-dioxide or (1S,3'R,6'R,7'S,8'E,10'R,11'S)-6-chloro-7'-hydroxy-10',11'-dimethyl-3,4-dihydro-2H,14'H-spiro[naphthalene-1,21'-[19]oxa[12]thia[1,13]diazatetracyclo[13.7.2.0³,⁶.0¹⁸,²³]tetracosa [8,15,17,23]tetraen]-14'-one 12',12'-dioxide Example 167. (1S,3'R,6'R,7'S,8'E,11'S,12'R)-6-chloro-7'-hydroxy-11'-methyl-12'-((2S)-tetrahydro-2-furanylmethyl)-3,4-dihydro-2H,15'H-spiro[naphthalene-1,22'-[20]oxa[13]thia[1,14]diazatetracyclo [14.7.2.0³,⁶.0¹⁹,²⁴]pentacosa[8,16,18,24]tetraen]-15'-one 13',13'-dioxide or (1S,3'R,6'R,7'S,8'E,11'S,12'R)-6-chloro-7'-hydroxy-11'-methyl-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

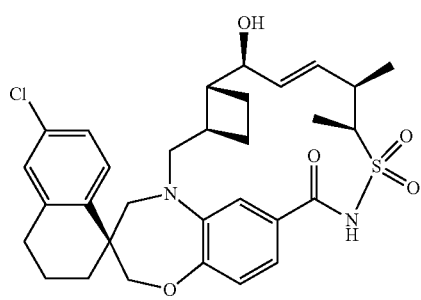 or

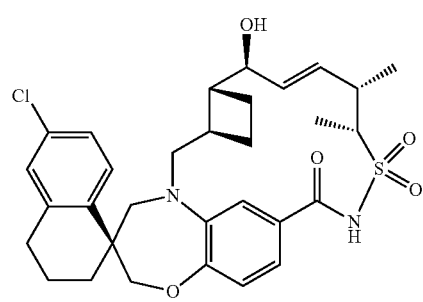

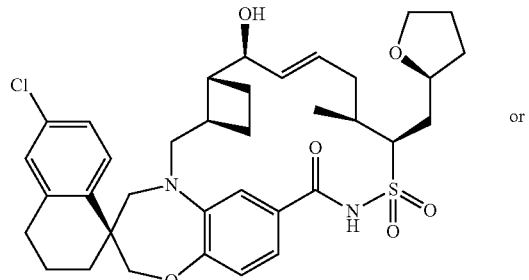 or

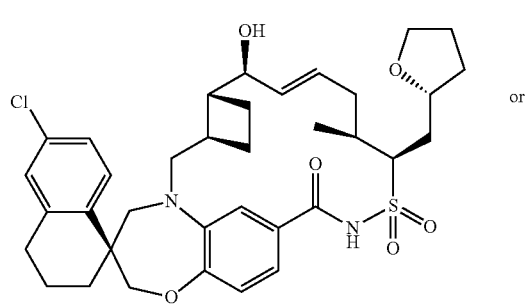 or

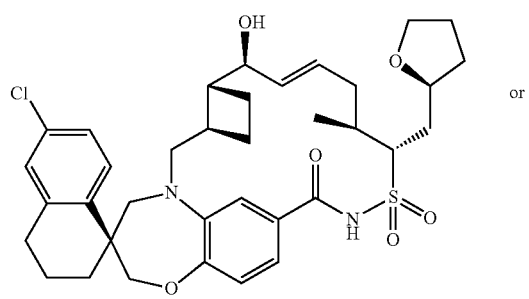 or

The title compound was obtained as the first eluting isomer (4 mg, 4.0%) from reversed phase preparatory HPLC in Example 144. ¹H NMR (400 MHz, CD$_2$Cl$_2$) δ 8.64-8.51 (m, 1H), 7.68 (m, 1H), 7.71-7.64 (m, 1H), 7.23 (d, J=8.41 Hz, 1H), 7.16 (dd, J=2.45, 8.51 Hz, 1H), 7.12-7.07 (m, 2H), 6.95 (d, J=8.22 Hz, 1H), 5.79 (ddq, J=5.87, 7.82, 15.45 Hz, 2H), 4.25-4.03 (m, 3H), 3.75-3.65 (m, J=7.04 Hz, 1H), 3.61-3.42 (m, 3H), 2.85-2.39 (m, 5H), 2.07-1.67 (m, 7H), 1.35-1.30 (m, 1H), 1.22-1.30 (m, 3H), 1.13 (d, J=6.85 Hz, 3H), 0.81-0.93 (m, 1H). m/z (ESI, +ve ion) 585.2 (M+H)⁺.

567
-continued

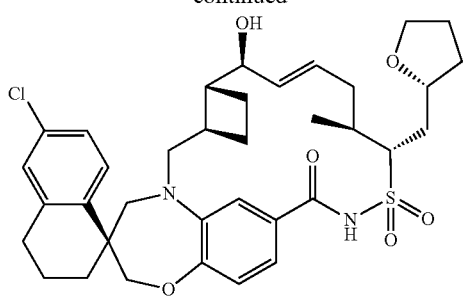

Step 1: (2S,3S)—N,N-bis(4-methoxybenzyl)-3-methyl-1-(tetrahydro-2-furanyl)-5-hexene-2-sulfonamide and (2R,3S)—N,N-bis(4-methoxybenzyl)-3-methyl-1-(tetrahydro-2-furanyl)-5-hexene-2-sulfonamide

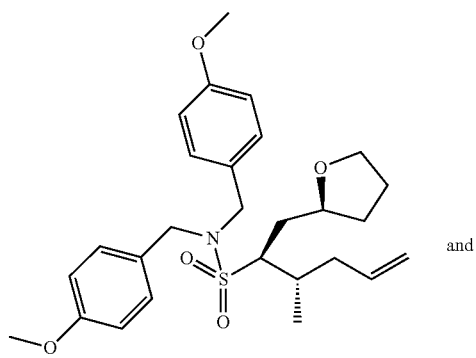

and and and

568
-continued

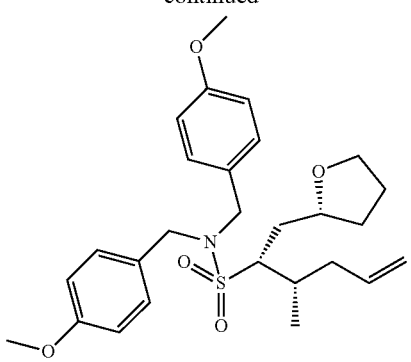

The title compound was prepared from (2S)—N, N-bis(4-methoxybenzyl)-2-methylpent-4-ene-1sulfonamide (Example 395, Step 3) using a similar procedure described in Example 395, Step 4, replacing ethylene oxide with 2-(bromomethyl)tetrahydrofuran.

Step 2: (2S,3S)-3-methyl-1-((2S)-(tetrahydro-2-furanyl)-5-hexene-2-sulfonamide and (2R,3S)-3-methyl-1-((2S)-(tetrahydro-2-furanyl)-5-hexene-2-sulfonamide and (2S,3S)-3-methyl-1-((2R)-(tetrahydro-2-furanyl)-5-hexene-2-sulfonamide and (2R,3S)-3-methyl-1-((2R)-(tetrahydro-2-furanyl)-5-hexene-2-sulfonamide

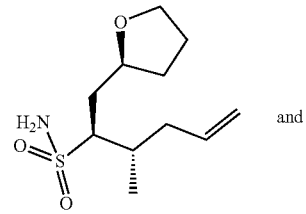

and

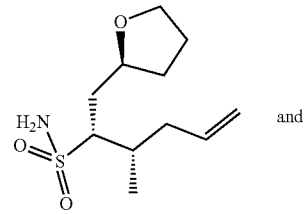

and

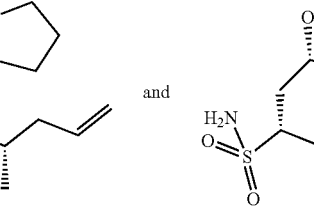

and

The title compounds were prepared from (2S,3S)—N,N-bis(4-methoxybenzyl)-3-methyl-1-(tetrahydro-2-furanyl)-5-hexene-2-sulfonamide and (2R,3S)—N,N-bis(4-methoxybenzyl)-3-methyl-1-(tetrahydro-2-furanyl)-5-hexene-2-sulfonamide using a similar procedure in Step 5 of Example 153.

Step 3: (1S,3'R,6'R,7'S,8'E,11'S,12'R)-6-chloro-7'-hydroxy-11'-methyl-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-7'-hydroxy-11'-methyl-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compound was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12) using a similar procedure described in Example 164, Step 5 to 6, replacing 2-methylbut-3-ene-1-sulfonamide in Step 5 with (2S,3S)-3-methyl-1-((2S)-(tetrahydro-2-furanyl)-5-hexene-2-sulfonamide and (2R,3S)-3-methyl-1-((2S)-(tetrahydro-2-furanyl)-5-hexene-2-sulfonamide and (2S,3S)-3-methyl-1-((2R)-(tetrahydro-2-furanyl)-5-hexene-2-sulfonamide and (2R,3S)-3-methyl-1-((2R)-(tetrahydro-2-furanyl)-5-hexene-2-sulfonamide. The crude residue of Step 6 was purified by reversed phase preparatory HPLC (Gemini™ Prep C$_{18}$ 5 μm column; Phenomenex, Torrance, CA; gradient elution of 50% to 90% MeCN in water, where both solvents contain 0.1% TFA, 30 min method) to afford the first eluting isomer (29 mg, 12%). $^{1}$H NMR (400 MHz, CD$_{2}$Cl$_{2}$) δ 8.33-8.13 (m, 1H), 7.70 (d, J=8.41 Hz, 1H), 7.17 (dd, J=2.35, 8.41 Hz, 1H), 7.09 (d, J=2.35 Hz, 1H), 7.05-6.96 (m, 1H), 6.91 (d, J=0.98 Hz, 2H), 5.82 (ddd, J=4.30, 8.61, 14.87 Hz, 1H), 5.68 (dd, J=7.43, 15.06 Hz, 1H), 4.23-4.02-(m, 5H), 3.88 (s, 1H), 3.82-3.58 (m, 3H), 3.35-3.24 (m, 1H), 3.20-3.02 (m, 1H), 2.77 (d, J=4.89 Hz, 2H), 2.32 (d, J=7.24 Hz, 3H), 2.22-1.75 (m, 12H), 1.59-1.42 (m, 5H), 1.05 (d, J=6.65 Hz, 3H). m/z (ESI, +ve ion) 669.2 (M+H)$^{+}$.

Example 168. (1S,3'R,6'R,7'S,8'E,11'S,12'R)-6-chloro-7'-hydroxy-11'-methyl-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-7'-hydroxy-11'-methyl-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

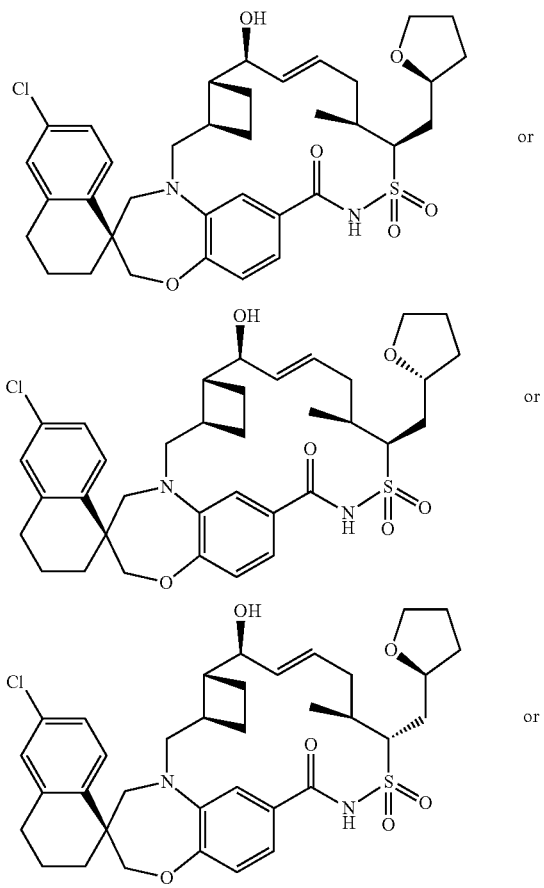

571

-continued

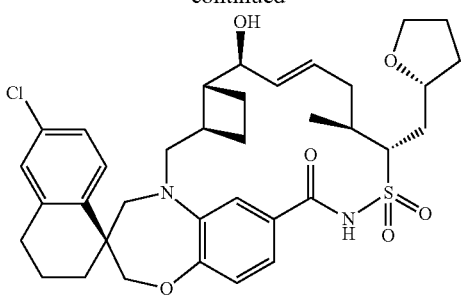

The title compound (16 mg, 6.7%) was obtained as the second eluting isomer from the reversed phase preparatory HPLC separation in Example 167. $^1$H NMR (400 MHz, CD$_2$Cl$_2$) δ 8.13 (br. s., 1H), 7.70 (d, J=8.6 Hz, 1H), 7.17 (dd, J=2.3, 8.6 Hz, 1H), 7.09 (d, J=2.3 Hz, 1H), 6.94 (s, 1H), 6.90 (s, 2H), 5.95-5.82 (m, 1H), 5.71 (dd, J=7.9, 15.2 Hz, 1H), 4.40 (d, J=9.2 Hz, 1H), 4.34-4.25 (m, 1H), 4.21 (dd, J=4.1, 8.0 Hz, 1H), 4.12-4.06 (m, 2H), 3.88-3.71 (m, 3H), 3.67 (d, J=14.3 Hz, 1H), 3.27 (d, J=14.1 Hz, 1H), 3.15-3.00 (m, 1H), 2.84-2.70 (m, 2H), 2.48-1.79 (m, 16H), 1.59-1.34 (m, 3H), 1.00 (d, J=6.8 Hz, 3H). m/z (ESI, +ve ion) 669.2 (M+H)$^+$.

Example 169. (1S,3'R,6'R,7'S,8'E,11'S,12'R)-6-chloro-7'-methoxy-11'-methyl-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-7'-methoxy-11'-methyl-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-methoxy-11'-methyl-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-methoxy-11'-methyl-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

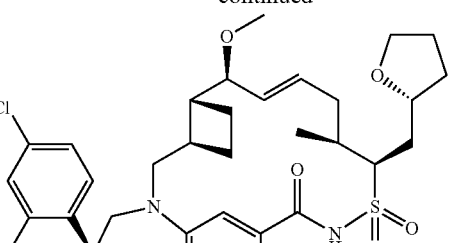

or

572

-continued

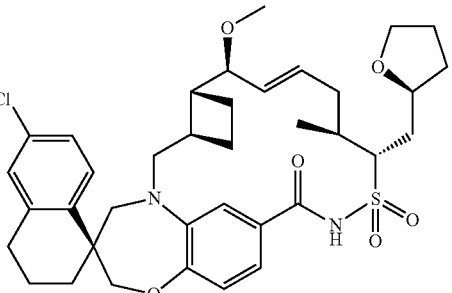

or

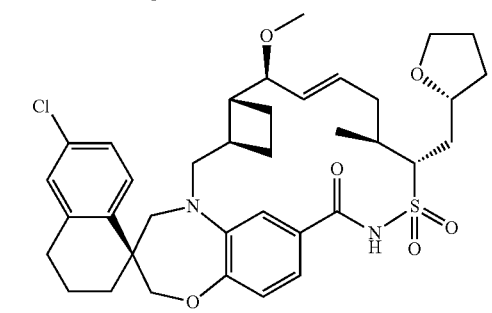

The title compound (9.5 mg, 62%) was prepared from (1S,3'R,6'R,7'S,8'E,11'S,12'R)-6-chloro-7'-hydroxy-11'-methyl-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-7'-hydroxy-11'-methyl-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methyl-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-methyl-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (Example 167) using a similar procedure described in Example 95. $^1$H NMR (400 MHz, CD$_2$Cl$_2$) δ 8.16 (s, 1H), 7.71 (d, J=8.4 Hz, 1H), 7.17 (d, J=8.4 Hz, 1H), 7.09 (s, 1H), 6.91 (s, 1H), 6.90-6.84 (m, 1H), 5.87-5.72 (m, 1H), 5.51 (dd, J=8.9, 15.4 Hz, 1H), 4.32-4.15 (m, 2H), 4.12-4.04 (m, 2H), 3.97-3.60 (m, 6H), 3.32-3.13 (m, 4H), 3.04 (dd, J=10.2, 15.1 Hz, 1H), 2.76 (dd, J=5.1, 10.4 Hz, 2H), 2.52-1.90 (m, 15H), 1.70-1.63 (m, 1H), 1.55-1.46 (m, 1H), 1.45-1.35 (m, 1H), 1.06 (d, J=7.0 Hz, 3H). m/z (ESI, +ve ion) 783.1 (M+H)$^+$.

Example 170. (1S,3'R,6'R,7'S,8'E,11'S,12'R)-6-chloro-7'-methoxy-11'-methyl-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-methoxy-11'-methyl-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-methoxy-11'-methyl-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-methoxy-11'-methyl-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

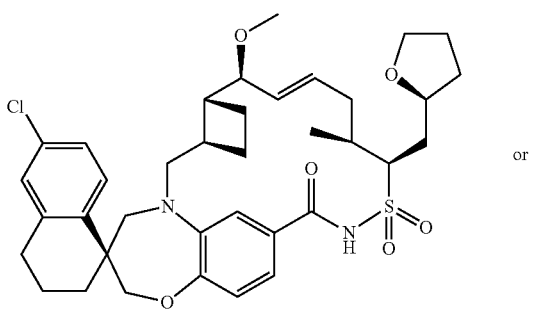

or

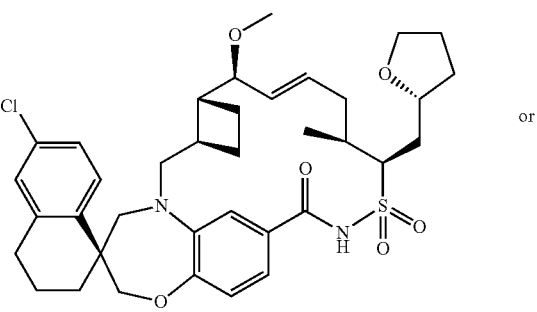

or

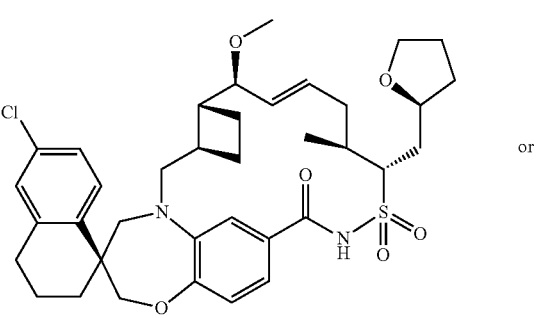

or

-continued

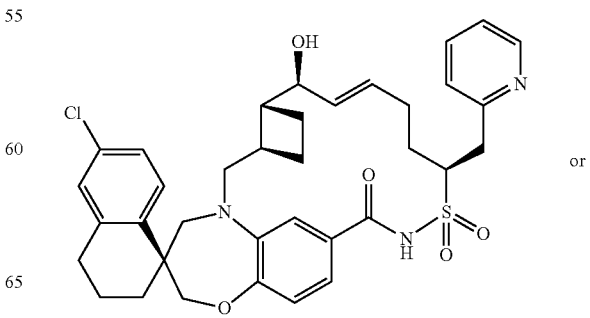

The title compound (7 mg, 53%) was prepared from (1S,3'R,6'R,7'S,8'E,11'S,12'R)-6-chloro-7'-hydroxy-1 r-methyl-12'-((2s)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-hydroxy-11'-methyl-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methyl-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (Example 168) using a similar procedure described in Example 95. $^{1}$H NMR (400 MHz, CD$_2$Cl$_2$) δ 8.08 (s, 1H), 7.71 (d, J=8.6 Hz, 1H), 7.17 (dd, J=2.2, 8.6 Hz, 1H), 7.09 (d, J=2.2 Hz, 1H), 6.90 (s, 2H), 6.86 (s, 1H), 5.87 (ddd, J=2.9, 10.0, 15.0 Hz, 1H), 5.50 (dd, J=9.5, 15.6 Hz, 1H), 4.51 (d, J=8.8 Hz, 1H), 4.37-4.26 (m, 1H), 4.08 (s, 2H), 3.87-3.59 (m, 5H), 3.25 (d, J=14.3 Hz, 1H), 3.19 (s, 3H), 3.03 (dd, J=10.2, 15.3 Hz, 1H), 2.84-2.71 (m, 2H), 2.52-1.75 (m, 16H), 1.52 (qd, J=7.5, 12.1 Hz, 1H), 1.44-1.34 (m, 1H), 1.01 (d, J=6.8 Hz, 3H). m/z (ESI, +ve ion) 783.2 (M+H)$^+$.

Example 176. (1S,3'R,6'R,7'S,8'E,12'S)-6-chloro-7'-hydroxy-12'-(2-pyridinylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-hydroxy-12'-(2-pyridinylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or -continued

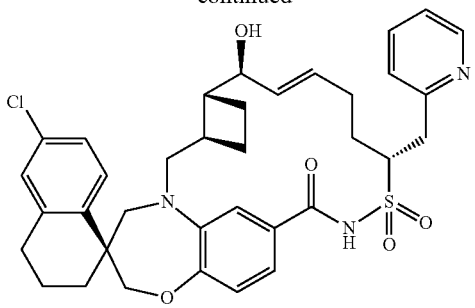

Step 1: (R)—N,N-bis(4-methoxybenzyl)-1-(pyridin-2-yl)hex-5-ene-2-sulfonamide and (S)—N,N-bis(4-methoxybenzyl)-1-(pyridin-2-yl)hex-5-ene-2-sulfonamide

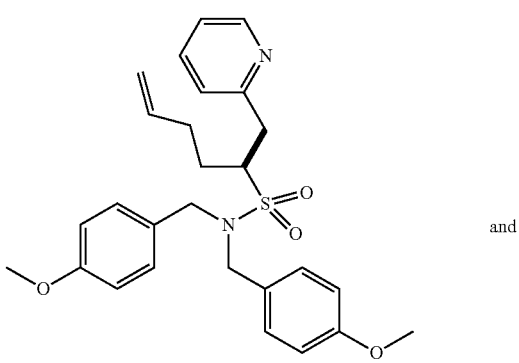

To a solution of N,N-bis(4-methoxybenzyl)pent-4-ene-1-sulfonamide (1.34 g, 3.44 mmol, Intermediate EE19) at −78° C. in THF (17.2 mL) was added butyllithium solution, 2.5 M in hexanes (1.38 mL, 3.44 mmol). The reaction mixture was stirred at this temperature for 30 minutes. In a separate flask, charged with a solution of 2-(bromomethyl)pyridine hydrobromide (1.74 g, 6.88 mmol) in DCM (4 mL) was added saturated NaHCO₃ (4 mL) and the biphasic mixture was stirred for 15 minutes. The aqueous layer was separated and extracted with DCM. The combined organic layers were dried (MgSO₄) and filtered, toluene (10 mL) was added, and the mixture was concentrated to a 1 mL solution. This solution was then added to the first flask containing the nucleophile. The resulting reaction mixture was stirred at −78° C. After 15 minutes, the reaction mixture was allowed to stir for an additional hour and then quenched with saturated aqueous NH₄Cl. The mixture was extracted with diethyl ether, the combined organic layers were washed with brine, dried (MgSO₄), filtered and concentrated. The residue was injected into a 40 g ISCO Gold column and purified by combi-flash, eluting with 0% to 100% EtOAc/hexanes to give the title compounds (960 mg, 1.99 mmol) as a light yellow solid.

Step 2. (R)-1-(pyridin-2-yl)hex-5-ene-2-sulfonamide and (S)-1-(pyridin-2-yl)hex-5-ene-2-sulfonamide

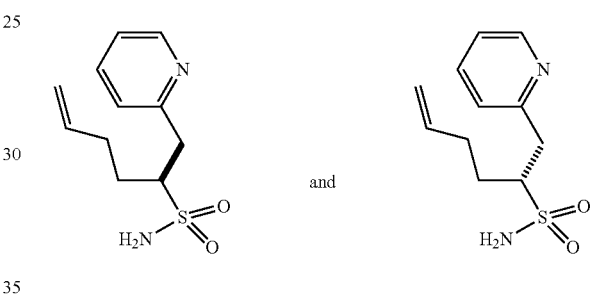

Following the same experiment procedure as Example 153, Step 5, (R)—N,N-bis(4-methoxybenzyl)-1-(pyridin-2-yl)hex-5-ene-2-sulfonamide and (S)—N,N-bis(4-methoxybenzyl)-1-(pyridin-2-yl)hex-5-ene-2-sulfonamide was treated with anisole and TFA to afford the title compounds.

Step 3: (S)-6'-chloro-5-(((1R,2R)-2-((S,E)-1-hydroxyhex-2-en-1-yl)cyclobutyl)methyl)-N—(((S)-1-(pyridin-2-yl)hex-5-en-2-yl)sulfonyl)-3',4,4',5-tetrahydro-2H,2'H-carboxamide and (S)-6'-chloro-5-(((1R,2R)-2-((S,E)-1-hydroxyhex-2-en-1-yl)cyclobutyl)methyl)-N—(((R)-1-(pyridin-2-yl)hex-5-en-2-yl)sulfonyl)-3',4,4',5-tetrahydro-2H,2'H-spiro[benzo[b][1,4]oxazepine-3,1'-naphthalene]-7-carboxamide

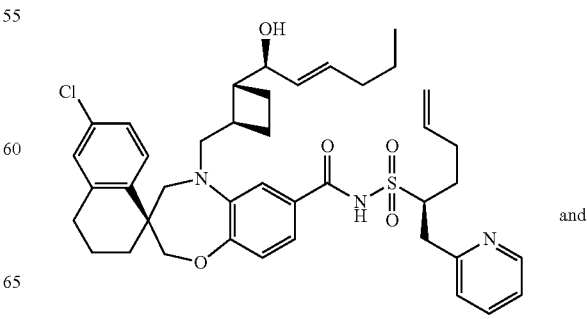

-continued

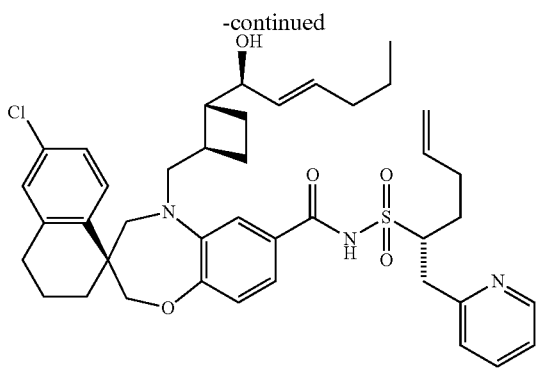

N,N-dimethylpyridin-4-amine (DMAP) (47.9 mg, 0.392 mmol) was added to a solution of (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (0.100 mg, 0.196 mmol, Intermediate AA12), triethylamine (0.082 mL, 0.588 mmol) and (R)-1-(pyridin-2-yl)hex-5-ene-2-sulfonamide and (S)-1-(pyridin-2-yl)hex-5-ene-2-sulfonamide (Example 176, Step 2) (0.094 g, 0.392 mmol) in DCM (2 mL). Then EDC (75 mg, 0.392 mmol) was added slowly in portions, and reaction mixture was stirred at ambient temperature overnight. The residue was injected into a 40 g ISCO Gold column and purified by combi-flash, eluting with 10% to 100% EtOAc (containing 1.0% AcOH)/hexanes to give the title compounds (100 mg, 0.137 mmol).

Step 4: (1S,3'R,6'R,7'S,8'E,12'S)-6-chloro-7'-hydroxy-12'-(2-pyridinylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-hydroxy-12'-(2-pyridinylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide A 100 mL round bottom flask was charged with the product from Example 176, Step 3 (0.100 g, 0.137 mmol) in AcOH (47.1 mL). It was stirred at ambient temperature sparging Ar through the reaction mixture for 15 min. To the homogeneous solution was added Hoveyda-Grubbs II (0.017 g, 0.027 mmol). The mixture was stirred at ambient temperature under reduced pressure overnight and then air was sparged through for 10 min. The reaction mixture was concentrated. The crude product was purified by reversed phase preparatory HPLC (Gemini™ Prep C$_{18}$ 5 µm column; Phenomenex, Torrance, CA; gradient elution of 35% to 95% MeCN in water, where both solvents contain 0.1% TFA, 30 min method) to provide one of the title compounds as white solid (0.0017 g, 0.0025 mmol). $^1$H NMR (400 MHz, CD$_2$Cl$_2$) δ ppm 8.76 (d, J=5.5 Hz, 1H), 8.23 (t, J=7.3 Hz, 1H), 7.82 (d, J=8.0 Hz, 1H), 7.71 (m, 1H), 7.70-7.68 (m, 1H), 7.16 (dd, J=2.1, 8.5 Hz, 1H), 7.09 (d, J=2.2 Hz, 1H), 6.93-6.87 (m, 3H), 5.86 (m, 1H), 5.74-5.66 (m, 1H), 4.63 (t, J=6.0 Hz, 1H), 4.21 (dd, J=4.3, 7.8 Hz, 1H), 4.07 (s, 2H), 3.81 (d, J=15.3 Hz, 1H), 3.72-3.58 (m, 3H), 3.25 (d, J=14.3 Hz, 1H), 3.04 (dd, J=9.6, 15.5 Hz, 1H), 2.81-2.24 (m, 6H), 2.10-1.88 (m, 5H), 1.88-1.72 (m, 3H), 1.72-1.61 (m, 1H), 1.40 (t, J=12.9 Hz, 1H); m/z (ESI, +ve ion) 662 (M+Na)$^+$.

Example 186. (1S,3'R,6'R,7'S,8'E,12'S)-6-chloro-7'-hydroxy-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide or (1S,3'R,6'R,7'S,8'E,12'R)-6-chloro-7'-hydroxy-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide

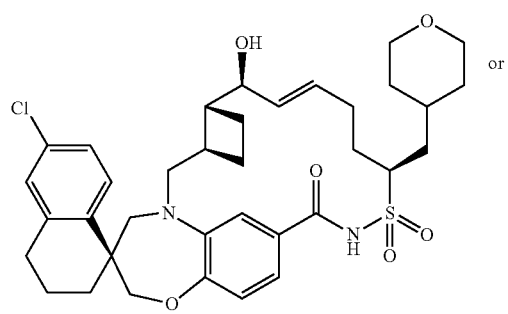

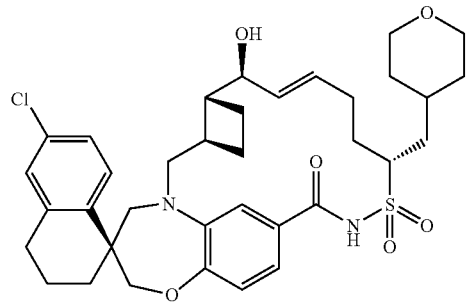

Step 1: (S)—N,N-bis(4-methoxybenzyl)-1-(tetrahydro-2H-pyran-4-yl)hex-5-ene-2-sulfonamide and (R)—N,N-bis(4-methoxybenzyl)-1-(tetrahydro-2H-pyran-4-yl)hex-5-ene-2-sulfonamide

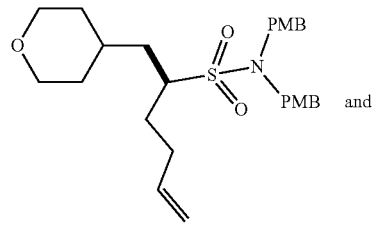

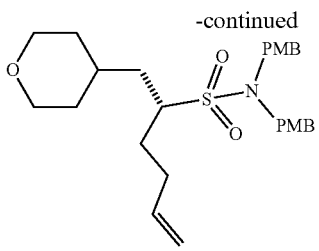

To a solution of N,N-bis(4-methoxybenzyl)pent-4-ene-1-sulfonamide (2.40 g, 6.16 mmol, Intermediate EE19) in THF (5 mL) was added butyllithium solution, 2.5 M in hexanes (3.20 mL, 8.01 mmol) at −78° C. dropwise. After being stirred at −78° C. for 10 min, 4-bromomethyltetrahydropyran (4.41 g, 24.6 mmol) was added into the reaction for 30 minutes at the same temp. After this time, the reaction was allowed to warm to room temperature. After being stirred at room temperature for 2 h, the reaction was quenched (sat.NH$_4$Cl), extracted (2×EtOAc), and washed (1× brine). The combined organic layer were dried (Na$_2$SO$_4$) and concentrated under the reduced pressure. The residue was injected into a 40 g ISCO Gold column and purified by combi-flash, eluting with 0% to 30% EtOAc/hexanes to give the title compound (1.5 g, 3.08 mmol).

Step 2: (1S,3'R,6'R,7'S,8'E,12'S)-6-chloro-7'-hydroxy-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-hydroxy-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compounds was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12) by a procedure analogous to that described in Example 176, Steps 2 through 4, replacing (R)—N,N-bis(4-methoxybenzyl)-1-(pyridin-2-yl)hex-5-ene-2-sulfonamide and (S)—N,N-bis(4-methoxybenzyl)-1-(pyridin-2-yl)hex-5-ene-2-sulfonamide in Step 2 with (S)—N,N-bis(4-methoxybenzyl)-1-(tetrahydro-2h-pyran-4-yl)hex-5-ene-2-sulfonamide and (R)—N,N-bis(4-methoxybenzyl)-1-(tetrahydro-2h-pyran-4-yl)hex-5-ene-2-sulfonamide (Example 186, Step 1). The residue was injected into a 40 g ISCO Gold column and purified by combi-flash, eluting with 10% to 100% EtOAc (containing 0.5% AcOH)/hexanes to give a crude product as the faster eluting isomer. This crude product was purified by reversed phase preparative HPLC (Gemini™ Prep C$_{18}$ 5 μm column; Phenomenex, Torrance, CA; gradient elution of 50% to 90% MeCN in water, where both solvents contain 0.1% TFA, 30 min method) to provide one of the title compounds as a white foam. $^1$H NMR (400 MHz, CD$_2$Cl$_2$) δ ppm 8.28 (br. s., 1H), 7.66 (d, J=8.4 Hz, 1H), 7.48 (m, 1H), 7.15 (dd, J=2.2, 8.5 Hz, 1H), 7.10 (m, 1H), 6.99-6.88 (m, 2H), 5.72-5.60 (m, 1H), 5.54 (m, 1H), 4.20 (s, 2H), 4.07-3.81 (m, 5H), 3.70 (d, J=13.9 Hz, 1H), 3.50-3.31 (m, 3H), 3.20 (m, 1H), 2.80-2.70 (m, 2H), 2.56-2.42 (m, 2H), 2.31 (m, 1H), 2.13 (m, 1H), 2.06-1.64 (m, 13H), 1.60-1.44 (m, 2H), 1.39-1.23 (m, 2H); m/z (ESI, +ve ion) 669 (M+H)$^+$.

Example 187. (1S,3'R,6'R,7'S,8'E,12'S)-6-chloro-7'-hydroxy-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-hydroxy-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

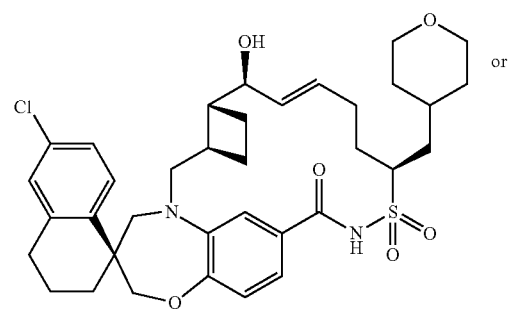

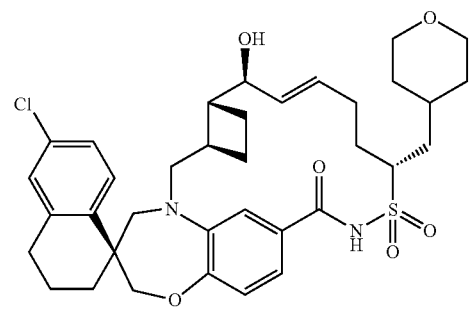

One of the title compounds was obtained as the second (slower) eluting isomer using combi-flash separation as described in Example 186. $^1$H NMR (400 MHz, CD$_2$Cl$_2$) δ ppm 8.24 (s, 1H), 7.71 (d, J=8.4 Hz, 1H), 7.17 (dd, 8.5 Hz, 1H), 7.09 (d, J=2.2 Hz, 1H), 6.94-6.87 (m, 3H), 5.83-5.68 (m, 2H), 4.19 (dd, J=4.0, 7.3 Hz, 1H), 4.16-4.05 (m, 3H), 4.00-3.88 (m, 2H), 3.82 (m, 1H), 3.70 (d, J=14.1 Hz, 1H), 3.41 (m, 2H), 3.25 (d, J=14.3 Hz, 1H), 3.03 (dd, J=9.4, 15.3 Hz, 1H), 2.82-2.69 (m, 2H), 2.46-2.27 (m, 3H), 2.20-1.63 (m, 13H), 1.52 (ddd, J=3.9, 8.9, 14.9 Hz, 1H), 1.44-1.19 (m, 4H); m/z (ESI, +ve ion) 669 (M+H)$^+$.

Example 188. (1S,3'R,6'R,7'S,8'E,11'S,12'R)-6-chloro-7'-hydroxy-11'-methyl-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'R,12'S)-6-chloro-7'-hydroxy-11'-methyl-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'R,12'R)-6-chloro-7'-hydroxy-11'-methyl-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

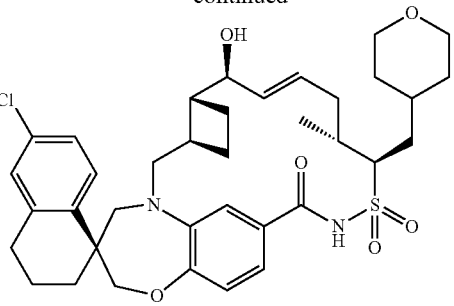

Step 1: (2R,3R)—N,N-bis(4-methoxybenzyl)-3-methyl-1-(tetrahydro-2H-pyran-4-yl)hex-5-ene-2-sulfonamide and (2S,3S)—N,N-bis(4-methoxybenzyl)-3-methyl-1-(tetrahydro-2H-pyran-4-yl)hex-5-ene-2-sulfonamide and (2S,3R)—N,N-bis(4-methoxybenzyl)-3-methyl-1-(tetrahydro-2H-pyran-4-yl)hex-5-ene-2-sulfonamide and (2R,3S)—N,N-bis(4-methoxybenzyl)-3-methyl-1-(tetrahydro-2H-pyran-4-yl)hex-5-ene-2-sulfonamide

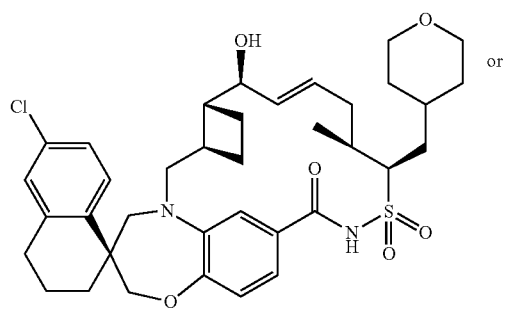
or

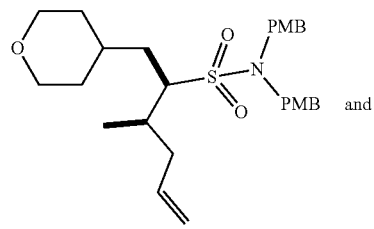
and

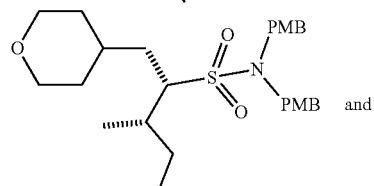
and

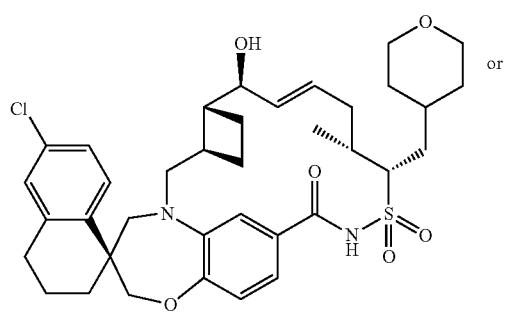
or

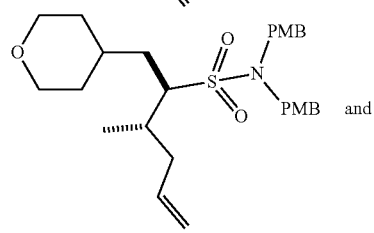
and

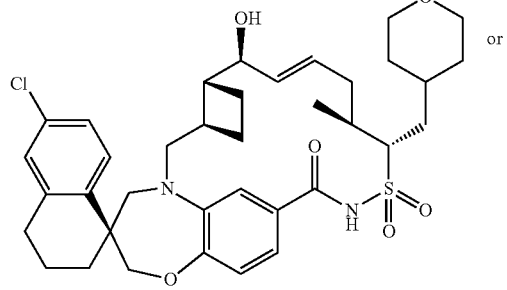
or

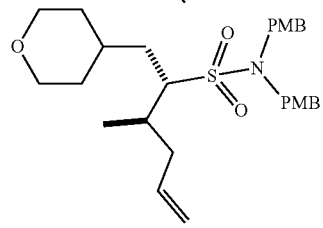

To a solution of (R)—N,N-bis(4-methoxybenzyl)-2-methylpent-4-ene-1-sulfonamide and (S)—N,N-bis(4-methoxybenzyl)-2-methylpent-4-ene-1-sulfonamide (2.0 g, 4.96 mmol, Example 647, Step 7) at −78° C. in THF (24.8 mL) was added butyllithium solution, 2.5m in hexanes (2.39 mL, 5.90 mmol). After the reaction was stirred at the same temperature for 30 minutes. 4-bromomethyltetrahydropyran (3.55 mL, 19.8 mmol) was added. Then the reaction was allowed to warm to ambient temperature and stirred for 3 hours. The reaction was quenched (saturated aqueous NH$_4$Cl), extracted (3× Et$_2$O), and washed (brine). The combined organic layers were dried (Na$_2$SO$_4$) and concentrated under reduced pressure. The residue was injected into a 80 g ISCO Gold column and purified by combi-flash, eluting with 0% to 20% EtOAc (containing 0.3% AcOH)/hexanes to give the title compounds (1.30 g, 2.59 mmol).

Step 2: (2R,3R)-3-methyl-1-(tetrahydro-2H-pyran-4-yl)hex-5-ene-2-sulfonamide and (2S,3S)-3-methyl-1-(tetrahydro-2H-pyran-4-yl)hex-5-ene-2-sulfonamide and (2S,3R)-3-methyl-1-(tetrahydro-2H-pyran-4-yl)hex-5-ene-2-sulfonamide and (2R,3S)-3-methyl-1-(tetrahydro-2H-pyran-4-yl)hex-5-ene-2-sulfonamide


and


and

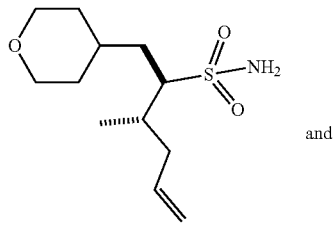

and

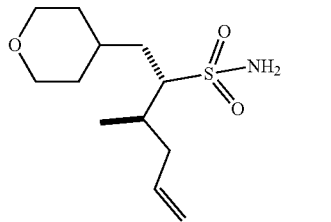

A solution of (2R,3R)—N,N-bis(4-methoxybenzyl)-3-methyl-1-(tetrahydro-2H-pyran-4-yl)hex-5-ene-2-sulfonamide and (2S,3S)—N,N-bis(4-methoxybenzyl)-3-methyl-1-(tetrahydro-2H-pyran-4-yl)hex-5-ene-2-sulfonamide and (2S,3R)—N,N-bis(4-methoxybenzyl)-3-methyl-1-(tetrahydro-2H-pyran-4-yl)hex-5-ene-2-sulfonamide and (2R,3S)—N,N-bis(4-methoxybenzyl)-3-methyl-1-(tetrahydro-2H-pyran-4-yl)hex-5-ene-2-sulfonamide (1.3 g, 2.59 mmol), trifluoroacetic acid (19.9 mL, 259 mmol) and anisole, anhydrous (28.2 mL, 259 mmol) was heated at 40° C. overnight. The crude mixture was cooled and concentrated under reduced pressure. The residue was injected into a 80 g ISCO Gold column and purified by combi-flash, eluting with 30% to 100% EtOAc (containing 0.3% AcOH)/hexanes to give the title compounds (540 mg, 2.06 mmol) as light-yellow oil.

Step 3: (1S,3'R,6'R,7'S,8'E,11'S,12'R)-6-chloro-7'-hydroxy-11'-methyl-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11R,12'S)-6-chloro-7'-hydroxy-11'-methyl-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-7'-hydroxy-11'-methyl-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compounds was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12) by a procedure analogous to that described in Example 176, Steps 3-4, replacing 1(R)-1-(pyridin-2-yl)hex-5-ene-2-sulfonamide and (S)-1-(pyridin-2-yl)hex-5-ene-2-sulfonamide in Step 3 with (2R,3R)-3-methyl-1-(tetrahydro-2H-pyran-4-yl)hex-5-ene-2-sulfonamide and (2S,3S)-3-methyl-1-(tetrahydro-2H-pyran-4-yl)hex-5-ene-2-sulfonamide and (2S,3R)-3-methyl-1-(tetrahydro-2H-pyran-4-yl)hex-5-ene-2-sulfonamide and (2R,3S)-3-methyl-1-(tetrahydro-2H-pyran-4-yl)hex-5-ene-2-sulfonamide (Example 179, Step 2). The residue was purified by reversed phase preparatory HPLC (Gemini™ Prep C$_{18}$ 5 μm column; Phenomenex, Torrance, CA; gradient elution of 50% to 90% MeCN in water, where both solvents contain 0.1% TFA, 30 min method) to provide one of the title compounds as the faster eluting isomer as a white foam. $^1$H NMR (400 MHz, CD$_2$Cl$_2$) δ ppm 8.29 (br. s., 1H), 7.72-7.57 (m, 2H), 7.15 (d, J=8.7 Hz, 1H), 7.10 (m, 1H), 6.95-6.89 (m, 2H), 5.73-5.63 (m, 1H), 5.60-5.46 (m, 1H), 4.23 (s, 2H), 4.18-4.07 (m, 1H), 4.06-3.83 (m, 4H), 3.81-3.62 (m, 1H), 3.48-3.28 (m, 3H), 3.12 (m, 1H), 2.80-2.69 (m, 2H), 2.58-2.35 (m, 3H), 2.20-2.11 (m, 1H), 2.05-1.54 (m, 12H), 1.49-1.14 (m, 4H), 1.11-0.99 (m, 3H); m/z (ESI, +ve ion) 683 (M+H)$^+$.

Example 189. (1S,3'R,6'R,7'S,8'E,11'S,12'R)-6-chloro-7'-hydroxy-11'-methyl-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-7'-hydroxy-11'-methyl-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-7'-hydroxy-11'-methyl-12'-(tetrahydro-2H-pyran-4-ylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

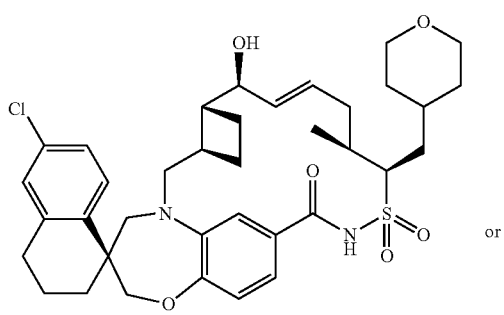 or

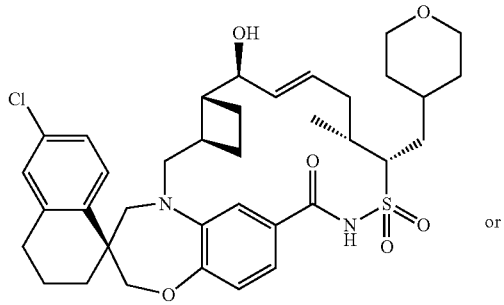 or

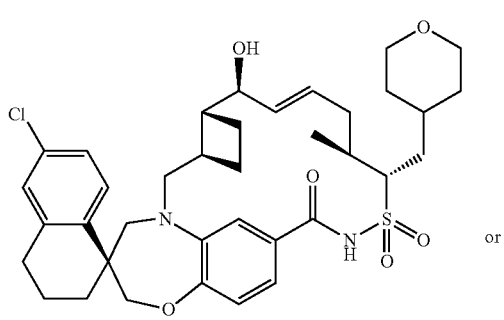 or

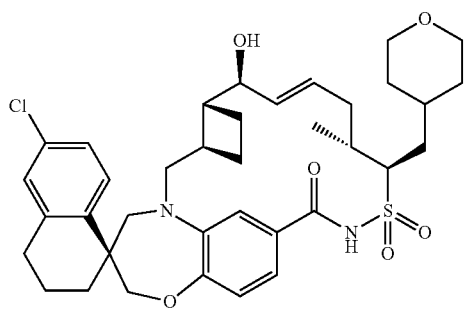

One of the title compounds was obtained as the second (slower) eluting isomer using reversed phase preparatory HPLC as described in Example 188. $^1$H NMR (400 MHz, CD$_2$Cl$_2$) δ ppm 10.28 (br. s., 1H), 7.72 (m, 1H), 7.43 (m, 1H), 7.28-7.13 (m, 2H), 7.10 (sm, 1H), 6.97 (d, J=7.8 Hz, 1H), 5.88-5.78 (m, 1H), 5.57-5.40 (m, 1H), 4.45 (m, 1H), 4.17-4.10 (m, 2H), 3.99-3.90 (m, 2H), 3.75 (m, 1H), 3.63 (d, J=13.9 Hz, 1H), 3.49-3.33 (m, 2H), 3.32-3.15 (m, 2H), 3.08 (m, 1H), 2.82-2.70 (m, 2H), 2.52 (m, 1H), 2.30 (m, 1H), 2.24-2.07 (m, 3H), 2.06-1.93 (m, 3H), 1.92-1.44 (m, 10H), 1.35-1.16 (m, 4H), 1.16-1.08 (m, 3H); m/z (ESI, +ve ion) 683 (M+H)$^+$.

Example 195. [(1S,3'S,6'R)-6-chloro-3,4-dihydro-2H,15'H-spiro[naphthalene-1,22'-[20]oxa[7,13]dithia[1,14]diazatetracyclo[14.7.2.0$^{3,6}$.0$^{19,24}$]pentacosa[16,18,24]trien]-15'-one 13',13'-dioxide] and (1S,3'R,6'S)-6-chloro-3,4-dihydro-2H,15'H-spiro[naphthalene-1,22'-[20]oxa[7,13]dithia[1,14]diazatetracyclo[14.7.2.0$^{3,6}$.0$^{19,24}$]pentacosa[16,18,24]trien]-15'-one 13',13'-dioxide] or [(1S,3'S,6'R)-6-chloro-3,4-dihydro-2H,15'H-spiro[naphthalene-1,22'-[20]oxa[7,13]dithia[1,14]diazatetracyclo[14.7.2.0$^{3,6}$.0$^{19,24}$]pentacosa[16,18,24]trien]-15'-one 13',13'-dioxide] and (1S,3'R,6'R)-6-chloro-3,4-dihydro-2H,15'H-spiro[naphthalene-1,22'-[20]oxa[7,13]dithia[1,14]diazatetracyclo[14.7.2.0$^{3,6}$.0$^{19,24}$]pentacosa[16,18,24]trien]-15'-one 13',13'-dioxide] or [(1S,3'S,6'R)-6-chloro-3,4-dihydro-2H,15'H-spiro[naphthalene-1,22'-[20]oxa[7,13]dithia[1,14]diazatetracyclo[14.7.2.0$^{3,6}$.0$^{19,24}$]pentacosa[16,18,24]trien]-15'-one 13',13'-dioxide] and (1S,3'S,6'S)-6-chloro-3,4-dihydro-2H,15'H-spiro[naphthalene-1,22'-[20]oxa[7,13]dithia[1,14]diazatetracyclo[14.7.2.0$^{3,6}$.0$^{19,24}$]pentacosa[16,18,24]trien]-15'-one 13',13'-dioxide]

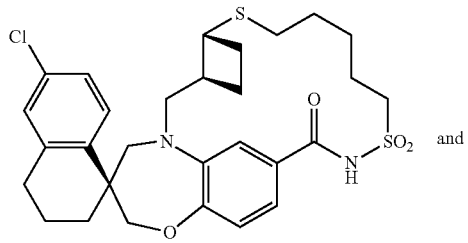 and

-continued

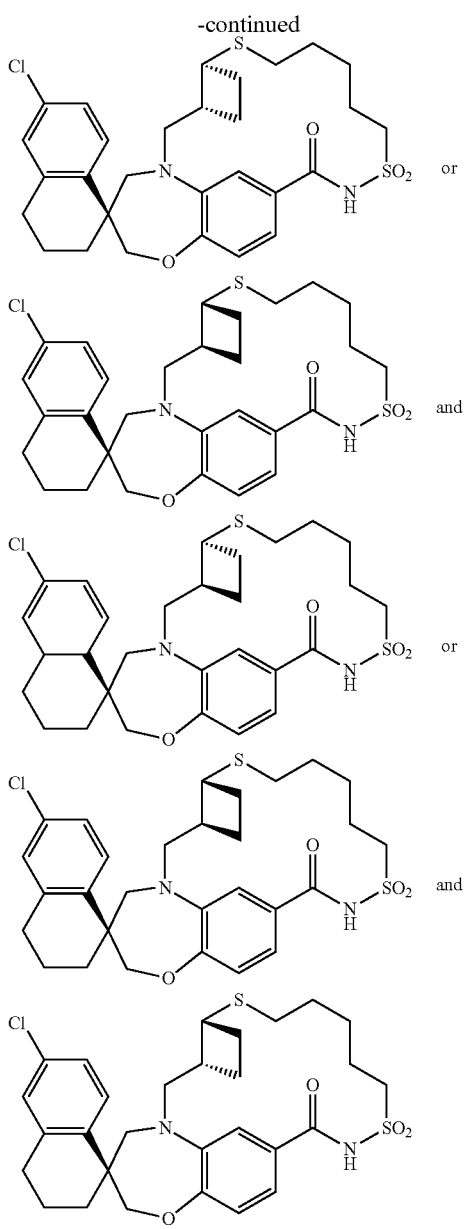

Step 1: benzyl 2-cyclopropylideneacetate

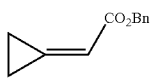

The cyclopropanone precursor, (1-ethoxycyclopropoxy) trimethylsilane (Wonda, 500 g, 2.866 mol), was dissolved in methanol (1.4 L) and the resulting solution was stirred at ambient temperature for two days. Methanol was removed in vacuo to provide the crude cyclopropanone ethyl hemiacetal intermediate. This material was redissolved in anhydrous chloroform (3 L), benzoic acid (63.7 g, 0.52 mol) was added, and the resulting reaction mixture was heated at reflux for 10 min under an atmosphere of dry nitrogen. A solution of benzyl 2-(triphenylphosphoranylidene) acetate (Wonda, 1.07 kg, 2.61 mol) dissolved in the minimum volume of chloroform was then added to the reaction mixture dropwise. On completion of the reaction as assessed by TLC analysis, the mixture was allowed to cool to room temperature and the solvent was removed on a rotary evaporator. The residue was purified by flash chromatography (60-120 mesh silica gel) using a solvent gradient of 0 to 5% ethyl acetate in hexanes to afford the title compound (331 g, 61% yield) as a colorless oil.

Step 2: (S)-benzyl 2-hydroxy-2-(1-hydroxycyclopropyl)acetate, predominantly and (R)-benzyl 2-hydroxy-2-(1-hydroxycyclopropyl)acetate (predominantly (S))

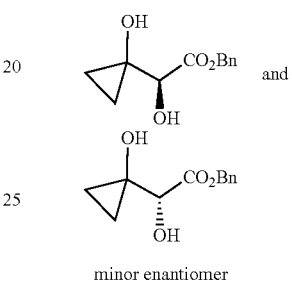

minor enantiomer

To an ice-cooled solution of benzyl 2-cyclopropylideneacetate (331 g, 1.76 mol) in a mixture of tert-butanol (8.8 L) and water (8.8 L) was added AD-mix β (Aldrich, 2.45 kg). The resulting orange suspension was vigorously stirred at 0° C. Ten minutes later, methanesulfonamide (Alfa Aesar, 167 g, 1.76 mol) was added and the reaction mixture was stirred at 0° C. for 16 h, after which time solid sodium sulfite (830 g, 6.58 mol) was added. Stirring at 0° C. for was continued for 15 minutes. The reaction mixture was diluted with ethyl acetate (10 L). Layers were separated and the aqueous layer was extracted with ethyl acetate (2×3 L). The combined organic layers was washed with brine again, dried over sodium sulfate, filtered and concentrated in vacuo to yield the crude material, which was purified by column chromatography (60-120 mesh silica), eluting with a gradient of 0 to 40% ethyl acetate in hexanes, to afford the title compound as a translucent oil (260 g, 66% yield). Predominantly (S) benzyl 2-hydroxy-2-(1-hydroxycyclopropyl)acetate prepared in this manner typically had 86-89% enantiomeric excess as determined by chiral HPLC [Chiral pak IC column (250 mm×4.6 mm); Mobile Phase: n-hexane:EtOH:90:10. Run Time: 20 min. Flow rate: 1 ml/min. Retention time (minor peak)-9.35 (5.4%); Retention time (major peak)-11.67 (94.6%)] and crystallized upon extended standing or cooling to give a white solid. An optional recrystallization procedure was implemented in some cases. For example, in one experiment, 37.9 g of predominantly (S) benzyl 2-hydroxy-2-(1-hydroxycyclopropyl)acetate was dissolved in 400 mL hot hexanes to which was added the minimum volume of ethyl acetate required to produce a solution upon cooling. Diethyl ether (10 mL) was added to the solution, and it was stored at ca. −20° C. overnight. On the following day, the white crystals were collected by vacuum filtration, dried under vacuum, and found to weigh 29.3 g (77% recovery for crystallization) and to have an enantiomeric excess of ca. 89% as assessed by chiral HPLC.

Step 3: (R)-1-(2-((tert-butyldiphenylsilyl)oxy)-1-hydroxyethyl)cyclopropanol and (S)-1-(2-((tert-butyldiphenylsilyl)oxy)-1-hydroxyethyl)cyclopropanol (predominantly (R))

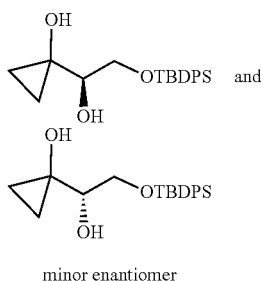

minor enantiomer

Predominantly (S) benzyl 2-hydroxy-2-(1-hydroxycyclopropyl)acetate (13.0 g, 58.5 mmol, recrystallized by the procedure described in Step 2) was dissolved in anhydrous tetrahydrofuran (200 mL) under an atmosphere of nitrogen and the resulting solution was cooled to ° C. in an ice water bath. Lithium borohydride (2 M solution in tetrahydrofuran, 120 ml, 240 mmol) was added to the reaction mixture over the course of ten minutes. The reaction mixture was then allowed to gradually warm to room temperature and aliquots were intermittently removed to facilitate reaction monitoring by NMR (aliquots were quenched by addition of methanol, acidified with acetic acid, concentrated to dryness, redissolved in THF-d8, filtered, concentrated to dryness again, and finally redissolved in the desired NMR solvent, methanol-d4). After 110 minutes, the reaction had gone to completion and the mixture was again cooled to 0° C. After 45 minutes, the reaction was quenched by gradual addition of methanol (150 mL) followed by dropwise addition of a solution of ammonium acetate (119 g) in methanol (500 mL). The mixture was then acidified by addition of acetic acid (25 mL) and all volatiles were removed in vacuo. Three successive evaporations of methanol (250 mL) from the resulting residue were performed to remove boron byproducts as (volatile) trimethylborate. The boron-depleted residue was suspended in tetrahydrofuran and filtered under vacuum, washing the filter cake copiously with tetrahydrofuran (total volume of THF used=1 L). The filtrate was concentrated in vacuo to provide 14.1 g of the crude triol intermediate as a viscous, pale-yellow syrup containing benzyl alcohol and small amounts of residual acetic acid.

The crude triol was redissolved in anhydrous N,N-dimethylformamide (290 mL), and 1H-imidazole (20.21 g, 297 mmol) and tert-butylchlorodiphenylsilane (37 mL, 144 mmol) were sequentially added to this solution. The resulting reaction mixture was stirred at ambient temperature for 19 hours under an atmosphere of dry nitrogen. On completion of the reaction (as assessed by GC analysis), the mixture was diluted in ether (250 mL) and washed with 5% (w/w) aqueous LiCl (250 mL). The aqueous layer was back-extracted with three 100 mL portions of ether and the combined organics were subjected to a second wash with aqueous LiCl as described above. The organics were then sequentially washed with water (250 mL) and brine (250 mL), and were then dried over magnesium sulfate, filtered, and concentrated in vacuo. The resulting residue was purified by flash chromatography (330 g silica gel column eluted with a gradient of 0 to 40% ethyl acetate in hexanes) to provide the title compounds (17.7 g, 85% yield from benzyl 2-hydroxy-2-(1-hydroxycyclopropyl)acetate) as a waxy, white crystalline solid.

Step 4: (S)-2-(((tert-butyldiphenylsilyl)oxy)methyl) cyclobutanone, predominantly and (R)-2-(((tert-butyldiphenylsilyl)oxy)methyl)cyclobutanone (Predominantly (S), 78-81% ee)

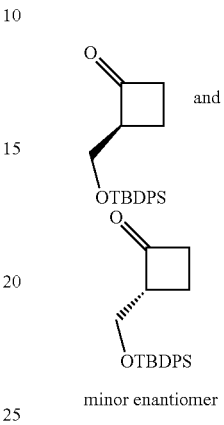

minor enantiomer

An oven-dried 500 mL RBF containing a stir bar was sealed with a septum and placed under an atmosphere of dry nitrogen using a dual-manifold. The flask was charged with 1-(2-((tert-butyldiphenylsilyl)oxy)-1-hydroxyethyl)cyclopropanol (predominantly (R) enantiomer mixture, 11.970 g, 33.6 mmol) and 300 mL pyridine. Once all of the diol starting material had dissolved, the resulting solution was cooled in an acetonitrile/dry ice mixture to ca. −40° C., and the nitrogen line was replaced with an Argon balloon. Methanesulfonyl chloride (5.30 mL, 68.5 mmol) was added to the reaction mixture via syringe over the course of five minutes. The reaction mixture was stirred at −35° C. for 18 h inside a cryocool apparatus using acetone as the coolant medium. The reaction mixture was then allowed to warm to ambient temperature over the course of thirty minutes, after which time additional mesyl chloride (530 μL, 784 mg, 6.85 mmol) was added. Stirring at room temperature was continued for forty minutes. The reaction mixture was then cooled to ca. −10° C. in an acetonitrile/dry ice slurry and poured into 250 mL of ice-water. The crude product was extracted into ether from the water layer via multiple rounds of extraction with fresh solvent, with the total volume of ether used being 800 mL. The combined organics were then washed with brine, dried over magnesium sulfate, filtered and concentrated in vacuo to give a crude residue that was further purified by chromatography on a 220 g silica gel column eluted with a gradient of 0 to 25% ethyl acetate in hexanes to provide the title compounds (8.12 g, 71% yield) as a semi-crystalline white solid. The cyclobutanone prepared in this manner typically had enantiomeric excesses ranging from 78-81% as assessed by Chiral SFC, corresponding to enantiomer ratios ranging from 8.1:1 to 9.5:1. Absolute stereochemistry of the major enantiomer of the cyclobutanone was confirmed by stereospecific conversion to (1R,2R)-2-(((tert-butyldiphenylsilyl)oxy)methyl)cyclobutanecarbaldehyde, reductive amination of the aldehyde with Intermediate AA11A, Step 12B and subsequent desilylation to provide a sample of Intermediate AA11A, Step 19B; the NMR spectral features of this material were identical to those of an authentic sample of Intermediate AA11A, Step 19B.

Step 5: (1S,2S)-2-(((tert-butyldiphenylsilyl)oxy)methyl)cyclobutanol and (1R,2R)-2-(((tert-butyldiphenylsilyl)oxy)methyl)cyclobutanol (predominantly (1S,2S))

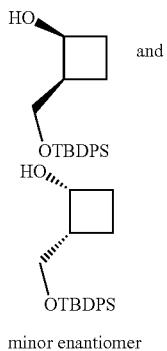

minor enantiomer

An oven-dried 100 mL round bottom flask was charged with 2-W(ien-butyldiphenylsilyl)oxy)methyl)cyclobutanone (predominantly (S) with an enantiomer ratio of ca. 9:1, prepared in Step 4, 1.20 g, 3.54 mmol) and placed under a nitrogen atmosphere. The cyclobutanone was dissolved in anhydrous tetrahydrofuran (35 mL) and the resulting solution was cooled to −78° C. in a dry ice/acetone bath. L-Selectride (1 M in THF, 5.40 ml, 5.40 mmol) was added via syringe, and the reaction mixture was allowed to gradually warm to ambient temperature. After 1 hour, 20 minutes, the reaction was quenched by cautious addition of saturated ammonium chloride and partitioned between ethyl acetate and saturated ammonium chloride, back-extracting the aqueous phase with several portions of ethyl acetate. The combined organics were washed with brine, dried over magnesium sulfate, filtered, and concentrated in vacuo to give the crude product, which was further purified by silica gel chromatography to provide the title compounds (1.14 g, 94% yield).

Step 6: (((1S,2R)-2-(allylthio)cyclobutyl)methoxy)(tert-butyl)diphenylsilane and (((1R,2S)-2-(allylthio)cyclobutyl)methoxy)(tert-butyl)diphenylsilane (predominantly (1S,2R))

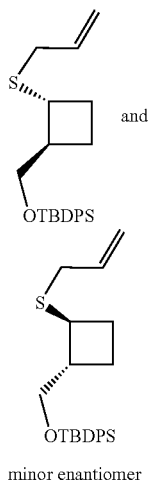

minor enantiomer

Methanesulfonyl chloride (0.270 mL, 3.49 mmol) was added to a stirred, ice-cooled solution of cis-2-(((tert-butyl-diphenylsilyl)oxy)methyl)cyclobutanol (predominantly (1S, 2S) enantiomer mixture, prepared in Step 5, 1.13 g, 3.33 mmol) and N-ethyl-N-isopropylpropan-2-amine (Hünig's base, 1.2 ml, 6.89 mmol) in anhydrous dichloromethane (16 mL) under an atmosphere of nitrogen. The mixture was allowed to gradually warm to room temperature. After three hours, 35 minutes, the mixture was cooled again to ° C. in an ice-water bath. Fifteen minutes later, the mixture was diluted in 75 mL of ice-cooled dichloromethane and the resulting solution was washed with ice-cooled 1 M aqueous hydrochloric acid (2×). The combined aqueous layers were back-extracted with two portions of dichloromethane and the combined organics were sequentially washed with ice-cooled water, ice-cooled saturated sodium bicarbonate, and brine. The organics were dried over magnesium sulfate, filtered and concentrated in vacuo to provide the crude mesylate ester intermediate as a yellow syrup (1.395 g, 100% crude yield).

Technical grade prop-2-ene-1-thiol, (Sigma Aldrich, 1.1 mL, 10.68 mmol) was added cautiously via syringe to a stirred slurry of sodium hydride (60% dispersion in mineral oil, 0.36 g, 9.00 mmol) in ice-cooled, degassed anhydrous N,N-dimethylformamide under an argon atmosphere. Once the addition was complete, the reaction mixture was allowed to warm to room temperature over the course of 22 minutes, after which a solution of the crude mesylate generated above (1.38 g, the amount remaining after analytical samples had been taken) in anhydrous, degassed N,N-dimethylformamide (12 mL) was added to the allyl thiolate solution. After five minutes, the resulting stirred reaction mixture was heated in an oil bath at 65° C. for two hours, 30 minutes. Upon cooling, 14 g of maleimide-functionalized silica gel (0.66 mmol/g maleimide loading; obtained from Silicycle) was added to the reaction mixture, giving a dark red slurry that was stirred at ambient temperature for 30 minutes and subsequently filtered, washing the filter cake with copious amounts of ethyl acetate. The filtrate was washed with 5% (w/w) aqueous LiCl, and the LiCl layer was back-extracted with two 75 mL portions of diethyl ether. The combined organics were washed sequentially with water, 15% (w/w) aqueous citric acid, water (once more), saturated sodium bicarbonate (2×), brine, and were dried over magnesium sulfate, filtered and concentrated in vacuo to give the crude thioether product, which was further purified by chromatography on silica gel using an eluent gradient of 0 to 20% ethyl acetate in hexanes. Fractions containing predominantly the desired product along with small amounts of nearly co-eluting impurities were pooled and stripped of solvents in vacuo to give the title compound as 1.7 g of an oil, a mixture of compounds containing minor quantities of an unidentified impurity that was removed much more readily after Step 7.

Step 7: ((1S,2R)-2-(allylthio)cyclobutyl)methanol and ((1R,2S)-2-(allylthio)cyclobutyl)methanol (predominantly (1S,2R))

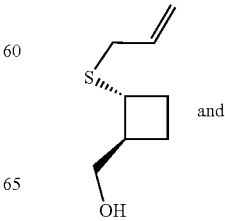

593

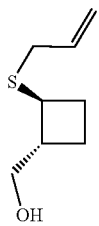

minor enantiomer

Tetrabutylammonium fluoride (1 M in THF, 5.40 ml, 5.40 mmol) was added to a stirred, ice-cooled solution of trans-42-(allylthio)cyclobutyl)methoxy)(tert-butyl)diphenylsilane, predominantly (1S,2R) (1.07 g, 2.70 mmol) in anhydrous tetrahydrofuran (18 mL) under an atmosphere of dry nitrogen. Following addition, the reaction mixture was allowed to warm to room temperature. After 4 h, the reaction mixture was partitioned between ether and saturated aqueous ammonium chloride. The aqueous layer was back-extracted with three portions of ether, and the combined organics were washed with brine, dried over magnesium sulfate, filtered and concentrated in vacuo to give the crude alcohol, which was further purified by flash chromatography (80 g silica gel column eluted with a gradient of 0 to 30% ethyl acetate in hexanes) to provide 445 mg of a clear oil. NMR analysis showed this material to be the desired product, containing ca. 21 mol % residual ethyl acetate of chromatography. The mass of desired product present in the sample could therefore be estimated as 387 mg, corresponding to a 91% yield.

Step 8: (S)-tert-butyl 5-(((1S,2R)-2-(allylthio)cyclobutyl)methyl)-6'-chloro-3',4,4',5-tetrahydro-2H,2'H-spiro[benzo[b][1,4]oxazepine-3,1'-naphthalene]-7-carboxylate and (S)-tert-butyl 5-(((1R,2S)-2-(allylthio)cyclobutyl)methyl)-6'-chloro-3',4,4',5-tetrahydro-2H,2'H-spiro[benzo[b][1,4]oxazepine-3,1'-naphthalene]-7-carboxylate or (S)-tert-butyl 5-(((1S,2R)-2-(allylthio)cyclobutyl)methyl)-6'-chloro-3',4,4',5-tetrahydro-2H,2'H-spiro[benzo[b][1,4]oxazepine-3,1'-naphthalene]-7-carboxylate and (S)-tert-butyl 5-(((1S,2S)-2-(allylthio)cyclobutyl)methyl)-6'-chloro-3',4,4',5-tetrahydro-2H,2'H-spiro[benzo[b][1,4]oxazepine-3,1'-naphthalene]-7-carboxylate or [(S)-tert-butyl 5-(((1S,2R)-2-(allylthio)cyclobutyl)methyl)-6'-chloro-3',4,4',5-tetrahydro-2H,2'H-spiro[benzo[b][1,4]oxazepine-3,1'-naphthalene]-7-carboxylate and (S)-tert-butyl 5-(((1R,2R)-2-(allylthio)cyclobutyl)methyl)-6'-chloro-3',4,4',5-tetrahydro-2H,2'H-spiro[benzo[b][1,4]oxazepine-3,1'-naphthalene]-7-carboxylate

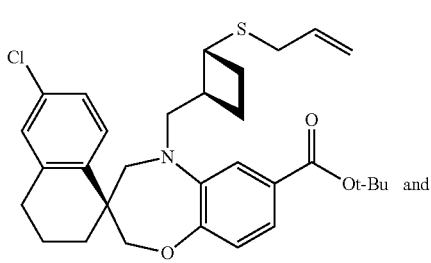

594

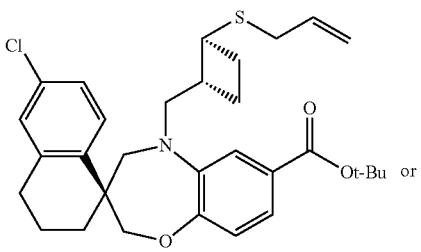

Ot-Bu or

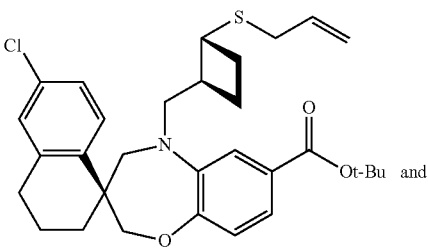

Ot-Bu and

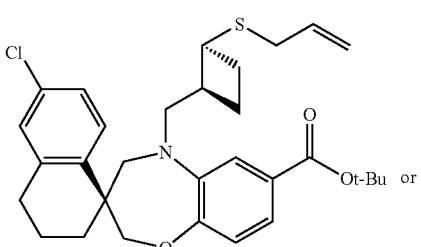

Ot-Bu or

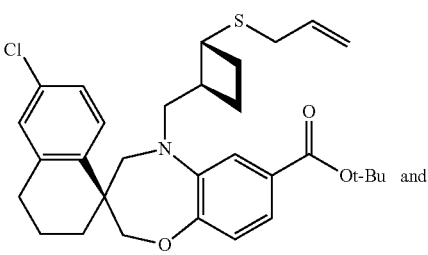

Ot-Bu and

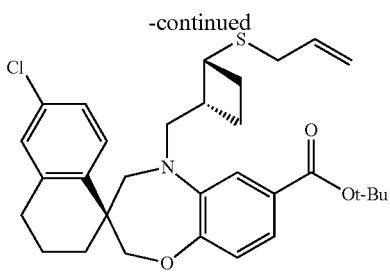

Water (504) was suspended in a solution of trans-(2-(allylthio)cyclobutyl)methanol (predominantly (1S,2R), prepared in Step 7, 222 mg, 1.403 mmol) in dichloromethane (13 mL), and the resulting biphasic mixture was vigorously stirred at ambient temperature. After 15 minutes, the water appeared to be thoroughly dispersed throughout the reaction medium, and 1,1,1-Triacetoxy-1,1-dihydro-1,2-benziodoxol-3(1H)-one (Dess-Martin periodinane, 1.18 g, 2.78 mmol) was added. The stirred reaction mixture was aged for 3.5 h and then diluted in additional dichloromethane. The excess oxidant was quenched by addition of 1 M aqueous sodium thiosulfate (a volume roughly equal to that of the organics). The resulting biphasic mixture was stirred at room temperature until both phases became clear and was then partitioned between ether and 1 M sodium thiosulfate. The organic phase was washed with sequentially with 1 M sodium thiosulfate, saturated sodium bicarbonate (6×) and brine, dried over magnesium sulfate and concentrated in vacuo cautiously (so as not to evaporate the desired aldehyde). The resulting oil weighed 161 mg and appeared by proton NMR to contain principally the desired aldehyde intermediate, along with minor amounts of residual ether.

(S)-tert-butyl 6'-chloro-3',4,4',5-tetrahydro-2H,2'H-spiro[benzo[b][1,4]oxazepine-3,1'-naphthalene]-7-carboxylate (Intermediate AA11A, Step 12B, 237 mg, 0.593 mmol) and a solution of the crude intermediate aldehyde trans-2-(allylthio)cyclobutane carbaldehyde (predominantly (1S,2R), 151.7 mg, 0.884 mmol) were dissolved in a mixture of anhydrous dichloromethane (4400 µL) and acetic acid (2200 µL). The resulting stirred reaction mixture was cooled to 0° C. in an ice-water bath. After the mixture had been aged for 20 minutes at this temperature, a solution of sodium cyanoborohydride (18.5 mg, 0.295 mmol) in anhydrous tetrahydrofuran (500 µL) was added to it over the course of 90 minutes using a dry gas-tight syringe mounted on a syringe pump. The reaction mixture was then allowed to warm to ambient temperature and was aged for an additional 11 h, after which it was diluted in ethyl acetate and poured into a slurry of ca. 40 g of ice suspended in 70 mL 1 M aqueous sodium hydroxide. The crude product mixture was extracted into ethyl acetate and the aqueous layer was back-extracted with two portions of ethyl acetate. The combined organics were sequentially washed with two portions of pH 7 phosphate buffer and two portions of brine, dried over magnesium sulfate, filtered, and stripped in vacuo to give a residue which was further purified by flash chromatography (24 g silica gel column eluting with a gradient of 0 to 40% (99:1 ethyl acetate:acetic acid) in hexanes) to provide the title compounds as a white foam (229 mg, 30% combined yield over two steps based on trans-(2-(allylthio)cyclobutyl) methanol, 72% combined yield for the reductive amination based on Intermediate AA11A, Step 12B).

Step 9: (S)-tert-butyl 6'-chloro-5-(((1S,2R)-2-((5-sulfamoylpentyl)thio)cyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1R,2S)-2-((5-sulfamoylpentyl)thio)cyclobutyl)methyl)-3',4,4',5-tetrahydro-2H,2'H-spiro[benzo[b][1,4]oxazepine-3,1'-naphthalene]-7-carboxylate or (S)-tert-butyl 6'-chloro-5-(((1S,2R)-2-((5-sulfamoylpentyl)thio)cyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1S,2S)-2-((5-sulfamoylpentyl)thio)cyclobutyl)methyl)-3',4,4',5-tetrahydro-2H,2'H-spiro[benzo[b][1,4]oxazepine-3,1'-naphthalene]-7-carboxylate or (S)-tert-butyl 6'-chloro-S-(((1S,2R)-2-((5-sulfamoylpentyl)thio)cyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1R,2R)-2-((5-sulfamoylpentyl)thio)cyclobutyl)methyl)-3',4,4',5-tetrahydro-2H,2'H-spiro[benzo[b][1,4]oxazepine-3,1'-naphthalene]-7-carboxylate

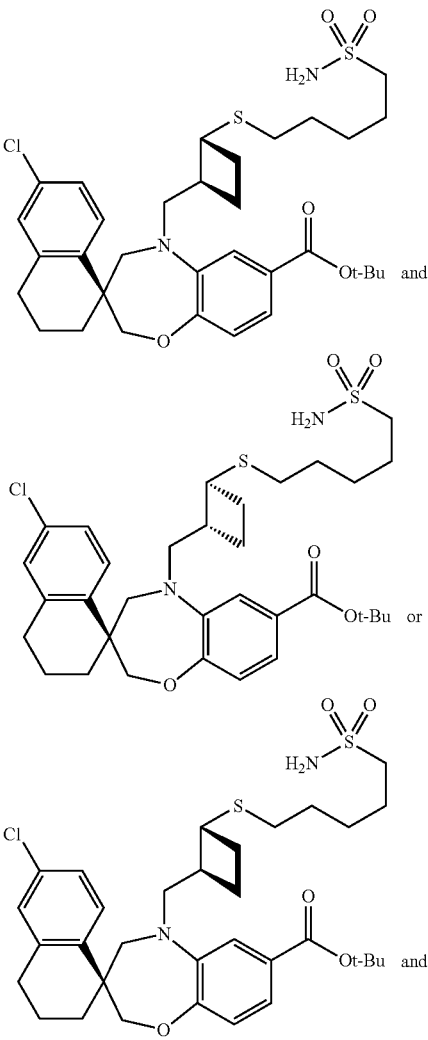

-continued

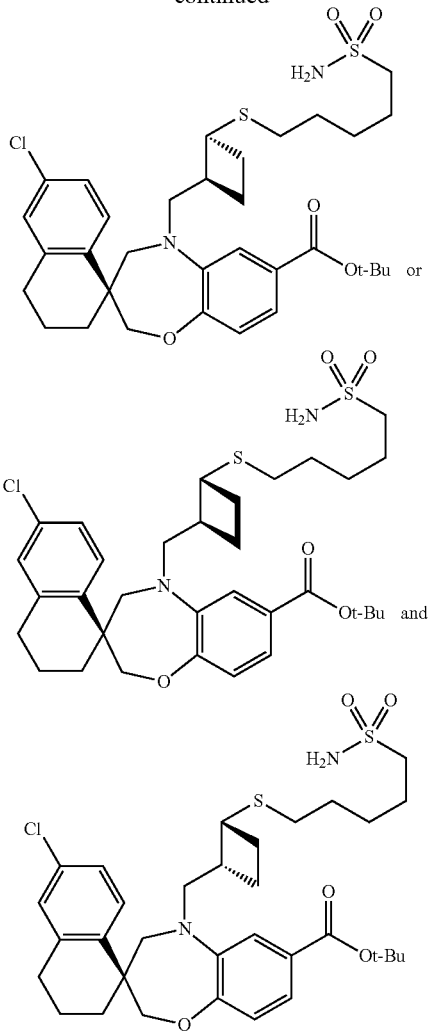

(1,3-Bis-(2,4,6-trimethylphenyl)-2-imidazolidinylidene)dichloro(o-isopropoxyphenylmethylene)ruthenium (Hoveyda-Grubbs catalyst, second generation, 153 mg, 0.244 mmol) was added to a room-temperature, stirred solution containing but-3-ene-1-sulfonamide (170 mg, 1.258 mmol) and a sample comprised of a ca. 6:1 mixture of (S)-tert-butyl 5-(((1S,2R)-2-(allylthio)cyclobutyl)methyl)-6'-chloro-3',4,4',5-tetrahydro-2H,2'H-spiro[benzo[b][1,4]oxazepine-3,1'-naphthalene]-7-carboxylate and a minor diastereomer (mixture obtained in Step 8, 131.9 mg, 0.244 mmol total) in degassed dichloroethane (3.5 mL) under an argon atmosphere. Additional quantities of sulfonamide (51.4 mg, 0.38 mmol) and catalyst (7.0 mg, 0.011 mmol) were added at reaction times of 22 and 33 minutes, respectively. After a total reaction time of 90 minutes, the mixture was concentrated in vacuo and purified by silica gel chromatography, using a solvent gradient of 0 to 40% (99:1 ethyl acetate:acetic acid) in hexanes, to provide a mixture of isomeric metathesis cross-coupling products as a semi-solid yellow residue (90.4 mg, 57% material recovery).

A stirred solution of the isomeric mixture of olefinic metathesis products (90.4 mg, 0.140 mmol) in anhydrous, degassed dichloromethane (2 mL) was charged with (1,5-cyclooctadiene)(pyridine)(tricyclohexylphosphine)-iridium(I)hexafluorophosphate (Crabtree's catalyst, 22 mg, 0.027 mmol) and stirred under an atmosphere of hydrogen at ambient temperature. After ca. 1.5 hours, an additional 1 mL of dichloromethane was added to the mixture, 20 h after the reaction was commenced, an additional 9 mg increment of Crabtree's catalyst was added to the solution. The reaction mixture was stirred for an additional 2 h before being concentrated in vacuo and purified by flash chromatography (12 g silica gel column eluted with a gradient of 0 to 40% [99:1 ethyl acetate:acetic acid] in hexanes) to provide the title compounds as a semi-solid white residue (54.6 mg, 34% overall combined yield, 60% material recovery for the hydrogenation).

Step 10: (1S,3'S,6'R)-6-chloro-3,4-dihydro-2H,15'H-spiro[naphthalene-1,22'-[20]oxa[7,13]dithia[1,14]diazatetracyclo[14.7.2.0$^{3,6}$.0$^{19,24}$]pentacosa[16,18,24]trien]-15'-one 13',13'-dioxide and (1S,3'R,6'S)-6-chloro-3,4-dihydro-2H,15'H-spiro[naphthalene-1,22'-[20]oxa[7,13]dithia[1,14]diazatetracyclo[14.7.2.0$^{3,6}$.0$^{19,24}$]pentacosa[16,18,24]trien]-15'-one 13',13'-dioxide or (1S,3'S,6'R)-6-chloro-3,4-dihydro-2H,15'H-spiro[naphthalene-1,22'-[20]oxa[7,13]dithia[1,14]diazatetracyclo[14.7.2.0$^{3,6}$.0$^{19,24}$]pentacosa[16,18,24]trien]-15'-one 13',13'-dioxide and (1S,3'R,6'R)-6-chloro-3,4-dihydro-2H,15'H-spiro[naphthalene-1,22'-[20]oxa[7,13]dithia[1,14]diazatetracyclo[14.7.2.0$^{3,6}$.0$^{19,24}$]pentacosa[16,18,24]trien]-15'-one 13',13'-dioxide or [(1S,3'S,6'R)-6-chloro-3,4-dihydro-2H,15'H-spiro[naphthalene-1,22'-[20]oxa[7,13]dithia[1,14]diazatetracyclo[14.7.2.0$^{3,6}$.0$^{19,24}$]pentacosa[16,18,24]trien]-15'-one 13',13'-dioxide and (1S,3'S,6'S)-6-chloro-3,4-dihydro-2H,15'H-spiro[naphthalene-1,22'-[20]oxa[7,13]dithia[1,14]diazatetracyclo[14.7.2.0$^{3,6}$.0$^{19,24}$]pentacosa[16,18,24]trien]-15'-one 13',13'-dioxide Trifluoroacetic acid (600 µL, 7.84 mmol) was added to a stirred, room-temperature solution of an isomer mixture containing (S)-tert-butyl 6'-chloro-5-(((1S,2R)-2-((5-sulfamoylpentyl)thio)cyclobutyl)methyl)-3',4,4',5-tetrahydro-2H,2'H-spiro[benzo[b][1,4]oxazepine-3,1'-naphthalene]-7-carboxylate and a minor diastereomer (mixture obtained in Step 9, 17.3 mg, 0.027 mmol total) in dichloromethane (600 µL). After 2 h, the reaction mixture was concentrated in vacuo and three aliquots of anhydrous toluene were evaporated from the resulting residue to remove moisture from the crude carboxylic acid intermediates prior to macrocyclization. The crude intermediates exhibited the mass of the desired carboxylic acid intermediate by LC-MS, and this material was used in the macrocyclization reaction without further characterization.

A solution of N1-((ethylimino)methylene)-N3,N3-dimethylpropane-1,3-diamine hydrochloride (12 mg, 0.063 mmol) in anhydrous dichloromethane (1 mL) was added portionwise over the course of seven minutes to an ice-cold, stirred solution of the crude carboxylic acid intermediates generated above and N,N-dimethylpyridin-4-amine (6 mg, 0.049 mmol) in anhydrous dichloromethane (12 mL) under an atmosphere of dry nitrogen. The resulting stirred reaction mixture was allowed to gradually warm to rt and was aged for ca. 20 hours at this temperature, after which time it was partitioned between dichloromethane and 1 M aqueous hydrochloric acid. The organic layer was washed with brine, dried over magnesium sulfate, filtered and concentrated in vacuo to give a residue that was further purified by flash chromatography (4 g silica gel column eluted with a gradient of 0 to 25% [99:1 ethyl acetate:acetic acid) in hexanes] to provide the title compounds as a flaky white solid (8.9 mg, 56% overall combined yield). By comparison of NMR integrals and peak heights, the two isomers comprising the sample were present in a ratio of ca. 6:1. Co-integration of NMR signals for the major and minor species supported the assignment of the minor compound as a diastereomer, consistent with expectations based on the means of preparation, the known enantiomer ratio of the cyclobutane precursor described in Step 4, identical masses and retention times for both compounds observed by LC-MS and HPLC, respectively, and other considerations described in Step 7. $^1$H NMR (500 MHz, CD$_2$Cl$_2$) δ ppm 8.22 (br. s, 1H), 7.72 (d, J=8.6 Hz, 0.13 H), 7.72 (d, J=8.6 Hz, 0.81 H), 7.16-7.20 (m, 1H), 7.08-7.12 (m, 1.8 H), 7.08 (apparent d, J=2.0 Hz, 0.07 H), 7.04-7.07 (m, 1H), 6.95 (d, J=8.3 Hz, 0.86 H), 6.95 (d, J=8.3 Hz, 0.14H), 4.23 (d, J=12.0 Hz, 0.16 H), 4.08-4.14 (m, 1.84 H), 3.81-3.91 (m, 2H), 3.72 (d, J=14.2 Hz, 1H), 3.34 (dt, J=14.8, 7.3 Hz, 1H), 3.21 (d, J=14.2 Hz, 1H), 3.01-3.11 (m, 2H), 2.74-2.79 (m, 2H), 2.57-2.67 (m, 1H), 2.49-2.55 (m, 2H), 2.01-2.12 (m, 4H), 1.78-1.96 (m, 3H), 1.56-1.76 (m, 7H), 1.39-1.47 (m, 1H). m/z (ESI, +ve ion) 575.0 (M+H)$^+$, 597.1 (M+Na)$^+$.

Example 196. (1S,3'S,6'R)-6-chloro-3,4-dihydro-2H, 15'H-spiro[naphthalene-1,22'-[20]oxa[7,13]dithia[1, 14]diazatetracyclo[14.7.2.0$^{3,6}$.0$^{19,24}$]pentacosa[16, 18,24]trien]-15'-one 7',7',13',13'-tetraoxide and (1S, 3'R,6'S)-6-chloro-3,4-dihydro-2H,15'H-spiro [naphthalene-1,22'-[20]oxa[7,13]dithia[1,14] diazatetracyclo[14.7.2.0$^{3,6}$.0$^{19,24}$]pentacosa[16,18, 24]trien]-15'-one 7',7',13',13'-tetraoxide or (1S,3'S, 6'R)-6-chloro-3,4-dihydro-2H,15'H-spiro [naphthalene-1,22'-[20]oxa[7,13]dithia[1,14] diazatetracyclo[14.7.2.0$^{3,6}$.0$^{19,24}$]pentacosa[16,18, 24]trien]-15'-one 7',7',13',13'-tetraoxide and (1S,3'S, 6'S)-6-chloro-3,4-dihydro-2H,15'H-spiro [naphthalene-1,22'-[20]oxa[7,13]dithia[1,14] diazatetracyclo[14.7.2.0$^{3,6}$.0$^{19,24}$]pentacosa[16,18, 24]trien]-15'-one 7',7',13',13'-tetraoxide or [(1S,3'S, 6'R)-6-chloro-3,4-dihydro-2H,15'H-spiro [naphthalene-1,22'-[20]oxa[7,13]dithia[1,14] diazatetracyclo[14.7.2.0$^{3,6}$.0$^{19,24}$]pentacosa[16,18, 24]trien]-15'-one 7',7',13',13'-tetraoxide and (1S,3'R, 6'R)-6-chloro-3,4-dihydro-2H,15'H-spiro [naphthalene-1,22'-[20]oxa[7,13]dithia[1,14] diazatetracyclo[14.7.2.0$^{3,6}$.0$^{19,24}$]pentacosa[16,18, 24]trien]-15'-one 7',7',13',13'-tetraoxide

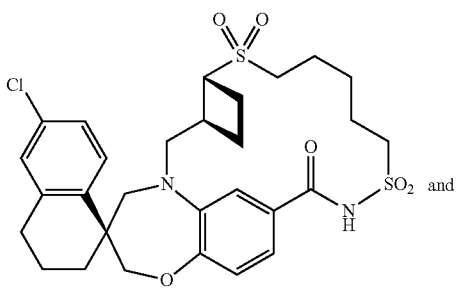

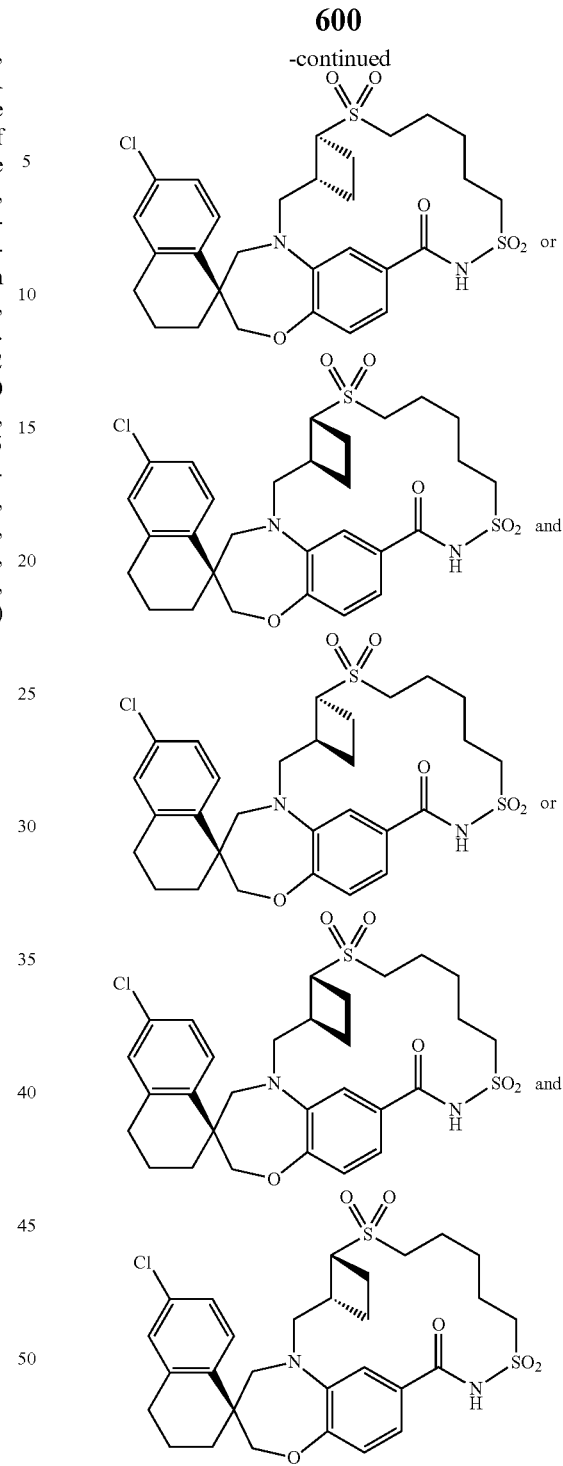

N-methylmorpholine oxide (30 mg, 0.256 mmol) was weighed into a flask containing a mixture of (1S,3'S,6'R)-6-chloro-3,4-dihydro-2H,15'H-spiro[naphthalene-1,22'-[20] oxa[7,13]dithia[1,14]diazatetracyclo[14.7.2.0$^{3,6}$.0$^{19,24}$]pentacosa[16,18,24]-trien]-15'-one 13',13'-dioxide and a minor diastereomer (obtained in Step 10 of Example 195, 23.2 mg, 0.040 mmol total). A solution of osmium tetroxide (2.1 mg, 8.26 µmol) in 600 µL acetone was added followed by water (300 µL), and the resulting reaction mixture was vigorously stirred at ambient temperature for one hour. The oxidant was quenched by addition of 6 mL 1 M aqueous sodium thiosulfate and the crude product mixture was extracted into 1:5.7 isopropanol:dichloromethane. The aqueous layer was back-extracted 3× with 1:5.7 isopropanol:dichloromethane and the combined organics were washed with 1 M aqueous sodium thiosulfate that had been saturated in sodium chloride followed by brine, dried over magnesium sulfate, filtered and concentrated in vacuo to give a crude residue that was further purified by flash chromatography (4 g silica gel column eluted with a gradient of 30 to 100% [99:1 ethyl acetate:acetic acid] in hexanes) to provide a mixture of the title compounds as a flaky white solid (16.7 mg, 68% yield). Integration of aryl resonances in the proton NMR spectrum of this material showed it to be composed of a ca. 11:1 mixture of isomers containing the desired (3'S,6'R) diastereomer as the major compound along with a minor diastereomer inferred to arise from the minor enantiomer present in the cyclobutane starting material; however, as a purified sample of the minor compound was not obtained for exhaustive characterization, alternative structural assignments (as depicted above) for the minor diastereomer could not be definitively excluded. Co-integration of NMR signals for the two compounds supported assignment of the minor component as a stereoisomer, consistent with expectations based on the considerations described in Steps 7 and 10 of Example 195. $^1$H NMR (500 MHz, (CD$_3$)$_2$CO) δ ppm 10.26 (br. s., 1H), 7.80 (d, J=8.6 Hz, 0.08 H), 7.75 (d, J=8.6 Hz, 0.91 H), 7.37 (d, J=1.7 Hz, 0.08 H), 7.30 (d, J=2.0 Hz, 0.91 H), 7.26 (dd, J=8.2, 2.1 Hz, 0.09 H), 7.23 (dd, J=8.4, 2.3 Hz, 0.95 H), 7.20 (dd, J=8.1, 2.0 Hz, 0.89 H), 7.14-7.15 (m, 0.08 H), 7.11-7.14 (m, 0.87 H), 6.95 (d, J=8.1 Hz, 0.1 H), 6.94 (d, J=8.1 Hz, 0.85 H), 4.17 (s, 0.14 H), 4.14 (s, 0.17 H), 4.12 (s, 0.77 H), 4.10 (s, 0.71 H), 4.03-4.09 (m, 1H), 3.87 (ddd, J=14.5, 9.9, 4.4 Hz, 1H), 3.75 (d, J=14.2 Hz, 1H), 3.66 (q, J=9.3 Hz, 1H), 3.49 (s, 0.15 H), 3.29-3.43 (m, 2.82 H), 3.26 (dd, J=14.9, 10.3 Hz, 0.11), 3.03-3.20 (m, 3H), 2.71-2.86 (m, 3H; signal partially obscured by residual water peak), 2.19-2.35 (m, 2H), 2.17 (dt, J=4.5, 2.3 Hz, 1H), 2.08-2.16 (m, 2H), 1.98-2.08 (m, 3H; signal partially obscured by residual acetone peak), 1.86-1.98 (m, 5H), 1.68-1.86 (m, 3H), 1.45-1.54 (m, 1H). m/z (ESI, +ve ion) 607.2 (M+H)$^+$.

Example 197. (1S,3'R,6'S,7'E,9'S,12'R)-6-chloro-12'-ethyl-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [7,16,18,24]tetraen]-15'-one 13',13'-dioxide or (1S,3'R,6'S,7'E,9'R,12'R)-6-chloro-12'-ethyl-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [7,16,18,24]tetraen]-15'-one 13',13'-dioxide

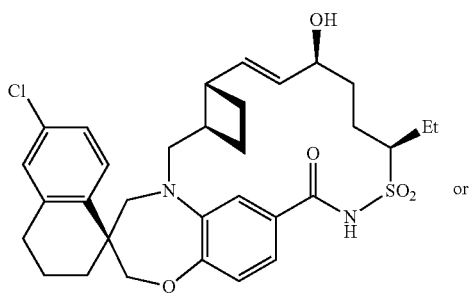

or

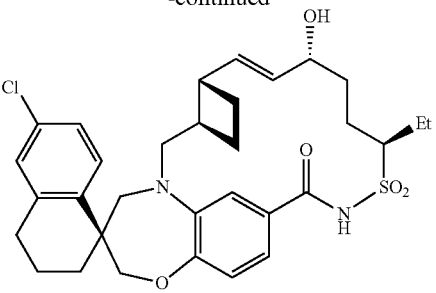

Step 1: (S)-tert-butyl 4-hydroxyhexanoate

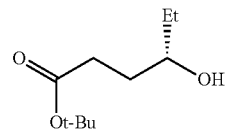 [SMILES: CC[C@H](O)CCC(=O)OC(C)(C)C]

The title compound was prepared in yields ranging from 49-51% from (S)-2-ethyloxirane and tert-butyl acetate by the method described in *Journal of Organic Chemistry*, 1989, 54, 2039.

Step 2: (R)-tert-butyl 4-(pyrimidin-2-ylthio)hexanoate

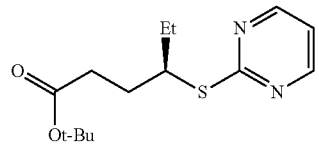 [SMILES: CC[C@H](CCC(=O)OC(C)(C)C)Sc1ncccn1]

Methanesulfonyl chloride (2.1 mL, 27.1 mmol) was added dropwise to a stirred, ice-cooled solution of (S)-tert-butyl 4-hydroxyhexanoate (4.729 g, 25.1 mmol, prepared in Step 1) and N-ethyl-N-isopropylpropan-2-amine (9.0 mL, 53.1 mmol) in anhydrous dichloromethane (125 mL) under an atmosphere of dry nitrogen. The resulting reaction mixture was allowed to gradually warm to ambient temperature and was aged overnight for a total of 17 h. The mixture was diluted in DCM, washed sequentially with ice-cooled 1 M aqueous hydrochloric acid, saturated aqueous sodium bicarbonate and brine, and then the combined organics were dried over magnesium sulfate, filtered and concentrated in vacuo to give the crude mesylate intermediate as a reddish-orange oil weighing 6.88 g.

Pyrimidine-2-thiol (3.24 g, 28.9 mmol) was suspended in degassed absolute ethanol (200 mL) under an argon atmosphere in a round-bottom flask equipped with a reflux condenser, and the resulting mixture was vigorously stirred at ambient temperature. Sodium ethoxide (21% w/w in ethanol, 10.00 ml, 26.8 mmol) was gradually added to the slurry, inducing dissolution of the thiol as its sodium salt. After 13 minutes, a solution of the crude mesylate intermediate generated above in degassed ethanol (50 mL) was added the mixture over the course of five minutes. The reaction mixture was heated at 60° C. in an oil bath for ca.

2 h. The reaction temperature was then increased to 100° C. and maintained at this temperature for one hour, after which solvents were removed in vacuo. The residue was taken back up into diethyl ether (100 mL) and washed sequentially with 1 M aqueous sodium hydroxide (2×) and brine. The organics were dried over magnesium sulfate, filtered and concentrated to give the crude product, which was further purified by flash chromatography (330 g silica gel column eluted with a gradient of 0 to 20% ethyl acetate in hexanes) to give the title compound as an orange oil (3.20 g, 45% yield).

Step 3: (R)—N-methoxy-N-methyl-4-(pyrimidin-2-ylthio)hexanamide

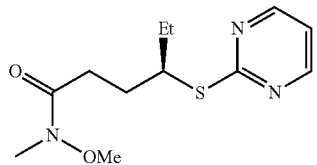 [SMILES: CC[C@H](CCC(=O)N(C)OC)Sc1ncccn1]

Trifluoroacetic acid (10 mL, 130 mmol) was added to a stirred, room-temperature solution of (R)-tert-butyl 4-(pyrimidin-2-ylthio)hexanoate (3.09 g, 10.9 mmol) in dichloromethane (10 mL). After 2 h, the reaction mixture was concentrated to give the crude carboxylic acid intermediate. Trace moisture and residual trifluoroacetic acid were liberated from this material by successive azeotropic co-distillations of anhydrous toluene (4×24 mL) from the reaction pot using a rotary evaporator, giving a pinkish-orange syrup that was redissolved in anhydrous dichloromethane (30 mL). The resulting stirred, solution was cooled to 0° C. in an ice-water bath under an atmosphere of dry nitrogen. Triethylamine (12.2 mL, 88 mmol), N,O-dimethylhydroxylamine hydrochloride (1.32 g, 13.53 mmol) and 1H-benzo[d][1,2,3]triazol-1-ol (2.24 g, 16.58 mmol) were added to the solution, followed by N1-((ethylimino)methylene)-N3,N3-dimethylpropane-1,3-diamine hydrochloride (EDCI, 3.18 g, 16.59 mmol). An aliquot of anhydrous dichloromethane (3 mL) was used to rinse all solid reactants of the joint of the flask into solution. The stirred mixture was allowed to gradually warm to ambient temperature. After ca. 13.5 hours, the reaction mixture was partitioned between dichloromethane and 15% (w/w) aqueous citric acid. The organics were sequentially washed with water, saturated aqueous sodium bicarbonate and brine, and were dried over magnesium sulfate, filtered and concentrated in vacuo. The resulting residue was further purified by flash chromatography (220 g silica gel column eluted with a gradient of 50 to 80% ethyl acetate in heptanes) to provide the title compound as a pale pink oil (2.66 g, 90% yield).

Step 4: (R)-5-(pyrimidin-2-ylthio)heptan-2-one

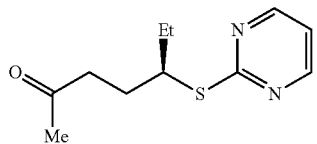 [SMILES: CC[C@H](CCC(C)=O)Sc1ncccn1]

Methylmagnesium bromide (3M in diethyl ether, 7.4 mL, 22.20 mmol) was added over the course of six minutes to a stirred, −45° C. solution of (R)—N-methoxy-N-methyl-4-(pyrimidin-2-ylthio)hexanamide (1.958 g, 7.27 mmol) in a mixture of anhydrous diethyl ether (33 ml) and anhydrous tetrahydrofuran (17 mL). After three hours, the reaction was quenched by cautious addition of saturated aqueous ammonium chloride (ca. 50 mL). The crude product was extracted into diethyl ether, washed with brine, dried over magnesium sulfate, filtered and concentrated in vacuo to provide a residue that was further purified by silica gel chromatography (eluent=5 to 40% ethyl acetate in heptanes) to give the title compound as a clear oil (968 mg, 54% yield).

Step 5: (S)-methyl 6'-chloro-5-(((1R,2R)-2-((1S,6R)-1-hydroxy-3-oxo-6-(pyrimidin-2-ylthio)octyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((1R,6R)-1-hydroxy-3-oxo-6-(pyrimidin-2-ylthio)octyl)cyclobutyl)methyl)-3',4,4',5-tetrahydro-2H,2'H-spiro[benzo[b][1,4]oxazepine-3,1'-naphthalene]-7-carboxylate

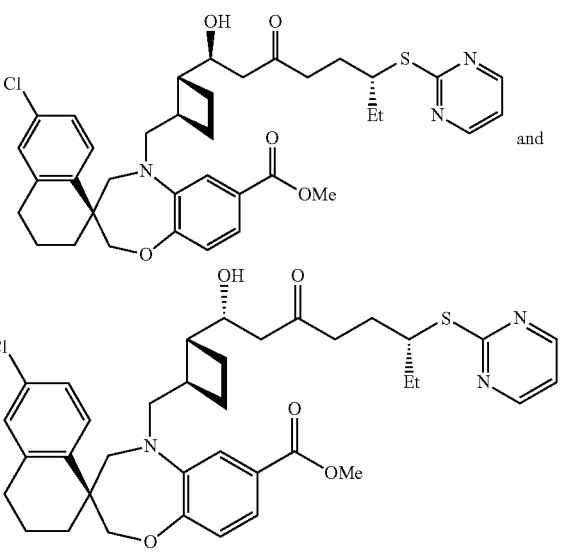

N-butyllithium (2.5 M in hexanes, 295 µL, 0.738 mmol) was added dropwise over the course of four minutes to a stirred, −78° C. solution of diisopropylamine (108 µL, 0.770 mmol) in anhydrous diethyl ether (2.5 mL) under an atmosphere of dry nitrogen. Six minutes later, the solution was warmed to 0° C. and maintained at this temperature for 0.5 hours before being cooled again to −78° C. A solution of (R)-5-(pyrimidin-2-ylthio)heptan-2-one (157 mg, 0.700 mmol) in 1:1 diethyl ether:tetrahydrofuran (1 mL total) was added dropwise to the LDA solution over six minutes. The resulting ketone enolate solution was aged at −78° C. for ca. 1 hour, 45 minutes. A solution of (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A, 160 mg, 0.352 mmol) in anhydrous tetrahydrofuran (1.2 mL total volume) was then added to the ketone enolate over the course of 0.5 hours. The mixture was aged for an additional 36 minutes at −78° C. and was then gradually cannulated while at this temperature into a vigorously stirred suspension of crushed ice (ca. 50 mL) in 0.5 M pH 7 phosphate buffer (25 mL). The crude product was extracted into ether and the organic layer was sequentially washed with 0.5 M pH 7 phosphate buffer and brine, dried over magnesium sulfate, filtered, and concentrated in vacuo to give a residue that was further purified by flash chromatography (12 g silica gel column eluted with a gradient of 10 to 70% (99:1 ethyl acetate:acetic acid) in heptanes) to afford the product as a ca. 2.5:1 mixture of diastereomeric alcohol epimers containing additional isomeric impurities at a total level of ca. 10% by NMR and HPLC. m/z (ESI, +ve ion) 678.2 (M+H)$^+$, 700.2 (M+Na)$^+$.

Step 6: (S)-methyl 6'-chloro-5-(((1R,2S)-2-((R,E)-3-oxo-6-(pyrimidin-2-ylthio)oct-1-en-1-yl)cyclobutyl)methyl)-3',4,4',5-tetrahydro-2H,2'H-spiro[benzo[b][1,4]oxazepine-3,1'-naphthalene]-7-carboxylate

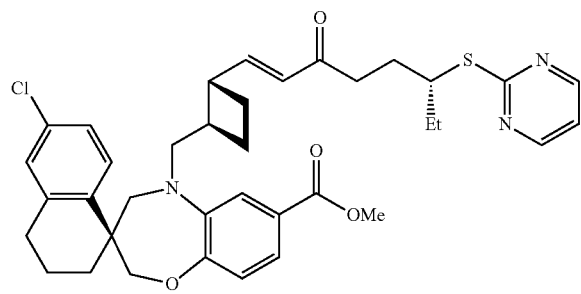

Methanesulfonyl chloride (90 µL, 1.158 mmol) was added dropwise to a stirred, 0° C. solution of a mixture of (S)-methyl 6'-chloro-5-(((1R,2R)-2-((1S,6R)-1-hydroxy-3-oxo-6-(pyrimidin-2-ylthio)octyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((1R,6R)-1-hydroxy-3-oxo-6-(pyrimidin-2-ylthio)octyl)cyclobutyl)methyl)-3',4,4',5-tetrahydro-2H,2'H-spiro[benzo[b][1,4]oxazepine-3,1'-naphthalene]-7-carboxylate (748 mg, 1.103 mmol total) in anhydrous pyridine (7.8 mL). The mixture was allowed to gradually warm to ambient temperature. One hour later, an additional 900 µL aliquot of mesyl chloride (11.6 mmol) was added dropwise over the course of three minutes. Stirring at ambient temperature was continued for one more hour, after which time the mixture was partitioned between water and methyl tert-butyl ether. The organic layer was washed sequentially with 15 (w/w) aqueous citric acid, water and brine, dried over magnesium sulfate, filtered and concentrated in vacuo to give the crude mixture of mesylate esters as a viscous yellow syrup. This material was redissolved in anhydrous benzene (10 mL) and the resulting stirred solution was cooled in an ice-water bath until it began to freeze. 1,8-Diazabicycloundec-7-ene (990 µL, 6.62 mmol) was added to this mixture dropwise over the course of seven minutes. After 1 h, 37 minutes, the mixture was diluted in ethyl acetate and washed sequentially with 15% (w/w) aqueous citric acid, water and brine. The organics were dried over magnesium sulfate, filtered, and concentrated in vacuo to give a residue that was further purified by flash chromatography (80 g silica gel column eluted with a gradient of 10 to 45% (99:1 ethyl acetate:acetic acid) in heptanes) to provide the title compound as a white foam (576 mg, 79% overall yield).

Step 7: (S)-methyl 6'-chloro-5-(((1R,2S)-2-((R,E)-3-oxo-6-(pyrimidin-2-ylsulfonyl)oct-1-en-1-yl)cyclobutyl)methyl)-3',4,4',5-tetrahydro-2H,2'H-spiro[benzo[b][1,4]oxazepine-3,1'-naphthalene]-7-carboxylate

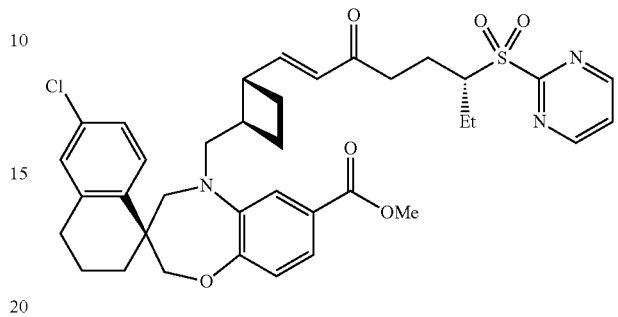

Aqueous hydrogen peroxide (30% w/w in water, 220 µL, 2.154 mmol) was added dropwise over the course of ca. two minutes to a vigorously stirred, room temperature mixture of (S)-methyl 6'-chloro-5-(((1R,2S)-2-((R,E)-3-oxo-6-(pyrimidin-2-ylthio)oct-1-en-1-yl)cyclobutyl)methyl)-3',4,4',5-tetrahydro-2H,2'H-spiro[benzo[b][1,4]oxazepine-3,1'-naphthalene]-7-carboxylate (558 mg, 0.845 mmol), sodium tungstate dihydrate (27.9 mg, 0.085 mmol), tetrabutylammonium sulfate (50 weight % solution in water, 49 µL, 0.085 mmol) and phenylphosphonic acid (13.36 mg, 0.085 mmol) in toluene (3500 µL):water (350 µL). When the addition was finished, the stirred reaction mixture was heated at 50-55° C. in an oil bath. After four hours, 41 minutes, the mixture was allowed to cool to room temperature and was partitioned between ethyl acetate and water. The combined organics were washed sequentially with water and brine, dried over magnesium sulfate, filtered, and concentrated in vacuo to give a residue that was further purified by flash chromatography (50 g silica gel column eluted with a gradient of 15 to 60% (99:1 ethyl acetate:acetic acid) in heptanes) to provide the title compound as a foamy white solid (478 mg, 82% yield). m/z (ESI, +ve ion) 692.2 (M+H)$^+$, 714.2 (M+Na)$^+$.

Step 8: (S)-methyl 6'-chloro-5-(((1R,2S)-2-((3S,6R,E)-3-hydroxy-6-(pyrimidin-2-ylsulfonyl)oct-1-en-1-yl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2S)-2-((3R,6R,E)-3-hydroxy-6-(pyrimidin-2-ylsulfonyl)oct-1-en-1-yl)cyclobutyl)methyl)-3',4,4',5-tetrahydro-2H,2'H-spiro[benzo[b][1,4]oxazepine-3,1'-naphthalene]-7-carboxylate

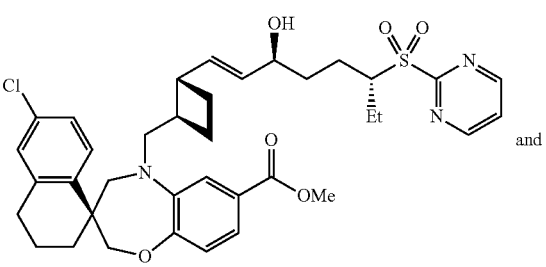

and

607
-continued

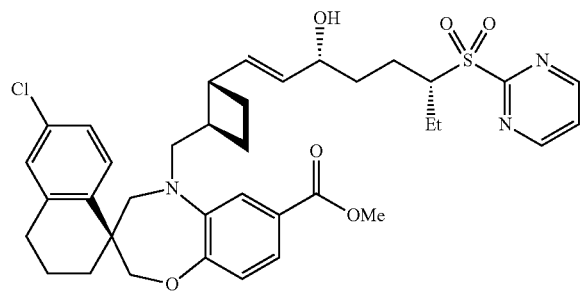

A stirred solution of (S)-methyl 6'-chloro-5-(((1R,2S)-2-((R,E)-3-oxo-6-(pyrimidin-2-ylsulfonyl)oct-1-en-1-yl)cyclobutyl)methyl)-3',4,4',5-tetrahydro-2H,2'H-spiro[benzo[b][1,4]oxazepine-3,1'-naphthalene]-7-carboxylate (480 mg, 0.693 mmol) in methanol (10.00 mL) and tetrahydrofuran (3000 μL) was cooled to ca. −10° C. in an ice/brine bath under an atmosphere of nitrogen. Cerium(III) chloride (188 mg, 0.763 mmol) was added to the solution as the solid. Sodium borohydride (58.4 mg, 1.544 mmol) was added to the reaction mixture portionwise over the course of two minutes. The reaction mixture was aged for 1.5 h at −10° C. and was subsequently quenched by addition of 15% (w/w) aqueous citric acid (20 mL) and partitioned between ethyl acetate and brine. The organics were washed once more with brine, dried over magnesium sulfate, filtered and concentrated in vacuo to give a residue that was further purified by flash chromatography (40 g silica gel column eluted with a gradient of 50 to 80% (99:1 ethyl acetate:acetic acid) in heptanes) to afford the desired alcohol epimer mixture as a white foam (363 mg, 75% yield). By HPLC, the ratio of epimers appeared to be 57:43. m/z (ESI, +ve ion) 694.2 (M+H)⁺, 716.3 (M+Na)⁺.

Step 9: (S)-methyl 6'-chloro-5-(((1R,2S)-2-((3S,6R,E)-6-(pyrimidin-2-ylsulfonyl)-3-((triisopropylsilyl)oxy)oct-1-en-1-yl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2S)-2-((3R,6R,E)-6-(pyrimidin-2-ylsulfonyl)-3-((triisopropylsilyl)oxy)oct-1-en-1-yl)cyclobutyl)methyl)-3',4,4',5-tetrahydro-2H,2'H-spiro[benzo[b][1,4]oxazepine-3,1'-naphthalene]-7-carboxylate

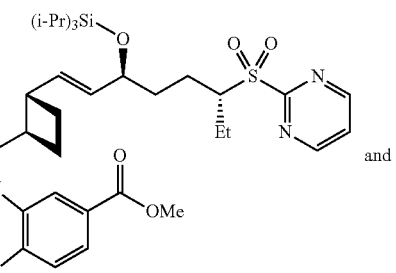

608
-continued

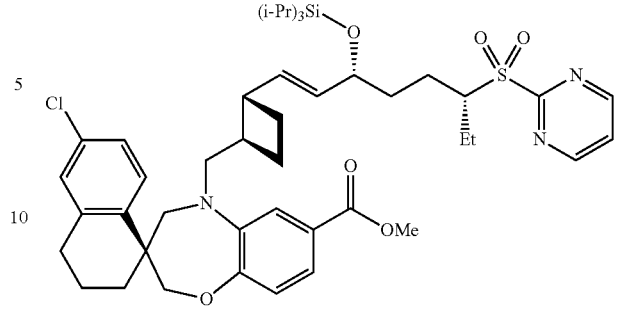

Triisopropylsilyl trifluoromethanesulfonate (0.490 ml, 1.823 mmol) was added dropwise to a stirred, 0° C. solution of (S)-methyl 6'-chloro-5-(((1R,2S)-2-((3S,6R,E)-3-hydroxy-6-(pyrimidin-2-ylsulfonyl)oct-1-en-1-yl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2S)-2-((3R,6R,E)-3-hydroxy-6-(pyrimidin-2-ylsulfonyl)oct-1-en-1-yl)cyclobutyl)methyl)-3',4,4',5-tetrahydro-2H,2'H-spiro[benzo[b][1,4]oxazepine-3,1'-naphthalene]-7-carboxylate (315.8 mg, 0.455 mmol total) and 2,6-lutidine (0.430 mL, 3.69 mmol) in anhydrous dichloromethane (4.5 mL) under an atmosphere of dry nitrogen. After 19 minutes, the reaction was quenched by cautious addition of 20 mL saturated aqueous sodium bicarbonate. The resulting mixture was partitioned between dichloromethane and saturated sodium bicarbonate, washing the organic layer sequentially with 15% (w/w) aqueous citric acid and brine. The organics were dried over magnesium sulfate, filtered and concentrated in vacuo to give a residue that was further purified by flash chromatography (24 g silica gel column eluted with a gradient of 10 to 40% (99:1 ethyl acetate:acetic acid) in heptanes) to provide a mixture of the title compounds as a white foam (348 mg, 90%). m/z (ESI, +ve ion) 849.8 (M+H)⁺.

Step 10: (S)-methyl 6'-chloro-5-(((1R,2S)-2-((3S,6R,E)-6-sulfamoyl-3-((triisopropylsilyl)oxy)oct-1-en-1-yl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2S)-2-((3R,6R,E)-6-sulfamoyl-3-((triisopropylsilyl)oxy)oct-1-en-1-yl)cyclobutyl)methyl)-3',4,4',5-tetrahydro-2H,2'H-spiro[benzo[b][1,4]oxazepine-3,1'-naphthalene]-7-carboxylate

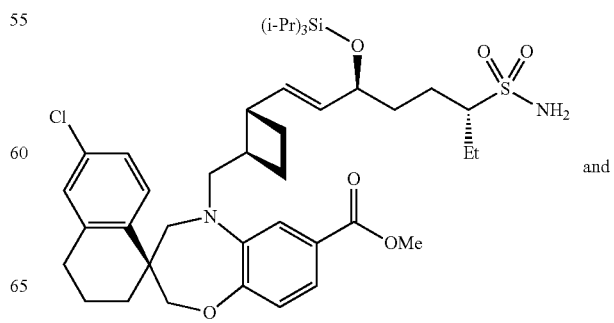

-continued

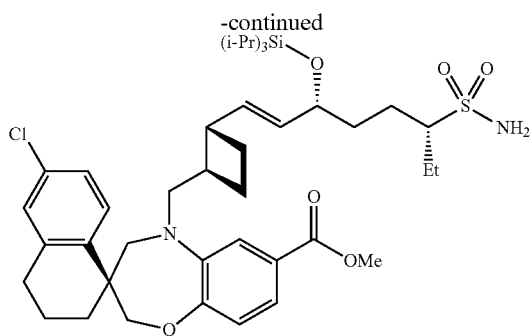

Potassium carbonate (312 mg, 2.258 mmol) was added as the solid to an ice-cooled solution of (S)-methyl 6'-chloro-5-(((1R,2S)-2-((3S,6R,E)-6-(pyrimidin-2-ylsulfonyl)-3-((triisopropylsilyl)oxy)oct-1-en-1-yl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2S)-2-((3R,6R,E)-6-(pyrimidin-2-ylsulfonyl)-3-((triisopropylsilyl)oxy)oct-1-en-1-yl)cyclobutyl)methyl)-3',4,4',5-tetrahydro-2H,2'H-spiro[benzo[b][1,4]oxazepine-3,1'-naphthalene]-7-carboxylate (382.6 mg, 0.450 mmol) in 8 mL 1:1 methanol:tetrahydrofuran and the resulting reaction mixture was vigorously stirred for 49 minutes. A solution of hydroxylamine-O-sulfonic acid (283 mg, 2.25 mmol) and sodium acetate (192 mg, 2.34 mmol) in water (4 mL) was added over the course of three minutes, and the mixture was stirred at room temperature. Additional increments of hydroxylamine-O-sulfonic acid (59.6 mg, 0.474 mmol) and sodium acetate (39.7 mg, 0.484 mmol) were added as a solution in water (0.4 mL) after one hour. Twenty minutes later, the mixture was partitioned between ethyl acetate and 15% (w/w) aqueous citric acid. The organic layer was washed with brine, dried over magnesium sulfate, filtered, and concentrated in vacuo to give a residue that was further purified by flash chromatography (24 g silica gel column eluted with a gradient of 25 to 70% (99:1 ethyl acetate:acetic acid) in heptanes and concentrated from dichloromethane to provide the desired epimer mixture as a white foam (335 mg, 95% yield). m/z (ESI, +ve ion) 788.8 (M+H)$^+$.

Step 11: (S)-6'-chloro-5-(((1R,2S)-2-((3S,6R,E)-6-sulfamoyl-3-((triisopropylsilyl)oxy)oct-1-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2S)-2-((3R,6R,E)-6-sulfamoyl-3-((triisopropylsilyl)oxy)oct-1-en-1-yl)cyclobutyl)methyl)-3',4,4',5-tetrahydro-2H,2'H-spiro[benzo[b][1,4]oxazepine-3,1'-naphthalene]-7-carboxylic acid

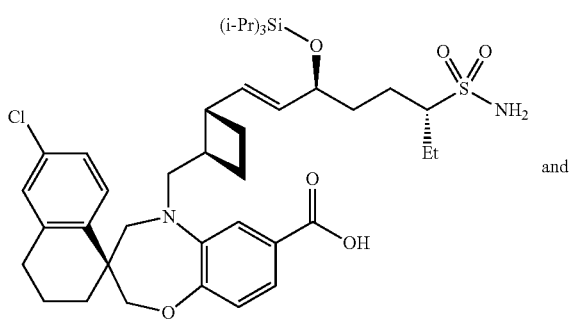

and

-continued

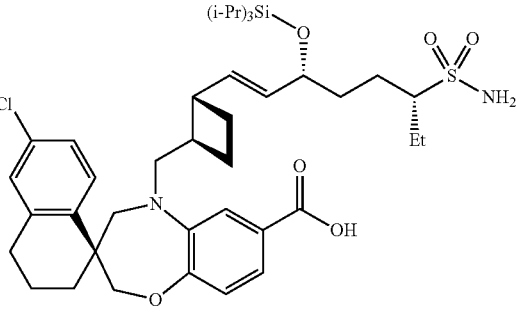

A solution of (S)-methyl 6'-chloro-5-(((1R,2S)-2-((3S,6R,E)-6-sulfamoyl-3-((triisopropylsilyl)oxy)oct-1-en-1-yl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2S)-2-((3R,6R,E)-6-sulfamoyl-3-((triisopropylsilyl)oxy)oct-1-en-1-yl)cyclobutyl)methyl)-3',4,4',5-tetrahydro-2H,2'H-spiro[benzo[b][1,4]oxazepine-3,1'-naphthalene]-7-carboxylate (epimer mixture obtained in Step 10, 321.9 mg, 0.409 mmol) in tetrahydrofuran (2.0 mL) and methanol (1.0 mL) was charged with lithium hydroxide (49.0 mg, 2.05 mmol) and water (1.0 mL) and the resulting reaction mixture was heated at 50° C. in an oil bath. After 2 h the temperature of the oil bath was increased to 60° C. Five minutes later, an additional increment of lithium hydroxide (29.0 mg, 1.21 mmol) was added. The reaction mixture was heated for an additional period of 1.5 h. It was then combined with a mixture generated in the same way starting with a smaller quantity of (1'S)-methyl 6'-chloro-5-(((1R,2S)-2-((6R,E)-6-sulfamoyl-3-((triisopropylsilyl)oxy)oct-1-en-1-yl)cyclobutyl)methyl)-3',4,4',5-tetrahydro-2H,2'H-spiro[benzo[b][1,4]oxazepine-3,1'-naphthalene]-7-carboxylate (epimer mixture, 10.2 mg, 0.013 mmol) for joint work-up and purification. The combined mixtures were partitioned between ethyl acetate and 15% (w/w) citric acid and the organic layer was washed with brine, dried over sodium sulfate, filtered, and concentrated in vacuo to give a residue which was further purified by silica gel chromatography (eluent=15 to 100% (99:1 ethyl acetate:acetic acid) in heptanes) to give the desired epimer mixture as an off-white foam (318 mg, 97% yield based on 0.422 mmol of the methyl ester). m/z (ESI, +ve ion) 774.8 (M+H)$^+$.

Step 12: (1S,3'R,6'S,7'E,9'S,12'R)-6-chloro-12'-ethyl-9'-((triisopropylsilyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [7,16,18,24]tetraen]-15'-one 13',13'-dioxide and (1S,3'R,6'S,7'E,9'R,12'R)-6-chloro-12'-ethyl-9'-((triisopropylsilyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [7,16,18,24]tetraen]-15'-one 13',13'-dioxide

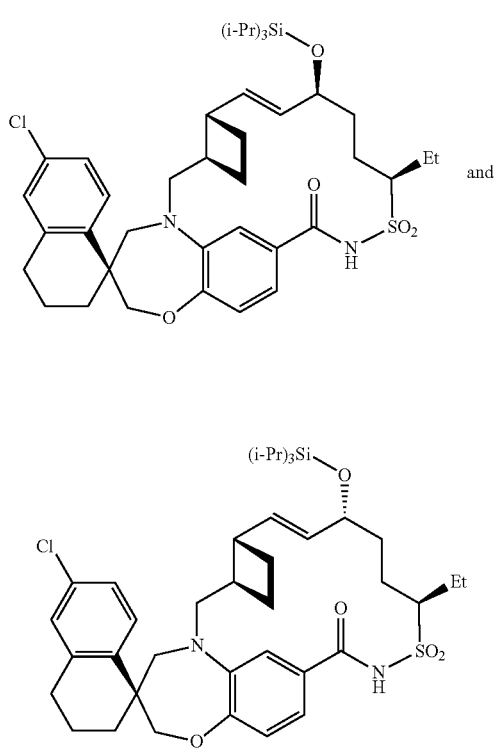

A solution of N1-((ethylimino)methylene)-N3,N3-dimethylpropane-1,3-diamine hydrochloride (126.4 mg, 0.659 mmol) in a anhydrous dichloromethane (37 mL) was added dropwise over the course of 25 minutes to a stirred, ice-cooled solution of (S)-6'-chloro-5-(((1R,2S)-2-((3S,6R,E)-6-sulfamoyl-3-((triisopropylsilyl)oxy)oct-1-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2S)-2-((3R,6R,E)-6-sulfamoyl-3-((triisopropylsilyl)oxy)oct-1-en-1-yl)cyclobutyl)methyl)-3',4,4',5-tetrahydro-2H,2'H-spiro[benzo[b][1,4]oxazepine-3,1'-naphthalene]-7-carboxylic acid (epimer mixture, 252 mg, 0.326 mmol) and N,N-dimethylpyridin-4-amine (68.8 mg, 0.563 mmol) in anhydrous dichloromethane (123 mL). The reaction mixture was allowed to gradually warm to room temperature, and after ca. 15 hours, it was partitioned between ethyl acetate and 15% (w/w) citric acid. The aqueous layer was saturated in sodium-chloride and back-extracted with ethyl acetate. The combined organics were washed with brine, dried over magnesium sulfate, filtered and concentrated in vacuo to give a residue that was further purified by silica gel chromatography (eluent=0 to 50% acetone in dichloromethane). Fractions containing predominantly the early diastereomer were pooled, concentrated in vacuo, and dried under high vacuum to give an off-white powder arbitrarily assigned as the 9'S epimer (103 mg, 42% yield). m/z (ESI, +ve ion) 755.9 (M+H)$^+$. Fractions containing predominantly the late diastereomer were concentrated to obtain an off-white powder arbitrarily assigned as the 9'R epimer (73 mg, 30% yield). m/z (ESI, +ve ion) 755.9 (M+H)$^+$.

Step 13: (1S,3'R,6'S,7'E,9'S,12'R)-6-chloro-12'-ethyl-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [7,16,18,24]tetraen]-15'-one 13',13'-dioxide or (1S,3'R,6'S,7'E,9'R,12'R)-6-chloro-12'-ethyl-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [7,16,18,24]tetraen]-15'-one 13',13'-dioxide Tetrabutylammonium fluoride (1 M in tetrahydrofuran, 1.33 mL, 1.330 mmol) was added to a stirred, ice-cooled solution of either (1S,3'R,6'S,7'E,9'S,12'R)-6-chloro-12'-ethyl-9'-((triisopropylsilyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide or (1S,3'R,6'S,7'E,9'R,12'R)-6-chloro-12'-ethyl-9'-((triisopropylsilyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide (the early, major diastereomer from Step 12, 100 mg, 0.132 mmol) in tetrahydrofuran (1.3 mL). The ice-bath was removed upon completion of the addition, and an additional aliquot of tetrabutylammonium fluoride (600 µL, 0.6 mmol) was added after ca. 1.75 hours. After a total reaction time of ca. 5 hours, the reaction mixture was combined with a mixture generated in same way starting with a smaller quantity (19.1 mg, 0.025 mmol) of the silyl ether for joint workup and purification. The combined reaction mixtures were partitioned between ethyl acetate and 15% (w/w) aqueous citric acid. The organic layer was washed with brine, dried over magnesium sulfate, filtered and concentrated in vacuo to give a residue that was further purified by silica gel chromatography, eluting with a gradient of 10 to 40% (99:1 ethyl acetate:acetic acid) in heptanes, to provide the title compound as a white powder (66 mg, 70% yield based on 0.157 mmol of the silyl ether). $^1$H NMR (500 MHz, CD$_2$Cl$_2$) δ ppm 8.12 (br. s., 1H), 7.71 (d, J=8.6 Hz, 1H), 7.17 (dd, J=8.6, 2.4 Hz, 1H), 7.09 (d, J=2.4 Hz, 1H), 6.94-6.99 (m, 1H), 6.90-6.93 (m, 1H), 6.85 (d, J=1.7 Hz, 1H), 6.09 (dd, J=15.5, 5.5 Hz, 1H), 5.54 (ddd, J=15.6, 7.6, 1.2 Hz, 1H), 4.14-4.21 (m, 1H), 4.10 (s, 2H), 3.76-3.87 (m, 1H), 3.67 (d, J=14.2 Hz, 1H), 3.18 (d, J=14.2 Hz, 1H), 3.07 (dd, J=15.7, 8.3 Hz, 1H), 2.69-2.83 (m, 2H), 2.56-2.66 (m, 1H), 2.17 (dqd, J=14.4, 7.4, 7.4, 7.4, 4.5 Hz, 1H), 1.76-2.10 (m, 11H), 1.60-1.71 (m, 2H), 1.54-1.57 (m, 1H), 1.40-1.47 (m, 1H), 1.15 (t, J=7.5 Hz, 3H). m/z (ESI, +ve ion) 598.9 (M+H)$^+$.

Example 198. (1S,3'R,6'S,7'E,9'R,12'R)-6-chloro-12'-ethyl-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [7,16,18,24]tetraen]-15'-one 13',13'-dioxide or (1S,3'R,6'S,7'E,9'S,12'R)-6-chloro-12'-ethyl-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [7,16,18,24]tetraen]-15'-one 13',13'-dioxide

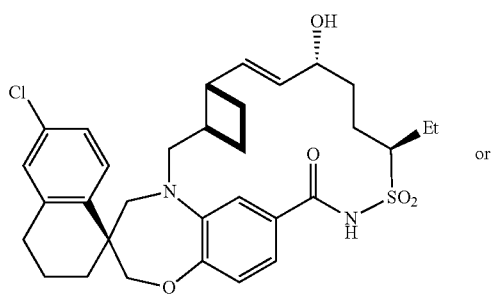

or

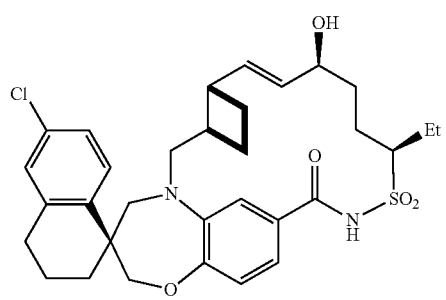

This compound was prepared in the same manner as in Step 13 of Example 197, starting instead from the late, minor diastereomer (85.2 mg, 0.113 mmol) from Step 12 of Example 197, and was obtained in the amount of 31 mg (46% yield for the desilylation reaction). $^1$H NMR (500 MHz, CD$_2$Cl$_2$) δ ppm 8.01 (br. s., 1H), 7.71 (d, J=8.6 Hz, 1H), 7.17 (dd, J=8.4, 2.3 Hz, 1H), 7.09 (d, J=2.4 Hz, 1H), 6.95-7.00 (m, 1H), 6.91-6.94 (m, 1H), 6.74 (d, J=1.7 Hz, 1H), 5.83 (dd, J=15.5, 7.0 Hz, 1H), 5.54 (dd, J=15.4, 6.1 Hz, 1H), 4.14 (quin, J=5.6 Hz, 1H), 4.05-4.12 (m, 2H), 3.68-3.79 (m, 3H), 3.27 (d, J=14.4 Hz, 1H), 3.14 (dd, J=15.4, 9.3 Hz, 1H), 2.70-2.84 (m, 2H), 2.61 (quin, J=8.3 Hz, 1H), 2.34 (quin, J=8.6 Hz, 1H), 2.09-2.19 (m, 1H), 2.01-2.09 (m, 3H), 1.80-1.97 (m, 5H), 1.67-1.79 (m, 5H), 1.40-1.48 (m, 1H), 1.14 (t, J=7.5 Hz, 3H). m/z (ESI, +ve ion) 598.9 (M+H)$^+$.

Example 199. (1S,3'R,6'S,7'E,9'S,12'R)-6-chloro-12'-ethyl-9'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [7,16,18,24]tetraen]-15'-one 13',13'-dioxide or (1S,3'R,6'S,7'E,9'R,12'R)-6-chloro-12'-ethyl-9'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [7,16,18,24]tetraen]-15'-one 13',13'-dioxide

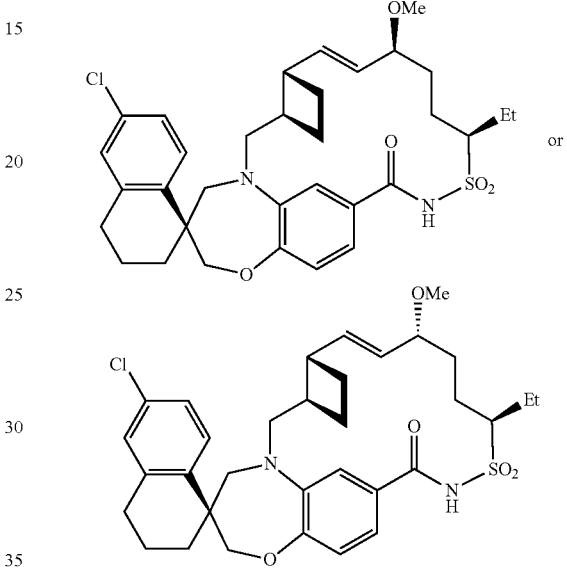

An ice-cooled solution of either (1S,3'R,6'S,7'E,9'S,12'R)-6-chloro-12'-ethyl-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide or (1S,3'R,6'S,7'E,9'R,12'R)-6-chloro-12'-ethyl-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide (Example 183, 14.6 mg, 0.024 mmol) in anhydrous tetrahydrofuran (500 μL) was charged with sodium hydride (60% dispersion in mineral oil, 9.4 mg, 0.235 mmol) and the resulting stirred suspension was allowed to warm to room temperature. After seven minutes, iodomethane (8 μL, 0.129 mmol) was added and the resulting reaction mixture was stirred at ambient temperature for 21 hours, after which time it was partitioned between ethyl acetate and saturated ammonium chloride. The organics were washed with brine, dried over magnesium sulfate, filtered and concentrated in vacuo to give a residue that was further purified by silica gel chromatography (4 g silica gel column eluted with a gradient of 0 to 40% (99:1 ethyl acetate:acetic acid) in heptanes to provide the title compound as a white powder (8.7 mg, 58% yield). $^1$H NMR (500 MHz, CD$_2$Cl$_2$) δ ppm 8.09 (s, 1H), 7.63 (d, J=8.6 Hz, 1H), 7.08 (dd, J=8.6, 2.2 Hz, 1H), 7.01 (d, J=2.2 Hz, 1H), 6.87-6.91 (m, 1H), 6.81-6.85 (m, 1H), 6.79 (d, J=2.0 Hz, 1H), 6.09 (dd, J=15.5, 5.3 Hz, 1H), 5.27 (ddd, J=15.5, 8.3, 1.0 Hz, 1H), 4.02 (s, 2H), 3.70-3.78 (m, 2H), 3.53-3.61 (m, 2H), 3.11 (s, 3H), 3.08 (d, J=14.2 Hz, 1H), 2.99 (dd, J=15.5, 7.7 Hz, 1H), 2.61-2.76 (m, 2H), 2.51-2.60 (m, 1H), 2.05-2.17 (m, 1H), 1.88-1.97 (m, 4H), 1.68-1.88

(m, 5H), 1.52-1.68 (m, 3H), 1.29-1.39 (m, 2H), 1.06 (t, J=7.5 Hz, 3H). m/z (ESI, +ve ion) 612.8 (M+H)+.

Example 200. (1S,3'R,6'S,7'E,9'S,12'R)-6-chloro-12'-ethyl-9'-(2-methoxyethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [7,16,18,24]tetraen]-15'-one 13',13'-dioxide or (1S,3'R,6'S,7'E,9'R,12'R)-6-chloro-12'-ethyl-9'-(2-methoxyethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [7,16,18,24]tetraen]-15'-one 13',13'-dioxide

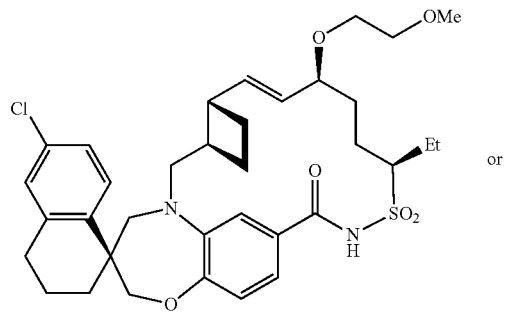

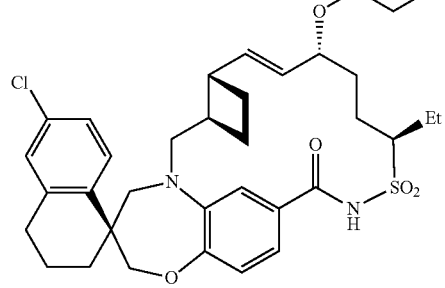

A stirred, ice-cooled solution of either (1S,3'R,6'S,7'E,9'S,12'R)-6-chloro-12'-ethyl-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide or (1S,3'R,6'S,7'E,9'R,12'R)-6-chloro-12'-ethyl-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide (Example 183, 15.2 mg, 0.025 mmol) in anhydrous N,N-dimethylformamide (0.50 mL) was charged with sodium hydride (60% dispersion in mineral oil, 11 mg, 0.275 mmol), and the resulting suspension was allowed to warm to room temperature. After three minutes, 1-bromo-2-methoxyethane (12 μL, 0.128 mmol) was added via microsyringe. The resulting reaction mixture was stirred for 18 hours and then partitioned between partitioned between ethyl acetate and saturated ammonium chloride. The organic layer was washed sequentially with 5% (w/w) lithium chloride, 15% (w/w) citric acid and brine, dried over magnesium sulfate, filtered and concentrated in vacuo to give a residue that was further purified by silica gel chromatography (same method as in Example 185) to provide the title compound as a white powder (8.9 mg, 53% yield). $^1$H NMR (500 MHz, CD$_2$Cl$_2$) δ ppm 8.19 (s, 1H), 7.71 (d, J=8.6 Hz, 1H), 7.17 (dd, J=8.6, 2.2 Hz, 1H), 7.09 (d, J=2.2 Hz, 1H), 6.94-7.00 (m, 1H), 6.89-6.93 (m, 1H), 6.87 (d, J=2.0 Hz, 1H), 6.16 (dd, J=15.6, 5.4 Hz, 1H), 5.38 (ddd, J=15.7, 8.4, 1.1 Hz, 1H), 4.10 (s, 2H), 3.74-3.87 (m, 3H), 3.66 (d, J=14.2 Hz, 1H), 3.56 (ddd, J=10.4, 6.3, 3.7 Hz, 1H), 3.41-3.51 (m, 2H), 3.32 (ddd, J=10.5, 5.7, 3.8 Hz, 1H), 3.30 (s, 3H), 3.16 (d, J=14.2 Hz, 1H), 3.07 (dd, J=15.5, 7.7 Hz, 1H), 2.68-2.83 (m, 2H), 2.58-2.68 (m, 1H), 2.13-2.23 (m, 1H), 1.96-2.07 (m, 3H), 1.60-1.95 (m, 9H), 1.39-1.48 (m, 2H), 1.14 (t, J=7.5 Hz, 3H). m/z (ESI, +ve ion) 656.8 (M+H)+.

Example 201. 2944012 (1S,3'R,6'R,7'S,8'E,10'S)-6-chloro-7'-hydroxy-10'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

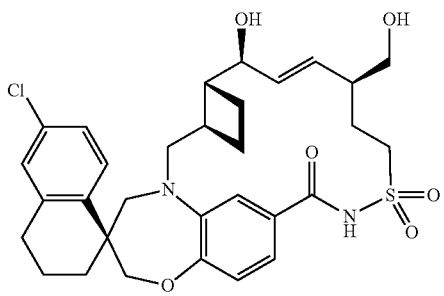

Step 1: (S)-3-(((tert-butyldiphenylsilyl)oxy)methyl)pent-4-en-1-ol

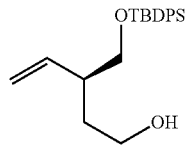

To a solution of (S)-methyl 3-(((tert-butyldiphenylsilyl)oxy)methyl)pent-4-enoate (0.14 g, 0.366 mmol) prepared according to the method of Helmchen et al.[1] dissolved in THF (4 mL) at room temperature was added lithium borohydride (0.366 mL, 0.732 mmol) as a 2 M solution in THF all at once. After 5 minutes no reaction was observed by TLC. To the reaction was added methanol (0.059 mL, 1.464 mmol). After 16 hours TLC indicated a small amount of starting material remained. An additional equivalent of lithium borohydride was added followed by an additional 2 equivalents of methanol. After 2 hours TLC indicated no starting material remained. To the reaction solution was added 5 ml saturated aqueous sodium bicarbonate solution and 5 ml water. The mixture was extracted with 2×25 ml diethyl ether. The combined organic extracts were washed with 20 ml brine, stirred over anhydrous magnesium sulfate, filtered and the filtrate concentrated under reduced pressure to afford (S)-3-(((tert-butyldiphenylsilyl)oxy)methyl)pent-4-en-1-ol as a colorless oil (135 mg, 0.37 mmol, 100% yield).

[1] Helmchen et al. *Synlett* 2007, 790.

Step 2: (S)-3-(((tert-butyldiphenylsilyl)oxy)methyl)pent-4-en-1-yl methanesulfonate

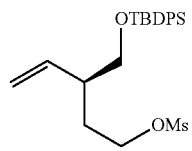

To a solution of (S)-3-(((tert-butyldiphenylsilyl)oxy)methyl)pent-4-en-1-ol (0.13 g, 0.367 mmol), 4-dimethylaminopyridine (1.344 mg, 11.00 μmol) and triethylamine (0.056 mL, 0.403 mmol) in DCM (3.67 mL) at room temperature was added neat methanesulfonyl chloride (0.028 mL, 0.367 mmol). The reaction was stirred at ambient temperature for 60 minutes then partitioned between 20 mL each DCM and saturated aqueous ammonium chloride. The aqueous separation was extracted again with 20 ml DCM. The combined organic extracts were stirred over anhydrous magnesium sulfate, filtered and the filtrate concentrated under reduced pressure to afford (S)-3-(((tert-butyldiphenylsilyl)oxy)methyl)pent-4-en-1-yl methanesulfonate as a colorless oil (156 mg, 0.36 mmol, 98% yield).

Step 3: (S)-3-(((tert-butyldiphenylsilyl)oxy)methyl)pent-4-en-1-yl)thio)pyrimidine

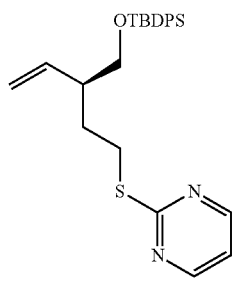

To a mixture of (S)-3-(((tert-butyldiphenylsilyl)oxy)methyl)pent-4-en-1-yl methanesulfonate (0.15 g, 0.347 mmol) and 2-mercaptopyrimidine (0.047 g, 0.416 mmol) in DMF (3 mL) at room temperature was added potassium carbonate (0.025 mL, 0.416 mmol) all at once. The resulting yellow mixture was stirred at ambient temperature for 60 minutes then partitioned between 25 mL each 1:1 saturated aqueous ammonium chloride:water and diethyl ether. The aqueous separation was extracted again with 25 mL diethyl ether. The combined ethereal layers were washed with 25 mL water followed by 25 mL brine, stirred over anhydrous magnesium sulfate, filtered and the filtrate concentrated under reduced pressure to afford a pale yellow oil (159 mg). The product was isolated by chromatography on 40 g RediSep Rf column eluting with 20% ethyl acetate in hexane at 40 ml/min. to afford (S)-2-((3-(((tert-butyldiphenylsilyl)oxy)-methyl)pent-4-en-1-yl)thio)pyrimidine as a colorless oil (127 mg, 0.28 mmol, 82% yield).

Step 4: (S)-3-(((tert-butyldiphenylsilyl)oxy)methyl)pent-4-en-1-yl)sulfonyl)-pyrimidine

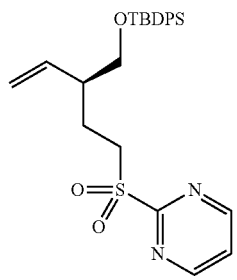

To a mixture of sodium tungstate, dihydrate (0.016 mL, 0.158 mmol), phenylphosphonic acid (0.018 mL, 0.158 mmol) and tetrabutylammonium sulfate, 50 wt. % solution in water (0.182 mL, 0.158 mmol) was added hydrogen peroxide solution, 30% wt. % in water (0.485 mL, 4.75 mmol) all at once. The mixture was stirred for 5 minutes before a solution of (S)-2-((3-(((tert-butyldiphenylsilyl)oxy)methyl)pent-4-en-1-yl)thio)pyrimidine (0.71 g, 1.582 mmol) dissolved in toluene (4 mL) was added. The mixture was heated to 50° C. After 60 minutes TLC indicated very little product. Heat was increased to 60° C. and the mixture was stirred overnight at this temperature. After 18 hours TLC indicated no starting material remained and LCMS confirmed complete consumption of SM and formation of desired product. The reaction was equilibrated to RT and partitioned between 30 mL each water and ethyl acetate. The aqueous separation was extracted again with 30 mL ethyl acetate. The combined organic extracts were washed with 30 ml brine, stirred over anhydrous magnesium sulfate, filtered and the filtrate concentrated under reduced pressure to afford a colorless oil. The product was isolated by chromatography on 40 g RediSep Rf Gold column eluting with 33-50% ethyl acetate gradient in hexane at 40 ml/min to afford (S)-2-((3-(((tert-butyldiphenylsilyl)oxy)methyl)pent-4-en-1-yl)sulfonyl)-pyrimidine as a colorless oil (600 mg, 1.25 mmol, 79% yield).

Step 5: (S)-3-(((tert-butyldiphenylsilyl)oxy)methyl)pent-4-en-1-sulfonamide

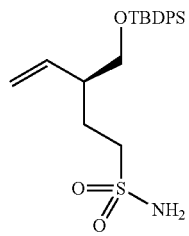

To a solution of (S)-2-((3-(((tert-butyldiphenylsilyl)oxy)methyl)pent-4-en-1-yl)sulfonyl)pyrimidine (0.6 g, 1.248 mmol) dissolved in MeOH (12 mL) at room temperature was added sodium ethoxide, 21 w/w solution in ethanol (0.466 mL, 1.248 mmol) all at once. The resulting solution was stirred at ambient temperature for 30 minutes then concentrated under reduced pressure. The sulfinate was dissolved in MeOH (3.00 mL) and water (3 mL) and this solution added all at once to a solution of hydroxylamine-o-sulfonic acid (0.282 g, 2.496 mmol) and sodium acetate (0.134 mL, 2.496 mmol) dissolved in MeOH (3.00 mL) and water (3 mL) heated to 50° C. After 2 hours the reaction was concentrated under reduced pressure and the concentrate partitioned between 30 mL each water and ethyl acetate. The aqueous separation was extracted again with 30 mL ethyl acetate. The combined organic layers were stirred over anhydrous magnesium sulfate, filtered and the filtrate concentrated under reduced pressure to afford a colorless oil. The product was isolated by chromatography on 40 g RediSep Rf Gold column eluting with 35% ethyl acetate in hexane at 40 ml/min to afford (S)-3-(((tert-butyldiphenylsilyl)oxy)methyl)pent-4-ene-1-sulfonamide as a colorless oil (405 mg, 0.97 mmol, 78% yield).

Step 6: (S)-5-(((1R,2R)-2-((1S,((S,E)-4-(((tert-butyldiphenylsilyl)oxy)methyl)-1-hydroxy-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid

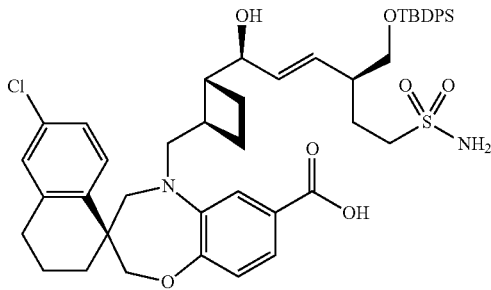

A mixture of (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (0.1 g, 0.196 mmol, Intermediate AA11A) and (S)-3-(((tert-butyldiphenylsilyl)oxy)methyl)pent-4-ene-1-sulfonamide (0.279 g, 0.668 mmol, Step 5) dissolved in 1,2-dichloroethane (5 mL) was degassed with a stream of argon for 10 minutes before Hoveyda-Grubbs catalyst 2nd generation (0.018 g, 0.029 mmol) was added. The reaction was left stirring overnight at room temperature. After 18 hours 100 µL ethyl vinyl ether was added and air bubbled through the reaction solution for 10 minutes. The solution was concentrated under reduced pressure then purified by chromatography as described. The products were isolated by chromatography on 24 g RediSep Rf Gold column eluting with 30 TO 100% ethyl acetate in hexane at 40 ml/min to afford (S)-5-(((1R,2R)-2-((1S,((S,E)-4-(((tert-butyldiphenylsilyl)oxy)methyl)-1-hydroxy-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid as a colorless film (50 mg, 0.058 mmol, 30% yield).

Step 7: (1S,3'R,6'R,7'S,8'E,10'S)-6-chloro-7'-hydroxy-10'-((((2-methyl-2-propanyl)(diphenyl)silyl)oxy)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

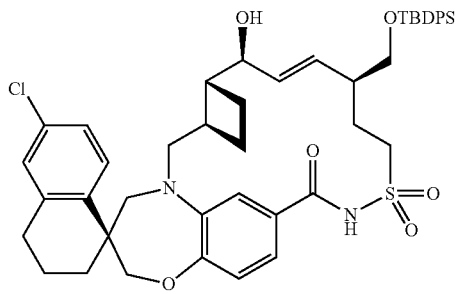

A mixture of (S)-5-(((1R,2R)-2-((1S,((S,E)-4-(((tert-butyldiphenylsilyl)oxy)methyl)-1-hydroxy-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid (0.05 g, 0.058 mmol), 4-dimethylaminopyridine (0.012 g, 0.099 mmol) and 1-ethyl-(3-dimethylaminopropyl)carbodiimide hydrochloride (0.022 g, 0.117 mmol) in DCM (29.2 mL) at room temperature was stirred for 4 days then concentrated under reduced pressure. The product was isolated by chromatography on 12 g RediSep Rf Gold column eluting with 60% ethyl acetate in hexane+0.5% acetic acid to afford (1S,3'R,6'R,7'S,8'E,10'S)-6-chloro-7'-hydroxy-10'-((((2-methyl-2-propanyl)(diphenyl)silyl)oxy)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as a colorless film (17 mg, 0.020 mmol, 35% yield).

Step 8: (1S,3'R,6'R,7'S,8'E,10'S)-6-chloro-7'-hydroxy-10'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide To a solution of (1S,3'R,6'R,7'S,8'E,10'S)-6-chloro-7'-hydroxy-10'-((((2-methyl-2-propanyl)(diphenyl)silyl)oxy)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (0.017 g, 0.020 mmol) dissolved in THF (2 mL) at room temperature was added tetrabutylammonium fluoride, 1.0m in tetrahydrofuran (0.061 mL, 0.061 mmol). The reaction was stirred at ambient temperature overnight. After 24 hours the reaction was concentrated under reduced pressure then isolated by chromatography on 12 g RediSep Rf Gold column eluting with 30% acetone in DCM at 35 ml/min to afford (1S,3'R,6'R,7'S,8'E,10'S)-6-chloro-7'-hydroxy-10'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as a colorless film. $^1$H NMR (400 MHz, CD$_2$Cl$_2$) δ ppm 7.75 (d, J=8.41 Hz, 1H), 7.21 (dd, J=8.41, 2.35 Hz, 1H), 7.14 (d, J=2.35 Hz, 1H), 7.12 (br. s., 1H), 7.00-7.05 (m, 1H), 6.95-7.00 (m, 1H), 5.73-5.83 (m, 1H), 5.64-5.73 (m, 1H), 4.35 (br. s., 1H), 4.17 (s, 2H), 3.98 (t, J=11.15 Hz, 1H), 3.74-3.84 (m, 1H), 3.59-3.73 (m, 3H), 3.48 (dd, J=10.66, 6.75 Hz, 1H), 3.34 (d, J=14.48 Hz, 2H), 3.21 (d, J=16.63 Hz, 1H), 2.74-2.88 (m, 2H), 2.32-2.58 (m, 3H), 1.52-1.78 (m, 12H); m/z (ESI, +ve ion) 601.2 (M+H)+.

Example 202. (1S,3'R,6'R,7'S,8'E,10'R,12'R)-6-chloro-10'-(2-hydroxyethyl)-7'-methoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

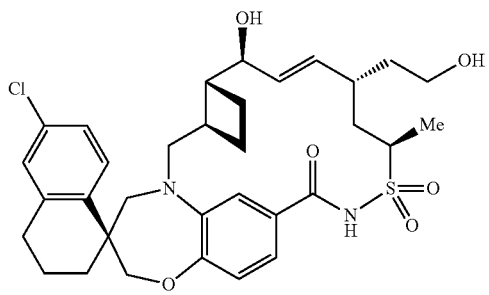

Step 1:
(4S,6S)-6-methyl-4-vinyltetrahydro-2H-pyran-2-one

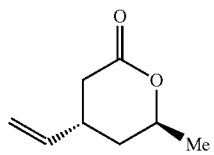

Prepared according to the method of Kido et al.[2] using (S)-(+)-parasorbic acid which is prepared by the method of Dupont and Donato.[3]

[2] Kido et al. *Tetrahedron* 1990, 46(13-14), 4887.
[3] Dupont, J. and Donato, A. J. *Tetrahedron: Asymmetry* 1998, 9(6), 949.

Step 2: (3R,5S)-3-vinylhexane-1,5-diol

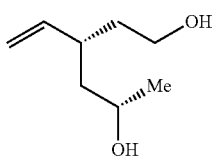

To a solution of (4S,6S)-6-methyl-4-vinyltetrahydro-2H-pyran-2-one (0.677 g, 4.83 mmol) in MeOH (24.15 mL) cooled by an ice bath was added solid sodium borohydride (0.851 mL, 24.15 mmol) in portions over 10 minutes. After 15 minutes the cold bath was removed and the reaction equilibrated to room temperature. The reaction was stirred at room temperature for 2 hours then 3 mL saturated aqueous sodium bicarbonate was added and the resulting mixture stirred for 15 minutes before the methanol was removed under reduced pressure on a rotary evaporator. The concentrate was partitioned between 25 ml each water and ethyl acetate. The aqueous separation was extracted with 2×25 mL ethyl acetate. The combined organic extracts were stirred over anhydrous magnesium sulfate, filtered and the filtrate concentrated under reduced pressure to afford (3R,5S)-3-vinylhexane-1,5-diol as a colorless oil (618 mg, 4.29 mmol, 89% yield).

Step 3: (2S,4R)-4-(2-((tert-butyldimethylsilyl)oxy)ethyl)hex-5-en-2-ol

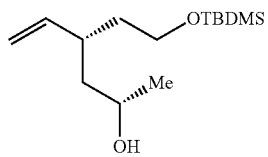 [SMILES: C=C[C@H](CCO[Si](C)(C)C(C)(C)C)C[C@H](C)O]

To a solution of (3R,5S)-3-vinylhexane-1,5-diol (0.6 g, 4.16 mmol) and imidazole (0.274 mL, 4.16 mmol) in DMF (20.80 mL) cooled by an ice bath was added solid tert-butyldimethylsilyl chloride (0.627 g, 4.16 mmol) all at once. The cold bath was removed and the reaction equilibrated to room temperature. The reaction was stirred at room temperature overnight. After ca. 18 hours the reaction was partitioned between 50 mL water and 30 mL hexane. The aqueous layer was extracted twice again with 30 ml hexane each. The combined organic extracts were washed with 3×20 mL water followed by 20 mL brine, stirred over anhydrous magnesium sulfate, filtered and the filtrate concentrated under reduced pressure to afford a colorless oil (1 g). The product was isolated by chromatography on 80 g RediSep Rf column eluting with 20% ethyl acetate in hexane at 60 ml/min to afford (2S,4R)-4-(2-((tert-butyldimethylsilyl)oxy)ethyl)hex-5-en-2-ol as a colorless oil (670 mg, 2.59 mmol, 62% yield).

Step 4: (2S,4R)-4-(2-((tert-butyldimethylsilyl)oxy)ethyl)hex-5-en-2-yl methanesulfonate

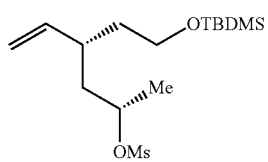 [SMILES: C=C[C@H](CCO[Si](C)(C)C(C)(C)C)C[C@H](C)OS(C)(=O)=O]

To a solution of (2S,4R)-4-(2-((tert-butyldimethylsilyl)oxy)ethyl)hex-5-en-2-ol (0.72 g, 2.79 mmol), triethylamine (0.426 mL, 3.06 mmol) and 4-(dimethylamino)pyridine (0.017 g, 0.139 mmol) dissolved in DCM (18.57 mL) cooled by an ice bath was added neat methanesulfonyl chloride (0.226 mL, 2.92 mmol) all at once. The cold bath was removed and the reaction equilibrated to room temperature. TLC after 15 and 75 minutes was identical—starting material remained. After 90 minutes additional methanesulfonyl chloride (0.15 equiv) and triethylamine (0.2 equiv) was added to the room temperature solution. The reaction was stirred for an additional 60 minutes then TLC indicated no starting material remained. The reaction was washed with 30 mL 0.1N citric acid solution followed by 25 mL water and 25 mL brine, stirred over anhydrous magnesium sulfate, filtered and the filtrate concentrated under reduced pressure to afford (2S,4R)-4-(2-((tert-butyldimethylsilyl)oxy)ethyl)

hex-5-en-2-yl methanesulfonate as a pale yellow oil (950 mg, 2.82 mmol, 100% yield).

Step 5: 2-(((2R,4R)-4-(2-((tert-butyldimethyl silyl)oxy)ethyl)hex-5-en-2-yl)thio)pyrimidine

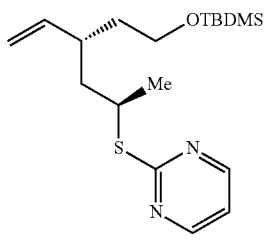 [SMILES: C=C[C@H](CCO[Si](C)(C)C(C)(C)C)C[C@@H](C)Sc1ncccn1]

To a suspension of 2-mercaptopyrimidine (0.360 g, 3.21 mmol) in EtOH (8.91 mL) at room temperature was added sodium ethoxide, 21% weight solution in ethanol (1.148 mL, 3.08 mmol) all at once. The resulting orange, homogeneous solution was stirred at ambient temperature for ten minutes before a solution of (2S,4R)-4-(2-((tert-butyldimethylsilyl)oxy)ethyl)hex-5-en-2-yl methanesulfonate (0.9 g, 2.67 mmol) dissolved in EtOH (4.46 ml) was added all at once. The reaction was heated to 50° C. overnight. After sixteen hours thin layer chromatography indicated no starting material remained. The reaction was concentrated under reduced pressure and the concentrate partitioned between 30 mL ethyl acetate and 30 mL 0.1N aqueous sodium carbonate solution. The aqueous layer was extracted again with 2×30 mL ethyl acetate. The combined organic extracts were washed with 30 mL brine, stirred over anhydrous magnesium sulfate, filtered and the filtrate concentrated under reduced pressure to afford a yellow oil (1 g). The product was isolated by chromatography on 80 g RediSep Rf column eluting with 15% ethyl acetate in hexane at 60 mL/min to afford 2-(((2R,4R)-4-(2-((tert-butyldimethylsilyl)oxy)ethyl)hex-5-en-2-yl)thio)pyrimidine as a colorless oil (667 mg, 1.89 mmol, 71% yield).

Step 6: 2-(((2R,4R)-4-(2-((tert-butyldimethyl silyl)oxy)ethyl)hex-5-en-2-yl)sulfonyl)pyrimidine

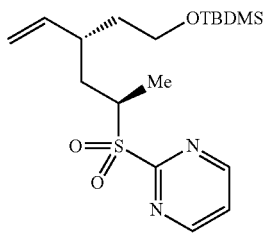 [SMILES: C=C[C@H](CCO[Si](C)(C)C(C)(C)C)C[C@@H](C)S(=O)(=O)c1ncccn1]

Into a 25 mL round bottom flask were charged sequentially sodium tungstate oxide dihydrate (0.019 mL, 0.184 mmol), phenylphosphonic acid (0.021 mL, 0.184 mmol), tetrabutylammonium sulfate, 50% weight solution in water (0.212 mL, 0.184 mmol) and hydrogen peroxide 30% in water (0.471 mL, 4.61 mmol) at room temperature. The gummy mixture was aged for five minutes (NOTE: stir bar stopped for first couple minutes then returned to stirring as the mixture thinned and solids deposited on the inside of the reaction flask). To the mixture at room temperature was added a solution of 2-(((2R,4R)-4-(2-((tert-butyldimethylsilyl)oxy)ethyl)hex-5-en-2-yl)thio)pyrimidine (0.65 g, 1.843 mmol) dissolved in toluene (3.5 mL). The reaction mixture was heated to 50° C. with rapid stirring. After 90 minutes at 50° C. thin layer chromatography and LCMS indicated no starting material remained and a single product peak with mass corresponding to sulfone predominated. After two hours total reaction time the reaction was removed from heat and equilibrated to room temperature. The reaction mixture was partitioned between 25 mL each water and ethyl acetate. The aqueous layer was extracted again with 2×25 mL ethyl acetate. The combined organic layers were washed with 25 mL brine, stirred over anhydrous magnesium sulfate, filtered and the filtrate concentrated under reduced pressure to afford 2-(((2R,4R)-4-(2-((tert-butyldimethylsilyl)oxy)ethyl)hex-5-en-2-yl)sulfonyl)pyrimidine as a colorless oil (700 mg, 1.82 mmol, 99% yield).

Step 7: (2R,4R)-4-(2-((tert-butyldimethylsilyl)oxy)ethyl)hex-5-ene-2-sulfonamide

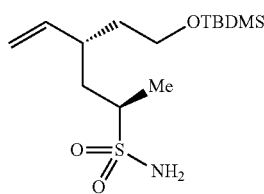 [SMILES: C=C[C@H](CCO[Si](C)(C)C(C)(C)C)C[C@@H](C)S(N)(=O)=O]

To a room temperature solution of 2-(((2R,4R)-4-(2-((tert-butyldimethylsilyl)oxy)ethyl)hex-5-en-2-yl)sulfonyl)pyrimidine (0.65 g, 1.690 mmol) dissolved in MeOH (10 mL) was added sodium ethoxide, 21% weight solution in ethanol (0.631 mL, 1.690 mmol) all at once. The solution was stirred at room temperature for 30 minutes then concentrated under reduced pressure. The sodium sulfinate intermediate could not be precipitated with either diethyl ether or hexane. The concentrate was used without removal of the 2-methoxypyrimidine by-product. The concentrate was dissolved in MeOH (15 mL) and water (3 mL) and heated to 50° C., at which temperature a solution of hydroxylamine-o-sulphonic acid (0.382 g, 3.38 mmol) and sodium acetate (0.181 mL, 3.38 mmol) dissolved in water (5 mL) was added over one minute. A turbid solution developed within five minutes. Stirring at 50° C. was continued for 70 minutes after which time LCMS indicated no sulfinate remained. The reaction mixture was concentrated under reduced pressure and the concentrate partitioned between 25 mL each water and ethyl acetate. The aqueous separation was extracted again with 2×25 mL ethyl acetate. The combined organic layers were washed with 25 mL brine, stirred over anhydrous magnesium sulfate, filtered and the filtrate concentrated under reduced pressure to afford a pale yellow oil (500 mg). The product was isolated by chromatography on 40 g RediSep Rf Gold column eluting with 35-100% ethyl acetate gradient in hexane at 40 mL/min to afford (2R,4R)-4-(2-((tert-butyldimethylsilyl)oxy)ethyl)hex-5-ene-2-sulfonamide as a colorless oil (324 mg, 1.01 mmol, 60% yield).

Step 8: (S)-5-(((1R,2R)-2-((1S,4R,6R,E)-4-(2-((tert-butyldimethylsilyl)oxy)ethyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid

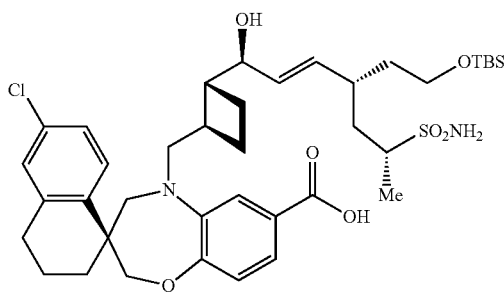

A solution of (2R,4R)-4-(2-((tert-butyldimethylsilyl)oxy)ethyl)hex-5-ene-2-sulfonamide (0.32 g, 0.995 mmol) and (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (0.14 g, 0.299 mmol, Intermediate AA11A) dissolved in 1,2-dichloroethane (3 mL) was degassed by sparging a stream of argon through the solution at room temperature for ten minutes. To the solution was added solid Hoveyda-Grubbs catalyst 2nd generation (0.019 g, 0.030 mmol) all at once. The reaction was stirred at room temperature for 30 minutes after which time LCMS indicated no starting material remained. Air was sparged through the reaction for ten minutes at room temperature and the reaction was stirred open to air for two hours before concentrating under reduced pressure. The product was isolated by chromatography on 24 g RediSep Rf Gold column eluting with 35% acetone in hexane at 30 mL/min to afford (S)-5-(((1R,2R)-2-((1S,4R,6R,E)-4-(2-((tert-butyldimethylsilyl)oxy)ethyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid as a colorless film (40 mg, 0.053 mmol, 18% yield).

Step 9: (1S,3'R,6'R,7'S,8'E,10'R,12'R)-6-chloro-10'-(2-((dimethyl(2-methyl-2-propanyl)silyl)oxy)ethyl)-7'-hydroxy-12'-methyl-3,4-dihydro-2H,15'H-spiro[naphthalene-1,22'-[20]oxa[13]thia[1,14]diazatetracyclo-[14.7.2.0$^{3,6}$.0$^{19,24}$]pentacosa[8,16,18,24]tetraen]-15'-one 13',13'-dioxide

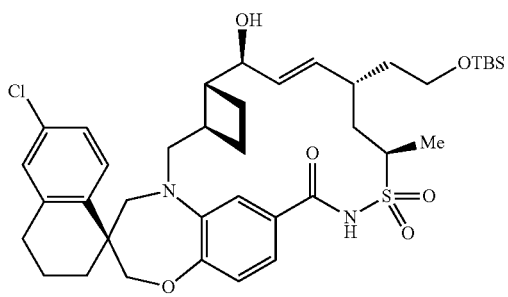

To a solution of 4-(dimethylamino)pyridine (0.022 g, 0.179 mmol) and (S)-5-(((1R,2R)-2-((1S,4R,6R,E)-4-(2-((tert-butyldimethylsilyl)oxy)ethyl)-1-hydroxy-6-sulfamoylhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid (0.08 g, 0.105 mmol) dissolved in DCM (52.5 mL) cooled by an ice bath was added solid 1-(3-dimethylaminopropyl)-3-ethylcarbodiimide hydrochloride (0.040 g, 0.210 mmol) all at once. The reaction slowly equilibrated to room temperature and was stirred overnight. After 20 hours the reaction was concentrated under reduced pressure and the concentrate partitioned between 25 mL each DCM and 0.1N aqueous citric acid solution. The aqueous separation was extracted again with DCM (2×15 mL). The combined organic extracts were washed with 2×15 mL water then 15 mL brine, stirred over anhydrous magnesium sulfate, filtered and the filtrate concentrated under reduced pressure to afford a colorless film. The product was isolated by chromatography on 24 g RediSep Rf Gold column eluting with 30% acetone in hexane at 40 mL/min to afford (1S,3'R,6'R,7'S,8'E,10'R,12'R)-6-chloro-10'-(2-((dimethyl(2-methyl-2-propanyl)silyl)oxy)ethyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa-[8,16,18,24]tetraen]-15'-one 13',13'-dioxide as a colorless film (55 mg, 0.074 mmol, 70% yield).

Step 10: (1S,3'R,6'R,7'S,8'E,10'R,12'R)-6-chloro-10'-(2-((dimethyl(2-methyl-2-propanyl)silyl)oxy)ethyl)-7'-methoxy-12'-methyl-3,4-dihydro-2H,15'H-spiro[naphthalene-1,22'-[20]oxa[13]thia[1,14]diazatetracyclo-[14.7.2.0$^{3,6}$.0$^{19,24}$]pentacosa[8,16,18,24]tetraen]-15'-one 13',13'-dioxide

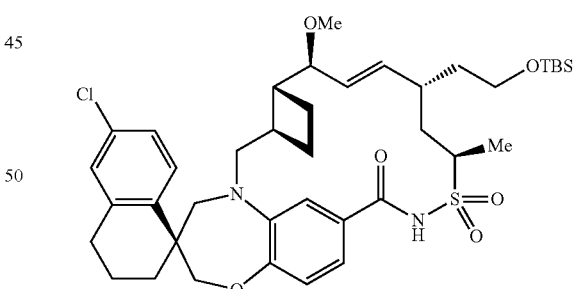

To a room temperature solution of (1S,3'R,6'R,7'S,8'E,10'R,12'R)-6-chloro-10'-(2-((dimethyl(2-methyl-2-propanyl)silyl)oxy)ethyl)-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa-[8,16,18,24]

tetraen]-15'-one 13',13'-dioxide (0.04 g, 0.054 mmol) dissolved in THF (2.5 mL) was added sodium hydride, 60% dispersion in mineral oil (5.66 µL, 0.269 mmol) all at once. The mixture was stirred at room temperature for 30 minutes before neat iodomethane (0.017 mL, 0.269 mmol) was added all at once. The reaction mixture was stirred at room temperature for three hours, after which time TLC indicated no starting material remained and 10 mL saturated aqueous ammonium chloride solution was added followed by 10 mL water. The aqueous mixture was extracted with 2×25 mL ethyl acetate. The combined organic extracts were washed with 20 mL water then 20 mL brine, stirred over anhydrous magnesium sulfate, filtered and the filtrate concentrated under reduced pressure to afford a colorless film (48 mg). The product was isolated by chromatography on 24 g RediSep Rf Gold column eluting with 25% ethyl acetate in hexane at 30 ml/min to afford (1S,3'R,6'R,7'S,8'E,10'R,12'R)-6-chloro-10'-(2-((dimethyl(2-methyl-2-propanyl)silyl)oxy)ethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as a colorless film (19 mg, 0.025 mmol, 47% yield).

Step 11: (1S,3'R,6'R,7'S,8'E,10'R,12'R)-6-chloro-10'-(2-hydroxyethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide To a room temperature solution of (1S,3'R,6'R,7'S,8'E,10'R,12'R)-6-chloro-10'-(2-((dimethyl(2-methyl-2-propanyl)silyl)oxy)ethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa-[8,16,18,24]tetraen]-15'-one 13',13'-dioxide (0.017 g, 0.022 mmol) dissolved in THF (2 mL) was added tetrabutylammonium fluoride, 1.0 M in tetrahydrofuran (0.224 mL, 0.224 mmol) all at once. The reaction was stirred at room temperature for 4.5 hours then partitioned between 20 mL each ethyl acetate and 1:1 saturated aqueous ammonium chloride solution: water. The organic layer was washed with 3×10 mL water followed by 10 mL brine, stirred over anhydrous magnesium sulfate, filtered and the filtrate concentrated under reduced pressure to afford a colorless film. The product was isolated by chromatography on 12 g RediSep Rf Gold column eluting with 10-25% acetone in dichloromethane at 30 ml/min to afford (1S,3'R,6'R,7'S,8'E,10'R,12'R)-6-chloro-10'-(2-hydroxyethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]-pentacosa[8,16,18,24]tetraen]-15'-one 13',13'-dioxide as a colorless film (11 mg, 0.017 mmol, 76% yield). $^1$H NMR (400 MHz, CDCl$_3$) δ ppm 8.93 (br. s., 1H), 7.63 (d, J=8.41 Hz, 1H), 7.19 (s, 1H), 7.10 (dd, J=8.51, 2.05 Hz, 1H), 7.01 (d, J=2.15 Hz, 1H), 6.80-6.96 (m, 2H), 6.74 (s, 1H), 5.71 (dd, J=15.45, 6.85 Hz, 1H), 5.42 (dd, J=15.55, 7.14 Hz, 1H), 4.25 (br. s., 1H), 3.92-4.11 (m, 2H), 3.48-3.83 (m, 5H), 3.22 (s, 3H), 3.10 (d, J=14.09 Hz, 1H), 2.95 (dd, J=15.16, 8.71 Hz, 1H), 2.60-2.80 (m, 2H), 2.36-2.56 (m, 2H), 2.13-2.28 (m, 2H), 1.80-2.02 (m, 3H), 1.28-1.79 (m, 11H), m/z (ESI, +ve ion) 642.8 (M+H)$^+$.

Example 203. ((1S,3'R,6'R,7'S,8'E,10'R,12'R)-6-chloro-7'-methoxy-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-10'-yl)acetonitrile

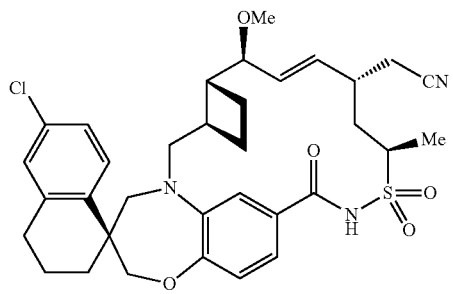

Step 1: ((1S,3'R,6'R,7'S,8'E,10'R,12'R)-6-chloro-7'-methoxy-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-10'-yl)acetaldehyde

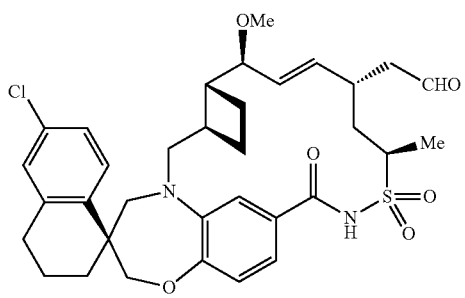

To a mixture of sodium bicarbonate (2.178 µL, 0.056 mmol) and (1S,3'R,6'R,7'S,8'E,10'R,12'R)-6-chloro-10'-(2-hydroxy ethyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (0.0072 g, 0.011 mmol, Example 202) in wet DCM (1.5 mL) cooled by an ice bath was added solid dess-martin periodinane (5.70 mg, 0.013 mmol) all at once. The reaction mixture was stirred at 0-5° C. for ten minutes after which time TLC and LCMS indicated only starting material present. The reaction was equilibrated to room temperature and stirred for 90 minutes, after which time TLC indicated mostly starting material with a faint, less polar spot. An additional 1 equivalent of DM periodinane was added and stirring continued at room temperature. After 3.5 hours mostly starting material with a single less polar spot by TLC. An additional equivalent of DM periodinane was added (total=3.2 equivalents) and stirring at room temperature continued. After 6.5 hours total time TLC and LCMS indicated no starting material remained and a single peak with mass corresponding to desired product predominated. To the reaction mixture was added 3 mL saturated aqueous bicarb solution, 3 mL saturated aqueous sodium thiosulfate solution and 3 mL DCM. This biphasic mixture was stirred rapidly for 30 minutes, after which time the phases were clear. The layers were separated and the aqueous layer extracted again with 2×10 mL DCM. The combined organic layers were washed with 10 mL bicarbonate solution then stirred over anhydrous magnesium sulfate, filtered and the filtrate concentrated under reduced pressure to afford a colorless film (7.3 mg). The product was isolated by chromatography on 4 g RediSep Rf Gold column eluting (manually) with 30% acetone in hexane in 5 ml volumes (by syringe) to afford ((1S,3'R,6'R,7'S,8'E,10'R,12'R)-6-chloro-7'-methoxy-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]-tetraen]-10'-yl)acetaldehyde as a colorless film (7.2 mg, 0.011 mmol, 100%).

Step 2: ((1S,3'R,6'R,7'S,8'E,10'R,12'R)-6-chloro-7'-methoxy-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-10'-yl)acetonitrile A mixture of ((1S,3'R,6'R,7'S,8'E,10'R,12'R)-6-chloro-7'-methoxy-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-10'-yl)acetaldehyde (4.9 mg, 7.64 μmol) and hydroxylamine hydrochloride (1.590 μL, 0.038 mmol) in MeCN (0.8 mL) was heated for 20 minutes at 100° C. in a microwave reactor, after which time TLC and LCMS indicated no starting aldehyde remained and a single peak with mass corresponding to intermediate oxime predominated. The reaction mixture was partitioned between 10 mL each ethyl acetate and 2M aqueous sodium carbonate solution. The aqueous separation was extracted again with 2×10 mL ethyl acetate. The combined organic layers were washed with 10 mL brine and the brine back-extracted with 10 ml ethyl acetate. All combined organic layers were stirred over anhydrous magnesium sulfate, filtered and the filtrate concentrated under reduced pressure to afford a colorless film (5 mg). To a solution of triphenylphosphine oxide (3.71 μL, 0.016 mmol) dissolved in CHCl$_3$ (0.5 mL) at room temperature was added oxalyl chloride, 2.0 M solution in dichloromethane (4.97 μL, 9.93 μmol) all at once. The resulting solution was stirred at ambient temperature for 5 minutes before a solution of the oxime in CHCl$_3$ (0.5 mL) was added all at once. After 5 minutes TLC and LCMS indicated no starting material remained and a single less polar spot predominated with mass corresponding to desired nitrile. The reaction was stirred at room temperature for 60 minutes then concentrated under reduced pressure. The product was isolated by chromatography on 4 g RediSep Rf Gold column eluting with 50% ethyl acetate in hexane+1% acetic acid in 5 ml volumes (manually, by syringe) to afford ((1S,3'R,6'R,7'S,8'E,10'R,12'R)-6-chloro-7'-methoxy-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-10'-yl)acetonitrile as a colorless film (3.2 mg, 0.005 mmol, 66% yield). $^1$H NMR (400 MHz, CDCl$_3$) δ ppm 8.28 (br. s., 1H), 7.62 (d, J=8.61 Hz, 1H), 7.10 (dd, J=8.51, 2.25 Hz, 1H), 7.01 (d, J=2.15 Hz, 1H), 6.88 (s, 2H), 6.72 (s, 1H), 5.74 (dd, J=15.65, 6.06 Hz, 1H), 5.57 (dd, J=15.75, 6.75 Hz, 1H), 4.28 (t, J=6.65 Hz, 1H), 3.94-4.11 (m, 2H), 3.56-3.79 (m, 3H), 3.20-3.30 (m, 3H), 3.11 (d, J=14.08 Hz, 1H), 2.97 (dd, J=15.06, 9.00 Hz, 1H), 2.58-2.80 (m, 3H), 2.41-2.54 (m, 1H), 2.39 (d, J=6.85 Hz, 2H), 2.21-2.32 (m, 1H), 2.07-2.20 (m, 1H), 1.79-2.03 (m, 4H), 1.59-1.78 (m, 4H), 1.43-1.59 (m, 3H), 1.30-1.42 (m, 1H); m/z (ESI, +ve ion) 637.9 (M+H)$^+$.

Example 204. (1S,3'R,6'R,7'S,8'E,10'R,12'R)-6-chloro-7'-methoxy-10'-(2-methoxyethyl)-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

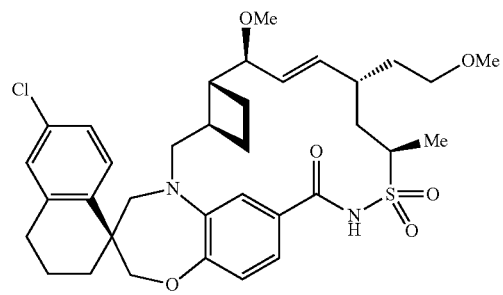

To a solution of (1S,3'R,6'R,7'S,8'E,10'R,12'R)-6-chloro-10'-(2-hydroxyethyl)-7'-methoxy-12'-methyl-3,4-dihydro-2H,15'H-spiro[naphthalene-[20]oxa[13]thia[1,14]diazatetracyclo[14.7.2.0$^{3,6}$.0$^{19,24}$]pentacosa[8,16,18,24]tetraen]-15'-one 13',13'-dioxide (0.005 g, 7.77 μmol, Example 202) dissolved in THF (1.8 mL) at room temperature was added sodium hydride, 60% dispersion in mineral oil (6.32 μL, 0.300 mmol) all at once. The mixture was stirred at room temperature for 30 minutes before neat iodomethane (0.019 mL, 0.311 mmol) was added all at once. The reaction mixture was stirred at room temperature for 3 hours then 5 mL saturated aqueous ammonium chloride solution was added followed by 5 mL water. The mixture was extracted with 3×10 mL ethyl acetate volumes. The combined organic layers were washed with 10 mL brine, stirred over anhydrous magnesium sulfate, filtered and the filtrate concentrated under reduced pressure to afford a colorless film (17 mg). The product was isolated by chromatography on 4 g RediSep Rf Gold eluting with 25% acetone in hexane in 4 mL volumes, manually by syringe, to afford (1S,3'R,6'R,7'S,8'E,10'R,12'R)-6-chloro-7'-methoxy-10'-(2-methoxyethyl)-12'-methyl-3,4-dihydro-2H,15'H-spiro[naphthalene-1,22'-[20]oxa[13]thia[1,14]diazatetracyclo[14.7.2.0$^{3,6}$.0$^{19,24}$] pentacosa[8,16,18,24]tetraen]-15'-one 13',13'-dioxide as a colorless film (4.8 mg, 0.0073 mmol, 94% yield). $^1$H NMR (400 MHz, CDCl$_3$) δ ppm 8.72 (br. s., 1H), 7.62 (d, J=8.61 Hz, 1H), 7.10 (dd, J=8.41, 2.15 Hz, 1H), 7.01 (d, J=2.15 Hz, 1H), 6.81-6.95 (m, 2H), 6.77 (br. s., 1H), 5.67 (dd, J=15.55, 6.75 Hz, 1H), 5.40 (dd, J=15.36, 7.53 Hz, 1H), 4.20 (br. s., 1H), 3.93-4.12 (m, 2H), 3.50-3.83 (m, 3H), 3.23-3.43 (m, 2H), 3.21 (s, 3H), 3.05-3.17 (m, 4H), 2.95 (dd, J=15.26, 9.00 Hz, 1H), 2.59-2.81 (m, 2H), 2.45 (d, J=4.11 Hz, 2H), 2.16 (ddd, J=14.97, 8.51, 3.52 Hz, 2H), 1.80-1.99 (m, 3H), 1.40-1.78 (m, 10H), 1.29-1.40 (m, 1H); m/z (ESI, +ve ion) 657.3 (M+H)$^+$.

Example 205. (1S,3'R,6'R,7'S,8'E,10'R,12'R)-6-chloro-10'-((2S)-2-hydroxypropyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,10'R,12'R)-6-chloro-10'-((2R)-2-hydroxypropyl)-7'-methoxy-12'-methyl-3,4-dihydro-2H,15'H-spiro[naphthalene-1,22'-[20]oxa[13]thia[1,14]diazatetracyclo-[14.7.2.0$^{3,6}$.0$^{19,24}$]pentacosa[8,16,18,24]tetraen]-15'-one 13',13'-dioxide

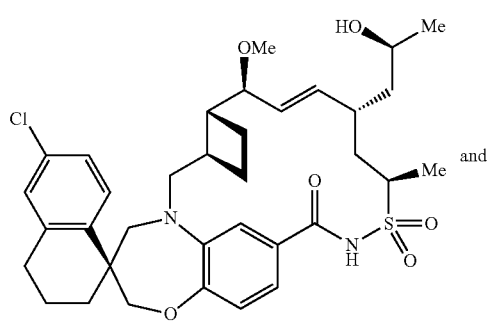

and

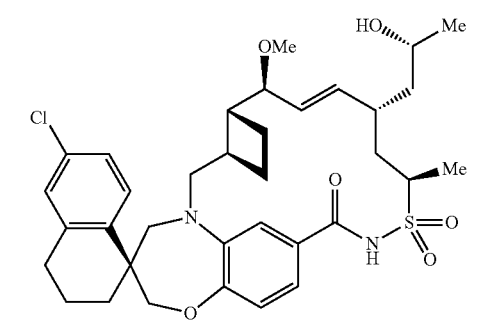

To a solution of ((1S,3'R,6'R,7'S,8'E,10'R,12'R)-6-chloro-7'-methoxy-12'-methyl-13',13'-dioxido-15'-oxo-3,4-dihydro-2H-spiro[naphthalene-1,22'-[20]oxa[13]thia[1,14]diazatetracyclo-[14.7.2.0$^{3,6}$.0$^{19,24}$]pentacosa[8,16,18,24]tetraen]-10'-yl)acetaldehyde (0.0065 g, 10.14 μmol, Example 203, Step 1) dissolved in THF (2 mL) was added methylmagnesium bromide 3.0 M in diethyl ether (0.017 mL, 0.051 mmol) all at once. The reaction solution was stirred at room temperature for 5 minutes after which time LCMS indicated no starting material remained and a single peak with mass corresponding to desired product predominated. To the reaction mixture was added 5 mL each saturated aqueous ammonium chloride solution and water. The aqueous layer was extracted with 3×15 mL volumes ethyl acetate. The combined organic layers were stirred over anhydrous magnesium sulfate, filtered and the filtrate concentrated under reduced pressure to afford a colorless film (9.6 mg). The products were isolated by chromatography on 4 g RediSep Rf Gold column eluting manually with 10 to 20% acetone in DCM to afford a mixture of (1S,3'R,6'R, 7'S,8'E,10'R,12'R)-6-chloro-10'-((2S)-2-hydroxypropyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,10'R,12'R)-6-chloro-10'-((2R)-2-hydroxypropyl)-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as a colorless film (5.1 mg, 0.0078 mmol, 77% yield). $^1$H NMR (500 MHz, CDCl$_3$) δ ppm 7.64 (m, 2H), 7.10 (m, 2H), 7.01 (m, 2H), 6.68-6.94 (m, 6H), 5.82 (d, J=11.74 Hz, 1H), 5.59 (dd, J=15.28, 7.46 Hz, 1H), 5.33-5.50 (m, 2H), 4.29 (br. s., 1H), 4.10-4.22 (m, 1H), 3.94-4.10 (m, 4H), 3.87 (br. s., 1H), 3.55-3.80 (m, 8H), 3.22 (m, 6H), 3.05-3.15 (m, 2H), 2.86-3.03 (m, 2H), 2.62-2.79 (m, 4H), 2.56 (br. s., 2H), 2.38-2.49 (m, 2H), 2.03-2.34 (m, 5H), 1.80-2.01 (m, 7H), 1.67-1.79 (m, 5H), 1.45-1.67 (m, 12H), 1.27-1.45 (m, 2H), 1.13-1.26 (m, 4H), 1.05-1.12 (m, 6H); m/z (ESI, +ve ion) 657.3 (M+H)$^+$.

Example 206. ((1S,3'R,6'S,7'E,9'R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)acetic acid or ((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)acetic acid

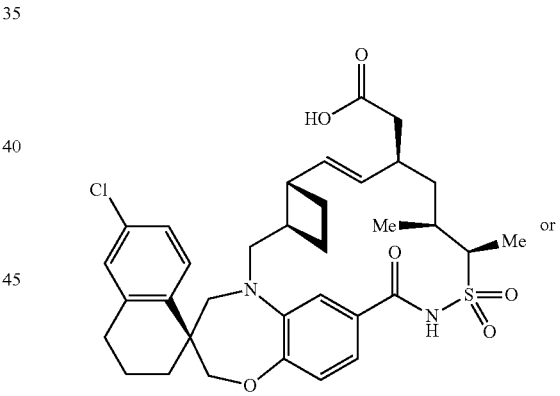

or

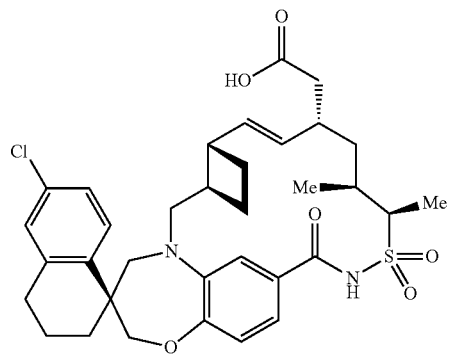

Step 1: (1S,3'R,6'R,7'S,8'E,11'S,12'R)-6-chloro-11',
12'-dimethyl-13',13'-dioxido-15'-oxo-3,4-dihydro-
2H-spiro[naphthalene-1,22'-[20]oxa[13]thia[1,14]
diazateracyclo-[14.7.2.0$^{3,6}$.0$^{19,24}$]pentacosa[8,16,18,
24]tetraen]-7'-yl acetate

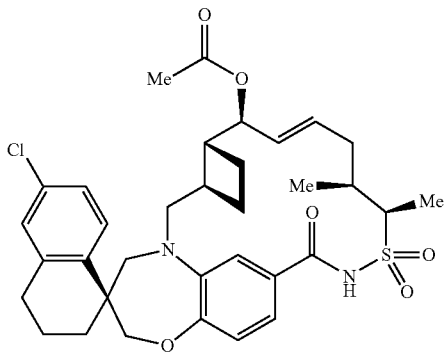

To a mixture of (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo-[14.7.2.0$^{3,6}$.0$^{19,24}$]pentacosa[8,16,18,24]tetraen]-15'-one 13',13'-dioxide (0.05 g, 0.083 mmol, Example 719, Step 2), 4-dimethylaminopyridine (1.019 mg, 8.34 µmol) and triethylamine (0.041 mL, 0.292 mmol) in DCM (0.417 mL) at room temperature was added neat acetic anhydride (0.024 mL, 0.250 mmol) all at once. The reaction was stirred at room temperature for two hours then partitioned between 20 mL each DCM and water. The aqueous separation was extracted again with 20 mL DCM. The combined organic extracts were stirred over anhydrous magnesium sulfate, filtered and the filtrate concentrated under reduced pressure to afford a colorless film. The product was isolated by chromatography on 12 g RediSep Rf Gold column eluting with 25% acetone in hexane at 30 mL/min to afford (1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo-[14.7.2.0$^{3,6}$.0$^{19,24}$]pentacosa[8,16,18,24]tetraen]-7'-yl acetate as a colorless film (47 mg, 0.073 mmol, 88% yield).

Step 2: ((1S,3'R,6'S,7'E,9'R,11'S,12'R)-6-chloro-11',
12'-dimethyl-13',13'-dioxido-15'-oxo-3,4-dihydro-
2H-spiro[naphthalene-1,22'-[20]oxa[13]thia[1,14]
diazatetracyclo[14.7.2.0$^{3,6}$.0$^{19,24}$]pentacosa[7,16,18,
24]tetraen]-9'-yl)acetic acid or ((1S,3'R,6'S,7'E,9'S,
11'S,12'R)-6-chloro-11',12'-dimethyl-13',13'-dioxido-
15'-oxo-3,4-dihydro-2H-spiro[naphthalene-1,22'-
[20]oxa[13]thia[1,14]diazatetracyclo[14.7.2.0$^{3,6}$.
0$^{19,24}$]pentacosa[7,16,18,24]tetraen]-9'-yl)acetic
Acid To a solution of (1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo-[14.7.2.0$^{3,6}$.0$^{19,24}$]pentacosa[8,16,18,24]tetraen]-7'-yl acetate (0.045 g, 0.070 mmol) and tert-butyl(chloro)dimethylsilane (0.053 g, 0.351 mmol) dissolved in THF (2 mL) cooled by an acetone-dry ice bath was added a 1M solution of potassium bis(trimethylsilyl)amide in tetrahydrofuran (0.211 mL, 0.211 mmol) all at once. The reaction was left stirring at −78° C. for 3 hours then the cold bath was removed and the reaction equilibrated to room temperature over 30 minutes. The reaction was stirred at room temperature for 2 hours then partitioned between 20 mL each saturated aqueous ammonium chloride and ethyl acetate. The aqueous separation was extracted again with 20 mL ethyl acetate. The combined organic extracts were stirred over anhydrous magnesium sulfate, filtered and the filtrate concentrated under reduced pressure to afford a colorless film (49 mg). The crude product was dissolved in 2 mL methanol and 2 mL THF and a solution of 50 mg LiOH dissolved in 500 µL water was added all at once at room temperature. After 30 minutes the reaction was concentrated under reduced pressure. The concentrate was partitioned between 10 mL each 1N aqueous hydrochloric acid and ethyl acetate. The aqueous separation was extracted twice again with 10 mL ethyl acetate. The combined organic extracts were stirred over anhydrous magnesium sulfate, filtered and the filtrate concentrated under reduced pressure to afford a colorless film. The product was isolated by chromatography on 4 g RediSep Rf Gold column eluting with 30% acetone in hexane at 18 mL/min to afford ((1S,3'R,6'S,7'E,9'R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]-pentacosa[7,16,18,24]tetraen]-9'-yl)acetic acid or ((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia-[1,14]diazatetracyclo[14.7.2.0$^{3,6}$.0$^{19,24}$]pentacosa[7,16,18,24]tetraen]-9'-yl)acetic acid as a colorless film (20 mg, 0.031 mmol, 44% yield). $^1$H NMR (400 MHz, CDCl$_3$) δ ppm 8.19 (br. s., 1H), 7.49 (d, J=8.61 Hz, 1H), 6.95 (dd, J=8.51, 2.25 Hz, 1H), 6.87 (d, J=2.15 Hz, 1H), 6.77-6.85 (m, 2H), 6.67-6.77 (m, 1H), 5.68 (dd, J=15.45, 4.89 Hz, 1H), 5.06 (dd, J=15.06, 7.04 Hz, 1H), 4.05 (d, J=6.85 Hz, 1H), 3.85-3.94 (m, 2H), 3.62 (d, J=15.26 Hz, 1H), 3.42 (d, J=14.09 Hz, 1H), 2.97 (d, J=14.09 Hz, 1H), 2.82 (dd, J=15.45, 8.41 Hz, 1H), 2.49-2.63 (m, 2H), 2.39-2.49 (m, 1H), 2.26-2.39 (m, 1H), 2.13-2.24 (m, 1H), 2.06 (dd, J=15.94, 9.29 Hz, 2H), 1.64-1.91 (m, 5H), 1.46-1.64 (m, 2H), 1.16-1.46 (m, 6H), 1.00-1.14 (m, 2H), 0.77 (d, J=7.04 Hz, 3H); m/z (ESI, +ve ion) 641.2 (M+H)$^+$.

Example 207. ((1S,3'R,6'R,9'R,11'S,12'R)-6-chloro-
11',12'-dimethyl-13',13'-dioxido-15'-oxo-3,4-di-
hydro-2H-spiro[naphthalene-1,22'-[20]oxa[13]thia
[1,14]diazatetracyclo[14.7.2.0$^{3,6}$.0$^{19,24}$]pentacosa
[16,18,24]trien]-9'-yl)acetic acid or ((1S,3'R,6'R,9'S,
11'S,12'R)-6-chloro-11',12'-dimethyl-13',13'-dioxido-
15'-oxo-3,4-dihydro-2H-[20]oxa[13]thia[1,14]diaza-
tetracyclo[14.7.2.0$^{3,6}$.0$^{19,24}$]pentacosa [16,18,24]
trien]-9'-yl)acetic acid

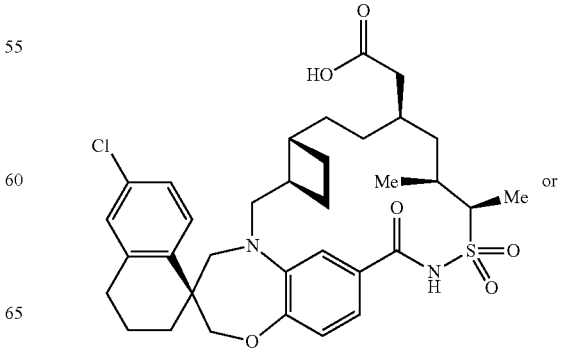

-continued

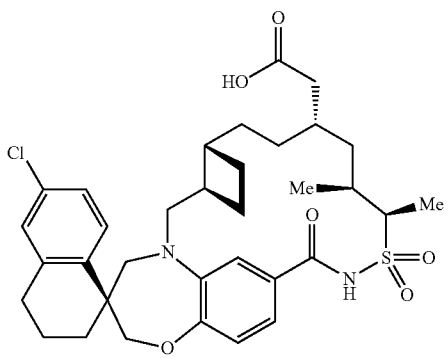

Hydrogen gas was introduced by balloon to a mixture of (((1S,3'R,6'S,7'E,9'R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]-pentacosa[7,16,18,24]tetraen]-9'-yl)acetic acid or ((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia-[1,14]diazatetracyclo[14.7.2.0$^{3,6}$.0$^{19,24}$]pentacosa[7,16,18,24]tetraen]-9'-yl)acetic acid (0.0067 g, 10.45 μmol, Example 206) and platinum (iv) oxide (4.75 mg, 0.021 mmol) in EtOAc (2 mL) at room temperature. The mixture was stirred at room temperature for 2 hours then filtered through a pad of celite, rinsing with ethyl acetate. The filtrate was concentrated under reduced pressure to afford ((1S,3'R,6'R,9'R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo-[14.7.2.0$^{3,6}$.0$^{19,24}$]pentacosa[16,18,24]trien]-9'-yl)acetic acid or ((1S,3'R,6'R,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo-[14.7.2.0$^{3,6}$.0$^{19,24}$]pentacosa[16,18,24]trien]-9'-yl)acetic acid as a colorless film (5.8 mg, 0.009 mmol, 86% yield). $^1$H NMR (400 MHz, CDCl$_3$) δ ppm 8.18 (br. s., 1H), 7.64 (d, J=8.61 Hz, 1H), 7.10 (dd, J=8.41, 2.15 Hz, 1H), 7.01 (d, J=1.57 Hz, 2H), 6.82-6.97 (m, 2H), 4.13-4.28 (m, 1H), 3.96-4.11 (m, 2H), 3.69 (d, J=15.26 Hz, 1H), 3.59 (d, J=14.28 Hz, 1H), 3.12 (d, J=14.28 Hz, 1H), 2.91 (dd, J=15.36, 8.31 Hz, 1H), 2.61-2.77 (m, 2H), 2.48 (dd, J=15.85, 2.74 Hz, 1H), 2.14-2.35 (m, 2H), 1.90-2.07 (m, 5H), 1.78-1.89 (m, 3H), 1.28-1.77 (m, 11H), 0.96-1.11 (m, 2H), 0.91 (d, J=6.85 Hz, 3H); m/z (ESI, +ve ion) 643.2 (M+H)$^+$.

Example 208. (1S,3'R,6'R,7'R,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

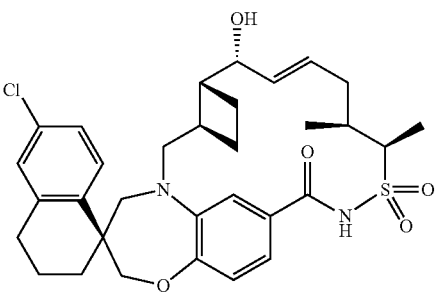 [SMILES: C[C@@H]1[C@@H](C)C/C=C/[C@@H](O)[C@@H]2CC[C@H]2CN2C[C@@]3(CCCc4cc(Cl)ccc43)COc3ccc(cc32)C(=O)NS1(=O)=O]

Step 1: (S)-methyl 6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate

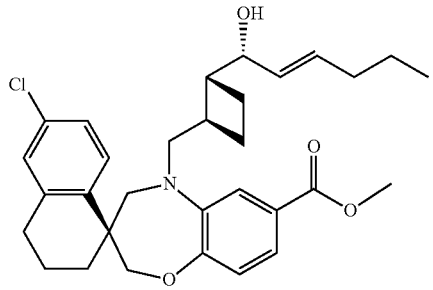 [SMILES: CCC/C=C/[C@@H](O)[C@@H]1CC[C@H]1CN1C[C@@]2(CCCc3cc(Cl)ccc32)COc2ccc(C(=O)OC)cc21]

To borane dimethyl sulfide (0.522 mL, 5.51 mmol) in hexane (6 mL) under argon at 0° C. was added cyclohexene (1.116 mL, 11.01 mmol). After 3 h of stirring at rt, pent-1-yne (0.543 mL, 5.51 mmol, Aldrich) was added and the reaction was allowed to warm up to rt for 30 min (during this period of time the cloudy mixture became a clear solution, and a slightly exothermal reaction occurred). The reaction was cooled to −78° C. and treated with diethylzinc (1 M in hexanes, 5.51 mL, 5.51 mmol, Aldrich). The solution was warmed to 0° C. for 3 min. then it was cooled back to −78° C. Separately, Intermediate AA11A, Step 20A (500 mg, 1.10 mmol), and (1R,2S,3S,4S)-1,7,7-trimethyl-3-morpholinobicyclo[2.2.1]heptan-2-ol (52.7 mg, 0.220 mmol, Aldrich) were combined in hexane (6 mL) at 0° C. under argon. To this solution was added 8.4 mL of the prepared zinc reagent via syringe. After 50 minutes, the solution was warmed to rt for 10 minutes. The reaction was quenched with 20 mL sat. NH$_4$Cl, diluted with 200 mL of EtOAc, and stirred at rt for 15 minutes to afford two clear and colorless layers. The layers were separated and the aqueous layer was extracted with ether. The combined ether layers were washed with brine, dried over MgSO$_4$, filtered, and concentrated to a pale yellow oil. The oil was deposited on 2.5 g silica gel and purified using an 80 g RediSep gold column eluted with 0 to 40% EtOAc:Hexanes to give (S)-methyl 6'-chloro-5-(((1R,2R)-2-((R,E)-1-hydroxyhex-2-en-1-yl)cyclobutyl)methyl)-

3',4,4',5-tetrahydro-2H,2'H-spiro[benzo[b][1,4]oxazepine-3,1'-naphthalene]-7-carboxylate (316 mg, 0.603 mmol, 27.4% yield). m/z (ESI, +ve ion) 524.2 (M+H)⁺.

Step 2: (S)-6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid

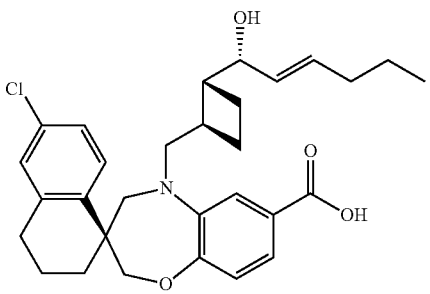 [SMILES: CCC/C=C/[C@@H](O)[C@@H]1CC[C@H]1CN1C[C@@]2(CCCc3cc(Cl)ccc32)COc2ccc(C(=O)O)cc21]

(S)-methyl 6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (2.10 g, 4.01 mmol) was dissolved in a 2:1 mixture of MeOH (53.4 mL) and THF (26.7 mL), then lithium hydroxide (2 M; 20.03 mL, 40.1 mmol) was added. The reaction was stirred at room temperature overnight. The reaction mixture was then concentrated and the residue was partitioned between 1N HCl soln (~50 mL) and EtOAc (3×150 mL). The combined organic layers were then washed with brine (1×25 mL) and dried over magnesium sulfate. The filtrate was concentrated to give (S)-6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (1.79 g, 3.51 mmol, 88% yield). m/z (ESI, +ve ion) 510.2 (M+H)⁺.

Step 3: (S)-6'-chloro-5-(((1R,2R)-2-((R,E)-1-hydroxyhex-2-en-1-yl)cyclobutyl)methyl)-N-(((2R,3S)-3-methylhex-5-en-2-yl)sulfonyl)-3',4,4',5-tetrahydro-2H,2'H-spiro[benzo[b][1,4]oxazepine-3,1'-naphthalene]-7-carboxamide

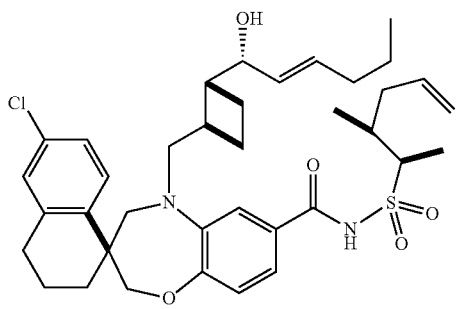 [SMILES: C=CC[C@H](C)[C@@H](C)S(=O)(=O)NC(=O)c1ccc2c(c1)N(C[C@@H]1CC[C@H]1[C@H](O)/C=C/CCC)C[C@@]1(CCCc3cc(Cl)ccc31)CO2]

4-Dimethylaminopyridine (DMAP) (0.305 g, 2.500 mmol) was added to a solution of (S)-6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (0.75 g, 1.470 mmol) and (2R,3S)-3-methylhex-5-ene-2-sulfonamide (0.521 g, 2.94 mmol, Intermediate EE22) in dichloromethane (37 mL) cooled to 0° C. EDC hydrochloride (EDC) (0.564 g, 2.94 mmol) was then added slowly. The mixture was stirred while allowing to reach rt overnight. The mixture was then washed with 1N HCl and brine and the aqueous layer was back-extracted with EtOAc. The combined organics were dried over MgSO₄, filtered and concentrated. The yellow oily residue was then purified by medium pressure chromatography (silica, 5 to 50% EtOAc (+0.3% HOAc):Hexanes) to give (S)-6'-chloro-5-(((1R,2R)-2-((R,E)-1-hydroxyhex-2-en-1-yl)cyclobutyl)methyl)-N-(((2R,3S)-3-methylhexan-2-yl)sulfonyl)-3',4,4',5-tetrahydro-2H,2'H-spiro[benzo[b][1,4]oxazepine-3,1'-naphthalene]-7-carboxamide (0.320 g, 0.478 mmol, 32.5% yield). m/z (ESI, +ve ion) 669.3 (M+H)⁺.

Step 4: (1S,3'R,6'R,7'R,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (S)-6'-chloro-5-(((1R,2R)-2-((R,E)-1-hydroxyhex-2-en-1-yl)cyclobutyl)methyl)-N-(((2R,3S)-3-methylhex-5-en-2-yl)sulfonyl)-3',4,4',5-tetrahydro-2H,2'H-spiro[benzo[b][1,4]oxazepine-3,1'-naphthalene]-7-carboxamide (320 mg, 0.478 mmol) was weighed out into a 250 mL RB flask and purged with argon. 1,2-dichloroethane (255 mL) was added via cannula followed by the addition of (1,3-dimesitylimidazolidin-2-ylidene)(2-isopropoxybenzylidene)ruthenium(VI) chloride (Grubbs-Hoveyda Catalyst, 2nd Generation, Aldrich) (30.0 mg, 0.048 mmol) as a solid. The reaction mixture was heated to 80° C. and after 2 h, it was cooled to rt. 2-(2-(vinyloxy)ethoxy)ethanol (0.026 mL, 0.191 mmol, Aldrich) was added and the resulting mixture was stirred for 20 min at rt and concentrated at 40° C. under vacuum. The crude product was purified by silica gel chromatography (40% to 90% EtOAc (+0.3% HOAc):Hexanes) to give (1S,3'R,6'R,7'R,8'E,11'S,12'R)-6-chloro-7'-hydroxy-11',12'-dimethyl-3,4-dihydro-2h,15'h-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (37 mg, 0.062 mmol, 12.92% yield). ¹H NMR (400 MHz, CD₃OD) δ 7.75 (d, J=8.6 Hz, 1H), 7.50 (d, J=2.0 Hz, 1H), 7.19 (dd, J=8.4, 2.2 Hz, 1H), 7.14 (dd, J=8.2, 2.0 Hz, 1H), 7.11 (d, J=2.2 Hz, 1H), 6.93 (d, J=8.2 Hz, 1H), 5.39-5.59 (m, 2H), 4.08 (s, 2H), 3.88-4.00 (m, 2H), 3.64-3.74 (m, 2H), 3.30 (d, J=14.5 Hz, 1H), 3.04 (dd, J=15.6, 5.0 Hz, 1H), 2.70-2.88 (m, 2H), 2.51-2.65 (m, 2H), 2.14-2.28 (m, 1H), 2.03-2.14 (m, 2H), 1.57-2.00 (m, 7H), 1.42 (br. s, 1H), 1.39 (d, J=7.2 Hz, 3H), 1.32-1.36 (m, 1H), 1.09 (d, J=6.8 Hz, 3H). m/z (ESI, +ve ion) 599.2 (M+H)⁺

Example 209. (1S,3'R,6'R,7'R,8'E)-6-chloro-7'-ethoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

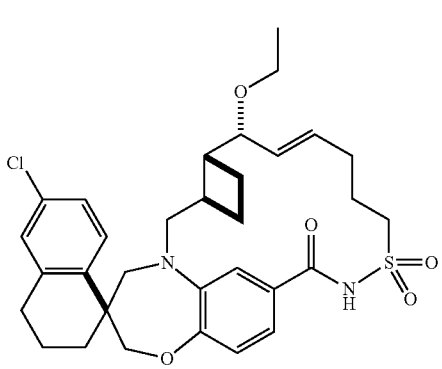

A solution of allylic alcohol (20 mg, 0.035 mmol, Example 952) in THF (1.00 mL) was cooled to 0° C. Sodium hydride (60% dispersion) (14.01 mg, 0.350 mmol) was added and the resulting slurry was stirred for 30 minutes. Iodoethane (0.014 mL, 0.175 mmol) was then added and the slurry was stirred overnight. The reaction was then acidified by adding 1N HCl and this mixture was filtered. The crude material was purified by reverse-phase preparative HPLC using a Phenomenex Luna column, 10 micron, C8(2), 100 Å, 150×30 mm, 0.1% TFA in CH$_3$CN/H$_2$O, gradient 40% to 70% over 20 min to provide (1S,3'R,6'R,7'R,8'E)-6-chloro-7'-ethoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (6 mg, 10.01 μmol, 28.6% yield). $^1$H NMR (400 MHz, CDCl$_3$) δ 8.57 (br. s. 1H), 7.72 (d, J=8.4 Hz, 1H), 7.32 (d, J=1.8 Hz, 1H), 7.19 (dd, J=8.5, 2.2 Hz, 1H), 7.09 (d, J=2.2 Hz, 1H), 7.07 (dd, J=8.1, 1.9 Hz, 1H), 6.95 (d, J=8.0 Hz, 1H), 5.78 (dt, J=15.7, 5.4 Hz, 1H), 5.49 (dd, J=15.7 Hz, 8.0 Hz, 1H), 4.06-4.17 (m, 2H), 3.94-4.05 (m, 2H), 3.63-3.78 (m, 3H), 3.31-3.46 (m, 2H), 3.19 (d, J=14.3 Hz, 1H), 2.97 (dd, J=15.2, 9.1 Hz, 1H), 2.68-2.86 (m, 2H), 2.48-2.63 (m, 1H), 2.39-2.48 (m, 1H), 2.29-2.38 (m, 1H), 2.00-2.13 (m, 3H), 1.88-1.98 (m, 3H), 1.77-1.87 (m, 1H), 1.67-1.77 (m, 1H), 1.53-1.66 (m, 1H), 1.41-1.52 (m, 2H), 0.78-0.97 (m, 5H). m/z (ESI, +ve ion) 600.2 (M+H)$^+$.

Example 210. (1S,3'R,6'R,7'R,8'E)-6-chloro-7'-(2-methoxyethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

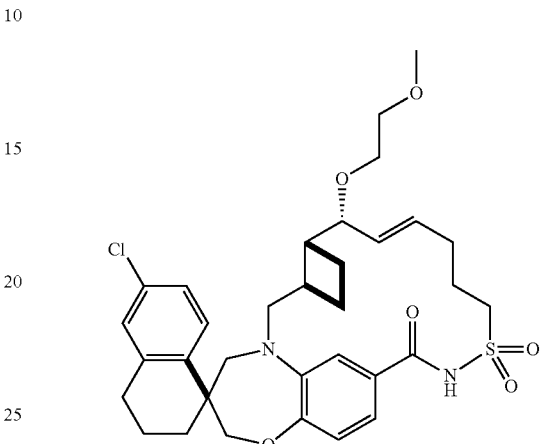

A solution of allylic alcohol (20 mg, 0.035 mmol, Example 952) was dissolved in THF (1.00 mL) and cooled to 0° C. Sodium hydride (60% dispersion; 14.01 mg, 0.350 mmol) was added and the resulting slurry was stirred at 0° C. for 30 minutes. 2-bromoethyl methyl ether (0.016 mL, 0.175 mmol) was then added and the mixture was stirred overnight. LCMS indicated the reaction was 35% complete. Two more aliquots of sodium hydride (60% dispersion; 14.01 mg, 0.350 mmol) and 2-bromoethyl methyl ether (0.016 mL, 0.175 mmol) were added and the mixture was stirred for an additional three days at r.t. Another aliquot of each reagent was added and stirred for an additional 2.5 days until 90% complete. The reaction mixture was then acidified with a few drops of 1N HCl and then diluted with DMSO and filtered. The crude material was purified by reverse-phase preparative HPLC using a Phenomenex Luna column, 5 micron, C8(2), 100 A, 150×21.2 mm, 0.1% TFA in CH$_3$CN/H$_2$O, gradient 45% to 75% over 20 min to provide (1S,3'R,6'R,7'R,8'E)-6-chloro-7'-(2-methoxyethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (7.0 mg, 0.011 mmol, 32% yield). $^1$H NMR (400 MHz, CDCl$_3$) δ 8.65 (br. s., 1H), 7.72 (d, J=8.4 Hz, 1H), 7.29 (d, J=2.0 Hz, 1H), 7.19 (dd, J=8.4, 2.3 Hz, 1H), 7.09 (d, J=2.2 Hz, 1H), 7.06 (dd, J=8.2, 2.0 Hz, 1H), 6.95 (d, J=8.0 Hz, 1H), 5.81 (dt, J=15.8, 5.4 Hz, 1H), 5.48 (dd, J=15.9, 8.1 Hz, 1H), 4.07-4.18 (m, 2H), 4.03 (d, J=14.9, 1H), 3.96 (ddd, J=15.0, 9.3, 5.2 Hz, 1H), 3.85 (ddd, J=10.3, 4.7, 3.2 Hz, 1H), 3.72-3.81 (m, 2H), 3.61-3.71 (m, 2H), 3.43-3.51 (m, 1H), 3.39 (s, 3H), 3.18 (d, J=14.1 Hz, 1H), 2.96 (dd, J=15.3, 9.0 Hz, 1H), 2.74-2.86 (m, 3H), 2.44-2.59 (m, 2H), 2.36 (dd, J=9.3, 5.6 Hz, 1H), 2.12-2.28 (m, 1H), 1.88-2.09 (m, 4H), 1.76-1.87 (m, 1H), 1.66-1.76 (m, 1H), 1.52-1.66 (m, 1H), 1.36-1.51 (m, 3H). m/z (ESI, +ve ion) 629.2 (M+H)$^+$.

Example 211. 3-(((1S,3'R,6'R,7'R,8'E)-6-chloro-13', 13'-dioxido-15'-oxo-3,4-dihydro-2H-spiro[naphthalene-1,22'-[20]oxa[13]thia[1,14]diazatetracyclo [14.7.2.0³,⁶.0¹⁹,²⁴]pentacosa [8,16,18,24]tetraen]-7'-yl)oxy)-N,N-dimethylpropanamide

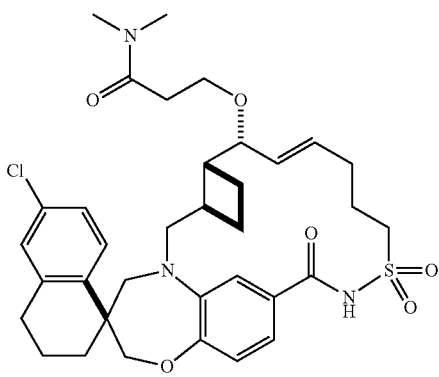

Step 1: 3-(((1S,3'R,6'R,7'R,8'E)-6-chloro-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-7'-yl)oxy)-propionic acid

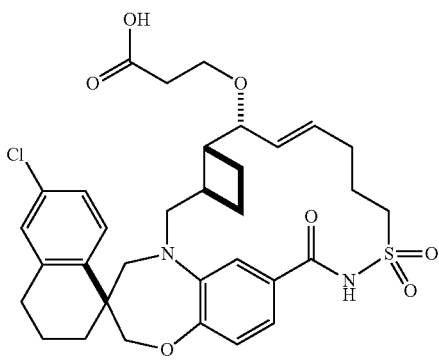

A solution of allylic alcohol (60 mg, 0.11 mmol, Example 952) was dissolved in THF (1.00 mL) and sodium hydride (60% dispersion; 25.2 mg, 1.05 mmol) was added after cooling the solution to 0° C. The slurry was stirred for 30 minutes then ethyl acrylate (0.057 mL, 0.525 mmol) was added and the reaction mixture was stirred overnight. After 16 hours, the mixture had congealed to a brown solid. Another 2 mL of THF was added to facilitate stirring. Another two aliquots of reagents were added and stirred for an additional 24 hours. The reaction was quenched with water, then acidified with 1N HCl to pH~5 and extracted with ethyl acetate (3×20 mL). The combined organic layers were washed with brine (1×30 mL) and dried over magnesium sulfate. The crude material was purified by reverse-phase preparative HPLC using a Phenomenex Luna column, 10 micron, C8(2), 100 Å, 150×30 mm, 0.1% TFA in CH$_3$CN/H$_2$O, gradient 40% to 70% over 25 min to provide 3-((((1S,3'R,6'R,7'R,8'E)-6-chloro-13',13'-dioxido-15'-oxo-3,4-dihydro-2h-spiro[naphthalene-1,22'-[20]oxa[13]thia[1,14]diazatetracyclo[14.7.2.0³,⁶.0¹⁹,²⁴]pentacosa[8,16,18,24] tetraen]-7'-yl)oxy)-propionic acid (5.5 mg, 8.6 µmol, 8.1% yield). $^1$H NMR (400 MHz, CDCl$_3$) δ 8.55 (br. s, 1H), 7.71 (d, J=8.6 Hz, 1H), 7.13-7.23 (m, 2H), 7.09 (d, J=2.2 Hz, 1H), 6.84-7.00 (m, 2H), 5.81 (dt, J=15.7, 5.3 Hz, 1H), 5.44 (dd, J=15.7, 7.2 Hz, 1H), 3.83-4.18 (m, 7H), 3.71-3.78 (m, 1H), 3.68 (d, J=13.9 Hz, 1H), 3.51-3.64 (m, 2H), 3.26-3.35 (m, 3H), 3.18 (d, J=13.9 Hz, 5H), 2.94 (dd, J=15.5, 9.6 Hz, 2H), 2.67-2.85 (m, 6H), 2.33-2.60 (m, 5H), 2.00-2.25 (m, 6H), 1.67-1.98 (m, 8H), 1.54-1.66 (m, 2H), 1.37-1.48 (m, 2H). m/z (ESI, +ve ion) 644.2 (M+H)$^+$.

Step 2: 3-(((1S,3'R,6'R,7'R,8'E)-6-chloro-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-7'-yl)oxy)-N,N-dimethylpropanamide The carboxylic acid (20 mg, 0.031 mmol) was dissolved in DMF (1.0 mL). HATU (28.4 mg, 0.075 mmol) was added followed by addition of dimethylamine (2M THF solution; 0.311 mL, 0.622 mmol) along with a small amount of water (1 drop). The reaction was stirred for 3.5 h. The crude reaction mixture was purified by reverse-phase preparative HPLC using a Phenomenex Luna column, 10 micron, C8(2), 100 Å, 150×30 mm, 0.1% TFA in CH$_3$CN/H$_2$O, gradient 40% to 80% over 25 min to provide 3-((((1S,3'R,6'R,7'R, 8'E)-6-chloro-13',13'-dioxido-15'-oxo-3,4-dihydro-2H-spiro [naphthalene-1,22'-[20]oxa[13]thia[1,14]diazatetracyclo [14.7.2.0³,⁶.0¹⁹,²⁴]pentacosa[8,16,18,24]tetraen]-7'-yl)oxy)-propionic acid (8.0 mg, 0.012 mmol, 38% yield). $^1$H NMR (400 MHz, CDCl$_3$) δ 8.62 (br. s, 1H), 7.72 (d, J=8.6 Hz, 1H), 7.25 (d, J=1.8 Hz, 1H), 7.19 (dd, J=8.4, 2.3 Hz, 1H), 7.09 (d, J=2.2 Hz, 1H), 7.02-7.08 (m, 1H), 6.92-6.98 (m, 1H), 5.81 (dt, J=15.6, 5.4 Hz, 1H), 5.48 (dd, J=15.9, 7.9 Hz, 1H), 4.06-4.16 (m, 3H), 4.01 (ddd, J=15.1, 9.8, 5.0 Hz, 1H), 3.93 (d, J=15.3 Hz, 1H), 3.86 (ddd, J=8.8, 6.3, 6.3 Hz, 1H), 3.62-3.75 (m, 3H), 3.25-3.39 (m, 5H), 3.18 (d, J=14.1 Hz, 2H), 3.11 (s, 3H), 3.01-3.08 (m, 1H), 2.94 (s, 3H), 2.90-2.99 (m, 2H), 2.69-2.90 (m, 5H), 2.32-2.56 (m, 4H), 1.88-2.26 (m, 8H), 1.77-1.86 (m, 1H), 1.67-1.76 (m, 1H), 1.49-1.65 (m, 1H), 1.36-1.45 (m, 2H). m/z (ESI, +ve ion) 670.3 (M+H)$^+$.

Example 212. 2-(((1S,3'R,6'R,7'R,8'E)-6-chloro-13', 13'-dioxido-15'-oxo-3,4-dihydro-2H-spiro[naphthalene-1,22'-[20]oxa[13]thia[1,14]diazatetracyclo [14.7.2.0³,⁶.0¹⁹,²⁴]pentacosa [8,16,18,24]tetraen]-7'-yl)oxy)-N-(2-(dimethylamino)ethyl)acetamide

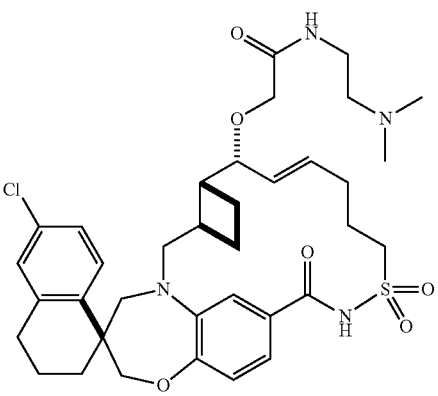

The carboxylic acid (9.5 mg, 0.015 mmol, Example 211, Step 1) was dissolved in DMF (1.0 mL) and then N,N-dimethylethylenediamine (2.0 µL, 0.018 mmol), HATU (6.9 mg, 0.018 mmol) and a drop of water were added and the reaction mixture was stirred for 4.5 hours. The crude material was purified by reverse-phase preparative HPLC using a Phenomenex Luna column, 10 micron, C8(2), 100 Å, 150×30 mm, 0.1% TFA in CH$_3$CN/H$_2$O, gradient 20% to 60% over 25 min to provide 2-(((1S,3'R,6'R,7'R,8'E)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-(2-(dimethylamino)ethyl)acetamide (8.0 mg, 9.84 µmol, 65.1% yield). $^1$H NMR (400 MHz, CDCl$_3$) δ 11.26 (br. s, 1H), 8.51 (br. s, 1H), 7.70 (d, J=8.6 Hz, 1H), 7.15-7.22 (m, 2H), 7.10 (d, J=2.2 Hz, 1H), 6.96 (s, 2H), 5.88-5.99 (m, 1H), 5.54 (dd, J=15.9, 5.6 Hz, 1H), 4.64-5.25 (m, 3H), 4.19-4.29 (m, 2H), 3.99-4.16 (m, 3H), 3.80-3.90 (m, 2H), 3.69 (d, J=14.1 Hz, 1H), 3.41 (d, J=6.5 Hz, 2H), 3.22-3.33 (m, 2H), 3.18 (d, J=14.3 Hz, 1H), 2.88-3.06 (m, 6H), 2.68-2.86 (m, 2H), 2.44-2.60 (m, 2H), 2.35 (d, J=16.8 Hz, 1H), 1.89-2.23 (m, 5H), 1.79 (d, J=9.6 Hz, 3H), 1.58-1.71 (m, 1H), 1.46-1.57 (m, 1H), 1.40 (t, J=11.8 Hz, 1H). m/z (ESI, +ve ion) 669.3 (M+H)$^+$.

Example 213. (1S,3'R,6'R,7'R,8'E)-6-chloro-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

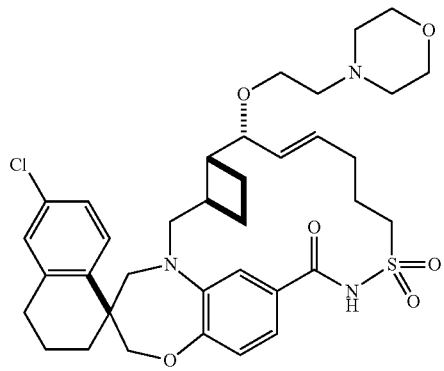

The allyl alcohol (20 mg, 0.035 mmol, Example 952) was dissolved in THF (1.00 mL) and cooled to 0° C. Sodium hydride (60% dispersion; 14.0 mg, 0.350 mmol) was added and the resulting slurry was stirred for 30 minutes. 4-(2-bromoethyl) morpholine hydrobromide (48.1 mg, 0.175 mmol) was then added and the slurry was stirred overnight. To the slurry was added DMF (1.00 mL) followed by another aliquot of sodium hydride (60% dispersion; 14.0 mg, 0.350 mmol) and 4-(2-bromoethyl) morpholine hydrobromide (48.1 mg, 0.175 mmol) and stirred overnight. The reaction was then acidified by adding 1N HCl and this mixture was filtered. The crude material was purified by reverse-phase preparative HPLC using a Phenomenex Luna column, 10 micron, C8(2), 100 Å, 150×30 mm, 0.1% TFA in CH$_3$CN/H$_2$O, gradient 30% to 60% over 20 min to provide (1s,3'r,6'r,7'r,8'e)-6-chloro-7'-(2-(4-morpholinyl)ethoxy)-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (14 mg, 0.018 mmol, 50% yield). $^1$H NMR (400 MHz, CDCl$_3$) δ 8.26 (br. s, 1H), 7.70 (d, J=8.6 Hz, 1H), 7.13-7.23 (m, 2H), 7.10 (d, J=2.2 Hz, 1H), 6.90-6.99 (m, 2H), 5.75 (dt, J=15.6, 4.5 Hz, 1H), 5.36 (dd, J=15.8, 8.2 Hz, 1H), 4.07-4.22 (m, 2H), 3.92-4.05 (m, 5H), 3.81-3.91 (m, 2H), 3.60-3.76 (m, 5H), 3.54 (br. s., 3H), 3.02-3.22 (m, 3H), 2.98 (dd, J=15.1, 8.6 Hz, 1H), 2.66-2.88 (m, 2H), 2.34-2.58 (m, 3H), 2.00-2.21 (m, 3H), 1.87-1.99 (m, 3H), 1.67-1.86 (m, 2H), 1.50-1.66 (m, 1H), 1.31-1.49 (m, 2H). m/z (ESI, +ve ion) 684.3 (M+H)$^+$.

Example 214. (1S,3'R,6'R,7'R,8'E)-6-chloro-7'-((3,5-dimethyl-4-isoxazolyl)methoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

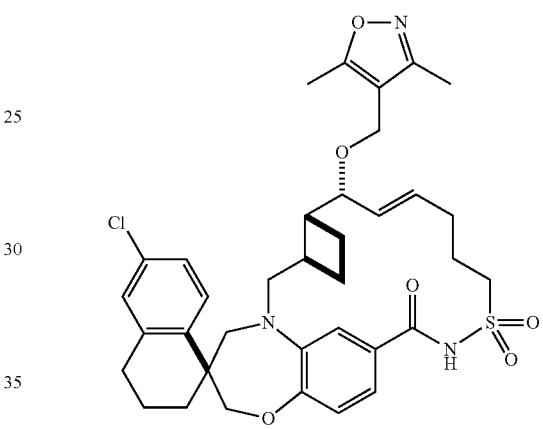

The allyl alcohol (20 mg, 0.035 mmol, Example 952) was dissolved in THF (1.00 mL) and cooled to 0° C. Sodium hydride (60% dispersion; 8.40 mg, 0.350 mmol) was added and the mixture was stirred for 30 minutes. 4-(chloromethyl)-3,5-dimethylisoxazole (0.022 mL, 0.175 mmol) was then added and the resulting mixture was stirred for 4.5 hours. Three more aliquot of reagents were added and the slurry was stirred at room temperature for 4.5 days. The reaction was quenched with water and acidified with 1N HCl to pH~5. The mixture was extracted with ethyl acetate (2×30 mL). The combined organic layers were washed with brine (1×20 mL) and dried over magnesium sulfate. The crude material was purified by reverse-phase preparative HPLC using a Phenomenex Luna column, 10 micron, C8(2), 100 Å, 150×30 mm, 0.1% TFA in CH$_3$CN/H$_2$O, gradient 50% to 80% over 25 min to provide (1S,3'R,6'R,7'R,8'E)-6-chloro-7'-((3,5-dimethyl-4-isoxazolyl)methoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (10 mg, 0.015 mmol, 42% yield). $^1$H NMR (400 MHz, CDCl$_3$) δ 8.16 (s, 1H), 7.71 (d, J=8.4 Hz, 1H), 7.30 (s, 1H), 7.18 (dd, J=8.4, 2.3 Hz, 1H), 7.09 (d, J=2.3 Hz, 1H), 6.95 (s, 2H), 5.72 (dt, J=16.0, 4.7 Hz, 1H), 5.46 (dd, J=15.8, 8.4 Hz, 1H), 4.65 (d, J=12.1 Hz, 1H), 4.13-4.26 (m, 1H), 4.11 (s, 2H), 4.03 (d, J=12.1 Hz, 1H), 3.96 (d, J=14.7 Hz, 1H), 3.59-3.71 (m, 2H), 3.19-3.30 (m, 1H), 3.16 (d, J=14.3 Hz, 1H), 2.86-2.98 (m, 1H), 2.66-2.84 (m, 2H), 2.42-2.58 (m, 2H), 2.40 (s, 3H), 2.32 (s, 3H), 2.08-2.22 (m, 3H), 1.85-2.07 (m, 4H), 1.75-1.85 (m, 1H), 1.65-1.74 (m, 1H), 1.50-1.64 (m, 1H), 1.38-1.47 (m, 2H). m/z (ESI, +ve ion) 680.3 (M+H)⁺.

Example 215. (1S,3'R,6'R,7'R,8'E)-6-chloro-7'-((1-methyl-1H-1,2,4-triazol-3-yl)methoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

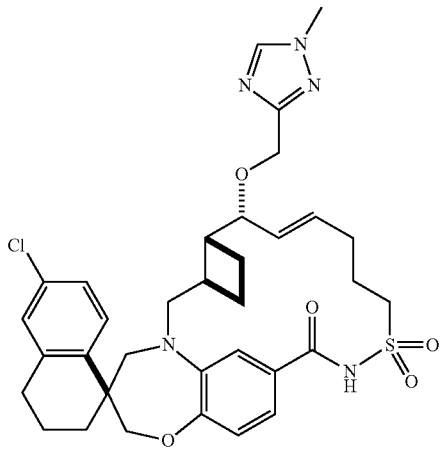

All the reagents were first azeotroped with toluene to remove any residual water or acetic acid. The allyl alcohol (27 mg, 0.047 mmol, Example 952) was dissolved in THF (0.3 mL) and cooled to 0° C. Sodium hydride (60% dispersion; 11.3 mg, 0.47 mmol) was added and the resulting light pink slurry was stirred for 30 minutes. The 3-chloromethyl-1-methyl-1h-[1,2,4]triazole, hydrochloride (0.029 mL, 0.24 mmol) was dissolved in DMF (0.5 mL) and added to the reaction mixture and allowed to warm to room temperature over a period of five hours. The reaction was quenched with water (hydrogen evolution occurred from residual hydride) and acidified with 1N HCl to pH~5. This mixture was extracted with ethyl acetate (3×30 mL). The combined organic layers were washed with 1N LiCl solution (1×20 mL) and brine (1×20 mL). The organic layer was then dried over magnesium sulfate and the crude product was purified by medium pressure chromatography (silica, 0 to 100% EtOAc (+0.3% HOAc):Hexanes) to give (1S,3'R,6'R,7'R,8'E)-6-chloro-7'-((1-methyl-1H-1,2,4-triazol-3-yl)methoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (11 mg, 0.017 mmol, 35% yield). ¹H NMR (400 MHz, CDCl₃) δ 10.46 (br. s., 1H), 8.10 (br. s., 1H), 7.71 (d, J=8.4 Hz, 1H), 7.29 (d, J=1.8 Hz, 1H), 7.12-7.22 (m, 2H), 7.08 (d, J=2.2 Hz, 1H), 6.94 (d, J=8.2 Hz, 1H), 6.09 (dt, J=15.7, 5.8 Hz, 1H), 5.53 (dd, J=15.6, 6.8 Hz, 1H), 4.85 (d, J=12.1 Hz, 1H), 4.49 (d, J=11.9 Hz, 1H), 4.02-4.16 (m, 2H), 3.99 (d, J=14.7 Hz, 1H), 3.89 (s, 3H), 3.67-3.77 (m, 2H), 3.64 (d, J=14.3 Hz, 1H), 3.19 (d, J=14.3 Hz, 1H), 2.90-2.96 (m, 1H), 2.68-2.83 (m, 2H), 2.55-2.68 (m, 1H), 2.23-2.53 (m, 3H), 1.97-2.17 (m, 4H), 1.86-1.96 (m, 2H), 1.67-1.86 (m, 2H), 1.44-1.67 (m, 2H), 1.36 (t, J=12.3 Hz, 1H). m/z (ESI, +ve ion) 666.2 (M+H)⁺.

Example 216. (1S,3'R,6'R,7'R,8'E)-6-chloro-7'-(1,3-thiazol-2-ylmethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24] tetraen]-15'-one 13',13'-dioxide

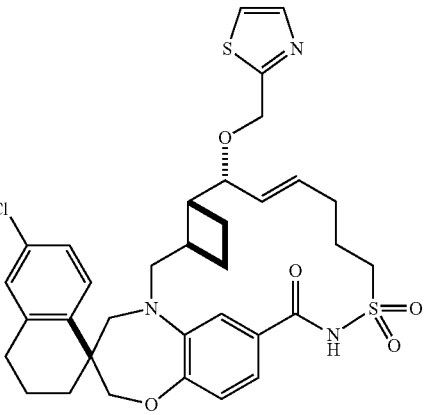

The allyl alcohol (20 mg, 0.035 mmol, Example 952) was dissolved in THF (1.00 mL) and cooled to 0° C. Sodium hydride (60% dispersion; 8.40 mg, 0.350 mmol) was added and the mixture was stirred for 30 minutes. 2-(chloromethyl)thiazole hydrochloride (30.0 mg, 0.175 mmol) was then added and the resulting mixture was stirred at room temperature overnight. LCMS now indicated reaction was ~95% complete. The reaction was quenched with water and acidified with 1N HCl to pH~5. The mixture was extracted with ethyl acetate (2×30 mL). The combined organic layers were washed with brine (1×20 mL) and dried over magnesium sulfate. The crude material was purified by reverse-phase preparative HPLC using a Phenomenex Luna column, 5 micron, C18(2), 100 Å, 150×30 mm, 0.1% TFA in CH₃CN/H₂O, gradient 50% to 80% over 25 min to provide (1S,3'R,6'R,7'R,8'E)-6-chloro-7'-((1-methyl-1H-1,2,4-triazol-3-yl)methoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]-tetraen]-15'-one 13',13'-dioxide (17 mg, 0.025 mmol, 73% yield). ¹H NMR (400 MHz, CDCl₃) δ 8.20 (br. s., 1H), 7.92 (d, J=3.3 Hz, 1H), 7.71 (d, J=8.6 Hz, 1H), 7.46 (d, J=3.5 Hz, 1H), 7.33 (s, 1H), 7.19 (dd, J=8.4, 2.2 Hz, 1H), 7.10 (d, J=2.2 Hz, 1H), 6.87-6.98 (m, 2H), 5.82 (dt, J=16.0, 4.9 Hz, 1H), 5.48 (dd, J=15.9, 8.3 Hz, 1H), 5.19 (d, J=14.3 Hz, 1H), 4.85 (d, J=14.3 Hz, 1H), 4.06-4.21 (m, 3H), 4.02 (d, J=14.9 Hz, 1H), 3.86 (dd, J=8.5, 3.2 Hz, 1H), 3.68 (d, J=14.1 Hz, 1H), 3.57 (t, J=6.3 Hz, 1H), 3.23 (dt, J=10.4, 5.2 Hz, 1H), 3.18 (d, J=14.3 Hz, 1H), 3.00 (dd, J=15.4, 8.5 Hz, 1H), 2.67-2.88 (m, 3H), 2.36-2.66 (m, 2H), 1.88-2.28 (m, 5H), 1.70-1.88 (m, 2H), 1.55-1.69 (m, 1H), 1.36-1.53 (m, 2H). m/z (ESI, +ve ion) 668.2 (M+H)⁺.

Example 217. ethyl(((1S,3'R,6'R,7'R,8'E)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)acetate

Example 218. (((1S,3'R,6'R,7'R,8'E)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)acetic acid

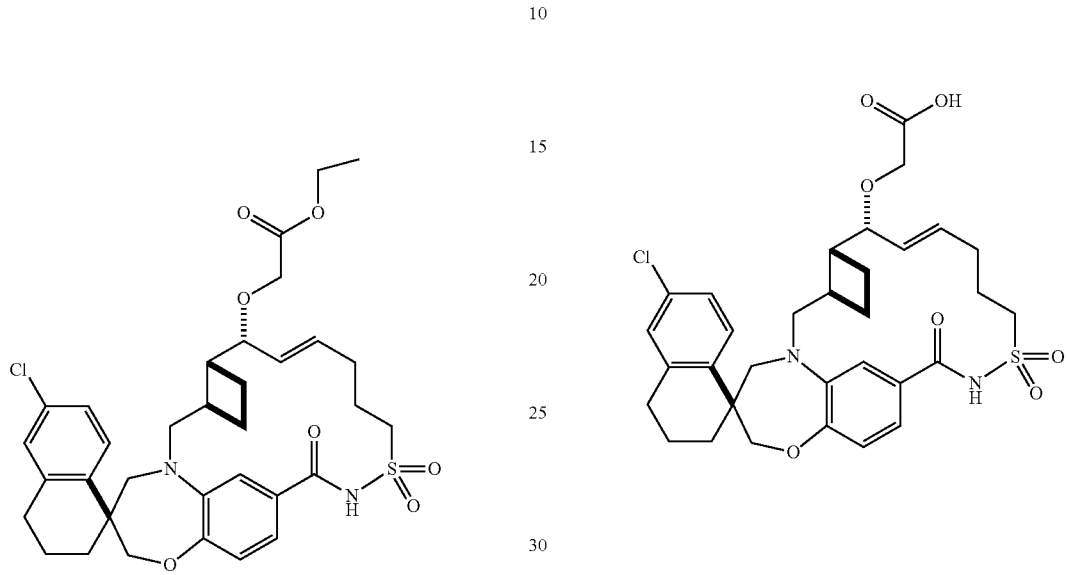

The allyl alcohol (40 mg, 0.070 mmol, Example 952) was dissolved in DCM (3.0 mL) and rhodium (ii) acetate dimer (6.2 mg, 0.014 mmol) along with ethyl diazoacetate (0.054 mL, 0.53 mmol) was added. The mixture was stirred at room temperature for two days. Upon adding the ethyl diazoacetate, rapid N2 evolution occurred. Over the two days of stirring three more aliquots of ethyl diazoacetate (0.054 mL, 0.525 mmol) and rhodium (ii) acetate dimer (6.2 mg, 0.014 mmol) were added to drive the reaction to completion. The mixture was then concentrated. The crude material was purified by reverse-phase preparative HPLC using a Phenomenex Luna column, 10 micron, C8(2), 100 Å, 150×30 mm, 0.1% TFA in CH$_3$CN/H$_2$O, gradient 50% to 80% over 25 min to provide ethyl(((1s,3'r,6'r,7'r,8'e)-6-chloro-13',13'-dioxido-15'-oxo-3,4-dihydro-2h-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetate (14.0 mg, 0.021 mmol, 29% yield). $^1$H NMR (400 MHz, CDCl$_3$) δ 8.34 (s, 1H), 7.71 (d, J=8.6 Hz, 1H), 7.31 (d, J=1.8 Hz, 1H), 7.17 (dd, J=8.4, 2.3 Hz, 1H), 6.95-7.15 (m, 3H), 5.80 (td, J=15.9, 4.8 Hz, 1H), 5.50 (dd, J=16.0, 8.4 Hz, 1H), 4.30-4.41 (m, 1H), 3.81-4.26 (m, 8H), 3.60-3.75 (m, 1H), 3.41 (ddd, J=15.3, 8.7, 6.9 Hz, 1H), 2.90-3.18 (m, 5H), 2.28-3.10 (m, 6H), 1.52-2.28 (m, 11H). m/z (ESI, +ve ion) 657.2 (M+H)$^+$.

The allylic alcohol (16 mg, 0.028 mmol, Example 952) was dissolved in THF (1.0 mL) and cooled to 0° C. Sodium hydride (60% dispersion; 3.36 mg, 0.140 mmol) was added and the slurry was stirred for 30 minutes. Methyl bromoacetate (5.2 µL, 0.056 mmol) was then added and the mixture was slowly allowed to warm to room temperature over 3.5 hours. The intermediate methyl ester was only transient during the reaction and was quickly hydrolyzed to the desired acid in situ. The reaction was quenched with 1N HCl to acidify to pH~5 and then extracted with ethyl acetate (3×15 mL). The combined organic layers were washed with brine (1×15 mL) and dried over magnesium sulfate. The crude product was then purified by medium pressure chromatography (silica, 25 to 75% EtOAc (+0.3% HOAc):Hexanes) to give (((1S,3'R,6'R,7'R,8'E)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetic acid (3.5 mg, 5.6 µmol, 20% yield). $^1$H NMR (400 MHz, CDCl$_3$) δ 8.34 (s, 1H), 7.71 (d, J=8.6 Hz, 1H), 7.31 (d, J=1.6 Hz, 1H), 7.19 (dd, J=8.5, 2.2 Hz, 1H), 7.10 (d, J=2.3 Hz, 1H), 6.98-7.02 (m, 1H), 6.92-6.97 (m, 1H), 5.81 (dt, J=15.9, 4.8 Hz, 1H), 5.50 (dd, J=16.0, 8.4 Hz, 1H), 4.32 (d, J=15.8 Hz, 1H), 4.03-4.17 (m, 4H), 3.96 (d, J=15.3 Hz, 1H), 3.85 (dd, J=8.2, 2.9 Hz, 1H), 3.69 (d, J=14.3 Hz, 1H), 3.21-3.32 (m, 1H), 3.18 (d, J=14.1 Hz, 1H), 3.01 (dd J=15.3, 8.4 Hz, 1H), 2.68-2.86 (m, 2H), 2.50-2.61 (m, 2H), 2.42 (d, J=16.6 Hz, 1H), 2.12-2.25 (m, 2H), 1.89-2.05 (m, 4H), 1.70-1.88 (m, 3H), 1.57-1.69 (m, 2H), 1.37-1.51 (m, 2H). m/z (ESI, +ve ion) 629.2 (M+H)$^+$.

Example 219. 2-(((1S,3'R,6'R,7'R,8'E)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N,N-dimethylethanesulfonamide Example 220. (1S,3'R,6'R,7'R,8'E)-6-chloro-7'-(2-hydroxyethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

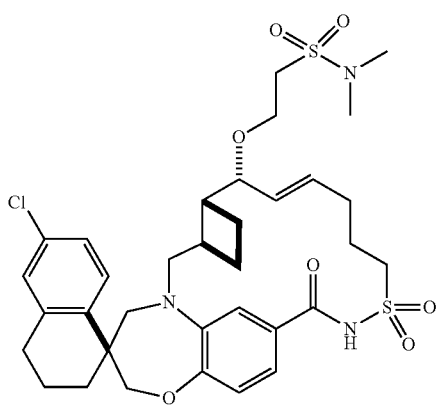

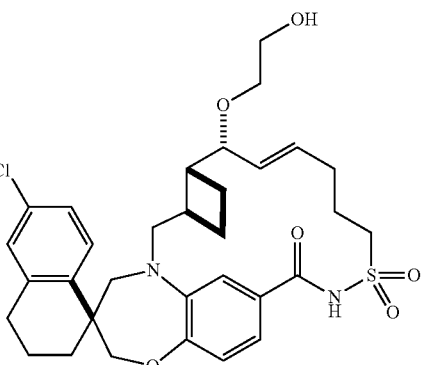

The allyl alcohol (30.0 mg, 0.053 mmol, Example 952) was dissolved in THF (1.5 mL) and cooled to 0° C. Sodium hydride (60% dispersion; 13.0 mg, 0.53 mmol) was added and the resulting slurry was stirred at 0° C. for 30 minutes. The N,N-dimethylvinylsulfonamide (0.031 mL, 0.26 mmol) was then added and the reaction mixture was stirred overnight to completion. The reaction was quenched with water and then acidified with 1N HCl to pH~5. This mixture was extracted with ethyl acetate (3×20 mL). The combined organic layers were washed with brine (1×20 mL) and dried over magnesium sulfate. The crude material was purified by reverse-phase preparative HPLC using a Phenomenex Luna column, 10 micron, C8(2), 100 Å, 150×30 mm, 0.1% TFA in CH$_3$CN/H$_2$O, gradient 45% to 75% over 20 min to provide epimeric 2-(((1S,3'R,6'R,7'R,8'E)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N,N-dimethylethanesulfonamide (17.0 mg, 0.023 mmol, 45% yield). $^1$H NMR (400 MHz, CDCl$_3$) δ 8.22 (s, 1H), 7.71 (d, J=8.6 Hz, 1H), 7.19 (dd, J=8.4, 2.2 Hz, 1H), 7.10 (d, J=2.2 Hz, 1H), 6.89-7.01 (m, 2H), 5.79 (dt, J=16.0, 4.9 Hz, 1H), 5.42 (dd, J=16.1, 8.1 Hz, 1H), 3.93-4.19 (m, 5H), 3.71-3.78 (m, 2H), 3.68 (d, J=15.1 Hz, 1H), 3.54-3.64 (m, 1H), 3.42 (dt, J=14.5, 7.1 Hz, 1H), 3.09-3.29 (m, 2H), 2.94-3.05 (m, 2H), 2.92 (s, 4H), 2.82-2.86 (m, 1H), 2.71-2.80 (m, 2H), 2.31-2.61 (m, 5H), 2.02-2.23 (m, 3H), 1.87-2.00 (m, 3H), 1.76-1.86 (m, 1H), 1.67-1.76 (m, 1H), 1.51-1.66 (m, 1H), 1.41 (q, J=10.5 Hz, 2H). m/z (ESI, +ve ion) 706.2 (M+H)$^+$.

The allyl alcohol (33 mg, 0.058 mmol, Example 952) was dissolved in THF (1.50 mL) and cooled to 0° C. Sodium hydride (60% dispersion; 23.0 mg, 0.57 mmol) was added and the resulting slurry was stirred for 30 minutes. 2-(2-bromoethoxy) tetrahydro-2H-pyran (60 mg, 0.29 mmol) was then added and the slurry was stirred overnight. The reaction was then acidified by adding 1N HCl and this mixture was filtered and concentrated in vacuo. The residue was dissolved in ether and 1 mL of 1:1 2N HCl:THF was added and the reaction was stirred for 2.5 days. LCMS indicated the reaction was 95% complete. The reaction was concentrated then dissolved in DMSO. The crude material was purified by reverse-phase preparative HPLC using a Phenomenex Luna column, 5 micron, C8(2), 100 Å, 150×21.2 mm, 0.1% TFA in CH$_3$CN/H$_2$O, gradient 30% to 70% over 20 min to provide (1S,3'R,6'R,7'R,8'E)-6-chloro-7'-(2-hydroxyethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (10 mg, 0.016 mmol, 33% yield). $^1$H NMR (400 MHz, CDCl$_3$) δ 8.72 (br. s., 1H), 7.71 (d, J=8.6 Hz, 1H), 7.31 (s, 1H), 7.18 (dd, J=8.4, 2.2 Hz, 1H), 7.09 (d, J=2.2 Hz, 1H), 6.96-7.05 (m, 1H), 6.88-6.96 (m, 1H), 5.78-5.86 (m, 1H), 5.49 (dd, J=15.8, 7.4 Hz, 1H), 3.98-4.20 (m, 4H), 3.90 (br. s., 2H), 3.77 (d, J=5.1 Hz, 2H), 3.67 (d, J=13.9 Hz, 1H), 3.49 (d, J=8.8 Hz, 1H), 3.10-3.31 (m, 2H), 2.91-3.04 (m, 1H), 2.44-2.57 (m, 2H), 2.40 (d, J=16.6 Hz, 1H), 1.98-2.22 (m, 3H), 1.93 (d, J=7.4 Hz, 2H), 1.67-1.86 (m, 1H), 1.53-1.66 (m, 1H), 1.34-1.51 (m, 2H), 1.24-1.33 (m, 3H). m/z (ESI, +ve ion) 615.2 (M+H)$^+$.

Example 221. (1S,3'R,6'R,7'R,8'E)-6-chloro-7'-hydroxy-3,4-dihydro-2H,14'H-spiro[naphthalene-1,21'-[19]oxa[12]thia[1,13]diazatetracyclo[13.7.2.0³,⁶.0¹⁸,²³]tetracosa [8,15,17,23]tetraen]-14'-one 12',12'-dioxide

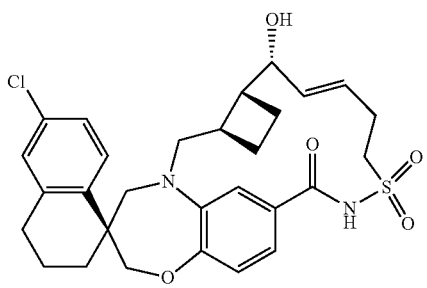 [SMILES: O=C1NS(=O)(=O)CC/C=C/[C@@H](O)[C@@H]2CC[C@H]2CN2C[C@@]3(CCCc4cc(Cl)ccc43)COc3ccc1cc32]

Step 1: (S)—N-(but-3-en-1-ylsulfonyl)-6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide

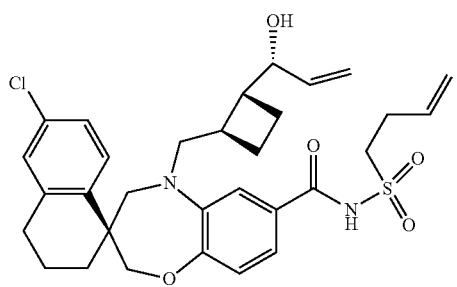 [SMILES: C=CCCS(=O)(=O)NC(=O)c1ccc2c(c1)N(C[C@@H]1CC[C@H]1[C@H](O)C=C)C[C@@]1(CCCc3cc(Cl)ccc31)CO2]

(S)-6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (89 mg, 0.17 mmol, Intermediate AA11B) was dissolved in DCM (6 mL) and cooled to 0° C. But-3-ene-1-sulfonamide (59.0 mg, 0.436 mmol Intermediate EE15), triethylamine (0.073 mL, 0.523 mmol) and DMAP (36.2 mg, 0.297 mmol) were added followed by slow addition of EDC (67 mg, 0.35 mmol). The reaction was allowed to slowly warm to room temperature and stirred for 3.5 days to completion. The reaction mixture was then concentrated to dryness and the residue was purified by medium pressure chromatography (silica, 0 to 40% EtOAc (+0.3% HOAc): Hexanes) to give (S)—N-(but-3-en-1-ylsulfonyl)-6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide (83 mg, 0.13 mmol, 76% yield). m/z (ESI, +ve ion) 627.3 (M+H)⁺.

Step 2: (1S,3'R,6'R,7'R,8'E)-6-chloro-7'-hydroxy-3,4-dihydro-2H,14'H-spiro[naphthalene-1,21'-[19]oxa[12]thia[1,13]diazatetracyclo[13.7.2.0³,⁶.0¹⁸,²³]tetracosa [8,15,17,23]tetraen]-14'-one 12',12'-dioxide (S)—N-(but-3-en-1-ylsulfonyl)-6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide (83 mg, 0.13 mmol) was dissolved in AcOH (25 mL) and sparged with argon. Hoveyda-Grubbs 2nd generation catalyst (17.0 mg, 0.026 mmol) was then added and the reaction was stirred under reduced pressure overnight. Another 8.0 mg of the RCM catalyst was added and the reaction mixture was stirred for three days under reduced pressure. Another 8.0 mg of catalyst was added and stirred overnight. The reaction mixture was concentrated under reduced pressure and purified by medium pressure chromatography (silica, 15 to 70% EtOAc (+0.3% HOAc):Hex) to give (1S,3'R,6'R,7'R,8'E)-6-chloro-7'-hydroxy-3,4-dihydro-2H,14'H-spiro[naphthalene-1,21'-[19]oxa[12]thia[1,13]diazatetracyclo[13.7.2.0³,⁶.0¹⁸,²³]tetracosa[8,15,17,23]tetraen]-14'-one 12',12'-dioxide (35 mg, 0.063 mmol, 48% yield). ¹H NMR (400 MHz, CD₃OD) δ 7.75 (d, J=8.4 Hz, 1H), 7.20 (dd, J=8.5, 2.2 Hz, 1H), 7.13 (dd, J=3.1, 2.3 Hz, 2H), 7.07 (dd, J=8.2, 2.0 Hz, 1H), 6.94 (d, J=8.2 Hz, 1H), 5.45-5.72 (m, 2H), 4.03-4.18 (m, 2H), 3.84 (dd, J=15.6, 7.9 Hz, 1H), 3.66-3.77 (m, 2H), 3.51-3.65 (m, 2H), 3.26-3.33 (m, 1H), 3.11 (dd, J=15.6, 3.6 Hz, 1H), 2.69-2.91 (m, 2H), 2.38-2.67 (m, 4H), 2.08 (d, J=13.5 Hz, 1H), 1.84-2.01 (m, 4H), 1.75-1.84 (m, 1H), 1.55-1.73 (m, 1H), 1.39-1.52 (m, 1H). m/z (ESI, +ve ion) 557.2 (M+H)⁺.

Example 222. (1S,3'R,6'R,7'R)-6-chloro-7'-hydroxy-3,4-dihydro-2H,14'H-spiro[naphthalene-1,21'-[19]oxa[12]thia[1,13]diazatetracyclo[13.7.2.0³,⁶.0¹⁸,²³] tetracosa [15,17,23]trien]-14'-one 12',12'-dioxide

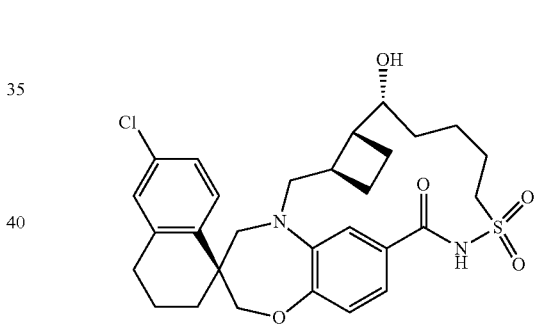

(1S,3'R,6'R,7'R,8'E)-6-chloro-7'-hydroxy-3,4-dihydro-2h,14'h-spiro[naphthalene-1,21'-[19]oxa[12]thia[1,13]diazatetracyclo[13.7.2.0³,⁶.0¹⁸,²³]tetracosa[8,15,17,23]tetraen]-14'-one 12',12'-dioxide (11 mg, 0.020 mmol, Example 207) was dissolved in EtOAc (1.0 mL) and then platinum (IV) oxide (4.5 mg, 0.020 mmol) was added. The reaction vessel was flushed with hydrogen and kept under balloon pressure for 4.5 hours. The reaction mixture was then directly loaded onto a column and purified by medium pressure chromatography (silica, 0 to 60% EtOAc (+0.3% HOAc):Hexanes) to give (1S,3'R,6'R,7'R)-6-chloro-7'-hydroxy-3,4-dihydro-2H,14'H-spiro[naphthalene-1,21'-[19]oxa[12]thia[1,13]diazatetracyclo[13.7.2.0³,⁶.0¹⁸,²³]tetracosa[15,17,23]trien]-14'-one 12',12'-dioxide (10.5 mg, 0.019 mmol, 95% yield). ¹H NMR (400 MHz, CDCl₃) δ 8.59 (s, 1H), 7.70 (d, J=8.6 Hz, 1H), 7.18 (dd, J=8.5, 2.2 Hz, 1H), 7.08 (d, J=2.2 Hz, 1H), 7.00-7.06 (m, 2H), 6.93 (d, J=7.8 Hz, 1H), 4.11 (s, 2H), 3.76-3.90 (m, 2H), 3.72 (d, J=14.5 Hz, 1H), 3.45-3.52 (m, 1H), 3.24-3.37 (m, 1H), 3.20 (d, J=14.3 Hz, 1H), 3.08 (dd, J=15.7, 2.9 Hz, 1H), 2.66-2.88 (m, 2H), 2.31-2.50 (m, 2H), 1.87-2.04 (m, 4H), 1.64-1.85 (m, 4H), 1.29-1.63 (m, 6H). m/z (ESI, +ve ion) 559.2 (M+H)⁺.

Example 225. (1S,3'R,6'R,7'R,8'E)-6-chloro-7'-methoxy-3,4-dihydro-2H,14'H-spiro[naphthalene-1,21'-[19]oxa[12]thia[1,13]diazatetracyclo[13.7.2.0$^{3,6}$.0$^{18,23}$]tetracosa [8,15,17,23]tetraen]-14'-one 12',12'-dioxide

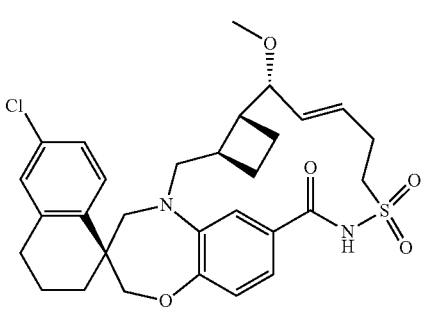 [SMILES: CO[C@@H]1/C=C/CCS(=O)(=O)NC(=O)c2ccc3c(c2)N(C[C@@H]2CC[C@H]21)C[C@@]1(CCCc2cc(Cl)ccc21)CO3]

(1S,3'R,6'R,7'R,8'E)-6-chloro-7'-hydroxy-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide (25 mg, 0.043 mmol, Example 221) was dissolved in THF (1.0 mL) and cooled to 0° C. Sodium hydride (60% dispersion) (10.3 mg, 0.43 mmol) was added and the slurry was stirred at 0° C. for 20 minutes. The slurry was taken out of the ice bath for about three minutes to ensure anion formation (slurry turns slightly green in color) and iodomethane (0.013 mL, 0.214 mmol) was then added after reemerging in the ice bath. The slurry was allowed to slowly warm to room temperature and stirred overnight. The reaction was then quenched with water (10 mL) and extracted with ethyl acetate (3×20 mL). The combined organic layers were washed with brine (1×25 mL) and dried over magnesium sulfate. The filtrate was concentrated and the residue was purified by medium pressure chromatography (silica, 0 to 40% EtOAc (+0.3% HOAc):Hexanes) to give (1S,3'R,6'R,7'R,8'E)-6-chloro-7'-methoxy-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen ]-14'-one 12',12'-dioxide (15 mg, 0.026 mmol, 74% yield). $^1$H NMR (400 MHz, CDCl$_3$) δ 8.36 (s, 1H), 7.52-7.75 (m, 1H), 6.97-7.17 (m, 3H), 6.78-6.95 (m, 2H), 5.27-5.56 (m, 2H), 3.93-4.13 (m, 3H), 3.51-3.76 (m, 4H), 3.12-3.28 (m, 1H), 2.97-3.09 (m, 4H), 2.70-2.77 (m, 1H), 2.49-2.62 (m, 2H), 2.30-2.46 (m, 2H), 1.94-2.08 (m, 3H), 1.81-1.94 (m, 3H), 1.62-1.81 (m, 3H). m/z (ESI, +ve ion) 571.2 (M+H)$^+$.

Example 226. (1S,3'R,6'R,7'R,8'E)-6-chloro-7'-methoxy-3,4-dihydro-2H,14'H-spiro[naphthalene-1,21'-[19]oxa[12]thia[1,13]diazatetracyclo[13.7.2.0$^{3,6}$.0$^{18,23}$]tetracosa [8,15,17,23]tetraen]-14'-one 12',12'-dioxide

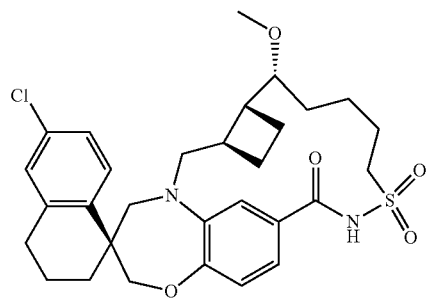 [SMILES: CO[C@@H]1CCCCS(=O)(=O)NC(=O)c2ccc3c(c2)N(C[C@@H]2CC[C@H]21)C[C@@]1(CCCc2cc(Cl)ccc21)CO3]

(1S,3'R,6'R,7'R,8'E)-6-chloro-7'-methoxy-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide (11 mg, 0.019 mmol, Example 225) was dissolved in EtOAc (1.0 mL) and platinum(iv) oxide (4.4 mg, 0.019 mmol) was then added. The reaction vessel was flushed with hydrogen and kept under balloon pressure for 4.5 hours. The reaction mixture was then directly loaded onto a column and purified by medium pressure chromatography (silica, 0 to 60% EtOAc (+0.3% HOAc):Hexanes) to give (1S,3'R,6'R,7'R,8'E)-6-chloro-7'-methoxy-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide (9.0 mg, 0.016 mmol, 82% yield). $^1$H NMR (400 MHz, CDCl$_3$) δ 8.74 (s, 1H), 7.63-7.83 (m, 1H), 7.09-7.27 (m, 4H), 6.89-7.05 (m, 1H), 4.08-4.23 (m, 3H), 3.60-3.90 (m, 3H), 3.36-3.54 (m, 1H), 3.15-3.40 (m, 5H), 2.98-3.16 (m, 2H), 2.67-2.88 (m, 2H), 2.34-2.59 (m, 2H), 1.52-2.11 (m, 12H). m/z (ESI, +ve ion) 573.2 (M+H)$^+$.

Example 227. (1S,3'R,6'R,7'R,8'E)-6-chloro-7'-hydroxy-3,4-dihydro-2H,16'H-spiro[naphthalene-1,23'-[21]oxa[14]thia[1,15]diazatetracyclo[15.7.2.0$^{3,6}$.0$^{20,25}$]hexacosa[8,17,19,25]tetraen]-16'-one 14',14'-dioxide

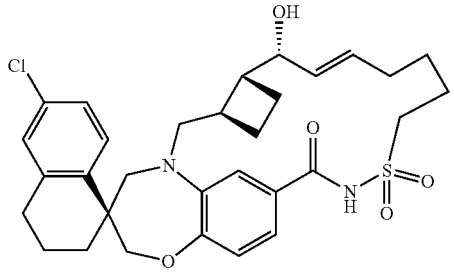 [SMILES: O=C1NS(=O)(=O)CCCC/C=C/[C@@H](O)[C@@H]2CC[C@H]2CN2C[C@@]3(CCCc4cc(Cl)ccc43)COc3ccc1cc32]

Step 1: Sodium hex-5-ene-1-sulfonate

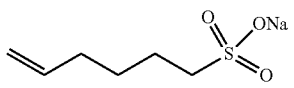

A mixture of 6-bromo-1-hexene (2.1 mL, 13 mmol, Aldrich) and sodium sulfite (1.7 g, 14 mmol) in water (11 mL) was stirred at 110° C. for 10 hrs. The water was then removed under reduced pressure. The residue was triturated with acetone (10 mL) and the resulting slurry was filtered to collect sodium hex-5-ene-1-sulfonate as a white solid (2.3 g, 12 mmol, 95% yield). $^1$H NMR (400 MHz, DMSO-d6) δ 5.78 (tdd, J=6.8, 10.3, 17.0 Hz, 1H), 5.00 (qd, J=1.7, 17.2 Hz, 1H), 4.93 (td, J=1.0, 10.2 Hz, 1H), 2.41-2.35 (m, 2H), 2.00 (q, J=7.1 Hz, 2H), 1.60-1.51 (m, 2H), 1.43-1.33 (m, 2H).

Step 2: hex-5-ene-1-sulfonamide

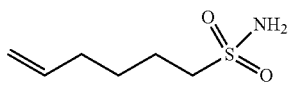

A mixture of sodium hex-5-ene-1-sulfonate (1.6 g, 8.8 mmol) and phosphorus oxychloride (32 mL, 350 mmol) was stirred at 130° C. for 6 hrs. The phosphorous oxychloride was then removed under reduced pressure. The residue was triturated with CH$_3$CN (20 mL) and the precipitate was removed via filtration. To the filtrate was added a 30% aqueous solution of NH$_3$ (15 mL) slowly at 0° C. The mixture was stirred for 30 minutes. The mixture was then diluted EtOAc (240 mL) and then washed with brine and dried over anhydrous sodium sulfate. The solvent was then removed under reduced pressure and the residue was purified on a short silica gel plug eluting with 1:1 EtOAc:hexanes to give hex-5-ene-1-sulfonamide (750 mg, 4.6 mmol, 52% yield). $^1$H NMR (400 MHz, DMSO-d6) δ 6.73 (s, 2H), 5.88-5.67 (m, 1H), 5.04 (qd, J=1.8, 17.2 Hz, 1H), 4.98 (tdd, J=1.1, 2.2, 10.2 Hz, 1H), 3.01-2.91 (m, 2H), 2.10-2.00 (m, 2H), 1.75-1.63 (m, 2H), 1.52-1.42 (m, 2H).

Step 3: (S)-6'-chloro-N-(hex-5-en-1-ylsulfonyl)-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide

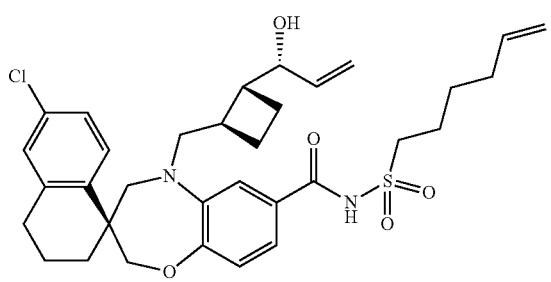 [SMILES: C=CCCCCS(=O)(=O)NC(=O)c1ccc2c(c1)N(C[C@@H]1CC[C@H]1[C@H](O)C=C)C[C@@]1(CCCc3cc(Cl)ccc31)CO2]

(S)-6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (89 mg, 0.174 mmol, Intermediate AA11B) was dissolved in DCM (6 mL) and cooled to 0° C. Hex-5-ene-1-sulfonamide (71 mg, 0.436 mmol; Example 227, Step 2), triethylamine (0.073 mL, 0.52 mmol), DMAP (36 mg, 0.297 mmol) were added followed by slow addition of EDC (67 mg, 0.35 mmol). The reaction was allowed to slowly warm to room temperature and stirred for 3.5 days to completion. The reaction mixture was then concentrated to dryness and the residue was purified by medium pressure chromatography (silica, 0 to 40% EtOAc (+0.3% HOAc):Hexanes) to give (S)-6'-chloro-N-(hex-5-en-1-ylsulfonyl)-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide (83 mg, 0.13 mmol, 73% yield). m/z (ESI, +ve ion) 655.3 (M+H)$^+$.

Step 4: (1S,3'R,6'R,7'R,8'E)-6-chloro-7'-hydroxy-3,4-dihydro-2H,16'H-spiro[naphthalene-1,23'-[21]oxa[14]thia[1,15]diazatetracyclo[15.7.2.0$^{3,6}$.0$^{2",5}$]hexacosa[8,17,19,25]tetraen]-16'-one 14',14'-dioxide (S)-6'-chloro-N-(hex-5-en-1-ylsulfonyl)-5-(((1R,2R)-2-((R)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide (83 mg, 0.13 mmol) was dissolved in AcOH (25 mL) and sparged with argon. Hoveyda-grubbs catalyst 2$^{nd}$ generation (16.0 mg, 0.025 mmol) was then added and the reaction was stirred under reduced pressure overnight. The reaction was complete and the reaction mixture was sparged with air to inactivate the catalyst. The reaction mixture was then concentrated to dryness and then purified by medium pressure chromatography (silica, 15 to 70% EtOAc (+0.3% HOAc):hexanes) to give (1S,3'R,6'R,7'R,8'E)-6-chloro-7'-hydroxy-3,4-dihydro-2H,16'H-spiro[naphthalene-1,23'-[21]oxa[14]thia[1,15]diazatetracyclo[15.7.2.0$^{3,6}$.0$^{20,25}$]hexacosa[8,17,19,25]tetraen]-16'-one 14',14'-dioxide (44 mg, 0.075 mmol, 59% yield). $^1$H NMR (400 MHz, CD$_3$OD) δ 7.76 (d, J=8.6 Hz, 1H), 7.29-7.43 (m, 1H), 7.05-7.27 (m, 3H), 6.87-7.00 (m, 1H), 5.33-5.61 (m, 2H), 4.00-4.19 (m, 2H), 3.63-3.93 (m, 4H), 3.25-3.44 (m, 5H), 3.17 (dd, J=5.2, 15.4 Hz, 1H), 2.66-2.86 (m, 2H), 2.52-2.66 (m, 1H), 2.46 (dq, J=3.2, 8.6 Hz, 1H), 1.58-2.18 (m, 13H). m/z (ESI, +ve ion) 585.2 (M+H)$^+$.

Example 228. (1S,3'R,6'R,7'R)-6-chloro-7'-hydroxy-3,4-dihydro-2H,16'H-spiro[naphthalene-1,23'-[21]oxa[14]thia[1,15]diazatetracyclo[15.7.2.0$^{3,6}$.0$^{20,25}$]hexacosa[17,19,25]trien]-16'-one 14',14'-dioxide

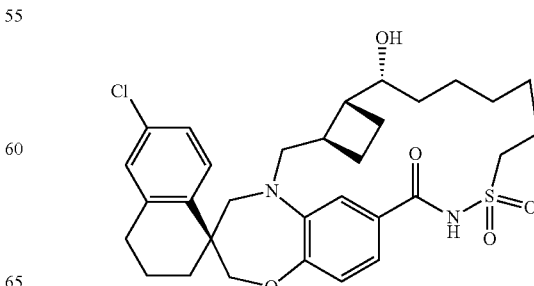

(1S,3'R,6'R,7'R,8'E)-6-chloro-7'-hydroxy-3,4-dihydro-2H,16'H-spiro[naphthalene-1,23'-[21]oxa[14]thia[1,15]diazatetracyclo[15.7.2.0³,⁶.0²⁰,²⁵]hexacosa[8,17,19,25]tetraen]-16'-one 14',14'-dioxide (15 mg, 0.026 mmol, Example 227) was dissolved in EtOAc (1.0 mL) and platinum(iv) oxide (5.8 mg, 0.026 mmol) was then added. The reaction vessel was flushed with hydrogen and kept under balloon pressure for 4.5 hours. The reaction mixture was then directly loaded on a column and purified by medium pressure chromatography (silica, 0 to 60% EtOAc (+0.3% HOAc):Hexanes) to give (1S,3'R,6'R,7'R)-6-chloro-7'-hydroxy-3,4-dihydro-2H,16'H-spiro[naphthalene-1,23'-[21]oxa[14]thia[1,15]diazatetracyclo[15.7.2.0³,⁶.0²⁰,²⁵]hexacosa[17,19,25]trien]-16'-one 14',14'-dioxide (8.5 mg, 0.014 mmol, 57% yield)). ¹H NMR (400 MHz, CDCl₃) δ 9.49 (s, 1H), 7.72 (d, J=8.6 Hz, 1H), 7.36 (dd, J=8.3, 2.1 Hz, 1H), 7.14-7.21 (m, 2H), 7.09 (d, J=2.2 Hz, 1H), 6.97 (d, J=8.2 Hz, 1H), 4.10 (d, J=5.3 Hz, 2H), 3.74-3.88 (m, 2H), 3.71 (d, J=14.3 Hz, 1H), 3.59 (dd, J=8.7, 3.2 Hz, 1H), 3.51 (dt, J=15.4, 5.6 Hz, 1H), 3.23 (d, J=14.3 Hz, 1H), 3.12 (dd, J=15.5, 6.8 Hz, 1H), 2.66-2.87 (m, 2H), 2.30-2.56 (m, 2H), 1.88-2.10 (m, 4H), 1.73-1.87 (m, 3H), 1.29-1.73 (m, 11H). m/z (ESI, +ve ion) 587.2 (M+H)⁺.

Example 229. (1S,3'R,6'R,7'R,8'E)-6-chloro-7'-methoxy-3,4-dihydro-2H,16'H-spiro[naphthalene-1,23'-[21]oxa[14]thia[1,15]diazatetracyclo[15.7.2.0³,⁶.0²⁰,²⁵]hexacosa[8,17,19,25]tetraen]-16'-one 14',14'-dioxide

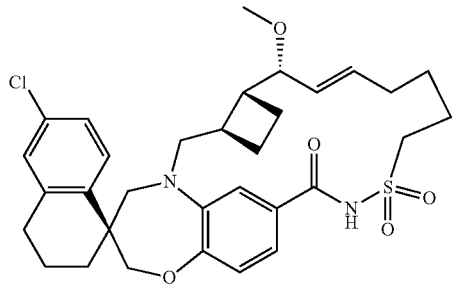 [SMILES: CO[C@@H]1/C=C/CCCCS(=O)(=O)NC(=O)c2ccc3c(c2)N(C[C@@H]2CC[C@H]21)C[C@@]1(CCCc2cc(Cl)ccc21)CO3]

(1S,3'R,6'R,7'R,8'E)-6-chloro-7'-hydroxy-3,4-dihydro-2H,16'H-spiro[naphthalene-1,23'-[21]oxa[14]thia[1,15]diazatetracyclo[15.7.2.0³,⁶.0²⁰,²⁵]hexacosa[8,17,19,25]tetraen]-16'-one 14',14'-dioxide (25 mg, 0.043 mmol, Example 227) was dissolved in THF (1.0 mL) and cooled to 0° C. Sodium hydride (60% dispersion; 17.0 mg, 0.43 mmol) was added and the slurry was stirred at 0° C. for 20 minutes. The slurry was taken out of the ice bath for about three minutes to ensure anion formation (slurry turns slightly green in color) and the iodomethane (0.013 mL, 0.214 mmol) was added after reemerging in the ice bath. The slurry was allowed to slowly warm to room temperature and stirred overnight. The reaction was then quenched with water (10 mL) and extracted with ethyl acetate (3×20 mL). The combined organic layers were washed with brine (1×25 mL) and dried over magnesium sulfate. The filtrate was concentrated and the residue was purified by medium pressure chromatography (silica, 0 to 40% EtOAc (+0.3% HOAc):Hexanes) to give (1S,3'R,6'R,7'R,8'E)-6-chloro-7'-methoxy-3,4-dihydro-2H,16'H-spiro[naphthalene-1,23'-[21]oxa[14]thia[1,15]diazatetracyclo[15.7.2.0³,⁶.0²⁰,²⁵]hexacosa[8,17,19,25]tetraen]-16'-one 14',14'-dioxide (22 mg, 0.037 mmol, 86% yield). ¹H NMR (400 MHz, CDCl₃) δ 9.35 (s, 1H), 7.57-7.73 (m, 1H), 7.29 (dd, J=2.1, 8.3 Hz, 1H), 7.21 (d, J=2.2 Hz, 1H), 7.11 (dd, J=2.2, 8.5 Hz, 1H), 6.81-6.97 (m, 1H), 5.70 (td, J=15.0, 7.3 Hz, 1H), 5.42-5.55 (m, 1H), 3.96-4.10 (m, 2H), 3.69-3.81 (m, 1H), 3.57-3.69 (m, 2H), 3.50 (dd, J=8.3, 4.4 Hz, 1H), 3.26-3.39 (m, 5H), 3.13-3.24 (m, 1H), 2.97-3.10 (m, 1H), 2.62-2.79 (m, 2H), 2.40-2.61 (m, 2H), 1.49-2.18 (m, 13H). m/z (ESI, +ve ion) 599.2 (M+H)⁺.

Example 216. (1S,3'R,6'R,7'R)-6-chloro-7'-methoxy-3,4-dihydro-2H,16'H-spiro[naphthalene-1,23'-[21]oxa[14]thia[1,15]diazatetracyclo[15.7.2.0³,⁶.0²⁰,²⁵]hexacosa[17,19,25]trien]-16'-one 14',14'-dioxide

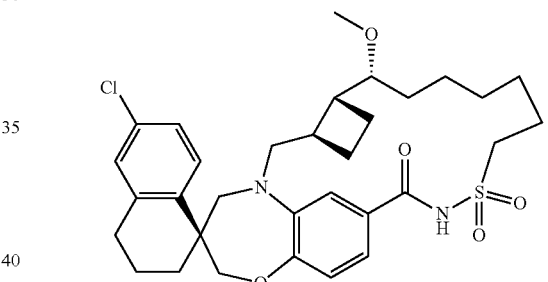

(1S,3'R,6'R,7'R,8'E)-6-chloro-7'-methoxy-3,4-dihydro-2H,16'H-spiro[naphthalene-1,23'-[21]oxa[14]thia[1,15]diazatetracyclo[15.7.2.0³,⁶.0²⁰,²⁵]hexacosa[8,17,19,25]tetraen]-16'-one 14',14'-dioxide (19 mg, 0.032 mmol, Example 229) was dissolved in EtOAc (1.0 mL) and platinum(iv) oxide (7.2 mg, 0.032 mmol) was then added. The reaction vessel was flushed with hydrogen and kept under balloon pressure for 4.5 hours. The reaction mixture was then directly loaded on a column and purified by medium pressure chromatography (silica, 0 to 60% EtOAc (+0.3% HOAc):Hexanes) to give (1S,3'R,6'R,7'R)-6-chloro-7'-methoxy-3,4-dihydro-2H,16'H-spiro[naphthalene-1,23'-[21]oxa[14]thia[1,15]diazatetracyclo[15.7.2.0³,⁶.0²⁰,²⁵]hexacosa[17,19,25]trien]-16'-one 14',14'-dioxide (12 mg, 0.020 mmol, 63% yield). ¹H NMR (400 MHz, CDCl₃) δ 9.62 (s, 1H), 7.59-7.74 (m, 1H), 7.37-7.53 (m, 1H), 6.99-7.15 (m, 3H), 6.79-6.97 (m, 1H), 3.98-4.14 (m, 2H), 3.54-3.94 (m, 3H), 3.25-3.39 (m, 1H), 2.97-3.15 (m, 3H), 2.50-2.80 (m, 3H), 2.21-2.45 (m, 1H), 1.36-2.08 (m, 20H). m/z (ESI, +ve ion) 601.2 (M+H)⁺.

Example 231. (1S,3'R,6'R,7'R,8'E,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'R,8'E,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

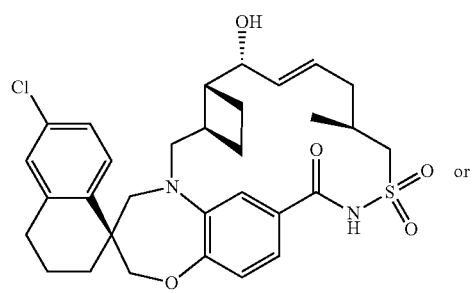

or

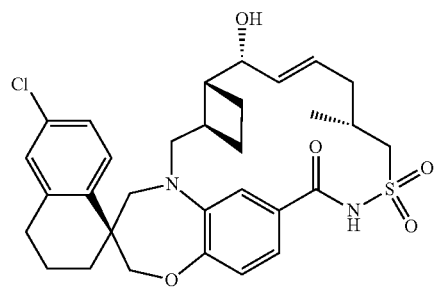

Step 1: (S)-6'-chloro-5-((((1R,2R)-2-((R,E)-1-hydroxyhex-2-en-1-yl)cyclobutyl)methyl)-N—(((S)-2-methylpent-4-en-1-yl)sulfonyl)-3',4,4',5-tetrahydro-2H,2'H-spiro[benzo[b][1,4]oxazepine-3,1'-naphthalene]-7-carboxamide and (S)-6'-chloro-5-((((1R,2R)-2-((R,E)-1-hydroxyhex-2-en-1-yl)cyclobutyl)methyl)-N—(((R)-2-methylpent-4-en-1-yl)sulfonyl)-3',4,4',5-tetrahydro-2H,2'H-spiro[benzo[b][1,4]oxazepine-3,1'-naphthalene]-7-carboxamide

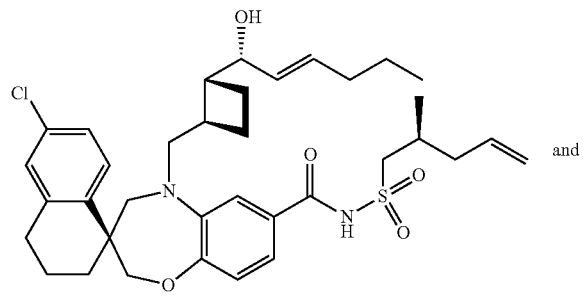

and

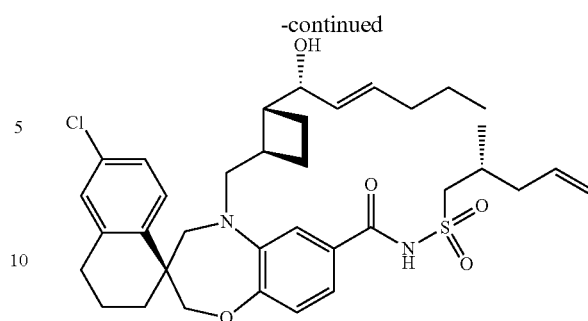

(S)-6'-chloro-5-((((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (0.600 g, 1.18 mmol, Intermediate AA12B), a racemic mixture of (S)-2-methylpent-4-ene-1-sulfonamide and (R)-2-methylpent-4-ene-1-sulfonamide (0.326 g, 2.000 mmol, Example 376, Step 2) and 4-dimethylaminopyridine (DMAP) (0.244 g, 2.000 mmol) were dissolved in DCM (12 mL). To the reaction mixture was added edc hydrochloride (EDC; 0.451 g, 2.35 mmol) and stirred overnight. The reaction mixture was then purified by medium pressure chromatography with no work-up (silica, 10 to 60% EtOAc (+0.3% HOAc):Hexanes) to give (S)-6'-chloro-5-((((1R,2R)-2-((R,E)-1-hydroxyhex-2-en-1-yl)cyclobutyl)methyl)-N—(((S)-2-methylpent-4-en-1-yl)sulfonyl)-3',4,4',5-tetrahydro-2H,2'H-spiro[benzo[b][1,4]oxazepine-3,r-naphthalene]-7-carboxamide and (S)-6'-chloro-5-((((1R,2R)-2-((R,E)-1-hydroxyhex-2-en-1-yl)cyclobutyl)methyl)-N—(((R)-2-methylpent-4-en-1-yl)sulfonyl)-3',4,4',5-tetrahydro-2H,2'H-spiro[benzo[b][1,4]oxazepine-3,1'-naphthalene]-7-carboxamide as a 1:1 mixture (390 mg, 0.60 mmol, 51% combined yield). m/z (ESI, +ve ion) 655.2 (M+H)⁺.

Step 2: (1S,3'R,6'R,7'R,8'E,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'R,8'E,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide The 1:1 mixture of (S)-6'-chloro-5-((((1R,2R)-2-((R,E)-1-hydroxyhex-2-en-1-yl)cyclobutyl)methyl)-N—(((S)-2-methylpent-4-en-1-yl)sulfonyl)-3',4,4',5-tetrahydro-2H,2'H-spiro[benzo[b][1,4]oxazepine-3,1'-naphthalene]-7-carboxamide and (S)-6'-chloro-5-((((1R,2R)-2-((R,E)-1-hydroxyhex-2-en-1-yl)cyclobutyl)methyl)-N—(((R)-2-methylpent-4-en-1-yl)sulfonyl)-3',4,4',5-tetrahydro-2H,2'H-spiro[benzo[b][1,4]oxazepine-3,1'-naphthalene]-7-carboxamide (390 mg, 0.595 mmol) was dissolved in 1,2-dichloroethane (300 mL) and the vessel was flushed with argon. (1,3-dimesitylimidazolidin-2-ylidene)(3-phenyl-1H-inden-1-ylidene)ruthenium(VI) chloride (39.8 mg, 0.060 mmol) was then added and the solution was stirred at 80° C. for 2.5 hours (more catalyst was added as needed to drive the reaction to completion). 2-(2-(vinyloxy)ethoxy)ethanol (0.024 mL, 0.18 mmol) was then added and the mixture was stirred for 30 minutes to quench the catalyst; the reaction was then concentrated and the residue was purified by medium pressure chromatography (silica, 30 to 80% EtOAc (+0.3% HOAc):Hexanes) to give (1S,3'R,6'R,7'R,8'E,11'S)-

6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'R,8'E,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (56 mg, 0.096 mmol, 16% yield) ¹H NMR (400 MHz, CDCl₃) δ 9.26 (br. s., 1H), 7.61 (d, J=8.4 Hz, 1H), 7.28-7.48 (m, 1H), 6.95-7.17 (m, 3H), 6.74-6.93 (m, 1H), 5.67-5.90 (m, 1H), 5.48-5.66 (m, 1H), 3.79-4.12 (m, 5H), 3.57 (d, J=14.3 Hz, 1H), 2.96-3.16 (m, 2H), 2.59-2.89 (m, 3H), 2.43 (br. s., 2H), 2.12-2.23 (m, 1H), 1.38-2.07 (m, 11H), 1.10 (d, J=6.3 Hz, 3H). m/z (ESI, +ve ion) 584.7 (M+H)⁺.

Example 232. (1S,3'R,6'R,7'R,8'Z,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'R,8'Z,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

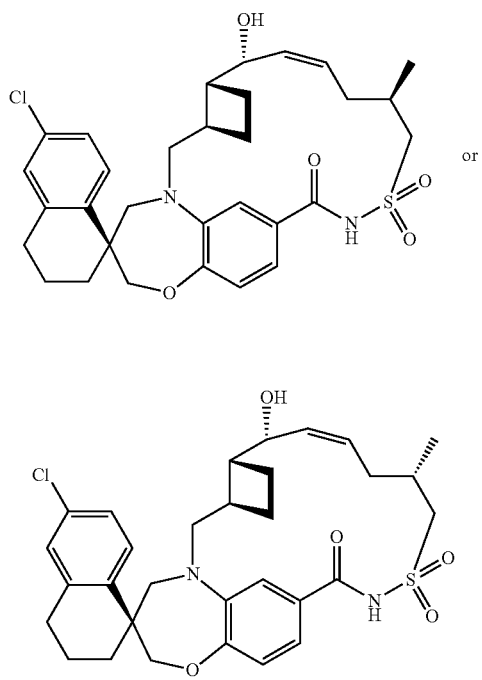

The title compound was obtained as the second eluting isomer from medium pressure chromatography (silica, 30 to 80% EtOAc (+0.3% HOAc):Hexanes) in Example 231, Step 2 (32 mg, 0.055 mmol, 9.2% yield). ¹H NMR (400 MHz, CDCl₃) δ 9.66 (d, J=17.6 Hz, 1H), 7.55-7.67 (m, 1H), 7.18-7.28 (m, 1H), 7.08 (dd, J=2.3, 8.4 Hz, 1H), 7.00 (d, J=2.3 Hz, 1H), 6.74-6.93 (m, 2H), 5.43-5.82 (m, 2H), 4.47 (t, J=6.0 Hz, 1H), 3.84-4.14 (m, 3H), 3.48-3.73 (m, 4H), 3.32 (dd, J=3.5, 15.7 Hz, 1H), 2.87-3.16 (m, 2H), 2.27-2.77 (m, 6H), 1.48-1.98 (m, 8H), 1.00-1.09 (m, 3H). m/z (ESI, +ve ion) 584.7 (M+H)⁺.

Example 233. (1S,3'R,6'R,7'R,8'Z,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'R,8'Z,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

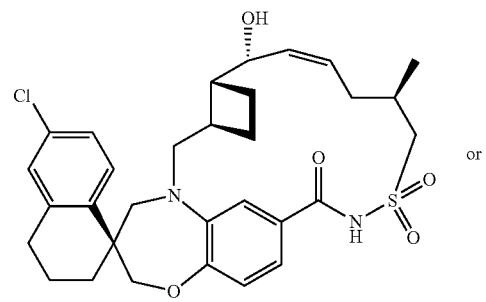

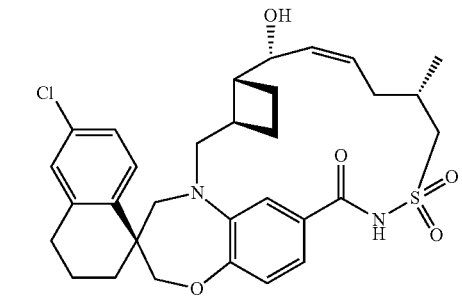

The title compound was obtained as the third eluting isomer from medium pressure chromatography (silica, 30 to 80% EtOAc (+0.3% HOAc):Hexanes) in Example 231, Step 2 (10 mg, 0.014 mmol, 2.4% yield). ¹H NMR (400 MHz, CDCl₃) δ 9.22 (s, 1H), 7.73 (d, J=8.4 Hz, 1H), 7.21 (dt, J=8.6, 2.2 Hz, 2H), 7.11 (d, J=2.2 Hz, 1H), 6.83-7.08 (m, 2H), 5.79-5.94 (m, 1H), 5.69 (dd, J=6.5, 11.2 Hz, 1H), 4.49 (t, J=5.9 Hz, 1H), 3.95-4.22 (m, 2H), 3.67-3.90 (m, 3H), 3.40-3.59 (m, 1H), 3.01-3.29 (m, 2H), 2.69-2.90 (m, 3H), 2.18-2.54 (m, 2H), 1.79-2.21 (m, 10H), 1.43 (t, J=12.7 Hz, 1H), 1.24 (d, J=6.8 Hz, 3H). m/z (ESI, +ve ion) 584.7 (M+H)⁺.

Example 235. (1S,3'R,6'R,7'R,8'Z,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

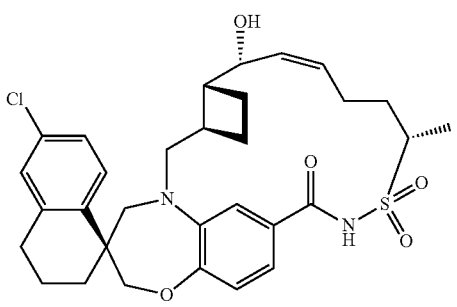

Step 1: (S)-6'-chloro-N—((S)-hex-5-en-2-ylsulfonyl)-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide

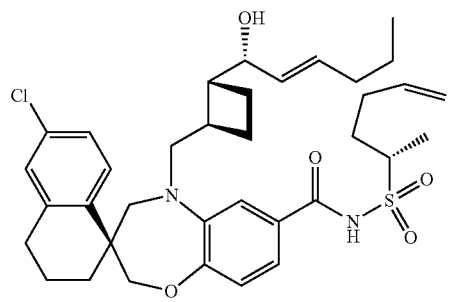

(S)-6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (0.300 g, 0.588 mmol, Intermediate AA12B), (S)-hex-5-ene-2-sulfonamide (0.144 g, 0.882 mmol, Intermediate EE202) and 4-dimethylaminopyridine (DMAP) (0.12 g, 1.00 mmol) were dissolved in DCM (12 mL). To the reaction mixture was added EDC (0.23 g, 1.18 mmol) and stirred overnight. The reaction mixture was then purified by medium pressure chromatography with no work-up (silica, 10 to 60% EtOAc (+0.3% HOAc):hexanes) to give (S)-6'-chloro-N—((S)-hex-5-en-2-ylsulfonyl)-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide (290 mg, 0.44 mmol, 75% yield). m/z (ESI, +ve ion) 655.2 (M+H)$^+$.

Step 2: (1S,3'R,6'R,7'R,8'Z,12'S)-6-chloro-7'-hydroxy-12'-methyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide (S)-6'-chloro-N—((S)-hex-5-en-2-ylsulfonyl)-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide (290 mg, 0.44 mmol) was dissolved in 1,2-dichloroethane (200 mL) and the vessel was flushed with argon. The (1,3-dimesitylimidazolidin-2-ylidene)(3-phenyl-1H-inden-1-ylidene)ruthenium(VI) chloride (29.6 mg, 0.044 mmol) was then added and the solution was stirred at 80° C. for 2.5 hours (more catalyst was added as needed to drive the reaction to completion). The 2-(2-(vinyloxy)ethoxy)ethanol (0.024 mL, 0.177 mmol) was added and stirred for 30 minutes to quench the catalyst and the reaction was then concentrated and the residue was purified by medium pressure chromatography (silica, 30 to 80% EtOAc (+0.3% HOAc):Hexanes) to give (1S,3'R,6'R,7'R,8'Z,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as the first eluting isomer (44 mg, 0.075 mmol, 17% yield). $^1$H NMR (400 MHz, CDCl$_3$) δ 7.57-7.67 (m, 1H), 7.25-7.38 (m, 1H), 7.30 (dd, J=2.1, 8.3 Hz, 1H), 7.07-7.17 (m, 1H), 6.97-7.04 (m, 1H), 6.93 (s, 2H), 6.76-6.93 (m, 2H), 5.54-5.69 (m, 1H), 5.41-5.54 (m, 1H), 4.67-4.76 (m, 1H), 4.47 (t, J=5.3 Hz, 1H), 3.73-4.09 (m, 3H), 3.50-3.72 (m, 4H), 2.95-3.18 (m, 1H), 2.56-2.76 (m, 3H), 2.16-2.50 (m, 3H), 1.66-2.02 (m, 7H), 1.46-1.56 (m, 3H). m/z (ESI, +ve ion) 584.7 (M+H)$^+$.

Example 236. (1S,3'R,6'R,7'S,8'E)-6-chloro-7'-hydroxy-9'-bromo-3,4-dihydro-2H,15'H-spiro[naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide or (1S,3'R,6'R,7'R,8'E)-6-chloro-7'-hydroxy-9'-bromo-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

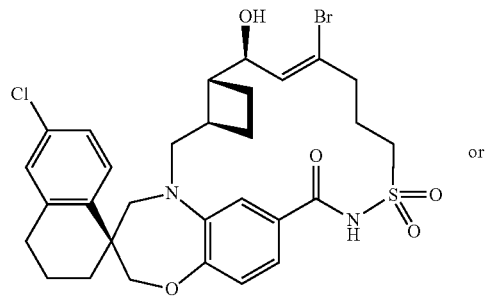

or

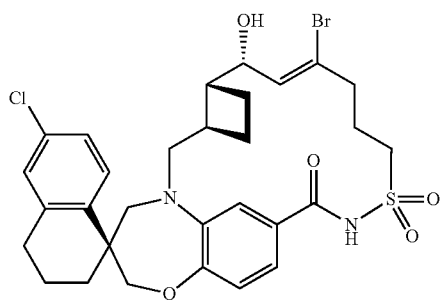

Step 1: Potassium (Z)-(2-bromo-5-chloropent-1-en-1-yl)trifluoroborate

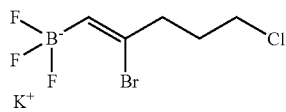 [SMILES: F[B-](F)(F)/C=C(\Br)CCCCl ; [K+]]

Boron tribromide (1.0 M in DCM) (23 mL, 23 mmol) soln. was cooled to −78° C. 5-chloropent-1-yne (2.4 g, 23 mmol) was dissolved in DCM (47 mL) and added dropwise to the boron tribromide solution. The reaction mixture immediately turned to a dark orange solution. This solution was stirred at −78° C. for one hour. Then, the diisopropylether (6.64 mL, 46.8 mmol) was added and the ice bath was removed and the solution was allowed to warm to room temperature and stirred for 2.5 days. The reaction mixture was then concentrated to give the desired crude product (Z)-diisopropyl(2-bromo-5-chloropent-1-en-1-yl)boronate. The crude isopropyl boronate ester (4300 mg, 14 mmol) was dissolved in THF (27 mL). 2 mL of KFHF (400 mg/mL soln.; 6500 mg, 83 mmol) was added and the resulting yellow solution was stirred overnight. The reaction mixture was then concentrated to dryness under reduced pressure and the residue was first slurried in warm acetone and filtered. The filtrate was then triturated with diethyl ether and a white precipitate formed that was filtered, washed with ether and dried to give potassium (Z)-(2-bromo-5-chloropent-1-en-1-yl)trifluoroborate (4.00 g, 13.8 mmol, 100% yield). m/z (ESI, +ve ion) 269.9 (M−K+H)$^+$, 157.1 (M−K$^+$-112)$^+$ (base peak).

Step 2: (S)-methyl-5-(((1R,2R)-2-((R,Z)-3-bromo-6-chloro-1-hydroxyhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate or (S)-methyl-5-(((1R,2R)-2-((S,Z)-3-bromo-6-chloro-1-hydroxyhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate

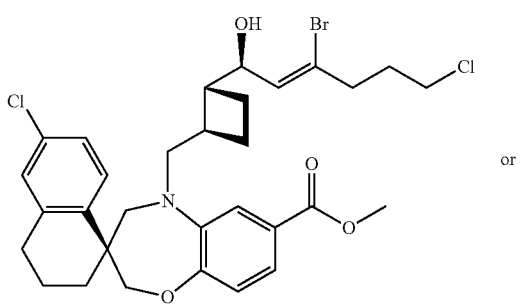

or

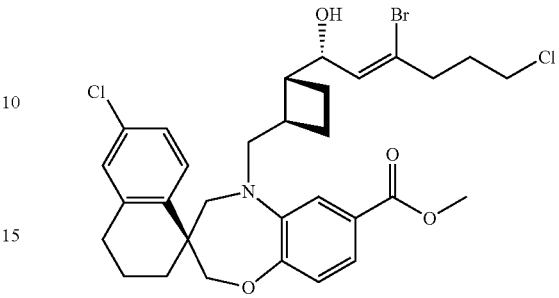

The (Z)-(2-bromo-5-chloropent-1-en-1-yl)trifluoroborate (2.2 g, 7.7 mmol) was slurried in 10 mL of DCM and cooled to 0° C. The boron trifluoride etherate (0.98 mL, 7.7 mmol) was added and the slurry was stirred at 0° C. for 10 minutes. Intermediate AA11A, Step 20A (1.00 g, 2.20 mmol) was dissolved in 5 mL of DCM and added slowly at 0° C. The ice bath was then removed and the mixture was allowed to warm to room temperature over 3.5 hours. The resulting yellow mixture was diluted with DCM (~100 mL) and water (45 mL) was added. The layers were separated and the aqueous layer was extracted (1×150 mL) with DCM. The combined organic layers were dried over magnesium sulfate and the crude product was purified by medium pressure chromatography (silica, 0 to 30% EtOAc:Hexanes) to give (S)-methyl 5-(((1R,2R)-2-((R,Z)-3-bromo-6-chloro-1-hydroxyhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate or (S)-methyl 5-(((1R,2R)-2-((S,Z)-3-bromo-6-chloro-1-hydroxyhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate (340 mg, 0.53 mmol. 24%) as the first eluting and major isomer. Further elution provided (S)-methyl 5-(((1R,2R)-2-((R,Z)-3-bromo-6-chloro-1-hydroxyhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate or (S)-methyl 5-(((1R,2R)-2-((S,Z)-3-bromo-6-chloro-1-hydroxyhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate (230 mg, 0.36 mmol, 16% yield) as the second eluting and minor isomer. m/z (ESI, +ve ion) 638.0 (M+H)$^+$.

Step 3: (S)-methyl 5-(((1R,2R)-2-4S,Z)-3-bromo-1-hydroxy-6-(pyrimidin-2-ylthio)hex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate or (S)-methyl 5-(((1R,2R)-2-((R,Z)-3-bromo-1-hydroxy-6-(pyrimidin-2-ylthio)hex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate Step 4: (S)-methyl 5-(((1R,2R)-2-((R,Z)-3-bromo-1-hydroxy-6-(pyrimidin-2-ylsulfonyl)hex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate or (S)-methyl 5-(((1S,2R)-2-4S,Z)-3-bromo-1-hydroxy-6-(pyrimidin-2-ylsulfonyl)hex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate

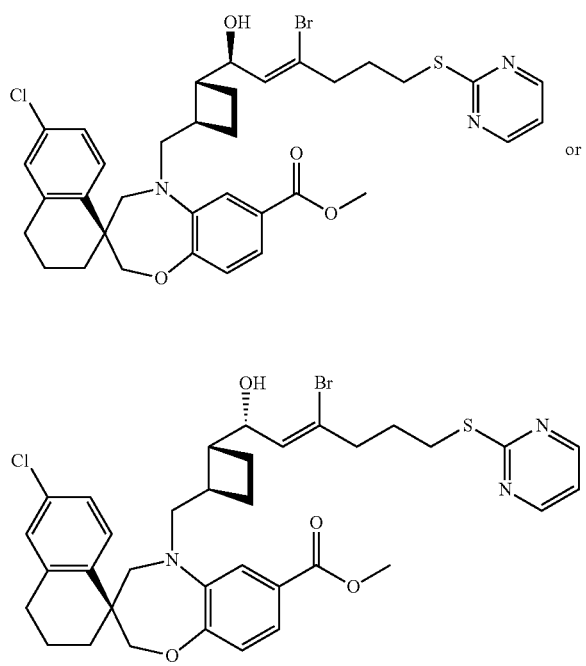

or

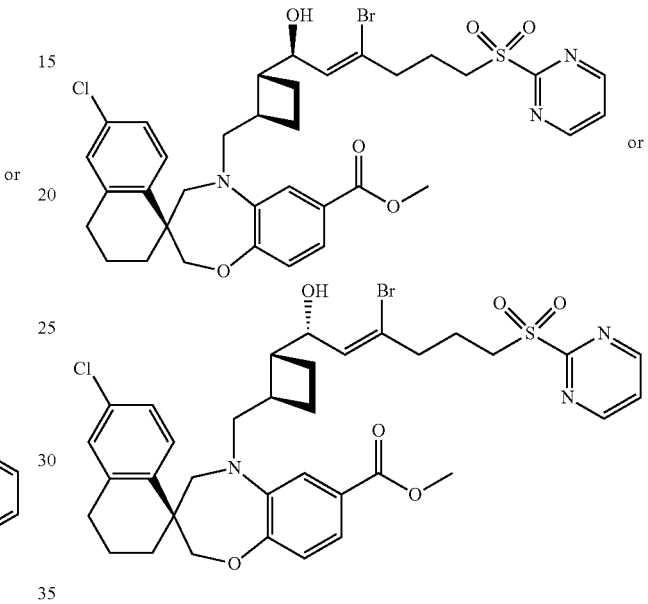

(S)-methyl 5-(((1R,2R)-2-((R,Z)-3-bromo-6-chloro-1-hydroxyhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate or (S)-methyl 5-(((1R,2R)-2-((S,Z)-3-bromo-6-chloro-1-hydroxyhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate (280 mg, 0.44 mmol, Example 236, Step 2, second eluting isomer) was dissolved in DMF (9 mL) and potassium carbonate (240 mg, 1.8 mmol) and 2-mercaptopyrimidine (200 mg, 1.8 mmol) were added. The mixture was stirred for 4.5 hours to completion. The reaction was quenched with water and extracted with ethyl acetate (2×20 mL). The combined organic layers were washed with brine (1×10 mL) and dried over magnesium sulfate. The crude product was then purified by medium pressure chromatography (silica, 0 to 40% EtOAc:Hexanes) to give (S)-methyl 5-(((1R,2R)-2-((S,Z)-3-bromo-1-hydroxy-6-(pyrimidin-2-ylthio)hex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate or (S)-methyl 5-(((1R,2R)-2-((R,Z)-3-bromo-1-hydroxy-6-(pyrimidin-2-ylthio)hex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate (190 mg, 0.26 mmol, 59% yield). m/z (ESI, +ve ion) 713.1 (M+H)$^+$ Hydrogen peroxide 30% in water (0.24 mL, 2.3 mmol), phenylphosphonic acid (8.7 µL, 0.078 mmol), sodium tungstate, dihydrate (8.0 µL, 0.078 mmol) and tetrabutylammonium sulfate, 50 wt. % solution in water (0.090 mL, 0.078 mmol) were added together and (S)-methyl 5-(((1R,2R)-2-4S,Z)-3-bromo-1-hydroxy-6-(pyrimidin-2-ylthio)hex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate or (S)-methyl 5-(((1R,2R)-2-((R,Z)-3-bromo-1-hydroxy-6-(pyrimidin-2-ylthio)hex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate (190 mg, 0.26 mmol, from step 3) dissolved in toluene (2.0 mL) was added. The mixture was heated to 60° C. and stirred for 3.5 hours to completion. The mixture was then cooled to room temperature and diluted with ethyl acetate and water. The layers were separated and the aqueous layer was extracted with ethyl acetate (1×15 mL). The combined organic layers were washed with brine (1×10 mL) and dried over magnesium sulfate. The crude product was purified by medium pressure chromatography (silica, 0 to 100% EtOAc:Hexanes) to give (S)-methyl 5-(((1R,2R)-2-((R,Z)-3-bromo-1-hydroxy-6-(pyrimidin-2-ylsulfonyl)hex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate or (S)-methyl 5-(((1S,2R)-2-((S,Z)-3-bromo-1-hydroxy-6-(pyrimidin-2-ylsulfonyl)hex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate (46 mg, 0.062 mmol, 24% yield). m/z (ESI, +ve ion) 746.0 (M+H)$^+$.

669

Step 5: (S)-methyl 5-(((1R,2R)-2-((R,Z)-3-bromo-1-hydroxy-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate or (S)-methyl 5-(((1R,2R)-2-((S,Z)-3-bromo-1-hydroxy-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate

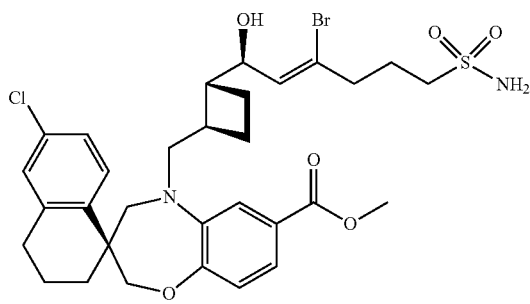

or

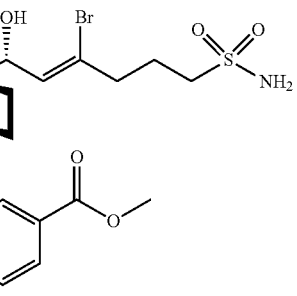

(S)-methyl 5-(((1R,2R)-2-((R,Z)-3-bromo-1-hydroxy-6-(pyrimidin-2-ylsulfonyl)hex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate or (S)-methyl 5-(((1S,2R)-2-4S,Z)-3-bromo-1-hydroxy-6-(pyrimidin-2-ylsulfonyl)hex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate (45 mg, 0.060 mmol, from step 4) was dissolved in MeOH (6.5 mL) and potassium carbonate (41.7 mg, 0.302 mmol) was added. The mixture was stirred for 1.5 hours. The hydroxylamine-o-sulfonic acid (34 mg, 0.30 mmol) was then added and the resulting cloudy reaction mixture was stirred for two hours. The reaction was concentrated and then partitioned between water (15 mL) and ethyl acetate (25 mL). The aqueous layer was extracted (1×25 mL) with EtOAc and the combined organic layers were washed with brine and dried over magnesium sulfate. The crude product was purified by medium pressure chromatography (silica, 30 to 100% EtOAc:Hexanes) to give (S)-methyl 5-(((1R,2R)-2-((R,Z)-3-bromo-1-hydroxy-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate or (S)-methyl 5-(((1R,2R)-2-((S,Z)-3-bromo-1-hydroxy-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate. (41 mg, 0.060 mmol, 100% yield). m/z (ESI, +ve ion) 683.0 (M+H)⁺.

670

Step 6: (S)-5-(((1R,2R)-2-((R,Z)-3-bromo-1-hydroxy-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((S,Z)-3-bromo-1-hydroxy-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid

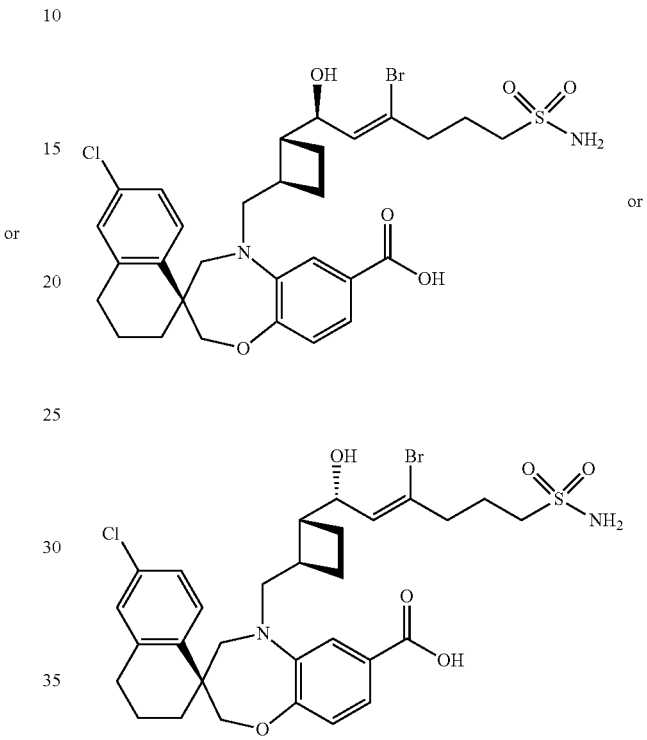

(S)-methyl 5-(((1R,2R)-2-((R,Z)-3-bromo-1-hydroxy-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate or (S)-methyl 5-(((1R,2R)-2-((S,Z)-3-bromo-1-hydroxy-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate (41 mg, 0.060 mmol) was dissolved in a 2:1 mixture of MeOH (3.00 mL) and THF (1.5 mL). To the solution was added lithium hydroxide (2 M; 0.30 mL, 0.60 mmol) and the resulting mixture was stirred for overnight. The reaction was then heated to 50° C. and stirred for 7.5 hours. The reaction mixture was then concentrated to a reduced volume in vacuo. The residue was then acidified to pH~5 and this mixture was extracted with ethyl acetate (3×25 mL). The combined organic layers were washed with brine (1×15 mL) and dried over magnesium sulfate to give (S)-5-(((1R,2R)-2-((R,Z)-3-bromo-1-hydroxy-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((S,Z)-3-bromo-1-hydroxy-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid (40 mg, 0.060 mmol, 100% yield). m/z (ESI, +ve ion) 669.1 (M+H)⁺.

Step 7. (1S,3'R,6'R,7'S,8'E)-6-chloro-7'-hydroxy-9'-bromo-3,4-dihydro-2H,15'H-spiro[naphthalene-1, 22'-[20]oxa[13]thia[1,14]diazatetracyclo[14.7.2. 0$^{3,6}$.0$^{19,24}$]pentacosa [8,16,18,24]tetraen]-15'-one 13',13'-dioxide or (1S,3'R,6'R,7'R,8'E)-6-chloro-7'-hydroxy-9'-bromo-3,4-dihydro-2H,15'H-spiro[naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide EDC (34 mg, 0.18 mmol), triethylamine (36 mg, 0.36 mmol), DMAP (22 mg, 0.18 mmol) and (S)-5-(((1R,2R)-2-((R,Z)-3-bromo-1-hydroxy-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((S,Z)-3-bromo-1-hydroxy-6-sulfamoylhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid (40 mg, 0.60 mmol) were combined in DCM (12 mL) and stirred overnight at room temperature. The reaction mixture was concentrated. The crude material was purified by reverse-phase preparative HPLC using a Phenomenex Luna column, 10 micron, C8(2), 100 Å, 150×30 mm, 0.1% TFA in CH$_3$CN/H$_2$O, gradient 40% to 70% over 20 min to provide (1S,3'R,6'R,7'S,8'E)-6-chloro-7'-hydroxy-9'-bromo-3,4-dihydro-2H, 15'H-spiro[naphthalene-1,22'-[20]oxa[13]thia[1,14] diazatetracyclo[14.7.2.0$^{3,6}$.0$^{19,24}$]pentacosa[8,16,18,24] tetraen]-15'-one 13',13'-dioxide or (1S,3'R,6'R,7'R,8'E)-6-chloro-7'-hydroxy-9'-bromo-3,4-dihydro-2H,15'H-spiro [naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide. (5.1 mg, 7.9 μmol, 13% yield). $^1$H NMR (400 MHz, CDCl$_3$) δ ppm 8.76 (br. s., 1H), 7.68 (d, J=8.4 Hz, 1H), 7.18 (dd, J=8.5, 2.2 Hz, 1H), 7.13-7.16 (m, 1H), 7.07-7.13 (m, 2H), 6.96 (d, J=8.0 Hz, 1H), 5.96 (d, J=7.8 Hz, 1H), 4.51 (dd, J=7.6, 5.1 Hz, 1H), 4.06-4.24 (m, 2H), 3.85-4.02 (m, 1H), 3.40-3.71 (m, 4H), 2.57-2.87 (m, 5H), 2.08-2.20 (m, 3H), 1.97-2.07 (m, 1H), 1.69-1.96 (m, 6H), 1.49-1.67 (m, 1H), 1.30-1.45 (m, 1H). m/z (ESI, +ve ion) 651.1 (M+H)$^+$.

Example 238. (1S,3'R,6'R,7'R,8'E)-6-chloro-7'-hydroxy-9'-methyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide or (1S,3'R,6'R,7'S,8'E)-6-chloro-7'-hydroxy-9'-methyl-3,4-dihydro-2H,15'H-spiro[naphthalene-1,22'-[20]oxa[13]thia[1,14] diazatetracyclo[14.7.2.0$^{3,6}$.0$^{19,24}$]pentacosa [8,16,18,24]tetraen]-15'-one 13',13'-dioxide

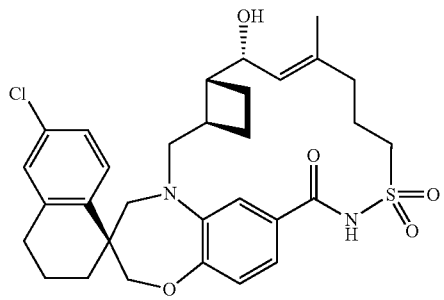

The vinyl bromide (1S,3'R,6'R,7'S,8'E)-6-chloro-7'-hydroxy-9'-bromo-3,4-dihydro-2h,15'H-spiro[naphthalene-1, 22'-[20]oxa[13]thia[1,14]diazatetracyclo[14.7.2.0$^{3,6}$.0$^{19,24}$] pentacosa[8,16,18,24]tetraen]-15'-one 13',13'-dioxide or (1S,3'R,6'R,7'R,8'E)-6-chloro-7'-hydroxy-9'-bromo-3,4-dihydro-2H,15'H-spiro[naphthalene-1,22'-[20]oxa[13]thia[1, 14]diazatetracyclo[14.7.2.0$^{3,6}$.0$^{19,24}$]pentacosa[8,16,18,24] tetraen]-15'-one 13',13'-dioxide (9.0 mg, 0.014 mmol, Example 236) was dissolved in 1,4-dioxane (0.3 mL) and cesium carbonate (16 mg, 0.048 mmol), PdCl$_2$(dppf)-CH$_2$Cl$_2$ (2.3 mg, 2.8 μmol) and methaneboronic acid (2.5 mg, 0.042 mmol) were then added and the reaction was heated at 100° C. for one hour. The reaction was then cooled and diluted with EtOAc. The mixture was then filtered and the filtrate was concentrated to dryness. The crude product was purified using SFC chromatography (AS column, 35% MeOH/CO2) to give (1S,3'R,6'R,7'R,8'E)-6-chloro-7'-hydroxy-9'-methyl-3,4-dihydro-2H,15'H-spiro[naphthalene-1, 22'-[20]oxa[13]thia[1,14]diazatetracyclo[14.7.2.0$^{3,6}$.0$^{19,24}$] pentacosa[8,16,18,24]tetraen]-15'-one 13',13'-dioxide or (1S,3'R,6'R,7'S,8'E)-6-chloro-7'-hydroxy-9'-methyl-3,4-dihydro-2H,15'H-spiro[naphthalene-1,22'-[20]oxa[13]thia[1, 14]diazatetracyclo[14.7.2.0$^{3,6}$.0$^{19,24}$]pentacosa[8,16,18,24] tetraen]-15'-one 13',13'-dioxide (2.3 mg, 28%). $^1$H NMR (400 MHz, CDCl$_3$) δ ppm 7.79 (d, J=8.6 Hz, 1H), 7.49 (s, 1H), 7.35 (d, J=7.6 Hz, 1H), 7.18 (dd, J=8.5, 2.2 Hz, 1H), 7.12 (d, J=2.2 Hz, 1H), 6.81 (d, J=8.0 Hz, 1H), 5.74 (d, J=9.6 Hz, 1H), 4.32 (d, J=7.6 Hz, 1H), 4.05-4.11 (m, 1H), 3.93-4.02 (m, 1H), 3.67-3.81 (m, 2H), 3.38-3.51 (m, 2H), 3.38-3.52 (m, 2H), 3.17 (dd, J=15.0, 10.7 Hz, 1H), 2.70-2.97 (m, 4H), 2.49-2.63 (m, 1H), 2.25-2.42 (m, 1H), 2.00-2.20 (m, 3H), 1.87-1.99 (m, 4H), 1.82 (t, J=7.9 Hz, 2H), 1.68-1.72 (m, 3H), 1.39-1.54 (m, 1H). m/z (ESI, +ve ion) 585.1 (M+H)$^+$, 567.3 (M–H$_2$O+H)$^+$ (base peak).

Example 239. (1S,3'R,6'R,7'R,8'E)-6-chloro-7'-hydroxy-9'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E)-6-chloro-7'-hydroxy-9'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

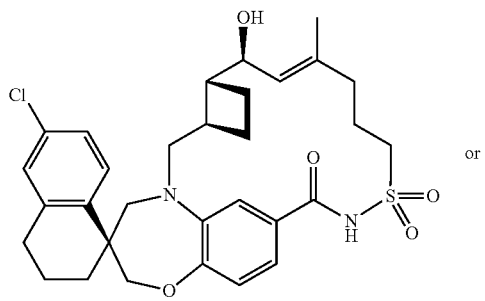

or

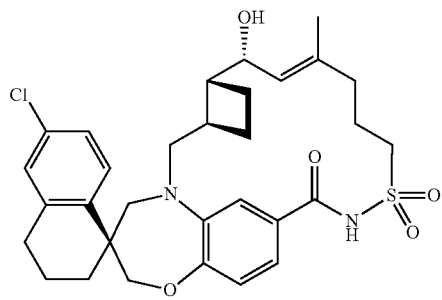

Step 1: (1S,3'R,6'R,7'S,8'E)-6-chloro-7'-hydroxy-9'-bromo-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'R,8'E)-6-chloro-7'-hydroxy-9'-bromo-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

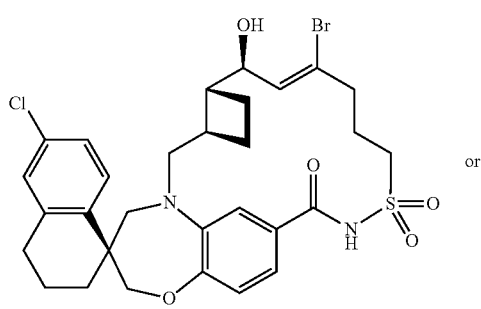

or

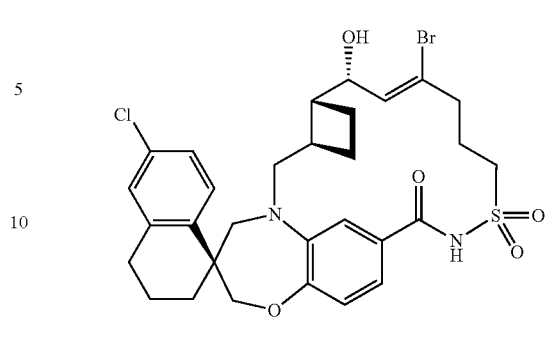

The title compound was obtained from Example 236 Step 3, first eluting isomer following a similar procedure as outlined in example 236, Steps 4-7.

Step 2: (1S,3'R,6'R,7'R,8'E)-6-chloro-7'-hydroxy-9'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E)-6-chloro-7'-hydroxy-9'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The vinyl bromide (1S,3'R,6'R,7'S,8'E)-6-chloro-7'-hydroxy-9'-bromo-3,4-dihydro-2h,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'R,8'E)-6-chloro-7'-hydroxy-9'-bromo-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (55 mg, 0.085 mmol, Example 238, step 1) was dissolved in 1,4-dioxane (2.0 mL) and cesium carbonate (96 mg, 0.30 mmol), PdCl$_2$(dppf)-CH$_2$Cl$_2$ (14 mg, 17 μmop and methaneboronic acid (15 mg, 0.250 mmol) were then added and the reaction was heated at 100° C. for one hour. The reaction was then cooled and diluted with EtOAc. The mixture was then filtered and the filtrate was concentrated to dryness. The crude product was purified using SFC chromatography (AS column, 35% MeOH/CO2) to give (1S,3'R,6'R,7'R,8'E)-6-chloro-7'-hydroxy-9'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E)-6-chloro-7'-hydroxy-9'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (5.0 mg, 33%). $^1$H NMR (400 MHz, CDCl$_3$) δ ppm 1.79 (t, J=8.02 Hz, 2H) 1.85-1.99 (m, 4H) 1.99-2.17 (m, 4H) 2.24-2.36 (m, 1H) 2.49-2.61 (m, 1H) 2.69-2.97 (m, 4H) 3.14 (dd, J=14.87, 10.56 Hz, 1H) 3.37-3.49 (m, 2H) 3.65-3.78 (m, 2H) 3.92-4.00 (m, 1H) 4.03-4.13 (m, 1H) 4.30 (d, J=7.63 Hz, 1H) 5.71 (d, J=9.59 Hz, 1H) 6.58-6.66 (m, 1H) 6.78 (d, J=8.02 Hz, 1H) 7.09 (d, J=2.15 Hz, 1H) 7.16 (dd, J=8.61, 2.15 Hz, 1H) 7.33 (d, J=7.63 Hz, 1H) 7.47 (s, 1H) 7.71-7.81 (m, 1H). m/z (ESI, +ve ion) 585.3 (M+H)$^+$.

Example 240. (1S,3'R,6'R,7'S,9'S)-6-chloro-7'-hydroxy-9'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide and (1S,3'R,6'R,7'S,9'R)-6-chloro-7'-hydroxy-9'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide or (1S,3'R,6'R,7'R,9'S)-6-chloro-7'-hydroxy-9'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide and (1S,3'R,6'R,7'R,9'R)-6-chloro-7'-hydroxy-9'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide

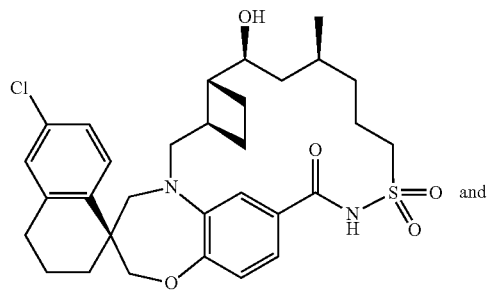 and

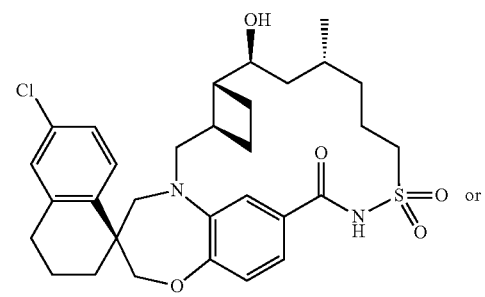 or

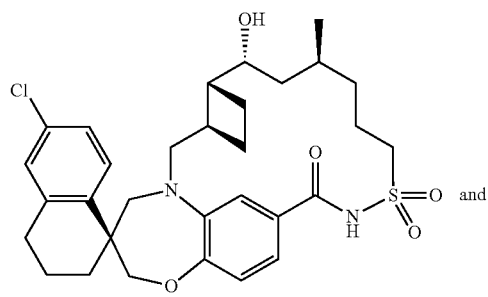 and

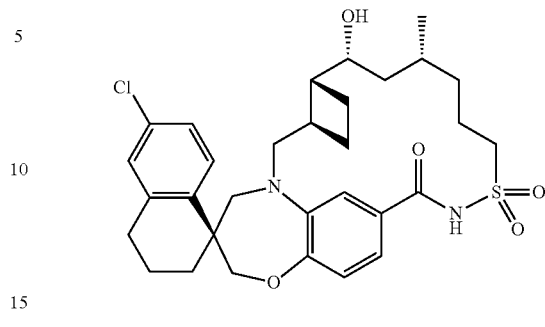

To a solution of (1S,3'R,6'R,7'R,8'E)-6-chloro-7'-hydroxy-9'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E)-6-chloro-7'-hydroxy-9'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (40 mg, 0.062 mmol, Example 238) in EtOAc (2.0 mL) and MeOH (1.0 mL) was added platinum(iv) oxide (34.9 mg, 0.154 mmol) and the reaction flask was flushed with hydrogen and kept under balloon pressure overnight. LCMS indicated 70% conversion, so another aliquot of platinum(iv) oxide (35 mg, 0.15 mmol) and MeOH (1.0 mL) was added and the mixture was stirred again under hydrogen for an additional 5.5 hours to completion. The slurry was then filtered and then concentrated to dryness. The crude material was purified by reverse-phase preparative HPLC using a Phenomenex Luna column, 5 micron, C18(2), 100 Å, 150×30 mm, 0.1% TFA in $CH_3CN/H_2O$, gradient 40% to 70% over 20 min to provide (1S,3'R,6'R,7'S,9'S)-6-chloro-7'-hydroxy-9'-methyl-3,4-dihydro-2h,15'h-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide and (1S,3'R,6'R,7'S,9'R)-6-chloro-7'-hydroxy-9'-methyl-3,4-dihydro-2h,15'h-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'R,9'S)-6-chloro-7'-hydroxy-9'-methyl-3,4-dihydro-2h,15'h-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide and (1S,3'R,6'R,7'R,9'R)-6-chloro-7'-hydroxy-9'-methyl-3,4-dihydro-2h,15'h-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide as the first eluting isomer (12.0 mg, 0.020 mmol, 33% yield). ¹H NMR (400 MHz, CHLOROFORM-d) δ ppm 9.81 (br. s. 1H), 7.68 (d, J=8.4 Hz, 1H), 7.34 (d, J=8.2 Hz, 1H), 7.17 (dd, J=8.5, 2.2 Hz, 1H), 7.04-7.13 (m, 2H), 6.93 (d, J=8.2 Hz, 1H), 4.01-4.14 (m, 2H), 3.84 (br. s. 1H), 3.44-3.76 (m, 4H), 3.03-3.43 (m, 2H), 2.61-2.90 (m, 2H), 2.06-2.18 (m, 2H), 1.73-2.05 (m, 9H), 1.60-1.72 (m, 1H), 1.38-1.59 (m, 4H), 1.28-1.38 (m, 1H), 0.90-1.03 (m, 3H). m/z (ESI, +ve ion) 587.2 (M+H)⁺.

Example 241. (1S,3'R,6'R,7'S,9'S)-6-chloro-7'-hydroxy-9'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide and (1S,3'R,6'R,7'S,9'R)-6-chloro-7'-hydroxy-9'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide or (1S,3'R,6'R,7'R,9'S)-6-chloro-7'-hydroxy-9'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide and (1S,3'R,6'R,7'R,9'R)-6-chloro-7'-hydroxy-9'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide

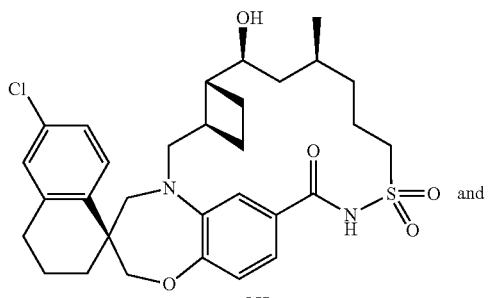

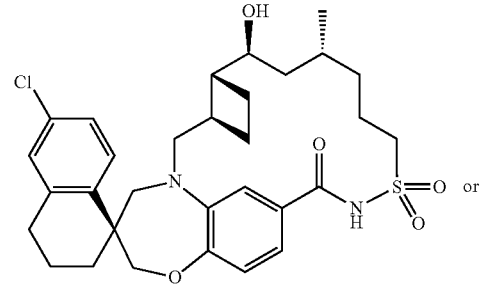

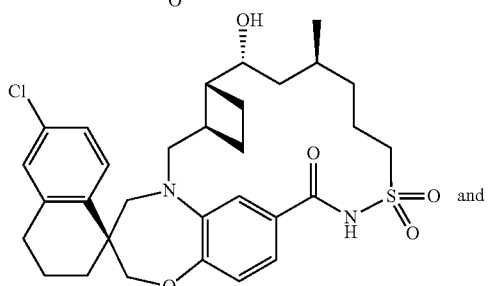

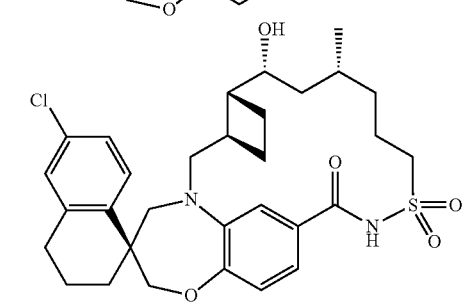

The title compound was obtained as the second eluting isomer from reverse-phase preparative HPLC using a Phenomenex Luna column, 5 micron, C18(2), 100 Å, 150×30 mm, 0.1% TFA in CH₃CN/H₂O, gradient 40% to 70% over 20 min in Example 240 (6.0 mg, 0.020 mmol, 17% yield). $^1$H NMR (400 MHz, CDCl$_3$) δ 9.93 (br. s., 1H), 7.49-7.63 (m, 1H), 7.15-7.34 (m, 2H), 6.90-7.11 (m, 2H), 6.67-6.82 (m, 1H), 3.80-4.12 (m, 2H), 3.32-3.70 (m, 4H), 2.86-3.26 (m, 3H), 2.51-2.74 (m, 3H), 2.11-2.47 (m, 5H), 0.96-2.05 (m, 11H), 0.75-0.88 (m, 3H). m/z (ESI, +ve ion) 587.2 (M+H)⁺.

Example 242. (1S,3'R,6'R,7'S,9'S)-6-chloro-7'-hydroxy-9'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide and (1S,3'R,6'R,7'S,9'R)-6-chloro-7'-hydroxy-9'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide or (1S,3'R,6'R,7'R,9'S)-6-chloro-7'-hydroxy-9'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide and (1S,3'R,6'R,7'R,9'R)-6-chloro-7'-hydroxy-9'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide

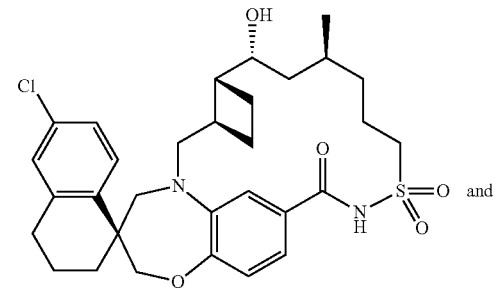

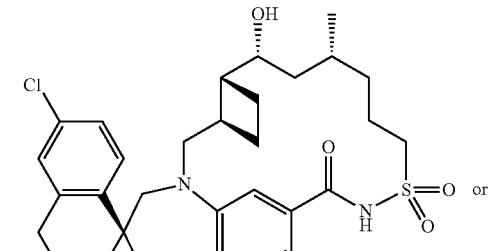

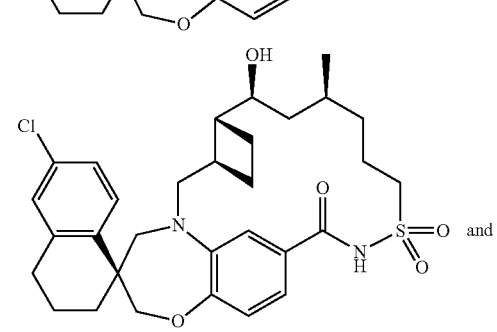

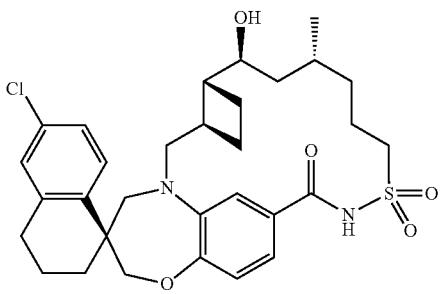

To a solution of (1S,3'R,6'R,7'R,8'E)-6-chloro-7'-hydroxy-9'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E)-6-chloro-7'-hydroxy-9'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (40 mg, 0.062 mmol, Example 239) in EtOAc (2.0 mL) and MeOH (1.0 mL) was added platinum(iv) oxide (35 mg, 0.15 mmol) and the reaction flask was flushed with hydrogen and kept under balloon pressure overnight. LCMS indicated 70% conversion, so another aliquot of platinum(iv) oxide (35 mg, 0.15 mmol) and MeOH (1.0 mL) was added and the mixture was stirred again under hydrogen for an additional 5.5 hours to completion. The slurry was then filtered and then concentrated to dryness. The crude material was purified by reverse-phase preparative HPLC using a Phenomenex Luna column, 5 micron, C18(2), 100 Å, 150×30 mm, 0.1% TFA in CH$_3$CN/H$_2$O, gradient 40% to 70% over 20 min to provide (1S,3'R,6'R,7'S,9'S)-6-chloro-7'-hydroxy-9'-methyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide and (1S,3'R,6'R,7'S,9'R)-6-chloro-7'-hydroxy-9'-methyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'S)-6-chloro-7'-hydroxy-9'-methyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide and (1S,3'R,6'R,7'R,9'R)-6-chloro-7'-hydroxy-9'-methyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide as the first eluting isomer (1.3 mg, 2.2 μmol, 2.6% yield). $^1$H NMR (400 MHz, CDCl$_3$) δ 9.15-9.34 (m, 1H), 7.60-7.71 (m, 1H), 7.27-7.37 (m, 1H), 7.04-7.13 (m, 2H), 7.02-7.16 (m, 3H), 6.88-6.96 (m, 1H), 3.83-4.12 (m, 3H), 3.63-3.77 (m, 2H), 3.06-3.36 (m, 4H), 2.59-2.84 (m, 4H), 2.26-2.48 (m, 3H), 1.37-1.81 (m, 9H), 1.13-1.28 (m, 5H). m/z (ESI, +ve ion) 587.2 (M+H)$^+$.

Example 243. (1S,3'R,6'R,7'S,9'S)-6-chloro-7'-hydroxy-9'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide and (1S,3'R,6'R,7'S,9'R)-6-chloro-7'-hydroxy-9'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'S)-6-chloro-7'-hydroxy-9'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide and (1S,3'R,6'R,7'R,9'R)-6-chloro-7'-hydroxy-9'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide

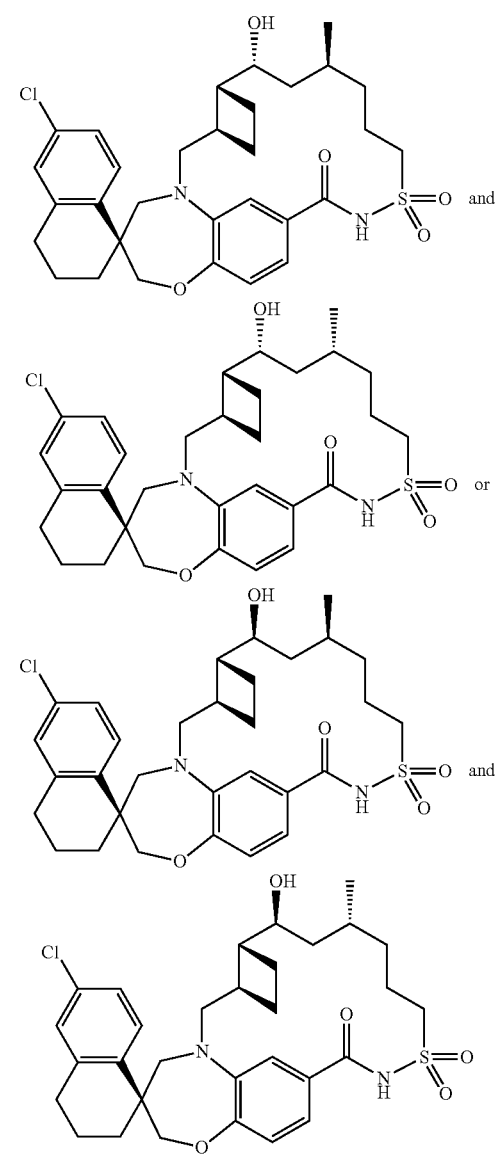

The title compound was obtained as the second eluting isomer from reverse-phase preparative HPLC using a Phenomenex Luna column, 5 micron, C18(2), 100 Å, 150×30 mm, 0.1% TFA in CH$_3$CN/H$_2$O, gradient 40% to 70% over 20 min in Example 242 (12.0 mg, 0.020 mmol, 24% yield). $^1$H NMR (400 MHz, CDCl$_3$) δ 8.79 (br. s., 1H), 7.50-7.66 (m, 1H), 7.12-7.19 (m, 3H), 7.06 (ddd, J=2.15, 8.36, 12.18 Hz, 2H), 6.91-6.99 (m, 1H), 6.73-6.87 (m, 1H), 3.94-3.97 (m, 2H), 3.67-3.83 (m, 2H), 3.50-3.67 (m, 2H), 3.32-3.45 (m, 1H), 3.04 (d, J=14.28 Hz, 1H), 2.93 (dd, J=8.22, 15.26 Hz, 1H), 2.58-2.71 (m, 2H), 2.26-2.41 (m, 3H), 1.26-2.02 (m, 13H), 0.71-0.83 (m, 3H). m/z (ESI, +ve ion) 587.2 (M+H)$^+$.

Example 244. dimethyl ((1S,3'R,6'R,7'S,9'S,11'S, 12'R)-6-chloro-7'-hydroxy-11', 1 2'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-9'-yl) propanedioate or dimethyl ((1S,3'R,6'R,7'S,9'S,11'R, 12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-9'-yl) propanedioate or dimethyl ((1S,3'R,6'R,7'S,9'R, 11'R,12'R)-6-chloro-7'-hydroxy-11',12'-dimethyl-13', 13'-dioxido-15'-oxo-3,4-dihydro-2H-spiro [naphthalene-1,22'-[20]oxa[13]thia[1,14] diazatetracyclo[14.7.2.0$^{3,6}$.0$^{19,24}$]pentacosa [16,18, 24]trien]-9'-yl)propanedioate or dimethyl ((1S,3'R, 6'R,7'R,9'R,10'R,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14] diazatetracyclo[14.7.2.0$^{3,6}$.0$^{19,24}$]pentacosa [16,18, 24]trien]-9'-yl)propanedioate

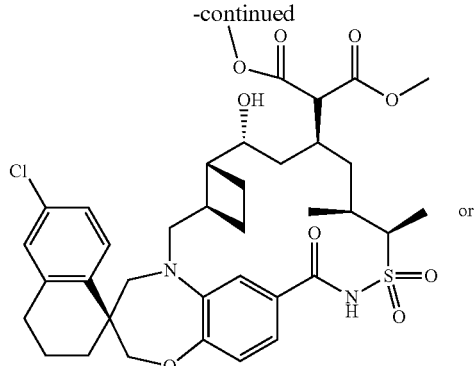

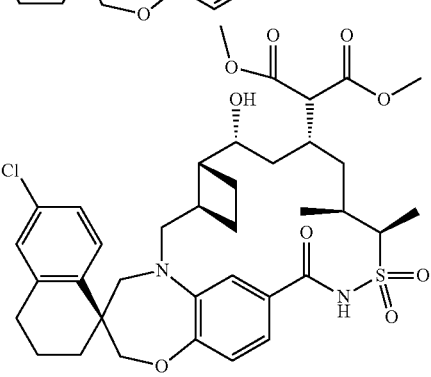

Step 1: (1S,3'R,6'R,8'E,12'S)-6-chloro-12'-methyl-3, 4-dihydro-2H,7'H,15'H-spiro[naphthalene-1,22'-[20] oxa[13]thia[1,14]diazatetracyclo[14.7.2.0$^{3,6}$.0$^{19,24}$] pentacosa [8,16,18,24]tetraene]-7',15'-dione 13',13'-dioxide

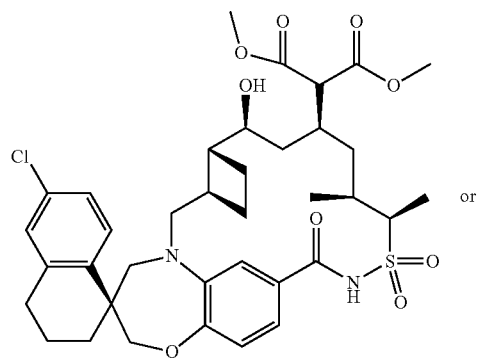

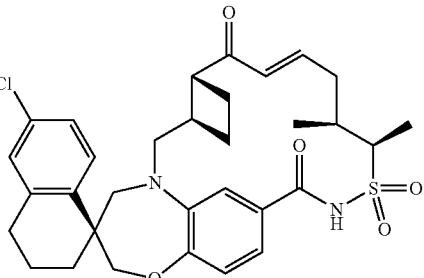

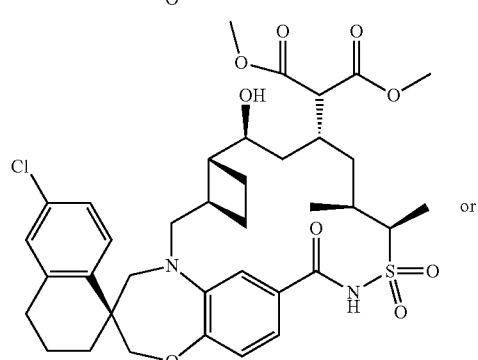

The allyl alcohol (310 mg, 0.520 mmol, Example 719, Step 2) was dissolved in DCM (6.0 mL) and cooled to 0° C. Dess-Martin periodinane (270 mg, 0.63 mmol) was then added and the reaction mixture was stirred for 1.5 hours. Another 90 mg of Dess-Martin reagent was added at 0° C. and stirred for an additional 45 minutes. The reaction was quenched with 20 mL of 1M Na$_2$S$_2$O$_3$ and allowed to warm to room temperature. The mixture was extracted (3×40 mL) with DCM. The combined organic layers were washed with water (1×30 mL) and then dried over magnesium sulfate. The crude product was purified by medium pressure chromatography (silica, 10 to 100% EtOAc (+0.3% HOAc): Hexanes) to give (1S,3'R,6'R,8'E,12'S)-6-chloro-12'-methyl-3,4-dihydro-2H,7'H,15'H-spiro[naphthalene-1,22'-[20]oxa [13]thia[1,14]diazatetracyclo[14.7.2.0$^{3,6}$.0$^{19,24}$]pentacosa [8,16,18,24]tetraene]-7',15'-dione 13',13'-dioxide (230 mg, 0.385 mmol, 74.0% yield). $^1$H NMR (400 MHz, CDCl$_3$) δ 8.32-9.05 (m, 1H), 7.69-7.90 (m, 1H), 7.35-7.48 (m, 1H), 7.17-7.27 (m, 1H), 7.06-7.16 (m, 1H), 6.81-6.99 (m, 2H), 6.59-6.72 (m, 1H), 5.93 (d, J=15.65 Hz, 1H), 4.01-4.24 (m, 3H), 3.74-3.97 (m, 3H), 3.26 (d, J=14.48 Hz, 1H), 2.92-3.16 (m, 2H), 2.69-2.89 (m, 2H), 1.70-2.26 (m, 9H), 1.48-1.56 (m, 3H), 1.35-1.46 (m, 1H), 1.29 (t, J=7.14 Hz, 1H), 1.07-1.19 (m, 3H). m/z (ESI, +ve ion) 596.7 (M+H)$^+$.

Step 2: 1S,3'R,6'R,9'S,11'S,12'R)-6-chloro-9'-(dimethylpropanedioate)-11',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 13',13'-dioxide and/or (1S,3'R,6'R,9'R,11'S,12'R)-6-chloro-9'-(dimethylpropanedioate)-11',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [16,18,24]triene]-7',15'-dione 13',13'-dioxide

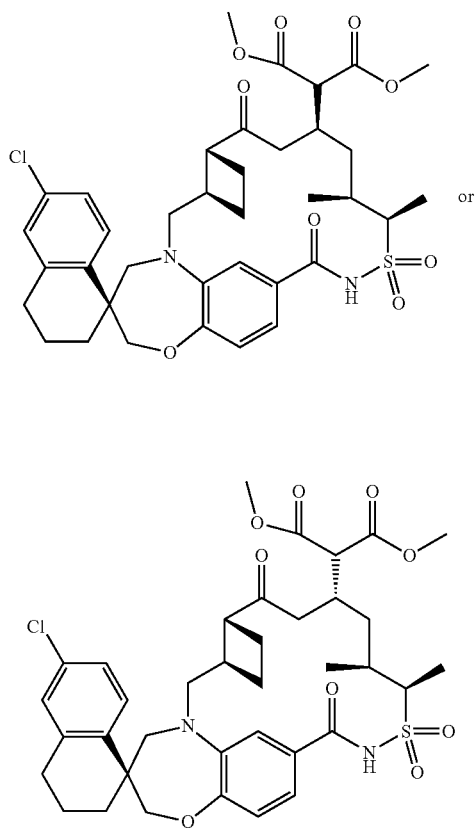 [SMILES: COC(=O)C(C(=O)OC)[C@@H]1CC(=O)[C@@H]2CC[C@H]2CN2C[C@@]3(CCCc4cc(Cl)ccc43)COc3ccc(cc32)C(=O)NS(=O)(=O)[C@H](C)[C@@H](C)C1 ; COC(=O)C(C(=O)OC)[C@H]1CC(=O)[C@@H]2CC[C@H]2CN2C[C@@]3(CCCc4cc(Cl)ccc43)COc3ccc(cc32)C(=O)NS(=O)(=O)[C@H](C)[C@@H](C)C1]

(1S,3'R,6'R,8'E,12'S)-6-chloro-12'-methyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dione 13',13'-dioxide (30 mg, 0.050 mmol, Step 1) was dissolved in THF (1.0 mL). Dimethyl malonate (0.057 mL, 0.50 mmol) and DBU (0.075 mL, 0.50 mmol) were then added and the reaction was stirred overnight. The reaction mixture was then concentrated under reduced pressure and the residue was dissolved in DMSO. The crude material was purified by reverse-phase preparative HPLC using a Phenomenex Gemini column, 10 micron, C18, 100 Å, 150×30 mm, 0.1% TFA in CH$_3$CN/H$_2$O, gradient 50% to 95% over 40 min to provide (1S,3'R,6'R,9'S,11'S,12'R)-6-chloro-9'-(dimethylpropanedioate)-11',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 13',13'-dioxide and/or (1S,3'R,6'R,9'R,11'S,12'R)-6-chloro-9'-(dimethylpropanedioate)-11',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]-triene]-7',15'-dione 13',13'-dioxide as the first eluting isomer (13 mg, 0.015 mmol, 31% yield). $^1$H NMR (400 MHz, CD$_3$OD) δ 7.75 (d, J=8.61 Hz, 1H), 7.10-7.40 (m, 3H), 6.89-7.04 (m, 1H), 6.80 (d, J=1.96 Hz, 1H), 4.09-4.30 (m, 3H), 3.57-3.90 (m, 5H), 3.04-3.43 (m, 8H), 2.51-3.08 (m, 5H), 1.78-2.44 (m, 8H), 1.47-1.71 (m, 2H), 1.45 (d, J=7.24 Hz, 3H), 1.26-1.37 (m, 2H), 0.99-1.11 (m, 3H). m/z (ESI, +ve ion) 728.7 (M+H)$^+$.

Step 3: dimethyl ((1S,3'R,6'R,7'S,9'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-9'-yl)propanedioate or dimethyl ((1S,3'R,6'R,7'S,9'S,11'R,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-9'-yl)propanedioate or dimethyl ((1S,3'R,6'R,7'S,9'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-9'-yl)propanedioate or dimethyl ((1S,3'R,6'R,7'R,9'R,10'R,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-9'-yl)propanedioate The ketone (7.0 mg, 8.30 μmol, Example 244, Step 2) was dissolved in MeOH (1.0 mL) and cooled to 0° C. Sodium borohydride (3.1 mg, 0.083 mmol) was then added and the solution was stirred for 30 minutes. The reaction was quenched by adding a few drops of 1N HCl solution and then concentrated under reduced pressure. The residue was then purified by medium pressure chromatography (silica, 20 to 60% EtOAc (+0.3% HOAc):Hexanes) to give exclusively a single isomer of the alcohol (4.3 mg, 5.9 μmol, 71% yield). $^1$H NMR (400 MHz, Solvent) δ ppm 7.77 (d, J=8.4 Hz, 1H), 7.44-7.59 (m, 1H), 7.07-7.28 (m, 3H), 6.88-7.01 (m, 1H), 4.00-4.24 (m, 4H), 3.59-3.90 (m, 9H), 3.27 (d, J=14.1 Hz, 1H), 3.06 (dd, J=15.3, 9.0 Hz, 1H), 2.71-2.90 (m, 2H), 2.39-2.63 (m, 3H), 1.49-2.19 (m, 12H), 1.41-1.47 (m, 3H), 1.23-1.34 (m, 3H), 0.98-1.07 (m, 3H). m/z (ESI, +ve ion) 730.6 (M+H)$^+$.

Example 245. dimethyl ((1S,3'R,6'R,7'S,9'S,10'S, 12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [16,18,24]trien]-9'-yl)propanedioate or dimethyl ((1S,3'R,6'R,7'S,9'S,11'R,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [16,18,24]trien]-9'-yl)propanedioate or dimethyl ((1S,3'R,6'R,7'S,9'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [16,18,24]trien]-9'-yl)propanedioate or dimethyl ((1S,3'R,6'R,7'R,9'R,11'R,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [16,18,24]trien]-9'-yl)propanedioate

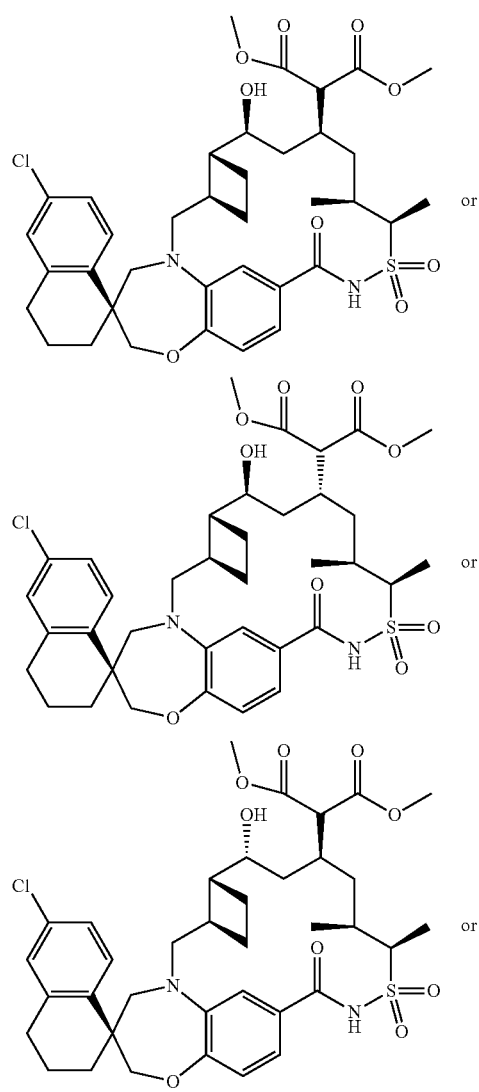

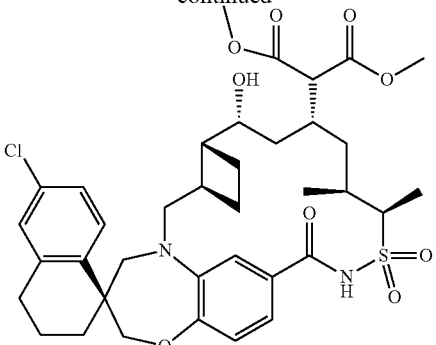

Step 1: 1S,3'R,6'R,9'S,10'S,12'R)-6-chloro-9'-(dimethylpropanedioate)-11',12'-dimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa [16,18,24]triene]-7',15'-dione 13',13'-dioxide or (1S,3'R,6'R,9'R,11'S,12'R)-6-chloro-9'-(dimethylpropanedioate)-11',12'-dimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa [16,18,24]triene]-7',15'-dione 13',13'-dioxide

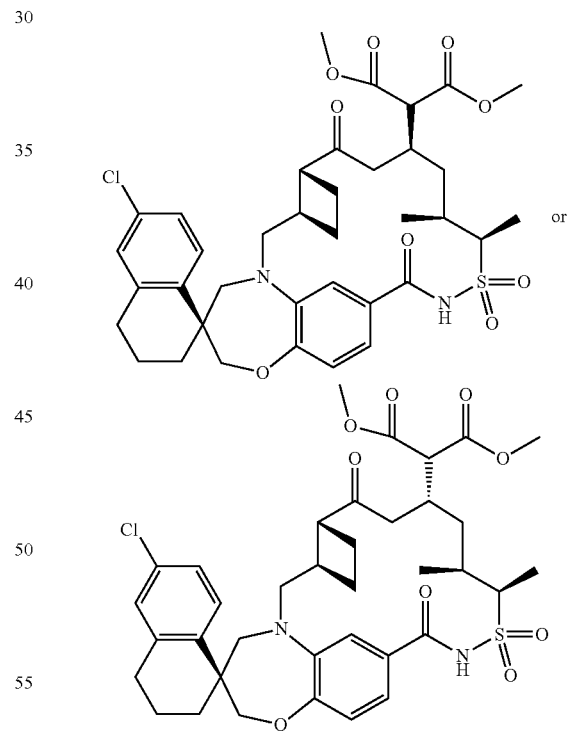

The title compound was obtained as the second eluting isomer from reverse-phase preparative HPLC using a Phenomenex Luna column, 5 micron, C18(2), 100 Å, 150×30 mm, 0.1% TFA in CH$_3$CN/H$_2$O, gradient 50% to 95% over 40 min in Example 244, Step 2 (8.5 mg, 10 μmol, 20% yield). $^1$H NMR (400 MHz, CD$_3$OD) δ 7.66-7.91 (m, 1H), 7.06-7.38 (m, 3H), 6.65-6.99 (m, 2H), 4.06-4.18 (m, 2H), 3.64-3.91 (m, 10H), 3.38-3.48 (m, 2H), 3.20-3.33 (m, 2H), 2.54-2.95 (m, 6H), 2.41 (dd, J=2.74, 19.17 Hz, 1H), 2.14-

2.27 (m, 1H), 1.97-2.13 (m, 2H), 1.71-1.96 (m, 4H), 1.44-1.61 (m, 1H), 1.30-1.43 (m, 4H), 1.19-1.29 (m, 1H), 1.08-1.16 (m, 2H). m/z (ESI, +ve ion) 728.7 (M+H)$^+$.

Step 2: dimethyl ((1S,3'R,6'R,7'S,9'S,10'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-9'-yl)propanedioate or dimethyl ((1S,3'R,6'R,7'S,9'S,10'R,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-9'-yl)propanedioate or dimethyl ((1S,3'R,6'R,7'S,9'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-9'-yl)propanedioate or dimethyl ((1S,3'R,6'R,7'R,9'R,10'R,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-9'-yl)propanedioate The ketone (8.0 mg, 9.5 µmol; from step 1) was dissolved in MeOH (1.0 mL) and cooled to 0° C. The sodium borohydride (3.6 mg, 0.095 mmol) was added and the solution was stirred for 30 minutes to completion. The reaction was quenched with a few drop of 1N HCl solution and then concentrated under reduced pressure. The residue was taken up in DMSO and filtered into a Preparative LC vial. The crude material was purified by reverse-phase preparative HPLC using a Phenomenex Gemini column, 10 micron, C18, 100 Å, 150×30 mm, 0.1% TFA in CH$_3$CN/H$_2$O, gradient 50% to 85% over 40 min to provide a 65:35 alcohol mixture of the title compound (1.3 mg, 1.5 µmol, 16% yield)). $^1$H NMR (400 MHz, MeOD) δ ppm 7.65 (d, J=8.6 Hz, 1H), 7.01-7.14 (m, 3H), 6.90 (d, J=6.5 Hz, 1H), 6.82-6.87 (m, 1H), 6.76 (d, J=2.0 Hz, 1H), 3.98-4.08 (m, 2H), 3.92 (d, J=12.1 Hz, 1H), 3.67-3.79 (m, 3H), 3.63 (d, J=2.7 Hz, 3H), 3.37-3.50 (m, 1H), 3.27-3.37 (m, 3H), 1.88-2.81 (m, 15H), 1.70-1.81 (m, 3H), 1.27-1.31 (m, 5H), 0.98-1.03 (m, 3H). m/z (ESI, +ve ion) 730.6 (M+H)$^+$.

Example 246. (1S,3'R,6'R,7'R,8'E,11'S,12'R)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The allylic alcohol (4.0 mg, 6.7 µmol, Example 208) was dissolved in THF (0.5 mL) and cooled to 0° C. To the solution was added sodium hydride (60% dispersion; 2.7 mg, 0.067 mmol) and the mixture was stirred for 30 minutes. Iodomethane (2.1 µL, 0.033 mmol) was then added and the mixture was removed from the ice bath and stirred for three hours. The reaction was then acidified with a few drops of 1N HCl solution and then diluted with water. The mixture was extracted with ethyl acetate (2×10 mL). The combined organic layers were washed with brine (1×10 mL) and dried over magnesium sulfate. The crude product was purified by medium pressure chromatography (silica, 0 to 50% EtOAc (+0.3% HOAc):Hexanes) to give (1S,3'R,6'R,7'R,8'E,11'S,12'R)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (3.3 mg, 5.4 µmol, 81% yield). $^1$H NMR (400 MHz, CHLOROFORM-d) δ ppm 8.08 (br. s., 1H), 7.72 (d, J=8.4 Hz, 1H), 7.45 (d, J=1.4 Hz, 1H), 7.19 (dd, J=8.4, 2.3 Hz, 1H), 7.09 (d, J=2.3 Hz, 1H), 6.83-6.96 (m, 2H), 5.26-5.50 (m, 2H), 4.02-4.15 (m, 3H), 3.96 (dd, J=15.5, 4.1 Hz, 1H), 3.68 (d, J=14.5 Hz, 1H), 3.16-3.24 (m, 2H), 2.95 (dd, J=15.4, 6.7 Hz, 1H), 2.69-2.87 (m, 3H), 2.52 (br. s., 2H), 2.17 (d, J=18.0 Hz, 1H), 2.11 (dd, J=4.7, 1.6 Hz, 1H), 2.03 (dd, J=15.6, 4.1 Hz, 1H), 1.85-1.99 (m, 3H), 1.77-1.84 (m, 1H), 1.64-1.77 (m, 3H), 1.45 (d, J=7.2 Hz, 3H), 1.31-1.43 (m, 3H), 1.09 (d, J=6.8 Hz, 3H). m/z (ESI, +ve ion) 612.7 (M+H)$^+$.

Example 247. (1S,3'R,6'R,7'S,9'S,10'S,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'S,11R,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11'S,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'S,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

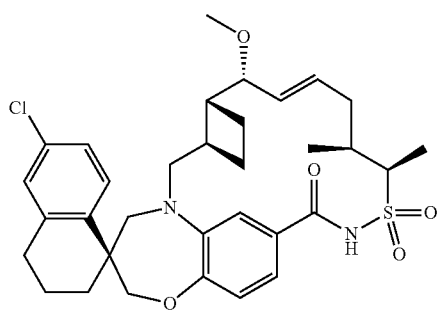 [SMILES: CO[C@@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]
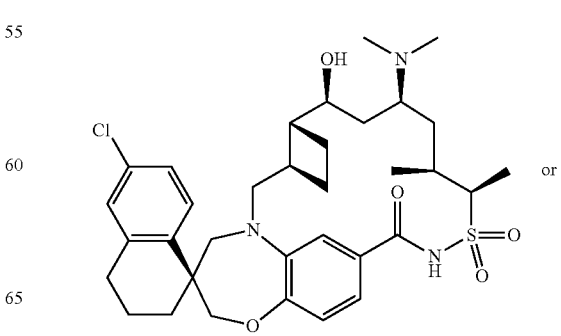

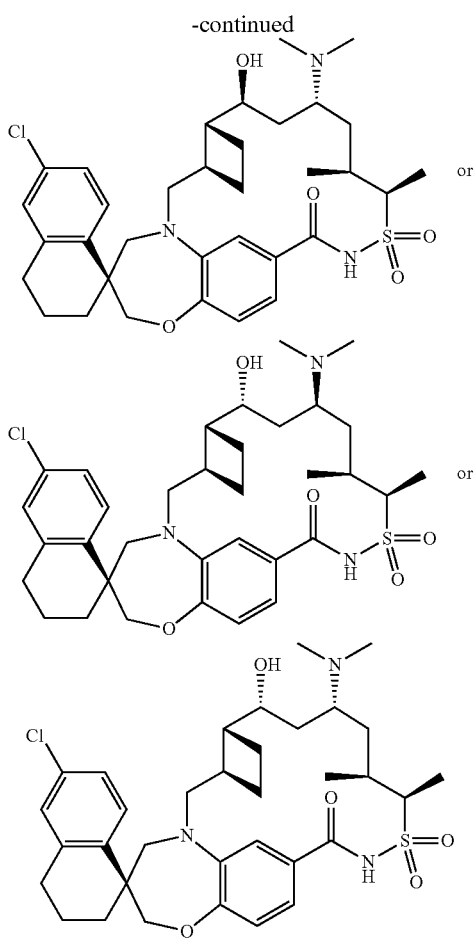

The ketone (16.5 mg, 0.019 mmol, Example 244, Step 1) bis-trifluoroacetate was dissolved in MeOH (1.5 mL) and sodium borohydride (7.2 mg, 0.190 mmol) was added. The reaction was complete after 10 minutes and the mixture was allowed to stir at room temperature over the weekend. The reaction was then concentrated and the residue was dissolved in DMSO. The crude material was purified by reverse-phase preparative HPLC using a Phenomenex Gemini column, 10 micron, C18, 100 Å, 150×30 mm, 0.1% TFA in CH$_3$CN/H$_2$O, gradient 25% to 75% over 30 min to provide (1S,3'R,6'R,7'S,9'S,11'S,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S,9'S,11'R,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]-trien]-15'-one 13',13'-dioxide or (1S,3'R,6'R,7'R,9'S,11'S,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]-trien]-15'-one 13',13'-dioxide or (1S,3'R,6'R,7'R,9'R,11'S,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide as the first eluting isomer (2.8 mg, 3.2 μmol, 17% yield). $^1$H NMR (400 MHz, MeOD) δ ppm 1.21 (s, 2H) 1.40-1.51 (m, 2H) 1.54 (d, J=7.24 Hz, 3H) 1.65-2.02 (m, 11H) 2.04-2.17 (m, 3H) 2.26-2.41 (m, 1H) 2.68-2.84 (m, 3H) 2.87 (s, 3H) 2.92 (s, 3H) 3.11 (dd, J=15.26, 9.39 Hz, 1H) 3.35-3.43 (m, 1H) 3.55 (br. s., 1H) 3.70 (d, J=14.28 Hz, 1H) 3.88 (dd, J=7.14, 3.42 Hz, 1H) 3.95-4.14 (m, 3H) 6.91-6.99 (m, 1H) 7.00-7.07 (m, 1H) 7.13 (d, J=2.15 Hz, 1H) 7.15-7.23 (m, 2H) 7.73 (d, J=8.61 Hz, 1H). m/z (ESI, +ve ion) 643.8 (M+H)$^+$.

Example 248. (1S,3'R,6'R,7'S,9'S,11'S,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S,9'S,11'R,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'S,11'S,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'R,11'S,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide

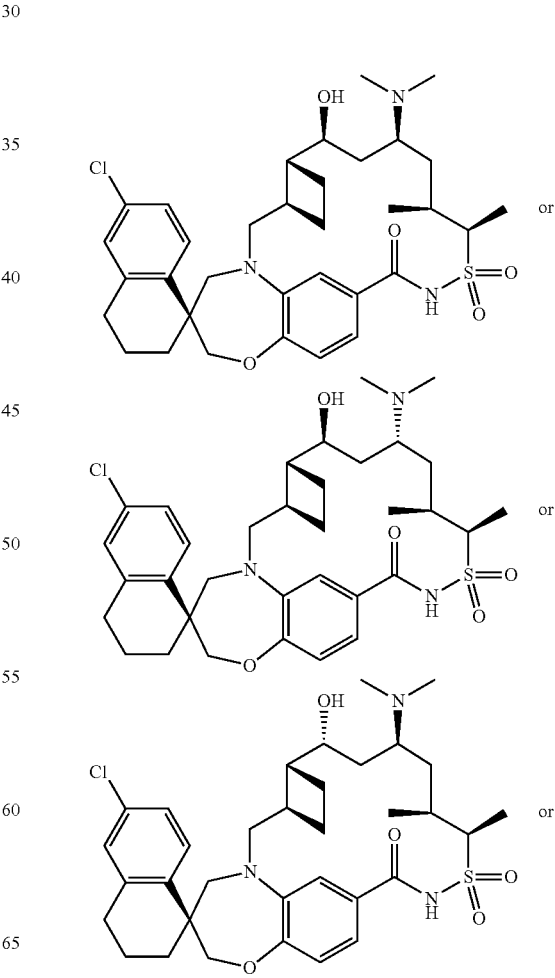

-continued

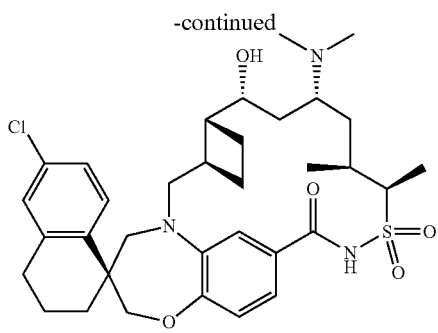

The title compound was obtained as the second eluting isomer from reverse-phase preparative HPLC using a Phenomenex Gemini column, 10 micron, C18, 100 Å, 150×30 mm, 0.1% TFA in CH$_3$CN/H$_2$O, gradient 25% to 75% over 30 min in Example 247 (6.3 mg, 7.2 μmol, 38% yield). $^1$H NMR (400 MHz, MeOD) δ ppm 7.75 (d, J=8.6 Hz, 1H), 7.35 (d, J=7.8 Hz, 1H), 7.14 (d, J=9.6 Hz, 1H), 7.10 (d, J=11.0 Hz, 2H), 6.81 (d, J=8.0 Hz, 1H), 4.58 (br. s., 1H), 4.21 (dd, J=5.8, 3.6 Hz, 1H), 3.96-4.09 (m, 2H), 3.73-3.89 (m, 2H), 3.59 (d, J=13.9 Hz, 1H), 3.25 (d, J=13.7 Hz, 1H), 3.18 (br. s., 1H), 3.04 (dd, J=14.8, 9.5 Hz, 1H), 2.66-2.88 (m, 2H), 2.46 (br. s., 6H), 2.33-2.43 (m, 1H), 2.22-2.32 (m, 1H), 1.52-2.19 (m, 11H), 1.44 (t, J=13.0 Hz, 1H), 1.37 (d, J=6.8 Hz, 3H), 1.13 (t, J=11.5 Hz, 1H), 1.05 (d, J=6.5 Hz, 3H). m/z (ESI, +ve ion) 643.8 (M+H)$^+$.

Example 249. (1S,3'R,6'R,7'S,9'S,11'S,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'S,11R,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11'S,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'S,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

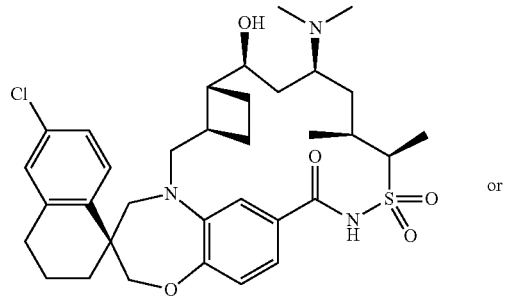

-continued

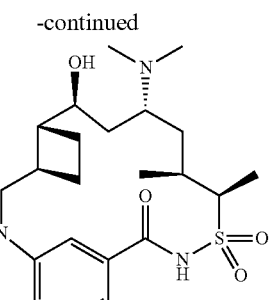

or

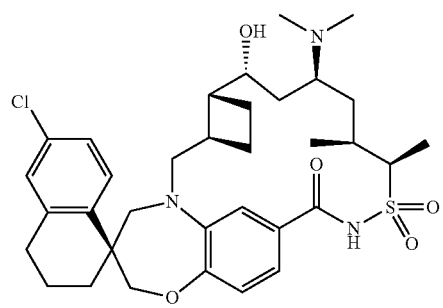

or

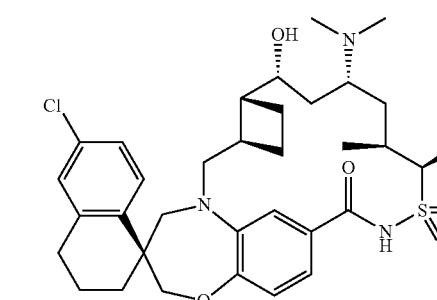

Step 1: (1S,3'R,6'R,9'S,11'S,12'R)-6-chloro-9'-(dimethylamino)-11',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [16,18,24]triene]-7',15'-dione 13',13'-dioxide and (1S,3'R,6'R,9'R,11'S,12'R)-6-chloro-9'-(dimethylamino)-11',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [16,18,24]triene]-7',15'-dione 13',13'-dioxide

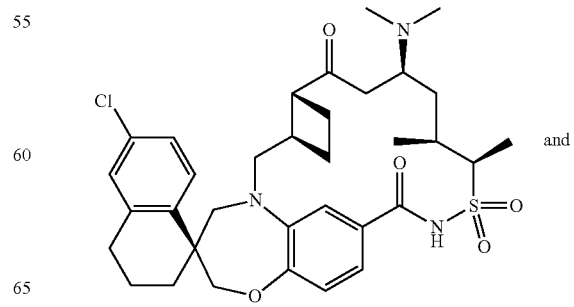

and or

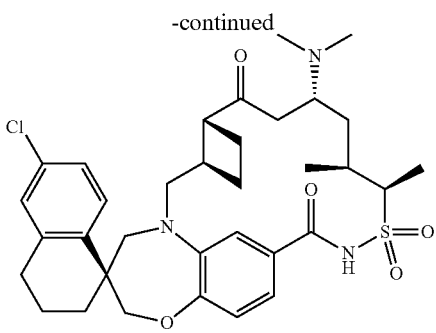

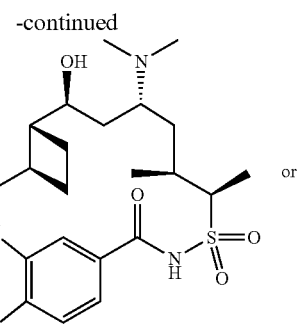

The enone (30 mg, 0.050 mmol, Example 244, Step 1) was dissolved in THF (1.00 mL) and dimethylamine (2.0 M in THF; 2.0 mL, 4.0 mmol) was added and the solution was stirred for 30 minutes. The reaction mixture was then concentrated to dryness and the residue was taken up in DMSO. The crude material was purified by reverse-phase preparative HPLC using a Phenomenex Gemini column, 10 micron, C18, 100 Å, 150×30 mm, 0.1% TFA in CH$_3$CN/H$_2$O, gradient 25% to 75% over 30 min to provide a mixture of (1S,3'R,6'R,9'S,11'S,12'R)-6-chloro-9'-(dimethylamino)-11',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]-triene]-7',15'-dione 13',13'-dioxide and (1S,3'R,6'R,9'R,11'S,12'R)-6-chloro-9'-(dimethylamino)-11',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 13',13'-dioxide (19 mg, 0.022 mmol, 44% yield). m/z (ESI, +ve ion) 641.7 (M+H)$^+$.

Step 2: (1S,3'R,6'R,7'S,9'S,11'S,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'S,11R,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'S,11'S,12'R)-6-chloro-9'-(dimethylamino)-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

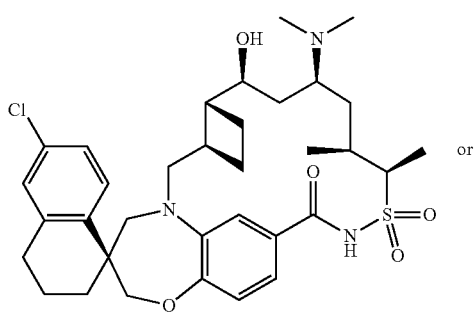

or

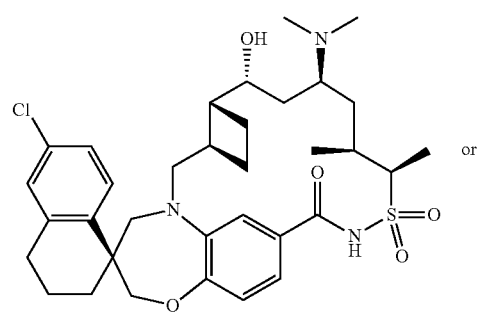

or

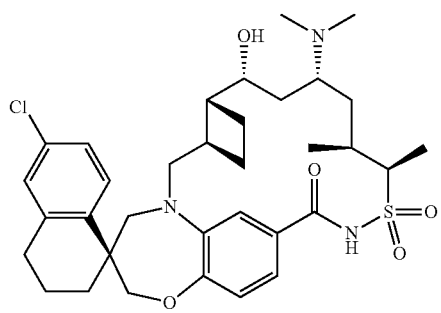

The title compound was synthesized from (1S,3'R,6'R,9'S,11'S,12'R)-6-chloro-9'-(dimethylamino)-11',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 13',13'-dioxide or (1S,3'R,6'R,9'R,11'S,12'R)-6-chloro-9'-(dimethylamino)-11',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 13',13'-dioxide (Step 1) by a procedure similar to the one described in Example 247 and it was obtained as the only eluting isomer from reverse-phase preparative HPLC using a Phenomenex Luna column, 5 micron, C18(2), 100 Å, 150×30 mm, 0.1% TFA in CH$_3$CN/H$_2$O, gradient 40% to 70% over 20 min. (3.1 mg, 3.6 µmol, 52% yield). $^1$H NMR (400 MHz, MeOD) δ ppm 1.14-1.21 (m, 6H) 1.46-1.54 (m, 5H) 1.70-1.81 (m, 4H) 1.83-2.16 (m, 5H) 2.19-2.30 (m, 3H) 2.35-2.47 (m, 2H) 2.74-2.95 (m, 6H) 3.38-3.45 (m, 1H) 3.68-3.89 (m, 4H) 3.89-3.99 (m, 1H) 4.03-4.11 (m, 1H) 4.11-4.23 (m, 2H) 6.90-7.00 (m, 1H) 7.04 (d, J=2.0 Hz, 1H) 7.06-7.16 (m, 2H) 7.16-7.27 (m, 1H) 7.70-7.82 (m, 1H). m/z (ESI, +ve ion) 643.8 (M+H)$^+$.

Example 256. (1S,3'R,6'R,7'S,9'S,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide


or


or


or

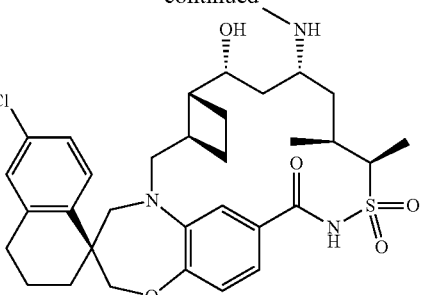

Step 1: (1S,3'R,6'R,9'S,11'S,12'R)-6-chloro-9'-(dimethylamino)-11',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [16,18,24]triene]-7',15'-dione 13',13'-dioxide and/or (1S,3'R,6'R,9'R,11'S,12'R)-6-chloro-9'-(dimethylamino)-11',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [16,18,24]triene]-7',15'-dione 13',13'-dioxide

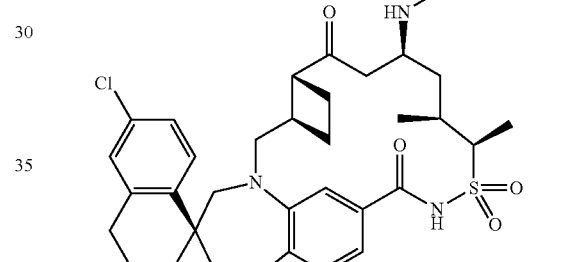

and

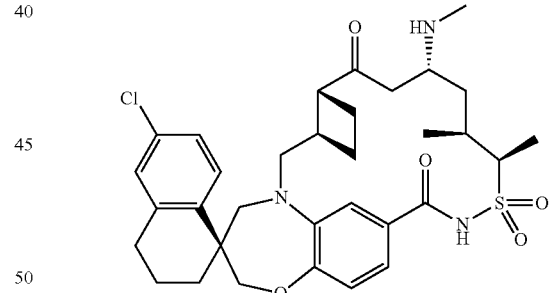

The enone (30 mg, 0.050 mmol, Example 244, Step 1) was dissolved in THF (1.0 mL). Methylamine (2.0 M in THF; 1.0 mL, 2.0 mmol) was then added and the reaction was stirred overnight. Another aliquot of methylamine (2.0M in THF; 1.0 mL, 2.0 mmol) was added to drive the reaction to completion within another 30 minutes. The reaction mixture was then concentrated under reduced pressure and the residue was dissolved in DMSO and filtered into a Preparative LC vial. The crude material was purified by reverse-phase preparative HPLC using a Phenomenex Gemini column, 10 micron, C18, 100 Å, 150×30 mm, 0.1% TFA in CH$_3$CN/H$_2$O, gradient 30% to 60% over 40 min to provide ketone (1S,3'R,6'R,9'S,11'S,12'R)-6-chloro-9'-(dimethylamino)-11',12'-dimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[16,18,24]triene]-7',15'-dione 13',13'-dioxide and (1S,3'R,6'R,9'R,11'S,12'R)-6-chloro-9'-(dimethylamino)-11',12'-dimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[16,18,24]triene]-7',15'-dione 13',13'-dioxide) as the first eluting isomer (17 mg, 0.020 mmol, 40% yield). m/z (ESI, +ve ion) 627.7 (M+H)⁺.

Step 2: (1S,3'R,6'R,7'S,9'S,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide or (1S,3'R,6'R,7'S,9'R,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide or (1S,3'R,6'R,7'R,9'S,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide or (1S,3'R,6'R,7'R,9'R,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide

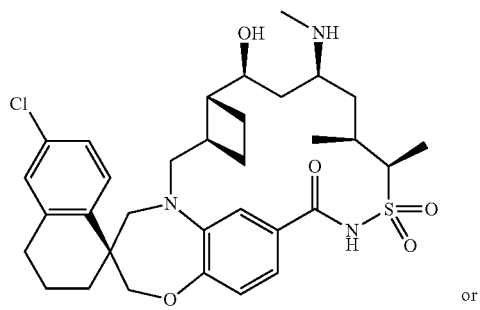

or

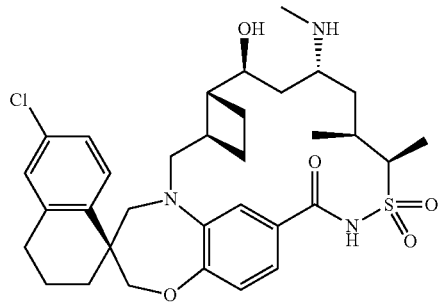

or


or

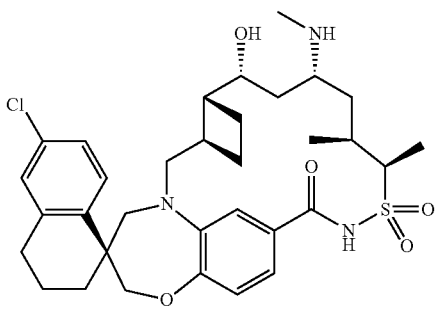

The ketone (60 mg, 0.070 mmol, Step 1) was dissolved in MeOH (2.0 mL) and cooled to 0° C. Sodium borohydride (26 mg, 0.70 mmol) was then added and the mixture was allowed to stir for 30 minutes. The reaction went from a clear solution to forming a white precipitate upon completion. The mixture was then quenched with saturated sodium bicarbonate solution and concentrated under reduced pressure and then extracted between organic (EtOAc, DCM, DCM/MeOH) and water (15 mL). It was noted that a white precipitate was never solubilized throughout the workup and was saved. The combined organic layers were dried over magnesium sulfate and concentrated. The material was purified by Preparative LC, but low recovery was observed. The white insoluble precipitate from the work up was then analyzed and determined to be the free base of the desired product. This material was then dissolved in DMSO and combined with the material collected after the first purification. The crude material was purified by reverse-phase preparative HPLC using a Phenomenex Gemini column, 10 micron, C18, 100 Å, 150×30 mm, 0.1% TFA in CH₃CN/H₂O, gradient 35% to 48% over 40 min to provide (1S,3'R,6'R,7'S,9'S,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'S,9'R,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'R,9'S,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'R,9'R,11'S,12'R)-6-chloro-7'-hydroxy-7',11',12'-trimethyl-9'-(methylamino)-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide (27 mg, 0.031 mmol, 44.9% yield). ¹H NMR (400 MHz, MeOD) δ ppm 1.15 (d, J=6.9 Hz, 2H) 1.46-1.52 (m, 3H) 1.57 (d, J=13.1 Hz, 1H) 1.63-2.18 (m, 10H) 2.23-2.49 (m, 2H) 2.69-2.91 (m, 4H) 3.05-3.21 (m, 1H) 3.23-3.36 (m, 4H) 3.40-3.54 (m, 1H) 3.62 (d, J=13.9 Hz, 1H) 3.65-3.74 (m, 1H) 3.76-3.79 (m, 1H) 3.77-3.88 (m, 1H) 3.98 (d, J=15.1 Hz, 1H) 4.02-4.17 (m, 3H) 4.20 (dd, J=11.3, 5.6 Hz, 1H) 6.94-7.03 (m, 1H) 7.05-7.15 (m, 2H) 7.17-7.26 (m, 2H) 7.73-7.78 (m, 1H). m/z (ESI, +ve ion) 629.8 (M+H)⁺.

Example 257. (1S,3'R,6'R,7'S,9'S,11'S,12'R)-6-chloro-7'-hydroxy-11',12'-dimethyl-9'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11'S,12'R)-6-chloro-7'-hydroxy-11',12'-dimethyl-9'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11'S,12'R)-6-chloro-7'-hydroxy-11',12'-dimethyl-9'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'S,12'R)-6-chloro-7'-hydroxy-11',12'-dimethyl-9'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide


or

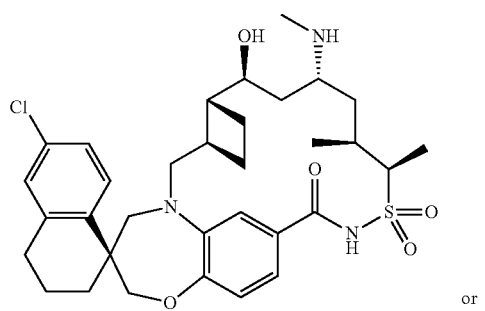

or

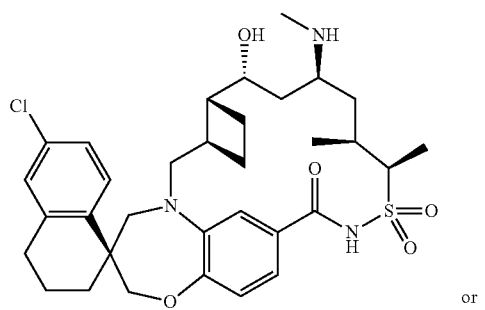

or

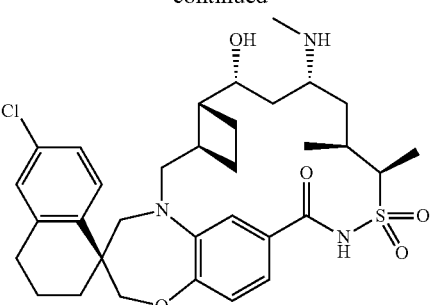

The title compound was obtained as the second eluting isomer from reverse-phase preparative HPLC using a Phenomenex Gemini column, 10 micron, C18, 100 Å, 150×30 mm, 0.1% TFA in CH$_3$CN/H$_2$O, gradient 30% to 60% over 30 min in Example 256, Step 2 (15 mg, 0.017 mmol, 74.8% yield). $^1$H NMR (400 MHz, Solvent) δ ppm 1.10-1.21 (m, 3H) 1.42-1.64 (m, 5H) 1.64-1.82 (m, 3H) 1.86-2.15 (m, 7H) 2.15-2.27 (m, 1H) 2.31-2.47 (m, 1H) 2.64-2.90 (m, 4H) 3.20 (t, J=9.7 Hz, 1H) 3.26-3.46 (m, 7H) 3.66-4.02 (m, 3H) 4.02-4.21 (m, 2H) 6.93-7.01 (m, 1H) 7.04-7.16 (m, 3H) 7.19 (dd, J=8.4, 2.2 Hz, 1H) 7.75 (d, J=8.4 Hz, 1H). m/z (ESI, +ve ion) 629.8 (M+H)$^+$.

Example 259. (1S,3'R,6'R,7'S,9'S,11'S,12'R)-6-chloro-7'-hydroxy-9',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11'S,12'R)-6-chloro-7'-hydroxy-9',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11'S,12'R)-6-chloro-7'-hydroxy-9',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'S,12'R)-6-chloro-7'-hydroxy-9',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

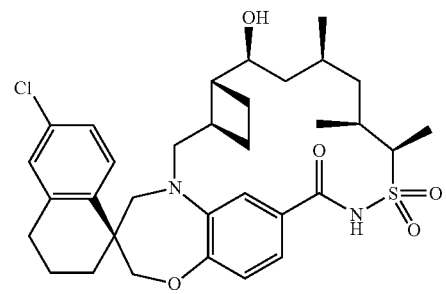

or

701

-continued

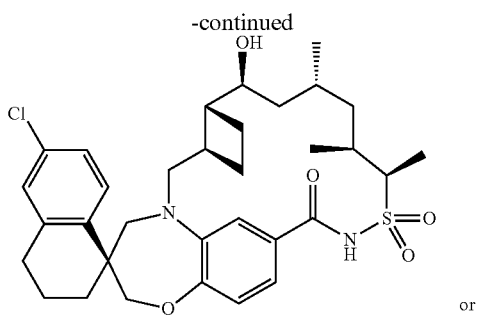

or

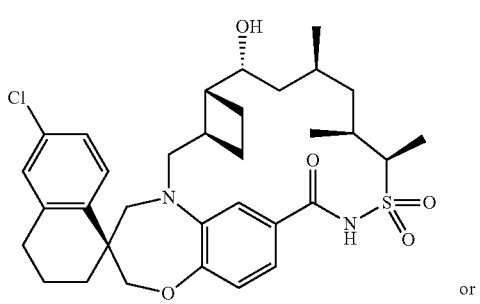

or

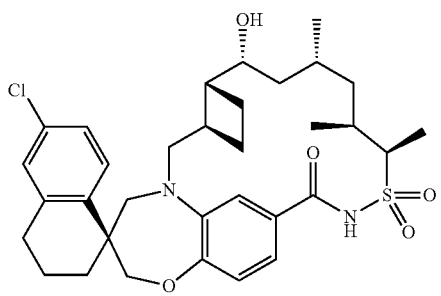

Step 1: (1S,3'R,6'R,9'S,11'S,12'R)-6-chloro-9',11', 12'-trimethyl-3,4-dihydro-2H,7'H,15'H-spiro[naphthalene-1,22'-[20]oxa[13]thia[1,14]diazatetracyclo [14.7.2.0$^{3,6}$.0$^{19,24}$]pentacosa [16,18,24]triene]-7',15'-dione 13',13'-dioxide and (1S,3'R,6'R,9'R,11'S,12'R)-6-chloro-9',11',12'-dimethyl-3,4-dihydro-2H, 7'H,15'H-spiro[naphthalene-1,22'-[20]oxa[13]thia[1, 14]diazatetracyclo[14.7.2.0$^{3,6}$.0$^{19,24}$]pentacosa [16, 18,24]triene]-7',15'-dione 13',13'-dioxide

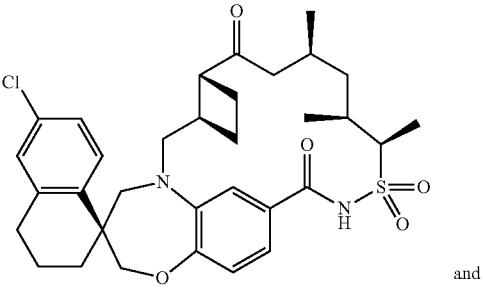

and

702

-continued

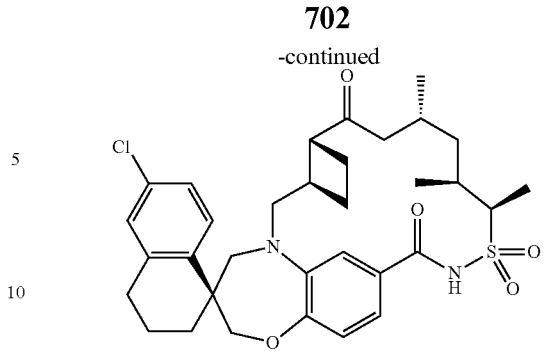

A stock solution of methyl cuprate was made by slurrying copper (I) iodide (48 μL, 1.4 mmol) in 1.0 mL of Et$_2$O and cooling to −78° C. and adding methyllithium (1.6 M solution in diethyl ether; 1.8 mL, 2.9 mmol) dropwise forming a bright yellow slurry. The mixture was stirred at −78° C. for 10 minutes. The enone (17 mg, 0.028 mmol, Example 244, Step 1) was dissolved in 1.0 mL of THF and cooled to −78° C. 0.6 mL of the cuprate stock solution was added to the THF solution and the resulting bright yellow solution was stirred at −78° C. for 30 minutes. The mixture was then warmed to 0° C. and stirred for an additional 1.5 hours. The reaction was quenched with saturated ammonium chloride and the mixture was extracted with ethyl acetate (2×30 mL). The combined organic layers were washed with brine (1×20 mL) and dried over magnesium sulfate. The crude product was purified by medium pressure chromatography (silica, 15 to 40% EtOAc (+0.3% HOAc):hexanes) to give a mixture of (1S,3'R,6'R,9'S,11'S,12'R)-6-chloro-9',11',12'-trimethyl-3,4-dihydro-2H,7'H,15'H-spiro[naphthalene-1,22'-[20]oxa[13] thia[1,14]diazatetracyclo[14.7.2.0$^{3,6}$.0$^{19,24}$]pentacosa[16, 18,24]triene]-7',15'-dione 13',13'-dioxide and (1S,3'R,6'R, 9'R,11'S,12'R)-6-chloro-9',11',12'-dimethyl-3,4-dihydro-2H, 7'H,15'H-spiro[naphthalene-1,22'-[20]oxa[13]thia[1,14] diazatetracyclo[14.7.2.0$^{3,6}$.0$^{19,24}$]pentacosa[16,18,24] triene]-7',15'-dione 13',13'-dioxide (11 mg, 0.018 mmol, 63% yield). m/z (ESI, +ve ion) 612.7 (M+H)$^+$.

Step 2: (1S,3'R,6'R,7'S,9'S,11'S,12'R)-6-chloro-7'-hydroxy-9',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24] trien]-15'-one 13',13'-dioxide or (1S,3'R,6'R,7'S,9'R, 11'S,12'R)-6-chloro-7'-hydroxy-9',11',12'-trimethyl-3,4-dihydro-2H,15'H-spiro[naphthalene-1,22'-[20] oxa[13]thia[1,14]diazatetracyclo[14.7.2.0$^{3,6}$.0$^{19,24}$] pentacosa [16,18,24]trien]-15'-one 13',13'-dioxide or (1S,3'R,6'R,7'R,9'S,11'S,12'R)-6-chloro-7'-hydroxy-9',11',12'-trimethyl-3,4-dihydro-2H,15'H-spiro [naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'S, 12'R)-6-chloro-7'-hydroxy-9',11',12'-trimethyl-3,4-dihydro-2H,15'H-spiro[naphthalene-1,22'-[20]oxa [13]thia[1,14]diazatetracyclo[14.7.2.0$^{3,6}$.0$^{19,24}$] pentacosa [16,18,24]trien]-15'-one 13',13'-dioxide (1S,3'R,6'R,9'S,11'S,12'R)-6-chloro-9',11',12'-trimethyl-3,4-dihydro-2H,7'H,15'H-spiro[naphthalene-1,22'-[20]oxa [13]thia[1,14]diazatetracyclo[14.7.2.0$^{3,6}$.0$^{19,24}$]pentacosa [16,18,24]triene]-7',15'-dione 13',13'-dioxide and (1S,3'R, 6'R,9'R,11'S,12'R)-6-chloro-9',11',12'-dimethyl-3,4-dihydro-2H,7'H,15'H-spiro[naphthalene-1,22'-[20]oxa[13] thia[1,14]diazatetracyclo[14.7.2.0$^{3,6}$.0$^{19,24}$]pentacosa[16, 18,24]triene]-7',15'-dione 13',13'-dioxide (11 mg, 0.018 mmol) was dissolved in MeOH (1.0 mL) and cooled to 0° C. Sodium borohydride (1.4 mg, 0.036 mmol) was added and the mixture was stirred for 10 minutes. LCMS showed 20% conversion. The mixture was warmed to room temperature and another aliquot of sodium borohydride (1.4 mg, 0.036 mmol) was added and stirred for 30 minutes. The reaction was then quenched with saturated ammonium chloride solution and then extracted with ethyl acetate (2×20 mL). The material was purified by reverse-phase preparative HPLC using a Phenomenex Luna column, 10 micron, C8(2), 100 Å, 150×30 mm, 0.1% TFA in CH$_3$CN/H$_2$O, gradient 20% to 70% over 40 min to provide (1S,3'R,6'R,7'S,9'S,11'S,12'R)-6-chloro-7'-hydroxy-9',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S,9'R,11'S,12'R)-6-chloro-7'-hydroxy-9',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'S,11'S,12'R)-6-chloro-7'-hydroxy-9',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'R,11'S,12'R)-6-chloro-7'-hydroxy-9',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide as the first eluting isomer (0.5 mg, 0.7 μmol, 3% yield). $^1$H NMR (400 MHz, CDCl$_3$) δ 7.62 (d, J=8.4 Hz, 1H), 6.90-7.16 (m, 2H), 6.54-6.89 (m, 3H), 3.77-3.80 (m, 4H), 3.59-3.95 (m, 5H), 2.54 (s, 2H), 2.01-2.44 (m, 6H), 1.48-1.96 (m, 15H), 0.84-1.00 (m, 4H). m/z (ESI, +ve ion) 614.8 (M+H)$^+$.

Example 260. (1S,3'R,6'R,7'S,9'S,11'S,12'R)-6-chloro-7'-hydroxy-9',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11'S,12'R)-6-chloro-7'-hydroxy-9',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'S,11'S,12'R)-6-chloro-7'-hydroxy-9',11',12'-trimethyl-3,4-dihydro-2H,15'H-spiro[naphthalene-1,22'-[20]oxa[13]thia[1,14]diazatetracyclo [16,18,24]trien]-15'-one 13',13'-dioxide or (1S,3'R,6'R,7'R,9'R,11'S,12'R)-6-chloro-7'-hydroxy-9',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

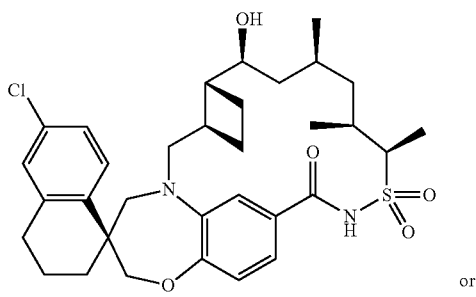

or

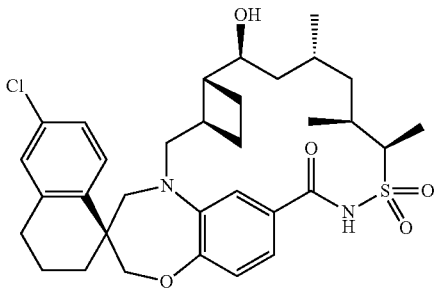

or

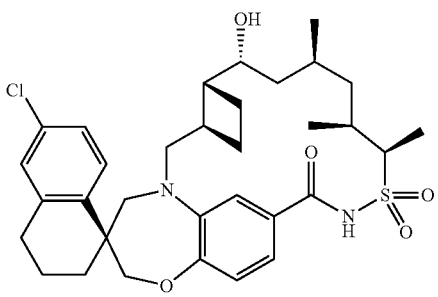

or

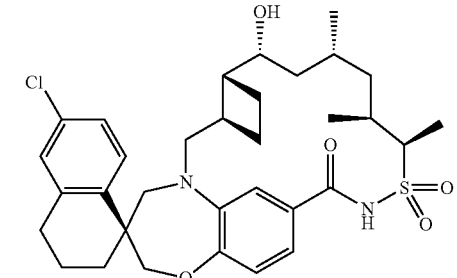

The title compound was obtained as the second pure eluting isomer (other two isomers could not be completely purified) from reverse-phase preparative HPLC using a Phenomenex Luna column, 10 micron, C18, 100 Å, 150×30 mm, 0.1% TFA in CH$_3$CN/H$_2$O, gradient 20% to 70% over 40 min in Example 259, Step 2 (0.3 mg, 0.4 μmol, 2.0% yield). $^1$H NMR (400 MHz, CD$_3$OD) δ 7.66 (d, J=8.4 Hz, 1H), 7.33 (d, J=2.2 Hz, 1H), 6.99-7.15 (m, 3H), 6.85 (d, J=8.2 Hz, 1H), 4.87 (s, 1H), 3.87-4.12 (m, 3H), 3.67 (d, J=9.8 Hz, 1H), 3.55 (d, J=13.9 Hz, 1H), 3.16 (d, J=13.7 Hz, 1H), 2.97 (dd, J=8.8, 15.3 Hz, 1H), 2.64-2.77 (m, 2H), 2.30-2.50 (m, 2H), 1.90-2.13 (m, 5H), 1.85 (s, 8H), 1.47-1.83 (m, 7H), 1.08 (t, J=11.5 Hz, 2H), 0.91-0.97 (m, 2H). m/z (ESI, +ve ion) 614.8 (M+H)$^+$.

Example 261. (1S,3'R,6'R,7'S,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

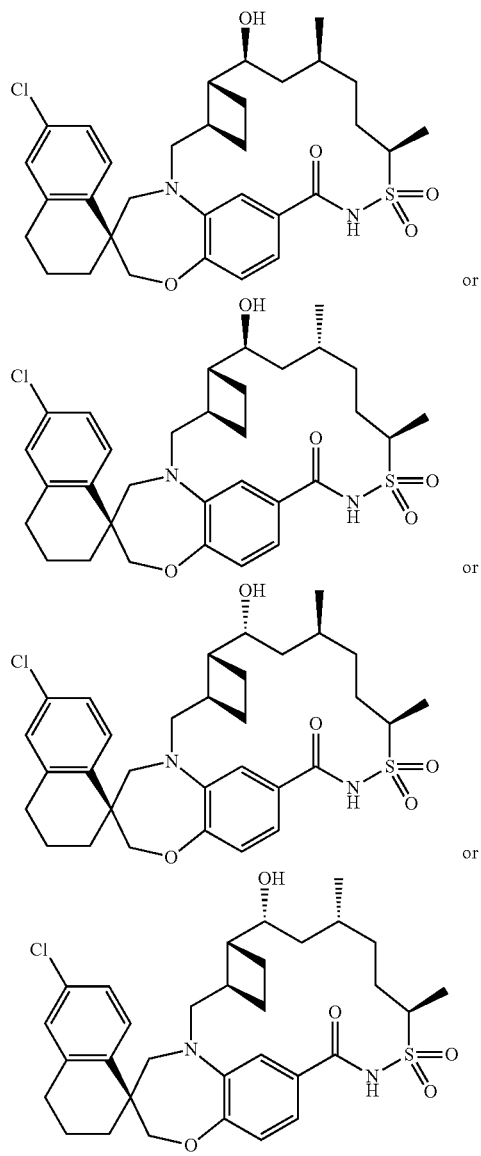

Step 1: (1S,3'R,6'R,9'S,12'R)-6-chloro-9',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [16,18,24]triene]-7',15'-dione 13',13'-dioxide and (1S,3'R,6'R,9'R,12'R)-6-chloro-9',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [16,18,24]triene]-7',15'-dione 13',13'-dioxide

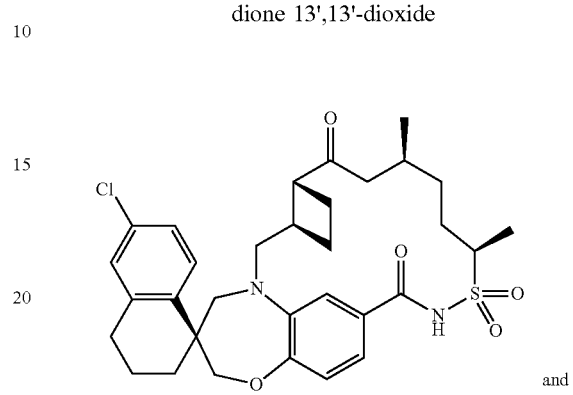

and

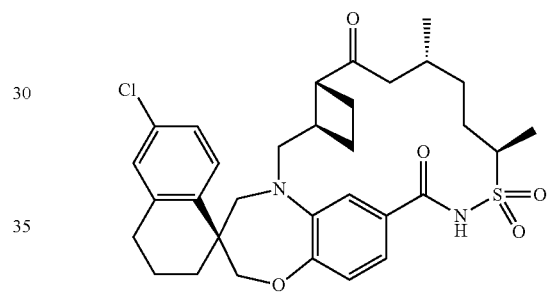

A stock solution of methyl cuprate was made by slurrying copper (I) iodide (270 mg, 1.4 mmol) in 1.0 mL of Et$_2$O and cooling to −78° C. and adding methyllithium (1.8 mL, 2.8 mmol) dropwise forming a bright yellow slurry. The mixture was stirred at −78° C. for 10 minutes. (1S,3'R,6'R,8'E,12'R)-6-chloro-12'-methyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dione 13',13'-dioxide (33 mg, 0.057 mmol, Example 604) was dissolved in 1.0 mL of THF and cooled to −78° C. 1.0 mL of the cuprate stock solution was added to the THF solution and the resulting bright yellow solution was stirred at −78° C. for 30 minutes. The reaction was quenched with saturated ammonium chloride and the mixture was extracted with ethyl acetate (2×30 mL). The combined organic layers were washed with brine (1×20 mL) and dried over magnesium sulfate. The crude product was purified by medium pressure chromatography (silica, 10 to 60% EtOAc (+0.3% HOAc):hexanes) to give a mixture of (1S,3'R,6'R,9'S,12'R)-6-chloro-9',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 13',13'-dioxide and (1S,3'R,6'R,9'R,12'R)-6-chloro-9',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 13',13'-dioxide (22 mg, 0.037 mmol, 65% yield). m/z (ESI, +ve ion) 598.8 (M+H)$^+$.

Step 2: (1S,3'R,6'R,7'S,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$] pentacosa [16,18,24]trien]-15'-one 13',13'-dioxide or (1S,3'R,6'R,7'R,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide The mixture of (1S,3'R,6'R,9'S,12'R)-6-chloro-9',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 13',13'-dioxide and (1S,3'R,6'R,9'R,12'R)-6-chloro-9',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 13',13'-dioxide (11 mg, 0.018 mmol, Step 1) was dissolved in MeOH (1.0 mL) and cooled to 0° C. Sodium borohydride (1.4 mg, 0.036 mmol) was added and the mixture was stirred for 10 minutes. LCMS showed ~20% conversion. The mixture was warmed to room temperature and another aliquot of sodium borohydride (1.4 mg, 0.036 mmol) was added and stirred for 30 minutes. The reaction was then quenched with saturated ammonium chloride solution and then extracted with ethyl acetate (2×20 mL). The material was purified by reverse-phase preparative HPLC using a Phenomenex Luna column, 10 micron, C8(2), 100 Å, 150×30 mm, 0.1% TFA in CH$_3$CN/H$_2$O, gradient 20% to 70% over 40 min to provide (1S,3'R,6'R,7'S,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide as the first eluting isomer (2.3 mg, 3.8 μmol, 10% yield). $^1$H NMR (500 MHz, CD$_3$OD) δ 7.66-7.83 (m, 1H), 7.19 (dd, J=2.2, 8.6 Hz, 1H), 7.06-7.15 (m, 2H), 7.01 (s, 1H), 6.96 (d, J=8.1 Hz, 1H), 4.05-4.16 (m, 2H), 3.90-4.00 (m, 1H), 3.75-3.90 (m, 2H), 3.64-3.75 (m, 1H), 3.25 (d, J=14.2 Hz, 2H), 2.70-2.89 (m, 2H), 2.27-2.40 (m, 1H), 2.16-2.25 (m, 1H), 1.99-2.16 (m, 3H), 1.93-1.99 (m, 2H), 1.56-1.91 (m, 6H), 1.44-1.53 (m, 3H), 1.25-1.44 (m, 5H), 0.95-1.02 (m, 3H). m/z (ESI, +ve ion) 600.7 (M+H)$^+$.

Example 262. (1S,3'R,6'R,7'S,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

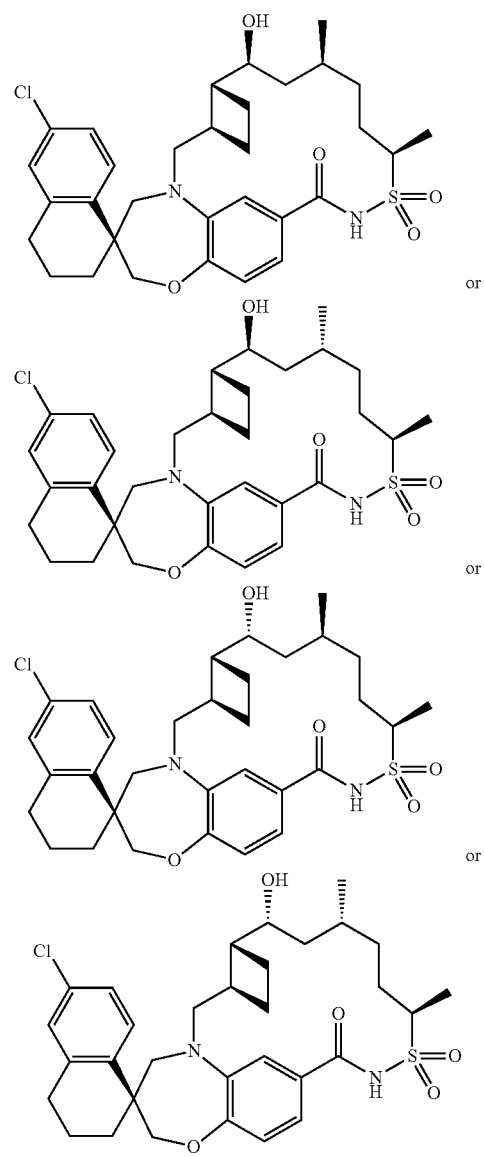

The title compound was obtained as the second eluting isomer from reverse-phase preparative HPLC using a Phenomenex Luna column, 10 micron, C18, 100 Å, 150×30 mm, 0.1% TFA in CH$_3$CN/H$_2$O, gradient 20% to 70% over 40 min in Example 261, Step 2 (13 mg, 21 μmol, 57% yield). $^1$H NMR (500 MHz, CDCl$_3$) δ 9.94-10.20 (m, 1H), 7.67 (s, 1H), 7.59-7.69 (m, 1H), 7.33-7.40 (m, 1H), 7.10 (dd, J=2.32, 8.44 Hz, 1H), 6.98-7.06 (m, 1H), 6.85-6.89 (m, 1H), 3.93-4.05 (m, 3H), 3.41-3.68 (m, 3H), 2.99-3.19 (m, 2H), 2.61-2.84 (m, 3H), 2.43-2.56 (m, 1H), 1.90-2.04 (m, 4H), 1.64-1.90 (m, 8H), 1.06-1.31 (m, 9H). m/z (ESI, +ve ion) 600.7 (M+H)$^+$.

Example 263. (1S,3'R,6'R,7'S,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

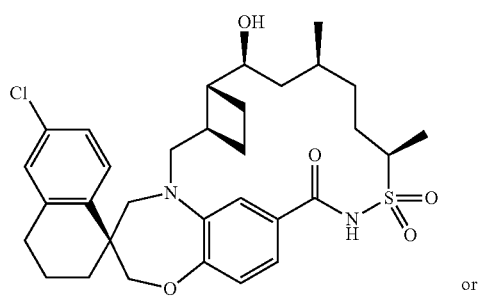

or

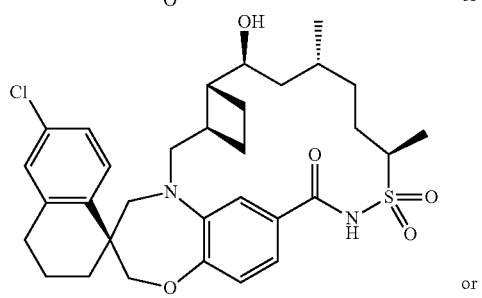

or

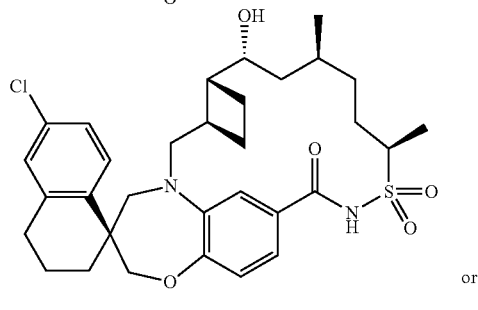

or

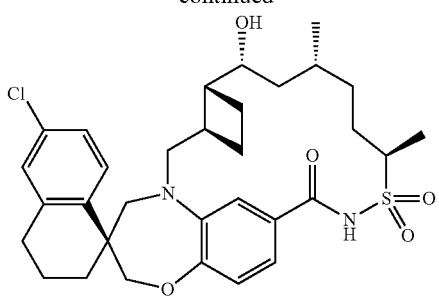

The title compound was obtained as the third eluting isomer from reverse-phase preparative HPLC using a Phenomenex Luna column, 10 micron, C18, 100 Å, 150×30 mm, 0.1% TFA in CH$_3$CN/H$_2$O, gradient 20% to 70% over 40 min in Example 261, Step 2 (1.1 mg, 1.5 μmol, 4.2% yield). $^1$H NMR (400 MHz, CDCl$_3$) δ 7.69-7.79 (m, 1H), 7.42 (d, J=2.0 Hz, 1H), 7.20 (dd, J=2.3, 8.5 Hz, 1H), 7.11 (d, J=2.4 Hz, 1H), 7.00-7.08 (m, 1H), 6.95 (d, J=8.2 Hz, 1H), 4.08-4.19 (m, 3H), 4.02 (d, J=15.3 Hz, 1H), 3.82 (dd, J=3.8, 10.1 Hz, 1H), 3.68 (d, J=14.3 Hz, 1H), 3.20 (d, J=14.1 Hz, 1H), 3.05 (dd, J=8.6, 15.3 Hz, 1H), 2.66-2.86 (m, 2H), 2.37-2.59 (m, 2H), 2.12 (s, 1H), 1.58-2.09 (m, 10H), 1.52-1.58 (m, 4H), 1.37-1.47 (m, 2H), 1.26-1.34 (m, 2H), 1.10-1.21 (m, 1H), 0.92-0.98 (m, 3H). m/z (ESI, +ve ion) 600.7 (M+H)$^+$.

Example 264. (1S,3'R,6'R,7'S,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

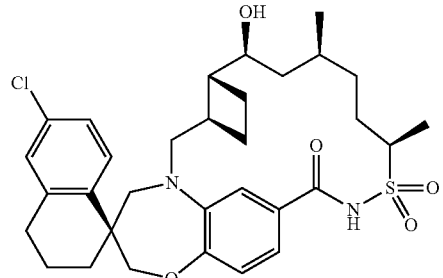

or

-continued

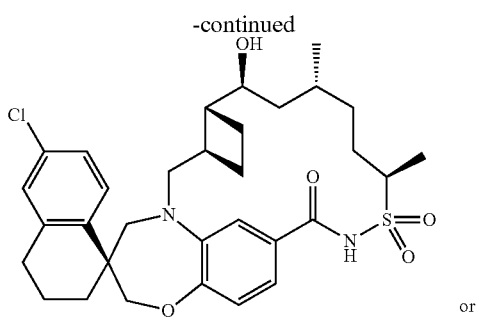

or

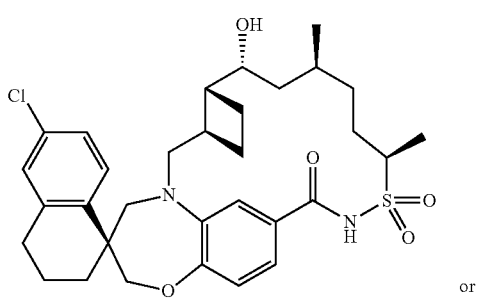

or

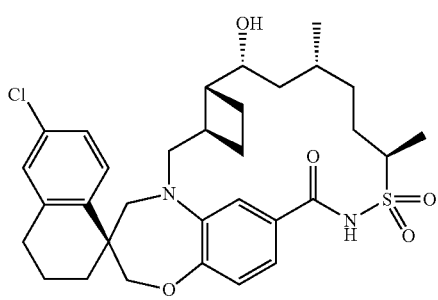

The title compound was obtained as the fourth eluting isomer from reverse-phase preparative HPLC using a Phenomenex Luna column, 10 micron, C18, 100 Å, 150×30 mm, 0.1% TFA in CH$_3$CN/H$_2$O, gradient 20% to 70% over 40 min in Example 261, Step 2 (2.0 mg, 2.8 µmol, 7.6% yield). $^1$H NMR (500 MHz, CD$_3$OD) δ 7.69-7.85 (m, 1H), 7.06-7.28 (m, 2H), 6.82-7.06 (m, 3H), 4.03-4.23 (m, 2H), 3.36-3.87 (m, 5H), 3.11-3.25 (m, 1H), 2.72-2.92 (m, 3H), 1.85-2.21 (m, 9H), 1.58-1.85 (m, 5H), 1.44-1.58 (m, 3H), 1.17-1.41 (m, 6H). m/z (ESI, +ve ion) 600.7 (M+H)$^+$.

Example 265. (1S,3'R,6'R,7'S,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

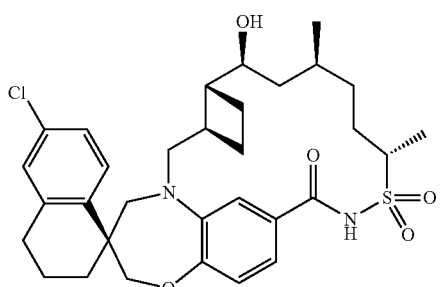

or

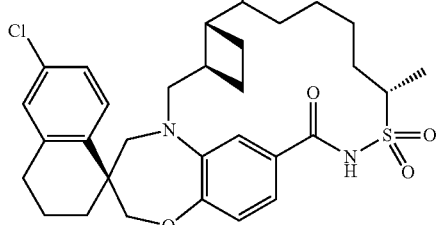

or

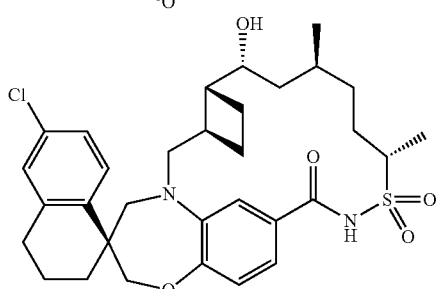

or

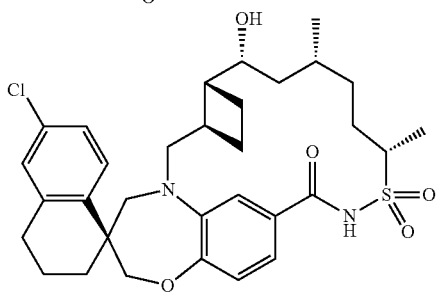

713

Step 1: (1S,3'R,6'R,8'E,12'S)-6-chloro-12'-methyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[8,16,18,24]tetraene]-7',15'-dione 13',13'-dioxide

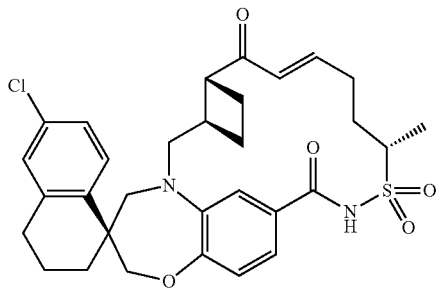 [SMILES: C[C@H]1CC/C=C/C(=O)[C@@H]2CC[C@H]2CN2C[C@@]3(CCCc4cc(Cl)ccc43)COc3ccc(cc32)C(=O)NS1(=O)=O]

(1S,3'R,6'R,7'R,8'E,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (67 mg, 0.12 mmol, Example 995) was dissolved in DCM (2.0 ml) and cooled to 0° C. Dess-Martin periodinane (97 mg, 0.23 mmol) was added and the reaction mixture was stirred for 45 minutes. The reaction was then diluted with dichloromethane (25 mL) and then quenched with saturated Na$_2$S$_2$O$_3$ (15 mL). The layers were separated and the aqueous layer was extracted with dichloromethane (1×25 mL). The combined organic layers were then dried over magnesium sulfate. The crude product was purified by medium pressure chromatography (silica, 20 to 100% EtOAc (+0.3% HOAc):hexanes) to give (1S,3'R,6'R,8'E,12'S)-6-chloro-12'-methyl-3,4-dihydro-2h,7'h,15'h-spiro[naphthalene-1,22'-[20]oxa[13]thia[1,14]diazatetracyclo[14.7.2.0³,⁶.0¹⁹,²⁴]pentacosa[8,16,18,24]tetraene]-7',15'-dione 13',13'-dioxide (39 mg, 0.067 mmol, 58% yield) that was used in the next reaction. m/z (ESI, +ve ion) 582.7 (M+H)⁺.

Step 2: (1S,3'R,6'R,9'S,12'S)-6-chloro-9',12'-dimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa [16,18,24]triene]-7',15'-dione 13',13'-dioxide and (1S,3'R,6'R,9'R,12'S)-6-chloro-9',12'-dimethyl-3,4-dihydro-2H,7'H,15'H-spiro[naphthalene-1,22'-[20]oxa[13]thia[1,14]diazatetracyclo [14.7.2.0³,⁶.0¹⁹,²⁴]pentacosa [16,18,24]triene]-7',15'-dione 13',13'-dioxide

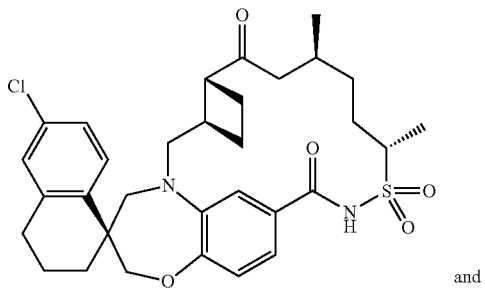

and

714

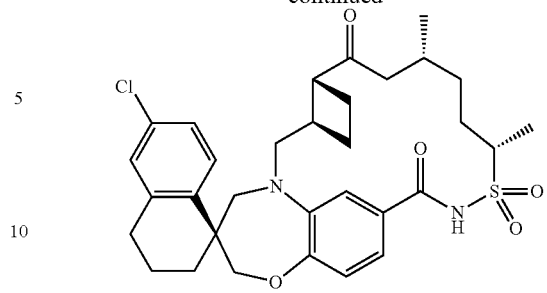

A stock solution of 3 mmol of Cu(LiMe)$_2$ in 5 mL of solvent (~0.6M solution) was formed at −78° C. In a separate flask the enone (5.0 mg, 8.6 µmol, Step 1) was dissolved in 0.5 mL of THF and cooled to 0° C. 0.5 mL of the cuprate stock solution was added and the reaction mixture was stirred at 0° C. for 30 minutes. The reaction was then quenched with saturated ammonium chloride solution and extracted with ethyl acetate (2×20 mL). The combined organic layers were washed with brine and dried over magnesium sulfate. The crude product was then purified by medium pressure chromatography (silica, 20 to 60% EtOAc (+0.3% HOAc):hexanes) to give a mixture of (1S,3'R,6'R,9'S,12'S)-6-chloro-9',12'-dimethyl-3,4-dihydro-2H,7'H,15'H-spiro [naphthalene-1,22'-[20]oxa[13]thia[1,14]diazatetracyclo[14.7.2.0³,⁶.0¹⁹,²⁴]pentacosa[16,18,24]triene]-7',15'-dione 13',13'-dioxide and (1S,3'R,6'R,9'R,12'S)-6-chloro-9',12'-dimethyl-3,4-dihydro-2H,7'H,15'H-spiro [naphthalene-1,22'-[20]oxa[13]thia[1,14]diazatetracyclo [14.7.2.0³,⁶.0¹⁹,²⁴]pentacosa[16,18,24]triene]-7',15'-dione 13',13'-dioxide (3.2 mg, 6.3 µmol, 64% yield). m/z (ESI, +ve ion) 598.8 (M+H)⁺.

Step 3: (1S,3'R,6'R,7'S,9'S,12'R)-6-chloro-7'-hydroxy-9',12'-dimethyl-3,4-dihydro-2H,15'H-spiro [naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide or (1S,3'R,6'R,7'S,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide or (1S,3'R,6'R,7'R,9'S,12'R)-6-chloro-7'-hydroxy-9',12'-dimethyl-3,4-dihydro-2H,15'H-spiro[naphthalene-1,22'-[20]oxa [13]thia[1,14]diazatetracyclo[14.7.2.0³,⁶.0¹⁹,²⁴] pentacosa [16,18,24]trien]-15'-one 13',13'-dioxide or (1S,3'R,6'R,7'R,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo [14.7.2.0³,⁶.0¹⁹,²⁴]pentacosa [16,18,24]trien]-15'-one 13',13'-dioxide A mixture of (1S,3'R,6'R,9'S,12'S)-6-chloro-9',12'-dimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[16,18,24]triene]-7',15'-dione 13',13'-dioxide and (1S,3'R,6'R,9'R,12'S)-6-chloro-9',12'-dimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[16,18,24]triene]-7',15'-dione 13',13'-dioxide (16 mg, 0.027 mmol; Step 2) was dissolved in MeOH (1.0 mL) and sodium borohydride (10 mg, 0.27 mmol) was added (or enough to drive the reaction to completion). The reaction mixture was concentrated to dryness and then diluted with ethyl acetate and 1N HCl soln. (5 mL). The mixture was extracted with ethyl acetate (2×10 mL) and the combined organic layers were washed with brine (1×10 mL) and dried over magnesium sulfate. The crude product was purified by medium pressure chromatography (silica, 10-60% EtOAc (+0.3% HOAc):Hexanes) to give the title compound as the first eluting isomer (0.2 mg, 0.3 μmol, 1.2% yield). $^1$H NMR (500 MHz, CD$_3$OD) δ 7.70-7.86 (m, 1H), 7.07-7.37 (m, 3H), 6.88-6.99 (m, 1H), 5.68-5.94 (m, 1H), 4.97-5.20 (m, 2H), 4.00-4.20 (m, 2H), 3.43-3.85 (m, 4H), 2.58-3.06 (m, 3H), 1.76-2.35 (m, 10H), 1.41-1.76 (m, 6H), 1.33-1.41 (m, 3H), 0.90-1.03 (m, 4H). m/z (ESI, +ve ion) 600.8 (M+H)$^+$.

Example 266. (1S,3'R,6'R,7'S,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

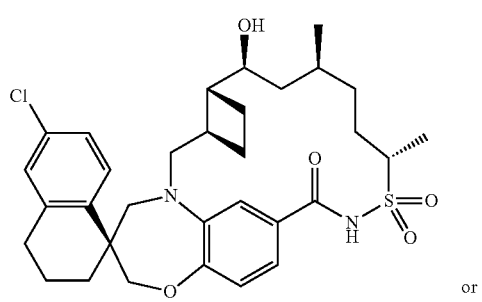

or

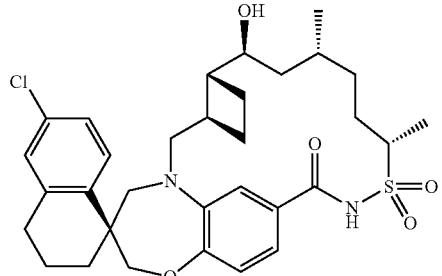

or

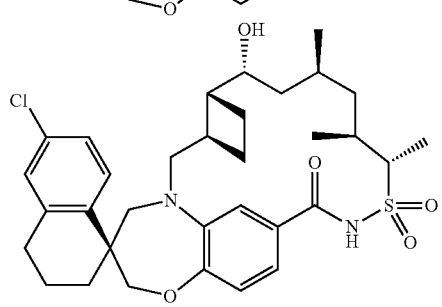

or

-continued

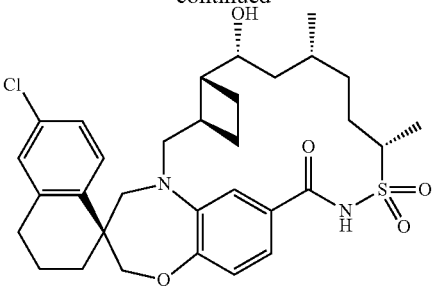

The title compound was synthesized as described in example 265, step 3 and was obtained as the second eluting isomer (6.0 mg, 10.0 μmol, 37% yield). $^1$H NMR (400 MHz, CD$_3$OD) δ 7.67-7.87 (m, 1H), 7.11-7.25 (m, 2H), 7.05-7.42 (m, 2H), 6.88-7.03 (m, 1H), 3.97-4.25 (m, 3H), 3.71-3.85 (m, 1H), 3.41-3.71 (m, 2H), 3.24-3.41 (m, 5H), 3.15 (dd, J=7.6, 15.4 Hz, 1H), 2.68-2.98 (m, 2H), 2.45-2.65 (m, 1H), 2.19-2.45 (m, 1H), 2.08-2.19 (m, 2H), 1.99-2.08 (m, 2H), 1.61-1.99 (m, 8H), 1.41-1.61 (m, 6H). m/z (ESI, +ve ion) 600.8 (M+H)$^+$.

Example 267. (1S,3'R,6'R,7'S,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,12'R)-6-chloro-7'-hydroxy-9',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

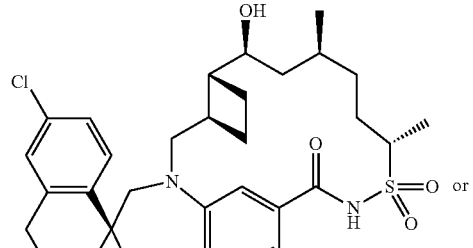 or

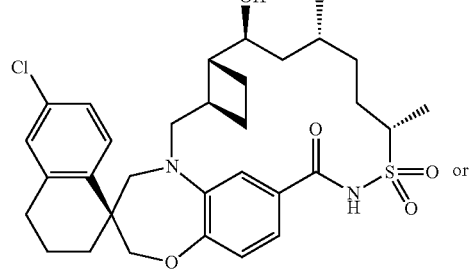 or

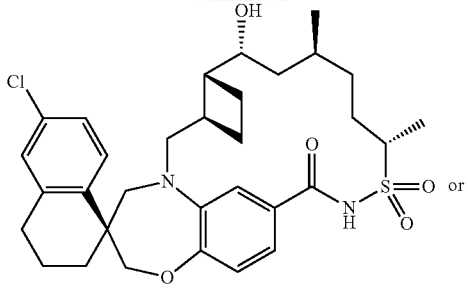

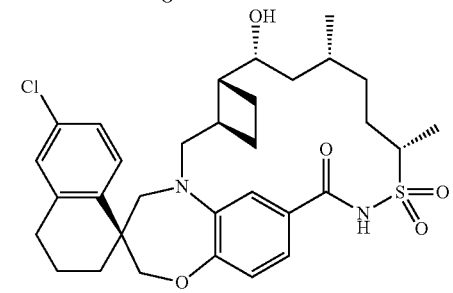

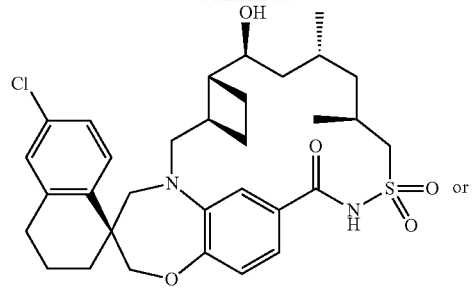

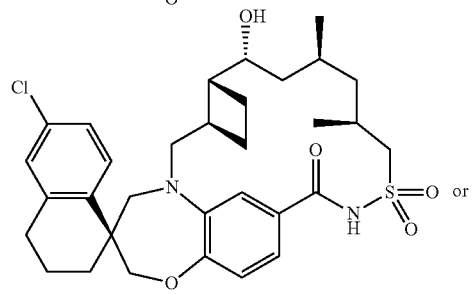

The title compound was synthesized as described in Example 265, Step 3 and was obtained as the third eluting isomer (2.0 mg, 3.3 μmol, 13% yield). $^1$H NMR (400 MHz, CD$_3$OD) δ 7.70-7.88 (m, 1H), 7.09-7.33 (m, 3H), 6.82-7.04 (m, 2H), 4.60 (br. s., 1H), 3.97-4.26 (m, 3H), 3.62-3.87 (m, 3H), 3.14 (dd, J=9.7, 15.4 Hz, 1H), 2.67-2.96 (m, 2H), 1.65-2.47 (m, 11H), 1.24-1.54 (m, 9H), 0.97-1.06 (m, 3H), 0.86-0.89 (m, 1H). m/z (ESI, +ve ion) 600.8 (M+H)$^+$.

Example 268. (1S,3'R,6'R,7'S,9'S,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide Step 1: (1S,3'R,6'R,8'E,11'S)-6-chloro-12'-methyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [8,16,18,24]tetraene]-7',15'-dione 13',13'-dioxide

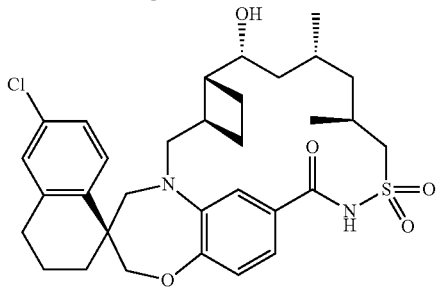

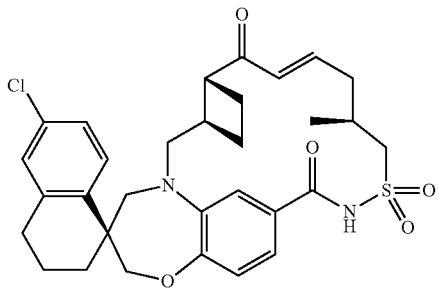 [SMILES: C[C@H]1C/C=C/C(=O)[C@@H]2CC[C@H]2CN2C[C@@]3(CCCc4cc(Cl)ccc43)COc3ccc(cc32)C(=O)NS(=O)(=O)C1]

(1S,3'R,6'R,7'R,8'E,11'S)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (53 mg, 0.091 mmol, Example 231) was dissolved in DCM (2.0 ml) and cooled to 0° C. Dess-Martin periodinane (77 mg, 0.18 mmol) was added and the reaction mixture was stirred for 45 minutes. The reaction was then diluted with dichloromethane (25 mL) and then quenched with saturated Na$_2$S$_2$O$_3$ (15 mL). The layers were separated and the aqueous layer was extracted with dichloromethane (1×25 mL). The combined

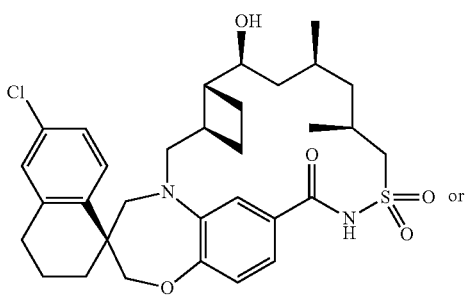

organic layers were then dried over magnesium sulfate. The crude product was purified by medium pressure chromatography (silica, 20 to 100% EtOAc (+0.3% HOAc):hexanes) to give (1S,3'R,6'R,8'E,11'S)-6-chloro-12'-methyl-3,4-dihydro-2h,7'h,15'h-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dione 13',13'-dioxide (32 mg, 0.055 mmol, 61% yield) that was used in the next reaction. m/z (ESI, +ve ion) 582.7 (M+H)$^+$.

Step 2: (1S,3'R,6'R,9'S,11'S)-6-chloro-9',11'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [16,18,24]triene]-7',15'-dione 13',13'-dioxide and (1S,3'R,6'R,9'R,11'S)-6-chloro-9',11'-dimethyl-3,4-dihydro-2H,7'H,15'H-spiro[naphthalene-1,22'-[20]oxa[13]thia[1,14]diazatetracyclo [14.7.2.0$^{3,6}$.0$^{19,24}$]pentacosa [16,18,24]triene]-7',15'-dione 13',13'-dioxide

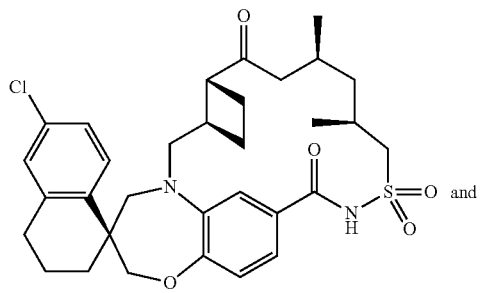

and

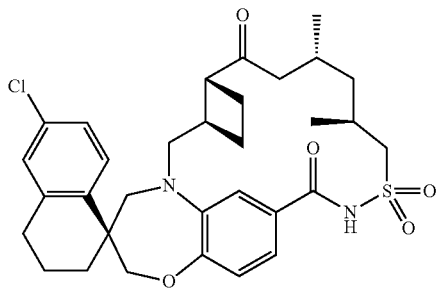

A stock solution of the methyl cuprate solution was made by slurrying copper (I) iodide (270 mg, 1.4 mmol) in 1.0 mL of Et$_2$O and cooling to −78° C. and adding methyllithium (1.8 mL, 2.8 mmol) dropwise forming a bright yellow slurry. The mixture was stirred at −78° C. for 10 minutes. The enone (33 mg, 0.057 mmol, Step 1) was dissolved in 1.0 mL of THF and cooled to −78° C. 1.0 mL of the cuprate stock solution was added to the THF solution and the resulting bright yellow solution was stirred at −78° C. for 30 minutes. The reaction was quenched with saturated ammonium chloride and the mixture was extracted with ethyl acetate (2×30 mL). The combined organic layers were washed with brine (1×20 mL) and dried over magnesium sulfate. The crude product was purified by medium pressure chromatography (silica, 10 to 60% EtOAc (+0.3% HOAc):Hexanes) to give a mixture of (1S,3'R,6'R,9'S,11'S)-6-chloro-9',11'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [16,18,24]triene]-7',15'-dione 13',13'-dioxide and (1S,3'R,6'R,9'R,11'S)-6-chloro-9',11'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 13',13'-dioxide. m/z (ESI, +ve ion) 598.8 (M+H)$^+$.

Step 3: (1S,3'R,6'R,7'S,9'S,1 VS)-6-chloro-7'-hydroxy-9',11'-dimethyl-3,4-dihydro-2H,15'H-spiro [naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$] pentacosa [16,18,24]trien]-15'-one 13',13'-dioxide or (1S,3'R,6'R,7'R,9'R,11'S)-6-chloro-7'-hydroxy-9',11'-dimethyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa [16,18,24]trien]-15'-one 13',13'-dioxide The mixture of ketones (25 mg, 0.042 mmol, Step 2) was dissolved in MeOH (2.0 mL) and sodium borohydride (16 mg, 0.42 mmol) was added and stirred for 30 minutes. (More NaBH$_4$ was added as needed to push the reaction to completion). The reaction mixture was then concentrated and extracted between EtOAc (2×20 mL) and 1N HCl (10 mL). The combined organic layers were washed with brine (1×10 mL) and dried over magnesium sulfate. The filtrate was concentrated and the residue was purified by medium pressure chromatography (silica, 20 to 75% EtOAc (+0.3% HOAc):hexanes) to give (1S,3'R,6'R,7'S,9'S,11'S)-6-chloro-7'-hydroxy-9',11'-dimethyl-3,4-dihydro-2H,15'H-spiro [naphthalene-1,22'-[20]oxa[13]thia[1,14]diazatetracyclo [14.7.2.0$^{3,6}$.0$^{19,24}$]pentacosa[16,18,24]trien]-15'-one 13',13'-dioxide or (1S,3'R,6'R,7'S,9'R,11'S)-6-chloro-7'-hydroxy-9',11'-dimethyl-3,4-dihydro-2H,15'H-spiro [naphthalene-1,22'-[20]oxa[13]thia[1,14]diazatetracyclo [14.7.2.0$^{3,6}$.0$^{19,24}$]pentacosa[16,18,24]trien]-15'-one 13',13'-dioxide or (1S,3'R,6'R,7'R,9'S,11'S)-6-chloro-7'-hydroxy-9',11'-dimethyl-3,4-dihydro-2H,15'H-spiro [naphthalene-1,22'-[20]oxa[13]thia[1,14]diazatetracyclo [14.7.2.0$^{3,6}$.0$^{19,24}$]pentacosa[16,18,24]trien]-15'-one 13',13'-dioxide or (1S,3'R,6'R,7'R,9'R,11'S)-6-chloro-7'-hydroxy-9',11'-dimethyl-3,4-dihydro-2H,15'H-spiro [naphthalene-1,22'-[20]oxa[13]thia[1,14]diazatetracyclo [14.7.2.0$^{3,6}$.0$^{19,24}$]pentacosa[16,18,24]trien]-15'-one 13',13'-dioxide (2.4 mg, 4.00 µmol, 9.6% yield) as the first eluting isomer. $^1$H NMR (500 MHz, CDCl$_3$) δ 10.41 (br. s., 1H), 7.56-7.74 (m, 1H), 7.34-7.50 (m, 1H), 7.23-7.31 (m, 1H), 6.82-7.10 (m, 3H), 3.90-4.06 (m, 2H), 3.46-3.79 (m, 2H), 2.94-3.17 (m, 3H), 2.58-2.70 (m, 2H), 2.15-2.53 (m, 3H), 1.74-2.10 (m, 6H), 1.22-1.41 (m, 7H), 0.82-1.04 (m, 9H). m/z (ESI, +ve ion) 600.8 (M+H)$^+$.

Example 269. (1S,3'R,6'R,7'S,9'S,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

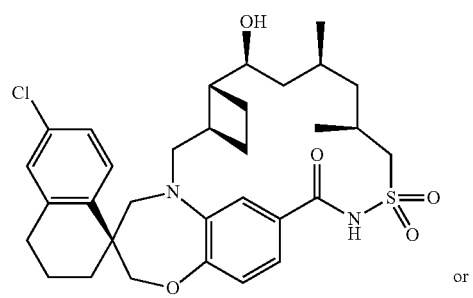

or


or


or


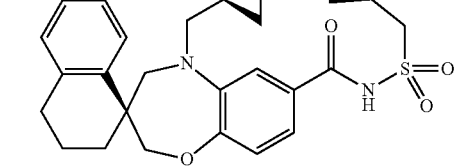

The title compound was obtained as the second eluting isomer using medium pressure chromatography (silica, 20 to 75% EtOAc (+0.3% HOAc):Hexanes) in Example 268, Step 3 (1.5 mg, 2.5 μmol, 6.0% yield). $^1$H NMR (500 MHz, CDCl$_3$) δ 9.75 (s, 1H), 7.58-7.75 (m, 1H), 7.37-7.53 (m, 1H), 6.80-7.17 (m, 4H), 3.90-4.11 (m, 3H), 3.47-3.82 (m, 3H), 2.91-3.24 (m, 3H), 2.59-2.78 (m, 2H), 2.07-2.48 (m, 3H), 2.04-2.07 (m, 1H), 1.60-2.01 (m, 6H), 1.19-1.39 (m, 7H), 0.87-1.01 (m, 6H). m/z (ESI, +ve ion) 600.8 (M+H)$^+$.

Example 270. (1S,3'R,6'R,7'S,9'S,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

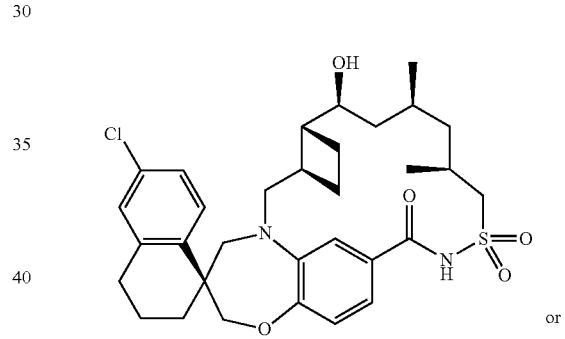

or

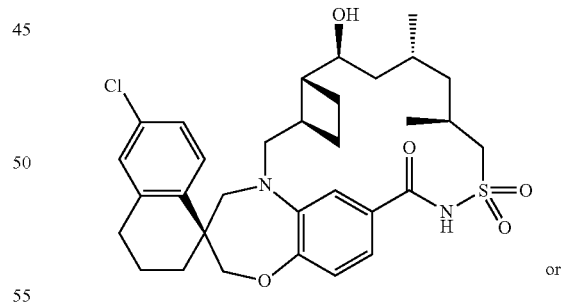

or

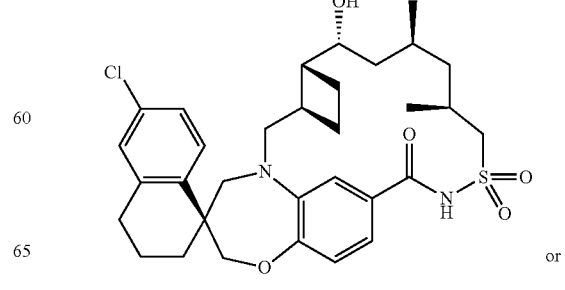

or

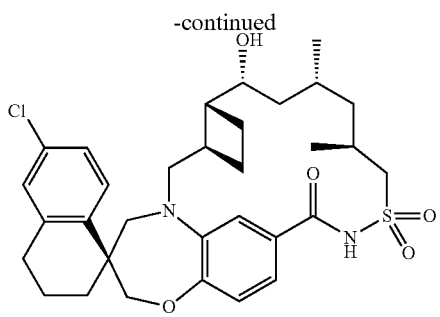

The title compound was obtained as the third eluting isomer using medium pressure chromatography (silica, 20 to 75% EtOAc (+0.3% HOAc):Hexanes) in Example 268, Step 3 (18 mg, 0.030 mmol, 72% yield). $^1$H NMR (400 MHz, CDCl$_3$) δ 8.93 (br. s., 1H), 7.57-7.99 (m, 1H), 7.36-7.55 (m, 1H), 6.88-7.26 (m, 4H), 3.80-4.31 (m, 5H), 3.57-3.74 (m, 1H), 3.11-3.34 (m, 2H), 2.90-3.11 (m, 2H), 2.67-2.88 (m, 3H), 2.38-2.67 (m, 2H), 1.48-2.02 (m, 12H), 1.10-1.19 (m, 4H), 0.90-1.00 (m, 3H). m/z (ESI, +ve ion) 600.8 (M+H)$^+$.

Example 271. (1S,3'R,6'R,7'S,9'S,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'S)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

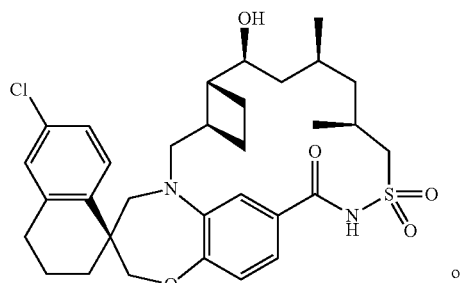

or

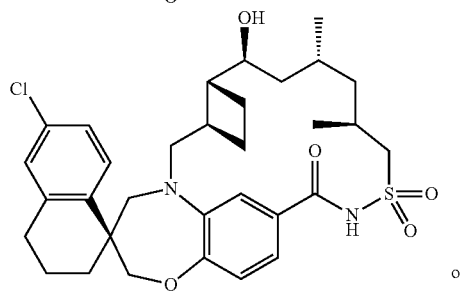

or

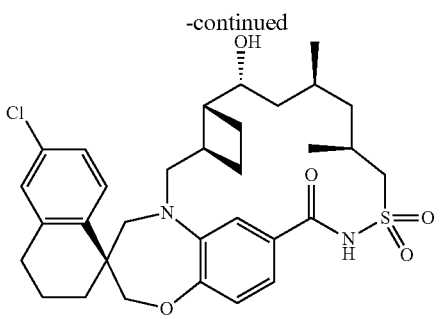

or

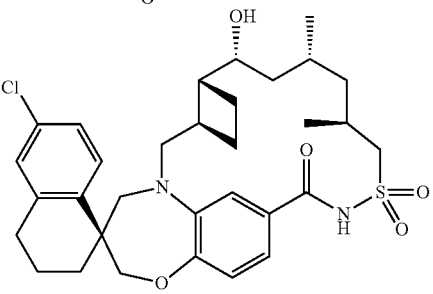

The title compound was obtained as the fourth eluting isomer using medium pressure chromatography (silica, 20 to 75% EtOAc (+0.3% HOAc):Hexanes) in Example 268, Step 3 (1.0 mg, 1.7 μmol, 4.0% yield). $^1$H NMR (500 MHz, CDCl$_3$) δ 9.32 (br. s., 1H), 7.56-7.75 (m, 1H), 7.39-7.39 (m, 1H), 7.33-7.45 (m, 1H), 6.81-7.16 (m, 3H), 3.99-4.31 (m, 3H), 3.46-3.86 (m, 4H), 2.90-3.22 (m, 3H), 2.60-2.75 (m, 2H), 1.66-2.30 (m, 10H), 1.28-1.36 (m, 4H), 0.96-1.13 (m, 8H). m/z (ESI, +ve ion) 600.8 (M+H)$^+$.

Example 272. (1S,3'R,6'R,7'S,9'S,11'R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

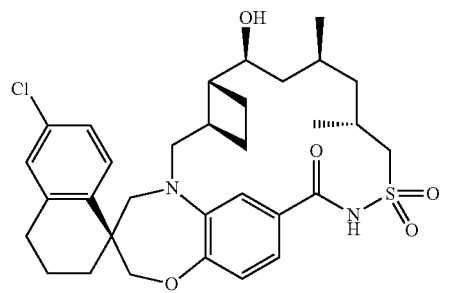

or

-continued

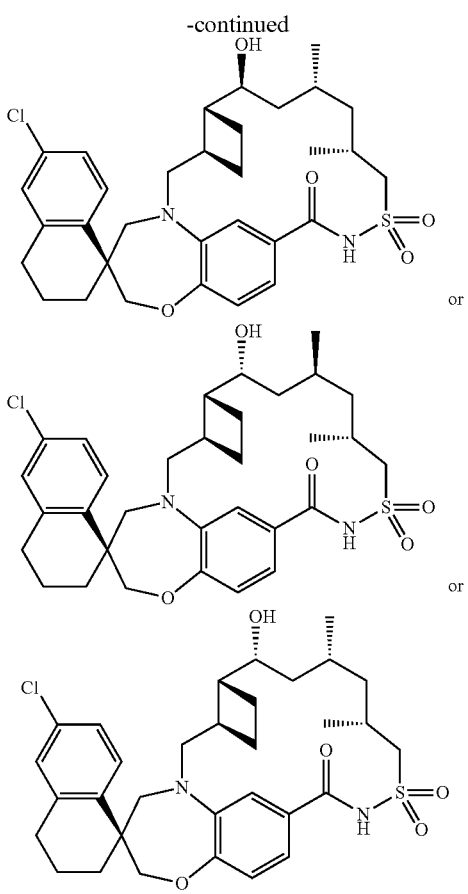

The ketone derived in essentially the same manner as described in Example 268, Step 1 from the alcohol (10 mg, 0.017 mmol, Example 233) was dissolved in MeOH (1.0 mL) and sodium borohydride (6.3 mg, 0.17 mmol) was added (or enough to drive the reaction to completion). The reaction mixture was concentrated to dryness and then diluted with ethyl acetate and 1N HCl soln. (5 mL). The mixture was extracted with ethyl acetate (2×10 mL) and the combined organic layers were washed with brine (1×10 mL) and dried over magnesium sulfate. The crude product was purified by a combination of medium pressure chromatography (silica, 10-60% EtOAc (+0.3% HOAc):hexanes) and reverse-phase preparative HPLC using a Phenomenex Gemini column, 10 micron, C18, 100 Å, 150×30 mm, 0.1% TFA in CH3CN/H2O, gradient 40% to 75% over 30 min to give (1S,3'R,6'R,7'S,9'S,11'R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S,9'R,11'R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'S,11'R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'R,11'R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (1.2 mg, 1.7 μmol, 10% yield) as the first eluting isomer by HPLC. $^1$H NMR (500 MHz, CD$_3$OD) δ 7.74 (d, J=8.56 Hz, 1H), 7.25-7.46 (m, 2H), 7.06-7.23 (m, 2H), 6.87-7.06 (m, 1H), 4.04-4.28 (m, 2H), 3.71-3.84 (m, 2H), 3.61-3.71 (m, 1H), 3.54 (dd, J=9.1, 15.2 Hz, 1H), 3.35-3.39 (m, 2H), 2.72-2.90 (m, 2H), 2.29-2.41 (m, 1H), 2.14-2.28 (m, 2H), 2.04-2.13 (m, 2H), 1.84-2.03 (m, 4H), 1.72-1.82 (m, 2H), 1.51-1.67 (m, 2H), 1.22-1.44 (m, 4H), 1.14 (d, J=6.9 Hz, 3H), 0.98-1.04 (m, 3H), 0.86-0.96 (m, 1H). m/z (ESI, +ve ion) 600.8 (M+H)$^+$.

Example 273. (1S,3'R,6'R,7'S,9'S,11'R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S,9'R,11'R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11'R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

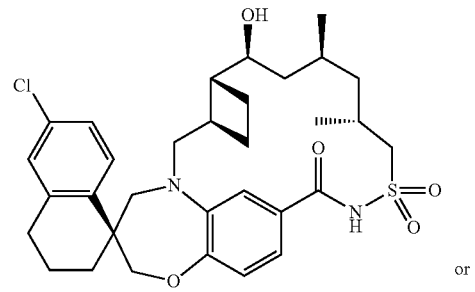

or

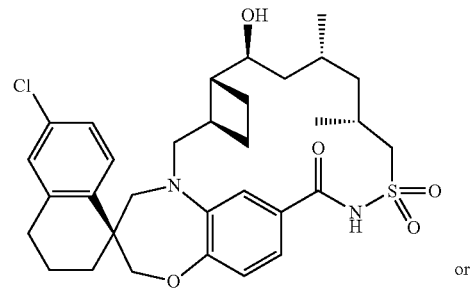

or

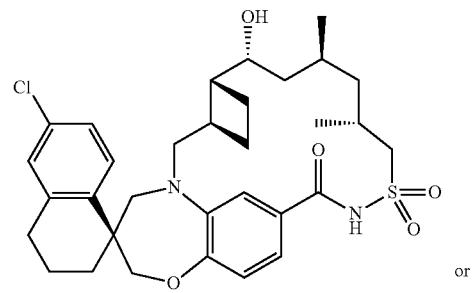

or

727

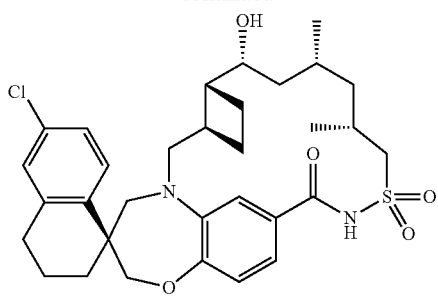

The title compound was obtained as the second eluting isomer by HPLC in the separations described in Example 272 (2.0 mg, 2.8 μmol, 17% yield). $^1$H NMR (500 MHz, CD$_3$OD) δ 7.66-7.85 (m, 1H), 7.25-7.64 (m, 1H), 7.07-7.23 (m, 3H), 6.84-7.01 (m, 1H), 4.10-4.35 (m, 2H), 3.90-4.04 (m, 1H), 3.50-3.69 (m, 3H), 2.98 (dd, J=9.8, 14.9 Hz, 1H), 2.59-2.91 (m, 3H), 1.80-2.23 (m, 8H), 1.61-1.80 (m, 3H), 1.21-1.61 (m, 5H), 1.17 (d, J=6.4 Hz, 3H), 0.90-1.01 (m, 5H). m/z (ESI, +ve ion) 600.8 (M+H)$^+$.

Example 274. (1S,3'R,6'R,7'S,9'S,11'R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

728

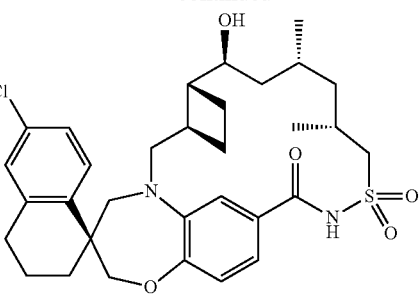

or

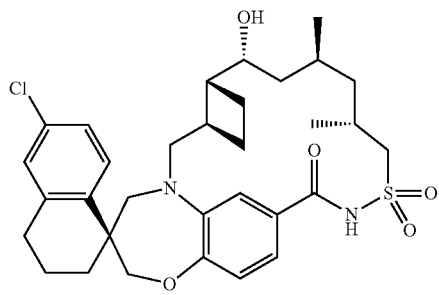

or

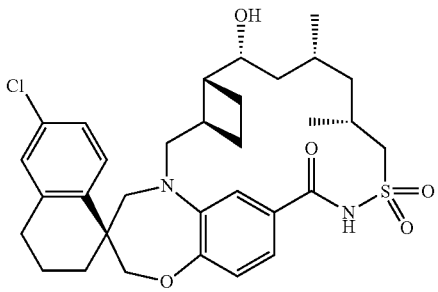

or

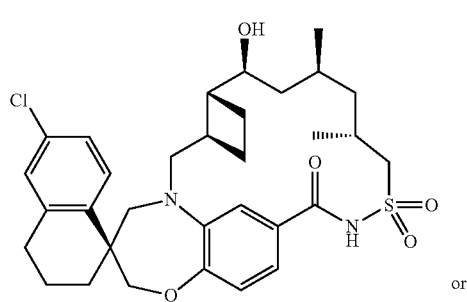

or

The title compound was obtained as the third eluting isomer by HPLC in the separations described in Example 272 (0.9 mg, 1.5 μmol, 9.0% yield). $^1$H NMR (400 MHz, CD$_3$OD) δ 7.76 (d, J=8.4 Hz, 1H), 7.16-7.23 (m, 2H), 7.09-7.15 (m, 2H), 6.93 (d, J=8.2 Hz, 1H), 4.03-4.13 (m, 2H), 3.99 (d, J=15.3 Hz, 1H), 3.73 (d, J=13.9 Hz, 1H), 3.58-3.68 (m, 1H), 3.52 (dd, J=15.0, 6.2 Hz, 1H), 3.24-3.29 (m, 1H), 3.12-3.21 (m, 1H), 2.72-2.91 (m, 3H), 2.19-2.34 (m, 2H), 2.07-2.19 (m, 3H), 1.96 (d, J=9.4 Hz, 1H), 1.88 (br. s., 1H), 1.66-1.80 (m, 2H), 1.55-1.65 (m, 1H), 1.42-1.55 (m, 2H), 1.18-1.28 (m, 2H), 1.15 (d, J=6.8 Hz, 3H), 1.07 (d, J=6.5 Hz, 1H), 0.92 (d, J=6.7 Hz, 3H), 0.84-0.89 (m, 1H). m/z (ESI, +ve ion) 600.8 (M+H)$^+$.

Example 275. (1S,3'R,6'R,7'S,9'S,11'R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11'R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'R)-6-chloro-7'-hydroxy-9',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

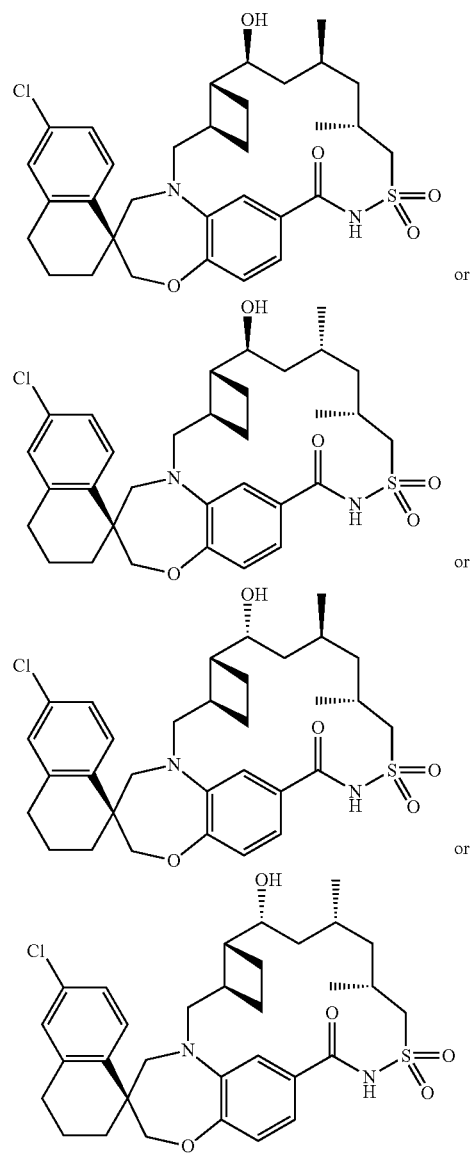

The title compound was obtained as the fourth eluting isomer by HPLC in the separations described in Example 272 (0.5 mg, 0.7 µmol, 4.2% yield). $^1$H NMR (500 MHz, CD$_3$OD) δ 7.75 (d, J=8.56 Hz, 1H), 7.06-7.25 (m, 2H), 6.74-7.06 (m, 3H), 3.94-4.26 (m, 2H), 3.73-3.84 (m, 1H), 3.62-3.73 (m, 1H), 3.40-3.55 (m, 2H), 2.73-2.91 (m, 1H), 2.68 (s, 1H), 2.42-2.54 (m, 1H), 2.29-2.42 (m, 1H), 1.97-2.14 (m, 2H), 1.47-1.97 (m, 11H), 1.17 (br. s., 3H), 0.97-1.12 (m, 4H), 0.92-1.04 (m, 4H). m/z (ESI, +ve ion) 600.8 (M+H)$^+$.

Example 276. (1S,3'R,6'R,9'R)-6-chloro-9'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide and (1S,3'R,6'R,9'S)-6-chloro-9'-methyl-3,4-dihydro-2H,15'H-spiro[naphthalene-[20]oxa[13]thia[1,14]diazatetracyclo[14.7.2.0$^{3,6}$.0$^{19,24}$]pentacosa [16,18,24]trien]-15'-one 13',13'-dioxide

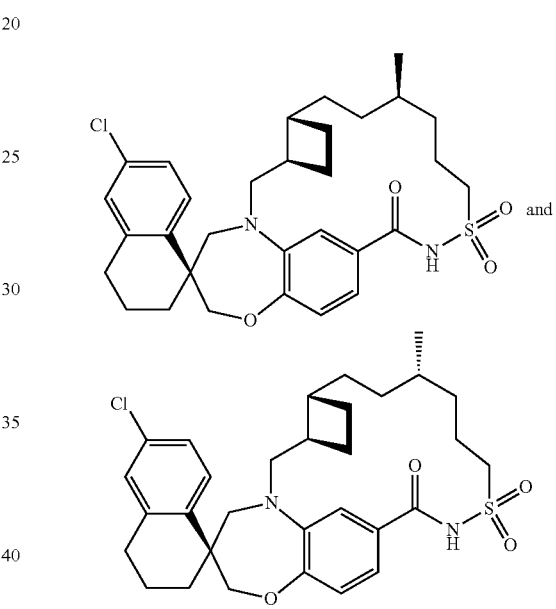

The vinyl bromide (1S,3'R,6'R,7'S,8'E)-6-chloro-7'-hydroxy-9'-bromo-3,4-dihydro-2h,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'R,8'E)-6-chloro-7'-hydroxy-9'-bromo-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (9.0 mg, 0.014 mmol, Example 236) was dissolved in 1,4-dioxane (0.3 mL) and the cesium carbonate (15.79 mg, 0.048 mmol), PdCl$_2$(dppf)-CH$_2$Cl$_2$ (2.261 mg, 2.77 µmop and methaneboronic acid (2.486 mg, 0.042 mmol) were added and the reaction was heated at 100° C. for one hour. The reaction was then cooled and diluted with EtOAc. The mixture was then filtered and the filtrate was concentrated to dryness. The crude product was purified using SFC chromatography (AS column, 35% MeOH/CO2) To give an unidentified mixture of products (7 mg). The product mixture (7.0 mg, 0.012 mmol) was dissolved in EtOAc (1.0 mL). The platinum (IV) oxide (2.7 mg, 0.012 mmol) was added and the reaction vessel was flushed with hydrogen and stirred over night under balloon pressure. The reaction mixture was then filtered and the filtrate was concentrated and the residue was taken up in DMSO. The crude material was purified by reverse-phase preparative

731

HPLC using a Phenomenex Luna column, 10 micron, C8(2), 100 Å, 150×30 mm, 0.1% TFA in CH$_3$CN/H$_2$O, gradient 50% to 70% over 20 min to provide (1S,3'R,6'R,9'R)-6-chloro-9'-methyl-3,4-dihydro-2H,15'H-spiro[naphthalene-1, 22'-[20]oxa[13]thia[1,14]diazatetracyclo[14.7.2.0$^{3,6}$.0$^{19,24}$] pentacosa[16,18,24]trien]-15'-one 13',13'-dioxide and (1S, 3'R,6'R,9'S)-6-chloro-9'-methyl-3,4-dihydro-2H,15'H-spiro [naphthalene-1,22'-[20]oxa[13]thia[1,14]diazatetracyclo [14.7.2.0$^{3,6}$.0$^{19,24}$]pentacosa[16,18,24]trien]-15'-one 13', 13'-dioxide. (0.9 mg, 0.8 μmol, 6.6% yield) as the third eluting isomer. $^1$H NMR (400 MHz, CDCl$_3$) δ 7.79-8.02 (m, 1H), 7.47-7.66 (m, 1H), 6.64-6.72 (m, 1H), 6.64-7.08 (m, 4H), 3.81-4.16 (m, 2H), 3.47-3.69 (m, 2H), 3.22-3.47 (m, 1H), 2.98-3.22 (m, 1H), 2.87 (dd, J=8.1, 15.4 Hz, 1H), 2.55-2.70 (m, 2H), 1.96-2.28 (m, 2H), 1.89-1.96 (m, 1H), 1.74-1.89 (m, 3H), 1.27-1.53 (m, 9H), 0.65-0.87 (m, 7H). m/z (ESI, +ve ion) 571.3 (M+H)$^+$.

Example 279. (1S,3'R,6'R,7'S,9'S,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11'S,12'R)-6-chloro-7'-hydroxy-11',12'-dimethyl-9'-(4-morpholinyl)-3,4-dihydro-2H,15'H-spiro[naphthalene-1,22'-[20]oxa [13]thia[1,14]diazatetracyclo[14.7.2.0$^{3,6}$.0$^{19,24}$] pentacosa [16,18,24]trien]-15'-one 13',13'-dioxide or (1S,3'R,6'R,7'R,9'S,11'S,12'R)-6-chloro-7'-hydroxy-11',12'-dimethyl-9'-(4-morpholinyl)-3,4-dihydro-2H,15'H-spiro[naphthalene-1,22'-[20]oxa[13] thia[1,14]diazatetracyclo[14.7.2.0$^{3,6}$.0$^{19,24}$]pentacosa [16,18,24]trien]-15'-one 13',13'-dioxide or (1S,3'R, 6'R,7'R,9'R,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14] diazatetracyclo[14.7.2.0$^{3,6}$.0$^{19,24}$]pentacosa [16,18, 24]trien]-15'-one 13',13'-dioxide

732

-continued

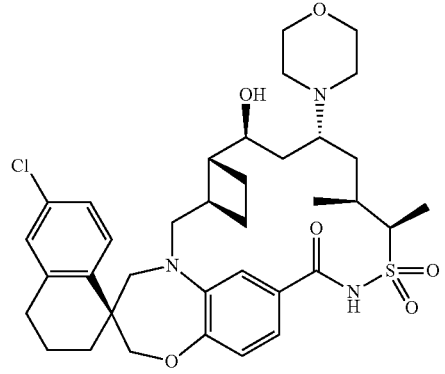

or


or

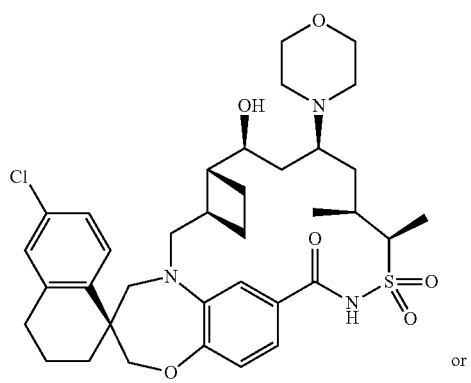

or

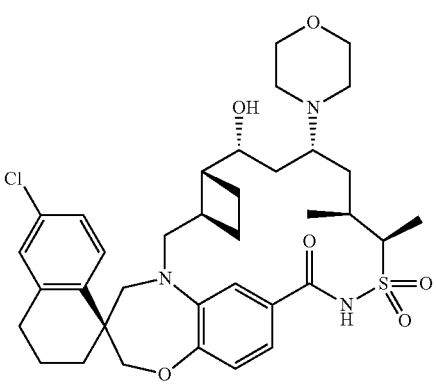

Step 1: (1S,3'R,6'R,9'S,11'S,12'R)-6-chloro-11',12'-dimethyl-9'-(4-morpholinyl)-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa [16,18,24]triene]-7',15'-dione 13',13'-dioxide and (1S,3'R,6'R,9'R,11'S,12'R)-6-chloro-11',12'-dimethyl-9'-(4-morpholinyl)-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa [16,18,24]triene]-7',15'-dione 13',13'-dioxide

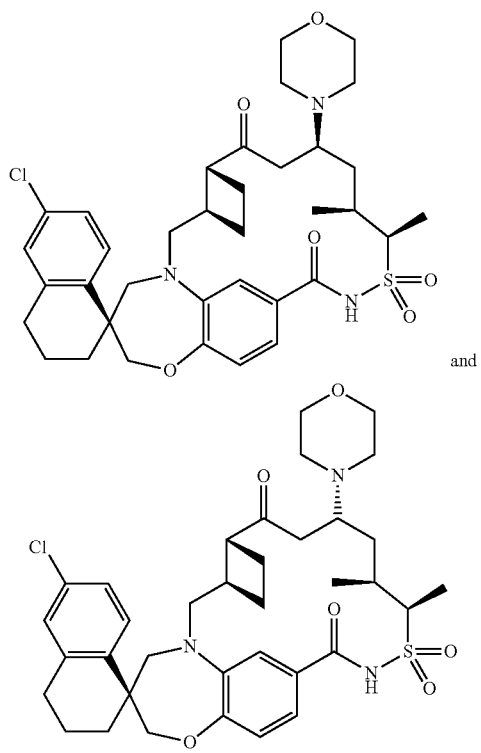

The enone (50 mg, 0.084 mmol, Example 244, Step 1) was dissolved in THF (2.5 mL) and morpholine (0.15 mL, 1.7 mmol) was added and the resulting solution was stirred for 2.5 hours to completion. The reaction mixture was then concentrated and placed under high vacuum. The residue was dissolved in MeOH (2.0 mL) and cooled to 0° C. The sodium borohydride (16 mg, 0.42 mmol) was added and the reaction was stirred for 15 minutes to completion. The mixture was concentrated to dryness and the residue was taken up in EtOAc (20 mL) and washed with saturated sodium bicarbonate solution (1×10 mL). The organic layer was washed with brine (1×10 mL) and dried over magnesium sulfate. The crude material was purified by reverse-phase preparative HPLC using a Phenomenex Gemini column, 10 micron, C18, 100 Å, 150×30 mm, 0.1% TFA in CH₃CN/H₂O, gradient 35% to 55% over 45 min to provide (1S,3'R,6'R,9'S,11'S,12'R)-6-chloro-11',12'-dimethyl-9'-(4-morpholinyl)-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[16,18,24]triene]-7',15'-dione 13',13'-dioxide or (1S,3'R,6'R,9'R,11'S,12'R)-6-chloro-11',12'-dimethyl-9'-(4-morpholinyl)-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[16,18,24]triene]-7',15'-dione 13',13'-dioxide (45 mg; 0.049 mmol, 59%) as the first eluting isomer. Further elution provided 1S,3'R,6'R,9'S,11'S,12'R)-6-chloro-11',12'-dimethyl-9'-(4-morpholinyl)-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[16,18,24]triene]-7',15'-dione 13',13'-dioxide or (1S,3'R,6'R,9'R,11'S,12'R)-6-chloro-11',12'-dimethyl-9'-(4-morpholinyl)-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[16,18,24]triene]-7',15'-dione 13',13'-dioxide (14 mg; 0.015 mmol, 18%) as the second eluting isomer.

Step 2: (1S,3'R,6'R,7'S,9'S,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide or (1S,3'R,6'R,7'S,9'R,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide or (1S,3'R,6'R,7'R,9'S,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide or (1S,3'R,6'R,7'R,9'R,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide The ketone (Example 279, Step 1, first eluting isomer) (38 mg, 0.042 mmol) was dissolved in MeOH (2.0 mL) and cooled to 0° C. The sodium borohydride (15.76 mg, 0.417 mmol) was added and the reaction was stirred for 15 minutes to completion. The mixture was concentrated to dryness and the residue was taken up in EtOAc (20 ml) and washed with saturated sodium bicarbonate solution (1×10 mL). The organic layer was washed with brine (1×10 mL) and dried over magnesium sulfate. The crude material was purified by reverse-phase preparative HPLC using a Phenomenex Gemini column, 10 micron, C18, 100 Å, 150×30 mm, 0.1% TFA in CH₃CN/H₂O, gradient 35% to 55% over 45 min to provide (1S,3'R,6'R,7'S,9'S,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'S,9'R,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'R,9'S,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'R,9'R,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide as the first eluting isomer (5.0 mg, 5.5 µmol, 13% yield). ¹H NMR (400 MHz, CD₃OD) δ 7.75 (d, J=8.6 Hz, 1H), 7.31-7.36 (m, 1H), 7.06-7.31 (m, 3H), 6.93-7.06 (m, 2H), 3.40-4.47 (m, 11H), 3.04-3.30 (m, 3H), 2.74-2.91

(m, 2H), 2.61-2.74 (m, 2H), 2.34-2.53 (m, 2H), 1.67-2.21 (m, 13H), 1.37-1.63 (m, 5H), 1.07-1.25 (m, 3H). m/z (ESI, +ve ion) 685.8 (M+H)⁺

Example 280. (1S,3'R,6'R,7'S,9'S,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$] pentacosa [16,18,24]trien]-15'-one 13',13'-dioxide or (1S,3'R,6'R,7'R,9'S,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R, 6'R,7'R,9'R,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14] diazatetracyclo[14.7.2.0$^{3,6}$.0$^{19,24}$]pentacosa [16,18, 24]trien]-15'-one 13',13'-dioxide

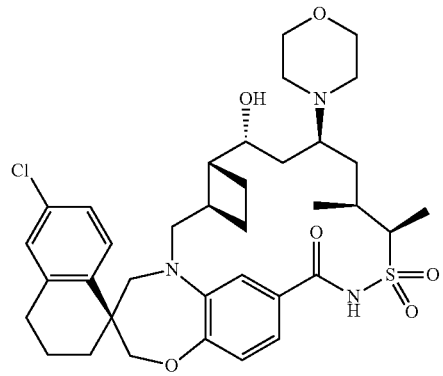

or

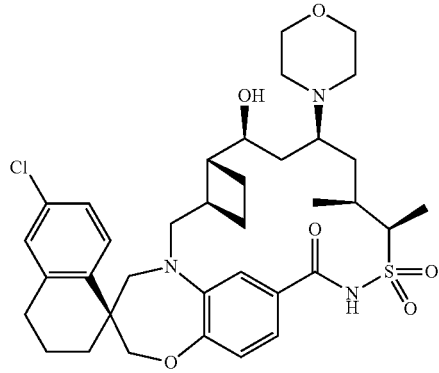

or

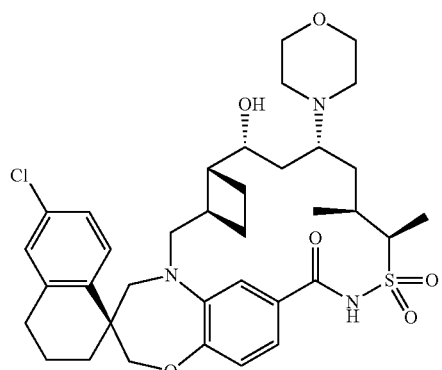

or

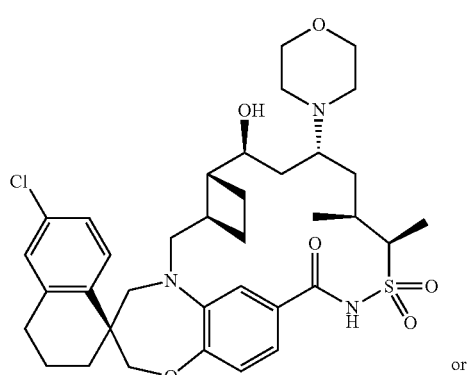

or

The title compound was obtained as the second eluting isomer using reverse-phase preparative HPLC using a Phenomenex Gemini column, 10 micron, C18, 100 Å, 150×30 mm, 0.1% TFA in CH₃CN/H₂O, gradient 35% to 55% over 45 min in Example 279 (6.0 mg, 8.7 µmol, 21% yield). ¹H NMR (400 MHz, MeOD) δ 7.75 (d, J=8.41 Hz, 1H), 7.17-7.25 (m, 1H), 7.14 (d, J=2.15 Hz, 1H), 7.08 (dd, J=1.86, 8.12 Hz, 1H), 6.93-7.01 (m, 2H), 4.09-4.22 (m, 3H), 4.01-4.09 (m, 1H), 3.63-4.01 (m, 6H), 3.14-3.58 (m, 17H), 2.71-2.91 (m, 2H), 2.41 (br. s., 1H), 2.01-2.22 (m, 5H), 1.70-2.01 (m, 7H), 1.44-1.67 (m, 5H), 1.11-1.24 (m, 3H). m/z (ESI, +ve ion) 686.3 (M+H)⁺.

Example 281. (1S,3'R,6'R,7'S,9'S,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$] pentacosa [16,18,24]trien]-15'-one 13',13'-dioxide or (1S,3'R,6'R,7'R,9'S,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

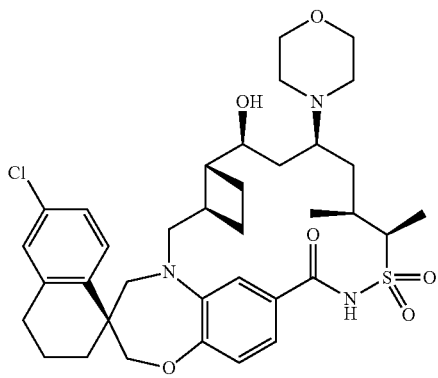

or

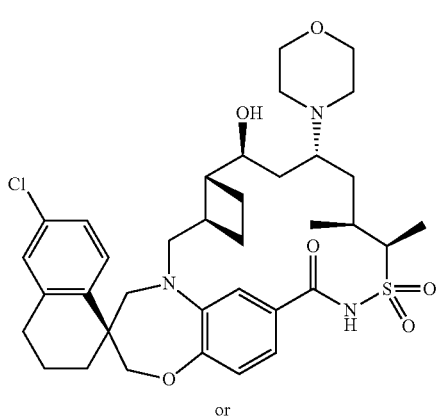

or

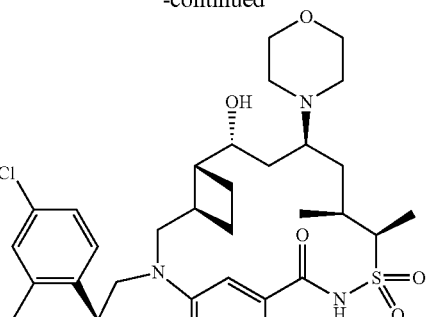

or

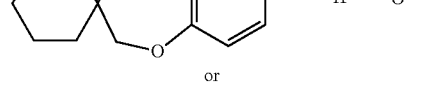

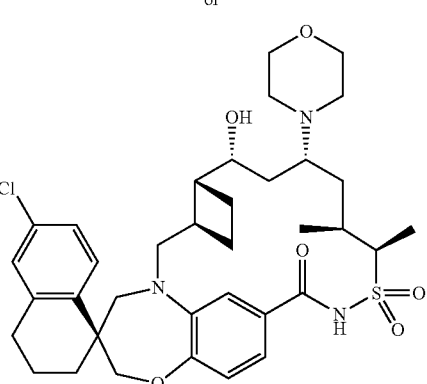

The ketone (Example 279, Step 1, second eluting isomer) (14 mg, 0.015 mmol) was dissolved in MeOH (1.0 mL) and cooled to 0° C. The sodium borohydride (5.6 mg, 0.15 mmol) was added and the reaction was stirred for 15 minutes to completion. The mixture was concentrated to dryness and the residue was taken up in EtOAc (20 ml) and washed with saturated sodium bicarbonate solution (1×10 mL). The organic layer was washed with brine (1×10 mL) and dried over magnesium sulfate. The crude material was purified by reverse-phase preparative HPLC using a Phenomenex Gemini column, 10 micron, C18, 100 Å, 150×30 mm, 0.1% TFA in CH$_3$CN/H$_2$O, gradient 35% to 55% over 45 min to provide (1S,3'R,6'R,7'S,9'S,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S,9'R,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]-trien]-15'-one 13',13'-dioxide or (1S,3'R,6'R,7'R,9'S,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'R,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]-trien]-15'-one 13',13'-dioxide as the first eluting isomer (7.0 mg, 0.0077 mmol, 52% yield). $^1$H NMR (400 MHz, CD$_3$OD) δ 7.77 (d, J=8.02 Hz, 1H), 7.43 (br. s., 2H), 6.72-7.19 (m, 3H), 5.13-5.46 (m, 1H), 3.96-4.22 (m, 4H), 3.60-3.75 (m, 5H), 2.42-3.17 (m, 9H), 1.63-2.19 (m, 10H), 1.32 (s, 5H). m/z (ESI, +ve ion) 686.3 (M+H)$^+$.

Example 282. (1S,3'R,6'R,7'S,9'S,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$] pentacosa [16,18,24]trien]-15'-one 13',13'-dioxide or (1S,3'R,6'R,7'R,9'S,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'S,12'R)-6-chloro-7'-hydroxy-11',12'-dimethyl-9'-(4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide -continued

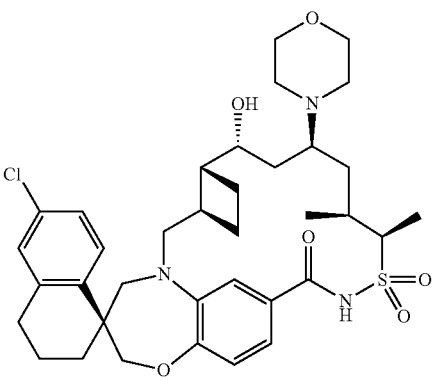

or

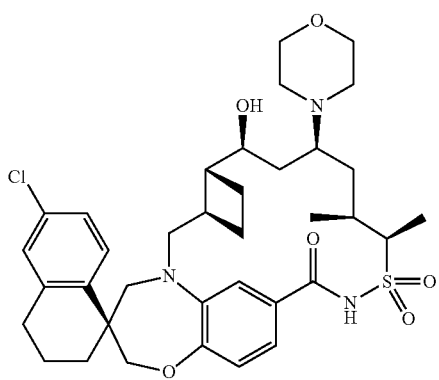

or

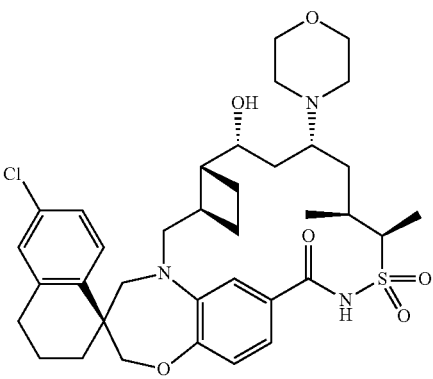

or

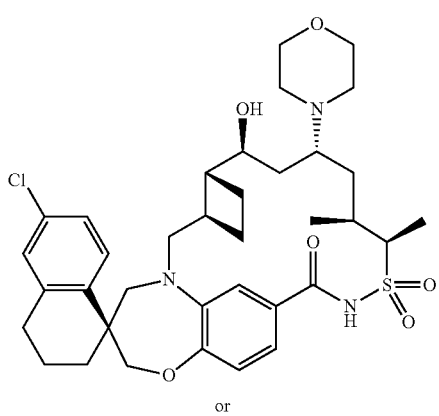

The title compound was obtained as the second eluting isomer using reverse-phase preparative HPLC using a Phenomenex Gemini column, 10 micron, C18, 100 Å, 150×30 mm, 0.1% TFA in CH$_3$CN/H$_2$O, gradient 35% to 55% over 45 min in Example 281 (0.7 mg, 0.7 μmol, 5% yield). $^1$H NMR (500 MHz, CD$_3$OD) δ 7.60 (dd, J=5.50, 8.44 Hz, 1H), 6.97-7.06 (m, 3H), 6.86-6.94 (m, 1H), 6.76-6.83 (m, 1H), 3.89-4.05 (m, 5H), 3.53-3.73 (m, 7H), 3.26-3.31 (m, 4H), 2.56-2.74 (m, 1H), 2.27-2.42 (m, 1H), 2.14 (br. s., 1H), 1.95 (d, J=9.29 Hz, 2H), 1.77-1.88 (m, 11H), 1.60-1.70 (m, 4H), 1.29-1.39 (m, 5H), 1.00-1.09 (m, 4H). m/z (ESI, +ve ion) 686.3 (M+H)$^+$.

Example 283. (1S,3'R,6'R,7'S,9'S,11'S,12'R)-6-chloro-7'-hydroxy-11',12'-dimethyl-9'-(1-piperidinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S,9'R,11'S,12'R)-6-chloro-7'-hydroxy-11',12'-dimethyl-9'-(1-piperidinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'S,11'S,12'R)-6-chloro-7'-hydroxy-11',12'-dimethyl-9'-(1-piperidinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'R,11'S,12'R)-6-chloro-7'-hydroxy-11',12'-dimethyl-9'-(1-piperidinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide

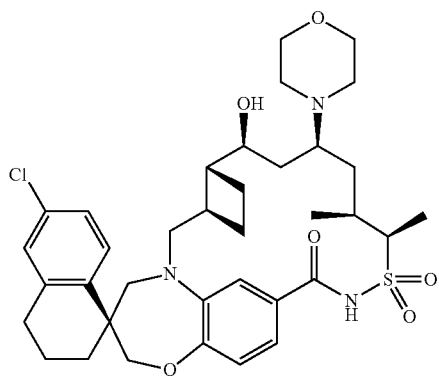

or

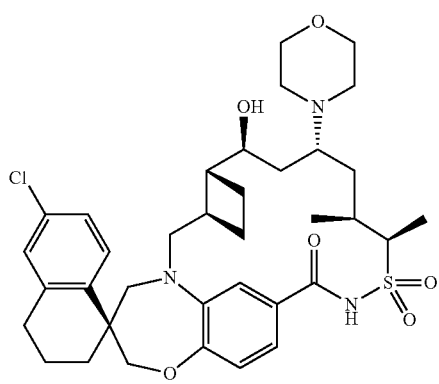

or

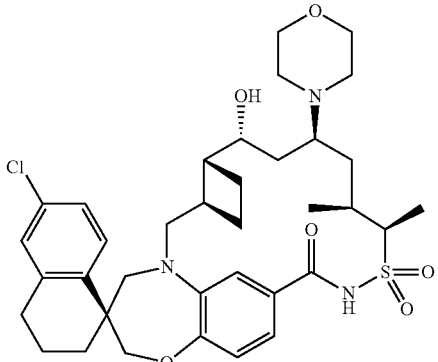

or

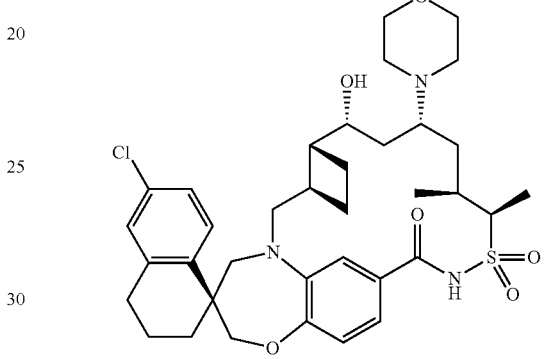

The enone (50 mg, 0.084 mmol, Example 230, Step 1) was dissolved in THF (2.5 mL) and piperidine (0.17 mL, 1.7 mmol) was added and the resulting solution was stirred for 2.5 hours to completion. The reaction mixture was then concentrated and placed under high vacuum. The crude ketone (~50 mg) was dissolved in MeOH (2 mL) and sodium borohydride (32 mg, 0.84 mmol) was added and stirred for 20 minutes. The mixture was then concentrated and then quenched with saturated sodium bicarbonate after diluting with ethyl acetate. The mixture was extracted with EtOAc (2×25 mL). The combined organic layers were washed with brine (1×20 mL) and dried over magnesium sulfate. The residue was then dissolved in DMSO. The crude material was purified by reverse-phase preparative HPLC using a Phenomenex Gemini column, 10 micron, C18, 100 Å, 150×30 mm, 0.1% TFA in CH3CN/H2O, gradient 35% to 55% over 45 min to provide (1S,3'R,6'R,7'S,9'S,11'S,12'R)-6-chloro-7'-hydroxy-11',12'-dimethyl-9'-(1-piperidinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S,9'R,11'S,12'R)-6-chloro-7'-hydroxy-11',12'-dimethyl-9'-(1-piperidinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'S,11'S,12'R)-6-chloro-7'-hydroxy-11',12'-dimethyl-9'-(1-piperidinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'R,11'S,12'R)-6-chloro-7'-hydroxy-11',12'-dimethyl-9'-(1-piperidinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide as the first eluting and minor isomer (11 mg, 0.016 mmol, 19% yield). $^1$H NMR (400

MHz, CD$_3$OD) δ 7.77 (d, J=8.4 Hz, 1H), 7.53 (d, J=1.4 Hz, 1H), 7.31-7.36 (m, 1H), 7.21 (dd, J=2.3, 8.5 Hz, 1H), 7.12 (d, J=2.2 Hz, 1H), 6.82 (d, J=8.2 Hz, 1H), 3.96-4.17 (m, 3H), 3.78-3.89 (m, 1H), 3.62 (d, J=14.5 Hz, 1H), 3.37-3.56 (m, 3H), 3.32 (d, J=14.7 Hz, 1H), 3.12-3.22 (m, 2H), 2.98-3.08 (m, 2H), 2.42-2.60 (m, 5H), 2.23-2.41 (m, 5H), 1.89-2.10 (m, 9H), 1.68-1.77 (m, 1H), 1.36-1.43 (m, 4H), 1.29 (d, J=7.2 Hz, 3H), 1.04 (d, J=6.9 Hz, 3H). m/z (ESI, +ve ion) 683.7 (M+H)$^+$.

Example 284. (1S,3'R,6'R,7'S,9'S,11'S,12'R)-6-chloro-7'-hydroxy-11',12'-dimethyl-9'-(1-piperidinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11'S,12'R)-6-chloro-7'-hydroxy-11',12'-dimethyl-9'-(1-piperidinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11'S,12'R)-6-chloro-7'-hydroxy-11',12'-dimethyl-9'-(1-piperidinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'S,12'R)-6-chloro-7'-hydroxy-11',12'-dimethyl-9'-(1-piperidinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

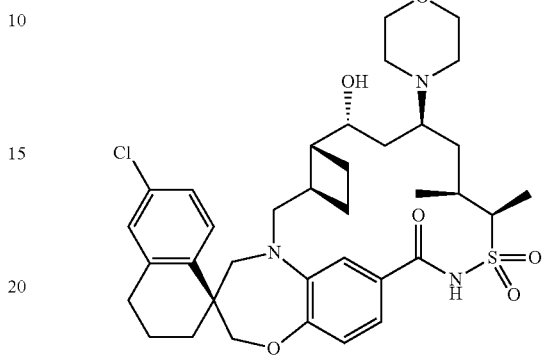

or

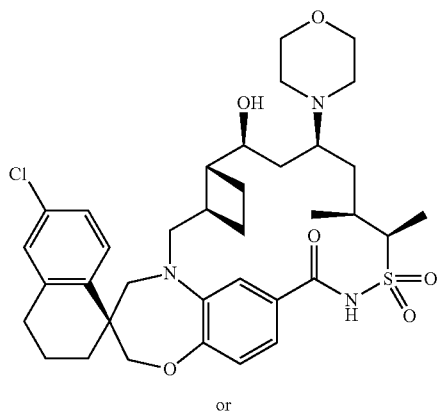

or

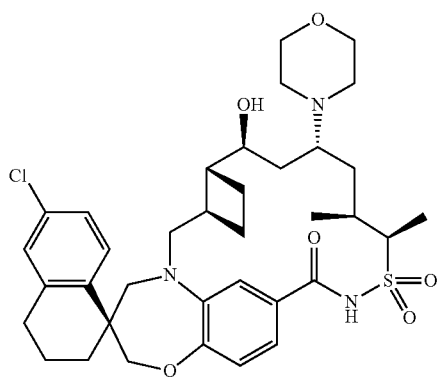

or

The title compound was obtained as the second eluting and major isomer using reverse-phase preparative HPLC using a Phenomenex Gemini column, 10 micron, C18, 100 Å, 150×30 mm, 0.1% TFA in CH$_3$CN/H$_2$O, gradient 35% to 55% over 45 min in Example 283 (16 mg, 0.023 mmol, 28% yield). $^1$H NMR (400 MHz, CD$_3$OD) δ 7.66-7.87 (m, 1H), 7.25-7.51 (m, 1H), 6.99-7.25 (m, 3H), 6.76-6.99 (m, 1H), 4.37 (d, J=10.2 Hz, 1H), 3.98-4.19 (m, 3H), 3.72-3.94 (m, 3H), 3.43-3.66 (m, 2H), 3.13-3.28 (m, 2H), 3.07 (dd, J=8.6, 15.3 Hz, 1H), 2.66-2.96 (m, 4H), 2.27-2.51 (m, 3H), 1.57-2.12 (m, 18H), 1.27-1.57 (m, 6H). m/z (ESI, +ve ion) 683.7 (M+H)$^+$.

Example 285. (1S,3'R,6'R,7'S,9'S,11'S,12'R)-6-chloro-7'-hydroxy-11',12'-dimethyl-9'-(3-oxo-4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11'S,12'R)-6-chloro-7'-hydroxy-11',12'-dimethyl-9'-(3-oxo-4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11'S,12'R)-6-chloro-7'-hydroxy-11',12'-dimethyl-9'-(3-oxo-4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'S,12'R)-6-chloro-7'-hydroxy-11',12'-dimethyl-9'-(3-oxo-4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

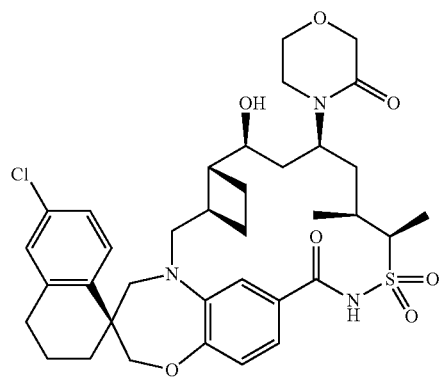

or

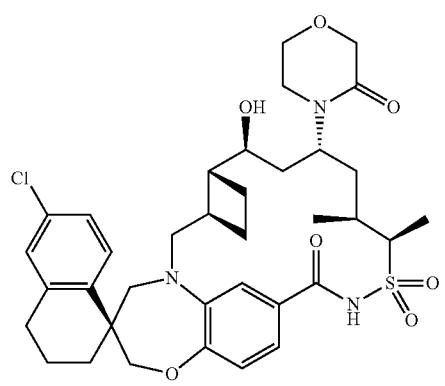

or

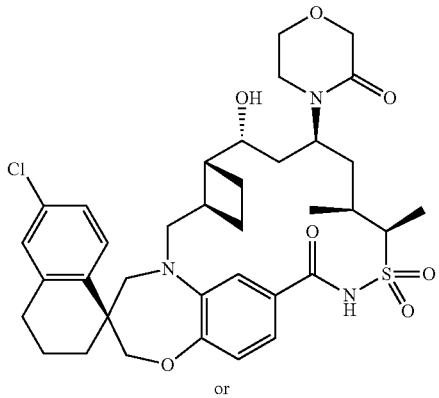

or

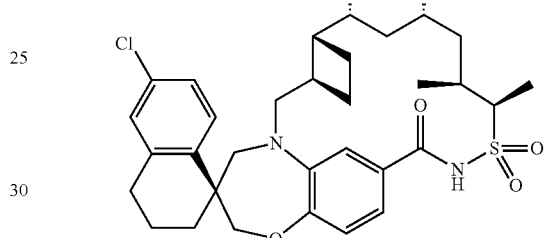

The enone (48 mg, 0.080 mmol, Example 244, Step 1) was dissolved in THF (2.5 mL) and morpholin-3-one (8.94 mg, 0.088 mmol) was added followed by dropwise addition of lithium bis(trimethylsilyl)amide, 1.0M solution in tetrahydrofuran (0.17 mL, 0.17 mmol). The reaction was stirred for 90 minutes until completion. The reaction was quenched with saturated ammonium chloride solution and extracted with ethyl acetate (2×30 mL). The combined organic layers were washed with brine (1×15 mL) and dried over magnesium sulfate to give crude ketone. The crude ketone was dissolved in MeOH (2 mL) and sodium borohydride (30.4 mg, 0.804 mmol) was added. The reaction was stirred for 45 minutes then concentrated to dryness. The residue was take up in EtOAc and acidified with TFA. The mixture was concentrated. The crude material was purified by reverse-phase preparative HPLC using a Phenomenex Gemini column, 10 micron, C18, 100 Å, 150×30 mm, 0.1% TFA in CH$_3$CN/H$_2$O, gradient 50% to 85% over 45 min to provide (1S,3'R,6'R,7'S,9'S,11'S,12'R)-6-chloro-7'-hydroxy-11',12'-dimethyl-9'-(3-oxo-4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13', 13'-dioxide or (1S,3'R,6'R,7'S,9'R,11'S,12'R)-6-chloro-7'-hydroxy-11',12'-dimethyl-9'-(3-oxo-4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'S,11'S,12'R)-6-chloro-7'-hydroxy-11',12'-dimethyl-9'-(3-oxo-4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R,9'R,11'S,12'R)-6-chloro-7'-hydroxy-11',12'-dimethyl-9'-(3-oxo-4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]

trien]-15'-one 13',13'-dioxide as the first eluting and minor isomer (4.4 mg, 5.40 µmol, 6.7% yield). $^1$H NMR (400 MHz, MeOH-d$_4$) δ 7.76 (d, J=8.6 Hz, 1H), 7.20 (dd, J=2.3, 8.5 Hz, 1H), 7.13 (d, J=2.2 Hz, 1H), 6.97-7.01 (m, 1H), 6.94-6.97 (m, 1H), 6.93 (d, J=1.6 Hz, 1H), 4.64-4.80 (m, 1H), 4.12-4.18 (m, 3H), 3.99 (d, J=12.1 Hz, 1H), 3.87-3.97 (m, 4H), 3.80 (d, J=14.1 Hz, 1H), 3.35-3.46 (m, 5H), 3.25-3.32 (m, 1H), 2.73-2.90 (m, 2H), 2.44-2.55 (m, J=3.9 Hz, 1H), 2.01-2.28 (m, 5H), 1.84-1.94 (m, 2H), 1.70-1.82 (m, 2H), 1.61-1.69 (m, 2H), 1.46-1.54 (m, 2H), 1.43 (d, J=7.24 Hz, 3H), 1.14 (d, J=6.65 Hz, 3H). m/z (ESI, +ve ion) 699.7 (M+H)$^+$.

Example 286. (1S,3'R,6'R,7'S,9'S,11'S,12'R)-6-chloro-7'-hydroxy-11',12'-dimethyl-9'-(3-oxo-4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R,11'S,12'R)-6-chloro-7'-hydroxy-11',12'-dimethyl-9'-(3-oxo-4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'S,11'S,12'R)-6-chloro-7'-hydroxy-11',12'-dimethyl-9'-(3-oxo-4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R,9'R,11'S,12'R)-6-chloro-7'-hydroxy-11',12'-dimethyl-9'-(3-oxo-4-morpholinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

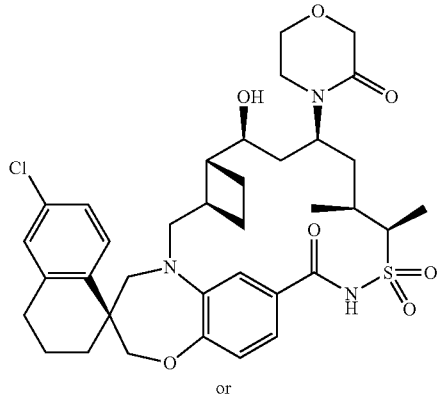

or

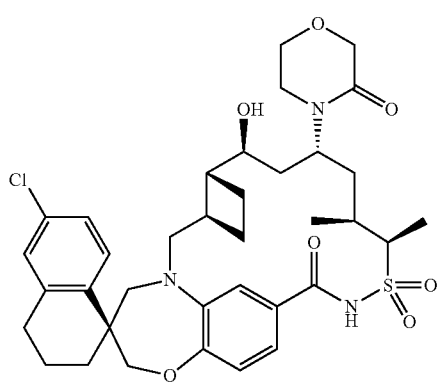

or

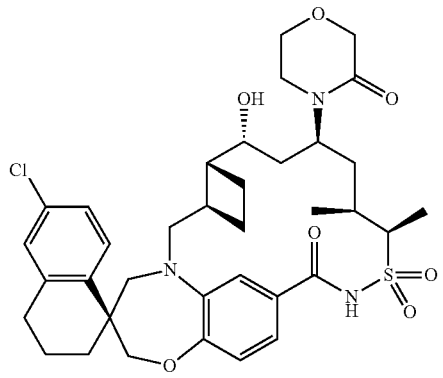

or

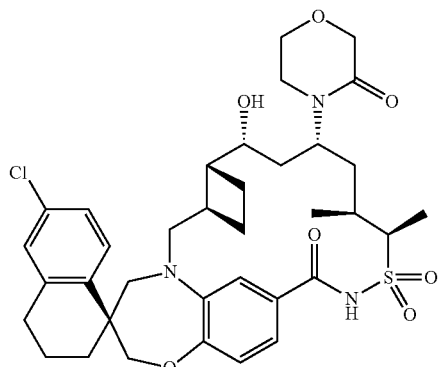

The title compound was obtained as the second eluting and major isomer using reverse-phase preparative HPLC using a Phenomenex Gemini column, 10 micron, C18, 100 Å, 150×30 mm, 0.1% TFA in CH$_3$CN/H$_2$O, gradient 35% to 55% over 45 min in Example 285 (19.5 mg, 0.024 mmol, 29.8% yield). $^1$H NMR (400 MHz, MeOH-d$_4$) δ 7.76 (d, J=8.4 Hz, 1H), 7.55 (d, J=1.6 Hz, 1H), 7.18 (dd, J=8.5, 2.3 Hz, 1H), 7.10-7.15 (m, 2H), 6.95 (d, J=8.2 Hz, 1H), 4.02-4.25 (m, 6H), 3.81-3.94 (m, 2H), 3.64 (d, J=14.1 Hz, 1H), 3.47-3.54 (m, 1H), 3.37-3.46 (m, 1H), 3.24 (d, J=14.1 Hz, 1H), 3.13-3.20 (m, J=1.6 Hz, 1H), 3.04 (dd, J=8.9, 15.2 Hz, 1H), 2.70-2.88 (m, 2H), 2.42-2.60 (m, 2H), 1.57-2.14 (m, 13H), 1.48 (d, J=2.2 Hz, 1H), 1.43 (d, J=7.0 Hz, 3H), 1.10 (d, J=6.9 Hz, 3H). m/z (ESI, +ve ion) 699.7 (M+H)$^+$.

Example 287. N-((1S,3'R,6'R,7'S,9'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-9'-yl)-N-methyl glycine or N-((1S,3'R,6'R,7'S,9'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-9'-yl)-N-methylglycine or N-((1S,3'R,6'R,7'R,9'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-9'-yl)-N-methyl glycine or N-((1S,3'R,6'R,7'R,9'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-9'-yl)-N-methyl glycine

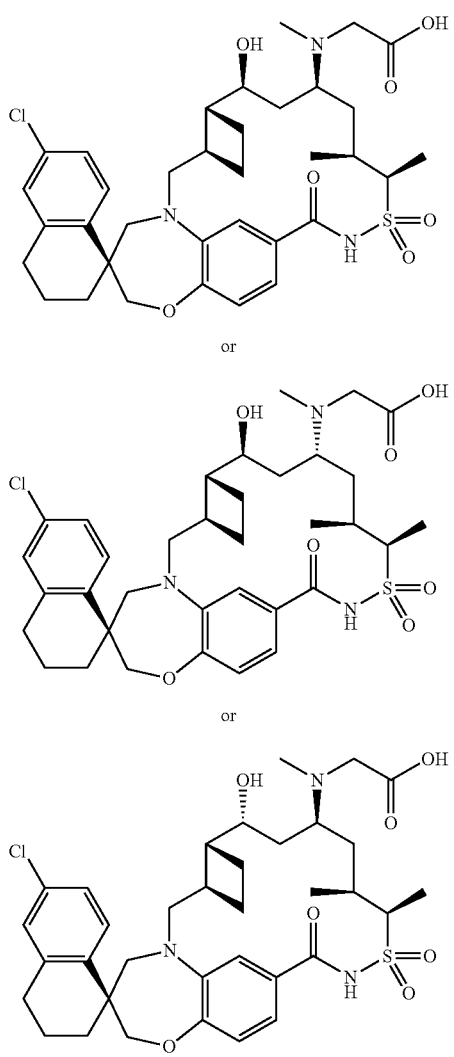

or

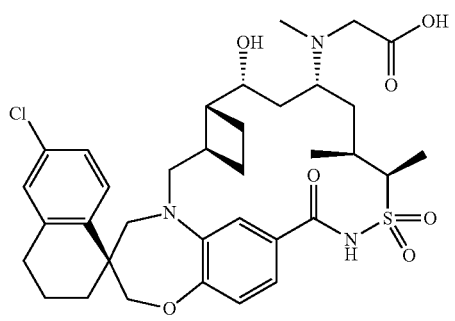

The methyl amino alcohol (12 mg, 0.014 mmol, Example 256) was dissolved in 1,2-dichloroethane (140 μL) and a drop of acetic acid (0.80 μL, 0.014 mmol) was added followed by ethyl glyoxalated, ca 50% soln. in toluene (5.5 μL, 0.028 mmol) and sodium triacetoxyborohydride (5.9 mg, 0.028 mmol). The mixture was stirred for several days after adding several more equivalents of ethyl glyoxylate, ca 50% soln. in toluene (5.5 μL, 0.028 mmol) and sodium triacetoxyborohydride (5.9 mg, 0.028 mmol). Sodium cyanoborohydride (0.88 mg, 0.014 mmol) and MeOH was then added and the reaction was completed after stirring overnight. The reaction was then quenched with saturated sodium bicarbonate solution and extracted with EtOAc to give 6.5 mg of a crude mixture. This mixture (6.5 mg, 9.07 μmol) was dissolved in THF (1.0 mL) and sodium hydroxide (5 N soln.) (0.5 mL, 2.5 mmol) was added and the mixture was stirred overnight. The reaction was then acidified by addition of TFA (0.21 mL, 2.7 mmol). The mixture was concentrated and then dissolved in DMSO. The crude material was purified by reverse-phase preparative HPLC using a Phenomenex Gemini column, 10 micron, C18, 100 Å, 150×30 mm, 0.1% TFA in CH$_3$CN/H$_2$O, gradient 20% to 50% over 30 min to provide N-((1S,3'R,6'R,7'S,9'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-9'-yl)-N-methylglycine or N-((1S,3'R,6'R,7'S,9'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-9'-yl)-N-methylglycine or N-((1S,3'R,6'R,7'R,9'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-9'-yl)-N-methylglycine or N-((1S,3'R,6'R,7'R,9'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-9'-yl)-N-methylglycine as the first eluting and major isomer (0.6 mg, 0.6 μma 7% yield). $^1$H NMR (400 MHz, MeOH-d$_4$) δ 7.75 (dd, J=3.30, 8.44 Hz, 1H), 7.35 (s, 1H), 7.19 (dd, J=1.96, 8.31 Hz, 1H), 7.12 (t, J=2.45 Hz, 1H), 6.98 (d, J=1.71 Hz, 1H), 6.94-6.97 (m, 1H), 4.16 (d, J=12.23 Hz, 1H), 4.08-4.13 (m, 1H), 3.90-4.05 (m, 3H), 3.77-3.89 (m, 2H), 3.66 (d, J=14.67 Hz, 1H), 3.42 (d, J=14.18 Hz, 1H), 2.94 (s, 3H), 2.72-2.91 (m, 4H), 2.34 (br. s., 1H), 2.07-2.16 (m, 3H), 1.86-2.01 (m, 6H), 1.55-1.83 (m, 5H), 1.48 (d, J=7.09 Hz, 3H), 1.14 (d, J=6.60 Hz, 3H). m/z (ESI, +ve ion) 687.7 (M+H)$^+$.

Example 288. N-((1S,3'R,6'R,7'S,9'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [16,18,24]trien]-9'-yl)-N-methyl glycine or N-((1S,3'R,6'R,7'S,9'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [16,18,24]trien]-9'-yl)-N-methyl glycine or N-((1S,3'R,6'R,7'R,9'S,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [16,18,24]trien]-9'-yl)-N-methyl glycine or N-((1S,3'R,6'R,7'R,9'R,11'S,12'R)-6-chloro-7'-hydroxy-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [16,18,24]trien]-9'-yl)-N-methyl-glycine

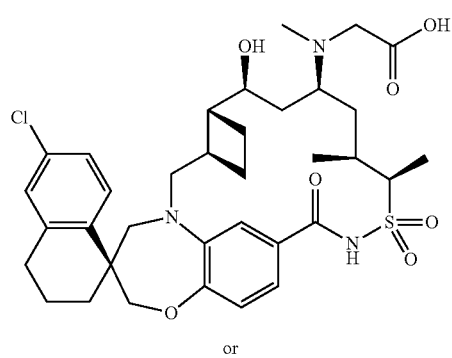

or

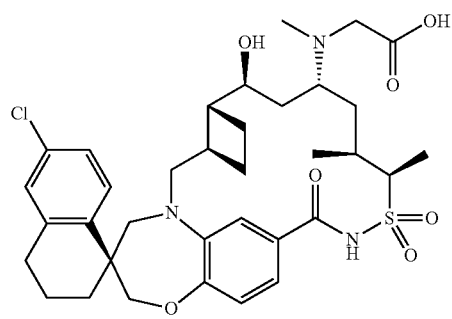

or

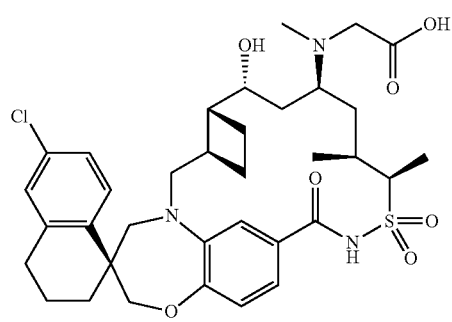

or

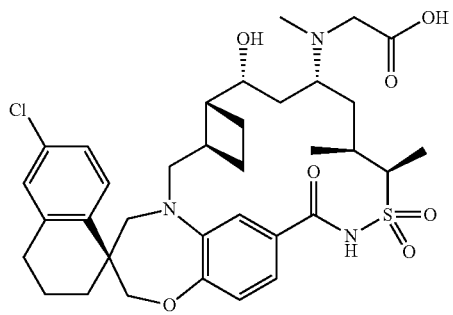

The title compound was obtained as the second eluting and minor isomer using reverse-phase preparative HPLC using a Phenomenex Gemini column, 10 micron, C18, 100 Å, 150×30 mm, 0.1% TFA in CH₃CN/H₂O, gradient 20% to 50% over 30 min in Example 287 (0.3 mg, 0.3 μmol, 4% yield). ¹H NMR (500 MHz, MeOH-d₄) δ 7.74 (d, J=8.56 Hz, 1H), 7.35 (d, J=1.71 Hz, 1H), 7.17 (d, J=8.31 Hz, 1H), 7.11 (d, J=2.20 Hz, 1H), 7.08 (dd, J=1.96, 8.31 Hz, 1H), 6.94 (d, J=8.07 Hz, 1H), 4.10 (dd, J=2.93, 4.16 Hz, 2H), 3.97-4.03 (m, J=17.12 Hz, 2H), 3.87-3.96 (m, 1H), 3.67-3.79 (m, 2H), 3.65 (d, J=13.69 Hz, 1H), 3.07 (dd, J=9.05, 15.89 Hz, 1H), 2.92 (s, 3H), 2.73-2.82 (m, 2H), 2.54-2.63 (m, 1H), 2.47 (s, 1H), 2.04-2.13 (m, J=13.20 Hz, 3H), 1.95-2.00 (m, 3H), 1.57-1.91 (m, 9H), 1.50 (d, J=7.34 Hz, 3H), 1.12 (d, J=6.85 Hz, 3H). m/z (ESI, +ve ion) 687.7 (M+H)⁺.

Example 292. (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-7'-yl)oxy)acetic acid

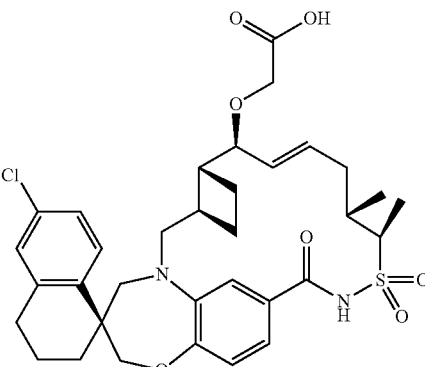

Step 1: (((1S,3'R,6'R,7'S,8'E,11'S,12'R)-6-chloro-11', 12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)acetic acid ethyl ester and ethyl ((1S,3'R,6'R,7'S,8'E,11'S,12'R)-6-chloro-7'-(2-ethoxy-2-oxoethoxy)-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-17'-yl)acetate

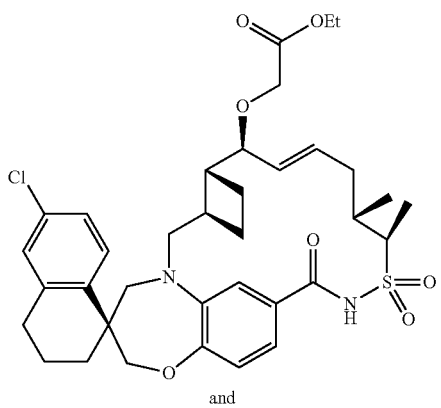

and

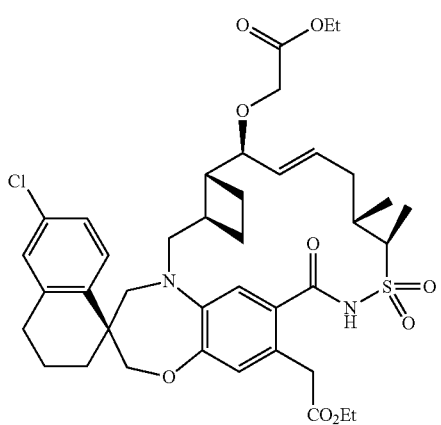

To a stirred solution of (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]-tetraen]-15'-one 13',13'-dioxide (304 mg, 0.507 mmol, Example 719, Step 2) and rhodium (ii) acetate dimer (44.8 mg, 0.101 mmol) in DCM (5.0 mL) was added dropwise ethyl diazoacetate (0.263 mL, 2.54 mmol). Note that strong bubbling occurred during and after the addition. The mixture was stirred at rt for a period of 1 h 10 min at which time the LC-MS showed complete conversion. The mixture was loaded onto silica gel precolumn and subjected to combiflash column chromatography (EtOAc/Hexanes, 30 min from 0 to 60%, 24 g ISCO silica gel column) to give a mixture of the title compounds (290 mg, 0.423 mmol, 83% yield) as a orange-colored solid, impure and taken onto the next step directly. Note that the mono-ester was the major product.

Step 2: (((1S,3'R,6'R,7'S,8'E,11'S,12'R)-6-chloro-11', 12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)acetic Acid To a stirred suspension of the impure mixture of (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetic acid ethyl ester and ethyl ((1S,3'R,6'R,7'S,8'E,11'S,12'R)-6-chloro-7'-(2-ethoxy-2-oxoethoxy)-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-17'-yl)acetate (0.290 g, 0.423 mmol) in a mixed solvent comprising MeOH (5.0 mL), THF (5.0 mL), and water (1.0 mL) was added lithium hydroxide monohydrate (0.044 g, 1.058 mmol) at rt. The resulting mixture was stirred at 50° C. in a preheated oil bath for a period of 1 h 20 min. The LC-MS showed clean completion. The volume was reduced and the residue was taken up in DMSO and subjected to preparative reverse-phase HPLC (Gemini™ Prep C$_{18}$ 5 μm column; Phenomenex, Torrance, CA; gradient elution of 45-95% acetonitrile in water, where both solvents contained 0.1% TFA, 30 min method) to give, after lyophilization, the title compound (120 mg, 0.152 mmol, 43% yield) as the second eluting fraction as an off-white solid. $^1$H NMR (500 MHz, CDCl$_3$) δ 8.03 (s, 1H), 7.69 (d, J=8.3 Hz, 1H), 7.19 (dd, J=2.2, 8.3 Hz, 1H), 7.10 (d, J=2.2 Hz, 1H), 6.96-6.88 (m, 2H), 6.83 (d, J=1.2 Hz, 1H), 5.97-5.88 (m, 1H), 5.57 (dd, J=9.4, 15.0 Hz, 1H), 4.33 (q, J=6.8 Hz, 1H), 4.14-3.97 (m, 4H), 3.95 (dd, J=3.3, 9.4 Hz, 1H), 3.83 (d, J=15.2 Hz, 1H), 3.70 (d, J=14.2 Hz, 1H), 3.23 (d, J=14.4 Hz, 1H), 3.03 (dd, J=10.3, 15.2 Hz, 1H), 2.87-2.50 (m, 4H), 2.34 (td, J=9.1, 18.3 Hz, 1H), 2.24-1.78 (m, 8H), 1.69 (quin, J=9.6 Hz, 1H), 1.51 (d, J=7.3 Hz, 3H), 1.40 (t, J=13.0 Hz, 1H), 1.07 (d, J=6.8 Hz, 3H). m/z (ESI, +ve ion) 657.2 (M+H)$^+$.

Example 293. ((1S,3'R,6'R,7'S,8'E,11'S,12'R)-7'-(carboxymethoxy)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-17'-yl)acetic acid

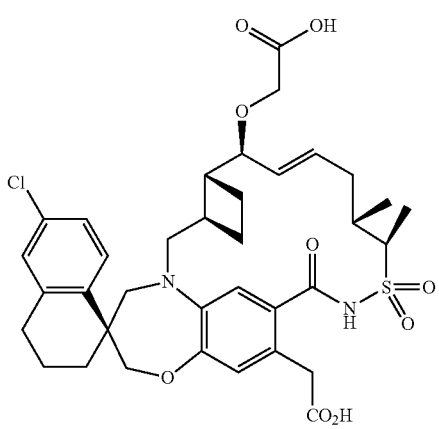 [SMILES: C[C@@H]1[C@@H](C)C/C=C/[C@H](OCC(=O)O)[C@@H]2CC[C@H]2CN2C[C@@]3(CCCc4cc(Cl)ccc43)COc3cc(CC(=O)O)c(cc32)C(=O)NS1(=O)=O]

The title compound (6.5 mg) was obtained as an off-white solid as the first eluting isomer from preparative reverse-phase HPLC (Gemini Prep C$_{18}$ 5 μm column; Phenomenex, Torrance, CA; gradient elution of 45-95% acetonitrile in water, where both solvents contained 0.1% TFA, 30 min method) in Example 292. $^1$H NMR (400 MHz, CDCl$_3$) δ 10.79 (s, 1H), 7.66 (d, J=8.6 Hz, 1H), 7.16 (dd, J=2.2, 8.6 Hz, 1H), 7.09 (d, J=2.2 Hz, 1H), 6.80 (s, 1H), 6.70 (s, 1H), 5.99-5.78 (m, 1H), 5.58 (dd, J=9.3, 15.2 Hz, 1H), 4.23 (q, J=6.8 Hz, 1H), 4.09-3.99 (m, 5H), 3.91 (dd, J=3.1, 9.6 Hz, 1H), 3.83-3.59 (m, 3H), 3.27 (d, J=14.3 Hz, 1H), 3.05 (dd, J=10.7, 15.4 Hz, 1H), 2.89-1.77 (m, 13H), 1.75-1.64 (m, 1H), 1.50 (d, J=7.2 Hz, 3H), 1.39 (t, J=12.9 Hz, 1H), 1.09 (d, J=6.3 Hz, 3H). m/z (ESI, +ve ion) 715.0 (M+H)$^+$.

Example 294. 2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-methylacetamide

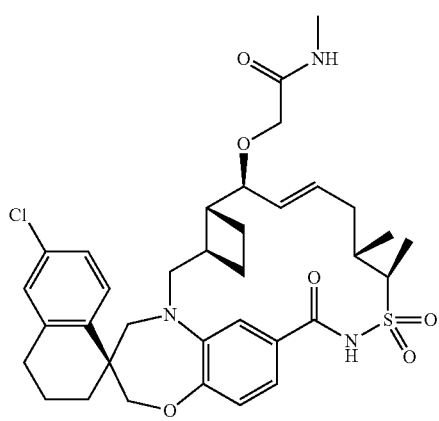 [SMILES: CNC(=O)CO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

To a stirred solution of impure (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetic acid (10 mg, 0.015 mmol, Example 292) and HATU (11.57 mg, 0.030 mmol, in excess) in DMF (1.2 mL) was added methylamine, 2.0 M solution in tetrahydrofuran (0.076 mL, 0.152 mmol) (0.4 mL, actual) at rt. The resulting mixture was stirred at rt for a period of 0.5 h. The crude mixture was taken up in DMSO and subjected to preparative reverse-phase HPLC (Gemini Prep C$_{18}$ 5 μm column; Phenomenex, Torrance, CA; gradient elution of 50-95% acetonitrile in water, where both solvents contained 0.1% TFA, 30 min method) to give, after lyophilization, 5.0 mg of the title compound as an off-white solid. $^1$H NMR (400 MHz, CDCl$_3$) δ 7.97 (s, 1H), 7.69 (d, J=8.4 Hz, 1H), 7.19 (dd, J=2.3, 8.4 Hz, 1H), 7.10 (d, J=2.2 Hz, 1H), 6.97-6.79 (m, 3H), 5.93-5.79 (m, 1H), 5.56 (dd, J=8.9, 15.6 Hz, 1H), 4.43-4.26 (m, 1H), 4.17-3.96 (m, 4H), 3.90-3.78 (m, 2H), 3.71 (d, J=14.3 Hz, 1H), 3.23 (d, J=14.3 Hz, 1H), 3.09-2.94 (m, 7H), 2.87-2.73 (m, 2H), 2.65-2.54 (m, 1H), 2.31 (quin, J=8.9 Hz, 1H), 2.24-1.76 (m, 7H), 1.74-1.58 (m, 1H), 1.50 (d, J=7.2 Hz, 3H), 1.45-1.31 (m, 1H), 1.06 (d, J=6.8 Hz, 3H). m/z (ESI, +ve ion) 670.1 (M+H)$^+$.

Example 295. 2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N,N-dimethylacetamide

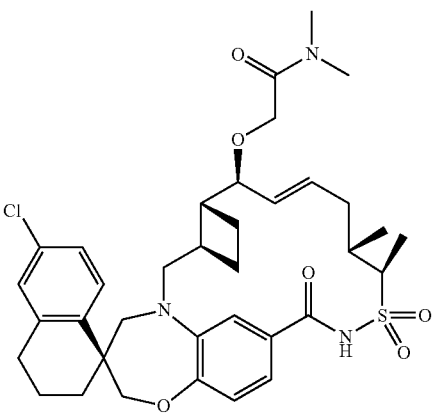 [SMILES: C[C@@H]1[C@@H](C)C/C=C/[C@H](OCC(=O)N(C)C)[C@@H]2CC[C@H]2CN2C[C@@]3(CCCc4cc(Cl)ccc43)COc3ccc(cc32)C(=O)NS1(=O)=O]

The title compound was synthesized according to the procedure exemplified in Example 294. The crude mixture was subjected to preparative reverse-phase HPLC (Gemini™ Prep C$_{18}$ 5 μm column; Phenomenex, Torrance, CA; gradient elution of 20-95% acetonitrile in water, where both solvents contained 0.1% TFA, 30 min method) to give, after lyophilization, 4.5 mg of the title compound as an off-white solid. $^1$H NMR (400 MHz, CDCl$_3$) δ 7.97 (s, 1H), 7.69 (d, J=8.4 Hz, 1H), 7.19 (dd, J=2.3, 8.4 Hz, 1H), 7.10 (d, J=2.2 Hz, 1H), 6.97-6.78 (m, 3H), 5.94-5.77 (m, 1H), 5.56 (dd, J=8.9, 15.6 Hz, 1H), 4.43-4.26 (m, 1H), 4.17-3.96 (m, 4H), 3.88-3.78 (m, 2H), 3.71 (d, J=14.3 Hz, 1H), 3.23 (d, J=14.3 Hz, 1H), 3.07-2.95 (m, 7H), 2.87-2.73 (m, 2H), 2.70 (s, 2H), 2.66-2.54 (m, 1H), 2.41-1.74 (m, 8H), 1.72-1.59 (m, 1H), 1.50 (d, J=7.2 Hz, 3H), 1.43-1.33 (m, 1H), 1.06 (d, J=6.8 Hz, 3H). m/z (ESI, +ve ion) 684.0 (M+H)$^+$.

Example 296. 2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-(1-methylethyl)acetamide

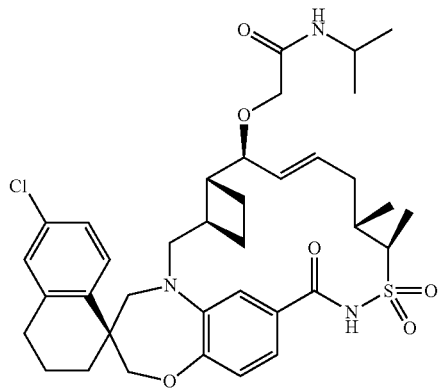 [SMILES: CC(C)NC(=O)CO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

The title compound (6.5 mg as an off-white solid) was synthesized and purified according to the procedure exemplified in Example 294. ¹H NMR (400 MHz, CDCl₃) δ 7.99 (s, 1H), 7.70 (d, J=8.4 Hz, 1H), 7.19 (dd, 8.5 Hz, 1H), 7.10 (d, J=2.2 Hz, 1H), 6.97-6.88 (m, 2H), 6.84 (s, 1H), 6.33 (d, J=7.0 Hz, 1H), 6.02-5.82 (m, 1H), 5.54 (dd, J=9.2, 14.5 Hz, 1H), 4.33 (q, J=7.1 Hz, 1H), 4.20-4.02 (m, 3H), 3.95-3.63 (m, 5H), 3.24 (d, J=14.3 Hz, 1H), 3.03 (dd, J=10.2, 15.3 Hz, 1H), 2.87-2.64 (m, 2H), 2.55-2.42 (m, 1H), 2.41-2.26 (m, 1H), 2.25-1.76 (m, 9H), 1.75-1.64 (m, 1H), 1.51 (d, J=7.2 Hz, 3H), 1.41 (t, J=12.6 Hz, 1H), 1.19 (t, J=6.1 Hz, 6H), 1.06 (d, J=6.8 Hz, 3H). m/z (ESI, +ve ion) 698.0 (M+H)⁺.

Example 297. 2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl)oxy)-N-(2,2,2-trifluoroethyl)acetamide

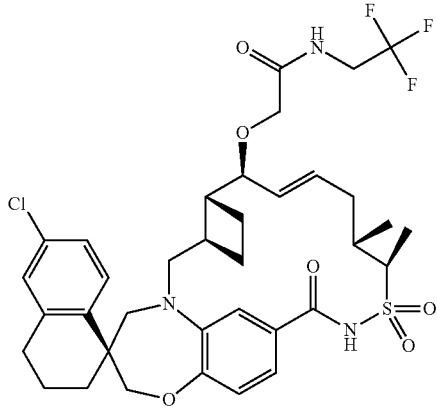 [SMILES: C[C@@H]1[C@@H](C)C/C=C/[C@H](OCC(=O)NCC(F)(F)F)[C@@H]2CC[C@H]2CN2C[C@@]3(CCCc4cc(Cl)ccc43)COc3ccc(cc32)C(=O)NS1(=O)=O]

The title compound was synthesized according to the procedure exemplified in Example 294. Note that triethylamine was used as the general base in the reaction. The crude mixture was subjected to preparative reverse-phase HPLC (Gemini Prep C₁₈ 5 μm column; Phenomenex, Torrance, CA; gradient elution of 45-95% acetonitrile in water, where both solvents contained 0.1% TFA, 30 min method) to give, after lyophilization, 7.0 mg of the title compound as an off-white solid. ¹H NMR (500 MHz, CDCl₃) δ 8.01 (s, 1H), 7.70 (d, J=8.3 Hz, 1H), 7.19 (dd, J=2.2, 8.6 Hz, 1H), 7.10 (d, J=2.0 Hz, 1H), 6.98-6.89 (m, 2H), 6.83 (d, J=1.2 Hz, 1H), 6.75 (br. s., 1H), 5.99-5.84 (m, 1H), 5.55 (dd, J=9.5, 15.2 Hz, 1H), 4.32 (q, J=7.2 Hz, 1H), 4.14-4.06 (m, 2H), 4.04-3.86 (m, 5H), 3.82 (d, J=15.2 Hz, 1H), 3.71 (d, J=14.2 Hz, 1H), 3.24 (d, J=14.2 Hz, 1H), 3.03 (dd, J=10.3, 15.2 Hz, 1H), 2.87-2.71 (m, 2H), 2.55-2.44 (m, 1H), 2.36 (quin, J=9.2 Hz, 1H), 2.23-1.62 (m, 10H), 1.51 (d, J=7.3 Hz, 3H), 1.44-1.37 (m, 1H), 1.06 (d, J=6.8 Hz, 3H). m/z (ESI, +ve ion) 738.0 (M+H)⁺.

Example 298. 2-(((1S,3'R,6'R,7'S,8'E,11'S,12'R)-6-chloro-11',12'-dimethyl-13',13'-dioxido-15'-oxo-3,4-dihydro-2H-[spiro[naphthalene-1,22'-20]oxa[13]thia[1,14]diazatetracyclo[14.7.2.0³,⁶.0¹⁹,²⁴]pentacosa[8,16,18,24]tetraen]-7'-yl)oxy)-N-(2-methoxyethyl)acetamide

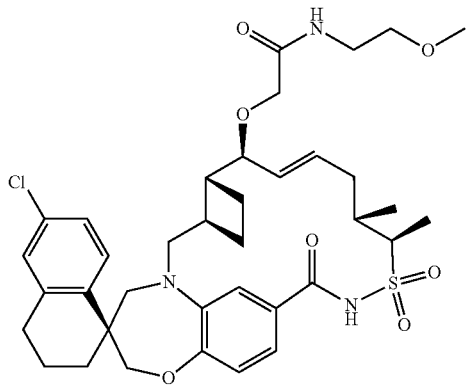 [SMILES: COCCNC(=O)CO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

The title compound (6.0 mg as a white solid) was synthesized and purified according to the procedure exemplified in Example 294. ¹H NMR (500 MHz, CDCl₃) δ 8.02 (s, 1H), 7.70 (d, J=8.6 Hz, 1H), 7.19 (dd, J=2.3, 8.4 Hz, 1H), 7.10 (d, J=2.2 Hz, 1H), 6.97-6.80 (m, 4H), 5.97-5.83 (m, 1H), 5.54 (dd, J=9.8, 14.7 Hz, 1H), 4.38-4.26 (m, 1H), 4.15-4.03 (m, 2H), 3.97-3.89 (m, 1H), 3.88-3.77 (m, 3H), 3.70 (d, J=14.2 Hz, 1H), 3.52-3.44 (m, 4H), 3.39 (s, 3H), 3.24 (d, J=14.2 Hz, 1H), 3.02 (dd, J=10.0, 15.2 Hz, 1H), 2.89-2.67 (m, 2H), 2.56-2.44 (m, 1H), 2.35 (quin, J=9.1 Hz, 1H), 2.24-2.13 (m, 1H), 2.11-1.60 (m, 9H), 1.51 (d, J=7.3 Hz, 3H), 1.40 (t, J=12.8 Hz, 1H), 1.06 (d, J=6.8 Hz, 3H). m/z (ESI, +ve ion) 714.1 (M+H)⁺.

Example 299. 2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl)oxy)-N-(2-methoxyethyl)-N-methylacetamide

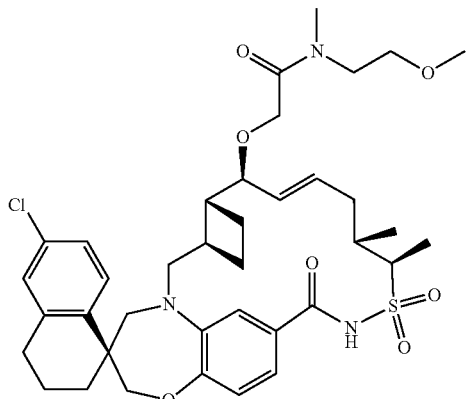

The title compound (5.0 mg as a white solid) was synthesized and purified according to the procedure exemplified in Example 294. Note that DIEA was utilized as the general base in the reaction. $^1$H NMR (400 MHz, CDCl$_3$) δ 8.00 (s, 1H), 7.69 (d, J=8.6 Hz, 1H), 7.18 (dd, J=2.2, 8.5 Hz, 1H), 7.10 (d, J=2.2 Hz, 1H), 6.97-6.76 (m, 3H), 5.98-5.74 (m, 1H), 5.66-5.46 (m, 1H), 4.33 (q, J=7.2 Hz, 1H), 4.22-3.96 (m, 4H), 3.83 (d, J=13.7 Hz, 2H), 3.74-3.62 (m, 2H), 3.61-3.55 (m, 1H), 3.54-3.42 (m, 2H), 3.37 (d, J=5.1 Hz, 3H), 3.23 (d, J=14.3 Hz, 1H), 3.09-2.95 (m, 4H), 2.88-2.68 (m, 2H), 2.60 (d, J=8.4 Hz, 1H), 2.39-2.24 (m, 1H), 2.24-1.74 (m, 9H), 1.65 (quin, J=9.4 Hz, 1H), 1.50 (d, J=7.0 Hz, 3H), 1.39 (t, J=12.7 Hz, 1H), 1.06 (d, J=6.8 Hz, 3H). m/z (ESI, +ve ion) 728.1 (M+H)$^+$.

Example 300. 2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-(2-(dimethylamino)ethyl)-N-methylacetamide 1H), 4.24-4.02 (m, 5H), 3.92 (dd, J=2.9, 9.3 Hz, 1H), 3.85-3.69 (m, 3H), 3.65 (d, J=14.2 Hz, 1H), 3.37 (t, J=6.0 Hz, 2H), 3.33-3.26 (m, 3H), 3.11 (dd, J=10.3, 15.4 Hz, 1H), 3.07 (s, 3H), 2.97 (s, 6H), 2.86-2.70 (m, 2H), 2.61-2.50 (m, 1H), 2.31 (quin, J=9.3 Hz, 1H), 2.24-1.66 (m, 8H), 1.53-1.38 (m, 4H), 1.06 (d, J=6.8 Hz, 3H). m/z (ESI, +ve ion) 741.1 (M+H)$^+$.

Example 301. 2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-methoxyacetamide

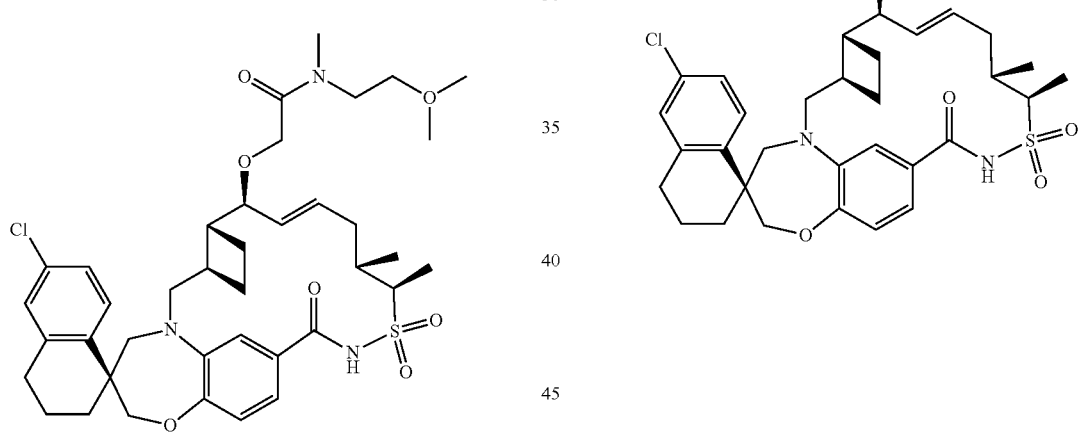

The title compound was synthesized according to the procedure exemplified in Example 294. The crude mixture was subjected to preparative reverse-phase HPLC (Gemini Prep C$_{18}$ 5 μm column; Phenomenex, Torrance, CA; gradient elution of 30-95% acetonitrile in water, where both solvents contained 0.1% TFA, 30 min method) to give, after lyophilization, 6.5 mg of the title compound as an off-white solid. $^1$H NMR (500 MHz, CD$_3$OD) δ 7.72 (d, J=8.6 Hz, 1H), 7.17 (dd, J=2.2, 8.6 Hz, 1H), 7.11 (d, J=2.2 Hz, 1H), 7.05 (dd, J=2.0, 8.1 Hz, 1H), 6.93 (d, J=8.1 Hz, 1H), 6.86 (d, J=1.7 Hz, 1H), 5.88-5.76 (m, 1H), 5.60 (dd, J=9.2, 15.3 Hz, The title compound was synthesized according to the procedure exemplified in Example 294. Note that DIEA was utilized as the general base in the reaction. The crude mixture was subjected to preparative reverse-phase HPLC (Gemini™ Prep C$_{18}$ 5 μm column; Phenomenex, Torrance, CA; gradient elution of 45-95% acetonitrile in water, where both solvents contained 0.1% TFA, 30 min method) to give, after lyophilization, 2.0 mg of the title compound as an off-white solid. $^1$H NMR (400 MHz, CDCl$_3$) δ 8.79 (br. s., 1H), 7.99 (s, 1H), 7.69 (d, J=8.4 Hz, 1H), 7.19 (dd, J=2.2, 8.5 Hz, 1H), 7.10 (d, J=2.2 Hz, 1H), 6.99-6.73 (m, 3H), 5.98-5.83 (m, 1H), 5.52 (dd, J=10.0, 15.1 Hz, 1H), 4.44-4.24 (m, 1H), 4.16-4.04 (m, 2H), 4.03-3.86 (m, 2H), 3.86-3.77 (m, 5H), 3.70 (d, J=14.7 Hz, 1H), 3.23 (d, J=14.3 Hz, 1H), 3.03 (dd, J=10.0, 15.3 Hz, 1H), 2.88-2.66 (m, 3H), 2.54-2.27 (m, 2H), 2.25-1.57 (m, 9H), 1.55-1.34 (m, 4H), 1.07 (d, J=6.8 Hz, 3H). m/z (ESI, +ve ion) 686.1 (M+H)$^+$.

761

Example 302. 2-((((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N,N-bis(2-methoxyethyl)acetamide

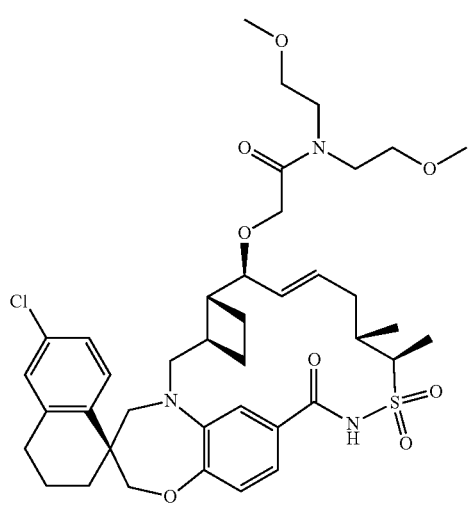 [SMILES: COCCN(CCOC)C(=O)CO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

The title compound (5.5 mg as an off-white solid) was synthesized and purified according to the procedure exemplified in Example 294. Note that DIEA was utilized as the general base in the reaction. $^1$H NMR (500 MHz, CDCl$_3$) δ 7.99 (s, 1H), 7.73-7.67 (m, 1H), 7.18 (dd, J=2.3, 8.4 Hz, 1H), 7.10 (d, J=2.2 Hz, 1H), 6.95-6.81 (m, 3H), 5.93-5.76 (m, 1H), 5.57 (dd, J=9.2, 14.8 Hz, 1H), 4.34 (q, J=6.9 Hz, 1H), 4.24-4.17 (m, 1H), 4.13-4.01 (m, 3H), 3.90-3.78 (m, 2H), 3.70 (d, J=14.2 Hz, 1H), 3.66-3.44 (m, 8H), 3.35 (d, J=7.6 Hz, 6H), 3.23 (d, J=14.4 Hz, 1H), 3.01 (dd, J=10.5, 15.4 Hz, 1H), 2.87-2.55 (m, 3H), 2.31 (quin, J=9.0 Hz, 1H), 2.24-1.72 (m, 9H), 1.70-1.59 (m, 1H), 1.50 (d, J=7.1 Hz, 3H), 1.38 (t, J=12.7 Hz, 1H), 1.06 (d, J=6.8 Hz, 3H). m/z (ESI, +ve ion) 772.0 (M+H)$^+$.

762

Example 303. 2-((((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-3-oxetanylacetamide

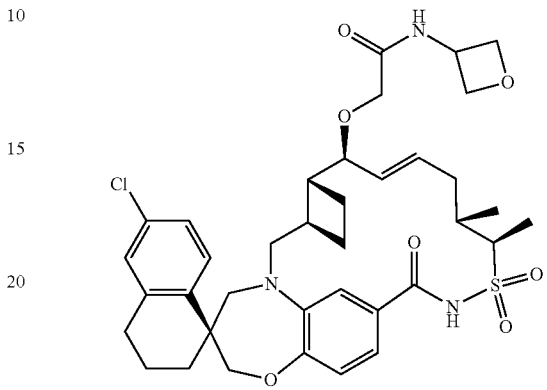

The title compound (3.0 mg as an off-white solid) was synthesized and purified according to the procedure exemplified in Example 294. Note that DIEA was utilized as the general base in the reaction. $^1$H NMR (400 MHz, CDCl$_3$) δ 8.01 (s, 1H), 7.70 (d, J=8.6 Hz, 1H), 7.19 (dd, J=2.3, 8.4 Hz, 1H), 7.10 (d, J=2.2 Hz, 1H), 7.06-6.87 (m, 3H), 6.84 (s, 1H), 5.99-5.84 (m, 1H), 5.56 (dd, J=9.1, 15.6 Hz, 1H), 5.18-5.05 (m, 1H), 5.02-4.90 (m, 2H), 4.54 (dt, J=4.2, 6.3 Hz, 2H), 4.32 (q, J=7.2 Hz, 1H), 4.16-4.03 (m, 2H), 3.98-3.61 (m, 5H), 3.25 (d, J=14.3 Hz, 1H), 3.05 (dd, J=10.4, 15.1 Hz, 1H), 2.87-2.71 (m, 2H), 2.60-2.45 (m, 1H), 2.37 (quin, J=9.0 Hz, 1H), 2.25-1.61 (m, 10H), 1.51 (d, J=7.2 Hz, 3H), 1.41 (t, J=12.9 Hz, 1H), 1.07 (d, J=6.8 Hz, 3H). m/z (ESI, +ve ion) 712.1 (M+H)$^+$.

Example 304. (1S,3'R,6'R,7'S,8'E,11'S,12'R)-6-chloro-7'-(2-(3-hydroxy-1-azetidinyl)-2-oxoethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

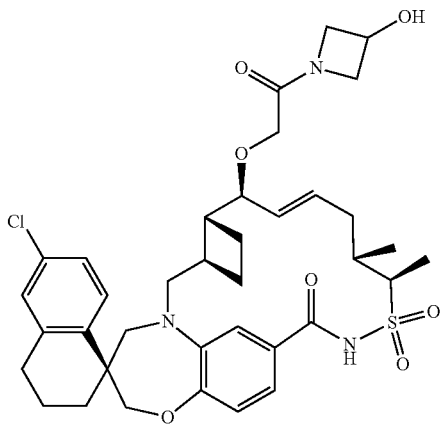 [SMILES: C[C@@H]1[C@@H](C)C/C=C/[C@H](OCC(=O)N2CC(O)C2)[C@@H]2CC[C@H]2CN2C[C@@]3(CCCc4cc(Cl)ccc43)COc3ccc(cc32)C(=O)NS1(=O)=O]

The title compound (6.0 mg as a white solid) was synthesized and purified according to the procedure exemplified in Example 294. Note that DIEA was utilized as the general base in the reaction. ¹H NMR (400 MHz, CDCl₃) δ 8.15-7.96 (m, 1H), 7.71 (d, J=8.6 Hz, 1H), 7.20 (dd, J=2.2, 8.4 Hz, 1H), 7.11 (d, J=2.2 Hz, 1H), 6.99-6.79 (m, 3H), 5.96-5.72 (m, 1H), 5.62-5.45 (m, 1H), 4.71 (br. s., 1H), 4.49 (d, J=6.3 Hz, 1H), 4.40-4.24 (m, 2H), 4.21-3.64 (m, 9H), 3.24 (d, J=14.3 Hz, 1H), 3.04 (dd, J=10.5, 15.0 Hz, 1H), 2.91-2.64 (m, 2H), 2.54 (d, J=8.4 Hz, 1H), 2.40-2.26 (m, 1H), 2.25-1.75 (m, 10H), 1.74-1.58 (m, 1H), 1.52 (d, J=7.2 Hz, 3H), 1.41 (t, J=12.6 Hz, 1H), 1.08 (d, J=6.7 Hz, 3H). m/z (ESI, +ve ion) 712.1 (M+H)⁺.

Example 305. (1S,3'R,6'R,7'S,8'E,11'S,12'R)-6-chloro-7'-(2-(3-hydroxy-3-methyl-1-azetidinyl)-2-oxoethoxy)-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide The title compound was synthesized according to the procedure exemplified in Example 294. Note that DIEA was utilized as the general base in the reaction. The crude mixture was subjected to preparative reverse-phase HPLC (Gemini Prep C₁₈ 5 μm column; Phenomenex, Torrance, CA; gradient elution of 45-95% acetonitrile in water, where both solvents contained 0.1% TFA, 30 min method) to give, after lyophilization, 3.0 mg of the title compound as an off-white solid. ¹H NMR (400 MHz, CDCl₃) δ 8.16-7.93 (m, 1H), 7.69 (d, J=8.4 Hz, 1H), 7.19 (dd, J=2.2, 8.4 Hz, 1H), 7.10 (d, J=2.2 Hz, 1H), 6.98-6.76 (m, 3H), 5.98-5.71 (m, 1H), 5.52 (dd, J=9.0, 14.9 Hz, 1H), 4.42-4.23 (m, 1H), 4.22-3.77 (m, 11H), 3.70 (d, J=14.9 Hz, 1H), 3.22 (d, J=14.3 Hz, 1H), 3.09-2.94 (m, 1H), 2.88-2.70 (m, 2H), 2.52 (br. s., 1H), 2.37-2.26 (m, 1H), 2.23-1.74 (m, 9H), 1.73-1.63 (m, 1H), 1.57 (d, J=4.3 Hz, 3H), 1.50 (d, J=7.0 Hz, 3H), 1.40 (t, J=12.6 Hz, 1H), 1.06 (d, J=6.8 Hz, 3H). m/z (ESI, +ve ion) 726.0 (M+H)⁺.

Example 306. (1S,3'R,6'R,7'S,8'E,11'S,12'R)-6-chloro-7'-(2-(3-hydroxy-3-(trifluoromethyl)-1-azetidinyl)-2-oxoethoxy)-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

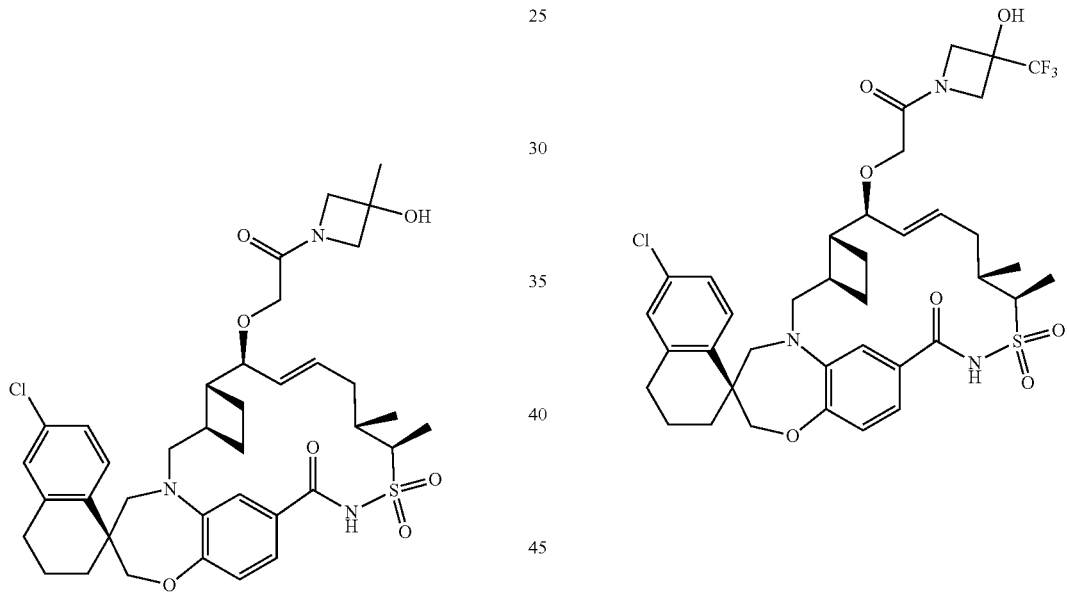

The title compound was synthesized according to the procedure exemplified in Example 294. Note that DIEA was utilized as the general base in the reaction. The crude mixture was subjected to preparative reverse-phase HPLC (Gemini™ Prep C₁₈ 5 μm column; Phenomenex, Torrance, CA; gradient elution of 45-95% acetonitrile in water, where both solvents contained 0.1% TFA, 30 min method) to give, after lyophilization, 3.0 mg of the title compound as an off-white solid. ¹H NMR (400 MHz, CDCl₃) δ 8.11-7.96 (m, 1H), 7.69 (d, J=8.6 Hz, 1H), 7.19 (dd, J=2.2, 8.5 Hz, 1H), 7.10 (d, J=2.2 Hz, 1H), 6.99-6.78 (m, 3H), 5.98-5.74 (m, 1H), 5.52 (dd, J=9.0, 15.3 Hz, 1H), 4.62-4.48 (m, 1H), 4.37-4.21 (m, 3H), 4.11-3.91 (m, 5H), 3.88-3.66 (m, 3H), 3.23 (dd, J=3.2, 14.4 Hz, 1H), 3.09-2.96 (m, 1H), 2.88-2.71 (m, 2H), 2.50 (dd, J=7.6, 16.0 Hz, 1H), 2.39-1.57 (m, 12H), 1.50 (dd, J=3.9, 7.0 Hz, 3H), 1.40 (t, J=12.5 Hz, 1H), 1.07 (d, J=6.7 Hz, 3H). m/z (ESI, +ve ion) 779.9 (M+H)⁺.

Example 307. (1S,3'R,6'R,7'S,8'E,11'S,12'R)-6-chloro-7'-(2-(3-methoxy-1-azetidinyl)-2-oxoethoxy)-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

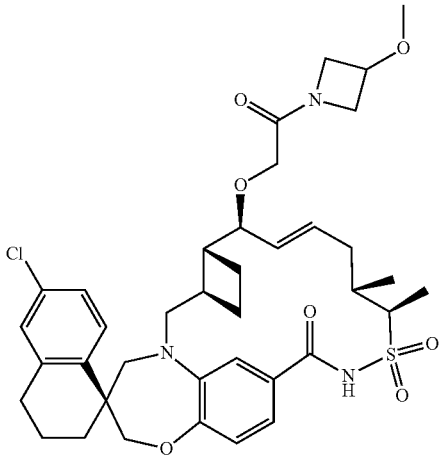 [SMILES: COC1CN(C(=O)CO[C@H]2/C=C/C[C@H](C)[C@@H](C)S(=O)(=O)NC(=O)c3ccc4c(c3)N(C[C@@H]3CC[C@H]32)C[C@@]2(CCCc3cc(Cl)ccc32)CO4)C1]

The title compound (6.0 mg as a white solid) was synthesized and purified according to the procedure exemplified in Example 294. Note that DIEA was utilized as the general base in the reaction. ¹H NMR (400 MHz, CDCl₃) δ 8.02 (d, J=14.9 Hz, 1H), 7.69 (d, J=8.6 Hz, 1H), 7.19 (dd, J=2.1, 8.5 Hz, 1H), 7.10 (d, J=2.0 Hz, 1H), 6.96-6.78 (m, 3H), 5.95-5.79 (m, 1H), 5.60-5.43 (m, 1H), 4.48-4.29 (m, 2H), 4.27-4.17 (m, 2H), 4.15-3.66 (m, 9H), 3.32 (s, 3H), 3.23 (d, J=14.3 Hz, 1H), 3.01 (dd, J=10.2, 15.3 Hz, 1H), 2.87-2.69 (m, 2H), 2.51 (d, J=8.6 Hz, 1H), 2.33 (d, J=7.4 Hz, 1H), 2.25-1.74 (m, 9H), 1.73-1.59 (m, 1H), 1.50 (d, J=7.0 Hz, 3H), 1.40 (t, J=12.6 Hz, 1H), 1.06 (d, J=6.7 Hz, 3H). m/z (ESI, +ve ion) 726.1 (M+H)⁺.

Example 308. (1S,3'R,6'R,7'S,8'E,11'S,12'R)-6-chloro-7'-(2-(3,3-difluoro-1-azetidinyl)-2-oxoethoxy)-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

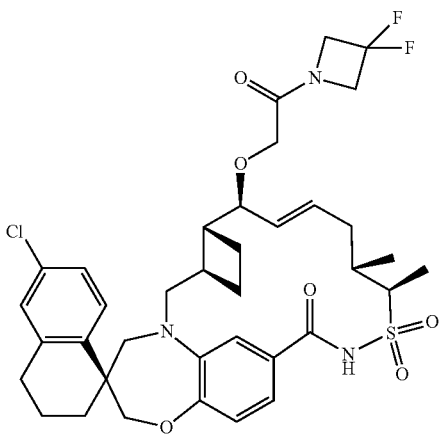 [SMILES: C[C@@H]1[C@@H](C)C/C=C/[C@H](OCC(=O)N2CC(F)(F)C2)[C@@H]2CC[C@H]2CN2C[C@@]3(CCCc4cc(Cl)ccc43)COc3ccc(cc32)C(=O)NS1(=O)=O]

The title compound was synthesized according to the procedure exemplified in Example 294. Note that DIEA was utilized as the general base in the reaction. The crude mixture was subjected to preparative reverse-phase HPLC (Gemini Prep C₁₈ 5 μm column; Phenomenex, Torrance, CA; gradient elution of 45-95% acetonitrile in water, where both solvents contained 0.1% TFA, 30 min method) to give, after lyophilization, 4.5 mg of the title compound as an off-white solid. ¹H NMR (400 MHz, CDCl₃) δ 8.02 (s, 1H), 7.69 (d, J=8.4 Hz, 1H), 7.19 (dd, J=2.2, 8.5 Hz, 1H), 7.10 (d, J=2.2 Hz, 1H), 6.97-6.88 (m, 2H), 6.83 (s, 1H), 5.98-5.84 (m, 1H), 5.51 (dd, J=9.6, 15.1 Hz, 1H), 4.57 (t, J=11.8 Hz, 2H), 4.43-4.28 (m, 3H), 4.19-4.02 (m, 3H), 3.99-3.89 (m, 1H), 3.86-3.78 (m, 2H), 3.71 (d, J=14.3 Hz, 1H), 3.23 (d, J=14.3 Hz, 1H), 3.02 (dd, J=10.3, 15.4 Hz, 1H), 2.88-2.69 (m, 2H), 2.55-2.42 (m, 1H), 2.35 (quin, J=9.2 Hz, 1H), 2.25-1.60 (m, 10H), 1.51 (d, J=7.2 Hz, 3H), 1.40 (t, J=12.7 Hz, 1H), 1.07 (d, J=6.8 Hz, 3H). m/z (ESI, +ve ion) 732.0 (M+H)⁺.

Example 309. (1S,3'R,6'R,7'S,8'E,11'S,12'R)-6-chloro-11',12'-dimethyl-7'-(2-oxo-2-(3-(1-pyrrolidinyl)-1-azetidinyl)ethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

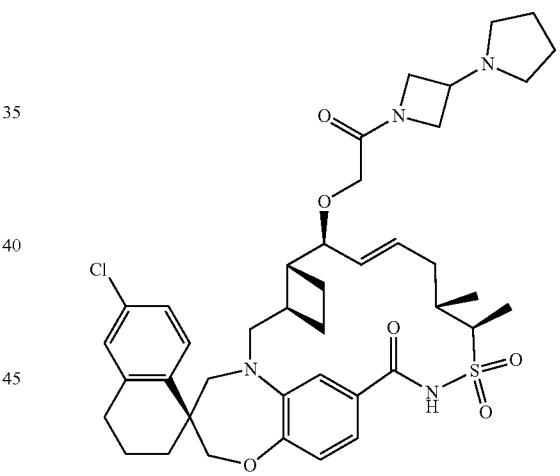

The title compound was synthesized according to the procedure exemplified in Example 294. Note that DIEA was utilized as the general base in the reaction. The crude mixture was subjected to preparative reverse-phase HPLC (Gemini™ Prep C₁₈ 5 μm column; Phenomenex, Torrance, CA; gradient elution of 30-95% acetonitrile in water, where both solvents contained 0.1% TFA, 30 min method) to give, after lyophilization, 3.0 mg of the title compound as an off-white solid. ¹H NMR (500 MHz, CD₃OD) δ 7.73 (d, J=8.6 Hz, 1H), 7.17 (dd, J=2.3, 8.4 Hz, 1H), 7.11 (d, J=2.2 Hz, 1H), 7.05 (d, J=8.1 Hz, 1H), 6.93 (d, J=8.3 Hz, 1H), 6.86 (d, J=3.4 Hz, 1H), 5.93-5.79 (m, 1H), 5.66-5.53 (m, 1H), 4.73-4.63 (m, 1H), 4.47-4.34 (m, 2H), 4.29-3.51 (m, 13H), 3.30-3.25 (m, 2H), 3.10 (dd, J=10.3, 15.4 Hz, 1H), 2.87-2.70 (m, 2H), 2.61-2.49 (m, 1H), 2.40-1.67 (m, 15H), 1.53-1.39 (m, 4H), 1.06 (d, J=6.8 Hz, 3H). m/z (ESI, +ve ion) 765.2 (M+H)⁺.

Example 310. (1S,3'R,6'R,7'S,8'E,11'S,12'R)-6-chloro-7'-(2-((3S)-3-hydroxy-1-pyrrolidinyl)-2-oxoethoxy)-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide Example 311. (1S,3'R,6'R,7'S,8'E,11'S,12'R)-6-chloro-7'-(2-((3R)-3-hydroxy-1-pyrrolidinyl)-2-oxoethoxy)-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

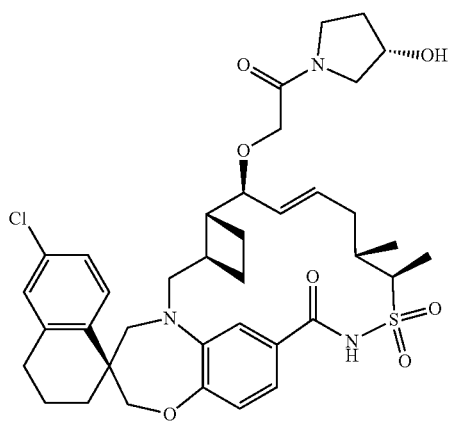 [SMILES: C[C@@H]1[C@@H](C)C/C=C/[C@H](OCC(=O)N2CC[C@H](O)C2)[C@@H]2CC[C@H]2CN2C[C@@]3(CCCc4cc(Cl)ccc43)COc3ccc(cc32)C(=O)NS1(=O)=O]

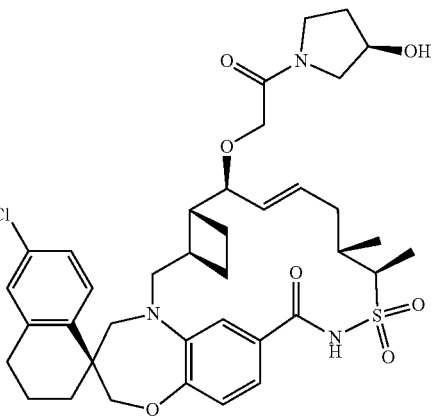

The title compound was synthesized according to the procedure exemplified in Example 294. Note that DIEA was utilized as the general base in the reaction. The crude mixture was subjected to preparative reverse-phase HPLC (Gemini Prep $C_{18}$ 5 μm column; Phenomenex, Torrance, CA; gradient elution of 40-95% acetonitrile in water, where both solvents contained 0.1% TFA, 30 min method) to give, after lyophilization, 1.2 mg of the title compound as an off-white solid. $^1$H NMR (500 MHz, CDCl$_3$) δ 8.17-7.87 (m, 1H), 7.69 (d, J=8.3 Hz, 1H), 7.18 (dd, J=2.2, 8.6 Hz, 1H), 7.10 (d, J=2.2 Hz, 1H), 6.97-6.81 (m, 3H), 5.87-5.75 (m, 1H), 5.57 (dd, J=9.3, 14.9 Hz, 1H), 4.63-4.49 (m, 1H), 4.29 (dd, J=3.4, 7.1 Hz, 1H), 4.15-3.94 (m, 4H), 3.84 (d, J=11.7 Hz, 2H), 3.76-3.42 (m, 5H), 3.23 (d, J=14.4 Hz, 1H), 3.02 (dd, J=10.5, 15.4 Hz, 1H), 2.91-2.70 (m, 2H), 2.66-2.53 (m, 1H), 2.42-1.59 (m, 14H), 1.50 (dd, J=4.4, 7.1 Hz, 3H), 1.44-1.34 (m, 1H), 1.06 (d, J=6.8 Hz, 3H). m/z (ESI, +ve ion) 726.1 (M+H)$^+$.

The title compound was synthesized according to the procedure exemplified in Example 294. Note that DIEA was utilized as the general base in the reaction. The crude mixture was subjected to preparative reverse-phase HPLC (Gemini Prep $C_{18}$ 5 μm column; Phenomenex, Torrance, CA; gradient elution of 40-95% acetonitrile in water, where both solvents contained 0.1% TFA, 30 min method) to give, after lyophilization, 4.5 mg of the title compound as a white solid. $^1$H NMR (500 MHz, CDCl$_3$) δ 7.99 (d, J=7.8 Hz, 1H), 7.69 (d, J=8.3 Hz, 1H), 7.18 (d, J=8.6 Hz, 1H), 7.10 (d, J=2.2 Hz, 1H), 6.98-6.80 (m, 3H), 5.87-5.76 (m, 1H), 5.58 (br. s., 1H), 4.70-4.47 (m, 1H), 4.31 (quin, J=7.2 Hz, 1H), 4.14-4.00 (m, 4H), 3.97-3.39 (m, 10H), 3.23 (d, J=14.4 Hz, 1H), 3.03 (dd, J=10.1, 15.3 Hz, 1H), 2.85-2.70 (m, 2H), 2.61 (br. s., 1H), 2.36-1.57 (m, 9H), 1.53-1.34 (m, 6H), 1.06 (d, J=6.8 Hz, 3H). m/z (ESI, +ve ion) 726.1 (M+H)$^+$.

Example 312. (1S,3'R,6'R,7'S,8'E,11'S,12'R)-6-chloro-7'-(2-(4-hydroxy-1-piperidinyl)-2-oxoethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

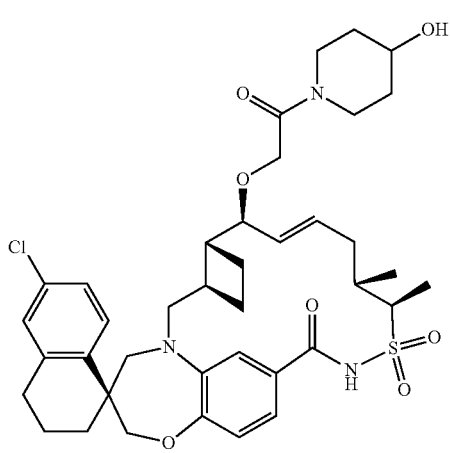 [SMILES: C[C@@H]1[C@@H](C)C/C=C/[C@H](OCC(=O)N2CCC(O)CC2)[C@@H]2CC[C@H]2CN2C[C@@]3(CCCc4cc(Cl)ccc43)COc3ccc(cc32)C(=O)NS1(=O)=O]

The title compound was synthesized according to the procedure exemplified in Example 294. Note that DIEA was utilized as the general base in the reaction. The crude mixture was subjected to preparative reverse-phase HPLC (Gemini Prep $C_{18}$ 5 μm column; Phenomenex, Torrance, CA; gradient elution of 45-95% acetonitrile in water, where both solvents contained 0.1% TFA, 30 min method) to give, after lyophilization, 2.5 mg of the title compound as an off-white solid. $^1$H NMR (400 MHz, CDCl$_3$) δ 7.99 (d, J=12.3 Hz, 1H), 7.69 (d, J=8.6 Hz, 1H), 7.19 (dd, J=2.2, 8.5 Hz, 1H), 7.10 (d, J=2.2 Hz, 1H), 6.98-6.81 (m, 3H), 5.92-5.74 (m, 1H), 5.56 (dd, J=8.8, 15.3 Hz, 1H), 4.31 (dd, J=7.5, 13.8 Hz, 1H), 4.19-3.64 (m, 10H), 3.31-3.09 (m, 3H), 3.03 (t, J=11.8 Hz, 1H), 2.88-2.70 (m, 2H), 2.59 (br. s., 1H), 2.39-1.54 (m, 16H), 1.50 (d, J=7.2 Hz, 3H), 1.39 (t, J=12.9 Hz, 1H), 1.06 (d, J=6.8 Hz, 3H). m/z (ESI, +ve ion) 740.1 (M+H)$^+$.

Example 313. (1S,3'R,6'R,7'S,8'E,11'S,12'R)-6-chloro-11',12'-dimethyl-7'-(2-(4-morpholinyl)-2-oxoethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacos [8,16,18,24]tetraen]-15'-one 13',13'-dioxide

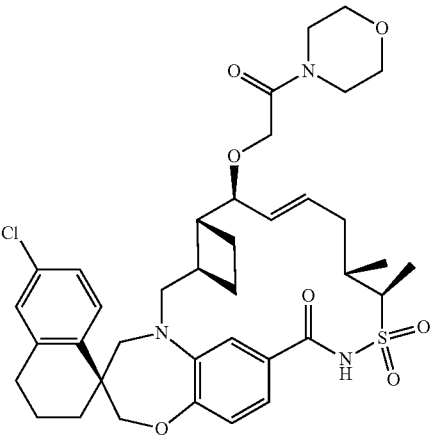 [SMILES: C[C@@H]1[C@@H](C)C/C=C/[C@H](OCC(=O)N2CCOCC2)[C@@H]2CC[C@H]2CN2C[C@@]3(CCCc4cc(Cl)ccc43)COc3ccc(cc32)C(=O)NS1(=O)=O]

The title compound was synthesized according to the procedure exemplified in Example 294. Note that DIEA was utilized as the general base in the reaction. The crude mixture was subjected to preparative reverse-phase HPLC (Gemini Prep $C_{18}$ 5 μm column; Phenomenex, Torrance, CA; gradient elution of 45-95% acetonitrile in water, where both solvents contained 0.1% TFA, 30 min method) to give, after lyophilization, 3.5 mg of the title compound as an off-white solid. $^1$H NMR (400 MHz, CDCl$_3$) δ 7.97 (s, 1H), 7.69 (d, J=8.4 Hz, 1H), 7.19 (dd, J=2.2, 8.5 Hz, 1H), 7.10 (d, J=2.2 Hz, 1H), 6.96-6.81 (m, 3H), 5.97-5.78 (m, 1H), 5.55 (dd, J=8.4, 15.3 Hz, 1H), 4.39-4.28 (m, 1H), 4.16-3.95 (m, 4H), 3.87-3.79 (m, 2H), 3.78-3.56 (m, 8H), 3.50 (br. s., 2H), 3.23 (d, J=14.3 Hz, 1H), 3.02 (dd, J=10.3, 15.2 Hz, 1H), 2.88-2.70 (m, 2H), 2.62-2.48 (m, 1H), 2.39-2.26 (m, 1H), 2.25-1.60 (m, 9H), 1.51 (d, J=7.2 Hz, 3H), 1.39 (t, J=12.9 Hz, 1H), 1.06 (d, J=6.8 Hz, 3H). m/z (ESI, +ve ion) 726.0 (M+H)$^+$.

Example 314. (1S,3'R,6'R,7'S,8'E,11'S,12'R)-6-chloro-11',12'-dimethyl-7'-(2-oxo-2-(3-oxo-1-piperazinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide Example 315. (1S,3'R,6'R,7'S,8'E,11'S,12'R)-6-chloro-7'-(2-(4,4-difluoro-1-piperidinyl)-2-oxoethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

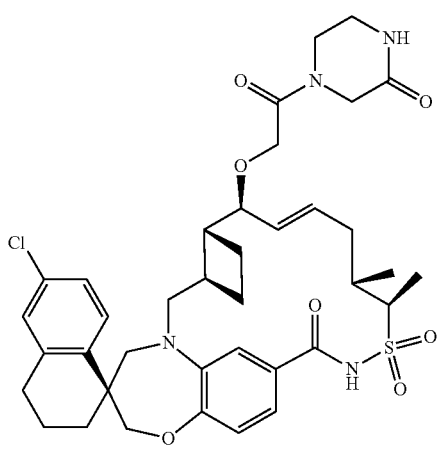 [SMILES: C[C@@H]1[C@@H](C)C/C=C/[C@H](OCC(=O)N2CCNC(=O)C2)[C@@H]2CC[C@H]2CN2C[C@@]3(CCCc4cc(Cl)ccc43)COc3ccc(cc32)C(=O)NS1(=O)=O]

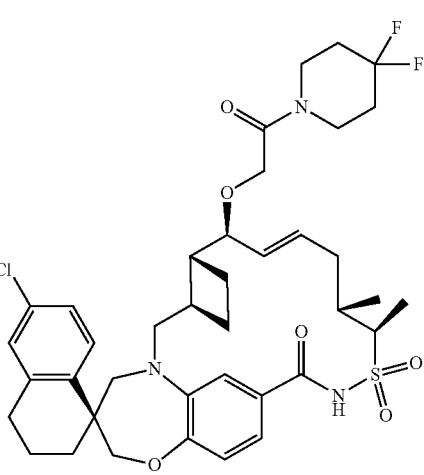

The title compound was synthesized according to the procedure exemplified in Example 294. Note that DIEA was utilized as the general base in the reaction. The crude mixture was subjected to preparative reverse-phase HPLC (Gemini Prep C$_{18}$ 5 µm column; Phenomenex, Torrance, CA; gradient elution of 40-95% acetonitrile in water, where both solvents contained 0.1% TFA, 30 min method) to give, after lyophilization, 3.5 mg of the title compound as an off-white solid. $^1$H NMR (400 MHz, CDCl$_3$) δ 8.53-7.93 (m, 1H), 7.68 (d, J=8.4 Hz, 1H), 7.19 (dd, J=2.2, 8.5 Hz, 1H), 7.09 (d, J=2.0 Hz, 1H), 6.94-6.50 (m, 3H), 5.98-5.77 (m, 1H), 5.64-5.47 (m, 1H), 4.36-3.66 (m, 12H), 3.47 (br. s., 2H), 3.23 (d, J=14.3 Hz, 1H), 3.04 (dd, J=9.6, 15.1 Hz, 1H), 2.86-2.69 (m, 2H), 2.67-2.43 (m, 1H), 2.34 (t, J=8.6 Hz, 1H), 2.25-1.59 (m, 11H), 1.51 (d, J=7.0 Hz, 3H), 1.39 (t, J=13.1 Hz, 1H), 1.06 (d, J=6.8 Hz, 3H). m/z (ESI, +ve ion) 739.0 (M+H)$^+$.

The title compound was synthesized according to the procedure exemplified in Example 294. Note that DIEA was utilized as the general base in the reaction. The crude mixture was subjected to preparative reverse-phase HPLC (Gemini Prep C$_{18}$ 5 µm column; Phenomenex, Torrance, CA; gradient elution of 45-95% acetonitrile in water, where both solvents contained 0.1% TFA, 30 min method) to give, after lyophilization, 6.0 mg of the title compound as an off-white solid. $^1$H NMR (400 MHz, CDCl$_3$) δ 8.04 (s, 1H), 7.69 (d, J=8.6 Hz, 1H), 7.19 (dd, J=2.3, 8.4 Hz, 1H), 7.10 (d, J=2.2 Hz, 1H), 6.97-6.79 (m, 3H), 5.95-5.79 (m, 1H), 5.54 (dd, J=9.4, 15.3 Hz, 1H), 4.46-4.26 (m, 1H), 4.18-3.96 (m, 4H), 3.89-3.50 (m, 7H), 3.23 (d, J=14.3 Hz, 1H), 3.07-2.98 (m, 1H), 2.85-2.74 (m, 2H), 2.68-1.76 (m, 15H), 1.73-1.60 (m, 1H), 1.50 (d, J=7.2 Hz, 3H), 1.39 (t, J=12.5 Hz, 1H), 1.06 (d, J=6.8 Hz, 3H). m/z (ESI, +ve ion) 760.0 (M+H)$^+$.

Example 316. (1S,3'R,6'R,7'S,8'E,11'S,12'R)-6-chloro-11',12'-dimethyl-7'-(2-(4-methyl-1-piperazinyl)-2-oxoethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

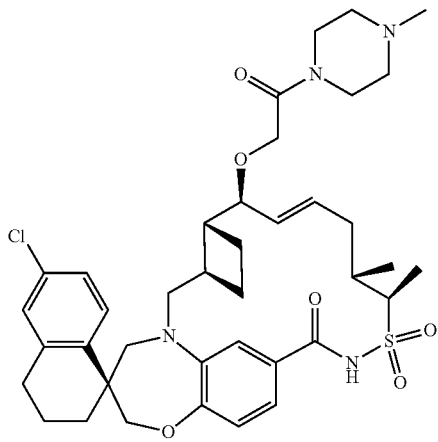 [SMILES: C[C@@H]1[C@@H](C)C/C=C/[C@H](OCC(=O)N2CCN(C)CC2)[C@@H]2CC[C@H]2CN2C[C@@]3(CCCc4cc(Cl)ccc43)COc3ccc(cc32)C(=O)NS1(=O)=O]

The title compound was synthesized according to the procedure exemplified in Example 294. The crude mixture was subjected to preparative reverse-phase HPLC (Gemini™ Prep C$_{18}$ 5 μm column; Phenomenex, Torrance, CA; gradient elution of 35-95% acetonitrile in water, where both solvents contained 0.1% TFA, 30 min method) to give, after lyophilization, 5.5 mg of the title compound as a white solid. $^1$H NMR (400 MHz, CDCl$_3$) δ 8.12 (br. s., 1H), 7.69 (d, J=8.4 Hz, 1H), 7.19 (dd, J=2.2, 8.6 Hz, 1H), 7.10 (d, J=2.2 Hz, 1H), 6.99-6.78 (m, 3H), 6.08-5.60 (m, 1H), 5.53 (dd, J=8.4, 15.5 Hz, 1H), 4.72 (br. s., 1H), 4.42-1.58 (m, 34H), 1.49 (d, J=5.1 Hz, 3H), 1.45-1.35 (m, 1H), 1.07 (d, J=6.5 Hz, 3H). m/z (ESI, +ve ion) 739.1 (M+H)$^+$.

Example 317. (1S,3'R,6'R,7'S,8'E,11'S,12'R)-6-chloro-11',12'-dimethyl-7'-(2-pyrimidinylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

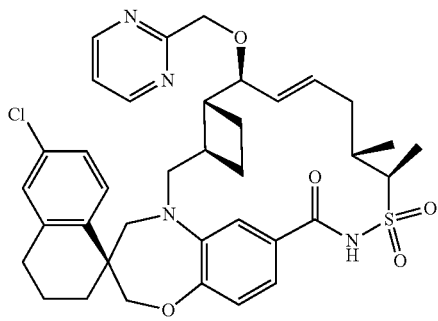 [SMILES: C[C@@H]1[C@@H](C)C/C=C/[C@H](OCc2ncccn2)[C@@H]2CC[C@H]2CN2C[C@@]3(CCCc4cc(Cl)ccc43)COc3ccc(cc32)C(=O)NS1(=O)=O]

To a stirred solution of (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (22 mg, 0.037 mmol, Example 719, Step 2) in DMF (1.5 mL) was added sodium hydride, 60% in mineral oil (7.34 mg, 0.184 mmol) (in excess) at rt. The resulting mixture was stirred at rt for a period of 20 min before 2-(chloromethyl)pyrimidine (14.16 mg, 0.110 mmol) was added. The resulting mixture was stirred at rt for a period of 19 h. The desired product was only the minor. The reaction was quenched with MeOH and the crude mixture was taken up in DMSO and subjected to preparative reverse-phase HPLC (Gemini™ Prep C$_{18}$ 5 μm column; Phenomenex, Torrance, CA; gradient elution of 50-95% acetonitrile in water, where both solvents contained 0.1% TFA, 30 min method) to give, after lyophilization, 0.5 mg of the title compound as a colorless film. $^1$H NMR (500 MHz, CDCl$_3$) δ 8.89 (d, J=4.2 Hz, 2H), 7.92 (s, 1H), 7.70 (d, J=8.3 Hz, 1H), 7.37 (br. s., 1H), 7.19 (dd, J=2.3, 8.4 Hz, 1H), 7.10 (d, J=2.2 Hz, 1H), 6.97-6.83 (m, 3H), 5.99-5.80 (m, 1H), 5.65 (dd, J=9.4, 15.0 Hz, 1H), 4.83-4.72 (m, 1H), 4.70-4.54 (m, 1H), 4.31 (q, J=6.8 Hz, 1H), 4.15-4.04 (m, 2H), 4.01 (d, J=8.8 Hz, 1H), 3.83 (d, J=14.9 Hz, 1H), 3.71 (d, J=14.4 Hz, 1H), 3.24 (d, J=14.4 Hz, 1H), 3.02 (dd, J=10.4, 15.0 Hz, 1H), 2.87-2.66 (m, 3H), 2.41-2.29 (m, 1H), 2.25-1.56 (m, 10H), 1.50 (d, J=7.3 Hz, 3H), 1.39 (t, J=13.0 Hz, 1H), 1.07 (d, J=6.8 Hz, 3H). m/z (ESI, +ve ion) 691.0 (M+H)$^+$.

Example 318. (3R,6R,7S,8E,11R,16R,26S)-6'-chloro-7-hydroxy-3',4'-dihydro-2'H,19H-spiro[13,24-dioxa-17-thia-1,18-diazapentacyclo[18.7.2.0$^{3,6}$.0$^{11,16}$.0$^{23,28}$]nonacosa-8,20,22,28-tetraene-26,1'-naphthalen]-19-one 17,17-dioxide

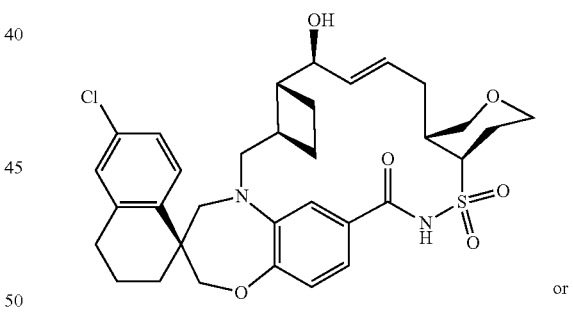

or

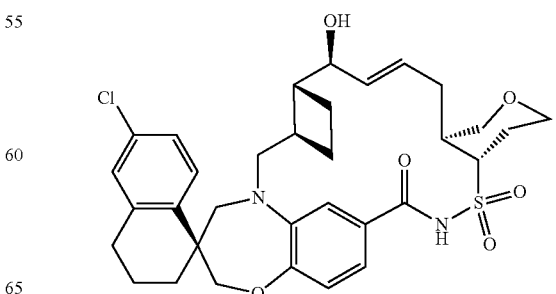

Step 1: (R)-3-allyldihydro-2H-pyran-(((3H)-one and (S)-3-allyldihydro-2H-pyran-(((3H)-one

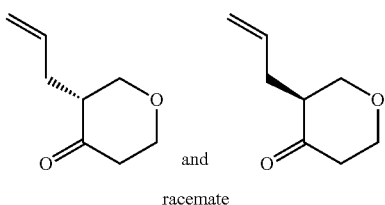

racemate

Into a single-necked round-bottomed 250-mL flask were placed allylpalladium(II) chloride (0.630 g, 1.722 mmol), 4,5-bis(diphenylphosphino)-9,9-dimethylxanthene (1.993 g, 3.44 mmol), and dl-proline (1.189 g, 10.33 mmol). The flask was subjected to 3 cycles of evacuation and back-filling with nitrogen. Then tetrahydropyran-4-one (9.54 mL, 103 mmol), allyl alcohol (2.342 mL, 34.4 mmol), and DMSO (100 mL) were introduced sequentially at rt under nitrogen. The resulting mixture was stirred at rt for 10 min and 75° C. for a period of 24 h. After cooled, the crude mixture was poured into ice and saturated sodium bicarbonate aqueous solution and extracted with 25% i-PrOH/DCM (3×). The combined organics were washed with water (2×), dried over anhydrous sodium sulfate, and concentrated in vacuo. The residue was subjected to combi-flash column chromatography (EtOAc/Hexanes, 8 min at 0% and 35 min from 0 to 40%, 80 g ISCO silica gel column) to give a racemic mixture of (R)-3-allyldihydro-2H-pyran-(((3H)-one and (S)-3-allyldihydro-2H-pyran-(((3H)-one (3.85 g, 27.46 mmol, 80% yield) as a colorless liquid, impure and directly taken onto the next step.

Step 2: (3R,4S)-3-allyltetrahydro-2H-pyran-4-ol and (3S,4R)-3-allyltetrahydro-2H-pyran-4-ol

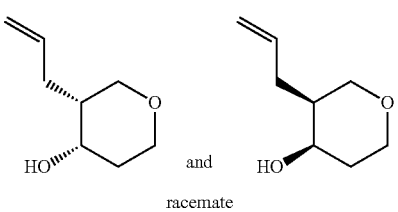

racemate

To a stirred solution of impure 3-allyldihydro-2H-pyran-(((3H)-one (3.100 g, 22.11 mmol) in THF (60 mL) cooled in an MeOH-dry ice bath (~78° C.) was slowly added L-selectride, 1.0 M solution in tetrahydrofuran (31.0 mL, 31.0 mmol) via a syringe. After the addition was complete, the resulting mixture was stirred at −78° C. for 1 h. The MeOH-dry ice was replaced with ice-water bath and the mixture was stirred for 15 min before carefully quenched with saturated ammonium chloride aqueous solution. The mixture was further diluted with saturated ammonium chloride aqueous solution and extracted with 25% i-PrOH/DCM (3×). The combined organics were dried over anhydrous sodium sulfate and concentrated in vacuo. The residue was subjected to combi-flash column chromatography (EtOAc/Hexanes, 5 min at 0% and 35 min from 0 to 60%, 40 g ISCO silica gel column) to give a racemic mixture of (3R,4S)-3-allyltetrahydro-2H-pyran-4-ol and (3S,4R)-3-allyltetrahydro-2H-pyran-4-ol (2.60 g, 18.28 mmol, 83% yield) as a colorless liquid, impure and directly taken onto the next step.

Step 3: (3R,4S)-3-allyltetrahydro-2H-pyran-4-yl methanesulfonate and (3S,4R)-3-allyltetrahydro-2H-pyran-4-yl methanesulfonate

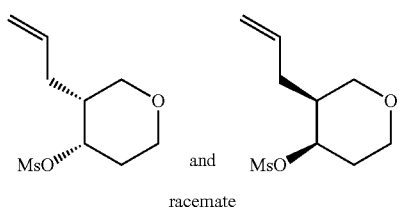

racemate

To a stirred ice-cooled solution of impure racemic (3R,4S)-3-allyltetrahydro-2H-pyran-4-ol and (3S,4R)-3-allyltetrahydro-2H-pyran-4-ol (2.00 g, 14.07 mmol) and anhydrous triethylamine (4.30 mL, 30.9 mmol) in DCM (30 mL) was slowly added methanesulfonyl chloride (1.667 mL, 21.10 mmol) through a syringe. The resulting mixture was stirred at 0° C. for a period of 1 h 20 min. The crude mixture was poured into ice and 1 N aqueous HCl solution and extracted with DCM (2×). The combined organics were washed once again with 1 N aqueous HCl solution followed by brine (2×), dried over anhydrous sodium sulfate, and concentrated in vacuo to give a racemic mixture of (3R,4S)-3-allyltetrahydro-2H-pyran-4-yl methanesulfonate and (3S,4R)-3-allyltetrahydro-2H-pyran-4-yl methanesulfonate (2.8 g, 12.72 mmol, 90%) as a colorless oil, impure and taken onto the next step without purification.

Step 4: 2-(((3R,4R)-3-allyltetrahydro-2H-pyran-4-yl)thio)pyrimidine and 2-(((3S,4S)-3-allyltetrahydro-2H-pyran-4-yl)thio)pyrimidine

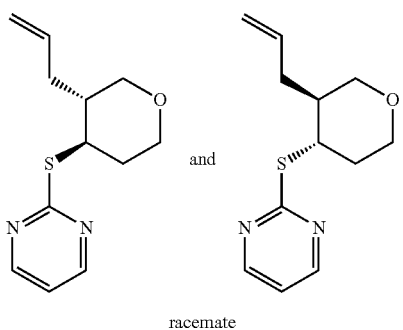 [SMILES: C=CC[C@@H]1COCC[C@H]1Sc1ncccn1 ; C=CC[C@H]1COCC[C@@H]1Sc1ncccn1]

racemate

A mixture of 2-mercapto-pyrimidine (2.467 g, 21.99 mmol) and potassium carbonate anhydrous (4.47 g, 32.3 mmol) in DMF (30 mL) was stirred at rt for 10 min before a solution of the impure racemic mixture of (3R,4S)-3-allyltetrahydro-2H-pyran-4-yl methanesulfonate and (3S,4R)-3-allyltetrahydro-2H-pyran-4-yl methanesulfonate (2.85 g, 12.94 mmol) was added at rt. The resulting mixture was stirred at rt for 10 min, at 75° C. for a period of 1 h, 85° C. for 1.5 h, and at 95° C. for 1 h. The crude mixture was poured into ice and saturated sodium carbonate aqueous solution and extracted with EtOAc (2×). The combined organics were washed with saturated sodium carbonate aqueous solution (1×) followed by water (1×), dried over anhydrous sodium sulfate, and concentrated in vacuo. The residue was subjected to combi-flash column chromatography (EtOAc/hexanes, 40 min from 0 to 60%, 40 g ISCO silica gel column) to give 0.58 g of a racemic mixture of 2-(((3R,4R)-3-allyltetrahydro-2H-pyran-4-yl)thio)pyrimidine and 2-(((3S,4S)-3-allyltetrahydro-2H-pyran-4-yl)thio)pyrimidine as a colorless film, impure and taken onto the next step.

Step 5: 2-(((3R,4R)-3-allyltetrahydro-2H-pyran-4-yl)sulfonyl)pyrimidine and 2-(((3S,4S)-3-allyltetrahydro-2H-pyran-4-yl)sulfonyl)pyrimidine

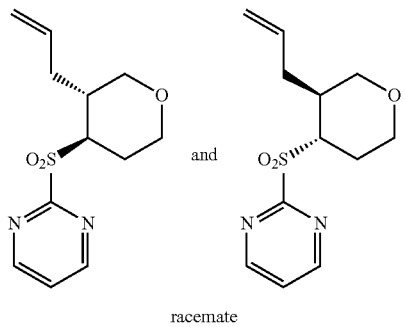 [SMILES: C=CC[C@@H]1COCC[C@H]1S(=O)(=O)c1ncccn1 ; C=CC[C@H]1COCC[C@@H]1S(=O)(=O)c1ncccn1]

racemate

To a stirred ice-cooled solution of the impure racemic mixture of 2-(((3R,4R)-3-allyltetrahydro-2H-pyran-4-yl)thio)pyrimidine and 2-(((3S,4S)-3-allyltetrahydro-2H-pyran-4-yl)thio)pyrimidine (0.58 g, 2.454 mmol) in DCM (10 mL) and DMF (0.5 mL) was added 3-chlorobenzoperoxoic acid (1.155 g, 5.15 mmol) in 2 portions as a solid over 5 min. The resulting mixture was stirred at 0° C. for 10 min. The ice bath was then removed and the mixture was stirred at rt for 2 h 15 min. The crude mixture was directly loaded onto a silica gel precolumn and subjected to combi-flash column chromatography (EtOAc/Hexanes, 5 min at 0% and 40 min from 0 to 100%, 40 g ISCO silica gel column) to give a racemic mixture of 2-(((3R,4R)-3-allyltetrahydro-2H-pyran-4-yl)sulfonyl)pyrimidine and 2-(((3S,4S)-3-allyltetrahydro-2H-pyran-4-yl)sulfonyl)pyrimidine (0.31 g, 1.155 mmol, 47.1% yield) as a colorless oil. m/z (ESI, +ve ion) 269.1 (M+H)$^+$.

Step 6: (3R,4R)-3-allyltetrahydro-2H-pyran-4-sulfonamide and (3S,4S)-3-allyltetrahydro-2H-pyran-4-sulfonamide

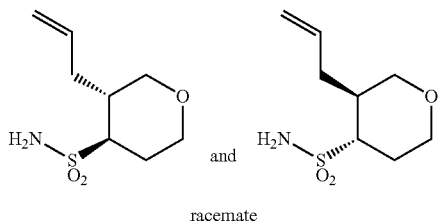

racemate

The 1$^{st}$ step: To a stirred solution of the racemic mixture of 2-(((3S,4S)-3-allyltetrahydro-2H-pyran-4-yl)sulfonyl)pyrimidine and 2-(((3R,4R)-3-allyltetrahydro-2H-pyran-4-yl)sulfonyl)pyrimidine (0.31 g, 1.155 mmol) in MeOH (8 mL) was added at rt sodium methoxide, 25 wt % solution in methanol (0.257 mL, 1.155 mmol) via a syringe. The resulting mixture was stirred at rt for 40 min when LC-MS showed near completion. The volatiles were removed in vacuo and the residue was subjected to high vacuum. The 2$^{nd}$ step: To the above residue was added at rt water (8 mL) followed by sodium acetate trihydrate (0.217 mL, 2.311 mmol) and amidoperoxymonosulfuric acid (0.261 g, 2.311 mmol). The resulting clear solution was stirred at 75° C. in a preheated oil bath for a period of 40 min. The mixture was cooled, basified using ice cold saturated sodium carbonate, and extracted with 20% i-PrOH/DCM (3×). The combined organics were dried over anhydrous sodium sulfate and concentrated in vacuo. The residue was subjected to combi-flash column chromatography (EtOAc/Hexanes, 3 min at 0 and 40 min from 0 to 80%, 24 g ISCO silica gel column) to give a racemic mixture of (3R,4R)-3-allyltetrahydro-2H-pyran-4-sulfonamide and (3S,4S)-3-allyltetrahydro-2H-pyran-4-sulfonamide (0.20 g, 0.974 mmol, 84% yield) as a colorless oil, directly taken onto the next step.

Step 7: (S)-6'-chloro-5-0(1R,2R)-2-((S,E)-1-hydroxy-4-((3R,4R)-4-sulfamoyltetrahydro-2H-pyran-3-yl)but-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((3S,4S)-4-sulfamoyltetrahydro-2H-pyran-3-yl)but-2-en-1-yl)cyclobutyl)methyl)-3',4,4',5-tetrahydro-2H,2'H-spiro[benzo[b][1,4]oxazepine-3,1'-naphthalene]-7-carboxylic acid

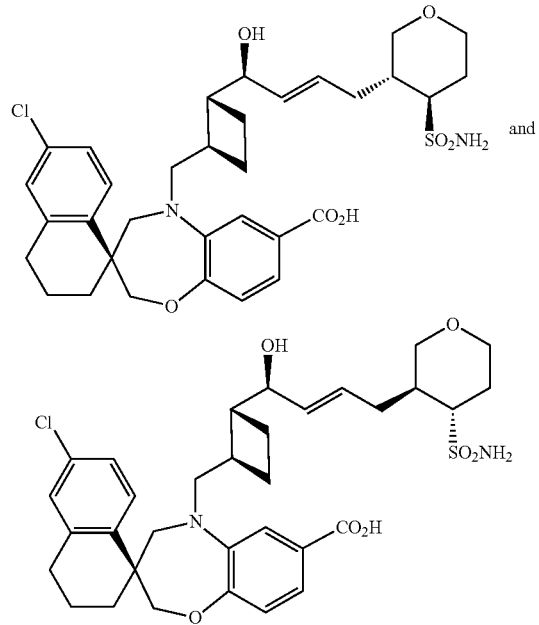

To a 25 mL single-necked round-bottomed flask were placed (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (150 mg, 0.294 mmol, Intermediate AA12A), a racemic mixture of (3R,4R)-3-allyltetrahydro-2H-pyran-4- sulfonamide and (3S,4S)-3-allyltetrahydro-2H-pyran-4-sulfonamide (121 mg, 0.588 mmol), and 2<sup>nd</sup> generation hoveyda-grubbs catalyst (18.43 mg, 0.029 mmol). The flask was subjected to 3 cycles of evacuation and back-filling with nitrogen before DCE (4.5 mL) was introduced through a syringe under nitrogen. The resulting mixture was stirred at rt under nitrogen for a period of 3 h. The crude mixture was loaded onto a silica gel precolumn and subjected to combi-flash column chromatography ((10% MeOH/DCM with 0.3% AcOH)/DCM), 30 min from 0 to 70%, 24 g ISCO silica gel column) to give a mixture of the title compounds (73 mg, 0.113 mmol, 38.5% yield) as an off-white solid.

Step 8: (3R,6R,7S,8E,11R,16R,26S)-6'-chloro-7-hydroxy-3',4'-dihydro-2'H,19H-spiro[13,24-dioxa-17-thia-1,18-diazapentacyclo[18.7.2.0$^{3,6}$.0$^{11,16}$.0$^{23,28}$]nonacosa-8,20,22,28-tetraene-26,1'-naphthalen]-19-one 17,17-dioxide or (3R,6R,7S,8E,11S,16S,26S)-6'-chloro-7-hydroxy-3',4'-dihydro-2'H,19H-spiro[13,24-dioxa-17-thia-1,18-diazapentacyclo[18.7.2.0$^{3,6}$.0$^{11,16}$.0$^{23,28}$]nonacosa-8,20,22,28-tetraene-26,1'-naphthalen]-19-one 17,17-dioxide To a stirred ice-cooled solution of (S)-6'-chloro-5-(((1R,2R)-2-((S,E)-1-hydroxy-4-((3R,4R)-4-sulfamoyltetrahydro-2H-pyran-3-yl)but-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((3S,4S)-4-sulfamoyltetrahydro-2H-pyran-3-yl)but-2-en-1-yl)cyclobutyl)methyl)-3',4,4',5-tetrahydro-2H,2'H-spiro[benzo[b][1,4]oxazepine-3,1'-naphthalene]-7-carboxylic acid (73 mg, 0.113 mmol), N,N-dimethylpyridin-4-amine (30.4 mg, 0.249 mmol) in DCM (60 mL) was added 1-(3-dimethylaminopropyl)-3-ethylcarbodiimide hydrochloride (54.2 mg, 0.283 mmol) in one portion. The resulting mixture was stirred at 0° C. for 20 min and at ambient temperature for 4 h. The volatiles were removed in vacuo. The crude residue was taken up in DMSO and subjected to preparative reverse-phase HPLC (Gemini™ Prep C$_{18}$ 5 µm column; Phenomenex, Torrance, CA; gradient elution of 50-95% acetonitrile in water, where both solvents contained 0.1% TFA, 30 min method) to give, after lyophilization, 23 mg of the title compound as the first eluting fraction (Example 318) as a white solid. $^1$H NMR (400 MHz, CDCl$_3$) δ 8.46 (br. s., 1H), 7.70 (d, J=8.6 Hz, 1H), 7.19 (dd, J=2.2, 8.5 Hz, 1H), 7.09 (d, J=2.2 Hz, 1H), 7.00-6.92 (m, 2H), 6.79 (s, 1H), 5.93 (td, J=7.0, 14.6 Hz, 1H), 5.70 (dd, J=8.0, 15.3 Hz, 1H), 4.29-4.17 (m, 2H), 4.14-3.99 (m, 3H), 3.92 (dd, J=4.0, 11.8 Hz, 1H), 3.74 (dd, J=14.8, 19.1 Hz, 2H), 3.64-3.54 (m, 1H), 3.31 (dd, J=8.0, 11.9 Hz, 1H), 3.23 (d, J=14.3 Hz, 1H), 3.03 (dd, J=9.0, 15.5 Hz, 1H), 2.85-2.73 (m, 2H), 2.50-1.75 (m, 14H), 1.67 (q, J=9.5 Hz, 1H), 1.41 (t, J=12.1 Hz, 1H). m/z (ESI, +ve ion) 627.0 (M+H)$^+$.

Further elution provided the title compound (29 mg) as the second eluting fraction (Example 319) as a white solid. $^1$H NMR (400 MHz, CDCl$_3$) δ 8.46 (br. s., 1H), 7.66 (d, J=8.4 Hz, 1H), 7.17 (dd, J=2.2, 8.5 Hz, 1H), 7.12-6.99 (m, 3H), 6.95 (d, J=8.2 Hz, 1H), 6.11-5.61 (m, 2H), 4.41-1.34 (m, 30H). m/z (ESI, +ve ion) 627.0 (M+H)$^+$.

Example 320. (3R,6R,7S,8E,11R,16R,26S)-6'-chloro-7-methoxy-3',4'-dihydro-2'H,19H-spiro[13,24-dioxa-17-thia-1,18-diazapentacyclo[18.7.2.0$^{3,6}$.0$^{11,16}$.0$^{23,28}$]nonacosa-8,20,22,28-tetraene-26,1'-naphthalen]-19-one 17,17-dioxide or (3R,6R,7S,8E,11S,16S,26S)-6'-chloro-7-methoxy-3',4'-dihydro-2'H,19H-spiro[13,24-dioxa-17-thia-1,18-diazapentacyclo[18.7.2.0$^{3,6}$.0$^{11,16}$.0$^{23,28}$]nonacosa-8,20,22,28-tetraene-26,1'-naphthalen]-19-one 17,17-dioxide

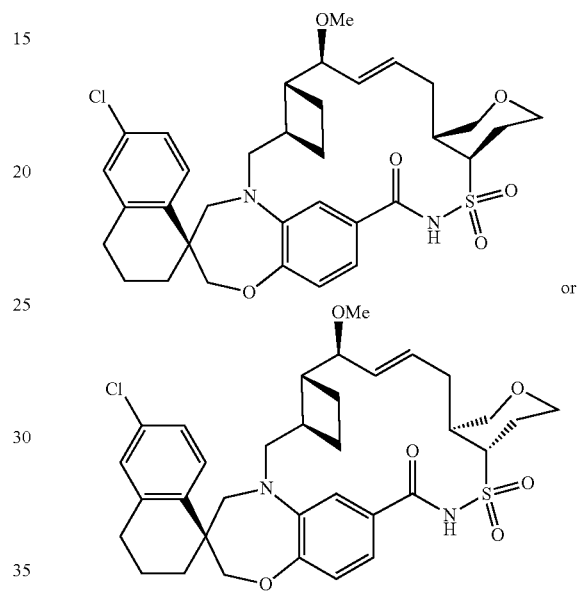

To a stirred ice-cooled solution of a mixture of (3R,6R,7S,8E,11R,16R,26S)-6'-chloro-7-hydroxy-3',4'-dihydro-2'H,19H-spiro[13,24-dioxa-17-thia-1,18-diazapentacyclo[18.7.2.0$^{3,6}$.0$^{11,16}$.0$^{23,28}$]nonacosa-8,20,22,28-tetraene-26,1'-naphthalen]-19-one 17,17-dioxide and (3R,6R,7S,8E,11S,16S,26S)-6'-chloro-7-hydroxy-3',4'-dihydro-2'H,19H-spiro[13,24-dioxa-17-thia-1,18-diazapentacyclo[18.7.2.0$^{3,6}$.0$^{11,16}$.0$^{23,28}$]nonacosa-8,20,22,28-tetraene-26,1'-naphthalen]-19-one 17,17-dioxide (not weighed, Examples 318) in DMF (2 mL) was added sodium hydride, 60% dispersion in mineral oil (in excess) at rt. The resulting mixture was stirred at 0° C. for 10 min and at rt for 20 min before iodomethane (in excess) was added at rt. The resulting mixture was stirred at rt for a period of 1.5 h. The reaction mixture was cooled in an ice-water bath before quenched with methanol. It was taken up in DMSO and subjected to preparative reverse-phase HPLC (Gemini Prep C$_{18}$ 5 µm column; Phenomenex, Torrance, CA; gradient elution of 50-95% acetonitrile in water, where both solvents contained 0.1% TFA, 30 min method) to give, after lyophilization, 0.6 mg of the title compound as the first eluting fraction as a white solid. $^1$H NMR (500 MHz, CDCl$_3$) δ 8.12 (s, 1H), 7.71 (d, J=8.6 Hz, 1H), 7.20 (dd, J=2.2, 8.6 Hz, 1H), 7.11 (d, J=2.2 Hz, 1H), 6.98-6.89 (m, 2H), 6.74 (d, J=1.5 Hz, 1H), 5.97-5.83 (m, 1H), 5.55 (dd, J=9.0, 15.4 Hz, 1H), 4.39 (dt, J=4.9, 9.0 Hz, 1H), 4.17-4.03 (m, 3H), 3.93 (dd, J=4.0, 11.9 Hz, 1H), 3.80 (d, J=15.2 Hz, 1H), 3.73 (d, J=14.2 Hz, 1H), 3.69 (dd, J=3.7, 9.0 Hz, 1H), 3.60-3.53 (m, 1H), 3.33 (dd, J=8.8, 11.7 Hz, 1H), 3.27 (s, 3H), 3.20 (d, J=14.2 Hz, 1H), 2.99 (dd, J=10.3, 15.2 Hz, 1H), 2.86-2.73 (m, 2H), 2.59

(d, J=15.4 Hz, 1H), 2.50-1.53 (m, 13H), 1.40 (t, J=12.7 Hz, 1H). m/z (ESI, +ve ion) 641.0 (M+H)+.

Example 321. (3R,6R,7S,8E,11S,16S,26S)-6'-chloro-7-methoxy-3',4'-dihydro-2'H,19H-spiro[13,24-dioxa-17-thia-1,18-diazapentacyclo[18.7.2.0$^{3,6}$.0$^{11,16}$.0$^{23,28}$]nonacosa-8,20,22,28-tetraene-26,1'-naphthalen]-19-one 17,17-dioxide or (3R,6R,7S,8E,11R,16R,26S)-6'-chloro-7-methoxy-3',4'-dihydro-2'H,19H-spiro[13,24-dioxa-17-thia-1,18-diazapentacyclo[18.7.2.0$^{3,6}$.0$^{11,16}$.0$^{23,28}$]nonacosa-8,20,22,28-tetraene-26,1'-naphthalen]-19-one 17,17-dioxide

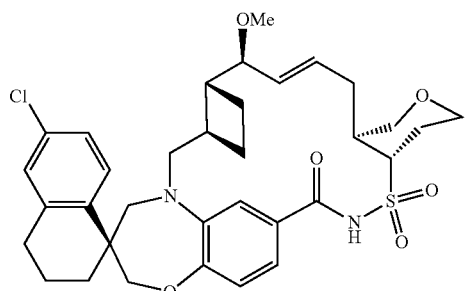

or

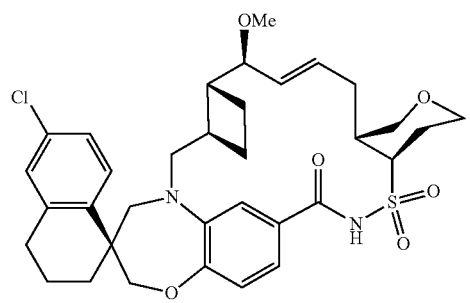

The title compound (0.8 mg) was obtained as a white solid as the second eluting isomer from preparative reverse-phase HPLC (Gemini™ Prep C$_{18}$ 5 µm column; Phenomenex, Torrance, CA; gradient elution of 50-95% acetonitrile in water, where both solvents contained 0.1% TFA, 30 min method) in Example 320. $^1$H NMR (500 MHz, CDCl$_3$) δ 8.12 (s, 1H), 7.69 (d, J=8.3 Hz, 1H), 7.24 (d, J=9.0 Hz, 1H), 7.19 (dd, J=2.1, 8.4 Hz, 1H), 7.09 (d, J=2.0 Hz, 1H), 6.98 (d, J=8.3 Hz, 1H), 6.60 (br. s., 1H), 6.09-5.93 (m, 1H), 5.56 (dd, J=8.3, 15.2 Hz, 1H), 4.22-4.08 (m, 2H), 4.07-4.01 (m, 1H), 3.98-3.88 (m, 2H), 3.69 (d, J=14.4 Hz, 1H), 3.64 (dd, J=3.4, 8.1 Hz, 1H), 3.57 (d, J=14.9 Hz, 1H), 3.51 (dt, 11.4 Hz, 1H), 3.37-3.24 (m, 4H), 3.18-3.03 (m, 2H), 2.86-2.71 (m, 2H), 2.52-2.30 (m, 4H), 2.28-2.16 (m, 1H), 2.14-1.58 (m, 9H), 1.44 (t, J=12.1 Hz, 1H). m/z (ESI, +ve ion) 641.0 (M+H)+.

Example 322. (3R,6R,7S,8E,11R,16R,26S)-6'-chloro-7-(2-methoxyethoxy)-3',4'-dihydro-2'H,19H-spiro[13,24-dioxa-17-thia-1,18-diazapentacyclo[18.7.2.0$^{3,6}$.0$^{11,16}$.0$^{23,28}$]nonacosa-8,20,22,28-tetraene-26,1'-naphthalen]-19-one 17,17-dioxide or (3R,6R,7S,8E,11S,16S,26S)-6'-chloro-7-(2-methoxyethoxy)-3',4'-dihydro-2'H,19H-spiro[13,24-dioxa-17-thia-1,18-diazapentacyclo[18.7.2.0$^{3,6}$.0$^{11,16}$.0$^{23,28}$]nonacosa-8,20,22,28-tetraene-26,1'-naphthalen]-19-one 17,17-dioxide

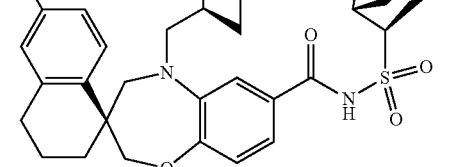

or

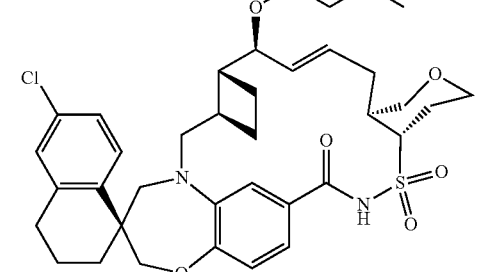

To a stirred solution of a mixture of (3R,6R,7S,8E,11R,16R,26S)-6'-chloro-7-hydroxy-3',4'-dihydro-2'H,19H-spiro[13,24-dioxa-17-thia-1,18-diazapentacyclo[18.7.2.0$^{3,6}$.0$^{11,16}$.0$^{23,28}$]nonacosa-8,20,22,28-tetraene-26,1'-naphthalen]-19-one 17,17-dioxide and (3R,6R,7S,8E,11S,16S,26S)-6'-chloro-7-hydroxy-3',4'-dihydro-2'H,19H-spiro[13,24-dioxa-17-thia-1,18-diazapentacyclo[18.7.2.0$^{3,6}$.0$^{11,16}$.0$^{23,28}$]nonacosa-8,20,22,28-tetraene-26,1'-naphthalen]-19-one 17,17-dioxide (6.2 mg, 9.89 µmol, Example 318) in DMF (1 mL) was added sodium hydride, 60% dispersion in mineral oil (3.95 mg, 0.099 mmol) (in excess) at rt. The mixture was stirred at rt for 25 min before 2-bromoethyl methyl ether (9.30 µl, 0.099 mmol) (in excess) was added. The resulting mixture was stirred at rt for 2.5 h. The reaction mixture was cooled in an ice-water bath before quenched with methanol. It was taken up in DMSO and subjected to preparative reverse-phase HPLC (Gemini Prep C$_{18}$ 5 µm column; Phenomenex, Torrance, CA; gradient elution of 50-95% acetonitrile in water, where both solvents contained 0.1% TFA, 30 min method) to give, after lyophilization, 5.0 mg of the title compound as a white solid. $^1$H NMR (400 MHz, CDCl$_3$) δ 8.47 (br. s., 1H), 7.69 (d, J=8.6 Hz, 1H), 7.18 (dd, J=2.3, 8.4 Hz, 1H), 7.09 (d, J=2.3 Hz, 1H), 6.93 (s, 2H), 6.72 (s, 1H), 5.91 (td, J=7.2, 14.6 Hz, 1H), 5.54 (dd, J=8.3, 15.4 Hz, 1H), 4.30 (dt, J=4.7, 9.0 Hz, 1H), 4.15-4.00 (m, 3H), 3.90 (dd, J=4.1, 11.7 Hz, 1H), 3.81 (dd, J=3.3, 8.4 Hz, 1H), 3.79-3.67 (m, 2H), 3.64-3.49 (m, 4H), 3.48-3.42 (m, 1H), 3.39 (s, 3H), 3.32-3.15 (m, 2H), 2.96 (dd, J=10.4, 15.3 Hz, 1H), 2.86-2.69 (m, 2H), 2.54-1.51 (m, 14H), 1.39 (t, J=12.4 Hz, 1H). m/z (ESI, +ve ion) 685.1 (M+H)+.

Example 323. (1S,3'R,6'R,7'S,8'E,11R,15'R)-6-chloro-7'-hydroxy-3,4-dihydro-2H,18'H-spiro[naphthalene-1,25'-[23]oxa[16]thia[1,17]diazapentacyclo [17.7.2.0$^{3,6}$.0$^{11,15}$.0$^{22,27}$]octacosa[8,19,21,27]tetraen]-18'-one 16',16'-dioxide or (1S,3'R,6'R,7'S,8'E, 11'S,15'S)-6-chloro-7'-hydroxy-3,4-dihydro-2H, 18'H-spiro[naphthalene-1,25'-[23]oxa[16]thia[1,17] diazapentacyclo [17.7.2.0$^{3,6}$.0$^{11,15}$.0$^{22,27}$]octacosa[8, 19,21,27]tetraen]-18'-one 16',16'-dioxide

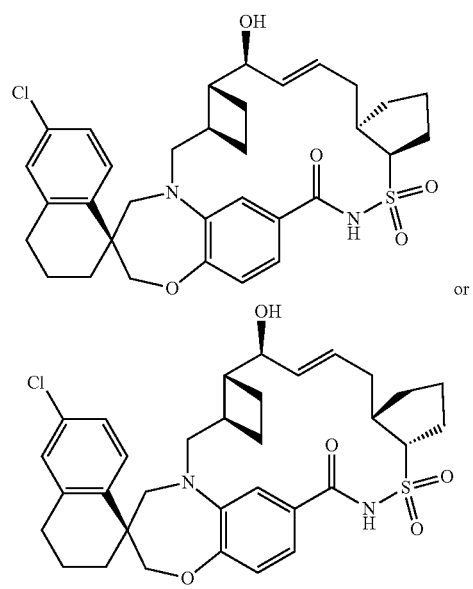

Step 1: (1R,2S)-2-allylcyclopentanol and (1S,2R)-2-allylcyclopentanol

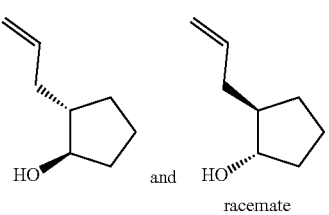

racemate

To allylmagnesium bromide, 1.0 M solution in diethyl ether (100 mL, 100 mmol) stirred at −10 to −18° C. in a 500-mL single-necked round-bottomed flask was added slowly 1,2-epoxycyclopentane (4.12 mL, 47.6 mmol) through a syringe over a period of 30 min. The resulting mixture was stirred at this temperature and allowed to slowly warm up to rt and stirred at rt overnight (18 h). The reaction mixture was thoroughly cooled in an ice bath before slowly and very carefully quenched with ice cold saturated ammonium chloride aqueous solution. Strong gas evolution was observed. Some chunky and gummy precipitate formed at the bottom of the flask. This mixture was further diluted with ether and ice cold ammonium chloride aqueous solution. It was stirred and occasionally sonicated to give a clear two-phase mixture. The layers were separated and the aqueous phase was extracted with ether (2×). The combined organics were combined and washed with saturated ammonium chloride aqueous solution (1×), dried over anhydrous sodium sulfate, and concentrated in vacuo to give a racemic mixture of (1R,2S)-2-allylcyclopentanol and (1S,2R)-2-allylcyclopentanol (6.6 g, 52.3 mmol, 110% yield) as a colorless oil.

Step 2: (1S,2R)-2-allylcyclopentyl methanesulfonate and (1R,2S)-2-allylcyclopentyl methanesulfonate

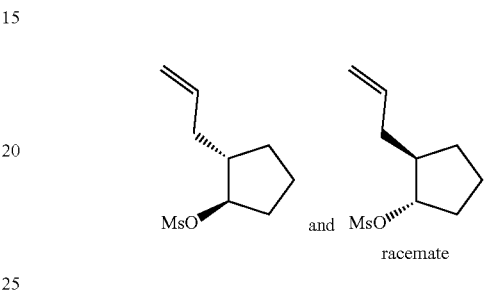

racemate

To a stirred ice-cooled solution of a racemic mixture of (1S,2R)-2-allylcyclopentanol and (1S,2R)-2-allylcyclopentanol (3.0 g, 23.77 mmol) and triethylamine (7.27 mL, 52.3 mmol) in DCM (50 mL) was slowly added methanesulfonyl chloride (2.82 mL, 35.7 mmol) through a syringe. The resulting mixture was stirred at 0° C. for a period of 1 h. The crude mixture was poured into ice and 1 N aqueous HCl solution and extracted with DCM (2×). The combined organics were once again washed with 1 N aqueous HCl solution followed by brine (2×) and dried over anhydrous sodium sulfate. The residue after concentration in vacuo gave a racemic mixture of (1S,2R)-2-allylcyclopentyl methanesulfonate and (1R,2S)-2-allylcyclopentylmethanesulfonate (5.0 g, 24.48 mmol, 103% yield) as a nearly colorless oil, directly taken onto the next step.

Step 3: 2-(((1R,2R)-2-allylcyclopentyl)thio)pyrimidine and 2-(((1S,2S)-2-allylcyclopentyl)thio)pyrimidine

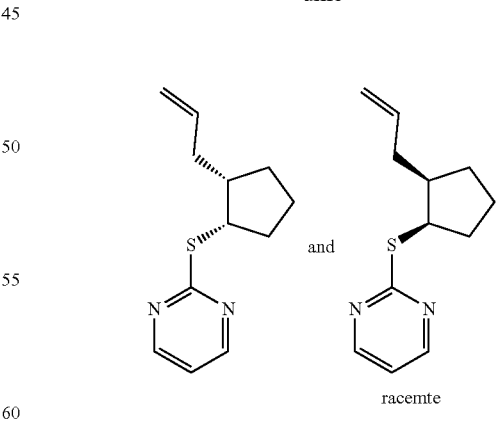

racemte

To a stirred mixture of 2-mercapto-pyrimidine (3.64 g, 32.5 mmol) and potassium carbonate anhydrous (5.52 g, 39.9 mmol) in DMF (20 mL) was added at rt a solution of a racemic mixture of (1S,2R)-2-allylcyclopentyl methanesulfonate and (1R,2S)-2-allylcyclopentyl methanesulfonate (5.1 g, 24.96 mmol) in DMF (20 mL). The resulting mixture was stirred at rt for a period of 17 h. Within the first 1.5 h or so, the reaction mixture got so creamy that the stirring became nearly ineffective. More DMF (3×10 mL) was added and the mixture was stirred at rt overnight. It was observed the next morning the stirring had been disabled due to the fact that the mixture became a very thick paste. The crude mixture was poured into ice and saturated sodium bicarbonate aqueous solution and extracted with ether (3×). The combined organics were washed with water (1×) followed by brine (1×), dried over anhydrous sodium sulfate, and concentrated in vacuo. The residue was subjected to combi-flash column chromatography (EtOAc/hexanes, 20 min at 10%, 80 g ISCO silica gel column) to give 4.3 g of an impure racemic mixture of 2-(((1R,2R)-2-allylcyclopentyl)thio)pyrimidine and 2-(((1S,2S)-2-allylcyclopentyl)thio)pyrimidine, directly taken onto the next step.

Step 4: 2-(((1R,2R)-2-allylcyclopentyl)sulfonyl)pyrimidine and 2-(((1S,2S)-2-allylcyclopentyl)sulfonyl)pyrimidine

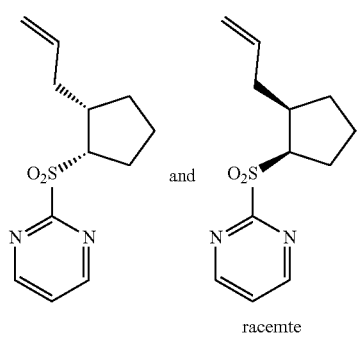 [SMILES: C=CC[C@@H]1CCC[C@@H]1S(=O)(=O)c1ncccn1 ; C=CC[C@H]1CCC[C@H]1S(=O)(=O)c1ncccn1]

racemte

To a stirred ice-cooled solution of the above impure racemic mixture of 2-(((1R,2R)-2-allylcyclopentyl)thio)pyrimidine and 2-(((1S,2S)-2-allylcyclopentyl)thio)pyrimidine (2.1 g, 9.53 mmol) in DCM (30 mL) was added 3-chlorobenzoperoxoic acid (3.45 g, 20.02 mmol) in two portion over a period of 10 min. The resulting mixture was stirred at 0° C. for about 2 h. (Note that there was a major peak on LC-MS which gave rise a mass consistent with the intermediate sulfoxide. So the reaction was allowed to go for a much extended duration). The reaction mixture appeared a white heterogeneous paste. DMF (1.0 mL) was added and the reaction mixture became a clear solution and it was stirred at rt for 2.5 h. The reaction mixture was then poured into ice and saturated sodium bicarbonated aqueous solution and extracted with DCM (3×). The combined organics were washed with ice-cold sodium bicarbonate aqueous solution (1×) followed by brine (1×), dried over anhydrous sodium sulfate, and concentrated in vacuo. The residue was subjected to combi-flash column chromatography (EtOAc/hexanes, 35 min from 0 to 100% and 10 min at 100%, 40 g ISCO silica gel column) to give 1.05 g of a racemic mixture of 2-(((1R,2R)-2-allylcyclopentyl)sulfonyl)pyrimidine and 2-(((1S,2S)-2-allylcyclopentyl)sulfonyl)pyrimidine as a colorless oil.

Step 5: (1R,2R)-2-allylcyclopentane-1-sulfonamide and (1S,2S)-2-allylcyclopentane-1-sulfonamide

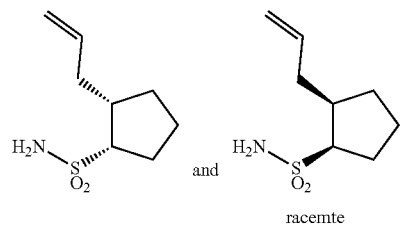

racemte

To a stirred solution of a racemic mixture of 2-(((1R,2R)-2-allylcyclopentyl)sulfonyl)pyrimidine and 2-(((1S,2S)-2-allylcyclopentyl)sulfonyl)pyrimidine (0.641 g, 2.54 mmol) in MeOH (15 mL) was added at rt potassium carbonate (1.053 g, 7.62 mmol) in one portion as a solid. The resulting mixture was stirred at rt for 75 min. The LC-MS indicated the complete consumption of the sm. Amidoperoxymonosulfuric acid (1.436 g, 12.70 mmol) was added at rt in one portion as a solid followed by water (18 mL). The resulting mixture was stirred at rt for 2 min and at 90° C. in a preheated oil bath for 5 min and at rt for 1 h 45 min. The mixture was poured into ice and 1 N sodium hydroxide aqueous solution and extracted with EtOAc (3×). The combined organics were dried over anhydrous sodium sulfate and concentrated in vacuo to give an impure mixture of the title compounds with the major contaminant being 2-methoxypyrimidine, directly taken onto the next step.

Step 6: (S)-6'-chloro-5-(((1R,2R)-2-((S,E)-1-hydroxy-4-((1S,2S)-2-sulfamoyl cyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((1R,2R)-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic

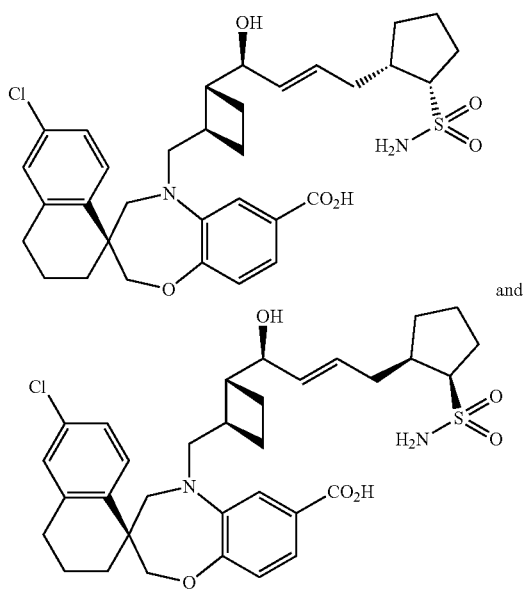

To a 25 mL single-necked round-bottomed flask were placed (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (0.085 g, 0.167 mmol, Intermediate AA12A) and the impure racemic 2-allylcyclopentane-1-sulfonamide (0.095 g, 0.500 mmol). The flask was subjected to 3 cycles of evacuation and back-filling with nitrogen before DCE (2.1 mL) was introduced via syringe under argon at rt. To this stirred solution was added via a syringe a solution of 2$^{nd}$ generation hoveyda-grubbs catalyst (10.44 mg, 0.017 mmol) in DCE (1.2 mL) at rt under argon. The resulting mixture was stirred at rt under argon for a period of 1 h 45 min. The crude mixture was loaded onto a silica gel precolumn and subjected to combi-flash column chromatography ((10% MeOH/DCM with 0.3% AcOH)/DCM, 20 min from 50 to 100% and 20 min at 100%, 24 g ISCO silica gel column) to give a mixture of the title compounds (30 mg, 0.048 mmol, 28.6% yield) as a gray film, taken onto the next step.

Step 7: (1S,3'R,6'R,7'S,8'E,11R,15'R)-6-chloro-7'-hydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'S)-6-chloro-7'-hydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide To a stirred ice-cooled solution of (S)-6'-chloro-5-(((1R,2R)-2-((S,E)-1-hydroxy-4-((1S,2S)-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((1R,2R)-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid (30 mg, 0.048 mmol) and N,N-dimethylpyridin-4-amine (12.81 mg, 0.105 mmol) (14 mg actual) in DCM (25 mL) was added 1-(3-dimethylaminopropyl)-3-ethylcarbodiimide hydrochloride (22.85 mg, 0.119 mmol) in two portions over a period of 5 min. The resulting mixture was stirred in the ice bath for 40 min at ambient temperature for a period of 15 h. The LC-MS and HPLC spectra indicated an epimeric ratio of 3:2. The volatiles were removed. The residue was taken up in DMSO and subjected to preparative reverse-phase HPLC (Gemini™ Prep C$_{18}$ 5 μm column; Phenomenex, Torrance, CA; gradient elution of 55-95% acetonitrile in water, where both solvents contained 0.1% TFA, 30 min method) to give, after lyophilization, 4.0 mg of the title compound as the first eluting fraction as a white solid. $^1$H NMR (500 MHz, CDCl$_3$) δ 8.87 (br. s., 1H), 7.69 (d, J=8.3 Hz, 1H), 7.21-7.12 (m, 2H), 7.10 (d, J=2.2 Hz, 1H), 6.95 (d, J=8.1 Hz, 2H), 6.06-5.93 (m, 1H), 5.71 (dd, J=7.0, 15.5 Hz, 1H), 4.38 (td, J=5.5, 8.1 Hz, 1H), 4.18 (dd, J=3.8, 6.5 Hz, 1H), 4.16-4.07 (m, 2H), 3.61 (t, J=14.5 Hz, 2H), 3.43-3.18 (m, 2H), 2.86-2.71 (m, 2H), 2.58-2.39 (m, 4H), 2.38-2.14 (m, 3H), 2.04-1.64 (m, 12H), 1.56-1.44 (m, 1H). m/z (ESI, +ve ion) 611.2 (M+H)$^+$.

Example 324. (1S,3'R,6'R,7'S,8'E,11'S,15'S)-6-chloro-7'-hydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'R,15'R)-6-chloro-7'-hydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide

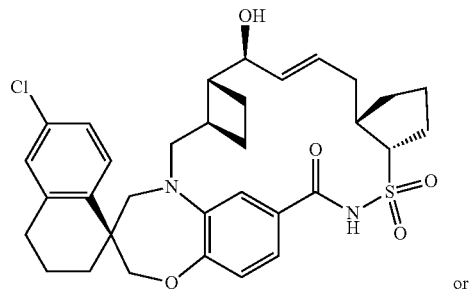

or

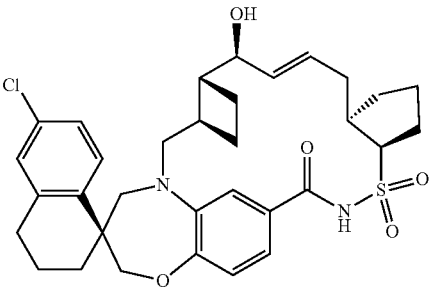

The title compound (4.0 mg) was obtained as a white solid as the second eluting isomer from preparative reverse-phase HPLC (Gemini Prep C$_{18}$ 5 μm column; Phenomenex, Torrance, CA; gradient elution of 55-95% acetonitrile in water, where both solvents contained 0.1% TFA, 30 min method) in Example 323. $^1$H NMR (400 MHz, CDCl$_3$) δ 8.16 (br. s., 1H), 7.71 (d, J=8.6 Hz, 1H), 7.24 (d, J=7.8 Hz, 1H), 7.19 (dd, J=2.3, 8.4 Hz, 1H), 7.09 (d, J=2.2 Hz, 1H), 6.97 (d, J=8.2 Hz, 1H), 6.75 (br. s., 1H), 6.09-5.94 (m, 1H), 5.73 (dd, J=5.8, 15.4 Hz, 1H), 4.33-4.19 (m, 1H), 4.17-4.00 (m, 3H), 3.74 (d, J=14.5 Hz, 1H), 3.65 (d, J=12.9 Hz, 1H), 3.35 (d, J=14.5 Hz, 1H), 3.18 (dd, J=8.7, 14.6 Hz, 1H), 2.87-2.71 (m, 2H), 2.68-2.49 (m, 2H), 2.46-2.14 (m, 5H), 2.05-1.63 (m, 12H), 1.46 (t, J=12.0 Hz, 1H). m/z (ESI, +ve ion) 611.2 (M+H)$^+$.

Example 325. (1S,3′R,6′R,7′S,8′E,11′S,15′R)-6-chloro-7′-hydroxy-3,4-dihydro-2H,18′H-spiro[naphthalene-1,25′-[23]oxa[16]thia[1,17]diazapentacyclo[17.7.2.0³,⁶.0¹¹,¹⁵.0²²,²⁷]octacosa[8,19,21,27]tetraen]-18′-one 16′,16′-dioxide or (1S,3′R,6′R,7′S,8′E,11′R,15′S)-6-chloro-7′-hydroxy-3,4-dihydro-2H,18′H-spiro[naphthalene-1,25′-[23]oxa[16]thia[1,17]diazapentacyclo[17.7.2.0³,⁶.0¹¹,¹⁵.0²²,²⁷]octacosa[8,19,21,27]tetraen]-18′-one 16′,16′-dioxide

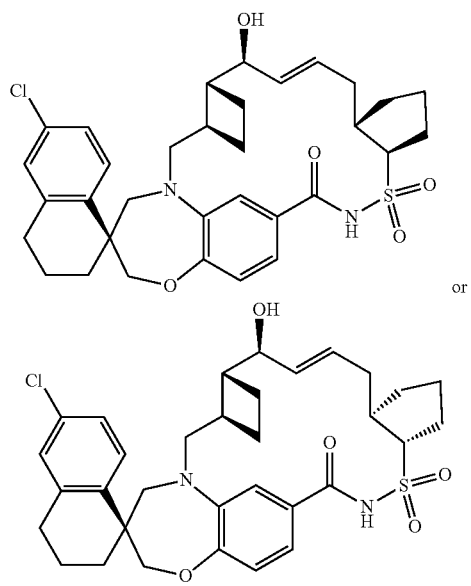

Step 1: (1S,2S)-2-allylcyclopentyl formate and (1R,2R)-2-allylcyclopentyl formate

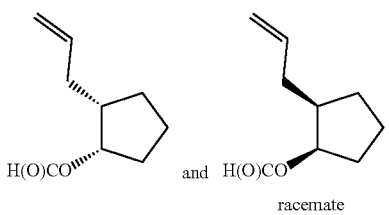

To a stirred ice-cooled solution of a racemic mixture of (1R,2S)-2-allylcyclopentanol and (1S,2R)-2-allylcyclopentanol (3.5 g, 27.7 mmol) and triphenylphosphine (9.09 g, 34.7 mmol) in THF (100 mL) was added 98% formic acid (1.308 mL, 34.7 mmol) followed by slow addition of (E)-diisopropyl diazene-1,2-dicarboxylate (6.87 mL, 34.7 mmol) through a syringe. The resulting mixture was stirred at 0° C. for 15 min and at ambient temperature for a period of 16 h. After the volatiles were removed in vacuo, the residue was subjected to combi-flash column chromatography (EtOAc/Hexanes, 5 min at 0% and 25 min from 0 to 5%, 80 g ISCO silica gel column) to give a racemic mixture of (1S,2S)-2-allylcyclopentyl formate and (1R,2R)-2-allylcyclopentyl formate (3.25 g, 21.08 mmol, 76% yield) as a colorless oil, taken onto the next step.

Step 2: (1S,2S)-2-allylcyclopentanol and (1R,2R)-2-allylcyclopentanol

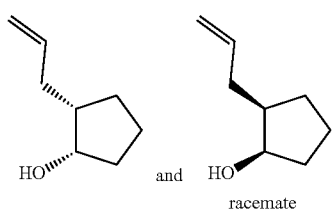

To a stirred solution of a racemic mixture of (1S,2S)-2-allylcyclopentyl formate and (1R,2R)-2-allylcyclopentyl formate (3.25 g, 21.08 mmol) in MeOH (40 mL) was added ammonia hydrate, 27% aqueous solution (4.0 mL, 21.08 mmol) via a syringe at rt. The resulting mixture was stirred at rt for a period of 4 h when TLC showed completion. Note that more commercial ammonium hydroxide (about 10 mL) was added over the course of the reaction. The mixture was poured into ice and saturated ammonium chloride aqueous solution and extracted with Et₂O (3×). The combined organics were dried over anhydrous sodium sulfate and concentrated in vacuo. The residue appeared rather wet and was subjected to combi-flash column chromatography (EtOAc/Hexanes, 5 min at 0% and 25 min from 0 to 30%, 40 g ISCO silica gel column) to give a racemic mixture of (1S,2S)-2-allylcyclopentanol and (1R,2R)-2-allylcyclopentanol (2.30 g, 18.23 mmol, 86% yield) as a colorless oil, taken onto the next step.

Step 3: (1S,2S)-2-allylcyclopentyl methanesulfonate and (1R,2R)-2-allylcyclopentyl methanesulfonate

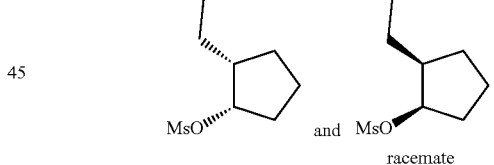

To a stirred ice-cooled solution of a racemic mixture of (1S,2S)-2-allylcyclopentanol and (1R,2R)-2-allylcyclopentanol (2.3 g, 18.23 mmol) and triethylamine (5.58 mL, 40.1 mmol) in DCM (60 mL) was slowly added methanesulfonyl chloride (2.160 mL, 27.3 mmol) through a syringe. The resulting mixture was stirred at 0° C. for a period of 1.5 h. The crude mixture was poured into ice and 1 N aqueous HCl solution and extracted with DCM (2×). The combined organics were washed once again with 1 N aqueous HCl solution followed by brine (2×) and dried over anhydrous sodium sulfate. Concentration in vacuo gave a racemic mixture of (1S,2S)-2-allylcyclopentyl methanesulfonate and (1R,2R)-2-allylcyclopentyl methanesulfonate (3.83 g, 18.75 mmol, 103% yield) as a nearly colorless oil, taken onto the step.

Step 4: 2-(((1R,2S)-2-allylcyclopentyl)thio)pyrimidine and 2-(((1S,2R)-2-allylcyclopentyl)thio)pyrimidine

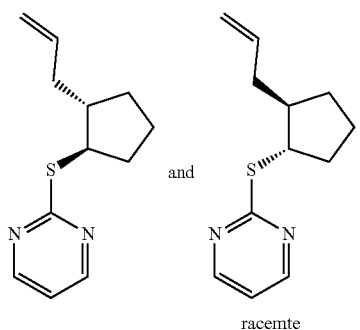

racemte

A mixture of 2-mercapto-pyrimidine (3.15 g, 28.1 mmol) and potassium carbonate anhydrous (4.4 g, 31.9 mmol) in DMF (40 mL) was stirred at rt for 10 min before a solution of a mixture racemic mixture of (1S,2S)-2-allylcyclopentyl methanesulfonate and (1R,2R)-2-allylcyclopentyl methanesulfonate (3.83 g, 18.75 mmol) in THF (40.0 mL) was added at rt. The resulting mixture was stirred at rt for 10 min and at 70° C. for a period of 16 h. The crude mixture was poured into ice and saturated sodium carbonate aqueous solution and extracted with EtOAc (3×). The combined organics were washed with saturated sodium carbonate aqueous solution (1×) followed by water (1×), dried over anhydrous sodium sulfate, and concentrated in vacuo. The residue was subjected to combi-flash column chromatography (EtOAc/hexanes, 5 min at 0% and 25 min from 0 to 30%, 80 g ISCO silica gel column) to give a racemic mixture of 2-(((1R,2S)-2-allylcyclopentyl)thio)pyrimidine and 2-(((1S,2R)-2-allylcyclopentyl)thio)pyrimidine (1.92 g, 8.71 mmol, 46.5% yield) as a colorless oil, taken onto the next step.

Step 5: 2-(((1R,2S)-2-allylcyclopentyl)sulfonyl)pyrimidine and 2-(((1S,2R)-2-allylcyclopentyl)sulfonyl)pyrimidine

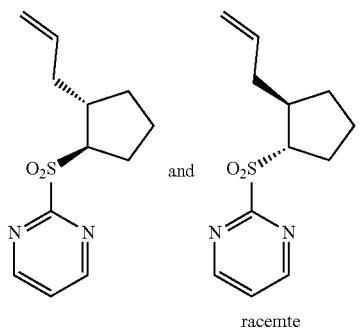 [SMILES: C=CC[C@@H]1CCC[C@H]1S(=O)(=O)c1ncccn1 ; C=CC[C@H]1CCC[C@@H]1S(=O)(=O)c1ncccn1]

racemte

To a stirred ice-cooled solution of a racemic mixture of 2-(((1R,2S)-2-allylcyclopentyl)thio)pyrimidine and 2-(((1S,2R)-2-allylcyclopentyl)thio)pyrimidine (0.87 g, 3.95 mmol) in DCM (20 mL) and DMF (2.00 mL) was added 3-chlorobenzoperoxoic acid (1.858 g, 8.29 mmol) in 3 portions as a solid over 10 min. The resulting mixture was stirred at 0° C. for about 1 h 15 min. The ice bath was then removed and the mixture was stirred at rt for 2 h. The reaction was then poured into ice and saturated sodium carbonate aqueous solution and extracted with DCM (3×). The combined organics were washed with ice-cold sodium carbonate aqueous solution (1×), dried over anhydrous sodium sulfate, and concentrated in vacuo. The residue was subjected to combi-flash column chromatography (EtOAc/Hexanes, 25 min from 0 to 100%, 24 g ISCO silica gel column) to give a racemic mixture of 2-(((1R,2S)-2-allylcyclopentyl)sulfonyl)pyrimidine and 2-(((1S,2R)-2-allylcyclopentyl)sulfonyl)pyrimidine (0.90 g, 3.57 mmol, 90% yield) as a colorless oil, taken onto the next step.

Step 6: (1R,2S)-2-allylcyclopentane-1-sulfonamide and (1S,2R)-2-allylcyclopentane-1-sulfonamide

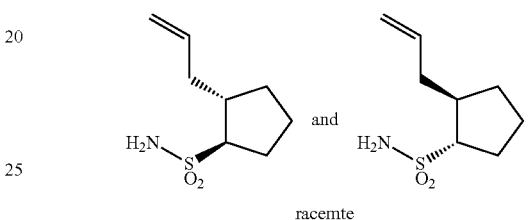

racemte

The 1$^{st}$ step: To a stirred solution of a racemic mixture of 2-(((1R,2S)-2-allylcyclopentyl)sulfonyl)pyrimidine and 2-(((1S,2R)-2-allylcyclopentyl)sulfonyl)pyrimidine (0.90 g, 3.57 mmol) in MeOH (35 mL) was added at rt sodium methoxide, 25 wt % solution in methanol (0.795 mL, 3.57 mmol) via a syringe. The resulting mixture was stirred at rt for 25 min and on rotavap at 52° C. for 10 min to remove the volatiles. The residue was subjected to high vacuum.

The 2$^{nd}$ step: To the above residue was added water (30 mL) followed by sodium acetate trihydrate (0.67 mL, 7.13 mmol) and amidoperoxymonosulfuric acid (0.81 g, 7.13 mmol) at rt. The resulting clear solution was stirred at 50° C. in a preheated oil bath for a period of 40 min. The LC-MS showed this time that the desired product was the minor while still the intermediate sulfinate was the overwhelmingly major. The temperature was raised to 95° C. and the reaction mixture was stirred at this temperature for 10 min. The LC-MS showed this time that the desired product became the major with some of the intermediate sulfinate still remaining. The reaction was put back into the 95° C. oil bath and stirred for 10 min. The LC-MS showed the reaction stalled with some of the fulfinate still remaining. After briefly cooled, one equivalent each of sodium acetate and amidoperoxymonosulfuric acid was added. The mixture was stirred at 95° C. for 10 min and became cloudy upon cooling. It was basified using ice cold saturated sodium carbonate and extracted with 20% i-PrOH/DCM (5×). The combined organics were dried over anhydrous sodium sulfate and concentrated in vacuo. The residue was subjected to combi-flash column chromatography (EtOAc/Hexanes, 20 min from 0 to 70%, 24 g ISCO silica gel column) to give, as a colorless crystalline solid, 0.61 g of a mixture of the title compound and 2-methoxypyrimidine (the by-product) in a ratio of 3.5 to 1. This was triturated with EtOAc/hexanes to give a pure racemic mixture of (1R,2S)-2-allylcyclopentane-1-sulfonamide and (1S,2R)-2-allylcyclopentane-1-sulfonamide (0.4668 g, 2.69 mmol, 76% yield) as a white solid.

Step 7: (S)-6'-chloro-5-(((1R,2R)-2-((S,E)-1-hydroxy-4-((1S,2R)-2-sulfamoyl cyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((1R,2S)-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic

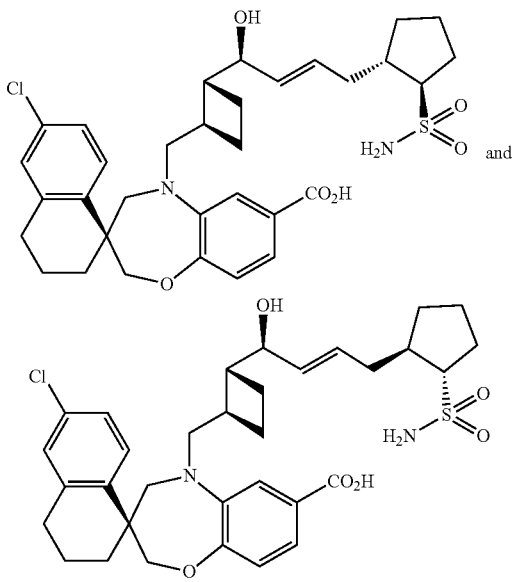

To a 25 mL single-necked round-bottomed flask were placed (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (0.194 g, 0.380 mmol, Intermediate AA12A), a racemic mixture (1R,2S)-2-allylcyclopentane-1-sulfonamide and (1S,2R)-2-allylcyclopentane-1-sulfonamide (0.180 g, 0.951 mmol), and $2^{nd}$ generation hoveyda-grubbs catalyst (0.024 g, 0.038 mmol). The flask was subjected to 3 cycles of evacuation and back-filling with nitrogen before DCE (5 mL) was introduced through a syringe under nitrogen. The resulting mixture was stirred under nitrogen at rt for a period of 4 h. The crude mixture was loaded onto a silica gel precolumn and subjected to combi-flash column chromatography ((10% MeOH/DCM with 0.3% AcOH)/DCM), 25 min from 0 to 100%, 24 g ISCO silica gel column) to give a mixture of the title compounds (0.19 g, 0.302 mmol, 79% yield) as a gray solid, taken onto the next step.

Step 8: (1S,3'R,6'R,7'S,8'E,11'S,15'R)-6-chloro-7'-hydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'R,15'S)-6-chloro-7'-hydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide To a stirred ice-cooled solution of (S)-6'-chloro-5-(((1R,2R)-2-((S,E)-1-hydroxy-4-((1S,2R)-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((1R,2S)-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid (190 mg, 0.302 mmol) and N,N-dimethylpyridin-4-amine (81 mg, 0.664 mmol) in DCM (150 mL) was added 1-(3-dimethylaminopropyl)-3-ethylcarbodiimide hydrochloride (145 mg, 0.755 mmol) in one portion. The resulting mixture was stirred at 0° C. and gradually warmed up to ambient temperature overnight (12 h). The volatiles were removed in vacuo. A portion (⅓) of the crude residue was taken up in DMSO and subjected to preparative reverse-phase HPLC (Gemini Prep $C_{18}$ 5 μm column; Phenomenex, Torrance, CA; gradient elution of 55-95% acetonitrile in water, where both solvents contained 0.1% TFA, 30 min method) to give, after lyophilization, 10 mg of the title compound as the first eluting fraction as an off-white solid. $^1$H NMR (500 MHz, CDCl$_3$) δ 8.33 (br. s., 1H), 7.70 (d, J=8.6 Hz, 1H), 7.18 (dd, J=2.2, 8.6 Hz, 1H), 7.09 (d, J=2.2 Hz, 1H), 7.01-6.89 (m, 3H), 5.82-5.73 (m, 1H), 5.72-5.62 (m, 1H), 4.25 (td, J=6.4, 8.8 Hz, 1H), 4.18 (dd, J=5.1, 7.1 Hz, 1H), 4.14-4.03 (m, 2H), 3.81 (dd, J=2.2, 15.2 Hz, 1H), 3.72 (d, J=14.4 Hz, 1H), 3.23 (d, J=14.4 Hz, 1H), 3.04 (dd, J=8.4, 15.3 Hz, 1H), 2.86-2.71 (m, 2H), 2.54-2.22 (m, 6H), 2.19-1.58 (m, 12H), 1.55-1.45 (m, 1H), 1.42 (t, J=12.5 Hz, 1H). m/z (ESI, +ve ion) 611.3 (M+H)$^+$.

Example 326. (1S,3'R,6'R,7'S,8'E,11'S,15'R)-6-chloro-7'-hydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'R,15'S)-6-chloro-7'-hydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide

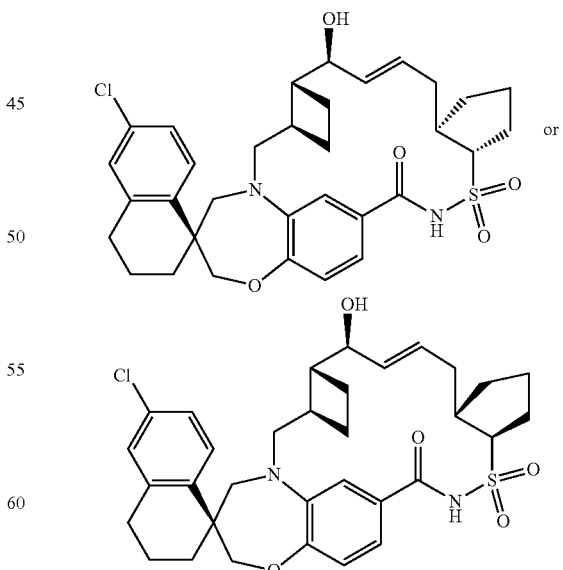

The title compound (15 mg) was obtained as an off-white solid as the second eluting isomer from preparative reverse-phase HPLC (Gemini Prep $C_{18}$ 5 μm column; Phenomenex, Torrance, CA; gradient elution of 55-95% acetonitrile in water, where both solvents contained 0.1% TFA, 30 min method) in Example 325. $^1$H NMR (500 MHz, CDCl$_3$) δ 8.18 (s, 1H), 7.66 (d, J=8.6 Hz, 1H), 7.54 (br. s., 1H), 7.16 (dd, J=2.2, 8.6 Hz, 1H), 7.10 (d, J=2.4 Hz, 1H), 6.98-6.84 (m, 2H), 5.72 (dd, J=5.1, 15.7 Hz, 1H), 5.54 (br. s., 1H), 4.29-4.16 (m, 2H), 4.11-3.94 (m, 2H), 3.69 (br. s., 1H), 3.49-3.10 (m, 2H), 2.81-2.73 (m, 2H), 2.62-2.35 (m, 4H), 2.27 (dtd, J=6.1, 8.8, 14.9 Hz, 1H), 2.20-1.63 (m, 14H), 1.51-1.34 (m, 2H). m/z (ESI, +ve ion) 611.3 (M+H)$^+$.

Example 328. (1S,3'R,6'R,7'S,8'E,11'S,15'R)-6-chloro-7'-((1-methyl-1H-1,2,4-triazol-3-yl)methoxy)-3,4-dihydro-2H,18'H-spiro[naphthalene-1,25'-[23]oxa[16]thia[1,17]diazapentacyclo [17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11R,15'S)-6-chloro-7'-((1-methyl-1H-1,2,4-triazol-3-yl)methoxy)-3,4-dihydro-2H,18'H-spiro[naphthalene-1,25'-[23]oxa[16]thia[1,17]diazapentacyclo [17.7.2.0$^{3,6}$.0$^{11,15}$.0$^{22,27}$]octacosa[8,19,21,27]tetraen]-18'-one 16',16'-dioxide

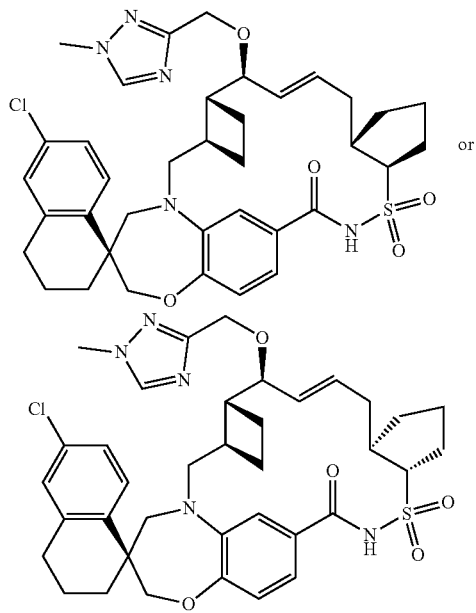

or

To a stirred solution of (1S,3'R,6'R,7'S,8'E,11'S,15'R)-6-chloro-7'-hydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide and (1S,3'R,6'R,7'S,8'E,11'R,15'S)-6-chloro-7'-hydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide (14 mg, 0.023 mmol, Examples 326) in DMF (2 mL) was added sodium hydride, 60% dispersion in mineral oil (9.16 mg, 0.229 mmol) (20 mg actually) at rt. The resulting mixture was stirred at rt for 30 min before 3-chloromethyl-1-methyl-1h-[1,2,4]triazole, hydrochloride (0.014 mL, 0.115 mmol) was added as a solid at rt. The resulting mixture was stirred at rt for a period of 3 days. Note that more NaH (not weighed) was added after 6 h. The reaction was quenched with methanol and the resulting mixture was taken up in DMSO and subjected to preparative reverse-phase HPLC (Gemini Prep C$_{18}$ 5 lam column; Phenomenex, Torrance, CA; gradient elution of 50-95% acetonitrile in water, where both solvents contained 0.1% TFA, 30 min method) to give, after lyophilization, 2.0 mg of the title compound as the first eluting fraction as a white solid. $^1$H NMR (400 MHz, CDCl$_3$) δ 8.33 (s, 1H), 8.20 (s, 1H), 7.70 (d, J=8.6 Hz, 1H), 7.18 (dd, J=2.3, 8.4 Hz, 1H), 7.09 (d, J=2.2 Hz, 1H), 6.93-6.81 (m, 2H), 6.77 (s, 1H), 5.92-5.75 (m, 1H), 5.59 (dd, J=9.0, 15.3 Hz, 1H), 4.67-4.55 (m, 1H), 4.50-4.38 (m, 2H), 4.13-4.01 (m, 2H), 3.99 (s, 3H), 3.86 (dd, J=3.8, 8.7 Hz, 1H), 3.81-3.68 (m, 2H), 3.17 (d, J=14.3 Hz, 1H), 2.96 (dd, J=9.6, 15.3 Hz, 1H), 2.84-2.69 (m, 2H), 2.60-2.20 (m, 6H), 2.08-1.72 (m, 9H), 1.68-1.49 (m, 3H), 1.38 (t, J=12.6 Hz, 1H). m/z (ESI, +ve ion) 706.3 (M+H)$^+$.

Example 329. (1S,3'R,6'R,7'S,8'E,11'R,15'S)-6-chloro-7'-((1-methyl-1H-1,2,4-triazol-3-yl)methoxy)-3,4-dihydro-2H,18'H-spiro[naphthalene-1,25'-[23]oxa[16]thia[1,17]diazapentacyclo [17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'R)-6-chloro-7'-((1-methyl-1H-1,2,4-triazol-3-yl)methoxy)-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide

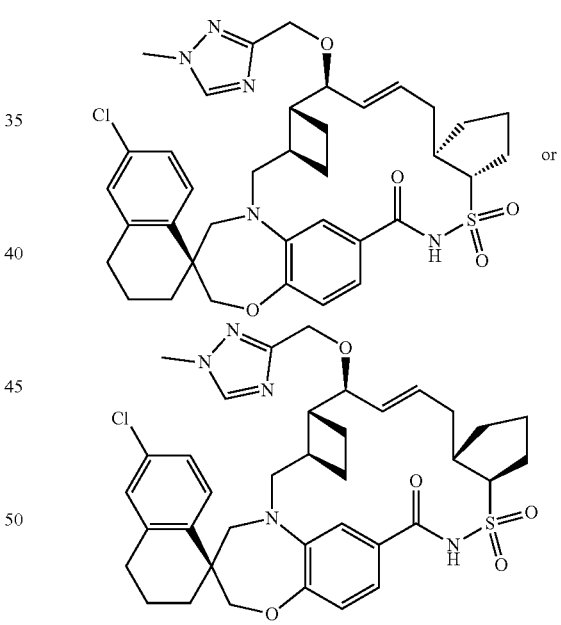

The title compound (2.0 mg) was obtained as a white solid as the second eluting isomer from preparative reverse-phase HPLC (Gemini Prep C$_{18}$ 5 μm column; Phenomenex, Torrance, CA; gradient elution of 50-95% acetonitrile in water, where both solvents contained 0.1% TFA, 30 min method) in Example 328. $^1$H NMR (500 MHz, CDCl$_3$) δ 8.27 (br. s., 2H), 7.68 (d, J=8.6 Hz, 1H), 7.21-7.16 (m, J=2.3, 8.4 Hz, 1H), 7.09 (d, J=2.0 Hz, 1H), 6.98 (d, J=8.3 Hz, 1H), 6.90 (d, J=8.1 Hz, 1H), 6.84 (br. s., 1H), 6.00-5.82 (m, 1H), 5.54 (dd, J=7.9, 15.3 Hz, 1H), 4.66-4.56 (m, 1H), 4.50 (d, J=12.5 Hz, 1H), 4.13-4.02 (m, 2H), 3.98 (s, 3H), 3.88 (br. s., 1H), 3.77-3.54 (m, 3H), 3.31 (d, J=14.4 Hz, 1H), 3.16 (br. s., 1H), 2.86-2.69 (m, 3H), 2.51-1.55 (m, 16H), 1.49-1.34 (m, 2H). m/z (ESI, +ve ion) 706.3 (M+H)+.

Example 330. (1S,3'R,6'R,7'S,11R,15'R)-6-chloro-7'-hydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[19,21,27]trien]-18'-one 16',16'-dioxide or (1S,3'R,6'R,7'S,11'S,15'S)-6-chloro-7'-hydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[19,21,27]trien]-18'-one 16',16'-dioxide

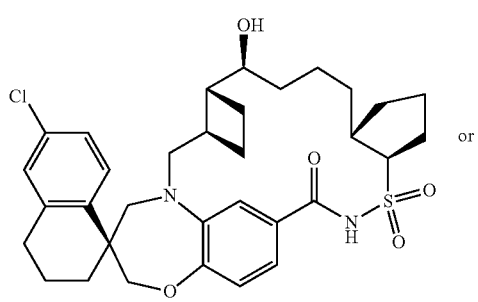

or

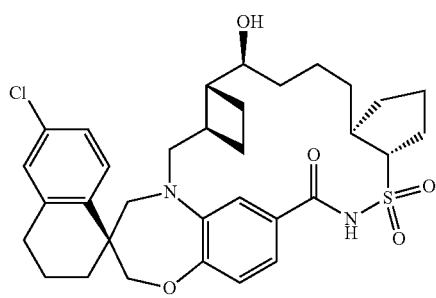

A mixture of (1S,3'R,6'R,7'S,8'E,11'S,15'R)-6-chloro-7'-hydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'R,15'S)-6-chloro-7'-hydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide (12 mg, 0.020 mmol, Example 326) and platinum (iv) oxide (0.892 mg, 3.93 μmol) (in excess) in EtOAc (8 mL) was degassed and purged with hydrogen for multiple times and balloon hydrogenated for a period of 3.5 h. The reaction was quenched with DCM. The solid was filtered off and the residue after concentration in vacuo was taken up in DMSO and subjected to preparative reverse-phase HPLC (Gemini Prep C$_{18}$ 5 μm column; Phenomenex, Torrance, CA; gradient elution of 55-95% acetonitrile in water, where both solvents contained 0.1% TFA, 30 min method) to give, after lyophilization, 3.5 mg of the title compound as a white solid. $^{1}$H NMR (400 MHz, CDCl$_3$) δ 9.27 (br. s., 1H), 7.68 (d, J=8.6 Hz, 1H), 7.41 (d, J=1.6 Hz, 1H), 7.22 (d, J=7.8 Hz, 1H), 7.17 (dd, J=2.3, 8.4 Hz, 1H), 7.09 (d, J=2.2 Hz, 1H), 6.95 (d, J=8.2 Hz, 1H), 4.19-4.03 (m, 2H), 3.86 (td, J=6.6, 9.5 Hz, 1H), 3.78-3.58 (m, 3H), 3.39-3.11 (m, 2H), 2.85-2.71 (m, 2H), 2.55-1.18 (m, 24H). m/z (ESI, +ve ion) 706.3 (M+H)+.

Example 331. (1S,3'R,6'R,7'S,8'E,11'S,16'R)-6-chloro-7'-hydroxy-3,4-dihydro-2H,19'H-spiro[naphthalene-1,26'-[24]oxa[17]thia[1,18]diazapentacyclo[18.7.2.0$^{3,6}$.0$^{11,16}$.0$^{23,28}$]nonacosa[8,20,22,28]tetraen]-19'-one 17',17'-dioxide

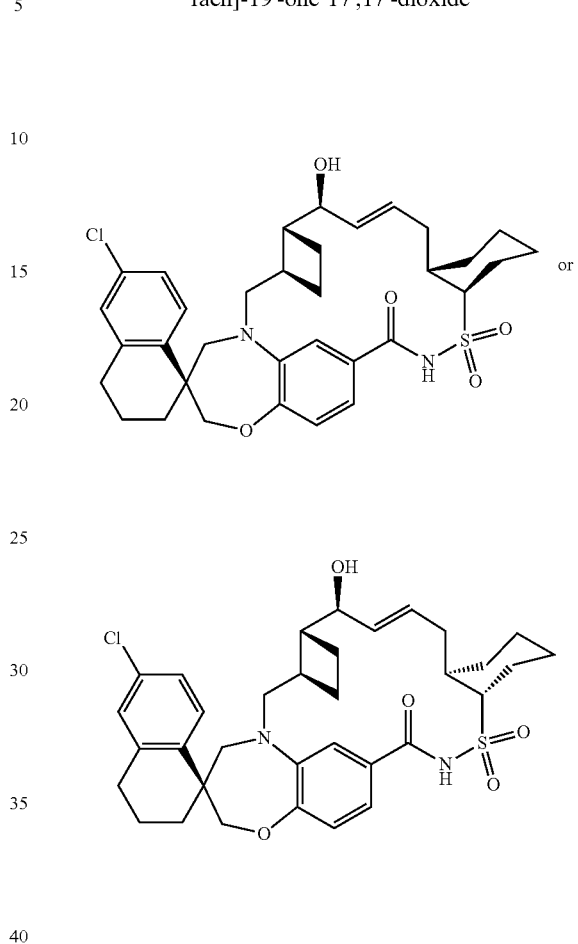

Step 1: (1R,2S)-2-allylcyclohexanol and (1S,2R)-2-allylcyclohexanol

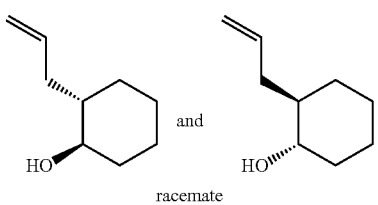

racemate

To a stirred ice-cooled allylmagnesium bromide, 1.0 M solution in diethyl ether (44.9 mL, 44.9 mmol) was slowly added a solution of cyclohexene oxide (2.165 mL, 21.40 mmol) in diethyl ether (45 mL) via a syringe over a period of 10 min. The resulting mixture was stirred at 0° C. for a period of 0.5 h. The reaction mixture was carefully quenched and further diluted with ice cold saturated ammonium chloride aqueous solution and extracted with Et$_2$O (3×). The combined organics were dried over anhydrous sodium sulfate and concentrated in vacuo to give a racemic mixture of (1R,2S)-2-allylcyclohexanol and (1S,2R)-2-allylcyclohexanol (3.1 g, 22.11 mmol, 103% yield) as a colorless oil, taken directly onto the next step.

Step 2: (1S,2S)-2-allylcyclohexyl formate and (1R,2R)-2-allylcyclohexyl formate

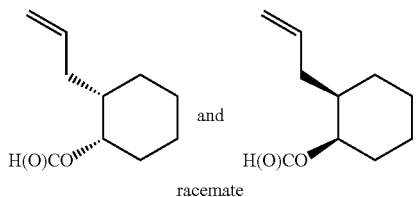
racemate

To a stirred ice-cooled solution of a racemic mixture of (1R,2S)-2-allylcyclohexanol and (1S,2R)-2-allylcyclohexanol (3.100 g, 22.11 mmol) and triphenylphosphine (7.25 g, 27.6 mmol) in THF (100 mL) was added 98% formic acid (1.043 mL, 27.6 mmol) followed by slow addition of (E)-diisopropyl diazene-1,2-dicarboxylate (5.48 mL, 27.6 mmol) through a syringe over a period of 15 min. Note that the mixture turned cloudy toward the end of the addition. The ice bath was removed upon the completion of addition. The resulting mixture was stirred at ambient temperature for a period of 20 h. Note that the cloudy mixture gradually became clear within the first hour or so and the reaction did not go to completion by the time of workup. After the volatiles were removed in vacuo, the residue was subjected to combi-flash column chromatography (EtOAc/Hexanes, 5 min at 0% and 30 min from 0 to 30%, 80 g ISCO silica gel column) to give a racemic mixture of (1S,2S)-2-allylcyclohexyl formate and (1R,2R)-2-allylcyclohexyl formate (2.0 g, 11.89 mmol, 53.8% yield) as a nearly colorless oil, taken onto the next step.

Step 3: (1S,2S)-2-allylcyclohexanol and (1R,2R)-2-allylcyclohexanol

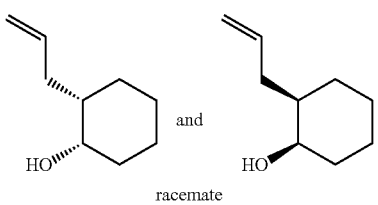
racemate

To a stirred solution of a racemic mixture of (1S,2S)-2-allylcyclohexyl formate and (1R,2R)-2-allylcyclohexyl formate (2.0 g, 11.89 mmol) in MeOH (70 mL) was added ammonia hydrate, 27% aqueous solution (10 mL, 11.89 mmol) via a syringe at rt. The resulting mixture was stirred at rt for a period of 18 h when TLC showed completion. The volatiles were removed and the residue was subjected to combi-flash column chromatography (EtOAc/Hexanes, 4 min at 0% and 25 min from 0 to 30%, 40 g ISCO silica gel column) to give a racemic mixture (1S,2S)-2-allylcyclohexanol and (1R,2R)-2-allylcyclohexanol (1.13 g, 8.06 mmol, 67.8% yield) as a colorless oil, taken onto the next step.

Step 4: (1S,2S)-2-allylcyclohexyl methanesulfonate and (1R,2R)-2-allylcyclohexyl methanesulfonate

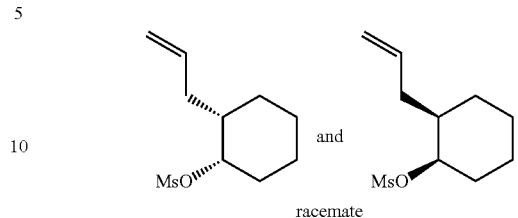
racemate

To a stirred ice-cooled solution of a racemic mixture of (1S,2S)-2-allylcyclohexanol and (1R,2R)-2-allylcyclohexanol (1.13 g, 8.06 mmol) and triethylamine (2.47 mL, 17.73 mmol) in DCM (40 mL) was slowly added methanesulfonyl chloride (0.955 mL, 12.09 mmol) through a syringe. The resulting mixture was stirred at 0° C. for a period of 1.5 h. The crude mixture was poured into ice and 1 N aqueous HCl solution and extracted with DCM (2×). The combined organics were once again washed with 1 N aqueous HCl solution followed by brine (2×) and dried over anhydrous sodium sulfate. Concentration in vacuo gave a racemic mixture of (1S,2S)-2-allylcyclohexyl methanesulfonate and (1R,2R)-2-allylcyclohexyl methanesulfonate (1.83 g, 8.38 mmol, 104% yield) as a colorless oil, directly taken onto the step.

Step 5: 2-(((1R,2S)-2-allylcyclohexyl)thio)pyrimidine and 2-(((1S,2R)-2-allylcyclohexyl)thio)pyrimidine

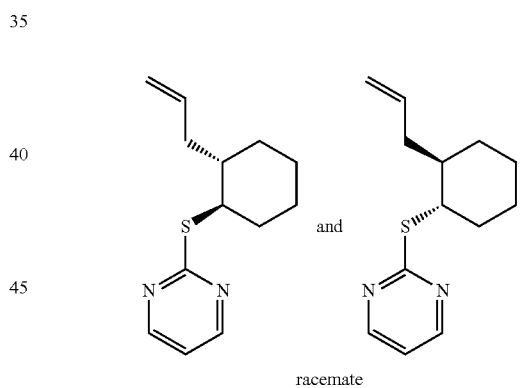
racemate

A mixture of 2-mercapto-pyrimidine (1.598 g, 14.25 mmol) and potassium carbonate anhydrous (1.265 mL, 20.96 mmol) in DMF (30 mL) was stirred at rt for 15 min before a solution of a racemic mixture of (1S,2S)-2-allylcyclohexyl methanesulfonate and (1R,2R)-2-allylcyclohexyl methanesulfonate (1.830 g, 8.38 mmol) THF (30 mL) was added at rt. The resulting mixture was stirred at rt for 30 min and at 75° C. for a period of 5 h. The crude mixture was poured into ice and saturated sodium carbonate aqueous solution and extracted with EtOAc (2×). The combined organics were washed with saturated sodium carbonate aqueous solution (1×) followed by water (1×), dried over anhydrous sodium sulfate, and concentrated in vacuo. The residue was subjected to combi-flash column chromatography (EtOAc/hexanes, 5 min at 0% and 25 min from 0 to 30%, 40 g silica gel, 18 mm tubes) to give a racemic mixture of 2-(((1R,2S)-2-allylcyclohexyl)thio)pyrimidine and 2-(((1S,2R)-2-allylcyclohexyl)thio)pyrimidine (not weighed) as a colorless oil, directly taken onto the next step.

Step 6: 2-(((1R,2S)-2-allylcyclohexyl)sulfonyl)pyrimidine and 2-(((1S,2R)-2-allylcyclohexyl)sulfonyl)pyrimidine

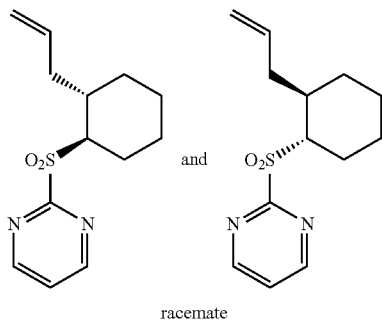 [SMILES: C=CC[C@@H]1CCCC[C@H]1S(=O)(=O)c1ncccn1 ; C=CC[C@H]1CCCC[C@@H]1S(=O)(=O)c1ncccn1]

racemate

To a stirred ice-cooled solution of a racemic mixture of 2-(((1R,2S)-2-allylcyclohexyl)thio)pyrimidine and 2-(((1S,2R)-2-allylcyclohexyl)thio)pyrimidine (0.27 g, 1.152 mmol) in DCM (6 mL) and DMF (0.2 mL) was added 3-chlorobenzoperoxoic acid (0.542 g, 2.419 mmol) in one portion as a solid. The resulting mixture was stirred at 0° C. for 5 min and at rt for a period of 3 h 40 min. The mixture was directly loaded onto silica gel precolumn and was subjected to combi-flash column chromatography (EtOAc/Hexanes, 25 min from 0 to 100%, 24 g ISCO silica gel column) to give a racemic mixture of 2-(((1R,2S)-2-allylcyclohexyl)sulfonyl)pyrimidine and 2-(((1S,2R)-2-allylcyclohexyl)sulfonyl)pyrimidine (0.224 g, 0.841 mmol, 73.0% yield) as a colorless oil, taken onto the next step.

Step 7: (1R,2S)-2-allylcyclohexane-1-sulfonamide and (1S,2R)-2-allylcyclohexane-1-sulfonamide

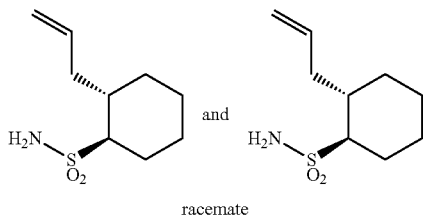

racemate

The 1$^{st}$ step: To a stirred solution of a racemic mixture of 2-(((1R,2S)-2-allylcyclohexyl)sulfonyl)pyrimidine and 2-(((1S,2R)-2-allylcyclohexyl)sulfonyl)pyrimidine (0.224 g, 0.841 mmol) in MeOH (9 mL) was added at rt sodium methoxide, 25 wt % solution in methanol (0.187 mL, 0.841 mmol) via a syringe. The resulting mixture was stirred at rt for 30 min when LC-MS showed completion. The volatiles were removed in vacuo and the residue was subjected to high vacuum.

The 2$^{nd}$ step: To the above residue was added water (9 mL) followed by sodium acetate trihydrate (0.158 mL, 1.682 mmol) and amidoperoxymonosulfuric acid (0.190 g, 1.682 mmol) at rt. The resulting clear solution was stirred at 75° C. in a preheated oil bath for a period of 40 min. The mixture became cloudy upon cooling. It was basified using ice cold saturated sodium carbonate and extracted with 20% i-PrOH/DCM (5×). The combined organics were dried over anhydrous sodium sulfate and concentrated in vacuo to give 0.27 g of the crude product. This was subjected to combi-flash column chromatography (EtOAc/Hexanes, 3 min at 0 and 27 min from 0 to 60%, 24 g silica gel column, 13 mm tubes) to give a racemic mixture of (1R,2S)-2-allylcyclohexane-1-sulfonamide and (1S,2R)-2-allylcyclohexane-1-sulfonamide as a colorless solid, taken onto the next step.

Step 8: (S)-6'-chloro-5-(((1R,2R)-2-((S,E)-1-hydroxy-4-((1S,2R)-2-sulfamoylcyclohexyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((1R,2S)-2-sulfamoylcyclohexyl)but-2-en-1-yl)cyclobutyl)methyl)-3',4,4',5-tetrahydro-2H,2'H-spiro[benzo[b][1,4]oxazepine-3,1'-naphthalene]-7-carboxylic

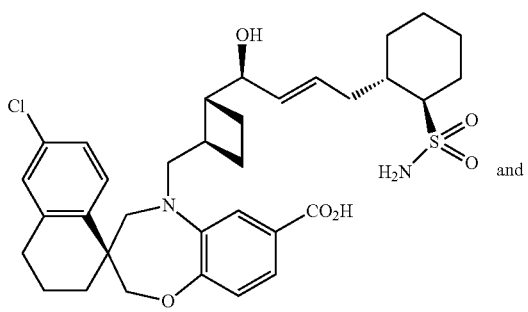

and

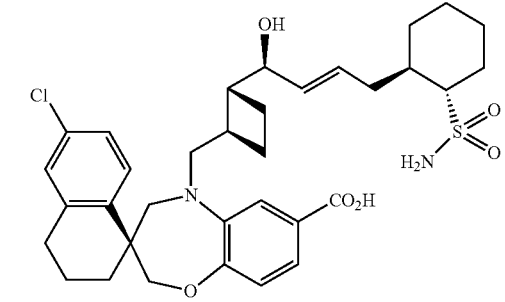

To a 25 mL single-necked round-bottomed flask were placed (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (0.20 g, 0.392 mmol, Intermediate AA12A), racemic (1R,2S)-2-allylcyclohexane-1-sulfonamide (0.128 g, 0.627 mmol), and 2$^{nd}$ generation hoveyda-grubbs catalyst (0.025 g, 0.039 mmol). The flask was subjected to 3 cycles of evacuation and back-filling with nitrogen before DCE (5 mL) was introduced through a syringe under nitrogen. The resulting mixture was stirred under nitrogen at rt for a period of 3 h. The crude mixture was loaded onto a silica gel precolumn and subjected to combi-flash column chromatography ((10% MeOH/DCM with 0.3% AcOH)/DCM), 25 min from 0 to 60%, 24 g ISCO silica gel column) to give a mixture of the title compounds (0.15 g, 0.233 mmol, 59.5% yield) as an off-white solid, taken onto the next step.

803

Step 9: (1S,3'R,6'R,7'S,8'E,11'S,16'R)-6-chloro-7'-hydroxy-3,4-dihydro-2H,19'H-spiro[naphthalene-1,26'-[24]oxa[17]thia[1,18]diazapentacyclo [18.7.2.0$^{3,6}$.0$^{11,16}$.0$^{23,28}$]nonacosa[8,20,22,28]tetraen]-19'-one 17',17'-dioxide or (1S,3'R,6'R,7'S,8'E,11'R,16'S)-6-chloro-7'-hydroxy-3,4-dihydro-2H,19'H-spiro[naphthalene-1,26'-[24]oxa[17]thia[1,18]diazapentacyclo [18.7.2.0$^{3,6}$.0$^{11,16}$.0$^{23,28}$]nonacosa[8,20,22,28]tetraen]-19'-one 17',17'-dioxide To a stirred ice-cooled solution of (S)-6'-chloro-5-(((1R,2R)-2-((S,E)-1-hydroxy-4-((1S,2R)-2-sulfamoylcyclohexyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((1R,2S)-2-sulfamoylcyclohexyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid (150 mg, 0.233 mmol) and N,N-dimethylpyridin-4-amine (62.7 mg, 0.513 mmol) in DCM (120 mL) was added 1-(3-dimethylaminopropyl)-3-ethylcarbodiimide hydrochloride (112 mg, 0.583 mmol) in one portion. The resulting mixture was stirred at 0° C. and gradually warmed up to ambient temperature overnight (16 h). The volatiles were removed in vacuo. The crude residue was taken up in DMSO and subjected to preparative reverse-phase HPLC (Gemini Prep C$_{18}$ 5 μm column; Phenomenex, Torrance, CA; gradient elution of 55-95% acetonitrile in water, where both solvents contained 0.1% TFA, 30 min method) to give, after lyophilization, 20 mg of the title compound as the first eluting fraction as an off-white solid. $^1$H NMR (500 MHz, CDCl$_3$) δ 8.16 (s, 1H), 7.70 (d, J=8.6 Hz, 1H), 7.19 (dd, J=2.2, 8.6 Hz, 1H), 7.09 (d, J=2.2 Hz, 1H), 6.93 (s, 2H), 6.78 (s, 1H), 5.94-5.82 (m, 1H), 5.67 (dd, J=8.2, 15.0 Hz, 1H), 4.24 (dd, J=3.8, 8.2 Hz, 1H), 4.15-4.00 (m, 3H), 3.79 (d, J=15.2 Hz, 1H), 3.71 (d, J=14.2 Hz, 1H), 3.20 (d, J=14.2 Hz, 1H), 3.00 (dd, J=9.8, 15.4 Hz, 1H), 2.85-2.71 (m, 2H), 2.49-2.23 (m, 5H), 2.13-1.58 (m, 13H), 1.51-1.29 (m, 4H). m/z (ESI, +ve ion) 625.2 (M+H)$^+$.

Example 332. (1S,3'R,6'R,7'S,8'E,11'R,16'S)-6-chloro-7'-hydroxy-3,4-dihydro-2H,19'H-spiro[naphthalene-1,26'-[24]oxa[17]thia[1,18]diazapentacyclo [18.7.2.0$^{3,6}$.0$^{11,16}$.0$^{23,28}$]nonacosa[8,20,22,28]tetraen]-19'-one 17',17'-dioxide

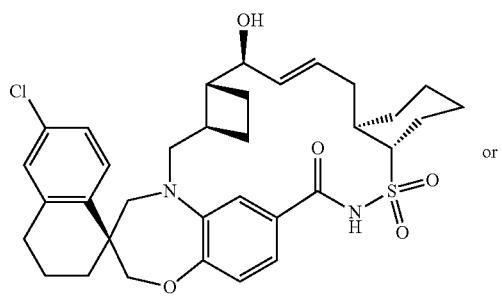

or

804

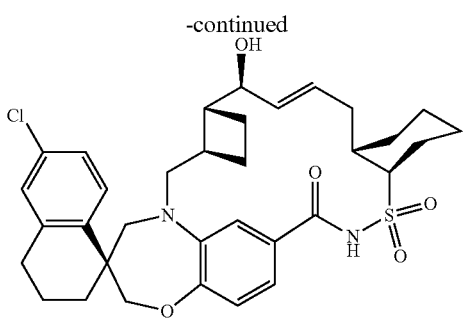

The title compound (30 mg) was obtained as an off-white solid as the second eluting isomer from preparative reverse-phase HPLC (Gemini Prep C$_{18}$ 5 μm column; Phenomenex, Torrance, CA; gradient elution of 55-95% acetonitrile in water, where both solvents contained 0.1% TFA, 30 min method) in Example 331. $^1$H NMR (500 MHz, CDCl$_3$) δ 8.25 (br. s., 1H), 7.66 (d, J=8.6 Hz, 1H), 7.17 (dd, J=2.2, 8.6 Hz, 1H), 7.10 (d, J=2.2 Hz, 1H), 7.02 (d, J=7.1 Hz, 1H), 6.93 (d, J=8.1 Hz, 1H), 5.94-5.41 (m, 2H), 4.29-3.88 (m, 4H), 3.73-3.21 (m, 3H), 2.76 (br. s., 2H), 2.66-1.31 (m, 23H). m/z (ESI, +ve ion) 625.2 (M+H)$^+$.

Example 333. (1S,3'R,6'R,7'S,11'S,16'R)-6-chloro-7'-hydroxy-3,4-dihydro-2H,19'H-spiro[naphthalene-1,26'-[24]oxa[17]thia[1,18]diazapentacyclo [18.7.2.0$^{3,6}$.0$^{11,16}$.0$^{23,28}$]nonacosa[20,22,28]trien]-19'-one 17',17'-dioxide or (1S,3'R,6'R,7'S,11'R,16'S)-6-chloro-7'-hydroxy-3,4-dihydro-2H,19'H-spiro[naphthalene-1,26'-[24]oxa[17]thia[1,18]diazapentacyclo [18.7.2.0$^{3,6}$.0$^{11,16}$.0$^{23,28}$]nonacosa[20,22,28]trien]-19'-one 17',17'-dioxide

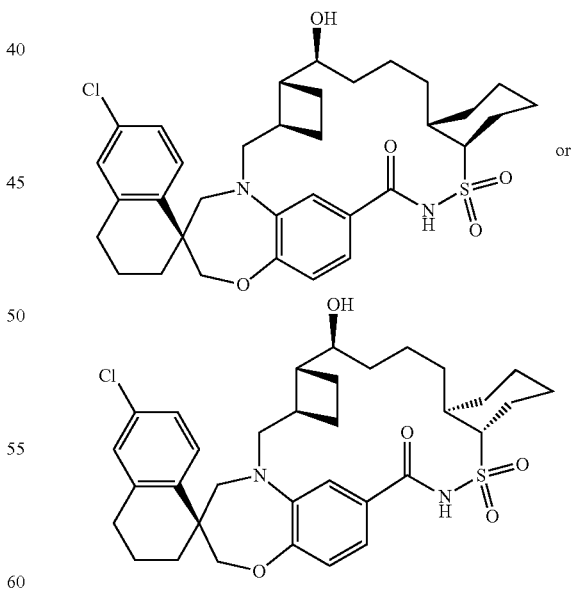

A mixture of (1S,3'R,6'R,7'S,8'E,11'S,16'R)-6-chloro-7'-hydroxy-3,4-dihydro-2H,19'H-spiro[naphthalene-1,26'-[24]oxa[17]thia[1,18]diazapentacyclo[18.7.2.0$^{3,6}$.0$^{11,16}$.0$^{23,28}$]nonacosa[8,20,22,28]tetraen]-19'-one 17',17'-dioxide and (1S,3'R,6'R,7'S,8'E,11'R,16'S)-6-chloro-7'-hydroxy-3,4-dihydro-2H,19'H-spiro[naphthalene-1,26'-[24]oxa[17]thia[1, 18]diazapentacyclo[18.7.2.0³,⁶.0¹¹,¹⁶.0²³,²⁸]nonacosa[8,20,22,28]tetraen]-19'-one 17',17'-dioxide (8.0 mg, 0.013 mmol, Examples 331) and platinum (iv) oxide (0.581 mg, 2.56 µmol) (in excess) in EtOAc (8 mL) was degassed and purged with hydrogen for multiple times and balloon hydrogenated for a period of 2 h. The reaction was quenched with DCM. The solid was filtered off and the residue after concentration in vacuo was taken up in DMSO and subjected to preparative reverse-phase HPLC (Gemini Prep $C_{18}$ 5 µm column; Phenomenex, Torrance, CA; gradient elution of 55-95% acetonitrile in water, where both solvents contained 0.1% TFA, 30 min method) to give, after lyophilization, 1.5 mg of the title compound as the first eluting fraction as a white solid. ¹H NMR (400 MHz, CDCl₃) δ 9.59 (br. s., 1H), 7.69 (d, J=8.4 Hz, 1H), 7.31 (d, J=7.8 Hz, 1H), 7.22-7.14 (m, 2H), 7.09 (d, J=2.2 Hz, 1H), 6.96 (d, J=8.2 Hz, 1H), 4.21-3.99 (m, 2H), 3.79-3.46 (m, 4H), 3.40-3.09 (m, 2H), 2.86-2.72 (m, 2H), 2.61-2.37 (m, 2H), 2.36-2.15 (m, 2H), 2.13-0.97 (m, 20H). m/z (ESI, +ve ion) 627.3 (M+H)⁺.

Example 334. (1S,3'R,6'R,7'S,11R,16'S)-6-chloro-7'-hydroxy-3,4-dihydro-2H,19'H-spiro[naphthalene-1,26'-.[24]oxa[17]thia[1,18]diazapentacyclo[18.7.2.0³,⁶.0¹¹,¹⁶.0²³,²⁸]nonacosa[20,22,28]trien]-19'-one 17',17'-dioxide or (1S,3'R,6'R,7'S,11'S,16'R)-6-chloro-7'-hydroxy-3,4-dihydro-2H,19'H-spiro[naphthalene-1,26'-[24]oxa[17]thia[1,18]diazapentacyclo [18.7.2.0³,⁶.0¹¹,¹⁶.0²³,²⁸]nonacosa[20,22,28]trien]-19'-one 17',17'-dioxide

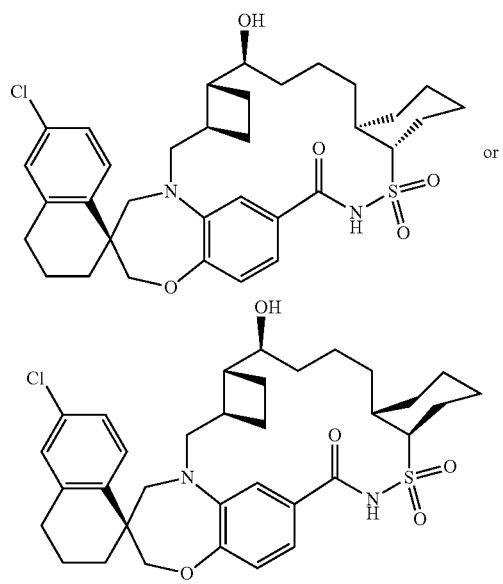

The title compound (3.5 mg) was obtained as a white solid as the second eluting isomer from preparative reverse-phase HPLC (Gemini™ Prep $C_{18}$ 5 µm column; Phenomenex, Torrance, CA; gradient elution of 55-95% acetonitrile in water, where both solvents contained 0.1% TFA, 30 min method) in Example 333. ¹H NMR (400 MHz, CDCl₃) δ 10.52 (br. s., 1H), 7.70 (d, J=8.6 Hz, 1H), 7.59-7.50 (m, 1H), 7.25 (br. s., 1H), 7.17 (dd, J=2.3, 8.4 Hz, 1H), 7.09 (d, J=2.2 Hz, 1H), 6.98 (d, J=8.4 Hz, 1H), 4.19-3.98 (m, 2H), 3.87-3.69 (m, 2H), 3.62-3.45 (m, 2H), 3.14 (d, J=14.1 Hz, 2H), 2.85-2.71 (m, 2H), 2.55 (d, J=11.9 Hz, 1H), 2.41-0.88 (m, 25H). m/z (ESI, +ve ion) 627.3 (M+H)⁺.

Example 335. (1S,3'R,6'R,7'S,8'E,10'R,13'R,15'R)-6-chloro-7',13'-dihydroxy-3,4-dihydro-2H,18'H-spiro[naphthalene-1,25'-[23]oxa[16]thia[1,17]diazapentacyclo [17.7.2.0³,⁶.0¹¹,¹⁵.0²²,²⁷]octacosa[8,19,21,27]tetraen]-18'-one 16',16'-dioxide or (1S,3'R,6'R,7'S,8'E,11'S,13'S,15'S)-6-chloro-7',13'-dihydroxy-3,4-dihydro-2H,18'H-spiro[naphthalene-1,25'-[23]oxa[16]thia[1,17]diazapentacyclo [17.7.2.0³,⁶.0¹¹,¹⁵.0²²,²⁷]octacosa[8,19,21,27]tetraen]-18'-one 16',16'-dioxide

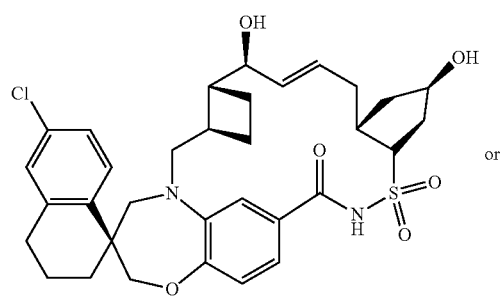

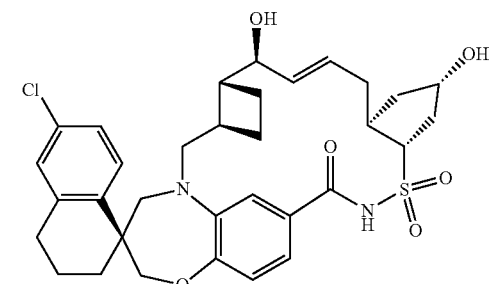

Step 1:
tert-butyl(cyclopent-3-en-1-yloxy)dimethylsilane

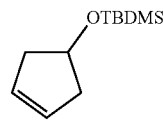 [SMILES: CC(C)(C)[Si](C)(C)OC1CC=CC1]

To a stirred ice-cooled solution of 3-cyclopentene-1-ol (3.60 mL, 42.8 mmol) in DCM (80 mL) was added imidazole, 99+%, crystalline (6.70 g, 98 mmol) followed by slow addition of tert-butyldimethylsilyl chloride, 1.0 M solution in dichloromethane (47.1 mL, 47.1 mmol) via a syringe. The resulting mixture was stirred at 0° C. for 0.5 h and at ambient temperature overnight (16 h). The reaction was poured into ice water and extracted with DCM (3×). The combined organics were washed with brine (1×), dried over anhydrous sodium sulfate and concentrated in vacuo. The crude residue was purified by silica gel chromatography (EtOAc/Hexanes, 5 min at 0% and 30 min from 0 to 10%, 80 g ISCO silica gel column) to give tert-butyl(cyclopent-3-en-1-yloxy)dimethylsilane in nearly quantitative yield as a colorless liquid, taken directly onto the next step.

Step 2: ((1R,3S,5S)-6-oxabicyclo[3.1.0]hexan-3-yloxy)(tert-butyl)dimethylsilane and ((1R,3R,5S)-6-oxabicyclo[3.1.0]hexan-3-yloxy)(tert-butyl)dimethylsilane

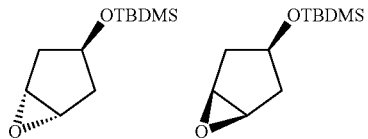 [SMILES: CC(C)(C)[Si](C)(C)O[C@H]1C[C@@H]2O[C@@H]2C1 ; CC(C)(C)[Si](C)(C)O[C@@H]1C[C@@H]2O[C@@H]2C1]

To a stirred ice-cooled solution of tert-butyl(cyclopent-3-en-1-yloxy)dimethylsilane (8.49 g, 42.8 mmol) in DCM (150 mL) was added 3-chlorobenzoperoxoic acid (11.99 g, 53.5 mmol) in 3 portions as a solid over 10 min. The resulting mixture was stirred at 0° C. and allowed to warm up to rt gradually overnight (18 h). It appeared to be a milky white suspension. DMF (3 mL) was added resulting in a clear solution. The mixture was stirred at rt for an additional 5 h and then poured into ice and 10% NaHSO₃ aqueous solution and extracted with DCM (2×). The combined organics were washed sequentially with 10% NaHSO₃ aqueous solution (1×), saturated sodium bicarbonate aqueous solution (2×), water (1×) and brine (1×), dried over anhydrous sodium sulfate, and concentrated in vacuo to give 9.15 g of a crude product mixture of two stereoisomers. This was subjected to combi-flash column chromatography (EtOAc/Hexanes, 25 min from 0 to 20%, 80 g ISCO silica gel column) to give, as the first peak out, pure ((1R,3S,5S)-6-oxabicyclo[3.1.0]hexan-3-yloxy)(tert-butyl)dimethylsilane (1.78 g, 8.30 mmol, 19.40% yield) as a colorless liquid, which solidified upon standing at rt, and, as the second peak out, ((1R,3R,5S)-6-oxabicyclo[3.1.0]hexan-3-yloxy)(tert-butyl)dimethylsilane (5.28 g, 24.63 mmol, 57.5% yield) as a colorless liquid contaminated with the first peak in a ratio of 12:1. The stereochemistry was assigned according to the reference of Bull. Chem. Soc. Jpn. 1990, 63, 1402-1408. (ref: Bull. Chem. Soc. Jpn. 1990, 63, 1402-1408; J. Med. Chem. 2008, 51, 5176-5197)

Step 3: (1R,2R,4R)-2-allyl-4-((tert-butyldimethylsilyl)oxy)cyclopentanol and (1S,2S,4S)-2-allyl-4-((tert-butyldimethyl silyl)oxy)cyclopentanol

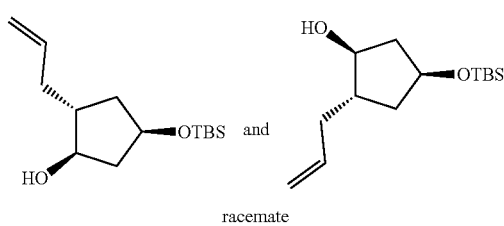 [SMILES: C=CC[C@@H]1C[C@@H](O[Si](C)(C)C(C)(C)C)C[C@H]1O ; C=CC[C@H]1C[C@H](O[Si](C)(C)C(C)(C)C)C[C@@H]1O]

racemate

To a stirred ice-cooled allylmagnesium bromide, 1.0 M solution in diethyl ether (51.7 mL, 51.7 mmol) was slowly added a solution of ((1R,3R,5S)-6-oxabicyclo[3.1.0]hexan-3-yloxy)(tert-butyl)dimethylsilane (5.28 g, 24.63 mmol) in THF (70 mL) via a cannula over a period of 20 min. The resulting mixture was stirred at 0° C. for a period of 0.5 h. The reaction mixture was carefully quenched and further diluted with ice cold saturated ammonium chloride aqueous solution and extracted with Et₂O (3×). The combined organics were dried over anhydrous sodium sulfate and concentrated in vacuo to give a racemic mixture of (1R,2R,4R)-2-allyl-4-((tert-butyldimethylsilyl)oxy)cyclopentanol and (1S,2S,4S)-2-allyl-4-((tert-butyldimethylsilyl)oxy) cyclopentanol (6.39 g, 24.92 mmol, 101% yield) as a colorless oil, taken directly onto the next step.

Step 4: (1S,2R,4R)-2-allyl-4-((tert-butyldimethylsilyl)oxy)cyclopentyl formate and (1R,2S,4S)-2-allyl-4-((tert-butyldimethylsilyl)oxy)cyclopentyl formate

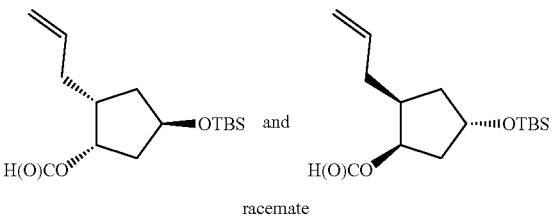

racemate

To a stirred ice-cooled solution of a racemic mixture of (1R,2R,4R)-2-allyl-4-((tert-butyldimethylsilyl)oxy)cyclopentanol and (1S,2S,4S)-2-allyl-4-((tert-butyldimethylsilyl)oxy)cyclopentanol (6.39 g, 24.92 mmol) and triphenylphosphine (8.17 g, 31.1 mmol) in THF (100 mL) was added 98% formic acid (1.175 mL, 31.1 mmol) followed by slow addition of (E)-diisopropyl diazene-1,2-dicarboxylate (6.17 mL, 31.1 mmol) through a syringe over a period of 15 min. The resulting mixture was stirred at 0° C. for 30 min and at ambient temperature for a period of 10 h. After the volatiles were removed in vacuo, the residue was subjected to combi-flash column chromatography (EtOAc/Hexanes, 5 min at 0% and 25 min from 0 to 5%, 80 g ISCO silica gel column) to give a racemic mixture of (1S,2R,4R)-2-allyl-4-((tert-butyldimethylsilyl)oxy)cyclopentyl formate and (1R,2S,4S)-2-allyl-4-((tert-butyldimethylsilyl)oxy)cyclopentyl formate (6.48 g, 22.78 mmol, 91% yield) as a nearly colorless liquid, taken directly onto the next step.

Step 5: (1S,2R,4R)-2-allyl-4-((tert-butyldimethylsilyl)oxy)cyclopentanol and (1R,2S,4S)-2-allyl-4-((tert-butyldimethylsilyl)oxy)cyclopentanol

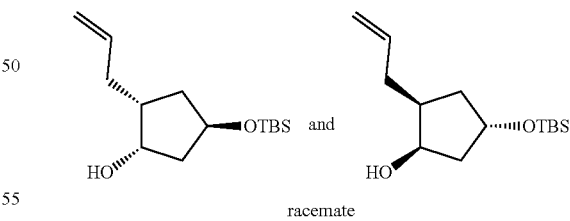

racemate

To a stirred solution of a racemic mixture of (1S,2R,4R)-2-allyl-4-((tert-butyldimethylsilyl)oxy)cyclopentyl formate and (1R,2S,4S)-2-allyl-4-((tert-butyldimethylsilyl)oxy)cyclopentyl formate (6.480 g, 22.78 mmol) in MeOH (70 mL) was added ammonia hydrate, 27% aqueous solution (15 mL, 22.78 mmol) via a syringe at rt. The resulting mixture was stirred at rt for a period of 12 h when TLC showed completion. The volatiles were removed and the residue was subjected to combi-flash column chromatography (EtOAc/Hexanes, 5 min at 0% and 30 min from 0 to 30%, 80 g ISCO silica gel column) to give a pure racemic mixture of (1S,2R,4R)-2-allyl-4-((tert-butyldimethylsilyl)oxy)cyclopentanol and (1R,2S,4S)-2-allyl-4-((tert-butyldimethylsilyl)oxy)cyclopentanol (4.81 g, 18.76 mmol, 82% yield) as a colorless oil, taken onto the next step.

Step 6: (1S,2R,4R)-2-allyl-4-((tert-butyldimethylsilyl)oxy)cyclopentyl methanesulfonate and (1R,2S,4S)-2-allyl-4-((tert-butyldimethylsilyl)oxy)cyclopentyl methanesulfonate

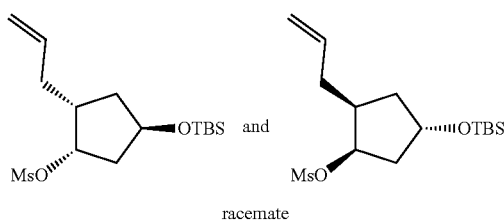 [SMILES: C=CC[C@@H]1C[C@@H](O[Si](C)(C)C(C)(C)C)C[C@@H]1OS(C)(=O)=O ; C=CC[C@H]1C[C@H](O[Si](C)(C)C(C)(C)C)C[C@H]1OS(C)(=O)=O]

racemate

To a stirred ice-cooled solution of a racemic mixture of (1S,2R,4R)-2-allyl-4-((tert-butyldimethylsilyl)oxy)cyclopentanol and (1R,2S,4S)-2-allyl-4-((tert-butyldimethylsilyl)oxy)cyclopentanol (4.81 g, 18.76 mmol) and triethylamine (5.74 mL, 41.3 mmol) in DCM (70 mL) was slowly added methanesulfonyl chloride (2.223 mL, 28.1 mmol) through a syringe. The resulting mixture was stirred at 0° C. for a period of 1 h. The crude mixture was poured into ice and 1 N aqueous HCl solution and extracted with DCM (2×). The combined organics were once again washed with 1 N aqueous HCl solution followed by brine (2×) and dried over anhydrous sodium sulfate. Concentration in vacuo gave a racemic mixture of (1S,2R,4R)-2-allyl-4-((tert-butyldimethylsilyl)oxy)cyclopentyl methanesulfonate and (1R,2S,4S)-2-allyl-4-((tert-butyldimethylsilyl)oxy)cyclopentyl methanesulfonate (6.56 g, 19.61 mmol, 105% yield) as a nearly colorless oil, directly taken onto the step.

Step 7: 2-(((1R,2R,4R)-2-allyl-4-((tert-butyldimethylsilyl)oxy)cyclopentyl)thio)pyrimidine and 2-(((1S,2S,4S)-2-allyl-4-((tert-butyldimethylsilyl)oxy)cyclopentyl)thio)pyrimidine

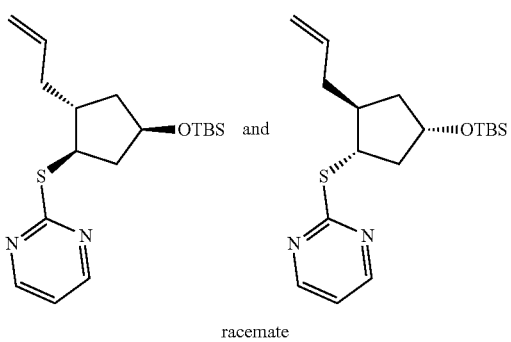 [SMILES: C=CC[C@@H]1C[C@@H](O[Si](C)(C)C(C)(C)C)C[C@H]1Sc1ncccn1 ; C=CC[C@H]1C[C@H](O[Si](C)(C)C(C)(C)C)C[C@@H]1Sc1ncccn1]

racemate

A mixture of 2-mercapto-pyrimidine (3.74 g, 33.3 mmol) and potassium carbonate anhydrous (2.96 mL, 49.0 mmol) in DMF (70 mL) was stirred at rt for 10 min before a solution of a racemic mixture of (1S,2R,4R)-2-allyl-4-((tert-butyldimethylsilyl)oxy)cyclopentyl methanesulfonate (6.560 g, 19.61 mmol) and (1R,2S,4S)-2-allyl-4-((tert-butyldimethylsilyl)oxy)cyclopentyl methanesulfonate in THF (70 mL) was added. The resulting mixture was stirred at rt for 10 min and at 75° C. for a period of 20 h. The crude mixture was poured into ice and saturated sodium carbonate aqueous solution and extracted with EtOAc (2×). The combined organics were washed with saturated sodium carbonate aqueous solution (1×) followed by water (1×), dried over anhydrous sodium sulfate, and concentrated in vacuo. The residue was subjected to combi-flash column chromatography (EtOAc/hexanes, 5 min at 0% and 25 min from 0 to 30%, 80 g ISCO silica gel column) to give a racemic mixture of 2-(((1R,2R,4R)-2-allyl-4-((tert-butyldimethylsilyl)oxy)cyclopentyl)thio)pyrimidine and 2-(((1S,2S,4S)-2-allyl-4-((tert-butyldimethylsilyl)oxy)cyclopentyl)thio)pyrimidine (4.17 g, 11.89 mmol, 60.7% yield) as a colorless oil, taken onto the next step.

Step 8: 2-(((1R,2R,4R)-2-allyl-4-((tert-butyldimethylsilyl)oxy)cyclopentyl)sulfonyl)pyrimidine and 2-(((1S,2S,4S)-2-allyl-4-((tert-butyldimethylsilyl)oxy)cyclopentyl)sulfonyl)pyrimidine

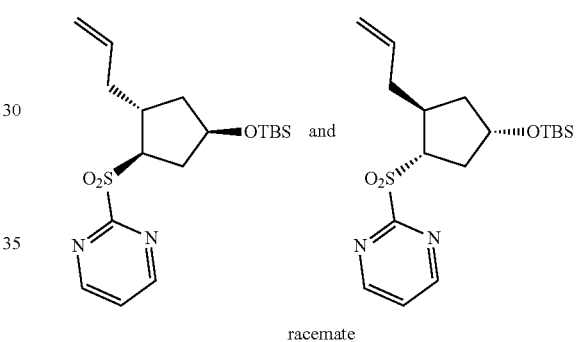

racemate

To a stirred ice-cooled solution of a racemic mixture of 2-(((1R,2R,4R)-2-allyl-4-((tert-butyldimethylsilyl)oxy)cyclopentyl)thio)pyrimidine and 2-(((1S,2S,4S)-2-allyl-4-((tert-butyldimethylsilyl)oxy)cyclopentyl)thio)pyrimidine (1.05 g, 2.99 mmol) in DCM (20 mL) and DMF (2.00 mL) was added 3-chlorobenzoperoxoic acid (1.410 g, 6.29 mmol) in 2 portions as a solid over 10 min. The resulting mixture was stirred at 0° C. for about 2 h and at rt for a period of 5.5 h. The reaction stalled without completion. The reaction mixture was cooled again in an ice-water bath. Based on LC-MS estimate, 0.48 g more of m-CPBA was added and the resulting mixture was stirred at 0° C. and allowed to warm up gradually to rt overnight (11 h). It was poured into ice and 10% NaHSO₃ aqueous solution and extracted with DCM (2×). The combined organics were washed sequentially with 10% NaHSO₃ aqueous solution (1×), saturated sodium bicarbonate aqueous solution (1×) and brine (1×), dried over anhydrous sodium sulfate, and concentrated in vacuo. The residue was subjected to combi-flash column chromatography (EtOAc/Hexanes, 25 min from 0 to 100%, 40 g ISCO silica gel column) to give a racemic mixture of 2-(((1R,2R,4R)-2-allyl-4-((tert-butyldimethylsilyl)oxy)cyclopentyl)sulfonyl)pyrimidine and 2-(((1S,2S,4S)-2-allyl-4-((tert-butyldimethylsilyl)oxy)cyclopentyl)sulfonyl)pyrimidine (1.04 g, 2.72 mmol, 91% yield) as a colorless oil which solidified upon standing at rt over time, taken onto the next step.

811

Step 9: (1R,2R,4R)-2-allyl-4-hydroxycyclopentane-1-sulfonamide and (1S,2S,4S)-2-allyl-4-hydroxycyclopentane-1-sulfonamide

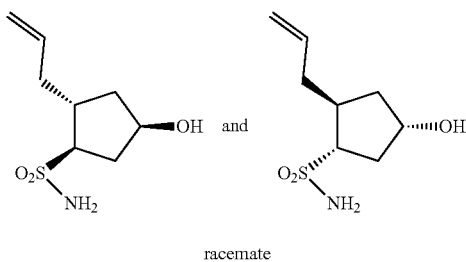

racemate

The 1st step: To a stirred solution of a racemic mixture of 2-(((1R,2R,4R)-2-allyl-4-((tert-butyldimethylsilyl)oxy)cyclopentyl)sulfonyl)pyrimidine and 2-(((1S,2S,4S)-2-allyl-4-((tert-butyldimethylsilyl)oxy)cyclopentyl)sulfonyl)pyrimidine (1.04 g, 2.72 mmol) in MeOH (40 mL) was added at rt sodium methoxide, 25 wt % solution in methanol (0.606 mL, 2.72 mmol) via a syringe. The resulting mixture was stirred at rt for 30 min when LC-MS showed completion. The volatiles were removed in vacuo and the residue was subjected to high vacuum. The 2nd step: To the above residue was added water (40 mL) followed by sodium acetate trihydrate (0.510 mL, 5.44 mmol) and amidoperoxymonosulfuric acid (0.615 g, 5.44 mmol) at rt. The resulting clear solution was stirred at 75° C. in a preheated oil bath for a period of 3 h. Note that the mixture remain clear after cooled. It was basified with ice cold saturated sodium carbonate and extracted with 25% i-PrOH/DCM (5×). The combined organics were dried over anhydrous sodium sulfate and concentrated in vacuo. The residue was subjected to combi-flash column chromatography ((10% MeOH/DCM with 0.3% AcOH)/DCM, 25 min from 0 to 70%, 24 g ISCO silica gel column) to give a racemic mixture of (1R,2R,4R)-2-allyl-4-hydroxycyclopentane-1-sulfonamide and (1S,2S,4S)-2-allyl-4-hydroxycyclopentane-1-sulfonamide (0.46 g, 2.241 mmol, 82% yield) as a colorless sticky oil, taken onto the next step.

812

Step 10: (S)-6'-chloro-5-(((1R,2R)-2-((S,E)-1-hydroxy-4-((1R,2R,4R)-4-hydroxy-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((1S,2S,4S)-4-hydroxy-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid

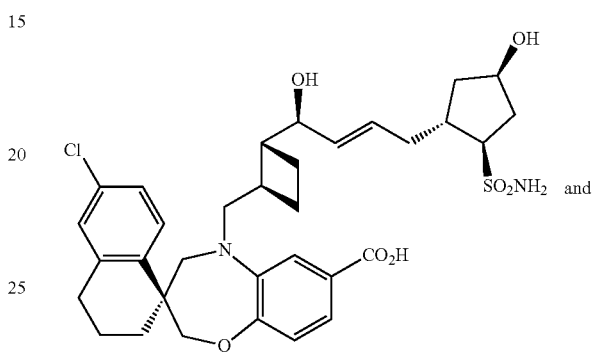

To a 25 mL single-necked round-bottomed flask were placed (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (0.145 g, 0.284 mmol, Intermediate AA12A), a racemic mixture of (1R,2R,4R)-2-allyl-4-hydroxycyclopentane-1-sulfonamide and (1S,2S,4S)-2-allyl-4-hydroxycyclopentane-1-sulfonamide (0.093 g, 0.455 mmol), and 2nd generation hoveyda-grubbs catalyst (0.018 g, 0.028 mmol). The flask was subjected to 3 cycles of evacuation and back-filling with nitrogen before DCE (4 mL) was introduced through a syringe under nitrogen. The resulting mixture was stirred at rt under nitrogen for a period of 4 h. The crude mixture was loaded onto a silica gel precolumn and subjected to combi-flash column chromatography ((10% MeOH/DCM with 0.3% AcOH)/DCM), 50 min from 0 to 100%, 24 g ISCO silica gel column) to give a mixture of the title compounds (0.0884 g, 0.137 mmol, 48.2%) as a gray solid.

Step 11: (1S,3'R,6'R,7'S,8'E,11R,13'R,15'R)-6-chloro-7',13'-dihydroxy-3,4-dihydro-2H,18'H-spiro[naphthalene-1,25'-[23]oxa[16[thia]1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,13'S,15'S)-6-chloro-7',13'-dihydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide To a stirred ice-cooled solution of (S)-6'-chloro-5-(((1R,2R)-2-((S,E)-1-hydroxy-4-((1R,2R,4R)-4-hydroxy-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S,E)-1-hydroxy-4-((1S,2S,4S)-4-hydroxy-2-sulfamoylcyclopentyl)but-2-en-1-yl)cyclobutyl)methyl)-3',4,4',5-tetrahydro-2H,2'H-spiro[benzo[b][1,4]oxazepine-3,1'-naphthalene]-7-carboxylic acid (88 mg, 0.136 mmol) and N,N-dimethylpyridin-4-amine (36.7 mg, 0.30 mmol) in DCM (70 mL) was added 1-(3-dimethylaminopropyl)-3-ethylcarbodiimide hydrochloride (65.4 mg, 0.341 mmol) in one portion. The resulting mixture was stirred at 0° C. for 0.5 h and at ambient temperature for 5.5 h. The volatiles were removed in vacuo. The crude residue was taken up in DMSO and subjected to preparative reverse-phase HPLC (Gemini™ Prep C$_{18}$ 5 μm column; Phenomenex, Torrance, CA; gradient elution of 50-95% acetonitrile in water, where both solvents contained 0.1% TFA, 30 min method) to give, after lyophilization, 7 mg pure of the title compound as the first eluting fraction as an off-white solid. About 10 mg slightly impure of this title compound was collected in the second crop. $^1$H NMR (500 MHz, CDCl$_3$) δ 8.56 (br. s., 1H), 7.70 (d, J=8.6 Hz, 1H), 7.18 (dd, J=2.0, 8.6 Hz, 1H), 7.10 (d, J=1.7 Hz, 1H), 7.03-6.90 (m, 3H), 5.88-5.75 (m, 1H), 5.74-5.66 (m, 1H), 4.43 (br. s., 1H), 4.32-4.24 (m, 1H), 4.23-4.18 (m, 1H), 4.16-4.03 (m, 2H), 3.76 (d, J=14.9 Hz, 1H), 3.69 (d, J=14.4 Hz, 1H), 3.25 (d, J=13.9 Hz, 1H), 3.09 (dd, J=7.6, 14.7 Hz, 1H), 2.89-1.54 (m, 20H), 1.44 (t, J=12.3 Hz, 1H). m/z (ESI, +ve ion) 627.3 (M+H)$^+$.

Example 336. (1S,3'R,6'R,7'S,8'E,11'S,13'S,15'S)-6-chloro-7',13'-dihydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'R,13'R,15'R)-6-chloro-7',13'-dihydroxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide

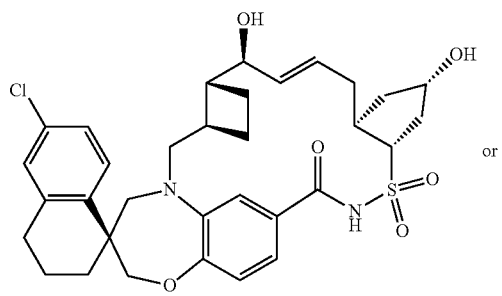

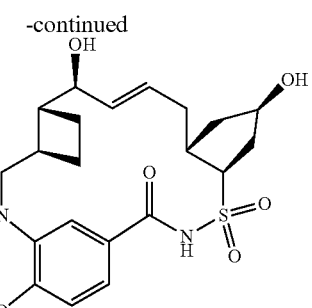

The title compound (18 mg) was obtained as an off-white solid as the second eluting isomer from preparative reverse-phase HPLC (Gemini Prep C$_{18}$ 5 μm column; Phenomenex, Torrance, CA; gradient elution of 50-95% acetonitrile in water, where both solvents contained 0.1% TFA, 30 min method) in Example 335. About 10 mg impure of the title compound was harvested in the second crop. $^1$H NMR (500 MHz, CDCl$_3$) δ 8.56 (br. s., 1H), 7.67 (d, J=8.6 Hz, 1H), 7.17 (dd, J=2.2, 8.6 Hz, 1H), 7.10 (d, J=2.0 Hz, 1H), 7.02 (d, J=8.3 Hz, 1H), 6.94 (d, J=8.1 Hz, 1H), 5.72 (br. s., 2H), 4.44 (d, J=2.7 Hz, 1H), 4.26-4.12 (m, 2H), 4.10-3.90 (m, 2H), 3.84-3.23 (m, 4H), 2.76 (br. s., 3H), 2.67-2.42 (m, 4H), 2.32-1.39 (m, 14H). m/z (ESI, +ve ion) 627.3 (M+H)$^+$.

Example 337. (1S,3'R,6'R,7'S,8'E,11'R,13'R,15'R)-6-chloro-7',13'-dimethoxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,13'S,15'S)-6-chloro-7',13'-dimethoxy-3,4-dihydro-2H,18'H-spiro[naphthalene-1,25'-[23]oxa[16]thia[1,17]diazapentacyclo[17.7.2.0$^{3,6}$.0$^{11,15}$.0$^{22,27}$]octacosa[8,19,21,27]tetraen]-18'-one 16',16'-dioxide

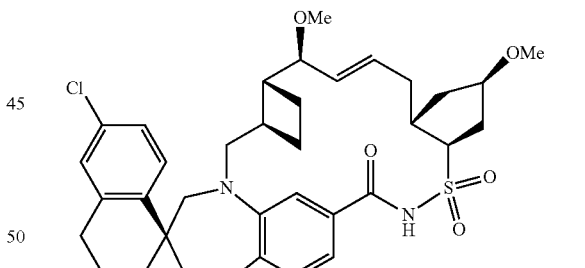

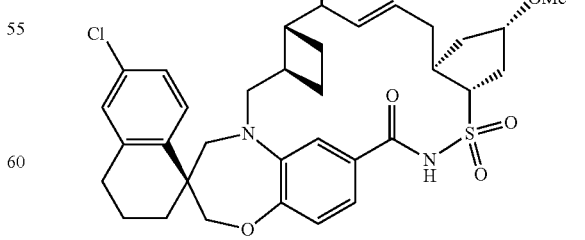

To a stirred ice-cooled solution of (1S,3'R,6'R,7'S,8'E,11'R,13'R,15'R)-6-chloro-7',13'-dihydroxy-3,4-dihydro-2H,18'H-spiro[naphthalene-1,25'-[23]oxa[16]thia[1,17]diazapentacyclo[17.7.2.0³,⁶.0¹¹,¹⁵.0²²,²⁷]octacosa[8,19,21,27]tetraen]-18'-one 16',16'-dioxide or (1S,3'R,6'R,7'S,8'E,11's,13's,15's)-6-chloro-7',13'-dihydroxy-3,4-dihydro-2H,18'H-spiro[naphthalene-1,25'-[23]oxa[16]thia[1,17]diazapentacyclo[17.7.2.0³,⁶.0¹¹,¹⁵.0²²,²⁷]octacosa[8,19,21,27]tetraen]-18'-one 16',16'-dioxide (not weighed, Example 335) in DMF (2 mL) was added sodium hydride, 60% dispersion in mineral oil (in excess). The resulting mixture was stirred at 0° C. for 10 min and at rt for 20 min before iodomethane (in excess) was added. The resulting mixture was stirred at rt for a period of 1 h. It was cooled in an ice-water bath before quenched with methanol. The crude mixture was taken up in DMSO and subjected to preparative reverse-phase HPLC (Gemini Prep C₁₈ 5 μm column; Phenomenex, Torrance, CA; gradient elution of 50-95% acetonitrile in water, where both solvents contained 0.1% TFA, 30 min method) to give, after lyophilization, 5.5 mg of the title compound as a white solid. ¹H NMR (400 MHz, CDCl₃) δ 8.23 (s, 1H), 7.70 (d, J=8.6 Hz, 1H), 7.18 (dd, J=2.3, 8.6 Hz, 1H), 7.09 (d, J=2.3 Hz, 1H), 6.98-6.85 (m, 2H), 6.77 (s, 1H), 5.86-5.74 (m, 1H), 5.56 (dd, J=8.4, 14.7 Hz, 1H), 4.45 (q, J=9.3 Hz, 1H), 4.07 (q, J=12.2 Hz, 2H), 3.91-3.66 (m, 4H), 3.31 (s, 3H), 3.26 (s, 3H), 3.18 (d, J=14.3 Hz, 1H), 2.98 (dd, J=10.3, 15.2 Hz, 1H), 2.85-2.60 (m, 4H), 2.57-1.55 (m, 14H), 1.39 (t, J=12.7 Hz, 1H). m/z (ESI, +ve ion) 655.0 (M+H)⁺.

Example 338. (1S,3'R,6'R,7'S,8'E,11'R,15'S)-13'-acetyl-6-chloro-7'-hydroxy-3,4-dihydro-2H,18'H-spiro[naphthalene-1,25'-[23]oxa[16]thia[1,13,17]triazapentacyclo[17.7.2.0³,⁶.0¹¹,¹⁵.0²²,²⁷]octacosa[8,19,21,27]tetraen]-18'-one 16',16'-dioxide or (1S,3'R,6'R,7'S,8'E,11'S,15'R)-13'-acetyl-6-chloro-7'-hydroxy-3,4-dihydro-2H,18'H-spiro[naphthalene-1,25'-[23]oxa[16]thia[1,13,17]triazapentacyclo[17.7.2.0³,⁶.0¹¹,¹⁵.0²²,²⁷]octacosa[8,19,21,27]tetraen]-18'-one 16',16'-dioxide

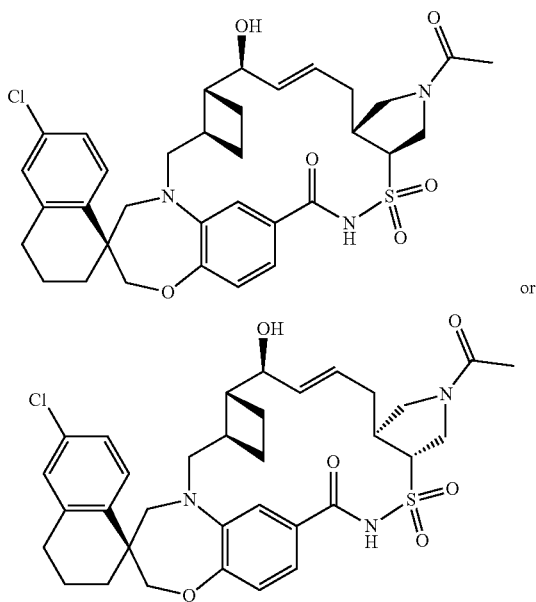

or

Step 1: (3R,4S)-tert-butyl 3-allyl-4-hydroxypyrrolidine-1-carboxylate and (3S,4R)-tert-butyl 3-allyl-4-hydroxypyrrolidine-1-carboxylate

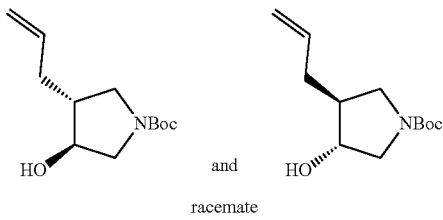 [SMILES: C=CC[C@@H]1CN(C(=O)OC(C)(C)C)C[C@H]1O ; C=CC[C@H]1CN(C(=O)OC(C)(C)C)C[C@@H]1O]

racemate

To a heat-gun-dried single-necked round-bottomed flask (250 mL) was charged dry diethyl ether (20 mL) and allylmagnesium bromide, 1.0 M solution in diethyl ether (11.34 mL, 11.34 mmol). The mixture was cooled to 0° C. in an ice bath. To this was slowly added a solution of 3-boc-6-oxa-3-aza-bicyclo[3.1.0]hexane (1.0 g, 5.40 mmol) in dry ethyl ether (20 mL) via a syringe. A white precipitate formed immediately upon addition. After the addition was complete, the mixture was stirred for 15 min at 0° C. before quenched with saturated ammonium chloride aqueous solution (25 mL, slow addition with caution). The resulting mixture was extracted with diethyl ether (3×). The combined organics were dried over anhydrous sodium sulfate and concentrated in vacuo to give a racemic mixture of (3R,4S)-tert-butyl 3-allyl-4-hydroxypyrrolidine-1-carboxylate and (3S,4R)-tert-butyl 3-allyl-4-hydroxypyrrolidine-1-carboxylate (1.2 g, 5.28 mmol, 98% yield) as a nearly colorless oil, directly taken onto the next step.

Step 2: (3R,4R)-tert-butyl 3-allyl-4-(formyloxy)pyrrolidine-1-carboxylate and (3S,4S)-tert-butyl 3-allyl-4-(formyloxy)pyrrolidine-1-carboxylate

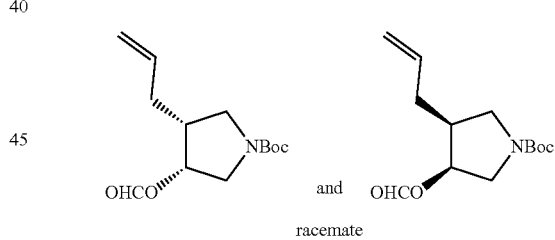

racemate

To a stirred ice-cooled solution of a racemic mixture of (3R,4S)-tert-butyl 3-allyl-4-hydroxypyrrolidine-1-carboxylate and (3S,4R)-tert-butyl 3-allyl-4-hydroxypyrrolidine-1-carboxylate (0.980 g, 4.31 mmol) and triphenylphosphine (1.414 g, 5.39 mmol) in THF (28 mL) was added 98% formic acid (0.203 mL, 5.39 mmol) followed by slow addition of (E)-diisopropyl diazene-1,2-dicarboxylate (1.068 mL, 5.39 mmol) through a syringe. The resulting mixture was stirred at ambient temperature for a period of 26 h. After the volume was reduced, the crude mixture was subjected to combi-flash column chromatography (EtOAc/Hexanes, 25 min at 20%, 40 g ISCO silica gel column) to give a racemic mixture of (3R,4R)-tert-butyl 3-allyl-4-(formyloxy)pyrrolidine-1-carboxylate and (3S,4S)-tert-butyl 3-allyl-4-(formyloxy)pyrrolidine-1-carboxylate (0.75 g, 2.94 mmol, 68.1% yield) as a colorless film, directly taken onto the next step.

Step 3: (3R,4R)-tert-butyl 3-allyl-4-hydroxypyrrolidine-1-carboxylate and (3S,4S)-tert-butyl 3-allyl-4-hydroxypyrrolidine-1-carboxylate

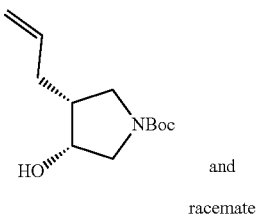

racemate

To a stirred ice-cooled solution of a racemic mixture of (3R,4R)-tert-butyl 3-allyl-4-(formyloxy)pyrrolidine-1-carboxylate and (3S,4S)-tert-butyl 3-allyl-4-(formyloxy)pyrrolidine-1-carboxylate (1.0 g, 3.92 mmol) in MeOH (15 mL) was added ammonia hydrate, 27% aqueous solution (1.1 mL, 3.92 mmol) via a syringe. The resulting mixture was stirred at rt for a period of 1.5 h. The volatiles were removed and the residue was subjected to high vacuum to give a racemic mixture of (3R,4R)-tert-butyl 3-allyl-4-hydroxypyrrolidine-1-carboxylate and (3S,4S)-tert-butyl 3-allyl-4-hydroxypyrrolidine-1-carboxylate (0.94 g, 4.14 mmol, 106% yield) as a colorless film, directly taken onto the next step.

Step 4: (3R,4R)-tert-butyl 3-allyl-4-((methylsulfonyl)oxy)pyrrolidine-1-carboxylate and (3S,4S)-tert-butyl 3-allyl-4-((methylsulfonyl)oxy)pyrrolidine-1-carboxylate

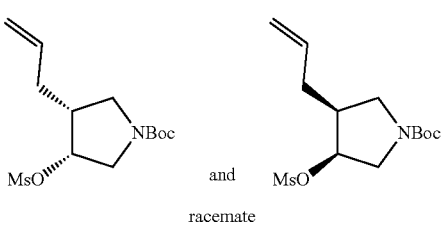 [SMILES: C=CC[C@@H]1CN(C(=O)OC(C)(C)C)C[C@@H]1OS(C)(=O)=O ; C=CC[C@H]1CN(C(=O)OC(C)(C)C)C[C@H]1OS(C)(=O)=O]

racemate

To a stirred ice-cooled solution of a racemic mixture of (3R,4R)-tert-butyl 3-allyl-4-hydroxypyrrolidine-1-carboxylate and (3S,4S)-tert-butyl 3-allyl-4-hydroxypyrrolidine-1-carboxylate (0.940 g, 4.14 mmol) and triethylamine (1.265 mL, 9.10 mmol) in DCM (15 mL) was slowly added methanesulfonyl chloride (0.490 mL, 6.20 mmol) through a syringe. The resulting mixture was stirred at 0° C. for a period of 1.5 h. The crude mixture was poured into ice and 1 N aqueous HCl solution and extracted with DCM (2×). The combined organics were once again washed with 1 N aqueous HCl solution followed by brine (2×) and dried over anhydrous sodium sulfate. Concentration in vacuo gave a racemic mixture of (3R,4R)-tert-butyl 3-allyl-4-((methylsulfonyl)oxy)pyrrolidine-1-carboxylate and (3S,4S)-tert-butyl 3-allyl-4-((methylsulfonyl)oxy)pyrrolidine-1-carboxylate (1.22 g, 3.99 mmol, 97% yield) as a nearly colorless oil, directly taken onto the step.

Step 5: (3R,4S)-tert-butyl 3-allyl-4-(pyrimidin-2-ylthio)pyrrolidine-1-carboxylate and (3S,4R)-tert-butyl 3-allyl-4-(pyrimidin-2-ylthio)pyrrolidine-1-carboxylate

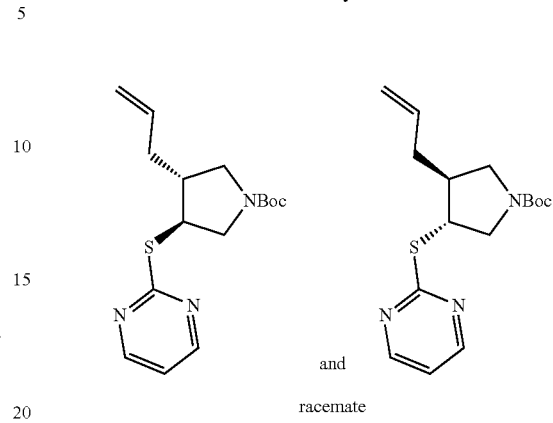

racemate

A mixture of 2-mercapto-pyrimidine (0.582 g, 5.19 mmol) and potassium carbonate anhydrous (0.94 g, 6.79 mmol) in DMF (15 mL) was stirred at rt for 10 min before a racemic mixture of (3R,4R)-tert-butyl 3-allyl-4-((methylsulfonyl)oxy)pyrrolidine-1-carboxylate and (3S,4S)-tert-butyl 3-allyl-4-((methylsulfonyl)oxy)pyrrolidine-1-carboxylate (1.220 g, 3.99 mmol) in DMF (15.0 mL) was added at rt. The resulting mixture was stirred at rt for 10 min and at 80° C. for a period of 3 h. The crude mixture was poured into ice and saturated sodium carbonate aqueous solution and extracted with ether (3×). The combined organics were washed with water (1×) followed by brine (1×), dried over anhydrous sodium sulfate, and concentrated in vacuo. The residue was subjected to combi-flash column chromatography (EtOAc/hexanes, 20 min from 0 to 100%, 24 g ISCO silica gel column) to give a racemic mixture of (3R,4S)-tert-butyl 3-allyl-4-(pyrimidin-2-ylthio)pyrrolidine-1-carboxylate and (3S,4R)-tert-butyl 3-allyl-4-(pyrimidin-2-ylthio)pyrrolidine-1-carboxylate (0.69 g, 2.147 mmol, 53.7% yield) as a yellow oil, directly taken onto the next step.

Step 6: 2-(((3S,4R)-4-allylpyrrolidin-3-yl)thio)pyrimidine 2,2,2-trifluoroacetate and 2-(((3R,4S)-4-allylpyrrolidin-3-yl)thio)pyrimidine 2,2,2-trifluoroacetate

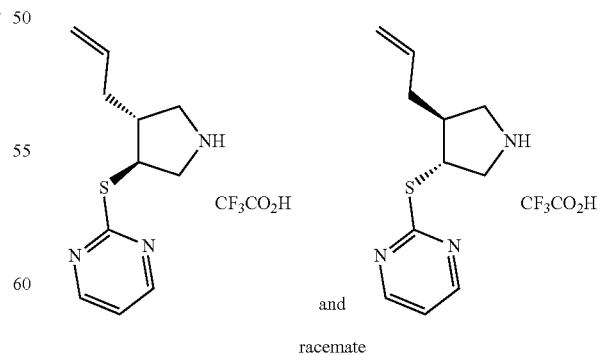

racemate

To a stirred solution of a racemic mixture of (3R,4S)-tert-butyl 3-allyl-4-(pyrimidin-2-ylthio)pyrrolidine-1-carboxylate and (3S,4R)-tert-butyl 3-allyl-4-(pyrimidin-2-ylthio)

pyrrolidine-1-carboxylate (0.69 g, 2.147 mmol) in DCM (10 mL) was added trifluoroacetic acid (0.638 mL, 8.59 mmol) at rt. The resulting mixture was stirred at rt for a period of 1.5 h. The LC-MS indicated the majority was still the sm. More TFA (2.0 mL) was added and the mixture was stirred for 1.5 h, at which time the reaction became complete. The volatiles were removed and the residue was subjected to high vacuum to give a crude racemic mixture of 2-(((3S,4R)-4-allylpyrrolidin-3-yl)thio)pyrimidine 2,2,2-trifluoroacetate and 2-(((3R,4S)-4-allylpyrrolidin-3-yl)thio)pyrimidine 2,2,2-trifluoroacetate as a light orange oil, directly taken onto the next step.

Step 7: 1-((3R,4S)-3-allyl-4-(pyrimidin-2-ylthio) pyrrolidin-1-yl)ethanone and 1-((3S,4R)-3-allyl-4-(pyrimidin-2-ylthio)pyrrolidin-1-yl)ethanone

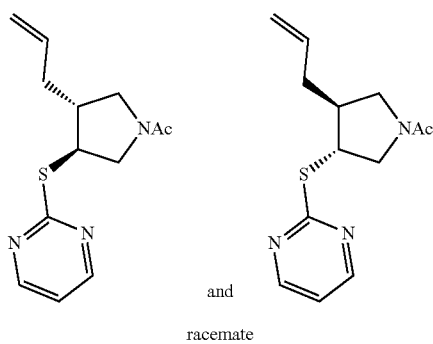

and racemate

To a stirred ice-cooled solution of the above crude racemic mixture of 2-(((3S,4R)-4-allylpyrrolidin-3-yl)thio)pyrimidine 2,2,2-trifluoroacetate and 2-(((3R,4S)-4-allylpyrrolidin-3-yl)thio)pyrimidine 2,2,2-trifluoroacetate (0.475 g, 2.147 mmol) in DCM (12 mL) was added triethylamine (0.747 mL, 5.37 mmol) followed by 2,5-dioxopyrrolidin-1-yl acetate (0.405 g, 2.58 mmol). The resulting mixture was stirred at ambient temperature for 15 h. The LC-MS showed that there was still a bit sm remained. More Et₃N (0.2 mL) was added followed by more of 2,5-dioxopyrrolidin-1-yl acetate (90 mg). The resulting mixture was stirred at rt for 20 min, at which time it reached completion. After the volatiles were removed, the residue was subjected to combi-flash column chromatography (EtOAc/hexanes, 15 min from 20 to 100% and 20 min at 100%, 24 g ISCO silica gel column) to give a racemic mixture of 1-((3R,4S)-3-allyl-4-(pyrimidin-2-ylthio)pyrrolidin-1-yl)ethanone and 1-((3S,4R)-3-allyl-4-(pyrimidin-2-ylthio)pyrrolidin-1-yl)ethanone (0.54 g, 2.05 mmol, 96% yield) as a colorless oil, directly taken onto the next step.

Step 8: 1-((3R,4S)-3-allyl-4-(pyrimidin-2-ylsulfonyl)pyrrolidin-1-yl)ethanone and 1-((3S,4R)-3-allyl-4-(pyrimidin-2-ylsulfonyl)pyrrolidin-1-yl)ethanone

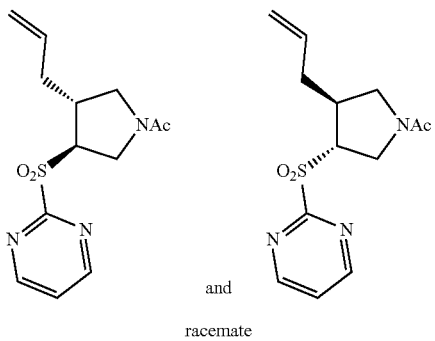

and racemate

To a stirred ice-cooled solution of a racemic mixture of 1-((3R,4S)-3-allyl-4-(pyrimidin-2-ylthio)pyrrolidin-1-yl)ethanone and 1-((3S,4R)-3-allyl-4-(pyrimidin-2-ylthio)pyrrolidin-1-yl)ethanone (0.54 g, 2.05 mmol) in DCM (12 mL) was added 3-chlorobenzoperoxoic acid (0.965 g, 4.31 mmol) in one portion as a solid. The resulting mixture was stirred at 0° C. for about 1 h. DMF (1.2 mL) was added to attain complete dissolution and the mixture was further stirred at 0° C. for 45 min. Note that the reaction was closely monitored by LC-MS and went through a few rounds of adding more m-CPBA as follows. More m-CPBA (0.6 g) was added at 0° C. and the mixture was stirred at this temperature for 20 min before the ice bath was removed. It was stirred at rt for 20 min. The mixture was cooled again in an ice bath and more m-CPBA (0.55 g) was added and the mixture was stirred at 0° C. for 1 h. Again, more m-CPBA (0.26 g) was added at 0° C. and the mixture was stirred at this temperature for 1 h. The reaction mixture was then poured into ice and saturated sodium bicarbonate aqueous solution and extracted with DCM (3×). The combined organics were washed with ice cold sodium bicarbonate aqueous solution (1×), dried over anhydrous sodium sulfate, and concentrated in vacuo. The residue was subjected to combi-flash column chromatography ((10% MeOH/DCM)/DCM, 35 min from 0 to 60%, 40 g ISCO silica gel column) to give a racemic mixture of 1-((3R,4S)-3-allyl-4-(pyrimidin-2-ylsulfonyl)pyrrolidin-1-yl)ethanone and 1-((3S,4R)-3-allyl-4-(pyrimidin-2-ylsulfonyl)pyrrolidin-1-yl)ethanone (0.436 g, 1.476 mmol, 72.0% yield) as a colorless film, taken onto the next step.

Step 9: (3S,4R)-1-acetyl-4-allylpyrrolidine-3-sulfonamide and (3R,4S)-1-acetyl-4-allylpyrrolidine-3-sulfonamide

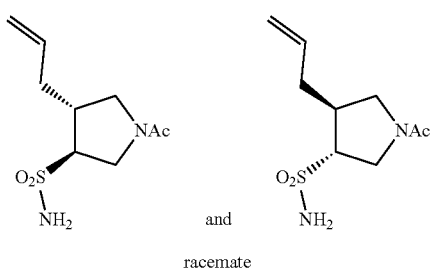

and racemate

The 1st step: To a stirred solution of a racemic mixture of 1-((3R,4S)-3-allyl-4-(pyrimidin-2-ylsulfonyl)pyrrolidin-1-yl)ethanone and 1-((3S,4R)-3-allyl-4-(pyrimidin-2-ylsulfonyl)pyrrolidin-1-yl)ethanone (0.203 g, 0.687 mmol) in MeOH (4 mL) was added at rt sodium methoxide, 25 wt % solution in methanol (0.153 mL, 0.687 mmol) via a syringe. The resulting mixture was stirred at rt for 35 min. The volatiles were removed in vacuo and the residue was subjected to high vacuum.

The 2nd step: To the above residue was added water (5 mL) followed by sodium acetate trihydrate (0.129 mL, 1.375 mmol) and amidoperoxymonosulfuric acid (0.155 g, 1.375 mmol) at rt. The resulting clear solution was stirred at 50° C. in a preheated oil bath for a period of 40 min. No precipitation occurred after cooling. The mixture was basified using ice cold saturated sodium carbonate. Initial multiple extractions using EtOAc was not effective and some of the desired product remained in the aqueous layer. Then the extraction was carried out with 20% i-PrOH/DCM (4×). The combined organics were dried over anhydrous sodium sulfate and concentrated in vacuo. The residue was subjected to combi-flash column chromatography ((10% MeOH/DCM)/DCM, 25 min from 10 to 100%, 12 g ISCO silica gel column) to give a racemic mixture of (3S,4R)-1-acetyl-4-allylpyrrolidine-3-sulfonamide and (3R,4S)-1-acetyl-4-allylpyrrolidine-3-sulfonamide (0.120 g, 0.517 mmol, 75% yield) as a colorless film, taken onto the next step.

Step 10: (S)-5-(((1R,2R)-2-((S,E)-4-((3R,4S)-1-acetyl-4-sulfamoylpyrrolidin-3-yl)-1-hydroxybut-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid and (S)-5-(((1R,2R)-2-((S,E)-4-((3S,4R)-1-acetyl-4-sulfamoylpyrrolidin-3-yl)-1-hydroxybut-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid

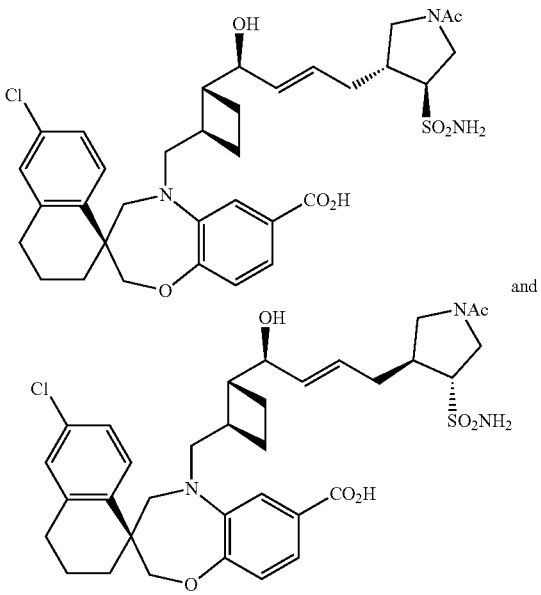

To a 25 mL single-necked round-bottomed flask were placed (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (0.135 g, 0.265 mmol, Intermediate AA12A), a racemic mixture of (3S,4R)-1-acetyl-4-allylpyrrolidine-3-sulfonamide and (3R,4S)-1-acetyl-4-allylpyrrolidine-3-sulfonamide (0.123 g, 0.529 mmol), and 2nd generation hoveyda-grubbs catalyst (0.017 g, 0.026 mmol). The flask was subjected to 3 cycles of evacuation and back-filling with nitrogen before DCE (3.2 mL) was introduced via a syringe under nitrogen. The resulting mixture was stirred under nitrogen at rt for a period of 3.5 h. The crude mixture was loaded onto a silica gel precolumn and subjected to combi-flash column chromatography ((10% MeOH/DCM with 0.3% AcOH)/DCM)), 20 min from 0 to 100%, 24 g ISCO silica gel column) to give a mixture of the title compounds (105 mg, 0.156 mmol, 59.0% yield) as a gray solid. The material was azetroped with toluene and dried on high vacuum before taken onto the next step.

Step 11: (1S,3'R,6'R,7'S,8'E,11R,15'S)-13'-acetyl-6-chloro-7'-hydroxy-3,4-dihydro-2H,18'H-spiro[naphthalene-1,25'-[23]oxa[16]thia[1,13,17]triazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'R)-13'-acetyl-6-chloro-7'-hydroxy-3,4-dihydro-2H,18'H-spiro[naphthalene-1,25'-[23]oxa[16]thia[1,13,17]triazapentacyclo[17.7.2.0$^{3,6}$.0$^{11,15}$.0$^{22,27}$]octacosa[8,19,21,27]tetraen]-18'-one 16',16'-dioxide To a stirred ice-cooled solution of (S)-5-(((1R,2R)-2-((S,E)-4-((3R,4S)-1-acetyl-4-sulfamoylpyrrolidin-3-yl)-1-hydroxybut-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid and (S)-5-(((1R,2R)-2-((S,E)-4-((3S,4R)-1-acetyl-4-sulfamoylpyrrolidin-3-yl)-1-hydroxybut-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid (105 mg, 0.156 mmol) and N,N-dimethylpyridin-4-amine (42.0 mg, 0.344 mmol) in DCM (75 mL) was added 1-(3-dimethylaminopropyl)-3-ethylcarbodiimide hydrochloride (74.9 mg, 0.390 mmol) in one portion. The resulting mixture was stirred at ambient temperature for 12 h. The volatiles were removed and the residue was subjected to preparative reverse-phase HPLC (Gemini™ Prep C$_{18}$ 5 μm column; Phenomenex, Torrance, CA; gradient elution of 45-95% acetonitrile in water, where both solvents contained 0.1% TFA, 30 min method) to give in major bands, after lyophilization, 15 mg of the title compound as the first eluting fraction as an off-white solid. $^1$H NMR (500 MHz, CDCl$_3$) δ 9.03-8.26 (m, 1H), 7.70 (d, J=8.6 Hz, 1H), 7.19 (dd, J=2.2, 8.6 Hz, 1H), 7.10 (d, J=2.0 Hz, 1H), 7.04-6.90 (m, 3H), 5.86-5.65 (m, 2H), 4.74-4.54 (m, 1H), 4.34-3.99 (m, 5H), 3.94-3.74 (m, 2H), 3.70 (dd, J=6.0, 14.3 Hz, 1H), 3.36 (dd, J=5.7, 11.9 Hz, 1H), 3.31-3.14 (m, 2H), 3.14-2.97 (m, 1H), 2.86-2.65 (m, 3H), 2.54-2.30 (m, 3H), 2.27-1.59 (m, 11H), 1.50-1.35 (m, 1H). m/z (ESI, +ve ion) 654.3 (M+H)$^+$.

Example 339. (1S,3'R,6'R,7'S,8'E,11'S,15'R)-13'-acetyl-6-chloro-7'-hydroxy-3,4-dihydro-2H,18'H-spiro[naphthalene-1,25'-[23]oxa[16]thia[1,13,17]triazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'R,15'S)-13'-acetyl-6-chloro-7'-hydroxy-3,4-dihydro-2H,18'H-spiro[naphthalene-1,25'-[23]oxa[16]thia[1,13,17]triazapentacyclo[17.7.2.0$^{3,6}$.0$^{11,15}$.0$^{22,27}$]octacosa[8,19,21,27]tetraen]-18'-one 16',16'-dioxide

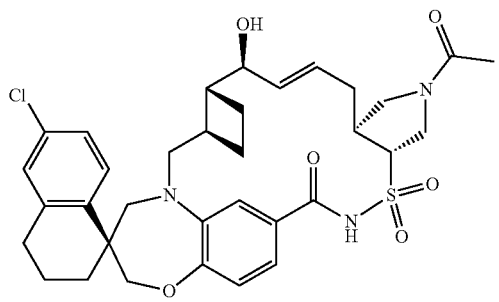

or

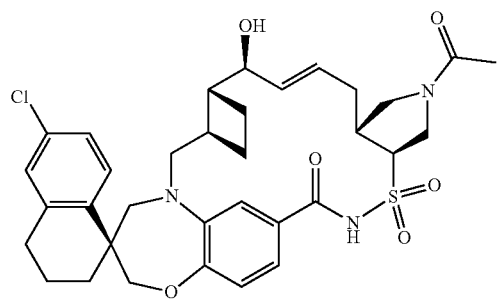

The title compound (19 mg) was obtained as an off-white solid as the second eluting isomer from preparative reverse-phase HPLC (Gemini Prep C$_{18}$ 5 μm column; Phenomenex, Torrance, CA; gradient elution of 45-95% acetonitrile in water, where both solvents contained 0.1% TFA, 30 min method) in Example 338. $^1$H NMR (500 MHz, CDCl$_3$) δ 9.20-8.27 (m, 1H), 7.63 (dd, J=4.6, 8.6 Hz, 1H), 7.15 (dd, J=2.1, 8.4 Hz, 1H), 7.10 (d, J=2.2 Hz, 1H), 7.04 (d, J=8.1 Hz, 1H), 7.00-6.96 (m, 1H), 6.95-6.90 (m, 1H), 5.77 (dd, J=3.7, 15.4 Hz, 1H), 5.54 (d, J=18.8 Hz, 1H), 4.62-4.49 (m, 1H), 4.42-1.29 (m, 30H). m/z (ESI, +ve ion) 654.3 (M+H)$^+$.

Example 340. (1S,3'R,6'R,7'S,8'E,11R,15'S)-13'-acetyl-6-chloro-7'-methoxy-3,4-dihydro-2H,18'H-spiro[naphthalene-1,25'-[23]oxa[16]thia[1,13,17]triazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'R)-13'-acetyl-6-chloro-7'-methoxy-3,4-dihydro-2H,18'H-spiro[naphthalene-1,25'-[23]oxa[16]thia[1,13,17]triazapentacyclo[17.7.2.0$^{3,6}$.0$^{11,15}$.0$^{22,27}$]octacosa[8,19,21,27]tetraen]-18'-one 16',16'-dioxide

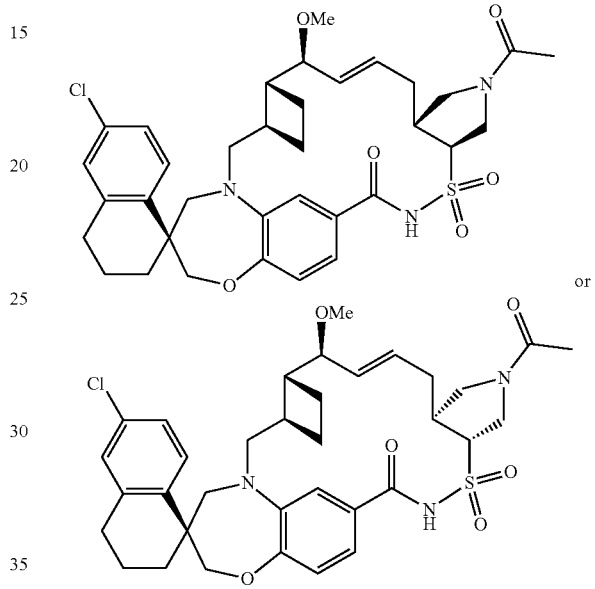

To a stirred solution of impure (1S,3'R,6'R,7'S,8'E,11'R,15'S)-13'-acetyl-6-chloro-7'-hydroxy-3,4-dihydro-2H,18'H-spiro[naphthalene-1,25'-[23]oxa[16]thia[1,13,17]triazapentacyclo[17.7.2.0$^{3,6}$.0$^{11,15}$.0$^{22,27}$]octacosa[8,19,21,27]tetraen]-18'-one 16',16'-dioxide or (1S,3'R,6'R,7'S,8'E,11'S,15'R)-13'-acetyl-6-chloro-7'-hydroxy-3,4-dihydro-2H,18'H-spiro[naphthalene-1,25'-[23]oxa[16]thia[1,13,17]triazapentacyclo[17.7.2.0$^{3,6}$.0$^{11,15}$.0$^{22,27}$]octacosa[8,19,21,27]tetraen]-18'-one 16',16'-dioxide (8.0 mg, 0.012 mmol, Example 338) in DMF (2 mL) was added sodium hydride, 60% dispersion in mineral oil (4.89 mg, 0.122 mmol) (in excess) at rt. The resulting mixture was stirred at rt for 30 min before iodomethane (0.760 μl, 0.012 mmol) (not weighed, much in excess) was added. The resulting mixture was stirred at rt for a period of 1.5 h. The reaction was quenched with methanol and the resulting mixture taken up in DMSO and subjected to preparative reverse-phase HPLC (Gemini™ Prep C$_{18}$ 5 μm column; Phenomenex, Torrance, CA; gradient elution of 50-95% acetonitrile in water, where both solvents contained 0.1% TFA, 30 min method) to give, after lyophilization, 0.7 mg of the title compound as an off-white solid. $^1$H NMR (500 MHz, CD$_3$OD) δ 7.73 (d, J=8.6 Hz, 1H), 7.17 (dd, J=2.2, 8.6 Hz, 1H), 7.10 (d, J=2.0 Hz, 1H), 7.03 (d, J=8.1 Hz, 1H), 6.93 (d, J=8.1 Hz, 1H), 6.88 (s, 1H), 5.96-5.80 (m, 1H), 5.62 (dd, J=9.0, 14.7 Hz, 1H), 4.79-4.65 (m, 1H), 4.21-3.59 (m, 8H), 3.40-3.32 (m, 2H), 3.25-3.21 (m, 3H), 3.13-3.01 (m, 1H), 2.87-2.61 (m, 4H), 2.56-2.25 (m, 4H), 2.16-2.02 (m, 4H), 1.99-1.67 (m, 6H), 1.50-1.39 (m, 1H). m/z (ESI, +ve ion) 668.3 (M+H)$^+$.

Example 341. (1S,3'R,6'R,7'S,8'E)-6-chloro-7'-hydroxy-3,4-dihydro-2H,13'H-spiro[naphthalene-1,20'-[18]oxa[11]thia[1,12]diazatetracyclo[12.7.2.0$^{3,6}$.0$^{17,22}$]tricosa[8,14,16,22]tetraen]-13'-one 11',11'-dioxide

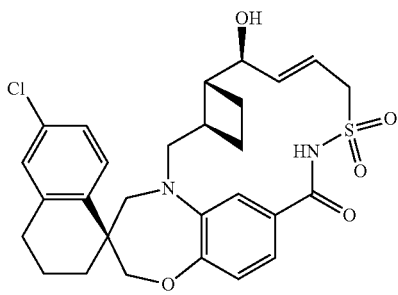 [SMILES: O=C1NS(=O)(=O)C/C=C/[C@H](O)[C@@H]2CC[C@H]2CN2C[C@@]3(CCCc4cc(Cl)ccc43)COc3ccc1cc32]

Step 1: (S)—N-(allylsulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide

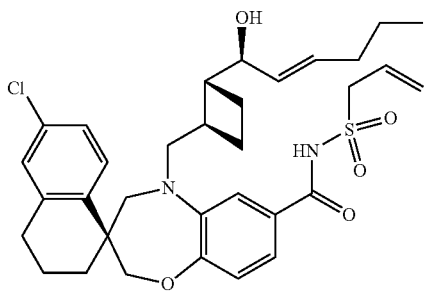 [SMILES: C=CCS(=O)(=O)NC(=O)c1ccc2c(c1)N(C[C@@H]1CC[C@H]1[C@@H](O)/C=C/CCC)C[C@@]1(CCCc3cc(Cl)ccc31)CO2]

To a stirred ice-cooled solution of (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (69 mg, 0.135 mmol, Intermediate AA12A), prop-2-ene-1-sulfonamide (82 mg, 0.676 mmol), and N,N-dimethylpyridin-4-amine (36.4 mg, 0.298 mmol) in DCM (8 mL) was added 1-(3-dimethylaminopropyl)-3-ethylcarbodiimide hydrochloride (64.8 mg, 0.338 mmol) in one portion. The resulting mixture was stirred at 0° C. and allowed to gradually warm up to ambient temperature overnight (18 h). The volatiles were removed in vacuo. The residue was subjected to combi-flash column chromatography ((EtOAc with 0.3% AcOH)/Hexanes, 25 min from 0 to 40%, 24 g ISCO silica gel column) to give 50 mg of the title compound as a white solid.

Step 2: (1S,3'R,6'R,7'S,8'E)-6-chloro-7'-hydroxy-3,4-dihydro-2H,13'H-spiro[naphthalene-1,20'-[18]oxa[11]thia[1,12]diazatetracyclo[12.7.2.0$^{3,6}$.0$^{17,22}$]tricosa[8,14,16,22]tetraen]-13'-one 11',11'-dioxide To a 25 mL single-necked round-bottomed flask were placed (S)—N-(allylsulfonyl)-6'-chloro-5-(((1R,2R)-2-((S,Z)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide (25 mg, 0.041 mmol) and 2$^{nd}$ generation hoveyda-grubbs catalyst (5.11 mg, 8.15 µmol). The flask was subjected to 3 cycles of evacuation and back-filling with nitrogen before DCM (20 mL) was introduced through a syringe under nitrogen. The resulting mixture was stirred at 45° C. in a preheated oil bath under nitrogen for a period of 20 h. The crude mixture was subjected to combi-flash column chromatography ((EtOAc with 0.3% AcOH)/Hexanes, 60 min from 0 to 100%, 24 g silica gel column, 13 mm tubes) to give the title compound as an off-white solid. $^1$H NMR (500 MHz, CDCl$_3$) δ 8.35 (br. s., 1H), 7.71 (d, J=8.6 Hz, 1H), 7.19 (dd, J=2.0, 8.6 Hz, 1H), 7.14-7.07 (m, 2H), 6.96 (d, J=8.1 Hz, 1H), 6.58 (br. s., 1H), 6.02 (br. s., 2H), 4.41-3.89 (m, 5H), 3.77-3.61 (m, 2H), 3.32 (d, J=14.2 Hz, 2H), 2.89-2.68 (m, 2H), 2.59-1.53 (m, 10H), 1.45 (t, J=12.5 Hz, 1H). m/z (ESI, +ve ion) 543.2 (M+H)$^+$.

Example 342. (1S,3'R,6'R,7'S)-6-chloro-7'-hydroxy-3,4-dihydro-2H,13'H-spiro[naphthalene-1,20'-[18]oxa[11]thia[1,12]diazatetracyclo[12.7.2.0$^{3,6}$.0$^{17,22}$]tricosa[14,16,22]trien]-13'-one 11',11'-dioxide

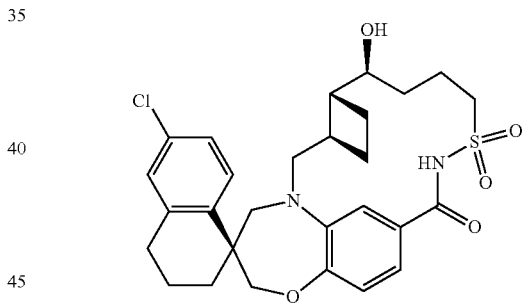

A mixture of (1S,3'R,6'R,7'S,8'E)-6-chloro-7'-hydroxy-3,4-dihydro-2H,13'H-spiro[naphthalene-1,20'-[18]oxa[11]thia[1,12]diazatetracyclo[12.7.2.0$^{3,6}$.0$^{17,22}$]tricosa[8,14,16,22]tetraen]-13'-one 11',11'-dioxide (not weighed, Example 341) and platinum (iv) oxide (in excess) in EtOAc (8 mL) was degassed and purged with hydrogen for multiple times and balloon hydrogenated for a period of 3 h. The reaction was quenched with DCM. The solid was filtered off and the residue after concentration in vacuo was taken up in DMSO and subjected to preparative reverse-phase HPLC (Gemini Prep C$_{18}$ 5 µm column; Phenomenex, Torrance, CA; gradient elution of 40-95% acetonitrile in water, where both solvents contained 0.1% TFA, 30 min method) to give, after lyophilization, 2.5 mg of the title compound as a white solid. $^1$H NMR (400 MHz, CDCl$_3$) δ 9.52 (br. s., 1H), 7.70 (d, J=8.4 Hz, 1H), 7.33 (d, J=8.0 Hz, 1H), 7.18 (dd, J=2.2, 8.5 Hz, 1H), 7.10 (d, J=2.2 Hz, 2H), 6.98 (d, J=8.2 Hz, 1H), 4.27-4.17 (m, 1H), 4.16-4.08 (m, 1H), 3.87-3.27 (m, 7H), 2.88-2.73 (m, 2H), 2.66 (br. s., 1H), 2.37-2.16 (m, 2H), 2.12-1.35 (m, 12H). m/z (ESI, +ve ion) 545.2 (M+H)$^+$.

Example 343. (3R,6R,7S,8E,11R,26S)-6'-chloro-7-hydroxy-3',4'-dihydro-2'H,19H-spiro[13,24-dioxa-17-thia-1,16,18-triazapentacyclo[18.7.2.0$^{3,6}$.11,16.u 0$^{23,28}$]nonacosa-8,20,22,28-tetraene-26,1'-naphthalen]-19-one 17,17-dioxide

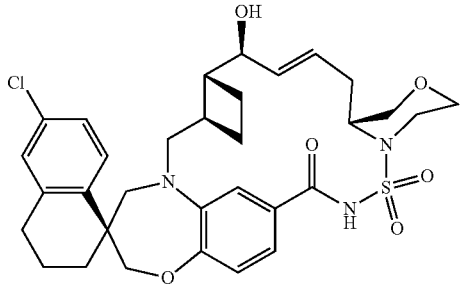

Step 1: (R)-3-allylmorpholine-4-sulfonamide

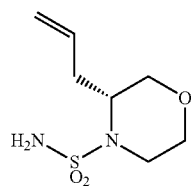

A mixture of (R)-3-allylmorpholine hydrochloride (0.700 g, 4.28 mmol), sulfamide (1.233 g, 12.83 mmol), and potassium carbonate (0.258 mL, 4.28 mmol) in 1,4-dioxane (20 mL) was stirred under nitrogen at 85° C. (a preheated oil bath) for a period of 16.5 h. Some sm was still remaining. More sulfamide (not weighed) was added and the stirring continued at 85° C. for another 2 h. After the volatiles were removed, saturated ammonium chloride aqueous solution was added to the residue. The mixture was extracted with DCM (3×). The combined organics were dried over anhydrous sodium sulfate and concentrated in vacuo. The residue was subjected to combi-flash column chromatography (EtOAc/Hexanes, 35 min from 0 to 100%, 40 g ISCO silica gel column) to give (R)-3-allylmorpholine-4-sulfonamide (0.422 g, 2.046 mmol, 47.8% yield) as a colorless oil, taken onto the next step.

Step 2: (S)—N—(((R)-3-allylmorpholino)sulfonyl)-6'-chloro-5-(((1R,2R)-2-((S)-1-hydroxyallyl)cyclobutyl)methyl)-3',4,4',5-tetrahydro-2H,2'H-Step 3. spiro[benzo[b][1,4]oxazepine-3,1'-naphthalene]-7-carboxamide

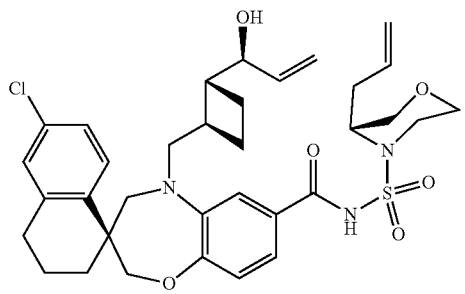

To a stirred ice-cooled solution of impure (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (190 mg, 0.406 mmol, Intermediate AA11A), (R)-3-allylmorpholine-4-sulfonamide (126 mg, 0.609 mmol) (140 mg actual), and N,N-dimethylpyridin-4-amine (124 mg, 1.015 mmol) in DCM (8 mL) was added 1-(3-dimethylaminopropyl)-3-ethylcarbodiimide hydrochloride (195 mg, 1.015 mmol) (210 mg actual) in one portion. The resulting mixture was stirred at ambient temperature for a period of 2.5 h. The crude mixture was subjected to combi-flash column chromatography ((EtOAc with 0.35% AcOH)/Hexanes, 35 min from 0 to 70%, 24 g ISCO silica gel column) to give 150 mg of impure title compound as a colorless film, taken onto the next step.

Step 3. (3R,6R,7S,8E,11R,26S)-6'-chloro-7-hydroxy-3',4'-dihydro-2'H,19H-spiro[13,24-dioxa-17-thia-1,16,18-triazapentacyclo[18.7.2.0$^{3,6}$.0$^{11,16}$.0$^{23,28}$]nonacosa-8,20,22,28-tetraene-26,1'-naphthalen]-19-one 17,17-dioxide To a 250-mL single-necked round-bottomed flask was placed (S)—N—(((R)-3-allylmorpholino)sulfonyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide (150 mg, 0.229 mmol) and 2$^{nd}$ generation hoveyda-grubbs catalyst (14.32 mg, 0.023 mmol). The flask was subjected to 3 cycles of evacuation and back-filling with nitrogen followed by addition of DCM (100 mL). The mixture was stirred at rt for a period of 8 h. The unreacted sm appeared to be the major in the crude reaction mixture. The volume was reduced and the crude was directly loaded onto a silica gel precolumn and subjected to combi-flash column chromatography ((EtOAc with 0.35% AcOH)/Hexanes, 50 min from 0 to 100%, 24 g ISCO silica gel column) to give, in the major band, 10 mg of the title compound as the second eluting fraction as an off-white solid. $^1$H NMR (400 MHz, CDCl$_3$) δ 8.61 (br. s., 1H), 7.69 (d, J=8.4 Hz, 1H), 7.18 (dd, J=2.2, 8.5 Hz, 1H), 7.11-7.05 (m, 2H), 6.93 (d, J=8.2 Hz, 1H), 6.87 (br. s., 1H), 5.98-5.78 (m, 1H), 5.72 (dd, J=7.8, 15.6 Hz, 1H), 4.15-3.85 (m, 6H), 3.80-3.57 (m, 5H), 3.46 (dt, J=3.1, 12.8 Hz, 1H), 3.36 (d, J=14.3 Hz, 1H), 3.23 (br. s., 1H), 2.87-2.70 (m, 2H), 2.68-2.50 (m, 2H), 2.41 (br. s., 2H), 2.11 (s, 1H), 2.02-1.75 (m, 5H), 1.73-1.59 (m, 2H), 1.51-1.43 (m, 1H). m/z (ESI, +ve ion) 628.0 (M+H)$^+$.

Example 344. (3R,6R,7S,8Z,11R,26S)-6'-chloro-7-hydroxy-3',4'-dihydro-2'H,19H-spiro[13,24-dioxa-17-thia-1,16,18-triazapentacyclo[18.7.2.0$^{3,6}$.0$^{11,16}$.0$^{23,28}$]nonacosa-8,20,22,28-tetraene-26,1'-naphthalen]-19-one 17,17-dioxide

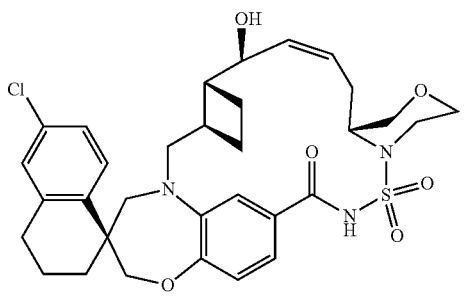

The title compound was synthesized as described in example 343 and was isolated as the first eluting isomer. This material was dissolved in DMSO and further purified by preparative reverse-phase HPLC (Gemini™ Prep C$_{18}$ 5 μm column; Phenomenex, Torrance, CA; gradient elution of 20-95% acetonitrile in water, where both solvents contained 0.1% TFA, 30 min method) to give, after lyophilization, 2.1 mg of the title compound as a white solid. $^1$H NMR (400 MHz, CDCl$_3$) δ 10.41 (s, 1H), 7.73 (d, J=8.4 Hz, 1H), 7.55 (dd, J=2.1, 8.3 Hz, 1H), 7.21 (d, J=2.0 Hz, 1H), 7.18 (dd, J=2.3, 8.4 Hz, 1H), 7.09 (d, J=2.2 Hz, 1H), 6.99 (d, J=8.2 Hz, 1H), 5.90-5.77 (m, 1H), 5.70 (dd, J=7.7, 10.3 Hz, 1H), 4.50 (t, J=7.5 Hz, 1H), 4.20-4.11 (m, 1H), 4.09-4.03 (m, 1H), 4.02-3.88 (m, 3H), 3.85-3.56 (m, 5H), 3.47-3.30 (m, 1H), 3.14-2.98 (m, 2H), 2.85-2.66 (m, 4H), 2.29-2.12 (m, 2H), 2.10-1.59 (m, 7H), 1.52-1.31 (m, 2H). m/z (ESI, +ve ion) 628.0 (M+H)$^+$.

Example 345. (1S,3'R,6'R,7'S,8'E,11'S)-6-chloro-7'-hydroxy-3,4-dihydro-2H,18'H-spiro[naphthalene-1,25'-[23]oxa[16]thia[1,15,17]triazapentacyclo[17.7.2.0$^{3,6}$.0$^{11,15}$.0$^{22,27}$]octacosa[8,19,21,27]tetraen]-18'-one 16',16'-dioxide

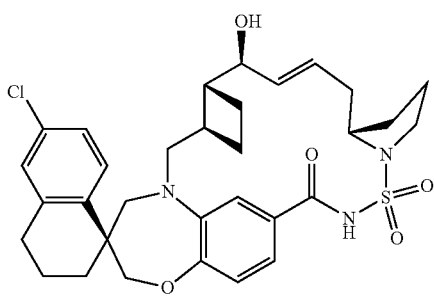

Step 1: (S)-2-allylpyrrolidine-1-sulfonamide

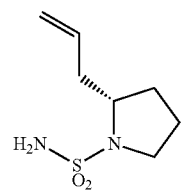

A mixture of (S)-2-allylpyrrolidine hydrochloride (1.00 g, 6.77 mmol), sulfamide (2.60 g, 27.1 mmol), and triethylamine (1.41 mL, 10.16 mmol) in 1,4-dioxane (20 mL) was stirred under nitrogen at 85° C. (a preheated oil bath) for a period of 17 h. The volatiles were removed and the residue was subjected to combi-flash column chromatography (EtOAc/Hexanes, 35 min from 0 to 100%, 40 g ISCO silica gel column) to give (S)-2-allylpyrrolidine-1-sulfonamide (0.80 g, 4.20 mmol, 62.1% yield) as a white crystal solid, taken onto the next step.

Step 2: (S)-6'-chloro-5-(((1R,2R)-2-((S,E)-1-hydroxy-4-((S)-1-sulfamoylpyrrolidin-2-yl)but-2-en-1-yl)cyclobutyl)methyl)-3',4,4',5-tetrahydro-2H,2'H-spiro[benzo[b][1,4]oxazepine-3,1'-naphthalene]-7-carboxylic acid

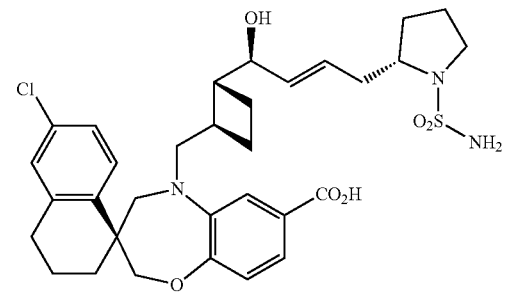 [SMILES: NS(=O)(=O)N1CCC[C@H]1C/C=C/[C@H](O)[C@@H]1CC[C@H]1CN1C[C@@]2(CCCc3cc(Cl)ccc32)COc2ccc(C(=O)O)cc21]

To a 25 mL single-necked round-bottomed flask were placed (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (75.5 mg, 0.148 mmol, Intermediate AA12A), (S)-2-allylpyrrolidine-1-sulfonamide (84 mg, 0.444 mmol), and 2$^{nd}$ generation hoveyda-grubbs catalyst (9.28 mg, 0.015 mmol). The flask was subjected to 3 cycles of evacuation and back-filling with nitrogen before DCE (2.0 mL) was introduced through a syringe under nitrogen. The resulting mixture was stirred under nitrogen at rt for a period of 4 h. The crude mixture was subjected to combi-flash column chromatography ((EtOAc with 0.35% AcOH)/Hexanes, 35 min from 0 to 100%, 24 g ISCO silica gel column) to give 90 mg of the title compound as a colorless film, impure and directly taken onto the next step.

Step 3: (1S,3'R,6'R,7'S,8'E,11'S)-6-chloro-7'-hydroxy-3,4-dihydro-2H,18'H-spiro[naphthalene-1,25'-[23]oxa[16]thia[1,15,17]triazapentacyclo[17.7.2.0$^{3,6}$.0$^{11,15}$.0$^{22,27}$]octacosa[8,19,21,27]tetraen]-18'-one 16',16'-dioxide To a stirred ice-cooled solution of (S)-6'-chloro-5-(((1R,2R)-2-((S,E)-1-hydroxy-4-((S)-1-sulfamoylpyrrolidin-2-yl)

but-2-en-1-yl)cyclobutyl)methyl)-3',4,4',5-tetrahydro-2H,2'H-spiro[benzo[b][1,4]oxazepine-3,1'-naphthalene]-7-carboxylic acid (95 mg, 0.151 mmol) and N,N-dimethylpyridin-4-amine (55.2 mg, 0.452 mmol) in DCM (75 mL) was added 1-(3-dimethylaminopropyl)-3-ethylcarbodiimide hydrochloride (87 mg, 0.452 mmol) in one portion. The resulting mixture was stirred at 0° C. for 10 min and at ambient temperature for a period of 6 h. After the volume was reduced, the crude mixture was subjected to combi-flash column chromatography ((EtOAc with 0.35% AcOH)/Hexanes, 35 min from 10 to 100%, 24 g ISCO silica gel column) to give the title compound as the second eluting fraction which was not pure. This was further purified by preparative reverse-phase HPLC (Gemini Prep C$_{18}$ 5 μm column; Phenomenex, Torrance, CA; gradient elution of 40-95% acetonitrile in water, where both solvents contained 0.1% TFA, 30 min method) to give, after lyophilization, 12 mg of the title compound (Example 345) as a white solid. $^1$H NMR (500 MHz, CDCl$_3$) δ 8.94 (br. s., 1H), 7.70 (d, J=8.6 Hz, 1H), 7.18 (dd, J=2.2, 8.6 Hz, 1H), 7.09 (d, J=2.0 Hz, 1H), 7.01 (d, J=7.8 Hz, 1H), 6.92 (d, J=8.1 Hz, 1H), 6.77 (br. s., 1H), 5.95 (ddd, J=4.2, 10.3, 14.9 Hz, 1H), 5.73 (dd, J=8.8, 15.2 Hz, 1H), 4.28 (dd, J=3.2, 8.6 Hz, 1H), 4.16-4.00 (m, 3H), 3.97-3.81 (m, 2H), 3.76-3.62 (m, 2H), 3.23 (d, J=14.2 Hz, 1H), 3.08 (br. s., 1H), 2.85-2.69 (m, 2H), 2.63-1.71 (m, 15H), 1.70-1.60 (m, 1H), 1.43 (t, J=12.3 Hz, 1H). m/z (ESI, +ve ion) 612.0 (M+H)$^+$.

Example 346. (1S,3'R,6'R,7'S,8'E,11'S)-6-chloro-16',16'-dioxido-18'-oxo-3,4-dihydro-2H-spiro[naphthalene-1,25'-[23]oxa[16]thia[1,15,17]triazapentacyclo[17.7.2.0$^{3,6}$.0$^{11,15}$.0$^{22,27}$]octacosa[8,19,21,27]tetraen]-7'-yl acetate

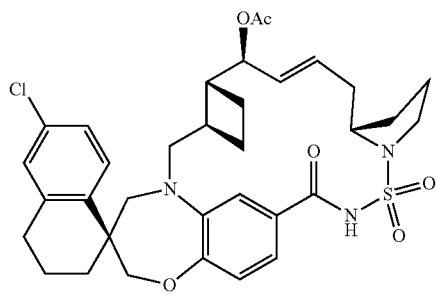

The first eluting fraction from combi-flash column chromatography ((EtOAc with 0.35% AcOH)/Hexanes, 35 min from 10 to 100%, 24 g ISCO silica gel column) in Example 345 gave the impure title compound. It was further purified by preparative reverse-phase HPLC (Gemini Prep C$_{18}$ 5 μm column; Phenomenex, Torrance, CA; gradient elution of 45-95% acetonitrile in water, where both solvents contained 0.1% TFA, 30 min method) to give, after lyophilization, 2 mg of the title compound as a white solid. Note that the title compound was formed in situ by reacting under the reaction condition with the residual acetic acid brought in with the starting material. $^1$H NMR (400 MHz, CDCl$_3$) δ 8.28 (s, 1H), 7.71 (d, J=8.6 Hz, 1H), 7.18 (dd, J=2.3, 8.6 Hz, 1H), 7.09 (d, J=2.3 Hz, 1H), 6.95-6.84 (m, 2H), 6.74 (d, J=1.8 Hz, 1H), 6.04-5.90 (m, 1H), 5.63-5.51 (m, 1H), 5.31 (dd, J=3.7, 9.0 Hz, 1H), 4.16 (dd, J=4.0, 8.1 Hz, 1H), 4.12-3.96 (m, 3H), 3.90-3.79 (m, 2H), 3.73 (d, J=14.3 Hz, 1H), 3.18 (d, J=14.3 Hz, 1H), 2.98 (dd, J=9.9, 15.2 Hz, 1H), 2.86-2.71 (m, 2H), 2.68-2.59 (m, 1H), 2.48-2.25 (m, 2H), 2.20-1.52 (m, 15H), 1.45-1.34 (m, 1H). m/z (ESI, +ve ion) 654.1 (M+H)$^+$.

Example 347. (1S,3'R,6'R,7'S,8'E,11R)-6-chloro-7'-hydroxy-3,4-dihydro-2H,18'H-spiro[naphthalene-1,25'-[23]oxa[16]thia[1,15,17]triazapentacyclo[17.7.2.0$^{3,6}$.0$^{11,15}$.0$^{22,27}$]octacosa[8,19,21,27]tetraen]-18'-one 16',16'-dioxide

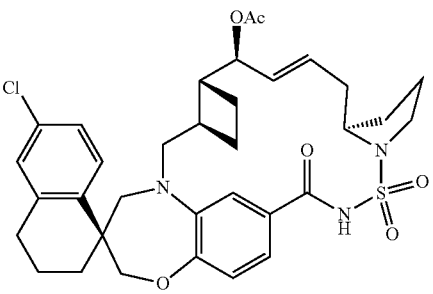

Step 1: (R)-2-allylpyrrolidine-1-sulfonamide

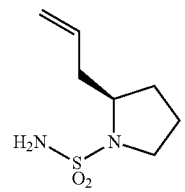

A mixture of (R)-2-allylpyrrolidine hydrochloride (1.00 g, 6.77 mmol), sulfamide (1.953 g, 20.32 mmol), and triethylamine (1.413 mL, 10.16 mmol) in 1,4-dioxane (20 mL) was stirred under nitrogen at 85° C. (a preheated oil bath) for a period of 16 h. It appeared that still some sm was remaining. The volume was reduced in vacuo and the residue was subjected to combi-flash column chromatography (EtOAc/Hexanes, 35 min from 0 to 100%, 40 g ISCO silica gel column) to give (R)-2-allylpyrrolidine-1-sulfonamide (0.75 g, 3.94 mmol, 58.2% yield) as a white crystalline solid, taken onto the next step.

Step 2: (S)-6'-chloro-5-(((1R,2R)-2-((S,E)-1-hydroxy-4-((R)-1-sulfamoylpyrrolidin-2-yl)but-2-en-1-yl)cyclobutyl)methyl)-3',4,4',5-tetrahydro-2H,2'H-spiro[benzo[b][1,4]oxazepine-3,1'-naphthalene]-7-carboxylic

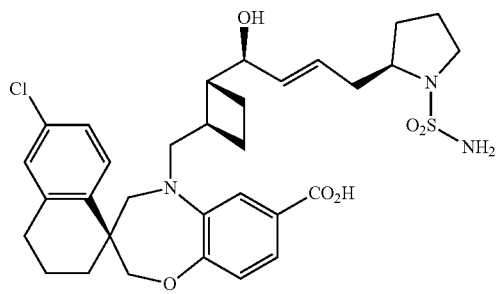 [SMILES: NS(=O)(=O)N1CCC[C@@H]1C/C=C/[C@H](O)[C@@H]1CC[C@H]1CN1C[C@@]2(CCCc3cc(Cl)ccc32)COc2ccc(C(=O)O)cc21]

To a 25 mL single-necked round-bottomed flask were placed (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (74.0 mg, 0.145 mmol, Intermediate AA12A), (R)-2-allylpyrrolidine-1-sulfonamide (83 mg, 0.435 mmol), and 2$^{nd}$ generation hoveyda-grubbs catalyst (9.09 mg, 0.015 mmol). The flask was subjected to 3 cycles of evacuation and back-filling with nitrogen before DCE (2.0 mL) was introduced through a syringe under nitrogen. The resulting mixture was stirred under nitrogen at rt for a period of 3 h. The crude mixture was subjected to combi-flash column chromatography ((EtOAc with 0.35% AcOH)/Hexanes, 35 min from 0 to 100%, 24 g ISCO silica gel column) to give 70 mg of the title compound as a colorless film, impure and taken onto the next step directly.

Step 3: (1S,3'R,6'R,7'S,8'E,11R)-6-chloro-7'-hydroxy-3,4-dihydro-2H,18'H-spiro[naphthalene-1,25'-[23]oxa[16]thia[1,15,17]triazapentacyclo[17.7.2.0$^{3,6}$.0$^{11,15}$.0$^{22,27}$]octacosa[8,19,21,27]tetraen]-18'-one 16',16'-dioxide To a stirred ice-cooled solution of (S)-6'-chloro-5-(((1R,2R)-2-((S,E)-1-hydroxy-4-((R)-1-sulfamoylpyrrolidin-2-yl)but-2-en-1-yl)cyclobutyl)methyl)-3',4,4',5-tetrahydro-2H,2'H-spiro[benzo[b][1,4]oxazepine-3,1'-naphthalene]-7-carboxylic acid (70 mg, 0.111 mmol) and N,N-dimethylpyridin-4-amine (40.7 mg, 0.333 mmol) in DCM (55 mL) was added 1-(3-dimethylaminopropyl)-3-ethylcarbodiimide hydrochloride (63.9 mg, 0.333 mmol) in one portion. The resulting mixture was stirred at 0° C. for 10 min and at ambient temperature for a period of 7 h. After the volume was reduced, the crude mixture was subjected to preparative reverse-phase HPLC (Gemini™ Prep C$_{18}$ 5 μm column; Phenomenex, Torrance, CA; gradient elution of 45-95% acetonitrile in water, where both solvents contained 0.1% TFA, 30 min method) to give, after lyophilization, 4.5 mg of the title compound as a white solid. $^1$H NMR (400 MHz, CDCl$_3$) δ 8.84 (s, 1H), 7.71 (d, J=8.6 Hz, 1H), 7.18 (dt, J=2.2, 8.5 Hz, 2H), 7.09 (d, J=2.2 Hz, 1H), 6.96 (d, J=8.2 Hz, 1H), 6.74 (s, 1H), 6.30-6.13 (m, 1H), 5.73 (dd, J=6.9, 15.6 Hz, 1H), 4.23 (dd, J=2.8, 7.1 Hz, 1H), 4.14-3.81 (m, 5H), 3.75-3.57 (m, 2H), 3.32 (d, J=14.5 Hz, 1H), 3.13 (dd, J=10.3, 15.0 Hz, 1H), 2.89-2.59 (m, 3H), 2.50-1.60 (m, 15H), 1.45 (t, J=11.9 Hz, 1H). m/z (ESI, +ve ion) 612.0 (M+H)$^+$.

Example 348. (1S,3'R,6'R,7'S,8'E,11R)-6-chloro-16',16'-dioxido-18'-oxo-3,4-dihydro-2H-spiro[naphthalene-1,25'-[23]oxa[16]thia[1,15,17]triazapentacyclo[17.7.2.0$^{3,6}$.0$^{11,15}$.0$^{22,27}$]octacosa[8,19,21,27]tetraen]-7'-yl acetate

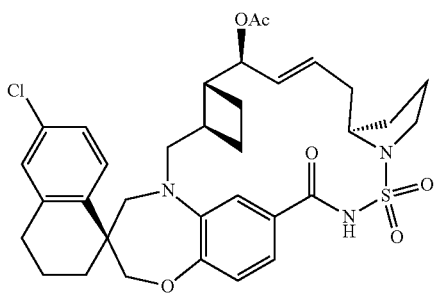

The title compound (7.0 mg) was obtained as a white solid as the second eluting isomer from preparative reverse-phase HPLC (Gemini Prep C$_{18}$ 5 μm column; Phenomenex, Torrance, CA; gradient elution of 45-95% acetonitrile in water, where both solvents contained 0.1% TFA, 30 min method) in Example 347. Note that the title compound was formed in situ by reacting under the reaction condition with the residual acetic acid brought in with the starting material. $^1$H NMR (500 MHz, CDCl$_3$) δ 8.51 (br. s., 1H), 7.70 (d, J=8.6 Hz, 1H), 7.19 (dd, J=2.2, 8.3 Hz, 1H), 7.09 (d, J=2.0 Hz, 1H), 7.04 (d, J=8.1 Hz, 1H), 6.94 (d, J=8.1 Hz, 1H), 6.77 (br. s., 1H), 6.12-5.97 (m, 1H), 5.59 (dd, J=5.9, 15.4 Hz, 1H), 5.27 (br. s., 1H), 4.16-4.01 (m, 3H), 3.92-3.79 (m, 2H), 3.69 (d, J=14.2 Hz, 1H), 3.61 (d, J=14.9 Hz, 1H), 3.30 (d, J=14.2 Hz, 1H), 3.17-3.06 (m, 1H), 2.88-1.58 (m, 20H), 1.45 (t, J=12.5 Hz, 1H). m/z (ESI, +ve ion) 654.1 (M+H)$^+$.

Example 349. (1S,3'R,6'R,8'E,11'S,12'R)-6-chloro-11',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dione 13',13'-dioxide

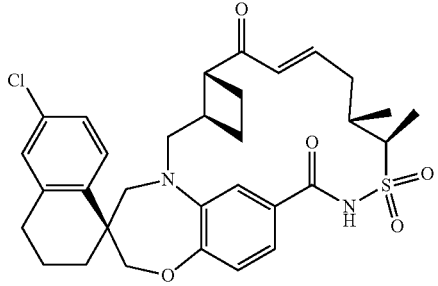 [SMILES: C[C@@H]1[C@@H](C)C/C=C/C(=O)[C@@H]2CC[C@H]2CN2C[C@@]3(CCCc4cc(Cl)ccc43)COc3ccc(cc32)C(=O)NS1(=O)=O]

To a stirred ice-cooled solution of (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (550 mg, 0.918 mmol, Example 719, Step 2) in DCM (10 mL) was added dess-martin periodinane (401 mg, 0.918 mmol) in one portion as a solid. The resulting mixture was stirred at 0° C. for a period of 0.5 h. The crude mixture was loaded onto a silica gel pre-column and subjected to combi-flash column chromatography (EtOAc/Hexanes, 40 min from 0 to 60%, 40 g ISCO silica gel column) to give the title compound (483.4 mg, 0.809 mmol, 88% yield) as a crystalline white solid. $^1$H NMR (500 MHz, CDCl$_3$) δ 8.02 (s, 1H), 7.76 (d, J=8.3 Hz, 1H), 7.36 (d, J=2.0 Hz, 1H), 7.20 (dd, J=2.3, 8.4 Hz, 1H), 7.08 (d, J=2.2 Hz, 1H), 6.88-6.81 (m, 1H), 6.77 (dd, J=2.0, 8.1 Hz, 1H), 6.69-6.58 (m, 1H), 5.91 (d, J=15.7 Hz, 1H), 4.21-3.98 (m, 3H), 3.94-3.81 (m, 2H), 3.76 (q, J=9.5 Hz, 1H), 3.25 (d, J=14.4 Hz, 1H), 3.12-3.01 (m, 1H), 2.98 (dd, J=3.1, 15.5 Hz, 1H), 2.85-2.66 (m, 2H), 2.25-1.53 (m, 10H), 1.50 (d, J=7.3 Hz, 3H), 1.43-1.35 (m, 1H), 1.15 (d, J=5.9 Hz, 3H). m/z (ESI, +ve ion) 597.1 (M+H)$^+$.

Example 350. (1S,3'R,6'R,9'R,11'S,12'R)-6-chloro-11',12'-dimethyl-9'-((1E)-1-propen-1-yl)-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 13',13'-dioxide

Example 353. (1S,3'R,6'R,9'S,11'S,12'R)-6-chloro-11',12'-dimethyl-9'-((1E)-1-propen-1-yl)-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [16,18,24]triene]-7',15'-dione 13',13'-dioxide

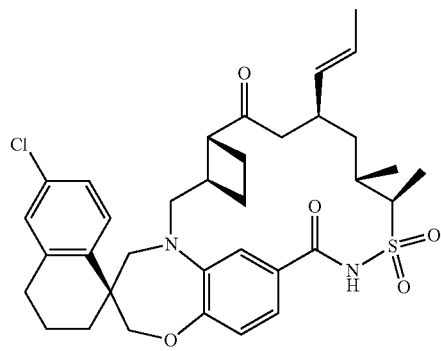 [SMILES: C/C=C/[C@@H]1CC(=O)[C@@H]2CC[C@H]2CN2C[C@@]3(CCCc4cc(Cl)ccc43)COc3ccc(cc32)C(=O)NS(=O)(=O)[C@H](C)[C@@H](C)C1]

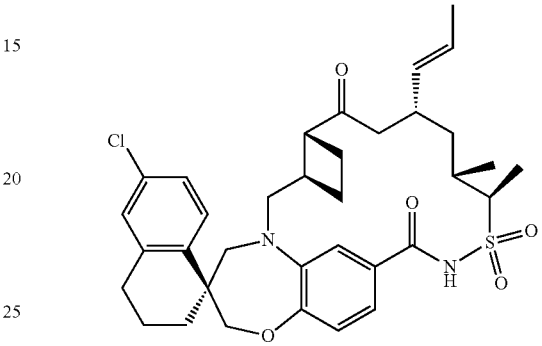

To a 25-mL single-necked round-bottomed flask were placed (1S,3'R,6'R,8'E,11'S,12'R)-6-chloro-11',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dione 13',13'-dioxide (190 mg, 0.318 mmol, Example 349), trans-propenylboronic acid (137 mg, 1.591 mmol), (acetylacetonato)bis(ethylene) rhodium (i) (16.43 mg, 0.064 mmol), and (R)-(+)-2,2'-bis(diphenylphosphino)-1,1'-binaphthyl (39.6 mg, 0.064 mmol). The flask was subjected to 3 cycles of evacuation and back-filling with nitrogen before dioxane (2.0 mL) was added followed by water (0.2 mL). The resulting mixture was stirred at 100° C. under nitrogen for a period of 5 h. After cooled, the mixture was filtered through a layer of celite and the cake was washed with EtOAc. The filtrate was concentrated in vacuo. The residue was loaded onto a silica gel precolumn and subjected to combi-flash column chromatography (EtOAc/Hexanes, 40 min at 20%, 40 g silica gel, 13 mm tubes) to give a major peak, which contained 3 compounds, presumably the desired product(s), the unreacted sm, and an unknown product. This was subjected to preparative reverse-phase HPLC (Gemini™ Prep C$_{18}$ 5 μm column; Phenomenex, Torrance, CA; gradient elution of 50-95% acetonitrile in water, where both solvents contained 0.1% TFA, 30 min method) to give, after lyophilization, 28 mg of the title compound as an off-white solid. $^1$H NMR (500 MHz, CDCl$_3$) δ 8.21 (s, 1H), 7.68 (d, J=8.6 Hz, 1H), 7.19 (dd, J=2.2, 8.6 Hz, 1H), 7.09 (d, J=2.2 Hz, 1H), 7.03-6.80 (m, 3H), 5.27-5.02 (m, 2H), 4.19-4.04 (m, 2H), 3.88 (dq, J=2.7, 7.3 Hz, 1H), 3.81-3.66 (m, 2H), 3.32-3.17 (m, 3H), 2.91-2.69 (m, 3H), 2.50-2.25 (m, 3H), 2.22-2.12 (m, 1H), 2.07-1.64 (m, 7H), 1.56 (d, J=5.6 Hz, 3H), 1.51-1.38 (m, 4H), 1.28-1.24 (m, 2H), 1.03 (d, J=6.8 Hz, 3H). m/z (ESI, +ve ion) 639.0 (M+H)$^+$.

To a 25-mL single-necked round-bottomed flask were placed (1S,3'R,6'R,8'E,11'S,12'R)-6-chloro-11',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dione 13',13'-dioxide (294 mg, 0.492 mmol, Example 349), trans-propenylboronic acid (211 mg, 2.46 mmol), (acetylacetonato)bis(ethylene) rhodium (i) (25 mg, 0.098 mmol), and (s)-(−)-2,2'-bis(diphenylphosphino)-1,1'-binaphthyl (61 mg, 0.098 mmol). The flask was subjected to 3 cycles of evacuation and back-filling with nitrogen before dioxane (3.0 mL) was added followed by water (0.3 mL). The resulting mixture was stirred under nitrogen at 100° C. for 5.5 h. After cooled, the mixture was loaded onto a silica gel precolumn and subjected to combi-flash column chromatography (EtOAc/Hexanes, 40 min at 20%, 40 g ISCO silica gel column) to give a major peak, which contained 3 compounds, presumably the desired product, the unreacted sm, and an unknown product. This was subjected to preparative reverse-phase HPLC (Gemini Prep C$_{18}$ 5 μm column; Phenomenex, Torrance, CA; gradient elution of 50-95% acetonitrile in water, where both solvents contained 0.1% TFA, 30 min method) to give 65 mg of the title compound as an off-white solid. $^1$H NMR (500 MHz, CDCl$_3$) δ 8.24 (s, 1H), 7.70 (d, J=8.6 Hz, 1H), 7.22-7.16 (m, 2H), 7.09 (d, J=2.2 Hz, 1H), 7.02-6.94 (m, 1H), 6.94-6.90 (m, 1H), 5.44-5.34 (m, 1H), 5.17 (ddd, J=1.5, 7.9, 15.3 Hz, 1H), 4.20-4.14 (m, 1H), 4.13-4.06 (m, 2H), 3.86 (dd, J=5.7, 15.5 Hz, 1H), 3.68 (d, J=14.4 Hz, 1H), 3.28-3.14 (m, 2H), 3.03 (dd, J=5.6, 15.7 Hz, 1H), 2.90-2.69 (m, 3H), 2.64-2.54 (m, 1H), 2.33-2.16 (m, 2H), 2.07-1.67 (m, 8H), 1.57 (dd, J=1.5, 6.4 Hz, 3H), 1.51-1.37 (m, 5H), 1.22 (ddd, J=2.8, 11.6, 14.5 Hz, 1H), 1.02 (d, J=6.8 Hz, 3H). m/z (ESI, +ve ion) 639.0 (M+H)$^+$.

Example 357. ethyl(2S)-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [7,16,18,24]tetraen]-9'-yl)(methoxy)ethanoate

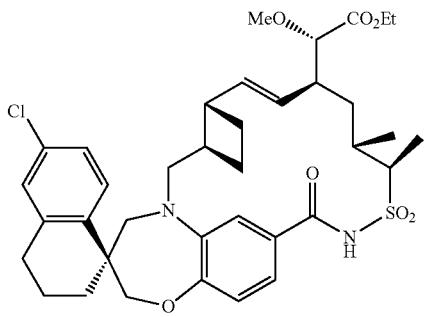

Step 1: (1S,3'R,6'R,7'S,8'E,11'S,12'R)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24] tetraen]-15'-one-13',13'-dioxide

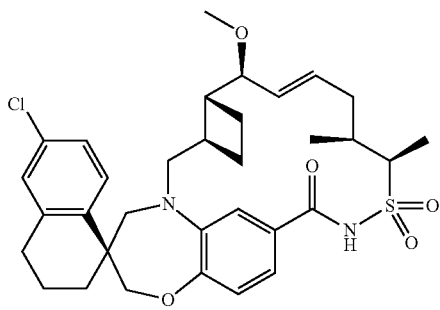 [SMILES: CO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

To a slurry of (1S,3'R,6'R,7'S,8'E,11'S,12'R)-6-chloro-7'-hydroxy-11',12'-dimethyl-3,4-dihydro-2h,15'h-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (Example 719, Step 2; 32.6 g, 49.1 mmol) (containing 9.8% toluene, starting material was not completely soluble in Me-THF) and MeI (15.2 ml, 245 mmol) in Me-THF (820 ml) was added KHMDS (1.0 M in THF, 167 ml, 167 mmol) dropwise for 30 min while maintaining reaction temperature between −44° C. and −38° C. under $N_2$. After the mixture was stirred at −44° C. for 30 min, the reaction was allowed to warm to ambient temperature and stirred for 1.5 h (LCMS confirmed the reaction was complete). The reaction mixture was cooled to 5° C., quenched (170 mL of saturated aqueous $NH_4Cl$ and 170 mL of water) carefully while maintaining temperature between 5° C. and 14° C., and acidified (340 mL of 10% aqueous citric acid). The organic layer was separated and the aqueous layer was back-extracted with EtOAc (500 mL). The combined organic layers were washed with brine (3×500 mL), dried ($MgSO_4$), and concentrated under reduced pressure to provide a crude target compound (30.1 g, 49.1 mmol, quantitatively) (purity >98% with no over 1% major impurity from HPLC) as a bright yellow solid. After the same scale reaction was repeated for four times, all the crude products (4×49.1 mmol=196 mmol) were dissolved in EtOAc, combined, and concentrated under reduced pressure. Then the combined crude product was recrystallized as follows: ethanol (800 mL) was added to the crude product and the resulting slurry solution was shaked well while heating the solution for 20 min. Water (250 mL) was added dropwise for 30 min at rt and the slurry was cool down to 0° C. After the slurry was kept in ice bath for 4 h, the solid product was filtered through filter paper. The filter cake was rinsed with ice-cold 30% water in EtOH (300 mL) and air-dried for 2 days. The product was further dried under high vacuum at 40° C. for 4 days to provide the pure target compound (115 g, 188 mmol, 96% yield) as a white solid: $^1$H NMR (600 MHz, DMSO-d6) δ 11.91 (s, 1H), 7.65 (d, J=8.6 Hz, 1H), 7.27 (dd, J=8.5, 2.3 Hz, 1H), 7.17 (d, J=2.4 Hz, 1H), 7.04 (dd, J=8.2, 2.0 Hz, 1H), 6.90 (d, J=8.2 Hz, 1H), 6.76 (d, J=1.8 Hz, 1H), 5.71 (ddd, J=15.1, 9.7, 3.5 Hz, 1H), 5.50 (ddd, J=15.2, 9.2, 1.1 Hz, 1H), 4.08 (qd, J=7.2, 7.2, 7.2, 1.5 Hz, 1H), 4.04 (d, J=12.3 Hz, 1H), 3.99 (d, J=12.3 Hz, 1H), 3.73 (d, J=14.9 Hz, 1H), 3.56 (d, J=14.1 Hz, 1H), 3.53 (dd, J=9.1, 3.3 Hz, 1H), 3.19 (d, J=14.1 Hz, 1H), 3.09 (s, 3H), 3.03 (dd, J=15.4, 10.4 Hz, 1H), 2.79 (dt, J=17.0, 3.5, 3.5 Hz, 1H), 2.69 (ddd, J=17.0, 10.7, 6.3 Hz, 1H), 2.44-2.36 (m, 1H), 2.24-2.12 (m, 2H), 2.09 (ddd, J=15.5, 9.6, 2.3 Hz, 1H), 1.97 (dt, J=13.6, 3.6, 3.6 Hz, 1H), 1.91-1.80 (m, 4H), 1.80-1.66 (m, 3H), 1.38 (td, J=12.3, 12.3, 3.5 Hz, 1H), 1.33 (d, J=7.2 Hz, 3H), 0.95 (d, J=6.8 Hz, 3H); [α]$_D$ (24° C., c=0.0103 g/mL, DCM)=−86.07°; m.p. 222.6-226.0° C.; FT-IR (KBr): 3230 (b), 2931 (b), 1688 (s), 1598 (s), 1570 (s), 1505 (s), 1435 (s), 1384 (s), 1335 (s), 1307 (s), 1259 (s), 1155 (s), 1113 (s), 877 (s), 736 (s) cm$^{-1}$; Anal. Calcd. for $C_{33}H_{41}ClN_2O_5S$: C, 64.64; H, 6.74; N, 4.57; Cl, 5.78; S, 5.23. Found: C, 64.71; H, 6.81; N, 4.65; Cl, 5.81; S, 5.11; HRMS (ESI) m/z 613.2493 [M+H]$^+$ ($C_{33}H_{41}ClN_2O_5S$ requires 613.2503). The mother liquor was concentrated under reduced pressure and further purification of the residue by flash column chromatography (200 g $SiO_2$, 10% and 10% to 45% and 45% EtOA/hexanes w/ 0.3% AcOH, gradient elution) provided additional pure product (3.1 g, 5.1 mmol, 2.6%) as a off-white solid.

Step 2: ethyl(2R)-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [7,16,18,24]tetraen]-9'-yl)(methoxy)ethanoate To a stirred solution of (1S,3'R,6'R,7'S,8'E,11'S,12'R)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (152 mg, 0.248 mmol) and rhodium (ii) acetate dimer (11 mg, 0.025 mmol) in DCM (3 mL) was added dropwise a solution of ethyl diazoacetate (0.077 mL, 0.74 mmol) in DCM (2 mL) at ambient temperature over 6 min. The resulting mixture was stirred at ambient temperature for 1 h 20 min. The reaction stalled and the mixture was loaded onto a silica gel precolumn and subjected to combi-flash column chromatography (EtOAc/Hexanes, 30 min from 0 to 100%, 24 g ISCO silica gel column) to give an impure product mixture. This was taken up in DMSO and subjected to preparative reverse-phase HPLC (Gemini Prep $C_{18}$ 5 μm column; Phenomenex, Torrance, CA; gradient elution of 50-95% acetonitrile in water, where both solvents contained 0.1% TFA, 30 min method) to give 7.0 mg of the title compound as the first eluting fraction as a light orange solid. ¹H NMR (400 MHz, CD₂Cl₂) δ 8.01 (s, 1H), 7.71 (d, J=8.4 Hz, 1H), 7.16 (dd, J=2.2, 8.5 Hz, 1H), 7.09 (d, J=2.2 Hz, 1H), 7.01-6.87 (m, 3H), 5.90 (dd, J=4.7, 15.5 Hz, 1H), 5.28-5.16 (m, 1H), 4.25-4.02 (m, 6H), 3.82 (d, J=15.5 Hz, 1H), 3.66-3.58 (m, 2H), 3.34 (s, 3H), 3.23-3.14 (m, 1H), 3.07 (dd, J=8.0, 15.5 Hz, 1H), 2.80-2.71 (m, 2H), 2.56 (dt, J=4.3, 8.7 Hz, 2H), 2.22-1.56 (m, 7H), 1.52-1.39 (m, 5H), 1.31-1.23 (m, 5H), 0.98 (d, J=6.8 Hz, 3H). m/z (ESI, +ve ion) 699.1 (M+H)⁺.

Example 358. ethyl(2R)-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [7,16,18,24]tetraen]-9'-yl)(methoxy)ethanoate

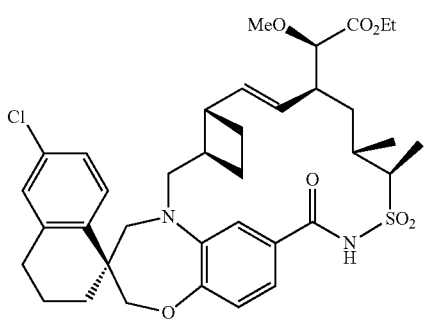

The title compound (4.0 mg) was obtained as the second eluting fraction as a light orange solid from the to preparative reverse-phase HPLC purification in Example 357, Step 2. ¹H NMR (400 MHz, CD₂Cl₂) δ 7.99 (s, 1H), 7.71 (d, J=8.6 Hz, 1H), 7.16 (dd, J=2.3, 8.4 Hz, 1H), 7.09 (d, J=2.3 Hz, 1H), 7.03-6.89 (m, 3H), 5.95 (dd, J=4.4, 15.6 Hz, 1H), 5.22 (ddd, J=1.6, 8.5, 15.4 Hz, 1H), 4.21-3.97 (m, 6H), 3.83 (d, J=15.5 Hz, 1H), 3.62 (d, J=14.5 Hz, 1H), 3.50 (d, J=6.5 Hz, 1H), 3.32 (s, 3H), 3.18 (d, J=14.1 Hz, 1H), 3.06 (dd, J=8.2, 15.5 Hz, 1H), 2.83-2.70 (m, 2H), 2.54 (br. s., 1H), 2.48-2.35 (m, 1H), 2.23-1.57 (m, 7H), 1.52-1.20 (m, 10H), 0.97 (d, J=6.8 Hz, 3H). m/z (ESI, +ve ion) 699.1 (M+H)⁺.

Example 359. (2S)-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [7,16,18,24]tetraen]-9'-yl)(methoxy)ethanoic acid

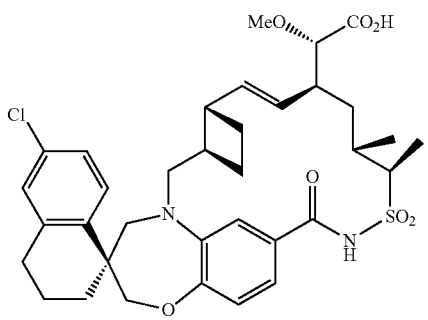 [SMILES: CO[C@H](C(=O)O)[C@@H]1/C=C/[C@@H]2CC[C@H]2CN2C[C@@]3(CCCc4cc(Cl)ccc43)COc3ccc(cc32)C(=O)NS(=O)(=O)[C@H](C)[C@@H](C)C1]

To a stirred solution of Ethyl(2S)-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[7,16,18,24]-tetraen]-9'-yl)(methoxy)ethanoate (3.0 mg, 4.3 μmol, Example 357) in a mixed solvent comprising MeOH (0.5 mL), THF (0.5 mL), and water (0.1 mL) was added lithium hydroxide monohydrate (0.45 mg, 11 μmol) at rt. The resulting mixture was stirred at 50° C. for 2 h and left stirred at ambient temperature over the weekend. The volatiles were removed, the residue was taken up in DMSO and subjected to preparative reverse-phase HPLC (Gemini™ Prep C₁₈ 5 μm column; Phenomenex, Torrance, CA; gradient elution of 50-95% acetonitrile in water, where both solvents contained 0.1% TFA, 30 min method) to give 0.3 mg of the title compound as a white solid. ¹H NMR (500 MHz, CD₂Cl₂) δ 7.99 (s, 1H), 7.71 (d, J=8.6 Hz, 1H), 7.16 (dd, J=2.3, 8.4 Hz, 1H), 7.09 (d, J=2.2 Hz, 1H), 7.02-6.87 (m, 3H), 6.00 (dd, J=4.5, 15.5 Hz, 1H), 5.28 (d, J=8.8 Hz, 1H), 4.19-4.09 (m, 2H), 4.09-4.02 (m, 1H), 3.83 (d, J=15.4 Hz, 1H), 3.69 (d, J=3.9 Hz, 1H), 3.61 (d, J=14.2 Hz, 1H), 3.47 (s, 3H), 3.18 (d, J=13.9 Hz, 1H), 3.07 (dd, J=8.2, 15.5 Hz, 1H), 2.82-2.68 (m, 2H), 2.58 (d, J=5.1 Hz, 2H), 2.21-1.33 (m, 15H), 0.99 (d, J=6.8 Hz, 3H). m/z (ESI, +ve ion) 671.0 (M+H)⁺.

Example 360. (2R)-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [7,16,18,24]tetraen]-9'-yl)(methoxy)ethanoic acid

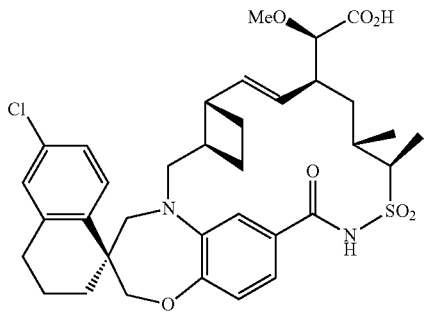 [SMILES: CO[C@@H](C(=O)O)[C@@H]1/C=C/[C@@H]2CC[C@H]2CN2C[C@@]3(CCCc4cc(Cl)ccc43)COc3ccc(cc32)C(=O)NS(=O)(=O)[C@H](C)[C@@H](C)C1]

The title compound (0.4 mg) was prepared as a white solid from Ethyl(2R)-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[7,16,18,24]tetraen]-9'-yl)(methoxy)ethanoate (Example 358) following the procedure described for Example 359. ¹H NMR (400 MHz, CD₂Cl₂) δ 8.00 (s, 1H), 7.71 (d, J=8.4 Hz, 1H), 7.16 (dd, J=2.3, 8.4 Hz, 1H), 7.09 (d, J=2.2 Hz, 1H), 7.02-6.89 (m, 3H), 6.01 (dd, J=4.8, 15.4 Hz, 1H), 5.26 (dd, J=8.0, 15.7 Hz, 1H), 4.21-4.08 (m, 2H), 4.03 (d, J=4.9 Hz, 1H), 3.83 (d, J=15.3 Hz, 1H), 3.68-3.56 (m, 2H), 3.43 (s, 3H), 3.19 (d, J=14.3 Hz, 1H), 3.08 (dd, J=8.0, 15.7 Hz, 1H), 2.85-2.69 (m, 2H), 2.63-2.47 (m, 2H), 2.24-1.29 (m, 15H), 0.99 (d, J=6.8 Hz, 3H). m/z (ESI, +ve ion) 671.0 (M+H)⁺.

Example 361. (2S)-2-(((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [7,16,18,24]tetraen]-9'-yl)-2-methoxy-N-methylethanamide or (2R)-2-(((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [7,16,18,24]tetraen]-9'-yl)-2-methoxy-N-methylethanamide Step 1: Sodium (2S)-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [7,16,18,24]tetraen]-9'-yl)(methoxy)ethanoate and sodium (2R)-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [7,16,18,24]tetraen]-9'-yl)(methoxy)ethanoate

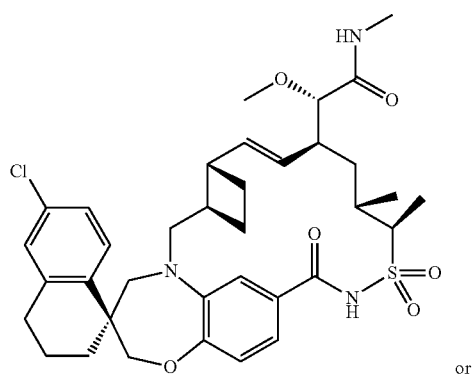

or

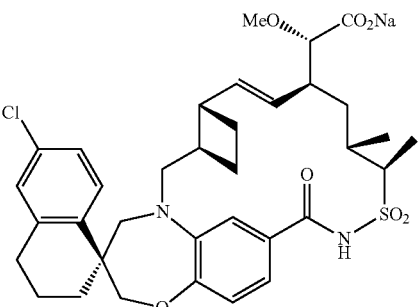

and

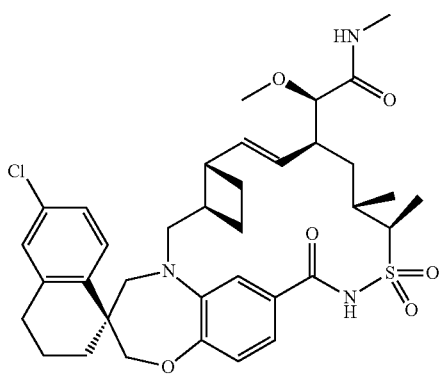

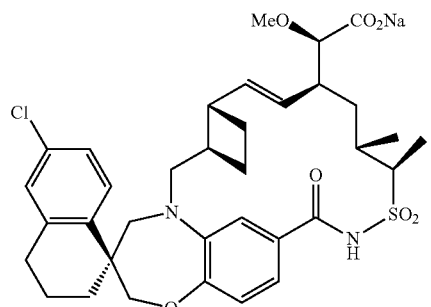

A mixture of ethyl(2S)-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]-tetraen]-9'-yl)(methoxy)ethanoate and ethyl(2R)-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]-tetraen]-9'-yl)(methoxy)ethanoate (54 mg, 0.080 mmol, Examples 357 and 358) and lithium hydroxide monohydrate (15 mg, 0.36 mmol) in a mixed solvent of MeOH (1 mL), THF (1 mL), and water (0.1 mL) was stirred at 50° C. for 20 min. The reaction appeared going rather slowly. More lithium hydroxide monohydrate was added followed by a bit more water. The mixture was stirred for another 40 min. The volatiles were removed, the residue was subjected to high vacuum before taken onto the next step.

Step 2: (2R)-2-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [7,16,18,24]tetraen]-9'-yl)-2-methoxy-N-methyl-ethanamide or (2S)-2-((1S,3'R,6'S,7'E,9'S,10'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$] pentacosa [7,16,18,24]tetraen]-9'-yl)-2-methoxy-N-methylethanamide To a stirred solution of a mixture of sodium (2S)-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)(methoxy)ethanoate and sodium (2R)-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)(methoxy)ethanoate (55 mg, 0.080 mmol) and hatu (91 mg, 0.24 mmol) in DMF (2 mL) was added methylamine, 2.0 M solution in THF (0.20 mL, 0.40 mmol) at ambient temperature followed by diisopropylethylamine (0.14 mL, 0.80 mmol). The resulting mixture was stirred at ambient temperature for 20 min. The volatiles were removed in vacuo and the residue was dissolved in DMSO/DMF and subjected to preparative reverse-phase HPLC (Gemini™ Prep C$_{18}$ 5 µm column; Phenomenex, Torrance, CA; gradient elution of 40-95% acetonitrile in water, where both solvents contained 0.1% TFA, 30 min method) to give 8.0 mg of the title compound as the second eluting fraction as a light yellow solid. $^1$H NMR (500 MHz, CD$_2$Cl$_2$) δ 7.99 (s, 1H), 7.71 (d, J=8.3 Hz, 1H), 7.16 (dd, J=2.4, 8.6 Hz, 1H), 7.09 (d, J=2.2 Hz, 1H), 7.02-6.95 (m, 2H), 6.94-6.89 (m, 1H), 6.64 (q, J=4.2 Hz, 1H), 5.92 (dd, J=5.0, 15.5 Hz, 1H), 5.27 (dd, J=7.7, 16.0 Hz, 1H), 4.19-4.06 (m, 2H), 4.04-3.95 (m, 1H), 3.82 (d, J=15.4 Hz, 1H), 3.62 (d, J=14.2 Hz, 1H), 3.49 (d, J=5.1 Hz, 1H), 3.36 (s, 3H), 3.18 (d, J=14.2 Hz, 1H), 3.08 (dd, J=8.1, 15.4 Hz, 1H), 2.82 (d, J=4.9 Hz, 3H), 2.79-2.72 (m, 2H), 2.63-2.39 (m, 2H), 2.13 (quin, J=8.9 Hz, 1H), 2.04-1.75 (m, 7H), 1.69-1.57 (m, 1H), 1.53-1.42 (m, 2H), 1.39-1.24 (m, 4H), 0.97 (d, J=7.1 Hz, 3H). m/z (ESI, +ve ion) 684.1 (M+H)$^+$.

Example 362. (2R)-2-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [7,16,18,24]tetraen]-9'-yl)-2-methoxy-N-methylethanamide and (2S)-2-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [7,16,18,24]tetraen]-9'-yl)-2-methoxy-N-methylethanamide

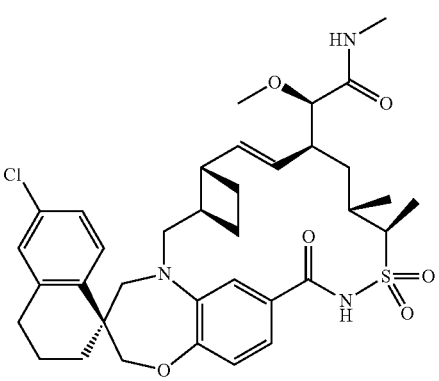

and

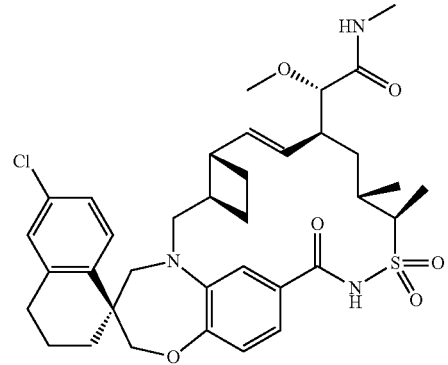

The first eluting fraction from the preparative reverse-phase HPLC purification in Example 361, Step 2 provided 5.0 mg of the title compound as a light yellow solid. It was a mixture of two epimers of a ratio of 44 to 56 (the first one eluting out of the reverse-phase HPLC column to the second one). $^1$H NMR (500 MHz, CD$_2$Cl$_2$) δ 8.01 (br. s., 1H), 7.71 (d, J=8.6 Hz, 1H), 7.16 (dd, J=2.3, 8.4 Hz, 1H), 7.09 (d, J=2.2 Hz, 1H), 7.03-6.85 (m, 3H), 6.61 (q, J=4.6 Hz, 0.56H) [from the second epimer coming out the reverse-phase HPLC column], 6.51 (br. s., 0.44H) [from the first epimer coming out of the reverse-phase HPLC column], 5.92 (dd, J=5.0, 15.5 Hz, 1H), 5.30-5.22 (m, 1H), 4.22-3.94 (m, 3H), 3.82 (d, J=15.4 Hz, 1H), 3.67-3.57 (m, 1H), 3.55-3.44 (m, 1H), 3.39 (s, 1.32H) [from the first epimer coming out of the reverse-phase HPLC column], 3.36 (s, 1.68H) [from the second epimer coming out of the reverse-phase HPLC column], 3.18 (d, J=14.2 Hz, 1H), 3.08 (dd, J=8.1, 15.2 Hz, 1H), 2.85-2.71 (m, 5H), 2.62-1.19 (m, 16H), 1.07-0.92 (m, 4H). m/z (ESI, +ve ion) 684.1 (M+H)$^+$.

Example 363. (2S)-2-((1S,3'R,6'S,9'R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-9'-yl)-2-methoxy-N-methylethanamide or (2R)-2-((1S,3'R,6'S,9'R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-9'-yl)-2-methoxy-N-methylethanamide

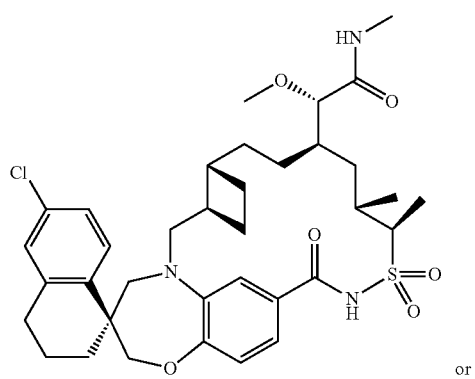

or

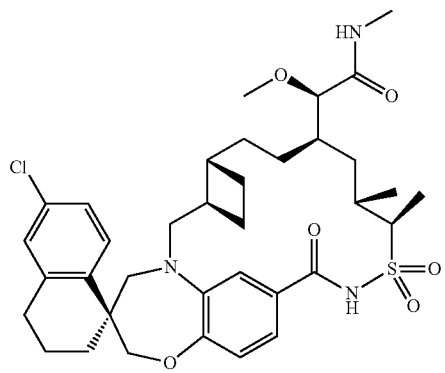

A vigorously stirred mixture of (2R)-2-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)-2-methoxy-N-methylethanamide or (2S)-2-((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)-2-methoxy-N-methylethanamide (not weighed, Example 361) and platinum (iv) oxide (in excess) in EtOAc (5 mL) was balloon-hydrogenated over a period of 2.5 h. The crude mixture was filtered and the filtrate was concentrated in vacuo. The residue was taken up in DMF/DMSO and subjected to preparative reverse-phase HPLC (Gemini Prep $C_{18}$ 5 μm column; Phenomenex, Torrance, CA; gradient elution of 50-95% acetonitrile in water, where both solvents contained 0.1% TFA, 30 min method) to give 2.0 mg of the title compound as a white solid. $^1$H NMR (500 MHz, CD$_2$Cl$_2$) δ 8.01 (s, 1H), 7.72 (d, J=8.6 Hz, 1H), 7.17 (dd, J=2.2, 8.6 Hz, 1H), 7.11-7.04 (m, 2H), 6.99-6.88 (m, 2H), 6.64 (d, J=4.9 Hz, 1H), 4.12 (q, J=12.0 Hz, 2H), 4.02-3.93 (m, 1H), 3.82-3.72 (m, 2H), 3.66 (d, J=14.4 Hz, 1H), 3.38 (s, 3H), 3.20 (d, J=14.2 Hz, 1H), 3.06-2.97 (m, 1H), 2.85 (d, J=4.9 Hz, 3H), 2.79-2.72 (m, 2H), 2.41-2.23 (m, 2H), 2.09-1.34 (m, 14H), 1.32-1.20 (m, 4H), 1.10-1.02 (m, 1H), 0.93 (d, J=6.8 Hz, 3H). m/z (ESI, +ve ion) 686.1 (M+H)$^+$.

Example 364. (1S,3'R,6'R,7'S,12'S)-6-chloro-7'-hydroxy-3,4-dihydro-2H,15'H-spiro[naphthalene-1,22'-[20]oxa[13]thia[1,14]diazapentacyclo[14.7.2.1$^{8,12}$.0$^{3,6}$.0$^{19,24}$]hexacosa[16,18,24]trien]-15'-one 13',13'-dioxide or (1S,3'R,6'R,7'S,12'R)-6-chloro-7'-hydroxy-3,4-dihydro-2H,15'H-spiro[naphthalene-1,22'-[20]oxa[13]thia[1,14]diazapentacyclo[14.7.2.1$^{8,12}$.0$^{3,6}$.0$^{19,24}$]hexacosa[16,18,24]trien]-15'-one 13',13'-dioxide

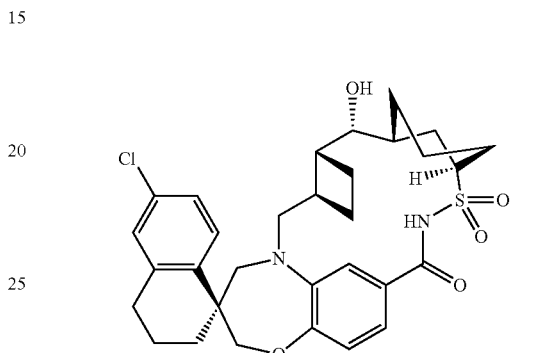

or

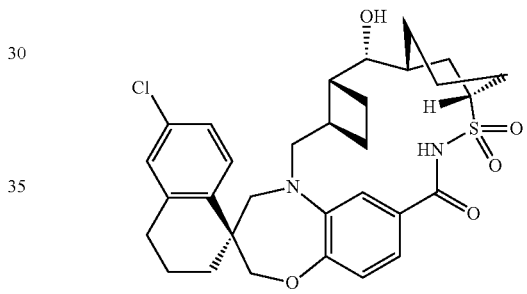

Step 1: (S)-methyl 6'-chloro-5-((((1R,2R)-2-((R)-((R)-cyclohex-2-en-1-yl)(hydroxy)methyl)cyclobutyl)methyl)-3',4',5-tetrahydro-2H,2'H-spiro[benzo[b][1,4]oxazepine-3,1'-naphthalene]-7-carboxylate

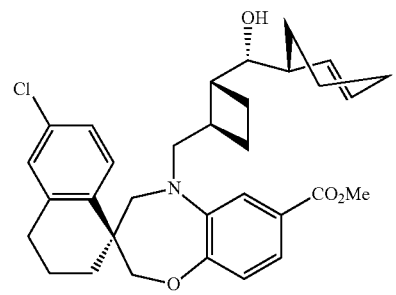

3-Bromocyclohexene (1.37 mL, 11.0 mmol) was added dropwise to a stirred suspension of indium (0.708 g, 6.17 mmol) in DMF (15 mL) under nitrogen at ambient temperature. The mixture was stirred at ambient temperature for 10 min before a solution of (S)-methyl 6'-chloro-5-(((1R,2R)-2-formylcyclobutyl)methyl)-3',4',5-tetrahydro-2H,2'H- spiro[benzo[b][1,4]oxazepine-3,1'-naphthalene]-7-carboxylate (2.00 g, 4.41 mmol, Intermediate AA11A, Step 20A) in DMF (10 mL) was added via a cannula. The resulting mixture was stirred at ambient temperature for 0.5 h. The mixture was poured into ice and saturated ammonium chloride aqueous solution and extracted with EtOAc (2×). The combined organics were washed with water and saturated ammonium chloride aqueous solution successively, dried over anhydrous sodium sulfate, and concentrated in vacuo. The residue was subjected to combi-flash column chromatography (EtOAc/Hexanes, 5 min at 0%, 5 min from 0 to 10% and 35 min at 10%, 80 g ISCO silica gel column) to give the title compound (0.328 g, 0.612 mmol, 14% yield) as a white solid. It was the last one among the total four isomeric products coming out of the silica gel column.

Step 2: (S)-methyl 5-(((1R,2R)-2-((R)-((tert-butyldimethylsilyl)oxy)((R)-cyclohex-2-en-1-yl)methyl)cyclobutyl)methyl)-6'-chloro-3',4,4',5-tetrahydro-2H,2'H-spiro[benzo[b][1,4]oxazepine-3,1'-naphthalene]-7-carboxylate Step 3: (S)-methyl 5-(((1R,2R)-2-((R)-((tert-butyldimethylsilyl)oxy)((1R,3S)-3-hydroxycyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((R)-((tert-butyldimethylsilyl)oxy)((1R,3R)-3-hydroxycyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylate

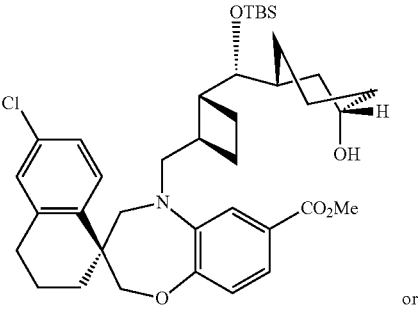

or

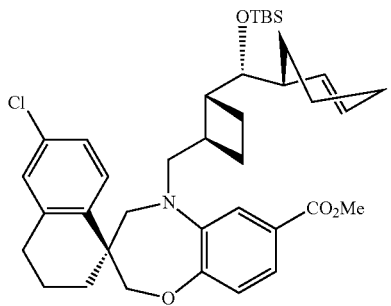

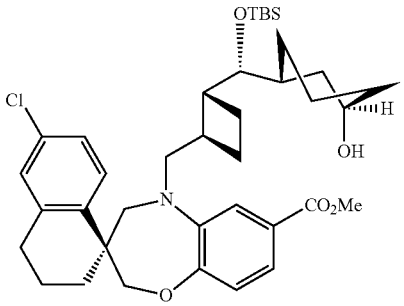

To a stirred solution of (S)-methyl 6'-chloro-5-(((1R,2R)-2-((S)-((R)-cyclohex-2-en-1-yl)(hydroxy)methyl)cyclobutyl)methyl)-3',4,4',5-tetrahydro-2H,2'H-spiro[benzo[b][1,4]oxazepine-3,1'-naphthalene]-7-carboxylate (0.303 g, 0.565 mmol) and 2,6-dimethylpyridine (0.138 mL, 1.19 mmol) in DCM (10 mL) cooled at −40° C. was added dropwise (1,1-dimethylethyl)dimethylsilyl trifluoromethanesulfonate (0.195 mL, 0.848 mmol) via a syringe. The resulting mixture was stirred at this temperature for 4 h. The crude mixture was loaded onto a silica gel precolumn and subjected to combi-flash column chromatography (EtOAc/Hexanes, 25 min from 0 to 15%, 40 g ISCO silica gel column) to give the title compound (0.320 g, 0.492 mmol, 87% yield) pure as a white solid.

To a stirred ice-cooled solution of (S)-methyl 5-(((1R,2R)-2-((S)-((tert-butyldimethylsilyl)oxy)((R)-cyclohex-2-en-1-yl)methyl)cyclobutyl)methyl)-6'-chloro-3',4,4',5-tetrahydro-2H,2'H-spiro[benzo[b][1,4]oxazepine-3,1'-naphthalene]-7-carboxylate (0.320 g, 0.492 mmol) in THF (5.0 mL) was added borane dimethyl sulfide complex, 1.0 M solution in THF (0.197 mL, 0.197 mmol) via a syringe under nitrogen. The resulting mixture was stirred at ambient temperature for 16 h. The mixture was cooled in ice-water bath before quenched with water (5.0 mL) followed by hydrogen peroxide, 30% aqueous (5.0 mL) and sodium hydroxide, 2 N aqueous (5.0 mL). The mixture was stirred at 0° C. for 5 min and at ambient temperature for 1.5 h. The mixture was diluted with water and extracted with EtOAc (3×). The combined organics were dried over anhydrous sodium sulfate and concentrated in vacuo to give a crude residue (0.33 g) as an off-white solid, directly taken onto the next step.

849

Step 4: (S)-methyl 5-(((1R,2R)-2-((R)-((tert-butyldimethylsilyl)oxy)((1R,3S)-3-((methylsulfonyl)oxy)cyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((R)-((tert-butyldimethylsilyl)oxy)((1R,3R)-3-((methylsulfonyl)oxy)cyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylate

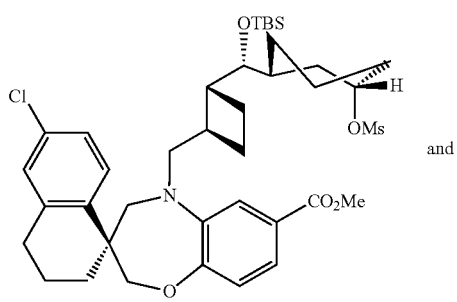

and

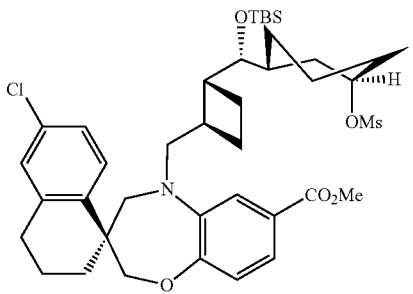

To a stirred ice-cooled solution of crude (S)-methyl 5-(((1R,2R)-2-((R)-((tert-butyldimethylsilyl)oxy)((1R,3S)-3-hydroxycyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((R)-((tert-butyldimethylsilyl)oxy)((1R,3R)-3-hydroxycyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylate (0.343 mL, 2.47 mmol) in DCM (8 mL) was slowly added methanesulfonyl chloride (0.078 mL, 0.99 mmol) through a syringe. The resulting mixture was stirred at 0° C. for 1.5 h. The crude mixture was directly subjected to combi-flash column chromatography (EtOAc/Hexanes, 30 min from 0 to 60%, 24 g ISCO silica gel column) to give a mixture of the title compounds (107 mg, 0.143 mmol, 29% yield) as a colorless film, taken onto the next step. Note that they were the major regio-isomeric product and the second regio-isomer peak coming out of the silica gel column.

850

Step 5: (S)-methyl 5-(((1R,2R)-2-((R)-((tert-butyldimethyl silyl)oxy)((1R,3S)-3-(pyrimidin-2-ylthio)cyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((R)-((tert-butyldimethyl silyl)oxy)((1R,3R)-3-(pyrimidin-2-ylthio)cyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylate

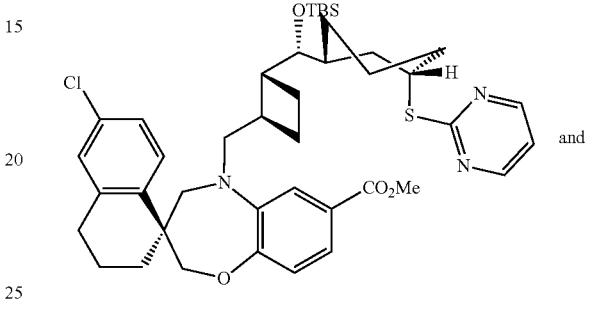

and

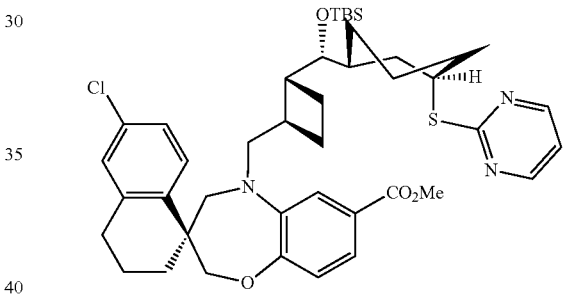

A mixture of 2-mercapto-pyrimidine (28 mg, 0.25 mmol) and potassium carbonate anhydrous (51 mg, 0.37 mmol) in DMF (3 mL) was stirred at rt for 10 min before a solution of (S)-methyl 5-(((1R,2R)-2-((R)-((tert-butyldimethylsilyl)oxy)((1R,3S)-3-((methylsulfonyl)oxy)cyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((R)-((tert-butyldimethylsilyl)oxy)((1R,3R)-3-((methylsulfonyl)oxy)cyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylate (110 mg, 0.147 mmol) in THF (4 mL) was added at ambient temperature. The resulting mixture was stirred at 75° C. in a preheated oil bath for 7 h. After cooled, the mixture was poured into ice and saturated sodium carbonate aqueous solution and extracted with DCM (2×). The combined organics were washed with the same aqueous solution (1×), dried over anhydrous sodium sulfate, and concentrated in vacuo.

The residue was subjected to combi-flash column chromatography (EtOAc/hexanes, 4 min at 0% and 30 min from 0 to 30%, 24 g ISCO silica gel column) to give a mixture of the title compounds (57 mg, 0.075 mmol, 51% yield) as a colorless film, not pure and directly taken onto the next step.

Step 6: (S)-methyl 5-(((1R,2R)-2-((R)-((tert-butyldimethylsilyl)oxy)((1R,3S)-3-(pyrimidin-2-ylsulfonyl)cyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((R)-((tert-butyldimethylsilyl)oxy)((1R,3R)-3-(pyrimidin-2-ylsulfonyl)cyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylate Step 7: (S)-5-(((1R,2R)-2-((R)-((tert-butyldimethylsilyl)oxy)((1R,3S)-3-sulfamoylcyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylic acid and (S)-5-(((1R,2R)-2-((R)-((tert-butyldimethylsilyl)oxy)((1R,3R)-3-sulfamoylcyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylic

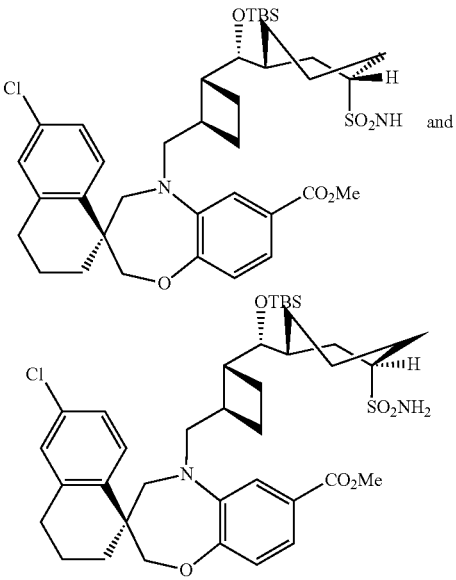

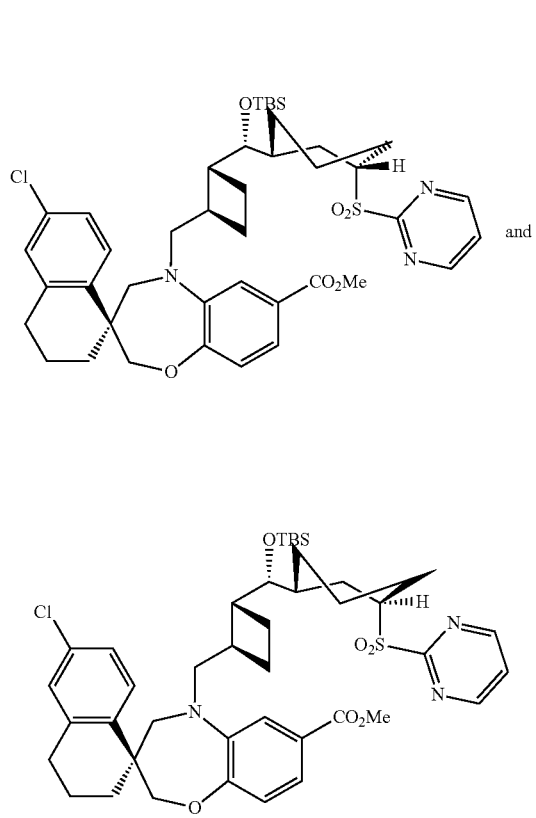

To a stirred ice-cooled solution of (S)-methyl 5-(((1R,2R)-2-((R)-((tert-butyldimethylsilyl)oxy)((1R,3S)-3-(pyrimidin-2-ylthio)cyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((R)-((tert-butyldimethylsilyl)oxy)((1R,3R)-3-(pyrimidin-2-ylthio)cyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylate (57 mg, 0.075 mmol) in DCM (4 mL) was added 3-chloroperbenzoic acid (37 mg, 0.15 mmol) in one portion as a solid. The resulting mixture was stirred at 0° C. for 10 min and at ambient temperature for 5 h. The crude reaction mixture was directly subjected to combi-flash column chromatography (EtOAc/Hexanes, 40 min from 0 to 70%, 24 g ISCO silica gel column) to give a mixture of the title compounds (30 mg, 0.038 mmol, 51% yield) as a colorless film.

The 1$^{st}$ step: To a stirred solution of (S)-methyl 5-(((1R,2R)-2-((R)-((tert-butyldimethylsilyl)oxy)((1R,3S)-3-(pyrimidin-2-ylsulfonyl)cyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((R)-((tert-butyldimethylsilyl)oxy)((1R,3R)-3-(pyrimidin-2-ylsulfonyl)cyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylate (30 mg, 0.038 mmol) in MeOH (3 mL) was added at rt sodium methoxide, 25 wt % solution in methanol (8.4 µl, 0.038 mmol) (in excess) via a syringe under nitrogen. The resulting mixture was stirred at ambient temperature for 45 min when LC-MS showed completion. The volatiles were removed in vacuo and the residue was subjected to high vacuum.

The 2$^{nd}$ step: To the above residue was added water (4 mL) followed by sodium acetate trihydrate (15.4 mg, 0.113 mmol) and amidoperoxymonosulfuric acid (14.2 mg, 0.113 mmol) at ambient temperature. The resulting clear solution was stirred at 55° C. for 1.5 h. The sulfinate intermediate was completely consumed. The reaction crude mixture was directly taken onto the next step.

The 3rd step: To the above reaction mixture was added lithium hydroxide monohydrate (16 mg, 0.038 mmol). The resulting mixture was stirred at 85° C. for 1 h. After cooled, the mixture was poured into ice-cold saturated ammonium chloride aqueous solution with some 2 N aqueous HCl added, and extracted with 25% i-PrOH/DCM (4×). The combined organics were dried over anhydrous sodium sulfate and concentrated in vacuo. The residue was subjected to combi-flash column chromatography ((10% MeOH/DCM with 0.3% AcOH)/DCM), 35 min from 0 to 70%, 12 g ISCO silica gel column) to give 15 mg of a mixture of the title compounds as a colorless film, which was directly taken onto the next step.

Step 8: (1S,3'R,6'R,7'S,12'S)-6-chloro-7'-(tert-butyldimethylsilyl)oxy-3,4-dihydro-2H,15'H-spiro [naphthalene-1,22'-[20]oxa[13]thia[1,14]diazapentacyclo[14.7.2.1$^{8,12}$.0$^{3,6}$.0$^{19,24}$]hexacosa[16,18,24] trien]-15'-one 13',13'-dioxide and (1S,3'R,6'R,7'S, 12'R)-6-chloro-7'-(tert-butyldimethylsilyl)oxy-3,4-dihydro-2H,15'H-spiro[naphthalene-1,22'-[20]oxa [13]thia[1,14]diazapentacyclo[14.7.2.1$^{8,12}$.0$^{3,6}$. 0$^{19,24}$]hexacosa[16,18,24]trien]-15'-one 13',13'-dioxide

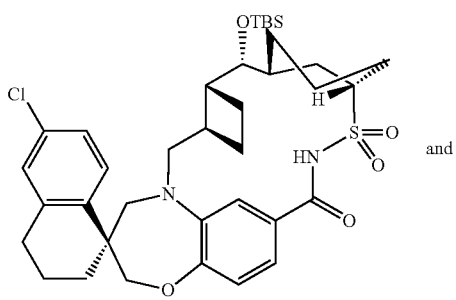

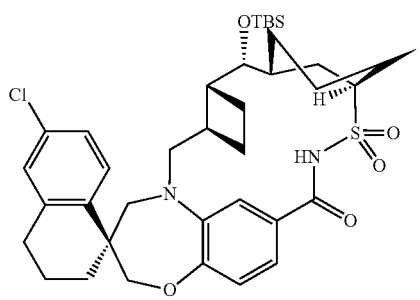

and

To a stirred ice-cooled solution of (S)-5-(((1R,2R)-2-((R)-((tert-butyldimethylsilyl)oxy)((1R,3S)-3-sulfamoylcyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylic acid and (S)-5-(((1R,2R)-2-((R)-((tert-butyldimethylsilyl)oxy)((1R,3R)-3-sulfamoylcyclohexyl)methyl)cyclobutyl)methyl)-6'-chloro-3',4,4',5-tetrahydro-2H,2'H-spiro[benzo[b][1,4]oxazepine-3,1'-naphthalene]-7-carboxylic acid (15 mg, 0.020 mmol) and N,N-dimethylpyridin-4-amine (5.5 mg, 0.045 mmol) in DCM (11 mL) was added 1-(3-dimethylaminopropyl)-3-ethylcarbodiimide hydrochloride (9.8 mg, 0.051 mmol) in one portion. The resulting mixture was stirred at ambient temperature for 5 h. Then the reaction solution was concentrated under reduced pressure and directly loaded onto a silica gel precolumn and subjected to combi-flash column chromatography (((10% MeOH with 0.35% AcOH)/DCM)/DCM, 30 min from 0 to 60%, 12 g silica gel) to give 12 mg of a mixture of the title compounds (12 mg, 0.017 mmol, 84% yield) as a colorless film.

Step 9: (1S,3'R,6'R,7'S,12'R)-6-chloro-7'-hydroxy-3, 4-dihydro-2H,15'H-spiro[naphthalene-1,22'-[20]oxa [13]thia[1,14]diazapentacyclo[14.7.2.1$^{8,12}$.0$^{3,6}$. 0$^{19,24}$]hexacosa[16,18,24]trien]-15'-one 13',13'-dioxide or (1S,3'R,6'R,7'S,12'S)-6-chloro-7'-hydroxy-3, 4-dihydro-2H,15'H-spiro[naphthalene-1,22'-[20]oxa [13]thia[1,14]diazapentacyclo[14.7.2.1$^{8,12}$.0$^{3,6}$. 0$^{19,24}$]hexacosa[16,18,24]trien]-15'-one 13',13'-dioxide To a stirred solution of (1S,3'R,6'R,7'S,12'S)-6-chloro-7'-(tert-butyldimethylsilyl)oxy-3,4-dihydro-2H,15'H-spiro [naphthalene-1,22'-[20]oxa[13]thia[1,14]diazapentacyclo [14.7.2.1$^{8,12}$.0$^{3,6}$.0$^{19,24}$]hexacosa[16,18,24]trien]-15'-one 13',13'-dioxide and (1S,3'R,6'R,7'S,12'R)-6-chloro-7'-(tert-butyldimethylsilyl)oxy-3,4-dihydro-2H,15'H-spiro[naphthalene-1,22'-[20]oxa[13]thia[1,14]diazapentacyclo [14.7.2.1$^{8,12}$.0$^{3,6}$.0$^{19,24}$]hexacosa[16,18,24]trien]-15'-one 13',13'-dioxide (12 mg, 0.017 mmol) in THF (2.5 mL) was added tetrabutylammonium fluoride, 1.0 M in tetrahydrofuran (0.17 mL, 0.17 mmol) at ambient temperature. The resulting mixture was stirred at ambient temperature for 17 h. Both LC-MS and HPLC showed still some sm was remaining. More tetrabutylammonium fluoride, 1.0 M in tetrahydrofuran solution (1.2 mL) was added and the mixture was stirred at ambient temperature for 6 h. The reaction mixture was concentrated under reduced pressure and the residue was taken up in DMSO and subjected to preparative reverse-phase HPLC (Gemini™ Prep C$_{18}$ 5 μm column; Phenomenex, Torrance, CA; gradient elution of 55-95% acetonitrile in water, where both solvents contained 0.1% TFA, 30 min method) to give 4.5 mg of the title compound as the first eluting fraction as a white solid. It was the major epimeric product. $^1$H NMR (400 MHz, CDCl$_3$) δ 8.67 (s, 1H), 7.72 (d, J=8.4 Hz, 1H), 7.20 (dd, J=2.2, 8.4 Hz, 1H), 7.15-7.07 (m, 2H), 7.00-6.91 (m, 2H), 4.23-4.07 (m, 2H), 4.00 (d, J=13.3 Hz, 1H), 3.74 (d, J=14.5 Hz, 1H), 3.58 (d, J=5.1 Hz, 1H), 3.37 (d, J=14.5 Hz, 1H), 3.29-3.12 (m, 2H), 2.88-2.71 (m, 2H), 2.53 (br. s., 1H), 2.39 (d, J=11.9 Hz, 1H), 2.32-2.17 (m, 2H), 2.15-1.32 (m, 16H). m/z (ESI, +ve ion) 585.2 (M+H)$^+$.

Example 365. (1S,3'R,6'R,7'S,12'S)-6-chloro-7'-hydroxy-3,4-dihydro-2H,15'H-spiro[naphthalene-1, 22'-[20]oxa[13]thia[1,14]diazapentacyclo[14.7. 2.1$^{8,12}$.0$^{3,6}$.0$^{19,24}$]hexacosa[16,18,24]trien]-15'-one 13',13'-dioxide and (1S,3'R,6'R,7'S,12'R)-6-chloro-7'-hydroxy-3,4-dihydro-2H,15'H-spiro[naphthalene-1,22'-[20]oxa[13]thia[1,14]diazapentacyclo[14.7. 2.1$^{8,12}$.0$^{3,6}$.0$^{19,24}$]hexacosa[16,18,24]trien]-15'-one 13',13'-dioxide

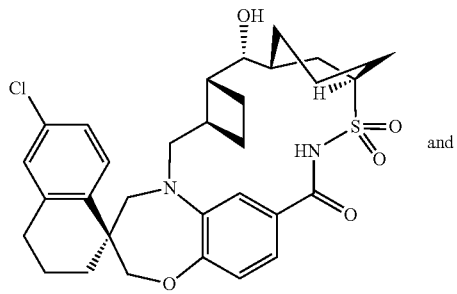

and

855

-continued

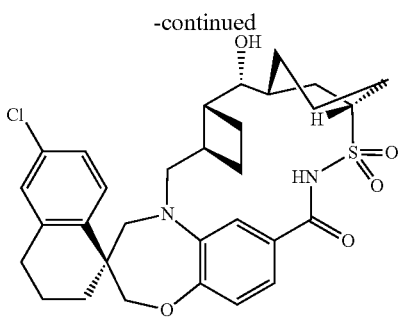

Further elution from the preparative reverse-phase HPLC purification in Example 364, Step 9 provided the title compound (1.2 mg) as the second eluting fraction as a white solid, which was an 11-to-9 mixture of the two epimeric products. $^1$H NMR (500 MHz, CDCl$_3$) δ 8.71 (br. s., 0.45H) [from the first epimer coming out of the reverse-phase HPLC column], 8.24 (br. s., 0.55H) [from the second epimer coming out of the reverse-phase HPLC column], 7.71 (d, J=8.6 Hz, 1H), 7.23-7.07 (m, 3H), 7.03-6.89 (m, 2H), 4.19-4.03 (m, 2H), 4.00-3.30 (m, 4H), 3.27-3.10 (m, 2H), 2.91-2.69 (m, 2H), 2.61-1.01 (m, 22H). m/z (ESI, +ve ion) 585.2 (M+H)$^+$.

Example 366. (1S,3'R,6'R,7'S,8'R,12'S)-6-chloro-7'-methoxy-3,4-dihydro-2H,15'H-spiro[naphthalene-1, 22'-[20]oxa[13]thia[1,14]diazapentacyclo[14.7. 2.1$^{8,12}$.0$^{3,6}$.0$^{19,24}$]hexacosa[16,18,24]trien]-15'-one 13',13'-dioxide or (1S,3'R,6'R,7'S,8'R,12'R)-6-chloro-7'-methoxy-3,4-dihydro-2H,15'H-spiro[naphthalene-[20]oxa[13]thia[1,14]diazapentacyclo [14.7. 2.1$^{8,12}$.0$^{3,6}$.0$^{19,24}$]hexacosa[16,18,24]trien]-15'-one 13',13'-dioxide or (1S,3'R,6'R,7'R,8'S,12'R)-6-chloro-7'-methoxy-3,4-dihydro-2H,15'H-spiro[naphthalene-1,22'-[20]oxa[13]thia[1,14]diazapentacyclo [14.7.2.1$^{8,12}$.0$^{3,6}$.0$^{19,24}$]hexacosa[16,18,24]trien]-15'-one 13',13'-dioxide or (1S,3'R,6'R,7'R,8'S,12'S)-6-chloro-7'-methoxy-3,4-dihydro-2H,15'H-spiro [naphthalene-1,22'-[20]oxa[13]thia[1,14] diazapentacyclo [14.7.2.1$^{8,12}$.0$^{3,6}$.0$^{19,24}$]hexacosa [16,18,24]trien]-15'-one 13',13'-dioxide or (1S,3'R, 6'R,7'S,8'S,12'R)-6-chloro-7'-methoxy-3,4-dihydro-2H,15'H-spiro[naphthalene-1,22'-[20]oxa[13]thia[1, 14]diazapentacyclo [14.7.2.1$^{8,12}$.0$^{3,6}$.0$^{19,24}$]hexacosa [16,18,24]trien]-15'-one 13',13'-dioxide or (1S,3'R, 6'R,7'S,8'S,12'S)-6-chloro-7'-methoxy-3,4-dihydro-2H,15'H-spiro[naphthalene-1,22'-[20]oxa[13]thia[1, 14]diazapentacyclo [14.7.2.1$^{8,12}$.0$^{3,6}$.0$^{19,24}$]hexacosa [16,18,24]trien]-15'-one 13',13'-dioxide

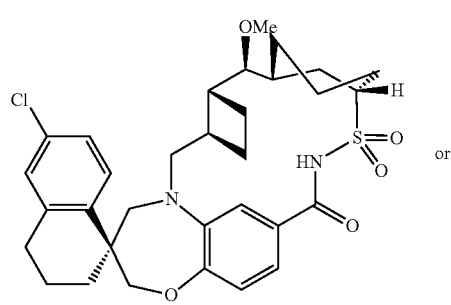 or

856

-continued

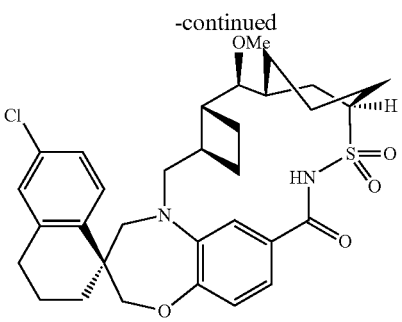 or

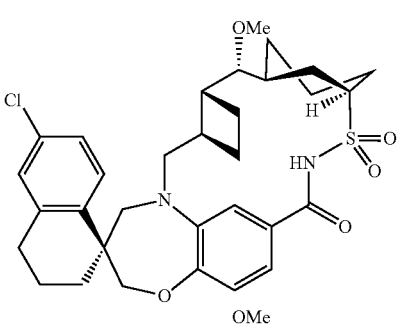 or

 or

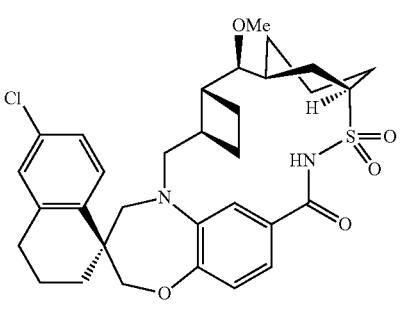 or

857

Step 1: (S)-methyl 6'-chloro-5-(((1R,2R)-2-((S)-((R)-cyclohex-2-en-1-yl)(hydroxy)methyl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((R)-((S)-cyclohex-2-en-1-yl)(hydroxy)methyl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((S)-((S)-cyclohex-2-en-1-yl)(hydroxy)methyl)cyclobutyl)methyl)-3',4,4',5-tetrahydro-2H,2'H-spiro[benzo[b][1,4]oxazepine-3,1'-naphthalene]-7-carboxylate

858

Step 2: (S)-methyl 6'-chloro-5-(((1R,2R)-2-((S)-((R)-cyclohex-2-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((R)-((S)-cyclohex-2-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((S)-((S)-cyclohex-2-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate

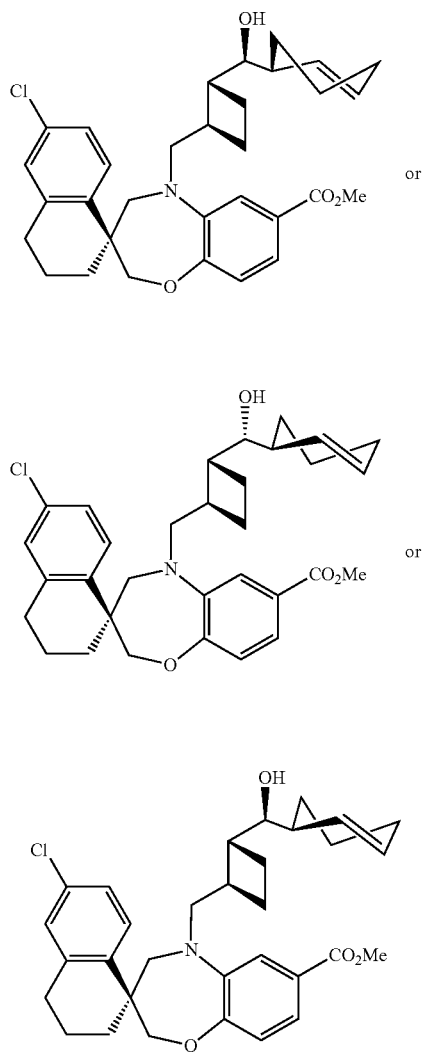

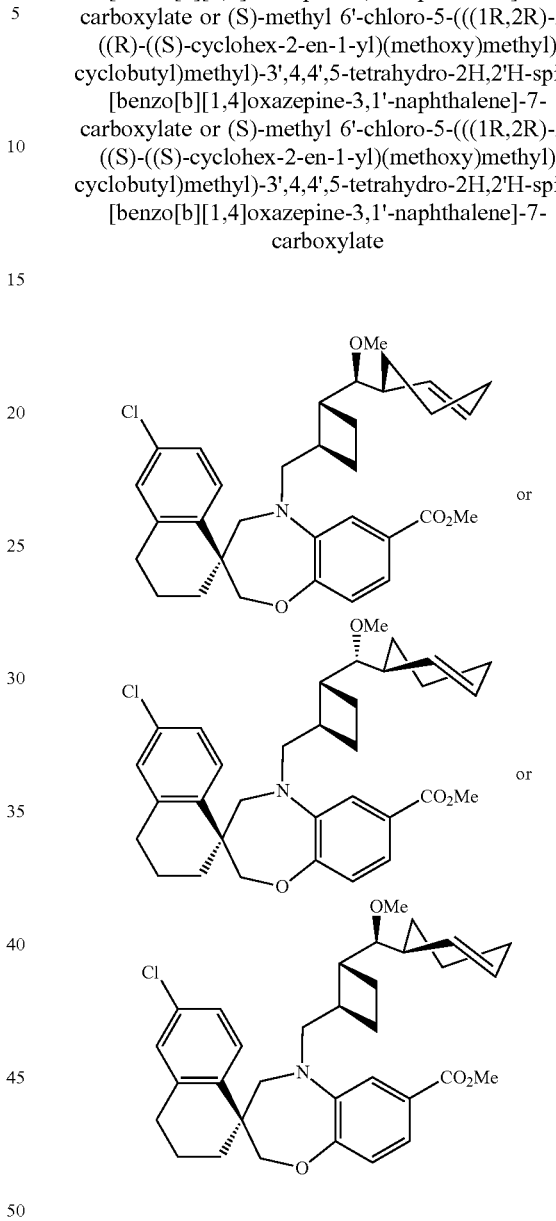

The title compound (0.38 g as a white solid) was synthesized and purified in Step 1 of Examples 364. It was the third isomeric product coming out of the silica gel column described therein.

To a stirred ice-cooled solution of (S)-methyl 6'-chloro-5-(((1R,2R)-2-((S)-((R)-cyclohex-2-en-1-yl)(hydroxy)methyl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((R)-((S)-cyclohex-2-en-1-yl)(hydroxy)methyl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((S)-((S)-cyclohex-2-en-1-yl)(hydroxy)methyl)cyclobutyl)methyl)-3',4,4',5-tetrahydro-2H,2'H-spiro[benzo[b][1,4]oxazepine-3,1'-naphthalene]-7-carboxylate (380 mg, 0.709 mmol) in THF (30 mL) was added sodium hydride, 60% dispersion in mineral oil (43 mg, 1.06 mmol). The resulting mixture was stirred at 0° C. for 10 min and at ambient temperature for 30 min before iodomethane (0.053 mL, 0.85 mmol) was added. The resulting mixture was stirred at 60° C. overnight. Essentially no reaction occurred. After cooled to rt, more sodium hydride (not weighed) was added. About 10 min later, more methyl iodide (not weighed) was added followed by more anhydrous DMF (20 mL). The mixture was heated up to 90° C. for 3.5 h. The reaction went to clean completion. The mixture was cooled in an ice-water bath and carefully quenched with methanol. The resulting mixture was poured into ice water and extracted with DCM (3×). The combined organics were washed with water (1×) followed by brine (1×), dried over anhydrous sodium sulfate, and concentrated in vacuo. The crude mixture was loaded onto a silica gel precolumn and subjected to combi-flash column chromatography (EtOAc/Hexanes, 5 min at 0% and 3 min from 0 to 30%, 40 g ISCO silica gel column) to give the title compound (352 mg, 0.640 mmol, 90% yield) as a colorless film.

Step 3: {(S)-methyl 6'-chloro-5-(((1R,2R)-2-((S)-((1R,3S)-3-hydroxycyclohexyl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-((1R,3R)-3-hydroxycyclohexyl)(methoxy)methyl)cyclobutyl)methyl-3',4,4',5-tetrahydro-2H,2'H-spiro[benzo[b][1,4]oxazepine-3,1'-naphthalene]-7-carboxylate} or {(S)-methyl 6'-chloro-5-(((1R,2R)-2-((R)-((1S,3R)-3-hydroxycyclohexyl)(methoxy)methyl)cyclobutyl)methyl-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-((1S,3S)-3-hydroxycyclohexyl)(methoxy)methyl)cyclobutyl)methyl-3',4,4',5-tetrahydro-2H,2'H-spiro[benzo[b][1,4]oxazepine-3,1'-naphthalene]-7-carboxylate} or {(S)-methyl 6'-chloro-S-(((1R,2R)-2-((S)-((1S,3R)-3-hydroxycyclohexyl)(methoxy)methyl)cyclobutyl)methyl-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-((1S,3S)-3-hydroxycyclohexyl)(methoxy)methyl)cyclobutyl)methyl)-3',4,4',5-tetrahydro-2H,2'H-spiro[benzo[b][1,4]oxazepine-3,1'-naphthalene]-7-carboxylate}

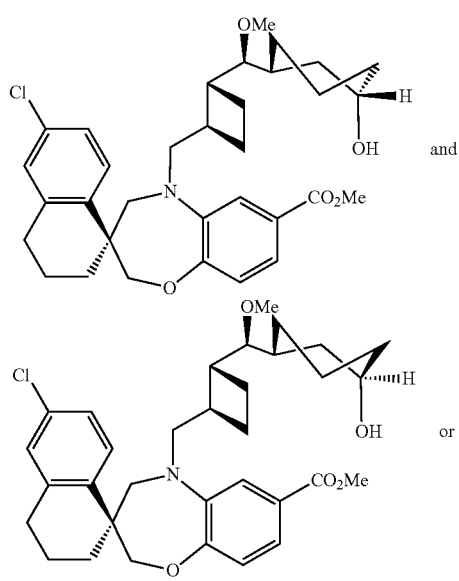
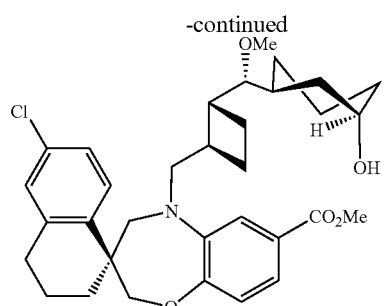
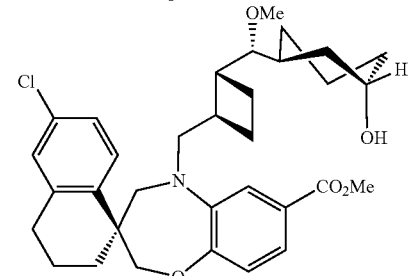
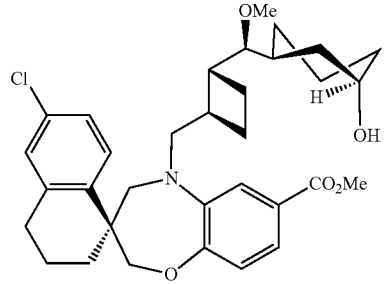
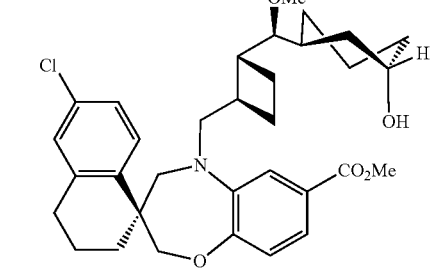

To a stirred ice-cooled solution of (S)-methyl 6'-chloro-5-(((1R,2R)-2-((S)-((R)-cyclohex-2-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((R)-((S)-cyclohex-2-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((S)-((S)-cyclohex-2-en-1-yl)(methoxy)methyl)cyclobutyl)methyl)-3',4,4',5-tetrahydro-2H,2'H-spiro[benzo[b][1,4]oxazepine-3,1'-naphthalene]-7-carboxylate (300 mg, 0.545 mmol) in THF (5.0 mL) was added borane dimethyl sulfide complex, 1.0 M solution in THF (0.218 mL, 0.218 mmol) via a syringe under nitrogen. The resulting mixture was stirred at ambient temperature for 13.5 h. TLC showed some sm was still remaining. The mixture was cooled in ice bath and more borane dimethyl sulfide complex, 1.0 M solution in THF (0.218 mL, 0.218 mmol) was added. The resulting mixture was stirred at ambient temperature for 1 h. TLC showed complete consumption of the sm. The mixture was cooled in an ice-water bath before quenched with water (5.0 mL) followed by sodium hydroxide, 2 N aqueous (5.0 mL) and hydrogen peroxide, 30% aqueous (5.0 mL). The mixture was stirred at 0° C. for 5 min and at ambient temperature for 1 h. The mixture was diluted with water and extracted with EtOAc (3×). The combined organics were dried over anhydrous sodium sulfate and concentrated in vacuo to give 0.29 g of a crude mixture of the title compounds as a white solid, directly taken onto the next step.

Step 4: {(S)-methyl 6'-chloro-5-(((1R,2R)-2-((S)-methoxy((1R,3S)-3-((methylsulfonyl)oxy)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-S-(((1R,2R)-2-((S)-methoxy((1R,3R)-3-((methylsulfonyl)oxy)cyclohexyl)methyl)cyclobutyl)methyl)-3',4,4',5-tetrahydro-2H,2'H-spiro[benzo[b][1,4]oxazepine-3,1'-naphthalene]-7-carboxylate} or {(S)-methyl 6'-chloro-5-(((1R,2R)-2-((R)-methoxy((1S,3R)-3-((methylsulfonyl)oxy)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy((1S,3S)-3-((methylsulfonyl)oxy)cyclohexyl)methyl)cyclobutyl)methyl)-3',4,4',5-tetrahydro-2H,2'H-spiro[benzo[b][1,4]oxazepine-3,1'-naphthalene]-7-carboxylate or {(S)-methyl 6'-chloro-5-(((1R,2R)-2-((S)-methoxy((1S,3R)-3-((methylsulfonyl)oxy)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((1S,3S)-3-((methylsulfonyl)oxy)cyclohexyl)methyl)cyclobutyl)methyl)-3',4,4',5-tetrahydro-2H,2'H-spiro[benzo[b][1,4]oxazepine-3,1'-naphthalene]-7-carboxylate}

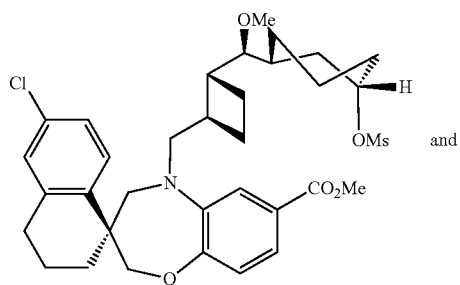

and

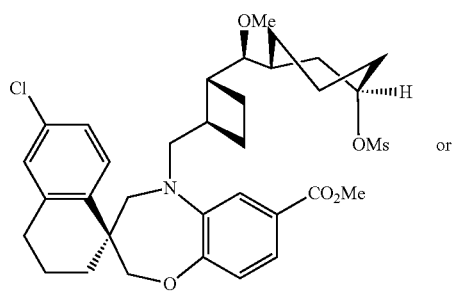

or

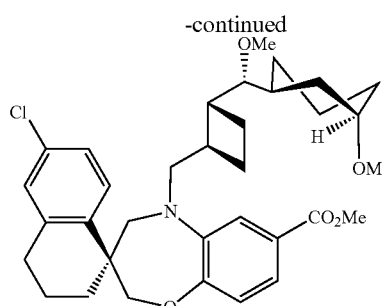

and

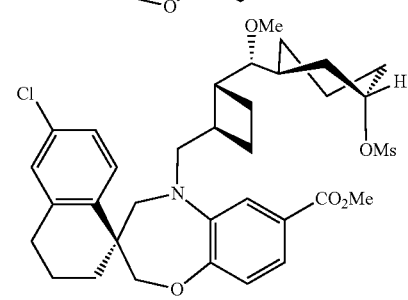

or

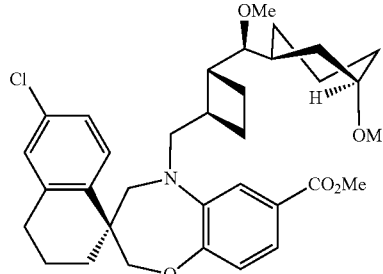

and

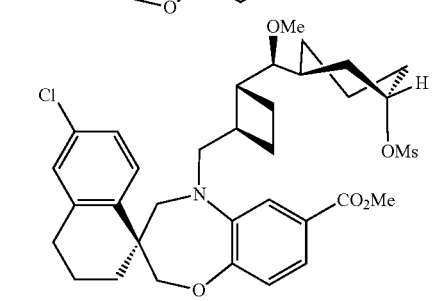

To a stirred ice-cooled solution of a mixture of {(S)-methyl 6'-chloro-5-(((1R,2R)-2-((S)-((1R,3S)-3-hydroxycyclohexyl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-((1R,3R)-3-hydroxycyclohexyl)(methoxy)methyl)cyclobutyl)methyl)-3',4,4',5-tetrahydro-2H,2'H-spiro[benzo[b][1,4]oxazepine-3,1'-naphthalene]-7-carboxylate} or {(S)-methyl 6'-chloro-5-(((1R,2R)-2-((R)-((1S,3R)-3-hydroxycyclohexyl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-((1S,3S)-3-hydroxycyclohexyl)(methoxy)methyl)cyclobutyl)methyl)-3',4,4',5-tetrahydro-2H,2'H-spiro[benzo[b][1,4]oxazepine-3,1'-naphthalene]-7-carboxylate} or {(S)-methyl 6'-chloro-5-(((1R,2R)-2-((S)-((1S,3R)-3-hydroxycyclohexyl)(methoxy)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-((1S,3S)-3-hydroxycyclohexyl)(methoxy)methyl)

cyclobutyl)methyl)-3',4,4',5-tetrahydro-2H,2'H-spiro[benzo[b][1,4]oxazepine-3,1'-naphthalene]-7-carboxylate} (290 mg, 0.510 mmol) and triethylamine (0.355 mL, 2.55 mmol) in DCM (15 mL) was slowly added methanesulfonyl chloride (0.081 mL, 1.02 mmol). The resulting mixture was stirred at 0° C. for 2 h. The crude mixture was directly subjected to combi-flash column chromatography (EtOAc/Hexanes, 5 min at 0% and 40 min from 0 to 70%, 40 g ISCO silica gel column) to give a mixture of the title compounds (121 mg, 0.187 mmol, 37% yield) as a colorless film. It was the second one of two regio-isomeric products coming out of the silica gel column.

Step 5: {(S)-methyl 6'-chloro-5-(((1R,2R)-2-((S)-methoxy((1R,3S)-3-(pyrimidin-2-ylthio)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((1R,3R)-3-(pyrimidin-2-ylthio)cyclohexyl)methyl)cyclobutyl)methyl)-3',4,4',5-tetrahydro-2H,2'H-spiro[benzo[b][1,4]oxazepine-3,1'-naphthalene]-7-carboxylate} or {(S)-methyl 6'-chloro-5-(((1R,2R)-2-((R)-methoxy((1S,3R)-3-(pyrimidin-2-ylthio)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy((1S,3S)-3-(pyrimidin-2-ylthio)cyclohexyl)methyl)cyclobutyl)methyl)-3',4,4',5-tetrahydro-2H,2'H-spiro[benzo[b][1,4]oxazepine-3,1'-naphthalene]-7-carboxylate} or {(S)-methyl 6'-chloro-5-(((1R,2R)-2-((S)-methoxy((1S,3R)-3-(pyrimidin-2-ylthio)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((1S,3S)-3-(pyrimidin-2-ylthio)cyclohexyl)methyl)cyclobutyl)methyl)-3',4,4',5-tetrahydro-2H,2'H-spiro[benzo[b][1,4]oxazepine-3,1'-naphthalene]-7-carboxylate}

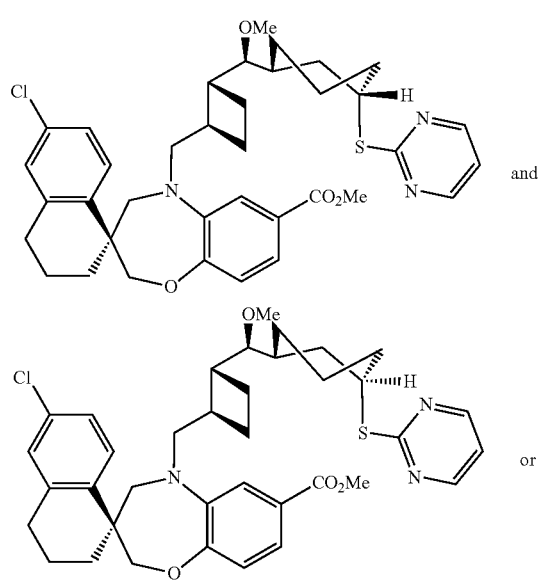

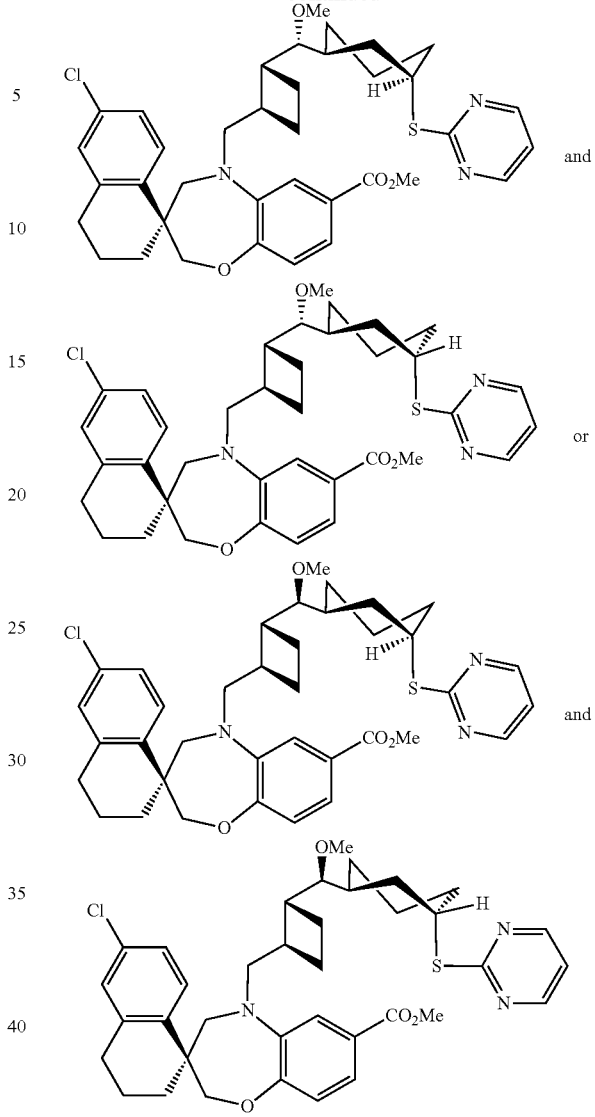

A mixture of 2-mercapto-pyrimidine (53 mg, 0.468 mmol) and potassium carbonate anhydrous (91 mg, 0.66 mmol) in DMF (3 mL) was stirred at ambient temperature under nitrogen for 10 min before a solution of {(S)-methyl 6'-chloro-5-(((1R,2R)-2-((S)-methoxy ((1R,3S)-3-((methylsulfonyl)oxy)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((1R,3R)-3-((methyl sulfonyl)oxy)cyclohexyl)methyl)cyclobutyl)methyl)-3',4,4',5-tetrahydro-2H,2'H-spiro[benzo[b][1,4]oxazepine-3,1'-naphthalene]-7-carboxylate} or {(S)-methyl 6'-chloro-5-(((1R,2R)-2-((R)-methoxy ((1S,3R)-3-((methylsulfonyl)oxy)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy((1S,3S)-3-((methylsulfonyl)oxy)cyclohexyl)methyl)cyclobutyl)methyl)-3',4,4',5-tetrahydro-2H,2'H-spiro[benzo[b][1,4]oxazepine-3,1'-naphthalene]-7-carboxylate} or {(S)-methyl 6'-chloro-5-(((1R,2R)-2-((S)-methoxy((1S,3R)-3-((methylsulfonyl)oxy)cyclohexyl)methyl)cyclobutyl)methyl)-3',4,4',5-tetrahydro-2H,2'H- spiro[benzo[b][1,4]oxazepine-3,1'-naphthalene]-7-carboxylate and (S)-methyl 6'-chloro-5-(((1R,2R)-2-((S)-methoxy((1S,3S)-3-((methylsulfonyl)oxy)cyclohexyl)methyl)cyclobutyl)methyl)-3',4,4',5-tetrahydro-2H,2'H-spiro[benzo[b][1,4]oxazepine-3,1'-naphthalene]-7-carboxylate} (121 mg, 0.187 mmol) in THF (4 mL) was added. The resulting mixture was stirred at 75° C. for 18 h. After the reaction mixture was concentrated under reduced pressure, the residue was directly subjected to combi-flash column chromatography (EtOAc/hexanes, 6 min at 0% and 35 min from 0 to 70%, 40 g ISCO silica gel column) to give a mixture of the title compounds (50 mg, 0.075 mmol, 40% yield) as a colorless film.

Step 6: {(S)-methyl 6'-chloro-5-(((1R,2R)-2-((S)-methoxy((1R,3S)-3-(pyrimidin-2-ylsulfonyl)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((1R,3R)-3-(pyrimidin-2-ylsulfonyl)cyclohexyl)methyl)cyclobutyl)methyl)-3',4,4',5-tetrahydro-2H,2'H-spiro[benzo[b][1,4]oxazepine-3,1'-naphthalene]-7-carboxylate} or {(S)-methyl 6'-chloro-5-(((1R,2R)-2-((R)-methoxy((1S,3R)-3-(pyrimidin-2-ylsulfonyl)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy((1S,3S)-3-(pyrimidin-2-ylsulfonyl)cyclohexyl)methyl)cyclobutyl)methyl)-3',4,4',5-tetrahydro-2H,2'H-spiro[benzo[b][1,4]oxazepine-3,1'-naphthalene]-7-carboxylate} or {(S)-methyl 6'-chloro-5-(((1R,2R)-2-((S)-methoxy((1S,3R)-3-(pyrimidin-2-ylsulfonyl)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-S-(((1R,2R)-2-((S)-methoxy((1S,3S)-3-(pyrimidin-2-ylsulfonyl)cyclohexyl)methyl)cyclobutyl)methyl)-3',4,4',5-tetrahydro-2H,2'H-spiro[benzo[b][1,4]oxazepine-3,1'-naphthalene]-7-carboxylate}

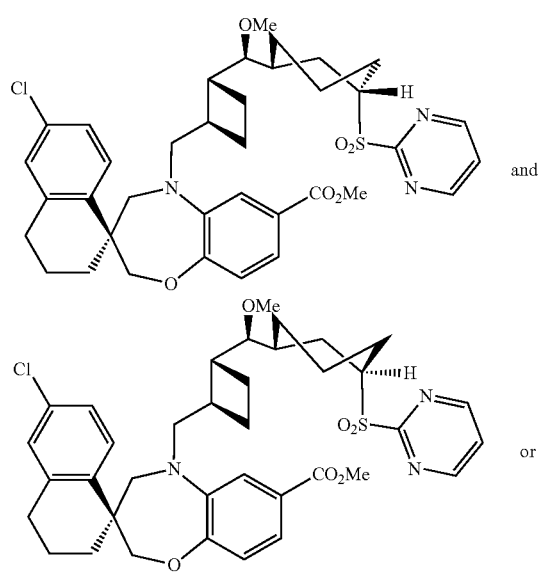

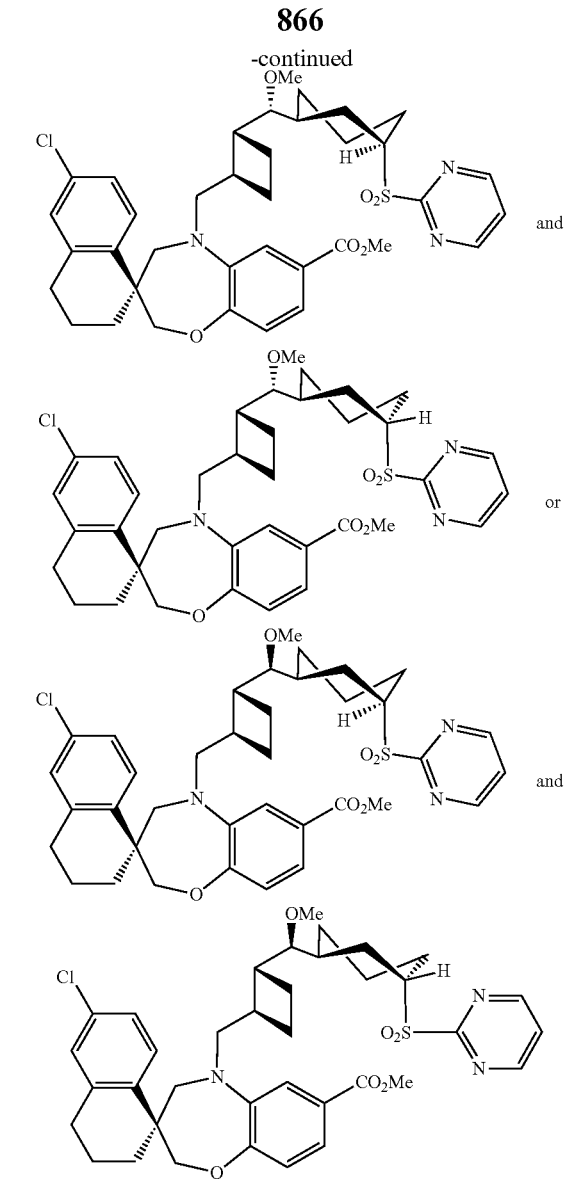

To a stirred ice-cooled solution of {(S)-methyl 6'-chloro-5-(((1R,2R)-2-((S)-methoxy((1R,3S)-3-(pyrimidin-2-ylthio)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((1R,3R)-3-(pyrimidin-2-ylthio)cyclohexyl)methyl)cyclobutyl)methyl)-3',4,4',5-tetrahydro-2H,2'H-spiro[benzo[b][1,4]oxazepine-3,1'-naphthalene]-7-carboxylate} or {(S)-methyl 6'-chloro-5-(((1R,2R)-2-((R)-methoxy((1S,3R)-3-(pyrimidin-2-ylthio)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy((1S,3S)-3-(pyrimidin-2-ylthio)cyclohexyl)methyl)cyclobutyl)methyl)-3',4,4',5-tetrahydro-2H,2'H-spiro[benzo[b][1,4]oxazepine-3,1'-naphthalene]-7-carboxylate} or {(S)-methyl 6'-chloro-5-(((1R,2R)-2-((S)-methoxy((1S,3R)-3-(pyrimidin-2-ylthio)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((1S,3S)-3-(pyrimidin-2-ylthio)cyclohexyl)

methyl)cyclobutyl)methyl)-3',4,4',5-tetrahydro-2H,2'H-spiro[benzo[b][1,4]oxazepine-3,1'-naphthalene]-7-carboxylate} (50 mg, 0.075 mmol) in DCM (4 mL) was added 3-chloroperbenzoic acid (41 mg, 0.166 mmol) in one portion. The resulting mixture was stirred at 0° C. for 5 min and at ambient temperature for 2 h. The crude reaction mixture was directly subjected to combi-flash column chromatography (EtOAc/Hexanes, 40 min from 0 to 70%, 24 g ISCO silica gel column) to give a mixture of the title compounds (31 mg, 0.045 mmol, 59% yield) as a colorless film.

Step 7: {(S)-6'-chloro-5-(((1R,2R)-2-((S)-methoxy ((1R,3S)-3-sulfamoylcyclohexyl)methyl)cyclobutyl) methyl)-3',4,4',5-tetrahydro-2H,2'H-spiro[benzo[b] [1,4]oxazepine-3,1'-naphthalene]-7-carboxylic acid and (S)-6'-chloro-5-(((1R,2R)-2-((S)-methoxy((1R, 3R)-3-sulfamoylcyclohexyl)methyl)cyclobutyl) methyl)-3',4,4',5-tetrahydro-2H,2'H-spiro[benzo[b] [1,4]oxazepine-3,1'-naphthalene]-7-carboxylic acid} or {(S)-6'-chloro-5-(((1R,2R)-2-((S)-methoxy((1R, 3R)-3-sulfamoylcyclohexyl)methyl)cyclobutyl) methyl)-3',4,4',5-tetrahydro-2H,2'H-spiro[benzo[b] [1,4]oxazepine-3,1'-naphthalene]-7-carboxylic acid and (S)-6'-chloro-5-(((1R,2R)-2-((R)-methoxy((1S, 3S)-3-sulfamoylcyclohexyl)methyl)cyclobutyl) methyl)-3',4,4',5-tetrahydro-2H,2'H-spiro[benzo[b] [1,4]oxazepine-3,1'-naphthalene]-7-carboxylic acid} or {(S)-6'-chloro-5-(((1R,2R)-2-((S)-methoxy((1S, 3R)-3-sulfamoylcyclohexyl)methyl)cyclobutyl) methyl)-3',4,4',5-tetrahydro-2H,2'H-spiro[benzo[b] [1,4]oxazepine-3,1'-naphthalene]-7-carboxylic acid and (S)-6'-chloro-5-(((1R,2R)-2-((S)-methoxy((1S, 3S)-3-sulfamoylcyclohexyl)methyl)cyclobutyl) methyl)-3',4,4',5-tetrahydro-2H,2'H-spiro[benzo[b] [1,4]oxazepine-3,1'-naphthalene]-7-carboxylic acid}

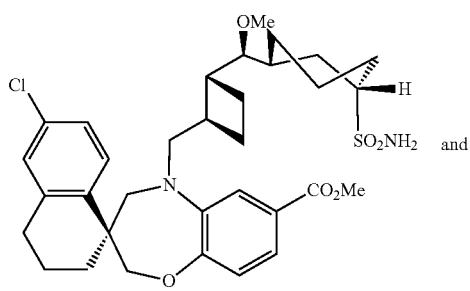 and

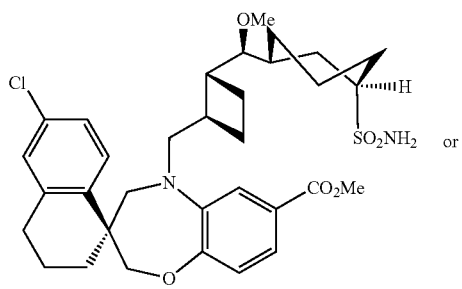 or

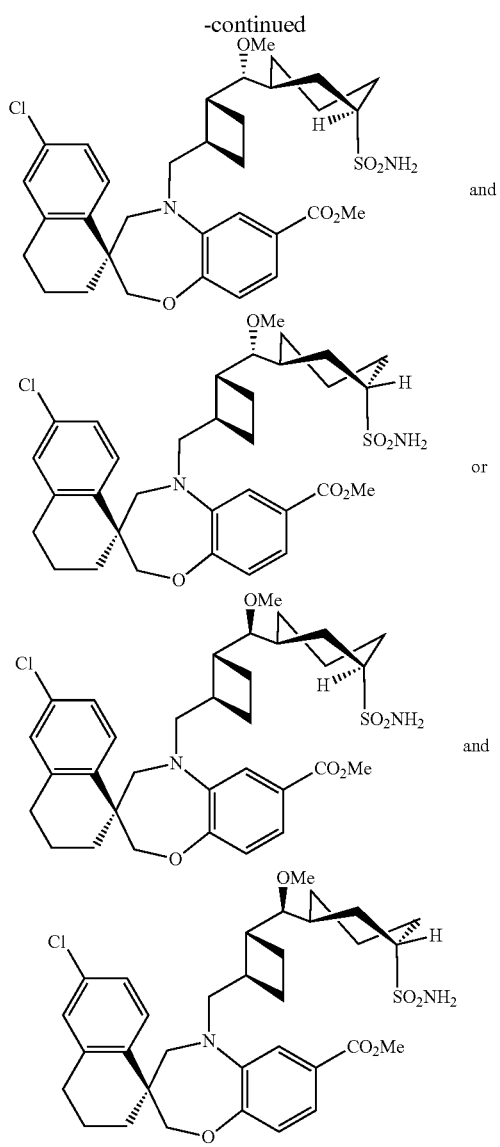

The title compounds were synthesized from {(S)-methyl 6'-chloro-5-(((1R,2R)-2-((S)-methoxy((1R,3S)-3-(pyrimidin-2-ylsulfonyl)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((1R,3R)-3-(pyrimidin-2-ylsulfonyl)cyclohexyl)methyl)cyclobutyl)methyl)-3',4,4',5-tetrahydro-2H,2'H-spiro[benzo[b][1,4]oxazepine-3,1'-naphthalene]-7-carboxylate} or {(S)-methyl 6'-chloro-5-(((1R,2R)-2-((R)-methoxy((1S,3R)-3-(pyrimidin-2-ylsulfonyl)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-methoxy((1S,3S)-3-(pyrimidin-2-ylsulfonyl)cyclohexyl)methyl)cyclobutyl)methyl)-3',4,4',5-tetrahydro-2H,2'H-spiro[benzo[b][1,4]oxazepine-3,1'-naphthalene]-7-carboxylate} or {(S)-methyl 6'-chloro-5-(((1R,2R)-2-((S)-methoxy((1S,3R)-3-(pyrimidin-2-ylsulfonyl)cyclohexyl)methyl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((S)-methoxy((1S,3S)-3-(pyrimidin-2- ylsulfonyl)cyclohexyl)methyl)cyclobutyl)methyl)-3',4,4',5-tetrahydro-2H,2'H-spiro[benzo[b][1,4]oxazepine-3,1'-naphthalene]-7-carboxylate} following the procedure described for Step 7 in Examples 364 and 365.

Step 8: (1S,3'R,6'R,7'S,8'R,12'S)-6-chloro-7'-methoxy-3,4-dihydro-2H,15'H-spiro[naphthalene-1,22'-[20]oxa[13]thia[1,14]diazapentacyclo[14.7.2.1$^{8,12}$.0$^{3,6}$.0$^{19,24}$]hexacosa[16,18,24]trien]-15'-one 13',13'-dioxide or (1S,3'R,6'R,7'S,8'R,12'R)-6-chloro-7'-methoxy-3,4-dihydro-2H,15'H-spiro[naphthalene-1,22'-[20]oxa[13]thia[1,14]diazapentacyclo[14.7.2.1$^{8,12}$.0$^{3,6}$.0$^{19,24}$]hexacosa[16,18,24]trien]-15'-one 13',13'-dioxide or (1S,3'R,6'R,7'R,8'S,12'R)-6-chloro-7'-methoxy-3,4-dihydro-2H,15'H-spiro[naphthalene-1,22'-[20]oxa[13]thia[1,14]diazapentacyclo[14.7.2.1$^{8,12}$.0$^{3,6}$.0$^{19,24}$]hexacosa[16,18,24]trien]-15'-one 13',13'-dioxide or (1S,3'R,6'R,7'R,8'S,12'S)-6-chloro-7'-methoxy-3,4-dihydro-2H,15'H-spiro[naphthalene-1,22'-[20]oxa[13]thia[1,14]diazapentacyclo[14.7.2.1$^{8,12}$.0$^{3,6}$.0$^{19,24}$]hexacosa[16,18,24]trien]-15'-one 13',13'-dioxide or (1S,3'R,6'R,7'S,8'R,12'R)-6-chloro-7'-methoxy-3,4-dihydro-2H,15'H-spiro[naphthalene-[20]oxa[13]thia[1,14]diazapentacyclo[14.7.2.1$^{8,12}$.0$^{3,6}$.0$^{19,24}$]hexacosa[16,18,24]trien]-15'-one 13',13'-dioxide or (1S,3'R,6'R,7'S,8'S,12'S)-6-chloro-7'-methoxy-3,4-dihydro-2H,15'H-spiro[naphthalene-1,22'-[20]oxa[13]thia[1,14]diazapentacyclo[14.7.2.1$^{8,12}$.0$^{3,6}$.0$^{19,24}$]hexacosa[16,18,24]trien]-15'-one 13',13'-dioxide To a stirred ice-cooled solution of {(S)-6'-chloro-5-(((1R,2R)-2-((S)-methoxy((1R,3S)-3-sulfamoylcyclohexyl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S)-methoxy((1R,3R)-3-sulfamoylcyclohexyl)methyl)cyclobutyl)methyl)-3',4,4',5-tetrahydro-2H,2'H-spiro[benzo[b][1,4]oxazepine-3,1'-naphthalene]-7-carboxylic acid} or {(S)-6'-chloro-5-(((1R,2R)-2-((S)-methoxy((1R,3R)-3-sulfamoylcyclohexyl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-methoxy((1S,3S)-3-sulfamoylcyclohexyl)methyl)cyclobutyl)methyl)-3',4,4',5-tetrahydro-2H,2'H-spiro[benzo[b][1,4]oxazepine-3,1'-naphthalene]-7-carboxylic acid} or {(S)-6'-chloro-5-(((1R,2R)-2-((S)-methoxy((1S,3R)-3-sulfamoylcyclohexyl)methyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((S)-methoxy((1S,3S)-3-sulfamoylcyclohexyl)methyl)cyclobutyl)methyl)-3',4,4',5-tetrahydro-2H,2'H-spiro[benzo[b][1,4]oxazepine-3,1'-naphthalene]-7-carboxylic acid} (23 mg, 0.036 mmol) and N,N-dimethylpyridin-4-amine (10 mg, 0.080 mmol) in DCM (20 mL) was added N1-((ethylimino)methylene)-N3,N3-dimethylpropane-1,3-diamine hydrochloride (17 mg, 0.091 mmol) in one portion. The resulting mixture was stirred at 0° C. for 5 min and at ambient temperature for 27 h. The reaction mixture was concentrated in reduced pressure and the residue was directly loaded onto a silica gel precolumn and subjected to combi-flash column chromatography ((EtOAc with 0.35% AcOH)/hexanes, 70 min from 0 to 100% and 15 min at 100%, 24 g ISCO silica gel column) to give 8.0 mg of the title compound as the first eluting fraction as a white solid. $^1$H NMR (500 MHz, CDCl$_3$) δ 7.85 (br. s., 1H), 7.70 (d, J=8.6 Hz, 1H), 7.19 (dd, J=2.3, 8.4 Hz, 1H), 7.09 (d, J=2.2 Hz, 1H), 7.03-6.91 (m, 2H), 6.89 (d, J=8.3 Hz, 1H), 4.15-4.10 (m, 1H), 4.07-3.99 (m, 1H), 3.72 (br. s., 2H), 3.51 (s, 3H), 3.39-3.28 (m, 1H), 3.07 (d, J=2.4 Hz, 1H), 2.91-2.70 (m, 3H), 2.39-1.16 (m, 20H). m/z (ESI, +ve ion) 617.1 (M+H)$^+$.

Example 367. (1S,3'R,6'R,7'S,8'R,12'R)-6-chloro-7'-methoxy-3,4-dihydro-2H,15'H-spiro[naphthalene-1,22'-[20]oxa[13]thia[1,14]diazapentacyclo[14.7.2.1$^{8,12}$.0$^{3,6}$.0$^{19,24}$]hexacosa[16,18,24]trien]-15'-one 13',13'-dioxide or (1S,3'R,6'R,7'S,8'R,12'S)-6-chloro-7'-methoxy-3,4-dihydro-2H,15'H-spiro[naphthalene-1,22'-[20]oxa[13]thia[1,14]diazapentacyclo[14.7.2.1$^{8,12}$.0$^{3,6}$.0$^{19,24}$]hexacosa[16,18,24]trien]-15'-one 13',13'-dioxide or (1S,3'R,6'R,7'R,8'S,12'R)-6-chloro-7'-methoxy-3,4-dihydro-2H,15'H-spiro[naphthalene-1,22'-[20]oxa[13]thia[1,14]diazapentacyclo[14.7.2.1$^{8,12}$.0$^{3,6}$.0$^{19,24}$]hexacosa[16,18,24]trien]-15'-one 13',13'-dioxide or (1S,3'R,6'R,7'R,8'S,12'S)-6-chloro-7'-methoxy-3,4-dihydro-2H,15'H-spiro[naphthalene-1,22'-[20]oxa[13]thia[1,14]diazapentacyclo[14.7.2.1$^{8,12}$.0$^{3,6}$.0$^{19,24}$]hexacosa[16,18,24]trien]-15'-one 13',13'-dioxide or (1S,3'R,6'R,7'S,8'S,12'R)-6-chloro-7'-methoxy-3,4-dihydro-2H,15'H-spiro[naphthalene-1,22'-[20]oxa[13]thia[1,14]diazapentacyclo[14.7.2.1$^{8,12}$.0$^{3,6}$.0$^{19,24}$]hexacosa[16,18,24]trien]-15'-one 13',13'-dioxide or (1S,3'R,6'R,7'S,8'S,12'S)-6-chloro-7'-methoxy-3,4-dihydro-2H,15'H-spiro[naphthalene-1,22'-[20]oxa[13]thia[1,14]diazapentacyclo[14.7.2.1$^{8,12}$.0$^{3,6}$.0$^{19,24}$]hexacosa[16,18,24]trien]-15'-one 13',13'-dioxide

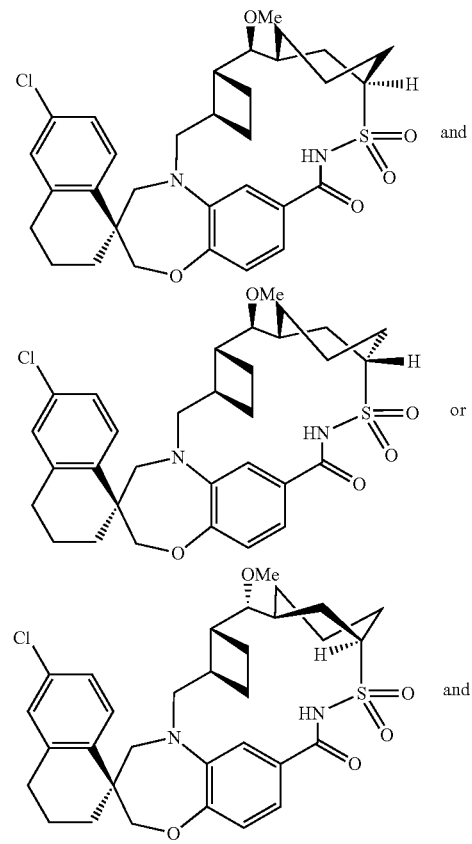

872

Step 1: (S)-tert-butyl 5-(((1R,2R)-2-((allyloxy)methyl)cyclobutyl)methyl)-6'-chloro-3',4,4',5-tetrahydro-2H,2'H-spiro[benzo[b][1,4]oxazepine-3,1'-naphthalene]-7-carboxylate

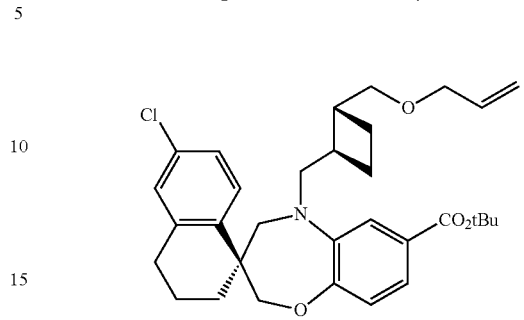

To a stirred solution of (S)-tert-butyl 6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate (0.240 g, 0.482 mmol, Intermediate AA11A, Step 19B) in THF (5 mL) was added at rt sodium hydride, 60% dispersion in mineral oil (0.014 g, 0.58 mmol) under nitrogen. The mixture was stirred at ambient temperature for 20 min before allyl bromide (0.044 mL, 0.506 mmol) was added. The resulting mixture was stirred at ambient temperature for 19 h. As LC-MS showed that the sm was still the major, the reaction mixture was then heated up to 70° C. for 2 h. LC-MS showed that the desired product was the major with still some sm remaining. The temperature was then raised to 80° C. and the mixture was stirred at this temperature for 1 h. After cooled, the mixture was poured into ice and brine and extracted with EtOAc (2×). The combined organics were dried over anhydrous sodium sulfate and concentrated in vacuo. The crude residue was loaded onto a silica gel precolumn and subjected to combi-flash column chromatography (EtOAc/Hexanes, 30 min from 0 to 30%, 24 g ISCO silica gel column) to give the title compound (0.239 g, 0.444 mmol, 92% yield) as a clear film, directly taken onto the next step.

Step 2: (S)-5-(((1R,2R)-2-((allyloxy)methyl)cyclobutyl)methyl)-6'-chloro-3',4,4',5-tetrahydro-2H,2'H-spiro[benzo[b][1,4]oxazepine-3,1'-naphthalene]-7-carboxylic acid

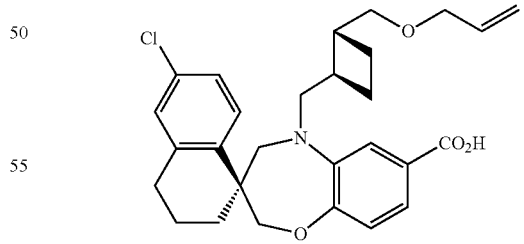

To a stirred solution of (S)-tert-butyl 5-(((1R,2R)-2-((allyloxy)methyl)cyclobutyl)methyl)-6'-chloro-3',4,4',5-tetrahydro-2H,2'H-spiro[benzo[b][1,4]oxazepine-3,1'-naphthalene]-7-carboxylate (0.239 g, 0.444 mmol) in THF (5.0 mL), MeOH (10.0 mL), and water (5.0 mL) was added lithium hydroxide monohydrate (0.380 g, 8.88 mmol) at ambient temperature. The mixture was heated at reflux (105° C.) for 18 h. After cooled, the mixture was poured into ice and

871

-continued

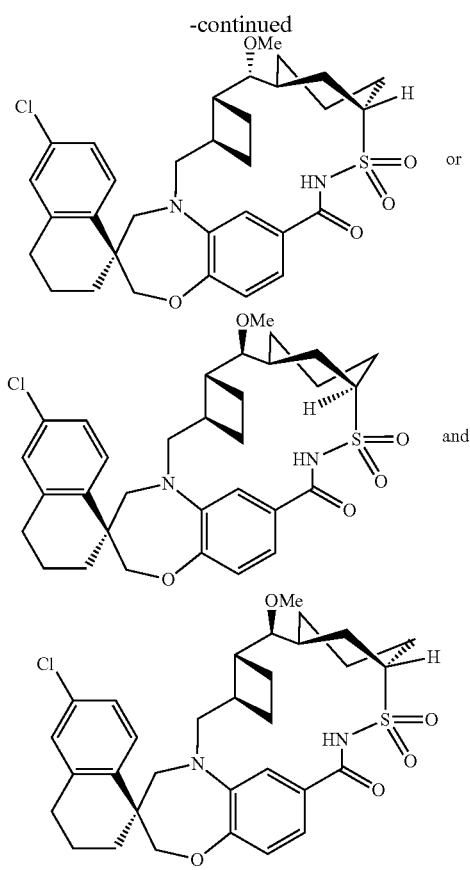

Further elution from the combi-flash column chromatography in Example 366, Step 8 provided the title compound as the second eluting fraction which was not pure. This was subjected to preparative reverse-phase HPLC (Gemini Prep $C_{18}$ 5 μm column; Phenomenex, Torrance, CA; gradient elution of 60-95% acetonitrile in water, where both solvents contained 0.1% TFA, 30 min method) to give, after lyophilization, 1.7 mg of the pure title compound in Example 367 as a white solid. $^1$H NMR (500 MHz, CDCl$_3$) δ 7.63 (br. s., 2H), 7.17 (d, J=8.6 Hz, 1H), 7.10 (d, J=2.2 Hz, 1H), 6.91 (d, J=7.8 Hz, 1H), 6.81 (br. s., 1H), 4.16 (br. s., 3H), 3.57 (d, J=8.6 Hz, 3H), 3.26-2.93 (m, 1H), 2.75 (br. s., 2H), 2.47 (t, J=8.2 Hz, 2H), 2.17-0.89 (m, 21H). m/z (ESI, +ve ion) 617.1 (M+H)$^+$.

Example 368. (3R,6R,12R,22S)-6'-chloro-12-ethyl-3',4'-dihydro-2'H,15H-spiro[8,20-dioxa-13-thia-1,14-diazatetracyclo[14.7.2.0$^{3,6}$.0$^{19,24}$]pentacosa-16,18,24-triene-22,1'-naphthalen]-15-one 13,13-dioxide

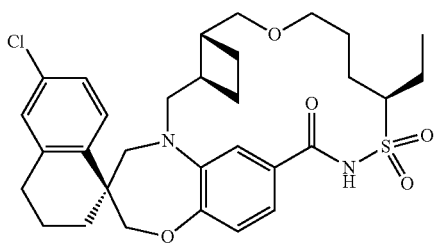 [SMILES: CC[C@@H]1CCCOC[C@@H]2CC[C@H]2CN2C[C@@]3(CCCc4cc(Cl)ccc43)COc3ccc(cc32)C(=O)NS1(=O)=O]

saturated ammonium chloride aqueous solution with a small volume of saturated citric aqueous solution added, and extracted with EtOAc (3×). The combined organics were dried over anhydrous sodium sulfate and concentrated in vacuo to give the title compound (0.180 g, 0.373 mmol, 84% yield) as a white solid, directly taken onto the next step.

Step 3: (S)-5-(((1R,2R)-2-((allyloxy)methyl)cyclobutyl)methyl)-6'-chloro-N—((S)-pent-1-en-3-ylsulfonyl)-3',4,4',5-tetrahydro-2H,2'H-spiro[benzo[b][1,4]oxazepine-3,1'-naphthalene]-7-carboxamide and (S)-5-(((1R,2R)-2-((allyloxy)methyl)cyclobutyl)methyl)-6'-chloro-N—((R)-pent-1-en-3-ylsulfonyl)-3',4,4',5-tetrahydro-2H,2'H-spiro[benzo[b][1,4]oxazepine-3,1'-naphthalene]-7-carboxamide

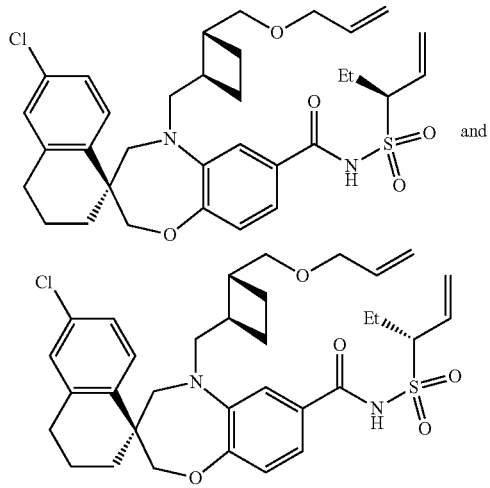

To a stirred solution of (S)-5-(((1R,2R)-2-((allyloxy)methyl)cyclobutyl)methyl)-6'-chloro-3',4,4',5-tetrahydro-2H,2'H-spiro[benzo[b][1,4]oxazepine-3,1'-naphthalene]-7-carboxylic acid (85 mg, 0.18 mmol), pent-1-ene-3-sulfonamide (53 mg, 0.35 mmol), and N,N-dimethylpyridin-4-amine (65 mg, 0.53 mmol) in DCM (10 mL) was added 1-(3-dimethylaminopropyl)-3-ethylcarbodiimide hydrochloride (101 mg, 0.529 mmol) at ambient temperature. The mixture was stirred at rt for a period of 3 h. The crude mixture was loaded onto a silica gel precolumn and subjected to combi-flash column chromatography (EtOAc/Hexanes, 4 min at 0% and 26 min from 0 to 100% and 15 min at 100%, 40 g ISCO silica gel column) to give a mixture of the title compounds (87 mg, 0.14 mmol, 78% yield) as a colorless film.

Step 4: (3R,6R,12R,22S)-6'-chloro-12-ethyl-3',4'-dihydro-2'H,15H-spiro[8,20-dioxa-13-thia-1,14-diazatetracyclo[14.7.2.0$^{3,6}$.0$^{19,24}$]pentacosa-16,18,24-triene-22,1'-naphthalen]-15-one 13,13-dioxide The 1st step: To a 50-mL single-necked round-bottomed flask were placed (S)-5-(((1R,2R)-2-((allyloxy)methyl)cyclobutyl)methyl)-6'-chloro-N—((S)-pent-1-en-3-ylsulfonyl)-3',4,4',5-tetrahydro-2H,2'H-spiro[benzo[b][1,4]oxazepine-3,1'-naphthalene]-7-carboxamide and (S)-5-(((1R,2R)-2-((allyloxy)methyl)cyclobutyl)methyl)-6'-chloro-N—((R)-pent-1-en-3-ylsulfonyl)-3',4,4',5-tetrahydro-2H,2'H-spiro[benzo[b][1,4]oxazepine-3,1'-naphthalene]-7-carboxamide (45 mg, 0.073 mmol) and hoveyda-grubbs catalyst second generation (9.2 mg, 0.015 mmol). The flask was subjected to evacuation and back-filling with nitrogen (3×). AcOH (24 mL) was added at rt under nitrogen atmosphere. The resulting mixture was stirred at ambient temperature under house vacuum for 23 h. The reaction mixture was concentrated under reduced pressure. The residue was loaded onto a silica gel precolumn and subjected to combi-flash column chromatography ((10% MeOH/DCM with 0.2% AcOH)/DCM, 30 min from 0 to 100%, 24 g ISCO silica gel) to give 25 mg of a diastereomeric mixture of products, directly taken onto the next step.

The 2nd step: A vigorously stirred mixture of the above impure product mixture and platinum(IV) oxide (15 mg) in EtOAc (15 mL) was balloon hydrogenated at ambient temperature for 3 h. The solid was removed by filtration and the filtrate was concentrated in vacuo. The residue was subjected to preparative reverse-phase HPLC (Gemini Prep C$_{18}$ 5 μm column; Phenomenex, Torrance, CA; gradient elution of 40-95% acetonitrile in water, where both solvents contained 0.1% TFA, 30 min method) to give 1.2 mg of the title compound as an off-white solid (the first eluting fraction). $^1$H NMR (500 MHz, CDCl$_3$) δ 8.16 (s, 1H), 7.73 (d, J=8.6 Hz, 1H), 7.19 (dd, J=2.3, 8.4 Hz, 1H), 7.09 (d, J=2.2 Hz, 1H), 7.03-6.98 (m, 2H), 6.95-6.90 (m, 1H), 4.17-4.04 (m, 2H), 3.85-3.67 (m, 3H), 3.60-3.51 (m, 2H), 3.42 (td, J=5.1, 9.9 Hz, 1H), 3.35 (dd, J=5.1, 10.5 Hz, 1H), 3.24 (d, J=14.2 Hz, 1H), 3.04 (dd, J=9.5, 15.4 Hz, 1H), 2.87-2.71 (m, 2H), 2.68-2.57 (m, 1H), 2.29-1.25 (m, 15H), 1.15 (t, J=7.5 Hz, 3H). m/z (ESI, +ve ion) 587.2 (M+H)$^+$.

Example 369. (3R,6R,12S,22S)-6'-chloro-12-ethyl-3',4'-dihydro-2'H,15H-spiro[8,20-dioxa-13-thia-1,14-diazatetracyclo[14.7.2.0$^{3,6}$.0$^{19,24}$]pentacosa-16,18,24-triene-22,1'-naphthalen]-15-one 13,13-dioxide

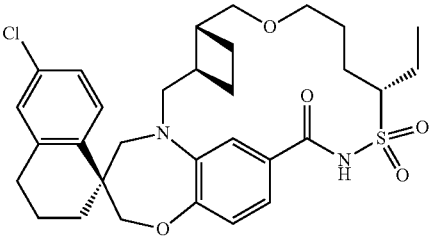 [SMILES: CC[C@H]1CCCOC[C@@H]2CC[C@H]2CN2C[C@@]3(CCCc4cc(Cl)ccc43)COc3ccc(cc32)C(=O)NS1(=O)=O]

Further elution from the to preparative reverse-phase HPLC purification in Example 368, Step 4 provided 0.7 mg of the title compound as an off-white solid (the second eluting fraction). $^1$H NMR (500 MHz, CDCl$_3$) δ 8.50 (s, 1H), 7.72 (d, J=8.6 Hz, 1H), 7.20 (ddd, J=2.2, 8.3, 10.3 Hz, 2H), 7.09 (d, J=2.4 Hz, 1H), 6.97 (d, J=8.3 Hz, 1H), 6.85 (d, J=2.0 Hz, 1H), 4.16-4.11 (m, 1H), 4.10-4.04 (m, 1H), 3.75 (d, J=14.2 Hz, 2H), 3.67 (qd, J=4.7, 9.2 Hz, 1H), 3.61-3.52 (m, 2H), 3.49-3.43 (m, 1H), 3.42-3.33 (m, 2H), 3.24 (dd, J=9.4, 15.3 Hz, 1H), 2.85-2.71 (m, 2H), 2.57-2.47 (m, 1H), 2.31-1.26 (m, 15H), 1.13 (t, J=7.6 Hz, 3H). m/z (ESI, +ve ion) 587.2 (M+H)$^+$.

Example 370. (1S,3'R,6'R)-6-chloro-3,4-dihydro-2H,9'H,15'H-spiro[naphthalene-1,22'-[20]oxa[13]thia[1,8,14]triazatetracyclo[14.7.2.0³,⁶.0¹⁹,²⁴]pentacosa[16,18,24]triene]-9',15'-dione 13',13'-dioxide

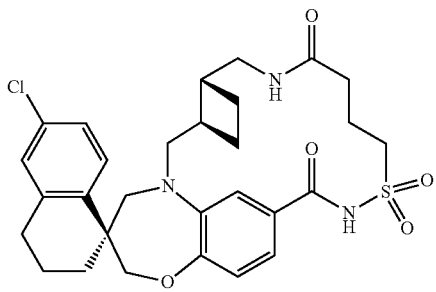 [SMILES: O=C1CCCS(=O)(=O)NC(=O)c2ccc3c(c2)N(C[C@@H]2CC[C@H]2CN1)C[C@@]1(CCCc2cc(Cl)ccc21)CO3]

Step 1: (S)-methyl 6'-chloro-5-(((1R,2R)-2-(((4-methoxybenzyl)amino)methyl)cyclobutyl)methyl)-3',4,4',5-tetrahydro-2H,2'H-spiro[benzo[b][1,4]oxazepine-3,1'-naphthalene]-7-carboxylate

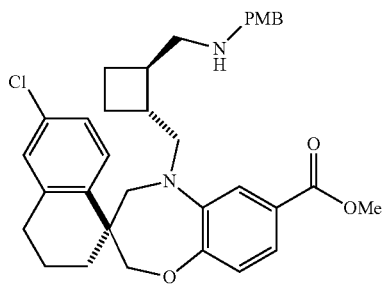

A mixture of (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (120 mg, 0.264 mmol, Intermediate AA11A, Step 20A) and 4-methoxybenzylamine (0.051 mL, 0.40 mmol) in DCM (3.0 mL) was stirred at ambient temperature for 15 min before sodium triacetoxyborohydride (168 mg, 0.793 mmol) was added in one portion. The resulting mixture was stirred at ambient temperature for 0.5 h. The reaction mixture was subjected to combi-flash column chromatography ((10% MeOH/DCM with 0.5% commercial ammonium hydroxide)/DCM, 35 min from 20 to 100%, 24 g ISCO silica gel column) to give the title compound (150 mg, 0.261 mmol, 99% yield) as a colorless film.

Step 2: (S)-methyl 6'-chloro-5-(((1R,2R)-2-((N-(4-methoxybenzyl)-4-sulfamoylbutanamido)methyl)cyclobutyl)methyl)-3',4,4',5-tetrahydro-2H,2'H-spiro[benzo[b][1,4]oxazepine-3,1'-naphthalene]-7-carboxylate

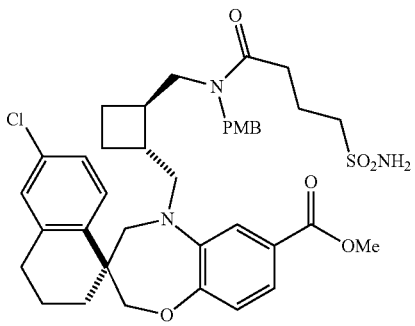

To a stirred mixture of (S)-methyl 6'-chloro-5-(((1R,2R)-2-(((4-methoxybenzyl)amino)methyl)cyclobutyl)methyl)-3',4,4',5-tetrahydro-2H,2'H-spiro[benzo[b][1,4]oxazepine-3,1'-naphthalene]-7-carboxylate (150 mg, 0.261 mmol) and 3-carboxypropanesulfonamide (46 mg, 0.27 mmol) in DCM (5 mL) was added HATU (104 mg, 0.274 mmol) at ambient temperature followed by n,n-diisopropylethylamine (0.054 mL, 0.313 mmol). The resulting mixture was stirred at ambient temperature for 1 h. The crude mixture was subjected to combi-flash column chromatography ((0.2% AcOH in EtOAc)/Hexanes), 40 min from 0 to 100%, 24 g ISCO silica gel column) to give the title compound (53 mg, 0.073 mmol, 28% yield) as a colorless film.

Step 3: (S)-6'-chloro-5-(((1R,2R)-2-((N-(4-methoxybenzyl)-4-sulfamoylbutanamido)methyl)cyclobutyl)methyl)-3',4,4',5-tetrahydro-2H,2'H-spiro[benzo[b][1,4]oxazepine-3,1'-naphthalene]-7-carboxylic acid

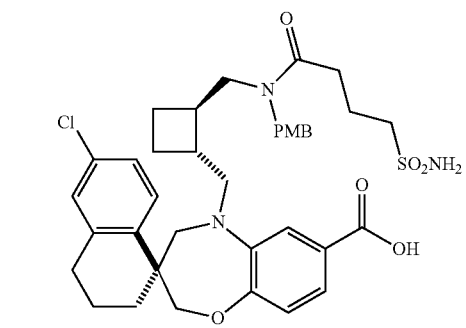

A mixture of (S)-methyl 6'-chloro-5-(((1R,2R)-2-4N-(4-methoxybenzyl)-4-sulfamoylbutanamido)methyl)cyclobutyl)methyl)-3',4,4',5-tetrahydro-2H,2'H-spiro[benzo[b][1,4]oxazepine-3,1'-naphthalene]-7-carboxylate (54 mg, 0.075 mmol) and lithium hydroxide hydrated (9.4 mg, 0.22 mmol) in a mixed solvent consisting of MeOH (3.0 mL), THF (1.0 mL) and Water (1.0 mL) was stirred at 80° C. for 2 h. After the reaction mixture was concentrated under reduced pressure, the residue was taken up in DMSO and subjected to preparative reverse-phase HPLC (Gemini Prep C$_{18}$ 5 μm column; Phenomenex, Torrance, CA; gradient elution of 20-95% acetonitrile in water, where both solvents contained 0.1% TFA, 30 min method) to give 16 mg of the title compound as a white solid.

Step 4: (1S,3'R,6'R)-6-chloro-8'-(4-methoxybenzyl)-3,4-dihydro-2H,9'H,15'H-spiro[naphthalene-1,22'-[20]oxa[13]thia[1,8,14]triazatetracyclo[14.7.2.0³,⁶.0¹⁹,²⁴]pentacosa[16,18,24]triene]-9',15'-dione 13',13'-dioxide

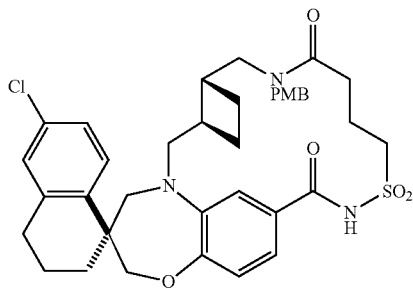

To a stirred solution of (S)-6'-chloro-5-(((1R,2R)-2-4N-(4-methoxybenzyl)-4-sulfamoylbutanamido)methyl)cyclobutyl)methyl)-3',4,4',5-tetrahydro-2H,2'H-spiro[benzo[b][1,4]oxazepine-3,1'-naphthalene]-7-carboxylic acid (30 mg, 0.042 mmol) in DCM (30 mL) was added EDCI HCl salt (20 mg, 0.13 mmol) at ambient temperature followed by N,N-dimethylpyridin-4-amine (15.5 mg, 0.127 mmol). The resulting mixture was stirred at ambient temperature for 4 h. After the reaction mixture was concentrated under reduced pressure, the residue was subjected to combi-flash column chromatography ((0.2% AcOH in EtOAc)/hexanes, 3 min at 0% and 40 min from 0 to 70%, 24 g ISCO silica gel column) to furnish 10 mg of the title compound as an off-white solid.

Step 5: (1S,3'R,6'R)-6-chloro-3,4-dihydro-2H,9'H,15'H-spiro[naphthalene-1,22'-[20]oxa[13]thia[1,8,14]triazatetracyclo[14.7.2.0³,⁶.0¹⁹,²⁴]pentacosa[16,18,24]triene]-9',15'-dione 13',13'-dioxide A solution of (1S,3'R,6'R)-6-chloro-8'-(4-methoxybenzyl)-3,4-dihydro-2H,9'H,15'H-spiro[naphthalene-1,22'-[20]oxa[13]thia[1,8,14]triazatetracyclo[14.7.2.0³,⁶.0¹⁹,²⁴]pentacosa[16,18,24]triene]-9',15'-dione 13',13'-dioxide (not weighed) in 2,2,2-trifluoroacetic acid (3.0 mL) was heated at reflux for 2 h. The crude mixture was taken up in DMSO and subjected to preparative reverse-phase HPLC (Gemini Prep $C_{18}$ 5 μm column; Phenomenex, Torrance, CA; gradient elution of 20-95% acetonitrile in water, where both solvents contained 0.1% TFA, 30 min method) to give 4.5 mg of the title compound as a white solid. $^1$H NMR (500 MHz, DMSO-d6) δ 7.75 (t, J=4.8 Hz, 1H), 7.66 (d, J=8.6 Hz, 1H), 7.26 (dd, J=2.3, 8.4 Hz, 1H), 7.17 (d, J=2.2 Hz, 1H), 7.03-6.94 (m, 2H), 6.89 (d, J=8.1 Hz, 1H), 3.91 (ddd, J=5.5, 8.9, 14.7 Hz, 1H), 3.71 (d, J=15.7 Hz, 1H), 3.57 (d, J=13.9 Hz, 1H), 3.49-3.15 (m, 5H), 3.08-2.92 (m, 2H), 2.83-2.65 (m, 2H), 2.45-2.32 (m, 2H), 2.27-2.07 (m, 2H), 2.02-1.59 (m, 9H), 1.49-1.34 (m, 1H). m/z (ESI, +ve ion) 572.3 (M+H)⁺.

Example 371. (1S,3'R,6'R,10'E)-8'-acetyl-6-chloro-3,4-dihydro-2H,15'H-spiro[naphthalene-1,22'-[20]oxa[13]thia[1,8,14]triazatetracyclo[14.7.2.0³,⁶.0¹⁹,²⁴]pentacosa[10,16,18,24]tetraen]-15'-one 13',13'-dioxide and (1S,3'R,6'R,10'Z)-8'-acetyl-6-chloro-3,4-dihydro-2H,15'H-spiro[naphthalene-1,22'-[20]oxa[13]thia[1,8,14]triazatetracyclo[14.7.2.0³,⁶.0¹⁹,²⁴]pentacosa[10,16,18,24]tetraen]-15'-one 13',13'-dioxide

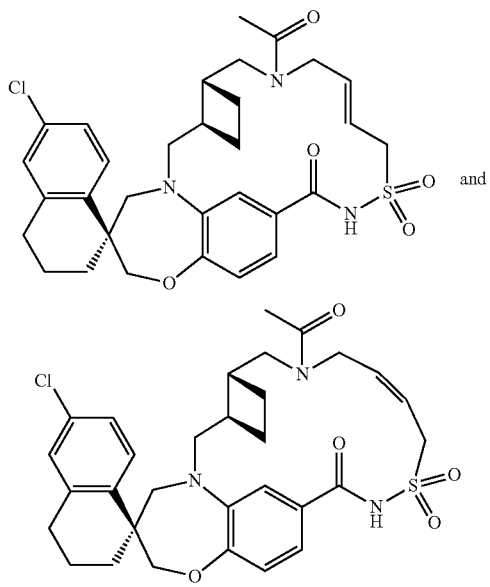

Step 1: (S)-methyl 5-(((1R,2R)-2-((allylamino)methyl)cyclobutyl)methyl)-6'-chloro-3',4,4',5-tetrahydro-2H,2'H-spiro[benzo[b][1,4]oxazepine-3,1'-naphthalene]-7-carboxylate

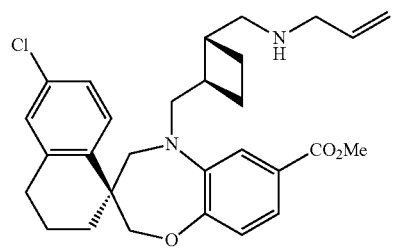 [SMILES: C=CCNC[C@@H]1CC[C@H]1CN1C[C@@]2(CCCc3cc(Cl)ccc32)COc2ccc(C(=O)OC)cc21]

A mixture of (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (110 mg, 0.242 mmol, Intermediate AA11A, Step 20A) and allylamine (0.036 mL, 0.485 mmol) in DCM (3.0 mL) was stirred at ambient temperature for 30 min before sodium triacetoxyborohydride (154 mg, 0.727 mmol) was added in one portion. After the resulting mixture was stirred at ambient temperature for 1 h, the reaction mixture was concentrated under reduced pressure and the residue was directly taken onto the next step.

Step 2: (S)-5-(((1R,2R)-2-((allylamino)methyl)cyclobutyl)methyl)-6'-chloro-3',4',5-tetrahydro-2H,2'H-spiro[benzo[b][1,4]oxazepine-3,1'-naphthalene]-7-carboxylic acid

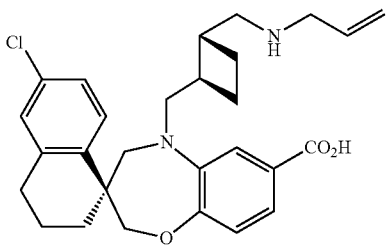 [SMILES: C=CCNC[C@@H]1CC[C@H]1CN1C[C@@]2(CCCc3cc(Cl)ccc32)COc2ccc(C(=O)O)cc21]

To the above crude residue was added lithium hydroxide monohydrate (150 mg, 3.63 mmol) followed by MeOH (5.0 mL), THF (2.0 mL) and water (2.0 mL). The resulting mixture was stirred at 100° C. for 1 h. The reaction mixture was concentrated under reduced pressure and the residue was directly taken onto the next step.

Step 3: (S)-5-(((1R,2R)-2-((N-allylacetamido)methyl)cyclobutyl)methyl)-6'-chloro-3',4',5-tetrahydro-2H,2'H-spiro[benzo[b][1,4]oxazepine-3,1'-naphthalene]-7-carboxylic acid

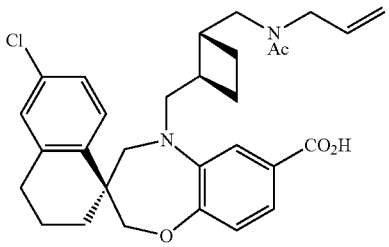

The above crude residue was dissolved in DMF (3.0 mL) and 2-Propanol (1.0 mL). To this stirred mixture was added 2,5-dioxopyrrolidin-1-yl acetate (114 mg, 0.727 mmol) followed by diisopropylethylamine (0.126 mL, 0.727 mmol). The resulting mixture was sonicated and stirred at ambient temperature for 1 h. Still some unreacted sm was observed. DMSO (1.500 mL) was added to facilitate the dissolution later followed by more 2,5-dioxopyrrolidin-1-yl acetate (not weighed). The mixture was stirred at ambient temperature for another 1.5 h. Upon workup, the mixture was poured into ice and saturated ammonium chloride. The pH of the resulting mixture was adjusted with 2 N aqueous HCl followed by extraction with EtOAc (2x). The combined organics were dried over anhydrous sodium sulfate and concentrated in vacuo. The crude residue (0.21 g) was taken onto the next step without purification.

Step 4: (S)-5-(((1R,2R)-2-((N-allylacetamido)methyl)cyclobutyl)methyl)-N-(allylsulfonyl)-6'-chloro-3',4',5-tetrahydro-2H,2'H-spiro[benzo[b][1,4]oxazepine-3,1'-naphthalene]-7-carboxamide

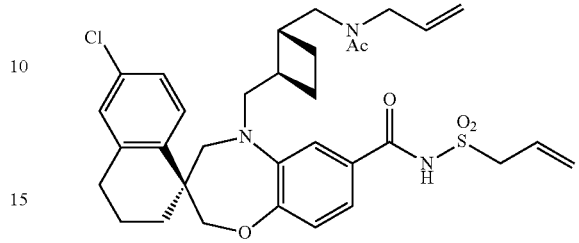

To a stirred mixture of (S)-5-(((1R,2R)-2-((N-allylacetamido)methyl)cyclobutyl)methyl)-6'-chloro-3',4',5-tetrahydro-2H,2'H-spiro[benzo[b][1,4]oxazepine-3,1'-naphthalene]-7-carboxylic acid (48 mg, 0.092 mmol) and prop-2-ene-1-sulfonamide (33 mg, 0.28 mmol) in DCM (2.0 mL) was added at rt EDCI HCl salt (43 mg, 0.28 mmol) followed by N,N-dimethylpyridin-4-amine (34 mg, 0.28 mmol). The resulting mixture was stirred at rt for a period of 16 h. The crude mixture was subjected to combi-flash column chromatography ((0.2% AcOH in EtOAc)/hexanes), 35 min from 0 to 100%, 24 g ISCO silica gel column) to furnish 30 mg of the title compound as a colorless film, directly taken onto the next step.

Step 5: (1S,3'R,6'R,10'E)-8'-acetyl-6-chloro-3,4-dihydro-2H,15'H-spiro[naphthalene-1,22'-[20]oxa[13]thia[1,8,14]triazatetracyclo[14.7.2.0$^{3,6}$.0$^{19,24}$]pentacosa[10,16,18,24]tetraen]-15'-one 13',13'-dioxide and (1S,3'R,6'R,10'Z)-8'-acetyl-6-chloro-3,4-dihydro-2H,15'H-spiro[naphthalene-1,22'-[20]oxa[13]thia[1,8,14]triazatetracyclo[14.7.2.0$^{3,6}$.0$^{19,24}$]pentacosa[10,16,18,24]tetraen]-15'-one 13',13'-dioxide A 250 mL single-necked round-bottomed flask charged with (S)-5-(((1R,2R)-2-((N-allylacetamido)methyl)cyclobutyl)methyl)-N-(allylsulfonyl)-6'-chloro-3',4',5-tetrahydro-2H,2'H-spiro[benzo[b][1,4]oxazepine-3,1'-naphthalene]-7-carboxamide (25 mg, 0.040 mmol) was subjected to 3 cycles of evacuation and back-filling with nitrogen. Toluene (40 mL) was introduced under nitrogen. The resulting mixture was stirred at ambient temperature for 10 min to allow the starting material to dissolve (but it didn't completely dissolved) before 2$^{nd}$ generation hoveyda-grubbs catalyst (5.0 mg, 8.0 μmop was added. The resulting mixture was stirred at 106° C. for 75 min. After the volatiles were removed, the crude residue was subjected to combi-flash column chromatography ((0.2% AcOH in EtOAc/hexanes), 35 min from 0 to 100%, 24 g ISCO silica gel column) to furnish 5 mg of a nearly 1-to-1 mixture of the title compounds as an off-white solid. $^1$H NMR (400 MHz, CDCl$_3$) δ 8.27 (br. d, J=1.0 Hz, 1H), 7.70 (t, J=8.9 Hz, 1H), 7.41 (s, 0.5H), 7.37 (s, 0.5H), 7.20 (td, J=3.0, 8.5 Hz, 1H), 7.12-7.06 (m, 1H), 7.00-6.88 (m, 2H), 5.69-5.43 (m, 2H), 4.75-4.57 (m, 1H), 4.20-4.04 (m, 4H), 4.00-3.90 (m, 2H), 3.83-3.68 (m, 2H), 3.22 (dd, J=11.2, 14.3 Hz, 2H), 3.05 (dd, J=9.0, 14.3 Hz, 1H), 2.86-2.65 (m, 4H), 2.31-1.37 (m, 11H). m/z (ESI, +ve ion) 598.3 (M+H)$^+$.

881

Example 372. (1S,3'R,6'S,7'E,9'E,11'S,12'R)-6-chloro-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [7,9,16,18,24]pentaen]-15'-one 13',13'-dioxide

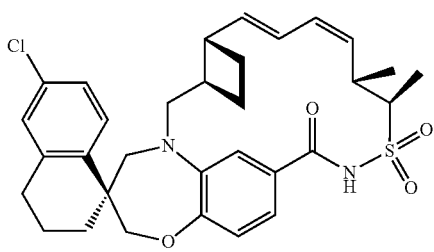

To a stirred solution of bis(2,2,2-trifluoroethoxy)triphenylphosphorane (11.52 mg, 0.025 mmol) in a mixed solvent comprising DCM (0.6 mL) and Et$_2$O (0.6 mL) was added a solution of (1S,3'R,6'R,7'S,8'E,11'S,12'R)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (15 mg, 0.025 mmol, Example 357, Step 1) in DCM (0.3 mL) at ambient temperature. The resulting mixture was stirred at ambient temperature for 2 h. More bis(2,2,2-trifluoroethoxy)triphenylphosphorane (not weighed) was added to the solution and the stirring continued for 2 h. After the reaction mixture was concentrated under reduced pressure, the residue was taken up in DMSO, and subjected to preparative reverse-phase HPLC (Gemini™ Prep C$_{18}$ 5 µm column; Phenomenex, Torrance, CA; gradient elution of 55-95% acetonitrile in water, where both solvents contained 0.1% TFA, 30 min method) to give 4.0 mg of the title compound as a white solid. $^1$H NMR (400 MHz, CDCl$_3$) δ 7.71-7.61 (m, 2H), 7.21 (ddd, J=2.2, 8.4, 19.6 Hz, 2H), 7.10 (d, J=2.2 Hz, 1H), 6.96 (d, J=8.2 Hz, 1H), 6.65 (d, J=2.0 Hz, 1H), 6.28 (dd, J=10.2, 15.3 Hz, 1H), 6.07 (dd, J=10.2, 16.0 Hz, 1H), 5.91 (dd, J=6.8, 16.0 Hz, 1H), 5.53 (dd, 15.2 Hz, 1H), 4.19-4.02 (m, 2H), 3.76-3.66 (m, 2H), 3.57 (d, J=15.5 Hz, 1H), 3.36-3.19 (m, 2H), 2.88-2.74 (m, 2H), 2.71-2.54 (m, 2H), 2.31 (quin, J=8.5 Hz, 1H), 2.17-1.66 (m, 6H), 1.60 (d, J=7.2 Hz, 3H), 1.58-1.45 (m, 2H), 1.17 (d, J=6.8 Hz, 3H). m/z (ESI, +ve ion) 581.1 (M+H)$^+$.

882

Example 373. (1S,3'R,6'R,7'S,8'E,12'S)-6-chloro-7'-hydroxy-12'-(1,3-thiazol-2-ylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,12'R)-6-chloro-7'-hydroxy-12'-(1,3-thiazol-2-ylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide Step 1: 2-(bromomethyl)thiazole

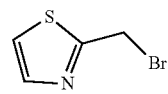

To a suspension of 1,3-thiazol-2-ylmethanol (1.52 g, 12.8 mmol) in Et$_2$O, carbon tetrabromide (1.37 mL, 14.1 mmol) and triphenylphosphine (3.69 g, 14.1 mmol) was added at ambient temperature. The mixture was stirred for 2 h, and a white precipitate was formed. The mixture was then filtered and the filtrate was concentrated under reduced pressure. The resulting residue was chromatographed (silica gel, hexane/EtOAc, 9:1 to 1:1) to afford the title compound as a colorless liquid which was used immediately for the next reaction without further purification. m/z (ESI, +ve ion) 178.2 (M+H)$^+$.

Step 2: (2S)—N,N-bis(4-methoxybenzyl)-1-(1,3-thiazol-2-yl)-5-hexene-2-sulfonamide and (2R)—N,N-bis(4-methoxybenzyl)-1-(1,3-thiazol-2-yl)-5-hexene-2-sulfonamide

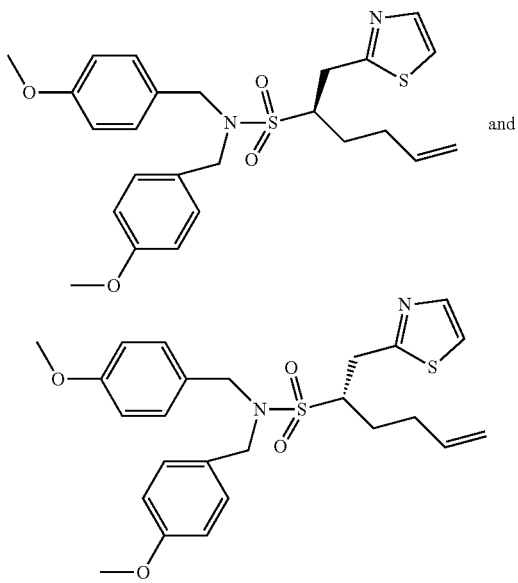

and

To a solution of N,N-bis(4-methoxybenzyl)pent-4-ene-1-sulfonamide (Intermediate EE19, 1.00 g, 2.57 mmol) in THF (10 mL) at −78° C. was added n-butyllithium, 2.5 M solution in hexanes (1.03 mL, 2.57 mmol). The mixture was stirred at this temperature for 30 minutes, and then added a solution of 2-(bromomethyl)thiazole (0.914 g, 5.13 mmol) in THF. The mixture was continued stirring at −78° C. for 1 h and then quenched with saturated aqueous NH$_4$Cl. The mixture was diluted with EtOAc, the organic layer was washed with water, brine and dried (MgSO$_4$). Solvent was evaporated, the crude residue was chromatographed (silica gel, hexane/EtOAc, 9:1 to 1:1) to afford a light oil as the title compounds.

Step 3: (2R)-1-(1,3-thiazol-2-yl)-5-hexene-2-sulfonamide and (2S)-1-(1,3-thiazol-2-yl)-5-hexene-2-sulfonamide

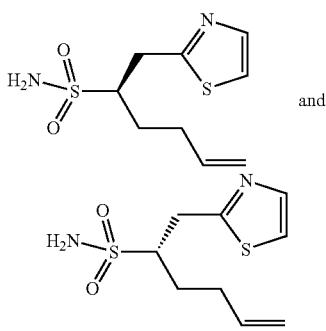

and

A solution of (2S)—N,N-bis(4-methoxybenzyl)-1-(thiazol-2-yl)hex-5-ene-2-sulfonamide and (2R)—N,N-bis(4-methoxybenzyl)-1-(thiazol-2-yl)hex-5-ene-2-sulfonamide (740 mg, 1.52 mmol) in 2,2,2-trifluoroacetic acid (13.9 ml, 122 mmol) was heated with anisole (8.26 ml, 76.0 mmol) at 40° C. for 18 h. The mixture was cooled, concentrated and the residue was chromatographed (silica gel, hexane/EtOAc, 1:0 to 3:1 to 0:1) to afford the title compounds as a colorless oil.

Step 4: (3S)-6'-chloro-5-(((1R,2S)-2-((1S,2E)-1-hydroxy-2-hexen-1-yl)cyclobutyl)methyl)-N-(((2S)-1-(1,3-thiazol-2-yl)-5-hexen-2-yl)sulfonyl)-3',4,4',5-tetrahydro-2'H-spiro[1,5-benzoxazepine-3,1'-naphthalene]-7-carboxamide and (3S)-6'-chloro-5-(((1R,2S)-2-((1S,2E)-1-hydroxy-2-hexen-1-yl)cyclobutyl)methyl)-N-(((2R)-1-(1,3-thiazol-2-yl)-5-hexen-2-yl)sulfonyl)-3',4,4',5-tetrahydro-2'H-spiro[1,5-benzoxazepine-3,1'-naphthalene]-7-carboxamide

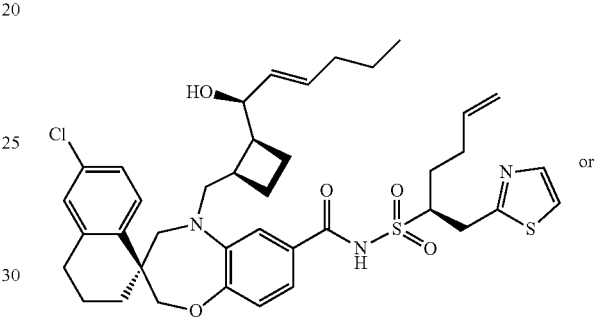

or

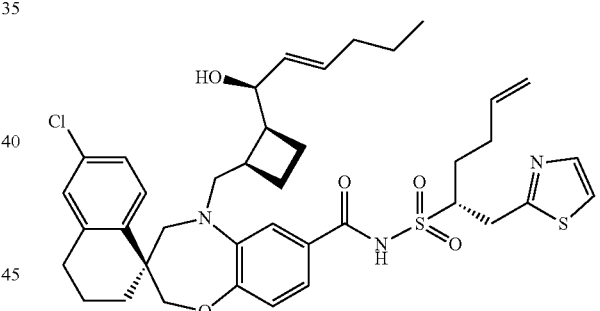

(S)-6'-Chloro-5-(((1R,2S)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A, 100 mg, 0.20 mmol) in CH$_2$Cl$_2$ (1 mL) was mixed with (2S)-1-(1,3-thiazol-2-yl)-5-hexene-2-sulfonamide, (2R)-1-(1,3-thiazol-2-yl)-5-hexene-2-sulfonamide (97 mg, 0.39 mmol), 1-(3-dimethylaminopropyl)-3-ethylcarbodiimide HCl (75 mg, 0.39 mmol), 4-dimethylamino pyridine (48 mg, 0.39 mmol) and triethylamine (0.068 mL, 0.49 mmol) at ambient temperature. The reaction mixture was stirred at ambient temperature for 3 days and quenched with water. The mixture was diluted with CH$_2$Cl$_2$, and the organic layer was dried (MgSO$_4$), filtrated and concentrated. The resulting residue was chromatographed (silica gel, hexane/EtOAc, 9:1 to 1:1) to afford the first eluting isomer as one title compound, m/z (ESI, +ve ion) 738.2 (M+H)$^+$; and the second eluting isomer as the other title compound. m/z (ESI, +ve ion) 738.2 (M+H)$^+$.

Step 5: (1S,3'R,6'R,7'S,8'E,12'S)-6-chloro-7'-hydroxy-12'-(1,3-thiazol-2-ylmethyl)-3,4-dihydro-2H,15'H-spiro[naphthalene-1,22'-[20]oxa[13]thia [1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,12'R)-6-chloro-7'-hydroxy-12'-(1,3-thiazol-2-ylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide A round bottom flask was charged with the first isomer (50 mg, 0.068 mmol) in AcOH (40 mL). After bubbling argon gas into the flask for 15 min, the homogeneous solution was added Hoveyda-Grubbs catalyst II (22 mg, 0.034 mmol) and stirred at ambient temperature under reduced pressure (with a intermediate needle going through a septum into the flask and its other end connecting to the house vacuum) for 18 h. The mixture was quenched with ultrapure silica gel (loading-0.61 mmol/1 g), stirred for 20 min, and filtered. The filtrate was concentrated, and the crude residue was purified by reversed phase preparatory HPLC (Gemini™ Prep $C_{18}$ 5 μm column; Phenomenex, Torrance, CA; gradient elution of 25% to 75% MeCN in water, where both solvents contain 0.1% TFA, 30 min method) to afford the title compound as a white solid. $^1$H NMR (500 MHz, CDCl$_3$) δ ppm 8.45 (br s, 1H), 7.78 (d, J=3.4 Hz, 1H), 7.70 (d, J=8.3 Hz, 1H), 7.35 (d, J=3.4 Hz, 1H), 7.18 (dd, J=2.2, 8.6 Hz, 1H), 7.12-7.06 (m, 1H), 6.96-6.90 (m, 3H), 5.86-5.78 (m, 1H), 5.67 (dd, J=7.2, 15.3 Hz, 1H), 4.64-4.76 (m, 1H), 4.22 (dd, J=4.3, 6.7 Hz, 1H), 4.15-4.05 (m, 3H), 3.91 (d, J=5.7, 15.5 Hz, 1H), 3.79 (d, J=15.4 Hz, 1H), 3.70 (d, J=14.2 Hz, 1H), 3.59 (dd, J=7.0, 15.5 Hz, 1H), 3.25 (d, J=14.2 Hz, 1H), 3.06 (dd, J=8.7, 15.0 Hz, 1H), 2.83-2.71 (m, 2H), 2.50-2.25 (m, 6H), 2.25-1.60 (m, 5H), 1.42 (m, 2H). m/z (ESI, +ve ion) 668.2 (M+H)⁺.

Example 374. (1S,3'R,6'R,7'S,8'Z,12'S)-6-chloro-7'-hydroxy-12'-(1,3-thiazol-2-ylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'Z,12'R)-6-chloro-7'-hydroxy-12'-(1,3-thiazol-2-ylmethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

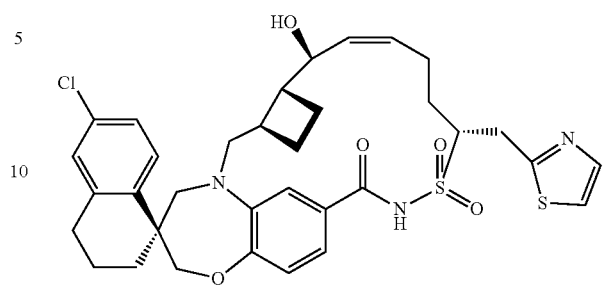

The title compound was prepared from the second eluting isomer in Step 5 of Example 373, using a similar procedure described in the Step 5. $^1$H NMR (500 MHz, CDCl$_3$) δ ppm 7.77 (d, J=3.4 Hz, 1H), 7.72 (d, J=8.3 Hz, 1H), 7.44 (dd, J=2.0, 8.3 Hz, 1H), 7.33 (d, J=3.4 Hz, 1H), 7.18 (dd, J=2.3, 8.4 Hz, 2H), 7.10 (d, J=2.2 Hz, 1H), 7.07-7.03 (m, 1H), 7.00 (d, J=8.3 Hz, 1H), 5.68 (dt, J=5.1, 10.6 Hz, 1H), 5.51 (dd, J=7.1, 10.8 Hz, 1H), 4.51 (t, J=5.6 Hz, 1H), 4.28-4.20 (m, 1H), 4.17-4.04 (m, 3H), 4.04-3.83 (m, 3H), 3.97 (dd, J=3.9, 15.2 Hz, 1H), 3.89 (d, J=14.9 Hz, 1H), 3.75-3.60 (m, 1H), 3.49 (dd, J=10.6, 15.3 Hz, 1H), 3.28-3.19 (m, 1H), 3.13 (dd, J=8.3, 15.7 Hz, 1H), 2.80-2.70 (m, 2H), 2.38-1.73 (m, 6H), 1.73-1.57 (m, 2H), 1.53-1.37 (m, 2H). m/z (ESI, +ve ion) 668.2 (M+H)⁺.

Example 375. (1S,3'R,6'R,7'S,8'E,11R)-6-chloro-7'-(2-methoxyethoxy)-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'S)-6-chloro-7'-(2-methoxyethoxy)-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

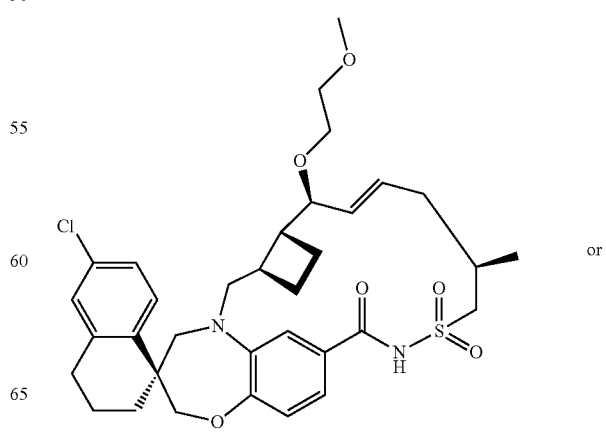

Step 1: (1S,3'R,6'R,7'S,8'E,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

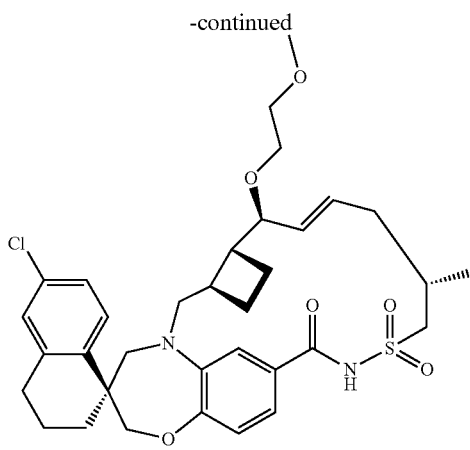

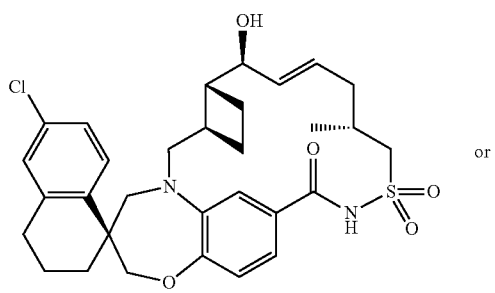

or

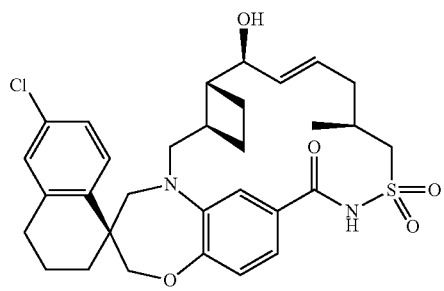

The title compound was synthesized as described for Example 376, Step 5. (1S,3'R,6'R,7'S,8'E,11'R)-6-chloro-7'-hydroxy-11'-methyl-3,4-dihydro-2H,15'H-spiro [naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide was isolated as the second eluting major isomer (12 mg, 0.020 mmol, 21% yield). $^1$H NMR (400 MHz, CD$_2$Cl$_2$) δ 8.44 (br. s., 1H), 7.71 (d, J=8.4 Hz, 1H), 7.17 (dd, J=2.3, 8.6 Hz, 1H), 7.09 (d, J=2.3 Hz, 1H), 6.95-6.90 (m, 2H), 6.89 (s, 1H), 5.82 (ddd, J=5.1, 7.6, 15.1 Hz, 1H), 5.70 (dd, J=8.2, 15.3 Hz, 1H), 4.24 (dd, J=3.9, 12.3 Hz, 1H), 4.20 (dd, J=4.7, 8.8 Hz, 1H), 4.10-4.05 (m, 2H), 3.82 (d, J=14.9 Hz, 1H), 3.69 (d, J=14.3 Hz, 1H), 3.25 (d, J=14.3 Hz, 1H), 3.05 (dd, J=9.6, 15.1 Hz, 1H), 2.98 (dd, J=8.0, 15.3 Hz, 1H), 2.84-2.67 (m, 2H), 2.41 (ddd, J=4.3, 9.8, 18.0 Hz, 1H), 2.36-2.28 (m, 1H), 2.24 (ddd, 7.9, 15.2 Hz, 1H), 2.08-1.99 (m, 2H), 1.98-1.87 (m, 3H), 1.87-1.74 (m, 4H), 1.68 (dd, J=9.4, 18.8 Hz, 1H), 1.46-1.35 (m, 1H), 1.15 (d, J=6.5 Hz, 3H). MS (ESI, +ve ion) m/z 585.1 (M+H)$^+$.

Step 2: (1S,3'R,6'R,7'S,8'E,11R)-6-chloro-7'-(2-methoxyethoxy)-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'S)-6-chloro-7'-(2-methoxyethoxy)-11'-methyl-3,4-dihydro-2H,15'H-spiro[naphthalene-1,22'-[20]oxa[13]thia[1,14]diazatetracyclo[14.7.2.0³,⁶.0¹⁹,²⁴] pentacosa[8,16,18,24]tetraen]-15'-one 13',13'-dioxide To a round bottom flask was added sodium hydride, 60% dispersion in mineral oil (21 mg, 0.51 mmol) and DMF (1 mL) at 0° C. (1S,3'R,6'R,7'S,8'E,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-on or (1S,3'R,6'R,7'S,8'E,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-on (the first isomer, 30 mg, 0.051 mmol) was then added. After the reaction mixture was stirred at 0° C. for 30 min, 2-bromoethyl methyl ether (36 mg, 0.26 mmol) was added. The reaction mixture was allowed to warm up to ambient temperature and stirred for 18 h. The mixture was quenched with 1.0 N aqueous HCl, and diluted with EtOAc. The organic layer was dried (MgSO$_4$) and concentrated. The resulting residue was chromatographed (silica gel, 0-50%, EtOAc+0.5% HOAc/hexane) to afford a solid, 30 mg. This solid was further purified by reversed phase preparatory HPLC (Gemini™ Prep C$_{18}$ 5 μm column; Phenomenex, Torrance, CA; gradient elution of 25% to 75% MeCN in water, where both solvents contain 0.1% TFA, 30 min method) to afford the title compound. $^1$H NMR (500 MHz, CDCl$_3$) δ ppm 8.32 (s, 1H), 7.68 (d, J=8.6 Hz, 1H), 7.17 (dd, J=2.2, 8.6 Hz, 1H), 7.09 (d, J=2.0 Hz, 1H), 7.05-6.97 (m, 1H), 6.92 (d, J=8.1 Hz, 1H), 5.94-5.85 (m, 1H), 5.51 (dd, J=7.0, 15.3 Hz, 1H), 4.17-4.04 (m, 2H), 3.75-3.68 (m, 2H), 3.66-3.46 (m, 7H), 3.44-3.34 (m, 4H), 2.80-2.72 (m 2H), 2.45-2.40 (m, 2H), 2.22-2.10 (m, 3H), 2.00-1.75 (m, 6H), 1.75-1.55 (m, 2H), 1.53-1.48 (m, 1H), 1.18 (d, J=6.4 Hz, 3H). m/z (ESI, +ve ion) 643.2 (M+H)$^+$.

Example 376. (1S,3'R,6'R,7'S,8'E,11'S)-6-chloro-7'-(2-methoxyethoxy)-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'R)-6-chloro-7'-(2-methoxyethoxy)-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

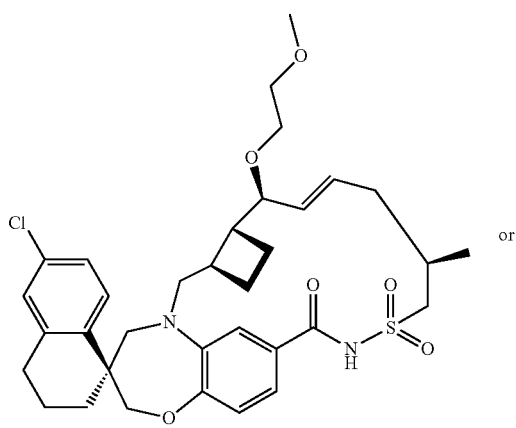

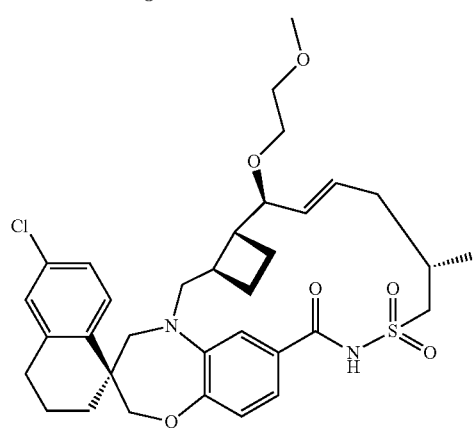

Step 1: (S)—N,N-bis(4-methoxybenzyl)-2-methylpent-4-ene-1-sulfonamide and (R)—N,N-bis(4-methoxybenzyl)-2-methylpent-4-ene-1-sulfonamide

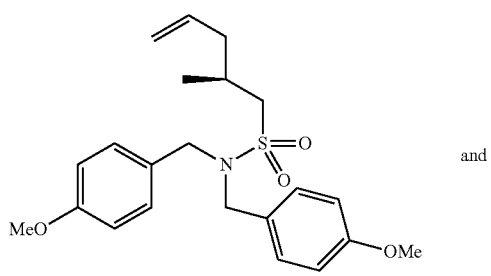 and 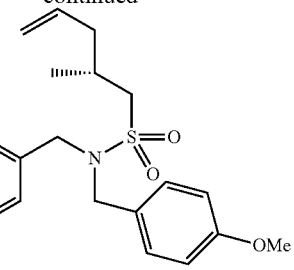

N,N-bis(4-methoxybenzyl)methanesulfonamide (intermediate EE12; 1.05 g, 3.13 mmol) was azeotroped in PhMe under vacuum for 12 h, then, under Ar, THF (21 mL) was added and the solution was cooled to −78° C. Butyllithium solution, (2.5 M in hexanes; 1.63 mL, 4.07 mmol) was then added and the mixture (turned immediately dark) was stirred at −78° C. for 30 min. Pent-4-en-2-yl 4-methylbenzenesulfonate (prepared according to the procedure by Sigman, M. S. et al.; *J. Am. Chem. Soc.*, 2012, 134(28), 11408-11411; 1.3 g, 5.41 mmol) was then added as a solution in 1.5 mL THF. After complete addition the mixture was allowed to warm to ambient temperature and stir overnight. LC/MS analysis showed 50% conversion to the desired product; prolonged stirring for a further 24 h did not improve the conversion. The mixture was then quenched with sat. NH₄Cl, and extracted with EtOAc, dried over MgSO₄ and concentrated. The crude material was purified by chromatography through a 24 g ISCO column, eluting with 10% to 20% to 60% EtOAc in hexanes, to provide a racemic mixture of (S)—N,N-bis(4-methoxybenzyl)-2-methylpent-4-ene-1-sulfonamide and (R)—N,N-bis(4-methoxybenzyl)-2-methylpent-4-ene-1-sulfonamide (408 mg, 1.01 mmol, 32% yield).

Step 2: (S)-2-methylpent-4-ene-1-sulfonamide and (R)-2-methylpent-4-ene-1-sulfonamide

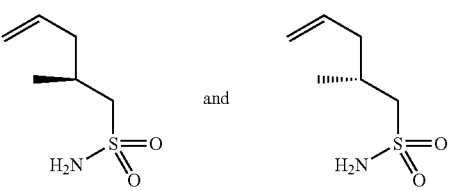

The title compounds were synthesized from (S)—N,N-bis(4-methoxybenzyl)-2-methylpent-4-ene-1-sulfonamide and (R)—N,N-bis(4-methoxybenzyl)-2-methylpent-4-ene-1-sulfonamide (506 mg, 1.25 mmol) following the procedure described for Example 26, Step 2. (S)-2-methylpent-4-ene-1-sulfonamide and (R)-2-methylpent-4-ene-1-sulfonamide were obtained as a racemic mixture (152 mg, 0.930 mmol, 74% yield).

Step 3: (1'S)-tert butyl 6'-chloro-5-(((1R,2R)-2-((1S,5S,E)-1-hydroxy-5-methyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylate and (1'S)-tert butyl 6'-chloro-5-(((1R,2R)-2-((1S,5R,E)-1-hydroxy-5-methyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylate Step 4: (S)-6'-chloro-5-(((1R,2R)-2-((1S,5S,E)-1-hydroxy-5-methyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5R,E)-1-hydroxy-5-methyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic acid

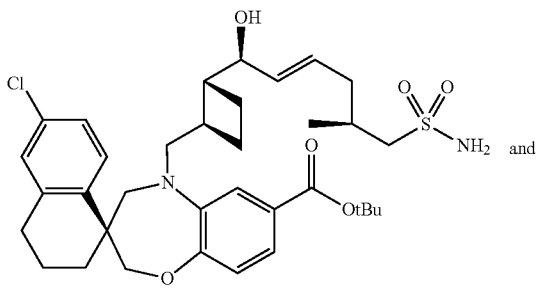 and

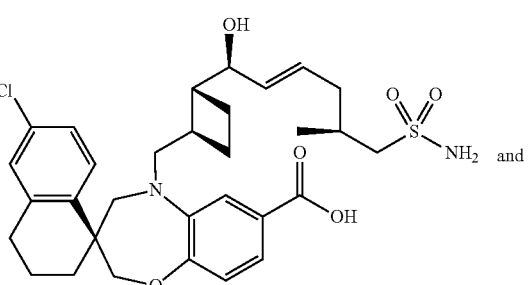 and

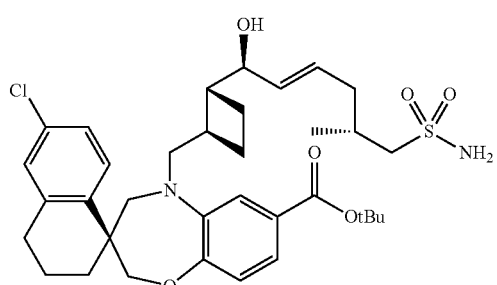

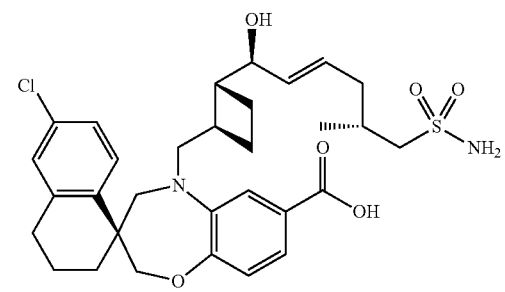

A vial was charged with ((S)-tert-butyl 6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (Intermediate AA12A, Step 1B, first eluting isomer; 120 mg, 0.212 mmol) and a racemic mixture of (S)-2-methylpent-4-ene-1-sulfonamide and (R)-2-methylpent-4-ene-1-sulfonamide (156 mg, 0.954 mmol) in 1,2-DCE (3.03 mL). The solution was sparged with argon and Hoveyda-Grubbs II (13.28 mg, 0.021 mmol) was added as a solution in 1.5 mL 1,2-DCE at ambient temperature. The mixture was stirred (sparging with Ar and venting the vial) at ambient temperature (the clear solution becomes increasingly darker) for 1.5 h (70% conversion by LC/MS analysis). The reaction mixture was then sparged with air for 5 min, concentrated and directly injected into a 24 g ISCO Gold column, and purified eluting with 0-20-50-100% EtOAc/hexane over 16 min to give a mixture of (1'S)-tert butyl 6'-chloro-5-(((1R,2R)-2-((1S,5S,E)-1-hydroxy-5-methyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylate and (1'S)-tert butyl 6'-chloro-5-(((1R,2R)-2-((1S,5R,E)-1-hydroxy-5-methyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylate (63 mg, 0.096 mmol, 45% yield).

To a solid mixture of (1'S)-tert butyl 6'-chloro-5-(((1R,2R)-2-((1S,5S,E)-1-hydroxy-5-methyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylate and (1'S)-tert butyl 6'-chloro-5-(((1R,2R)-2-((1S,5R,E)-1-hydroxy-5-methyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylate (63 mg, 0.096 mmol) and lithium hydroxide monohydrate (0.013 mL, 0.48 mmol) was added a 1:1 mixture of Dioxane/MeOH (1.9 mL). The reaction was heated to 70° C. Virtually no reaction was observed after 1.5 h; water (~0.4 mL) was added and the mixture was stirred for 40 h (still incomplete reaction). The mixture was then quenched with 1 N HCl (1.0 mL), diluted with brine, extracted with EtOAc, dried over MgSO4 and concentrated. The crude material thus obtained (containing traces of starting material) was taken on to the next step without further purification.

Step 5. (1S,3'R,6'R,7'S,8'E,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

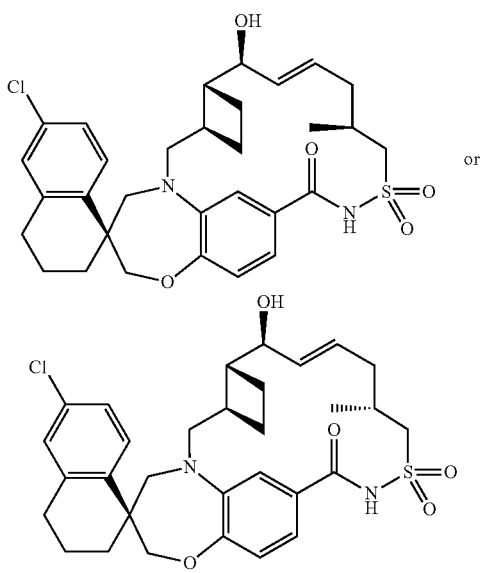

The title compound was synthesized from (S)-6'-chloro-5-(((1R,2R)-2-((1S,5S,E)-1-hydroxy-5-methyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5R,E)-1-hydroxy-5-methyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic acid (57 mg, 0.095 mmol) following the procedure described for Example 323, Step 7. The crude material was purified by chromatography through a 12 g ISCO gold column, eluting with 10-50% EtOAc (containing 0.3% AcOH) in hexanes over 24 min, to provide (1S,3'R,6'R,7'S,8'E,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as the first eluting minor isomer (11 mg, 0.019 mmol, 20% yield, 90% purity). $^1$H NMR (400 MHz, CD$_2$Cl$_2$) δ 8.41 (s, 1H), 7.66 (d, J=8.4 Hz, 1H), 7.50 (br. s., 1H), 7.15 (dd, J=2.3, 8.4 Hz, 1H), 7.10 (d, J=2.3 Hz, 1H), 6.95 (dd, J=2.0, 8.2 Hz, 1H), 6.90 (d, J=8.0 Hz, 1H), 5.69 (dd, J=4.3, 15.8 Hz, 1H), 5.63-5.54 (m, 1H), 4.20 (s, 2H), 4.04 (d, J=15.3 Hz, 1H), 3.94 (dd, J=2.2, 5.2 Hz, 1H), 3.89-3.81 (m, 1H), 3.74-3.63 (m, 1H), 3.39 (d, J=15.3 Hz, 1H), 3.26-3.17 (m, 1H), 3.09-2.96 (m, 1H), 2.81-2.71 (m, 2H), 2.57-2.41 (m, 2H), 2.16 (dd, J=6.5, 11.7 Hz, 1H), 1.92-1.76 (m, 6H), 1.75-1.63 (m, 3H), 1.62-1.41 (m, 2H), 1.19 (d, J=6.1 Hz, 3H). MS (ESI, +ve ion) m/z 585.1 (M+H)$^+$.

Step 6: (1S,3'R,6'R,7'S,8'E,11'S)-6-chloro-7'-(2-methoxyethoxy)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R)-6-chloro-7'-(2-methoxyethoxy)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide The title compound was prepared from (1S,3'R,6'R,7'S,8'E,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]-tetraen]-15'-one 13',13'-dioxide or (1S,3'R,6'R,7'S,8'E,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (30 mg, 0.051 mmol) using a similar procedure described in Example 375, Step 2, reacting with 2-bromoethyl methyl ether (36 mg, 0.26 mmol). Purification by reversed phase preparatory HPLC (Gemini™ Prep C$_{18}$ 5 μm column; Phenomenex, Torrance, CA; gradient elution of 25% to 75% MeCN in water, where both solvents contain 0.1% TFA, 30 min method) to afford the title compound as a white solid. $^1$H NMR (500 MHz, CDCl$_3$) δ ppm 8.22 (s, 1H), 7.70 (d, J=8.6 Hz, 1H), 7.18 (dd, J=2.1, 8.4 Hz, 1H), 7.09 (d, J=2.0 Hz, 1H), 6.95-6.88 (m, 2H), 6.83 (s, 1H), 5.88-5.80 (m, 1H), 5.56 (dd, J=9.0, 15.2 Hz, 1H), 4.36 (dd, J=4.8, 15.3 Hz, 1H), 4.14-4.04 (m, 2H), 3.85-3.78 (m, 2H), 3.71 (d, J=14.2 Hz, 1H), 3.60-3.48 (m, 3H), 3.45-3.34 (m, 4H), 3.23 (d, J=14.4 Hz, 1H), 3.09-2.91 (m, 2H), 2.84-2.71 (m, 2H), 2.53-2.44 (m, 1H), 2.36-2.23 (m, 2H), 2.13-1.92 (m, 5H), 1.89-1.74 (m, 3H), 1.69-1.54 (m, 1H), 1.39 (t, J=12.6 Hz, 1H), 1.16 (d, J=6.6 Hz, 3H). m/z (ESI, +ve ion) 643.2 (M+H)$^+$.

Example 377. (1S,3'R,6'R,7'S,8'E,11'S,12'R)-6-chloro-7'-(2-(2-methoxyethoxy)ethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

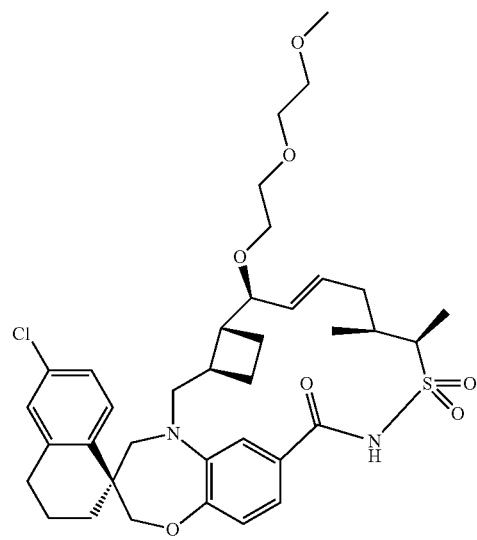 [SMILES: COCCOCCO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

A mixture of dry (1S,3'R,6'R,7'S,8'E,11'S,12'R)-6-chloro-7'-hydroxy-11',12'-dimethyl-3,4-dihydro-2H,15'H-spiro[naphthalene-1,22'[20]oxa[13]thia[1,14]diazatetracyclo[14.7.2.0³,⁶.0¹⁹,²⁴]pentacosa[8,16,18,24]tetraen]-15'-one 13',13'-dioxide (15 mg, 0.025 mmol) from Examples 719, Step 2 and sodium hydride, 60% dispersion in mineral oil (9.9 mg, 0.43 mmol) in DMF was stirred under argon for 10 min. 1-(2-bromoethoxy)-2-methoxyethane (22.6 mg, 0.124 mmol) was added at ambient temperature. The reaction mixture was stirred for 18 h, quenched with saturated aqueous NH₄Cl, and extracted with EtOAc (×3). The combined organic layers were dried (MgSO₄) and concentrated. The residue was chromatographed (silica gel, 0-50%, EtOAc+0.3% HOAc/hexane) to afford the title compound as a white solid. ¹H NMR (400 MHz, CDCl₃) δ ppm 8.09 (s, 1H), 7.70 (d, J=8.6 Hz, 1H), 7.18 (dd, J=2.2, 8.5 Hz, 1H), 7.09 (d, J=2.2 Hz, 1H), 6.95-6.87 (m, 3H), 5.82 (ddd, J=3.2, 9.4, 15.1 Hz, 1H), 5.54 (dd, J=9.1, 15.2 Hz, 1H), 4.35-4.24 (m, 1H), 4.16-4.05 (m, 2H), 3.87-3.74 (m, 2H), 3.70-3.54 (m, 8H), 3.45-3.44 (m, 1H), 3.40 (s, 3H), 3.23 (d, J=14.3 Hz, 1H), 2.99 (dd, J=10.2, 15.3 Hz, 1H), 2.84-2.71 (m, 2H), 2.53-2.42 (m, 1H), 2.38-2.24 (m, 1H), 2.15-1.93 (m, 4H), 1.90-1.72 (m, 3H), 1.72-1.57 (m, 3H), 1.49 (d, J=7.2 Hz, 3H), 1.42-1.35 (m, 1H), 1.05 (d, J=6.8 Hz, 3H). m/z (ESI, +ve ion) 701.2 (M+H)⁺.

Example 378. (1S,3'R,6'R,7'S,8'E,11'S,12'R)-6-chloro-7'-(2-(2-(2-methoxyethoxy)ethoxy)ethoxy)-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

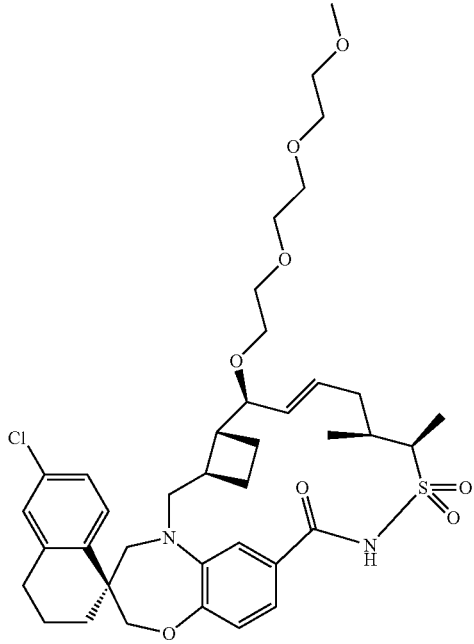 [SMILES: COCCOCCOCCO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

The title compound was prepared from (1S,3'R,6'R,7'S,8'E,11'S,12'R)-6-chloro-7'-hydroxy-11',12'-dimethyl-3,4-dihydro-2H,15'H-spiro[naphthalene-1,22'[20]oxa[13]thia[1,14]diazatetracyclo[14.7.2.0³,⁶.0¹⁹,²⁴]pentacosa[8,16,18,24]tetraen]-15'-one 13',13'-dioxide (Examples 719, Step 2) using a similar procedure described in Example 377 replacing 1-(2-bromoethoxy)-2-methoxyethane with 1-bromo-2-[2-(2-methoxyethoxy)ethoxy]ethane. ¹H NMR (400 MHz, CDCl₃) δ ppm 7.97 (s, 1H), 7.70 (d, J=8.4 Hz, 1H), 7.19 (dd, J=2.2, 8.4 Hz, 1H), 7.10 (d, J=2.0 Hz, 1H), 6.95-6.87 (m, 3H), 5.86-5.75 (m, 1H), 5.54 (dd, J=9.0, 15.1 Hz, 1H), 4.35-4.22 (m, 1H), 4.13-4.05 (m, 2H), 3.86-3.76 (m, 2H), 3.72-3.63 (m, 7H), 3.63-3.54 (m, 5H), 3.44-3.42 (m, 1H), 3.40 (s, 3H), 3.23 (d, J=14.3 Hz, 1H), 2.99 (dd, J=10.1, 15.4 Hz, 1H), 2.84-2.71 (m, 2H), 2.48 (d, J=10.6 Hz, 1H), 2.38-2.26 (m, 1H), 2.21-1.90 (m, 4H), 1.89-1.72 (m, 3H), 1.70-1.58 (m, 3H), 1.50 (d, J=7.2 Hz, 3H), 1.45-1.32 (m, 1H), 1.06 (d, J=6.8 Hz, 3H). m/z (ESI, +ve ion) 745.2 (M+H)⁺.

Example 379. (1S,3'R,6'R,7'S,8'E,11'S,12'R)-6-chloro-11',12'-dimethyl-7'-(3,6,9,12-tetraoxatridec-1-yloxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

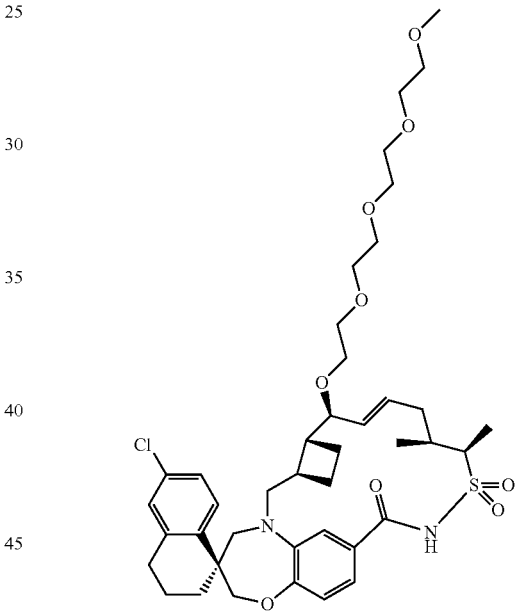

The title compound was prepared from (1S,3'R,6'R,7'S,8'E,11'S,12'R)-6-chloro-7'-hydroxy-11',12'-dimethyl-3,4-dihydro-2H,15'H-spiro[naphthalene-1,22'[20]oxa[13]thia[1,14]diazatetracyclo[14.7.2.0³,⁶.0¹⁹,²⁴]pentacosa[8,16,18,24]tetraen]-15'-one 13',13'-dioxide (Example 719, Step 2) using a similar procedure described in Example 377, replacing 1-(2-bromoethoxy)-2-methoxyethane with triethylene glycol 2-bromoethyl methyl ether. ¹H NMR (400 MHz, CDCl₃) δ ppm 8.02 (s, 1H), 7.70 (d, J=8.6 Hz, 1H), 7.19 (dd, J=2.2, 8.4 Hz, 1H), 7.09 (d, J=2.2 Hz, 1H), 6.94-6.88 (m, 3H), 5.85-5.77 (m, 1H), 5.54 (dd, J=8.5, 15.4 Hz, 1H), 4.31 (q, J=7.4 Hz, 1H), 4.09 (s, 2H), 3.85-3.75 (m, 2H), 3.74-3.62 (m, 11H), 3.62-3.50 (m, 5H), 3.45-3.42 (m, 1H), 3.39 (s, 3H), 3.23 (d, J=14.3 Hz, 1H), 3.03-2.95 (m, 1H), 2.83-2.72 (m, 2H), 2.52-2.43 (m, 1H), 2.32 (t, J=9.5 Hz, 1H), 2.21-1.92 (m, 4H), 1.90-1.74 (m, 3H), 1.68-1.56 (m, 3H), 1.50 (d, J=7.2 Hz, 3H), 1.40 (t, J=13.2 Hz, 1H), 1.06 (d, J=6.8 Hz, 3H). m/z (ESI, +ve ion) 789.2 (M+H)⁺.

Example 385. (1S,3'R,6'R,7'S,8'E,11'S,12'R)-6-chloro-12'-(cyclopropylmethyl)-7'-(2-methoxyethoxy)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-12'-(cyclopropylmethyl)-7'-(2-methoxyethoxy)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-12'-(cyclopropylmethyl)-7'-(2-methoxyethoxy)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-12'-(cyclopropylmethyl)-7'-(2-methoxyethoxy)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

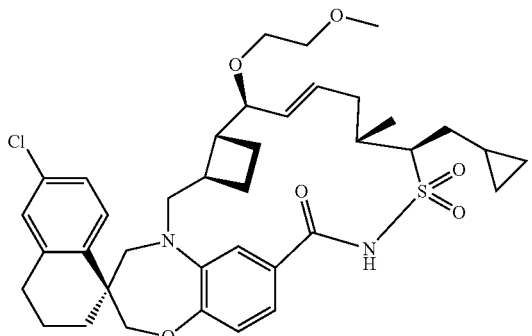

Step 1: (2S)—N,N-bis(4-methoxybenzyl)-2-methyl-pent-4-ene-1-sulfonamide and (2R)—N,N-bis(4-methoxybenzyl)-2-methyl-4-pentene-1-sulfonamide

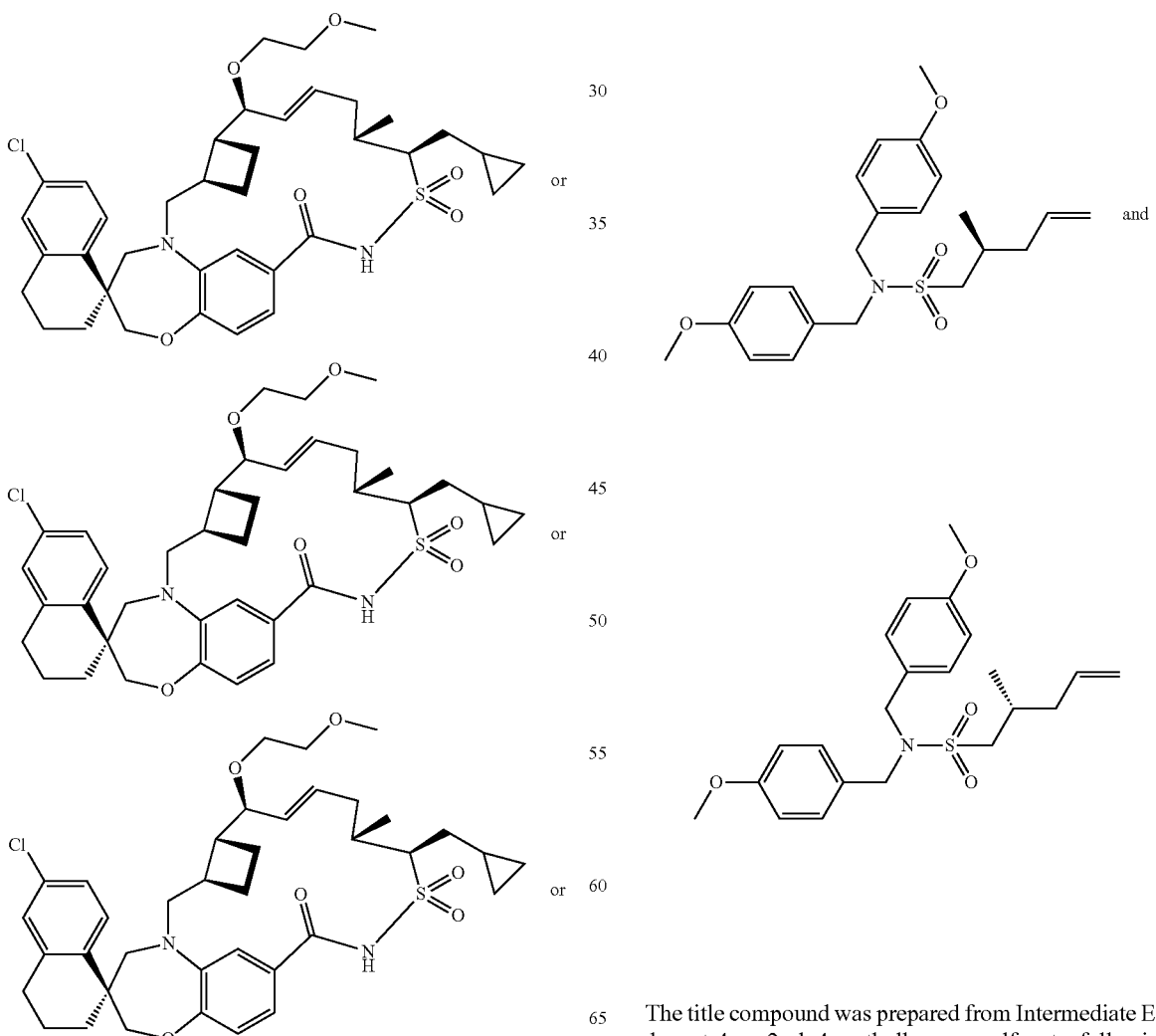

The title compound was prepared from Intermediate EE12 and pent-4-en-2-yl 4-methylbenzenesulfonate following a similar procedure described in Example 434, Step 1.

Step 2: (2S,3R)-1-cyclopropyl-N,N-bis(4-methoxy-benzyl)-3-methyl-5-hexene-2-sulfonamide and (2R,3S)-1-cyclopropyl-N,N-bis(4-methoxybenzyl)-3-methyl-5-hexene-2-sulfonamide and (2R,3R)-1-cyclopropyl-N,N-bis(4-methoxybenzyl)-3-methyl-5-hexene-2-sulfonamide and (2S,3S)-1-cyclopropyl-N,N-bis(4-methoxybenzyl)-3-methyl-5-hexene-2-sulfonamide

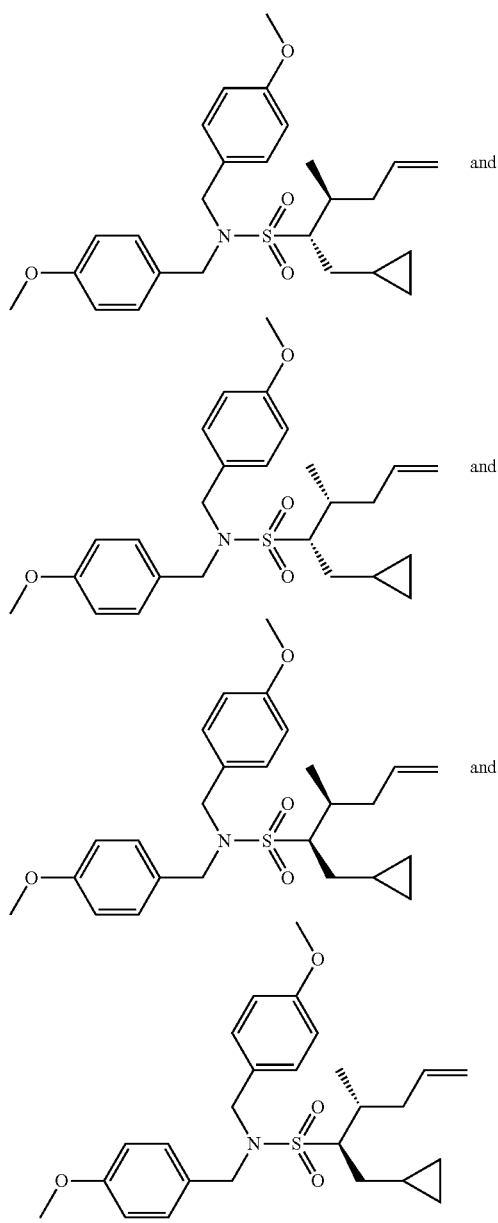

To a solution of (2S)—N,N-bis(4-methoxybenzyl)-2-methylpent-4-ene-1-sulfonamide and (2R)—N,N-bis(4-methoxybenzyl)-2-methylpent-4-ene-1-sulfonamide (600 mg, 1.49 mmol) in THF was added butyllithium solution, 2.5 N in hexanes (0.624 mL, 1.56 mmol) at −78° C. under N₂. After the reaction was stirred at this temperature for 15 min, a solution of (bromomethyl)-cyclopropane (0.288 mL, 2.97 mmol) in THF (1 mL) was added. The reaction mixture was stirred at −78° C. for 1 h and then allowed to warm up to ambient temperature. The mixture was quenched with water, and extracted with EtOAc. The organic layer was washed with water and dried (Na₂SO₄). Solvent was evaporated, the resulting residue was chromatographed (silica gel, 10 to 50%, EtOAc/Hexanes) to afford the title compounds as a colorless liquid.

Step 3: (2S,3S)-1-cyclopropyl-3-methylhex-5-ene-2-sulfonamide and (2S,3R)-1-cyclopropyl-3-methyl-hex-5-ene-2-sulfonamide and (2R,3S)-1-cyclopropyl-3-methylhex-5-ene-2-sulfonamide and (2R,3R)-1-cyclopropyl-3-methylhex-5-ene-2-sulfonamide

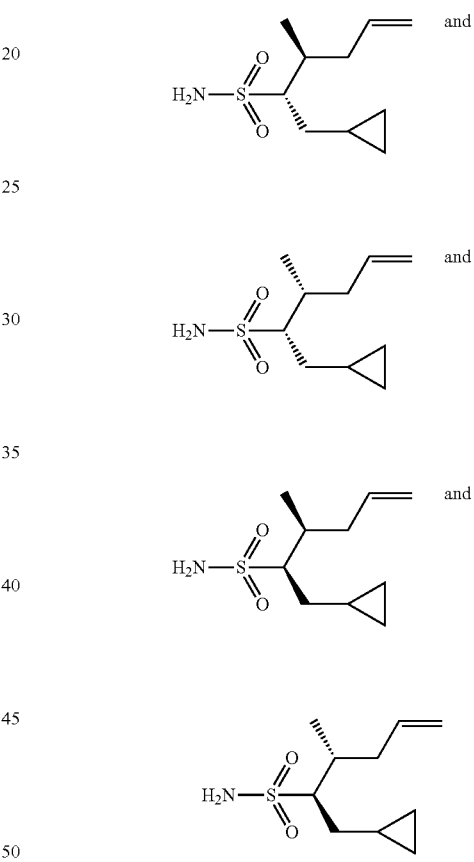

A mixture of (2S,3R)-1-Cyclopropyl-N,N-bis(4-methoxybenzyl)-3-methyl-5-hexene-2-sulfonamide and (2R,3S)-1-cyclopropyl-N,N-bis(4-methoxybenzyl)-3-methyl-5-hexene-2-sulfonamide and (2R,3R)-1-cyclopropyl-N,N-bis(4-methoxybenzyl)-3-methyl-5-hexene-2-sulfonamide and (2S,3S)-1-cyclopropyl-N,N-bis(4-methoxybenzyl)-3-methyl-5-hexene-2-sulfonamide (510 mg, 1.11 mmol) was treated with anisole (1.81 g, 16.7 mmol) in 2,2,2-trifluoroacetic acid (3.81 g, 33.4 mmol). The mixture was stirred, heated at 40° C. for 18 h and then concentrated. The resulting residue was chromatographed (silica gel, hexane/EtOAc, 9:1 to 1:1) to afford the title compounds as a light brown oil.

Step 4: (3S)-6'-chloro-N-(((2R,3S)-1-cyclopropyl-3-methyl-5-hexen-2-yl)sulfonyl)-5-(((1R,2R)-2-((1S,2E)-1-hydroxy-2-hexen-1-yl)cyclobutyl)methyl)-3',4,4',5-tetrahydro-2'H-spiro[1,5-benzoxazepine-3,1'-naphthalene]-7-carboxamide and (3S)-6'-chloro-N-(((2R,3R)-1-cyclopropyl-3-methyl-5-hexen-2-yl)sulfonyl)-5-(((1R,2R)-2-((1S,2E)-1-hydroxy-2-hexen-1-yl)cyclobutyl)methyl)-3',4,4',5-tetrahydro-2'H-spiro[1,5-benzoxazepine-3,1'-naphthalene]-7-carboxamide and (3S)-6'-chloro-N-(((2S,3S)-1-cyclopropyl-3-methyl-5-hexen-2-yl)sulfonyl)-5-(((1R,2R)-2-((1S,2E)-1-hydroxy-2-hexen-1-yl)cyclobutyl)methyl)-3',4,4',5-tetrahydro-2'H-spiro[1,5-benzoxazepine-3,1'-naphthalene]-7-carboxamide and (3S)-6'-chloro-N-(((2S,3R)-1-cyclopropyl-3-methyl-5-hexen-2-yl)sulfonyl)-5-(((1R,2R)-2-((1S,2E)-1-hydroxy-2-hexen-1-yl)cyclobutyl)methyl)-3',4,4',5-tetrahydro-2'H-spiro[1,5-benzoxazepine-3,1'-naphthalene]-7-carboxamide

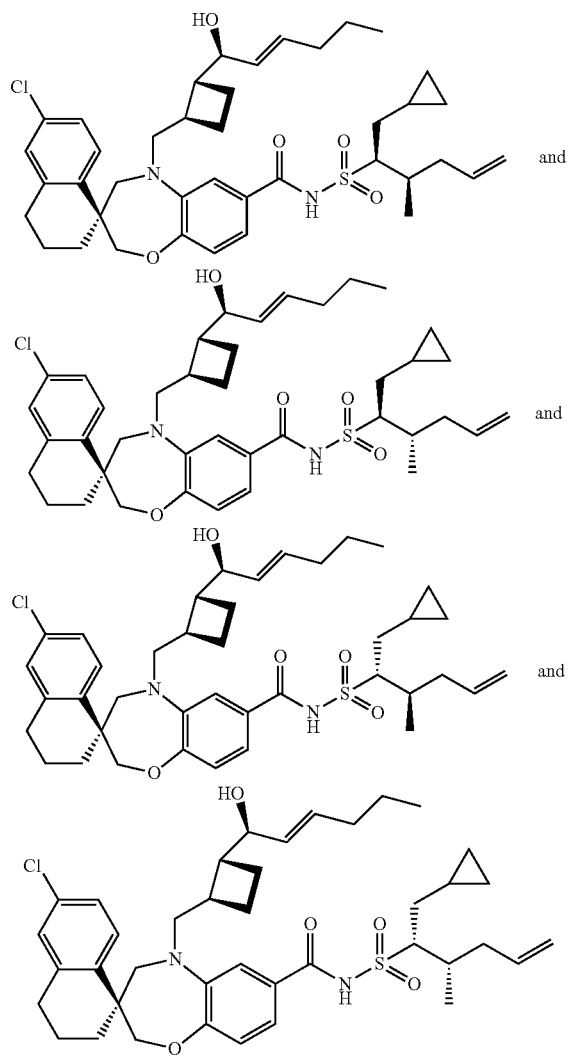

A mixture of (2S,3S)-1-cyclopropyl-3-methylhex-5-ene-2-sulfonamide, (2S,3R)-1-cyclopropyl-3-methylhex-5-ene-2-sulfonamide, (2R,3S)-1-cyclopropyl-3-methylhex-5-ene-2-sulfonamide, and (2R,3R)-1-cyclopropyl-3-methylhex-5-ene-2-sulfonamide (160 mg, 0.74 mmol) was added (S)-6'-chloro-5-(((1R,2S)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A 250 mg, 0.49 mmol), 1-(3-dimethylaminopropyl)-3-ethylcarbodiimide hydrochloride (141 mg, 0.74 mmol), 4-dimethylaminopyridine (90 mg, 0.74 mmol) and triethylamine (0.20 mL, 1.5 mmol) in $CH_2Cl_2$ (1 mL). The reaction mixture was stirred at ambient temperature for 3 days. The mixture was then diluted with $CH_2Cl_2$, and added water. The organic layer was dried ($MgSO_4$), and concentrated. The resulting residue was chromatographed (silica gel, 1:0 to 1:1, hexane/EtOAc+0.5% HOAc) to afford the title compounds.

Step 5: (1S,3'R,6'R,7'S,8'E,11'S,12'R)-6-chloro-12'-(cyclopropyl methyl)-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-12'-(cyclopropylmethyl)-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-12'-(cyclopropylmethyl)-7'-hydroxy-11'-methyl-3,4-dihydro-2H,15'H-spiro[naphthalene-1,22'-[20]oxa[13]thia [1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-12'-(cyclopropylmethyl)-7'-hydroxy-11'-methyl-3,4-dihydro-2H,15'H-spiro[naphthalene-1,22'-[20]oxa[13]thia [1,14]diazatetracyclo[14.7.2.0$^{3,6}$.0$^{19,24}$]pentacosa[8,16,18,24]tetraen]-15'-one 13',13'-dioxide

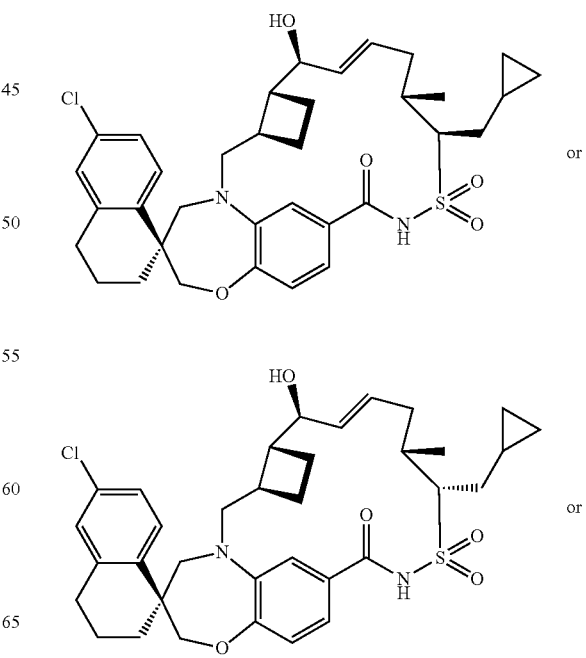

903

-continued

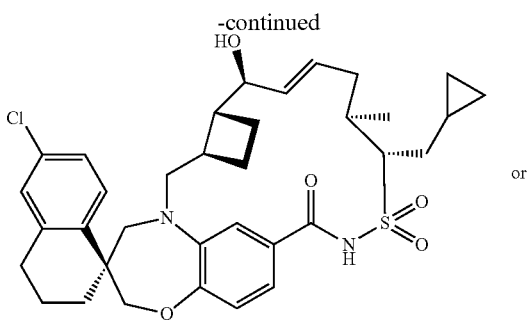

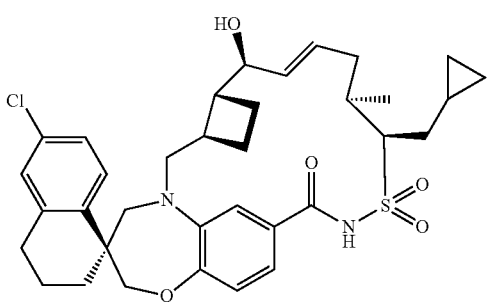

A round bottom flask was charged with above mixture of (3S)-6'-chloro-n-(((2R,3S)-1-cyclopropyl-3-methyl-5-hexen-2-yl)sulfonyl)-5-(((1R,2R)-2-((1S,2E)-1-hydroxy-2-hexen-1-yl)cyclobutyl)methyl)-3',4,4',5-tetrahydro-2'H-spiro[1,5-benzoxazepine-3,1'-naphthalene]-7-carboxamide, (3S)-6'-chloro-n-(((2R,3R)-1-cyclopropyl-3-methyl-5-hexen-2-yl)sulfonyl)-5-(((1R,2R)-2-((1S,2E)-1-hydroxy-2-hexen-1-yl)cyclobutyl)methyl)-3',4,4',5-tetrahydro-2'H-spiro[1,5-benzoxazepine-3,1'-naphthalene]-7-carboxamide, (3S)-6'-chloro-n-(((2S,3S)-1-cyclopropyl-3-methyl-5-hexen-2-yl)sulfonyl)-5-(((1R,2R)-2-((1S,2E)-1-hydroxy-2-hexen-1-yl)cyclobutyl)methyl)-3',4,4',5-tetrahydro-2'H-spiro[1,5-benzoxazepine-3,1'-naphthalene]-7-carboxamide and (3S)-6'-chloro-n-(((2S,3R)-1-cyclopropyl-3-methyl-5-hexen-2-yl)sulfonyl)-5-(((1R,2R)-2-((1S,2E)-1-hydroxy-2-hexen-1-yl)cyclobutyl)methyl)-3',4,4',5-tetrahydro-2'H-spiro[1,5-benzoxazepine-3,1'-naphthalene]-7-carboxamide (210 mg, 0.30 mmol) in DCE (100 mL). After bubbling into the flask with Argon for 15 min, the homogeneous solution was added Hoveyda-Grubbs catalyst II (65 mg, 0.35 mmol) and stirred at 50° C. for 18 h. The reaction mixture was cooled and introduced air by bubbling air into the flask for 2 min. Solvent was evaporated, and the crude residue was purified by reversed phase preparatory HPLC (Gemini™ Prep $C_{18}$ 5 μm column; Phenomenex, Torrance, CA; gradient elution of 25% to 75% MeCN in water, where both solvents contain 0.1% TFA, 30 min method) to afford the title compound as the first eluenting isomer. $^1$H NMR (500 MHz, CDCl$_3$) δ ppm 8.08 (s, 1H), 7.70 (d, J=8.3 Hz, 1H), 7.19 (dd, J=2.2, 8.6 Hz, 1H), 7.10 (d, J=2.0 Hz, 1H), 6.99 (br s, 1H), 6.97-6.89 (m, 2H), 5.97-5.88 (m, 1H), 5.72 (dd, J=8.1, 15.2 Hz, 1H), 4.30-4.22 (m, 2H), 4.10 (s, 2H), 3.82 (d, J=14.9 Hz, 1H), 3.69 (d, J=14.2 Hz, 1H), 3.26 (d, J=14.2 Hz, 1H), 3.06 (br s, 1H), 2.85-2.71 (m, 2H), 2.53-2.39 (m, 1H), 2.33 (quin, J=8.7 Hz, 1H), 2.27-2.12 (m, 2H), 2.09-1.86 (m, 5H), 1.86-1.77 (m, 3H), 1.75-1.61 (m, 1H), 1.50-1.31 (m, 2H), 1.23-1.12 (m, 1H), 1.05 (d, J=6.8 Hz, 3H), 0.63 (d, J=7.8 Hz, 2H), 0.35-0.25 (m, 1H), 0.13-0.06 (m, 1H). m/z (ESI, +ve ion) 639.2 (M+H)$^+$.

904

Step 6: (1S,3'R,6'R,7'S,8'E,11'S,12'R)-6-chloro-12'-(cyclopropylmethyl)-7'-(2-methoxyethoxy)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-12'-(cyclopropylmethyl)-7'-(2-methoxyethoxy)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-12'-(cyclopropylmethyl)-7'-(2-methoxyethoxy)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-12'-(cyclopropylmethyl)-7'-(2-methoxyethoxy)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

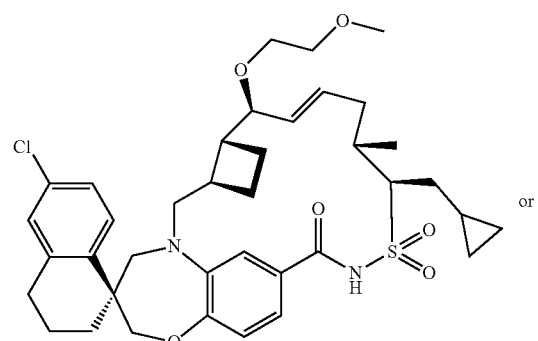

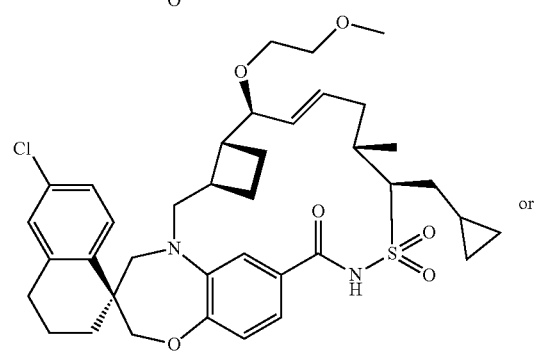

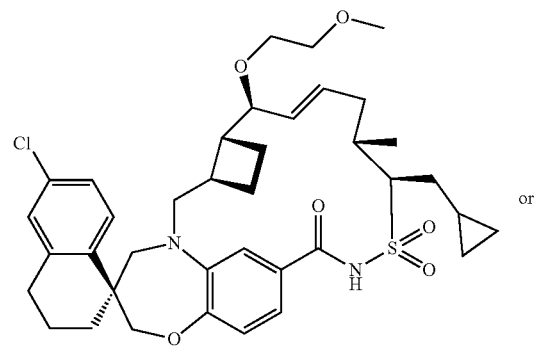

-continued

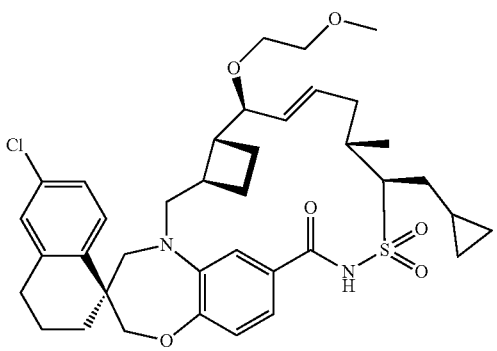

The title compound was prepared from (1S,3'R,6'R,7'S,8'E,11'S,12'R)-6-chloro-12'-(cyclopropylmethyl)-7'-hydroxy-11'-methyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-12'-(cyclopropylmethyl)-7'-hydroxy-11'-methyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11R,12'R)-6-chloro-12'-(cyclopropylmethyl)-7'-hydroxy-11'-methyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11R,12'S)-6-chloro-12'-(cyclopropylmethyl)-7'-hydroxy-11'-methyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Step 5) by a similar procedure described in Example 720, replacing 4-(2-bromoethyl)morpholine hydrobromide with 2-bromoethyl methyl ether (0.012 mL, 0.125 mmol). $^1$H NMR (400 MHz, CDCl$_3$) δ ppm 8.05 (s, 1H), 7.70 (d, J=8.6 Hz, 1H), 7.18 (dd, J=2.2, 8.5 Hz, 1H), 7.09 (d, J=2.2 Hz, 1H), 6.96-6.90 (m, 3H), 5.91-5.83 (m, 1H), 5.56 (dd, J=9.0, 15.1 Hz, 1H), 4.30 (dd, J=4.5, 7.2 Hz, 1H), 4.09 (s, 2H), 3.87-3.79 (m, 2H), 3.74-3.67 (m, 1H), 3.59-3.50 (m, 3H), 3.48-3.41 (m, 1H), 3.41-3.35 (s, 3H), 3.23 (d, J=14.5 Hz, 1H), 3.00 (dd, J=10.2, 15.3 Hz, 1H), 2.84-2.71 (m, 2H), 2.50 (d, J=10.6 Hz, 1H), 2.37-2.16 (m, 3H), 2.13-1.92 (m, 4H), 1.91-1.73 (m, 3H), 1.71-1.52 (m, 2H), 1.51-1.34 (m, 2H), 1.23-1.14 (m, 1H), 1.05 (d, J=6.8 Hz, 3H), 0.67-0.58 (m, 2H), 0.29 (dd, J=4.4, 9.1 Hz, 1H), 0.08 (dd, J=4.1, 9.0 Hz, 1H). m/z (ESI, +ve ion) 697.3 (M+H)$^+$.

Example 386. (1S,3'R,6'R,7'S,8'E,11'S,12'R)-6-chloro-12'-(cyclopropylmethyl)-11'-methyl-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-12'-(cyclopropylmethyl)-11'-methyl-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-12'-(cyclopropylmethyl)-11'-methyl-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-12'-(cyclopropylmethyl)-11'-methyl-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

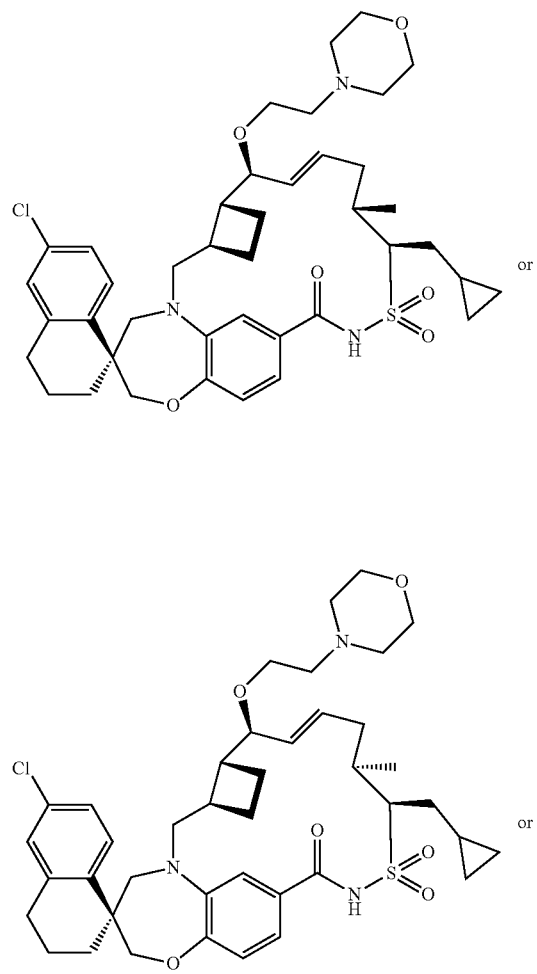

907

-continued

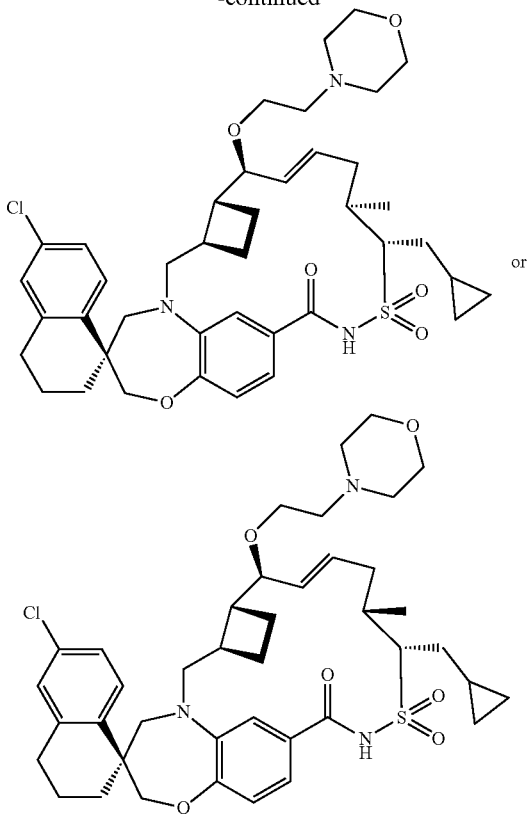

The title compound was prepared from (1S,3'R,6'R,7'S,8'E,11'S,12'R)-6-chloro-12'-(cyclopropylmethyl)-7'-hydroxy-11'-methyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-12'-(cyclopropylmethyl)-7'-hydroxy-11'-methyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-12'-(cyclopropylmethyl)-7'-hydroxy-11'-methyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-12'-(cyclopropylmethyl)-7'-hydroxy-11'-methyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 385, Step 5, 11 mg, 0.017 mmol) by a similar procedure described in Example 720, replacing 4-(2-bromoethyl)morpholine hydrobromide with 4-(2-bromoethyl)morpholine hydrobromide. $^1$H NMR (500 MHz, CDCl$_3$) δ ppm 8.03 (s, 1H), 7.70 (d, J=8.6 Hz, 1H), 7.19 (dd, J=2.2, 8.6 Hz, 1H), 7.10 (d, J=2.0 Hz, 1H), 6.95-6.89 (m, 3H), 5.92-5.83 (m, 1H), 5.54 (dd, J=8.9, 15.3 Hz, 1H), 4.30-4.20 (m, 1H), 4.10 (s, 2H), 3.88-3.66 (m, 7H), 3.58 (br s, 1H), 3.46 (br s, 1H), 3.23 (d, J=14.2 Hz, 1H), 3.01 (dd, J=10.1, 15.3 Hz, 1H), 2.97 (s, 1H), 2.89 (s, 1H), 2.84-2.63 (m, 2H), 2.60-2.48 (m, 4H), 2.46-2.40 (m, 1H), 2.37-2.28 (m, 1H), 2.28-2.15 (m, 2H), 2.13-1.91 (m, 5H), 1.89-1.73 (m, 3 H), 1.70-1.60 (m, 1H), 1.53-1.35 (m, 2H), 1.25-1.15 (m, 1H), 1.05 (d, J=7.1 Hz, 3H), 0.66-0.58 (m, 2H), 0.32-0.26 (m, 1H), 0.11-0.04 (m, 1H). m/z (ESI, +ve ion) 752.3 (M+H)$^+$.

908

Example 387. (1S,3'R,6'R,7'S,8'E,11'S,12'R)-6-chloro-12'-(cyclopropylmethyl)-11'-methyl-7'-(((2R)-2-(4-morpholinyl)propyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,11'S,12'S)-6-chloro-12'-(cyclopropylmethyl)-11'-methyl-7'-(((2R)-2-(4-morpholinyl)propyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,11'R,12'R)-6-chloro-12'-(cyclopropylmethyl)-11'-methyl-7'-(((2R)-2-(4-morpholinyl)propyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,11'R,12'S)-6-chloro-12'-(cyclopropylmethyl)-11'-methyl-7'-(((2R)-2-(4-morpholinyl)propyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

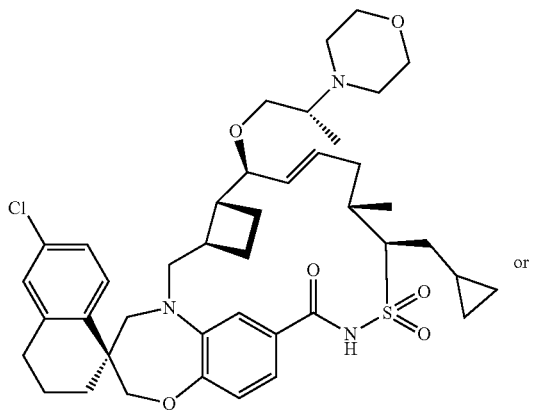

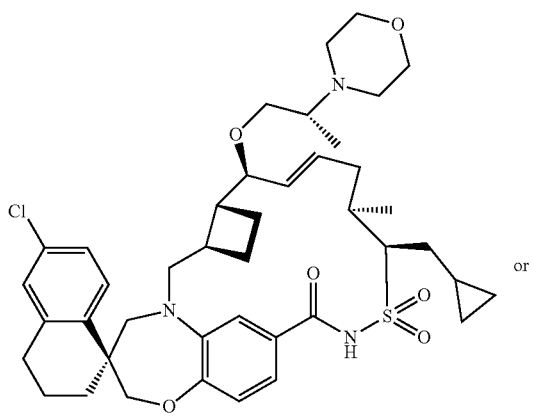

-continued

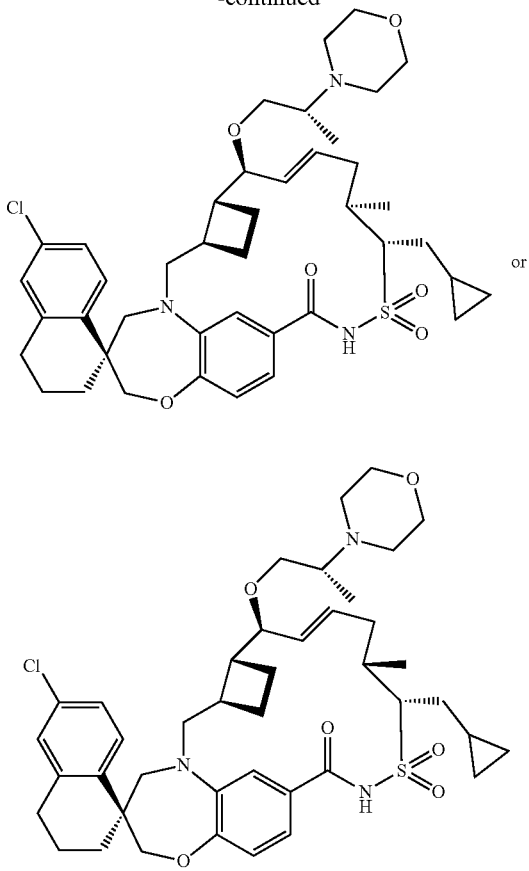

or

Step 1: (R)-2-morpholinopropan-1-ol

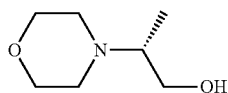

2-Bromoethyl ether (8.20 mL, 35.4 mmol) in DCM was added (R)-2-aminopropan-1-ol (13.3 g, 177 mmol) at ambient temperature with vigorous stirring. The highest internal temperature was 42° C. after 19 min. The reaction mixture was stirred for 24 h and diluted with dichloromethane (10 mL). The mixture was quenched with saturated aqueous potassium carbonate (10 mL), and extracted with dichloromethane. The combined organic layers were dried (MgSO$_4$), and filtered. The filtrate was concentrated, and chromatographed gel. 0 to 20%, MeOH/DCM) to afford the title compound.

Step 2: (R)-4-(1-chloropropan-2-yl)morpholine hydrochloride

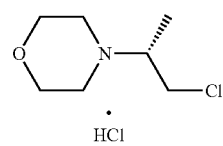

(R)-2-Morpholinopropan-1-ol (2.85 g, 19.6 mmol) was dissolved in toluene (15 mL) and added sulfurous dichloride (1.71 mL, 23.6 mmol). The reaction mixture was heated at 80° C. for 3 h, cooled, and concentrated under reduced pressure. Additional anhydrous toluene was added and concentrated. This process was repeated with toluene three times and then switched to isohexane (1×). The resulting residue was slurried in diethyl ether, filtered, and the solid was washed with copious amount of diethyl ether. The stick solid was dried under vacuum at ambient temperature to afford the title compound (1.60 g, 50%).

Step 3: (1S,3'R,6'R,7'S,8'E,11'S,12'R)-6-chloro-12'-(cyclopropylmethyl)-11'-methyl-7'-(((2R)-2-(4-morpholinyl)propyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide and (1S,3'R,6'R, 7'S,8'E,11'S,12'S)-6-chloro-12'-(cyclopropylmethyl)-11'-methyl-7'-(((2R)-2-(4-morpholinyl)propyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,11'R,12'R)-6-chloro-12'-(cyclopropylmethyl)-11'-methyl-7'-(((2R)-2-(4-morpholinyl)propyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R, 7'S,8'E,11'R,12'S)-6-chloro-12'-(cyclopropylmethyl)-11'-methyl-7'-(((2R)-2-(4-morpholinyl)propyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide The title compound was prepared from (1S,3'R,6'R,7'S,8'E,11'S,12'R)-6-chloro-12'-(cyclopropylmethyl)-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$] pentacosa[8,16,18,24]tetraen]-15'-one 13',13'-dioxide or (1S,3'R,6'R,7'S,8'E,11'S,12'S)-6-chloro-12'-(cyclopropylmethyl)-7'-hydroxy-11'-methyl-3,4-dihydro-2H, 15'H-spiro[naphthalene-1,22'-[20]oxa[13]thia[1,14] diazatetracyclo[14.7.2.0$^{3,6}$.0$^{19,24}$]pentacosa [8,16,18,24] tetraen]-15'-one 13',13'-dioxide or (1S,3'R,6'R,7'S,8'E,11'R, 12'R)-6-chloro-12'-(cyclopropylmethyl)-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-12'-(cyclopropylmethyl)-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 385, Step 5, 22 mg, 0.034 mmol) by a similar procedure described in Example 720, replacing 4-(2-bromoethyl)morpholine hydrobromide with (R)-4-(1-chloropropan-2-yl)morpholine hydrochloride. $^1$H NMR (500 MHz, CDCl$_3$) δ ppm 8.11 (br s, 1H), 7.69 (d, J=8.6 Hz, 1H), 7.23-7.17 (m, 1H), 7.10 (d, J=2.0 Hz, 1H), 6.96-6.84 (m, 3H), 5.98-5.92 (m, 1H), 5.54 (dd, J=9.3, 15.2 Hz, 1H), 4.29-4.19 (m, 1H), 4.10 (s, 2H), 4.07-3.92 (m, 4H), 3.84-3.69 (m, 4H), 3.55 (br s, 1H), 3.51-3.35 (m, 3H), 3.23 (d, J=14.4 Hz, 2H), 3.16-2.98 (m, 2H), 2.85-2.67 (m, 2H), 2.50-2.40 (m, 1H), 2.38-2.15 (m, 4H), 2.14-1.60 (m, 10H), 1.50-1.41 (m, 1H), 1.39 (d, J=6.8 Hz, 3H), 1.25-1.20 (m, 1H), 1.15-0.99 (m, 3H), 0.65-0.58 (m, 2H), 0.29 (dd, J=4.4, 9.0 Hz, 1H), 0.09-0.04 (m, 1H). m/z (ESI, +ve ion) 766.2 (M+H)$^+$.

Example 393. (1S,3'R,6'R,7'S,8'E,11'S,12'R)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

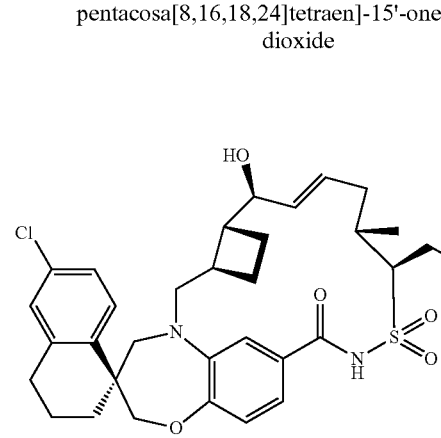

or

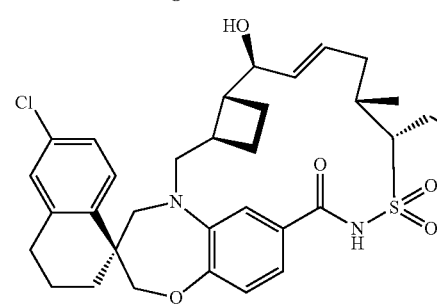

or

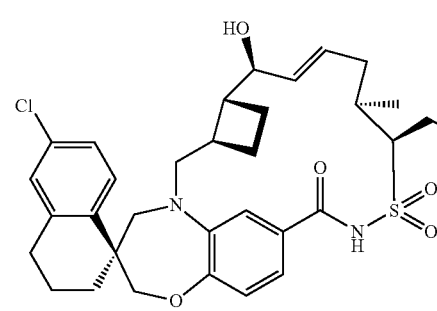

or

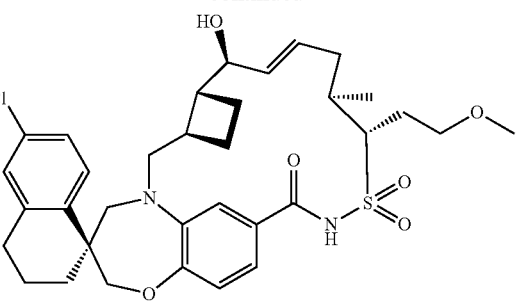

Step 1: (3R,4S)-1-hydroxy-N,N-bis(4-methoxybenzyl)-4-methyl-6-heptene-3-sulfonamide and (3R,4S)-1-hydroxy-N,N-bis(4-methoxybenzyl)-4-methyl-6-heptene-3-sulfonamide and (3R,4S)-1-hydroxy-N,N-bis(4-methoxybenzyl)-4-methyl-6-heptene-3-sulfonamide and (3R,4S)-1-hydroxy-N,N-bis(4-methoxybenzyl)-4-methyl-6-heptene-3-sulfonamide

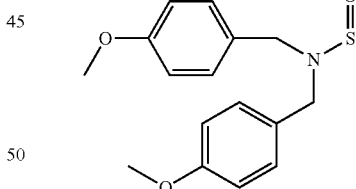

and

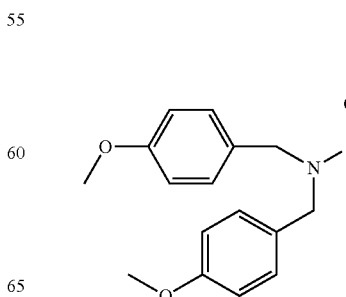

and

913
-continued

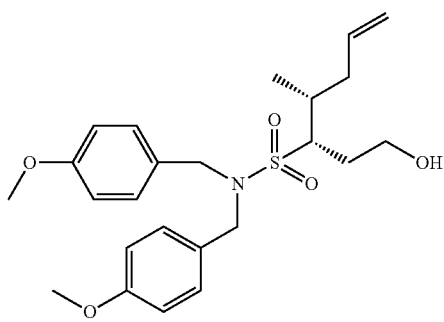

The title compounds were prepared from (2S)—N, N-bis (4-methoxybenzyl)-2-methylpent-4-ene-1-sulfonamide and (2R)—N, N-bis(4-methoxybenzyl)-2-methylpent-4-ene-1-sulfonamide using a similar procedure described in Step 2, of Example 380, replacing (bromomethyl)-cyclopropane with ethylene oxide gas.

Step 2: (3R,4S)-1-methoxy-N,N-bis(4-methoxybenzyl)-4-methyl-6-heptene-3-sulfonamide and (3R, 4S)-1-methoxy-N,N-bis(4-methoxybenzyl)-4-methyl-6-heptene-3-sulfonamide and (3R,4S)-1-methoxy-N,N-bis(4-methoxybenzyl)-4-methyl-6-heptene-3-sulfonamide and (3R,4S)-1-methoxy-N,N-bis(4-methoxybenzyl)-4-methyl-6-heptene-3-sulfonamide

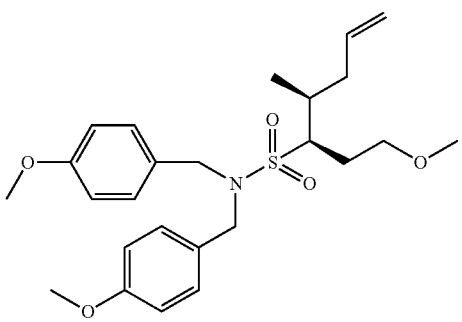

and

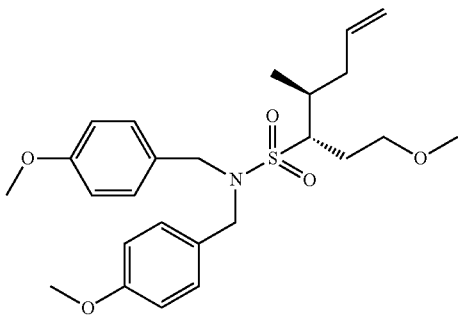

and

914
-continued

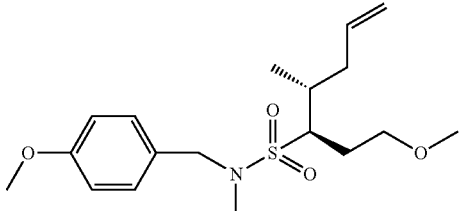

and

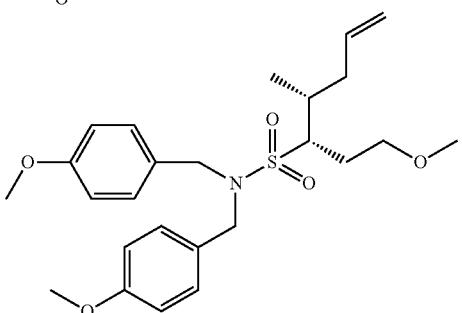

To a suspension of sodium hydride, 60% in oil (0.086 mL, 4.09 mmol) in THF at 0° C., was added a solution of (3R,4S)-1-hydroxy-N,N-bis(4-methoxybenzyl)-4-methyl-6-heptene-3-sulfonamide, (3R,4S)-1-hydroxy-N,N-bis(4-methoxybenzyl)-4-methyl-6-heptene-3-sulfonamide, (3R,4S)-1-hydroxy-N,N-bis(4-methoxybenzyl)-4-methyl-6-heptene-3-sulfonamide and (3R,4S)-1-hydroxy-N,N-bis(4-methoxybenzyl)-4-methyl-6-heptene-3-sulfonamide (610 mg, 1.36 mmol) in THF. The mixture was stirred for 25 min at 0° C., and then iodomethane (0.169 mL, 2.73 mmol) was added. The mixture was allowed to warm up to ambient temperature and kept stirring for 1 day. The mixture was quenched with aqueous saturated NH$_4$Cl, and diluted with EtOAc. The organic layer was washed with water, dried (Na$_2$SO$_4$) and concentrated. The crude residue was chromatographed (silica gel, hexane/EtOAc, 9:1 to 3:1) to afford the title compounds as an oil.

Step 3: (3R,4S)-1-methoxy-4-methyl-6-heptene-3-sulfonamide and (3R,4S)-1-methoxy-4-methyl-6-heptene-3-sulfonamide and (3R,4S)-1-methoxy-4-methyl-6-heptene-3-sulfonamide and (3R,4S)-1-methoxy-4-methyl-6-heptene-3-sulfonamide

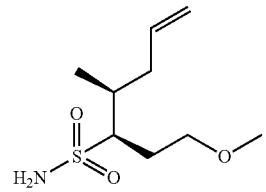

and

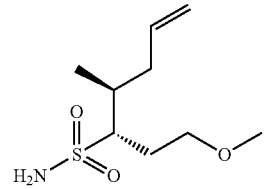

and

915
-continued

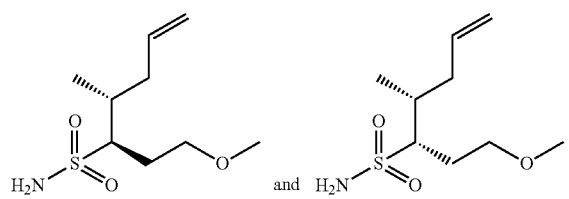

The title compounds were prepared from a mixture of (3R,4S)-1-methoxy-N,N-bis(4-methoxybenzyl)-4-methyl-6-heptene-3-sulfonamide and (3R,4S)-1-methoxy-N,N-bis(4-methoxybenzyl)-4-methyl-6-heptene-3-sulfonamide and (3R,4S)-1-methoxy-N,N-bis(4-methoxybenzyl)-4-methyl-6-heptene-3-sulfonamide and (3R,4S)-1-methoxy-N,N-bis(4-methoxybenzyl)-4-methyl-6-heptene-3-sulfonamide using a similar procedure described in Step 3, of Example 380.

Step 4: (3S)-6'-chloro-5-(((1R,2S)-2-((1S,2E)-1-hydroxy-2-hexen-1-yl)cyclobutyl)methyl)-N-(((3R,4S)-1-methoxy-4-methyl-6-hepten-3-yl)sulfonyl)-3',4,4',5-tetrahydro-2'H-spiro[1,5-benzoxazepine-3,1'-naphthalene]-7-carboxamide and (3S)-6'-chloro-5-(((1R,2S)-2-((1S,2E)-1-hydroxy-2-hexen-1-yl)cyclobutyl)methyl)-N-(((3R,4R)-1-methoxy-4-methyl-6-hepten-3-yl)sulfonyl)-3',4,4',5-tetrahydro-2'H-spiro[1,5-benzoxazepine-3,1'-naphthalene]-7-carboxamide and (3S)-6'-chloro-5-(((1R,2S)-2-((1S,2E)-1-hydroxy-2-hexen-1-yl)cyclobutyl)methyl)-N-(((3S,4S)-1-methoxy-4-methyl-6-hepten-3-yl)sulfonyl)-3',4,4',5-tetrahydro-2'H-spiro[1,5-benzoxazepine-3,1'-naphthalene]-7-carboxamide and (3S)-6'-chloro-5-(((1R,2S)-2-((1S,2E)-1-hydroxy-2-hexen-1-yl)cyclobutyl)methyl)-N-(((3S,4R)-1-methoxy-4-methyl-6-hepten-3-yl)sulfonyl)-3',4,4',5-tetrahydro-2'H-spiro[1,5-benzoxazepine-3,1'-naphthalene]-7-carboxamide

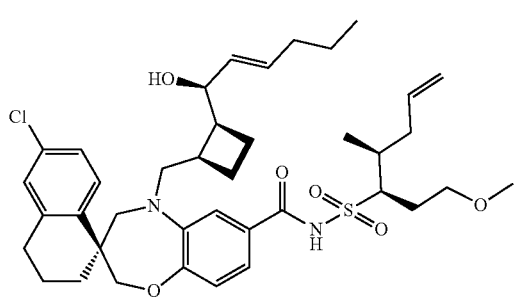

and

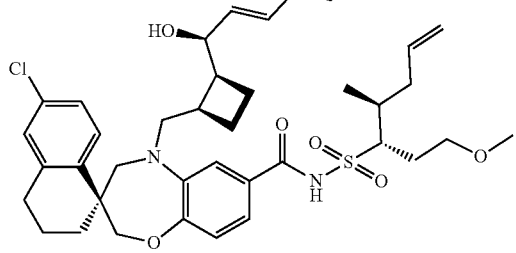

and

916
-continued

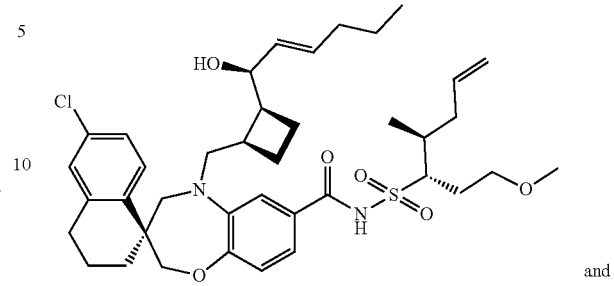

and

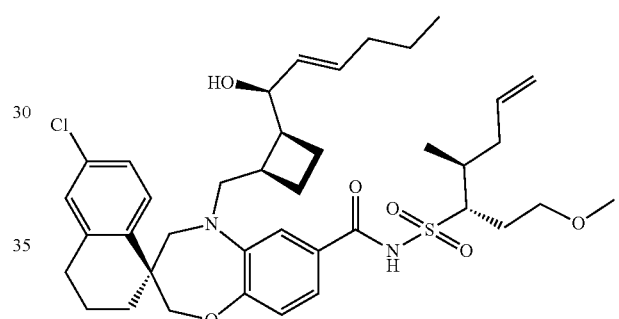

The reaction of (S)-6'-chloro-5-(((1R,2S)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A, 300 mg, 0.59 mmol) with 1-(3-dimethylaminopropyl)-3-ethylcarbodiimide HCl (192, mg, 1.00 mmol), 4-dimethylaminopyridine (122 mg, 1.00 mmol), triethylamine (179 mg, 1.76 mmol), and a mixture of (3R,4S)-1-methoxy-4-methyl-6-heptene-3-sulfonamide and (3R,4S)-1-methoxy-4-methyl-6-heptene-3-sulfonamide and (3R,4S)-1-methoxy-4-methyl-6-heptene-3-sulfonamide and (3R,4S)-1-methoxy-4-methyl-6-heptene-3-sulfonamide (221 mg, 1.00 mmol, Step 3) in CH$_2$Cl$_2$ (2 mL) was stirred at ambient temperature for 3 days. The mixture was quenched with water, and diluted with CH$_2$Cl$_2$. The combined organic layers were concentrated and chromatographed (silica gel, 9:1 to 1:1, hexane/EtOAc+0.5% HOAc) to afford the title compounds as an oil.

Step 5: (1S,3'R,6'R,7'S,8'E,11'S,12'R)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11R,12'S)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide A mixture of (3S)-6'-chloro-5-(((1R,2S)-2-((1S,2E)-1-hydroxy-2-hexen-1-yl)cyclobutyl)methyl)-N-(((3R,4S)-1-methoxy-4-methyl-6-hepten-3-yl)sulfonyl)-3',4,4',5-tetrahydro-2'H-spiro[1,5-benzoxazepine-3,1'-naphthalene]-7-carboxamide, (3S)-6'-chloro-5-(((1R,2S)-2-((1S,2E)-1-hydroxy-2-hexen-1-yl)cyclobutyl)methyl)-N-(((3R,4R)-1-methoxy-4-methyl-6-hepten-3-yl)sulfonyl)-3',4,4',5-tetrahydro-2'H-spiro[1,5-benzoxazepine-3,1'-naphthalene]-7-carboxamide, (3S)-6'-chloro-5-(((1R,2S)-2-((1S,2E)-1-hydroxy-2-hexen-1-yl)cyclobutyl)methyl)-N-(((3S,4S)-1-methoxy-4-methyl-6-hepten-3-yl)sulfonyl)-3',4,4',5-tetrahydro-2'H-spiro[1,5-benz oxazepine-3,1'-naphthalene]-7-carboxamide and (3S)-6'-chloro-5-(((1R,2S)-2-((1S,2E)-1-hydroxy-2-hexen-1-yl)cyclobutyl)methyl)-N-(((3S,4R)-1-methoxy-4-methyl-6-hepten-3-yl)sulfonyl)-3',4,4',5-tetrahydro-2'H-spiro[1,5-benzoxazepine-3,1'-naphthalene]-7-carboxamide (310 mg, 0.44 mmol) in 1,2-dichloroethane (120 mL) was introduced argon by bubbling argon into the flask for 10 min. Hoveyda-Grubbs catalyst II was added and the reaction mixture was heated at 50° C. for 48 h. The reaction mixture was then introduced air by bubbling air into the flask for 5 min. the crude material was concentrated and chromatographed (silica gel 9:1 to 0:1, hexane/EtOAc+0.5% HOAc) to afford an oil. This oil was further purified by reversed phase preparatory HPLC (Gemini™ Prep C$_{18}$ 5 µm column; Phenomenex, Torrance, CA; gradient elution of 25% to 75% MeCN in water, where both solvents contain 0.1% TFA, 30 min method) to afford the first eluenting isomer as the title compound (23 mg, 8.2%) as a white solid, $^1$H NMR (400 MHz, CDCl$_3$) δ ppm 8.00 (s, 1H), 7.73-7.68 (m, 1H), 7.19 (d, J=8.7 Hz, 1H), 7.10 (d, J=2.2 Hz, 1H), 7.02-6.95 (m, 1H), 6.95-6.80 (m, 2H), 5.93-5.78 (m, 1H), 5.71 (dd, J=8.0, 15.5 Hz, 1H), 4.32 (d, J=9.0 Hz, 1H), 4.25 (dd, J=4.4, 7.9 Hz, 1H), 4.15-4.07 (m, 2H), 3.81 (d, J=14.7 Hz, 1H), 3.76-3.64 (m, 3H), 3.40 (s, 3H), 3.27 (d, J=14.3 Hz, 1H), 3.08 (br s, 1H), 2.84-2.71 (m, 2H), 2.46 (dd, J=4.1, 8.0 Hz, 1H), 2.39-2.23 (m, 2H), 2.20-2.06 (m, 1H), 2.06-1.88 (m, 7H), 1.88-1.77 (m, 2H), 1.73-1.61 (m, 1H), 1.52-1.36 (m, 1H), 1.07 (d, J=6.3 Hz, 3H). m/z (ESI, +ve ion) 643.2 (M+H)$^+$.

Example 394. (1S,3'R,6'R,7'S,8'Z,11'S,12'R)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide or (1S,3'R,6'R,7'S,8'Z,11'R,12'S)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$] pentacosa[8,16,18,24]tetraen]-15'-one 13',13'-dioxide or (1S,3'R,6'R,7'S,8'Z,11'S,12'S)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$] pentacosa[8,16,18,24]tetraen]-15'-one 13',13'-dioxide or (1S,3'R,6'R,7'S,8'Z,11'R,12'R)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$] pentacosa[8,16,18,24]tetraen]-15'-one 13',13'-dioxide

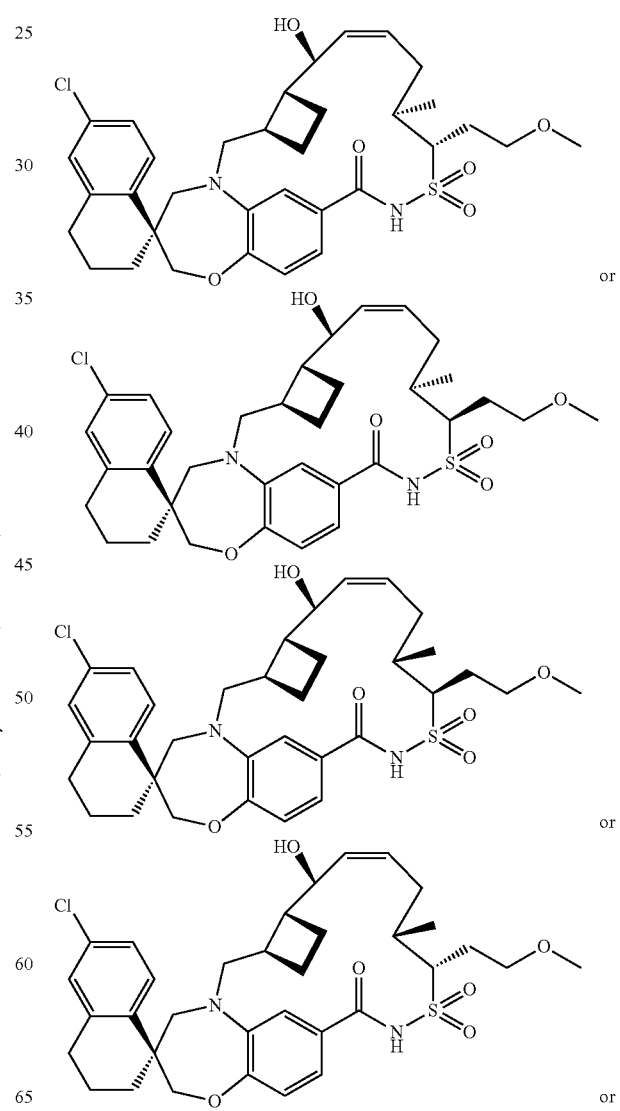

or or or

The title compound was obtained as the third eluenting isomer from the reversed phase preparatory HPLC separation in Example 393. $^1$H NMR (400 MHz, CDCl$_3$) δ ppm 7.72 (d, J=8.4 Hz, 1H), 7.54-7.37 (m, 1H), 7.23-7.12 (m, 2H), 7.12-7.07 (m, 1H), 6.99 (d, J=8.2 Hz, 1H), 5.76 (br s, 1H), 5.52 (dd, J=2.4, 11.8 Hz, 1H), 4.41 (br s, 1H), 4.25-4.04 (m, 2H), 3.89 (d, J=15.5 Hz, 1H), 3.78-3.57 (m, 4H), 3.50 (s, 3H), 3.21-2.96 (m, 2H), 2.91-2.67 (m, 2H), 2.39-2.11 (m, 2H), 2.10-1.88 (m, 2H), 1.73-1.50 (br s, 10H), 1.50-1.40 (m, 1H), 1.08-1.03 (d, J=6.8 Hz, 3H). m/z (ESI, +ve ion) 643.2 (M+H)$^+$.

Example 395. (1S,3'R,6'R,7'S,8'E,11'S,12'S)-6-chloro-7'-hydroxy-12'-(2-methoxyethyl)-11'-methyl-3,4-dihydro-2H,15'H-spiro [naphthalene-1,22'-[20] oxa[13]thia[1,14]diazatetracyclo[14.7.2.0$^{3,6}$.0$^{19,24}$] pentacosa[8,16,18,24]tetraen]-15'-one 13',13'-dioxide or (1S,3'R,6'R,7'S,8'E,11'S,12'R)-6-chloro-7'-hydroxy-12'-(2-methoxyethyl)-11'-methyl-3,4-dihydro-2H,15'H-spiro[naphthalene-1,22'-[20]oxa [13]thia[1,14]diazatetracyclo[14.7.2.0$^{3,6}$.0$^{19,24}$] pentacosa[8,16,18,24]tetraen]-15'-one 13',13'-dioxide

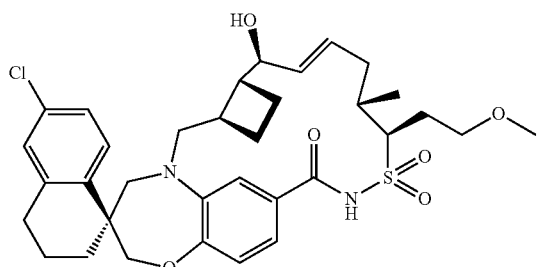

or

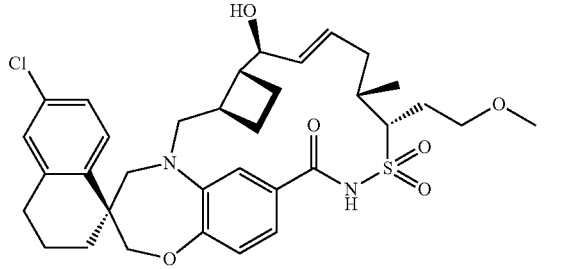

Step 1:
(R)-pent-4-en-2-yl-4-methylbenzenesulfonate

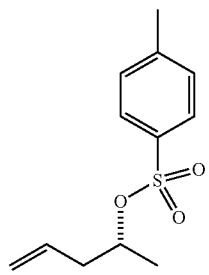

To a solution of p-toluenesulfonyl chloride (12.2 g, 63.9 mmol) and DMAP (3.55 g, 29.0 mmol) in DCM (150 mL) at 0° C. was added triethylamine (16.2 mL, 116 mmol), and then followed by the dropwise addition of (R)-(−)-4-penten-2-ol (2) (5.97 mL, 58.1 mmol) in DCM (100 mL). The reaction mixture was stirred and allowed to reach ambient temperature. After completion, the mixture was washed with 1.0 N HCl, saturated aqueous NaHCO$_3$ and H$_2$O. The organic layer was dried (MgSO$_4$), filtered, concentrated and chromatographed (silica gel, 0 to 70%, EtOAc/hexane) to afford (R)-pent-4-en-2-yl 4-methylbenzenesulfonate (11.0 g, 79%). m/z (ESI, +ve ion) 263.2 (M+Na)$^+$.

Step 2:
N,N-bis(4-methoxybenzyl)methanesulfonamide

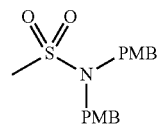

To a solution of methanesulfonamide (6.30 g, 66.2 mmol) in 2-butanone (331 mL) was added potassium iodide (1.10 g, 6.62 mmol), anhydrous potassium carbonate (36.6 g, 265 mmol), and PMBCl (22.5 mL, 166 mmol) successively. The resulting mixture was stirred at 81° C. for 18 h and then cooled, filtered through Celite to remove solids. The filter cake was washed with DCM and the filtrate was concentrated. Ether was added to the residue and a solid was formed to afford the title compound (18.0 g, 81%). m/z (ESI, +ve ion) 358.2 (M+H)$^+$.

Step 3: (S)—N,N-bis(4-methoxybenzyl)-2-methyl-pent-4-ene-1-sulfonamide

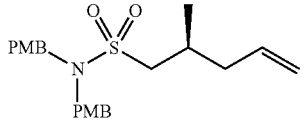

To a solution of N,N-bis(4-methoxybenzyl)methanesulfonamide (8.00 g, 23.9 mmol) in THF (68 mL) under N$_2$ at −78° C. was added butyllithium solution, 2.5 M in hexanes (10.5 mL, 26.2 mmol). This mixture was stirring for 10 min and then added a solution of (R)-pent-4-en-2-yl 4-methyl benzene sulfonate (8.60 g, 35.8 mmol) in THF (6 mL). The resulting mixture was stirred for 20 h from −78° C. to ambient temperature, and then added saturated aqueous NH$_4$Cl. The mixture was extracted with diethyl ether twice, and the combined organic layers were concentrated. the residue was chromatographed (silica gel, 0 to 60%, EtOAc/Hexane) to afford the title compound (3.0 g, 31%). m/z (ESI, +ve ion) 426.2 (M+H)$^+$.

Step 4: (3S,4S)-1-hydroxy-N,N-bis(4-methoxybenzyl)-4-methyl-6-heptene-3-sulfonamide and (3R,4S)-1-hydroxy-N,N-bis(4-methoxybenzyl)-4-methyl-6-heptene-3-sulfonamide

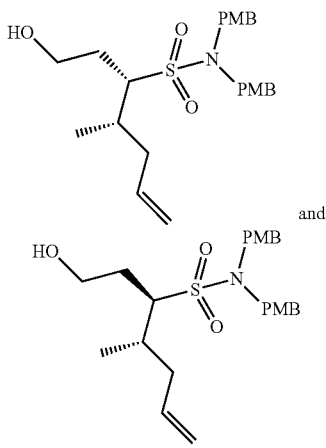

and

To a solution of (S)—N,N-bis(4-methoxybenzyl)-2-methylpent-4-ene-1-sulfonamide (2.80 g, 6.94 mmol) in THF (15 mL) was added n-butyllithium solution, 2.5 M in hexanes (3.05 mL, 7.63 mmol) at −78° C. dropwise. The mixture was stirred at −78° C. for 5 min, and ethylene oxide, 2.5 M solution in THF (5.55 mL, 13.9 mmol) was then added. The mixture was allowed to warm up to ambient temperature and stirred for 18 h. The mixture was quenched with saturated aqueous NH$_4$Cl, and extracted with EtOAc (2×). The organic layer was washed with brine, dried (MgSO$_4$), and filtered. The filtrate was concentrated and the resulting residue was chromatographed (silica gel, 20 to 60%, EtOAc/Hexane) to afford the title compounds (2.3 g, 74%). m/z (ESI, +ve ion) 470.2 (M+H)$^+$.

Step 5: (3S,4S)-1-methoxy-N,N-bis(4-methoxybenzyl)-4-methylhept-6-ene-3-sulfonamide and (3R,4S)-1-methoxy-N,N-bis(4-methoxybenzyl)-4-methylhept-6-ene-3-sulfonamide

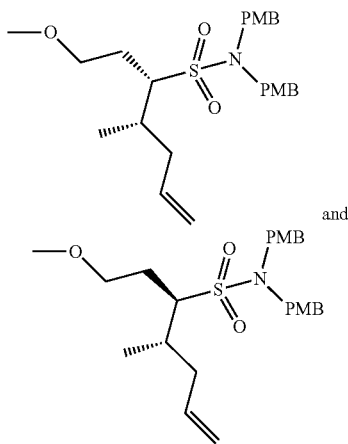

To a suspension of sodium hydride, 60% in oil (0.570 g, 14.3 mmol) in THF (10 mL) was added a solution of (3R,4S)-1-hydroxy-N,N-bis(4-methoxybenzyl)-4-methylhept-6-ene-3-sulfonamide and (3S,4S)-1-hydroxy-N,N-bis(4-methoxybenzyl)-4-methylhept-6-ene-3-sulfonamide (2.13 g, 4.47 mmol) in THF (4 mL). The mixture was stirred for 20 min at ambient temperature, and iodomethane (0.59 mL, 9.52 mmol) was added. The mixture was stirred at this temperature for 4 h and monitored by LCMS. More NaH and MeI were added in portions to reach the completion of the reaction. The mixture was quenched with saturated aqueous NH$_4$Cl, and extracted with EtOAc. The organic layer was washed with water, dried (MgSO$_4$) and concentrated. The resulting residue was chromatographed (silica gel, hexane/EtOAc, 1:0 to 1:1) to afford the title compounds as a yellow oil (1.87 g, 91%). m/z (ESI, +ve ion) 484.2 (M+H)$^+$.

Step 6: (3S,4S)-1-methoxy-4-methylhept-6-ene-3-sulfonamide and (3R,4S)-1-methoxy-4-methylhept-6-ene-3-sulfonamide

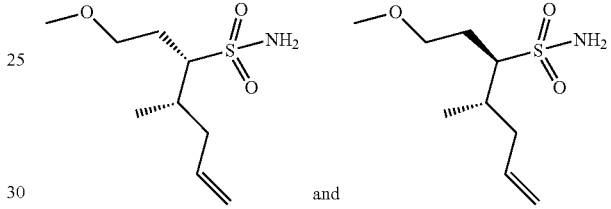

and

A mixture of (3R,4S)-1-methoxy-N,N-bis(4-methoxybenzyl)-4-methylhept-6-ene-3-sulfonamide and (3S,4S)-1-methoxy-N,N-bis(4-methoxybenzyl)-4-methylhept-6-ene-3-sulfonamide (1.86 g, 4.03 mmol) in TFA (23.0 g, 201 mmol) and anisole (22.0 g, 201 mmol) was stirred at 40° C. for 18 h. Then the reaction mixture was cooled and concentrated under reduced pressure and the residue was chromatographed (silica gel, hexane/EtOAc, 1:0 to 0:1) to afford the title compounds as an oil (0.81 g, 91%). m/z (ESI, +ve ion) 244.2 (M+H)$^+$.

Step 7: (3S)-6'-chloro-5-(((1R,2R)-2-((1S,2E,5S,6R)-1-hydroxy-8-methoxy-5-methyl-6-sulfamoyl-2-octen-1-yl)cyclobutyl)methyl)-3',4,4',5-tetrahydro-2'H-spiro[1,5-benzoxazepine-3,1'-naphthalene]-7-carboxylic acid and (3S)-6'-chloro-5-(((1R,2R)-2-((1S,2E,5S,6S)-1-hydroxy-8-methoxy-5-methyl-6-sulfamoyl-2-octen-1-yl)cyclobutyl)methyl)-3',4,4',5-tetrahydro-2'H-spiro[1,5-benzoxazepine-3,1'-naphthalene]-7-carboxylic acid

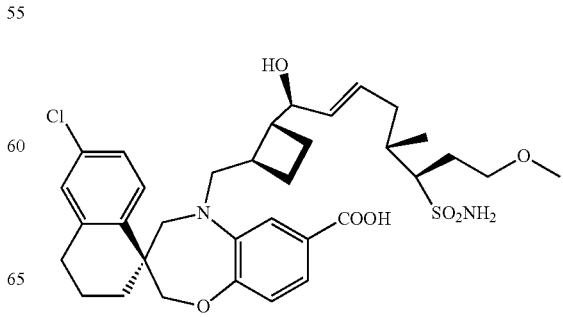

and

-continued

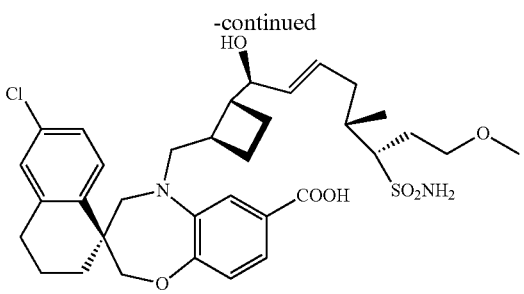

A mixture of (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A, 200 mg, 0.39 mmol) and (3R,4S)-1-methoxy-4-methylhept-6-ene-3-sulfonamide and (3S,4S)-1-methoxy-4-methylhept-6-ene-3-sulfonamide (304 mg, 1.37 mmol, Step 6) in 1,2-dichloroethane (2 mL) was introduced argon by bubbling argon into the reaction flask for 10 min. Hoveyda-Grubbs catalyst II (61 mg, 0.098 mmol) in 1,2-dichloroethane (2 mL) was added and the reaction was stirred at ambient temperature for 1.5 h. Air was then introduced by bubbling air into the reaction for 3 min. The mixture was then concentrated, and the resulting residue was chromatographed (silica gel, 9:1 to 0:1, hexane/EtOAc+0.3% HOAc) to afford the title compounds.

Step 8: (1S,3'R,6'R,7'S,8'E,11'S,12'S)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide A mixture of (3S)-6'-chloro-5-(((1R,2R)-2-((1S,2E,5S,6R)-1-hydroxy-8-methoxy-5-methyl-6-sulfamoyl-2-octen-1-yl)cyclobutyl)methyl)-3',4,4',5-tetrahydro-2'H-spiro[1,5-benzoxazepine-3,1'-naphthalene]-7-carboxylic acid and (3S)-6'-chloro-5-(((1R,2R)-2-((1S,2E,5S,6S)-1-hydroxy-8-methoxy-5-methyl-6-sulfamoyl-2-octen-1-yl)cyclobutyl)methyl)-3',4,4',5-tetrahydro-2'H-spiro[1,5-benzoxazepine-3,1'-naphthalene]-7-carboxylic acid (250 mg, 0.38 mmol) was reacted with 1-(3-dimethylaminopropyl)-3-ethylcarbodiimide HCl (145 mg, 0.76 mmol) and 4-dimethylaminopyridine (92.0 mg, 0.76 mmol) in DCM (150 mL) at ambient temperature for 3 days. Concentrated, the crude residue was chromatographed (silica gel, hexane/EtOAc+0.3% HOAc, 9:1 to 1:9) to afford a grey oil. This oil was further purified by reversed phase preparatory HPLC (Gemini™ Prep C$_{18}$ 5 µm column; Phenomenex, Torrance, CA; gradient elution of 25% to 75% MeCN in water, where both solvents contain 0.1% TFA, 30 min method) to afford the title compound as the second eluting isomer (15 mg, 6.2%) as a white solid. $^1$H NMR (500 MHz, CDCl$_3$) δ ppm 8.25 (br s, 1H), 7.69 (d, J=8.1 Hz, 1H), 7.20 (s, 1H), 7.19 (d, J=8.0 Hz, 1H), 7.10 (d, J=2.2 Hz, 1H), 7.00-6.91 (m, 1H), 6.68 (br s, 1H), 6.04 (br s, 1H), 5.67 (dd, J=6.4, 15.4 Hz, 1H), 4.20 (br s, 1H), 4.17-4.01 (m, 2H), 3.90 (br s, 1H), 3.78-3.59 (m, 4H), 3.50-3.41 (m, 1H), 3.40 (s, 3H), 3.29-3.01 (m, 1H), 2.85-2.72 (m, 2H), 2.61-2.47 (m, 2H), 2.41-2.32 (m, 1H), 2.31-2.20 (m, 2H), 2.15-1.80 (m, 8H), 1.78-1.62 (m, 1H), 1.52-1.40 (m, 1H), 1.17-1.09 (d, J=7.1 Hz, 3H). m/z (ESI, +ve ion) 657.2 (M+H)$^+$.

Example 396. (1S,3'R,6'R,7'S,8'E,11'S,12'S)-6-chloro-7'-methoxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one or (1S,3'R,6'R,7'S,8'E,11'S,12'R)-6-chloro-7'-methoxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

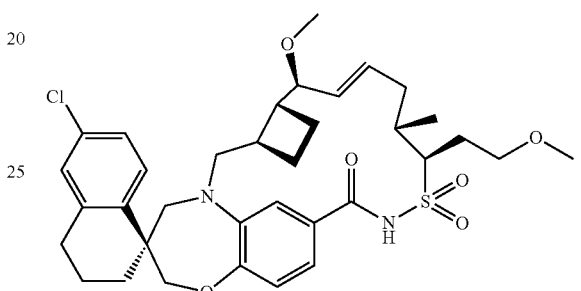

Or

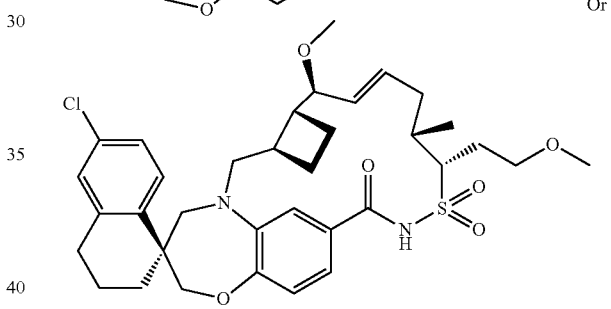

To a suspension of sodium hydride, 60% in oil (8.7 mg, 0.22 mmol) in DMF at 0° C. was added a solution of (1S,3'R,6'R,7'S,8'E,11'S,12'S)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (the first eluenting isomer in Example 395.12 mg, 0.019 mmol) in DMF. The mixture was stirred for 20 min at this temperature, and iodomethane (5.8 µl, 0.093 mmol) was added. The ice bath was then removed and the mixture was allowed to stir at ambient temperature for 18 h. The reaction was quenched with water, and added EtOAc. The organic layer was washed with water (3x), dried (MgSO$_4$), and filtered. The filtrate was concentrated and chromatographed (silica gel, 9:1 to 1:1, hexane/EtOAc+ 0.5% HOAc) to afford an oil. Further purification of the oil by reversed phase preparatory HPLC (Gemini™ Prep C$_{18}$ 5 µm column; Phenomenex, Torrance, CA; gradient elution of 25% to 75% MeCN in water, where both solvents contain 0.1% TFA, 30 min method) afforded the title compound as a white solid. $^1$H NMR (500 MHz, CDCl$_3$) δ ppm 7.95 (s, 1H), 7.70 (d, J=8.6 Hz, 1H), 7.19 (dd, J=2.1, 8.4 Hz, 1H), 7.13-7.06 (m, 1H), 6.96-6.86 (m, 3H), 5.92-5.85 (m, 1H), 5.52 (dd, J=10.6, 15.3 Hz, 1H), 5.31 (s, 1H), 4.40 (d, J=7.8 Hz, 1H), 4.10 (s, 2H), 3.82 (d, J=15.2 Hz, 1H), 3.76-3.63 (m, 4H), 3.41 (s, 3H), 3.28-3.18 (m, 4H), 3.01 (dd, J=10.3, 15.2 Hz, 1H), 2.84-2.72 (m, 2H), 2.50-2.41 (m, 1H), 2.38-2.19 (m, 3H), 2.11-1.90 (m, 6H), 1.89-1.80 (m, 3H), 1.75-1.40 (m, 1H), 1.44-1.35 (m, 1H), 1.09-1.03 (d, J=6.8 Hz, 3H). m/z (ESI, +ve ion) 657.2 (M+H)$^+$.

Example 397. (1S,3'R,6'R,7'S,8'E,11'S,12'R)-6-chloro-7'-(2-methoxyethoxy)-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-(2-methoxyethoxy)-12'-(2-methoxy ethyl)-11'-methyl-3,4-dihydro-2H,15'H-spiro[naphthalene-1,22'-[20]oxa [13]thia[1,14]diazatetracyclo [14.7.2.0$^{3,6}$.0$^{19,24}$]pentacosa[8,16,18,24]tetraen]-15'-one 13',13'-dioxide

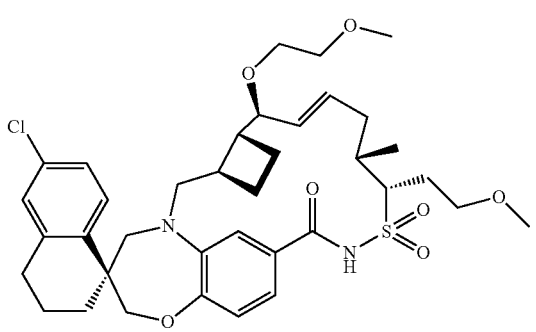

or

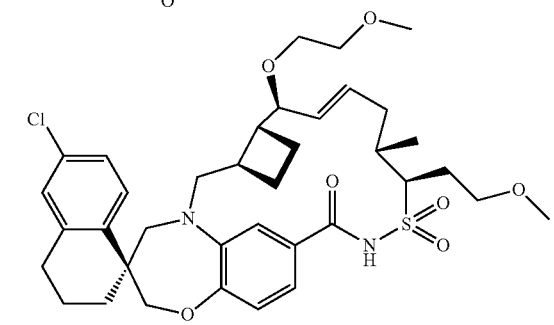

The title compound was prepared from (1S,3'R,6'R,7'S,8'E,11'S,12'S)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-hydroxy-12'-(2-methoxyethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (the first eluenting isomer in Example 395) by the similar procedure described in Example 396, replacing iodomethane with 2-bromoethyl methyl ether. $^1$H NMR (500 MHz, CDCl$_3$) δ ppm 8.03 (s, 1H), 7.70 (d, J=8.6 Hz, 1H), 7.18 (dd, J=2.3, 8.4 Hz, 1H), 7.09 (d, J=2.2 Hz, 1H), 6.94-6.88 (m, 3H), 5.85 (ddd, J=3.1, 9.8, 15.2 Hz, 1H), 5.54 (dd, J=9.2, 15.3 Hz, 1H), 4.37 (d, J=8.1 Hz, 1H), 4.09 (s, 2H), 3.85-3.77 (m, 2H), 3.76-3.67 (m, 3H), 3.60-3.48 (m, 3H), 3.44-3.40 (m, 4H), 3.39 (s, 3H), 3.23 (d, J=14.2 Hz, 1H), 2.99 (dd, J=10.3, 15.2 Hz, 1H), 2.83-2.72 (m, 2H), 2.53-2.45 (m, 1H), 2.37-2.20 (m, 3H), 2.07-1.92 (m, 6H), 1.91-1.74 (m, 3H), 1.68-1.50 (m, 1H), 1.39 (t, J=12.7 Hz, 1H), 1.05 (d, J=6.8 Hz, 3H). m/z (ESI, +ve ion) 701.2 (M+H)$^+$.

Example 398. (1S,3'R,6'R,7'S,8'E,11'S,12'R)-6-chloro-12'-(2-methoxyethyl)-11'-methyl-7'-(2-(4-morpholinyl)ethoxy)-3,4-dihydro-2H,15'H-spiro [naphthalene-1,22'-[20]oxa[13]thia[1,14] diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-12'-(2-methoxyethyl)-11'-methyl-7'-(2-(4-morpholinyl)ethoxy)-3,4-dihydro-2H,15'H-spiro[naphthalene-1,22'-[20]oxa [13]thia[1,14]diazatetracyclo[14.7.2.0$^{3,6}$.0$^{19,24}$] pentacosa 8,16,18,24]tetraen]-15'-one 13',13'-dioxide

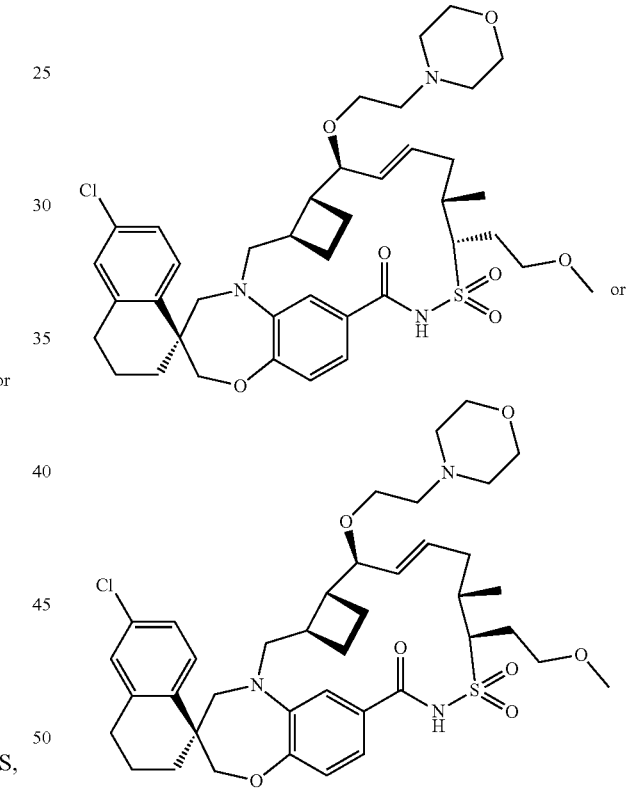

The title compound was prepared from (1S,3'R,6'R,7'S,8'E,11'S,12'S)-6-chloro-7'-hydroxy-12'-(2-methoxyethyl)-11'-methyl-3,4-dihydro-2h,15'h-spiro[naphthalene-1,22'-[20]oxa[13]thia[1,14]diazatetracyclo[14.7.2.0$^{3,6}$.0$^{19,24}$] pentacosa[8,16,18,24]tetraen]-15'-one 13',13'-dioxide or (1S,3'R,6'R,7'S,8'E,11'S,12'R)-6-chloro-7'-hydroxy-12'-(2-methoxyethyl)-11'-methyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide, the first eluenting isomer in Example 395 by a similar procedure described in Example 396, replacing iodomethane with 4-(2-bromoethyl)morpholine hydrobromide. $^1$H NMR (500 MHz, CDCl$_3$) δ=7.70 (d, J=8.3 Hz, 1H), 7.18 (dd, J=2.2, 8.6 Hz, 1H), 7.09 (d, J=2.2 Hz, 1H), 6.93 (s, 2H), 6.88 (s, 1H), 5.90-5.83 (m, 1H), 5.53 (dd, J=9.2, 15.3 Hz, 1H), 4.34 (d, J=8.3 Hz, 1H), 4.14-4.06 (m, 2H), 3.85-3.65 (m, 9H), 3.60 (br s, 1H), 3.47 (br s, 1H), 3.41 (s, 3H), 3.24 (d, J=14.2 Hz, 1H), 3.01 (dd, J=10.1, 15.3 Hz, 1H), 2.84-2.71 (m, 2H), 2.60 (br s, 6H), 2.49-2.40 (m, 1H), 2.39-2.19 (m, 3H), 2.08-1.91 (m, 6H), 1.88-1.76 (m, 3H), 1.64 (t, J=9.7 Hz, 1H), 1.39 (t, J=12.8 Hz, 1H), 1.05 (d, J=6.8 Hz, 3H). m/z (ESI, +ve ion) 756.2 (M+H)+.

Example 399. (1S,3'R,6'R,7'S,8'E,11'S,12'R)-6-chloro-7'-hydroxy-12'-(2-(2-methoxyethoxy)ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-12'-(2-(2-methoxyethoxy) ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-12'-(2-(2-methoxyethoxy) ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11R,12'S)-6-chloro-7'-hydroxy-12'-(2-(2-methoxyethoxy) ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

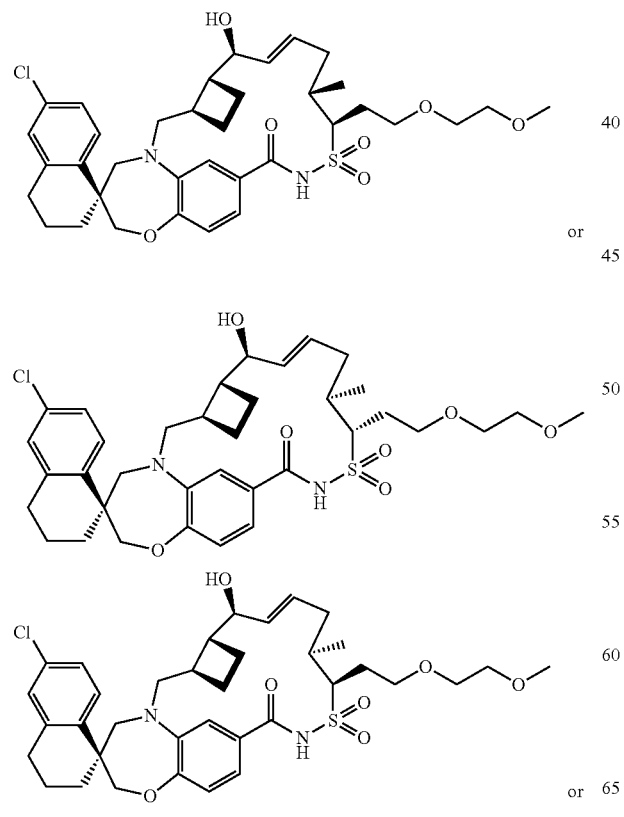

or

-continued

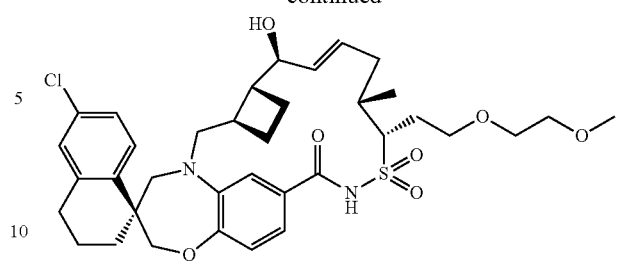

Step 1: (3R,4S)—N,N-bis(4-methoxybenzyl)-1-(2-methoxyethoxy)-4-methyl-6-heptene-3-sulfonamide and (3R,4R)—N,N-bis(4-methoxybenzyl)-1-(2-methoxyethoxy)-4-methyl-6-heptene-3-sulfonamide and (3S,4S)—N,N-bis(4-methoxybenzyl)-1-(2-methoxyethoxy)-4-methyl-6-heptene-3-sulfonamide and (3S,4R)—N,N-bis(4-methoxybenzyl)-1-(2-methoxyethoxy)-4-methyl-6-heptene-3-sulfonamide

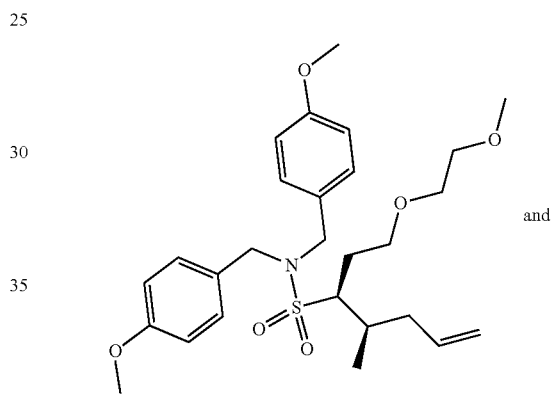

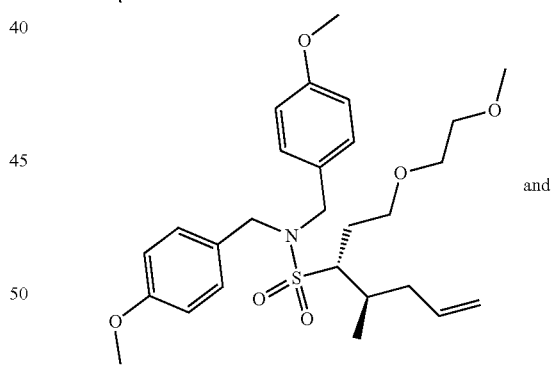

929
-continued

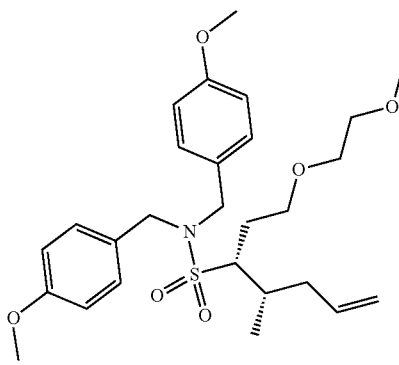

To a suspension of sodium hydride, 60% in oil (164 mg, 4.09 mmol) in THF at 0° C. was added a solution of (3R,4S)-1-hydroxy-N,N-bis(4-methoxybenzyl)-4-methyl-6-heptene-3-sulfonamide, (3R,4S)-1-hydroxy-N,N-bis(4-methoxybenzyl)-4-methyl-6-heptene-3-sulfonamide, (3R,4S)-1-hydroxy-N,N-bis(4-methoxybenzyl)-4-methyl-6-heptene-3-sulfonamide and (3R,4S)-1-hydroxy-N,N-bis(4-methoxybenzyl)-4-methyl-6-heptene-3-sulfonamide (From Example 393, Step 1, 610 mg, 1.36 mmol) in THF. The mixture was stirred for 25 min at this temperature, and 2-bromoethyl methyl ether (0.256 mL, 2.73 mmol) was added. The mixture was allowed to warm up to ambient temperature and stirred for 3 day. The mixture was quenched with saturated aqueous NH$_4$Cl, and diluted with EtOAc. The organic layer was dried (MgSO$_4$), filtered and the filtrate was concentrated. The resulting residue was chromatographed (silica gel, 9:1 to 3:2, hexane/EtOAc) to afford the title compound as an oil.

Step 2: (3S,4R)-1-(2-methoxyethoxy)-4-methylhept-6-ene-3-sulfonamide and (3R,4R)-1-(2-methoxyethoxy)-4-methylhept-6-ene-3-sulfonamide and (3S,4S)-1-(2-methoxyethoxy)-4-methylhept-6-ene-3-sulfonamide and (3R,4S)-1-(2-methoxyethoxy)-4-methylhept-6-ene-3-sulfonamide

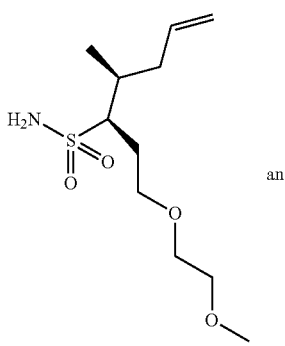
and

930
-continued

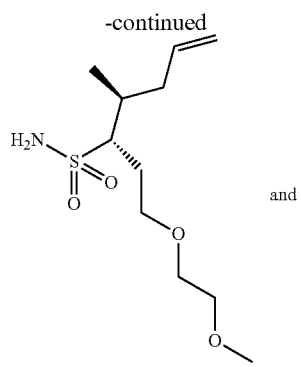
and

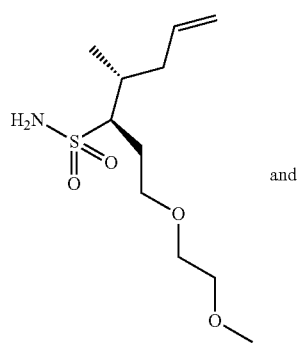
and

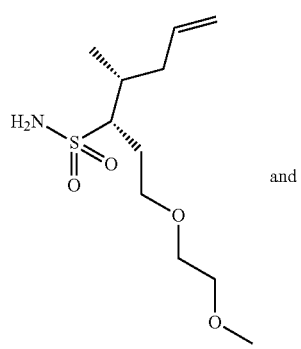
and

The title compounds were prepared from a mixture of (3R,4S)—N,N-bis(4-methoxybenzyl)-1-(2-methoxyethoxy)-4-methyl-6-heptene-3-sulfonamide, (3R,4R)—N,N-bis(4-methoxybenzyl)-1-(2-methoxyethoxy)-4-methyl-6-heptene-3-sulfonamide, (3S,4R)—N,N-bis(4-methoxybenzyl)-1-(2-methoxyethoxy)-4-methyl-6-heptene-3-sulfonamide and (3S,4S)—N,N-bis(4-methoxybenzyl)-1-(2-methoxyethoxy)-4-methyl-6-heptene-3-sulfonamide by using a similar procedure described in Step 3 of Example 393.

Step 3: (3S)-6'-chloro-5-(((1R,2R)-2-((1S,2E)-1-hydroxy-2-hexen-1-yl)cyclobutyl)methyl)-N-(((3R,4S)-1-(2-methoxyethoxy)-4-methyl-6-hepten-3-yl)sulfonyl)-3',4',4',5-tetrahydro-2'H-spiro[1,5-benzoxazepine-3,1'-naphthalene]-7-carboxamide and (3S)-6'-chloro-5-(((1R,2R)-2S,2E)-1-hydroxy-2-hexen-1-yl)cyclobutyl)methyl)-N-(((3S,4S)-1-(2-methoxyethoxy)-4-methyl-6-hepten-3-yl) sulfonyl)-3',4',4',5-tetrahydro-2'H-spiro[1,5-benzoxazepine-3,1'-naphthalene]-7-carboxamide and (3S)-6'-chloro-5-(((1R,2R)-2S,2E)-1-hydroxy-2-hexen-1-yl)cyclobutyl)methyl)-N-(((3R,4S)-1-(2-methoxyethoxy)-4-methyl-6-hepten-3-yl) sulfonyl)-3',4',4',5-tetrahydro-2'H-spiro[1,5-benzoxazepine-3,1'-naphthalene]-7-carboxamide and (3S)-6'-chloro-5-(((1R,2R)-2S,2E)-1-hydroxy-2-hexen-1-yl)cyclobutyl)methyl)-N-(((3S,4R)-1-(2-methoxyethoxy)-4-methyl-6-hepten-3-yl) sulfonyl)-3',4',4',5-tetrahydro-2'H-spiro[1,5-benzoxazepine-3,1'-naphthalene]-7-carboxamide

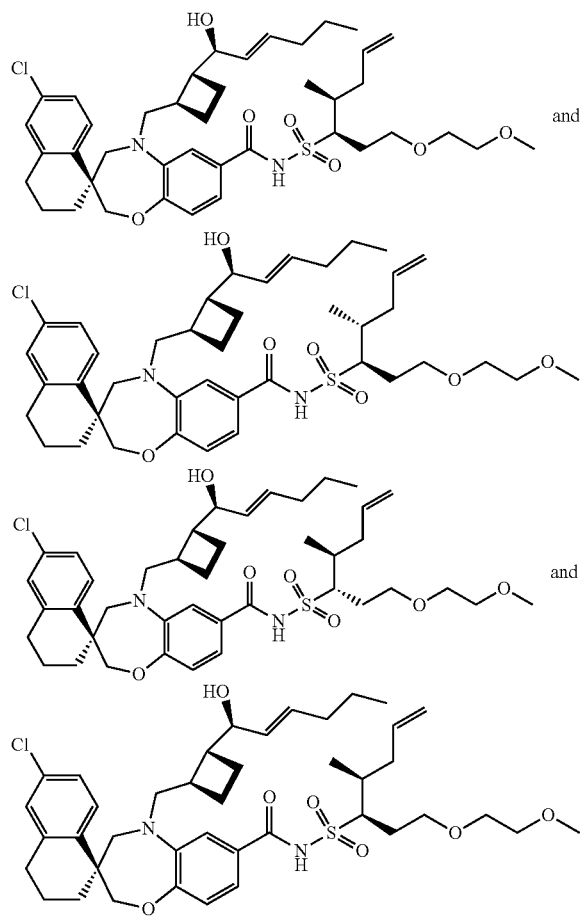

The title compounds were prepared from a mixture of (3S,4R)-1-(2-methoxyethoxy)-4-methylhept-6-ene-3-sulfonamide, (3S,4R)-1-(2-methoxyethoxy)-4-methylhept-6-ene-3-sulfonamide, (3S,4R)-1-(2-methoxyethoxy)-4-methylhept-6-ene-3-sulfonamide and (3S,4R)-1-(2-methoxyethoxy)-4-methylhept-6-ene-3-sulfonamide with Intermediate AA12A by a similar procedure described in Step 4 of Example 380.

Step 4: (1S,3'R,6'R,7'S,8'E,11'S,12'R)-6-chloro-7'-hydroxy-12'-(2-(2-methoxyethoxy)ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'S)-6-chloro-7'-hydroxy-12'-(2-(2-methoxyethoxy) ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-12'-(2-(2-methoxyethoxy)ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11R,12'S)-6-chloro-7'-hydroxy-12'-(2-(2-methoxyethoxy)ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide The title compound was prepared from a mixture of (3S)-6'-chloro-5-(((1R,2R)-2-((1S,2E)-1-hydroxy-2-hexen-1-yl)cyclobutyl)methyl)-N-(43R,4S)-1-(2-methoxyethoxy)-4-methyl-6-hepten-3-yl)sulfonyl)-3',4',4',5-tetrahydro-2'H-spiro[1,5-benzoxazepine-3,1'-naphthalene]-7-carboxamide, (3S)-6'-chloro-5-(((1R,2R)-2-((1S,2E)-1-hydroxy-2-hexen-1-yl)cyclobutyl)methyl)-N-(((3S,4S)-1-(2-methoxyethoxy)-4-methyl-6-hepten-3-yl)sulfonyl)-3',4',4',5-tetrahydro-2'H-spiro [1,5-benzoxazepine-3,1'-naphthalene]-7-carboxamide, (3S)-6'-chloro-5-(((1R,2R)-2-((1S,2E)-1-hydroxy-2-hexen-1-yl)cyclobutyl)methyl)-N-(43R,4S)-1-(2-methoxy ethoxy)-4-methyl-6-hepten-3-yl)sulfonyl)-3',4',4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((3S,4R)-1-(2-methoxyethoxy)-4-methyl-6-hepten-3-yl)sulfonyl)-3',4',4',5-tetrahydro-2'H-spiro[1,5-benzoxazepine-3,1'-naphthalene]-7-carboxamide by a similar procedure described in Step 5 of Example 380, and as the first eluenting isomer from the reversed phase preparatory HPLC (Gemini™ Prep $C_{18}$ 5 μm column; Phenomenex, Torrance, CA; gradient elution of 25% to 75% MeCN in water, where both solvents contain 0.1% TFA, 30 min method). $^1$H NMR (500 MHz, CDCl$_3$) δ ppm 8.05 (br s, 1H), 7.70 (d, J=8.6 Hz, 1H), 7.18 (dd, J=2.0, 8.6 Hz, 1H), 7.12-7.06 (m, 1H), 7.01-6.86 (m, 3H), 5.92-5.80 (m, 1H), 5.71 (dd, J=7.6, 15.2 Hz, 1H), 4.39 (d, J=8.6 Hz, 1H), 4.28 (br s, 1H), 4.10 (s, 2H), 3.85-3.76 (m, 3H), 3.73-3.57 (m, 6H), 3.45-3.40 (m, 3H), 3.25 (d, J=14.2 Hz, 1H), 3.06 (br s, 1H), 2.86-2.71 (m, 2H), 2.50-2.40 (m, 1H), 2.37-2.21 (m, 3H), 2.20 (m, 6H), 1.92-1.75 (m, 2H), 1.73-1.62 (m, 1H), 1.42 (t, J=12.6 Hz, 1H), 1.13-1.00 (d, J=6.6 Hz, 3H) m/z (ESI, +ve ion) 687.2 (M+H)$^+$.

Example 400. (1S,3'R,6'R,7'S,8'Z,11'S,12'R)-6-chloro-7'-hydroxy-12'-(2-(2-methoxyethoxy)ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'S)-6-chloro-7'-hydroxy-12'-(2-(2-methoxyethoxy) ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'Z,11'R,12'R)-6-chloro-7'-hydroxy-12'-(2-(2-methoxyethoxy) ethyl)-11'-methyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide or (1S,3'R,6'R,7'S,8'Z,11R,12'S)-6-chloro-7'-hydroxy-12'-(2-(2-methoxyethoxy) ethyl)-11'-methyl-3,4-dihydro-2H,15'H-spiro[naphthalene-1,22'-[20]oxa [13]thia[1,14]diazatetracyclo [14.7.2.0$^{3,6}$.0$^{19,24}$]pentacosa[8,16,18,24]tetraen]-15'-one 13',13'-dioxide or

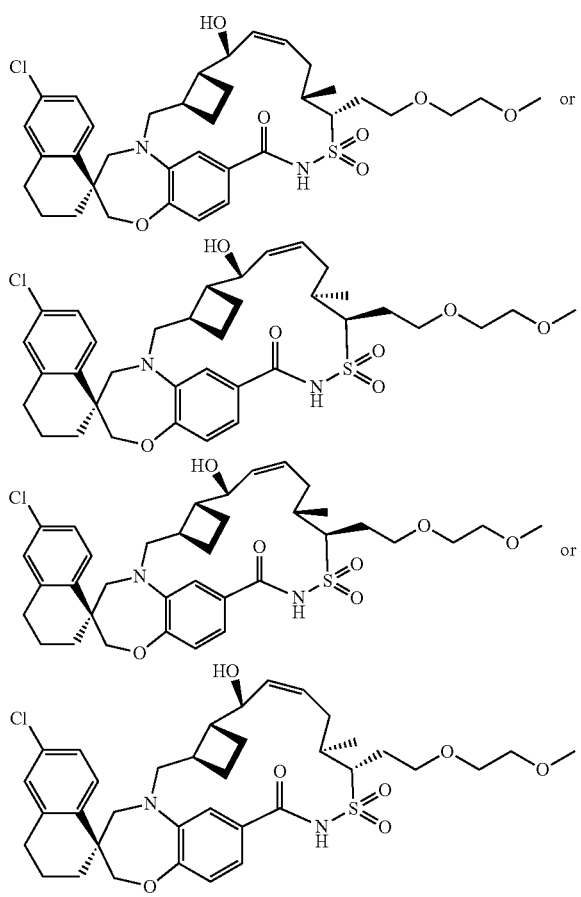

The title compound was obtained as the second eluenting isomer from the reversed phase preparatory HPLC separation in Example 399. $^1$H NMR (400 MHz, CDCl$_3$) δ ppm 8.99 (br s, 1H), 7.71 (d, J=8.4 Hz, 1H), 7.19 (d, J=8.5 Hz, 2H), 7.10 (s, 2H), 6.95 (d, J=8.3 Hz, 1H), 5.78 (br s, 1H), 5.66 (dd, J=7.0, 11.3 Hz, 1H), 4.45 (t, J=5.9 Hz, 1H), 4.18-4.10 (m, 1H), 4.10 (s, 2H), 3.89-3.73 (m, 3H), 3.73-3.57 (m, 6H), 3.46-3.39 (m, 3H), 3.30-3.10 (m, 2H), 2.84-2.71 (m, 2H), 2.50-2.36 (m, 1H), 2.35-2.24 (m, 2H), 2.12 (br s, 1H), 2.09-1.96 (m, 4H), 1.92-1.61 (m, 5H), 1.45 (t, J=12.4 Hz, 1H), 1.15-1.04 (d, J=6.1 Hz, 3H). m/z (ESI, +ve ion) 687.2 (M+H)$^+$.

Example 401. (1S,3'R,6'R,7'S,8'E,11'S,12'R)-6-chloro-7'-hydroxy-12'-(2-(2-methoxyethoxy)ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-12'-(2-(2-methoxyethoxy) ethyl)-11'-methyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-12'-(2-(2-methoxyethoxy) ethyl)-11'-methyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide or (1S,3'R,6'R,7'S,8'E,11R,12'S)-6-chloro-7'-hydroxy-12'-(2-(2-methoxyethoxy) ethyl)-11'-methyl-3,4-dihydro-2H,15'H-spiro[naphthalene-1,22'-[20]oxa [13]thia[1,14]diazatetracyclo [14.7.2.0$^{3,6}$.0$^{19,24}$]pentacosa[8,16,18,24]tetraen]-15'-one 13',13'-dioxide

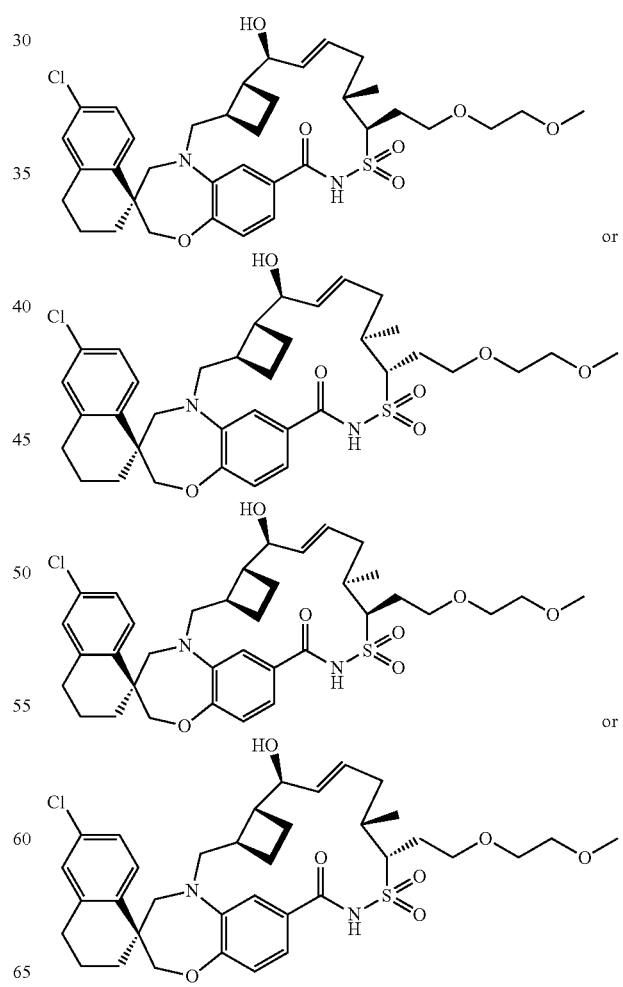

The title compound was obtained as the third eluenting isomer from the reversed phase preparatory HPLC separation in Example 399. $^1$H NMR (500 MHz, CDCl$_3$) δ ppm 8.28 (br s, 1H), 7.70 (d, J=8.6 Hz, 1H), 7.21-7.14 (m, 2H), 7.14-7.06 (m, 1H), 6.96 (d, J=8.6 Hz, 1H), 6.69 (br s, 1H), 6.05 (br s, 1H), 5.67 (dd, J=5.4, 15.2 Hz, 1H), 4.24-4.00 (m, 4H), 3.95-3.52 (m, 9H)), 3.47-3.37 (m, 4H), 3.34-3.15 (m, 1H), 2.86-2.70 (m, 2H), 2.61-2.45 (m, 2H), 2.38 (br s, 1H), 2.26 (br s, 2H), 2.15-1.65 (m, 8H), 1.47 (m 1H), 1.13 (d, J=7.1 Hz, 3H). m/z (ESI, +ve ion) 687.2 (M+H)$^+$.

Example 402. (1S,3'R,6'R,7'S,8'E,11'S,12'R)-6-chloro-7'-hydroxy-12'-(2-(2-methoxyethoxy)ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-12'-(2-(2-methoxyethoxy)ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-7'-hydroxy-12'-(2-(2-methoxyethoxy)ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11R,12'S)-6-chloro-7'-hydroxy-12'-(2-(2-methoxyethoxy)ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

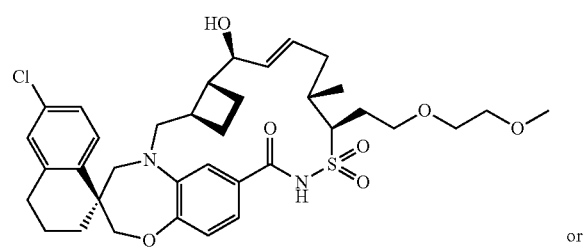

or

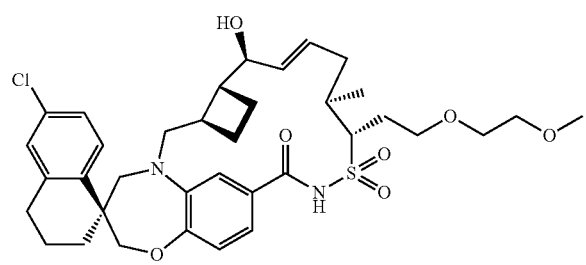

or

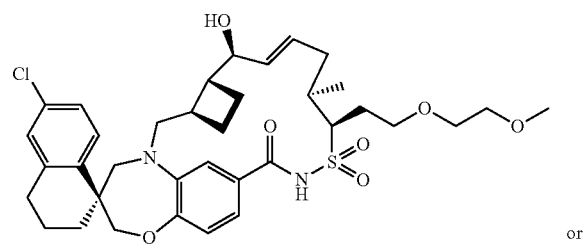

or

-continued

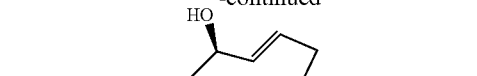

The title compound was obtained as the fifth eluenting isomer from the reversed phase preparatory HPLC separation in Example 399. $^1$H NMR (400 MHz, CDCl$_3$) δ ppm 8.24 (br s, 1H), 7.75 (br s, 1H), 7.64 (d, J=8.4 Hz, 1H), 7.15 (dd, J=2.2, 8.5 Hz, 1H), 7.10 (d, J=2.2 Hz, 1H), 6.94-6.88 (m, 2H), 5.75 (dd, J=3.7, 15.7 Hz, 1H), 5.51 (m, 1H), 4.32 (d, J=7.6 Hz, 1H), 4.30-4.19 (m, 2H), 4.12 (br s, 1H), 3.94-3.68 (m, 7H), 3.65-3.58 (m, 1H), 3.50-3.37 (m, 3H), 3.30 (d, J=14.3 Hz, 1H), 3.10 (d, J=16.0 Hz, 1H), 2.75 (m, 2H), 2.61-2.39 (m, 2H), 2.37-2.13 (m, 1H), 2.06-1.60 (m, 11H), 1.50-1.34 (m, 1H), 1.07 (d, J=5.9 Hz, 3H). m/z (ESI, +ve ion) 687.2 (M+H)$^+$.

Example 403. (1S,3'R,6'R,7'S,8'E,11'S,12'R)-6-chloro-7'-methoxy-12'-(2-(2-methoxyethoxy)ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-12'-(2-(2-methoxyethoxy)ethyl)-11'-methyl-3,4-dihydro-2H,15'H-spiro[naphthalene-1,22'-[20]oxa [13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-12'-(2-(2-methoxyethoxy)ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11R,12'S)-6-chloro-7'-hydroxy-12'-(2-(2-methoxyethoxy)ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

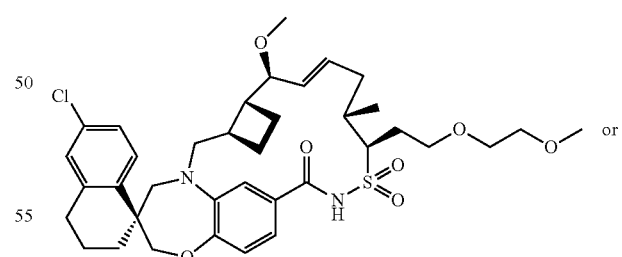

or

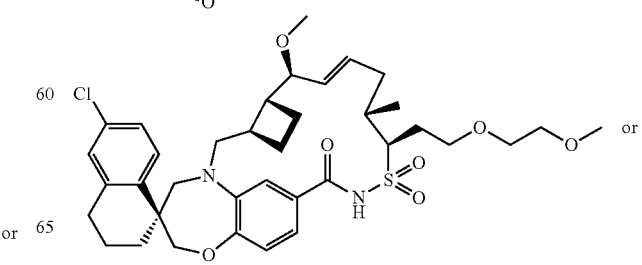

or

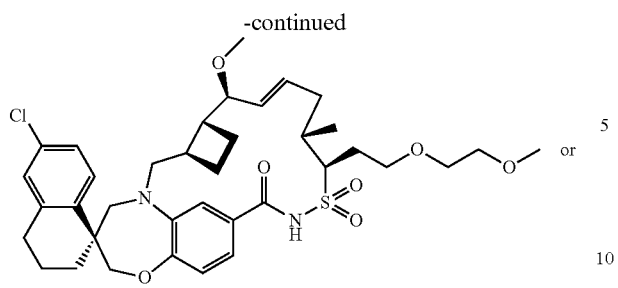

or

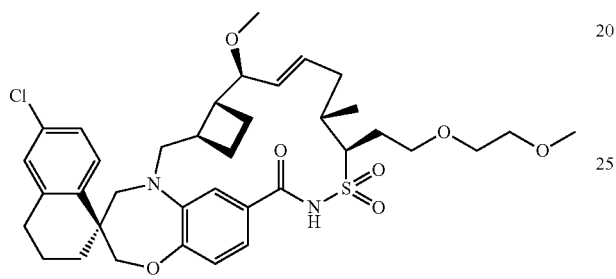

The title compound was prepared from (1S,3'R,6'R,7'S, 8'E,11'S,12'R)-6-chloro-7'-hydroxy-12'-(2-(2-methoxy-ethoxy)ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-12'-(2-(2-methoxyethoxy) ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S, 8'E,11'R,12'R)-6-chloro-7'-hydroxy-12'-(2-(2-methoxyethoxy) ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24] tetraen]-15'-one 13',13'-dioxide or (1S,3'R,6'R,7'S,8'E,11'R, 12'S)-6-chloro-7'-hydroxy-12'-(2-(2-methoxyethoxy) ethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (from Example 399) by a similar procedure described in Example 396. $^1$H NMR (500 MHz, CDCl$_3$) δ ppm 8.00 (s, 1H), 7.70 (d, J=8.6 Hz, 1H), 7.19 (dd, J=2.2, 8.6 Hz, 1H), 7.10 (d, J=2.2 Hz, 1H), 6.96-6.85 (m, 3H), 5.92-5.85 (m, 1H), 5.55-5.49 (d, J=8.3, 14.4 Hz, 1H), 4.36 (d, J=9.3 Hz, 1H), 4.09 (s, 2H), 3.91-3.86 (m, 1H), 3.86-3.61 (m, 7H), 3.60-3.57 (m, 2H), 3.45-3.36 (m, 3H), 3.29-3.18 (m, 4H), 3.01 (dd, J=10.3, 15.4 Hz, 1H), 2.84-2.72 (m, 2H), 2.46 (m, 1H), 2.39-2.25 (m, 3H), 2.08-1.92 (m, 6H), 1.90-1.75 (m, 2H), 1.75-1.63 (m, 1H), 1.46-1.25 (m, 1H), 1.05 (d, J=6.8 Hz, 3H). m/z (ESI, +ve ion) 623.2 (M+Na)$^+$.

Example 404. 2-(((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-methylacetamide

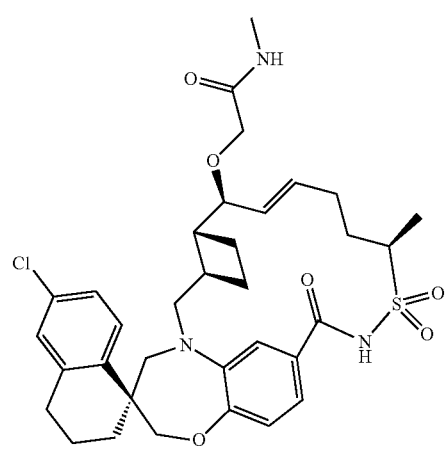 [SMILES: CNC(=O)CO[C@H]1/C=C/CC[C@@H](C)S(=O)(=O)NC(=O)c2ccc3c(c2)N(C[C@@H]2CC[C@H]21)C[C@@]1(CCCc2cc(Cl)ccc21)CO3]

Step 1: (1S,3'R,6'R,7'S,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

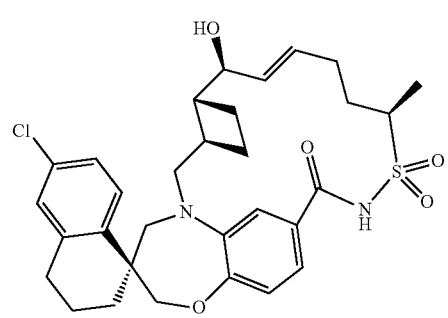 [SMILES: C[C@@H]1CC/C=C/[C@H](O)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 719, Step 2 using a mixture of (R)-hex-5-ene-sulfonamide (Intermediate EE20) and of (S)-hex-5-ene-sulfonamide (Intermediate EE202), and the desired product, (1S,3'R,6'R,7'S,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (the 1st epimer out of preparative reverse phase HPLC) and (1S,3'R,6'R,7'S,8'E,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (the 2nd epimer out of preparative reverse phase HPLC) were isolated. (1S,3'R,6'R,7'S,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide: $^1$H NMR (400 MHz, CD$_3$OD) δ 7.74 (d, J=8.0 Hz, 1H), 7.19 (dd, J=3.5, 11.5 Hz, 1H), 7.12 (d, J=1.8 Hz, 1H), 7.01 (d, J=9.2 Hz, 1H), 7.01 (d, J=7.6 Hz, 1H), 6.94 (d, J=8.0 Hz, 1H), 6.88 (s, 1H), 5.89-5.81 (m, 1H), 5.73 (dd, 14.5 Hz, 1H), 4.22 (dd, J=3.5, 7.6 Hz, 1H), 4.18-4.12 (m, 1H), 4.09 (d, J=2.0 Hz, 2H), 3.85 (d, J=15.1 Hz, 1H), 3.85 (d, J=15.3 Hz, 1H), 3.68 (d, J=14.1 Hz, 1H), 3.08 (dd, J=10.2, 15.1 Hz, 1H), 2.87-2.73 (m, 2H), 2.48-2.18 (m, 4H), 2.11 (d, J=13.7 Hz, 1H), 2.05-1.65 (m, 8H), 1.52 (d, J=6.8 Hz, 3H), 1.47-1.41 (m, 1H). m/z (ESI, +ve ion) 585.2 (M+H)$^+$.

Step 2: 2-(((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N-methylacetamide To a 5-mL round-bottomed flask were added (1S,3'R,6'R,7'S,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (15 mg, 0.026 mmol, Example 404, Step 1) and sodium hydride, 60% dispersion in mineral oil (3.1 mg, 0.13 mmol) in 1 mL of THF at 0° C. The reaction mixture was stirred at 0° C. for 30 min, and then 2-chloro-N-methylacetamide (8.3 mg, 0.077 mmol) was added. The reaction mixture was stirred at ambient temperature overnight. The reaction mixture was quenched with saturated NH$_4$Cl aqueous solution, and diluted with 40 mL of EtOAc. The organic layer was separated and concentrated. The crude product was purified by the reversed phase preparatory HPLC (Gemini™ Prep C$_{18}$ 5 μm column; Phenomenex, Torrance, CA; gradient elution of 40% to 95% MeCN in water, where both solvents contain 0.1% TFA, 30 min method) to provide the title compound. The structure was confirmed by the co-crystal structure of Example 404 with Mcl-1. $^1$H NMR (400 MHz, CDCl$_3$) δ 8.12 (s, 1H), 7.70 (d, J=8.4 Hz, 1H), 7.19 (dd, J=8.5, 2.4 Hz, 1H), 7.07-7.12 (m, 1H), 6.88-6.95 (m, 2H), 6.80 (1H, s), 5.87 (ddd, J=15.3, 9.2, 4.3 Hz, 1H), 5.55 (dd, J=15.7, 9.4 Hz, 1H), 4.22-4.32 (m, 1H), 4.02-4.14 (m, 2H), 3.69-3.96 (m, 5H), 3.23 (d, J=14.5 Hz, 1H), 3.00 (dd, J=15.2, 10.3 Hz, 1H), 2.86 (d, J=5.1 Hz, 3H), 2.71-2.82 (m, 2H), 2.44-2.54 (m, 1H), 2.20-2.41 (m, 3H), 1.91-2.10 (m, 3H), 1.63-1.89 (m, 7H), 1.59 (d, J=7.0 Hz, 3H). m/z (ESI, +ve ion) 656.2 (M+H)$^+$.

Example 405. (1S,3'R,6'R,7'S,8'E,12'R)-6-chloro-7'-(2-methoxyethoxy)-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

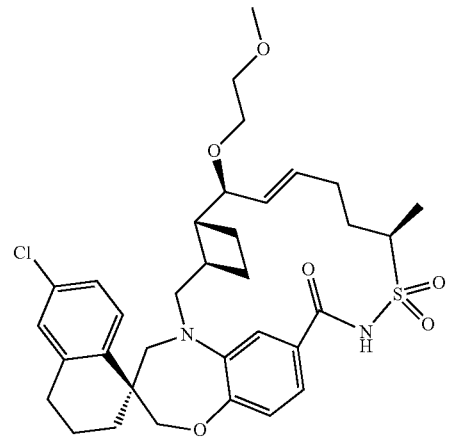 [SMILES: COCCO[C@H]1/C=C/CC[C@@H](C)S(=O)(=O)NC(=O)c2ccc3c(c2)N(C[C@@H]2CC[C@H]21)C[C@@]1(CCCc2cc(Cl)ccc21)CO3]

The title compound was prepared in an analogous manner to that described in Example 404 using 1-bromo-2-methoxyethane instead of 2-chloro-N-methylacetamide. $^1$H NMR (400 MHz, CD$_3$OD) δ 7.72 (d, J=8.6 Hz, 1H), 7.16 (dd, J=8.5, 2.2 Hz, 1H), 7.10 (d, J=2.2 Hz, 1H), 6.98 (d, J=8.3 Hz, 1H), 6.91 (d, J=8.2 Hz, 1H), 6.85 (d, J=1.8 Hz, 1H), 5.80-5.87 (m, 1H), 5.58 (dd, J=15.5, 8.8 Hz, 1H), 4.03-4.18 (m, 3H), 3.80-3.86 (m, 2H), 3.41-3.68 (m, 5H), 3.35 (s, 3H), 3.06 (dd, J=15.3, 10.4 Hz, 1H), 2.70-2.81 (m, 2H), 2.24-2.53 (m, 4H), 2.09 (d, J=13.7 Hz, 1H), 1.68-1.96 (m, 7H), 1.50 (d, J=7.0 Hz, 3H), 1.39-1.47 (m, 2H). m/z (ESI, +ve ion) 643.2 (M+H)$^+$.

Example 406. (1S,3'R,6'R,7'S,8'E,12'R)-6-chloro-12'-methyl-7'-(2-(methylsulfonyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

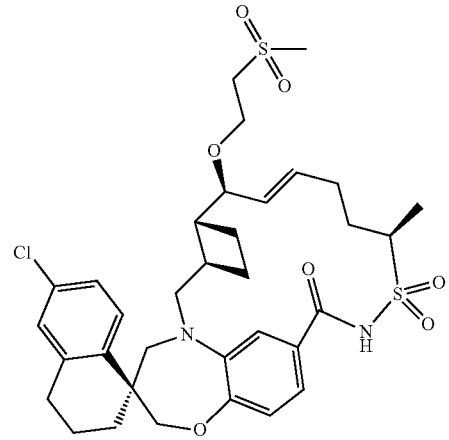 [SMILES: C[C@@H]1CC/C=C/[C@H](OCCS(C)(=O)=O)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 404 using 2-bromoethyl methyl sulfone instead of 2-chloro-N-methylacetamide. $^1$H NMR (500 MHz, CDCl$_3$) δ 7.91 (s, 1H), 7.70 (d, J=8.6 Hz, 1H), 7.19 (dd, J=8.6, 2.2 Hz, 1H), 7.08 (1H, s), 6.87-6.95 (m, 2H), 6.79 (d, J=1.7 Hz, 1H), 5.87 (ddd, J=15.2, 9.3, 3.9 Hz, 1H), 5.56 (dd, J=15.2, 9.3 Hz, 1H), 4.19-4.31 (m, 1H), 4.01-4.16 (m, 2H), 3.77-3.91 (m, 3H), 3.63-3.77 (m, 2H), 3.14-3.27 (m, 3H), 2.95-3.00 (m, 4H), 2.72-2.84 (m, 2H), 2.25-2.48 (m, 4H), 1.73-2.06 (m, 9H), 1.65-1.73 (m, 1H), 1.59 (d, J=7.1 Hz, 3H). m/z (ESI, +ve ion) 691.2 (M+H)$^+$.

Example 407. (((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diaza-tetracyclo[14.7.2.0$^{3,6}$.0$^{19,24}$]pentacosa [8,16,18,24]tetraen]-7'-yl)oxy)acetic acid

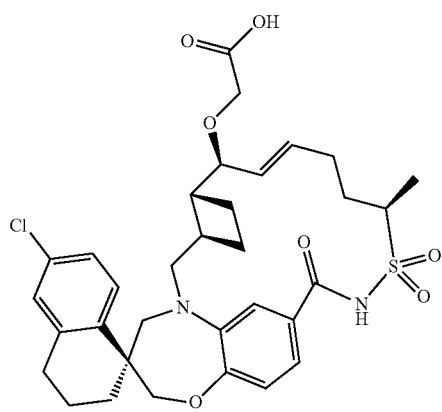 [SMILES: C[C@@H]1CC/C=C/[C@H](OCC(=O)O)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 404 using bromoacetic acid instead of 2-chloro-N-methylacetamide. $^1$H NMR (500 MHz, CD$_3$OD) δ 7.73 (d, J=8.6 Hz, 1H), 7.17 (dd, J=8.4, 2.3 Hz, 1H), 7.11 (1H, d, J=2.2 Hz, 1H), 6.91-6.99 (m, 2H), 6.82 (d, J=2.0 Hz, 1H), 5.84-5.90 (m, 1H), 5.60 (dd, J=15.2, 9.3 Hz, 1H), 4.04-4.20 (m, 3H), 3.99 (s, 2H), 3.93 (dd, J=9.2, 3.5 Hz, 1H), 3.84 (d, J=14.9 Hz, 1H), 3.67 (d, J=14.2 Hz, 1H), 3.08 (dd, J=15.3, 10.4 Hz, 1H), 2.72-2.85 (m, 2H), 2.54-2.63 (m, 1H), 2.26-2.46 (m, 3H), 2.10 (d, J=13.4 Hz, 1H), 1.71-2.02 (m, 9H), 1.51 (d, J=6.8 Hz, 3H). m/z (ESI, +ve ion) 643.2 (M+H)$^+$.

Example 408. methyl(((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)acetate

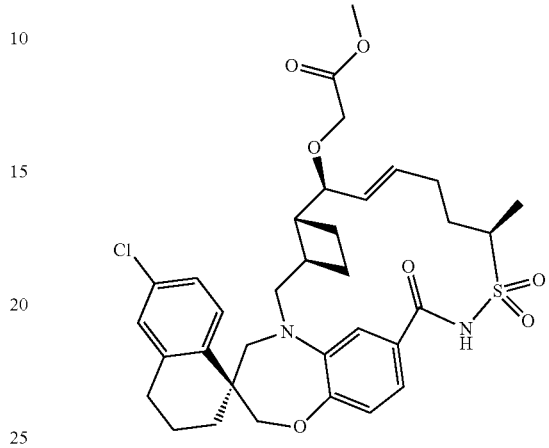

The title compound was prepared in an analogous manner to that described in Example 404 using methyl 2-bromoacetate instead of 2-chloro-N-methylacetamide. $^1$H NMR (500 MHz, CD$_3$OD) δ 7.72 (d, J=8.56 Hz, 1H), 7.17 (dd, J=8.56, 2.20 Hz, 1H), 7.11 (s, 1H), 6.98 (d, J=8.29 Hz, 1H), 6.90-6.94 (m, 1H), 6.82 (s, 1H), 5.81-5.88 (m, 1H), 5.58 (dd, J=15.16, 9.29 Hz, 1H), 4.12-4.19 (m, 1H), 4.05-4.09 (m, 2H), 4.01-4.05 (m, 2H), 3.87-3.94 (m, 1H), 3.83 (d, J=14.92 Hz, 1H), 3.74 (s, 3H), 3.66 (d, J=14.18 Hz, 1H), 3.07 (dd, J=15.41, 10.27 Hz, 1H), 2.72-2.85 (m, 2H), 2.51-2.60 (m, 1H), 2.24-2.43 (m, 3H), 2.10 (d, J=13.69 Hz, 1H), 1.79-1.97 (m, 7H), 1.69-1.78 (m, 2H) 1.51 (d, J=6.85 Hz, 3H). m/z (ESI, +ve ion) 657.2 (M+H)$^+$.

Example 409. (1S,3'R,6'R,7'S,8'E,12'R)-6-chloro-7'-((3,5-dimethyl-4-isoxazolyl)methoxy)-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

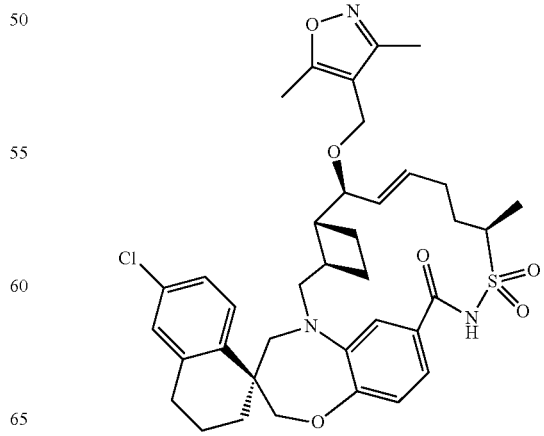

The title compound was prepared in an analogous manner to that described in Example 404 using 4-(chloromethyl)-3,5-dimethylisoxazole instead of 2-chloro-N-methylacetamide. $^1$H NMR (500 MHz, CD$_3$OD) δ 7.72 (d, J=8.6 Hz, 1H), 7.17 (dd, J=8.6, 2.2 Hz, 1H), 7.10 (d, J=2.2 Hz, 1H), 6.98 (dd, J=8.1, 2.0 Hz, 1H), 6.92 (d, J=8.3 Hz, 1H), 6.84 (d, J=1.7 Hz, 1H), 5.82-5.88 (m, 1H), 5.62 (dd, J=15.4, 8.8 Hz, 1H), 4.32 (d, J=12.0 Hz, 1H), 4.13-4.21 (m, 2H), 4.03-4.09 (m, 2H), 3.79-3.87 (m, 2H), 3.65 (d, J=14.2 Hz, 1H), 3.06 (dd, J=15.3, 10.1 Hz, 1H), 2.71-2.84 (m, 2H), 2.39-2.49 (m, 2H), 2.37 (s, 3H), 2.25-2.36 (m, 2H), 2.22 (s, 3H), 2.09 (d, J=13.7 Hz, 1H), 1.64-2.01 (m, 8H), 1.52 (d, J=6.8 Hz, 4H), 1.43 (br. s., 1H). m/z (ESI, +ve ion) 694.2 (M+H)$^+$.

Example 410. (1S,3'R,6'R,7'S,8'E,12'R)-6-chloro-12'-methyl-7'-((l-methyl-1H-1,2,4-triazol-3-yl)methoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide Example 411. (1S,3'R,6'R,7'S,8'E,12'R)-6-chloro-12'-methyl-7'-((5-methyl-3-isoxazolyl)methoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

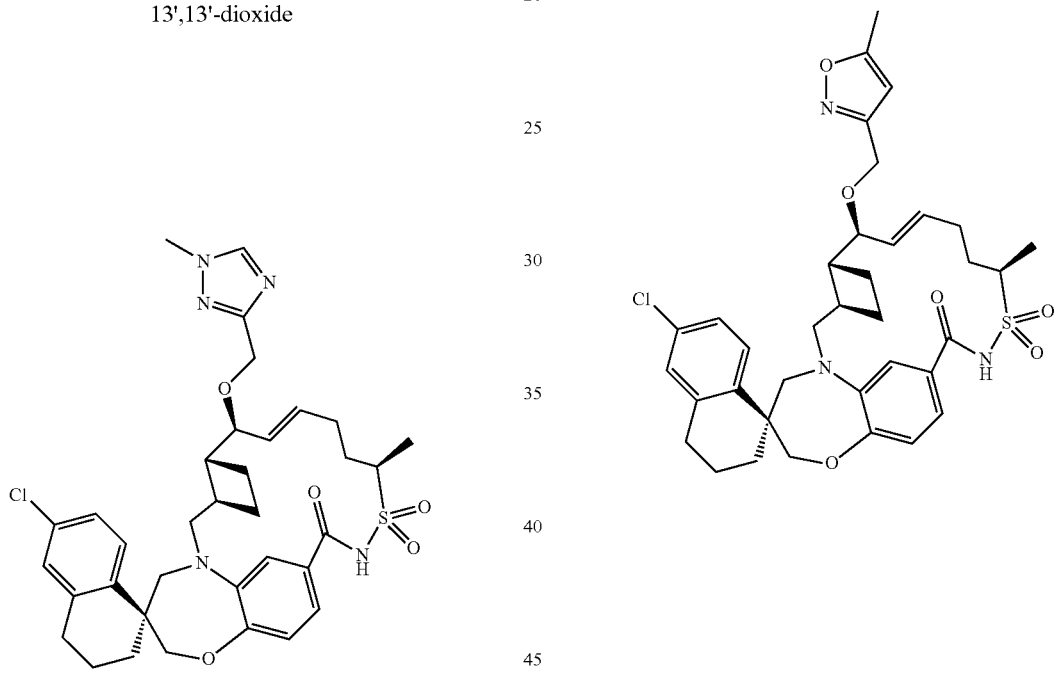

The title compound was prepared in an analogous manner to that described in Example 404 using 3-(chloromethyl)-1-methyl-1H-1,2,4-triazole hydrochloride instead of 2-chloro-N-methylacetamide. $^1$H NMR (500 MHz, CD$_3$OD) δ 8.53 (s, 1H), 7.72 (d, J=8.6 Hz, 1H), 7.17 (dd, J=2.3, 8.4 Hz, 1H), 7.10 (d, J=2.2 Hz, 1H), 6.97 (dd, J=2.0, 8.1 Hz, 1H), 6.90 (d, J=8.1 Hz, 1H), 6.79 (d, J=1.7 Hz, 1H), 5.89-5.83 (m, 1H), 5.59 (dd, J=8.9, 15.3 Hz, 1H), 4.58-4.50 (m, 1H), 4.49-4.34 (m, 1H), 4.20-4.14 (m, 1H), 4.09-4.02 (m, 2H), 3.97 (s, 3H), 3.89 (dd, J=3.4, 8.8 Hz, 1H), 3.80-3.72 (m, 1H), 3.65 (d, J=14.2 Hz, 1H), 3.26 (d, J=13.9 Hz, 1H), 3.05 (dd, J=10.3, 15.4 Hz, 1H), 2.84-2.71 (m, 2H), 2.53-2.47 (m, 1H), 2.45-2.37 (m, 1H), 2.35-2.27 (m, 2H), 2.08 (d, J=13.7 Hz, 1H), 1.95-1.78 (m, 7H), 1.77-1.69 (m, 2H), 1.52 (d, J=7.1 Hz, 3H). m/z (ESI, +ve ion) 680.2 (M+H)$^+$.

The title compound was prepared in an analogous manner to that described in Example 404 using 3-chloromethyl-5-methylisoxazole instead of 2-chloro-N-methylacetamide. $^1$H NMR (500 MHz, CD$_3$OD) δ 7.71 (d, J=8.3 Hz, 1H), 7.17 (dd, J=2.3, 8.4 Hz, 1H), 7.10 (d, J=2.2 Hz, 1H), 6.98 (dd, J=1.8, 8.2 Hz, 1H), 6.91 (d, J=8.1 Hz, 1H), 6.83 (d, J=1.7 Hz, 1H), 6.11 (s, 1H), 5.89-5.82 (m, 1H), 5.60 (dd, J=8.9, 15.3 Hz, 1H), 4.46 (d, J=12.7 Hz, 1H), 4.39 (d, J=13.0 Hz, 1H), 4.16 (ddd, J=3.3, 6.7, 9.8 Hz, 1H), 4.09-4.02 (m, 2H), 3.90 (dd, J=3.8, 8.9 Hz, 1H), 3.81 (d, J=14.4 Hz, 1H), 3.65 (d, J=14.2 Hz, 1H), 3.27 (d, J=14.2 Hz, 1H), 3.05 (dd, J=10.0, 15.4 Hz, 1H), 2.84-2.71 (m, 2H), 2.56-2.46 (m, 1H), 2.44-2.28 (m, 6H), 2.08 (d, J=13.7 Hz, 1H), 1.97-1.79 (m, 6H), 1.76-1.70 (m, 2H), 1.51 (d, J=6.8 Hz, 3H), 1.48-1.36 (m, 1H). m/z (ESI, +ve ion) 680.2 (M+H)$^+$.

945

Example 412. (1S,3'R,6'R,7'S,8'E,12'R)-6-chloro-12'-methyl-7'-((5-methyl-1,3,4-oxadiazol-2-yl)methoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

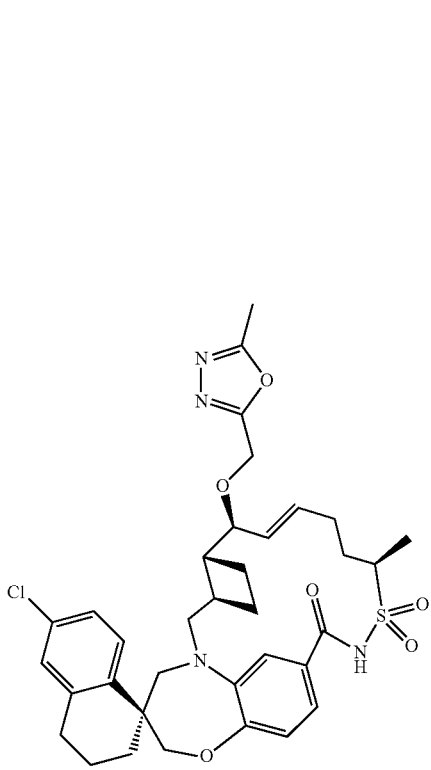 [SMILES: Cc1nnc(CO[C@H]2/C=C/CC[C@@H](C)S(=O)(=O)NC(=O)c3ccc4c(c3)N(C[C@@H]3CC[C@H]32)C[C@@]2(CCCc3cc(Cl)ccc32)CO4)o1]

The title compound was prepared in an analogous manner to that described in Example 404 using 2-(chloromethyl)-5-methyl-1,3,4-oxadiazole instead of 2-chloro-N-methylacetamide. ¹H NMR (500 MHz, CD₃OD) δ 7.74 (d, J=8.6 Hz, 1H), 7.19 (dd, J=2.3, 8.4 Hz, 1H), 7.12 (d, J=2.2 Hz, 1H), 7.00 (dd, J=2.0, 8.1 Hz, 1H), 6.92 (d, J=8.1 Hz, 1H), 6.86 (d, J=2.0 Hz, 1H), 5.95-5.89 (m, 1H), 5.61 (dd, J=8.9, 15.3 Hz, 1H), 4.66-4.61 (m, 1H), 4.61-4.54 (m, 1H), 4.22-4.16 (m, 1H), 4.09-4.05 (m, 2H), 3.99 (dd, J=3.8, 8.9 Hz, 1H), 3.85 (d, J=14.9 Hz, 1H), 3.68 (d, J=14.2 Hz, 1H), 3.32-3.28 (m, 1H), 3.28-3.31 (m, 1H), 3.08 (dd, J=10.3, 15.4 Hz, 1H), 2.86-2.73 (m, 2H), 2.58-2.55 (m, 4H), 2.46-2.27 (m, 3H), 2.11 (d, J=13.7 Hz, 1H), 1.98-1.81 (m, 7H), 1.79-1.71 (m, 2H), 1.54 (d, J=7.1 Hz, 3H). m/z (ESI, +ve ion) 681.2 (M+H)⁺.

946

Example 413. (1S,3'R,6'R,7'S,8'E,12'R)-6-chloro-12'-methyl-7'-(((3S)-2-oxotetrahydro-3-furanyl)oxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa 8,16,18,24]tetraen]-15'-one 13',13'-dioxide

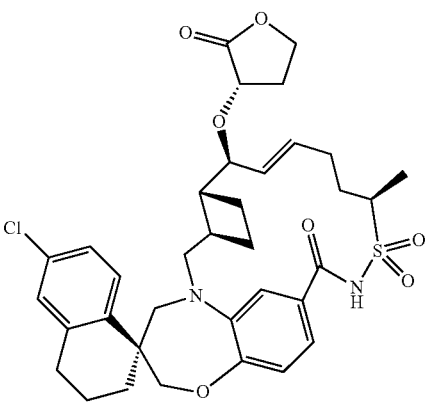 [SMILES: C[C@@H]1CC/C=C/[C@H](O[C@H]2CCOC2=O)[C@@H]2CC[C@H]2CN2C[C@@]3(CCCc4cc(Cl)ccc43)COc3ccc(cc32)C(=O)NS1(=O)=O]

Step 1: (R)-3-azidodihydrofuran-2(3H)-one and (S)-3-azidodihydrofuran-2(3H)-one

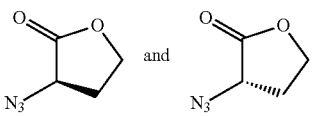 [SMILES: [N-]=[N+]=N[C@@H]1CCOC1=O ; [N-]=[N+]=N[C@H]1CCOC1=O]

To a 25-mL round-bottomed flask were added alpha-bromo-gamma-butyrolactone (0.168 mL, 1.82 mmol) and sodium azide (177 mg, 2.73 mmol) in DMSO (6.1 mL). The mixture was stirred at ambient temperature for 2 days. The reaction mixture was diluted with saturated NaHCO₃ solution (10 mL) and extracted with Et₂O (2×10 mL). The organic extract was washed with saturated NaCl (10 mL) and dried over MgSO₄. The solution was filtered and concentrated in vacuo to give the title compound (200 mg, 87%) as a colorless oil. ¹H NMR (500 MHz, CDCl₃) δ 4.41-4.51 (m, 1H), 4.25-4.37 (m, 2H), 2.59 (dddd, J=3.67, 6.72, 8.47, 13.17 Hz, 1H), 2.12-2.28 (m, 1H).

Step 2: 2,5-dioxopyrrolidin-1-yl 3-(diphenylphosphino)propanoate

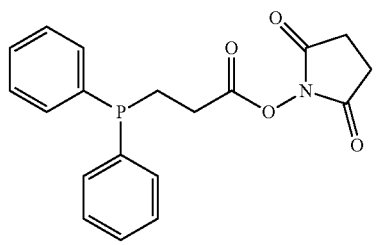 [SMILES: O=C(CCP(c1ccccc1)c1ccccc1)ON1C(=O)CCC1=O]

To a 100-mL round-bottomed flask were added 3-(diphenylphosphino)propanoic acid (2.50 g, 9.68 mmol) and n-hydroxysuccinimide (1.23 g, 10.7 mmol) in DCM (19.4 ml), and then N,N'-methanediylidenebis(propan-2-amine) (1.34 g, 10.7 mmol). The mixture was stirred at ambient temperature overnight. The reaction mixture was diluted with Et$_2$O and the solid was removed by filtration. The filtrate was concentrated. The residue was redissolved in a mixture of EtOAc and hexane, and solid was precipitated. Filtration provided the title compound (2.00 g, 58%). m/z (ESI, +ve ion) 356.1 (M+H)$^+$.

Step 3: 3-diazodihydrofuran-2(3H)-one

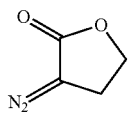

To a 25-mL round-bottomed flask were added 2,5-dioxopyrrolidin-1-yl 3-(diphenylphosphino)propanoate (288 mg, 0.810 mmol, Step 2) and (R)-3-azidodihydrofuran-2(3H)-one and (S)-3-azidodihydrofuran-2(3H)-one (100 mg, 0.787 mmol, Step 1) in THF (1.4 mL) and water (0.21 mL). The mixture was stirred at ambient temperature for 3 h, and then 3 mL of saturated NaHCO$_3$ aqueous solution was added. After stirred another 15 min. the solution became yellow. The reaction mixture was diluted with saturated NaCl aqueous solution, extracted with DCM. The combined DCM solution was dried over MgSO$_4$, filtered and concentrated. The residue was purified by chromatography using DCM as an eluent to provide the title compound (70 mg, 79%). $^1$H NMR (400 MHz, CDCl$_3$) δ 4.38-4.46 (m, 2H), 3.36-3.43 (m, 2H).

Step 4: (1S,3'R,6'R,7'S,8'E,12'R)-6-chloro-12'-methyl-7'-(((3S)-2-oxotetrahydro-3-furanyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide To a 25-mL round-bottomed flask were added (1S,3'R,6'R,7'S,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (12 mg, 0.021 mmol, Example 404, Step 1) and rhodium (ii) acetate dimer (2.7 mg, 6.2 μmol) in DCM (680 μl), and then 3-diazodihydrofuran-2(3H)-one (5.8 mg, 0.051 mmol, Step 3). The reaction mixture was stirred at ambient temperature overnight. The reaction mixture was filtered, filtrate was concentrated. The crude product was purified by the reversed phase preparatory HPLC (Gemini™ Prep C$_{18}$ 5 μm column; Phenomenex, Torrance, CA; gradient elution of 40% to 95% MeCN in water, where both solvents contain 0.1% TFA, 30 min method) to provide the title compound as the second eluting isomer. $^1$H NMR (500 MHz, MeOH) δ 7.74 (d, J=8.31 Hz, 1H), 7.19 (dd, J=2.20, 8.56 Hz, 1H), 7.12 (d, J=2.20 Hz, 1H), 6.99-7.02 (m, 1H), 6.92-6.95 (m, 1H), 6.91 (d, J=1.71 Hz, 1H), 5.86-5.94 (m, 1H), 5.61 (dd, J=8.80, 15.16 Hz, 1H), 4.30-4.40 (m, 3H), 4.21-4.27 (m, 1H), 4.14-4.21 (m, 1H), 4.05-4.12 (m, 2H), 3.88 (d, J=13.45 Hz, 1H), 3.68 (d, J=14.18 Hz, 1H), 3.35-3.40 (m, 1H), 3.28-3.31 (m, 1H), 3.10 (dd, J=9.90, 15.28 Hz, 1H), 2.73-2.88 (m, 2H), 2.59 (dq, J=3.91, 9.21 Hz, 1H), 2.36-2.48 (m, 3H), 2.27-2.35 (m, 1H), 2.09-2.15 (m, 1H), 2.01-2.08 (m, 1H), 1.80-2.00 (m, 6H), 1.71-1.80 (m, 2H), 1.53 (d, J=6.85 Hz, 3H), 1.41-1.49 (m, 1H). m/z (ESI, +ve ion) 669.2 (M+H)$^+$.

Example 414. (1S,3'R,6'R,7'S,8'E,12'R)-6-chloro-12'-methyl-7'-(((3R)-2-oxotetrahydro-3-furanyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

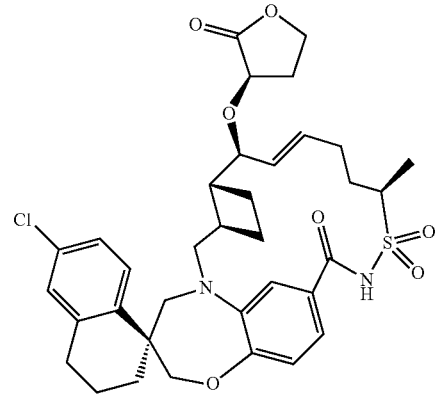 [SMILES: C[C@@H]1CC/C=C/[C@H](O[C@@H]2CCOC2=O)[C@@H]2CC[C@H]2CN2C[C@@]3(CCCc4cc(Cl)ccc43)COc3ccc(cc32)C(=O)NS1(=O)=O]

The title compound was obtained as the first eluting isomer from the reversed phase preparatory HPLC separation in Example 413, Step 4. $^1$H NMR (500 MHz, CD$_3$OD) δ 7.75 (d, J=8.31 Hz, 1H), 7.19 (dd, J=2.20, 8.56 Hz, 1H), 7.13 (d, J=1.96 Hz, 1H), 7.01 (dd, J=1.83, 8.19 Hz, 1H), 6.91-6.96 (m, 1H), 6.86 (d, J=1.71 Hz, 1H), 5.88-5.98 (m, 1H), 5.62-5.73 (m, 1H), 4.38-4.45 (m, 2H), 4.27 (dt, J=6.36, 9.41 Hz, 1H), 4.15-4.23 (m, 1H), 4.03-4.13 (m, 3H), 3.87 (d, J=15.16 Hz, 1H), 3.69 (d, J=14.18 Hz, 1H), 3.34-3.38 (m, 1H), 3.28-3.34 (m, 1H), 3.09 (dd, J=10.27, 15.16 Hz, 1H), 2.73-2.87 (m, 2H), 2.61-2.69 (m, 1H), 2.48-2.56 (m, 1H), 2.40-2.48 (m, 1H), 2.28-2.40 (m, 2H), 2.08-2.22 (m, 2H), 1.81-1.99 (m, 6H), 1.71-1.80 (m, 2H), 1.53 (d, J=6.85 Hz, 3H), 1.42-1.50 (m, 1H). m/z (ESI, +ve ion) 669.2 (M+H)$^+$.

Example 415. (1S,3'R,6'R,7'S,8'E,12'R)-6-chloro-7'-(((2R)-2,3-dihydroxypropyl)oxy)-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide and (1S,3'R,6'R,7'S,8'E,12'R)-6-chloro-7'-(((2S)-2,3-dihydroxypropyl)oxy)-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

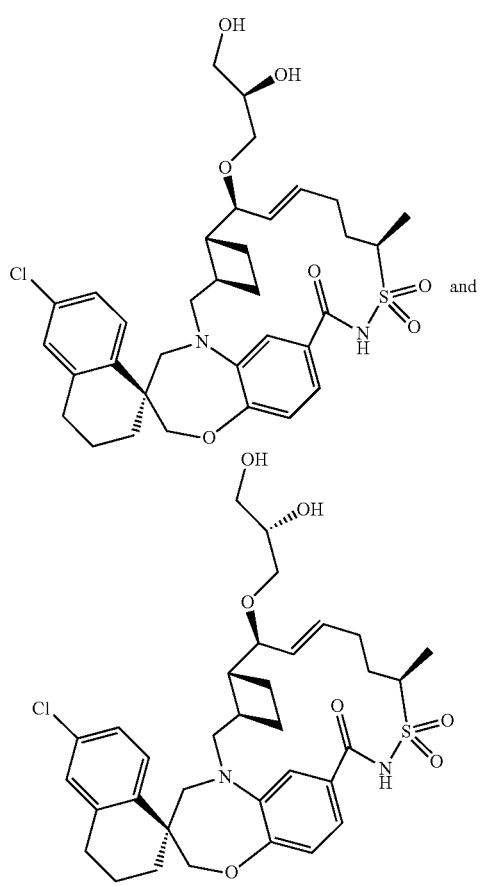

To a 25-mL round-bottomed flask were added (1S,3'R,6'R,7'S,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (40 mg, 0.068 mmol, Example 404, Step 1) and sodium hydride, 60% dispersion in mineral oil (27 mg, 0.68 mmol) in 1 mL of THF at ambient temperature. The reaction mixture was stirred for 30 min, and then (+)/(−)-epichlorohydrin (53.5 μl, 0.684 mmol) was added. The reaction mixture was stirred at ambient temperature overnight. The reaction was quenched with 2 N HCl. The crude material was purified by chromatography through a Redi-Sep pre-packed silica gel column (12 g), eluting with a gradient of 0% to 45% EtOAc in hexane to provide the product as the precursor of the title compound. The compound obtained above was dissolved in 100 mL of water/ACN mixture with 0.3% HOAc, and stirred at ambient temperature for 6 hours. The mixture was concentrated, and repeated twice. The crude material was purified by reversed phase preparatory HPLC (Gemini™ Prep C$_{18}$ 5 μm column; Phenomenex, Torrance, CA; gradient elution of 40% to 95% MeCN in water, where both solvents contain 0.1% TFA, 30 min method) to provide the title compound. $^1$H NMR (500 MHz, CD$_3$OD) δ 7.75 (d, J=8.56 Hz, 1H), 7.19 (dd, J=2.32, 8.44 Hz, 1H), 7.12 (d, J=2.20 Hz, 1H), 6.97-7.03 (m, 1H), 6.90-6.96 (m, 1H), 6.87 (d, J=1.71 Hz, 1H), 5.80-5.92 (m, 1H), 5.61 (dd, J=9.29, 15.41 Hz, 1H), 4.14-4.24 (m, 1H), 4.03-4.13 (m, 2H), 3.80-3.92 (m, 2H), 3.65-3.77 (m, 2H), 3.55-3.62 (m, 1H), 3.28-3.34 (m, 2H), 3.35-3.40 (m, 1H), 3.28-3.33 (m, 1H), 3.08 (dd, J=10.39, 15.28 Hz, 1H), 2.73-2.88 (m, 2H), 2.48-2.58 (m, 1H), 2.26-2.47 (m, 3H), 2.12 (d, J=13.69 Hz, 1H), 1.79-2.01 (m, 6H), 1.69-1.79 (m, 2H), 1.52 (d, J=6.85 Hz, 3H), 1.46 (t, J=14.18 Hz, 1H). m/z (ESI, +ve ion) 659.2 (M+H)$^+$.

Example 416. (1S,3'R,6'R,7'S,8'E,12'R)-6-chloro-12'-methyl-7'-((1-methyl-1H-1,2,3-triazol-5-yl)methoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

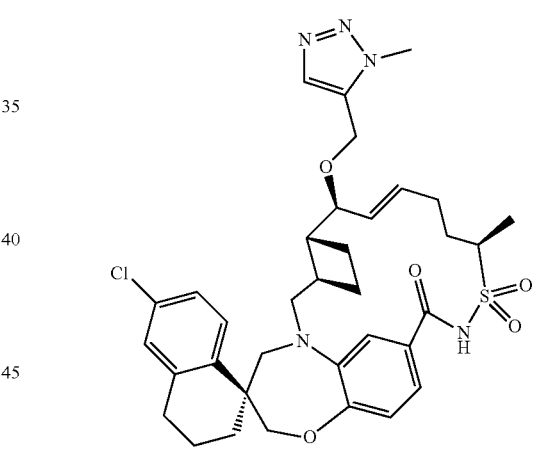

The title compound was prepared in an analogous manner to that described in Example 404 using 5-(chloromethyl)-1-methyl-1H-1,2,3-triazole hydrochloride. $^1$H NMR (400 MHz, DCCl$_3$) δ 8.01 (s, 1H), 7.69 (d, J=8.41 Hz, 1H), 7.64 (s, 1H), 7.19 (dd, J=2.35, 8.61 Hz, 1H), 7.10 (d, J=2.15 Hz, 1H), 6.88-6.96 (m, 2H), 6.80 (d, J=1.56 Hz, 1H), 5.84-5.94 (m, 1H), 5.59 (dd, J=9.29, 15.36 Hz, 1H), 4.54 (d, J=12.52 Hz, 1H), 4.40 (d, J=12.52 Hz, 1H), 4.22-4.32 (m, 1H), 4.03-4.13 (m, 5H), 3.89 (dd, J=3.33, 9.00 Hz, 1H), 3.68-3.84 (m, 2H), 3.50 (q, J=7.04 Hz, 1H), 3.22 (d, J=14.48 Hz, 1H), 2.99 (dd, J=10.17, 15.06 Hz, 1H), 2.71-2.81 (m, 2H), 2.21-2.48 (m, 3H), 1.92-2.12 (m, 3H), 1.75-1.87 (m, 5H), 1.63-1.71 (m, 1H), 1.61 (d, J=7.04 Hz, 3H), 1.40 (t, J=12.72 Hz, 1H). m/z (ESI, +ve ion) 680.2 (M+H)$^+$.

Example 417. (1S,3'R,6'R,7'S,8'E,12'R)-6-chloro-12'-methyl-7'-(((1-methyl-1H-1,2,3-triazol-4-yl)methoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

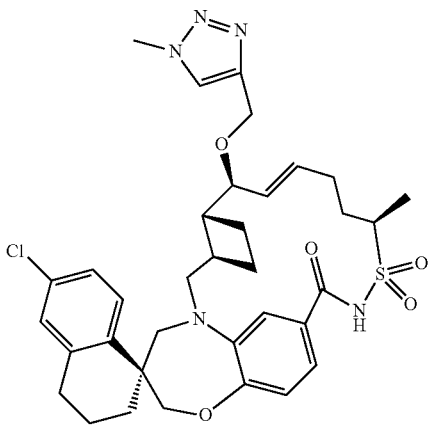 [SMILES: C[C@@H]1CC/C=C/[C@H](OCc2cn(C)nn2)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 404 using 4-(chloromethyl)-1-methyl-1H-1,2,3-triazole hydrochloride. $^1$H NMR (500 MHz, CD$_3$OD) δ 7.88 (s, 1H), 7.66-7.76 (m, 1H), 7.19 (dd, J=2.32, 8.44 Hz, 1H), 7.12 (d, J=2.20 Hz, 1H), 7.00 (dd, J=1.96, 8.31 Hz, 1H), 6.93 (d, J=8.07 Hz, 1H), 6.86 (d, J=1.96 Hz, 1H), 5.81-5.92 (m, 1H), 5.63 (dd, J=8.56, 15.41 Hz, 1H), 4.54-4.60 (m, 1H), 4.47 (d, J=11.98 Hz, 1H), 4.09-4.19 (m, 4H), 4.04-4.09 (m, 2H), 3.94 (dd, J=3.67, 8.56 Hz, 1H), 3.82 (d, J=15.16 Hz, 1H), 3.66 (d, J=14.18 Hz, 1H), 3.25-3.32 (m, 1H), 3.07 (dd, J=10.03, 15.16 Hz, 1H), 2.72-2.87 (m, 2H), 2.26-2.55 (m, 4H), 2.10 (d, J=13.69 Hz, 1H), 1.68-1.99 (m, 8H), 1.54 (d, J=6.85 Hz, 3H), 1.40-1.49 (m, 1H). m/z (ESI, +ve ion) 680.2 (M+H)$^+$.

Example 418. (1S,3'R,6'R,7'S,8'E,12'R)-6-chloro-12'-methyl-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

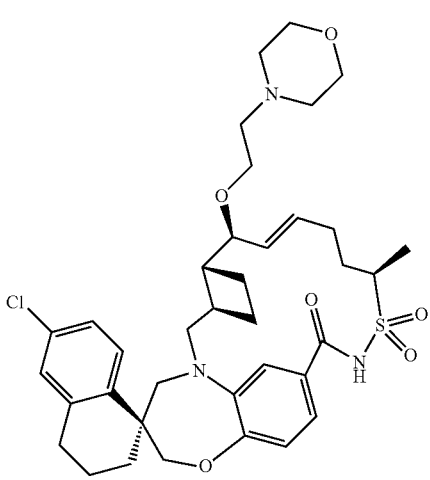 [SMILES: C[C@@H]1CC/C=C/[C@H](OCCN2CCOCC2)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 404 using 4-(2-bromoethyl)morpholine hydrobromide. $^1$H NMR (500 MHz, CDCl$_3$) δ 8.22 (br. s., 1H), 7.70 (d, J=8.56 Hz, 1H), 7.19 (dd, J=2.20, 8.31 Hz, 1H), 7.09 (d, J=1.96 Hz, 1H), 6.86-6.96 (m, 2H), 6.77 (s, 1H), 5.84-5.96 (m, 1H), 5.52 (dd, J=8.80, 14.92 Hz, 1H), 4.24 (dd, J=7.09, 12.72 Hz, 1H), 3.94-4.12 (m, 6H), 3.86 (br. s., 1H), 3.68-3.82 (m, 3H), 3.60-3.66 (m, 2H), 3.16-3.33 (m, 3H), 2.88-3.04 (m, 2H), 2.70-2.85 (m, 2H), 2.26-2.48 (m, 4H), 1.92-2.07 (m, 5H), 1.74-1.87 (m, 5H), 1.62-1.70 (m, 1H), 1.58 (d, J=6.85 Hz, 3H), 1.39 (t, J=12.96 Hz, 1H). m/z (ESI, +ve ion) 698.2 (M+H)$^+$.

Example 419. (2S)-2-(((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N,N-dimethylbutanamide or (2R)-2-(((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N,N-dimethylbutanamide

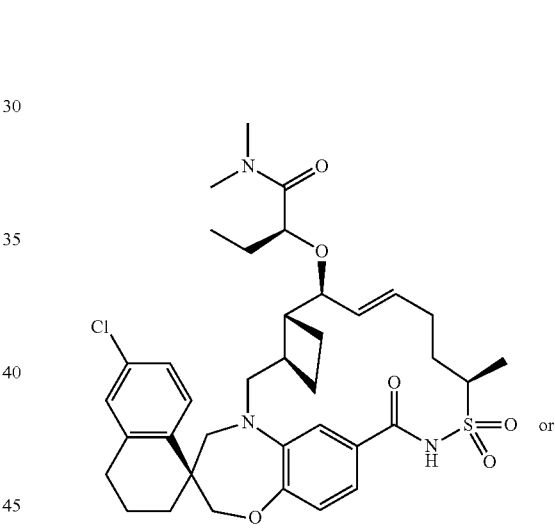

or

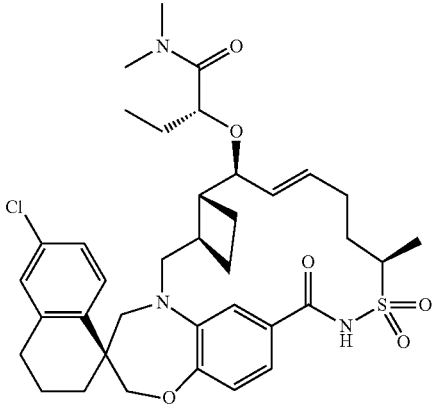

Step 1: (R)-2-bromo-N,N-dimethylbutanamide and (S)-2-bromo-N,N-dimethylbutanamide

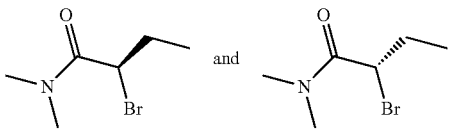

To a 100-mL round-bottomed flask were added 2-(1h-benzotriazol-1-yl)-1,1,3,3-tetramethyluronium hexafluorophosphate (5.79 g, 15.3 mmol) DIEA (3.56 ml, 20.4 mmol), 2-bromo butyric acid (1.70 g, 10.2 mmol) and dimethylamine, 2.0 M solution in tetrahydrofuran (7.63 ml, 15.3 mmol) in THF (40.7 ml). The mixture was stirred at ambient temperature overnight. The reaction mixture was diluted with water (30 mL) and extracted with $CH_2CL_2$ (2×30 mL). The organic solution was concentrated. The crude material was purified by chromatography through a Redi-Sep pre-packed silica gel column (40 g), eluting with a gradient of 0% to 65% EtOAc in heptane, to provide the title compound (1.10 g, 56%). $^1$H NMR (400 MHz, $CDCl_3$) δ 4.31-4.42 (m, 1H), 3.13 (s, 3H), 3.03 (s, 3H), 2.00-2.28 (m, 2H), 1.04 (t, J=7.24 Hz, 3H).

Step 2: (2S)-2-(((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N,N-dimethylbutanamide or (2R)-2-(((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N,N-dimethylbutanamide The title compound was prepared in an analogous manner to that described in Example 404 using (R)-2-bromo-N,N-dimethylbutanamide and (S)-2-bromo-N,N-dimethylbutanamide (Step 1), and was isolated as the first eluting isomer from the reversed phase preparatory HPLC separation. $^1$H NMR (500 MHz, $CDCl_3$) δ 7.90-7.98 (m, 1H), 7.65-7.73 (m, 1H), 7.18 (dd, J=2.20, 8.56 Hz, 1H), 7.09 (d, J=2.20 Hz, 1H), 6.89-6.94 (m, 1H), 6.85-6.88 (m, 1H), 6.78 (d, J=1.71 Hz, 1H), 5.69-5.78 (m, 1H), 5.55 (dd, J=9.17, 15.53 Hz, 1H), 4.21-4.30 (m, 1H), 4.01-4.13 (m, 3H), 3.81 (d, J=15.16 Hz, 1H), 3.66-3.74 (m, 2H), 3.22 (d, J=14.18 Hz, 2H), 3.10-3.15 (m, 3H), 3.06 (s, 3H), 2.92-3.01 (m, 2H), 2.70-2.84 (m, 2H), 2.50-2.58 (m, 1H), 2.34-2.43 (m, 1H), 2.22-2.32 (m, 2H), 2.04 (d, J=13.94 Hz, 1H), 1.91-2.00 (m, 2H), 1.73-1.87 (m, 4H), 1.61-1.72 (m, 2H), 1.58 (d, J=6.85 Hz, 3H), 1.37 (t, J=12.72 Hz, 1H), 0.93 (t, J=7.46 Hz, 3H). m/z (ESI, +ve ion) 698.2 (M+H)$^+$.

Example 420. 2-(((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N,N-dimethylacetamide

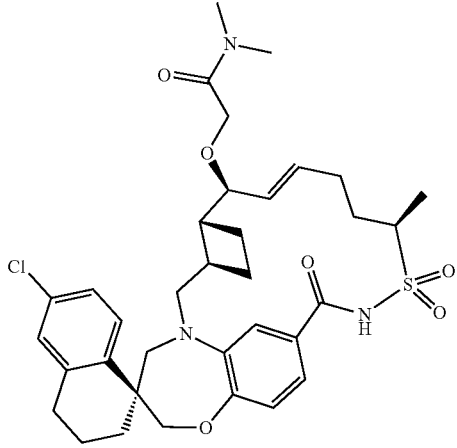 [SMILES: C[C@@H]1CC/C=C/[C@H](OCC(=O)N(C)C)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 404 using 2-chloro-N,N-dimethylacetamide instead of 2-chloro-N-methylacetamide. $^1$H NMR (400 MHz, $CD_3OD$) δ 7.75 (d, J=8.4 Hz, 1H), 7.19 (dd, J=2.2, 8.6 Hz, 1H), 7.12 (d, J=2.2 Hz, 1H), 7.01 (dd, J=1.6, 8.2 Hz, 1H), 6.93 (d, J=8.0 Hz, 1H), 6.86 (d, J=1.8 Hz, 1H), 5.95-5.86 (m, 1H), 5.62 (dd, J=9.2, 15.3 Hz, 1H), 4.23-4.04 (m, 5H), 3.90 (dd, J=3.5, 9.0 Hz, 1H), 3.86 (d, J=15.5 Hz, 1H), 3.68 (d, J=14.1 Hz, 1H), 3.11 (dd, J=10.6, 16.0 Hz, 1H), 3.06-3.01 (m, 3H), 2.97 (s, 3H), 2.88-2.72 (m, 2H), 2.64-2.54 (m, 1H), 2.48-2.26 (m, 3H), 2.12 (d, J=13.5 Hz, 1H), 1.99-1.71 (m, 9H), 1.53 (d, J=7.0 Hz, 3H), 1.50-1.41 (m, 1H) m/z (ESI, +ve ion) 670.2 (M+H)$^+$.

Example 421. (2R)-2-(((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N,N-dimethylbutanamide or (2S)-2-(((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N,N-dimethylbutanamide

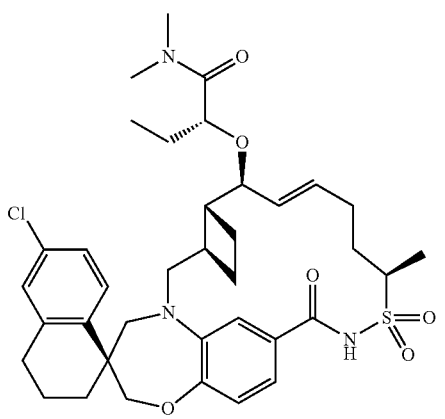

or

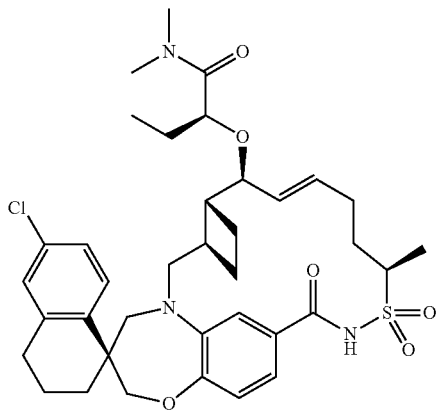

The title compound was obtained as the second eluting isomer from the reversed phase preparatory HPLC separation in Example 419, Step 2. $^1$H NMR (500 MHz, CDCL$_3$) δ 7.91-7.96 (m, 1H), 7.67-7.73 (m, 1H), 7.19 (dd, J=2.20, 8.56 Hz, 1H), 7.09 (d, J=2.20 Hz, 1H), 6.90-6.94 (m, 1H), 6.85-6.89 (m, 1H), 6.79 (d, J=1.71 Hz, 1H), 5.79-5.89 (m, 1H), 5.52-5.61 (m, 1H), 4.22-4.31 (m, 1H), 4.02-4.12 (m, 2H), 3.98 (dd, J=5.62, 8.07 Hz, 1H), 3.78-3.87 (m, 2H), 3.68-3.75 (m, 1H), 3.23 (d, J=14.43 Hz, 1H), 3.07-3.14 (m, 3H), 2.96-3.06 (m, 2H), 2.94 (s, 3H), 2.70-2.84 (m, 3H), 2.47-2.57 (m, 1H), 2.25-2.34 (m, 2H), 2.09-2.19 (m, 1H), 1.87-2.08 (m, 3H), 1.73-1.85 (m, 4H), 1.62-1.72 (m, 2H), 1.58 (d, J=6.85 Hz, 3H), 1.38 (t, J=12.59 Hz, 1H), 0.99 (t, J=7.34 Hz, 3H). m/z (ESI, +ve ion) 698.2 (M+H)$^+$.

Example 422. 2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-(1-methylethyl)acetamide

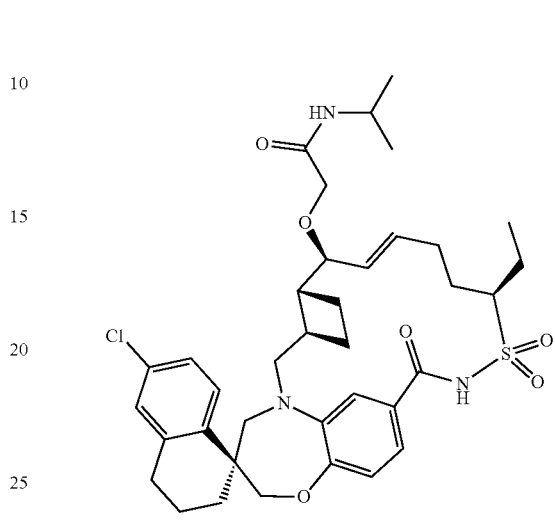

Step 1: (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

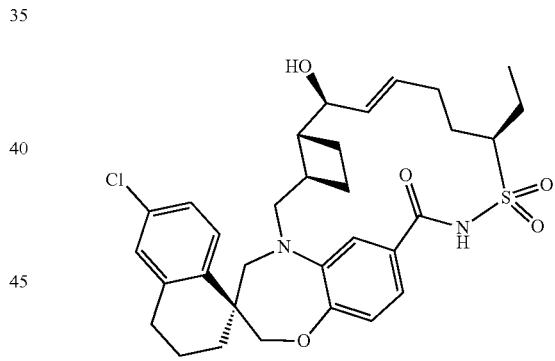

The title compound was prepared in an analogous manner to that described in Example 719, Step 1 and Step 2 using a racemic mixture of (R)-hept-6-ene-3-sulfonamide (Intermediate EE21) and (S)-hept-6-ene-3-sulfonamide (Intermediate EE212), and the desired products, (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]-tetraen]-15'-one 13',13'-dioxide as the first eluting major isomer out of preparative reverse phase HPLC. $^1$H NMR (400 MHz, CD$_3$OD) δ 7.75 (d, J=8.4 Hz, 1H), 7.19 (dd, J=2.0, 8.8 Hz, 1H), 7.12 (d, J=2.2 Hz, 1H), 7.00 (dd, J=1.8, 8.0 Hz, 1H), 6.93 (d, J=8.2 Hz, 1H), 6.87 (d, J=1.6 Hz, 1H), 5.90-5.82 (m, 1H), 5.73 (dd, J=7.8, 15.1 Hz, 1H), 4.21 (dd, J=3.7, 7.8 Hz, 1H), 4.09 (dd, J=12.1, 14.7 Hz, 2H), 4.02 (dd, J=6.5, 13.5 Hz, 1H), 3.85 (d, J=15.1 Hz, 1H), 3.68 (d, J=14.1 Hz, 1H), 3.29 (d, J=14.3 Hz, 1H), 3.08 (dd, J=10.0, 15.3 Hz, 1H), 2.88-2.73 (m, 2H), 2.46-2.22 (m, 4H), 2.16-2.05 (m, 2H), 2.02-1.79 (m, 8H), 1.73 (dd, J=9.0, 17.6 Hz, 1H), 1.46 (t, J=12.6 Hz, 1H), 1.20 (t, J=7.5 Hz, 3H). m/z (ESI, +ve ion) 599.2 (M+H)+.

Step 2: 2-(((1S,3'R,6'R,7'S,8'E,12'R)-6-chloro-12'-ethyl-13',13'-dioxido-15'-oxo-3,4-Step 2: dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N-(1-methylethyl)acetamide The title compound was prepared in an analogous manner to that described in Example 404 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]-tetraen]-15'-one 13',13'-dioxide (Example 422, Step 1) and 2-bromo-N-isopropylacetamide, and isolated by chromatography eluting with a gradient of 0% to 100% EtOAc (containing 0.1% AcOH) in hexane. $^1$H NMR (500 MHz, CD$_3$OD) δ 7.75 (d, J=8.56 Hz, 1H), 7.19 (dd, J=2.32, 8.44 Hz, 1H), 7.12 (d, J=2.20 Hz, 1H), 6.96-7.03 (m, 1H), 6.91-6.95 (m, 1H), 6.83 (d, J=1.96 Hz, 1H), 5.86-5.96 (m, 1H), 5.59-5.69 (m, 1H), 4.02-4.10 (m, 4H), 3.92 (dd, J=3.67, 9.05 Hz, 1H), 3.83-3.88 (m, 3H), 3.68 (d, J=14.18 Hz, 1H), 3.30 (d, J=14.18 Hz, 1H), 3.09 (dd, J=10.39, 15.28 Hz, 1H), 2.73-2.87 (m, 2H), 2.55-2.64 (m, 1H), 2.39-2.48 (m, 1H), 2.28-2.38 (m, 2H), 2.07-2.17 (m, 2H), 1.92-2.02 (m, 3H), 1.82-1.92 (m, 5H), 1.72-1.81 (m, 1H), 1.41-1.49 (m, 1H), 1.17-1.22 (m, 9H). m/z (ESI, +ve ion) 698.2 (M+H)+.

Example 423. (1S,3'R,6'R,7'S,8'E,12'R)-6-chloro-12'-ethyl-7'-((1-methyl-1H-1,2,4-triazol-3-yl)methoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

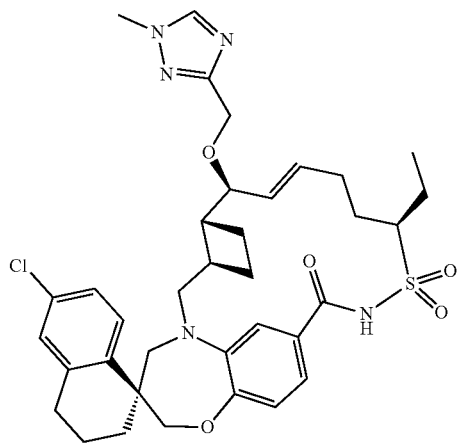 [SMILES: CC[C@@H]1CC/C=C/[C@H](OCc2ncn(C)n2)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 404 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 3-(chloromethyl)-1-methyl-1H-1,2,4-triazole hydrochloride. $^1$H NMR (500 MHz, CD$_3$OD) δ 8.39-8.57 (m, 1H), 7.74 (d, J=8.56 Hz, 1H), 7.19 (dd, J=2.32, 8.44 Hz, 1H), 7.12 (d, J=2.20 Hz, 1H), 6.96-7.02 (m, 1H), 6.87-6.95 (m, 1H), 6.81 (d, J=1.71 Hz, 1H), 5.85-5.94 (m, 1H), 5.61 (dd, J=8.93, 15.28 Hz, 1H), 4.41-4.57 (m, 2H), 4.03-4.12 (m, 3H), 3.99 (s, 3H), 3.90 (dd, J=3.67, 8.80 Hz, 1H), 3.75-3.81 (m, 1H), 3.67 (d, J=14.18 Hz, 1H), 3.24-3.30 (m, 1H), 3.07 (dd, J=10.03, 15.41 Hz, 1H), 2.71-2.86 (m, 2H), 2.53 (dq, J=3.55, 9.33 Hz, 1H), 2.39-2.47 (m, 1H), 2.26-2.38 (m, 2H), 2.06-2.19 (m, 2H), 1.85-2.02 (m, 6H), 1.82 (dd, J=8.19, 10.39 Hz, 2H), 1.67-1.78 (m, 1H), 1.39-1.50 (m, 1H), 1.23 (t, J=7.46 Hz, 3H). m/z (ESI, +ve ion) 694.2 (M+H)+.

Example 424. (1S,3'R,6'R,7'S,8'E,12'R)-6-chloro-12'-ethyl-7'-(((3R)-2-oxotetrahydro-3-furanyl)oxy)-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide or (1S,3'R,6'R,7'S,8'E,12'R)-6-chloro-12'-ethyl-7'-(((3S)-2-oxotetrahydro-3-furanyl)oxy)-3,4-dihydro-2H,15'H-spiro[naphthalene-1,22'-[20]oxa[13]thia[1,14]diazatetracyclo[14.7.2.0$^{3,6}$.0$^{19,24}$] pentacosa 8,16,18,24]tetraen]-15'-one 13',13'-dioxide

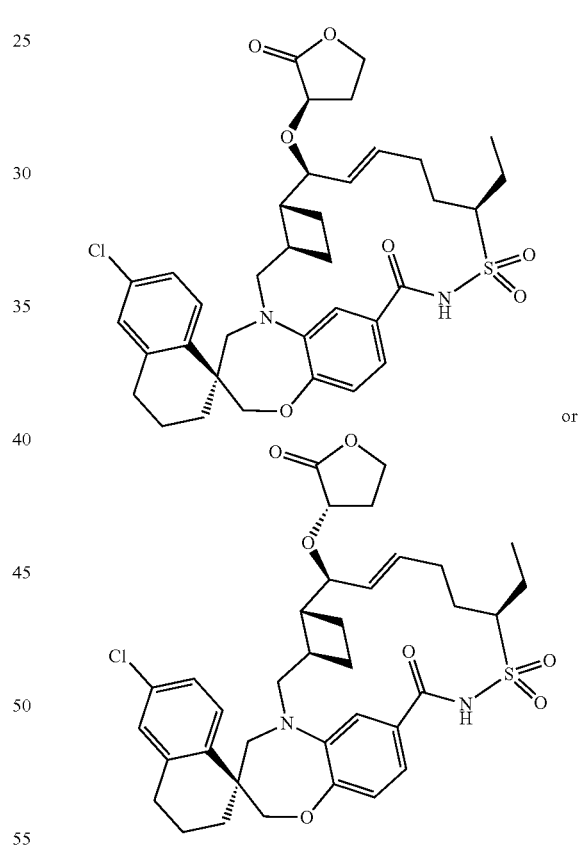

The title compound was prepared in an analogous manner to that described in Example 413, Step 4 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1), and isolated as the first eluting isomer from the reversed phase preparatory HPLC. $^1$H NMR (500 MHz, CD$_3$OD) δ 7.75 (d, J=8.56 Hz, 1H), 7.18-7.22 (m, 1H), 7.12 (d, J=2.20 Hz, 1H), 6.98-7.03 (m, 1H), 6.92-6.97 (m, 1H), 6.86 (d, J=1.96 Hz, 1H), 5.88-5.99 (m, 1H), 5.68 (dd, J=8.93, 15.28 Hz, 1H), 4.35-4.45 (m, 2H), 4.23-4.30 (m, 1H), 4.00-4.13 (m, 4H), 3.86 (d, J=14.67 Hz, 1H), 3.68 (d, J=14.18 Hz, 1H), 3.26-3.33 (m, 1H), 3.09 (dd, J=10.15, 15.28 Hz, 1H), 2.73-2.88 (m, 2H), 2.63 (dddd, J=2.81, 6.36, 7.89, 12.53 Hz, 1H), 2.53 (dq, J=3.67, 9.21 Hz, 1H), 2.40-2.48 (m, 1H), 2.29-2.39 (m, 2H), 2.07-2.22 (m, 3H), 1.80-2.04 (m, 8H), 1.68-1.79 (m, 1H), 1.41-1.50 (m, 1H), 1.21 (t, J=7.58 Hz, 3H). m/z (ESI, +ve ion) 683.2 (M+H)+.

Example 425. (1S,3'R,6'R,7'S,8'E,12'R)-6-chloro-12'-ethyl-7'-(((3S)-2-oxotetrahydro-3-furanyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-12'-ethyl-7'-(((3R)-2-oxotetrahydro-3-furanyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

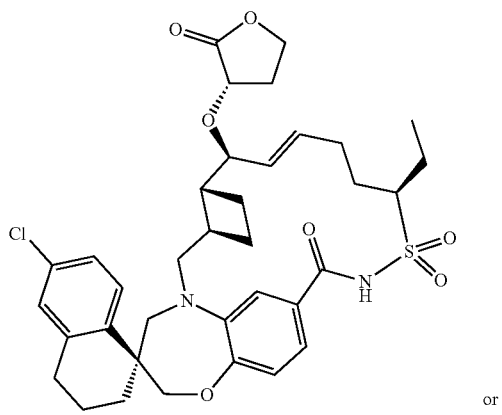

or

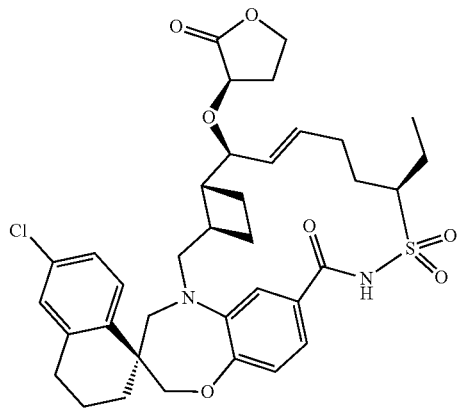

The title compound was obtained as the later eluting isomer from the reversed phase preparatory HPLC separation in Example 424. ¹H NMR (500 MHz, CD$_3$OD) δ 7.74 (d, J=8.56 Hz, 1H), 7.16-7.22 (m, 1H), 7.12 (s, 1H), 7.00 (dd, J=1.22, 8.07 Hz, 1H), 6.89-6.95 (m, 2H), 5.83-5.94 (m, 1H), 5.61 (dd, J=8.56, 15.16 Hz, 1H), 4.28-4.40 (m, 3H), 4.24 (dt, J=6.72, 9.11 Hz, 1H), 4.05-4.11 (m, 2H), 4.02 (quin, J=5.93 Hz, 1H), 3.87 (d, J=14.18 Hz, 1H), 3.67 (d, J=14.18 Hz, 1H), 3.29 (d, J=14.18 Hz, 1H), 3.09 (dd, J=9.66, 15.28 Hz, 1H), 2.72-2.87 (m, 2H), 2.60 (dq, J=4.16, 9.05 Hz, 1H), 2.35-2.48 (m, 3H), 2.26-2.35 (m, 1H), 1.80-2.16 (m, 11H), 1.69-1.79 (m, 1H), 1.45 (t, J=11.98 Hz, 1H), 1.21 (t, J=7.46 Hz, 3H). m/z (ESI, +ve ion) 683.2 (M+H)+.

Example 426. (1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl acetate

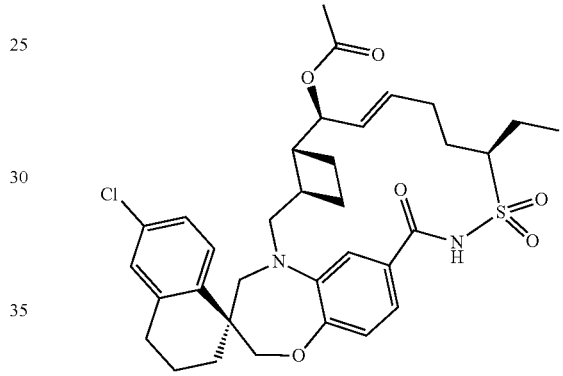

To a 25-mL round-bottomed flask were added (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (20 mg, 0.033 mmol, Example 422, Step 1) and acetic anhydride (100 μl, 1.06 mmol) in DCM (500 μl), and pyridine (200 μl, 2.48 mmol). The reaction mixture was stirred at ambient temperature overnight. The reaction mixture was diluted with 1N HCl (5 mL) and extracted with EtOAc (2×10 mL). The organic solution was separated and concentrated. The crude material was purified by chromatography through a Redi-Sep prepacked silica gel column (12 g), eluting with a gradient of 0% to 45% EtOAc in hexane, to provide the title compound as a white powder. ¹H NMR (400 MHz, CDCl$_3$) δ 7.88 (s, 1H), 7.71 (d, J=8.41 Hz, 1H), 7.20 (dd, J=2.35, 8.41 Hz, 1H), 7.10 (d, J=2.35 Hz, 1H), 6.84-6.97 (m, 2H), 5.88-5.98 (m, 1H), 5.66 (dd, J=8.31, 15.36 Hz, 1H), 5.33 (dd, J=4.21, 8.31 Hz, 1H), 4.01-4.17 (m, 3H), 3.92 (d, J=13.69 Hz, 1H), 3.69-3.77 (m, 1H), 3.22 (d, J=14.08 Hz, 1H), 3.00 (dd, J=9.49, 15.36 Hz, 1H), 2.72-2.85 (m, 2H), 2.50 (dd, J=4.11, 9.39 Hz, 1H), 2.17-2.42 (m, 3H), 1.88-2.16 (m, 7H), 1.75-1.87 (m, 3H), 1.62-1.72 (m, 1H), 1.33-1.46 (m, 2H), 1.17-1.26 (m, 3H), 0.80-0.95 (m, 3H). m/z (ESI, +ve ion) 641.2 (M+H)+.

Example 427. (1S,3'R,6'R,7'S,8'E,11'S,12'R)-6-chloro-11',12'-dimethyl-7'-(((3S)-2-oxotetrahydro-3-furanyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-11',12'-dimethyl-7'-(((3R)-2-oxotetrahydro-3-furanyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide Example 428. (1S,3'R,6'R,7'S,8'E,11'S,12'R)-6-chloro-11',12'-dimethyl-7'-(((3R)-2-oxotetrahydro-3-furanyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-11',12'-dimethyl-7'-(((3S)-2-oxotetrahydro-3-furanyl)oxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

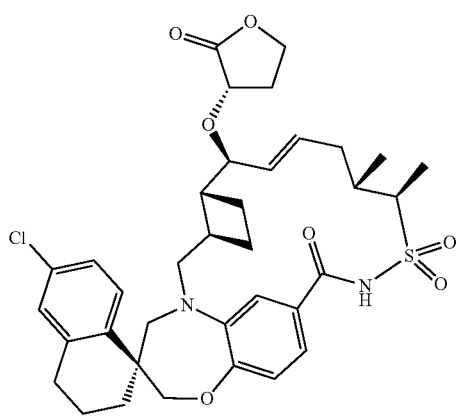

or

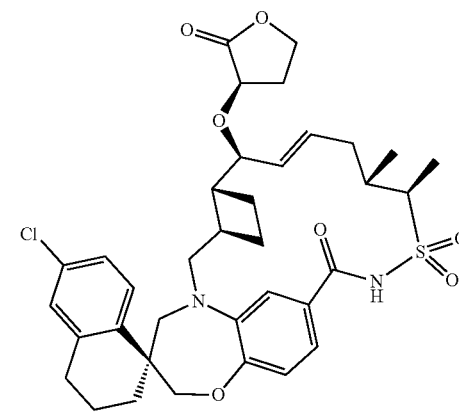

or

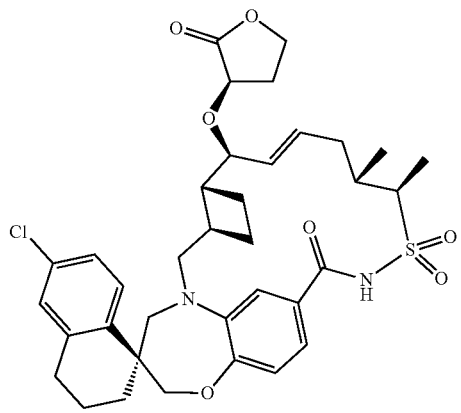

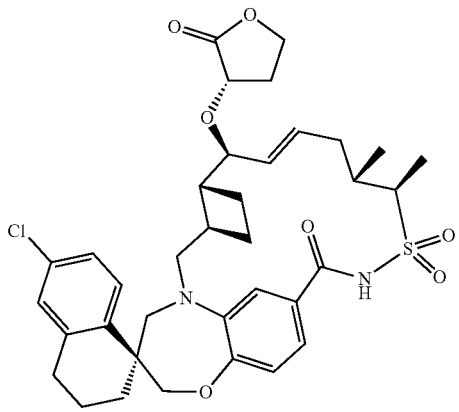

The title compound was prepared in an analogous manner to that described in Example 413, Step 4 using (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 719, Step 2), and isolated as the second eluting isomer from the reversed phase preparatory HPLC. $^1$H NMR (400 MHz, CDCl$_3$) δ 8.14 (br. s., 1H), 7.69 (d, J=8.41 Hz, 1H), 7.18 (dd, J=2.25, 8.51 Hz, 1H), 7.09 (d, J=2.15 Hz, 1H), 6.84-6.98 (m, 3H), 5.80-5.98 (m, 1H), 5.55 (dd, J=9.00, 15.26 Hz, 1H), 4.28-4.43 (m, 3H), 4.13-4.26 (m, 2H), 4.03-4.12 (m, 2H), 3.90 (d, J=15.26 Hz, 1H), 3.70 (d, J=14.28 Hz, 1H), 3.23 (d, J=14.28 Hz, 1H), 3.02 (dd, J=10.17, 15.26 Hz, 1H), 2.65-2.86 (m, 3H), 2.53-2.64 (m, 1H), 2.25-2.45 (m, 2H), 2.08-2.24 (m, 3H), 1.91-2.08 (m, 3H), 1.74-1.90 (m, 3H), 1.60-1.72 (m, 1H), 1.50 (d, J=7.24 Hz, 3H), 1.32-1.46 (m, 1H), 1.06 (d, J=6.85 Hz, 3H). m/z (ESI, +ve ion) 683.2 (M+H)$^+$.

The title compound was obtained as the first eluting isomer from the reversed phase preparatory HPLC separation in Example 427. $^1$H NMR (400 MHz, CDCl$_3$) δ 8.00 (s, 1H), 7.63-7.75 (m, 1H), 7.19 (dd, J=2.35, 8.41 Hz, 1H), 7.10 (d, J=2.15 Hz, 1H), 6.89-6.99 (m, 2H), 6.87 (d, J=1.56 Hz, 1H), 5.82-5.94 (m, 1H), 5.68 (dd, J=9.29, 15.55 Hz, 1H), 4.43 (dt, J=2.84, 8.85 Hz, 1H), 4.27-4.34 (m, 1H), 4.18-4.27 (m, 2H), 4.12-4.18 (m, 1H), 4.05-4.12 (m, 2H), 3.92 (dd, J=3.23, 9.29 Hz, 1H), 3.83 (d, J=14.87 Hz, 1H), 3.71 (d, J=14.28 Hz, 1H), 3.20-3.27 (m, 1H), 3.02 (dd, J=10.07, 15.36 Hz, 1H), 2.72-2.84 (m, 2H), 2.52-2.63 (m, 1H), 2.41-2.51 (m, 1H), 2.30-2.40 (m, 1H), 2.11-2.25 (m, 3H), 1.96-2.05 (m, 3H), 1.82-1.95 (m, 3H), 1.62-1.71 (m, 1H), 1.47-1.52 (m, 3H), 1.35-1.44 (m, 1H), 1.06 (d, J=6.85 Hz, 3H). m/z (ESI, +ve ion) 683.2 (M+H)$^+$.

Example 429. (2S)-2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N,N,4-trimethylpentanamide or (2R)-2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N,N,4-trimethylpentanamide

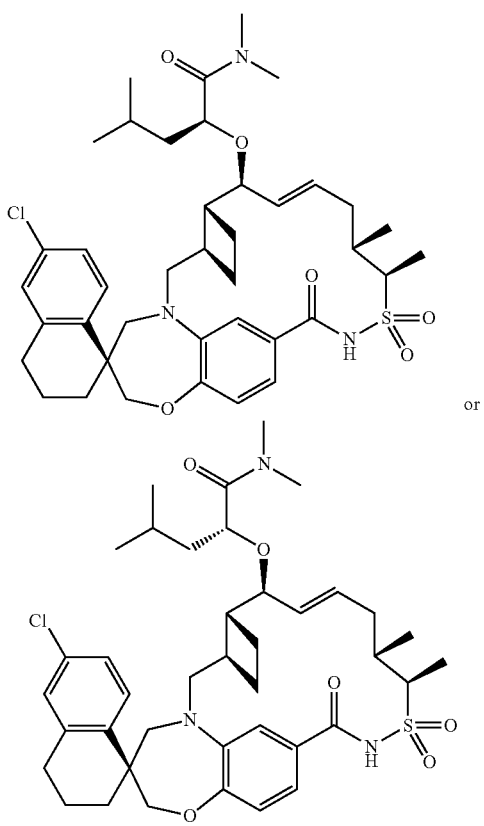

or

Step 1: (R)-1-(dimethylamino)-4-methyl-1-oxopentan-2-yl methanesulfonate and (S)-1-(dimethylamino)-4-methyl-1-oxopentan-2-yl methanesulfonate

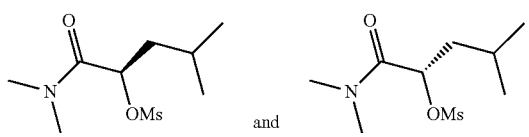

To a mixture of methanesulfonyl chloride (0.408 ml, 5.28 mmol) and 2-hydroxy-N,N,4-trimethylpentanamide (0.800 g, 5.02 mmol) in 10 mL of DCM in a 100-mL round-bottomed flask at 0° C. was added a mixture of triethylamine (1.05 ml, 7.54 mmol) and N,N-dimethylpyridin-4-amine (0.307 g, 2.51 mmol) in 10 mL of DCM through an addition funnel. The mixture was stirred at ambient temperature overnight. The reaction mixture was diluted with 1N HCl (10 mL) and extracted with Et$_2$O (3×20 mL). The organic extract was washed with saturated NaCl (20 mL) and dried over MgSO$_4$. The solution was filtered and concentrated in vacuo. The crude material was purified by chromatography through a Redi-Sep pre-packed silica gel column (40 g), eluting with a gradient of 0% to 80% EtOAc in hexane, to provide the title compound (0.250 g, 21%) as a white solid. m/z (ESI, +ve ion) 238.2 (M+H)$^+$.

Step 2: (R)-2-bromo-N,N,4-trimethylpentanamide and (S)-2-bromo-N,N,4-trimethylpentanamide

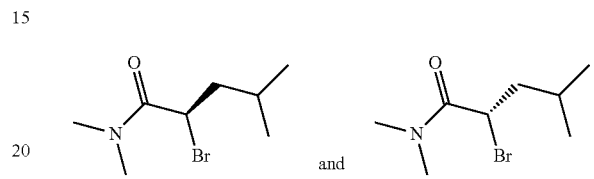

To a 25-mL round-bottomed flask were added (R)-1-(dimethylamino)-4-methyl-1-oxopentan-2-yl methanesulfonate and (S)-1-(dimethylamino)-4-methyl-1-oxopentan-2-yl methanesulfonate (100 mg, 0.421 mmol) and bromide salt of sodium (131 mg, 1.26 mmol) in DMF (4.2 mL). The reaction mixture was stirred at 50° C. overnight. The reaction was quenched with aq. NH$_4$Cl (5 mL) and extracted with EtOAc (2×10 mL). The organic layer was combined and dried over MgSO$_4$. The solvent was removed. The crude material was purified by chromatography through a Redi-Sep pre-packed silica gel column (12 g), eluting with a gradient of 0% to 40% EtOAc in hexane, to provide the title compound (76 mg, 81%) as a colorless oil. $^1$H NMR (500 MHz, CDCl$_3$) δ 4.47-4.59 (m, 1H), 3.09-3.20 (m, 3H), 2.95-3.05 (m, 3H), 1.94-2.05 (m, 2H), 1.72-1.85 (m, 1H), 0.89-1.00 (m, 6H).

Step 3. (2S)-2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N,N,4-trimethylpentanamide or (2R)-2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N,N,4-trimethylpentanamide The title compound was prepared in an analogous manner to that described in Example 404 using (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]-tetraen]-15'-one 13',13'-dioxide (Example 719, Step 2) and (R)-2-bromo-N,N,4-trimethylpentanamide and (S)-2-bromo-N,N,4-trimethylpentanamide (Step 2), and isolated as the major isomer from the reversed phase preparatory HPLC. $^1$H NMR (500 MHz, CDCl$_3$) δ 7.92 (s, 1H), 7.69 (d, J=8.3 Hz, 1H), 7.18 (dd, J=2.2, 8.6 Hz, 1H), 7.09 (d, J=2.2 Hz, 1H), 6.94-6.91 (m, 1H), 6.89-6.86 (m, 1H), 6.82 (d, J=1.7 Hz, 1H), 5.80-5.69 (m, 1H), 5.53 (dd, J=9.5, 15.2 Hz, 1H), 4.36-4.28 (m, 1H), 4.23 (dd, J=2.7, 10.8 Hz, 1H), 4.12-4.02 (m, 2H), 3.81 (d, J=15.2 Hz, 1H), 3.70 (d, J=14.4 Hz, 1H), 3.64 (dd, J=3.2, 9.3 Hz, 1H), 3.22 (d, J=14.2 Hz, 1H), 3.10 (s, 3H), 3.05 (s, 3H), 3.02-2.93 (m, 1H), 2.86-2.70 (m, 2H), 2.61-2.52 (m, 1H), 2.34-2.23 (m, 1H), 2.21-1.58 (m, 13H), 1.50 (d, J=7.3 Hz, 3H), 1.41-1.34 (m, 1H), 1.07 (d, J=6.8 Hz, 3H), 0.91 (d, J=6.8 Hz, 3H), 0.85 (d, J=6.4 Hz, 3H). m/z (ESI, +ve ion) 740.4 (M+H)+.

Example 430. (2S)-2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N,N-dimethylbutanamide or (2R)-2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N,N-dimethylbutanamide

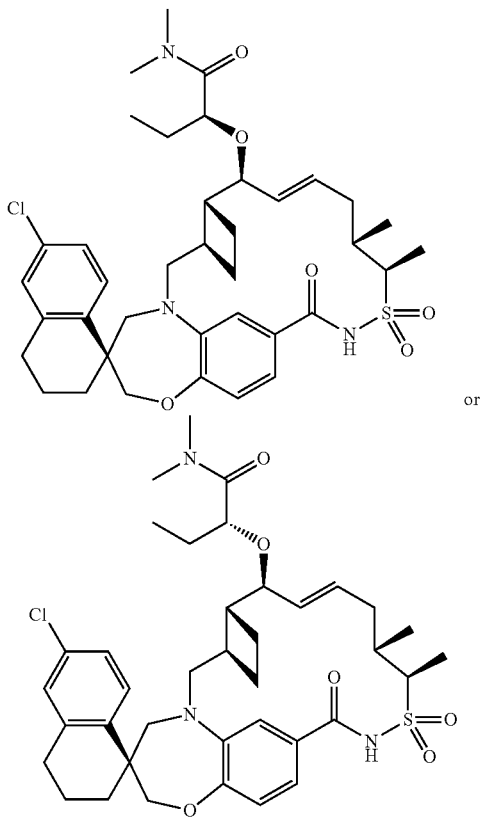

The title compound was prepared in an analogous manner to that described in Example 404 using (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 719, Step 2) and (R)-2-bromo-N,N-dimethylbutanamide and (R)-2-bromo-N,N-dimethylbutanamide (Example 419, Step 1), and isolated as the first eluting isomer out of reversed phase preparatory HPLC. $^1$H NMR (400 MHz, CD$_3$OD) δ 7.72 (d, J=8.4 Hz, 1H), 7.17 (dd, J=2.2, 8.5 Hz, 1H), 7.10 (d, J=2.2 Hz, 1H), 7.03 (dd, J=1.9, 8.1 Hz, 1H), 6.91 (d, J=8.2 Hz, 1H), 6.86 (d, J=1.8 Hz, 1H), 5.90-5.78 (m, 1H), 5.60 (dd, J=9.4, 15.5 Hz, 1H), 4.25-4.17 (m, 1H), 4.09-4.03 (m, 3H), 3.88 (dd, J=2.9, 9.4 Hz, 1H), 3.81 (d, J=14.3 Hz, 1H), 3.67-3.62 (m, 1H), 3.27 (s, 1H), 3.16-3.05 (m, 4H), 2.91 (s, 3H), 2.87-2.72 (m, 2H), 2.58-2.47 (m, 1H), 2.35-2.25 (m, 1H), 2.15-1.57 (m, 13H), 1.43 (d, J=7.2 Hz, 3H), 1.04 (d, J=6.5 Hz, 3H), 1.00 (t, J=7.4 Hz, 3H). m/z (ESI, +ve ion) 712.3 (M+H)+.

Example 431. (2R)-2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N,N-dimethylbutanamide or (2S)-2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N,N-dimethylbutanamide

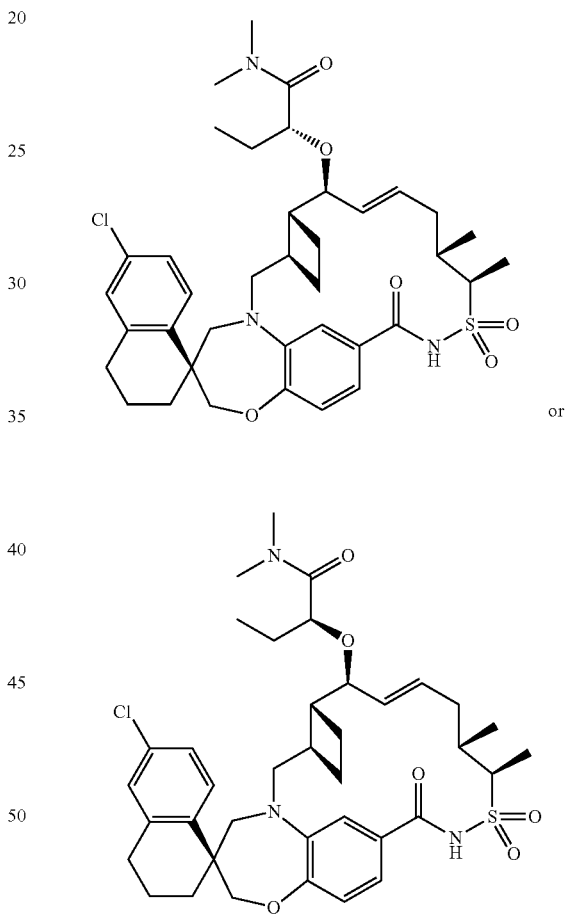

The title compound was obtained as the second eluting isomer from the reversed phase preparatory HPLC separation in Example 430. $^1$H NMR (400 MHz, CD$_3$OD) δ 7.72 (d, J=8.4 Hz, 1H), 7.16 (dd, J=2.2, 8.5 Hz, 1H), 7.10 (d, J=2.3 Hz, 1H), 7.03 (dd, J=1.9, 8.1 Hz, 1H), 6.90 (d, J=8.2 Hz, 1H), 6.84 (d, J=1.8 Hz, 1H), 5.82-5.67 (m, 1H), 5.62-5.52 (m, 1H), 4.25-4.13 (m, 2H), 4.07 (s, 2H), 3.77 (d, J=15.3 Hz, 1H), 3.70 (dd, J=3.1, 9.0 Hz, 1H), 3.63 (d, J=14.7 Hz, 1H), 3.15 (s, 3H), 3.13-3.04 (m, 1H), 3.02 (s, 3H), 2.86-2.67 (m, 2H), 2.59-2.47 (m, 1H), 2.39-1.56 (m, 15H), 1.43 (d, J=7.2 Hz, 3H), 1.06 (d, J=6.8 Hz, 3H), 0.92 (t, J=7.3 Hz, 3H). m/z (ESI, +ve ion) 712.3 (M+H)+.

Example 432. (1S,3'R,6'R,7'S,12'S)-6-chloro-7'-hydroxy-12'-(trifluoromethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide or (1S,3'R,6'R,7'S,12'R)-6-chloro-7'-hydroxy-12'-(trifluoromethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide

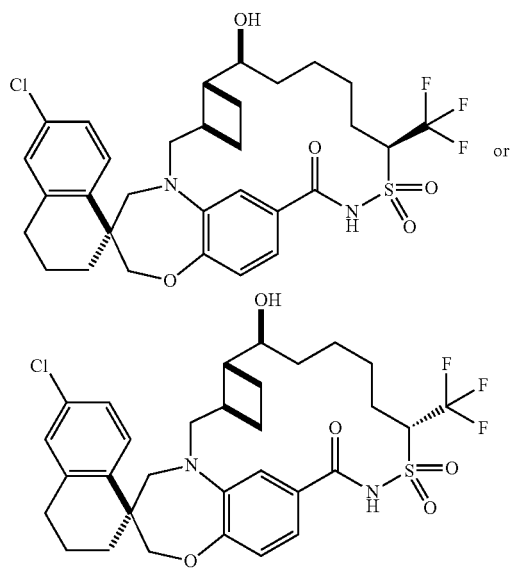

Step 1: 2,2,2-trifluoro-N,N-bis(4-methoxybenzyl)ethanesulfonamide

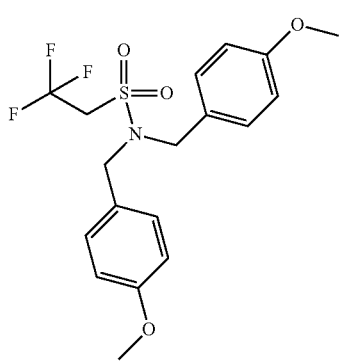 [SMILES: COc1ccc(CN(Cc2ccc(OC)cc2)S(=O)(=O)CC(F)(F)F)cc1]

To a 250-mL round-bottomed flask were added bis(4-methoxybenzyl)amine (4.23 g, 16.4 mmol, Intermediate EE11) and triethylamine (4.57 mL, 32.9 mmol) in DCM (40 mL). 2,2,2-trifluoroethanesulfonyl chloride (2.00 g, 11.0 mmol) was added to the solution at 0° C. slowly. The white precipitate came out. The mixture was stirred at ambient temperature overnight. The reaction mixture was diluted with 1N HCl (10 mL) and extracted with EtOAc (2×50 mL). The combined EtOAc solution was concentrated. The crude material was purified by chromatography through a Redi-Sep pre-packed silica gel column (40 g), eluting with a gradient of 10% to 60% EtOAc in hexane, to provide the title compound (1.10 g, 25% yield). m/z (ESI, +ve ion) 406.0 (M+Na)⁺.

Step 2: (S)-1,1,1-trifluoro-N,N-bis(4-methoxybenzyl)pent-4-ene-2-sulfonamide and (R)-1,1,1-trifluoro-N,N-bis(4-methoxybenzyl)pent-4-ene-2-sulfonamide

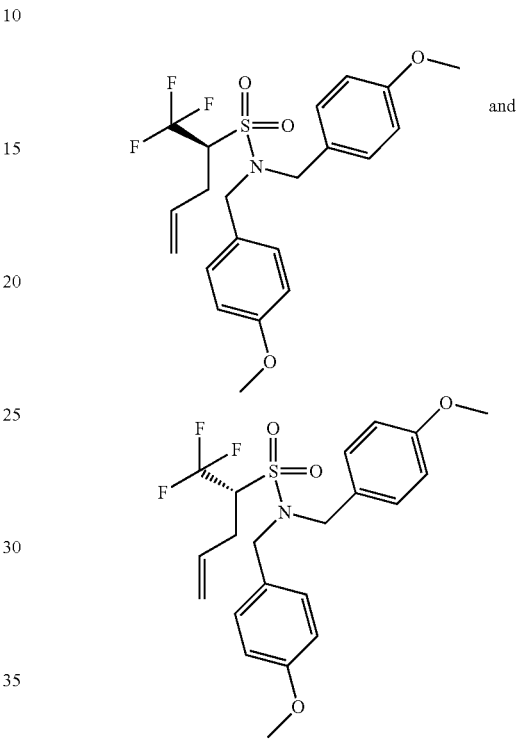

To a dried vial containing 1.0 g of molecular sieve 5A were added tris(dibenzylideneacetone)dipalladium (0) chloroform adduct (32 mg, 0.031 mmol), allyl methyl carbonate (0.173 mL, 1.49 mmol), 2,2,2-trifluoro-N,N-bis(4-methoxybenzyl)ethanesulfonamide (500 mg, 1.24 mmol) and (−)-binap (77 mg, 0.12 mmol) in 3 mL of THF. The mixture was stirred at 50° C. for 6 hrs. The mixture was cooled to ambient temperature and filtered through a pad of celite. The filtrate was concentrated. The crude material was purified by chromatography through a Redi-Sep pre-packed silica gel column (40 g), eluting with a gradient of 20% to 40% EtOAc in hexane, to provide the title compound (500 mg, 91% yield) as slight yellow oil. m/z (ESI, +ve ion) 466.0 (M+Na)⁺.

Step 3: (S)-1,1,1-trifluoropent-4-ene-2-sulfonamide and (R)-1,1,1-trifluoropent-4-ene-2-sulfonamide

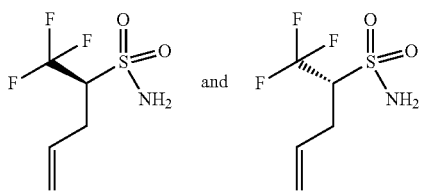

To a solution of (S)-1,1,1-trifluoro-N,N-bis(4-methoxybenzyl)pent-4-ene-2-sulfonamide and (R)-1,1,1-trifluoro-N,N-bis(4-methoxybenzyl)pent-4-ene-2-sulfonamide (300 mg, 0.676 mmol) in 6 mL of DCM was added thioanisole (0.794 mL, 6.76 mmol), followed by trifluoroacetic acid (2.01 mL, 27.1 mmol) dropwise. The reaction mixture was stirred at ambient temperature for 24 h, and concentrated. The crude material was purified by chromatography through a Redi-Sep pre-packed silica gel column (40 g), eluting with a gradient of 20% to 80% EtOAc in hexane, to provide the title compound (96 mg, 70% yield) as a white solid. $^1$H NMR (400 MHz, CDCl$_3$) δ 5.78-6.06 (m, 1H), 5.15-5.39 (m, 2H), 4.96 (br. s., 2H), 3.68-3.90 (m, 1H), 2.74-3.02 (m, 2H).

Step 4: (S)-6'-chloro-5-(((1R,2R)-2-((S)-1-hydroxybut-3-en-1-yl)cyclobutyl)methyl)-N—(((S)-1,1,1-trifluoropent-4-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxybut-3-en-1-yl)cyclobutyl)methyl)-N—(((R)-1,1,1-trifluoropent-4-en-2-yl)sulfonyl)-3',4,4',5-tetrahydro-2H,2'H-spiro[benzo[b][1,4]oxazepine-3,1'-naphthalene]-7-carboxamide

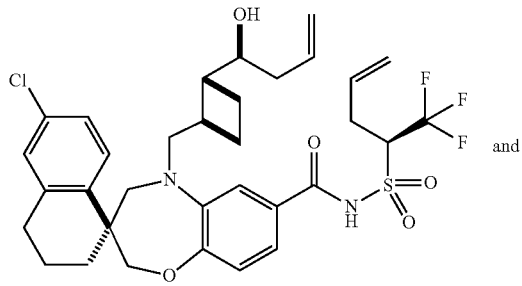

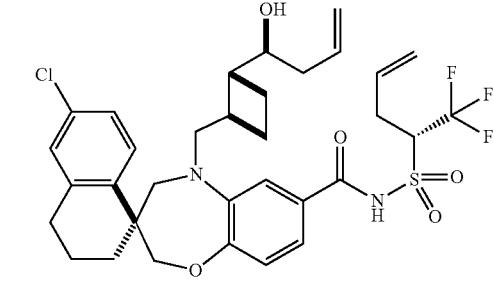

To a solution of (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (50.0 mg, 0.104 mmol, Intermediate AA13A) and (S)-1,1,1-trifluoropent-4-ene-2-sulfonamide and (R)-1,1,1-trifluoropent-4-ene-2-sulfonamide (42.2 mg, 0.207 mmol) in 3 mL of DCM (5 mL) at 0° C. were added N,N-dimethylpyridin-4-amine (DMAP) (25.3 mg, 0.207 mmol) and n-(3-dimethylaminopropyl)-n'-ethylcarbodiimide hydrochloride (39.8 mg, 0.207 mmol). The resulting mixture was stirred at ambient temperature overnight. The reaction mixture was diluted with EtOAc (30 ml), washed with 1N HCl (5 ml), brine (3 ml), dried over anhydrous sodium sulfate and concentrated. The crude product was purified by chromatography through a Redi-Sep pre-packed silica gel column (24 g), eluting with a gradient of 0% to 100% EtOAc in hexane (containing 0.1% HOAc), to provide the title compounds (50.0 mg, 72%). m/z (ESI, +ve ion) 667.0 (M+H)$^+$.

Step 5: (1S,3'R,6'R,7'S,9'Z,12'S)-6-chloro-7'-hydroxy-12'-(trifluoromethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide and (1S,3'R,6'R,7'S,9'Z,12'R)-6-chloro-7'-hydroxy-12'-(trifluoromethyl)-3,4-dihydro-2H,15'H-spiro[naphthalene-[20]oxa[13]thia[1,14]diazatetracyclo[14.7.2.0$^{3,6}$.0$^{19,24}$]pentacosa [9,16,18,24]tetraen]-15'-one 13',13'-dioxide and (1S,3'R,6'R,7'S,9'E,12'S)-6-chloro-7'-hydroxy-12'-(trifluoromethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide and (1S,3'R,6'R,7'S,9'E,12'R)-6-chloro-7'-hydroxy-12'-(trifluoromethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide

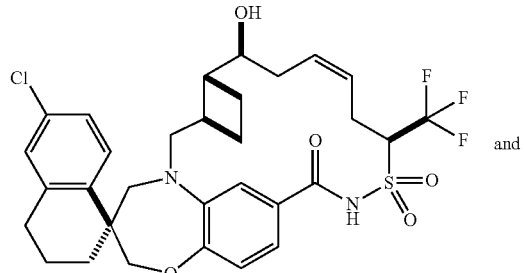

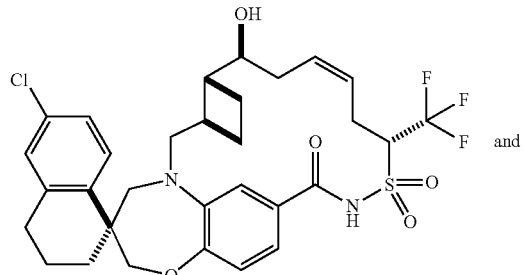

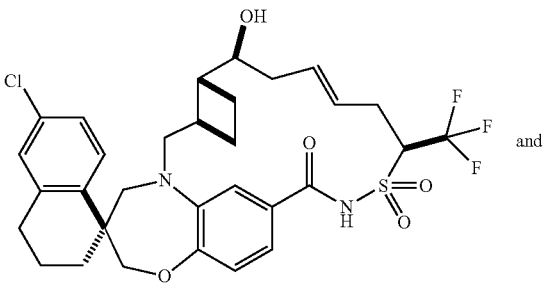

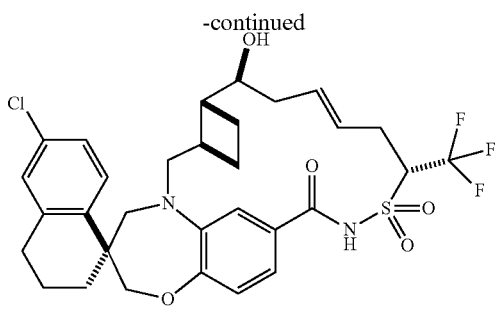

A 50 mL round bottom flask was charged with (S)-6'-chloro-5-(((1R,2R)-2-((S)-1-hydroxybut-3-en-1-yl)cyclobutyl)methyl)-N-(4S)-1,1,1-trifluoropent-4-en-2-yl)sulfonyl)-3',4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxybut-3-en-1-yl)cyclobutyl)methyl)-N—(((R)-1,1,1-trifluoropent-4-en-2-yl)sulfonyl)-3',4',5-tetrahydro-2H,2'H-spiro[benzo[b][1,4]oxazepine-3,1'-naphthalene]-7-carboxamide (50 mg, 0.075 mmol) in toluene (30 mL), and the solution was subjected to three cycles of evacuation/back-filling with nitrogen. To the homogeneous solution was added a solution of Hoveyda-Grubbs $2^{nd}$ generation (9.4 mg, 0.015 mmol) in toluene (1 mL) at room temperature. The mixture was stirred at 101° C. under nitrogen for 60 min. Air was blown through the solution for 5 min to deactivate the catalyst, and then the mixture was concentrated. The crude dark oil was purified by chromatography through a Redi-Sep pre-packed silica gel column (4 g), eluting with 10% to 50% EtOAc (containing 0.1% AcOH) in hexanes to provide the title compounds (30 mg, 63%). m/z (ESI, +ve ion) 639.0 (M+H)$^+$.

Step 6: (1S,3'R,6'R,7'S,12'S)-6-chloro-7'-hydroxy-12'-(trifluoromethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,12'R)-6-chloro-7'-hydroxy-12'-(trifluoromethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide A mixture of (1S,3'R,6'R,7'S,9'Z,12'S)-6-chloro-7'-hydroxy-12'-(trifluoromethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9'Z,12'R)-6-chloro-7'-hydroxy-12'-(trifluoromethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9'E,12'S)-6-chloro-7'-hydroxy-12'-(trifluoromethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9'E,12'R)-6-chloro-7'-hydroxy-12'-(trifluoromethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (30 mg, 0.047 mmol) and platinum (iv) oxide (6.4 mg, 0.028 mmol) in EtOAc (2 mL) were stirred under H$_2$ at ambient temperature for 30 min. The solid was filtered off and filtrate was concentrated. The crude material was purified by reversed phase preparatory HPLC (Gemini™ Prep C$_{18}$ 5 μm column; Phenomenex, Torrance, CA; gradient elution of 40% to 95% MeCN in water, where both solvents contain 0.1% TFA, 30 min method) to provide one of the title compound as the first eluting isomer. $^1$H NMR (400 MHz, CDCl$_3$) δ 9.71 (br. s., 1H), 7.66 (d, J=8.6 Hz, 1H), 7.35-7.26 (m, 2H), 7.18 (dd, J=2.2, 8.5 Hz, 1H), 7.10 (d, J=2.3 Hz, 1H), 6.98 (d, J=8.2 Hz, 1H), 4.53-4.34 (m, 1H), 4.22-4.05 (m, 2H), 3.70 (d, J=6.7 Hz, 1H), 3.65-3.50 (m, 2H), 3.38 (d, J=13.1 Hz, 2H), 2.85-2.68 (m, 2H), 2.51 (br. s., 1H), 2.40-1.14 (m, 18H). m/z (ESI, +ve ion) 641.0 (M+H)$^+$.

Example 433. (1S,3'R,6'R,7'S,12'R)-6-chloro-7'-hydroxy-12'-(trifluoromethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,12'S)-6-chloro-7'-hydroxy-12'-(trifluoromethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

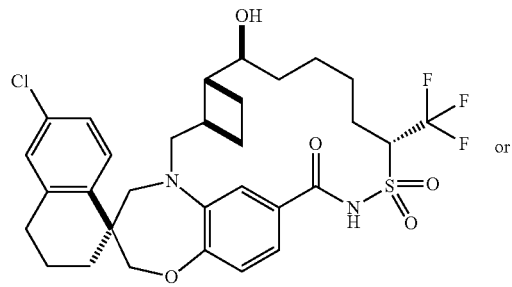

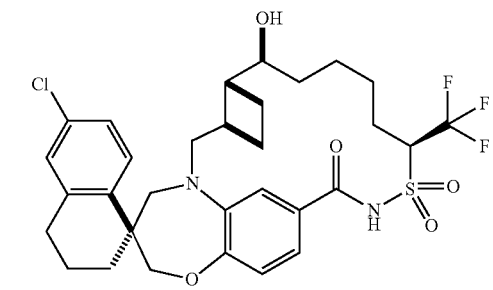

The title compound was obtained as the second eluting isomer from the reversed phase preparatory HPLC separation in Example 432, Step 6. $^1$H NMR (400 MHz, CDCl$_3$) δ 10.61 (br. s., 1H), 7.70 (d, J=8.4 Hz, 1H), 7.49 (dd, 8.2 Hz, 1H), 7.32-7.25 (m, 1H), 7.18 (dd, J=2.3, 8.4 Hz, 1H), 7.09 (d, J=2.2 Hz, 1H), 6.98 (d, J=8.4 Hz, 1H), 4.39 (br. s., 1H), 4.16-4.08 (m, 1H), 4.07-3.98 (m, 1H), 3.81 (d, J=15.7 Hz, 1H), 3.69-3.57 (m, 2H), 3.20-3.04 (m, 2H), 2.77 (br. s., 2H), 2.40-1.15 (m, 19H). m/z (ESI, +ve ion) 641.0 (M+H)$^+$.

Example 434. (1S,3'R,6'R,7'S,8'E,12'S)-6-chloro-7'-hydroxy-12'-(methoxymethyl)-3,4-dihydro-2H,15'H-spiro[naphthalene-[20]oxa[13]thia[1,14]diazatetracyclo[14.7.2.0$^{3,6}$.0$^{19,24}$]pentacosa [8,16,18,24]tetraen]-15'-one 13',13'-dioxide

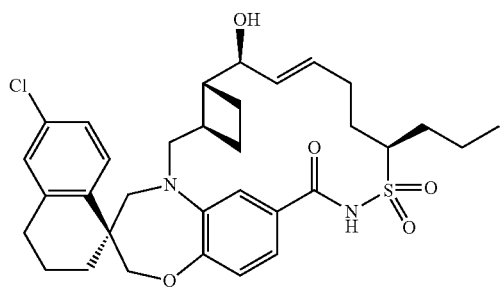 [SMILES: CCC[C@@H]1CC/C=C/[C@H](O)[C@@H]2CC[C@H]2CN2C[C@@]3(CCCc4cc(Cl)ccc43)COc3ccc(cc32)C(=O)NS1(=O)=O]

Step 1: (R)-methyl 2-(N,N-bis(4-methoxybenzyl)sulfamoyl)hex-5-enoate and (S)-methyl 2-(N,N-bis(4-methoxybenzyl)sulfamoyl)hex-5-enoate

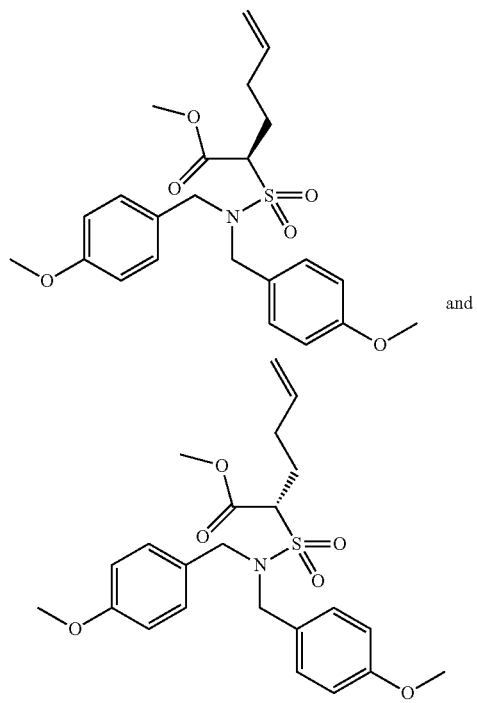

To a solution of N,N-bis(4-methoxybenzyl)pent-4-ene-1-sulfonamide (3.00 g, 7.70 mmol, Intermediate EE19) in THF (40 mL) at −78° C. was added butyllithium solution, 2.5 M in hexanes (3.39 mL, 8.47 mmol). The resulting mixture was stirred at −78° C. for 5 min, and then chlorocarbonic acid, methyl ester (0.583 mL, 7.55 mmol) was added. The reaction was stirred at −78° C. for another 20 min, and allowed to warm up to ambient temperature overnight. The reaction mixture was diluted with saturated NH$_4$Cl (10 mL), and extracted with EtOAc (2×30 mL). The organic extract was washed with saturated NaCl (10 mL) and dried over MgSO$_4$, filtered and concentrated in vacuo to give the title compound as a colorless oil (3.40 g, 99%). m/z (ESI, +ve ion) 470.2 (M+Na)$^+$.

Step 2: (R)-1-hydroxy-N,N-bis(4-methoxybenzyl)hex-5-ene-2-sulfonamide and (S)-1-hydroxy-N,N-bis(4-methoxybenzyl)hex-5-ene-2-sulfonamide

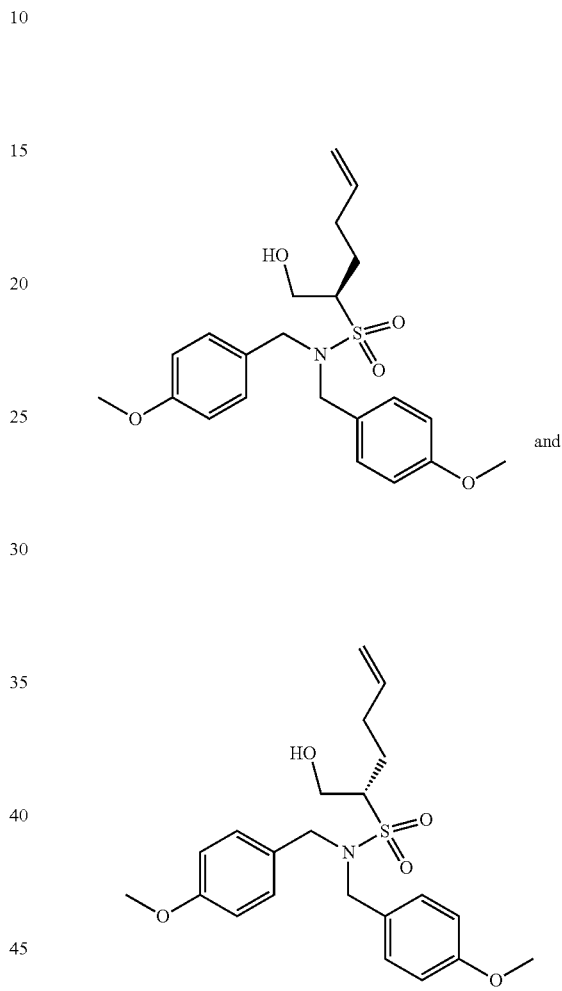

To a 100-mL round-bottomed flask were added (R)-methyl 2-(N,N-bis(4-methoxybenzyl)sulfamoyl)hex-5-enoate and (S)-methyl 2-(N,N-bis(4-methoxybenzyl)sulfamoyl)hex-5-enoate (2.20 g, 4.92 mmol) and lithium borohydride (0.214 g, 9.83 mmol) in THF (24.6 ml). A few drop of water was added. The mixture was stirred at ambient temperature overnight. The reaction mixture was diluted with 1N HCl (10 mL) and water, and extracted with EtOAc (2×20 mL). The organic extract was washed with saturated NaCl (10 mL) and dried over MgSO$_4$, filtered and concentrated in vacuo to give the crude material. The crude material was purified by chromatography through a Redi-Sep pre-packed silica gel column (40 g), eluting with a gradient of 20% to 60% EtOAc in hexane, to provide the title compound (1.30 g, 63%). m/z (ESI, +ve ion) 442.2 (M+Na)$^+$.

Step 3: (R)-1-methoxy-N,N-bis(4-methoxybenzyl) hex-5-ene-2-sulfonamide and (S)-1-methoxy-N,N-bis(4-methoxybenzyl)hex-5-ene-2-sulfonamide

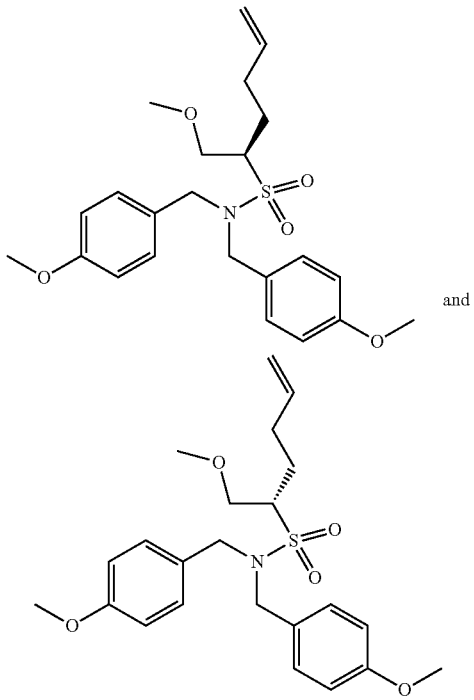

To a 25-mL round-bottomed flask were added (R)-1-hydroxy-N,N-bis(4-methoxybenzyl)hex-5-ene-2-sulfonamide and (S)-1-hydroxy-N,N-bis(4-methoxybenzyl)hex-5-ene-2-sulfonamide (190 mg, 0.453 mmol) and iodomethane (0.563 mL, 9.06 mmol) in THF (5.7 mL), and then potassium tert-butoxide, 1.0 M solution in tetrahydrofuran (0.444 mL, 0.444 mmol) slowly over 30 min. The reaction mixture was stirred for 1 h. The reaction mixture was diluted with 1N HCl (10 mL), and extracted with EtOAc (2×10 mL). The organic solution was concentrated. The crude material was purified by chromatography through a Redi-Sep pre-packed silica gel column (40 g), eluting with a gradient of 20% to 40% EtOAc in hexane, to provide the title compound (0.170 g, 87% yield). m/z (ESI, +ve ion) 456.2 (M+Na)$^+$.

Step 4: (R)-1-methoxyhex-5-ene-2-sulfonamide and (S)-1-methoxyhex-5-ene-2-sulfonamide

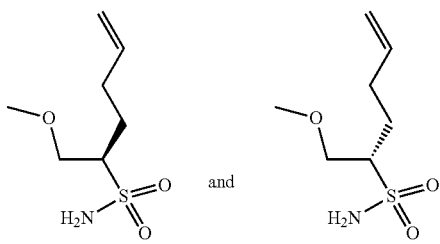

The title compound was prepared in an analogous manner to that described in Example 432, Step 3 using (R)-1-methoxy-N,N-bis(4-methoxybenzyl)hex-5-ene-2-sulfonamide and (S)-1-methoxy-N,N-bis(4-methoxybenzyl)hex-5-ene-2-sulfonamide. m/z (ESI, +ve ion) 194.2 (M+H)$^+$.

Step 5: (S)-6'-chloro-5-(((1R,2R)-2-((S)-1-hydroxyallyl)cyclobutyl)methyl)-N—(((S)-1-methoxyhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxyallyl)cyclobutyl)methyl)-N—(((R)-1-methoxyhex-5-en-2-yl)sulfonyl)-3',4,4',5-tetrahydro-2H,2'H-spiro[benzo[b][1,4]oxazepine-3,1'-naphthalene]-7-carboxamide

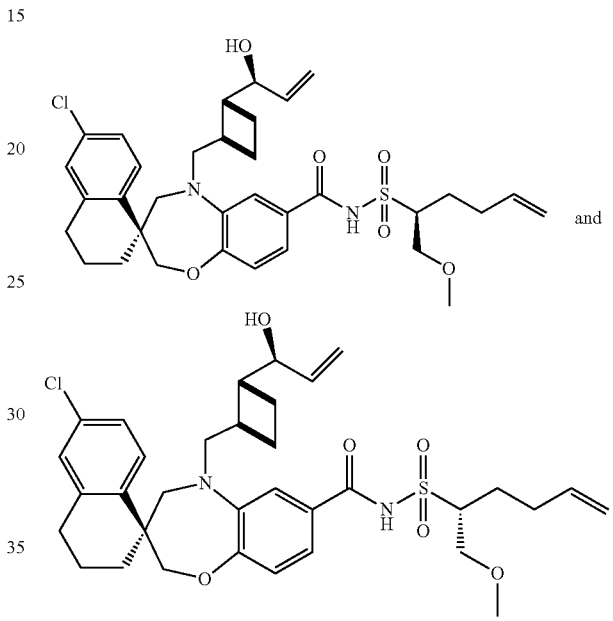

The title compound was prepared in an analogous manner to that described in Example 432, Step 4 using (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Intermediate AA11A) and (R)-1-methoxyhex-5-ene-2-sulfonamide and (S)-1-methoxyhex-5-ene-2-sulfonamide. m/z (ESI, +ve ion) 643.2 (M+H)$^+$.

Step 6: (1S,3'R,6'R,7'S,8'E,12'S)-6-chloro-7'-hydroxy-12'-(methoxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24] tetraen]-15'-one 13',13'-dioxide The title compound was prepared in an analogous manner to that described in Example 432, Step 5 using (S)-6'-chloro-5-(((1R,2R)-2-((S)-1-hydroxyallyl)cyclobutyl)methyl)-N—(((S)-1-methoxyhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxyallyl)cyclobutyl)methyl)-N—(((R)-1-methoxyhex-5-en-2-yl)sulfonyl)-3',4,4',5-tetrahydro-2H,2'H spiro[benzo[b][1,4]oxazepine-3,1'-naphthalene]-7-carboxamide, and isolated as first eluting isomer from the reversed phase preparatory HPLC separation. $^1$H NMR (400 MHz, CDCl$_3$) δ 8.19 (s, 1H), 7.70 (d, J=8.4 Hz, 1H), 7.19 (dd, J=2.2, 8.4 Hz, 1H), 7.09 (d, J=2.2 Hz, 1H), 6.97-6.86

(m, 3H), 5.87-5.76 (m, 1H), 5.75-5.66 (m, 1H), 4.29 (dd, J=4.0, 8.9 Hz, 1H), 4.20 (dd, J=4.5, 6.7 Hz, 1H), 4.15-3.99 (m, 3H), 3.96-3.88 (m, 1H), 3.82 (d, J=15.5 Hz, 1H), 3.71 (d, J=14.5 Hz, 1H), 3.45 (s, 3H), 3.24 (d, J=14.3 Hz, 1H), 3.03 (dd, J=8.5, 15.4 Hz, 1H), 2.86-2.66 (m, 2H), 2.51-1.58 (m, 14H), 1.41 (t, J=12.2 Hz, 1H). m/z (ESI, +ve ion) 615.2 (M+H)+.

Example 435. (1S,3'R,6'R,7'S,8'E,12'R)-6-chloro-7'-hydroxy-12'-(methoxymethyl)-3,4-dihydro-2H,15'H-spiro[naphthalene-1,22'-[20]oxa[13]thia[1,14]diaza-tetracyclo[14.7.2.0³,⁶.0¹⁹,²⁴]pentacosa [8,16,18,24] tetraen]-15'-one 13',13'-dioxide

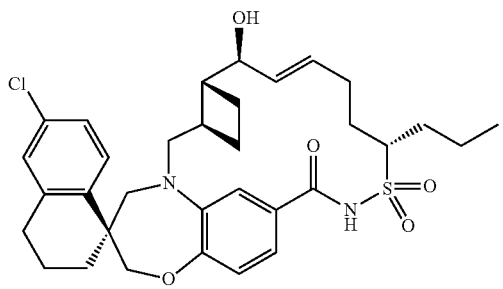 [SMILES: CCC[C@H]1CC/C=C/[C@H](O)[C@@H]2CC[C@H]2CN2C[C@@]3(CCCc4cc(Cl)ccc43)COc3ccc(cc32)C(=O)NS1(=O)=O]

The title compound was obtained as the second eluting isomer from the reversed phase preparatory HPLC separation in Example 434, Step 6. ¹H NMR (400 MHz, CDCl₃) δ 8.33 (br. s., 1H), 7.64 (d, J=8.4 Hz, 2H), 7.15 (dd, J=2.2, 8.4 Hz, 1H), 7.10 (d, J=2.2 Hz, 1H), 6.99-6.86 (m, 2H), 5.68 (dd, J=4.5, 15.8 Hz, 1H), 5.56-5.38 (m, 1H), 4.31-4.10 (m, 3H), 4.04 (dd, J=4.1, 10.6 Hz, 2H), 3.97-3.86 (m, 2H), 3.76 (d, J=14.7 Hz, 1H), 3.46 (s, 3H), 3.38-3.25 (m, 1H), 3.14 (d, J=15.8 Hz, 1H), 2.86-2.67 (m, 2H), 2.60-2.43 (m, 2H), 2.40-1.05 (m, 13H). m/z (ESI, +ve ion) 615.2 (M+H)+.

Example 436. (1S,3'R,6'R,7'S,8'E,12'S)-6-chloro-7'-hydroxy-N,N-dimethyl-15'-oxo-3,4-dihydro-2H-spiro[naphthalene-1,22'-[20]oxa[13]thia[1,14]diaza-tetracyclo[14.7.2.0³,⁶.0¹⁹,²⁴]pentacosa [8,16,18,24] tetraene]-12'-carboxamide 13',13'-dioxide

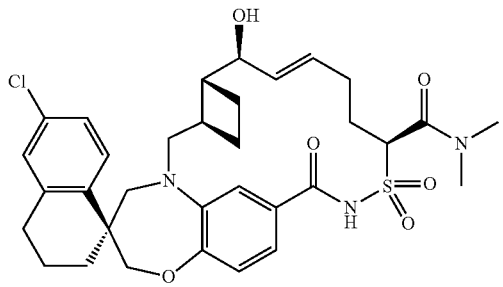 [SMILES: CN(C)C(=O)[C@@H]1CC/C=C/[C@H](O)[C@@H]2CC[C@H]2CN2C[C@@]3(CCCc4cc(Cl)ccc43)COc3ccc(cc32)C(=O)NS1(=O)=O]

Step 1: (R)-2-(N,N-bis(4-methoxybenzyl)sulfamoyl) hex-5-enoic acid and (S)-2-(N,N-bis(4-methoxybenzyl)sulfamoyl)hex-5-enoic acid

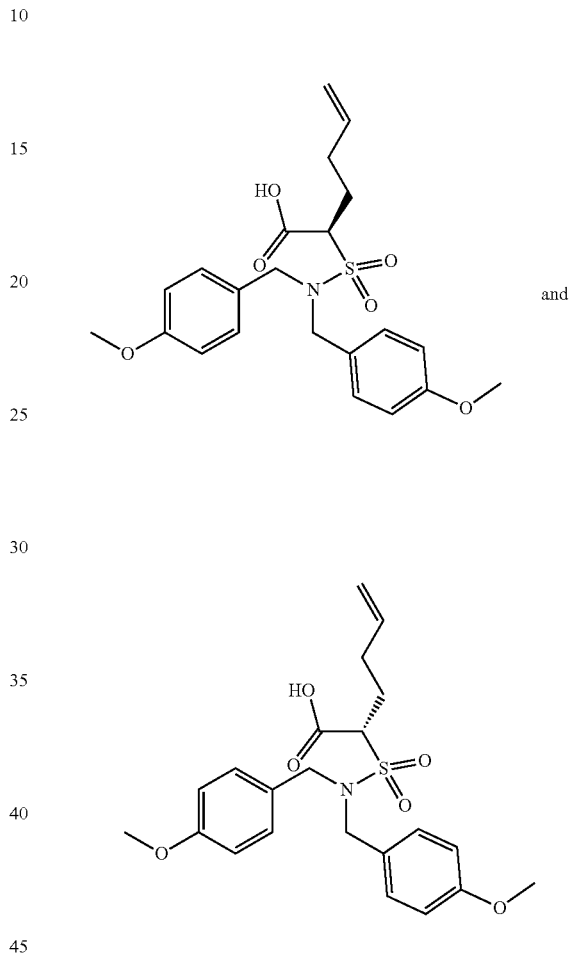

To a 100-mL round-bottomed flask were added (R)-methyl 2-(N,N-bis(4-methoxybenzyl)sulfamoyl)hex-5-enoate and (S)-methyl 2-(N,N-bis(4-methoxybenzyl)sulfamoyl) hex-5-enoate (1.10 g, 2.46 mmol, Example 434, Step 1) in THF (10.2 ml) and sodium hydroxide (0.393 g, 9.83 mmol) in Water (2.05 ml). The reaction mixture was stirred at 50° C. overnight. The reaction mixture was cooled to ambient temperature and neutralized with 1N HCl, and extracted with EtOAc (2×20 mL). The organic extract was washed with saturated NaCl (10 mL) and dried over MgSO₄, filtered and concentrated in vacuo to give the crude material. The crude material was purified by chromatography through a Redi-Sep pre-packed silica gel column (40 g), eluting with a gradient of 0% to 100% EtOAc (containing 0.1% AcOH) in hexane, to provide the title compounds (0.64 g, 60%). m/z (ESI, +ve ion) 456.2 (M+Na)+.

Step 2: (R)-2-(N,N-bis(4-methoxybenzyl)sulfa-
moyl)-N,N-dimethylhex-5-enamide and (S)-2-(N,N-
bis(4-methoxybenzyl)sulfamoyl)-N,N-dimethylhex-
5-enamide

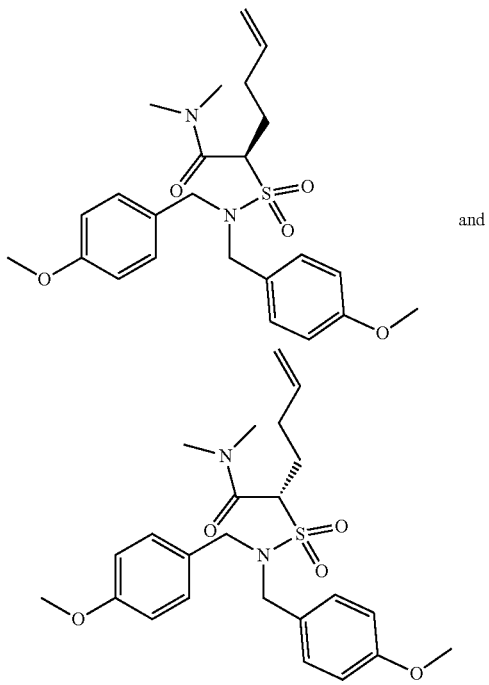

and

To a 250-mL round-bottomed flask were added (R)-2-(N,N-bis(4-methoxybenzyl)sulfamoyl)hex-5-enoic acid and (S)-2-(N,N-bis(4-methoxybenzyl)sulfamoyl)hex-5-enoic acid (228 mg, 0.526 mmol) dipea (184 µl, 1.05 mmol), 2-(1h-benzotriazol-1-yl)-1,1,3,3-tetramethyluronium hexafluorophosphate (299 mg, 0.789 mmol) and dimethylamine, 2.0 M solution in tetrahydrofuran (789 µl, 1.58 mmol) in DMF (5.3 ml). The mixture was stirred at ambient temperature overnight. The reaction mixture was diluted with water (100 mL), and extracted with DCM (2×100 mL). The organic solution was concentrated. The crude material was purified by chromatography through a Redi-Sep pre-packed silica gel column (40 g), eluting with a gradient of 30% to 80% EtOAc in hexane to provide the title compound (200 mg, 83% yield). m/z (ESI, +ve ion) 483.2 (M+Na)⁺.

Step 3: (R)—N,N-dimethyl-2-sulfamoylhex-5-ena-
mide and (S)—N,N-dimethyl-2-sulfamoylhex-5-
enamide

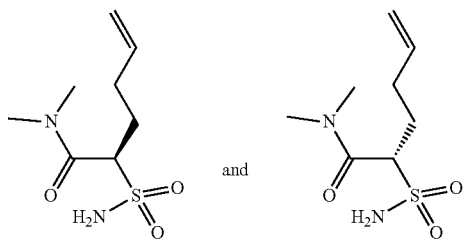

and

The title compound was prepared in an analogous manner to that described in Example 432, Step 3 using (R)-2-(N,N-bis(4-methoxybenzyl)sulfamoyl)-N,N-dimethylhex-5-enamide and (S)-2-(N,N-bis(4-methoxybenzyl)sulfamoyl)-N,N-dimethylhex-5-enamide. m/z (ESI, +ve ion) 221.2 (M+H)⁺.

Step 4: (S)-6'-chloro-N—(((S)-1-(dimethylamino)-1-
oxohex-5-en-2-yl)sulfonyl)-5-(((1R,2R)-2-((S)-1-
hydroxyallyl)cyclobutyl)methyl)-3',4,4',5-tetrahydro-
2H,2'H-spiro[benzo[b][1,4]oxazepine-3,1'-
naphthalene]-7-carboxamide and (S)-6'-chloro-N—
(((R)-1-(dimethylamino)-1-oxohex-5-en-2-yl)
sulfonyl)-5-(((1R,2R)-2-((S)-1-hydroxyallyl)
cyclobutyl)methyl)-3',4,4',5-tetrahydro-2H,2'H-spiro
[benzo[b][1,4]oxazepine-3,1'-naphthalene]-7-
carboxamide

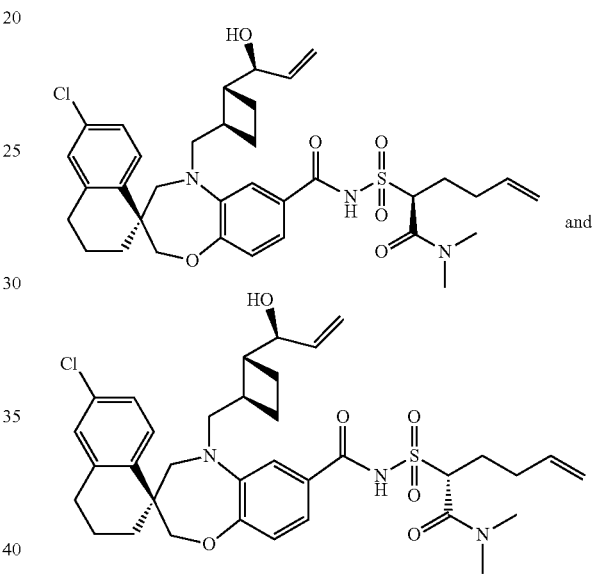

The title compounds were prepared in an analogous manner to that described in Example 432, Step 4 using (S)-6'-chloro-5-(((1R,2R)-2-((S)-1-hydroxyallyl)cy-clobutyl)methyl)-3',4,4',5-tetrahydro-2H,2'H-spiro[benzo[b][1,4]oxazepine-3,1'-naphthalene]-7-carboxylic acid (Intermediate, AA11A) and (R)—N,N-dimethyl-2-sulfamoylhex-5-enamide and (S)—N,N-dimethyl-2-sulfamoylhex-5-enamide. m/z (ESI, +ve ion) 670.2 (M+H)⁺.

Step 5: (1S,3'R,6'R,7'S,8'E,12'S)-6-chloro-7'-hy-
droxy-N,N-dimethyl-15'-oxo-3,4-dihydro-2H-spiro
[naphthalene-1,22'-[20]oxa[13]thia[1,14]diazatetra-
cyclo[14.7.2.0³,⁶.0¹⁹,²⁴]pentacosa [8,16,18,24]
tetraene]-12'-carboxamide 13',13'-dioxide The title compound was prepared in an analogous manner to that described in Example 432, Step 5 using (S)-6'-chloro-N—(((S)-1-(dimethylamino)-1-oxohex-5-en-2-yl)sulfonyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide and (S)-6'-chloro-N—(((R)-1-(dimethylamino)-1-oxohex-5-en-2-yl)sulfonyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide, and isolated as first eluting isomer from the reversed phase preparatory HPLC separation. ¹H NMR (500 MHz, CDCl₃) δ 8.35 (br. s., 1H), 7.70 (d, J=8.6 Hz, 1H), 7.19 (dd, J=2.2, 8.6 Hz, 1H), 7.10 (d, J=2.2 Hz, 1H), 6.98-6.80 (m, 3H), 5.83-5.68 (m, 2H), 5.58 (dd, J=2.7, 10.3 Hz, 1H), 4.32-4.23 (m, 1H), 4.17-4.05 (m, 2H), 3.84 (d, J=14.2 Hz, 1H), 3.72 (d, J=14.4 Hz, 1H), 3.38 (s, 3H), 3.24 (d, J=14.2 Hz, 1H), 3.11 (s, 3H), 3.01 (dd, J=9.3, 15.4 Hz, 1H), 2.87-2.64 (m, 3H), 2.53-2.25 (m, 3H), 2.09-1.49 (m, 10H), 1.41 (t, J=12.7 Hz, 1H).

Example 437. (1S,3'R,6'R,7'S,8'E,12'R)-6-chloro-7'-hydroxy-N,N-dimethyl-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraene]-12'-carboxamide 13',13'-dioxide

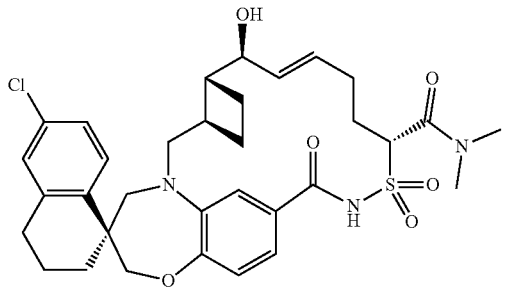 [SMILES: CN(C)C(=O)[C@H]1CC/C=C/[C@H](O)[C@@H]2CC[C@H]2CN2C[C@@]3(CCCc4cc(Cl)ccc43)COc3ccc(cc32)C(=O)NS1(=O)=O]

The title compound was obtained as the second eluting isomer from the reversed phase preparatory HPLC separation in Example 436, Step 5. ¹H NMR (500 MHz, CDCl₃) δ 8.92 (br. s., 1H), 7.72 (br. s., 1H), 7.64 (d, J=8.6 Hz, 1H), 7.15 (dd, J=2.1, 8.4 Hz, 1H), 7.11 (d, J=2.0 Hz, 1H), 7.03-6.97 (m, 1H), 6.95-6.90 (m, 1H), 5.66 (dd, J=4.2, 15.6 Hz, 1H), 5.47-5.29 (m, 2H), 4.35-4.22 (m, 2H), 4.19-4.06 (m, 1H), 3.90 (d, J=4.6 Hz, 1H), 3.82 (d, J=13.9 Hz, 1H), 3.42 (s, 3H), 3.29 (d, J=13.9 Hz, 1H), 3.18-3.03 (m, 4H), 2.89-2.70 (m, 3H), 2.65-1.20 (m, 14H).

Example 438. (1S,3'R,6'R,7'S,8'E,12'S)-6-chloro-12'-(difluoromethyl)-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,12'R)-6-chloro-12'-(difluoromethyl)-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa 8,16,18,24]tetraen]-15'-one 13',13'-dioxide

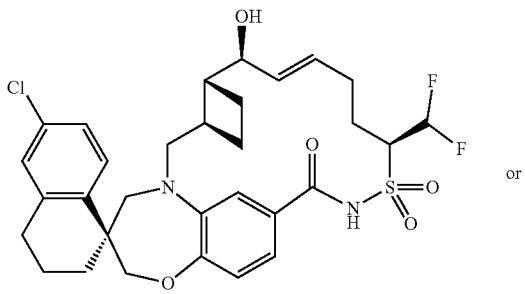

or

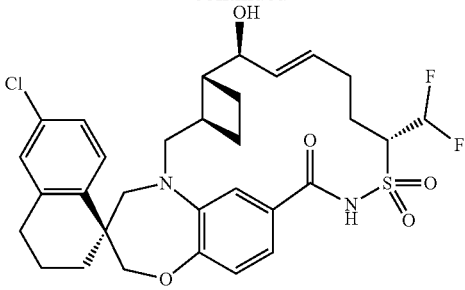

Step 1: (R)—N,N-bis(4-methoxybenzyl)-1-oxohex-5-ene-2-sulfonamide and (S)—N,N-bis(4-methoxybenzyl)-1-oxohex-5-ene-2-sulfonamide

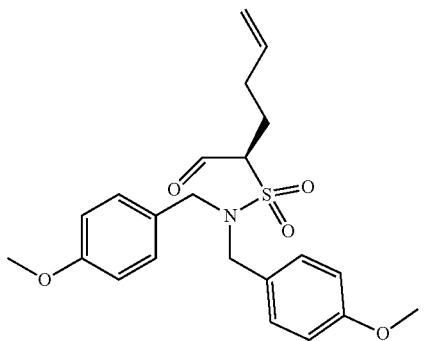

and

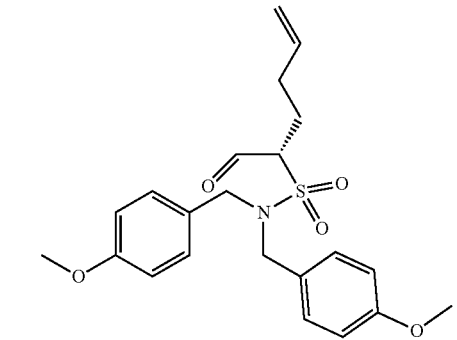

In a 250 mL round-bottomed flask with stirbar was charged with (R)-1-hydroxy-N,N-bis(4-methoxybenzyl) hex-5-ene-2-sulfonamide and (S)-1-hydroxy-N,N-bis(4-methoxybenzyl)hex-5-ene-2-sulfonamide (0.730 g, 1.74 mmol, Example 434, Step 2) in 20 mL of DCM. To this solution was added dess-martin periodinane (1.11 g, 2.61 mmol). The reaction mixture was stirred at ambient temperature for 4 hrs. The reaction mixture was diluted with saturated Na₂S₂O₃ solution (30 mL), and extracted with Et₂O (2×50 mL). The combined organic solution was further washed with saturated NaHCO₃ and brine, and dried over MgSO₄, concentrated. The crude material was purified by chromatography through a Redi-Sep pre-packed silica gel column (40 g), eluting with a gradient of 10% to 50% EtOAc in hexane, to provide the title compound (0.700 g, 96% yield) as a colorless oil. m/z (ESI, +ve ion) 440.2 (M+Na)⁺.

Step 2: (R)-1,1-difluoro-N,N-bis(4-methoxybenzyl)hex-5-ene-2-sulfonamide and (S)-1,1-difluoro-N,N-bis(4-methoxybenzyl)hex-5-ene-2-sulfonamide

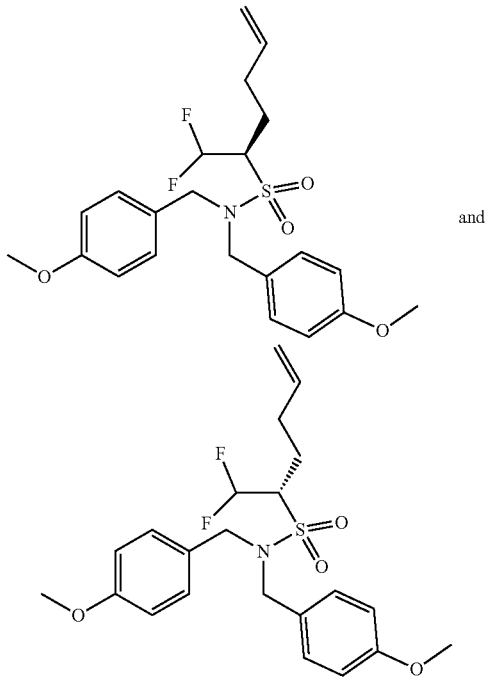

To a 100-mL round-bottomed flask were added (R)—N,N-bis(4-methoxybenzyl)-1-oxohex-5-ene-2-sulfonamide and (S)—N,N-bis(4-methoxybenzyl)-1-oxohex-5-ene-2-sulfonamide (0.230 g, 0.551 mmol) and diethylaminosulfur trifluoride (0.29 ml, 2.2 mmol) in DCM (5.5 ml), and then EtOH, 200 proof, tax-free (3.22 µl, 0.055 mmol). The reaction mixture was stirred at ambient temperature overnight, and neutralized with saturated NaHCO$_3$ solution, and extracted with EtOAc (2×20 mL). The organic extract was washed with saturated NaCl (10 mL), dried over MgSO$_4$, filtered and concentrated in vacuo to the title compound as a yellowish oil. m/z (ESI, +ve ion) 462.2 (M+Na)$^+$.

Step 3: (R)-1,1-difluorohex-5-ene-2-sulfonamide and (S)-1,1-difluorohex-5-ene-2-sulfonamide

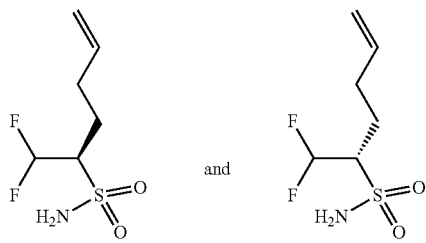

The title compound was prepared in an analogous manner to that described in Example 432, Step 3 using (R)-1,1-difluoro-N,N-bis(4-methoxybenzyl)hex-5-ene-2-sulfonamide and (S)-1,1-difluoro-N,N-bis(4-methoxybenzyl)hex-5-ene-2-sulfonamide. $^1$H NMR (400 MHz, CDCl$_3$) δ 5.80 (tdd, J=6.65, 10.32, 17.07 Hz, 1H), 4.99-5.24 (m, 2H), 4.55-4.82 (m, 2H), 3.48 (dtdd, J=3.33, 5.97, 7.46, 19.34 Hz, 1H), 2.51-2.70 (m, 1H), 2.28-2.47 (m, 2H), 2.00-2.20 (m, 2H).

Step 4: (S)-6'-chloro-N—(((S)-1,1-difluorohex-5-en-2-yl)sulfonyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide and (S)-6'-chloro-N—(((R)-1,1-difluorohex-5-en-2-yl)sulfonyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide

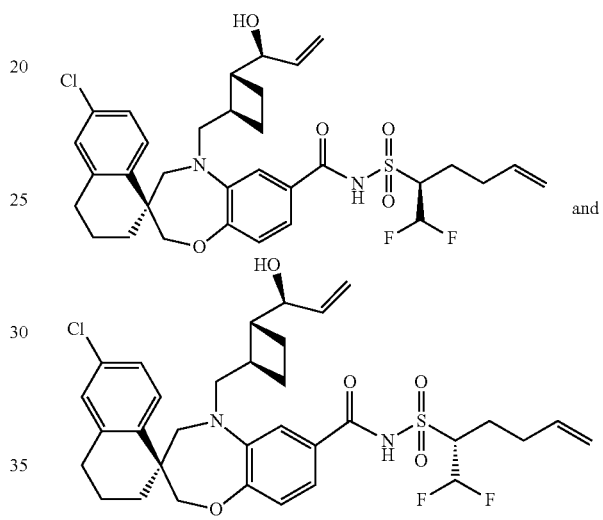

The title compound was prepared in an analogous manner to that described in Example 432, Step 4 using (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Intermediate, AA11A) and (R)-1,1-difluorohex-5-ene-2-sulfonamide and (S)-1,1-difluorohex-5-ene-2-sulfonamide. m/z (ESI, +ve ion) 649.2 (M+H)$^+$.

Step 5: (1S,3'R,6'R,7'S,8'E,12'S)-6-chloro-12'-(difluoromethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-12'-(difluoromethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compound was prepared in an analogous manner to that described in Example 432, Step 5 using (S)-6'-chloro-N—(((S)-1,1-difluorohex-5-en-2-yl)sulfonyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide and (S)-6'-chloro-N—(((R)-1,1-difluorohex-5-en-2-yl)sulfonyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7- carboxamide, and isolated as first eluting isomer from the reversed phase preparatory HPLC separation. $^1$H NMR (500 MHz, CDCl$_3$) δ 8.80 (br. s., 1H), 7.70 (d, J=8.6 Hz, 1H), 7.19 (dd, J=2.1, 8.4 Hz, 1H), 7.22-7.16 (m, 1H), 7.10 (d, J=2.0 Hz, 1H), 7.04-6.89 (m, 3H), 6.75-6.29 (m, 1H), 5.86-5.50 (m, 2H), 4.54-4.36 (m, 1H), 4.22-4.06 (m, 3H), 3.82-3.63 (m, 2H), 3.27 (d, J=13.9 Hz, 1H), 3.11 (d, J=9.8 Hz, 1H), 2.87-2.67 (m, 2H), 2.52-1.06 (m, 15H). m/z (ESI, +ve ion) 621.2 (M+H)$^+$.

Example 439. (1S,3'R,6'R,7'S,8'E,12'S)-6-chloro-12'-(ethoxymethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-12'-(ethoxymethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

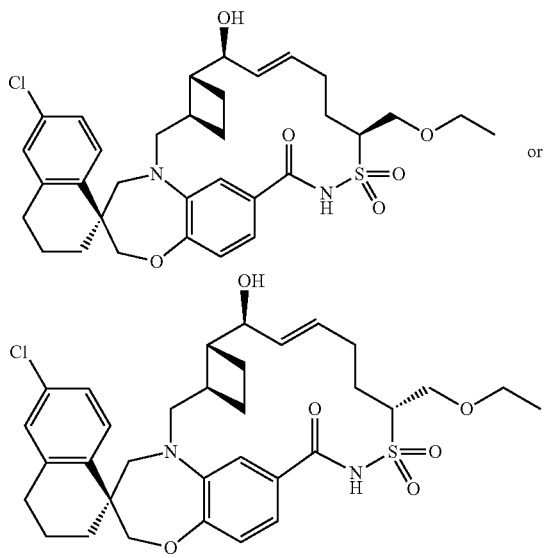

Step 1: (R)-1-ethoxy-N,N-bis(4-methoxybenzyl)hex-5-ene-2-sulfonamide and (S)-1-ethoxy-N,N-bis(4-methoxybenzyl)hex-5-ene-2-sulfonamide and N,N-bis(4-methoxybenzyl)hexa-1,5-diene-2-sulfonamide

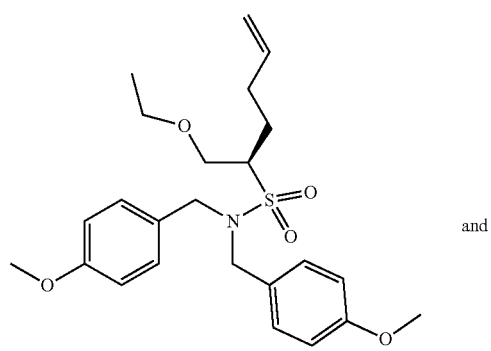

and

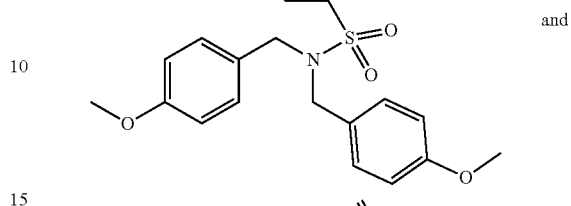

and

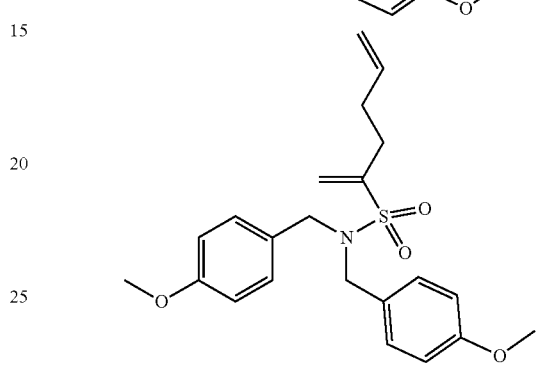

or

The title compounds were prepared in an analogous manner to that described in Example 434, Step 3 using iodoethane. m/z (ESI, +ve ion) 470.2 (M+Na)$^+$ and m/z (ESI, +ve ion) 424.2 (M+Na)$^+$.

Step 2: (R)-1-ethoxyhex-5-ene-2-sulfonamide and (S)-1-ethoxyhex-5-ene-2-sulfonamide and hexa-1,5-diene-2-sulfonamide

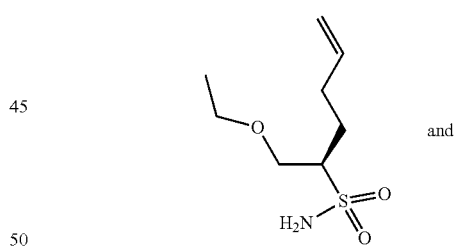

and

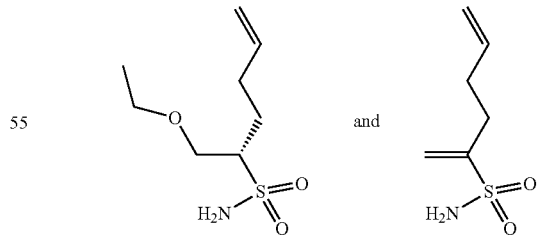

The title compound were prepared in an analogous manner to that described in Example 432, Step 3 using (R)-1-ethoxyhex-5-ene-2-sulfonamide and (S)-1-ethoxyhex-5-ene-2-sulfonamide and hexa-1,5-diene-2-sulfonamide. m/z (ESI, +ve ion) 208.2 (M+H)$^+$ and m/z (ESI, +ve ion) 184.2 (M+NO$^+$.

Step 3: (S)-6'-chloro-N—(((S)-1-ethoxyhex-5-en-2-yl)sulfonyl)-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N—(((R)-1-ethoxyhex-5-en-2-yl)sulfonyl)-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N-(hexa-1,5-dien-2-ylsulfonyl)-5-(((1R,2R)-2-((S,E)-1-hydroxyhex-2-en-1-yl)cyclobutyl)methyl)-3',4,4',5-tetrahydro-2H,2'H-carboxamide

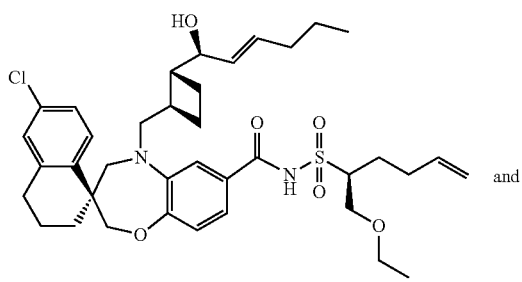

and

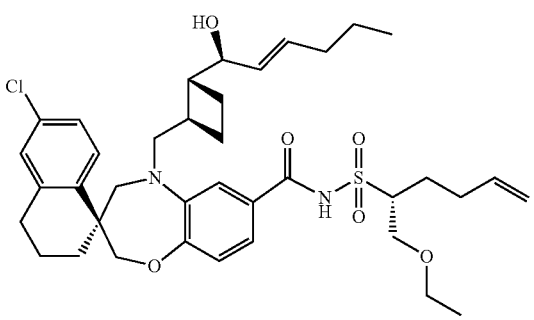

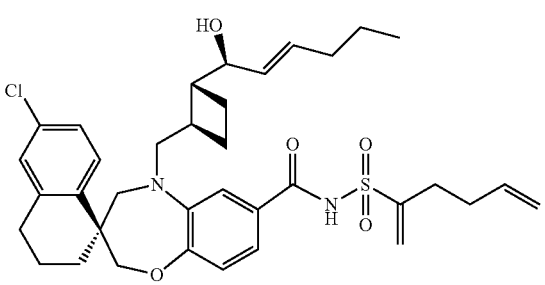

The title compound was prepared in an analogous manner to that described in Example 432, Step 4 using (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate, AA12A) and (R)-1-ethoxyhex-5-ene-2-sulfonamide and (S)-1-ethoxyhex-5-ene-2-sulfonamide and hexa-1,5-diene-2-sulfonamide. m/z (ESI, +ve ion) 699.2 (M+H)+ and m/z (ESI, +ve ion) 653.2 (M+H)+.

Step 4: (1S,3'R,6'R,7'S,8'E,12'S)-6-chloro-12'-(ethoxymethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-12'-(ethoxymethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide The title compound was prepared in an analogous manner to that described in Example 432, Step 5 using (S)-6'-chloro-N—(((S)-1-ethoxyhex-5-en-2-yl)sulfonyl)-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N—(((R)-1-ethoxyhex-5-en-2-yl)sulfonyl)-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N-(hexa-1,5-dien-2-ylsulfonyl)-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide, and isolated as the second eluting isomer from the reversed phase preparatory HPLC separation. $^1$H NMR (400 MHz, CDCl$_3$) δ 8.18 (s, 1H), 7.70 (d, J=8.4 Hz, 1H), 7.19 (dd, J=2.2, 8.5 Hz, 1H), 7.09 (d, J=2.2 Hz, 1H), 6.96-6.88 (m, 3H), 5.90-5.77 (m, 1H), 5.75-5.63 (m, 1H), 4.28 (qd, J=4.2, 8.8 Hz, 1H), 4.21 (dd, J=4.3, 6.8 Hz, 1H), 4.15-3.94 (m, 4H), 3.82 (d, J=13.7 Hz, 1H), 3.71 (d, J=14.3 Hz, 1H), 3.66-3.55 (m, 2H), 3.25 (d, J=14.3 Hz, 1H), 3.04 (dd, J=8.5, 15.4 Hz, 1H), 2.89-2.65 (m, 2H), 2.52-1.59 (m, 14H), 1.42 (t, J=11.6 Hz, 1H), 1.24 (t, J=7.0 Hz, 3H). m/z (ESI, +ve ion) 629.2 (M+H)+.

Example 440. (1S,3'R,6'R,7'S,8'E,12'R)-6-chloro-12'-(ethoxymethyl)-7'-hydroxy-3,4-dihydro-2H,15'H-spiro[naphthalene-1,22'-[20]oxa[13]thia[1,14] diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'S)-6-chloro-12'-(ethoxymethyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

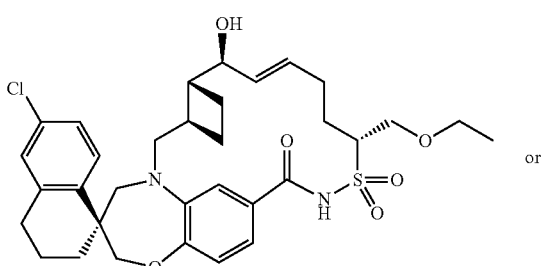

or

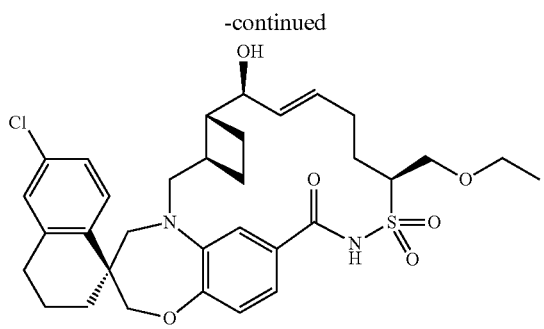

The title compound was obtained as the third eluting isomer from the reversed phase preparatory HPLC separation in Example 439, Step 4. $^1$H NMR (400 MHz, CDCl$_3$) δ 8.10 (br. s., 1H), 7.68-7.49 (m, 2H), 7.16 (dd, J=2.2, 8.5 Hz, 1H), 7.10 (d, J=2.3 Hz, 1H), 6.93 (s, 2H), 5.74-5.62 (m, 1H), 5.48 (d, J=14.5 Hz, 1H), 4.28-3.92 (m, 8H), 3.76 (d, J=13.9 Hz, 1H), 3.65-3.56 (m, 2H), 3.33 (d, J=14.9 Hz, 1H), 3.15 (d, J=15.1 Hz, 1H), 2.85-2.69 (m, 2H), 2.61-2.44 (m, 2H), 2.40-1.06 (m, 15H). m/z (ESI, +ve ion) 629.2 (M+H)$^+$.

Example 441. (1S,3'R,6'R,7'S,8'E)-6-chloro-7'-hydroxy-12'-methylidene-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24] tetraen]-15'-one 13',13'-dioxide

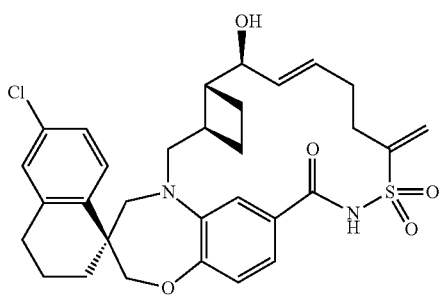 [SMILES: C=C1CC/C=C/[C@H](O)[C@@H]2CC[C@H]2CN2C[C@@]3(CCCc4cc(Cl)ccc43)COc3ccc(cc32)C(=O)NS1(=O)=O]

The title compound was obtained as the first eluting isomer from the reversed phase preparatory HPLC separation in Example 439, Step 4. $^1$H NMR (500 MHz, CDCl$_3$) δ 8.33 (s, 1H), 7.70 (d, J=8.6 Hz, 1H), 7.18 (dd, J=2.2, 8.3 Hz, 1H), 7.09 (d, J=2.0 Hz, 1H), 6.99-6.91 (m, 2H), 6.87 (br. s., 1H), 6.73 (s, 1H), 6.04 (s, 1H), 5.83-5.60 (m, 2H), 4.16 (dd, J=4.2, 7.3 Hz, 1H), 4.09 (q, J=12.2 Hz, 2H), 3.75-3.63 (m, 2H), 3.27 (d, J=14.2 Hz, 1H), 3.12 (br. s., 1H), 2.86-2.71 (m, 2H), 2.67-2.54 (m, 2H), 2.47-2.29 (m, 4H), 2.05-1.19 (m, 9H). m/z (ESI, +ve ion) 583.2 (M+H)$^+$.

Example 442. (1S,3'R,6'R,7'S,8'E,12'S)-6-chloro-7'-hydroxy-12'-(2-methoxyethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24] tetraen]-15'-one 13',13'-dioxide or (1S,3'R,6'R,7'S, 8'E,12'R)-6-chloro-7'-hydroxy-12'-(2-methoxyethyl)-3,4-dihydro-2H,15'H-spiro[naphthalene-1,22'-[20] oxa[13]thia[1,14]diazatetracyclo[14.7.2.0$^{3,6}$.0$^{19,24}$] pentacosa 8,16,18,24]tetraen]-15'-one 13',13'-dioxide

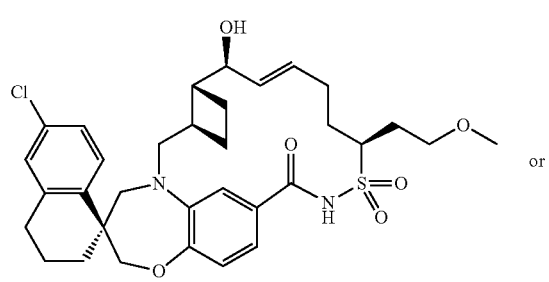

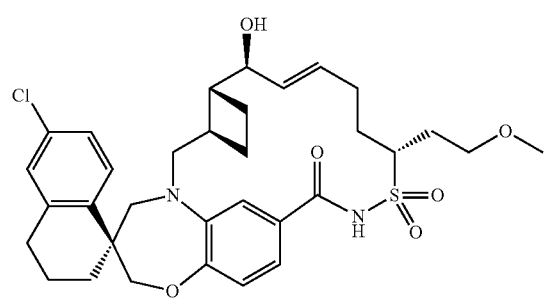

Step 1: 3-chloro-N,N-bis(4-methoxybenzyl)propane-1-sulfonamide

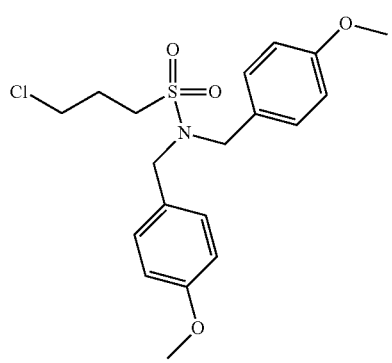 [SMILES: COc1ccc(CN(Cc2ccc(OC)cc2)S(=O)(=O)CCCCl)cc1]

The title compound was prepared in an analogous manner to that described in Example 432, Step 1 using 3-chloropropanesulfonyl chloride. m/z (ESI, +ve ion) 420.2 (M+Na)$^+$.

Step 2: 3-methoxy-N,N-bis(4-methoxybenzyl)propane-1-sulfonamide

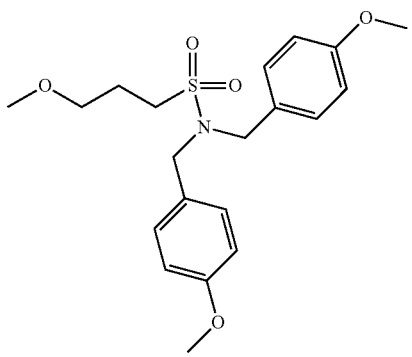

To a 100-mL round-bottomed flask were added sodium methoxide, 0.5 M in methanol (23.4 mL, 11.7 mmol) and 3-chloro-N,N-bis(4-methoxybenzyl)propane-1-sulfonamide (3.10 g, 7.79 mmol) in DMSO (10 mL). The reaction was stirred at 50° C. overnight. The reaction mixture was diluted with 1N HCl (10 mL), and extracted with Et$_2$O (2×30 mL). The organic extract was washed with saturated NaCl (10 mL) and dried over MgSO$_4$, filtered and concentrated in vacuo. The crude material was purified by chromatography through a Redi-Sep pre-packed silica gel column (40 g), eluting with a gradient of 30% to 70% EtOAc in hexane, to provide the title compound (2.40 g, 78% yield) as a yellow oil. m/z (ESI, +ve ion) 416.2 (M+Na)$^+$.

Step 3: (R)-1-methoxy-N,N-bis(4-methoxybenzyl)hept-6-ene-3-sulfonamide and (S)-1-methoxy-N,N-bis(4-methoxybenzyl)hept-6-ene-3-sulfonamide

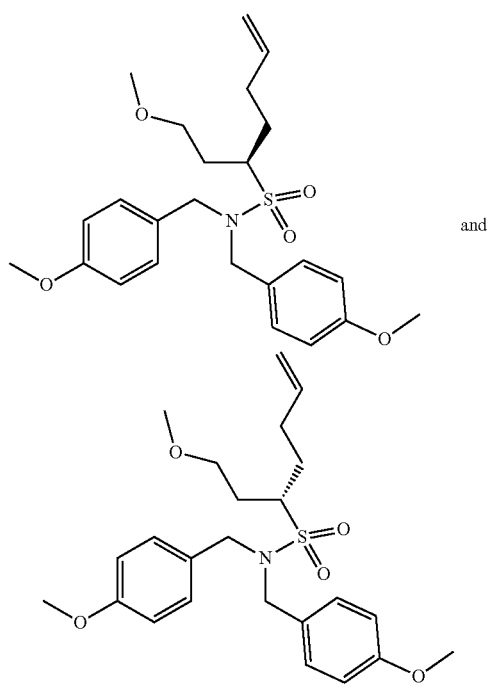

The title compound was prepared in an analogous manner to that described in Example 434, Step 1 using 3-methoxy-N,N-bis(4-methoxybenzyl)propane-1-sulfonamide and 4-bromobut-1-ene, and purified by chromatography eluting with a gradient of 15% to 40% EtOAc in hexane. m/z (ESI, +ve ion) 470.2 (M+Na)$^+$.

Step 4: (R)-1-methoxyhept-6-ene-3-sulfonamide and (S)-1-methoxyhept-6-ene-3-sulfonamide

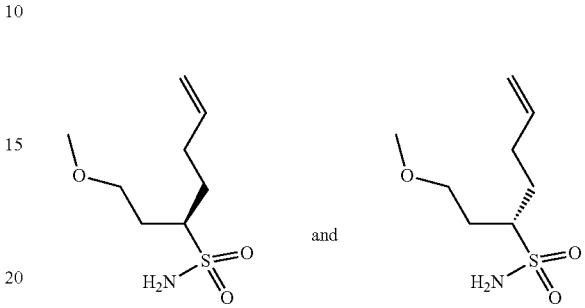

The title compound were prepared in an analogous manner to that described in Example 432, Step 3 using (R)-1-methoxy-N,N-bis(4-methoxybenzyl)hept-6-ene-3-sulfonamide and (S)-1-methoxy-N,N-bis(4-methoxybenzyl)hept-6-ene-3-sulfonamide. m/z (ESI, +ve ion) 230.2 (M+Na)$^+$.

Step 5: (S)-6'-chloro-5-(((1R,2R)-2-((S,E)-1-hydroxyhex-2-en-1-yl)cyclobutyl)methyl)-N—(((S)-1-methoxyhept-6-en-3-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N—(((R)-1-methoxyhept-6-en-3-yl)sulfonyl)-3',4,4',5-tetrahydro-2H,2'H-spiro[benzo[b][1,4]oxazepine-3,1'-naphthalene]-7-carboxamide

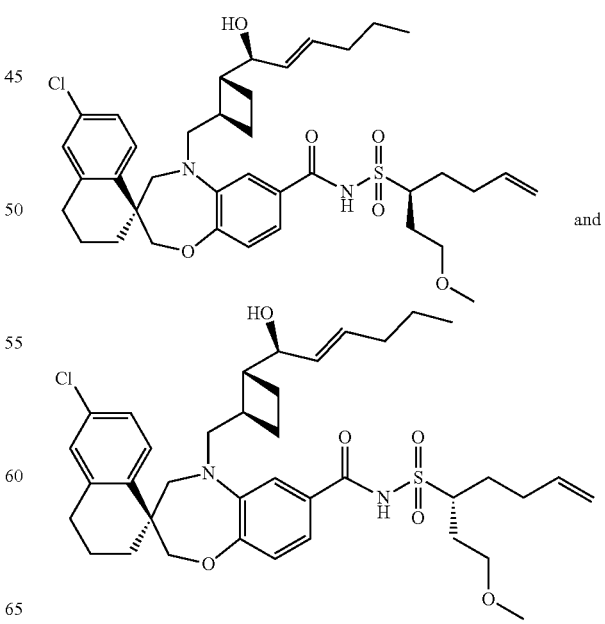

993

The title compound was prepared in an analogous manner to that described in Example 432, Step 4 using (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate, AA12A) and (R)-1-methoxyhept-6-ene-3-sulfonamide and (S)-1-methoxyhept-6-ene-3-sulfonamide. m/z (ESI, +ve ion) 699.2 (M+H)+.

Step 6: (1S,3'R,6'R,7'S,8'E,12'S)-6-chloro-7'-hydroxy-12'-(2-methoxyethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-hydroxy-12'-(2-methoxyethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compound was prepared in an analogous manner to that described in Example 432, Step 5 using (S)-6'-chloro-5-(((1R,2R)-2-((S,E)-1-hydroxyhex-2-en-1-yl)cyclobutyl)methyl)-N—(((S)-1-methoxyhept-6-en-3-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N—(((R)-1-methoxyhept-6-en-3-yl)sulfonyl)-3',4,4',5-tetrahydro-2H,2'H-spiro[benzo[b][1,4]oxazepine-3,1'-naphthalene]-7-carboxamide, and isolated as the first eluting isomer from the reversed phase preparatory HPLC separation. $^1$H NMR (400 MHz, CDCl$_3$) δ 8.19 (s, 1H), 7.70 (d, J=8.4 Hz, 1H), 7.19 (dd, J=2.3, 8.4 Hz, 1H), 7.09 (d, J=2.2 Hz, 1H), 6.92 (s, 3H), 5.94-5.81 (m, 1H), 5.77-5.67 (m, 1H), 4.33-4.18 (m, 2H), 4.14-4.03 (m, 2H), 3.82 (d, J=14.1 Hz, 1H), 3.75-3.60 (m, 3H), 3.40 (s, 3H), 3.24 (d, J=14.3 Hz, 1H), 3.03 (dd, J=9.3, 15.4 Hz, 1H), 2.88-2.67 (m, 2H), 2.51-1.60 (m, 16H), 1.41 (t, J=12.4 Hz, 1H). m/z (ESI, +ve ion) 629.2 (M+H)+.

Example 443. (1S,3'R,6'R,7'S,8'E,12'R)-6-chloro-7'-hydroxy-12'-(2-methoxyethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'S)-6-chloro-7'-hydroxy-12'-(2-methoxyethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

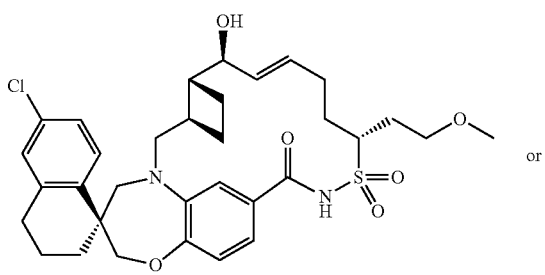

or

994

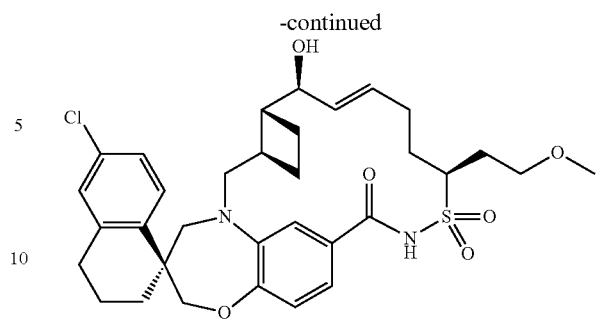

The title compound was obtained as the second eluting isomer from the reversed phase preparatory HPLC separation in Example 442, Step 6. $^1$H NMR (400 MHz, CDCl$_3$) δ 8.12 (br. s., 1H), 7.68-7.47 (m, 2H), 7.16 (dd, J=2.2, 8.4 Hz, 1H), 7.10 (d, J=2.2 Hz, 1H), 6.93 (s, 2H), 5.73 (dd, J=4.5, 15.8 Hz, 1H), 5.55-5.34 (m, 1H), 4.32-4.18 (m, 2H), 4.15-3.88 (m, 4H), 3.83-3.59 (m, 4H), 3.42 (s, 3H), 3.40-3.28 (m, 2H), 3.17 (d, J=16.0 Hz, 1H), 2.80-2.72 (m, 2H), 2.56-2.36 (m, 4H), 2.25 (br. s., 1H), 2.10-1.35 (m, 9H). m/z (ESI, +ve ion) 629.2 (M+H)+.

Example 444. (1S,3'R,6'R,7'S,8'E,12'S)-6-chloro-7'-methoxy-12'-(methoxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

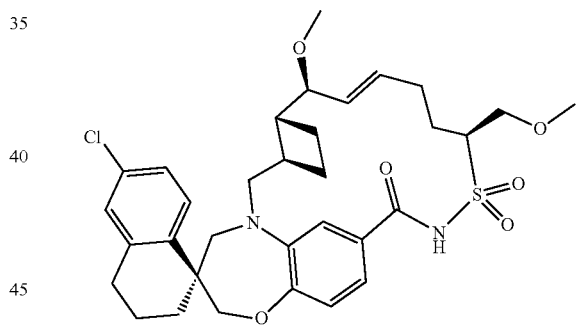

The title compound was prepared in an analogous manner to that described in Example 404 using (1S,3'R,6'R,7'S,8'E,12'S)-6-chloro-7'-hydroxy-12'-(methoxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 434, Step 6, the first eluting isomer) and iodomethane. $^1$H NMR (500 MHz, CDCl$_3$) δ 7.99 (s, 1H), 7.70 (d, J=8.6 Hz, 1H), 7.19 (dd, J=2.3, 8.4 Hz, 1H), 7.09 (d, J=2.0 Hz, 1H), 6.96-6.91 (m, 1H), 6.90-6.86 (m, 1H), 6.81 (d, J=1.7 Hz, 1H), 5.90-5.78 (m, 1H), 5.55 (dd, J=8.7, 15.3 Hz, 1H), 4.48-4.37 (m, 1H), 4.16-4.02 (m, 3H), 4.00-3.92 (m, 1H), 3.82 (d, J=14.9 Hz, 1H), 3.71 (d, J=14.2 Hz, 1H), 3.65 (dd, J=3.7, 8.8 Hz, 1H), 3.45 (s, 3H), 3.29-3.18 (m, 4H), 2.99 (dd, J=10.1, 15.3 Hz, 1H), 2.85-2.69 (m, 2H), 2.54-1.17 (m, 14H). m/z (ESI, +ve ion) 629.2 (M+H)+.

Example 445. (1S,3'R,6'R,7'S,8'E,12'S)-6-chloro-7'-hydroxy-12'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa 8,16,18,24]tetraen]-15'-one 13',13'-dioxide

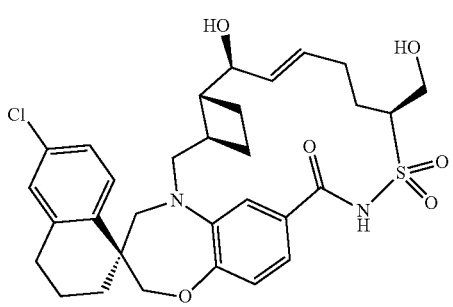 [SMILES: O=C1NS(=O)(=O)[C@H](CO)CC/C=C/[C@H](O)[C@@H]2CC[C@H]2CN2C[C@@]3(CCCc4cc(Cl)ccc43)COc3ccc1cc32]

Step 1: (R)-1-hydroxyhex-5-ene-2-sulfonamide and (S)-1-hydroxyhex-5-ene-2-sulfonamide

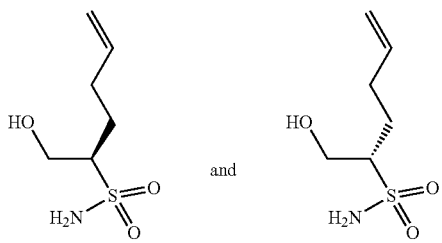

The title compound was prepared in an analogous manner to that described in Example 432, Step 3 using (R)-1-hydroxy-N,N-bis(4-methoxybenzyl)hex-5-ene-2-sulfonamide and (S)-1-hydroxy-N,N-bis(4-methoxybenzyl)hex-5-ene-2-sulfonamide (Example 434, Step 2), and isolated from chromatography through a Redi-Sep pre-packed silica gel column, eluting with a gradient of 50% to 100% EtOAc in hexane. m/z (ESI, +ve ion) 202.1 (M+Na)$^+$.

Step 2: (R)-1-((tert-butyldimethylsilyl)oxy)hex-5-ene-2-sulfonamide and (S)-1-((tert-butyldimethylsilyloxy)hex-5-ene-2-sulfonamide

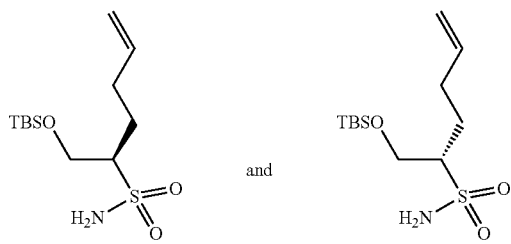 [SMILES: C=CCC[C@H](CO[Si](C)(C)C(C)(C)C)S(N)(=O)=O ; C=CCC[C@@H](CO[Si](C)(C)C(C)(C)C)S(N)(=O)=O]

To a solution of (R)-1-hydroxyhex-5-ene-2-sulfonamide and (S)-1-hydroxyhex-5-ene-2-sulfonamide (170 mg, 0.948 mmol) in 6 mL of DCM was added tert-butyldimethylsilyl chloride (157 mg, 1.04 mmol), followed by imidazole (71.0 mg, 1.04 mmol). The resulting mixture was stirred at ambient temperature overnight. The reaction mixture was concentrated. The residue was diluted with 1N HCl (1 mL) and water (10 mL), extracted with Et$_2$O (2×20 mL).

The organic extract was washed with saturated NaCl (10 mL) and dried over MgSO$_4$, filtered and concentrated in vacuo to give the title compound (270 mg, 97%) as a colorless oil. m/z (ESI, +ve ion) 316.3 (M+Na)$^+$.

Step 3: (1S,3'R,6'R,7'S,8'E,12'S)-6-chloro-12'-(((dimethyl(2-methyl-2-propanyl)silyl)oxy)methyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide and (1S,3'R,6'R,7'S,8'E,12'R)-6-chloro-12'-(((dimethyl(2-methyl-2-propanyl)silyl)oxy)methyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

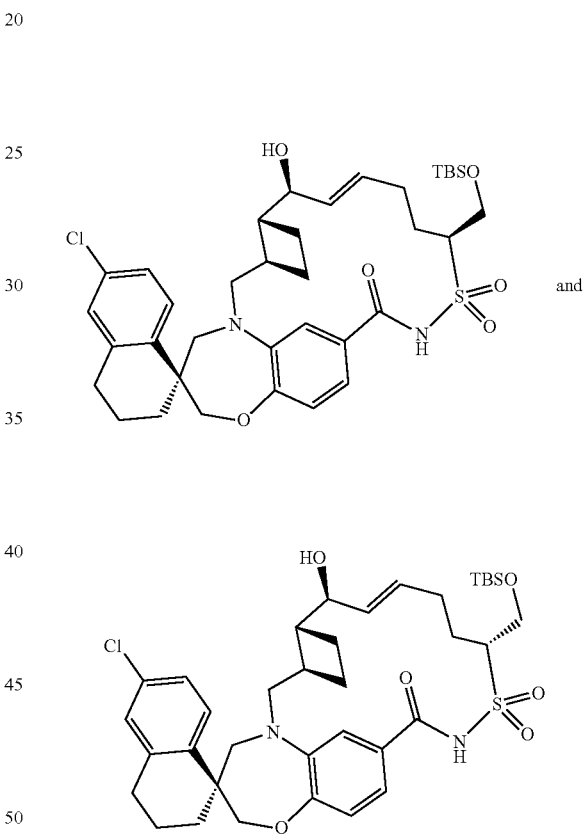

The title compound was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate, AA12A) and (R)-1-((tert-butyldimethylsilyl)oxy)hex-5-ene-2-sulfonamide and (S)-1-((tert-butyldimethylsilyl)oxy)hex-5-ene-2-sulfonamide by similar procedures described in Example 432, Steps 4-5, and isolated from chromatography through a Redi-Sep pre-packed silica gel column, eluting with a gradient of 20% to 50% EtOAc (containing 0.1% AcOH) in hexane. m/z (ESI, +ve ion) 715.2 (M+H)$^+$.

Step 4: (1S,3'R,6'R,7'S,8'E,12'S)-6-chloro-7'-hydroxy-12'-(hydroxymethyl)-3,4-dihydro-2H,15'H-spiro[naphthalene-[20]oxa[13]thia[1,14]diazatetracyclo[14.7.2.0$^{3,6}$.0$^{19,24}$]pentacosa [8,16,18,24] tetraen]-15'-one 13',13'-dioxide To a solution of (1S,3'R,6'R,7'S,8'E,12'S)-6-chloro-12'-(((dimethyl(2-methyl-2-propanyl)silyl)oxy)methyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,12'R)-6-chloro-12'-(((dimethyl(2-methyl-2-propanyl)silyl)oxy)methyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (0.038 g, 0.053 mmol) in tetrahydrofuran (0.53 ml) at 0° C. was added tetra-N-butylammonium fluoride, 1M solution. In THF (0.106 ml, 0.106 mmol) dropwise, and the reaction mixture was stirred at ambient temperature for 1 h. The reaction mixture was concentrated. The residue was purified by reversed phase preparatory HPLC (Gemini™ Prep C$_{18}$ 5 µm column; Phenomenex, Torrance, CA; gradient elution of 40% to 95% MeCN in water, where both solvents contain 0.1% TFA, 30 min method) to provide the title compound as the first eluting isomer. $^1$H NMR (500 MHz, CDCl$_3$) δ 8.27 (br. s., 1H), 7.70 (d, J=8.6 Hz, 1H), 7.19 (dd, J=2.1, 8.4 Hz, 1H), 7.10 (d, J=2.0 Hz, 1H), 6.99-6.84 (m, 3H), 5.86-5.77 (m, 1H), 5.76-5.66 (m, 1H), 4.26 (d, J=11.0 Hz, 1H), 4.23-4.05 (m, 5H), 3.86-3.68 (m, 4H), 3.25 (d, J=14.4 Hz, 1H), 3.04 (dd, J=8.9, 15.3 Hz, 1H), 2.86-2.68 (m, 2H), 2.50-1.36 (m, 14H). m/z (ESI, +ve ion) 601.2 (M+H)$^+$.

Example 446. (1S,3'R,6'R,7'S,8'E,12'S)-6-chloro-12'-(hydroxymethyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-12'-(hydroxymethyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

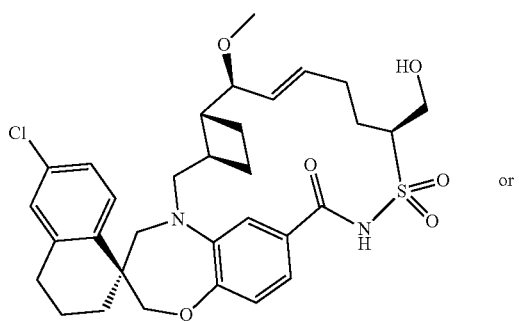

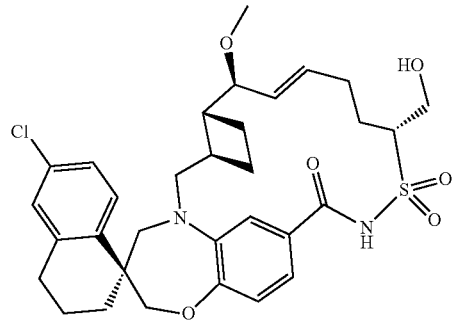

To a 5-mL round-bottomed flask were added sodium hydride, 60% dispersion in mineral oil (3.4 mg, 0.084 mmol) and (1S,3'R,6'R,7'S,8'E,12'S)-6-chloro-12'-(((dimethyl(2-methyl-2-propanyl)silyl)oxy)methyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,12'R)-6-chloro-12'-(((dimethyl(2-methyl-2-propanyl)silyl)oxy)methyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (20 mg, 0.028 mmol, Example 445, Step 3) in 2 mL of THF at 0° C. The reaction mixture was stirred at 0° C. for 30 min, and then MeI (3.50 µl, 0.056 mmol) was added. The reaction mixture was stirred at ambient temperature for 2 h. The reaction mixture was diluted with 1N HCl (5 mL), and extracted with EtOAc (2×10 mL). The organic extract was washed with saturated NaCl (10 mL) and dried over MgSO$_4$, filtered and concentrated in vacuo to give the crude material. The crude material was redissolved in 1 mL of THF and treated with tetrabutylammonium fluoride, 1.0 M solution in tetrahydrofuran (0.056 mL, 0.056 mmol) and the mixture was stirred overnight. The reaction mixture was concentrated, and the residue was purified by reversed phase preparatory HPLC (Gemini™ Prep C$_{18}$ 5 µm column; Phenomenex, Torrance, CA; gradient elution of 40% to 95% MeCN in water, where both solvents contain 0.1% TFA, 30 min method) to provide the title compound as the first eluting isomer. $^1$H NMR (500 MHz, CDCl$_3$) δ 8.05 (br. s., 1H), 7.70 (d, J=8.6 Hz, 1H), 7.19 (d, J=8.6 Hz, 1H), 7.10 (s, 1H), 6.96-6.80 (m, 3H), 5.84 (d, J=5.4 Hz, 1H), 5.56 (dd, J=9.0, 14.9 Hz, 1H), 4.38-4.27 (m, 2H), 4.24-4.16 (m, 1H), 4.14-4.03 (m, 2H), 3.82 (d, J=14.7 Hz, 1H), 3.72 (d, J=13.9 Hz, 1H), 3.64 (d, J=6.1 Hz, 1H), 3.24 (s, 4H), 3.06-2.94 (m, 1H), 2.87-2.67 (m, 2H), 2.56-1.21 (m, 15H). m/z (ESI, +ve ion) 615.2 (M+H)$^+$.

Example 447. (1S,3'R,6'R,7'S,8'E,12'S)-6-chloro-7'-hydroxy-12'-((2-methoxyethoxy)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-7'-hydroxy-12'-((2-methoxyethoxy)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'S)-6-chloro-7'-hydroxy-12'-((2-methoxyethoxy)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'R)-6-chloro-7'-hydroxy-12'-((2-methoxyethoxy)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

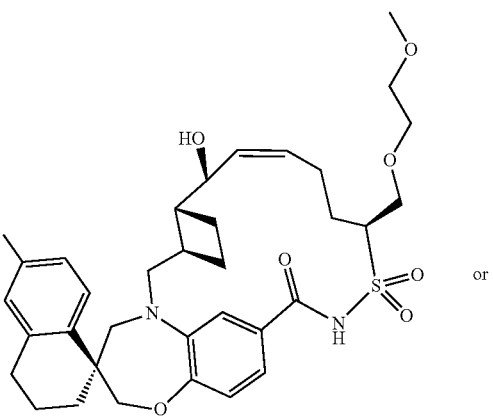

or

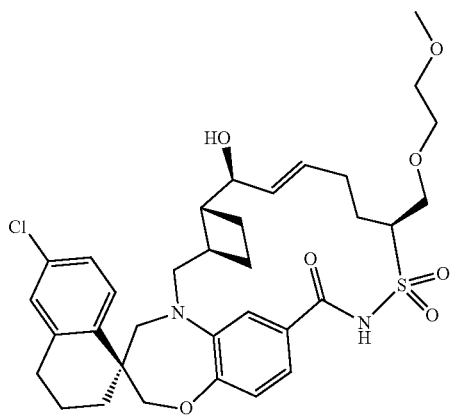

or

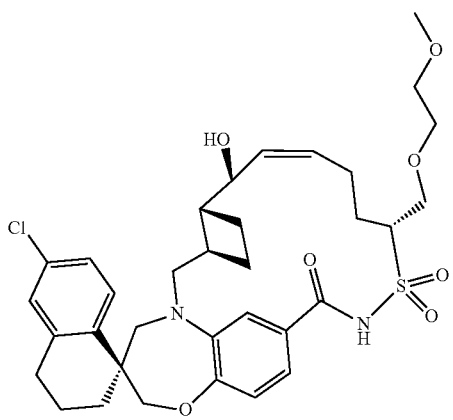

or

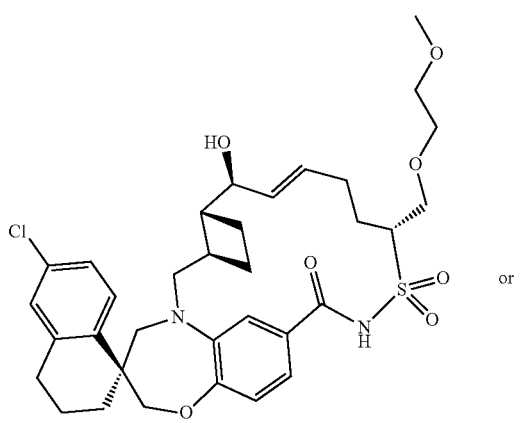

or

Step 1: (R)—N,N-bis(4-methoxybenzyl)-1-(2-methoxyethoxy)hex-5-ene-2-sulfonamide and (S)—N,N-bis(4-methoxybenzyl)-1-(2-methoxyethoxy)hex-5-ene-2-sulfonamide

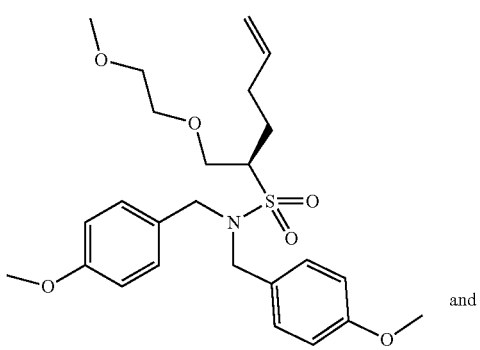

and

1001

-continued

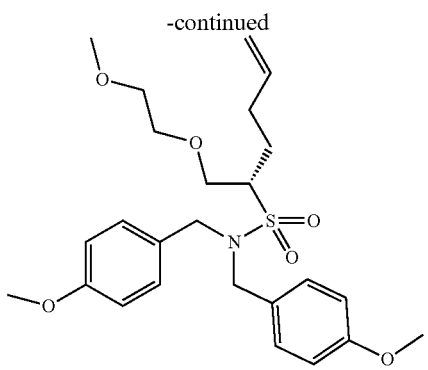

The title compound was prepared in an analogous manner to that described in Example 434, Step 3 using 2-methoxyethyl methanesulfonate. m/z (ESI, +ve ion) 500.2 (M+Na)⁺.

Step 2: (R)-1-(2-methoxyethoxy)hex-5-ene-2-sulfonamide and (S)-1-(2-methoxyethoxy)hex-5-ene-2-sulfonamide

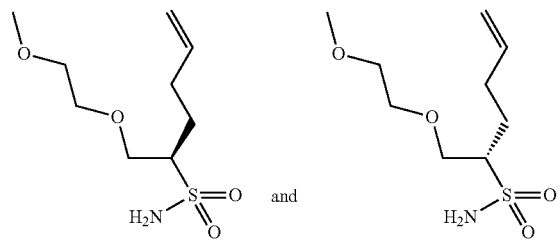

The title compound was prepared in an analogous manner to that described in Example 432, Step 3 using (R)—N,N-bis(4-methoxybenzyl)-1-(2-methoxy ethoxy)hex-5-ene-2-sulfonamide and (S)—N,N-bis(4-methoxybenzyl)-1-(2-methoxy ethoxy)hex-5-ene-2-sulfonamide. m/z (ESI, +ve ion) 238.2 (M+H)⁺.

1002

Step 3: (S)-6'-chloro-5-(((1R,2R)-2-((S,E)-1-hydroxyhex-2-en-1-yl)cyclobutyl)methyl)-N—(((S)-1-(2-methoxyethoxy)hex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N—(((R)-1-(2-methoxyethoxy)hex-5-en-2-yl)sulfonyl)-3',4,4',5-tetrahydro-2H,2'H-spiro[benzo[b][1,4]oxazepine-3,1'-naphthalene]-7-carboxamide

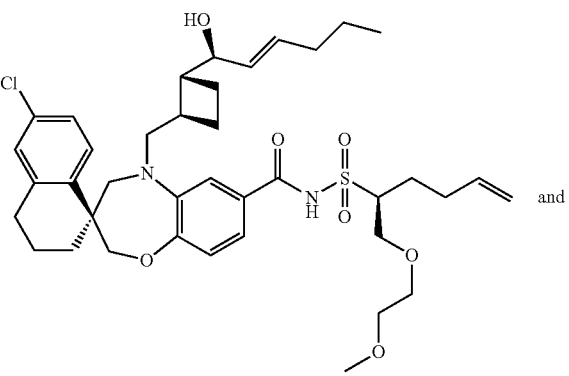

The title compound was prepared in an analogous manner to that described in Example 432, Step 4 using (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate, AA12A) and (R)-1-(2-methoxyethoxy)hex-5-ene-2-sulfonamide and (S)-1-(2-methoxyethoxy)hex-5-ene-2-sulfonamide. m/z (ESI, +ve ion) 729.3 (M+H)⁺.

Step 4: (1S,3'R,6'R,7'S,8'E,12'S)-6-chloro-7'-hydroxy-12'-((2-methoxyethoxy)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-7'-hydroxy-12'-((2-methoxyethoxy)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'S)-6-chloro-7'-hydroxy-12'-((2-methoxyethoxy)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'R)-6-chloro-7'-hydroxy-12'-((2-methoxyethoxy)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide The title compound was prepared in an analogous manner to that described in Example 432, Step 5 using (S)-6'-chloro-5-(((1R,2R)-2-((S,E)-1-hydroxyhex-2-en-1-yl)cyclobutyl)methyl)-N—(((S)-1-(2-methoxyethoxy)hex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N—(((R)-1-(2-methoxyethoxy)hex-5-en-2-yl)sulfonyl)-3',4,4',5-tetrahydro-2H,2'H-spiro[benzo[b][1,4]oxazepine-3,1'-naphthalene]-7-carboxamide, and isolated as the first eluting isomer from the reversed phase preparatory HPLC separation. $^1$H NMR (400 MHz, CDCl$_3$) δ 8.47 (br. s., 1H), 7.70 (d, J=8.6 Hz, 1H), 7.18 (dd, J=2.2, 8.5 Hz, 1H), 7.09 (d, J=2.2 Hz, 1H), 7.02-6.85 (m, 3H), 5.88-5.77 (m, 1H), 5.73-5.60 (m, 1H), 4.27-4.18 (m, 2H), 4.15-4.01 (m, 4H), 3.86-3.65 (m, 4H), 3.61-3.55 (m, 2H), 3.41 (s, 3H), 3.27 (d, J=14.5 Hz, 1H), 3.15-3.03 (m, 1H), 2.89-2.64 (m, 2H), 2.51-1.55 (m, 14H), 1.43 (t, J=12.0 Hz, 1H). m/z (ESI, +ve ion) 659.2 (M+H)$^+$.

Example 448. (1S,3'R,6'R,7'S,8'Z,12'R)-6-chloro-7'-hydroxy-12'-((2-methoxyethoxy)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'S)-6-chloro-7'-hydroxy-12'-((2-methoxyethoxy)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-7'-hydroxy-12'-((2-methoxyethoxy)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-6-chloro-7'-hydroxy-12'-((2-methoxyethoxy)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

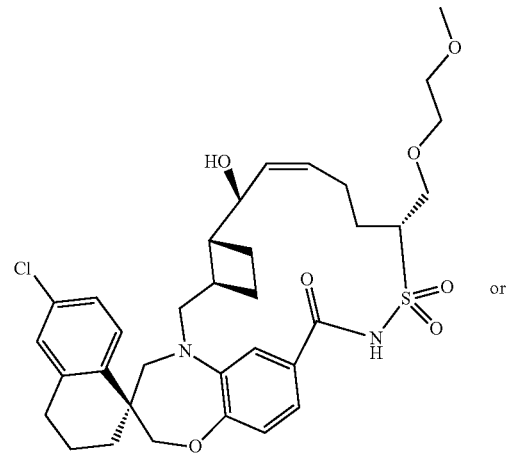

or

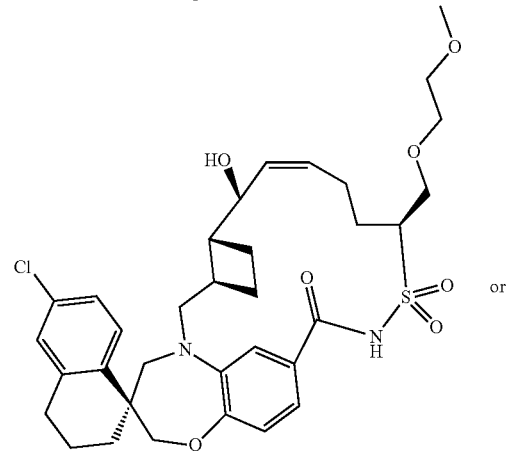

or

-continued

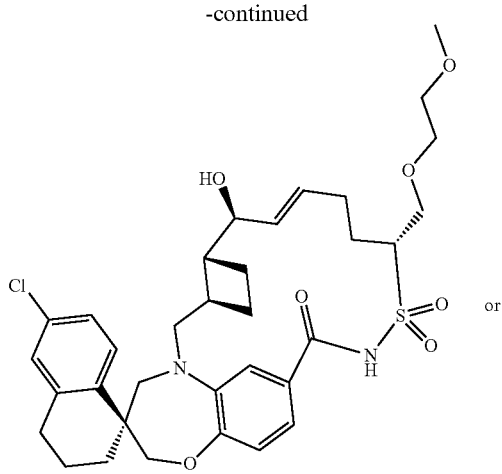

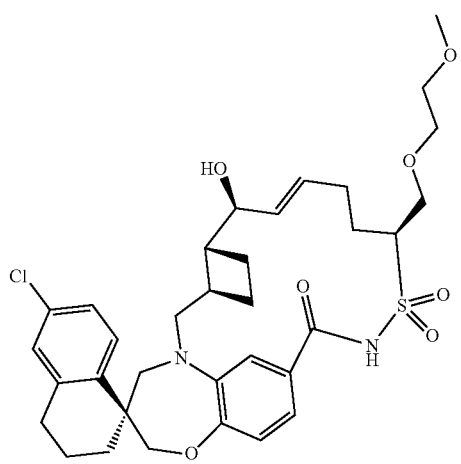 [SMILES: COCCOC[C@@H]1CC/C=C/[C@H](O)[C@@H]2CC[C@H]2CN2C[C@@]3(CCCc4cc(Cl)ccc43)COc3ccc(cc32)C(=O)NS1(=O)=O]

The title compound was obtained as the third eluting isomer from the reversed phase preparatory HPLC separation in Example 447, Step 4. ¹H NMR (400 MHz, CDCl₃) δ 7.72 (d, J=8.4 Hz, 1H), 7.32 (d, J=8.8 Hz, 1H), 7.18 (dd, J=2.0, 8.6 Hz, 1H), 7.09 (d, J=1.8 Hz, 1H), 7.01 (s, 1H), 6.96 (d, J=8.2 Hz, 1H), 5.66 (br. s., 1H), 5.56-5.41 (m, 1H), 4.67 (br. s., 1H), 4.16-4.04 (m, 3H), 3.97 (d, J=13.9 Hz, 3H), 3.79-3.53 (m, 5H), 3.38 (s, 3H), 3.26 (d, J=14.3 Hz, 1H), 3.11 (dd, J=10.0, 14.9 Hz, 1H), 2.90-2.65 (m, 3H), 2.43-1.18 (m, 14H). m/z (ESI, +ve ion) 659.2 (M+H)⁺.

Example 449. 4-(((1S,3'R,6'R,7'S,8'E,12'S)-6-chloro-7'-methoxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-12'-yl)carbonyl)-N,N-dimethyl-1-piperazinesulfonamide or 4-(((1S,3'R,6'R,7'S,8'E,12'R)-6-chloro-7'-methoxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-12'-yl)carbonyl)-N,N-dimethyl-1-piperazinesulfonamide

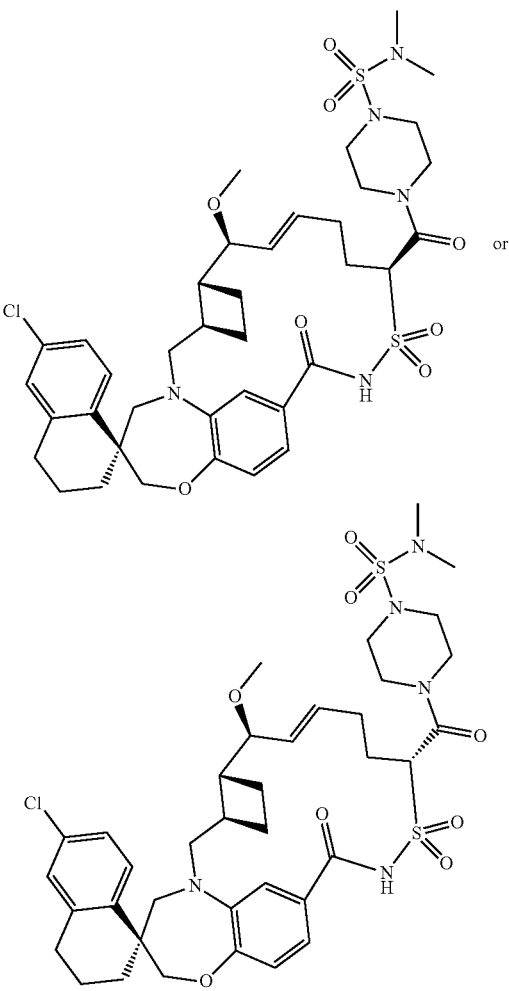

Step 1: N,N-dimethylpiperazine-1-sulfonamide hydrochloride

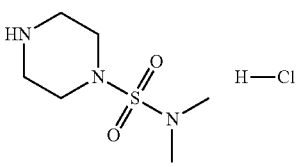

To a solution of tert-butyl 4-(chlorosulfonyl)piperazine-1-carboxylate (1.00 g, 3.51 mmol) in DCM (17.6 ml) were added triethylamine (0.977 ml, 7.02 mmol), 4-dimethylaminopyridine (0.215 g, 1.76 mmol) and dimethylamine, 2.0 M solution in tetrahydrofuran (3.51 ml, 7.02 mmol). The solution was stirred at room temperature overnight. The reaction mixture was diluted with 1N HCl (10 mL) and extracted with EtOAc (2×10 mL). The organic extract was washed with saturated NaCl (10 mL) and dried over MgSO$_4$, filtered and concentrated in vacuo. The crud material was dissolved in DCM (10 mL) and treated with trifluoroacetic acid (1.35 ml, 17.6 mmol). The mixture was stirred overnight, and concentrated. The residue was dissolved in 10 mL of 1N HCl and freeze to dry to give the title compound (0.806 g, 100%). m/z (ESI, +ve ion) 194.1 (M+H)$^+$.

Step 2: (R)-4-(2-(N,N-bis(4-methoxybenzyl)sulfamoyl)hex-5-enoyl)-N,N-dimethylpiperazine-1-sulfonamide and (S)-4-(2-(N,N-bis(4-methoxybenzyl)sulfamoyl)hex-5-enoyl)-N,N-dimethylpiperazine-1-sulfonamide

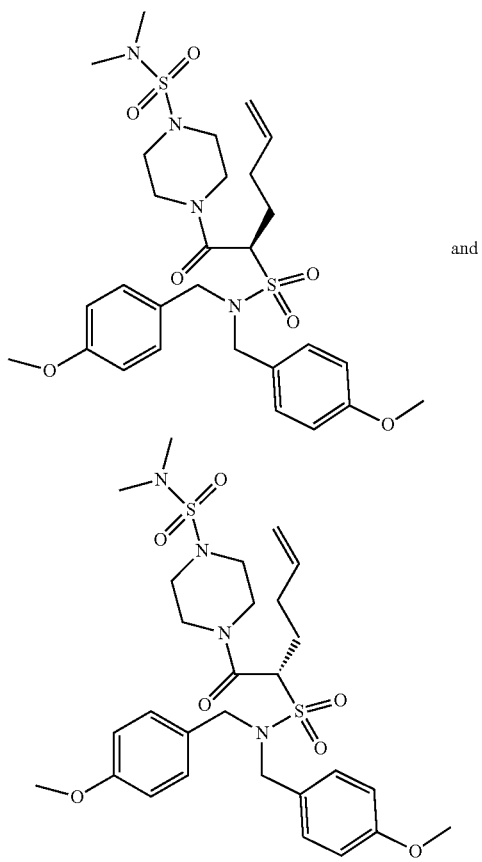

To a 250-mL round-bottomed flask were added (R)-2-(N,N-bis(4-methoxybenzyl)sulfamoyl)hex-5-enoic acid and (S)-2-(N,N-bis(4-methoxybenzyl)sulfamoyl)hex-5-enoic acid (0.650 g, 1.50 mmol, Example 436, Step 1). dipea (0.786 ml, 4.50 mmol), 2-(1h-benzotriazol-1-yl)-1,1,3,3-tetramethyluronium hexafluorophosphate (0.853 g, 2.25 mmol) and N,N-dimethylpiperazine-1-sulfonamide hydrochloride (0.344 g, 1.50 mmol) in DMF (10 ml). The mixture was stirred at ambient temperature overnight. The reaction mixture was diluted with 1N HCl (10 mL) and extracted with Et$_2$O (2×30 mL). The organic extract was washed with saturated NaCl (10 mL) and dried over MgSO$_4$, filtered and concentrated in vacuo to give the title compound (0.852 g, 93%). m/z (ESI, +ve ion) 631.2 (M+Na)$^+$.

Step 3: (R)—N,N-dimethyl-4-(2-sulfamoylhex-5-enoyl)piperazine-1-sulfonamide and (S)—N,N-dimethyl-4-(2-sulfamoylhex-5-enoyl)piperazine-1-sulfonamide

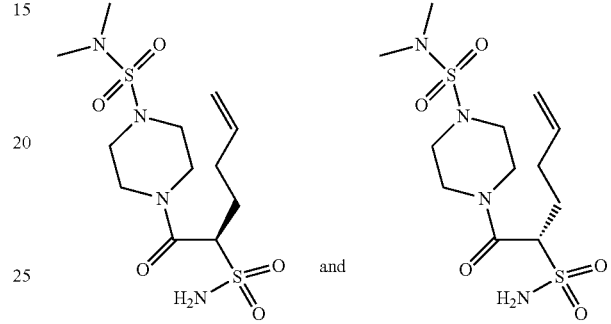

The title compound was prepared in an analogous manner to that described in Example 432, Step 3 using (R)-4-(2-(N,N-bis(4-methoxybenzyl)sulfamoyl)hex-5-enoyl)-N,N-dimethylpiperazine-1-sulfonamide and (S)-4-(2-(N,N-bis(4-methoxybenzyl)sulfamoyl)hex-5-enoyl)-N,N-dimethylpiperazine-1-sulfonamide. m/z (ESI, +ve ion) 391.1 (M+Na)$^+$.

Step 4: (S)-6'-chloro-N—(((S)-1-(4-(N,N-dimethylsulfamoyl)piperazin-1-yl)-1-oxohex-5-en-2-yl)sulfonyl)-5-(((1R,2R)-2-((S,E)-1-methoxypent-2-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N—(((R)-1-(4-(N,N-dimethylsulfamoyl)piperazin-1-yl)-1-oxohex-5-en-2-yl)sulfonyl)-5-(((1R,2R)-2-((S,E)-1-methoxypent-2-en-1-yl)cyclobutyl)methyl)-3',4,4',5-tetrahydro-2H,2'H-spiro[benzo[b][1,4]oxazepine-3,1'-naphthalene]-7-carboxamide

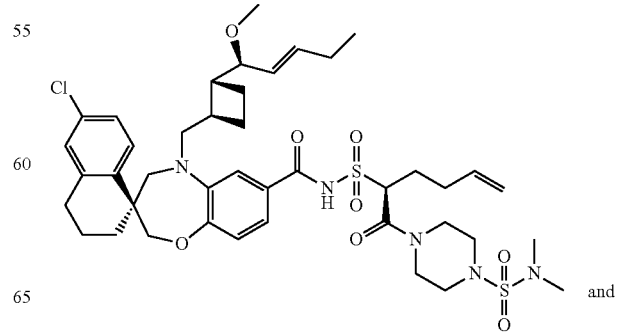

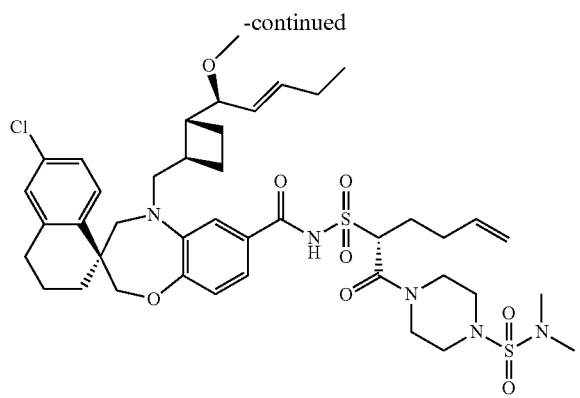

The title compound was prepared in an analogous manner to that described in Example 432, Step 4 using (S)-6'-chloro-5-(((1R,2R)-2-((S,E)-1-methoxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Example 724, Step 1) and (R)—N,N-dimethyl-4-(2-sulfamoylhex-5-enoyl)piperazine-1-sulfonamide and (S)—N,N-dimethyl-4-(2-sulfamoylhex-5-enoyl)piperazine-1-sulfonamide.

Step 5: 4-(((1S,3'R,6'R,7'S,8'E,12'S)-6-chloro-7'-methoxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)carbonyl)-N,N-dimethyl-1-piperazinesulfonamide or 4-(((1S,3'R,6'R,7'S,8'E,12'R)-6-chloro-7'-methoxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)carbonyl)-N,N-dimethyl-1-piperazinesulfonamide The title compound was prepared in an analogous manner to that described in Example 432, Step 5 using (S)-6'-chloro-N—(((S)-1-(4-(N,N-dimethylsulfamoyl)piperazin-1-yl)-1-oxohex-5-en-2-yl)sulfonyl)-5-(((1R,2R)-2-((S,E)-1-methoxypent-2-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N—(((R)-1-(4-(N,N-dimethylsulfamoyl)piperazin-1-yl)-1-oxohex-5-en-2-yl)sulfonyl)-5-(((1R,2R)-2-((S,E)-1-methoxypent-2-en-1-yl)cyclobutyl)methyl)-3',4,4',5-tetrahydro-2H,2'H-spiro[benzo[b][1,4]oxazepine-3,1'-naphthalene]-7-carboxamide, and isolated as the first eluting isomer from the reversed phase preparatory HPLC separation. $^1$H NMR (500 MHz, CD$_3$OD) δ 7.73 (d, J=8.6 Hz, 1H), 7.17 (dd, J=2.1, 8.4 Hz, 1H), 7.11 (s, 1H), 7.03-6.97 (m, 1H), 6.95-6.91 (m, 1H), 6.87 (s, 1H), 5.81-5.71 (m, 1H), 5.64 (dd, J=3.5, 9.7 Hz, 1H), 5.57 (dd, J=8.2, 15.3 Hz, 1H), 4.19 (d, J=13.9 Hz, 1H), 4.12-4.01 (m, 3H), 3.91-3.78 (m, 2H), 3.74 (dd, J=3.4, 7.8 Hz, 1H), 3.67 (d, J=14.2 Hz, 1H), 3.60-3.52 (m, 1H), 3.45-3.36 (m, 3H), 3.28 (s, 1H), 3.23 (s, 3H), 3.21-3.13 (m, 1H), 3.07 (dd, J=10.1, 15.3 Hz, 1H), 2.89-2.82 (m, 6H), 2.82-2.72 (m, 2H), 2.59-2.29 (m, 4H), 2.14-1.99 (m, 2H), 1.92 (dd, J=7.1, 13.4 Hz, 4H), 1.81-1.65 (m, 3H), 1.44 (t, J=12.2 Hz, 1H).

Example 450. (1S,3'R,6'S,8'E,12'S)-6-chloro-12'-(hydroxymethyl)-3,4-dihydro-2H,15'H-spiro[naphthalene-1,22'-[20]oxa[13]thia[1,14]diazatetracyclo[14.7.2.0$^{3,6}$.0$^{9,24}$]pentacosa[8,16,18,24]tetraen]-15'-one 13',13'-dioxide or (1S,3'R,6'S,8'Z,12'S)-6-chloro-12'-(hydroxymethyl)-3,4-dihydro-2H,15'H-spiro[naphthalene-1,22'-[20]oxa[13]thia[1,14]diazatetracyclo[14.7.2.0$^{3,6}$.0$^{9,24}$]pentacosa [8,16,18,24]tetraen]-15'-one 13',13'-dioxide or (1S,3'R,6'S,8'E,12'R)-6-chloro-12'-(hydroxymethyl)-3,4-dihydro-2H,15'H-spiro[naphthalene-1,22'-[20]oxa[13]thia[1,14]diazatetracyclo[14.7.2.0$^{3,6}$.0$^{9,24}$]pentacosa[8,16,18,24]tetraen]-15'-one 13',13'-dioxide or (1S,3'R,6'S,8'Z,12'R)-6-chloro-12'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

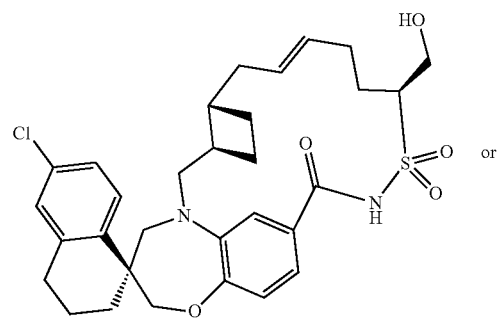

or


or


or

-continued

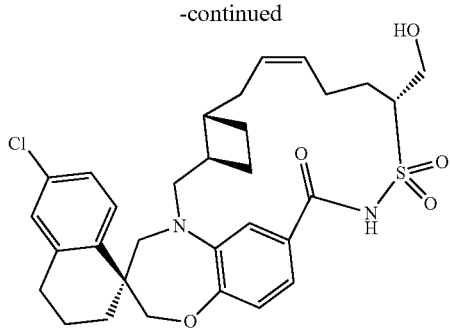

Step 1: (S)-tert-butyl 6'-chloro-5-(((1R,2R)-2-((E)-2-methoxyvinyl)cyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1R,2R)-2-((Z)-2-methoxyvinyl)cyclobutyl)methyl)-3',4,4',5-tetrahydro-2H,2'H-spiro[benzo[b][1,4]oxazepine-3,1'-naphthalene]-7-carboxylate

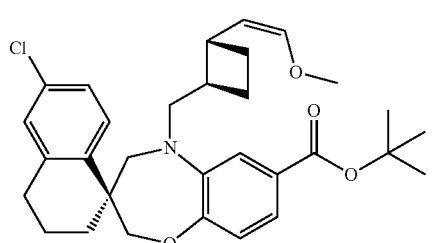

and

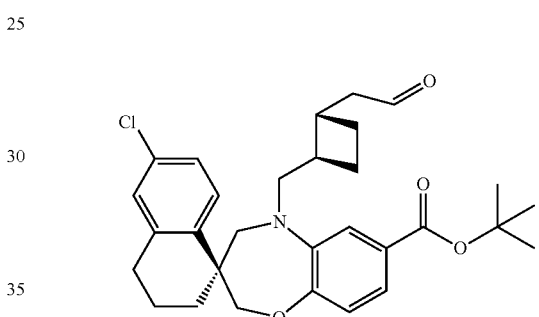

A solution of (methoxymethyl)triphenylphosphonium chloride (1.74 g, 5.08 mmol) in THF (10 mL) was cooled to −78° C. The 2.5 M butyllithium in THF solution (1.36 ml, 3.40 mmol) was added dropwise and the mixture was stirred at −78° C. for 30 min, and then (S)-tert-butyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (0.420 g, 0.847 mmol, Intermediate, Intermediate AA11A, Step 20B) in THF (5 ml) was added slowly. The resulting mixture was stirred at −78° C. overnight. Water (10 mL) was added to quench the reaction. The mixture was extracted with diethyl ether (2×30 mL). The combined organics were concentrated. The crude material was purified by chromatography through a Redi-Sep prepacked silica gel column (12 g), eluting with a gradient of 0% to 30% EtOAc in hexane, to provide the title compound as a white powder. m/z (ESI, +ve ion) 524.2 (M+H)$^+$.

Step 2: (S)-tert-butyl 6'-chloro-5-(((1R,2S)-2-(2-oxoethyl)cyclobutyl)methyl)-3',4,4',5-tetrahydro-2H,2'H-spiro[benzo[b][1,4]oxazepine-3,1'-naphthalene]-7-carboxylate To a 25-mL round-bottomed flask were added (S)-tert-butyl 6'-chloro-5-(((1R,2R)-2-((E)-2-methoxyvinyl)cyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1R,2R)-2-((Z)-2-methoxyvinyl)cyclobutyl)methyl)-3',4,4',5-tetrahydro-2H,2'H-spiro[benzo[b][1,4]oxazepine-3,1'-naphthalene]-7-carboxylate (180 mg, 0.343 mmol), 1 N HCl (0.515 ml, 0.515 mmol) in 1,4-dioxane (4 ml) and sodium iodide (257 mg, 1.72 mmol). The reaction mixture was stirred at ambient temperature overnight. The reaction mixture was treated with sodium thiosulfate solution until mixture became clear. The reaction mixture was diluted with water (10 mL) and extracted with Et$_2$O (2×10 mL). The organic extract was washed with saturated NaCl (10 mL) and dried over MgSO$_4$, filtered and concentrated in vacuo to give the crude material. The crude material was purified by chromatography through a Redi-Sep pre-packed silica gel column (40 g), eluting with a gradient of 0% to 40% EtOAc in hexane, to provide the title compound (170 mg, 97% yield) as a colorless oil. m/z (ESI, +ve ion) 501.2 (M+H)$^+$.

Step 3: (S)-5-(((1R,2S)-2-allylcyclobutyl)methyl)-6'-chloro-3',4,4',5-tetrahydro-2H,2'H-spiro[benzo[b][1,4]oxazepine-3,1'-naphthalene]-7-carboxylic acid

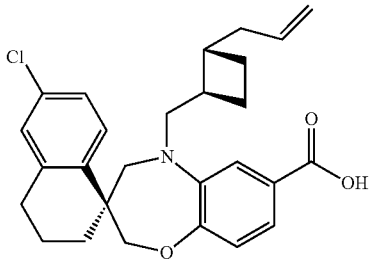 [SMILES: C=CC[C@@H]1CC[C@H]1CN1C[C@@]2(CCCc3cc(Cl)ccc32)COc2ccc(C(=O)O)cc21]

To a solution of methyl phenylphosphonium bromide (490 mg, 1.37 mmol) in THF (3 ml) was added potassium tert-butoxide, 1.0 M solution in THF (0.823 ml, 0.823 mmol) and stirred at ambient temperature 30 min, and the mixture was cooled to 0° C. To this solution was added (S)-tert-butyl 6'-chloro-5-(((1R,2S)-2-(2-oxoethyl)cyclobutyl)methyl)-3',4,4',5-tetrahydro-2H,2'H-spiro[benzo[b][1,4]oxazepine-3,1'-naphthalene]-7-carboxylate (140 mg, 0.274 mmol) in THF (1.5 ml) slowly. The resulting mixture was stirred at 0° C. for 30 min and then at ambient temperature overnight. The reaction mixture was diluted with 1N HCl (10 mL) and extracted with Et₂O (2×30 mL). The organic extract was washed with saturated NaCl (20 mL) and dried over MgSO₄, filtered and concentrated in vacuo. The residue was dissolved in 5 mL of DCM and treated with 2 mL of TFA. The mixture was stirred at ambient temperature for 2h, and then concentrated. The crude material was purified by chromatography through a Redi-Sep pre-packed silica gel column (12 g), eluting with a gradient of 0% to 50% EtOAc in hexane, to provide the title compound (100 mg, 81%) as a clear oil. m/z (ESI, +ve ion) 452.2 (M+H)⁺.

Step 4: (S)-5-(((1R,2S)-2-allylcyclobutyl)methyl)-6'-chloro-N—(((S)-1-hydroxyhex-5-en-2-yl)sulfonyl)-3',4,4',5-tetrahydro-2H,2'H-spiro[benzo[b][1,4]oxazepine-3,1'-naphthalene]-7-carboxamide and (S)-5-(((1R,2S)-2-allylcyclobutyl)methyl)-6'-chloro-N—(((R)-1-hydroxyhex-5-en-2-yl)sulfonyl)-3',4,4',5-tetrahydro-2H,2'H-spiro[benzo[b][1,4]oxazepine-3,1'-naphthalene]-7-carboxamide

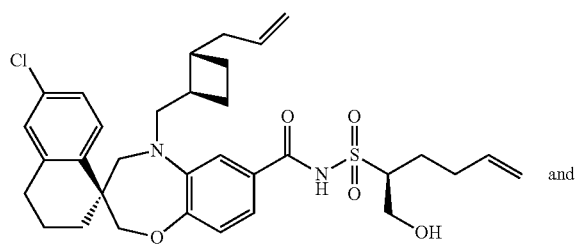

and

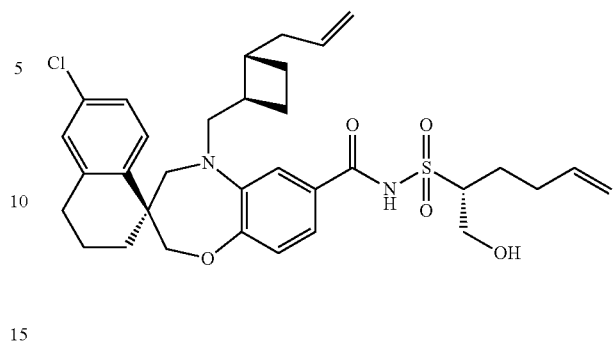

The title compound was prepared in an analogous manner to that described in Example 432, Step 4 using (S)-5-(((1R,2S)-2-allylcyclobutyl)methyl)-6'-chloro-3',4,4',5-tetrahydro-2H,2'H-spiro[benzo[b][1,4]oxazepine-3,1'-naphthalene]-7-carboxylic acid and (S)-1-((tert-butyldimethylsilyl)oxy)hex-5-ene-2-sulfonamide and (R)-1-((tert-butyldimethylsilyl)oxy)hex-5-ene-2-sulfonamide (Example 445, Step 2), and then the crude material was treated with tetrabutylammonium fluoride in THF. m/z (ESI, +ve ion) 613.2 (M+H)⁺.

Step 5: (1S,3'R,6'S,8'E,12'S)-6-chloro-12'-(hydroxymethyl)-3,4-dihydro-2H,15'H-spiro[naphthalene-1,22'-[20]oxa[13]thia[1,14]diazatetracyclo[14.7.2.0³,⁶.0⁹,²⁴]pentacosa[8,16,18,24]tetraen]-15'-one 13',13'-dioxide or (1S,3'R,6'S,8'Z,12'S)-6-chloro-12'-(hydroxymethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'S,8'E,12'R)-6-chloro-12'-(hydroxymethyl)-3,4-dihydro-2H,15'H-spiro[naphthalene-1,22'-[20]oxa[13]thia[1,14]diazatetracyclo[14.7.2.0³,⁶.0⁹,²⁴]pentacosa[8,16,18,24]tetraen]-15'-one 13',13'-dioxide or (1S,3'R,6'S,8'Z,12'R)-6-chloro-12'-(hydroxymethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide The title compound was prepared in an analogous manner to that described in Example 432, Step 5 using (S)-5-(((1R,2S)-2-allylcyclobutyl)methyl)-6'-chloro-N—(((S)-1-hydroxyhex-5-en-2-yl)sulfonyl)-3',4,4',5-tetrahydro-2H,2'H-spiro[benzo[b][1,4]oxazepine-3,1'-naphthalene]-7-carboxamide and (S)-5-(((1R,2S)-2-allylcyclobutyl)methyl)-6'-chloro-N—(((R)-1-hydroxyhex-5-en-2-yl)sulfonyl)-3',4,4',5-tetrahydro-2H,2'H-spiro[benzo[b][1,4]oxazepine-3,r-naphthalene]-7-carboxamide, and isolated as the first eluting isomer from the reversed phase preparatory HPLC separation. ¹H NMR (500 MHz, CDCl₃) δ 8.12 (s, 1H), 7.73 (d, J=8.6 Hz, 1H), 7.29 (d, J=2.0 Hz, 1H), 7.20 (dd, J=2.2, 8.3 Hz, 1H), 7.09 (d, J=2.2 Hz, 1H), 6.96-6.90 (m, 1H), 6.89-6.85 (m, 1H), 5.45 (td, J=6.9, 14.2 Hz, 1H), 5.27-5.13 (m, 1H), 4.24-4.05 (m, 6H), 3.81 (dd, J=6.4, 15.4 Hz, 1H), 3.72 (d, J=14.2 Hz, 1H), 3.22 (d, J=14.4 Hz, 1H), 2.95 (dd, 15.4 Hz, 1H), 2.84-2.69 (m, 2H), 2.44-0.65 (m, 16H). m/z (ESI, +ve ion) 585.2 (M+H)⁺.

Example 451. (1S,3'R,6'S,8'Z,12'R)-6-chloro-12'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'S,8'E,12'S)-6-chloro-12'-(hydroxymethyl)-3,4-dihydro-2H,15'H-spiro[naphthalene-1,22'-[20]oxa[13]thia[1,14]diazatetracyclo[14.7.2.0$^{3,6}$.0$^{9,24}$]pentacosa[8,16,18,24]tetraen]-15'-one 13',13'-dioxide or (1S,3'R,6'S,8'Z,12'S)-6-chloro-12'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'S,8'E,12'R)-6-chloro-12'-(hydroxymethyl)-3,4-dihydro-2H,15'H-spiro[naphthalene-1,22'-[20]oxa[13]thia[1,14]diazatetracyclo[14.7.2.0$^{3,6}$.0$^{9,24}$]pentacosa[8,16,18,24]tetraen]-15'-one 13',13'-dioxide

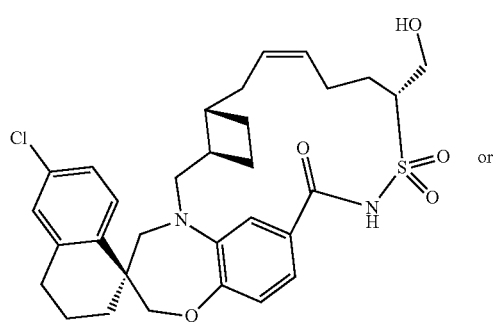 or

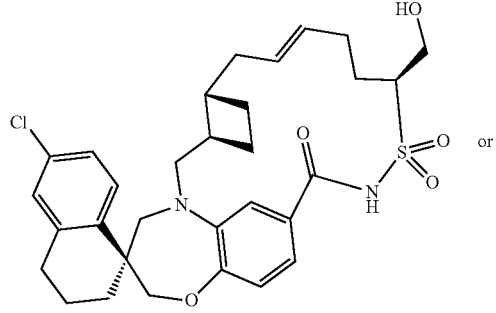 or

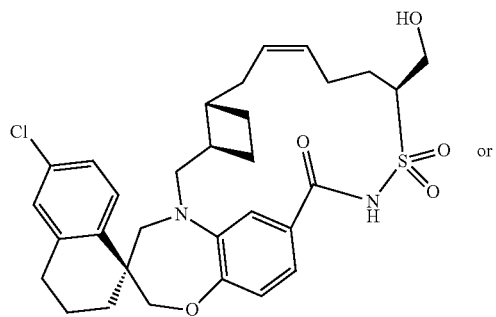 or

-continued

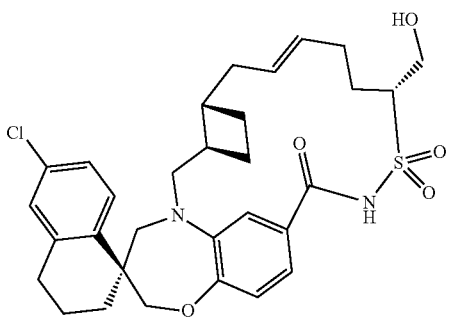

The title compound was obtained as the second eluting isomer from the reversed phase preparatory HPLC separation in Example 450, Step 5. $^1$H NMR (400 MHz, CDCl$_3$) δ 8.31 (br. s., 1H), 7.71 (d, J=8.4 Hz, 1H), 7.23-7.15 (m, 2H), 7.09 (d, J=2.2 Hz, 1H), 6.98 (d, J=8.2 Hz, 1H), 6.70 (s, 1H), 5.48 (br. s., 2H), 4.20-4.02 (m, 4H), 3.86 (dd, J=4.5, 8.2 Hz, 1H), 3.78-3.66 (m, 2H), 3.30 (d, J=14.5 Hz, 1H), 3.10 (dd, J=8.0, 15.5 Hz, 1H), 2.87-2.69 (m, 2H), 2.60-2.46 (m, 1H), 2.39-1.56 (m, 15H), 1.44 (t, J=12.3 Hz, 1H). m/z (ESI, +ve ion) 585.2 (M+H)$^+$.

Example 452. (1S,3'R,6'R,7'S,8'E,12'S)-6-chloro-7'-methoxy-N,N-dimethyl-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraene]-12'-carboxamide 13',13'-dioxide or (1S,3'R,6'R,7'S,8'E,12'R)-6-chloro-7'-methoxy-N,N-dimethyl-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraene]-12'-carboxamide 13',13'-dioxide

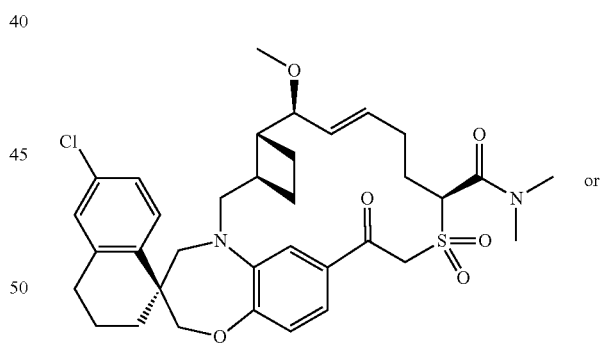 or

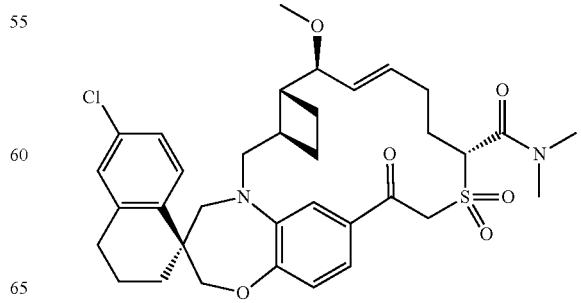

Step 1: (S)-6'-chloro-5-(((1R,2R)-2-((S,E)-1-hydroxy-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic acid

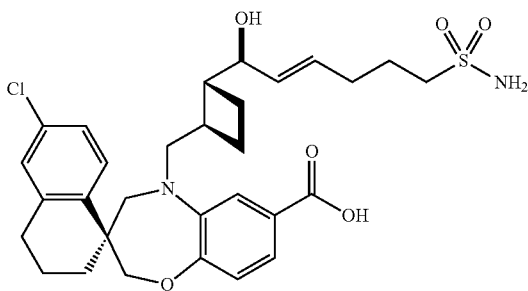

To a 100 mL flask was added (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A; 500 mg, 0.980 mmol), pent-4-ene-1-sulfonamide (Intermediate EE19; 878 mg, 5.88 mmol), and DCE (14 mL). The solution was sparged with argon for 15 min at which time Hoveyda-Grubbs II (61 mg, 0.098 mmol) was added as a 0.2 mL solution in DCE at rt. The mixture was stirred at rt and sparged with argon (the vial was vented) for 2 h. The reaction mixture was then bubbled with air for 5 minutes and filtered to separate the insoluble sulfonamide homodimer. The crude product was purified on a Combiflash® (24 g gold SiO$_2$ column), eluting with 50%-90% EtOAc in heptanes+0.2% AcOH to give (S)-6'-chloro-5-(((1R,2R)-2-((S,E)-1-hydroxy-6-sulfamoylhex-2-en-1-yl)cyclobutyl)methyl)-3',4,4',5-tetrahydro-2h,2'h-spiro[benzo[b][1,4]oxazepine-3,1'-naphthalene]-7-carboxylic acid (439 mg, 0.745 mmol, 76% yield) as a white solid.

Step 2: (1S,3'R,6'R,7'S,8'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

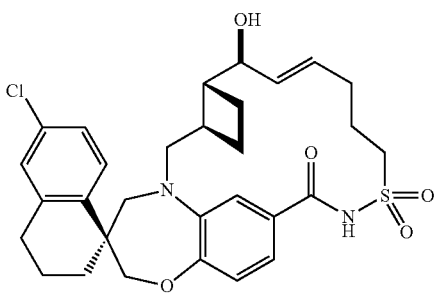

To a 1 L flask containing (S)-6'-chloro-5-(((1R,2R)-2-((S,E)-1-hydroxy-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic acid (from Step 1, 449 mg, 0.745 mmol), which was previously dried by azeotroping twice with 10 mL of toluene, was added N,N-dimethylpyridin-4-amine (155 mg, 1.27 mmol) and 400 mL of DCM. The reaction mixture was cooled to 0° C. at which time N-(3-dimethylaminopropyl)-N'-ethylcarbodiimide hydrochloride (286 mg, 1.490 mmol) was slowly added. The reaction was then stirred at rt for 18 h. The mixture was quenched with 200 mL of 1N HCl and extracted with 600 mL of EtOAc. The organic layer was dried over anhydrous Na$_2$SO$_4$, filtered, and concentrated by rotary evaporation. The crude product was purified on a Combiflash® (24 g gold SiO$_2$ column), eluting with 30%-70% EtOAc in heptanes, to give the title compound as a white solid. $^1$H NMR (500 MHz, CD$_3$OD) δ 7.75 (d, J=8.3 Hz, 1H), 7.20 (dd, J=2.9, 7.6 Hz, 1H), 7.12 (d, J=3.7 Hz, 1H), 7.00 (dd, J=1.7, 8.8 Hz, 1H), 6.94 (d, J=8.3 Hz, 1H), 6.88 (d, J=2.2 Hz, 1H), 5.95-5.86 (m, 1H), 5.70 (dd, J=8.8, 15.9 Hz, 1H), 4.25-4.19 (m, 1H), 4.22 (dd, J=4.4, 8.6 Hz, 1H), 4.14-4.06 (m, 3H), 4.14-4.05 (m, 3H), 3.84 (d, J=15.2 Hz, 1H), 3.68 (d, J=15.2 Hz, 1H), 3.09 (dd, J=8.3, 15.9 Hz, 1H), 2.87-2.74 (m, 2H), 2.45-2.30 (m, 3H), 2.14-1.88 (m, 5H), 1.86-1.69 (m, 4H). m/z (ESI, +ve ion) 571.2 (M+H)$^+$.

Step 3: (1S,3'R,6'R,7'S,8'E)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide To a 100 mL flask was added (1S,3'R,6'R,7'S,8'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (from Step 2, 138 mg, 0.242 mmol), THF (10 mL), and sodium hydride (29.0 mg, 1.208 mmol). The reaction was stirred at rt for 15 min at which time MeI (0.092 mL, 1.480 mmol) was added. The reaction was stirred at rt for 2 h at which time additional sodium hydride (58.0 mg, 2.42 mmol) and MeI (0.092 mL, 1.480 mmol) were added and the reaction was stirred at rt for an additional 16 h. The reaction was quenched with 100 mL of satd NH$_4$Cl and extracted with 400 mL of EtOAc. The organic layer was dried over Na$_2$SO$_4$, filtered, and the solvent was removed by rotary evaporation. The crude product was purified on a Combiflash® (12 g gold SiO$_2$ column), eluting with 10% to 50% EtOAc in heptanes, to give (1S,3'R,6'R,7'S,8'E)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (120 mg, 0.205 mmol, 85% yield) as an off white solid. $^1$H NMR (400 MHz, CDCl$_3$) δ 8.02 (s, 1H), 7.70 (d, J=8.6 Hz, 1H), 7.19 (dd, J=2.2, 8.5 Hz, 1H), 7.10 (d, J=2.2 Hz, 1H), 6.97-6.87 (m, 2H), 6.84 (d, J=1.6 Hz, 1H), 5.88 (ddd, J=5.2, 8.1, 15.1 Hz, 1H), 5.53 (dd, J=8.7, 15.4 Hz, 1H), 4.30 (ddd, J=4.8, 9.8, 15.0 Hz, 1H), 4.15-3.98 (m, 2H), 3.84-3.69 (m, 2H), 3.67 (dd, J=3.8, 8.7 Hz, 1H), 3.36-3.21 (m, 2H), 3.25 (s, 3H), 3.01 (dd, J=10.3, 15.2 Hz, 1H), 2.87-2.64 (m, 2H), 2.52-2.29 (m, 3H), 2.25-1.91 (m, 5H), 1.88-1.75 (m, 3H), 1.71-1.60 (m, 2H), 1.41 (t, J=12.4 Hz, 1H). m/z (ESI, +ve ion) 585.0 (M+H)$^+$.

Step 4: (1S,3'R,6'R,7'S,8'E,12'S)-6-chloro-7'-methoxy-N,N-dimethyl-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraene]-12'-carboxamide 13',13'-dioxide or (1S,3'R,6'R,7'S,8'E,12'R)-6-chloro-7'-methoxy-N,N-dimethyl-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraene]-12'-carboxamide 13',13'-dioxide To a solution of diisopropylamine (96 µL, 0.68 mmol) in THF (2 mL) at −78° C. under argon was added butyllithium solution, 2.5 M in hexanes (273 µL, 0.684 mmol) dropwise and the resulting mixture stirred at −78° C. for 10 min, at 0° C. for 30 min then recooled to −78° C. This solution (0.55 M; 0.15 mL 3 eq.) was then added to a solution of (1S,3'R,6'R,7'S,8'E)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (from Step 3, 10 mg, 0.017 mmol) in 0.5 mL THF at −78° C. under argon. The mixture was stirred at −78° for 30 min, and (dimethylamino)carbonyl chloride (16 µL, 0.17 mmol) was added. The resulting mixture was stirred at −78° C. for 20 min. The reaction was quenched with 2 N HCl solution and mixture concentrated. The crude product was purified by reversed phase preparatory HPLC (Gemini™ Prep C$_{18}$ 5 µm column; Phenomenex, Torrance, CA; gradient elution of 40% to 95% MeCN in water, where both solvents contain 0.1% TFA, 30 min method) to provide the title compounds as the first eluting isomer. $^1$H NMR (400 MHz, CDCl$_3$) δ 8.33 (br. s., 1H), 7.70 (d, J=8.4 Hz, 1H), 7.19 (dd, J=2.2, 8.5 Hz, 1H), 7.10 (d, J=2.2 Hz, 1H), 6.98-6.86 (m, 2H), 6.82 (s, 1H), 5.88-5.71 (m, 1H), 5.65 (dd, J=2.9, 10.4 Hz, 1H), 5.56 (dd, J=8.5, 15.2 Hz, 1H), 4.17-4.03 (m, 2H), 3.82 (d, J=14.7 Hz, 1H), 3.76-3.61 (m, 2H), 3.37 (s, 3H), 3.35-3.29 (m, 1H), 3.25 (s, 3H), 3.24-3.19 (m, 1H), 3.12 (s, 3H), 3.11-3.06 (m, 1H), 3.00 (dd, J=10.5, 15.2 Hz, 1H), 2.85-2.68 (m, 3H), 2.54-1.55 (m, 10H), 1.40 (t, J=12.3 Hz, 1H). m/z (ESI, +ve ion) 656.1 (M+H)$^+$.

Example 453. (1S,3'R,6'R,7'S,8'E,12'R)-6-chloro-7'-methoxy-N,N-dimethyl-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraene]-12'-carboxamide 13',13'-dioxide or (1S,3'R,6'R,7'S,8'E,12'S)-6-chloro-7'-methoxy-N,N-dimethyl-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraene]-12'-carboxamide 13',13'-dioxide

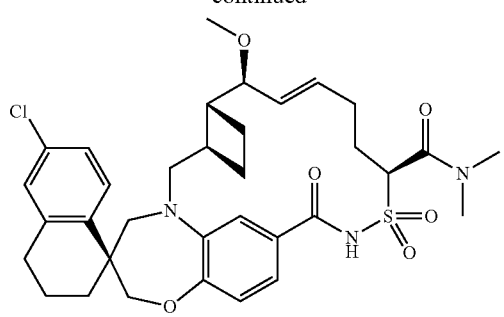

-continued

The title compound was obtained as the second eluting isomer from the reversed phase preparatory HPLC separation in Example 452, Step 4. $^1$H NMR (400 MHz, CDCl$_3$) δ 8.52 (br. s., 1H), 7.65 (d, J=8.4 Hz, 1H), 7.43 (br. s., 1H), 7.16 (dd, J=2.2, 8.5 Hz, 1H), 7.10 (d, J=2.2 Hz, 1H), 7.03-6.96 (m, 1H), 6.94-6.90 (m, 1H), 5.71 (td, J=5.3, 15.6 Hz, 1H), 5.37-5.16 (m, 2H), 4.28-4.07 (m, 2H), 3.77-3.61 (m, 2H), 3.51-3.19 (m, 9H), 3.10 (s, 3H), 2.76 (br. s., 2H), 2.67-2.54 (m, 1H), 2.51-1.48 (m, 13H). m/z (ESI, +ve ion) 656.1 (M+H)$^+$.

Example 454. (1S,3'R,6'R,7'S,8'E,11'S,12'R)-6-chloro-7'-hydroxy-11'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-7'-hydroxy-11'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-7'-hydroxy-11'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

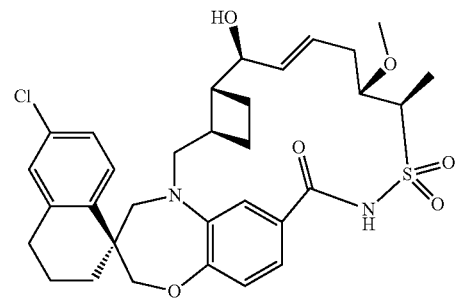

or

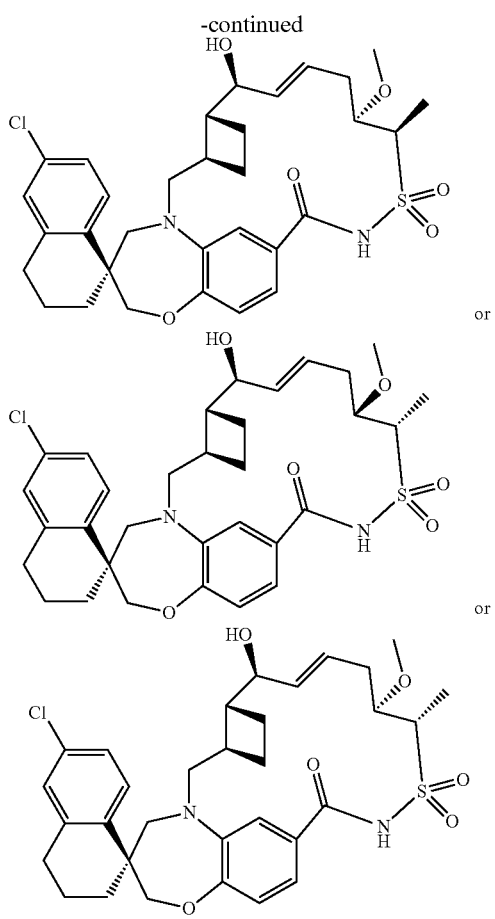

or

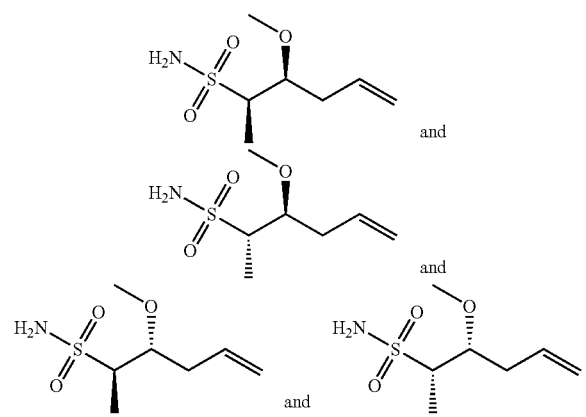

Step 1: (2R,3S)-3-methoxyhex-5-ene-2-sulfonamide and (2S,3S)-3-methoxyhex-5-ene-2-sulfonamide and (2R,3R)-3-methoxyhex-5-ene-2-sulfonamide and (2S,3R)-3-methoxyhex-5-ene-2-sulfonamide To a 25-mL round-bottomed flask were added iodomethane (0.477 mL, 7.63 mmol) and (2R,3S)-3-hydroxy-N,N-bis(4-methoxybenzyl)hex-5-ene-2-sulfonamide and (2S,3S)-3-hydroxy-N,N-bis(4-methoxybenzyl)hex-5-ene-2-sulfonamide and (2R,3R)-3-hydroxy-N,N-bis(4-methoxybenzyl)hex-5-ene-2-sulfonamide and (2S,3R)-3-hydroxy-N,N-bis(4-methoxybenzyl)hex-5-ene-2-sulfonamide (400 mg, 0.953 mmol, Example 714, Step 4) in THF (5 mL), and then sodium hydride, 60% dispersion in mineral oil (114 mg, 2.86 mmol). The resulting mixture was stirred at ambient temperature for 2 h. The reaction mixture was diluted with 1N HCl (5 mL) and extracted with EtOAc (2×10 mL). The organic extract was washed with saturated NaCl and dried over MgSO$_4$, filtered and concentrated in vacuo to give the crude material. The crude material was dissolved in 3 mL of DCM and treated with 3 mL of TFA. The mixture was stirred overnight, and concentrated. The crude material was purified by chromatography through a Redi-Sep pre-packed silica gel column (40 g), eluting with a gradient of 0% to 60% EtOAc in hexane, to provide the title compound. m/z (ESI, +ve ion) 194.2 (M+H)$^+$.

Step 2: (S)-6'-chloro-5-(((1R,2R)-2-((S,E)-1-hydroxyhex-2-en-1-yl)cyclobutyl)methyl)-N-(((2R,3S)-3-methoxyhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N-(((2S,3S)-3-methoxyhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N-(((2R,3R)-3-methoxyhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N-(((2S,3R)-3-methoxyhex-5-en-2-yl)sulfonyl)-3',4,4',5-tetrahydro-2H,2'H-spiro[benzo[b][1,4]oxazepine-3,1'-naphthalene]-7-carboxamide

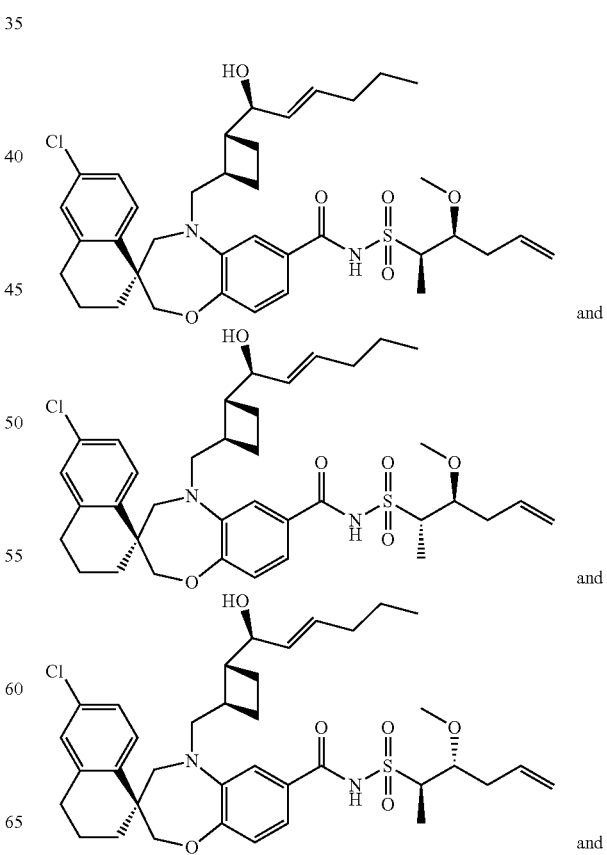

and

1023

-continued

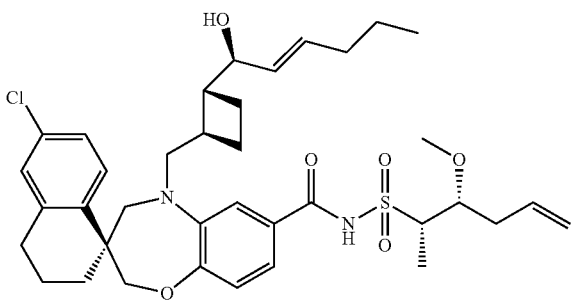

The title compound was prepared in an analogous manner to that described in Example 432, Step 4 using (S)-6'-chloro-5-(((1R,2R)-2-((S,E)-1-hydroxyhex-2-en-1-yl)cyclobutyl)methyl)-3',4,4',5-tetrahydro-2H,2'H-spiro [benzo[b][1,4]oxazepine-3,1'-naphthalene]-7-carboxyc acid (Intermediate, AA12A) and (2R,3S)-3-methoxyhex-5-ene-2-sulfonamide and (2S,3S)-3-methoxyhex-5-ene-2-sulfonamide and (2R,3R)-3-methoxyhex-5-ene-2-sulfonamide and (2S,3R)-3-methoxyhex-5-ene-2-sulfonamide. m/z (ESI, +ve ion) 685.2 (M+H)+.

Step 3: (1S,3'R,6'R,7'S,8'E,11'S,12'R)-6-chloro-7'-hydroxy-11'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-7'-hydroxy-11'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-7'-hydroxy-11'-methoxy-12'-methyl-3,4-dihydro-2H,15'H-spiro [naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compound was prepared in an analogous manner to that described in Example 432, Step 5 using (S)-6'-chloro-5-(((1R,2R)-2-((S,E)-1-hydroxyhex-2-en-1-yl)cyclobutyl)methyl)-N-(((2R,3S)-3-methoxyhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N-(((2S,3S)-3-methoxyhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N-(((2R,3R)-3-methoxyhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N-

1024

(((2S,3R)-3-methoxyhex-5-en-2-yl)sulfonyl)-3',4,4',5-tetrahydro-2H,2'H-spiro[benzo[b][1,4]oxazepine-3,1'-naphthalene]-7-carboxamide, and isolated as the first eluting isomer from the reversed phase preparatory HPLC separation. $^1$H NMR (400 MHz, CDCl$_3$) δ 8.18 (s, 1H), 7.70 (d, J=8.6 Hz, 1H), 7.18 (dd, J=2.2, 8.5 Hz, 1H), 7.10 (d, J=2.2 Hz, 1H), 7.02-6.86 (m, 3H), 5.87-5.77 (m, 1H), 5.72-5.60 (m, 1H), 4.31-4.09 (m, 4H), 3.82 (d, J=15.5 Hz, 1H), 3.72 (d, J=14.5 Hz, 1H), 3.51 (d, J=10.2 Hz, 1H), 3.39 (s, 3H), 3.26 (d, J=14.3 Hz, 1H), 3.07 (br. s., 1H), 2.87-2.68 (m, 2H), 2.58-1.63 (m, 12H), 1.58 (d, J=7.2 Hz, 3H), 1.42 (t, J=12.2 Hz, 1H). m/z (ESI, +ve ion) 615.2 (M+H)+.

Example 455. (1S,3'R,6'R,7'S,8'E,11'S,12'S)-6-chloro-7'-hydroxy-12'-(methoxymethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

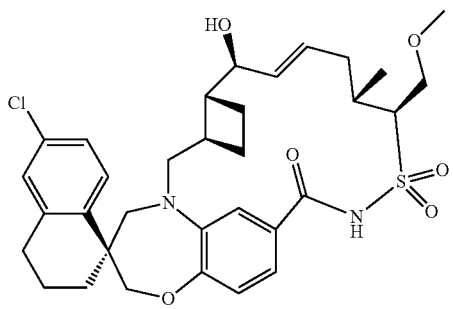 [SMILES: COC[C@@H]1[C@@H](C)C/C=C/[C@H](O)[C@@H]2CC[C@H]2CN2C[C@@]3(CCCc4cc(Cl)ccc43)COc3ccc(cc32)C(=O)NS1(=O)=O]

Step 1: (2S,3S)-1-methoxy-3-methylhex-5-ene-2-sulfonamide and (2R,3S)-1-methoxy-3-methylhex-5-ene-2-sulfonamide

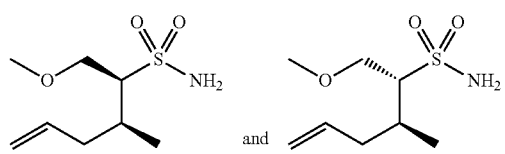

The title compound was prepared from (S)—N,N-bis(4-methoxybenzyl)-2-methylpent-4-ene-1-sulfonamide (Example 395, Step 3) by similar procedures described in Example 434, Steps 1-4. m/z (ESI, +ve ion) 208.2 (M+H)+.

Step 2: (S)-6'-chloro-5-(((1R,2R)-2-((S,E)-1-hydroxyhex-2-en-1-yl)cyclobutyl)methyl)-N-(((2S,3R)-1-methoxy-3-methylhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N-(((2R,3R)-1-methoxy-3-methylhex-5-en-2-yl)sulfonyl)-3',4,4',5-tetrahydro-2H,2'H-spiro[benzo[b][1,4]oxazepine-3,1'-naphthalene]-7-carboxamide

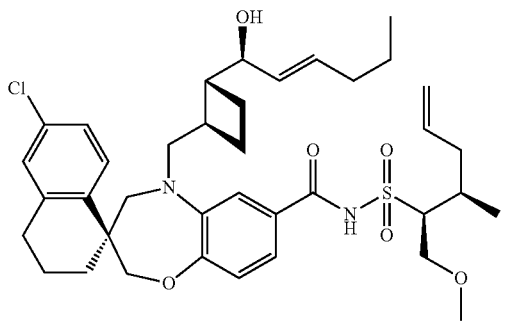

and

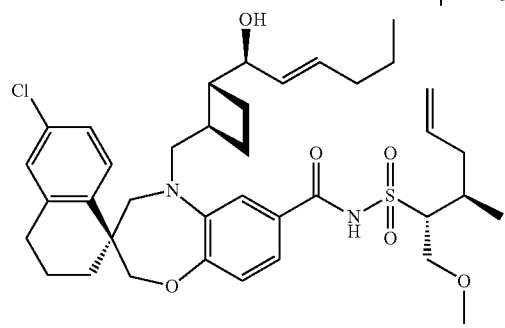

The title compound was prepared in an analogous manner to that described in Example 432, Step 4 using (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate, AA12A) and (2S,3S)-1-methoxy-3-methyl-hex-5-ene-2-sulfonamide and (2R,3S)-1-methoxy-3-methylhex-5-ene-2-sulfonamide. m/z (ESI, +ve ion) 699.2 (M+H)+.

Step 3: (1S,3'R,6'R,7'S,8'E,11'S,12'S)-6-chloro-7'-hydroxy-12'-(methoxymethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-дioxide The title compound was prepared in an analogous manner to that described in Example 432, Step 5 using (S)-6'-chloro-5-(((1R,2R)-2-((S,E)-1-hydroxyhex-2-en-1-yl)cyclobutyl)methyl)-N-(((2S,3R)-1-methoxy-3-methylhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N-(((2R,3R)-1-methoxy-3-methylhex-5-en-2-yl)sulfonyl)-3',4,4',5-tetrahydro-2H,2'H-spiro[benzo[b][1,4]oxazepine-3,1'-naphthalene]-7-carboxamide, and isolated as the first eluting isomer from the reversed phase preparatory HPLC separation. $^1$H NMR (400 MHz, CDCl$_3$) δ 8.15 (s, 1H), 7.69 (d, J=8.4 Hz, 1H), 7.18 (dd, J=2.3, 8.4 Hz, 1H), 7.10 (d, J=2.2 Hz, 1H), 7.06-6.98 (m, 1H), 6.96-6.87 (m, 2H), 5.94-5.81 (m, 1H), 5.69 (dd, J=7.3, 15.2 Hz, 1H), 4.47-4.35 (m, 1H), 4.25-4.18 (m, 1H), 4.15-4.02 (m, 3H), 3.98-3.91 (m, 1H), 3.77 (d, J=15.1 Hz, 1H), 3.66 (d, J=14.1 Hz, 1H), 3.41 (s, 3H), 3.29 (d, J=14.3 Hz, 1H), 3.13 (br. s., 1H), 2.87-2.67 (m, 2H), 2.51-1.36 (m, 14H), 1.14 (d, J=6.8 Hz, 3H). m/z (ESI, +ve ion) 629.2 (M+H)+.

Example 456. (1S,3'R,6'R,7'S,8'E,11'S,12'R)-6-chloro-7'-hydroxy-12'-(methoxymethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'S)-6-chloro-7'-hydroxy-12'-(methoxymethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

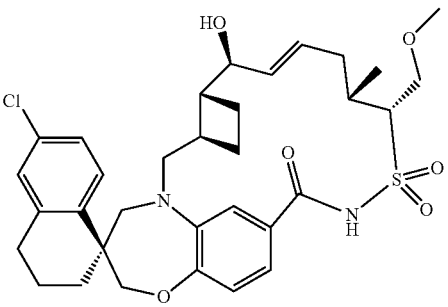

or

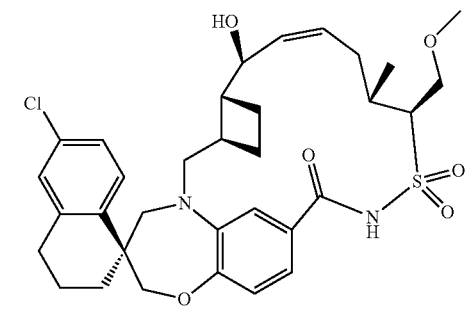

The title compound was obtained as the second eluting isomer from the reversed phase preparatory HPLC separation in Example 455, Step 3. $^1$H NMR (400 MHz, CDCl$_3$) δ 8.02 (br. s., 1H), 7.67 (d, J=8.4 Hz, 1H), 7.18 (d, J=8.6 Hz, 1H), 7.14-7.07 (m, 2H), 6.95 (d, J=8.0 Hz, 1H), 6.86 (br. s., 1H), 5.87 (br. s., 1H), 5.66 (dd, J=5.3, 15.8 Hz, 1H), 4.19-4.07 (m, 3H), 4.03-3.83 (m, 3H), 3.66 (d, J=15.5 Hz, 1H), 3.53-3.33 (m, 6H), 2.79 (br. s., 2H), 2.65-1.41 (m, 14H), 1.20 (d, J=7.0 Hz, 3H). m/z (ESI, +ve ion) 629.2 (M+H)+.

Example 457. (1S,3'R,6'R,7'S,8'Z,11'S,12'R)-6-chloro-7'-hydroxy-12'-(methoxymethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

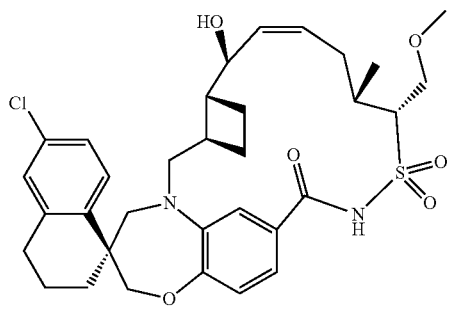 [SMILES: COC[C@H]1[C@@H](C)C/C=C\[C@H](O)[C@@H]2CC[C@H]2CN2C[C@@]3(CCCc4cc(Cl)ccc43)COc3ccc(cc32)C(=O)NS1(=O)=O]

The title compound was obtained as the third eluting isomer from the reversed phase preparatory HPLC separation in Example 455, Step 3. $^1$H NMR (400 MHz, CDCl$_3$) δ 9.70 (br. s., 1H), 7.72 (d, J=8.4 Hz, 1H), 7.45 (dd, J=2.0, 8.2 Hz, 1H), 7.19 (dd, J=2.2, 8.5 Hz, 1H), 7.09 (d, J=2.2 Hz, 1H), 7.06 (s, 1H), 6.99 (d, J=8.2 Hz, 1H), 5.74 (d, J=8.6 Hz, 1H), 5.54 (ddd, J=2.3, 5.2, 11.8 Hz, 1H), 4.42 (br. s., 1H), 4.17-3.95 (m, 4H), 3.92-3.82 (m, 2H), 3.67 (d, J=14.3 Hz, 1H), 3.43 (s, 3H), 3.20 (d, J=14.1 Hz, 1H), 3.15-3.02 (m, 2H), 2.93-2.69 (m, 3H), 2.40-1.35 (m, 12H), 1.16 (d, J=6.8 Hz, 3H). m/z (ESI, +ve ion) 629.2 (M+H)$^+$.

Example 458. (1S,3'R,6'R,7'S,8'E,11'S,12'R)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11R,12'S)-6-chloro-12'-ethyl-7'-hydroxy-11'-methoxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

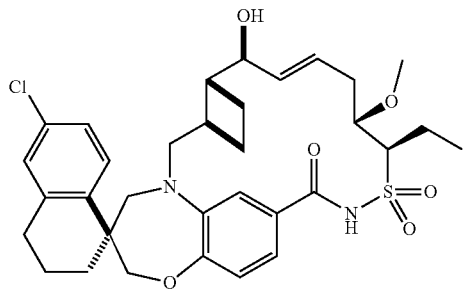

or

-continued

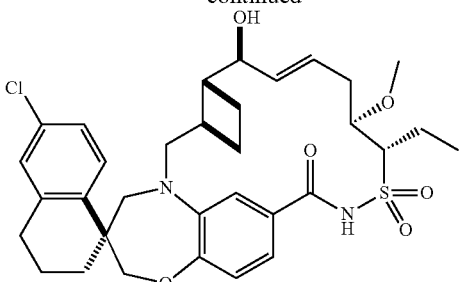

or

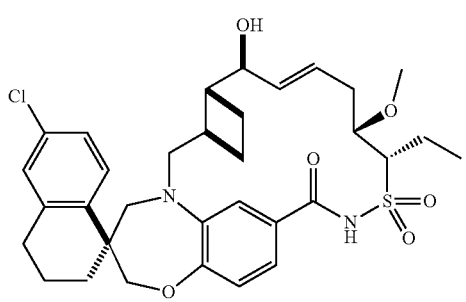

or

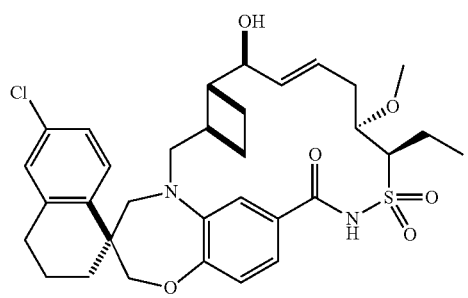

Step 1: (S)-ethyl 2-(N,N-bis(4-methoxybenzyl)sulfamoyl)butanoate and (R)-ethyl 2-(N,N-bis(4-methoxybenzyl)sulfamoyl)butanoate

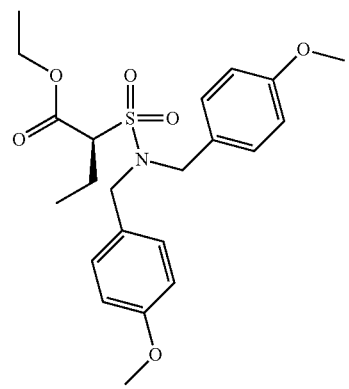

and

-continued

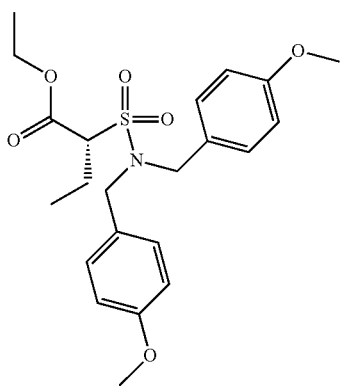

The title compound was prepared in an analogous manner to that described in Example 432, Step 1 using (R)-ethyl 2-(chlorosulfonyl)butanoate and (S)-ethyl 2-(chlorosulfonyl)butanoate. m/z (ESI, +ve ion) 458.2 (M+Na)$^+$.

Step 2: (S)-1-hydroxy-N,N-bis(4-methoxybenzyl) butane-2-sulfonamide and (R)-1-hydroxy-N,N-bis (4-methoxybenzyl)butane-2-sulfonamide

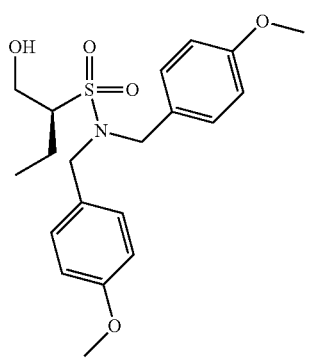

and

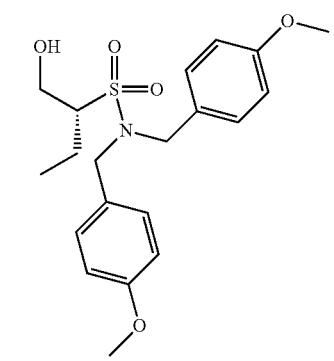

The title compound was prepared in an analogous manner to that described in Example 434, Step 2 using (S)-ethyl 2-(N,N-bis(4-methoxybenzyl)sulfamoyl)butanoate and (R)-ethyl 2-(N,N-bis(4-methoxybenzyl)sulfamoyl)butanoate. m/z (ESI, +ve ion) 416.2 (M+Na)$^+$.

Step 3: (S)—N,N-bis(4-methoxybenzyl)-1-oxobutane-2-sulfonamide and (R)—N,N-bis(4-methoxybenzyl)-1-oxobutane-2-sulfonamide

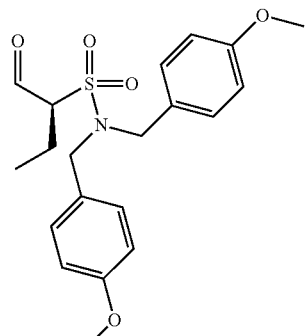

and

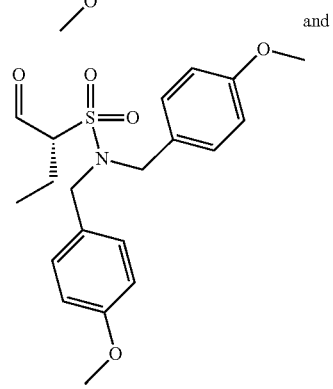

The title compound was prepared in an analogous manner to that described in Example 438, Step 1 using (S)-1-hydroxy-N,N-bis(4-methoxybenzyl)butane-2-sulfonamide and (R)-1-hydroxy-N,N-bis(4-methoxybenzyl)butane-2-sulfonamide. m/z (ESI, +ve ion) 414.2 (M+Na)$^+$.

Step 4: (3S,4S)-4-hydroxy-N,N-bis(4-methoxybenzyl)hept-6-ene-3-sulfonamide and (3S,4S)-4-hydroxy-N,N-bis(4-methoxybenzyl)hept-6-ene-3-sulfonamide and (3S,4R)-4-hydroxy-N,N-bis(4-methoxybenzyl)hept-6-ene-3-sulfonamide and (3R,4S)-4-hydroxy-N,N-bis(4-methoxybenzyl)hept-6-ene-3-sulfonamide

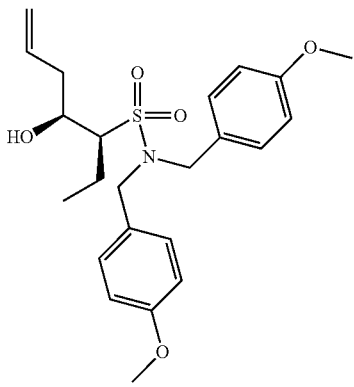

and

1031

-continued

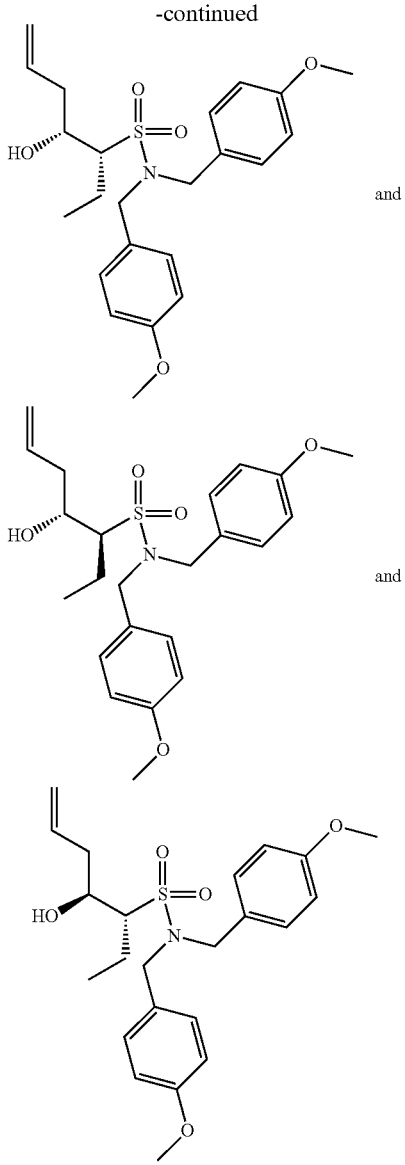

and

The title compound was prepared in an analogous manner to that described in Example 714, Step 4 using (S)—N,N-bis(4-methoxybenzyl)-1-oxobutane-2-sulfonamide and (R)—N,N-bis(4-methoxybenzyl)-1-oxobutane-2-sulfonamide. m/z (ESI, +ve ion) 456.2 (M+Na)$^+$.

Step 5: (3S,4S)-4-methoxyhept-6-ene-3-sulfonamide and (3R,4R)-4-methoxyhept-6-ene-3-sulfonamide and (3S,4R)-4-methoxyhept-6-ene-3-sulfonamide and (3R,4S)-4-methoxyhept-6-ene-3-sulfonamide

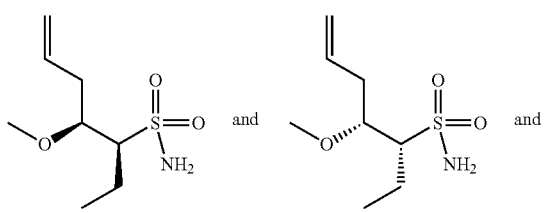

1032

-continued

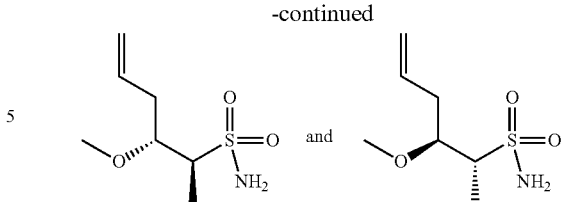

The title compound was prepared from (3S,4S)-4-hydroxy-N,N-bis(4-methoxybenzyl)hept-6-ene-3-sulfonamide and (3S,4S)-4-hydroxy-N,N-bis(4-methoxybenzyl)hept-6-ene-3-sulfonamide and (3S,4R)-4-hydroxy-N,N-bis(4-methoxybenzyl)hept-6-ene-3-sulfonamide and (3R,4S)-4-hydroxy-N,N-bis(4-methoxybenzyl)hept-6-ene-3-sulfonamide by similar procedures described in Example 434, Steps 3-4. m/z (ESI, +ve ion) 208.2 (M+H)$^+$.

Step 6: (S)-6'-chloro-5-(((1R,2R)-2-((1S,5R,6R,E)-1-hydroxy-5-methoxy-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,6S,E)-1-hydroxy-5-methoxy-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5R,6S,E)-1-hydroxy-5-methoxy-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,6R,E)-1-hydroxy-5-methoxy-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid

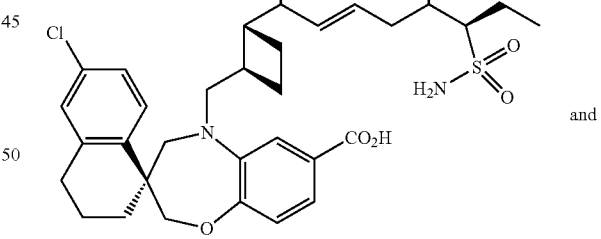

and

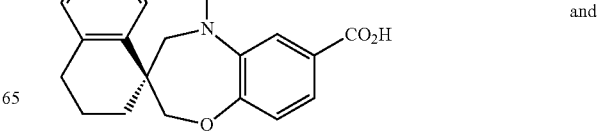

and

-continued

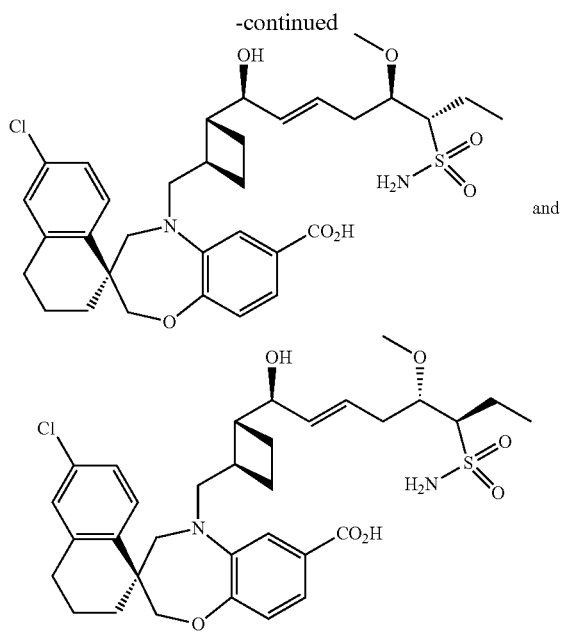

To a 25 mL single-necked round-bottomed flask were placed (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (70 mg, 0.15 mmol, Intermediate, AA11A) and (3S,4S)-4-methoxyhept-6-ene-3-sulfonamide and (3R,4R)-4-methoxyhept-6-ene-3-sulfonamide and (3S,4R)-4-methoxyhept-6-ene-3-sulfonamide and (3R,4S)-4-methoxyhept-6-ene-3-sulfonamide (155 mg, 0.748 mmol) in DCE (2 mL). The mixture was stirred under argon for 10 min before Hoveyda-Grubbs catalyst 2nd generation (19 mg, 0.030 mmol) was added, and then the resulting mixture was stirred under argon at ambient temperature for 2 h. The reaction mixture was bubbled with air for 10 min and then concentrated. The crude material was purified by chromatography through a Redi-Sep pre-packed silica gel column (40 g), eluting with a gradient of 50% to 100% EtOAc (containing 0.3% AcOH) in hexane, to provide the title compound (52 mg, 54%). m/z (ESI, +ve ion) 647.2 (M+H)$^+$.

Step 7: (1S,3'R,6'R,7'S,8'E,11'S,12'R)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'S)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compound was prepared in an analogous manner to that described in Example 323, Step 7 using (S)-6'-chloro-5-(((1R,2R)-2-((1S,5R,6R,E)-1-hydroxy-5-methoxy-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,6S,E)-1-hydroxy-5-methoxy-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5R,6S,E)-1-hydroxy-5-methoxy-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,6R,E)-1-hydroxy-5-methoxy-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid, and isolated as the first eluting isomer from the reversed phase preparatory HPLC separation. $^1$H NMR (500 MHz, CD$_3$OD) δ 7.73 (d, J=8.6 Hz, 1H), 7.17 (dd, J=2.2, 8.6 Hz, 1H), 7.11 (s, 1H), 7.05 (dd, J=2.0, 8.1 Hz, 1H), 6.93 (d, J=8.1 Hz, 1H), 6.87 (d, J=1.5 Hz, 1H), 5.82 (dd, J=8.3, 15.2 Hz, 1H), 5.74-5.61 (m, 1H), 4.18 (dd, J=3.4, 8.1 Hz, 1H), 4.08 (s, 2H), 3.99 (dt, J=2.1, 4.6 Hz, 1H), 3.81 (d, J=15.2 Hz, 1H), 3.65 (d, J=14.4 Hz, 1H), 3.54 (d, J=10.3 Hz, 1H), 3.35 (s, 3H), 3.08 (dd, J=9.9, 15.3 Hz, 1H), 2.87-2.68 (m, 2H), 2.60 (ddd, J=2.7, 8.7, 15.0 Hz, 1H), 2.45-2.24 (m, 3H), 2.18-1.79 (m, 8H), 1.72 (td, J=9.5, 18.7 Hz, 1H), 1.49-1.40 (m, 1H), 1.35-1.30 (m, 2H), 1.24 (t, J=7.5 Hz, 3H). m/z (ESI, +ve ion) 629.2 (M+H)$^+$.

Example 459. (1S,3'R,6'R,7'S,8'E,11R,12'S)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

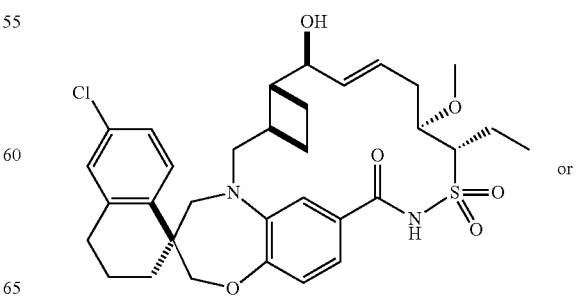

1035

-continued

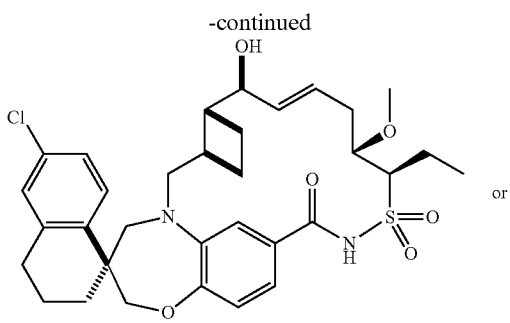

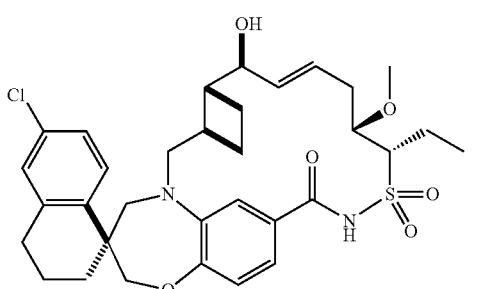

or

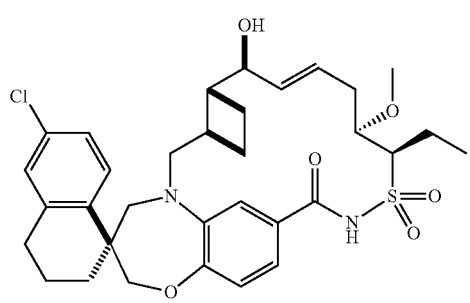

The title compound was obtained as the second eluting isomer from the reversed phase preparatory HPLC separation in Example 458, Step 7. $^1$H NMR (500 MHz, CDCl$_3$) δ 8.31 (br. s., 1H), 7.64 (d, J=8.6 Hz, 2H), 7.16 (dd, J=2.3, 8.4 Hz, 1H), 7.10 (d, J=2.2 Hz, 1H), 7.03-6.96 (m, 1H), 6.96-6.90 (m, 1H), 5.75 (dd, J=3.9, 15.7 Hz, 1H), 5.46 (br. s., 1H), 4.37-4.18 (m, 2H), 4.16-3.91 (m, 3H), 3.76 (d, J=12.0 Hz, 1H), 3.49 (d, J=8.6 Hz, 1H), 3.38 (s, 3H), 3.37-3.29 (m, 1H), 3.14 (d, J=15.4 Hz, 1H), 2.81-2.72 (m, 2H), 2.65-1.13 (m, 18H). m/z (ESI, +ve ion) 629.2 (M+H)$^+$.

1036

Example 460. (1S,3'R,6'R,7'S,8'E,11'S,12'S)-6-chloro-7'-methoxy-12'-(methoxymethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-methoxy-12'-(methoxymethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

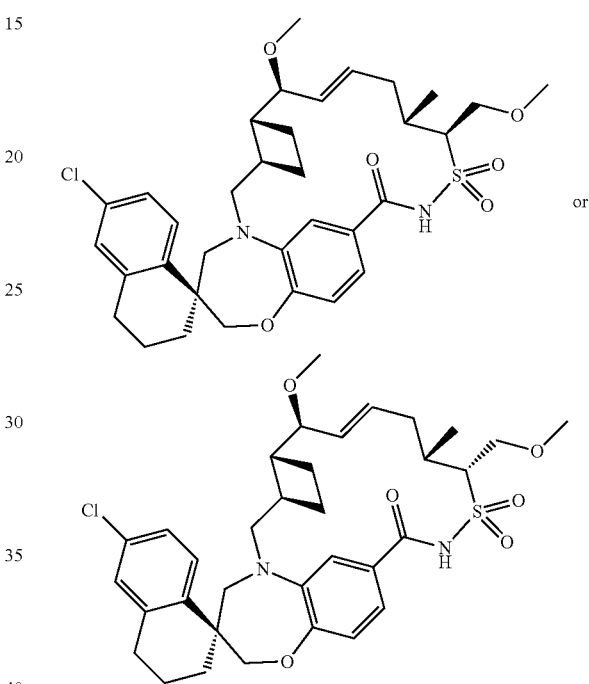

The title compound was prepared in an analogous manner to that described in Example 404, Step 2 using (1S,3'R,6'R,7'S,8'E,11'S,12'S)-6-chloro-7'-hydroxy-12'-(methoxymethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-hydroxy-12'-(methoxymethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'S)-6-chloro-7'-hydroxy-12'-(methoxymethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'R)-6-chloro-7'-hydroxy-12'-(methoxymethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 455, Step 3, the crude material before HPLc purification) and iodomethane, and isolated as the first eluting isomer from the reversed phase preparatory HPLC separation. $^1$H NMR (500 MHz, CDCl$_3$) δ 7.99 (s, 1H), 7.70 (d, J=8.6 Hz, 1H), 7.19 (dd, J=2.2, 8.6 Hz, 1H), 7.10 (d, J=2.0 Hz, 1H), 6.96-6.87 (m, 2H), 6.85 (d, J=1.5 Hz, 1H), 5.93-5.83 (m, 1H), 5.52 (dd, J=9.4, 15.3 Hz, 1H), 4.53-4.45

(m, 1H), 4.18-3.99 (m, 4H), 3.82 (d, J=15.2 Hz, 1H), 3.74-3.61 (m, 2H), 3.44 (s, 3H), 3.29-3.16 (m, 4H), 3.00 (dd, J=10.3, 15.4 Hz, 1H), 2.87-2.67 (m, 2H), 2.54-1.18 (m, 13H), 1.14 (d, J=6.8 Hz, 3H). m/z (ESI, +ve ion) 643.2 (M+H)$^+$.

Example 461. (1S,3'R,6'R,7'S,8'E,11'S,12'R)-6-chloro-7'-methoxy-12'-(methoxymethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-methoxy-12'-(methoxymethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide Example 462. (1S,3'R,6'R,7'S,8'E,11'S,12'R)-6-chloro-12'-ethyl-7',11'-dimethoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-12'-ethyl-7',11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-12'-ethyl-7',11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-12'-ethyl-7',11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

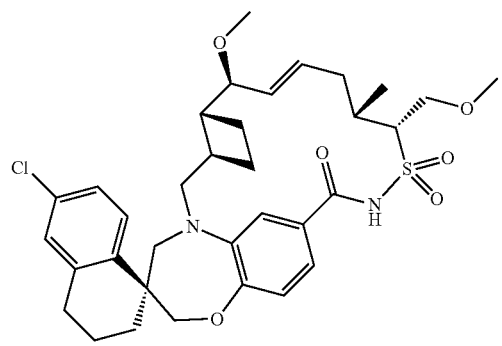

or

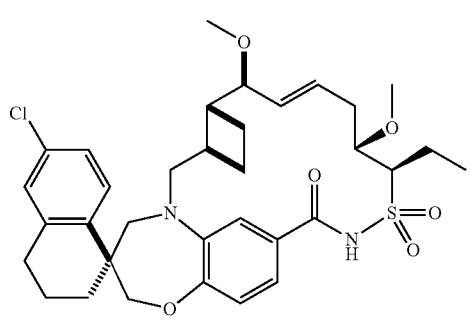

or

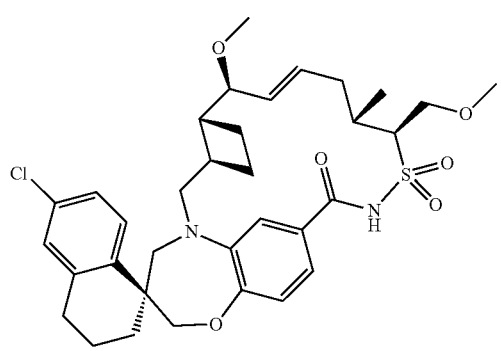

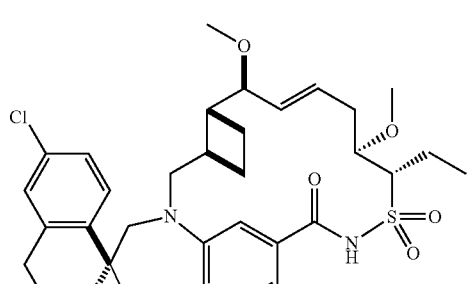

or

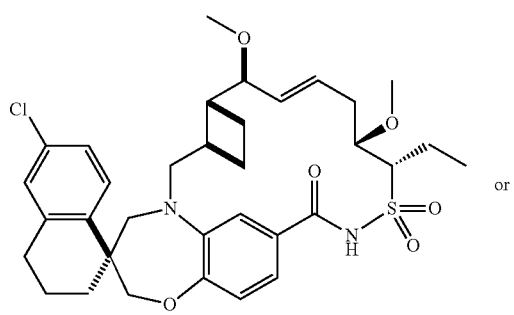

or

The title compound was obtained as the second eluting isomer from the reversed phase preparatory HPLC separation in Example 460. $^1$H NMR (400 MHz, CDCl$_3$) δ 8.22 (br. s., 1H), 7.66 (d, J=8.4 Hz, 1H), 7.18 (dd, J=2.3, 8.4 Hz, 2H), 7.10 (d, J=2.2 Hz, 1H), 6.97 (d, J=8.2 Hz, 1H), 6.72 (br. s., 1H), 5.92 (br. s., 1H), 5.48 (dd, J=7.9, 15.6 Hz, 1H), 4.15-4.01 (m, 3H), 3.95-3.81 (m, 2H), 3.70 (d, J=14.7 Hz, 1H), 3.63-3.52 (m, 2H), 3.41 (s, 3H), 3.35 (d, J=14.5 Hz, 1H), 3.27 (s, 3H), 2.89-2.71 (m, 2H), 2.70-2.43 (m, 3H), 2.42-2.27 (m, 2H), 2.11-1.76 (m, 7H), 1.66 (quin, J=9.1 Hz, 1H), 1.49 (t, J=11.7 Hz, 1H), 1.20 (d, J=7.0 Hz, 3H). m/z (ESI, +ve ion) 643.2 (M+H)$^+$.

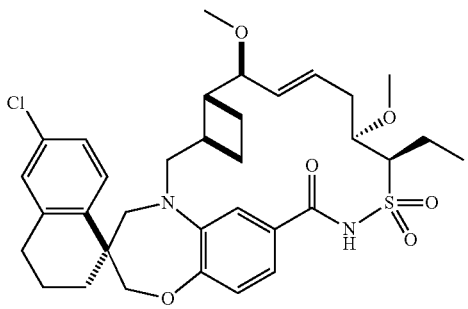

The title compound was prepared in an analogous manner to that described in Example 404, Step 2 using (1S,3'R,6'R,7'S,8'E,11'S,12'R)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'R,12'S)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'S,12'S)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'R,12'R)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 458, Step 7) and iodomethane, and isolated as the first eluting isomer from the reversed phase preparatory HPLC separation. ¹H NMR (500 MHz, CDCl₃) δ 8.18 (s, 1H), 7.70 (d, J=8.6 Hz, 1H), 7.18 (dd, J=2.3, 8.4 Hz, 1H), 7.10 (d, J=2.2 Hz, 1H), 6.94 (s, 2H), 6.85 (s, 1H), 5.77-5.67 (m, 1H), 5.66-5.59 (m, 1H), 4.15-4.08 (m, 3H), 3.81 (d, J=15.2 Hz, 1H), 3.73 (d, J=14.2 Hz, 1H), 3.66 (dd, J=3.4, 8.6 Hz, 1H), 3.55-3.50 (m, 1H), 3.37 (s, 3H), 3.26-3.21 (m, 4H), 3.01 (dd, J=10.0, 15.2 Hz, 1H), 2.85-2.71 (m, 2H), 2.61-2.53 (m, 1H), 2.51-2.40 (m, 2H), 2.33 (quin, J=9.0 Hz, 1H), 2.24 (quind, J=7.5, 15.2 Hz, 1H), 2.16-1.60 (m, 8H), 1.41 (t, J=12.7 Hz, 1H), 1.30 (t, J=7.5 Hz, 3H). m/z (ESI, +ve ion) 643.2 (M+H)⁺.

Example 463. (1S,3'R,6'R,7'S,8'E,11'S,12'S)-6-chloro-7'-(2-methoxyethoxy)-12'-(methoxymethyl)-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'S,12'R)-6-chloro-7'-(2-methoxyethoxy)-12'-(methoxymethyl)-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

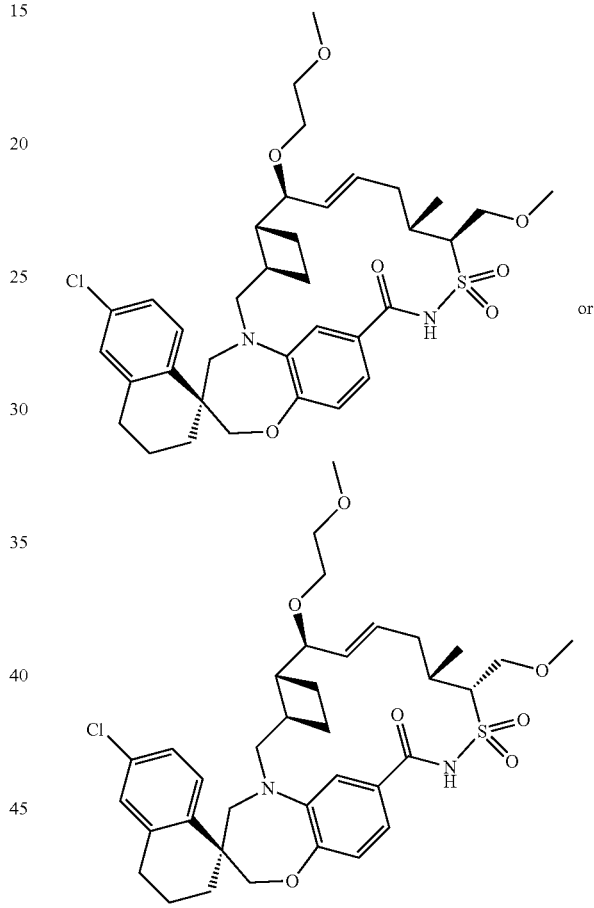

The title compound was prepared in an analogous manner to that described in Example 404, Step 2 using (1S,3'R,6'R,7'S,8'E,11'S,12'S)-6-chloro-7'-hydroxy-12'-(methoxymethyl)-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'S,12'R)-6-chloro-7'-hydroxy-12'-(methoxymethyl)-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'Z,11'S,12'S)-6-chloro-7'-hydroxy-12'-(methoxymethyl)-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'Z,11'S,12'R)-6-chloro-7'-hydroxy-12'-(methoxymethyl)-11'-methyl-3,4-dihydro-2H,15'H-spiro

[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 455, Step 3, the crude material before HPLC purification) and 2-bromoethyl methyl ether, and isolated as the first eluting isomer from the reversed phase preparatory HPLC separation. $^1$H NMR (400 MHz, CDCl$_3$) δ 8.05 (s, 1H), 7.70 (d, J=8.6 Hz, 1H), 7.18 (dd, J=2.2, 8.4 Hz, 1H), 7.09 (d, J=2.2 Hz, 1H), 6.95-6.84 (m, 3H), 5.94-5.79 (m, 1H), 5.64-5.48 (m, 1H), 4.45 (dt, J=2.4, 5.2 Hz, 1H), 4.11-3.97 (m, 4H), 3.88-3.75 (m, 2H), 3.70 (d, J=14.3 Hz, 1H), 3.62-3.54 (m, 1H), 3.53-3.48 (m, 2H), 3.46-3.40 (m, 4H), 3.39 (s, 3H), 3.22 (d, J=14.3 Hz, 1H), 2.98 (dd, J=10.2, 15.5 Hz, 1H), 2.87-2.67 (m, 2H), 2.56-0.60 (m, 16H). m/z (ESI, +ve ion) 687.2 (M+H)$^+$.

Example 464. (1S,3'R,6'R,7'S,8'E,11'S,12'R)-6-chloro-7'-(2-methoxyethoxy)-12'-(methoxymethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-(2-methoxyethoxy)-12'-(methoxymethyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

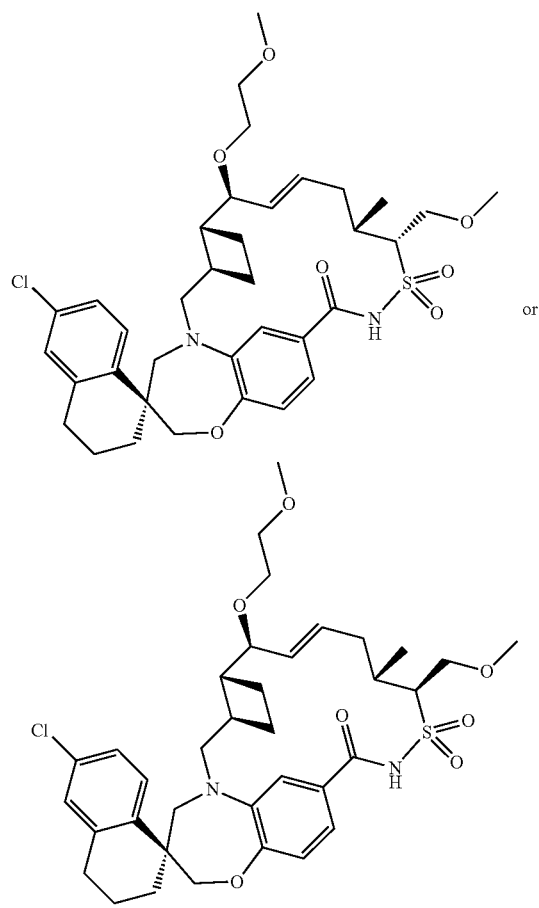

The title compound was obtained as the second eluting isomer from the reversed phase preparatory HPLC separation in Example 463. $^1$H NMR (400 MHz, CDCl$_3$) δ 8.29 (br. s., 1H), 7.66 (d, J=8.6 Hz, 1H), 7.18 (dd, J=2.4, 8.5 Hz, 2H), 7.09 (d, J=2.2 Hz, 1H), 6.96 (d, J=8.0 Hz, 1H), 6.74 (br. s., 1H), 5.91 (br. s., 1H), 5.49 (dd, J=7.5, 15.6 Hz, 1H), 4.20-4.01 (m, 3H), 3.95-3.82 (m, 2H), 3.79-3.49 (m, 6H), 3.47-3.32 (m, 8H), 3.30-3.17 (m, 1H), 2.87-2.45 (m, 5H), 2.33 (d, J=5.5 Hz, 2H), 2.12-1.76 (m, 6H), 1.71-1.59 (m, 1H), 1.49 (t, J=11.9 Hz, 1H), 1.19 (d, J=7.2 Hz, 3H). m/z (ESI, +ve ion) 687.2 (M+H)$^+$.

Example 465. (1S,3'R,6'R,7'S,8'E,11'S,12'R)-6-chloro-12'-ethyl-11'-methoxy-7'-(2-(4-morpholinyl)ethoxy)-3,4-dihydro-2H,15'H-spiro[naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-12'-ethyl-11'-methoxy-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-12'-ethyl-11'-methoxy-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-12'-ethyl-11'-methoxy-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

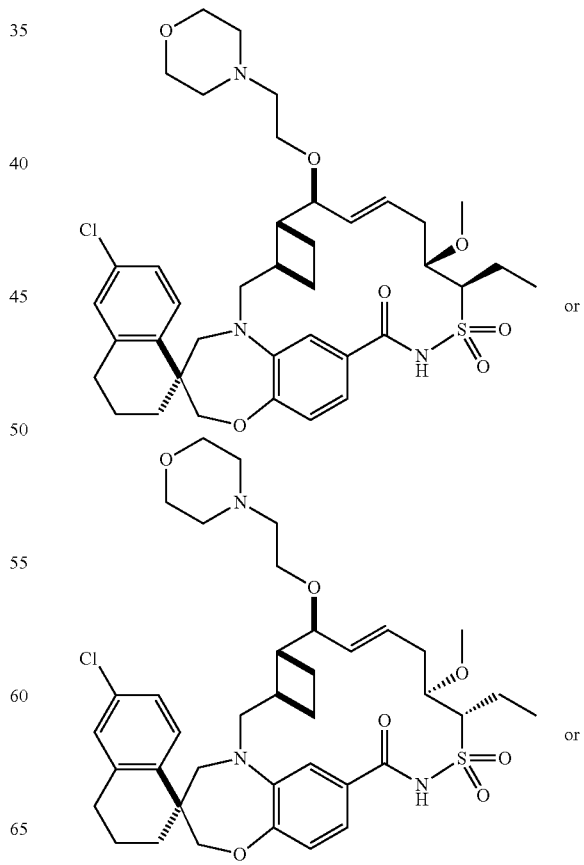

-continued

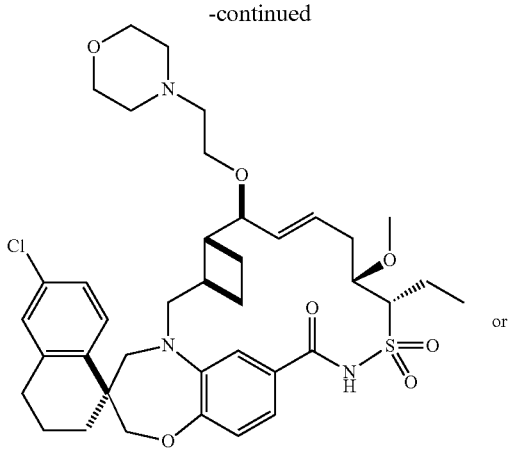

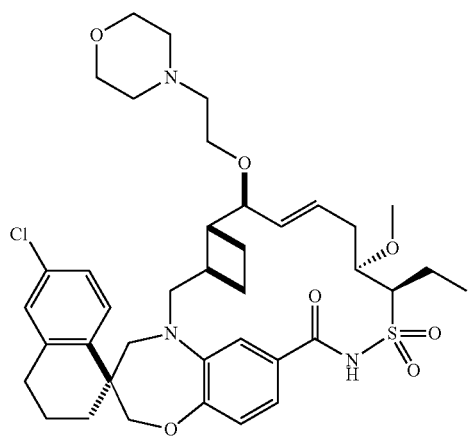

The title compound was prepared in an analogous manner to that described in Example 404 using (((1S,3'R,6'R,7'S,8'E,11'S,12'R)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-12'-ethyl-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 458, Step 7) and 4-(2-bromoethyl)morpholine hydrobromide. $^1$H NMR (400 MHz, CDCl$_3$) δ 8.57 (br. s., 1H), 7.70 (d, J=8.6 Hz, 1H), 7.18 (dd, J=2.2, 8.4 Hz, 1H), 7.10 (d, J=2.2 Hz, 1H), 7.00-6.90 (m, 2H), 6.79 (s, 1H), 5.89-5.74 (m, 1H), 5.60 (dd, J=8.5, 15.0 Hz, 1H), 4.16-3.94 (m, 7H), 3.85-3.58 (m, 7H), 3.54-3.45 (m, 1H), 3.35 (s, 3H), 3.31-1.74 (m, 20H), 1.73-1.57 (m, 1H), 1.40 (t, J=12.4 Hz, 1H), 1.28 (t, J=7.4 Hz, 3H). m/z (ESI, +ve ion) 742.4 (M+H)$^+$.

Example 466. (1S,3'R,6'R,7'S,8'E,11'S,12'S)-6-chloro-12'-(ethoxymethyl)-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-12'-(ethoxymethyl)-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

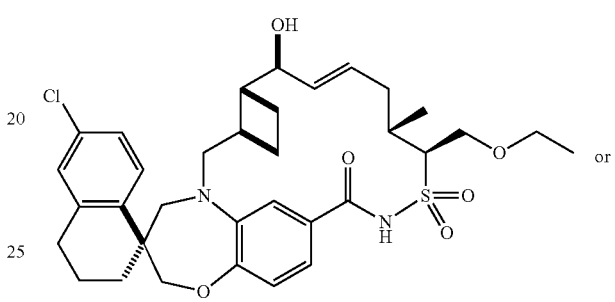

Step 1: (2R,3S)-1-hydroxy-N,N-bis(4-methoxybenzyl)-3-methylhex-5-ene-2-sulfonamide and (2S,3S)-1-hydroxy-N,N-bis(4-methoxybenzyl)-3-methylhex-5-ene-2-sulfonamide

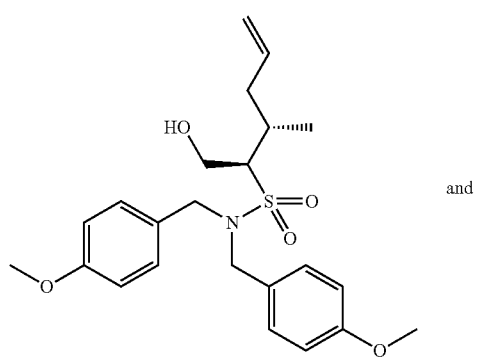

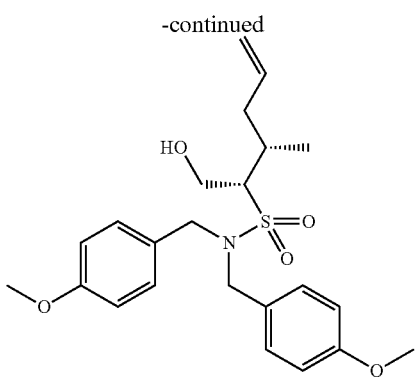

The title compound was prepared from (S)—N,N-bis(4-methoxybenzyl)-2-methylpent-4-ene-1-sulfonamide (Example 395, Step 3) by similar procedures described in Example 434, Steps 1-2.

Step 2: (2S,3S)-1-ethoxy-3-methylhex-5-ene-2-sulfonamide and (2R,3S)-1-ethoxy-3-methylhex-5-ene-2-sulfonamide and (S)-3-methylhexa-1,5-diene-2-sulfonamide

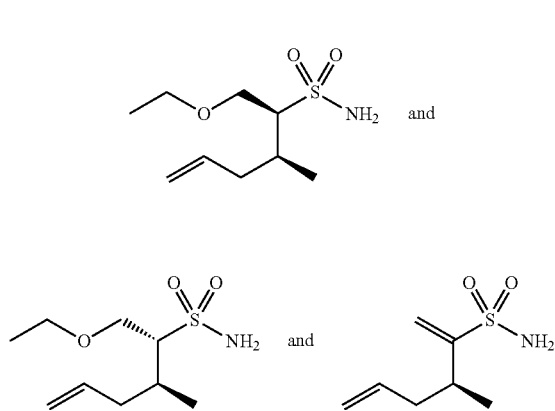

The title compound was prepared from (2R,3S)-1-hydroxy-N,N-bis(4-methoxybenzyl)-3-methylhex-5-ene-2-sulfonamide and (2S,3S)-1-hydroxy-N,N-bis(4-methoxybenzyl)-3-methylhex-5-ene-2-sulfonamide by similar procedures described in Example 439, Steps 1-2.

Step 3: (1S,3'R,6'R,7'S,8'E,11'S,12'S)-6-chloro-12'-(ethoxymethyl)-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'S,12'R)-6-chloro-12'-(ethoxymethyl)-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide The title compound was prepared from (2S,3S)-1-ethoxy-3-methylhex-5-ene-2-sulfonamide and (2R,3S)-1-ethoxy-3-methylhex-5-ene-2-sulfonamide and (S)-3-methylhexa-1,5-diene-2-sulfonamide by similar procedures described in Example 458, Steps 6-7, and isolated as the second eluting isomer from the reversed phase preparatory HPLC separation. $^1$H NMR (400 MHz, CDCl$_3$) δ 8.14 (br. s., 1H), 7.69 (d, J=8.4 Hz, 1H), 7.18 (dd, J=2.1, 8.5 Hz, 1H), 7.10 (d, J=2.0 Hz, 2H), 6.92 (s, 2H), 5.95-5.83 (m, 1H), 5.67 (dd, J=6.6, 15.2 Hz, 1H), 4.47-4.35 (m, 1H), 4.20 (br. s., 1H), 4.15-4.03 (m, 3H), 3.94 (br. s., 1H), 3.79-3.47 (m, 4H), 3.39-3.11 (m, 2H), 2.88-2.68 (m, 2H), 2.51-1.05 (m, 20H). m/z (ESI, +ve ion) 643.2 (M+H)$^+$.

Example 467. (1S,3'R,6'R,7'S,8'E,11'S,12'R)-6-chloro-12'-(ethoxymethyl)-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'S,12'S)-6-chloro-12'-(ethoxymethyl)-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

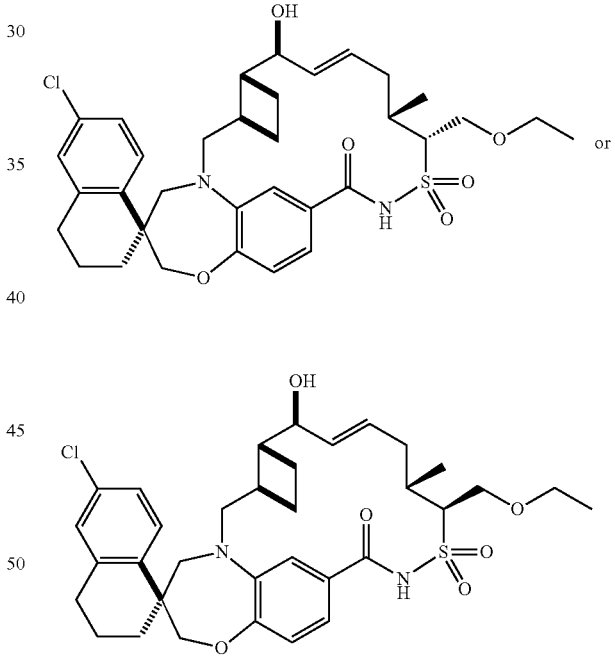

The title compound was obtained as the third eluting isomer from the reversed phase preparatory HPLC separation in Example 466, Step 3. $^1$H NMR (400 MHz, CDCl$_3$) δ 8.28 (br. s., 1H), 7.67 (d, J=8.4 Hz, 1H), 7.18 (dd, J=2.2, 8.5 Hz, 1H), 7.14-7.09 (m, 2H), 6.95 (d, J=8.2 Hz, 1H), 6.85 (br. s., 1H), 5.90 (br. s., 1H), 5.65 (dd, J=5.7, 15.5 Hz, 1H), 4.21-3.96 (m, 7H), 3.85 (br. s., 1H), 3.66 (d, J=14.3 Hz, 1H), 3.59-3.22 (m, 7H), 2.93-2.70 (m, 3H), 2.58 (br. s., 2H), 2.47 (d, J=3.9 Hz, 1H), 2.36-1.08 (m, 12H). m/z (ESI, +ve ion) 643.2 (M+H)$^+$.

Example 468. (1S,3'R,6'R,7'S,8'E,11'S)-6-chloro-7'-hydroxy-11'-methyl-12'-methylidene-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

Example 469. (1S,3'R,6'R,7'S,8'E,11'S,12'S)-6-chloro-12'-(ethoxymethyl)-7'-methoxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'S,12'R)-6-chloro-12'-(ethoxymethyl)-7'-methoxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

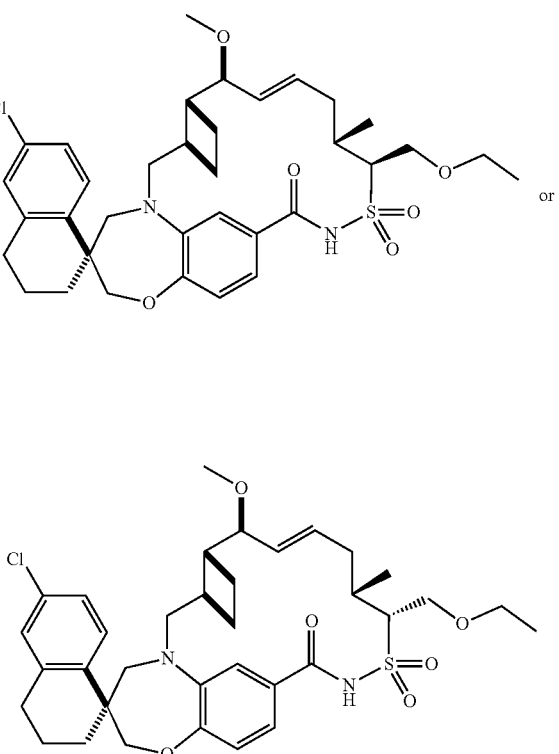

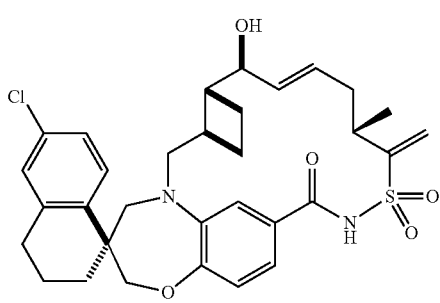

The title compound was obtained as the first eluting isomer from the reversed phase preparatory HPLC separation in Example 466, Step 3. ¹H NMR (400 MHz, CDCl₃) δ 8.30 (s, 1H), 7.70 (d, J=8.4 Hz, 1H), 7.18 (dd, 8.5 Hz, 1H), 7.09 (d, J=2.0 Hz, 1H), 6.92 (s, 2H), 6.86 (s, 1H), 6.79 (d, J=0.8 Hz, 1H), 6.03 (s, 1H), 5.78-5.56 (m, 2H), 4.20-4.02 (m, 3H), 3.78 (d, J=13.3 Hz, 1H), 3.70 (d, J=14.1 Hz, 1H), 3.21 (d, J=14.3 Hz, 1H), 3.01 (dd, J=8.9, 15.4 Hz, 1H), 2.87-2.64 (m, 3H), 2.49-2.22 (m, 4H), 2.08-1.57 (m, 8H), 1.40 (t, J=12.6 Hz, 1H), 1.28 (d, J=7.0 Hz, 3H). m/z (ESI, +ve ion) 597.2 (M+H)⁺.

The title compound was prepared in an analogous manner to that described in Example 404, Step 2 using (1S,3'R,6'R,7'S,8'E,11'S,12'S)-6-chloro-12'-(ethoxymethyl)-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'S,12'R)-6-chloro-12'-(ethoxymethyl)-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 466) and iodomethane. ¹H NMR (400 MHz, CDCl₃) δ 7.82 (s, 1H), 7.50 (d, J=8.6 Hz, 1H), 6.99 (dd, J=2.2, 8.5 Hz, 1H), 6.90 (d, J=2.3 Hz, 1H), 6.77-6.62 (m, 3H), 5.76-5.62 (m, 1H), 5.32 (dd, J=9.2, 14.9 Hz, 1H), 4.30 (ddd, J=2.4, 4.4, 6.7 Hz, 1H), 4.00-3.83 (m, 4H), 3.62 (d, J=15.3 Hz, 1H), 3.54-3.44 (m, 2H), 3.43-3.33 (m, 2H), 3.11-2.99 (m, 4H), 2.81 (dd, J=10.1, 15.4 Hz, 1H), 2.68-2.48 (m, 2H), 2.42-1.35 (m, 19H). m/z (ESI, +ve ion) 657.2 (M+H)⁺.

Example 470. (1S,3'R,6'R,7'S,8'E,11'S,12'R)-6-chloro-12'-ethyl-7'-hydroxy-11'-(2-methoxyethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-12'-ethyl-7'-hydroxy-11'-(2-methoxyethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-12'-ethyl-7'-hydroxy-11'-(2-methoxyethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11R,12'S)-6-chloro-12'-ethyl-7'-hydroxy-11'-(2-methoxyethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

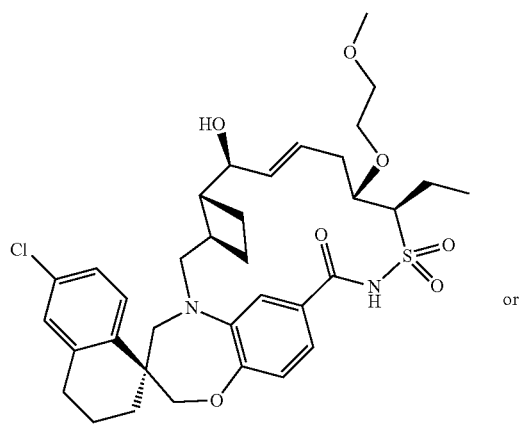 or

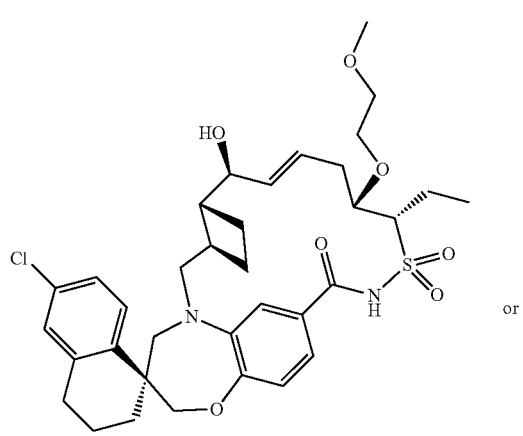 or

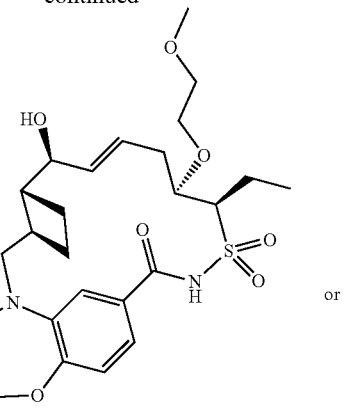 or

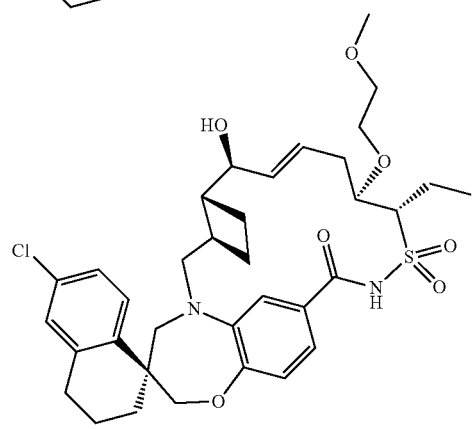

Step 1: (3S,4S)-4-(2-methoxyethoxy)hept-6-ene-3-sulfonamide and (3R,4R)-4-(2-methoxyethoxy)hept-6-ene-3-sulfonamide and (3S,4R)-4-(2-methoxyethoxy)hept-6-ene-3-sulfonamide and (3R,4S)-4-(2-methoxyethoxy)hept-6-ene-3-sulfonamide

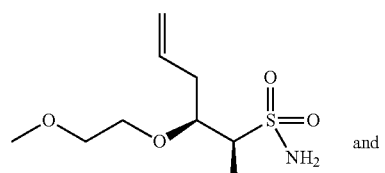 and

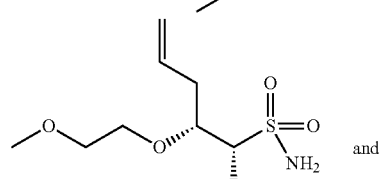 and

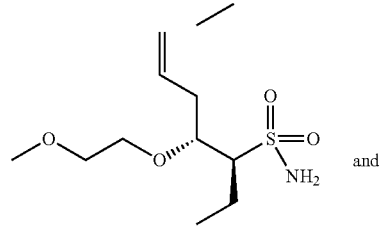 and

-continued

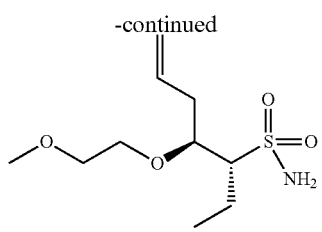

The title compound was prepared from (3S,4S)-4-hydroxy-N,N-bis(4-methoxybenzyl)hept-6-ene-3-sulfonamide and (3S,4S)-4-hydroxy-N,N-bis(4-methoxybenzyl)hept-6-ene-3-sulfonamide and (3S,4R)-4-hydroxy-N,N-bis(4-methoxybenzyl)hept-6-ene-3-sulfonamide and (3R,4S)-4-hydroxy-N,N-bis(4-methoxybenzyl)hept-6-ene-3-sulfonamide (Example 458, Step 4) and 2-bromoethyl methyl ether by similar procedures described in Example 434, Steps 3-4. m/z (ESI, +ve ion) 252.2 (M+H)$^+$.

Step 2: (1S,3'R,6'R,7'S,8'E,11'S,12'R)-6-chloro-12'-ethyl-7'-hydroxy-11'-(2-methoxyethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-12'-ethyl-7'-hydroxy-11'-(2-methoxyethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-12'-ethyl-7'-hydroxy-11'-(2-methoxyethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11R,12'S)-6-chloro-12'-ethyl-7'-hydroxy-11'-(2-methoxyethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compound was prepared from (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Intermediate, AA11A) and (3S,4S)-4-(2-methoxyethoxy)hept-6-ene-3-sulfonamide and (3R,4R)-4-(2-methoxyethoxy)hept-6-ene-3-sulfonamide and (3S,4R)-4-(2-methoxyethoxy)hept-6-ene-3-sulfonamide and (3R,4S)-4-(2-methoxyethoxy)hept-6-ene-3-sulfonamide by similar procedures described in Example 432, Steps 4-5, and isolated as the major isomer from the reversed phase preparatory HPLC separation. $^1$H NMR (400 MHz, CDCl$_3$) δ 8.95 (s, 1H), 7.71 (d, J=8.4 Hz, 1H), 7.18 (dd, J=2.2, 8.5 Hz, 1H), 7.10 (d, J=2.2 Hz, 1H), 6.99-6.81 (m, 3H), 5.89-5.78 (m, 1H), 5.77-5.64 (m, 1H), 4.26 (dd, J=4.4, 7.1 Hz, 1H), 4.18-4.03 (m, 2H), 3.90 (dd, J=3.9, 8.0 Hz, 1H), 3.83 (d, J=15.1 Hz, 1H), 3.77-3.66 (m, 4H), 3.60-3.51 (m, 1H), 3.43-3.35 (m, 1H), 3.29-3.21 (m, 4H), 3.10-2.99 (m, 1H), 2.87-2.69 (m, 2H), 2.54-0.74 (m, 18H). m/z (ESI, +ve ion) 673.2 (M+H)$^+$.

Example 471. (1S,3'R,6'R,7'S,8'E,10'R,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

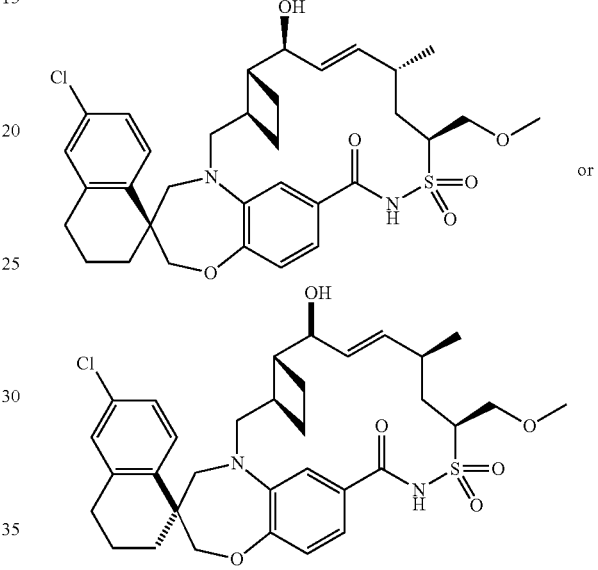

Step 1: (2R,4S)-1-methoxy-4-methylhex-5-en-2-ol and (2R,4R)-1-methoxy-4-methylhex-5-en-2-ol

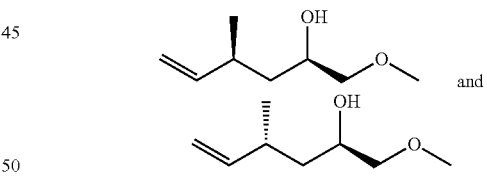

To 1-methyl-2-propenylmagnesium chloride (95.0 ml, 47.7 mmol), 0.5 M solution in THF stirred at –10° C. to –18° C. in a 500-mL single-necked round-bottomed flask was added slowly (r)-(–)-glycidyl methyl ether, 97% (2.00 ml, 22.7 mmol) in THF (45.4 ml) over 1 h. The resulting mixture was allowed to slowly warm up to ambient temperature and stirred overnight. The reaction mixture was cooled in an ice bath before slowly quenched with ice-cold saturated ammonium chloride aqueous solution. This mixture was further diluted with ether and ice-cold water. The organic layer was separated and concentrated. The residue was purified by chromatography eluting with a gradient of 0% to 35% EtOAc in hexane to give the title compound (3.21 g, 98% yield). $^1$H NMR (400 MHz, CDCl$_3$) δ 5.61-5.87 (m, 1H), 4.90-5.13 (m, 2H), 3.78-3.94 (m, 1H), 3.35-3.48 (m, 4H), 3.18-3.32 (m, 1H), 2.34-2.52 (m, 1H), 2.23-2.34 (m, 1H), 1.44-1.62 (m, 1H), 1.26-1.39 (m, 1H), 1.01-1.10 (m, 3H).

Step 2: (2S,4S)-1-methoxy-4-methylhex-5-ene-2-sulfonamide and (2S,4R)-1-methoxy-4-methylhex-5-ene-2-sulfonamide

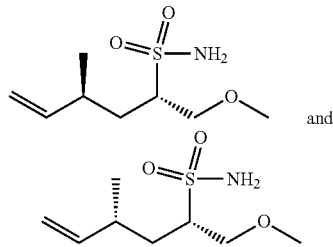

The title compound was prepared from (2R,4S)-1-methoxy-4-methylhex-5-en-2-ol and (2R,4R)-1-methoxy-4-methylhex-5-en-2-ol by similar procedures described in Example 703, Steps 3-5. m/z (ESI, +ve ion) 230.2 (M+Na)+.

Step 3: (1S,3'R,6'R,7'S,8'E,10'R,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'S,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide The title compound was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate, AA12A) and (2S,4S)-1-methoxy-4-methyl-hex-5-ene-2-sulfonamide and (2S,4R)-1-methoxy-4-methylhex-5-ene-2-sulfonamide by similar procedures described in Example 458, Steps 6-7, and isolated as the first isomer from the reversed phase preparatory HPLC separation. ¹H NMR (400 MHz, CD₃OD) δ 7.73 (d, J=8.6 Hz, 1H), 7.16 (dd, J=2.3, 8.4 Hz, 1H), 7.10 (d, J=2.2 Hz, 1H), 7.00-6.95 (m, 1H), 6.95-6.91 (m, 1H), 6.80 (d, J=1.6 Hz, 1H), 5.80 (dd, J=5.5, 15.8 Hz, 1H), 5.68-5.54 (m, 1H), 4.39-4.30 (m, 1H), 4.29-4.24 (m, 1H), 4.15-4.00 (m, 2H), 3.90-3.74 (m, 3H), 3.63 (d, J=13.9 Hz, 1H), 3.37 (s, 3H), 3.19 (d, J=14.1 Hz, 1H), 3.04 (dd, J=9.4, 15.3 Hz, 1H), 2.86-2.68 (m, 2H), 2.58-1.60 (m, 12H), 1.52-1.40 (m, 1H), 1.07 (d, J=6.5 Hz, 3H). m/z (ESI, +ve ion) 629.2 (M+H)+.

Example 472. (1S,3'R,6'R,7'S,8'E,10'S,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'R,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide The title compound was obtained as the second eluting isomer from the reversed phase preparatory HPLC separation in Example 471, Step 3. ¹H NMR (400 MHz, CD₃OD) δ 7.73 (d, J=8.6 Hz, 1H), 7.16 (dd, J=2.3, 8.4 Hz, 1H), 7.10 (d, J=2.2 Hz, 1H), 7.05-7.00 (m, 1H), 6.97-6.89 (m, 2H), 5.93-5.84 (m, 1H), 5.63 (ddd, J=1.6, 6.7, 15.8 Hz, 1H), 4.28-4.17 (m, 2H), 4.11-4.07 (m, 2H), 4.00-3.89 (m, 2H), 3.82 (d, J=14.9 Hz, 1H), 3.65 (d, J=14.1 Hz, 1H), 3.40 (s, 3H), 3.09 (dd, J=9.5, 15.4 Hz, 1H), 2.89-2.64 (m, 2H), 2.49-1.55 (m, 13H), 1.50-1.39 (m, 1H), 1.09 (d, J=6.7 Hz, 3H). m/z (ESI, +ve ion) 629.2 (M+H)+.

Example 473. (1S,3'R,6'R,7'S,8'E,10'R,12'S)-6-chloro-7'-methoxy-12'-(methoxymethyl)-10'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'S,12'S)-6-chloro-7'-methoxy-12'-(methoxymethyl)-10'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

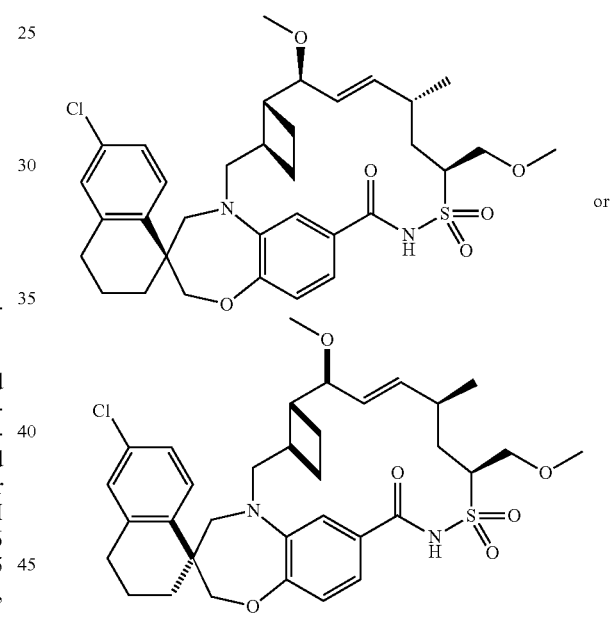

The title compound was prepared in an analogous manner to that described in Example 404, Step 2 using (1S,3'R,6'R,7'S,8'E,10'R,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'S,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 471) and iodomethane. ¹H NMR (500 MHz, CD₃OD) δ 7.72 (d, J=8.6 Hz, 1H), 7.16 (dd, J=2.2, 8.6 Hz, 1H), 7.10 (d, J=2.2 Hz, 1H), 6.98-6.95 (m, 1H), 6.93-6.91 (m, 1H), 6.79 (d, J=1.7 Hz, 1H), 5.95 (dd, J=4.8, 15.5 Hz, 1H), 5.46 (ddd, J=1.5, 8.2, 15.5 Hz, 1H), 4.50-4.36 (m, 1H), 4.12-4.01 (m, 2H), 3.88-3.83 (m, 2H), 3.77 (dd, J=3.8, 8.2 Hz, 1H), 3.64 (d, J=14.2 Hz, 1H), 3.37 (s, 3H), 3.25 (s, 3H), 3.20 (d, J=14.2 Hz, 1H), 3.05 (dd, J=9.7, 15.3 Hz, 1H), 2.86-2.65 (m, 2H), 2.60-2.43 (m, 2H), 2.39-1.65 (m, 11H), 1.49-1.39 (m, 1H), 1.10 (d, J=6.6 Hz, 3H). m/z (ESI, +ve ion) 657.2 (M+H)+.

Example 474. (1S,3'R,6'R,7'S,8'E,10'R,12'S)-6-chloro-7'-hydroxy-10'-methyl-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'S)-6-chloro-7'-hydroxy-10'-methyl-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'R)-6-chloro-7'-hydroxy-10'-methyl-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'R)-6-chloro-7'-hydroxy-10'-methyl-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide


or

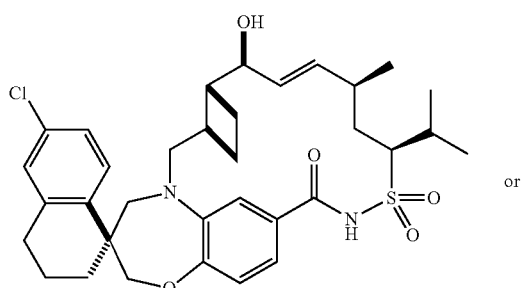

or

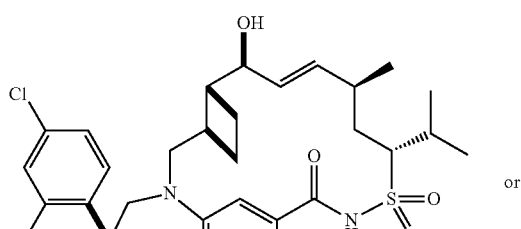

or

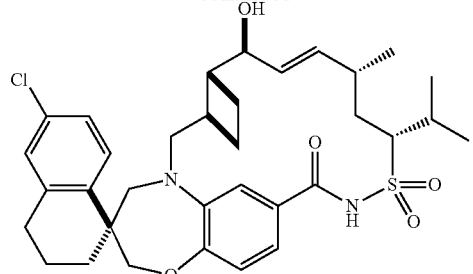

Step 1: (S)-3-methylpent-4-en-1-ol and (S)-3-methylpent-4-en-1-ol

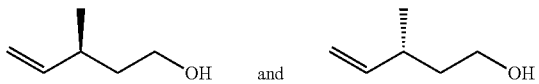

and

To a 500-mL round-bottomed flask was added 3-methyl-4-pentenoic acid (6.38 ml, 52.6 mmol) in THF (210 ml). The solution was cooled to 0° C., and lithium aluminum hydride, 1.0 M solution in tetrahydrofuran (60.0 ml, 60.0 mmol) was added to the solution through an addition funnel. The resulting mixture was stirred at this temperature for 4 h. The reaction was quenched by addition of 2.28 mL of water, 4.56 mL of 10% NaOH, and 6.84 mL of water in order. The solid was filtered off, and the solution was dried over MgSO$_4$, filtered and concentrated to provide the crude title compound as colorless oil (3.40 g, 65%). $^1$H NMR (400 MHz, CDCl$_3$) δ 5.63-5.88 (m, 1H), 4.86-5.11 (m, 2H), 3.57-3.77 (m, 2H), 2.24-2.43 (m, 1H), 1.54-1.71 (m, 2H), 0.95-1.09 (m, 3H).

Step 2: (S)-3-methylpent-4-enal and (R)-3-methylpent-4-enal

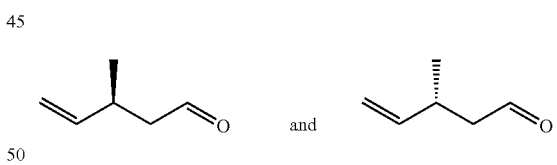

and

To a solution of oxalyl chloride (12.7 ml, 25.5 mmol) in DCM (50 mL) at −78° C. was added dimethyl sulfoxide anhydrous (3.61 ml, 50.9 mmol) under N$_2$. After the solution was stirred for 2 min, a solution of (S)-3-methylpent-4-en-1-ol and (S)-3-methylpent-4-en-1-ol (1.70 g, 17.0 mmol) in DCM (10 mL) was added, and the resulting mixture was stirred at this temperature for 15 min. Triethylamine (11.8 ml, 85.0 mmol) was added, and the mixture was stirred at ambient temperature for 20 min. The reaction mixture was diluted with DCM, washed with 1 M HCl aqueous solution, saturated NaHCO$_3$ aqueous solution, saturated NaCl solution, dried over MgSO$_4$ and concentrated to give the title compound (1.30 g, 78% yield). $^1$H NMR (400 MHz, CDCl$_3$) δ 9.28-9.97 (m, 1H), 5.80 (ddd, J=6.85, 10.37, 17.22 Hz, 1H), 4.91-5.14 (m, 2H), 2.68-2.86 (m, 1H), 2.30-2.54 (m, 2H), 1.10 (d, J=6.85 Hz, 3H).

Step 3: (3S,5S)-2,5-dimethylhept-6-en-3-ol and (3S,5R)-2,5-dimethylhept-6-en-3-ol and (3R,5S)-2,5-dimethylhept-6-en-3-ol and (3R,5R)-2,5-dimethylhept-6-en-3-ol

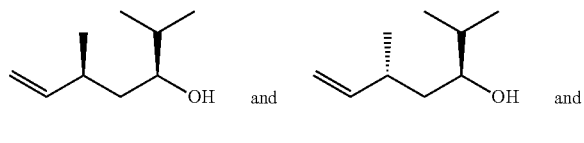

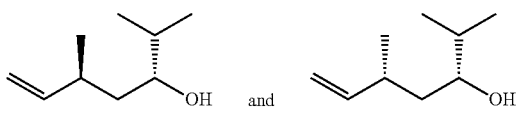

To the solution of (S)-3-methylpent-4-enal and (R)-3-methylpent-4-enal (1.50 g, 15.3 mmol) in THF (61.1 ml) in a 250-mL round-bottomed flask at −78° C. was added isopropylmagnesium chloride (15.3 ml, 30.6 mmol). The resulting mixture was stirred at this temperature for 1 h and gradually warmed up to ambient temperature. The reaction mixture was diluted with saturated NH$_4$Cl (20 mL), and extracted with EtOAc (2×30 mL). The organic extract was washed with saturated NaCl (10 mL), and dried over MgSO$_4$. The solution was filtered and concentrated in vacuo to give the crude material. The crude material was purified by chromatography through a Redi-Sep pre-packed silica gel column (40 g), eluting with a gradient of 0% to 35% EtOAc in hexane to provide the title compound (1.10 g, 51% yield) as colorless oil. $^1$H NMR (500 MHz, CDCl$_3$) δ 5.55-5.91 (m, 1H), 4.84-5.13 (m, 2H), 3.33-3.53 (m, 1H), 2.28-2.47 (m, 1H), 1.58-1.72 (m, 1H), 1.35-1.51 (m, 2H), 1.04 (dd, J=5.87, 6.85 Hz, 3H), 0.83-0.94 (m, 6H).

Step 4: (3S,5S)-2,5-dimethylhept-6-ene-3-sulfonamide and (3S,5R)-2,5-dimethylhept-6-ene-3-sulfonamide and (3R,5S)-2,5-dimethylhept-6-ene-3-sulfonamide and (3R,5R)-2,5-dimethylhept-6-ene-3-sulfonamide

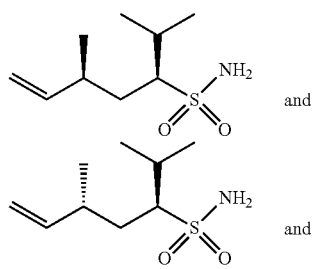

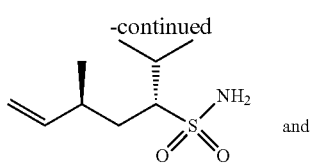

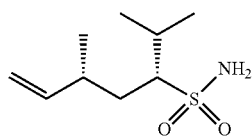

The title compound was prepared from (3S,5S)-2,5-dimethylhept-6-en-3-ol and (3S,5R)-2,5-dimethylhept-6-en-3-ol and (3R,5S)-2,5-dimethylhept-6-en-3-ol and (3R,5R)-2,5-dimethylhept-6-en-3-ol by similar procedures described in Example 703, Steps 3-5. m/z (ESI, +ve ion) 206.6 (M+H)$^+$.

Step 5: (1S,3'R,6'R,7'S,8'E,10'R,12'S)-6-chloro-7'-hydroxy-10'-methyl-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'S)-6-chloro-7'-hydroxy-10'-methyl-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'R)-6-chloro-7'-hydroxy-10'-methyl-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'R)-6-chloro-7'-hydroxy-10'-methyl-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compound was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate, AA12A) and (3S,5S)-2,5-dimethylhept-6-ene-3-sulfonamide and (3S,5R)-2,5-dimethylhept-6-ene-3-sulfonamide and (3R,5S)-2,5-dimethylhept-6-ene-3-sulfonamide and (3R,5R)-2,5-dimethylhept-6-ene-3-sulfonamide by similar procedures described in Example 458, Steps 6-7, and isolated as the first isomer from the reversed phase preparatory HPLC separation. $^1$H NMR (400 MHz, CDCl$_3$) δ 8.21 (br. s., 1H), 7.71 (d, J=8.6 Hz, 1H), 7.18 (dd, J=2.3, 8.4 Hz, 1H), 7.09 (d, J=2.3 Hz, 1H), 6.94 (s, 2H), 6.78 (s, 1H), 5.80 (dd, J=5.3, 15.5 Hz, 1H), 5.67-5.57 (m, 1H), 4.38-4.31 (m, 1H), 4.17-4.00 (m, 3H), 3.80 (d, J=15.1 Hz, 1H), 3.71 (d, J=13.9 Hz, 1H), 3.17 (d, J=14.1 Hz, 1H), 3.02 (dd, J=9.0, 15.1 Hz, 1H), 2.88 (dtd, J=2.6, 6.9, 13.8 Hz, 1H), 2.82-2.69 (m, 2H), 2.53-0.78 (m, 23H). m/z (ESI, +ve ion) 627.2 (M+H)$^+$.

Example 475. (1S,3'R,6'R,7'S,8'E,10'S,12'S)-6-chloro-7'-hydroxy-10'-methyl-12'-(1-methylethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'R,12'S)-6-chloro-7'-hydroxy-10'-methyl-12'-(1-methylethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'S,12'R)-6-chloro-7'-hydroxy-10'-methyl-12'-(1-methylethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'R,12'R)-6-chloro-7'-hydroxy-10'-methyl-12'-(1-methylethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

 or

 or

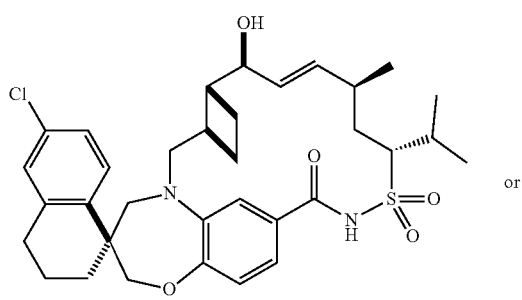 or

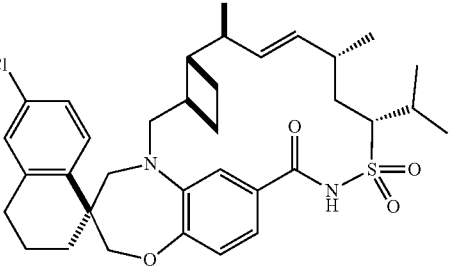

The title compound was obtained as the second eluting isomer from the reversed phase preparatory HPLC separation in Example 474, Step 5. $^1$H NMR (400 MHz, CDCl$_3$) δ 8.51 (br. s., 1H), 7.71 (d, J=8.6 Hz, 1H), 7.22-7.14 (m, 2H), 7.09 (d, J=1.8 Hz, 1H), 7.03-6.98 (m, 1H), 6.97-6.91 (m, 1H), 5.74-5.50 (m, 2H), 4.24-3.97 (m, 3H), 3.91-3.77 (m, 2H), 3.73 (d, J=14.7 Hz, 1H), 3.27 (d, J=14.3 Hz, 1H), 3.08 (dd, J=6.3, 15.5 Hz, 1H), 2.85-2.60 (m, 3H), 2.58-2.42 (m, 2H), 2.25 (br. s., 1H), 2.07-1.59 (m, 10H), 1.44 (t, J=12.3 Hz, 1H), 1.24 (d, J=6.8 Hz, 3H), 1.18 (d, J=7.0 Hz, 3H), 1.06 (d, J=6.7 Hz, 3H). m/z (ESI, +ve ion) 627.2 (M+H)$^+$.

Example 476. (1S,3'R,6'R,7'S,8'E,10'S,12'R)-6-chloro-7'-hydroxy-10'-methyl-12'-(1-methylethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'R,12'S)-6-chloro-7'-hydroxy-10'-methyl-12'-(1-methylethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'S,12'S)-6-chloro-7'-hydroxy-10'-methyl-12'-(1-methylethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'R,12'R)-6-chloro-7'-hydroxy-10'-methyl-12'-(1-methylethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

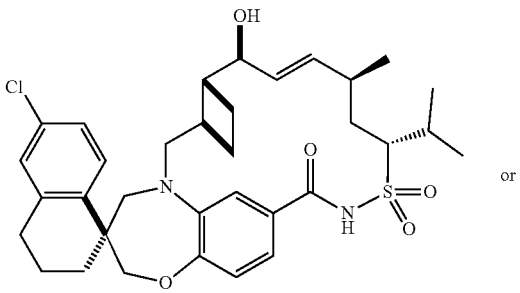 or

1061

-continued

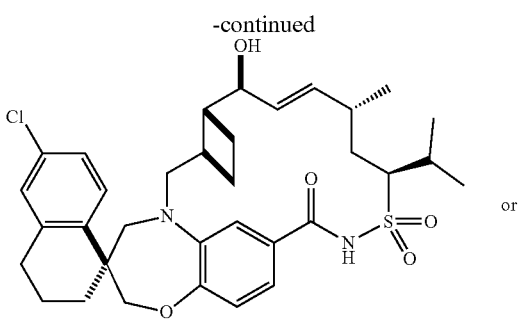

or

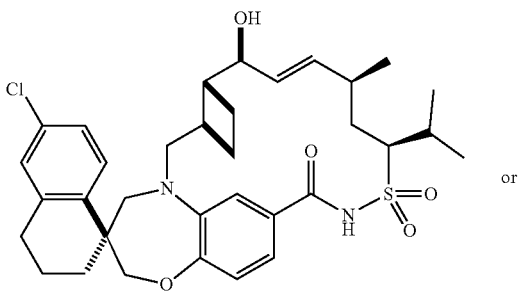

or

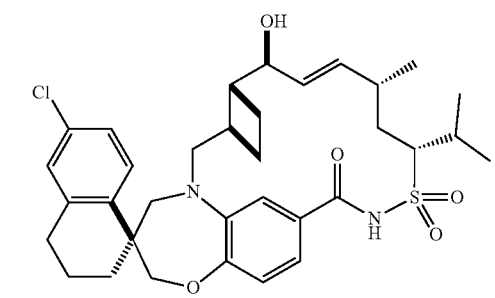

The title compound was obtained as the third eluting isomer from the reversed phase preparatory HPLC separation in Example 474, Step 5. $^1$H NMR (400 MHz, CDCl$_3$) δ 8.17 (s, 1H), 8.03-7.68 (m, 1H), 7.65 (d, J=8.6 Hz, 1H), 7.19-7.13 (m, 1H), 7.10 (d, J=2.3 Hz, 1H), 6.99-6.86 (m, 2H), 5.70 (dd, J=5.5, 15.8 Hz, 1H), 5.18 (br. s., 1H), 4.42-1.19 (m, 28H), 1.10 (d, J=6.7 Hz, 3H), 1.00 (d, J=6.7 Hz, 3H). m/z (ESI, +ve ion) 627.2 (M+H)$^+$.

1062

Example 477. (1S,3'R,6'R,7'S,8'E,10'R,12'S)-6-chloro-7'-hydroxy-12'-(2-methoxyethyl)-10'-methyl-3,4-dihydro-2H,15'H-spiro[naphthalene-1,22'-[20] oxa[13]thia[1,14]diazatetracyclo[14.7.2.0$^{3,6}$.0$^{19,24}$] pentacosa [8,16,18,24]tetraen]-15'-one 13',13'-dioxide or (1S,3'R,6'R,7'S,8'E,10'S,12'S)-6-chloro-7'-hydroxy-12'-(2-methoxyethyl)-10'-methyl-3,4-dihydro-2H,15'H-spiro[naphthalene-1,22'-[20]oxa [13]thia[1,14]diazatetracyclo[14.7.2.0$^{3,6}$.0$^{19,24}$] pentacosa [8,16,18,24]tetraen]-15'-one 13',13'-dioxide or (1S,3'R,6'R,7'S,8'E,10'S,12'R)-6-chloro-7'-hydroxy-12'-(2-methoxyethyl)-10'-methyl-3,4-dihydro-2H,15'H-spiro[naphthalene-1,22'-[20]oxa [13]thia[1,14]diazatetracyclo[14.7.2.0$^{3,6}$.0$^{19,24}$] pentacosa [8,16,18,24]tetraen]-15'-one 13',13'-dioxide or (1S,3'R,6'R,7'S,8'E,10'R,12'R)-6-chloro-7'-hydroxy-12'-(2-methoxyethyl)-10'-methyl-3,4-dihydro-2H,15'H-spiro[naphthalene-1,22'-[20]oxa [13]thia[1,14]diazatetracyclo[14.7.2.0$^{3,6}$.0$^{19,24}$] pentacosa [8,16,18,24]tetraen]-15'-one 13',13'-dioxide

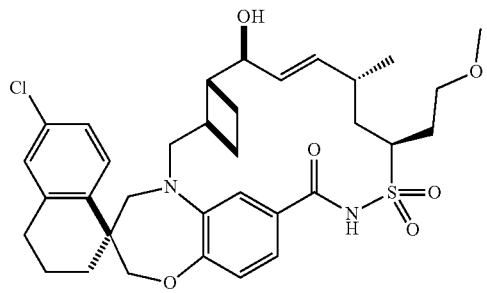

or

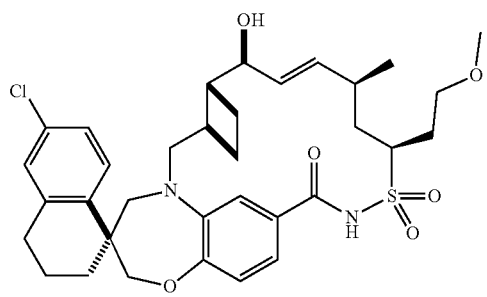

or

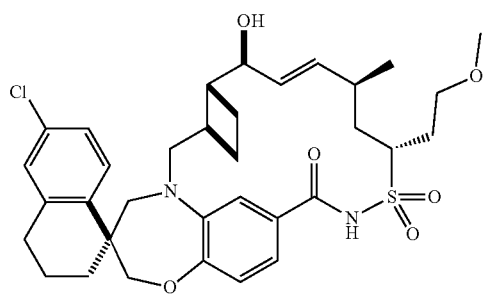

or

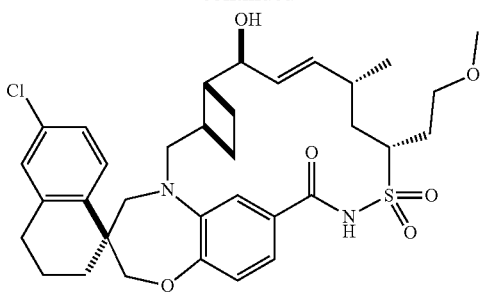

Step 1: (3R,5S)-1-methoxy-5-methylhept-6-en-3-ol and (3R,5R)-1-methoxy-5-methylhept-6-en-3-ol and (3S,5R)-1-methoxy-5-methylhept-6-en-3-ol and (3S,5S)-1-methoxy-5-methylhept-6-en-3-ol

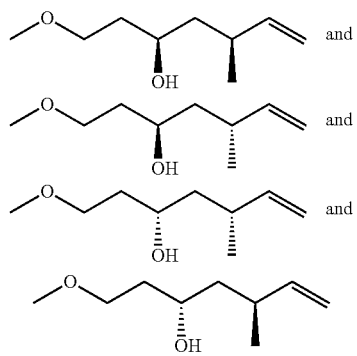

A mixture of magnesium (1.49 g, 61.4 mmol) in THF (10.0 mL) with a catalytic amount of iodine and 1,2 dibromoethane (0.176 ml, 2.05 mmol) was sonicated for 35 min. To this suspension solution was added one fifth amount of 4-bromo-3-methylbut-1-ene (6.10 g, 40.9 mmol) in THF (20 ml) at 50° C. over 30 min, and rest of 4-bromo-3-methylbut-1-ene was dropwise added at 20-30° C., and the resulting mixture was stirred at ambient temperature for 1.5 h. The mixture containing (2-methylbut-3-en-1-yl) magnesium bromide was used to next step directly.

To 3-methoxy-propionaldehyde (3.61 ml, 41.0 mmol) in THF (2 mL) at −15° C. was added (2-methylbut-3-en-1-yl) magnesium bromide prepared above (7.11 g, 40.9 mmol) in THF (14 ml) slowly over 1 h. The resulting mixture was allowed to warm up to ambient temperature and stirred overnight. The reaction mixture was cooled in an ice bath, and quenched with ice-cold saturated ammonium chloride aqueous solution. This mixture was further diluted with ether and ice-cold water. The organic layer was separated and concentrated. The residue was purified by chromatography through a Redi-Sep pre-packed silica gel column (24 g), eluting with a gradient of 0% to 35% EtOAc in hexane to provide the title compound (3.00 g, 46% yield). $^1$H NMR (400 MHz, CDCl$_3$) δ 5.60-5.88 (m, 1H), 4.83-5.11 (m, 2H), 3.87 (tdd, J=3.62, 12.59, 16.55 Hz, 1H), 3.49-3.69 (m, 2H), 3.30-3.42 (m, 3H), 2.69-2.89 (m, 1H), 2.30-2.51 (m, 1H), 1.64-1.80 (m, 2H), 1.53 (dt, J=4.69, 9.19 Hz, 1H), 1.25-1.45 (m, 1H), 1.05 (dd, J=2.64, 6.75 Hz, 3H).

Step 2: 2-(((3R,5S)-1-methoxy-5-methylhept-6-en-3-yl)thio)pyrimidine and 2-(((3R,5R)-1-methoxy-5-methylhept-6-en-3-yl)thio)pyrimidine and 2-(((3S,5R)-1-methoxy-5-methylhept-6-en-3-yl)thio)pyrimidine and 2-(((3S,5S)-1-methoxy-5-methylhept-6-en-3-yl)thio)pyrimidine

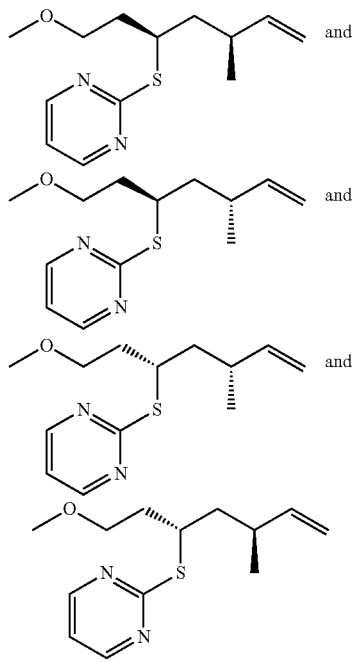

To an ice-cold solution of tributylphosphine (3.98 ml, 16.1 mmol) in 15 mL of anhydrous and degassed THF was added diethyl azodicarboxylate, 40% w/w in toluene (7.34 ml, 16.1 mmol) dropwise. During the addition, the mixture became the orange color immediately. To this solution was added (3R,5S)-1-methoxy-5-methylhept-6-en-3-ol and (3R,5R)-1-methoxy-5-methylhept-6-en-3-ol and (3S,5R)-1-methoxy-5-methylhept-6-en-3-ol and (3S,5S)-1-methoxy-5-methylhept-6-en-3-ol (1.50 g, 9.48 mmol) dropwise via a syringe. The resulting mixture was aged at 0° C. for 1 h, and then a suspension of pyrimidine-2-thiol (2.66 g, 23.7 mmol) in 15 mL of anhydrous THF was added. The reaction mixture was stirred at ambient temperature overnight. The yellow solid was filtered off, and the filtrate concentrated. The residue was purified by chromatography through a Redi-Sep pre-packed silica gel column (40 g), eluting with a gradient of 0% to 35% EtOAc in hexane, to provide the title compound (1.85 g, 77% yield) as colorless oil. m/z (ESI, +ve ion) 253.2 (M+H)$^+$.

Step 3: (3R,5S)-1-methoxy-5-methylhept-6-ene-3-sulfonamide and (3R,5R)-1-methoxy-5-methylhept-6-ene-3-sulfonamide and (3S,5R)-1-methoxy-5-methylhept-6-ene-3-sulfonamide and (3S,5S)-1-methoxy-5-methylhept-6-ene-3-sulfonamide

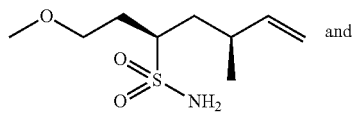

1065

-continued

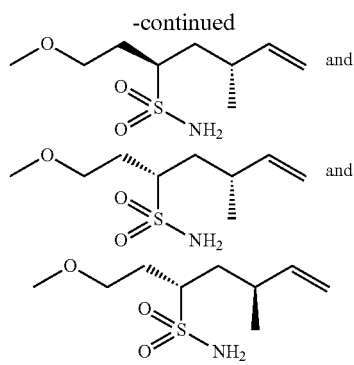

and

The title compound was prepared from 2-(((3R,5S)-1-methoxy-5-methylhept-6-en-3-yl)thio)pyrimidine and 2-(((3R,5R)-1-methoxy-5-methylhept-6-en-3-yl)thio)pyrimidine and 2-(((3S,5R)-1-methoxy-5-methylhept-6-en-3-yl)thio)pyrimidine and 2-(((3S,5S)-1-methoxy-5-methylhept-6-en-3-yl)thio)pyrimidine by similar procedures described in Example 703, Steps 4-5. m/z (ESI, +ve ion) 244.2 (M+Na)$^+$.

Step 4: (1S,3'R,6'R,7'S,8'E,10'R,12'S)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'S)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'R)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'R)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compound was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate, AA12A) and (3R,5S)-1-methoxy-5-methylhept-6-ene-3-sulfonamide and (3R,5R)-1-methoxy-5-methylhept-6-ene-3-sulfonamide and (3S,5R)-1-methoxy-5-methylhept-6-ene-3-sulfonamide and (3S,5S)-1-methoxy-5-methylhept-6-ene-3-sulfonamide by similar procedures described in Example 458, Steps 6-7, and isolated as the first isomer from the reversed phase preparatory HPLC separation. $^1$H NMR (500 MHz, CDCl$_3$) δ 8.48 (br. s., 1H), 7.71 (d, J=8.6 Hz, 1H), 7.18 (dd, J=2.1, 8.4 Hz, 1H), 7.09 (d, J=2.0 Hz, 1H), 7.01 (d, J=7.8 Hz, 1H), 6.97-6.91 (m, 1H), 6.86 (br. s., 1H), 5.94 (dd, J=5.6, 15.4 Hz, 1H), 5.66 (dd, J=7.0, 15.5 Hz, 1H), 4.40-4.25 (m, 2H), 4.18-4.02 (m, 2H), 3.76 (d, J=15.2 Hz, 1H), 3.69 (d, J=14.2 Hz, 1H), 3.63 (t, J=6.4 Hz, 2H), 3.39 (s, 3H), 3.22 (d, J=14.2 Hz, 1H), 3.14-3.03 (m, 1H), 2.87-2.68 (m, 2H), 2.57-2.41 (m, 3H), 2.40-2.28 (m, 1H), 2.18 (ddd, J=3.3, 9.4, 15.2 Hz, 1H), 2.07-1.59 (m, 10H), 1.45 (t, J=12.3 Hz, 1H), 1.06 (d, J=6.6 Hz, 3H). m/z (ESI, +ve ion) 643.2 (M+H)$^+$.

Example 478. (1S,3'R,6'R,7'S,8'E,10'S,12'S)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'S)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'R)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'R)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide


or


or

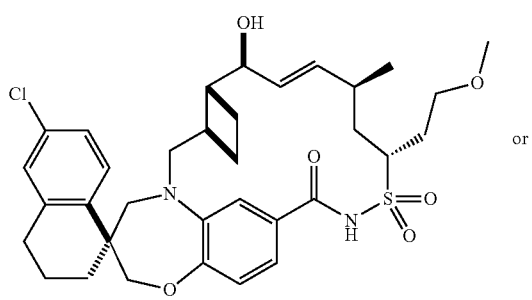

or

1067

-continued

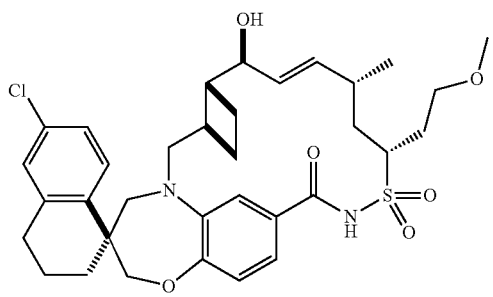

The title compound was obtained as the second eluting isomer from the reversed phase preparatory HPLC separation in Example 477, Step 4. $^1$H NMR (400 MHz, CDCl$_3$) δ 8.11 (s, 1H), 7.71 (d, J=8.6 Hz, 1H), 7.18 (dd, J=2.2, 8.5 Hz, 1H), 7.12-7.03 (m, 2H), 6.97-6.86 (m, 2H), 5.83-5.73 (m, 1H), 5.67-5.54 (m, 1H), 4.24-4.07 (m, 4H), 3.83 (dd, J=3.2, 15.4 Hz, 1H), 3.77-3.65 (m, 3H), 3.39 (s, 3H), 3.26 (d, J=14.1 Hz, 1H), 3.06 (dd, 15.5 Hz, 1H), 2.88-2.67 (m, 2H), 2.52-1.54 (m, 15H), 1.42 (t, J=12.5 Hz, 1H), 1.08 (d, J=6.8 Hz, 3H). m/z (ESI, +ve ion) 643.2 (M+H)$^+$. 120954-23

Example 479. (1S,3'R,6'R,7'S,8'E,10'S,12'R)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'S)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'S)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'R)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

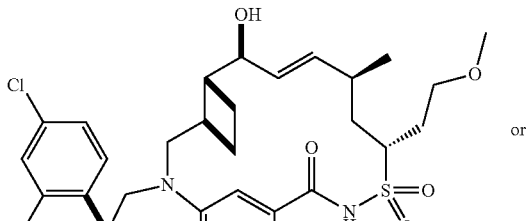

1068

-continued

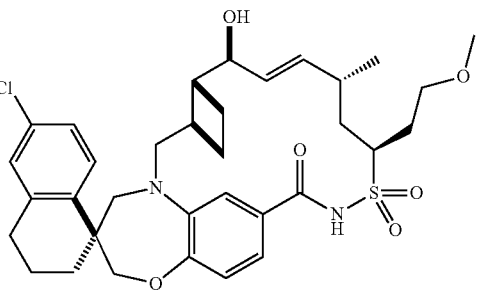

or

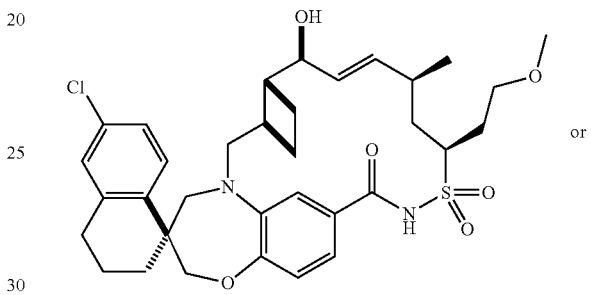

or

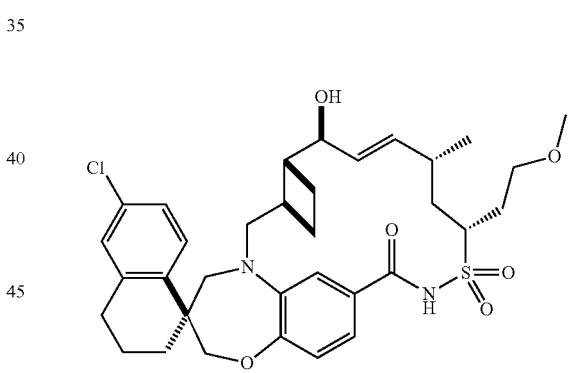

The title compound was obtained as the third eluting isomer from the reversed phase preparatory HPLC separation in Example 477, Step 4. $^1$H NMR (500 MHz, CDCl$_3$) δ 8.17 (s, 1H), 7.81 (br. s., 1H), 7.64 (d, J=8.6 Hz, 1H), 7.16 (dd, J=2.2, 8.3 Hz, 1H), 7.11 (d, J=2.2 Hz, 1H), 6.97-6.82 (m, 2H), 5.73 (dd, J=4.6, 15.9 Hz, 1H), 5.10 (br. s., 1H), 4.39-4.22 (m, 2H), 4.08 (br. s., 1H), 3.93-3.78 (m, 2H), 3.74-3.61 (m, 2H), 3.43 (s, 3H), 3.27 (d, J=14.4 Hz, 1H), 3.08 (d, J=13.9 Hz, 1H), 2.75 (t, J=5.6 Hz, 2H), 2.65-2.54 (m, 1H), 2.52-2.38 (m, 2H), 2.24-1.11 (m, 14H), 0.99 (d, J=6.6 Hz, 3H). m/z (ESI, +ve ion) 643.2 (M+H)$^+$.

Example 480. (1S,3'R,6'R,7'S,8'E,10'R,12'R)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'S,12'R)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'R,12'S)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'S,12'S)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

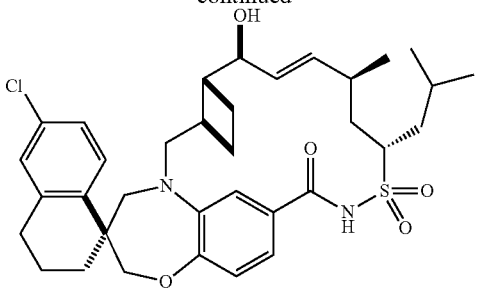

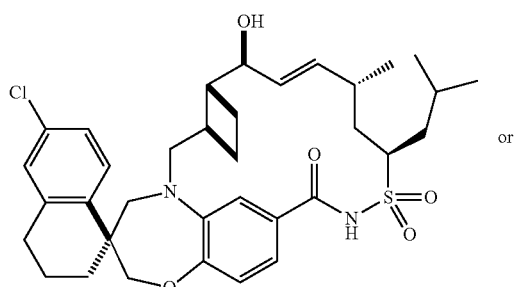 or

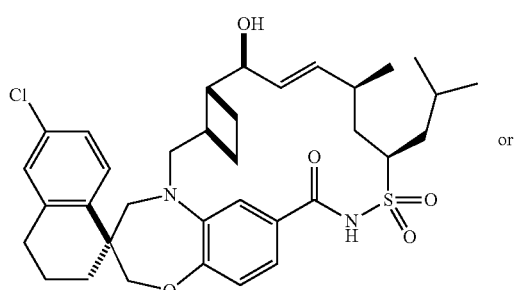 or

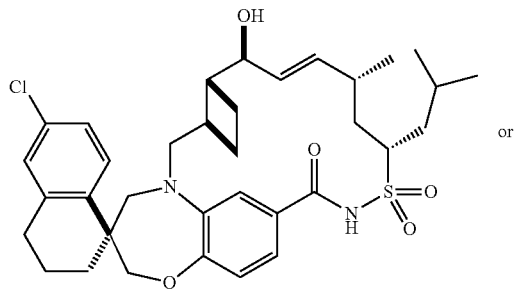 or

Step 1: (4S,6S)-2,6-dimethyloct-7-en-4-ol and (4S,6R)-2,6-dimethyloct-7-en-4-ol and (4R,6S)-2,6-dimethyloct-7-en-4-ol and (4R,6R)-2,6-dimethyloct-7-en-4-ol

 and

 and

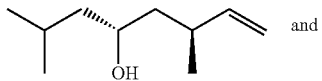 and

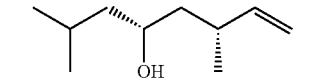

The title compound was prepared in an analogous manner to that described in Example 471, Step 1 using 2-isobutyloxirane. $^1$H NMR (400 MHz, CDCl$_3$) δ 5.59-5.94 (m, 1H), 4.79-5.18 (m, 2H), 3.77 (dtd, J=4.40, 8.40, 16.55 Hz, 1H), 2.29-2.53 (m, 1H), 1.69-1.92 (m, 1H), 1.31-1.56 (m, 4H), 1.19-1.30 (m, 1H), 1.02-1.09 (m, 3H), 0.90-0.98 (m, 6H).

Step 2: (4S,6S)-2,6-dimethyloct-7-ene-4-sulfonamide and (4S,6R)-2,6-dimethyloct-7-ene-4-sulfonamide and (4R,6R)-2,6-dimethyloct-7-ene-4-sulfonamide and (4R,6S)-2,6-dimethyloct-7-ene-4-sulfonamide

 and

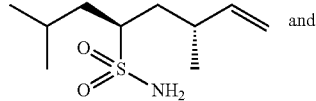 and

-continued

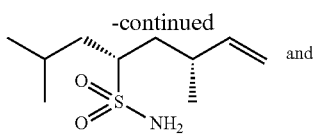

and

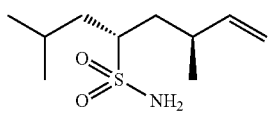

The title compound was prepared from (4S,6S)-2,6-dimethyloct-7-en-4-ol and (4S,6R)-2,6-dimethyloct-7-en-4-ol and (4R,6S)-2,6-dimethyloct-7-en-4-ol and (4R,6R)-2,6-dimethyloct-7-en-4-ol by similar procedures described in Example 477, Steps 2-3. m/z (ESI, +ve ion) 220.2 (M+H)$^+$.

Step 3: (1S,3'R,6'R,7'S,8'E,10'R,12'R)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'R)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'S)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'S)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[18,16,18,24]tetraen]-15'-one 13',13'-dioxide The title compound was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate, AA12A) and (4S,6S)-2,6-dimethyloct-7-ene-4-sulfonamide and (4S,6R)-2,6-dimethyloct-7-ene-4-sulfonamide and (4R,6R)-2,6-dimethyloct-7-ene-4-sulfonamide and (4R,6S)-2,6-dimethyloct-7-ene-4-sulfonamide by similar procedures described in Example 458, Steps 6-7, and isolated as the first isomer from the reversed phase preparatory HPLC separation. $^1$H NMR (500 MHz, CDCl$_3$) δ 8.38 (br. s., 1H), 7.71 (d, J=8.6 Hz, 1H), 7.18 (dd, J=2.2, 8.3 Hz, 1H), 7.10 (d, J=2.0 Hz, 1H), 7.02 (d, J=8.1 Hz, 1H), 6.97-6.91 (m, 1H), 6.84 (br. s., 1H), 6.01 (dd, J=5.4, 15.7 Hz, 1H), 5.68 (dd, J=6.8, 15.9 Hz, 1H), 4.30 (dd, 7.1 Hz, 1H), 4.25-4.17 (m, 1H), 4.16-4.06 (m, 2H), 3.82-3.66 (m, 2H), 3.22 (d, J=13.9 Hz, 1H), 3.16-3.02 (m, 1H), 2.83-2.69 (m, 2H), 2.50-2.32 (m, 3H), 2.18-1.16 (m, 14H), 1.06 (d, J=6.6 Hz, 3H), 1.04 (d, J=6.6 Hz, 3H), 0.99 (d, J=6.4 Hz, 3H). m/z (ESI, +ve ion) 641.2 (M+H)$^+$.

Example 481. (1S,3'R,6'R,7'S,8'E,10'S,12'R)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide or (1S,3'R,6'R,7'S,8'E,10'R,12'R)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide or (1S,3'R,6'R,7'S,8'E,10'R,12'S)-6-chloro-7'-hydroxy-10'-methyl-12'-(2-methylpropyl)-3,4-dihydro-2H,15'H-spiro[naphthalene-1,22'-[20]oxa [13]thia[1,14]diazatetracyclo[14.7.2.0$^{3,6}$.0$^{19,24}$] pentacosa [8,16,18,24]tetraen]-15'-one 13',13'-dioxide or (1S,3'R,6'R,7'S,8'E,10'S,12'S)-6-chloro-7'-hydroxy-10'-methyl-12'-(2-methylpropyl)-3,4-dihydro-2H,15'H-spiro[naphthalene-1,22'-[20]oxa [13]thia[1,14]diazatetracyclo[14.7.2.0$^{3,6}$.0$^{19,24}$] pentacosa [8,16,18,24]tetraen]-15'-one 13',13'-dioxide


or


or

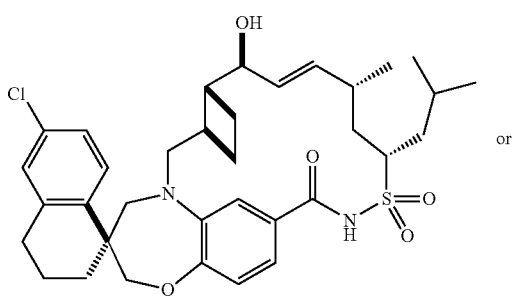

or

1073
-continued

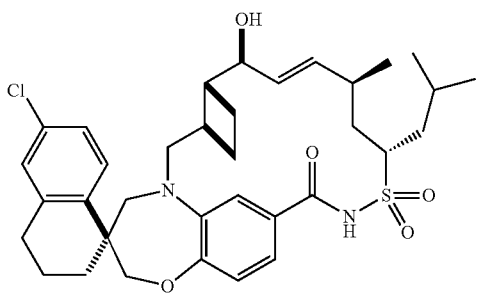

The title compound was obtained as the second eluting isomer from the reversed phase preparatory HPLC separation in Example 480, Step 3. ¹H NMR (400 MHz, CDCl₃) δ 8.18 (s, 1H), 7.71 (d, J=8.6 Hz, 1H), 7.18 (dd, J=2.2, 8.4 Hz, 1H), 7.12-7.05 (m, 2H), 6.98-6.82 (m, 2H), 5.88-5.73 (m, 1H), 5.70-5.57 (m, 1H), 4.18 (t, J=5.7 Hz, 1H), 4.11 (s, 2H), 4.07-3.96 (m, 1H), 3.85 (dd, J=2.9, 15.3 Hz, 1H), 3.73 (d, J=14.3 Hz, 1H), 3.25 (d, J=14.3 Hz, 1H), 3.04 (dd, J=8.1, 15.4 Hz, 1H), 2.90-2.65 (m, 2H), 2.53-1.55 (m, 15H), 1.49-1.36 (m, 2H), 1.08 (d, J=6.7 Hz, 3H), 1.02 (t, J=5.8 Hz, 6H). m/z (ESI, +ve ion) 641.2 (M+H)⁺.

Example 482. (1S,3'R,6'R,7'S,8'E,10'R,12'S)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'R,12'R)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'S,12'R)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'S,12'S)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

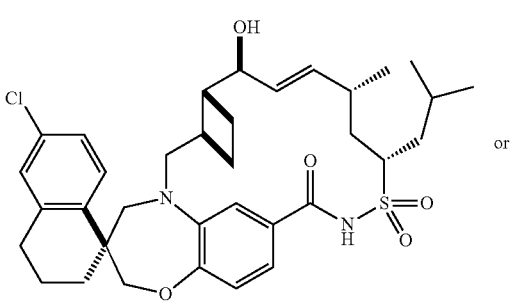

or

1074
-continued

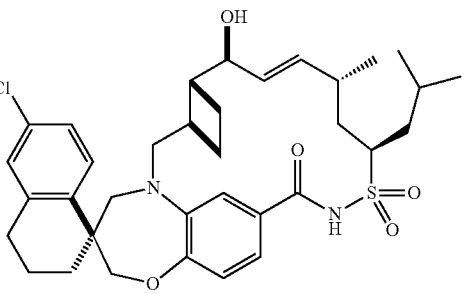

or

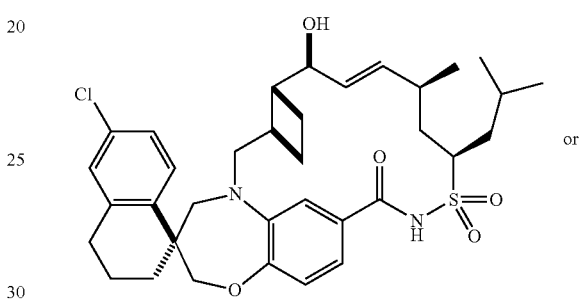

or

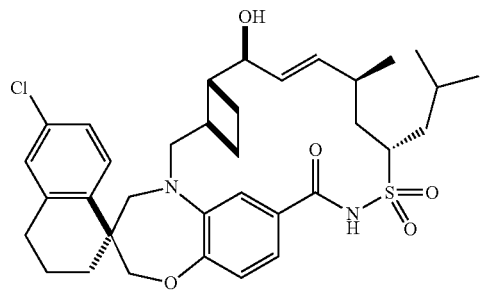

The title compound was obtained as the third eluting isomer from the reversed phase preparatory HPLC separation in Example 480, Step 3. ¹H NMR (400 MHz, CDCl₃) δ 8.15 (s, 1H), 7.68 (d, J=8.6 Hz, 1H), 7.18 (dd, J=2.2, 8.5 Hz, 1H), 7.12-7.04 (m, 3H), 6.95 (d, J=8.2 Hz, 1H), 5.95 (dd, J=5.7, 15.3 Hz, 1H), 5.66 (dd, J=4.2, 15.7 Hz, 1H), 4.19-4.08 (m, 3H), 4.01 (br. s., 1H), 3.63-3.54 (m, 1H), 3.52-3.35 (m, 2H), 2.78 (br. s., 2H), 2.69-2.48 (m, 2H), 2.35 (d, J=5.3 Hz, 1H), 2.23-2.10 (m, 1H), 2.02-1.52 (m, 14H), 1.10 (d, J=6.8 Hz, 3H), 1.05 (d, J=6.5 Hz, 3H), 0.99 (d, J=6.5 Hz, 3H). m/z (ESI, +ve ion) 641.2 (M+H)⁺.

Example 483. (1S,3'R,6'R,7'S,8'E,10'S,12'S)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'R)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'R)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'S)-6-chloro-7'-hydroxy-10'-methyl-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

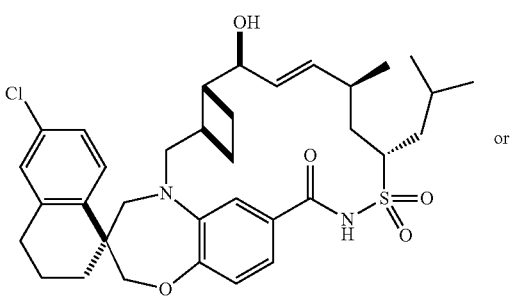

or


or


or

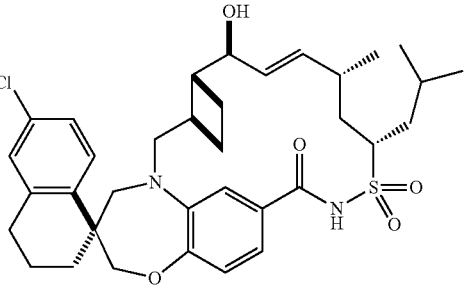

The title compound was obtained as the fourth eluting isomer from the reversed phase preparatory HPLC separation in Example 480, Step 3. $^{1}$H NMR (400 MHz, CDCl$_3$) δ 8.15 (s, 1H), 7.68 (d, J=8.4 Hz, 1H), 7.18 (dd, J=2.2, 8.4 Hz, 1H), 7.12-7.02 (m, 3H), 6.95 (d, J=8.2 Hz, 1H), 5.95 (dd, J=6.0, 16.7 Hz, 1H), 5.66 (dd, J=5.8, 15.9 Hz, 1H), 4.24-4.06 (m, 3H), 4.01 (br. s., 1H), 3.63-3.54 (m, 1H), 3.52-3.40 (m, 2H), 2.78 (br. s., 2H), 2.69-2.48 (m, 2H), 2.36 (br. s., 1H), 2.23-2.10 (m, 1H), 2.01-1.49 (m, 14H), 1.10 (d, J=6.8 Hz, 3H), 1.05 (d, J=6.7 Hz, 3H), 0.99 (d, J=6.5 Hz, 3H). m/z (ESI, +ve ion) 641.2 (M+H)$^{+}$.

Example 484. (1S,3'R,6'R,7'S,8'E,10'R,12'S)-6-chloro-7'-methoxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'S)-6-chloro-7'-methoxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'R)-6-chloro-7'-methoxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'R)-6-chloro-7'-methoxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

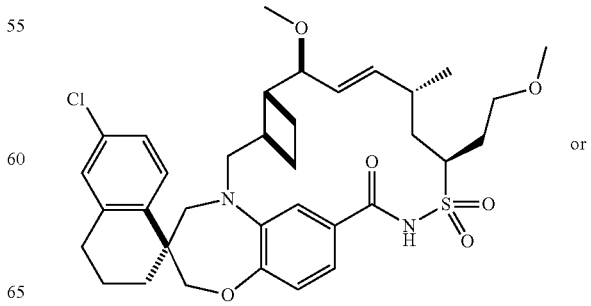

or

-continued

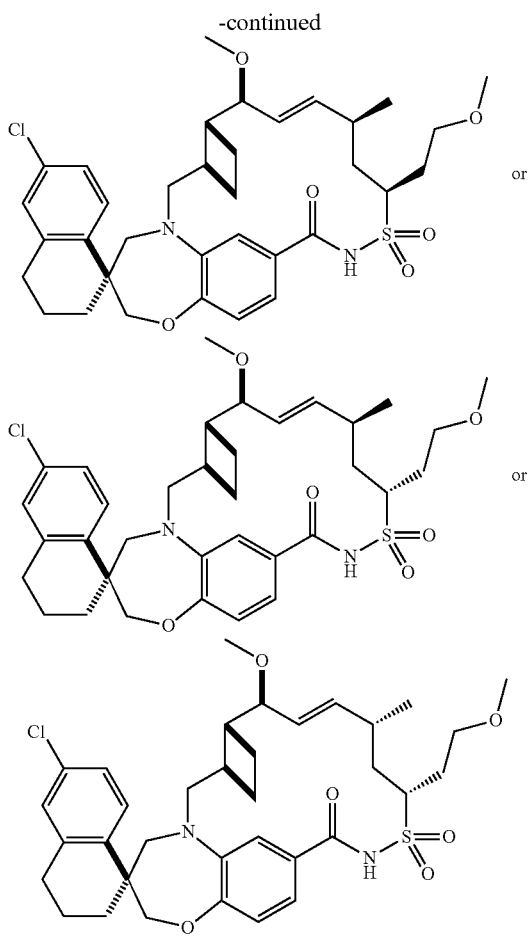

The title compound was prepared in an analogous manner to that described in Example 404, Step 2 using (1S,3'R,6'R,7'S,8'E,10'R,12'S)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'S)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 477) and iodomethane. $^1$H NMR (400 MHz, CDCl$_3$) δ 8.07 (br. s., 1H), 7.70 (d, J=8.4 Hz, 1H), 7.18 (dd, J=2.2, 8.6 Hz, 1H), 7.09 (d, J=2.2 Hz, 1H), 6.97-6.87 (m, 2H), 6.78 (s, 1H), 6.00 (dd, J=4.4, 15.6 Hz, 1H), 5.55-5.41 (m, 1H), 4.47 (dd, J=3.0, 7.3 Hz, 1H), 4.14-4.01 (m, 2H), 3.83-3.67 (m, 3H), 3.66-3.53 (m, 2H), 3.33 (s, 3H), 3.27 (s, 3H), 3.17 (d, J=14.3 Hz, 1H), 3.01 (dd, J=9.3, 15.2 Hz, 1H), 2.84-2.69 (m, 2H), 2.60-2.35 (m, 3H), 2.27-2.11 (m, 2H), 2.07-1.17 (m, 10H), 1.10 (d, J=6.7 Hz, 3H). m/z (ESI, +ve ion) 657.2 (M+H)$^+$.

Example 485. (1S,3'R,6'R,7'S,8'E,10'S,12'S)-6-chloro-7'-methoxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'S)-6-chloro-7'-methoxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'R)-6-chloro-7'-methoxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'R)-6-chloro-7'-methoxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

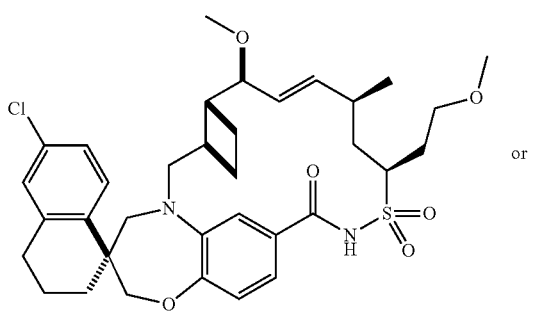

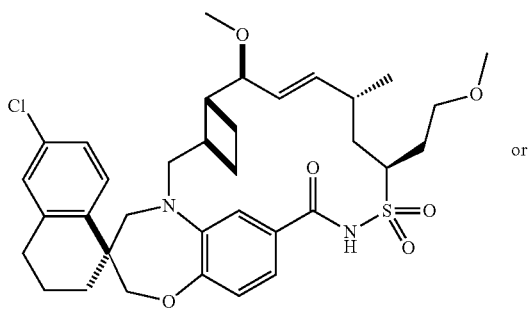


-continued

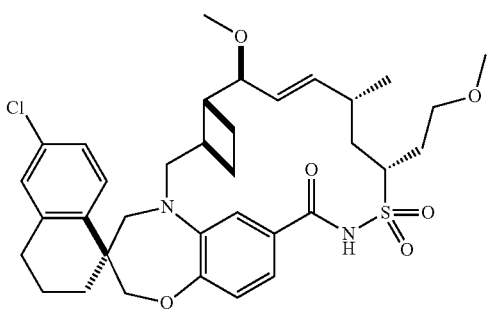

The title compound was prepared in an analogous manner to that described in Example 404, Step 2 using (1S,3'R,6'R,7'S,8'E,10'S,12'S)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 478) and iodomethane. $^1$H NMR (400 MHz, CDCl$_3$) δ 8.03 (br. s., 1H), 7.71 (d, J=8.4 Hz, 1H), 7.18 (dd, J=2.2, 8.4 Hz, 1H), 7.09 (d, J=2.0 Hz, 1H), 6.95-6.86 (m, 3H), 5.95 (dd, J=3.2, 15.7 Hz, 1H), 5.53-5.41 (m, 1H), 4.32 (t, J=8.3 Hz, 1H), 4.10 (s, 2H), 3.82 (d, J=15.1 Hz, 1H), 3.76-3.62 (m, 4H), 3.38 (s, 3H), 3.25 (s, 3H), 3.15 (d, J=6.7 Hz, 1H), 3.01 (dd, J=9.9, 15.2 Hz, 1H), 2.87-2.68 (m, 2H), 2.54-2.36 (m, 3H), 2.30-2.22 (m, 1H), 2.13-1.23 (m, 11H), 1.12 (d, J=6.7 Hz, 3H). m/z (ESI, +ve ion) 657.2 (M+H)$^+$.

Example 486. (1S,3'R,6'R,7'S,8'E,10'S,12'R)-6-chloro-7'-methoxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-7'-methoxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'S)-6-chloro-7'-methoxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-7'-methoxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

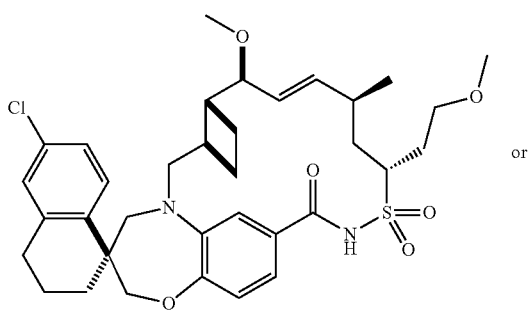

or

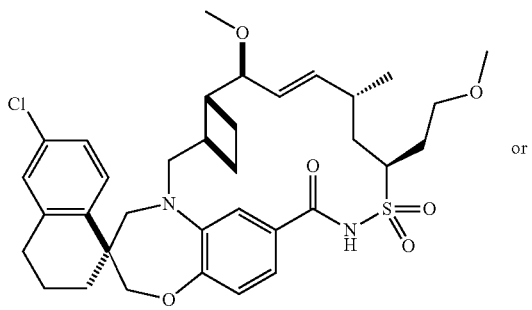

or

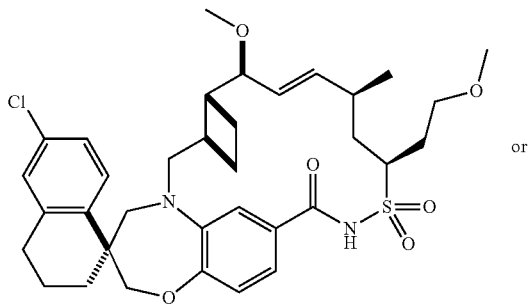

or

1081
-continued

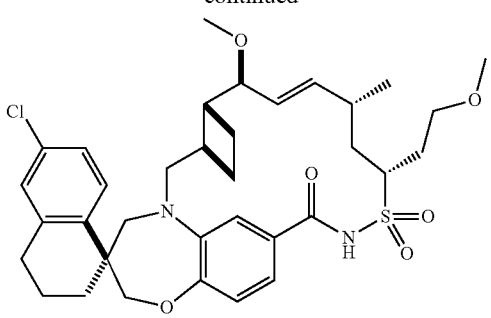

The title compound was prepared in an analogous manner to that described in Example 404, Step 2 using (1S,3'R,6'R,7'S,8'E,10'S,12'R)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'S)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'R)-6-chloro-7'-hydroxy-12'-(2-methoxyethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 479) and iodomethane. $^1$H NMR (500 MHz, CDCl$_3$) δ 8.05 (br. s., 1H), 7.67 (d, J=8.3 Hz, 1H), 7.22-7.03 (m, 3H), 7.01-6.81 (m, 2H), 5.74 (d, J=13.0 Hz, 1H), 5.40 (dd, J=8.1, 15.6 Hz, 1H), 4.19-4.04 (m, 2H), 3.85-0.61 (m, 34H). m/z (ESI, +ve ion) 657.2 (M+H)$^+$.

Example 487. (1S,3'R,6'R,7'S,8'E,10'R,12'R)-6-chloro-7'-hydroxy-10'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-7'-hydroxy-10'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

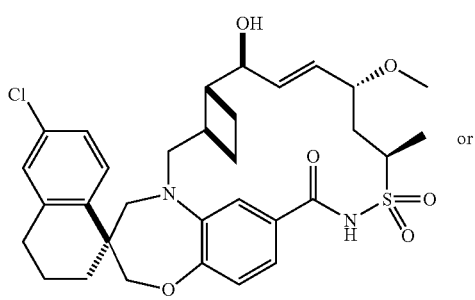

1082
-continued

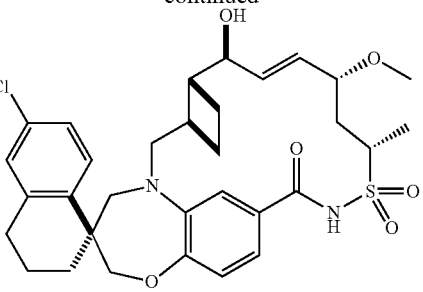

Step 1: (2S,4R)-4-hydroxy-N,N-bis(4-methoxybenzyl)hex-5-ene-2-sulfonamide and (2R,4R)-4-hydroxy-N,N-bis(4-methoxybenzyl)hex-5-ene-2-sulfonamide

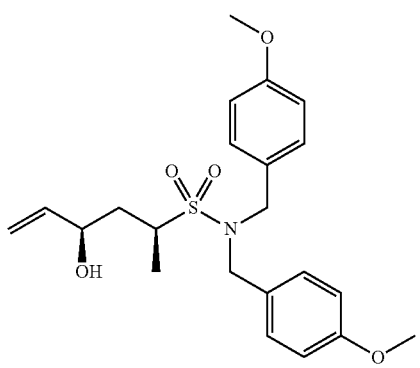

and

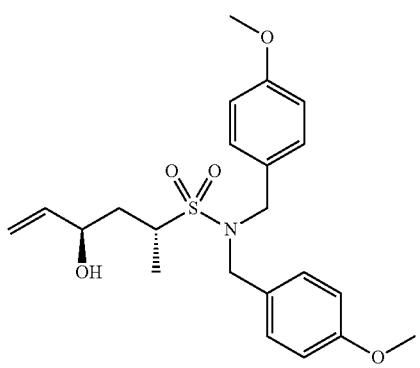

To a solution of N,N-bis(4-methoxybenzyl)ethanesulfonamide (1.00 g, 2.86 mmol, Intermediate, EE13) in THF (9.5 ml) in a 150-mL round-bottomed flask at −78° C. was added butyllithium, 2.5 M solution in THF (1.26 ml, 3.15 mmol) slowly. The resulting mixture was stirred at this temperature for 15 min, and then (r)-2-vinyl-oxirane (0.346 ml, 4.29 mmol) was added. The mixture was stirred at ambient temperature overnight. The reaction mixture was diluted with saturated NH$_4$Cl (10 mL) and extracted with EtOAc (2×20 mL). The organic extract was washed with saturated NaCl (10 mL) and dried over MgSO$_4$. The solution was filtered and concentrated in vacuo to give the crude material. The crude material was purified by chromatography through a Redi-Sep pre-packed silica gel column (40 g), eluting with a gradient of 0% to 35% EtOAc in hexane, to provide the title compound (0.42 g, 35%). $^1$H NMR (500 MHz, CDCl$_3$)

δ 7.20-7.24 (m, 4H), 6.86-6.91 (m, 4H), 5.79 (ddd, J=6.11, 10.58, 17.06 Hz, 1H), 5.14-5.32 (m, 2H), 4.37-4.47 (m, 3H), 4.17-4.22 (m, 2H), 3.82-3.86 (m, 6H), 3.18 (sxt, J=6.75 Hz, 1H), 2.19 (td, J=5.96, 14.24 Hz, 1H), 2.03-2.07 (m, 1H), 1.71-1.81 (m, 1H), 1.32 (d, J=7.09 Hz, 3H).

Step 2: (2S,4R)-4-methoxyhex-5-ene-2-sulfonamide and (2R,4R)-4-methoxyhex-5-ene-2-sulfonamide

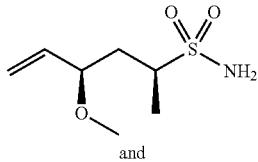

and

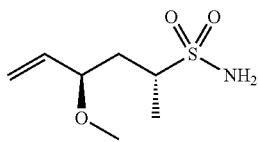

The title compound was prepared from (2S,4R)-4-hydroxy-N,N-bis(4-methoxybenzyl)hex-5-ene-2-sulfonamide and (2R,4R)-4-hydroxy-N,N-bis(4-methoxybenzyl)hex-5-ene-2-sulfonamide by similar procedures described in Example 434, Steps 3-4. m/z (ESI, +ve ion) 216.2 (M+Na)$^+$.

Step 3: (1S,3'R,6'R,7'S,8'E,10'R,12'R)-6-chloro-7'-hydroxy-10'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'S)-6-chloro-7'-hydroxy-10'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compound was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate, AA12A) and (2S,4R)-4-methoxyhex-5-ene-2-sulfonamide and (2R,4R)-4-methoxyhex-5-ene-2-sulfonamide by similar procedures described in Example 458, Steps 6-7, and isolated as the first isomer from the reversed phase preparatory HPLC separation. $^1$H NMR (500 MHz, CDCl$_3$) δ 8.37 (br. s., 1H), 7.71 (d, J=8.6 Hz, 1H), 7.19 (dd, J=2.3, 8.4 Hz, 1H), 7.09 (d, J=2.2 Hz, 1H), 7.02 (s, 1H), 6.95-6.86 (m, 2H), 5.90 (dd, J=6.1, 15.4 Hz, 1H), 5.63 (dd, J=6.4, 15.4 Hz, 1H), 4.28 (t, J=5.5 Hz, 1H), 4.16-4.03 (m, 2H), 3.99 (dt, J=4.3, 7.5 Hz, 1H), 3.85 (dd, J=3.3, 15.3 Hz, 1H), 3.70 (d, J=14.4 Hz, 1H), 3.67-3.61 (m, 1H), 3.18 (s, 3H), 3.02 (dd, J=8.1, 15.4 Hz, 1H), 2.84-2.69 (m, 2H), 2.55-2.44 (m, 1H), 2.43-2.31 (m, 1H), 2.26-1.63 (m, 11H), 1.59 (d, J=6.8 Hz, 3H), 1.40 (t, J=13.2 Hz, 1H). m/z (ESI, +ve ion) 615.2 (M+H)$^+$.

Example 488. (1S,3'R,6'R,7'S,8'E,10'R,12'S)-6-chloro-7'-hydroxy-10'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'R)-6-chloro-7'-hydroxy-10'-methoxy-12'-methyl-3,4-dihydro-2H,15'H-spiro [naphthalene-1,22'-[20]oxa[13]thia[1,14] diazatetracyclo[14.7.2.0$^{3,6}$.0$^{19,24}$]pentacosa [8,16,18,24]tetraen]-15'-one 13',13'-dioxide

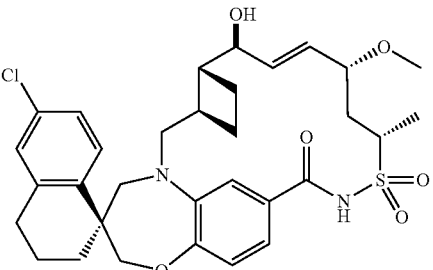

or

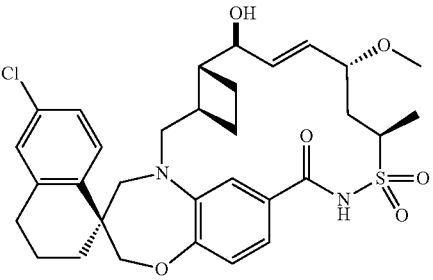

The title compound was obtained as the later eluting isomer from the reversed phase preparatory HPLC separation in Example 487, Step 3. $^1$H NMR (500 MHz, CDCl$_3$) δ 8.10 (s, 1H), 7.64 (d, J=8.6 Hz, 1H), 7.58 (br. s., 1H), 7.16 (dd, J=2.4, 8.6 Hz, 1H), 7.10 (d, J=2.2 Hz, 1H), 6.96-6.89 (m, 2H), 5.83-5.78 (m, 1H), 5.75-5.66 (m, 1H), 4.34-4.25 (m, 1H), 4.23 (s, 2H), 4.08 (d, J=8.3 Hz, 1H), 3.95-3.89 (m, 1H), 3.37-3.28 (m, 1H), 3.23 (s, 3H), 3.20-3.03 (m, 2H), 2.79-2.73 (m, 2H), 2.55 (d, J=8.3 Hz, 1H), 2.34 (quin, J=8.9 Hz, 1H), 2.22-1.38 (m, 15H). m/z (ESI, +ve ion) 615.2 (M+H)$^+$.

Example 489. (1S,3'R,6'R,7'S,8'E,10'S,12'R)-6-chloro-7'-hydroxy-10'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'S)-6-chloro-7'-hydroxy-10'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide Example 490. (1S,3'R,6'R,7'S,8'E,10'S,12'S)-6-chloro-7'-hydroxy-10'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-7'-hydroxy-10'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

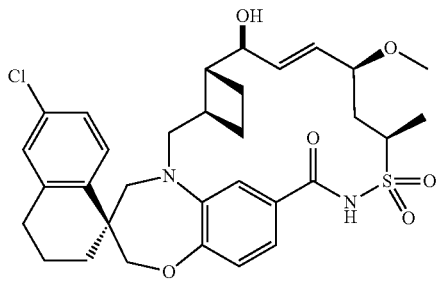

or

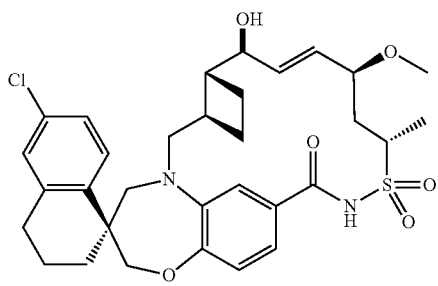

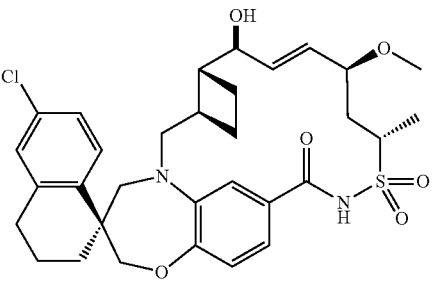

or

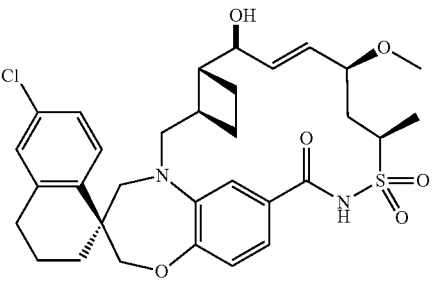

The title compound was prepared from (s)-2-vinyloxirane by similar procedures described in Example 487, Steps 1-3, and isolated as the first isomer from the reversed phase preparatory HPLC separation. $^1$H NMR (500 MHz, CDCl$_3$) δ 8.21 (br. s., 1H), 7.70 (d, J=8.3 Hz, 1H), 7.18 (dd, J=2.1, 8.4 Hz, 1H), 7.10 (d, J=2.0 Hz, 1H), 7.02-6.89 (m, 3H), 5.96-5.87 (m, 1H), 5.85-5.74 (m, 1H), 4.38-4.22 (m, 2H), 4.16-4.04 (m, 2H), 3.89 (t, J=5.3 Hz, 1H), 3.83 (d, J=15.2 Hz, 1H), 3.70 (d, J=14.4 Hz, 1H), 3.25 (s, 3H), 3.06 (dd, J=8.3, 15.4 Hz, 1H), 2.86-2.70 (m, 2H), 2.61-2.46 (m, 1H), 2.37 (t, J=8.2 Hz, 1H), 2.18-1.56 (m, 14H), 1.43 (t, J=12.6 Hz, 1H). m/z (ESI, +ve ion) 615.2 (M+H)$^+$.

The title compound was obtained as the later eluting isomer from the reversed phase preparatory HPLC separation in Example 489. $^1$H NMR (500 MHz, CDCl$_3$) δ 8.16 (s, 1H), 7.77 (br. s., 1H), 7.63 (d, J=8.6 Hz, 1H), 7.15 (dd, J=2.2, 8.6 Hz, 1H), 7.11 (d, J=2.2 Hz, 1H), 6.95-6.88 (m, 2H), 5.92 (dd, J=4.4, 16.1 Hz, 1H), 5.24 (dd, J=7.9, 16.0 Hz, 1H), 4.31-4.15 (m, 3H), 3.97 (dd, J=4.0, 9.7 Hz, 1H), 3.91-3.80 (m, 2H), 3.55-3.45 (m, 1H), 3.28 (d, J=14.4 Hz, 1H), 3.20 (s, 3H), 3.08 (dd, J=3.3, 16.0 Hz, 1H), 2.75 (t, J=5.7 Hz, 2H), 2.68-2.58 (m, 1H), 2.55-2.45 (m, J=8.8 Hz, 1H), 2.03-1.66 (m, 10H), 1.63 (d, J=7.1 Hz, 3H), 1.42-1.31 (m, 1H). m/z (ESI, +ve ion) 615.2 (M+H)$^+$.

1087

Example 491. (1S,3'R,6'R,7'S,8'E,10'R)-6-chloro-7'-hydroxy-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S)-6-chloro-7'-hydroxy-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

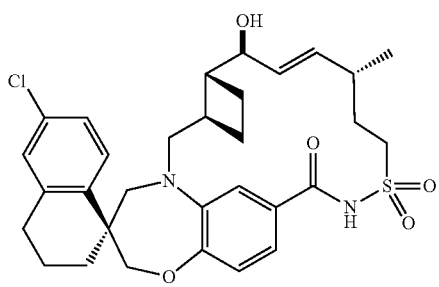

or

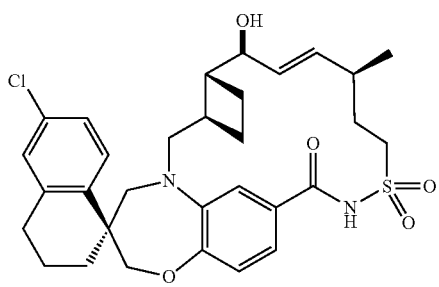

The title compound was prepared from oxirane by similar procedures described in Example 480, Steps 1-3, and isolated as the first isomer from the reversed phase preparatory HPLC separation. $^1$H NMR (500 MHz, CDCl$_3$) δ 8.16 (s, 1H), 7.68 (d, J=8.6 Hz, 1H), 7.18 (dd, J=2.3, 8.4 Hz, 1H), 7.10 (d, J=2.2 Hz, 1H), 6.98-6.86 (m, 2H), 5.74-5.51 (m, 2H), 4.21-4.09 (m, 3H), 3.90 (br. s., 1H), 3.68-3.22 (m, 5H), 2.85-2.70 (m, 2H), 2.56-2.34 (m, 3H), 2.22-1.24 (m, 11H). 1.04 (d, J=6.8 Hz, 3H). m/z (ESI, +ve ion) 585.2 (M+H)$^+$.

1088

Example 492. (1S,3'R,6'R,7'S,8'E,10'S)-6-chloro-7'-hydroxy-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R)-6-chloro-7'-hydroxy-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

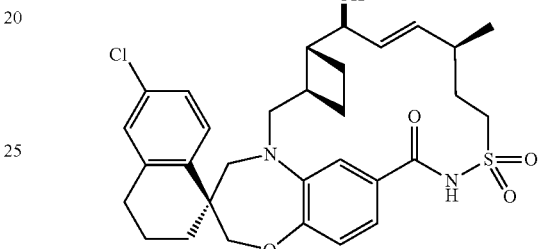

or

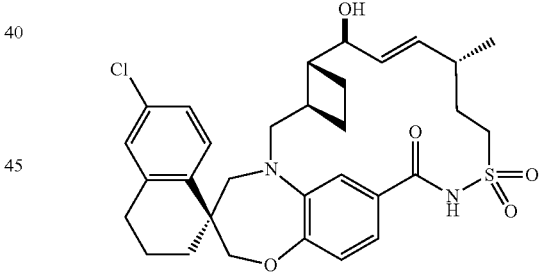

The title compound was obtained as the later eluting isomer from the reversed phase preparatory HPLC separation in Example 491. $^1$H NMR (500 MHz, CDCl$_3$) δ 8.19 (br. s., 1H), 7.69 (d, J=8.6 Hz, 1H), 7.18 (dd, J=2.2, 8.6 Hz, 1H), 7.10 (d, J=2.2 Hz, 2H), 6.95 (s, 2H), 5.87 (dd, J=5.1, 14.9 Hz, 1H), 5.64 (ddd, J=1.3, 6.1, 15.8 Hz, 1H), 4.25 (br. s., 1H), 4.19-4.10 (m, 2H), 4.00 (d, J=10.8 Hz, 1H), 3.65 (d, J=14.9 Hz, 2H), 3.50-3.19 (m, 3H), 2.85-2.68 (m, 2H), 2.44 (br. s., 2H), 2.29 (br. s., 1H), 2.06-1.43 (m, 11H), 1.09 (d, J=6.8 Hz, 3H). m/z (ESI, +ve ion) 615.2 (M+H)$^+$.

Example 493. (1S,3'R,6'R,7'S,8'E,10'S)-6-chloro-7'-hydroxy-10',11',11'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'R,8'E,10'S)-6-chloro-7'-hydroxy-10',11',11'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R)-6-chloro-7'-hydroxy-10',11',11'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'R,8'E,10'S)-6-chloro-7'-hydroxy-10',11',11'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

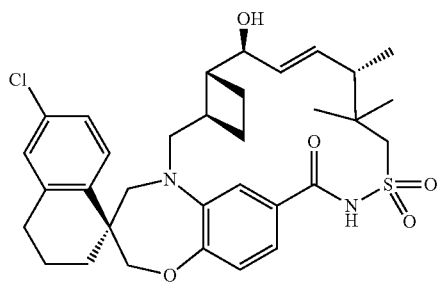

or

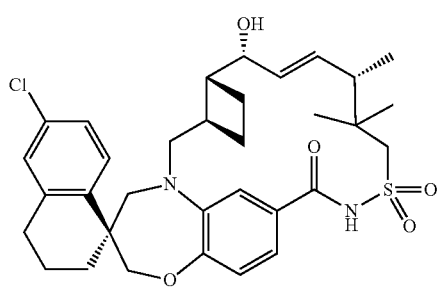

or

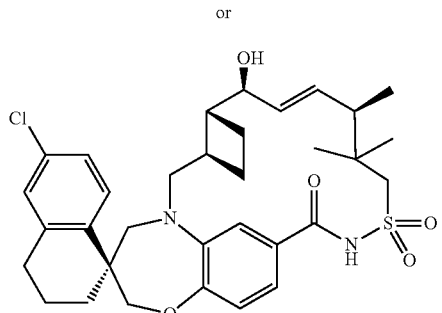

or

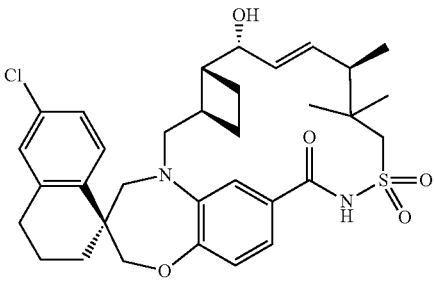

Step 1: (S)-2,2,3-trimethylpent-4-en-1-ol and (R)-2,2,3-trimethylpent-4-en-1-ol

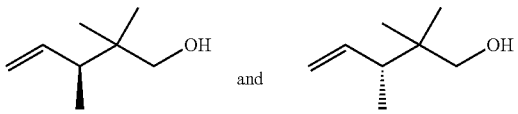

The title compound was prepared from (S)-2,2,3-trimethylpent-4-enoic acid and (R)-2,2,3-trimethylpent-4-enoic acid (prepared according to reference: *Tetrahedron*, 63(51), 12616-12620, 2007) by the similar procedure described in Example 474, Step 1. m/z (ESI, +ve ion) 129.2 (M+H)$^+$.

Step 2: (S)-2,2,3-trimethylpent-4-ene-1-sulfonamide and (R)-2,2,3-trimethylpent-4-ene-1-sulfonamide

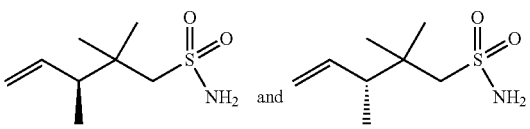

The title compound was prepared from (S)-2,2,3-trimethylpent-4-en-1-ol and (R)-2,2,3-trimethylpent-4-en-1-ol by similar procedures described in Example 703, Steps 3-5. m/z (ESI, +ve ion) 192.1 (M+H)$^+$.

Step 3: (S)-6'-chloro-5-(((1R,2R)-2-((S)-1-hydroxy-allyl)cyclobutyl)methyl)-N—(((R)-2,2,3-trimethyl-pent-4-en-1-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxyallyl)cyclobutyl)methyl)-N—(((S)-2,2,3-trimethylpent-4-en-1-yl)sulfonyl)-3',4,4',5-tetrahydro-2H,2'H-spiro[benzo[b][1,4]oxazepine-3,1'-naphthalene]-7-carboxamide

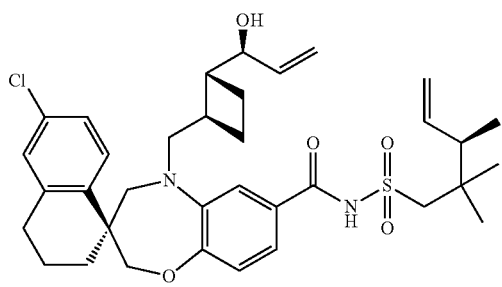

and

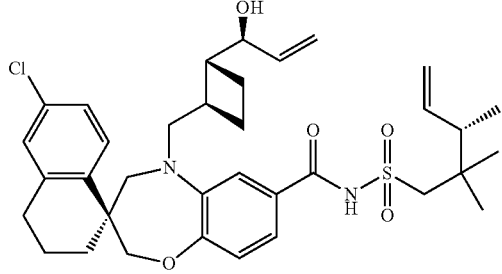

The title compound was prepared from (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Intermediate, AA11A) and (S)-2,2,3-trimethylpent-4-ene-1-sulfonamide and (R)-2,2,3-trimethylpent-4-ene-1-sulfonamide by the similar procedure described in Example 432, Step 4. m/z (ESI, +ve ion) 641.2 (M+H)$^+$.

Step 4: (S)-5-(((1R,2R)-2-acryloylcyclobutyl)methyl)-6'-chloro-N—(((R)-2,2,3-trimethylpent-4-en-1-yl)sulfonyl)-3',4,4',5-tetrahydro-2H,2'H-spiro[benzo[b][1,4]oxazepine-3,1'-naphthalene]-7-carboxamide and (S)-5-(((1R,2R)-2-acryloylcyclobutyl)methyl)-6'-chloro-N—(((S)-2,2,3-trimethylpent-4-en-1-yl)sulfonyl)-3',4,4',5-tetrahydro-2H,2'H-spiro[benzo[b][1,4]oxazepine-3,1'-naphthalene]-7-carboxamide

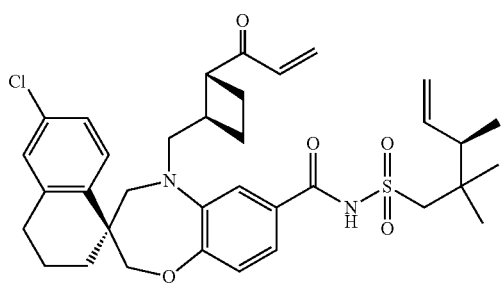

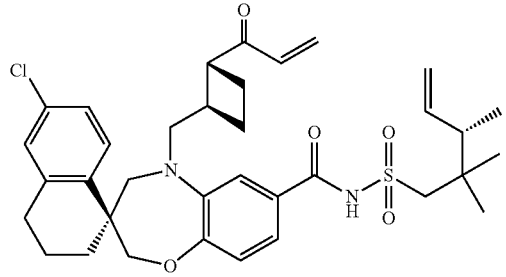

and

To a solution of (S)-6'-chloro-5-(((1R,2R)-2-((S)-1-hydroxy allyl)cyclobutyl)methyl)-N—(((R)-2,2,3-trimethyl-pent-4-en-1-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxyallyl)cyclobutyl)methyl)-N—(((S)-2,2,3-trimethylpent-4-en-1-yl)sulfonyl)-3',4,4',5-tetrahydro-2H,2'H-spiro[benzo[b][1,4]oxazepine-3,1'-naphthalene]-7-carboxamide (0.430 g, 0.671 mmol) in DCM (6.7 ml) was added dess-martin periodinane (0.341 g, 0.805 mmol). The resulting mixture was stirred at ambient temperature for 1 h. The reaction mixture was loaded on the column and purified by chromatography through a Redi-Sep pre-packed silica gel column (40 g), eluting with a gradient of 0% to 30% EtOAc in hexane, to provide the title compound (0.250 g, 58%). m/z (ESI, +ve ion) 639.2 (M+H)$^+$.

Step 5: (1S,3'R,6'R,8'E,10'R)-6-chloro-10',11',11'-trimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dion 13',13'-dioxide and (1S,3'R,6'R,8'E,10'S)-6-chloro-10',11',11'-trimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dione 13',13'-dioxide

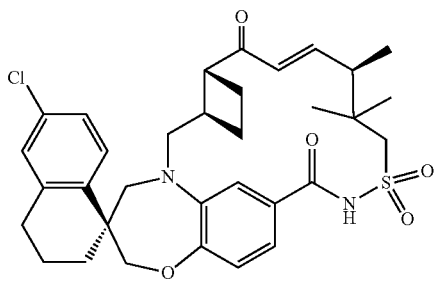

and

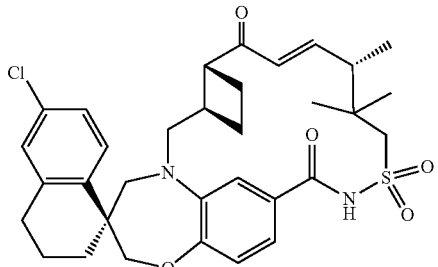

The title compound was prepared from (S)-5-(((1R,2R)-2-acryloylcyclobutyl)methyl)-6'-chloro-N—(((R)-2,2,3-trimethylpent-4-en-1-yl)sulfonyl)-3',4,4',5-tetrahydro-2H,2'H-spiro[benzo[b][1,4]oxazepine-3,1'-naphthalene]-7-carboxamide and (S)-5-(((1R,2R)-2-acryloylcyclobutyl)methyl)-6'-chloro-N—(((S)-2,2,3-trimethylpent-4-en-1-yl)sulfonyl)-3',4,4',5-tetrahydro-2H,2'H-spiro[benzo[b][1,4]oxazepine-3,1'-naphthalene]-7-carboxamide by the similar procedure described in Example 432, Step 5. m/z (ESI, +ve ion) 611.2 (M+H)+.

Step 6: (1S,3'R,6'R,7'S,8'E,10'S)-6-chloro-7'-hydroxy-10',11',11'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'R,8'E,10'S)-6-chloro-7'-hydroxy-10',11',11'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R)-6-chloro-7'-hydroxy-10',11',11'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'R,8'E,10'S)-6-chloro-7'-hydroxy-10',11',11'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide To a solution of (1S,3'R,6'R,8'E,10'R)-6-chloro-10',11',11'-trimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dion 13',13'-dioxide and (1S,3'R,6'R,8'E,10'S)-6-chloro-10',11',11'-trimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dione 13',13'-dioxide (70 mg, 0.12 mmol) in 3 mL of THF under N$_2$ at 0° C. was added borane tetrahydrofuran complex, 1.0 M in tetrahydrofuran (0.17 mL, 0.17 mmol). The reaction mixture was stirred at 0° C. for 1 h, and then quenched with MeOH at 0° C. The reaction mixture was diluted with saturated NH$_4$Cl solution and 30 mL of EtOAc. The organic layer was separated and concentrated. The residue was purified by chromatography, eluting with a gradient of 0% to 40% EtOAc (containing 0.3% AcOH) in hexane to provide the title compound as the first eluting isomer (12 mg, 34%). $^1$H NMR (400 MHz, CDCl$_3$) δ 8.99 (br. s., 1H), 7.73 (d, J=8.4 Hz, 1H), 7.26-7.21 (m, 2H), 7.18 (dd, J=2.3, 8.4 Hz, 1H), 7.10 (d, J=2.3 Hz, 1H), 6.96 (d, J=8.6 Hz, 1H), 6.01-5.90 (m, 1H), 5.86-5.76 (m, 1H), 4.31 (br. s., 1H), 4.11 (s, 2H), 3.99 (d, J=15.1 Hz, 1H), 3.91 (d, J=15.8 Hz, 1H), 3.68 (d, J=14.3 Hz, 1H), 3.58 (d, J=15.8 Hz, 1H), 3.22 (d, J=14.3 Hz, 1H), 3.02 (dd, J=8.7, 15.4 Hz, 1H), 2.85-2.69 (m, 2H), 2.65-2.44 (m, 3H), 2.26-2.14 (m, 1H), 2.08-1.37 (m, 8H), 1.24 (s, 3H), 1.09 (s, 3H), 1.01 (d, J=6.8 Hz, 3H). m/z (ESI, +ve ion) 613.2 (M+H)+.

Example 494. (1S,3'R,6'R,7'R,8'E,10'S)-6-chloro-7'-hydroxy-10',11',11'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S)-6-chloro-7'-hydroxy-10',11',11'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R)-6-chloro-7'-hydroxy-10',11',11'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'R,8'E,10'S)-6-chloro-7'-hydroxy-10',11',11'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

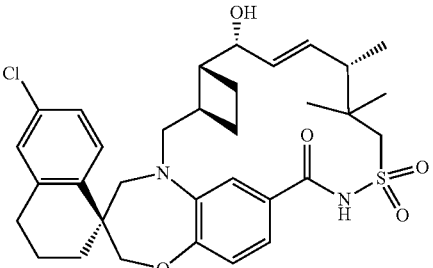

or

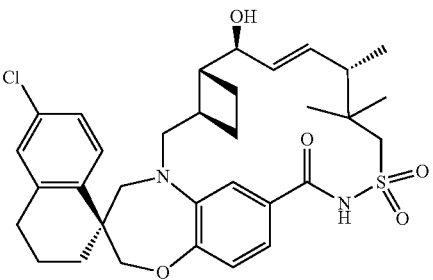

or

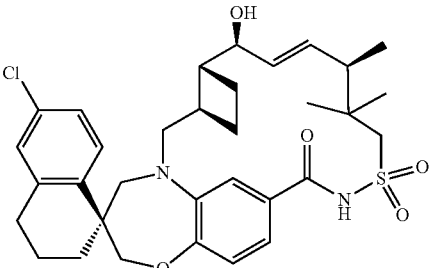

-continued

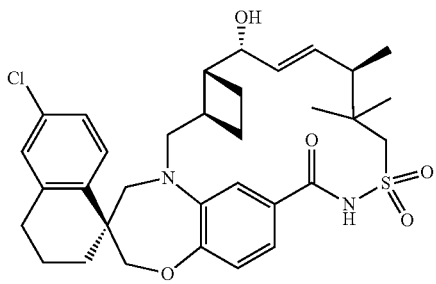

The title compound was obtained as the second eluting isomer from chromatography separation in Example 493, Step 6 (2.2 mg, 6%). $^1$H NMR (500 MHz, CD$_3$OD) δ 7.71 (d, J=8.6 Hz, 1H), 7.16 (dd, J=2.1, 8.4 Hz, 1H), 7.10 (d, J=2.0 Hz, 1H), 7.05 (br. s., 1H), 6.97 (d, J=8.1 Hz, 1H), 6.90 (d, J=8.1 Hz, 1H), 5.98 (d, J=9.5 Hz, 1H), 5.52-5.44 (m, 1H), 4.08 (s, 2H), 4.01 (t, J=7.0 Hz, 1H), 3.87 (d, J=15.9 Hz, 1H), 3.62 (d, J=14.7 Hz, 2H), 3.50-3.39 (m, 2H), 2.88-2.69 (m, 2H), 2.63-2.53 (m, 1H), 2.36-2.20 (m, 2H), 2.10-1.68 (m, 8H), 1.50 (t, J=11.2 Hz, 1H), 1.29 (s, 3H), 1.22 (s, 3H), 1.02 (d, J=7.1 Hz, 3H). m/z (ESI, +ve ion) 613.2 (M+H)$^+$.

Example 495. (1S,3'R,6'S,8'E)-6-chloro-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and
Example 496. (1S,3'R,6'R,9'E)-6-chloro-3,4-dihydro-2H,15'H-spiro[naphthalene-1,22'-[20]oxa[13]thia[1,14]diazatetracyclo[14.7.2.0$^{3,6}$.0$^{19,24}$]pentacosa[10,16,18,24]tetraen]-15'-one 13',13'-dioxide and
Example 497. (1S,3'R,6'R,10'Z)-6-chloro-3,4-dihydro-2H,15'H-spiro[naphthalene-1,22'-[20]oxa[13]thia[1,14]diazatetracyclo[14.7.2.0$^{3,6}$.0$^{19,24}$]pentacosa[10,16,18,24]tetraen]-15'-one 13',13'-dioxide and
Example 498. (1S,3'R,6'R,10'E)-6-chloro-3,4-dihydro-2H,15'H-spiro[naphthalene-1,22'-[20]oxa[13]thia[1,14]diazatetracyclo[14.7.2.0$^{3,6}$.0$^{19,24}$]pentacosa[10,16,18,24]tetraen]-15'-one 13',13'-dioxide and
Example 499. (1S,3'R,6'R,9'Z)-6-chloro-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide

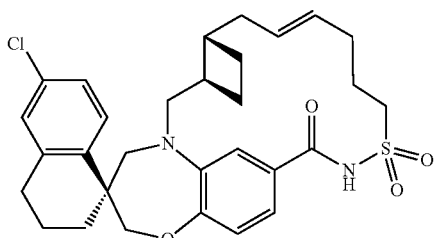

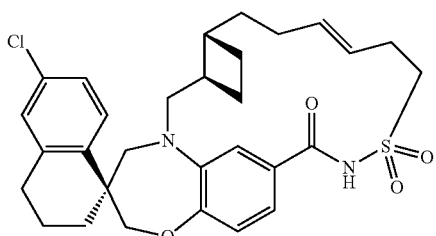

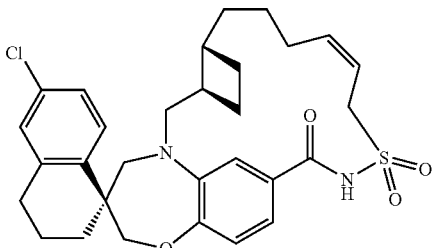

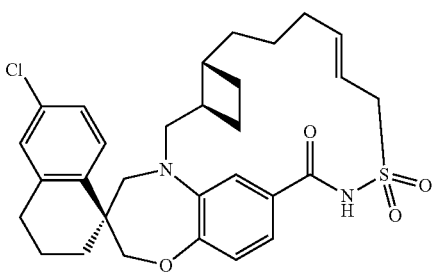

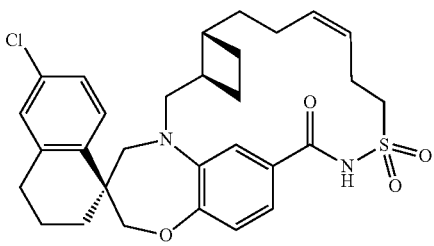

Step 1. (S)-methyl 6'-chloro-5-(((1R,2S)-2-((E)-3-oxoprop-1-en-1-yl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2S)-2-((Z)-3-oxoprop-1-en-1-yl)cyclobutyl)methyl)-3',4,4',5-tetrahydro-2H,2'H-spiro[benzo[b][1,4]oxazepine-3,1'-naphthalene]-7-carboxylate

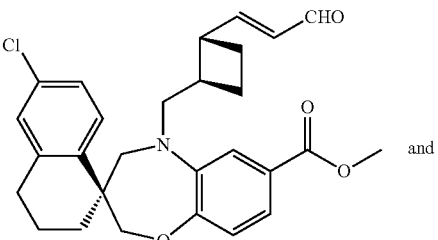

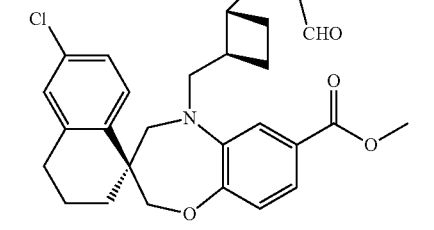

A solution of (1,3-dioxolan-2-ylmethyl)triphenylphosphonium bromide (2.18 g, 5.09 mmol, Avocado Research) in 1.5 mL of THF was cooled to −78° C., butyllithium solution, 2.5 M in hexanes (1.45 ml, 3.63 mmol, Aldrich) was added dropwise. The reaction mixture was stirred at −78° C. for 25 min, (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (0.330 g, 0.727 mmol, Intermediate, Intermediate AA11A, Step 20A) in THF (0.5 ml) was added slowly and it was stirred at −78° C. for 30 min and then r.t. overnight. The reaction mixture was diluted with water (50 mL) and extracted with EtOAc (2×50 mL). The organic solution was concentrated, and the residue was dissolved in 10 mL of THF and was treated with 2 mL of 1N HCl aq solution, stirred at ambient temperature for 2 hrs. The reaction mixture was diluted with water (50 mL) and extracted with EtOAc (2×50 mL). The organic extract was washed with saturated aqueous NaCl (30 mL) solution and dried over MgSO$_4$. The solution was filtered and concentrated in vacuo. The crude material was purified by chromatography through a Redi-Sep pre-packed silica gel column (40 g), eluting with a gradient of 0% to 60% EtOAc in hexane to provide a mixture of the title compound (0.260 g, 75%) as a white solid. m/z (ESI, +ve ion) 480.2 (M+H)$^+$.

Step 2: (S)-methyl 6'-chloro-5-(((1R,2S)-2-(3-hydroxypropyl)cyclobutyl)methyl)-3',4,4',5-tetrahydro-2H,2'H-spiro[benzo[b][1,4]oxazepine-3,1'-naphthalene]-7-carboxylate

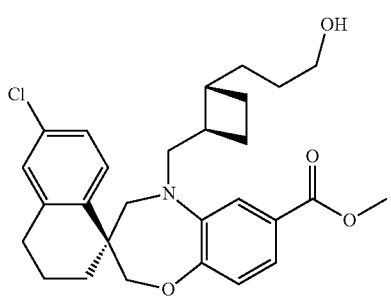 [SMILES: COC(=O)c1ccc2c(c1)N(C[C@@H]1CC[C@H]1CCCO)C[C@@]1(CCCc3cc(Cl)ccc31)CO2]

A mixture of (S)-methyl 6'-chloro-5-(((1R,2S)-2-((E)-3-oxoprop-1-en-1-yl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2S)-2-((Z)-3-oxoprop-1-en-1-yl)cyclobutyl)methyl)-3',4,4',5-tetrahydro-2H,2'H-spiro[benzo[b][1,4]oxazepine-3,1'-naphthalene]-7-carboxylate (0.260 g, 0.542 mmol) from Step 1 above and platinum (iv) oxide (60 mg, 0.26 mmol, Omega) in EtOAc (10 mL) were stirred under H$_2$ at ambient temperature for 3 h. The solid was filtered off and the filtrate concentrated. The crude material was purified by chromatography through a Redi-Sep pre-packed silica gel column (40 g), eluting with a gradient of 0% to 100% EtOAc in hexane, to provide the title compound (0.240 g, 92%). m/z (ESI, +ve ion) 484.2 (M+H)$^+$.

Step 3: (S)-methyl 6'-chloro-5-(((1R,2S)-2-(3-oxopropyl)cyclobutyl)methyl)-3',4,4',5-tetrahydro-2H,2'H-spiro[benzo[b][1,4]oxazepine-3,1'-naphthalene]-7-carboxylate

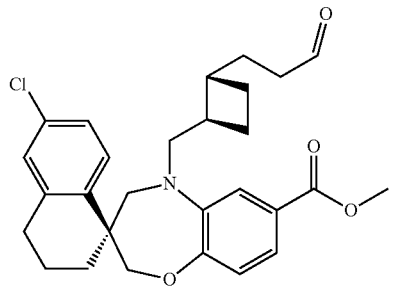 [SMILES: COC(=O)c1ccc2c(c1)N(C[C@@H]1CC[C@H]1CCC=O)C[C@@]1(CCCc3cc(Cl)ccc31)CO2]

A flask charged dimethyl sulfoxide (0.352 mL, 4.96 mmol, Aldrich) and DCM (1 mL) was cooled to −78° C., oxalyl chloride, 2.0 M solution in dichloromethane (1.24 mL, 2.48 mmol, Aldrich) was added dropwise and the reaction stirred for 30 min. A solution of (S)-methyl 6'-chloro-5-(((1R,2S)-2-(3-hydroxypropyl)cyclobutyl)methyl)-3',4,4',5-tetrahydro-2H,2'H-spiro[benzo[b][1,4]oxazepine-3,1'-naphthalene]-7-carboxylate (240 mg, 0.496 mmol) from Step 2 above in DCM (1 ml) was added dropwise and the reaction was stirred at −78° C. for 30 min, and then triethylamine (1.38 mL, 9.92 mmol, Aldrich) was added dropwise and it was stirred for 10 min at −78° C. and then ambient temperature for 30 min. The reaction mixture was quenched with water (5 ml), extracted with EtOAc (50 ml). The organic layer was washed with 1N HCl aq solution and brine, dried over anhydrous sodium sulfate, and concentrated and purified by chromatography through a Redi-Sep pre-packed silica gel column (40 g), eluting with a gradient of 0% to 60% EtOAc in hexane to give the title compound (0.220 g, 92%). m/z (ESI, +ve ion) 482.2 (M+H)$^+$.

Step 4: (S)-methyl 5-(((1R,2R)-2-(but-3-en-1-yl)cyclobutyl)methyl)-6'-chloro-3',4,4',5-tetrahydro-2H,2'H-spiro[benzo[b][1,4]oxazepine-3,1'-naphthalene]-7-carboxylate

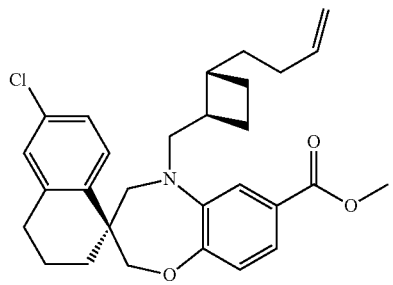 [SMILES: C=CCC[C@@H]1CC[C@H]1CN1C[C@@]2(CCCc3cc(Cl)ccc32)COc2ccc(C(=O)OC)cc21]

A solution of methyl phenylphosphonium bromide (741 mg, 2.08 mmol, Avocado Research) in THF (10 ml) was added potassium tert-butoxide, 1.0 M solution in tetrahydrofuran (1.25 ml, 1.25 mmol, Aldrich) and stirred at ambient temperature for 30 min. (S)-methyl 6'-chloro-5-(((1R,2S)-2-(3-oxopropyl)cyclobutyl)methyl)-3',4,4',5-tetrahydro-2H,2'H-spiro[benzo[b][1,4]oxazepine-3,1'-naphthalene]-7-carboxylate (200 mg, 0.420 mmol) from Step 3 above in THF (1.5 ml) was added slowly and the resulting mixture was stirred at 0° C. for 30 min and then ambient temperature overnight. The reaction mixture was diluted with 1N HCl (10 mL) and extracted with Et$_2$O (2×30 mL). The organic extract was washed with saturated aqueous NaCl solution (20 mL) and dried over MgSO$_4$. The solution was filtered and concentrated in vacuo to give the crude title compound as a white solid. m/z (ESI, +ve ion) 480.2 (M+H)$^+$.

Step 5: (S)-5-(((1R,2R)-2-(but-3-en-1-yl)cyclobutyl) methyl)-6'-chloro-3',4,4',5-tetrahydro-2H,2'H-spiro [benzo[b][1,4]oxazepine-3,1'-naphthalene]-7-carboxylic Acid

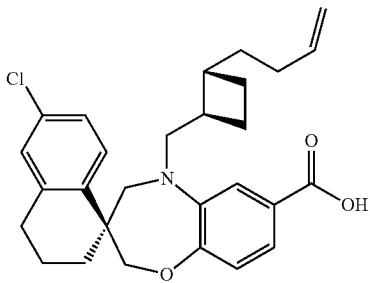 [SMILES: C=CCC[C@@H]1CC[C@H]1CN1C[C@@]2(CCCc3cc(Cl)ccc32)COc2ccc(C(=O)O)cc21]

A mixture of (S)-methyl 5-(((1R,2R)-2-(but-3-en-1-yl) cyclobutyl)methyl)-6'-chloro-3',4,4',5-tetrahydro-2H,2'H-spiro[benzo[b][1,4]oxazepine-3,1'-naphthalene]-7-carboxylate (180 mg, 0.375 mmol) from Step 4 above and lithium hydroxide monohydrate (142 mg, 3.37 mmol, Aldrich) in 1 mL of water dissolved in MeOH (2 mL) and THF (3.00 mL) was stirred at 40° C. overnight, and then the solvents were removed, acidified with 1 N HCl aq solution to pH 2-3, extracted with EtOAc (3×60 ml), washed with brine (3 ml), dried over anhydrous sodium sulfate, and then concentrated to give the title compound (0.175 g, 100%). m/z (ESI, +ve ion) 466.2 (M+H)$^+$.

Step 6: (S)-5-(((1R,2R)-2-(but-3-en-1-yl)cyclobutyl) methyl)-N-(but-3-en-1-ylsulfonyl)-6'-chloro-3',4,4', 5-tetrahydro-2H,2'H-spiro[benzo[b][1,4]oxazepine-3,1'-naphthalene]-7-carboxamide

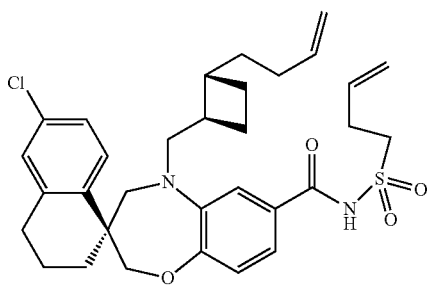 [SMILES: C=CCC[C@@H]1CC[C@H]1CN1C[C@@]2(CCCc3cc(Cl)ccc32)COc2ccc(C(=O)NS(=O)(=O)CCC=C)cc21]

N,N-dimethylpyridin-4-amine (DMAP) (78.0 mg, 0.638 mmol, Aldrich) was added to a solution of (S)-5-(((1R,2R)-2-(but-3-en-1-yl)cyclobutyl)methyl)-6'-chloro-3',4,4',5-tetrahydro-2H,2'H-spiro[benzo[b][1,4]oxazepine-3,1'-naphthalene]-7-carboxylic acid (0.175 g, 0.375 mmol) from Step 5 above and but-3-ene-1-sulfonamide (0.203 g, 1.50 mmol, Intermediate, EE15) in DCM (13 ml) at 0° C., and then n-(3-dimethylaminopropyl)-n'-ethylcarbodiimide hydrochloride (0.144 g, 0.750 mmol, Aldrich) was added at ambient temperature ion by portions slowly and the reaction mixture was stirred at ambient temperature overnight. The reaction was diluted with EtOAc (60 ml), washed with 1N HCl aq solution (2×5 ml), brine (3 ml), dried over anhydrous sodium sulfate, concentrated. The residue was purified by chromatography through a Redi-Sep pre-packed silica gel column (40 g), eluting with a gradient of 0% to 20% EtOAc in hexane to provide the title compound (0.175 g, 80%). m/z (ESI, +ve ion) 583.2 (M+H)$^+$.

Step 7: (1S,3'R,6'S,8'E)-6-chloro-3,4-dihydro-2H, 15'H-spiro[naphthalene-1,22'-[20]oxa[13]thia[1,14] diazatetracyclo[14.7.2.0$^{3,6}$.0$^{19,24}$]pentacosa [8,16,18, 24]tetraen]-15'-one 13',13'-dioxide and (1S,3'R,6'R, 9'E)-6-chloro-3,4-dihydro-2H,15'H-spiro [naphthalene-1,22'-[20]oxa[13]thia[1,14] diazatetracyclo[14.7.2.0$^{3,6}$.0$^{19,24}$]pentacosa [10,16, 18,24]tetraen]-15'-one 13',13'-dioxide and (1S,3'R, 6'R,10'Z)-6-chloro-3,4-dihydro-2H,15'H-spiro [naphthalene-1,22'-[20]oxa[13]thia[1,14] diazatetracyclo[14.7.2.0$^{3,6}$.0$^{19,24}$]pentacosa [10,16, 18,24]tetraen]-15'-one 13',13'-dioxide and (1S,3'R, 6'R,10'E)-6-chloro-3,4-dihydro-2H,15'H-spiro [naphthalene-1,22'-[20]oxa[13]thia[1,14] diazatetracyclo[14.7.2.0$^{3,6}$.0$^{19,24}$]pentacosa [10,16, 18,24]tetraen]-15'-one 13',13'-dioxide and (1S,3'R, 6'R,9'Z)-6-chloro-3,4-dihydro-2H,15'H-spiro [naphthalene-1,22'-[20]oxa[13]thia[1,14] diazatetracyclo[14.7.2.0$^{3,6}$.0$^{19,24}$]pentacosa [9,16,18, 24]tetraen]-15'-one 13',13'-dioxide A 100 mL round bottom flask was charged with (S)-5-(((1R,2R)-2-(but-3-en-1-yl)cyclobutyl)methyl)-N-(but-3-en-1-ylsulfonyl)-6'-chloro-3',4,4',5-tetrahydro-2H,2'H-spiro [benzo[b][1,4]oxazepine-3,1'-naphthalene]-7-carboxamide (135 mg, 0.230 mmol) from Step 6 in 20 mL of toluene. The solution was stirred at ambient temperature for 10 min to dissolve the solid starting material and then subjected to three cycles of evacuation/back-filling with nitrogen. To the homogeneous solution was added a solution of Hoveyda-Grubbs 2$^{nd}$ generation (29 mg, 0.046 mmol, Aldrich) in toluene (10 mL) at room temperature. The mixture was stirred at 106° C. under nitrogen for 70 min. Air was blown for 10 min to deactivate the catalyst, and then concentrated. The residue was purified by chromatography through a Redi-Sep pre-packed silica gel column (40 g), eluting with a gradient of 0% to 100% EtOAc to give two fractions with the desired mass. The first fraction was further purified by the reversed phase preparatory HPLC (Gemini™ Prep C$_{18}$ 5 μm column; Phenomenex, Torrance, CA; gradient elution of 40% to 95% MeCN in water, where both solvents contain 0.1% TFA, 30 min method) to give (1S,3'R,6'S,8'E)-6-chloro-3,4-dihydro-2H,15'H-spiro[naphthalene-1,22'-[20] oxa[13]thia[1,14]diazatetracyclo[14.7.2.0$^{3,6}$.0$^{19,24}$]pentacosa[8,16,18,24]tetraen]-15'-one 13',13'-dioxide (Example 495, 14 mg, 0.025 mmol) as the first eluting major isomer, (1S,3'R,6'R,9'E)-6-chloro-3,4-dihydro-2H,15'H-spiro[naphthalene-1,22'-[20]oxa[13]thia[1,14]diazatetracyclo [14.7.2.0$^{3,6}$.0$^{19,24}$]pentacosa[10,16,18,24]tetraen]-15'-one 13',13'-dioxide (Example 496, 10 mg, 0.018 mmol) as the third eluting major isomer, (1S,3'R,6'R,10'Z)-6-chloro-3,4-dihydro-2H,15'H-spiro[naphthalene-1,22'-[20]oxa[13]thia [1,14]diazatetracyclo[14.7.2.0$^{3,6}$.0$^{19,24}$]pentacosa[10,16,18, 24]tetra en]-15'-one 13',13'-dioxide (Example 497, 10 mg, 0.018 mmol) as the second eluting major isomer, (1S,3'R,6'R,10'E)-6-chloro-3,4-dihydro-2H,15'H-spiro[naphthalene-1,22'-[20]oxa[13]thia[1,14]diazatetracyclo[14.7.2.0³,⁶.0¹⁹,²⁴]pentacosa[10,16,18,24]tetra en]-15'-one 13',13'-dioxide (Example 498, 23 mg, 0.041 mmol) as the fourth eluting major isomer. The second fraction from chromatography purification was also further purified by the reversed phase preparatory HPLC (Gemini™ Prep C₁₈ 5 µm column; Phenomenex, Torrance, CA; gradient elution of 40% to 95% MeCN in water, where both solvents contain 0.1% TFA, 30 min method) to give (1S,3'R,6'R,9'Z)-6-chloro-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide (Example 499, 5 mg, 0.009 mmol). (1S,3'R,6'S,8'E)-6-chloro-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide: ¹H NMR (500 MHz, CDCl₃) δ 8.00 (s, 1H), 8.04-7.96 (m, 1H), 7.72 (d, J=8.6 Hz, 1H), 7.19 (dd, J=2.2, 8.6 Hz, 1H), 7.08 (dd, J=2.0, 8.3 Hz, 2H), 6.95-6.91 (m, 1H), 6.90-6.86 (m, 1H), 5.55-5.40 (m, 2H), 4.18-4.03 (m, 3H), 3.82-3.66 (m, 2H), 3.37-3.20 (m, 2H), 2.98 (dd, J=8.1, 15.4 Hz, 1H), 2.85-2.69 (m, 2H), 2.37-2.18 (m, 4H), 2.12-1.21 (m, 12H). m/z (ESI, +ve ion) 555.2 (M+H)⁺; (1S,3'R,6'R,9'E)-6-chloro-3,4-dihydro-2H,15'H-spiro[naphthalene-1,22'-[20]oxa[13]thia[1,14]diazatetracyclo[14.7.2.0³,⁶.0¹⁹,²⁴]pentacosa[10,16,18,24]tetra en]-15'-one 13',13'-dioxide: ¹H NMR (500 MHz, CDCl₃) δ 8.04 (s, 1H), 7.73 (d, J=8.6 Hz, 1H), 7.21 (ddd, J=2.1, 8.2, 14.9 Hz, 2H), 7.09 (d, J=2.2 Hz, 1H), 6.97 (d, J=8.3 Hz, 1H), 6.83 (d, J=1.7 Hz, 1H), 5.62 (td, J=7.2, 14.7 Hz, 1H), 5.45-5.33 (m, 1H), 4.19-4.04 (m, 3H), 3.85 (ddd, J=2.7, 10.2, 15.5 Hz, 1H), 3.78-3.61 (m, 3H), 3.20 (d, J=14.4 Hz, 1H), 3.05 (dd, J=5.5, 15.5 Hz, 1H), 2.86-2.51 (m, 4H), 2.34-1.23 (m, 13H). m/z (ESI, +ve ion) 555.2 (M+H)⁺; (1S,3'R,6'R,10'Z)-6-chloro-3,4-dihydro-2H,15'H-spiro[naphthalene-1,22'-[20]oxa[13]thia[1,14]diazatetracyclo[14.7.2.0³,⁶.0¹⁹,²⁴]pentacosa[10,16,18,24]tetra en]-15'-one 13',13'-dioxide: ¹H NMR (500 MHz, CDCl₃) δ 7.90 (s, 1H), 7.71 (d, J=8.6 Hz, 1H), 7.19 (dd, J=2.3, 8.4 Hz, 1H), 7.07 (dd, J=1.7, 19.1 Hz, 2H), 6.95-6.90 (m, 2H), 5.79 (dt, J=3.1, 10.8 Hz, 1H), 5.48 (dt, J=3.3, 11.1 Hz, 1H), 5.07-4.91 (m, 1H), 4.18-4.07 (m, 2H), 3.85 (d, J=15.4 Hz, 1H), 3.77-3.62 (m, 2H), 3.17 (d, J=14.2 Hz, 1H), 2.99 (dd, J=6.7, 15.3 Hz, 1H), 2.84-2.66 (m, 2H), 2.37-1.06 (m, 16H). m/z (ESI, +ve ion) 555.2 (M+H)⁺; (1S,3'R,6'R,10'E)-6-chloro-3,4-dihydro-2H,15'H-spiro[naphthalene-1,22'-[20]oxa[13]thia[1,14]diazatetracyclo[14.7.2.0³,⁶.0¹⁹,²⁴]pentacosa[10,16,18,24]tetra en]-15'-one 13',13'-dioxide: ¹H NMR (500 MHz, CDCl₃) δ 8.04 (s, 1H), 7.70 (d, J=8.6 Hz, 1H), 7.18 (dd, J=2.3, 8.4 Hz, 1H), 7.14 (dd, J=2.0, 8.1 Hz, 1H), 7.09 (d, J=2.2 Hz, 1H), 6.97 (d, J=8.1 Hz, 1H), 6.74 (d, J=1.7 Hz, 1H), 5.89 (td, J=7.5, 15.1 Hz, 1H), 5.56 (td, J=7.4, 15.2 Hz, 1H), 4.31-4.23 (m, 1H), 4.22-4.16 (m, 1H), 4.14-4.07 (m, 2H), 3.69 (d, J=14.2 Hz, 1H), 3.60 (d, J=15.7 Hz, 1H), 3.28-3.14 (m, 2H), 2.85-2.69 (m, 2H), 2.25-1.20 (m, 16H). m/z (ESI, +ve ion) 555.2 (M+H)⁺; 1S,3'R,6'R,9'Z)-6-chloro-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide: ¹H NMR (400 MHz, CDCl₃) δ 7.98 (br. s., 1H), 7.71 (d, J=8.6 Hz, 1H), 7.19 (dd, J=2.2, 8.6 Hz, 1H), 7.12-7.04 (m, 2H), 6.98 (d, J=8.2 Hz, 1H), 6.89 (s, 1H), 5.62-5.49 (m, 1H), 5.41-5.31 (m, 1H), 4.22-4.02 (m, 2H), 3.80-3.53 (m, 4H), 3.34 (d, J=14.3 Hz, 1H), 3.18 (dd, J=8.8, 15.5 Hz, 1H), 2.90-2.69 (m, 2H), 2.66-1.17 (m, 16H). m/z (ESI, +ve ion) 555.2 (M+H)⁺.

Example 500. (1S,3'R,6'S,9'R,10'E)-6-chloro-9'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa [10,16,18,24]tetraen]-15'-one 13',13'-dioxide or (1S,3'R,6'S,9'S,10'E)-6-chloro-9'-hydroxy-3,4-dihydro-2H,15'H-spiro[naphthalene-1,22'-[20]oxa[13]thia[1,14]diazatetracyclo [14.7.2.0³,⁶.0¹⁹,²⁴]pentacosa [10,16,18,24]tetraen]-15'-one 13',13'-dioxide

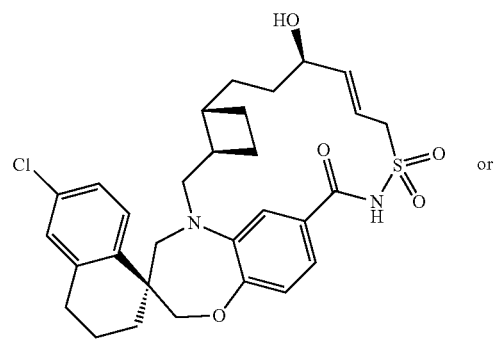

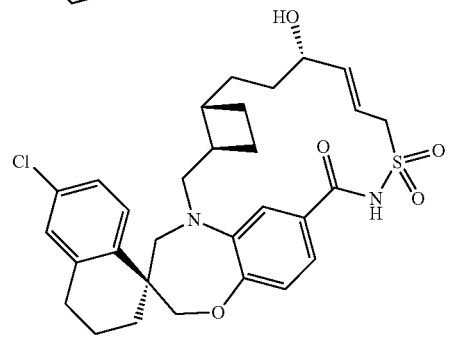

Step 1: (S)-tert-butyl 6'-chloro-5-(((1R,2S)-2-(3-oxopropyl)cyclobutyl)methyl)-3',4,4',5-tetrahydro-2H,2'H-spiro[benzo[b][1,4]oxazepine-3,1'-naphthalene]-7-carboxylat

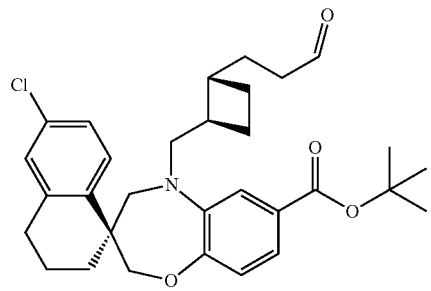 [SMILES: CC(C)(C)OC(=O)c1ccc2c(c1)N(C[C@@H]1CC[C@H]1CCC=O)C[C@@]1(CCCc3cc(Cl)ccc31)CO2]

The title compound was prepared in an analogous manner to that described in Example 495 from Step 1 to Step 3 using Intermediate AA11A, Step 20B. (S)-tert-butyl 6'-chloro-5-(((1R,2S)-2-(3-oxopropyl)cyclobutyl)methyl)-3',4,4',5-tetrahydro-2H,2'H-spiro[benzo[b][1,4]oxazepine-3,1'-naphthalene]-7-carboxylate. m/z (ESI, +ve ion) 524.2 (M+H)⁺.

1103

Step 2: (S)-6'-chloro-5-(((1R,2S)-2-((R)-3-hydroxypent-4-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2S)-2-((S)-3-hydroxypent-4-en-1-yl)cyclobutyl)methyl)-3',4,4',5-tetrahydro-2H,2'H-spiro[benzo[b][1,4]oxazepine-3,1'-naphthalene]-7-carboxylic Acid

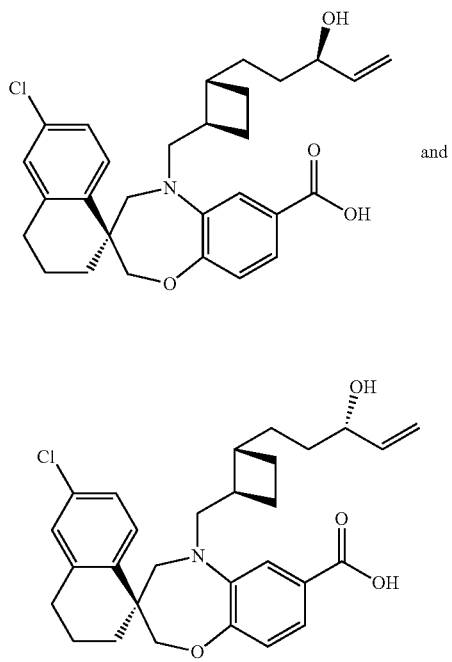 [SMILES: C=C[C@H](O)CC[C@@H]1CC[C@H]1CN1C[C@@]2(CCCc3cc(Cl)ccc32)COc2ccc(C(=O)O)cc21 ; C=C[C@@H](O)CC[C@@H]1CC[C@H]1CN1C[C@@]2(CCCc3cc(Cl)ccc32)COc2ccc(C(=O)O)cc21]

To a 100 mL round-bottomed flask was added (S)-tert-butyl 6'-chloro-5-(((1R,2S)-2-(3-oxopropyl)cyclobutyl)methyl)-3',4,4',5-tetrahydro-2H,2'H-spiro[benzo[b][1,4]oxazepine-3,1'-naphthalene]-7-carboxylate (180 mg, 0.343 mmol) from Step 1 above in THF (3 mL), and the solution was cooled to −78° C., vinylmagnesium bromide, 1.0 M solution in tetrahydrofuran (0.446 mL, 0.446 mmol, Aldrich) was added dropwise. The reaction mixture was allowed to warmed up to ambient temperature, and stirred for 3 h. The reaction mixture was diluted with ether, and quenched with the saturated aqueous NH$_4$Cl solution. The organic layer was separated, and washed with brine, concentrated. The residue was purified by chromatography through a Redi-Sep pre-packed silica gel column (40 g), eluting with a gradient of 0% to 50% EtOAc in hexane to give the desired intermediate. The intermediate was treated with 4 mL of 50% TFA/DCM. The mixture was stirred at ambient temperature for 4 h, and then concentrated. The residue was dissolved in MeCN and water, and then a few drop of NaHCO$_3$ was added. The resulting mixture was stirred at ambient temperature for 2 h, and then the organic solvent was removed. The mixture was acidified with 1N HCl aq solution to pH 2-3, extracted with EtOAc (3×60 mL). The organic solution was separated and washed with brine (3 ml), dried over anhydrous sodium sulfate, and then concentrated to give the title compound (0.045 g, 26%). m/z (ESI, +ve ion) 496.2 (M+H)$^+$.

1104

Step 3: (S)—N-(allylsulfonyl)-6'-chloro-5-(((1R,2S)-2-((R)-3-hydroxypent-4-en-1-yl)cyclobutyl)methyl)-3',4,4',5-tetrahydro-2H,2'H-spiro[benzo[b][1,4]oxazepine-3,1'-naphthalene]-7-carboxamide and (S)—N-(allylsulfonyl)-6'-chloro-5-(((1R,2S)-2-((S)-3-hydroxypent-4-en-1-yl)cyclobutyl)methyl)-3',4,4',5-tetrahydro-2H,2'H-spiro[benzo[b][1,4]oxazepine-3,1'-naphthalene]-7-carboxamide

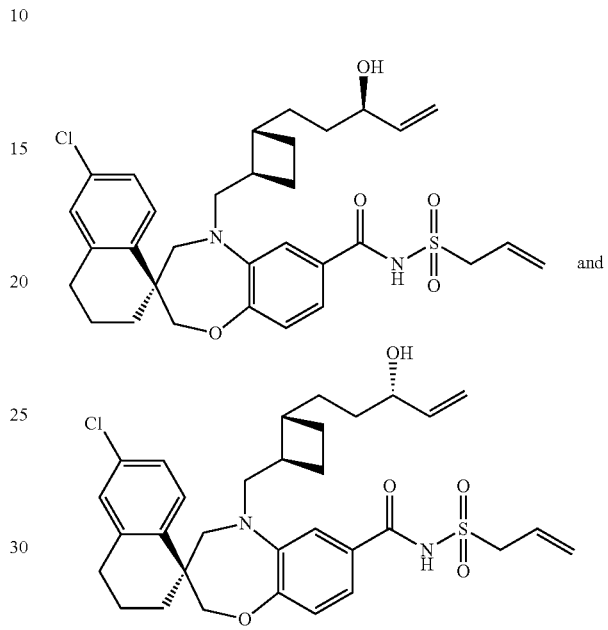

The title compounds were prepared in an analogous manner to that described in Example 495, Step 6 using (S)-6'-chloro-5-(((1R,2S)-2-((R)-3-hydroxypent-4-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2S)-2-((S)-3-hydroxypent-4-en-1-yl)cyclobutyl)methyl)-3',4,4',5-tetrahydro-2H,2'H-spiro[benzo[b][1,4]oxazepine-3,1'-naphthalene]-7-carboxylic Acid from Step 2 above and prop-2-ene-1-sulfonamide (prepared according to the procedure by Hanson, Paul R.; Jimenez-Hopkins, Maria; *Organic Letters*. 2008, 10, 2223-2226). m/z (ESI, +ve ion) 599.2 (M+H)$^+$.

Step 4: (1S,3'R,6'S,9'R,10'E)-6-chloro-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[10,16,18,24]tetraen]-15'-one 13',13'-dioxide or (1S,3'R,6'S,9'S,10'E)-6-chloro-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[10,16,18,24]tetraen]-15'-one 13',13'-dioxide The title compound was prepared from (S)—N-(allylsulfonyl)-6'-chloro-5-(((1R,2S)-2-((R)-3-hydroxypent-4-en-1-yl)cyclobutyl)methyl)-3',4,4',5-tetrahydro-2H,2'H-spiro[benzo[b][1,4]oxazepine-3,1'-naphthalene]-7-carboxamide and (S)—N-(allylsulfonyl)-6'-chloro-5-(((1R,2S)-2-((S)-3-hydroxypent-4-en-1-yl)cyclobutyl)methyl)-3',4,4',5-tetrahydro-2H,2'H-spiro[benzo[b][1,4]oxazepine-3,1'-naphthalene]-7-carboxamide by the similar procedure described in Example 432, Step 5, and isolated as the second eluting major isomer from the reversed phase preparatory HPLC separation. $^1$H NMR (500 MHz, CD$_2$Cl$_2$) δ 8.13 (br.

s., 1H), 7.71 (d, J=8.6 Hz, 1H), 7.17 (dd, J=2.3, 8.4 Hz, 1H), 7.12-7.06 (m, 2H), 6.95 (d, J=8.3 Hz, 1H), 6.72 (d, J=2.0 Hz, 1H), 5.92 (dd, J=5.9, 15.4 Hz, 1H), 5.83-5.74 (m, 1H), 4.34-4.18 (m, 3H), 4.09 (s, 2H), 3.74-3.54 (m, 2H), 3.27-3.07 (m, 2H), 2.84-2.65 (m, 2H), 2.25-0.76 (m, 15H). m/z (ESI, +ve ion) 571.2 (M+H)$^+$.

Example 501. (1S,3'R,6'S,9'S,10'E)-6-chloro-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [10,16,18,24]tetraen]-15'-one 13',13'-dioxide or (1S,3'R,6'S,9'R,10'E)-6-chloro-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [10,16,18,24]tetraen]-15'-one 13',13'-dioxide

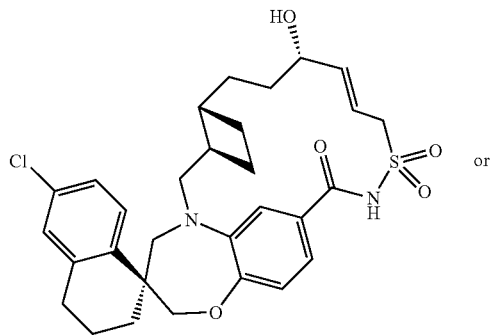

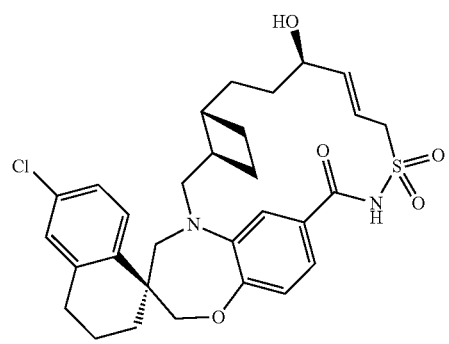

The title compound was obtained as the first eluting isomer from the reversed phase preparatory HPLC separation in Example 500, Step 4. $^1$H NMR (500 MHz, CD$_2$Cl$_2$) δ 8.05 (s, 1H), 7.68 (d, J=8.6 Hz, 1H), 7.16 (dd, J=2.3, 8.4 Hz, 1H), 7.09 (dt, J=2.2, 4.0 Hz, 2H), 6.95 (d, J=8.1 Hz, 1H), 6.78 (d, J=2.0 Hz, 1H), 5.96 (dd, J=6.4, 15.7 Hz, 1H), 5.82-5.71 (m, 2H), 4.31-4.17 (m, 2H), 4.16-4.05 (m, 3H), 3.65 (d, J=14.4 Hz, 1H), 3.53 (d, J=15.7 Hz, 1H), 3.34-3.23 (m, 2H), 2.84-2.65 (m, 2H), 2.11-0.50 (m, 15H). m/z (ESI, +ve ion) 571.2 (M+H)$^+$.

Example 502. (1S,3'R,6'S,9'R)-6-chloro-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'S,9'S)-6-chloro-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

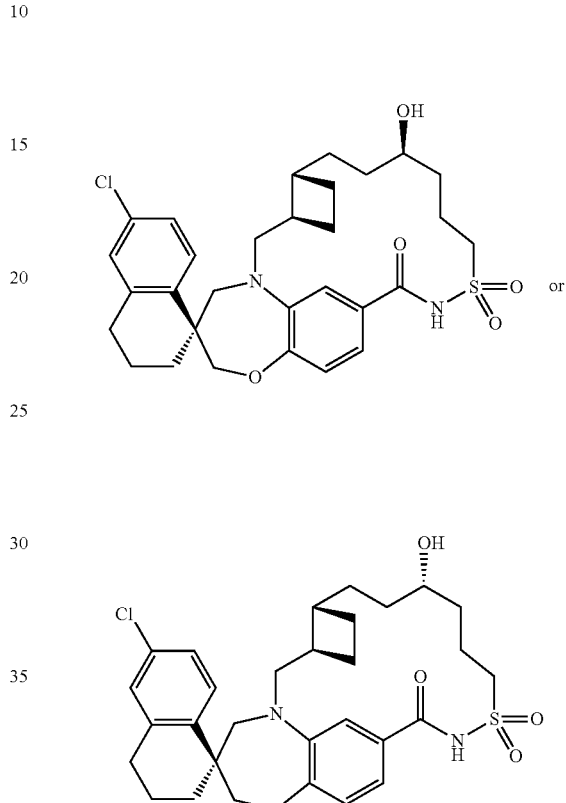

A mixture of (1S,3'R,6'S,9'R,10'E)-6-chloro-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[10,16,18,24]tetra en]-15'-one 13',13'-dioxide or (1S,3'R,6'S,9'S,10'E)-6-chloro-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[10,16,18,24]tetra en]-15'-one 13',13'-dioxide (Example 500, 15 mg, 0.026 mmol) and platinum (iv) oxide (3.6 mg, 0.016 mmol) in EtOAc (1 mL) was stirred was stirred under an atmosphere of H$_2$ (balloon) at ambient temperature for 45 min. The reaction mixture was then filtered through a syringe filter and. The crude product was further purified by the reversed phase preparatory HPLC (Gemini™ Prep C$_{18}$ 5 µm column; Phenomenex, Torrance, CA; gradient elution of 40% to 95% MeCN in water, where both solvents contain 0.1% TFA, 30 min method) to give the title compound as a white solid. $^1$H NMR (500 MHz, CDCl$_3$) δ 8.08 (s, 1H), 7.72 (d, J=8.3 Hz, 1H), 7.19 (dd, J=2.2, 8.6 Hz, 1H), 7.10 (d, J=2.0 Hz, 1H), 7.00-6.94 (m, 2H), 6.91 (s, 1H), 4.16-3.97 (m, 3H), 3.79-3.67 (m, 3H), 3.46-3.35 (m, 1H), 3.20 (d, J=14.4 Hz, 1H), 3.02 (dd, J=7.6, 15.4 Hz, 1H), 2.84-2.69 (m, 2H), 2.34-1.21 (m, 19H). m/z (ESI, +ve ion) 573.2 (M+H)$^+$.

Example 503. (1S,3'R,6'S,9'S)-6-chloro-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'S,9'R)-6-chloro-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

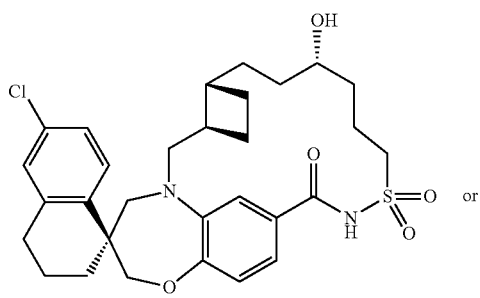

or

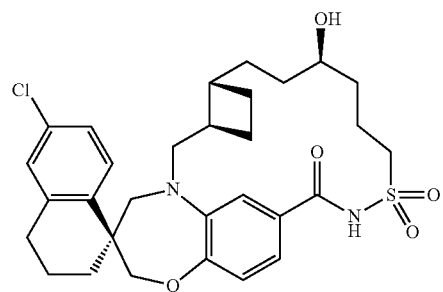

The title compound was prepared in an analogous manner to that described in Example 502 using (1S,3'R,6'S,9'S,10'E)-6-chloro-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[10,16,18,24]tetraen]-15'-one 13',13'-dioxide or (1S,3'R,6'S,9'R,10'E)-6-chloro-9'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[10,16,18,24]tetraen]-15'-one 13',13'-dioxide (Example 501). $^1$H NMR (500 MHz, CDCl$_3$) δ 8.10 (s, 1H), 7.71 (d, J=8.6 Hz, 1H), 7.20 (dd, J=2.2, 8.3 Hz, 1H), 7.13-7.08 (m, 2H), 7.00-6.89 (m, 2H), 4.17-4.04 (m, 2H), 3.95-3.85 (m, 1H), 3.79-3.47 (m, 4H), 3.31 (d, J=14.4 Hz, 1H), 3.13 (dd, J=6.1, 15.4 Hz, 1H), 2.86-2.70 (m, 2H), 2.31-1.14 (m, 19H). m/z (ESI, +ve ion) 573.2 (M+H)$^+$.

Example 504. (1S,3'R,6'S,8'E,11'S,12'R)-6-chloro-11'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'S,8'E,11'S,12'S)-6-chloro-11'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'S,8'E,11'R,12'R)-6-chloro-11'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'S,8'E,11'R,12'S)-6-chloro-11'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

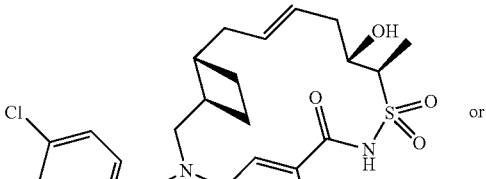

or

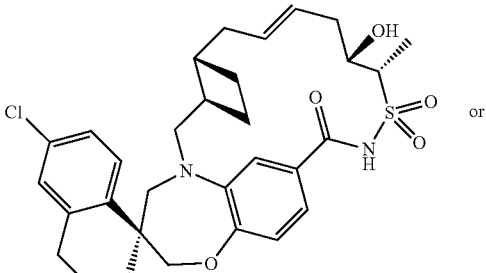

or

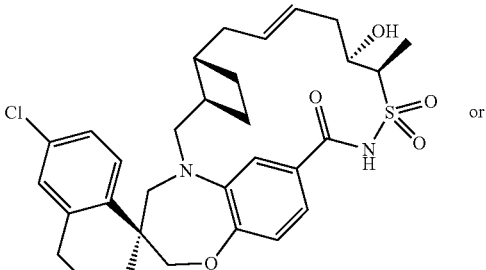

or

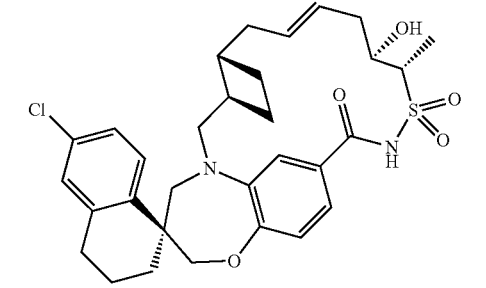

The title compound was prepared from (S)-5-(((1R,2S)-2-allylcyclobutyl)methyl)-6'-chloro-3',4,4',5-tetrahydro-2H,2'H-spiro[benzo[b][1,4]oxazepine-3,1'-naphthalene]-7-carboxylic acid (Example 450, Step 3) and (2R,3S)-3-hydroxyhex-5-ene-2-sulfonamide and (2S,3S)-3-hydroxyhex-5-ene-2-sulfonamide and (2R,3R)-3-hydroxyhex-5-ene-2-sulfonamide and (2S,3R)-3-hydroxyhex-5-ene-2-sulfonamide (Example 714, Step 5) by similar procedures described in Example 432, Steps 4-5, and isolated as the third eluting isomer from the reversed phase preparatory HPLC separation. $^1$H NMR (400 MHz, CDCl$_3$) δ 8.17 (s, 1H), 7.72 (d, J=8.4 Hz, 1H), 7.20 (dd, J=2.2, 8.4 Hz, 1H), 7.16-7.06 (m, 2H), 6.96-6.83 (m, 2H), 5.62-5.50 (m, 1H), 5.29-5.14 (m, 1H), 4.26 (q, J=7.1 Hz, 1H), 4.15-4.03 (m, 3H), 3.87-3.76 (m, 1H), 3.71 (d, J=13.9 Hz, 1H), 3.22 (d, J=14.3 Hz, 1H), 2.95 (dd, J=6.6, 15.4 Hz, 1H), 2.86-2.66 (m, 2H), 2.44-1.17 (m, 18H). m/z (ESI, +ve ion) 585.2 (M+H)$^+$.

Example 505. (1S,3'R,6'S,8'E,11'S,12'S)-6-chloro-11'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24] tetraen]-15'-one 13',13'-dioxide or (1S,3'R,6'S,8'E, 11'S,12'R)-6-chloro-11'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide or (1S,3'R,6'S,8'E,11'R,12'R)-6-chloro-11'-hydroxy-12'-methyl-3,4-dihydro-2H,15'H-spiro [naphthalene-1,22'-[20]oxa[13]thia[1,14] diazatetracyclo[14.7.2.0$^{3,6}$.0$^{19,24}$]pentacosa [8,16,18, 24]tetraen]-15'-one 13',13'-dioxide or (1S,3'R,6'S, 8'E,11'R,12'S)-6-chloro-11'-hydroxy-12'-methyl-3,4-dihydro-2H,15'H-spiro[naphthalene-1,22'-[20]oxa [13]thia[1,14]diazatetracyclo[14.7.2.0$^{3,6}$.0$^{19,24}$] pentacosa [8,16,18,24]tetraen]-15'-one 13',13'-dioxide

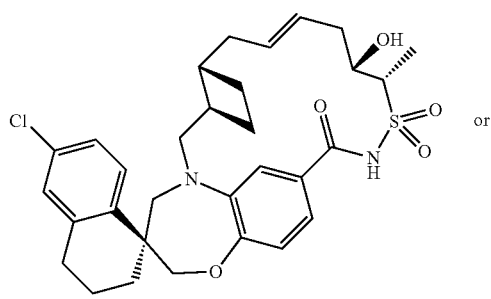

or

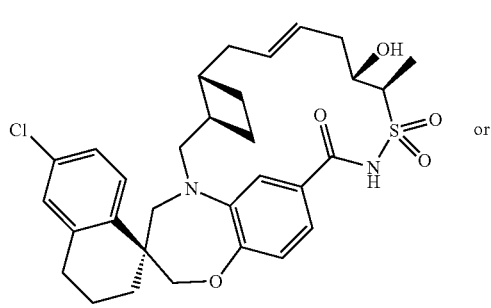

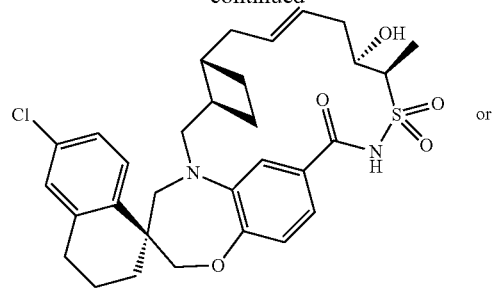

or

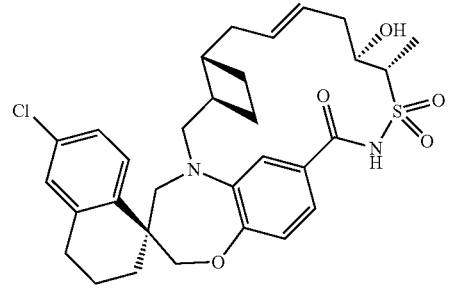

The title compound was obtained as the second eluting isomer from the reversed phase preparatory HPLC separation in Example 504. $^1$H NMR (400 MHz, CDCl$_3$) δ 8.22 (br. s., 1H), 7.70 (d, J=8.4 Hz, 1H), 7.19 (dd, J=2.2, 8.6 Hz, 1H), 7.12-7.03 (m, 2H), 6.96 (d, J=8.2 Hz, 1H), 6.68 (br. s., 1H), 5.73-5.61 (m, 1H), 5.60-5.51 (m, 1H), 4.29 (t, J=6.7 Hz, 1H), 4.18-4.03 (m, 2H), 3.91-3.77 (m, 1H), 3.68 (t, J=14.5 Hz, 2H), 3.28 (d, J=14.3 Hz, 1H), 3.16 (dd, J=7.6, 15.3 Hz, 1H), 2.89-2.65 (m, 2H), 2.53-1.06 (m, 19H). m/z (ESI, +ve ion) 585.2 (M+H)$^+$.

Example 506. (1S,3'R,6'S,8'E,11'R,12'R)-6-chloro-11'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24] tetraen]-15'-one 13',13'-dioxide or (1 S,3'R,6'S, 8'E, 11'S,12'R)-6-chloro-11'-hydroxy-12'-methyl-3,4-dihydro-2H,15'H-spiro[naphthalene-1,22'-[20]oxa [13]thia[1,14]diazatetracyclo[14.7.2.0$^{3,6}$.0$^{19,24}$] pentacosa [8,16,18,24]tetraen]-15'-one 13',13'-dioxide or (1S,3'R,6'S,8'E,11'S,12'S)-6-chloro-11'-hydroxy-12'-methyl-3,4-dihydro-2H,15'H-spiro [naphthalene-1,22'-[20]oxa[13]thia[1,14] diazatetracyclo[14.7.2.0$^{3,6}$.0$^{19,24}$]pentacosa [8,16,18, 24]tetraen]-15'-one 13',13'-dioxide or (1S,3'R,6'S, 8'E,11'R,12'S)-6-chloro-11'-hydroxy-12'-methyl-3,4-dihydro-2H,15'H-spiro[naphthalene-1,22'-[20]oxa [13]thia[1,14]diazatetracyclo[14.7.2.0$^{3,6}$.0$^{19,24}$] pentacosa [8,16,18,24]tetraen]-15'-one 13',13'-dioxide

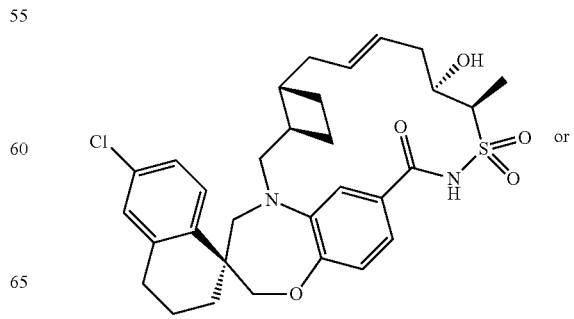

or

-continued

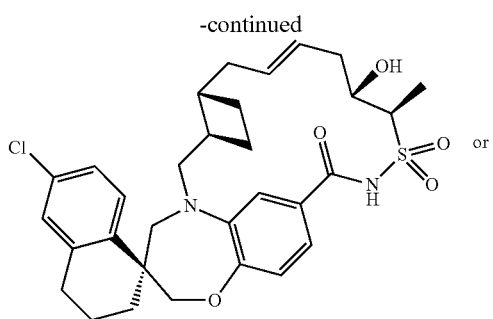

or

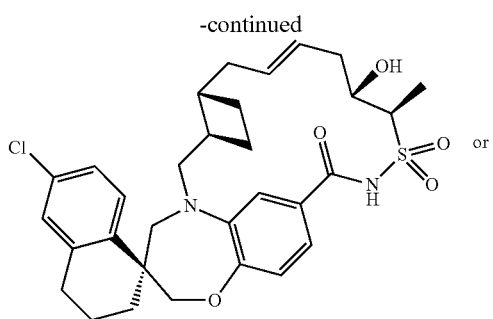

or

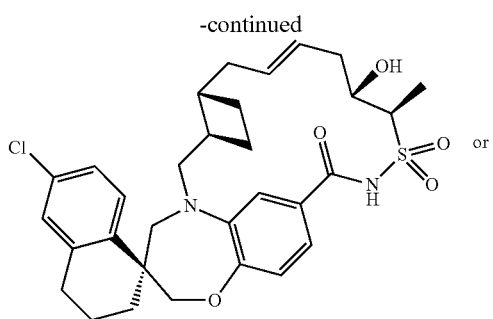

The title compound was obtained as the first eluting isomer from the reversed phase preparatory HPLC separation in Example 504. $^1$H NMR (400 MHz, CDCl$_3$) δ 8.10 (br. s., 1H), 7.71 (d, J=8.6 Hz, 1H), 7.20 (dd, J=2.2, 8.4 Hz, 1H), 7.09 (d, J=2.0 Hz, 1H), 6.98-6.85 (m, 2H), 6.78 (s, 1H), 5.64-5.52 (m, 1H), 5.50-5.36 (m, 1H), 4.28 (d, J=6.7 Hz, 1H), 4.16-3.96 (m, 3H), 3.88-3.73 (m, 2H), 3.24 (d, J=14.3 Hz, 1H), 3.04 (dd, J=8.4, 15.1 Hz, 1H), 2.89-2.67 (m, 2H), 2.66-2.55 (m, 1H), 2.44-1.13 (m, 17H). m/z (ESI, +ve ion) 585.2 (M+H)$^+$.

Example 507. (1S,3'R,6'S,8'E,11'R,12'S)-6-chloro-11'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'S,8'E,11'S,12'R)-6-chloro-11'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'S,8'E,11'S,12'S)-6-chloro-11'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'S,8'E,11'R,12'R)-6-chloro-11'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

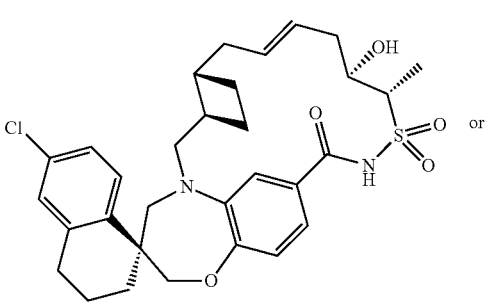

or

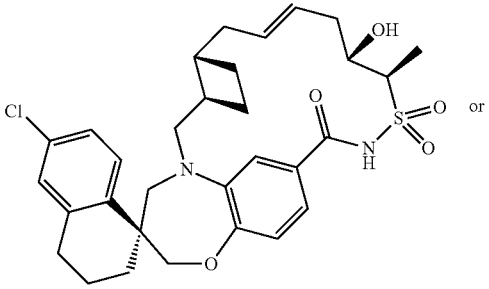

or

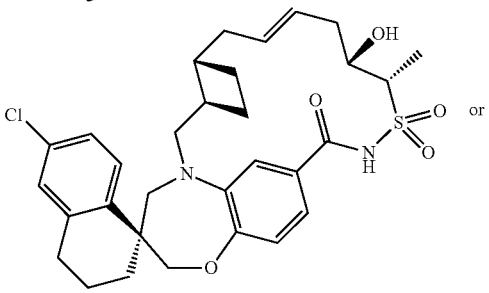

or

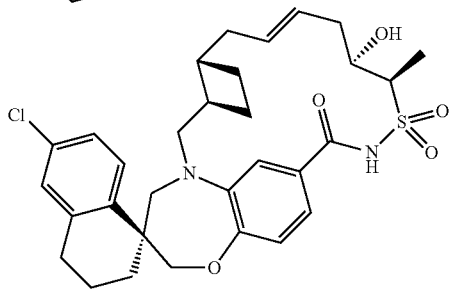

1113

The title compound was obtained as the fourth eluting isomer from the reversed phase preparatory HPLC separation in Example 504. $^1$H NMR (400 MHz, CDCl$_3$) δ 8.09 (br. s., 1H), 7.65 (d, J=8.4 Hz, 1H), 7.16 (dd, J=2.0, 8.4 Hz, 1H), 7.10 (d, J=1.8 Hz, 1H), 6.99 (s, 1H), 6.95-6.82 (m, 2H), 5.55-5.42 (m, 1H), 5.36-5.20 (m, 1H), 4.26-4.02 (m, 4H), 3.72-3.38 (m, 3H), 3.26 (d, J=14.1 Hz, 1H), 2.76 (br. s., 2H), 2.43-1.18 (m, 18H). m/z (ESI, +ve ion) 585.2 (M+H)$^+$.

Example 508. (1S,3'R,6'R,7'S,8'E,12'R)-6-chloro-7'-hydroxy-12'-((2R)-2-methoxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-6-chloro-7'-hydroxy-12'-((2R)-2-methoxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

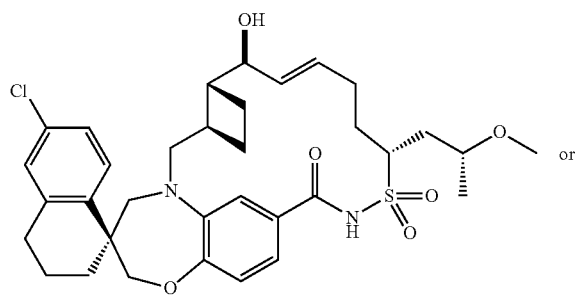

or

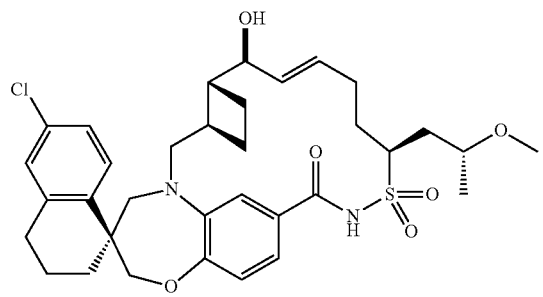

Step 1: (2R,4R)-2-hydroxy-N,N-bis(4-methoxybenzyl)oct-7-ene-4-sulfonamide and (2R,4S)-2-hydroxy-N,N-bis(4-methoxybenzyl)oct-7-ene-4-sulfonamide

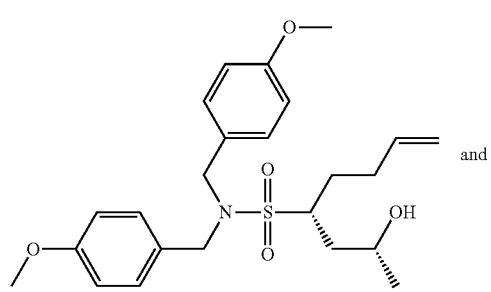

and

1114

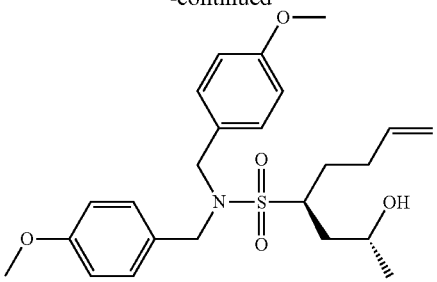

To a –78° C. solution of N,N-bis(4-methoxybenzyl)pent-4-ene-1-sulfonamide (from Intermediate EE19) (2.00 g, 5.13 mmol) in THF (20 mL) under argon was added n-butyllithium, 2.5 M solution in hexane (2.47 mL, 6.16 mmol) over 5 minutes. The mixture was stirred at –78° C. for 2 hours (solution turned red-pink) at which time (R)-(+)-1,2-epoxypropane (Sigma-Aldrich, Milwaukee, WI)(0.540 mL, 7.70 mmol) was added and stirred at 0° C. for 17 hours. The reaction was then quenched with 100 ml of saturated ammonium chloride and extracted with 300 ml of EtOAc. The organic layer was dried over sodium sulfate, filtered and the solvent removed by rotary evaporation. The crude product was purified on a Combiflash (40 g gold silica column), eluting with 10% to 50% EtOAc in heptanes, to give [(2R,4R)-2-hydroxy-N,N-bis(4-methoxybenzyl)oct-7-ene-4-sulfonamide and (2R,4S)-2-hydroxy-N,N-bis(4-methoxybenzyl)oct-7-ene-4-sulfonamide] (1.85 g, 4.13 mmol, 80% yield) as a light yellow oil.

Step 2: (2R,4S)-2-((tert-butyldiphenylsilyl)oxy)-N,N-bis(4-methoxybenzyl)oct-7-ene-4-sulfonamide or (2R,4R)-2-((tert-butyldiphenylsilyl)oxy)-N,N-bis(4-methoxybenzyl)oct-7-ene-4-sulfonamide

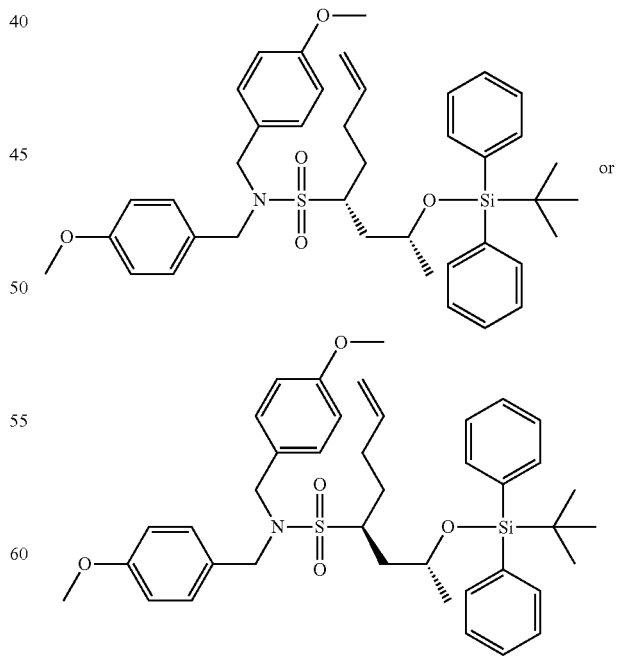

To a 100 ml flask was added [(2R,4R)-2-hydroxy-N,N-bis(4-methoxybenzyl)oct-7-ene-4-sulfonamide and (2R, 4S)-2-hydroxy-N,N-bis(4-methoxybenzyl)oct-7-ene-4-sulfonamide] (from Step 1) (2.58 g, 5.76 mmol), DMF (40 ml), imidazole (785 mg, 11.5 mmol) and tert-butylchlorodiphenylsilane (2.25 ml, 8.65 mmol). The reaction was stirred at 65° C. for 16 hours at which time reaction was then quenched with 200 ml of saturated ammonium chloride and extracted with 600 ml of diethyl ether. The organic layer was dried over sodium sulfate, filtered and the solvent removed by rotary evaporation. The crude product was first purified on a Combiflash (40 g gold silica column), eluting with 10% to 30% EtOAc in heptanes. The racemic mixture (1:1) was then purified by preparatory SCF chromatography (Chiralpak AD 250 mm×30 mm column, Phenomenex, Torrance, CA; 16 g/minute EtOH+(20 mM Ammonia)+64 g/minute $CO_2$ (20% co-solvent) on Thar 80 SFC; outlet pressure=100 bar; temperature=22° C.; wavelength=220 nm; used 1.0 mL injections of 3647 mg/41 mL (89 mg/mL) sample solution of MeOH (35 mL) and DCM (5 mL); run time=13 minutes & cycle time 10 minutes) to provide [(2R,4S)-2-((tert-butyldiphenylsilyl)oxy)-N,N-bis(4-methoxybenzyl)oct-7-ene-4-sulfonamide or (2R,4R)-2-((tert-butyldiphenylsilyl)oxy)-N,N-bis(4-methoxybenzyl)oct-7-ene-4-sulfonamide] (1651 mg, 2.407 mmol, 46% yield) as the faster eluting isomer as a yellow liquid ($t_R$=1.10 minutes on analytical SFC; AD-H column; 15% EtOH in $CO_2$).

Step 3: (2R,4S)-2-hydroxy-N,N-bis(4-methoxybenzyl)oct-7-ene-4-sulfonamide or (2R,4R)-2-hydroxy-N,N-bis(4-methoxybenzyl)oct-7-ene-4-sulfonamide

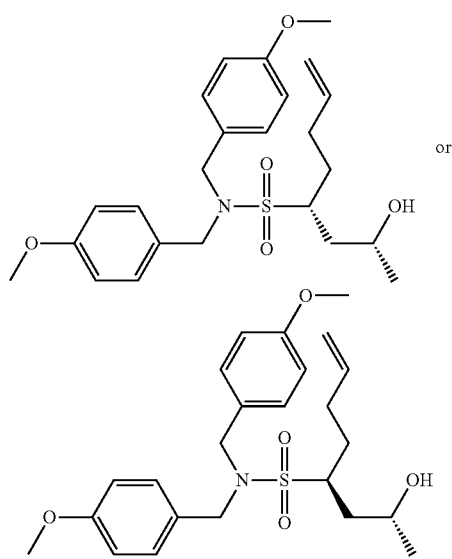

To a 100 ml flask was added [(2R,4S)-2-((tert-butyldiphenylsilyl)oxy)-N,N-bis(4-methoxybenzyl)oct-7-ene-4-sulfonamide or (2R,4R)-2-((tert-butyldiphenylsilyl)oxy)-N,N-bis(4-methoxybenzyl)oct-7-ene-4-sulfonamide](from Step 2) (600 mg, 0.875 mmol) and tetrabutylammonium fluoride, 1.0 M in tetrahydrofuran (10 ml, 10 mmol). The reaction was stirred at room temperature for 3 hours at which time the reaction was quenched with 100 ml of brine and extracted with 400 ml of EtOAc. The organic layer was dried over sodium sulfate, filtered and the solvent was removed by rotary evaporation. The crude product was purified on a Combiflash (12 g gold silica column), eluting with 10% to 50% EtOAc in heptanes, to give [(2R,4S)-2-hydroxy-N,N-bis(4-methoxybenzyl)oct-7-ene-4-sulfonamide or (2R,4R)-2-hydroxy-N,N-bis(4-methoxybenzyl)oct-7-ene-4-sulfonamide] (313 mg, 0.699 mmol, 80% yield) as a clear oil.

Step 4: (2R,4S)-2-methoxy-N,N-bis(4-methoxybenzyl)oct-7-ene-4-sulfonamide and (2R,4R)-2-methoxy-N,N-bis(4-methoxybenzyl)oct-7-ene-4-sulfonamide

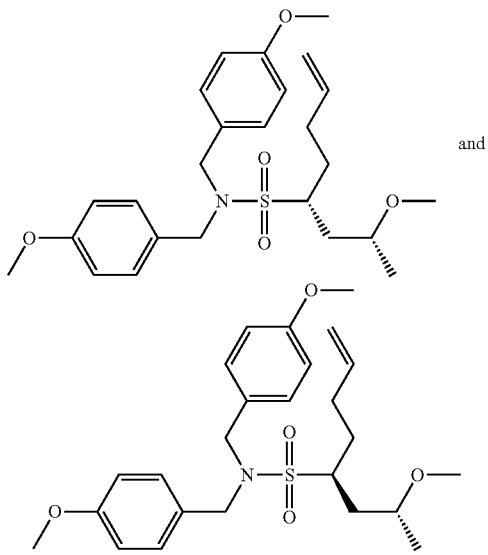

To a 100 ml flask was added [(2R,4S)-2-hydroxy-N,N-bis(4-methoxybenzyl)oct-7-ene-4-sulfonamide or (2R,4R)-2-hydroxy-N,N-bis(4-methoxybenzyl)oct-7-ene-4-sulfonamide] (from Step 3) (313 mg, 0.699 mmol), THF (5 mL) and NaH (50 mg, 2.1 mmol). The reaction was stirred at room temperature for 15 minutes at which time MeI (0.066 ml, 1.1 mmol) was added. The reaction was stirred at room temperature for an additional 3 hours and then the reaction was quenched with 100 ml of saturated ammonium chloride and extracted with 400 ml of EtOAc. The organic layer was dried over sodium sulfate, filtered, and the solvent was removed by rotary evaporation. The crude product was purified on a Combiflash (12 g gold silica column), eluting with 10% to 50% EtOAc in heptanes, to give [(2R,4S)-2-methoxy-N,N-bis(4-methoxybenzyl)oct-7-ene-4-sulfonamide and (2R,4R)-2-methoxy-N,N-bis(4-methoxybenzyl)oct-7-ene-4-sulfonamide] (255 mg, 0.552 mmol, 79% yield) as a light yellow oil.

Step 5: (2R,4S)-2-methoxyoct-7-ene-4-sulfonamide or (2R,4R)-2-methoxyoct-7-ene-4-sulfonamide

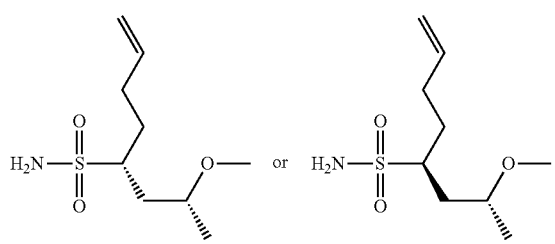

To a 100 ml flask was added [(2R,4S)-2-methoxy-N,N-bis(4-methoxybenzyl)oct-7-ene-4-sulfonamide and (2R,4R)-2-methoxy-N,N-bis(4-methoxybenzyl)oct-7-ene-4-sulfonamide] (from Step 4)(255 mg, 0.552 mmol) anisole (0.603 ml, 5.52 mmol), DCM (8 ml) and then TFA (4 ml). The reaction was stirred at 22° C. for 6 hours at which time the solvent was removed. The crude product was purified on a Combiflash (12 g gold silica column), eluting with 10% to 50% EtOAc in heptanes, to give [(2R,4S)-2-methoxyoct-7-ene-4-sulfonamide or (2R,4R)-2-methoxyoct-7-ene-4-sulfonamide] (21 mg, 0.096 mmol, 17% yield) as the faster eluting isomer as a yellow liquid.

Step 6: (S)-6'-chloro-5-(((1R,2R)-2-((1S,6R,8R,E)-1-hydroxy-8-methoxy-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1R,2R)-2-((1S,6S,8R,E)-1-hydroxy-8-methoxy-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic Acid

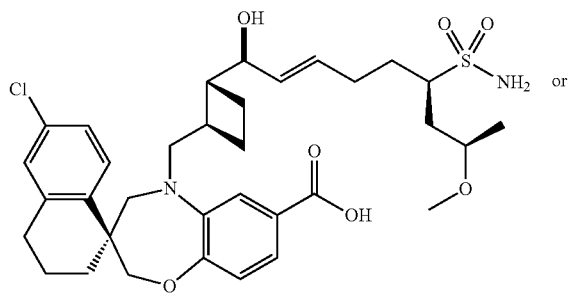

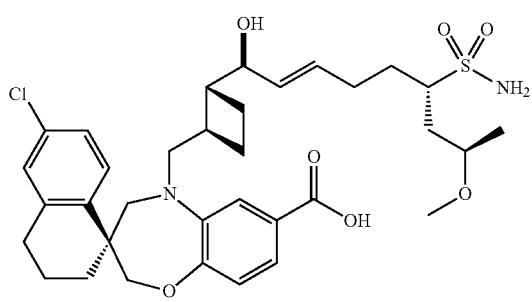

To a 100 ml flask was added (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (from Intermediate AA12A) (20 mg, 0.039 mmol), [(2R,4S)-2-methoxyoct-7-ene-4-sulfonamide or (2R,4R)-2-methoxyoct-7-ene-4-sulfonamide] (from Step 5)(22 mg, 0.098 mmol) and DCE (2 mL). The solution was sparged with argon for 15 minutes at which time (1,3-dimesitylimidazolidin-2-ylidene)(2-isopropoxybenzylidene)ruthenium(VI) chloride (2.5 mg, 3.9 μmol) was added as a 0.2 mL solution in DCE at room temperature. The mixture was stirred at room temperature for additional 16 hours. Note: the clear solution becomes slowly darker. The reaction mixture was then bubbled with air for 5 minutes and filtered. The solvent was removed from the filtrate and was directly purified on a Combiflash (4 g gold silica column), eluting with 50%-90% EtOAc in heptanes+0.2% AcOH, to give [(S)-6'-chloro-5-(((1R,2R)-2-((1S,6R,8R,E)-1-hydroxy-8-methoxy-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1R,2R)-2-((1S,6S,8R,E)-1-hydroxy-8-methoxy-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic acid] (25.9 mg, 0.039 mmol, 100% yield) as white solids. Rf=0.16 eluting with 90% EtOAc in heptanes.

Step 7: (1S,3'R,6'R,7'S,8'E,12'R)-6-chloro-7'-hydroxy-12'-((2R)-2-methoxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-6-chloro-7'-hydroxy-12'-((2R)-2-methoxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide To a 100 ml flask containing [((S)-6'-chloro-5-(((1R,2R)-2-((1S,6R,8R,E)-1-hydroxy-8-methoxy-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((1S,6S,8R,E)-1-hydroxy-8-methoxy-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic acid] (from Step 6)(26 mg, 0.039 mmol), which was previously dried by rotovaping twice with 10 ml of toluene, was added N,N-dimethylpyridin-4-amine (DMAP) (8.1 mg, 0.067 mmol), 45 ml of DCM and N-(3-dimethylaminopropyl)-N'-ethylcarbodiimide hydrochloride (15 mg, 0.078 mmol). The reaction was stirred at room temperature for 18 hour at which time the mixture was quenched with 100 ml of 1N HCl and extracted with 300 ml of EtOAc. The organic layer were dried over anhydrous sodium sulfate, filtered, and concentrated by rotary evaporation. The crude product was purified on a Combiflash (4 g gold silica column), eluting with 30%-70% EtOAc in heptanes, to give the title compound (6.8 mg, 11 μmol, 27% yield) as a white solid. $^1$H NMR (400 MHz, CDCl$_3$) δ 8.21 (br. s., 1H), 7.77-7.68 (m, 1H), 7.64 (d, J=8.4 Hz, 1H), 7.20-7.14 (m, 1H), 7.10 (d, J=2.2 Hz, 1H), 6.92 (s, 2H), 5.78 (dd, J=4.3, 15.8 Hz, 1H), 5.48-5.33 (m, 1H), 4.24 (m, 3H), 4.15-4.05 (m 1H), 3.92 (br. s., 1H), 3.87-3.71 (m, 2H), 3.51 (s, 3H), 3.41-3.24 (m, 1H), 3.12 (d, J=15.5 Hz, 1H), 3.01-2.93 (m, 1H), 2.78-2.72 (m, 2H), 2.61-2.41 (m, 2H), 2.31-2.14 (m, 2H), 2.12-1.97 (m, 1H), 1.90-1.61 (m, 8H), 1.39 (d, J=9.8 Hz, 2H), 1.31-1.24 (m, 1H), 1.21 (d, J=6.1 Hz, 3H). m/z (ESI, +ve ion) 643.0 (M+H)$^+$.

Example 509. (1S,3'R,6'R,7'S,8'E,11'S,12'R)-6-chloro-7'-(3-hydroxypropoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

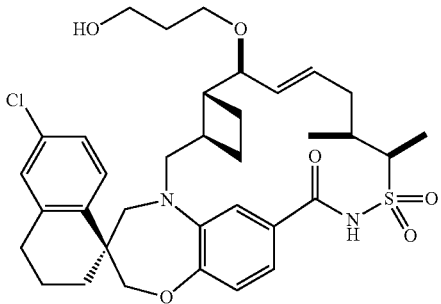 [SMILES: C[C@@H]1[C@@H](C)C/C=C/[C@H](OCCCO)[C@@H]2CC[C@H]2CN2C[C@@]3(CCCc4cc(Cl)ccc43)COc3ccc(cc32)C(=O)NS1(=O)=O]

Step 1: (1S,3'R,6'R,7'S,8'E,11'S,12'R)-6-chloro-11',12'-dimethyl-7'-(3-((2S)-tetrahydro-2H-pyran-2-yloxy)propoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide and (1S,3'R,6'R,7'S,8'E,11'S,12'R)-6-chloro-11',12'-dimethyl-7'-(3-((2R)-tetrahydro-2H-pyran-2-yloxy)propoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

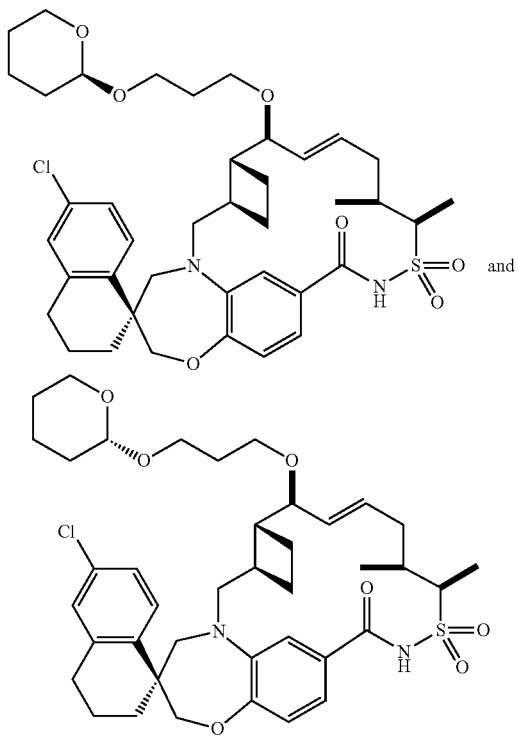

To a 100 ml round-bottomed flask was added (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (from Example 719, Step 2) (88.0 mg, 0.147 mmol), 15 mL of DMF and then sodium hydride, 60% dispersion in mineral oil (0.031 ml, 1.469 mmol). The reaction mixture was stirred at room for 15 minutes at which time 2-(3-bromopropoxy)tetrahydro-2h-pyran (0.125 ml, 0.734 mmol) (Sigma-Aldrich, Milwaukie, WI) was added. The reaction mixture was then stirred at 50° C. for 16 hours and at 60° C. for 4 hours. The reaction was then quenched with 100 ml of saturated aqueous ammonium chloride and 100 ml of 1 N HCl and then extracted with 400 mL of diethyl ether. The organic layer was back extract twice with 100 ml brine. The organic layer was dried over sodium sulfate, concentrated by rotary evaporation and the crude product was purified on a Combiflash (12 g gold silica column), eluting with 0%-50% EtOAc in heptanes, give a 1 to 1 mixture of [(1S,3'R,6'R,7'S,8'E,11'S,12'R)-6-chloro-11',12'-dimethyl-7'-(3-((2S)-tetrahydro-2H-pyran-2-yloxy)propoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,11'S,12'R)-6-chloro-11',12'-dimethyl-7'-(3-((2R)-tetrahydro-2H-pyran-2-yloxy)propoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (39 mg, 0.053 mmol, 36% yield) as a white solid.

Step 2: (1S,3'R,6'R,7'S,8'E,11'S,12'R)-6-chloro-7'-(3-hydroxypropoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide To a 25-mL round-bottomed flask was added [(1S,3'R,6'R,7'S,8'E,11'S,12'R)-6-chloro-11',12'-dimethyl-7'-(3-((2S)-tetrahydro-2H-pyran-2-yloxy)propoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,11'S,12'R)-6-chloro-11',12'-dimethyl-7'-(3-((2R)-tetrahydro-2H-pyran-2-yloxy)propoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (from Step 1)(39 mg, 0.053 mmol), 1 ml of THF and 1 mL of 1 N aqueous HCl. The reaction mixture was heated to 55° C. for 60 minutes at which time the reaction was diluted with 100 ml of EtOAc and washed with 50 ml of 1N HCl and 50 ml of brine. The aqueous layer was back extracted with 100 ml of EtOAc and the combined organic phase was dried over sodium sulfate, filtered and concentrated by rotary evaporation. The crude product was purified on a Combiflash (4 g gold silica column), eluting with 50%-90% EtOAc in heptanes, to give the title compound (13 mg, 0.020 mmol, 38% yield) as a white solid. $^1$H NMR (400 MHz, CD$_2$Cl$_2$) δ 8.28 (br. s., 1H), 7.70 (d, J=8.4 Hz, 1H), 7.16 (dd, J=2.2, 8.4 Hz, 1H), 7.09 (d, J=2.0 Hz, 1H), 6.92 (s, 2H), 6.86 (s, 1H), 5.89-5.75 (m, 1H), 5.54 (dd, J=9.2, 14.3 Hz, 1H), 4.33-4.22 (m, 1H), 4.08 (s, 2H), 3.89-3.65 (m, 5H), 3.60 (ddd, J=4.9, 6.7, 9.3 Hz, 1H), 3.43 (ddd, J=4.8, 6.6, 9.3 Hz, 1H), 3.25 (d, J=14.3 Hz, 1H), 3.03 (dd, J=10.2, 15.3 Hz, 1H), 2.85-2.60 (m, 2H), 2.52-2.39 (m, 1H), 2.39-2.27 (m, 2H), 2.26-2.02 (m, 3H), 2.00-1.63

(m, 8H), 1.45 (d, J=7.2 Hz, 3H), 1.40-1.34 (m, 1H), 1.02 (d, J=6.8 Hz, 3H). m/z (ESI, +ve ion) 657.3 (M+H)+.

Example 510. (1S,3'R,6'R,7'S,8'E,11'S,12'R)-6-chloro-11',12'-dimethyl-7'-((2R)-tetrahydro-2-furanylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

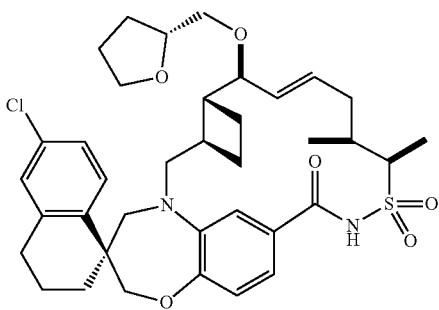 [SMILES: C[C@@H]1[C@@H](C)C/C=C/[C@H](OC[C@H]2CCCO2)[C@@H]2CC[C@H]2CN2C[C@@]3(CCCc4cc(Cl)ccc43)COc3ccc(cc32)C(=O)NS1(=O)=O]

Step 1: (R)-(tetrahydrofuran-2-yl)methyl 4-methylbenzenesulfonate

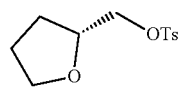

To a solution of 4-methylbenzene-1-sulfonyl chloride (2.05 g, 10.8 mmol) and N,N-dimethylpyridin-4-amine (0.598 g, 4.90 mmol) in 30 mL DCM, cooled to 0° C. was added triethylamine (2.05 ml, 14.7 mmol) followed by the drop wise addition (R)-tetrahydrofurfuryl alcohol (ASTATECH, INC., Bristol, PA)(0.949 ml, 9.79 mmol) as a solution in 5 mL DCM. The solution was stirred at room temperature for 24 hours at which time the reaction was filtered and concentrated. The crude material was resuspended in 200 ml of EtOAc and was then washed with 100 ml of 1 N HCl, 100 ml saturated sodium bicarbonate and 100 ml of brine. The organic phase was dried over sodium sulfate, filtered and concentrated by rotary evaporation. The crude oil was purified on a Combiflash (40 gram gold silica column), eluting with 0% to 50% EtOAc in heptanes to give (R)-(tetrahydrofuran-2-yl)methyl 4-methylbenzenesulfonate (2.20 g, 8.58 mmol, 88% yield) as a clear oil.

Step 2: (1S,3'R,6'R,7'S,8'E,11'S,12'R)-6-chloro-11',12'-dimethyl-7'-((2R)-tetrahydro-2-furanylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide To a 25-mL round-bottomed flask was added (1S,3'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (from Example 719, Step 2) (9.0 mg, 0.015 mmol), 2 ml of DMF and sodium hydride, 60% dispersion in mineral oil (6.0 mg, 0.15 mmol) at 0° C. The reaction mixture was stirred at 0° C. for 30 minutes at which time (R)-(tetrahydrofuran-2-yl)methyl 4-methylbenzenesulfonate (from Step 1)(19 mg, 0.075 mmol) was added. The reaction mixture was stirred at 50° C. for 4 hours and at 60° for 2 hours, and was then quenched with 1 ml of MeOH and 50 ml of 1 N HCl. The quenched reaction was extracted with 200 mL of EtOAc, the organic layer dried over sodium sulfate, filtered and the solvent removed by rotary evaporation. The crude product was purified by reversed phase preparatory HPLC (Gemini™ Prep C$_{18}$ 5 μm column; Phenomenex, Torrance, CA; gradient elution of 50% to 90% MeCN in water, where both solvents contain 0.1% TFA, 45 minute method) to give the title compound (2.4 mg, 3.5 μmol, 23% yield) as a white film. $^1$H NMR (400 MHz, CD$_2$Cl$_2$) δ 8.08 (s, 1H), 7.71 (d, J=8.6 Hz, 1H), 7.17 (dd, J=2.2, 8.6 Hz, 1H), 7.09 (d, J=2.2 Hz, 1H), 6.91 (d, J=0.8 Hz, 2H), 6.85 (s, 1H), 5.79 (ddd, J=3.2, 9.5, 15.0 Hz, 1H), 5.61-5.44 (m, 1H), 4.34-4.14 (m, 1H), 4.08 (s, 2H), 3.97-3.88 (m, 1H), 3.87-3.65 (m, 5H), 3.37 (dd, J=10.0, 4.1 Hz, 1H), 3.30-3.15 (m, 2H), 3.02 (dd, J=10.3, 15.4 Hz, 1H), 2.84-2.63 (m, 2H), 2.53-2.41 (m, 1H), 2.32 (m, 1H), 2.25-2.02 (m, 3H), 2.01-1.90 (m, 4H), 1.89-1.76 (m, 6H), 1.58-1.48 (m, 2H), 1.45 (d, J=7.2 Hz, 3H) 1.02 (d, J=6.8 Hz, 3H). m/z (ESI, +ve ion) 682.9 (M+H)+.

Example 511. (1S,3'R,6'R,7'S,8'E,11'S,12'R)-6-chloro-7'-(2-chloroethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

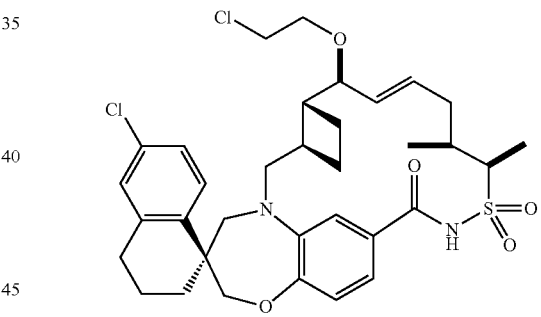

To a 1 dram pressure relief vial was added (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (from Example 14) (20 mg, 0.028 mmol), 1 ml of DMSO, (R)-3-(methoxymethyl)morpholine hydrochloride (Frontier Scientific, Logan, UT) (23 mg, 0.14 mmol) and DIEA (0.023 ml, 0.14 mmol). The reaction was sealed with a pressure release fitted cap and heated to 55° C. for 16 hours. The crude was purified by reversed phase preparatory HPLC (Gemini™ Prep C$_{18}$ 5 μm column; Phenomenex, Torrance, CA; gradient elution of 50% to 90% MeCN in water, where both solvents contain 0.1% TFA, 45 minute method) to give the title compound (2.9 mg, 4.4 μmol, 15% yield) as a white films. $^1$H NMR (400 MHz, CD$_2$Cl$_2$) δ 8.07 (s, 1H), 7.70 (d, J=8.6 Hz, 1H), 7.17 (dd, J=2.2, 8.5 Hz, 1H), 7.09 (d, J=2.2 Hz, 1H), 6.91 (d, J=1.0 Hz, 2H), 6.85 (s, 1H), 5.84-5.78 (m, 1H), 5.55 (dd, J=9.7, 15.7 Hz, 1H), 4.34-4.20 (m, 1H), 4.09 (s, 2H), 3.88-3.77 (m, 2H), 3.70 (d, J=14.3 Hz, 1H), 3.67-

3.61 (m, 1H), 3.60-3.56 (m, 2H), 3.56-3.49 (m, 1H), 3.25 (d, J=14.3 Hz, 1H), 3.04 (dd, J=10.1, 15.4 Hz, 1H), 2.73-2.60 (m, 2H), 2.44-2.32 (m, 1H), 2.31-2.18 (m, 1H), 2.17-1.93 (m, 4H), 1.93-1.81 (m, 3H), 1.79-1.68 (m, 2H), 1.65-1.53 (m, 1H), 1.37 (d, J=7.0 Hz, 3H), 1.31 (s, 1H), 0.95 (d, J=6.8 Hz, 3H). m/z (ESI, +ve ion) 661.3 (M+H)+.

Example 512. (1S,3'R,6'R,7'S,8'E,11'S,12'R)-6-chloro-7'-(3-methoxypropoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

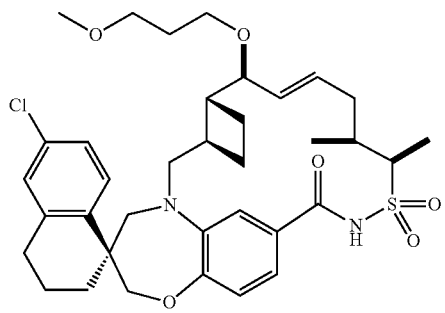 [SMILES: COCCCO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

To a 100 ml round-bottomed flask was added (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (from Example 719, Step 2) (50 mg, 0.083 mmol), 5 mL of DMF and then NaH (60% in mineral oil, 33 mg, 0.83 mmol) at room temperature. The reaction mixture was stirred at room temperature for 15 minutes at which time 1-bromo-3-methoxypropane (Matrix Scientific, Columbia, SC) (0.048 ml, 0.42 mmol) was added. The reaction mixture was stirred at 60° C. for 24 hours. The reaction was then quenched with 20 ml of saturated aqueous ammonium chloride and 20 ml of 1 N HCl and then extracted with 100 mL of diethyl ether. The organic layer was back extract twice with 50 ml brine. The organic layer was then dried over sodium sulfate, concentrated by rotary evaporation and the crude product was purified by reversed phase preparatory HPLC (Gemini™ Prep C$_{18}$ 5 µm column; Phenomenex, Torrance, CA; gradient elution of 10% to 90% MeCN in water, where both solvents contain 0.1% TFA, 45 minute method) to give the title compound (12 mg, 0.17 mmol, 20% yield) as a white solid. $^1$H NMR (400 MHz, CD$_2$Cl$_2$) δ 8.12 (br. s., 1H), 7.70 (d, J=8.4 Hz, 1H), 7.17 (dd, J=2.3, 8.4 Hz, 1H), 7.09 (d, J=2.3 Hz, 1H), 6.91 (d, J=1.0 Hz, 2H), 6.86 (s, 1H), 5.77 (ddd, J=3.3, 9.5, 15.2 Hz, 1H), 5.58-5.42 (m, 1H), 4.34-4.20 (m, 1H), 4.08 (s, 2H), 3.82 (d, J=15.1 Hz, 1H), 3.76-3.59 (m, 2H), 3.50-3.35 (m, 3H), 3.33-3.23 (m, 5H), 3.02 (dd, J=10.3, 15.4 Hz, 1H), 2.86-2.64 (m, 2H), 2.48-2.38 (m, 1H), 2.32 (quin, J=9.0 Hz, 1H), 2.22-2.01 (m, 3H), 1.99-1.90 (m, 3H), 1.89-1.61 (m, 6H), 1.44 (d, J=7.2 Hz, 3H), 1.41-1.34 (m, 1H), 1.02 (d, J=6.8 Hz, 3H). m/z (ESI, +ve ion) 671.3 (M+H)+.

Example 513. (1S,3'R,6'R,7'S,8'E,11'S,12'R)-6-chloro-7'-(2-(dimethylamino)ethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

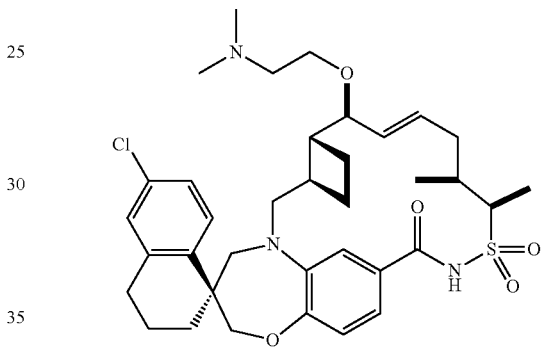

To a 2 dram pressure relief vial was added (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (from Example 14) (47 mg, 0.067 mmol), 2 ml of DMSO and dimethylamine (2.o M in THF, 0.15 ml, 0.30 mmol). The reaction was sealed with a pressure release fitted cap and heated to 55° C. for 16 hours. The reaction was then quenched with 20 ml of 1 N HCl and extracted with 100 ml of EtOAc. The organic layer was dried over sodium sulfate, filtered and the solvent was removed by rotary evaporation. The crude was purified on a Combiflash (4 g gold silica column), eluting with 10% MeOH in DCM), to give the title compound (27 mg, 0.040 mmol, 60% yield) as a white solid. $^1$H NMR (400 MHz, CD$_2$Cl$_2$) δ 7.72 (d, J=8.4 Hz, 1H), 7.20-7.03 (m, 3H), 6.97 (s, 1H), 6.82 (d, J=8.0 Hz, 1H), 6.13-5.84 (m, 1H), 5.53 (dd, J=8.2, 15.1 Hz, 1H), 4.02 (s, 2H), 3.93-3.63 (m, 5H), 3.63-3.52 (m, 1H), 3.26 (d, J=14.1 Hz, 1H), 3.08-2.88 (m, 3H), 2.82-2.72 (m, 2H), 2.66 (s, 6H), 2.49-2.35 (m, 2H), 2.20-1.98 (m, 4H), 1.88-1.61 (m, 4H), 1.35 (d, J=7.2 Hz, 3H), 1.37-1.29 (m, 3H), 0.99 (d, J=5.3 Hz, 3H). m/z (ESI, +ve ion) 670.4 (M+H)+.

Example 514. (1S,3'R,6'R,7'S,8'E,12'R)-6-chloro-7'-hydroxy-12'-((2R)-2-methoxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-6-chloro-7'-hydroxy-12'-((2R)-2-methoxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

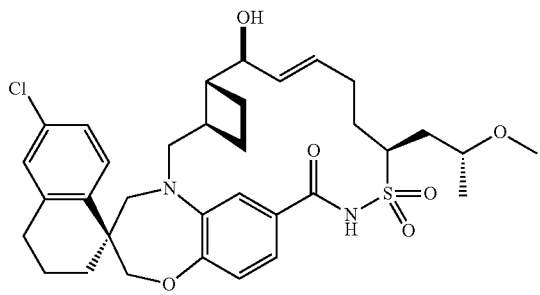

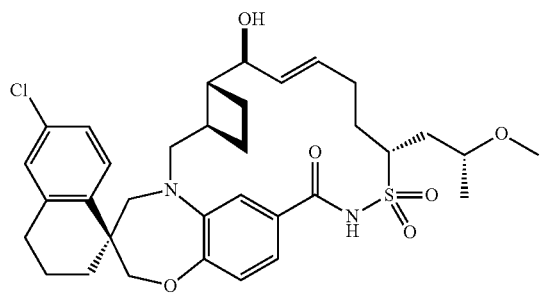

Step 1: (2R,4S)-2-methoxyoct-7-ene-4-sulfonamide or (2R,4R)-2-methoxyoct-7-ene-4-sulfonamide

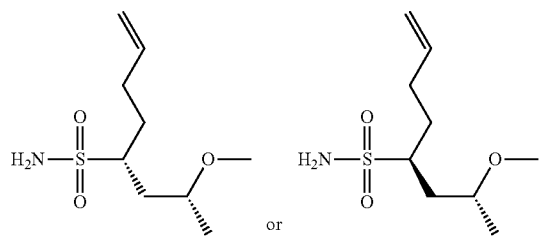

(2R,4S)-2-methoxyoct-7-ene-4-sulfonamide or (2R,4R)-2-methoxyoct-7-ene-4-sulfonamide was obtained as the slower eluting isomer in Example 508, Step 5.

Step 2: (S)-6'-chloro-5-(((1R,2R)-2-((1S,6R,8R,E)-1-hydroxy-8-methoxy-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((1S,6S,8R,E)-1-hydroxy-8-methoxy-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic Acid

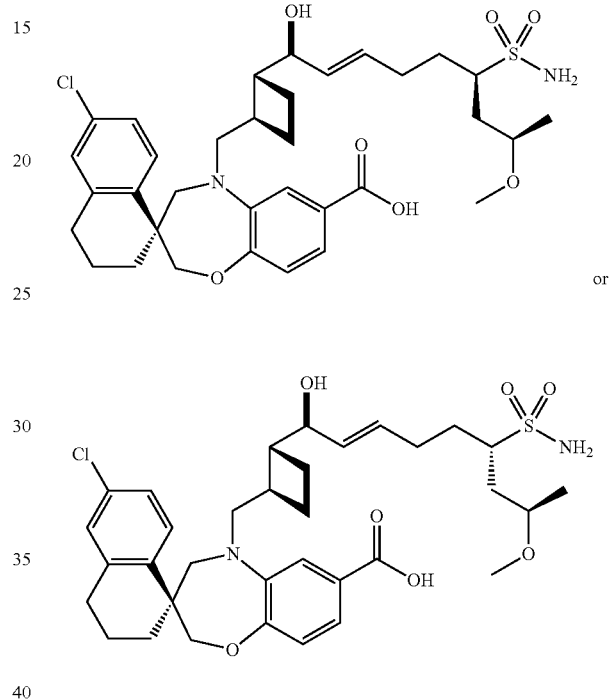

To a 100 ml flask was added (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (from Intermediate AA12A) (20 mg, 0.039 mmol), [(2R,4S)-2-methoxyoct-7-ene-4-sulfonamide or (2R,4R)-2-methoxyoct-7-ene-4-sulfonamide] (from Step 1)(22 mg, 0.098 mmol) and DCE (2 mL). The solution was sparged with argon for 15 minutes at which time (1,3-dimesitylimidazolidin-2-ylidene)(2-isopropoxybenzylidene)ruthenium(VI) chloride (2.5 mg, 3.9 μmol) was added as a 0.2 mL solution in DCE at room temperature. The mixture was stirred at room temperature for additional 16 hours. Note: the clear solution becomes slowly darker. The reaction mixture was then bubbled with air for 5 minutes and filtered. The solvent was removed from the filtrate and was directly purified on a Combiflash (4 g gold silica column), eluting with 50%-90% EtOAc in heptanes+0.2% AcOH, to give [(S)-6'-chloro-5-(((1R,2R)-2-((1S,6R,8R,E)-1-hydroxy-8-methoxy-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1R,2R)-2-((1S,6S,8R,E)-1-hydroxy-8-methoxy-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic acid] (19 mg, 0.029 mmol, 73% yield) as white solids.

Step 3: (1S,3'R,6'R,7'S,8'E,12'R)-6-chloro-7'-hydroxy-12'-((2R)-2-methoxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'S)-6-chloro-7'-hydroxy-12'-((2R)-2-methoxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide To a 100 ml flask containing [((S)-6'-chloro-5-(((1R,2R)-2-((1S,6R,8R,E)-1-hydroxy-8-methoxy-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((1S,6S,8R,E)-1-hydroxy-8-methoxy-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic acid] (from Step 2)(19 mg, 0.029 mmol), which was previously dried by rotovaping twice with 10 ml of toluene, was added N,N-dimethylpyridin-4-amine (6.0 mg, 0.049 mmol), 45 ml of DCM and N-(3-dimethylaminopropyl)-N'-ethylcarbodiimide hydrochloride (11 mg, 0.057 mmol). The reaction was stirred at room temperature for 18 hour at which time the mixture was quenched with 100 ml of 1N HCl and extracted with 300 ml of EtOAc. The organic layer were dried over anhydrous sodium sulfate, filtered, and concentrated by rotary evaporation. The crude product was purified on a Combiflash (4 g gold silica column), eluting with 30%-70% EtOAc in heptanes, to give the title compound (1.5 mg, 2.3 μmol, 8% yield) as a white solid Rf=0.16 eluting with 50% EtOAc in Heptanes. $^1$H NMR (400 MHz, CDCl$_3$) δ 8.20 (s, 1H), 7.70 (d, J=8.6 Hz, 1H), 7.19 (dd, J=2.3, 8.4 Hz, 1H), 7.09 (d, J=2.2 Hz, 1H), 6.96-6.83 (m, 3H), 5.90-5.81 (m, 1H), 5.76-5.64 (m, 1H), 4.22 (dd, J=4.2, 7.5 Hz, 2H), 4.14-4.02 (m, 3H), 3.87-3.68 (m, 3H), 3.36 (s, 3H), 3.24 (d, J=14.3 Hz, 1H), 3.03 (dd, J=9.1, 15.4 Hz, 1H), 2.85-2.68 (m, 2H), 2.53-2.19 (m, 5H), 2.08-1.74 (m, 8H), 1.49-1.35 (m, 2H), 1.28 (d, J=6.1 Hz, 3H). m/z (ESI, +ve ion) 643.0 (M+H)$^+$.

Example 515. (1S,3'R,6'R,7'S,8'E,11'S,12'R)-6-chloro-7'-(2-(3,3-difluoro-1-piperidinyl)ethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

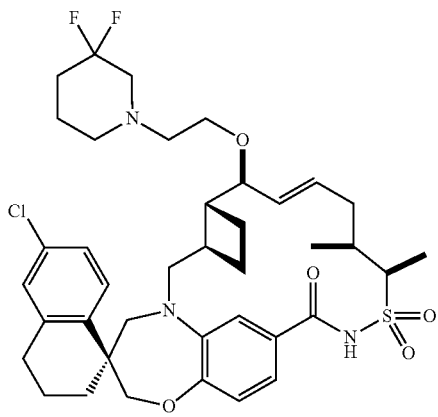

To a 4 ml vial was added (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24] tetraen]-7'-yl)oxy)acetaldehyde (from 527, Step 1) (20 mg, 0.031 mmol), DCE (4 ml), 3,3-difluoropiperidine hydrochloride (Frontier Scientific, Logan, UT)(19 mg, 0.13 mmol) and triethylamine (0.017 ml, 0.13 mmol). The reaction was heated at 50° C. for 5 minutes, at which time the reaction was cooled to room temperature and sodium triacetoxyborohydride (33 mg, 0.16 mmol) was added. The reaction was then stirred at 50° C. for 16 hours at which time the reaction was quenched with 0.2 ml of MeOH and 50 ml of saturated sodium bicarbonate. The aqueous solution was extracted with 100 ml of EtOAc and the EtOAc layer was washed with 50 ml of brine. The organic layer was dried over sodium sulfate, filtered and the solvent removed by rotary evaporation. The crude product was purified by reversed phase preparatory HPLC (Gemini™ Prep C$_{18}$ 5 μm column; Phenomenex, Torrance, CA; gradient elution of 10% to 90% MeCN in water, where both solvents contain 0.1% TFA, 45 minute method) to give the title compound (1.6 mg, 2.1 μmol, 6.9% yield) as an amorphous solid. $^1$H NMR (400 MHz, CD$_2$Cl$_2$) δ 8.14 (br.s., 1H), 7.70 (d, J=8.6 Hz, 1H), 7.17 (dd, J=2.4, 8.5 Hz, 1H), 7.09 (d, J=2.2 Hz, 1H), 6.91 (d, J=1.0 Hz, 2H), 6.83 (s, 1H), 5.98-5.80 (m, 1H), 5.65-5.46 (m, 1H), 4.32-4.22 (m, 1H), 4.16 (d, J=16.8 Hz, 1H), 4.08 (s, 2H), 3.89-3.75 (m, 3H), 3.69 (d, J=14.7 Hz, 1H), 3.64-3.56 (m, 1H), 3.50-3.38 (m 2H), 3.37-3.32 (m, 2H), 3.25 (d, J=14.3 Hz, 2H), 3.04 (dd, J=10.2, 15.5 Hz, 1H), 2.83-2.66 (m, 2H), 2.52-2.39 (m, 1H), 2.34 (t, J=8.8 Hz, 1H), 2.23-1.90 (m, 14H), 1.45 (d, J=7.2 Hz, 3H), 1.41-1.32 (m, 1H), 1.03 (d, J=6.8 Hz, 3H). m/z (ESI, +ve ion) 746.3 (M+H)$^+$.

Example 516. (1S,3'R,6'R,7'S,8'E,11'S,12'R)-6-chloro-7'-(2-hydroxyethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

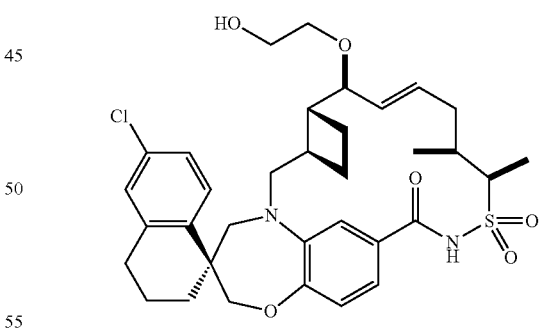

To a 25-mL round-bottomed flask was added a mixture of (1S,3'R,6'R,7'S,8'E,11'S,12'R)-6-chloro-11',12'-dimethyl-7'-(2-((2S)-tetrahydro-2H-pyran-2-yloxy)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,11'S,12'R)-6-chloro-11',12'-dimethyl-7'-(2-((2R)-tetrahydro-2H-pyran-2-yloxy)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (from Example 517) (185 mg, 0.254 mmol), 2 ml THF, and of 2 mL 2 N aqueous HCl. The reaction mixture was heated to 55° C. for 45 minutes at which time the reaction was diluted with 100 ml of EtOAc and washed with 50 ml of 1N HCl and 50 ml of brine. The aqueous layer was back extracted with 200 ml of EtOAc and the combined organic phase was dried over sodium sulfate, filtered and concentrated by rotary evaporation. The crude material was purified on a Combiflash (12 gram gold silica column), eluting with 50%-90% EtOAc in heptanes to give the title compound (107 mg, 0.166 mmol, 65% yield) as a white solid. Rf=0.51 eluting with 90% EtOAc in heptanes. $^1$H NMR (400 MHz, CD$_2$Cl$_2$) δ 8.05 (br. s., 1H), 7.63 (d, J=8.4 Hz, 1H), 7.09 (dd, J=2.3, 8.6 Hz, 1H), 7.01 (d, J=2.2 Hz, 1H), 6.88-6.75 (m, 3H), 5.73 (ddd, J=3.4, 9.5, 15.1 Hz, 1H), 5.47 (dd, J=9.2, 15.3 Hz, 1H), 4.17 (m, 1H), 4.00 (s, 2H), 3.80-3.67 (m, 2H), 3.65-3.48 (m, 3H), 3.42 (ddd, J=3.2, 6.2, 9.8 Hz, 1H), 3.27 (ddd, J=3.4, 6.1, 9.9 Hz, 1H), 3.17 (d, J=14.1 Hz, 1H), 2.95 (dd, J=10.2, 15.3 Hz, 1H), 2.78-2.50 (m, 2H), 2.46-2.33 (m, 1H), 2.26 (m, 1H), 2.15-1.82 (m, 6H), 1.80-1.68 (m, 4H), 1.66-1.53 (m, 1H), 1.36 (d, J=7.2 Hz, 3H), 0.95 (d, J=6.8 Hz, 3H). m/z (ESI, +ve ion) 643.0 (M+H)$^+$.

Example 517. (1S,3'R,6'R,7'S,8'E,11'S,12'R)-6-chloro-11',12'-dimethyl-7'-(2-((2S)-tetrahydro-2H-pyran-2-yloxy)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide and (1S,3'R,6'R,7'S,8'E,11'S,12'R)-6-chloro-11',12'-dimethyl-7'-(2-((2R)-tetrahydro-2H-pyran-2-yloxy)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

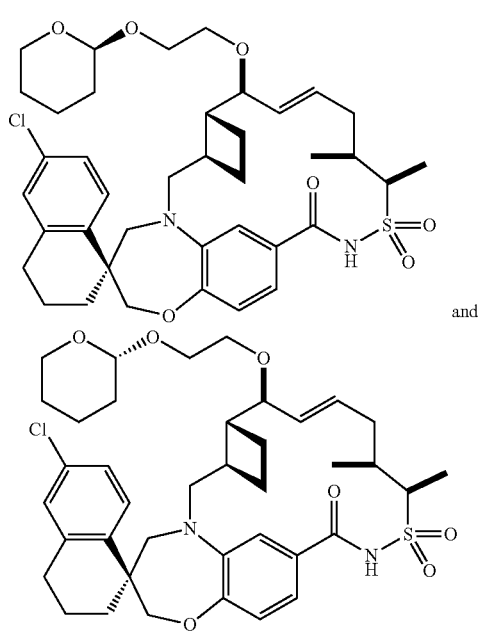

To a 250 ml round-bottomed flask was added (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (from Example 719, Step 2) (650 mg, 1.09 mmol), 60 mL of DMF and then sodium hydride, 60% dispersion in mineral oil (434 mg, 10.9 mmol) at room temperature. The reaction mixture was stirred at room temperature for 15 minutes at which time 2-(2-bromoethoxy)tetrahydro-2H-pyran (0.819 ml, 5.42 mmol) was added. The reaction mixture was stirred at 50° C. for 16 hours. The reaction was then quenched with 100 ml of saturated aqueous ammonium chloride and 100 ml of 1 N HCl and then extracted with 400 mL of diethyl ether. The organic layer was back extract twice with 100 ml brine. The organic layer was then dried over sodium sulfate, concentrated by rotary evaporation and was purified on a Combiflash (12 gram gold silica column), eluting with 10%-50% EtOAc in heptanes, to give a mixture of title compounds (650 mg, 1.09 mmol) as a white solid. $^1$H NMR (400 MHz, CD$_2$Cl$_2$) δ 8.07 (d, J=6.3 Hz, 1H), 7.71 (d, J=8.6 Hz, 1H), 7.17 (dd, J=2.3, 8.4 Hz, 1H), 7.09 (d, J=2.3 Hz, 1H), 6.93-6.90 (m, 2H), 6.87 (s, 1H), 5.89-5.74 (m, 1H), 5.62-5.47 (m, 1H), 4.63-4.54 (m, 1H), 4.32-4.20 (m, 1H), 4.15-4.00 (m, 2H), 3.91-3.65 (m, 5H), 3.60-3.36 (m, 4H), 3.26 (d, J=14.3 Hz, 1H), 3.03 (dd, J=10.1, 15.4 Hz, 1H), 2.85-2.66 (m, 2H), 2.53-2.41 (m, 1H), 2.33 (m, 1H), 2.25-2.02 (m, 3H), 2.02-1.89 (m, 3H), 1.87-1.76 (m, 4H), 1.75-1.62 (m, 2H), 1.59-1.49 (m, 4H), 1.45 (d, J=7.2 Hz, 3H), 1.40-1.37 (m, 1H), 1.03 (d, J=6.8 Hz, 3H). m/z (ESI, +ve ion) 727.4 (M+H)$^+$.

Example 518. (1S,3'R,6'R,7'S,8'E,11'S,12'R)-6-chloro-11',12'-dimethyl-7'-(2-(2-oxa-6-azaspiro[3.3]hept-6-yl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

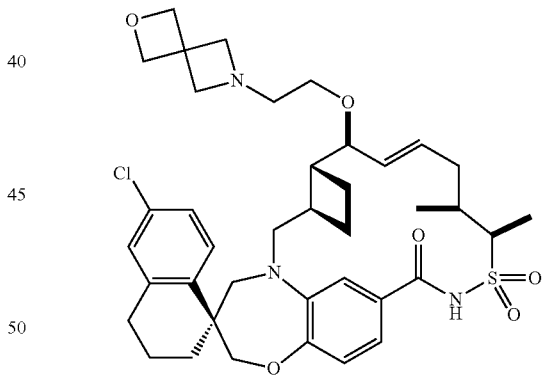

To a 100 ml flask was added (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetaldehyde (from 527, Step 1) (10 mg, 0.016 mmol), DCE (2 ml), 2-oxa-6-azaspiro[3.3]heptane (AMRI, Albany, NY) (6.37 mg, 0.064 mmol), and sodium triacetoxyborohydride (17 mg, 0.080 mmol). The reaction was stirred at 55° C. for 5 hours at which time the reaction was quenched with 0.5 ml of MeOH and 100 ml of saturated sodium bicarbonate. The aqueous solution was extracted with 300 ml of EtOAc and the EtOAc layer was washed with 100 ml of brine. The organic layer was dried over sodium sulfate, filtered and the solvent removed by rotary evaporation. The crude product was purified by reversed phase preparatory HPLC (Gemini™ Prep $C_{18}$ 5 μm column; Phenomenex, Torrance, CA; gradient elution of 10% to 90% MeCN in water, where both solvents contain 0.1% TFA, 45 minute method) to give the title compound (1.6 mg, 2.1 μmol, 13% yield) as a white film. $^1$H NMR (400 MHz, $CD_2Cl_2$) δ 8.12 (br. s., 1H), 7.70 (d, J=8.6 Hz, 1H), 7.17 (dd, J=2.3, 8.4 Hz, 1H), 7.09 (d, J=2.3 Hz, 1H), 6.91 (s, 2H), 6.81 (s, 1H), 5.94-5.78 (m, 1H), 5.58-5.44 (m, 1H), 4.84 (s, 2H), 4.69 (s, 2H), 4.62 (s, 2H), 4.31-4.17 (m, 1H), 4.08 (s, 2H), 3.98 (d, J=11.0 Hz, 2H), 3.84-3.62 (m, 4H), 3.48 (s, 1H), 3.25 (d, J=14.3 Hz, 1H), 3.19 (s, 2H), 3.03 (dd, J=10.0, 15.3 Hz, 1H), 2.87-2.66 (m, 2H), 2.50-2.38 (m, 1H), 2.36-2.23 (m, 1H), 2.20-2.09 (m, 2H), 1.86-1.77 (m, 6H), 1.74-1.63 (m, 2H), 1.44 (d, J=7.2 Hz, 3H), 1.41-1.41 (m, 1H), 1.02 (d, J=6.8 Hz, 3H). m/z (ESI, +ve ion) 724.3 (M+H)$^+$.

Example 519. (1S,3'R,6'R,7'S,8'E,11'S,12'R)-6-chloro-7'-(((2R)-2-methoxypropyl)oxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide and (1S,3'R,6'R,7'S,8'E,11'S,12'R)-6-chloro-7'-(((2S)-2-methoxypropyl)oxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide Step 1: (1S,3'R,6'R,7'S,8'E,11'S,12'R)-6-chloro-7'-(((2R)-2-hydroxypropyl)oxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide and (1S,3'R,6'R,7'S,8'E,11'S,12'R)-6-chloro-7'-(((2S)-2-hydroxypropyl)oxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13' 13'-dioxide

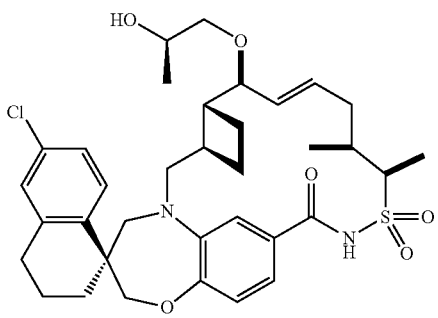

and

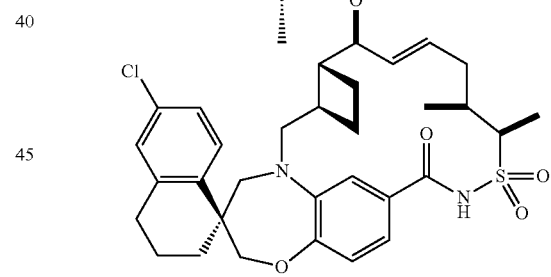

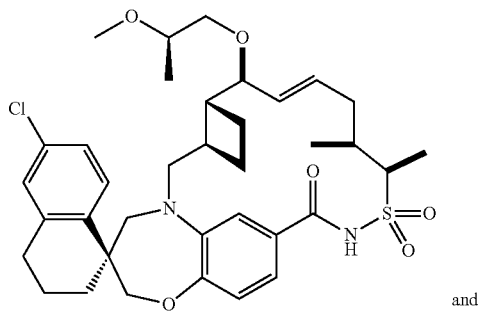

and

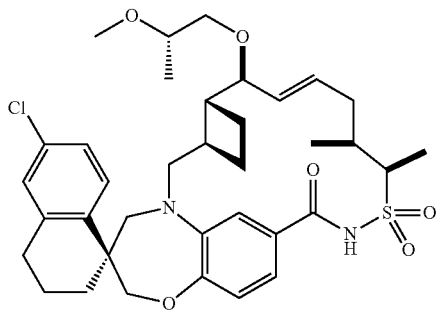

To a 100 ml flask containing (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetaldehyde (from 527, Step 1) (240 mg, 0.374 mmol) was added 20 ml of THF and the reaction was cooled to −78° C. at which time methylmagnesium bromide 3.0 M in diethyl ether (0.37 ml, 1.1 mmol) was added. The reaction was stirred at room temperature for 1 hour, then quenched with 100 ml of saturated ammonium chloride and extracted once with 400 ml of EtOAc. The organic layer was dried over sodium sulfate, filtered and the solvent removed by rotary evaporation. The crude was purified on a Combiflash (12 g gold silica column), eluting with 10%-70% EtOAc in heptanes) to give [(1S,3'R,6'R,7'S,8'E,11'S,12'R)-6-chloro-7'-(((2R)-2-hydroxypropyl)oxy)-11',12'-dimethyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,11'S,12'R)-6-chloro-7'-(((2S)-2-hydroxypropyl)oxy)-11',12'-dimethyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (26 mg, 0.040 mmol) as a white solid.

Step 2: (1S,3'R,6'R,7'S,8'E,11'5,12'R)-6-chloro-7'-(((2R)-2-methoxypropyl)oxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide and (1S,3'R,6'R,7'S,8'E,11'S,12'R)-6-chloro-7'-(((2S)-2-methoxypropyl)oxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide To a 100 ml flask was added [(1S,3'R,6'R,7'S,8'E,11'S,12'R)-6-chloro-7'-(((2R)-2-hydroxypropyl)oxy)-11',12'-dimethyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,11'S,12'R)-6-chloro-7'-(((2S)-2-hydroxypropyl)oxy)-11',12'-dimethyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (from Step 1) (26 mg, 0.040 mmol), DMF (2 mL) and NaH, 60% in oil (50.3 mg, 2.098 mmol). The reaction was stirred at room temperature for 20 minutes at which time MeI (0.025 ml, 0.40 mmol) was added. The reaction was then stirred at room temperature for 4 hours at which time the reaction was quenched with 50 ml of saturated ammonium chloride and extracted with 200 ml of EtOAc. The organic layer was dried over sodium sulfate, filtered and the solvent was removed by rotary evaporation. The crude product was purified by reversed phase preparatory HPLC (Gemini™ Prep C$_{18}$ 5 μm column; Phenomenex, Torrance, CA; gradient elution of 50% to 90% MeCN in water, where both solvents contain 0.1% TFA, 45 minute method) to give a 1:1 mixture of the title compounds (4.0 mg, 6.0 μmol, 15% yield) as a white solid. $^1$H NMR (400 MHz, CD$_2$Cl$_2$) δ 8.08 (s, 1H), 7.71 (d, J=8.4 Hz, 1H), 7.17 (dd, J=2.3, 8.4 Hz, 1H), 7.09 (d, J=2.2 Hz, 1H), 6.91 (m, 2H), 6.86 (s, 1H), 5.86-5.68 (m, 1H), 5.61-5.45 (m, 1H), 4.34-4.19 (m, 1H), 4.08 (s, 2H), 3.82 (d, J=14.7 Hz, 1H), 3.77-3.64 (m, 2H), 3.45-3.35 (m, 1.5, H), 3.33 (s, 1.5H), 3.32 (s, 1.5H), 3.30-3.21 (m, 2H), 3.17 (dd, J=3.8, 9.5 Hz, 0.5H), 3.03 (dd, J=10.5, 15.2 Hz, 1H), 2.87 (s, 1H), 2.83-2.71 (m, 2H), 2.51-2.39 (m, 1H), 2.38-2.26 (m, 1H), 2.23-2.01 (m, 3H), 2.00-1.90 (m, 3H), 1.88-1.77 (m, 3H), 1.45 (d, J=7.2 Hz, 3H), 1.39 (m, 1H), 1.09 (d, J=5.2 Hz, 1.5H), 1.07 (d, J=5.2 Hz, 1.5H), 1.03 (d, J=6.8 Hz, 3H). m/z (ESI, +ve ion) 671.5 (M+H)$^+$.

Example 520. (1S,3'R,6'R,7'S,8'E,11'S,12'R)-6-chloro-11,12'-dimethyl-7'-(2-((1S,4S)-2-oxa-5-azabicyclo[2.2.1]hept-5-yl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide 2,2,2-trifluoroacetic Acid

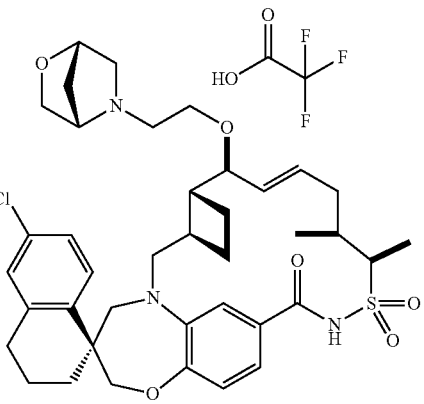

To a 4 ml vial was added (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetaldehyde (from 527, Step 1) (20 mg, 0.031 mmol), DCE (4 ml), (1S,4S)-2-oxa-5-azabicyclo[2.2.1]heptane hydrochloride (4.2 mg, 0.031 mmol) (Frontier Scientific, Logan, UT) and triethylamine (0.017 ml, 0.13 mmol). The reaction was heated at 50° C. for 5 minutes, the reaction was cooled to room temperature and sodium triacetoxyborohydride (33 mg, 0.16 mmol) was then added. The reaction was stirred at 50° C. for 16 hours at which time the reaction was quenched with 0.2 ml of MeOH and 50 ml of saturated sodium bicarbonate. The aqueous solution was extracted with 100 ml of EtOAc and the EtOAc layer was washed with 50 ml of brine. The organic layer was dried over sodium sulfate, filtered and the solvent removed by rotary evaporation. The crude product was purified by reversed phase preparatory HPLC (Gemini™ Prep C$_{18}$ 5 μm column; Phenomenex, Torrance, CA; gradient elution of 10% to 90% MeCN in water, where both solvents contain 0.1% TFA, 45 minute method) to give the title compound (2.1 mg, 2.5 μmol, 8% yield) as an amorphous solid. $^1$H NMR (400 MHz, CD$_2$Cl$_2$) δ 8.07 (br. s., 1H), 7.62 (d, J=8.6 Hz, 1H), 7.09 (dd, J=2.3, 8.4 Hz, 1H), 7.01 (d, J=2.3 Hz, 1H), 6.88-6.82 (m, 2H), 6.74 (s, 1H), 5.86-5.67 (m, 1H), 5.53-5.35 (m, 1H), 4.63-4.43 (m, 1H), 4.39-4.28 (m, 1H), 4.27-4.03 (m, 3H), 4.02-3.93 (m, 2H), 3.83-3.54 (m, 6H), 3.44 (d, J=10.2 Hz, 1H), 3.39-3.31 (m, 1H), 3.26 (d, J=6.5 Hz, 1H), 2.98-2.86 (m, 2H), 2.72-2.59 (m, 2H), 2.40-2.31 (m, 1H), 2.26 (d, J=9.8 Hz, 2H), 2.11 (d, J=12.1 Hz, 2H), 2.03-1.89 (m, 5H), 1.78-1.70 (m, 2H), 1.68-1.49 (m, 2H), 1.36 (d, J=7.2 Hz, 3H), 1.33-1.27 (m, 1H), 0.94 (d, J=6.8 Hz, 3H). m/z (ESI, +ve ion) 724.4 (M+H)$^+$.

Example 521. (1S,3'R,6'R,7'S,8'E,11'S,12'R)-6-chloro-11',12'-dimethyl-7'-(2-((1R,4R)-2-oxa-5-azabicyclo[2.2.1]hept-5-yl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide 2,2,2-trifluoroacetic Acid

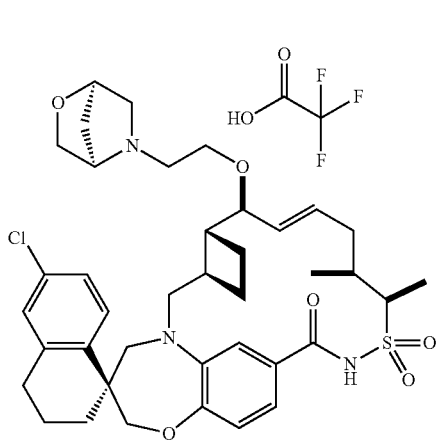

To a 4 ml vial was added ((((1S,3'R,6'R,7'S,8'E,11'S,12'R)-6-chloro-11', 12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetaldehyde (from 527, Step 1) (20 mg, 0.031 mmol), DCE (4 ml), (1R,4R)-2-oxa-5-azabicyclo[2.2.1]heptane hydrochloride (4.2 mg, 0.031 mmol) (Frontier Scientific, Logan, UT) and triethylamine (0.017 ml, 0.13 mmol). The reaction was heated at 50° C. for 5 minutes the reaction was cooled to room temperature and sodium triacetoxyborohydride (33 mg, 0.16 mmol) was then added. The reaction was stirred at 50° C. for 16 hours at which time the reaction was quenched with 0.2 ml of MeOH and 50 ml of saturated sodium bicarbonate. The aqueous solution was extracted with 100 ml of EtOAc and the EtOAc layer was washed with 50 ml of brine. The organic layer was dried over sodium sulfate, filtered and the solvent removed by rotary evaporation. The crude product was purified by reversed phase preparatory HPLC (Gemini™ Prep C$_{18}$ 5 µm column; Phenomenex, Torrance, CA; gradient elution of 10% to 90% MeCN in water, where both solvents contain 0.1% TFA, 45 minute method) to give the title compound (1.7 mg, 2.0 µmol, 6.5% yield) as an amorphous solid. $^1$H NMR (400 MHz, CD$_2$Cl$_2$) δ 8.15 (br. s., 1H), 7.69 (d, J=8.4 Hz, 1H), 7.16 (dd, J=2.3, 8.4 Hz, 1H), 7.08 (d, J=2.3 Hz, 1H), 6.90 (s, 2H), 6.81 (s, 1H), 5.92-5.71 (m, 1H), 5.59-5.40 (m, 1H), 4.61-4.42 (m, 2H), 4.34-4.12 (m, 2H), 4.07 (s, 2H), 3.86-3.73 (m, 5H), 3.68 (d, J=14.5 Hz, 1H), 3.62-3.53 (m, 1H), 3.41 (d, J=4.7 Hz, 1H), 3.36-3.17 (m, 2H), 3.07-2.92 (m, 2H), 2.83-2.66 (m, 2H), 2.47-2.28 (m, 3H), 2.19-2.00 (m, 5H), 1.97-1.87 (m, 6H), 1.43 (d, J=7.2 Hz, 3H), 1.39 (m, 1H), 1.01 (d, J=6.8 Hz, 3H). m/z (ESI, +ve ion) 724 (M+H)$^+$.

Example 522. (1S,3'R,6'R,7'S,8'E,11'S,12'R)-6-chloro-11',12'-dimethyl-7'-(2-(3-oxetanylamino)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide 2,2,2-trifluoroacetic Acid

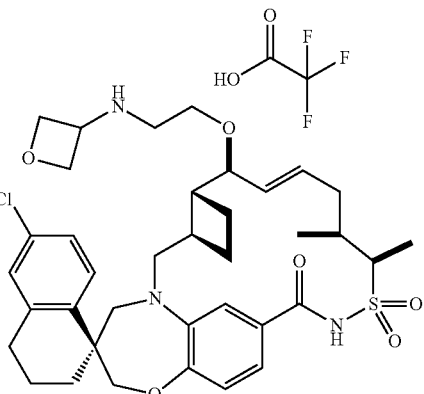

To a 4 ml vial was added ((((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetaldehyde (from 527, Step 1) (20 mg, 0.031 mmol), DCE (4 ml), oxetan-3-amine hydrochloride (14 mg, 0.13 mmol)(Frontier Scientific, Logan, UT) and triethylamine (0.017 ml, 0.13 mmol). The reaction was heated at 50° C. for 5 minutes at which time the reaction was cooled to room temperature and sodium triacetoxyborohydride (33 mg, 0.16 mmol) was added. The reaction was stirred at 50° C. for 16 hours at which time the reaction was quenched with 0.2 ml of MeOH and 50 ml of saturated sodium bicarbonate. The aqueous solution was extracted with 100 ml of EtOAc and the EtOAc layer was washed with 50 ml of brine. The organic layer was dried over sodium sulfate, filtered and the solvent removed by rotary evaporation. The crude product was purified by reversed phase preparatory HPLC (Gemini™ Prep C$_{18}$ 5 µm column; Phenomenex, Torrance, CA; gradient elution of 10% to 90% MeCN in water, where both solvents contain 0.1% TFA, 45 minute method) to give the title compound (5.8 mg, 7.1 µmol, 23% yield) as an amorphous solid as an amorphous solid. $^1$H NMR (500 MHz, CD$_2$Cl$_2$) δ 8.41 (br. s., 1H), 7.69 (d, J=8.6 Hz, 1H), 7.17 (dd, J=2.3, 8.4 Hz, 1H), 7.09 (d, J=2.4 Hz, 1H), 6.99-6.89 (m, 2H), 6.82 (s, 1H), 5.95-5.75 (m, 1H), 5.60-5.46 (m, 1H), 4.90-4.75 (m, 4H), 4.41-4.33 (m, 1H), 4.29-4.17 (m, 1H), 4.06 (s, 2H), 3.86-3.75 (m, 2H), 3.72-3.61 (m, 2H), 3.49 (d, J=7.6 Hz, 1H), 3.24 (d, J=14.4 Hz, 1H), 3.21-3.14 (m, 1H), 3.10 (d, J=3.7 Hz, 1H), 3.02 (dd, J=10.5, 15.4 Hz, 1H), 2.85-2.68 (m, 2H), 2.52-2.42 (m, 1H), 2.33 (td, J=9.2, 18.2 Hz, 1H), 2.21-1.90 (m, 6H), 1.88-1.76 (m, 3H), 1.73-1.61 (m, 1H), 1.44 (d, J=7.1 Hz, 3H), 1.39 (t, J=12.8 Hz, 1H), 1.02 (d, J=6.8 Hz, 3H). m/z (ESI, +ve ion) 698.4 (M+H)$^+$.

Example 523. (1S,3'R,6'R,7'S,8'E,11'S,12'R)-6-chloro-11',12'-dimethyl-7'-(2-((3R)-3-methyl-4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide Example 524. (1S,3'R,6'R,7'S,8'E,11'S,12'R)-6-chloro-7'-(2-(1,1-dioxido-4-thiomorpholinyl)ethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

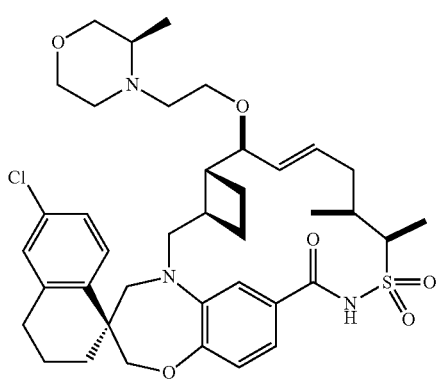

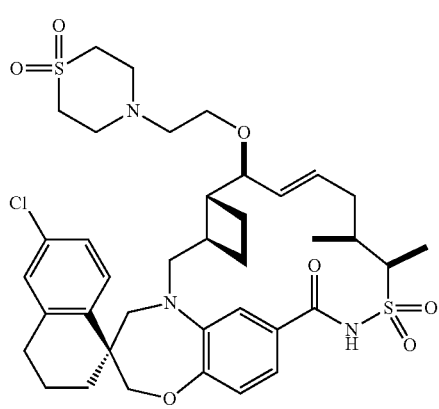

To a 100 ml flask were added (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetaldehyde (from 527, Step 1) (16 mg, 0.025 mmol), DCE (2 ml), (R)-3-methylmorpholine (J & W PharmLab, Levittown, PA) (5.8 µl, 0.051 mmol) and sodium triacetoxyborohydride (27 mg, 0.13 mmol). The reaction was stirred at 55° C. for 5 hours at which time the reaction was quenched with 0.5 ml of MeOH and 100 ml of saturated sodium bicarbonate. The aqueous solution was extracted with 300 ml of EtOAc and the EtOAc layer was washed with 100 ml of brine. The organic layer was dried over sodium sulfate, filtered and the solvent removed by rotary evaporation. The crude product was purified by reversed phase preparatory HPLC (Gemini™ Prep C$_{18}$ 5 µm column; Phenomenex, Torrance, CA; gradient elution of 10% to 90% MeCN in water, where both solvents contain 0.1% TFA, 45 minute method) to give the title compound (2.9 mg, 4.0 µmol, 16% yield) as a white film. $^1$H NMR (400 MHz, CD$_2$Cl$_2$) δ 8.19 (br. s., 1H), 7.70 (d, J=8.6 Hz, 1H), 7.17 (dd, J=2.3, 8.4 Hz, 1H), 7.09 (d, J=2.2 Hz, 1H), 6.92 (s, 2H), 6.83 (s, 1H), 5.96-5.80 (m, 1H), 5.62-5.44 (m, 1H), 4.26 (q, J=6.8 Hz, 1H), 4.08 (s, 2H), 4.02-3.90 (m, 2H), 3.81 (d, J=14.3 Hz, 4H), 3.74-3.65 (m, 2H), 3.60-3.51 (m, 1H), 3.45 (t, J=11.4 Hz, 2H), 3.32-3.21 (m, 3H), 3.19-3.10 (m, 1H), 3.05 (dd, J=10.0, 15.5 Hz, 1H), 2.84-2.71 (m, 2H), 2.51-2.40 (m, 1H), 2.40-2.28 (m, 1H), 2.26-2.15 (m, 1H), 2.15-2.01 (m, 2H), 2.01-1.89 (m, 2H), 1.88-1.76 (m, 5H), 1.45 (d, J=7.2 Hz, 3H), 1.41-1.38 (m, 1H), 1.33 (d, J=6.5 Hz, 3H), 1.03 (d, J=6.7 Hz, 3H). m/z (ESI, +ve ion) 726.3 (M+H)$^+$.

To a 100 ml flask was added (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetaldehyde (Example 527, Step 1) (10 mg, 0.016 mmol), DCE (2 ml), thiomorpholine dioxide (TCI America, Portland, OR) (8.7 mg, 0.064 mmol) and sodium triacetoxyborohydride (17 mg, 0.080 mmol). The reaction was stirred at 55° C. for 5 hours at which time the reaction was quenched with 0.5 ml of MeOH and 100 ml of saturated sodium bicarbonate. The aqueous solution was extracted with 300 ml of EtOAc and the EtOAc layer was washed with 100 ml of brine. The organic layer was dried over sodium sulfate, filtered and the solvent removed by rotary evaporation. The crude product was purified by reversed phase preparatory HPLC (Gemini™ Prep C$_{18}$ 5 µm column; Phenomenex, Torrance, CA; gradient elution of 10% to 90% MeCN in water, where both solvents contain 0.1% TFA, 45 minute method) to give the title compound (1.7 mg, 2.2 mmol, 14% yield) as a white film. $^1$H NMR (400 MHz, CD$_2$Cl$_2$) δ 8.03 (br. s., 1H), 7.62 (d, J=8.4 Hz, 1H), 7.09 (dd, J=2.3, 8.4 Hz, 1H), 7.01 (d, J=2.2 Hz, 1H), 6.83 (s, 2H), 6.74 (s, 1H), 5.89-5.71 (m, 1H), 5.52-5.36 (m, 1H), 4.23-4.09 (m, 1H), 4.00 (s, 2H), 3.79-3.57 (m, 8H), 3.56-3.47 (m, 1H), 3.39 (s, 4H), 3.24-3.10 (m, 3H), 2.96 (dd, J=10.3, 15.4 Hz, 1H), 2.76-2.62 (m, 2H), 2.43-2.32 (m, 1H), 2.31-2.21 (m, 1H), 2.14-1.81 (m, 6H), 1.79-1.56 (m, 5H), 1.37 (d, J=7.0 Hz, 3H), 0.95 (d, J=6.8 Hz, 3H). m/z (ESI, +ve ion) 760.3 (M+H)$^+$.

Example 525. (1S,3'R,6'R,7'S,8'E,11'S,12'R)-6-chloro-7'-(2-(3-methoxy-1-azetidinyl)ethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide 2,2,2-trifluoroacetic Acid

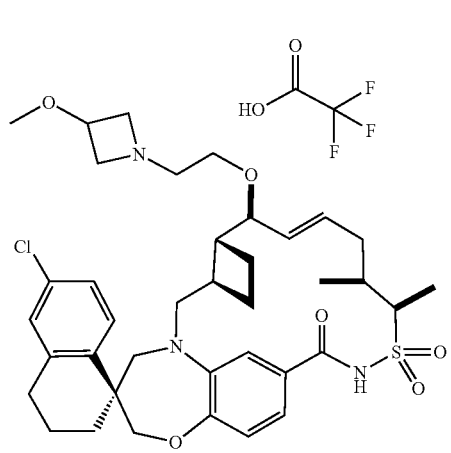

To a 4 ml vial was added (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetaldehyde (from 527, Step 1) (19 mg, 0.030 mmol), DCE (4 ml) and 3-methoxyazetidine (Frontier Scientific, Logan, UT)(10 mg, 0.12 mmol). The reaction was heated at 50° C. for 5 minutes, was cooled to room temperature and sodium triacetoxyborohydride (31 mg, 0.15 mmol) was added. The reaction was stirred at 50° C. for 16 hours at which time the reaction was quenched with 0.2 ml of MeOH and 50 ml of saturated sodium bicarbonate. The aqueous solution was extracted with 100 ml of EtOAc and the EtOAc layer was washed with 50 ml of brine. The organic layer was dried over sodium sulfate, filtered and the solvent removed by rotary evaporation. The crude product was purified by reversed phase preparatory HPLC (Gemini™ Prep C$_{18}$ 5 µm column; Phenomenex, Torrance, CA; gradient elution of 10% to 90% MeCN in water, where both solvents contain 0.1% TFA, 45 minute method) to give the title compound (2.8 mg, 3.4 µmol, 11% yield) as an amorphous solid. $^1$H NMR (400 MHz, CD$_2$Cl$_2$) δ 8.17 (br. s., 1H), 7.70 (d, J=8.6 Hz, 1H), 7.17 (dd, J=2.2, 8.4 Hz, 1H), 7.09 (d, J=2.3 Hz, 1H), 6.91 (s, 2H), 6.82 (s, 1H), 5.93-5.75 (m, 1H), 5.51 (dd, J=8.7, 14.4 Hz, 1H), 4.62-4.64 (m, 2H), 4.33 (d, J=6.1 Hz, 1H), 4.29-4.16 (m, 2H), 4.08 (s, 2H), 3.84-3.59 (m, 5H), 3.54-3.45 (m, 2H), 3.37-3.20 (m, 5H), 3.03 (dd, J=10.3, 15.4 Hz, 1H), 2.85-2.70 (m, 2H), 2.44 (d, J=9.6 Hz, 1H), 2.32 (td, J=8.8, 17.7 Hz, 1H), 2.22-1.72 (m, 9H), 1.71-1.62 (m, 1H), 1.44 (d, J=7.2 Hz, 3H), 1.41-1.32 (m, 1H), 1.02 (d, J=6.8 Hz, 3H). m/z (ESI, +ve ion) 712.4 (M+H)$^+$.

Example 526. (1S,3'R,6'R,7'S,8'E,11'S,12'R)-7'-(2-(1-azetidinyl)ethoxy)-6-chloro-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide 2,2,2-trifluoroacetic Acid

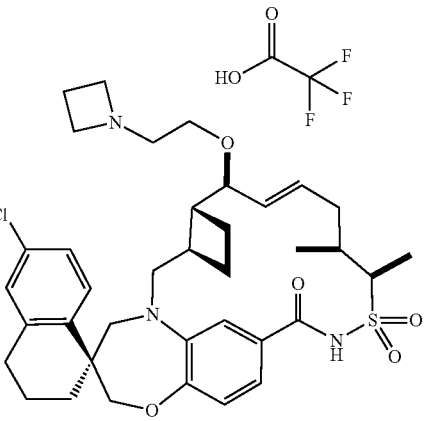

To a 4 ml vial was added (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetaldehyde (from 527, Step 1) (19 mg, 0.030 mmol), DCE (4 ml), azetidine hydrochloride (Frontier Scientific, Logan, UT) (11 mg, 0.12 mmol) and triethylamine (0.016 ml, 0.12 mmol). The reaction was heated at 50° C. for 5 minutes, the reaction was cooled to room temperature and sodium triacetoxyborohydride (31 mg, 0.15 mmol) was added. The reaction was stirred at 50° C. for 16 hours at which time the reaction was quenched with 0.2 ml of MeOH and 50 ml of saturated sodium bicarbonate. The aqueous solution was extracted with 100 ml of EtOAc and the EtOAc layer was washed with 50 ml of brine. The organic layer was dried over sodium sulfate, filtered and the solvent removed by rotary evaporation. The crude product was purified by reversed phase preparatory HPLC (Gemini™ Prep C$_{18}$ 5 µm column; Phenomenex, Torrance, CA; gradient elution of 10% to 90% MeCN in water, where both solvents contain 0.1% TFA, 45 minute method) to give the title compound (1.6 mg, 2.0 µmol, 6.8% yield) as an amorphous solid. $^1$H NMR (400 MHz, CD$_2$Cl$_2$) δ 8.11 (br. s., 1H), 7.70 (d, J=8.6 Hz, 1H), 7.17 (dd, J=2.3, 8.4 Hz, 1H), 7.09 (d, J=2.2 Hz, 1H), 6.98-6.88 (m, 2H), 6.82 (s, 1H), 5.93-5.74 (m, 1H), 5.56-5.47 (m, 1H), 4.39-4.29 (m, 2H), 4.25 (d, J=8.0 Hz, 1H), 4.08 (s, 2H), 3.94-3.73 (m, 4H), 3.69 (d, J=14.3 Hz, 2H), 3.51-3.41 (m, 1H), 3.24 (d, J=14.5 Hz, 3H), 3.02 (dd, J=10.3, 15.2 Hz, 1H), 2.82-2.64 (m, 3H), 2.44 (d, J=6.7 Hz, 1H), 2.36-2.24 (m, 2H), 2.22-2.01 (m, 3H), 2.01-1.49 (m, 7H), 1.44 (d, J=7.0 Hz, 3H), 1.40-1.35 (m, 1H), 1.02 (d, J=6.8 Hz, 3H). m/z (ESI, +ve ion) 682.4 (M+H)$^+$.

Example 527. (1S,3'R,6'R,7'S,8'E,11'S,12'R)-6-chloro-7'-(((2R)-2-hydroxypropyl)oxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-7'-(((2S)-2-hydroxypropyl)oxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

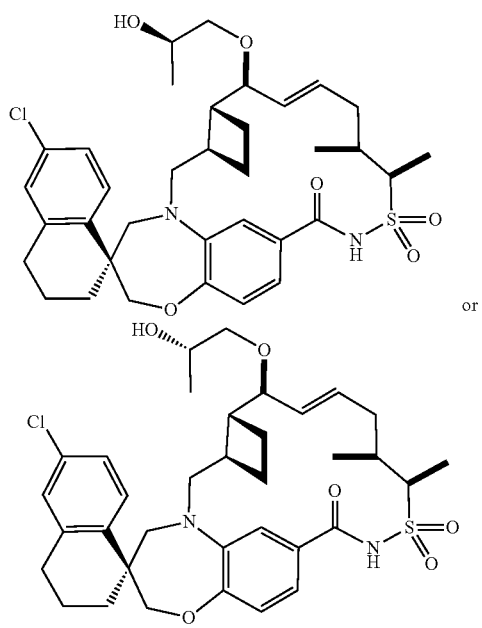

Step 1: (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)acetaldehyde

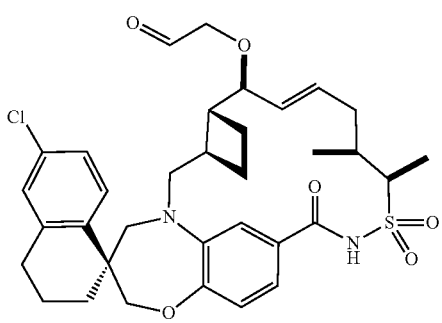

To a 100 ml flask containing (1S,3'R,6'R,7'S,8'E,11'S,12'R)-6-chloro-7'-(2-hydroxyethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (from Example 516) (380 mg, 0.591 mmol) was added 30 ml of wet DCM, the reaction was cooled to 0° C. and then dess-martin periodinane (501 mg, 1.18 mmol) was added. The white slurry was stirred at 0° C. for 30 minutes at which time the ice bath was removed and the reaction was stirred for an additional 8 hours. The reaction was then quenched with 100 ml of saturated aqueous sodium bicarbonate and extracted with 400 mL of EtOAc. The organic layer was extracted once more with 100 ml of brine, dried over sodium sulfate, concentrated by rotary evaporation and was purified on a Combiflash (12 gram gold silica column), eluting with 10%-50% EtOAc in heptanes, to give (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetaldehyde (240 mg, 0.374 mmol, 63% yield) as a white solid.

Step 2: (1S,3'R,6'R,7'S,8'E,11'S,12'R)-6-chloro-7'-(((2R)-2-hydroxypropyl)oxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-7'-(((2S)-2-hydroxypropyl)oxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide To a 100 ml flask containing (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetaldehyde (from Step 1) (240 mg, 0.374 mmol) was added 20 ml of THF and the reaction was cooled to −78° C. at which time methylmagnesium bromide 3.0 m in diethyl ether (0.374 ml, 1.12 mmol) was added. The reaction was stirred at room temperature for 1 hour, then quenched with 100 ml of saturated ammonium chloride and extracted once with 400 ml of EtOAc. The organic layer was dried over sodium sulfate, filtered and the solvent removed by rotary evaporation. The crude was first was purified on a Combiflash (12 gram gold silica column), eluting with 10%-70% EtOAc in heptanes. Rf=0.19 eluting with 50% EtOAc in heptanes. The racemic mixture (1:1) was then purified by preparatory SCF chromatography (Chiralpak AD-H 4.6×250 mM column, Phenomenex, Torrance, CA; elution of 35% EtOH in liquid CO$_2$; flow rate=3 mL/minute, 100 Bar BPR; 20 minute method, 0.5 mL stacked injections, 6 mg/mL) to provide the title compound (40 mg, 0.061 mmol, 33% yield), as the slower eluting isomer as a white solid (t$_R$=7.7 minutes). $^1$H NMR (400 MHz, CD$_2$Cl$_2$) δ 8.20 (br. s., 1H), 7.62 (d, J=8.4 Hz, 1H), 7.08 (dd, J=2.2, 8.6 Hz, 1H), 7.01 (d, J=2.0 Hz, 1H), 6.89-6.72 (m, 3H), 5.71 (ddd, J=3.3, 9.6, 15.1 Hz, 1H), 5.46 (dd, J=9.0, 15.1 Hz, 1H), 4.25-4.09 (m, 1H), 4.05-3.90 (m, 2H), 3.85-3.69 (m, 3H), 3.61 (d, J=14.1 Hz, 1H), 3.24-3.05 (m, 3H), 2.95 (dd, J=10.1, 15.4 Hz, 1H), 2.76-2.59 (m, 2H), 2.43-2.32 (m, 1H), 2.25 (td, J=8.9, 18.2 Hz, 1H), 2.17-1.93 (m, 4H), 1.93-1.71 (m, 6H), 1.65-1.55 (m, 1H), 1.36 (d, J=7.0 Hz, 3H), 0.99 (d, J=6.3 Hz, 3H), 0.94 (d, J=6.8 Hz, 3H). m/z (ESI, +ve ion) 657.3 (M+H)$^+$.

Example 528. (1S,3'R,6'R,7'S,8'E,11'S,12'R)-6-chloro-7'-(((2R)-2-hydroxypropyl)oxy)-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13', 13'-dioxide or (1S,3'R,6'R,7'S,8'E,11'S,12'R)-6-chloro-7'-(((2S)-2-hydroxypropyl)oxy)-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13', 13'-dioxide

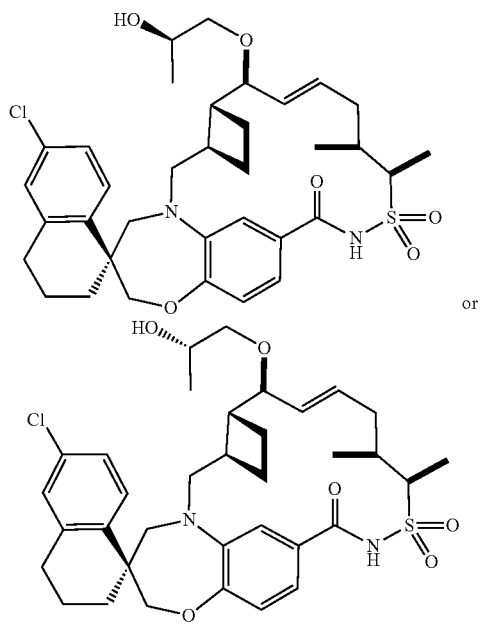

To a 100 ml flask containing (((1S,3'R,6'R,7'S,8'E,11'S, 12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl)oxy)acetaldehyde (from 527, Step 1) (240 mg, 0.374 mmol) was added 20 ml of THF and the reaction was cooled to −78° C. at which time methylmagnesium bromide 3.0 m in diethyl ether (0.374 ml, 1.12 mmol) was added. The reaction was stirred at room temperature for 1 hour, then quenched with 100 ml of saturated ammonium chloride and extracted once with 400 ml of EtOAc. The organic layer was dried over sodium sulfate, filtered and the solvent removed by rotary evaporation. The crude was first was purified on a Combiflash (12 gram gold silica column), eluting with 10%-70% EtOAc in heptanes. Rf=0.19 eluting with 50% EtOAc in heptanes. The racemic mixture (1:1) was then purified by preparatory SCF chromatography (Chiralpak AD-H 4.6×250 mM column, Phenomenex, Torrance, CA; elution of 35% EtOH in liquid CO₂; flow rate=3 mL/minute, 100 Bar BPR; 20 minute method, 0.5 mL stacked injections, 6 mg/mL) to provide the title compound (25 mg, 0.038 mmol, 20% yield), as the faster eluting isomer as a white solid. (t$_R$=6.5 minutes). ¹H NMR (400 MHz, CD₂Cl₂) δ 8.20 (br. s., 1H), 7.62 (d, J=8.4 Hz, 1H), 7.08 (dd, J=2.2, 8.6 Hz, 1H), 7.01 (d, J=2.0 Hz, 1H), 6.89-6.76 (m, 3H), 5.71 (ddd, J=3.3, 9.6, 15.1 Hz, 1H), 5.46 (dd, J=9.0, 15.1 Hz, 1H), 4.18 (q, J=7.3 Hz, 1H), 4.00 (s, 2H), 3.85-3.67 (m, 3H), 3.61 (d, J=14.1 Hz, 1H), 3.21-3.13 (m, 2H), 3.13-3.04 (m, 1H), 2.95 (dd, J=10.2, 15.3 Hz, 1H), 2.76-2.56 (m, 2H), 2.45-2.32 (m, 1H), 2.25 (td, J=8.9, 18.1 Hz, 1H), 2.19-1.82 (m, 7H), 1.81-1.68 (m, 2H), 1.64-1.48 (m, 2H), 1.36 (d, J=7.2 Hz, 3H), 0.99 (d, J=6.3 Hz, 3H), 0.97-0.89 (d, J=6.8 Hz, 3H). m/z (ESI, +ve ion) 657.3 (M+H)⁺.

Example 529. (1S,3'R,6'R,7'S,8'E,11'S,12'S)-6-chloro-7'-hydroxy-12'-((2R)-2-methoxypropyl)-11'-methyl-3,4-dihydro-2H,15'H-spiro[naphthalene-1, 22'-[20]oxa[13]thia[1,14]diazatetracyclo [14.7.2.0³,⁶.0¹⁹,²⁴]pentacosa [8,16,18,24]tetraen]-15'-one 13',13'-dioxide or (1S,3'R,6'R,7'S,8'E,11'S, 12'R)-6-chloro-7'-hydroxy-12'-((2R)-2-methoxypropyl)-11'-methyl-3,4-dihydro-2H,15'H-spiro [naphthalene-1,22'-[20]oxa[13]thia[1,14] diazatetracyclo[14.7.2.0³,⁶.0¹⁹,²⁴]pentacosa [8,16,18, 24]tetraen]-15'-one 13',13'-dioxide

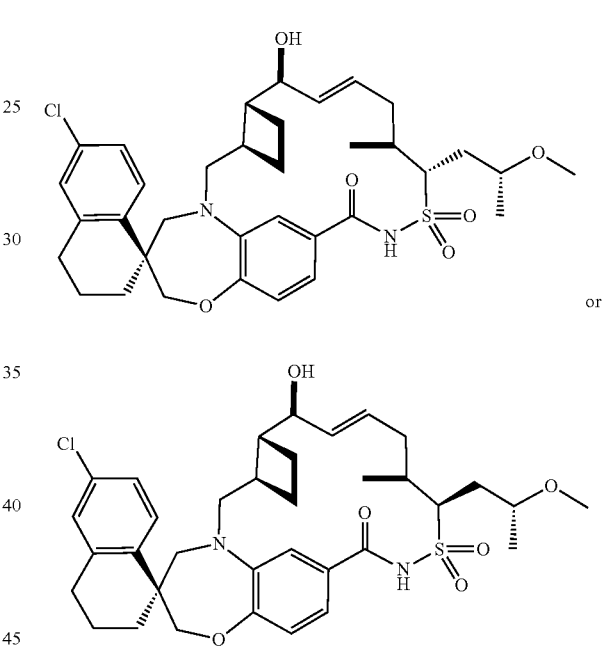

Step 1 (2R,4S,5S)-2-hydroxy-N, N-bis(4-methoxybenzyl)-5-methyloct-7-ene-4-sulfonamide and (2R, 4R,5S)-2-hydroxy-N,N-bis(4-methoxybenzyl)-5-methyloct-7-ene-4-sulfonamide

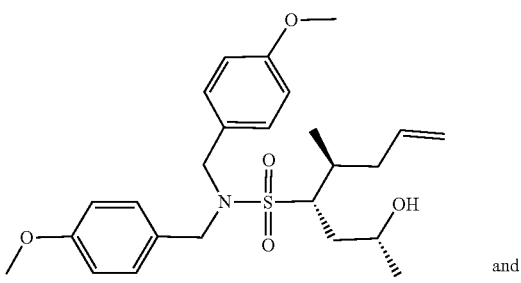

and

-continued

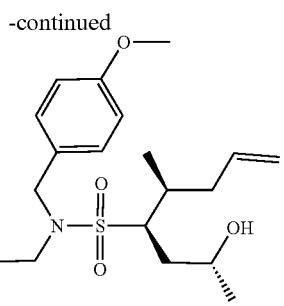

To a −78° C. solution of (S)—N,N-bis(4-methoxybenzyl)-2-methylpent-4-ene-1-sulfonamide (from Example 395, Step 3) (700 mg, 1.74 mmol) in THF (10 mL) under argon was added n-butyllithium (2.5M solution in hexane, 0.833 mL, 2.08 mmol) over 5 minutes. The mixture was stirred at −78° C. for 1 hours at which time (R)-(+)-1,2-epoxypropane (Sigma-Aldrich, Milwaukee, WI)(0.182 mL, 2.60 mmol) was added and stirred at 0° C. for 5 hours. The reaction was then quenched with 100 ml of saturated ammonium chloride and extracted with 300 ml of EtOAc. The organic layer was dried over sodium sulfate, filtered and the solvent removed by rotary evaporation. The crude was purified on a Combiflash (24 gram gold silica column), eluting with 10% to 50% EtOAc in heptanes, to give a 2:1 mixture of [(2R,4S,5S)-2-hydroxy-N,N-bis(4-methoxybenzyl)-5-methyloct-7-ene-4-sulfonamide and (2R,4R,5S)-2-hydroxy-N,N-bis(4-methoxybenzyl)-5-methyloct-7-ene-4-sulfonamide] (570 mg, 1.24 mmol, 71% yield) as light yellow oils.

Step 2: (2R,4S,5S)-2-methoxy-N,N-bis(4-methoxybenzyl)-5-methyloct-7-ene-4-sulfonamide and (2R, 4R, 5S)-2-methoxy-N,N-bis(4-methoxybenzyl)-5-methyloct-7-ene-4-sulfonamide

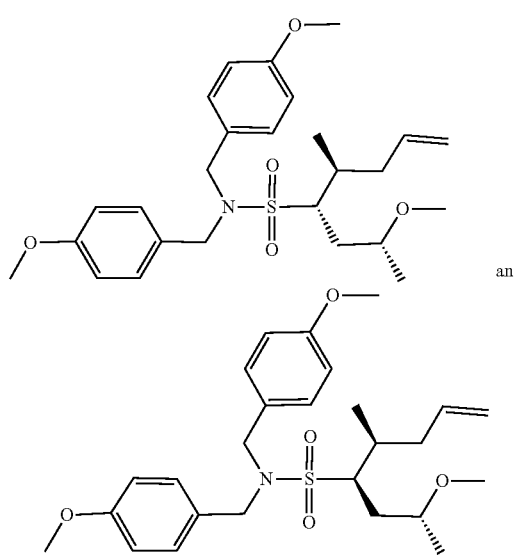

To a 100 ml flask was added [(2R,4S,5S)-2-hydroxy-N,N-bis(4-methoxybenzyl)-5-methyloct-7-ene-4-sulfonamide and (2R,4R,5S)-2-hydroxy-N,N-bis(4-methoxybenzyl)-5-methyloct-7-ene-4-sulfonamide] (from Step 1) (570 mg, 1.24 mmol) and THF (10 mL). The reaction flask was cooled to 0° C. and NaH (50 mg, 2.1 mmol) was added. The reaction was stirred at room temperature for 20 minutes at which time MeI (0.066 ml, 1.0 mmol) was added. The reaction was then stirred at room temperature for 4 hours then the reaction was quenched with 100 ml of saturated ammonium chloride and extracted with 400 ml of EtOAc. The organic layer was dried over sodium sulfate, filtered and the solvent was removed by rotary evaporation. The crude was purified on a Combiflash (24 gram gold silica column), eluting with 10% to 50% EtOAc in heptanes, to give a 1:1 mixture of [(2R,4S,5S)-2-methoxy-N,N-bis(4-methoxybenzyl)-5-methyloct-7-ene-4-sulfonamide and (2R,4R,5S)-2-methoxy-N,N-bis(4-methoxybenzyl)-5-methyloct-7-ene-4-sulfonamide] (510 mg, 1.07 mmol, 87% yield) as a light yellow oil.

Step 3: (2R,4R,5S)-2-methoxy-5-methyloct-7-ene-4-sulfonamide or (2R,4S,5S)-2-methoxy-5-methyloct-7-ene-4-sulfonamide

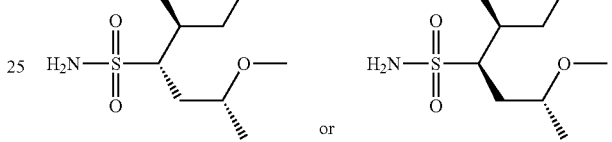

To a 100 ml flask was added [(2R,4S,5S)-2-methoxy-N,N-bis(4-methoxybenzyl)-5-methyloct-7-ene-4-sulfonamide and (2R,4R,5S)-2-methoxy-N,N-bis(4-methoxybenzyl)-5-methyloct-7-ene-4-sulfonamide] (from Step 2) (500 mg, 1.05 mmol), anisole (1.15 ml, 10.5 mmol), DCM (10 ml), and then TFA (4 ml). The reaction was stirred at 22° C. for 8 hours at which time the solvent was removed. The crude was purified on a Combiflash (12 gram gold silica column), eluting with 10% to 50% EtOAc in heptanes) to give [(2R,4R,5S)-2-methoxy-5-methyloct-7-ene-4-sulfonamide or (2R,4S,5S)-2-methoxy-5-methyloct-7-ene-4-sulfonamide](108 mg, 0.459 mmol, 87% yield) as the faster eluting isomer, as a light yellow oil.

Step 4: (S)-6'-chloro-5-(((1R,2R)-2-((1S,5S,6S,8R,E)-1-hydroxy-8-methoxy-5-methyl-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((1S,5S,6R,8R,E)-1-hydroxy-8-methoxy-5-methyl-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic Acid

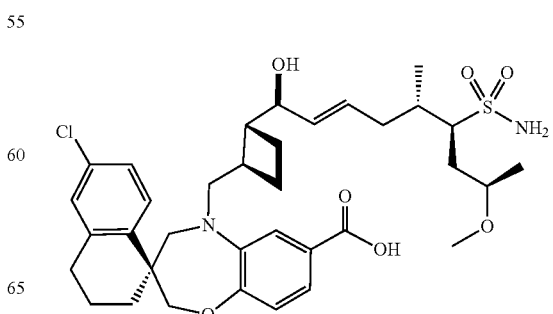

or

-continued

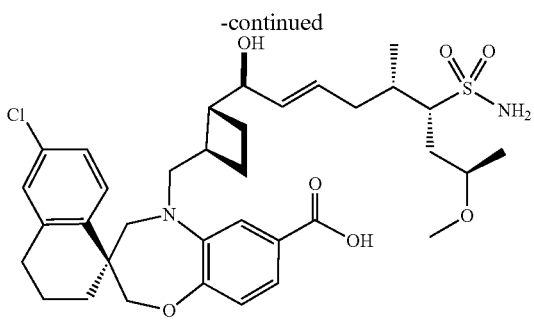

To a 100 ml flask was added (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A) (51.6 mg, 0.101 mmol), [(2R,4R,5S)-2-methoxy-5-methyloct-7-ene-4-sulfonamide or (2R,4S,5S)-2-methoxy-5-methyloct-7-ene-4-sulfonamide] (from Step 3)(71.4 mg, 0.303 mmol), and DCE (4 mL). The solution was sparged with argon for 15 minutes at which time Hoveyda-Grubbs II (6.3 mg, 10 µmol) was added as a 0.2 mL solution in DCE at room temperature. The mixture was stirred at room temperature for 16 hours. Note: the clear solution becomes slowly darker. The reaction mixture was then bubbled with air for 5 minutes and filtered. The solvent was removed from the filtrate and was directly purified on a Combiflash (12 gram gold silica column), eluting with 50%-90% EtOAc in heptanes+0.2% AcOH, to give [(S)-6'-chloro-5-(((1R,2R)-2-((1S,5S,6S,8R,E)-1-hydroxy-8-methoxy-5-methyl-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((1S,5S,6R,8R,E)-1-hydroxy-8-methoxy-5-methyl-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic acid] (46 mg, 0.068 mmol, 67% yield) as white solids.

Step 5: (1S,3'R,6'R,7'S,8'E,11'5,12'S)-6-chloro-7'-hydroxy-12'-((2R)-2-methoxypropyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-7'-hydroxy-12'-((2R)-2-methoxypropyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide To a 25 ml flask containing [(S)-6'-chloro-5-(((1R,2R)-2-((1S,5S,6S,8R,E)-1-hydroxy-8-methoxy-5-methyl-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1R,2R)-2-((1S,5S,6R,8R,E)-1-hydroxy-8-methoxy-5-methyl-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic acid] (from Step 4) (46 mg, 0.068 mmol) which was previously dried by rotovaping twice with 5 ml of toluene, was added N,N-dimethylpyridin-4-amine (DMAP) (14 mg, 0.12 mmol) and 100 ml of DCM. The reaction mixture was cooled to 0° C. at which N-(3-dimethylaminopropyl)-N'-ethylcarbodiimide hydrochloride (26 mg, 0.14 mmol) was slowly added. The reaction was stirred at room temperature for 18 hour. The mixture was then quenched with 50 ml of 1N HCl and extracted with 200 ml of EtOAc. The organic layer were dried over anhydrous sodium sulfate, filtered, and concentrated by rotary evaporation. The crude product was purified by reversed phase preparatory HPLC (Gemini™ Prep C$_{18}$ 5 µm column; Phenomenex, Torrance, CA; gradient elution of 10% to 90% MeCN in water, where both solvents contain 0.1% TFA, 45 minute method) to give the title compound (7.6 mg, 0.012 mmol, 17% yield) as a white solid. $^1$H NMR (400 MHz, CDCl$_3$) δ 8.22 (br. s., 1H), 7.70 (d, J=8.6 Hz, 1H), 7.19 (dd, J=2.3, 8.4 Hz, 2H), 7.10 (d, J=2.2 Hz, 1H), 6.97 (d, J=8.2 Hz, 1H), 6.78-6.62 (m 1H), 6.10-5.97 (m, 1H), 5.67 (dd, J=6.3, 15.5 Hz, 1H), 4.23-3.99 (m, 4H), 3.88-3.69 (m, 2H), 3.62 (d, J=13.9 Hz, 1H), 3.48-3.44 (m, 1H), 3.43 (s, 3H), 3.34-3.15 (m, 1H), 2.89-2.67 (m, 2H), 2.61-2.39 (m, 2H), 2.34-2.11 (m, 3H), 2.08-1.67 (m, 9H), 1.49 (d, J=11.7 Hz, 1H), 1.21 (d, J=6.1 Hz, 3H), 1.11 (d, J=7.0 Hz, 3H). m/z (ESI, +ve ion) 657.0 (M+H)$^+$.

Example 530. (1S,3'R,6'R,7'S,8'E,11'S,12'R)-6-chloro-7'-(2-((3R)-3-(methoxymethyl)-4-morpholinyl)ethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide and (1S,3'R,6'R,7'S,8'E,11'S,12'R)-6-chloro-7'-(2-((3S)-3-(methoxymethyl)-4-morpholinyl)ethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

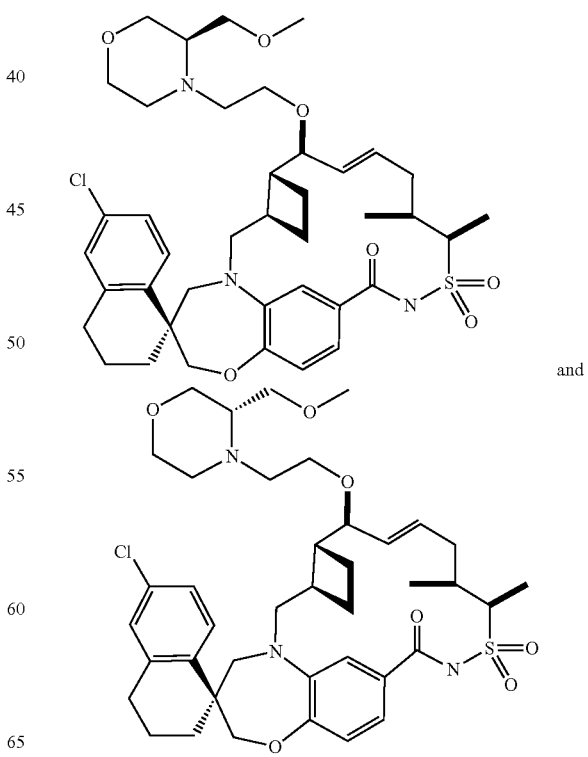

1149

To a 100 ml flask was added (((1S,3'R,6'R,7'S,8'E,11'S, 12'R)-6-chloro-11',12'-dimethyl-13',13'-dioxido-15'-oxo-3, 4-dihydro-2H-spiro[naphthalene-1,22'-[20]oxa[13]thia[1, 14]diazatetracyclo[14.7.2.0$^{3,6}$.0$^{19,24}$]pentacosa[8,16,18,24] tetraen]-7'-yl)oxy)acetaldehyde (from Example 527, Step 1) (10 mg, 0.016 mmol), DCE (2 ml), 3-(methoxymethyl)morpholine hydrochloride (Frontier Scientific, Logan, UT) (11 mg, 0.064 mmol), and sodium triacetoxyborohydride (17 mg, 0.080 mmol). The reaction was stirred at 55° C. for 5 hours at which time the reaction was quenched with 0.5 ml of MeOH and 100 ml of saturated sodium bicarbonate. The aqueous solution was extracted with 300 ml of EtOAc and the EtOAc layer was washed with 100 ml of brine. The organic layer was dried over sodium sulfate, filtered and the solvent removed by rotary evaporation. The crude product was purified by reversed phase preparatory HPLC (Gemini™ Prep C$_{18}$ 5 µm column; Phenomenex, Torrance, CA; gradient elution of 10% to 90% MeCN in water, where both solvents contain 0.1% TFA, 45 minute method) to give a 1:1 mixture of the title compounds (1.8 mg, 2.4 µmol, 15% yield) as a white film. $^1$H NMR (400 MHz, CD$_2$Cl$_2$) δ 8.11 (br. s., 1H), 7.70 (d, J=8.6 Hz, 1H), 7.17 (dd, J=2.2, 8.5 Hz, 1H), 7.09 (d, J=2.3 Hz, 1H), 6.91 (s, 2H), 6.83 (s, 1H), 5.98-5.77 (m, 1H), 5.62-5.45 (m, 1H), 4.26 (d, J=7.4 Hz, 1H), 4.08 (s, 2H), 4.01-3.89 (m, 4H), 3.88-3.73 (m, 5H), 3.69 (d, J=14.5 Hz, 2H), 3.64-3.43 (m, 4H), 3.37 (m, 1.5H), 3.36 (m, 1.5H), 3.24 (d, J=14.3 Hz, 2H), 3.04 (dd, J=10.1, 15.4 Hz, 1H), 2.84-2.69 (m, 2H), 2.49-2.39 (m, 1H), 2.38-2.26 (m, 1H), 2.23-1.89 (m, 6H), 1.88-1.75 (m, 3H), 1.75-1.62 (m, 1H), 1.45 (d, J=7.0 Hz, 3H), 1.42-1.35 (m, 1H), 1.08-0.91 (m, 3H). m/z (ESI, +ve ion) 756.4 (M+H)$^+$.

Example 531. (1S,3'R,6'R,7'S,8'E,11'S,12'R)-6-chloro-11',12'-dimethyl-7'-(2-((3R)-3-(1-methylethyl)-4-morpholinyl)ethoxy)-3,4-dihydro-2H,15'H-spiro[naphthalene-1,22'-[20]oxa[13]thia[1,14] diazatetracyclo[14.7.2.0$^{3,6}$.0$^{19,24}$]pentacosa [8,16,18,24]tetraen]-15'-one 13',13'-dioxide 2,2,2-trifluoroacetic Acid and (1S,3'R,6'R,7'S,8'E,11'S, 12'R)-6-chloro-11,12'-dimethyl-7'-(2-((3S)-3-(1-methylethyl)-4-morpholinyl)ethoxy)-3,4-dihydro-2H,15'H-spiro[naphthalene-1,22'-[20]oxa[13]thia[1, 14]diazatetracyclo[14.7.2.0$^{3,6}$.0$^{19,24}$]pentacosa [8,16,18,24]tetraen]-15'-one 13',13'-dioxide 2,2,2-trifluoroacetic Acid

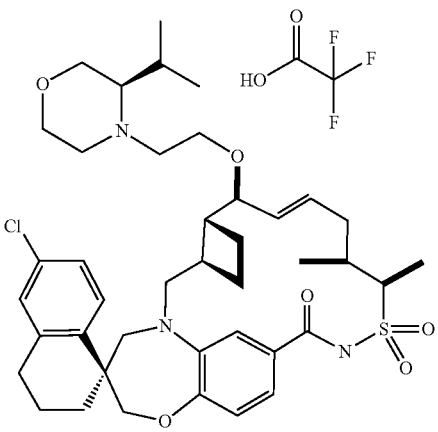

and

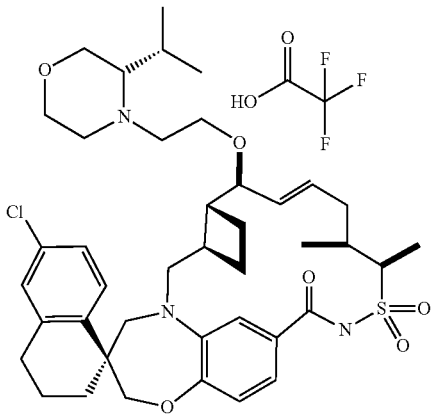

To a 4 ml vial was added (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24] tetraen]-7'-yl)oxy)acetaldehyde (from 527, Step 1) (20 mg, 0.031 mmol), DCE (4 ml), 3-isopropylmorpholine hydrochloride (Frontier Scientific, Logan, UT)(21 mg, 0.13 mmol) and triethylamine (0.017 ml, 0.13 mmol). The reaction was heated at 50° C. for 5 minutes at which time the reaction was cooled to room temperature and sodium triacetoxyborohydride (33 mg, 0.16 mmol) was added. The reaction was stirred at 50° C. for 16 hours at which time the reaction was quenched with 0.2 ml of MeOH and 50 ml of saturated sodium bicarbonate. The aqueous solution was extracted with 100 ml of EtOAc and the EtOAc layer was washed with 50 ml of brine. The organic layer was dried over sodium sulfate, filtered and the solvent removed by rotary evaporation. The crude product was purified by reversed phase preparatory HPLC (Gemini™ Prep C$_{18}$ 5 µm column; Phenomenex, Torrance, CA; gradient elution of 10% to 90% MeCN in water, where both solvents contain 0.1% TFA, 45 minute method) to give a 1:1 mixture of the title compounds (1.8 mg, 2.1 µmol, 6.7% yield) as an amorphous solid. $^1$H NMR (400 MHz, CD$_2$Cl$_2$) δ 8.20 (br. s., 1H), 7.70 (d, J=8.6 Hz, 1H), 7.17 (dd, J=2.2, 8.5 Hz, 1H), 7.09 (d, J=2.3 Hz, 1H), 6.92 (s, 2H), 6.83 (s, 1H), 5.99-5.79 (m, 1H), 5.63-5.46 (m, 1H), 4.27 (q, J=6.9 Hz, 1H), 4.2-4.1 (m, 0.5H), 4.08 (s, 2H), 4.04-3.89 (m, 3.5H), 3.82 (d, J=14.3 Hz, 3H), 3.69 (d, J=14.3 Hz, 2H), 3.57-3.47 (m, 1.5H), 3.46-3.37 (m, 1.5H), 3.24 (d, J=14.1 Hz, 2H), 3.20 (s, 1H), 3.10-2.97 (m, 1H), 2.84-2.67 (m, 3H), 2.44 (s, 2H), 2.38-2.27 (m, 1H), 2.24-1.90 (m, 9H), 1.46 (d, J=7.0 Hz, 1.5H), 1.45 (d, J=7.0 Hz, 1.5H), 1.33-1.27 (m, 1H), 1.04 (td, J=4.7, 6.8 Hz, 9H). m/z (ESI, +ve ion) 698.4 (M+H)$^+$.

Example 532. (1S,3'R,6'R,7'S,8'E,11'S,12'R)-6-chloro-7'-(2-(3-fluoro-1-azetidinyl)ethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide Example 533. 2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N,N,N-triethyl-ethanaminium 2,2,2-trifluoroacetate

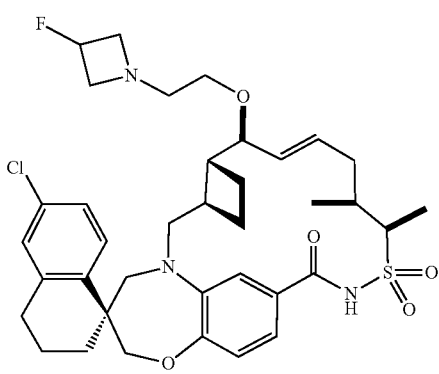

To a 8 ml vial was added (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetaldehyde (from 527, Step 1) (19 mg, 0.030 mmol), DCE (4 ml), 3-fluoroazetidine hydrochloride (Frontier Scientific, Logan, UT)(13 mg, 0.12 mmol) and triethylamine (0.016 ml, 0.12 mmol). The reaction was heated at 50° C. for 5 minutes and sodium triacetoxyborohydride (31 mg, 0.15 mmol) was added. The reaction was stirred at 50° C. for 16 hours at which time the reaction was quenched with 0.2 ml of MeOH and 50 ml of saturated sodium bicarbonate. The aqueous solution was extracted with 100 ml of EtOAc and the EtOAc layer was washed with 50 ml of brine. The organic layer was dried over sodium sulfate, filtered and the solvent removed by rotary evaporation. The crude was purified on a Combiflash (4 gram gold silica column), eluting with 2%-10% MeOH in DCM, to give the title compound (9.0 mg, 0.011 mmol, 37% yield) as an off white solid. Rf=0.28 eluting with 10% MeOH in DCM. $^{1}$H NMR (400 MHz, CD$_2$Cl$_2$) δ 7.71 (d, J=8.6 Hz, 1H), 7.17 (dd, J=2.2, 8.5 Hz, 1H), 7.09 (d, J=2.3 Hz, 1H), 6.99-6.93 (m, 1H), 6.92-6.82 (m, 2H), 5.89-5.71 (m, 1H), 5.52 (dd, J=9.1, 15.4 Hz, 1H), 5.19 (dq, J$_{H,F}$=57.7 & J=5.2, 1H), 4.26-4.15 (m, 1H), 4.07 (s, 2H), 3.88-3.63 (m, 5H), 3.50-3.38 (m, 2H), 3.31-3.18 (m, 5H), 3.02 (dd, J=10.0, 15.3 Hz, 1H), 2.81 (d, J=3.1 Hz, 2H), 2.72-2.62 (m, 2H), 2.48-2.28 (m, 2H), 2.20-1.74 (m, 7H), 1.73-1.62 (m, 1H), 1.42 (d, J=7.0 Hz, 3H), 1.38 (m, 1H), 1.01 (d, J=6.8 Hz, 3H). m/z (ESI, +ve ion) 700.4 (M+H)$^{+}$.

To a 1 dram pressure relief vial was added (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (from Example 14) (10 mg, 0.014 mmol), 0.5 ml of DMSO and 6-oxa-1-azaspiro[3.3]heptane (Synthonix, Wake Forest, NC) (14 mg, 0.14 mmol). The reaction was sealed with a pressure release fitted cap and heated to 70° C. for 2 hours then triethylamine (40 µl, 0.28 mmol) was added and heated to 70° C. for an additional 16 hours The reaction was then quenched with 0.2 ml of MeOH and was directly by reversed phase preparatory HPLC (Gemini™ Prep C$_{18}$ 5 µm column; Phenomenex, Torrance, CA; gradient elution of 10% to 90% MeCN in water, where both solvents contain 0.1% TFA, 45 minute method) to give the title compound (2.1 mg, 2.5 µmol, 18% yield) as clear film. $^{1}$H NMR (400 MHz, CD$_2$Cl$_2$) δ 7.70 (d, J=8.4 Hz, 1H), 7.17 (dd, J=2.4, 8.5 Hz, 1H), 7.09 (d, J=2.3 Hz, 1H), 7.00-6.85 (m, 2H), 6.80 (s, 1H), 6.00-5.81 (m, 1H), 5.61-5.44 (m, 1H), 4.31-4.19 (m, 1H), 4.13-4.02 (m, 2H), 3.90-3.77 (m, 2H), 3.69 (d, J=14.9 Hz, 2H), 3.60 (m, 2H), 3.36-3.21 (m, 8H), 3.10-2.98 (m, 1H), 2.74-2.64 (m, 2H), 2.38-2.20 (m, 2H), 2.16-1.98 (m, 3H), 1.98-1.82 (m, 4H), 1.81-1.58 (m, 3H), 1.37 (d, J=7.2 Hz, 3H), 1.34-1.28 (m, 1H), 1.23 (t, J=7.1 Hz, 9H), 0.95 (d, J=6.8 Hz, 3H). m/z (ESI, +ve ion) 726.5 (M+H)$^{+}$.

1153

Example 534. (1S,3'R,6'R,7'S,8'E,11'S,12'R)-6-chloro-11',12'-dimethyl-7'-(2-((3S)-3-methyl-4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

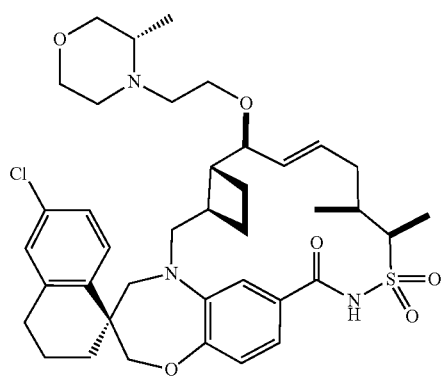

To a 100 ml flask was added (((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetaldehyde (from 527, Step 1) (16 mg, 0.025 mmol), DCE (2 ml), (S)-3-methylmorpholine (Frontier Scientific, Logan, UT) (5.1 mg, 0.051 mmol), and sodium triacetoxyborohydride (27 mg, 0.13 mmol). The reaction was stirred at 55° C. for 5 hours at which time the reaction was quenched with 0.5 ml of MeOH and 100 ml of saturated sodium bicarbonate. The aqueous solution was extracted with 300 ml of EtOAc and the EtOAc layer was washed with 100 ml of brine. The organic layer was dried over sodium sulfate, filtered and the solvent removed by rotary evaporation. The crude product was purified by reversed phase preparatory HPLC (Gemini™ Prep C$_{18}$ 5 μm column; Phenomenex, Torrance, CA; gradient elution of 10% to 90% MeCN in water, where both solvents contain 0.1% TFA, 45 minute method) to give the title compound (2.7 mg, 3.7 μmol, 15% yield) as a white film. $^1$H NMR (400 MHz, CD$_2$Cl$_2$) δ 8.16 (br. s., 1H), 7.71 (d, J=8.4 Hz, 1H), 7.17 (dd, J=2.3, 8.4 Hz, 1H), 7.09 (d, J=2.3 Hz, 1H), 6.92 (s, 2H), 6.83 (s, 1H), 5.96-5.77 (m, 1H), 5.61-5.42 (m, 1H), 4.27 (d, J=6.8 Hz, 1H), 4.09 (s, 2H), 4.05-3.87 (m, 3H), 3.87-3.59 (m, 6H), 3.52-3.10 (m, 6H), 3.04 (dd, J=10.3, 15.4 Hz, 1H), 2.85-2.68 (m, 2H), 2.45 (d, J=9.0 Hz, 1H), 2.39-2.27 (m, 1H), 2.23-2.01 (m, 2H), 2.01-1.90 (m, 3H), 1.90-1.75 (m, 2H), 1.73-1.62 (m, 1H), 1.45 (d, J=7.2 Hz, 3H), 1.41-1.39 (m, 1H), 1.33 (d, J=6.7 Hz, 2H), 1.36-1.29 (m, 3H), 1.03 (d, J=6.7 Hz, 3H). m/z (ESI, +ve ion) 726.3 (M+H)$^+$.

1154

Example 535. (1S,3'R,6'R,7'S,8'E,11'S,12'R)-6-chloro-7'-methoxy-12'-((2R)-2-methoxypropyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-methoxy-12'-((2R)-2-methoxypropyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

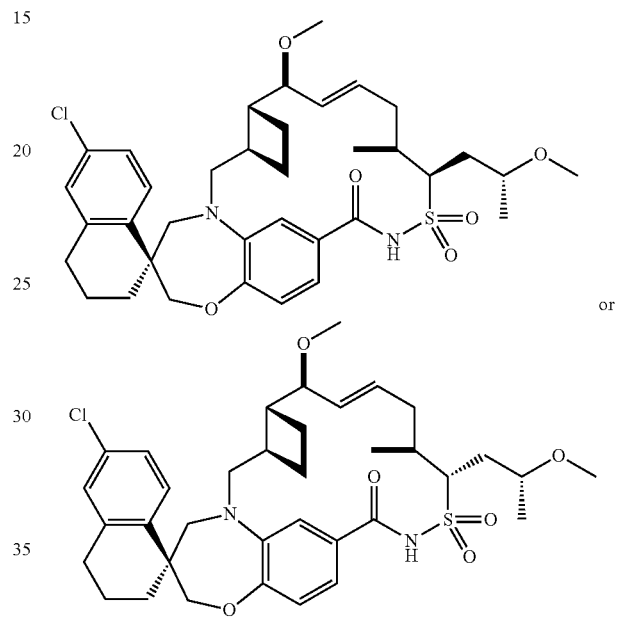

To a solution of [(1S,3'R,6'R,7'S,8'E,11'S,12'S)-6-chloro-7'-hydroxy-12'-((2R)-2-methoxypropyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-hydroxy-12'-((2R)-2-methoxypropyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (from Example 540)(16 mg, 0.024 mmol) in 1 ml of THF cooled to 0° C. was added NaH (5.8 mg, 0.24 mmol). After 15 minutes, MeI (7.6 μl, 0.12 mmol) was added to the reaction mixture at 0° C. The reaction mixture was stirred at room temperature for 45 minutes at which time the reaction was quenched with 25 ml of saturated ammonium chloride and extracted with 100 ml of EtOAc. The organic layer was dried over sodium sulfate and concentrated. The crude was purified on a Combiflash (4 gram gold silica column), eluting with 10%-40% EtOAc in heptanes+0.2% AcOH, to give the title compound (8.0 mg, 0.012 mmol, 49% yield). $^1$H NMR (400 MHz, CDCl$_3$) δ 8.05 (s, 1H), 7.70 (d, J=8.4 Hz, 1H), 7.19 (dd, J=2.2, 8.5 Hz, 1H), 7.10 (d, J=2.3 Hz, 1H), 6.99-6.82 (m, 3H), 5.86 (ddd, J=3.0, 9.4, 15.2 Hz, 1H), 5.54 (dd, J=9.2, 15.3 Hz, 1H), 4.31 (dd, J=3.6, 8.5 Hz, 1H), 4.10 (s, 2H), 3.91-3.77 (m, 2H), 3.74-3.62 (m, 3H), 3.39 (s, 3H), 3.29-3.18 (m, 1H), 3.23 (s, 3H), 3.01 (dd, J=10.2, 15.3 Hz, 1H), 2.85-2.66 (m, 2H), 2.57-2.41 (m, 2H), 2.38-2.18 (m, 2H), 2.17-2.10 (m, 1H), 2.09-1.92 (m, 4H), 1.88-1.75

(m, 3H), 1.75-1.57 (m, 2H), 1.40 (t, J=12.6 Hz, 1H), 1.28 (d, J=6.8 Hz, 3H), 1.08 (d, J=6.8 Hz, 3H). m/z (ESI, +ve ion) 671.0 (M+H)+.

Example 536. (1S,3'R,6'R,7'S,8'E,10'S)-6-chloro-7'-hydroxy-10'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

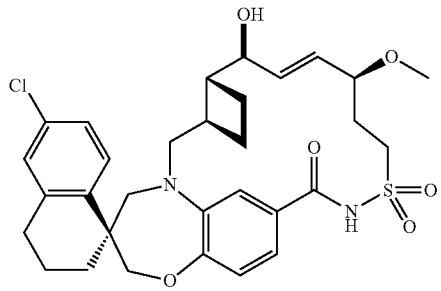

Step 1: (S)-3-hydroxy-N,N-bis(4-methoxybenzyl)pent-4-ene-1-sulfonamide

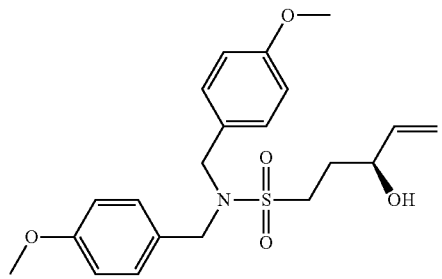 [SMILES: C=C[C@@H](O)CCS(=O)(=O)N(Cc1ccc(OC)cc1)Cc1ccc(OC)cc1]

To a −78° C. solution of N,N-bis(4-methoxybenzyl)methanesulfonamide (from Example EE12)(2.00 g, 5.96 mmol) in THF (25 mL) under argon was added n-butyllithium (2.5 M solution in hexane, 3.58 mL, 8.94 mmol) over 5 minutes. The mixture was stirred at −78° C. for 2 hours (solution turned red-pink) at which time (R)-2-vinyl-oxirane (Sigma-Aldrich, Milwaukee, WI)(0.84 mL, 10 mmol) was added and stirred at 0° C. for 16 hours. The reaction was then quenched with 100 ml of saturated ammonium chloride and extracted with 400 ml of EtOAc. The organic layer was dried over sodium sulfate, filtered and the solvent removed by rotary evaporation. The crude was purified on a Combiflash (40 gram gold silica column), eluting with 10% to 50% EtOAc in heptanes, to give (S)-3-hydroxy-N,N-bis(4-methoxybenzyl)pent-4-ene-1-sulfonamide (1.35 g, 3.34 mmol, 56% yield) as light yellow oils.

Step 2: (S)-3-methoxy-N,N-bis(4-methoxybenzyl)pent-4-ene-1-sulfonamide

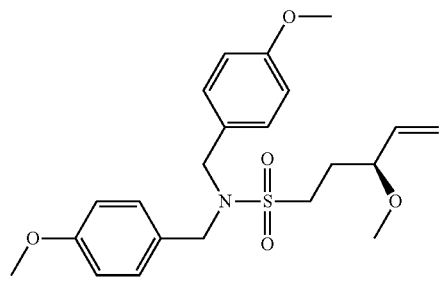 [SMILES: C=C[C@H](CCS(=O)(=O)N(Cc1ccc(OC)cc1)Cc1ccc(OC)cc1)OC]

To a 100 ml flask was added (S)-3-hydroxy-N,N-bis(4-methoxybenzyl)pent-4-ene-1-sulfonamide (from Step 1) (200 mg, 0.493 mmol) DMF (4 mL) and NaH (59 mg, 2.5 mmol). The reaction was stirred at room temperature for 15 minutes at which time iodomethane (0.092 ml, 1.5 mmol) was added. The reaction was then stirred at room temperature for 2 hours, the reaction was quenched with 50 ml of saturated ammonium chloride and extracted with 200 ml of EtOAc. The organic layer was dried over sodium sulfate, filtered, the solvent was removed by rotary evaporation, and the crude was purified on a Combiflash (12 gram gold silica column), eluting with 10% to 50% EtOAc in heptanes, to give (S)-3-methoxy-N,N-bis(4-methoxybenzyl)pent-4-ene-1-sulfonamide (91 mg, 0.22 mmol, 44% yield) as an off white solid.

Step 3: (S)-3-methoxypent-4-ene-1-sulfonamide

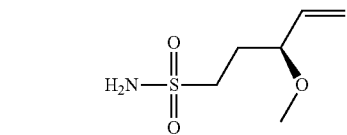

To a 100 ml flask containing (S)-3-methoxy-N,N-bis(4-methoxybenzyl)pent-4-ene-1-sulfonamide (from Step 2)(91.3 mg, 0.218 mmol, 44.1% yield) was added DCM (8 ml), anisole (0.539 ml, 4.93 mmol) and then TFA (2 ml). The reaction was stirred at 22° C. for 5 hours at which time the solvent was removed. The crude was purified on a Combiflash (12 gram gold silica column), eluting with 10% to 50% EtOAc in heptanes, to give ((S)-3-methoxypent-4-ene-1-sulfonamide (24.9 mg, 0.139 mmol, 64% yield) as white solid.

Step 4: (S)-6'-chloro-5-(((1R,2R)-2-((S,E)-1-hydroxyhex-2-en-1-yl)cyclobutyl)methyl)-N—(((S)-3-methoxypent-4-en-1-yl)sulfonyl)-3',4,4',5-tetrahydro-2H,2'H-spiro[benzo[b][1,4]oxazepine-3,1'-naphthalene]-7-carboxamide

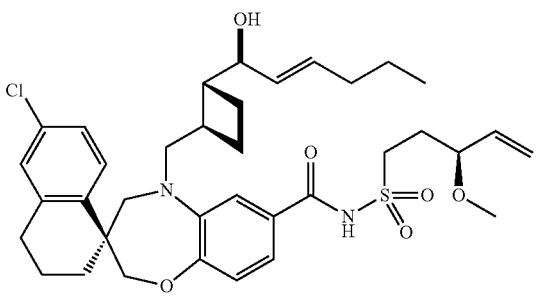

To a 100 ml flask was added (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (from Example AA12A) (30 mg, 0.059 mmol), (S)-3-methoxypent-4-ene-1-sulfonamide (from Step 3) (25 mg, 0.14 mmol), N,N-dimethylpyridin-4-amine (14 mg, 0.12 mmol), 3 ml of DCM, and then N-(3-dimethylaminopropyl)-N'-ethylcarbodiimide hydrochloride (23 mg, 0.12 mmol). The reaction was stirred at room temperature for 16 hours at which time the reaction was quenched with 50 ml of 1 N HCl and extracted with 200 ml of EtOAc. The organic layer was dried over sodium sulfate, filtered, the solvent was removed by rotary evaporation, and the crude was purified on a Combiflash (12 gram gold silica column), eluting with 10%-40% EtOAc in heptanes+0.2% AcOH, to give ((S)-6'-chloro-5-(((1R,2R)-2-((S,E)-1-hydroxyhex-2-en-1-yl)cyclobutyl)methyl)-N—(((S)-3-methoxypent-4-en-1-yl)sulfonyl)-3',4,4',5-tetrahydro-2H,2'H-spiro[benzo[b][1,4]oxazepine-3,1'-naphthalene]-7-carboxamide (31 mg, 0.046 mmol, 78% yield) as a thick yellow oil.

Step 5: (1S,3'R,6'R,7'S,8'E,10'S)-6-chloro-7'-hydroxy-10'-methoxy-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide To a 100 ml flask was added (S)-6'-chloro-5-(((1R,2R)-2-((S,E)-1-hydroxyhex-2-en-1-yl)cyclobutyl)methyl)-N—(((S)-3-methoxypent-4-en-1-yl)sulfonyl)-3',4,4',5-tetrahydro-2H,2'H-spiro[benzo[b][1,4]oxazepine-3,1'-naphthalene]-7-carboxamide (from Step 4) (26 mg, 0.039 mmol) and DCM (25 ml). The mixture was stirred at room temperature while argon was bubbled through the reaction mixture for 15 minutes. To the homogeneous solution was then added titanium(iv) isopropoxide (9.1 µl, 0.031 mmol) and the reaction mixture was stirred at 45° C. for 1 hour at which time ((1,3-dimesitylimidazolidin-2-ylidene)(2-isopropoxybenzylidene)ruthenium(VI) chloride (4.9 mg, 7.8 µmol) was added and the mixture was stirred to 45° C. for 16 hours. The reaction was then sparged with argon again for 15 minutes, (1,3-dimesitylimidazolidin-2-ylidene)(2-isopropoxybenzylidene)ruthenium(VI) chloride (4.9 mg, 7.8 µmol) was added again and the reaction was stirred at 80° C. for an additional 6 hours. The reaction was then filtered, concentrated and crude product was purified by reversed phase preparatory HPLC (Gemini™ Prep $C_{18}$ 5 µm column; Phenomenex, Torrance, CA; gradient elution of 10% to 90% MeCN in water, where both solvents contain 0.1% TFA, 45 minute method) to give th title compound (2.5 mg, 4.2 µmol, 11% yield) as a white solid. $^1$H NMR (400 MHz, CDCl$_3$) δ 8.30 (br. s., 1H), 7.69 (d, J=8.4 Hz, 1H), 7.18 (dd, J=2.3, 8.4 Hz, 1H), 7.13-7.05 (m, 1H), 7.01-6.88 (m, 2H), 5.92-5.81 (m, 1H), 5.86 (dd, J=5.7, 15.6 Hz, 1H), 5.75 (dd, J=6.8, 15.5 Hz, 1H), 4.30-4.23 (m, 1H), 4.13 (q, J=12.1 Hz, 2H), 3.95-3.83 (m, 1H), 3.82-3.78 (m, 1H), 3.60 (d, J=11.5 Hz, 3H), 3.47-3.23 (m, 2H), 3.12 (s, 3H), 2.86-2.65 (m, 2H), 2.55-2.37 (m, 2H), 2.36-2.23 (m, 1H), 2.04-1.92 (m, 3H), 1.90-1.65 (m, 5H), 1.62-1.43 (m, 1H). m/z (ESI, +ve ion) 601.0 (M+H)$^+$.

Example 539. (1S,3'R,6'R,7'S,8'E,12'R)-6-chloro-7'-hydroxy-12'-((2R)-2-hydroxypropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,12'S)-6-chloro-7'-hydroxy-12'-((2R)-2-hydroxypropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

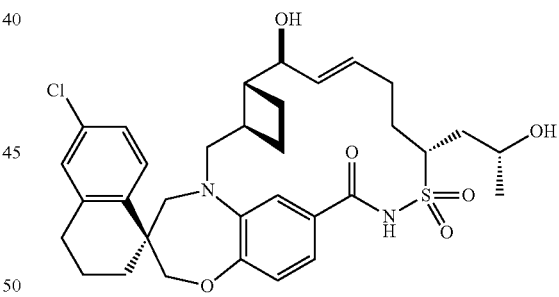

or

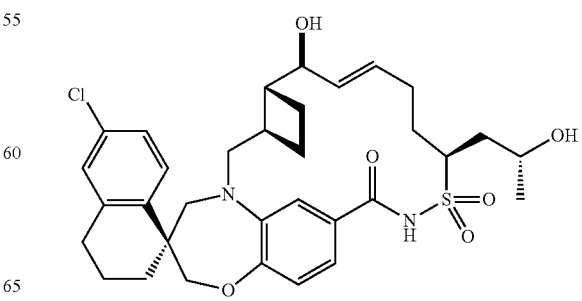

Step 1: (2R,4S)-2-((tert-butyldiphenylsilyl)oxy)-N,N-bis(4-methoxybenzyl)oct-7-ene-4-sulfonamide or (2R,4R)-2-((tert-butyldiphenylsilyl)oxy)-N,N-bis(4-methoxybenzyl)oct-7-ene-4-sulfonamide Step 2: (2R,4S)-2-((tert-butyldiphenylsilyl)oxy)oct-7-ene-4-sulfonamide or (2R,4R)-2-((tert-butyldiphenylsilyl)oxy)oct-7-ene-4-sulfonamide

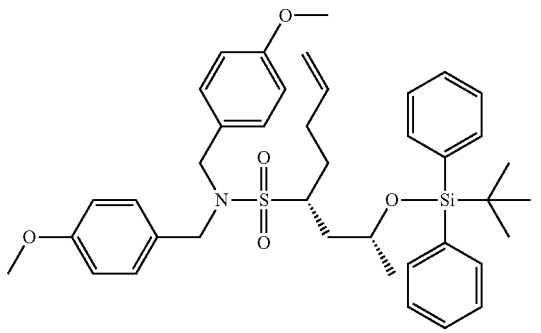

or

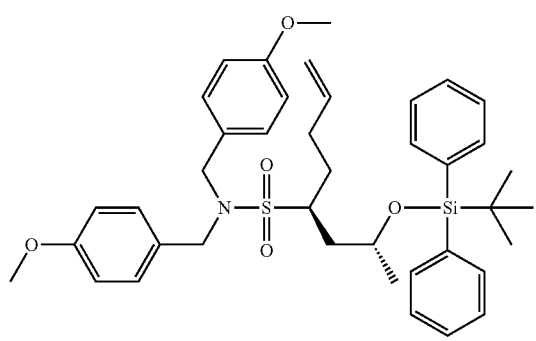

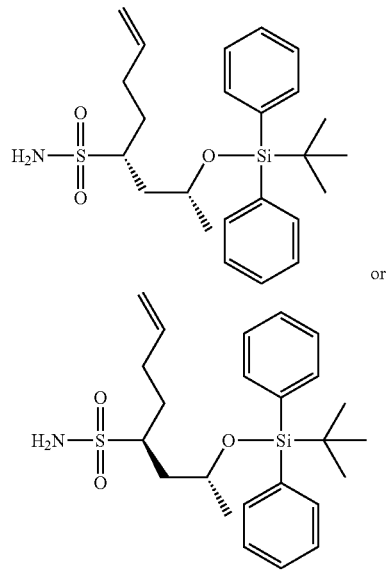

To a 100 ml flask was added [(2R,4R)-2-hydroxy-N,N-bis(4-methoxybenzyl)oct-7-ene-4-sulfonamide and (2R,4S)-2-hydroxy-N,N-bis(4-methoxybenzyl)oct-7-ene-4-sulfonamide] (from Example 508, Step 1) (2.58 g, 5.76 mmol), DMF (40 ml), imidazole (785 mg, 11.5 mmol) and tert-butylchlorodiphenylsilane (2.25 ml, 8.65 mmol). The reaction was stirred at 65° C. for 16 hours at which time reaction was then quenched with 200 ml of saturated ammonium chloride and extracted with 600 ml of diethyl ether. The organic layer was dried over sodium sulfate, filtered and the solvent removed by rotary evaporation. The crude product was first purified on a Combiflash (40 g gold silica column), eluting with 10% to 30% EtOAc in heptanes. The racemic mixture (1:1) was then purified by preparatory SCF chromatography (Chiralpak AD 250 mm×30 mm column, Phenomenex, Torrance, CA; 16 g/minute EtOH+(20 mM Ammonia)+64 g/minute CO$_2$ (20% co-solvent) on Thar 80 SFC; outlet pressure=100 bar; temperature=22° C.; wavelength=220 nm; used 1.0 mL injections of 3647 mg/41 mL (89 mg/mL) sample solution of MeOH (35 mL) and DCM (5 mL); run time=13 minutes & cycle time 10 minutes.) to provide [(2R,4S)-2-((tert-butyldiphenylsilyl)oxy)-N,N-bis(4-methoxybenzyl)oct-7-ene-4-sulfonamide or (2R,4R)-2-((tert-butyldiphenylsilyl)oxy)-N,N-bis(4-methoxybenzyl)oct-7-ene-4-sulfonamide as the slower eluting isomer as a yellow liquid (t$_R$=2.34 minutes on analytical SFC; AD-H column; 15% EtOH in CO$_2$).

To a 100 ml flask was added [(2R,4S)-2-((tert-butyldiphenylsilyl)oxy)-N,N-bis(4-methoxybenzyl)oct-7-ene-4-sulfonamide or (2R,4R)-2-((tert-butyldiphenylsilyl)oxy)-N,N-bis(4-methoxybenzyl)oct-7-ene-4-sulfonamide](from Step 1) (260 mg, 0.379 mmol), anisole (0.414 ml, 3.79 mmol), DCM (4 ml) and then TFA (2 ml). The reaction was stirred at 22° C. for 3 hours at which time the solvent was removed. The crude product was purified on a Combiflash (12 g gold silica column), eluting with 10% to 50% EtOAc in heptanes, to give [(2R,4S)-2-((tert-butyldiphenylsilyl)oxy)oct-7-ene-4-sulfonamide or (2R,4R)-2-((tert-butyldiphenylsilyl)oxy)oct-7-ene-4-sulfonamide] (73.4 mg, 0.165 mmol, 44% yield) as a light yellow oil.

Step 3: (S)—N-(((2R,4S)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(((2R,4R)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide

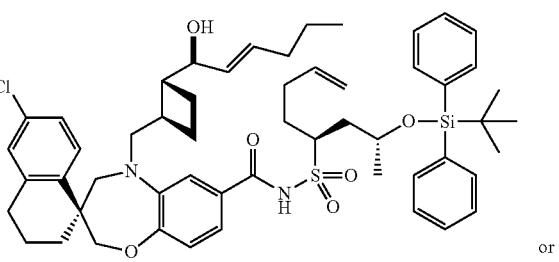

or

1161
-continued

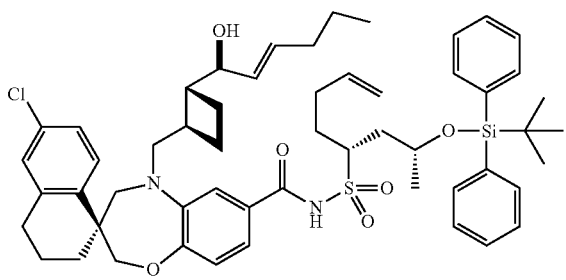

To a 100 ml flask was added (S)-6'-chloro-5-((((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (from Intermediate AA12A) (55 mg, 0.11 mmol), N,N-dimethylpyridin-4-amine (26 mg, 0.22 mmol), [(2R,4S)-2-((tert-butyldiphenylsilyl)oxy)oct-7-ene-4-sulfonamide or (2R,4R)-2-((tert-butyldiphenylsilyl)oxy)oct-7-ene-4-sulfonamide] (from Step 2) (72 mg, 0.22 mmol) and N-(3-dimethylaminopropyl)-N'-ethylcarbodiimide hydrochloride (42 mg, 0.59 mmol). The reaction was stirred at room temperature for 16 hours at which time the solvent was removed and the crude product was purified on a Combiflash (12 g gold silica column), eluting with 2%-10% EtOAc in heptanes+0.2% AcOH, to give [(S)—N-(((2R,4S)-2-((tert-butyldiphenylsilyl)oxy)oct-7-en-4-yl)sulfonyl)-6'-chloro-5-((((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(((2R,4R)-2-((tert-butyldiphenylsilyl)oxy)oct-7-en-4-yl)sulfonyl)-6'-chloro-5-((((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide] (57 mg, 0.061 mmol, 56% yield) as a thick yellow oil.

Step 4: (1S,3'R,6'R,7'S,8'E,12'S)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

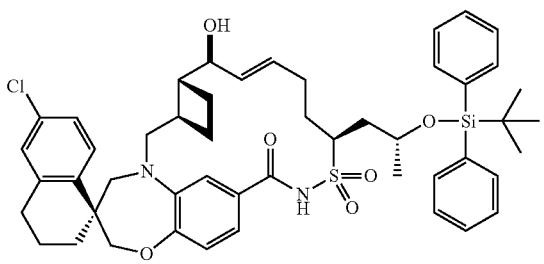

or

1162
-continued

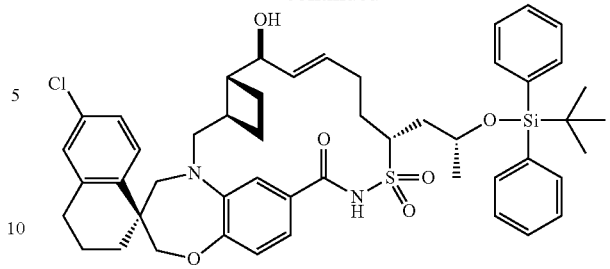

To a 100 ml flask was added [(S)—N-(((2R,4S)-2-((tert-butyldiphenylsilyl)oxy)oct-7-en-4-yl)sulfonyl)-6'-chloro-5-((((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(((2R,4R)-2-((tert-butyldiphenylsilyl)oxy)oct-7-en-4-yl)sulfonyl)-6'-chloro-5-((((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide] (from Step 3) (57 mg, 0.061 mmol) and DCM (40 ml). The mixture was stirred at room temperature while argon was bubbled through the reaction mixture for 15 minutes. To the homogeneous solution was then added Hoveyda-Grubbs II (3.8 mg, 6.1 μmol) and the mixture was stirred to 45° C. for 6 hours. The reaction mixture was filtered and concentrated. The crude product was purified on a Combiflash (12 g gold silica column), eluting with 10%-40% EtOAc in heptanes+0.2% AcOH, to give [(1S,3'R,6'R,7'S,8'E,12'S)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (10 mg, 0.012 mmol, 20% yield) as the faster eluting olefin isomer as a white solids.

Step 5: (1S,3'R,6'R,7'S,8'E,12'R)-6-chloro-7'-hydroxy-12'-((2R)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-6-chloro-7'-hydroxy-12'-((2R)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide To a 100 ml flask was added [(1S,3'R,6'R,7'S,8'E,12'S)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (from Step 4) (8.6 mg, 9.9 μmol) and TBAF (1 M in THF, 2.00 ml, 1.982 mmol). The reaction was stirred at 65° C. for 3.5 hours at which time the reaction was quenched with 50 ml of brine and extracted with 200 ml of EtOAc. The organic layer was dried over sodium sulfate and filtered. The solvent was removed by rotary evaporation, and the crude product was purified on a Combiflash (4 g gold silica column), eluting with 50% to 90% EtOAc in heptanes+0.2% AcOH), to give the title compound (2.6 mg, 4.1 µmol, 42% yield) as an off white solid. $^1$H NMR (400 MHz, CDCl$_3$) δ 7.63 (d, J=8.6 Hz, 2H), 7.14 (dd, J=2.1, 8.5 Hz, 1H), 7.10 (d, J=2.2 Hz, 1H), 7.00-6.93 (m, 1H), 6.93-6.87 (m, 1H), 5.76 (dd, J=3.8, 15.7 Hz, 1H), 5.58-5.44 (m, 1H), 4.43-4.30 (m, 1H), 4.26-4.14 (m, 3H), 3.98-3.89 (m, 2H), 3.80-3.62 (m, 1H), 3.44-3.28 (m, 1H), 3.25-3.05 (m, 1H), 2.83-2.66 (m, 2H), 2.54-2.44 (m, 2H), 2.25 (d, J=14.1 Hz, 2H), 2.15-2.00 (m, 1H), 1.94-1.40 (m, 9H), 1.35-1.17 m, 5H). m/z (ESI, +ve ion) 629.0 (M+H)$^+$.

Example 540. (1S,3'R,6'R,7'S,8'E,11'S,12'R)-6-chloro-7'-hydroxy-12'-((2R)-2-methoxypropyl)-11'-methyl-3,4-dihydro-2H,15'H-spiro[naphthalene-1, 22'-[20]oxa[13]thia[1,14]diazatetracyclo [14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-12'-((2R)-2-methoxypropyl)-11'-methyl-3,4-dihydro-2H,15'H-spiro[naphthalene-1,22'-[20]oxa[13]thia[1,14] diazatetracyclo[14.7.2.0$^{3,6}$.0$^{19,24}$]pentacosa [8,16,18, 24]tetraen]-15'-one 13',13'-dioxide To a 100 ml flask was added ([2R, 4S, 5S)-2-methoxy-N,N-bis(4-methoxybenzyl)-5-methyloct-7-ene-4-sulfonamide and (2R, 4R, 5S)-2-methoxy-N,N-bis(4-methoxybenzyl)-5-methyloct-7-ene-4-sulfonamide] (from Example 529 Step 2) (500 mg, 1.05 mmol), anisole (1.15 ml, 10.5 mmol), DCM (10 ml) and then TFA (4 ml). The reaction was stirred at 22° C. for 8 hours at which time the solvent was removed. The crude was purified on a Combiflash (12 gram gold silica column), eluting with 10% to 50% EtOAc in heptanes) to give [(2R,4R,5S)-2-methoxy-5-methyloct-7-ene-4-sulfonamide or (2R,4S,5S)-2-methoxy-5-methyloct-7-ene-4-sulfonamide] (127 mg, 0.540 mmol, 52% yield) as the slower eluting isomer, as a light yellow oil.

Step 2: (S)-6'-chloro-5-(((1R,2R)-2-((1S,5S,6S,8R,E)-1-hydroxy-8-methoxy-5-methyl-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((1S,5S,6R,8R,E)-1-hydroxy-8-methoxy-5-methyl-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic Acid

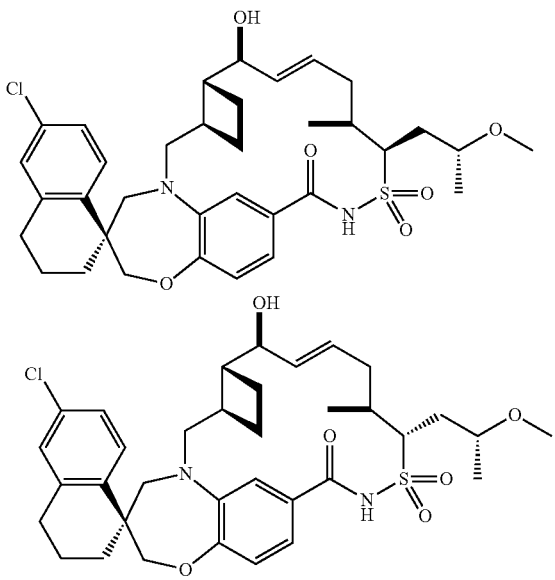

Step 1: (2R,4R,5S)-2-methoxy-5-methyloct-7-ene-4-sulfonamide or (2R,4S,5S)-2-methoxy-5-methyloct-7-ene-4-sulfonamide

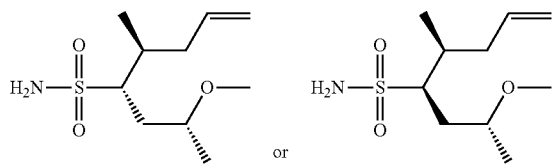

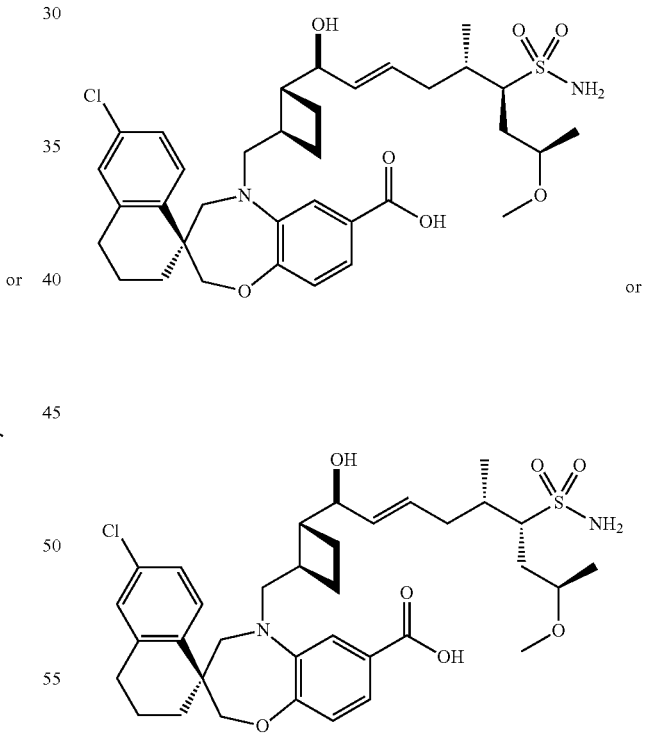

To a 100 ml flask was added (S)-6'-chloro-5-(((1R,2R)-2-((S,E)-1-hydroxyhex-2-en-1-yl)cyclobutyl)methyl)-3',4, 4',5-tetrahydro-2H,2'H-spiro[benzo[b][1,4]oxazepine-3,1'-naphthalene]-7-carboxylic acid (from Intermediate AA12A)

(27 mg, 0.051 mmol), [(2R,4R,5S)-2-methoxy-5-methyloct-7-ene-4-sulfonamide or (2R,4S,5S)-2-methoxy-5-methyloct-7-ene-4-sulfonamide](from Step 1) (42 mg, 0.18 mmol) and DCE (4 mL). The solution was sparged with argon for 15 minutes at which time Hoveyda-Grubbs II (3.2 mg, 5.1 µmol) was added as a 0.2 mL solution in DCE at room temperature. The mixture was stirred at room temperature for 16 hours. The solvent was removed from the filtrate and was directly purified on a Combiflash (12 gram gold silica column), eluting with 50%-90% EtOAc in heptanes+0.2% AcOH, to give [(S)-6'-chloro-5-(((1R,2R)-2-((1S,5S,6S,8R,E)-1-hydroxy-8-methoxy-5-methyl-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1R,2R)-2-((1S,5S,6R,8R,E)-1-hydroxy-8-methoxy-5-methyl-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic acid] (19 mg, 0.028 mmol, 56% yield) as white solids.

Step 3: (1S,3'R,6'R,7'S,8'E,11'S,12'S)-6-chloro-7'-hydroxy-12'-((2R)-2-methoxypropyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-7'-hydroxy-12'-((2R)-2-methoxypropyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide To a 25 ml flask containing [(S)-6'-chloro-5-(((1R,2R)-2-((1S,5S,6S,8R,E)-1-hydroxy-8-methoxy-5-methyl-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1R,2R)-2-((1S,5S,6R,8R,E)-1-hydroxy-8-methoxy-5-methyl-6-sulfamoylnon-2-en-1-yl)cyclobutyl)methyl)-3',4,4',5-tetrahydro-2H,2'H-spiro[benzo[b][1,4]oxazepine-3,1'-naphthalene]-7-carboxylic acid] (from Step 2) (19 mg, 0.088 mmol) was added N,N-dimethylpyridin-4-amine (5.8 mg, 0.048 mmol) and 40 ml of DCM. The reaction mixture was cooled to 0° C. at which time N-(3-dimethylaminopropyl)-N'-ethylcarbodiimide hydrochloride (11 mg, 0.056 mmol) was slowly added. The reaction was stirred at room temperature for 18 hour. The mixture was then quenched with 50 ml of 1N HCl and extracted with 200 ml of EtOAc. The organic layer were dried over anhydrous sodium sulfate, filtered and concentrated by rotary evaporation. The crude was purified on a Combiflash (4 gram gold silica column), eluting with 50%-90% EtOAc in heptanes, to give the title compound (8.0 mg, 0.012 mmol, 43% yield) as a white solid. $^1$H NMR (500 MHz, CDCl$_3$) δ 8.08 (br. s., 1H), 7.70 (d, J=8.6 Hz, 1H), 7.19 (dd, J=2.2, 8.6 Hz, 1H), 7.10 (d, J=2.2 Hz, 1H), 7.01-6.97 (m, 1H), 6.95-6.84 (m, 2H), 5.89-5.79 (m, 1H), 5.77-5.71 19 (dd, J=7.6, 15.4 Hz, 1H), 4.23 (dd, J=4.4, 7.6 Hz, 1H), 4.19 (dd, J=3.1, 9.4 Hz, 1H), 4.10 (s, 2H), 3.83 (d, J=16.1 Hz, 2H), 3.69 (d, J=14.4 Hz, 1H), 3.39 (s, 3H), 3.25 (d, J=14.2 Hz, 1H), 3.09-3.00 (m, 1H), 2.86-2.68 (m, 2H), 2.45 (ddd, J=5.0, 9.4, 14.7 Hz, 1H), 2.33 (t, J=8.8 Hz, 1H), 2.21-1.95 (m, 6H), 1.92-1.71 (m, 3H), 1.69-1.57 (m, 2H), 1.41 (t, J=12.3 Hz, 1H), 1.28 (d, J=5.9 Hz, 3H), 1.07 (d, J=6.6 Hz, 3H). m/z (ESI, +ve ion) 657.0 (M+H)$^+$.

Example 543. (1S,3'R,6'R,7'S,8'Z,12'S)-6-chloro-12'-((2R)-2-hydroxypropyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'Z,12'R)-6-chloro-12'-((2R)-2-hydroxypropyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

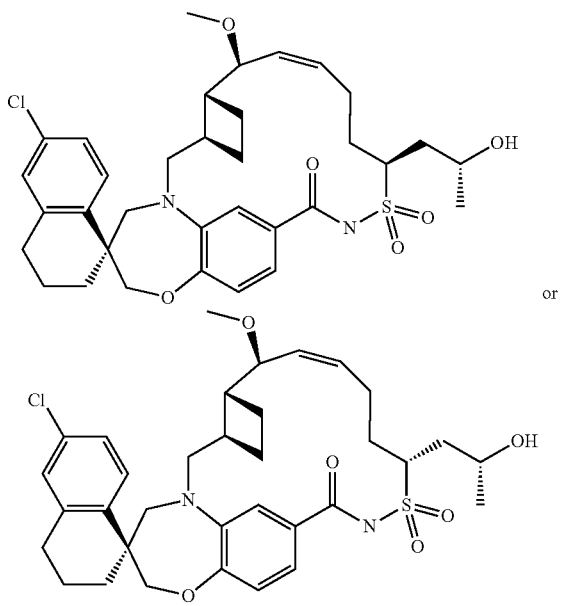

Step 1: (2R,4S)-2-((tert-butyldiphenylsilyl)oxy)oct-7-ene-4-sulfonamide or (2R,4R)-2-((tert-butyldiphenylsilyl)oxy)oct-7-ene-4-sulfonamide

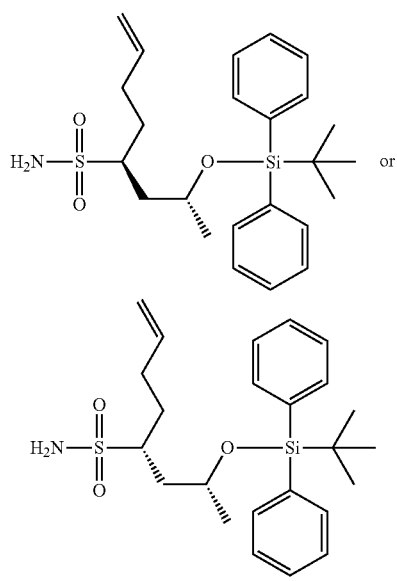

To a 100 ml flask was added [(2R,4S)-2-((tert-butyldiphenylsilyl)oxy)-N,N-bis(4-methoxybenzyl)oct-7-ene-4-sulfonamide or (2R,4R)-2-((tert-butyldiphenylsilyl)oxy)-N,N-bis(4-methoxybenzyl)oct-7-ene-4-sulfonamide](from Example 508 Step 2) (565 mg, 0.824 mmol), anisole (0.90 ml, 8.2 mmol), DCM (4 ml) and then TFA (2 ml). The reaction was stirred at 22° C. for 3 hours at which time the solvent was removed. The crude product was purified on a Combiflash (24 g gold silica column), eluting with 10% to 50% EtOAc in heptanes, to give [(2R,4S)-2-((tert-butyldiphenylsilyl)oxy)oct-7-ene-4-sulfonamide or (2R,4R)-2-((tert-butyldiphenylsilyl)oxy)oct-7-ene-4-sulfonamide] (90.0 mg, 0.159 mmol, 19% yield) as a light yellow oil.

Step 2: (S)—N-(((2R,4R)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(((2R,4S)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide

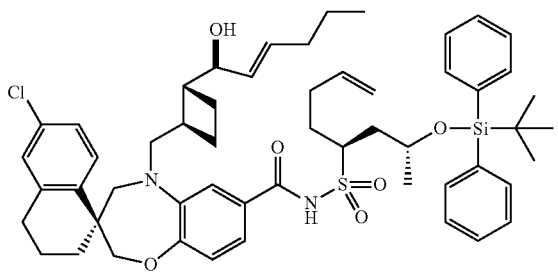

or

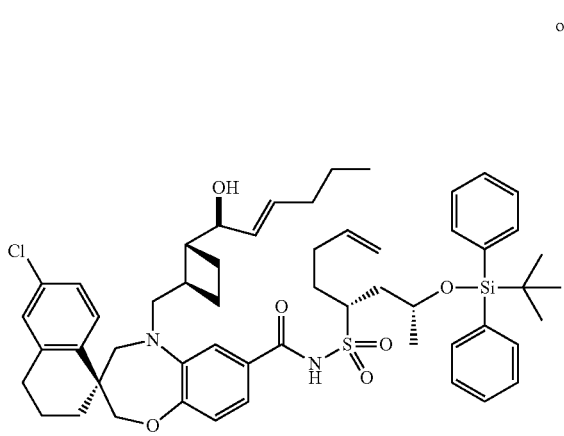

To a 100 ml flask was added (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (from Intermediate AA12A) (150 mg, 0.294 mmol), N,N-dimethylpyridin-4-amine (71.9 mg, 0.588 mmol) and [(2R,4R)-2-((tert-butyldiphenylsilyl)oxy)oct-7-ene-4-sulfonamide or (2R,4S)-2-((tert-butyldiphenylsilyl)oxy)oct-7-ene-4-sulfonamide](from Step 1) (262 mg, 0.588 mmol) and then N-(3-dimethylaminopropyl)-N'-ethylcarbodiimide hydrochloride (113 mg, 0.588 mmol). The reaction was stirred at room temperature for 16 hours at which time the solvent was removed and the crude product was purified on a Combiflash (12 g gold silica column), eluting with 2%-10% EtOAc in heptanes+0.2% AcOH, to give [(S)—N-(((2R,4R)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(((2R,4S)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide carboxamide] (142 mg, 0.151 mmol, 52% yield) as a thick yellow oil.

Step 3: [(1S,3'R,6'R,7'S,8'Z,12'R)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide and (1S,3'R,6'R,7'S,8'E,12'R)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or [(1S,3'R,6'R,7'S,8'Z,12'S)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide and (1S,3'R,6'R,7'S,8'E,12'S)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide]

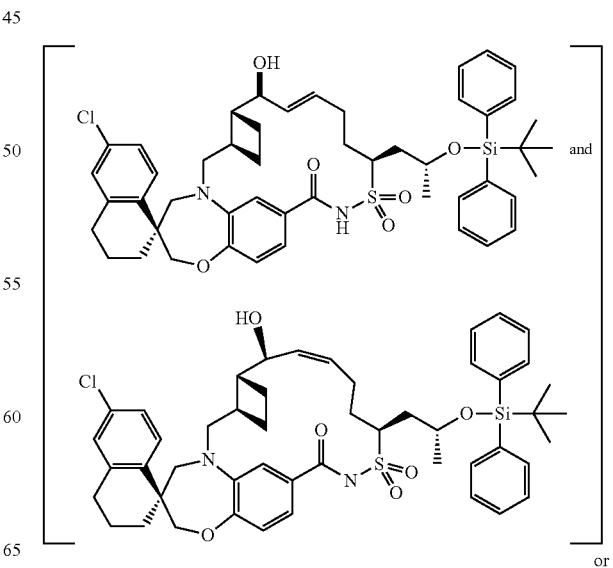

or

1169

-continued

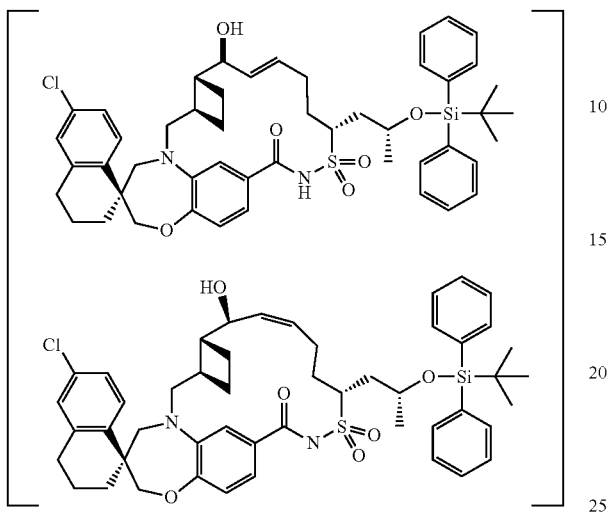

To a 100 ml flask was added [(((S)—N-(((2R,4R)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl) methyl)-3',4,4',5-tetrahydro-2H,2'H-spiro[benzo[b][1,4] oxazepine-3,1'-naphthalene]-7-carboxamide or (S)—N-(((2R,4S)-2-((tert-butyldiphenylsilyl)oxy)oct-7-en-4-yl) sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide carboxamide] (from Step 2) (142 mg, 0.151 mmol % yield) and DCM (100 ml). The mixture was stirred at room temperature while argon was bubbled through the reaction mixture for 15 minutes. To the homogeneous solution was then added Hoveyda-Grubbs II (19 mg, 0.030 mmol) and the mixture was stirred at 45° C. for 6 hours. The reaction mixture was then filtered, concentrated and the crude product was purified on a Combiflash (12 g gold silica column), eluting with 10%-40% EtOAc in heptanes+0.2% AcOH, to give[[(1S,3'R,6'R,7'S,8'Z,12'R)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1, 14]diazatetracyclo[14.7.2.0$^{3,6}$.0$^{19,24}$]pentacosa[8,16,18,24] tetraen]-15'-one 13',13'-dioxide] and (1S,3'R,6'R,7'S,8'E, 12'R)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$. 0$^{19,24}$]pentacosa[8,16,18,24]tetraen]-15'-one 13',13'-dioxide] or [(1S,3'R,6'R,7'S,8'Z,12'S)-12'-((2R)-2-((tert-butyl (diphenyl)silyl)oxy)propyl)-6-chloro-7'-hydroxy-3,4-dihydro-2h,15'h-spiro[naphthalene-1,22'-[20]oxa[13]thia[1, 14]diazatetracyclo[14.7.2.0$^{3,6}$.0$^{19,24}$]pentacosa[8,16,18,24] tetraen]-15'-one 13',13'-dioxide and (1S,3'R,6'R,7'S,8'E,

1170

12'S)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,}$ $^{24}$]pentacosa[8,16,18,24]tetraen]-15'-one  13',13'-dioxide]] (68.3 mg, 0.079 mmol, 52.0% yield) as a 9:1 mixture of E to Z isomers, as a white solids.

Step 4: (1S,3'R,6'R,7'S,8'Z,12'S)-12'-((2R)-2-((tert-butyl(diphenyl)silyl)oxy)propyl)-6-chloro-7'-methoxy-3,4-dihydro-2H,15'H-spiro[naphthalene-1, 22'-[20]oxa[13]thia[1,14]diazatetracyclo [14.7.2.0$^{3,6}$.0$^{19,24}$]pentacosa [8,16,18,24]tetraen]-15'-one 13',13'-dioxide or (1S,3'R,6'R,7'S,8'Z,12'R)-12'-((2R)-2-((tert-butyl(diphenyl)silyl)oxy)propyl)-6-chloro-7'-methoxy-3,4-dihydro-2H,15'H-spiro [naphthalene-1,22'-[20]oxa[13]thia[1,14] diazatetracyclo[14.7.2.0$^{3,6}$.0$^{19,24}$]pentacosa [8,16, 18, 24]tetraen]-15'-one 13',13'-dioxide

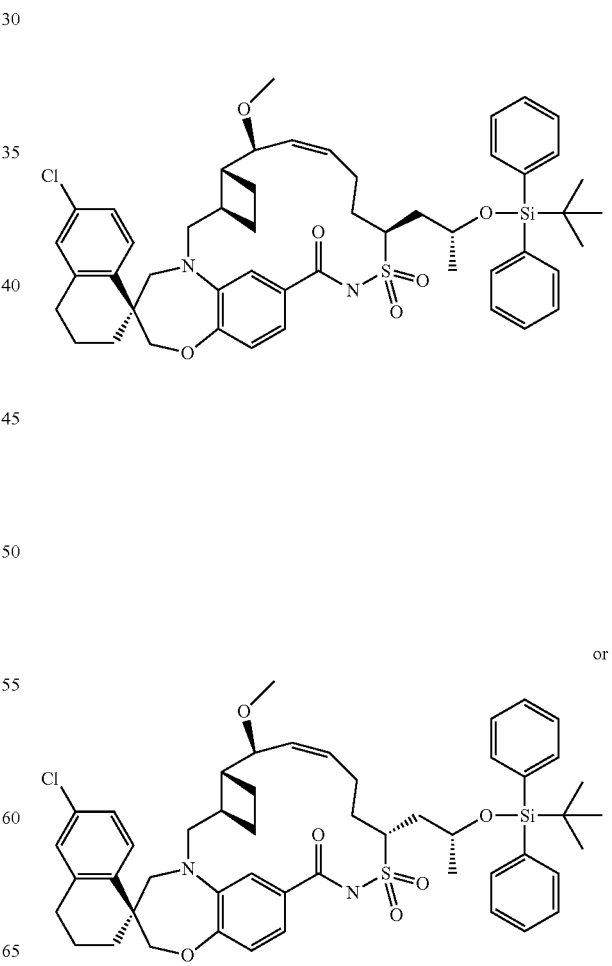

To a 100 ml flask was added [[(1S,3'R,6'R,7'S,8'Z,12'R)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,12'R)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] or [(1S,3'R,6'R,7'S,8'Z,12'S)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,12'S)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide]] (from Step 3) (50 mg, 0.058 mmol), THF (3 mL) and NaH (14 mg, 0.58 mmol). The reaction was stirred at room temperature for 15 minutes at which time MeI (0.018 ml, 0.29 mmol) was added. The reaction was stirred at room temperature for 3 hours and then the reaction was quenched with 100 ml of saturated ammonium chloride and extracted with 400 ml of EtOAc. The organic layer was dried over sodium sulfate, filtered, the solvent was removed by rotary evaporation, and the crude was purified on a Combiflash (12 gram gold silica column), eluting with 10% to 50% EtOAc in heptanes, to give [(1S,3'R,6'R,7'S,8'Z,12'S)-12'-((2R)-2-((tert-butyl(diphenyl)silyl)oxy)propyl)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'R)-12'-((2R)-2-((tert-butyl(diphenyl)silyl)oxy)propyl)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (6.0 mg, 6.81 μmol, 12% yield) as the slower eluting olefin isomer as a light yellow oil.

Step 5: (1S,3'R,6'R,7'S,8'Z,12'S)-6-chloro-12'-((2R)-2-hydroxypropyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'Z,12'R)-6-chloro-12'-((2R)-2-hydroxypropyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide To a 100 ml flask was added [(1S,3'R,6'R,7'S,8'Z,12'S)-12'-((2R)-2-((tert-butyl(diphenyl)silyl)oxy)propyl)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'R)-12'-((2R)-2-((tert-butyl(diphenyl)silyl)oxy)propyl)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (6.0 mg, 6.9 μmol) and TBAF 1 M in THF (0.86 ml, 0.86 mmol). The reaction was stirred at room temperature for 16 hours at which time the reaction was quenched with 50 ml of brine and extracted with 200 ml of EtOAc. The organic layer was dried over sodium sulfate, filtered, the solvent was removed by rotary evaporation and the crude was purified on a Combiflash (4 gram gold silica column), eluting with 10% to 50% EtOAc in heptanes, to give the title compound (2.9 mg, 4.5 μmol, 65% yield) as an off white solid. $^{1}$H NMR (400 MHz, CDCl$_3$) δ 8.92 (br. s., 1H), 7.69 (d, J=8.6 Hz, 1H), 7.25-7.14 (m, 2H), 7.09 (d, J=1.8 Hz, 1H), 7.02-6.92 (m, 2H), 5.78-5.63 (m, 1H), 5.39 (dd, J=8.0, 10.6 Hz, 1H), 4.18-4.06 (m, 3H), 4.02-3.93 (m, 2H), 3.83-3.61 (m, 2H), 3.35 (s, 3H), 3.32-3.23 (m, 2H), 2.86-2.71 (m, 2H), 2.58-2.35 (m, 4H), 2.33-2.20 (m, 1H), 2.09-1.98 (m, 3H), 1.97-1.79 (m, 6H), 1.77-1.67 (m, 1H), 1.51-1.43 (m 1H), 1.34 (d, J=6.1 Hz, 3H). m/z (ESI, +ve ion) 643.0 (M+H)$^{+}$.

Example 544. (1S,3'R,6'R,7'S,8'E,12'S)-6-chloro-7'-hydroxy-12'-((2R)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-hydroxy-12'-((2R)-2-hydroxypropyl)-3,4-dihydro-2H,15'H-spiro[naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide

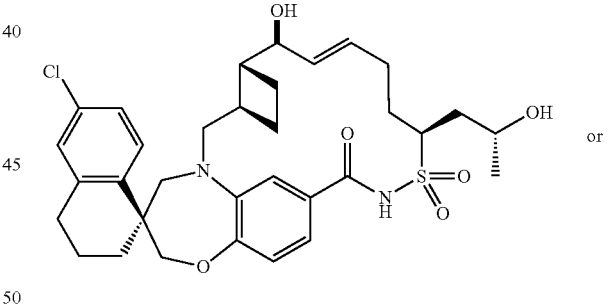

or

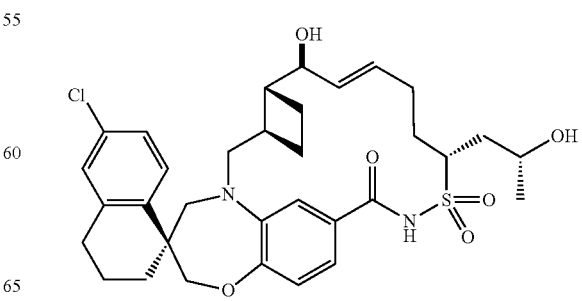

Step 1: [(1S,3'R,6'R,7'S,8'Z,12'R)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide and (1S,3'R,6'R,7'S,8'E,12'R)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide] or [(1S,3'R,6'R,7'S,8'Z,12'S)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide and (1S,3'R,6'R,7'S,8'E,12'S)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide]

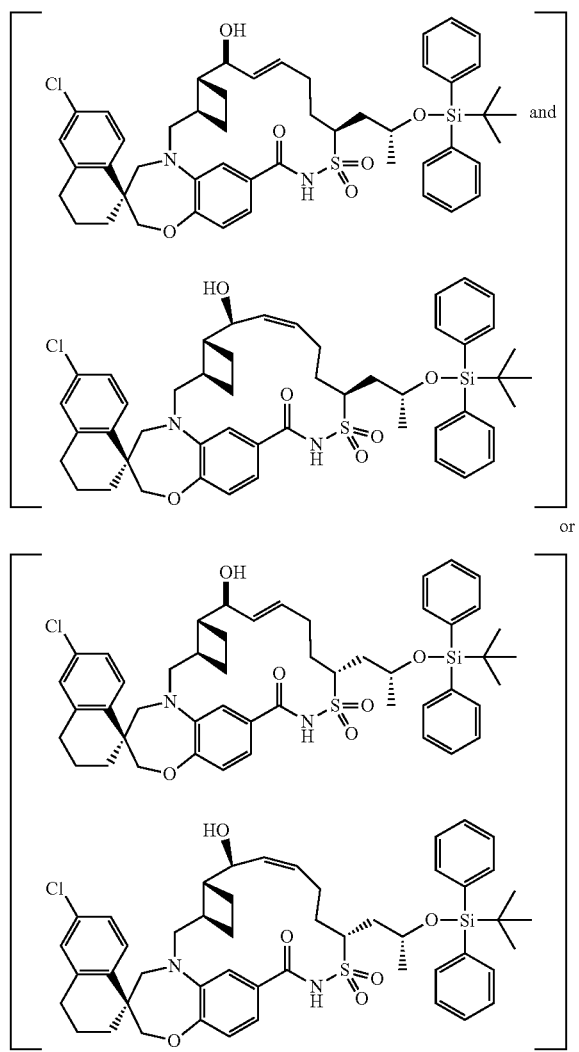

To a 100 ml flask was added [((S)—N-(((2R,4R)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(((2R,4S)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide carboxamide] (from Example 543 Step 2) (64 mg, 0.069 mmol) and DCM (50 ml). The mixture was stirred at room temperature while argon was bubbled through the reaction mixture for 15 minutes. To the homogeneous solution was then added Hoveyda-Grubbs II (4.3 mg, 6.9 μmol) and the mixture was stirred to 45° C. for 6 hours. The reaction mixture was then filtered, concentrated and the crude product was purified on a Combiflash (12 g gold silica column), eluting with 10%-40% EtOAc in heptanes+0.2% AcOH, to give [[(1S,3'R,6'R,7'S,8'Z,12'R)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,12'R)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] or [(1S,3'R,6'R,7'S,8'Z,12'S)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,12'S)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide]] (33 mg, 0.054 mmol, 38% yield) as a 3:1 mixture of E to Z isomers, as a white solids.

Step 2: (1S,3'R,6'R,7'S,8'E,12'S)-6-chloro-7'-hydroxy-12'-((2R)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-hydroxy-12'-((2R)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide To a 100 ml flask was added [[(1S,3'R,6'R,7'S,8'Z,12'R)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,12'R)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] or [(1S,3'R,6'R,7'S,8'Z,12'S)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,12'S)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide]] (from Step 1) (20 mg, 0.023 mmol), and TBAF 1 M in THF (2.1 ml, 2.1 mmol). The reaction was stirred at room temperature for 5 hours (No reaction observed by LCMS) at which time 1 ml of AcOH was added and the reaction was stirred at room temperature for an additional 16 hours (no reaction observed). The temperature of the reaction was then raised to 60° C. and the reaction was stirred for an additional 6 hours at which time the reaction was quenched with 50 ml of brine and extracted with 200 ml of EtOAc. The organic layer was dried over sodium sulfate, filtered, the solvent was removed by rotary evaporation, and the crude product was purified on a Combiflash (4 g gold silica column), eluting with 50% to 90% EtOAc in heptanes+0.2% AcOH) to give the title compound (2.2 mg, 3.5 μmol, 15% yield) as an off white solid. $^1$H NMR (400 MHz, CDCl$_3$) δ 7.70 (d, J=8.4 Hz, 1H), 7.18 (dd, J=2.2, 8.5 Hz, 1H), 7.09 (d, J=2.2 Hz, 1H), 6.99-6.87 (m, 3H), 5.96-5.80 (m, 1H), 5.72 (dd, J=7.4, 15.3 Hz, 1H), 4.36-4.22 (m, 2H), 4.18-4.02 (m, 3H), 3.70 (d, J=14.1 Hz, 2H), 3.23 (d, J=14.3 Hz, 1H), 3.09-2.92 (m, 1H), 2.82-2.69 (m, 2H), 2.49-2.19 (m, 7H), 2.08-1.53 (m, 8H), 1.46-1.37 (m, 1H), 1.34 (d, J=6.3 Hz, 3H). m/z (ESI, +ve ion) 629.0 (M+H)$^+$.

Example 546. (1S,3'R,6'R,7'S,8'E,12'S)-6-chloro-7'-hydroxy-12'-((2S)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-7'-hydroxy-12'-((2S)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

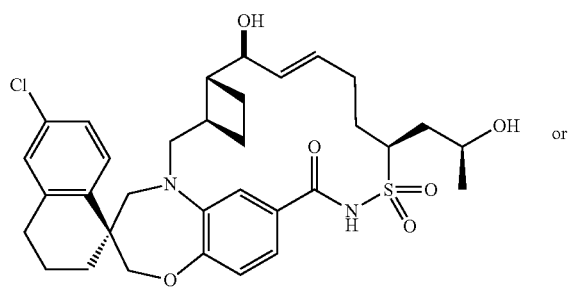

Step 1: (2S,4S)-2-hydroxy-N,N-bis(4-methoxybenzyl)oct-7-ene-4-sulfonamide and (2S,4R)-2-hydroxy-N,N-bis(4-methoxybenzyl)oct-7-ene-4-sulfonamide

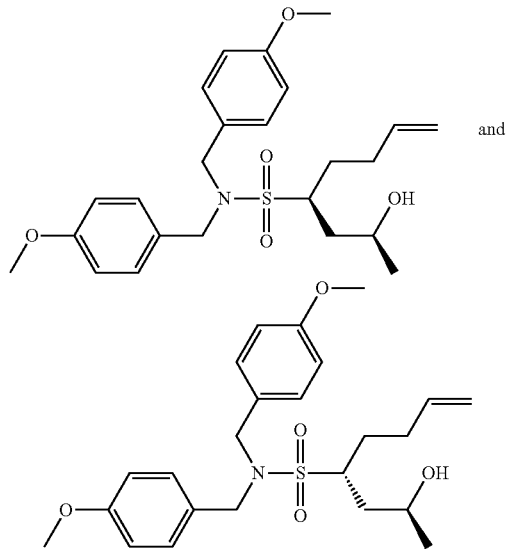

To a −78° C. solution of N,N-bis(4-methoxybenzyl)pent-4-ene-1-sulfonamide (from Intermediate EE19) (4.00 g, 10.3 mmol) in THF (40 mL) under argon was added n-butyllithium (2.5 M solution in hexane, 4.93 mL, 12.3 mmol) over 5 minutes. The mixture was stirred at −78° C. for 2 hours (solution turned red-pink) at which time (S)-(+)-1,2-epoxypropane (Sigma-Aldrich, Milwaukee, WI) (1.079 mL, 15.4 mmol) was added and stirred at 0° C. for 16 hours. The reaction was then quenched with 100 ml of saturated ammonium chloride and extracted with 300 ml of EtOAc. The organic layer was dried over sodium sulfate, filtered and the solvent removed by rotary evaporation. The crude product was purified on a Combiflash (80 g gold silica column), eluting with 10% to 50% EtOAc in heptanes, to give [(2S,4S)-2-hydroxy-n,n-bis(4-methoxybenzyl)oct-7-ene-4-sulfonamide and (2S,4R)-2-hydroxy-n,n-bis(4-methoxybenzyl)oct-7-ene-4-sulfonamide] (3.88 g, 8.67 mmol, 84% yield) as a light yellow oil.

Step 2: (2S,4R)-2-((tert-butyldiphenylsilyl)oxy)-N,N-bis(4-methoxybenzyl)oct-7-ene-4-sulfonamide or (2S,4S)-2-((tert-butyldiphenylsilyl)oxy)-N,N-bis(4-methoxybenzyl)oct-7-ene-4-sulfonamide

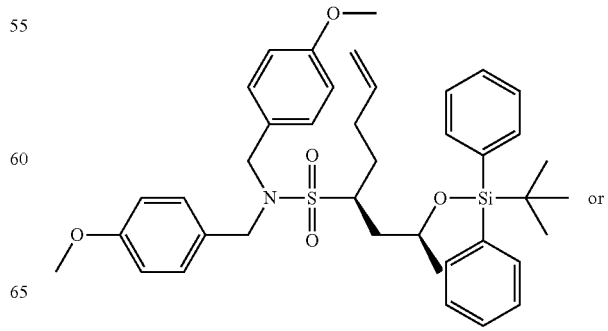

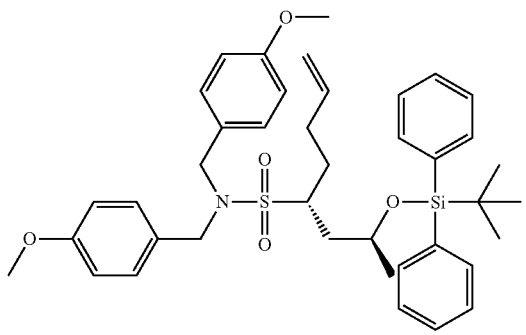

To a 100 ml flask was added [(2S,4S)-2-hydroxy-n,n-bis(4-methoxybenzyl)oct-7-ene-4-sulfonamide and (2S,4R)-2-hydroxy-n,n-bis(4-methoxybenzyl)oct-7-ene-4-sulfonamide] (from Step 1) (3.88 g, 8.67 mmol), DMF (60 ml), imidazole (1.18 g, 17.3 mmol) and tert-butylchlorodiphenylsilane (3.38 ml, 13.0 mmol). The reaction was stirred at 65° C. for 16 hours at which time reaction was then quenched with 200 ml of saturated ammonium chloride and extracted with 600 ml of diethyl ether. The organic layer was dried over sodium sulfate, filtered and the solvent removed by rotary evaporation. The crude product was first purified on a Combiflash (80 g gold silica column), eluting with 10% to 30% EtOAc in heptanes. The racemic mixture (1:1) was then purified by preparatory SCF chromatography (Chiralpak AD 250 mm×30 mm column, Phenomenex, Torrance, CA; 16 g/minute EtOH+(20 mM Ammonia)+64 g/minute $CO_2$ (20% co-solvent) on Thar 80 SFC; outlet pressure=100 bar; temperature=22° C.; wavelength=220 nm; used 1.0 mL injections of 3647 mg/41 mL (89 mg/mL) sample solution of MeOH (35 mL) and DCM (5 mL); run time=13 minutes & cycle time 10 minutes.) to provide [(2S,4R)-2-((tert-butyldiphenylsilyl)oxy)-N,N-bis(4-methoxybenzyl)oct-7-ene-4-sulfonamide or (2S,4S)-2-((tert-butyldiphenylsilyl)oxy)-N,N-bis(4-methoxybenzyl)oct-7-ene-4-sulfonamide] (2.10 g, 3.06 mmol, 44% yield) as the faster eluting isomer as a yellow liquid.

Step 3: (2S,4R)-2-((tert-butyldiphenylsilyl)oxy)oct-7-ene-4-sulfonamide or (2S,4S)-2-((tert-butyldiphenylsilyl)oxy)oct-7-ene-4-sulfonamide

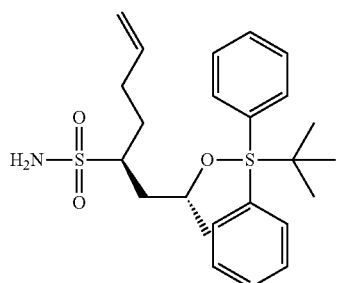

or

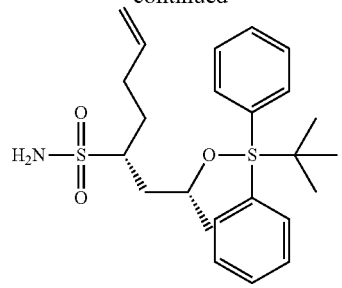

To a 100 ml flask was added [(2S,4R)-2-((tert-butyldiphenylsilyl)oxy)-N,N-bis(4-methoxybenzyl)oct-7-ene-4-sulfonamide or (2S,4S)-2-((tert-butyldiphenylsilyl)oxy)-N,N-bis(4-methoxybenzyl)oct-7-ene-4-sulfonamide](from Step 2) (450 mg, 0.656 mmol), anisole (0.717 ml, 6.56 mmol), DCM (20 ml) and then TFA (5 ml). The reaction was stirred at 22° C. for 3 hours at which time the solvent was removed. The crude product was purified on a Combiflash (24 g gold silica column), eluting with 10% to 50% EtOAc in heptanes, to give [(2S,4R)-2-((tert-butyldiphenylsilyl)oxy)oct-7-ene-4-sulfonamide or (2S,4S)-2-((tert-butyldiphenylsilyl)oxy)oct-7-ene-4-sulfonamide] (150 mg, 0.337 mmol, 51% yield) as a light yellow oil.

Step 4: (S)—N-(((2S,4R)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(((2S,4S)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide

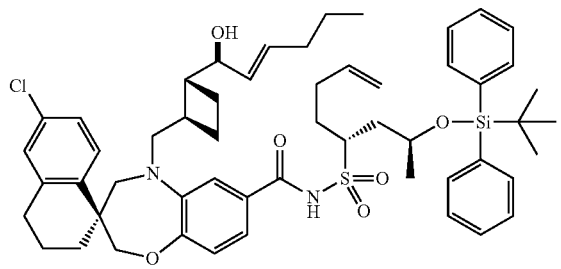

or

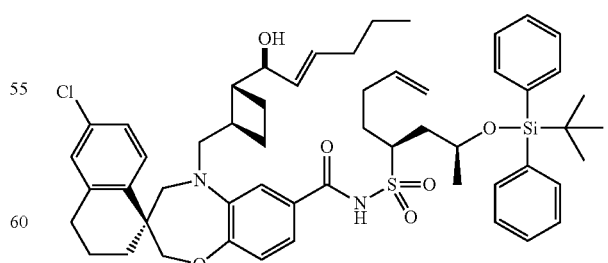

To a 100 ml flask was added (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (from Intermediate AA12A)

(85 mg, 0.17 mmol), N,N-dimethylpyridin-4-amine (41 mg, 0.33 mmol) and [(2S,4R)-2-((tert-butyldiphenylsilyl)oxy)oct-7-ene-4-sulfonamide or (2S,4S)-2-((tert-butyldiphenylsilyl)oxy)oct-7-ene-4-sulfonamide] (from Step 3) (149 mg, 0.333 mmol) and then N-(3-dimethylaminopropyl)-N'-ethylcarbodiimide hydrochloride (64 mg, 0.33 mmol). The reaction was stirred at room temperature for 16 hours at which time the solvent was removed and the crude product was purified on a Combiflash (12 g gold silica column), eluting with 2%-10% EtOAc in heptanes+0.2% AcOH, to give [(S)—N-(((2S,4R)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(((2S,4S)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide] (100 mg, 0.107 mmol, 64% yield) as a thick yellow oil.

Step 5: (1S,3'R,6'R,7'S,8'E,12'R)-12'-((2S)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide] or (1S,3'R,6'R,7'S,8'E,12'S)-12'-((2S)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

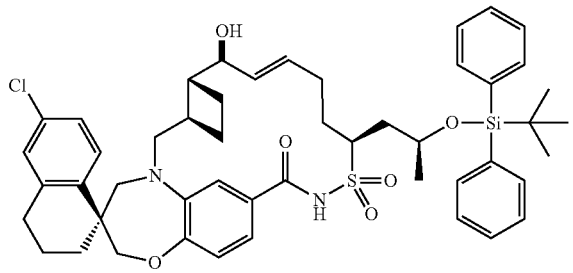

or

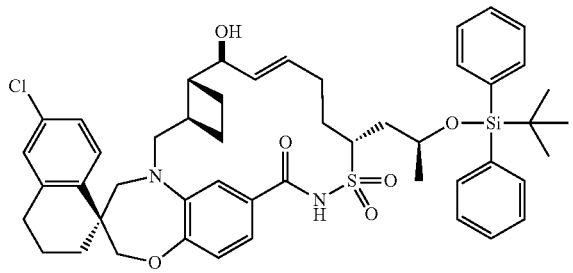

To a 100 ml flask was added [(S)—N-(((2S,4R)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(((2S,4S)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide] (from Step 4) (100 mg, 0.107 mmol) and DCM (40 ml). The mixture was stirred at room temperature while argon was bubbled through the reaction mixture for 15 minutes. To the homogeneous solution was then added Hoveyda-Grubbs II (13 mg, 0.021 mmol) and the mixture was stirred to 45° C. for 6 hours. The reaction mixture was then filtered, concentrated and the crude product was purified on a Combiflash (12 g gold silica column), eluting with 10%-40% EtOAc in heptanes+0.2% AcOH, to give [(1S,3'R,6'R,7'S,8'E,12'R)-12'-((2S)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-12'-((2S)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (29 mg, 0.034 mmol, 32% yield) as the faster eluting olefin isomer, as a white solids.

Step 6: (1S,3'R,6'R,7'S,8'E,12'S)-6-chloro-7'-hydroxy-12'-((2S)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-hydroxy-12'-((2S)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide To a 100 ml flask was added [(1S,3'R,6'R,7'S,8'E,12'R)-12'-((2S)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-12'-((2S)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (from Step 5) (13 mg, 0.015 mmol) and TBAF (1 M in THF, 3.04 ml, 3.04 mmol). The reaction was stirred at 65° C. for 3.5 hours at which time the reaction was quenched with 50 ml of brine and extracted with 200 ml of EtOAc. The organic layer was dried over sodium sulfate, filtered, the solvent was removed by rotary evaporation, and the crude product was purified on a Combiflash (4 g gold silica column), eluting with 50% to 90% EtOAc in heptanes) to give the title compound (6.0 mg, 9.5 µmol, 63% yield) as an off white solid. $^1$H NMR (400 MHz, CDCl$_3$) δ 8.45 (s, 1H), 7.70 (d, J=8.4 Hz, 1H), 7.19 (dd, J=2.2, 8.5 Hz, 1H), 7.09 (d, J=2.2 Hz, 1H), 6.95-6.88 (m, 3H), 5.96-5.85 (m, 1H), 5.72 (dd, J=7.3, 15.2 Hz, 1H), 4.37 (ddd, J=2.4, 6.1, 10.5 Hz, 2H), 4.24 (dd, J=3.9, 7.4 Hz, 1H), 4.12-4.02 (m, 2H), 3.81 (d, J=13.7 Hz, 1H), 3.71 (d, J=14.3 Hz, 1H), 3.24 (d, J=14.3 Hz, 1H), 3.02 (dd, J=9.4, 15.3 Hz, 1H), 2.85-2.65 (m, 3H), 2.51-2.16 (m, 6H), 2.07-1.72 (m, 6H), 1.71-1.59 (m, 2H), 1.40 (t, J=12.9 Hz, 1H), 1.26 (d, J=6.1 Hz, 3H). m/z (ESI, +ve ion) 628.9 (M+H)$^+$.

Example 547. (1S,3'R,6'R,7'S,8'Z,12'S)-6-chloro-7'-hydroxy-12'-((2S)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'R)-6-chloro-7'-hydroxy-12'-((2S)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

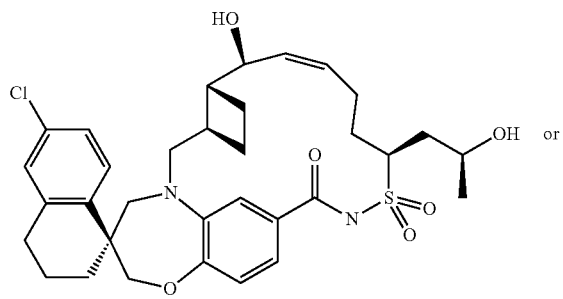

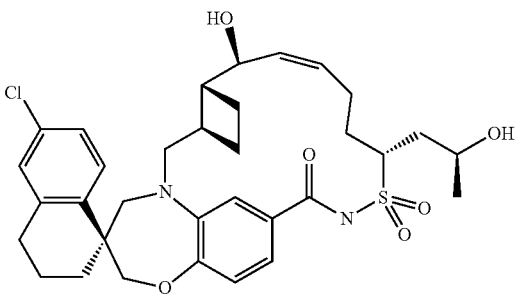

Step 1: (1S,3'R,6'R,7'S,8'Z,12'R)-12'-((2S)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] or (1S,3'R,6'R,7'S,8'Z,12'S)-12'-((2S)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide]

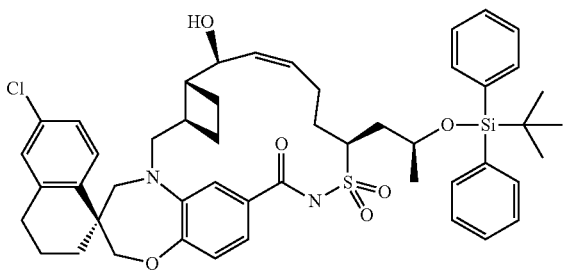

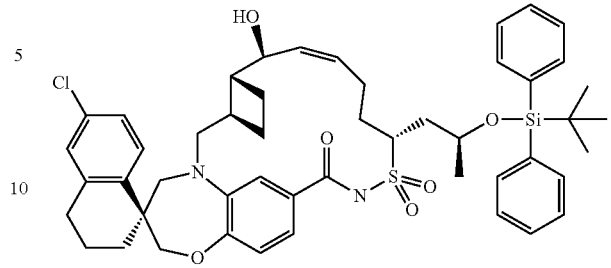

To a 100 ml flask was added [(S)—N-(((2S,4R)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(((2S,4S)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide] (from Example 546, Step 4) (100 mg, 0.107 mmol) and DCM (40 ml). The mixture was stirred at room temperature while argon was bubbled through the reaction mixture for 15 minutes. To the homogeneous solution was then added Hoveyda-Grubbs II (13 mg, 0.021 mmol) and the mixture was stirred at 45° C. for 6 hours. The reaction mixture was then filtered, concentrated and the crude product was purified on a Combiflash (12 g gold silica column), eluting with 10%-40% EtOAc in heptanes+0.2% AcOH, to give [(1S,3'R,6'R,7'S,8'Z,12'R)-12'-((2S)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] or (1S,3'R,6'R,7'S,8'Z,12'S)-12'-((2S)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (29 mg, 0.034 mmol, 32% yield) as the slower eluting olefin isomer, as a white solids.

Step 2: (1S,3'R,6'R,7'S,8'Z,12'S)-6-chloro-7'-hydroxy-12'-((2S)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'R)-6-chloro-7'-hydroxy-12'-((2S)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide To a 100 ml flask was added [(1S,3'R,6'R,7'S,8'Z,12'R)-12'-((2S)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'S)-12'-((2S)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (from Step 1) (14 mg, 0.016 mmol) and TBAF (1 M in THF, 2.02 ml, 2.02 mmol). The reaction was stirred at 65° C. for 3 hours at which time the reaction was quenched with 50 ml of brine and extracted with 200 ml of EtOAc. The organic layer was dried over sodium sulfate, filtered, the solvent was removed by rotary evaporation and the crude product was purified on a Combiflash (4 g gold silica column), eluting with 50% to 90% EtOAc in heptanes, to give the title compound [(1S,3'R,6'R,7'S,8'Z,12'S)-6-chloro-7'-hydroxy-12'-((2S)-2-hydroxypropyl)-3,4-dihydro-2H,15'H (6.1 mg, 9.7 μmol, 60% yield) as an off white solid. $^1$H NMR (400 MHz, CDCl$_3$) δ 9.94 (br. s., 1H), 7.68 (d, J=8.6 Hz, 1H), 7.32 (dd, J=1.8, 8.2 Hz, 1H), 7.18 (d, J=2.3 Hz, 1H), 7.13-7.05 (m, 2H), 6.94 (d, J=8.2 Hz, 1H), 5.69-5.59 (m, 1H), 5.50 (dd, J=5.7, 11.2 Hz, 1H), 4.48 (t, J=5.6 Hz, 1H), 4.41-4.29 (m, 1H), 4.13-4.02 (m, 2H), 4.00-3.90 (m, 1H), 3.68 (d, J=15.1 Hz, 1H), 3.60 (d, J=14.1 Hz, 1H), 3.25-3.5 (m, 2H), 2.84-2.73 (m, 2H), 2.73-2.61 (m, 1H), 2.50-2.33 (m, 3H), 2.33-2.21 (m, 1H), 2.21-2.12 (m, 1H), 2.06-1.77 (m, 5H), 1.76-1.61 (m, 4H), 1.48 (t, J=11.5 Hz, 1H), 1.28 (d, J=6.3 Hz, 3H). m/z (ESI, +ve ion) 629.0 (M+H)$^+$.

Example 548. (1S,3'R,6'R,7'S,8'E,12'S)-6-chloro-12'-((2R)-2-hydroxypropyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-12'-((2R)-2-hydroxypropyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

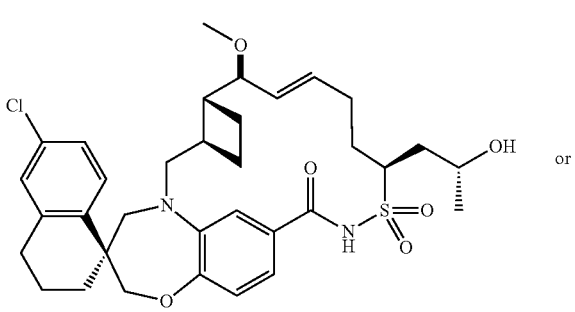

or

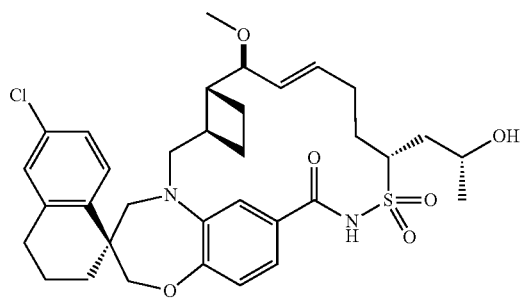

Step 1: (1S,3'R,6'R,7'S,8'E,12'S)-12'-((2R)-2-((tert-butyl(diphenyl)silyl)oxy)propyl)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-12'-((2R)-2-((tert-butyl(diphenyl)silyl)oxy)propyl)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

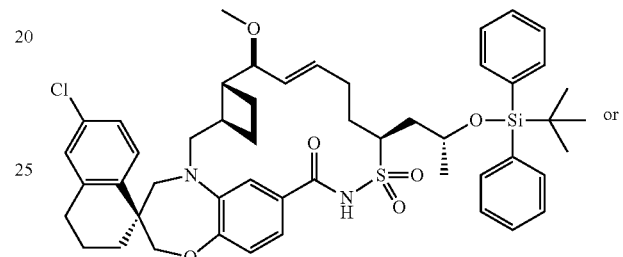

or

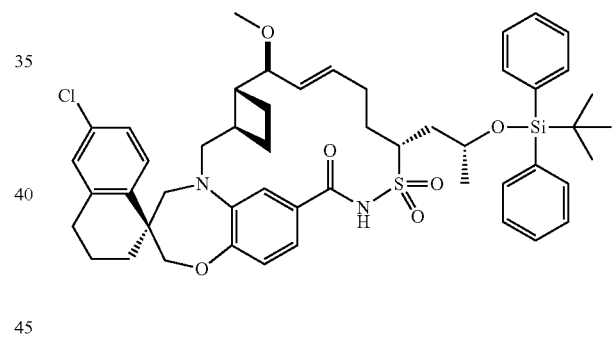

To a 100 ml flask was added [[(1S,3'R,6'R,7'S,8'Z,12'R)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,12'R)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] or [(1S,3'R,6'R,7'S,8'Z,12'S)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,12'S)-12'-((2R)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]

tetraen]-15'-one 13',13'-dioxide]] (from Example 543, Step 3) (50 mg, 0.058 mmol), THF (3 mL) and NaH (14 mg, 0.58 mmol). The reaction was stirred at room temperature for 15 minutes at which time MeI (0.018 ml, 0.29 mmol) was added. The reaction was stirred at room temperature for 3 hours and then the reaction was quenched with 100 ml of saturated ammonium chloride and extracted with 400 ml of EtOAc. The organic layer was dried over sodium sulfate, filtered, the solvent was removed by rotary evaporation, and the crude was purified on a Combiflash (12 gram gold silica column), eluting with 10% to 50% EtOAc in heptanes, to give [(1S,3'R,6'R,7'S,8'E,12'S)-12'-((2R)-2-((tert-butyl(diphenyl)silyl)oxy)propyl)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-12'-((2R)-2-((tert-butyl(diphenyl)silyl)oxy)propyl)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (35 mg, 0.040 mmol, 70% yield) as the faster eluting olefin isomer as a light yellow oil.

Step 2: (1S,3'R,6'R,7'S,8'E,12'S)-6-chloro-12'-((2R)-2-hydroxypropyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-12'-((2R)-2-hydroxypropyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide To a 100 ml flask was added [(1S,3'R,6'R,7'S,8'E,12'S)-12'-((2R)-2-((tert-butyl(diphenyl)silyl)oxy)propyl)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-12'-((2R)-2-((tert-butyl(diphenyl)silyl)oxy)propyl)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (from Step 1) (38 mg, 0.044 mmol) and TBAF (1 M in THF, 3.27 ml, 3.27 μmol). The reaction was stirred at room temperature for 3 hours (No reaction observed by LCMS) at which time 0.2 ml of AcOH was added and the reaction was stirred at 65° C. for an additional 20 hours and then was quenched with 50 ml of brine and extracted with 200 ml of EtOAc. The organic layer was dried over sodium sulfate, filtered, the solvent was removed by rotary evaporation and the crude was purified on a Combiflash (12 gram gold silica column), eluting with 10% to 50% EtOAc in heptanes, to give the title compound (20 mg, 0.030 mmol, 70% yield) as an off white solid. $^1$H NMR (400 MHz, CDCl$_3$) δ 8.25 (s, 1H), 7.70 (d, J=8.4 Hz, 1H), 7.18 (dd, J=2.2, 8.5 Hz, 1H), 7.09 (d, J=2.2 Hz, 1H), 6.98-6.86 (m, 2H), 6.83 (s, 1H), 5.93-5.74 (m, 1H), 5.55 (dd, J=8.8, 15.3 Hz, 1H), 4.40-4.28 (m, 1H), 4.21-4.11 (m, 1H), 4.12-3.98 (m, 2H), 3.80 (d, J=14.9 Hz, 1H), 3.74-3.59 (m, 2H), 3.24 (s, 3H), 3.23-3.16 (m, 1H), 2.99 (dd, J=10.2, 15.3 Hz, 1H), 2.84-2.65 (m, 2H), 2.52-2.42 (m, 1H), 2.41-2.24 (m, 4H), 2.05-1.74 (m, 7H), 1.71-1.54 (m, 3H), 1.46-1.37 (m, 1H), 1.34 (d, J=6.1 Hz, 3H). m/z (ESI, +ve ion) 643.0 (M+H)$^+$.

Example 549. (1S,3'R,6'R,7'S,8'E,12'S)-6-chloro-7'-methoxy-12'-((2R)-2-methoxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-methoxy-12'-((2R)-2-methoxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

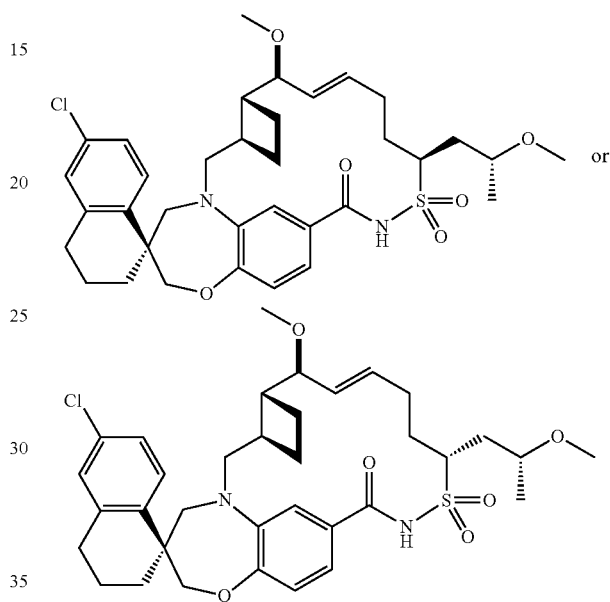

To a 100 ml flask was added [(1S,3'R,6'R,7'S,8'E,12'S)-6-chloro-12'-((2R)-2-hydroxypropyl)-7'-methoxy-3,4-dihydro-2h,15'h-spiro[naphthalene-1,22'-25 [20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-12'-((2R)-2-hydroxypropyl)-7'-methoxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (from Example 548) (10 mg, 0.016 mmol), THF (2 mL) and NaH (3.8 mg, 0.16 mmol). The reaction was stirred at room temperature for 15 minutes at which time MeI (0.020 mL, 0.32 mmol) was added. The reaction was stirred at room temperature for 3 hours and then the reaction was quenched with 100 ml of saturated ammonium chloride and extracted with 400 ml of EtOAc. The organic layer was dried over sodium sulfate, filtered, the solvent was removed by rotary evaporation, and the crude was purified on a Combiflash (4 gram gold silica column), eluting with 10% to 50% EtOAc in heptanes, to give the title compound (6.6 mg, 10 μmol, 63% yield) as a white film. $^1$H NMR (500 MHz, CDCl$_3$) δ 8.04 (s, 1H), 7.70 (d, J=8.6 Hz, 1H), 7.19 (dd, J=2.2, 8.3 Hz, 1H), 7.10 (d, J=2.0 Hz, 1H), 6.97-6.87 (m, 2H), 6.82 (d, J=1.5 Hz, 1H), 5.94-5.70 (m, 1H), 5.54 (dd, J=8.8, 15.2 Hz, 1H), 4.36 (dd, J=4.9, 8.3 Hz, 1H), 4.16-3.97 (m, 2H), 3.81 (d, J=15.2 Hz, 1H), 3.76-3.61 (m, 3H), 3.37-3.30 (m, 3H), 3.24 (s, 3H), 3.24-3.18 (m, 1H), 3.00 (dd, J=10.3, 15.2 Hz, 1H), 2.85-2.66 (m, 2H), 2.46-2.41 (m, 1H), 2.39-2.24 (m, 3H), 2.07-1.75 (m, 9H), 1.69-1.62 (m, 2H), 1.39 (t, J=12.8 Hz, 1H), 1.2 7 (d, J=5.9 Hz, 3H) m/z (ESI, +ve ion) 657.0 (M+H)$^+$.

Example 550. (1S,3'R,6'R,7'S,8'Z,12'S)-6-chloro-7'-hydroxy-12'-((2R)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'R)-6-chloro-7'-hydroxy-12'-((2R)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

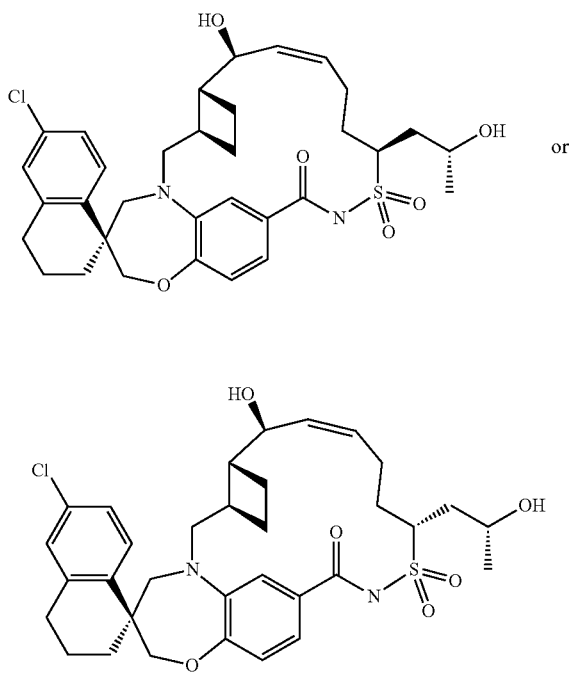

Step 1: (1S,3'R,6'R,7'S,8'Z,12'S)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'R)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

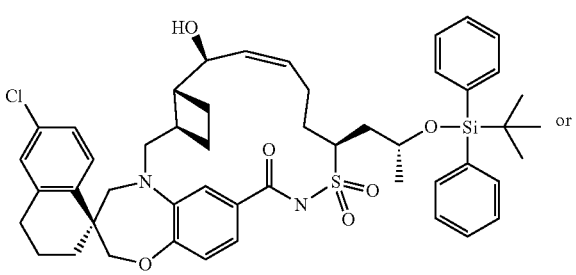

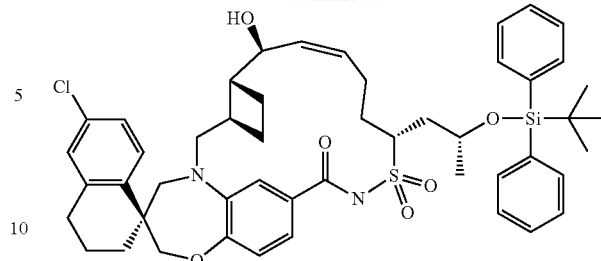

To a 100 ml flask was added [(S)—N-(((2R,4S)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(((2R,4R)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide] (from Example 539, Step 3) (57 mg, 0.061 mmol) and DCM (40 ml). The mixture was stirred at room temperature while argon was bubbled through the reaction mixture for 15 minutes. To the homogeneous solution was then added Hoveyda-Grubbs II (3.8 mg, 6.1 μmol) and the mixture was stirred to 45° C. for 6 hours. The reaction mixture was filtered, concentrated and the crude product was purified on a Combiflash (12 g gold silica column), eluting with 10%-40% EtOAc in heptanes+0.2% AcOH, to give [(1S,3'R,6'R,7'S,8'Z,12'S)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'R)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (16 mg, 0.018 mmol, 30% yield) as the slower eluting olefin isomer as a white solids.

Step 2: (1S,3'R,6'R,7'S,8'Z,12'S)-6-chloro-7'-hydroxy-12'-((2R)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'R)-6-chloro-7'-hydroxy-12'-((2R)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide To a 100 ml flask was added [(1S,3'R,6'R,7'S,8'Z,12'S)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,12'R)-12'-((2R)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (from Step 1) (14 mg, 16 μmol) and TBAF (1 M in THF, 2.02 ml, 2.02 mmol). The reaction was stirred at 65° C. for 3.5 hours at which time the reaction was quenched with 50 ml of brine and extracted with 200 ml of EtOAc. The organic layer was dried over sodium sulfate, filtered and the solvent was removed by rotary evaporation. The crude product was purified on a Combiflash (4 g gold silica column), eluting with 50% to 90% EtOAc in heptanes+0.2% AcOH, to give the title compound (3.7 mg, 5.9 μmol, 36% yield) as an off white solid. ¹H NMR (400 MHz, MeOH) δ 7.75 (d, J=8.4 Hz, 1H), 7.81-7.70 (m, 1H), 7.27-7.06 (m, 3H), 7.03-6.90 (m, 2H), 5.73-5.50 (m, 2H), 4.63 (dd, J=2.5, 9.0 Hz, 1H), 4.22-4.04 (m, 4H), 4.00-3.87 (m, 1H), 3.74 (d, J=14.7 Hz, 1H), 3.49-3.36 (m, 1H), 3.30-3.16 (m, 1H), 2.96-2.72 (m, 3H), 2.50-2.32 (m, 1H), 2.32-1.78 (m, 11H), 1.65 (ddd, J=6.1, 8.7, 14.6 Hz, 1H), 1.53-1.43 (m, 1H), 1.27 (d, J=6.3 Hz, 4H). m/z (ESI, +ve ion) 629.0 (M+H)⁺.

Example 551. (1S,3'R,6'R,7'S,8'E,12'R)-6-chloro-7'-hydroxy-12'-((2S)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-6-chloro-7'-hydroxy-12'-((2S)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

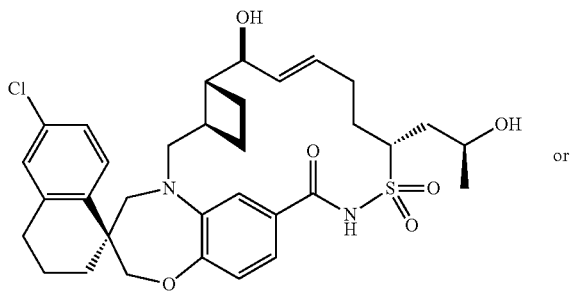

or

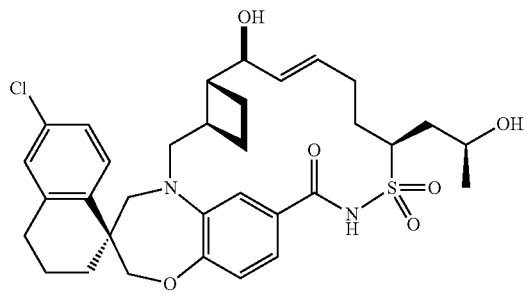

Step 1: (2S,4R)-2-((tert-butyldiphenylsilyl)oxy)-N,N-bis(4-methoxybenzyl)oct-7-ene-4-sulfonamide or (2S,4S)-2-((tert-butyldiphenylsilyl)oxy)-N,N-bis(4-methoxybenzyl)oct-7-ene-4-sulfonamide

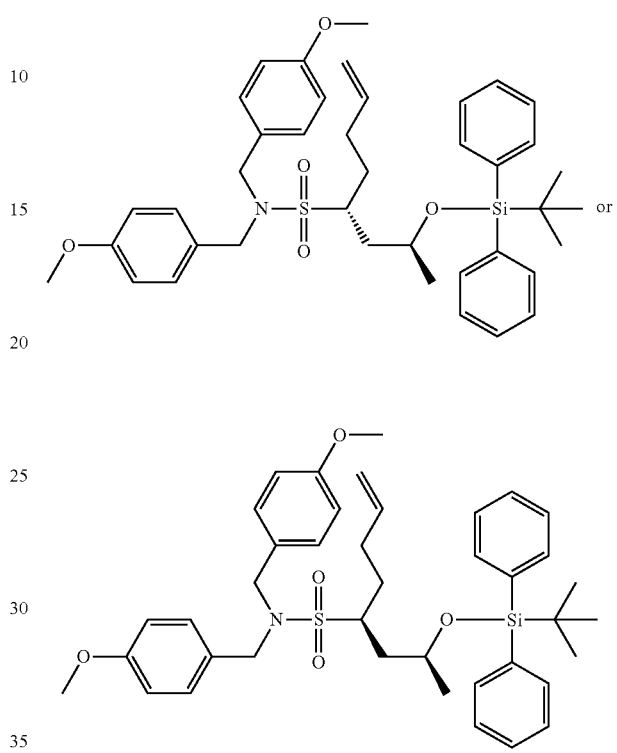

To a 100 ml flask was added [(2S,4S)-2-hydroxy-n,n-bis(4-methoxybenzyl)oct-7-ene-4-sulfonamide and (2S,4R)-2-hydroxy-n,n-bis(4-methoxybenzyl)oct-7-ene-4-sulfonamide] (from 546, Step 1) (3.88 g, 8.67 mmol), DMF (60 ml), imidazole (1.18 g, 17.3 mmol) and tert-butylchlorodiphenylsilane (3.38 ml, 13.0 mmol). The reaction was stirred at 65° C. for 16 hours at which time reaction was then quenched with 200 ml of saturated ammonium chloride and extracted with 600 ml of diethyl ether. The organic layer was dried over sodium sulfate, filtered and the solvent removed by rotary evaporation. The crude product was first purified on a Combiflash (80 g gold silica column), eluting with 10% to 30% EtOAc in heptanes. Rf product=0.19 eluting with 10% EtOAc in heptanes. The racemic mixture (1:1) was then purified by preparatory SCF chromatography (Chiralpak AD 250 mm×30 mm column, Phenomenex, Torrance, CA; 16 g/minute EtOH+(20 mM Ammonia)+64 g/minute CO₂ (20% co-solvent) on Thar 80 SFC; outlet pressure=100 bar; temperature=22° C.; wavelength=220 nm; used 1.0 mL injections of 3647 mg/41 mL (89 mg/mL) sample solution of MeOH (35 mL) and DCM (5 mL); run time=13 minutes & cycle time 10 minutes.) to provide [(2S,4R)-2-((tert-butyldiphenylsilyl)oxy)-N,N-bis(4-methoxybenzyl)oct-7-ene-4-sulfonamide or (2S,4S)-2-((tert-butyldiphenylsilyl)oxy)-N,N-bis(4-methoxybenzyl)oct-7-ene-4-sulfonamide](1761 mg, 2.57 mmol, 37% yield) as the slower eluting isomer as a yellow liquid (t$_R$=2.34 minutes on analytical SFC; AD-H column; 15% EtOH in CO₂).

Step 2: (2S,4R)-2-((tert-butyldiphenylsilyl)oxy)oct-7-ene-4-sulfonamide or (2S,4S)-2-((tert-butyldiphenylsilyl)oxy)oct-7-ene-4-sulfonamide

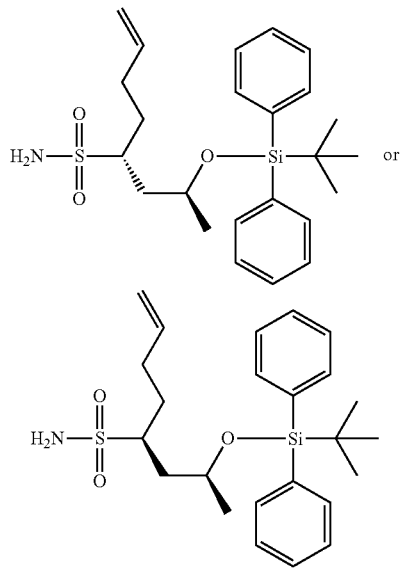

To a 100 ml flask was added [(2S,4R)-2-((tert-butyldiphenylsilyl)oxy)-N,N-bis(4-methoxybenzyl)oct-7-ene-4-sulfonamide or (2S,4S)-2-((tert-butyldiphenylsilyl)oxy)-N,N-bis(4-methoxybenzyl)oct-7-ene-4-sulfonamide](from Step 1) (450 mg, 0.656 mmol), anisole (0.717 ml, 6.56 mmol), DCM (20 ml) and then TFA (5 ml). The reaction was stirred at 22° C. for 3 hours at which time the solvent was removed. The crude product was purified on a Combiflash (24 g gold silica column), eluting with 10% to 50% EtOAc in heptanes, to give [(2S,4R)-2-((tert-butyldiphenylsilyl)oxy)oct-7-ene-4-sulfonamide or (2S,4S)-2-((tert-butyldiphenylsilyl)oxy)oct-7-ene-4-sulfonamide] (137 mg, 0.307 mmol, 47% yield) as a light yellow oil.

Step 3: (S)—N-(((2S,4R)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(((2S,4S)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide

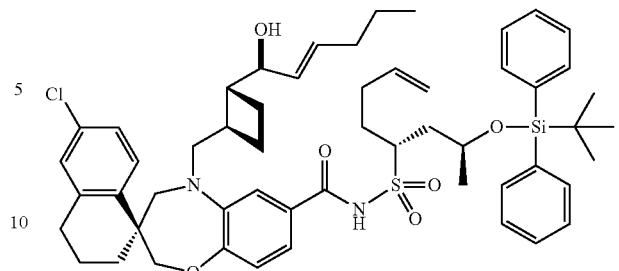

To a 100 ml flask was added (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (from Intermediate AA12A) (50 mg, 0.098 mmol), N,N-dimethylpyridin-4-amine (24 mg, 0.20 mmol) and [(2S,4R)-2-((tert-butyldiphenylsilyl)oxy)oct-7-ene-4-sulfonamide or (2S,4S)-2-((tert-butyldiphenylsilyl)oxy)oct-7-ene-4-sulfonamide](from Step 2) (131 mg, 0.294 mmol) and then N-(3-dimethylaminopropyl)-N'-ethylcarbodiimide hydrochloride (38 mg, 0.20 mmol). The reaction was stirred at room temperature for 16 hours at which time the solvent was removed and the crude product was purified on a Combiflash (12 g gold silica column), eluting with 2%-10% EtOAc in heptanes+0.2% AcOH, to give [(S)—N-(((2S,4R)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(((2S,4S)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide] (55 mg, 0.058 mmol, 59% yield) as a thick yellow oil.

Step 4: (1S,3'R,6'R,7'S,8'E,12'R)-12'-((2S)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] or (1S,3'R,6'R,7'S,8'E,12'S)-12'-((2S)-2-((tert-butyl(diphenyl)silyl)oxy)propyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide]

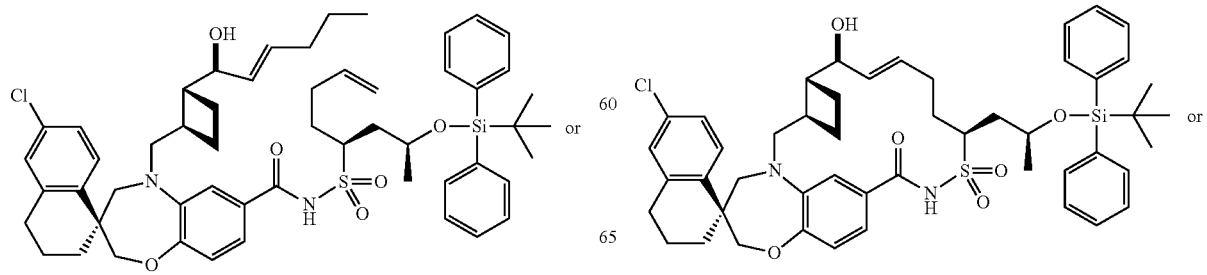

-continued

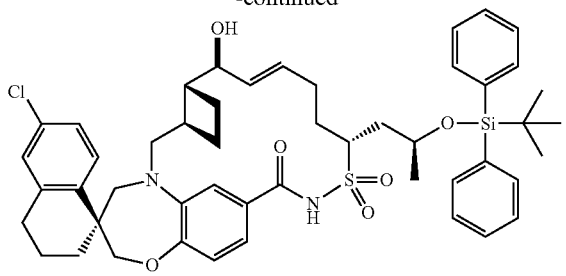

To a 100 ml flask was added [(S)—N-(((2S,4R)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(((2S,4S)-2-((tert-butyldiphenylsilyl)oxy)oct-7-en-4-yl)sulfonyl)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide] (from Step 3) (55 mg, 0.59 mmol) and DCM (40 ml). The mixture was stirred at room temperature while argon was bubbled through the reaction mixture for 15 minutes. To the homogeneous solution was then added Hoveyda-Grubbs II (7.4 mg, 0.012 mmol) and the mixture was stirred to 45° C. for 6 hours. The reaction mixture was then filtered, concentrated and the crude product was purified on a Combiflash (12 g gold silica column), eluting with 10%-40% EtOAc in heptanes+0.2% AcOH, to give [(1S,3'R,6'R,7'S,8'E,12'R)-12'-((2S)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] or (1S,3'R,6'R,7'S,8'E,12'S)-12'-((2S)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (14 mg, 0.016 mmol, 27% yield) as the faster eluting olefin isomer, as a white solids.

Step 5: (1S,3'R,6'R,7'S,8'E,12'R)-6-chloro-7'-hydroxy-12'-((2S)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'S)-6-chloro-7'-hydroxy-12'-((2S)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide To a 100 ml flask was added [(1S,3'R,6'R,7'S,8'E,12'R)-12'-((2S)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] or (1S,3'R,6'R,7'S,8'E,12'S)-12'-((2S)-2-((tert-butyl(diphenyl)silyl)oxy)propyl)-6-chloro-7'-hydroxy-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (from Step 4) (13 mg, 0.015 mmol) and TBAF (1 M in THF, 3.04 ml, 3.04 mmol). The reaction was stirred at 65° C. for 3 hours at which time the reaction was quenched with 50 ml of brine and extracted with 200 ml of EtOAc. The organic layer was dried over sodium sulfate, filtered, the solvent was removed by rotary evaporation, and the crude product was purified on a Combiflash (4 g gold silica column), eluting with 50% to 90% EtOAc in heptanes) to give the title compound (1.7 mg, 2.7 µmol, 18% yield) as an off white solid. $^1$H NMR (400 MHz, CDCl$_3$) δ 8.23 (br. s., 1H), 7.65 (d, J=8.4 Hz, 1H), 7.54 (d, J=8.4 Hz, 1H), 7.16 (dd, J=2.3, 8.4 Hz, 1H), 7.11 (d, J=2.2 Hz, 1H), 7.00-6.82 (m, 2H), 5.74 (dd, J=4.9, 15.8 Hz, 1H), 5.66-5.46 (m., 1H), 4.29-4.07 (m, 4H), 4.00-3.88 (m, 2H), 3.64 (d, J=14.7 Hz, 1H), 3.30 (d, J=13.5 Hz, 1H), 3.13 (d, J=13.7 Hz, 1H), 2.78-2.73 (m, 2H), 2.65-2.47 (m, 2H), 2.26 (ddd, J=5.8, 8.8, 14.6 Hz, 2H), 2.03 (s, 2H), 1.89-1.60 (m, 9H), 1.39 (d, J=7.6 Hz, 1H), 1.28 (d, J=6.1 Hz, 3H). m/z (ESI, +ve ion) 628.9 (M+H)$^+$.

Example 552. (1S,3'R,6'R,7'S,8'E,12'S)-6-chloro-7'-methoxy-12'-((2S)-2-methoxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-methoxy-12'-((2S)-2-methoxypropyl)-3,4-dihydro-2H,15'H-spiro[naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide

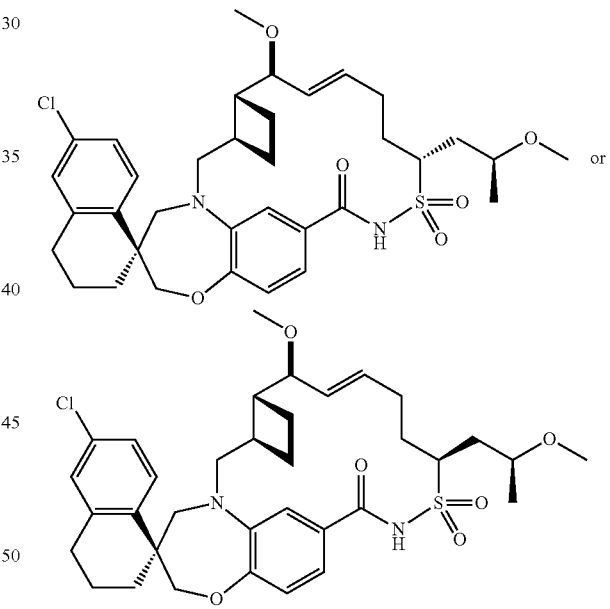

To a 4 ml vial containing 2 mg of [(1S,3'R,6'R,7'S,8'E,12'S)-6-chloro-7'-hydroxy-12'-((2S)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-7'-hydroxy-12'-((2S)-2-hydroxypropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide] (from Example 546) was added 1 ml of DMF and NaH (3.7 mg, 0.15 mmol). The reaction was stirred at room temperature for 15 minutes at which time MeI (4.8 µl, 0.076 mmol) was added and stirred for 2 hours. The reaction was then quenched with 10 ml of brine and extracted with 40 ml of EtOAc. The organic layer was dried over sodium sulfate, filtered and the solvent was removed by rotary evaporation. The crude product was purified on a Combiflash (4 g gold silica column), eluting with 50% to 90% EtOAc in heptanes, to give the title compound (2.0 mg, 3.0 μmol, 32% yield) as a white film. $^1$H NMR (400 MHz, CDCl$_3$) δ 7.94 (s, 1H), 7.70 (d, J=8.4 Hz, 1H), 7.19 (dd, J=2.3, 8.6 Hz, 1H), 7.10 (d, J=2.2 Hz, 1H), 6.97-6.80 (m, 3H), 5.98-5.78 (m, 1H), 5.53 (dd, J=9.1, 15.4 Hz, 1H), 4.46 (t, J=9.4 Hz, 1H), 4.09 (d, J=1.6 Hz, 2H), 3.88-3.62 (m, 4H), 3.49-3.38 (m, 3H), 3.27-3.21 (m, 1H), 3.24 (s, 3H), 2.99 (dd, J=10.3, 15.4 Hz, 1H), 2.86-2.66 (m, 2H), 2.52-2.41 (m, 1H), 2.40-2.19 (m, 4H), 2.04-1.61 (m, 10H), 1.46-1.35 (m, 1H), 1.22 (d, J=6.1 Hz, 3H). m/z (ESI, +ve ion) 657.0 (M+H)$^+$.

Example 553. (1S,3'R,6'R,7'S,9'E,13'R)-6-chloro-13'-ethyl-7'-hydroxy-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide

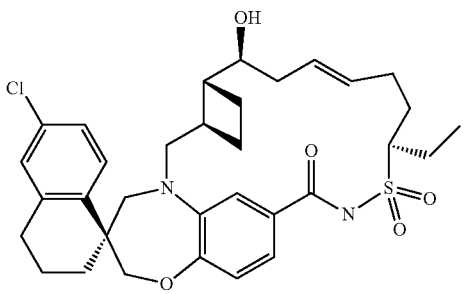 [SMILES: CC[C@@H]1CC/C=C/C[C@H](O)[C@@H]2CC[C@H]2CN2C[C@@]3(CCCc4cc(Cl)ccc43)COc3ccc(cc32)C(=O)NS1(=O)=O]

Step 1: (S)-6'-chloro-N—((R)-hept-6-en-3-ylsulfonyl)-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide

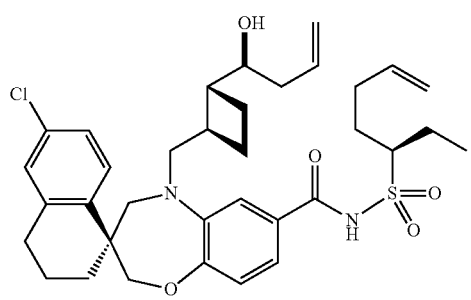

To a 100 ml flask was added (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (from Intermediate AA13A) (72 mg, 0.15 mmol), N,N-dimethylpyridin-4-amine (37 mg, 0.30 mmol), (R)-hept-6-ene-3-sulfonamide (from Intermediate EE18)(79 mg, 0.45 mmol), DCM (5 ml) and then N-(3-dimethylaminopropyl)-N'-ethylcarbodiimide hydrochloride (57 mg, 0.30 mmol). The reaction was stirred at room temperature for 16 hours at which time the solvent was removed and the crude product was purified on a Combiflash (12 g gold silica column), eluting with 2%-10% EtOAc in heptanes, to give (S)-6'-chloro-N—((R)-hept-6-en-3-ylsulfonyl)-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide (90 mg, 0.14 mmol, 94% yield) as a white solid.

Step 2: (1S,3'R,6'R,7'S,9'E,13'R)-6-chloro-13'-ethyl-7'-hydroxy-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide To a 200 ml flask was added (S)-6'-chloro-N—((R)-hept-6-en-3-ylsulfonyl)-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide (from Step 1) (90 mg, 0.14 mmol) and DCM (100 ml). The mixture was stirred at room temperature and argon was through bubbled through the reaction mixture for 15 minutes. To the homogeneous solution was then added Hoveyda-Grubbs II (8.8 mg, 0.014 mmol, as a 200 uL solution in DCM) and the mixture was stirred to 45° C. for 6 hours. The reaction mixture was concentrated and crude product was purified on a Combiflash (12 g gold silica column), eluting with 10%-40% EtOAc in heptanes+0.2% AcOH, to give the title compound (33 mg, 0.054 mmol, 38% yield) as a off white solid. $^1$H NMR (400 MHz, CDCl$_3$) δ 9.33 (s, 1H), 7.72 (d, J=8.4 Hz, 1H), 7.32 (dd, J=2.1, 8.3 Hz, 1H), 7.25-7.15 (m, 2H), 7.10 (d, J=2.0 Hz, 1H), 6.97 (d, J=8.2 Hz, 1H), 5.54-5.45 (m, 1H), 5.44-5.36 (m, 1H), 4.26-4.02 (m, 2H), 3.97-3.89 (m, 1H), 3.84-3.58 (m, 3H), 3.34-3.11 (m, 2H), 2.84-2.74 (m, 2H), 2.72-2.62 (m, 1H), 2.43-2.31 (m, 1H), 2.29-2.10 (m, 4H), 2.06-1.88 (m, 6H), 1.85-1.69 (m, 3H), 1.68-1.42 (m, 3H), 1.15 (t, J=7.4 Hz, 3H). m/z (ESI, +ve ion) 613.0 (M+H)$^+$.

Example 554. (1S,3'R,6'R,7'S,13'R)-6-chloro-13'-ethyl-7'-hydroxy-3,4-dihydro-2H,16'H-spiro[naphthalene-1,23'-[21]oxa[14]thia[1,15]diazatetracyclo[15.7.2.0$^{3,6}$.0$^{20,25}$]hexacosa[17,19,25]trien]-16'-one 14',14'-dioxide

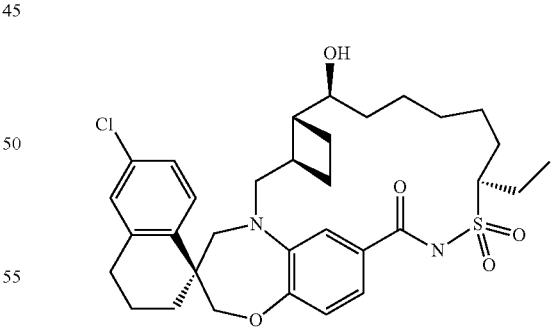

A 100 ml flask was charged with (1S,3'R,6'R,7'S,9'E,13'R)-6-chloro-13'-ethyl-7'-hydroxy-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide (from Example 553) (30 mg, 0.050 mmol), 20 ml of EtOAc, and 11 mg of platinum(IV) oxide. The mixture was degassed by H$_2$ three times at which time the reaction was stirred at room temperature under a hydrogen balloon for 3.0 hrs. The reaction was then filtered and the solvent was removed by rotary evaporation. The crude was purified by reversed phase preparatory HPLC (Gemini™ Prep C$_{18}$ 5 μm column; Phenomenex, Torrance, CA; gradient elution of 10% to 90% MeCN in water, where both solvents contain 0.1% TFA, 45 minute method) to give the title compound (6.7 mg, 11 μmol, 22% yield) as a clear film. $^1$H NMR (400 MHz, CDCl$_3$) δ 9.99 (br. s., 1H), 7.67 (d, J=8.4 Hz, 1H), 7.41 (dd, J=1.8, 8.2 Hz, 1H), 7.32 (s, 1H), 7.17 (dd, J=2.2, 8.5 Hz, 1H), 7.09 (d, J=2.2 Hz, 1H), 6.98 (d, J=8.2 Hz, 1H), 4.21-4.11 (m, 2H), 3.70 (d, J=5.1 Hz, 2H), 3.61-3.37 (m, 4H), 2.83-2.70 (m, 2H), 2.58-2.49 (m, 1H), 2.33-2.22 (m, 1H), 2.22-2.12 (m, 1H), 2.01-1.70 (m, 9H), 1.66-1.51 (m, 4H), 1.49-1.43 (m, 4H), 1.35-1.25 (m, 2H), 1.19-1.06 (m, 3H). m/z (ESI, +ve ion) 615.0 (M+H)$^+$.

Example 555. (1S,3'R,6'R,7'S,9'E,12'S,13'R)-6-chloro-7'-hydroxy-12',13'-dimethyl-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide or (1S,3'R,6'R,7'S,9'E,12'S,13'S)-6-chloro-7'-hydroxy-12',13'-dimethyl-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide

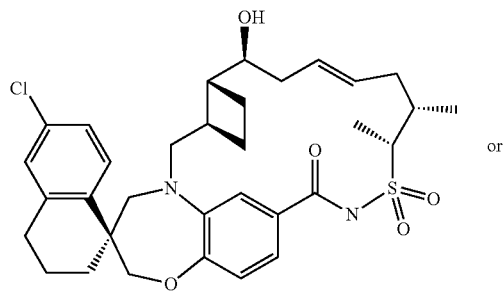

Step 1: (2R, 3S)—N,N-bis(4-methoxybenzyl)-3-methylhex-5-ene-2-sulfonamide or (2S, 3S)—N,N-bis(4-methoxybenzyl)-3-methylhex-5-ene-2-sulfonamide

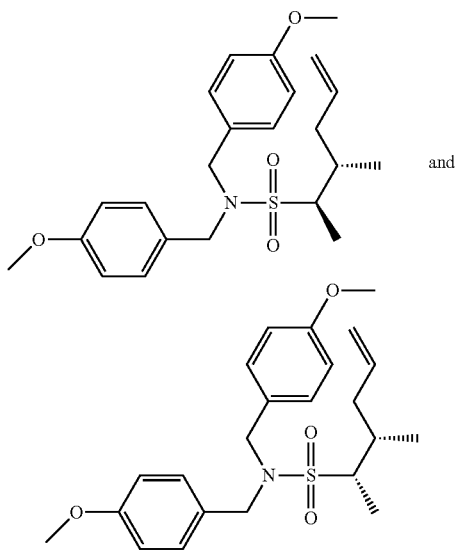

To a −78° C. solution of (S)—N,N-bis(4-methoxybenzyl)-2-methylpent-4-ene-1-sulfonamide (from Example 395, Step 3) (334 mg, 0.828 mmol) in THF (5 mL) under argon was added butyllithium (0.828 ml, 2.07 mmol) over 5 minutes (reaction turns bright pink). The mixture was stirred at −78° C. for 5 minutes at which time MeI (0.155 ml, 2.48 mmol) was added and stirred at 0° C. for 2 hours. The reaction was then quenched with 100 ml of saturated ammonium chloride and extracted with 300 ml of EtOAc. The organic layer was dried over sodium sulfate, filtered and the solvent removed by rotary evaporation. The crude product was purified on a Combiflash (12 g gold silica column), eluting with 2% to 10% EtOAc in heptanes, to give [(2R, 3S)—N,N-bis(4-methoxybenzyl)-3-methylhex-5-ene-2-sulfonamide and (2S, 3S)—N,N-bis(4-methoxybenzyl)-3-methylhex-5-ene-2-sulfonamide] (185 mg, 0.443 mmol, 534% yield) as a light yellow oils.

Step 2: (2R, 3S)-3-methylhex-5-ene-2-sulfonamide and (2S, 3S)-3-methylhex-5-ene-2-sulfonamide

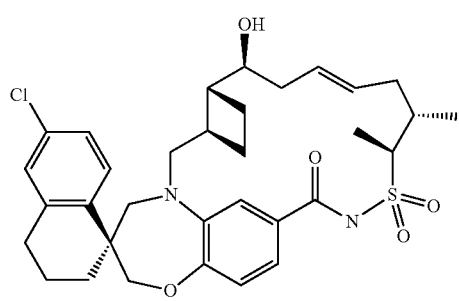

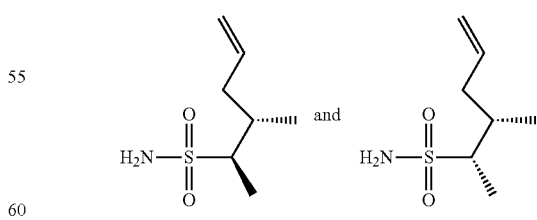

To a 100 ml flask was added [(2R, 3S)—N,N-bis(4-methoxybenzyl)-3-methylhex-5-ene-2-sulfonamide and (2S, 3S)—N,N-bis(4-methoxybenzyl)-3-methylhex-5-ene-2-sulfonamide)](from Step 1)(185 mg, 0.443 mmol), anisole (0.484 ml, 4.43 mmol), DCM (8 ml) and then TFA (4 ml). The reaction was stirred at 22° C. for 6 hours at which time the solvent was removed. The crude product was purified on a Combiflash (12 g gold silica column), eluting with 10% to 50% EtOAc in heptanes, to give [(2R, 3S)-3-methylhex-5-ene-2-sulfonamide and (2S, 3S)-3-methylhex-5-ene-2-sulfonamide] (63 mg, 0.36 mmol, 80% yield) as a light yellow oil. Note: the desired peak off of Combiflash look very small compared to undesired peaks. Note: Use KMNO₄ stain to visualize product after chromatography.

Step 3: (S)-6'-chloro-5-(((1R,2R)-2-((S)-1-hydroxy-but-3-en-1-yl)cyclobutyl)methyl)-N-(((2R,3S)-3-methylhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxybut-3-en-1-yl)cyclobutyl)methyl)-N-(((2S,3S)-3-methylhex-5-en-2-yl)sulfonyl)-3',4,4',5-tetrahydro-2H,2'H-spiro[benzo[b][1,4]oxazepine-3,1'-naphthalene]-7-carboxamide

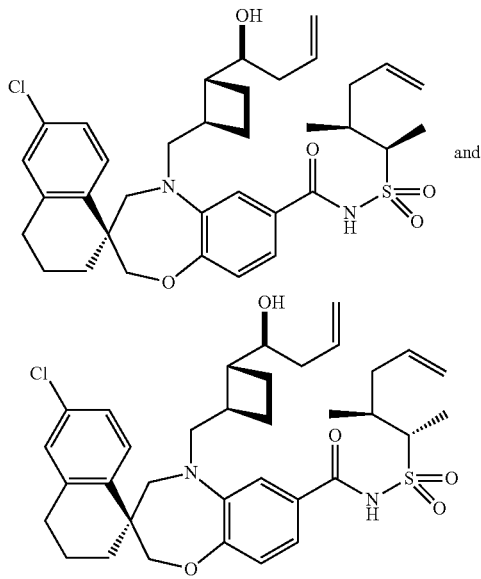

To a 100 ml flask was added (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (71 mg, 0.15 mmol, Intermediate AA13A), [(2R, 3S)-3-methylhex-5-ene-2-sulfonamide and (2S, 3S)-3-methylhex-5-ene-2-sulfonamide] (57 mg, 0.32 mmol), N,N-dimethylpyridin-4-amine (36 mg, 0.30 mmol), 3 ml of DCM and then N-(3-dimethylaminopropyl)-N'-ethylcarbodiimide hydrochloride (57 mg, 0.30 mmol). The reaction was stirred at room temperature for 16 hours at which time the reaction was quenched with 50 ml of 1 N HCl and extracted with 200 ml of EtOAc. The organic layer was dried over sodium sulfate, filtered and the solvent was removed by rotary evaporation. The crude product was purified on a Combiflash (12 g gold silica column), eluting with 10%-40% EtOAc in heptanes+0.2% AcOH to give [(S)-6'-chloro-5-(((1R,2R)-2-((S)-1-hydroxybut-3-en-1-yl)cyclobutyl)methyl)-N-(((2R,3S)-3-methylhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxybut-3-en-1-yl)cyclobutyl)methyl)-N-(((2S,3S)-3-methylhex-5-en-2-yl)sulfonyl)-3',4,4',5-tetrahydro-2H,2'H-spiro[benzo[b][1,4]oxazepine-3,1'-naphthalene]-7-carboxamide] (63 mg, 0.098 mmol, 67% yield) as a thick yellow oil.

Step 4: (1S,3'R,6'R,7'S,9'E,12'S,13'R)-6-chloro-7'-hydroxy-12',13'-dimethyl-3,4-dihydro-2H,16'H-spiro[naphthalene-1,23'-[21]oxa[14]thia[1,15]diazatetracyclo[15.7.2.0³,⁶.0²⁰,²⁵]hexacosa[9,17,19,25]tetraen]-16'-one 14',14'-dioxide or (1S,3'R,6'R,7'S,9'E,12'S,13'S)-6-chloro-7'-hydroxy-12',13'-dimethyl-3,4-dihydro-2H,16'H-spiro[naphthalene-1,23'-[21]oxa[14]thia[1,15]diazatetracyclo[15.7.2.0³,⁶.0²⁰,²⁵]hexacosa[9,17,19,25]tetraen]-16'-one 14',14'-dioxide To a 200 ml flask was added [(S)-6'-chloro-5-(((1R,2R)-2-((S)-1-hydroxybut-3-en-1-yl)cyclobutyl)methyl)-N-(((2R,3S)-3-methylhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxybut-3-en-1-yl)cyclobutyl)methyl)-N-(((2S, 3S)-3-methylhex-5-en-2-yl)sulfonyl)-3',4,4',5-tetrahydro-2H,2'H-spiro[benzo[b][1,4]oxazepine-3,1'-naphthalene]-7-carboxamide] (from Step 3) (63 mg, 0.098 mmol) and DCM (60 ml). The mixture was stirred at room temperature while argon was bubbled through the reaction mixture for 15 minutes. To the homogeneous solution was then added Hoveyda-Grubbs II (6.2 mg, 9.8 µmol) as a solution in DCM (0.2 ml) and the mixture was stirred at 45° C. for 6 hours. The reaction mixture was concentrated and crude product was purified on a Combiflash (12 g gold silica column), eluting with 10%-40% EtOAc in heptanes+0.2% AcOH, to give the title compound (15 mg, 0.024 mmol, 25% yield) as the slower eluting isomer, as an off white solids. ¹H NMR (400 MHz, CDCl₃) δ 8.41 (s, 1H), 7.72 (d, J=8.6 Hz, 1H), 7.32 (d, J=2.0 Hz, 1H), 7.18 (dd, J=2.3, 8.4 Hz, 1H), 7.09 (d, J=2.3 Hz, 1H), 7.06-7.00 (m, 1H), 6.93 (d, J=8.2 Hz, 1H), 5.65 (dd, J=5.9, 15.3 Hz, 1H), 5.40-5.13 (m, 1H), 4.25-4.01 (m, 3H), 3.84 (d, J=15.8 Hz, 2H), 3.68 (d, J=14.1 Hz, 1H), 3.24-3.04 (m, 2H), 2.86-2.61 (m, 2H), 2.44-2.38 (m, 1H), 2.34-2.23 (m, 1H), 2.23-1.97 (m, 6H), 1.96-1.61 (m, 6H), 1.49-1.40 (m, 1H), 1.45 (d, J=7.2 Hz, 3H), 1.11 (d, J=7.0 Hz, 3H). m/z (ESI, +ve ion) 613.0 (M+H)⁺.

Example 556. (1S,3'R,6'R,7'S,12'S,13'R)-6-chloro-7'-hydroxy-12',13'-dimethyl-3,4-dihydro-2H,16'H-spiro[naphthalene-1,23'-[21]oxa[14]thia[1,15]diazatetracyclo[15.7.2.0³,⁶.0²⁰,²⁵]hexacosa[17,19,25]trien]-16'-one 14',14'-dioxide or (1S,3'R,6'R,7'S,12'S,13'S)-6-chloro-7'-hydroxy-12',13'-dimethyl-3,4-dihydro-2H,16'H-spiro[naphthalene-1,23'-[21]oxa[14]thia[1,15]diazatetracyclo[15.7.2.0³,⁶.0²⁰,²⁵]hexacosa[17,19,25]trien]-16'-one 14',14'-dioxide

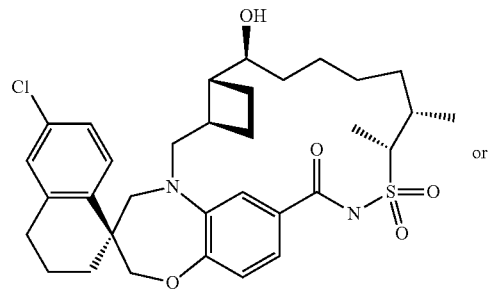

-continued

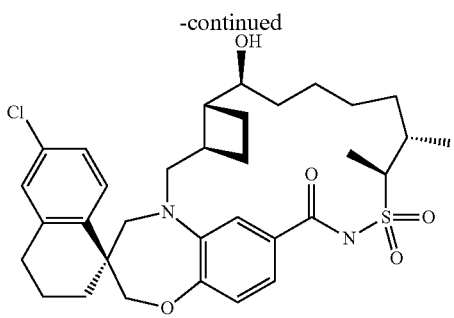

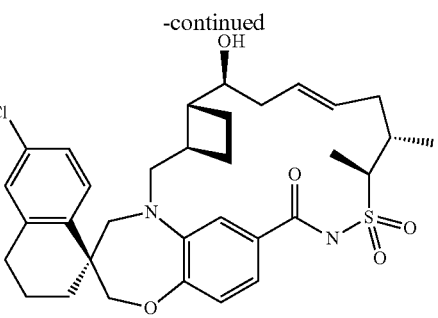

A 100 ml flask was charged with [(1S,3'R,6'R,7'S,9'E,12'S,13'R)-6-chloro-7'-hydroxy-12',13'-dimethyl-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide or (1S,3'R,6'R,7'S,9'E,12'S,13'S)-6-chloro-7'-hydroxy-12',13'-dimethyl-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide] (from Example 555) (13 mg, 0.021 mmol), 10 ml of EtOAc, and platinum(iv) oxide (4.8 mg, 0.021 mmol). The mixture was degassed by H$_2$ three times at which time the reaction was stirred at room temperature under a hydrogen balloon for 3.0 hrs. The reaction was then filtered and the solvent was removed by rotary evaporation. The crude product was purified on a Combiflash (4 g gold silica column), eluting with 10%-50% EtOAc in heptanes, to give the title compound (8.7 mg, 0.014 mmol, 67% yield) as a white solid. $^1$H NMR (400 MHz, CDCl$_3$) δ 8.49 (br. s., 1H), 7.62 (d, J=8.6 Hz, 1H), 7.17 (d, J=2.0 Hz, 1H), 7.11 (dd, J=2.3, 8.4 Hz, 1H), 7.05-6.93 (m, 2H), 6.87 (d, J=8.2 Hz, 1H), 4.04 (s, 2H), 3.95 (dq, J=2.9, 7.2 Hz, 1H), 3.73-3.51 (m, 3H), 3.19 (d, J=14.5 Hz, 1H), 3.11 (dd, J=7.2, 15.3 Hz, 1H), 2.80-2.55 (m, 2H), 2.35-2.17 (m, 2H), 2.06-1.89 (m, 3H), 1.88-1.59 (m, 5H), 1.39 (d, J=7.4 Hz, 3H), 1.39-1.30 (m, 6H), 1.28-1.20 (m, 3H), 0.95 (d, J=6.8 Hz, 3H). m/z (ESI, +ve ion) 615.0 (M+H)$^+$.

Example 557. (1S,3'R,6'R,7'S,9'E,12'S,13'S)-6-chloro-7'-hydroxy-12',13'-dimethyl-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide or (1S,3'R,6'R,7'S,9'E,12'S,13'R)-6-chloro-7'-hydroxy-12',13'-dimethyl-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide To a 200 ml flask was added [(S)-6'-chloro-5-(((1R,2R)-2-((S)-1-hydroxybut-3-en-1-yl)cyclobutyl)methyl)-N-(((2R,3S)-3-methylhex-5-en-2-yl)sulfonyl)-3',4,4',5-tetrahydro-2H,2'H-spiro[benzo[b][1,4]oxazepine-3,1'-naphthalene]-7-carboxamide and (1'S)-6'-chloro-5-(((1R,2R)-2-((S)-1-hydroxybut-3-en-1-yl)cyclobutyl)methyl)-N-(((2S,3S)-3-methylhex-5-en-2-yl)sulfonyl)-3',4,4',5-tetrahydro-2H,2'H-spiro[benzo[b][1,4]oxazepine-3,1'-naphthalene]-7-carboxamide] (Example 555, Step 3) (63 mg, 0.098 mmol) and DCM (60 ml). The mixture was stirred at room temperature while argon was bubbled through the reaction mixture for 15 minutes. To the homogeneous solution was then added Hoveyda-Grubbs II (6.16 mg, 9.82 µmol) as a solution in DCM (0.2 ml) and the mixture was stirred at 45° C. for 6 hours. The reaction mixture was concentrated and crude product was purified on a Combiflash (12 g gold silica column), eluting with 10%-40% EtOAc in heptanes+0.2% AcOH, to give the title compound (15 mg, 0.024 mmol, 25%) yield as the faster eluting isomer as an off white solids. $^1$H NMR (400 MHz, CDCl$_3$) δ 8.81 (br. s., 1H), 7.55-7.44 (m, 1H), 7.22 (d, J=2.0 Hz, 1H), 6.99 (dt, J=2.1, 8.2 Hz, 2H), 6.90 (d, J=2.2 Hz, 1H), 6.77 (d, J=8.2 Hz, 1H), 5.55-5.39 (m, 1H), 5.38-5.24 (m, 1H), 4.07-3.88 (m, 2H), 3.79-3.73 (m, 1H), 3.56-3.30 (m, 3H), 3.22-3.04 (m, 2H), 2.66-2.52 (m, 2H), 2.44 (br. s., 1H), 2.36-2.12 (m, 2H), 2.07-1.46 (m, 12H), 1.33 (d, J=7.2 Hz, 3H), 0.95-0.85 (m, 3H). m/z (ESI, +ve ion) 613.0 (M+H)$^+$.

Example 558. (1S,3'R,6'R,7'S,8'E,12'S)-6-chloro-7'-hydroxy-12'-(2-hydroxy-2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-7'-hydroxy-12'-(2-hydroxy-2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (Isomer 1)

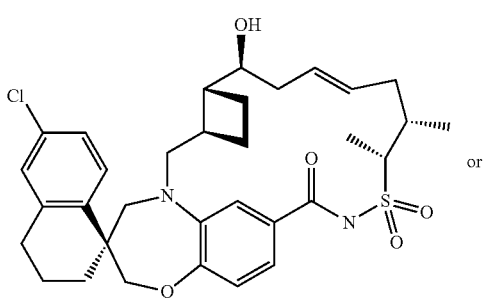

or

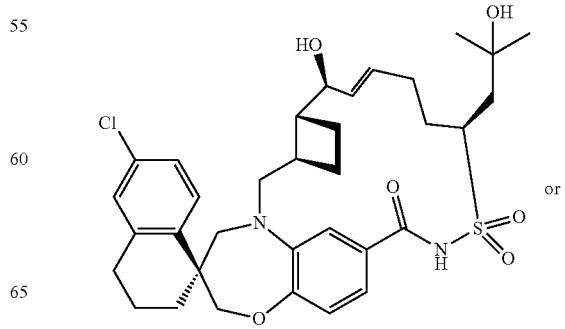

or

-continued

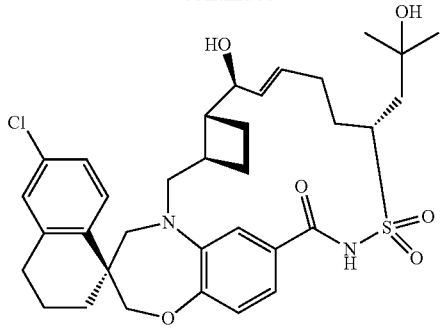

Step 1: (S)-2-hydroxy-N,N-bis(4-methoxybenzyl)-2-methyloct-7-ene-4-sulfonamide and and (R)-2-hydroxy-N,N-bis(4-methoxybenzyl)-2-methyloct-7-ene-4-sulfonamide

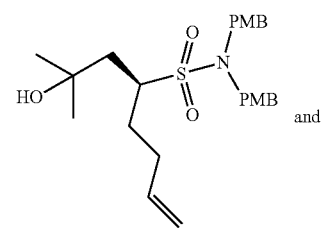

and

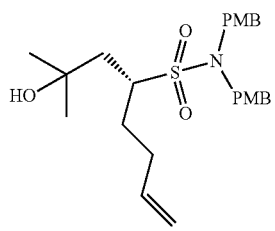

To a solution of N,N-bis(4-methoxybenzyl)pent-4-ene-1-sulfonamide (Intermediate EE19) (500 mg, 1.28 mmol) in THF (5 mL) was added n-BuLi (2.5 M solution in hexanes, 565 μL, 1.41 mmol) at −78° C. dropwise. After the reaction was stirred at −78° C. for 10 min, excess 1,2-epoxy-2-methylpropane was bubbled into the reaction at the same temp. The reaction was allowed to warm to ambient temperature and stirred for 2h. The reaction was quenched (saturated aqueous NH₄Cl), extracted (2×EtOAc), and washed (brine). The combined organic layers were dried (Na₂SO₄) and concentrated under reduced pressure. The residue was injected into a 24 g ISCO Gold column and purified by combi-flash, eluting with 15% to 30% EtOAc/hexanes to give the title compounds (411 mg, 0.890 mmol) as a colorless oil.

Step 2: (S)-2-hydroxy-2-methyloct-7-ene-4-sulfonamide and (R)-2-hydroxy-2-methyloct-7-ene-4-sulfonamide

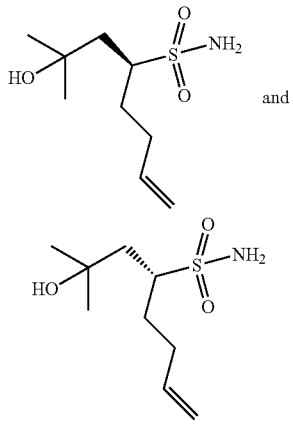

and

To a solution of (S)-2-hydroxy-N,N-bis(4-methoxybenzyl)-2-methyloct-7-ene-4-sulfonamide and and (R)-2-hydroxy-N,N-bis(4-methoxybenzyl)-2-methyloct-7-ene-4-sulfonamide (Step 1) (322 mg, 0.698 mmol) in DCM (4.6 mL) was added anisole (758 μL, 6.98 mmol) and TFA (1.55 mL, 20.9 mmol) at ambient temperature. After the reaction mixture was stirred for 40 hours, the reaction was concentrated and the residue was injected into a 20 g ISCO Gold column and purified by combi-flash, eluting with 10% to 100% EtOAc/hexanes to give the tile compounds (96 mg, 0.43 mmol, 62% yield) as a colorless film.

Step 3: (1S,3'R,6'R,7'S,8'E,12'S)-6-chloro-7'-hydroxy-12'-(2-hydroxy-2-methylpropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,12'R)-6-chloro-7'-hydroxy-12'-(2-hydroxy-2-methylpropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Isomer 1)

One of the title compounds (isomer 1) was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic Acid (Intermediate AA12A) by a procedure analogous to that described in Example 610, Steps 1 through 2, replacing (R)-hept-6-ene-3-sulfonamide in Step 1 with (S)-2-hydroxy-2-methyloct-7-ene-4-sulfonamide and (R)-2-hydroxy-2-methyloct-7-ene-4-sulfonamide (Example 558, Step 2). The crude product was purified by reversed phase preparatory HPLC (Gemini™ Prep $C_{18}$ 5 μm column; Phenomenex, Torrance, CA; gradient elution of 45% to 70% MeCN in water, where both solvents contain 0.1% TFA, 30 min method) to provide one of the title compounds as the faster eluting isomer as a white foam. ¹H NMR (400 MHz, CDCl₃) δ ppm 8.21 (br. s, 1H), 7.70 (d, J=8.6 Hz, 1H), 7.19 (dd, J=2.2, 8.5 Hz, 1H), 7.09 (d, J=2.2 Hz, 1H), 6.96-6.88 (m, 3H), 5.94-5.85 (m, 1H), 5.72 (dd, J=7.6, 15.3 Hz, 1H), 4.39 (m, 1H), 4.24 (dd, J=3.8, 7.5 Hz, 1H), 4.14-4.04 (m, 2H), 3.80 (d, J=14.9 Hz, 1H), 3.71 (d, J=14.3 Hz, 1H), 3.25 (d, J=14.3 Hz, 1H), 3.03 (dd, J=9.2, 15.3 Hz, 1H), 2.84-2.70 (m, 2H), 2.55-2.27 (m, 5H), 2.17-1.61 (m, 9H), 1.41 (s, 3H), 1.35 (s, 3H), 1.45-1.32 (m, 2H); m/z (ESI, +ve ion) 643.2 (M+H)+.

Example 559. (1S,3'R,6'R,7'S,8'E,12'S)-6-chloro-7'-hydroxy-12'-(2-hydroxy-2-methylpropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,12'R)-6-chloro-7'-hydroxy-12'-(2-hydroxy-2-methylpropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Isomer 2)

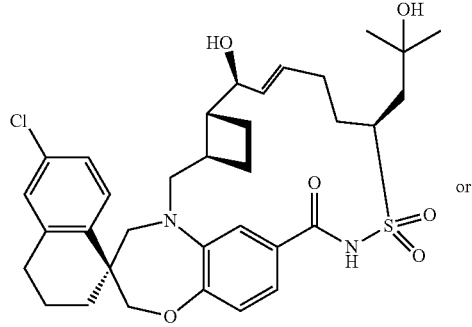

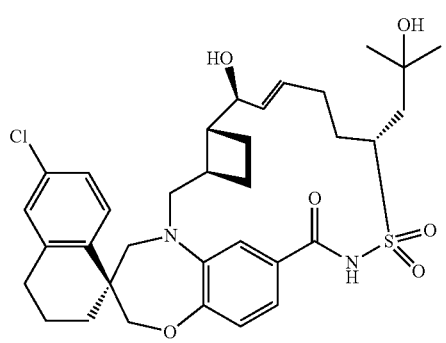

One of the title compounds (isomer 2) was obtained as the second (slower) eluting isomer from reversed phase preparatory HPLC purification in Example 558, Step 3. ¹H NMR (400 MHz, CDCl₃) δ ppm 9.70 (br. s, 1H), 7.71 (d, J=8.4 Hz, 1H), 7.36 (m, 1H), 7.19 (dd, J=2.2, 8.4 Hz, 1H), 7.09 (d, J=2.2 Hz, 1H), 6.98 (d, J=8.2 Hz, 1H), 6.92 (m, 1H), 5.73-5.62 (m, 1H), 5.59-5.47 (m, 1H), 4.59 (m, 1H), 4.14-4.03 (m, 3H), 3.96 (m, 1H), 3.72 (d, J=14.5 Hz, 1H), 3.25 (d, J=14.1 Hz, 1H), 3.11 (dd, J=10.0, 14.7 Hz, 1H), 2.84-2.69 (m, 3H), 2.47 (m, 1H), 2.33 (m, 2H), 2.28-1.68 (m, 10H), 1.42 (s, 3H), 1.38 (s, 3H), 1.49-1.27 (m, 2H); m/z (ESI, +ve ion) 643.2 (M+H)+.

Example 560. methyl 3-((1S,3'R,6'R,7'S,8'E,12'S)-6-chloro-7'-hydroxy-12'-methyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-12'-yl)propanoate or methyl 3-((1S,3'R,6'R,7'S,8'E,12'R)-6-chloro-7'-hydroxy-12'-methyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-12'-yl)propanoate (Isomer 1)

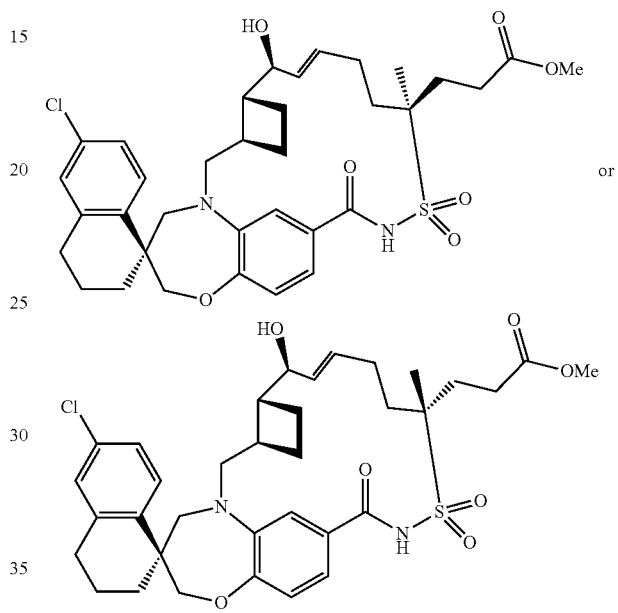

Step 1: (S)-1-((tert-butyldimethylsilyl)oxy)-N,N-bis(4-methoxybenzyl)oct-7-ene-4-sulfonamide and (R)-1-((tert-butyldimethylsilyl)oxy)-N,N-bis(4-methoxybenzyl)oct-7-ene-4-sulfonamide

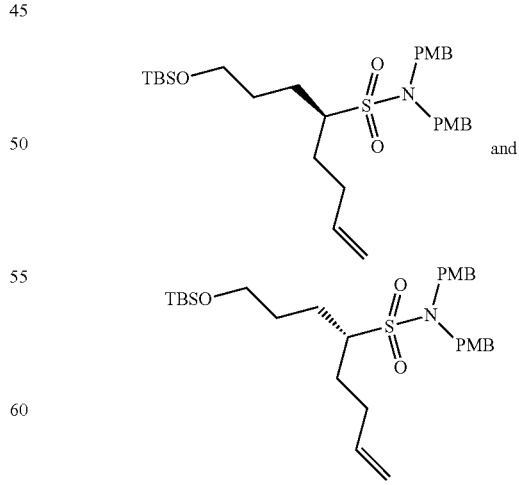

To a solution of N,N-bis(4-methoxybenzyl)pent-4-ene-1-sulfonamide (Intermediate EE19) (3.00 g, 7.70 mmol) in THF (17.1 mL) was added n-BuLi (2.5 M solution in hexanes, 3.70 mL, 9.24 mmol) at −78° C. After the reaction mixture was stirred for 5 min, tert-butyl(3-iodopropoxy)dimethylsilane (6.94 g, 23.1 mmol) was added at the same temperature. The reaction was stirred at −78° C. for 20 min and then allowed to warm to ambient temperature. After the reaction mixture was stirred at ambient temperature for 3h, the reaction was quenched (saturated aqueous NH₄Cl), extracted (2×EtOAc), and washed (brine). The combined organic layers were dried (Na₂SO₄) and concentrated under reduced pressure. The residue was injected into a 80 g ISCO Gold column and purified by combi-flash, eluting with 0% to 30% EtOAc/hexanes to give the title compounds (3.94 g, 7.01 mmol).

Step 2: (S)-1-((tert-butyldimethylsilyl)oxy)-N,N-bis(4-methoxybenzyl)-4-methyloct-7-ene-4-sulfonamide and (R)-1-((tert-butyldimethylsilyl)oxy)-N,N-bis(4-methoxybenzyl)-4-methyloct-7-ene-4-sulfonamide

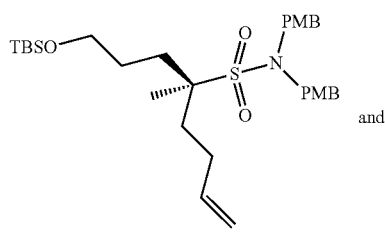

and

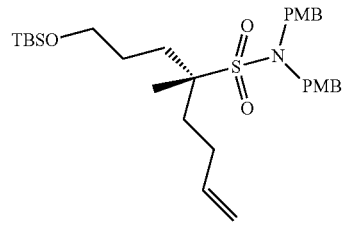

To a solution of (S)-1-((tert-butyldimethylsilyl)oxy)-N,N-bis(4-methoxybenzyl)oct-7-ene-4-sulfonamide and (R)-1-((tert-butyldimethylsilyl)oxy)-N,N-bis(4-methoxybenzyl)oct-7-ene-4-sulfonamide (Example 560, Step 1) (1.96 g, 3.49 mmol) in THF (12 mL) was added n-BuLi (2.5 M solution in hexanes, 1.53 mL, 3.84 mmol) at −78° C. After the reaction mixture was stirred at −78° C. for 3 min, iodomethane (0.65 mL, 11 mmol) was added. The resulting reaction was stirred for another 20 min at the same temperature, then allowed to warm to ambient temperature and stirred for 3 h. Then the reaction was quenched (saturated aqueous NH₄Cl), extracted (2×EtOAc), and washed (brine). The combined organic layers were dried (Na₂SO₄) and concentrated under reduced pressure. The residue was injected into a 80 g ISCO Gold column and purified by combi-flash, eluting with 0% to 20% EtOAc/hexanes to give the title compounds (1.45 g, 2.52 mmol) as a colorless oil Step 3: (S)-1-hydroxy-N,N-bis(4-methoxybenzyl)-4-methyloct-7-ene-4-sulfonamide and (R)-1-hydroxy-N,N-bis(4-methoxybenzyl)-4-methyloct-7-ene-4-sulfonamide

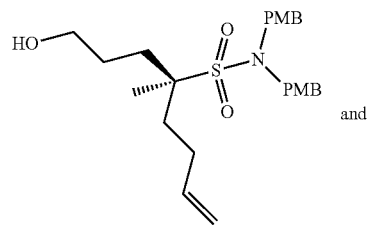

and

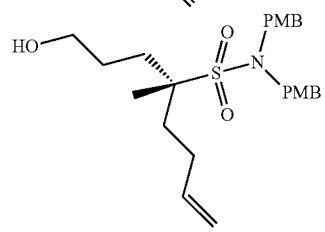

To a solution of (S)-1-((tert-butyldimethylsilyl)oxy)-N,N-bis(4-methoxybenzyl)-4-methyloct-7-ene-4-sulfonamide and (R)-1-((tert-butyldimethylsilyl)oxy)-N,N-bis(4-methoxybenzyl)-4-methyloct-7-ene-4-sulfonamide (Example 560, Step 2) (1.45 g, 2.52 mmol) in THF (12.6 mL) was added TBAF (1.0 M in THF, 6.29 mL, 6.29 mmol) at ambient temperature. After the reaction mixture was stirred for 24 h, the reaction was quenched (brine), extracted (2×EtOAc), and washed (1×brine). The combined organic layers were dried (Na₂SO₄) and concentrated under reduced pressure. The residue was injected into a 40 g ISCO Gold column and purified by combi-flash, eluting with 0% to 60% EtOAc/hexanes to give the title compounds (1.16 g, 2.51 mmol) as a colorless oil.

Step 4: (S)-4-(N,N-bis(4-methoxybenzyl)sulfamoyl)-4-methyloct-7-enoic Acid and (R)-4-(N,N-bis(4-methoxybenzyl)sulfamoyl)-4-methyloct-7-enoic Acid

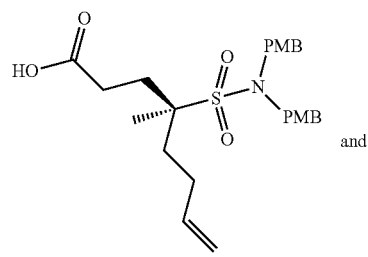

and

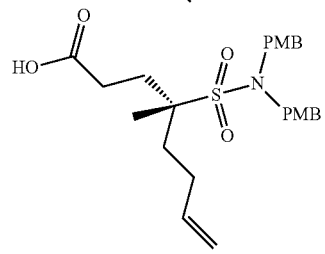

To a solution of (S)-1-hydroxy-N,N-bis(4-methoxybenzyl)-4-methyloct-7-ene-4-sulfonamide and (R)-1-hydroxy-N,N-bis(4-methoxybenzyl)-4-methyloct-7-ene-4-sulfonamide (Example 560, Step 3) (1.07 g, 2.32 mmol) in acetone (23 mL) were added KBr (0.028 g, 0.23 mmol), NaHCO₃ (5% w/w aqueous solution, 10.9 mL, 6.49 mmol), TEMPO (0.398 g, 2.55 mmol), and NaClO (6% w/w aqueous solution, 3.17 mL, 2.55 mmol) at 0° C. and the resulting mixture was stirred at the same temp for 2 h. Then the reaction was concentrated under reduced pressure, diluted (EtOAc and ice-cold 1N aqueous HCl), extracted (2×EtOAc), and washed (brine). The combined organic layers were dried (Na₂SO₄) and concentrated under reduced pressure. The residue was injected into a 12 g ISCO Gold column and purified by combi-flash, eluting with 20% to 100% EtOAc/hexanes to give the title compounds (880 mg, 1.85 mmol) as a colorless syrup.

Step 5: (S)-methyl 4-(N,N-bis(4-methoxybenzyl)sulfamoyl)-4-methyloct-7-enoate and (R)-methyl 4-(N,N-bis(4-methoxybenzyl)sulfamoyl)-4-methyloct-7-enoate

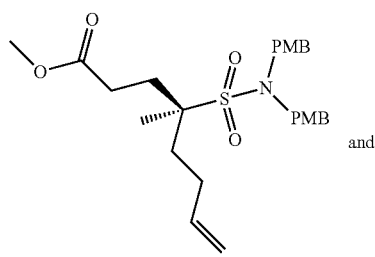
and

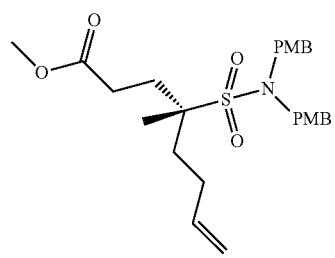

To a solution of (S)-4-(N,N-bis(4-methoxybenzyl)sulfamoyl)-4-methyloct-7-enoic acid and (R)-4-(N,N-bis(4-methoxybenzyl)sulfamoyl)-4-methyloct-7-enoic acid (Example 560, Step 4) (880 mg, 1.85 mmol) in MeOH (6 mL) was added thionyl chloride (0.27 mL, 3.7 mmol) at 0° C. dropwise. Then the reaction was allowed to warm to ambient temperature and stirred for 3 h. Then, the reaction was diluted (EtOAc and ice-cold water), extracted (2×EtOAc), and washed (saturated aqueous NaHCO₃ and brine). The combined organic layers were dried (Na₂SO₄) and concentrated under reduced pressure to provide a crude product, which was used for next step without any further purification.

Step 6: (S)-methyl 4-methyl-4-sulfamoyloct-7-enoate and (R)-methyl 4-methyl-4-sulfamoyloct-7-enoate

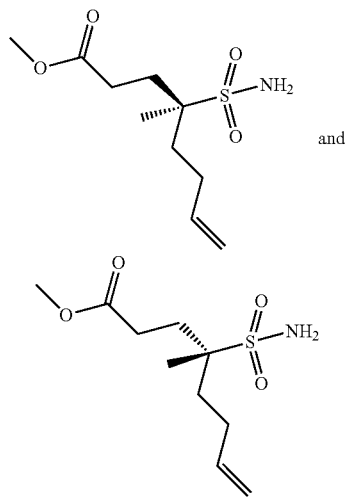

To a solution of (S)-methyl 4-(N,N-bis(4-methoxybenzyl)sulfamoyl)-4-methyloct-7-enoate and (R)-methyl 4-(N,N-bis(4-methoxybenzyl)sulfamoyl)-4-methyloct-7-enoate (Example 560, Step 5) (880 mg, 1.80 mmol) in DCM (12 mL) was added anisole (1.95 mL, 18.0 mmol) and TFA (4.01 mL, 53.9 mmol) at ambient temperature. After the reaction was stirred for 16 h, the reaction was concentrated under reduced pressure. The residue was injected into a 24 g ISCO Gold column and purified by combi-flash, eluting with 0% to 20% MeOH (containing 0.3% AcOH)/DCM to give the title compounds (132 mg, 0.529 mmol, 30%) as a colorless film.

Step 7: methyl 3-((1S,3'R,6'R,7'S,8'E,12'S)-6-chloro-7'-hydroxy-12'-methyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-12'-yl)propanoate or methyl 3-((1S,3'R,6'R,7'S,8'E,12'R)-6-chloro-7'-hydroxy-12'-methyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-12'-yl)propanoate (Isomer 1)

One of the title compounds (isomer 1) was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic Acid (Intermediate AA12A) by a procedure analogous to that described in Example 610, Steps 1 through 2, replacing (R)-hept-6-ene-3-sulfonamide in Step 1 with (S)-methyl 4-methyl-4-sulfamoyloct-7-enoate and (R)-methyl 4-methyl-4-sulfamoyloct-7-enoate (Example 560, Step 6). The crude product was purified by reversed phase preparatory HPLC (Gemini™ Prep C₁₈ 5 μm column; Phenomenex, Torrance, CA; gradient elution of 50% to 80% MeCN in water, where both solvents contain 0.1% TFA, 30 min method) to provide one of the title compounds as the faster eluting isomer as a white foam (isomer 1). ¹H NMR (400 MHz, CDCl₃) δ ppm 8.05 (br. s., 1H), 7.73-7.67 (m, 1H), 7.19 (dd, J=2.2, 8.4 Hz, 1H), 7.09 (d, J=2.2 Hz, 1H), 7.01

(m, 1H), 6.97-6.92 (m, 1H), 6.78 (m, 1H), 5.85 (m, 1H), 5.64 (m, 1H), 4.23 (m, 1H), 4.15-4.08 (m, 1H), 4.07-4.00 (m, 1H), 3.79-3.68 (m, 2H), 3.71 (s, 3H), 3.30 (d, J=14.3 Hz, 1H), 3.04 (dd, J=10.9, 15.2 Hz, 1H), 2.85-2.69 (m, 2H), 2.61 (m, 2H), 2.47 (m, 1H), 2.33 (m, 3H), 2.25-1.88 (m, 6H), 1.87-1.72 (m, 4H), 1.71-1.61 (m, 1H), 1.48-1.39 (m, 1H) 1.45 (s, 3H); m/z (ESI, +ve ion) 671.2 (M+H)+.

Example 561. methyl 3-((1S,3'R,6'R,7'S,8'E,12'S)-6-chloro-7'-hydroxy-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)propanoate or methyl 3-((1S,3'R,6'R,7'S,8'E,12'R)-6-chloro-7'-hydroxy-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)propanoate (Isomer 2)

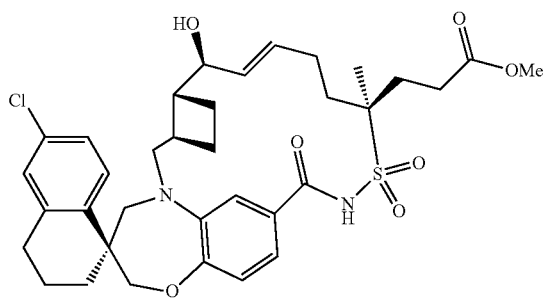

or

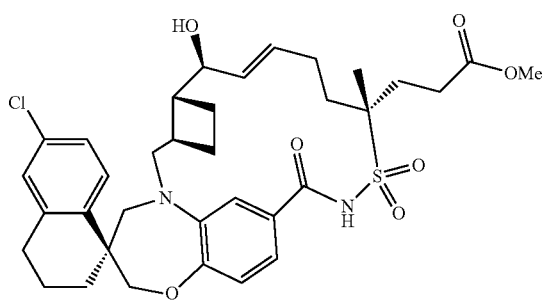

One of the title compounds (isomer 2) was obtained as the second (slower) eluting isomer from reversed phase preparatory HPLC purification in Example 560. $^1$H NMR (400 MHz, CDCl$_3$) δ ppm 8.57 (br. s., 1H), 7.73-7.69 (m, 1H), 7.24-7.15 (m, 1H), 7.10 (m, 2H), 6.98-6.92 (m, 1H), 6.85 (m, 1H), 5.92 (m, 1H), 5.68 (m, 1H), 4.26 (m, 1H), 4.15-4.09 (m, 1H), 4.08-4.01 (m, 1H), 3.77-3.69 (m, 5H), 3.29 (m, 1H), 3.05 (dd, J=10.4, 15.3 Hz, 1H), 2.84-2.62 (m, 3H), 2.56-2.15 (m, 7H), 2.16-1.83 (m, 10H), 1.70-1.60 (m, 1H), 1.54-1.35 (m, 1H), 1.50 (s, 1H); m/z (ESI, +ve ion) 671.2 (M+H)+.

Example 562. methyl 3-((1S,3'R,6'R,7'S,8'Z,12'S)-6-chloro-7'-hydroxy-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)propanoate or methyl 3-((1S,3'R,6'R,7'S,8'Z,12'R)-6-chloro-7'-hydroxy-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)propanoate (Isomer 1)

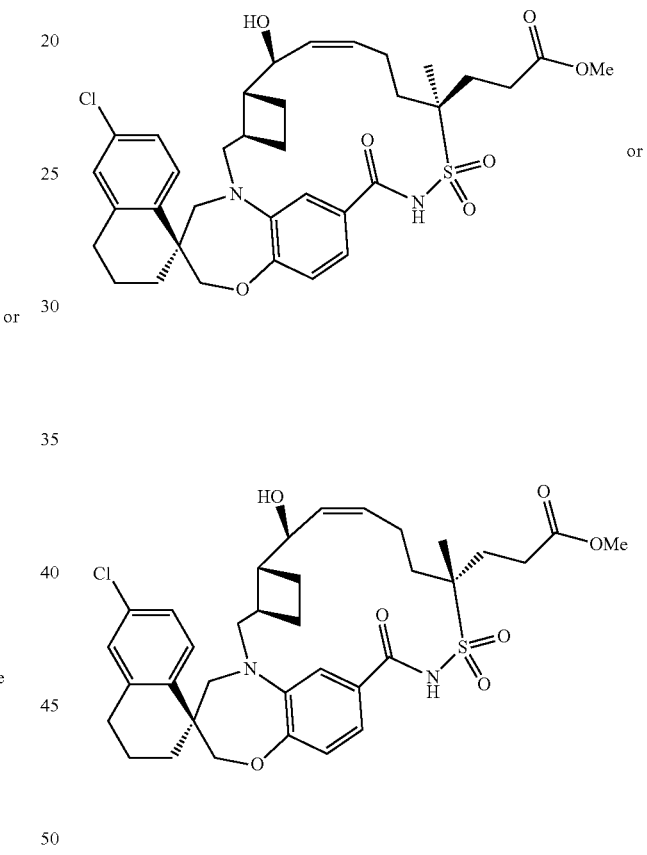

One of the title compounds (isomer 1) was obtained as the third (slower) eluting isomer from reversed phase preparatory HPLC purification in Example 560. $^1$H NMR (400 MHz, CDCl$_3$) δ ppm 10.56 (br. s., 1H), 7.70 (d, J=8.6 Hz, 1H), 7.58 (dd, J=1.6, 8.2 Hz, 1H), 7.27 (m, 1H), 7.17 (dd, J=2.2, 8.5 Hz, 1H), 7.09 (d, J=2.2 Hz, 1H), 6.96 (d, J=8.2 Hz, 1H), 5.78-5.68 (m, 1H), 5.48 (dd, J=4.1, 11.0 Hz, 1H), 4.41 (m, 1H), 4.10 (d, J=11.7 Hz, 1H), 4.00 (d, J=11.9 Hz, 1H), 3.77 (d, J=15.3 Hz, 1H), 3.72 (s, 3H), 3.56 (d, J=14.3 Hz, 1H), 3.17-2.99 (m, 2H), 2.89-2.68 (m, 3H), 2.64-2.41 (m, 4H), 2.35-2.18 (m, 5H), 2.16-2.00 (m, 3H), 1.94-1.72 (m, 3H), 1.70-1.64 (m, 1H), 1.55-1.42 (m, 1H), 1.50 (s, 3H); m/z (ESI, +ve ion) 671.2 (M+H)+.

Example 563. methyl 3-((1S,3'R,6'R,7'S,8'Z,12'R)-6-chloro-7'-hydroxy-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)propanoate or methyl 3-((1S,3'R,6'R,7'S,8'Z,12'S)-6-chloro-7'-hydroxy-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)propanoate (Isomer 2)

Example 564. (1S,3'R,6'R,7'S,8'E,12'S)-6-chloro-7'-hydroxy-12'-((5-methyl-1,3,4-oxadiazol-2-yl)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-7'-hydroxy-12'-((5-methyl-1,3,4-oxadiazol-2-yl)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Isomer 1)

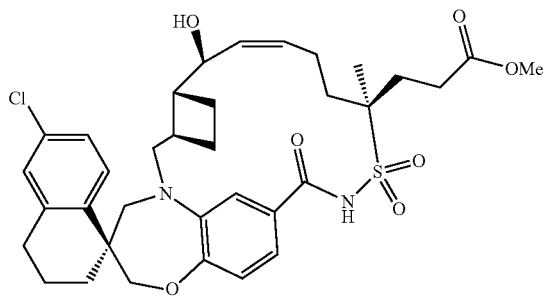

or

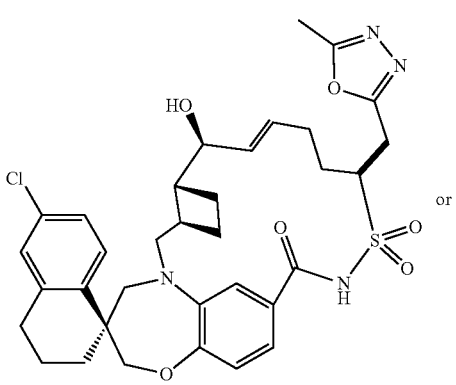

or

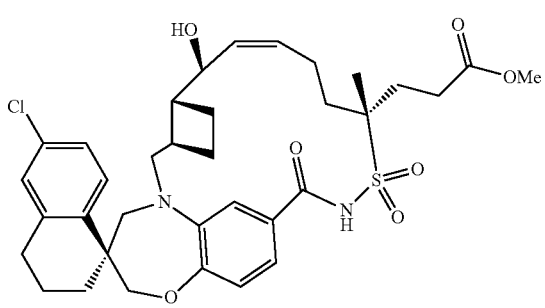

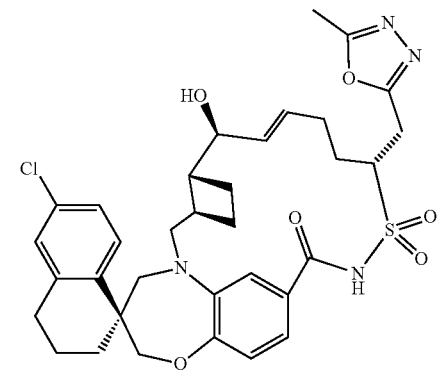

One of the title compounds (isomer 2) was obtained as the fourth (slowest) eluting isomer from reversed phase preparatory HPLC purification in Example 560. $^1$H NMR (400 MHz, CDCl$_3$) δ ppm 10.59 (s, 1H), 7.70 (d, J=8.4 Hz, 1H), 7.60 (dd, J=1.6, 8.4 Hz, 1H), 7.32 (d, J=1.8 Hz, 1H), 7.16 (dd, J=2.2, 8.5 Hz, 1H), 7.08 (d, J=2.2 Hz, 1H), 6.96 (d, J=8.4 Hz, 1H), 5.82-5.74 (m, 1H), 5.50 (dd, J=2.6, 11.1 Hz, 1H), 4.41 (m, 1H), 4.08 (d, J=11.9 Hz, 1H), 3.97 (d, J=11.7 Hz, 1H), 3.81 (d, J=15.5 Hz, 1H), 3.71 (s, 3H), 3.57 (d, J=14.1 Hz, 1H), 3.11-2.99 (m, 2H), 2.78-2.49 (m, 5H), 2.40-2.31 (m, 2H), 2.30-1.70 (m, 10H), 1.70-1.63 (m, 1H), 1.58 (s, 3H), 1.53-1.38 (m, 2H); m/z (ESI, +ve ion) 671.2 (M+H)$^+$.

Step 1: (R)-1-hydroxy-N,N-bis(4-methoxybenzyl)hept-6-ene-3-sulfonamide and (S)-1-hydroxy-N,N-bis(4-methoxybenzyl)hept-6-ene-3-sulfonamide

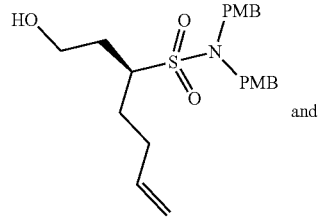

and

-continued

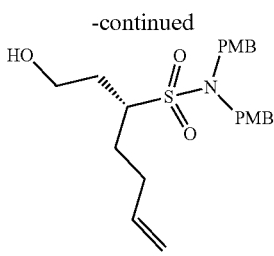

To a solution of N,N-bis(4-methoxybenzyl)pent-4-ene-1-sulfonamide (Intermediate EE19) (2.55 g, 6.55 mmol) in THF (26 mL) was added n-BuLi (2.5 M solution in hexanes, 2.88 mL, 7.20 mmol) at −78° C. dropwise. After the reaction mixture was stirred at −78° C. for 10 min, excess ethylene oxide was bubbled into the reaction. Then the reaction was stirred at the same temperature for 1 h, allowed to warm to ambient temperature, and stirred for 16 h. The reaction was quenched (saturated aqueous NH$_4$Cl), extracted (2×EtOAc), and washed (brine). The combined organic layers were dried (Na$_2$SO$_4$) and concentrated under reduced pressure. The residue was injected into a 120 g ISCO Gold column and purified by combi-flash, eluting with 30% to 60% EtOAc/hexanes to give the title compounds (1.80 g, 4.15 mmol) as a colorless oil.

Step 2: (1S,3'R,6'R,7'S,8'E,12'S)-6-chloro-7'-hydroxy-12'-((5-methyl-1,3,4-oxadiazol-2-yl)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-hydroxy-12'-((5-methyl-1,3,4-oxadiazol-2-yl)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (Isomer 1)

One of the title compounds (isomer 1) was prepared by a procedure analogous to that described in Example 632, Steps 3 through 7, replacing 1-hydroxy-N,N-bis(4-methoxybenzyl)oct-7-ene-4-sulfonamide in Step 3 with (R)-1-hydroxy-N,N-bis(4-methoxybenzyl)hept-6-ene-3-sulfonamide and (S)-1-hydroxy-N,N-bis(4-methoxybenzyl)hept-6-ene-3-sulfonamide (Example 564, Step 1). The crude product was purified by reversed phase preparatory HPLC (Gemini™ Prep C$_{18}$ 5 μm column; Phenomenex, Torrance, CA; gradient elution of 45% to 70% MeCN in water, where both solvents contain 0.1% TFA, 30 min method) to provide one of the title compounds (isomer 1) as the faster eluting isomer as a white foam. $^1$H NMR (400 MHz, CDCl$_3$) δ ppm 8.37 (br. s, 1H), 7.71 (d, J=8.6 Hz, 1H), 7.20 (dd, J=2.3, 8.7 Hz, 1H), 7.11 (d, J=2.2 Hz, 1H), 7.02-6.92 (m, 3H), 5.84 (m, 1H), 5.77-5.70 (m, 1H), 4.59 (m, 1H), 4.28-4.23 (m, 1H), 4.16-4.07 (m, 2H), 3.80 (d, J=14.1 Hz, 1H), 3.75-3.65 (m, 2H), 3.40 (dd, J=7.4, 16.0 Hz, 1H), 3.27 (d, J=14.1 Hz, 1H), 3.13-3.05 (m, 1H), 2.85-2.73 (m, 2H), 2.58 (s, 3H), 2.41 (m, 3H), 2.15-1.65 (m, 7H), 1.45 (t, J=11.4 Hz, 1H), 1.28 (s, 3H); m/z (ESI, +ve ion) 667.2 (M+H)$^+$.

Example 565. (1S,3'R,6'R,7'S,8'E,12'R)-6-chloro-7'-hydroxy-12'-((5-methyl-1,3,4-oxadiazol-2-yl)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'S)-6-chloro-7'-hydroxy-12'-((5-methyl-1,3,4-oxadiazol-2-yl)methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (Isomer 2)

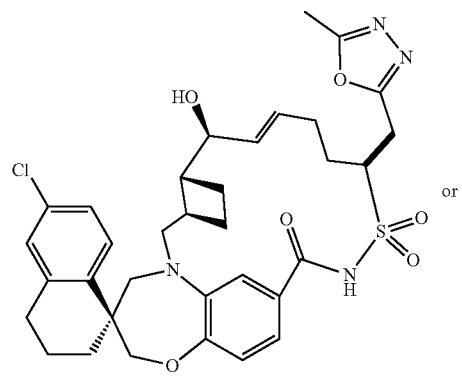

or

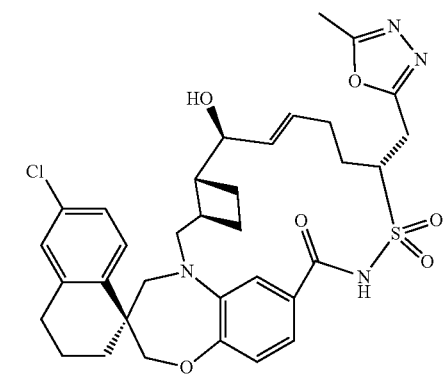

One of the title compounds (isomer 2) was obtained as the second (slower) eluting isomer from reversed phase preparatory HPLC purification in Example 564. $^1$H NMR (400 MHz, CDCl$_3$) δ ppm 10.04 (br. s, 1H), 7.74-7.68 (m, 1H), 7.49-7.43 (m, 1H), 7.24-7.15 (m, 1H), 7.10 (m, 2H), 7.02-6.97 (m, 1H), 5.73 (m, 1H), 5.56-5.47 (m, 1H), 4.48 (m, 1H), 4.22-4.06 (m, 3H), 3.89 (d, J=15.3 Hz, 1H), 3.80-3.63 (m, 2H), 3.34-3.18 (m, 2H), 3.14 (m, 1H), 2.82-2.73 (m, 2H), 2.56 (s, 3H), 2.49-2.31 (m, 1H), 2.23 (m, 3H), 2.12-1.42 (m, 10H); m/z (ESI, +ve ion) 667.2 (M+H)$^+$.

1217

Example 566. 1-methylethyl ((1S,3'R,6'R,7'S,8'E, 11'S,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-12'-yl) acetate or 1-methylethyl ((1S,3'R,6'R,7'S,8'E,11'R, 12'S)-6-chloro-7'-hydroxy-11'-methyl-13',13'-dioxido-15'-oxo-3,4-dihydro-2H-spiro[naphthalene-1, 22'-[20]oxa[13]thia[1,14]diazatetracyclo[14.7.2.0³,⁶.0¹⁹,²⁴]pentacosa [8,16,18,24]tetraen]-12'-yl) acetate or 1-methylethyl ((1S,3'R,6'R,7'S,8'E,11'R, 12'R)-6-chloro-7'-hydroxy-11'-methyl-13',13'-dioxido-15'-oxo-3,4-dihydro-2H-spiro[naphthalene-1, 22'-[20]oxa[13]thia[1,14]diazatetracyclo[14.7.2.0³,⁶.0¹⁹,²⁴]pentacosa [8,16,18,24]tetraen]-12'-yl) acetate or 1-methylethyl ((1S,3'R,6'R,7'S,8'E,11'S, 12'S)-6-chloro-7'-hydroxy-11'-methyl-13',13'-dioxido-15'-oxo-3,4-dihydro-2H-spiro[naphthalene-1, 22'-[20]oxa[13]thia[1,14]diazatetracyclo[14.7.2.0³,⁶.0¹⁹,²⁴]pentacosa [8,16,18,24]tetraen]-12'-yl) acetate (Isomer 1)

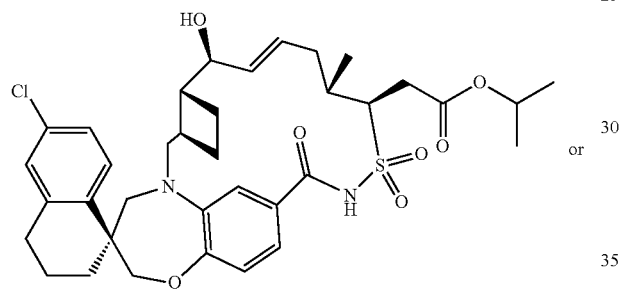

or

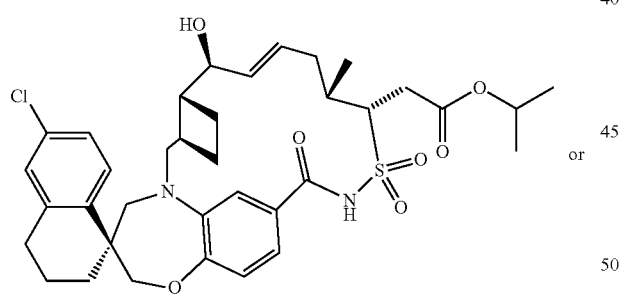

or

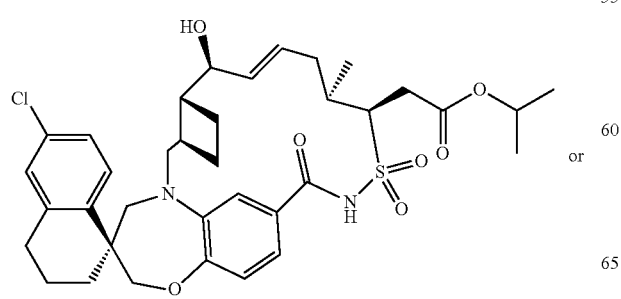

or

1218

-continued

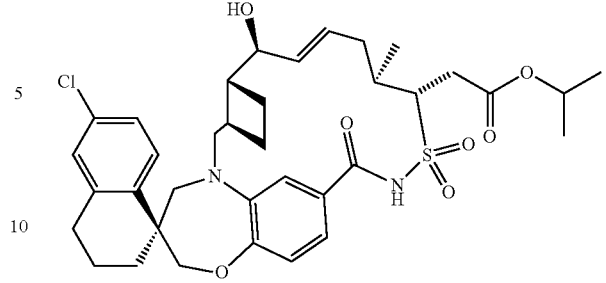

Step 1: (3R,4R)-isopropyl 3-(N,N-bis(4-methoxybenzyl)sulfamoyl)-4-methylhept-6-enoate and (3R, 4S)-isopropyl 3-(N,N-bis(4-methoxybenzyl)sulfamoyl)-4-methylhept-6-enoate and (3S,4R)-isopropyl 3-(N,N-bis(4-methoxybenzyl)sulfamoyl)-4-methylhept-6-enoate and (3S,4S)-isopropyl 3-(N,N-bis(4-methoxybenzyl)sulfamoyl)-4-methylhept-6-enoate


and

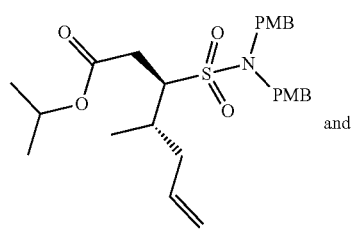

and


and

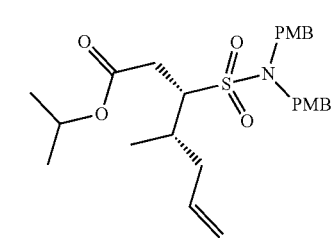

The title compounds were prepared from (3R,4R)-3-(N,N-bis(4-methoxybenzyl)sulfamoyl)-4-methylhept-6-enoic acid and (3R,4S)-3-(N,N-bis(4-methoxybenzyl)sulfamoyl)-4-methylhept-6-enoic acid and (3S,4R)-3-(N,N-bis(4-methoxybenzyl)sulfamoyl)-4-methylhept-6-enoic acid and (3S,4S)-3-(N,N-bis(4-methoxybenzyl)sulfamoyl)-4-methylhept-6-enoic acid (Example 647, Steps 9) by a procedure analogous to that described in Example 647, Steps 10, replacing MeOH in Step 10 with 2-propanol. The crude product was used for next step without any further purification.

Step 2: 1-methylethyl ((1S,3'R,6'R,7'S,8'E,11',12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate or 1-methylethyl ((1S,3'R,6'R,7'S,8'E,11'R,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate or 1-methylethyl ((1S,3'R,6'R,7'S,8'E,11'R,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate or 1-methylethyl ((1S,3'R,6'R,7'S,8'E,11'S,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate (Isomer 1)

One of the title compounds (isomer 1) was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic Acid (Intermediate AA12A) by a procedure analogous to that described in Example 611, Steps 2 through 3, replacing (S)-2-(N,N-bis(4-methoxybenzyl)sulfamoyl)hex-5-en-1-yl carbamate in Step 2 with (3R,4R)-isopropyl 3-(N,N-bis(4-methoxybenzyl)sulfamoyl)-4-methylhept-6-enoate and (3R,4S)-isopropyl 3-(N,N-bis(4-methoxybenzyl)sulfamoyl)-4-methylhept-6-enoate and (3S,4R)-isopropyl 3-(N,N-bis(4-methoxybenzyl)sulfamoyl)-4-methylhept-6-enoate and (3S,4S)-isopropyl 3-(N,N-bis(4-methoxybenzyl)sulfamoyl)-4-methylhept-6-enoate (Example 566, Step 1). The crude product was purified by reversed phase preparatory HPLC (Gemini™ Prep C$_{18}$ 5 μm column; Phenomenex, Torrance, CA; gradient elution of 50% to 80% MeCN in water, where both solvents contain 0.1% TFA, 30 min method) to provide one of the title compounds (isomer 1) as the faster eluting isomer as a white foam. $^1$H NMR (400 MHz, CDCl$_3$) δ ppm 8.01 (br. s., 1H), 7.72-7.67 (m, 1H), 7.18 (dd, J=2.2, 8.5 Hz, 1H), 7.10 (d, J=2.2 Hz, 1H), 7.01 (m, 1H), 6.96-6.88 (m, 2H), 5.98 (m, 1H), 5.73 (dd, J=7.6, 15.1 Hz, 1H), 5.10 (quin, J=6.3 Hz, 1H), 4.86 (m, 1H), 4.26 (m, 1H), 4.14-4.06 (m, 2H), 3.81 (d, J=15.1 Hz, 1H), 3.68 (d, J=14.5 Hz, 1H), 3.27 (d, J=14.3 Hz, 1H), 3.02 (dd, J=7.3, 16.7 Hz, 1H), 2.83-2.71 (m, 2H), 2.64 (dd, J=5.3, 16.8 Hz, 1H), 2.53-2.39 (m, 1H), 2.38-2.27 (m, 2H), 2.12-1.74 (m, 9H), 1.72-1.64 (m, 1H), 1.43 (t, J=13.1 Hz, 1H), 1.30 (m, 6H), 1.08 (d, J=6.3 Hz, 3H); m/z (ESI, +ve ion) 685.3 (M+H)$^+$.

Example 567. 1-methylethyl ((1S,3'R,6'R,7'S,8'E,11'S,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate or 1-methylethyl ((1S,3'R,6'R,7'S,8'E,11'R,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate or 1-methylethyl ((1S,3'R,6'R,7'S,8'E,11'R,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate or 1-methylethyl ((1S,3'R,6'R,7'S,8'E,11'S,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate (Isomer 2)

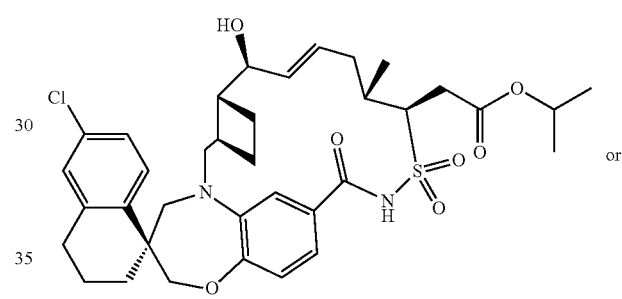

or

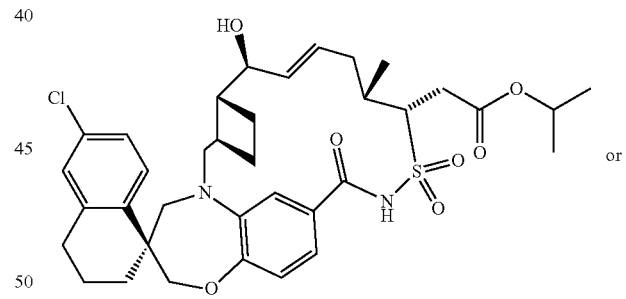

or

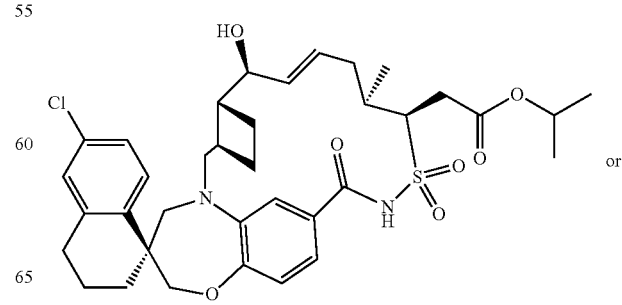

or

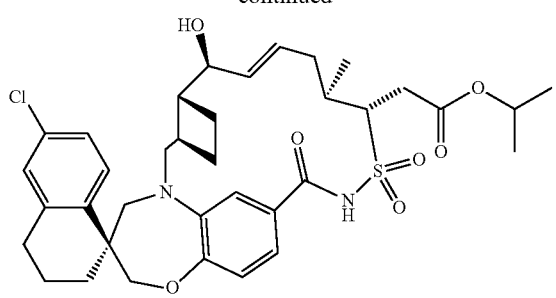

One of the title compounds (isomer 2) was obtained as the second (slower) eluting isomer from reversed phase preparatory HPLC purification in Example 566, Step 2. $^1$H NMR (400 MHz, CDCl$_3$) δ ppm 9.75 (br. S, 1H), 7.69 (d, J=8.6 Hz, 1H), 7.22-7.15 (m, 1H), 7.15-7.06 (m, 2H), 6.99-6.91 (m, 1H), 6.82 (m, 1H), 5.94 (m, 1H), 5.66 (dd, J=5.6, 15.4 Hz, 1H), 5.07 (td, J=6.3, 12.5 Hz, 1H), 4.33 (m, 1H), 4.24-4.15 (m, 1H), 4.09 (q, J=12.1 Hz, 2H), 3.71 (m, 1H), 3.56 (m, 1H), 3.48-3.22 (m, 2H), 3.14 (dd, J=5.9, 17.0 Hz, 1H), 2.84-2.73 (m, 2H), 2.73-2.57 (m, 2H), 2.53-2.40 (m, 1H), 2.35 (m, 9H), 1.70 (quin, J=9.2 Hz, 1H), 1.58-1.41 (m, 1H), 1.31-1.23 (m, 6H), 1.14 (d, J=7.0 Hz, 3H); m/z (ESI, +ve ion) 685.3 (M+H)$^+$.

Example 568. 1-methylethyl ((1S,3'R,6'R,7'S,8'Z,11'S,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$pentacosa[8,16,18,24]tetraen]-12'-yl)acetate or 1-methylethyl ((1S,3'R,6'R,7'S,8'Z,11'R,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$pentacosa[8,16,18,24]tetraen]-12'-yl)acetate or 1-methylethyl ((1S,3'R,6'R,7'S,8'Z,11'R,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$pentacosa[8,16,18,24]tetraen]-12'-yl)acetate or 1-methylethyl ((1S,3'R,6'R,7'S,8'Z,11'S,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$pentacosa[8,16,18,24]tetraen]-12'-yl)acetate (Isomer 1)

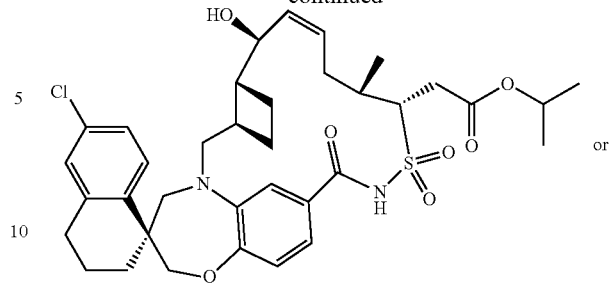

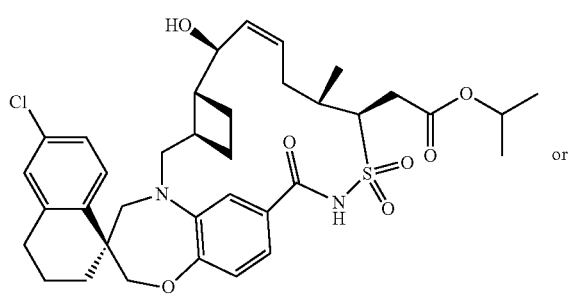

One of the title compounds (isomer 1) was obtained as the third (slower) eluting isomer from reversed phase preparatory HPLC purification in Example 566, Step 2. $^1$H NMR (400 MHz, CDCl$_3$) δ ppm 9.56 (br. s, 1H), 7.70 (d, J=8.6 Hz, 1H), 7.35-7.28 (m, 1H), 7.18 (dd, J=2.3, 8.4 Hz, 1H), 7.12-7.06 (m, 2H), 6.94 (d, J=8.2 Hz, 1H), 5.81-5.70 (m, 1H), 5.61 (dd, J=5.3, 11.3 Hz, 1H), 5.07 (td, J=6.3, 12.5 Hz, 1H), 4.44 (m, 1H), 4.19-4.03 (m, 3H), 3.79 (d, J=15.1 Hz, 1H), 3.64 (d, J=14.1 Hz, 1H), 3.38 (dd, J=4.5, 17.2 Hz, 1H), 3.27-3.10 (m, 2H), 3.04 (m, 1H), 2.83-2.58 (m, 3H), 2.48-1.63 (m, 11H), 1.45 (t, J=12.6 Hz, 1H), 1.30-1.24 (m, 6H), 1.08 (d, J=6.7 Hz, 3H); m/z (ESI, +ve ion) 685.3 (M+H)$^+$.

Example 569. 1-methylethyl ((1S,3'R,6'R,7'S,9'Z, 11'S,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo [14.7.2.0$^{3,6}$.0$^{19,24}$]pentacosa [9,16,18,24]tetraen]-12'-yl)acetate or 1-methylethyl ((1S,3'R,6'R,7'S,9'Z, 11'R,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo [14.7.2.0$^{3,6}$.0$^{19,24}$]pentacosa [9,16,18,24]tetraen]-12'-yl)acetate or 1-methylethyl ((1S,3'R,6'R,7'S,9'Z, 11'R,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo [14.7.2.0$^{3,6}$.0$^{19,24}$]pentacosa [9,16,18,24]tetraen]-12'-yl)acetate or 1-methylethyl ((1S,3'R,6'R,7'S,9'Z, 11'S,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [9,16,18,24]tetraen]-12'-yl) acetate


or


or

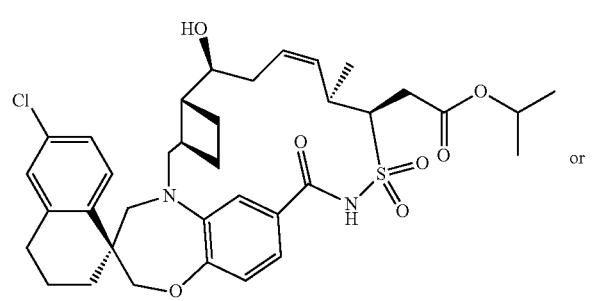

or

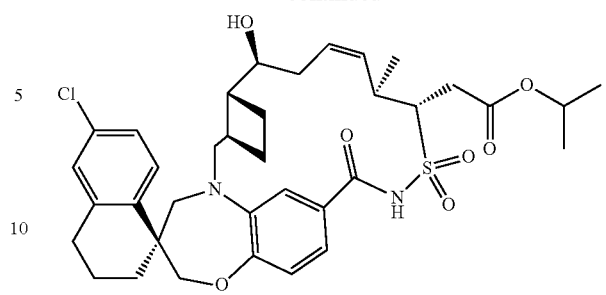

One of the title compounds was obtained as the fourth (slower) eluting isomer from reversed phase preparatory HPLC purification in Example 566, Step 2. $^1$H NMR (400 MHz, CDCl$_3$) δ ppm 10.07 (br. S, 1H), 7.70 (d, J=8.4 Hz, 1H), 7.48 (m, 1H), 7.18 (dd, J=2.2, 8.5 Hz, 1H), 7.13 (m, 1H), 7.09 (d, J=2.2 Hz, 1H), 6.97 (d, J=8.4 Hz, 1H), 5.78-5.70 (m, 1H), 5.57-5.49 (m, 1H), 5.10 (td, J=6.2, 12.5 Hz, 1H), 4.40 (m, 1H), 4.24 (m, 1H), 4.14-3.98 (m, 2H), 3.85 (d, J=15.1 Hz, 1H), 3.62 (d, J=14.1 Hz, 1H), 3.20-2.98 (m, 4H), 2.89-2.72 (m, 3H), 2.66 (m, 1H), 2.29-2.17 (m, 2H), 2.13-2.00 (m, 1H), 1.99-1.86 (m, 4H), 1.83-1.55 (m, 3H), 1.50-1.36 (m, 1H), 1.34-1.24 (m, 6H), 11.08 (d, J=6.7 Hz, 3H); m/z (ESI, +ve ion) 685.3 (M+H)$^+$.

Example 570. 1-methylethyl ((1S,3'R,6'R,7'S,8'Z, 11'S,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo [14.7.2.0$^{3,6}$.0$^{19,24}$pentacosa[8,16,18,24]tetraen]-12'-yl)acetate or 1-methylethyl ((1S,3'R,6'R,7'S,8'Z, 11'R,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo [14.7.2.0$^{3,6}$.0$^{19,24}$pentacosa[8,16,18,24]tetraen]-12'-yl)acetate or 1-methylethyl ((1S,3'R,6'R,7'S,8'Z, 11'R,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo [14.7.2.0$^{3,6}$.0$^{19,24}$pentacosa[8,16,18,24]tetraen]-12'-yl)acetate or 1-methylethyl ((1S,3'R,6'R,7'S,8'Z, 11'S,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo [14.7.2.0$^{3,6}$.0$^{19,24}$pentacosa[8,16,18,24]tetraen]-12'-yl)acetate (Isomer 2)

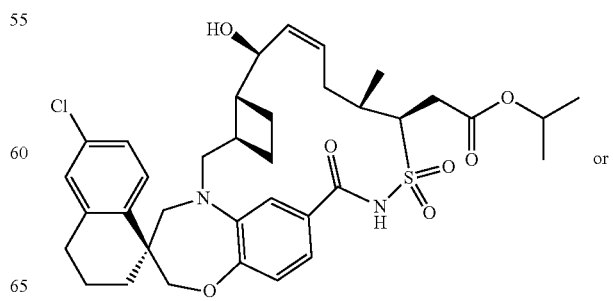

or

-continued

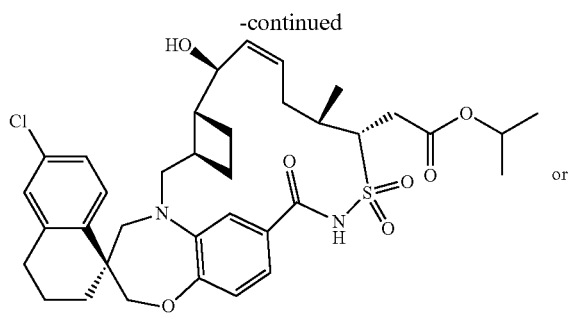

or

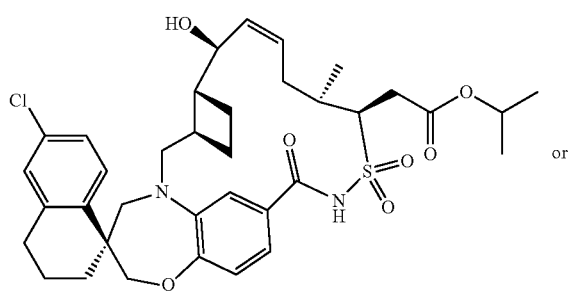

or

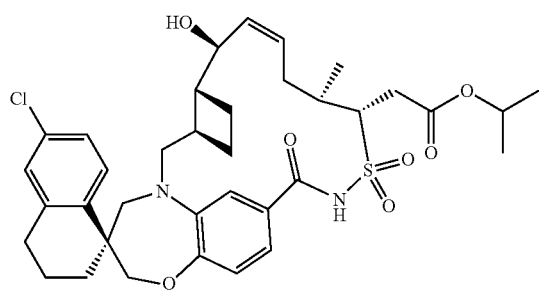

One of the title compounds (isomer 2) was obtained as the fifth (slowest) eluting isomer from reversed phase preparatory HPLC purification in Example 566, Step 2. $^1$H NMR (400 MHz, CDCl$_3$) δ ppm 10.58 (br. s., 1H), 7.63 (d, J=8.6 Hz, 1H), 7.47 (m, 1H), 7.15 (m, 1H), 7.09 (dd, J=2.2, 8.5 Hz, 1H), 7.01 (d, J=2.3 Hz, 1H), 6.89 (d, J=8.2 Hz, 1H), 5.84-5.76 (m, 1H), 5.50 (dd, J=6.3, 10.6 Hz, 1H), 5.01 (quin, J=6.3 Hz, 1H), 4.32 (m, 1H), 4.03 (d, J=11.7 Hz, 1H), 3.96 (d, J=11.9 Hz, 1H), 3.93-3.87 (m, 1H), 3.71 (d, J=15.3 Hz, 1H), 3.60-3.46 (m, 1H), 3.07-2.82 (m, 3H), 2.73-2.63 (m, 2H), 2.56 (dd, J=8.5, 16.7 Hz, 1H), 2.45-2.32 (m, 1H), 2.31-1.67 (m, 8H), 1.64-1.54 (m, 2H), 1.47-1.32 (m, 2H), 1.23-1.17 (m, 6H), 1.08 (d, J=7.0 Hz, 3H); m/z (ESI, +ve ion) 685.3 (M+H)$^+$.

Example 571. (1S,3'R,6'R,7'S,8'E,11'S,12'R)-6-chloro-7'-hydroxy-11'-methoxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-7'-hydroxy-11'-methoxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-7'-hydroxy-11'-methoxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methoxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (Isomer 1)

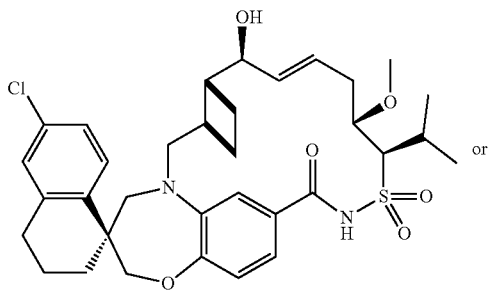

or

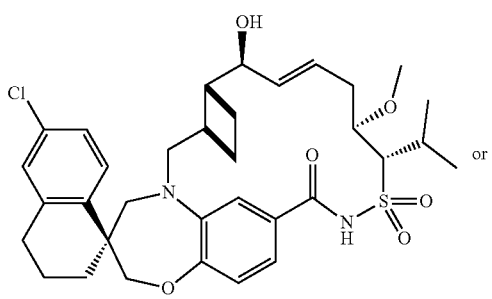

or

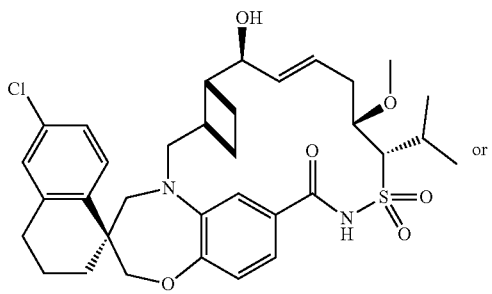

or

1227

-continued

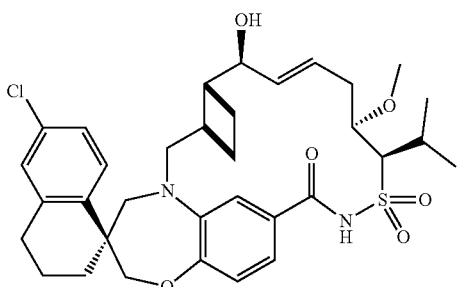

Step 1: N,N-bis(4-methoxybenzyl)-2-methylpropane-1-sulfonamide

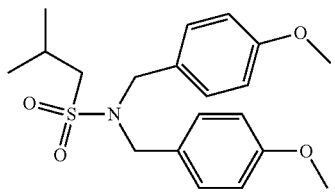 [SMILES: COc1ccc(CN(Cc2ccc(OC)cc2)S(=O)(=O)CC(C)C)cc1]

To a solution of bis(4-methoxybenzyl)amine (Intermediate EE11) (3.35 g, 13.0 mmol) and TEA (6.34 ml, 45.6 mmol) in DCM2 (65 ml) was added isobutanesulfonyl chloride (1.70 mL, 13.0 mmol) dropwise over 5 minutes at 0° C. and the resulting cloudy mixture was stirred at the same temperature for 1 h. The reaction was then diluted (DCM) and washed (2×brine). The aqueous layer was back extracted once (EtOAc) and the combined organic layers were dried (MgSO₄) and concentrated under reduced pressure. The residue was injected into a 80 g ISCO Gold column and purified by combi-flash, eluting with 100% to 40% EtOAc/hexanes to provide the product (2.00 g, 5.30 mmol, 41%).

Step 2: (R)-methyl 2-(N,N-bis(4-methoxybenzyl)sulfamoyl)-3-methylbutanoate and (S)-methyl 2-(N,N-bis(4-methoxybenzyl)sulfamoyl)-3-methylbutanoate

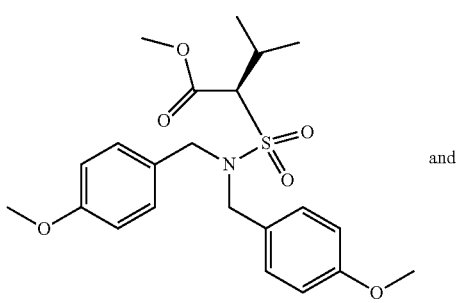

and

1228

-continued

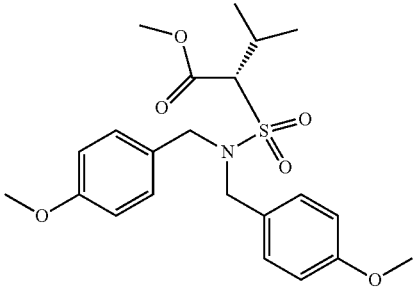

To a solution of N,N-bis(4-methoxybenzyl)-2-methylpropane-1-sulfonamide (Example 571, Step 1) (1.93 g, 5.11 mmol) in THF (10 ml) was added n-BuLi (2.0 M solution in hexanes, 2.25 mL, 5.50 mmol) dropwise at −78° C. After the reaction mixture was stirred at the same temperature for 5 min, chlorocarbonic acid methyl ester (0.593 ml, 7.67 mmol) was added and the resulting reaction mixture was stirred for another 20 min, and then allowed to warm to ambient temperature. The reaction mixture was quenched (saturated aqueous NH₄Cl, 10 mL) and extracted (Et₂O, 2×30 mL). The combined organic layers were washed (brine, 10 mL and, dried (MgSO₄), concentrated under reduced pressure to give the crude material (2.22 g, 5.11 mmol, 100%) as a colorless oil. The product was used in the next step without further purification.

Step 3: (R)-1-hydroxy-N,N-bis(4-methoxybenzyl)-3-methylbutane-2-sulfonamide and (S)-1-hydroxy-N,N-bis(4-methoxybenzyl)-3-methylbutane-2-sulfonamide

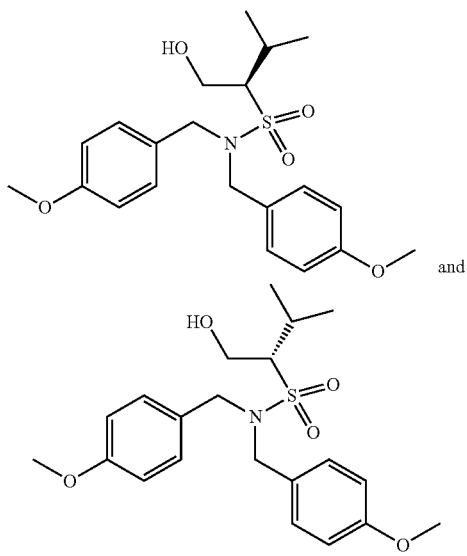

To a solution of (R)-methyl 2-(N,N-bis(4-methoxybenzyl)sulfamoyl)-3-methylbutanoate and (S)-methyl 2-(N,N-bis(4-methoxybenzyl)sulfamoyl)-3-methylbutanoate (Example 571, Step 2) (2.25 g, 5.17 mmol) in THF (12 ml) was added lithium borohydride (0.225 g, 10.3 mmol) with very small amount of water at 0° C. The reaction mixture was allowed to warm to ambient temperature and stirred overnight. Then, the reaction mixture was quenched (0.5 N aqueous HCl, 50 mL) and extracted (EtOAc, 3×100 mL). The combined organic layers were dried (Na₂SO₄) and concentrated under reduced pressure. The crude product was injected into a 80 g ISCO Gold column and purified by combi-flash, eluting with 20% to 80% EtOAc/hexanes to provide the product (1.10 g, 2.70 mmol, 52%) as a colorless oil.

Step 4: (R)—N,N-bis(4-methoxybenzyl)-3-methyl-1-oxobutane-2-sulfonamide and (S)—N,N-bis(4-methoxybenzyl)-3-methyl-1-oxobutane-2-sulfonamide

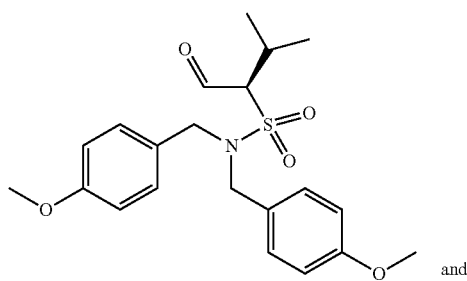

and

To a solution of (R)-1-hydroxy-N,N-bis(4-methoxybenzyl)-3-methylbutane-2-sulfonamide and (S)-1-hydroxy-N,N-bis(4-methoxybenzyl)-3-methylbutane-2-sulfonamide (Example 571, Step 3) (1.10 g, 2.70 mmol) in DCM (10 mL) was added Dess-Martin periodinane (2.29 g, 5.40 mmol) at ambient temperature. After the reaction was stirred for 12 h, the reaction mixture was diluted (saturated aqueous Na₂S₂O₃ solution, 15 mL) and extracted (Et₂O, 2×50 mL). The combined organic layers were washed (saturated aqueous NaHCO₃×3 and brine×3), dried (MgSO₄), and concentrated under reduced pressure. The crude product was injected into a 40 g ISCO Gold column and purified by combi-flash, eluting with 10% to 40% EtOAc/hexanes to provide the product (1.00 g, 2.47 mmol, 91%) as a colorless oil.

Step 5: [(3R,4S)-4-hydroxy-N,N-bis(4-methoxybenzyl)-2-methylhept-6-ene-3-sulfonamide and (3S,4R)-4-hydroxy-N,N-bis(4-methoxybenzyl)-2-methylhept-6-ene-3-sulfonamide] and [(3S,4S)-4-hydroxy-N,N-bis(4-methoxybenzyl)-2-methylhept-6-ene-3-sulfonamide and (3R,4R)-4-hydroxy-N,N-bis(4-methoxybenzyl)-2-methylhept-6-ene-3-sulfonamide]

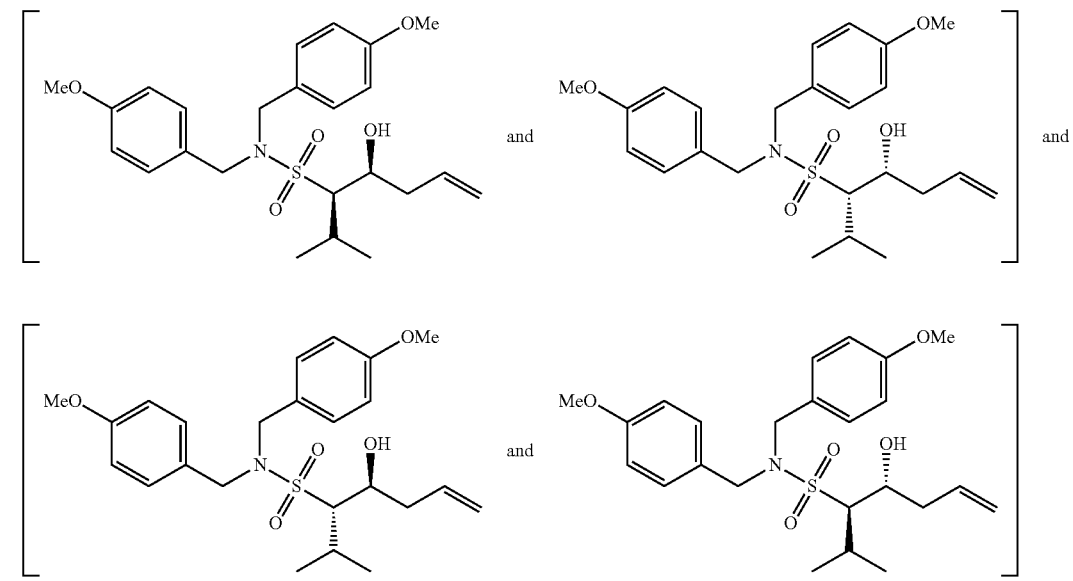

-continued

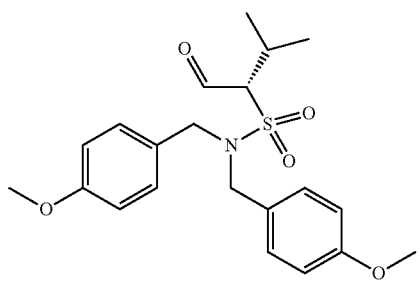

To a solution of (R)—N,N-bis(4-methoxybenzyl)-3-methyl-1-oxobutane-2-sulfonamide and (S)—N,N-bis(4-methoxybenzyl)-3-methyl-1-oxobutane-2-sulfonamide (Example 571, Step 4) (1.00 g, 2.47 mmol) and allyl iodide (0.908 ml, 9.86 mmol) in DMF (25 ml) was added indium (1.13 g, 9.86 mmol). The reaction mixture was stirred at ambient temperature for 2 days. The inorganic solid was filtered through celite to remove and the filter cake was rinsed (EtOAc). The filtrate was diluted (EtOAc, 200 mL) and washed (a mixture of water/saturated aqueous NaHCO₃/brine, v/v/v=2/1/1, 100 mL, water and brine). The organic layers were dried (Na₂SO₄) and concentrated under reduced pressure. The crude product was injected into a 40 g ISCO Gold column and purified by combi-flash, eluting with 0% to 30% EtOAc/hexanes to provide one enantiomeric mixture (enantiomeric mixture 1) (320 mg, 0.715 mmol, 29%, the faster eluting enantiomeric mixtures) and the other enantiomeric mixture (enantiomeric mixture 2) (230 mg, 0.514 mmol, 21%, the slower eluting enantiomeric mixtures) as a colorless oil.

Step 6: [(3R,4S)-4-methoxy-N,N-bis(4-methoxybenzyl)-2-methylhept-6-ene-3-sulfonamide and (3S,4R)-4-methoxy-N,N-bis(4-methoxybenzyl)-2-methylhept-6-ene-3-sulfonamide] or [(3S,4S)-4-methoxy-N,N-bis(4-methoxybenzyl)-2-methylhept-6-ene-3-sulfonamide and (3R,4R)-4-methoxy-N,N-bis(4-methoxybenzyl)-2-methylhept-6-ene-3-sulfonamide]

Step 7: [(3R,4S)-4-methoxy-2-methylhept-6-ene-3-sulfonamide and (3S,4R)-4-methoxy-2-methylhept-6-ene-3-sulfonamide] or [(3S,4S)-4-methoxy-2-methylhept-6-ene-3-sulfonamide and (3R,4R)-4-methoxy-2-methylhept-6-ene-3-sulfonamide]

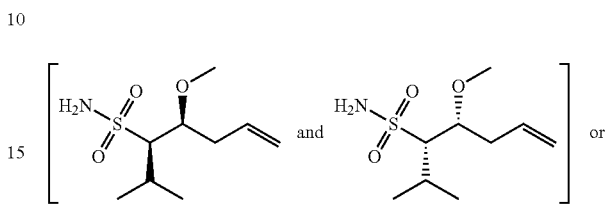

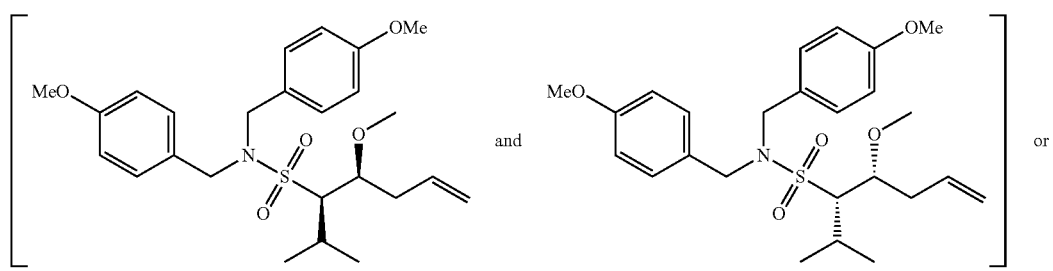

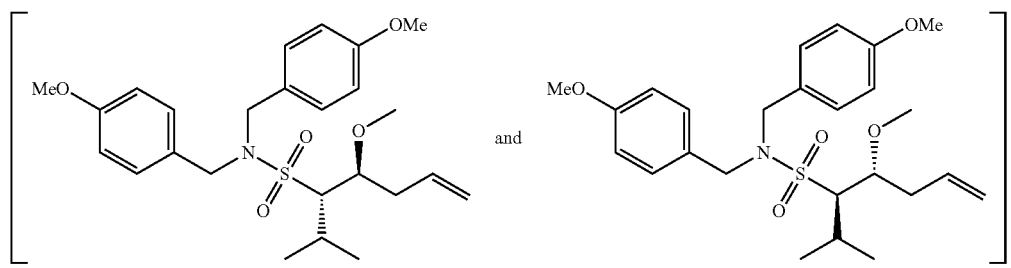

To a solution of [(3R,4S)-4-hydroxy-N,N-bis(4-methoxybenzyl)-2-methylhept-6-ene-3-sulfonamide and (3S,4R)-4-hydroxy-N,N-bis(4-methoxybenzyl)-2-methylhept-6-ene-3-sulfonamide] or [(3S,4S)-4-hydroxy-N,N-bis(4-methoxybenzyl)-2-methylhept-6-ene-3-sulfonamide and (3R,4R)-4-hydroxy-N,N-bis(4-methoxybenzyl)-2-methylhept-6-ene-3-sulfonamide](enantiomeric mixture 1 in Example 571, Step 5) (242 mg, 0.541 mmol) and iodomethane (0.336 ml, 5.41 mmol) in THF (5.4 mL) was added t-BuOK (1 M solution in THF, 0.65 mL, 0.65 mmol) at 0° C. The reaction was allowed to warm to ambient temperature and stirred overnight. The reaction was quenched (brine), extracted (2×EtOAc), and washed (brine). The combined organic layers were dried (MgSO₄) and concentrated under reduced pressure to provide crude products (250 mg, 0.542 mmol, 100%) as a colorless film, which were used in the next step without further purification.

-continued

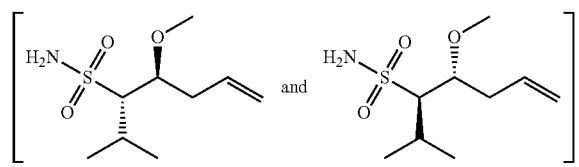

To a solution of [(3R,4S)-4-methoxy-N,N-bis(4-methoxybenzyl)-2-methylhept-6-ene-3-sulfonamide and (3S,4R)-4-methoxy-N,N-bis(4-methoxybenzyl)-2-methylhept-6-ene-3-sulfonamide] or [(3S,4S)-4-methoxy-N,N-bis(4-methoxybenzyl)-2-methylhept-6-ene-3-sulfonamide and (3R,4R)-4-methoxy-N,N-bis(4-methoxybenzyl)-2-methylhept-6-ene-3-sulfonamide](Example 571, Step 6) (250 mg, 0.542 mmol) in anisole (5.89 mL, 54.2 mmol) was added 2,2,2-trifluoroacetic acid (4.02 mL, 54.2 mmol) at ambient temperature. After the reaction was stirred for 3 h, the reaction was heated to 50° C. for 22 h. Then reaction mixture was cooled to ambient temperature, concentrated under reduced pressure. The crude product was injected into a 4 g ISCO Gold column and purified by combi-flash, eluting with 0% to 20% MeOH/DCM with 0.3% AcOH provided the products (97.4 mg, 0.440 mmol, 81% yield) as a pale brown liquid.

Step 8: [(S)-6'-chloro-5-(((1R,2R)-2-((1S,5R,6R,E)-1-hydroxy-5-methoxy-7-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,6S,E)-1-hydroxy-5-methoxy-7-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid] or [(S)-6'-chloro-5-(((1R,2R)-2-((1S,5S,6R,E)-1-hydroxy-5-methoxy-7-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5R,6S,E)-1-hydroxy-5-methoxy-7-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid]

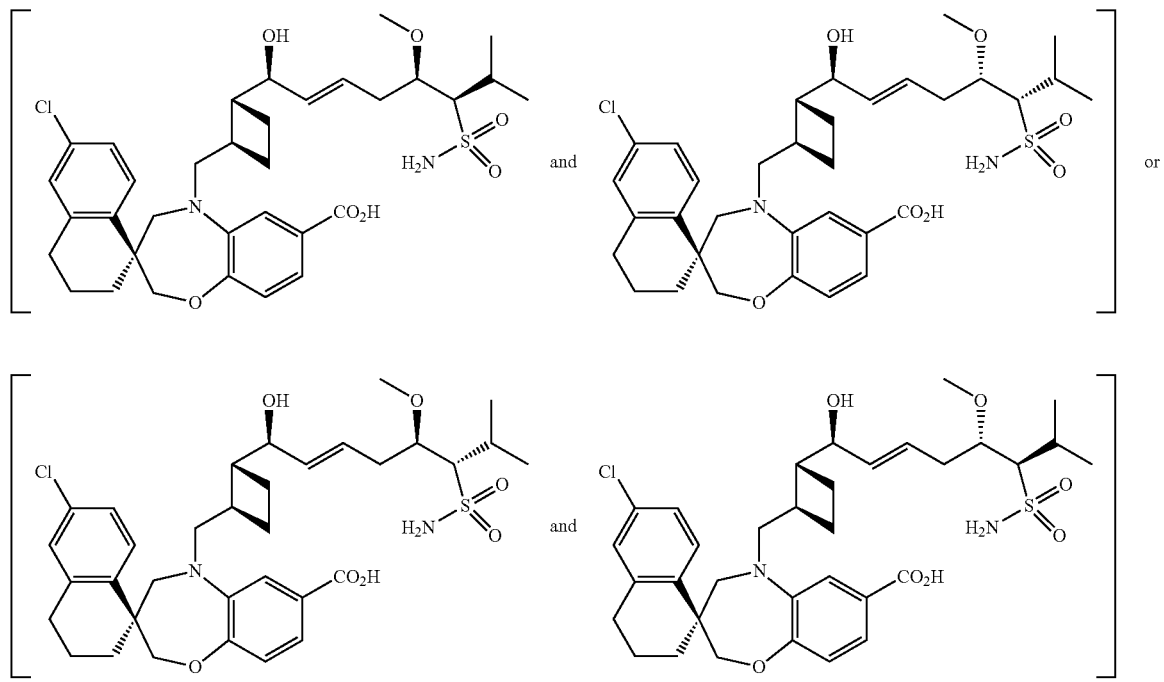

(S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A) (55.9 mg, 0.110 mmol) and [(3R,4S)-4-methoxy-2-methylhept-6-ene-3-sulfonamide and (3S,4R)-4-methoxy-2-methylhept-6-ene-3-sulfonamide] or [(3S,4S)-4-methoxy-2-methylhept-6-ene-3-sulfonamide and (3R,4R)-4-methoxy-2-methylhept-6-ene-3-sulfonamide] (Example 571, Step 7) (97 mg, 0.438 mmol) were dissolved in DCE (1.2 mL) under Ar. The solution was sparged with Ar for 5 min and Hoveyda-Grubbs 2nd generation catalyst (14 mg, 0.022 mmol) was added at ambient temperature. The mixture was stirred at ambient temperature for 2.5 h while sparging the reaction with Ar (the clear green solution becomes increasingly darker). Then, after air was bubbling through the reaction for 10 min, the reaction was concentrated under reduced pressure, and directly absorbed to silica-gel. Purification of the residue by flash column chromatography (4 g SiO₂, 20% to 100% EtOAc/Hex with 0.3% AcOH) provided the products (72.5 mg, 0.110 mmol, 100%) as a off-white film.

Step 9: (1S,3'R,6'R,7'S,8'E,11'S,12'R)-6-chloro-7'-hydroxy-11'-methoxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-7'-hydroxy-11'-methoxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-11'-methoxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methoxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Isomer 1)

To a solution of [(S)-6'-chloro-5-(((1R,2R)-2-((1S,5R,6R,E)-1-hydroxy-5-methoxy-7-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,6S,E)-1-hydroxy-5-methoxy-7-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid] or [(S)-6'-chloro-5-(((1R,2R)-2-((1S,5S,6R,E)-1-hydroxy-5-methoxy-7-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5R,6S,E)-1-hydroxy-5-methoxy-7-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid] (Example 571, Step 8) (72.5 mg, 0.110 mmol) in DCM (3.7 mL) was added EDC (63.1 mg, 0.329 mmol), DMAP (40.2 mg, 0.329 mmol), and triethylamine (45.8 µl, 0.329 mmol) at ambient temperature. After the reaction was stirred for 18 h, the reaction was directly loaded into silica-gel and purification by flash column chromatography (4 g SiO$_2$, 0% to 100% EA/hexanes) provided a crude product as a pale brown film. The crude product was purified by chiral SFC (AS-H 21×250 mm column, Phenomenex, Torrance, CA; using gradient elution of 18%-50% EtOH (20 mM NH$_3$)/CO$_2$) to provide one of the title compounds (isomer 1) as the third (slowest) eluting isomer. $^1$H NMR (400 MHz, CDCl$_3$) δ ppm 7.72 (d, J=8.4 Hz, 1H), 7.58 (s, 1H), 7.43 (d, J=8.2 Hz, 1H), 7.18 (dd, J=2.2, 8.5 Hz, 1H), 7.09 (d, J=2.2 Hz, 1H), 6.93 (d, J=7.5 Hz, 1H), 5.77-5.58 (m, 2H), 5.08 (br. s., 1H), 4.21-4.02 (m, 3H), 3.97-3.85 (m, 1H), 3.80 (m, 1H), 3.73-3.60 (m, 1H), 3.40 (s, 3H), 3.28 (d, J=14.3 Hz, 1H), 3.22-3.05 (m, 2H), 2.86-2.70 (m, 2H), 2.68-2.50 (m, 2H), 2.48-2.23 (m, 2H), 2.20-2.10 (m, 1H), 2.10-1.98 (m, 2H), 1.97-1.88 (m, 1H), 1.83 (m, 2H), 1.76-1.57 (m, 2H), 1.48 (t, J=11.6 Hz, 1H), 1.32-1.23 (d, J=7.0 Hz, 3H), 1.23-1.14 (d, J=7.0 Hz, 3H); m/z (ESI, +ve ion) 661.2 (M+Na)$^+$.

Example 572. (1S,3'R,6'R,7'S,8'E,11'S,12'R)-6-chloro-7'-hydroxy-11'-methoxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-7'-hydroxy-11'-methoxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-11'-methoxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methoxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Isomer 2)

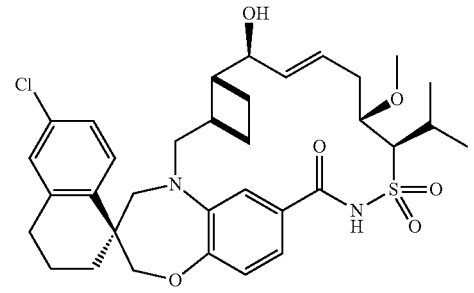

or

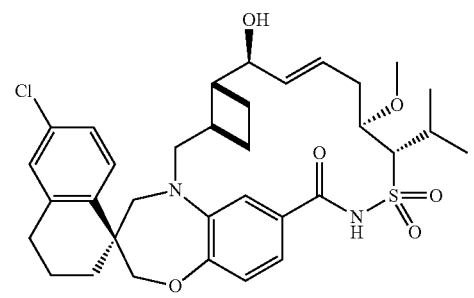

or

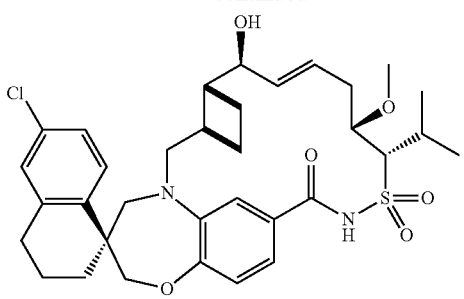

or

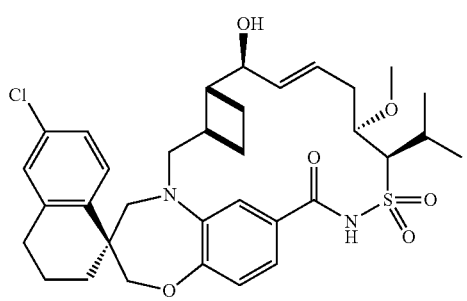

One of the title compounds was prepared by a procedure analogous to that described in Example 571, Steps 6 through 9, replacing [(3R,4S)-4-hydroxy-N,N-bis(4-methoxybenzyl)-2-methylhept-6-ene-3-sulfonamide and (3S,4R)-4-hydroxy-N,N-bis(4-methoxybenzyl)-2-methylhept-6-ene-3-sulfonamide] or [(3R,4R)-4-hydroxy-N,N-bis(4-methoxybenzyl)-2-methylhept-6-ene-3-sulfonamide and (3S,4S)-4-hydroxy-N,N-bis(4-methoxybenzyl)-2-methylhept-6-ene-3-sulfonamide] (enantiomeric mixture 1 in Example 571, Step 5) with [(3R,4S)-4-hydroxy-N,N-bis(4-methoxybenzyl)-2-methylhept-6-ene-3-sulfonamide and (3S,4R)-4-hydroxy-N,N-bis(4-methoxybenzyl)-2-methylhept-6-ene-3-sulfonamide] or [(3R,4R)-4-hydroxy-N,N-bis(4-methoxybenzyl)-2-methylhept-6-ene-3-sulfonamide and (3S,4S)-4-hydroxy-N,N-bis(4-methoxybenzyl)-2-methylhept-6-ene-3-sulfonamide] (enantiomeric mixture 2 in Example 571, Step 5). The crude product from silica-gel column chromatography was purified by chiral SFC (AD-H 21×250 mm column, Phenomenex, Torrance, CA; using 14 g/min MeOH(neat)+56 g/min $CO_2$, 25% co-solvent at 70 g/min, isocratic.) to provide one of the title compounds (isomer 2) as the faster eluting isomer as a white foam. $^1$H NMR (400 MHz, CDCl$_3$) δ ppm 7.69 (d, J=8.4 Hz, 1H), 7.61 (m, 1H), 7.48-7.37 (m, 1H), 7.15 (d, J=8.7 Hz, 1H), 7.10-7.09 (m, 1H), 6.93 (d, J=8.0 Hz, 1H), 5.73-5.53 (m, 2H), 5.25 (m, 1H), 4.16-4.03 (m, 3H), 3.88-3.77 (m, 1H), 3.70-3.57 (m, 2H), 3.43 (s, 3H), 3.28 (d, J=14.5 Hz, 1H), 3.22-3.08 (m, 2H), 2.83-2.62 (m, 3H), 2.52 (m, 1H), 2.37-2.11 (m, 3H), 2.06-1.44 (m, 8H), 1.17 (d, J=7.0 Hz, 3H), 1.11 (d, J=7.0 Hz, 3H); m/z (ESI, +ve ion) 661.2 (M+Na)$^+$.

Example 573. (1S,3'R,6'R,7'S,8'E,11'S,12'R)-6-chloro-7'-hydroxy-11'-methoxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-7'-hydroxy-11'-methoxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-11'-methoxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methoxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

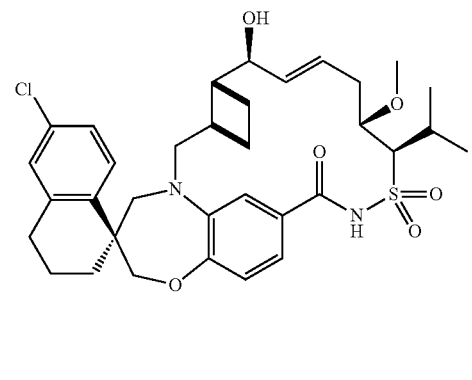

or

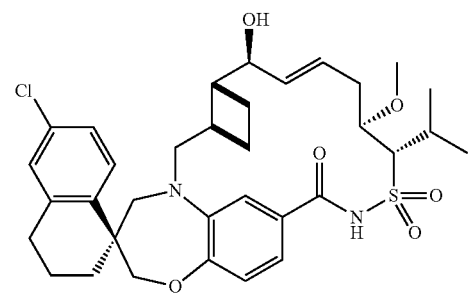

or

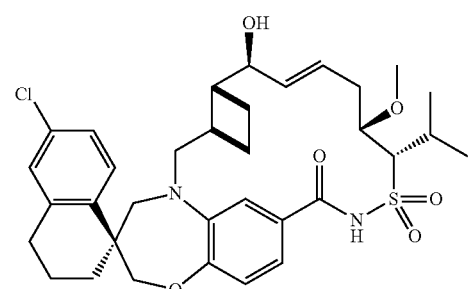

or

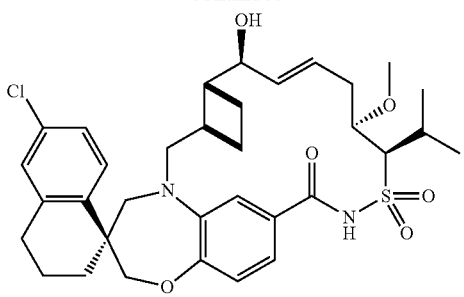

One of the title compounds (isomer 3) was obtained as the second (slower) eluting isomer from SFC purification in Example 572. $^1$H NMR (400 MHz, CDCl$_3$) δ ppm 7.71 (d, J=8.6 Hz, 1H), 7.65 (m, 1H), 7.44 (m, 1H), 7.18 (dd, J=2.2, 8.5 Hz, 1H), 7.10 (d, J=2.2 Hz, 1H), 6.93 (d, J=8.2 Hz, 1H), 5.79-5.68 (m, 1H), 5.66-5.56 (m, 1H), 5.24 (m, 1H), 4.20-4.04 (m, 3H), 3.74 (m, 1H), 3.70-3.56 (m, 2H), 3.43 (s, 3H), 3.39-3.15 (m, 3H), 2.90-2.64 (m, 3H), 2.60-2.39 (m, 1H), 2.37-2.11 (m, 3H), 2.07-1.47 (m, 8H), 1.19 (d, J=7.2 Hz, 3H), 1.12 (d, J=7.2 Hz, 3H); m/z (ESI, +ve ion) 661.2 (M+Na)$^+$.

Example 574. (1S,3'R,6'R,7'S,8'E,11'S,12'R)-6-chloro-12'-(cyclopropylmethyl)-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-12'-(cyclopropylmethyl)-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-12'-(cyclopropylmethyl)-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-12'-(cyclopropylmethyl)-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (Isomer 1)

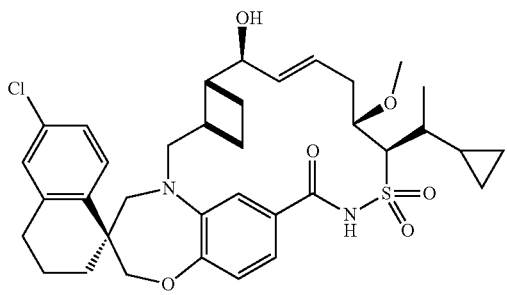

or

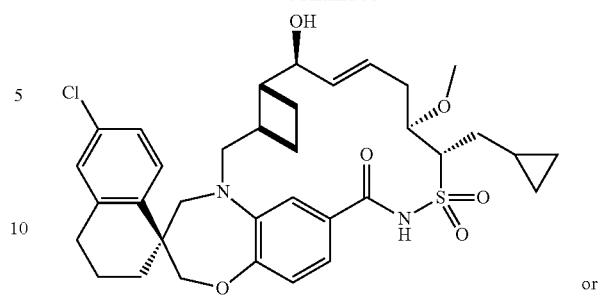

or

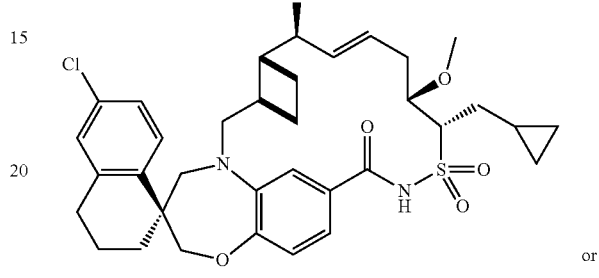

or

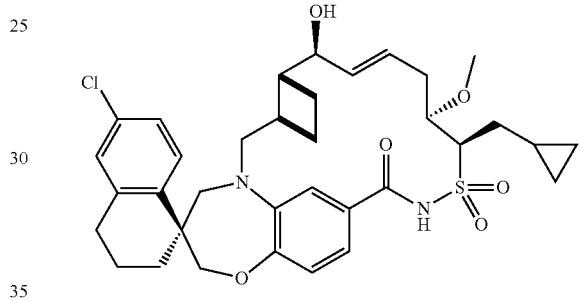

Step 1: 2-cyclopropyl-N,N-bis(4-methoxybenzyl)ethanesulfonamide

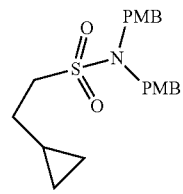

To a solution of N,N-bis(4-methoxybenzyl)methanesulfonamide (Intermediate EE12) (3.15 g, 9.39 mmol) in THF (12 mL) was added n-BuLi (2.5 M solution in hexanes, 4.88 ml, 12.2 mmol) at −78° C. dropwise. After the reaction was stirred at the same temperature for 10 min, (bromomethyl)cyclopropane (3.64 ml, 37.6 mmol) was added into the reaction for 30 minutes at the same temperature. Then, the reaction was allowed to warm to ambient temperature and stirred for 2 h. The reaction was quenched (Saturated aqueous NH$_4$Cl) and extracted (2×EtOAc). The combined organic layers were washed (brine), dried (MgSO$_4$), and concentrated under reduced pressure. Purification of the residue by flash column chromatography (4 g SiO$_2$, 0% to 30% EA/hexanes) provided the product (2.70 g, 6.93 mmol, 74%).

Step 2: (2R,3S)-1-cyclopropyl-3-methoxyhex-5-ene-2-sulfonamide and (2S,3R)-1-cyclopropyl-3-methoxyhex-5-ene-2-sulfonamide and (2R,3R)-1-cyclopropyl-3-methoxyhex-5-ene-2-sulfonamide and (2S,3S)-1-cyclopropyl-3-methoxyhex-5-ene-2-sulfonamide

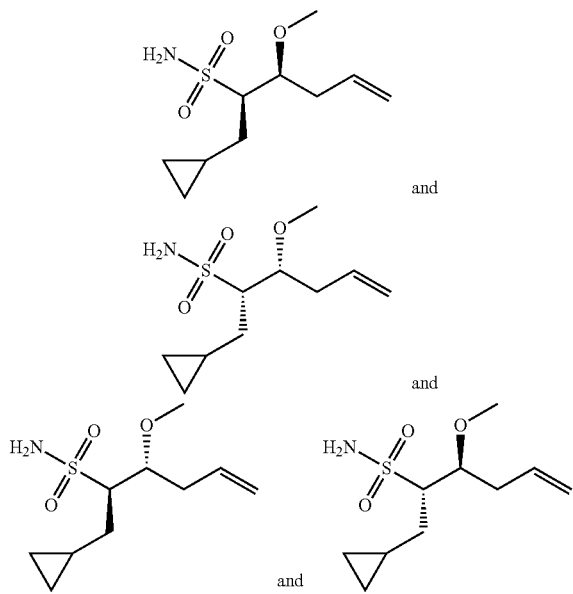

and and and

Title compounds were prepared as a mixture of four diastereomers by a procedure analogous to that described in Example 571, Steps 2 through 7, replacing N,N-bis(4-methoxybenzyl)-2-methylpropane-1-sulfonamide in Step 2 with 2-cyclopropyl-N,N-bis(4-methoxybenzyl)ethanesulfonamide (Example 574, Step 1).

Step 3: (1S,3'R,6'R,7'S,8'E,11'S,12'R)-6-chloro-12'-(cyclopropylmethyl)-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-12'-(cyclopropylmethyl)-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-12'-(cyclopropylmethyl)-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-12'-(cyclopropylmethyl)-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (Isomer 1)

One of the title compounds was prepared by a procedure analogous to that described in Example 571, Steps 8 and 9, replacing [(3R,4S)-4-methoxy-2-methylhept-6-ene-3-sulfonamide and (3S,4R)-4-methoxy-2-methylhept-6-ene-3-sulfonamide] or [(3S,4S)-4-methoxy-2-methylhept-6-ene-3-sulfonamide and (3R,4R)-4-methoxy-2-methylhept-6-ene-3-sulfonamide] in Step 8 with (2R,3S)-1-cyclopropyl-3-methoxyhex-5-ene-2-sulfonamide and (2S,3R)-1-cyclopropyl-3-methoxyhex-5-ene-2-sulfonamide and (2R,3R)-1-cyclopropyl-3-methoxyhex-5-ene-2-sulfonamide and (2S,3S)-1-cyclopropyl-3-methoxyhex-5-ene-2-sulfonamide (Example 574, Step 2). The crude product was purified by reversed phase preparatory HPLC (Gemini™ Prep C$_{18}$ 5 μm column; Phenomenex, Torrance, CA; gradient elution of 50% to 75% MeCN in water, where both solvents contain 0.1% TFA, 30 min method) to provide one of the title compounds (isomer 1) the faster eluting isomer. $^1$H NMR (400 MHz, CDCl$_3$) δ ppm 8.32 (br. s., 1H), 7.70 (d, J=8.4 Hz, 1H), 7.18 (dd, J=2.3, 8.4 Hz, 1H), 7.10 (d, J=2.2 Hz, 2H), 7.00-6.90 (m, 2H), 5.83-5.69 (m, 2H), 4.25-4.16 (m, 2H), 4.16-4.09 (m, 2H), 3.75 (m, 1H), 3.67 (m, 2H), 3.48-3.26 (m, 4H), 3.20 (m, 1H), 2.86-2.70 (m, 2H), 2.60-2.30 (m, 4H), 2.20 (m, 1H), 2.05-1.63 (m, 8H), 1.58-1.38 (m, 1H), 1.11 (m, 1H), 0.64-0.51 (m, 2H), 0.32-0.20 (m, 1H), 0.19-0.07 (m, 1H); m/z (ESI, +ve ion) 655.2 (M+H)$^+$.

Example 575. (1S,3'R,6'R,7'S,8'E,11'S,12'R)-6-chloro-12'-(cyclopropylmethyl)-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-12'-(cyclopropylmethyl)-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-12'-(cyclopropylmethyl)-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-12'-(cyclopropylmethyl)-7'-hydroxy-11'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (Isomer 2)

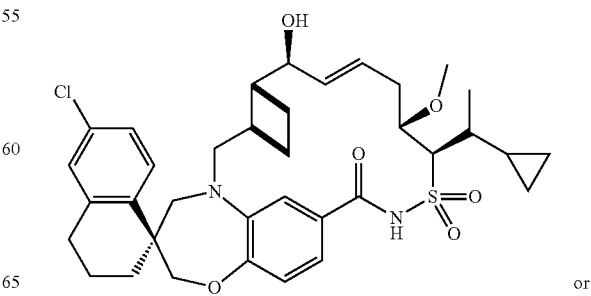

or

-continued

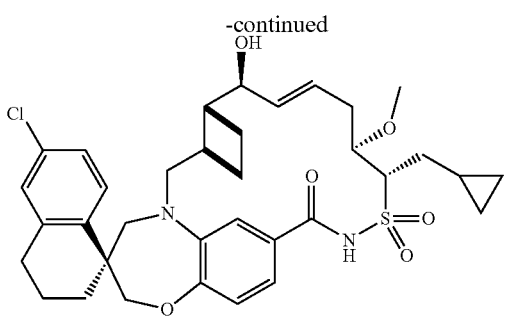

or

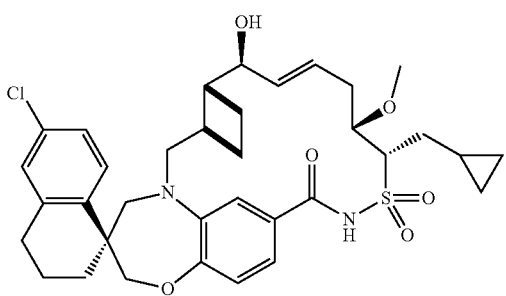

or

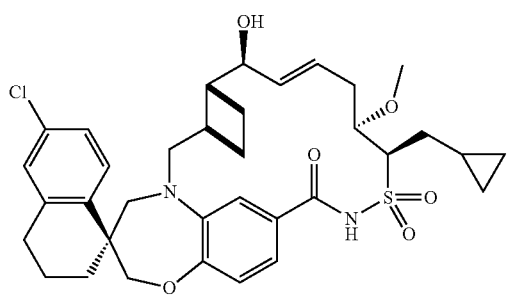

One of the title compounds (isomer 2) was obtained as the second (slower) eluting isomer from the reversed phase preparatory HPLC purification in Example 574, Step 3. $^1$H NMR (400 MHz, CDCl$_3$) δ ppm 7.84 (br. s., 1H), 7.78-7.68 (m, 1H), 7.18 (dd, J=2.2, 8.5 Hz, 1H), 7.09 (d, J=2.2 Hz, 1H), 6.97-6.87 (m, 3H), 5.91-5.70 (m., 2H), 4.37 (m, 1H), 4.20 (m, 1H), 4.17-4.01 (m, 2H), 3.77 (m, 3H), 3.34-2.97 (m, 5H), 2.85-2.68 (m, 3H), 2.48-2.30 (m, 2H), 2.09-1.61 (m, 10H), 1.50-1.35 (m, 1H), 1.18-1.05 (m, 1H), 0.61 (m, 2H), 0.25-0.15 (m, 2H); m/z (ESI, +ve ion) 655.2 (M+H)$^+$.

Example 576. methyl ((1S,3'R,6'R,7'S,8'E,11'S,12'R)-6-chloro-7'-methoxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetate or methyl ((1 S,3'R,6'R,7'S,8'E,11'R,12'S)-6-chloro-7'-methoxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetate or methyl ((1S,3'R,6'R,7'S,8'E,11'R,12'R)-6-chloro-7'-methoxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetate or methyl ((1S,3'R,6'R,7'S,8'E,11'S,12'S)-6-chloro-7'-methoxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetate

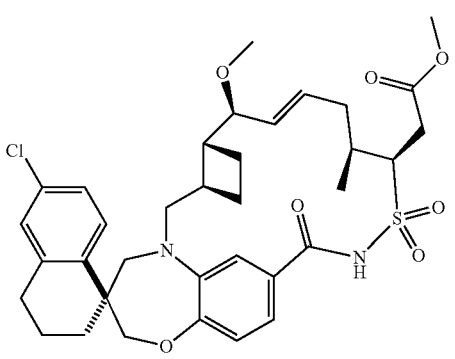

or

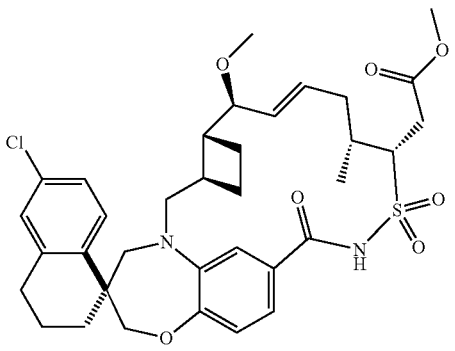

or

or

-continued

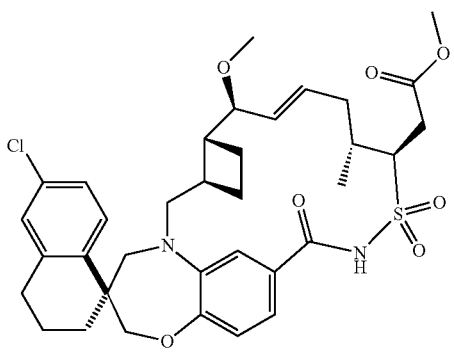

To a vigorously stirring solution of methyl ((1S,3'R,6'R, 7'S,8'E,11'S,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetate or methyl ((1S,3'R,6'R,7'S,8'E,11'R,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetate or methyl ((1S,3'R,6'R,7'S,8'E,11'R,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetate or methyl ((1S,3'R,6'R,7'S,8'E,11'S,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetate (Example 647) (22 mg, 0.033 mmol) and tetrafluoroboric acid (48% w/w % in water, 5.1 µL, 0.039 mmol) in DCM (0.66 mL) was added (trimethylsilyl) diazomethane (2.0 M solution in Et$_2$O, 20 µL, 0.039 mmol) at 0° C. After the reaction was stirred at 0° C. for 1 h, the reaction was quenched (MeOH), diluted (cold water), extracted (2×EtOAc). The combined organic layers were washed (brine), dried (MgSO$_4$), concentrated under reduced pressure. The crude product was purified by reversed phase preparatory HPLC (Gemini™ Prep C$_{18}$ 5 µm column; Phenomenex, Torrance, CA; gradient elution of 50% to 80% MeCN in water, where both solvents contain 0.1% TFA, 30 min method) to provide one of the title compounds as a white foam (8.1 mg, 0.012 mmol). $^1$H NMR (400 MHz, CDCl$_3$) δ ppm 7.99 (br. s., 1H), 7.70 (d, J=8.6 Hz, 1H), 7.19 (dd, J=2.2, 8.5 Hz, 1H), 7.10 (d, J=2.3 Hz, 1H), 6.95-6.88 (m, 3H), 5.99-5.91 (m, 1H), 5.54 (dd, J=9.3, 15.2 Hz, 1H), 4.95 (t, J=6.4 Hz, 1H), 4.10 (s, 2H), 3.83 (d, J=15.1 Hz, 1H), 3.78 (s, 3H), 3.74-3.67 (m, 2H), 3.29-3.21 (m, 4H), 3.15-2.96 (m, 2H), 2.84-2.67 (m, 3H), 2.52-2.42 (m, 1H), 2.41-2.26 (m, 1H), 2.16-1.76 (m, 9H), 1.74-1.60 (m, 1H), 1.40 (m, 1H), 1.09 (d, J=6.1 Hz, 3H); m/z (ESI, +ve ion) 671.2 (M+H)$^+$.

Example 581. (1S,3'R,6'R,11'S,12'R)-6-chloro-11',12'-dimethyl-7'-methylidene-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24] trien]-15'-one 13',13'-dioxide

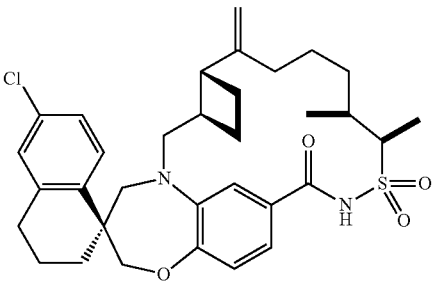

Step 1: (1S,3'R,6'R,11'S,12'R)-6-chloro-11',12'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [16,18,24]triene]-7',15'-dione 13',13'-dioxide

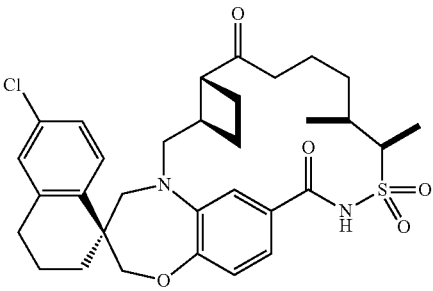

To a solution of (1S,3'R,6'R,7'S,8'E,11'S,12'R)-6-chloro-7'-hydroxy-11',12'-dimethyl-3,4-dihydro-2h,15'h-spiro [naphthalene-1,22'-[20]oxa[13]thia[1,14]diazatetracyclo [14.7.2.03,6.019,24]pentacosa[8,16,18,24]tetraen]-15'-one 13',13'-dioxide (1.20 g, 2.02 mmol, Example 719, Step 2) in EtOAc (50 mL) was added platinum (IV) oxide (92 g, 0.40 mmol, Aldrich) and the reaction was fitted with a H$_2$ balloon and stirred vigorously for 15 h. The reaction mixture was filtered through Celite and concentrated to a yellow glaze. The yellow glaze was dissolved in dichloromethane (20 mL) and then Dess-Martin periodinane (0.95 g, 2.2 mmol, Aldrich) was added in four portions over 5 min at 0° C. After the reaction was stirred at 0° C. for 15 min, the reaction was quenched with 1N sodium thiosulfate solution at 0° C. (10 mL) and stirred vigorously at rt for 30 min. Then the reaction mixture was extracted (EtOAc). The separated organic layer was washed (brine), dried (Na$_2$SO$_4$), and concentrated under reduced pressure. The residue was purified by silica-gel chromatography (0-25% EtOAc/hexs, 0.1% AcOH) to provide (1S,3'R,6'R,11'S,12'R)-6-chloro-11',12'-dimethyl-3,4-dihydro-2H,7'H,15'H-spiro[naphthalene-1,22'-[20]oxa[13] thia[1,14]diazatetracyclo[14.7.2.0$^{3,6}$.0$^{19,24}$]pentacosa[16,18,24]triene]-7',15'-dione 13',13'-dioxide as an off-white solid (0.85 g, 70% yield). m/z (ESI, +ve ion) 599.2 (M+H)$^+$.

1247

Step 2: (1S,3'R,6'R,11'S,12'R)-6-chloro-11',12'-dimethyl-7'-methylidene-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide To a solution of (1S,3'R,6'R,11'S,12'R)-6-chloro-11',12'-dimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[16,18,24]triene]-7',15'-dione 13',13'-dioxide (60 mg, 0.100 mmol) in THF (5.00 mL) was added Tebbe reagent (285 mg, 1.00 mmol, Aldrich) at rt. After the reaction was stirred at rt for 30 min, the reaction was quenched with saturated sodium bicarbonate solution (10 mL). Then the reaction mixture was extracted (Et₂O). The separated organic layer was washed (brine), dried (Na₂SO₄), and concentrated under reduced pressure. The residue was purified by silica-gel chromatography (5-30% EtOAc/heptanes with 0.1% AcOH) to give the title compound as an off-white solid (12 mg, 0.018 mmol, 18% yield). ¹H NMR (400 MHz, CD₂Cl₂) δ 8.20-7.91 (m, 1H), 7.68-7.58 (m, 1H), 7.16-6.95 (m, 2H), 6.89-6.73 (m, 3H), 4.83-4.55 (m, 2H), 4.09-3.93 (m, 3H), 3.74-3.49 (m, 2H), 3.23-3.04 (m, 1H), 2.92 (dd, J=8.3, 15.4 Hz, 1H), 2.79-2.62 (m, 3H), 2.55-2.42 (m, 1H), 2.05-1.68 (m, 9H), 1.57-1.34 (m, 6H), 1.31 (d, J=7.2 Hz, 3H), 0.91 (d, J=6.8 Hz, 3H). m/z (ESI, +ve ion) 597.2 (M+H)⁺.

Example 597. (1S,3'R,6'R,7'S,9'E,11'S)-6-chloro-7',11'-dihydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa [9,16,18,24]tetraen]-15'-one 13',13'-dioxide or (1S,3'R,6'R,7'S,9'E,11'R)-6-chloro-7',11'-dihydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa [9,16,18,24]tetraen]-15'-one 13',13'-dioxide

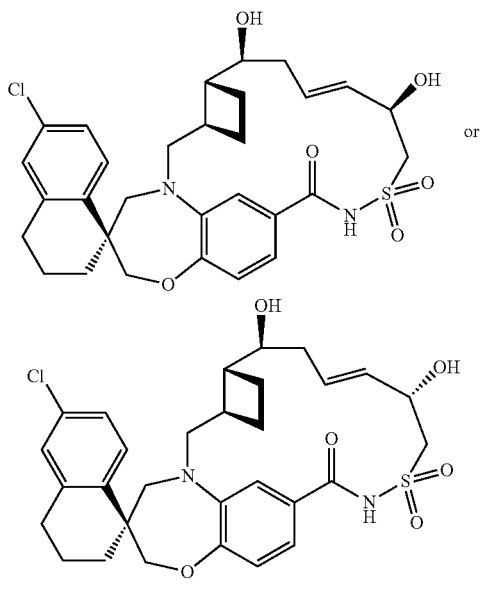

1248

Step 1: 2-(benzylthio)acetaldehyde

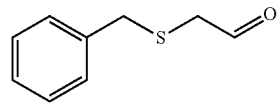 [SMILES: O=CCSCc1ccccc1]

To a solution of sodium ethoxide (18.4 ml, 49.3 mmol) in EtOH (10 ml) was added benzyl mercaptan (5.82 ml, 49.3 mmol). potassium iodide (0.250 g, 1.51 mmol) and 2-chloro-1,1-dimethoxyethane (5.61 ml, 49.3 mmol). The reaction mixture was heated to reflux for 4h. The precipitate was filtered off, washed with ethanol. The filtrate was concentrated in vacuo, and purified by column chromatography on silica gel (20% EtOAc/hexanes) to afford benzyl (2,2-dimethoxyethyl)sulfane (9.00 g) as a slightly yellow oil. The oil (6.00 g) was heated at 60° C. with 0.5 M aqueous H₂SO₄ (30 mL) for 2h. The reaction mixture was neutralized with solid NaHCO₃ and extracted three times with 20 mL portions of DCM. The organic phase was dried over Na₂SO₄ and concentrated to afford 2-(benzylthio)acetaldehyde (4.84 g) as a slightly yellow liquid. ¹H NMR (500 MHz, CDCl₃) δ 9.43 (1H, t, J=3.3 Hz), 7.37-7.25 (5H, m), 3.64 (2H, s), 3.09 (2H, d, J=3.4 Hz).

Step 2: (R)-1-(benzylthio)but-3-en-2-ol and (S)-1-(benzylthio)but-3-en-2-ol

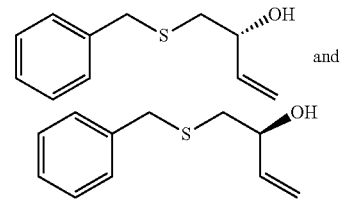

To a solution of 2-(benzylthio)acetaldehyde from Step 1 (4.78 g, 28.8 mmol) in THF (10 mL) at 0° C. was slowly added vinylmagnesium bromide, 0.7m solution in tetrahydrofuran (49.3 mL, 34.5 mmol). After stirring at 0° C. for 30 min, the reaction was quenched with saturated aqueous NH₄Cl solution. The precipitated solids were dissolved with water and extracted with EtOAc. After drying and concentration, the residue was purified by column chromatography (20% EtOAc/hexanes) to give (R)-1-(benzylthio)but-3-en-2-ol and (S)-1-(benzylthio)but-3-en-2-ol (1.39 g). ¹H NMR (500 MHz, CDCl₃) δ 7.30-7.25 (m, 3H), 7.24-7.19 (m, 2H), 5.82-5.74 (m, 1H), 5.24 (dt, J=17.1, 1.3 Hz, 1H), 5.11 (dt, J=10.3, 1.2 Hz, 1H), 4.13-4.07 (m, 1H), 3.71 (s, 2H), 2.61 (dd, J=13.7, 3.9 Hz, 1H), 2.47 (dd, J=13.7, 8.3 Hz, 1H), 2.38 (br. s., 1H).

Step 3: (R)-((1-(benzylthio)but-3-en-2-yl)oxy)(tert-butyl)diphenylsilane and (S)-((1-(benzylthio)but-3-en-2-yl)oxy)(tert-butyl)diphenylsilane

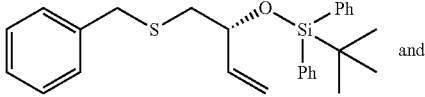

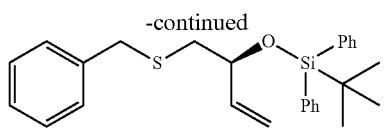

To a solution of (±)1-(benzylthio)but-3-en-2-ol from Step 2 (1.0 g, 5.15 mmol) in CH₂Cl₂ (25.7 ml) was added 2,6-lutidine (1.20 ml, 10.3 mmol), followed by tert-butyldiphenylsilyl triflate (2.40 g, 6.20 mmol). The reaction mixture was stirred at ambient temperature for 2h. The volume of the reaction was reduced to half by concentration under vacuum, and then the reaction mixture was loaded directly to a cartridge of silica gel and purified by column chromatography, (0-20% EtOAc/hexanes, 40 g SiO₂) to give (R)-((1-(benzylthio)but-3-en-2-yl)oxy)(tert-butyl)diphenylsilane and (S)-((1-(benzylthio)but-3-en-2-yl)oxy)(tert-butyl)diphenylsilane (2.10 g). ¹H NMR (500 MHz, CDCl₃) δ 7.72-7.67 (2H, m), 7.67-7.62 (2H, m), 7.46-7.40 (2H, m), 7.37 (4H, q, J=6.9 Hz), 7.26-7.17 (3H, m), 7.17-7.11 (2H, m), 5.87 (1H, ddd, J=17.1, 10.6, 6.4 Hz), 5.09-5.01 (2H, m), 4.24 (1H, q, J=6.2 Hz), 3.52-3.42 (2H, m), 2.60-2.52 (1H, m), 2.52-2.45 (1H, m), 1.09-1.05 (9H, m).

Step 4: (S)-2-((tert-butyldiphenylsilyl)oxy)but-3-ene-1-sulfonamide and (R)-2-((tert-butyldiphenylsilyl)oxy)but-3-ene-1-sulfonamide

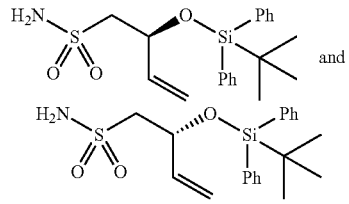

To a mixture of (R)-((1-(benzylthio)but-3-en-2-yl)oxy)(tert-butyl)diphenylsilane and (S)-((1-(benzylthio)but-3-en-2-yl)oxy)(tert-butyl)diphenylsilane from Step 3 (2.10 g, 4.85 mmol) and iodosylbenzene (3.52 g, 16.0 mmol) in 300 ml of ether was added concentrated aqueous hydrogen chloride (35.6 mL, 427 mmol) gradually with vigorously stirring. The resulting mixture was stirred for 3h and the layers was separated. The organic layer was washed with water and dried over Na₂SO₄, concentrated under reduced pressure to give the crude sulfonylchloride product as a pale-yellow oil. The oil was dissolved in 100 mL of DCM, and this solution was slowly added to a stirring solution of aqueous NH₃OH (23%) (67.5 mL, 485 mmol), chilled in an ice-water bath. After the addition, the mixture was stirred at ambient temperature for 0.5h. The layers were separated and the aqueous layer was extracted with DCM. The combined organic layers were dried over Na₂SO₄ and then concentrated under reduced pressure. The residue was purified by column chromatography, (0-70% EtOAc/hexanes, 80 g SiO₂) to give (S)-2-((tert-butyldiphenylsilyl)oxy)but-3-ene-1-sulfonamide and (R)-2-((tert-butyldiphenylsilyl)oxy)but-3-ene-1-sulfonamide. ¹H NMR (500 MHz, CDCl₃) δ 7.74-7.69 (m, 2H), 7.69-7.65 (m, 2H), 7.50-7.44 (m, 2H), 7.43-7.37 (m, 4H), 5.92 (ddd, J=17.2, 10.3, 7.2 Hz, 1H), 5.06 (dt, J=5.1, 1.0 Hz, 1H), 5.03 (dt, J=11.9, 1.0 Hz, 1H), 4.75-4.70 (m, 1H), 4.43 (s, 2H), 3.38-3.32 (m, 1H), 3.29-3.23 (m, 1H), 1.11-1.07 (m, 9H).

The enantiomers were separated by SFC (OJ-H column with 22.5 g/min IPA (20 mM NH₃)+127 g/min CO₂).

Step 5: (S)—N—(((S)-2-((tert-butyldiphenylsilyl)oxy)but-3-en-1-yl)sulfonyl)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide or (S)—N—(((R)-2-((tert-butyldiphenylsilyl)oxy)but-3-en-1-yl)sulfonyl)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide

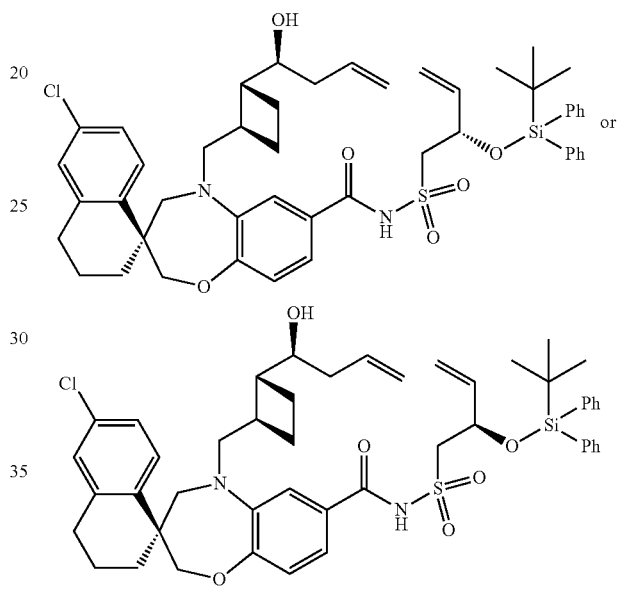

N-(3-dimethylaminopropyl)-N'-ethylcarbodiimide hydrochloride (31.8 mg, 0.166 mmol) was added portionwise to a solution of (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA13A) (50.0 mg, 0.104 mmol) and N,N-dimethylpyridin-4-amine (DMAP) (38.0 mg, 0.311 mmol) in CH₂Cl₂ (2 ml) at 0° C. and stirred at 0° C. for 30 min. (S)-2-((tert-butyldiphenylsilyl)oxy)but-3-ene-1-sulfonamide or (R)-2-((tert-butyldiphenylsilyl)oxy)but-3-ene-1-sulfonamide (first eluting enantiomer from chiral separation in Step 4, 96 mg, 0.246 mmol) was added and the reaction was stirred at 0° C. for 3h then at ambient temperature for 63h. The reaction mixture was loaded directly to silica gel cartridge and purified by column chromatography (0-50% EtOAc/hexane, 12 g SiO₂) to provide (S)—N—(((S)-2-((tert-butyldiphenylsilyl)oxy)but-3-en-1-yl)sulfonyl)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide or (S)—N—(((R)-2-((tert-butyldiphenylsilyl)oxy)but-3-en-1-yl)sulfonyl)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide.

Step 6: (S)-6'-chloro-5-(((1R,2R)-2-((S)-1-hydroxy-but-3-en-1-yl)cyclobutyl)methyl)-N—(((S)-2-hydroxybut-3-en-1-yl)sulfonyl)-3',4',4',5-tetrahydro-2H,2'H-spiro[benzo[b][1,4]oxazepine-3,1'-naphthalene]-7-carboxamide or (S)-6'-chloro-5-(((1R,2R)-2-((R)-1-hydroxybut-3-en-1-yl)cyclobutyl)methyl)-N—(((S)-2-hydroxybut-3-en-1-yl)sulfonyl)-3',4',4',5-tetrahydro-2H,2'H-spiro[benzo[b][1,4]oxazepine-3,1'-naphthalene]-7-carboxamide Step 7: (1S,3'R,6'R,7'S,9'E,11'S)-6-chloro-7',11'-dihydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide or (1S,3'R,6'R,7'S,9'E,11'R)-6-chloro-7',11'-dihydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide

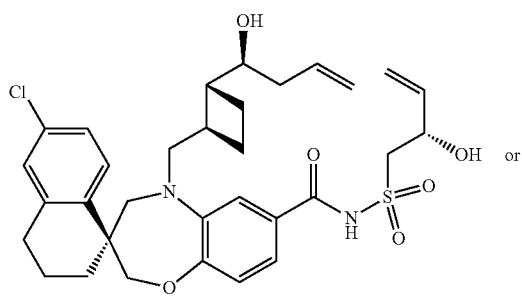

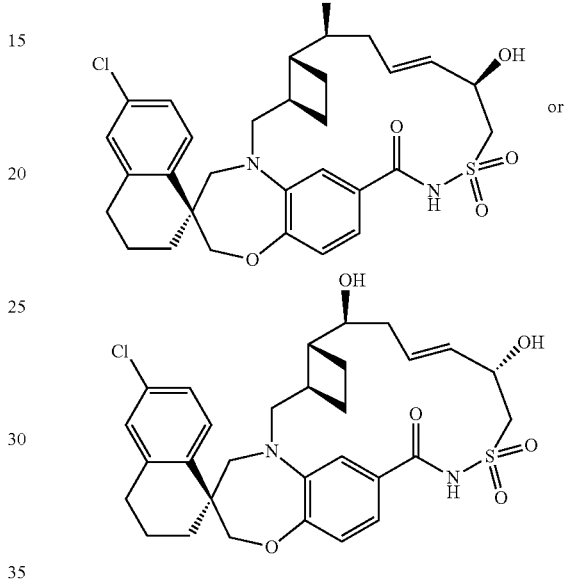

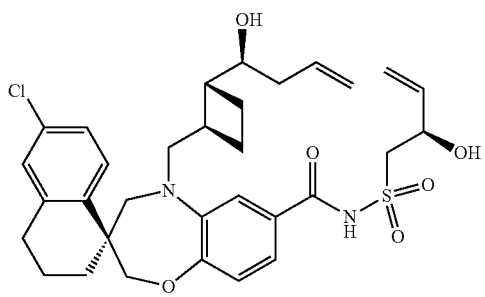

A solution of (S)—N—(((S)-2-((tert-butyldiphenylsilyl)oxy)but-3-en-1-yl)sulfonyl)-6'-chloro-5-(((1R,2R)-2-((S)-1-hydroxybut-3-en-1-yl)cyclobutyl)methyl)-3',4',4',5-tetrahydro-2H,2'H-spiro[benzo[b][1,4]oxazepine-3,1'-naphthalene]-7-carboxamide or (S)—N—(((R)-2-((tert-butyldiphenylsilyl)oxy)but-3-en-1-yl)sulfonyl)-6'-chloro-5-(((1R,2R)-2-((S)-1-hydroxybut-3-en-1-yl)cyclobutyl)methyl)-3',4',4',5-tetrahydro-2H,2'H-spiro[benzo[b][1,4]oxazepine-3,1'-naphthalene]-7-carboxamide from Step 5 (44 mg, 0.051 mmol) in THF (1.0 mL) was treated with TBAF, 1.0M in THF (0.040 mL, 0.15 mmol) and the resulting solution was stirred at ambient temperature for 80 h. The solution was absorbed onto a cartridge of SiO$_2$ and purified by column chromatography, to give (S)-6'-chloro-5-(((1R,2R)-2-((S)-1-hydroxybut-3-en-1-yl)cyclobutyl)methyl)-N—(((S)-2-hydroxybut-3-en-1-yl)sulfonyl)-3',4',4',5-tetrahydro-2H,2'H-spiro[benzo[b][1,4]oxazepine-3,1'-naphthalene]-7-carboxamide or (S)-6'-chloro-5-(((1R,2R)-2-((R)-1-hydroxybut-3-en-1-yl)cyclobutyl)methyl)-N—(((S)-2-hydroxybut-3-en-1-yl)sulfonyl)-3',4',4',5-tetrahydro-2H,2'H-spiro[benzo[b][1,4]oxazepine-3,1'-naphthalene]-7-carboxamide (31 mg). MS (ESI) m/z=637.1 [M+Na]$^+$.

(S)-6'-chloro-5-(((1R,2R)-2-((S)-1-hydroxybut-3-en-1-yl)cyclobutyl)methyl)-N—(((S)-2-hydroxybut-3-en-1-yl)sulfonyl)-3',4',4',5-tetrahydro-2H,2'H-spiro[benzo[b][1,4]oxazepine-3,1'-naphthalene]-7-carboxamide or (S)-6'-chloro-5-(((1R,2R)-2-((R)-1-hydroxybut-3-en-1-yl)cyclobutyl)methyl)-N—(((S)-2-hydroxybut-3-en-1-yl)sulfonyl)-3',4',4',5-tetrahydro-2H,2'H-spiro[benzo[b][1,4]oxazepine-3,1'-naphthalene]-7-carboxamide from Step 6 (31 mg, 0.051 mmol) was dissolved in degassed toluene (26 mL). To this solution was added Hoveyda-Grubbs 2$^{nd}$ Generation catalyst (3.0 mg, 4.8 µmol) at room temperature. The mixture was stirred at 110° C. under argon for 60 min. Air was bubbled through the reaction mixture for 10 min, then the solution was concentrated. The residue was purified by HPLC (5 to 95% MeCN/H$_2$O with 0.1% TFA) to give a product containing an E-olefin. This material was further purified by column chromatography (0-5% MeOH/DCM, 8 g SiO$_2$) to give one of the title compound (5.1 mg). $^1$H NMR (500 MHz, CDCl$_3$) δ 10.14 (br. s., 1H), 7.71 (d, J=8.3 Hz, 1H), 7.41 (dd, J=8.3, 1.7 Hz, 1H), 7.18 (dd, J=8.6, 2.2 Hz, 1H), 7.10 (d, J=2.2 Hz, 1H), 6.98 (d, J=8.3 Hz, 2H), 5.88 (ddd, J=14.7, 10.1, 4.0 Hz, 1H), 5.65 (dd, J=15.2, 8.3 Hz, 1H), 4.68 (d, J=6.8 Hz, 1H), 4.19-4.12 (m, 2H), 4.07 (dd, J=15.2, 9.0 Hz, 1H), 3.94 (d, J=9.8 Hz, 1H), 3.78 (dd, J=15.3, 5.3 Hz, 1H), 3.63 (d, J=14.2 Hz, 2H), 3.38-3.22 (m, 2H), 2.96 (br. s., 1H), 2.87 (br. s., 1H), 2.83-2.74 (m, 2H), 2.52-2.43 (m, 1H), 2.43-2.32 (m, 1H), 2.22-2.11 (m, 1H), 2.05-2.00 (m, 2H), 1.99-1.87 (m, 2H), 1.87-1.71 (m, 3H), 1.71-1.58 (m, 2H), 1.52 (br. s., 1H); MS (ESI) m/z=587.1 [M+H]$^+$.

Example 598. (1S,3'R,6'R,7'S,9'E,11'R)-6-chloro-7',11'-dihydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa [9,16,18,24]tetraen]-15'-one 13',13'-dioxide or (1S,3'R,6'R,7'S,9'E,11'S)-6-chloro-7',11'-dihydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa [9,16,18,24]tetraen]-15'-one 13',13'-dioxide

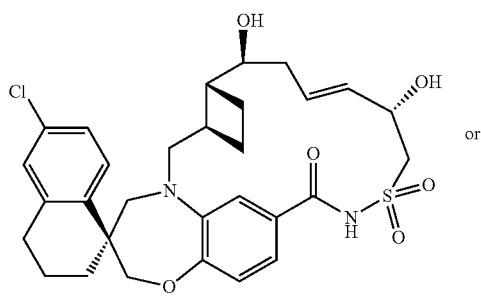

or

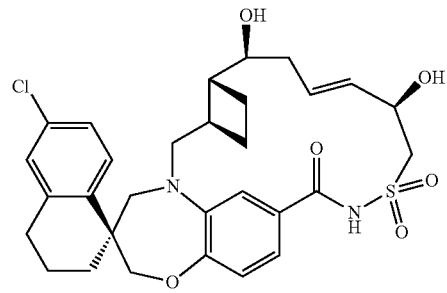

The title compound was synthesized following the same manner as Example 597 Step 5-Step 7 with the second eluting enantiomer isolated from Step 4. ¹H NMR (500 MHz, CDCl₃) δ 10.16 (br. s., 1H), 7.71 (d, J=8.6 Hz, 1H), 7.43 (dd, J=8.3, 1.7 Hz, 1H), 7.18 (dd, J=8.4, 2.3 Hz, 1H), 7.10 (d, J=2.4 Hz, 1H), 6.94-7.03 (m, 2H), 5.80-5.91 (m, 1H), 5.76 (dd, J=15.2, 2.0 Hz, 1H), 4.62 (d, J=8.3 Hz, 1H), 4.27 (dd, J=15.7, 4.2 Hz, 1H), 4.22-4.10 (m, 2H), 3.92 (d, J=9.8 Hz, 1H), 3.68 (dd, J=15.7, 3.9 Hz, 1H), 3.66-3.52 (m, 2H), 3.41-3.26 (m, 2H), 3.01 (br. s., 2H), 2.87-2.69 (m, 3H), 2.55-2.38 (m, 2H), 2.18 (q, J=8.6 Hz, 1H), 2.08-1.99 (m, 1H), 1.98-1.87 (m, 2H), 1.86-1.75 (m, 3H), 1.73-1.63 (m, 1H), 1.61-1.43 (m, 1H); MS (ESI) m/z=587.0 [M+H]⁺.

Example 599. methyl N-(((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl)glycinate-trifluoroacetic Acid

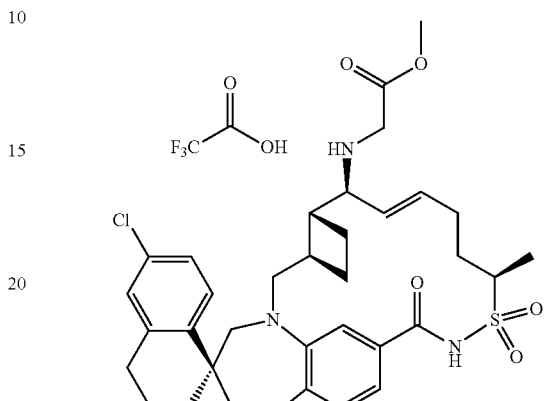

Step 1: (S)-methyl 5-(((1R,2R)-2-((E)-(((R)-tert-butylsulfinyl)imino)methyl)cyclobutyl)methyl)-6'-chloro-3',4,4',5-tetrahydro-2H,2'H-spiro[benzo[b][1,4]oxazepine-3,1'-naphthalene]-7-carboxylate

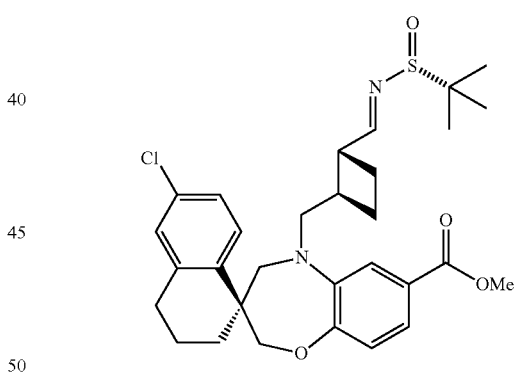

To an oven-dried 100 ml round bottom flask was added (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A) (1.20 g, 2.64 mmol), (R)-(+)-2-methyl-2-propanesulfinamide (961 mg, 7.93 mmol) and CuSO₄ (1.52 g, 15.9 mmol) followed by DCM (15 ml). The resulting mixture was stirred at ambient temperature for 66 h. The crude reaction mixture was filtered, concentrated and the residue purified by column chromatography (0 to 30% EtOAc/hexanes, 40 g SiO₂) to provide (S)-methyl 5-(((1R,2R)-2-((E)-(((R)-tert-butylsulfinyl)imino)methyl)cyclobutyl)methyl)-6'-chloro-3',4,4',5-tetrahydro-2H,2'H-spiro[benzo[b][1,4]oxazepine-3,1'-naphthalene]-7-carboxylate as a white solid. MS (ESI) m/z=579.3 [M+Na]⁺.

Step 2: (S)-methyl 6'-chloro-5-(((1R,2R)-2-((S)-1-((R)-1,1-dimethylethylsulfinamido)allyl)cyclobutyl)methyl)-3',4,4',5-tetrahydro-2H,2'H-spiro[benzo[b][1,4]oxazepine-3,1'-naphthalene]-7-carboxylate Step 3: (S)-6'-chloro-5-(((1R,2R)-2-((S)-1-((R)-1,1-dimethylethylsulfinamido)allyl)cyclobutyl)methyl)-3',4,4',5-tetrahydro-2H,2'H-spiro[benzo[b][1,4]oxazepine-3,1'-naphthalene]-7-carboxylic Acid

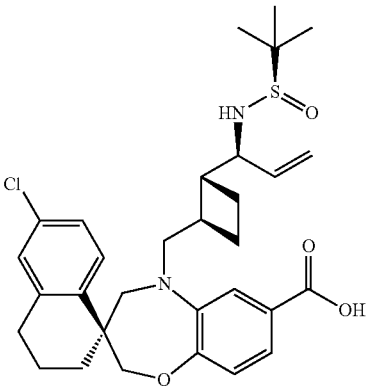

(S)-methyl 6'-chloro-5-(((1R,2R)-2-((S)-1-((R)-1,1-dimethylethylsulfinamido)allyl)cyclobutyl)methyl)-3',4,4',5-tetrahydro-2H,2'H-spiro[benzo[b][1,4]oxazepine-3,1'-naphthalene]-7-carboxylate from Step 2 (493 mg, 0.842 mmol), 1M aqueous LiOH (4.2 mL, 4.2 mmol), THF (5 mL) and EtOH (5 mL) were mixed and stirred at 50° C. for 2h. After cooling to ambient temperature, the mixture was acidified by addition of saturated aqueous NH$_4$Cl, and then extracted with EtOAc. The extract was dried over MgSO$_4$, filtered and concentrated to yield (S)-6'-chloro-5-(((1R,2R)-2-((S)-1-((R)-1,1-dimethylethylsulfinamido)allyl)cyclobutyl)methyl)-3',4,4',5-tetrahydro-2H,2'H-spiro[benzo[b][1,4]oxazepine-3,1'-naphthalene]-7-carboxylic acid as a white solid. MS (ESI) m/z=571.2 [M+H]$^+$.

Step 4: (S)-6'-chloro-5-(((1R,2R)-2-((S)-1-((R)-1,1-dimethylethylsulfinamido)allyl)cyclobutyl)methyl)-N—((R)-hex-5-en-2-ylsulfonyl)-3',4,4',5-tetrahydro-2H,2'H-spiro[benzo[b][1,4]oxazepine-3,1'-naphthalene]-7-carboxamide

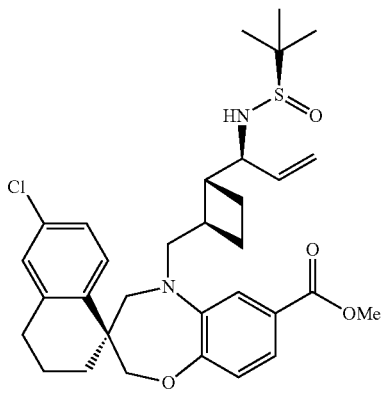 [SMILES: C=C[C@H](N[S@](=O)C(C)(C)C)[C@@H]1CC[C@H]1CN1C[C@@]2(CCCc3cc(Cl)ccc32)COc2ccc(C(=O)OC)cc21]

To a solution of (S)-methyl 5-(((1R,2R)-2-((E)-(((S)-tert-butylsulfinyl)imino)methyl)cyclobutyl)methyl)-6'-chloro-3',4,4',5-tetrahydro-2H,2'H-spiro[benzo[b][1,4]oxazepine-3,1'-naphthalene]-7-carboxylate from Step 1 (0.980 g, 1.76 mmol) in DCM (18 ml) at −10° C. (cooled in an dry ice-acetone bath by controlling small amount of dry ice added every 5 min or so) was added vinylmagnesium bromide, 1.0 M in THF (2.1 mL, 2.1 mmol) dropwise. The reaction mixture was stirred at this temperature for 1h. More vinylmagnesium bromide, 1.0M in THF (2.0 mL, 2.0 mmol) was added and stirred for 30 min more before the reaction was quenched by addition of saturated aqueous NH$_4$Cl (50 ml). The solution was extracted with DCM (80 mL). The separated organic solution was dried over anhydrous Na$_2$SO$_4$ and concentrated under reduced pressure. The residue was purified by column chromatography (0-60% EtOAc/hexanes, 80 g SiO$_2$) to give (S)-methyl 6'-chloro-5-(((1R,2R)-2-((S)-1-((R)-1,1-dimethylethylsulfinamido)allyl)cyclobutyl)methyl)-3',4,4',5-tetrahydro-2H,2'H-spiro[benzo[b][1,4]oxazepine-3,1'-naphthalene]-7-carboxylate. MS (ESI) m/z=585.2 [M+H]$^+$. The other diastereomer was detected but not isolated.

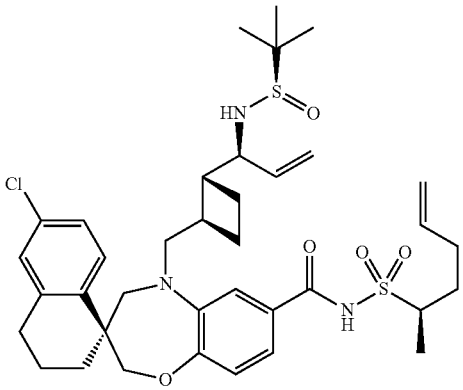 [SMILES: C=CCC[C@@H](C)S(=O)(=O)NC(=O)c1ccc2c(c1)N(C[C@@H]1CC[C@H]1[C@H](C=C)N[S@](=O)C(C)(C)C)C[C@@]1(CCCc3cc(Cl)ccc31)CO2]

(S)-6'-chloro-5-(((1R,2R)-2-((S)-1-((R)-1,1-dimethylethylsulfinamido)allyl)cyclobutyl)methyl)-3',4,4',5-tetrahydro-2H,2'H-spiro[benzo[b][1,4]oxazepine-3,1'-naphthalene]-7-carboxylic acid from Step 3 (480 mg, 0.840 mmol) was azeotroped with toluene. (R)-hex-5-ene-2-sulfonamide (Intermediate EE20) (330 mg, 2.02 mmol), DMAP (257 mg, 2.101 mmol), triethylamine (0.351 mL, 2.52 mmol), and N1-((ethylimino)methylene)-N3,N3-dimethylpropane-1,3-diamine hydrochloride (322 mg, 1.68 mmol) (added at 0° C.) in DCM (20 mL) was stirred at ambient temperature for 17 h. The mixture was concentrated under reduced pressure and purified by column chromatography (0-10% MeOH/DCM, 40 g SiO$_2$) to give (S)-6'-chloro-5-(((1R,2R)-2-((S)-1-((R)-1,1-dimethylethylsulfinamido)allyl)cyclobutyl)methyl)-N—((R)-hex-5-en-2-ylsulfonyl)-3',4,4',5-tetrahydro-2H,2'H-spiro[benzo[b][1,4]oxazepine-3,1'-naphthalene]-7-carboxamide. MS (ESI) m/z=738 [M+Na]$^+$.

Step 5: (S)-1-(((1R,2R)-2-(((S)-6'-chloro-7-(((R)-hex-5-en-2-ylsulfonyl)carbamoyl)-3',4'-dihydro-2H,2'H-spiro[benzo[b][1,4]oxazepine-3,1'-naphthalen]-5 (4H)-yl)methyl)cyclobutyl)prop-2-en-1-aminium chloride

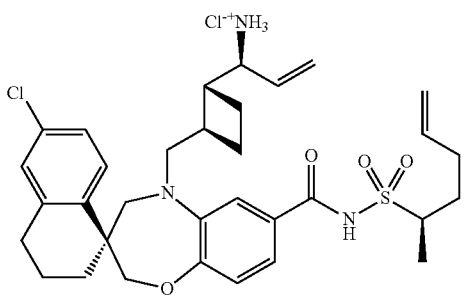

To a solution of (S)-6'-chloro-5-(((1R,2R)-2-((S)-1-((R)-1,1-dimethylethylsulfinamido)allyl)cyclobutyl)methyl)-N—((R)-hex-5-en-2-ylsulfonyl)-3',4,4',5-tetrahydro-2H,2'H-spiro[benzo[b][1,4]oxazepine-3,1'-naphthalene]-7-carboxamide from Step 4 (700 mg, 0.977 mmol) in t-BuOH (10 mL) at ambient temperature, was added a solution of HCl (4 M in 1,4-dioxane, 489 µl, 1.95 mmol), dropwise. The reaction mixture was stirred at for 30 min, then was concentrated under reduced pressure. Purification by column chromatography gave (S)-1-(((1R,2R)-2-(((S)-6'-chloro-7-(((R)-hex-5-en-2-ylsulfonyl)carbamoyl)-3',4'-dihydro-2H,2'H-spiro[benzo[b][1,4]oxazepine-3,1'-naphthalen]-5 (4H)-yl)methyl)cyclobutyl)prop-2-en-1-aminium chloride. MS (ESI) m/z=612.3 [M+H]$^+$.

Step 6: 2-(trimethylsilyl)ethyl ((S)-1-((1R,2R)-2-(((S)-6'-chloro-7-(((R)-hex-5-en-2-ylsulfonyl)carbamoyl)-3',4'-dihydro-2H,2'H-spiro[benzo[b][1,4]oxazepine-3,1'-naphthalen]-5 (4H)-yl)methyl)cyclobutyl)allyl)carbamate

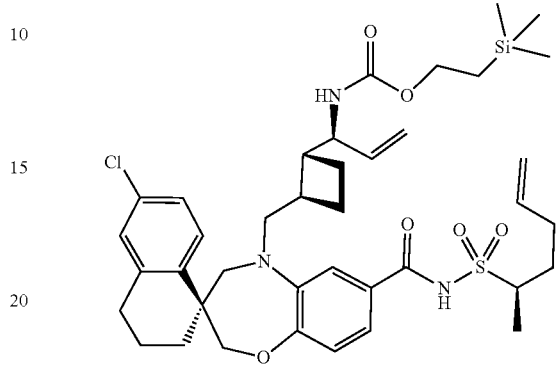

(S)-1-((1R,2R)-2-(((S)-6'-chloro-7-(((R)-hex-5-en-2-ylsulfonyl)carbamoyl)-3',4'-dihydro-2H,2'H-spiro[benzo[b][1,4]oxazepine-3,1'-naphthalen]-5 (4H)-yl)methyl)cyclobutyl)prop-2-en-1-aminium chloride from Step 5 (240 mg, 0.392 mmol) in 1,4-dioxane (3.9 mL) was added 1-[(2-trimethylsilyl)ethoxycarbonyloxy]pyrrolidin-2,5-dione (132 mg, 0.510 mmol), followed by triethylamine (0.164 mL, 1.18 mmol). The mixture was stirred at ambient temperature for 20 minutes then was loaded into a silica gel cartridge and purified by column chromatography (0-30% EtOAc/hexanes, 24 g SiO$_2$) to afford 2-(trimethylsilyl)ethyl ((S)-1-((1R,2R)-2-(((S)-6'-chloro-7-(((R)-hex-5-en-2-ylsulfonyl)carbamoyl)-3',4'-dihydro-2H,2'H-spiro[benzo[b][1,4]oxazepine-3,1'-naphthalen]-5 (4H)-yl)methyl)cyclobutyl)allyl)carbamate.

Step 7: 2-(trimethylsilyl)ethyl ((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)carbamate

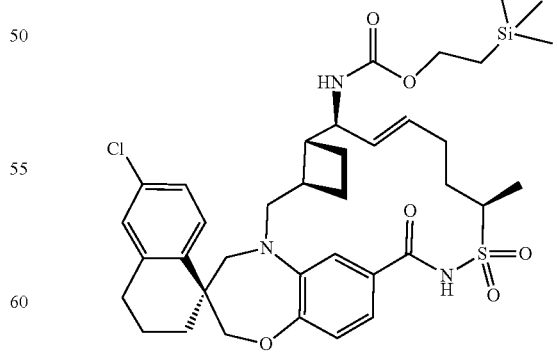

A solution of 2-(trimethylsilyl)ethyl ((S)-1-((1R,2R)-2-(((S)-6'-chloro-7-(((R)-hex-5-en-2-ylsulfonyl)carbamoyl)-3',4'-dihydro-2H,2'H-spiro[benzo[b][1,4]oxazepine-3,1'-naphthalen]-5 (4H)-yl)methyl)cyclobutyl)allyl)carbamate from Step 6 (152 mg, 0.201 mmol) in 1,2-dichloroethane (70 mL) was sparged with argon for 10 min. To this solution was added Ti(O$^i$Pr)$_4$ (17 mg, 0.060 mmol), and the mixture was heated at 50° C. for 15 min under and atmosphere of argon. Hoveyda-Grubbs 2$^{nd}$ Generation catalyst (25 mg, 0.040 mmol) was added, and the reaction mixture was continued to heat at this temperature for 19h. The reaction mixture was cooled to ambient temperature and then air was bubbled through the reaction mixture for 5 min. The solution was concentrated and then the residue was purified by column chromatography (0% to 60% (0.3% AcOH/EtOAc)/hexanes, 24 g SiO$_2$), affording 2-(trimethylsilyl)ethyl ((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)carbamate. MS (ESI) m/z=728.2 [M+H]$^+$.

Step 8: (1S,3'R,6'R,7'S,8'E,12'R)-7'-amino-6-chloro-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide trifluoroacetate

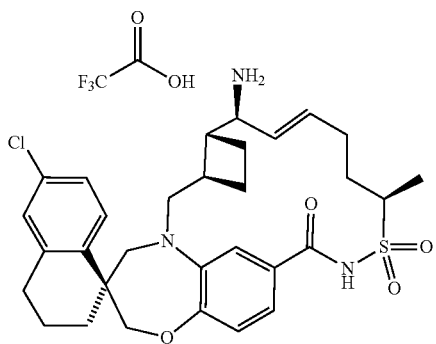 [SMILES: C[C@@H]1CC/C=C/[C@H](N)[C@@H]2CC[C@H]2CN2C[C@@]3(CCCc4cc(Cl)ccc43)COc3ccc(cc32)C(=O)NS1(=O)=O ; O=C(O)C(F)(F)F]

2-(trimethylsilyl)ethyl ((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl) carbamate from Step 7 (51 mg, 0.070 mmol) was dissolved into TFA (0.1 mL) and DCM (0.3 mL) and stirred at room temperature for for 2 h. The reaction mixture was loaded directly onto a cartridge of SiO$_2$ and was purified by column chromatography (0-20% MeOH/DCM, 20 g SiO$_2$) to give (1S,3'R,6'R,7'S,8'E,12'R)-7'-amino-6-chloro-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide trifluoroacetate. MS (ESI) m/z=584.3 [M-CF$_3$CO$_2$]$^+$.

Step 9: methyl N-((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)glycinate-trifluoroacetic Acid

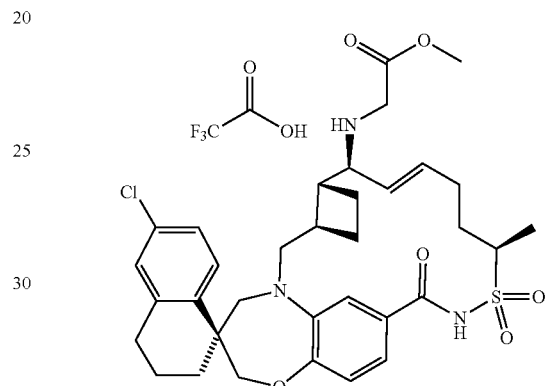

(1S,3'R,6'R,7'S,8'E,12'R)-7'-amino-6-chloro-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide trifluoroacetate (12 mg, 0.017 mmol), triethylamine (0.029 mL, 0.21 mmol) and methyl bromoacetate (0.020 mL, 2.1 mmol) were stirred in THF (0.2 mL) for 3 hours. Concentration of the reaction mixture was followed by purification by HPLC (5 to 95% MeCN/H$_2$O with 0.1% TFA) to give the mono-alkylated title product. $^1$H NMR (500 MHz, CDCl$_3$) δ 7.67 (d, J=8.6 Hz, 1H), 7.18 (dd, J=8.4, 2.1 Hz, 1H), 7.09 (d, J=2.0 Hz, 1H), 6.97-6.88 (m, 2H), 6.75 (s, 1H), 6.09 (ddd, J=14.5, 10.2, 3.7 Hz, 1H), 5.72 (dd, J=15.2, 9.8 Hz, 1H), 4.24 (t, J=9.5 Hz, 1H), 4.14-4.07 (m, 1H), 4.06-4.00 (m, 1H), 3.87 (s, 3H), 3.85-3.78 (m, 3H), 3.77-3.66 (m, 2H), 3.19 (d, J=14.2 Hz, 1H), 3.00 (dd, J=15.4, 10.5 Hz, 1H), 2.85-2.73 (m, 2H), 2.73-2.65 (m, 1H), 2.51-2.36 (m, 3H), 2.30-2.18 (m, 2H), 2.09-1.91 (m, 6H), 1.85-1.68 (m, 4H), 1.59 (d, J=6.8 Hz, 3H), 1.38 (t, J=12.7 Hz, 1H); MS (ESI) m/z=656.3 [M-CF$_3$CO$_2$]$^+$.

Example 600. dimethyl 2,2'-(((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)imino)diacetate-trifluoroacetic Acid

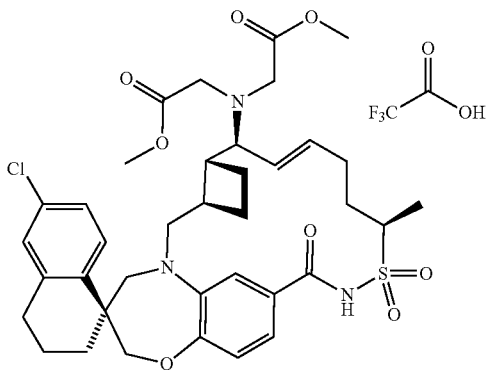

This was prepared as outlined in Example 599. The title compound was isolated from the reaction mixture of Step 9. $^1$H NMR (500 MHz, CDCl$_3$) δ 7.83 (s, 1H), 7.60 (d, J=8.8 Hz, 1H), 7.09 (d, J=8.6 Hz, 1H), 7.01 (s, 1H), 6.83 (d, J=8.6 Hz, 1H), 6.81-6.76 (m, 1H), 6.71 (s, 1H), 5.74 (br. s., 1H), 5.58-5.47 (m, 1H), 4.17 (br. s., 1H), 4.03-3.98 (m, 1H), 3.98-3.92 (m, 1H), 3.77 (d, J=15.4 Hz, 1H), 3.67 (s, 7H), 3.66-3.57 (m, 6H), 3.48 (br. s., 1H), 3.12 (d, J=14.7 Hz, 1H), 2.94-2.85 (m, 1H), 2.77-2.64 (m, 2H), 2.51 (br. s., 1H), 2.27 (br. s., 3H), 2.11 (d, J=14.2 Hz, 1H), 1.94 (d, J=14.7 Hz, 2H), 1.88 (d, J=7.8 Hz, 5H), 1.50 (d, J=6.8 Hz, 3H), 1.25-1.33 (m, 1H).

Example 601. 3-((1S,3'R,6'R,7'S,8'E,12'R)-6-chloro-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)-1,1-dimethylurea-trifluoroacetate

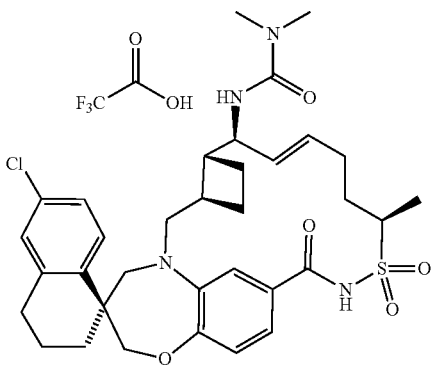 [SMILES: C[C@@H]1CC/C=C/[C@H](NC(=O)N(C)C)[C@@H]2CC[C@H]2CN2C[C@@]3(CCCc4cc(Cl)ccc43)COc3ccc(cc32)C(=O)NS1(=O)=O ; O=C(O)C(F)(F)F]

To a 2 mL vial was added hunig's base (12.86 μl, 0.074 mmol) and (1S,3'R,6'R,7'S,8'E,12'R)-6-chloro-12'-methyl-7'-amino-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide trifluoroacetate from Example 599, step 8 (4.3 mg, 7.4 μmol) in DCM (0.25 ml) at rt. The reaction mixture was stirred at ambient temperature for 5 min, and then dimethylcarbamic chloride (7.9 mg, 0.074 mmol) was added. The reaction mixture was stirred for 21 h. The reaction mixture was diluted with MeOH, filtered and purified by HPLC (5% to 95% MeCN/H$_2$O with 0.1% TFA) to give the title compound. $^1$H NMR (500 MHz, CDCl$_3$) δ 8.04 (br. s., 1H), 7.68 (d, J=8.4 Hz, 1H), 7.18 (dd, J=8.4, 2.3 Hz, 1H), 7.09 (d, J=2.2 Hz, 1H), 7.06 (s, 1H), 6.93-6.90 (m, 1H), 6.88-6.84 (m, 1H), 5.82-5.72 (m, 1H), 5.56 (dd, J=14.9, 7.6 Hz, 1H), 4.38 (br. s., 1H), 10 4.14-4.03 (m, 2H), 3.93 (d, J=12.5 Hz, 1H), 3.69 (d, J=14.4 Hz, 1H), 3.22 (d, J=14.4 Hz, 1H), 2.98 (dd, J=15.3, 8.7 Hz, 1H), 2.86-2.80 (m, 6H), 2.79-2.70 (m, 2H), 2.62-2.52 (m, 1H), 2.51-2.39 (m, 1H), 2.35-2.25 (m, 1H), 2.21-2.09 (m, 1H), 1.99 (d, J=18.6 Hz, 4H), 1.85-1.76 (m, 8H), 1.55 (d, J=6.8 Hz, 3H), 1.41-1.33 (m, 1H); MS (ESI) m/z=654.8 [M+H]$^+$.

Example 602. (1S,3'R,6'R,7'S,8'E,12'R)-7'-(bis((5-methyl-1,2,4-oxadiazol-3-yl)methyl)amino)-6-chloro-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

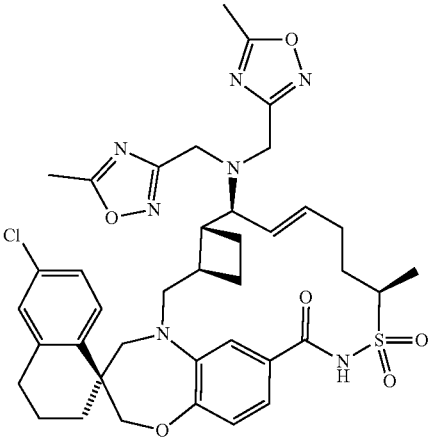 [SMILES: Cc1nc(CN(Cc2noc(C)n2)[C@H]2/C=C/CC[C@@H](C)S(=O)(=O)NC(=O)c3ccc4c(c3)N(C[C@@H]3CC[C@H]32)C[C@@]2(CCCc3cc(Cl)ccc32)CO4)no1]

To a 2 mL vial was added N,N-diisopropylethyl amine (5.38 μl, 0.031 mmol) and (1S,3'R,6'R,7'S,8'E,12'R)-6-chloro-12'-methyl-7'-amino-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide trifluoroacetate from Example 599, step 8 (6.0 mg, 10 μmol) in MeCN (0.34 ml) at ambient temperature. The reaction mixture was stirred for 5 min, and then 3-(chloromethyl)-5-methyl-1,2,4-oxadiazole (4.1 mg, 0.031 mmol) was added. The reaction mixture was stirred at 70° C. for 16 h. The solution was diluted with MeOH, filtered and purified by HPLC (5% to 95% MeCN/H$_2$O with 0.1% TFA) to give the dialkylated product. $^1$H NMR (500 MHz, CDCl$_3$) δ 7.86 (s, 1H), 7.69 (d, J=8.6 Hz, 1H), 7.18 (dd, J=8.4, 2.3 Hz, 1H), 7.09 (d, J=2.2 Hz, 1H), 6.94-6.89 (m, 1H), 6.87-6.82 (m, 1H), 6.74 (d, J=1.5 Hz, 1H), 5.83-5.74 (m, 1H), 5.63 (dd, J=14.9, 8.8 Hz, 1H), 4.23-4.15 (m, 1 H), 4.12-3.92 (m, 6H), 3.80 (d, J=15.9 Hz, 1H), 3.71 (d, J=13.7 Hz, 1H), 3.43 (d, J=9.8 Hz, 1H), 3.20 (d, J=13.9 Hz, 1H), 2.98 (dd, J=15.5, 10.4 Hz, 1H), 2.85-2.73 (m, 2H), 2.72-2.65 (m, 1H), 2.63 (s, 6H), 2.32 (t, J=8.2 Hz, 2H), 2.21 (d, J=16.1 Hz, 1H), 2.07-1.89 (m, 5H), 1.88-1.67 (m, 4H), 1.58 (d, J=6.8 Hz, 3H), 1.38 (t, J=12.3 Hz, 1H); MS (ESI) m/z=775.8 [M+H]+.

Example 603. (1S,3'R,6'R,7'S,8'E,12'R)-6-chloro-12'-methyl-7'-((5-methyl-1,2,4-oxadiazol-3-yl)methoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

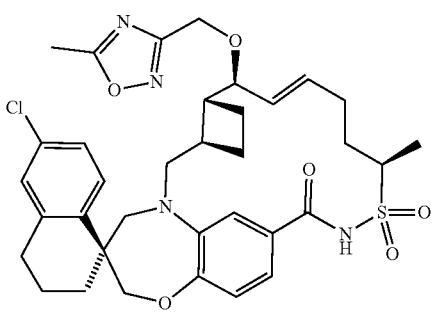 [SMILES: Cc1nc(CO[C@H]2/C=C/CC[C@@H](C)S(=O)(=O)NC(=O)c3ccc4c(c3)N(C[C@@H]3CC[C@H]32)C[C@@]2(CCCc3cc(Cl)ccc32)CO4)no1]

To a 2 mL vial was added sodium hydride, 60% dispersion in mineral oil (2.0 mg, 0.049 mmol) and (1S,3'R,6'R,7'S,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 404, Step 1) (5.7 mg, 9.7 μmol) in THF (0.33 ml) at ambient temperature. The reaction mixture was stirred for 5 min, and then 3-(chloromethyl)-5-methyl-1,2,4-oxadiazole (3.9 mg, 0.029 mmol) was added. The reaction mixture was stirred at ambient temperature for 17h. The reaction mixture was diluted with MeOH, filtered and purified by HPLC (5% to 95% MeCN/H$_2$O with 0.1% TFA) to give the title product, (2.6 mg, 39%). $^1$H NMR (500 MHz, CDCl$_3$) δ 7.95 (s, 1H), 7.70 (d, J=8.6 Hz, 1H), 7.19 (dd, J=8.6, 2.2 Hz, 1H), 7.09 (d, J=2.2 Hz, 1H), 6.92 (d, J=8.1 Hz, 1H), 6.87 (dd, J=8.1, 2.0 Hz, 1H), 6.80 (d, J=1.7 Hz, 1H), 5.88 (ddd, J=15.2, 9.3, 3.9 Hz, 1H), 5.61 (dd, J=15.4, 9.0 Hz, 1H), 4.57 (d, J=13.2 Hz, 1H), 4.45 (d, J=13.2 Hz, 1H), 4.34-4.22 (m, 1H), 4.07 (q, J=12.1 Hz, 2H), 3.93 (dd, J=9.0, 3.4 Hz, 1H), 3.83 (d, J=14.9 Hz, 1H), 3.72 (d, J=14.4 Hz, 1H), 3.22 (d, J=14.2 Hz, 1H), 2.98 (dd, J=15.3, 10.4 Hz, 1H), 2.85-2.70 (m, 2H), 2.63 (s, 3H), 2.60-2.51 (m, 1H), 2.44-2.21 (m, 3H), 2.09-1.91 (4H, m), 1.91-1.74 (3H, m), 1.70-1.62 (m, 1H), 1.60 (d, J=6.8 Hz, 3H), 1.39 (t, J=13.0 Hz, 1H); MS (ESI) m/z [M+H]=680.8.

Example 604. (1S,3'R,6'R,8'E,12'R)-6-chloro-12'-methyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [8,16,18,24]tetraene]-7',15'-dione 13',13'-dioxide

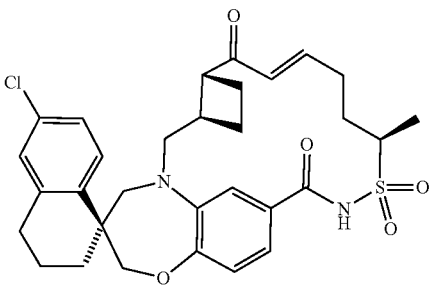 [SMILES: C[C@@H]1CC/C=C/C(=O)[C@@H]2CC[C@H]2CN2C[C@@]3(CCCc4cc(Cl)ccc43)COc3ccc(cc32)C(=O)NS1(=O)=O]

A 2-dram vial was charged with (1S,3'R,6'R,7'S,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 404, Step 1) (80 mg, 0.14 mmol) in DCM (2 mL) was added dess-martin periodinane (73 mg, 0.17 mmol) and NaHCO$_3$ (46 mg, 0.55 mmol). The reaction mixture was stirred at ambient temperature for 2 h. The mixture was directly loaded onto a cartridge of SiO$_2$, and then purified by column chromatography (0-10% MeOH/DCM, 4 g SiO$_2$) to give the title compound (65 mg). $^1$H NMR (500 MHz, CDCl$_3$) δ 8.08 (s, 1H), 7.75 (d, J=8.6 Hz, 1H), 7.32 (d, J=2.0 Hz, 1H), 7.20 (dd, J=8.4, 2.3 Hz, 1H), 7.08 (d, J=2.2 Hz, 1H), 6.87-6.83 (m, 1H), 6.81-6.76 (m, 1H), 6.65 (ddd, J=15.8, 8.6, 7.2 Hz, 1H), 5.95 (d, J=15.9 Hz, 1H), 4.16-3.98 (m, 3H), 3.92-3.79 (m, 2H), 3.73 (q, J=9.5 Hz, 1H), 3.25 (d, J=14.4 Hz, 1H), 3.13-3.03 (m, 1H), 2.99 (dd, J=15.4, 2.9 Hz, 1H), 2.85-2.69 (m, 2H), 2.43-2.31 (m, 1H), 2.21-2.04 (m, 3H), 2.03-1.96 (m, 1H), 1.95-1.87 (m, 5H), 1.60 (d, J=7.1 Hz, 3H), 1.40 (t, J=12.3 Hz, 1H); MS (ESI) m/z=583.2 [M+H]+.

Example 605. (1S,3'R,6'R,7'Z,9'S,12'R)-6-chloro-9'-hydroxy-12'-methyl-7'-(1-propyn-1-yl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide or (1S,3'R,6'R,7'Z,9'R,12'R)-6-chloro-9'-hydroxy-12'-methyl-7'-(1-propyn-1-yl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide

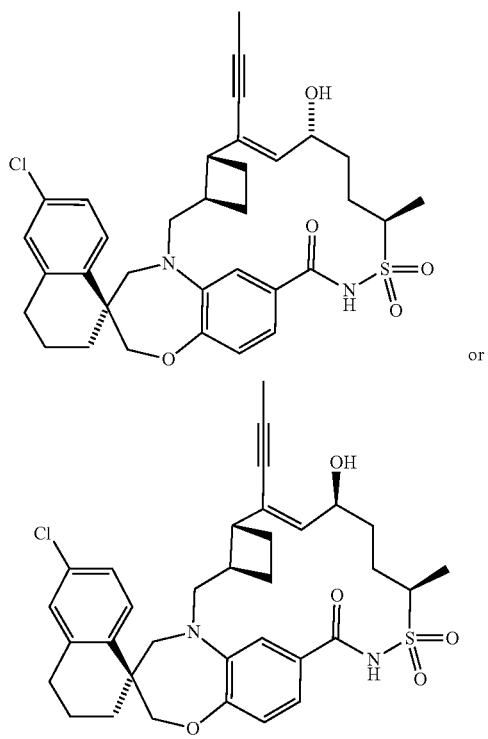

A 2-dram was charged with (1S,3'R,6'R,8'E,12'R)-6-chloro-12'-methyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dione 13',13'-dioxide (Example 604) (20 mg, 0.034 mmol) and THF (0.69 ml). The reaction mixture was cooled to 0° C. and a solution of prop-1-yn-1-yl magnesium bromide (0.5 M in THF, 171 µl, 0.086 mmol) was added dropwise, and the reaction mixture was stirred at 0° C. for 15 min. The reaction mixture was diluted with MeOH (0.2 mL) & DCM (1 mL) and quenched with 0.04 mL of 4N HCl solution in dioxane. The mixture was loaded directly onto a silica gel cartridge and purified by column chromatography (0-50-100% EtOAc/(0.3% v/v AcOH/hexanes), 4 g SiO$_2$). The desired fractions were pooled and then repurified by HPLC (5% to 95% MeCN/H$_2$O with 0.1% TFA) to give as the first eluting compound, one of the title compounds. $^1$H NMR (500 MHz, CD$_3$OD) δ 7.73 (d, J=8.6 Hz, 1H), 7.17 (dd, J=8.6, 2.2 Hz, 1H), 7.15 (d, J=1.5 Hz, 1H), 7.10 (d, J=2.2 Hz, 1H), 6.96-6.89 (m, 2H), 5.48 (d, J=8.8 Hz, 1H), 4.58 (td, J=8.6, 4.6 Hz, 1H), 4.18 (d, J=14.9 Hz, 1H), 4.07 (s, 2H), 3.89-3.80 (m, 1H), 3.66 (d, J=14.2 Hz, 1H), 3.24-3.18 (m, 1H), 3.12 (dd, J=15.0, 9.7 Hz, 1H), 2.86-2.70 (m, 2H), 2.70-2.62 (m, 1H), 2.28-2.17 (m, 1H), 2.15-2.08 (m, 4H), 2.00-1.82 (m, 8H), 1.80-1.59 (m, 4H), 1.51-1.40 (m, 4H); MS (ESI) m/z=623.2 [M+H]$^+$.

Example 606. (1S,3'R,6'R,7'Z,9'R,12'R)-6-chloro-9'-hydroxy-12'-methyl-7'-(1-propyn-1-yl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide or (1S,3'R,6'R,7'Z,9'S,12'R)-6-chloro-9'-hydroxy-12'-methyl-7'-(1-propyn-1-yl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide

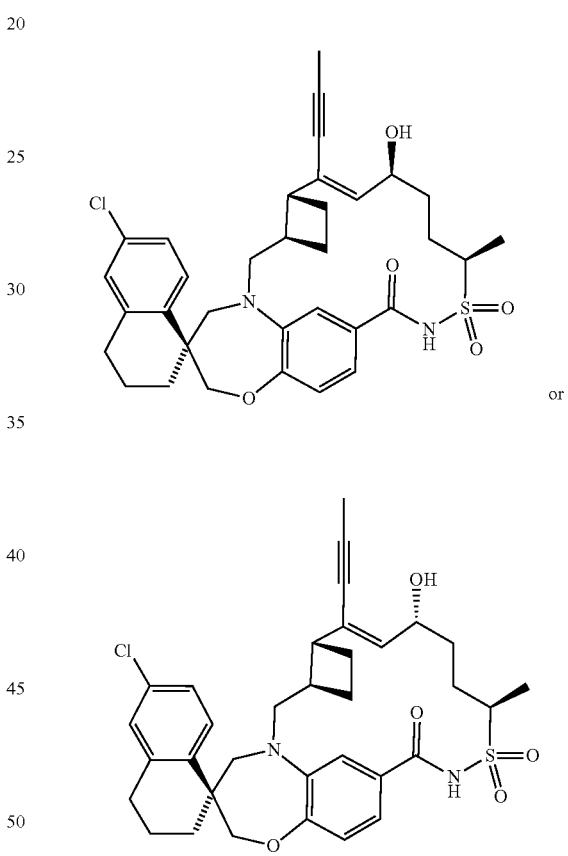

This example was prepared as in Example 605 but the isolated compound was the second eluting isomer. $^1$H NMR (500 MHz, CDCl$_3$) δ 7.98 (br. s., 1H), 7.72 (d, J=8.6 Hz, 1H), 7.19 (dd, J=8.3, 2.2 Hz, 1H), 7.10 (d, J=2.0 Hz, 1H), 7.06-7.00 (m, 1H), 6.96 (d, J=8.1 Hz, 1H), 6.65 (s, 1H), 5.67 (d, J=7.8 Hz, 1H), 4.77-4.69 (m, 1H), 4.14-4.08 (m, 1H), 4.08-4.02 (m, 1H), 3.90-3.80 (m, 1H), 3.75 (d, J=14.2 Hz, 1H), 3.68 (d, J=15.4 Hz, 1H), 3.35-3.24 (m, 1H), 3.16 (dd, J=15.5, 8.7 Hz, 1H), 2.87-2.72 (m, 2H), 2.71-2.57 (m, 2H), 2.17-2.05 (m, 4H), 2.04-1.92 (m, 4H), 1.92-1.77 (m, 6H), 1.61-1.54 (d, J=6.8 Hz, 3H), 1.44 (t, J=13.1 Hz, 1H); MS (ESI) m/z=623.2 [M+H]$^+$.

Example 609. (3R,6R,7R,13R,23S)-6'-chloro-13-methyl-3',4'-dihydro-2'H,16H-spiro[8,21-dioxa-14-thia-1,9,15-triazapentacyclo[15.7.2.1⁷,¹⁰.0³,⁶.0²⁰,²⁵]heptacosa-9,17,19,25-tetraene-23,1'-naphthalen]-16-one 14,14-dioxide or (3R,6R,7S,13R,23S)-6'-chloro-13-methyl-3',4'-dihydro-2'H,16H-spiro[8,21-dioxa-14-thia-1,9,15-triazapentacyclo[15.7.2.1⁷,¹⁰.0³,⁶.0²⁰,²⁵]heptacosa-9,17,19,25-tetraene-23,1'-naphthalen]-16-one 14,14-dioxide

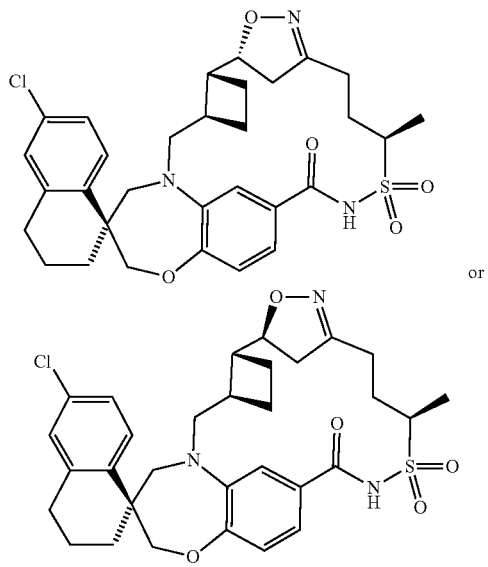

Step 1: (R)-5-hydroxy-N,N-bis(4-methoxybenzyl)pentane-2-sulfonamide

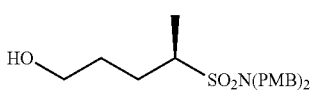

A solution of (R)—N,N-bis(4-methoxybenzyl)hex-5-ene-2-sulfonamide (200 mg, 0.496 mmol, Intermediate EE20, Step 1, second eluting enantiomer) in MeOH (20 mL) was cooled to −78° C. Ozone was bubbled though the reaction mixture until a blue color persisted in the solution (about 15 minutes). Nitrogen was bubbled through the reaction to remove the blue color before sodium borohydride (22.5 mg, 0.595 mmol) was added. The reaction mixture was stirred at ambient temperature under a positive argon pressure for 3 h. More sodium borohydride (50 mg) was added and stirring continued for another 2 h. The reaction was concentrated and the residue was absorbed onto SiO₂ then purified by flash chromatography, 0-30-100% EtOAc/hexanes, to give (R)-5-hydroxy-N,N-bis(4-methoxybenzyl)pentane-2-sulfonamide (109 mg). ¹H NMR (500 MHz, CDCl₃) δ 7.22-7.12 (m, 4H), 6.85 (d, J=8.8 Hz, 4H), 4.32 (d, J=15.2 Hz, 2H), 4.21 (d, J=15.2 Hz, 2H), 3.79 (s, 6H), 3.60 (t, J=6.2 Hz, 2H), 3.01-2.88 (m, 1H), 2.43 (br. s, 1H), 2.01-1.95 (m, 1H), 1.77-1.66 (m, 1H), 1.66-1.56 (m, 1H), 1.56-1.46 (m, 1H), 1.30 (d, J=6.8 Hz, 3H); ¹³C NMR (126 MHz, CDCl₃) δ 159.06, 129.83, 127.95, 113.83, 61.97, 58.90, 55.13, 49.79, 29.33, 26.73, 13.84; MS (ESI) m/z=430.1 [M+Na]⁺.

Step 2: (R)-5-IODO-N,N-bis(4-methoxybenzyl)pentane-2-sulfonamide

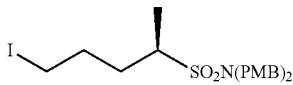

Procedure adapted from J Org. Chem. 2002, 67, 772. To a solution of (R)-5-hydroxy-N,N-bis(4-methoxybenzyl)pentane-2-sulfonamide from Step 1 (500 mg, 1.23 mmol) in THF (15 mL) was added imidazole (251 mg, 3.68 mmol), triphenylphosphine (644 mg, 2.45 mmol) and iodine (934 mg, 3.68 mmol) at 0° C. The mixture was stirred for 24 h at ambient temperature. The solution was directly loaded onto a cartridge of SiO₂ and was purified by column chromatography, 0-30-100% EtOAc/hexanes, to give (R)-5-iodo-N,N-bis(4-methoxybenzyl)pentane-2-sulfonamide (270 mg). ¹H NMR (500 MHz, CDCl₃) δ 7.24-7.18 (m, 4H), 6.91-6.85 (m, 4H), 4.35 (d, J=15.2 Hz, 2H), 4.25 (d, J=15.2 Hz, 2H), 3.83 (s, 6H), 3.13 (t, J=6.5 Hz, 2H), 2.80-2.89 (m, 1H), 2.05-1.92 (m, 2H), 1.82-1.72 (m, 1H), 1.70-1.62 (m, 1H), 1.31 (d, J=6.8 Hz, 3H); MS (ESI) m/z=540.0 [M+Na]⁺.

Step 3: (R)—N,N-bis(4-methoxybenzyl)-5-nitropentane-2-sulfonamide

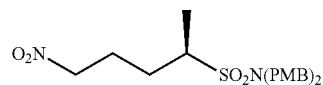

Urea (219 mg, 3.65 mmol) was added to a stirring solution of (R)-5-iodo-N,N-bis(4-methoxybenzyl)pentane-2-sulfonamide from Step 2 (270 mg, 0.522 mmol) in DMSO (5 mL). After 5 minutes, sodium nitrite (252 mg, 3.65 mmol) was added to the mixture and stirring continued for 2 h. The reaction mixture was loaded to directly onto a cartridge of SiO₂ and was then purified by column chromatography, 0-100% EtOAc/hexanes, to give (R)—N,N-bis(4-methoxybenzyl)-5-nitropentane-2-sulfonamide. MS (ESI)=459.1 [M+Na]⁺.

Step 4: (S)-methyl 6'-chloro-5-(((1R,2S)-2-vinylcyclobutyl)methyl)-3',4,4',5-tetrahydro-2H,2'H-spiro[benzo[b][1,4]oxazepine-3,1'-naphthalene]-7-carboxylate

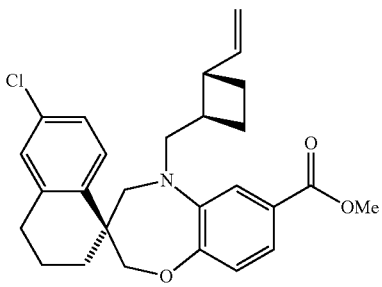

A solution of methyltriphenylphosphonium bromide (2.91 g, 8.15 mmol) in THF (12 ml) was cooled to 0° C. n-Butyllithium solution, 2.5m in hexanes (2.93 ml, 7.34 mmol) was added dropwise to the cooled solution. Following the addition the reaction mixture was for 10 min. This solution was slowly added to a cold (0° C.) solution of (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (370 mg, 0.815 mmol, Intermediate Intermediate AA11A, Step 20A) in THF (4 ml) until the yellow color persisted. After the addition was complete the mixture was stirred for 15 minutes. The reaction mixture was quenched by pouring the contents of the flask into ice-water (30 mL). The organic phase was separated and the aqueous phase was extracted with EtOAc (30 mL). The combined organic extracts were dried with anhydrous sodium sulfate, and then concentrated. The residue was purified by column chromatography, 10% EtOAc/hexanes, 24 g SiO$_2$ to yield (S)-methyl 6'-chloro-5-(((1R,2S)-2-vinylcyclobutyl)methyl)-3',4,4',5-tetrahydro-2H,2'H-spiro[benzo[b][1,4]oxazepine-3,1'-naphthalene]-7-carboxylate (239 mg, 0.529 mmol). MS (ESI) m/z=452.1 [M+H]$^+$.

Step 5: (S)-methyl 5-(((1R,2R)-2-((S)-3-((R)-3-(N,N-bis(4-methoxybenzyl)sulfamoyl)butyl)-4,5-dihydroisoxazol-5-yl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((R)-3-((R)-3-(N,N-bis(4-methoxybenzyl)sulfamoyl)butyl)-4,5-dihydroisoxazol-5-yl)cyclobutyl)methyl)-6'-chloro-3',4,4',5-tetrahydro-2H,2'H-spiro[benzo[b][1,4]oxazepine-3,1'-naphthalene]-7-carboxylate

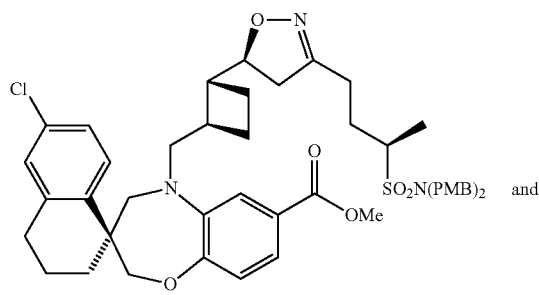

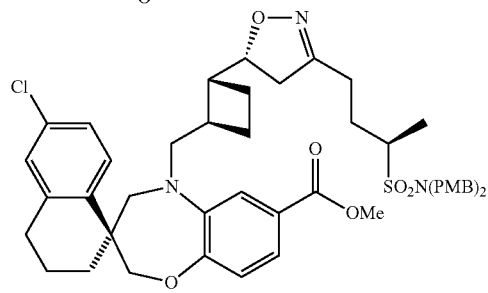

Procedure adapted from *J. Org. Chem.* 2002, 67, 772. A mixture of (S)-methyl 6'-chloro-5-(((1R,2S)-2-vinylcyclobutyl)methyl)-3',4,4',5-tetrahydro-2H,2'H-spiro[benzo[b][1,4]oxazepine-3,1'-naphthalene]-7-carboxylate from Step 4 (90 mg, 0.199 mmol), (R)—N,N-bis(4-methoxybenzyl)-5-nitropentane-2-sulfonamide from Step 3 (87 mg, 0.199 mmol), 4-chlorophenyl isocyanate (183 mg, 1.20 mmol), and triethylamine (0.061 mL, 0.44 mmol) in benzene (1 mL) was refluxed for 1h. The reaction mixture was loaded directly into a solid cartridge of silica gel and purified by column chromatography, 0-20-50% EtOAc/hexanes, to give a mixture of the desired dihydroisoxazole diastereomers (109 mg), MS (ESI) m/z=870.3 [M+H]$^+$.

Step 6: (S)-methyl 6'-chloro-5-(((1R,2R)-2-((S)-3-((R)-3-sulfamoylbutyl)-4,5-dihydroisoxazol-5-yl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-3-((R)-3-sulfamoylbutyl)-4,5-dihydroisoxazol-5-yl)cyclobutyl)methyl)-3',4,4',5-tetrahydro-2H,2'H-spiro[benzo[b][1,4]oxazepine-3,1'-naphthalene]-7-carboxylate

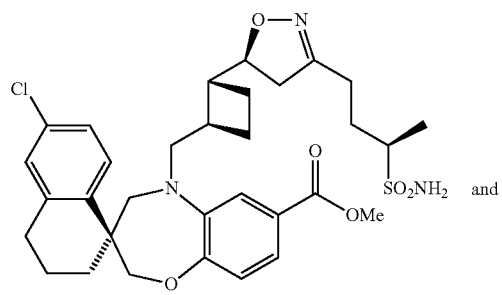

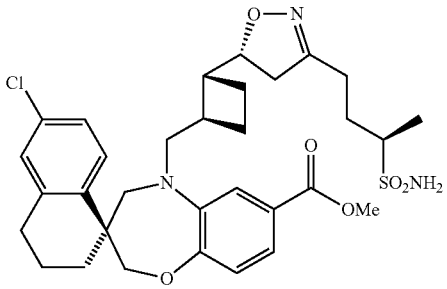

(S)-methyl 5-(((1R,2R)-2-((S)-3-((R)-3-(N,N-bis(4-methoxybenzyl)sulfamoyl)butyl)-4,5-dihydroisoxazol-5-yl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((R)-3-((R)-3-(N,N-bis(4-methoxybenzyl)sulfamoyl)butyl)-4,5-dihydroisoxazol-5-yl)cyclobutyl)methyl)-6'-chloro-3',4,4',5-tetrahydro-2H,2'H-spiro[benzo[b][1,4]oxazepine-3,1'-naphthalene]-7-carboxylate mixture from Step 5 (109 mg, 0.125 mmol) in anisole (684 µl, 6.26 mmol) and trifluoroacetic acid (482 µl, 6.26 mmol) was stirred at 40° C. for 22h. The reaction mixture was loaded directly into a cartridge of silica gel, and purified by column chromatography, 0-100% EtOAc/hexanes, 24 g SiO$_2$, to give (S)-methyl 6'-chloro-5-(((1R,2R)-2-((S)-3-((R)-3-sulfamoylbutyl)-4,5-dihydroisoxazol-5-yl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-3-((R)-3-sulfamoylbutyl)-4,5-dihydroisoxazol-5-yl)cyclobutyl)methyl)-3',4,4',5-tetrahydro-2H,2'H-spiro[benzo[b][1,4]oxazepine-3,1'-naphthalene]-7-carboxylate (83.8 mg). MS (ESI) m/z=630.2 [M+H]$^+$.

Step 7: (S)-6'-chloro-5-(((1R,2R)-2-((S)-3-((R)-3-sulfamoylbutyl)-4,5-dihydroisoxazol-5-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((R)-3-((R)-3-sulfamoylbutyl)-4,5-dihydroisoxazol-5-yl)cyclobutyl)methyl)-3',4,4',5-tetrahydro-2H,2'H-spiro[benzo[b][1,4]oxazepine-3,1'-naphthalene]-7-carboxylic Acid Step 8: (3R,6R,7R,13R,23S)-6'-chloro-13-methyl-3',4'-dihydro-2'H,16H-spiro[8,21-dioxa-14-thia-1,9,15-triazapentacyclo[15.7.2.1$^{7,10}$.0$^{3,6}$.0$^{20,25}$]heptacosa-9,17,19,25-tetraene-23,1'-naphthalen]-16-one 14,14-dioxide or (3R,6R,7S,13R,23S)-6'-chloro-13-methyl-3',4'-dihydro-2'H,16H-spiro[8,21-dioxa-14-thia-1,9,15-triazapentacyclo[15.7.2.1$^{7,10}$.0$^{3,6}$.0$^{20,25}$]heptacosa-9,17,19,25-tetraene-23,1'-naphthalen]-16-one 14,14-dioxide

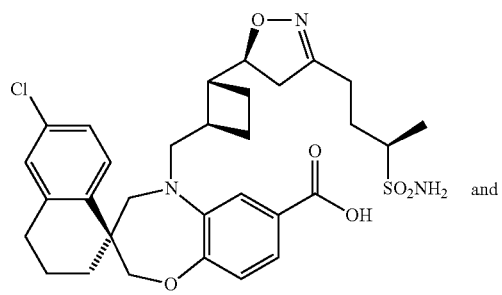

and

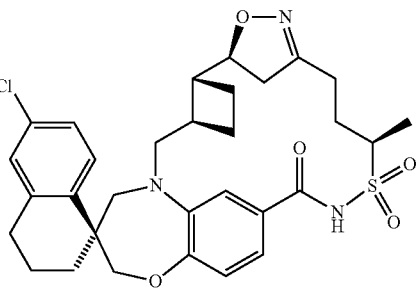

or

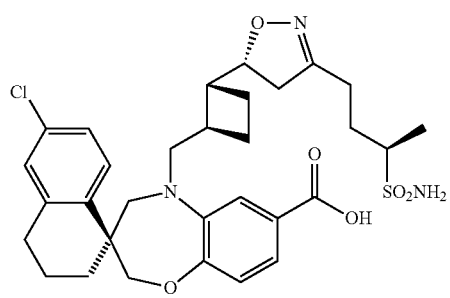

(S)-methyl 6'-chloro-5-(((1R,2R)-2-((S)-3-((R)-3-sulfamoylbutyl)-4,5-dihydroisoxazol-5-yl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((R)-3-((R)-3-sulfamoylbutyl)-4,5-dihydroisoxazol-5-yl)cyclobutyl)methyl)-3',4,4',5-tetrahydro-2H,2'H-spiro[benzo[b][1,4]oxazepine-3,1'-naphthalene]-7-carboxylate from Step 6 (83.8 mg, 0.133 mmol) was stirred in a mixture of 1M aqueous LiOH (0.67 mL), THF (1.5 mL) and ethanol (1.5 mL) at 50° C. for 3 h. The pH of the mixture was adjusted to pH=5 by addition of 1M aqueous HCl. The resulting solution was directly loaded into a cartridge of silica gel and purified by column chromatography, 0-10% MeOH/DCM, 12 g SiO$_2$, to give (S)-6'-chloro-5-(((1R,2R)-2-((S)-3-((R)-3-sulfamoylbutyl)-4,5-dihydroisoxazol-5-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-3-((R)-3-sulfamoylbutyl)-4,5-dihydroisoxazol-5-yl)cyclobutyl)methyl)-3',4,4',5-tetrahydro-2H,2'H-spiro[benzo[b][1,4]oxazepine-3,1'-naphthalene]-7-carboxylic acid (82 mg).

N,N-dimethylpyridin-4-amine (28 mg, 0.23 mmol) was added to a solution of (S)-6'-chloro-5-(((1R,2R)-2-((S)-3-((R)-3-sulfamoylbutyl)-4,5-dihydroisoxazol-5-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-3-((R)-3-sulfamoylbutyl)-4,5-dihydroisoxazol-5-yl)cyclobutyl)methyl)-3',4,4',5-tetrahydro-2H,2'H-spiro[benzo[b][1,4]oxazepine-3,1'-naphthalene]-7-carboxylic acid from Step 7 (82 mg, 0.13 mmol, previously azeotroped with 5 mL toluene) in CH$_2$Cl$_2$ (67 ml) at 0° C. N-(3-dimethylaminopropyl)-N'-ethylcarbodiimide hydrochloride (51 mg, 0.27 mmol) was added and the mixture was stirred at ambient temperature for 17 h. The reaction mixture was concentrated, dissolved in MeCN, and then purified by HPLC (10-95% ACN/water with 0.1% TFA) to give one of the title compounds. $^1$H NMR (500 MHz, CDCl$_3$) δ 8.04 (br. s., 1H), 7.71 (d, J=8.6 Hz, 1H), 7.19 (dd, J=8.6, 2.2 Hz, 1H), 7.09 (d, J=2.2 Hz, 1H), 7.02 (s, 1H), 6.97-6.86 (m, 2H), 4.60 (ddd, J=11.5, 9.9, 6.7 Hz, 1H), 4.39 (br. s., 1H), 4.15-4.09 (m, 1H), 4.08-4.02 (m, 2H), 3.73 (d, J=14.4 Hz, 1H), 3.22 (d, J=14.4 Hz, 1H), 3.14 (dd, J=15.4, 7.6 Hz, 1H), 2.84-2.74 (m, 3H), 2.74-2.63 (m, 2H), 2.58-2.41 (m, 2H), 2.33-2.23 (m, 1H), 2.23-1.87 (m, 5H), 1.87-1.77 (m, 2H), 1.77-1.69 (m, 1H), 1.64-1.57 (m, 1H), 1.56 (d, J=7.1 Hz, 3H), 1.41 (t, J=12.6 Hz, 1H); MS (ESI) m/z=598.2 [M+H]$^+$.

Example 610. (1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl carbamate

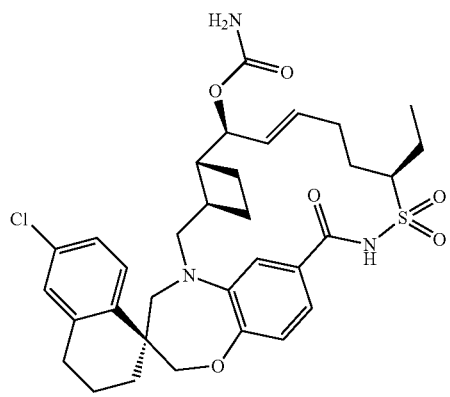 [SMILES: CC[C@@H]1CC/C=C/[C@H](OC(N)=O)[C@@H]2CC[C@H]2CN2C[C@@]3(CCCc4cc(Cl)ccc43)COc3ccc(cc32)C(=O)NS1(=O)=O]

Step 1: (S)-6'-chloro-N—((R)-hept-6-en-3-ylsulfonyl)-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide

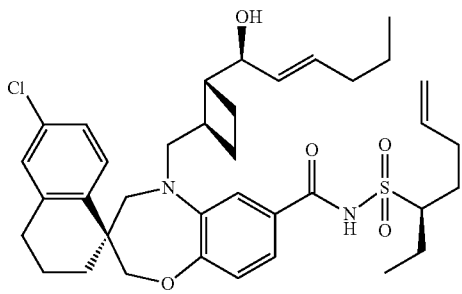 [SMILES: C=CCC[C@@H](CC)S(=O)(=O)NC(=O)c1ccc2c(c1)N(C[C@@H]1CC[C@H]1[C@@H](O)/C=C/CCC)C[C@@]1(CCCc3cc(Cl)ccc31)CO2]

4-Dimethylaminopyridine (DMAP) (0.041 g, 0.33 mmol) was added to a solution of (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A) (0.100 g, 0.196 mmol), triethylamine (0.082 mL, 0.59 mmol) and (R)-hept-6-ene-3-sulfonamide (Intermediate EE21) (0.094 g, 0.53 mmol) in DCM (1.0 mL). Then EDC (0.075 g, 0.39 mmol) was added slowly in portions, and reaction mixture was stirred at ambient temperature overnight. The reaction mixture was concentrated. The residue was injected into a 12 g ISCO Gold column and purified by combi-flash, eluting with 0% to 20% EtOAc (containing 0.3% AcOH)/hexanes to give (S)-6'-chloro-N—((R)-hept-6-en-3-ylsulfonyl)-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide (0.080 g, 0.12 mmol).

Step 2: (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

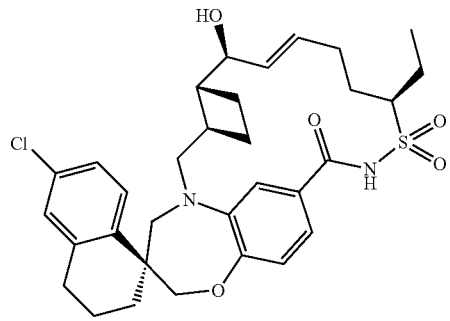 [SMILES: CC[C@@H]1CC/C=C/[C@H](O)[C@@H]2CC[C@H]2CN2C[C@@]3(CCCc4cc(Cl)ccc43)COc3ccc(cc32)C(=O)NS1(=O)=O]

A 100 mL round bottom flask was charged with (S)-6'-chloro-N—((R)-hept-6-en-3-ylsulfonyl)-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide (Example 610, Step 1) (0.080 g, 0.12 mmol) in AcOH (41 mL). It was stirred at ambient temperature under Ar bubbling through the reaction mixture for 15 min. To the homogeneous solution was added Hoveyda-Grubbs 2nd generation catalyst (0.015 g, 0.024 mmol). The mixture was stirred at ambient temperature under reduced pressure overnight and then air was bubbling through for 10 min. The reaction mixture was concentrated. The residue was injected into a 4 g ISCO Gold column and purified by combi-flash, eluting with 20% to 40% EtOAc (containing 0.3% AcOH)/hexanes to give the title compound (0.034 g, 0.057 mmol).

Step 3: (1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl carbamate To a solution of (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 610, Step 2) (0.034 g, 0.057 mmol) in a mixture of CHCl$_3$/DMF (2 mL, v/v=1/1) was added a solution of 2,2,2-trichloroacetyl isocyanate (0.021 g, 0.11 mmol) in chloroform (0.5 mL) at ambient temperature. After the mixture was stirred at ambient temperature for 1.5 h, MeOH (1.0 mL) and water (0.5 mL) were added to the reaction mixture, followed by LiOH (10 mg). Then the reaction was stirred overnight. The reaction mixture was diluted with DCM, extracted (2×DCM), and washed (brine). The combined organic layers were dried (Na$_2$SO$_4$) and concentrated under reduced pressure. The crude product was purified by reversed phase preparatory HPLC (Gemini™ Prep C$_{18}$ 5 μm column; Phenomenex, Torrance, CA; gradient elution of 50% to 70% MeCN in water, where both solvents contain 0.1% TFA, 30 min method) to provide the title compound as a white solid (0.015 g, 0.023 mmol). $^1$H NMR (500 MHz, CDCl$_3$) δ ppm 7.97 (s, 1H), 7.68 (d, J=8.6 Hz, 1H), 7.18 (dd, J=2.3, 8.4 Hz, 1H), 7.09 (d, J=2.2 Hz, 1H), 7.07-7.03 (m, 1H), 6.95-6.86 (m, 2H), 5.84-5.70 (m, 1H), 5.61 (dd, J=7.2, 15.3 Hz, 1H), 5.13 (t, J=6.4 Hz, 1H), 4.58 (br. s., 2H), 4.13-4.01 (m, 3H), 3.92 (dd, J=4.0, 15.5 Hz, 1H), 3.75 (d, J=14.4 Hz, 1H), 3.20 (d, J=14.4 Hz, 1H), 2.99 (dd, J=8.3, 15.4 Hz, 1H), 2.80-2.73 (m, 2H), 2.67-2.54 (m, 1H), 2.41-2.25 (m, 3H), 2.12-1.75 (m, 7H), 1.70-1.62 (m, 1H), 1.39 (t, J=12.7 Hz, 1H), 1.24-1.17 (m, 3H); m/z (ESI, +ve ion) 664.2 (M+Na)$^+$.

Example 611. ((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diaza-tetracyclo[14.7.2.0$^{3,6}$.0$^{19,24}$]pentacosa [8,16,18,24] tetraen]-12'-yl)methyl carbamate Step 1: (S)-2-(N,N-bis(4-methoxybenzyl)sulfamoyl)hex-5-en-1-yl carbamate

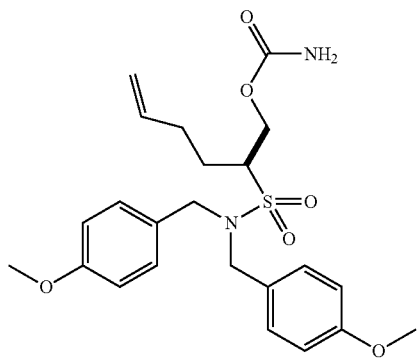

A racemic mixture of (S)-1-hydroxy-N,N-bis(4-methoxybenzyl)hex-5-ene-2-sulfonamide and (R)-1-hydroxy-N,N-bis(4-methoxybenzyl)hex-5-ene-2-sulfonamide (Example 434, Step 2) was purified by Thar 350 SFC (150×50 mm AD column; with 105 g/min MeOH+(20 mM NH$_3$)+105 g/min CO$_2$, Runtime=20 min) to give a pure (S)-1-hydroxy-N,N-bis(4-methoxybenzyl)hex-5-ene-2-sulfonamide as the slower eluting isomer.

To a solution of (S)-1-hydroxy-N,N-bis(4-methoxybenzyl)hex-5-ene-2-sulfonamide (0.800 g, 1.91 mmol) in a mixture of CHCl$_3$/DMF (20 mL, v/v=1/1) was added a solution of 2,2,2-trichloroacetyl isocyanate (0.467 g, 2.48 mmol) in CHCl$_3$ (3 mL) at ambient temperature. After the reaction was stirred for 0.5 h, MeOH (5 mL), water (2 mL), and LiOH (100 mg) were added to the reaction mixture successively. The mixture was stirred at ambient temperature overnight. Then the reaction mixture was diluted (DCM), extracted (2×DCM), and washed (brine). The combined organic layers were dried (Na$_2$SO$_4$) and concentrated under reduced pressure. The residue was injected into a 80 g ISCO Gold column and purified by combi-flash, eluting with 30% to 45% EtOAc (containing 0.3% AcOH)/hexanes to give (S)-2-(N,N-bis(4-methoxybenzyl)sulfamoyl)hex-5-en-1-yl carbamate (0.82 g, 1.8 mmol).

Step 2: (S)-2-sulfamoylhex-5-en-1-yl carbamate

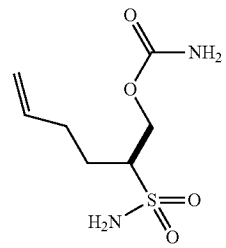

To a solution of (S)-2-(N,N-bis(4-methoxybenzyl)sulfamoyl)hex-5-en-1-yl carbamate (0.820 g, 1.77 mmol) (Example 611, Step 1) in DCM (8.9 mL) was added anisole (0.96 mL, 8.9 mmol), followed by dropwise addition of TFA (3.2 mL, 43 mmol). After the reaction mixture was stirred at 40° C. overnight, the reaction mixture was concentrated. The residue was injected into a 40 g ISCO Gold column and purified by combi-flash, eluting with 30% to 60% EtOAc (containing 0.3% AcOH)/hexanes to give (S)-2-sulfamoylhex-5-en-1-yl carbamate (0.36 g, 1.6 mmol).

Step 3: ((1S,3'R,6'R,7'S,8'E,12'S)-6-chloro-7'-hydroxy-13',13'-dioxido-15'-oxo-3,4-dihydro-2H-spiro [naphthalene-1,22'-[20]oxa[13]thia[1,14]diazatetra-cyclo[14.7.2.0$^{3,6}$.0$^{19,24}$]pentacosa [8,16,18,24] tetraen]-12'-yl)methyl carbamate The title compound was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A) by a procedure analogous to that described in Example 610, Steps 1 through 2, replacing (R)-hept-6-ene-3-sulfonamide in Step 1 with (S)-2-sulfamoylhex-5-en-1-yl carbamate (Example 611, Step 2). The crude product was purified by reversed phase preparatory HPLC (Gemini™ Prep C$_{18}$ 5 μm column; Phenomenex, Torrance, CA; gradient elution of 45% to 70% MeCN in water, where both solvents contain 0.1% TFA, 30 min method) to provide the title compound as the faster eluting isomer as a white foam. $^1$H NMR (500 MHz, CDCl$_3$) δ ppm 8.06 (s, 1H), 7.70 (d, J=8.6 Hz, 1H), 7.19 (d, J=8.3 Hz, 1H), 7.10 (d, J=2.4 Hz, 1H), 6.96-6.90 (m, 3H), 5.82-5.70 (m, 2H), 4.71-4.65 (m, 2H), 4.37 (d, J=4.9 Hz, 1H), 4.22-4.15 (m, 1H), 4.13-4.06 (m, 2H), 3.83 (d, J=14.9 Hz, 1H), 3.71 (d, J=14.2 Hz, 1H), 3.25 (d, J=14.4 Hz, 1H), 3.07-3.00 (m, 1H), 2.83-2.72 (m, 2H), 2.44 (m, 1H), 2.41-2.26 (m, 3H), 2.06-1.60 (m, 9H), 1.42 (m, 1H); m/z (ESI, +ve ion) 644.2 (M+H)$^+$.

Example 612. ((1S,3'R,6'R,7'S,8'Z,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-12'-yl)methyl carbamate

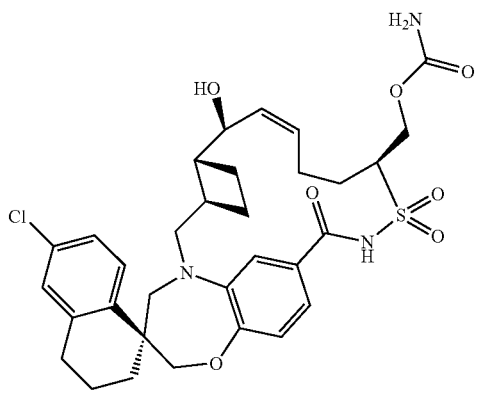 [SMILES: NC(=O)OC[C@@H]1CC/C=C\[C@H](O)[C@@H]2CC[C@H]2CN2C[C@@]3(CCCc4cc(Cl)ccc43)COc3ccc(cc32)C(=O)NS1(=O)=O]

The title compound was obtained as the second eluting isomer from the reversed phase preparatory HPLC separation in Example 611, Step 3. ¹H NMR (500 MHz, CDCl₃) δ ppm 9.58 (br. s, 1H), 7.70 (d, J=8.6 Hz, 1H), 7.34 (d, J=8.1 Hz, 1H), 7.18 (dd, J=2.4, 8.6 Hz, 1H), 7.15 (m, 1H), 7.10 (d, J=2.2 Hz, 1H), 6.98 (d, J=8.3 Hz, 1H), 5.63 (m, 1H), 5.53 (dd, J=5.9, 11.2 Hz, 1H), 4.71 (dd, J=5.6, 12.0 Hz, 1H), 4.56 (dd, J=5.7, 11.9 Hz, 1H), 4.45 (t, J=5.9 Hz, 1H), 4.14 (s, 2H), 4.02-3.96 (m, 1H), 3.75-3.60 (m, 2H), 3.32 (m, 2H), 2.81-2.74 (m, 2H), 2.62-2.51 (m, 2H), 2.48 (m, 1H), 2.31-2.23 (m, 1H), 2.23-2.13 (m, 1H), 2.04-1.58 (m, 8H), 1.53 (m, 1H); m/z (ESI, +ve ion) 644.2 (M+H)⁺.

Example 613. 3-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-12'-yl)propanenitrile or 3-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-12'-yl)propanenitrile (Isomer 1)

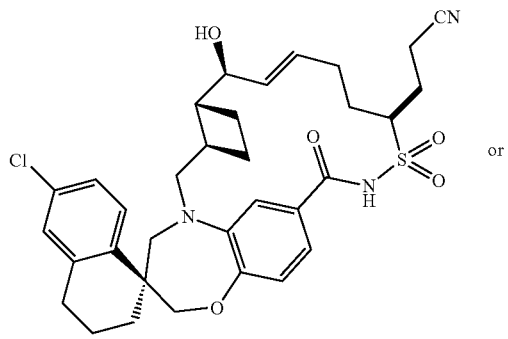

or

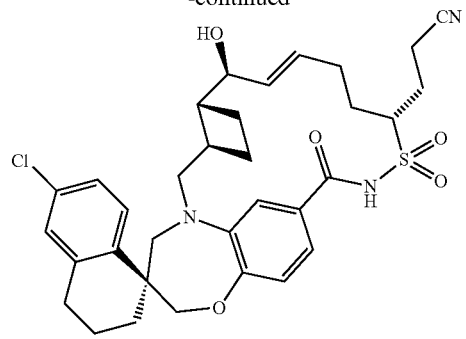

Step 1: (S)-3-(N,N-bis(4-methoxybenzyl)sulfamoyl)hept-6-en-1-yl methanesulfonate and (R)-3-(N,N-bis(4-methoxybenzyl)sulfamoyl)hept-6-en-1-yl methanesulfonate

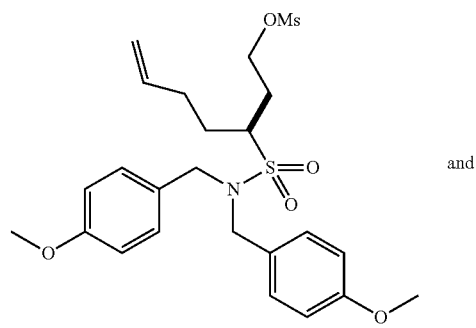

and

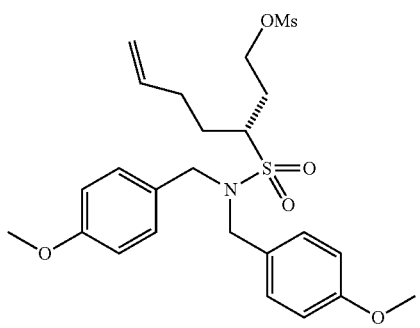

To a solution of (S)-1-hydroxy-N,N-bis(4-methoxybenzyl)hept-6-ene-3-sulfonamide and (R)-1-hydroxy-N,N-bis(4-methoxybenzyl)hept-6-ene-3-sulfonamide (Example 564, Step 1) (50 mg, 0.11 mmol) and triethylamine (32 µl, 0.23 mmol) in THF (1 mL) was added methanesulfonyl chloride (13 µL, 0.17 mmol) at 0° C. The reaction was allowed to warm up to room temperature. After being stirred at room temperature for 1h, the reaction was quenched (sat.NH₄Cl), extracted (DCM) and washed (brine). The combined organic layers were dried (Na₂SO₄) and concentrated under reduced pressure to give the title compound (58 mg, 0.11 mmol).

Step 2: (S)-1-cyano-N,N-bis(4-methoxybenzyl)hept-6-ene-3-sulfonamide and (R)-1-cyano-N,N-bis(4-methoxybenzyl)hept-6-ene-3-sulfonamide

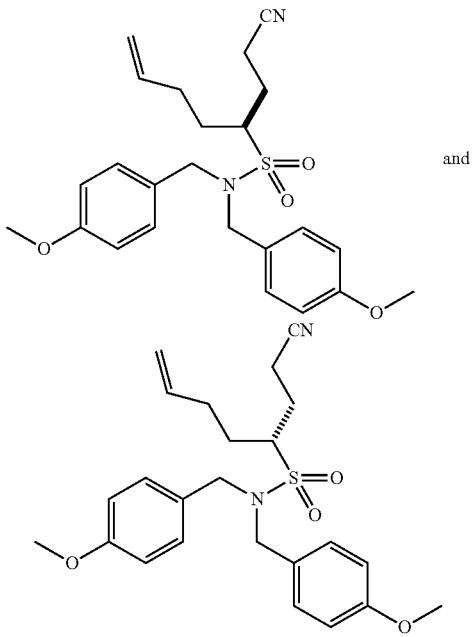

To a solution of (S)-3-(n,n-bis(4-methoxybenzyl)sulfamoyl)hept-6-en-1-yl methanesulfonate and (R)-3-(n,n-bis(4-methoxybenzyl)sulfamoyl)hept-6-en-1-yl methanesulfonate (Example 613, Step 1) (58 mg, 0.11 mmol) in MeCN (1 mL) was added tetraethylammonium cyanide (89 mg, 0.57 mmol). After being stirred at 80° C. for 1 h, the reaction was quenched (sat.NH$_4$Cl), extracted (DCM) and washed (brine). The combined organic layers were dried (Na$_2$SO$_4$) and concentrated under reduced pressure. The residue was injected into a 4 g ISCO Gold column and purified by combi-flash, eluting with 0% to 40% EtOAc/hexanes to give the title compound (50 mg, 0.11 mmol).

Step 3: 3-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)propanenitrile or 3-((1S,3'R,6'R,7'S, 8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$] pentacosa [8,16,18,24]tetraen]-12'-yl)propanenitrile (Isomer 1)

One of the title compounds was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A) by a procedure analogous to that described in Example 611, Steps 2 through 3, replacing (S)-2-(N,N-bis(4-methoxybenzyl)sulfamoyl)hex-5-en-1-yl carbamate in Step 2 with (S)-1-cyano-n,n-bis(4-methoxybenzyl)hept-6-ene-3-sulfonamide and (R)-1-cyano-n,n-bis(4-methoxybenzyl)hept-6-ene-3-sulfonamide (Example 613, Step 2). The crude product was purified by reversed phase preparatory HPLC (Gemini™ Prep C$_{18}$ 5 μm column; Phenomenex, Torrance, CA; gradient elution of 45% to 70% MeCN in water, where both solvents contain 0.1% TFA, 30 min method) to provide one of the title compounds as the faster eluting isomer as a white foam. $^1$H NMR (500 MHz, CDCl$_3$) δ ppm 8.08 (s, 1H), 7.70 (d, J=8.6 Hz, 1H), 7.19 (d, J=8.3 Hz, 1H), 7.13-7.06 (m, 1H), 6.98-6.89 (m, 3H), 5.82-5.70 (m, 2H), 4.26 (t, J=5.4 Hz, 1H), 4.20 (m, 1H), 4.16-4.06 (m, 2H), 3.84 (m, 1H), 3.72 (d, J=14.4 Hz, 1H), 3.24 (d, J=14.4 Hz, 1H), 3.04 (dd, J=8.9, 15.3 Hz, 1H), 2.90-2.72 (m, 4H), 2.51-2.31 (m, 4H), 2.25-2.13 (m, 2H), 2.06-1.67 (m, 9H), 1.41 (m, 1H); m/z (ESI, +ve ion) 624.2 (M+H)$^+$.

Example 614. 3-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24] tetraen]-12'-yl)propanenitrile or 3-((1S,3'R,6'R,7'S, 8'E,12'S)-6-chloro-7'-hydroxy-13',13'-dioxido-15'-oxo-3,4-dihydro-2H-spiro[naphthalene-1,22'-[20]oxa [13]thia[1,14]diazatetracyclo[14.7.2.0$^{3,6}$.0$^{19,24}$] pentacosa [8,16,18,24]tetraen]-12'-yl)propanenitrile (Isomer 2)

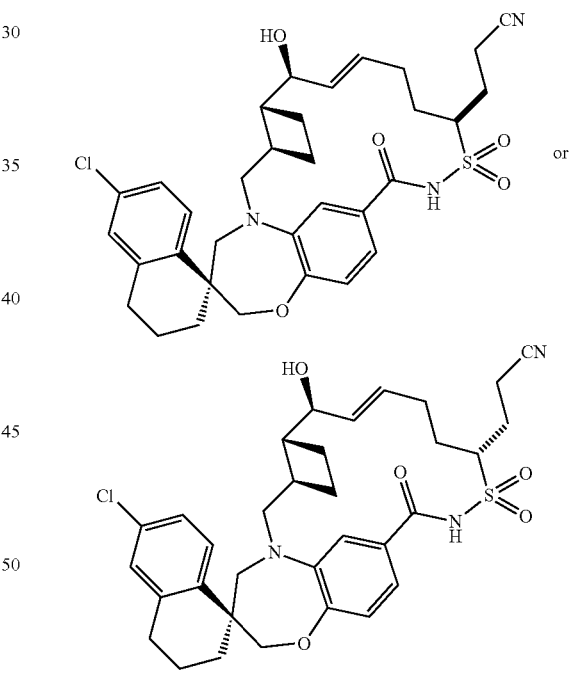

One of the title compounds was obtained as the second eluting isomer from the reversed phase preparatory HPLC separation in Example 613 as a white foam. $^1$H NMR (500 MHz, CDCl$_3$) δ ppm 9.70 (s, 1H), 7.72 (d, J=8.6 Hz, 1H), 7.44 (dd, J=2.0, 8.3 Hz, 1H), 7.19 (dd, J=2.3, 8.4 Hz, 1H), 7.10 (d, J=2.2 Hz, 1H), 7.07-6.96 (m, 2H), 5.79-5.67 (m, 1H), 5.57 (m, 1H), 4.50 (t, J=6.0 Hz, 1H), 4.18-4.08 (m, 2H), 3.88 (d, J=15.4 Hz, 1H), 3.82-3.74 (m, 1H), 3.69 (d, J=14.2 Hz, 1H), 3.22 (d, J=14.2 Hz, 1H), 3.14 (m, 1H), 2.81-2.72 (m, 4H), 2.66-2.39 (m, 4H), 2.28-1.52 (m, 11H), 1.52-1.42 (m, 1H); m/z (ESI, +ve ion) 624.2 (M+H)$^+$.

Example 615. (1S,3'R,6'R,7'S,8'E,12'S)-6-chloro-7'-methoxy-12'-(2-methoxy-2-methylpropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,12'R)-6-chloro-7'-methoxy-12'-(2-methoxy-2-methylpropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

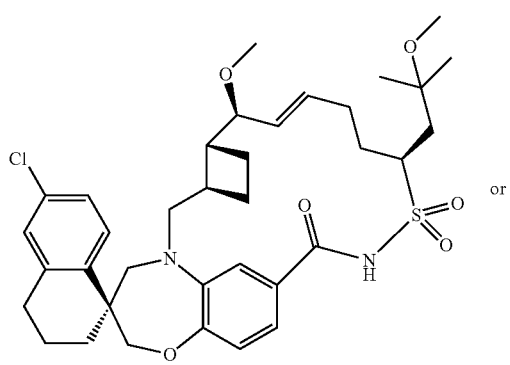

or

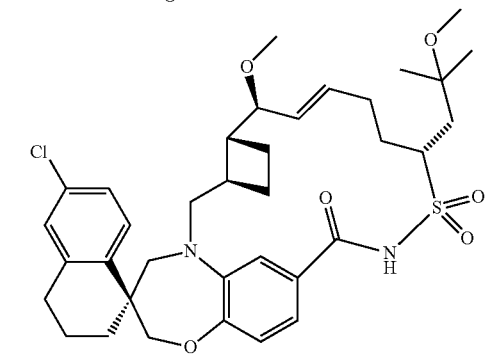

To a solution of (1S,3'R,6'R,7'S,8'E,12'S)-6-chloro-7'-hydroxy-12'-(2-hydroxy-2-methylpropyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,12'R)-6-chloro-7'-hydroxy-12'-(2-hydroxy-2-methylpropyl)-3,4-dihydro-2H,15'H-spiro[naphthalene-1,22'-[20]oxa[13]thia[1,14]diazatetracyclo[14.7.2.0³,⁶.0¹⁹,²⁴ ]pentacosa[8,16,18,24]tetraen]-15'-one 13',13'-dioxide (Example 558) (10 mg, 0.016 mmol) in THF (0.5 mL) was added NaH (60% dispersion in mineral oil, 3.1 mg, 0.078 mmol) at 0° C. After the reaction mixture was stirred at 0° C. for 30 min, a solution of iodomethane (6.6 mg, 0.047 mmol) in THF (0.5 mL) was added. The reaction mixture was stirred at ambient temperature for 2 h and then was quenched (water and 1 N aqueous HCl solution). The reaction mixture was diluted with EtOAc. The organics were extracted (2×EtOAc), and washed (brine). The combined organic layers were dried (Na₂SO₄) and concentrated under reduced pressure. The residue was injected into a 4 g ISCO Gold column and purified by combi-flash, eluting with 0% to 30% EtOAc (containing 0.3% AcOH)/hexanes to give one of the title compounds (4.8 mg, 7.2 µmol). ¹H NMR (500 MHz, CDCl₃) δ ppm 7.80 (s, 1H), 7.62 (d, J=8.6 Hz, 1H), 7.11 (m, 1H), 7.01 (d, J=2.4 Hz, 1H), 6.86-6.81 (m, 1H), 6.81-6.77 (m, 1H), 6.71 (d, J=1.7 Hz, 1H), 5.83 (m, 1H), 5.43 (dd, J=9.2, 15.3 Hz, 1H), 4.41 (dd, J=3.7, 8.1 Hz, 1H), 4.06-3.94 (m, 2H), 3.72 (d, J=14.9 Hz, 1H), 3.64 (d, J=14.4 Hz, 1H), 3.60 (dd, J=3.8, 9.2 Hz, 1H), 3.19-3.11 (m, 4H), 3.11-3.08 (s, 3H), 2.90 (dd, J=10.3, 15.4 Hz, 1H), 2.76-2.63 (m, 2H), 2.52-2.42 (m, 1H), 2.42-2.34 (m, 2H), 2.28-2.11 (m, 2H), 1.97 (m, 1H), 1.91-1.65 (m, 8H), 1.63-1.51 (m, 2H), 1.29 (s, 3H), 1.18 (s, 3H); m/z (ESI, +ve ion) 671.2 (M+H)⁺.

Example 616. methyl 3-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-12'-yl)propanoate or methyl 3-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-12'-yl)propanoate

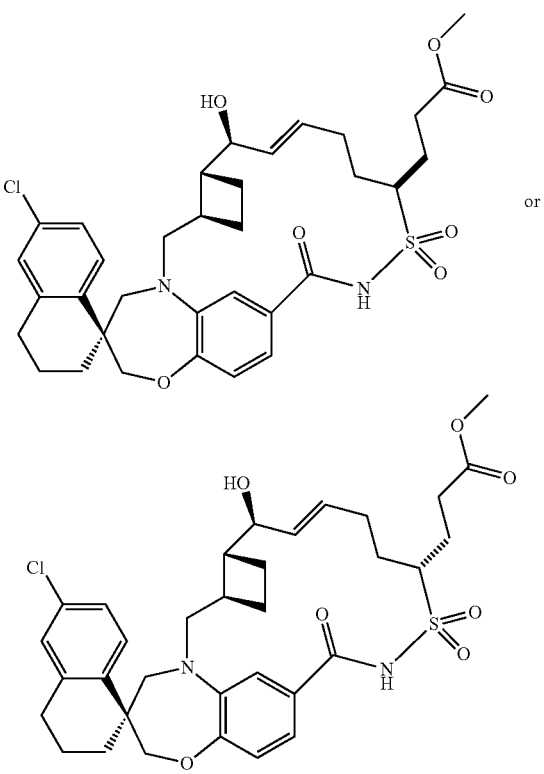

Step 1: (S)-1-hydroxy-N,N-bis(4-methoxybenzyl)oct-7-ene-4-sulfonamide and (R)-1-hydroxy-N,N-bis(4-methoxybenzyl)oct-7-ene-4-sulfonamide

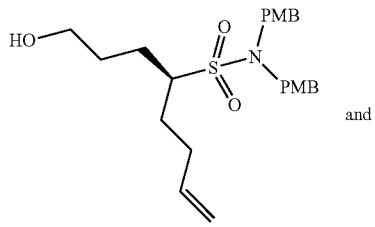

and

-continued

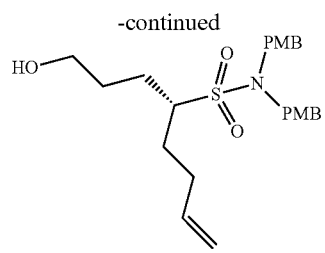

To a solution of (R)-1-((tert-butyldimethylsilyl)oxy)-N,N-bis(4-methoxybenzyl)oct-7-ene-4-sulfonamide and (S)-1-((tert-butyldimethylsilyl)oxy)-N,N-bis(4-methoxybenzyl)oct-7-ene-4-sulfonamide (80 mg, 0.14 mmol) (Example 560, Step 1) in THF (1 mL) was added TBAF (1 M solution in THF, 290 μL, 0.290 mmol) at 0° C. The reaction was allowed to warm up to ambient temperature. After the reaction mixture was stirred overnight, the reaction was quenched (saturated aqueous NH$_4$Cl), extracted (DCM) and washed (brine). The combined organic layers were dried (Na$_2$SO$_4$) and concentrated under reduced pressure. The residue was injected into a 12 g ISCO Gold column and purified by combi-flash, eluting with 20% to 80% EtOAc/hexanes to give the title compound (51 mg, 0.11 mmol).

Step 2: (S)-4-(N,N-bis(4-methoxybenzyl)sulfamoyl)oct-7-enoic Acid and (R)-4-(N,N-bis(4-methoxybenzyl)sulfamoyl)oct-7-enoic Acid

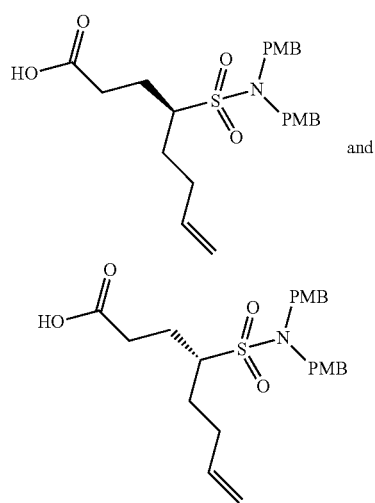

To a solution of (S)-1-hydroxy-N,N-bis(4-methoxybenzyl)oct-7-ene-4-sulfonamide and (R)-1-hydroxy-N,N-bis(4-methoxybenzyl)oct-7-ene-4-sulfonamide (Example 616, Step 1) (125 mg, 0.279 mmol) in acetone (2.8 mL) were added KBr (3.3 mg, 0.028 mmol), 5% sodium bicarbonate in water (1.3 mL, 0.78 mmol), TEMPO (48 mg, 0.31 mmol), and 6% sodium hypochlorite in water (0.45 mL, 0.36 mmol) at 0° C. After the reaction mixture was stirred at 0° C. for 3.5 h, the reaction was concentrated under reduced pressure, diluted (EtOAc and ice-cold 1 N aqueous HCl), extracted (2×EtOAc), and washed (brine). The combined organic layers were dried (Na$_2$SO$_4$) and concentrated under reduced pressure. The residue was injected into a 12 g ISCO Gold column and purified by combi-flash, eluting with 20% to 100% EtOAc/hexanes to give the title compound (100 mg, 0.217 mmol).

Step 3: (S)-methyl 4-(N,N-bis(4-methoxybenzyl)sulfamoyl)oct-7-enoate and (R)-methyl 4-(N,N-bis(4-methoxybenzyl)sulfamoyl)oct-7-enoate

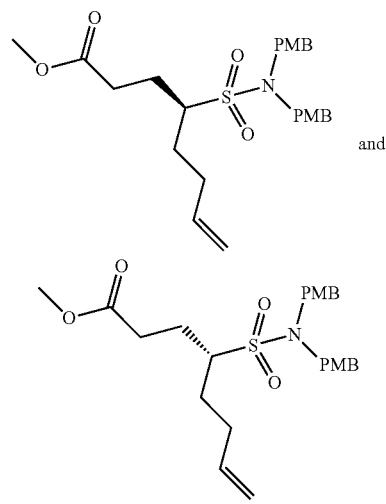

To a solution of (S)-4-(N,N-bis(4-methoxybenzyl)sulfamoyl)oct-7-enoic acid and (R)-4-(N,N-bis(4-methoxybenzyl)sulfamoyl)oct-7-enoic acid (Example 616, Step 2) (439 mg, 0.951 mmol) in MeOH (3.17 mL) was added thionyl chloride (139 μL, 1.90 mmol) at 0° C. dropwise. Then the reaction was allowed to warm to ambient temperature. After the reaction mixture was stirred overnight, the reaction was diluted (EtOAc and ice-cold water), extracted (2×EtOAc), and washed (saturated aqueous NaHCO$_3$ and brine). The combined organic layers were dried (Na$_2$SO$_4$) and concentrated under reduced pressure to provide the title compound (452 mg, 0.950 mmol) which was used in the next step without further purification.

Step 4: methyl 3-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)propanoate or methyl 3-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)propanoate One of the title compounds was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12) by a procedure analogous to that described in Example 611, Steps 2 through 3, replacing (S)-2-(N,N-bis(4-methoxybenzyl)sulfamoyl)hex-5-en-1-yl carbamate in Step 2 with (S)-methyl 4-(N,N-bis(4-methoxybenzyl)sulfamoyl)oct-7-enoate and (R)-methyl 4-(N,N-bis(4-methoxybenzyl)sulfamoyl)oct-7-enoate (Example 616, Steps 3). The crude product was purified by reversed phase preparatory HPLC (Gemini™ Prep C$_{18}$ 5 μm column; Phenomenex, Torrance, CA; gradient elution of 45% to 70% MeCN in water, where both solvents contain 0.1% TFA, 30 min method) to provide one of the title compounds as the faster eluting isomer as a white foam. $^1$H NMR (500 MHz, CDCl$_3$) δ ppm 8.03 (s, 1H), 7.70 (d, J=8.6 Hz, 1H), 7.19 (dd, J=2.2, 8.6 Hz, 1H), 7.10 (d, J=2.2 Hz, 1H), 6.96-6.87 (m, 3H), 5.89-5.81 (m, 1H), 5.78-5.70 (m, 1H), 4.24 (m, 1H), 4.20-4.14 (m, 1H), 4.14-4.06 (m, 2H), 3.83 (m, 1H), 3.77-3.68 (m, 4H), 3.24 (d, J=14.4 Hz, 1H), 3.02 (dd, J=9.4, 15.3 Hz, 1H), 2.87-2.70 (m, 4H), 2.51-2.40 (m, 1H), 2.39-2.21 (m, 5H), 2.06-1.93 (m, 3H), 1.91-1.74 (m, 3H), 1.72-1.57 (m, 1H), 1.43-1.38 (m, 1H); m/z (ESI, +ve ion) 657.2 (M+H)$^+$.

Example 617. (1S,3'R,6'R,7'S,8'E,12'S)-6-chloro-12'-(2-hydroxyethyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-12'-(2-hydroxyethyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

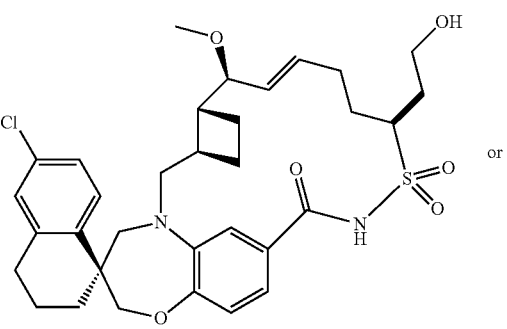

or

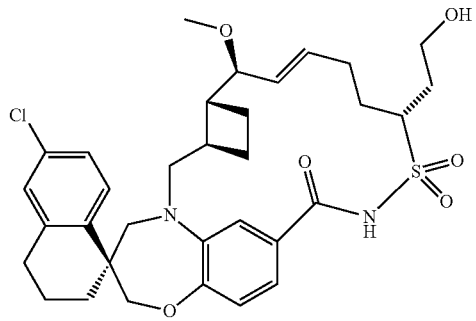

Step 1: (S)-1-hydroxyhept-6-ene-3-sulfonamide and (R)-1-hydroxyhept-6-ene-3-sulfonamide

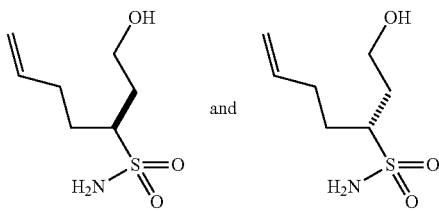

To a solution of (S)-1-hydroxy-N,N-bis(4-methoxybenzyl)hept-6-ene-3-sulfonamide and (R)-1-hydroxy-N,N-bis(4-methoxybenzyl)hept-6-ene-3-sulfonamide (Example 564, Step 1) (419 mg, 0.966 mmol) in DCM (6.4 mL) was added anisole (105 mg, 0.966 mmol) and 2,2,2-trifluoroacetic acid (110 mg, 0.966 mmol) at ambient temperature. After the reaction mixture was stirred at ambient temperature overnight, the reaction was heated at 40° C. for 5 h and the excess TFA was removed under reduced pressure. The residue was dissolved in THF/MeOH/H$_2$O (2.4 mL, v/v/v=1/1/1) and lithium hydroxide (231 mg, 9.66 mmol) was added at ambient temperature. After the reaction was stirred for 1 h, the reaction was quenched (saturated aqueous NH$_4$Cl), extracted (2×EtOAc), and washed (brine). The combined organic layers were dried (Na$_2$SO$_4$) and concentrated under reduced pressure. The residue was injected into a 40 g ISCO Gold column and purified by combi-flash, eluting with 0% to 20% MeOH/DCM to give the title compounds (55 mg, 0.29 mmol)

Step 2: (S)-1-((tert-butyldiphenylsilyl)oxy)hept-6-ene-3-sulfonamide and (R)-1-((tert-butyldiphenylsilyl)oxy)hept-6-ene-3-sulfonamide

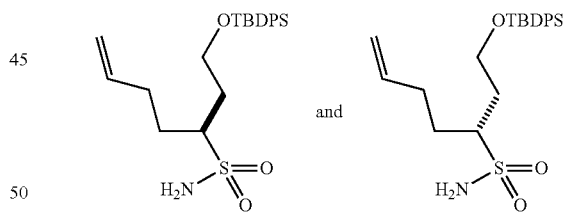

To a solution of (S)-1-hydroxyhept-6-ene-3-sulfonamide and (R)-1-hydroxyhept-6-ene-3-sulfonamide (Example 617, Step 1) (50 mg, 0.26 mmol) and imidazole (53 mg, 0.77 mmol) in DMF (1 mL) was added tert-butylchlorodiphenylsilane (0.10 mL, 0.38 mmol) at ambient temperature under Ar. After the reaction mixture was stirred overnight, the reaction was quenched (saturated aqueous NH$_4$Cl), extracted (2×EtOAc), and washed (brine). The combined organic layers were dried (Na$_2$SO$_4$) and concentrated under reduced pressure. The residue was injected into a 12 g ISCO Gold column and purified by combi-flash, eluting with 0% to 40% EtOAc/hexane to give the title compounds (65 mg, 0.15 mmol).

Step 3: (1S,3'R,6'R,7'S,8'E,12'S)-6-chloro-7'-hydroxy-12'-(2-(((2-methyl-2-propanyl)(diphenyl)silyl)oxy)ethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,12'R)-6-chloro-7'-hydroxy-12'-(2-(((2-methyl-2-propanyl)(diphenyl)silyl)oxy)ethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide Step 4: (1S,3'R,6'R,7'S,8'E,12'S)-6-chloro-7'-methoxy-12'-(2-(((2-methyl-2-propanyl)(diphenyl)silyl)oxy)ethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,12'R)-6-chloro-7'-methoxy-12'-(2-(((2-methyl-2-propanyl)(diphenyl)silyl)oxy)ethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

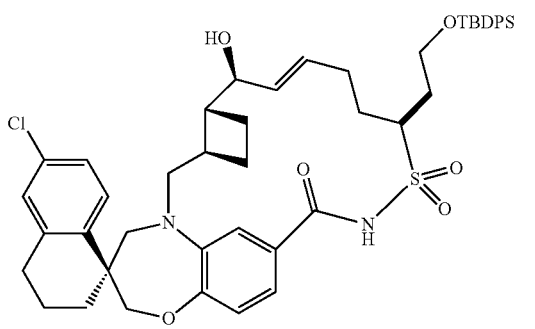

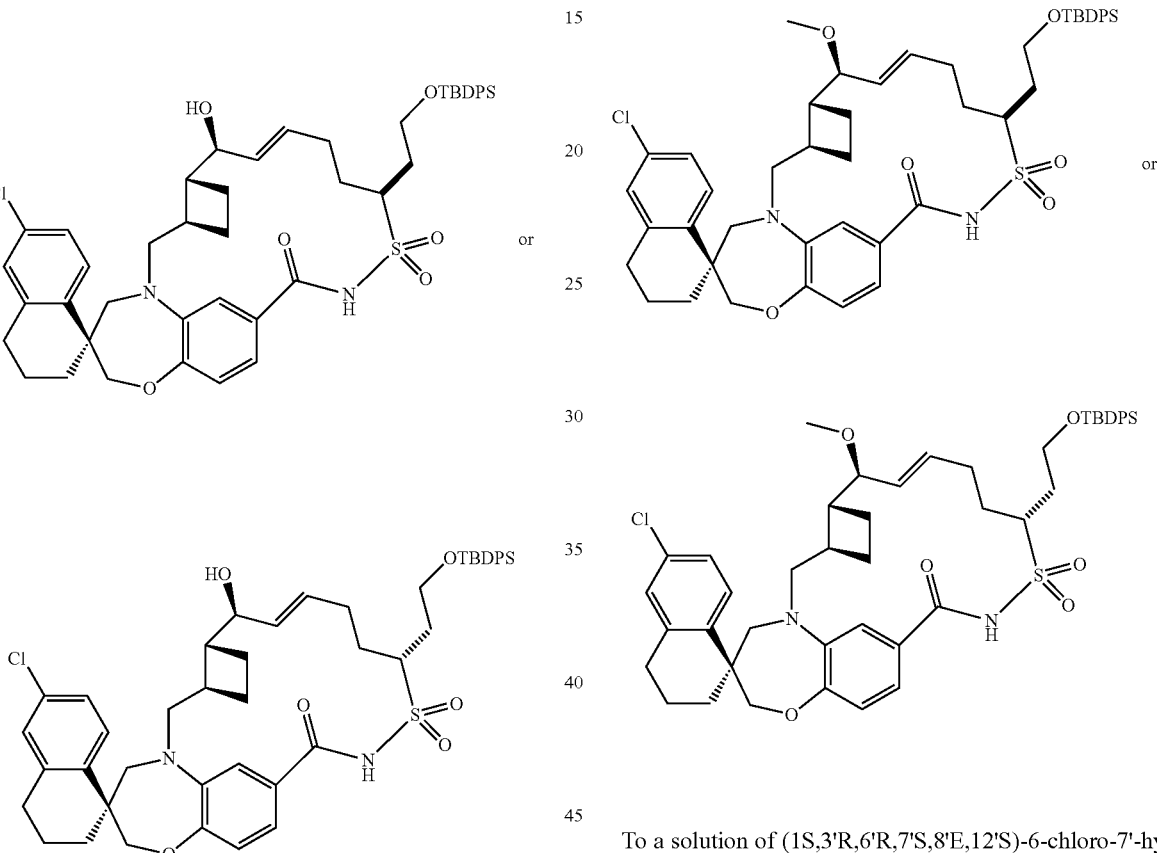

One of the title compounds was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A) by a procedure analogous to that described in Example 610, Steps 1 through 2, replacing (R)-hept-6-ene-3-sulfonamide in Step 1 with (S)-1-((tert-butyldiphenylsilyl)oxy)hept-6-ene-3-sulfonamide and (R)-1-((tert-butyldiphenylsilyl)oxy)hept-6-ene-3-sulfonamide (Example 617, Step 2). The crude product was purified by reversed phase preparatory HPLC (Gemini™ Prep C$_{18}$ 5 µm column; Phenomenex, Torrance, CA; gradient elution of 50% to 90% MeCN in water, where both solvents contain 0.1% TFA, 30 min method) to provide the title compound as the faster eluting isomer as a white foam.

To a solution of (1S,3'R,6'R,7'S,8'E,12'S)-6-chloro-7'-hydroxy-12'-(2-(((2-methyl-2-propanyl)(diphenyl)silyl)oxy)ethyl)-3,4-dihydro-2h,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,12'R)-6-chloro-7'-hydroxy-12'-(2-(((2-methyl-2-propanyl)(diphenyl)silyl)oxy)ethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 617, Step 3) (10 mg, 0.012 mmol) in THF (0.5 mL) was added NaH (60% dispersion in mineral oil, 2.3 mg, 0.059 mmol) at 0° C. After the reaction mixture was stirred at 0° C. for 30 min, a solution of iodomethane (2.2 µL, 0.035 mmol) in THF (0.5 mL) was added. The reaction mixture was stirred at ambient temperature for 2 h and then was quenched (water and 1 N aqueous HCl solution). The reaction mixture was diluted (EtOAc). The organics were extracted (2×EtOAc), and washed (brine). The combined organic layers were dried (Na$_2$SO$_4$) and concentrated under reduced pressure to provide the crude title compound which was used in next step without further purification.

1289

Step 5: (1S,3'R,6'R,7'S,8'E,12'S)-6-chloro-12'-(2-hydroxyethyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-12'-(2-hydroxyethyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide To a solution of the crude product from Example 617, Step 4 in THF (1 mL) was added TBAF (1.0 M in THF, 0.58 mL, 0.58 mmol). After the reaction mixture was stirred at 37° C. for 5 h, the reaction was quenched (saturated aqueous NH$_4$Cl), extracted (2×EtOAc), and washed (brine). The combined organic layers were dried (Na$_2$SO$_4$) and concentrated under reduced pressure to provide a crude product. The crude product was purified by reversed phase preparatory HPLC (Gemini™ Prep C$_{18}$ 5 µm column; Phenomenex, Torrance, CA; gradient elution of 45% to 70% MeCN in water, where both solvents contain 0.1% TFA, 30 min method) to provide one of the title compounds as a white foam (3.0 mg, 4.8 µmol). $^1$H NMR (500 MHz, CDCl$_3$) δ ppm 7.94 (s, 1H), 7.70 (d, J=8.3 Hz, 1H), 7.19 (dd, J=2.2, 8.6 Hz, 1H), 7.10 (d, J=2.2 Hz, 1H), 6.95-6.91 (m, 1H), 6.91-6.88 (m, 1H), 6.84 (d, J=2.0 Hz, 1H), 5.90-5.82 (m, 1H), 5.55 (dd, J=9.0, 15.2 Hz, 1H), 4.39 (m, 1H), 4.14-4.02 (m, 3H), 3.97-3.87 (m, 1H), 3.82 (d, J=15.2 Hz, 1H), 3.72 (d, J=14.2 Hz, 1H), 3.66 (dd, J=3.4, 9.0 Hz, 1H), 3.27-3.21 (m, 4H), 3.00 (dd, J=10.1, 15.3 Hz, 1H), 2.85-2.71 (m, 2H), 2.50-2.41 (m, 1H), 2.41-2.27 (m, 4H), 2.23-2.12 (m, 1H), 2.10-1.93 (m, 4H), 1.90-1.54 (m, 5H), 1.45-1.34 (m, 1H); m/z (ESI, +ve ion) 629.2 (M+H)$^+$.

Example 618. 3-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)-N,N-dimethylpropanamide or 3-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)-N,N-dimethylpropanamide

1290

-continued

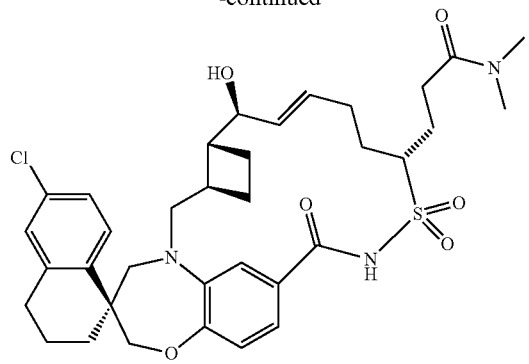

Step 1: 3-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)propanoic Acid or 3-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)propanoic Acid

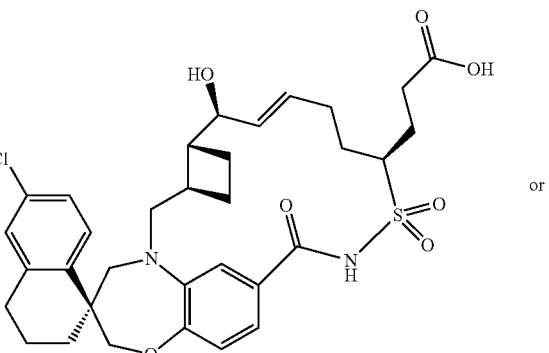

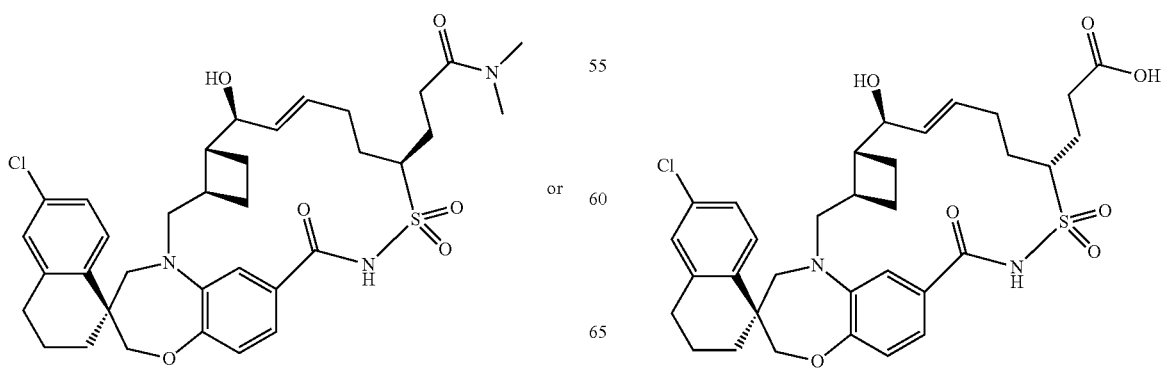

To a solution of methyl 3-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)propanoate or methyl 3-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)propanoate (23 mg, 0.035 mmol) (Example 616) in a mixture of THF/water/MeOH (4 mL, v/v/v=2/1/1) was added LiOH (8.4 mg, 0.35 mmol). After the reaction mixture was stirred at ambient temperature for 2 h, the reaction mixture was acidified (1 N aqueous HCl solution), diluted (EtOAc), extracted (2×EtOAc). The combined organic layers were washed (brine), dried (Na$_2$SO$_4$), and concentrated under reduced pressure to provide the crude title compound which was used in next step without further purification.

Step 2: 3-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)-N,N-dimethylpropanamide or 3-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo [14.7.2.0$^{3,6}$.0$^{19,24}$]pentacosa [8,16,18,24]tetraen]-12'-yl)-N,N-dimethylpropanamide To a solution of 3-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo [14.7.2.0$^{3,6}$.0$^{19,24}$]pentacosa[8,16,18,24]tetraen]-12'-yl)propanoic acid or 3-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo [14.7.2.0$^{3,6}$.0$^{19,24}$]pentacosa[8,16,18,24]tetraen]-12'-yl)propanoic acid (0.020 g, 0.031 mmol) (Example 618, Step 1) in DMF (1.0 mL) was added N-ethyl-N-isopropylpropan-2-amine (0.012 g, 0.093 mmol), hatu (0.018 g, 0.047 mmol), and dimethylamine (2.0 M solution in THF, 0.078 mL, 0.16 mmol). After the reaction mixture was stirred at ambient temperature for 5 h, the reaction mixture was diluted (MeOH) and purified by reversed phase preparatory HPLC (Gemini™ Prep C$_{18}$ 5 μm column; Phenomenex, Torrance, CA; gradient elution of 45% to 70% MeCN in water, where both solvents contain 0.1% TFA, 30 min method) to provide one of the title compounds as a white foam (0.016 g, 0.024 mmol). $^1$H NMR (500 MHz, CDCl$_3$) δ ppm 8.07 (s, 1H), 7.72 (d, J=8.6 Hz, 1H), 7.21 (m, 1H), 7.11 (d, J=2.2 Hz, 1H), 6.96-6.90 (m, 3H), 5.90-5.82 (m, 1H), 5.78-5.71 (m, 1H), 4.26 (dd, J=4.2, 7.6 Hz, 1H), 4.17-4.07 (m, 3H), 3.84 (d, J=14.2 Hz, 1H), 3.73 (d, J=14.2 Hz, 1H), 3.26 (d, J=14.4 Hz, 1H), 3.13 (s, 3H), 3.09-3.00 (m, 4H), 3.00-2.91 (m, 1H), 2.86-2.68 (m, 3H), 2.49-2.44 (m, 1H), 2.40-2.27 (m, 5H), 2.09-1.95 (m, 3H), 1.92-1.74 (m, 5H), 1.72-1.63 (m, 1H), 1.42 (t, J=12.6 Hz, 1H); m/z (ESI, +ve ion) 670.2 (M+H)$^+$.

Example 619. methyl ((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetate or methyl ((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl) acetate (Isomer 1)

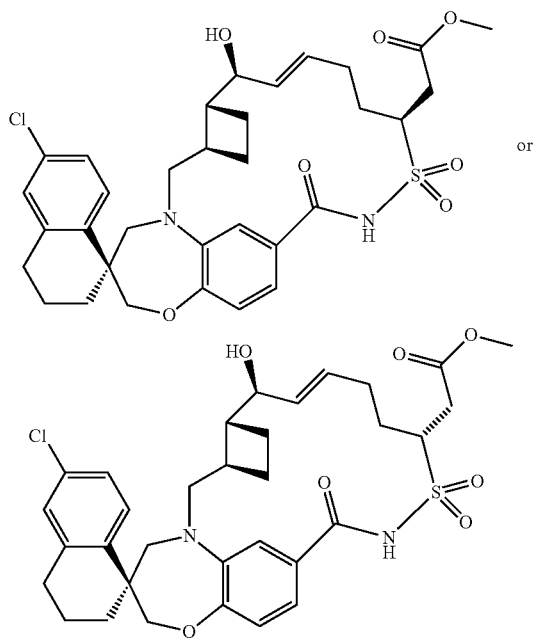

Step 1: (R)-methyl 3-(N,N-bis(4-methoxybenzyl)sulfamoyl)hept-6-enoate and (S)-methyl 3-(N,N-bis(4-methoxybenzyl)sulfamoyl)hept-6-enoate

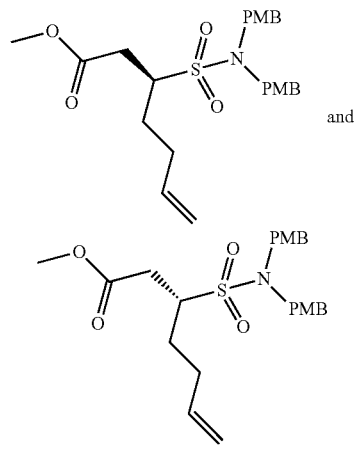

The title compounds were prepared from (S)-1-hydroxy-N,N-bis(4-methoxybenzyl)hept-6-ene-3-sulfonamide and (R)-1-hydroxy-N,N-bis(4-methoxybenzyl)hept-6-ene-3- sulfonamide (Example 564, Step 1) by a procedure analogous to that described in Example 616, Steps 2 through 3.

Step 2: methyl ((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-12'-yl)acetate or methyl ((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-12'-yl)acetate (Isomer 1)

One of the title compounds was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A) by a procedure analogous to that described in Example 611, Steps 2 through 3, replacing (S)-2-(N,N-bis(4-methoxybenzyl)sulfamoyl)hex-5-en-1-yl carbamate in step 2 with (R)-methyl 3-(N,N-bis(4-methoxybenzyl)sulfamoyl)hept-6-enoate and (S)-methyl 3-(N,N-bis(4-methoxybenzyl)sulfamoyl)hept-6-enoate (Example 619, Steps 1). The crude product was purified by reversed phase preparatory HPLC (Gemini™ Prep C$_{18}$ 5 μm column; Phenomenex, Torrance, CA; gradient elution of 45% to 70% MeCN in water, where both solvents contain 0.1% TFA, 30 min method) to provide one of the title compounds as the faster eluting isomer as a white foam. ¹H NMR (400 MHz, CDCl$_3$) δ ppm 8.30 (br. s., 1H), 7.72 (d, J=8.4 Hz, 1H), 7.21 (dd, J=2.2, 8.5 Hz, 1H), 7.12 (d, J=2.2 Hz, 1H), 6.99-6.91 (m, 3H), 5.99-5.90 (m, 1H), 5.76 (dd, J=7.6, 15.3 Hz, 1H), 4.68 (m, 1H), 4.29 (dd, J=4.1, 7.6 Hz, 1H), 4.16-4.07 (m, 2H), 3.86-3.77 (m, 4H), 3.73 (d, J=14.1 Hz, 1H), 3.31-3.22 (m, 2H), 3.08 (dd, J=8.9, 15.2 Hz, 1H), 2.86-2.69 (m, 3H), 2.52-2.31 (m, 3H), 2.22-2.12 (m, 1H), 2.07-1.79 (m, 8H), 1.75-1.66 (m, 1H), 1.44 (m, 1H); m/z (ESI, +ve ion) 643.2 (M+H)⁺.

Example 620. methyl ((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-12'-yl)acetate or methyl ((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-12'-yl)acetate (Isomer 2)

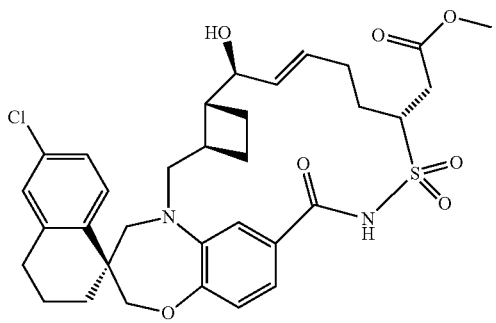

One of the title compounds was obtained as the second (slower) eluting isomer from the reverse phase preparatory HPLC purification in Example 619, Step 2 as a white foam. ¹H NMR (400 MHz, CDCl$_3$) δ ppm 7.72 (d, J=8.6 Hz, 1H), 7.42 (dd, J=1.6, 8.2 Hz, 1H), 7.18 (dd, J=2.2, 8.4 Hz, 1H), 7.09 (d, J=2.0 Hz, 1H), 7.04-6.96 (m, 2H), 5.75-5.64 (m, 1H), 5.59-5.43 (m, 1H), 4.55 (m, 1H), 4.21 (m, 1H), 4.18-4.04 (m, 2H), 3.90 (m, 1H), 3.77 (s, 3H), 3.73-3.61 (m, 1H), 3.34-3.18 (m, 2H), 3.13 (dd, J=8.6, 15.3 Hz, 1H), 2.84-2.66 (m, 4H), 2.41-1.78 (m, 10H), 1.78-1.58 (m, 2H), 1.54-1.35 (m, 1H); m/z (ESI, +ve ion) 643.2 (M+H)⁺.

Example 621. 2-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-12'-yl)-N,N-dimethylacetamide or 2-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-12'-yl)-N,N-dimethylacetamide

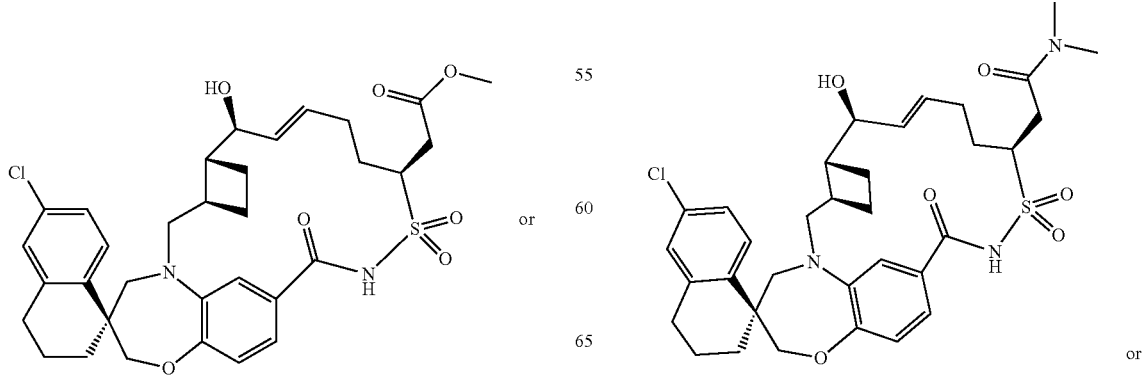

-continued

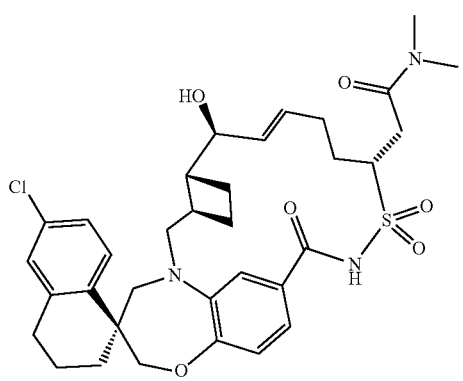

One of the title compounds was prepared from methyl ((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetate or methyl ((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetate (isomer 1) (Example 619) by a procedure analogous to that described in Example 618, Steps 1 through 2. The crude product was purified by reversed phase preparatory HPLC (Gemini™ Prep C$_{18}$ 5 μm column; Phenomenex, Torrance, CA; gradient elution of 45% to 70% MeCN in water, where both solvents contain 0.1% TFA, 30 min method) to provide one of the title compounds as a white foam. $^1$H NMR (500 MHz, CDCl$_3$) δ ppm 8.22 (br. s., 1H), 7.63 (d, J=8.6 Hz, 1H), 7.11 (m, 1H), 7.02 (d, J=2.2 Hz, 1H), 6.89-6.81 (m, 3H), 5.94-5.87 (m, 1H), 5.64 (dd, J=7.8, 15.4 Hz, 1H), 4.65 (m, 1H), 4.19 (dd, J=3.9, 7.6 Hz, 1H), 4.08-3.95 (m, 2H), 3.71 (d, J=15.4 Hz, 1H), 3.62 (d, J=14.4 Hz, 1H), 3.27 (dd, J=3.7, 16.4 Hz, 1H), 3.18 (d, J=14.2 Hz, 1H), 3.09-2.96 (m, 4H), 2.93 (s, 3H), 2.77-2.63 (m, 2H), 2.56 (dd, J=8.3, 16.4 Hz, 1H), 2.40-2.20 (m, 3H), 2.20-2.08 (m, 1H), 1.96-1.84 (m, 4H), 1.81-1.66 (m, 4H), 1.64-1.53 (m, 1H), 1.35 (t, J=12.5 Hz, 1H); m/z (ESI, +ve ion) 656.2 (M+H)$^+$.

Example 622. 3-((1S,3'R,6'R,7'S,8'E,12'S)-6-chloro-7'-methoxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)-N,N-dimethylpropanamide or 3-((1S,3'R,6'R,7'S,8'E,12'R)-6-chloro-7'-methoxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)-N,N-dimethylpropanamide

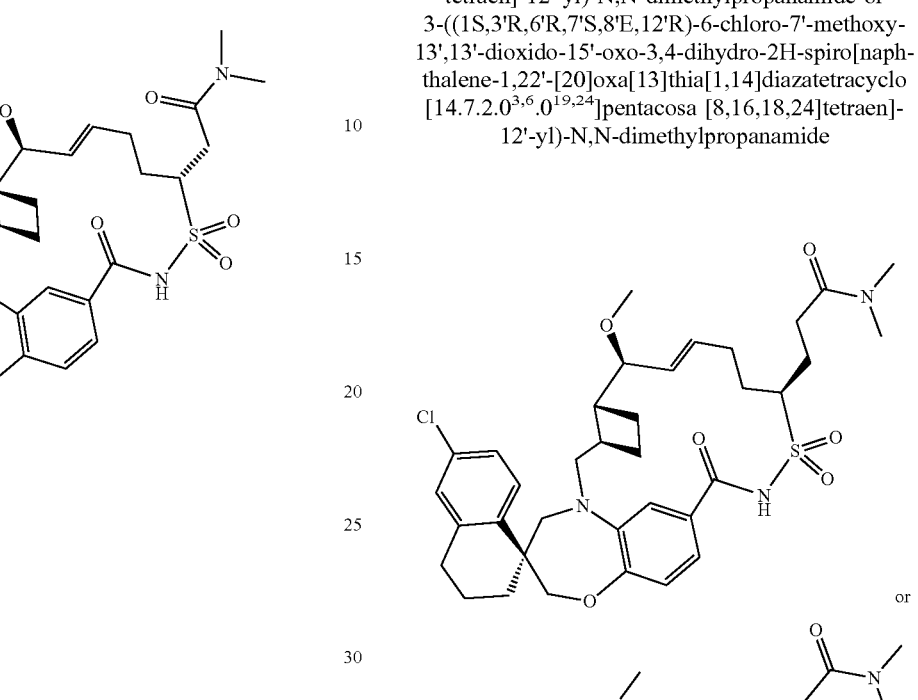

One of the title compounds was prepared from 3-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)-N,N-dimethylpropanamide or 3-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)propyl acid (Example 618) by a procedure analogous to that described in Example 617, Step 4. The crude product was purified by reversed phase preparatory HPLC (Gemini™ Prep C$_{18}$ 5 μm column; Phenomenex, Torrance, CA; gradient elution of 45% to 70% MeCN in water, where both solvents contain 0.1% TFA, 30 min method) to provide one of the title compounds as a white foam. $^1$H NMR (500 MHz, CDCl$_3$) δ ppm 7.93 (s, 1H), 7.70 (d, J=8.6 Hz, 1H), 7.19 (dd, J=2.2, 8.6 Hz, 1H), 7.14-7.05 (m, 1H), 6.94-6.90 (m, 1H), 6.90-6.86 (m, 1H), 6.82 (d, J=1.7 Hz, 1H), 5.86-5.78 (m, 1H), 5.53 (dd, J=9.2, 15.3 Hz, 1H), 4.19 (m, 1H), 4.14-4.02 (m, 2H), 3.81 (d, J=15.2 Hz, 1H), 3.71 (d, J=14.4 Hz, 1H), 3.68-3.60 (m, 1H), 3.28-3.21 (m, 4H), 3.10 (s, 3H), 3.04-2.95 (m, 4H), 2.88-

2.72 (m, 4H), 2.49-2.26 (m, 7H), 2.08-1.92 (m, 4H), 1.87-1.59 (m, 3H), 1.39 (m, 1H); m/z (ESI, +ve ion) 684.2 (M+H)$^+$.

Example 623. methyl ((1S,3'R,6'R,7'S,8'E,12'S)-6-chloro-7'-(2-ethoxy-2-oxoethoxy)-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate or methyl ((1S,3'R,6'R,7'S,8'E,12'S)-6-chloro-7'-(2-ethoxy-2-oxoethoxy)-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate

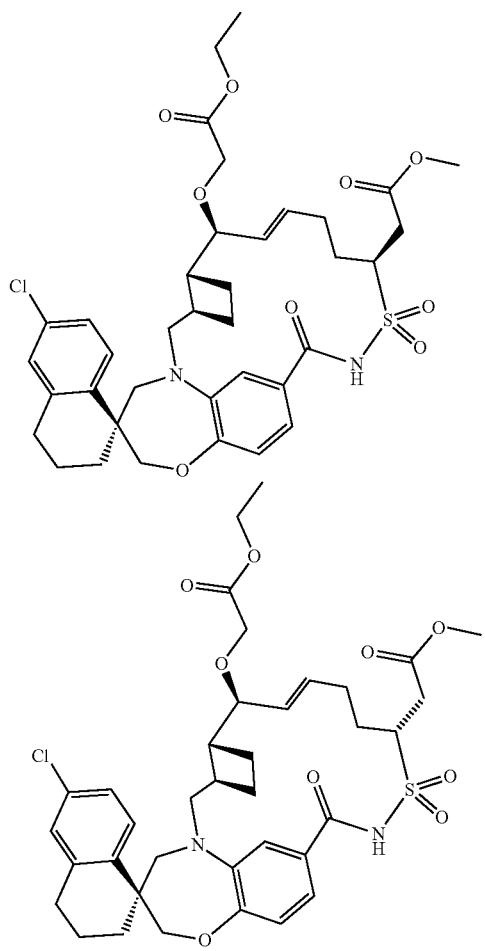

or

To a solution of methyl ((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetate or methyl ((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetate (isomer 1) (Example 619) (8.0 mg, 0.012 mmol) and rhodium (ii) acetate dimer (0.55 mg, 1.2 µmol) in DCM (0.5 mL) was added ethyl diazoacetate (0.015 mL, 0.15 mmol) slowly. After the reaction mixture was stirred at room temperature for 1 hour, the reaction solution was concentrated under reduced pressure and purified by reversed phase preparatory HPLC (Gemini™ Prep C$_{18}$ 5 µm column; Phenomenex, Torrance, CA; gradient elution of 45% to 70% MeCN in water, where both solvents contain 0.1% TFA, 30 min method) to provide one of the title compounds as a white foam (2.0 mg, 2.7 µmol). $^1$H NMR (500 MHz, CDCl$_3$) δ ppm 8.03 (br. s., 1H), 7.69 (d, J=8.6 Hz, 1H), 7.19 (dd, J=2.3, 8.4 Hz, 1H), 7.10 (d, J=2.2 Hz, 1H), 6.95-6.91 (m, 1H), 6.91-6.87 (m, 1H), 6.81 (s, 1H), 5.94-5.86 (m, 1H), 5.57 (dd, J=8.9, 15.3 Hz, 1H), 4.78 (m, 1H), 4.24 (q, J=7.1 Hz, 2H), 4.12-3.98 (m, 4H), 3.90 (dd, J=3.8, 8.9 Hz, 1H), 3.83-3.80 (m, 1H), 3.78 (s, 3H), 3.75-3.66 (m, 1H), 3.27-3.20 (m, 2H), 3.02 (dd, J=10.1, 15.3 Hz, 1H), 2.83-2.73 (m, 2H), 2.70 (dd, J=7.5, 16.5 Hz, 1H), 2.65-2.58 (m, 1H), 2.39-2.27 (m, 2H), 2.27-2.15 (m, 1H), 2.06-2.02 (m, 1H), 2.00-1.78 (m, 7H), 1.75-1.66 (m, 1H), 1.44-1.38 (m, 1H), 1.32 (t, J=7.2 Hz, 3H); m/z (ESI, +ve ion) 729.2 (M+H)$^+$.

Example 624. methyl ((1S,3'R,6'R,7'S,8'E,12'S)-6-chloro-7'-methoxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate or methyl ((1S,3'R,6'R,7'S,8'E,12'R)-6-chloro-7'-methoxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate

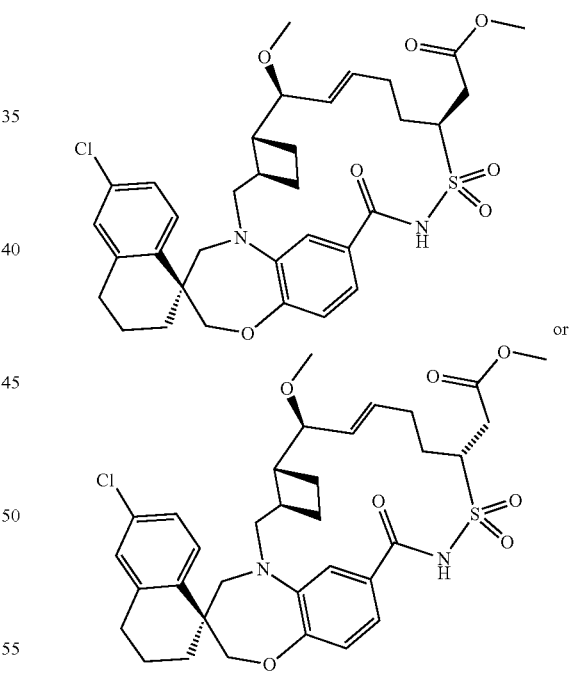

To a vigorously stirred solution of methyl ((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetate or methyl ((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetate (isomer 1) (Example 619) (8.0 mg, 0.012 mmol) and fluoroboric acid (50 wt % solution in water, 1.6 µL, 0.012 mmol) in DCM (0.5 mL) was added (trimethylsilyl)diazomethane (2.0 M in diethyl ether, 6.2 µl, 0.012 mmol) dropwise at 0° C. After the reaction mixture was stirred at 0° C. for 1 h, another 0.5 equv. of (trimethylsilyl)diazomethane (2.0 M in diethyl ether, 0.8 µL, 0.006 mmol) was added to the reaction mixture. Then, the reaction mixture was stirred at 0° C. for 10 min, quenched (MeOH), and purified by reversed phase preparatory HPLC (Gemini™ Prep $C_{18}$ 5 µm column; Phenomenex, Torrance, CA; gradient elution of 40% to 90% MeCN in water, where both solvents contain 0.1% TFA, 30 min method) to provide one of the title compounds as a white foam (1.5 mg, 2.3 µmol). $^1$H NMR (500 MHz, CDCl$_3$) δ ppm $^1$H NMR (500 MHz, CD3Cl) δ 8.00 (s, 1H), 7.74-7.67 (m, 1H), 7.22-7.15 (m, 1H), 7.10 (d, J=2.2 Hz, 1H), 6.95-6.91 (m, 1H), 6.91-6.87 (m, 1H), 6.82 (d, J=1.7 Hz, 1H), 5.98-5.86 (m, 1H), 5.54 (dd, J=8.9, 15.3 Hz, 1H), 4.81 (m, 1H), 4.14-4.02 (m, 2H), 3.83-3.66 (m, 6H), 3.32-3.19 (m, 5H), 3.00 (dd, J=10.1, 15.3 Hz, 1H), 2.83-2.74 (m, 2H), 2.70 (dd, J=7.5, 16.5 Hz, 1H), 2.52-2.40 (m, 1H), 2.39-2.19 (m, 3H), 2.07-1.74 (m, 8H), 1.71-1.64 (m, 1H), 1.40 (t, J=12.7 Hz, 1H); m/z (ESI, +ve ion) 657.2 (M+H)$^+$.

Example 625. (1S,3'R,6'R,7'S,8'E,12'S)-12'-(2-(4-bromophenoxy)ethyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-12'-(2-(4-bromophenoxy)ethyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

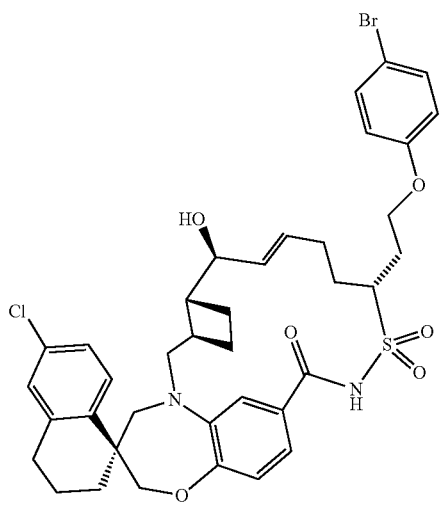

Step 1: (S)-1-(4-bromophenoxy)-N,N-bis(4-methoxybenzyl)hept-6-ene-3-sulfonamide and (R)-1-(4-bromophenoxy)-N,N-bis(4-methoxybenzyl)hept-6-ene-3-sulfonamide

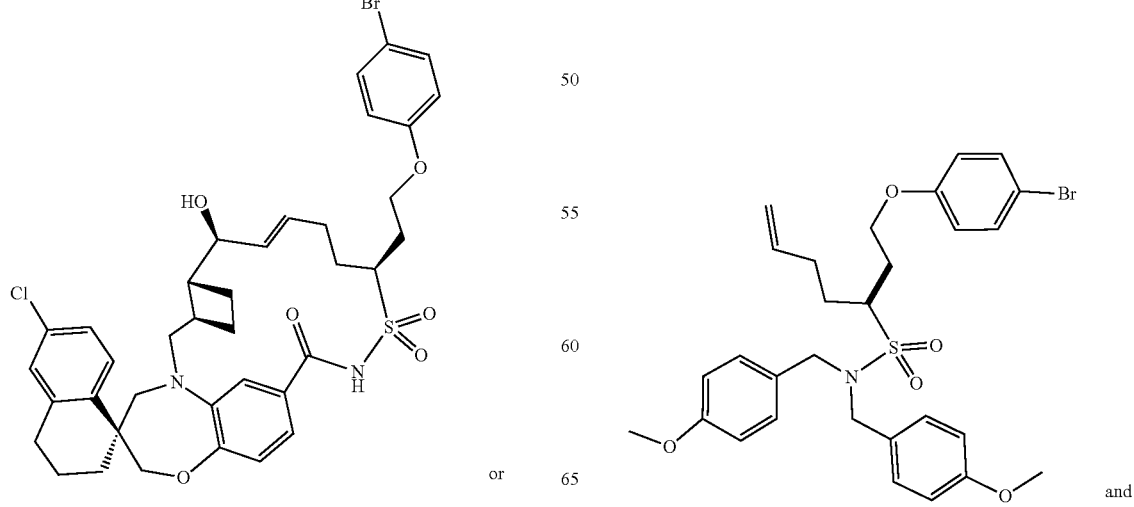

-continued

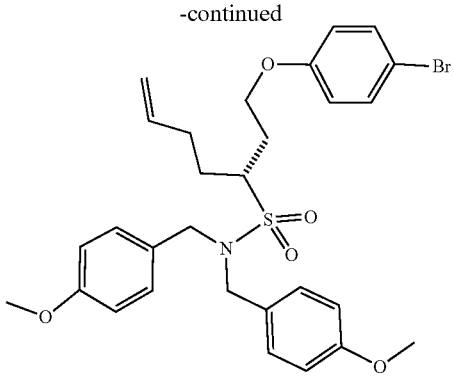

To a solution of (S)-1-hydroxy-N,N-bis(4-methoxybenzyl)hept-6-ene-3-sulfonamide and (R)-1-hydroxy-N,N-bis(4-methoxybenzyl)hept-6-ene-3-sulfonamide (Example 564, Step 1). (550 mg, 1.27 mmol) in toluene (8 mL) was added 4-bromophenol (219 mg, 1.27 mmol), triphenylphosphine (399 mg, 1.52 mmol), and di-tert-butyl azodicarboxylate (351 mg, 1.52 mmol) successively at ambient temperature. After the reaction mixture was stirred for 24 h, the reaction solution was concentrated under reduced pressure. The residue was injected into a 24 g ISCO Gold column and purified by combi-flash, eluting with 10% to 40% EtOAc/hexanes to give the title compounds (450 mg, 0.765 mmol).

Step 2: (1S,3'R,6'R,7'S,8'E,12'S)-12'-(2-(4-bromophenoxy)ethyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-12'-(2-(4-bromophenoxy)ethyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide One of the title compounds was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A) by a procedure analogous to that described in Example 611, Steps 2 through 3, replacing (S)-2-(N,N-bis(4-methoxybenzyl)sulfamoyl)hex-5-en-1-yl carbamate in Step 2 with (S)-1-(4-bromophenoxy)-N,N-bis(4-methoxybenzyl)hept-6-ene-3-sulfonamide and (R)-1-(4-bromophenoxy)-N,N-bis(4-methoxybenzyl)hept-6-ene-3-sulfonamide (Example 625, Step 1). The crude product was purified by reversed phase preparatory HPLC (Gemini™ Prep C$_{18}$ 5 µm column; Phenomenex, Torrance, CA; gradient elution of 45% to 70% MeCN in water, where both solvents contain 0.1% TFA, 30 min method) to provide one of the title compounds as the faster eluting isomer as a white foam. $^1$H NMR (500 MHz, CDCl$_3$) δ ppm 8.02 (s, 1H), 7.70 (d, J=8.6 Hz, 1H), 7.40 (d, J=8.0 Hz, 2H), 7.19 (dd, J=2.2, 8.3 Hz, 1H), 7.10 (d, J=2.0 Hz, 1H), 6.96-6.87 (m, 3H), 6.87-6.80 (m, 2H), 5.83 (m, 1H), 5.77-5.68 (m, 1H), 4.38-4.31 (m, 1H), 4.30-4.20 (m, 3H), 4.16-4.05 (m, 2H), 3.83 (d, J=14.7 Hz, 1H), 3.72 (d, J=14.4 Hz, 1H), 3.24 (d, J=14.2 Hz, 1H), 3.03 (dd, J=9.5, 15.2 Hz, 1H), 2.83-2.72 (m, 2H), 2.62 (dd, J=7.5, 15.5 Hz, 1H), 2.49-2.40 (m, 1H), 2.39-2.19 (m, 5H), 2.11-1.61 (m, 8H), 1.41 (t, J=12.8 Hz, 1H); m/z (ESI, +ve ion) 771.0 (M+H)$^+$.

Example 626. 4-(3-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)propanoyl)-N,N-dimethyl-1-piperazinesulfonamide or 4-(3-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)propanoyl)-N,N-dimethyl-1-piperazinesulfonamide

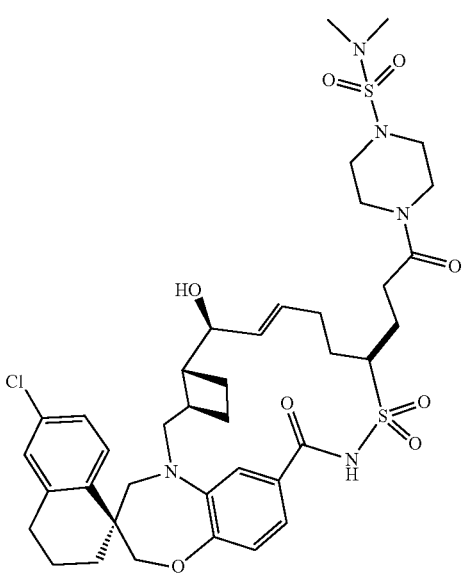

or

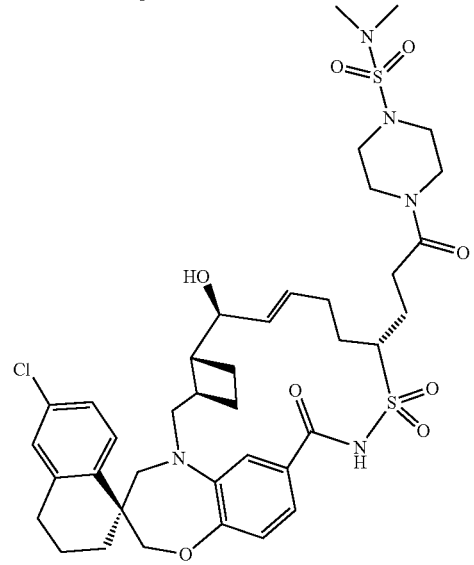

One of the title compounds was prepared from 3-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)propyl acid or 3-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)propyl acid (Example 618, Step 1) by a procedure analogous to that described in Example 618, Steps 2, replacing dimethylamine in Step 2 with N,N-dimethylpiperazine-1-sulfonamide. The crude product was purified by reversed phase preparatory HPLC (Gemini™ Prep $C_{18}$ 5 μm column; Phenomenex, Torrance, CA; gradient elution of 45% to 70% MeCN in water, where both solvents contain 0.1% TFA, 30 min method) to provide one of the title compounds as a white foam. $^1$H NMR (500 MHz, CDCl$_3$) δ ppm 8.50 (br. s, 1H) 7.70 (d, J=8.31 Hz, 1H) 7.18 (dd, J=8.44, 2.08 Hz, 1H) 7.09 (d, J=1.96 Hz, 1H) 6.95-6.90 (m, 2H) 6.88 (s, 1H) 5.90-5.79 (m, 1H) 5.70 (dd, J=15.28, 7.21 Hz, 1H) 4.23 (dd, J=7.09, 4.16 Hz, 1H) 4.15-4.04 (m, 3H) 3.92-3.84 (m, 1H) 3.79 (d, J=14.67 Hz, 1H) 3.75-3.65 (m, 2H) 3.63-3.51 (m, 2H) 3.40-3.19 (m, 5H) 3.07-2.92 (m, 2H) 2.85 (s, 6H) 2.81-2.70 (m, 2H) 2.69-2.60 (m, 1H) 2.47-2.23 (m, 6H) 2.07-1.88 (m, 4H) 1.88-1.71 (m, 6H) 1.71-1.60 (m, 1H) 1.47-1.35 (m, 1H); m/z (ESI, +ve ion) 840.2 (M+Na)$^+$.

Example 627. 2-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)-N-(3-chlorophenyl)acetamide or 2-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)-N-(3-chlorophenyl)acetamide

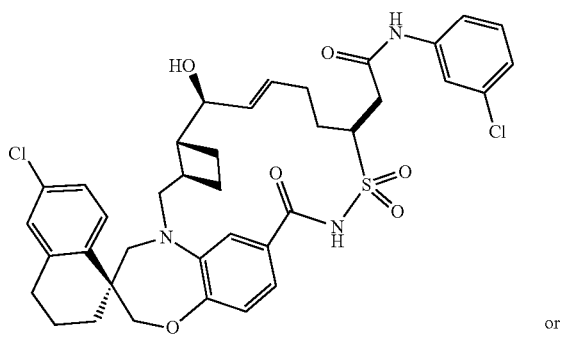

or

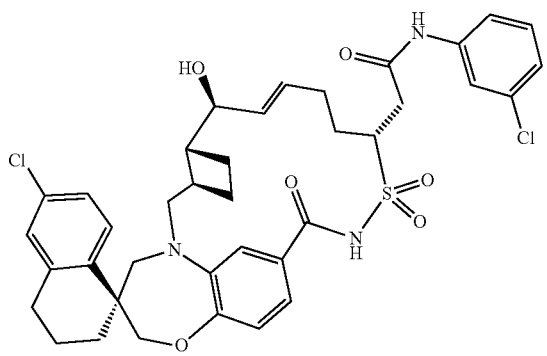

Step 1: ((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetic Acid or ((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetic Acid

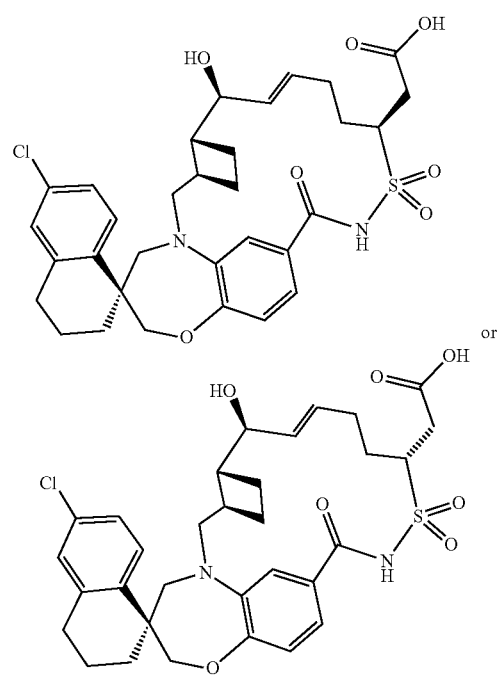

To a solution of methyl ((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,2 4]tetraen]-12'-yl)acetate or methyl ((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24] tetraen]-12'-yl)acetate (isomer 1) (330 mg, 0.51 mmol) (Example 619) in THF/water/MeOH (4 mL, v/v/v=2/1/1) was added LiOH (61 mg, 2.6 mmol). After the reaction mixture was stirred at ambient temperature for 2 h, the reaction mixture was acidified (1 N aqueous HCl solution), diluted (EtOAc), and extracted (2×EtOAc). The combined organic layers were washed (brine), dried (Na$_2$SO$_4$), and concentrated under reduced pressure to provide a crude product which was used in the next step without purification.

Step 2: 2-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)-N-(3-chlorophenyl)acetamide or 2-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)-N-(3-chlorophenyl)acetamide To a solution of ((1S,3'R,6'R,7'S,8'E,12'S)-6-chloro-7'-hydroxy-13',13'-dioxido-15'-oxo-3,4-dihydro-2H-spiro

[naphthalene-1,22'-[20]oxa[13]thia[1,14]diazatetracyclo[14.7.2.0³,⁶.0¹⁹,²⁴]pentacosa[8,16,18,24]tetraen]-12'-yl)acetic acid or ((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-12'-yl)acetic acid (Example 627, Step 1) (0.020 g, 0.032 mmol) and 3-chloroaniline (10 µL, 0.095 mmol) in pyridine (0.5 mL) was added EDC (0.018 g, 0.095 mmol). The reaction mixture was stirred at ambient temperature overnight and purified by reversed phase preparatory HPLC (Gemini™ Prep C$_{18}$ 5 µm column; Phenomenex, Torrance, CA; gradient elution of 45% to 70% MeCN in water, where both solvents contain 0.1% TFA, 30 min method) to provide one of the title compounds as a white foam (8.0 mg, 11 µmol). ¹H NMR (500 MHz, CDCl$_3$) δ ppm 8.38 (br. s., 1H), 8.03-7.93 (m, 1H), 7.75-7.65 (m, 2H), 7.39 (d, J=7.8 Hz, 1H), 7.19 (dd, J=2.3, 8.4 Hz, 1H), 7.13-7.09 (m, 2H), 7.02-6.88 (m, 3H), 5.84 (dd, J=7.6, 14.4 Hz, 1H), 5.72 (dd, J=7.3, 15.2 Hz, 1H), 4.63-4.54 (m, 1H), 4.21 (dd, J=4.2, 7.1 Hz, 1H), 4.16-4.03 (m, 2H), 3.79 (d, J=14.4 Hz, 1H), 3.70 (d, J=14.2 Hz, 1H), 3.32-3.21 (m, 2H), 3.06 (dd, J=8.3, 15.2 Hz, 1H), 2.84-2.65 (m, 3H), 2.50-2.33 (m, 3H), 2.26 (dd, J=5.3, 9.4 Hz, 1H), 2.04-1.60 (m, 9H), 1.43 (t, J=12.2 Hz, 1H); m/z (ESI, +ve ion) 738.2 (M+H)⁺.

Example 628. 2-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-12'-yl)-N-(3-methoxyphenyl)acetamide or 2-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-12'-yl)-N-(3-methoxyphenyl)acetamide One of the title compounds were prepared from ((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-12'-yl)acetic acid or ((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-12'-yl)acetic acid (Example 627, Step 1) by a procedure analogous to that described in Example 627, Steps 2, replacing 3-chloroaniline with 3-methoxyaniline. The crude product was purified by reversed phase preparatory HPLC (Gemini™ Prep C$_{18}$ 5 µm column; Phenomenex, Torrance, CA; gradient elution of 45% to 70% MeCN in water, where both solvents contain 0.1% TFA, 30 min method) to provide one of the title compounds as a white foam. ¹H NMR (500 MHz, CDCl$_3$) δ ppm 8.35 (br. s., 1H), 7.84 (s, 1H), 7.70 (d, J=8.6 Hz, 1H), 7.26-7.21 (m, 1H), 7.21-7.16 (m, 1H), 7.11-7.08 (m, 1H), 7.07-7.02 (m, 1H), 7.00-6.88 (m, 3H), 6.70 (d, J=8.0 Hz, 1H), 5.91-5.83 (m, 1H), 5.71 (dd, J=7.3, 15.4 Hz, 1H), 4.66-4.59 (m, 1H), 4.21 (dd, J=4.2, 7.3 Hz, 1H), 4.14-4.05 (m, 2H), 3.83-3.77 (m, 4H), 3.70 (d, J=14.4 Hz, 1H), 3.33-3.22 (m, 2H), 3.06 (dd, J=8.7, 15.3 Hz, 1H), 2.84-2.69 (m, 3H), 2.46-2.33 (m, 3H), 2.32-2.22 (m, 1H), 2.03-1.72 (m, 8H), 1.70-1.59 (m, 1H), 1.42 (m, 1H); m/z (ESI, +ve ion) 734.2 (M+H)⁺.

Example 629. 2-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-12'-yl)-N-(5-methoxy-2-methylphenyl)acetamide or 2-((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-12'-yl)-N-(5-methoxy-2-methylphenyl)acetamide

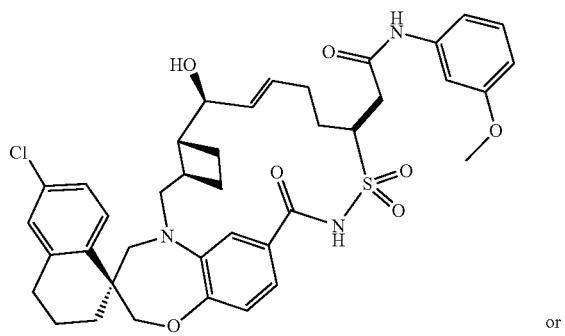

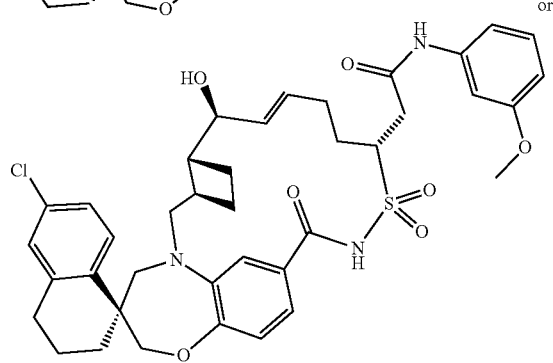

or

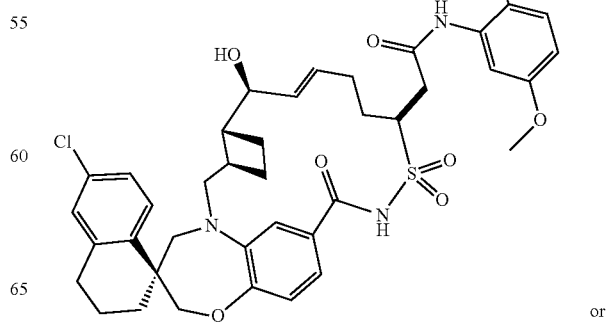

or

1307
-continued

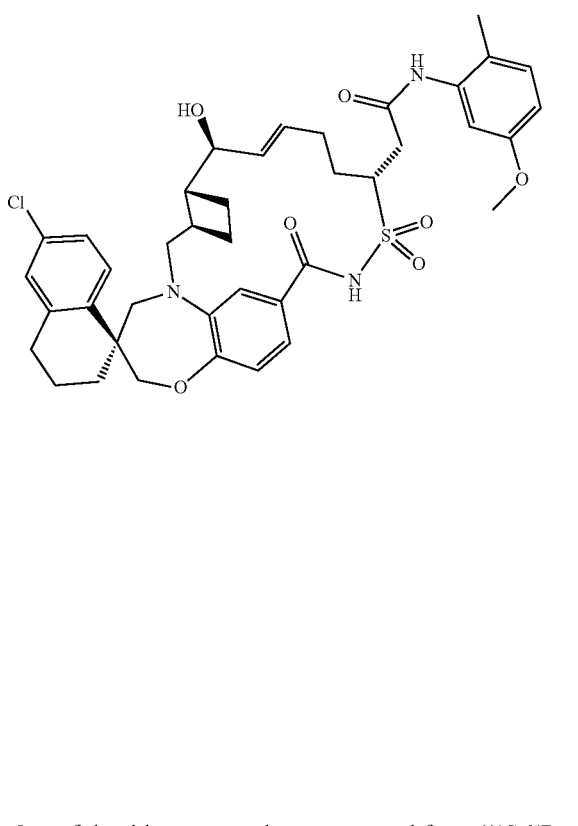

One of the title compounds was prepared from ((1S,3'R, 6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetic acid or ((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetic acid (Example 627, Step 1) by a procedure analogous to that described in Example 627, Steps 2, replacing 3-chloroaniline with 5-methoxy-2-methylaniline. The crude product was purified by reversed phase preparatory HPLC (Gemini™ Prep C$_{18}$ 5 μm column; Phenomenex, Torrance, CA; gradient elution of 45% to 70% MeCN in water, where both solvents contain 0.1% TFA, 30 min method) to provide one of the title compounds as a white foam. $^1$H NMR (500 MHz, CDCl$_3$) δ ppm 8.27 (br. s., 1H), 7.70 (d, J=8.6 Hz, 1H), 7.60 (s, 1H), 7.57-7.51 (m, 1H), 7.19 (dd, J=2.2, 8.6 Hz, 1H), 7.10 (s, 1H), 7.09 (d, J=7.1 Hz, 2H), 6.99-6.86 (m, 3H), 6.67 (m, 1H), 5.92-5.81 (m, 1H), 5.73 (dd, J=7.6, 15.4 Hz, 1H), 4.64 (m, 1H), 4.22 (m, 1H), 4.14-4.05 (m, 2H), 3.83-3.77 (m, 4H), 3.70 (d, J=14.2 Hz, 1H), 3.33 (dd, J=5.6, 15.7 Hz, 1H), 3.26 (d, J=14.4 Hz, 1H), 3.06 (dd, J=8.8, 15.2 Hz, 1H), 2.83-2.72 (m, 3H), 2.47-2.34 (m, 3H), 2.34-2.28 (m, 1H), 2.26 (s, 3H), 2.05-1.72 (m, 8H), 1.70-1.64 (m, 1H), 1.42 (t, J=12.3 Hz, 1H); m/z (ESI, +ve ion) 748.2 (M+H)$^+$.

Example 630. 2-((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24] tetraen]-12'-yl)-N-phenylacetamide or 2-((1S,3'R, 6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)-N-phenylacetamide

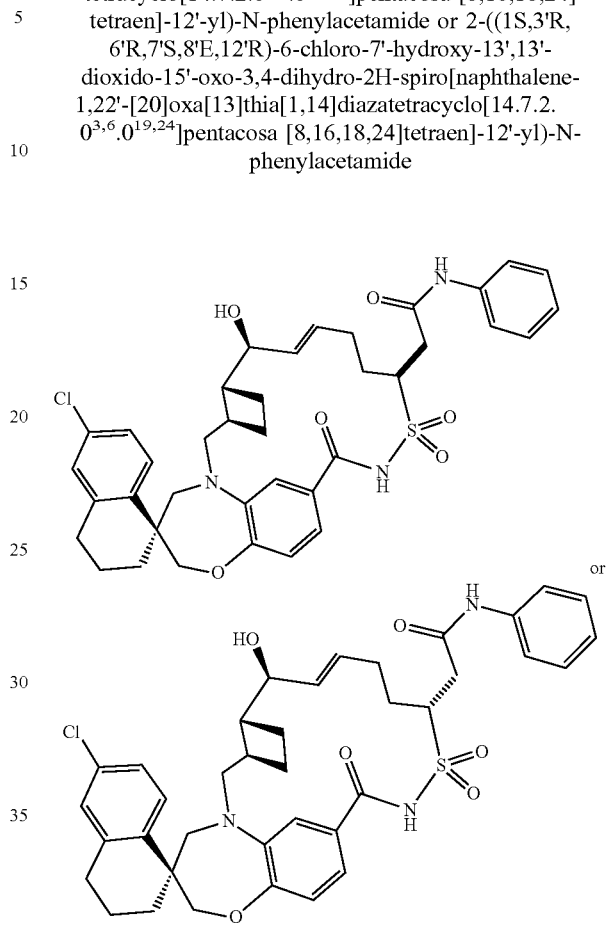

One of the title compounds was prepared from ((1S,3'R, 6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16, 18,24]tetraen]-12'-yl)acetic acid or ((1S,3'R,6'R,7'S,8'E, 12'R)-6-chloro-7'-hydroxy-13',13'-dioxido-15'-oxo-3,4-dihydro-2H-spiro[naphthalene-1,22'-[20]oxa[13]thia[1,14] diazatetracyclo[14.7.2.0$^{3,6}$.0$^{19,24}$]pentacosa[8,16,18,24] tetraen]-12'-yl)acetic acid (Example 627, Step 1) by a procedure analogous to that described in Example 627, Steps 2, replacing 3-chloroaniline with aniline. The crude product was purified by reversed phase preparatory HPLC (Gemini™ Prep C$_{18}$ 5 μm column; Phenomenex, Torrance, CA; gradient elution of 45% to 70% MeCN in water, where both solvents contain 0.1% TFA, 30 min method) to provide one of the title compounds as a white foam. $^1$H NMR (500 MHz, CDCl$_3$) δ ppm 8.32 (br. s., 1H), 7.82 (s, 1H), 7.72 (d, J=8.6 Hz, 1H), 7.57 (d, J=8.1 Hz, 2H), 7.36 (t, J=7.8 Hz, 2H), 7.25-7.13 (m, 2H), 7.11 (d, J=2.0 Hz, 1H), 7.00-6.93 (m, 3H), 5.93-5.84 (m, 1H), 5.74 (dd, J=7.5, 15.3 Hz, 1H), 4.64 (m, 1H), 4.23 (dd, J=4.3, 7.2 Hz, 1H), 4.17-4.06 (m, 2H), 3.81 (d, J=14.7 Hz, 1H), 3.72 (d, J=14.2 Hz, 1H), 3.36-3.24 (m, 2H), 3.08 (dd, J=8.4, 15.0 Hz, 1H), 2.85-2.72 (m, 3H), 2.48-2.36 (m, 3H), 2.36-2.20 (m, 1H), 2.07-1.94 (m, 5H), 1.90-1.60 (m, 4H), 1.44 (t, J=12.3 Hz, 1H); m/z (ESI, +ve ion) 704.2 (M+H)$^+$.

Example 631. 4-(((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetyl)-N,N-dimethyl-1-piperazinesulfonamide or 4-(((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetyl)-N,N-dimethyl-1-piperazinesulfonamide

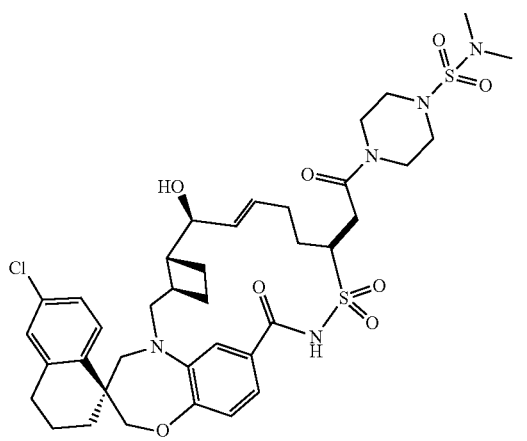

or

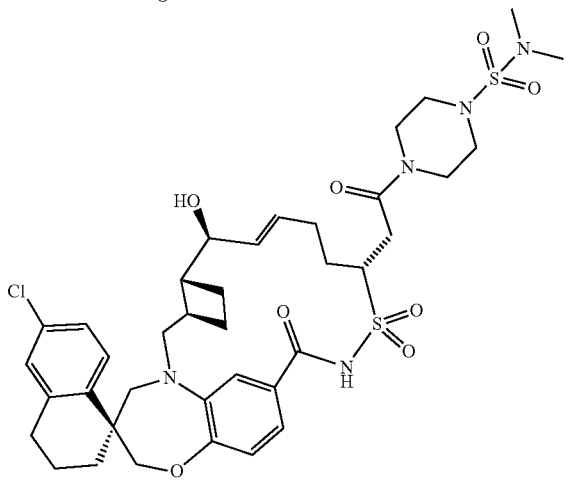

One of the title compounds was prepared from ((1S,3'R,6'R,7'S,8'E,12'S)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetic acid or ((1S,3'R,6'R,7'S,8'E,12'R)-6-chloro-7'-hydroxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)acetic acid (Example 627, Step 1) by a procedure analogous to that described in Example 627, Steps 2, replacing 3-chloroaniline with N,N-dimethylpiperazine-1-sulfonamide. The crude product was purified by reversed phase preparatory HPLC (Gemini™ Prep C$_{18}$ 5 μm column; Phenomenex, Torrance, CA; gradient elution of 45% to 70% MeCN in water, where both solvents contain 0.1% TFA, 30 min method) to provide one of the title compounds as a white foam. $^1$H NMR (500 MHz, CDCl$_3$) δ ppm 8.22 (br. s., 1H), 7.70 (d, J=8.6 Hz, 1H), 7.19 (m, 1H), 7.10 (d, J=2.0 Hz, 1H), 6.97-6.92 (m, 2H), 6.90 (s, 1H), 5.89 (m, 1H), 5.72 (dd, J=7.3, 15.2 Hz, 1H), 4.62 (m, 1H), 4.29 (dd, J=4.0, 7.2 Hz, 1H), 4.15-4.05 (m, 2H), 3.98 (m, 1H), 3.78 (m, 2H), 3.70 (d, J=14.4 Hz, 1H), 3.63-3.53 (m, 1H), 3.50-3.41 (m, 2H), 3.39-3.23 (m, 4H), 3.21-3.15 (m, 1H), 3.07 (m, 1H), 2.87 (s, 6H), 2.82-2.71 (m, 2H), 2.63 (dd, J=8.3, 15.7 Hz, 1H), 2.46-2.23 (m, 4H), 2.06-1.91 (m, 5H), 1.89-1.71 (m, 3H), 1.70-1.63 (m, 1H), 1.43 (t, J=12.5 Hz, 1H); m/z (ESI, +ve ion) 804.2 (M+H)$^+$.

Example 632. (1S,3'R,6'R,7'S,8'E,12'S)-6-chloro-7'-hydroxy-12'-(2-(5-methyl-1,3,4-oxadiazol-2-yl)ethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-7'-hydroxy-12'-(2-(5-methyl-1,3,4-oxadiazol-2-yl)ethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

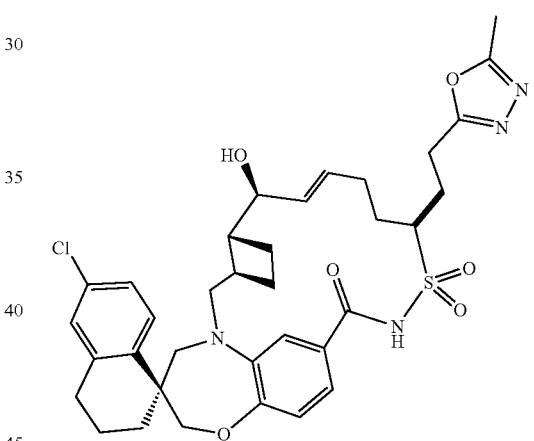

or

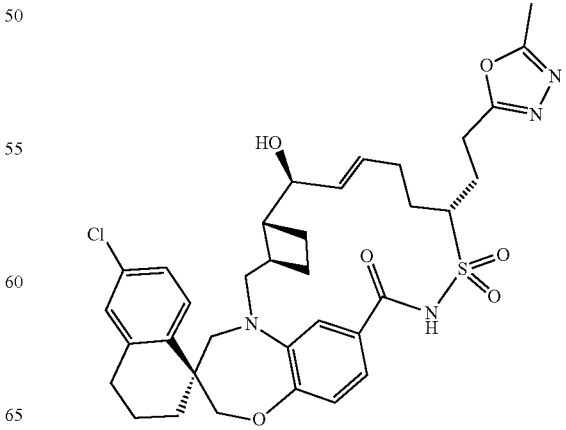

Step 1: (S)-1-((tert-butyldimethylsilyl)oxy)-N,N-bis(4-methoxybenzyl)oct-7-ene-4-sulfonamide and (R)-1-((tert-butyldimethylsilyl)oxy)-N,N-bis(4-methoxybenzyl)oct-7-ene-4-sulfonamide

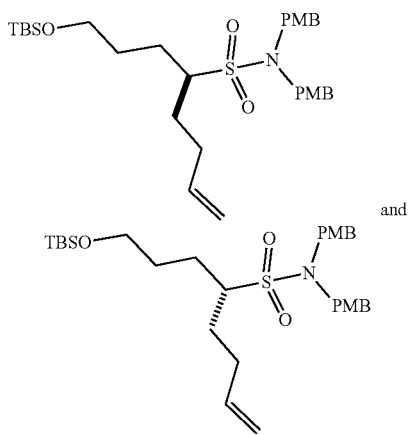

and

To a solution of N,N-bis(4-methoxybenzyl)pent-4-ene-1-sulfonamide (Intermediate EE19) (3.00 g, 7.70 mmol) in THF (17 mL) was added n-BuLi (2.5 M solution in hexanes, 3.70 mL, 9.24 mmol) at −78° C. After the reaction mixture was stirred for 5 min, tert-butyl(3-iodopropoxy)dimethylsilane (6.94 g, 23.1 mmol) was added at the same temp. The reaction was stirred at −78° C. for 20 min and then allowed to warm to ambient temperature. The reaction was quenched (saturated aqueous NH₄Cl solution), extracted (2×EtOAc), and washed (brine). The combined organic layers were dried (Na₂SO₄), and concentrated under reduced pressure to provide a crude product. The residue was injected into a 80 g ISCO Gold column and purified by combi-flash, eluting with 0% to 30% EtOAc/hexanes to give the title compounds (3.94 g, 7.01 mmol) as a colorless liquid.

Step 2: (S)-1-hydroxy-N,N-bis(4-methoxybenzyl)oct-7-ene-4-sulfonamide and (R)-1-hydroxy-N,N-bis(4-methoxybenzyl)oct-7-ene-4-sulfonamide

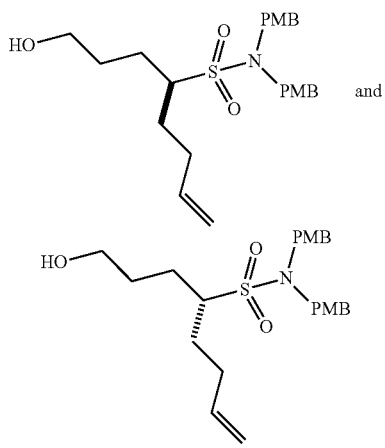

To a solution of (S)-1-((tert-butyldimethylsilyl)oxy)-N,N-bis(4-methoxybenzyl)oct-7-ene-4-sulfonamide and (R)-1-((tert-butyldimethylsilyl)oxy)-N,N-bis(4-methoxybenzyl)oct-7-ene-4-sulfonamide (Example 632, Step 1) (16.2 g, 28.8 mmol) in THF (30 mL) was added TBAF (1.0 M in THF, 57.7 mL, 57.7 mmol) at 0° C. After the reaction mixture was stirred at ambient temperature for 18 hours, the reaction was quenched (saturated aqueous NH₄Cl solution), extracted (2×EtOAc), and washed (brine). The combined organic layers were dried (Na₂SO₄) and concentrated under reduced pressure to provide a crude product. The residue was injected into a 220 g ISCO Gold column and purified by combi-flash, eluting with 30% to 50% EtOAc/hexanes to give the title compounds (12.9 g, 28.8 mmol)

Step 3: (S)-4-(N,N-bis(4-methoxybenzyl)sulfamoyl)oct-7-enoic Acid and (R)-4-(N,N-bis(4-methoxybenzyl)sulfamoyl)oct-7-enoic Acid

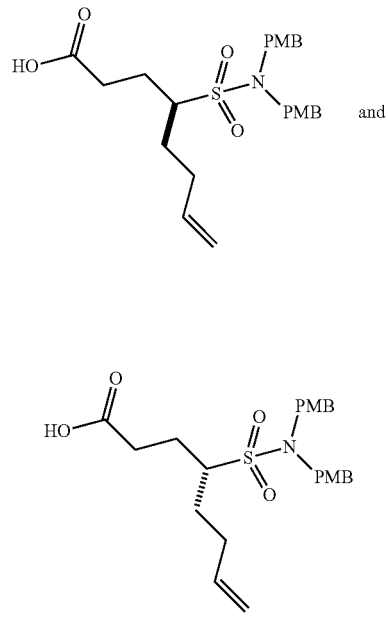

To a solution of (S)-1-hydroxy-N,N-bis(4-methoxybenzyl)oct-7-ene-4-sulfonamide and (R)-1-hydroxy-N,N-bis(4-methoxybenzyl)oct-7-ene-4-sulfonamide (10.0 g, 22.3 mmol) (Example 632, Step 2), KBr (0.266 g, 2.23 mmol), 5% sodium bicarbonate in water (105 mL, 62.6 mmol) and TEMPO (3.84 g, 24.6 mmol) in acetone (112 mL) was added 6% sodium hypochlorite in water (30.5 mL, 24.6 mmol) at 0° C. and the resulting mixture was stirred vigorously at the same temp for 3.5 hours. The reaction was diluted (EtOAc and ice-cold 1N aqueous HCl), extracted (2×EtOAc), and washed (brine). The combined organic layers were dried (Na₂SO₄) and concentrated under reduced pressure. The residue was injected into a 220 g ISCO Gold column and purified by combi-flash, eluting with 40% to 100% EtOAc/hexanes to give the title compounds (7.10 g, 15.4 mmol).

1313

Step 4: (S)-1-(2-acetylhydrazinyl)-N,N-bis(4-methoxybenzyl)-1-oxooct-7-ene-4-sulfonamide and (R)-1-(2-acetylhydrazinyl)-N,N-bis(4-methoxybenzyl)-1-oxooct-7-ene-4-sulfonamide

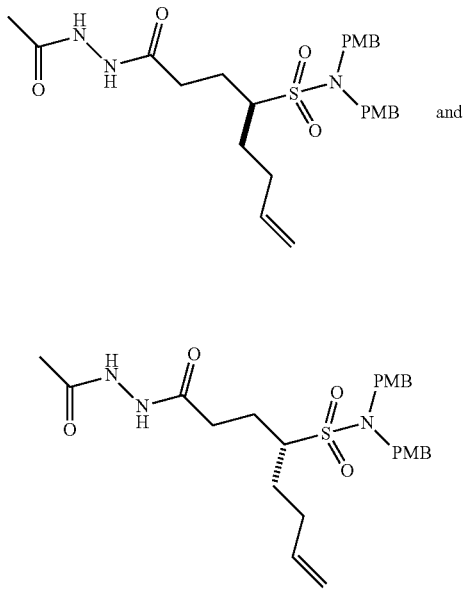

A solution of (S)-4-(N,N-bis(4-methoxybenzyl)sulfamoyl)oct-7-enoic acid and (R)-4-(N,N-bis(4-methoxybenzyl)sulfamoyl)oct-7-enoic acid (0.80 g, 1.73 mmol) (Example 632, Step 3) and acetic hydrazide (0.260 g, 3.47 mmol) in DCM (5.8 mL) was treated with EDC (0.997 g, 5.20 mmol), HOAt (0.708 g, 5.20 mmol) and TEA (0.725 mL, 5.20 mmol) successively at 0° C. Then the reaction was allowed to warm to ambient temperature. After the reaction mixture was stirred overnight, the reaction was diluted (1 N aqueous HCl), extracted (2×EtOAc), and washed (1×brine, 1×saturated NaHCO₃, and 1×brine). The combined organic layers were dried (Na₂SO₄) and concentrated under reduced pressure to provide a crude product, which was used in the next step without purification.

Step 5: (S)—N,N-bis(4-methoxybenzyl)-1-(5-methyl-1,3,4-oxadiazol-5-yl)hept-6-ene-3-sulfonamide and (R)—N,N-bis(4-methoxybenzyl)-1-(5-methyl-1,3,4-oxadiazol-5-yl)hept-6-ene-3-sulfonamide

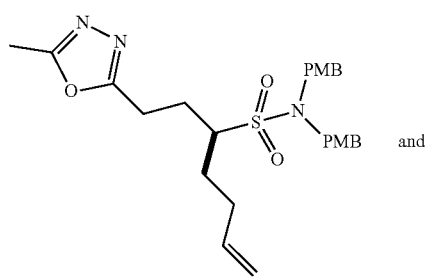

1314

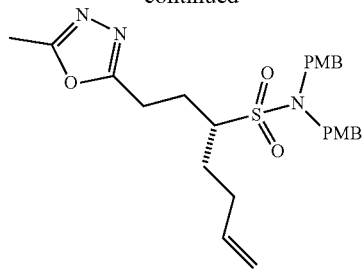

A solution of (S)-1-(2-acetylhydrazinyl)-N,N-bis(4-methoxybenzyl)-1-oxooct-7-ene-4-sulfonamide and (R)-1-(2-acetylhydrazinyl)-N,N-bis(4-methoxybenzyl)-1-oxooct-7-ene-4-sulfonamide (0.730 g, 1.41 mmol) (Example 632, Step 4) and burgess reagent (1.34 g, 5.64 mmol) in THF (14 mL) was refluxed under N₂ for 36 hours. Then the reaction was diluted (water), extracted (2×DCM), and washed (1×brine). The combined organic layer were dried (Na₂SO₄) and concentrated under reduced pressure. The residue was injected into a 24 g ISCO Gold column and purified by combi-flash, eluting with 30% to 50% EtOAc/hexanes to give the title compounds (0.350 g, 0.701 mmol)

Step 6: (S)-1-(5-methyl-1,3,4-oxadiazol-2-yl)hept-6-ene-3-sulfonamide and (R)-1-(5-methyl-1,3,4-oxadiazol-2-yl)hept-6-ene-3-sulfonamide

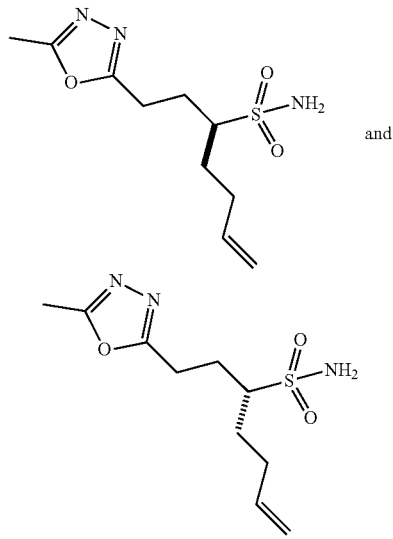

To a solution of (S)—N,N-bis(4-methoxybenzyl)-1-(5-methyl-1,3,4-oxadiazol-5-yl)hept-6-ene-3-sulfonamide and (R)—N,N-bis(4-methoxybenzyl)-1-(5-methyl-1,3,4-oxadiazol-5-yl)hept-6-ene-3-sulfonamide (0.350 g, 0.700 mmol) (Example 632, Step 5) in DCM (3.5 mL) was added anisole (0.75 mL, 7.0 mmol) and TFA (1.35 mL, 17.5 mmol) at room temperature. After the reaction mixture was stirred at 40° C. overnight, the excess TFA was removed under reduced pressure. The residue was injected into a 12 g ISCO Gold column and purified by combi-flash, eluting with 0% to 10% MeOH/DCM (containing 0.3% AcOH) to give the title compounds (0.140 g, 0.540 mmol)

Step 7: (1S,3'R,6'R,7'S,8'E,12'S)-6-chloro-7'-hydroxy-12'-(2-(5-methyl-1,3,4-oxadiazol-2-yl)ethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-hydroxy-12'-(2-(5-methyl-1,3,4-oxadiazol-2-yl)ethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide One of the title compounds was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12) by a procedure analogous to that described in Example 610, Steps 1 through 2, replacing (R)-hept-6-ene-3-sulfonamide in Step 1 with (S)-1-(5-methyl-1,3,4-oxadiazol-2-yl)hept-6-ene-3-sulfonamide and (R)-1-(5-methyl-1,3,4-oxadiazol-2-yl)hept-6-ene-3-sulfonamide (Example 632, Step 6). The crude product was purified by reversed phase preparatory HPLC (Gemini™ Prep C$_{18}$ 5 μm column; Phenomenex, Torrance, CA; gradient elution of 45% to 70% MeCN in water, where both solvents contain 0.1% TFA, 30 min method) to provide one of the title compounds as the faster eluting isomer as a white foam. $^1$H NMR (500 MHz, CDCl$_3$) δ ppm 8.11 (s, 1H), 7.70 (d, J=8.6 Hz, 1H), 7.18 (dd, J=2.2, 8.6 Hz, 1H), 7.13-7.05 (m, 1H), 6.96-6.84 (m, 3H), 5.75-5.64 (m, 2H), 4.25-4.21 (m, 1H), 4.21-4.15 (m, 1H), 4.15-4.04 (m, 2H), 3.81 (d, J=14.4 Hz, 1H), 3.71 (d, J=14.4 Hz, 1H), 3.35-3.26 (m, 1H), 3.26-3.17 (m, 2H), 3.02 (dd, J=9.4, 15.3 Hz, 1H), 2.83-2.72 (m, 2H), 2.60-2.53 (m, 4H), 2.45 (m, 1H), 2.42-2.24 (m, 4H), 2.08-1.91 (m, 3H), 1.90-1.70 (m, 5H), 1.70-1.60 (m, 1H), 1.40 (t, J=13.0 Hz, 1H); m/z (ESI, +ve ion) 703.2 (M+Na)$^+$.

Example 633. (1S,3'R,6'R,7'S,8'E,12'S)-12'-(4-bromobenzyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-12'-(4-bromobenzyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

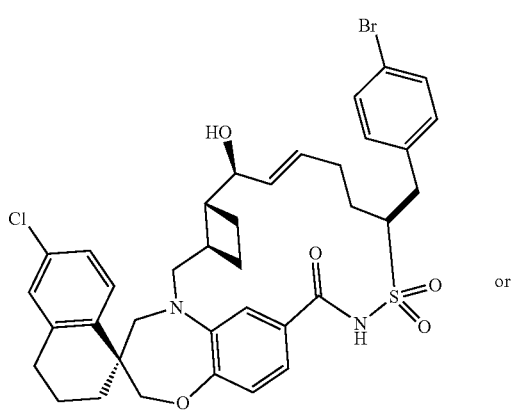

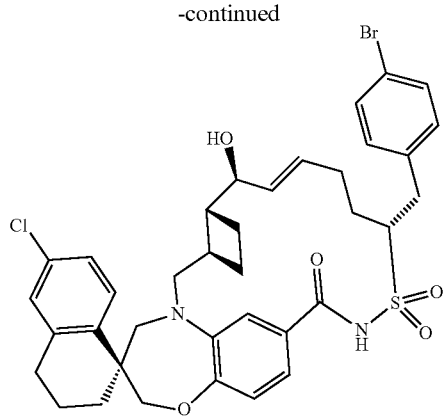

Step 1: (S)-1-(4-bromophenyl)-N,N-bis(4-methoxybenzyl)hex-5-ene-2-sulfonamide and (R)-1-(4-bromophenyl)-N,N-bis(4-methoxybenzyl)hex-5-ene-2-sulfonamide

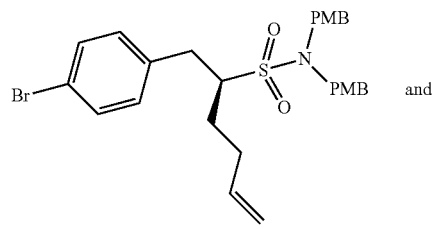

and

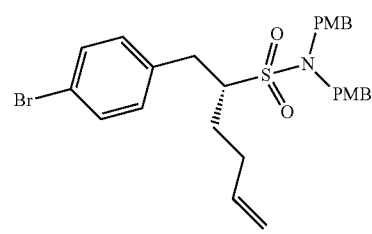

To a solution of N,N-bis(4-methoxybenzyl)pent-4-ene-1-sulfonamide (1.50 g, 3.85 mmol, Intermediate EE19) at −78° C. in THF (10 mL) was added n-BuLi (2.5 M solution in hexanes, 1.5 mL, 3.9 mmol). The reaction mixture was stirred at the same temperature for 15 minutes. Then a solution of 1-bromo-4-(bromomethyl)benzene (1.92 g, 7.70 mmol) in THF (3.0 mL) was added and the reaction mixture was stirred at −78° C. for 1 h. The reaction was quenched (aqueous saturated NH$_4$Cl), extracted (2×DCM), and washed (1×brine). The combined organic layers were dried (Na$_2$SO$_4$) and concentrated under reduced pressure. The residue was injected into a 80 g ISCO Gold column and purified by combi-flash, eluting with 10% to 30% EtOAc/hexanes to give the title compounds (1.70 g, 3.04 mmol)

1317

Step 2: (S)-1-(4-bromophenyl)hex-5-ene-2-sulfonamide and (R)-1-(4-bromophenyl)hex-5-ene-2-sulfonamide

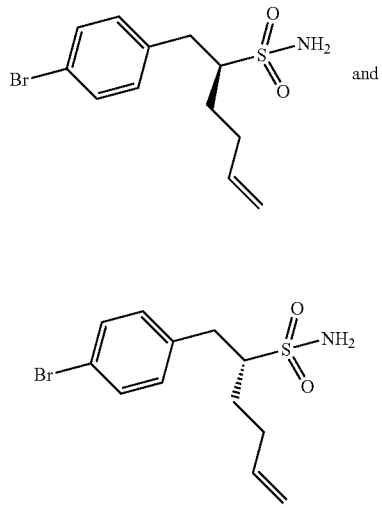

To a solution of (S)-1-(4-bromophenyl)-N,N-bis(4-methoxybenzyl)hex-5-ene-2-sulfonamide and (R)-1-(4-bromophenyl)-N,N-bis(4-methoxybenzyl)hex-5-ene-2-sulfonamide (Example 633, Step 1) (1.70 g, 3.04 mmol) in DCM (8.0 mL) was added anisole (3.30 mL, 30.4 mmol) and TFA (11.7 mL, 152 mmol) at room temperature. After the reaction mixture was stirred over 2 days, the excess TFA was removed under reduced pressure. The residue was injected into a 40 g ISCO Gold column and purified by combi-flash, eluting with 10% to 40% EtOAc (containing 03% AcOH)/hexanes to give the title compounds (0.75 g, 2.35 mmol).

Step 3: (1S,3'R,6'R,7'S,8'E,12'S)-12'-(4-bromobenzyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-12'-(4-bromobenzyl)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide One of the title compounds was prepared from (S)-6'-chloro-5-(((1R,2R)-2-((S,E)-1-hydroxyhex-2-en-1-yl)cyclobutyl)methyl)-3',4',5-tetrahydro-2H,2'H-spiro[benzo[b][1,4]oxazepine-3,1'-naphthalene]-7-carboxylic acid (Intermediate AA12) by a procedure analogous to that described in Example 610, Steps 1 through 2, replacing (R)-hept-6-ene-3-sulfonamide in Step 1 with (S)-1-(4-bromophenyl)hex-5-ene-2-sulfonamide and (R)-1-(4-bromophenyl)hex-5-ene-2-sulfonamide (Example 633, Step 2). The crude product was purified by reversed phase preparatory HPLC (Gemini™ Prep C$_{18}$ 5 μm column; Phenomenex, Torrance, CA; gradient elution of 50% to 80% MeCN in water, where both solvents contain 0.1% TFA, 30 min method) to provide one of the title compounds as the faster eluting isomer as a white foam. $^1$H NMR (500 MHz, CDCl$_3$) δ ppm 8.20 (br. s., 1H) 7.69 (d, J=8.31 Hz, 1H) 7.46 (d, J=8.07 Hz, 2H) 7.24-7.15 (m, 3H) 7.09 (d, J=1.96 Hz, 1H) 6.96-6.88 (m, 3H) 5.72 (dt, J=15.16, 5.75 Hz, 1H) 5.62 (dd, J=15.41, 7.34 Hz, 1H) 4.41-4.28 (m, 1H) 4.19 (dd, J=7.21, 4.52 Hz, 1H) 4.15-4.03 (m, 2H) 3.78 (d, J=14.67 Hz, 1H) 3.69 (d, J=14.18 Hz, 1H) 3.56 (dd, J=14.43, 4.89 Hz, 1H) 3.25 (d, J=14.43 Hz, 1H) 3.11-2.95 (m, 2H) 2.82-2.72 (m, 2H) 2.57-2.34 (m, 2H) 2.30-2.17 (m, 1H) 2.03-1.80 (m, 9H) 1.78-1.61 (m, 2H) 1.43 (t, J=12.59 Hz, 1H) m/z (ESI, +ve ion) 741.0 (M+H)$^+$.

Example 634. (1S,3'R,6'R,7'S,8'E,11'R,12'S)-6-chloro-7'-hydroxy-11'-methyl-12'-(2-thiophenylmethyl)-3,4-dihydro-2H,15'H-spiro[naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-7'-hydroxy-11'-methyl-12'-(2-thiophenylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-7'-hydroxy-11'-methyl-12'-(2-thiophenylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-(2-thiophenylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (Isomer 1)

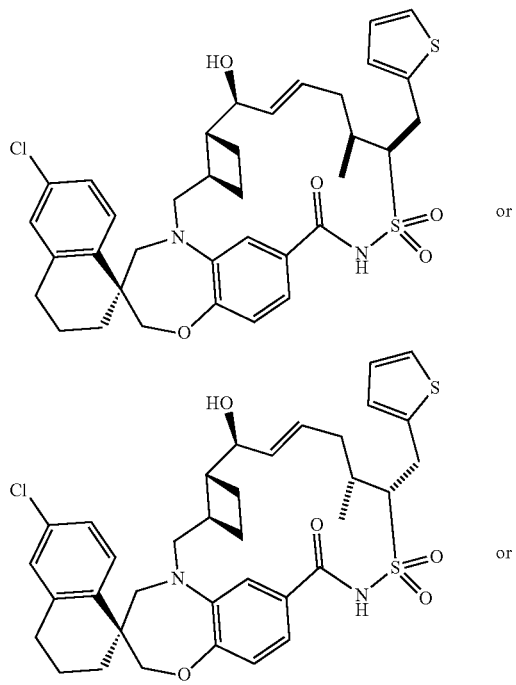

1319
-continued

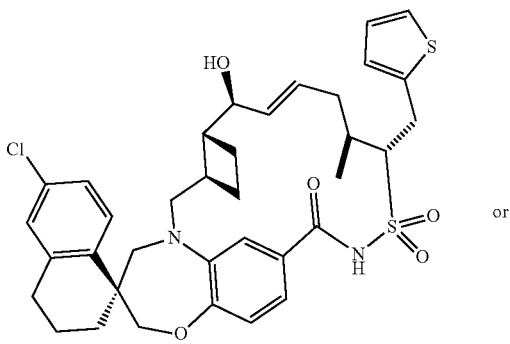

or

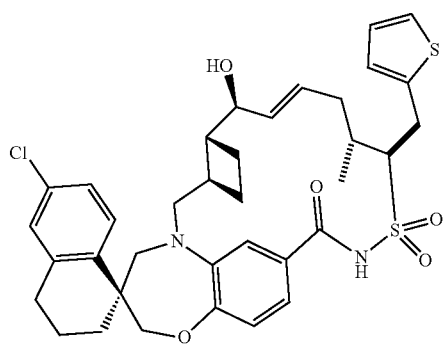

Step 1: (2R,3S)—N,N-bis(4-methoxybenzyl)-3-methyl-1-(thiophen-2-yl)hex-5-ene-2-sulfonamide and (2R,3R)—N,N-bis(4-methoxybenzyl)-3-methyl-1-(thiophen-2-yl)hex-5-ene-2-sulfonamide and (2S,3S)—N,N-bis(4-methoxybenzyl)-3-methyl-1-(thiophen-2-yl)hex-5-ene-2-sulfonamide and (2S,3R)—N,N-bis(4-methoxybenzyl)-3-methyl-1-(thiophen-2-yl)hex-5-ene-2-sulfonamide

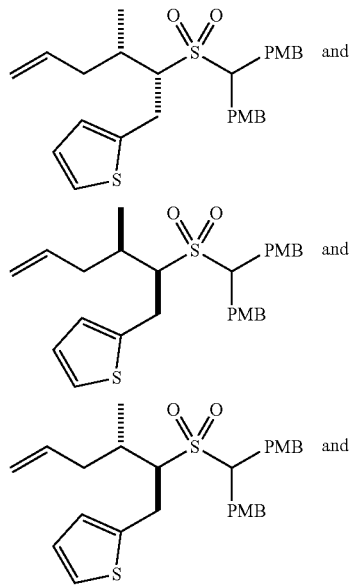

1320
-continued

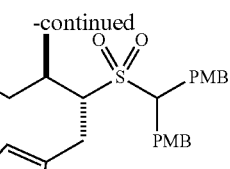

To a solution of (R)—N,N-bis(4-methoxybenzyl)-2-methylpent-4-ene-1-sulfonamide and (S)—N,N-bis(4-methoxybenzyl)-2-methylpent-4-ene-1-sulfonamide (1.07 g, 2.65 mmol) (Example 647, Step 7) in THF (6.5 mL) was added n-BuLi (2.5 M solution in hexanes, 1.06 mL, 2.65 mmol) at −78° C. After the reaction was stirred at the same temperature for 20 min, a solution of 2-(chloromethyl)thiophene (0.703 g, 5.30 mmol) in THF (3.5 mL) was added and the resulting solution was stirred at −78° C. for 1 h. Then the reaction was allowed to warm to ambient temperature and stirred for 16 hours. The reaction was quenched (saturated aqueous NH$_4$Cl), extracted (2×EtOAc), and washed (brine). The combined organic layers were dried (Na$_2$SO$_4$) and concentrated under reduced pressure. The residue was injected into a 40 g ISCO Gold column and purified by combi-flash, eluting with 0% to 20% EtOAc (containing 0.3% AcOH)/hexanes to give the title compounds (800 mg, 1.60 mmol) as a pale yellow oil.

Step 2: (2R,3S)-3-methyl-1-(thiophen-2-yl)hex-5-ene-2-sulfonamide and (2R,3R)-3-methyl-1-(thiophen-2-yl)hex-5-ene-2-sulfonamide and (2S,3S)-3-methyl-1-(thiophen-2-yl)hex-5-ene-2-sulfonamide and (2S,3R)-3-methyl-1-(thiophen-2-yl)hex-5-ene-2-sulfonamide

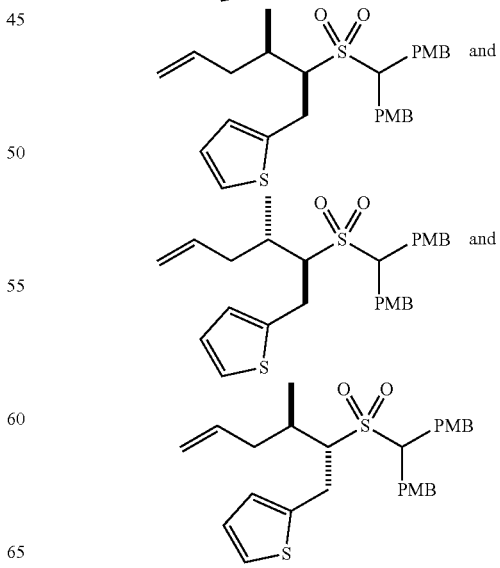

To a solution of (2R,3S)—N,N-bis(4-methoxybenzyl)-3-methyl-1-(thiophen-2-yl)hex-5-ene-2-sulfonamide and (2R,3R)—N,N-bis(4-methoxybenzyl)-3-methyl-1-(thiophen-2-yl)hex-5-ene-2-sulfonamide and (2S,3S)—N,N-bis(4-methoxybenzyl)-3-methyl-1-(thiophen-2-yl)hex-5-ene-2-sulfonamide and (2S,3R)—N,N-bis(4-methoxybenzyl)-3-methyl-1-(thiophen-2-yl)hex-5-ene-2-sulfonamide (0.680 g, 1.36 mmol) (Example 634, Step 1) in anisole (14.8 mL, 136 mmol) was added TFA (10.1 mL, 136 mmol) at room temperature. After the reaction mixture was stirred overnight, the excess TFA was removed under reduced pressure. The residue was injected into a 12 g ISCO Gold column and purified by combi-flash, eluting with 0% to 20% MeOH/DCM (containing 0.3% AcOH) to give the title compounds (302 mg, 1.16 mmol).

Step 3: (1S,3'R,6'R,7'S,8'E,11'R,12'S)-6-chloro-7'-hydroxy-11'-methyl-12'-(2-thiophenylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-7'-hydroxy-11'-methyl-12'-(2-thiophenylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-7'-hydroxy-11'-methyl-12'-(2-thiophenylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-(2-thiophenylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (Isomer 1)

One of the title compounds was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12) by a procedure analogous to that described in Example 610, Steps 1 through 2, replacing (R)-hept-6-ene-3-sulfonamide in Step 1 with (2R,3S)-3-methyl-1-(thiophen-2-yl)hex-5-ene-2-sulfonamide and (2R,3R)-3-methyl-1-(thiophen-2-yl)hex-5-ene-2-sulfonamide and (2S,3S)-3-methyl-1-(thiophen-2-yl)hex-5-ene-2-sulfonamide and (2S,3R)-3-methyl-1-(thiophen-2-yl)hex-5-ene-2-sulfonamide (Example 634, Step 2). The crude product was purified by reversed phase preparatory HPLC (Gemini™ Prep C$_{18}$ 5 μm column; Phenomenex, Torrance, CA; gradient elution of 45% to 70% MeCN in water, where both solvents contain 0.1% TFA, 30 min method) to provide one of the title compounds as the faster eluting isomer as a white foam. $^1$H NMR (500 MHz, CDCl$_3$) δ ppm 7.63 (d, J=8.3 Hz, 1H), 7.15-7.07 (m, 2H), 7.06-7.00 (m, 1H), 6.96-6.85 (m, 4H), 6.79-6.66 (m, 1H), 6.20-5.42 (m, 1H), 4.16 (dd, J=3.1, 7.9 Hz, 1H), 4.09-3.93 (m, 2H), 3.82-3.54 (m, 3H), 3.34-2.89 (m, 3H), 2.76-2.62 (m, 2H), 2.35-2.19 (m, 2H), 2.05 (m, 4H), 1.79-1.67 (m, 3H), 1.57-0.79 (m, 8H), 0.04--0.04 (m, 1H); m/z (ESI, +ve ion) 681.2 (M+H)$^+$.

Example 635. (1S,3'R,6'R,7'S,8'E,11'R,12'S)-6-chloro-7'-hydroxy-11'-methyl-12'-(2-thiophenylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-7'-hydroxy-11'-methyl-12'-(2-thiophenylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-7'-hydroxy-11'-methyl-12'-(2-thiophenylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-(2-thiophenylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (Isomer 2)

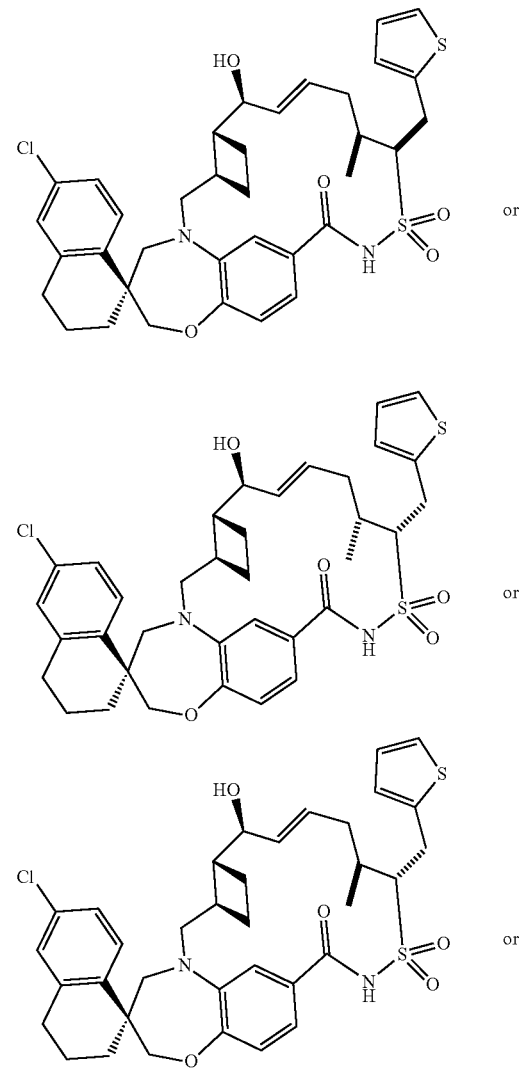

1323
-continued

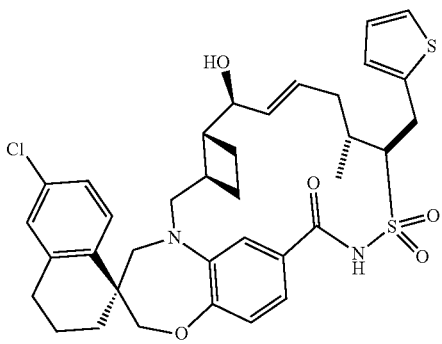

One of the title compounds was obtained as the second (slower) eluting isomer in the reversed phase preparatory HPLC purification of Example 634 Step 3 as a white foam. $^1$H NMR (500 MHz, CDCl$_3$) δ ppm 7.60 (d, J=8.31 Hz, 1H) 6.81-7.09 (m, 8H) 5.75 (m, 1H) 5.54 (dd, J=14.92, 5.38 Hz, 1H) 4.37 (m, 1H) 4.04 (m, 3H) 3.67-3.56 (m, 2H) 3.18 (br. s., 2H) 2.82-2.60 (m, 2H) 2.38-2.28 (m, 2H) 1.95-1.77 (m, 6H) 1.61-1.49 (m, 7H) 1.15-1.01 (m, 3H); m/z (ESI, +ve ion) 681.2 (M+H)$^+$.

Example 636. (1S,3'R,6'R,7'S,8'E,11'S,12'R)-6-chloro-7'-hydroxy-11'-methyl-12'-(3-thiophenylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-7'-hydroxy-11'-methyl-12'-(3-thiophenylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-(3-thiophenylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-7'-hydroxy-11'-methyl-12'-(3-thiophenylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

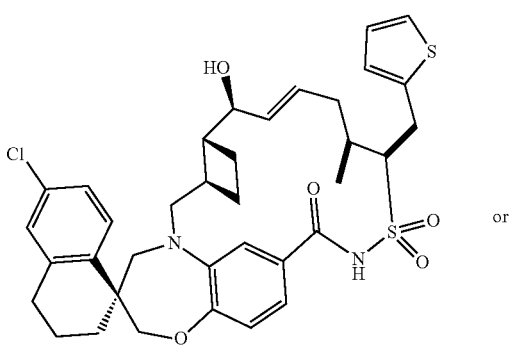

1324
-continued


or


or

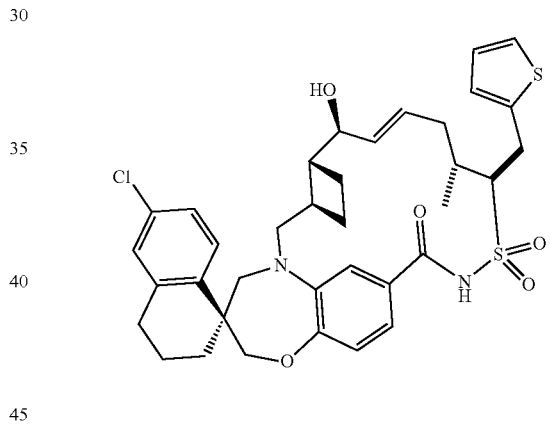

One of the title compounds was prepared by a procedure analogous to that described in Example 634, Steps 1 through 3, replacing 2-(chloromethyl)thiophene in Step 1 with 3-(chloromethyl)thiophene. The crude product was injected into a 4 g ISCO Gold column and purified by combi-flash, eluting with 20% to 60% EtOAc (containing 0.3% AcOH)/hexanes to give a mixture, which was further purified by reversed phase preparatory HPLC (Gemini™ Prep C$_{18}$ 5 µm column; Phenomenex, Torrance, CA; gradient elution of 45% to 70% MeCN in water, where both solvents contain 0.1% TFA, 30 min method) to provide one of the title compounds as the faster eluting isomer as a white foam. $^1$H NMR (500 MHz, CDCl$_3$) δ ppm 7.99 (br. s., 1H), 7.65 (d, J=8.3 Hz, 1H), 7.35-7.30 (m, 1H), 7.22-7.12 (m, 4H), 7.12-7.08 (m, 1H), 6.94-6.89 (m, 1H), 6.89-6.84 (m, 1H), 5.53-5.35 (m, 2H), 4.43-4.37 (m, 1H), 4.29-4.19 (m, 2H), 4.07 (m, 1H), 3.88 (m, 1H), 3.77 (m, 1H), 3.55 (dd, J=4.9, 14.9 Hz, 1H), 3.32 (m, 1H), 3.15 (dd, J=8.6, 14.9 Hz, 2H), 2.79-2.72 (m, 2H), 2.57-2.45 (m, 2H), 2.12 (m, 1H), 1.92-1.75 (m, 9H), 1.50-1.36 (m, 1H), 1.26-1.19 (m, 3H); m/z (ESI, +ve ion) 681.2 (M+H)$^+$.

Example 637. (1S,3'R,6'R,7'S,8'E,11'S,12'R)-6-chloro-7'-hydroxy-11'-methoxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-7'-hydroxy-11'-methoxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-7'-hydroxy-11'-methoxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-7'-hydroxy-11'-methoxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methoxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methoxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-7'-hydroxy-11'-methoxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-7'-hydroxy-11'-methoxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (Isomer 1)

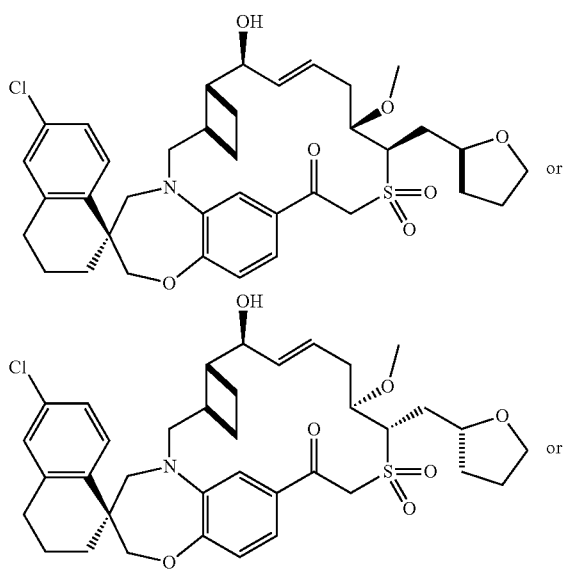

Step 1: (R)—N,N-bis(4-methoxybenzyl)-2-(tetrahydrofuran-2-yl)ethanesulfonamide and (S)—N,N-bis(4-methoxybenzyl)-2-(tetrahydrofuran-2-yl)ethanesulfonamide

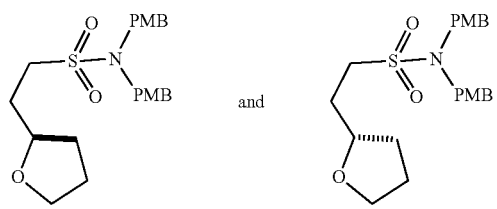

To a solution of N,N-bis(4-methoxybenzyl)methanesulfonamide (6.00 g, 17.9 mmol) (Intermediate EE12) in THF (60 mL) was added n-BuLi (2.5 M in hexanes, 9.30 mL, 23.2 mmol) at −78° C. dropwise. After the reaction was stirred at −78° C. for 10 min, 2-(bromomethyl)tetrahydrofuran (8.14 mL, 71.6 mmol) in THF (10 mL) was added into the reaction for 30 minutes at the same temp. Then the reaction was allowed to warm to ambient temperature and stirred over 2 days. The reaction was quenched (Saturated aqueous NH$_4$Cl), extracted (2×EtOAc), and washed (brine). The combined organic layers were dried (MgSO$_4$) and concentrated under reduced pressure. The residue was injected into a 80 g ISCO Gold column and purified by combi-flash, eluting with 0% to 50% EtOAc/hexanes to give the title compounds (4.30 g, 10.2 mmol).

Step 2: (S)-methyl 2-(N,N-bis(4-methoxybenzyl)sulfamoyl)-3-((R)-tetrahydrofuran-2-yl)propanoate and (R)-methyl 2-(N,N-bis(4-methoxybenzyl)sulfamoyl)-3-((S)-tetrahydrofuran-2-yl)propanoate and (S)-methyl 2-(N,N-bis(4-methoxybenzyl)sulfamoyl)-3-((S)-tetrahydrofuran-2-yl)propanoate and (R)-methyl 2-(N,N-bis(4-methoxybenzyl)sulfamoyl)-3-((R)-tetrahydrofuran-2-yl)propanoate

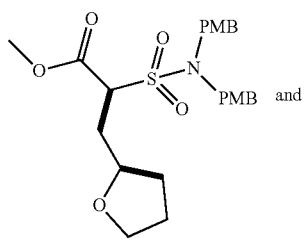

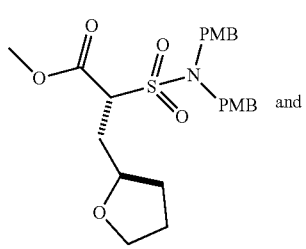

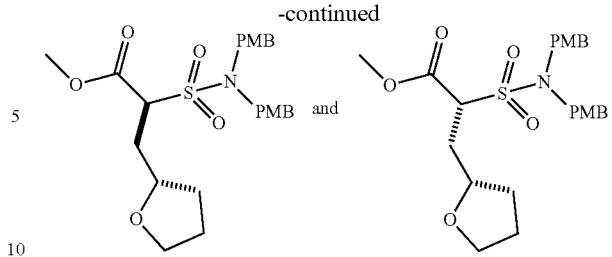

To a solution of (R)—N,N-bis(4-methoxybenzyl)-2-(tetrahydrofuran-2-yl)ethanesulfonamide and (S)—N,N-bis(4-methoxybenzyl)-2-(tetrahydrofuran-2-yl)ethanesulfonamide (Example 637, Step 1) (5.40 g, 12.8 mmol) in THF (64.4 mL) was added n-BuLi (2.5 M in hexanes, 6.18 mL, 15.5 mmol) at −78° C. After the reaction was stirred for 5 min, chlorocarbonic acid methyl ester (1.99 mL, 25.7 mmol) was added and stirred for another 20 min, and then the reaction was allowed to warm to ambient temperature. After the reaction was stirred at ambient temperature for 2 h, the reaction was quenched (saturated aqueous NH$_4$Cl), extracted (2×EtOAc), and washed (brine). The combined organic layers were dried (MgSO$_4$) and concentrated under reduced pressure. The products were used in the next step without further purification.

Step 3: (S)-1-hydroxy-N,N-bis(4-methoxybenzyl)-3-((R)-tetrahydrofuran-2-yl)propane-2-sulfonamide and (R)-1-hydroxy-N,N-bis(4-methoxybenzyl)-3-((S)-tetrahydrofuran-2-yl)propane-2-sulfonamide and (S)-1-hydroxy-N,N-bis(4-methoxybenzyl)-3-((S)-tetrahydrofuran-2-yl)propane-2-sulfonamide and (R)-1-hydroxy-N,N-bis(4-methoxybenzyl)-3-((R)-tetrahydrofuran-2-yl)propane-2-sulfonamide


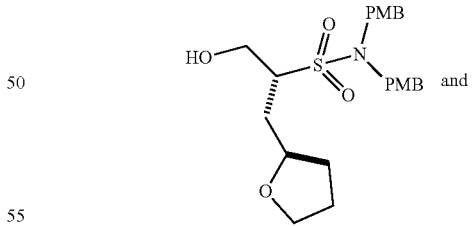

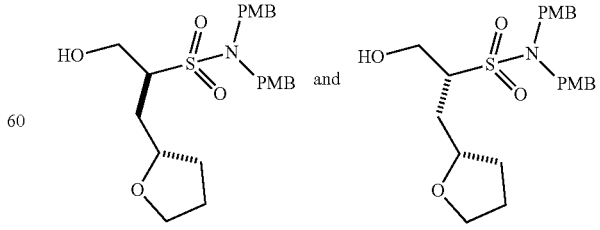

To a solution of (S)-methyl 2-(N,N-bis(4-methoxybenzyl)sulfamoyl)-3-((R)-tetrahydrofuran-2-yl)propanoate and (R)- methyl 2-(N,N-bis(4-methoxybenzyl)sulfamoyl)-3-((S)-tet-rahydrofuran-2-yl)propanoate and (S)-methyl 2-(N,N-bis(4-methoxybenzyl)sulfamoyl)-3-((S)-tetrahydrofuran-2-yl) propanoate and (R)-methyl 2-(N,N-bis(4-methoxybenzyl) sulfamoyl)-3-((R)-tetrahydrofuran-2-yl)propanoate (Example 637, Step 2) (6.15 g, 12.9 mmol) in THF (64 mL) (with very small amount of water) was added lithium borohydride (0.842 g, 38.6 mmol) at 0° C. The reaction mixture was allowed to warm to ambient temperature and stirred overnight. The reaction was quenched (50 mL of 0.5 N aqueous HCl solution), extracted (2×EtOAc), and washed (brine). The combined organic layers were dried (MgSO₄) and concentrated under reduced pressure. The residue was injected into a 80 g ISCO Gold column and purified by combi-flash, eluting with 20% to 50% EtOAc/hexanes to give the title compounds (4.50 g, 10.0 mmol)

Step 4: (S)—N,N-bis(4-methoxybenzyl)-1-oxo-3-((R)-tetrahydrofuran-2-yl)propane-2-sulfonamide and (R)—N,N-bis(4-methoxybenzyl)-1-oxo-3-((S)-tetrahydrofuran-2-yl)propane-2-sulfonamide and (S)—N,N-bis(4-methoxybenzyl)-1-oxo-3-((S)-tetrahydrofuran-2-yl)propane-2-sulfonamide and (R)—N,N-bis(4-methoxybenzyl)-1-oxo-3-((R)-tetrahydrofuran-2-yl)propane-2-sulfonamide

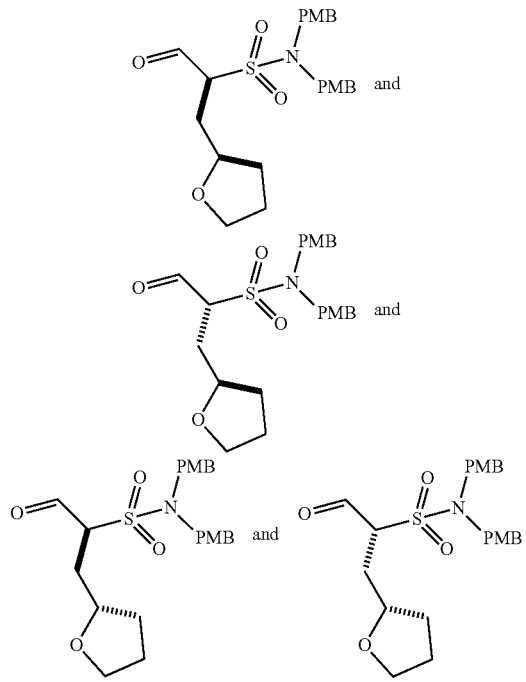

To a solution of (S)-1-hydroxy-N,N-bis(4-methoxybenzyl)-3-((R)-tetrahydrofuran-2-yl)propane-2-sulfonamide and (R)-1-hydroxy-N,N-bis(4-methoxybenzyl)-3-((S)-tetrahydrofuran-2-yl)propane-2-sulfonamide and (S)-1-hydroxy-N,N-bis(4-methoxybenzyl)-3-((S)-tetrahydrofuran-2-yl) propane-2-sulfonamide and (R)-1-hydroxy-N,N-bis(4-methoxybenzyl)-3-((R)-tetrahydrofuran-2-yl)propane-2-sulfonamide (Example 637, Step 3) (4.50 g, 10.0 mmol) in DCM (50 mL) was added Dess-Martin periodinane (8.49 g, 20.0 mmol) at ambient temperature. After the reaction mixture was stirred for 12 hrs, the reaction was diluted (saturated aqueous Na₂S₂O₃ solution), extracted (2×Et₂O), and washed (3×saturated aqueous NaHCO₃ and 1×brine). The combined organic layers were dried (MgSO₄) and concentrated under reduced pressure. The residue was injected into a 120 g ISCO Gold column and purified by combi-flash, eluting with 10% to 40% EtOAc/hexanes to give the title compounds (2.36 g, 5.27 mmol) as colorless oil.

Step 5: [(2R,3S)-3-hydroxy-N,N-bis(4-methoxybenzyl)-1-((R)-tetrahydrofuran-2-yl)hex-5-ene-2-sulfonamide and (2S,3R)-3-hydroxy-N,N-bis(4-methoxybenzyl)-1-((S)-tetrahydrofuran-2-yl)hex-5-ene-2-sulfonamide] or [(2R,3S)-3-hydroxy-N,N-bis(4-methoxybenzyl)-1-((S)-tetrahydrofuran-2-yl)hex-5-ene-2-sulfonamide and (2S,3R)-3-hydroxy-N,N-bis(4-methoxybenzyl)-1-((R)-tetrahydrofuran-2-yl)hex-5-ene-2-sulfonamide] or [(2S,3S)-3-hydroxy-N,N-bis(4-methoxybenzyl)-1-((R)-tetrahydrofuran-2-yl)hex-5-ene-2-sulfonamide and (2R,3R)-3-hydroxy-N,N-bis(4-methoxybenzyl)-1-((S)-tetrahydrofuran-2-yl)hex-5-ene-2-sulfonamide] or [(2R,3R)-3-hydroxy-N,N-bis(4-methoxybenzyl)-1-((S)-tetrahydrofuran-2-yl)hex-5-ene-2-sulfonamide and (2S,3S)-3-hydroxy-N,N-bis(4-methoxybenzyl)-1-((R)-tetrahydrofuran-2-yl)hex-5-ene-2-sulfonamide] (Racemic Mixtures 1 and 2)

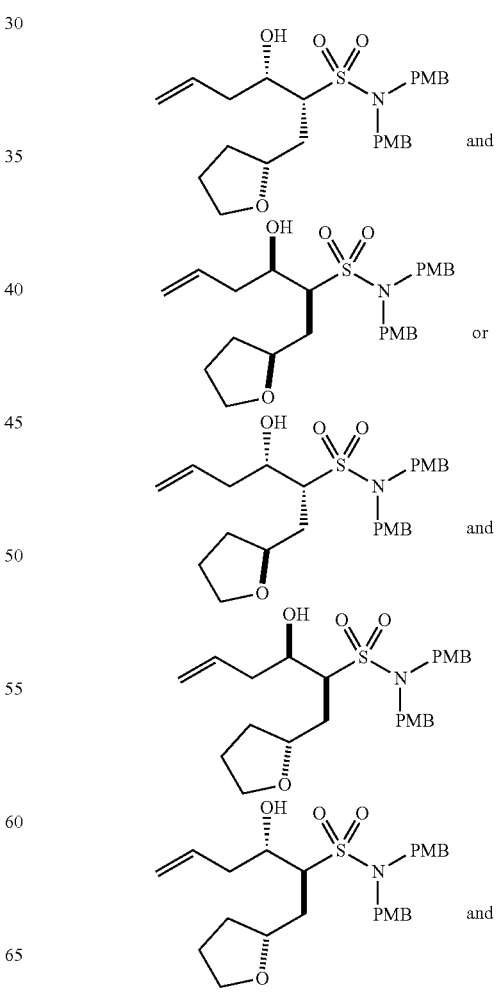

1331

-continued

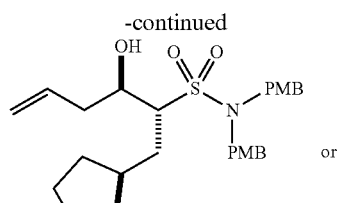

or

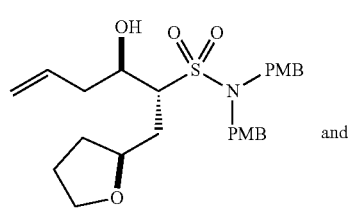

and

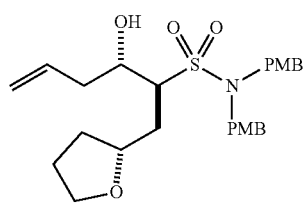

To a mixture of (S)—N,N-bis(4-methoxybenzyl)-1-oxo-3-((R)-tetrahydrofuran-2-yl)propane-2-sulfonamide and (R)—N,N-bis(4-methoxybenzyl)-1-oxo-3-((S)-tetrahydrofuran-2-yl)propane-2-sulfonamide and (S)—N,N-bis(4-methoxybenzyl)-1-oxo-3-((S)-tetrahydrofuran-2-yl)propane-2-sulfonamide and (R)—N,N-bis(4-methoxybenzyl)-1-oxo-3-((R)-tetrahydrofuran-2-yl)propane-2-sulfonamide (Example 637, Step 4) (2.36 g, 5.27 mmol) and allyl iodide (1.94 mL, 21.1 mmol) in DMF (21 mL) was added indium (2.42 g, 21.1 mmol) at ambient temperature. After the reaction was stirred overnight, the reaction was diluted (EtOAc and saturated aqueous NaHCO₃) and filtered through Celite to remove solid precipitates. Then the organic layer was separated from the filtrates, dried (MgSO₄), and concentrated under reduced pressure. The residue was injected into a 220 g ISCO Gold column and purified by combi-flash, eluting with 20% to 30% EtOAc/hexanes to give one racemic mixture from the title compounds (0.840 g, 1.72 mmol) (racemic mixture 1) as the faster eluting products and another racemic mixture of the title compounds was obtained as the second (slower) eluting products (0.840 g, 1.72 mmol) (racemic mixture 2)

1332

Step 6: [(2R,3S)-3-mythoxy-N,N-bis(4-methoxybenzyl)-1-((R)-tetrahydrofuran-2-yl)hex-5-ene-2-sulfonamide and (2S,3R)-3-mythoxy-N,N-bis(4-methoxybenzyl)-1-((S)-tetrahydrofuran-2-yl)hex-5-ene-2-sulfonamide] or [(2R,3S)-3-mythoxy-N,N-bis(4-methoxybenzyl)-1-((S)-tetrahydrofuran-2-yl)hex-5-ene-2-sulfonamide and (2S,3R)-3-mythoxy-N,N-bis(4-methoxybenzyl)-1-((R)-tetrahydrofuran-2-yl)hex-5-ene-2-sulfonamide] or [(2S,3S)-3-mythoxy-N,N-bis(4-methoxybenzyl)-1-((R)-tetrahydrofuran-2-yl)hex-5-ene-2-sulfonamide and (2R,3R)-3-mythoxy-N,N-bis(4-methoxybenzyl)-1-((S)-tetrahydrofuran-2-yl)hex-5-ene-2-sulfonamide] or [(2R,3R)-3-mythoxy-N,N-bis(4-methoxybenzyl)-1-((S)-tetrahydrofuran-2-yl)hex-5-ene-2-sulfonamide and (2S,3S)-3-mythoxy-N,N-bis(4-methoxybenzyl)-1-((R)-tetrahydrofuran-2-yl)hex-5-ene-2-sulfonamide]

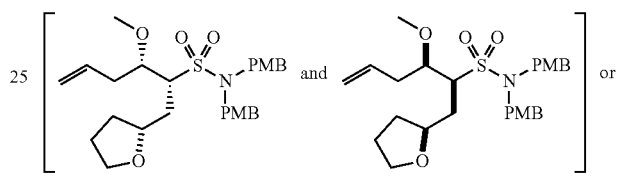 or

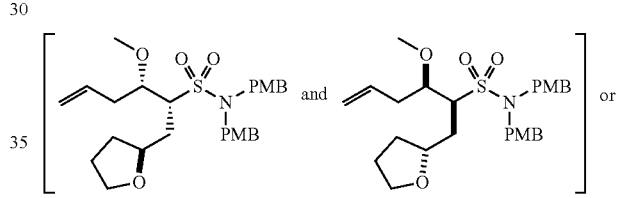 or

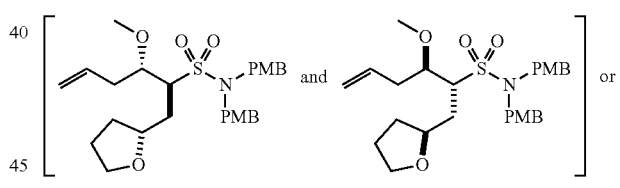 or


To a solution of the racemic mixture 1 from Example 637, Step 5 (840 mg, 1.72 mmol) and iodomethane (1.06 mL, 17.2 mmol) in THF (17 mL) was added t-BuOK (1.0 M solution in THF, 1.89 mL, 1.89 mmol) at 0° C. After the reaction mixture was stirred overnight at ambient temperature, the reaction was quenched (brine), extracted (EtOAc), and washed (brine). The combined organic layers were dried (Na₂SO₄) and concentrated under reduced pressure to provide a crude product which was used in next step without purification.

Step 7: [(2R,3S)-3-mythoxy-((R)-tetrahydrofuran-2-yl)hex-5-ene-2-sulfonamide and (2S,3R)-3-mythoxy-((S)-tetrahydrofuran-2-yl)hex-5-ene-2-sulfonamide] or [(2R,3S)-3-mythoxy-((S)-tetrahydrofuran-2-yl)hex-5-ene-2-sulfonamide and (2S,3R)-3-mythoxy-((R)-tetrahydrofuran-2-yl)hex-5-ene-2-sulfonamide] or [(2S,3S)-3-mythoxy-((R)-tetrahydrofuran-2-yl)hex-5-ene-2-sulfonamide and (2R,3R)-3-mythoxy-((S)-tetrahydrofuran-2-yl)hex-5-ene-2-sulfonamide] or [(2R,3R)-3-mythoxy-((S)-tetrahydrofuran-2-yl)hex-5-ene-2-sulfonamide and (2S,3S)-3-mythoxy-((R)-tetrahydrofuran-2-yl)hex-5-ene-2-sulfonamide]

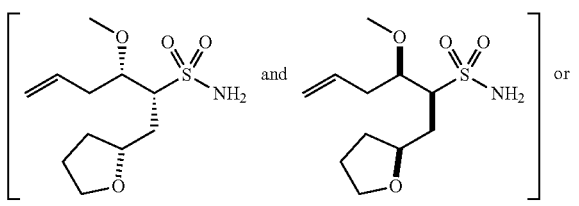

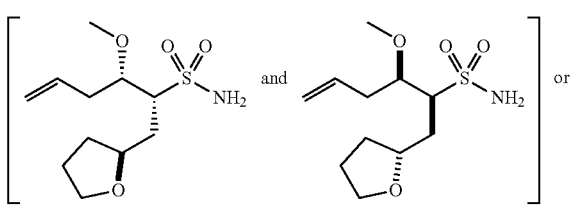

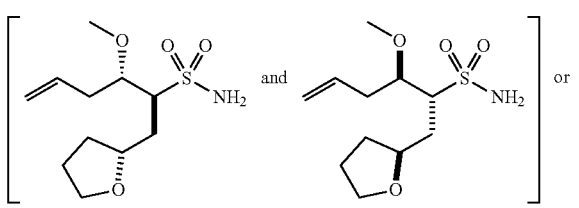

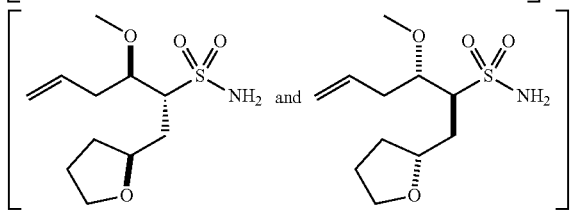

To a solution of the products from Example 637, Step 6 (864 mg, 1.72 mmol) in anisole (9.3 mL, 86 mmol) was added TFA (6.4 mL, 86 mmol) at ambient temperature. After the reaction was stirred over 2 days, the reaction was concentrated under reduced pressure. The residue was injected into a 12 g ISCO Gold column and purified by combi-flash, eluting with 20% to 70% EtOAc (containing 0.3% AcOH)/hexanes to give one racemic mixture of the title compounds (0.365 g, 1.38 mmol).

Step 8: [(S)-6'-chloro-5-(((1R,2R)-2-((1S,5R,6R,E)-1-hydroxy-5-methoxy-6-sulfamoyl-7-((S)-tetrahydrofuran-2-yl)hept-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1S,5S,6S,E)-1-hydroxy-5-methoxy-6-sulfamoyl-7-((R)-tetrahydrofuran-2-yl)hept-2-en-1-yl)cyclobutyl)methyl)-3',4,4',5-tetrahydro-2H,2'H-spiro[benzo[b][1,4]oxazepine-3,1'-naphthalene]-7-carboxylic Acid] or [(S)-6'-chloro-5-(((1R,2R)-2-((1S,5R,6R,E)-1-hydroxy-5-methoxy-6-sulfamoyl-7-((R)-tetrahydrofuran-2-yl)hept-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1S,5S,6S,E)-1-hydroxy-5-methoxy-6-sulfamoyl-7-((S)-tetrahydrofuran-2-yl)hept-2-en-1-yl)cyclobutyl)methyl)-3',4,4',5-tetrahydro-2H,2'H-spiro[benzo[b][1,4]oxazepine-3,1'-naphthalene]-7-carboxylic Acid] or [(S)-6'-chloro-5-(((1R,2R)-2-((1S,5R,6S,E)-1-hydroxy-5-methoxy-6-sulfamoyl-7-((S)-tetrahydrofuran-2-yl)hept-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1S,5S,6R,E)-1-hydroxy-5-methoxy-6-sulfamoyl-7-((R)-tetrahydrofuran-2-yl)hept-2-en-1-yl)cyclobutyl)methyl)-3',4,4',5-tetrahydro-2H,2'H-spiro[benzo[b][1,4]oxazepine-3,1'-naphthalene]-7-carboxylic Acid] or [(S)-6'-chloro-5-(((1R,2R)-2-((1S,5S,6R,E)-1-hydroxy-5-methoxy-6-sulfamoyl-7-((S)-tetrahydrofuran-2-yl)hept-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1S,5R,6S,E)-1-hydroxy-5-methoxy-6-sulfamoyl-7-((R)-tetrahydrofuran-2-yl)hept-2-en-1-yl)cyclobutyl)methyl)-3',4,4',5-tetrahydro-2H,2'H-spiro[benzo[b][1,4]oxazepine-3,1'-naphthalene]-7-carboxylic Acid]

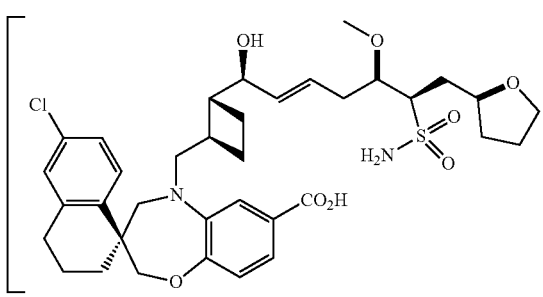 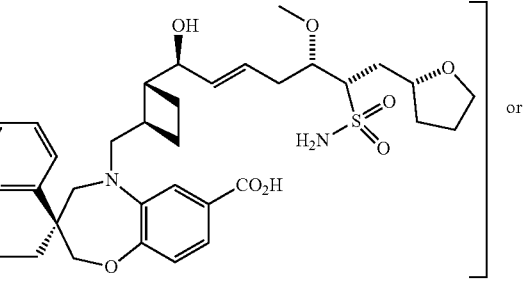

1335 1336

-continued

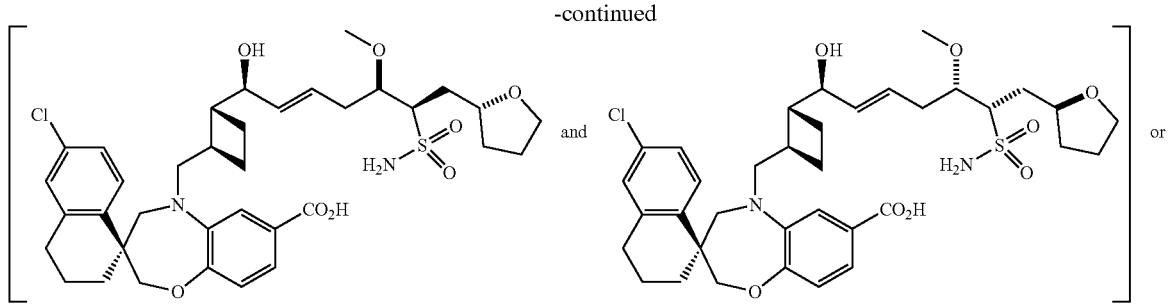

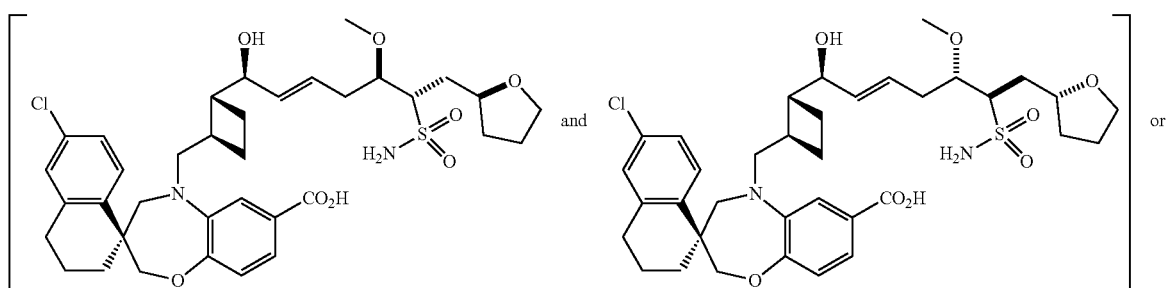

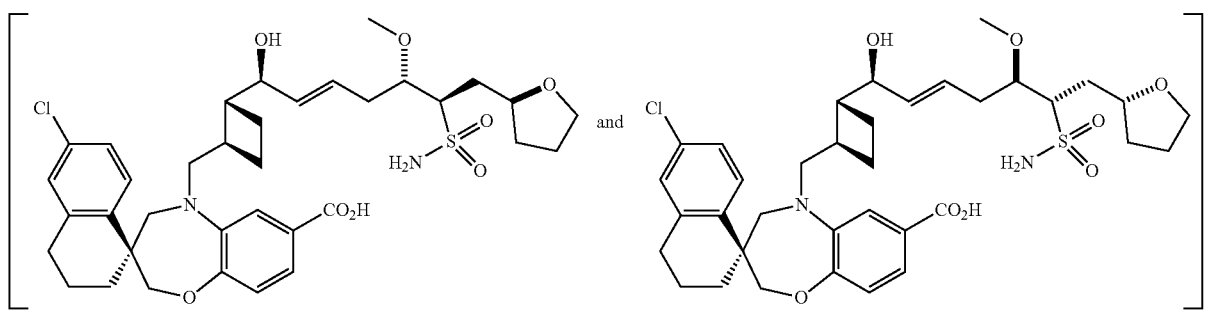

To a solution of (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (200 mg, 0.392 mmol) (Intermediate AA12) in DCM (4.5 mL) was added the products from Example 637, Step 7 (361 mg, 1.37 mmol). The solution was sparged with Ar for 15 min and Hoveyda-Grubbs 2nd generation catalyst (49 mg, 0.078 mmol) was added at ambient temperature. After the reaction mixture was stirred at ambient temperature for 2.5 hours, air was bubbling through the reaction solution for 10 min. After the reaction was concentrated under reduced pressure, the residue was injected into a 12 g ISCO Gold column and purified by combi-flash, eluting with 20% to 100% EtOAc (containing 0.3% AcOH)/hexanes to give one of the title compounds as a dark brown oil.

Step 9: (1S,3'R,6'R,7'S,8'E,11'S,12'R)-6-chloro-7'-hydroxy-11'-methoxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-hydroxy-11'-methoxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-7'-hydroxy-11'-methoxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-7'-hydroxy-11'-methoxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methoxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methoxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-11'-methoxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-11'-methoxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Isomer 1)

To a solution of the product from Example 637, Step 8 (310 mg, 0.441 mmol) in DCM (30 mL) was added EDC (380 mg, 1.98 mmol), N,N-dimethylpyridin-4-amine (DMAP) (242 mg, 1.98 mmol), and triethylamine (0.276 mL, 1.98 mmol) successively at ambient temperature. After the reaction was stirred over 2 days, the reaction mixture was injected into a 4 g ISCO Gold column and purified by combi-flash, eluting with 0% to 100% EtOAc (containing 0.3% AcOH)/hexanes to give a mixture of two diastereomers as a pale brown film. The resulting mixture of two diastereomers was further purified by reversed phase preparatory HPLC (Gemini™ Prep C$_{18}$ 5 μm column; Phenomenex, Torrance, CA; gradient elution of 45% to 85% MeCN in water, where both solvents contain 0.1% TFA, 30 min method) to provide one of the title compounds as the faster eluting isomer as a white foam. (60 mg, 0.088 mmol). $^1$H NMR (500 MHz, CDCl$_3$) δ ppm 8.12 (br. s., 1H) 7.72-7.65 (m, 1H) 7.23-7.13 (m, 2H) 7.10 (d, J=2.20 Hz, 1H) 6.97-6.84 (m, 2H) 5.75 (m, 2H) 4.42 (d, J=8.07 Hz, 1H) 4.22 (d, J=12.23 Hz, 1H) 4.20-4.06 (m, 3H) 3.73 (br. s., 2H) 3.63 (br. s., 2H) 3.46-3.33 (m, 4H) 2.84-2.70 (m, 2H) 2.56-2.35 (m, 3H) 2.35-2.22 (m, 2H) 2.14-2.01 (m, 4H) 1.98-1.76 (m, 7H) 1.76-1.61 (m, 2H) 1.55-1.43 (m, 2H); m/z (ESI, +ve ion) 685.2 (M+H)$^+$.

Example 638. (1S,3'R,6'R,7'S,8'E,11'S,12'R)-6-chloro-7'-hydroxy-11'-methoxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-hydroxy-11'-methoxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-7'-hydroxy-11'-methoxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-7'-hydroxy-11'-methoxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methoxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methoxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-11'-methoxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-11'-methoxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Isomer 2)

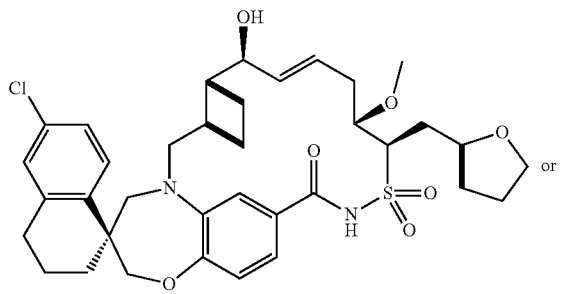

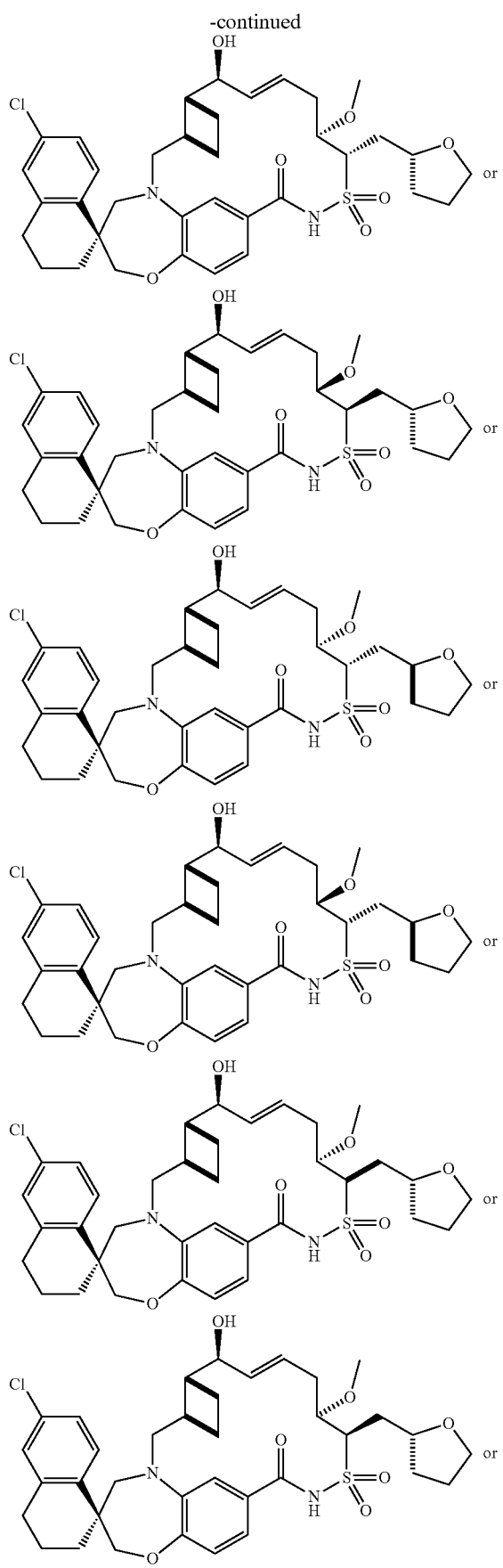

One of the title compounds was prepared by a procedure analogous to that described in Example 637, Steps 6 through 9, replacing the racemic mixture 1 in Step 6 with the racemic mixture 2 from Example 637, Step 5. The crude product was purified by reversed phase preparatory HPLC (Gemini™ Prep $C_{18}$ 5 μm column; Phenomenex, Torrance, CA; gradient elution of 45% to 75% MeCN in water, where both solvents contain 0.1% TFA, 30 min method) to provide one of the title compounds as the faster eluting isomer as a white foam. $^1$H NMR (500 MHz, CDCl$_3$) δ ppm 8.40 (br. s., 1H) 7.74-7.66 (m, 1H) 7.24-7.16 (m, 2H) 7.12 (d, J=1.96 Hz, 1H) 7.00-6.88 (m, 2H) 5.87-5.64 (m, 2H) 4.25 (m, 1H) 4.22-4.02 (m, 4H) 3.86-3.57 (m, 4H) 3.50-3.36 (m, 4H) 2.87-2.69 (m, 2H) 2.58 (m, 1H) 2.44-2.26 (m, 4H) 2.21 (m, 1H) 2.17-1.78 (m, 11H) 1.77-1.50 (m, 4H); m/z (ESI, +ve ion) 685.2 (M+H)$^+$.

Example 639. (1S,3'R,6'R,7'S,8'E,11'S,12'R)-6-chloro-12'-(cyclobutylmethyl)-7'-hydroxy-11'-methoxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-12'-(cyclobutylmethyl)-7'-hydroxy-11'-methoxy-3,4-dihydro-2H,15'H-spiro [naphthalene-1,22'-[20]oxa[13]thia[1,14] diazatetracyclo[14.7.2.0$^{3,6}$.0$^{19,24}$]pentacosa [8,16,18, 24]tetraen]-15'-one 13',13'-dioxide or (1S,3'R,6'R, 7'S,8'E,11'S,12'S)-6-chloro-12'-(cyclobutylmethyl)-7'-hydroxy-11'-methoxy-3,4-dihydro-2H,15'H-spiro [naphthalene-1,22'-[20]oxa[13]thia[1,14] diazatetracyclo[14.7.2.0$^{3,6}$.0$^{19,24}$]pentacosa [8,16,18, 24]tetraen]-15'-one 13',13'-dioxide or (1S,3'R,6'R, 7'S,8'E,11'R,12'R)-6-chloro-12'-(cyclobutylmethyl)-7'-hydroxy-11'-methoxy-3,4-dihydro-2H,15'H-spiro [naphthalene-1,22'-[20]oxa[13]thia[1,14] diazatetracyclo[14.7.2.0$^{3,6}$.0$^{19,24}$]pentacosa [8,16,18, 24]tetraen]-15'-one 13',13'-dioxide (Isomer 1)

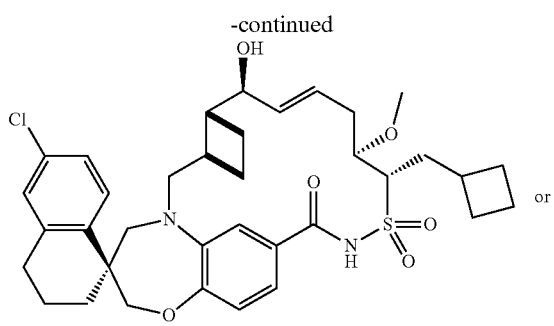

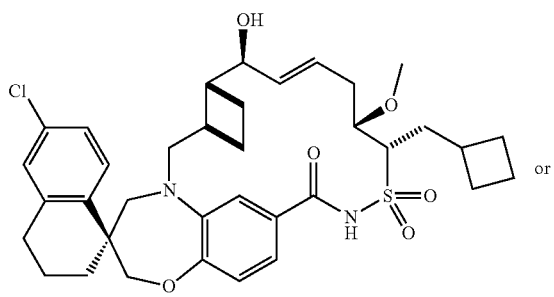

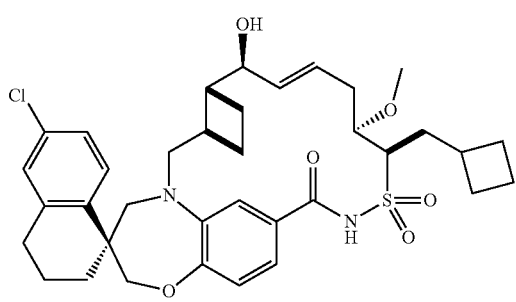

One of the title compounds was prepared by a procedure analogous to that described in Example 574, Steps 1 through 3, replacing (bromomethyl)cyclopropane in Step 1 with (bromomethyl)cyclobutane. The crude product was purified by reversed phase preparatory HPLC (Gemini™ Prep $C_{18}$ 5 μm column; Phenomenex, Torrance, CA; gradient elution of 50% to 85% MeCN in water, where both solvents contain 0.1% TFA, 30 min method) to provide one crude containing the faster eluting isomer. The crude was further purified by combi-flash (4 g ISCO Gold column), eluting with 10% to 60% EtOAc (containing 0.3% AcOH)/hexanes to give one of the title compounds. $^1$H NMR (500 MHz, CDCl$_3$) δ ppm 8.26 (br. s., 1H) 7.70 (d, J=8.56 Hz, 1H) 7.18 (dd, J=8.56, 2.20 Hz, 1H) 7.14-7.02 (m, 2H) 6.94 (s, 2H) 5.78 (dd, J=15.16, 6.60 Hz, 1H) 5.65 (dt, J=13.94, 6.72 Hz, 1H) 4.20-4.06 (m, 3H) 3.95 (dd, J=7.34, 4.16 Hz, 1H) 3.77 (m, 1H) 3.69 (m, 1H) 3.52 (m, 1H) 3.41-3.34 (s, 3H) 3.30 (d, J=11.49 Hz, 1H) 3.12 (br. s., 1H) 2.85-2.69 (m, 3H) 2.58-2.48 (m, 1H) 2.48-2.33 (m, 2H) 2.33-2.22 (m, 2H) 2.22-2.06 (m, 2H) 2.03-1.80 (m, 8H) 1.78-1.66 (m, 3H) 1.50-1.39 (m, 2H); m/z (ESI, +ve ion) 669.2 (M+H)$^+$.

Example 640. (1S,3'R,6'R,7'S,8'E,11'S,12'R)-6-chloro-12'-(cyclobutylmethyl)-7'-hydroxy-11'-methoxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide or (1S,3'R,6'R,7'S,8'E,11'R, 12'S)-6-chloro-12'-(cyclobutylmethyl)-7'-hydroxy-11'-methoxy-3,4-dihydro-2H,15'H-spiro [naphthalene-1,22'-[20]oxa[13]thia[1,14] diazatetracyclo[14.7.2.0$^{3,6}$.0$^{19,24}$]pentacosa [8,16,18, 24]tetraen]-15'-one 13',13'-dioxide or (1S,3'R,6'R, 7'S,8'E,11'S,12'S)-6-chloro-12'-(cyclobutylmethyl)-7'-hydroxy-11'-methoxy-3,4-dihydro-2H,15'H-spiro [naphthalene-1,22'-[20]oxa[13]thia[1,14] diazatetracyclo[14.7.2.0$^{3,6}$.0$^{19,24}$]pentacosa [8,16,18, 24]tetraen]-15'-one 13',13'-dioxide or (1S,3'R,6'R, 7'S,8'E,11'R,12'R)-6-chloro-12'-(cyclobutylmethyl)-7'-hydroxy-11'-methoxy-3,4-dihydro-2H,15'H-spiro [naphthalene-1,22'-[20]oxa[13]thia[1,14] diazatetracyclo[14.7.2.0$^{3,6}$.0$^{19,24}$]pentacosa [8,16,18, 24]tetraen]-15'-one 13',13'-dioxide (Isomer 2)

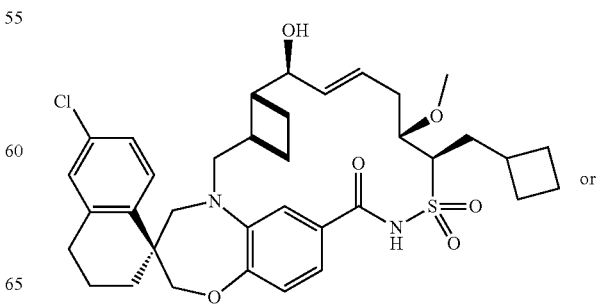

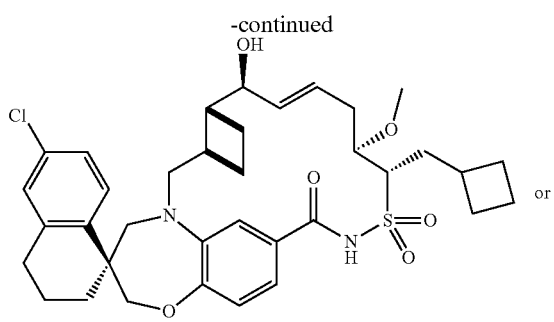

One of the title compounds was obtained as the second (slower) eluting isomer from reversed phase preparatory HPLC in Example 639. ¹H NMR (500 MHz, CDCl₃) δ ppm 8.15 (s, 1H) 7.49-7.71 (m, 2H) 7.08 (dd, J=8.56, 2.20 Hz, 1H) 7.03 (d, J=2.20 Hz, 1H) 6.92-6.77 (m, 2H) 5.68 (dd, J=15.77, 4.03 Hz, 1H) 5.31 (br. s., 1H) 4.23-4.10 (m, 2H) 4.02 (d, J=3.67 Hz, 1H) 3.90-3.76 (m, 2H) 3.70 (d, J=14.67 Hz, 1H) 3.42-3.32 (m, 1H) 3.30 (s, 3H) 3.27-3.18 (m, 1H) 3.04 (d, J=14.18 Hz, 1H) 2.80-2.61 (m, 3H) 1.93 (m, 1H) 2.50-2.34 (m, 3H) 2.24-2.13 (m, 2H) 2.13-1.98 (m, 3H) 1.86-1.62 (m, 5H) 1.62-1.39 (m, 4H) 1.37-1.26 (m, 2H); m/z (ESI, +ve ion) 669.2 (M+H)⁺.

Example 641. (1S,3'R,6'R,7'S,8'E,11'S,12'R)-6-chloro-7',11'-dimethoxy-12'-((2S)-tetrahydro-2-furanylmethyl)-3,4-dihydro-2H,15'H-spiro[naphthalene-1,22'-[20]oxa[13]thia[1,14]diazatetracyclo [14.7.2.0³,⁶.0¹⁹,²⁴]pentacosa [8,16,18,24]tetraen]-15'-one 13',13'-dioxide or (1S,3'R,6'R,7'S,8'E,11'S,12'R)-6-chloro-7',11'-dimethoxy-12'-((2R)-tetrahydro-2-furanylmethyl)-3,4-dihydro-2H,15'H-spiro[naphthalene-1,22'-[20]oxa[13]thia[1,14] diazatetracyclo[14.7.2.0³,⁶.0¹⁹,²⁴]pentacosa [8,16,18, 24]tetraen]-15'-one 13',13'-dioxide or (1S,3'R,6'R, 7'S,8'E,11'R,12'S)-6-chloro-7',11'-dimethoxy-12'-((2S)-tetrahydro-2-furanylmethyl)-3,4-dihydro-2H, 15'H-spiro[naphthalene-1,22'-[20]oxa[13]thia[1,14] diazatetracyclo[14.7.2.0³,⁶.0¹⁹,²⁴]pentacosa [8,16,18, 24]tetraen]-15'-one 13',13'-dioxide or (1S,3'R,6'R, 7'S,8'E,11'R,12'S)-6-chloro-7',11'-dimethoxy-12'-((2R)-tetrahydro-2-furanylmethyl)-3,4-dihydro-2H, 15'H-spiro[naphthalene-1,22'-[20]oxa[13]thia[1,14] diazatetracyclo[14.7.2.0³,⁶.0¹⁹,²⁴]pentacosa [8,16,18, 24]tetraen]-15'-one 13',13'-dioxide or (1S,3'R,6'R, 7'S,8'E,11'S,12'S)-6-chloro-7',11'-dimethoxy-12'-((2S)-tetrahydro-2-furanylmethyl)-3,4-dihydro-2H, 15'H-spiro[naphthalene-1,22'-[20]oxa[13]thia[1,14] diazatetracyclo[14.7.2.0³,⁶.0¹⁹,²⁴]pentacosa [8,16,18, 24]tetraen]-15'-one 13',13'-dioxide or (1S,3'R,6'R, 7'S,8'E,11'S,12'S)-6-chloro-7',11'-dimethoxy-12'-((2R)-tetrahydro-2-furanylmethyl)-3,4-dihydro-2H, 15'H-spiro[naphthalene-1,22'-[20]oxa[13]thia[1,14] diazatetracyclo[14.7.2.0³,⁶.0¹⁹,²⁴]pentacosa [8,16,18, 24]tetraen]-15'-one 13',13'-dioxide or (1S,3'R,6'R, 7'S,8'E,11'R,12'R)-6-chloro-7',11'-dimethoxy-12'-((2S)-tetrahydro-2-furanylmethyl)-3,4-dihydro-2H, 15'H-spiro[naphthalene-1,22'-[20]oxa[13]thia[1,14] diazatetracyclo[14.7.2.0³,⁶.0¹⁹,²⁴]pentacosa [8,16,18, 24]tetraen]-15'-one 13',13'-dioxide or (1S,3'R,6'R, 7'S,8'E,11'R,12'R)-6-chloro-7',11'-dimethoxy-12'-((2R)-tetrahydro-2-furanylmethyl)-3,4-dihydro-2H, 15'H-spiro[naphthalene-1,22'-[20]oxa[13]thia[1,14] diazatetracyclo[14.7.2.0³,⁶.0¹⁹,²⁴]pentacosa [8,16,18, 24]tetraen]-15'-one 13',13'-dioxide

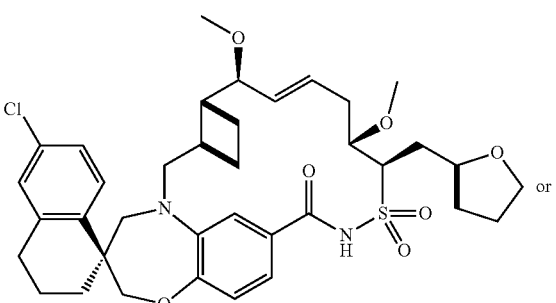

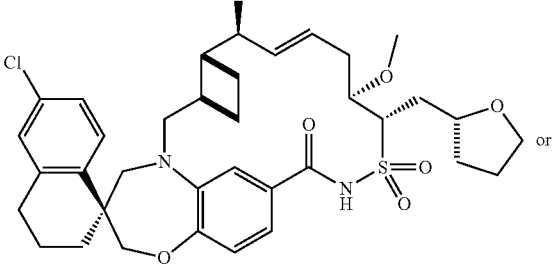

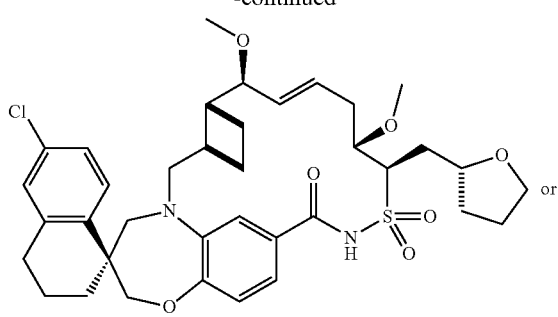

or

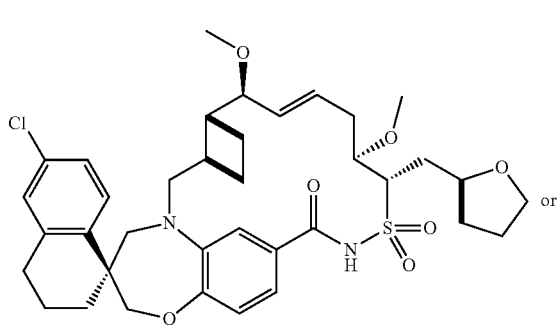

or

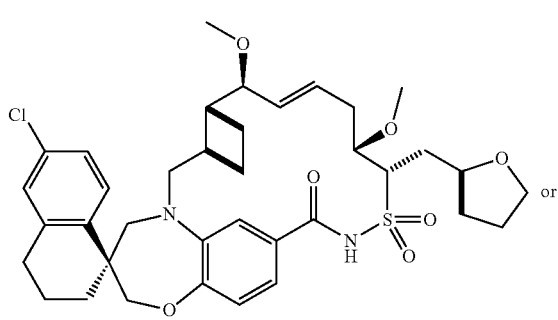

or

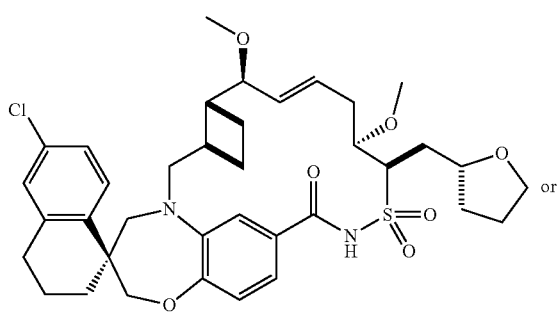

or

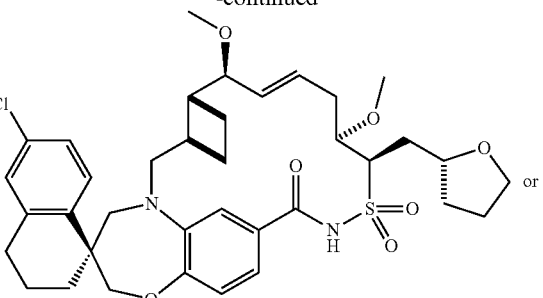

or

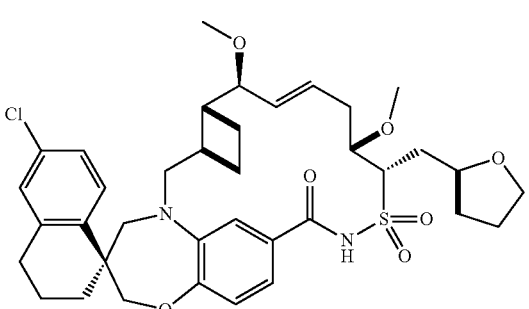

To a solution of product of Example 637 in THF (0.5 mL) was added NaH (60% dispersion in mineral oil, 2.6 mg, 0.066 mmol) at 0° C. After the reaction mixture was stirred at 0° C. for 30 min, a solution of MeI (2.5 µL, 0.039 mmol) in THF (0.5 mL) was added. The reaction mixture was stirred at ambient temperature for 2 h. Then the reaction was quenched (water and 1 N aqueous HCl), extracted (EtOAc), and washed (brine). The combined organic layers were dried ($Na_2SO_4$) and concentrated under reduced pressure to provide a crude product. The crude product was purified by reversed phase preparatory HPLC (Gemini™ Prep $C_{18}$ 5 µm column; Phenomenex, Torrance, CA; gradient elution of 50% to 85% MeCN in water, where both solvents contain 0.1% TFA, 30 min method) to provide one of the title compounds (5.0 mg, 7.1 µmol) as a white foam. $^1$H NMR (400 MHz, $CDCl_3$) δ ppm 8.18 (s, 1H) 7.70 (d, J=8.41 Hz, 1H) 7.18 (dd, J=8.41, 2.35 Hz, 1H) 7.10 (d, J=2.35 Hz, 1H) 6.99-6.89 (m, 2H) 6.89-6.82 (m, 1H) 5.85-5.69 (m, 1H) 5.61 (dd, J=15.36, 8.90 Hz, 1H) 4.58 (d, J=6.46 Hz, 1H) 4.40-4.26 (m, 1H) 4.10 (s, 2H) 3.86-3.64 (m, 5H) 3.52-3.39 (m, 1H) 3.39-3.33 (m, 3H) 3.28-3.20 (m, 4H) 3.01 (dd, J=15.26, 9.98 Hz, 1H) 2.88-2.69 (m, 2H) 2.54-2.40 (m, 3H) 2.40-2.26 (m, 2H) 2.13-2.09 (m, 1H) 2.07-1.81 (m, 9H) 1.75-1.60 (m, 1H) 1.60-1.48 (m, 1H) 1.40 (t, J=12.52 Hz, 1H); m/z (ESI, +ve ion) 699.2 $(M+H)^+$.

1347

Example 642. (1S,3'R,6'R,7'S,8'E,11'S,12'R)-6-chloro-7',11'-dimethoxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-7',11'-dimethoxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-7',11'-dimethoxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-7',11'-dimethoxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7',11'-dimethoxy-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'5,12'S)-6-chloro-7',11'-dimethoxy-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-7',11'-dimethoxy-12'-((2S)-tetrahydro-2-furanylmethyl)-3,4-dihydro-2H,15'H-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7',11'-dimethoxy-12'-((2R)-tetrahydro-2-furanylmethyl)-3,4-dihydro-2H,15'H-spiro[naphthalene-1,22'[20]oxa [13]thia[1,14]diazatetracyclo[14.7.2.0$^{3,6}$.0$^{19,24}$]pentacosa[8,16,18,24]tetraen]-15'-one 13',13'-dioxide

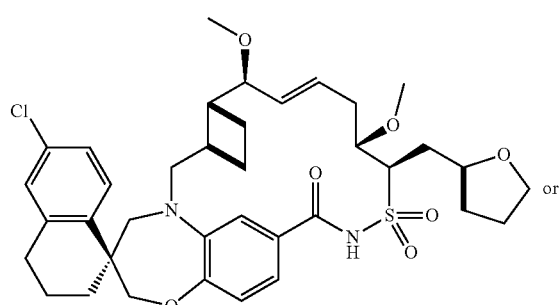

or

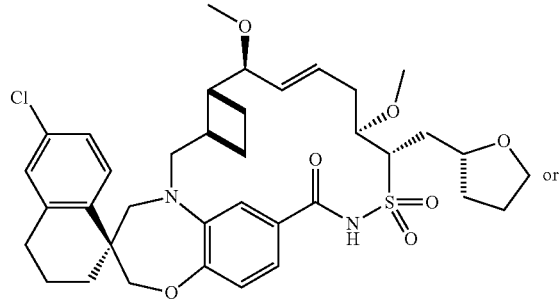

or

1348

-continued

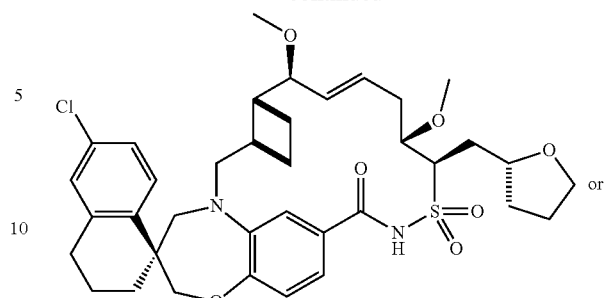

or

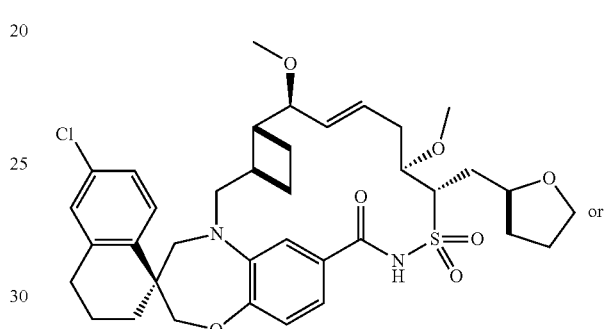

or

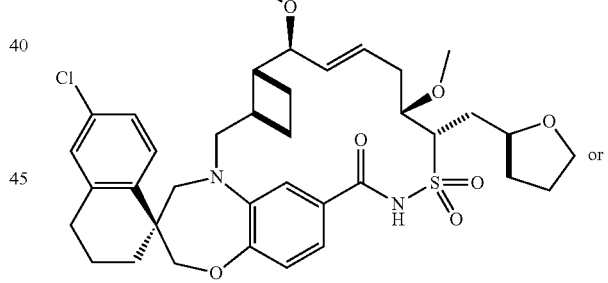

or

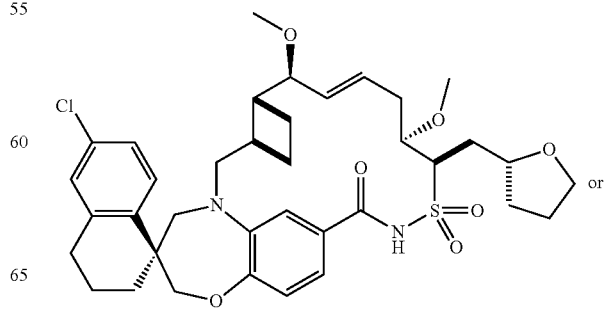

or

-continued

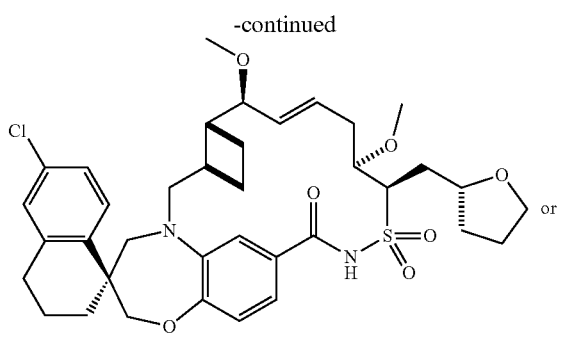

or

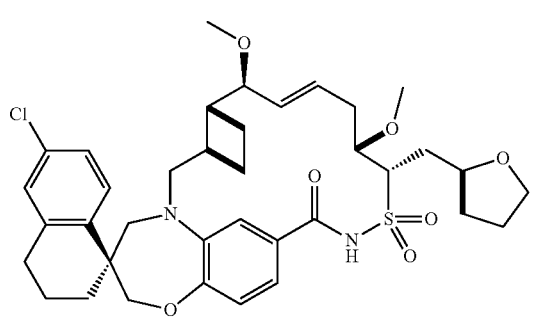

To a solution of Example 638 (5 mg, 0.007 mmol) in THF (0.5 mL) was added NaH (60% dispersion in mineral oil, 1.4 mg, 0.036 mmol) at 0° C. After the reaction mixture was stirred at 0° C. for 30 min, a solution of MeI (1.4 µL, 0.022 mmol) in THF (0.5 mL) was added. The reaction mixture was stirred at ambient temperature for 2 h. Then the reaction was quenched (water and 1 N aqueous HCl), extracted (EtOAc), and washed (brine). The combined organic layers were dried (Na$_2$SO$_4$) and concentrated under reduced pressure to provide a crude product. The crude product was purified by reversed phase preparatory HPLC (Gemini™ Prep C$_{18}$ 5 µm column; Phenomenex, Torrance, CA; gradient elution of 50% to 85% MeCN in water, where both solvents contain 0.1% TFA, 30 min method) to provide one of the title compounds. $^1$H NMR (400 MHz, CDCl$_3$) δ ppm 8.07 (s, 1H) 7.62 (d, J=8.41 Hz, 1H) 7.10 (dd, J=8.61, 2.15 Hz, 1H) 7.02 (d, J=1.96 Hz, 1H) 6.91-6.81 (m, 2H) 6.78 (s, 1H) 5.70-5.57 (m, 1H) 5.57-5.44 (m, 1H) 4.33 (t, J=5.97 Hz, 1H) 4.13 (quin, J=6.50 Hz, 1H) 4.02 (s, 2H) 3.83 (q, J=7.30 Hz, 1H) 3.78-3.55 (m, 4H) 3.48 (t, J=7.43 Hz, 1H) 3.32 (s, 3H) 3.23-3.09 (m, 4H) 2.95 (dd, J=15.26, 9.78 Hz, 1H) 2.79-2.63 (m, 2H) 2.49 (t, J=6.75 Hz, 2H) 2.42-2.32 (m, 1H) 2.32-2.17 (m, 3H) 2.10-2.00 (m, 1H) 1.97-1.78 (m, 8H) 1.66-1.51 (m, 2H) 1.33 (t, J=12.52 Hz, 1H); m/z (ESI, +ve ion) 699.2 (M+H)$^+$.

Example 643. (1S,3'R,6'R,7'S,8'E,11'S,12'R)-6-chloro-7'-hydroxy-11'-methoxy-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-7'-hydroxy-11'-methoxy-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methoxy-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-11'-methoxy-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Isomer 1)

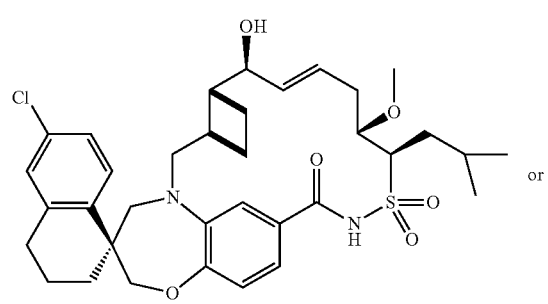

or

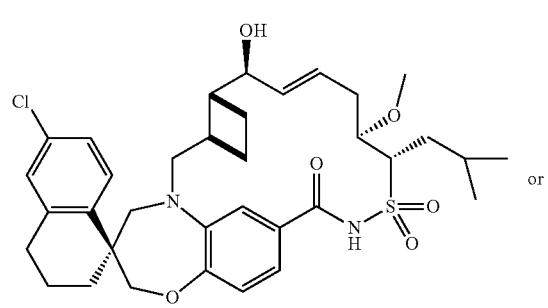

or

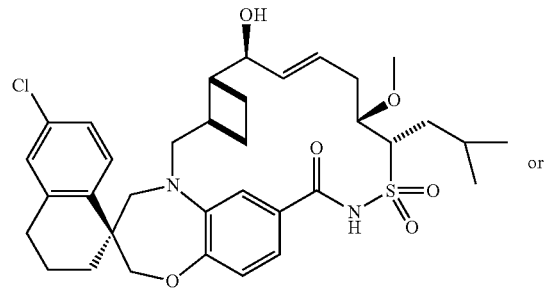

or

1351

-continued

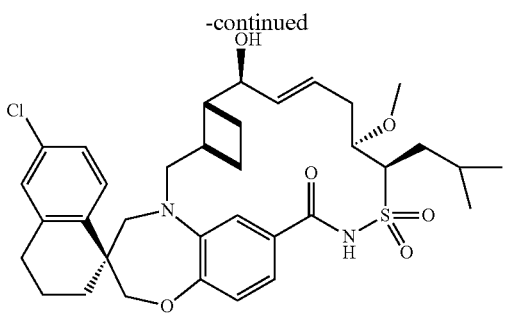

One of the title compounds was prepared by a procedure analogous to that described in Example 574, Steps 1 through 3, replacing (bromomethyl)cyclopropane in Step 1 with 1-bromo-2-methylpropane. The crude product was purified by reversed phase preparatory HPLC (Gemini™ Prep $C_{18}$ 5 µm column; Phenomenex, Torrance, CA; gradient elution of 50% to 75% MeCN in water, where both solvents contain 0.1% TFA, 30 min method) to provide one of the title compounds as the faster eluting isomer. $^1$H NMR (400 MHz, CDCl$_3$) δ ppm 8.15 (s, 1H) 7.70 (d, J=8.61 Hz, 1H) 7.18 (dd, J=8.51, 2.25 Hz, 1H) 7.12-7.02 (m, 2H) 6.97-6.92 (m, 2H) 5.86-5.74 (m, 1H) 5.74-5.62 (m, 1H) 4.21-4.06 (m, 4H) 3.80 (d, J=15.26 Hz, 1H) 3.70 (d, J=14.48 Hz, 1H) 3.54 (d, J=12.32 Hz, 1H) 3.38 (s, 3H) 3.29 (d, J=14.28 Hz, 1H) 3.10 (br. s., 1H) 2.85-2.71 (m, 2H) 2.58-2.33 (m, 3H) 2.32-2.19 (m, 1H) 2.19-2.06 (m, 2H) 2.05-1.38 (m, 9H) 1.08-0.93 (m, 6H); m/z (ESI, +ve ion) 657.2 (M+H)$^+$.

Example 644. (1S,3'R,6'R,7'S,8'E,11'S,12'R)-6-chloro-7'-hydroxy-11'-methoxy-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-7'-hydroxy-11'-methoxy-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methoxy-12'-(2-methylpropyl)-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide or (1S,3'R,6'R,7'S,8'E,11'R,12'R)-6-chloro-7'-hydroxy-11'-methoxy-12'-(2-methylpropyl)-3,4-dihydro-2H,15'H-spiro[naphthalene-1,22'-[20]oxa [13]thia[1,14]diazatetracyclo[14.7.2.0$^{3,6}$.0$^{19,24}$] pentacosa [8,16,18,24]tetraen]-15'-one 13',13'-dioxide (Isomer 2)

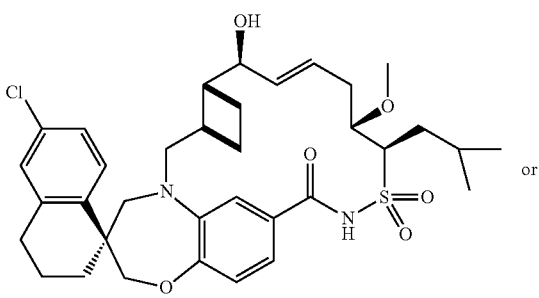

1352

-continued

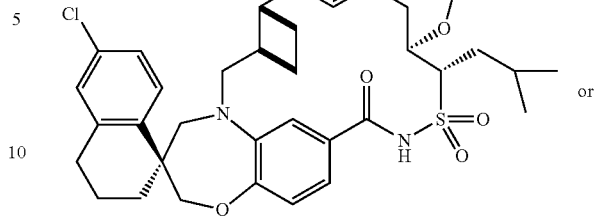

or

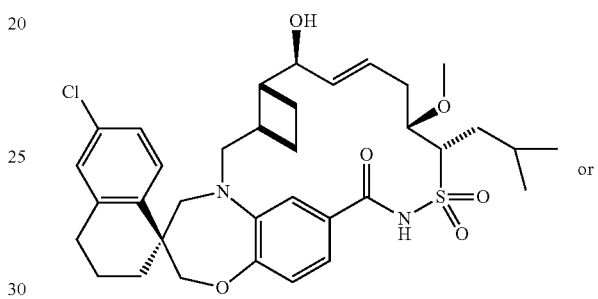

or

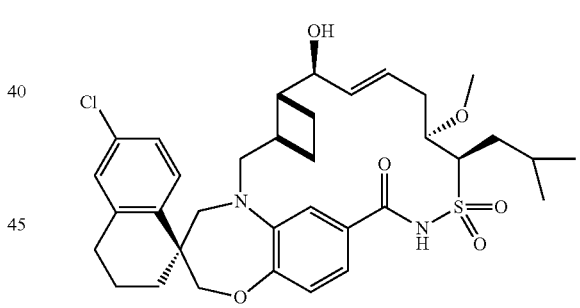

One of the title compounds was obtained as the second (slower) eluting isomer from reversed phase preparatory HPLC in Example 643. $^1$H NMR (400 MHz, CDCl$_3$) δ ppm 8.17 (s, 1H) 7.76-7.59 (m, 2H) 7.19-7.13 (m, 1H) 7.11 (d, J=2.35 Hz, 1H) 6.98-6.90 (m, 2H) 5.78 (dd, J=15.75, 4.21 Hz, 1H) 5.50-5.33 (m, 1H) 4.30-4.19 (m, 2H) 4.19-4.01 (m, 2H) 3.97-3.87 (m, 1H) 3.79 (d, J=13.69 Hz, 1H) 3.47 (dd, J=10.96, 2.93 Hz, 1H) 3.44-3.26 (m, 4H) 3.12 (d, J=14.67 Hz, 1H) 2.75 (br. s., 2H) 2.59-2.44 (m, 3H) 2.23-2.04 (m, 3H) 1.87-1.57 (m, 8H) 1.46-1.34 (m, 1H) 1.08-0.99 (m, 6H); m/z (ESI, +ve ion) 657.2 (M+H)$^+$.

Example 645. (1S,3'R,6'R,7'S,8'E,11'S,12'R)-6-chloro-11'-methoxy-7'-(2-(4-morpholinyl)ethoxy)-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-11'-methoxy-7'-(2-(4-morpholinyl)ethoxy)-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-11'-methoxy-7'-(2-(4-morpholinyl)ethoxy)-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-11'-methoxy-7'-(2-(4-morpholinyl)ethoxy)-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-11'-methoxy-7'-(2-(4-morpholinyl)ethoxy)-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-11'-methoxy-7'-(2-(4-morpholinyl)ethoxy)-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-11'-methoxy-7'-(2-(4-morpholinyl)ethoxy)-12'-((2S)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-11'-methoxy-7'-(2-(4-morpholinyl)ethoxy)-12'-((2R)-tetrahydro-2-furanylmethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

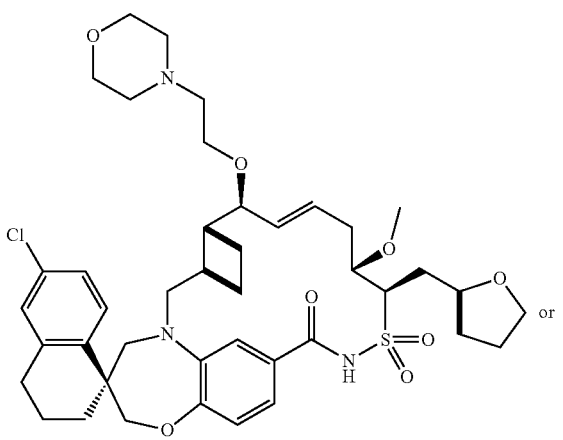

-continued

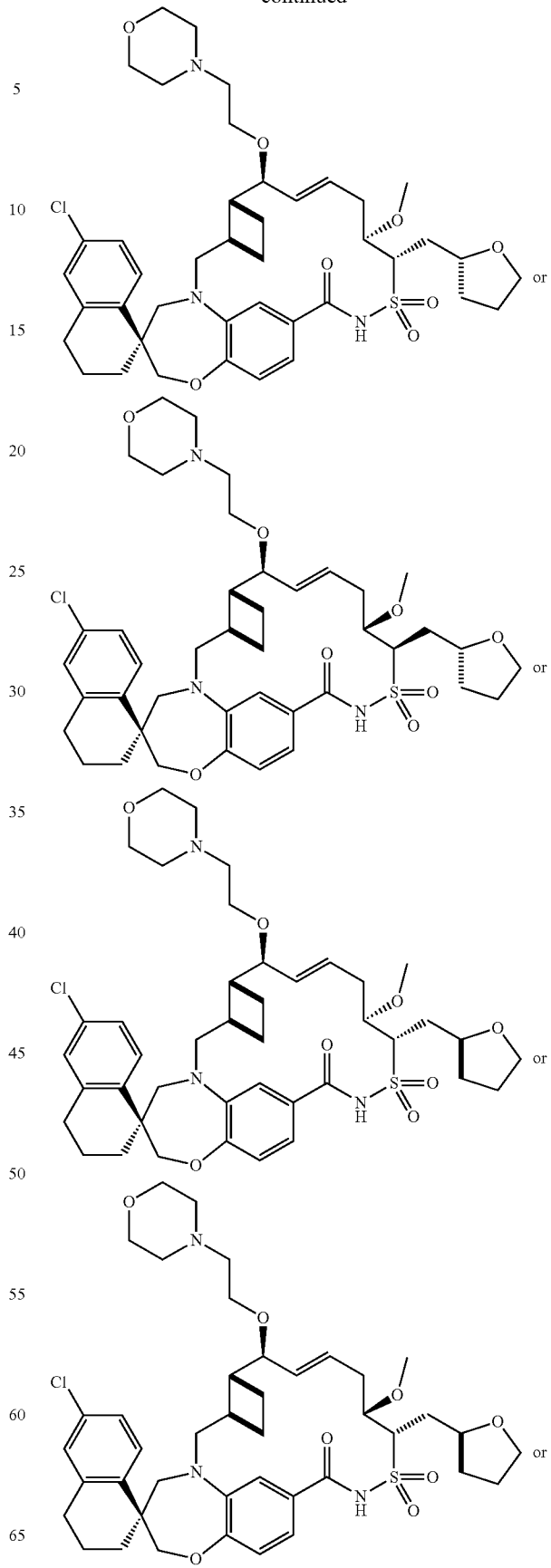

-continued


or


or

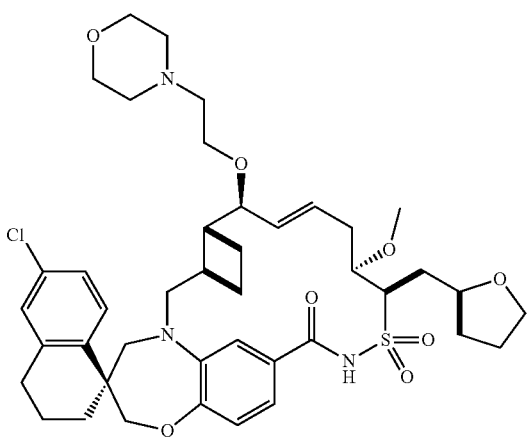

To a solution of the product in Example 637 in DMF (0.67 mL) was added NaH (60% dispersion in mineral oil, 5.8 mg, 0.15 mmol) at 0°C. After the reaction mixture was stirred at 0° C. for 15 min, 4-(2-bromoethyl)morpholine hydrobromide (20 mg, 0.073 mmol) was added. The reaction mixture was stirred at ambient temperation over 2 days. Then, the reaction was quenched (aqueous NH₄Cl), extracted (EtOAc), and washed (brine). The combined organic layers were dried (Na₂SO₄) and concentrated under reduced pressure to provide a crude product. The crude product was purified by reversed phase preparatory HPLC (Gemini™ Prep $C_{18}$ 5 μm column; Phenomenex, Torrance, CA; gradient elution of 40% to 70% MeCN in water, where both solvents contain 0.1% TFA, 30 min method) to provide one of the title compounds (8.0 mg, 10 μmol). ¹H NMR (500 MHz, CDCl₃) δ ppm 8.32 (br. s., 1H) 7.70 (d, J=8.56 Hz, 1H) 7.18 (d, J=8.56 Hz, 1H) 7.14-7.08 (m, 1H) 7.00-6.88 (m, 2H) 6.82 (s, 1H) 5.88-5.74 (m, 1H) 5.60 (dd, J=14.79, 8.44 Hz, 1H) 4.49 (d, J=7.09 Hz, 1H) 4.36-4.25 (m, 1H) 4.16-3.99 (m, 5H) 3.89-3.66 (m, 6H) 3.61 (m, 1H) 3.54-3.43 (m, 1H) 3.43-3.33 (m, 4H) 3.33-3.16 (m, 3H) 3.05-2.90 (m, 3H) 2.87-2.71 (m, 2H) 2.58-2.27 (m, 5H) 2.14-1.45 (m, 13H) 1.40 (t, J=12.72 Hz, 2H); m/z (ESI, +ve ion) 798.2 (M+H)⁺.

Example 646. (1S,3'R,6'R,7'S,8'E,11'S)-11'-benzyl-6-chloro-7'-hydroxy-3,4-dihydro-2H,14'H-spiro[naphthalene-1,21'-[19]oxa[12]thia[1,13]diazatetracyclo[13.7.2.0³,⁶.0¹⁹,²⁴]tetracosa [8,15,17,23]tetraen]-14'-one 12',12'-dioxide or (1S,3'R,6'R,7'S,8'E,11'R)-11'-benzyl-6-chloro-7'-hydroxy-3,4-dihydro-2H,14'H-spiro[naphthalene-1,21'-[19]oxa[12]thia[1,13]diazatetracyclo[13.7.2.0³,⁶.0¹⁹,²⁴]tetracosa [8,15,17,23]tetraen]-14'-one 12',12'-dioxide

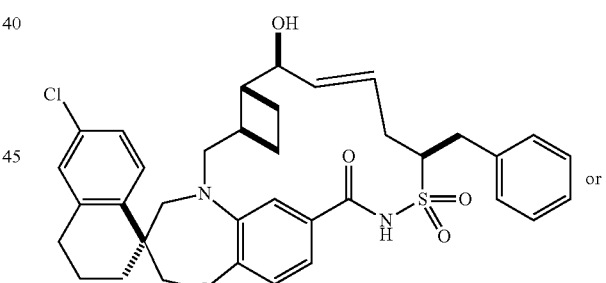

or

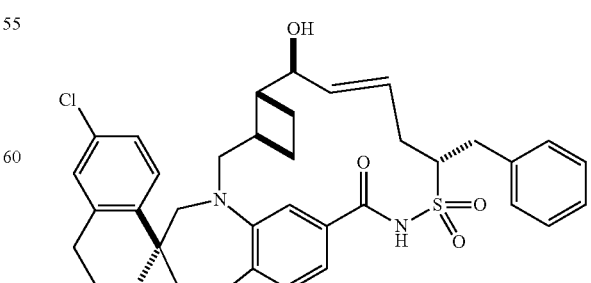

Step 1: (S)—N,N-bis(4-methoxybenzyl)-1-phenyl-pent-4-ene-2-sulfonamide and (R)—N,N-bis(4-methoxybenzyl)-1-phenylpent-4-ene-2-sulfonamide

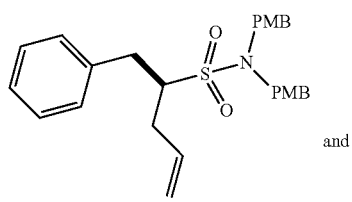

and

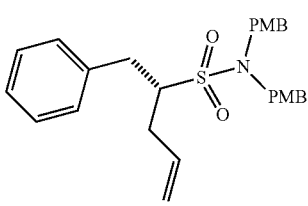

The title compound was prepared from N,N-bis(4-methoxybenzyl)but-3-ene-1-sulfonamide (Intermediate EE16) by a procedure analogous to that described in Example 648, Step 1.

Step 2: (1S,3'R,6'R,7'S,8'E,11'S)-11'-benzyl-6-chloro-7'-hydroxy-3,4-dihydro-2H,14'H-spiro[naphthalene-1,21'-[19]oxa[12]thia[1,13]diazatetracyclo[13.7.2.0$^{3,6}$.0$^{19,24}$]tetracosa [8,15,17,23]tetraen]-14'-one 12',12'-dioxide or (1S,3'R,6'R,7'S,8'E,11'R)-11'-benzyl-6-chloro-7'-hydroxy-3,4-dihydro-2H,14'H-spiro[naphthalene-1,21'-[19]oxa[12]thia[1,13]diazatetracyclo[13.7.2.0$^{3,6}$.0$^{19,24}$]tetracosa [8,15,17,23]tetraen]-14'-one 12',12'-dioxide The title compound was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12) by a procedure analogous to that described in Example 611, Steps 2 and 3, replacing (S)-2-(N,N-bis(4-methoxybenzyl)sulfamoyl)hex-5-en-1-yl carbamate in Step 2 with (S)—N,N-bis(4-methoxybenzyl)-1-phenylpent-4-ene-2-sulfonamide and (R)—N,N-bis(4-methoxybenzyl)-1-phenylpent-4-ene-2-sulfonamide (Example 646, Steps 1). The crude product was purified by combi-flash (4 g ISCO Gold column), eluting with 20% to 60% EtOAc (containing 0.3% AcOH)/hexanes to give one of the title compounds as a white foam. $^1$H NMR (500 MHz, CDCl$_3$) δ ppm 8.21 (br. s., 1H), 7.70 (d, J=8.6 Hz, 1H), 7.38-7.33 (m, 2H), 7.32-7.25 (m, 4H), 7.21-7.15 (m, 1H), 7.09 (d, J=2.2 Hz, 1H), 7.03-6.96 (m, 1H), 6.71 (m, 1H), 5.90-5.76 (m, 2H), 4.18-4.08 (m, 3H), 4.06-3.94 (m, 1H), 3.74-3.62 (m, 3H), 3.30 (d, J=14.4 Hz, 1H), 3.23-3.12 (m, 1H), 2.90 (dd, J=11.7, 13.4 Hz, 1H), 2.84-2.71 (m, 3H), 2.63-2.44 (m, 3H), 2.43-2.32 (m, 1H), 2.26-1.88 (m, 3H), 1.88-1.70 (m, 3H), 1.70-1.57 (m, 1H), 1.45 (t, J=12.5 Hz, 1H); m/z (ESI, +ve ion) 647.2 (M+H)$^+$.

Example 647. methyl ((1S,3'R,6'R,7'S,8'E,11'S,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate or methyl ((1S,3'R,6'R,7'S,8'E,11'R,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate or methyl ((1S,3'R,6'R,7'S,8'E,11'R,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate or methyl ((1S,3'R,6'R,7'S,8'E,11'S,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate

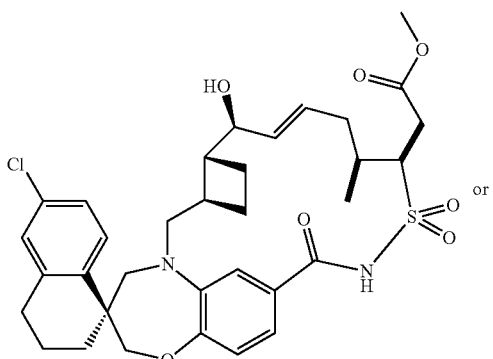

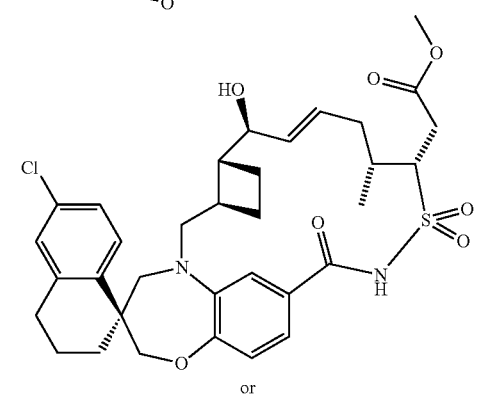

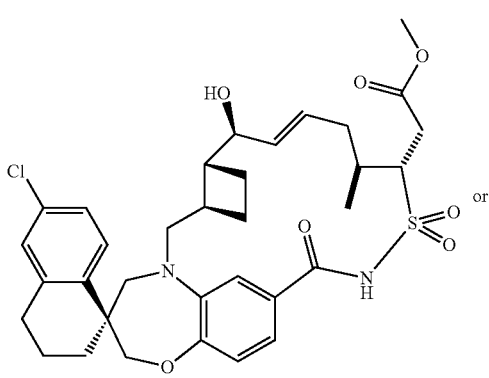

-continued

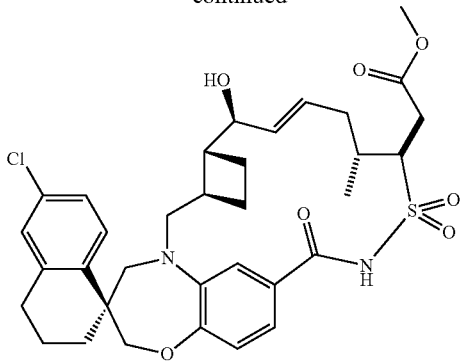

Step 1: (R)-2-methylpent-4-en-1-ol and (S)-2-methylpent-4-en-1-ol

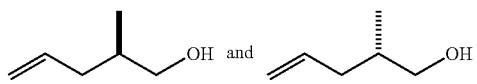

To a solution of (R)-2-methyl-4-pentenoic acid and (S)-2-methyl-4-pentenoic acid (22.8 mL, 200 mmol) in THF (300 mL) was added LiAlH$_4$ (1.0 M in THF, 200 mL, 200 mmol) at 0° C. dropwise and the resulting solution was allowed to warm to ambient temperature. After the reaction mixture was stirred at ambient temperature for 18 h, the reaction mixture was cooled to 0° C. and cautiously treated with water (7.6 mL), 15% aqueous solution of NaOH (7.6 mL), and water (22.8 mL) successively. After the resulting slurry was vigorously stirred for 1 h at ambient temperature, the suspension was filtered through Celite and the filter cake was washed with diethyl ether (2×100 mL). The combined filterate were dried (Na$_2$SO$_4$) and concentrated under reduced pressure to provide crude title compounds as a colorless liquid which were directly engaged in the next step without further purification.

Step 2: (R)-2-methylpent-4-en-1-yl methanesulfonate and (S)-2-methylpent-4-en-1-yl methanesulfonate

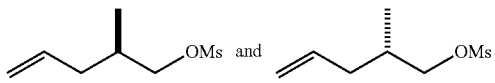

To a solution of (R)-2-methylpent-4-en-1-ol and (S)-2-methylpent-4-en-1-ol (Example 647, Step 1) (18.8 g, 188 mmol) and triethylamine (52.2 ml, 375 mmol) in Et$_2$O (300 mL) was added MsCl (16.0 mL, 206 mmol) at −78° C. After the reaction mixture was stirred for 20 min at the same temperature, the reaction was allowed to warm to ambient temperature and stirred for 30 min. Then the mixture was diluted (water), extracted (2×Et$_2$O), and washed (ice-cold 1 N aqueous HCl, water, saturated aqueous NaHCO$_3$, and water). The combined organic layers were dried (MgSO$_4$) and concentrated under reduced pressure to provide crude title compounds, which were used for next step without further purification.

Step 3: (R)-2-((2-methylpent-4-en-1-yl)thio)pyrimidine and (S)-2-((2-methylpent-4-en-1-yl)thio)pyrimidine

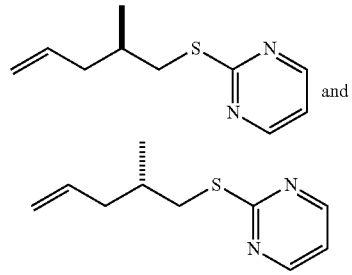

To a solution of (R)-2-methylpent-4-en-1-yl methanesulfonate and (S)-2-methylpent-4-en-1-yl methanesulfonate (Example 647, Step 2) (30.3 g, 170 mmol) and 2-mercaptopyrimidine (28.6 g, 255 mmol) in EtOH (240 mL) was added EtONa (21% w/w solution in EtOH, 82.0 mL, 221 mmol) at ambient temperature and the resulting mixture was stirred at 60° C. for 17 h. The reaction mixture was concentrated under reduced pressure and the resulting pale yellow solid was suspended in Et$_2$O (400 mL). After the suspension was stirred vigorously for 1 h, the slurry was filtered through Celite and the filter cake was washed (Et$_2$O). The combined filtrates were dried (Na$_2$SO$_4$) and concentrated under reduced pressure to provide crude title compounds, which were directly engaged in the next step without further purification.

Step 4: (R)-2-((2-methylpent-4-en-1-yl)sulfonyl)pyrimidine and (S)-2-((2-methylpent-4-en-1-yl)sulfonyl)pyrimidine

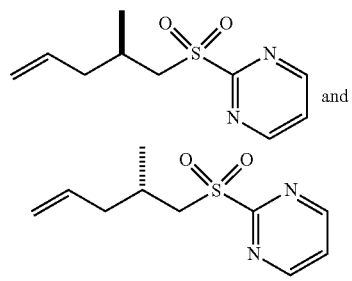

To a solution of (R)-2-((2-methylpent-4-en-1-yl)thio)pyrimidine and (S)-2-((2-methylpent-4-en-1-yl)thio)pyrimidine (Example 647, Step 3) (32.4 g, 167 mmol) in DCM (240 mL) was added 3-chloroperbenzoic acid (77% max, 78.0 g, 350 mmol) at 0° C. The reaction was allowed to warm to ambient temperature and stirred for 1 h. The mixture was filtered through Celite and the filter cake was washed (DCM). The combined filtrates were washed (saturated aqueous NaHCO$_3$ and brine), dried (Na$_2$SO$_4$), and concentrated under reduced pressure. The residue was injected into a 330 g ISCO Gold column and purified by combi-flash, eluting with 20% to 80% EtOAc/hexanes to give the title compounds (28.9 g, 128 mmol) as a colorless liquid.

Step 5: Sodium (R)-2-methylpent-4-ene-1-sulfinate and Sodium (S)-2-methylpent-4-ene-1-sulfinate

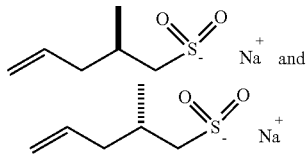

A solution of (R)-2-((2-methylpent-4-en-1-yl)sulfonyl)pyrimidine and (S)-2-((2-methylpent-4-en-1-yl)sulfonyl)pyrimidine (Example 647, Step 4) (28.9 g, 128 mmol) in MeOH (430 mL) was treated with MeONa (25 wt. % solution in MeOH, 29.2 mL, 128 mmol) at ambient temperature and the resulting solution was stirred for 3 h. The reaction was concentrated under reduced pressure and the residue was triturated with Et$_2$O. The slurry was filtered though filter paper and the filter cake was rinsed with hexanes to provide crude products (21.7 g, 128 mmol) as a pale yellow solid, which were used for next step without any further purification.

Step 6: (R)-2-methylpent-4-ene-1-sulfonamide and (S)-2-methylpent-4-ene-1-sulfonamide

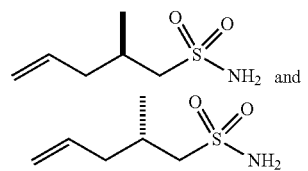

To a solution of sodium (R)-2-methylpent-4-ene-1-sulfinate and sodium (S)-2-methylpent-4-ene-1-sulfinate (Example 647, Step 5) (21.7 g, 128 mmol) in water (511 mL) was added potassium acetate (12.5 g, 128 mmol) and hydroxylamine-o-sulfonic acid (28.9 g, 255 mmol) successively at ambient temperature. Then the reaction was heated to 50° C. for 2 h. The reaction mixture was cooled to ambient temperature and stirred overnight. The reaction was extracted (2×15% iPA/DCM) and washed (brine). The combined organic layers were dried (Na$_2$SO$_4$) and concentrated under reduced pressure to provide the title compounds (19.5 g, 119 mmol) as colorless oil, which were used for next step without further purification.

Step 7: (R)—N,N-bis(4-methoxybenzyl)-2-methylpent-4-ene-1-sulfonamide and (S)—N,N-bis(4-methoxybenzyl)-2-methylpent-4-ene-1-sulfonamide

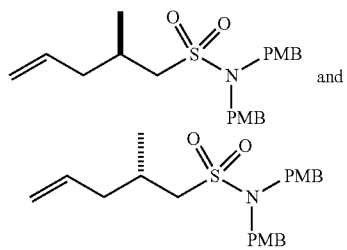

To a solution of (R)-2-methylpent-4-ene-1-sulfonamide and (S)-2-methylpent-4-ene-1-sulfonamide (Example 647, Step 6) (19.5 g, 119 mmol) in 2-butanone (600 mL) were added KI (1.98 g, 11.9 mmol), anhydrous K$_2$CO$_3$ (66.0 g, 478 mmol), and PMBCl (40.5 mL, 299 mmol) successively and the resulting solution was stirred at 80° C. overnight. The reaction was cooled to ambient temperature and filtered through Celite to remove inorganic solids. The filter cake was washed with DCM and the combined filtrates were concentrated. The residue was injected into a 330 g ISCO Gold column and purified by combi-flash, eluting with 0% to 25% EtOAc/hexanes to give the title compounds (39.7 g, 98.0 mmol) as a colorless oil.

Step 8: (3R,4R)-1-hydroxy-N,N-bis(4-methoxybenzyl)-4-methylhept-6-ene-3-sulfonamide and (3S,4S)-1-hydroxy-N,N-bis(4-methoxybenzyl)-4-methylhept-6-ene-3-sulfonamide and (3R,4S)-1-hydroxy-N,N-bis(4-methoxybenzyl)-4-methylhept-6-ene-3-sulfonamide and (3S,4R)-1-hydroxy-N,N-bis(4-methoxybenzyl)-4-methylhept-6-ene-3-sulfonamide

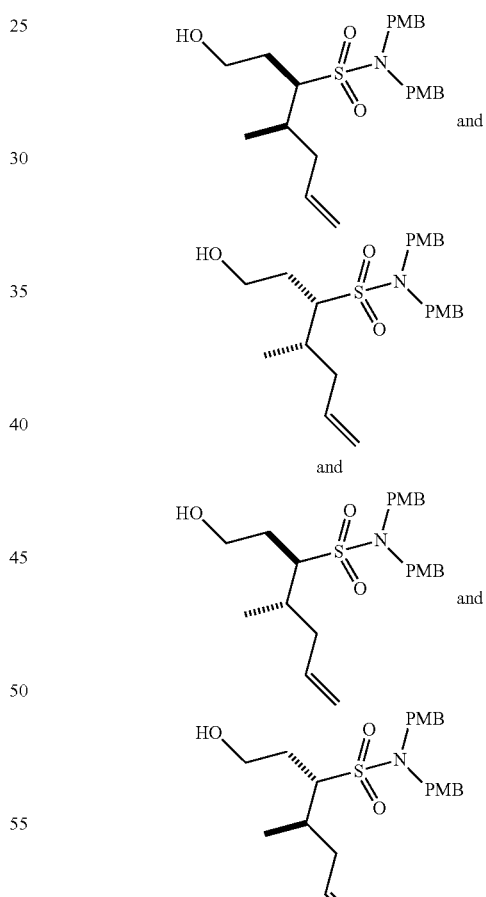

To a solution of (R)—N,N-bis(4-methoxybenzyl)-2-methylpent-4-ene-1-sulfonamide and (S)—N,N-bis(4-methoxybenzyl)-2-methylpent-4-ene-1-sulfonamide (Example 647, Step 7) (4.50 g, 11.1 mmol) in THF (25 mL) was added n-BuLi (2.5 M solution in hexanes, 4.68 mL, 11.7 mmol) at −78° C. dropwise. After the reaction mixture was stirred at −78° C. for 25 min, excess ethylene oxide was bubbled into the reaction for 15 min at the same temp. The reaction was allowed to warm to ambient temperature and stirred overnight. The reaction was quenched (sat. aqueous NH₄Cl), extracted (2×EtOAc), and washed (brine). The combined organic layers were dried (Na₂SO₄) and concentrated under reduced pressure. The residue was injected into a 80 g ISCO Gold column and purified by combi-flash, eluting with 20% to 60% EtOAc/hexanes to provide the products (4.00 g, 8.94 mmol) (dr=2:3) as a colorless oil.

Step 9: (3R,4R)-3-(N,N-bis(4-methoxybenzyl)sulfamoyl)-4-methylhept-6-enoic Acid and (3S,4S)-3-(N,N-bis(4-methoxybenzyl)sulfamoyl)-4-methylhept-6-enoic Acid and (3R,4S)-3-(N,N-bis(4-methoxybenzyl)sulfamoyl)-4-methylhept-6-enoic Acid and (3S,4R)-3-(N,N-bis(4-methoxybenzyl)sulfamoyl)-4-methylhept-6-enoic Acid

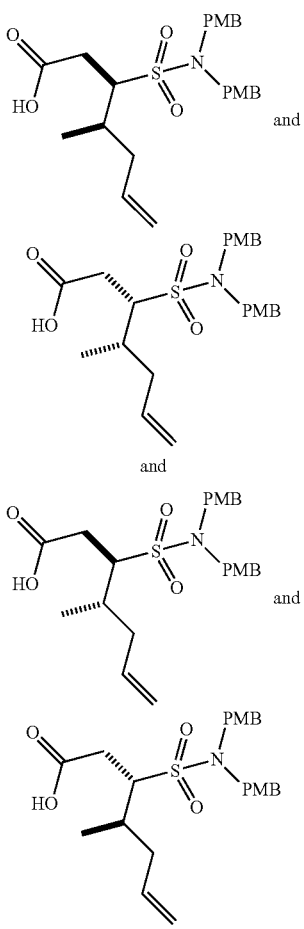

vigorously stirred at the same temp for 1h. The reaction was concentrated under reduced pressure (water bath <10° C.), diluted (EtOAc and ice-cold 1N aqueous HCl), extracted (2×EtOAc), and washed (brine). The combined organic layers were dried (Na₂SO₄) and concentrated under reduced pressure. The residue was injected into a 80 g ISCO Gold column and purified by combi-flash, eluting with 25% to 100% EtOAc/hexanes to provide the title compounds (1.90 g, 4.12 mmol) as a colorless syrup.

Step 10: (3R,4R)-methyl-3-(N,N-bis(4-methoxybenzyl)sulfamoyl)-4-methylhept-6-enoic Acid and (3S,4S)-methyl-3-(N,N-bis(4-methoxybenzyl)sulfamoyl)-4-methylhept-6-enoic Acid and (3R,4S)-methyl-3-(N,N-bis(4-methoxybenzyl)sulfamoyl)-4-methylhept-6-enoic Acid and (3S,4R)-methyl-3-(N,N-bis(4-methoxybenzyl)sulfamoyl)-4-methylhept-6-enoic Acid

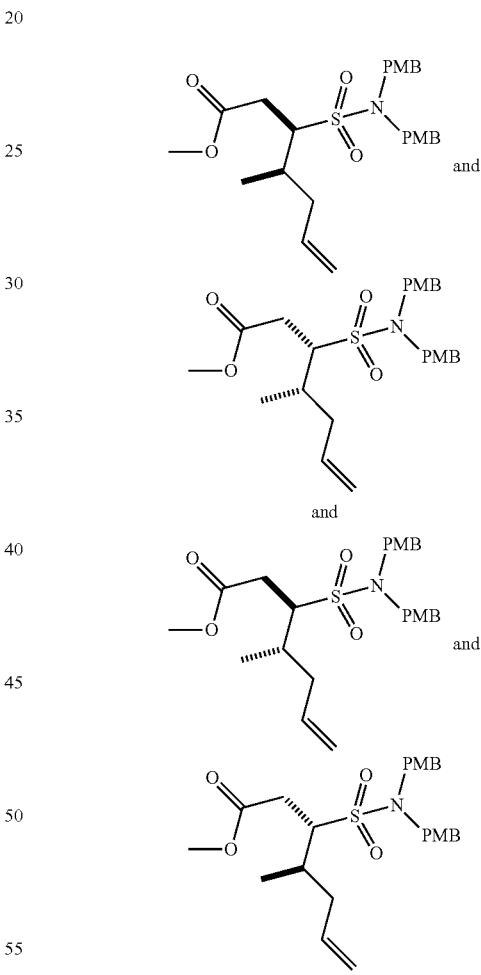

To a solution of (3R,4R)-1-hydroxy-N,N-bis(4-methoxybenzyl)-4-methylhept-6-ene-3-sulfonamide and (3S,4S)-1-hydroxy-N,N-bis(4-methoxybenzyl)-4-methylhept-6-ene-3-sulfonamide and (3R,4S)-1-hydroxy-N,N-bis(4-methoxybenzyl)-4-methylhept-6-ene-3-sulfonamide and (3S,4R)-1-hydroxy-N,N-bis(4-methoxybenzyl)-4-methylhept-6-ene-3-sulfonamide (Example 647, Step 8) (4.00 g, 8.94 mmol), KBr (0.106 g, 0.894 mmol), NaHCO₃ (5% w/w in water, 42.0 mL, 25.0 mmol), TEMPO (1.54 g, 9.83 mmol) in acetone (89 mL) was added NaClO (6% w/w in water, 12.2 mL, 9.83 mmol) at 0° C. and the resulting reaction was To a solution of (3R,4R)-3-(N,N-bis(4-methoxybenzyl)sulfamoyl)-4-methylhept-6-enoic acid and (3S,4S)-3-(N,N-bis(4-methoxybenzyl)sulfamoyl)-4-methylhept-6-enoic acid and (3R,4S)-3-(N,N-bis(4-methoxybenzyl)sulfamoyl)-4-methylhept-6-enoic acid and (3S,4R)-3-(N,N-bis(4-methoxybenzyl)sulfamoyl)-4-methylhept-6-enoic acid (Example 647, Step 9) (595 mg, 1.29 mmol) in MeOH (6.4 mL) was added SOCl₂ (188 μL, 2.58 mmol) at 0° C. dropwise. Then the reaction was allowed to warm to ambient temperature. The reaction was diluted (EtOAc and ice-cold water), extracted (2×EtOAc), and washed (saturated aqueous NaHCO$_3$ and brine). The combined organic layers were dried (Na$_2$SO$_4$) and concentrated under reduced pressure to provide crude products, which were used for next step without any further purification.

Step 11: methyl ((1S,3'R,6'R,7'S,8'E,11'S,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate or methyl ((1S,3'R,6'R,7'S,8'E,11'R,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate or methyl ((1S,3'R,6'R,7'S,8'E,11'R,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate or methyl ((1S,3'R,6'R,7'S,8'E,11'S,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)acetate One of the title compounds was prepared from (S)-6'-chloro-5-(((1R,2R)-2-((S,E)-1-hydroxyhex-2-en-1-yl)cyclobutyl)methyl)-3',4',5-tetrahydro-2H,2'H-spiro[benzo[b][1,4]oxazepine-3,1'-naphthalene]-7-carboxylic acid (Intermediate AA12A) by a procedure analogous to that described in Example 571, Step 7 through 9, replacing (3R,4S)-4-methoxy-N,N-bis(4-methoxybenzyl)-2-methylhept-6-ene-3-sulfonamide and (3S,4R)-4-methoxy-N,N-bis(4-methoxybenzyl)-2-methylhept-6-ene-3-sulfonamide] or [(3R,4R)-4-methoxy-N,N-bis(4-methoxybenzyl)-2-methylhept-6-ene-3-sulfonamide and (3S,4S)-4-methoxy-N,N-bis(4-methoxybenzyl)-2-methylhept-6-ene-3-sulfonamide in Step 7 with (3R,4R)-methyl-3-(N,N-bis(4-methoxybenzyl)sulfamoyl)-4-methylhept-6-enoic acid and (3S,4S)-methyl-3-(N,N-bis(4-methoxybenzyl)sulfamoyl)-4-methylhept-6-enoic acid and (3R,4S)-methyl-3-(N,N-bis(4-methoxybenzyl)sulfamoyl)-4-methylhept-6-enoic acid and (3S,4R)-methyl-3-(N,N-bis(4-methoxybenzyl)sulfamoyl)-4-methylhept-6-enoic acid (Example 647, Step 10). The crude products were purified by reversed phase preparatory HPLC (Gemini™ Prep C$_{18}$ 5 µm column; Phenomenex, Torrance, CA; gradient elution of 45% to 70% MeCN in water, where both solvents contain 0.1% TFA, 30 min method) to provide one of the title compound as the fastest eluting isomer as a white foam. $^1$H NMR (500 MHz, CDCl$_3$) δ ppm 7.97 (br, s, 1H), 7.70 (d, J=8.4 Hz, 1H), 7.19 (dd, J=8.31, 2.20 Hz, 1H), 7.10 (d, J=2.20 Hz, 1H), 7.04 (d, J=15.41 Hz, 1H), 6.98-6.87 (m, 2H), 6.04-5.98 (m, 1H), 5.73 (dd, J=15.04, 7.95 Hz, 1H), 4.86 (br. s., 1H), 4.25 (dd, J=6.72, 4.77 Hz, 1H), 4.15-4.04 (m, 2H), 3.88-3.71 (m, 4H), 3.71-3.58 (m, 1H), 3.29 (d, J=14.67 Hz, 1H), 3.07 (dd, J=16.87, 7.58 Hz, 1H), 2.84-2.63 (m, 3H), 2.52-2.39 (m, 1H), 2.33 (t, J=8.80 Hz, 1H), 2.15-2.07 (m, 2H), 2.06-1.64 (m, 9H), 1.44 (t, J=12.72 Hz, 1H), 1.09 (d, J=6.60 Hz, 3H); m/z (ESI, +ve ion) 657.2 (M+H)$^+$.

Example 648. (1S,3'R,6'R,7'S,8'E,11'S,12'R)-12'-benzyl-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-12'-benzyl-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-12'-benzyl-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-12'-benzyl-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Isomer 1)

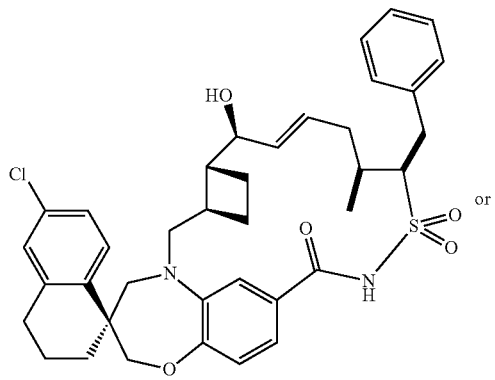

or

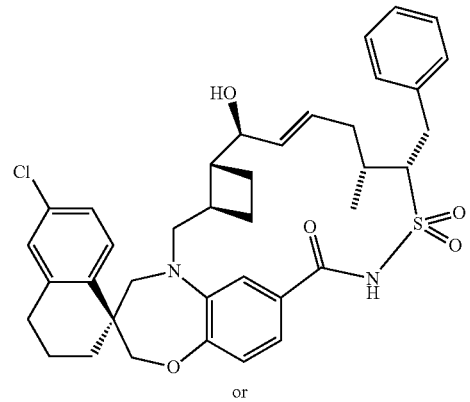

or

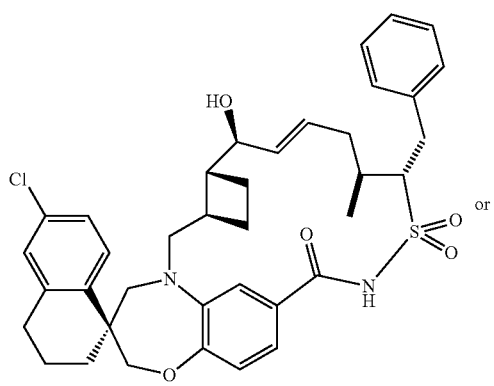

-continued

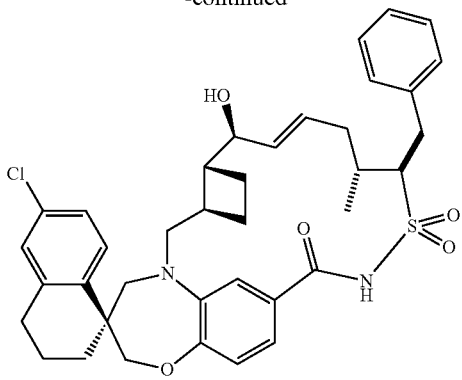

Step 1. (3R,4R)—N,N-bis(4-methoxybenzyl)-3-methyl-1-phenylhex-5-ene-2-sulfonamide and (3S,4S)—N,N-bis(4-methoxybenzyl)-3-methyl-1-phenylhex-5-ene-2-sulfonamide and (3S,4R)—N,N-bis(4-methoxybenzyl)-3-methyl-1-phenylhex-5-ene-2-sulfonamide and (3R,4S)—N,N-bis(4-methoxybenzyl)-3-methyl-1-phenylhex-5-ene-2-sulfonamide

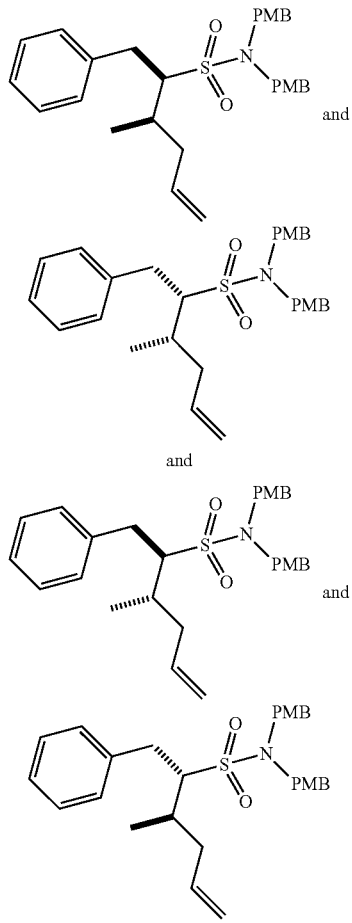

To a solution of (R)—N,N-bis(4-methoxybenzyl)-2-methylpent-4-ene-1-sulfonamide and (S)—N,N-bis(4-methoxybenzyl)-2-methylpent-4-ene-1-sulfonamide (Example 647, Steps 7) (796 mg, 1.97 mmol) in THF (6.5 mL) was added n-BuLi (2.5 M solution in hexanes, 0.79 mL, 1.97 mmol) at −78° C. After the reaction was stirred at the same temperature for 15 min, a solution of benzyl bromide (0.468 mL, 3.95 mmol) in THF (2.5 mL) was added and the resulting solution was stirred −78° C. for 1 h. Then the reaction was allowed to warm to ambient temperature and stirred overnight. The reaction was quenched (saturated aqueous NH$_4$Cl), extracted (2×EtOAc), and washed (brine). The combined organic layers were dried (Na$_2$SO$_4$) and concentrated under reduced pressure. The residue was injected into a 24 g ISCO Gold column and purified by combi-flash, eluting with 0% to 20% EtOAc/hexanes to provide the title compounds (859 mg, 1.74 mmol) as a colorless liquid.

Step 2. (1S,3'R,6'R,7'S,8'E,11'S,12'R)-12'-benzyl-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-12'-benzyl-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-12'-benzyl-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-12'-benzyl-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Isomer 1)

One of the title compounds was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A) by a procedure analogous to that described in Example 571, Step 7 through 9, replacing (3R,4S)-4-methoxy-N,N-bis(4-methoxybenzyl)-2-methylhept-6-ene-3-sulfonamide and (3S,4R)-4-methoxy-N,N-bis(4-methoxybenzyl)-2-methylhept-6-ene-3-sulfonamide] or [(3R,4R)-4-methoxy-N,N-bis(4-methoxybenzyl)-2-methylhept-6-ene-3-sulfonamide and (3S,4S)-4-methoxy-N,N-bis(4-methoxybenzyl)-2-methylhept-6-ene-3-sulfonamide in Step 7 with (3R,4R)—N,N-bis(4-methoxybenzyl)-3-methyl-1-phenylhex-5-ene-2-sulfonamide and (3S,4S)—N,N-bis(4-methoxybenzyl)-3-methyl-1-phenylhex-5-ene-2-sulfonamide and (3S,4R)—N,N-bis(4-methoxybenzyl)-3-methyl-1-phenylhex-5-ene-2-sulfonamide and (3R,4S)—N,N-bis(4-methoxybenzyl)-3-methyl-1-phenylhex-5-ene-2-sulfonamide (Example 648, Step 1). The crude product was purified by reversed phase preparatory HPLC (Gemini™ Prep C$_{18}$ 5 μm column; Phenomenex, Torrance, CA; gradient elution of 50% to 80% MeCN in water, where both solvents contain 0.1% TFA, 30 min method) to provide a mixture as the faster eluting peak, which was further purified by chiral Thar 80 SFC (IC 30×250 mm column, Phenomenex, Torrance, CA; using 40 g/min MeOH (20 mM ammonia)+40 g/min CO$_2$, 50% co-solvent at 80 g/min, isocratic.) to provide one of the title compounds as the faster eluting isomer. $^1$H NMR (400 MHz, CDCl$_3$) δ ppm 7.59 (d, J=8.61 Hz, 1H), 7.24-6.97 (m, 9H), 6.87-6.74 (m, 1H), 5.70 (m, 1H), 5.60-5.39 (m, 1H), 4.41 (m, 1H), 4.06 (m, 3H), 3.57-3.19 (m, 3H), 2.95 (m, 1H), 2.69 (m, 2H), 2.37-2.28 (m, 2H), 1.90-1.52 (m, 13H), 1.17-1.04 (m, 3H); m/z (ESI, +ve ion) 675.2 (M+H)+.

Example 649. (1S,3'R,6'R,7'S,8'E,11'S,12'R)-12'-benzyl-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-12'-benzyl-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-12'-benzyl-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-12'-benzyl-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Isomer 2)

-continued

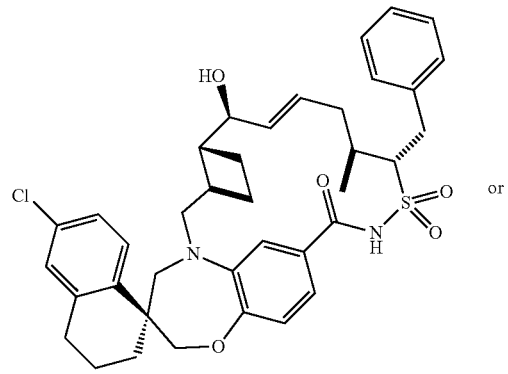

or

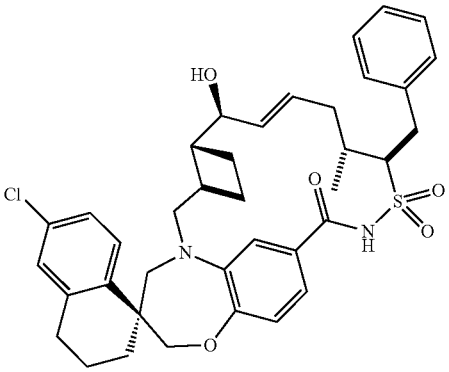

or

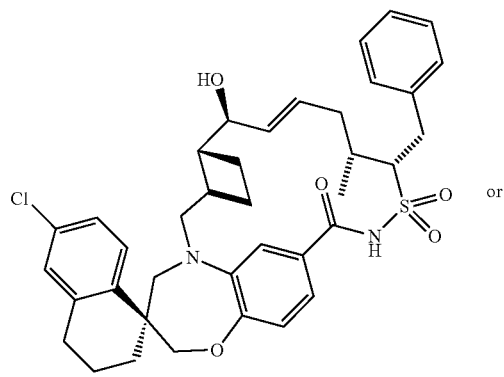

or

One of the title compounds was obtained as the second (slower) eluting isomer from chiral SFC in Example 648. $^1$H NMR (500 MHz, CDCl$_3$) δ ppm 8.55 (br. s., 1H), 7.74-7.64 (m, 1H), 7.36-7.31 (m, 4H), 7.26-7.23 (m, 1H), 7.21-7.14 (m, 2H), 7.09 (d, J=2.2 Hz, 1H), 6.96 (d, J=8.1 Hz, 1H), 6.72 (m, 1H), 6.01 (m, 1H), 5.72-5.55 (m, 1H), 4.20-3.99 (m, 3H), 3.76-3.55 (m, 3H), 3.49-3.34 (m, 1H), 3.06 (dd, J=7.6, 14.9 Hz, 1H), 2.84-2.68 (m, 2H), 2.63 (br. s., 1H), 2.50 (m, 1H), 2.32-2.18 (m, 2H), 2.11 (s, 3H), 2.08-1.55 (m, 9H), 1.52-1.43 (m, 1H), 1.05 (d, J=6.4 Hz, 1H); m/z (ESI, +ve ion) 675.2 (M+H)+.

Example 650. (1S,3'R,6'R,7'S,9'Z,11'S,12'R)-6-chloro-12'-(cyclopropylmethyl)-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide or (1S,3'R,6'R,7'S,9'Z,11'R,12'S)-6-chloro-12'-(cyclopropylmethyl)-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide or (1S,3'R,6'R,7'S,9'Z,11'R,12'R)-6-chloro-12'-(cyclopropylmethyl)-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide or (1S,3'R,6'R,7'S,9'Z,11'S,12'S)-6-chloro-12'-(cyclopropylmethyl)-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide


or

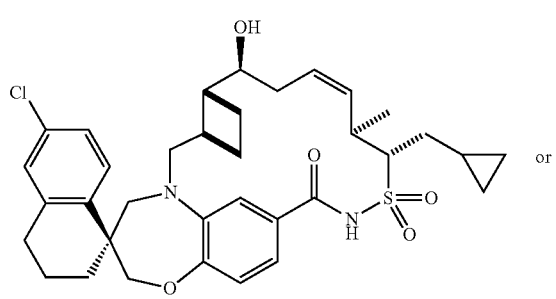

or

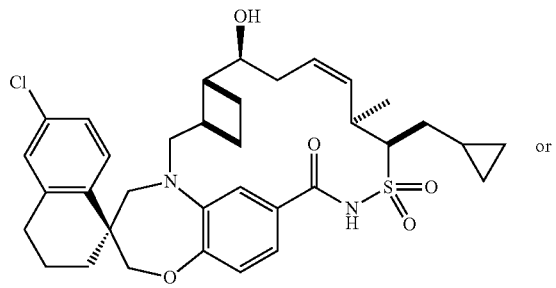

or

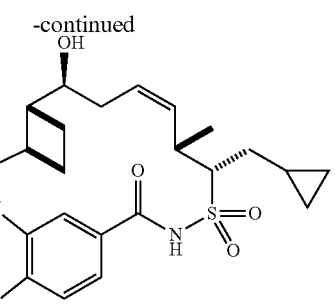

One of the title compounds was obtained as the second (slower) eluting isomer from reversed phase preparatory HPLC in Example 380. $^1$H NMR (500 MHz, CDCl$_3$) δ ppm 7.72 (d, J=8.3 Hz, 1H), 7.31-7.25 (m, 1H), 7.23-7.15 (m, 1H), 7.10 (d, J=2.2 Hz, 1H), 7.00-6.89 (m, 1H), 6.84 (m, 1H), 6.11 (m, 1H), 5.81 (m, 1H), 4.38-4.19 (m, 1H), 4.19-4.03 (m, 2H), 3.85-3.63 (m, 3H), 3.35-3.10 (m, 2H), 2.92-2.72 (m, 3H), 2.52-2.30 (m, 2H), 2.27-1.76 (m, 9H), 1.75-1.57 (m, 2H), 1.47 (m, 1H), 1.20-1.04 (m, 4H), 0.66-0.55 (m, 2H), 0.26 (m, 1H), 0.18-0.05 (m, 1H).

Example 651. (1S,3'R,6'R,7'S,8'E,12'S)-6-chloro-12'-((2R)-2-hydroxy-3-methoxypropyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide or (1S,3'R,6'R,7'S,8'E,12'R)-6-chloro-12'-((2R)-2-hydroxy-3-methoxypropyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide

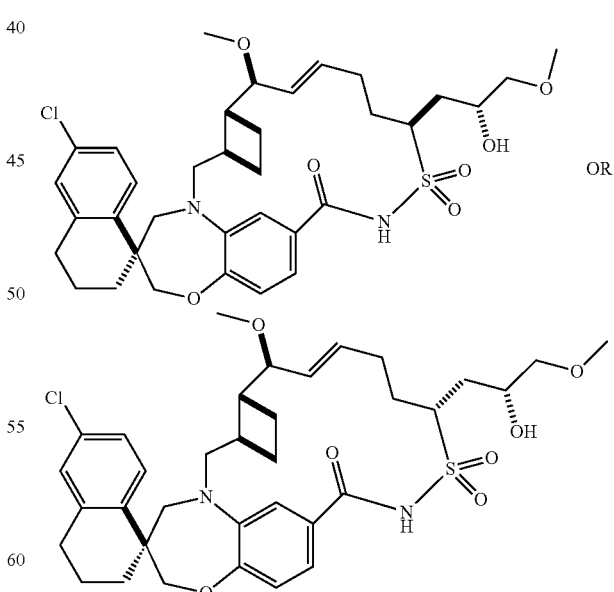

Step 1: (S)-6'-chloro-5-(((1R,2R)-2-((S,E)-1-hydroxy-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic Acid

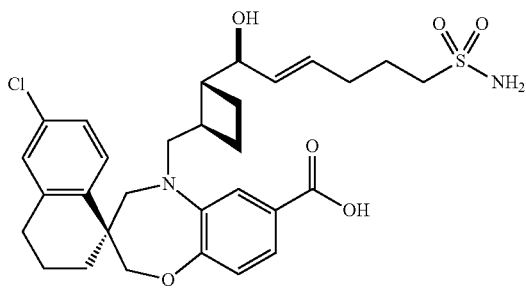

To a 100 mL flask was added (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A; 500 mg, 0.980 mmol), pent-4-ene-1-sulfonamide (Intermediate EE19; 878 mg, 5.88 mmol), and DCE (14 mL). The solution was sparged with argon for 15 min at which time Hoveyda-Grubbs II (61.4 mg, 0.098 mmol) was added as a 0.2 mL solution in DCE at rt. The mixture was stirred at rt and sparged with argon (the vial was vented) for 2 h. The reaction mixture was then bubbled with air for 5 minutes and filtered to separate the insoluble sulfonamide homodimer. The crude product was purified on a Combiflash® (24 g gold SiO$_2$ column), eluting with 50%-90% EtOAc in heptanes+ 0.2% AcOH) to give (S)-6'-chloro-5-(((1R,2R)-2-((S,E)-1-hydroxy-6-sulfamoylhex-2-en-1-yl)cyclobutyl)methyl)-3',4,4',5-tetrahydro-2h,2'h-spiro[benzo[b][1,4]oxazepine-3,1'-naphthalene]-7-carboxylic acid (439 mg, 0.745 mmol, 76% yield) as a white solid.

Step 2: (1S,3'R,6'R,7'S,8'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

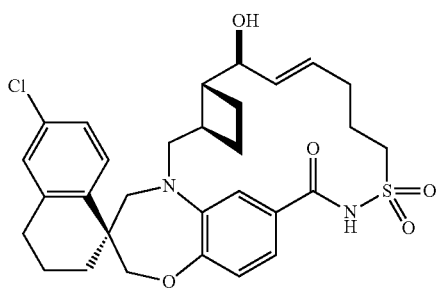

To a 1 L flask containing (S)-6'-chloro-5-(((1R,2R)-2-((S,E)-1-hydroxy-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic acid (from Step 1, 439 mg, 0.745 mmol), which was previously dried by azeotroping twice with 10 mL of toluene, was added N,N-dimethylpyridin-4-amine (155 mg, 1.27 mmol) and 400 mL of DCM. The reaction mixture was cooled to 0° C. at which time N-(3-dimethylaminopropyl)-N'-ethylcarbodiimide hydrochloride (286 mg, 1.49 mmol) was slowly added. The reaction was then stirred at rt for 18 h. The mixture was quenched with 200 mL of 1N HCl and extracted with 600 mL of EtOAc. The organic layer was dried over anhydrous Na$_2$SO$_4$, filtered, and concentrated by rotary evaporation. The crude product was purified on a Combiflash® (24 g gold SiO$_2$ column), eluting with 30%-70% EtOAc in heptanes, to give (1S,3'R,6'R,7'S,8'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide a white solid. $^1$H NMR (500 MHz, CD$_3$OD) δ 7.75 (d, J=8.3 Hz, 1H), 7.20 (dd, J=2.9, 7.6 Hz, 1H), 7.12 (d, J=3.7 Hz, 1H), 7.00 (dd, J=1.7, 8.8 Hz, 1H), 6.94 (d, J=8.3 Hz, 1H), 6.88 (d, J=2.2 Hz, 1H), 5.95-5.86 (m, 1H), 5.70 (dd, J=8.8, 15.9 Hz, 1H), 4.25-4.19 (m, 1H), 4.22 (dd, J=4.4, 8.6 Hz, 1H), 4.14-4.06 (m, 3H), 4.14-4.05 (m, 3H), 3.84 (d, J=15.2 Hz, 1H), 3.68 (d, J=15.2 Hz, 1H), 3.09 (dd, J=8.3, 15.9 Hz, 1H), 2.87-2.74 (m, 2H), 2.45-2.30 (m, 3H), 2.14-1.88 (m, 5H), 1.86-1.69 (m, 4H). m/z (ESI, +ve ion) 571.2 (M+H)$^+$.

Step:3 (1S,3'R,6'R,7'S,8'E)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

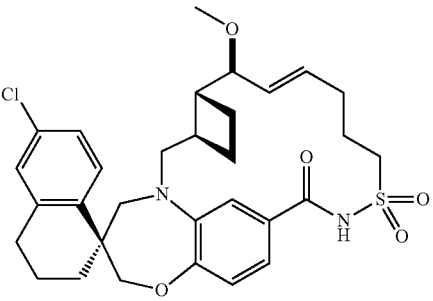

To a 100 mL flask was added (1S,3'R,6'R,7'S,8'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Step 2, 138 mg, 0.242 mmol), THF (10 mL), and sodium hydride (29.0 mg, 1.208 mmol). The reaction was stirred at rt for 15 min at which time MeI (0.092 mL, 1.480 mmol) was added. The reaction was stirred at rt for 2 h at which time additional sodium hydride (58.0 mg, 2.42 mmol) and MeI (0.092 mL, 1.480 mmol) were added and the reaction was stirred at rt for an additional 16 h. The reaction was quenched with 100 mL of satd NH$_4$Cl and extracted with 400 mL of EtOAc. The organic layer was dried over Na$_2$SO$_4$, filtered, and the solvent was removed by rotary evaporation. The crude product was purified on a Combiflash® (12 g gold SiO$_2$ column), eluting with 10% to 50% EtOAc in heptanes, to give (1S,3'R,6'R,7'S,8'E)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (120 mg, 0.205 mmol, 85% yield) as an off white solid. $^1$H NMR (400 MHz, CDCl$_3$) δ 8.02 (s, 1H), 7.70 (d, J=8.6 Hz, 1H), 7.19 (dd, J=2.2, 8.5 Hz, 1H), 7.10 (d, J=2.2 Hz, 1H), 6.97-6.87 (m, 2H), 6.84 (d, J=1.6 Hz, 1H), 5.88 (ddd, J=5.2, 8.1, 15.1 Hz, 1H), 5.53 (dd, J=8.7, 15.4 Hz, 1H), 4.30 (ddd, J=4.8, 9.8, 15.0 Hz, 1H), 4.15-3.98 (m, 2H), 3.84-3.69 (m, 2H), 3.67 (dd, J=3.8, 8.7 Hz, 1H), 3.36-3.21 (m, 2H), 3.25 (s, 3H), 3.01 (dd, J=10.3, 15.2 Hz, 1H), 2.87-2.64 (m, 2H), 2.52-2.29 (m, 3H), 2.25-1.91 (m, 5H), 1.88-1.75 (m, 3H), 1.71-1.60 (m, 2H), 1.41 (t, J=12.4 Hz, 1H). m/z (ESI, +ve ion) 585.0 (M+H)$^+$.

Step 4: (1S,3'R,6'R,7'S,8'E,12'S)-6-chloro-12'-((2R)-2-hydroxy-3-methoxypropyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-12'-((2R)-2-hydroxy-3-methoxypropyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide To a solution of (1S,3'R,6'R,7'S,8'E)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (from Step 3, 42 mg, 0.072 mmol) in THF (2 mL) under Ar in −50° C. bath was added "BuLi (0.201 mL, 2.5 M in hexanes, 0.502 mmol, Sigma-Aldrich Chemical Company, Inc.). The solution was allowed to stir in the −50° C. bath for 30 min. To the mixture was added (R)-(−)-glycidyl methyl ether (0.202 mL, 2.297 mmol, 97%, Sigma-Aldrich), the resultant mixture was allowed to warm with the bath to 0° C. over 45 min. To the reaction mixture was added saturated aqueous NH$_4$Cl (1.0 mL), the resulting mixture was diluted with water (3 mL) and extracted with EtOAc (3×5 mL). The organic layers were combined. After removal of organic solvents under reduced pressure, the residue was re-dissolved in DMSO (2 mL) and subjected to reverse phase preparatory HPLC (Gemini™ Prep C18 5 μm column; Phenomenex, Torrance, CA; gradient elution of 10% MeCN in water to 90% MeCN in water over a 20 min period, where both solvents contain 0.1% TFA) to provide one of the title compounds as the first eluting fraction as a white foam. $^1$H NMR (400 MHz, CDCl$_3$) δ 8.03 (s, 1H), 7.63-7.76 (m, 1H), 7.19 (dd, J=8.51, 2.05 Hz, 1H), 7.10 (s, 1H), 6.81-6.97 (m, 2H), 5.82-5.96 (m, 1H), 5.53 (dd, J=15.16, 9.10 Hz, 1H), 4.49 (d, J=9.59 Hz, 1H), 4.25-4.37 (m, 1H), 3.99-4.17 (m, 2H), 3.56-3.89 (m, 3H), 3.50 (dd, J=9.59, 3.52 Hz, 1H), 3.33-3.46 (m, 4H), 3.18-3.33 (m, 3H), 2.90-3.08 (m, 1H), 2.66-2.88 (m, 2H), 2.15-2.55 (m, 5H), 1.54-2.12 (m, 10H), 1.20-1.47 (m, 3H). m/z (ESI, +ve ion) 673.1 (M+H)$^+$.

Example 652. (1S,3'R,6'R,7'S,8'E,12'S)-6-chloro-12'-((2R)-2-hydroxy-3-methoxypropyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-12'-((2R)-2-hydroxy-3-methoxypropyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

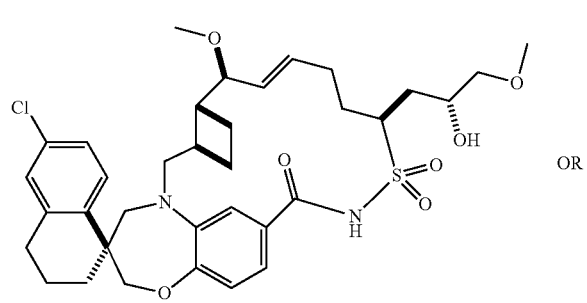

OR

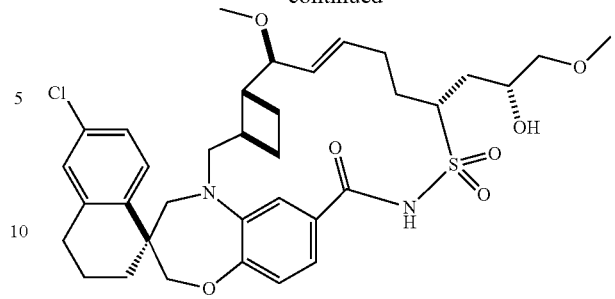

The title compound was obtained as a white foam as the second eluting isomer from the reversed phase preparatory HPLC separation in the synthesis of Example 651. $^1$H NMR (400 MHz, CDCl$_3$) δ 8.06 (s., 1H), 7.60-7.88 (m, 1H), 7.14-7.26 (m, 1H), 6.87-7.11 (m, 3H), 5.73-5.93 (m, 1H), 5.46 (dd, J=15.65, 8.02 Hz, 1H), 4.02-4.19 (m, 2H), 3.99 (d, J=3.52 Hz, 1H), 3.99-3.87 (m, 1H), 3.45-3.68 (m, 3H), 3.22-3.44 (m, 6H), 2.70-2.86 (m, 2H), 2.64 (s, 1H), 2.46 (m., 1H), 2.25-1.38 (m, 19H). m/z (ESI, +ve ion) 673.1 (M+H)$^+$.

Example 653. (1S,3'R,6'R,7'S,8'E,11'S,12'S)-6-chloro-7'-hydroxy-11'-methyl-12'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7'-hydroxy-11'-methyl-12'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

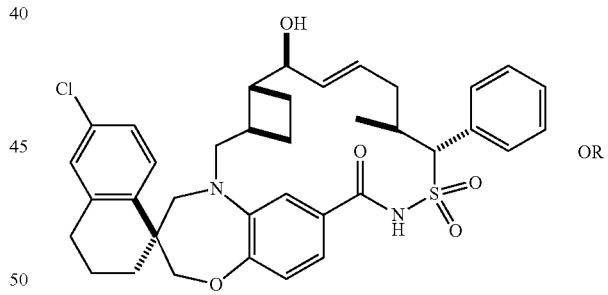

OR

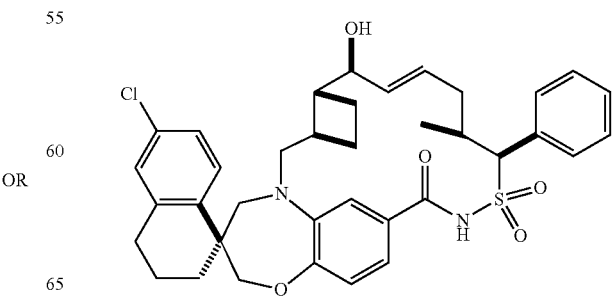

1377

Step 1: N,N-bis(4-methoxybenzyl)-1-phenylmethanesulfonamide

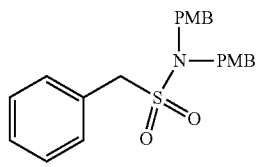

The title compound was prepared from phenylmethanesulfonamide following a procedure similar to the one described for the synthesis of EE12.

Step 2: (1S,2S)—N,N-bis(4-methoxybenzyl)-2-methyl-1-phenylpent-4-ene-1-sulfonamide and (1R,2S)—N,N-bis(4-methoxybenzyl)-2-methyl-1-phenylpent-4-ene-1-sulfonamide

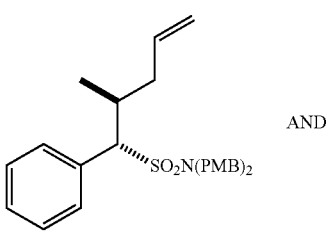

To a −78° C. solution of N,N-bis(4-methoxybenzyl)-1-phenylmethanesulfonamide (1.47 g, 3.58 mmol, Step 1) in THF (7.2 mL) under $N_2$ was added "BuLi (1.43 ml, 2.5 M in hexanes, 3.58 mmol) over 1.0 min. The mixture was allowed to stir in the −78° C. bath for 15 min. To the mixture was added (R)-pent-4-en-2-yl 4-methylbenzenesulfonate (1.72 g, 7.15 mmol, prepared according to the procedure reported by Sigman, M. S. et al.; *J. Am. Chem. Soc.*, 2012, 134, 11408-11411) in one shot. After stirring in the bath for 2 min, the resulting mixture was removed from the cold bath and allowed to stir in ambient atmosphere for 40 min. The mixture was quenched with saturated aqueous $NH_4Cl$ solution (10 mL), diluted with water (10 mL) and extracted with EtOAc (3×18 mL). The organic layers were combined. After removal of organic solvents under reduced pressure, purification of the residue by flash chromatography on ISCO Gold silica gel column using 0-50% EtOAc/Hexanes as the eluent provided the title compound as a white solid.

1378

Step 3: (1S,2S)-2-methyl-1-phenylpent-4-ene-1-sulfonamide and (1R,2S)-2-methyl-1-phenylpent-4-ene-1-sulfonamide

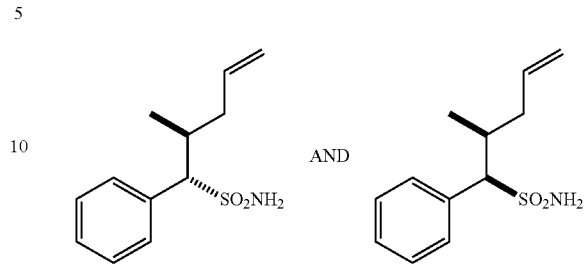

The title compounds were prepared as a mixture from (1S,2S)—N,N-bis(4-methoxybenzyl)-2-methyl-1-phenylpent-4-ene-1-sulfonamide and (1R,2S)—N,N-bis(4-methoxybenzyl)-2-methyl-1-phenylpent-4-ene-1-sulfonamide (Step 2) following a procedure similar to the one described for the synthesis of EE17 (Step 2).

Step 4: (3S)-6'-chloro-5-(((1R,2R)-2-((1S,2E,5S,6S)-1-hydroxy-5-methyl-6-phenyl-6-sulfamoyl-2-hexen-1-yl)cyclobutyl)methyl)-3',4,4',5-tetrahydro-2'H-spiro[1,5-benzoxazepine-3,1'-naphthalene]-7-carboxylic Acid and (3S)-6'-chloro-5-(((1R,2R)-2-((1S,2E,5S,6R)-1-hydroxy-5-methyl-6-phenyl-6-sulfamoyl-2-hexen-1-yl)cyclobutyl)methyl)-3',4,4',5-tetrahydro-2'H-spiro[1,5-benzoxazepine-3,1'-naphthalene]-7-carboxylic Acid

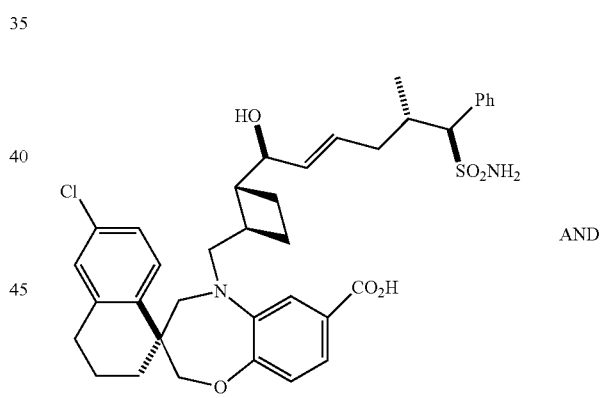

AND

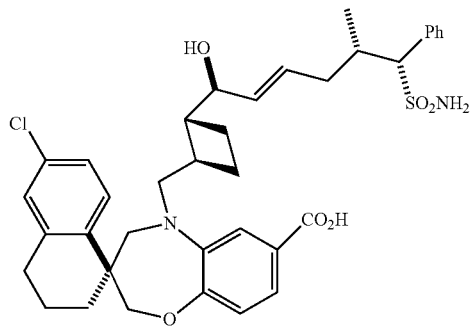

A solution of (S)-6'-chloro-5-(((1R,2R)-2-((S)-1-hydroxy-allyl)cyclobutyl)methyl)-3',4,4',5-tetrahydro-2H,2'H-spiro[benzo[b][1,4]oxazepine-3,1'-naphthalene]-7-carboxylic acid (Intermediate AA1 TA, 350 mg, 0.748 mmol) and (1S,2S)-2-methyl-1-phenylpent-4-ene-1-sulfonamide and (1R,2S)-2-methyl-1-phenylpent-4-ene-1-sulfonamide (Step 3, 384 mg, 1.60 mmol) in 1,2-dichloroethane (10.7 mL) was purged with Ar for 20 min at rt. To the mixture was added Hoveyda-Grubbs catalyst 2nd generation (47 mg, 0.075 mmol, Sigma-Aldrich Chemical Company, Inc.). The mixture was purged with Ar for 5 min, sealed under Ar balloon, and then placed into 47° C. bath. After stirring at 47° C. for 1.5 h, the mixture was cooled to rt, and purged with air for 5 min. After removal of organic solvents under reduced pressure, purification of the residue by flash chromatography on ISCO Gold silica gel column with 0-100% EtOAc/Hexanes (EtOAc contained 0.1% HOAc) provided the title compounds as white solid.

Step 5: (1S,3'R,6'R,7'S,8'E,11'S,12'S)-6-chloro-7'-hydroxy-11'-methyl-12'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-7'-hydroxy-11'-methyl-12'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide To a solution of (3S)-6'-chloro-5-(((1R,2R)-2-((1S,2E,5S,6S)-1-hydroxy-5-methyl-6-phenyl-6-sulfamoyl-2-hexen-1-yl)cyclobutyl)methyl)-3',4,4',5-tetrahydro-2'h-spiro[1,5-benzoxazepine-3,1'-naphthalene]-7-carboxylic acid and (3S)-6'-chloro-5-(((1R,2R)-2-((1S,2E,5S,6R)-1-hydroxy-5-methyl-6-phenyl-6-sulfamoyl-2-hexen-1-yl)cyclobutyl)methyl)-3',4,4',5-tetrahydro-2'h-spiro[1,5-benzoxazepine-3,1'-naphthalene]-7-carboxylic acid (280 mg, 0.412 mmol, Step 4) and 4-(dimethylamino)pyridine (151 mg, 1.237 mmol, ZZ—Alfa Aesar) in CHCl$_3$ was added 1-(3-dimethylaminopropyl)-3-ethylcarbodiimide hydrochloride (198 mg, 1.03 mmol, Thermo Fisher Scientific) at rt. The mixture was allowed to stir at rt for 72 h. After removal of organic solvents under reduced pressure, the crude product was re-dissolved in DMF (5 mL) and subjected to reverse phase preparatory HPLC (Gemini™ Prep C18 10 μm column; Phenomenex, Torrance, CA; gradient elution of 10% MeCN in water to 90% MeCN in water over a 30 min period, where both solvents contain 0.1% TFA) to provide one of the title compounds as the first eluting fraction as a white foam. $^1$H NMR (400 MHz, CDCl$_3$) δ 8.16 (m, 1H), 7.71 (d, J=7.24 Hz, 1H), 7.36-7.61 (m, 4H), 7.26 (m, 1H), 7.19 (m, 1H) 7.10 (m., 1H), 6.95 (m 2H), 6.07 (d, J=6.65 Hz, 1H), 5.76 (dd, J=15.06, 8.22 Hz, 1H), 5.43 (m, 1H), 4.34 (m, 1H), 4.11 (m, 2H), 3.87 (d, J=14.67 Hz, 1H), 3.73 (d, J=13.69 Hz, 1H), 3.25 (d, J=14.09 Hz, 1H), 2.96-3.12 (m, 1H), 2.66-2.88 (m, 2H), 2.26-2.55 (m, 3H), 1.57-2.15 (m, 10H), 1.19-1.48 (m, 2H), 1.05 (d, J=6.46 Hz, 3H). m/z (ESI, +ve ion) 661.1 (M+H)$^+$.

Example 654. (1S,3'R,6'R,7'S,8'E,11'S,12'S)-6-chloro-7'-hydroxy-11'-methyl-12'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-7'-hydroxy-11'-methyl-12'-phenyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide

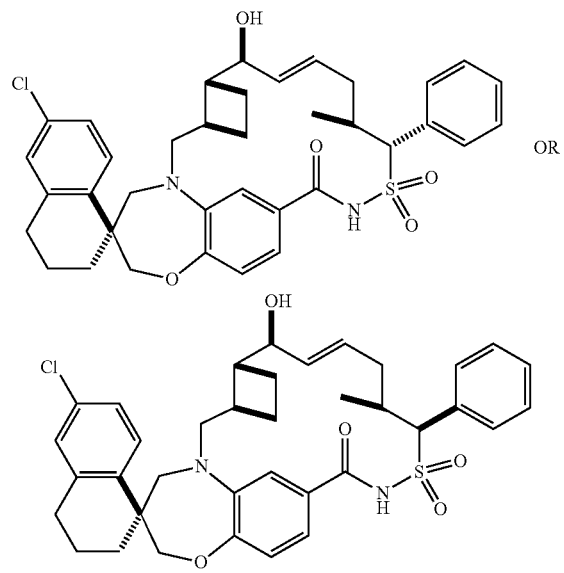

The title compound was obtained as a white foam as the second eluting isomer from the reversed phase preparatory HPLC separation in Example 653, Step 5. $^1$H NMR (400 MHz, CDCl$_3$) δ $^1$H NMR (400 MHz, CDCl$_3$) δ 8.22 (br. s., 1H), 7.69 (d, J=8.61 Hz, 1H), 7.51-7.62 (m, 2H), 7.39-7.51 (m, 3H), 7.08-7.24 (m, 3H), 6.94-7.01 (m, 1H), 5.97 (m, 1H), 5.74 (dd, J=15.75, 4.99 Hz, 1H), 5.09 (m., 1H), 4.05-4.27 (m, 3H), 3.40-3.74 (m, 3H), 2.72-2.87 (m, 3H), 2.55 (br. s., 2H), 2.37 (br. s., 1H), 2.00-2.14 (m, 3H), 1.69-1.99 (m, 7H), 1.61 (m, 2H), 0.93-1.14 (m, 3H). m/z (ESI, +ve ion) 661.1 (M+H)$^+$.

Example 655. (1S,3'R,6'R,7'S,8'E,12'R)-6-chloro-12'-ethyl-17'-fluoro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

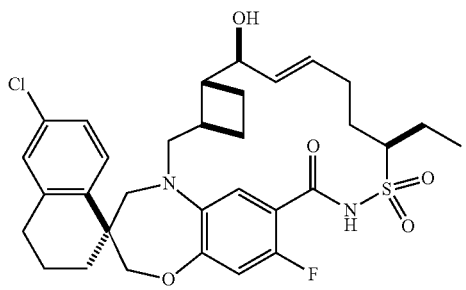

Step 1: (S)-6'-chloro-8-fluoro-N—((R)-hept-6-en-3-ylsulfonyl)-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide

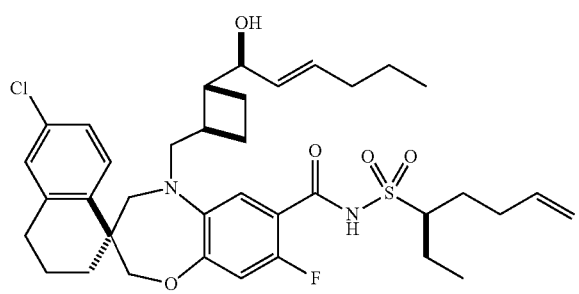

The title compound was prepared from (S)-6'-chloro-8-fluoro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA16) and (R)-hept-6-ene-3-sulfonamide (Intermediate EE21) following a procedure similar to the one described in Step 2 for the synthesis of Example 660.

Step 2: (1S,3'R,6'R,7'S,8'E,12'R)-6-chloro-12'-ethyl-17'-fluoro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compound was prepared from (S)-6'-chloro-8-fluoro-N—((R)-hept-6-en-3-ylsulfonyl)-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide (Step 1) following a procedure similar to the one described in Step 3 for the synthesis of Example 660. $^1$H NMR (400 MHz, CDCl$_3$) δ 8.30 (d, J=8.80 Hz, 1H), 7.66 (d, J=8.61 Hz, 1H), 7.18 (dd, J=8.51, 2.25 Hz, 1H), 7.09 (d, J=2.15 Hz, 1H), 6.99 (d, J=7.24 Hz, 1H), 6.72 (d, J=11.54 Hz, 1H), 5.61-5.79 (m, 2H), 4.05-4.20 (m, 3H), 4.01 (d, J=4.50 Hz, 1H), 3.77-3.88 (m, 1H), 3.57-3.68 (m, 1H), 3.23 (d, J=14.48 Hz, 1H), 2.99 (dd, J=15.16, 8.51 Hz, 1H), 2.69-2.85 (m, 2H), 2.42-2.55 (m, 1H), 2.34 (d, J=11.93 Hz, 2H), 1.86-2.21 (m, 8H), 1.59-1.77 (m, 4H), 1.41 (t, J=12.52 Hz, 1H), 1.25-1.32 (m, 1H), 1.18-1.25 (m, 3H). m/z (ESI, +ve ion) 617.0 (M+H)$^+$.

Example 656. (1S,3'R,6'R,7'S,8'E,11'S,12'R)-6-chloro-11'-methyl-7'-(2-(4-morpholinyl)ethoxy)-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-11'-methyl-7'-(2-(4-morpholinyl)ethoxy)-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'Z,11'S,12'R)-6-chloro-11'-methyl-7'-(2-(4-morpholinyl)ethoxy)-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'Z,11'S,12'S)-6-chloro-11'-methyl-7'-(2-(4-morpholinyl)ethoxy)-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

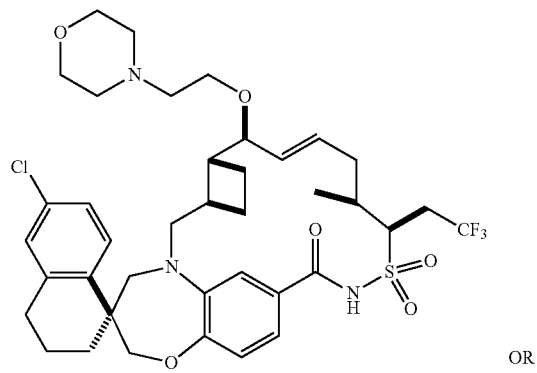

OR

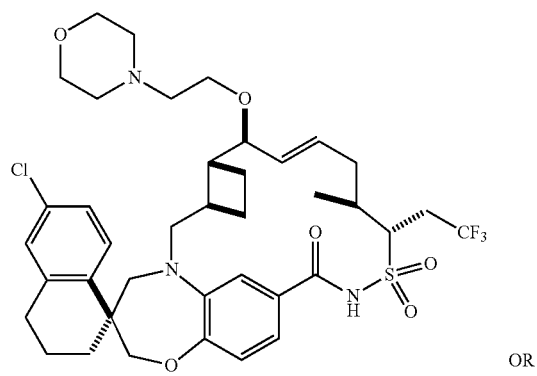

OR

-continued

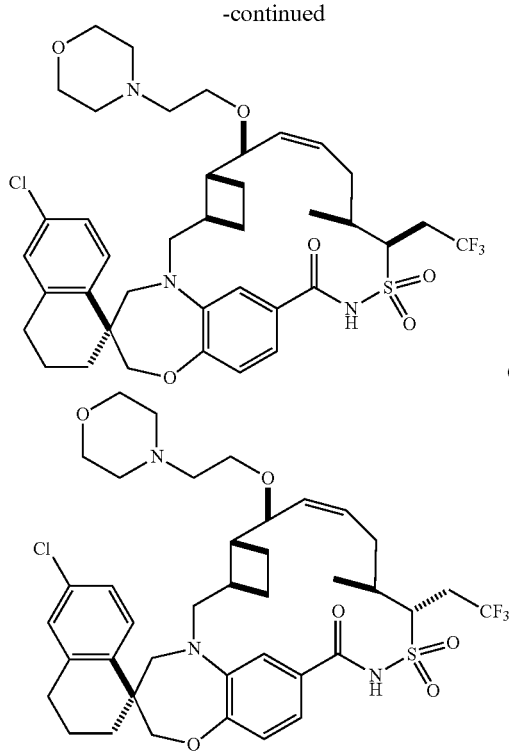

OR

To a 0° C. flask charged with (1S,3'R,6'R,7'S,8'E,11'S,12'R)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'S,12'S)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo [14.7.2.0³,⁶.0¹⁹,²⁴]pentacosa[8,16,18,24]tetraen]-15'-one 13',13'-dioxide or (1S,3'R,6'R,7'S,8'Z,11'S,12'R)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'Z,11'S,12'S)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (30 mg, 0.045 mmol, Example 663) and sodium hydride (18 mg, 60% dispersion in mineral oil 0.45 mmol, Strem Chemicals, Inc.) was added DMF (1.3 mL). This mixture was allowed to stir in the ice bath under $N_2$ for 15 min, to the mixture was added 4-(2-bromoethyl)morpholine hydrobromide (62 mg, 0.23 mmol, Accela ChemBio Inc.). The mixture was allowed to stir at rt for 2.0 h. To the reaction mixture was added saturated aqueous $NH_4Cl$ solution (1.0 mL) and water (4 mL). The resulting mixture was extracted with EtOAc (3×5 mL). The organic layers were combined. After removal of organic solvents under reduced pressure, purification of the residue by flash chromatography on ISCO Gold silica gel column with 0-100% EtOAc/Hexanes (EtOAc contained 0.1% HOAc) provided the title compound as a colorless film. $^1$H NMR (400 MHz, $CDCl_3$) δ 7.63 (d, J=8.6 Hz, 1H), 7.17-7.07 (m, 1H), 7.07-6.97 (m, 2H), 6.93 (s, 1H), 6.81 (d, J=8.0 Hz, 1H), 5.82-5.70 (m, 1H), 5.48 (dd, J=8.1, 15.6 Hz, 1H), 4.15 (br. s., 1H), 4.04-3.93 (m, 2H), 3.84-1.64 (m, 32H), 1.57 (td, J=8.8, 17.9 Hz, 1H), 1.31 (t, J=11.4 Hz, 1H), 1.00 (d, J=6.8 Hz, 3H). m/z (ESI, +ve ion) 780.3 (M+H)⁺.

Example 657. (1S,3'R,6'R,7'S,8'E,12'R)-6,17'-dichloro-12'-ethyl-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24] tetraen]-15'-one 13',13'-dioxide

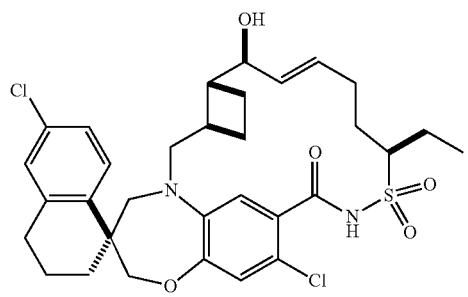

Step 1 (S)-6',8-dichloro-N—((R)-hept-6-en-3-ylsulfonyl)-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide

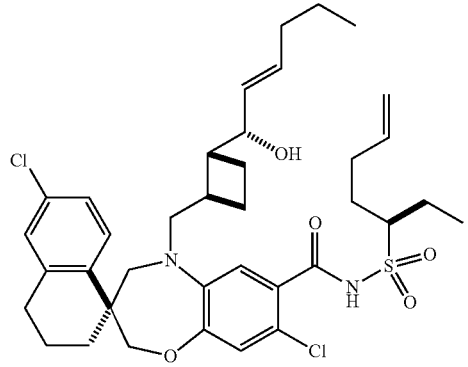

The title compound was prepared from (S)-6',8-dichloro-5-(((1R,2R)-2-((S,E)-1-hydroxyhex-2-en-1-yl)cyclobutyl) methyl)-3',4,4',5-tetrahydro-2H,2'H-spiro[benzo[b][1,4] oxazepine-3,1'-naphthalene]-7-carboxylic acid (Intermediate AA17) and (R)-hex-5-ene-3-sulfonamide (Intermediate EE21) following a procedure similar to the one described in Example 660, Step 1, except that the crude product was purified by flash chromatography on ISCO Gold silica gel column using 0-60% EtOAc/Hexanes (EtOAc contained 0.1% HOAc) to provide the title compound as a white solid.

Step 2. (1S,3'R,6'R,7'S,8'E,12'R)-6,17'-dichloro-12'-ethyl-7'-hydroxy-3,4-dihydro-2H,15'H-spiro[naphthalene-1,22'-[20]oxa[13]thia[1,14]diazatetracyclo [14.7.2.0³,⁶.0¹⁹,²⁴]pentacosa [8,16,18,24]tetraen]-15'-one 13',13'-dioxide The title compound was prepared from (S)-6',8-dichloro-N—((R)-hept-6-en-3-ylsulfonyl)-5-(((1R,2R)-2-((S,E)-1- hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide (Step 1) following a procedure similar to the one described in Example 660, Step 3, except that the crude product was purified by reversed phase preparatory HPLC (Gemini™ Prep C18 10 μm column; Phenomenex, Torrance, CA; gradient elution of 45% to 90% MeCN in water, where both solvents contain 0.1% TFA, 25 min method) to provide the title compound as a white foam. $^1$H NMR (400 MHz, CDCl$_3$) δ 8.48-8.34 (s, 1H), 7.66 (d, J=8.6 Hz, 1H), 7.19 (d, J=5.9 Hz, 1H), 7.09 (br. s., 1H), 6.99-6.90 (m, 1H), 6.83 (m, 1H), 5.87-5.62 (m, 2H), 4.18 (d, J=4.1 Hz, 1H), 4.16-3.96 (m, 3H), 3.84-3.62 (m, 2H), 3.25 (m, 1H), 3.01 (dd, J=9.4, 15.3 Hz, 1H), 2.90-21.26 (m, 19H), 1.25-1.13 (m, 3H). m/z (ESI, +ve ion) 615.0 (M−H$_2$O+H)$^+$.

Example 658. (1S,3'R,6'R,7'S,8'E,12'S)-6-chloro-12'-((2S)-2-hydroxy-3-methoxypropyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-12'-((2S)-2-hydroxy-3-methoxypropyl)-7'-methoxy-3,4-dihydro-2H,15'H-spiro[naphthalene-1,22' [20]oxa[13]thia[1,14]diazatetracyclo[14.7.2.0$^{3,6}$.0$^{19,24}$]pentacosa[8,16,18,24]tetraen]-15'-one 13',13'-dioxide

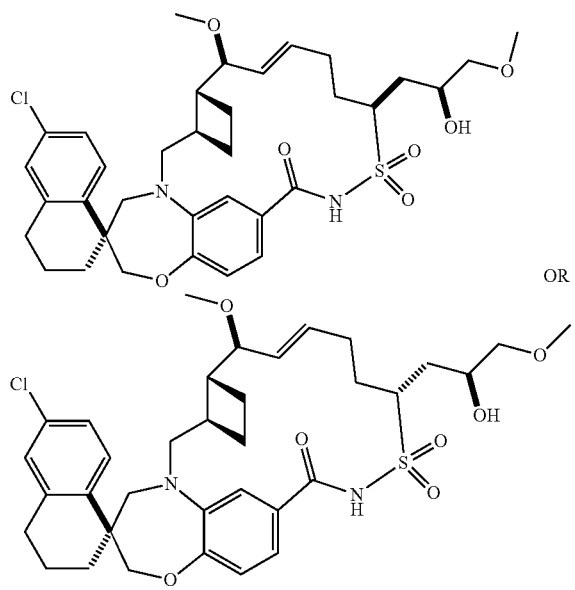

OR

The title compounds were prepared from (1S,3'R,6'R,7'S,8'E)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 651, Step 3) following a procedure similar to the one described for the synthesis of Example 651, Step 4, except that (s)-(+)-glycidyl methyl ether (TCI—Tokyo Chemical Industry Co., Ltd.) was used in place of (R)-(−)-glycidyl methyl ether. The crude product was subjected to reverse phase preparatory HPLC (Gemini™ Prep C18 5 μm column; Phenomenex, Torrance, CA; gradient elution of 10% MeCN in water to 90% MeCN in water over a 20 min period, where both solvents contain 0.1% TFA) to provide one of the title compounds as the first eluting fraction as a white foam. $^1$H NMR (400 MHz, CDCl$_3$) δ 8.10 (br. s., 1H), 7.70 (d, J=8.6 Hz, 1H), 7.22-7.15 (m, 1H), 7.10-6.89 (m, 3H), 6.82 (s, 1H), 5.86 (dd, J=6.3, 14.1 Hz, 1H), 5.53 (dd, J=8.7, 15.4 Hz, 1H), 4.41 (d, J=4.7 Hz, 1H), 4.20-4.01 (m, 4H), 3.86-3.60 (m, 4H), 3.56-3.48 (m, 2H), 3.42 (s, 3H), 3.24 (s, 3H), 3.45-1.26 (m, 19H). m/z (ESI, +ve ion) 673.0 (M+H)$^+$.

Example 659. (1S,3'R,6'R,7'S,8'E,12'S)-6-chloro-12'-((2S)-2-hydroxy-3-methoxypropyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-12'-((2S)-2-hydroxy-3-methoxypropyl)-7'-methoxy-3,4-dihydro-2H,15'H-spiro[naphthalene-1,22' [20]oxa[13]thia[1,14]diazatetracyclo[14.7.2.0$^{3,6}$.0$^{19,24}$]pentacosa[8,16,18,24]tetraen]-15'-one 13',13'-dioxide

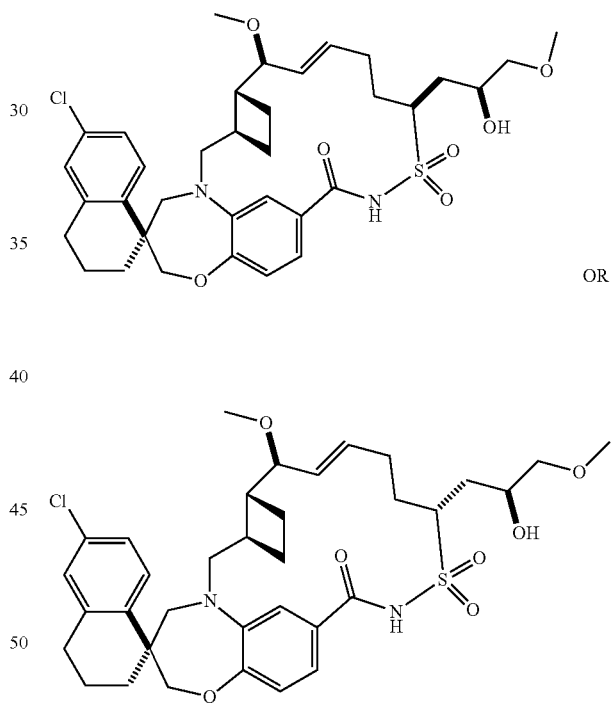

The title compound was obtained as a white foam as the second eluting isomer from the reversed phase preparatory HPLC separation in the synthesis of Example 658. $^1$H NMR (400 MHz, CDCl$_3$) δ 7.63-7.75 (m, 1H), 7.13-7.25 (m, 1H), 6.97-7.13 (m, 3H), 6.93 (d, J=8.02 Hz, 1H), 5.74-5.88 (m, 1H), 5.43 (dd, J=15.36, 7.73 Hz, 1H), 4.22 (dd, J=6.55, 3.23 Hz, 1H), 4.11 (m, 2H), 4.00 (m, 1H), 3.44-3.66 (m, 5H), 3.41 (s, 3H), 3.24-3.38 (m, 5H), 2.78 (m., 2H), 2.31-2.59 (m, 3H), 2.12-2.31 (m, 4H), 1.73-2.12 (m, 5H), 1.61-1.73 (m, 2H), 1.48-1.26 (m, 3H). m/z (ESI, +ve ion) 673.0 (M+H)$^+$.

1387

Example 660. (1S,3'R,6'R,7'S,8'E)-6-chloro-7'-hydroxy-3,4-dihydro-2H,16'H-spiro[naphthalene-1,23'-[21]oxa[14]thia[1,13,15]triazatetracyclo[15.7.2.0³,⁶.0²⁰,²⁵]hexacosa[8,17,19,25]tetraen]-16'-one 14',14'-dioxide

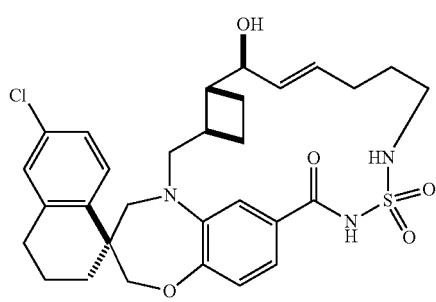

Step 1: N-4-penten-1-ylsulfuric diamide

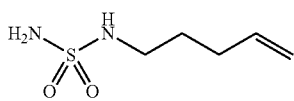

A mixture of pent-4-en-1-amine (343 mg, 4.03 mmol, Sigma-Aldrich Chemical Company, Inc.) and sulfuric diamide (7.74 g, 81.0 mmol, Accela ChemBio Inc.) in 1,4-dioxane (7 mL) was refluxed under $N_2$ for 44 h. The resulting mixture was allowed to cool to rt, diluted with EtOAc (15 mL) and washed with water (4×15 mL). After removal of organic solvents under reduced pressure, purification of the residue by flash chromatography on ISCO Gold silica gel column using 0-100% EtOAc/Hexanes (EtOAc contained 0.1% HOAc) as the eluent provided the title compound as a colorless wax.

1388

Step 2: (S)-6'-chloro-5-(((1R,2R)-2-((S)-1-hydroxyallyl)cyclobutyl)methyl)-N—(N-(pent-4-en-1-yl)sulfamoyl)-3',4,4',5-tetrahydro-2H,2'H-spiro[benzo[b][1,4]oxazepine-3,1'-naphthalene]-7-carboxamide

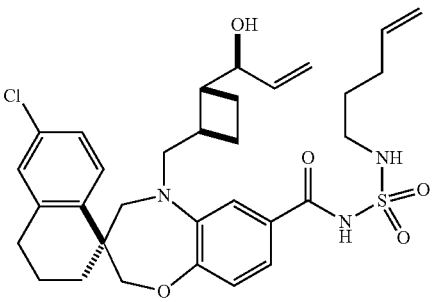

To a solution of N-4-penten-1-ylsulfuric diamide (47 mg, 0.29 mmol, Step 1), (S)-6'-chloro-5-(((1R,2R)-2-((S)-1-hydroxyallyl)cyclobutyl)methyl)-3',4,4',5-tetrahydro-2h,2'h-spiro[benzo [b][1,4]oxazepine-3,1'-naphthalene]-7-carboxylic Acid (67 mg, 0.14 mmol, AA11A), and 4-(dimethylamino)pyridine (17 mg, 0.14 mmol, Alfa Aesar) in dichloromethane (2.9 mL) under Ar was added triethylamine (119 µl, 0.859 mmol, Sigma-Aldrich Chemical Company, Inc.) followed by 1-(3-dimethylaminopropyl)-3-ethylcarbodiimide hydrochloride (55 mg, 0.29 mmol, Sigma-Aldrich Chemical Company, Inc.) at rt. The resulting mixture was allowed to stir at rt overnight. The reaction solution was directly purified by flash chromatography on ISCO Gold silica gel column using 0-100% EtOAc/Hexanes (EtOAc contained 0.1% HOAc) as the eluent to provide the title compound as a white solid.

Step 3: (1S,3'R,6'R,7'S,8'E)-6-chloro-7'-hydroxy-3,4-dihydro-2H,16'H-spiro[naphthalene-1,23'-[21]oxa[14]thia[1,13,15]triazatetracyclo[15.7.2.0³,⁶.0²⁰,²⁵]hexacosa[8,17,19,25]tetraen]-16'-one 14',14'-dioxide A solution of (S)-6'-chloro-5-(((1R,2R)-2-((S)-1-hydroxyallyl)cyclobutyl)methyl)-N—(N-(pent-4-en-1-yl)sulfamoyl)-3',4,4',5-tetrahydro-2H,2'H-spiro[benzo[b][1,4]oxazepine-3,1'-naphthalene]-7-carboxamide (51 mg, 0.083 mmol, Step 2) in 1,2-dichloroethane (25 mL) was purged with Ar for 15 min. To the solution was added Hoveyda-Grubbs 2$^{nd}$ generation catalyst (5.0 mg, 8.0 µmol, Sigma-Aldrich Chemical Company, Inc.) After the reaction solution was purged with Ar for 5 min, the resulting solution was allowed to stir at 55° C. under running Ar line for 4.0 h. The reaction solution was removed from the bath and allowed to cool to rt with air purge. After removal of organic solvents under reduced pressure, purification of the residue by flash chromatography on ISCO Gold silica gel column using 20-50% EtOAc/Hexanes (EtOAc contained 0.1% HOAc) as the eluent provided the title compound as a white foam. $^1$H NMR (400 MHz, CDCl$_3$) δ 7.69 (d, J=8.4 Hz, 1H), 7.17 (dd, J=2.2, 8.5 Hz, 1H), 7.12-7.03 (m, 3H), 7.00-6.79 (m, 1H), 5.85-5.58 (m, 2H), 4.22-4.01 (m, 3H), 3.71-3.49 (m, 2H), 3.36 (d, J=14.5 Hz, 1H), 3.30-3.14 (m, 2H), 2.86-2.70 (m, 2H), 2.64 (d, J=5.7 Hz, 1H), 2.56-2.28 (m, 2H), 2.21-1.42 (m, 13H), 1.33-1.21 (m, 1H). m/z (ESI, +ve ion) 596.3 (M+H)$^+$.

Example 661. (1S,3'R,6'R,7'S,8'E,11'S,12'R)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'Z,11'S,12'R)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'Z,11'S,12'S)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

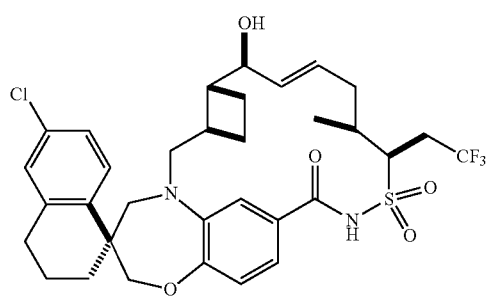

OR

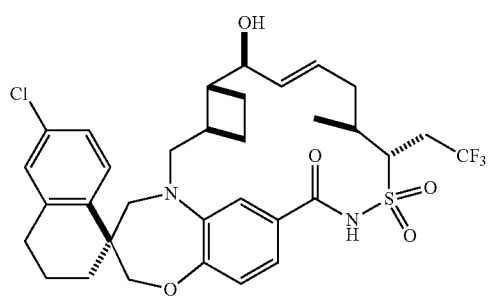

OR

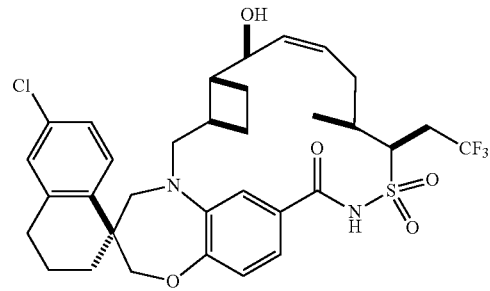

OR

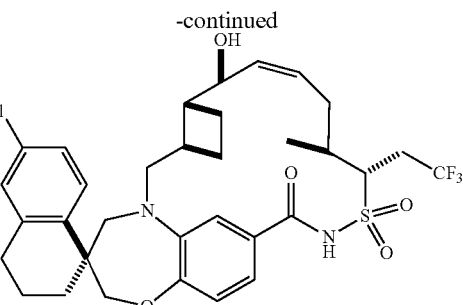

Step 1: 3,3,3-trifluoro-N,N-bis(4-methoxybenzyl)propane-1-sulfonamide

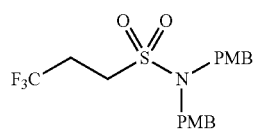

The title compound was prepared from 3,3,3-trifluoropropane-1-sulfonamide (SynQuest Lab, Inc.) following a procedure similar to the one described for the synthesis of EE12.

Step 2: ((3R,4S)-1,1,1-trifluoro-N,N-bis(4-methoxybenzyl)-4-methylhept-6-ene-3-sulfonamide and (3S,4S)-1,1,1-trifluoro-N,N-bis(4-methoxybenzyl)-4-methylhept-6-ene-3-sulfonamide

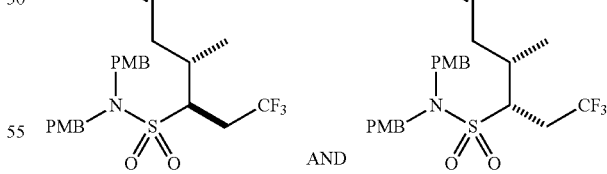

The title compounds were prepared from 3,3,3-trifluoro-N,N-bis(4-methoxybenzyl)propane-1-sulfonamide (Step 1) and (R)-pent-4-en-2-yl 4-methylbenzenesulfonate (prepared according to the procedure reported by Sigman, M. S. et al.; *J. Am. Chem. Soc.*, 2012, 134, 11408-11411) following a procedure similar to the one described in Step 2 for the synthesis of EXAMPLE 653.

1391

Step 3: (3R,4S)-1,1,1-trifluoro-4-methylhept-6-ene-3-sulfonamide and (3S,4S)-1,1,1-trifluoro-4-methyl-hept-6-ene-3-sulfonamide

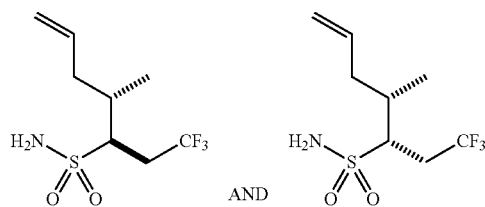

The title compounds were prepared from ((3R,4S)-1,1,1-trifluoro-N,N-bis(4-methoxybenzyl)-4-methylhept-6-ene-3-sulfonamide and (3S,4S)-1,1,1-trifluoro-N,N-bis(4-methoxybenzyl)-4-methylhept-6-ene-3-sulfonamide (Step 2) following a procedure similar to the one described for the synthesis of EE17 (Step 2).

Step 4: ((S)-6'-chloro-5-(((1R,2R)-2-((S)-1-hydroxyallyl)cyclobutyl)methyl)-N-(((3R,4S)-1,1,1-trifluoro-4-methylhept-6-en-3-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxyallyl)cyclobutyl)methyl)-N-(((3S,4S)-1,1,1-trifluoro-4-methylhept-6-en-3-yl)sulfonyl)-3',4,4',5-tetrahydro-2H,2'H-spiro[benzo[b][1,4]oxazepine-3,1'-naphthalene]-7-carboxamide

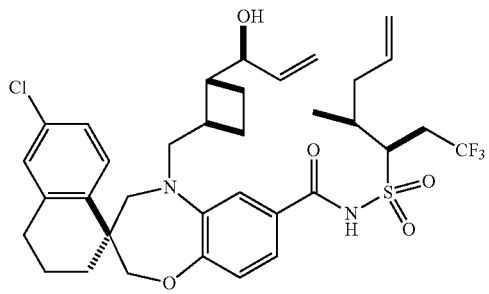

AND

1392

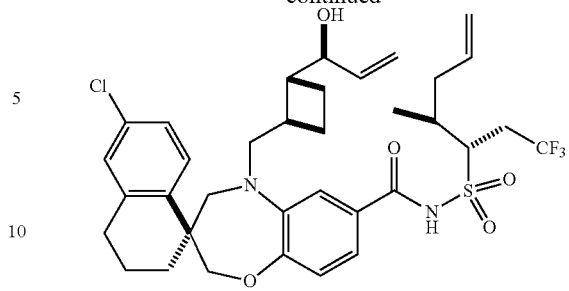

The title compounds were prepared from (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (AA11A) and (3R,4S)-1,1,1-trifluoro-4-methylhept-6-ene-3-sulfonamide and (3S,4S)-1,1,1-trifluoro-4-methylhept-6-ene-3-sulfonamide (Step 3) following a procedure similar to the one described in Step 2 for the synthesis of Example 660.

Step 5: (1S,3'R,6'R,7'S,8'E,11'S,12'R)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'R)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S,12'S)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide The title compounds were prepared from ((S)-6'-chloro-5-(((1R,2R)-2-((S)-1-hydroxyallyl)cyclobutyl)methyl)-N-(((3R,4S)-1,1,1-trifluoro-4-methylhept-6-en-3-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxyallyl)cyclobutyl)methyl)-N-(((3S,4S)-1,1,1-trifluoro-4-methylhept-6-en-3-yl)sulfonyl)-3',4,4',5-tetrahydro-2H,2'H-spiro[benzo[b][1,4]oxazepine-3,1'-naphthalene]-7-carboxamide (Step 4) following a procedure similar to the one described in Step 3 for the synthesis of Example 660. Portion of the crude product was purified by reverse phase preparatory HPLC (Gemini™ Prep C18 10 μm column; Phenomenex, Torrance, CA; gradient elution of 45% MeCN in water to 95% MeCN in water over a 30 min period, where both solvents contain 0.1% TFA) to provide one of the title compounds as the third eluting fraction as a white foam. $^1$H NMR (400 MHz, CDCl$_3$) δ 8.57 (br. s., 1H), 7.80-7.61 (m, 1H), 7.18 (d, J=8.2 Hz, 2H), 7.10 (s, 1H), 7.02-6.86 (m, 1H), 6.84-6.63 (m, 1H), 5.96 (d, J=10.0 Hz, 1H), 5.81-5.55 (m, 2H), 4.28-3.87 (m, 5H), 3.76-3.46 (m, 3H), 3.39 (m, 1H), 3.33-2.99 (m, 3H), 2.89-1.46 (m, 14H), 1.22-1.11 (m, 3H). m/z (ESI, +ve ion) 667.3 (M+H)$^+$.

Example 662. (1S,3'R,6'R,7'S,8'E,11'S,12'R)-6-chloro-7'-hydroxy-11'-methyl-12'-(2,2,2-trifluoroethyl)-3,4-dihydro-2H,15'H-spiro [naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-(2,2,2-trifluoroethyl)-3,4-dihydro-2H,15'H-spiro [naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'Z,11'S,12'R)-6-chloro-7'-hydroxy-11'-methyl-12'-(2,2,2-trifluoroethyl)-3,4-dihydro-2H,15'H-spiro [naphthalene-1,22'-[20]oxa[13]thia[1,14] diazatetracyclo[14.7.2.0$^{3,6}$.0$^{19,24}$]pentacosa [8,16,18,24]tetraen]-15'-one 13',13'-dioxide or (1S,3'R,6'R,7'S,8'Z,11'S,12'S)-6-chloro-7'-hydroxy-11'-methyl-12'-(2,2,2-trifluoroethyl)-3,4-dihydro-2H,15'H-spiro [naphthalene-1,22'-[20]oxa[13]thia[1,14] diazatetracyclo[14.7.2.0$^{3,6}$.0$^{19,24}$]pentacosa [8,16,18,24]tetraen]-15'-one 13',13'-dioxide

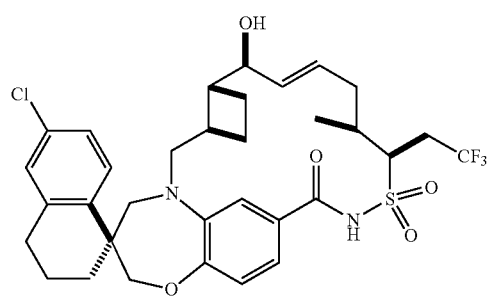

OR

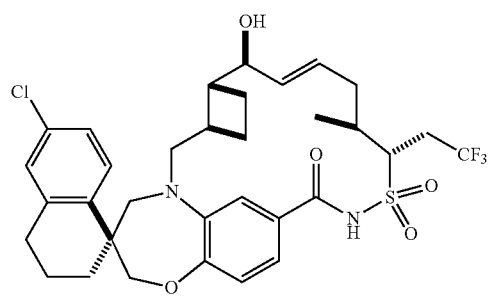

OR

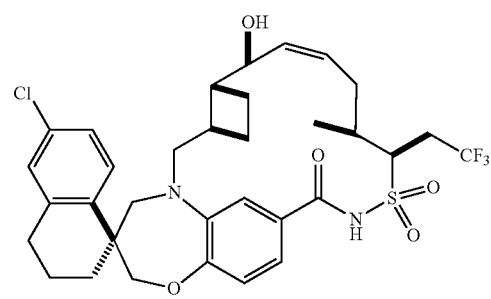

OR

-continued

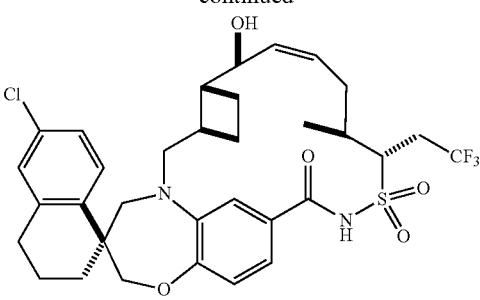

The title compound was obtained as a white foam as the fourth eluting isomer from the reversed phase preparatory HPLC separation in Example 661. $^1$H NMR (400 MHz, CDCl$_3$) δ 10.31-10.01 (m, 1H), 7.77-7.66 (m, 1H), 7.53-7.42 (m, 1H), 7.18 (dd, J=2.1, 8.5 Hz, 1H), 7.14-7.07 (m, 2H), 7.03-6.95 (m, 1H), 5.82-5.68 (m, 1H), 5.56 (d, J=9.6 Hz, 1H), 4.41 (m, 1H), 4.17-3.98 (m, 2H), 3.95-3.78 (m, 2H), 3.62 (d, J=13.9 Hz, 1H), 3.19-2.96 (m, 4H), 2.95-1.36 (m, 17H), 1.16-1.06 (m, 3H); m/z (ESI, +ve ion) 667.2 (M+H)$^+$.

Example 663. (1S,3'R,6'R,7'S,8'E,11'S,12'R)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'Z,11'S,12'R)-6-chloro-7'-hydroxy-11'-methyl-12'-(2,2,2-trifluoroethyl)-3,4-dihydro-2H,15'H-spiro[naphthalene-1,22'-[20]oxa [13]thia[1,14]diazatetracyclo[14.7.2.0$^{3,6}$.0$^{19,24}$] pentacosa [8,16,18,24]tetraen]-15'-one 13',13'-dioxide or (1S,3'R,6'R,7'S,8'Z,11'S,12'S)-6-chloro-7'-hydroxy-11'-methyl-12'-(2,2,2-trifluoroethyl)-3,4-dihydro-2H,15'H-spiro[naphthalene-1,22'-[20]oxa [13]thia[1,14]diazatetracyclo[14.7.2.0$^{3,6}$.0$^{19,24}$] pentacosa [8,16,18,24]tetraen]-15'-one 13',13'-dioxide

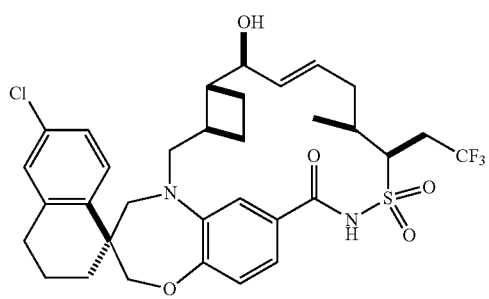

OR

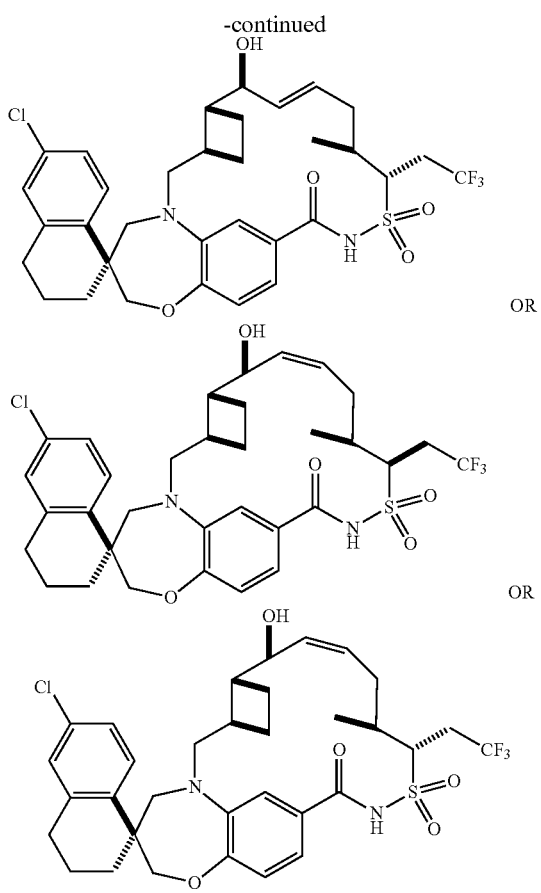

Portion of the crude product from Step 5 in the synthesis of Example 661 was purified by flash chromatography on ISCO Gold silica gel column with 0-80% EtOAc/Hexanes (EtOAc contained 0.1% HOAc) to provide one of the title compounds (the third eluting fraction) as a white foam. $^1$H NMR (400 MHz, CDCl$_3$) δ 8.30 (br. s., 1H), 7.69 (d, J=8.4 Hz, 1H), 7.18 (dd, J=2.2, 8.4 Hz, 1H), 7.10 (d, J=2.2 Hz, 2H), 6.99-6.87 (m, 2H), 5.91-5.77 (m, 1H), 5.78-5.64 (m, 1H), 4.47 (m, 1H), 4.20 (br. s., 1H), 4.28-4.03 (m, 2H), 3.86-3.55 (m, 2H), 3.47-3.08 (m, 2H), 3.08-1.68 (m, 18H), 1.11 (d, J=8.4, 3H). m/z (ESI, +ve ion) 667.0 (M+H)$^+$.

Example 664. (S)-6'-chloro-5-(((1R,2R)-2-((S)-1-hydroxyallyl)cyclobutyl)methyl)-N—(N—((S)-pent-4-en-2-yl)-N-(pyridin-2-ylmethyl)sulfamoyl)-3',4,4',5-tetrahydro-2H,2'H-spiro[benzo[b][1,4]oxazepine-3,1'-naphthalene]-7-carboxamide

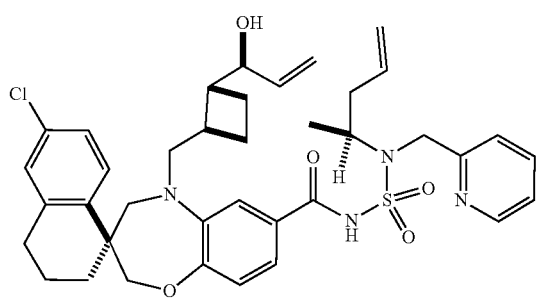 [SMILES: C=CC[C@H](C)N(Cc1ccccn1)S(=O)(=O)NC(=O)c1ccc2c(c1)N(C[C@@H]1CC[C@H]1[C@@H](O)C=C)C[C@@]1(CCCc3cc(Cl)ccc31)CO2]

Step 1: (S)-2-(pent-4-en-2-yl)isoindoline-1,3-dione

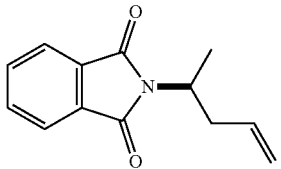

A solution of triphenylphosphine (24.4 g, 93.0 mmol, Acros Organics), phthalimide (8.54 g, 58.1 mmol, Alfa Aesar, A Johnson Matthey Company) and (R)-(−)-4-penten-2-ol (5.97 mL, 58.1 mmol, Sigma-Aldrich Chemical Company, Inc.) in THF (30 mL) under N$_2$ was allowed to stir at 0° C. for 30 min. To the resulting milky mixture was slowly added diethyl azodicarboxylate (42.3 mL, 93.0 mmol, 40 wt. % solution in toluene). The resulting solution was allowed to warm with the bath to rt and stirred at rt for 4.5 h. After removal of organic solvents under reduced pressure, to the residue was added a mixture solvent of diethyl ether/Hexanes (2:1, 100 mL). The precipitate was filtered off through a pad of Celite® (diatomaceous earth) and rinsed with cold diethyl ether (2×15 mL). The organic solutions were combined. After removal of organic solvents under reduced pressure, purification of the residue by flash chromatography on ISCO Gold silica gel column using 0-40% EtOAc/Hexanes as the eluent provided the title compound as a white solid.

Step 2: (S)-pent-4-en-2-amine hydrochloride

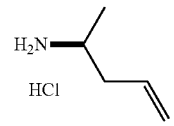

A solution of (S)-2-(pent-4-en-2-yl)isoindoline-1,3-dione (12.0 g, 55.7 mmol, Step 1) and ethanolamine (16.7 ml, 279 mmol, Sigma-Aldrich Chemical Company, Inc.) in EtOH (22 ml) was allowed to stir under Ar with condenser in 40° C. oil bath overnight. The reaction flask was equipped with distill short path apparatus. Slow fraction distillation of the solution in oil bath in an increasing temperature range of 85° C. to 120° C. provided the desired fractions (99.8° C. to 102° C.). The desired fractions were combined, placed into ice bath, and treated with HCl (10 mL, 4.0 N in 1,4-dioxane, Sigma-Aldrich Chemical Company, Inc.) under N$_2$. The resultant milky mixture was allowed to stir at rt for 20 min. After removal of organic solvents under reduced pressure, the residue was left under high vacuum for overnight to provide the title product as white solid.

Step 3: (S)-pent-4-en-2-amine

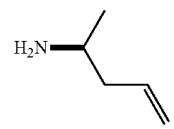

To a rt mixture of (S)-pent-4-en-2-amine hydrochloride (7.10 g, 58.4 mmol, Step 2) in water (15 mL) and diethyl ether (25 mL) was treated aqueous NaOH (6.0 N) to PH=14. The organic layer was separated, and aqueous layer was back extracted with diethyl ether (3×15 mL). The organic layers were combined, washed with water (5 mL), brine (5 mL) and dried over MgSO₄. The solid was filtered off through a small pad of a Celite® (diatomaceous earth) pad, the organic solution was placed into a flask equipped with distill short path apparatus. After distillation at 49° C., the remaining residue was collected as a solution of the title product (56%) in diethyl ether.

Step 4: (S)—N-(pyridin-2-ylmethyl)pent-4-en-2-amine

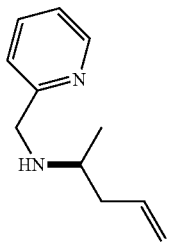

To a 0° C. solution of picolinaldehyde (135 mg, 1.26 mmol, Sigma-Aldrich Chemical Company, Inc.) and (S)-pent-4-en-2-amine (320 mg, 2.105 mmol, Step 3) in 1,2-dichloroethane (10 mL) was slowly added sodium cyanoborohydride (2.11 mL, 1.0 M in THF, 2.11 mmol, Sigma-Aldrich Chemical Company, Inc.). The mixture was allowed to warm with the ice bath to rt over 2.0 h. After stirring at rt for 1.0 h, the mixture was treated with saturated aqueous NH₄Cl (3 mL) and water (4 mL). The organic layer was separated, and the aqueous layer was back extracted with EtOAc (3×15 mL).The organic solutions were combined. After removal of organic solvents under reduced pressure, purification of the residue by flash chromatography on ISCO Gold silica gel column using 0-10% MeOH/dichloromethane (MeOH containing 1% NH₄₀H) as the eluent provided the title compound as a white solid.

Step 5: N-((2S)-4-penten-2-yl)-N-(2-pyridinylmethyl)sulfuric diamide

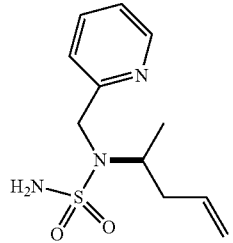

The title compound was prepared from (S)—N-(pyridin-2-ylmethyl)pent-4-en-2-amine (Step 4) following a procedure similar to the one described for the synthesis of N-4-penten-1-ylsulfuric diamide as described in Step 1 for the synthesis of Example 660), except that the crude product was purified by flash chromatography on ISCO Gold silica gel column using 0-90% EtOAc/Hexanes to provide the title compound as a white solid.

Step 6: (S)-6'-chloro-5-((((1R,2R)-2-((S)-1-hydroxyallyl)cyclobutyl)methyl)-N—(N—((S)-pent-4-en-2-yl)-N-(pyridin-2-ylmethyl)sulfamoyl)-3',4,4',5-tetrahydro-2H,2'H-spiro[benzo[b][1,4]oxazepine-3,1'-naphthalene]-7-carboxamide The title compound was prepared from N-((2S)-4-penten-2-yl)-N-(2-pyridinylmethyl)sulfuric diamide (Step 5) and (S)-6',8-dichloro-5-((((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (67 mg, 0.143 mmol, AA11A), following a procedure similar to the one described for the synthesis of (S)-6'-chloro-5-((((1R,2R)-2-((S)-1-hydroxyallyl)cyclobutyl)methyl)-N—(N-(pent-4-en-1-yl)sulfamoyl)-3',4,4',5-tetrahydro-2H,2'H-spiro[benzo[b][1,4]oxazepine-3,1'-naphthalene]-7-carboxamide (Step 2 in the synthesis of Example 660), except that the crude product was purified by flash chromatography on ISCO Gold silica gel column using 0-90% EtOAc/Hexanes to provide the title compound as a white solid. ¹H NMR (400 MHz, CDCl₃) δ 8.55-8.44 (m, 1H), 7.74 (d, J=8.6 Hz, 1H), 7.67 (dt, J=1.7, 7.7 Hz, 1H), 7.55 (d, J=7.8 Hz, 1H), 7.44 (dd, J=1.8, 8.4 Hz, 1H), 7.31 (br. s., 1H), 7.23-7.14 (m, 2H), 7.09 (d, J=2.0 Hz, 1H), 7.01-6.93 (m, 1H), 5.86-5.74 (m, 1H), 5.73-5.60 (m, 1H), 5.33-5.19 (m, 1H), 5.11 (d, J=10.4 Hz, 1H), 5.00-4.88 (m, 2H), 4.88-4.70 (m, 2H), 4.23-4.04 (m, 3H), 3.94-3.80 (m, 1H), 3.73-3.62 (m, 1H), 3.24 (d, J=14.3 Hz, 1H), 3.18-3.03 (m, 1H), 2.83-2.71 (m, 2H), 2.53-2.40 (m, 1H), 2.42-2.28 (m, 1H), 2.21-1.98 (m, 6H), 1.98-1.75 (m, 4H), 1.67 (td, J=9.4, 19.0 Hz, 1H), 1.61-1.50 (m, 1H), 1.49-1.39 (m, 1H), 1.14 (d, J=6.7 Hz, 3H). m/z (ESI, +ve ion) 705.1 (M+H)⁺.

Example 665. (1S,3'R,6'R,7'S,8'E)-6-chloro-7'-hydroxy-13'-(2-methoxyethyl)-3,4-dihydro-2H,16'H-spiro[naphthalene-1,23'-[21]oxa[14]thia[1,13,15]triazatetracyclo[15.7.2.0³,⁶.0²⁰,²⁵]hexacosa[8,17,19,25]tetraen]-16'-one 14',14'-dioxide

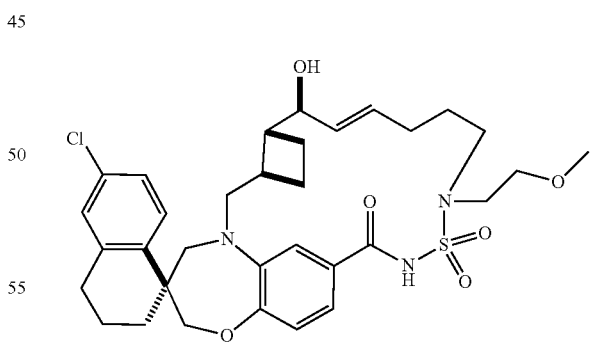

Step 1: N-(2-methoxyethyl)pent-4-en-1-amine

To a rt solution of pent-4-enylamine (0.822 mL, 9.65 mmol, J & W PharmLab, LLC) in CH$_2$Cl$_2$ (20 mL) was added 2-bromoethyl methyl ether (0.908 mL, 9.65 mmol, Sigma-Aldrich Chemical Company, Inc.) followed by diisopropylethylamine (2.5 mL, Sigma-Aldrich Chemical Company, Inc.). The mixture was allowed to stir at rt for 20 h. To the mixture was added potassium carbonate (0.583 mL, 9.65 mmol, Sigma-Aldrich Chemical Company, Inc.) followed by acetonitrile (20 mL), the mixture was refluxed in a 70° C. bath overnight. The reaction vessel was removed from the bath and allowed to cool to rt. The solid was filtered off through a Celite® (diatomaceous earth) pad, and washed with acetonitrile (2×20 mL). The organic solutions were combined. After removal of organic solvents under reduced pressure, purification of the residue by flash chromatography on ISCO Gold silica gel column with 0-100% MeOH in CH$_2$Cl$_2$ (MeOH containing 0.1% NH$_{40}$H) provided the title compound as a colorless syrup.

Step 2: N-(2-methoxyethyl)-N-4-penten-1-ylsulfuric diamide

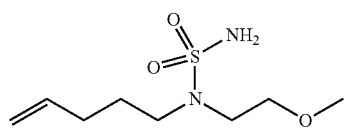

The title compound was prepared from N-(2-methoxyethyl)pent-4-en-1-amine (Step 1) following a procedure similar to the one described for the synthesis of N-4-penten-1-ylsulfuric diamide (Step 1 in Example 660), except that the crude product was purified by flash chromatography on ISCO Gold silica gel column using 0-100% EtOAc/Hexanes to provide the title compound as a white solid.

Step 3: (S)-6'-chloro-5-(((1R,2R)-2-((S)-1-hydroxyallyl)cyclobutyl)methyl)-N—(N-(2-methoxyethyl)-N-(pent-4-en-1-yl)sulfamoyl)-3',4,4',5-tetrahydro-2H,2'H-spiro[benzo[b][1,4]oxazepine-3,1'-naphthalene]-7-carboxamide

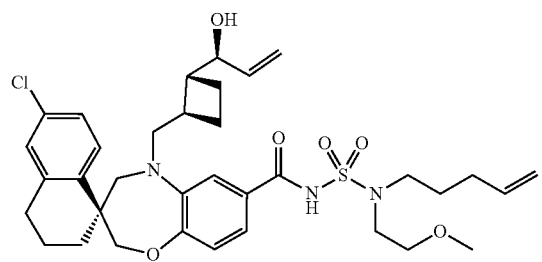 [SMILES: C=CCCCN(CCOC)S(=O)(=O)NC(=O)c1ccc2c(c1)N(C[C@@H]1CC[C@H]1[C@@H](O)C=C)C[C@@]1(CCCc3cc(Cl)ccc31)CO2]

The title compound was prepared from N-(2-methoxyethyl)-N-4-penten-1-ylsulfuric diamide (Step 2) and (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (AA11A), following a procedure similar to the one described for the synthesis of (S)-6'-chloro-5-(((1R,2R)-2-((S)-1-hydroxyallyl)cyclobutyl)methyl)-N—(N-(pent-4-en-1-yl)sulfamoyl)-3',4,4',5-tetrahydro-2H,2'H-spiro[benzo[b][1,4]oxazepine-3,1'-naphthalene]-7-carboxamide (Step 2 in the synthesis of Example 660), except that the crude product was purified by flash chromatography on ISCO Gold silica gel column using 0-70% EtOAc/Hexanes (EtOAc contained 0.1% HOAc) to provide the title compound as a white solid.

Step 4: (1S,3'R,6'R,7'S,8'E)-6-chloro-7'-hydroxy-13'-(2-methoxyethyl)-3,4-dihydro-2H,16'H-spiro[naphthalene-1,23'-[21]oxa[14]thia[1,13,15]triazatetracyclo[15.7.2.0$^{3,6}$.0$^{20,25}$]hexacosa[8,17,19,25]tetraen]-16'-one 14',14'-dioxide The title compound was prepared from (S)-6'-chloro-5-(((1R,2R)-2-((S)-1-hydroxyallyl)cyclobutyl)methyl)-N—(N-(2-methoxyethyl)-N-(pent-4-en-1-yl)sulfamoyl)-3',4,4',5-tetrahydro-2H,2'H-spiro[benzo[b][1,4]oxazepine-3,1'-naphthalene]-7-carboxamide (Step 3), following a procedure similar to the one described in Step 3 for the synthesis of (1S,3'R,6'R,7'S,8'E)-6-chloro-7'-hydroxy-3,4-dihydro-2H,16'H-spiro[naphthalene-1,23'-[21]oxa[14]thia[1,13,15]triazatetracyclo[15.7.2.0$^{3,6}$.0$^{20,25}$]hexacosa[8,17,19,25]tetraen]-16'-one 14',14'-dioxide (Example 660), except that the crude product was purified by flash chromatography on ISCO Gold silica gel column using 0-70% EtOAc/Hexanes (EtOAc contained 0.1% HOAc) to provide the title compound as a white solid. $^1$H NMR (400 MHz, CDCl$_3$) δ 9.36 (br. s., 1H), 7.71 (d, J=8.6 Hz, 1H), 7.24 (dd, J=1.8, 8.2 Hz, 1H), 7.18 (dd, J=2.2, 8.4 Hz, 1H), 7.10 (d, J=2.2 Hz, 1H), 7.02-6.92 (m, 2H), 5.92-5.62 (m, 2H), 4.25-4.01 (m, 4H), 3.78-3.22 (m, 13H), 3.00-1.58 (m, 15H), 1.52 (t, J=11.8 Hz, 1H). m/z (ESI, +ve ion) 644.0 (M+H)$^+$.

Example 666. (2S)-1-((1S,3'R,6'R,7'S,8'E,11'S,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)-3-methoxy-2-propanyl benzoate or (2S)-1-((1S,3'R,6'R,7'S,8'E,11'S,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)-3-methoxy-2-propanyl benzoate

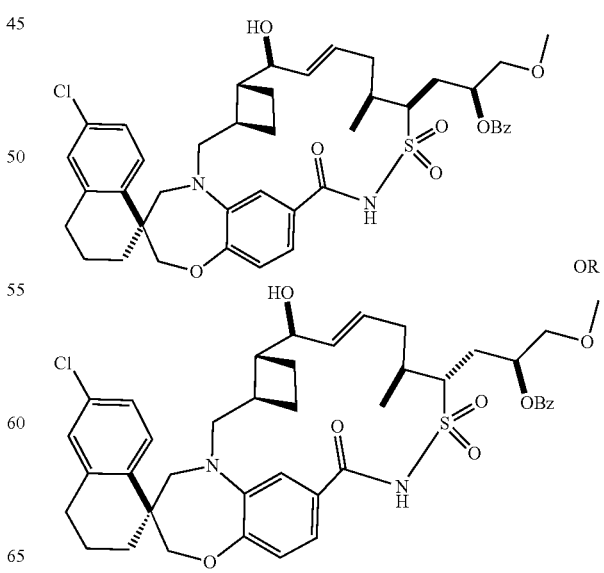

Step 1: (S)—N,N-bis(4-methoxybenzyl)-2-methyl-pent-4-ene-1-sulfonamide

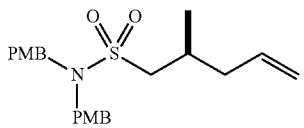

To a solution of N,N-bis(4-methoxybenzyl)methane sulfonamide (9.10 g, 27.1 mmol, EE12) in THF (78 ml) under N₂ in a −78° C. bath was added "BuLi solution (11.9 ml, 2.5 M in hexanes, 29.8 mmol, Sigma-Aldrich Chemical Company, Inc.). The mixture was allowed to stir in the cold bath for 25 min. To the mixture was added a solution of (R)-pent-4-en-2-yl 4-methylbenzenesulfonate (9.78 g, 40.7 mmol) (prepared according to the procedure reported by Sigman, M. S. et al.; *J. Am. Chem. Soc.*, 2012, 134, 11408-11411) in THF (12 mL). The mixture was allowed to stir in the ice bath for 30 min, removed from ice bath, and allowed to stir at rt for 72 h. To the mixture was added 1.0 aqueous HCl (5 mL), the resulting mixture was diluted with water (12 mL) and extracted with EtOAc (2×18 mL). After removal of organic solvents under reduced pressure, purification of the residue by flash chromatography on ISCO Gold silica gel column with 0-25-60% EtOAc/Hexanes provided the title compound as a white solid.

Step 2: (2R,4R,5S)-2-hydroxy-1-methoxy-N,N-bis(4-methoxybenzyl)-5-methyloct-7-ene-4-sulfonamide and (2R,4S,5S)-2-hydroxy-1-methoxy-N,N-bis(4-methoxybenzyl)-5-methyloct-7-ene-4-sulfonamide

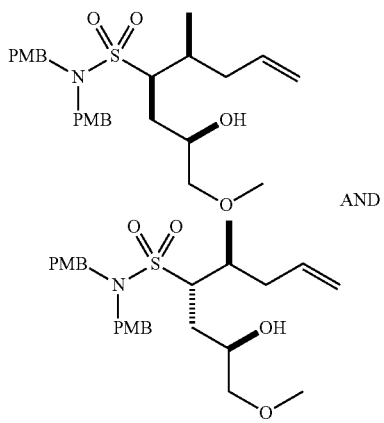

To a solution of (S)—N,N-bis(4-methoxybenzyl)-2-methylpent-4-ene-1-sulfonamide (1.25 g, 3.10 mmol, Step 1) in THF (10.33 ml) under N2 in −78° C. bath was added "BuLi (1.43 ml, 2.5 M in hexanes, 3.56 mmol, Sigma-Aldrich Chemical Company, Inc.) drop wise. The mixture was allowed to stir in the bath for 35 min. To the mixture was added (R)-(−)-glycidyl methyl ether (0.819 ml, 9.29 mmol, Sigma-Aldrich Chemical Company, Inc.) in one shot. The resulting solution was allowed to warm with the ice bath to rt and left to stir at rt overnight. The reaction mixture was quenched with saturated aqueous NH₄Cl (5 mL), diluted with water (12 mL) and extracted with EtOAc (2×15 mL). After removal of organic solvents under reduced pressure, purification of the residue by flash chromatography on ISCO Gold silica gel column with 0-100% EtOAc/Hexanes (EtOAc contained 0.1% HOAc) provided the title compounds as a white solid.

Step 3: (2R,4R,5S)-4-(N,N-bis(4-methoxybenzyl)sulfamoyl)-1-methoxy-5-methyloct-7-en-2-yl benzoate and (2R,4S,5S)-4-(N,N-bis(4-methoxybenzyl)sulfamoyl)-1-methoxy-5-methyloct-7-en-2-yl benzoate

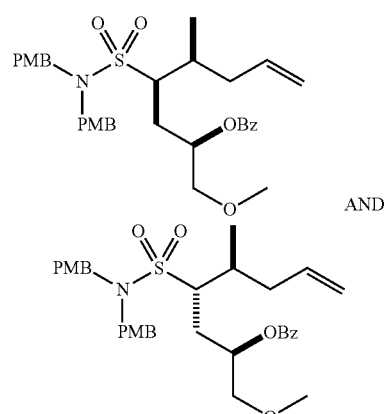

To a 0° C. solution of (2R,4R,5S)-2-hydroxy-1-methoxy-N,N-bis(4-methoxybenzyl)-5-methyloct-7-ene-4-sulfonamide and (2R,4S,5S)-2-hydroxy-1-methoxy-N,N-bis(4-methoxybenzyl)-5-methyloct-7-ene-4-sulfonamide (670 mg, 1.36 mmol, Step 2) and 4-(dimethylamino)pyridine (200 mg, 1.64 mmol, Sigma-Aldrich Chemical Company, Inc.) in CHCl₃ (13 mL) under N₂ in ice bath was added triethylamine, anhydrous (0.569 mL, 4.09 mmol, Sigma-Aldrich Chemical Company, Inc.) followed by benzoyl chloride (0.237 mL, 2.04 mmol, Sigma-Aldrich Chemical Company, Inc.). The mixture was allowed to warm with ice bath to rt and to left to stir at rt overnight. The mixture was quenched with saturated aqueous NaHCO₃ (3 mL), diluted with water (2 mL) and extracted with dichloromethane (3×15 mL). After removal of organic solvents under reduced pressure, purification of the residue by flash chromatography on ISCO Gold silica gel column with 0-80% EtOAc/Hexanes (EtOAc contained 0.1% HOAc) provided the title compounds as a syrup.

Step 4: (2R,4R,5S)-1-methoxy-5-methyl-4-sulfamoyloct-7-en-2-yl benzoate and (2R,4S,5S)-1-methoxy-5-methyl-4-sulfamoyloct-7-en-2-yl benzoate

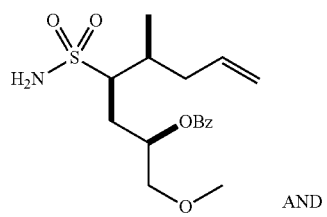

-continued

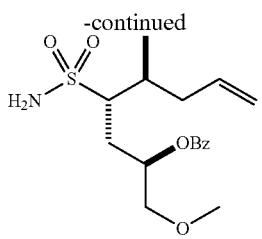

The title compound was prepared from ((2R,4R,5S)-4-(N,N-bis(4-methoxybenzyl)sulfamoyl)-1-methoxy-5-methyloct-7-en-2-yl benzoate and (2R,4S,5S)-4-(N,N-bis(4-methoxybenzyl)sulfamoyl)-1-methoxy-5-methyloct-7-en-2-yl benzoate (Step 3) following a procedure similar to the one described for the synthesis of EE17 (Step 2).

Step 5. (2S,4R,5S)-4-(N—((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-ylcarbonyl)sulfamoyl)-1-methoxy-5-methyloct-7-en-2-yl benzoate and (2S,4S,5S)-4-(N—((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-ylcarbonyl)sulfamoyl)-1-methoxy-5-methyloct-7-en-2-yl benzoate

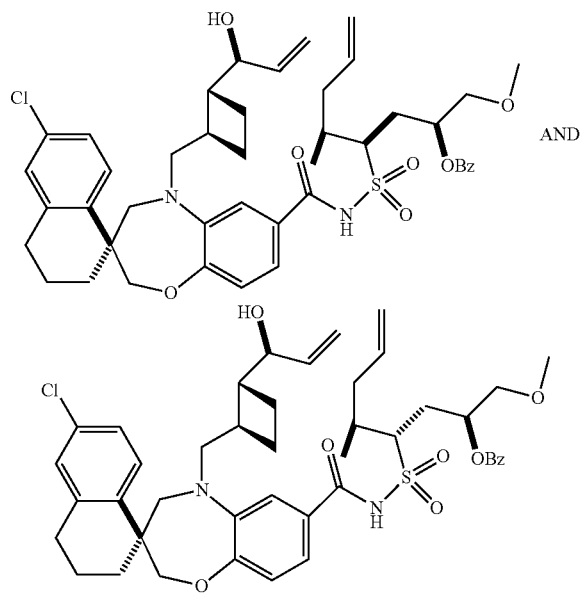

The title compound was prepared from (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (AA11A) and (2R,4R,5S)-1-methoxy-5-methyl-4-sulfamoyloct-7-en-2-yl benzoate and (2R,4S,5S)-1-methoxy-5-methyl-4-sulfamoyloct-7-en-2-yl benzoate (Step 4) following a procedure similar to the one described in Example 660, Step 2, except that the crude product was purified by flash chromatography on ISCO Gold silica gel column using 0-100% EtOAc/Hexanes (EtOAc contained 0.1% HOAc) to provide the title compounds as a white solid.

Step 6. (2S)-1-((1S,3'R,6'R,7'S,8'E,11'S,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)-3-methoxy-2-propanyl benzoate or (2S)-1-((1S,3'R,6'R,7'S,8'E,11'S,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)-3-methoxy-2-propanyl benzoate The title compound was prepared from (2S,4R,5S)-4-(N—((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-ylcarbonyl)sulfamoyl)-1-methoxy-5-methyloct-7-en-2-yl benzoate and (2S,4S,5S)-4-(N—((S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalen]-7-ylcarbonyl)sulfamoyl)-1-methoxy-5-methyloct-7-en-2-yl benzoate (Step 5) following a procedure similar to the one described in Example 660, Step 3, except that the crude product was purified by reversed phase preparatory HPLC (Gemini™ Prep C18 10 μm column; Phenomenex, Torrance, CA; gradient elution of 45% to 90% MeCN in water, where both solvents contain 0.1% TFA, 25 min method) to provide one of the title compounds as the faster eluting isomer as a white foam. $^1$H NMR (400 MHz, CDCl$_3$) δ 8.12 (d, J=7.2 Hz, 2H), 7.67 (d, J=8.6 Hz, 1H), 7.64-7.56 (m, 1H), 7.52-7.45 (m, 2H), 7.22-7.13 (m, 2H), 7.13-7.06 (m, 1H), 6.94-6.86 (m, 2H), 6.82 (s, 1H), 5.82-5.70 (m, 1H), 5.65-5.49 (m, 2H), 4.39 (d, J=8.2 Hz, 1H), 4.20-3.96 (m, 2H), 3.90-3.80 (m, 1H), 3.80-3.56 (m, 4H), 3.51-3.35 (m, 3H), 3.31-3.11 (m, 1H), 2.97 (dd, J=9.3, 14.6 Hz, 1H), 2.88-2.71 (m, 2H), 2.52-1.19 (m, 17H), 1.09-1.02 (d, J=8.2 Hz, 3H). m/z (ESI, +ve ion) 776.9 (M+H)$^+$.

Example 667 (1S,3'R,6'R,7'S,8'E,11'S)-6-chloro-7'-hydroxy-11'-methyl-12'-(2-pyridinylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide or (1S,3'R,6'R,7'S,8'Z,11'S)-6-chloro-7'-hydroxy-11'-methyl-12'-(2-pyridinylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

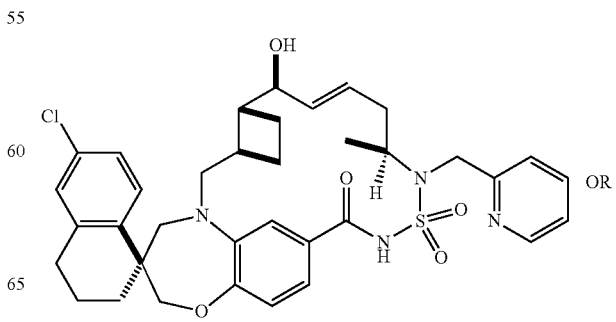

OR

1405
-continued

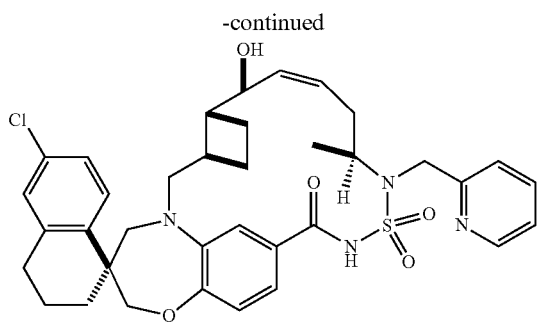

The title compounds were prepared from (S)-6'-chloro-5-(((1R,2R)-2-((S)-1-hydroxyallyl)cyclobutyl)methyl)-N—(N—((S)-pent-4-en-2-yl)-N-(pyridin-2-ylmethyl)sulfamoyl)-3',4,4',5-tetrahydro-2H,2'H-spiro[benzo[b][1,4]oxazepine-3,1'-naphthalene]-7-carboxamide (Example 664) following a procedure similar to Step 3 in the synthesis of Example 660, except that HOAc (10.0 eq.) was added as a co-solvent and the reaction was prolonged to 96 h to completion. The crude product was purified by reversed phase preparatory HPLC (Gemini™ Prep C18 10 μm column; Phenomenex, Torrance, CA; gradient elution of 40% to 95% MeCN in water, where both solvents contain 0.1% TFA, 35 min method) to provide one of the title compounds as the first eluting isomer as a white foam. ¹H NMR (400 MHz, CDCl₃) δ 8.72 (d, J=5.5 Hz, 1H), 8.39 (t, J=7.5 Hz, 1H), 8.26-8.18 (m, 1H), 7.83-7.75 (m, 1H), 7.74-7.65 (m, 1H), 7.18 (dd, J=2.2, 8.5 Hz, 1H), 7.10 (d, J=2.2 Hz, 1H), 7.00-6.85 (m, 3H), 5.92-5.66 (m, 3H), 5.21 (d, J=19.2 Hz, 1H), 4.39-4.26 (m, 2H), 4.16-4.06 (s, 2H), 3.83 (d, J=14.7 Hz, 1H), 3.75-3.66 (d, J=14.5 Hz, 1H), 3.19 (d, J=14.3 Hz, 1H), 3.03 (dd, J=8.8, 15.5 Hz, 1H), 2.86-2.69 (m, 2H), 2.66-2.49 (m, 2H), 2.41-2.13 (m, 3H), 2.11-1.58 (m, 8H), 1.46-1.36 (m, 1H), 1.17-1.08 (m, 3H). m/z (ESI, +ve ion) 677.0 (M+H)⁺;

Example 668. (1S,3'R,6'R,7'S,8'E,11'S)-6-chloro-7'-hydroxy-11'-methyl-12'-(2-pyridinylmethyl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide or (1S,3'R,6'R,7'S,8'Z,11'S)-6-chloro-7'-hydroxy-11'-methyl-12'-(2-pyridinylmethyl)-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide 1406
-continued

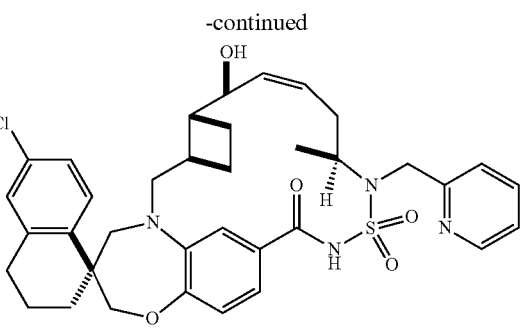

The title compound was obtained as a white foam as the second eluting isomer from the reversed phase preparatory HPLC separation in Example 667. ¹H NMR (400 MHz, CDCl₃) δ 8.43 (d, J=3.9 Hz, 1H), 7.81-7.66 (m, 2H), 7.61 (d, J=8.0 Hz, 1H), 7.26-7.16 (m, 2H), 7.08 (dd, J=2.0, 11.0 Hz, 2H), 7.03-6.96 (m, 1H), 6.94-6.86 (m, 1H), 6.56 (dd, J=7.7, 15.2 Hz, 1H), 5.97 (d, J=15.6 Hz, 1H), 5.26 (d, J=16.2 Hz, 1H), 4.54 (d, J=17.2 Hz, 1H), 4.32-0.82 (m, 29H); 677.0 (M+H)⁺.

Example 669. (1S,3'R,6'R,7'S,8'E,11'S,12'R)-6-chloro-7'-(2-methoxyethoxy)-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'S,12'S)-6-chloro-7'-(2-methoxyethoxy)-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'Z,11'S,12'R)-6-chloro-7'-(2-methoxyethoxy)-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'Z,11'S,12'S)-6-chloro-7'-(2-methoxyethoxy)-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

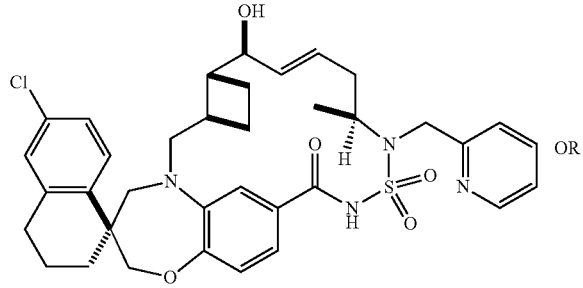 OR 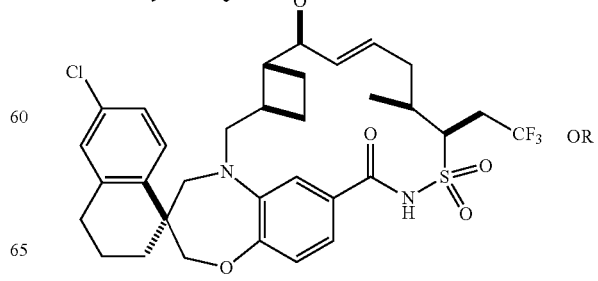 OR

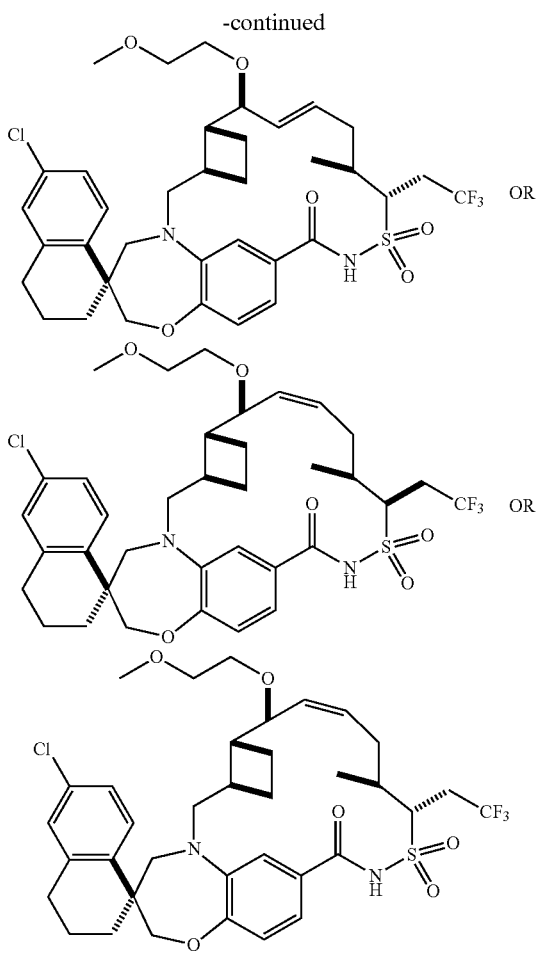

To a solution of (1S,3'R,6'R,7'S,8'E,11'S,12'R)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide or (1S,3'R,6'R,7'S,8'Z,11'S,12'R)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one or (1S,3'R,6'R,7'S,8'Z,11'S,12'S)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (32 mg, 0.048 mmol, Example 663) in DMF (2 mL) under $N_2$ was added sodium hydride (19 mg, 60% dispersion in mineral oil, 0.480 mmol, Strem Chemicals, Inc.) at 0° C. The mixture was allowed to stir in the ice bath for 15 min, followed by addition of 2-bromoethyl methyl ether (0.023 mL, 0.24 mmol, 96%, stabilized with sodium carbonate, Sigma-Aldrich Chemical Company, Inc.). The resulting mixture was removed from the ice bath and continued to stir at rt for overnight. The reaction mixture was quenched with saturated aqueous $NH_4Cl$ solution (3 mL), diluted with water (3 mL) and extracted with EtOAc (3×5 mL). The organic layers were combined, washed with water (2×5 mL), brine and dried over $MgSO_4$. After removal of organic solvents under reduced pressure, purification of the residue by flash chromatography on ISCO Gold silica gel column with 40-100% EtOAc/Hexanes (EtOAc containing 0.1% HOAc) provided the title compound as a white solid. $^1$H NMR (400 MHz, CDCl$_3$) δ 8.21 (br. s., 1H), 7.69 (d, J=8.6 Hz, 1H), 7.18 (dd, J=2.2, 8.6 Hz, 1H), 7.10 (d, J=2.0 Hz, 1H), 6.99-6.87 (m, 3H), 5.77 (m, 1H), 5.58 (m, 1H), 4.55 (t, J=4.7 Hz, 1H), 4.17-4.06 (m, 2H), 3.88-3.76 (m, 2H), 3.74-3.66 (m, 1H), 3.60-3.40 (m, 4H), 3.29-1.40 (m 22H), 1.16-1.05 (m, 3H). m/z (ESI, +ve ion) 725.2 (M+H)$^+$.

Example 670. (1S,3'R,6'R,7'S,8'E,11'S,12'R)-6-chloro-7'-(2-methoxyethoxy)-11'-methyl-12'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-(2-methoxyethoxy)-11'-methyl-12'-phenyl-3,4-dihydro-2H,15'H-spiro[naphthalene-1,22'-[20]oxa [13]thia[1,14]diazatetracyclo[14.7.2.0$^{3,6}$.0$^{19,24}$] pentacosa [8,16,18,24]tetraen]-15'-one 13',13'-dioxide

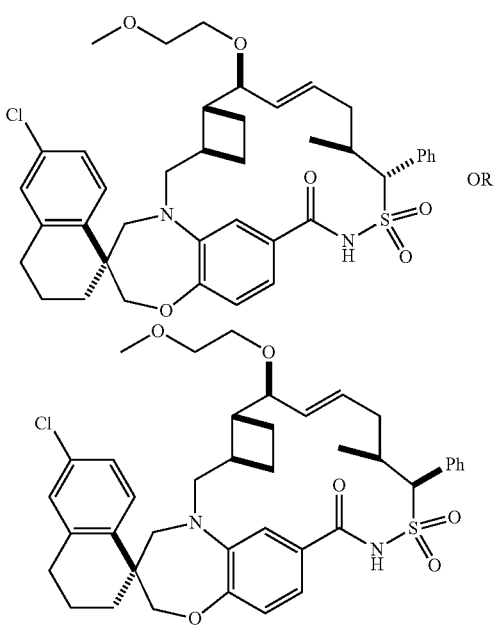

The title compounds were prepared from 2-bromoethyl methyl ether (96%, stabilized with sodium carbonate, Sigma-Aldrich Chemical Company, Inc.) and the crude product obtained from Step 5 in the synthesis of (1S,3'R,6'R,7'S,8'E,11'S,12'R)-6-chloro-7'-hydroxy-11'-methyl-12'-phenyl-3,4-dihydro-2H,15'H-spiro[naphthalene-1,22'-[20]oxa[13]thia[1,14]diazatetracyclo[14.7.2.0$^{3,6}$.0$^{19,24}$] pentacosa[8,16,18,24]tetraen]-15'-one 13',13'-dioxide and (1S,3'R,6'R,7'S,8'E,11'S,12'S)-6-chloro-7'-hydroxy-11'-methyl-12'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 653), following a procedure similar to the one described for the synthesis of Example 669, except that the crude product after removal of organic solvents was redissolved in DMF (3 mL) and subjected to reverse phase preparatory HPLC (Gemini™ Prep C18 10 μm column; Phenomenex, Torrance, CA; gradient elution of 10% MeCN in water to 90% MeCN in water over a 30 min period, where both solvents contain 0.1% TFA) for purification to provide one of the title compounds as the first eluting fraction as a white foam. $^1$H NMR (400 MHz, CDCl$_3$) δ 8.14 (s, 1H), 7.71 (d, J=8.41 Hz, 1H), 7.48-7.58 (m, 2H), 7.39-7.47 (m, 3H), 7.19 (dd, J=8.51, 2.25 Hz, 1H), 7.10 (d, J=2.15 Hz, 1H), 6.85-6.99 (m, 3H), 5.93-6.08 (m, 1H), 5.59 (dd, J=15.26, 9.00 Hz, 1H), 5.44 (d, J=4.11 Hz, 1H), 4.02-4.19 (m, 2H), 3.79-3.95 (m, 2H), 3.73 (d, J=13.89 Hz, 1H), 3.46-3.67 (m, 4H), 3.37-3.44 (m, 3H), 3.23 (d, J=14.28 Hz, 1H), 3.00 (m, 1H), 2.74-2.83 (m, 2H), 2.47-2.61 (m, 1H), 2.13-2.46 (m, 2H), 1.91-2.13 (m, 4H), 1.83 (m, 3H), 1.63 (m, 1H), 1.21-1.48 (m, 2H), 1.01 (d, J=6.85 Hz, 3H). m/z (ESI, +ve ion) 719.1 (M+H)$^+$.

Example 671. (1S,3'R,6'R,7'S,8'E,11'S,12'R)-6-chloro-7'-(2-methoxyethoxy)-11'-methyl-12'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-(2-methoxyethoxy)-11'-methyl-12'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

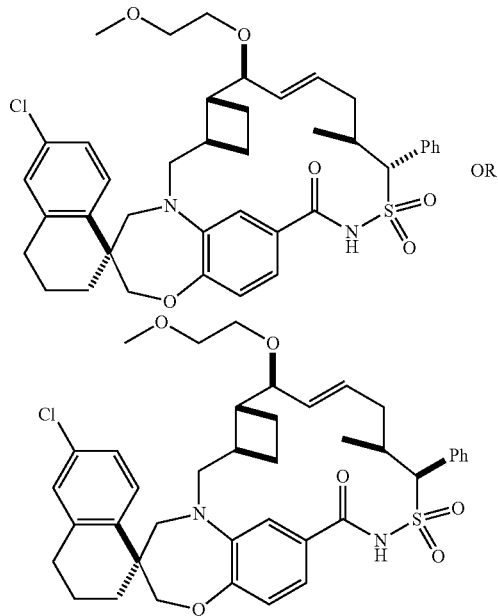

The title compound was obtained as a white foam as the second eluting isomer from the reversed phase preparatory HPLC separation in Example 670. $^1$H NMR (400 MHz, CDCl$_3$) δ $^1$H NMR (400 MHz, CDCl$_3$) δ 8.08 (br. s., 1H), 7.70 (d, J=8.41 Hz, 1H), 7.52-7.61 (m, 2H), 7.38-7.50 (m, 3H), 7.16-7.25 (m, 2H), 7.10 (d, J=2.15 Hz, 1H), 7.00 (d, J=8.22 Hz, 1H), 6.74 (m, 1H), 6.11 (m, 1H), 5.54 (dd, J=15.65, 7.83 Hz, 1H), 4.96 (br. s., 1H), 4.03-4.20 (m, 2H), 3.71-3.84 (m, 2H), 3.59-3.70 (m, 2H), 3.51-3.59 (m, 2H), 3.41-3.51 (m, 2H), 3.38 (s, 3H), 2.97 (m, 1H), 2.73-2.86 (m, 2H), 2.45-2.64 (m, 2H), 2.33 (m, 1H), 1.63-2.15 (m, 9H), 1.50 (m, 1H), 0.97 (d, J=6.85 Hz, 3H). m/z (ESI, +ve ion) 719.1 (M+H)$^+$.

Example 672. (1S,3'R,6'R,7'S,8'E,11'S,12'R)-6-chloro-7'-hydroxy-12'-((2S)-2-hydroxy-3-methoxypropyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-12'-((2S)-2-hydroxy-3-methoxypropyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

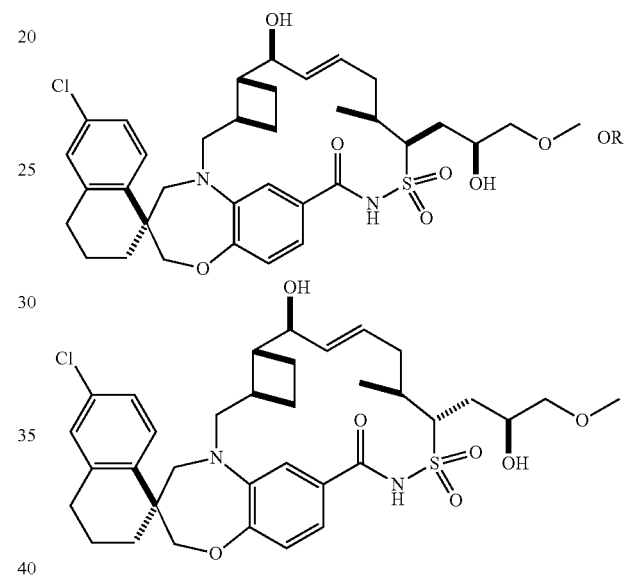

Step 1: (2S)-1-((1S,3'R,6'R,7'S,8'E,11'S,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)-3-methoxy-2-propanyl benzoate and (2S)-1-((1S,3'R,6'R,7'S,8'E,11'S,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)-3-methoxy-2-propanyl benzoate

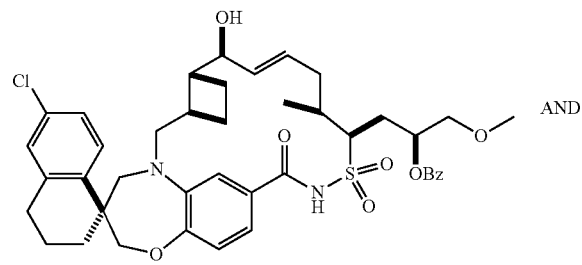

-continued

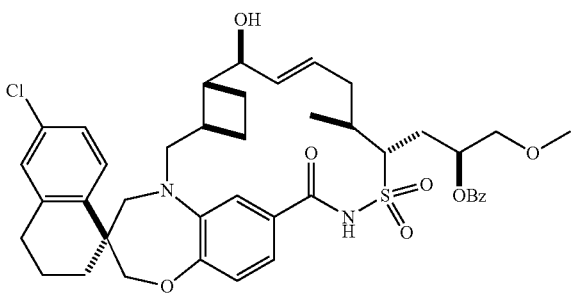

The title compounds were prepared as a mixture following the procedure described in Step 6 for the synthesis of Example 666, except that the crude product was purified by flash chromatography on ISCO Gold silica gel column using 0-100% EtOAc/Hexanes (EtOAc contained 0.1% HOAc) to provide the title compounds as a mixture as a white solid. m/z (ESI, +ve ion) 777.3 (M+H)+.

Step 2. (1S,3'R,6'R,7'S,8'E,11'S,12'R)-6-chloro-7'-hydroxy-12'-((2S)-2-hydroxy-3-methoxypropyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-12'-((2S)-2-hydroxy-3-methoxypropyl)-11'-methyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide A mixture of crude (2S)-1-((1S,3'R,6'R,7'S,8'E,12'S)-6-chloro-7'-methoxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)-3-methoxy-2-propanyl benzoate or (2S)-1-((1S,3'R,6'R,7'S,8'E,12'R)-6-chloro-7'-methoxy-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)-3-methoxy-2-propanyl benzoate (Step 1) (32 mg, 0.041 mmol) and lithium hydroxide monohydrate (69.2 mg, 1.65 mmol, Sigma-Aldrich Chemical Company, Inc.) in THF/MeOH/water (3:1:1, 3 mL) was allowed to stir in a 55° C. bath for 1.5 h. The reaction mixture was removed from the bath and allowed to stir at rt for overnight. The organic solvents were removed under reduced pressure. The resultant mixture was treated with AcOH (0.1 mL), diluted with water (3 mL), and extracted with 30% PrOH/chloroform (3×6 mL). The organic solutions were combined. After removal of organic solvents under reduced pressure, the crude product was re-dissolved in DMF (1 mL) and subjected to reverse phase preparatory HPLC (Gemini™ Prep C18 10 μm column; Phenomenex, Torrance, CA; gradient elution of 10% MeCN in water to 90% MeCN in water over a 30 min period, where both solvents contain 0.1% TFA) for purification to provide one of the title compounds as the first eluting fraction as a white foam. ¹H NMR (400 MHz, CDCl₃) δ 8.19 (br. s., 1H), 7.69 (d, J=8.6 Hz, 1H), 7.18 (dd, J=2.1, 8.5 Hz, 1H), 7.10 (s, 1H), 7.00-6.87 (m, 3H), 5.89 (d, J=9.0 Hz, 1H), 5.72 (dd, J=7.4, 14.7 Hz, 1H), 4.54 (d, J=10.2 Hz, 1H), 4.40 (br. s., 1H), 4.27 (br. s., 1H), 4.09 (s, 2H), 3.81 (d, J=15.7 Hz, 1H), 3.69 (d, J=14.3 Hz, 1H), 3.51 (m, 1H), 3.42 (m, 4H), 3.24 (d, J=14.3 Hz, 1H), 3.09-2.95 (m, 1H), 2.88-1.17 (m, 19H), 1.05 (d, J=6.5 Hz, 3H). m/z (ESI, +ve ion) 673.3 (M+H)+.

Example 673. (1S,3'R,6'R,7'S,8'E,11'S,12'R)-6-chloro-7'-hydroxy-12'-((2S)-2-hydroxy-3-methoxypropyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-7'-hydroxy-12'-((2S)-2-hydroxy-3-methoxypropyl)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

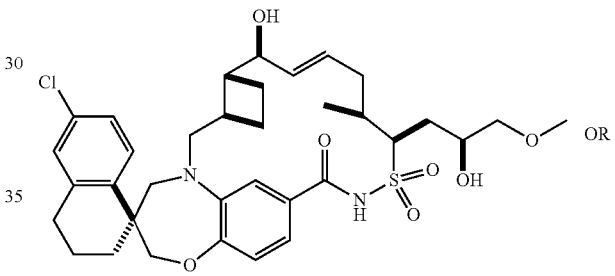

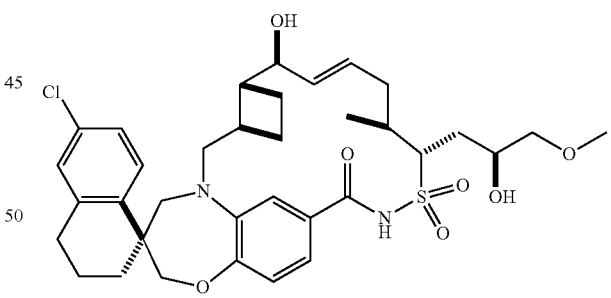

The title compound was obtained as a white foam as the second eluting isomer from the reversed phase preparatory HPLC separation in Example 672, Step 2. ¹H NMR (400 MHz, CDCl₃) δ 8.19 (br. s., 1H), 7.78-7.59 (m, 1H), 7.18 (d, J=6.8 Hz, 1H), 7.09 (s., 1H), 7.03-6.84 (m, 3H), 5.84-5.61 (m, 1H), 5.60-5.54 (m, 1H), 4.61-4.31 (m, 1H), 4.23 (d, J=18.2 Hz, 1H), 4.17-3.97 (m, 3H), 4.00-3.61 (m, 4H), 3.61-1.21 (m, 24H), 1.20-0.98 (m, 3H). m/z (ESI, +ve ion) 673.3 (M+H)+.

Example 674. (1S,3'R,6'R,7'S,8'E,12'S)-6-chloro-7'-hydroxy-12'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-hydroxy-12'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

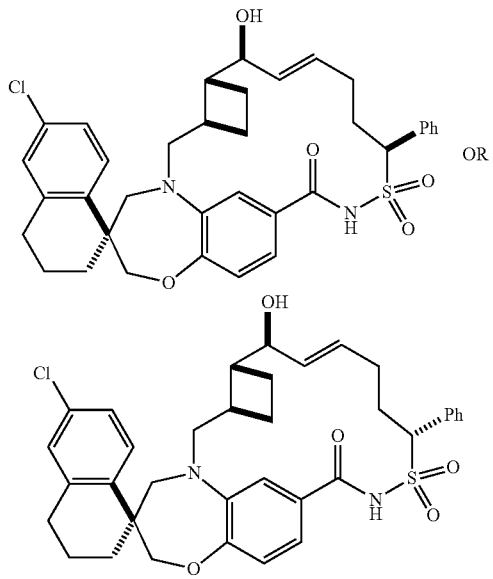

Step 1: ((S)—N,N-bis(4-methoxybenzyl)-1-phenyl-pent-4-ene-1-sulfonamide and (R)—N,N-bis(4-methoxybenzyl)-1-phenylpent-4-ene-1-sulfonamide

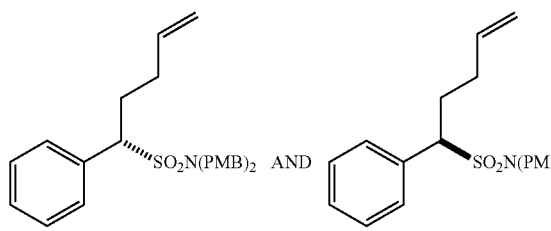

To a solution of N,N-bis(4-methoxybenzyl)-1-phenyl-methanesulfonamide (3.00 g, 7.29 mmol, prepared in Step 1 in the synthesis of Example 653) in THF (36.5 mL) under $N_2$ in bath was added sodium bis(trimethylsilyl)amide (8.02 mL, 1.0 M solution in THF, 8.02 mmol, Sigma-Aldrich Chemical Company, Inc.) at −78° C. After stirring in −78° C. bath for 10 min, to the solution was added 4-bromobut-1-ene (0.757 mL, 7.29 mmol, Sigma-Aldrich Chemical Company, Inc.). The resulting mixture was removed from the bath and was allowed to warm to rt over 1.0 h. Additional sodium bis(trimethylsilyl)amide (8.02 mL, 1.0 M solution in THF, 8.02 mmol, Sigma-Aldrich Chemical Company, Inc.) was added, and the solution was allowed to stir at rt for 1.5 h. The solution was quenched with saturated aqueous $NH_4Cl$ (10 mL), diluted with water (10 mL) and extracted with EtOAc (3×15 mL). The organic layers were combined. After removal of organic solvents under reduced pressure, purification of the residue by flash chromatography on ISCO Gold silica gel column with 0-70% EtOAc/Hexanes provided the title compound as a white solid.

Step 2: (S)-1-phenylpent-4-ene-1-sulfonamide and (R)-1-phenylpent-4-ene-1-sulfonamide

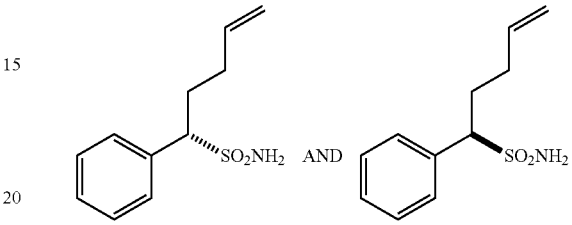

The title compounds were prepared as a mixture two isomers from ((S)—N,N-bis(4-methoxybenzyl)-1-phenyl-pent-4-ene-1-sulfonamide and (R)—N,N-bis(4-methoxybenzyl)-1-phenylpent-4-ene-1-sulfonamide (Step 1) following a procedure similar to the one described for the synthesis of EE17 (Step 2).

Step 3: (S)-6'-chloro-5-(((1R,2R)-2-((S)-1-hydroxyallyl)cyclobutyl)methyl)-N—(((S)-1-phenylpent-4-en-1-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxyallyl)cyclobutyl)methyl)-N—(((R)-1-phenylpent-4-en-1-yl)sulfonyl)-3',4,4',5-tetrahydro-2H,2'H-spiro[benzo[b][1,4]oxazepine-3,1'-naphthalene]-7-carboxamide

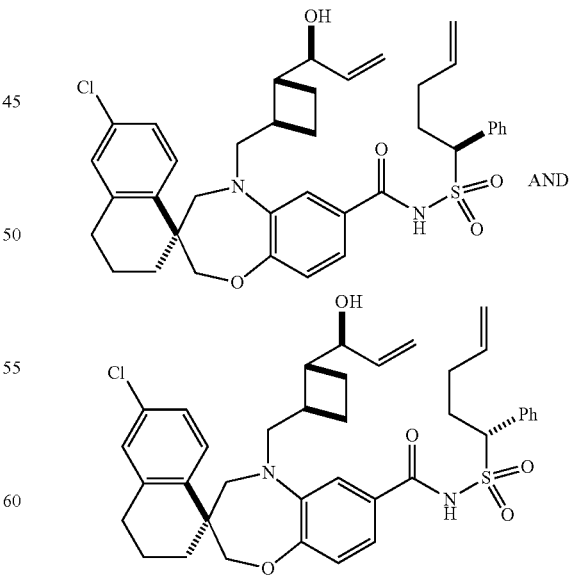

The title compounds were prepared as a mixture of two isomers from (S)-1-phenylpent-4-ene-1-sulfonamide and (R)-1-phenylpent-4-ene-1-sulfonamide (Step 2), and (S)-6'-

1415 chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (AA11A), following a procedure similar to the one described in Step 2 for the synthesis of Example 660, except that the crude product was purified by flash chromatography on ISCO Gold silica gel column using 0-60% EtOAc/Hexanes (EtOAc contained 0.1% HOAc) to provide the title compound as a white solid. m/z (ESI, +ve ion) 675.2 (M+H)+.

Step 4: (1S,3'R,6'R,7'S,8'E,12'S)-6-chloro-7'-hydroxy-12'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-hydroxy-12'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compound was prepared from (S)-6'-chloro-5-(((1R,2R)-2-((S)-1-hydroxyallyl)cyclobutyl)methyl)-N—(((S)-1-phenylpent-4-en-1-yl)sulfonyl)-3',4,4',5-tetrahydro-2H,2'H-spiro[benzo [b][1,4]oxazepine-3,1'-naphthalene]-7-carboxamide and (S)-6'-chloro-5-(((1R,2R)-2-((S)-1-hydroxyallyl)cyclobutyl)methyl)-N—(((R)-1-phenylpent-4-en-1-yl)sulfonyl)-3',4,4',5-tetrahydro-2H,2'H-spiro[benzo[b][1,4]oxazepine-3,1'-naphthalene]-7-carboxamide (Step 3) following a procedure similar to the one described in Step 3 for the synthesis of Example 660, except that the crude product was purified by reversed phase preparatory HPLC (Gemini™ Prep C18 5 μm column; Phenomenex, Torrance, CA; gradient elution of 50% to 90% MeCN in water, where both solvents contain 0.1% TFA, 25 min method) to provide one of one of the title compounds as the first eluting isomer as a white foam. $^1$H NMR (400 MHz, CDCl$_3$) δ 8.25 (br. s., 1H), 7.77-7.62 (m, 2H), 7.62-7.52 (m, 2H), 7.52-7.39 (m, 3H), 7.23-7.14 (m, 2H), 7.11 (d, J=2.2 Hz, 1H), 6.99-6.91 (m, 1H), 5.71 (dd, J=4.2, 15.9 Hz, 1H), 5.62-5.48 (m, 1H), 5.19 (d, J=10.8 Hz, 1H), 4.31-4.20 (m, 2H), 4.18-4.03 (m, 1H), 3.96 (br. s., 1H), 3.87-3.75 (m, 1H), 3.40-3.28 (m, 1H), 3.15 (d, J=16.2 Hz, 1H), 2.76 (br. s., 2H), 2.65-2.51 (m, 2H), 2.51-2.39 (m, 1H), 2.38-1.22 (m, 12H). m/z (ESI, +ve ion) 647.0 (M+H)+.

Example 675. (1S,3'R,6'R,7'S,8'E,12'S)-6-chloro-7'-hydroxy-12'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-hydroxy-12'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

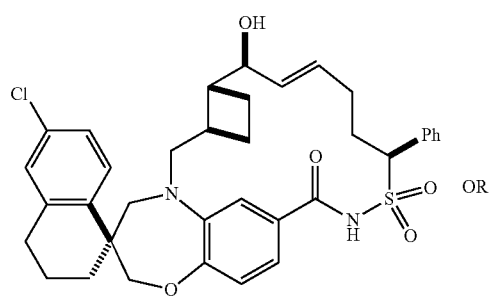

1416

-continued

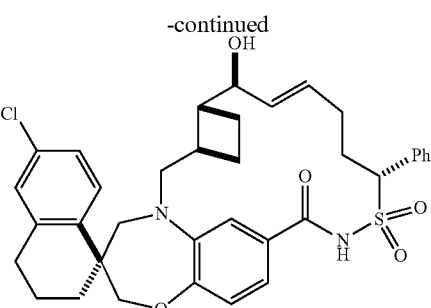

The title compound was obtained as a white foam as the second eluting isomer from the reversed phase preparatory HPLC separation in Example 674, Step 4. $^1$H NMR (400 MHz, CDCl$_3$) δ 8.15-8.00 (m, 1H), 7.72 (d, J=8.0 Hz, 1H), 7.54 (d, J=14.9 Hz, 2H), 7.42 (d, J=19.4 Hz, 3H), 7.25-7.00 (m, 3H), 6.94 (d, J=6.3 Hz, 2H), 5.90 (d, J=10.8 Hz, 1H), 5.75-5.70 (m, 1H), 5.45-5.26 (m, 1H), 4.32-3.97 (m, 3H), 3.93-3.62 (m, 2H), 3.31-3.14 (m, 1H), 2.99-1.22 (m, 18H); m/z (ESI, +ve ion) 647.0 (M+H)+.

Example 676. (1S,3'R,6'R,7'S,8'E,11'R,12'R)-6-chloro-11'-cyclopropyl-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-11'-cyclopropyl-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-11'-cyclopropyl-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-11'-cyclopropyl-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

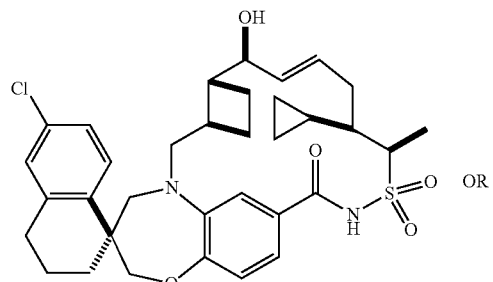

OR

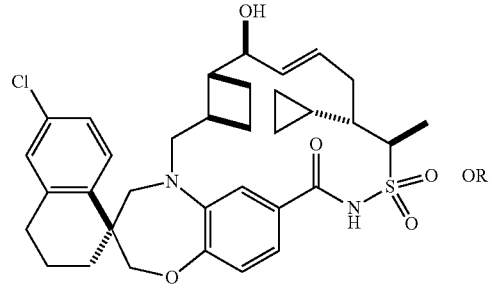

OR

1417

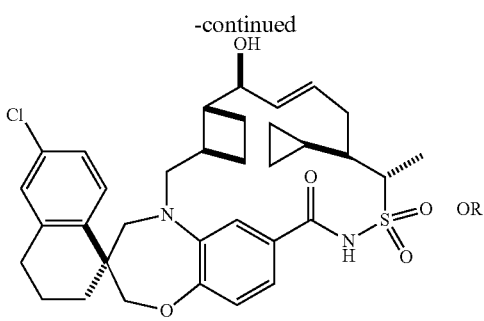

Step 1: (R)-2-cyclopropyl-N,N-bis(4-methoxybenzyl)pent-4-ene-1-sulfonamide and (S)-2-cyclopropyl-N,N-bis(4-methoxybenzyl)pent-4-ene-1-sulfonamide

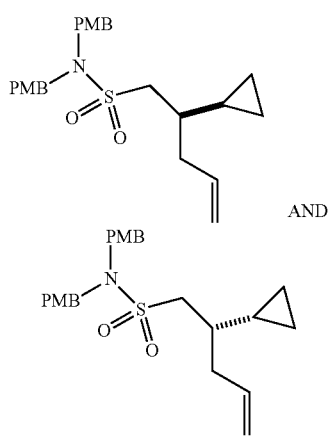

The title compounds were prepared from (R)-2-cyclopropylpent-4-ene-1-sulfonamide and (S)-2-cyclopropylpent-4-ene-1-sulfonamide (prepared in Step 8 for the synthesis of Example 690) following a procedure similar to the one described for the synthesis of EE12, except that the crude product was purified by flash chromatography on ISCO Gold silica gel column using 0-60% EtOAc/Hexanes to provide the title compounds as a mixture of two isomers.

1418

Step 2: (2S,3R)-3-cyclopropyl-N,N-bis(4-methoxybenzyl)hex-5-ene-2-sulfonamide and (2R,3R)-3-cyclopropyl-N,N-bis(4-methoxybenzyl)hex-5-ene-2-sulfonamide and (2S,3S)-3-cyclopropyl-N,N-bis(4-methoxybenzyl)hex-5-ene-2-sulfonamide and (2R,3S)-3-cyclopropyl-N,N-bis(4-methoxybenzyl)hex-5-ene-2-sulfonamide

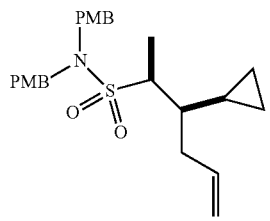

AND

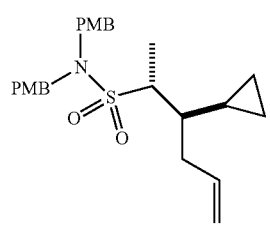

AND

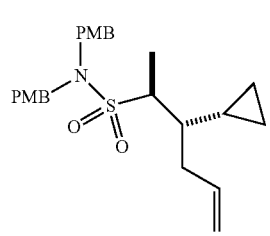

AND

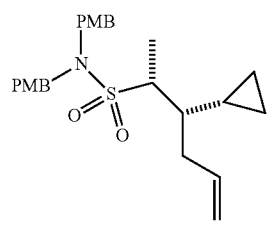

The title compounds were prepared from (R)-2-cyclopropyl-N,N-bis(4-methoxybenzyl)pent-4-ene-1-sulfonamide and (S)-2-cyclopropyl-N,N-bis(4-methoxybenzyl)pent-4-ene-1-sulfonamide (Step 1) following a procedure similar to the one described for the synthesis of EE17 (Step 1), except that the crude product was purified by flash chromatography on ISCO Gold silica gel column using 0-30% EtOAc/Hexanes to provide the title compounds as a mixture of four isomers. m/z (ESI, +ve ion) 444.1 (M+H)$^+$.

1419

Step 3: (2S,3R)-3-cyclopropylhex-5-ene-2-sulfonamide and (2R,3R)-3-cyclopropylhex-5-ene-2-sulfonamide and (2S,3S)-3-cyclopropylhex-5-ene-2-sulfonamide and (2R,3S)-3-cyclopropylhex-5-ene-2-sulfonamide

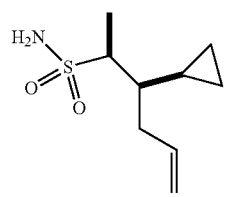
AND
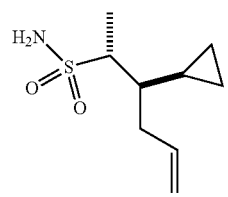
AND

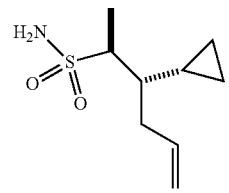
AND
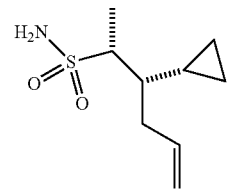

The title compounds were prepared from (2S,3R)-3-cyclopropyl-N,N-bis(4-methoxybenzyl)hex-5-ene-2-sulfonamide and (2R,3R)-3-cyclopropyl-N,N-bis(4-methoxybenzyl)hex-5-ene-2-sulfonamide and (2S,3S)-3-cyclopropyl-N,N-bis(4-methoxybenzyl)hex-5-ene-2-sulfonamide and (2R,3S)-3-cyclopropyl-N,N-bis(4-methoxybenzyl)hex-5-ene-2-sulfonamide (Step 2) following a procedure similar to the one described for the synthesis of EE17 (Step 2), except that the crude product was purified by flash chromatography on ISCO Gold silica gel column using 0-100% EtOAc/Hexanes (EtOAc contained 0.1% HOAc) to provide the title compounds as a mixture.

1420

Step 4: (S)-6'-chloro-5-(((1R,2R)-2-((1S,5S,6S,E)-5-cyclopropyl-1-hydroxy-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1S,5S,6R,E)-5-cyclopropyl-1-hydroxy-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1S,5R,6S,E)-5-cyclopropyl-1-hydroxy-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1S,5R,6R,E)-5-cyclopropyl-1-hydroxy-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic Acid

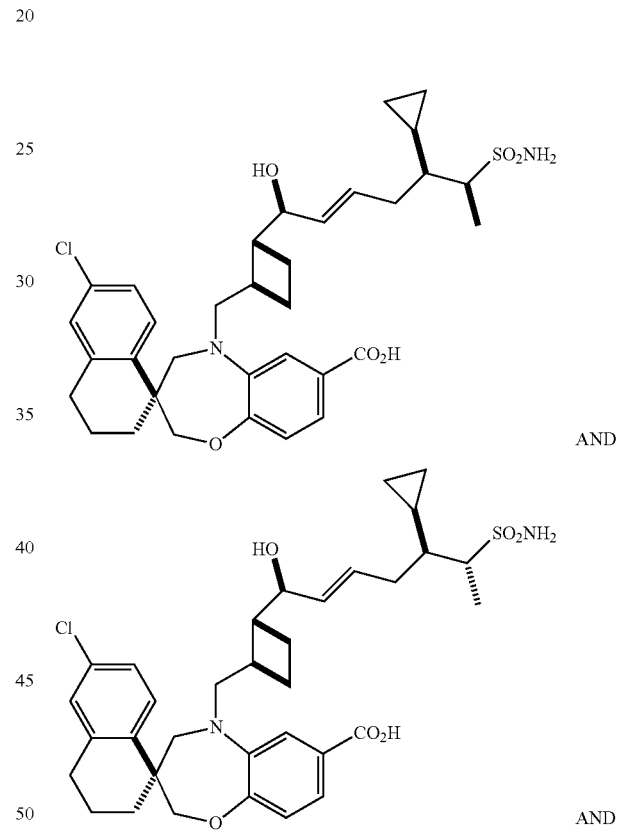
AND

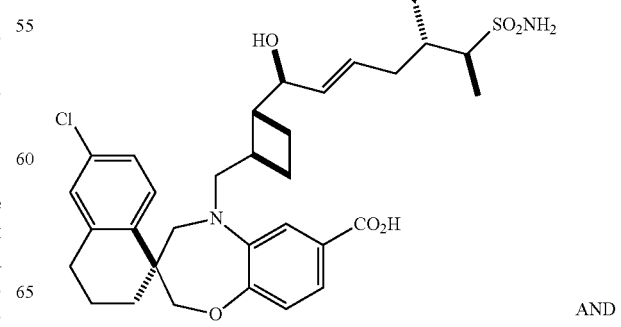
AND

1421

-continued

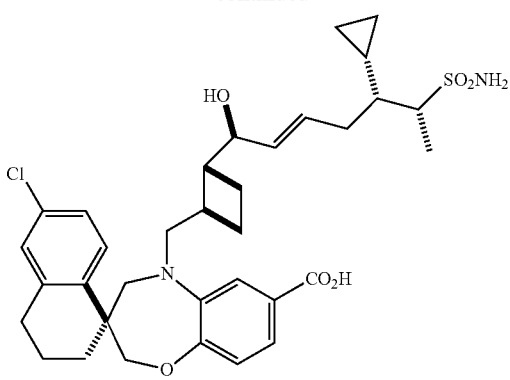

The title compounds were prepared as a mixture from (S)-6'-chloro-5-(((1R,2R)-2-((S)-1-hydroxyallyl)cyclobutyl)methyl)-3',4',4',5-tetrahydro-2H,2'H-spiro[benzo[b][1,4]oxazepine-3,1'-naphthalene]-7-carboxylic acid (AA11A) and (2S,3R)-3-cyclopropylhex-5-ene-2-sulfonamide and (2R,3R)-3-cyclopropylhex-5-ene-2-sulfonamide and (2S,3S)-3-cyclopropylhex-5-ene-2-sulfonamide and (2R,3S)-3-cyclopropylhex-5-ene-2-sulfonamide (Step 3) following a procedure similar to the one described in Step 4 for the synthesis of Example 653.

Step 5: (1S,3'R,6'R,7'S,8'E,11'R,12'R)-6-chloro-11'-cyclopropyl-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl acetate and (1S,3'R,6'R,7'S,8'E,11'R,12'S)-6-chloro-11'-cyclopropyl-12'-methyl-13',13'-dioxido-15'-oxo-3,4-dihydro-2H-spiro[naphthalene-1,22'-[20]oxa[13]thia[1,14]diazatetracyclo [14.7.2.0$^{3,6}$.0$^{19,24}$]pentacosa[8,16,18,24]tetraen]-7'-yl acetate and (1S,3'R,6'R,7'S,8'E,11'S,12'R)-6-chloro-11'-cyclopropyl-12'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl acetate and (1S,3'R,6'R,7'S,8'E,11'S,12'S)-6-chloro-11'-cyclopropyl-12'-methyl-13',13'-dioxido-15'-oxo-3,4-dihydro-2H-spiro[naphthalene-1,22'-[20]oxa[13]thia[1,14]diazatetracyclo [14.7.2.0$^{3,6}$.0$^{19,24}$]pentacosa[8,16,18,24]tetraen]-7'-yl acetate

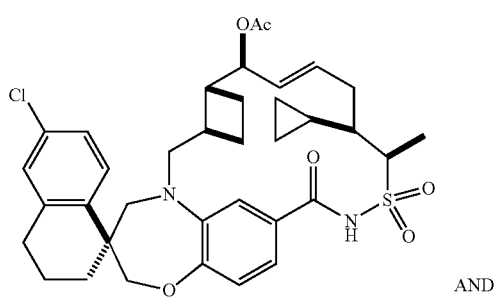

AND

1422

-continued

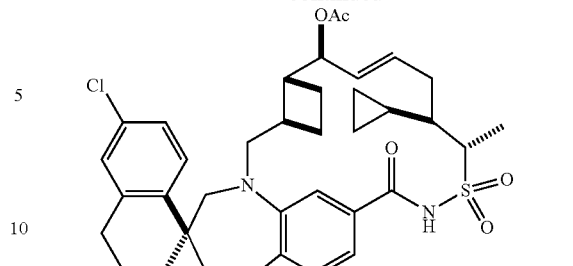

AND

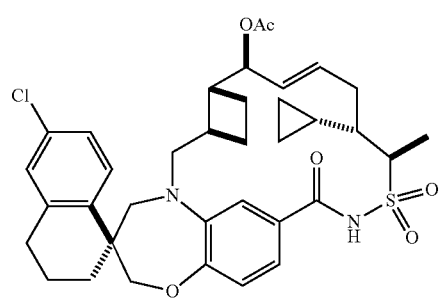

AND

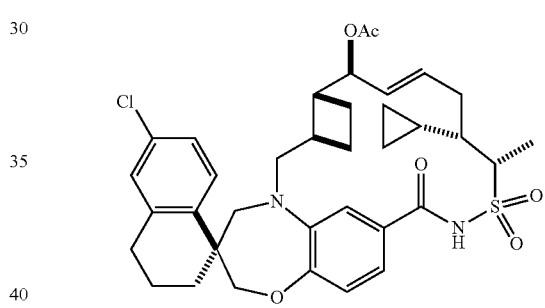

The title compounds were prepared from (S)-6'-chloro-5-(((1R,2R)-2-((1S,5S,6S,E)-5-cyclopropyl-1-hydroxy-6-sulfamoylhept-2-en-1-yl)cyclobutyl)methyl)-3',4',4',5-tetrahydro-2H,2'H-spiro[benzo[b][1,4]oxazepine-3,1'-naphthalene]-7-carboxylic acid and (S)-6'-chloro-5-(((1R,2R)-2-((1S,5s,6R,E)-5-cyclopropyl-1-hydroxy-6-sulfamoylhept-2-en-1-yl)cyclobutyl)methyl)-3',4',4',5-tetrahydro-2H,2'H-spiro[benzo[b][1,4]oxazepine-3,1'-naphthalene]-7-carboxylic acid and (S)-6'-chloro-5-(((1R,2R)-2-((1S,5R,6S,E)-5-cyclopropyl-1-hydroxy-6-sulfamoylhept-2-en-1-yl)cyclobutyl)methyl)-3',4',4',5-tetrahydro-2H,2'H-spiro[benzo[b][1,4]oxazepine-3,1'-naphthalene]-7-carboxylic acid and (S)-6'-chloro-5-(((1R,2R)-2-((1S,5R,6R,E)-5-cyclopropyl-1-hydroxy-6-sulfamoylhept-2-en-1-yl)cyclobutyl)methyl)-3',4',4',5-tetrahydro-2H,2'H-spiro[benzo[b][1,4]oxazepine-3,1'-naphthalene]-7-carboxylic acid (Step 4) following a procedure similar to the one described for the synthesis of Example 690, Step 10, except that the crude product was purified by reversed phase preparatory HPLC (Gemini® 10 μm NX—C18 110 Å column; gradient elution of 50% to 90% MeCN in water, where both solvents contain 0.1% TFA, 25 min method) to provide the title compounds as a mixture.

Step 6: (1S,3'R,6'R,7'S,8'E,11'R,12'R)-6-chloro-11'-cyclopropyl-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'S,12'R)-6-chloro-11'-cyclopropyl-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'R,12'S)-6-chloro-11'-cyclopropyl-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'S,12'S)-6-chloro-11'-cyclopropyl-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide The title compounds were prepared from (1S,3'R,6'R,7'S,8'E,11'R,12'R)-6-chloro-11'-cyclopropyl-12'-methyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl acetate and (1S,3'R,6'R,7'S,8'E,11'R,12'S)-6-chloro-11'-cyclopropyl-12'-methyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl acetate and (1S,3'R,6'R,7'S,8'E,11'S,12'R)-6-chloro-11'-cyclopropyl-12'-methyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl acetate and (1S,3'R,6'R,7'S,8'E,11'S,12'S)-6-chloro-11'-cyclopropyl-12'-methyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl acetate (Step 5) following a procedure similar to the one described for the synthesis of Example 683, except that the crude product was purified by reversed phase preparatory HPLC (Gemini™ Prep C18 5 µm column; Phenomenex, Torrance, CA; gradient elution of 50% to 90% MeCN in water, where both solvents contain 0.1% TFA, 25 min method) to provide one of the title compounds as the second eluting fraction as a white foam. ¹H NMR (400 MHz, CDCl₃) δ 8.01 (br. s., 1H), 7.71-7.51 (m, 2H), 7.16-7.05 (m, 2H), 7.03-6.99 (m, 1H), 6.94-6.80 (m, 1H), 5.79 (dd, J=8.3, 15.6 Hz, 1H), 5.43 (dd, J=7.9, 15.6 Hz, 1H), 4.44 (d, J=7.6 Hz, 1H), 4.15-3.76 (m, 4H), 3.76-3.52 (m, 3H), 3.30-0.95 (m, 19H), 0.80 (d, J=4.9 Hz, 1H), 0.65 (d, J=16.0 Hz, 1H), 0.48-0.35 (m, 1H), 0.19-0.08 (m, 1H), 0.08--0.01 (m, 1H). m/z (ESI, +ve ion) 607.0 (M–H₂O+H)⁺.

Example 677. (1S,3'R,6'R,7'S,8'E,11'R,12'R)-6-chloro-11'-cyclopropyl-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'S,12'R)-6-chloro-11'-cyclopropyl-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'R,12'S)-6-chloro-11'-cyclopropyl-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,11'S,12'S)-6-chloro-11'-cyclopropyl-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

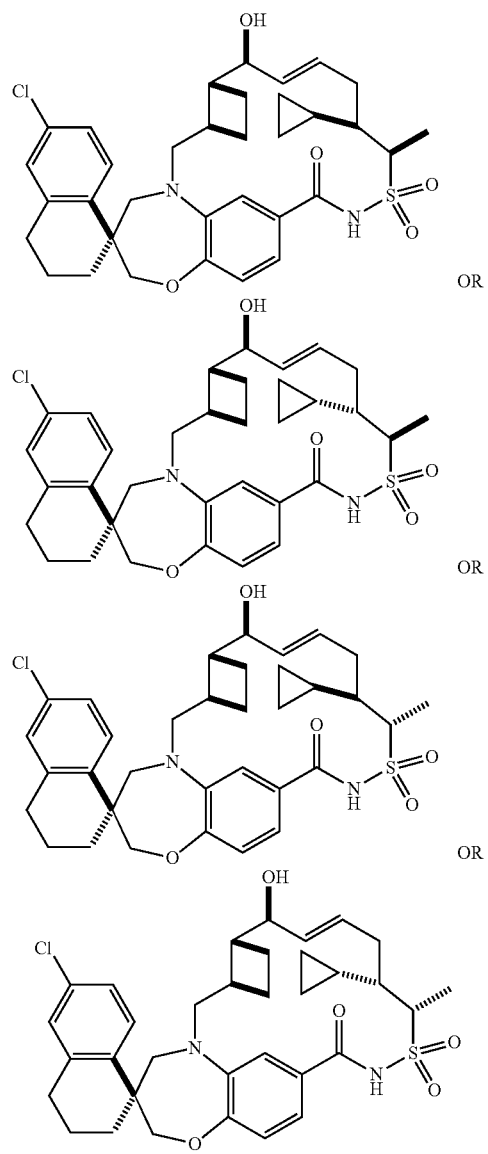

1425

The title compound was obtained as a white foam as the fourth eluting isomer from the reversed phase preparatory HPLC separation in Example 676, Step 6. $^1$H NMR (400 MHz, CDCl$_3$) δ 7.76-7.61 (m, 2H), 7.18 (dd, J=3.3, 6.7 Hz, 1H), 7.10 (s, 1H), 7.04-6.86 (m, 2H), 5.82-5.61 (m, 1H), 5.56-5.34 (m, 1H), 4.26-4.04 (m, 2H), 4.02-2.90 (m, 7H), 2.86-2.67 (m, 2H), 2.66-1.04 (m, 16H), 0.94-0.74 (m, 2H), 0.64-0.17 (m, 2H), 0.15-0.03 (m, 1H). m/z (ESI, +ve ion) 607.0 (M−H$_2$O+H)$^+$.

Example 678. (1S,3'R,6'R,7'S,8'E,11'R,12'R)-6-chloro-11'-cyclopropyl-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-11'-cyclopropyl-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-11'-cyclopropyl-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-11'-cyclopropyl-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

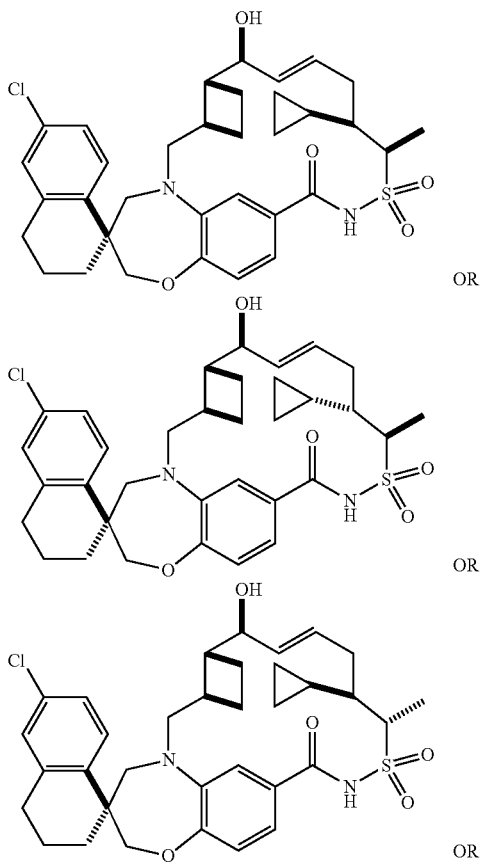

1426

-continued

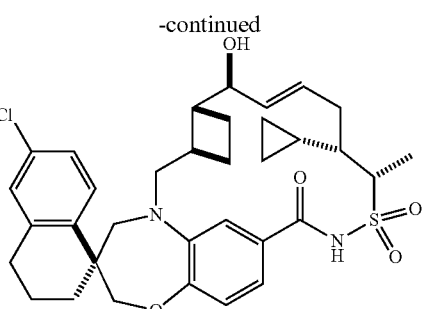

The title compound was obtained as a white foam as the fifth eluting isomer from the reversed phase preparatory HPLC separation in Example 676. $^1$H NMR (400 MHz, CDCl$_3$) δ 7.95 (d, J=8.4 Hz, 1H), 7.71 (d, J=8.6 Hz, 1H), 7.28-7.16 (m, 2H), 7.10 (s, 1H), 7.03-6.92 (m, 1H), 6.19-5.92 (m, 1H), 5.54-5.37 (m, 1H), 4.27-3.99 (m, 3H), 3.99-3.61 (m, 3H), 3.46-3.15 (m, 2H), 2.92-1.18 (m, 16H), 1.57 (d, J=8.4 Hz, 3H), 0.97-0.82 (m, 1H), 0.81-0.73 (m, 1H), 0.52 (dd, J=4.5, 9.2 Hz, 1H), 0.31-0.13 (m, 1H), 0.11-0.01 (m, 1H). m/z (ESI, +ve ion) 607.0 (M−H$_2$O+H)$^+$.

Example 679. (1S,3'R,6'R,7'S,8'E,11'S,12'R)-6-chloro-12'-((2S)-2-hydroxy-3-methoxypropyl)-7'-methoxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-12'-((2S)-2-hydroxy-3-methoxypropyl)-7'-methoxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

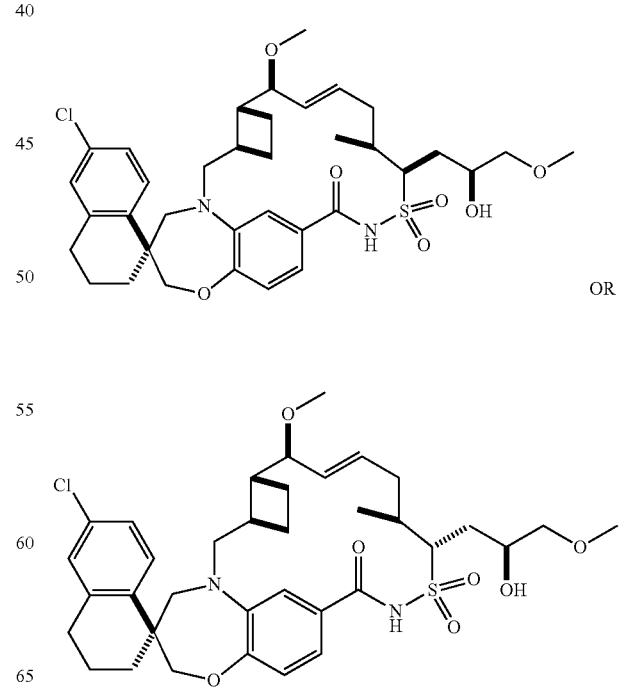

Step 1: (2S)-1-((1S,3'R,6'R,7'S,8'E,11'S,12'R)-6-chloro-7'-methoxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)-3-methoxy-2-propanyl benzoate and (2S)-1-((1S,3'R,6'R,7'S,8'E,11'S,12'S)-6-chloro-7'-methoxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-12'-yl)-3-methoxy-2-propanyl benzoate

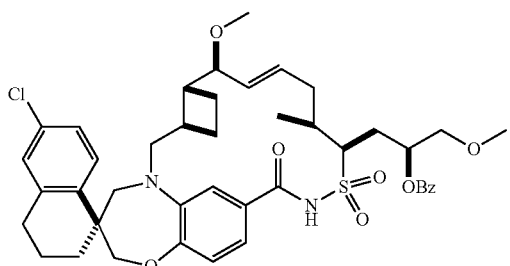

AND

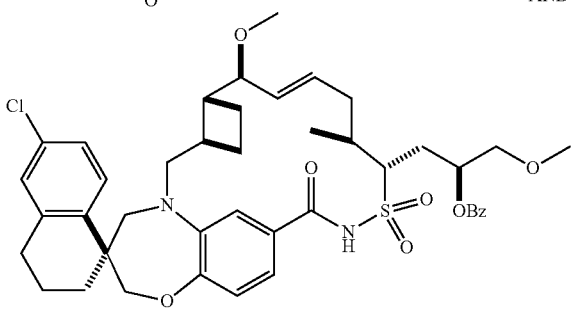

The title compounds were prepared from (2S)-1-((1S,3'R,6'R,7'S,8'E,11'S,12'R)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)-3-methoxy-2-propanyl benzoate and (2S)-1-((1S,3'R,6'R,7'S,8'E,11'S,12'S)-6-chloro-7'-hydroxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)-3-methoxy-2-propanyl benzoate (prepared in Step 1 for the synthesis of Example 672) following a procedure similar to the one described for the synthesis of Example 669 using methyl iodide instead of 2-bromoethyl methyl ether.

Step 2: (1S,3'R,6'R,7'S,8'E,11'S,12'R)-6-chloro-12'-((2S)-2-hydroxy-3-methoxypropyl)-7'-methoxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'S)-6-chloro-12'-((2S)-2-hydroxy-3-methoxypropyl)-7'-methoxy-11'-methyl-3,4-dihydro-2H,15'H-spiro [naphthalene-1,22'-[20]oxa[13]thia[1,14] diazatetracyclo[14.7.2.0$^{3,6}$.0$^{19,24}$]pentacosa [8,16,18,24]tetraen]-15'-one 13',13'-dioxide The title compound was prepared from (2S)-1-((1S,3'R,6'R,7'S,8'E,11'S,12'R)-6-chloro-7'-methoxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)-3-methoxy-2-propanyl benzoate and (2S)-1-((1S,3'R,6'R,7'S,8'E,11'S,12'S)-6-chloro-7'-methoxy-11'-methyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-12'-yl)-3-methoxy-2-propanyl benzoate (Step 1) following a procedure similar to the one described for the synthesis of Example 672 (Step 2), except that the crude product was purified by reversed phase preparatory HPLC (Gemini™ Prep C18 10 μm column; Phenomenex, Torrance, CA; gradient elution of 45% to 95% MeCN in water, where both solvents contain 0.1% TFA, 30 min method) to provide one of the title compounds as the second eluting fraction as a white foam. $^1$H NMR (400 MHz, CDCl$_3$) δ 7.77 (br. s., 1H), 7.73-7.64 (m, 1H), 7.22-7.15 (m, 1H), 7.13-6.97 (m, 2H), 6.96-6.83 (m, 2H), 6.01-5.86 (m, 1H), 5.50 (dd, J=9.1, 15.0 Hz, 1H), 4.61 (d, J=9.4 Hz, 1H), 4.37 (br. s., 1H), 4.21-4.02 (m, 3H), 3.90-3.60 (m, 4H), 3.55-3.22 (m, 2H), 3.41 (s, 3H), 3.20 (s, 3H), 2.88-1.09 (m, 18H), 1.03 (d, J=5.2 Hz, 3H). m/z (ESI, +ve ion) 687.1 (M+H)$^+$.

Example 680. (1S,3'R,6'R,7'S)-6-chloro-7'-hydroxy-3,4-dihydro-2H,9'H,15'H-spiro[naphthalene-1,22'-[20]oxa[13]thia[1,10,14]triazatetracyclo[14.7.2.0$^{3,6}$.0$^{19,24}$]pentacosa[16,18,24]triene]-9',15'-dione 13',13'-dioxide or (1S,3'R,6'R,7'R)-6-chloro-7'-hydroxy-3,4-dihydro-2H,9'H,15'H-spiro[naphthalene-1,22'-[20]oxa[13]thia[1,10,14]triazatetracyclo[14.7.2.0$^{3,6}$.0$^{19,24}$]pentacosa[16,18,24]triene]-9',15'-dione 13',13'-dioxide

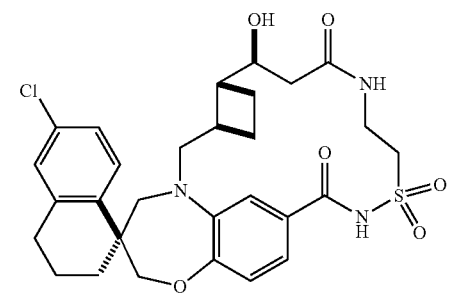

OR

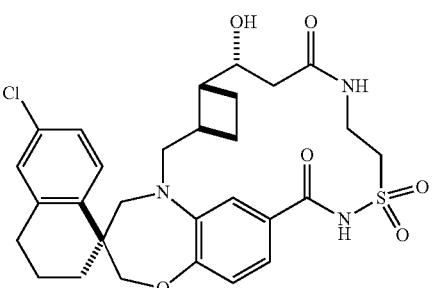

Step 1: (1R,2R)-cyclobutane-1,2-diyldimethanol and (1S,2S)-cyclobutane-1,2-diyldimethanol

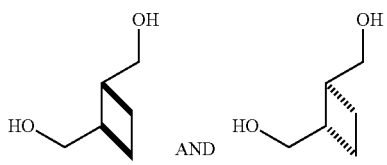 [SMILES: OC[C@@H]1CC[C@H]1CO ; OC[C@H]1CC[C@@H]1CO]

To a solution of racemic trans cyclobutane-1,2-dicarboxylic acid (20.2 g, 140 mmol, Atlantic Research Chemicals Ltd) in THF (699 ml) in a 2 L round flask under running $N_2$ line was added borane-THFcomplex (1.0 M, 559 ml, 559 mmol, Sigma-Aldrich Chemical Company, Inc.) drop wise via additional funnel over 65 min at 0° C. The resulting mixture was allowed to stir in the ice bath for 15 min, removed from ice bath and left to stir at rt for 36 h. The reaction flask was placed into 0° C. ice bath, to the solution under running $N_2$ line was slowly added ice (-300 g) over 45 min, vigorous gas formation was observed. The mixture was allowed to stir in ice bath for 2.0 h till gas formation ceased. The organic solvent and most of the water was removed under reduced pressure. To the residue was added 10% aqueous NaOH solution (200 mL), the mixture was allowed to stir at rt for 1.0 h. The resulting mixture was extracted with 30% $^i$PrOH/chloroform (3×200 mL). The organic solutions were combined. After removal of organic solvents under reduced pressure, purification of the residue by flash chromatograph on ISCO Gold silica gel column using 50% to 100% of solvent A in hexanes (solvent A is 1:3:6 MeOH/EtOAc/hexanes) as eluent provided the title compounds as colorless syrup (14.76 g, 91%).

Step 2: ((1R,2R)-2-(hydroxymethyl)cyclobutyl)methyl benzoate

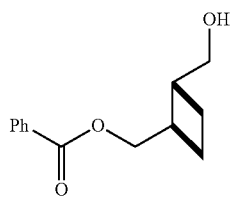 [SMILES: O=C(OC[C@@H]1CC[C@H]1CO)c1ccccc1]

To a suspension of sodium hydride (4.76 g, 119 mmol, 60% dispersed in mineral oil, Sigma-Aldrich Chemical Company, Inc.) in THF (298 ml) under running $N_2$ line in ice bath was added a solution of a mixture of (1R,2R)-cyclobutane-1,2-diyldimethanol and (1S,2S)-cyclobutane-1,2-diyldimethanol (13.8 g, 119 mmol, Step 1) in THF (100 mL) drop wise over 40 min. The resulting mixture was allowed to warm to rt over 30 min, heated in 50° C. oil bath for 2.5 h, then cooled to rt and allowed to stir at rt overnight. Large amount of precipitate was formed. The suspension was cooled to −50° C., to the mixture was slowly added a solution of benzoyl chloride (16.7 g, 119 mmol, Sigma-Aldrich Chemical Company, Inc.) in 50 mL THF over 30 min. The mixture was allowed to warm with the bath to rt, and was allowed to stir at rt for 3 h. To the mixture under running $N_2$ line was slowly added saturated aqueous $NH_4Cl$ (100 mL), and water (100 mL). The resulting mixture was extracted with EtOAc (3×150 mL). The organic layers were collected and combined. After removal of organic solvents under reduced pressure, purification of the residue by flash chromatograph on ISCO Gold silica gel column using 15-80% EtOAc/Hexanes as eluent provided the desired product as a mixture (19.7 g, 75%). LCMS (ES) [M+1]$^+$ m/z 221. This mixture product was dissolved in MeOH (164 mg/mL) and was purified by SFC (Method: 250×30 mm Chiralpak AD-H column, 2 in series w/ total length 500 mm, w/ 140 mL/min of 10% Ethanol (20 mM $NH_3$)/90% $CO_2$. Outlet pressure 100 bar; Temp. 20° C.; Wavelength 226 nm). The title compound was obtained as the second eluting stereoisomer (with retention time of 3.5-4.0 min) as a colorless syrup. m/z (ESI, +ve ion) 221.0 (M+H)$^+$.

Step 3. ((1R,2R)-2-formylcyclobutyl)methyl benzoate

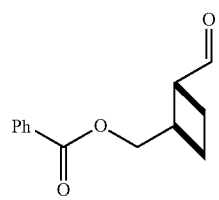 [SMILES: O=C[C@@H]1CC[C@H]1COC(=O)c1ccccc1]

To a solution of ((1R,2R)-2-(hydroxymethyl)cyclobutyl) methyl benzoate (3.32 g, 15.1 mmol, Step 2) in $CH_2Cl_2$ (30 mL) under $N_2$ was added (diacetoxyiodo)benzene (5.34 g, 16.6 mmol, Acros Organics) followed by 2,2,6,6-tetramethylpiperidinooxy (0.118 g, 0.754 mmol, Lancaster Synthesis Ltd.) at 0° C. The mixture was allowed to warm to rt and left stirring at rt. TLC (66% EtOAc/Hexanes) was used to monitor the reaction to completion (in 4 h). The reaction mixture was concentrated under reduced pressure, and the residue was purified flash chromatograph on ISCO Gold silica gel column using 20-45% EtOAc/Hexanes as eluent to provide the title compound as colorless syrup (2.98 g, 91%). $^1$H NMR (400 MHz, $CDCl_3$) δ 9.77 (d, J=1.37 Hz, 1H), 8.13-7.92 (m, 2H), 7.66-7.52 (m, 1H), 7.52-7.39 (m, 2H), 4.52-4.27 (m, 2H), 3.26-2.97 (m, 2H), 2.30-2.03 (m, 3H), 2.01-1.89 (m, 1H).

Step 4. ((1R,2R)-2-((R)-3-(tert-butoxy)-1-hydroxy-3-oxopropyl)cyclobutyl)methyl benzoate and ((1R,2R)-2-((S)-3-(tert-butoxy)-1-hydroxy-3-oxopropyl)cyclobutyl)methyl benzoate

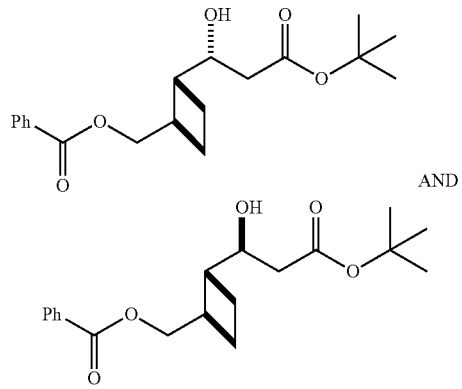

1431

To a solution of ((1R,2R)-2-formylcyclobutyl)methyl benzoate (1.40 g, 6.41 mmol, Step 3) in THF (80 mL) in ice bath under $N_2$ was added drop wise of 2-tert-butoxy-2-oxoethylzinc chloride (12.8 mL, 0.5 M in diethyl ether, 6.41 mmol, Rieke Metals, Inc.). The mixture was allowed to warm to rt with ice bath, and left stirring at rt for 14 h. To the rt solution was added additional 2-tert-butoxy-2-oxoethylzinc chloride (12.8 mL, 0.5 M in diethyl ether, 6.41 mmol, Rieke Metals, Inc) over 3 min. The mixture was allowed to stir at rt for additional 2.5 h, and was quenched with saturated aqueous $NH_4Cl$ (50 mL), diluted with water (60 mL). The organic layer was separated, and the aqueous layer was back extracted with EtOAc (3×35 mL). The organic solutions were combined. After removal of organic solvents under reduced pressure, purification of the residue by flash chromatograph on ISCO Gold silica gel column using 10-70% EtOAc/Hexanes as eluent provided the title compounds as a mixture.

Step 5. (R)-3-((1R,2R)-2-((benzoyloxy)methyl)cyclobutyl)-3-hydroxypropanoic Acid and (S)-3-((1R,2R)-2-((benzoyloxy)methyl)cyclobutyl)-3-hydroxypropanoic Acid

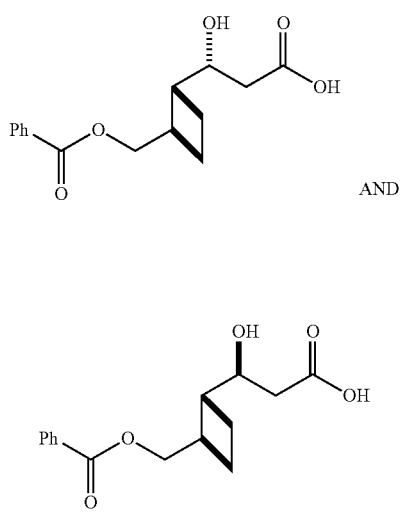

AND

A mixture of ((1R,2R)-2-((R)-3-(tert-butoxy)-1-hydroxy-3-oxopropyl)cyclobutyl)methyl benzoate and ((1R,2R)-2-((S)-3-(tert-butoxy)-1-hydroxy-3-oxopropyl)cyclobutyl) methyl benzoate (1.66 g, 4.96 mmol, Step 4) in $CH_2Cl_2$ (5.29 mL) and trifluoroacetic acid (1.32 ml, Acros Organics) was allowed to stir at for 5.0 h, Additional trifluoroacetic acid (1.32 ml, Acros Organics) was added and the resulting mixture was allowed to stir at rt for 1.5 h. After removal of organic solvents under reduced pressure, the residue was re-dissolved in 30% $^i$PrOH/chloroform, washed with saturated aqueous $NH_4Cl$ solution (4 mL). After removal of organic solvents under reduced pressure, purification of the residue by flash chromatograph on ISCO Gold silica gel column using 100% EtOAc to provide the title compounds.

1432

Step 6. ((1R,2R)-2-((R)-3-((2-(benzylthio)ethyl)amino)-1-hydroxy-3-oxopropyl)cyclobutyl)methyl benzoate and ((1R,2R)-2-((S)-3-((2-(benzylthio)ethyl)amino)-1-hydroxy-3-oxopropyl)cyclobutyl) methyl benzoate

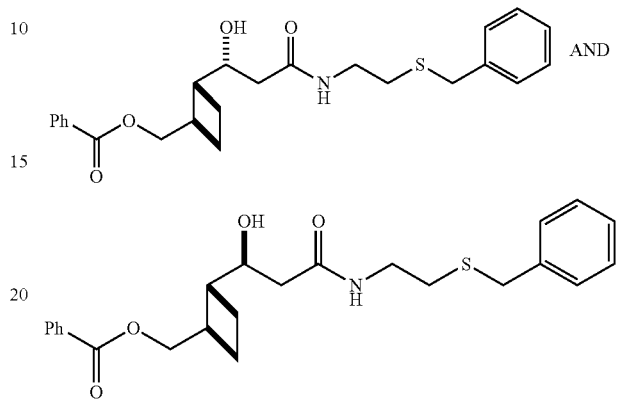

AND

To a solution of (R)-3-((1R,2R)-2-((benzoyloxy)methyl)cyclobutyl)-3-hydroxypropanoic acid and (S)-3-((1R,2R)-2-((benzoyloxy)methyl)cyclobutyl)-3-hydroxypropanoic acid (166 mg, 0.596 mmol, Step 5) in $CHCl_3$ (10 mL) and hunig's base (0.467 mL, 2.68 mmol, Sigma-Aldrich Chemical Company, Inc.) at rt under $N_2$ was added 4-(dimethylamino) pyridine (87.0 mg, 0.716 mmol, Sigma-Aldrich Chemical Company, Inc.), s-benzylcysteamine hydrochloride (365 mg, 1.79 mmol, Sigma-Aldrich Chemical Company, Inc.) and 1-(3-dimethylaminopropyl)-3-ethylcarbodiimide hydrochloride (343 mg, 1.79 mmol, Advanced ChemTech) in sequence. The mixture was allowed to stir at rt overnight. The mixture was quenched with saturated aqueous $NH_4Cl$ solution (2 mL), and extracted with $CH_2Cl_2$ (3×8 mL). Organic solutions were combined. After removal of organic solvents under reduced pressure, purification of the residue by flash chromatograph on ISCO Gold silica gel column using 0-80% EtOAc (EtOAc contained 0.1% HOAc) to provide the title compounds.

Step 7. ((1R,2R)-2-((R)-11,11-dimethyl-6-oxo-1,10,10-triphenyl-9-oxa-2-thia-5-aza-10-siladodecan-8-yl)cyclobutyl)methyl benzoate and ((1R,2R)-2-((S)-11,11-dimethyl-6-oxo-1,10,10-triphenyl-9-oxa-2-thia-5-aza-10-siladodecan-8-yl)cyclobutyl)methyl benzoate

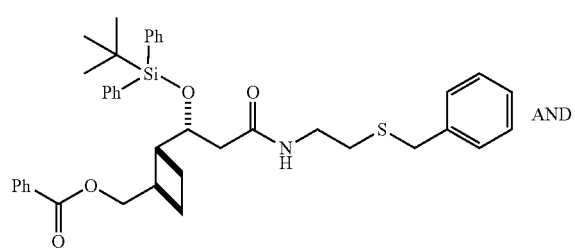

AND

-continued

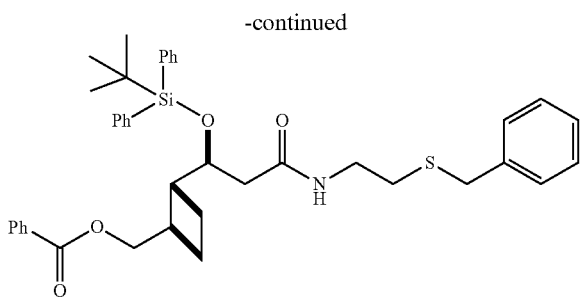

To a 0° C. solution of ((1R,2R)-2-((R)-3-((2-(benzylthio)ethyl)amino)-1-hydroxy-3-oxopropyl)cyclobutyl)methyl benzoate and ((1R,2R)-2-((S)-3-((2-(benzylthio)ethyl)amino)-1-hydroxy-3-oxopropyl)cyclobutyl)methyl benzoate (0.600 g, 1.40 mmol, Step 6) in CH$_2$Cl$_2$ (14 mL) was added 2,6-dimethylpyridine (0.326 ml, 2.81 mmol, Sigma-Aldrich Chemical Company, Inc.) followed by (1,1-dimethylethyl)diphenylsilyl trifluoromethanesulfonate (0.981 g, 2.53 mmol, TCI America). The mixture was allowed to warm with the ice bath to rt and to stir at rt for 2.5 h. The reaction solution was quenched with saturated aqueous NaHCO$_3$ solution (3 mL), diluted with water (5 mL), and extracted with 30% $^i$PrOH/chloroform (3×8 mL). The organic solutions were combined, washed with water (3 mL) and brine (3 mL). After removal of organic solvents under reduced pressure, purification of the residue by flash chromatograph on ISCO Gold silica gel column using 0-50% EtOAc provided the titled products as two fractions each containing one of the title compounds. Combined both fractions to provide the title compounds as a mixture.

Step 8. ((1R,2R)-2-((R)-1-((tert-butyldiphenylsilyl)oxy)-3-oxo-3-((2-sulfamoylethyl)amino)propyl)cyclobutyl)methyl benzoate and ((1R,2R)-2-((S)-1-((tert-butyldiphenylsilyl)oxy)-3-oxo-3-((2-sulfamoylethyl)amino)propyl)cyclobutyl)methyl benzoate

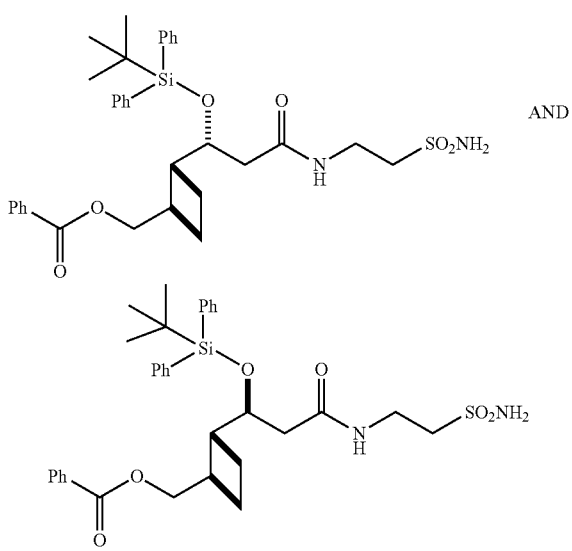

A mixture of ((1R,2R)-2-((R)-11,11-dimethyl-6-oxo-1,10,10-triphenyl-9-oxa-2-thia-5-aza-10-siladodecan-8-yl)cyclobutyl)methyl benzoate and ((1R,2R)-2-((S)-11,11-dimethyl-6-oxo-1,10,10-triphenyl-9-oxa-2-thia-5-aza-10-siladodecan-8-yl)cyclobutyl)methyl benzoate (227 mg, 0.341 mmol, Step 7) and iodosobenzene (300 mg, 1.36 mmol, TCI America) in CH$_2$Cl$_2$ (22 mL) was allowed to stir at rt for 8 min. To the mixture was added HCl (37%, 2.45 mL, Sigma-Aldrich Chemical Company, Inc.) drop wise over 4 min. After stirring at rt for 20 min, the mixture was added drop wise into a cold solution of ammonium hydroxide (221.3 mL, 28%, Sigma-Aldrich Chemical Company, Inc.) in ice bath over 12 min. The resulting mixture was allowed to stir in the ice bath for 40 min, diluted with water (10 mL) and 30% $^i$PrOH/chloroform (12 mL), and was let settled at rt overnight. The organic layer was collected and the aqueous layer was back extracted with 30% $^i$PrOH/chloroform (2×8 mL). The organic solutions were combined. After removal of organic solvents under reduced pressure, purification of the residue by flash chromatograph on ISCO Gold silica gel column using 0-80-100% EtOAc provided the title compounds as a mixture.

Step 9. (R)-3-((tert-butyldiphenylsilyl)oxy)-3-((1R,2R)-2-(hydroxymethyl)cyclobutyl)-N-(2-sulfamoylethyl)propanamide and (S)-3-((tert-butyldiphenylsilyl)oxy)-3-((1R,2R)-2-(hydroxymethyl)cyclobutyl)-N-(2-sulfamoylethyl)propanamide

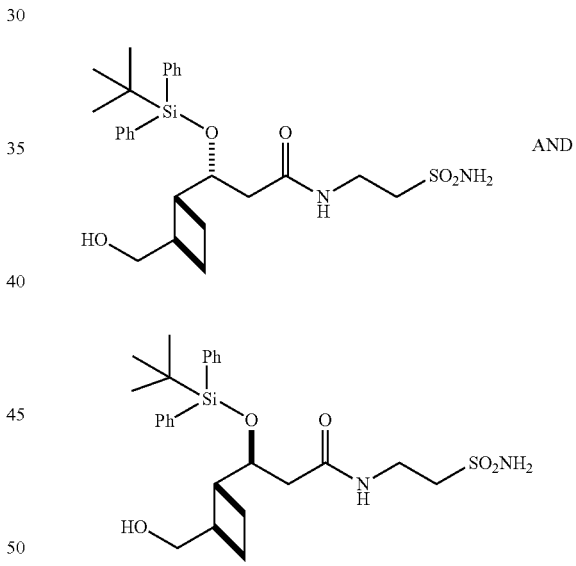

To a mixture of ((1R,2R)-2-((R)-1-((tert-butyldiphenylsilyl)oxy)-3-oxo-3-((2-sulfamoylethyl)amino)propyl)cyclobutyl)methyl benzoate and ((1R,2R)-2-((S)-1-((tert-butyldiphenylsilyl)oxy)-3-oxo-3-((2-sulfamoylethyl)amino)propyl)cyclobutyl)methyl benzoate (220 mg, 0.353 mmol, Step 8) in methanol (3.5 mL) was added sodium methylate (0.663 mL, 30%, Acros Organics). The mixture was allowed to stir at rt for 2.5 h and treated with water (6 mL). After removal of methanol solvent under reduced pressure, the resultant mixture was extracted with 30% PrOH/chloroform (2×8 mL). The organic fractions were combined. After removal of organic solvents under reduced pressure, purification of the residue by flash chromatograph on ISCO Gold silica gel column using 0-10% MeOH/CH$_2$Cl$_2$ to provide the title compounds as a mixture.

Step 10. (R)-3-((tert-butyldiphenylsilyl)oxy)-3-((1R,2R)-2-formylcyclobutyl)-N-(2-sulfamoylethyl)propanamide and (S)-3-((tert-butyldiphenylsilyl)oxy)-3-((1R,2R)-2-formylcyclobutyl)-N-(2-sulfamoylethyl)propanamide

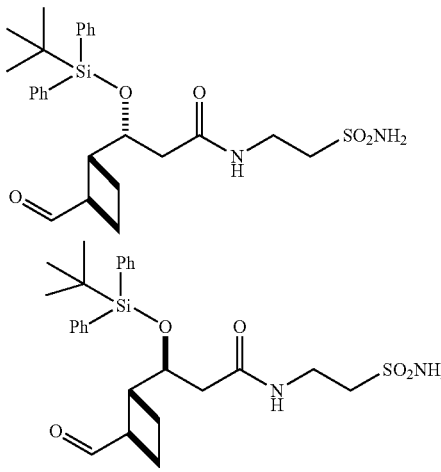

The title compounds were prepared as a mixture from (R)-3-((tert-butyldiphenylsilyl)oxy)-3-((1R,2R)-2-(hydroxymethyl)cyclobutyl)-N-(2-sulfamoylethyl)propanamide and (S)-3-((tert-butyldiphenylsilyl)oxy)-3-((1R,2R)-2-(hydroxymethyl)cyclobutyl)-N-(2-sulfamoylethyl)propanamide (Step 9), following a procedure similar to the one described above for the synthesis of ((1R,2R)-2-formylcyclobutyl)methyl benzoate (Step 3), except that the crude product was purified by flash chromatography on ISCO Gold silica gel column using 0-10% MeOH/CH$_2$Cl$_2$ to provide the title compounds as a white solid.

Step 11. (S)-methyl 5-(((1R,2R)-2-((S)-1-((tert-butyldiphenylsilyl)oxy)-3-oxo-3-((2-sulfamoylethyl)amino)propyl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((R)-1-((tert-butyldiphenylsilyl)oxy)-3-oxo-3-((2-sulfamoylethyl)amino)propyl)cyclobutyl)methyl)-6'-chloro-3',4,4',5-tetrahydro-2H,2'H-spiro[benzo[b][1,4]oxazepine-3,1'-naphthalene]-7-carboxylate

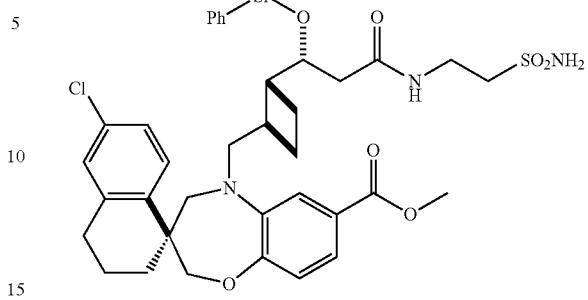

To a rt solution of (S)-methyl 6'-chloro-3',4,4',5-tetrahydro-2H,2'H-spiro[benzo[b][1,4]oxazepine-3,1'-naphthalene]-7-carboxylate (62.3 mg, 0.174 mmol, Intermediate AA11A, Step 12A), (R)-3-((tert-butyldiphenylsilyl)oxy)-3-((1R,2R)-2-formylcyclobutyl)-N-(2-sulfamoylethyl)propanamide and (S)-3-((tert-butyldiphenylsilyl)oxy)-3-((1R,2R)-2-formylcyclobutyl)-N-(2-sulfamoylethyl)propanamide (45.0 mg, 0.087 mmol, Step 10) in CH$_2$Cl$_2$ (1161 µl) was added acetic acid (0.38 mL, Sigma-Aldrich Chemical Company, Inc.). The mixture was allowed to stir at rt for 6 min, to the solution was added a solution of sodium cyanoborohydride (26 µl, 1.0 N in THF, 0.026 mmol, Sigma-Aldrich Chemical Company, Inc.) in THF (2.0 mL) drop wise over 1.0 h. The mixture was allowed to stir at rt for 1.0, treated with saturated aqueous NaHCO$_3$ (3 mL), diluted with water (3 mL), and extracted with CH$_2$Cl$_2$ (3×5 mL). The organic layers were combined, washed with water (3 mL) and brine (2 mL), and dried over MgSO$_4$. After removal of organic solvents under reduced pressure, purification of the residue by flash chromatography on ISCO Gold silica gel column with 0-80% EtOAc/Hexanes (EtOAc contained 0.1% HOAc) provided the title compounds as a white solid.

Step 12. (S)-5-(((1R,2R)-2-((S)-1-((tert-butyldiphenylsilyl)oxy)-3-oxo-3-((2-sulfamoylethyl)amino)propyl)cyclobutyl)methyl)-6'-chloro-3',4,4',5-tetrahydro-2H,2'H-spiro[benzo[b][1,4]oxazepine-3,1'-naphthalene]-7-carboxylic Acid and ((S)-5-(((1R,2R)-2-((R)-1-((tert-butyldiphenylsilyl)oxy)-3-oxo-3-((2-sulfamoylethyl)amino)propyl)cyclobutyl)methyl)-6'-chloro-3',4,4',5-tetrahydro-2H,2'H-spiro[benzo[b][1,4]oxazepine-3,1'-naphthalene]-7-carboxylic Acid

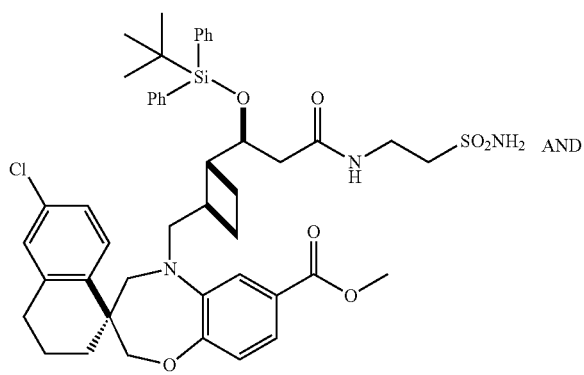

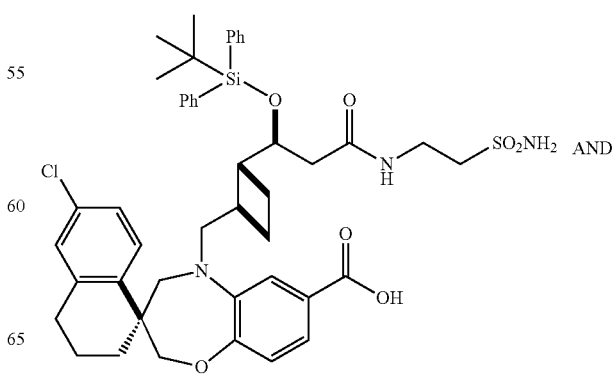

-continued

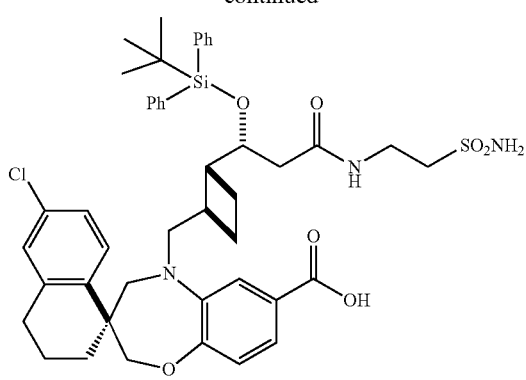

To a rt mixture of (S)-methyl 5-(((1R,2R)-2-((S)-1-((tert-butyldiphenylsilyl)oxy)-3-oxo-3-((2-sulfamoylethyl)amino)propyl)cyclobutyl)methyl)-6'-chloro-3',4,4',5-tetrahydro-2H,2'H-spiro[benzo[b][1,4]oxazepine-3,1'-naphthalene]-7-carboxylate and (S)-methyl 5-(((1R,2R)-2-((R)-1-((tert-butyldiphenylsilyl)oxy)-3-oxo-3-((2-sulfamoylethyl)amino)propyl)cyclobutyl)methyl)-6'-chloro-3',4,4',5-tetrahydro-2H,2'H-spiro[benzo[b][1,4]oxazepine-3,1'-naphthalene]-7-carboxylate (105 mg, 0.122 mmol, Step 11) in 1,4-dioxane (0.4 mL) and MeOH (0.100 mL) was added 0.5 M aqueous lithium hydroxide solution (0.978 mL, 0.489 mmol, Sigma-Aldrich Chemical Company, Inc.). After stirring at rt for 40 min, to the mixture was added 4 M aqueous lithium hydroxide solution (0.15 mL). The resulting mixture was allowed to stir at rt overnight. The reaction mixture was treated with 6.0 N HCl to PH=4.0. After removal of water and organic solvents under reduced pressure, purification of the residue by flash chromatograph on ISCO Gold silica gel column using 0-10% MeOH/CH$_2$Cl$_2$ provided the title compounds as a mixture.

Step 13. (S)-6'-chloro-5-(((1R,2R)-2-((S)-1-hydroxy-3-oxo-3-((2-sulfamoylethyl)amino)propyl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((R)-1-hydroxy-3-oxo-3-((2-sulfamoylethyl)amino)propyl)cyclobutyl)methyl)-3',4,4',5-tetrahydro-2H,2'H-spiro[benzo[b][1,4]oxazepine-3,1'-naphthalene]-7-carboxylic Acid

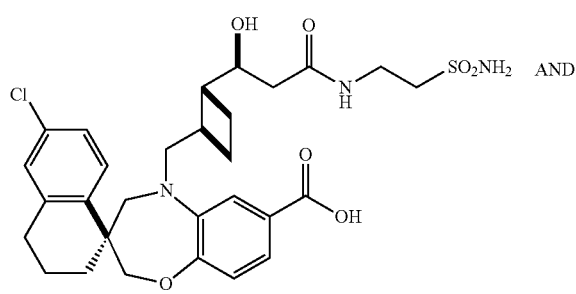

AND

-continued

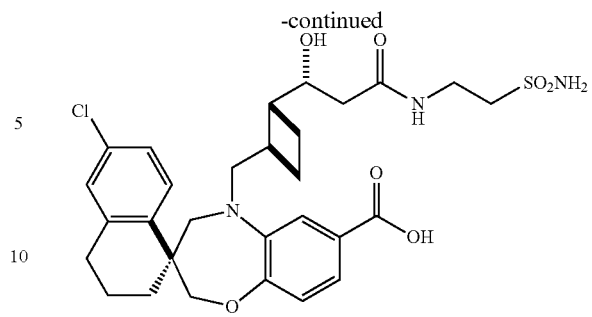

To a rt mixture of (S)-5-(((1R,2R)-2-((S)-1-((tert-butyldiphenylsilyl)oxy)-3-oxo-3-((2-sulfamoylethyl)amino)propyl)cyclobutyl)methyl)-6'-chloro-3',4,4',5-tetrahydro-2H,2'H-spiro[benzo[b][1,4]oxazepine-3,1'-naphthalene]-7-carboxylic Acid and ((S)-5-(((1R,2R)-2-((R)-1-((tert-butyldiphenylsilyl)oxy)-3-oxo-3-((2-sulfamoylethyl)amino)propyl)cyclobutyl)methyl)-6'-chloro-3',4,4',5-tetrahydro-2H,2'H-spiro[benzo[b][1,4]oxazepine-3,1'-naphthalene]-7-carboxylic acid (105 mg, 0.122 mmol, Step 11) in CH$_2$Cl$_2$ (0.4 mL) was added tetrabutylammonium fluoride (0.71 mL, 1.0 M in THF, 0.71 mmol, Sigma-Aldrich Chemical Company, Inc.) followed by water (0.1 mL). The mixture was allowed to stir at rt overnight, treated with water (3 mL), and extracted with 30% $^i$PrOH/chloroform (3×4 mL). The organic fractions were combined. After removal of organic solvents under reduced pressure, purification of the residue by flash chromatograph on ISCO Gold silica gel column using 0-10% MeOH/CH$_2$Cl$_2$ provided the title compounds as a mixture.

Step 14. (1S,3'R,6'R,7'S)-6-chloro-7'-hydroxy-3,4-dihydro-2H,9'H,15'H-spiro[naphthalene-1,22'-[20]oxa[13]thia[1,10,14]triazatetracyclo[14.7.2.0$^{3,6}$.0$^{19,24}$]pentacosa[16,18,24]triene]-9',15'-dione 13',13'-dioxide and (1S,3'R,6'R,7'R)-6-chloro-7'-hydroxy-3,4-dihydro-2H,9'H,15'H-spiro[naphthalene-1,22'-[20]oxa[13]thia[1,10,14]triazatetracyclo[14.7.2.0$^{3,6}$.0$^{19,24}$]pentacosa[16,18,24]triene]-9',15'-dione 13',13'-dioxide The title compounds were prepared from (2S,3R)-3-cyclopropylhex-5-ene-2-sulfonamide, and (S)-6'-chloro-5-(((1R,2R)-2-((S)-1-hydroxy-3-oxo-3-((2-sulfamoylethyl)amino)propyl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((R)-1-hydroxy-3-oxo-3-((2-sulfamoylethyl)amino)propyl)cyclobutyl)methyl)-3',4,4',5-tetrahydro-2H,2'H-spiro[benzo[b][1,4]oxazepine-3,1'-naphthalene]-7-carboxylic acid (Step 13) following a procedure similar to the one described for the synthesis of EXAMPLE 653, Step 4, except that the crude product was purified by reversed phase preparatory HPLC (Gemini™ Prep C18 10 μm column; Phenomenex, Torrance, CA; gradient elution of 45% MeCN in water to 70% MeCN in water over a 45 min period, where both solvents contain 0.1% TFA) to provide one of the title compounds as the first eluting isomer as a white foam. $^1$H NMR (400 MHz, CDCl$_3$) δ 17.76-7.65 (m, 2H), 7.56 (s, 1H), 7.18 (d, J=9.0 Hz, 2H), 7.11-7.08 (m, 2H), 7.07-6.98 (m, 1H), 6.19 (br. s., 1H), 4.23-4.08 (m, 3H), 3.98-0.89 (m, 22H). m/z (ESI, +ve ion) 588.1 (M+H)$^+$.

Example 681. (1S,3'R,6'R,7'S)-6-chloro-7'-hydroxy-3,4-dihydro-2H,9'H,15'H-spiro[naphthalene-1,22'-[20]oxa[13]thia[1,10,14]triazatetracyclo[14.7.2.0$^{3,6}$.0$^{19,24}$]pentacosa[16,18,24]triene]-9',15'-dione 13',13'-dioxide or (1S,3'R,6'R,7'R)-6-chloro-7'-hydroxy-3,4-dihydro-2H,9'H,15'H-spiro[naphthalene-1,22'-[20]oxa[13]thia[1,10,14]triazatetracyclo[14.7.2.0$^{3,6}$.0$^{19,24}$]pentacosa[16,18,24]triene]-9',15'-dione 13',13'-dioxide Example 682. (1S,3'R,6'R,7'S,8'E,12'S)-6-chloro-12'-(2-hydroxy-2-propanyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-12'-(2-hydroxy-2-propanyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

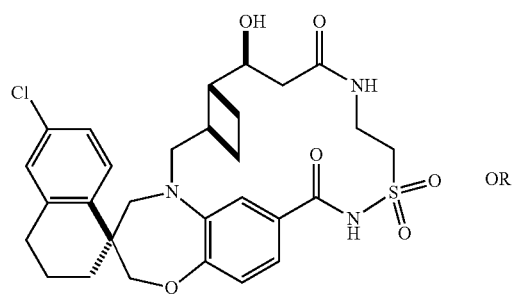

OR

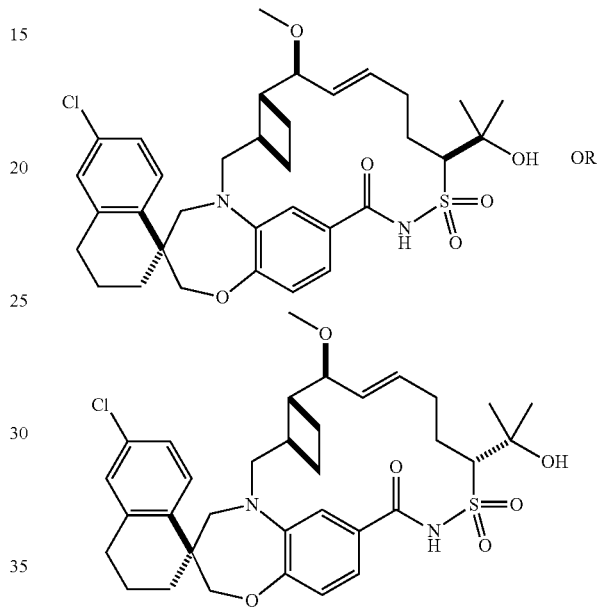

OR

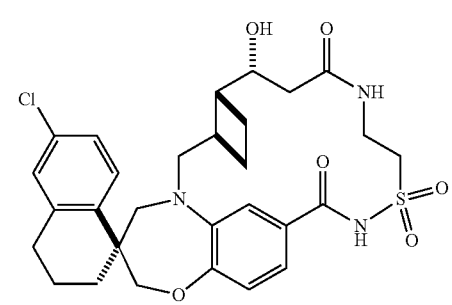

The title compound was obtained as a white foam as the second eluting isomer from the reversed phase preparatory HPLC separation in Example 680, Step 14. $^{1}$H NMR (400 MHz, CDCl$_3$) δ 10.10-9.56 (m, 1H), 7.74 (d, J=8.2 Hz, 1H), 7.52 (d, J=7.6 Hz, 1H), 7.23-7.15 (m, 2H), 7.10 (s., 1H), 7.05-6.97 (m, 1H), 5.86 (d, J=10.4 Hz, 1H), 4.68-4.63 (m, 1H), 4.58-4.53 (m, 1H), 4.25-4.05 (m, 3H), 3.92 (d, J=15.1 Hz, 1H), 3.71 (d, J=13.3 Hz, 1H), 3.52 (d, J=14.5 Hz, 1H), 3.31 (d, J=14.5 Hz, 1H), 3.25-3.06 (m, 2H), 2.78-1.32 (m, 15H). m/z (ESI, +ve ion) 588.1 (M+H)$^{+}$.

To a solution of diisopropylamine (240 μl, 1.71 mmol, Sigma-Aldrich Chemical Company, Inc.) in THF (6.0 mL) under N$_2$ was added $^n$BuLi (0.68 mL, 2.5 M in hexanes, 1.71 mmol, Sigma-Aldrich Chemical Company, Inc.) dropwise over 2 min at −78° C. The mixture was moved into a 0° C. ice bath and left stirring in the bath for 8 min. This freshly made lithium diisopropylamide solution was then placed into −40° C. bath for a temporary storage. To a −78° C. solution of (1S,3'R,6'R,7'S,8'E)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 651, Step 3) (25 mg, 0.043 mmol) in THF (1.0 mL) under Ar was added N,N,N',N'-tetramethylethylenediamine, redistilled (26 μl, 0.17 mmol, Sigma-Aldrich Chemical Company, Inc.) After stirring at −78° C. for 5 min, to this solution was added the freshly made lithium diisopropylamide solution as above (1.60 mL, 0.428 mmol). The resultant mixture was allowed to stir at −78° C. for 10 min, and then warmed to −10° C. over 40 min. To the −10° C. solution was added anhydrous acetone (dried over sieves, 1.0 mL, Sigma-Aldrich Chemical Company, Inc.) in one shot. The resulting solution was removed from the bath and left stirring at ambient atmosphere for 10 min before being quenched with saturated aqueous NH$_4$Cl (1.0 mL). The mixture was diluted with water (2 mL) and extracted with EtOAc (3×5 mL). Organic layers were combined and dried over MgSO$_4$. After removal of organic solvents under reduced pressure, the crude product was subjected to reverse phase preparatory HPLC (Gemini™ Prep C18 5 μm column; Phenomenex, Torrance, CA; gradient elution of 55% MeCN in water to 90% MeCN in water over a 20 min period, where both solvents contain 0.1% TFA) to provide the title compound as a white foam. $^1$H NMR (400 MHz, CDCl$_3$) δ 8.28 (br. s., 1H), 7.69-7.57 (m, 1H), 7.10 (dd, J=2.2, 8.5 Hz, 1H), 7.01 (d, J=2.2 Hz, 1H), 6.90-6.80 (m, 2H), 6.74 (s, 1H), 5.82-5.62 (m, 1H), 5.45 (dd, J=8.1, 15.4 Hz, 1H), 4.35-4.25 (m, 1H), 4.08-3.92 (m, 2H), 3.76-3.53 (m, 3H), 3.26-3.07 (m, 4H), 2.93 (dd, J=9.7, 15.2 Hz, 1H), 2.78-2.60 (m, 2H), 2.47-2.26 (m, 3H), 2.26-1.51 (m, 12), 1.45 (s, 3H), 1.34 (s, 3H). m/z (ESI, +ve ion) 643.0 (M+H)$^+$.

Example 683. (1S,3'R,6'R,7'S,8'E,11'R)-6-chloro-11'-cyclopropyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S)-6-chloro-11'-cyclopropyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide

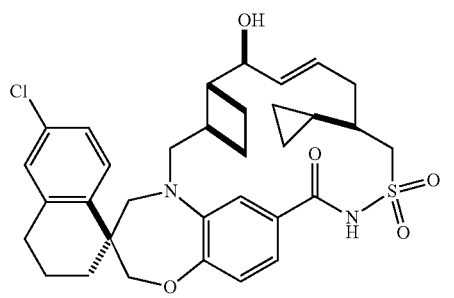

OR

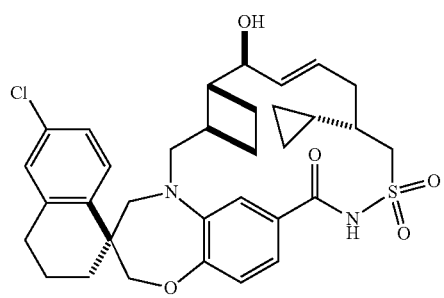

To a rt solution of (1S,3'R,6'R,7'S,8'E,11'S)-6-chloro-11'-cyclopropyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl acetate and (1S,3'R,6'R,7'S,8'E,11'R)-6-chloro-11'-cyclopropyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl acetate (35 mg, 0.054 mmol, Example 690) in anhydrous MeOH (2 mL) was added 5.4 M sodium methoxide in methanol (60 μL, 0.32 mmol, Acros). The mixture was allowed to stir at rt for 35 min. To the mixture was added HCl (0.1 mL, 4.0 N) and water (0.2 mL). The resulting solution was subjected to reversed phase preparatory HPLC (Gemini™ Prep C18 5 μm column; Phenomenex, Torrance, CA; gradient elution of 50% to 95% MeCN in water, where both solvents contain 0.1% TFA, 25 min method) to provide one of the title compounds as the first eluting isomer as a white foam. $^1$H NMR (400 MHz, CDCl$_3$) δ 8.37 (br. s., 1H), 7.70 (d, J=8.4 Hz, 1H), 7.18 (dd, J=2.0, 8.6 Hz, 1H), 7.10 (s, 1H), 7.02-6.90 (m, 2H), 6.84 (s, 1H), 5.95-5.82 (m, 1H), 5.74 (dd, J=7.9, 15.6 Hz, 1H), 4.35 (dd, J=9.8, 15.7 Hz, 1H), 4.26 (dd, J=3.5, 8.0 Hz, 1H), 4.15-4.02 (m, 2H), 3.83-3.64 (m, 2H), 3.46 (dd, J=3.7, 15.8 Hz, 1H), 3.23 (d, J=14.5 Hz, 1H), 3.06 (dd, J=9.7, 14.8 Hz, 1H), 2.87-2.66 (m, 2H), 2.53-2.29 (m, 3H), 2.29-1.39 (m, 11H), 0.79 (d, J=5.1 Hz, 1H), 0.64-0.51 (m, 2H), 0.31 (d, J=9.6 Hz, 1H), 0.25-0.16 (m, 1H). m/z (ESI, +ve ion) 611.1 (M+H)$^+$.

Example 684. (1S,3'R,6'R,7'S,8'E,11'R)-6-chloro-11'-cyclopropyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S)-6-chloro-11'-cyclopropyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide

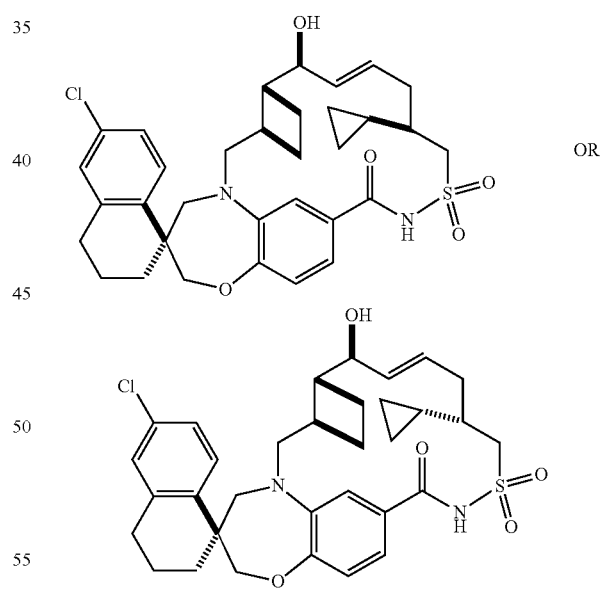

The title compound was obtained as a white foam as the second eluting isomer from the reversed phase preparatory HPLC separation in Example 683. $^1$H NMR (400 MHz, CDCl$_3$) δ 8.55 (br. s., 1H), 7.68 (d, J=8.4 Hz, 1H), 7.22-7.08 (m, 3H), 7.06-7.00 (m, 1H), 6.99-6.89 (m, 1H), 5.94-5.78 (m, 1H), 5.78-5.67 (m, 1H), 4.22-4.05 (m, 3H), 4.00-3.63 (m, 3H), 3.63-3.35 (m, 3H), 2.77-1.19 (m, 16H), 0.96-0.85 (m, 1H), 0.65-0.50 (m, 2H), 0.36-0.32 (m, 1H), 0.23-0.10 (m, 1H); m/z (ESI, +ve ion) 611.1 (M+H)$^+$.

1443

Example 685. (1S,3'R,6'R,7'S,8'E,11'S)-6-chloro-11'-ethyl-7'-hydroxy-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'R)-6-chloro-11'-ethyl-7'-hydroxy-3,4-dihydro-2H,15'H-spiro[naphthalene-1,22'-[20]oxa[13]thia[1,12,14]triazatetracyclo[14.7.2.0³,⁶.0¹⁹,²⁴]pentacosa[8,16,18,24]tetraen]-15'-one 13',13'-dioxide

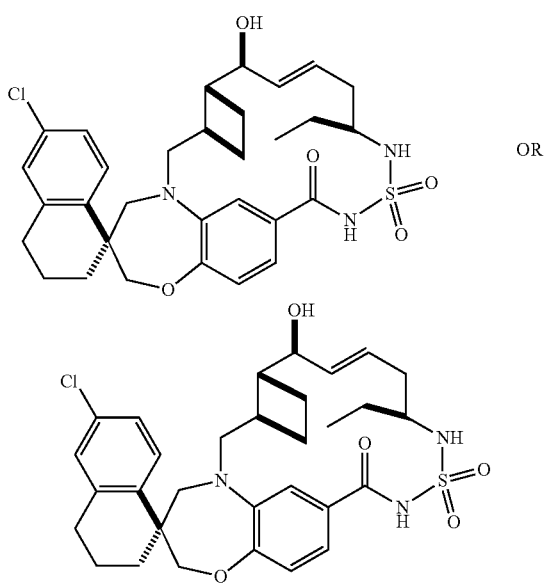

Step 1: (S)-2-(hex-5-en-3-yl)isoindoline-1,3-dione and (R)-2-(hex-5-en-3-yl)isoindoline-1,3-dione

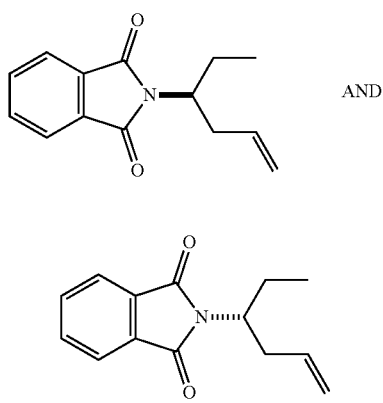

The title compounds were prepared from 5-hexen-3-ol (MP Biomedicals, Inc.) following a procedure similar to the one described for the synthesis of (S)-2-(pent-4-en-2-yl)isoindoline-1,3-dione (Step 1 for the synthesis of Example 664), except that the crude product was purified by flash chromatography on ISCO Gold silica gel column using 0-40% EtOAc/Hexanes (EtOAc containing 0.1% HOAc) to provide the title compound as white solid.

1444

Step 2: (S)-hex-5-en-3-amine and (R)-hex-5-en-3-amine

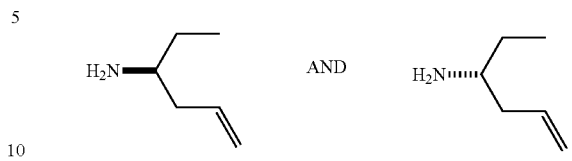

A mixture of (S)-2-(hex-5-en-3-yl)isoindoline-1,3-dione and (R)-2-(hex-5-en-3-yl)isoindoline-1,3-dione (11.2 g, 48.8 mmol, Step 1) in ethanolamine (29.3 ml, 488 mmol, Sigma-Aldrich Chemical Company, Inc.) under reflux condenser was allowed to stir for 3.0 h at 78° C., for 66 h at 45° C., and then for 3.0 h at 110° C. The reaction flask was equipped with distill short path apparatus, and slow fractional distillation of the solution in oil bath at 120° C. provided the title compounds (70-90° C.) which were directly carried to the next step.

Step 3: N-((3S)-5-hexen-3-yl)sulfuric diamide and N-((3R)-5-hexen-3-yl)sulfuric diamide

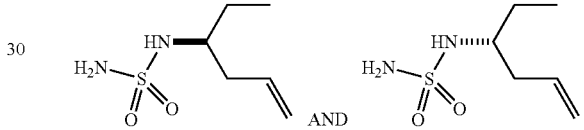

The title compounds were prepared from (S)-hex-5-en-3-amine and (R)-hex-5-en-3-amine (Step 2) following a procedure similar to the one described for the synthesis of N-4-penten-1-ylsulfuric diamide (Step 1 in the synthesis of Example 660), except that the crude product was purified by flash chromatography on ISCO Gold silica gel column using 0-100% EtOAc/Hexanes to provide the title compounds as a white solid.

Step 4: (S)-6'-chloro-N—(N—((R)-hex-5-en-3-yl)sulfamoyl)-5-(((1R,2R)-2-((S)-1-hydroxyallyl)cyclobutyl)methyl)-3',4',5-tetrahydro-2H,2'H-spiro[benzo[b][1,4]oxazepine-3,1'-naphthalene]-7-carboxamide and (S)-6'-chloro-N—(N—((S)-hex-5-en-3-yl)sulfamoyl)-5-(((1R,2R)-2-((S)-1-hydroxyallyl)cyclobutyl)methyl)-3',4',5-tetrahydro-2H,2'H-spiro[benzo[b][1,4]oxazepine-3,1'-naphthalene]-7-carboxamide

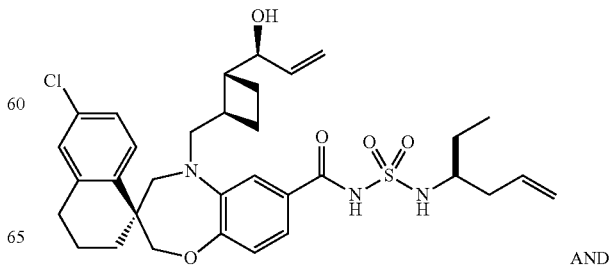

1445

-continued

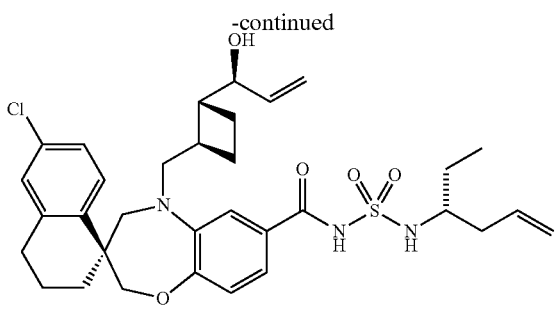

The title compounds were prepared from N-((3S)-5-hexen-3-yl)sulfuric diamide and N-((3R)-5-hexen-3-yl)sulfuric diamide (Step 2) and (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (AA11A), following a procedure similar to the one described for the synthesis of (S)-6'-chloro-5-(((1R,2R)-2-((S)-1-hydroxyallyl)cyclobutyl)methyl)-N—(N-(pent-4-en-1-yl)sulfamoyl)-3',4,4',5-tetrahydro-2H,2'H-spiro[benzo[b][1,4]oxazepine-3,1'-naphthalene]-7-carboxamide (Step 2 in the synthesis of Example 660), except that the crude product was purified by flash chromatography on ISCO Gold silica gel column using 0-100% EtOAc/Hexanes (EtOAc contained 0.1% HOAc) to provide the title compounds as a white solid.

Step 5: ((1S,3'R,6'R,7'S,8'E,11'S)-6-chloro-11'-ethyl-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide and (1S,3'R,6'R,7'S,8'E,11'R)-6-chloro-11'-ethyl-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide The title compounds were prepared from (S)-6'-chloro-N—(N—((R)-hex-5-en-3-yl)sulfamoyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide and (S)-6'-chloro-N—(N—((S)-hex-5-en-3-yl)sulfamoyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide (Step 3), following a procedure similar to the one described for the synthesis of (1S,3'R,6'R,7'S,8'E)-6-chloro-7'-hydroxy-3,4-dihydro-2H,16'H-spiro[naphthalene-1,23'-[21]oxa[14]thia[1,13,15]triazatetracyclo[15.7.2.0$^{3,6}$.0$^{20,25}$]hexacosa[8,17,19,25]tetraen]-16'-one 14',14'-dioxide (Example 660, Step 3), except that the crude product was purified by reversed phase preparatory HPLC (Gemini™ Prep C18 5 μm column; Phenomenex, Torrance, CA; gradient elution of 40% to 95% MeCN in water, where both solvents contain 0.1% TFA, 20 min method) to provide one of the title compounds as the first eluting isomer as a white foam. $^1$H NMR (400 MHz, CDCl$_3$) δ 7.69-7.63 (m, 1H), 7.15 (dd, J=2.2, 8.5 Hz, 1H), 7.09 (d, J=2.2 Hz, 1H), 7.00-6.86 (m, 3H), 5.93 (br. s., 1H), 5.87-5.64 (m, 2H), 4.71-4.55 (m, 2H), 4.05 (br. s., 1H), 3.83-3.71 (m, 1H), 3.59-3.09 (m, 3H), 2.84-2.70 (m, 2H), 2.59-2.49 (m, 1H), 2.47-2.28 (m, 2H), 1.97-1.43 (m, 13H), 1.05-0.80 (m, 3H); m/z (ESI, +ve ion) 600.1 (M+H)$^+$.

Example 686. (1S,3'R,6'R,7'S,8'E,11'S)-6-chloro-11'-ethyl-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R)-6-chloro-11'-ethyl-7'-hydroxy-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

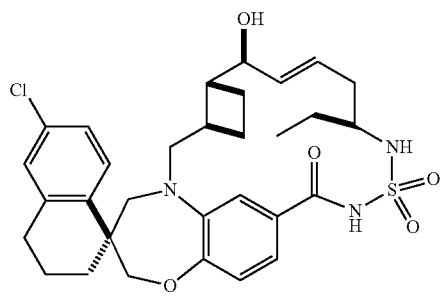

OR

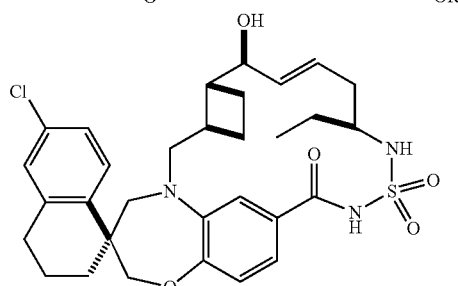

The title compound was obtained as a white foam as the second eluting isomer from the reversed phase preparatory HPLC separation in Example 685, Step 5. $^1$H NMR (400 MHz, CDCl$_3$) δ 8.70 (br. s., 1H), 7.69 (d, J=8.6 Hz, 1H), 7.18 (dd, J=2.3, 8.4 Hz, 1H), 7.09 (d, J=2.2 Hz, 1H), 6.95-6.86 (m, 2H), 6.84 (s, 1H), 5.94-5.80 (m, 1H), 5.73 (d, J=8.2 Hz, 2H), 4.27 (br. s., 1H), 4.11-4.02 (m, 3H), 3.83-3.66 (m, 2H), 3.52 (br. s., 1H), 3.20 (d, J=14.3 Hz, 1H), 3.00 (dd, J=9.6, 15.3 Hz, 1H), 2.86-2.69 (m, 2H), 2.55-2.36 (m, 2H), 2.30-1.32 (m, 12H), 1.16-0.80 (m, 3H). m/z (ESI, +ve ion) 600.0 (M+H)$^+$.

Example 687. (1S,3'R,6'R,7'S,8'E,11'S)-6-chloro-7'-hydroxy-12'-((2R)-2-hydroxy-3-methoxypropyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

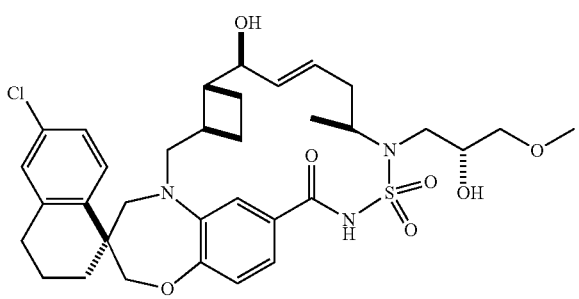

Step 1: (R)-1-methoxy-3-((S)-pent-4-en-2-ylamino)propan-2-ol

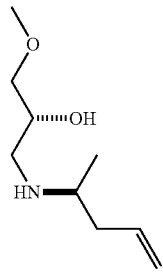

To (S)-pent-4-en-2-amine (0.916 g, 6.02 mmol, 56% in diethyl ether, prepared in Step 3 for the synthesis of Example 664) was added (R)-(−)-glycidyl methyl ether, 97% (0.531 mL, 6.02 mmol) followed by water (2 mL) at rt. The flask was sealed and allowed to stir vigorously at rt for 24 h. The mixture as diluted with water (8 mL) and extracted with diethyl ether (5×8 mL). The organic layers were combined, dried over $Na_2SO_4$. The solid was filtered off through a small pad of Celite® (diatomaceous earth). Removal of organic solvents provided the title compound as a crude colorless syrup.

Step 2: (S)—N—((R)-2-((tert-butyldimethylsilyl)oxy)-3-methoxypropyl)pent-4-en-2-amine

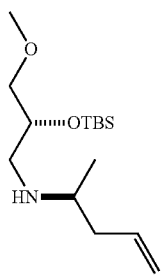

To a mixture of (R)-1-methoxy-3-((S)-pent-4-en-2-ylamino)propan-2-ol (0.957 g, 2.76 mmol, Step 1), imidazole (0.547 ml, 8.29 mmol) and tert-butyl-chlorodimethyl-silan (1.25 g, 8.29 mmol) was added DMF (9.2 ml) at rt. The mixture was allowed to stir at rt for 72 h, treated with water (25 mL) and extracted with EtOAc (3×15 mL). The organic layers were combined and washed with water (3×15 mL). Removal of organic solvents under reduced pressure provided the crude title compound.

Step 3: N-((2R)-2-((dimethyl(2-methyl-2-propanyl)silyl)oxy)-3-methoxypropyl)-N-((2S)-4-penten-2-yl)sulfuric diamide

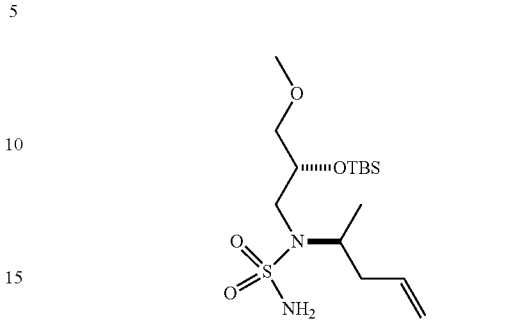

The title compound was prepared from (S)—N—((R)-2-((tert-butyldimethylsilyl)oxy)-3-methoxypropyl)pent-4-en-2-amine (Step 2) following a procedure similar to the one described for the synthesis of N-4-penten-1-ylsulfuric diamide (Step 1 in the synthesis of Example 660), except that the crude product was purified by flash chromatography on ISCO Gold silica gel column using 0-100% EtOAc/Hexanes (EtOAc containing 0.1% HOAc) to provide the title compound as a white solid.

Step 4: (S)—N—(N—((R)-2-((tert-butyldimethylsilyl)oxy)-3-methoxypropyl)-N—((S)-pent-4-en-2-yl)sulfamoyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide

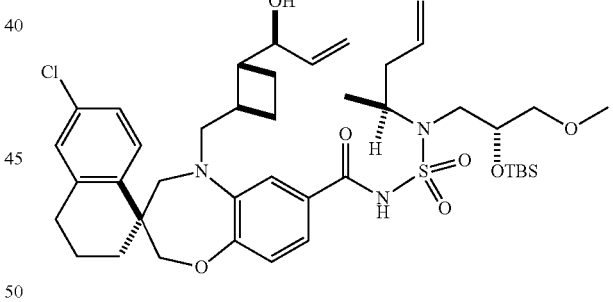

The title compounds were prepared as a mixture from N-((2R)-2-((dimethyl(2-methyl-2-propanyl)silyl)oxy)-3-methoxypropyl)-N-((2S)-4-penten-2-yl)sulfuric diamide (Step 3) and (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (AA11A), following a procedure similar to the one described for the synthesis of (S)-6'-chloro-5-(((1R,2R)-2-((S)-1-hydroxyallyl)cyclobutyl)methyl)-N—(N-(pent-4-en-1-yl)sulfamoyl)-3',4,4',5-tetrahydro-2H,2'H-spiro[benzo[b][1,4]oxazepine-3,1'-naphthalene]-7-carboxamide (Step 2 in the synthesis of Example 660), except that the crude product was purified by flash chromatography on ISCO Gold silica gel column using 0-100% EtOAc/Hexanes (EtOAc contained 0.1% HOAc) to provide the title compound as a white solid.

Step 5: (1S,3'R,6'R,7'S,8'E,11'S)-6-chloro-12'-((2R)-2-((dimethyl(2-methyl-2-propanyl)silyl)oxy)-3-methoxypropyl)-7'-hydroxy-11'-methyl-3,4-dihydro-2H,15'H-spiro[naphthalene-1,22'-[20]oxa[13]thia[1,12,14]triazatetracyclo[14.7.2.0~3,6~.0~19,24~]Pentacosa[8,16,18,24]tetraen]-15'-one 13',13'-dioxide

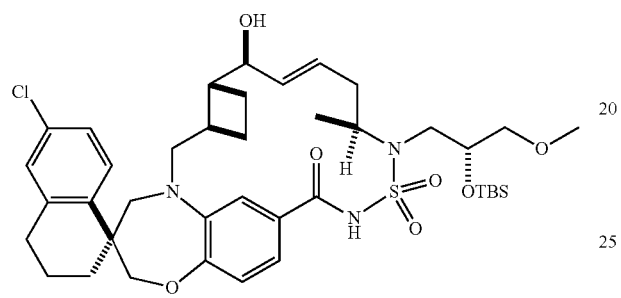

The title compound was prepared from (S)—N—(N—((R)-2-((tert-butyldimethylsilyl)oxy)-3-methoxypropyl)-N—((S)-pent-4-en-2-yl)sulfamoyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide (Step 4), following a procedure similar to the one described for the synthesis of (1S,3'R,6'R,7'S,8'E)-6-chloro-7'-hydroxy-3,4-dihydro-2H,16'H-spiro[naphthalene-1,23'-[21]oxa[14]thia[1,13,15]triazatetracyclo[15.7.2.0$^{3,6}$.0$^{20,25}$]hexacosa[8,17,19,25]tetraen]-16'-one 14',14'-dioxide (Example 660, Step 3), except that the crude product was purified by reversed phase preparatory HPLC (Gemini® 10 μm NX—C18 110 Å column; gradient elution of 50% to 95% MeCN in water, where both solvents contain 0.1% TFA, 20 min method) to provide the title compound as a white foam.

Step 6: (1S,3'R,6'R,7'S,8'E,11'S)-6-chloro-7'-hydroxy-12'-((2R)-2-hydroxy-3-methoxypropyl)-11'-methyl-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide To a flask containing (1S,3'R,6'R,7'S,8'E,11'S)-6-chloro-12'-((2R)-2-((dimethyl(2-methyl-2-propanyl)silyl)oxy)-3-methoxypropyl)-7'-hydroxy-11'-methyl-3,4-dihydro-2H,15'H-spiro[naphthalene-1,22'-[20]oxa[13]thia[1,12,14]triazatetracyclo[14.7.2.0~3,6~.0~19,24~]pentacosa[8,16,18,24]tetraen]-15'-one 13',13'-dioxide (37 mg, 0.047 mmol, Step 5) was added tetrabutylammonium fluoride (0.469 mL, 1.0 N in THF, 0.469 mmol, Sigma-Aldrich Chemical Company, Inc.) at rt. The solution was stirred at rt for 24 h. After removal of organic solvents under reduced pressure, purification of the residue by reversed phase preparatory HPLC (Gemini™ Prep C18 5 μm column; Phenomenex, Torrance, CA; gradient elution of 45% to 90% MeCN in water, where both solvents contain 0.1% TFA, 20 min method) provided the title compound as a white foam. $^1$H NMR (400 MHz, CDCl$_3$) δ 8.76 (br. s., 1H), 7.74-7.65 (m, 1H), 7.24-7.13 (m, 2H), 7.08 (d, J=2.2 Hz, 1H), 6.98-6.86 (m, 2H), 5.77-5.51 (m, 2H), 4.50-4.36 (m, 1H), 4.21-3.96 (m, 3H), 3.92 (t, J=5.6 Hz, 1H), 3.86-3.63 (m, 3H), 3.59-3.46 (m, 3H), 3.43-3.40 (m, 4H), 3.25 (d, J=14.3 Hz, 1H), 3.06 (dd, J=5.9, 15.5 Hz, 1H), 2.83-2.70 (m, 2H), 2.59-2.35 (m, 3H), 2.22-1.38 (m, 9H), 1.34 (d, J=6.7 Hz, 3H), 1.30-1.23 (m, 1H). m/z (ESI, +ve ion) 674.3 (M+H)$^+$.

Example 688. (1S,3'R,6'R,7'S,8'E,12'R)-6,17'-dichloro-12'-ethyl-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

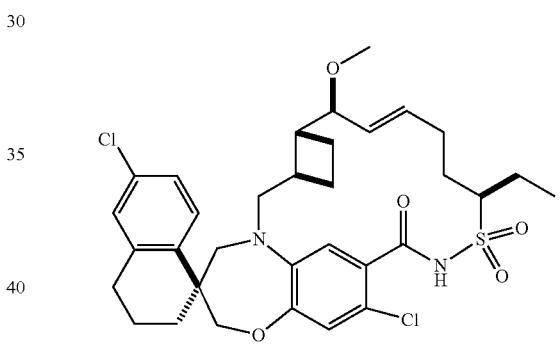

The title compound was prepared from (1S,3'R,6'R,7'S,8'E,12'R)-6,17'-dichloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 657) following a procedure similar to the one described for the synthesis of Example 669 using methyl iodide instead of 2-bromoethyl methyl ether, except that the crude product was purified by reversed phase preparatory HPLC (Gemini™ Prep C18 5 μm column; Phenomenex, Torrance, CA; gradient elution of 40% to 95% MeCN in water, where both solvents contain 0.1% TFA, 25 min method) to provide the title compound as a white film. $^1$H NMR (400 MHz, CDCl$_3$) δ 7.65 (d, J=8.4 Hz, 1H), 7.19 (dd, J=2.1, 8.5 Hz, 1H), 7.09 (s, 1H), 7.01-6.97 (m, 1H), 6.95-6.91 (m, 1H), 5.87-5.74 (m, 1H), 5.55 (dd, J=8.8, 15.5 Hz, 1H), 4.19-1.20 (m, 35H). m/z (ESI, +ve ion) 615.0 (M−MeOH+H)$^+$.

Example 689. (1S,3'R,6'R,7'S,8'E,11'S,12'R)-6-chloro-7'-methoxy-11'-methyl-12'-(2,2,2-trifluoroethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13', 13'-dioxide or (1S,3'R,6'R,7'S,8'E,11'S,12'S)-6-chloro-7'-methoxy-11'-methyl-12'-(2,2,2-trifluoroethyl)-3,4-dihydro-2H,15'H-spiro [naphthalene-1,22'-[20]oxa[13]thia[1,14] diazatetracyclo[14.7.2.0³,⁶.0¹⁹,²⁴]pentacosa [8,16,18, 24]tetraen]-15'-one 13',13'-dioxide or (1S,3'R,6'R, 7'S,8'Z,11'S,12'R)-6-chloro-7'-methoxy-11'-methyl-12'-(2,2,2-trifluoroethyl)-3,4-dihydro-2H,15'H-spiro [naphthalene-1,22'-[20]oxa[13]thia[1,14] diazatetracyclo[14.7.2.0³,⁶.0¹⁹,²⁴]pentacosa [8,16,18, 24]tetraen]-15'-one 13',13'-dioxide or (1S,3'R,6'R, 7'S,8'Z,11'S,12'S)-6-chloro-7'-methoxy-11'-methyl-12'-(2,2,2-trifluoroethyl)-3,4-dihydro-2H,15'H-spiro [naphthalene-1,22'-[20]oxa[13]thia[1,14] diazatetracyclo[14.7.2.0³,⁶.0¹⁹,²⁴]pentacosa [8,16,18, 24]tetraen]-15'-one 13',13'-dioxide

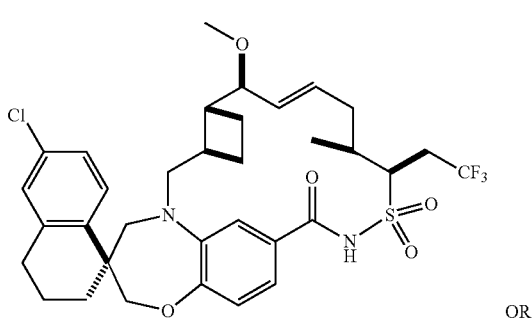

OR


OR

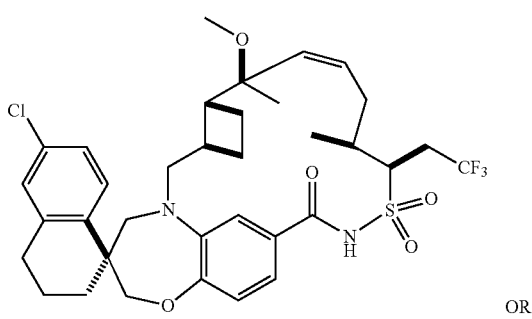

OR

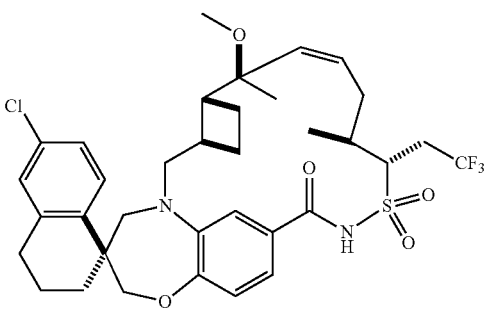

The title compound was prepared from 1S,3'R,6'R,7'S, 8'E,11'S,12'R)-6-chloro-7'-hydroxy-11'-methyl-12'-(2,2,2-trifluoroethyl)-3,4-dihydro-2H,15'H-spiro[naphthalene-1, 22'-[20]oxa[13]thia[1,14]diazatetracyclo[14.7.2.0³,⁶.0¹⁹,²⁴] pentacosa[8,16,18,24]tetraen]-15'-one 13',13'-dioxide and (1S,3'R,6'R,7'S,8'E,11'S,12'S)-6-chloro-7'-hydroxy-11'-methyl-12'-(2,2,2-trifluoroethyl)-3,4-dihydro-2H,15'H-spiro[naphthalene-1,22'-[20]oxa[13]thia[1,14]diazatetracyclo [14.7.2.0³,⁶.0¹⁹,²⁴]pentacosa[8,16,18,24]tetraen]-15'-one 13',13'-dioxide and (1S,3'R,6'R,7'S,8'Z,11'S,12'R)-6-chloro-7'-hydroxy-11'-methyl-12'-(2,2,2-trifluoroethyl)-3,4-dihydro-2H,15'H-spiro[naphthalene-1,22'-[20]oxa[13]thia [1,14]diazatetracyclo[14.7.2.0³,⁶.0¹⁹,²⁴]pentacosa[8,16,18, 24]tetraen]-15'-one 13',13'-dioxide and (1S,3'R,6'R,7'S,8'Z, 11'S,12'S)-6-chloro-7'-hydroxy-11'-methyl-12'-(2,2,2-trifluoroethyl)-3,4-dihydro-2H,15'H-spiro[naphthalene-1, 22'-[20]oxa[13]thia[1,14]diazatetracyclo[14.7.2.0³,⁶.0¹⁹,²⁴] pentacosa[8,16,18,24]tetraen]-15'-one 13',13'-dioxide (Example 663) following a procedure similar to the one described for the synthesis of Example 669 using methyl iodide instead of 2-bromoethyl methyl ether, except that the crude product was purified by reversed phase preparatory HPLC (Gemini™ Prep C18 10 μm column; Phenomenex, Torrance, CA; gradient elution of 40% to 95% MeCN in water, where both solvents contain 0.1% TFA, 30 min method) to provide one of the title compounds as the second eluting isomer as a white foam. $^1$H NMR (400 MHz, CDCl$_3$) δ 8.13 (s, 1H), 7.69 (d, J=8.6 Hz, 1H), 7.18 (d, J=8.4 Hz, 1H), 7.10 (s, 1H), 6.99-6.86 (m, 2H), 5.85-5.74 (m, 1H), 5.55 (dd, J=9.0, 15.7 Hz, 1H), 4.58 (d, J=5.3 Hz, 1H), 4.10 (m, 2H), 3.81 (d, J=14.9 Hz, 1H), 3.76-3.64 (m, 2H), 3.31-3.18 (s, 3H), 3.27-1.23 (m, 18H), 1.12 (d, J=6.7 Hz, 3H). m/z (ESI, +ve ion) 681.0 (M+H)$^+$.

Example 690. (1S,3'R,6'R,7'S,8'E,11'S)-6-chloro-11'-cyclopropyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-7'-yl acetate and (1S,3'R,6'R,7'S,8'E,11'R)-6-chloro-11'-cyclopropyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [8,16,18,24]tetraen]-7'-yl acetate

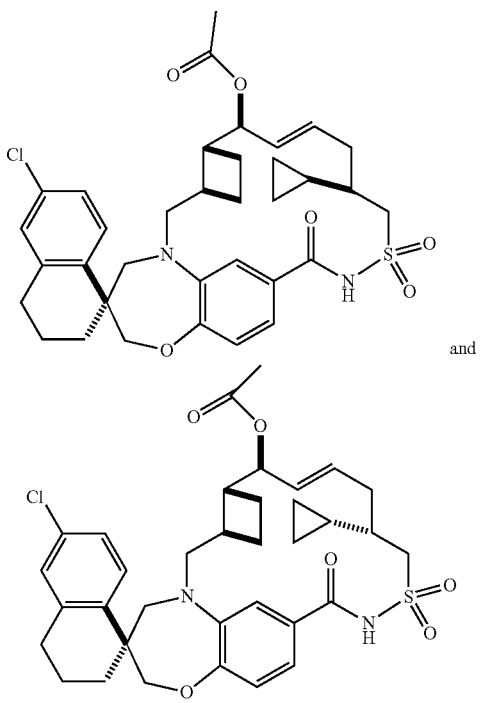

and

Step 1: benzyl 2-cyclopropylacetate

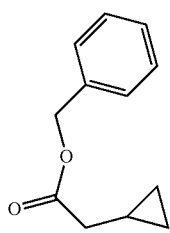 [SMILES: O=C(CC1CC1)OCc1ccccc1]

To a mixture of granular potassium iodide (19.9 g, 120 mmol, ZZ-INACTIVE-Mallinckrodt GmbH), potassium carbonate powder (41.5 g, 300 mmol, Fluka Chemie GmbH), and cyclopropylacetic acid (9.28 mL, 100 mmol, Alfa Aesar, Avocado, Lancaster) in DMF (100 mL) was added benzyl bromide (30.5 mL, 250 mmol, Sigma-Aldrich Chemical Company, Inc.) at rt. The mixture was allowed to stir at 90° C. under condenser and $N_2$ for overnight. The reaction mixture was cooled to rt, the solid was filtered off on a pad of Celite® (diatomaceous earth) and washed with EtOAc (3×20 mL). The combined organic solution was diluted with EtOAc (400 mL) and washed with water (4×200 mL) and brine (45 mL), and dried over $MgSO_4$. After removal of organic solvents under reduced pressure, purification of the residue by flash chromatography on ISCO Gold silica gel column with 0-40% EtOAc/Hexanes provided the title compound as a as a dark brown oil.

Step 2: (R)-benzyl 2-cyclopropylpent-4-enoate and (S)-benzyl 2-cyclopropylpent-4-enoate

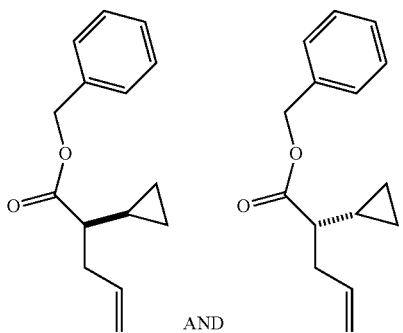 [SMILES: C=CC[C@@H](C(=O)OCc1ccccc1)C1CC1 ; C=CC[C@H](C(=O)OCc1ccccc1)C1CC1]

AND

To a solution of diisopropylamine (18.1 mL, 129 mmol, redistilled, 99.95%, Sigma-Aldrich Chemical Company, Inc.) in THF (100 mL) at −78° C. under $N_2$ was added ⁿBuLi (51.7 mL, 2.5 M solution in hexanes, 129 mmol, Sigma-Aldrich Chemical Company, Inc.) over 10 min. The mixture was allowed to stir in the cold bath for 20 min, then removed from the ice bath. After stirring at ambient atmosphere for 20 min, this freshly made lithium diisopropylamide solution was replaced into the −50° C. bath for temporary storage. To a solution of benzyl 2-cyclopropylacetate (16.200 g, 85 mmol, Step 1) in THF (170 ml) under $N_2$ in −78° C. bath was added allyl bromide (7.37 ml, 85 mmol, reagentplus, Sigma-Aldrich Chemical Company, Inc.) followed by slow addition of the freshly made lithium diisopropylamide solution (124 ml, 0.758 M, 94 mmol) over 15 min. The mixture was stirred at −78° C. for 30 min, and then was removed from the bath and allowed to stir at ambient temperature for 45 min. The reaction mixture was poured into saturated aqueous $NH_4Cl$ (150 mL), diluted with water (150 mL) and extracted with EtOAc (3×200 mL). The organic solutions were combined. After removal of organic solvents under reduced pressure, purification of the residue by flash chromatography on ISCO Gold silica gel column with 0-50% EtOAc/Hexanes provided the title compounds as as mixture. m/z (ESI, +ve ion) 231.1 (M+H)⁺.

Step 3: (R)-2-cyclopropylpent-4-en-1-ol and (S)-2-cyclopropylpent-4-en-1-ol

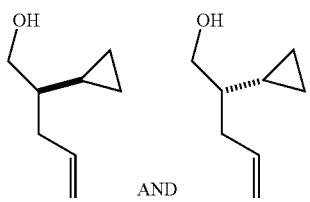

AND

To a solution of (R)-benzyl 2-cyclopropylpent-4-enoate and (S)-benzyl 2-cyclopropylpent-4-enoate (11.2 g, 48.6 mmol, Step 2) in THF (200 mL) under N$_2$ in 0° C. ice bath was slowly added lithium aluminum hydride (56.0 mL, 1.0 M in THF, 56.0 mmol, Sigma-Aldrich Chemical Company, Inc.) via syringe over 10 min. The mixture was allowed to stir in the ice bath for 3.0 h. To the mixture was slowly added EtOAc (45 mL), the solution was removed from ice bath followed by addition of saturated aqueous NH$_4$Cl (80 mL). The resulting mixture was treated with 60 mL of 1.0 N aqueous solution of citric acid (Sigma-Aldrich Chemical Company, Inc.), diluted with water (150 mL). The organic layer was separated and the aqueous layer was back extracted with EtOAc (3×200 mL). The organic layers were combined. After removal of organic solvents under reduced pressure, purification of the residue by flash chromatography on ISCO Gold silica gel column with 0-60% EtOAc/Hexanes provided the title compounds as a mixture.

Step 4: (R)-2-cyclopropylpent-4-en-1-yl methane-sulfonate and (S)-2-cyclopropylpent-4-en-1-yl methanesulfonate

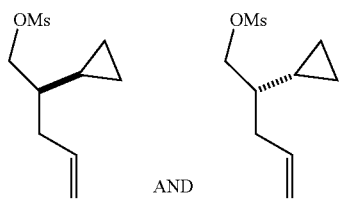

To a solution of (R)-2-cyclopropylpent-4-en-1-ol and (S)-2-cyclopropylpent-4-en-1-ol (7.00 g, 55.5 mmol, Step 3) in dichloromethane (80 mL) in 0° C. ice bath under N$_2$ was added triethylamine (9.26 mL, 66.6 mmol, Sigma-Aldrich Chemical Company, Inc.) followed by methanesulfonyl chloride (5.15 mL, 66.6 mmol, Sigma-Aldrich Chemical Company, Inc.). The resulting milky mixture was allowed to stir in the ice bath for 3.0 h. To the cloudy mixture was added cold water (50 mL). The organic layer was separated and the aqueous layer was back extracted with dichloromethane (3×40 mL). The organic layers were combined, washed subsequently with water (40 mL), brine (40 mL), and dried over MgSO$_4$. Removal of organic solvents under reduced pressure provided the crude titled compounds as a mixture, which was immediately used without further purification.

Step 5: (R)-2-((2-cyclopropylpent-4-en-1-yl)thio)pyrimidine and (S)-2-((2-cyclopropylpent-4-en-1-yl)thio)pyrimidine

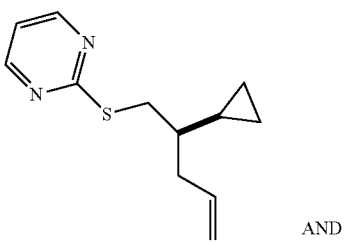

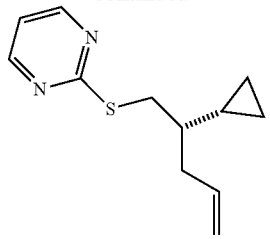

To a solution of (R)-2-cyclopropylpent-4-en-1-yl methanesulfonate and (S)-2-cyclopropylpent-4-en-1-yl methanesulfonate (10.0 g, 49.0 mmol, Step 4) and 2-mercaptopyrimidine (6.59 g, 58.7 mmol, Sigma-Aldrich Chemical Company, Inc) in DMF (98 ml) was added potassium carbonate anhydrous (8.11 g, 58.7 mmol, Fluka Chemie GmbH). The mixture was allowed to stir at 70° C. for 2.5 h, cooled to rt and poured in water (400 mL), extracted with EtOAc (3×100 mL). The combined organic layer was washed subsequently with water (4×80 mL), brine (30 mL), and dried over MgSO$_4$. After removal of organic solvents under reduced pressure, purification of the residue by flash chromatography on ISCO Gold silica gel column with 0-70% EtOAc/Hexanes provided the title compounds as a mixture.

Step 6: (R)-2-((2-cyclopropylpent-4-en-1-yl)sulfonyl)pyrimidine and (S)-2-((2-cyclopropylpent-4-en-1-yl)sulfonyl)pyrimidine

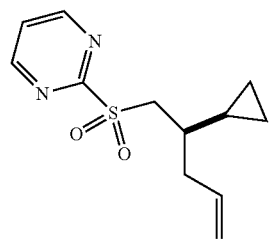

AND

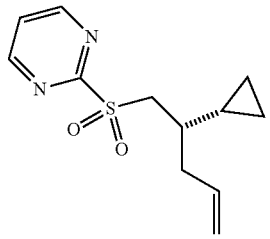

The title compounds were prepared from (R)-2-((2-cyclopropylpent-4-en-1-yl)thio)pyrimidine and (S)-2-((2-cyclopropylpent-4-en-1-yl)thio)pyrimidine (Step 5) following a procedure similar to the one described for the synthesis of 2-(((2r,3s)-3-methylhex-5-en-2-yl)sulfonyl)pyrimidine (Step 4 in the synthesis of EE22), except that the crude products was purified by flash chromatography on ISCO Gold silica gel column using 0-70% EtOAc/Hexanes provided the title compounds as a solid mixture. m/z (ESI, +ve ion) 253.1 (M+H)$^+$.

Step 7: Sodium (R)-2-cyclopropylpent-4-ene-1-sulfinate and Sodium (S)-2-cyclopropylpent-4-ene-1-sulfinate

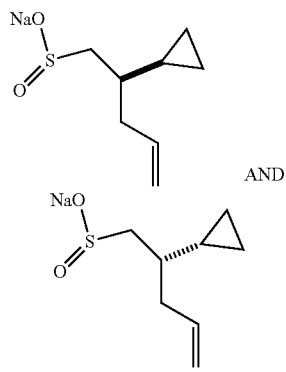

AND

The title compounds was prepared from (R)-2-((2-cyclopropylpent-4-en-1-yl)sulfonyl)pyrimidine and (S)-2-((2-cyclopropylpent-4-en-1-yl)sulfonyl)pyrimidine (Step 6) following a procedure similar to the one described for the synthesis of sodium (2r,3s)-3-methylhex-5-ene-2-sulfinate (Step 5 in the synthesis of EE22). The crude product mixture was directly used without further purification.

Step 8: (R)-2-cyclopropylpent-4-ene-1-sulfonamide and (S)-2-cyclopropylpent-4-ene-1-sulfonamide

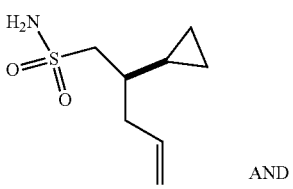

AND

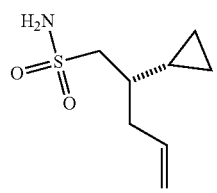

The title compound was prepared as a mixture from sodium (R)-2-cyclopropylpent-4-ene-1-sulfinate and sodium (S)-2-cyclopropylpent-4-ene-1-sulfinate (Step 7) following a procedure similar to the one described in Step 6 for the synthesis of (2R,3S)-3-methylhex-5-ene-2-sulfonamide EE22.

Step 9: (S)-6'-chloro-5-(((1R,2R)-2-((1S,5S,E)-5-cyclopropyl-1-hydroxy-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1S,5R,E)-5-cyclopropyl-1-hydroxy-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic Acid

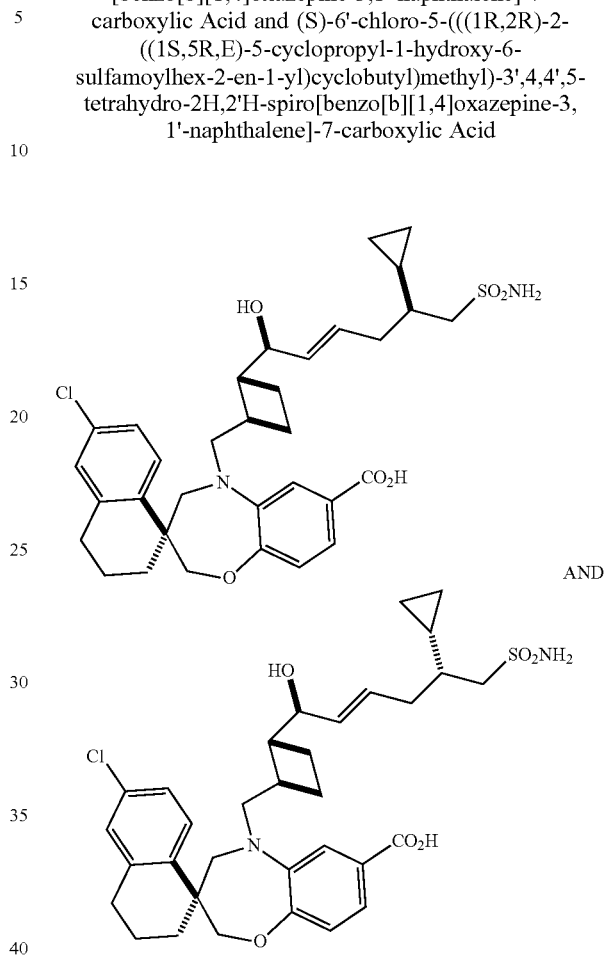

The title compounds were prepared as a mixture from (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (AA11A) and (R)-2-cyclopropylpent-4-ene-1-sulfonamide and (S)-2-cyclopropylpent-4-ene-1-sulfonamide (Step 8) following a procedure similar to the one described in Example 653, Step 4.

Step 10: (1S,3'R,6'R,7'S,8'E,11'S)-6-chloro-11'-cyclopropyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24] tetraen]-7'-yl acetate and (1S,3'R,6'R,7'S,8'E,11'R)-6-chloro-11'-cyclopropyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl acetate To a flask containing (S)-6'-chloro-5-(((1R,2R)-2-((1S,5S,E)-5-cyclopropyl-1-hydroxy-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1S,5R,E)-5-cyclopropyl-1-hydroxy-6-sulfamoylhex-2-en-1-yl)cyclobutyl)methyl)-3',4,4',5-tetrahydro-2H,2'H-spiro[benzo[b][1,4]oxazepine-3, 1'-naphthalene]-7-carboxylic acid (101 mg, 0.161 mmol, Step 9), 4-(dimethylamino)pyridine (58.8 mg, 0.482 mmol, ZZ—Alfa Aesar) and 1-(3-dimethylaminopropyl)-3-ethyl-carbodiimide hydrochloride (92.0 mg, 0.482 mmol, Thermo Fisher Scientific) was added CHCl₃. (40 mL) at rt. The mixture was allowed to stir at rt for 24 h. After removal of organic solvents under reduced pressure, the residue was re-dissolved in HOAc (4.0 mL) and left at rt for overnight. The mixture was subjected to reverse phase preparatory HPLC (Gemini™ Prep C18 5 µm column; Phenomenex, Torrance, CA; gradient elution of 45% MeCN in water to 95% MeCN in water over a 25 min period, where both solvents contain 0.1% TFA) to provide the titled compounds as a 1:1 mixture of two isomers. $^1$H NMR (400 MHz, CDCl₃) δ 8.24-8.03 (m, 1H), 7.78-7.62 (m, 1H), 7.18 (dd, J=2.3, 8.4 Hz, 1H), 7.10 (s, 1H), 7.04-6.82 (m, 3H), 6.03-5.88 (m, 1H), 5.72-5.54 (m, 1H), 5.36-5.22 (m, 1H), 4.43 (dd, J=10.0, 15.6 Hz, 0.5H), 4.18-3.98 (m, 2H), 3.96-3.54 (m, 3H), 3.48-2.89 (m, 3.5H), 2.89-2.68 (m, 2H), 2.57-1.20 (m, 14.5H), 0.93-0.72 (m, 1.5H), 0.66-0.44 (m, 2H), 0.39-0.06 (m, 2H). m/z (ESI, +ve ion) 653.0 (M+H)$^+$.

Example 691. (1S,3'R,6'R,7'S,8'E)-6-chloro-7'-hydroxy-11'-((2R)-tetrahydro-2-furanylmethyl)-3,4-dihydro-2H,14'H-spiro[naphthalene-1,21'-[19]oxa[12]thia[1,11,13]triazatetracyclo[13.7.2.0$^{3,6}$.0$^{18,23}$]tetracosa[8,15,17,23]tetraen]-14'-one 12',12'-dioxide and (1S,3'R,6'R,7'S,8'E)-6-chloro-7'-hydroxy-11'-((2S)-tetrahydro-2-furanylmethyl)-3,4-dihydro-2H,14'H-spiro[naphthalene-1,21'-[19]oxa[12]thia[1,11,13]triazatetracyclo[13.7.2.0$^{3,6}$.0$^{18,23}$]tetracosa[8,15,17,23]tetraen]-14'-one 12',12'-dioxide

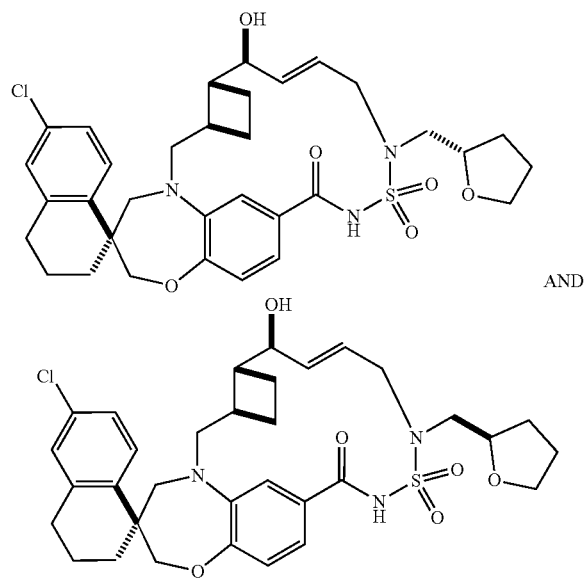

AND

Step 1: (R)—N-((tetrahydrofuran-2-yl)methyl)prop-2-en-1-amine and (S)—N-((tetrahydrofuran-2-yl)methyl)prop-2-en-1-amine

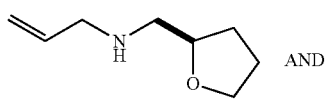

AND

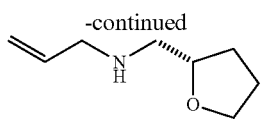

The title compounds were prepared as a mixture from tetrahydro-furan-2-carbaldehyde (J & W PharmLab, LLC) and allylamine (Sigma-Aldrich Chemical Company, Inc.) following a procedure similar to the one described for the procedure in Example 664, Step 4.

Step 2: N-2-propen-1-yl-N-((2R)-tetrahydro-2-furanylmethyl)sulfuric diamide and N-2-propen-1-yl-N-((2S)-tetrahydro-2-furanylmethyl)sulfuric diamide

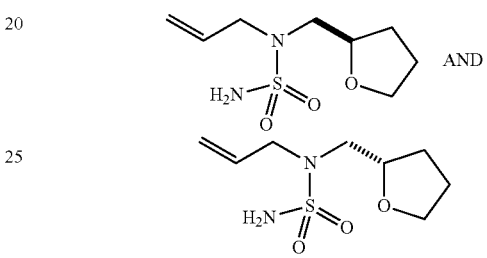

The title compounds were prepared as a mixture from (R)—N-((tetrahydrofuran-2-yl)methyl)prop-2-en-1-amine and (S)—N-((tetrahydrofuran-2-yl)methyl)prop-2-en-1-amine (Step 1) following a procedure similar to the one described for the synthesis of N-4-penten-1-ylsulfuric diamide (Step 1 in the synthesis of Example 660), except that the crude product was purified by flash chromatography on ISCO Gold silica gel column using 0-100% EtOAc/Hexanes to provide the title compounds as a white solid mixture.

Step 3: (S)—N—(N-allyl-N—(((R)-tetrahydrofuran-2-yl)methyl)sulfamoyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide and (S)—N—(N-allyl-N—(((S)-tetrahydrofuran-2-yl)methyl)sulfamoyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide

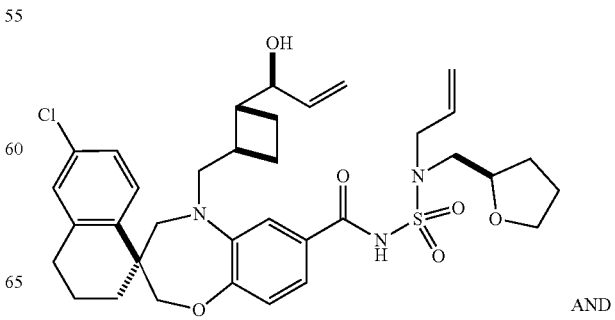

AND

-continued

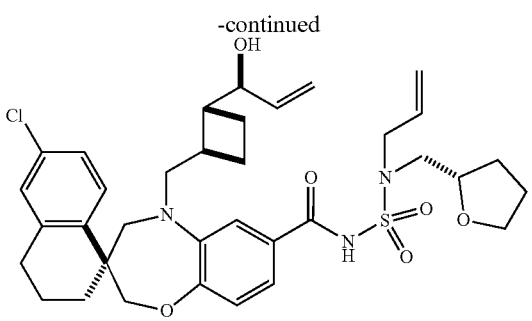

The title compounds were prepared as a mixture from N-2-propen-1-yl-N-((2R)-tetrahydro-2-furanylmethyl)sulfuric diamide and N-2-propen-1-yl-N-((2S)-tetrahydro-2-furanylmethyl)sulfuric diamide (Step 2) and (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (AA11A), following a procedure similar to the one described in Step 2 for the synthesis of Example 660, except that the crude product was purified by flash chromatography on ISCO Gold silica gel column using 0-70% EtOAc/Hexanes (EtOAc contained 0.1% HOAc) to provide the title compounds as a white solid.

Step 4: (1S,3'R,6'R,7'S,8'E)-6-chloro-7'-hydroxy-11'-((2R)-tetrahydro-2-furanylmethyl)-3,4-dihydro-2H,14'H-spiro[naphthalene-1,21'-[19]oxa[12]thia[1,11,13]triazatetracyclo[13.7.2.0$^{3,6}$.0$^{18,23}$]tetracosa[8,15,17,23]tetraen]-14'-one 12',12'-dioxide and (1S,3'R,6'R,7'S,8'E)-6-chloro-7'-hydroxy-11'-((2S)-tetrahydro-2-furanylmethyl)-3,4-dihydro-2H,14'H-spiro[naphthalene-1,21'-[19]oxa[12]thia[1,11,13]triazatetracyclo[13.7.2.0$^{3,6}$.0$^{18,23}$]tetracosa [8,15,17,23]tetraen]-14'-one 12',12'-dioxide The title compounds were prepared from (S)—N—(N-allyl-N—(((R)-tetrahydrofuran-2-yl)methyl)sulfamoyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide and (S)—N—(N-allyl-N—(((S)-tetrahydrofuran-2-yl)methyl)sulfamoyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide (Step 3), following a procedure similar to the one described in Step 3 for the synthesis of Example 660, except that the reaction was prolonged to 24 h, and the crude products were purified by reversed phase preparatory HPLC (Gemini™ Prep C18 10 μm column; Phenomenex, Torrance, CA; gradient elution of 45% to 95% MeCN in water, where both solvents contain 0.1% TFA, 30 min method) to provide the title compounds as a 1:1 mixture as a white foam. $^1$H NMR (400 MHz, CDCl$_3$) δ 9.87 (br. s., 0.5H), 8.83 (br. s., 0.5H), 7.70-7.56 (m, 1H), 7.11 (td, J=2.3, 8.5 Hz, 1H), 7.06-6.91 (m, 2H), 6.89-6.73 (m, 2H), 6.17-6.01 (m, 0.5H), 5.94-5.64 (m, 1.5H), 4.40 (dd, J=4.6, 15.9 Hz, 0.5H), 4.35-4.26 (m, 0.5H), 4.20 (d, J=15.7 Hz, 0.5H), 4.15-4.03 (m, 1.5H), 3.96-3.20 (m, 7H), 3.09-3.02 (m, 1H), 2.78-2.64 (m, 2H), 2.40-2.25 (m, 1H), 2.05-1.27 (m, 17H); (ESI, +ve ion) 642.3 (M+H)$^+$.

Example 692. (1S,3'R,6'R,7'S,8'E,12'S)-6-chloro-7'-hydroxy-12'-(2-pyridinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-hydroxy-12'-(2-pyridinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

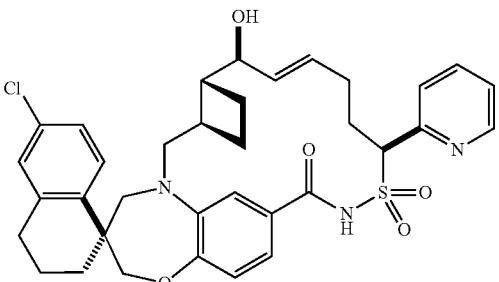

OR

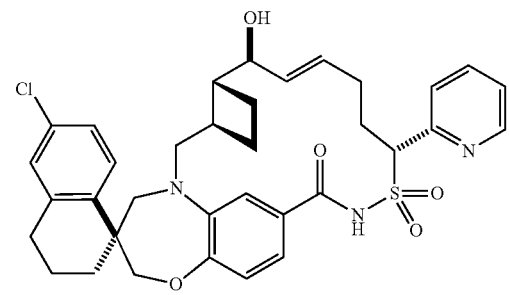

Step 1: N,N-bis(4-methoxybenzyl)-1-(pyridin-2-yl)methanesulfonamide

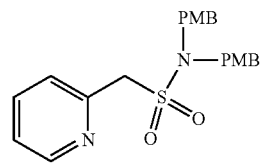

The title compound was prepared from pyridin-2-ylmethanesulfonamide (Princeton Bio) following a procedure similar to the one described for the synthesis of EE12.

Step 2: (S)—N,N-bis(4-methoxybenzyl)-1-(pyridin-2-yl)pent-4-ene-1-sulfonamide and (R)—N,N-bis(4-methoxybenzyl)-1-(pyridin-2-yl)pent-4-ene-1-sulfonamide

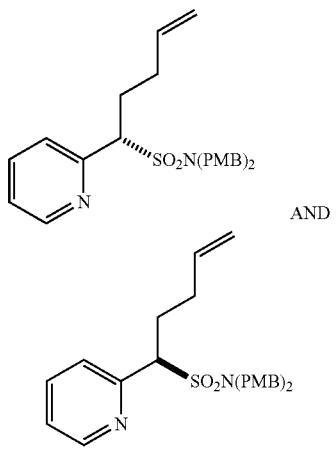

To a solution of N,N-bis(4-methoxybenzyl)-1-(pyridin-2-yl)methanesulfonamide (390 mg, 0.945 mmol, Step 1) and 4-bromo-1-butene (0.288 mL, 2.84 mmol, Matrix Scientific) in THF (8.0 mL) under Ar was added LiHMDS (0.993 mL, 1.0 M in THF, 0.993 mmol, Sigma-Aldrich Chemical Company, Inc.) over 2 min at −78° C. The resulting mixture was stirred in the −78° C. bath for 10 min, and then removed from the bath and was allowed to stir at ambient atmosphere for 4 h. The resulting mixture was quenched with saturated aqueous NH$_4$Cl (5 mL), diluted with water (10 mL) and extracted with EtOAc (14 mL×3). The organic layers were combined, washed with water (5 mL), brine (3 mL), and dried over MgSO$_4$. After removal of organic solvents under reduced pressure, purification of the residue by flash chromatography on ISCO Gold silica gel column using 0-100% EtOAc/Hexanes as eluent provided the title compounds as a colorless syrup.

Step 3: (S)-1-(pyridin-2-yl)pent-4-ene-1-sulfonamide and (R)-1-(pyridin-2-yl)pent-4-ene-1-sulfonamide

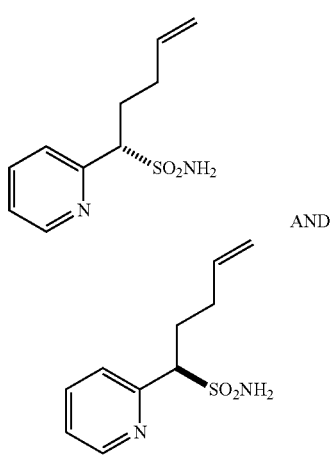

The title compounds were prepared as a mixture from a mixture of (S)—N,N-bis(4-methoxybenzyl)-1-(pyridin-2-yl)pent-4-ene-1-sulfonamide and (R)—N,N-bis(4-methoxybenzyl)-1-(pyridin-2-yl)pent-4-ene-1-sulfonamide (Step 2) following a procedure similar to the one described in Step 2 for the synthesis of EE17.

Step 4: (S)-6'-chloro-5-(((1R,2R)-2-((S)-1-hydroxyallyl)cyclobutyl)methyl)-N—(((S)-1-(pyridin-2-yl)pent-4-en-1-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxyallyl)cyclobutyl)methyl)-N—(((R)-1-(pyridin-2-yl)pent-4-en-1-yl)sulfonyl)-3',4,4',5-tetrahydro-2H,2'H-spiro[benzo[b][1,4]oxazepine-3,1'-naphthalene]-7-carboxamide

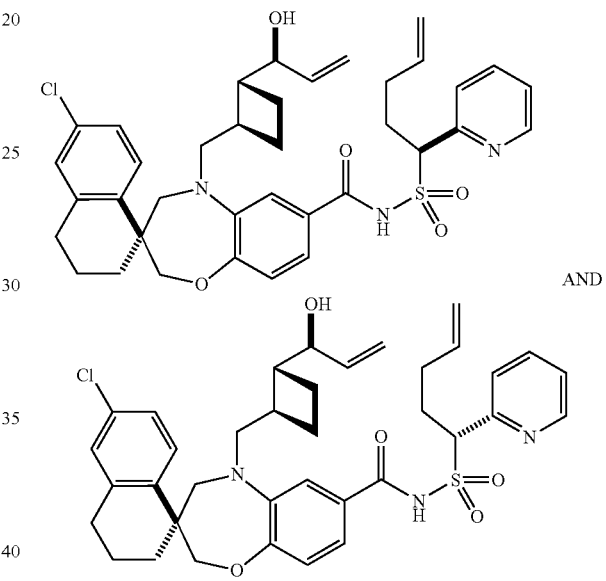

The title compounds were prepared as a mixture from (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (AA11A) and a mixture of (S)-1-(pyridin-2-yl)pent-4-ene-1-sulfonamide and (R)-1-(pyridin-2-yl)pent-4-ene-1-sulfonamide (Step 3), following a procedure similar to the one described in Step 2 for the synthesis of Example 660, except that the crude product was purified by flash chromatography on ISCO Gold silica gel column using 0-100% EtOAc/Hexanes to provide the title compounds as a mixture.

Step 5: (1S,3'R,6'R,7'S,8'E,12'S)-6-chloro-7'-hydroxy-12'-(2-pyridinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide and (1S,3'R,6'R,7'S,8'E,12'R)-6-chloro-7'-hydroxy-12'-(2-pyridinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compound was prepared from (S(S)-6'-chloro-5-(((1R,2R)-2-((S)-1-hydroxyallyl)cyclobutyl)methyl)-N—

(((S)-1-(pyridin-2-yl)pent-4-en-1-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxyallyl)cyclobutyl)methyl)-N—(((R)-1-(pyridin-2-yl)pent-4-en-1-yl)sulfonyl)-3',4,4',5-tetrahydro-2H,2'H-spiro[benzo[b][1,4]oxazepine-3,1'-naphthalene]-7-carboxamide (Step 4) following a procedure similar to the one described in Step 3 for the synthesis of Example 660, except that Ti(O$^i$Pr)$_4$ (3.0 eq., Sigma-Aldrich Chemical Company, Inc.) was added to the reaction solution immediately before the Hoveyda-Grubbs Catalyst (2nd generation). The crude product was purified by reversed phase preparatory HPLC (Gemini™ Prep C18 10 μm column; Phenomenex, Torrance, CA; gradient elution of 40% to 90% MeCN in water, where both solvents contain 0.1% TFA, 30 min method) to provide one of the title compounds as the first eluting isomer as a white foam. $^1$H NMR (400 MHz, CDCl$_3$) δ 8.78 (br. s., 1H), 7.89 (t, J=7.6 Hz, 1H), 7.74-7.69 (m, 2H), 7.50-7.41 (m, 1H), 7.20 (dd, J=2.2, 8.5 Hz, 1H), 7.10 (d, J=2.2 Hz, 1H), 7.00-6.93 (m, 3H), 5.99-5.87 (m, 1H), 5.81-5.60 (m, 2H), 4.32 (br. s., 1H), 4.21-4.04 (m, 2H), 3.98-3.86 (m, 1H), 3.73 (d, J=14.5 Hz, 1H), 3.28-3.22 (m, 1H), 3.03 (dd, J=7.6, 7.6 Hz, 1H), 2.88-1.22 (m, 17H). m/z (ESI, +ve ion) 648.0 (M+H)$^+$.

Example 693. (1S,3'R,6'R,7'S,8'E,12'S)-6-chloro-7'-hydroxy-12'-(2-pyridinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-7'-hydroxy-12'-(2-pyridinyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

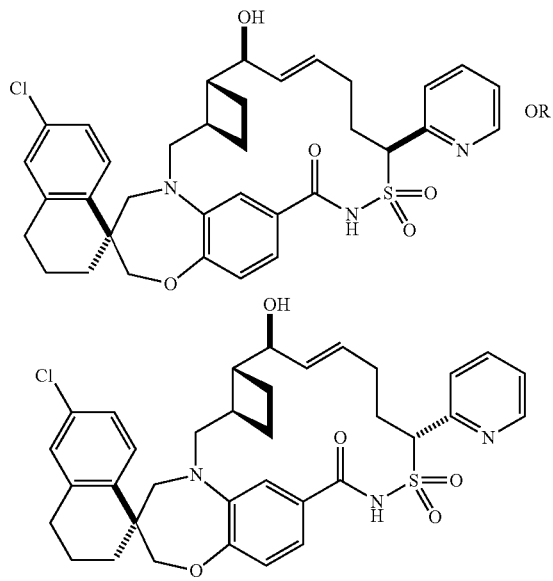

The title compound was obtained as a white foam as the second eluting isomer from the reversed phase preparatory HPLC separation in Example 692, Step 5. $^1$H NMR (400 MHz, CDCl$_3$) δ 8.83-8.75 (m, 1H), 7.98-7.83 (m, 1H), 7.79-7.62 (m, 2H), 7.54-7.39 (m, 1H), 7.24-7.06 (m, 3H), 7.04-6.91 (m, 2H), 5.96-5.83 (m, 1H), 5.80-5.43 (m, 2H), 4.37-4.21 (m, 2H), 4.19-4.07 (m, 2H), 4.03-3.84 (m, 2H), 3.78-3.66 (m, 1H), 3.50-1.32 (m, 17H). m/z (ESI, +ve ion) 648.0 (M+H)$^+$.

Example 694. (1S,3'R,6'R,7'S,8'E)-6-chloro-7'-hydroxy-12'-(1,3-oxazol-2-ylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide

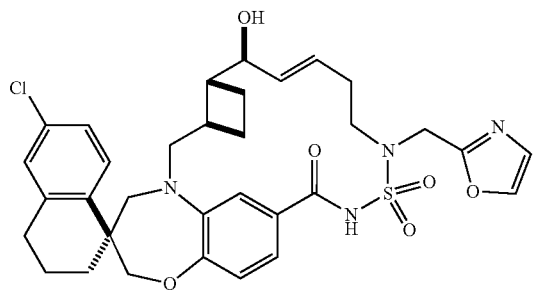

Step 1: N-(oxazol-2-ylmethyl)but-3-en-1-amine

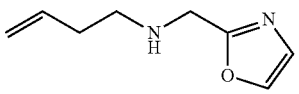

To a solution of 3-buten-1-amine (5.71 ml, 61.8 mmol, Alfa Aesar, A Johnson Matthey Company) and oxazole-2-carbaldehyde (2.00 ml, 20.6 mmol, J & W PharmLab, LLC) in dichloromethane (20 mL) in ice bath was added sodium cyanoborohydride (14.4 ml, 1.0 N in THF, 14.4 mmol, Sigma-Aldrich Chemical Company, Inc.) in three portions over 20 min at 0° C. The resulting solution was allowed to stir in the ice bath for 1.0 h. To the mixture was added NaBH(OAc)$_3$ (6.36 g, 20.0 mmol, Sigma-Aldrich Chemical Company, Inc.). The reaction solution was removed from the ice bath, and allowed to stir at ambient temperature for 1 h. The reaction mixture was treated with aqueous NaOH (2.0 N, 10 mL) and water (25 mL), and was extracted with dichloromethane (3×20 mL). The organic layers were combined, washed with aqueous HCl (3×10 mL). The aqueous layers were combined, basified with aqueous NaOH (2.0 N) to PH=14, and extracted with 30% $^i$PrOH//chloroform (3×25 mL). The $^i$PrOH//chloroform solutions were combined and washed with brine (8 mL). After removal of organic solvents under reduced pressure, the residue was left under high vacuum to provide the crude title compound, which was used without further purification.

Step 2: N-3-buten-1-yl-N-(1,3-oxazol-2-ylmethyl)sulfuric diamide

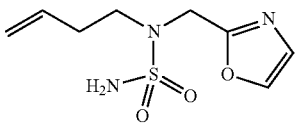

The title compound was prepared from (N-(oxazol-2-ylmethyl)but-3-en-1-amine (Step 1) following a procedure similar to the one described for the synthesis of N-4-penten-1-ylsulfuri (Step 1 in the synthesis of Example 660), except that the crude product was purified by flash chromatography on ISCO Gold silica gel column using 0-100% EtOAc/Hexanes to provide the title compound as a white solid.

Step 3: (S)—N—(N-(but-3-en-1-yl)-N-(oxazol-2-ylmethyl)sulfamoyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide

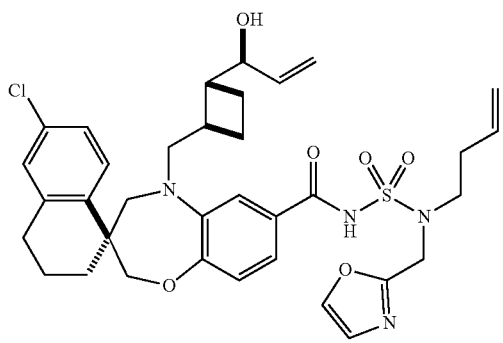

The title compounds was prepared from N-3-buten-1-yl-N-(1,3-oxazol-2-ylmethyl)sulfuric diamide (Step 2) and (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (AA11A), following a procedure similar to the one described for the synthesis of (S)-6'-chloro-5-(((1R,2R)-2-((S)-1-hydroxyallyl)cyclobutyl)methyl)-N—(N-(pent-4-en-1-yl)sulfamoyl)-3',4,4',5-tetrahydro-2H,2'H-spiro[benzo[b][1,4]oxazepine-3,1'-naphthalene]-7-carboxamide (Step 2 in the synthesis of Example 660), except that the crude product was purified by flash chromatography on ISCO Gold silica gel column using 0-80% EtOAc/Hexanes (EtOAc contained 0.1% HOAc) to provide the title compounds as a white solid.

Step 4: (1S,3'R,6'R,7'S,8'E)-6-chloro-7'-hydroxy-12'-(1,3-oxazol-2-ylmethyl)-3,4-dihydro-2H,15'H-spiro[naphthalene-1,22'-[20]oxa[13]thia[1,12,14]triazatetracyclo[14.7.2.0$^{3,6}$.0$^{19,24}$]pentacosa[8,16,18,24]tetraen]-15'-one 13',13'-dioxide The title compounds were prepared from (S)—N—(N-(but-3-en-1-yl)-N-(oxazol-2-ylmethyl)sulfamoyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide (Step 3), following a procedure similar to the one described in Step 3 in the synthesis of Example 660, except that Ti(O$^i$Pr)$_4$ (2.0 eq.) was added immediately before the Hoveyda-Grubbs catalyst (2nd generation), and the reaction was prolonged to 72 h. The crude product was purified by reversed phase preparatory HPLC (Gemini™ Prep C18 10 μm column; Phenomenex, Torrance, CA; gradient elution of 45% to 90% MeCN in water, where both solvents contain 0.1% TFA, 30 min method) to provide the title compound as a white foam. $^1$H NMR (400 MHz, CDCl$_3$) δ 8.87 (br. s., 1H), 7.76-7.65 (m, 2H), 7.18 (dd, J=2.3, 8.6 Hz, 1H), 7.14-7.07 (m, 2H), 7.02-6.89 (m, 3H), 5.94-5.81 (m, 1H), 5.79-5.67 (m, 1H), 5.42-5.27 (m, 1H), 4.71 (d, J=17.4 Hz, 1H), 4.25-4.19 (m, 1H), 4.17-4.04 (m, 2H), 3.84 (d, J=15.1 Hz, 1H), 3.77-3.64 (m, 2H), 3.33-3.21 (m, 2H), 3.20-3.08 (m, 1H), 2.84-2.72 (m, 2H), 2.70 (s, 1H), 2.55-2.19 (m, 4H), 2.01-1.60 (m, 5H), 1.65-1.56 (m, 2H), 1.46 (t, J=11.9 Hz, 1H). m/z (ESI, +ve ion) 653.0 (M+H)$^+$.

Example 695. (1S,3'R,6'R,7'S,12'R)-5-chloro-12'-ethyl-7'-hydroxy-2,3-dihydro-15'H-spiro[indene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,12'S)-5-chloro-12'-ethyl-7'-hydroxy-2,3-dihydro-15'H-spiro[indene-1,22'-[20]oxa[13]thia[1,14]diazatetracyclo[14.7.2.0$^{3,6}$.0$^{19,24}$]pentacosa [16,18,24]trien]-15'-one 13',13'-dioxide

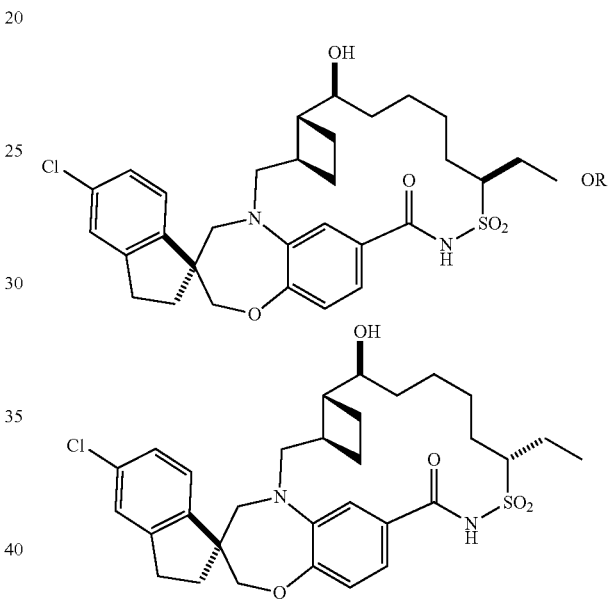

A flask containing a mixture of (1S,3'R,6'R,7'S,8'E,12'S)-5-chloro-12'-ethyl-7'-hydroxy-2,3-dihydro-15'H-spiro[indene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-5-chloro-12'-ethyl-7'-hydroxy-2,3-dihydro-15'H-spiro[indene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (10 mg, 0.017 mmol, Example 699) and PtO$_2$ (1.0 mg) in EtOAc (5 mL) was purged with H$_2$ balloon for 10 min. The mixture was allowed to stir at rt under H$_2$ for 3.5 h. The flask was then purged with air for 2 min, and the solid was filtered off through a small pad of a Celite® (diatomaceous earth), and washed with EtOAc (2×4 mL). The organic solutions were combined. After removal of organic solvents under reduced pressure, purification of the residue by flash chromatography on ISCO Gold silica gel column with 0-50% EtOAc/Hexanes (EtOAc contained 0.1% HOAc) provided the title compound as a film. $^1$H NMR (400 MHz, CDCl$_3$) δ 9.84 (br. s., 1H), 7.37 (d, J=8.0 Hz, 1H), 7.33 (br. s., 1H), 7.23-7.16 (m, 3H), 6.99-6.91 (m, 1H), 4.37-4.06 (m, 3H), 3.75-3.37 (m, 4H), 3.19 (d, J=14.1 Hz, 1H), 3.00-2.88 (m, 2H), 2.46 (br. s, 1H), 2.33-2.04 (m, 4H), 2.01-1.22 (m, 14), 1.16-1.10 (m, 3H). m/z (ESI, +ve ion) 587.2 (M+H)$^+$ Example 696. (1S,3'R,6'R,7'S,8'E,12'S)-6-chloro-7'-hydroxy-12'-(2-hydroxy-2-propanyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-7'-hydroxy-12'-(2-hydroxy-2-propanyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

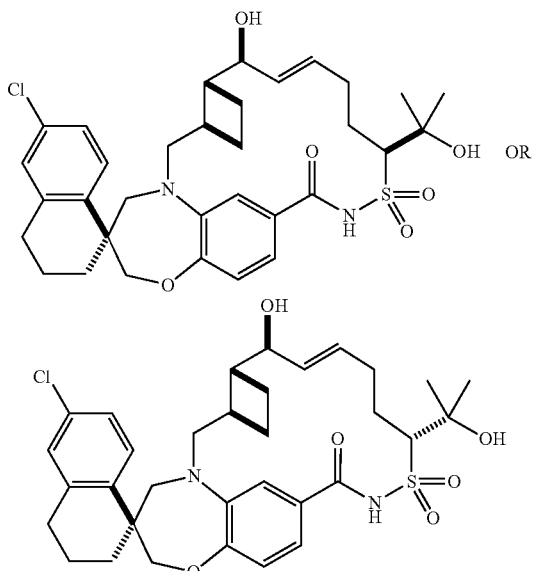

Step 1: (S)-2-hydroxy-N,N-bis(4-methoxybenzyl)-2-methylhept-6-ene-3-sulfonamide and (R)-2-hydroxy-N,N-bis(4-methoxybenzyl)-2-methylhept-6-ene-3-sulfonamide

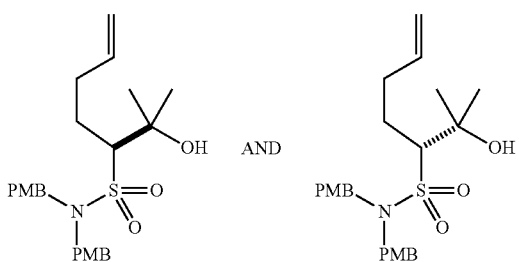

To a solution of N,N-bis(4-methoxybenzyl)pent-4-ene-1-sulfonamide (445 mg, 1.142 mmol, EE19) in THF (5.7 ml) under Ar was added $^n$BuLi (594 μl, 1.49 mmol, 2.5 M in hexanes, Sigma-Aldrich Chemical Company, Inc.) drop wise over 2 min at −78° C. The resulting mixture was stirred in the −78° C. bath for 30 min, followed by addition of anhydrous acetone (0.5 mL, Sigma-Aldrich Chemical Company, Inc.). The reaction flask was removed from the bath and was allowed to stir at ambient atmosphere for 25 min. The reaction mixture was quenched with saturated aqueous NH$_4$Cl (2 mL), diluted with water (10 mL) and extracted with EtOAc (3×12 mL). The organic layers were combined, washed with water (6 mL), brine (3 mL), and dried over MgSO$_4$. After removal of organic solvents under reduced pressure, purification of the residue by flash chromatography on silica gel using 0-20-30% EtOAc/Hexanes as eluent provided the title compounds as a colorless syrup.

Step 2: (S)-2-hydroxy-2-methylhept-6-ene-3-sulfonamide and (R)-2-hydroxy-2-methylhept-6-ene-3-sulfonamide

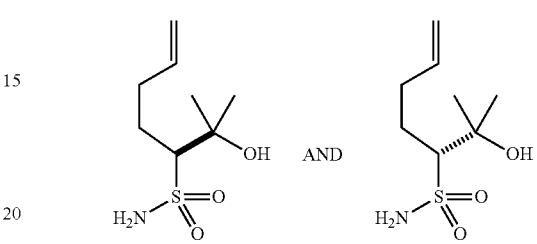

The title compound was prepared as a mixture from (S)-2-hydroxy-N,N-bis(4-methoxybenzyl)-2-methylhept-6-ene-3-sulfonamide and (R)-2-hydroxy-N,N-bis(4-methoxybenzyl)-2-methylhept-6-ene-3-sulfonamide (Step 1) following a procedure similar to the one described in Step 2 for the synthesis of EE17.

Step 3: (S)-6'-chloro-N—(((S)-2-hydroxy-2-methylhex-5-en-3-yl)sulfonyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide or (S)-6'-chloro-N—(((R)-2-hydroxy-2-methylhex-5-en-3-yl)sulfonyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide

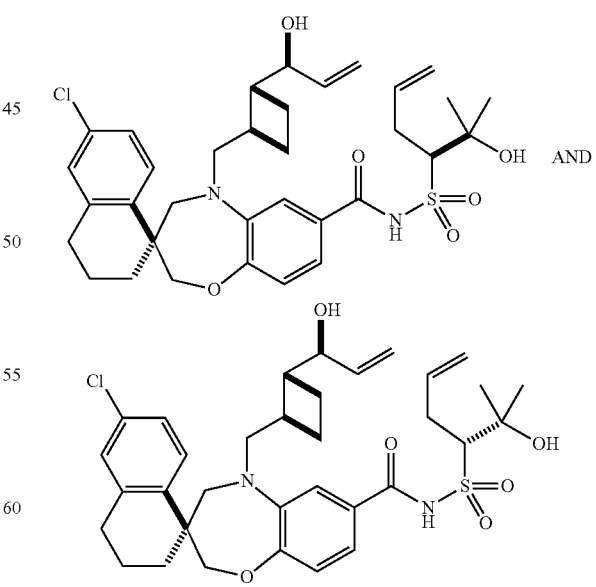

The title compounds were prepared as a mixture from (S)-6'-chloro-5-(((1R,2R)-2-((S)-1-hydroxyallyl)cyclobutyl)methyl)-3',4,4',5-tetrahydro-2H,2'H-spiro[benzo

[b][1,4]oxazepine-3,1'-naphthalene]-7-carboxylic acid (AA11A) and a mixture of (S)-2-hydroxy-N,N-bis(4-methoxybenzyl)-2-methylhept-6-ene-3-sulfonamide and (R)-2-hydroxy-N,N-bis(4-methoxybenzyl)-2-methylhept-6-ene-3-sulfonamide (Step 2), following a procedure similar to the one described in Step 2 for the synthesis of Example 660.

Step 4: (1S,3'R,6'R,7'S,8'E,12'S)-6-chloro-7'-hydroxy-12'-(2-hydroxy-2-propanyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide and (1S,3'R,6'R,7'S,8'E,12'R)-6-chloro-7'-hydroxy-12'-(2-hydroxy-2-propanyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide The title compound was prepared from a mixture of (S)-6'-chloro-N—(((S)-2-hydroxy-2-methylhex-5-en-3-yl)sulfonyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide and (S)-6'-chloro-N—(((R)-2-hydroxy-2-methylhex-5-en-3-yl)sulfonyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide (Step 3), following a procedure similar to the one described in Step 3 for the synthesis of Example 660, except that the crude product was purified by reversed phase preparatory HPLC (Gemini™ Prep C18 5 μm column; Phenomenex, Torrance, CA; gradient elution of 55% MeCN in water to 80% MeCN in water over a 20 min period, where both solvents contain 0.1% TFA) to provide one of the title compounds as the first eluting isomer as a white foam. ¹H NMR (400 MHz, CDCl₃): ¹H NMR (400 MHz, CDCl₃) δ 8.64 (br. s., 1H), 7.70 (d, J=8.4 Hz, 1H), 7.18 (dd, J=2.0, 8.4 Hz, 1H), 7.10-7.08 (m, 2H), 7.02-6.88 (m, 2H), 5.71-5.54 (m, 2H), 4.10 (dt, J=5.2, 12.1 Hz, 3H), 3.87-3.69 (m, 2H), 3.24 (d, J=14.1 Hz, 1H), 3.04 (dd, J=6.3, 15.5 Hz, 1H), 2.85-2.69 (m, 2H), 2.58-1.60 (m, 17H), 1.55 (s, 3H), 1.42 (s, 3H); (ESI, +ve ion) 629.2 (M+H)⁺.

Example 697. (1S,3'R,6'R,7'S,8'E,12'S)-6-chloro-7'-hydroxy-12'-(2-hydroxy-2-propanyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,12'R)-6-chloro-7'-hydroxy-12'-(2-hydroxy-2-propanyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

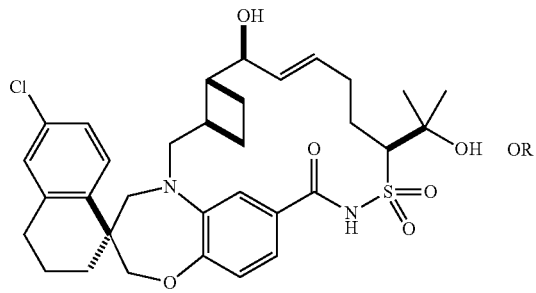

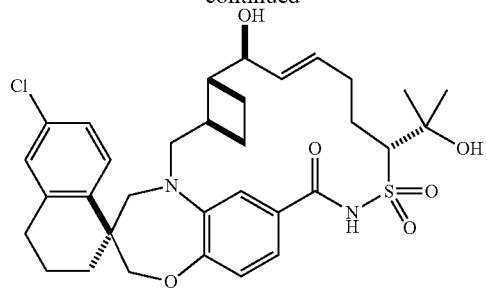

The title compound was obtained as a white foam as the second eluting isomer from the reversed phase preparatory HPLC separation in Example 696, Step 4. ¹H NMR (400 MHz, CDCl₃) δ 8.19 (br. s., 1H), 7.58 (d, J=8.4 Hz, 1H), 7.33 (br. s., 1H), 7.16-7.06 (m, 1H), 7.02 (s, 1H), 6.96-6.82 (m, 2H), 5.69 (dd, J=5.3, 15.8 Hz, 1H), 5.48 (d, J=6.1 Hz, 1H), 4.18-4.01 (m, 2H), 3.98-3.82 (m, 2H), 3.80-3.66 (m, 1H), 3.64-3.10 (m, 3H), 2.72-2.65 (m, 2H), 2.54-1.52 (m, 16H), 1.47 (s, 3H), 1.39 (s, 3H). m/z (ESI, +ve ion) 629.2 (M+H)⁺.

Example 698. (1S,3'R,6'R,7'S,8'E,12'R)-5-chloro-7'-hydroxy-12'-methyl-2,3-dihydro-15'H-spiro[indene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

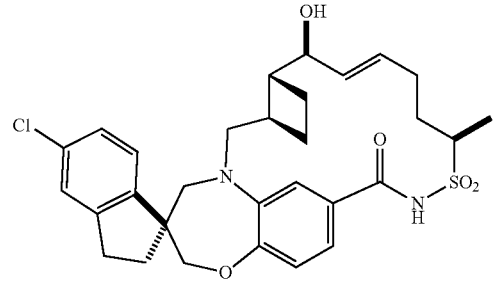

Step 1: (S)-5'-chloro-N—((R)-hex-5-en-2-ylsulfonyl)-5-(((1R,2R)-2-((S)-1-hydroxyallyl)cyclobutyl)methyl)-2',3',4,5-tetrahydro-2H-spiro[benzo[b][1,4]oxazepine-3,1'-indene]-7-carboxamide

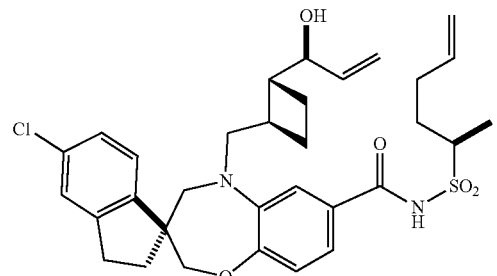

The title compound was prepared from (S)-5'-chloro-5-(((1R,2R)-2-((S)-1-hydroxyallyl)cyclobutyl)methyl)-2',3',4, 5-tetrahydro-2H-spiro[benzo[b][1,4]oxazepine-3,1'-indene]-7-carboxylic acid (AA20) and (R)-pent-4-ene-2-sulfonamide (EE17), following a procedure similar to the one described in Step 2 for the synthesis of Example 660, except that the crude product was purified by flash chromatography on ISCO Gold silica gel column using 0-20% EtOAc/Hexanes (EtOAc containing 0.3% HOAc) to provide the title compound as white solid.

Step 2: (1S,3'R,6'R,7'S,8'E,12'R)-5-chloro-7'-hydroxy-12'-methyl-2,3-dihydro-15'H-spiro[indene-1, 22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compound was prepared from (S)-5'-chloro-N—((R)-hex-5-en-2-ylsulfonyl)-5-(((1R,2R)-2-((S)-1-hydroxyallyl)cyclobutyl)methyl)-2',3',4,5-tetrahydro-2H-spiro[benzo[b][1,4]oxazepine-3,1'-indene]-7-carboxamide (Step 1), following a procedure similar to the one described in Step 3 for the synthesis of Example 660, except that the crude product was purified by reversed phase preparatory HPLC (Gemini™ Prep C18 10 μm column; Phenomenex, Torrance, CA; gradient elution of 50% MeCN in water to 80% MeCN in water over 40 min period, where both solvents contain 0.1% TFA) to provide the title compound as a white foam. $^1$H NMR (400 MHz, CDCl$_3$) δ 8.08 (s, 1H), 7.48-7.41 (m, 1H), 7.25-7.17 (m, 2H), 7.00-6.91 (m, 3H), 5.89-5.77 (m, 1H), 5.76-5.66 (m, 1H), 4.29-4.14 (m, 4H), 3.85 (d, J=13.7 Hz, 1H), 3.67-3.55 (m, 1H), 3.15-2.87 (m, 4H), 2.49-2.40 (m, 1H), 2.40-2.28 (m, 2H), 2.19 (ddd, J=3.1, 7.8, 13.1 Hz, 2H), 2.04-1.91 (m, 1H), 1.91-1.61 (m, 7H), 1.56 (d, J=5.4 Hz, 3H); (ESI, +ve ion) 571.2 (M+H)$^+$.

Example 699. (1S,3'R,6'R,7'S,8'E,12'S)-5-chloro-12'-ethyl-7'-hydroxy-2,3-dihydro-15'H-spiro[indene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-5-chloro-12'-ethyl-7'-hydroxy-2,3-dihydro-15'H-spiro[indene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

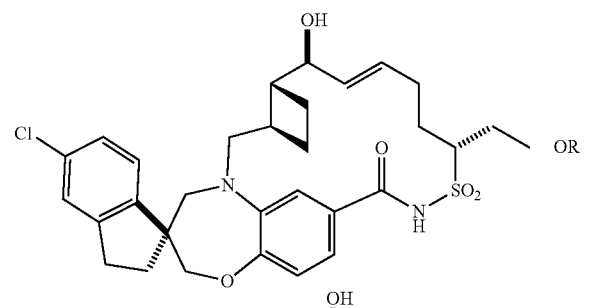

Step 1: (S)-5'-chloro-N—((S)-hept-6-en-3-ylsulfonyl)-5-(((1R,2R)-2-((S)-1-hydroxyallyl)cyclobutyl)methyl)-2',3',4,5-tetrahydro-2H-spiro[benzo[b][1,4]oxazepine-3,1'-indene]-7-carboxamide and (S)-5'-chloro-N—((R)-hept-6-en-3-ylsulfonyl)-5-(((1R,2R)-2-((S)-1-hydroxyallyl)cyclobutyl)methyl)-2',3',4,5-tetrahydro-2H-spiro[benzo[b][1,4]oxazepine-3,1'-indene]-7-carboxamide

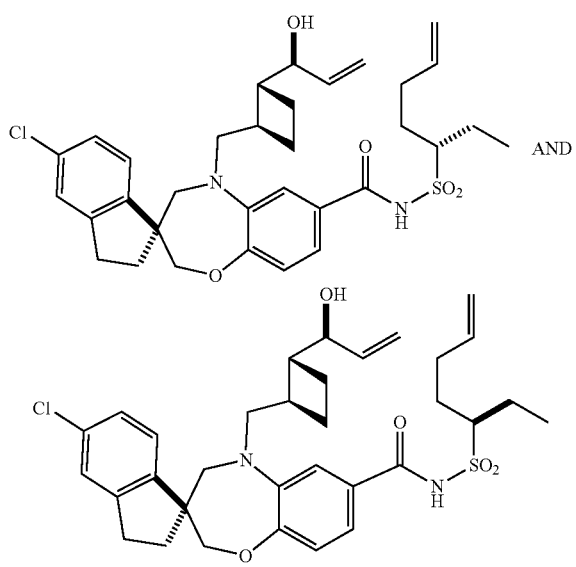

The title compounds were prepared from (S)-5'-chloro-5-(((1R,2R)-2-((S)-1-hydroxyallyl)cyclobutyl)methyl)-2',3',4,5-tetrahydro-2H-spiro[benzo[b][1,4]oxazepine-3,1'-indene]-7-carboxylic acid (AA20) and a mixture of (R)-hex-5-ene-3-sulfonamide and (S)-hex-5-ene-3-sulfonamide (EE21: EE212=1:1), following a procedure similar to the one described in Step 2 for the synthesis of Example 660, except that the crude product was purified by flash chromatography on ISCO Gold silica gel column using 0-40% EtOAc/Hexanes (EtOAc containing 0.3% HOAc) to provide the title compounds as a mixture.

Step 2: (1S,3'R,6'R,7'S,8'E,12'S)-5-chloro-12'-ethyl-7'-hydroxy-2,3-dihydro-15'H-spiro[indene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-5-chloro-12'-ethyl-7'-hydroxy-2,3-dihydro-15'H-spiro[indene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compounds were prepared from a mixture of (S)-5'-chloro-N—((S)-hept-6-en-3-ylsulfonyl)-5-(((1R,2R)-2-((S)-1-hydroxyallyl)cyclobutyl)methyl)-2',3',4,5-tetrahydro-2H-spiro[benzo[b][1,4]oxazepine-3,1'-indene]-7-carboxamide and (S)-5'-chloro-N—((R)-hept-6-en-3-ylsulfonyl)-5-(((1R,2R)-2-((S)-1-hydroxyallyl)cyclobutyl)methyl)-2',3',4,5-tetrahydro-2H-spiro[benzo[b][1,4]oxazepine-3,1'-indene]-7-carboxamide (Step 1), following a procedure similar to the one described in Step 3 for the synthesis of Example 660, except that the crude product was purified by reversed phase preparatory HPLC (Gemini™

Prep C18 5 μm column; Phenomenex, Torrance, CA; gradient elution of 55% MeCN in water to 80% MeCN in water over a 20 min period, where both solvents contain 0.1% TFA) to provide one of the title compounds as the first eluting isomer as a white foam. $^1$H NMR (400 MHz, CDCl$_3$) δ 8.25 (br. s., 1H), 7.44 (d, J=7.8 Hz, 1H), 7.26-7.17 (m, 2H), 7.09-6.88 (m, 3H), 5.97-5.78 (m, 1H), 5.78-5.64 (m, 1H), 4.36-4.14 (m, 3H), 4.06 (br. s., 1H), 3.83 (d, J=15.1 Hz, 1H), 3.61 (d, J=14.1 Hz, 1H), 3.21-2.85 (m, 4H), 2.54-2.30 (m, 3H), 2.30-1.52 (m, 12H), 1.35-1.13 (m, 3H); (ESI, +ve ion) 585.1 (M+H)$^+$.

Example 700. (1S,3'R,6'R,7'S,8'E,12'S)-5-chloro-12'-ethyl-7'-hydroxy-2,3-dihydro-15'H-spiro[indene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-5-chloro-12'-ethyl-7'-hydroxy-2,3-dihydro-15'H-spiro[indene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

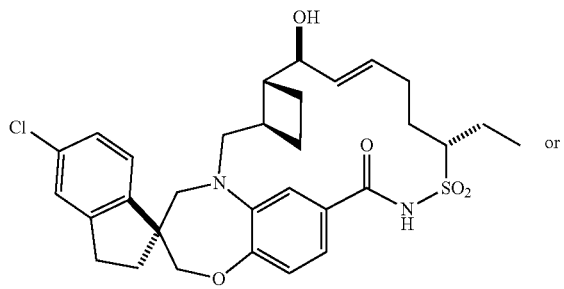

or

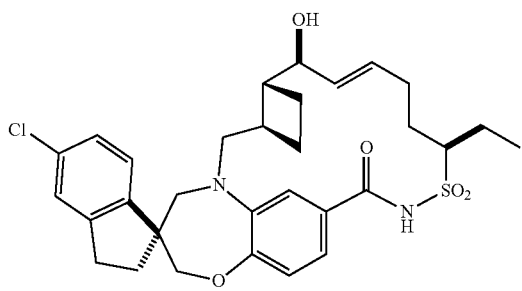

The title compound was obtained as a white foam as the second eluting isomer from the reversed phase preparatory HPLC separation in Example 699, Step 2. $^1$H NMR (400 MHz, CDCl$_3$) δ 8.26 (br. s., 1H), 7.67 (br. s., 1H), 7.36 (d, J=8.0 Hz, 1H), 7.25-7.15 (m, 3H), 7.04-6.87 (m, 2H), 5.67 (dd, J=4.3, 15.7 Hz, 1H), 5.47 (dd, J=7.3, 14.6 Hz, 1H), 4.37-4.16 (m, 3H), 4.10 (d, J=16.2 Hz, 1H), 3.93 (d, J=15.1 Hz, 2H), 3.74 (d, J=14.5 Hz, 1H), 3.46-3.35 (m, 1H), 3.12 (d, J=15.1 Hz, 1H), 3.01-2.88 (m, 3H), 2.67-1.36 (m, 11H), 1.22 (dd, J=6.4, 6.4 Hz, 3H). m/z (ESI, +ve ion) 585.2 (M+H)$^+$.

Example 701. (1S,3'R,6'R,7'S,8'E,12'R)-6-chloro-12'-ethyl-17'-fluoro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

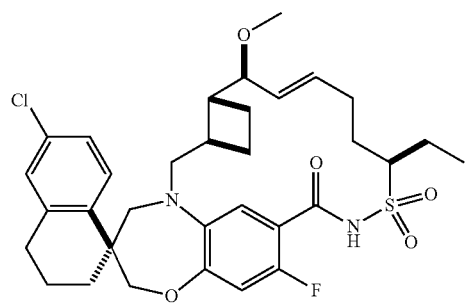

The title compound was prepared from (1S,3'R,6'R,7'S,8'E,12'R)-6-chloro-12'-ethyl-17'-fluoro-7'-hydroxy-3,4-dihydro-2H,15'H-spiro[naphthalene-1,22'-[20]oxa[13]thia[1,14]diazatetracyclo[14.7.2.0~3,6~.0.0~19,24~]pentacosa[8,16,18,2 4]tetraen]-15'-one 13',13'-dioxide (Example 656) following a procedure similar to the one described for the synthesis of Example 669 using methyl iodide instead of bromoethyl methyl ether, except that the crude product was purified by reversed phase preparatory HPLC (Gemini™ Prep C18 5 μm column; Phenomenex, Torrance, CA; gradient elution of 45% to 95% MeCN in water, where both solvents contain 0.1% TFA, 25 min method) to provide the title compound as a white foam. $^1$H NMR (400 MHz, CDCl$_3$) δ 8.21 (d, J=7.0 Hz, 1H), 7.66 (d, J=8.6 Hz, 1H), 7.18 (dd, J=2.3, 8.4 Hz, 1H), 7.10 (d, J=2.2 Hz, 1H), 6.88-6.79 (m, 1H), 6.72 (d, J=11.5 Hz, 1H), 5.80 (ddd, J=5.0, 8.0, 15.2 Hz, 1H), 5.53 (dd, J=8.6, 15.3 Hz, 1H), 4.19-4.03 (m, 3H), 3.79 (d, J=15.1 Hz, 1H), 3.70-3.55 (m, 2H), 3.30-3.17 (m, 4H), 2.97 (dd, J=10.2, 15.3 Hz, 1H), 2.87-2.68 (m, 3H), 2.61-1.56 (m, 13H), 1.47-1.36 (m, 1H), 1.27 (s, 1H), 1.23 (dd, J=8.3, 8.3 Hz, 3H). m/z (ESI, +ve ion) 631.2 (M+H)$^+$.

Example 702. (1S,3'R,6'R,7'S,8'E,12'S)-6-chloro-12'-((R)-hydroxy(1,3-thiazol-2-yl)methyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'S)-6-chloro-12'-((S)-hydroxy(1,3-thiazol-2-yl)methyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-12'-((R)-hydroxy(1,3-thiazol-2-yl)methyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-12'-((S)-hydroxy(1,3-thiazol-2-yl)methyl)-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

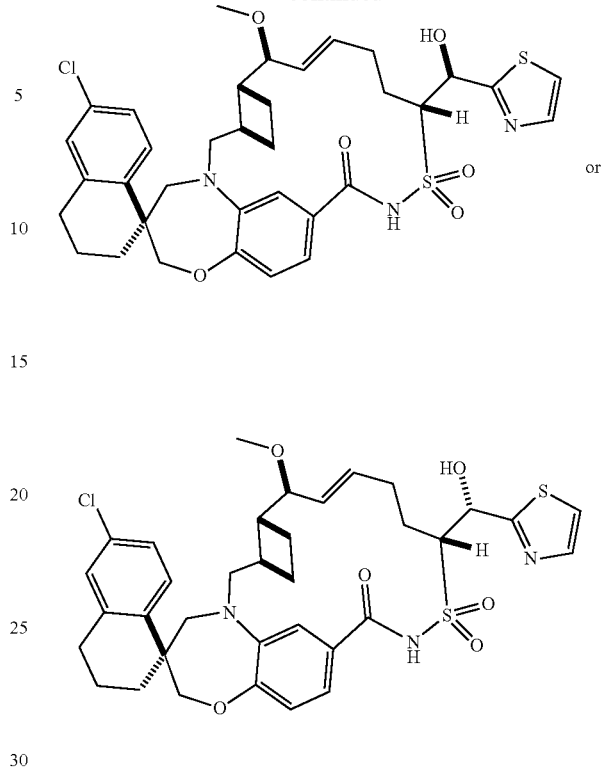

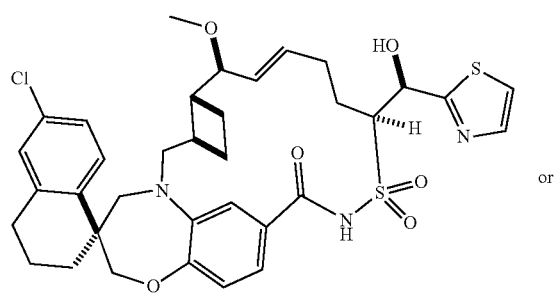

or

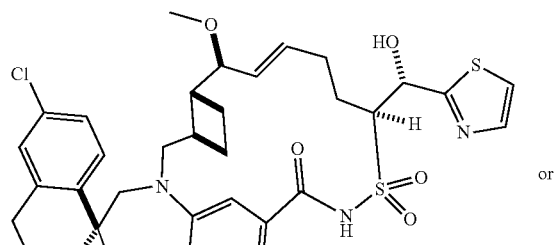

or

To a −78° C. solution of (1S,3'R,6'R,7'S,8'E)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (Example 651, Step 3) (25 mg, 0.043 mmol) in THF (2.0 mL) was added lithium diisopropylamide (0.17 ml, 0.26 M, 0.043 mmol, fresh solution prepared following a procedure similar to the one described in the synthesis of Example 682). The solution was allowed to stir at −78° C. to −30° C. for 30 min, to the mixture was added 2-thiazolecarboxaldehyde (48 mg, 0.43 mmol, Sigma-Aldrich Chemical Company, Inc.). The resulting solution was allowed to warm to rt over 20 min, and stirred at rt for 30 min. The reaction mixture was then quenched with saturated aqueous NH$_4$Cl (0.2 mL), diluted with water (3 mL) and extracted with EtOAc (3×4 mL). The organic layers were combined. After removal of organic solvents under reduced pressure, the residue was subjected to reverse phase preparatory HPLC (Gemini™ Prep C18 5 μm column; Phenomenex, Torrance, CA; gradient elution of 10% MeCN in water to 90% MeCN in water over a 20 min period, where both solvents contain 0.1% TFA) to provide one of the title compounds as a white foam. $^1$H NMR (400 MHz, CDCl$_3$) δ 8.70 (br. s., 1H), 7.81 (d, J=3.3 Hz, 1H), 7.72-7.64 (m, 1H), 7.44-7.38 (m, 1H), 7.23-7.13 (m, 2H), 7.10 (d, J=2.2 Hz, 1H), 7.04-6.91 (m, 2H), 6.01 (d, J=1.2 Hz, 1H), 5.88-5.75 (m, 1H), 5.49 (dd, J=7.2, 15.1 Hz, 1H), 4.33 (d, J=7.0 Hz, 1H), 4.20-4.04 (m, 2H), 3.69-3.23 (m, 5H), 3.36 (s, 3H), 2.89-1.27 (m, 17H). m/z (ESI, +ve ion) 666.3 (M−MeOH+H)$^+$ and 720.3 (M+Na)$^+$.

Example 703. (1S,3'R,6'R,7'S,8'E,11'R)-6-chloro-7'-hydroxy-11'-phenyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'S)-6-chloro-7'-hydroxy-11'-phenyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide Step 1: (R)-ethyl 2-phenylpent-4-enoate and (S)-ethyl 2-phenylpent-4-enoate

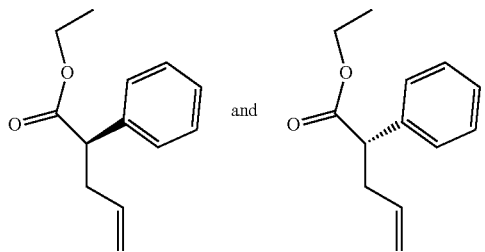

To a solution of 2-phenylacetic acid ethyl ester (11.7 ml, 73.1 mmol) in THF (146 ml) at −78° C. was added allyl bromide (6.32 ml, 73.1 mmol), followed by sodium bis(trimethylsilyl)amide, 0.6 M in toluene (122 ml, 73.1 mmol) over 5 min. The mixture was removed from ice bath and allowed to warm up to ambient temperature. After another 30 min, the mixture was poured into saturated ammonium chloride aqueous solution, diluted with water and extracted with EtOAc (3×). The combined organic solution was concentrated, and residue was purified by chromatography on silica gel eluting with 0% to 50% EtOAc in hexane to provide the title compounds (13.65 g, 91%). m/z (ESI, +ve ion) 205.1 (M+H)⁺.

Step 2: (R)-2-phenylpent-4-en-1-ol and (S)-2-phenylpent-4-en-1-ol

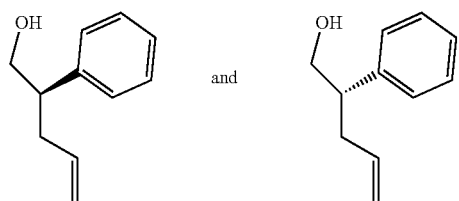

To a solution of (R)-ethyl 2-phenylpent-4-enoate and (S)-ethyl 2-phenylpent-4-enoate (13.65 g, 66.8 mmol) in Et₂O (200 mL) at 0° C. was added lithium aluminum hydride, 1.0 M solution in tetrahydrofuran (75 mL, 75 mmol) via a syringe over 15 min. The reaction mixture was stirred at this temperature for 2h. The reaction was monitored by TLC (EtOAc/Hexanes: 1/3). To the reaction mixture at 0° C. was added 2.85 mL of water, 2.85 mL of 15% sodium hydroxide aqueous solution and 8.25 mL of water in order. The mixture was stirred at room temperature for 40 min, and solid was filtered off. The filtrate was concentrated, and residue was purified by chromatography on silica gel eluting with 0% to 50% EtOAc in hexane to provide the title compounds (9.24 g, 85%). ¹H NMR (400 MHz, CDCl₃) δ 7.40-7.33 (m, 2H), 7.28-7.22 (m, 3H), 5.81-5.69 (m, 1H), 5.12-4.94 (m, 2H), 3.84-3.72 (m, 2H), 3.01-2.85 (m, 1H), 2.57-2.37 (m, 2H).

Step 3: (R)-2-((2-phenylpent-4-en-1-yl)thio)pyrimidine and (S)-2-((2-phenylpent-4-en-1-yl)thio)pyrimidine

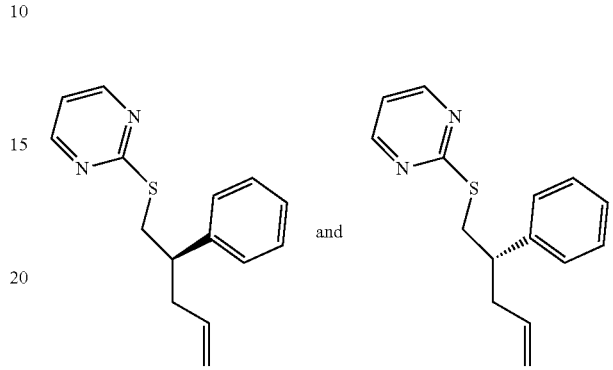

To a solution of (R)-2-phenylpent-4-en-1-ol and (S)-2-phenylpent-4-en-1-ol (9.24 g, 57.0 mmol) in DCM (100 ml) at 0° C. under N₂ was added triethylamine (9.51 ml, 68.3 mmol), followed by methanesulfonyl chloride (5.29 ml, 68.3 mmol) dropwise. The mixture became white milky during the addition of methanesulfonyl chloride. The mixture was left stirring at 0° C. for 1h. To the cloudy mixture was added water and the mixture was extracted with DCM (3×100 mL). The organic layers were combined, and washed with water, dried over magnesium sulfate. The solvent was removed under reduced pressure. To a solution of the residue obtained above (13.70 g, 57.0 mmol) in DMF (150 ml) was added 2-mercapto-pyrimidine (8.43 g, 75.2 mmol) and potassium carbonate (4.54 ml, 75.2 mmol). The mixture was heated at 70° C. for 2h, and then cooled to room temperature. The reaction mixture was poured in water, extracted with EtOAc (3×200 mL). The combined organic layer was washed with water and brine and concentrated. The crude product was purified by chromatography on silica gel eluting with 0% to 50% EtOAc in hexane to provide the title compounds (13.87 g, 95%). m/z (ESI, +ve ion) 257.0 (M+H)⁺.

Step 4: (R)-2-((2-phenylpent-4-en-1-yl)sulfonyl)pyrimidine and (S)-2-((2-phenylpent-4-en-1-yl)sulfonyl)pyrimidine

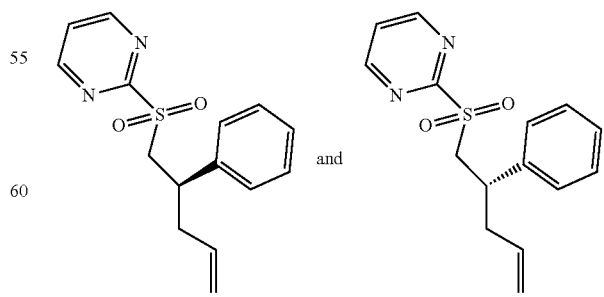

To a solution of (R)-2-((2-phenylpent-4-en-1-yl)thio)pyrimidine and (S)-2-((2-phenylpent-4-en-1-yl)thio)pyrimidine (2.16 g, 8.43 mmol) in DCM (40.0 ml) and DMF (2.0 ml) at 0° C. was added 3-chloroperbenzoic acid (4.62 g, 20.66 mmol) in one portion. The resulting mixture was stirred at 0° C. for 5 min and at room temperature for 16h, and then heated at 50° C. for 4h. The mixture was poured into a mixture of ice and saturated sodium bicarbonate aqueous solution. The layers were separated. The aqueous layer was extracted with DCM (3×). The combined organic solution was washed with brine, dried over magnesium sulfate, filtered and concentrated. The residue was purified by chromatography on silica gel eluting with 0% to 100% EtOAc in hexane to provide the title compounds (2.02 g, 83%). m/z (ESI, +ve ion) 289.0 (M+H)$^+$.

Step 5: (R)-2-phenylpent-4-ene-1-sulfonamide and (S)-2-phenylpent-4-ene-1-sulfonamide

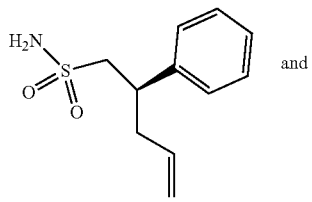
and

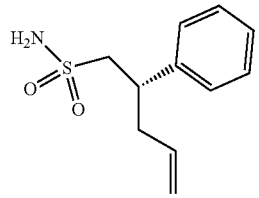

(R)-2-((2-phenylpent-4-en-1-yl)sulfonyl)pyrimidine and (S)-2-((2-phenylpent-4-en-1-yl)sulfonyl)pyrimidine (2.02 g, 7.01 mmol) in MeOH (40 mL) was heated at 35° C. until the solution became clear. To this solution was added sodium methoxide, 25 wt % solution in methanol (1.561 mL, 7.01 mmol) via a syringe slowly. The resulting mixture was stirred at room temperature for 30 min. The solvent was removed and residue was dried on high vacuum for 20 min. To the residue obtained was added water (40.0 mL), followed by sodium acetate trihydrate, granular (1.32 mL, 14.0 mmol) and amidoperoxymonosulfuric acid (1.58 g, 14.0 mmol) at room temperature. The resulting clear solution was stirred at 75° C. in a preheated oil bath for 30 min. then cooled to room temperature, basified using ice-cold saturated sodium carbonate, and extracted with 20% i-PrOH/DCM (3×). The combined organics were dried over sodium sulfate, filtered and concentrated. The residue was purified by chromatography on silica gel eluting with 20% to 80% EtOAc in hexane to provide the title compounds (0.92 g, 58.3%). m/z (ESI, +ve ion) 226.0 (M+H)$^+$.

Step 6: (S)-6'-chloro-5-(((1R,2R)-2-((1S,5S,E)-1-hydroxy-5-phenyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1S,5R,E)-1-hydroxy-5-phenyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic Acid

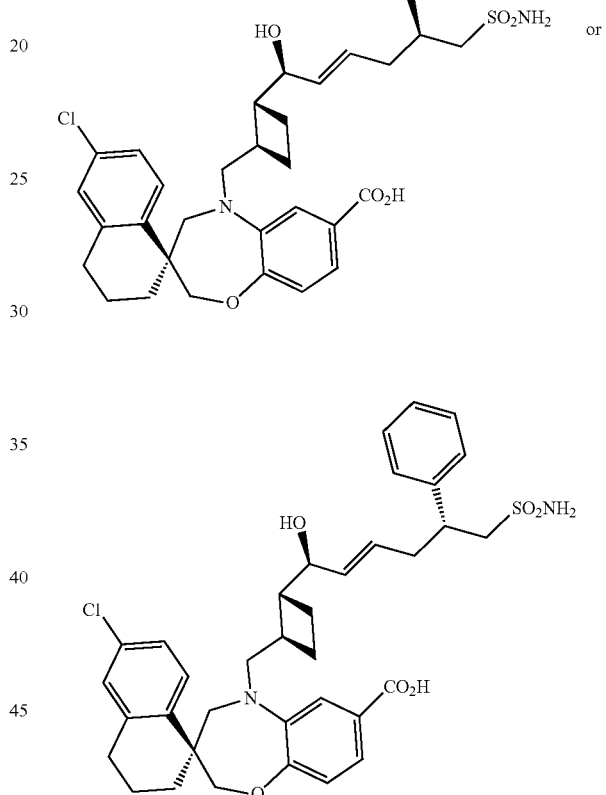

A mixture of (S)-6'-chloro-5-(((1R,2R)-2-((S)-1-hydroxy-allyl)cyclobutyl)methyl)-3',4,4',5-tetrahydro-2H,2'H-spiro[benzo[b][1,4]oxazepine-3,1'-naphthalene]-7-carboxylic acid (127 mg, 0.271 mmol, Intermediate AA11A) and (R)-2-phenylpent-4-ene-1-sulfonamide and (S)-2-phenylpent-4-ene-1-sulfonamide (183 mg, 0.814 mmol) in 1,2-dichloroethane (4.0 ml) was purged with argon for 10 min. To this solution was added Hoveyda-Grubbs catalyst (2nd generation) (17.01 mg, 0.027 mmol) in 1 mL of DCE slowly. The reaction mixture was stirred under argon balloon at room temperature for 16h. The mixture was subjected to column for purification by chromatography on silica gel eluting with 20% to 80% EtOAc (containing 0.3% AcOH) in hexane to provide the title compounds (0.115 g, 63.7%). m/z (ESI, +ve ion) 665.2 (M+H)$^+$.

Step 7: (1S,3'R,6'R,7'S,8'E,11'R)-6-chloro-7'-hydroxy-11'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S)-6-chloro-7'-hydroxy-11'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide To a solution of (S)-6'-chloro-5-(((1R,2R)-2-((1S,5S,E)-1-hydroxy-5-phenyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5R,E)-1-hydroxy-5-phenyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic acid (115 mg, 0.173 mmol) in DCM (50 ml) at 0° C. was added 4-(dimethylamino) pyridine (63.4 mg, 0.519 mmol), followed by 1-(3-dimethylaminopropyl)-3-ethylcarbodiimide hydrochloride (99 mg, 0.519 mmol) in 3 mL of DCM. The reaction mixture was stirred at this temperature for 20 min, and then warmed up to room temperature and stirred for 3h. The solvent was removed and residue was purified by chromatography on silica gel eluting with 20% to 100% EtOAc (containing 0.3% AcOH) in hexane to give the product with desired mass, and further purified by reversed phase preparatory HPLC (Gemini™ Prep C18 5 μm column; Phenomenex, Torrance, CA; gradient elution of 40% to 90% MeCN in water, where both solvents contained 0.1% TFA, 30 min method) to provide the first eluting isomer as a white solid as one of the title compounds. $^1$H NMR (400 MHz, CDCl$_3$) δ 8.59 (br s, 1H), 7.73 (d, J=8.61 Hz, 1H), 7.38-7.31 (m, 2H), 7.28-7.25 (m, 1H), 7.23-7.15 (m, 3H), 7.11 (d, J=2.15 Hz, 1H), 7.04-6.95 (m, 3H), 6.06-5.96 (m, 1H), 5.70 (dd, J=15.26, 7.83 Hz, 1H), 4.56 (dd, J=15.45, 5.67 Hz, 1H), 4.28 (d, J=5.28 Hz, 1H), 4.19-4.07 (m, 2H), 3.86-3.70 (m, 2H), 3.63 (dd, J=15.55, 7.34 Hz, 1H), 3.29 (d, J=14.28 Hz, 1H), 3.12 (d, J=16.04 Hz, 2H), 2.84-2.75 (m, 2H), 2.47 (dd, J=14.57, 5.77 Hz, 4H), 2.04 (d, J=9.39 Hz, 3H), 1.88-1.63 (m, 5H), 1.46 (t, J=12.72 Hz, 1H). m/z (ESI, +ve ion) 646.9 (M+H)$^+$.

Example 704. (1S,3'R,6'R,7'S,8'E,11'S)-6-chloro-7'-hydroxy-11'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R)-6-chloro-7'-hydroxy-11'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

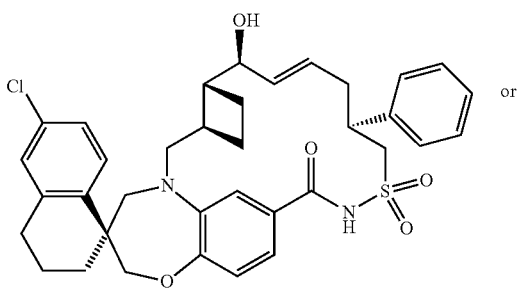 or

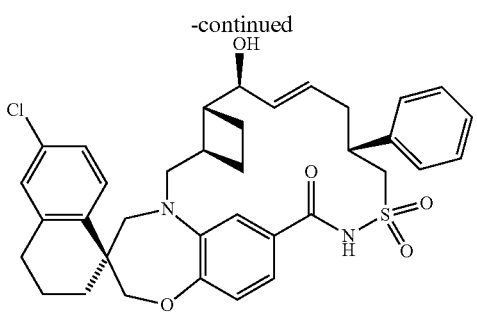

The other title compound as a white solid was obtained as the later eluting isomer from the reversed phase preparatory HPLC separation in Example 703, Step 7. $^1$H NMR (400 MHz, CDCl$_3$) δ 8.54 (br s, 1H), 7.68 (d, J=8.41 Hz, 1H), 7.38-7.32 (m, 2H), 7.29-7.25 (m, 2H), 7.24-7.16 (m, 3H), 7.12 (d, J=2.15 Hz, 1H), 7.04-6.95 (m, 2H), 5.80 (d, J=4.30 Hz, 2H), 4.36 (d, J=14.48 Hz, 1H), 4.30-4.20 (m, 2H), 4.05 (br s, 1H), 3.69 (dd, J=15.26, 8.02 Hz, 2H), 3.42 (d, J=13.50 Hz, 1H), 3.27 (d, J=15.45 Hz, 1H), 2.99 (br s, 1H), 2.78 (br s, 2H), 2.64-2.30 (m, 5H), 2.08-1.67 (m, 8H), 1.52 (br s, 1H). m/z (ESI, +ve ion) 646.9 (M+H)$^+$.

Example 705. (1S,3'R,6'R,7'S,11'R)-6-chloro-7'-hydroxy-11'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S,11'S)-6-chloro-7'-hydroxy-11'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide

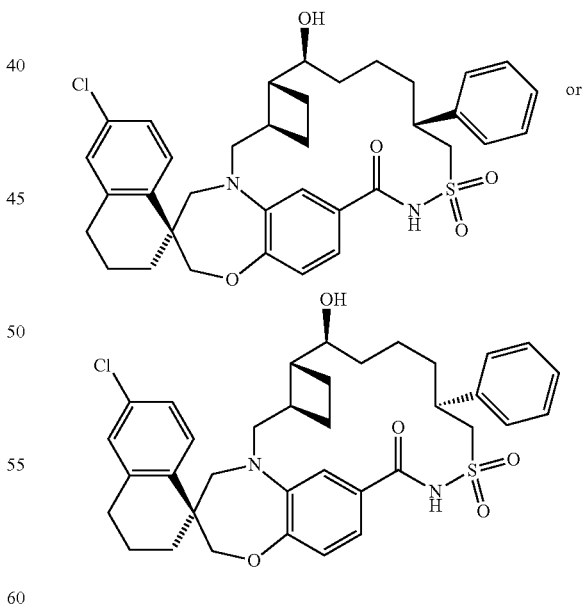

A mixture of the first eluting isomer from Example 703, Step 7 [(1S,3'R,6'R,7'S,8'E,11'R)-6-chloro-7'-hydroxy-11'-phenyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S)-6-chloro-7'-hydroxy-11'-phenyl-3,4-dihydro-2H,15'H-spiro[naphthalene-1,22'-[20]oxa[13]thia

[1,14]diazatetracyclo[14.7.2.0³,⁶.0¹⁹,²⁴]pentacosa[8,16,18, 24]tetraen]-15'-one 13',13'-dioxide] (4.9 mg, 7.57 μmol,) and platinum (iv) oxide (0.344 mg, 1.514 μmol) in EtOAc (6.0 mL) was stirred under hydrogen balloon at room temperature for 1h. The solid catalyst was filtered off through syringe filter, and filtrate was concentrated. The crude product was purified by reversed phase preparatory HPLC (Gemini™ Prep C18 5 μm column; Phenomenex, Torrance, CA; gradient elution of 40% to 90% MeCN in water, where both solvents contained 0.1% TFA, 30 min method) to provide one of the title compounds as a white solid. ¹H NMR (400 MHz, DMSO-d₆) δ 7.70 (d, J=8.61 Hz, 1H), 7.34-7.26 (m, 3H), 7.25-7.18 (m, 4H), 7.12-7.08 (m, 1H), 7.03 (m, 1H), 6.97 (d, J=8.02 Hz, 1H), 4.12-4.00 (m, 3H), 3.92 (d, J=14.48 Hz, 1H), 3.71-3.61 (m, 2H), 3.55 (d, J=9.39 Hz, 1H), 3.44-3.33 (m, 1H), 3.26 (d, J=14.48 Hz, 1H), 3.12 (dd, J=15.26, 9.39 Hz, 1H), 2.98-2.90 (m, 1H), 2.85-2.67 (m, 3H), 2.56-2.47 (m, 1H), 2.35-2.21 (m, 2H), 2.09-1.98 (m, 2H), 1.97-1.82 (m, 4H), 1.75-1.66 (m, 2H), 1.45-1.23 (m, 5H). m/z (ESI, +ve ion) 648.8 (M+H)⁺.

Example 706. (1S,3'R,6'R,7'S,9'E,11'S)-6-chloro-7'-hydroxy-11'-(hydroxymethyl)-3,4-dihydro-2H,15'H-spiro[naphthalene-1,22'-[20]oxa[13]thia[1,14]diaza-tetracyclo[14.7.2.0³,⁶.0¹⁹,²⁴]pentacosa [9,16,18,24] tetraen]-15'-one 13',13'-dioxide or (1S,3'R,6'R,7'S, 9'E,11'R)-6-chloro-7'-hydroxy-11'-(hydroxymethyl)-3,4-dihydro-2H,15'H-spiro[naphthalene-1,22' [20] oxa[13]thia[1,14]diazatetracyclo[14.7.2.0³,⁶.0¹⁹,²⁴] pentacosa [9,16,18,24]tetraen]-15'-one 13',13'-dioxide or (1S,3'R,6'R,7'S,9'Z,11'R)-6-chloro-7'-hydroxy-11'-(hydroxymethyl)-3,4-dihydro-2H,15'H-spiro[naphthalene-1,22'-[20]oxa[13]thia[1,14] diazatetracyclo [14.7.2.0³,⁶.0¹⁹,²⁴]pentacosa[9,16,18, 24]tetraen]-15'-one 13',13'-dioxide or (1S,3'R,6'R, 7'S,9'Z,11'S)-6-chloro-7'-hydroxy-11'-(hydroxymethyl)-3,4-dihydro-2H,15'H-spiro [naphthalene-1,22'-[20]oxa[13]thia[1,14] diazatetracyclo[14.7.2.0³,⁶.0¹⁹,²⁴]pentacosa[9,16,18, 24]tetraen]-15'-one 13',13'-dioxide

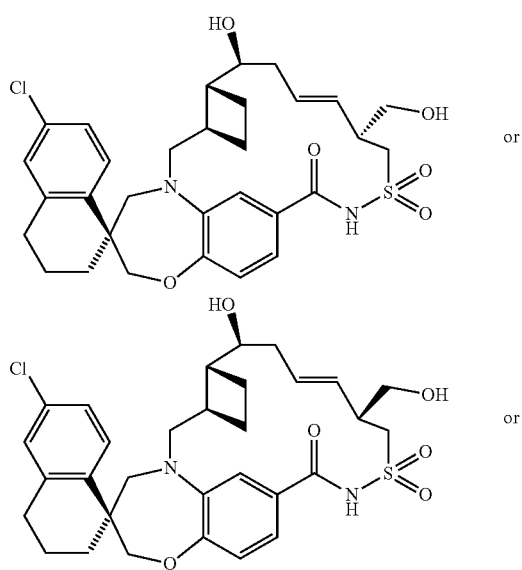

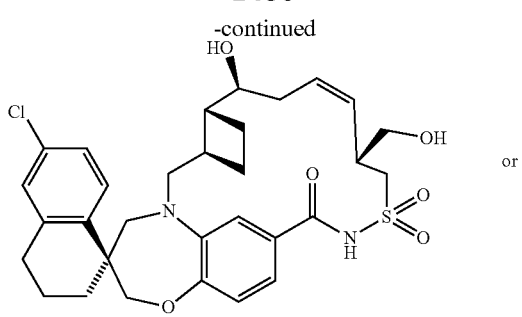

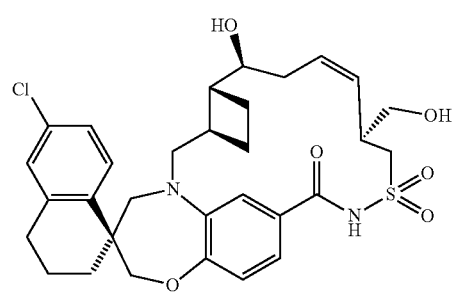

Step 1: (Z)-4-((tert-butyldiphenylsilyl)oxy)but-2-en-1-ol

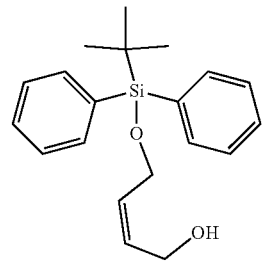 [SMILES: CC(C)(C)[Si](OC/C=C\CO)(c1ccccc1)c1ccccc1]

To a suspension of sodium hydride, 60% dispersion in mineral oil (0.478 mL, 22.70 mmol) in 20 mL of THF under nitrogen at room temperature was added a solution of cis-2-butene-1,4-diol (2.0 mL, 22.70 mmol) in 80 mL of THF slowly. The mixture was stirred at 50° C. for 1h, and then cooled to room temperature. To the cloudy mixture was added a solution of tert-butylchlorodiphenylsilane (5.90 mL, 22.70 mmol) in 20 mL of THF. The resulting mixture was stirred at room temperature for 16 h, and then 80 mL of saturated ammonium chloride aqueous and 100 mL of EtOAc were added. The mixture was stirred for 10 min and layers were separated. The aqueous layer was extracted with EtOAc (2×80 mL). The combined EtOAc solution was dried over sodium sulfate, filtered and concentrated to provide the crude product. The crude product was purified by chromatography on silica gel eluting with 0% to 40% EtOAc in hexane to provide the title compound (5.78 g, 78%). ¹H NMR (500 MHz, CDCl₃) δ 7.79-7.66 (m, 4 H), 7.50-7.35 (m, 6H), 5.83-5.60 (m, 2H), 4.37-4.24 (m, 2H), 4.10-3.96 (m, 2H), 1.16-1.04 (m, 9H).

Step 2: (Z)-11,11-dibutyl-2,2-dimethyl-3,3-diphenyl-4,9-dioxa-3-sila-11-stannapentadec-6-ene

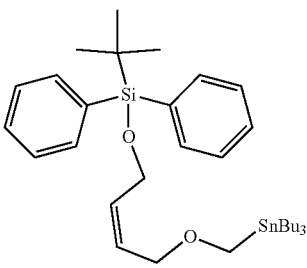

To a suspension of sodium hydride, 60% dispersion in mineral oil (1.303 g, 32.6 mmol) in THF (40 mL) at room temperature was added a solution of (Z)-4-((tert-butyldiphenylsilyl)oxy)but-2-en-1-ol (10.64 g, 32.6 mmol) in THF (50 mL) dropwise. After the reaction mixture was stirred for 15 min, tributyl(iodomethyl)stannane (7.02 g, 16.29 mmol, prepared according to the reference: *Synthetic Communication*, 24(8), 1117-1120, 1994) in THF (40 mL) was added, followed by HMPA (40 mL).The resulting mixture was stirred at room temperature for 16 h. The reaction was quenched by addition of water (300 mL) and brine (84 ml). The layers were separated, and then the aqueous layer was extracted with ether (3×200 mL). The combined organic solution was washed with brine, dried over sodium sulfate, filtered, and concentrated. The crude product was absorbed into 80 g of silica gel and dried, and then purified by chromatography on silica gel eluting with 0% to 5% EtOAc in hexane to provide the title compound (1.26 g, 12.4%). $^1$H NMR (400 MHz, CDCl$_3$) δ 7.77-7.70 (m, 4H), 7.47-7.40 (m, 6H), 5.83-5.75 (m, 1H), 5.62-5.53 (m, 1H), 4.33-4.29 (m, 2H), 3.81 (dd, J=6.26, 0.78 Hz, 2H), 3.68-3.61 (m, 2H), 1.58-1.47 (m, 6H), 1.38-1.27 (m, 6H), 1.12-1.08 (m, 9H), 0.96-0.88 (m, 15H).

Step 3: (S)-2-(((tert-butyldiphenylsilyl)oxy)methyl)but-3-en-1-ol and (R)-2-(((tert-butyldiphenylsilyl)oxy)methyl)but-3-en-1-ol

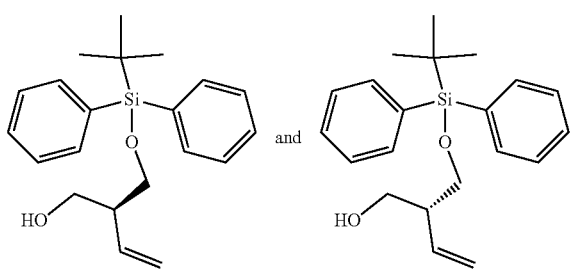 [SMILES: C=C[C@@H](CO)CO[Si](c1ccccc1)(c1ccccc1)C(C)(C)C ; C=C[C@H](CO)CO[Si](c1ccccc1)(c1ccccc1)C(C)(C)C]

To a solution of (Z)-11,11-dibutyl-2,2-dimethyl-3,3-diphenyl-4,9-dioxa-3-sila-11-stannapentadec-6-ene (1.26 g, 2.01 mmol) in THF (70 mL) at −78° C. was added butyllithium, 1.6 M in hexanes (3.76 mL, 6.02 mmol) slowly. The reaction mixture was stirred at −78° C. for 1h, before being quenched with water (30 mL). The layers were separated and aqueous layer was extracted with ether (3×80 mL). The combined organic solutions were washed with brine, dried over sodium sulfate, filtered, and concentrated under reduced pressure. The crude product was purified by chromatography on silica gel eluting with DCM to provide the title compounds (0.277 g, 40.5%). $^1$H NMR (400 MHz, CDCl$_3$) δ 7.78-7.69 (m, 4H), 7.52-7.40 (m, 6H), 5.84-5.65 (m, 1H), 5.24-5.11 (m, 2H), 3.92-3.74 (m, 4H), 2.68-2.54 (m, 1H), 1.17-1.08 (m, 9H).

Step 4: (R)-((2-((benzylthio)methyl)but-3-en-1-yl)oxy)(tert-butyl) diphenylsilane and (S)-((2-((benzylthio)methyl)but-3-en-1-yl)oxy) (tert-butyl)diphenylsilane

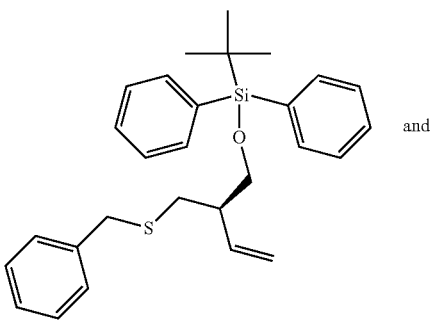

A mixture of (S)-2-(((tert-butyldiphenylsilyl)oxy)methyl)but-3-en-1-ol and (R)-2-(((tert-butyldiphenylsilyl)oxy)methyl)but-3-en-1-ol (0.277 g, 0.813 mmol), (mercaptomethyl)benzene (0.105 ml, 0.895 mmol) and cyanomethylenetri-n-butylphosphorane (0.353 ml, 1.464 mmol) in toluene (2.96 ml) was heated at 90° C. for 3h. The reaction mixture was cooled to room temperature, and diluted with EtOAc, washed with saturated ammonium chloride aqueous solution and brine, dried over sodium sulfate, concentrated. The crude product was absorbed into 10 g of silica gel and dried, and then purified by chromatography on silica gel eluting with 0% to 30% EtOAc in hexane to provide the title compounds (0.229 g, 63%). $^1$H NMR (400 MHz, CDCl$_3$) δ 7.75-7.70 (m, 4H), 7.52-7.42 (m, 6H), 7.35-7.26 (m, 5H), 5.82 (ddd, J=17.07, 10.51, 7.83 Hz, 1H), 5.20-5.11 (m, 2H), 3.81-3.66 (m, 4H), 2.86-2.79 (m, 1H), 2.60-2.46 (m, 2H), 1.14-1.09 (m, 9H). m/z (ESI, +ve ion) 469.1 (M+Na)$^+$.

1489

Step 5: (R)-2-(((tert-butyldiphenylsilyl)oxy)methyl)but-3-ene-1-sulfonamide and (S)-2-(((tert-butyldiphenylsilyl)oxy)methyl)but-3-ene-1-sulfonamide

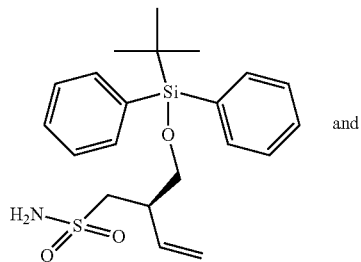

and

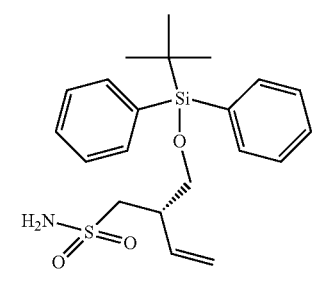

To a mixture of (R)-((2-((benzylthio)methyl)but-3-en-1-yl)oxy)(tert-butyl)diphenylsilane and (S)-((2-((benzylthio)methyl)but-3-en-1-yl)oxy)(tert-butyl)diphenylsilane (0.229 g, 0.513 mmol) and iodosylbenzene (0.372 g, 1.692 mmol) in 50 mL of ether was added hydrogen chloride (3.76 ml, 45.1 mmol) gradually with vigorously stirring. The resulting mixture was stirred for 2h. The reaction mixture was settled and layers were separated. The organic layer was washed with water, dried over sodium sulfate, filtered and concentrated under reduced pressure. The residue was dried on high vacuum for 1h. The solution of residue in 5 mL of DCM was added slowly into a solution of ammonium hydroxide, 28% (7.13 ml, 51.3 mmol) at 0° C. The resulting mixture was stirred at room temperature for 2h, and then settled. The layers were separated. The aqueous layer was extracted with DCM, and the combined organic layers were dried over sodium sulfate, filtered and concentrated. The residue was purified by chromatography on silica gel eluting with 0% to 60% EtOAc in hexane to provide the title compounds (0.138 g, 66.7%). m/z (ESI, +ve ion) 426.1 (M+Na)$^+$.

1490

Step 6: (3S)-6'-chloro-5-(((1R,2R)-2-((1S)-1-hydroxy-3-buten-1-yl) cyclobutyl)methyl)-N-(((2R)-2-((((2-methyl-2-propanyl) (diphenyl)silyl)oxy)methyl)-3-buten-1-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S)-1-hydroxy-3-buten-1-yl)cyclobutyl)methyl)-N-(((2S)-2-((((2-methyl-2-propanyl) (diphenyl)silyl)oxy)methyl)-3-buten-1-yl)sulfonyl)-3',4,4',5-tetrahydro-2'H-spiro[1,5-benzoxazepine-3,1'-naphthalene]-7-carboxamide

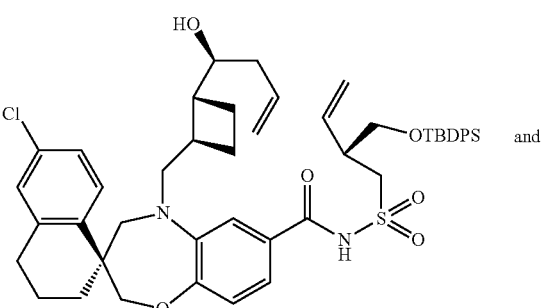

and

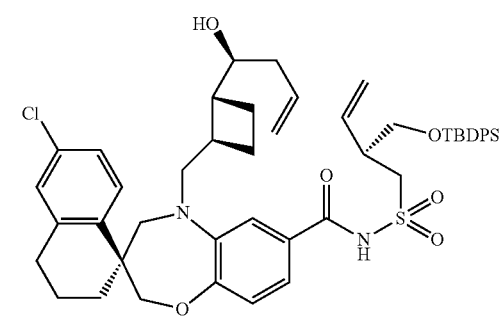

A mixture of (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (0.080 g, 0.166 mmol, Intermediate AA13A), (R)-2-(((tert-butyldiphenylsilyl)oxy)methyl)but-3-ene-1-sulfonamide and (S)-2-(((tert-butyldiphenylsilyl)oxy)methyl)but-3-ene-1-sulfonamide (0.134 g, 0.332 mmol), N,N-dimethylpyridin-4-amine (0.061 g, 0.498 mmol) and N1-((ethylimino)methylene)-N3,N3-dimethylpropane-1,3-diamine hydrochloride (0.064 g, 0.332 mmol) in 5 mL of DCE was stirred at room temperature for 16h. The solvent was removed under reduced pressure, and residue was purified by chromatography on silica gel eluting with 0% to 50% EtOAc (containing 0.2% AcOH) in hexane to provide the title compounds (0.168 g. 117%). m/z (ESI, +ve ion) 867.2 (M+H)$^+$.

Step 7: (S)-6'-chloro-5-(((1R,2R)-2-((S)-1-hydroxy-but-3-en-1-yl)cyclobutyl)methyl)-N—(((R)-2-(hydroxymethyl)but-3-en-1-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxybut-3-en-1-yl)cyclobutyl)methyl)-N—(((S)-2-(hydroxymethyl)but-3-en-1-yl)sulfonyl)-3',4,4',5-tetrahydro-2H,2'H-spiro[benzo[b][1,4]oxazepine-3,1'-naphthalene]-7-carboxamide

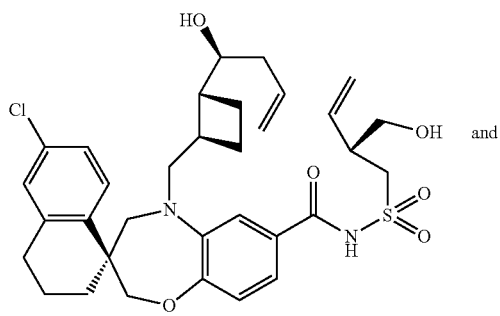

and

A solution of (3S)-6'-chloro-5-(((1R,2R)-2-((1S)-1-hydroxy-3-buten-1-yl)cyclobutyl)methyl)-N-(((2R)-2-((((2-methyl-2-propanyl)(diphenyl)silyl)oxy)methyl)-3-buten-1-yl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S)-1-hydroxy-3-buten-1-yl)cyclobutyl)methyl)-N-(((2S)-2-((((2-methyl-2-propanyl)(diphenyl)silyl)oxy)methyl)-3-buten-1-yl)sulfonyl)-3',4,4',5-tetrahydro-2'H-spiro[1,5-benzoxazepine-3,1'-naphthalene]-7-carboxamide (0.168 g, 0.194 mmol) in 1 mL of THF was treated with tetra-n-butylammonium fluoride, 1M solution in THF (3.87 ml, 3.87 mmol). The reaction mixture was stirred at room temperature for 24h. The solvent was removed under reduced pressure and residue was purified by chromatography on silica gel eluting with 0% to 10% MeOH in DCM to provide the title compounds (0.088 g, 72.2%). m/z (ESI, +ve ion) 629.2.1 (M+H)$^+$.

Step 8: (1S,3'R,6'R,7'S,9'E,11'S)-6-chloro-7'-hydroxy-11'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'R,7'S,9'E,11'R)-6-chloro-7'-hydroxy-11'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'R,7'S,9'Z,11'R)-6-chloro-7'-hydroxy-11'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'R,7'S,9'Z,11'S)-6-chloro-7'-hydroxy-11'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide A solution of (S)-6'-chloro-5-(((1R,2R)-2-((S)-1-hydroxybut-3-en-1-yl)cyclobutyl)methyl)-N—(((R)-2-(hydroxymethyl)but-3-en-1-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxybut-3-en-1-yl)cyclobutyl)methyl)-N—(((S)-2-(hydroxymethyl)but-3-en-1-yl)sulfonyl)-3',4,4',5-tetrahydro-2H,2'H-spiro[benzo[b][1,4]oxazepine-3,1'-naphthalene]-7-carboxamide (0.088 g, 0.140 mmol) in toluene (200 mL) was subjected to three cycles of evacuation/back-filling with nitrogen. To this solution was added a solution of Hoveyda-Grubbs catalyst (2nd generation) (0.018 g, 0.028 mmol) in 1 mL of Toluene at room temperature. The reaction mixture was stirred at 106° C. under nitrogen for 4h. Air was blown into mixture for deactivating the catalyst. The reaction was cooled to room temperature and concentrated. The crude product was purified by reversed phase preparatory HPLC (Gemini™ Prep C18 5 µm column; Phenomenex, Torrance, CA; gradient elution of 40% to 90% MeCN in water, where both solvents contained 0.1% TFA, 30 min method) to provide the first eluting isomer as one of the title compounds. $^1$H NMR (400 MHz, CDCl$_3$) δ 7.73 (d, J=8.61 Hz, 1H), 7.41 (dd, J=8.41, 1.96 Hz, 1H), 7.19 (dd, J=8.61, 2.15 Hz, 1H), 7.10 (d, J=2.35 Hz, 1H), 7.02-6.95 (m, 1H), 6.93 (s, 1H), 5.75 (ddd, J=14.67, 10.86, 3.23 Hz, 1H), 5.41 (dd, J=14.77, 10.07 Hz, 1H), 4.18-4.07 (m, 2H), 4.01-3.86 (m, 2H), 3.66 (d, J=14.28 Hz, 2H), 3.61-3.48 (m, 3H), 3.30 (d, J=14.48 Hz, 1H), 3.23-2.99 (m, 3H), 2.81-2.74 (m, 2H), 2.46-2.34 (m, 2H), 2.19-1.76 (m, 6H), 1.66-1.47 (m, 4H), 1.35-1.27 (m, 2H). m/z (ESI, +ve ion) 601.2 (M+H)$^+$.

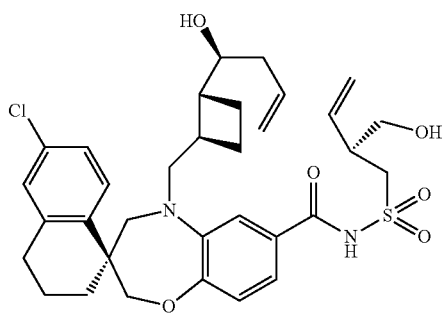

Example 707. (1S,3'R,6'R,7'S,9'E,11'R)-6-chloro-7'-hydroxy-11'-(hydroxymethyl)-3,4-dihydro-2H,15'H-spiro[naphthalene-1,22'-[20]oxa [13]thia[1,14]diazatetracyclo[14.7.2.0$^{3,6}$.0$^{19,24}$]pentacosa[9,16,18, 24]tetraen]-15'-one 13',13'-dioxide or (1S,3'R,6'R,7'S,9'E,11'S)-6-chloro-7'-hydroxy-11'-(hydroxymethyl)-3,4-dihydro-2H,15'H-spiro[naphthalene-1,22'-[20]oxa [13]thia[1,14]diazatetracyclo[14.7.2.0$^{3,6}$.0$^{19,24}$]pentacosa[9,16,18, 24]tetraen]-15'-one 13',13'-dioxide or (1S,3'R,6'R,7'S,9'Z,11'R)-6-chloro-7'-hydroxy-11'-(hydroxymethyl)-3,4-dihydro-2H,15'H-spiro[naphthalene-1,22'-[20]oxa [13]thia[1,14]diazatetracyclo[14.7.2.0$^{3,6}$.0$^{19,24}$]pentacosa[9,16,18, 24]tetraen]-15'-one 13',13'-dioxide or (1S,3'R,6'R,7'S,9'Z,11'S)-6-chloro-7'-hydroxy-11'-(hydroxymethyl)-3,4-dihydro-2H,15'H-spiro[naphthalene-1,22'-[20]oxa [13]thia[1,14]diazatetracyclo[14.7.2.0$^{3,6}$.0$^{19,24}$]pentacosa[9,16,18, 24]tetraen]-15'-one 13',13'-dioxide

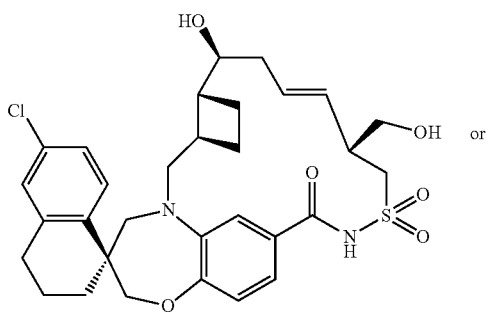
or

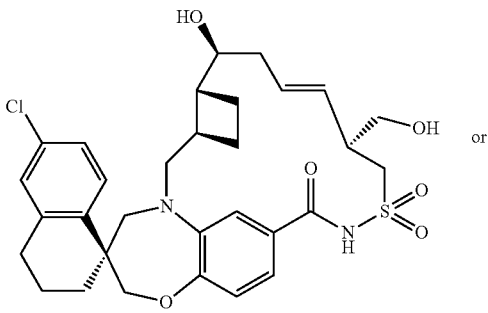
or

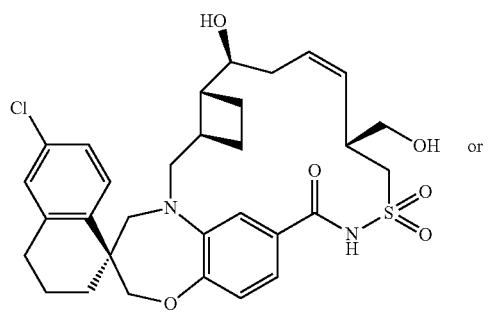
or

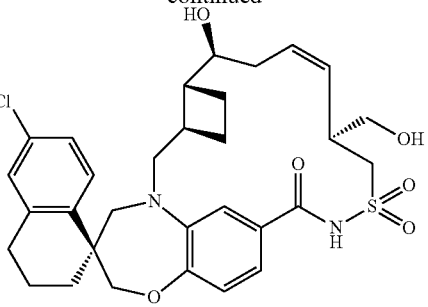

A second title compound as a white solid was obtained as the later eluting isomer from the reversed phase preparatory HPLC separation in Example 706, Step 8. $^1$H NMR (400 MHz, CDCl$_3$) δ 7.73 (d, J=8.41 Hz, 1H), 7.41 (dd, J=8.31, 2.05 Hz, 1H), 7.19 (dd, J=8.61, 2.35 Hz, 1H), 7.10 (d, J=2.35 Hz, 1H), 7.00 (d, J=8.22 Hz, 1H), 6.94-6.90 (m, 1H), 5.76 (ddd, J=14.62, 10.71, 4.01 Hz, 1H), 5.41 (dd, J=15.16, 10.66 Hz, 1H), 4.16-4.11 (m, 2H), 4.00-3.87 (m, 3H), 3.66 (d, J=14.28 Hz, 2H), 3.57-3.52 (m, 3H), 3.30 (d, J=14.48 Hz, 1H), 3.24-2.99 (m, 3H), 2.81-2.75 (m, 2H), 2.44-2.36 (m, 2H), 2.16-2.08 (m, 2H), 2.05-1.67 (m, 7H), 1.52-1.27 (m, 2H). m/z (ESI, +ve ion) 601.2 (M+H)$^+$.

Example 708. (1S,3'R,6'R,7'S,11'S)-6-chloro-7'-hydroxy-11'-(hydroxymethyl)-3,4-dihydro-2H,15'H-spiro[naphthalene-1,22'-[20]oxa[13]thia [1,14]diazatetracyclo[14.7.2.0$^{3,6}$.0$^{19,24}$]pentacosa[16,18,24]trien]-15'-one 13',13'-dioxide or (1S,3'R,6'R,7'S,11'R)-6-chloro-7'-hydroxy-11'-(hydroxymethyl)-3,4-dihydro-2H,15'H-spiro[naphthalene-1,22'-[20]oxa [13]thia[1,14]diazatetracyclo[14.7.2.0$^{3,6}$.0$^{19,24}$]pentacosa[16,18,24]trien]-15'-one 13',13'-dioxide

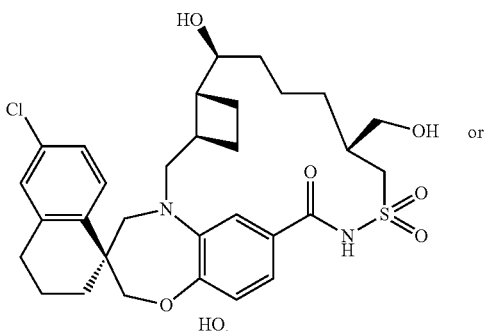
or

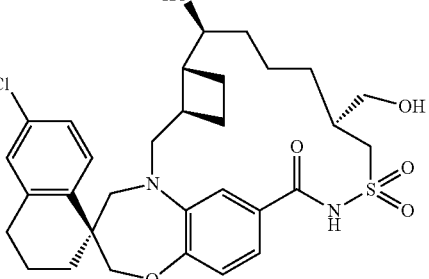

A mixture of the first eluting isomer from Example 706, Step 8 [(1S,3'R,6'R,7'S,9'E,11'S)-6-chloro-7'-hydroxy-11'-(hydroxymethyl)-3,4-dihydro-2H,15'H-spiro[naphthalene- 1,22'-[20]oxa[13]thia[1,14]diazatetracyclo [14.7.2.0³,⁶.0¹⁹,²⁴]pentacosa[9,16,18,24]tetraen]-15'-one 13',13'-dioxide or (1S,3'R,6'R,7'S,9'E,11'R)-6-chloro-7'-hydroxy-11'-(hydroxymethyl)-3,4-dihydro-2H,15'H-spiro[naphthalene-1,22'-[20]oxa[13]thia[1,14]diazatetracyclo [14.7.2.0³,⁶.0¹⁹,²⁴]pentacosa[9,16,18,24]tetraen]-15'-one 13',13'-dioxide or (1S,3'R,6'R,7'S,9'Z,11'R)-6-chloro-7'-hydroxy-11'-(hydroxymethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide or (1S,3'R,6'R,7'S,9'Z,11'S)-6-chloro-7'-hydroxy-11'-(hydroxymethyl)-3,4-dihydro-2H,15'H-spiro[naphthalene-1,22'-[20]oxa[13]thia[1,14]diazatetracyclo [14.7.2.0³,⁶.0¹⁹,²⁴]pentacosa[9,16,18,24]tetraen]-15'-one 13',13'-dioxide] (4.0 mg, 6.65 µmol) and platinum (iv) oxide (0.30 mg, 1.33 µmol) in ethyl acetate (2.0 mL) was stirred under hydrogen balloon at room temperature for 2h. The solid catalyst was filtered off through a syringe filter, and filtrate was concentrated. The crude product was purified by reversed phase preparatory HPLC (Gemini™ Prep C18 5 µm column; Phenomenex, Torrance, CA; gradient elution of 40% to 90% MeCN in water, where both solvents contained 0.1% TFA, 30 min method) to provide one of the title compounds. ¹H NMR (500 MHz, CDCl₃) δ 9.15 (br s, 1H), 7.71 (d, J=8.31 Hz, 1H), 7.23-7.13 (m, 3H), 7.11 (d, J=1.96 Hz, 1H), 6.99-6.92 (m, 1H), 4.17-4.07 (m, 2H), 3.88 (dd, J=15.28, 5.01 Hz, 1H), 3.82-3.71 (m, 3H), 3.70-3.63 (m, 2H), 3.55-3.45 (m, 1H), 3.26 (d, J=14.43 Hz, 1H), 3.14 (br s, 1H), 2.83-2.75 (m, 2H), 2.41-2.34 (m, 2H), 2.30-2.16 (m, 1H), 2.13-1.78 (m, 7H), 1.73-1.32 (m, 9H). m/z (ESI, +ve ion) 603.2 (M+H)⁺.

Example 709. (1S,3'R,6'R,7'S,9'Z,12'S)-6-chloro-7'-hydroxy-12'-(hydroxymethyl)-3,4-dihydro-2H,16'H-spiro[naphthalene-1,23'-[21]oxa [14]thia[1,15]diazatetracyclo[15.7.2.0³,⁶.0²⁰,²⁵]hexacosa[9,17,19,2 5]tetraen]-16'-one 14',14'-dioxide and (1S,3'R,6'R,7'S,9'Z,12'R)-6-chloro-7'-hydroxy-12'-(hydroxymethyl)-3,4-dihydro-2H,16'H-spiro[naphthalene-1,23'-[21]oxa [14]thia[1,15]diazatetracyclo[15.7.2.0³,⁶.0²⁰,²⁵]hexacosa[9,17,19,2 5]tetraen]-16'-one 14',14'-dioxide

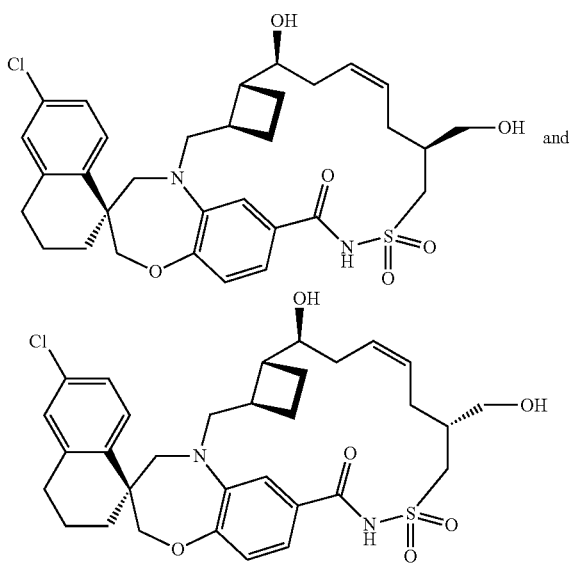

Step 1: 2-allylpropane-1,3-diol

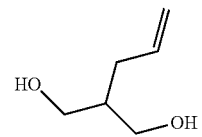

A solution of diethyl allylmalonate (7.93 ml, 40 mmol) in 40 mL of THF was added dropwise to a stirred solution of lithium aluminum hydride, 1.0 M solution in THF (100 ml, 100 mmol) in THF (250 mL) at 0° C. over 30 min. The ice bath was removed, and reaction mixture was stirred at room temperature for 4h. The reaction mixture was cooled to 0° C. To this mixture were added the 3.8 mL of water, 3.8 mL of 15% sodium hydroxide aqueous solution, and 11 mL of water in order. The reaction mixture was stirred at room temperature for 10 min, and filtered through celite. The filtrate was concentrated, and residue was purified by chromatography on silica gel eluting with 30% to 90% EtOAc in hexane to provide the title compound (4.43 g, 95%). ¹H NMR (400 MHz, CDCl₃) δ 5.84-5.62 (m, 1H), 5.09-4.89 (m, 2H), 4.14-4.08 (m, 2H), 3.70-3.61 (m, 2H), 3.54 (dd, J=7.24, 10.76 Hz, 2H), 2.04-1.95 (m, 2H), 1.81-1.68 (m, 1H).

Step 2: (R)-2-(((tert-butyldiphenylsilyl)oxy)methyl)pent-4-en-1-ol and (S)-2-(((tert-butyldiphenylsilyl)oxy)methyl)pent-4-en-1-ol

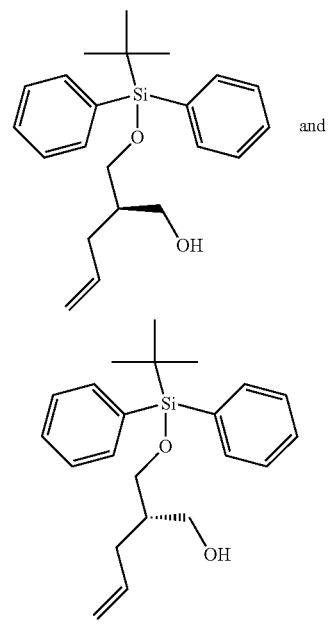

To a suspension of sodium hydride, 60% dispersion in mineral oil (0.589 g, 14.7 mmol) in 15 mL of THF under nitrogen at room temperature was added a solution of 2-allylpropane-1,3-diol (1.71 g, 14.7 mmol) in 45 mL of THF slowly. The mixture was stirred at 50° C. for 1h, and then cooled to room temperature. To the cloudy mixture was added a solution of tert-butylchlorodiphenylsilane (3.83 mL, 14.72 mmol) in 30 mL of THF. The resulting mixture was stirred at room temperature for 16h, and then 50 mL of saturated ammonium chloride aqueous and 100 mL of EtOAc were added. The mixture was stirred for 10 min and layers separated. The aqueous layer was extracted with EtOAc (2×100 mL); combined EtOAc solution was dried over sodium sulfate, filtered and concentrated. The crude product was purified by chromatography on silica gel eluting with 0% to 50% EtOAc in hexane to provide the title compounds (4.99 g, 84%). ¹H NMR (400 MHz, CDCl₃) δ 7.79-7.71 (m, 4H), 7.55-7.38 (m, 6H), 5.79 (ddt, J=17.12, 10.07, 7.04, 7.04 Hz, 1H), 5.13-4.96 (m, 2H), 3.92-3.67 (m, 4H), 2.62 (br s, 1H), 2.14 (t, J=7.04 Hz, 2H), 1.94 (quint, J=6.83, 6.83, 6.83, 6.83, 4.33, 4.33 Hz, 1H), 1.15 (s, 9H).

Step 3: (S)-((2-((benzylthio)methyl)pent-4-en-1-yl)oxy)(tert-butyl)diphenylsilane and (R)-((2-((benzylthio)methyl)pent-4-en-1-yl)oxy)(tert-butyl)diphenylsilane

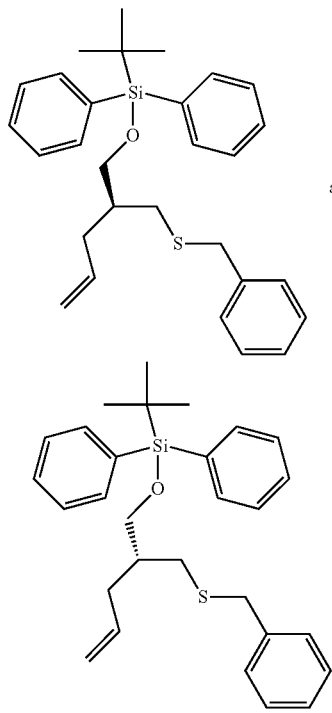

and

A mixture of (R)-2-(((tert-butyldiphenylsilyl)oxy)methyl)pent-4-en-1-ol and (S)-2-(((tert-butyldiphenylsilyl)oxy)methyl)pent-4-en-1-ol (4.39 g, 12.4 mmol), benzylmercaptan (1.60 mL, 13.6 mmol) and cyanomethylenetri-n-butylphosphorane (5.38 mL, 22.3 mmol) in toluene (45 mL) heated at 90° C. for 3h. The reaction mixture was cooled to room temperature and diluted with EtOAc. The mixture was washed with saturated ammonium chloride aqueous solution and brine, dried over sodium sulfate, filtered and concentrated. The crude product was absorbed into 80 g of silica gel and dried, and then purified by chromatography on silica gel eluting with 0% to 30% EtOAc in hexane to provide the title compounds (4.91 g, 86%). ¹H NMR (400 MHz, CDCl₃) δ 7.76-7.72 (m, 4H), 7.53-7.43 (m, 6H), 7.39-7.33 (m, 4H), 7.32-7.26 (m, 1H), 5.80-5.68 (m, 1H), 5.11-5.01 (m, 2H), 3.79-3.67 (m, 4H), 2.73-2.66 (m, 1H), 2.55 (dd, J=12.91, 6.26 Hz, 1H), 2.32-2.26 (m, 2H), 1.91-1.80 (m, 1H), 1.16-1.11 (m, 9H).

Step 4: (S)-2-(((tert-butyldiphenylsilyl)oxy)methyl)pent-4-ene-1-sulfonamide and (R)-2-(((tert-butyldiphenylsilyl)oxy)methyl)pent-4-ene-1-sulfonamide

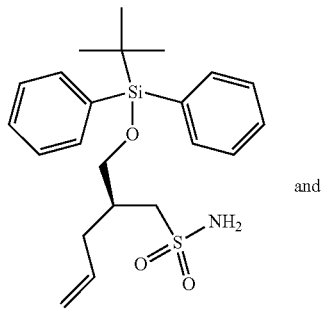

and

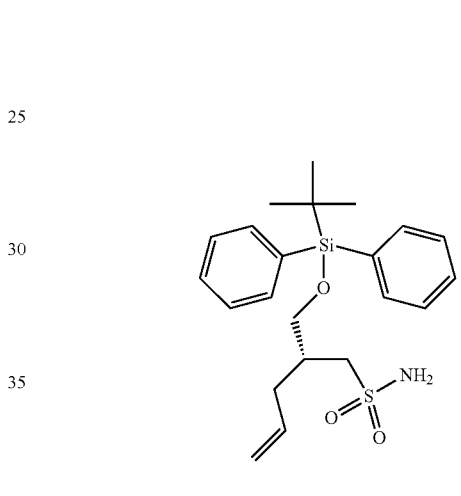

To a mixture of (S)-((2-((benzylthio)methyl)pent-4-en-1-yl)oxy)(tert-butyl)diphenylsilane and (R)-((2-((benzylthio)methyl)pent-4-en-1-yl)oxy)(tert-butyl)diphenylsilane (2.46 g, 5.34 mmol) and iodosylbenzene (3.88 g, 17.6 mmol) in ether (300 mL) was added concentrated hydrochloric acid (39.2 mL, 470 mmol) gradually with vigorous stirring. The resulting mixture was stirred for 2h. The reaction mixture was settled and layers separated. The organic layer was washed with water and dried over sodium sulfate, filtered and concentrated under reduced pressure. The residue was dried on high vacuum for 1h. The solution of residue in 5 mL of DCM was added slowly into a solution of ammonium hydroxide, 28% NH₃ (74.3 mL, 534 mmol) at 0° C. The resulting mixture was stirred at room temperature for 2h and settled. The layers were separated. The aqueous layer was extracted with DCM (3×), and the combined organic layers were dried over sodium sulfate, filtered and concentrated. The residue was purified by chromatography on silica gel eluting with 0% to 60% EtOAc in hexane to provide the title compounds (1.04 g, 46.5%). ¹H NMR (400 MHz, CDCl₃) δ 7.75-7.61 (m, 4H), 7.53-7.37 (m, 6H), 5.80-5.60 (m, 1H), 5.14-5.01 (m, 2H), 4.62 (s, 2H), 3.88-3.65 (m, 2H), 3.34 (dd, J=14.38, 6.36 Hz, 1H), 3.12 (dd, J=14.48, 5.28 Hz, 1H), 2.42-2.16 (m, 3H), 1.15-1.02 (m, 9H).

Step 5: (S)-6'-chloro-5-(((1R,2R)-2-((S)-1-hydroxy-but-3-en-1-yl)cyclobutyl)methyl)-N—(((R)-2-(hydroxymethyl)pent-4-en-1-yl) sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxybut-3-en-1-yl)cyclobutyl)methyl)-N—(((S)-2-(hydroxymethyl)pent-4-en-1-yl)sulfonyl)-3',4,4',5-tetrahydro-2H,2'H-spiro[benzo[b][1,4]oxazepine-3,1'-naphthalene]-7-carboxamide

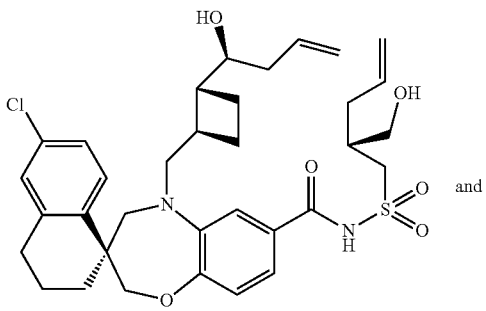

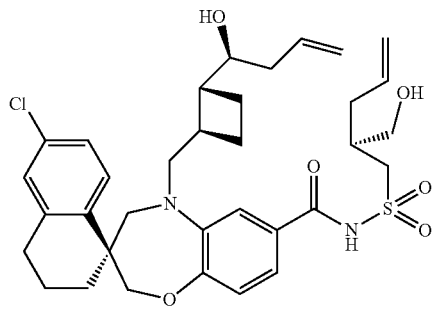

A mixture of (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (0.070 g, 0.145 mmol, Intermediate AA13A), (S)-2-(((tert-butyldiphenylsilyl)oxy)methyl)pent-4-ene-1-sulfonamide and (R)-2-(((tert-butyldiphenylsilyl)oxy)methyl)pent-4-ene-1-sulfonamide (0.121 g, 0.29 mmol), 4-(dimethylamino)pyridine (0.053 g, 0.436 mmol) and 1-(3-dimethylaminopropyl)-3-ethylcarbodiimide hydrochloride (0.056 g, 0.29 mmol) in 5 mL of DCE was stirred at room temperature for 16h. The reaction mixture was directly loaded on column (5 g silica gel) for purification by chromatography on silica gel eluting with 0% to 50% EtOAc (containing 0.2% AcOH) in hexane to provide the precursor of the title compound. The precursor of the title compound was treated with tetrabutylammonium fluoride, 1.0 M in THF (6.41 mL, 6.41 mmol) in 2 mL of THF was stirred at room temperature for 4.5 days. The solvent was removed under reduced pressure and residue was purified by chromatography on silica gel eluting with 0% to 10% MeOH in DCM to provide the title compounds (0.055 g, 59%). m/z (ESI, +ve ion) 643.2 (M+H)+.

Step 6: (1S,3'R,6'R,7'S,9'Z,12'S)-6-chloro-7'-hydroxy-12'-(hydroxymethyl)-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide and (1S,3'R,6'R,7'S,9'Z,12'R)-6-chloro-7'-hydroxy-12'-(hydroxymethyl)-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide A solution of (S)-6'-chloro-5-(((1R,2R)-2-((S)-1-hydroxybut-3-en-1-yl)cyclobutyl)methyl)-N—(((R)-2-(hydroxymethyl)pent-4-en-1-yl)sulfonyl)-3',4,4',5-tetrahydro-2H,2'H-spiro[benzo [b][1,4]oxazepine-3,1'-naphthalene]-7-carboxamide and (S)-6'-chloro-5-(((1R,2R)-2-((S)-1-hydroxybut-3-en-1-yl)cyclobutyl)methyl)-N—(((S)-2-(hydroxymethyl)pent-4-en-1-yl)sulfonyl)-3',4,4',5-tetrahydro-2H,2'H-spiro[benzo[b][1,4]oxazepine-3,1'-naphthalene]-7-carboxamide (0.055 g, 0.086 mmol) in toluene (130 mL) was subjected to three cycles of evacuation/back-filling with nitrogen. To the homogeneous solution was added a solution of Hoveyda-Grubbs catalyst (2nd generation) (10.7 mg, 0.017 mmol) in 1 mL of toluene at room temperature. The reaction mixture was stirred at 106° C. under nitrogen for 4h. Air was blown into mixture for 5 min. The reaction mixture was cooled to room temperature, and then concentrated. The residue was purified by reversed phase preparatory HPLC (Gemini™ Prep C18 5 µm column; Phenomenex, Torrance, CA; gradient elution of 40% to 90% MeCN in water, where both solvents contained 0.1% TFA, 30 min method) to provide the first eluting component as the Z olefin compounds. $^1$H NMR (400 MHz, CDCl$_3$) δ 7.73 (d, J=8.41 Hz, 1H), 7.38 (dd, J=8.31, 1.66 Hz, 1H), 7.29-7.26 (m, 1H), 7.18 (dd, J=8.41, 2.15 Hz, 1H), 7.09 (d, J=2.15 Hz, 1H), 6.96 (d, J=8.41 Hz, 1H), 5.58-5.44 (m, 2H), 4.13-4.07 (m, 2H), 3.88 (d, J=15.45 Hz, 1H), 3.80-3.46 (m, 6H), 3.20-3.06 (m, 2H), 2.80-2.73 (m, 2H), 2.50 (d, J=10.37 Hz, 3H), 2.40-2.29 (m, 2H), 2.14-1.76 (m, 9H), 1.70-1.39 (m, 4H). m/z (ESI, +ve ion) 615.1 (M+H)+.

Example 710. (1S,3'R,6'R,7'S,9'E,12'S)-6-chloro-7'-hydroxy-12'-(hydroxymethyl)-3,4-dihydro-2H,16'H-spiro [naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide and (1S,3'R,6'R,7'S,9'E,12'R)-6-chloro-7'-hydroxy-12'-(hydroxymethyl)-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide

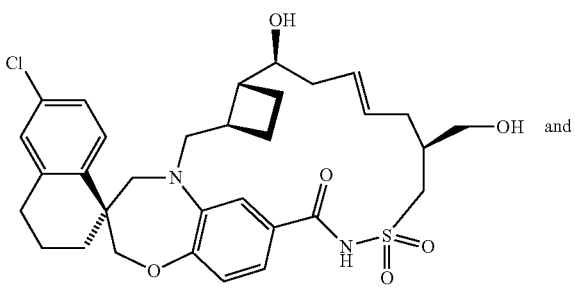

-continued

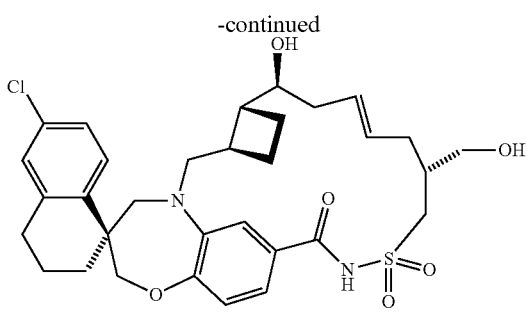

The E olefin title compounds were obtained as a white solid as the later eluting component from the reversed phase preparatory HPLC separation in Example 709, Step 6. $^1$H NMR (400 MHz, CDCl$_3$) δ 7.72 (d, J=8.41 Hz, 1H), 7.61 (dd, J=8.31, 2.05 Hz, 1H), 7.24 (d, J=2.15 Hz, 1H), 7.18 (dd, J=8.41, 2.35 Hz, 1H), 7.09 (d, J=2.35 Hz, 1H), 7.02-6.93 (m, 1H), 5.52-5.44 (m, 1H), 5.28 (t, J=11.74 Hz, 1H), 4.17-4.04 (m, 2H), 3.95-3.85 (m, 2H), 3.69-3.51 (m, 5H), 3.09 (d, J=13.89 Hz, 1H), 3.01 (dd, J=15.65, 8.02 Hz, 1H), 2.84-2.71 (m, 3H), 2.18-2.00 (m, 5H), 1.93-1.51 (m, 9H), 1.49-1.30 (m, 3H). m/z (ESI, +ve ion) 615.1 (M+H)$^+$.

Example 711. (1S,3'R,6'R,7'S,12'S)-6-chloro-7'-hydroxy-12'-(hydroxymethyl)-3,4-dihydro-2H,16'H-spiro[naphthalene-1,23'-[21]oxa[14]thia[1,15]diaza-tetracyclo[15.7.2.0$^{3,6}$.0$^{20,25}$]hexacosa[17,19,25]trien]-16'-one 14',14'-dioxide and (1S,3'R,6'R,7'S,12'R)-6-chloro-7'-hydroxy-12'-(hydroxymethyl)-3,4-dihydro-2H,16'H-spiro[naphthalene-1,23'-[21]oxa[14]thia[1,15]diazatetracyclo[15.7.2.0$^{3,6}$.0$^{20,25}$]hexacosa[17,19,25]trien]-16'-one 14',14'-dioxide

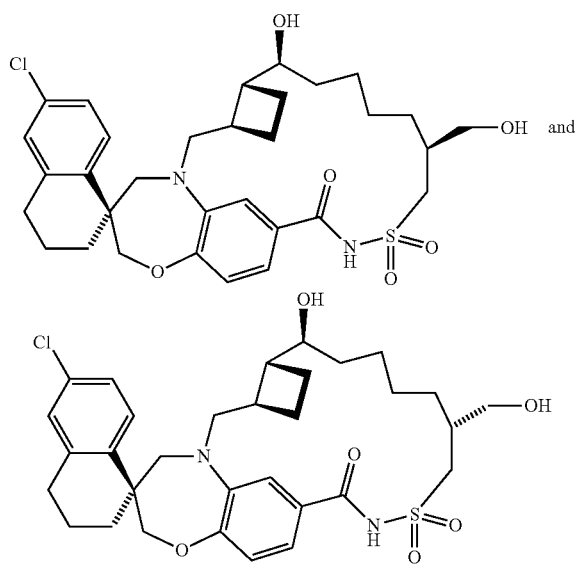

A mixture of the compounds from Example 709, Step 6 [(1S,3'R,6'R,7'S,9'Z,12'S)-6-chloro-7'-hydroxy-12'-(hydroxymethyl)-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide and (1S,3'R,6'R,7'S,9'Z,12'R)-6-chloro-7'-hydroxy-12'-(hydroxymethyl)-3,4-dihydro-2H,16'H-spiro[naphthalene-1, 23'-[21]oxa[14]thia[1,15]diazatetracyclo [15.7.2.0$^{3,6}$.0$^{20,25}$] hexacosa[9,17,19,25]tetraen]-16'-one 14',14'-dioxide (4 mg, 6.5 μmol) and platinum(IV) oxide (0.15 mg, 0.65 μmol) in ethyl acetate (2.5 mL) was stirred under hydrogen balloon at room temperature for 2 h. The solid catalyst was filtered off through a syringe filter, and filtrate was concentrated. The crude product was purified by reversed phase preparatory HPLC (Gemini™ Prep C18 5 μm column; Phenomenex, Torrance, CA; gradient elution of 40% to 90% MeCN in water, where both solvents contained 0.1% TFA, 30 min method) to provide the title compounds. $^1$H NMR (400 MHz, CDCl$_3$) δ 10.40 (br s, 1H), 7.72 (d, J=8.61 Hz, 1H), 7.54-7.46 (m, 1H), 7.35 (br s, 1H), 7.18 (dd, J=1.96, 8.61 Hz, 1H), 7.10 (s, 1H), 6.99 (d, J=8.61 Hz, 1H), 4.14 (s, 2H), 3.77 (dd, J=3.62, 10.86 Hz, 2H), 3.74-3.58 (m, 4H), 3.55-3.45 (m, 3H), 3.24 (d, J=15.06 Hz, 1H), 2.82-2.73 (m, 2H), 2.45-2.27 (m, 3H), 2.11-1.84 (m, 6H), 1.81-1.57 (m, 5H), 1.54-1.32 (m, 6H). m/z (ESI, +ve ion) 617.2 (M+H)$^+$.

Example 712. (1S,3'R,6'R,7'S,12'S)-6-chloro-7'-hydroxy-12'-(hydroxymethyl)-3,4-dihydro-2H,15'H-spiro[naphthalene-1,22'-[20]oxa[13]thia[1,14]diaza-tetracyclo[14.7.2.0$^{3,6}$.0$^{19,24}$]pentacosa[16,18,24]trien]-15'-one 13',13'-dioxide or (1S,3'R,6'R,7'S, 12'R)-6-chloro-7'-hydroxy-12'-(hydroxymethyl)-3,4-dihydro-2H,15'H-spiro[naphthalene-1,22'-[20]oxa [13]thia[1,14 diazatetracyclo[14.7.2.0$^{3,6}$.0$^{19,24}$] pentacosa]16,18,24]trien]-15'-one 13',13'-dioxide

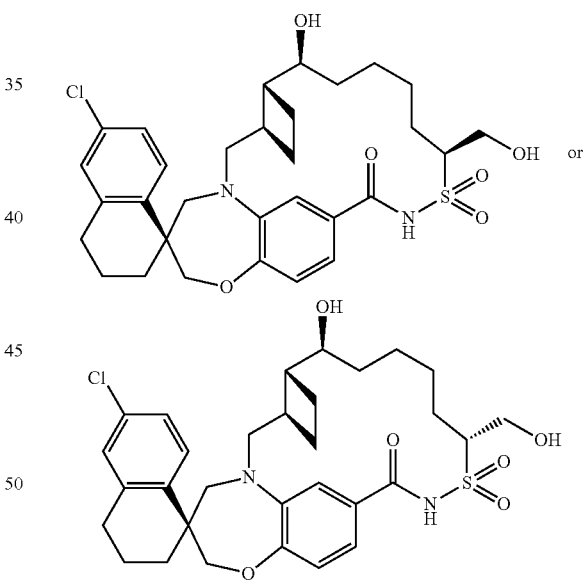

Step 1: (S)-1-((tert-butyldimethylsilyl)oxy)pent-4-en-2-ol and (R)-1-((tert-butyldimethylsilyl)oxy)pent-4-en-2-ol

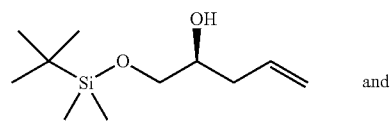

-continued

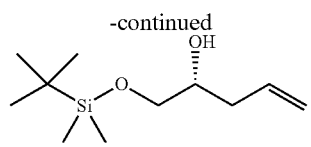

To a solution of (tert-butyldimethylsilyloxy)acetaldehyde (5.46 mL, 28.7 mmol) in THF (100 mL) at 0° C. was added allylmagnesium bromide, 1.0 M solution in diethyl ether (143 mL, 143 mmol) dropwise over 1h. The reaction was stirred at room temperature for 2h. The reaction was cooled to 0° C. and was quenched with saturated ammonium chloride (80 mL). The mixture was extracted with EtOAc (3×100 mL). The combined organic solution was washed with brine, dried over sodium sulfate and filtered, concentrated. The crude product was purified by chromatography on silica gel eluting with 0% to 60% EtOAc in hexane to provide the title compounds (3.70 g, 59.7%). $^1$H NMR (400 MHz, CDCl$_3$) δ 5.92-5.77 (m, 1H), 5.17-5.05 (m, 2H), 3.71 (qd, J=6.52, 3.72 Hz, 1H), 3.66-3.60 (m, 1H), 3.50-3.41 (m, 1H), 2.27-2.21 (m, 2H), 0.95-0.87 (m, 9H), 0.10-0.03 (m, 6H).

Step 2: (S)-((2-(benzylthio)pent-4-en-1-yl)oxy)(tert-butyl)dimethylsilane and (R)-((2-(benzylthio)pent-4-en-1-yl)oxy)(tert-butyl)dimethylsilane

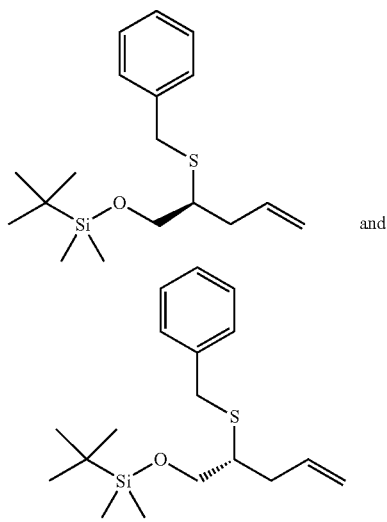

A mixture of (S)-1-((tert-butyldimethylsilyl)oxy)pent-4-en-2-ol and (R)-1-((tert-butyldimethylsilyl)oxy)pent-4-en-2-ol (1.03 g, 4.76 mmol), phenylmethanethiol (5.58 mL, 4.76 mmol) and 2-(tributylphosphoranylidene)acetonitrile (2.50 mL, 9.51 mmol) in toluene (2.0 mL) was heated at 110° C. for 5h. The reaction mixture was cooled to room temperature, and diluted with EtOAc, washed with saturated ammonium chloride and brine, dried over sodium sulfate, and filtered, concentrated. The crude product was absorbed into 30 g of silica gel and dried, and then purified by chromatography on silica gel eluting with 0% to 20% EtOAc in hexane to provide the title compounds (0.498 g, 32.5%). $^1$H NMR (400 MHz, CDCl$_3$) δ 7.35-7.14 (m, 5H), 5.84-5.64 (m, 1H), 5.07-4.95 (m, 2H), 3.77-3.50 (m, 4H), 2.69-2.15 (m, 3H), 0.89-0.80 (m, 9H), 0.07-0.04 (m, 6H).

Step 3: (S)-1-((tert-butyldimethylsilyl)oxy)pent-4-ene-2-sulfonamide and (R)-1-((tert-butyldimethylsilyl)oxy)pent-4-ene-2-sulfonamide

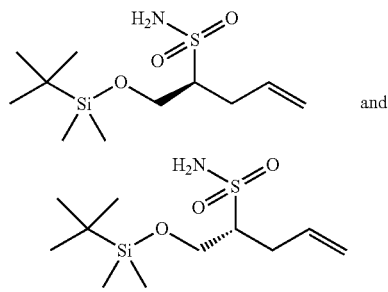

To a mixture of (S)-((2-(benzylthio)pent-4-en-1-yl)oxy)(tert-butyl)dimethylsilane and (R)-((2-(benzylthio)pent-4-en-1-yl)oxy)(tert-butyl)dimethylsilane (0.300 g, 0.93 mmol) and iodosylbenzene (0.675 g, 3.07 mmol) in diethyl ether (80 mL) was added hydrochloric acid (6.82 mL, 82 mmol) gradually with vigorously stirring. The resulting mixture was stirred for 1h. The reaction mixture was settled and layers separated. The organic layer was washed with water and dried over sodium sulfate, concentrated under reduced pressure and dried in vacuo for 1h. The residue obtained above was dissolved in 5 mL of DCM and added slowly into a solution of ammonium hydroxide (12.9 mL, 93 mmol) at 0° C. The resulting mixture was stirred at 0° C. to room temperature for 2h. The layers were separated. The aqueous layer was extracted with DCM (3×), and the combined organic solution was dried over sodium sulfate, filtered and concentrated. The residue was purified by chromatography on silica gel eluting with 0% to 60% EtOAc in hexane to provide the title compounds (0.114 g, 43.9%). m/z (ESI, +ve ion) 280.2 (M+H)$^+$.

Step 4: (S)—N—(((S)-1-((tert-butyldimethylsilyl)oxy)pent-4-en-2-yl)sulfonyl)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide and (S)—N—(((R)-1-((tert-butyldimethylsilyl)oxy)pent-4-en-2-yl)sulfonyl)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide

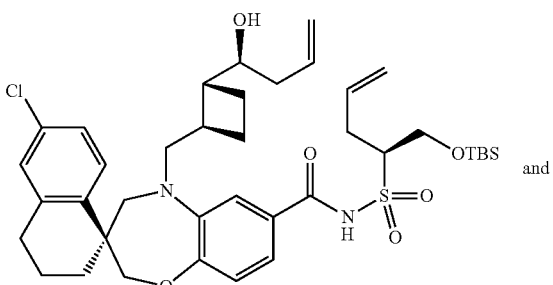

1505

-continued

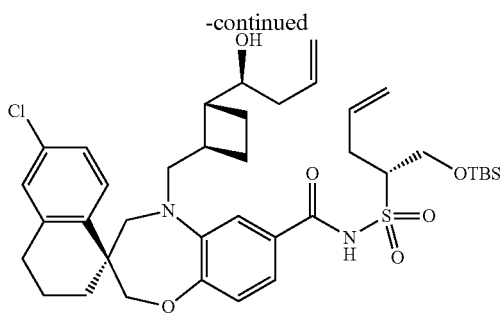

A mixture of (S)-6'-chloro-5-(((1R,2R)-2-((S)-1-hydroxy-but-3-en-1-yl)cyclobutyl) methyl)-3',4,4',5-tetrahydro-2H,2'H-spiro[benzo[b][1,4]oxazepine-3,1'-naphthalene]-7-carboxylic acid (0.060 g, 0.124 mmol, Intermediate AA13A), (S)-1-((tert-butyldimethylsilyl) oxy)pent-4-ene-2-sulfonamide and (R)-1-((tert-butyldimethylsilyl)oxy)pent-4-ene-2-sulfonamide (0.052 g, 0.187 mmol), N,N-dimethylpyridin-4-amine (0.046 g, 0.373 mmol) and N1-((ethylimino)methylene)-N3,N3-dimethylpropane-1,3-diamine hydrochloride (0.048 g, 0.249 mmol) in 3 mL of DCE was stirred at room temperature for 16h. The solvent was removed under reduced pressure, and residue was purified by chromatography on silica gel eluting with 0% to 50% EtOAc (containing 0.2% AcOH) in hexane to provide the title compounds (0.081 g. 88%). m/z (ESI, +ve ion) 743.3 (M+H)+.

Step 5: (1S,3'R,6'R,7'S,9'Z,12'S)-6-chloro-12'-(((dimethyl(2-methyl-2-propanyl)silyl)oxy)methyl)-7'-hydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa[9,16,18,24]tetraen]-15'-one 13',13'-dioxide and (1S,3'R,6'R,7'S,9'Z,12'R)-6-chloro-12'-(((dimethyl(2-methyl-2-propanyl) silyl)oxy)methyl)-7'-hydroxy-3,4-dihydro-2H,15'H-spiro [naphthalene-1,22'-[20]oxa[13]thia[1,14] diazatetracyclo[14.7.2.0$^{3,6}$.0$^{19,24}$]pentacosa [9,16,18,24]tetraen]-15'-one 13',13'-dioxide and (1S,3'R,6'R,7'S,9'E,12'S)-6-chloro-12'-(((dimethyl(2-methyl-2-propanyl)silyl)oxy)methyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9'E,12'R)-6-chloro-12'-(((dimethyl(2-methyl-2-propanyl)silyl)oxy)methyl)-7'-hydroxy-3,4-dihydro-2H,15'H-spiro [naphthalene-1,22'-[20]oxa [13]thia[1,14]diazatetracyclo[14.7.2.0$^{3,6}$.0$^{19,24}$]pentacosa[9,16,18,24]tetraen]-15'-one 13',13'-dioxide

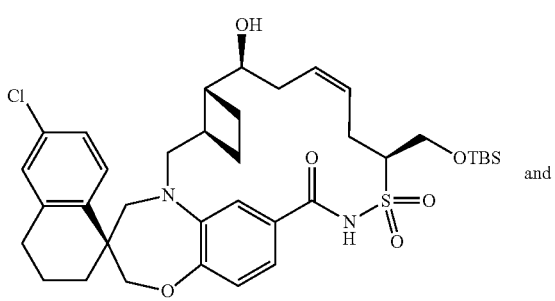

1506

-continued

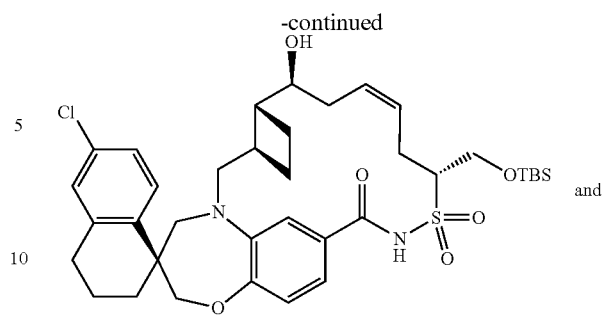
and

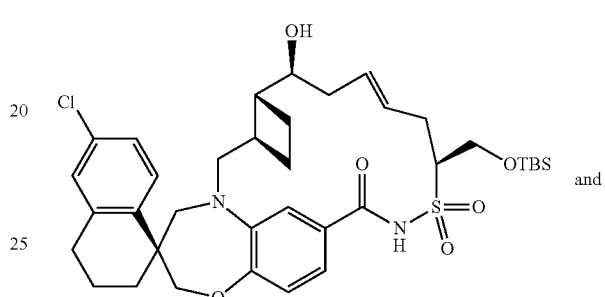
and

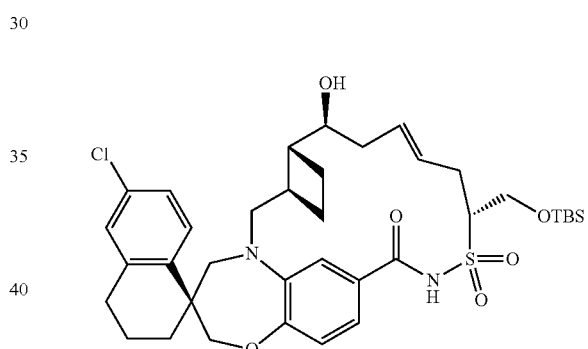

A solution of (S)—N—(((S)-1-((tert-butyldimethylsilyl)oxy)pent-4-en-2-yl)sulfonyl)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide and (S)—N—(((R)-1-((tert-butyldimethylsilyl)oxy)pent-4-en-2-yl)sulfonyl)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide (0.081 g, 0.109 mmol) in toluene (150 mL) was subjected to three cycles of evacuation/back-filling with nitrogen. To the homogeneous solution was added a solution of Hoveyda-Grubbs catalyst (2nd generation) (0.014 g, 0.022 mmol) in 1 mL of toluene at room temperature. The reaction mixture was stirred at 106° C. under nitrogen for 2h. The reaction mixture was cooled to room temperature, and air was blown into mixture for 5 min. The mixture was concentrated and the residue was purified by chromatography on silica gel eluting with 0% to 45% EtOAc in hexane to provide the title compounds (0.067 g, 85.9%). m/z (ESI, +ve ion) 715.3 (M+H)+.

1507

Step 6: (1S,3'R,6'R,7'S,9'Z,12'S)-6-chloro-7'-hydroxy-12'-(hydroxymethyl)-3,4-dihydro-2H,15'H-spiro[naphthalene-1,22' [20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9'Z,12'R)-6-chloro-7'-hydroxy-12'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide and (1S,3'R,6'R,7'S,9'E,12'S)-6-chloro-7'-hydroxy-12'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide and (1S,3'R,6'R,7'S,9'E,12'R)-6-chloro-7'-hydroxy-12'-(hydroxymethyl)-3,4-dihydro-2H,15'H-spiro[naphthalene-1,22'-[20]oxa[13]thia[1,14]diazatetracyclo [14.7.2.0$^{3,6}$.0$^{19,24}$]pentacosa[9,16,18,24]tetraen]-15'-one 13',13'-dioxide

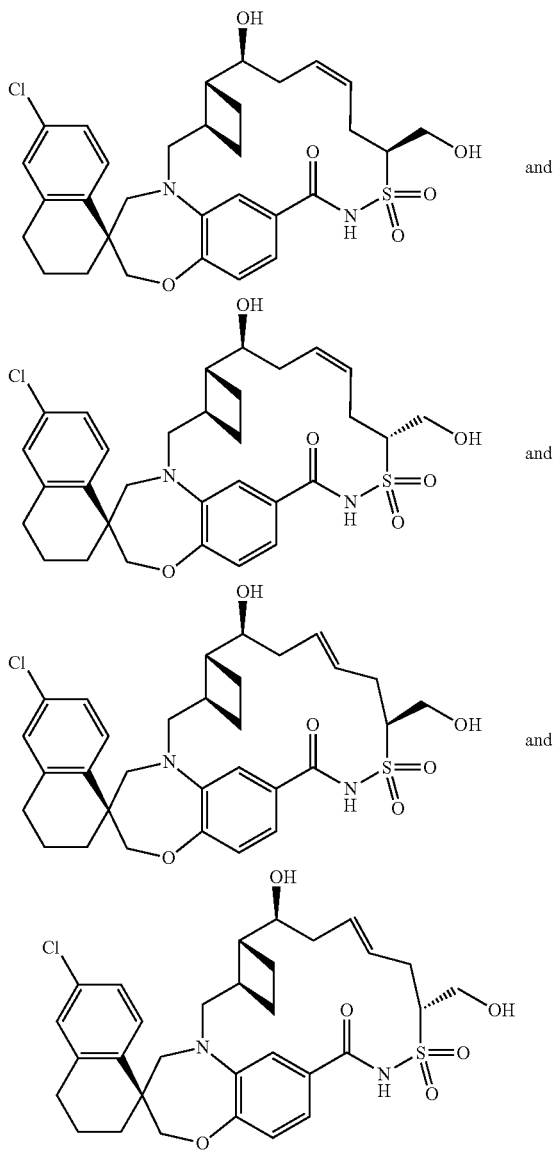

1508

A mixture of (1S,3'R,6'R,7'S,9'Z,12'S)-6-chloro-12'-(((dimethyl(2-methyl-2-propanyl)silyl)oxy)methyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9'Z,12'R)-6-chloro-12'-(((dimethyl(2-methyl-2-propanyl)silyl)oxy)methyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9'E,12'S)-6-chloro-12'-(((dimethyl(2-methyl-2-propanyl)silyl)oxy)methyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9'E,12'R)-6-chloro-12'-(((dimethyl(2-methyl-2-propanyl)silyl)oxy)methyl)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide from Step 5 (0.027 g, 0.038 mmol) and tetrabutylammonium fluoride, 1.0 M in THF (0.075 ml, 0.075 mmol) in 2 mL of THF was stirred at room temperature for 48h. The solvent was removed and residue was dissolved in 8 mL of DCM and washed with water. The solvent was removed and residue was purified by reversed phase preparatory HPLC (Gemini™ Prep C18 5 µm column; Phenomenex, Torrance, CA; gradient elution of 40% to 90% MeCN in water, where both solvents contained 0.1% TFA, 30 min method) to provide the title compounds. m/z (ESI, +ve ion) 601.2 (M+H)$^+$.

Step 7: (1S,3'R,6'R,7'S,12'S)-6-chloro-7'-hydroxy-12'-(hydroxymethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[16,18,24]trien]-15'-one 13',13'-dioxide or (1S,3'R,6'R,7'S,12'R)-6-chloro-7'-hydroxy-12'-(hydroxymethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[16,18,24]trien]-15'-one 13',13'-dioxide A mixture of (1S,3'R,6'R,7'S,9'Z,12'S)-6-chloro-7'-hydroxy-12'-(hydroxymethyl)-3,4-dihydro-2H,15'H-spiro[naphthalene-1,22' [20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9'Z,12'R)-6-chloro-7'-hydroxy-12'-(hydroxymethyl)-3,4-dihydro-2H,15'H-spiro[naphthalene-1,22'-[20]oxa[13]thia [1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9'E,12'S)-6-chloro-7'-hydroxy-12'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide and (1S,3'R,6'R,7'S,9'E,12'R)-6-chloro-7'-hydroxy-12'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide from Step 6 (4.2 mg, 6.99 µmol) and platinum (iv) oxide (0.317 mg, 1.40 µmol) in ethyl acetate (0.5 mL) was stirred under hydrogen balloon at room temperature for 1h. The solid catalyst was filtered off through syringe filter, and filtrate was concentrated and the residue was purified by reversed phase preparatory HPLC (Gemini™ Prep C18 5 µm column; Phenomenex, Torrance, CA; gradient elution of 40% to 90% MeCN in water, where both solvents contained 0.1% TFA, 30 min method) to provide the first eluting isomer as one of the title compounds. $^1$H NMR (500 MHz, CDCl$_3$) δ 7.69 (d, J=8.56 Hz, 1H), 7.24-7.14 (m, 3H), 7.09 (d, J=2.20 Hz, 1H), 7.00-6.90 (m, 1H), 4.25-4.16 (m, 1H), 4.16-4.04 (m, 4H), 3.82-3.62 (m, 3H), 3.62-3.57 (m, 1H), 3.53 (dd, J=15.16, 6.11 Hz, 1H), 3.27 (d, J=14.43 Hz, 1H), 3.24-3.14 (m, 1H), 2.85-2.70 (m, 3H), 2.49-2.38 (m, 1H), 2.26-2.13 (m, 1H), 2.06-1.87 (m, 2H), 1.87-1.76 (m, 2H), 1.75-1.58 (m, 4H), 1.57-1.41 (m, 5H), 1.40-1.30 (m, 3H). m/z (ESI, +ve ion) 603.2 (M+H)$^+$.

Example 713. (1S,3'R,6'R,7'S,12'R)-6-chloro-7'-hydroxy-12'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S,12'S)-6-chloro-7'-hydroxy-12'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide Example 714. (1S,3'R,6'R,7'S,8'E,11'S,12'R)-6-chloro-7',11'-dimethoxy-12'-methyl-3,4-dihydro-2H,15'H-spiro[naphthalene-1,22'-[20]oxa[13]thia [1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7',11'-dimethoxy-12'-methyl-3,4-dihydro-2H,15'H-spiro[naphthalene-1,22'-[20]oxa[13]thia [1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7',11'-dimethoxy-12'-methyl-3,4-dihydro-2H,15'H-spiro[naphthalene-1,22'-[20]oxa[13]thia [1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

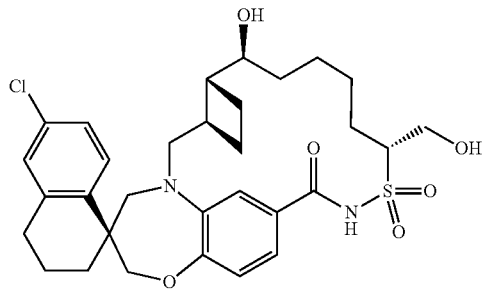

or

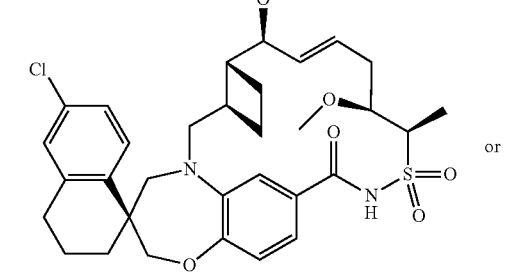

or

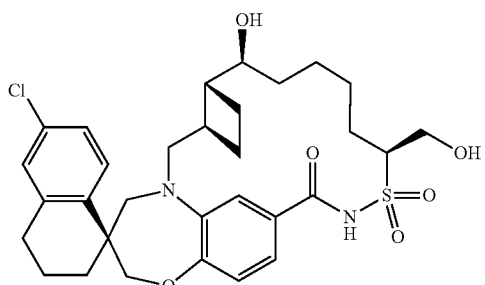

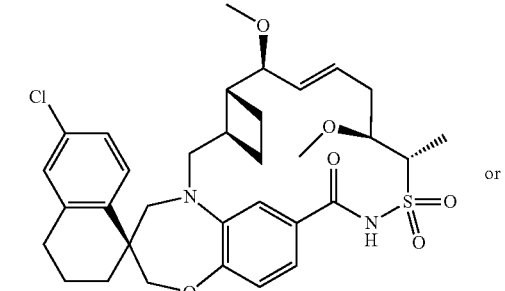

or

The second eluting isomer obtained from the reversed phase preparatory HPLC separation in Example 712, Step 7 is another of the title compounds. $^1$H NMR (500 MHz, CDCl$_3$) δ 7.71 (d, J=8.56 Hz, 1H), 7.45 (d, J=1.96 Hz, 1H), 7.30 (dd, J=8.19, 2.08 Hz, 1H), 7.18 (dd, J=8.44, 2.32 Hz, 1H), 7.10 (d, J=2.20 Hz, 1H), 6.97 (d, J=8.31 Hz, 1H), 4.54 (quin, J=6.17 Hz, 1H), 4.17-4.08 (m, 4H), 3.89 (dd, J=15.16, 5.87 Hz, 2H), 3.66-3.57 (m, 3H), 3.22 (d, J=14.43 Hz, 1H), 3.16-3.08 (m, 1H), 2.80-2.74 (m, 2H), 2.34-2.24 (m, 1H), 2.04-1.96 (m, 2H), 1.95-1.88 (m, 2H), 1.87-1.78 (m, 5H), 1.69-1.61 (m, 5H), 1.49-1.39 (m, 4H). m/z (ESI, +ve ion) 603.2 (M+H)$^+$.

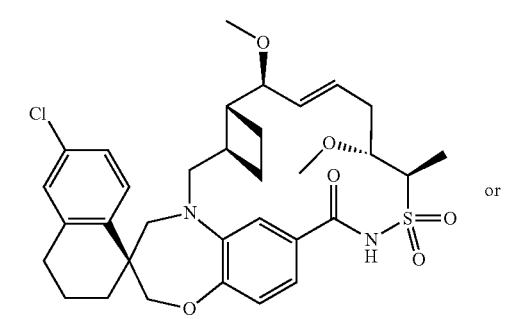

-continued

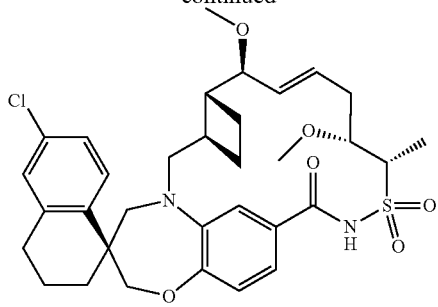

Step 1: (R)-methyl 2-(N,N-bis(4-methoxybenzyl)sulfamoyl)propanoate and (S)-methyl 2-(N,N-bis(4-methoxybenzyl)sulfamoyl)propanoate

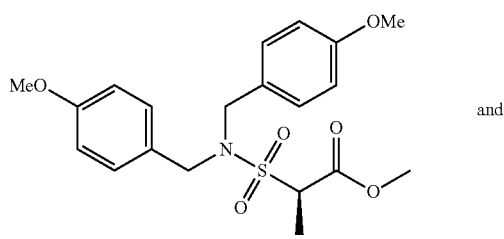

To a mixture of bis(4-methoxybenzyl)amine (8.96 g, 34.8 mmol, Intermediate EE11), 4-(dimethylamino) pyridine (0.327 g, 2.68 mmol) and triethylamine (11.2 mL, 80 mmol) in DCM (100 mL) at 0° C. was added methyl 2-(chlorosulfonyl)propanoate (5 g, 26.8 mmol) slowly over 30 min. The reaction mixture was stirred at room temperature for 16h. The reaction mixture was diluted with 300 mL of DCM and 100 mL of 0.5 N hydrochloric acid aqueous solutions. The layers were separated, and the aqueous layer was extracted with EtOAc (2×100 mL). The combined organic solution was dried over sodium sulfate, filtered, concentrated. The crude product was purified by chromatography on silica gel eluting with 0% to 70% EtOAc in hexane to provide the title compounds (9.14 g, 84%). m/z (ESI, +ve ion) 430.1 (M+Na)⁺.

Step 2: (R)-1-hydroxy-N,N-bis(4-methoxybenzyl)propane-2-sulfonamide and (S)-1-hydroxy-N,N-bis(4-methoxybenzyl)propane-2-sulfonamide

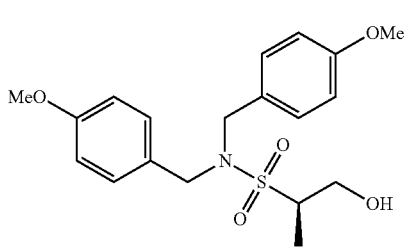

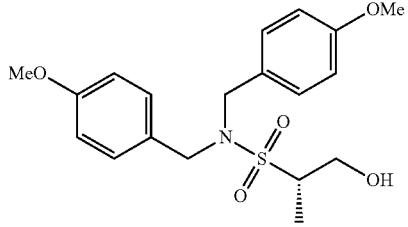

To a solution of (R)-methyl 2-(N,N-bis(4-methoxybenzyl)sulfamoyl)propanoate and (S)-methyl 2-(N,N-bis(4-methoxybenzyl)sulfamoyl)propanoate (4.57 g, 11.2 mmol) in THF (25 ml) at 0° C. was added lithium borohydride (0.734 ml, 22.4 mmol) with a few drops of water. The reaction mixture was stirred at 0° C. to room temperature for 16h. The reaction mixture was diluted with 50 mL of 0.5 N hydrochloric acid aqueous solution and 100 mL of EtOAc. The layers were separated and the aqueous layer was extracted with EtOAc (2×80 mL). The combined organic solution was dried over sodium sulfate, filtered, concentrated. The crude product was used in the next step without further purification. m/z (ESI, +ve ion) 402.1 (M+Na)⁺.

Step 3: (R)—N,N-bis(4-methoxybenzyl)-1-oxopropane-2-sulfonamide and (S)—N,N-bis(4-methoxybenzyl)-1-oxopropane-2-sulfonamide

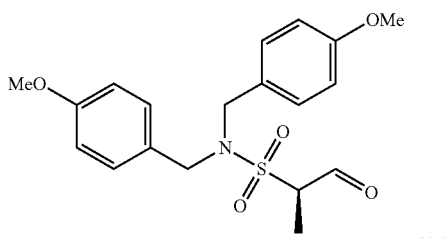

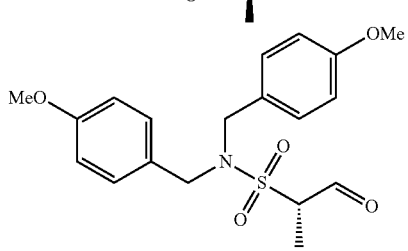

To a solution of (R)-1-hydroxy-N,N-bis(4-methoxybenzyl)propane-2-sulfonamide and (S)-1-hydroxy-N,N-bis(4-methoxybenzyl)propane-2-sulfonamide (4.26 g, 11.2 mmol) in DCM (112 mL) was added dess-martin periodinane (7.14 g, 16.8 mmol) slowly. The reaction mixture was stirred at room temperature for 3h. The reaction mixture was loaded in a column for purification by chromatography on silica gel eluting with 20% to 60% EtOAc in hexane to provide the title compounds (2.85 g, 67.3%). ¹H NMR (400 MHz, CDCl₃) δ 9.83-9.70 (m, 1H), 7.22-7.18 (m, 4H), 6.92-6.88 (m, 4H), 4.33 (d, J=1.96 Hz, 4H), 4.30-4.21 (m, 1H), 3.84 (s, 6H), 1.50 (d, J=6.85 Hz, 3H).

Step 4: (2R,3S)-3-hydroxy-N,N-bis(4-methoxybenzyl)hex-5-ene-2-sulfonamide and (2S,3S)-3-hydroxy-N,N-bis(4-methoxybenzyl)hex-5-ene-2-sulfonamide and (2R,3R)-3-hydroxy-N,N-bis(4-methoxybenzyl)hex-5-ene-2-sulfonamide and (2S,3R)-3-hydroxy-N,N-bis(4-methoxybenzyl)hex-5-ene-2-sulfonamide

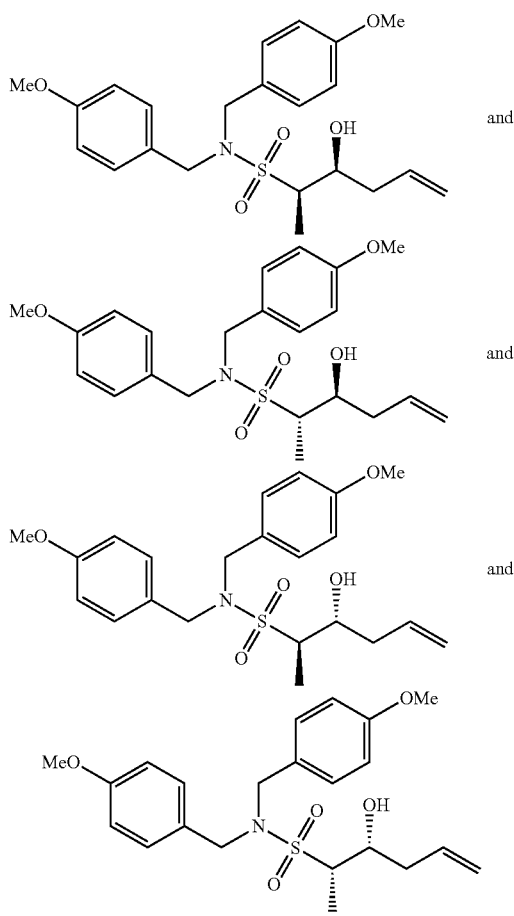

To a mixture of (R)—N,N-bis(4-methoxybenzyl)-1-oxopropane-2-sulfonamide and (S)—N,N-bis(4-methoxybenzyl)-1-oxopropane-2-sulfonamide (2.85 g, 7.55 mmol) and allyl iodide (2.78 ml, 30.2 mmol) in DMF (76 ml) was added indium (0.475 mL, 30.2 mmol). The reaction mixture was stirred at room temperature for 1h. The solid was filtered off, and filtrate was diluted with EtOAc (200 mL) and washed with a 100 mL of mixture of water/saturated sodium bicarbonate/brine (2:1:1), water and brine, dried over sodium sulfate, filtered, concentrated. The crude product was purified by chromatography on silica gel eluting with 0%-60% EtOAc in hexane to provide the title compounds (2.54 g, 80%). ¹H NMR (400 MHz, CDCl₃) δ 7.24-7.14 (m, 4H), 6.91-6.82 (m, 4H), 5.97-5.55 (m, 1H), 5.21-5.05 (m, 2H), 4.50-4.09 (m, 5H), 3.84-3.78 (m, 6H), 3.15-2.89 (m, 2H), 2.58-1.99 (m, 2H), 1.31-1.21 (m, 3H).

Step 5: (2R,3S)-3-hydroxyhex-5-ene-2-sulfonamide and (2S,3S)-3 hydroxyhex-5-ene-2-sulfonamide and (2R,3R)-3-hydroxyhex-5-ene-2-sulfonamide and (2S,3R)-3-hydroxyhex-5-ene-2-sulfonamide

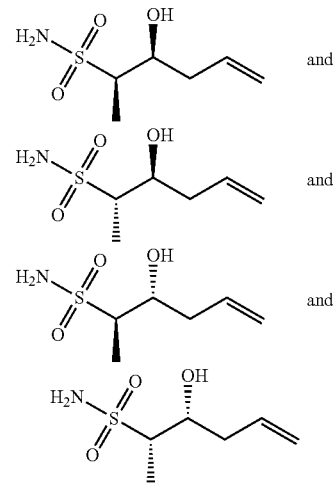

To a mixture of (2R,3S)-3-hydroxy-N,N-bis(4-methoxybenzyl)hex-5-ene-2-sulfonamide and (2S,3S)-3-hydroxy-N,N-bis(4-methoxybenzyl)hex-5-ene-2-sulfonamide and (2R,3R)-3-hydroxy-N,N-bis(4-methoxybenzyl)hex-5-ene-2-sulfonamide and (2S,3R)-3-hydroxy-N,N-bis(4-methoxybenzyl)hex-5-ene-2-sulfonamide (2.54 g, 6.05 mmol) and anisole (6.58 mL, 60.5 mmol) in DCM (30.3 mL) was added trifluoroacetic acid (18 ml, 242 mmol) slowly. The reaction mixture was stirred at room temperature for 16h. The reaction mixture was concentrated under reduced pressure. The residue was dissolved in EtOAc (100 mL) and saturated sodium bicarbonate solution. The layers were separated. The aqueous layer was extracted with IPA/DCM (1:3) (2×70 mL). The organic solution was dried over sodium sulfate and concentrated. The crude product was purified by chromatography on silica gel eluting with 10% to 100% EtOAc in hexane to provide the title compounds (0.818 g, 75%). m/z (ESI, +ve ion) 202.1 (M+Na)⁺.

Step 6: (2R,3S)-3-((tert-butyldimethylsilyl)oxy)hex-5-ene-2-sulfonamide and (2S,3S)-3-((tert-butyldimethylsilyl)oxy)hex-5-ene-2-sulfonamide and (2R,3R)-3-((tert-butyldimethylsilyl)oxy)hex-5-ene-2-sulfonamide and (2S,3R)-3-((tert-butyldimethylsilyl)oxy)hex-5-ene-2-sulfonamide

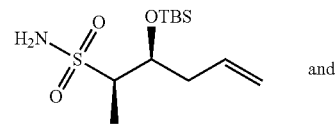

-continued

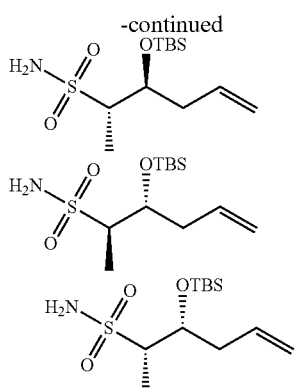

To a solution of (2R,3S)-3-hydroxyhex-5-ene-2-sulfonamide and (2S,3S)-3 hydroxyhex-5-ene-2-sulfonamide and (2R,3R)-3-hydroxyhex-5-ene-2-sulfonamide and (2S,3R)-3-hydroxyhex-5-ene-2-sulfonamide (302 mg, 1.68 mmol) in DCM (12.0 mL) was added tert-butylchlorodimethylsilane (279 mg, 1.85 mmol), followed by imidazole (0.167 mL, 2.53 mmol). The reaction mixture was stirred at room temperature for 16 h. The reaction mixture was concentrated under reduced pressure, and residue was diluted with 1N hydrogen chloride (1 mL) and water (10 mL), extracted with Et$_2$O (2×20 mL). The organic extract was washed with brine, dried over magnesium sulfate, filtered and concentrated under reduced pressure to give the crude title products. The mixture was used in the next step without further purification. m/z (ESI, +ve ion) 294.1 (M+H)$^+$.

Step 7: (S)-6'-chloro-5-(((1R,2R)-2-((S,E)-1-hydroxyhex-2-en-1-yl)cyclobutyl)methyl)-N-(((2R, 3S)-3-hydroxyhex-5-ene-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N-(((2S,3S)-3-hydroxyhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N-(((2R,3R)-3-hydroxyhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N-(((2S,3R)-3-hydroxyhex-5-en-2-yl)sulfonyl)-3',4,4',5-tetrahydro-2H,2'H-spiro[benzo[b][1,4]oxazepine-3,1'-naphthalene]-7-carboxamide

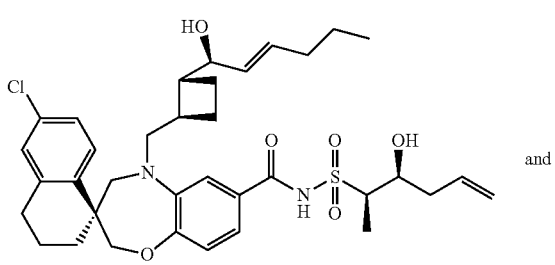

-continued

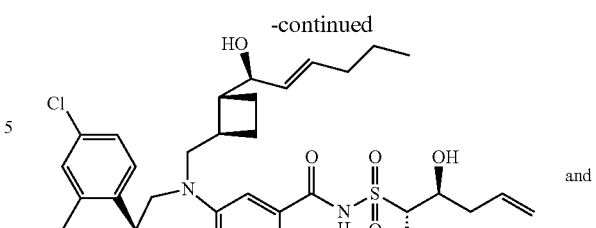

A mixture of (1'S)-6'-chloro-5-(((1R,2R)-2-((E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (150 mg, 0.294 mmol, Intermediate AA12A), (2R,3S)-3-((tert-butyldimethylsilyl)oxy)hex-5-ene-2-sulfonamide and (2S,3S)-3-((tert-butyldimethylsilyl)oxy)hex-5-ene-2-sulfonamide and (2R,3R)-3-((tert-butyldimethylsilyl)oxy)hex-5-ene-2-sulfonamide and (2S,3R)-3-((tert-butyldimethylsilyl)oxy)hex-5-ene-2-sulfonamide (129 mg, 0.441 mmol), 4-(dimethylamino) pyridine (108 mg, 0.882 mmol) and 1-(3-dimethylaminopropyl)-3-ethylcarbodiimide hydrochloride (113 mg, 0.588 mmol) in 4 mL of DCM was stirred at room temperature for 16 h (It was observed that the TBS group was lost during the period of reaction). The solvent was removed under reduced pressure, and residue was purified by chromatography on silica gel eluting with 0% to 60% EtOAc (containing 0.15% AcOH) in hexane to provide the title compounds (0.115 g, 58.3%). m/z (ESI, +ve ion) 671.2 (M+H)$^+$.

Step 8: (1S,3'R,6'R,7'S,8'E,11'S,12'R)-6-chloro-7',11'-dihydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide and (1S,3'R,6'R,7'S,8'E,11'S,12'S)-6-chloro-7',11'-dihydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide and (1S,3'R,6'R,7'S,8'E,11'R,12'R)-6-chloro-7,11'-dihydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide and (1S,3'R,6'R,7'S,8'E,11'R,12'S)-6-chloro-7,11'-dihydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

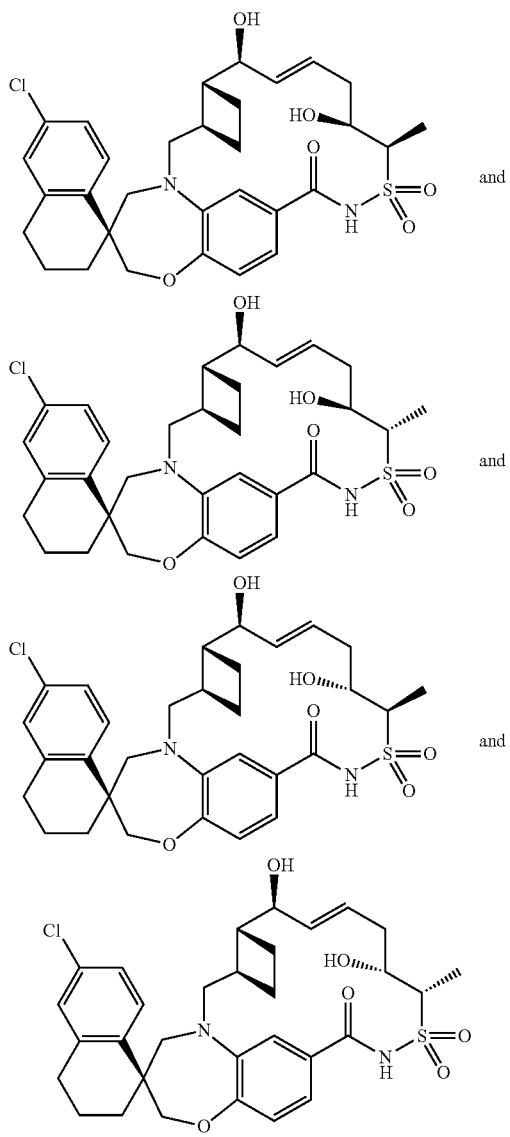

A solution of (S)-6'-chloro-5-(((1R,2R)-2-((S,E)-1-hydroxyhex-2-en-1-yl)cyclobutyl)methyl)-N-(((2R,3S)-3-hydroxyhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N-(((2S,3S)-3-hydroxyhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N-(((2R,3R)-3-hydroxyhex-5-en-2-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S,E)-1-hydroxyhex-2-en-1-yl)cyclobutyl)methyl)-N-(((2S,3R)-3-hydroxyhex-5-en-2-yl)sulfonyl)-3',4,4',5-tetrahydro-2H,2'H-spiro[benzo[b][1,4]oxazepine-3,1'-naphthalene]-7-carboxamide (115 mg, 0.171 mmol) in AcOH (20 mL) was blowed with argon for 10 min, and Hoveyda-Grubbs catalyst (2nd generation) (53.7 mg, 0.086 mmol) was added. The reaction mixture was stirred under reduced pressure at 60° C. for 3h. The solvent was removed under reduced pressure, residue was purified by chromatography on silica gel eluting with 40% to 100% EtOAc (containing 0.3% AcOH) in hexane to provide the title compounds (0.025 g, 24.5%). m/z (ESI, +ve ion) 601.2 (M+H)⁺.

Step 9: (1S,3'R,6'R,7'S,8'E,11'S,12'R)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'S,12'S)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'R,12'R)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'R,12'S)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide To a mixture of (1S,3'R,6'R,7'S,8'E,11'S,12'R)-6-chloro-7',11'-dihydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide and (1S,3'R,6'R,7'S,8'E,11'S,12'S)-6-chloro-7',11'-dihydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide and (1S,3'R,6'R,7'S,8'E,11'R,12'R)-6-chloro-7',11'-dihydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide and (1S,3'R,6'R,7'S,8'E,11'R,12'S)-6-chloro-7',11'-dihydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide from Step 8 (20.1 mg, 0.033 mmol) and methyl iodide (20.8 µl, 0.334 mmol) in THF (1 mL) was added sodium hydride, 60% dispersion in mineral oil (21.1 µl, 1.00 mmol) portionwise. The reaction mixture was stirred at room temperature for 1h. The reaction was quenched with water, mixture was subjected to purification by reversed phase preparatory HPLC (Gemini™ Prep C18 5 μm column; Phenomenex, Torrance, CA; gradient elution of 40% to 90% MeCN in water, where both solvents contained 0.1% TFA, 30 min method) to provide the first eluting isomer as one of the title compounds as a white solid. $^1$H NMR (400 MHz, CDCl$_3$) δ 8.11 (s, 1H), 7.72 (d, J=8.22 Hz, 1H), 7.20 (d, J=8.41 Hz, 1H), 7.12 (s, 1H), 7.01-6.91 (m, 2H), 6.85 (s, 1H), 5.72-5.59 (m, 2H), 4.37 (d, J=6.85 Hz, 1H), 4.12 (s, 2H), 3.91-3.71 (m, 3H), 3.66 (br s, 1H), 3.55-3.35 (m, 4H), 3.31-3.20 (m, 3H), 3.09-2.97 (m, 1H), 2.87-2.74 (m, 2H), 2.63-2.25 (m, 4H), 2.19-1.94 (m, 3H), 1.92-1.67 (m, 3H), 1.63 (d, J=7.24 Hz, 3H), 1.50-1.31 (m, 2H). m/z (ESI, +ve ion) 629.2 (M+H)$^+$.

Example 715. (1S,3'R,6'R,7'S,8'E,11'S,12'S)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'R)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'R,12'S)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,11'S,12'R)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

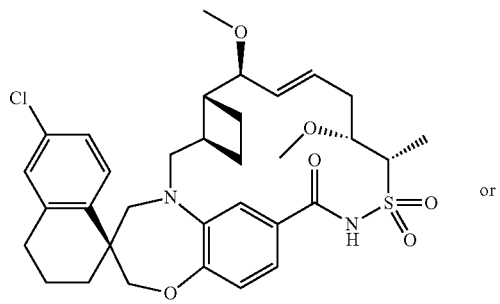

or

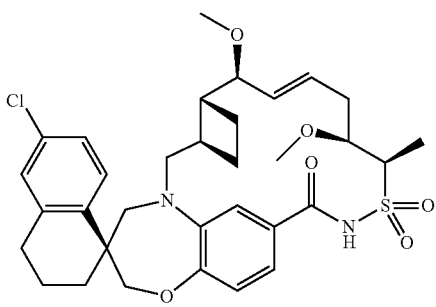

or

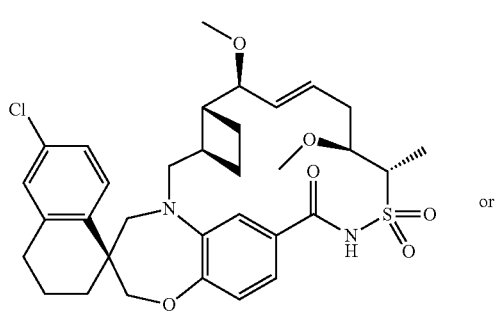

or

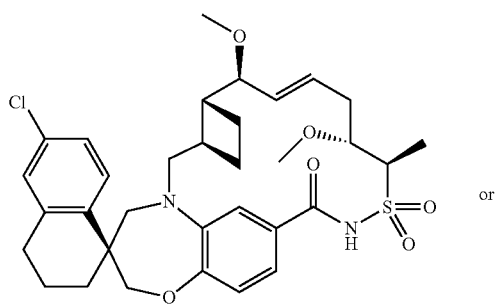

The second eluting isomer obtained as a white solid from the reversed phase preparatory HPLC separation in Example 714, Step 9 is another of the title compounds. $^1$H NMR (400 MHz, CDCl$_3$) δ 7.71-7.63 (m, 1H), 7.18 (dt, J=2.64, 5.62 Hz, 1H), 7.12-7.00 (m, 2H), 6.98-6.85 (m, 2H), 5.77 (br s, 1H), 5.54 (dd, J=7.34, 15.36 Hz, 1H), 4.26-4.19 (m, 1H), 4.16-4.03 (m, 2H), 3.93 (d, J=14.48 Hz, 1H), 3.88-3.83 (m, 1H), 3.78-3.65 (m, 2H), 3.58-3.44 (m, 3H), 3.44-3.34 (m, 3H), 3.34-3.23 (m, 3H), 2.93 (br s, 1H), 2.78 (m, 2H), 2.74-2.70 (m, 1H), 2.62 (d, J=7.43 Hz, 1H), 2.46-2.33 (m, 2H), 2.26-1.56 (m, 5H), 1.62-1.53 (m, 3H), 1.53-1.43 (m, 2H). m/z (ESI, +ve ion) 629.2 (M+H)$^+$.

Example 716. (1S,3'R,6'R,7'S,8'E,11'R,12'R)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

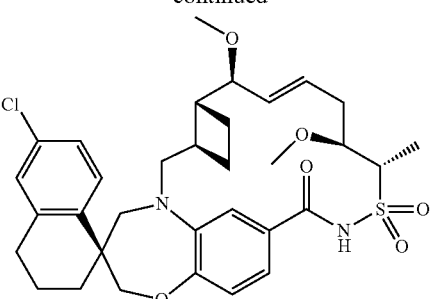

The third eluting isomer obtained as a white solid from the reversed phase preparatory HPLC separation in Example 714, Step 9 is another of the title compounds. $^1$H NMR (400 MHz, CDCl$_3$) δ 7.72 (d, J=8.41 Hz, 1H), 7.25 (br s, 1H), 7.19 (dd, J=2.45, 8.31 Hz, 1H), 7.10 (s, 1H), 6.96 (d, J=8.22 Hz, 1H), 6.77 (d, J=1.96 Hz, 1H), 5.78 (dd, J=5.09, 10.17 Hz, 1H), 5.51 (t, J=10.17 Hz, 1H), 4.24 (t, J=7.04 Hz, 1H), 4.14-4.04 (m, 2H), 3.88-3.73 (m, 3H), 3.43-3.32 (m, 2H), 3.31-3.22 (m, 3H), 3.22-3.14 (m, 3H), 2.91 (br s, 1H), 2.79 (d, J=5.48 Hz, 2H), 2.75-2.69 (m, 1H), 2.57-2.47 (m, 1H), 2.41-2.27 (m, 3H), 2.23-1.64 (m, 5H), 1.62-1.52 (m, 4H), 1.49-1.27 (m, 2H). m/z (ESI, +ve ion) 629.2 (M+H)$^+$.

Example 717. (1S,3'R,6'R,7'S,8'E,11'R,12'S)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'R)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7',11'-dimethoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

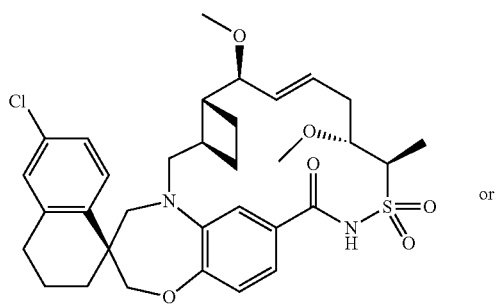

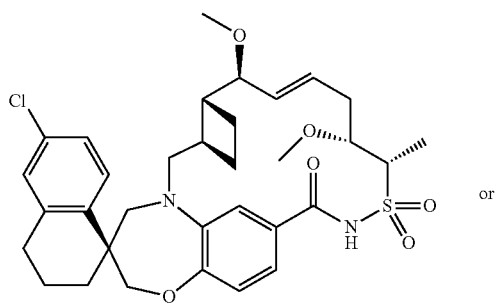

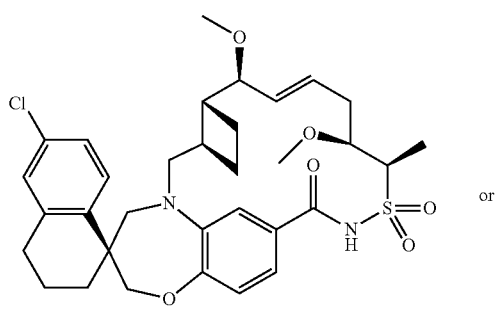

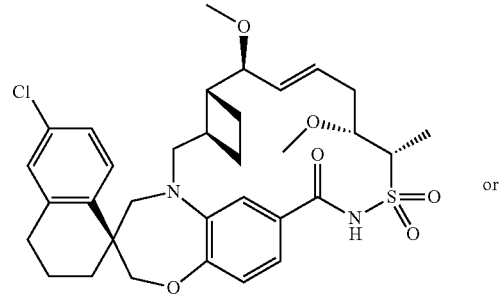

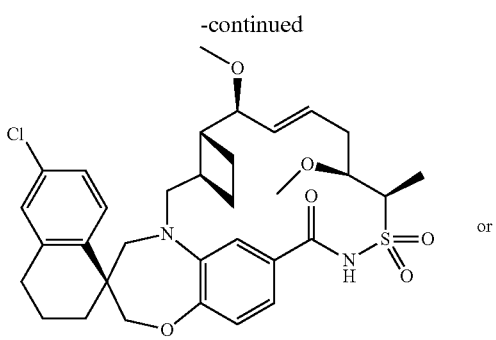


The fourth eluting isomer obtained as a white solid from the reversed phase preparatory HPLC separation in Example 714, Step 9 is another of the title compounds. $^1$H NMR (500 MHz, CDCl$_3$) δ 8.34-8.06 (m, 1H), 7.72 (d, J=8.56 Hz, 1H), 7.41 (dd, J=2.08, 8.19 Hz, 1H), 7.23-7.14 (m, 1H), 7.10 (d, J=2.20 Hz, 1H), 7.00 (d, J=8.31 Hz, 1H), 6.96-6.88 (m, 1H), 6.02-5.91 (m, 1H), 5.51 (dd, J=5.62, 10.76 Hz, 1H), 5.38-5.33 (m, 1H), 4.37 (m, 1H), 4.17-4.05 (m, 3H), 3.89-3.84 (m, 1H), 3.83-3.70 (m, 2H), 3.46-3.33 (m, 3H), 3.32-3.16 (m, 4H), 2.94 (dd, J=8.44, 15.04 Hz, 1H), 2.82-2.70 (m, 3H), 2.57-2.49 (m, 1H), 2.32-1.85 (m, 4H), 1.78-1.57 (m, 2H), 1.56-1.51 (m, 3H), 1.49-1.29 (m, 3H). m/z (ESI, +ve ion) 629.2 (M+H)$^+$.

Example 718. (1S,3'R,6'R,7'S,8'E,11'S,12'R)-6-chloro-11'-hydroxy-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-11'-hydroxy-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-11'-hydroxy-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'S)-6-chloro-11'-hydroxy-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

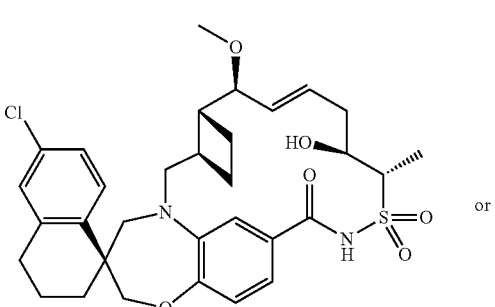

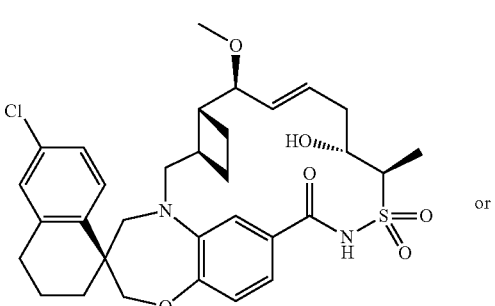

1525

-continued

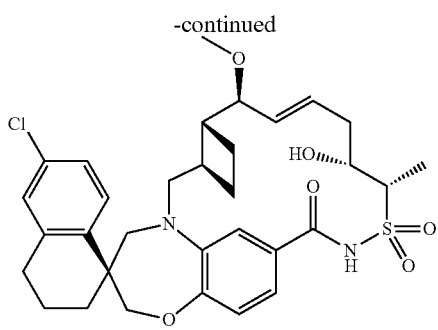

Step 1: (S)-6'-chloro-5-(((1R,2R)-2-((S,E)-1-methoxyhex-2-en-1-yl)cyclobutyl)methyl)-3',4,4',5-tetrahydro-2H,2'H-spiro[benzo[b][1,4]oxazepine-3,1'-naphthalene]-7-carboxylic Acid

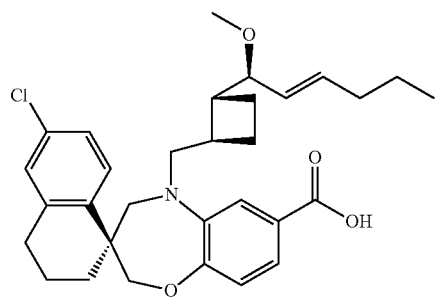 [SMILES: CCC/C=C/[C@H](OC)[C@@H]1CC[C@H]1CN1C[C@@]2(CCCc3cc(Cl)ccc32)COc2ccc(C(=O)O)cc21]

To a suspension of sodium hydride, 60% dispersion in mineral oil (6.2 µl, 0.294 mmol) in 0.5 mL of THF was added a solution of (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (50 mg, 0.098 mmol, Intermediate AA12A) in 2 mL of THF slowly. The reaction mixture was stirred at room temperature for 40 min, and then methyl iodide (12.18 µl, 0.196 mmol) was added. The mixture was stirred for 3h. The reaction was quenched with saturated ammonium chloride aqueous solution, and then 30 mL of EtOAc was added. The organic layer was separated, and dried over sodium sulfate, filtered and concentrated. The crude product was purified by chromatography on silica gel eluting with 0% to 60% EtOAc in hexane to provide the title product (47.3 mg, 92%). m/z (ESI, +ve ion) 524.2 (M+H)⁺.

1526

Step 2: (S)-6'-chloro-N-(((2R,3S)-3-hydroxyhex-5-en-2-yl)sulfonyl)-5-(((1R,2R)-2-((S,E)-1-methoxyhex-2-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N-(((2S,3S)-3-hydroxyhex-5-en-2-yl)sulfonyl)-5-(((1R,2R)-2-((S,E)-1-methoxyhex-2-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N-(((2R,3R)-3-hydroxyhex-5-en-2-yl)sulfonyl)-5-(((1R,2R)-2-((S,E)-1-methoxyhex-2-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N-(((2S,3R)-3-hydroxyhex-5-en-2-yl)sulfonyl)-5-(((1R,2R)-2-((S,E)-1-methoxyhex-2-en-1-yl)cyclobutyl)methyl)-3',4,4',5-tetrahydro-2H,2'H-spiro[benzo[b][1,4]oxazepine-3,1'-naphthalene]-7-carboxamide

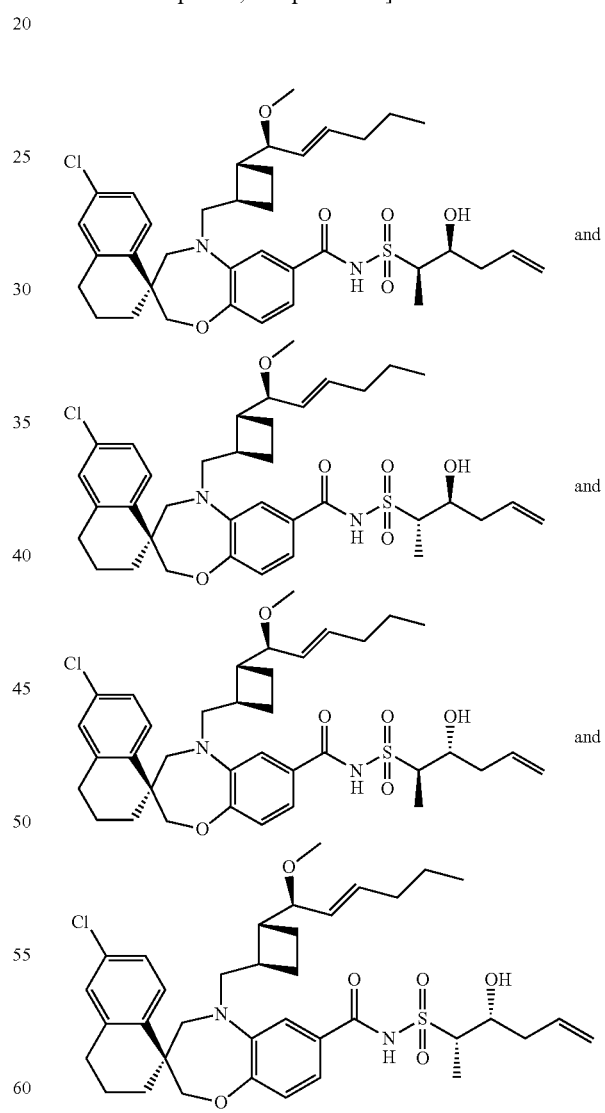

To a mixture of (S)-6'-chloro-5-(((1R,2R)-2-((S,E)-1-methoxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (82 mg, 0.156 mmol), (2R,3S)-3-hydroxyhex-5-ene-2-sulfonamide and (2S,3S)-3 hydroxyhex-5-ene-2-sulfonamide and (2R,3R)-3-hydroxyhex-5-ene-2-sulfonamide and (2S,3R)-3-hydroxyhex-5-ene-2-sulfonamide (33.7 mg, 0.188 mmol, Example 720, Step 5) in DCM (6 mL) at 0° C. was added N,N-dimethylpyridin-4-amine (57.3 mg, 0.469 mmol), followed by N1-((ethylimino)methylene)-N3,N3-dimethylpropane-1,3-diamine hydrochloride (90 mg, 0.469 mmol) in 2 ml of DCM dropwise. The ice-bath was removed and reaction mixture was stirred at room temperature for 5h. The solvent was removed under reduced pressure, and crude product was purified by chromatography on silica gel eluting with 0% to 80% EtOAc (containing 0.3% AcOH) in hexane to provide the title compounds (73.2 mg, 68.3%). m/z (ESI, +ve ion) 685.3 (M+H)+.

Step 3: (1S,3'R,6'R,7'S,8'E,11'S,12'R)-6-chloro-11'-hydroxy-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'5,12'S)-6-chloro-11'-hydroxy-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-11'-hydroxy-7'-methoxy-12'-methyl-3,4-dihydro-2H,15'H-spiro[naphthalene-1,22'-[20]oxa[13]thia[1,14]diazatetra cyclo[14.7.2.0$^{3,6}$.0$^{19,24}$]pentacosa[8,16,18,24]tetraen]-15'-one 13',13'-dioxide or (1S,3'R,6'R,7'S,8'E,11'S,12'S)-6-chloro-11'-hydroxy-7'-methoxy-12'-methyl-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[8,16,18,24]tetraen]-15'-one 13',13'-dioxide A solution of (S)-6'-chloro-N-(((2R,3S)-3-hydroxyhex-5-en-2-yl)sulfonyl)-5-(((1R,2R)-2-((S,E)-1-methoxyhex-2-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N-(((2S,3S)-3-hydroxyhex-5-en-2-yl)sulfonyl)-5-(((1R,2R)-2-((S,E)-1-methoxyhex-2-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N-(((2R,3R)-3-hydroxyhex-5-en-2-yl)sulfonyl)-5-(((1R,2R)-2-((S,E)-1-methoxyhex-2-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N-(((2S,3R)-3-hydroxyhex-5-en-2-yl)sulfonyl)-5-(((1R,2R)-2-((S,E)-1-methoxyhex-2-en-1-yl)cyclobutyl)methyl)-3',4,4',5-tetrahydro-2H,2'H-spiro[benzo[b][1,4]oxazepine-3,1'-naphthalene]-7-carboxamide from Step 2 (73.2 mg, 0.107 mmol) in 1,2-dichloroethane (12.0 mL) was sparged with argon for 10 min. To this solution was added tetraisopropoxytitanium (9.1 mg, 0.032 mmol), and the mixture was heated at 40° C. for 1h with stirring under argon balloon. (1,3-dimesitylimidazolidin-2-ylidene)(2-isopropoxybenzylidene)ruthenium (VI) chloride (13.4 mg, 0.021 mmol) in 1 mL of DCE was added slowly, and mixture was heated at 55° C. 1 h while 0.2 eq of catalyst in 1 ml of DCE was added dropwise. The reaction mixture was stirred at 50° C. for 16 h. The reaction mixture was cooled to room temperature and bubbled with air for 5 min, and concentrated. The residue was purified by chromatography on silica gel eluting with 0% to 80% EtOAc (containing 0.3% AcOH) in hexane to provide the crude product. Further purification by reversed phase preparatory HPLC (Gemini™ Prep C18 5 µm column; Phenomenex, Torrance, CA; gradient elution of 40% to 90% MeCN in water, where both solvents contained 0.1% TFA, 30 min method) to provide the first eluting isomer as one of the title compounds as a white solid. $^1$H NMR (500 MHz, CDCl$_3$) δ 8.00-8.16 (m, 1H), 7.70 (d, J=8.31 Hz, 1H), 7.24-7.15 (m, 1H), 7.10 (d, J=1.47 Hz, 1H), 6.96-6.85 (m, 2H), 6.77 (s, 1H), 5.70-5.63 (m, 1H), 5.61-5.53 (m, 1H), 4.46 (q, J=7.34 Hz, 1H), 4.12-4.02 (m, 2H), 3.86-3.69 (m, 2H), 3.62 (dd, J=3.42, 8.56 Hz, 1H), 3.30-3.18 (m, 3H), 2.99 (dd, J=10.51, 15.16 Hz, 1H), 2.84-2.71 (m, 2H), 2.51-2.41 (m, 2H), 2.36-2.22 (m, 2H), 2.05-1.93 (m, 3H), 1.83-1.78 (dd, J=9.54, 18.34 Hz, 3H), 1.77-1.64 (m, 2H), 1.63-1.58 (m, 3H), 1.42-1.27 (m, 3H). m/z (ESI, +ve ion) 615.2 (M+H)+.

Example 719. (1S,3'R,6'R,7'S,8'E,11'S,12'R)-6-chloro-7'-(2-methoxyethoxy)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one-13', 13'-dioxide

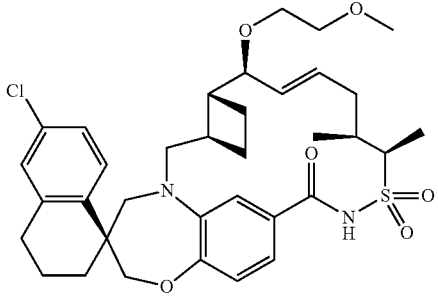

Step 1: (S)-6'-chloro-5-(((1R,2R)-2-((S)-1-hydroxyallyl)cyclobutyl) methyl)-N-(((2R,3S)-3-methylhex-5-en-2-yl)sulfonyl)-3',4,4',5-tetrahydro-2H,2'H-spiro[benzo[b][1,4]oxazepine-3,1'-naphthalene]-7-carboxamide

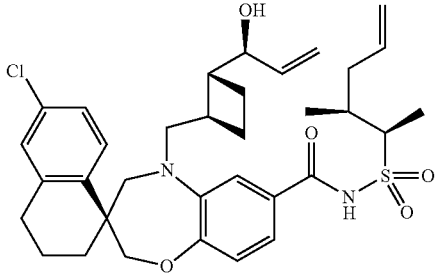

4-dimethylaminopyridine (DMAP) (3.42 g, 28.0 mmol) was added to a solution of (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Intermediate AA11A; 7.7 g, 16.4 mmol) and (2R,3S)-3-methylhex-5-ene-2-sulfonamide (Intermediate EE22; 5.83 g, 32.9 mmol) in DCM (411 ml) cooled to 0° C. EDC hydrochloride (6.31 g, 32.9 mmol) was then added slowly portionwise. The mixture was stirred while allowing to reach ambient temperature overnight. The mixture was then washed with 1N HCl and brine and the aqueous layer was back-extracted with EtOAc. The combined organics were dried over MgSO$_4$, filtered and concentrated. The yellow oily residue was loaded onto a 220 g ISCO Gold column and purified eluting with 0% to 20% EtOAc (containing 0.3% AcOH)/heptanes, to provide (S)-6'-chloro-5-(((1R,2R)-2-((S)-1-hydroxyallyl)cyclobutyl)methyl)-N-(((2R,3S)-3-methylhex-5-en-2-yl)sulfonyl)-3',4',5-tetrahydro-2H,2'H-spiro[benzo[b][1,4]oxazepine-3,1'-naphthalene]-7-carboxamide (7.89 g, 12.6 mmol, 76% yield, 88% pure).

Step 2. (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

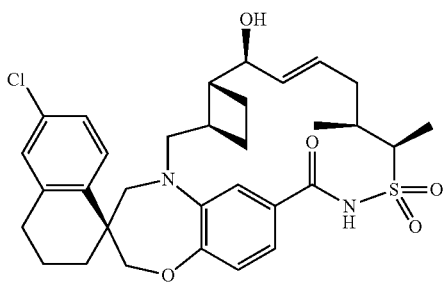

To a 20 L reactor blanketed in argon was charged 14 L of 1,2-dichloroethane (1,2-DCE). (S)-6'-chloro-5-(((1R,2R)-2-((S)-1-hydroxyallyl)cyclobutyl)methyl)-N-(((2R,3S)-3-methylhex-5-en-2-yl)sulfonyl)-3',4',5-tetrahydro-2H,2'H-spiro[benzo[b][1,4]oxazepine-3,1'-naphthalene]-7-carboxamide (18.75 g, 29.9 mmol) was added as a solution in 400 mL 1,2-DCE followed by a 400 mL rinse. The reactor was sealed and purged with argon. (1,3-dimesitylimidazolidin-2-ylidene)(2-isopropoxybenzylidene)ruthenium(VI) chloride ("Grubbs-Hoveyda II", 1.87 g, 2.99 mmol) was added as a solution in 150 mL of 1,2 DCE followed by a 50 mL rinse. The reactor was heated to 60° C. over 1 h with an argon sweep of the headspace and held at temperature for 9 h. The reaction was quenched by the addition of 2-(2-(vinyloxy)ethoxy)ethanol (1.50 g, 11.4 mmol), cooled to ambient temperature, and concentrated to ~200 mL volume by rotary evaporation. The reaction was transferred to a 1 L round-bottomed flask and diluted to 500 mL volume with 1,2-DCE. The reaction was treated with 52 g of Silicycle Si-Thiol (SiliCycle Inc., Quebec City, Quebec CANADA Cat #R51030B) with stirring for 9 h at 40° C., filtered and rinsed with 2×65 mL dichloromethane. The solution was passed through a Whatman GF/F filter cup (GE Healthcare Bio-Sciences Pittsburgh, PA, USA) to afford a transparent yellow solution. The reaction was concentrated to afford a crude product mass of 27.4 g. The residue was slurried in 250 mL isopropyl acetate and evaporated to dryness three times. The reaction was suspended in 270 mL isopropyl acetate, heated to dissolution, allowed to cool to ambient temperature and stirred for 18 h. The solids were filtered and washed with 65 mL isopropyl acetate. The solid was air-dried for 30 minutes then placed under high vacuum for 3 hours to afford 12.6 g of (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (91.7% weight purity). $^1$H NMR (500 MHz, CD$_2$Cl$_2$) δ 8.06 (s, 1H), 7.71 (d, J=8.56 Hz, 1H), 7.17 (dd, J=8.44, 2.32 Hz, 1H), 7.09 (d, J=2.20 Hz, 1H), 6.91 (s, 3H), 5.81 (ddd, J=14.92, 7.82, 4.16 Hz, 1H), 5.71 (dd, J=15.41, 8.31 Hz, 1H), 4.16-4.26 (m, 2H), 3.83 (d, J=14.43 Hz, 1H), 3.69 (d, J=14.43 Hz, 1H), 3.25 (d, J=14.43 Hz, 1H), 3.04 (dd, J=15.28, 9.66 Hz, 1H), 2.68-2.84 (m, 2H), 2.41 (app qd, J=9.80, 3.70 Hz, 1H), 2.25-2.34 (m, 1H), 1.93-2.00 (m, 5H), 1.74-2.11 (m, 9H), 1.62-1.73 (m, 1H), 1.43 (d, J=7.09 Hz, 3H) 1.35-1.42 (m, 1H) 1.03 (d, J=6.60 Hz, 3H). MS (ESI, +ve ion) m/z 599.2 (M+H)$^+$.

Step 3: (1S,3'R,6'R,7'S,8'E,11',12'R)-6-chloro-7'-(2-methoxyethoxy)-11',12'-dimethyl-3,4-dihydro-2H,15'H-spiro[naphthalene-1,22'-[20]oxa[13]thia [1,14]diazatetracyclo[14.7.2.0$^{3,6}$.0$^{19,24}$]pentacosa[8,16,18,24]tetraen]-15'-one-13', 13'-dioxide To a solution of (1S,3'R,6'R,7'S,8'E,11'S,12'R)-6-chloro-7'-hydroxy-11',12'-dimethyl-3,4-dihydro-2H,15'H-spiro [naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (Example 719, Step 2; 100 mg, 0.167 mmol) in DMF (3.34 mL) cooled to 0° C. was added sodium hydride, 60% dispersion in mineral oil (66.8 mg, 1.67 mmol). The reaction mixture was stirred at 0° C. for 15 min, and then 2-bromoethyl methyl ether (Alfa Aesar, 0.078 mL, 0.834 mmol) was added. The reaction mixture was stirred at ambient temperature. After 48 h, the mixture was quenched with aq. NH$_4$Cl and diluted with water, then extracted with EtOAc. The organic layer was dried over MgSO$_4$ and concentrated. The crude material was purified by chromatography through a Redi-Sep pre-packed silica gel column (12 g), eluting with 10-40% EtOAc (containing 0.3% AcOH)/heptanes to provide the title compound (61 mg, 0.093 mmol, 55.6% yield). $^1$H NMR (500 MHz, CD$_2$Cl$_2$) δ 8.02 (s, 1H), 7.70 (d, J=8.6 Hz, 1H), 7.17 (dd, J=2.2, 8.6 Hz, 1H), 7.09 (d, J=2.2 Hz, 1H), 6.91 (s, 2H), 6.86 (s, 1H), 5.79 (ddd, J=3.3, 9.6, 15.2 Hz, 1H), 5.54 (dd, J=9.8, 14.4 Hz, 1H), 4.26 (ddd, J=1.0, 7.3, 14.4 Hz, 1H), 4.12-4.04 (m, 2H), 3.82 (d, J=15.2 Hz, 1H), 3.75 (dd, J=3.3, 9.2 Hz, 1H), 3.69 (d, J=14.7 Hz, 1H), 3.53-3.49 (m, 1H), 3.48-3.41 (m, 2H), 3.39-3.34 (m, 1H), 3.32 (s, 3H), 3.25 (d, J=14.2 Hz, 1H), 3.02 (dd, J=10.3, 15.4 Hz, 1H), 2.83-2.70 (m, 2H), 2.49-2.41 (m, 1H), 2.36-2.28 (m, 1H), 2.21-2.13 (m, 1H), 2.13-2.07 (m, 1H), 2.05 (d, J=13.7 Hz, 1H), 1.99-1.91 (m, 3H), 1.89-1.77 (m, 3H), 1.71-1.59 (m, 1H), 1.44 (d, J=7.3 Hz, 3H), 1.39 (t, J=13.1 Hz, 1H), 1.02 (d, J=6.8 Hz, 3H). MS (ESI, +ve ion) m/z 657.1 (M+H)$^+$.

1531

Example 720. (1S,3'R,6'R,7'S,8'E,11'S,12'R)-6-chloro-11',12'-dimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one-13',13'-dioxide

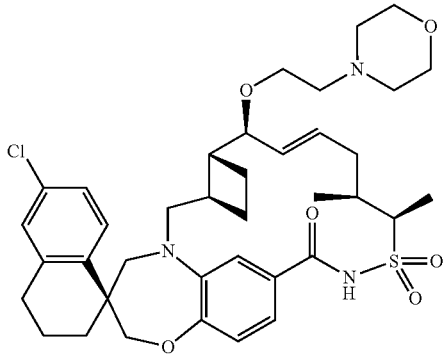

To a solution of (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 719, Step 2; 20 mg, 0.033 mmol) in DMF (0.668 mL) cooled to 0° C. was added sodium hydride, 60% dispersion in mineral oil (13.4 mg, 0.334 mmol). The reaction mixture was stirred at 0° C. for 15 min, and then 4-(2-bromoethyl)morpholine hydrobromide (Combi-Blocks Inc.; 45.9 mg, 0.167 mmol) was added. The reaction mixture was stirred at ambient temperature overnight then it was quenched with aq. NH$_4$Cl and diluted with water, then extracted with EtOAc (3×8 mL). The combined organic layer was dried over MgSO$_4$ and concentrated. The crude oily yellow residue was purified by chromatography through a Redi-Sep pre-packed silica gel column (4 g), eluting with 10-40-60% EtOAc (containing 0.3% AcOH)/heptanes; nothing eluted; the column was then flushed with 100% EtOAc to provide the title compound (17.5 mg, 0.025 mmol, 73.6% yield). $^1$H NMR (500 MHz, CD$_2$Cl$_2$) δ 7.71 (d, J=8.6 Hz, 1H), 7.17 (dd, J=2.2, 8.6 Hz, 1H), 7.09 (d, J=2.0 Hz, 1H), 6.93 (dd, J=1.5, 8.1 Hz, 1H), 6.90 (d, J=8.1 Hz, 1H), 6.87 (s, 1H), 5.80 (ddd, J=3.2, 9.5, 14.9 Hz, 1H), 5.53 (dd, J=9.0, 15.2 Hz, 1H), 4.23 (q, J=7.0 Hz, 1H), 4.11-4.05 (m, 3H), 3.82 (d, J=15.2 Hz, 1H), 3.74 (dd, J=3.2, 9.0 Hz, 1H), 3.72-3.66 (m, 5H), 3.58-3.50 (m, 1H), 3.42-3.36 (m, 1H), 3.25 (d, J=14.4 Hz, 1H), 3.03 (dd, J=10.1, 15.3 Hz, 1H), 2.84-2.70 (m, 2H), 2.59-2.50 (m, 6H), 2.47-2.39 (m, 1H), 2.33 (quin, J=9.0 Hz, 1H), 2.21-2.13 (m, 1H), 2.12-2.05 (m, 2H), 2.00-1.90 (m, 3H), 1.89-1.75 (m, 3H), 1.72-1.61 (m, 1H), 1.44 (d, J=7.1 Hz, 3H), 1.42-1.35 (m, 1H), 1.02 (d, J=6.8 Hz, 3H). MS (ESI, +ve ion) m/z 712.1 (M+H)$^+$.

1532

Example 721. (1S,3'R,6'R,7'S,8'E,11'S,12'R)-6-chloro-11',12'-dimethyl-7'-(3-(4-morpholinyl)propoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one-13', 13'-dioxide

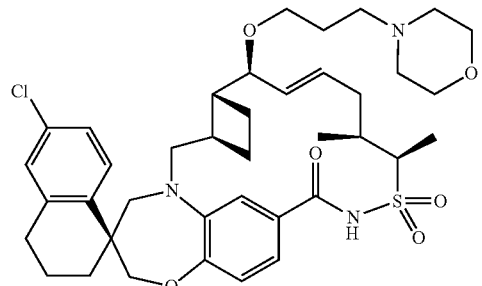

Step 1. 4-(3-iodopropyl)morpholine

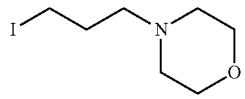

A solution of 4-(3-chloropropyl)morpholine hydrochloride (Aldrich; 124 mg, 0.62 mmol) and sodium iodide (a.c.s. reagent; 0.025 mL, 0.62 mmol) in DMF (3.1 mL) was heated to 60° C. for 3 h. The reaction mixture was carried on to the next step as is.

Step 2. (1S,3'R,6'R,7'S,8'E,11'S,12'R)-6-chloro-11',12'-dimethyl-7'-(3-(4-morpholinyl)propoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one-13', 13'-dioxide To a solution of (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 719, Step 2; 12 mg, 0.020 mmol) in DMF (0.734 mL) at ambient temperature was added sodium hydride, 60% dispersion in mineral oil (8.01 mg, 0.20 mmol). The reaction mixture was stirred at 0° C. for 15 min, and then 4-(3-iodopropyl)morpholine (25.5 mg, 0.100 mmol) (reagent assumed to be a 0.2M solution in DMF) was added. The reaction mixture was stirred at 70° C. overnight. LC/MS analysis of the reaction mixture showed complete conversion. The mixture was quenched with aq NH$_4$Cl and diluted with water, then extracted with EtOAc (4×4 mL). The combined organic layer was dried over MgSO$_4$ and concentrated. The crude oily residue was purified by chromatography through a Redi-Sep pre-packed silica gel column (4 g), eluting with 10-50% EtOAc (containing 0.3% AcOH)/heptanes to provide the title compound (12 mg, 0.017 mmol, 82% yield). $^1$H NMR (500 MHz, CD$_2$Cl$_2$) δ 7.71 (d, J=8.6 Hz, 1H), 7.17 (dd, J=2.2, 8.6 Hz, 1H), 7.09 (d, J=1.7 Hz, 1H), 6.91 (s, 2H), 6.87 (s, 1H), 5.77 (ddd, J=2.9, 9.3, 14.9 Hz, 1H), 5.53 (dd, J=8.8, 14.7 Hz, 1H), 4.25 (q, J=7.4 Hz, 1H), 4.10-4.07 (m, 2H), 3.82 (d, J=14.9 Hz, 1H), 3.75-3.66 (m, 7H), 3.46-3.39 (m, 1H), 3.31-3.25 (m, 1H), 3.25 (d, J=14.2 Hz, 1H), 3.02 (dd, J=10.3, 15.4 Hz, 1H), 2.83-2.70 (m, 2H), 2.55-2.38 (m, 7H), 2.37-2.28 (m, 1H), 2.21-2.08 (m, 2H), 1.99-1.90 (m, 2H), 1.89-1.75 (m, 3H), 1.75-1.61 (m, 4H), 1.44 (d, J=7.3 Hz, 3H), 1.40 (t, J=13.0 Hz, 1H), 1.03 (d, J=6.8 Hz, 3H). MS (ESI, +ve ion) m/z 726.1 (M+H)+.

Example 722. (1S,3'R,6'R,7'S,8'E,11'S,12'R)-6-chloro-11',12'-dimethyl-7'-(2-(tetrahydro-2H-pyran-4-yl)ethoxy)-3,4-dihydro-2H,15'H-spiro [naphthalene-1,22'-[20]oxa[13]thia[1,14]diazatetracyclo [14.7.2.0$^{3,6}$.0$^{19,24}$]pentacosa[8,16,18,24]tetraen]-15'-one-13', 13'-dioxide

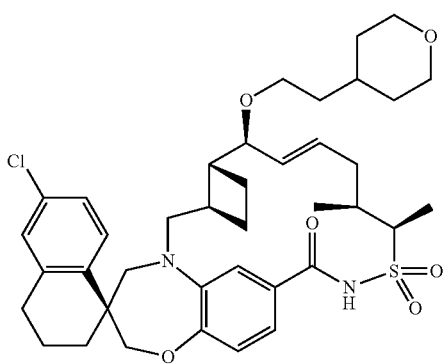

To a solution of (1S,3'R,6'R,7'S,8'E,11'S,12'R)-6-chloro-7'-hydroxy-11',12'-dimethyl-3,4-dihydro-2H,15'H-spiro [naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (Example 719, Step 2; 20 mg, 0.033 mmol) in DMF (0.668 mL) cooled to 0° C. was added sodium hydride (60% dispersion in mineral oil; 13.4 mg, 0.334 mmol). The reaction mixture was stirred at 0° C. for 15 min, and then 4-(2-bromoethyl)-tetrahydropyran (Maybridge Chemical Co., Ltd; 0.032 mL, 0.167 mmol) was added. The reaction mixture was stirred at ambient temperature overnight. The mixture was then quenched with aq NH$_4$Cl and diluted with water, then extracted with EtOAc (3×8 mL). The combined organic layer was dried over MgSO$_4$ and concentrated. The crude oily residue was loaded onto a silica gel cartridge and purified by chromatography through a Redi-Sep pre-packed silica gel column (4 g), eluting with 10-30-40-50% EtOAc (containing 0.3% AcOH)/heptanes to provide the title compound (20.7 mg, 0.029 mmol, 87% yield). $^1$H NMR (500 MHz, CD$_2$Cl$_2$) δ 8.18 (br s, 1H), 7.71 (d, J=8.6 Hz, 1H), 7.17 (dd, J=2.2, 8.6 Hz, 1H), 7.09 (d, J=2.2 Hz, 1H), 6.91 (s, 2H), 6.86 (s, 1H), 5.77 (ddd, J=3.4, 9.5, 15.2 Hz, 1H), 5.52 (dd, J=9.0, 15.2 Hz, 1H), 4.30-4.23 (m, 1H), 4.10-4.06 (m, 2H), 3.91-3.85 (m, 2H), 3.82 (d, J=15.2 Hz, 1H), 3.73-3.63 (m, 2H), 3.42 (td, J=6.7, 9.3 Hz, 1H), 3.34 (qt, J=2.2, 11.7 Hz, 2H), 3.29-3.24 (m, 1H), 3.25 (d, J=14.2 Hz, 1H), 3.02 (dd, J=10.1, 15.3 Hz, 1H), 2.84-2.70 (m, 2H), 2.45-2.38 (m, 1H), 2.32 (quin, J=9.0 Hz, 1H), 2.20-2.01 (m, 3H), 2.01-1.90 (m, 3H), 1.89-1.75 (m, 3H), 1.72-1.63 (m, 1H), 1.62-1.52 (m, 4H), 1.44 (d, J=7.3 Hz, 3H), 1.47-1.41 (m, 3H), 1.42-1.36 (m, 1H), 1.02 (d, J=6.8 Hz, 3H). MS (ESI, +ve ion) m/z 711.1 (M+H)+.

Example 723. (1S,3'R,6'R,7'S,8'E,11'5,12'R)-6-chloro-11',12'-dimethyl-7'-(2-(1-piperidinyl)ethoxy)-3,4-dihydro-2H,15'H-spiro[naphthalene-1,22'-[20] oxa[13]thia[1,14]diazatetracyclo[14.7.2.0$^{3,6}$.0$^{19,24}$] pentacosa [8,16,18,24]tetraen]-15'-one-13', 13'-dioxide

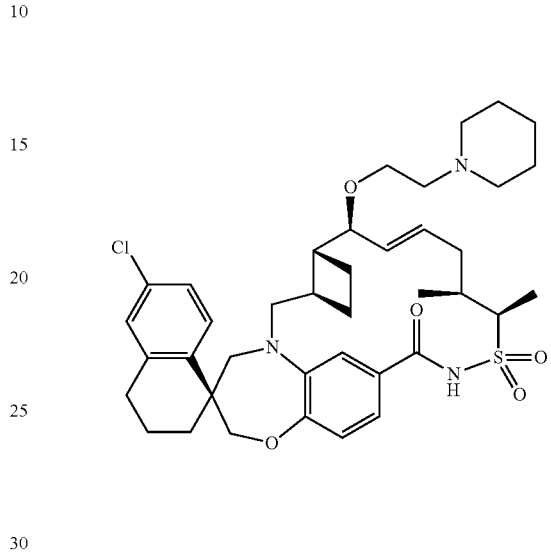

To a solution of (1S,3'R,6'R,7'S,8'E,11'S,12'R)-6-chloro-7'-hydroxy-11',12'-dimethyl-3,4-dihydro-2H,15'H-spiro [naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (Example 719, Step 2; 20 mg, 0.033 mmol) in DMF (0.668 mL) at ambient temperature was added sodium hydride (60% dispersion in mineral oil; 13.35 mg, 0.334 mmol). The reaction mixture was stirred at ambient temperature for 15 min, and then 1-(2-chloroethyl)piperidine monohydrochloride (Sigma-Aldrich Corporation; 30.7 mg, 0.167 mmol) was added followed by sodium iodide (a.c.s. reagent; 25 mg, 0.167 mmol). The reaction mixture was stirred at ambient temperature for 30 min then heated to 70° C. for 3.5 h. The mixture was then cooled to ambient temperature, quenched with aq NH$_4$Cl and diluted with water, then extracted with EtOAc (4×4 mL). The combined organic layer was dried over MgSO$_4$ and concentrated. The crude oily residue was purified by chromatography through a Redi-Sep pre-packed silica gel column (4 g), eluting with 10-50% EtOAc (containing 0.3% AcOH)/heptanes (nothing eluted) then with 100% EtOAc (nothing eluted) then 100% EtOAc/EtOH (3:1) to provide the title compound (16 mg, 0.023 mmol, 67.5% yield). $^1$H NMR (500 MHz, CD$_2$Cl$_2$) δ 7.65 (d, J=8.6 Hz, 1H), 7.08 (dd, J=2.2, 8.6 Hz, 1H), 7.02 (d, J=8.6 Hz, 1H), 6.99 (d, J=2.2 Hz, 1H), 6.87 (s, 1H), 6.74 (d, J=8.1 Hz, 1H), 6.06-5.99 (m, 1H), 5.40 (dd, J=8.6, 15.4 Hz, 1H), 3.97-3.90 (m, 2H), 3.82 (d, J=6.6 Hz, 1H), 3.76-3.67 (m, 2H), 3.66 (d, J=14.9 Hz, 1H), 3.59 (d, J=14.4 Hz, 1H), 3.55-3.46 (m, 1H), 3.15 (d, J=14.2 Hz, 1H), 2.93-2.80 (m, 5H), 2.73-2.60 (m, 2H), 2.39-2.25 (m, 2H), 2.03 (br s, 3H), 1.96-1.86 (m, 3H), 1.85-1.78 (m, 2H), 1.78-1.72 (m, 1H), 1.68 (br s, 6H), 1.57 (quin, J=9.3 Hz, 1H), 1.49-1.37 (m, 2H), 1.28 (d, J=6.8 Hz, 3H), 1.32-1.23 (m, 1H), 0.90 (d, J=6.1 Hz, 3H). MS (ESI, +ve ion) m/z 710.1 (M+H)+.

Example 724. (1S,3'R,6'R,7'S,8'Z,11'S,12'R)-6-chloro-11',12'-dimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

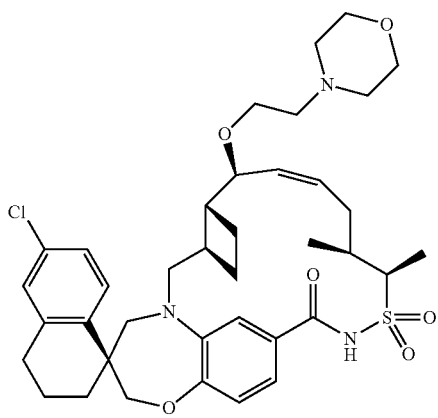

Step 1. (1S,3'R,6'R,7'S,8'Z,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

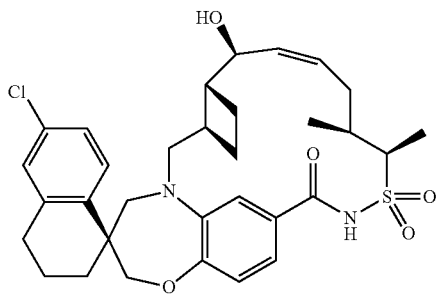

A 1000 mL RB flask was charged with (S)-6'-chloro-5-(((1R,2R)-2-((S)-1-hydroxyallyl)cyclobutyl)methyl)-N-(((2R,3S)-3-methylhex-5-en-2-yl)sulfonyl)-3',4',5-tetrahydro-2H,2'H-spiro[benzo[b][1,4]oxazepine-3,1'-naphthalene]-7-carboxamide (Example 719, Step 1; 710 mg, 1.13 mmol) and DCM (569 mL). The solution was sparged with argon for 15 min, then Hoveyda-Grubbs II (70.9 mg, 0.113 mmol) (solid) was added.

The mixture was stirred at 45° C. for 15 h. The reaction mixture was then sparged with air for 20 minutes while cooling to ambient temperature, then it was concentrated under reduced pressure. The crude oil was absorbed onto a plug of silica gel and purified through a 220 g ISCO Gold column, eluting with 10-20 (15 minutes)-50% EtOAc (containing 0.3% AcOH) in heptanes over 36 minutes to provide (1S,3'R,6'R,7'S,8'Z,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as the first eluting minor isomer followed by (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 719, Step 2) as the second eluting and major isomer. The semipure material thus obtained was loaded onto a silica gel column and purified eluting with 5% acetone in DCM to provide the title compound. $^{1}$H NMR (500 MHz, CD$_2$Cl$_2$) δ 8.83 (br s, 1H), 7.71 (d, J=8.3 Hz, 1H), 7.17 (dd, J=2.3, 8.4 Hz, 1H), 7.11 (dd, J=1.6, 8.2 Hz, 1H), 7.09 (d, J=2.2 Hz, 1H), 7.02 (s, 1H), 6.93 (d, J=8.1 Hz, 1H), 5.82-5.75 (m, 1H), 5.67 (dd, J=6.5, 11.4 Hz, 1H), 4.43 (s, 1H), 4.12-4.05 (m, 2H), 3.85-3.76 (m, 2H), 3.67 (d, J=14.4 Hz, 1H), 3.25 (d, J=14.4 Hz, 1H), 3.28-3.19 (m, 1H), 2.83-2.65 (m, 3H), 2.38-2.23 (m, 2H), 2.19-2.11 (m, 2H), 2.10-1.99 (m, 3H), 1.97-1.87 (m, 2H), 1.87-1.80 (m, 1H), 1.79-1.70 (m, 2H), 1.47 (d, J=7.3 Hz, 3H), 1.47-1.40 (m, 1H), 1.06 (d, J=6.6 Hz, 3H). MS (ESI, +ve ion) m/z 599.1 (M+H)$^{+}$.

Step 2: (1S,3'R,6'R,7'S,8'Z,11'S,12'R)-6-chloro-11',12'-dimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide The title compound was synthesized from (1S,3'R,6'R,7'S,8'Z,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 724, Step 1; 33 mg; 0.055 mmol) following the procedure described for Example 7. Purification of the crude material via column chromatography eluting with 3:1 EtOAc/EtOH provided (1S,3'R,6'R,7'S,8'Z,11'S,12'R)-6-chloro-11',12'-dimethyl-7'-(2-(4-morpholinyl)ethoxy)-3,4-dihydro-2H,15'H-spiro[naphthalene-1,22'-[20]oxa[13]thia[1,14]diazatetracyclo-[14.7.2.0$^{3,6}$.0$^{19,24}$]pentacosa[8,16,18,24]tetraen]-15'-one 13',13'-dioxide (21.6 mg, 0.03 mmol, 55.1%). $^{1}$H NMR (400 MHz, CD$_2$Cl$_2$) δ 7.68 (d, J=8.4 Hz, 1H), 7.21 (br s, 1H), 7.15 (d, J=7.6 Hz, 1H), 7.10 (dd, J=2.2, 8.4 Hz, 1H), 7.06 (d, J=2.2 Hz, 1H), 6.72 (d, J=8.2 Hz, 1H), 5.80-5.70 (m, 1H), 5.44 (t, J=10.2 Hz, 1H), 4.28-4.21 (m, 1H), 4.01 (dd, J=12.1, 19.4 Hz, 2H), 3.78-3.70 (m, 2H), 3.72 (d, J=13.9 Hz, 1H), 3.66 (t, J=4.4 Hz, 4H), 3.59 (ddd, J=2.7, 5.3, 7.8 Hz, 1H), 3.48-3.41 (m, 1H), 3.42 (d, J=14.5 Hz, 1H), 3.23 (dd, J=9.5, 14.8 Hz, 1H), 3.15-3.06 (m, 1H), 2.90-2.80 (m, 1H), 2.79-2.70 (m, 2H), 2.68-2.57 (m, 4H), 2.46-2.31 (m, 2H), 2.13 (s, 3H), 2.08-2.00 (m, 1H), 1.88 (br s, 3H), 1.84-1.67 (m, 3H), 1.49-1.38 (m, 1H), 1.32 (d, J=7.0 Hz, 3H), 1.01 (d, J=6.3 Hz, 3H). MS (ESI, +ve ion) m/z 712.1 (M+H)$^{+}$.

1537

Example 726. N-(2-(((1S,3'R,6'R,7'S,8'E,11'S,12'R)-6-chloro-11',12'-dimethyl-13', 13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraene]-7'-yl)oxy)ethyl)4-methylbenzenesulfonamide

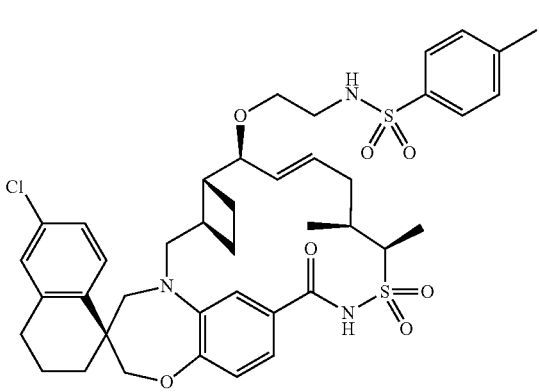

To a solution of (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 719, Step 2; 21 mg, 0.035 mmol) in DMSO (0.35 mL) at ambient temperature was added N-tosylaziridine (Sigma Aldrich; 6.9 mg, 0.035 mmol). After stirring at ambient temperature for 5 min, potassium t-butoxide (sublimed, 99.99% trace metals basis; Sigma Aldrich; 19.7 mg, 0.175 mmol) was added and the reaction mixture was stirred at ambient temperature for 2 h. The mixture was then quenched and diluted with water, then extracted with EtOAc (4×5 mL). The organic layer was dried over MgSO₄ and concentrated. The crude oily residue was loaded onto a silica gel cartridge and purified by chromatography through a Redi-Sep pre-packed silica gel column (4 g), eluting with 10-50% % EtOAc (containing 0.3% AcOH)/heptanes to provide the title compound (17.2 mg, 0.022 mmol, 61.6%). $^1$H NMR (400 MHz, CD$_2$Cl$_2$) δ 8.17 (s, 1H), 7.77 (d, J=8.4 Hz, 2H), 7.73 (d, J=9.2 Hz, 1H), 7.40 (d, J=7.8 Hz, 2H), 7.21 (dd, J=2.3, 8.4 Hz, 1H), 7.14 (d, J=2.2 Hz, 1H), 6.95 (s, 2H), 6.88 (s, 1H), 5.78 (ddd, J=3.7, 9.2, 15.1 Hz, 1H), 5.49 (dd, J=8.7, 15.0 Hz, 1H), 4.73 (t, J=6.0 Hz, 1H), 4.31-4.21 (m, 1H), 4.15-4.11 (m, 2H), 3.81 (d, J=14.3 Hz, 1H), 3.73 (d, J=14.5 Hz, 1H), 3.68 (dd, J=3.3, 9.2 Hz, 1H), 3.45 (ddd, J=4.3, 6.2, 10.0 Hz, 1H), 3.29 (d, J=14.5 Hz, 1H), 3.32-3.24 (m, 1H), 3.14-3.01 (m, 3H), 2.91-2.74 (m, 2H), 2.47 (s, 3H), 2.43-2.27 (m, 2H), 2.09 (d, J=10.2 Hz, 3H), 1.99 (dd, J=4.9, 9.8 Hz, 3H), 1.94-1.85 (m, 1H), 1.85-1.77 (m, 2H), 1.75-1.66 (m, 1H), 1.48 (d, J=7.0 Hz, 3H), 1.47-1.40 (m, 1H), 1.07 (d, J=6.8 Hz, 3H). MS (ESI, +ve ion) m/z 796.0 (M+H)⁺.

1538

Example 727. (1S,3'R,6'R,7'S,8'E,11'S,12'R)-6-chloro-11',12'-dimethyl-7'-(2-(3-oxo-4-morpholinyl)ethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one-13', 13'-dioxide

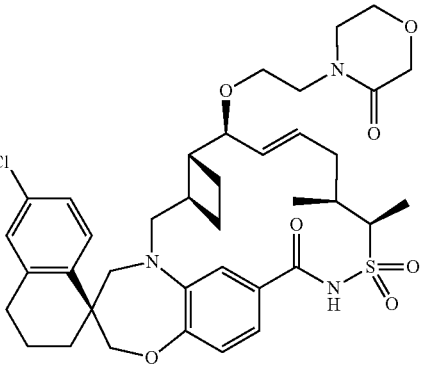

To a solution of (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo-[14.7.2.0³,⁶.0¹⁹,²⁴]pentacosa[8,16,18,24]tetraen]-15'-one 13',13'-dioxide (Example 14; 12 mg, 0.017 mmol) and morpholin-3-one (Sigma Aldrich; 8.59 mg, 0.085 mmol) in DMF (0.34 mL) at 0° C. was added sodium hydride (60% dispersion in mineral oil; 6.80 mg, 0.170 mmol). The reaction mixture was stirred at ambient temperature for 1 h then it was quenched with aq NH₄Cl and diluted with water, then extracted with EtOAc (3×3 mL). The organic layer was dried over MgSO₄ and concentrated. The crude material was purified by chromatography through a Redi-Sep pre-packed silica gel column (4 g), eluting with 10-50% % EtOAc (containing 0.3% AcOH)/heptanes then with 100% EtOAc to provide the desired product contaminated by unreacted morpholinone. This material was repurified eluting with 5-20% acetone in DCM; then with 20-100% EtOAc in DCM to provide the title compound (9.2 mg, 0.013 mmol, 74.5%). $^1$H NMR (400 MHz, CD$_2$Cl$_2$) δ 8.28 (br s, 1H), 7.71 (d, J=8.4 Hz, 1H), 7.17 (dd, J=2.3, 8.6 Hz, 1H), 7.09 (d, J=2.3 Hz, 1H), 6.95-6.89 (m, 2H), 6.85 (s, 1H), 5.81 (ddd, J=3.3, 9.6, 15.1 Hz, 1H), 5.52 (dd, J=9.1, 15.2 Hz, 1H), 4.30-4.22 (m, 1H), 4.12-4.06 (m, 4H), 3.83 (t, J=5.3 Hz, 2H), 3.81 (d, J=14.7 Hz, 1H), 3.77 (dd, J=3.1, 9.2 Hz, 1H), 3.69 (d, J=14.3 Hz, 1H), 3.58-3.52 (m, 2H), 3.47-3.38 (m, 4H), 3.25 (d, J=14.1 Hz, 1H), 3.03 (dd, J=10.1, 15.4 Hz, 1H), 2.85-2.69 (m, 2H), 2.47-2.38 (m, 1H), 2.38-2.26 (m, 1H), 2.22-2.10 (m, 1H), 2.10-2.01 (m, 2H), 2.00-1.90 (m, 3H), 1.90-1.75 (m, 3H), 1.73-1.63 (m, 1H), 1.44 (d, J=7.2 Hz, 3H), 1.43-1.34 (m, 1H), 1.02 (d, J=6.8 Hz, 3H). MS (ESI, +ve ion) m/z 726.1 (M+H)⁺.

Example 728. (1S,3'R,6'R,7'S,8'E,11'S,12'R)-6-chloro-11',12'-dimethyl-7'-(2-(2-oxo-1-piperidinyl)ethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one-13', 13'-dioxide Example 729. (1S,3'R,6'R,7'S,8'E,11'S,12'R)-6-chloro-11',12'-dimethyl-7'-(2-(2-oxo-1,3-oxazolidin-3-yl)ethoxy)-3,4-dihydro-2H,15'H-spiro[naphthalene-1,22'-[20]oxa[13]thia[1,14]diazatetracyclo [14.7.2.0³,⁶.0¹⁹,²⁴]pentacosa [8,16,18,24]tetraen]-15'-one-13', 13'-dioxide

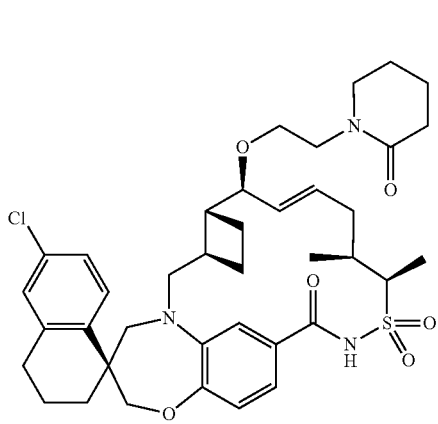

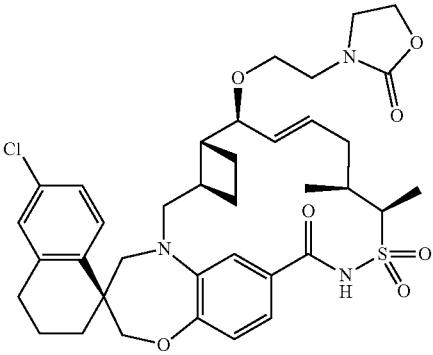

To a solution of (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo-[14.7.2.0³,⁶.0¹⁹,²⁴]pentacosa[8,16,18,24]tetraen]-15'-one 13',13'-dioxide (Example 14, 21 mg, 0.030 mmol) and delta-valerolactam (Sigma; 14.7 mg, 0.149 mmol) in DMF (0.595 mL) at 0° C. was added sodium hydride (60% dispersion in mineral oil; 11.89 mg, 0.297 mmol). The reaction mixture was stirred at ambient temperature for 3 h. The mixture was then quenched with aq NH₄Cl and diluted with water, then extracted with EtOAc (3×5 mL). The organic layer was dried over MgSO₄ and concentrated. The crude material was purified by chromatography through a Redi-Sep pre-packed silica gel column (4 g), eluting with 0-10-50-100% EtOAc/heptanes to provide the title compound (9 mg, 0.012 mmol, 41.8% yield). ¹H NMR (400 MHz, CD₂Cl₂) δ 8.47 (br s, 1H), 7.71 (d, J=8.4 Hz, 1H), 7.17 (dd, J=2.3, 8.4 Hz, 1H), 7.09 (d, J=2.3 Hz, 1H), 6.94 (dd, J=1.8, 8.0 Hz, 1H), 6.90 (d, J=8.0 Hz, 1H), 6.86 (d, J=1.6 Hz, 1H), 5.80 (ddd, J=3.3, 9.6, 15.1 Hz, 1H), 5.52 (dd, J=8.9, 15.0 Hz, 1H), 4.25 (q, J=6.8 Hz, 1H), 4.12-4.04 (m, 2H), 3.82 (d, J=14.9 Hz, 1H), 3.76 (dd, J=3.2, 9.1 Hz, 1H), 3.69 (d, J=14.3 Hz, 1H), 3.54-3.43 (m, 2H), 3.42-3.30 (m, 4H), 3.25 (d, J=14.3 Hz, 1H), 3.02 (dd, J=10.0, 15.3 Hz, 1H), 2.84-2.68 (m, 2H), 2.48-2.38 (m, 1H), 2.37-2.26 (m, 3H), 2.23-2.12 (m, 1H), 2.11-2.01 (m, 2H), 2.01-1.89 (m, 3H), 1.88-1.78 (m, 3H), 1.79-1.73 (m, 4H), 1.72-1.63 (m, 1H), 1.44 (d, J=7.0 Hz, 3H), 1.43-1.34 (m, 1H), 1.02 (d, J=6.8 Hz, 3H). MS (ESI, +ve ion) m/z 724.3 (M+H)⁺.

To a solution of (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo-[14.7.2.0³,⁶.0¹⁹,²⁴]pentacosa[8,16,18,24]tetraen]-15'-one 13',13'-dioxide (Example 14, 21 mg, 0.030 mmol) and 2-oxazolidone (Sigma; 13 mg, 0.149 mmol) in DMF (0.595 mL) at 0° C. was added sodium hydride (60% dispersion in mineral oil; 11.9 mg, 0.297 mmol). The reaction mixture was stirred at ambient temperature and after 3.5 h the mixture was quenched with aq NH₄Cl and diluted with water, then extracted with EtOAc (3×5 mL). The organic layer was dried over MgSO₄ and concentrated. The crude material was purified by chromatography through a Redi-Sep pre-packed silica gel column (4 g), eluting with 0-10-50-100% EtOAc/heptanes to provide 16.5 mg of desired product contaminated by a large amount of oxazolidone. This material was purified by chromatography through a Redi-Sep pre-packed silica gel column (4 g), eluting with 5-15% acetone in DCM, to provide the title compound (6.4 mg, 0.090 mmol, 30.2% yield). ¹H NMR (500 MHz, CD₂Cl₂) δ 8.16 (br s, 1H), 7.71 (d, J=8.6 Hz, 1H), 7.17 (dd, J=2.2, 8.6 Hz, 1H), 7.09 (d, J=2.2 Hz, 1H), 6.95-6.89 (m, 2H), 6.85 (s, 1H), 5.81 (ddd, J=3.2, 9.8, 15.1 Hz, 1H), 5.53 (ddd, J=1.2, 9.3, 15.2 Hz, 1H), 4.27 (t, J=8.1 Hz, 2H), 4.29-4.22 (m, 1H), 4.12-4.06 (m, 2H), 3.83 (d, J=15.4 Hz, 1H), 3.78 (dd, J=3.3, 9.2 Hz, 1H), 3.69 (d, J=14.2 Hz, 1H), 3.61 (dt, J=2.3, 8.0 Hz, 2H), 3.54 (ddd, J=2.9, 6.6, 13.9 Hz, 1H), 3.39 (ddd, J=2.4, 3.7, 9.5 Hz, 2H), 3.31 (ddd, J=2.9, 5.9, 13.9 Hz, 1H), 3.25 (d, J=14.4 Hz, 1H), 3.03 (dd, J=10.3, 15.4 Hz, 1H), 2.83-2.70 (m, 2H), 2.47-2.38 (m, 1H), 2.33 (quin, J=9.1 Hz, 1H), 2.22-2.14 (m, 1H), 2.12-2.01 (m, 2H), 2.00-1.90 (m, 3H), 1.89-1.74 (m, 3H), 1.72-1.63 (m, 1H), 1.45 (d, J=7.3 Hz, 3H), 1.43-1.35 (m, 1H), 1.02 (d, J=6.8 Hz, 3H). MS (ESI, +ve ion) m/z 712.0 (M+H)⁺.

1541

Example 730. (1S,3'R,6'R,7'S,8'E,11'S,12'R)-6-chloro-11',12'-dimethyl-7'-(2-(2-oxo-1-pyrrolidinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one-13',13'-dioxide

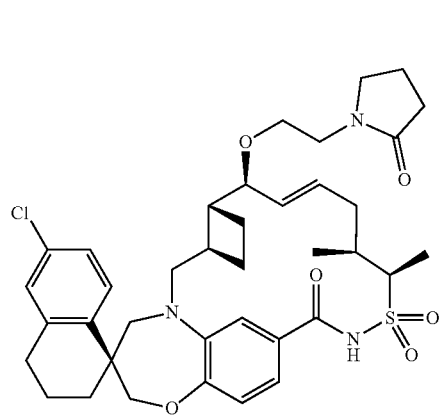

To a solution of (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo-[14.7.2.0$^{3,6}$.0$^{19,24}$]pentacosa[8,16,18,24]tetraen]-15'-one 13',13'-dioxide (Example 14, 24 mg, 0.034 mmol) and 2-pyrrolidinone (Sigma Aldrich; 0.013 mL, 0.17 mmol) in DMF (0.68 mL) at 0° C. was added sodium hydride (60% dispersion in mineral oil; 13.6 mg, 0.340 mmol). The reaction mixture was stirred at ambient temperature and after 3.5 h it was quenched with aq NH$_4$Cl and diluted with water, then extracted with EtOAc (3×5 mL). The combined organic layer was dried over MgSO$_4$ and concentrated. The crude material was purified by chromatography through a Redi-Sep pre-packed silica gel column (4 g), eluting with 0-10-50-100% EtOAc/heptanes to provide the title compound (9.8 mg, 0.014 mmol, 40.6% yield). $^1$H NMR (500 MHz, CD$_2$Cl$_2$) δ 8.53 (br s, 1H), 7.71 (d, J=8.6 Hz, 1H), 7.16 (dd, J=2.2, 8.6 Hz, 1H), 7.09 (d, J=2.2 Hz, 1H), 6.94 (dd, J=1.7, 8.1 Hz, 1H), 6.90 (d, J=7.8 Hz, 1H), 6.86 (d, J=1.5 Hz, 1H), 5.80 (ddd, J=3.3, 9.7, 15.1 Hz, 1H), 5.52 (dd, J=8.9, 15.0 Hz, 1H), 4.28-4.22 (m, 1H), 4.11-4.05 (m, 2H), 3.82 (d, J=15.2 Hz, 1H), 3.76 (dd, J=3.3, 9.2 Hz, 1H), 3.69 (d, J=14.4 Hz, 1H), 3.51-3.45 (m, 1H), 3.44-3.40 (m, 2H), 3.40-3.29 (m, 3H), 3.25 (d, J=14.2 Hz, 1H), 3.03 (dd, J=10.3, 15.4 Hz, 1H), 2.84-2.70 (m, 2H), 2.46-2.38 (m, 1H), 2.37-2.30 (m, 1H), 2.29 (t, J=8.1 Hz, 2H), 2.21-2.13 (m, 1H), 2.12-2.02 (m, 1H), 1.97 (dd, J=7.5, 15.3 Hz, 2H), 2.01-1.90 (m, 2H), 1.89-1.74 (m, 3H), 1.72-1.55 (m, 3H), 1.44 (d, J=7.1 Hz, 3H), 1.43-1.34 (m, 1H), 1.02 (d, J=6.8 Hz, 3H). MS (ESI, +ve ion) m/z 710.0 (M+H)$^+$.

1542

Example 731. (1S,3'R,6'R,7'S,8'E,11'S,12'R)-6-chloro-11',12'-dimethyl-7'-(2-(2-oxo-1-azetedinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one-13',13'-dioxide

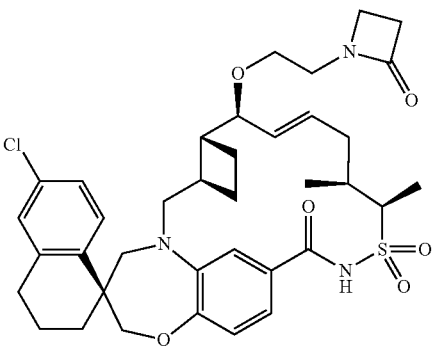

To a solution of (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo-[14.7.2.0$^{3,6}$.0$^{19,24}$]pentacosa[8,16,18,24]tetraen]-15'-one 13',13'-dioxide (Example 14, 21 mg, 0.030 mmol) and 2-azetidinone (Sigma Aldrich; 10.6 mg, 0.149 mmol) in DMF (0.595 mL) at 0° C. was added sodium hydride (60% dispersion in mineral oil; 11.9 mg, 0.297 mmol). The reaction mixture was stirred at ambient temperature. LC/MS analysis showed the desired mass but very low conversion after 1.5 h and still partial conversion after 12 h. More base and reagent were then added and the temperature was increased to 40° C. After 24 h the reaction mixture was quenched with aq NH$_4$Cl and diluted with water, then extracted with EtOAc (3×5 mL). The combined organic layer was dried over MgSO$_4$ and concentrated. The crude material was purified by chromatography through a Redi-Sep pre-packed silica gel column (4 g), eluting with 0-10-50-100% EtOAc/heptanes to provide the title compound (3.4 mg, 90% purity). $^1$H NMR (500 MHz, CD$_2$Cl$_2$) δ 8.21 (br s, 1H), 7.71 (d, J=8.6 Hz, 1H), 7.17 (dd, J=2.2, 8.6 Hz, 1H), 7.09 (d, J=2.2 Hz, 1H), 6.95-6.88 (m, 2H), 6.86 (s, 1H), 5.81 (ddd, J=3.3, 9.7, 15.1 Hz, 1H), 5.53 (dd, J=10.0, 14.9 Hz, 1H), 4.29-4.21 (m, 1H), 4.11-4.04 (m, 2H), 3.83 (d, J=15.2 Hz, 1H), 3.77 (dd, J=3.4, 9.0 Hz, 1H), 3.69 (d, J=14.4 Hz, 1H), 3.49 (ddd, J=4.5, 6.4, 9.8 Hz, 1H), 3.39-3.33 (m, 1H), 3.32-3.28 (m, 1H), 3.25 (d, J=14.2 Hz, 1H), 3.27-3.21 (m, 3H), 3.03 (dd, J=10.3, 15.4 Hz, 1H), 2.86 (t, J=4.0 Hz, 1H), 2.82 (d, J=5.9 Hz, 1H), 2.80-2.70 (m, 2H), 2.47-2.39 (m, 1H), 2.33 (quin, J=9.0 Hz, 1H), 2.22-2.13 (m, 1H), 2.13-2.02 (m, 2H), 2.00-1.89 (m, 3H), 1.89-1.75 (m, 3H), 1.72-1.63 (m, 1H), 1.44 (d, J=7.1 Hz, 3H), 1.43-1.36 (m, 1H), 1.02 (d, J=6.8 Hz, 3H). MS (ESI, +ve ion) m/z 696.3 (M+H)$^+$.

1543

Example 732. N-(2-(((1S,3'R,6'R,7'S,8'E,11'S,12'R)-6-chloro-11,12'-dimethyl-13', 13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl)oxy)ethyl)acetamide

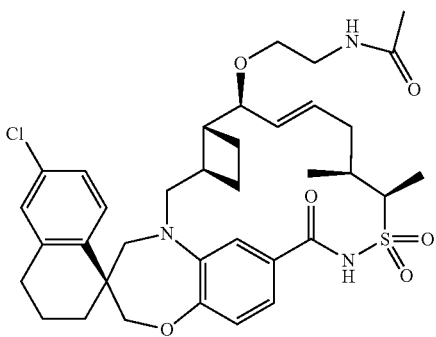

To a solution of (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo [14.7.2.0³,⁶.0¹⁹,²⁴]pentacosa[8,16,18,24]tetraen]-15'-one 13',13'-dioxide (Example 14, 17.5 mg, 0.025 mmol) and acetamide (Sigma; 6.32 µl, 0.124 mmol) in DMF (0.496 mL) at 0° C. was added sodium hydride (60% dispersion in mineral oil; 9.91 mg, 0.248 mmol). The reaction mixture was stirred at ambient temperature. After 3 h the reaction mixture was quenched with aq NH₄Cl and diluted with water, then extracted with EtOAc (3×5 mL). The combined organic layer was dried over MgSO₄ and concentrated. The crude material was purified by chromatography through a Redi-Sep pre-packed silica gel column (4 g), eluting with 0-10-50-100% EtOAc/heptanes to provide the title compound (7.9 mg, 0.012 mmol, 46.6% yield). ¹H NMR (500 MHz, CD₂Cl₂) δ 8.31 (s, 1H), 7.71 (d, J=8.6 Hz, 1H), 7.17 (dd, J=2.3, 8.4 Hz, 1H), 7.09 (d, J=2.2 Hz, 1H), 6.93 (dd, J=1.7, 8.1 Hz, 1H), 6.91 (d, J=8.1 Hz, 1H), 6.86 (d, J=1.5 Hz, 1H), 5.80 (ddd, J=3.3, 9.7, 15.1 Hz, 1H), 5.75 (br s, 1H), 5.54 (ddd, J=1.2, 9.3, 15.2 Hz, 1H), 4.29-4.22 (m, 1H), 4.12-4.05 (m, 2H), 3.83 (d, J=15.2 Hz, 1H), 3.77 (dd, J=3.3, 9.2 Hz, 1H), 3.69 (d, J=14.2 Hz, 1H), 3.47-3.42 (m, 1H), 3.39-3.33 (m, 1H), 3.33-3.27 (m, 2H), 3.25 (d, J=14.4 Hz, 1H), 3.04 (dd, J=10.1, 15.3 Hz, 1H), 2.83-2.70 (m, 2H), 2.44 (ddd, J=2.9, 9.8, 18.3 Hz, 1H), 2.34 (quin, J=9.0 Hz, 1H), 2.21-2.13 (m, 1H), 2.12-2.02 (m, 2H), 2.01-1.94 (m, 3H), 1.93 (s, 3H), 1.89-1.77 (m, 3H), 1.72-1.63 (m, 1H), 1.44 (d, J=7.1 Hz, 3H), 1.43-1.37 (m, 1H), 1.02 (d, J=6.8 Hz, 3H). MS (ESI, +ve ion) m/z 684.3 (M+H)⁺.

1544

Example 733. (1S,3'R,6'R,7'S,8'E,11'S,12'R)-7'-(2-(4-acetyl-1-piperazinyl)ethoxy)-6-chloro-11',12'-dimethyl-3,4-dihydro-2H,15'H-spiro[naphthalene-1,22'-[20]oxa[13]thia[1,14]diazatetracyclo [14.7.2.0³,⁶.0¹⁹,²⁴]pentacosa[8,16,18,24]tetraen]-15'-one-13', 13'-dioxide

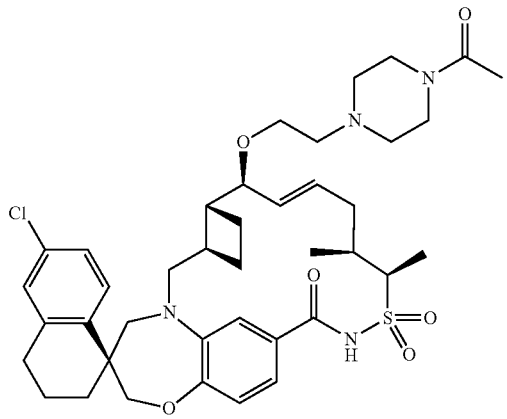

To a solution of (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo [14.7.2.0³,⁶.0¹⁹,²⁴]pentacosa[8,16,18,24]tetraen]-15'-one 13',13'-dioxide (Example 14, 30 mg, 0.042 mmol) and 1-acetylpiperazine (Alfa Aesar; 27.2 mg, 0.212 mmol) in DMSO (0.850 mL) was heated to 50° C. After 45 min the mixture was cooled to ambient temperature, quenched and diluted with water, then extracted with EtOAc (3×3 mL). The combined organic layer was dried over MgSO₄ and concentrated. The crude material was purified by chromatography through a Redi-Sep pre-packed silica gel column (4 g), eluting with 0-20-50-100% EtOAc/heptanes then with 100% 3:1 EtOAc/EtOH to provide semipure material. This material was repurified by chromatography through a Redi-Sep pre-packed silica gel column (4 g), eluting with 10-50-80% (3:1 EtOAc/EtOH)/heptanes to provide the title compound (13.7 mg, 0.018 mmol, 42.8% yield). ¹H NMR (500 MHz, CD₂Cl₂) δ 7.71 (d, J=8.3 Hz, 1H), 7.17 (dd, J=2.2, 8.6 Hz, 1H), 7.09 (d, J=2.2 Hz, 1H), 6.91 (s, 2H), 6.86 (s, 1H), 5.79 (ddd, J=3.4, 9.5, 14.9 Hz, 1H), 5.53 (dd, J=9.7, 14.3 Hz, 1H), 4.25 (br s, 1H), 4.11-4.05 (m, 2H), 3.82 (d, J=15.2 Hz, 1H), 3.74 (dd, J=2.9, 9.0 Hz, 1H), 3.69 (d, J=14.2 Hz, 1H), 3.56-3.52 (m, 2H), 3.50 (td, J=5.9, 10.0 Hz, 1H), 3.44-3.41 (m, 2H), 3.37 (td, J=6.1, 10.0 Hz, 1H), 3.25 (d, J=14.2 Hz, 1H), 3.03 (dd, J=10.1, 15.3 Hz, 1H), 2.84-2.70 (m, 2H), 2.52 (t, J=5.9 Hz, 2H), 2.48-2.44 (m, 2H), 2.41 (t, J=5.1 Hz, 2H), 2.44-2.38 (m, 1H), 2.37-2.29 (m, 1H), 2.16 (d, J=11.7 Hz, 1H), 2.13-2.03 (m, 2H), 2.02 (s, 3H), 2.01-1.90 (m, 3H), 1.90-1.75 (m, 3H), 1.71-1.62 (m, 1H), 1.44 (d, J=7.1 Hz, 3H), 1.43-1.35 (m, 1H), 1.03 (d, J=6.8 Hz, 3H). MS (ESI, +ve ion) m/z 753.1 (M+H)⁺.

Example 734. (1S,3'R,6'R,7'S,8'E,11'S,12'R)-6-chloro-11',12'-dimethyl-7'-(2-(4-methylsulfonyl)-1-piperazinyl)ethoxy)-3,4-dihydro-2H,15'H-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one-13', 13'-dioxide

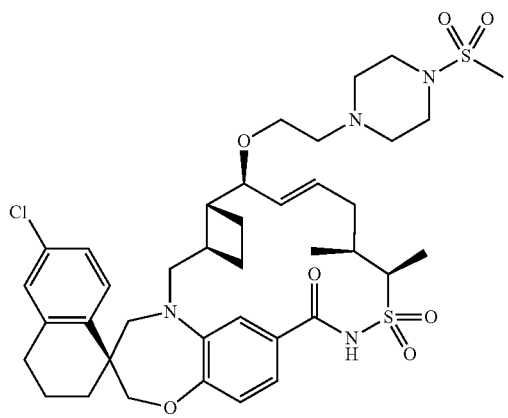

To a solution of (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (Example 14, 30 mg, 0.042 mmol) and 1-(methanesulfonyl)piperazine (Accela ChemBio Inc.; 34.9 mg, 0.212 mmol) in DMSO (0.850 mL) was heated to 50° C. After 4.5 h the mixture was cooled to ambient temperature, quenched and diluted with water, then extracted with EtOAc (4×3 mL). The combined organic layer was dried over MgSO$_4$ and concentrated. The crude material was purified by chromatography through a Redi-Sep pre-packed silica gel column (4 g), eluting with 0-10-50-100% EtOAc/heptanes to provide most of the desired product. The column was then flushed with 100% 3:1 EtOAc/EtOH to provide the rest of the desired product. This semipure material thus obtained was repurified through a Redi-Sep pre-packed silica gel column (4 g), eluting with 10-60% (3:1 EtOAc/EtOH)/heptanes to provide the title compound (22.1 mg, 0.028 mmol, 65.9% yield; 97% purity). $^1$H NMR (500 MHz, CD$_2$Cl$_2$) δ 7.62 (d, J=8.6 Hz, 1H), 7.08 (dd, J=2.2, 8.6 Hz, 1H), 7.01 (d, J=2.2 Hz, 1H), 6.88 (d, J=8.1 Hz, 1H), 6.83-6.76 (m, 2H), 5.73 (ddd, J=3.5, 9.2, 15.1 Hz, 1H), 5.45 (dd, J=8.9, 15.3 Hz, 1H), 4.16-4.07 (m, 1H), 4.01-3.97 (m, 2H), 3.73 (d, J=15.2 Hz, 1H), 3.69 (dd, J=3.2, 9.0 Hz, 1H), 3.61 (d, J=14.2 Hz, 1H), 3.43 (td, J=5.4, 10.5 Hz, 1H), 3.29 (td, J=5.6, 10.3 Hz, 1H), 3.18 (d, J=14.2 Hz, 1H), 3.15-3.09 (m, 5H), 2.94 (dd, J=10.1, 15.3 Hz, 1H), 2.66 (s, 3H), 2.75-2.61 (m, 2H), 2.55-2.48 (m, 5H), 2.33 (ddd, J=3.2, 10.0, 18.3 Hz, 1H), 2.29-2.21 (m, 1H), 2.12-2.00 (m, 2H), 2.00-1.92 (m, 2H), 1.91-1.81 (m, 1H), 1.80-1.65 (m, 3H), 1.63-1.54 (m, 1H), 1.34 (d, J=7.3 Hz, 3H), 1.34-1.27 (m, 1H), 0.94 (d, J=6.8 Hz, 3H). MS (ESI, +ve ion) m/z 789.1 (M+H)$^+$.

Example 735. N-(2-(((1S,3'R,6'R,7'S,8'E,11'S,12'R)-6-chloro-11',12'-dimethyl-13', 13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)ethyl) Methanesulfonamide

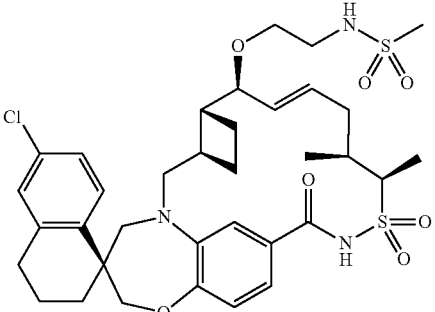

To a solution of (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (Example 14, 30 mg, 0.042 mmol) and methanesulfonamide (Matrix Scientific; 0.015 mL, 0.212 mmol) in DMF (0.850 mL) at 0° C. was added sodium hydride (60% dispersion in mineral oil; 16.99 mg, 0.425 mmol). The reaction mixture was stirred at ambient temperature overnight. The reaction mixture was then quenched with aq. NH$_4$Cl and diluted with water, then extracted with EtOAc (3×5 mL). The combined organic layer was dried over MgSO$_4$ and concentrated. The crude material was purified by chromatography through a Redi-Sep pre-packed silica gel column (4 g), eluting with 0-10-50-100% EtOAc/heptanes to provide the desired product contaminated by unreacted methanesulfonamide. The semipure material was taken up in DCM and washed twice with water, dried and concentrated. The material was repurified as above to provide the title compound (12.2 mg, 0.017 mmol, 39.9% yield, 92% purity). $^1$H NMR (500 MHz, CD$_2$Cl$_2$) δ 8.28 (br s, 1H), 7.70 (d, J=8.6 Hz, 1H), 7.17 (dd, J=2.3, 8.4 Hz, 1H), 7.09 (d, J=2.2 Hz, 1H), 6.93 (dd, J=1.7, 8.1 Hz, 1H), 6.91 (d, J=8.1 Hz, 1H), 6.89 (d, J=1.5 Hz, 1H), 5.81 (ddd, J=3.5, 9.4, 15.2 Hz, 1H), 5.54 (dd, J=8.9, 15.3 Hz, 1H), 4.51 (t, J=5.7 Hz, 1H), 4.23 (q, J=7.3 Hz, 1H), 4.11-4.05 (m, 2H), 3.82 (d, J=15.2 Hz, 1H), 3.77 (dd, J=3.7, 8.8 Hz, 1H), 3.69 (d, J=14.4 Hz, 1H), 3.53 (ddd, J=4.0, 6.3, 10.0 Hz, 1H), 3.36 (ddd, J=3.8, 6.0, 9.8 Hz, 1H), 3.25 (d, J=14.2 Hz, 1H), 3.26-3.17 (m, 2H), 3.04 (dd, J=10.0, 15.4 Hz, 1H), 2.94 (s, 3H), 2.84-2.70 (m, 2H), 2.46 (ddd, J=3.7, 9.3, 18.6 Hz, 1H), 2.39-2.30 (m, 1H), 2.20-2.02 (m, 3H), 2.01-1.90 (m, 3H), 1.89-1.75 (m, 3H), 1.72-1.63 (m, 1H), 1.44 (d, J=7.1 Hz, 3H), 1.42-1.36 (m, 1H), 1.02 (d, J=6.8 Hz, 3H). MS (ESI, +ve ion) m/z 720.0 (M+H)$^+$.

1547

Example 736. ethyl (2-(((1S,3'R,6'R,7'S,8'E,11'S,12'R)-6-chloro-11',12'-dimethyl-13', 13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)ethyl)carbamate

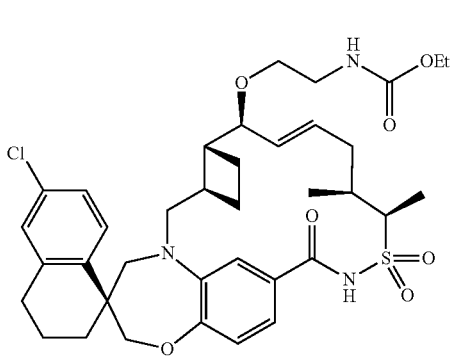

To a solution of (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (Example 14, 31 mg, 0.044 mmol) and urethane (0.020 mL, 0.220 mmol) in DMF (0.850 mL) at 0° C. was added sodium hydride (60% dispersion in mineral oil; 17.56 mg, 0.439 mmol). The reaction mixture was stirred at ambient temperature (no reaction after 15 min at 0° C.). After stirring overnight (still partial and sluggish reaction) the mixture was quenched with aq NH$_4$Cl and diluted with water, then extracted with EtOAc (3×5 mL). The combined organic layer was washed once with water, dried over MgSO$_4$ and concentrated. The crude material was purified by chromatography through a Redi-Sep pre-packed silica gel column (4 g), eluting with 0-20-40-100% EtOAc/heptanes to provide semipure desired product. This material was repurified as above to obtain the title compound (7.3 mg, 0.010 mmol, 23.3%, 94% pure). $^1$H NMR (500 MHz, Acetone-d6) δ 10.39 (br s, 1H), 7.75 (d, J=8.3 Hz, 1H), 7.22 (dd, J=2.3, 8.4 Hz, 1H), 7.15 (dd, J=2.0, 8.1 Hz, 1H), 7.13 (d, J=2.4 Hz, 1H), 6.95 (d, J=1.7 Hz, 1H), 6.90 (d, J=8.1 Hz, 1H), 5.99 (br s, 1H), 5.87 (ddd, J=3.2, 9.3, 14.7 Hz, 1H), 5.59 (dd, J=9.4, 14.5 Hz, 1H), 4.26 (q, J=7.2 Hz, 1H), 4.13-4.07 (m, 2H), 4.06-3.99 (m, 2H), 3.86 (d, J=15.4 Hz, 1H), 3.81 (dd, J=3.2, 9.0 Hz, 1H), 3.70 (d, J=14.2 Hz, 1H), 3.46 (td, J=5.9, 9.7 Hz, 1H), 3.34 (d, J=14.2 Hz, 1H), 3.34 (td, J=5.7, 9.8 Hz, 1H), 3.28-3.17 (m, 2H), 3.15 (dd, J=10.3, 15.4 Hz, 1H), 2.87-2.70 (m, 2H), 2.51 (ddd, J=2.7, 9.5, 16.9 Hz, 1H), 2.34 (quin, J=8.6 Hz, 1H), 2.29-2.21 (m, 1H), 2.19-2.08 (m, 2H), 1.99-1.89 (m, 3H), 1.86-1.71 (m, 4H), 1.50-1.42 (m, 1H), 1.40 (d, J=7.1 Hz, 3H), 1.18 (t, J=7.1 Hz, 3H), 0.99 (d, J=6.8 Hz, 3H). MS (ESI, +ve ion) m/z 714.3 (M+H)$^+$.

1548

Example 737. tert-butyl 4-(2-(((1S,3'R,6'R,7'S,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,24]tetraen]-7'-yl)oxy)ethyl)-1-piperidinecarboxylate

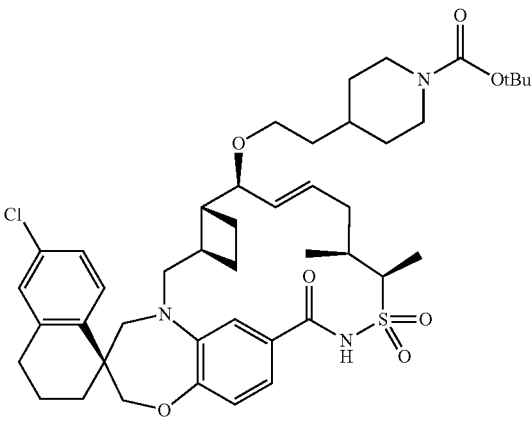

To a solution of (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (Example 719, Step 2; 30 mg, 0.050 mmol) in DMF (1.0 mL) cooled to 0° C. was added sodium hydride (60% dispersion in mineral oil; 20 mg, 0.50 mmol). The reaction mixture was stirred at 0° C. for 15 min, and then N-boc-4-(2-bromo-ethyl)-piperidine (Astatech, Inc.; 73.2 mg, 0.250 mmol) was added. The reaction mixture was stirred at ambient temperature for 4 d. The mixture was then quenched with aq NH$_4$Cl and diluted with water, then extracted with EtOAc (3×8 mL). The combined organic layer was dried over MgSO$_4$ and concentrated. The crude oily residue was purified by chromatography through a Redi-Sep pre-packed silica gel column (4 g), eluting with 10-50-100% EtOAc/heptanes to provide the desired material contaminated by a large amount of alkylating reagent. The semipure material was repurified eluting with 0-5-10% Acetone in DCM to provide the pure title compound (6.7 mg, 0.0083 mmol, 16.5% yield). $^1$H NMR (500 MHz, CD$_2$Cl$_2$) δ 8.16 (br s, 1H), 7.71 (d, J=8.6 Hz, 1H), 7.17 (dd, J=2.2, 8.6 Hz, 1H), 7.09 (d, J=2.4 Hz, 1H), 6.94-6.89 (m, 2H), 6.86 (s, 1H), 5.77 (ddd, J=3.2, 9.6, 15.1 Hz, 1H), 5.51 (ddd, J=1.0, 8.8, 14.9 Hz, 1H), 4.29-4.23 (m, 1H), 4.11-4.06 (m, 2H), 4.05-3.98 (m, 2H), 3.82 (d, J=15.2 Hz, 1H), 3.70 (dd, J=3.2, 9.0 Hz, 1H), 3.69 (d, J=14.9 Hz, 1H), 3.42 (td, J=6.6, 9.3 Hz, 1H), 3.26 (td, J=6.6, 9.3 Hz, 1H), 3.25 (d, J=14.2 Hz, 1H), 3.02 (dd, J=10.1, 15.3 Hz, 1H), 2.83-2.71 (m, 2H), 2.71-2.59 (m, 2H), 2.41 (ddd, J=3.2, 10.0, 18.3 Hz, 1H), 2.36-2.28 (m, 1H), 2.21-2.13 (m, 1H), 2.12-2.01 (m, 2H), 2.00-1.90 (m, 3H), 1.88-1.74 (m, 3H), 1.71-1.58 (m, 5H), 1.54-1.47 (m, 1H), 1.45 (d, J=7.1 Hz, 3H), 1.42 (s, 9H), 1.41-1.36 (m, 1H), 1.11-1.04 (m, 2H), 1.02 (d, J=6.8 Hz, 3H). MS (ESI, +ve ion) m/z 810.4 (M+H)$^+$.

1549

Example 738. ethyl (((1S,3'R,6'R,7'S,8'E,11'S,12'S)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetate

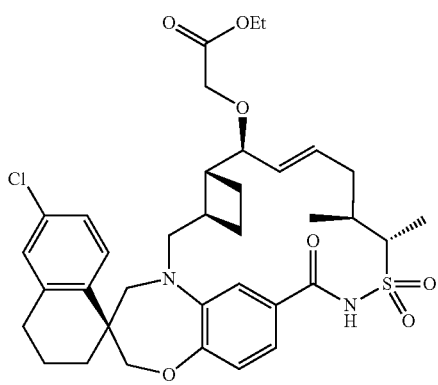

Step 1: (2R,3S)—N,N-bis(4-methoxybenzyl)-3-methylhex-5-ene-2-sulfonamide and (2S,3S)—N,N-bis(4-methoxybenzyl)-3-methylhex-5-ene-2-sulfonamide

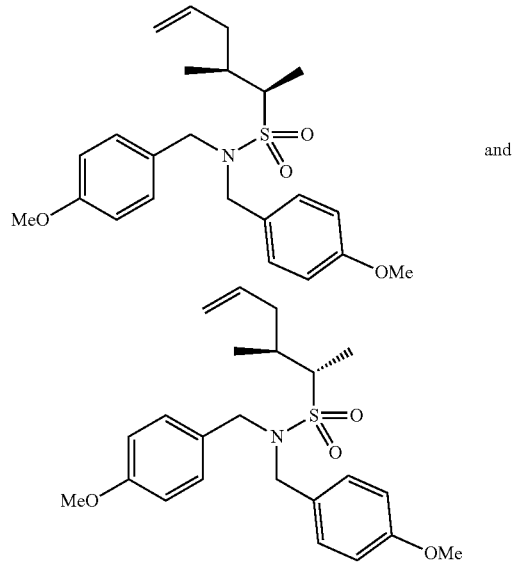

The title compounds were synthesized from N,N-bis(4-methoxybenzyl)ethanesulfonamide (Intermediate EE13; 1148 mg, 3.29 mmol) and (R)-pent-4-en-2-yl 4-methylbenzenesulfonate (prepared according to the procedure by Sigman, M. S. et al.; *J. Am. Chem. Soc.*, 2012, 134(28), 11408-11411; 1579 mg, 6.57 mmol) following the procedure described for Example 26, Step 1. (2R,3S)—N,N-bis(4-methoxybenzyl)-3-methylhex-5-ene-2-sulfonamide and (2S,3S)—N,N-bis(4-methoxybenzyl)-3-methylhex-5-ene-2-sulfonamide were obtained as a 2.4:1 mixture (539 mg, 1.29 mmol, 39.3% yield).

1550

Step 2: (2R,3S)-3-methylhex-5-ene-2-sulfonamide and (2S,3S)-3-methylhex-5-ene-2-sulfonamide

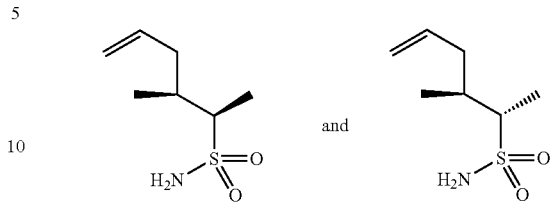

The title compounds were synthesized from (2R,3S)—N,N-bis(4-methoxybenzyl)-3-methylhex-5-ene-2-sulfonamide and (2S,3S)—N,N-bis(4-methoxybenzyl)-3-methylhex-5-ene-2-sulfonamide (539 mg; 1.29 mmol) following the procedure described for Example 26, Step 2. (2R,3S)-3-methylhex-5-ene-2-sulfonamide and (2S,3S)-3-methylhex-5-ene-2-sulfonamide were obtained as a 2.3:1 mixture (203 mg, 1.15 mmol, 89% yield).

Step 3: (S)-6'-chloro-5-(((1R,2R)-2-((1S,5S,6R,E)-1-hydroxy-5-methyl-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1S,5S,6S,E)-1-hydroxy-5-methyl-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic Acid

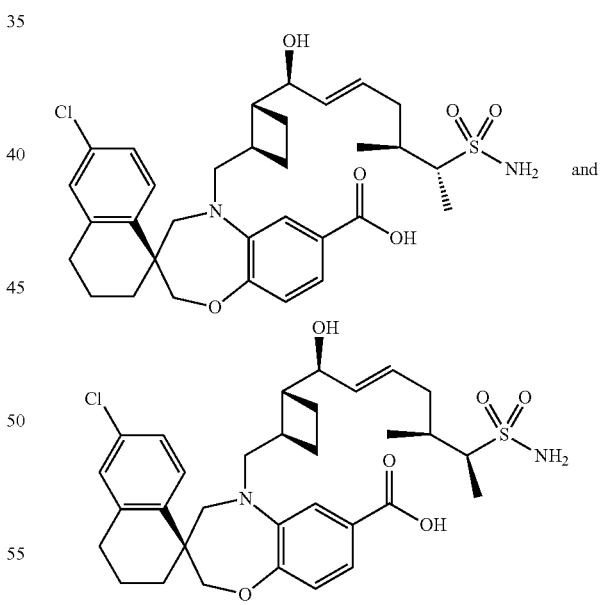

The title compounds were synthesized from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A; 75 mg, 0.147 mmol) and a 2.3:1 mixture of (2R,3S)-3-methylhex-5-ene-2-sulfonamide and (2S,3S)-3-methylhex-5-ene-2-sulfonamide (153 mg, 0.863 mmol) following the procedure described for Example 26, Step 3. The mixture of (S)-6'-chloro-5-(((1R,2R)-2-((1S,5S, 6R,E)-1-hydroxy-5-methyl-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,6S,E)-1-hydroxy-5-methyl-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic acid (73 mg, 0.118 mmol, 80% yield) was carried on to the next step.

Step 4. (1S,3'R,6'R,7'S,8'E,11'S,12'S)-6-chloro-7'-hydroxy-11',12'-dimethyl-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[8,16,18,24]tetraen]-15'-one 13',13'-dioxide

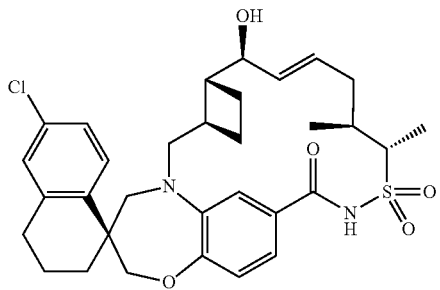

The title compound was synthesized from (S)-6'-chloro-5-(((1R,2R)-2-((1S,5S,6R,E)-1-hydroxy-5-methyl-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,6S,E)-1-hydroxy-5-methyl-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic acid (73 mg, 0.118 mmol) following the procedure described for Example 164, Step 6. The crude material was purified by chromatography through a 12 g ISCO gold column, eluting with 10-40-50% EtOAc (containing 0.3% AcOH) in hexanes over 24 min, to provide (1S,3'R,6'R,7'S,8'E,11'S,12'S)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as the first eluting minor isomer. This material was repurified via reverse-phase HPLC eluting with 50-70% acetonitrile (containing 0.1% TFA) in water (containing 0.1% TFA) to provide the title compound (5.8 mg, 0.0097 mmol, 8.2% yield, 90% purity). $^1$H NMR (400 MHz, CD$_2$Cl$_2$) δ 8.21 (s, 1H), 7.71 (d, J=8.4 Hz, 1H), 7.18 (dd, J=2.3, 8.4 Hz, 1H), 7.14 (dd, J=2.1, 8.1 Hz, 1H), 7.09 (d, J=2.3 Hz, 1H), 6.95 (d, J=8.2 Hz, 1H), 6.69 (br s, 1H), 6.10-5.99 (m, 1H), 5.67 (dd, J=6.4, 15.4 Hz, 1H), 4.20-4.14 (m, 1H), 4.11 (d, J=12.1 Hz, 1H), 4.06 (d, J=11.9 Hz, 1H), 3.84-3.74 (m, 1H), 3.76 (d, J=15.5 Hz, 1H), 3.65 (d, J=14.7 Hz, 1H), 3.44 (d, J=14.7 Hz, 1H), 3.33-3.20 (m, 1H), 2.86-2.70 (m, 2H), 2.60-2.48 (m, 2H), 2.31-2.20 (m, 2H), 2.08-1.98 (m, 2H), 1.97-1.80 (m, 4H), 1.79-1.68 (m, 1H), 1.67-1.49 (m, 2H), 1.46 (d, J=7.2 Hz, 3H), 1.42 (br s, 1H), 1.08 (d, J=7.0 Hz, 3H). MS (ESI, +ve ion) m/z 599.1 (M+H)$^+$.

Step 5: ethyl (((1S,3'R,6'R,7'S,8'E,11'S,12'S)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetate To a solution of (1S,3'R,6'R,7'S,8'E,11'S,12'S)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 738, Step 4; 21 mg, 0.035 mmol) in DCM (701 µl) at ambient temperature was added rhodium (II) acetate dimer (Sigma Aldrich; 0.387 mg, 0.876 µmol), followed by the dropwise addition of ethyl diazoacetate (Sigma Aldrich; 7.98 µl, 0.077 mmol). The reaction mixture was stirred at ambient temperature for 24 h adding more reagent as needed to drive the reaction. The reaction mixture was then directly injected onto a Redi-Sep pre-packed silica gel column (4 g), and purified eluting with 0% to 30% EtOAc(containing 0.3% AcOH) in heptanes, to provide ethyl (((1S,3'R,6'R,7'S,8'E,11'S,12'S)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetate (9.4 mg, 0.014 mmol, 39.1% yield, 90% purity). $^1$H NMR (400 MHz, CD$_2$Cl$_2$) δ 8.09 (br s, 1H), 7.71 (d, J=8.6 Hz, 1H), 7.19 (d, J=8.4 Hz, 1H), 7.17 (d, J=8.4 Hz, 1H), 7.09 (d, J=2.3 Hz, 1H), 6.96 (d, J=8.2 Hz, 1H), 6.64 (s, 1H), 6.13-6.02 (m, 1H), 5.51 (dd, J=9.0, 15.7 Hz, 1H), 4.15 (dq, J=2.2, 7.1 Hz, 2H), 4.11-4.03 (m, 2H), 4.04 (d, J=16.4 Hz, 1H), 3.95 (d, J=16.6 Hz, 1H), 3.86 (dd, J=3.6, 8.5 Hz, 1H), 3.82-3.77 (m, 1H), 3.77 (d, J=14.9 Hz, 1H), 3.68 (d, J=15.7 Hz, 1H), 3.42 (d, J=14.3 Hz, 1H), 3.22 (dd, J=10.9, 15.2 Hz, 1H), 2.87-2.70 (m, 2H), 2.66-2.48 (m, 2H), 2.40 (ddd, J=3.7, 8.6, 17.0 Hz, 1H), 2.29-2.18 (m, 1H), 2.09-1.98 (m, 3H), 1.97-1.81 (m, 4H), 1.73 (td, J=8.7, 17.4 Hz, 1H), 1.47 (d, J=7.2 Hz, 3H), 1.41 (d, J=12.1 Hz, 1H), 1.24 (t, J=6.8 Hz, 3H), 1.07 (d, J=7.0 Hz, 3H). MS (ESI, +ve ion) m/z 685.1 (M+H)$^+$.

Example 739. (((1S,3'R,6'R,7'S,8'E,11'S,12'S)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetic Acid

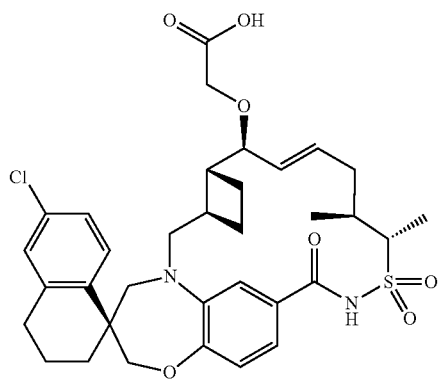

A vial was charged with ethyl (((1S,3'R,6'R,7'S,8'E,11'S,12'S)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetate (Example 738; 7.7 mg, 0.011 mmol), THF (150 μl), MeOH (75 μl) and 1 N LiOH (79 μl, 0.079 mmol). The mixture was stirred at ambient temperature for 45 min then it was quenched with 1 N HCl (157 μl, 0.157 mmol), diluted with brine and extracted with EtOAc. The combined organics were dried over MgSO$_4$ and concentrated. The crude material was purified by chromatography through a Redi-Sep pre-packed silica gel column (4 g), eluting with 15% to 50% EtOAc (containing 0.3% AcOH) in heptanes to provide (((1S,3'R,6'R,7'S,8'E,11'S,12'S)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetic acid (5.5 mg, 0.0084 mmol, 74.5% yield). $^1$H NMR (500 MHz, CD$_2$Cl$_2$) δ 8.91 (br s, 1H), 7.73 (d, J=8.6 Hz, 1H), 7.23 (dd, J=1.8, 8.2 Hz, 1H), 7.20 (dd, J=2.3, 8.4 Hz, 1H), 7.12 (d, J=2.2 Hz, 1H), 6.97 (d, J=8.3 Hz, 1H), 6.77 (br s, 1H), 6.28-6.18 (m, 1H), 5.53 (dd, J=9.2, 15.5 Hz, 1H), 4.12-4.08 (m, 2H), 4.06 (d, J=17.1 Hz, 1H), 3.98 (d, J=17.1 Hz, 1H), 4.01-3.92 (m, 1H), 3.90-3.85 (m, 2H), 3.80 (d, J=14.4 Hz, 1H), 3.43 (d, J=14.7 Hz, 1H), 3.22 (dd, J=10.8, 14.4 Hz, 1H), 2.83-2.71 (m, 2H), 2.64-2.56 (m, 1H), 2.52 (ddd, J=3.9, 8.8, 17.9 Hz, 1H), 2.24-2.16 (m, 1H), 2.11-2.01 (m, 2H), 1.99-1.93 (m, 2H), 1.90 (dt, J=5.0, 8.9 Hz, 4H), 1.76 (td, J=9.1, 18.6 Hz, 1H), 1.50 (d, J=7.1 Hz, 3H), 1.49-1.42 (m, 1H), 1.08 (d, J=7.1 Hz, 3H). MS (ESI, +ve ion) m/z 657.0 (M+H)$^+$.

Example 740. (1S,3'R,6'R,7'S,8'E,11'S,12'R)-6-chloro-12'-ethyl-7'-(2-methoxyethoxy)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one-13', 13'-dioxide

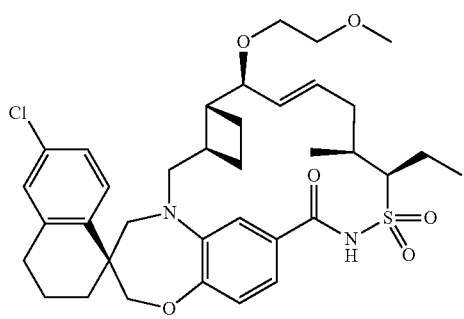

Step 1: (3R,4S)—N,N-bis(4-methoxybenzyl)-4-methylhept-6-ene-3-sulfonamide and (3S,4S)—N,N-bis(4-methoxybenzyl)-4-methylhept-6-ene-3-sulfonamide

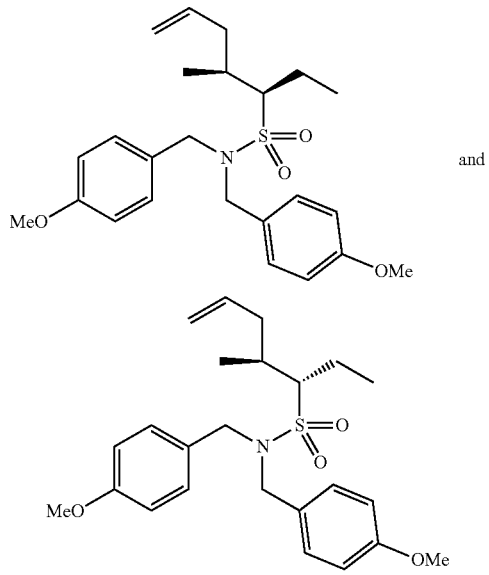

The title compounds were synthesized from N,N-bis(4-methoxybenzyl)propane-1-sulfonamide (Intermediate EE14; 1512 mg, 4.16 mmol) and (R)-pent-4-en-2-yl 4-methylbenzenesulfonate (prepared according to the procedure by Sigman, M. S. et al.; J. Am. Chem. Soc., 2012, 134(28), 11408-11411; 2.0 g, 8.32 mmol) following the procedure described for example 26, step 1. (3R,4S)—N,N-bis(4-methoxybenzyl)-4-methylhept-6-ene-3-sulfonamide and (3S,4S)—N,N-bis(4-methoxybenzyl)-4-methylhept-6-ene-3-sulfonamide were obtained as an inseparable mixture (335 mg, 0.776 mmol, 18.7% yield)

Step 2: (3R,4S)-4-methylhept-6-ene-3-sulfonamide and (3S,4S)-4-methylhept-6-ene-3-sulfonamide

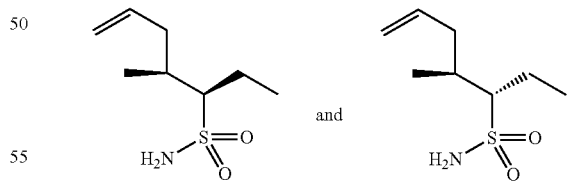

The title compounds were synthesized from (3R,4S)—N,N-bis(4-methoxybenzyl)-4-methylhept-6-ene-3-sulfonamide and (3S,4S)—N,N-bis(4-methoxybenzyl)-4-methylhept-6-ene-3-sulfonamide (335 mg, 0.776 mmol) following the procedure described for Example 26, Step 2. (3R,4S)-4-methylhept-6-ene-3-sulfonamide and (3S,4S)-4-methylhept-6-ene-3-sulfonamide were obtained as an inseparable mixture (67.6 mg, 0.35 mmol, 45.5% yield).

1555

Step 3: (S)-6'-chloro-5-(((1R,2R)-2-((1S,5S,6R,E)-1-hydroxy-5-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1S,5S,6S,E)-1-hydroxy-5-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic Acid

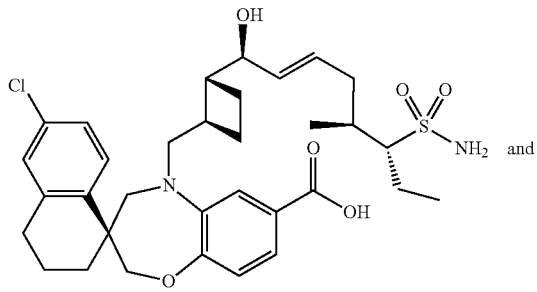

and

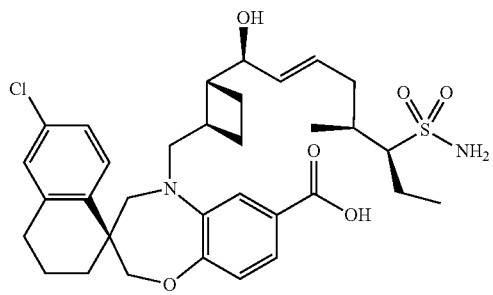

The title compounds were synthesized from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A; 40 mg, 0.078 mmol) and a mixture of (3R,4S)-4-methylhept-6-ene-3-sulfonamide and (3S,4S)-4-methylhept-6-ene-3-sulfonamide (67.6 mg, 0.35 mmol) following the procedure described for Example 164, Step 5. The mixture of (S)-6'-chloro-5-(((1R,2R)-2-((1S,5S,6R,E)-1-hydroxy-5-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,6S,E)-1-hydroxy-5-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid (46 mg, 0.073 mmol, 92% yield) was carried on to the next step.

1556

Step 4. (1S,3'R,6'R,7'S,8'E,11'S,12'R)-6-chloro-12'-ethyl-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

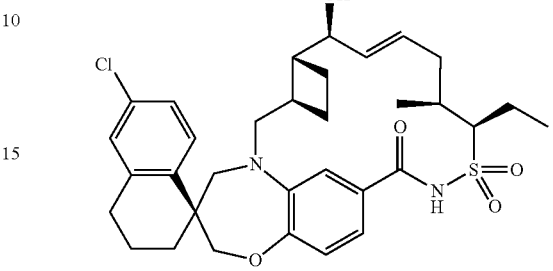

The title compound was synthesized from (S)-6'-chloro-5-(((1R,2R)-2-((1S,5S,6R,E)-1-hydroxy-5-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,6S,E)-1-hydroxy-5-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid (63 mg, 0.100 mmol) following the procedure described for Example 164, Step 6. The crude material was purified by chromatography through a 12 g ISCO gold column, eluting with 10-40-50% EtOAc (containing 0.3% AcOH) in hexanes over 24 min, to provide (1S,3'R,6'R,7'S,8'E,11'S,12'R)-6-chloro-12'-ethyl-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as the second eluting major isomer. This material was repurified by chromatography through a 12 g ISCO gold column, eluting with 0-10% acetone in DCM to provide the title compound (20 mg, 0.033 mmol, 32.7% yield). $^1$H NMR (400 MHz, CD$_2$Cl$_2$) δ 8.33 (br s, 1H), 7.71 (d, J=8.4 Hz, 1H), 7.17 (dd, J=2.3, 8.4 Hz, 1H), 7.09 (d, J=2.3 Hz, 1H), 6.96-6.88 (m, 3H), 5.86 (ddd, J=3.9, 9.0, 15.1 Hz, 1H), 5.71 (dd, J=8.2, 15.1 Hz, 1H), 4.22 (dd, J=3.9, 8.2 Hz, 1H), 4.09-4.08 (m, 2H), 3.98 (ddd, J=1.2, 3.7, 8.8 Hz, 1H), 3.82 (d, J=14.7 Hz, 1H), 3.69 (d, J=14.3 Hz, 1H), 3.25 (d, J=14.3 Hz, 1H), 3.04 (dd, J=9.5, 15.4 Hz, 1H), 2.85-2.69 (m, 2H), 2.41 (ddd, J=3.7, 9.8, 18.4 Hz, 1H), 2.35-2.24 (m, 1H), 2.21-2.11 (m, 1H), 2.10-2.03 (m, 2H), 1.99-1.90 (m, 3H), 1.90-1.74 (m, 5H), 1.67 (quin, J=9.5 Hz, 2H), 1.45-1.34 (m, 1H), 1.27 (t, J=7.4 Hz, 3H), 1.02 (d, J=6.8 Hz, 3H). MS (ESI, +ve ion) m/z 613.0 (M+H)$^+$.

Step 5: (1S,3'R,6'R,7'S,8'E,11'S,12'R)-6-chloro-12'-ethyl-7'-(2-methoxyethoxy)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one-13',13'-dioxide To a solution of (1S,3'R,6'R,7'S,8'E,11'S,12'R)-6-chloro-12'-ethyl-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (10 mg, 0.016 mmol) in THF cooled to 0° C. was added sodium hydride (60% dispersion in mineral oil; 6.52 mg, 0.163 mmol). The reaction mixture was stirred at 0° C. for 15 min, and then 2-bromoethyl methyl ether (Alfa Aesar; 7.7 μl, 0.082 mmol) was added. The reaction mixture was stirred at ambient temperature for several hours adding more reagents in small portions. Minimal reaction was observed and the reaction seemed to stall at about 50% conversion after 5 days. The mixture was then quenched with aq NH₄Cl and diluted with EtOAc. The organic layer was separated, dried over MgSO₄ and concentrated. The crude material was purified by chromatography through a Redi-Sep pre-packed silica gel column (4 g), eluting with 10-40% EtOAc (containing 0.3% AcOH) in heptanes to provide (1S,3'R,6'R,7'S,8'E,11'5,12'R)-6-chloro-12'-ethyl-7'-(2-methoxyethoxy)-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one-13', 13'-dioxide (1.8 mg, 0.0027 mmol, 16.4% yield). $^1$H NMR (500 MHz, CD₂Cl₂) δ 8.08 (s, 1H), 7.71 (d, J=8.6 Hz, 1H), 7.17 (dd, J=2.4, 8.6 Hz, 1H), 7.09 (d, J=2.2 Hz, 1H), 6.91 (d, J=0.7 Hz, 2H), 6.87 (s, 1H), 5.82 (ddd, J=3.4, 9.4, 15.3 Hz, 1H), 5.54 (dd, J=9.4, 15.8 Hz, 1H), 4.11-4.05 (m, 2H), 4.00 (dd, J=2.8, 9.4 Hz, 1H), 3.82 (d, J=14.9 Hz, 1H), 3.78 (dd, J=3.2, 9.0 Hz, 1H), 3.69 (d, J=14.4 Hz, 1H), 3.53 (ddd, J=3.4, 5.4, 9.3 Hz, 1H), 3.45 (dt, J=3.7, 5.0 Hz, 2H), 3.38 (ddd, J=3.4, 5.9, 9.5 Hz, 1H), 3.32 (s, 3H), 3.25 (d, J=14.4 Hz, 1H), 3.02 (dd, J=10.3, 15.4 Hz, 1H), 2.84-2.70 (m, 2H), 2.45 (ddd, J=3.7, 10.0, 19.1 Hz, 1H), 2.37-2.29 (m, 1H), 2.29-2.19 (m, 1H), 2.13-2.08 (m, 1H), 2.08-2.01 (m, 2H), 2.00-1.89 (m, 3H), 1.89-1.77 (m, 4H), 1.66 (quin, J=8.6 Hz, 1H), 1.44-1.35 (m, 1H), 1.28 (t, J=7.3 Hz, 3H), 1.02 (d, J=6.8 Hz, 3H). MS (ESI, +ve ion) m/z 671.1 (M+H)$^+$; 693.1 (M+Na)$^+$.

Example 741. methyl (((1S,3'R,6'R,7'S,8'E,11'R)-6-chloro-11'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl) oxy)acetate

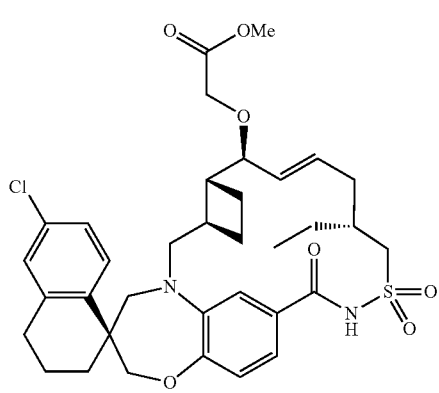

Step 1: (S)-2-ethyl-N,N-bis(4-methoxybenzyl)pent-4-ene-1-sulfonamide and (R)-2-ethyl-N,N-bis(4-methoxybenzyl)pent-4-ene-1-sulfonamide

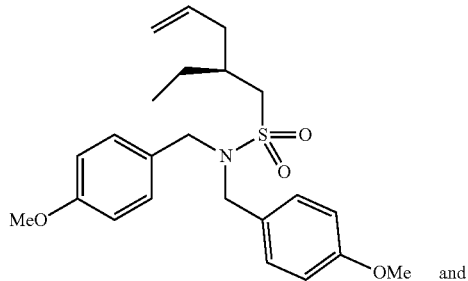

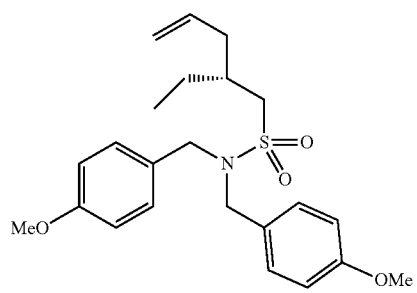

The title compound was synthesized from N,N-bis(4-methoxybenzyl) methanesulfonamide (intermediate EE12; 1.10 g, 3.28 mmol) and hex-5-en-3-yl 4-methylbenzenesulfonate (prepared according to the procedure by Sigman, M. S. et al.; *J. Am. Chem. Soc.*, 2012, 134(28), 11408-11411; 1.50 g, 5.90 mmol) according to the procedure described for Intermediate 38, Step 1. (S)-2-ethyl-N,N-bis(4-methoxybenzyl)pent-4-ene-1-sulfonamide and (R)-2-ethyl-N,N-bis(4-methoxybenzyl)pent-4-ene-1-sulfonamide were obtained as a racemic mixture (435 mg, 1.04 mmol, 31.8% yield).

Step 2: (S)-2-ethylpent-4-ene-1-sulfonamide and (R)-2-ethylpent-4-ene-1-sulfonamide

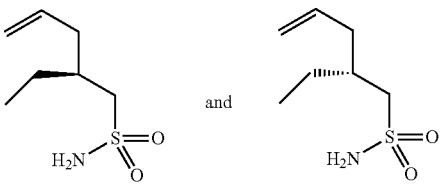

The title compound was synthesized from a racemic mixture of (S)-2-ethyl-N,N-bis(4-methoxybenzyl)pent-4-ene-1-sulfonamide and (R)-2-ethyl-N,N-bis(4-methoxybenzyl)pent-4-ene-1-sulfonamide (435 mg, 1.04 mmol) according to the procedure described for Example 26, Step 2. (S)-2-ethylpent-4-ene-1-sulfonamide and (R)-2-ethylpent-4-ene-1-sulfonamide were obtained as a racemic mixture (149 mg, 0.84 mmol, 81% yield).

Step 3: (S)-6'-chloro-5-(((1R,2R)-2-((1S,5S,E)-1-hydroxy-5-(sulfamoylmethyl)hept-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1S,5R,E)-1-hydroxy-5-(sulfamoylmethyl)hept-2-en-1-yl)cyclobutyl)methyl)-3',4,4',5-tetrahydro-2H,2'H-spiro[benzo[b][1,4]oxazepine-3,1'-naphthalene]-7-carboxylic Acid

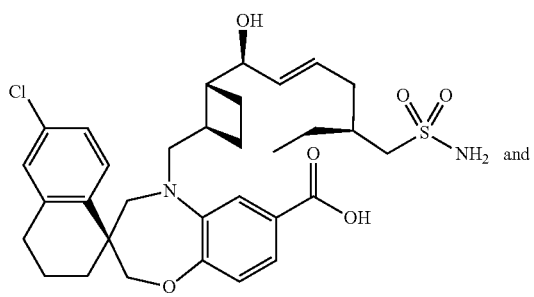

and

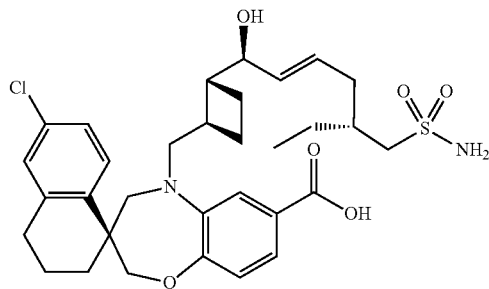

The title compounds were synthesized from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A; 80 mg, 0.157 mmol) and a mixture of (S)-2-ethylpent-4-ene-1-sulfonamide and (R)-2-ethylpent-4-ene-1-sulfonamide (149 mg, 0.84 mmol) following the procedure described for Example 164, Step 5. Purification of the crude material eluting with a gradient of 0-20-50-100% EtOAc in heptanes followed by a gradient of 20-50% EtOAc (containing 0.3% AcOH) in heptanes provided an inseparable mixture of (S)-6'-chloro-5-(((1R,2R)-2-((1S,5S,E)-1-hydroxy-5-(sulfamoylmethyl)hept-2-en-1-yl)cyclobutyl)methyl)-3',4,4',5-tetrahydro-2H,2'H-spiro [benzo [b][1,4]oxazepine-3,1'-naphthalene]-7-carboxylic Acid and (S)-6'-chloro-5-(((1R,2R)-2-((1S,5R,E)-1-hydroxy-5-(sulfamoylmethyl)hept-2-en-1-yl)cyclobutyl)methyl)-3',4,4',5-tetrahydro-2H,2'H-spiro[benzo[b][1,4]oxazepine-3,1'-naphthalene]-7-carboxylic acid (75 mg, 0.122 mmol, 77% yield).

Step 4. 1S,3'R,6'R,7'S,8'E,11'R)-6-chloro-11'-ethyl-7'-hydroxy-3,4-dihydro-2H,15'H-spiro[naphthalene-1,22'-[20]oxa[13]thia[1,14]diaza tetracyclo [14.7.2.0$^{3,6}$.0$^{19,24}$]pentacosa[8,16,18,24]tetraen]-15'-one 13',13'-dioxide

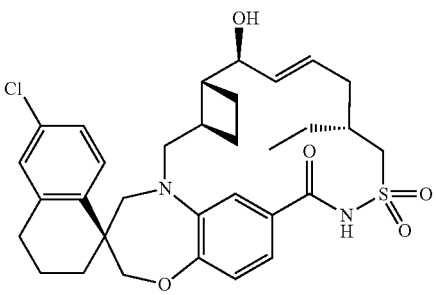

The title compound was synthesized from (S)-6'-chloro-5-(((1R,2R)-2-((1S,5S,E)-1-hydroxy-5-(sulfamoylmethyl)hept-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5R,E)-1-hydroxy-5-(sulfamoylmethyl)hept-2-en-1-yl)cyclobutyl)methyl)-3',4,4',5-tetrahydro-2H,2'H-spiro[benzo[b][1,4]oxazepine-3,1'-naphthalene]-7-carboxylic acid (75 mg, 0.122 mmol) following the procedure described for Example 164, Step 6. The crude material was purified by chromatography through a 12 g ISCO gold column, eluting with 10-30-50% EtOAc (containing 0.3% AcOH) in hexanes over 24 min, to provide (1S,3'R,6'R,7'S,8'E,11'R)-6-chloro-11'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as the first eluting isomer (20.4 mg, 0.034 mmol, 28.0% yield). $^1$H NMR (400 MHz, CD$_2$Cl$_2$) δ 8.45 (br s, 1H), 7.67 (d, J=8.6 Hz, 1H), 7.44 (br s, 1H), 7.15 (dd, J=2.3, 8.4 Hz, 1H), 7.10 (d, J=2.3 Hz, 1H), 6.96 (dd, J=1.8, 8.0 Hz, 1H), 6.91 (d, J=8.0 Hz, 1H), 5.71 (dd, J=4.7, 15.7 Hz, 1H), 5.66-5.55 (m, 1H), 4.24-4.13 (m, 2H), 3.96 (br s, 1H), 3.92 (d, J=15.7 Hz, 1H), 3.79 (br s, 1H), 3.64 (d, J=13.3 Hz, 1H), 3.42 (d, J=14.5 Hz, 1H), 3.30-3.11 (m, 2H), 2.79-2.71 (m, 2H), 2.56-2.41 (m, 2H), 2.29 (dd, J=5.5, 13.9 Hz, 1H), 1.91-1.75 (m, 7H), 1.75-1.63 (m, 4H), 1.45 (dt, J=7.6, 14.3 Hz, 2H), 0.92 (t, J=7.3 Hz, 3H). MS (ESI, +ve ion) m/z 599.0 (M+H)$^+$.

Step 5: methyl (((1S,3'R,6'R,7'S,8'E,11'R)-6-chloro-11'-ethyl-13',13'-dioxido-15'-oxo-3,4-dihydro-2H-spiro[naphthalene-1,22'-[20]oxa[13]thia[1,14]diaza tetracyclo[14.7.2.0$^{3,6}$.0$^{19,24}$]pentacosa[8,16,18,24] tetraen]-7'-yl)oxy) acetate To a solution of (1S,3'R,6'R,7'S,8'E,11'R)-6-chloro-11'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 765; 18 mg, 0.030 mmol) in THF (0.60 mL) cooled to 0° C. was added sodium hydride (60% dispersion in mineral oil; 6 mg, 0.150 mmol). The reaction mixture was stirred at 0° C. for 30 min, and then methyl bromoacetate (Alfa Aesar; 8.33 μl, 0.090 mmol) was added. The reaction mixture was stirred at ambient temperature for 6 h (more NaH was added to drive the reaction to near completion) and then was quenched with sat. NH$_4$Cl, extracted with EtOAc, dried over MgSO₄ and concentrated The crude material was purified by chromatography through a Redi-Sep pre-packed silica gel column (4 g), eluting with 0% to 30% EtOAc (containing 0.3% AcOH) in heptanes, to provide methyl ((((1S,3'R,6'R,7'S,8'E,11'R)-6-chloro-11'-ethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl)oxy)acetate (5.0 mg, 0.0075 mmol, 24.8% yield). ¹H NMR (400 MHz, CD₂Cl₂) δ 8.27 (br s, 1H), 7.70 (d, J=8.4 Hz, 1H), 7.16 (dd, J=2.2, 8.4 Hz, 1H), 7.09 (d, J=2.3 Hz, 1H), 7.00-6.96 (m, 1H), 6.91 (d, J=8.0 Hz, 1H), 6.91-6.87 (m, 1H), 5.88 (ddd, J=4.3, 8.0, 15.5 Hz, 1H), 5.52 (dd, J=7.8, 15.8 Hz, 1H), 4.13 (d, J=16.6 Hz, 1H), 4.13-4.04 (m, 3H), 3.99 (d, J=16.4 Hz, 1H), 3.85 (dd, J=3.5, 7.6 Hz, 1H), 3.72 (s, 3H), 3.64 (d, J=14.5 Hz, 1H), 3.59-3.52 (m, 2H), 3.37 (d, J=14.7 Hz, 1H), 3.27 (br s, 1H), 2.83-2.68 (m, 2H), 2.46 (br s, 2H), 2.32-2.16 (m, 2H), 2.13-2.04 (m, 1H), 2.02-1.95 (m, 1H), 1.95-1.84 (m, 3H), 1.83-1.74 (m, 3H), 1.70 (dd, J=9.0, 18.4 Hz, 1H), 1.61-1.42 (m, 2H), 0.96 (t, J=7.3 Hz, 3H). MS (ESI, +ve ion) m/z 671.0 (M+H)⁺.

Example 742. (1S,3'R,6'R,7'S,9'E,12'R)-6-chloro-7'-hydroxy-12'-methyl-3,4-dihydro-2H,15'H-spiro[naphthalene-1,22'-[20]oxa[13]thia[1,14]diaza tetracyclo[14.7.2.0³,⁶.0¹⁹,²⁴]pentacosa[9,16,18,24]tetraen]-15'-one 13',13'-dioxide

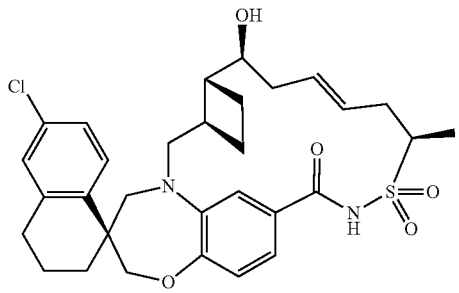

Step 1: (S)-6'-chloro-5-(((1R,2R)-2-((S)-1-hydroxybut-3-en-1-yl)cyclobutyl)methyl)-N—((R)-pent-4-en-2-ylsulfonyl)-3',4,4',5-tetrahydro-2H,2'H-spiro[benzo[b][1,4]oxazepine-3,1'-naphthalene]-7-carboxamide

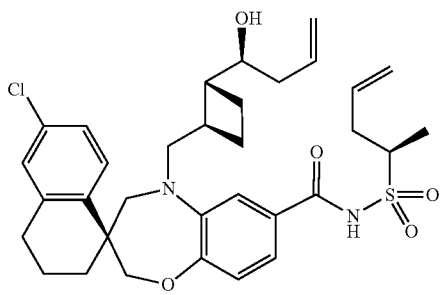

The title compound was synthesized from (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (intermediate AA13A; 166 mg, 0.344 mmol) and (R)-pent-4-ene-2-sulfonamide (intermediate EE17; 87 mg, 0.585 mmol) following the procedure described for Example 719, Step 2, Step 1. Purification of the crude material provided (S)-6'-chloro-5-(((1R,2R)-2-((S)-1-hydroxybut-3-en-1-yl)cyclobutyl)methyl)-N—((R)-pent-4-en-2-ylsulfonyl)-3',4,4',5-tetrahydro-2H,2'H-spiro[benzo[b][1,4]oxazepine-3,1'-naphthalene]-7-carboxamide (134 mg, 0.219 mmol, 63.5% yield).

Step 2. (1S,3'R,6'R,7'S,9'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide A 500 mL round bottom flask was charged with (S)-6'-chloro-5-(((1R,2R)-2-((S)-1-hydroxybut-3-en-1-yl)cyclobutyl)methyl)-N—((R)-pent-4-en-2-ylsulfonyl)-3',4,4',5-tetrahydro-2H,2'H-spiro[benzo[b][1,4]oxazepine-3,1'-naphthalene]-7-carboxamide (134 mg, 0.219 mmol) in toluene (146.00 mL). It was stirred at ambient temperature for 10 min to dissolve the solid starting material and then subjected to three cycles of evacuation/back-filling with nitrogen. To the homogeneous solution was added a solution of Hoveyda-Grubbs II (27.4 mg, 0.044 mmol) in toluene (8 mL) at ambient temperature. The mixture was stirred at 106° C. under nitrogen for 80 min. Air was blown through the solution for 10 min to deactivate the catalyst, and then the mixture was concentrated. The crude dark oil was absorbed onto a plug of silica gel and purified by chromatography through a 24 g ISCO column, eluting with 10% to 20% to 40% EtOAc (containing 0.3% AcOH) in hexanes over 90 min. The material thus obtained was further purified by reverse phase HPLC to provide (1S,3'R,6'R,7'S,9'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide as the first eluting and minor isomer. ¹H NMR (500 MHz, CDCl₃) δ 10.00 (br s, 1H), 7.71 (d, J=8.6 Hz, 1H), 7.44 (d, J=8.3 Hz, 1H), 7.18 (dd, J=2.1, 8.4 Hz, 1H), 7.10 (d, J=1.7 Hz, 1H), 6.99 (d, J=8.3 Hz, 2H), 5.63-5.52 (m, 2H), 4.17-4.12 (m, 2H), 4.07 (ddd, J=5.1, 7.1, 12.2 Hz, 1H), 3.90-3.84 (m, 1H), 3.62 (d, J=14.2 Hz, 1H), 3.58 (br s, 1H), 3.35 (d, J=14.2 Hz, 1H), 3.33-3.24 (m, 1H), 3.09-2.94 (m, 1H), 2.83-2.73 (m, 2H), 2.59 (dd, J=2.6, 13.8 Hz, 2H), 2.50 (td, J=9.7, 14.1 Hz, 2H), 2.41-2.29 (m, 2H), 2.17-2.11 (m, 1H), 2.02 (d, J=7.6 Hz, 1H), 1.98-1.87 (m, 2H), 1.79 (t, J=8.1 Hz, 3H), 1.72-1.61 (m, 1H), 1.56 (d, J=7.1 Hz, 3H). MS (ESI, +ve ion) m/z 585.1 (M+H)⁺.

Example 743. (1S,3'R,6'R,7'S,9'Z,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide

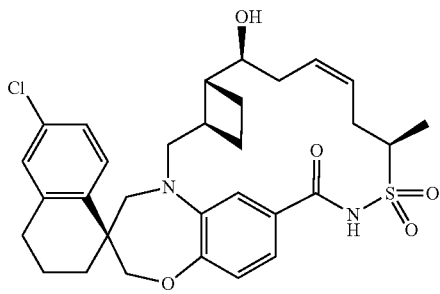

The title compound was synthesized as described for Example 742, Step 2. (1S,3'R,6'R,7'S,9'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide was obtained as the second eluting and major isomer. ¹H NMR (500 MHz, CDCl₃) δ 10.76 (br s, 1H), 7.60 (d, J=8.3 Hz, 1H), 7.50 (d, J=7.8 Hz, 1H), 7.45-7.36 (m, 1H), 7.15 (dd, J=2.2, 8.6 Hz, 1H), 7.10 (d, J=2.2 Hz, 1H), 6.99 (d, J=8.3 Hz, 1H), 5.67 (br s, 1H), 5.39 (br s, 1H), 4.31 (d, J=11.7 Hz, 1H), 4.14 (d, J=11.7 Hz, 1H), 4.06-3.97 (m, 1H), 3.77 (br s, 1H), 3.61 (br s, 1H), 3.45-3.35 (m, 1H), 3.08 (d, J=14.9 Hz, 1H), 3.04-2.87 (m, 3H), 2.76 (t, J=6.0 Hz, 2H), 2.68-2.48 (m, 2H), 2.35 (d, J=6.8 Hz, 2H), 1.94-1.84 (m, 2H), 1.83-1.67 (m, 5H), 1.62 (d, J=7.1 Hz, 3H), 1.57-1.45 (m, 2H). MS (ESI, +ve ion) m/z 585.1 (M+H)⁺.

Example 744. (1S,3'R,6'R,7'S,9'Z,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide

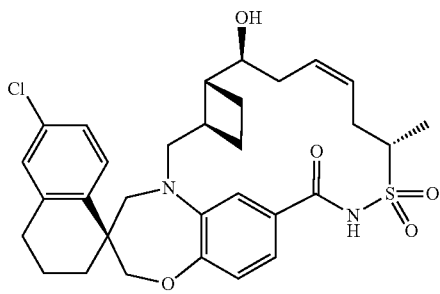

Step 1: (S)-6'-chloro-5-(((1R,2R)-2-((S)-1-hydroxybut-3-en-1-yl)cyclobutyl)methyl)-N—((S)-pent-4-en-2-ylsulfonyl)-3',4,4',5-tetrahydro-2H,2'H-spiro[benzo[b][1,4]oxazepine-3,1'-naphthalene]-7-carboxamide

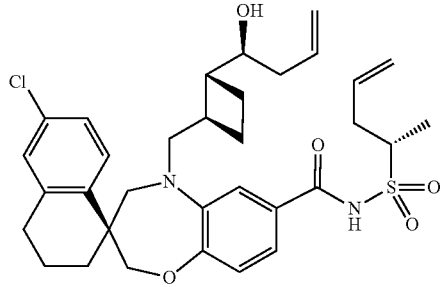

The title compound was synthesized from (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (intermediate AA13A; 15 mg, 0.031 mmol) and (S)-pent-4-ene-2-sulfonamide (intermediate EE172; 5.6 mg, 0.037 mmol) following the procedure described for Example 719, Step 2, Step 1. Purification of the crude material provided (S)-6'-chloro-5-(((1R,2R)-2-((S)-1-hydroxybut-3-en-1-yl)cyclobutyl)methyl)-N—((S)-pent-4-en-2-ylsulfonyl)-3',4,4',5-tetrahydro-2H,2'H-spiro[benzo[b][1,4]oxazepine-3,1'-naphthalene]-7-carboxamide (19 mg, 0.031 mmol).

Step 2. (1S,3'R,6'R,7'S,9'Z,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide The title compound was synthesized from (S)-6'-chloro-5-(((1R,2R)-2-((S)-1-hydroxybut-3-en-1-yl)cyclobutyl)methyl)-N—((S)-pent-4-en-2-ylsulfonyl)-3',4,4',5-tetrahydro-2H,2'H-spiro[benzo[b][1,4]oxazepine-3,1'-naphthalene]-7-carboxamide (42.5 mg, 0.067 mmol) following the procedure described for Example 742, Step 2. Purification by chromatography through a 24 g ISCO column, eluting with 10% to 20% to 40% EtOAc (containing 0.3% AcOH) in hexanes over 90 min. followed by a second purification through a 12 g ISCO column, eluting with 0% to 30% EtOAc (containing 0.3% AcOH) in hexanes provided (1S,3'R,6'R,7'S,9'Z,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide as the first eluting isomer (13.4 mg, 0.023 mmol 34.3% yield). ¹H NMR (400 MHz, CD₂Cl₂) δ 10.31 (br s, 1H), 7.65 (d, J=8.6 Hz, 1H), 7.42 (dd, J=2.0, 8.4 Hz, 1H), 7.37 (br s, 1H), 7.15 (dd, J=2.3, 8.6 Hz, 1H), 7.10 (d, J=2.2 Hz, 1H), 6.98 (d, J=8.4 Hz, 1H), 5.72 (dt, J=4.8, 10.7 Hz, 1H), 5.44 (td, J=5.5, 10.6 Hz, 1H), 4.27 (d, J=11.7 Hz, 1H), 4.14 (d, J=11.9 Hz, 1H), 3.69-3.54 (m, 2H), 3.53-3.41 (m, 2H), 3.27 (br s, 2H), 2.75 (t, J=6.1 Hz, 3H), 2.71-2.58 (m, 1H), 2.46 (br s, 1H), 2.34-2.18 (m, 2H), 2.13 (br s, 1H), 1.97-1.86 (m, 3H), 1.85-1.74 (m, 4H), 1.67 (d, J=6.1 Hz, 1H), 1.59 (d, J=7.0 Hz, 3H), 1.55-1.45 (m, 1H). MS (ESI, +ve ion) m/z 585.1 (M+H)⁺.

Example 745. (1S,3'R,6'R,7'S,9'E,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide

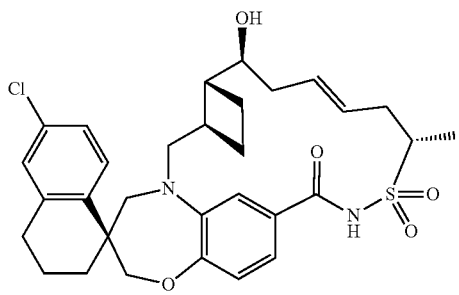

The title compound was synthesized as described for Example 744, Step 2. (1S,3'R,6'R,7'S,9'E,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide was obtained as the second eluting isomer (13.2 mg, 0.023 mmol 34.3% yield). $^1$H NMR (400 MHz, CD$_2$Cl$_2$) δ 9.92 (br s, 1H), 7.67 (d, J=8.6 Hz, 1H), 7.49 (dd, J=2.2, 8.4 Hz, 1H), 7.15 (dd, J=2.3, 8.4 Hz, 1H), 7.10 (d, J=2.3 Hz, 1H), 6.98 (d, J=8.2 Hz, 1H), 5.67 (ddd, J=4.7, 8.8, 14.5 Hz, 1H), 5.59-5.48 (m, 1H), 4.26 (d, J=11.7 Hz, 1H), 4.13 (d, J=11.9 Hz, 1H), 3.83 (td, J=4.9, 6.7 Hz, 1H), 3.76-3.65 (m, 1H), 3.55-3.41 (m, 2H), 2.80-2.72 (m, 3H), 2.72-2.64 (m, 1H), 2.52-2.38 (m, 3H), 2.31 (ddd, J=4.8, 8.4, 13.8 Hz, 3H), 2.14 (td, J=6.3, 13.9 Hz, 1H), 1.97-1.87 (m, 3H), 1.87-1.70 (m, 4H), 1.61 (d, J=7.0 Hz, 3H), 1.55-1.43 (m, 2H). MS (ESI, +ve ion) m/z 585.1 (M+H)$^+$.

Example 746. (1S,3'R,6'R,7'S,9'E,12'R)-6-chloro-12'-ethyl-7'-hydroxy-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[9,16,18,24]tetraen]-15'-one 13',13'-dioxide

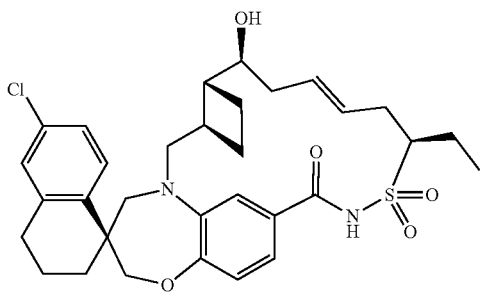

Step 1: (S)-6'-chloro-N—((R)-hex-5-en-3-ylsulfonyl)-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide

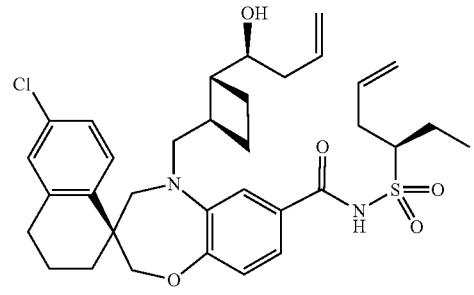

The title compound was synthesized from (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (intermediate AA13A; 140 mg, 0.290 mmol) and (R)-hex-5-ene-3-sulfonamide (intermediate EE18; 85 mg, 0.523 mmol) following the procedure described for Example 719, Step 2, Step 1. Purification of the crude material provided (S)-6'-chloro-N—((R)-hex-5-en-3-ylsulfonyl)-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide (150 mg, 0.239 mmol, 82% yield).

Step 2. (1S,3'R,6'R,7'S,9'E,12'R)-6-chloro-12'-ethyl-7'-hydroxy-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[9,16,18,24]tetraen]-15'-one 13',13'-dioxide The title compound was synthesized from (S)-6'-chloro-N—((R)-hex-5-en-3-ylsulfonyl)-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide (150 mg, 0.239 mmol) following the procedure described for Example 742, Step 2. The crude material was subjected to a first purification by chromatography through a 24 g ISCO column, eluting with 10% to 20% to 40% EtOAc (containing 0.3% AcOH) in hexanes over 90 min. The material thus obtained was further purified by reverse phase HPLC eluting with a gradient of 50-70-100% MeCN (containing 0.1% TFA) in water (containing 0.1% TFA) to provide (1S,3'R,6'R,7'S,9'E,12'R)-6-chloro-12'-ethyl-7'-hydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa[9,16,18,24]tetraen]-15'-one 13',13'-dioxide as the first eluting isomer. $^1$H NMR (500 MHz, CD$_2$Cl$_2$) δ 9.99 (br s, 1H), 7.71 (d, J=8.6 Hz, 1H), 7.36 (dd, J=1.8, 8.4 Hz, 1H), 7.16 (dd, J=2.4, 8.6 Hz, 1H), 7.09 (d, J=2.2 Hz, 1H), 7.01 (br s, 1H), 6.97 (d, J=8.3 Hz, 1H), 5.63-5.52 (m, 2H), 4.19 (d, J=12.0 Hz, 1H), 4.12 (d, J=12.0 Hz, 1H), 3.89-3.82 (m, 2H), 3.61 (d, J=14.4 Hz, 1H), 3.58-3.50 (m, 1H), 3.36 (d, J=13.9 Hz, 1H), 3.02-2.91 (m, 1H), 2.84-2.69 (m, 2H), 2.62-2.56 (m, 1H), 2.55-2.47 (m, 1H), 2.41-2.26 (m, 2H), 2.21-2.09 (m, 3H), 2.02-1.92 (m, 2H), 1.91-1.81 (m, 3H), 1.77 (t, J=8.3 Hz, 2H), 1.74-1.63 (m, 2H), 1.54 (t, J=11.1 Hz, 1H), 1.12 (t, J=7.5 Hz, 3H). MS (ESI, +ve ion) m/z 599.2 (M+H)$^+$.

Example 747. (1S,3'R,6'R,7'S,9'Z,12'S)-6-chloro-12'-ethyl-7'-hydroxy-3,4-dihydro-2H,15'H-spiro[naphthalene-1,22'-[20]oxa[13]thia[1,14]diaza tetracyclo[14.7.2.0³,⁶.0¹⁹,²⁴]pentacosa[9,16,18,24]tetraen]-15'-one 13',13'-dioxide

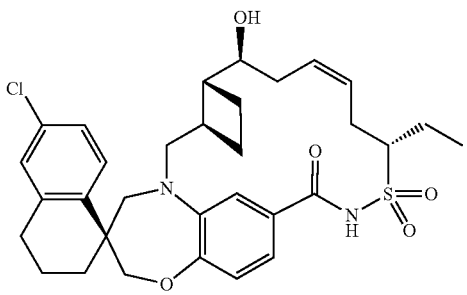

Step 1: (S)-6'-chloro-N—((R)-hex-5-en-3-ylsulfonyl)-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N—((S)-hex-5-en-3-ylsulfonyl)-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide

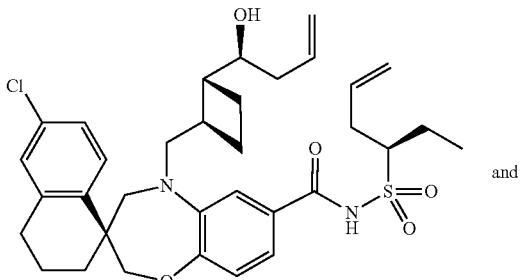

and

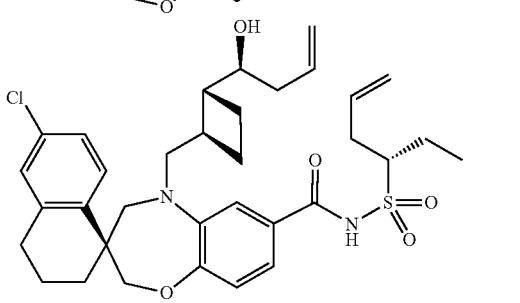

The title compounds were synthesized from (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (intermediate AA13A; 224 mg, 0.465 mmol) and a racemic mixture of (R)-hex-5-ene-3-sulfonamide (intermediate EE18) and (S)-hex-5-ene-3-sulfonamide (intermediate EE182) (167 mg, 1.02 mmol) following the procedure described for Example 1, Step 1. Purification of the crude material provided a mixture of (S)-6'-chloro-N—((R)-hex-5-en-3-ylsulfonyl)-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N—((S)-hex-5-en-3-ylsulfonyl)-5-(((1R,2R)-2-((S)-1-hydroxybut-3-en-1-yl)cyclobutyl) methyl)-3',4,4',5-tetrahydro-2H,2'H-spiro [benzo [b][1,4]oxazepine-3,1'-naphthalene]-7-carboxamide (235 mg, 0.375 mmol, 81% yield).

Step 2. (1S,3'R,6'R,7'S,9'Z,12'S)-6-chloro-12'-ethyl-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide The title compound was synthesized from a mixture of (S)-6'-chloro-N—((R)-hex-5-en-3-ylsulfonyl)-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-en-3-ylsulfonyl)-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide (235 mg, 0.375 mmol) following the procedure described for Example 45, Step 2. The crude material was subjected to purification by chromatography through a 24 g ISCO column, eluting with 10% to 20% to 40% EtOAc (containing 0.3% AcOH) in hexanes over 60 min. to provide (1S,3'R, 6'R,7'S,9'Z,12'S)-6-chloro-12'-ethyl-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide as the first eluting isomer. ¹H NMR (400 MHz, CD₂Cl₂) δ 10.25 (br. s, 1H), 7.66 (d, J=8.4 Hz, 1H), 7.41 (dd, J=2.0, 8.4 Hz, 1H), 7.36 (br s, 1H), 7.15 (dd, J=2.2, 8.5 Hz, 1H), 7.10 (d, J=2.3 Hz, 1H), 6.98 (d, J=8.4 Hz, 1H), 5.73-5.63 (m, 1H), 5.50-5.40 (m, 1H), 4.27 (d, J=11.7 Hz, 1H), 4.14 (d, J=11.9 Hz, 1H), 3.65 (br s, 2H), 3.55 (br s, 1H), 3.52-3.43 (m, 1H), 3.26 (br s, 1H), 3.20-3.10 (m, 1H), 2.76 (t, J=6.2 Hz, 2H), 2.64 (br s, 3H), 2.49 (ttd, J=3.7, 7.5, 18.2 Hz, 2H), 2.23 (br s, 2H), 1.96-1.86 (m, 3H), 1.85-1.73 (m, 4H), 1.72-1.60 (m, 3H), 1.09 (t, J=7.4 Hz, 3H). MS (ESI, +ve ion) m/z 599.2 (M+H)⁺.

Example 748. (1S,3'R,6'R,7'S,9'E,12'S)-6-chloro-12'-ethyl-7'-hydroxy-3,4-dihydro-2H,15'H-spiro[naphthalene-1,22'-[20]oxa[13]thia[1,14]diaza tetracyclo[14.7.2.0³,⁶.0¹⁹,²⁴]pentacosa[9,16,18,24]tetraen]-15'-one 13',13'-dioxide

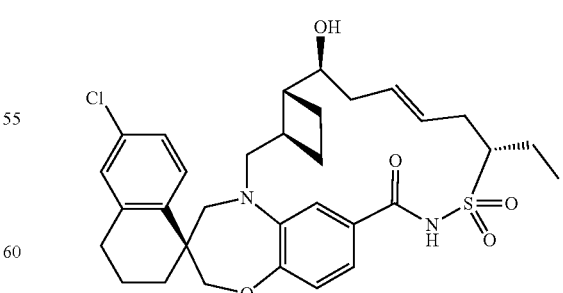

The title compound was synthesized as described for Example 747, Step 2. (1S,3'R,6'R,7'S,9'E,12'S)-6-chloro-12'-ethyl-7'-hydroxy-3,4-dihydro-2H,15'H-spiro[naphthalene-1,22'-[20]oxa[13]thia[1,14]diazatetracyclo[14.7.2.0³, 6.0¹⁹,²⁴]pentacosa[9,16,18,24]tetraen]-15'-one 13',13'-dioxide was obtained as the second eluting isomer. ¹H NMR (400 MHz, CD₂Cl₂) δ 9.90 (br s, 1H), 7.67 (d, J=8.6 Hz, 1H), 7.48 (dd, J=2.2, 8.4 Hz, 1H), 7.24 (br s, 1H), 7.15 (dd, J=2.3, 8.4 Hz, 1H), 7.09 (d, J=2.3 Hz, 1H), 6.98 (d, J=8.4 Hz, 1H), 5.64 (ddd, J=4.3, 8.6, 14.7 Hz, 1H), 5.60-5.49 (m, 1H), 4.24 (d, J=11.5 Hz, 1H), 4.12 (d, J=11.9 Hz, 1H), 4.17-4.05 (m, 1H), 3.86-3.77 (m, 1H), 3.58-3.36 (m, 3H), 2.82-2.67 (m, 3H), 2.50-2.36 (m, 3H), 2.35-2.22 (m, 2H), 2.18-2.07 (m, 2H), 1.97-1.87 (m, 3H), 1.86-1.71 (m, 4H), 1.66-1.55 (m, 2H), 1.54-1.44 (m, 1H), 1.09 (t, J=7.5 Hz, 3H). MS (ESI, +ve ion) m/z 599.2 (M+H)⁺.

Example 749. (1S,3'R,6'R,7'R,12'R)-6-chloro-7'-hydroxy-12'-methyl-3,4-dihydro-2H,15'H-spiro [naphthalene-1,22'-[20]oxa[13]thia[1,14]diaza tetracyclo[14.7.2.0³,⁶.0¹⁹,²⁴]pentacosa[16,18,24]trien]-15'-one 13',13'-dioxide or (1S,3'R,6'R,7'R,12'S)-6-chloro-7'-hydroxy-12'-methyl-3,4-dihydro-2H,15'H-spiro[naphthalene-1,22'-[20]oxa[13]thia[1,14] diazatetracyclo [14.7.2.0³,⁶.0¹⁹,²⁴]pentacosa[16,18,24]trien]-15'-one 13',13'-dioxide Step 1: (S)-6'-chloro-5-(((1R,2R)-2-((R)-1-hydroxy-but-3-en-1-yl)cyclobutyl)methyl)-N—((R)-pent-4-en-2-ylsulfonyl)-3',4,4',5-tetrahydro-2H,2'H-spiro [benzo[b][1,4]oxazepine-3,1'-naphthalene]-7-carboxamide and (S)-6'-chloro-5-(((1R,2R)-2-((R)-1-hydroxybut-3-en-1-yl)cyclobutyl)methyl)-N—((S)-pent-4-en-2-ylsulfonyl)-3',4,4',5-tetrahydro-2H, 2'H-spiro[benzo[b][1,4]oxazepine-3,1'-naphthalene]-7-carboxamide

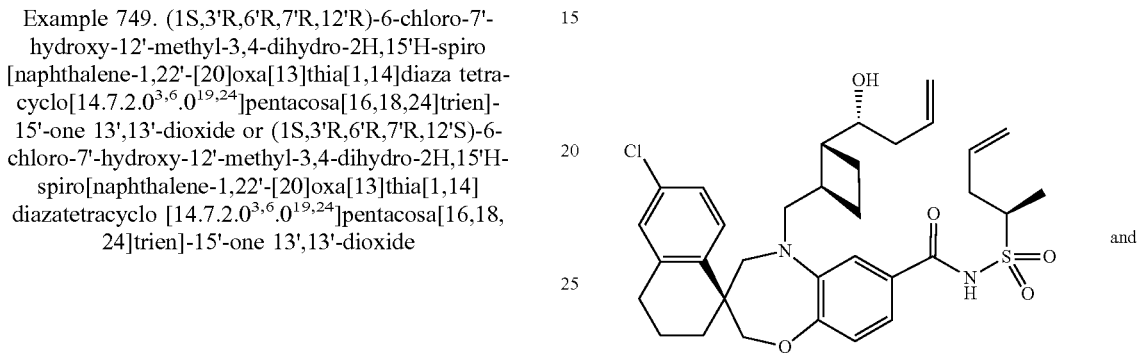

The title compound was synthesized from (S)-6'-chloro-5-(((1R,2R)-2-((R)-1-hydroxybut-3-en-1-yl)cyclobutyl) methyl)-3',4,4',5-tetrahydro-2H,2'H-spiro[benzo[b][1,4] oxazepine-3,1'-naphthalene]-7-carboxylic acid (Intermediate AA13B; 160 mg, 0.332 mmol) and a racemic mixture of (R)-pent-4-ene-2-sulfonamide (intermediate EE17) and (S)-pent-4-ene-2-sulfonamide (intermediate EE172) following the procedure described for Example 1, Step 1. Purification of the crude material provided a mixture of (S)-6'-chloro-5-(((1R,2R)-2-((R)-1-hydroxybut-3-en-1-yl)cyclobutyl)methyl)-N—((R)-pent-4-en-2-ylsulfonyl)-3', 4,4',5-tetrahydro-2H,2'H-spiro[benzo[b][1,4]oxazepine-3, 1'-naphthalene]-7-carboxamide and (S)-6'-chloro-5-(((1R, 2R)-2-((R)-1-hydroxybut-3-en-1-yl)cyclobutyl)methyl)-N—((S)-pent-4-en-2-ylsulfonyl)-3',4,4',5-tetrahydro-2H, 2'H-spiro[benzo[b][1,4]oxazepine-3,1'-naphthalene]-7-carboxamide (130 mg, 0.212 mmol, 63.9% yield).

Step 2. (1S,3'R,6'R,7'R, 9'E,12'R)-6-chloro-7'-hydroxy-12'-methyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa[9,16,18,24]tetraen]-15'-one 13',13'-dioxide and (1S,3'R,6'R,7'R, 9'Z,12'R)-6-chloro-7'-hydroxy-12'-methyl-3,4-dihydro-2H, 15'H-spiro[naphthalene-1,22'-[20]oxa[13]thia[1,14] diazatetracyclo [14.7.2.0$^{3,6}$.0$^{19,24}$]pentacosa[9,16,18, 24]tetraen]-15'-one 13',13'-dioxide or (1S,3'R,6'R, 7'R, 9'E,12'S)-6-chloro-7'-hydroxy-12'-methyl-3,4-dihydro-2H,15'H-spiro[naphthalene-1,22'-[20]oxa [13]thia[1,14]diazatetracyclo [14.7.2.0$^{3,6}$.0$^{19,24}$] pentacosa[9,16,18,24]tetraen]-15'-one 13',13'-dioxide and (1S,3'R,6'R,7'R, 9'Z,12'S)-6-chloro-7'-hydroxy-12'-methyl-3,4-dihydro-2H,15'H-spiro [naphthalene-1,22'-[20]oxa[13]thia[1,14] diazatetracyclo [14.7.2.0$^{3,6}$.0$^{19,24}$]pentacosa[9,16,18, 24]tetraen]-15'-one 13',13'-dioxide

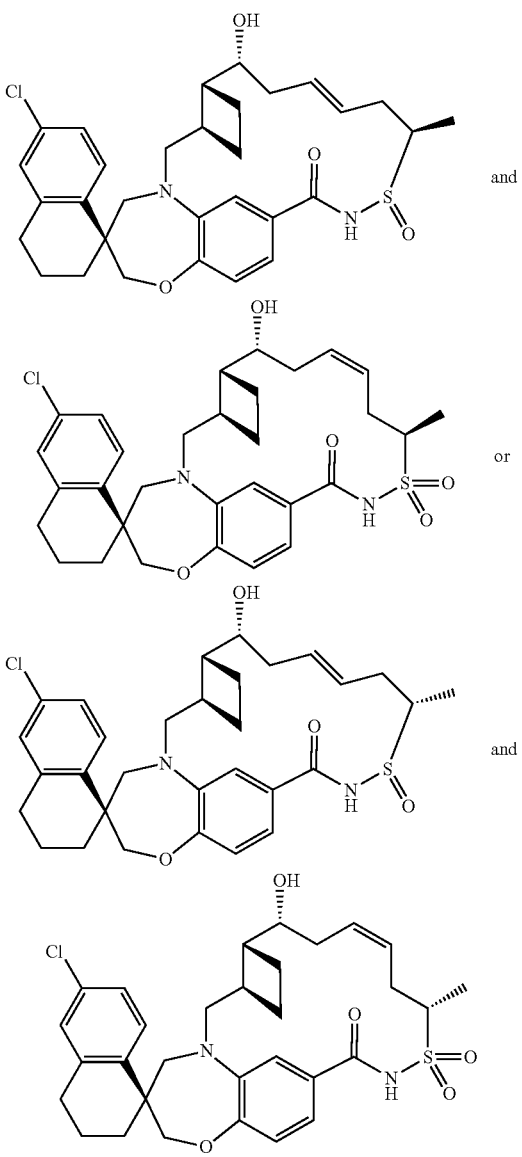

The title compounds were synthesized from a mixture of (S)-6'-chloro-5-(((1R,2R)-2-((R)-1-hydroxybut-3-en-1-yl) cyclobutyl)methyl)-N—((R)-pent-4-en-2-ylsulfonyl)-3',4, 4',5-tetrahydro-2H,2'H-spiro[benzo[b][1,4]oxazepine-3,1'-naphthalene]-7-carboxamide and (S)-6'-chloro-5-(((1R,2R)-2-((R)-1-hydroxybut-3-en-1-yl)cyclobutyl)methyl)-N—((S)-pent-4-en-2-ylsulfonyl)-3',4,4',5-tetrahydro-2H,2'H-spiro[benzo[b][1,4]oxazepine-3,1'-naphthalene]-7-carboxamide (130 mg, 0.212 mmol) following the procedure described for Example 748, Step 2. Purification of the crude material provided a mixture of (1S,3'R,6'R,7'R, 9'E,12'R)-6-chloro-7'-hydroxy-12'-methyl-3,4-dihydro-2H,15'H-spiro [naphthalene-1,22'-[20]oxa[13]thia[1,14]diaza tetracyclo [14.7.2.0$^{3,6}$.0$^{19,24}$]pentacosa[9,16,18,24]tetraen]-15'-one 13',13'-dioxide and (1S,3'R,6'R,7'R,9'Z,12'R)-6-chloro-7'-hydroxy-12'-methyl-3,4-dihydro-2H,15'H-spiro [naphthalene-1,22'-[20]oxa[13]thia[1,14]diazatetracyclo [14.7.2.0$^{3,6}$.0$^{19,24}$]pentacosa[9,16,18,24]tetraen]-15'-one 13',13'-dioxide or (1S,3'R,6'R,7'R,9'E,12'S)-6-chloro-7'-hydroxy-12'-methyl-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[9,16,18,24]tetraen]-15'-one 13',13'-dioxide and (1S,3'R,6'R,7'R,9'Z,12'S)-6-chloro-7'-hydroxy-12'-methyl-3,4-dihydro-2H,15'H-spiro [naphthalene-1,22'-[20] oxa[13]thia[1,14]diazatetracyclo[14.7.2.0$^{3,6}$.0$^{19,24}$]pentacosa[9,16,18,24]tetraen]-15'-one 13',13'-dioxide as the first eluting component (52.4 mg, 0.090 mmol, 42.2% yield). Further elution provided a mixture of (1S,3'R,6'R,7'R,9'E, 12'R)-6-chloro-7'-hydroxy-12'-methyl-3,4-dihydro-2H, 15'H-spiro[naphthalene-1,22'-[20]oxa[13]thia [1,14]diazatetracyclo[14.7.2.0$^{3,6}$.0$^{19,24}$]pentacosa[9,16,18,24]tetraen]-15'-one 13',13'-dioxide and (1S,3'R,6'R,7'R,9'Z,12'R)-6-chloro-7'-hydroxy-12'-methyl-3,4-dihydro-2H,15'H-spiro [naphthalene-1,22'-[20]oxa[13]thia[1,14]diazatetracyclo [14.7.2.0$^{3,6}$.0$^{19,24}$]pentacosa[9,16,18,24]tetraen]-15'-one 13',13'-dioxide or (1S,3'R,6'R,7'R,9'E,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$. 0$^{19,24}$]pentacosa[9,16,18,24]tetraen]-15'-one 13',13'-dioxide and (1S,3'R,6'R,7'R,9'Z,12'S)-6-chloro-7'-hydroxy-12'-methyl-3,4-dihydro-2H,15'H-spiro[naphthalene-1,22'-[20] oxa[13]thia[1,14]diaza tetracyclo[14.7.2.0$^{3,6}$.0$^{19,24}$]pentacosa [9,16,18,24]tetraen]-15'-one 13',13'-dioxide as the second eluting component (53.9 mg, 0.092 mmol, 43.4% yield).

Step 3. (1S,3'R,6'R,7'R,12'R)-6-chloro-7'-hydroxy-12'-methyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa[16,18,24]trien]-15'-one 13',13'-dioxide or (1S,3'R,6'R,7'R,12'S)-6-chloro-7'-hydroxy-12'-methyl-3,4-dihydro-2H,15'H-spiro [naphthalene-1,22'-[20]oxa[13]thia[1,14]diazatetracyclo [14.7.2.0$^{3,6}$.0$^{19,24}$]pentacosa[16,18,24]trien]-15'-one 13',13'-dioxide The title compound was synthesized from a mixture of (1S,3'R,6'R,7'R,9'E,12'R)-6-chloro-7'-hydroxy-12'-methyl-3,4-dihydro-2H,15'H-spiro[naphthalene-1,22'-[20]oxa[13] thia [1,14]diazatetracyclo[14.7.2.0$^{3,6}$.0$^{19,24}$]pentacosa[9,16,18,24]tetraen]-15'-one 13',13'-dioxide and (1S,3'R,6'R,7'R, 9'Z,12'R)-6-chloro-7'-hydroxy-12'-methyl-3,4-dihydro-2H, 15'H-spiro [naphthalene-1,22'-[20]oxa[13]thia[1,14] diazatetracyclo[14.7.2.0$^{3,6}$.0$^{19,24}$]pentacosa[9,16,18,24] tetraen]-15'-one 13',13'-dioxide or (1S,3'R,6'R,7'R,9'E, 12'S)-6-chloro-7'-hydroxy-12'-methyl-3,4-dihydro-2H, 15'H-spiro[naphthalene-1,22'-[20]oxa[13]thia[1,14] diazatetracyclo[14.7.2.0$^{3,6}$.0$^{19,24}$]pentacosa[9,16,18,24] tetraen]-15'-one 13',13'-dioxide and (1S,3'R,6'R,7'R,9'Z, 12'S)-6-chloro-7'-hydroxy-12'-methyl-3,4-dihydro-2H, 15'H-spiro[naphthalene-1,22'-[20]oxa[13]thia[1,14]diazatetracyclo[14.7.2.0³,⁶.0¹⁹,²⁴]pentacosa [9,16,18,24]tetraen]-15'-one 13',13'-dioxide (Step 2, first eluting component; 26 mg, 0.044 mmol) following the procedure described for Example 84 providing (1S,3'R,6'R,7'R,12'R)-6-chloro-7'-hydroxy-12'-methyl-3,4-dihydro-2H,15'H-spiro[naphthalene-1,22'-[20]oxa[13]thia [1,14]diazatetracyclo[14.7.2.0³,⁶.0¹⁹,²⁴]pentacosa [16,18,24]trien]-15'-one 13',13'-dioxide or (1S,3'R,6'R,7'R,12'S)-6-chloro-7'-hydroxy-12'-methyl-3,4-dihydro-2H,15'H-spiro[naphthalene-1,22'-[20]oxa[13]thia[1,14]diazatetracyclo [14.7.2.0³,⁶.0¹⁹,²⁴]pentacosa[16,18,24]trien]-15'-one 13',13'-dioxide. (23 mg, 0.039 mmol, 88% yield). $^1$H NMR (400 MHz, CD$_2$Cl$_2$) δ 9.25 (br s, 1H), 7.73 (d, J=8.6 Hz, 1H), 7.35 (dd, J=2.2, 8.2 Hz, 1H), 7.17 (dd, J=2.3, 8.6 Hz, 1H), 7.13 (d, J=2.2 Hz, 1H), 7.09 (d, J=2.3 Hz, 1H), 6.97 (d, J=8.2 Hz, 1H), 4.15-4.07 (m, 2H), 3.97-3.88 (m, 1H), 3.76 (d, J=15.7 Hz, 1H), 3.72 (br s, 1H), 3.68 (d, J=15.1 Hz, 1H), 3.28 (d, J=13.9 Hz, 1H), 3.21 (dd, J=8.0, 15.7 Hz, 1H), 2.85-2.71 (m, 2H), 2.44 (quin, J=7.8 Hz, 1H), 2.39-2.27 (m, 2H), 2.13-2.01 (m, 1H), 1.98-1.88 (m, 3H), 1.87-1.78 (m, 2H), 1.77-1.58 (m, 5H), 1.52 (br s, 2H), 1.50 (d, J=7.0 Hz, 3H), 1.48-1.39 (m, 3H). MS (ESI, +ve ion) m/z 587.2 (M+H)$^+$.

Example 750. (1S,3'R,6'R,7'R,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'R,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide

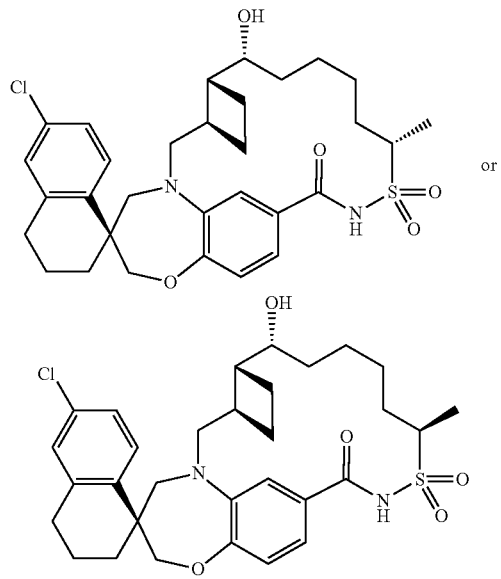

The title compound was synthesized from a mixture of (1S,3'R,6'R,7'R,9'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'R,6'R,7'R,9'Z,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [9,16,18,24]tetraen]-15'-one 13',13'-dioxide or (1S,3'R,6'R,7'R,9'E,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'R,6'R,7'R,9'Z,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [9,16,18,24]tetraen]-15'-one 13',13'-dioxide (Example 749, Step 2, the second eluting component; 26 mg, 0.044 mmol) following the procedure described for Example 84 providing (1S,3'R,6'R,7'R,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'R,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide. (24.5 mg, 0.042 mmol, 94% yield). $^1$H NMR (400 MHz, CD$_2$Cl$_2$) δ 8.14 (br s, 1H), 7.73 (d, J=8.4 Hz, 1H), 7.35 (d, J=2.0 Hz, 1H), 7.17 (dd, J=2.3, 8.6 Hz, 1H), 7.09 (d, J=2.2 Hz, 1H), 6.96 (dd, J=2.2, 8.0 Hz, 1H), 6.92 (d, J=8.0 Hz, 1H), 4.10 (s, 2H), 4.08-4.02 (m, 1H), 3.97 (d, J=15.7 Hz, 1H), 3.68 (d, J=13.7 Hz, 1H), 3.55-3.48 (m, 1H), 3.21 (d, J=14.3 Hz, 1H), 3.04 (dd, J=8.2, 15.5 Hz, 1H), 2.84-2.68 (m, 2H), 2.51-2.37 (m, 2H), 2.04-1.88 (m, 4H), 1.88-1.74 (m, 3H), 1.66-1.56 (m, 3H), 1.53 (br s, 3H), 1.48 (d, J=7.0 Hz, 3H), 1.45-1.31 (m, 4H). MS (ESI, +ve ion) m/z 587.2 (M+H)$^+$.

Example 751. (1S,3'R,6'R,12'R)-6-chloro-12'-methyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[16,18,24]trien]-7',15'-dione 13',13'-dioxide or (1S,3'R,6'R,12'S)-6-chloro-12'-methyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[16,18,24]trien]-7',15'-dione 13',13'-dioxide

A flask charged with dimethyl sulfoxide (0.044 mL, 0.622 mmol) in CH$_2$Cl$_2$ (0.777 mL) was cooled to −78° C. Oxalyl chloride, (2.0 M solution in dichloromethane; 0.155 mL, 0.311 mmol) was then added dropwise and the resulting mixture was stirred at −78° C. for 30 min. A solution of (1S,3'R,6'R,7'R,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide or (1S,3'R,6'R,7'R,12'S)-6-chloro-7'-hydroxy-12'-methyl-3,4-dihydro-2H,15'H-spiro [naphthalene-1,22'-[20]oxa[13]thia[1,14]diazatetracyclo [14.7.2.0³,⁶.0¹⁹,²⁴]pentacosa[16,18,24]trien]-15'-one 13',13'-dioxide (Example 749; 36.5 mg, 0.062 mmol) in CH₂Cl₂ (~0.3 mL) was then added dropwise and the mixture was stirred at −78° C. for 30 min. Triethylamine (0.173 mL, 1.243 mmol) was then added dropwise and the mixture was stirred at −78° C. for 10 min then allowed to reach ambient temperature. After 20 min. the mixture was quenched by the addition of water (1 mL) and extracted with EtOAc (added 1N HCl and brine to the aqueous layer) and the organic phase was dried over MgSO₄ and concentrated. The crude material was purified by chromatography through a Redi-Sep pre-packed silica gel column (4 g), eluting with 0% to 45% EtOAc (containing 0.3% AcOH)/hexanes, to provide (1S,3'R,6'R,12'R)-6-chloro-12'-methyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[16,18,24]trien]-7,15'-dione 13',13'-dioxide or (1S,3'R,6'R,12'S)-6-chloro-12'-methyl-3,4-dihydro-2H,7'H,15'H-spiro [naphthalene-1,22'-[20]oxa[13]thia[1,14]diazatetracyclo[14.7.2.0³,⁶.0¹⁹,²⁴] pentacosa [16,18,24]trien]-7',15'-dione 13',13'-dioxide (21 mg, 0.036 mmol, 57.7% yield). ¹H NMR (400 MHz, CD₂Cl₂) δ 8.27 (br s, 1H), 7.72 (d, J=8.4 Hz, 1H), 7.18 (dd, J=2.4, 8.5 Hz, 1H), 7.10 (d, J=2.3 Hz, 1H), 7.01-6.97 (m, 2H), 6.93 (d, J=8.6 Hz, 1H), 4.15-4.04 (m, 2H), 3.94-3.87 (m, 1H), 3.83 (dd, J=4.7, 15.7 Hz, 1H), 3.74 (d, J=14.5 Hz, 1H), 3.27 (d, J=14.5 Hz, 1H), 3.15 (dd, J=7.0, 15.5 Hz, 1H), 3.10 (dd, J=9.0, 18.2 Hz, 1H), 2.88-2.69 (m, 3H), 2.44-2.24 (m, 2H), 2.10 (dd, J=8.6, 17.6 Hz, 1H), 2.05-1.96 (m, 3H), 1.96-1.86 (m, 2H), 1.85-1.74 (m, 3H), 1.68-1.57 (m, 2H), 1.56-1.50 (m, 2H), 1.48 (d, J=7.0 Hz, 3H), 1.45-1.39 (m, 1H). MS (ESI, +ve ion) m/z 585.2 (M+H)⁺.

Example 752. (1S,3'R,6'R,7'S,12'S)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'S,12'R)-6-chloro-7'-hydroxy-12'-(1-methylethyl)-3,4-dihydro-2H,15'H-spiro[naphthalene-1,22'-[20]oxa [13]thia[1,14]diaza tetracyclo[14.7.2.0³,⁶.0¹⁹,²⁴] pentacosa[16,18,24]trien]-15'-one 13',13'-dioxide

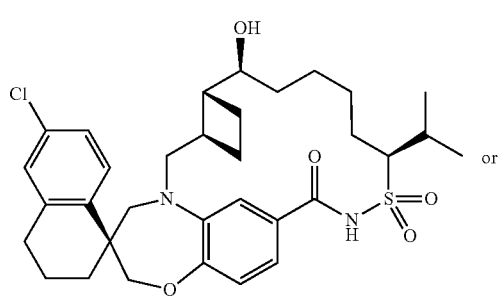

or

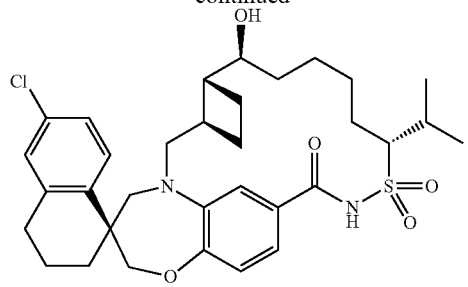

-continued

Step 1: N,N-bis(4-methoxybenzyl)-2-methylpropane-1-sulfonamide

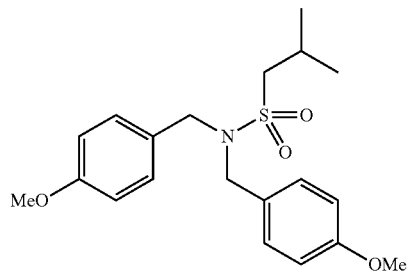 [SMILES: COc1ccc(CN(Cc2ccc(OC)cc2)S(=O)(=O)CC(C)C)cc1]

To a solution of bis(4-methoxybenzyl)amine (Intermediate EE11; 1.550 g, 6.02 mmol) and triethylamine (2.93 ml, 21.08 mmol) in CH₂Cl₂ (30.1 ml) cooled to 0° C. was added isobutanesulfonyl chloride (Sigma Aldrich; 0.786 ml, 6.02 mmol) dropwise over 5 minutes. The cloudy mixture was stirred at 0° C. for 1 h. TLC (50% EtOAc in hexanes) showed complete loss of both starting material and formation of a new product (LC/MS analysis was consistent with the desired product). The mixture was then diluted with CH₂Cl₂ and washed twice with brine. The aqueous phase was back extracted once with EtOAc and the combined organics were then dried over MgSO₄ and concentrated. The crude orange oil was purified by chromatography through a column (40 g), eluting with a gradient of 0% to 20% to 60% EtOAc in hexane, to provide N,N-bis(4-methoxybenzyl)-2-methylpropane-1-sulfonamide (1.563 g, 4.14 mmol, 68.7% yield) as a white solid.

Step 2: (S)—N,N-bis(4-methoxybenzyl)-2-methylhex-5-ene-3-sulfonamide and (R)—N,N-bis(4-methoxybenzyl)-2-methylhex-5-ene-3-sulfonamide

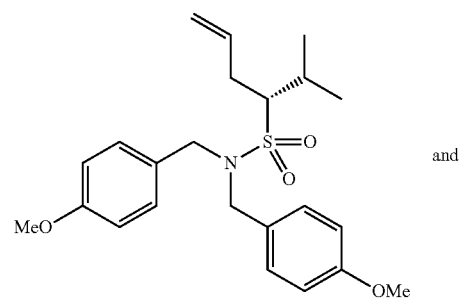

and

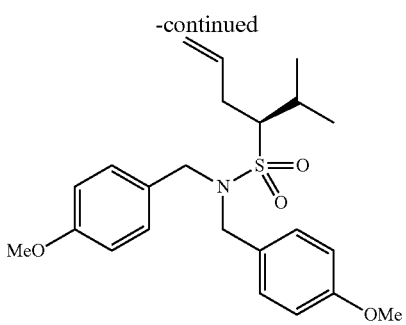

N,N-bis(4-methoxybenzyl)-2-methylpropane-1-sulfonamide (1560 mg, 4.13 mmol) was azeotroped in PhMe under vacuum for 2 h, then, under Ar, THF was added and the solution was cooled to −78° C. Butyllithium solution (2.5 M in hexanes; 1.984 mL, 4.96 mmol) was then added and the mixture was stirred at −78° C. for 60 min. In a separate flask, a solution of allyl iodide (0.761 mL, 8.26 mmol) in THF (8 mL) was cooled to −78° C. To this solution was added the light red anion solution slowly. After 30 min. the mixture was quenched with sat. NH$_4$Cl, allowed to reach ambient temperature and extracted with EtOAc, dried over MgSO$_4$ and concentrated. The orange crude oil was purified on a 40 g ISCO GOLD column eluting with a gradient of 5-10% EtOAc in hexanes to provide an inseparable mixture of (S)—N,N-bis(4-methoxybenzyl)-2-methylhex-5-ene-3-sulfonamide and (R)—N,N-bis(4-methoxybenzyl)-2-methylhex-5-ene-3-sulfonamide (1.26 g, 3.02 mmol, 73.0% yield).

Step 3: (S)-2-methylhex-5-ene-3-sulfonamide and (R)-2-methylhex-5-ene-3-sulfonamide

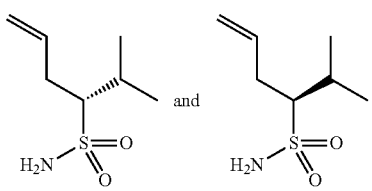

The title compounds were synthesized from (S)—N,N-bis(4-methoxybenzyl)-2-methylhex-5-ene-3-sulfonamide and (R)—N,N-bis(4-methoxybenzyl)-2-methylhex-5-ene-3-sulfonamide (630 mg, 1.51 mmol) following the procedure described for Example 58, Step 2 providing (S)-2-methylhex-5-ene-3-sulfonamide and (R)-2-methylhex-5-ene-3-sulfonamide (236 mg, 1.33 mmol, 88% yield).

Step 4: (S)-6'-chloro-5-(((1R,2R)-2-((S)-1-hydroxybut-3-en-1-yl)cyclobutyl)methyl)-N—(((R)-2-methylhex-5-en-3-yl)sulfonyl)-3',4',4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxybut-3-en-1-yl)cyclobutyl)methyl)-N—(((S)-2-methylhex-5-en-3-yl)sulfonyl)-3',4',4',5-tetrahydro-2H,2'H-spiro[benzo[b][1,4]oxazepine-3,1'-naphthalene]-7-carboxamide

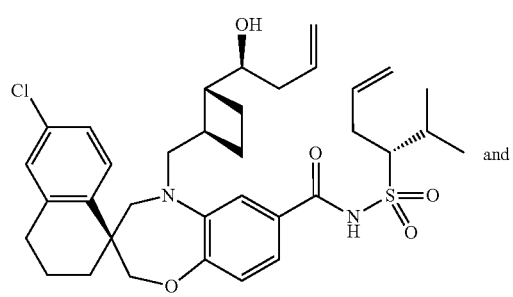

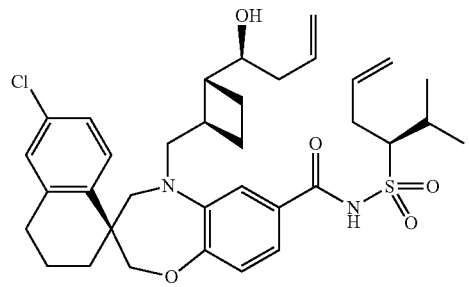

The title compound was synthesized from (S)-6'-chloro-5-(((1R,2R)-2-((S)-1-hydroxybut-3-en-1-yl)cyclobutyl)methyl)-3',4',4',5-tetrahydro-2H,2'H-spiro[benzo[b][1,4]oxazepine-3,1'-naphthalene]-7-carboxylic acid (Intermediate AA13A; 107 mg, 0.222 mmol) and a racemic mixture of (S)-2-methylhex-5-ene-3-sulfonamide and (R)-2-methylhex-5-ene-3-sulfonamide (136 mg, 0.767 mmol) following the procedure described for Example 1, Step 1. Purification of the crude material provided a mixture of (S)-6'-chloro-5-(((1R,2R)-2-((S)-1-hydroxybut-3-en-1-yl)cyclobutyl)methyl)-N—(((R)-2-methylhex-5-en-3-yl)sulfonyl)-3',4',4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxybut-3-en-1-yl)cyclobutyl)methyl)-N—(((S)-2-methylhex-5-en-3-yl)sulfonyl)-3',4',4',5-tetrahydro-2H,2'H-spiro[benzo[b][1,4]oxazepine-3,1'-naphthalene]-7-carboxamide (29 mg, 0.045 mmol, 20.4% yield).

Step 5. (1S,3'R,6'R,7'S,9E,12'R)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and ((1S,3'R,6'R,7'S,9Z,12'R)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'R,7'S,9E,12'S)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9Z,12'S)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide

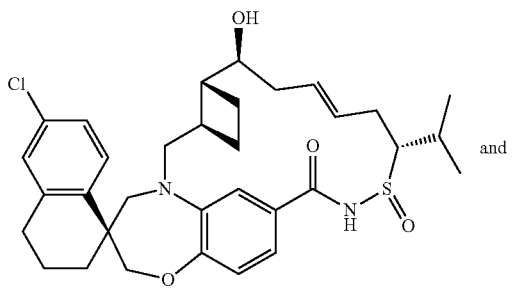
and

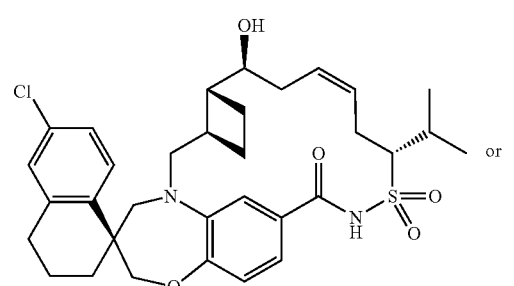
or

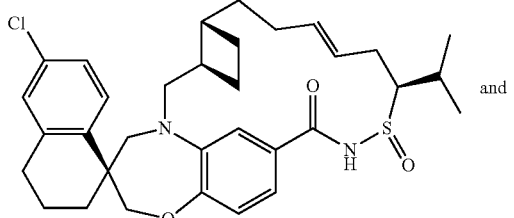
and

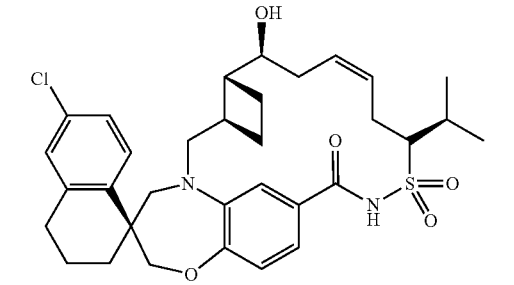

The title compounds were synthesized from a mixture of ((S)-6'-chloro-5-(((1R,2R)-2-((S)-1-hydroxybut-3-en-1-yl)cyclobutyl)methyl)-N—(((R)-2-methylhex-5-en-3-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxybut-3-en-1-yl)cyclobutyl)methyl)-N—(((S)-2-methylhex-5-en-3-yl)sulfonyl)-3',4,4',5-tetrahydro-2H,2'H-spiro[benzo[b][1,4]oxazepine-3,1'-naphthalene]-7-carboxamide (29 mg, 0.045 mmol) following the procedure described for Example 742, Step 2. Purification of the crude material provided a mixture of (1S,3'R,6'R,7'S,9E,12'R)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide and (1S,3'R,6'R,7'S,9Z,12'R)-6-chloro-7'-hydroxy-12'-(1-methylethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[9,16,18,24]tetraen]-15'-one 13',13'-dioxide or (1S,3'R,6'R,7'S,9E,12'S)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide and (1S,3'R,6'R,7'S,9Z,12'S)-6-chloro-7'-hydroxy-12'-(1-methylethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[9,16,18,24]tetraen]-15'-one 13',13'-dioxide as the first eluting component (12 mg, 0.020 mmol, 43.3% yield). Further elution provided a mixture of 1S,3'R,6'R,7'S,9E,12'R)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide and ((1S,3'R,6'R,7'S,9Z,12'R)-6-chloro-7'-hydroxy-12'-(1-methylethyl)-3,4-dihydro-2H,15'H-spiro[naphthalene-1,22'-[20]oxa[13]thia [1,14]diaza tetracyclo[14.7.2.0$^{3,6}$.0$^{19,24}$]pentacosa[9,16,18,24]tetraen]-15'-one 13',13'-dioxide or (1S,3'R,6'R,7'S,9E,12'S)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide and (1S,3'R,6'R,7'S,9Z,12'S)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide as the second eluting component (14 mg, 0.023 mmol, 50.5% yield).

Step 6. (1S,3'R,6'R,7'S,12'S)-6-chloro-7'-hydroxy-12'-(1-methylethyl)-3,4-dihydro-2H,15'H-spiro [naphthalene-1,22'-[20]oxa[13]thia[1,14]diaza tetracyclo[14.7.2.0$^{3,6}$.0$^{19,24}$]pentacosa[16,18,24]trien]-15'-one 13',13'-dioxide or (1S,3'R,6'R,7'S,12'R)-6-chloro-7'-hydroxy-12'-(1-methylethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[16,18,24]trien]-15'-one 13',13'-dioxide The title compound was synthesized from a mixture of (1S,3'R,6'R,7'S,9E,12'R)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9Z,12'R)-6-chloro-7'-hydroxy-12'-(1-methylethyl)-3,4-dihydro-2H,15'H-spiro[naphthalene-1,22'-[20]oxa[13]thia[1,14]diazatetracyclo [14.7.2.0$^{3,6}$.0$^{19,24}$] pentacosa[9,16,18,24]tetraen]-15'-one 13',13'-dioxide or (1S,3'R,6'R,7'S,9E,12'S)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide and (1S,3'R,6'R,7'S,9Z,12'S)-6-chloro-7'-hydroxy-12'-(1-methylethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[9,16,18,24]tetraen]-15'-one 13',13'-dioxide (Step 5, first eluting component; 12 mg, 0.020 mmol) following the procedure described for Example 84 providing (1S,3'R,6'R,7'S,12'S)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,12'R)-6-chloro-7'-hydroxy-12'-(1-methylethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[16,18,24]trien]-15'-one 13',13'-dioxide (7.8 mg, 0.013 mmol, 64.8% yield). $^1$H NMR (400 MHz, CD$_2$Cl$_2$) δ 9.12 (br s, 1H), 7.68 (d, J=8.4 Hz, 1H), 7.22 (s, 1H), 7.16 (app. dd, J=2.4, 8.5 Hz, 2H), 7.09 (d, J=2.3 Hz, 1H), 6.94 (d, J=8.2 Hz, 1H), 4.18-4.09 (m, 2H), 3.75-3.67 (m, 2H), 3.61 (d, J=14.3 Hz, 1H), 3.35 (d, J=13.7 Hz, 1H), 3.34-3.26 (m, 1H), 2.82-2.72 (m, 2H), 2.65 (dtd, J=3.6, 6.9, 13.9 Hz, 1H), 2.43-2.32 (m, 2H), 1.98-1.89 (m, 3H), 1.89-1.68 (m, 5H), 1.63-1.50 (m, 6H), 1.47-1.32 (m, 4H), 1.13 (d, J=7.0 Hz, 3H), 1.09 (d, J=6.8 Hz, 3H). MS (ESI, +ve ion) m/z 615.2 (M+H)$^+$.

Example 753. (1S,3'R,6'R,7'S,12'R)-6-chloro-7'-hydroxy-12'-(1-methylethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[16,18,24]trien]-15'-one 13',13'-dioxide or (1S,3'R,6'R,7'S,12'S)-6-chloro-7'-hydroxy-12'-(1-methylethyl)-3,4-dihydro-2H,15'H-spiro[naphthalene-1,22'-[20]oxa[13]thia[1,14]diazatetracyclo [14.7.2.0$^{3,6}$.0$^{19,24}$]pentacosa[16,18,24]trien]-15'-one 13',13'-dioxide

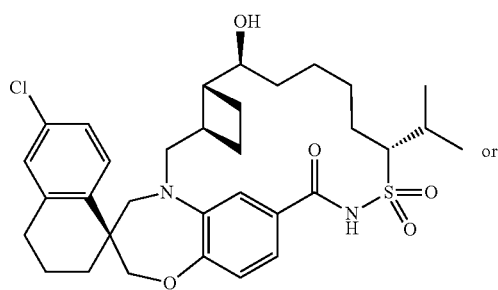

The title compound was synthesized from a mixture of (1S,3'R,6'R,7'S,9E,12'R)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9Z,12'R)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'R,7'S,9E,12'S)-6-chloro-7'-hydroxy-12'-(1-methylethyl)-3,4-dihydro-2H,15'H-spiro[naphthalene-1,22'-[20]oxa[13]thia [1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9Z,12'S)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide (Example 752, Step 5, the second eluting component; 14 mg, 0.023 mmol) following the procedure described for Example 84 providing (1S,3'R,6'R,7'S,12'R)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,12'S)-6-chloro-7'-hydroxy-12'-(1-methylethyl)-3,4-dihydro-2H,15'H-spiro[naphthalene-1,22'-[20]oxa[13]thia[1,14]diazatetracyclo [14.7.2.0$^{3,6}$.0$^{19,24}$]pentacosa[16,18,24]trien]-15'-one 13',13'-dioxide (8.5 mg, 0.014 mmol, 60.5% yield). $^1$H NMR (400 MHz, CD$_2$Cl$_2$) δ 9.67-9.31 (m, 1H), 7.72 (d, J=8.4 Hz, 1H), 7.26 (dd, J=2.0, 8.2 Hz, 1H), 7.17 (dd, J=2.3, 8.4 Hz, 1H), 7.09 (d, J=2.2 Hz, 1H), 7.00 (s, 1H), 6.95 (d, J=8.2 Hz, 1H), 4.13-4.03 (m, 2H), 3.79 (d, J=15.3 Hz, 1H), 3.73-3.69 (m, 1H), 3.66 (d, J=14.5 Hz, 1H), 3.64-3.60 (m, 1H), 3.25 (d, J=14.3 Hz, 1H), 3.15 (dd, J=8.1, 15.4 Hz, 1H), 2.84-2.71 (m, 2H), 2.65 (dtd, J=4.0, 6.9, 13.9 Hz, 1H), 2.31-2.15 (m, 2H), 2.05-1.95 (m, 2H), 1.94-1.88 (m, 3H), 1.87-1.75 (m, 3H), 1.67 (dd, J=8.2, 16.4 Hz, 2H), 1.59 (dd, J=9.4, 19.0 Hz, 2H), 1.54-1.36 (m, 5H), 1.15 (d, J=7.0 Hz, 3H), 1.10 (d, J=6.8 Hz, 3H). MS (ESI, +ve ion) m/z 615.3 (M+H)$^+$.

Example 754. (1S,3'R,6'R,7'R,12'S)-6-chloro-7'-hydroxy-12'-(1-methylethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[16,18,24]trien]-15'-one 13',13'-dioxide or (1S,3'R,6'R,7'R,12'R)-6-chloro-7'-hydroxy-12'-(1-methylethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[16,18,24]trien]-15'-one 13',13'-dioxide

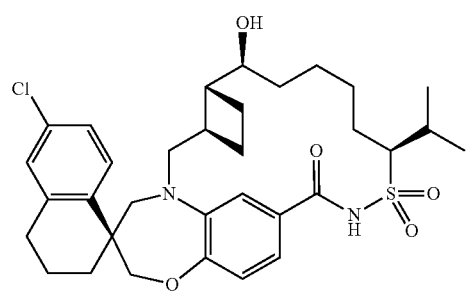

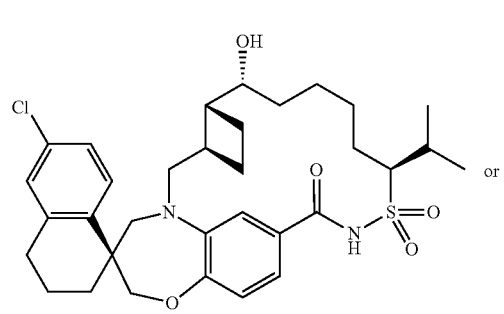

-continued

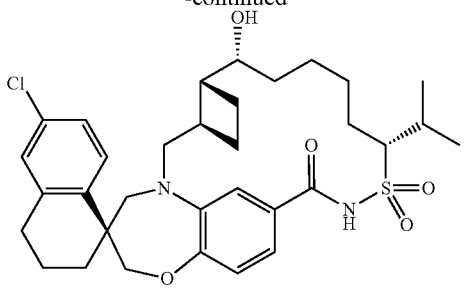

Step 1: S)-6'-chloro-5-(((1R,2R)-2-((R)-1-hydroxybut-3-en-1-yl) cyclobutyl)methyl)-N—(((R)-2-methylhex-5-en-3-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((R)-1-hydroxybut-3-en-1-yl)cyclobutyl)methyl)-N—(((S)-2-methylhex-5-en-3-yl)sulfonyl)-3',4,4',5-tetrahydro-2H,2'H-spiro[benzo[b][1,4]oxazepine-3,1'-naphthalene]-7-carboxamide

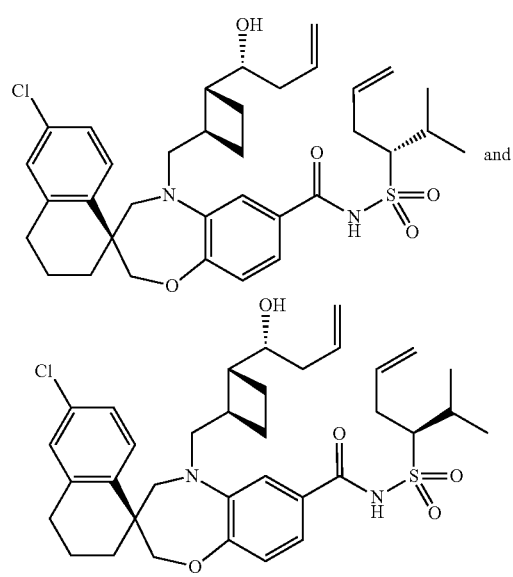

The title compound was synthesized from (S)-6'-chloro-5-(((1R,2R)-2-((R)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA13B; 100 mg, 0.207 mmol) and a racemic mixture of (S)-2-methylhex-5-ene-3-sulfonamide and (R)-2-methylhex-5-ene-3-sulfonamide (Example 752, Step 3; 99 mg, 0.560 mmol) following the procedure described for Example 719, Step 2, Step 1. Purification of the crude material provided a mixture of (S)-6'-chloro-5-(((1R,2R)-2-((R)-1-hydroxybut-3-en-1-yl)cyclobutyl)methyl)-N—(((R)-2-methylhex-5-en-3-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((R)-1-hydroxybut-3-en-1-yl)cyclobutyl)methyl)-N—(((S)-2-methylhex-5-en-3-yl)sulfonyl)-3',4,4',5-tetrahydro-2H,2'H-spiro[benzo[b][1,4]oxazepine-3,1'-naphthalene]-7-carboxamide (78 mg, 0.122 mmol, 58.6% yield).

Step 2. (1S,3'R,6'R,7'R,9E,12'R)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'R,9Z,12'R)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'R,7'R,9E,12'S)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'R,9Z,12'S)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide

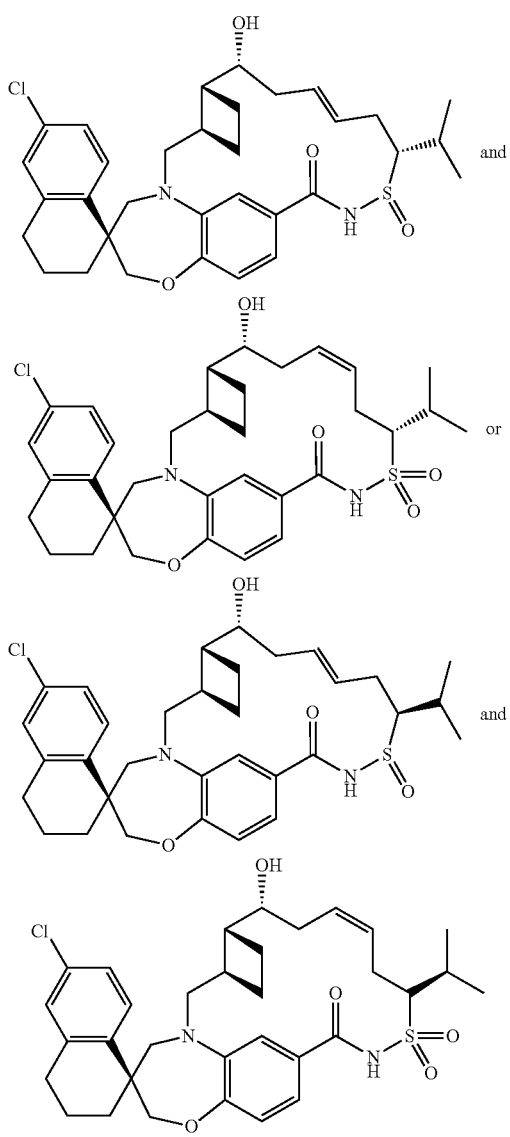

The title compounds were synthesized from a mixture of ((S)-6'-chloro-5-(((1R,2R)-2-((R)-1-hydroxybut-3-en-1-yl)cyclobutyl)methyl)-N—(((R)-2-methylhex-5-en-3-yl)sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((R)-1-hydroxybut-3-en-1-yl)cyclobutyl)methyl)-N—(((S)-2-methylhex-5-en-3-yl)sulfonyl)-3',4,4',5-tetrahydro-2H,2'H-spiro[benzo[b][1,4]oxazepine-3,1'-naphthalene]-7-carboxamide (78 mg, 0.122 mmol) following the procedure described for Example 742, Step 2. Purification of the crude material provided an E/Z mixture of isomers: (1S,3'R,6'R,7'R,9E,12'R)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and ((1S,3'R,6'R,7'R,9Z,12'R)-6-chloro-7'-hydroxy-12'-(1-methylethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[9,16,18,24]tetraen]-15'-one 13',13'-dioxide or (1S,3'R,6'R,7'R,9E,12'S)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'R,9Z,12'S)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide as the first eluting component (30.7 mg, 0.050 mmol, 41.2% yield). Further elution provided another E/Z mixture of isomers: (1S,3'R,6'R,7'R,9E,12'R)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'R,9Z,12'R)-6-chloro-7'-hydroxy-12'-(1-methylethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[9,16,18,24]tetraen]-15'-one 13',13'-dioxide or (1S,3'R,6'R,7'R,9E,12'S)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'R,9Z,12'S)-6-chloro-7'-hydroxy-12'-(1-methylethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[9,16,18,24]tetraen]-15'-one 13',13'-dioxide as the second eluting component (29.2 mg, 0.048 mmol, 39.1% yield).

Step 3. (1S,3'R,6'R,7'R,12'S)-6-chloro-7'-hydroxy-12'-(1-methylethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[16,18,24]trien]-15'-one 13',13'-dioxide or (1S,3'R,6'R,7'R,12'R)-6-chloro-7'-hydroxy-12'-(1-methylethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[16,18,24]trien]-15'-one 13',13'-dioxide The title compound was synthesized from the first eluting component of example 754 step 2; (30.7 mg, 0.050 mmol),a mixture of (1S,3'R,6'R,7'R,9E,12'R)-6-chloro-7'-hydroxy-12'-(1-methylethyl)-3,4-dihydro-2H,15'H-spiro[naphthalene-1,22'-[20]oxa[13]thia[1,14]diazatetracyclo [14.7.2.0$^{3,6}$.0$^{19,24}$]pentacosa[9,16,18,24]tetraen]-15'-one 13',13'-dioxide and (1S,3'R,6'R,7'R,9Z,12'R)-6-chloro-7'-hydroxy-12'-(1-methylethyl)-3,4-dihydro-2H,15'H-spiro[naphthalene-1,22'-[20]oxa[13]thia[1,14]diazatetracyclo [14.7.2.0$^{3,6}$.0$^{19,24}$]pentacosa[9,16,18,24]tetraen]-15'-one 13',13'-dioxide or (1S,3'R,6'R,7'R,9E,12'S)-6-chloro-7'-hydroxy-12'-(1-methylethyl)-3,4-dihydro-2H,15'H-spiro[naphthalene-1,22'-[20]oxa[13]thia[1,14]diazatetracyclo [14.7.2.0$^{3,6}$.0$^{19,24}$]pentacosa[9,16,18,24]tetraen]-15'-one 13',13'-dioxide and (1S,3'R,6'R,7'R,9Z,12'S)-6-chloro-7'-hydroxy-12'-(1-methylethyl)-3,4-dihydro-2H,15'H-spiro[naphthalene-1,22'-[20]oxa[13]thia[1,14]diazatetracyclo [14.7.2.0$^{3,6}$.0$^{19,24}$]pentacosa [9,16,18,24]tetraen]-15'-one 13',13'-dioxide following the procedure described for Example 84 providing (1S,3'R,6'R,7'R,12'S)-6-chloro-7'-hydroxy-12'-(1-methylethyl)-3,4-dihydro-2H,15'H-spiro[naphthalene-1,22'-[20]oxa[13]thia[1,14]diazatetracyclo [14.7.2.0$^{3,6}$.0$^{19,24}$]pentacosa [16,18,24]trien]-15'-one 13',13'-dioxide or (1S,3'R,6'R,7'R,12'R)-6-chloro-7'-hydroxy-12'-(1-methylethyl)-3,4-dihydro-2H,15'H-spiro[naphthalene-1,22'-[20]oxa[13]thia[1,14]diazatetracyclo [14.7.2.0$^{3,6}$.0$^{19,24}$]pentacosa [16,18,24]trien]-15'-one 13', 13'-dioxide (26.4 mg, 0.043 mmol, 86% yield). $^1$H NMR (400 MHz, CD$_2$Cl$_2$) δ 9.55 (br s, 1H), 7.72 (d, J=8.4 Hz, 1H), 7.33 (dd, J=2.1, 8.3 Hz, 1H), 7.17 (dd, J=2.3, 8.4 Hz, 1H), 7.08 (app. t, J=2.6 Hz, 2H), 6.95 (d, J=8.2 Hz, 1H), 4.10-4.01 (m, 2H), 3.78 (d, J=15.3 Hz, 1H), 3.68 (d, J=13.5 Hz, 1H), 3.71-3.62 (m, 1H), 3.56-3.50 (m, 1H), 3.22 (d, J=14.3 Hz, 1H), 3.13 (dd, J=7.2, 15.5 Hz, 1H), 2.84-2.68 (m, 2H), 2.50 (qd, J=6.7, 13.5 Hz, 1H), 2.43-2.30 (m, 2H), 2.10-1.96 (m, 2H), 1.95-1.75 (m, 6H), 1.73-1.48 (m, 6H), 1.47-1.36 (m, 3H), 1.20 (d, J=6.8 Hz, 3H), 1.10 (d, J=6.8 Hz, 3H). MS (ESI, +ve ion) m/z 615.2 (M+H)$^+$.

Example 755. (1S,3'R,6'R,7'R,12'R)-6-chloro-7'-hydroxy-12'-(1-methylethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[16,18,24]trien]-15'-one 13',13'-dioxide or (1S,3'R,6'R,7'R, 12'S)-6-chloro-7'-hydroxy-12'-(1-methylethyl)-3,4-dihydro-2H,15'H-spiro[naphthalene-1,22'-[20]oxa[13]thia[1,14]diaza tetracyclo[14.7.2.0$^{3,6}$.0$^{19,24}$]pentacosa[16,18,24]trien]-15'-one 13',13'-dioxide

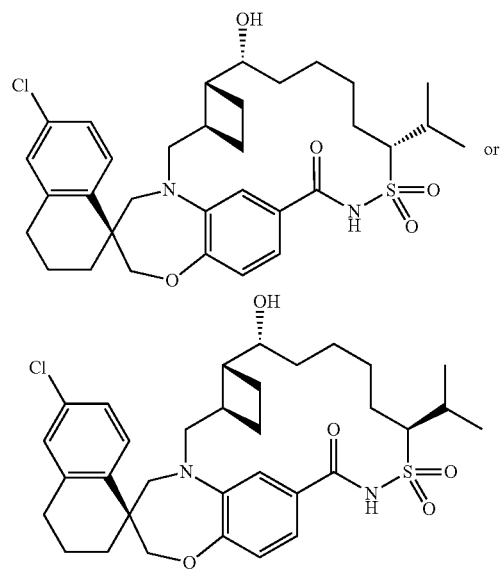

The title compound was synthesized from the second eluting component of Example 754, Step 2, (29.2 mg, 0.048 mmol), a mixture of (1S,3'R,6'R,7'R,9E,12'R)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'R,6'R,7'R,9Z,12'R)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [9,16,18,24]tetraen]-15'-one 13',13'-dioxide or (1S,3'R,6'R,7'R,9E,12'S)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'R,6'R,7'R,9Z,12'S)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [9,16,18,24]tetraen]-15'-one 13',13'-dioxide following the procedure described for Example 29 providing (1S,3'R,6'R,7'R,12'R)-6-chloro-7'-hydroxy-12'-(1-methylethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide or (1S,3'R,6'R,7'R,12'S)-6-chloro-7'-hydroxy-12'-(1-methylethyl)-3,4-dihydro-2H,15'H-spiro[naphthalene-1,22'-[20]oxa[13]thia[1,14]diaza tetracyclo[14.7.2.0³,⁶.0¹⁹,²⁴]pentacosa[16,18,24]trien]-15'-one 13',13'-dioxide (26.3 mg, 0.043 mmol, 90% yield). ¹H NMR (400 MHz, CD$_2$Cl$_2$) δ 7.72 (d, J=8.6 Hz, 1H), 7.33 (d, J=1.8 Hz, 1H), 7.17 (dd, J=2.3, 8.4 Hz, 1H), 7.09 (d, J=2.3 Hz, 1H), 6.96 (dd, J=2.2, 8.4 Hz, 1H), 6.90 (d, J=8.2 Hz, 1H), 4.14-4.03 (m, 2H), 3.94-3.84 (m, 2H), 3.69 (d, J=14.5 Hz, 1H), 3.24 (d, J=14.1 Hz, 1H), 3.28-3.20 (m, 1H), 3.04 (dd, J=6.1, 15.5 Hz, 1H), 2.83-2.68 (m, 2H), 2.63 (dtd, J=2.6, 7.0, 14.0 Hz, 1H), 2.57-2.40 (m, 2H), 2.06-2.02 (m, 1H), 1.95-1.78 (m, 5H), 1.76-1.69 (m, 1H), 1.68-1.59 (m, 3H), 1.57-1.46 (m, 1H), 1.44-1.34 (m, 3H), 1.31 (dd, J=5.7, 10.2 Hz, 3H), 1.16 (d, J=7.0 Hz, 3H), 1.13 (d, J=7.0 Hz, 3H). MS (ESI, +ve ion) m/z 615.3 (M+H)⁺.

Example 756. (1S,3'R,6'R,7'S,10'E,12'R)-6-chloro-12'-ethyl-7'-hydroxy-3,4-dihydro-2H,15'H-spiro[naphthalene-1,22'-[20]oxa[13]thia[1,14]diaza tetracyclo[14.7.2.0³,⁶.0¹⁹,²⁴]pentacosa[10,16,18,24]tetraen]-15'-one 13',13'-dioxide

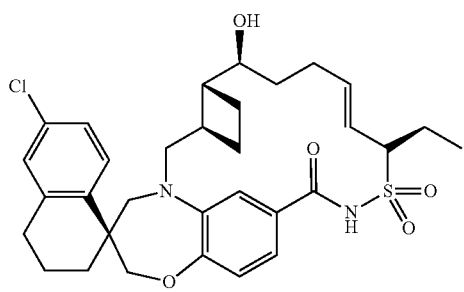

Step 1. (S)-tert-butyl 6'-chloro-5-(((1R,2R)-2-((S)-1-hydroxypent-4-en-1-yl)cyclobutyl)methyl)-3',4,4',5-tetrahydro-2H,2'H-spiro[benzo[b][1,4]oxazepine-3,1'-naphthalene]-7-carboxylate

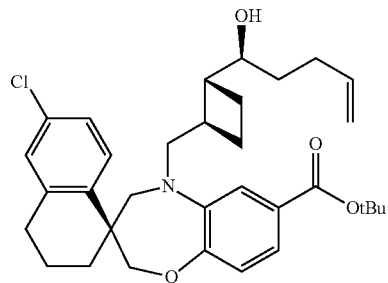 [SMILES: C=CCC[C@H](O)[C@@H]1CC[C@H]1CN1C[C@@]2(CCCc3cc(Cl)ccc32)COc2ccc(C(=O)OC(C)(C)C)cc21]

To a solution of (S)-tert-butyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, step 20B; 200 mg, 0.403 mmol) in THF (4 mL) under Ar, cooled to −78° C. was added 3-butenylmagnesium bromide, (Sigma Aldrich; 0.5 M solution in tetrahydrofuran; 0.806 mL, 0.403 mmol). More reagent was added to drive the reaction as needed. The mixture was then quenched with sat. NH$_4$Cl, allowed to reach ambient temperature and extracted with EtOAc, dried over MgSO$_4$ and concentrated. The crude material was absorbed onto a plug of silica gel and purified by chromatography (12 g ISCO gold; 5-15% EtOAc in hexanes) to provide (S)-tert-butyl 6'-chloro-5-(((1R,2R)-2-((S)-1-hydroxypent-4-en-1-yl)cyclobutyl)methyl)-3',4,4',5-tetrahydro-2H,2'H-spiro[benzo[b][1,4]oxazepine-3,1'-naphthalene]-7-carboxylate (55 mg, 0.10 mmol, 24.7% yield) as the first eluting and minor isomer.

Step 2. (S)-6'-chloro-5-(((1R,2R)-2-((S)-1-hydroxypent-4-en-1-yl) cyclobutyl)methyl)-3',4,4',5-tetrahydro-2H,2'H-spiro[benzo[b][1,4]oxazepine-3,1'-naphthalene]-7-carboxylic Acid

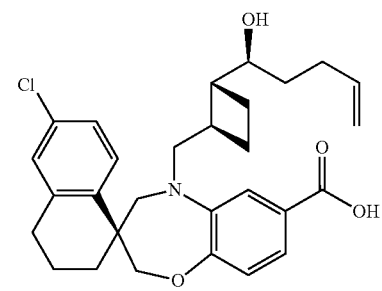 [SMILES: C=CCC[C@H](O)[C@@H]1CC[C@H]1CN1C[C@@]2(CCCc3cc(Cl)ccc32)COc2ccc(C(=O)O)cc21]

To a solution of (S)-tert-butyl 6'-chloro-5-(((1R,2R)-2-((S)-1-hydroxypent-4-en-1-yl)cyclobutyl)methyl)-3',4,4',5-tetrahydro-2H,2'H-spiro[benzo[b][1,4]oxazepine-3,1'-naphthalene]-7-carboxylate (Example 756, step 1, 55 mg, 0.10 mmol) in CH$_2$Cl$_2$ (0.8 mL) at ambient temperature, TFA (0.2 mL) was added and the mixture was stirred at ambient temperature for 3 h. The mixture was then diluted with EtOAc, washed once with sat. NaHCO$_3$, dried over MgSO$_4$, filtered and concentrated. The crude (S)-6'-chloro-5-(((1R,2R)-2-((S)-1-hydroxypent-4-en-1-yl)cyclobutyl)methyl)-3', 4,4',5-tetrahydro-2H,2'H-spiro[benzo[b][1,4]oxazepine-3,1'-naphthalene]-7-carboxylic acid thus obtained was used without further purification.

Step 3.
N,N-bis(4-methoxybenzyl)prop-2-ene-1-sulfonamide

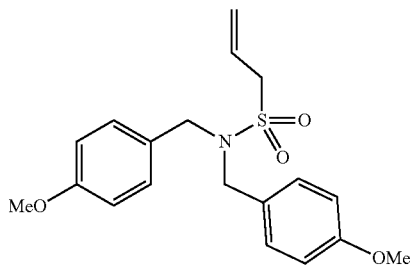 [SMILES: C=CCS(=O)(=O)N(Cc1ccc(OC)cc1)Cc1ccc(OC)cc1]

The title compound was synthesized from N,N-bis(4-methoxybenzyl)amine (Intermediate EE11; 2.5 g, 8.54 mmol) and 2-propene-1-sulfonyl chloride (Matrix Scientific; 1 g, 7.11 mmol) following the procedure described for Intermediate EE13. Purification of the crude material provided N,N-bis(4-methoxybenzyl)prop-2-ene-1-sulfonamide (1.15 g, 3.18 mmol, 44.7% yield).

Step 4. (R)—N,N-bis(4-methoxybenzyl)pent-1-ene-3-sulfonamide and (S)—N,N-bis(4-methoxybenzyl)pent-1-ene-3-sulfonamide

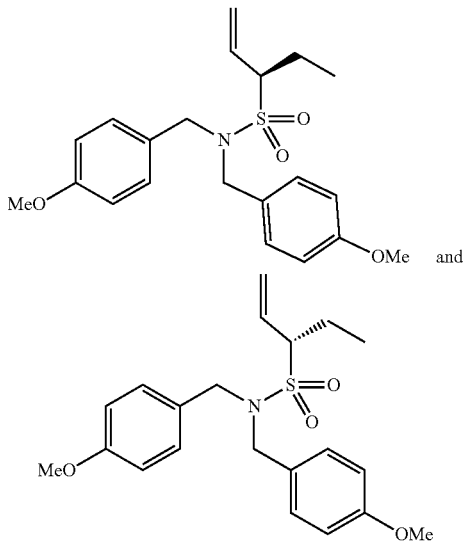

The title compounds were synthesized from N,N-bis(4-methoxybenzyl)prop-2-ene-1-sulfonamide (Example 756, step 3, 265 mg, 0.733 mmol) following the procedure described for Intermediate EE18, Step 1. (R)—N,N-bis(4-methoxybenzyl)pent-1-ene-3-sulfonamide and (S)—N,N-bis(4-methoxybenzyl)pent-1-ene-3-sulfonamide (161 mg, 0.413 mmol, 56.4% yield) were obtained as a racemic mixture.

Step 5. (R)-pent-1-ene-3-sulfonamide and (S)-pent-1-ene-3-sulfonamide

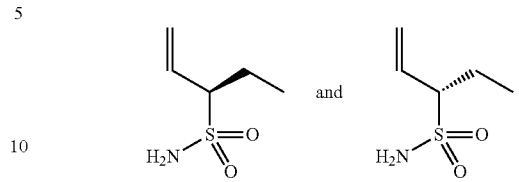

The title compounds were synthesized from (R)—N,N-bis(4-methoxybenzyl)pent-1-ene-3-sulfonamide and (S)—N,N-bis(4-methoxybenzyl)pent-1-ene-3-sulfonamide (Example 756, step 4, 160 mg, 0.411 mmol) following the procedure described for Intermediate EE17, Step 2. (R)-pent-1-ene-3-sulfonamide and (S)-pent-1-ene-3-sulfonamide (52 mg, 0.348 mmol, 85% yield) were obtained as a racemic mixture.

Step 6. (S)-6'-chloro-5-(((1R,2R)-2-((S)-1-hydroxypent-4-en-1-yl)cyclobutyl)methyl)-N—((R)-pent-1-en-3-ylsulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxypent-4-en-1-yl)cyclobutyl)methyl)-N—((S)-pent-1-en-3-ylsulfonyl)-3',4,4',5-tetrahydro-2H,2'H-spiro[benzo[b][1,4]oxazepine-3,1'-naphthalene]-7-carboxamide

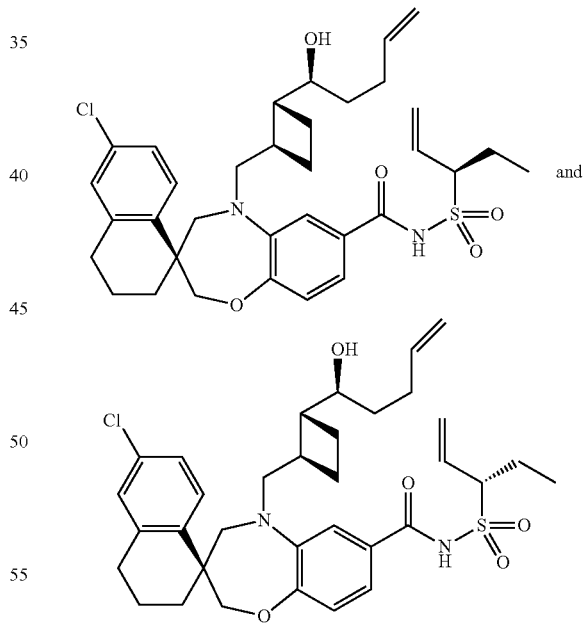

The title compound was synthesized from (S)-6'-chloro-5-(((1R,2R)-2-((S)-1-hydroxypent-4-en-1-yl)cyclobutyl)methyl)-3',4,4',5-tetrahydro-2H,2'H-spiro[benzo[b][1,4]oxazepine-3,1'-naphthalene]-7-carboxylic acid (Example 756, Step 2; 49 mg, 0.099 mmol) and a racemic mixture of (R)-pent-1-ene-3-sulfonamide and (S)-pent-1-ene-3-sulfonamide (Example 756, Step 5; 52 mg, 0.348 mmol) following the procedure described for Example 1, Step 1. Purification of the crude material provided a mixture of (S)-6'- chloro-5-(((1R,2R)-2-((S)-1-hydroxypent-4-en-1-yl)cyclobutyl)methyl)-N—((R)-pent-1-en-3-ylsulfonyl)-3',4,4',5-tetrahydro-2H,2'H-spiro [benzo[b][1,4]oxazepine-3,1'-naphthalene]-7-carboxamide and (S)-6'-chloro-5-(((1R,2R)-2-((S)-1-hydroxypent-4-en-1-yl)cyclobutyl)methyl)-N—((S)-pent-1-en-3-ylsulfonyl)-3',4,4',5-tetrahydro-2H,2'H-spiro[benzo[b][1,4]oxazepine-3,1'-naphthalene]-7-carboxamide (47 mg, 0.075 mmol, 76% yield).

Step 7. (1S,3'R,6'R,7'S,10'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[10,16,18,24]tetraen]-15'-one 13',13'-dioxide The title compound was synthesized from a mixture of (S)-6'-chloro-5-(((1R,2R)-2-((S)-1-hydroxypent-4-en-1-yl)cyclobutyl)methyl)-N—((R)-pent-1-en-3-ylsulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxypent-4-en-1-yl)cyclobutyl)methyl)-N—((S)-pent-1-en-3-ylsulfonyl)-3',4,4',5-tetrahydro-2H,2'H-spiro[benzo[b][1,4]oxazepine-3,1'-naphthalene]-7-carboxamide (Example 756, step 6, 47 mg, 0.075 mmol) following the procedure described for Example 742, Step 2. The crude material was subjected to a first purification by chromatography through a 12 g ISCO column, eluting with 10% to 20% to 50% EtOAc (containing 0.3% AcOH) in hexanes over 25 min. to provide the title compound (contaminated by unknown impurities) as the first eluting component. Purification of this material via reverse-phase HPLC provided (1S,3'R,6'R,7'S,10'E,12'R)-6-chloro-12'-ethyl-7'-hydroxy-3,4-dihydro-2H,15'H-spiro [naphthalene-1,22'-[20]oxa[13]thia[1,14]diazatetracyclo[14.7.2.0³,⁶.0¹⁹,²⁴]pentacosa [10,16,18,24]tetraen]-15'-one 13',13'-dioxide (2.2 mg, 0.004 mmol). $^1$H NMR (400 MHz, CD$_2$Cl$_2$) δ 9.88 (s, 1H), 7.72 (d, J=8.6 Hz, 1H), 7.39 (dd, J=2.2, 8.4 Hz, 1H), 7.18-7.14 (m, 2H), 7.09 (d, J=2.2 Hz, 1H), 6.96 (d, J=8.4 Hz, 1H), 6.07 (ddd, J=5.2, 10.5, 15.4 Hz, 1H), 5.37 (ddd, J=1.4, 8.0, 15.5 Hz, 1H), 4.17-4.05 (m, 2H), 3.83 (ddd, J=4.5, 8.2, 11.7 Hz, 1H), 3.75 (d, J=15.5 Hz, 1H), 3.64 (d, J=13.9 Hz, 1H), 3.65-3.58 (m, 1H), 3.23 (d, J=14.3 Hz, 1H), 3.15 (dd, J=8.5, 15.6 Hz, 1H), 2.81-2.71 (m, 2H), 2.52-2.44 (m, 2H), 2.40 (br s, 1H), 2.37-2.25 (m, 2H), 2.18-2.06 (m, 2H), 2.05-1.96 (m, 2H), 1.93-1.64 (m, 6H), 1.47-1.39 (m, 2H), 1.03 (t, J=7.4 Hz, 3H). MS (ESI, +ve ion) m/z 599.2 (M+H)$^+$.

Example 757. (1S,3'R,6'R,7'S,10'E,12'S)-6-chloro-12'-ethyl-7'-hydroxy-3,4-dihydro-2H,15'H-spiro [naphthalene-1,22'-[20]oxa[13]thia[1,14]diaza tetracyclo[14.7.2.0³,⁶.0¹⁹,²⁴]pentacosa[10,16,18,24] tetraen]-15'-one 13',13'-dioxide

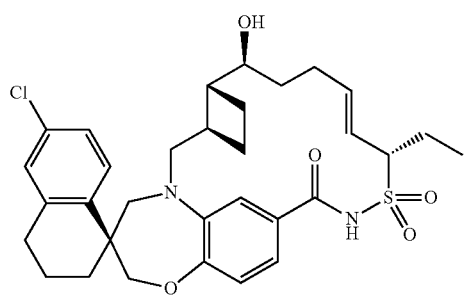 [SMILES: CC[C@H]1/C=C/CC[C@H](O)[C@@H]2CC[C@H]2CN2C[C@@]3(CCCc4cc(Cl)ccc43)COc3ccc(cc32)C(=O)NS1(=O)=O]

The title compound was synthesized as described for Example 756, Step 7. The crude material was subjected to a first purification by chromatography through a 12 g ISCO column, eluting with 10% to 20% to 50% EtOAc (containing 0.3% AcOH) in hexanes over 25 min. to provide the title compound (contaminated by unknown impurities) as the second eluting component. Purification of this material via reverse-phase HPLC provided (1S,3'R,6'R,7'S,10'E,12'S)-6-chloro-12'-ethyl-7'-hydroxy-3,4-dihydro-2H,15'H-spiro [naphthalene-1,22'-[20]oxa[13]thia[1,14]diazatetracyclo [14.7.2.0³,⁶.0¹⁹,²⁴]pentacosa[10,16,18,24]tetraen]-15'-one 13',13'-dioxide (1.9 mg, 0.003 mmol). $^1$H NMR (400 MHz, CD$_2$Cl$_2$) δ 10.03 (s, 1H), 7.73 (d, J=8.4 Hz, 1H), 7.41 (dd, J=2.1, 8.3 Hz, 1H), 7.19-7.15 (m, 2H), 7.09 (d, J=2.3 Hz, 1H), 6.96 (d, J=8.2 Hz, 1H), 6.18 (ddd, J=5.8, 9.8, 15.7 Hz, 1H), 5.69 (dd, J=8.0, 16.2 Hz, 1H), 4.13-4.06 (m, 2H), 4.01 (ddd, J=4.1, 8.2, 11.7 Hz, 1H), 3.87 (d, J=15.3 Hz, 1H), 3.65 (d, J=14.5 Hz, 1H), 3.48 (t, J=8.9 Hz, 1H), 3.13 (d, J=14.1 Hz, 1H), 3.04 (dd, J=8.2, 15.5 Hz, 1H), 2.82-2.68 (m, 2H), 2.50 (dd, J=5.0, 13.6 Hz, 1H), 2.29 (ddd, J=3.8, 7.4, 13.4 Hz, 1H), 2.21-2.14 (m, 1H), 2.12-2.04 (m, 2H), 2.04-1.97 (m, 2H), 1.92 (ddd, J=7.4, 11.0, 13.3 Hz, 2H), 1.85-1.77 (m, 2H), 1.73 (td, J=4.5, 15.0 Hz, 1H), 1.68-1.59 (m, 2H), 1.49-1.41 (m, 3H), 1.05 (t, J=7.3 Hz, 3H). MS (ESI, +ve ion) m/z 599.2 (M+H)$^+$.

Example 758. (1S,3'R,6'R,7'S,8'E,11'R)-6-chloro-7'-hydroxy-11'-methyl-3,4-dihydro-2H,14'H-spiro [naphthalene-1,21'-[19]oxa[12]thia[1,13]diazatetracyclo[13.7.2.0³,⁶.0¹⁸,²³]tetracosa[8,15,17,23] tetraen]-14'-one 12',12'-dioxide

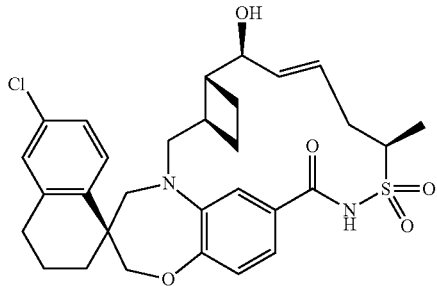 [SMILES: C[C@@H]1C/C=C/[C@H](O)[C@@H]2CC[C@H]2CN2C[C@@]3(CCCc4cc(Cl)ccc43)COc3ccc(cc32)C(=O)NS1(=O)=O]

Step 1. (S)-6'-chloro-5-(((1R,2R)-2-((S)-1-hydroxyallyl)cyclobutyl) methyl)-N—((R)-pent-4-en-2-ylsulfonyl)-3',4,4',5-tetrahydro-2H,2'H-spiro[benzo[b][1,4]oxazepine-3,1'-naphthalene]-7-carboxamide

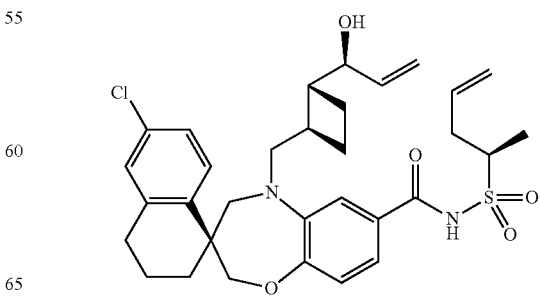

The title compound was synthesized from (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Intermediate AA11A; 165 mg, 0.353 mmol) and (R)-pent-4-ene-2-sulfonamide (Intermediate EE17; 79 mg, 0.529 mmol) following the procedure described for Example 719, Step 2, Step 1. Purification of the crude material provided (S)-6'-chloro-5-(((1R,2R)-2-((S)-1-hydroxyallyl)cyclobutyl)methyl)-N—((R)-pent-4-en-2-ylsulfonyl)-3',4,4',5-tetrahydro-2H,2'H-spiro[benzo[b][1,4]oxazepine-3,1'-naphthalene]-7-carboxamide (44 mg, 0.073 mmol, 20.8% yield).

Step 2. (1S,3'R,6'R,7'S,8'E,11'R)-6-chloro-7'-hydroxy-11'-methyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide A 100 mL round bottom flask was charged with (S)-6'-chloro-5-(((1R,2R)-2-((S)-1-hydroxyallyl)cyclobutyl)methyl)-N—((R)-pent-4-en-2-ylsulfonyl)-3',4,4',5-tetrahydro-2H,2'H-spiro[benzo[b][1,4]oxazepine-3,1'-naphthalene]-7-carboxamide (44 mg, 0.073 mmol) in DCM (24.5 mL). The solution was subjected to three cycles of evacuation/back-filling with nitrogen. To the homogeneous solution was added Hoveyda-Grubbs II (9.2 mg, 0.015 mmol) as a solution in 3 mL DCM at ambient temperature. The mixture was heated to reflux under nitrogen for 7 h. The mixture was then sparged with air for 10 min to deactivate the catalyst, and then it was concentrated. The crude material was absorbed onto a plug of silica gel and purified by chromatography through a Redi-Sep pre-packed silica gel column (12 g), eluting with a gradient of 10-55% EtOAc (containing 0.3% HOAc) in hexanes to provide the title compound. This material was repurified by column (4 g ISCO gold eluting with a gradient of 15-55% EtOAc (containing 0.3% AcOH) in hexanes) to provide partial separation of the impurities. The clean fractions were combined and concentrated to afford (1S,3'R,6'R,7'S,8'E,11'R)-6-chloro-7'-hydroxy-11'-methyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide (10 mg, 0.018 mmol, 23.8% yield). $^1$H NMR (500 MHz, MeOH-d4) δ 7.72 (d, J=8.6 Hz, 1H), 7.16 (dd, J=2.2, 8.6 Hz, 1H), 7.10 (d, J=2.2 Hz, 1H), 7.03 (dd, J=2.0, 8.3 Hz, 1H), 6.92 (d, J=8.1 Hz, 1H), 6.88 (d, J=2.0 Hz, 1H), 5.95 (td, J=6.2, 15.3 Hz, 1H), 5.77 (dd, J=6.8, 15.4 Hz, 1H), 4.08 (s, 2H), 4.06-4.01 (m, 1H), 3.86-3.77 (m, 1H), 3.68 (dd, J=3.4, 15.2 Hz, 1H), 3.67 (d, J=14.4 Hz, 1H), 3.38 (d, J=14.4 Hz, 1H), 3.22 (dd, J=9.4, 15.3 Hz, 1H), 2.86-2.71 (m, 2H), 2.70-2.53 (m, 3H), 2.41 (dq, J=4.5, 9.0 Hz, 1H), 2.08 (d, J=13.7 Hz, 1H), 2.02-1.96 (m, 1H), 1.95-1.88 (m, 2H), 1.87-1.79 (m, 2H), 1.69 (quin, J=9.4 Hz, 1H), 1.51 (d, J=7.1 Hz, 3H), 1.50-1.45 (m, 1H). MS (ESI, +ve ion) m/z 571.2 (M+H)$^+$.

Example 759. (1S,3'R,6'R,7'S,8'E,11'S)-6-chloro-7'-hydroxy-11'-methyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide

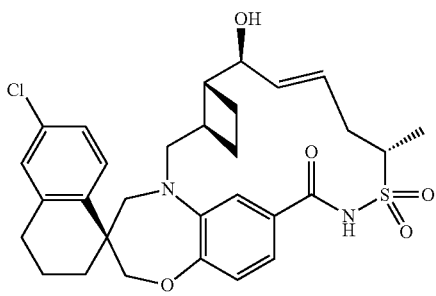 [SMILES: C[C@H]1C/C=C/[C@H](O)[C@@H]2CC[C@H]2CN2C[C@@]3(CCCc4cc(Cl)ccc43)COc3ccc(cc32)C(=O)NS1(=O)=O]

Step 1. (S)-6'-chloro-5-(((1R,2R)-2-((S)-1-hydroxyallyl)cyclobutyl) methyl)-N—((S)-pent-4-en-2-ylsulfonyl)-3',4,4',5-tetrahydro-2H,2'H-spiro[benzo[b][1,4]oxazepine-3,1'-naphthalene]-7-carboxamide

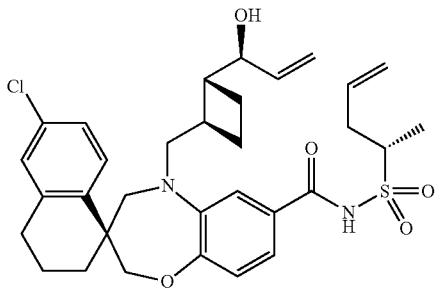 [SMILES: C=CC[C@H](C)S(=O)(=O)NC(=O)c1ccc2c(c1)N(C[C@@H]1CC[C@H]1[C@@H](O)C=C)C[C@@]1(CCCc3cc(Cl)ccc31)CO2]

The title compound was synthesized from (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Intermediate AA11A; 77 mg, 0.165 mmol) and (S)-pent-4-ene-2-sulfonamide (Intermediate EE172; 70 mg, 0.469 mmol) following the procedure described for Example 719, Step 2, Step 1. Purification of the crude material provided (S)-6'-chloro-5-(((1R,2R)-2-((S)-1-hydroxyallyl)cyclobutyl)methyl)-N—((S)-pent-4-en-2-ylsulfonyl)-3',4,4',5-tetrahydro-2H,2'H-spiro[benzo[b][1,4]oxazepine-3,1'-naphthalene]-7-carboxamide (74 mg, 0.124 mmol, 75% yield).

Step 2. (1S,3'R,6'R,7'S,8'E,11'S)-6-chloro-7'-hydroxy-11'-methyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide The title compound was synthesized from (S)-6'-chloro-5-(((1R,2R)-2-((S)-1-hydroxyallyl)cyclobutyl)methyl)-N—((S)-pent-4-en-2-ylsulfonyl)-3',4,4',5-tetrahydro-2H,2'H-spiro[benzo[b][1,4]oxazepine-3,1'-naphthalene]-7-carboxamide (Example 759, step 1, 74 mg, 0.124 mmol) following the procedure described for Example 758, Step 2. The crude material was absorbed onto a plug of silica gel and purified by chromatography through a Redi-Sep pre-packed silica gel column (12 g), eluting with a gradient of 10-55% EtOAc (containing 0.3% HOAc) in hexanes to provide a mixture of compounds. This material was repurified by reverse phase HPLC providing (1S,3'R,6'R,7'S,8'E,11'S)-6-chloro-7'-hydroxy-11'-methyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide as the first eluting major component (6.8 mg, 0.012 mmol, 9.6% yield). $^1$H NMR (400 MHz, CD$_2$Cl$_2$) δ 8.22 (br s, 1H), 7.71 (d, J=8.4 Hz, 1H), 7.21 (dd, J=2.1, 8.3 Hz, 1H), 7.17 (dd, J=2.3, 8.4 Hz, 1H), 7.09 (d, J=2.2 Hz, 1H), 6.96 (d, J=8.2 Hz, 1H), 6.75 (s, 1H), 5.89-5.85 (m, 1H), 5.82 (dd, J=4.9, 15.6 Hz, 1H), 4.14-4.07 (m, 3H), 3.91-3.78 (m, 1H), 3.71 (d, J=14.5 Hz, 1H), 3.70-3.60 (m, 1H), 3.33 (d, J=14.5 Hz, 1H), 3.19 (dd, J=7.6, 15.7 Hz, 1H), 2.85-2.70 (m, 2H), 2.66-2.52 (m, 3H), 2.44-2.33 (m, 1H), 2.05-1.96 (m, 2H), 1.96-1.88 (m, 2H), 1.86-1.80 (m, 1H), 1.79-1.73 (m, 1H), 1.72-1.56 (m, 2H), 1.53 (d, J=7.2 Hz, 3H), 1.49-1.40 (m, 1H). MS (ESI, +ve ion) m/z 571.2 (M+H)$^+$.

Example 760. (1S,3'R,6'R,11'S)-6-chloro-11'-methyl-3,4-dihydro-2H,7'H,14'H-spiro[naphthalene-1,21'-[19]oxa[12]thia[1,13]diazatetracyclo[13.7.2.0$^{3,6}$.0$^{18,23}$]tetracosa[15,17,23]trien]-7',14'-dione 12',12'-dioxide

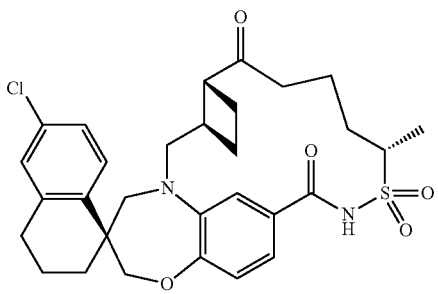 [SMILES: C[C@H]1CCCC(=O)[C@@H]2CC[C@H]2CN2C[C@@]3(CCCc4cc(Cl)ccc43)COc3ccc(cc32)C(=O)NS1(=O)=O]

The title compound was isolated as a side product of Example 759, Step 2. The crude material was absorbed onto a plug of silica gel and purified by chromatography through a Redi-Sep pre-packed silica gel column (12 g), eluting with a gradient of 10-55% EtOAc (containing 0.3% HOAc) in hexanes to provide a mixture of compounds. This material was repurified by reverse phase HPLC providing (1S,3'R,6'R,11'S)-6-chloro-11'-methyl-3,4-dihydro-2H,7',14'H-spiro[naphthalene-1,21'-[19]oxa[12]thia[1,13]diazatetracyclo[13.7.2.0$^{3,6}$.0$^{18,23}$]tetracosa[15,17,23]triene]-7',14'-dione 12',12'-dioxide as the second eluting minor component (3.4 mg, 0.006 mmol, 4.8% yield). $^1$H NMR (500 MHz, CD$_2$Cl$_2$) δ 8.88 (br s, 1H), 7.72 (d, J=8.3 Hz, 1H), 7.29 (dd, J=2.1, 8.2 Hz, 1H), 7.17 (dd, J=2.3, 8.4 Hz, 1H), 7.09 (d, J=2.4 Hz, 1H), 6.96 (d, J=8.3 Hz, 1H), 6.90 (d, J=2.0 Hz, 1H), 4.15 (d, J=12.5 Hz, 1H), 4.09 (d, J=12.0 Hz, 1H), 4.04 (d, J=15.4 Hz, 1H), 3.74 (td, J=3.7, 7.3 Hz, 1H), 3.69 (d, J=14.4 Hz, 1H), 3.23 (dd, J=8.8, 15.7 Hz, 1H), 3.18 (d, J=14.4 Hz, 1H), 2.91-2.84 (m, 1H), 2.75-2.69 (m, 1H), 2.83-2.68 (m, 2H), 2.66-2.56 (m, 1H), 2.52-2.43 (m, 1H), 2.36-2.24 (m, 1H), 2.13-2.00 (m, 4H), 1.97-1.89 (m, 2H), 1.86-1.66 (m, 4H), 1.50 (d, J=7.3 Hz, 3H), 1.48-1.41 (m, 1H). MS (ESI, +ve ion) m/z 571.2 (M+H)$^+$.

Example 761. (1S,3'R,6'R,7'S,11'R)-6-chloro-7'-hydroxy-11'-methyl-3,4-dihydro-2H,14'H-spiro[naphthalene-1,21'-[19]oxa[12]thia[1,13]diaza tetracyclo[13.7.2.0$^{3,6}$.0$^{18,23}$]tetracosa[15,17,23]trien]-14'-one 12',12'-dioxide

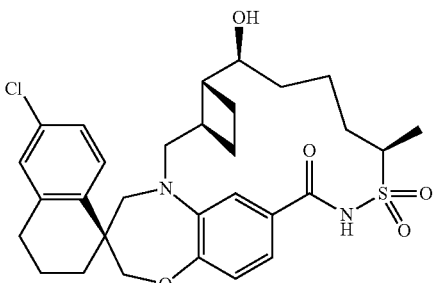

The title compound was synthesized from (1S,3'R,6'R,7'S,8'E,11'R)-6-chloro-7'-hydroxy-11'-methyl-3,4-dihydro-2H,14'H-spiro[naphthalene-1,21'-[19]oxa[12]thia[1,13]diazatetracyclo [13.7.2.0$^{3,6}$.0$^{18,23}$]tetracosa[8,15,17,23]tetraen]-14'-one 12',12'-dioxide (7.7 mg, 0.013 mmol, Example 758) following the procedure described for Example 84 providing (1S,3'R,6'R,7'S,11'R)-6-chloro-7'-hydroxy-11'-methyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[15,17,23]trien]-14'-one 12',12'-dioxide (4.9 mg, 0.0009 mmol, 63.4% yield). $^1$H NMR (400 MHz, CD$_2$Cl$_2$) δ 8.83 (br s, 1H), 7.71 (d, J=8.4 Hz, 1H), 7.17 (dd, J=2.3, 8.4 Hz, 1H), 7.13-7.05 (m, 3H), 6.92 (d, J=8.0 Hz, 1H), 4.12 (s, 2H), 3.78 (d, J=15.1 Hz, 1H), 3.75-3.67 (m, 2H), 3.63 (d, J=14.3 Hz, 1H), 3.35-3.27 (m, 1H), 3.28 (d, J=14.3 Hz, 1H), 2.84-2.68 (m, 2H), 2.37-2.24 (m, 2H), 2.06-1.98 (m, 2H), 1.99-1.85 (m, 3H), 1.85-1.76 (m, 1H), 1.76-1.61 (m, 3H), 1.59-1.50 (m, 4H), 1.48 (d, J=7.0 Hz, 3H), 1.44-1.32 (m, 2H). MS (ESI, +ve ion) m/z 573.1 (M+H)$^+$.

Example 762. (1S,3'R,6'R,7'S,8'E,11'R)-6-chloro-7'-hydroxy-11'-ethyl-3,4-dihydro-2H,14'H-spiro[naphthalene-1,21'-[19]oxa[12]thia[1,13]diaza tetracyclo[13.7.2.0$^{3,6}$.0$^{18,23}$]tetracosa[8,15,17,23]tetraen]-14'-one 12',12'-dioxide

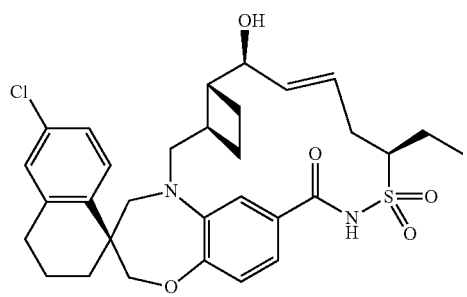 [SMILES: CC[C@@H]1C/C=C/[C@H](O)[C@@H]2CC[C@H]2CN2C[C@@]3(CCCc4cc(Cl)ccc43)COc3ccc(cc32)C(=O)NS1(=O)=O]

Step 1. (S)-tert-butyl 6'-chloro-5-(((1R,2R)-2-((1S,5R,E)-1-hydroxy-5-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylate

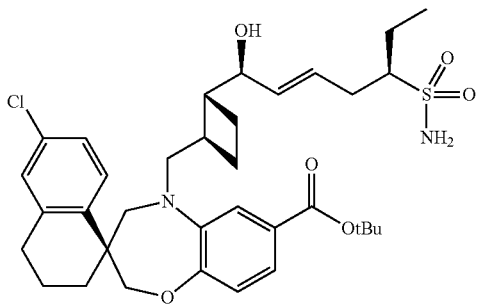 [SMILES: CC[C@H](C/C=C/[C@H](O)[C@@H]1CC[C@H]1CN1C[C@@]2(CCCc3cc(Cl)ccc32)COc2ccc(C(=O)OC(C)(C)C)cc21)S(N)(=O)=O]

A 50 mL RB flask was charged with (S)-tert-butyl 6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (Intermediate AA12B, Step 1B, first eluting isomer; 184 mg, 0.325 mmol) and (S)-hex-5-ene-3-sulfonamide (Intermediate EE18; 318 mg, 1.95 mmol) and DCM (4.6 mL) and the resulting solution was sparged with Ar. To the homogeneous solution was added Hoveyda-Grubbs II (20.36 mg, 0.032 mmol) as a solution in 2 mL DCM at ambient temperature. The mixture was stirred under Ar at ambient temperature (venting the flask and adding solvent as needed) overnight. The reaction mixture was directly injected into a 24 g ISCO Gold column, and purified eluting with a gradient of 0-20-100% EtOAc in hexanes over 20 min to give (S)-tert-butyl 6'-chloro-5-(((1R,2R)-2-((1S,5R,E)-1-hydroxy-5-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylate (80 mg, 0.121 mmol, 37.3% yield).

Step 2. (S)-6'-chloro-5-(((1R,2R)-2-((1S,5R,E)-1-hydroxy-5-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic Acid

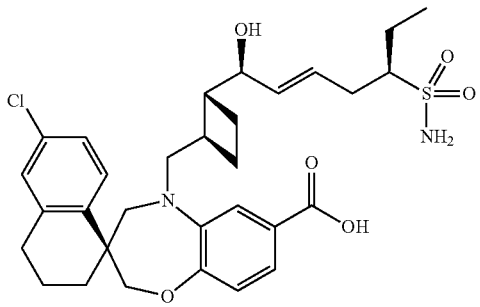 [SMILES: CC[C@H](C/C=C/[C@H](O)[C@@H]1CC[C@H]1CN1C[C@@]2(CCCc3cc(Cl)ccc32)COc2ccc(C(=O)O)cc21)S(N)(=O)=O]

To a solution of (S)-tert-butyl 6'-chloro-5-(((1R,2R)-2-((1S,5R,E)-1-hydroxy-5-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylate (80 mg, 0.121 mmol) in CH$_2$Cl$_2$ (1.94 mL) at ambient temperature, TFA (0.486 mL) was added and the reaction mixture was stirred at ambient temperature for 1.5 h. The reaction mixture was then diluted with EtOAc, washed once with sat. NaHCO$_3$, dried over MgSO$_4$, filtered and concentrated to give a brown foam. The crude material was used without further purification.

Step 3. (1S,3'R,6'R,7'S,8'E,11'R)-6-chloro-7'-hydroxy-11'-ethyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide N,N-dimethylpyridin-4-amine (25.1 mg, 0.206 mmol) was added to a solution of (S)-6'-chloro-5-(((1R,2R)-2-((1S,5R,E)-1-hydroxy-5-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic acid (Example 762, step 2, 73 mg, 0.121 mmol) (previously azeotroped with 2.5 mL toluene for 1 h) in CH$_2$Cl$_2$ (60.5 mL) at 0° C. N-(3-dimethylaminopropyl)-N'-ethylcarbodiimide hydrochloride (46.4 mg, 0.242 mmol) was then added portionwise slowly and the mixture was stirred while allowing to reach ambient temperature for 22 h. The mixture was then washed with 1N HCl and brine, the aqueous layer was back extracted with EtOAc and the combined organics were dried over anhydrous magnesium sulfate, then concentrated. The crude material was purified by chromatography through a ISCO gold column 24 g, eluting with a gradient of 10% to 55% EtOAc (containing 0.3% AcOH) in hexanes, to provide the title compound. This material was repurified by reverse phase HPLC to provide (1S,3'R,6'R,7'S,8'E,11'R)-6-chloro-7'-hydroxy-11'-ethyl-3,4-dihydro-2H,14'H-spiro[naphthalene-1,21'-[19]oxa[12]thia[1,13]diazatetracyclo [13.7.2.0$^{3,6}$.0$^{18,23}$]tetracosa[8,15,17,23]tetraen]-14'-one 12',12'-dioxide (21 mg, 0.036 mmol, 29.7% yield). $^1$H NMR (400 MHz, CD$_2$Cl$_2$) δ 8.21 (s, 1H), 7.70 (d, J=8.6 Hz, 1H), 7.17 (dd, J=2.4, 8.5 Hz, 1H), 7.09 (d, J=2.3 Hz, 1H), 7.02 (dd, J=2.3, 8.6 Hz, 1H), 6.93 (d, J=8.2 Hz, 1H), 6.91 (d, J=2.0 Hz, 1H), 5.80-5.76 (m, 2H), 4.17-4.06 (m, 2H), 4.01-3.96 (m, 1H), 3.73-3.62 (m, 3H), 3.34 (d, J=14.5 Hz, 1H), 3.22 (dd, J=6.7, 15.5 Hz, 1H), 2.86-2.70 (m, 2H), 2.67-2.45 (m, 4H), 2.27-2.15 (m, 1H), 2.04-1.96 (m, 2H), 1.94-1.86 (m, 2H), 1.86-1.76 (m, 2H), 1.76-1.62 (m, 3H), 1.52-1.43 (m, 1H), 1.13 (t, J=7.4 Hz, 3H). MS (ESI, +ve ion) m/z 585.1 (M+H)$^+$.

Example 763. (1S,3'R,6'R,7'S,8'E,11'R)-6-chloro-11'-ethyl-7'-methoxy-3,4-dihydro-2H,14'H-spiro[naphthalene-1,21'-[19]oxa[12]thia[1,13]diaza tetracyclo[13.7.2.0$^{3,6}$.0$^{18,23}$]tetracosa[8,15,17,23]tetraen]-14'-one 12',12'-dioxide

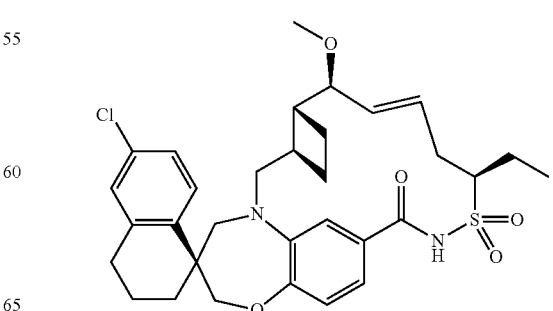

The title compound was synthesized from (1S,3'R,6'R,7'S,8'E,11'R)-6-chloro-7'-hydroxy-11'-ethyl-3,4-dihydro-2H,14'H-spiro[naphthalene-1,21'-[19]oxa[12]thia[1,13]diazatetracyclo [13.7.2.0$^{3,6}$.0$^{18,23}$]tetracosa[8,15,17,23]tetraen]-14'-one 12',12'-dioxide (6 mg, 0.0102 mmol, Example 762) following the procedure described for Example 735 providing (1S,3'R,6'R,7'S,8'E,11'R)-6-chloro-11'-ethyl-7'-methoxy-3,4-dihydro-2H,14'H-spiro[naphthalene-1,21'-[19]oxa[12]thia[1,13]diazatetracyclo[13.7.2.0$^{3,6}$.0$^{18,23}$]tetracosa [8,15,17,23]tetraen]-14'-one 12',12'-dioxide (4.7 mg, 0.008 mmol, 76% yield). $^1$H NMR (400 MHz, MeOH-d4) δ 7.72 (d, J=8.4 Hz, 1H), 7.15 (d, J=8.4 Hz, 1H), 7.10 (s, 1H), 7.04 (br s, 1H), 6.96 (br s, 1H), 6.88 (d, J=7.8 Hz, 1H), 6.01-5.85 (m, 1H), 5.58 (dd, J=8.5, 15.2 Hz, 1H), 4.06 (s, 2H), 3.71 (dd, J=2.9, 14.7 Hz, 1H), 3.65 (d, J=14.5 Hz, 1H), 3.60 (dd, J=3.9, 8.0 Hz, 1H), 3.48 (br s, 1H), 3.36 (d, J=15.1 Hz, 1H), 3.22 (s, 3H), 3.17 (dd, J=11.2, 15.3 Hz, 1H), 2.87-2.74 (m, 2H), 2.73-2.53 (m, 3H), 2.49-2.37 (m, 1H), 2.18 (br s, 1H), 2.12-2.04 (m, 1H), 2.01-1.84 (m, 3H), 1.84-1.65 (m, 4H), 1.54-1.43 (m, 1H), 1.11 (t, J=6.9 Hz, 3H). MS (ESI, +ve ion) m/z 599.0 (M+H)$^+$.

Example 764. (((1S,3'R,6'R,7'S,8'E,11'R)-6-chloro-11'-ethyl-12',12'-dioxido-14'-oxo-3,4-dihydro-2H-spiro[naphthalene-1,21'-[19]oxa[12]thia[1,13]diazatetracyclo[13.7.2.0$^{3,6}$.0$^{18,23}$]tetracosa[8,15,17,23]tetraen]-7'-yl)oxy)acetic Acid

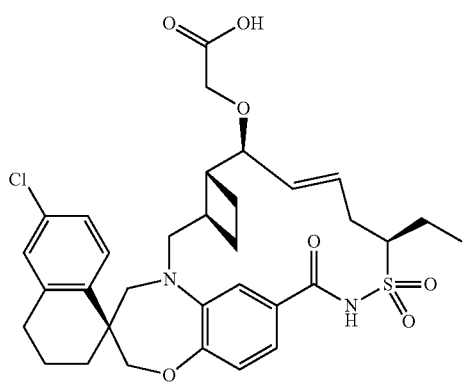 [SMILES: CC[C@@H]1C/C=C/[C@H](OCC(=O)O)[C@@H]2CC[C@H]2CN2C[C@@]3(CCCc4cc(Cl)ccc43)COc3ccc(cc32)C(=O)NS1(=O)=O]

To a solution of (1S,3'R,6'R,7'S,8'E,11'R)-6-chloro-11'-ethyl-7'-methoxy-3,4-dihydro-2H,14'H-spiro[naphthalene-1,21'-[19]oxa[12]thia[1,13]diazatetracyclo[13.7.2.0$^{3,6}$.0$^{18,23}$]tetracosa [8,15,17,23]tetraen]-14'-one 12',12'-dioxide (9.3 mg, 0.016 mmol, Example 762) in DCM (318 μl) at ambient temperature was added rhodium (II) acetate dimer (Sigma Aldrich; 0.176 mg, 0.397 μmol), followed by the dropwise addition of ethyl diazoacetate (Sigma Aldrich; 3.62 μl, 0.035 mmol). The reaction mixture was stirred at ambient temperature for 4 h adding more diazoacetate reagent as needed to drive the reaction to near completion. The reaction mixture was then directly injected onto a Redi-Sep pre-packed silica gel column (4 g), and purified eluting with 0% to 35% EtOAc (containing 0.3% AcOH) in heptanes. The material isolated was repurified eluting with 15-35% EtOAc (containing 0.3% AcOH) in heptanes. The intermediate ester was taken up in THF/MeOH (2:1) and treated with 10 eq of 1N LiOH at ambient temperature for 1 h. The mixture was then quenched with 1N HCl, diluted with brine, extracted with EtOAc, dried over MgSO4, filtered and concentrated. The crude material was purified by chromatography through a Redi-Sep pre-packed silica gel column (4 g), eluting with 20% to 50% EtOAc (containing 0.3% AcOH) in heptane, to provide (((1S,3'R,6'R,7'S,8'E,11'R)-6-chloro-11'-ethyl-12',12'-dioxido-14'-oxo-3,4-dihydro-2H-spiro[naphthalene-1,21'-[19]oxa[12]thia [1,13]diazatetracyclo[13.7.2.0$^{3,6}$.0$^{18,23}$]tetracosa[8,15,17,23]tetraen]-7'-yl)oxy)acetic acid (1.0 mg, 1.56 μmol, 9.78% yield). $^1$H NMR (400 MHz, CD$_2$Cl$_2$) δ 7.69 (d, J=8.6 Hz, 1H), 7.17 (dd, J=2.3, 8.6 Hz, 1H), 7.10 (d, J=2.3 Hz, 1H), 7.06 (d, J=8.4 Hz, 1H), 6.93 (d, J=8.2 Hz, 1H), 6.77 (br s, 1H), 5.79 (br s, 1H), 5.67 (dd, J=8.0, 15.8 Hz, 1H), 4.11 (s, 2H), 4.02 (d, J=15.8 Hz, 1H), 3.94 (d, J=16.2 Hz, 1H), 3.78 (t, J=5.9 Hz, 1H), 3.74-3.68 (m, 1H), 3.66 (d, J=14.9 Hz, 1H), 3.60 (br s, 1H), 3.33 (d, J=14.3 Hz, 1H), 3.23 (dd, J=7.8, 15.1 Hz, 1H), 2.84-2.71 (m, 2H), 2.66 (br s, 2H), 2.62-2.47 (m, 2H), 2.06-1.95 (m, 2H), 1.94-1.85 (m, 2H), 1.78 (dd, J=9.7, 19.5 Hz, 3H), 1.69 (dd, J=9.4, 18.2 Hz, 2H), 1.54-1.45 (m, 1H), 1.12 (t, J=7.4 Hz, 3H). MS (ESI, +ve ion) m/z 643.0 (M+H)$^+$.

Example 765. (1S,3'R,6'R,7'S,9'E,11'R)-6-chloro-7'-hydroxy-11'-methyl-3,4-dihydro-2H,14'H-spiro [naphthalene-1,21'-[19]oxa[12]thia[1,13]diaza tetracyclo[13.7.2.0$^{3,6}$.0$^{18,23}$]tetracosa[9,15,17,23]tetraen]-14'-one 12',12'-dioxide or (1S,3'R,6'R,7'S,9'E,11'S)-6-chloro-7'-hydroxy-11'-methyl-3,4-dihydro-2H,14'H-spiro[naphthalene-1,21'-[19]oxa[12]thia[1,13]diaza tetracyclo[13.7.2.0$^{3,6}$.0$^{18,23}$]tetracosa[9,15,17,23]tetraen]-14'-one 12',12'-dioxide

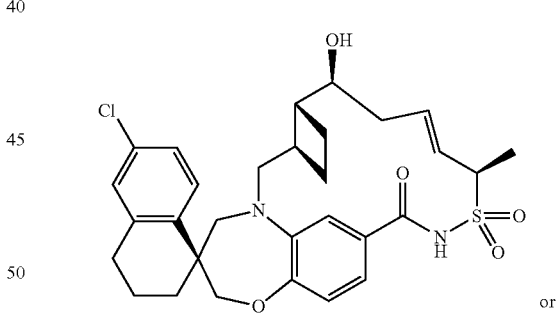

or

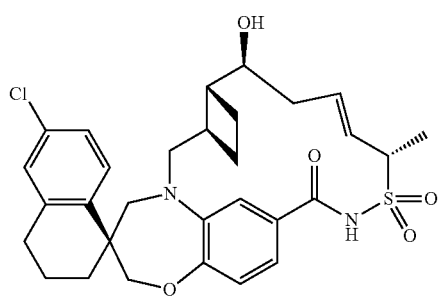

1601

Step 1. (R)—N,N-bis(4-methoxybenzyl)but-3-ene-2-sulfonamide and (S)—N,N-bis(4-methoxybenzyl)but-3-ene-2-sulfonamide

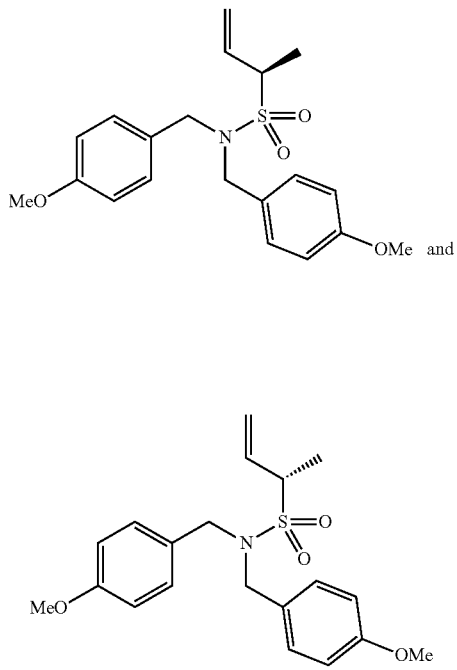

The title compounds were synthesized from N,N-bis(4-methoxybenzyl)prop-2-ene-1-sulfonamide (Example 756, Step 3; 230 mg, 0.636 mmol) following the procedure described for Intermediate EE18, Step 1. (R)—N,N-bis(4-methoxybenzyl)but-3-ene-2-sulfonamide and (S)—N,N-bis(4-methoxybenzyl)but-3-ene-2-sulfonamide (131 mg, 0.349 mmol, 54.8% yield) were obtained as a racemic mixture.

Step 2. (R)-but-3-ene-2-sulfonamide and (S)-but-3-ene-2-sulfonamide

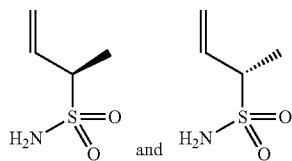

The title compounds were synthesized from (R)—N,N-bis(4-methoxybenzyl)but-3-ene-2-sulfonamide and (S)—N,N-bis(4-methoxybenzyl)but-3-ene-2-sulfonamide (131 mg, 0.349 mmol) following the procedure described for Intermediate EE17, step 2. (R)-but-3-ene-2-sulfonamide and (S)-but-3-ene-2-sulfonamide (32.4 mg, 0.240 mmol, 68.7% yield) were obtained as a racemic mixture.

1602

Step 3. (S)—N—((R)-but-3-en-2-ylsulfonyl)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide and (S)—N—((S)-but-3-en-2-ylsulfonyl)-6'-chloro-5-(((1R,2R)-2-((S)-1-hydroxybut-3-en-1-yl)cyclobutyl)methyl)-3',4,4',5-tetrahydro-2H,2'H-spiro [benzo[b][1,4]oxazepine-3,1'-naphthalene]-7-carboxamide

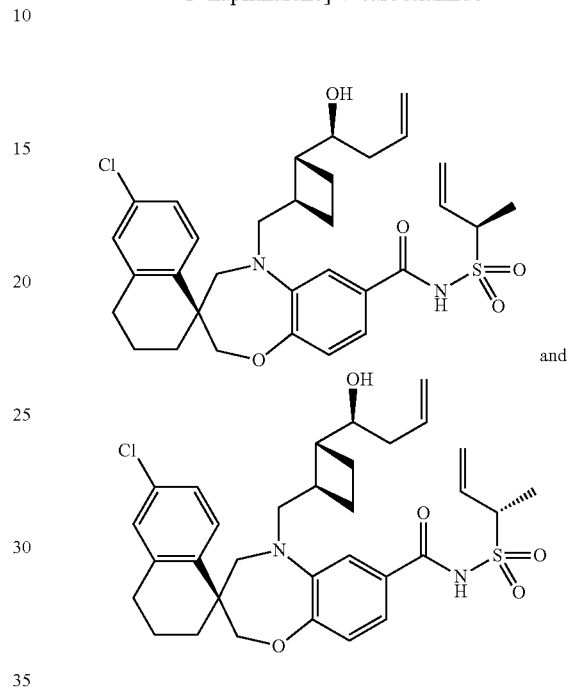

The title compound were synthesized from (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA13A; 73 mg, 0.151 mmol) and a mixture of (R)-but-3-ene-2-sulfonamide and (S)-but-3-ene-2-sulfonamide (Example 765, step 2, 32 mg, 0.237 mmol) following the procedure described for Example 719, Step 2, Step 1. Purification of the crude material provided (S)—N—((R)-but-3-en-2-ylsulfonyl)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide and (S)—N—((S)-but-3-en-2-ylsulfonyl)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide (68 mg, 0.113 mmol, 74.9% yield, 85% purity).

Step 4. (1S,3'R,6'R,7'S,9'E,11'R)-6-chloro-7'-hydroxy-11'-methyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[9,15,17,23]tetraen]-14'-one 12',12'-dioxide or (1S,3'R,6'R,7'S,9'E,11'S)-6-chloro-7'-hydroxy-11'-methyl-3,4-dihydro-2H,14'H-spiro[naphthalene-1,21'-[19]oxa[12]thia[1,13]diazatetracyclo [13.7.2.0$^{3,6}$.0$^{18,23}$]tetracosa[9,15,17,23]tetraen]-14'-one 12',12'-dioxide The title compound was synthesized from a mixture of (S)—N—((R)-but-3-en-2-ylsulfonyl)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3, 1'-naphthalene]-7-carboxamide and (S)—N—((S)-but-3-en-2-ylsulfonyl)-6'-chloro-5-(((1R,2R)-2-((S)-1-hydroxybut-3-en-1-yl)cyclobutyl) methyl)-3',4,4',5-tetrahydro-2H,2'H-spiro[benzo[b][1,4]oxazepine-3,1'-naphthalene]-7-carboxamide (Example 765, step 3, 68 mg, 0.113 mmol, 85% purity) following the procedure described for Example 45, Step 2. The crude material was purified by silica gel chromatography on a 12 g ISCO Gold column eluting with a gradient of 10-20-50% EtOAc (containing 0.3% AcOH) in hexanes over 22 min. to provide an inseparable mixture of isomers. This material was repurified by reverse phase HPLC providing (1S,3'R,6'R,7'S,9'E,11'R)-6-chloro-7'-hydroxy-11'-methyl-3,4-dihydro-2H,14'H-spiro[naphthalene-1,21'-[19]oxa[12]thia[1,13]diazatetracyclo [13.7.2.0$^{3,6}$.0$^{18,23}$]tetracosa[9,15,17,23]tetraen]-14'-one 12',12'-dioxide or (1S,3'R,6'R,7'S,9'E,11'S)-6-chloro-7'-hydroxy-11'-methyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa [9,15,17,23]tetraen]-14'-one 12',12'-dioxide as the first eluting isomer (1.3 mg, 0.0023 mmol, 2% yield). $^1$H NMR (400 MHz, CD$_2$Cl$_2$) δ 8.49 (br s, 1H), 7.71 (d, J=8.4 Hz, 1H), 7.27 (dd, J=2.2, 8.2 Hz, 1H), 7.18 (dd, J=2.4, 8.5 Hz, 1H), 7.09 (d, J=2.3 Hz, 1H), 7.03 (s, 1H), 6.96 (d, J=8.2 Hz, 1H), 5.74 (ddd, J=4.9, 10.0, 15.4 Hz, 1H), 5.49 (dd, J=8.9, 15.6 Hz, 1H), 4.32 (qd, J=6.8, 9.0 Hz, 1H), 4.18-4.09 (m, 2H), 3.72 (dd, J=8.0, 15.1 Hz, 1H), 3.69 (d, J=15.1 Hz, 1H), 3.64-3.58 (m, 1H), 3.34 (d, J=14.5 Hz, 1H), 3.23 (dd, J=2.2, 15.3 Hz, 1H), 2.85-2.69 (m, 2H), 2.58-2.45 (m, 2H), 2.42-2.32 (m, 1H), 2.05-2.00 (m, 1H), 2.00-1.93 (m, 2H), 1.93-1.85 (m, 1H), 1.85-1.78 (m, 1H), 1.71-1.64 (m, 2H), 1.57 (d, J=7.2 Hz, 3H), 1.52-1.40 (m, 3H). MS (ESI, +ve ion) m/z 571.1 (M+H)$^+$.

Example 766. (1S,3'R,6'R,7'S,9'E,11'R)-6-chloro-7'-hydroxy-11'-ethyl-3,4-dihydro-2H,14'H-spiro[naphthalene-1,21'-[19]oxa[12]thia[1,13]diaza tetracyclo [13.7.2.0$^{3,6}$.0$^{18,23}$]tetracosa[9,15,17,23]tetraen]-14'-one 12',12'-dioxide or (1S,3'R,6'R,7'S,9'E,11'S)-6-chloro-7'-hydroxy-11'-ethyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[9,15,17,23]tetraen]-14'-one 12',12'-dioxide

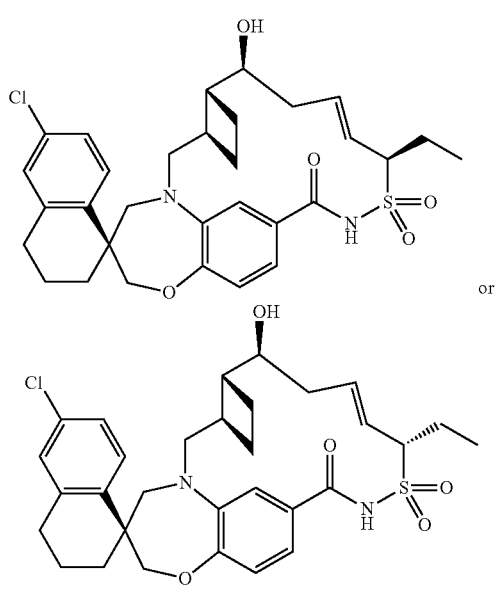

or

Step 1. (S)-6'-chloro-5-(((1R,2R)-2-((S)-1-hydroxybut-3-en-1-yl)cyclobutyl)methyl)-N—((R)-pent-1-en-3-ylsulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxybut-3-en-1-yl)cyclobutyl)methyl)-N—((S)-pent-1-en-3-ylsulfonyl)-3',4,4',5-tetrahydro-2H,2'H-spiro[benzo[b][1,4]oxazepine-3,1'-naphthalene]-7-carboxamide

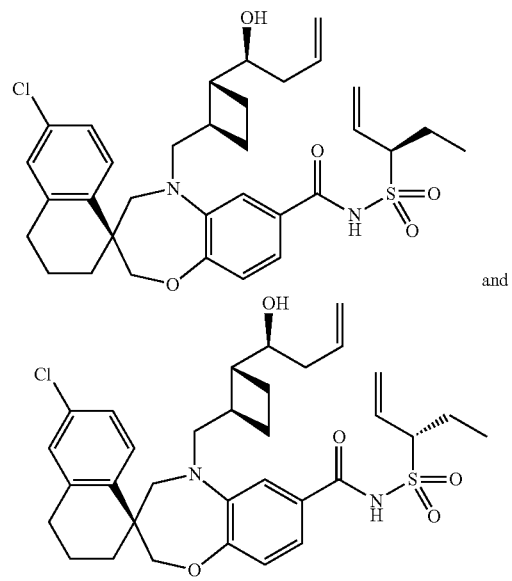

and

The title compound were synthesized from (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA13A; 239 mg, 0.496 mmol) and a racemic mixture of (R)-pent-1-ene-3-sulfonamide and (S)-pent-1-ene-3-sulfonamide (Example 756, Step 5; 127 mg, 0.851 mmol) following the procedure described for Example 719, Step 2, Step 1. Purification of the crude material provided (S)-6'-chloro-5-(((1R,2R)-2-((S)-1-hydroxybut-3-en-1-yl)cyclobutyl)methyl)-N—((R)-pent-1-en-3-ylsulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxybut-3-en-1-yl)cyclobutyl)methyl)-N—((S)-pent-1-en-3-ylsulfonyl)-3',4,4',5-tetrahydro-2H,2'H-spiro[benzo[b][1,4]oxazepine-3,1'-naphthalene]-7-carboxamide (214 mg, 0.349 mmol, 70.4% yield).

Step 2. (1S,3'R,6'R,7'S,9'E,11'R)-6-chloro-7'-hydroxy-11'-ethyl-3,4-dihydro-2H,14'H-spiro[naphthalene-1,21'-[19]oxa[12]thia[1,13]diazatetracyclo [13.7.2.0$^{3,6}$.0$^{18,23}$]tetracosa[9,15,17,23]tetraen]-14'-one 12',12'-dioxide or (1S,3'R,6'R,7'S,9'E,11'S)-6-chloro-7'-hydroxy-11'-ethyl-3,4-dihydro-2H,14'H-spiro[naphthalene-1,21'-[19]oxa[12]thia[1,13]diazatetracyclo [13.7.2.0$^{3,6}$.0$^{18,23}$]tetracosa[9,15,17,23]tetraen]-14'-one 12',12'-dioxide The title compound was synthesized from a mixture of (S)-6'-chloro-5-(((1R,2R)-2-((S)-1-hydroxybut-3-en-1-yl)cyclobutyl)methyl)-N—((R)-pent-1-en-3-ylsulfonyl)-3',4,4',5-tetrahydro-2H,2'H-spiro[benzo[b][1,4]oxazepine-3,1'- naphthalene]-7-carboxamide and (S)-6'-chloro-5-(((1R,2R)-2-((S)-1-hydroxybut-3-en-1-yl)cyclobutyl)methyl)-N—((S)-pent-1-en-3-ylsulfonyl)-3',4,4',5-tetrahydro-2H,2'H-spiro[benzo[b][1,4]oxazepine-3,1'-naphthalene]-7-carboxamide (Example 766, step 1, 214 mg, 0.349 mmol) following the procedure described for Example 742, Step 2. The crude material was purified by silica gel chromatography on a 40 g ISCO Gold column eluting with a gradient of 10-50% EtOAc (containing 0.3% AcOH) in hexanes over 30 min. to provide an inseparable mixture of isomers. This material was repurified by reverse phase HPLC providing (1S,3'R,6'R,7'S,9'E,11'R)-6-chloro-7'-hydroxy-11'-ethyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa [9,15,17,23]tetraen]-14'-one 12',12'-dioxide or (1S,3'R,6'R,7'S,9'E,11'S)-6-chloro-7'-hydroxy-11'-ethyl-3,4-dihydro-2H,14'H-spiro[naphthalene-1,21'-[19]oxa[12]thia[1,13]diazatetracyclo [13.7.2.0$^{3,6}$.0$^{18,23}$]tetracosa [9,15,17,23]tetraen]-14'-one 12',12'-dioxide as the first eluting and major isomer (13.3 mg, 0.023 mmol, 6.5% yield). $^{1}$H NMR (400 MHz, CD$_2$Cl$_2$) δ 8.68 (br s, 1H), 7.71 (d, J=8.4 Hz, 1H), 7.27 (dd, J=2.1, 8.3 Hz, 1H), 7.18 (dd, J=2.3, 8.4 Hz, 1H), 7.09 (d, J=2.2 Hz, 1H), 7.03 (s, 1H), 6.96 (d, J=8.2 Hz, 1H), 5.76 (ddd, J=5.2, 10.0, 15.4 Hz, 1H), 5.43 (dd, J=9.8, 15.8 Hz, 1H), 4.17-4.09 (m, 2H), 4.11-4.06 (m, 1H), 3.76 (dd, J=9.3, 15.7 Hz, 1H), 3.69 (d, J=14.7 Hz, 1H), 3.63 (ddd, J=2.2, 5.7, 8.5 Hz, 1H), 3.33 (d, J=14.7 Hz, 1H), 3.20 (dd, J=3.4, 15.7 Hz, 1H), 2.85-2.69 (m, 2H), 2.63-2.44 (m, 2H), 2.43-2.33 (m, 1H), 2.23 (qdd, J=3.9, 7.4, 13.3 Hz, 1H), 2.09-2.02 (m, 1H), 2.01-1.90 (m, 3H), 1.90-1.85 (m, 1H), 1.86-1.78 (m, 2H), 1.70-1.60 (m, 2H), 1.58-1.48 (m, 1H), 1.47-1.39 (m, 1H), 1.01 (t, J=7.4 Hz, 3H). MS (ESI, +ve ion) m/z 585.1 (M+H)$^+$.

Example 767. (1S,3'R,6'R,7'S,9'E,11'S)-6-chloro-7'-hydroxy-11'-ethyl-3,4-dihydro-2H,14'H-spiro[naphthalene-1,21'-[19]oxa[12]thia[1,13]diaza tetracyclo [13.7.2.0$^{3,6}$.0$^{18,23}$]tetracosa[9,15,17,23]tetraen]-14'-one 12',12'-dioxide or (1S,3'R,6'R,7'S,9'E,11'R)-6-chloro-7'-hydroxy-11'-ethyl-3,4-dihydro-2H,14'H-spiro[naphthalene-1,21'-[19]oxa[12]thia[1,13]diaza tetracyclo[13.7.2.0$^{3,6}$.0$^{18,23}$]tetracosa[9,15,17,23]tetraen]-14'-one 12',12'-dioxide The second eluting and minor isomer from the purifications described in Example 766, step 2 was contaminated by 18% olefin isomer. This material was further purified by SFC (Column: Chiralpak OD-H, 2.1×25 cm; Mobile phase: 35% Methanol/65% CO$_2$; Flow rate: 50 m/min; SFC Outlet pressure: 100 bar; Temp.=23 C; Wavelength: 260 nm; Sample dissolved to 2.6 mg/mL in 6:1 Methanol:DCM; introduced 0.15 mL of sample solution, or 0.4 mg crude sample in each preparative injection) to provide the pure title compound (5.5 mg, 0.0094 mmol, 2.7% yield). $^{1}$H NMR (400 MHz, CD$_2$Cl$_2$) δ 8.58 (br s, 1H), 7.67 (d, J=8.6 Hz, 1H), 7.27 (br s, 2H), 7.16 (dd, J=2.3, 8.6 Hz, 1H), 7.09 (d, J=2.3 Hz, 1H), 6.92 (d, J=8.2 Hz, 1H), 5.81-5.69 (m, 1H), 5.42 (dd, J=9.7, 15.2 Hz, 1H), 4.16 (br s, 3H), 3.67 (br s, 1H), 3.61-3.35 (m, 4H), 2.82-2.69 (m, 2H), 2.67-2.56 (m, 1H), 2.43-2.30 (m, 1H), 2.28-2.10 (m, 4H), 1.95-1.84 (m, 2H), 1.83-1.65 (m, 6H), 1.46-1.35 (m, 1H), 1.02 (t, J=7.4 Hz, 3H). MS (ESI, +ve ion) m/z 585.1 (M+H)$^+$.

Example 768. (1S,3'R,6'R,7'S,11'R)-6-chloro-11'-ethyl-7'-hydroxy-3,4-dihydro-2H,14'H-spiro[naphthalene-1,21'-[19]oxa[12]thia[1,13]diaza tetracyclo[13.7.2.0$^{3,6}$.0$^{18,23}$]tetracosa[15,17,23]trien]-14'-one 12',12'-dioxide or (1S,3'R,6'R,7'S,11'S)-6-chloro-11'-ethyl-7'-hydroxy-3,4-dihydro-2H,14'H-spiro[naphthalene-1,21'-[19]oxa[12]thia[1,13]diazatetracyclo [13.7.2.0$^{3,6}$.0$^{18,23}$]tetracosa[15,17,23]trien]-14'-one 12',12'-dioxide

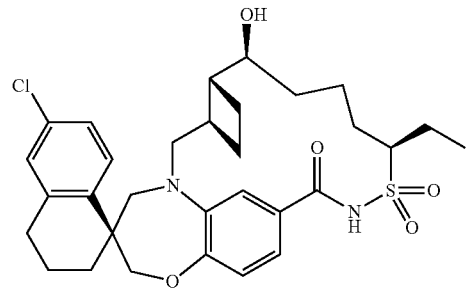

or

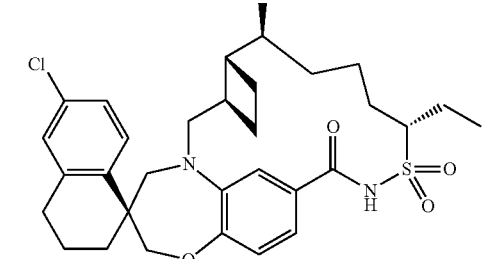

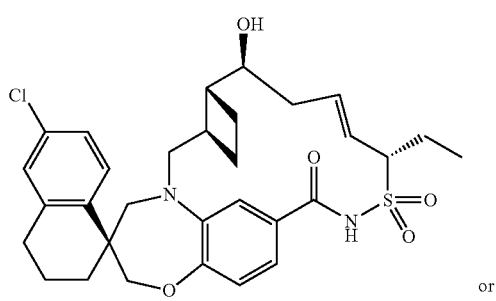

or

The title compound was synthesized from (1S,3'R,6'R,7'S,9'E,11'R)-6-chloro-7'-hydroxy-11'-ethyl-3,4-dihydro-2H,14'H-spiro[naphthalene-1,21'-[19]oxa[12]thia[1,13]diazatetracyclo [13.7.2.0$^{3,6}$.0$^{18,23}$]tetracosa[9,15,17,23]tetraen]-14'-one 12',12'-dioxide or (1S,3'R,6'R,7'S,9'E,11'S)-6-chloro-7'-hydroxy-11'-ethyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[9,15,17,23]tetraen]-14'-one 12,12'-dioxide (Example 766; 11 mg, 0.019 mmol) following the procedure described for Example 84 providing (1S,3'R,6'R,7'S,11'R)-6-chloro-11'-ethyl-7'-hydroxy-3,4-dihydro-2H,14'H-spiro[naphthalene-1,21'-[19]oxa[12]thia[1, 13]diazatetracyclo[13.7.2.0$^{3,6}$.0$^{18,23}$]tetracosa[15,17,23]

trien]-14'-one 12',12'-dioxide or (1S,3'R,6'R,7'S,11'S)-6-chloro-11'-ethyl-7'-hydroxy-3,4-dihydro-2H,14'H-spiro[naphthalene-1,21'-[19]oxa[12]thia[1,13]diazatetracyclo[13.7.2.0³,⁶.0¹⁸,²³]tetracosa[15,17,23]trien]-14'-one 12',12'-dioxide (3.5 mg, 0.006 mmol, 31.7% yield). ¹H NMR (400 MHz, CD₂Cl₂) δ 9.60 (s, 1H), 7.72 (d, J=8.6 Hz, 1H), 7.35 (dd, J=2.1, 8.3 Hz, 1H), 7.16 (dd, J=2.4, 8.5 Hz, 1H), 7.12 (d, J=1.8 Hz, 1H), 7.09 (d, J=2.2 Hz, 1H), 6.97 (d, J=8.2 Hz, 1H), 4.11 (s, 2H), 3.90-3.84 (m, 1H), 3.82 (d, J=15.5 Hz, 1H), 3.63 (d, J=14.1 Hz, 1H), 3.58-3.50 (m, 1H), 3.18 (d, J=14.1 Hz, 1H), 3.11 (dd, J=7.7, 15.4 Hz, 1H), 2.84-2.69 (m, 2H), 2.30-2.08 (m, 4H), 2.05-1.94 (m, 4H), 1.93-1.86 (m, 2H), 1.85-1.74 (m, 3H), 1.70-1.56 (m, 3H), 1.50-1.39 (m, 3H), 1.12 (t, J=7.4 Hz, 3H). MS (ESI, +ve ion) m/z 587.2 (M+H)⁺.

Example 769. (1S,3'R,6'R,7'S,8'E)-6-chloro-7'-hydroxy-11',11'-dimethyl-3,4-dihydro-2H,14'H-spiro[naphthalene-1,21'-[19]oxa[12]thia[1,13]diaza tetracyclo[13.7.2.0³,⁶.0¹⁸,²³]tetracosa[8,15,17,23]tetraen]-14'-one 12',12'-dioxide

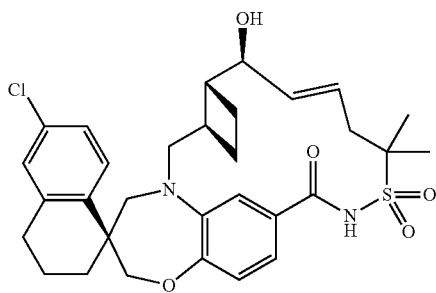 [SMILES: CC1(C)C/C=C/[C@H](O)[C@@H]2CC[C@H]2CN2C[C@@]3(CCCc4cc(Cl)ccc43)COc3ccc(cc32)C(=O)NS1(=O)=O]

Step 1. (S)-tert-butyl 6'-chloro-5-(((1R,2R)-2-((S,E)-1-hydroxy-5-methyl-5-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylate

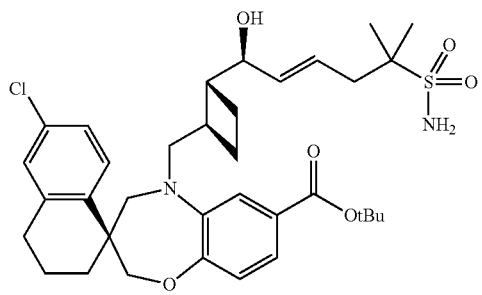 [SMILES: CC(C)(C)OC(=O)c1ccc2c(c1)N(C[C@@H]1CC[C@H]1[C@@H](O)/C=C/CC(C)(C)S(N)(=O)=O)C[C@@]1(CCCc3cc(Cl)ccc31)CO2]

The title compound was synthesized from (S)-tert-butyl 6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (Intermediate AA12B, step 1B, first eluting isomer; 171 mg, 0.302 mmol) and 2-methylpent-4-ene-2-sulfonamide (Example 781, Step 2, 99 mg, 0.604 mmol) following the procedure described for Example 762, step 1. The reaction mixture was directly injected into a 24 g ISCO Gold column, and purified eluting with a gradient of 0-20-80% EtOAc in hexanes over 18 min to give (S)-tert-butyl 6'-chloro-5-(((1R,2R)-2-((S,E)-1-hydroxy-5-methyl-5-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylate (39 mg, 0.059 mmol, 19.6% yield).

Step 2. (S)-6'-chloro-5-(((1R,2R)-2-((S,E)-1-hydroxy-5-methyl-5-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic Acid

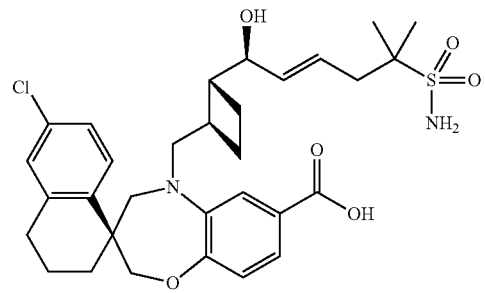 [SMILES: CC(C)(C/C=C/[C@H](O)[C@@H]1CC[C@H]1CN1C[C@@]2(CCCc3cc(Cl)ccc32)COc2ccc(C(=O)O)cc21)S(N)(=O)=O]

The title compound was synthesized from (S)-tert-butyl 6'-chloro-5-(((1R,2R)-2-((S,E)-1-hydroxy-5-methyl-5-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylate (Example 769, step 1, 39 mg, 0.059 mmol) following the procedure described for Example 762 Step 2. The crude material was used without further purification.

Step 3. (1S,3'R,6'R,7'S,8'E)-6-chloro-7'-hydroxy-11',11'-dimethyl-3,4-dihydro-2H,14'H-spiro[naphthalene-1,21'-[19]oxa[12]thia[1,13]diazatetracyclo[13.7.2.0³,⁶.0¹⁸,²³]tetracosa[8,15,17,23]tetraen]-14'-one 12',12'-dioxide The title compound was synthesized from (S)-6'-chloro-5-(((1R,2R)-2-((S,E)-1-hydroxy-5-methyl-5-sulfamoylhex-2-en-1-yl)cyclobutyl)methyl)-3',4,4',5-tetrahydro-2H,2'H-spiro [benzo[b][1,4]oxazepine-3,1'-naphthalene]-7-carboxylic acid (Example 769, step 2, 35 mg, 0.058 mmol) following the procedure described for Example 762, Step 3. The crude material was purified by silica gel chromatography through a 12 g ISCO gold column eluting with a gradient of 10-45-60% EtOAc (containing 0.3% AcOH) in hexanes to provide (1S,3'R,6'R,7'S,8'E)-6-chloro-7'-hydroxy-11',11'-dimethyl-3,4-dihydro-2H,14'H-spiro[naphthalene-1,21'-[19]oxa[12]thia[1,13]diaza tetracyclo[13.7.2.0³,⁶.0¹⁸,²³]tetracosa[8,15,17,23]tetraen]-14'-one 12',12'-dioxide (6.8 mg, 0.012 mg, 20% yield). ¹H NMR (400 MHz, CD₂Cl₂) δ 8.38 (br s, 1H), 7.71 (d, J=8.4 Hz, 1H), 7.23-7.17 (m, 1H), 7.17 (dd, J=2.3, 8.4 Hz, 1H), 7.09 (d, J=2.3 Hz, 1H), 6.94 (d, J=8.2 Hz, 1H), 6.74 (br s, 1H), 6.15 (td, J=5.7, 15.8 Hz, 1H), 5.93-5.82 (m, 1H), 4.18 (t, J=4.8 Hz, 1H), 4.12-4.05 (m, 2H), 3.71 (d, J=14.7 Hz, 1H), 3.66 (d, J=13.7 Hz, 1H), 3.36 (d, J=14.5 Hz, 1H), 3.20 (dd, J=9.5, 15.4 Hz, 1H), 2.86-2.72 (m, 2H), 2.67 (dt, J=3.1, 8.6 Hz, 1H), 2.60 (br s, 2H), 2.35 (dd, J=4.5, 8.8 Hz, 1H), 2.06-1.97 (m, 3H), 1.97-1.91 (m, 1H), 1.89-1.78 (m, 3H), 1.68 (td, J=9.4, 19.2 Hz, 2H), 1.56 (br s, 3H), 1.53 (s, 3H). MS (ESI, +ve ion) m/z 585.1 (M+H)⁺.

Example 770. (1S,3'R,6'R,7'S)-6-chloro-7'-hydroxy-11',11'-dimethyl-3,4-dihydro-2H,14'H-spiro[naphthalene-1,21'-[19]oxa[12]thia[1,13]diaza tetracyclo[13.7.2.0³,⁶.0¹⁸,²³]tetracosa[15,17,23]trien]-14'-one 12',12'-dioxide

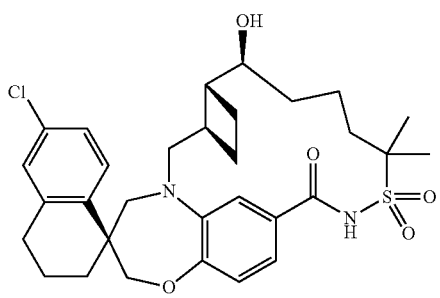 [SMILES: CC1(C)CCC[C@H](O)[C@@H]2CC[C@H]2CN2C[C@@]3(CCCc4cc(Cl)ccc43)COc3ccc(cc32)C(=O)NS1(=O)=O]

The title compound was synthesized from (1S,3'R,6'R,7'S,8'E)-6-chloro-7'-hydroxy-11',11'-dimethyl-3,4-dihydro-2H,14'H-spiro[naphthalene-1,21'-[19]oxa[12]thia[1,13]diaza tetracyclo[13.7.2.0³,⁶.0¹⁸,²³]tetracosa[8,15,17,23]tetraen]-14'-one 12',12'-dioxide (Example 769; 5 mg, 0.0086 mmol) following the procedure described for Example 84 providing (1S,3'R,6'R,7'S)-6-chloro-7'-hydroxy-11',11'-dimethyl-3,4-dihydro-2H,14'H-spiro[naphthalene-1,21'-[19]oxa[12]thia[1,13]diazatetracyclo[13.7.2.0³,⁶.0¹⁸,²³]tetracosa[15,17,23]trien]-14'-one 12',12'-dioxide (3.2 mg, 0.0054 mmol, 63.8% yield). ¹H NMR (500 MHz, CD₂Cl₂) δ 10.20 (br s, 1H), 7.71 (d, J=8.6 Hz, 1H), 7.47 (dd, J=2.1, 8.4 Hz, 1H), 7.28 (d, J=1.7 Hz, 1H), 7.15 (dd, J=2.3, 8.4 Hz, 1H), 7.09 (d, J=2.4 Hz, 1H), 6.95 (d, J=8.3 Hz, 1H), 4.10-4.05 (m, 2H), 3.94-3.85 (m, 1H), 3.81 (d, J=15.4 Hz, 1H), 3.58 (d, J=14.2 Hz, 1H), 3.15 (d, J=14.4 Hz, 1H), 3.08 (dd, J=8.2, 15.0 Hz, 1H), 2.82-2.70 (m, 3H), 2.62 (br s, 1H), 2.27 (quin, J=8.3 Hz, 1H), 2.11-2.07 (m, 1H), 2.04-1.97 (m, 2H), 1.96-1.85 (m, 3H), 1.82-1.74 (m, 3H), 1.70-1.56 (m, 5H), 1.51 (s, 3H), 1.48 (s, 3H). MS (ESI, +ve ion) m/z 587.1 (M+H)⁺.

Example 771. (1S,3'R,6'R,7'S,9'E)-6-chloro-7'-hydroxy-3,4-dihydro-2H,14'H-spiro[naphthalene-1,21'-[19]oxa[12]thia[1,13]diazatetracyclo [13.7.2.0³,⁶.0¹⁸,²³]tetracosa[9,15,17,23]tetraen]-14'-one 12',12'-dioxide

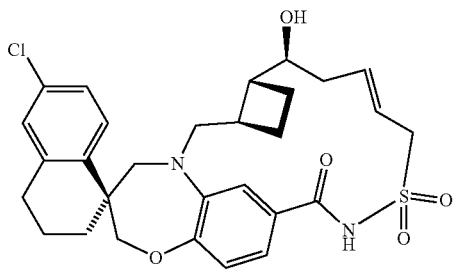

Step 1. Prop-2-ene-1-sulfonamide

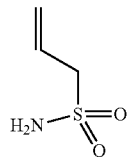

The title compound was synthesized from N,N-bis(4-methoxybenzyl)prop-2-ene-1-sulfonamide (Example 756, Step 3; 265 mg, 0.733 mmol) following the procedure described for Intermediate EE17, Step 2 providing prop-2-ene-1-sulfonamide (35 mg, 0.289 mmol, 39.4% yield).

Step 2. (S)—N-(allylsulfonyl)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide

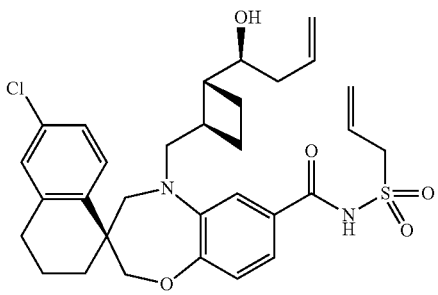 [SMILES: C=CC[C@H](O)[C@@H]1CC[C@H]1CN1C[C@@]2(CCCc3cc(Cl)ccc32)COc2ccc(C(=O)NS(=O)(=O)CC=C)cc21]

The title compound was synthesized from (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA13A; 49 mg, 0.102 mmol) and prop-2-ene-1-sulfonamide (Example 771, step 1, 35 mg, 0.289 mmol) following the procedure described for Example 719, Step 2, Step 1. Purification of the crude material provided (S)—N-(allylsulfonyl)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide (50 mg, 0.085 mmol, 84% yield).

Step 4. (1S,3'R,6'R,7'S,9'E)-6-chloro-7'-hydroxy-3,4-dihydro-2H,14'H-spiro[naphthalene-1,21'-[19]oxa[12]thia[1,13]diazatetracyclo [13.7.2.0³,⁶.0¹⁸,²³]tetracosa[9,15,17,23]tetraen]-14'-one 12',12'-dioxide or (1S,3'R,6'R,7'R,9'E)-6-chloro-7'-hydroxy-3,4-dihydro-2H,14'H-spiro [naphthalene-1,21'-[19]oxa[12]thia[1,13]diazatetracyclo[13.7.2.0³,⁶.0¹⁸,²³]tetracosa[9,15,17,23]tetraen]-14'-one 12',12'-dioxide The title compound was synthesized from (S)—N-(allylsulfonyl)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide (Example 771, step 3, 50 mg, 0.085 mmol) following the procedure described for Example 742, Step 2. The crude material was purified by silica gel chromatography on a 12 g ISCO Gold column eluting with a gradient of 10-20-50%

1611

EtOAc (containing 0.3% AcOH) in hexanes over 18 min to provide (1S,3'R,6'R,7'S,9'E)-6-chloro-7'-hydroxy-3,4-dihydro-2H,14'H-spiro[naphthalene-1,21'-[19]oxa[12]thia[1,13]diazatetracyclo[13.7.2.0³,⁶.0¹⁸,²³]tetracosa [9,15,17,23]tetraen]-14'-one 12',12'-dioxide (5.8 mg, 0.0010 mmol, 12.2% yield). ¹H NMR (400 MHz, CD₂Cl₂) δ 7.69 (d, J=8.4 Hz, 1H), 7.19-7.15 (m, 1H), 7.14 (br s, 1H), 7.12 (br s, 1H), 7.09 (d, J=2.2 Hz, 1H), 6.93 (d, J=8.2 Hz, 1H), 5.79 (td, J=6.7, 15.7 Hz, 1H), 5.59 (td, J=7.3, 15.0 Hz, 1H), 4.19 (dd, J=8.0, 14.3 Hz, 1H), 4.13 (s, 2H), 4.11-4.04 (m, 1H), 3.62 (br s, 3H), 3.37 (br s, 2H), 2.83-2.69 (m, 2H), 2.60 (quin, J=8.9 Hz, 1H), 2.47-2.35 (m, 1H), 2.28 (ddd, J=5.2, 8.6, 14.0 Hz, 1H), 2.18-2.10 (m, 1H), 1.98-1.74 (m, 6H), 1.67 (quin, J=10.6 Hz, 1H), 1.56-1.48 (m, 1H), 1.46 (dd, J=10.0, 20.0 Hz, 1H). MS (ESI, +ve ion) m/z 557.2 (M+H)⁺.

Example 772. (1S,3'R,6'R,7'S,8'E,11'R)-6-chloro-7'-hydroxy-11'-(methoxy methyl)-3,4-dihydro-2H,14'H-spiro[naphthalene-1,21'-[19]oxa[12]thia[1,13]diazatetracyclo[13.7.2.0³,⁶.0¹⁸,²³]tetracosa[8,15,17,23]tetraen]-14'-one 12',12'-dioxide or (1S,3'R,6'R,7'S,8'E,11'S)-6-chloro-7'-hydroxy-11'-(methoxy methyl)-3,4-dihydro-2H,14'H-spiro[naphthalene-1,21'-[19]oxa[12]thia[1,13]diazatetracyclo[13.7.2.0³,⁶.0¹⁸,²³]tetracosa[8,15,17,23]tetraen]-14'-one 12',12'-dioxide

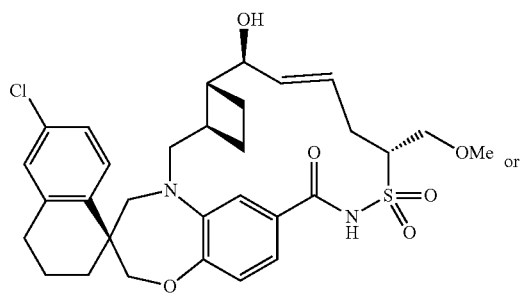

or

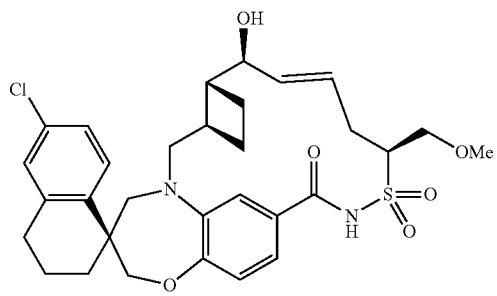

1612

Step 1. (R)-methyl 2-(N,N-bis(4-methoxybenzyl)sulfamoyl)pent-4-enoate and (S)-methyl 2-(N,N-bis(4-methoxybenzyl)sulfamoyl)pent-4-enoate

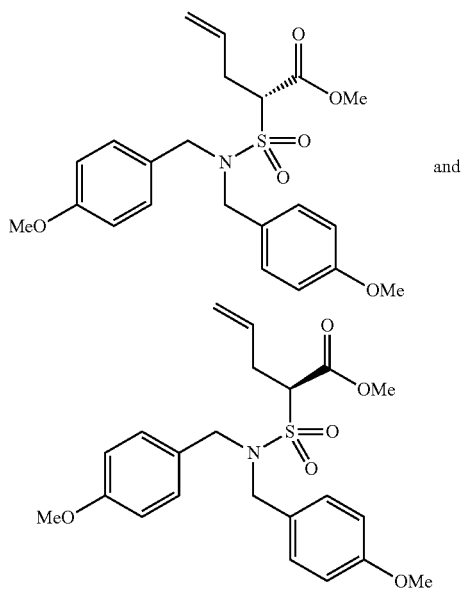

N,N-bis(4-methoxybenzyl)but-3-ene-1-sulfonamide (Intermediate EE16; 740 mg, 1.971 mmol) was azeotroped in PhMe under vacuum for 2 h, then, under Ar, THF was added and the solution was cooled to −78° C. Butyllithium solution (2.5 M in hexanes; 0.946 mL, 2.37 mmol) was then added and the mixture was stirred at −78° C. for 60 min. In a separate flask, a solution of methyl chloroformate (Sigma Aldrich; 0.305 mL, 3.94 mmol) in THF (4 mL) was cooled to −78° C. To this solution was added the anion solution slowly. After 10 min the mixture was quenched with sat. NH4Cl, allowed to reach ambient temperature and extracted with EtOAc, dried over MgSO₄ and concentrated. The crude mixture of (R)-methyl 2-(N,N-bis(4-methoxy benzyl)sulfamoyl)pent-4-enoate and (S)-methyl 2-(N,N-bis(4-methoxybenzyl)sulfamoyl)pent-4-enoate NMR showed a significant amount of unreacted starting material) was used without further purification.

Step 2. (R)-1-hydroxy-N,N-bis(4-methoxybenzyl)pent-4-ene-2-sulfonamide and (S)-1-hydroxy-N,N-bis(4-methoxybenzyl)pent-4-ene-2-sulfonamide

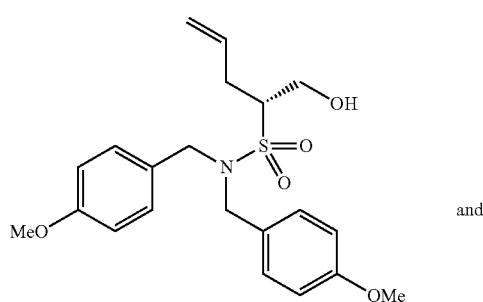

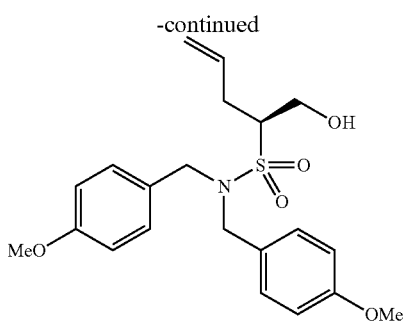

To a 50 mL round-bottomed flask charged with a mixture of (R)-methyl 2-(N,N-bis(4-methoxybenzyl)sulfamoyl) pent-4-enoate and (S)-methyl 2-(N,N-bis(4-methoxybenzyl) sulfamoyl)pent-4-enoate (Example 772, step 1, 854 mg, 1.97 mmol) in THF (9.85 mL) at ambient temperature was added lithium borohydride (2.0 M solution in tetrahydrofuran; 1.97 mL, 3.94 mmol) and a few drops of MeOH. The mixture was stirred at ambient temperature overnight. The reaction mixture was quenched with 1N HCl, diluted with NH4Cl and extracted with EtOAc. The organic phase was dried over MgSO$_4$, filtered and concentrated. The crude material was purified by chromatography through a 24 g ISCO Gold column, eluting with a gradient of 15% to 60% EtOAc in hexane, to provide a mixture of (R)-1-hydroxy-N,N-bis(4-methoxybenzyl)pent-4-ene-2-sulfonamide and (S)-1-hydroxy-N,N-bis(4-methoxybenzyl)pent-4-ene-2-sulfonamide (415 mg, 1.02 mmol, 52.0% yield for the two steps).

Step 3. (R)-1-methoxy-N,N-bis(4-methoxybenzyl) pent-4-ene-2-sulfonamide and (S)-1-methoxy-N,N-bis(4-methoxybenzyl)pent-4-ene-2-sulfonamide

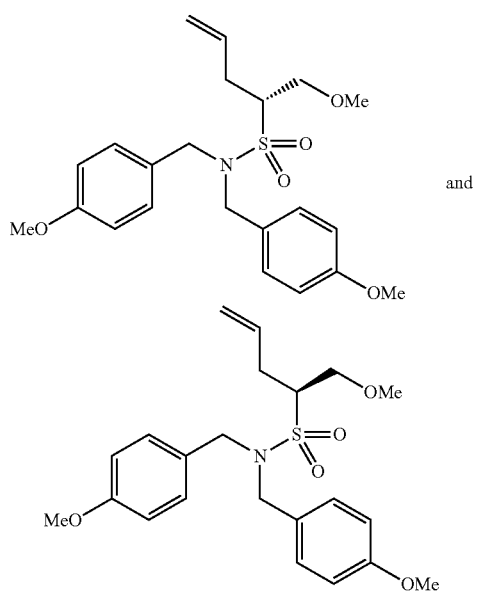

To a 50 mL round-bottomed flask was added a mixture of (R)-1-hydroxy-N,N-bis(4-methoxybenzyl)pent-4-ene-2-sulfonamide and (S)-1-hydroxy-N,N-bis(4-methoxybenzyl) pent-4-ene-2-sulfonamide (Example 772, step 2, 415 mg, 1.02 mmol) and iodomethane (1.27 mL, 20.5 mmol) in THF (6.82 mL) and the mixture was cooled to −78° C. Potassium tert-butoxide (1.0 M solution in tetrahydrofuran; 1.003 mL, 1.003 mmol) was added dropwise via a syringe slowly. The mixture was stirred for 1 hr then it was allowed to warm to ambient temperature. The mixture was then quenched with sat NH$_4$Cl and extracted with EtOAc. The organic phase was dried, filtered and concentrated. The crude material was purified by chromatography through a 24 g ISCO Gold column, eluting with a gradient of 10% to 40% EtOAc in hexane, to provide (R)-1-methoxy-N,N-bis(4-methoxybenzyl)pent-4-ene-2-sulfonamide and (S)-1-methoxy-N,N-bis(4-methoxybenzyl)pent-4-ene-2-sulfonamide (371 mg, 0.884 mmol, 86% yield).

Step 4. (R)-1-methoxypent-4-ene-2-sulfonamide and (S)-1-methoxypent-4-ene-2-sulfonamide

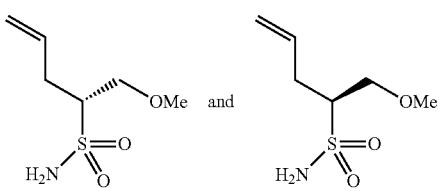

To a solution of (R)-1-methoxy-N,N-bis(4-methoxybenzyl)pent-4-ene-2-sulfonamide and (S)-1-methoxy-N,N-bis(4-methoxybenzyl)pent-4-ene-2-sulfonamide (371 mg, 0.884 mmol) and anisole (0.961 mL, 8.84 mmol) in CH$_2$Cl$_2$ (4.4 mL) at ambient temperature was added trifluoroacetic acid (2.63 mL, 35.4 mmol) slowly. After stirring for 5 h (TLC 30% EtOAc/hex showed complete loss of starting material) the mixture was concentrated. The residue was diluted with EtOAc, washed with sat. NaHCO$_3$, back extracted with EtOAc, dried over MgSO$_4$ and concentrated. The crude material was purified via chromatography through a 24 g ISCO gold column eluting with a gradient of 0-50% EtOAc in hexanes to provide (R)-1-methoxypent-4-ene-2-sulfonamide and (S)-1-methoxypent-4-ene-2-sulfonamide (139 mg, 0.776 mmol, 88% yield).

Step 5. (S)-methyl 6'-chloro-5-(((1R,2R)-2-((1S,5R,E)-1-hydroxy-6-methoxy-5-sulfamoylhex-2-en-1-yl) cyclobutyl)methyl)-3',4,4',5-tetrahydro-2H,2'H-spiro [benzo[b][1,4]oxazepine-3,1'-naphthalene]-7-carboxylate and (S)-methyl 6'-chloro-5-(((1R,2R)-2-((1S,5S,E)-1-hydroxy-6-methoxy-5-sulfamoylhex-2-en-1-yl)cyclobutyl)methyl)-3',4,4',5-tetrahydro-2H, 2'H-spiro[benzo[b][1,4]oxazepine-3,1'-naphthalene]-7-carboxylate

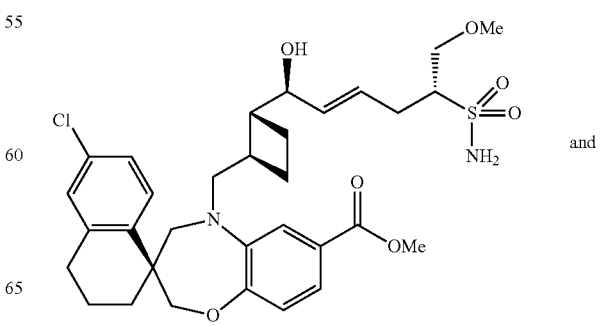

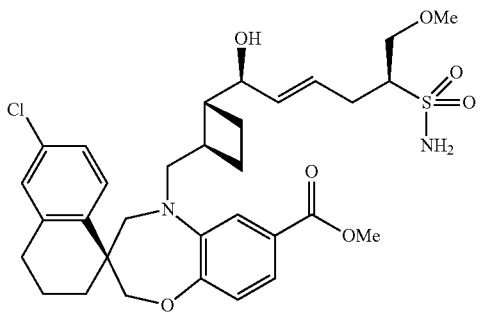

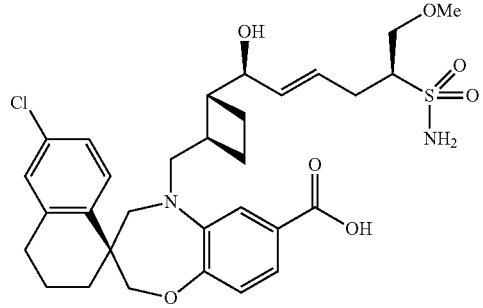

The title compound was synthesized from (S)-methyl 6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (Intermediate AA12A, Step 1A; 100 mg, 0.191 mmol) and a mixture of (R)-1-methoxypent-4-ene-2-sulfonamide and (S)-1-methoxypent-4-ene-2-sulfonamide (Example 772, Step 4; 137 mg, 0.763 mmol) following the procedure described for Example 762, Step 1. The reaction mixture was directly injected into a 12 g ISCO Gold column, and purified eluting with a gradient of 10-20-50-100% EtOAc in hexanes over 16 min to give (S)-methyl 6'-chloro-5-(((1R,2R)-2-((1S,5R,E)-1-hydroxy-6-methoxy-5-sulfamoylhex-2-en-1-yl) cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((1S,5S,E)-1-hydroxy-6-methoxy-5-sulfamoylhex-2-en-1-yl) cyclobutyl)methyl)-3',4,4',5-tetrahydro-2H,2'H-spiro[benzo[b][1,4]oxazepine-3,1'-naphthalene]-7-carboxylate (52 mg, 0.082 mmol, 43.0% yield).

Step 6. (S)-6'-chloro-5-(((1R,2R)-2-((1S,5R,E)-1-hydroxy-6-methoxy-5-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1S,5S,E)-1-hydroxy-6-methoxy-5-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic Acid

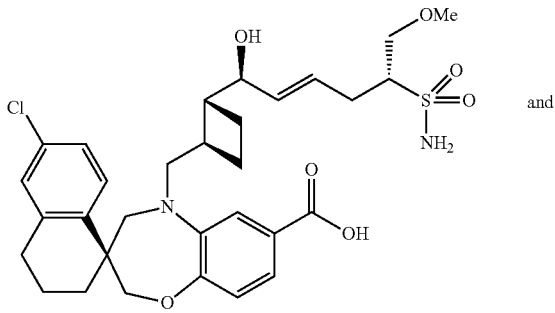

and

A RB flask was charged with (S)-methyl 6'-chloro-5-(((1R,2R)-2-((1S,5R,E)-1-hydroxy-6-methoxy-5-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylate and (S)-methyl 6'-chloro-5-(((1R,2R)-2-((1S,5S,E)-1-hydroxy-6-methoxy-5-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylate (Example 772, step 5, 52 mg, 0.082 mmol), THF (1.1 mL), MeOH (0.548 mL) and 1 N LiOH (0.575 mL, 0.575 mmol). The mixture was stirred at ambient temperature for 50 min. then at 50° C. for 1.5 h, then again at ambient temperature overnight then again at 50° C. for 2 h. The mixture was then quenched with 1 N HCl (1.15 mL, 1.15 mmol), diluted with brine (20 mL), then extracted with EtOAc (2×15 mL). The combined organics were dried (MgSO$_4$) and concentrated. The crude mixture of (S)-6'-chloro-5-(((1R,2R)-2-((1S,5R,E)-1-hydroxy-6-methoxy-5-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,E)-1-hydroxy-6-methoxy-5-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic acid was taken on to the next step without further purification.

Step 7. (1S,3'R,6'R,7'S,8'E,11'R)-6-chloro-7'-hydroxy-11'-(methoxymethyl)-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide or (1S,3'R,6'R,7'S,8'E,11'S)-6-chloro-7'-hydroxy-11'-(methoxymethyl)-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide The title compound was synthesized from a mixture of (S)-6'-chloro-5-(((1R,2R)-2-((1S,5R,E)-1-hydroxy-6-methoxy-5-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,E)-1-hydroxy-6-methoxy-5-sulfamoylhex-2-en-1-yl)cyclobutyl) methyl)-3',4,4',5-tetrahydro-2H,2'H-spiro[benzo[b][1,4]oxazepine-3,1'-naphthalene]-7-carboxylic Acid (Example 772, step 6, 50.8 mg, 0.082 mmol) following the procedure described for Example 74, Step 3. The crude material was purified by chromatography through a ISCO gold column 12 g, eluting with a gradient of 10-40-50% EtOAc (containing 0.3% AcOH) in hexanes over 20 min, to provide the inseparable mixture of the two epimers. This material was repurified via reverse-phase HPLC eluting with a gradient of 45-60% MeCN (containing 0.1% TFA) in water (containing 0.1% TFA) over 39 min. to provide (1S,3'R,6'R,7'S,8'E,11'R)-6-chloro-7'-hydroxy-11'-(methoxymethyl)-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide or (1S,3'R,6'R,7'S,8'E,11'R)-6-chloro-7'-hydroxy-11'-(methoxymethyl)-3,4-dihydro-2H,14'H-spiro[naphthalene-1,21'-[19]oxa[12]thia[1,13]diazatetracyclo[13.7.2.0$^{3,6}$.0$^{18,23}$]tetracosa [8,15,17,23]tetraen]-14'-one 12',12'-dioxide as the first eluting and major isomer (7.1 mg, 0.012 mmol, 14.4% yield). $^1$H NMR (400 MHz, CD$_2$Cl$_2$) δ 8.35 (br s, 1H), 7.71 (d, J=8.6 Hz, 1H), 7.18 (dt, J=2.2, 8.0 Hz, 2H), 7.09 (d, J=2.3 Hz, 1H), 6.95 (d, J=8.2 Hz, 1H), 6.73 (br s, 1H), 5.92 (td, J=5.9, 15.8 Hz, 1H), 5.84 (dd, J=5.3, 15.3 Hz, 1H), 4.14-4.07 (m, 3H), 3.93-3.81 (m, 3H), 3.71 (d, J=14.9 Hz, 1H), 3.66 (dd, J=4.7, 15.3 Hz, 1H), 3.40 (s, 3H), 3.33 (d, J=14.5 Hz, 1H), 3.16 (dd, J=8.1, 15.6 Hz, 1H), 2.89-2.67 (m, 4H), 2.59 (dt, J=4.9, 8.3 Hz, 1H), 2.38 (dq, J=5.8, 8.6 Hz, 1H), 2.04 (br s, 1H), 1.98-1.88 (m, 3H), 1.87-1.80 (m, 1H), 1.81-1.72 (m, 1H), 1.70-1.61 (m, 2H), 1.48-1.40 (m, 1H). MS (ESI, +ve ion) m/z 601.3 (M+H)$^+$.

Example 773. (1S,3'R,6'R,7'S,8'E,11'S)-6-chloro-7'-hydroxy-11'-(methoxymethyl)-3,4-dihydro-2H,14'H-spiro[naphthalene-1,21'-[19]oxa [12]thia[1,13]diazatetracyclo[13.7.2.0$^{3,6}$.0$^{18,23}$]tetracosa[8,15,17, 23]tetraen]-14'-one 12',12'-dioxide or (1S,3'R,6'R, 7'S,8'E,11'R)-6-chloro-7'-hydroxy-11'-(methoxymethyl)-3,4-dihydro-2H,14'H-spiro[naphthalene-1,21'-[19]oxa[12]thia[1,13]diazatetracyclo[13.7.2.0$^{3,6}$.0$^{18,23}$]tetracosa [8,15,17,23]tetraen]-14'-one 12',12'-dioxide

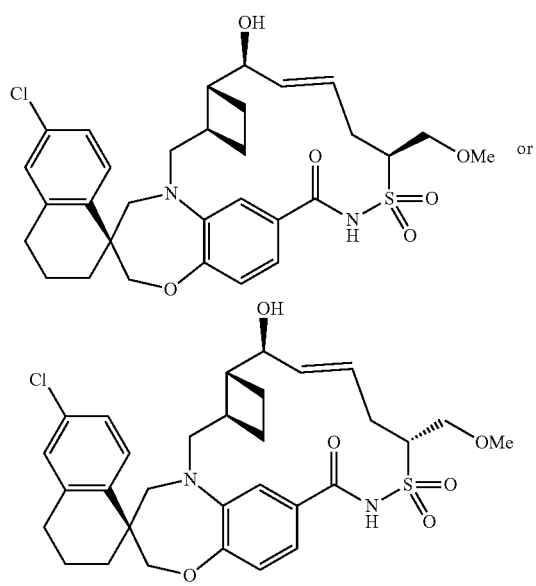

The title compound (5.7 mg, 0.0095 mmol, 11.6% yield) was obtained as the second eluting and minor isomer from the purification described in Example 772 step 7. $^1$H NMR (400 MHz, CD$_2$Cl$_2$) δ 7.70 (d, J=8.6 Hz, 1H), 7.17 (dd, J=2.3, 8.4 Hz, 1H), 7.09 (d, J=2.3 Hz, 1H), 7.07 (dd, J=2.0, 8.0 Hz, 1H), 6.95 (d, J=2.0 Hz, 1H), 6.93 (d, J=8.2 Hz, 1H), 5.88-5.81 (m, 1H), 5.79 (dd, J=4.3, 15.5 Hz, 1H), 4.11 (s, 2H), 4.03-3.98 (m, 1H), 3.95-3.87 (m, 2H), 3.86-3.81 (m, 1H), 3.66 (d, J=14.7 Hz, 1H), 3.64 (dd, J=5.4, 15.4 Hz, 1H), 3.38 (s, 3H), 3.37-3.33 (m, 1H), 3.25 (dd, J=7.0, 15.3 Hz, 1H), 2.84-2.66 (m, 4H), 2.62-2.43 (m, 3H), 2.02-1.96 (m, 1H), 1.94-1.81 (m, 3H), 1.77-1.60 (m, 3H), 1.48 (t, J=10.3 Hz, 1H). MS (ESI, +ve ion) m/z 601.3 (M+H)$^+$.

Example 774. (1S,3'R,6'R,7'S,8'E,11'R)-6-chloro-7'-hydroxy-11'-(methoxymethyl)-11'-methyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa [8,15,17,23]tetraen]-14'-one 12',12'-dioxide or (1S, 3'R,6'R,7'S,8'E,11'S)-6-chloro-7'-hydroxy-11'-(methoxymethyl)-11'-methyl-3,4-dihydro-2H,14'H-spiro [naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide

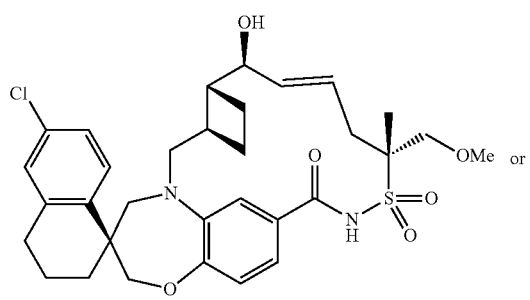

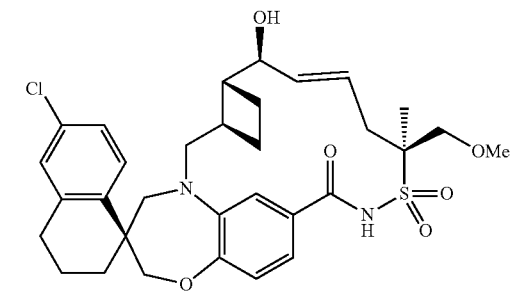

Step 1. (R)-methyl 2-(N,N-bis(4-methoxybenzyl)sulfamoyl)-2-methylpent-4-enoate and (S)-methyl 2-(N,N-bis(4-methoxybenzyl)sulfamoyl)-2-methylpent-4-enoate

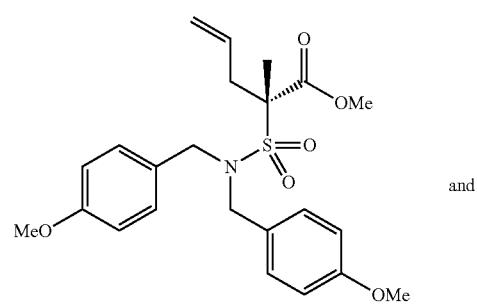

and

-continued

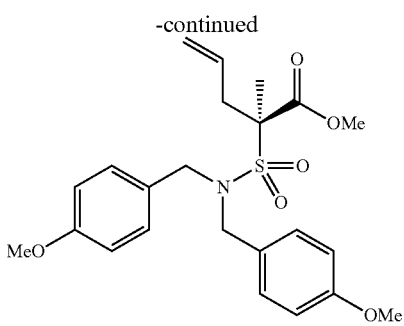

The title compounds were synthesized from (S)—N,N-bis(4-methoxybenzyl)pent-4-ene-2-sulfonamide (Intermediate EE17, Step 1, first eluting isomer; 515 mg, 1.322 mmol) following the procedure described for Example 772, Step 1. The crude mixture of (R)-methyl 2-(N,N-bis(4-methoxybenzyl)sulfamoyl)-2-methylpent-4-enoate and (S)-methyl 2-(N,N-bis(4-methoxy benzyl)sulfamoyl)-2-methylpent-4-enoate was taken on to the next step without purification.

Step 2. (R)-1-hydroxy-N,N-bis(4-methoxybenzyl)-2-methylpent-4-ene-2-sulfonamide and (S)-1-hydroxy-N,N-bis(4-methoxybenzyl)-2-methylpent-4-ene-2-sulfonamide

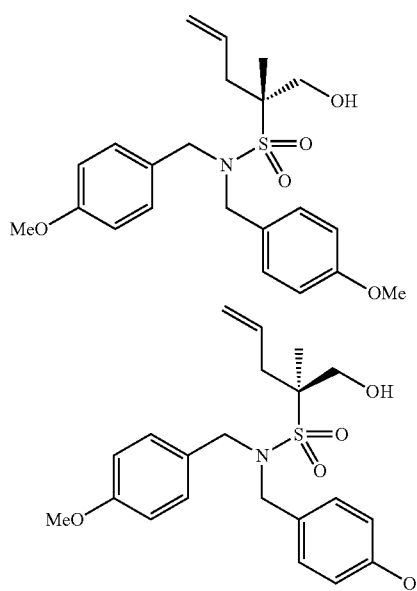

and

The title compounds were synthesized from the crude mixture of (R)-methyl 2-(N,N-bis(4-methoxybenzyl)sulfamoyl)-2-methylpent-4-enoate and (S)-methyl 2-(N,N-bis(4-methoxybenzyl)sulfamoyl)-2-methylpent-4-enoate (Example 774, step 1, 592 mg, 1.32 mmol) following the procedure described for Example 772, Step 2. Purification of the crude material by chromatography through a 24 g ISCO Gold column, eluting with a gradient of 20% to 60% EtOAc in hexane provided a mixture of (R)-1-hydroxy-N,N-bis(4-methoxybenzyl)-2-methylpent-4-ene-2-sulfonamide and (S)-1-hydroxy-N,N-bis(4-methoxybenzyl)-2-methylpent-4-ene-2-sulfonamide (292 mg, 0.696 mmol, 52.6% yield for the two steps).

Step 3. (R)-1-methoxy-N,N-bis(4-methoxybenzyl)-2-methylpent-4-ene-2-sulfonamide and (S)-1-methoxy-N,N-bis(4-methoxybenzyl)-2-methylpent-4-ene-2-sulfonamide

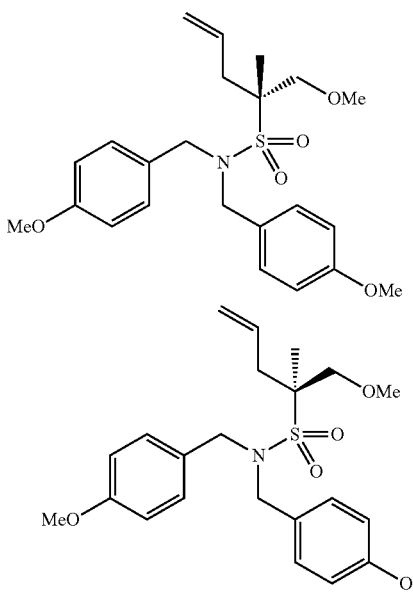

and

The title compounds were synthesized from a mixture of (R)-1-hydroxy-N,N-bis(4-methoxybenzyl)-2-methylpent-4-ene-2-sulfonamide and (S)-1-hydroxy-N,N-bis(4-methoxybenzyl)-2-methylpent-4-ene-2-sulfonamide (Example 774, step 2, 292 mg, 0.696 mmol) following the procedure described for Example 772, Step 3. The crude mixture of (R)-1-hydroxy-N,N-bis(4-methoxybenzyl)-2-methylpent-4-ene-2-sulfonamide and (S)-1-hydroxy-N,N-bis(4-methoxybenzyl)-2-methylpent-4-ene-2-sulfonamide was used without purification.

Step 4. (R)-1-methoxy-2-methylpent-4-ene-2-sulfonamide and (S)-1-methoxy-2-methylpent-4-ene-2-sulfonamide

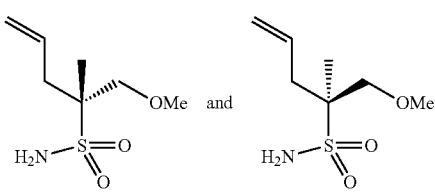

The title compounds were synthesized from a mixture of (R)-1-hydroxy-N,N-bis(4-methoxybenzyl)-2-methylpent-4-ene-2-sulfonamide and (S)-1-hydroxy-N,N-bis(4-methoxybenzyl)-2-methylpent-4-ene-2-sulfonamide (Example 774, step 3, 302 mg, 0.697 mmol) following the procedure described for Example 772, Step 4. Purification of the crude material by chromatography through a 24 g ISCO Gold column, eluting with a gradient of 0% to 50% EtOAc in hexane provided (R)-1-methoxy-2-methylpent-4-ene-2- sulfonamide and (S)-1-methoxy-2-methylpent-4-ene-2-sulfonamide (76 mg, 0.393 mmol, 56.5% yield for the two steps).

Step 5. (S)-6'-chloro-5-(((1R,2R)-2-((1S,5R,E)-1-hydroxy-6-methoxy-5-methyl-5-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1S,5S,E)-1-hydroxy-6-methoxy-5-methyl-5-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic Acid

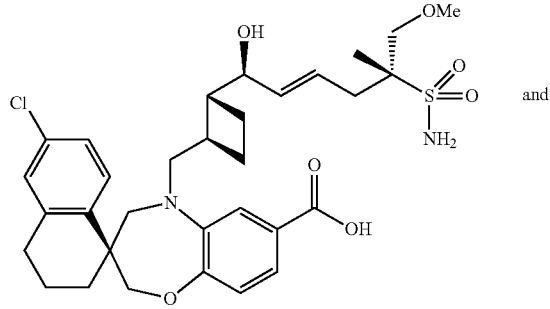

The title compound was synthesized from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A; 50 mg, 0.098 mmol) and a mixture of (R)-1-methoxy-2-methylpent-4-ene-2-sulfonamide and (S)-1-methoxy-2-methylpent-4-ene-2-sulfonamide (Example 774, Step 4; 76 mg, 0.393 mmol) following the procedure described for Example 762, Step 1 but using 1,2-DCE as solvent. The reaction mixture was directly injected into a 12 g ISCO Gold column, and purified eluting with a gradient of 10-20-50-100% EtOAc in hexanes over 16 min to provide partial purifcation of (S)-6'-chloro-5-(((1R,2R)-2-((1S,5R,E)-1-hydroxy-6-methoxy-5-methyl-5-sulfamoylhex-2-en-1-yl)cyclobutyl) methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,E)-1-hydroxy-6-methoxy-5-methyl-5-sulfamoylhex-2-en-1-yl)cyclobutyl) methyl)-3',4,4',5-tetrahydro-2H,2'H-spiro[benzo[b][1,4] oxazepine-3,1'-naphthalene]-7-carboxylic acid. This mixture was used without further purifcation.

Step 6. (1S,3'R,6'R,7'S,8'E,11'R)-6-chloro-7'-hydroxy-11'-(methoxymethyl)-11'-methyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide or (1S,3'R,6'R,7'S,8'E,11'S)-6-chloro-7'-hydroxy-11'-(methoxymethyl)-11'-methyl-3,4-dihydro-2H,14'H-spiro[naphthalene-1,21'-[19]oxa[12]thia[1,13]diazatetracyclo[13.7.2.0$^{3,6}$.0$^{18,23}$]tetracosa [8,15,17,23]tetraen]-14'-one 12',12'-dioxide The title compound was synthesized from a mixture of (S)-6'-chloro-5-(((1R,2R)-2-((1S,5R,E)-1-hydroxy-6-methoxy-5-methyl-5-sulfamoylhex-2-en-1-yl)cyclobutyl) methyl)-3',4,4',5-tetrahydro-2H,2'H-spiro[benzo[b][1,4] oxazepine-3,1'-naphthalene]-7-carboxylic acid and (S)-6'-chloro-5-(((1R,2R)-2-((1S,5S,E)-1-hydroxy-6-methoxy-5-methyl-5-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Example 774, step 5, 56 mg, 0.088 mmol) following the procedure described for Example 762, Step 3. The crude material was purified by chromatography through a ISCO gold column 12 g, eluting with a gradient of 10-40-50% EtOAc (containing 0.3% AcOH) in hexanes over 24 min, to provide the inseparable mixture of the two epimers. This material was repurified via reverse-phase HPLC eluting with a gradient of 45-60% MeCN (containing 0.1% TFA) in water (containing 0.1% TFA) over 36 min. to provide the first eluting and minor isomer (1S,3'R,6'R,7'S,8'E,11'R)-6-chloro-7'-hydroxy-11'-(methoxymethyl)-11'-methyl-3,4-dihydro-2H,14'H-spiro [naphthalene-1,21'-[19]oxa[12]thia [1,13]diazatetracyclo [13.7.2.0$^{3,6}$.0$^{18,23}$]tetracosa[8,15,17,23]tetraen]-14'-one 12',12'-dioxide or (1S,3'R,6'R,7'S,8'E,11'S)-6-chloro-7'-hydroxy-11'-(methoxymethyl)-11'-methyl-3,4-dihydro-2H, 14'H-spiro[naphthalene-1,21'-[19]oxa[12]thia[1,13] diazatetracyclo [13.7.2.0$^{3,6}$.0$^{18,23}$]tetracosa[8,15,17,23] tetraen]-14'-one 12',12'-dioxide (4.1 mg, 0.0067 mmol, 7.5% yield). $^1$H NMR (500 MHz, MeOH-d4) δ 7.73 (d, J=8.6 Hz, 1H), 7.17 (dd, 8.6 Hz, 1H), 7.12 (dd, J=2.1, 8.2 Hz, 1H), 7.10 (d, J=2.2 Hz, 1H), 6.93 (d, J=8.1 Hz, 1H), 6.90 (d, J=1.7 Hz, 1H), 6.20 (td, J=6.3, 15.2 Hz, 1H), 5.81 (dd, 15.3 Hz, 1H), 4.21 (dd, J=4.3, 7.7 Hz, 1H), 4.06 (s, 2H), 3.86 (d, J=13.7 Hz, 1H), 3.72 (d, J=14.2 Hz, 1H), 3.66 (q, J=10.0 Hz, 2H), 3.40 (d, J=14.4 Hz, 1H), 3.37 (s, 3H), 3.09 (dd, J=11.2, 15.2 Hz, 1H), 2.87 (dd, J=6.4, 16.9 Hz, 1H), 2.83-2.72 (m, 2H), 2.53 (dd, J=6.7, 17.0 Hz, 2H), 2.36 (dq, J=4.3, 9.3 Hz, 1H), 2.09 (d, J=13.4 Hz, 1H), 1.99-1.88 (m, 3H), 1.82 (dt, J=5.1, 9.2 Hz, 2H), 1.76-1.67 (m, 1H), 1.54 (s, 3H), 1.48-1.40 (m, 1H). MS (ESI, +ve ion) m/z 615.1 (M+H)$^+$.

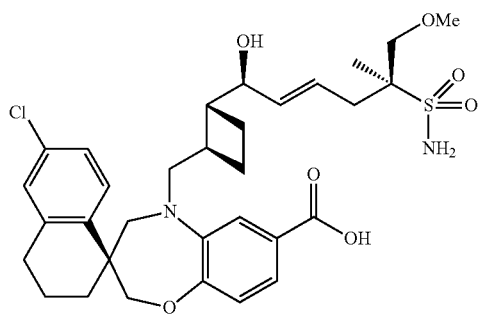

Example 775. (1S,3'R,6'R,7'S,8'E,11'S)-6-chloro-7'-hydroxy-11'-(methoxy methyl)-11'-methyl-3,4-dihydro-2H,14'H-spiro[naphthalene-1,21'-[19]oxa[12]thia[1,13]diazatetracyclo[13.7.2.0³,⁶.0¹⁸,²³]tetracosa[8,15,17,23]tetraen]-14'-one 12',12'-dioxide or (1S,3'R,6'R,7'S,8'E,11'R)-6-chloro-7'-hydroxy-11'-(methoxymethyl)-11'-methyl-3,4-dihydro-2H,14'H-spiro[naphthalene-1,21'-[19]oxa[12]thia[1,13]diazatetracyclo [13.7.2.0³,⁶.0¹⁸,²³]tetracosa[8,15,17,23]tetraen]-14'-one 12',12'-dioxide Example 776. (1S,3'R,6'R,7'S,8'E)-6-chloro-7'-hydroxy-3,4-dihydro-2H,14'H-spiro[naphthalene-1,21'-[19]oxa[12]thia[1,13]diazatetracyclo[13.7.2.0³,⁶.0¹⁸,²³]tetracosa[8,15,17,23]tetraen]-14'-one 12',12'-dioxide and (1S,3'R,6'R,7'S,8'Z)-6-chloro-7'-hydroxy-3,4-dihydro-2H,14'H-spiro[naphthalene-1,21'-[19]oxa[12]thia[1,13]diazatetracyclo[13.7.2.0³,⁶.0¹⁸,²³]tetracosa[8,15,17,23]tetraen]-14'-one 12',12'-dioxide

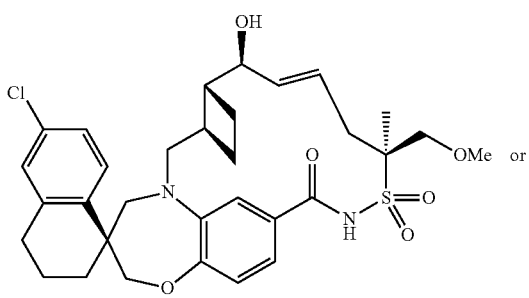

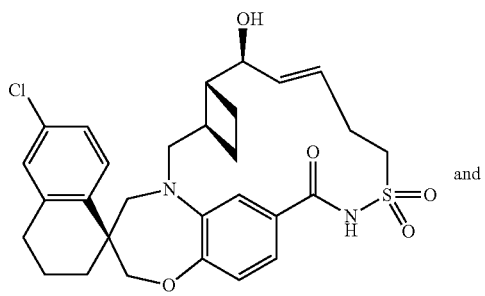

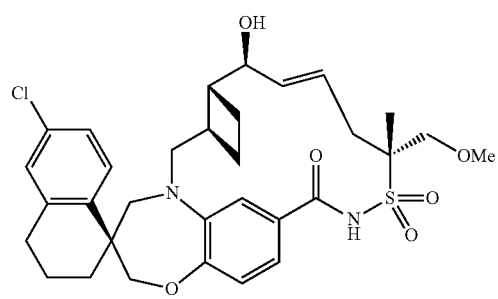

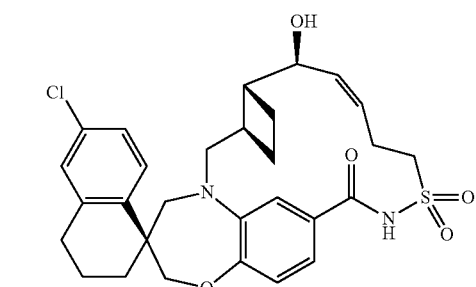

The title compound (4.8 mg, 0.0078 mmol, 8.8% yield) was obtained as the second eluting and major isomer from the purification described in Example 774 step 6. $^1$H NMR (500 MHz, MeOH-d4) δ 7.73 (d, J=8.6 Hz, 1H), 7.17 (dd, J=2.4, 8.6 Hz, 1H), 7.11-7.08 (m, 2H), 6.92 (d, J=8.1 Hz, 1H), 6.89 (br s, 1H), 6.24 (td, J=6.4, 15.6 Hz, 1H), 5.77 (dd, J=6.8, 15.4 Hz, 1H), 4.18 (dd, J=4.2, 5.9 Hz, 1H), 4.06 (s, 2H), 3.77 (d, J=9.8 Hz, 1H), 3.77-3.70 (m, 2H), 3.70 (d, J=9.5 Hz, 1H), 3.41 (d, J=14.7 Hz, 1H), 3.31 (s, 3H), 3.13 (dd, J=11.1, 15.3 Hz, 1H), 2.87-2.75 (m, 2H), 2.71 (dd, J=6.1, 17.9 Hz, 1H), 2.65 (dd, J=6.6, 16.9 Hz, 1H), 2.62-2.54 (m, 1H), 2.34 (qd, J=4.4, 8.8 Hz, 1H), 2.09 (d, J=13.4 Hz, 1H), 1.99-1.89 (m, 3H), 1.89-1.79 (m, 2H), 1.73 (quin, J=9.2 Hz, 1H), 1.49 (s, 3H), 1.47-1.40 (m, 1H). MS (ESI, +ve ion) m/z 615.1 (M+H)⁺.

Step 1. (S)-6'-chloro-5-(((1R,2R)-2-((S,E)-1-hydroxy-5-sulfamoylpent-2-en-1-yl)cyclobutyl)methyl)-3',4,4',5-tetrahydro-2H,2'H-spiro[benzo[b][1,4]oxazepine-3,1'-naphthalene]-7-carboxylic Acid

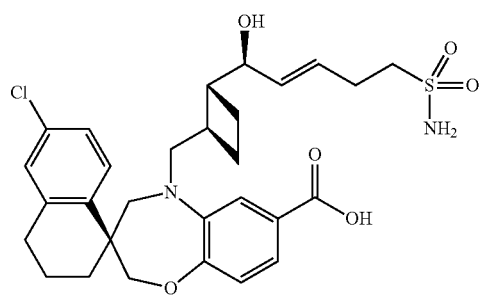 [SMILES: NS(=O)(=O)CC/C=C/[C@H](O)[C@@H]1CC[C@H]1CN1C[C@@]2(CCCc3cc(Cl)ccc32)COc2ccc(C(=O)O)cc21]

A vial was charged with (S)-tert-butyl 6'-chloro-5-(((1R,2R)-2-4S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (Intermediate AA12B, Step 1B, first eluting isomer; 42 mg, 0.074 mmol), but-3-ene-1-sulfonamide (Intermediate EE15; 60.2 mg, 0.445 mmol) and DCM (1 mL). The solution was sparged with argon then Hoveyda-Grubbs II (4.65 mg, 7.42 μmol) was added as a solution in 0.5 mL DCM at ambient temperature. The mixture was stirred under Ar (venting the vial and adding solvent as needed) at ambient tenperature. Aafter 2h more catalyst solution was added and the mixture was stirred for 1 additional hour. The reaction mixture was directly injected into a 12 g ISCO Gold column, and purified eluting with a gradient of 0-20-100% EtOAc in hexanes over 20 min to give the intemediate ester. This material (24 mg contaminated with unreacted sulfonamide) was taken up in 1.2 mL of DCM and treated with 0.15 mL TFA at ambient temperature for 5 h, then the mixture was diluted with EtOAc, washed once with NaHCO$_3$, dried and concentrated. The crude material was purified by chromatography through a Redi-Sep pre-packed silica gel column (12 g), eluting with 10 to 50 to 100% EtOAc in hexane, to provide (S)-6'-chloro-5-(((1R,2R)-2-((S,E)-1-hydroxy-5-sulfamoylpent-2-en-1-yl)cyclobutyl) methyl)-3',4,4',5-tetrahydro-2H,2'H-spiro [benzo[b][1,4]oxazepine-3,1'-naphthalene]-7-carboxylic acid (9.2 mg, 0.016 mmol, 21.6% yield).

Step 2. (1S,3'R,6'R,7'S,8'E)-6-chloro-7'-hydroxy-3,4-dihydro-2H,14'H-spiro[naphthalene-1,21'-[19]oxa[12]thia[1,13]diazatetracyclo [13.7.2.0$^{3,6}$.0$^{18,23}$] tetracosa[8,15,17,23]tetraen]-14'-one 12',12'-dioxide and (1S,3'R,6'R,7'S,8'Z)-6-chloro-7'-hydroxy-3,4-dihydro-2H,14'H-spiro[naphthalene-1,21'-[19]oxa[12]thia[1,13]diazatetracyclo[13.7.2.0$^{3,6}$.0$^{18,23}$]tetracosa[8,15,17,23]tetraen]-14'-one 12',12'-dioxide The title compounds were synthesized from (S)-6'-chloro-5-(((1R,2R)-2-((S,E)-1-hydroxy-5-sulfamoylpent-2-en-1-yl)cyclobutyl)methyl)-3',4,4',5-tetrahydro-2H,2'H-spiro [benzo[b][1,4]oxazepine-3,1'-naphthalene]-7-carboxylic Acid (Example 776, step 1, 9.2 mg, 0.016 mmol) following the procedure described for Example 762, Step 3. The crude material was purified by chromatography through a ISCO gold column 4 g, eluting with a gradient of 10-55% EtOAc (containing 0.3% AcOH) in hexanes, to provide the title compounds as a 5.4:1 mixture of olefin isomers (E:Z respectively; 4.5 mg, 0.008 mmol, 50.5% yield). Analytical data for the major isomer (1S,3'R,6'R,7'S,8'E)-6-chloro-7'-hydroxy-3,4-dihydro-2H,14'H-spiro[naphthalene-1,21'-[19] oxa[12]thia[1,13]diazatetracyclo[13.7.2.0$^{3,6}$.0$^{18,23}$]tetracosa[8,15,17,23]tetraen ]1-14'-one 12',12'-dioxide. $^1$H NMR (400 MHz, CD$_2$Cl$_2$) δ 8.46-8.11 (m, 1H), 7.70 (d, J=8.6 Hz, 1H), 7.17 (dd, J=2.3, 8.4 Hz, 1H), 7.12-7.07 (m, 2H), 6.94 (d, J=8.2 Hz, 1H), 6.89 (d, J=1.6 Hz, 1H), 5.80 (dd, 15.5 Hz, 1H), 5.72 (td, J=6.1, 15.6 Hz, 1H), 4.14-4.08 (m, 2H), 3.97 (t, J=5.2 Hz, 1H), 3.75-3.57 (m, 4H), 3.33 (d, J=14.3 Hz, 1H), 3.21 (dd, J=6.7, 15.5 Hz, 1H), 2.85-2.71 (m, 2H), 2.70-2.62 (m, 2H), 2.61-2.54 (m, 1H), 2.51-2.42 (m, 1H), 2.04-1.97 (m, 1H), 1.96-1.88 (m, 3H), 1.87-1.79 (m, 1H), 1.75-1.60 (m, 3H), 1.51-1.41 (m, 1H). MS (ESI, +ve ion) m/z 557.2 (M+H)$^+$.

Example 777. (1S,3'R,6'R,7'S,8'E,11'S,12'R)-6-chloro-7'-(2-((2,4-dimethoxy benzyl)amino)ethoxy)-11',12'-dimethyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one-13', 13'-dioxide

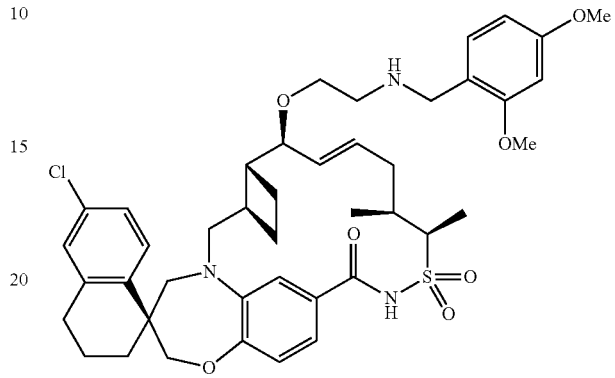

To a solution of (1S,3'R,6'R,7'S,8'E,11'S,12'R)-7'-(2-bromoethoxy)-6-chloro-11',12'-dimethyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (Example 14.15 mg, 0.021 mmol) and 2,4-dimethoxybenzylamine (Sigma Aldrich; 3.83 μl, 0.025 mmol) in THF (0.425 mL) at 0° C. was added triethylamine (8.86 μl, 0.064 mmol). The reaction mixture was stirred at 0° C. for 1 h (no reaction); then at ambient temperature overnight; no reaction. DMSO was then added (0.4 mL) followed by more reagent and base and the mixture was heated to 50° C. for 5 h. The mixture was the quenched and diluted with water, then extracted with EtOAc (3×3 mL). The organic layer was dried over MgSO$_4$ and concentrated. The crude material was purified by chromatography through a Redi-Sep pre-packed silica gel column (4 g), eluting with a gradient of 50-100% EtOAc in heptanes (nothing eluted); The column was then flushed with 100% 3:1 EtOAc/EtOH to provide the title compound but contaminated This material was further purified via Reverse-Phase HPLC providing (1S,3'R,6'R,7'S,8'E,11'S,12'R)-6-chloro-7'-(2-((2,4-dimethoxybenzyl)amino)ethoxy)-11',12'-dimethyl-3,4-dihydro-2H,15'H-spiro [naphthalene-1,22'-[20]oxa[13]thia[1,14]diazatetracyclo [14.7.2.0$^{3,6}$.0$^{19,24}$]pentacosa[8,16,18,24] tetraen]-15'-one-13', 13'-dioxide (trifluoroacetic acid salt; 10.6 mg, 0.013 mmol, 63% yield, 95% purity). $^1$H NMR (500 MHz, CD$_2$Cl$_2$) δ 8.49-8.35 (m, 1H), 8.26 (br s, 1H), 7.70 (d, J=8.6 Hz, 1H), 7.19 (br s, 1H), 7.17 (dd, J=2.4, 8.6 Hz, 1H), 7.09 (d, J=2.2 Hz, 1H), 6.95-6.89 (m, 2H), 6.81 (s, 1H), 6.54-6.50 (m, 2H), 5.83 (ddd, J=2.7, 9.8, 14.9 Hz, 1H), 5.48 (dd, J=9.2, 15.0 Hz, 1H), 4.28-4.21 (m, 1H), 4.19 (br s, 2H), 4.07 (s, 2H), 3.87 (s, 3H), 3.81 (s, 3H), 3.83-3.79 (m, 1H), 3.77 (br s, 1H), 3.68 (d, J=14.4 Hz, 1H), 3.63 (br s, 1H), 3.47 (br s, 1H), 3.24 (d, J=14.4 Hz, 1H), 3.13 (d, J=18.8 Hz, 2H), 3.00 (dd, J=10.1, 15.3 Hz, 1H), 2.84-2.70 (m, 2H), 2.45-2.37 (m, 1H), 2.37-2.28 (m, 1H), 2.18-2.10 (m, 1H), 2.09-2.01 (m, 2H), 2.00-1.90 (m, 3H), 1.89-1.73 (m, 3H), 1.72-1.64 (m, 1H), 1.43 (d, J=7.1 Hz, 3H), 1.41-1.35 (m, 1H), 1.00 (d, J=6.8 Hz, 3H). MS (ESI, +ve ion) m/z 792.1 (M+H)$^+$.

Example 778. (1S,3'R,6'R,7'S)-10'acetyl-6-chloro-7'-hydroxy-3,4-dihydro-2H,15'H-spiro[naphthalene-1,22'-[20]oxa[13]thia[1,10,14]triazatetracyclo [14.7.2.0³,⁶.0¹⁹,²⁴]pentacosa[16,18,24]trien]-15'-one-13', 13'-dioxide or (1S,3'R,6'R,7'R)-10'acetyl-6-chloro-7'-hydroxy-3,4-dihydro-2H,15'H-spiro[naphthalene-1,22'-[20]oxa[13]thia[1,10,14] triazatetracyclo [14.7.2.0³,⁶.0¹⁹,²⁴]pentacosa[16,18, 24]trien]-15'-one-13', 13'-dioxide

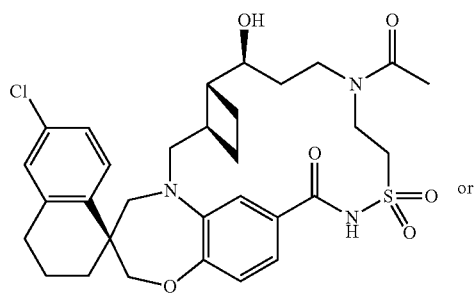

or

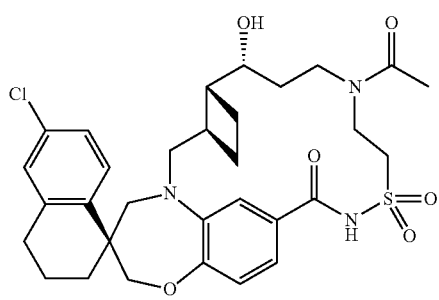

Step 1: bis(2,4-dimethoxybenzyl)amine

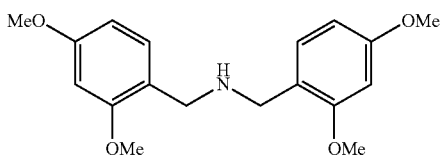 [SMILES: COc1ccc(CNCc2ccc(OC)cc2OC)c(OC)c1]

2,4-dimethoxybenzaldehyde (Sigma Aldrich; 1.1 g, 6.61 mmol) was dissolved in 20 mL THF at ambient temperature. To the solution was added 2,4-dimethoxybenzylamine (Sigma Aldrich; 1.5 mL, 9.98 mmol) followed by sodium triacetoxyborohydride (Sigma Aldrich; 1.7 g; 8.4 mmol) and the mixture (increasingly cloudy) was stirred at ambient temperature overnight. The mixture was then diluted with sat. NaHCO₃ and extracted with EtOAc, dried over MgSO₄ and concentrated. The residue was purified by chromatography on 40 g ISCO column eluting with a gradient of 0 to 100% EtOAc to deliver bis(2,4-dimethoxybenzyl)amine (2.08 g, 6.55 mmol, 99% yield, 96% purity)

Step 2: N,N-bis(2,4-dimethoxybenzyl)ethenesulfonamide

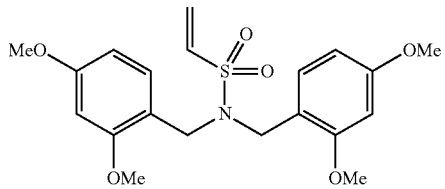 [SMILES: C=CS(=O)(=O)N(Cc1ccc(OC)cc1OC)Cc1ccc(OC)cc1OC]

To a solution of bis(2,4-dimethoxybenzyl)amine (Example 778, step 1, 1.500 g, 4.73 mmol) and triethylamine (2.301 ml, 16.54 mmol) in CH₂Cl₂ (23.63 ml) cooled to 0° C. was added 2-chloroethanesulfonyl chloride (0.494 ml, 4.73 mmol) dropwise over 5 minutes. The yellow mixture was stirred at 0° C. for 1 h. TLC (50% EtOAc/hexanes) showed complete loss of both starting materials and formation of a new product. The mixture was then diluted with CH₂Cl₂ and washed twice with brine, then dried over MgSO₄ and concentrated. The crude orange oil was purified by chromatography through a column (24 g), eluting with a gradient of 0% to 20% to 60% to 100% EtOAc in hexane, to provide N,N-bis(2,4-dimethoxybenzyl)ethenesulfonamide (1.162 g, 2.85 mmol, 60.3% yield)

Step 3: 2-amino-N,N-bis(2,4-dimethoxybenzyl)ethanesulfonamide

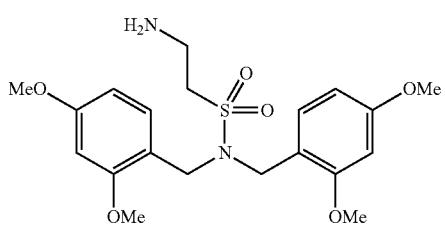 [SMILES: COc1ccc(CN(Cc2ccc(OC)cc2OC)S(=O)(=O)CCN)c(OC)c1]

To a solution of N,N-bis(2,4-dimethoxybenzyl)ethenesulfonamide (Example 778, step 2, 260 mg, 0.638 mmol) in MeOH (2.55 mL), was added triethylamine (0.097 mL, 0.702 mmol) followed by ammonia (7 N solution in methanol; 1.823 mL, 12.76 mmol). The mixture was heated to 60° C. overnight. The solvent was then removed under reduced pressure and the residue was dried under high vacuum. The crude material was purified via column chromatography eluting with a gradient of 0 to 100% CH₂Cl₂ (containing 10% MeOH and 0.2% Et₃N) in hexanes to provide 2-amino-N,N-bis(2,4-dimethoxybenzyl)ethanesulfonamide (60 mg, 0.141 mmol, 22.15% yield)

Step 4: (S)-6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylic Acid

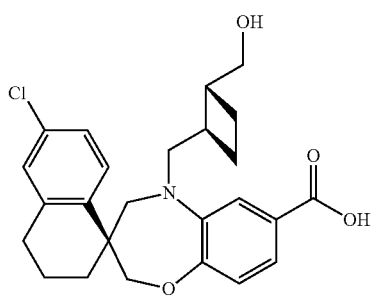 [SMILES: O=C(O)c1ccc2c(c1)N(C[C@@H]1CC[C@H]1CO)C[C@@]1(CCCc3cc(Cl)ccc31)CO2]

A vial was charged with (S)-methyl 6'-chloro-5-(((1R,2R)-2-(hydroxymethyl)cyclobutyl) methyl)-3',4,4',5-tetrahydro-2H,2'H-spiro[benzo[b][1,4]oxazepine-3,1'-naphthalene]-7-carboxylate (Intermediate AA1A, Step 19 A; 300 mg, 0.658 mmol), THF (8.77 mL), MeOH (4.39 mL) and 1 N LiOH (4.61 mL, 4.61 mmol). The mixture was stirred at 60° C. for 1 h then it was quenched with 1 N HCl (9.21 mL, 9.21 mmol), diluted with brine (50 mL) and extracted with EtOAc (3×30 mL). The combined organics were dried (MgSO₄) and concentrated. The crude (S)-6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylic acid was used without further purification.

Step 5: (S)-6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylic Acid

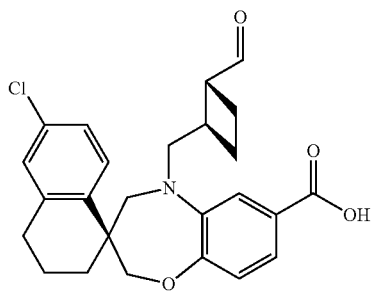 [SMILES: O=C[C@@H]1CC[C@H]1CN1C[C@@]2(CCCc3cc(Cl)ccc32)COc2ccc(C(=O)O)cc21]

A 100 mL round-bottom flask was charged with (S)-6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylic acid (Example 778, step 4, 290 mg, 0.656 mmol) and DCM (3.28 mL). To the solution, cooled to 0° C. was added Dess-Martin periodinane (417 mg, 0.984 mmol). The mixture was stirred while allowing to reach ambient temperature for 1 h then it was diluted with EtOAc (30 mL), washed with 1 N sodium thiosulfate (1×30 mL) and brine (1×30 mL). The aqueous layer was back extracted with EtOAc (1x 15 mL) and the combined organics were dried over MgSO₄ and concentrated. The crude red foam was purified by chromatography through a Redi-Sep pre-packed silica gel column (12 g), eluting with a gradient of 0% to 40% EtOAc in hexane, to provide (S)-6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylic Acid (201 mg, 0.457 mmol, 69.6% yield).

Step 6: (S)-5-(((1R,2R)-2-acryloylcyclobutyl)methyl)-6'-chloro-3',4,4',5-tetrahydro-2H,2'H-spiro[benzo[b][1,4]oxazepine-3,1'-naphthalene]-7-carboxylic Acid To a solution of (S)-6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylic acid (Example 778, step 5, 164 mg, 0.373 mmol) in tetrahydrofuran (1.86 mL) under an argon atmosphere at 0° C. was added vinylmagnesium bromide (1.0 M solution in tetrahydrofuran; 0.634 mL, 0.634 mmol) dropwise, via syringe. After 0.5 h the mixture was quenched with saturated aqueous ammonium chloride, diluted with brine and extracted with EtOAc. The organic phase was dried over MgSO₄ and concentrated. The crude material was taken up in 3 mL CH₂Cl₂ and treated directly with Dess-Martin periodinane (237 mg, 0.559 mmol) at 0° C. for 1.5 h then diluted with EtOAc, washed with saturated sodium thiosulfate and brine (once each). The aqueous layer was back-extracted once with EtOAc and the combined organics were dried over MgSO₄ and concentrated. The crude material was purified by chromatography through a Redi-Sep pre-packed silica gel column (4 g), eluting with a gradient of 0% to 50% EtOAc in hexane, to provide (S)-5-(((1R,2R)-2-acryloylcyclobutyl) methyl)-6'-chloro-3',4,4',5-tetrahydro-2H,2'H-spiro[benzo[b][1,4]oxazepine-3,1'-naphthalene]-7-carboxylic Acid (73 mg, 0.157 mmol, 42.0% yield for the three steps).

Step 7: (S)-5-(((1R,2R)-2-(3-((2-(N,N-bis(2,4-dimethoxybenzyl)sulfamoyl) ethyl)amino)propanoyl)cyclobutyl)methyl)-6'-chloro-3',4,4',5-tetrahydro-2H,2'H-spiro[benzo[b][1,4]oxazepine-3,1'-naphthalene]-7-carboxylic Acid and (S)-5-(((1R,2R)-2-(3-((2-(N (2,4-dimethoxybenzyl) sulfamoyl)ethyl)amino) propanoyl)cyclobutyl)methyl)-6'-chloro-3',4,4',5-tetrahydro-2H,2'H-spiro[benzo[b][1,4]oxazepine-3, 1'-naphthalene]-7-carboxylic Acid Step 8: (S)-6'-chloro-5-(((1R,2R)-2-(3-(N-(2-sulfamoylethyl)acetamido) propanoyl)cyclobutyl) methyl)-3',4,4',5-tetrahydro-2H,2'H-spiro[benzo[b][1,4]oxazepine-3,1'-naphthalene]-7-carboxylic Acid

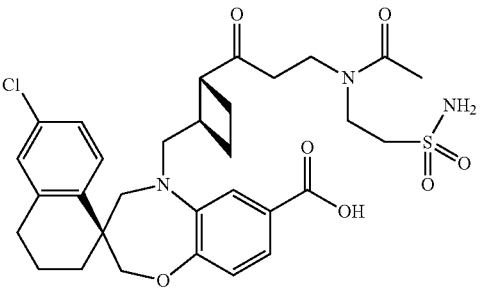 [SMILES: CC(=O)N(CCC(=O)[C@@H]1CC[C@H]1CN1C[C@@]2(CCCc3cc(Cl)ccc32)COc2ccc(C(=O)O)cc21)CCS(N)(=O)=O]

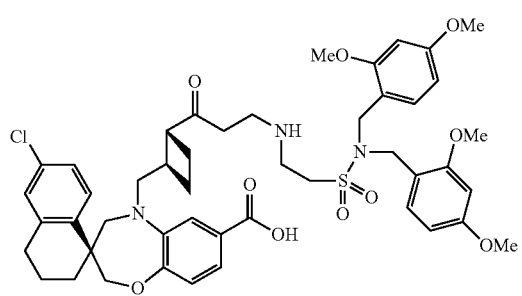

and

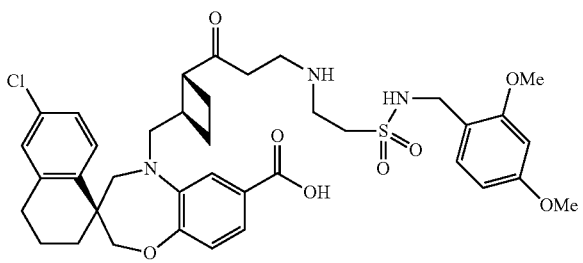

To a solution of (S)-5-(((1R,2R)-2-(3-((2-(N,N-bis(2,4-dimethoxybenzyl)sulfamoyl)ethyl)amino)propanoyl)cyclobutyl)methyl)-6'-chloro-3',4,4',5-tetrahydro-2H,2'H-spiro[benzo[b][1,4]oxazepine-3,1'-naphthalene]-7-carboxylic acid and (S)-5-(((1R,2R)-2-(3-((2-(N(2,4-dimethoxybenzyl)sulfamoyl)ethyl)amino)propanoyl) cyclobutyl)methyl)-6'-chloro-3',4,4',5-tetrahydro-2H,2'H-spiro[benzo[b][1,4]oxazepine-3,1'-naphthalene]-7-carboxylic acid (Example 778, step 7, 53 mg, 0.060 mmol) in $CH_2Cl_2$ (1.19 mL) at ambient temperature was added triethylamine (0.029 mL, 0.208 mmol) followed by acetic anhydride (6.18 µl, 0.065 mmol) and the mixture was stirred at ambient temperature for 30 min. The mixture was then diluted with EtOAc and washed with $NaHCO_3$. The aqueous phase was back extracted with EtOAc and the combined organics were dried over $MgSO_4$ and concentrated. The crude material was taken up in $CH_2Cl_2$ (1.5 mL) and thioanisole (0.070 mL, 0.595 mmol) was added followed by the dropwise addition of trifluoroacetic acid (0.5 mL, 6.73 mmol). After stirring for 30 min (bright blue color developed) LC/MS analysis showed complete conversion to the desired product. The mixture was then diluted with EtOAc, washed with sat. $NaHCO_3$, dried over MgSO4 and concentrated. The crude material was purified via reverse-phase HPLC to provide (S)-6'-chloro-5-(((1R,2R)-2-(3-(N-(2-sulfamoylethyl)acetamido)propanoyl)cyclobutyl)methyl)-3',4,4',5-tetrahydro-2H,2'H-spiro[benzo[b][1,4]oxazepine-3,1'-naphthalene]-7-carboxylic acid (26.8 mg, 0.042 mmol, 71.2% yield).

Step 9: (1S,3'R,6'R,7'S)-10'acetyl-6-chloro-7'-hydroxy-3,4-dihydro-2H,15'H-spiro[naphthalene-1,22'-[20]oxa[13]thia[1,10,14]triazatetracyclo [14.7.2.0$^{3,6}$.0$^{19,24}$]pentacosa[16,18,24]trien]-15'-one-13', 13'-dioxide or (1S,3'R,6'R,7'R)-10'acetyl-6-chloro-7'-hydroxy-3,4-dihydro-2H,15'H-spiro[naphthalene-1,22'-[20]oxa[13]thia[1,10,14]triazatetracyclo [14.7.2.0$^{3,6}$.0$^{19,24}$]pentacosa[16,18,24]trien]-15'-one-13', 13'-dioxide To a solution of (S)-5-(((1R,2R)-2-acryloylcyclobutyl) methyl)-6'-chloro-3',4,4',5-tetrahydro-2H,2'H-spiro[benzo [b][1,4]oxazepine-3,1'-naphthalene]-7-carboxylic acid (Example 778, Step 6; 63 mg, 0.135 mmol) and 2-amino-N,N-bis(2,4-dimethoxybenzyl) ethanesulfonamide (Example 778 Step 3; 60 mg, 0.141 mmol) in $CH_2Cl_2$ (2.7 mL) at ambient temperature was added N,N-diisopropylethylamine (0.071 mL, 0.406 mmol) dropwise, via syringe. After 3 h the mixture was concentrated in vacuo and the crude material was purified via reverse-phase HPLC (34 min.; 2 injections) to provide an inseparable mixture of (S)-5-(((1R,2R)-2-(3-((2-(N,N-bis(2,4-dimethoxybenzyl)sulfamoyl)ethyl)amino) propanoyl) cyclobutyl)methyl)-6'-chloro-3',4,4',5-tetrahydro-2H,2'H-spiro[benzo[b][1,4]oxazepine-3,1'-naphthalene]-7-carboxylic acid and (S)-5-(((1R,2R)-2-(3-((2-(N(2,4-dimethoxybenzyl) sulfamoyl)ethyl)amino) propanoyl)cyclobutyl) methyl)-6'-chloro-3',4,4',5-tetrahydro-2H,2'H-spiro[benzo[b][1,4]oxazepine-3,1'-naphthalene]-7-carboxylic acid (53 mg, 0.60 mmol). This material was used without further purification.

(S)-6'-chloro-5-(((1R,2R)-2-(3-(N-(2-sulfamoylethyl)acetamido)propanoyl)cyclobutyl) methyl)-3',4,4',5-tetrahydro-2H,2'H-spiro[benzo[b][1,4]oxazepine-3,1'-naphthalene]-7-carboxylic acid (Example 778, step 8, 26.8 mg, 0.042 mmol) was placed into a 100 mL round bottom flask and $CH_2Cl_2$ (84.8 mL) was added followed by N,N-dimethylpyridin-4-amine (7.77 mg, 0.064 mmol). The mixture was cooled to 0° C. and N-(3-dimethylaminopropyl)-N'-ethyl-carbodiimide hydrochloride (16.25 mg, 0.085 mmol) was added slowly portion-wise and the mixture was stirred while allowing to reach ambient temperature overnight, then it was concentrated. The crude material was purified by chromatography through a Redi-Sep pre-packed silica gel column (4 g), eluting with a gradient of 0% to 100% EtOAc (containing 0.3% AcOH) in hexanes, to provide the desired intermediate ketone (13 mg). This material was dissolved in 1.5 MeOH and to the cold solution (0° C.) was added sodium borohydrate (1.604 mg, 0.042 mmol) in one portion. LC/MS analysis after 10 min. showed complete conversion to the expected mixture of diastereomers. The mixture was quenched at 0° C. with sat. NH$_4$Cl and extracted with EtOAc (4×10 mL), dried over MgSO$_4$ and concentrated. The crude material was purified via reverse-phase HPLC to provide the title compounds as a 5:1 mixture of diastereomers. This material was repurified by SFC to provide (1S,3'R,6'R,7'S)-10'acetyl-6-chloro-7'-hydroxy-3,4-dihydro-2H,15'H-spiro[naphthalene-1,22'-[20]oxa[13]thia[1,10,14]triazatetracyclo[14.7.2.0$^{3,6}$.0$^{19,24}$]pentacosa[16,18,24]trien]-15'-one-13',13'-dioxide or (1S,3'R,6'R,7'R)-10'acetyl-6-chloro-7'-hydroxy-3,4-dihydro-2H,15'H-spiro[naphthalene-1,22'-[20]oxa[13]thia[1,10,14]triazatetracyclo[14.7.2.0$^{3,6}$.0$^{19,24}$]pentacosa[16,18,24]trien]-15'-one-13',13'-dioxide (0.9 mg, 0.001 mmol). $^1$H NMR (400 MHz, MeOH-d4) δ 7.75 (d, J=8.8 Hz, 1H), 7.28 (s, 1H), 7.21-7.12 (m, 2H), 7.10 (s, 1H), 6.87 (d, J=7.6 Hz, 1H), 4.14-4.10 (m, 1H), 4.10-4.02 (m, 2H), 3.94-3.83 (m, 2H), 3.71 (d, J=14.1 Hz, 1H), 3.67-3.63 (m, 1H), 3.59 (br s, 1H), 3.53-3.46 (m, 2H), 3.39 (d, J=13.3 Hz, 2H), 3.16-3.10 (m, 1H), 2.87-2.71 (m, 3H), 2.51 (br s, 1H), 2.13 (s, 3H), 2.09-2.03 (m, 1H), 2.01-1.82 (m, 4H), 1.79-1.64 (m, 3H), 1.62-1.50 (m, 1H), 1.50-1.41 (m, 1H). MS (ESI, +ve ion) m/z 616.1 (M+H)$^+$.

Example 779. (3'R,6'R,7S,22S)-6'-chloro-7-hydroxy-3',4'-dihydro-2'H,15H-spiro[10,20-dioxa-13-thia-1,14-diazatetracyclo[14.7.2.0$^{3,6}$.0$^{19,24}$]pentacosa-16,18,24-triene-22,1'-naphthalen]-15-one-13,13-dioxide or (3'R,6'R,7R,22S)-6'-chloro-7-hydroxy-3',4'-dihydro-2'H,15H-spiro[10,20-dioxa-13-thia-1,14-diazatetracyclo[14.7.2.0$^{3,6}$.0$^{19,24}$]pentacosa-16,18,24-triene-22,1'-naphthalen]-15-one-13,13-dioxide

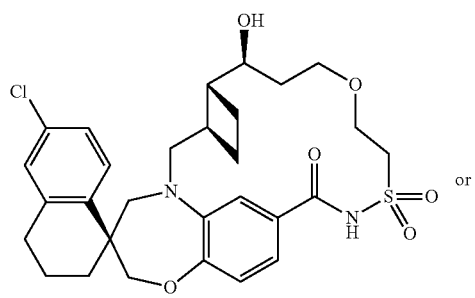

or

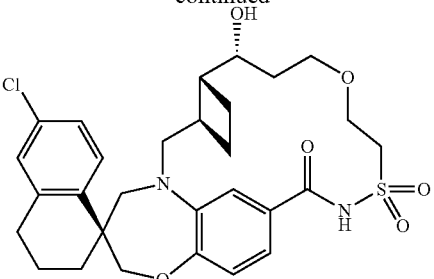

Step 1: ((1R,2S)-2-((E)-pent-1-en-1-yl)cyclobutyl)methyl acetate

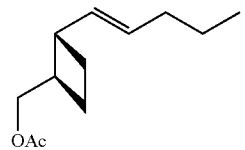

A solution of (butyl)triphenylphosphonium bromide (30.5 g, 76 mmol) in THF (271 ml) was cooled to 0° C. Butyllithium solution (2.5 M in hexanes; 29.2 ml, 73.0 mmol) was added dropwise and the resulting mixture was stirred at 0° C. for 12 min. ((1R,2S)-2-formylcyclobutyl) methyl acetate (Intermediate AA11A, Step 16; 5.30 g, 33.9 mmol) was added and the mixture was stirred for 60 min. TLC (1:2 EtOAc/hexane) showed complete disapperance of the starting material. The reaction mixture was added to stirred ice-water (60 mL), the organic phase was separated and the aqueous was extracted with EtOAc (200 mL). The combined organics were dried over MgSO$_4$ and concentrated to give a red oil. The crude material was purified by silica gel chromatography eluting with a gradient of 0-50% EtOAc in heptanes to give ((1R,2S)-2-((E)-pent-1-en-1-yl)cyclobutyl) methyl acetate (4.66 g, 23.8 mmol, 70% yield).

Step 2: (1R,2S)-2-((E)-pent-1-en-1-yl)cyclobutanecarbaldehyde

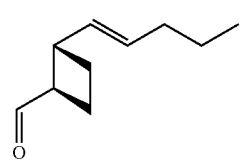

Lithium hydroxide (1 N, aq.; 53.5 mL, 53.5 mmol) was added to a solution of ((1R,2S)-2-((E)-pent-1-en-1-yl)cyclobutyl)methyl acetate (Example 779, step 1, 3.5 g, 17.8 mmol) in MeOH (100 mL) at ambient temperature. The reaction was warmed to 45° C. and left overnight. The mixture was then cooled and most of the solvent was removed in vacuo. The residue was dissolved in EtOAc (50 mL) and washed with 1N HCl and brine, dried over MgSO4, filtered and concentrated in vacuo. The residue was redissolved in DCM (40 mL), sodium bicarbonate (7.49 g, 89 mmol) was added and the mixture was stirred vigorously and cooled to 0° C. Dess-Martin periodinane (9.08 g, 21.4 mmol) was added in 10 portions over 20 min. The mixture was warmed to ambient temperature and stirred for an additional 4 h, quenched with 1N sodium thiosulfate and 1N sodium bicarbonate (1:1, 50 mL:50 mL) and then stirred vigorously for 2 h. The layers were separated and the organics were dried over MgSO4, filtered and concentrated in vacuo. The residue was dissolved in hexanes and filtered through celite to remove remaining light yellow solids. This material was used without further purification.

Step 3: (S)-methyl 6'-chloro-5-(((1R,2 S)-2-((E)-pent-1-en-1-yl) cyclobutyl)methyl)-3',4,4',5-tetrahydro-2H,2'H-spiro [benzo[b][1,4]oxazepine-3,1'-naphthalene]-7-carboxylate

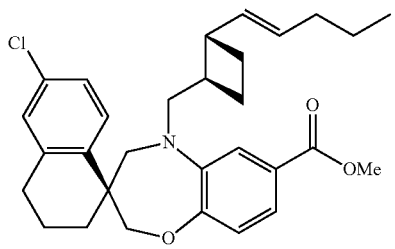 [SMILES: CCC/C=C/[C@@H]1CC[C@H]1CN1C[C@@]2(CCCc3cc(Cl)ccc32)COc2ccc(C(=O)OC)cc21]

(1S,2R)-2-((E)-pent-1-en-1-yl)cyclobutanecarbaldehyde (Example 779, step 2, 213 mg, 1.397 mmol) was added to a solution of (S)-methyl 6'-chloro-3',4,4',5-tetrahydro-2H,2'Hspiro[benzo[b][1,4]oxazepine-3,1'-naphthalene]-7-carboxylate (Intermediate AA11A, Step 11, 250 mg, 0.699 mmol) in DCM (3.88 mL) and AcOH (1.94 mL). The mixture was stirred at 0° C. for 10 min. then sodium cyanoborohydride (88 mg, 1.40 mmol) was added slowly portion wise during 40 min and maintained at 0° C. for 1 h. The mixture was then poured slowly into sat. Na₂CO₃ solution (50 ml) at 0° C. and extracted with EtOAc (3×30 mL). The combined organic phase was dried over anhydrous magnesium sulfate, filtered and concentrated. The crude material was purified by column chromatography on a 24 g column eluting with a gradient of 0 to 10 to 20% EtOAc in heptane) to provide (S)-methyl 6'-chloro-5-(((1R,2S)-2-((E)-pent-1-en-1-yl)cyclobutyl)methyl)-3',4,4',5-tetrahydro-2H,2'H-spiro[benzo[b][1,4]oxazepine-3,1'-naphthalene]-7-carboxylate (294 mg, 0.595 mmol, 85% yield).

Step 4: (S)-6'-chloro-5-(((1R,2S)-2-((E)-pent-1-en-1-yl)cyclobutyl)methyl)-3',4,4',5-tetrahydro-2H,2'H-spiro[benzo[b][1,4]oxazepine-3,1'-naphthalene]-7-carboxylic Acid

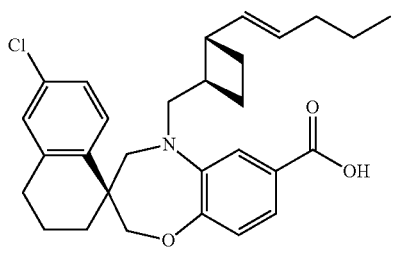 [SMILES: CCC/C=C/[C@@H]1CC[C@H]1CN1C[C@@]2(CCCc3cc(Cl)ccc32)COc2ccc(C(=O)O)cc21]

A solution of (S)-methyl 6'-chloro-5-(((1R,2S)-2-((E)-pent-1-en-1-yl)cyclobutyl)methyl)-3',4,4',5-tetrahydro-2H, 2'H-spiro[benzo[b][1,4]oxazepine-3,1'-naphthalene]-7-carboxylate (Example 779, step 3, 294 mg, 0.595 mmol) in THF (7.9 mL) and MeOH (3.97 mL) was treated with 1 N LiOH (4.17 mL, 4.17 mmol) at 50° C. for 1 h then at 60° C. for 3.5 h. The mixture was then cooled to ambient temperature, quenched with 1 N HCl (8.33 mL, 8.33 mmol), diluted with brine (50 mL), then extracted with EtOAc (3×30 mL). The combined organics were dried (MgSO₄) and concentrated to give a white foam. The crude (S)-6'-chloro-5-(((1R,2 S)-2-((E)-pent-1-en-1-yl)cyclobutyl)methyl)-3',4,4',5-tetrahydro-2H,2'H-spiro[benzo[b][1,4]oxazepine-3,1'-naphthalene]-7-carboxylic acid (268 mg, 0.558 mmol) was used without further purification.

Step 5: (S)—N-((2-(allyloxy)ethyl)sulfonyl)-6'-chloro-5-(((1R,2S)-2-((E)-pent-1-en-1-yl)cyclobutyl)methyl)-3',4,4',5-tetrahydro-2H,2'H-spiro[benzo[b][1,4]oxazepine-3,1'-naphthalene]-7-carboxamide

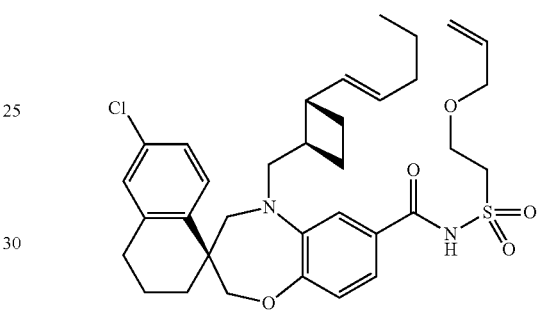

The title compound was synthesized from (S)-6'-chloro-5-(((1R,2S)-2-((E)-pent-1-en-1-yl)cyclobutyl)methyl)-3',4,4',5-tetrahydro-2H,2'H-spiro[benzo[b][1,4]oxazepine-3,1'-naphthalene]-7-carboxylic acid (Example 779, step 4, 170 mg, 0.354 mmol) and 2-(allyloxy)ethanesulfonamide (Example 817, Step 3, 398 mg, 2.41 mmol) following the procedure described for Example 1, Step 1. Purification of the crude material provided (S)—N-((2-(allyloxy)ethyl) sulfonyl)-6'-chloro-5-(((1R,2S)-2-((E)-pent-1-en-1-yl)cyclobutyl)methyl)-3',4,4',5-tetrahydro-2H,2'H-spiro[benzo [b][1,4]oxazepine-3,1'-naphthalene]-7-carboxamide (50 mg, 0.080 mmol, 22.5% yield).

Step 6: (3'R,6'R,7E, 22S)-6'-chloro-3',4'-dihydro-2'H,15H-spiro[10,20-dioxa-13-thia-1,14-diazatetracyclo [14.7.2.0$^{3,6}$.0$^{19,24}$]pentacosa-7-16,18,24-tetraene-22,1'-naphthalen]-15-one-13, 13-dioxide

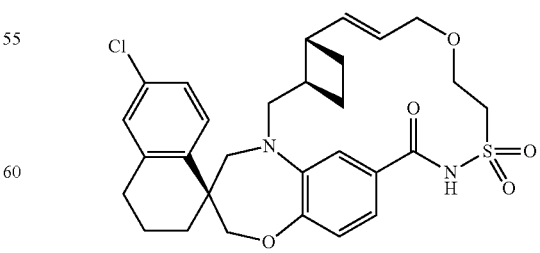

The title compound was synthesized from (S)—N-((2-(allyloxy)ethyl)sulfonyl)-6'-chloro-5-(((1R,2S)-2-((E)-pent-1-en-1-yl)cyclobutyl)methyl)-3',4,4',5-tetrahydro-2H,2'H- spiro[benzo[b][1,4]oxazepine-3,1'-naphthalene]-7-carboxamide (Example 779, step 5, 50 mg, 0.080 mmol) following the procedure described for Example 742, Step 2. Purification of the crude material provided (3'R,6'R,7E,22S)-6'-chloro-3',4'-dihydro-2'H,15H-spiro[10,20-dioxa-13-thia-1,14-diazatetracyclo[14.7.2.0$^{3,6}$.0$^{19,24}$]pentacosa-7-16,18,24-tetraene-22, 1'-naphthalen]-15-one-13, 13-dioxide (27 mg, 0.048 mmol, 60.8% yield).

Step 7. (3'R,6'R,7S,22S)-6'-chloro-7-hydroxy-3',4'-dihydro-2'H,15H-spiro[10,20-dioxa-13-thia-1,14-diazatetracyclo[14.7.2.0$^{3,6}$.0$^{19,24}$]pentacosa-16,18,24-triene-22, 1'-naphthalen]-15-one-13, 13-dioxide or (3'R,6'R,7R,22S)-6'-chloro-7-hydroxy-3',4'-dihydro-2'H,15H-spiro[10,20-dioxa-13-thia-1,14-diazatetracyclo[14.7.2.0$^{3,6}$.0$^{19,24}$]pentacosa-16,18,24-triene-22,1'-naphthalen]-15-one-13, 13-dioxide A solution of (3'R,6'R,7E, 22S)-6'-chloro-3',4'-dihydro-2'H,15H-spiro[10,20-dioxa-13-thia-1,14-diazatetracyclo[14.7.2.0$^{3,6}$.0$^{19,24}$]pentacosa-7-16,18,24-tetraene-22, 1'-naphthalen]-15-one-13, 13-dioxide (Example 779, step 6, 27 mg, 0.048 mmol) in THF (2.2 mL) under Ar was cooled to 0° C. and treated with borane tetrahydrofuran complex (1.0 M in tetrahydrofuran; 0.291 mL, 0.291 mmol). After 1 h N-methylmorpholine oxide (75 mg, 0.640 mmol) was added in one portion and the mixture was stirred while allowing to reach ambient temperature. After 24 h the mixture was diluted with water and brine and extracted with EtOAc and the combined organics were dried over MgSO4 and concentrated. The crude material contains a mixture of regioisomers at the 7 and 8 position each of which is a mixture of R/S isomers at the respective new sterocenter. The regioisomers were separated via reverse-phase HPLC to obtain a 3.8:1 mixture of epimers (3'R,6'R,7S,22S)-6'-chloro-7-hydroxy-3',4'-dihydro-2'H,15H-spiro[10,20-dioxa-13-thia-1,14-diazatetracyclo[14.7.2.0$^{3,6}$.0$^{19,24}$]pentacosa-16,18,24-triene-22, 1'-naphthalen]-15-one-13, 13-dioxide and (3'R,6'R,7R,22S)-6'-chloro-7-hydroxy-3',4'-dihydro-2'H,15H-spiro[10,20-dioxa-13-thia-1,14-diazatetracyclo[14.7.2.0$^{3,6}$.0$^{19,24}$]pentacosa-16,18,24-triene-22, 1'-naphthalen]-15-one-13, 13-dioxide as the second eluting component. This fraction was repurified by SFC to remove the minor epimer. (Sample preparation: 4.0 mg/2 mL (2.0 mg/mL) sample solution in MeOH. Preparative Purification: Column: Chiralpak OJ-H, 21×250 mm, 5 μm; Mobile Phase A: CO$_2$; Mobile Phase B: MeOH (20 mM NH$_3$); Composition: 40% B; Flow Rate: 50 mL/min; Loading: 0.5 mL of sample solution prepared as above (1.0 mg/injection); Detection: UV @ 244 nm; Total Elution Time: 6.2 min; Instrument: Thar 80 SFC) The 7-hydroxy regioisomer, (3'R, 6'R,7S,22S)-6'-chloro-7-hydroxy-3',4'-dihydro-2'H,15H-spiro[10,20-dioxa-13-thia-1,14-diazatetracyclo[14.7.2.0$^{3,6}$.0$^{19,24}$]pentacosa-16,18,24-triene-22, 1'-naphthalen]-15-one-13, 13-dioxide or (3'R,6'R,7R,22S)-6'-chloro-7-hydroxy-3',4'-dihydro-2'H,15H-spiro[10,20-dioxa-13-thia-1,14-diazatetracyclo[14.7.2.0$^{3,6}$.0$^{19,24}$]pentacosa-16,18,24-triene-22, 1'-naphthalen]-15-one-13, 13-dioxide (1.9 mg, 0.003 mmol, 6.8% yield) was isolated as the first eluting and major epimer. $^1$H NMR (400 MHz, CD$_2$Cl$_2$) δ 7.73 (d, J=8.4 Hz, 1H), 7.27 (dd, J=2.1, 8.3 Hz, 1H), 7.18 (s, 1H), 7.17 (dd, J=2.2, 8.8 Hz, 1H), 7.08 (d, J=2.2 Hz, 1H), 6.94 (d, J=8.2 Hz, 1H), 4.13-4.09 (m, 1H), 4.07 (s, 2H), 4.05-3.94 (m, 2H), 3.82 (dt, J=2.3, 11.1 Hz, 2H), 3.71 (d, J=14.1 Hz, 1H), 3.64-3.56 (m, 2H), 3.40 (td, J=2.7, 15.3 Hz, 1H), 3.19 (d, J=14.3 Hz, 1H), 3.01 (dd, J=8.1, 15.4 Hz, 1H), 2.82-2.72 (m, 2H), 2.20-1.86 (m, 6H), 1.85-1.76 (m, 1H), 1.69-1.36 (m, 6H). MS (ESI, +ve ion) m/z 575.0 (M+H)$^+$.

Example 780. (3R,6R,8S,22S)-6'-chloro-8-hydroxy-3',4'-dihydro-2'H,15H-spiro[10,20-dioxa-13-thia-1,14-diazatetracyclo[14.7.2.0$^{3,6}$.0$^{19,24}$]pentacosa-16,18,24-triene-22, 1'-naphthalen]-15-one-13, 13-dioxide or (3R,6R,8R,22S)-6'-chloro-8-hydroxy-3',4'-dihydro-2'H,15H-spiro[10,20-dioxa-13-thia-1,14-diazatetracyclo[14.7.2.0$^{3,6}$.0$^{19,24}$]pentacosa-16,18,24-triene-22, 1'-naphthalen]-15-one-13, 13-dioxide

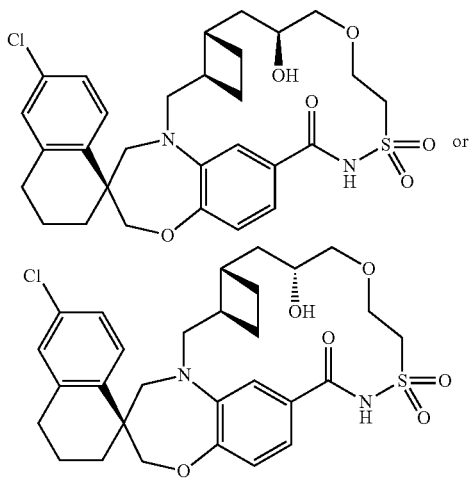

From the purification described in Example 779, step 7, the initial reverse phase separation gave the 8-hydroxy epimers with (3R,6R,8S,22S)-6'-chloro-8-hydroxy-3',4'-dihydro-2'H,15H-spiro[10,20-dioxa-13-thia-1,14-diazatetracyclo[14.7.2.0$^{3,6}$.0$^{19,24}$]pentacosa-16,18,24-triene-22, 1'-naphthalen]-15-one-13, 13-dioxide and (3R,6R,8R,22S)-6'-chloro-8-hydroxy-3',4'-dihydro-2'H,15H-spiro[10,20-dioxa-13-thia-1,14-diazatetracyclo[14.7.2.0$^{3,6}$.0$^{19,24}$]pentacosa-16,18,24-triene-22, 1'-naphthalen]-15-one-13, 13-dioxide as the first eluting component as a 7.5:1 mixture of epimers. This fraction was further purified by SFC (Sample preparation: 4.0 mg/3 mL (1.3 mg/mL) sample solution in MeOH: DCM (2:1). Preparative Purification: Column: Chiralpak IC, 21×250 mm, 5 μm; Mobile Phase A: CO$_2$; Mobile Phase B: MeOH(20 mM NH$_3$); Composition: 35% B; Flow Rate: 50 mL/min; Loading: 0.5 mL of sample solution prepared as above (0.7 mg/injection); Detection: UV @ 244 nm; Total Elution Time: 27.4 min; Instrument: Thar 80 SFC) to provide the first eluting and major isomer as (3R,6R,8S, 22S)-6'-chloro-8-hydroxy-3',4'-dihydro-2'H,15H-spiro[10, 20-dioxa-13-thia-1,14-diazatetracyclo [14.7.2.0$^{3,6}$.0$^{19,24}$]pentacosa-16,18,24-triene-22, 1'-naphthalen]-15-one-13, 13-dioxide or (3R,6R,8R,22S)-6'-chloro-8-hydroxy-3',4'-dihydro-2'H,15H-spiro[10,20-dioxa-13-thia-1,14-diazatetracyclo [14.7.2.0$^{3,6}$.0$^{19,24}$]pentacosa-16,18,24-triene-22, 1'-naphthalen]-15-one-13, 13-dioxide (2.2 mg, 0.004 mmol, 7.9% yield). $^1$H NMR (400 MHz, CD$_2$Cl$_2$) δ 7.72 (d, J=8.6 Hz, 1H), 7.23 (d, J=7.4 Hz, 1H), 7.17 (d, J=8.6 Hz, 1H), 7.08 (s, 1H), 7.04 (br s, 1H), 6.94 (d, J=8.0 Hz, 1H), 4.12-4.01 (m, 2H), 3.98-3.81 (m, 4H), 3.74 (d, J=14.7 Hz, 1H), 3.69-3.56 (m, 1H), 3.56-3.43 (m, 2H), 3.41-3.31 (m, 1H), 3.22 (d, J=14.3 Hz, 1H), 3.27-3.13 (m, 1H), 2.84-2.68 (m, 2H), 2.37-2.24 (m, 1H), 2.16 (br s, 2H), 2.10-1.99 (m, 3H), 1.90 (br s, 2H), 1.83 (br s, 1H), 1.75-1.67 (m, 1H), 1.54-1.43 (m, 3H). MS (ESI, +ve ion) m/z 575.0 (M+H)+.

Example 781. (1S,3'R,6'R,7'S,11R,13'R)-6-chloro-7'-hydroxy-3,4-dihydro-2H,16'H-spiro[naphthalene-1,23'-[21]oxa[14]thia[1,15]diazapentacyclo [15.7.2.0³,⁶.0¹¹,¹³.0²⁰,²⁵]hexacosa[17,19,25]trien]-16'-one 14',14'-dioxide or (1S,3'R,6'R,7'S,11'S,13'S)-6-chloro-7'-hydroxy-3,4-dihydro-2H,16'H-spiro[naphthalene-1,23'-[21]oxa[14]thia[1,15]diazapentacyclo [15.7.2.0³,⁶.0¹¹,¹³.0²⁰,²⁵]hexacosa[17,19,25]trien]-16'-one 14',14'-dioxide

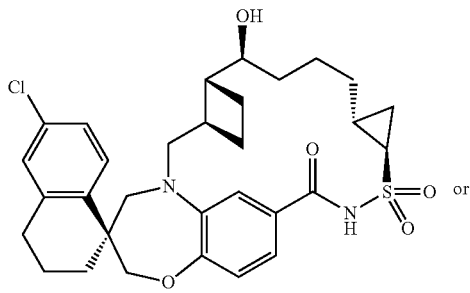

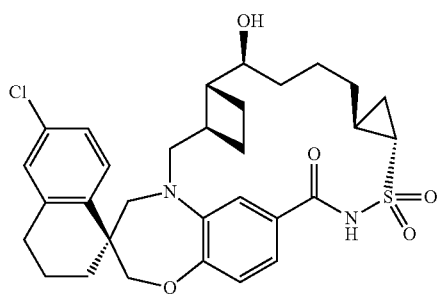

To a solution of Example 793 (1.8 mg, 3.1 µmol) in MeOH (10 mL) was added rhodium, 5 wt. % on carbon (0.5 µl, 3 µmol). The reaction mixture was subjected to three cycles of evacuation/back-filling with hydrogen and stirred at r.t. overnight under hydrogen balloon. After the catalyst was filtered off the filtrate was concentrated and the residue was purified by reverse phase preparatory HPLC (Gemini™ Prep C₁₈ 5 µm column; Phenomenex, Torrance, CA; MeCN in water with 0.1% TFA, gradient elution) to give 0.51 mg of the title compound as a white solid. ¹H NMR (500 MHz, CD₃CN) δ 7.70 (d, J=8.6 Hz, 1H), 7.47 (s, 1H), 7.18 (dd, J=2.3, 8.4 Hz, 1H), 7.14 (s, 1H), 7.03 (dd, J=2.0, 8.1 Hz, 1H), 6.89 (d, J=8.1 Hz, 1H), 4.20-4.10 (m, 2H), 3.67-3.52 (m, 3H), 3.51-3.41 (m, 3H), 2.78-2.73 (m, 2H), 2.69 (td, J=4.2, 8.4 Hz, 2H), 2.50-1.03 (m, 15H), 0.94-0.82 (m, 4H). 585.2 m/z (ESI, +ve ion).

Example 783. (1S,3'R,6'R,7'S,8'E,12'R)-6-chloro-12'-ethyl-7'-(3-oxetanyloxy)-3,4-dihydro-2H,15'H-spiro[naphthalene-1,22'-[20]oxa[13]thia[1,14]diazatetracyclo [14.7.2.0³,⁶.0¹⁹,²⁴]pentacosa[8,16,18,24] tetraen]-15'-one 13',13'-dioxide

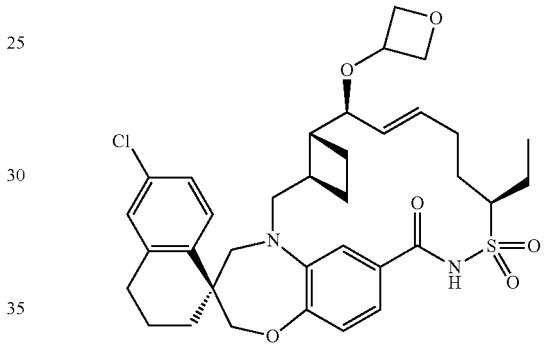

Sodium hydride, 60% dispersion in mineral oil (1.7 µL, 0.083 mmol) was added to a solution of Example 422, Step 1 (10.0 mg, 0.017 mmol) in 1.0 mL of THF at 0° C. The reaction mixture was stirred at 0° C. for 30 min and then 3-bromooxetane (22 µL, 0.27 mmol) was added. The reaction mixture was stirred at r.t. for 3 days and then queched with aq NH₄Cl solution. It was added 1 N HCl solution (1 mL) and EtOAc (40 mL). The organic layer was seperated and concentrated. The residue was purified by reversed phase preparatory HPLC (Gemini™ Prep C₁₈ 5 µm column; Phenomenex, Torrance, CA; gradient elution of 20% to 90% MeCN in water, where both solvents contain 0.1% TFA, 40 min method) to provide the title compound (1.4 mg, 2.14 µmol) as a white foam. ¹H NMR (400 MHz, CD₃CN) δ 9.40 (br s, 1H), 7.73 (d, J=8.4 Hz, 1H), 7.24-7.18 (m, 1H), 7.17-7.13 (m, 1H), 7.00-6.95 (m, 1H), 6.92-6.87 (m, 1H), 6.82-6.77 (m, 1H), 5.85-5.75 (m, 1H), 5.61-5.52 (m, 1H), 4.12-3.91 (m, 3H), 3.84-3.76 (m, 2H), 3.74-3.68 (m, 1H), 3.55 (dd, J=2.9, 11.5 Hz, 1H), 3.45-3.37 (m, 1H), 3.29-3.23 (m, 1H), 3.13-2.98 (m, 1H), 2.83-2.70 (m, 3H), 2.53-2.48 (m, 2H), 1.82-1.71 (m, 8H), 1.59-1.54 (m, 1H), 1.48-1.38 (m, 3H), 1.34-1.26 (m, 2H), 1.16 (s, 4H), 0.93-0.84 (m, 1H). MS (ESI) m/z 655.2 [M+H]+.

Example 784. (1S,3'R,6'R,7'S,8'E,10'R,12'R)-6-chloro-7'-hydroxy-3,4-dihydro-2H,16'H-spiro[naphthalene-1,23'-[21]oxa[14]thia[1,15]diazapentacyclo[15.7.2.0³,⁶.0¹⁰,¹².0²⁰,²⁵]hexacosa[8,17,19,25]tetraen]-16'-one 14',14'-dioxide or (1S,3'R,6'R,7'S,8'E,10'S,12'S)-6-chloro-7'-hydroxy-3,4-dihydro-2H,16'H-spiro[naphthalene-1,23'-[21]oxa[14]thia[1,15]diazapentacyclo [15.7.2.0³,⁶.0¹⁰,¹²0²⁰,²⁵]hexacosa[8,17,19,25]tetraen]-16'-one 14',14'-dioxide

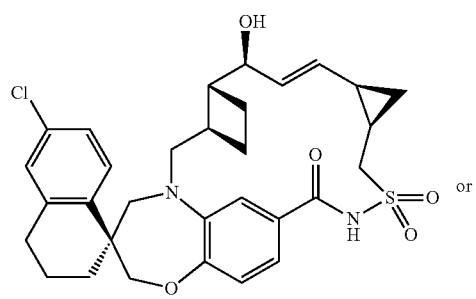

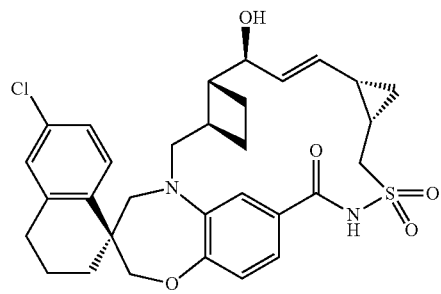

Step 1: (Z)-4-((tert-butyldiphenylsilyl)oxy)but-2-en-1-ol

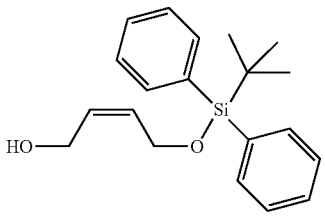 [SMILES: CC(C)(C)[Si](OC/C=C\CO)(c1ccccc1)c1ccccc1]

To a solution of cis-2-butene-1,4-diol (5.0 mL, 57 mmol) and N,N-diisopropylethylamine (11.9 mL, 68 mmol) in DCM (114 mL) was added tert-butyldiphenylsilyl chloride (14.8 mL, 56.8 mmol) at 0° C. The reaction mixture was stirred at 0° C. for 30 min and then at r.t. for 16 h. The reaction was quenched by sat. NH₄Cl solution (10 mL) at 0° C. and extracted with ethyl acetate (120 mL). The organic phase was washed with NH₄Cl solution (40 mL), NaHCO₃ solution (40 mL), brine (10 mL) and dried over anhydrous MgSO₄. After concentration the residue was loaded on a 4 g ISCO Gold column and eluted with 0% to 50% EtOAc/hexane to provide the title compound (12.0 g, 36.8 mmol, 65% yield).

Step 2: ((1S,2R)-2-((tert-butyldiphenylsilyl)oxy)methyl)cyclopropyl) methanol and ((1R,2S)-2-(((tert-butyldiphenylsilyl)oxy) methyl)cyclopropyl) methanol

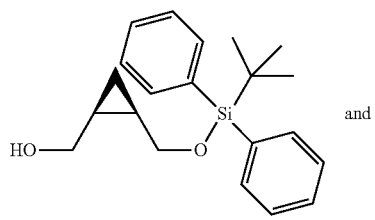

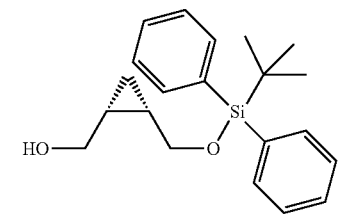

To a solution of diethylzinc, 1.0 M solution in hexanes, (29.4 mL, 29.4 mmol) in DCM (49 mL) was added dropwise diiodomethane (4.74 mL, 58.8 mmol) at −10° C. After 15 min of stirring, a white precipitate was formed and a solution of (4R,5R)-(−)-2,2-dimethyl-alpha,alpha,alpha',alpha'-tetraphenyl-1,3-dioxolane-4,5-dimethaolato[1,2-bis(dimethoxy)ethane] titanium(IV)dichloride (0.527 g, 0.735 mmol) and molecular sieves 4A (1.3 g) in DCM (8 mL) were added by cannula at −10° C. The solution was stirred at that temperature for 5 min and a solution of (Z)-4-((tert-butyldiphenylsilyl)oxy)but-2-en-1-ol (Example 784, Step 1) (8.0 g, 24.5 mmol) in DCM (49 mL) was added at −10° C. The resulting mixture was allowed to warm to 0° C. for 2 h with light exclusion. The reaction was quenched with 1 N HCl solution at −40° C. and extracted with DCM (2×60 mL). The combined organic layers were washed with brine (20 mL) and dried over anhydrous MgSO₄. After concentration the residue was loaded on a 4 g ISCO Gold column and eluted with 0% to 50% EtOAc/hexane to provide the title compound (5.72 g, 16.8 mmol, 69% yield).

Step 3: (1S,2R)-2-(((tert-butyldiphenylsilyl)oxy)methyl)cyclopropane carbaldehyde and (1R,2S)-2-(((tert-butyldiphenylsilyl)oxy) methyl)cyclopropanecarbaldehyde

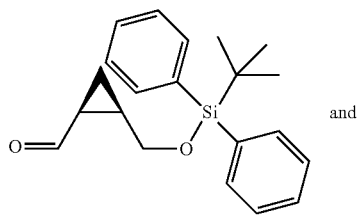

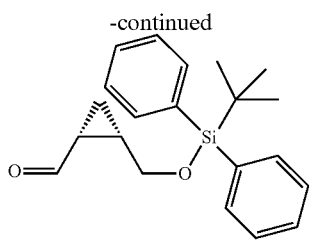

To a white slurry solution of (diacetoxyiodo)benzene (1.04 g, 3.2 mmol) and ((1S,2R)-2-(((tert-butyldiphenylsilyl)oxy)methyl)cyclopropyl)methanol (Example 784, Step 2) (1.0 g, 2.9 mmol) in DCM (9.8 mL) was added 2,2,6,6-tetramethylpiperidinooxy (0.023 g, 0.147 mmol) in one portion and it was stirred at r.t. for 2 h (The mixture became a homogeneous, bright pale orange solution). The reaction mixture was diluted with DCM (60 mL) and washed with sodium bicarbonate solution (30 mL), brine (30 mL) and dried over anhydrous MgSO$_4$. It was concentrated to provide the title compound, which was used without further purification.

Step 4: tert-butyldiphenyl(((1R,2R)-2-((E)-prop-1-en-1-yl)cyclopropyl) methoxy)silane and tert-butyldiphenyl(((1S,2S)-2-((E)-prop-1-en-1-yl)cyclopropyl)methoxy)silane

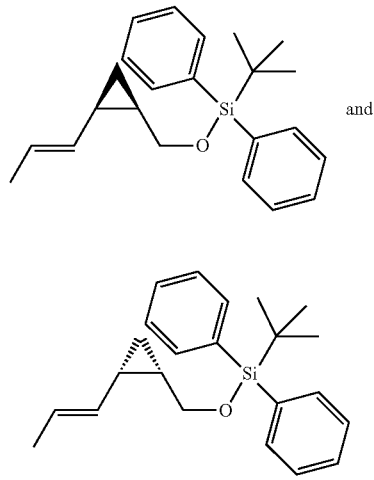

To a solution of (ethyl)triphenylethylphosphonium bromide (1.4 g, 3.76 mmol) in THF (15 mL) was slowly added n-butyllithium, 2.5 M solution in hexanes (1.3 mL, 3.2 mmol) at −78° C. (dry ice bath). The reaction mixture was stirred at −78° C. for 1 h, forming an orange solution. (1S,2R)-2-(((tert-Butyldiphenylsilyl)oxy)methyl)cyclopropanecarbaldehyde (Example 784, Step 3) (0.98 g, 2.89 mmol) in THF (4 mL) was added at −78° C. The temperature of the bath was slowly warmed up to r.t. The reaction was quenched by sat. NH$_4$Cl solution (20 mL), extracted with ethyl acetate (2×50 mL). The combined organic layers were washed with brine and dried over anhydrous MgSO$_4$. After concentration the residue was loaded on a 24 g ISCO Gold column and eluted with 0% to 30% EtOAc/hexane to provide the title compound (0.40 g, 1.14 mmol, 39% yield).

Step 5: ((1R,2R)-2-((E)-prop-1-en-1-yl)cyclopropyl)methanol and ((1S,2S)-2-((E)-prop-1-en-1-yl)cyclopropyl)methanol

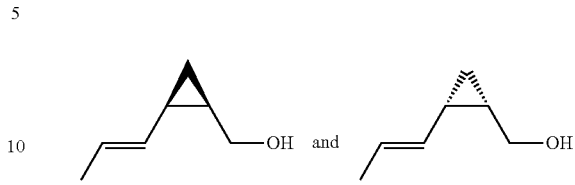

To a solution of tert-butyldiphenyl(((1R,2R)-2-((E)-prop-1-en-1-yl)cyclopropyl)methoxy)silane (Example 784, Step 4) (2.0 g, 5.7 mmol) in THF (28 mL) was added tetrabutylammonium fluoride solution, 1.0 M in THF (5.7 mL, 5.7 mmol). The resulting mixture was stirred at r.t. for 18 h. After concentration the residue was loaded on a 24 g ISCO Gold column and eluted with 0% to 50% EtOAc/hexane to provide the title compound (0.62 g, 5.5 mmol, 98% yield).

Step 6: 2-((((1R,2R)-2-((E)-prop-1-en-1-yl)cyclopropyl)methyl)thio) pyrimidine and 2-((((1S,2S)-2-((E)-prop-1-en-1-yl)cyclopropyl)methyl)thio) pyrimidine

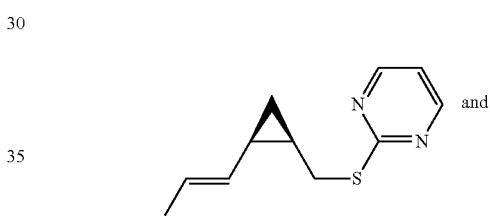

(E)-Diethyl diazene-1,2-dicarboxylate (DEAD), 40% w/w in toluene (0.78 mL, 4.3 mmol) was added dropwise to a solution of tributylphosphine (1.2 mL, 4.85 mmol) in THF (19 mL) at 0° C. After it was stirred at r.t. for 10 min, ((1R,2R)-2-((E)-prop-1-en-1-yl) cyclopropyl)methanol (Example 784, Step 5) (0.32 g, 2.85 mmol) was added dropwise to the phosphine/DEAD complex via syringe as the neat liquid. After the resulting ROH/DEAD/Bu$_3$P mixture was aged at 0° C. for 20 min, pyrimidine-2-thiol (0.640 g, 5.71 mmol) was added in small portions. The reaction mixture was stir at r.t. for 4 h. Hexane (40 mL) was added to the reaction mixture and it was stirred at r.t. for 15 min. The solid was removed by filtration and the filtrate was concentrated. The residue was loaded on a 12 g ISCO Gold column and eluted with 0% to 15% EtOAc/hexane to provide the title compound (0.35 g, 1.7 mmol, 60% yield).

Step 7: 2-((((1R,2R)-2-((E)-prop-1-en-1-yl)cyclopropyl)methyl)sulfonyl)pyrimidine and 2-((((1S,2S)-2-((E)-prop-1-en-1-yl)cyclopropyl)methyl)sulfonyl)pyrimidine

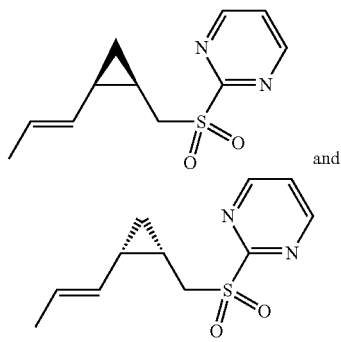

To a solution of 2-(4 (1R,2R)-2-((E)-prop-1-en-1-yl)cyclopropyl)methyl)thio)pyrimidine (Example 784, Step 6) (0.40 g, 1.9 mmol) in DCM (9.6 mL) was added 3-chlorobenzoperoxoic acid (0.863 g, 3.85 mmol) in three portions at 0° C. during a perion of 15 min and then it was stirred at r.t. for 3 h. The reaction was then poured into ice and saturated sodium carbonate solution and extracted with DCM. The combined organics were concentrated to provide the crude title compound (0.45 g, 1.9 mmol, 98% yield), which was used without futher purification.

Step 8: sodium ((1R,2R)-2-((E)-prop-1-en-1-yl)cyclopropyl)methanesulfinate and sodium ((1S,2S)-2-((E)-prop-1-en-1-yl)cyclopropyl)methanesulfinate

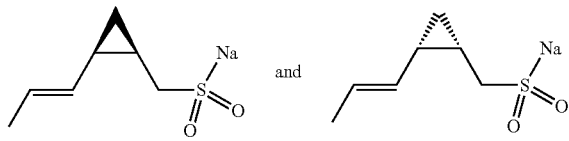

To a stirred solution of 2-((((1R,2R)-2-((E)-prop-1-en-1-yl)cyclopropyl)methyl) sulfonyl)pyrimidine (Example 784, Step 7) (0.45 g, 1.9 mmol) in MeOH (19 mL) was added sodium methoxide (0.43 mL, 1.9 mmol). After the mixture was stirred at r.t. for 1.5 h, it was concentrated and Et$_2$O was added to the mixture. The solid was collected by filtration and purified by washing with cold Et$_2$O to provide the title compound, which was used without futher purification.

Step 9: ((1R,2R)-2-((E)-prop-1-en-1-yl)cyclopropyl)methanesulfonamide and ((1S,2S)-2-((E)-prop-1-en-1-yl)cyclopropyl)methanesulfonamide

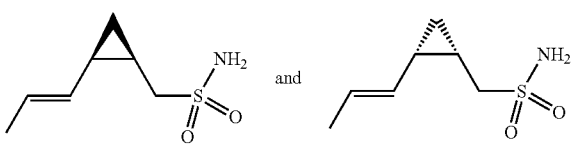

A solution of sodium 41R,2R)-2-((E)-prop-1-en-1-yl)cyclopropyl)methanesulfinate (Example 784, Step 8) (0.35 g, 1.9 mmol) in water (13 mL) was treated with sodium acetate (0.236 g, 2.88 mmol) and hydroxylamine-o-sulfonic acid (0.266 g, 2.11 mmol). The reaction was stirred at 50° C. for 0.5 h and at r.t. for 1.5 h. Then the reaction was cooled to 0° C., basified with NaOH solution. It was extracted with DCM (2×70 mL) and the combined organic phases were washed with brine and dried over anhydrous MgSO$_4$. After concentration the residue was loaded on a 12 g ISCO Gold column and eluted with 0% to 75% EtOAc/hexane to provide the title compound (0.022 g, 0.126 mmol).

Step 10: (S)-6'-chloro-5-(((1R,2R)-2-((S)-1-hydroxyallyl)cyclobutyl) methyl)-N-((((1R,2R)-2-((E)-prop-1-en-1-yl)cyclopropyl)methyl) sulfonyl)-3',4,4',5-tetrahydro-2H,2'H-spiro[benzo[b][1,4]oxazepine-3,1'-naphthalene]-7-carboxamide and (S)-6'-chloro-5-(((1R,2R)-2-((S)-1-hydroxyallyl)cyclobutyl)methyl)-N-(4 (1S,2S)-2-((E)-prop-1-en-1-yl)cyclopropyl)methyl)sulfonyl)-3',4,4',5-tetrahydro-2H,2'H-spiro[benzo[b][1,4]oxazepine-3,1'-naphthalene]-7-carboxamide

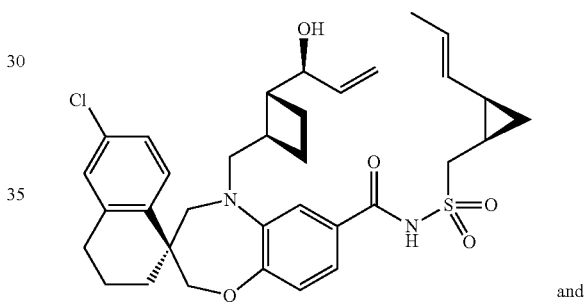

and

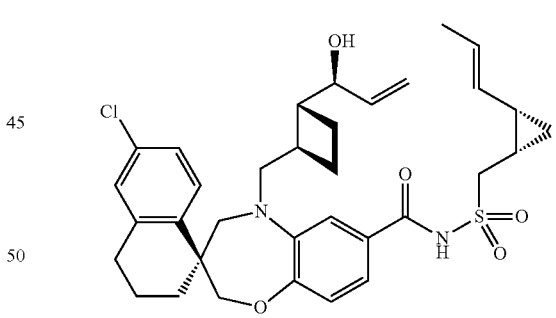

4-Pyrrolidinopyridine (19 mg, 0.13 mmol) was added (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Example 784, Step 9) (65 mg, 0.139 mmol) and DIEA (0.088 mL, 0.505 mmol) in DCM (1.3 ml). Then N-(3-dimethylaminopropyl)-N'-ethylcarbodiimide hydrochloride (121 mg, 0.631 mmol) was added slowly at 0° C. The reaction mixture was stirred at 0° C. to r.t. overnight. The reaction mixture was concentrated and the residue was loaded on a 4 g ISCO Gold column and eluted with 0% to 40% EtOAc (containing 0.3% AcOH)/hexane (containing 0.3% AcOH) to provide the title compound (58 mg, 0.093 mmol, 74% yield)

Step 11: (1S,3'R,6'R,7'S,8'E,10'R,12'R)-6-chloro-7'-hydroxy-3,4-dihydro-2H,16'H-spiro[naphthalene-1, 23'-[21]oxa[14]thia[1,15]diazapentacyclo [15.7.2.0$^{3,6}$.0$^{10,12}$.0$^{20,25}$]hexacosa[8,17,19,25]tetraen]-16'-one 14',14'-dioxide or (1S,3'R,6'R,7'S,8'E,10'S,12'S)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{10,12}$.0$^{20,25}$]hexacosa[8,17,19,25]tetraen]-16'-one 14',14'-dioxide A 100 mL round bottom flask was charged with (S)-6'-chloro-5-((((1R,2R)-2-((S)-1-hydroxyallyl)cyclobutyl)methyl)-N-((((1R,2R)-2-((E)-prop-1-en-1-yl)cyclopropyl)methyl) sulfonyl)-3',4,4',5-tetrahydro-2H,2'H-spiro[benzo[b][1,4]oxazepine-3,1'-naphthalene]-7-carboxamide (Example 784, Step 10) (72 mg, 0.115 mmol) and Hoveyda-Grubbs II (25 mg, 0.040 mmol) and DCE (58 mL). The reaction mixture was subjected to three cycles of evacuation/back-filling with nitrogen and heated at 60° C. for about 6 h under nitrogen. SiliaMetS (0.2 g, 0.62 mmol/g) was added and stirred at r.t. for 30 min. The scavenger was filtrated off and the filtrate was concentrated. The residue was loaded on a 4 g ISCO Gold column and eluted with 0% to 50% EtOAc (containing 0.3% AcOH)/hexane (containing 0.3% AcOH) to provide the title compound (1.3 mg, 2.2 µmol) as the second (slower) eluting isomer. $^1$H NMR (400 MHz, CD$_3$CN) δ 7.76-7.71 (m, 1H), 7.42 (d, J=2.0 Hz, 1H), 7.25-7.19 (m, 1H), 7.13 (s, 1H), 7.04-6.98 (m, 1H), 6.92-6.85 (m, 2H), 5.60 (dd, J=5.2, 15.6 Hz, 1H), 5.39-5.29 (m, 1H), 4.11-4.02 (m, 2H), 4.01-3.97 (m, 1H), 3.94-3.83 (m, 2H), 3.78-3.71 (m, 2H), 3.69-3.57 (m, 2H), 3.50-3.42 (m, 3H), 3.22 (d, J=14.1 Hz, 2H), 2.98 (dd, J=4.6, 15.0 Hz, 2H), 2.83-2.70 (m, 3H), 2.55-1.53 (m, 2H), 1.44-1.37 (m, 2H), 0.97 (dt, J=4.8, 8.9 Hz, 1H), 0.92-0.82 (m, 2H), 0.34-0.24 (m, 1H). m/z (ESI, +ve ion) 583.2 (M+H)$^+$.

Example 785. (1S,3'R,6'R,7'S,8'E,10'R,12'R)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{10,12}$.0$^{20,25}$]hexacosa[8,17,19,25]tetraen]-16'-one 14',14'-dioxide or (1S,3'R,6'R,7'S,8'E,10'S,12'S)-6-chloro-7'-hydroxy-3,4-dihydro-2H,16'H-spiro[naphthalene-1,23'-[21]oxa[14]thia[1,15] diazapentacyclo [15.7.2.0$^{3,6}$.0$^{10,12}$.0$^{20,25}$]hexacosa [8,17,19,25]tetraen]-16'-one 14',14'-dioxide

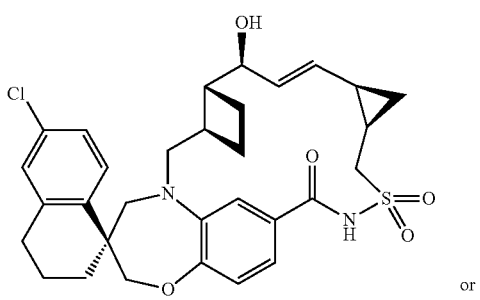

or

-continued

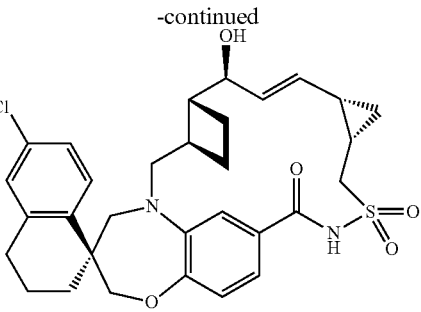

The title compound (2.1 mg, 3.60 µmol) was obtained as the first (faster) eluting isomer from Example 784 step 11, as a white solid. $^1$H NMR (400 MHz, CD$_3$CN) δ 9.48 (br s, 1H), 7.76-7.71 (m, 1H), 7.45-7.39 (m, 1H), 7.24-7.20 (m, 1H), 7.15 (s, 1H), 7.07-7.01 (m, 1H), 6.95-6.88 (m, 1H), 5.94 (dd, J=7.8, 15.1 Hz, 1H), 5.62-5.49 (m, 1H), 4.23-4.15 (m, 1H), 4.11-4.05 (m, 2H), 3.79-3.57 (m, 4H), 3.21 (d, J=13.9 Hz, 1H), 3.10-3.00 (m, 1H), 2.83-2.72 (m, 2H), 2.49-1.62 (m, 7H), 1.43 (d, J=10.4 Hz, 3H), 1.11 (dd, J=4.7, 9.0 Hz, 1H), 0.95-0.83 (m, 2H), 0.27-0.20 (m, 1H). m/z (ESI, +ve ion) 583.2 (M+H)$^+$.

Example 786. (1S,3'R,6'R,7'S,8'E,11'R,13'R)-6-chloro-7'-(2-methoxyethoxy)-3,4-dihydro-2H,16'H-spiro[naphthalene-1,23'-[21]oxa[14]thia[1,15]diazapentacyclo[15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E,11'S,13'S)-6-chloro-7'-(2-methoxyethoxy)-3,4-dihydro-2H,16'H-spiro [naphthalene-1,23'-[21]oxa[14]thia[1,15]diazapentacyclo[15.7.2.0$^{3,6}$.0$^{11,13}$.0$^{20,25}$]hexacosa[8,17,19,25]tetraen]-16'-one 14',14'-dioxide

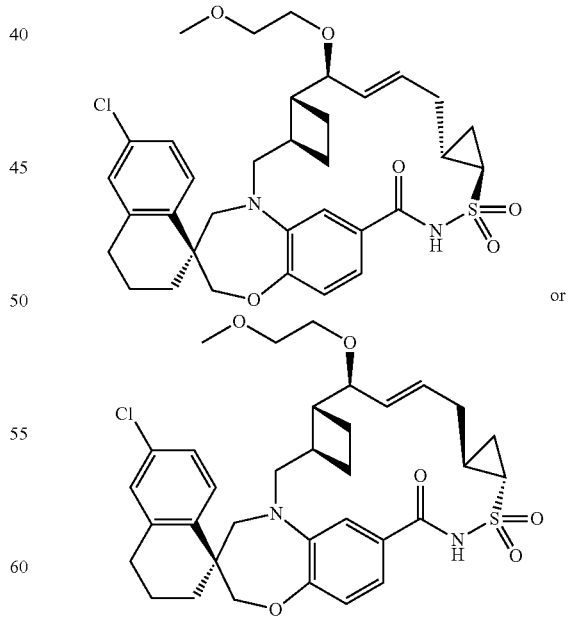

NaH (2.5 mg, 0.063 mmol) was added to a solution of Example 793 (7.3 mg, 0.013 mmol) in THF (1.0 mL) at 0° C. (ice bath) and it was stirred at this temperature for 30 min. Then 1-bromo-2-methoxyethane (3.5 µl, 0.038 mmol) was added slowly and it was stirred at r.t. overnight. The reaction mixture was quenched with water (15 mL) and acidified with 1N HCl solution to pH 1-2. It was extracted with EtOAc (30 mL) and the organic phase was washed with brine, dried over anhydrous MgSO$_4$ and concentrated. The residue was purified by reverse phase preparatory HPLC (Gemini™ Prep C$_{18}$ 5 μm column; Phenomenex, Torrance, CA; MeCN in water with 0.1% TFA, gradient elution) to give the title compound (2.1 mg, 1.8 μmol, 26% yield) as a white solid. $^1$H NMR (500 MHz, CD$_3$CN) δ 9.39 (br s, 1H), 7.74 (d, J=8.6 Hz, 1H), 7.23-7.19 (m, 2H), 7.17-7.14 (m, 1H), 7.08 (dd, J=2.0, 8.1 Hz, 1H), 6.92-6.88 (m, 1H), 5.57 (td, J=6.2, 15.6 Hz, 1H), 5.44 (dd, J=6.5, 15.8 Hz, 1H), 4.19-4.07 (m, 2H), 3.66 (d, J=14.2 Hz, 1H), 3.54 (dd, J=6.7, 15.0 Hz, 1H), 3.43-3.33 (m, 4H), 3.23-3.20 (m, 3H), 3.19-3.14 (m, 2H), 2.82-2.73 (m, 4H), 2.72-2.67 (m, 2H), 2.62-2.52 (m, 2H), 2.07-2.01 (m, 2H), 1.91-1.87 (m, 2H), 1.82-1.77 (m, 1H), 1.74-1.51 (m, 5H), 1.45 (td, J=5.0, 9.5 Hz, 1H), 1.05 (ddd, J=5.4, 6.7, 8.5 Hz, 1H). m/z (ESI, +ve ion) 641.2 (M+H)$^+$.

Example 787. (1S,3'R,6'R,7'S,10'S,12'R)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{10,12}$.0$^{20,25}$]hexacosa[17,19,25]trien]-16'-one 14',14'-dioxide and (1S,3'R,6'R,7'S,10'R,12'S)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{10,12}$.0$^{20,25}$]hexacosa[17,19,25]trien]-16'-one 14',14'-dioxide

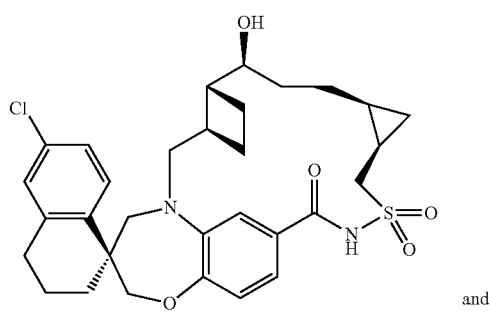

and

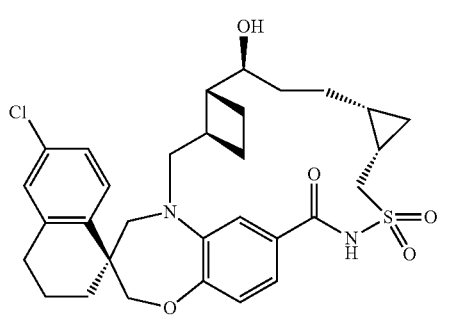

Step 1: (1S,3'R,6'R,7'S,8'E,10'R,12'R)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{10,12}$.0$^{20,25}$]hexacosa[8,17,19,25]tetraen]-16'-one 14',14'-dioxide and (1S,3'R,6'R,7'S,8'E,10'S,12'S)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{10,12}$.0$^{20,25}$]hexacosa[8,17,19,25]tetraen]-16'-one 14',14'-dioxide

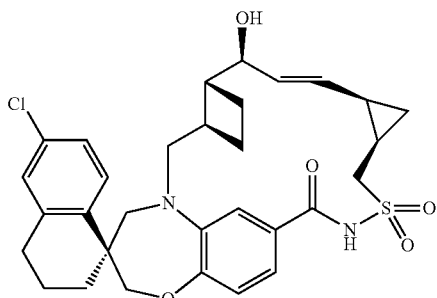

and

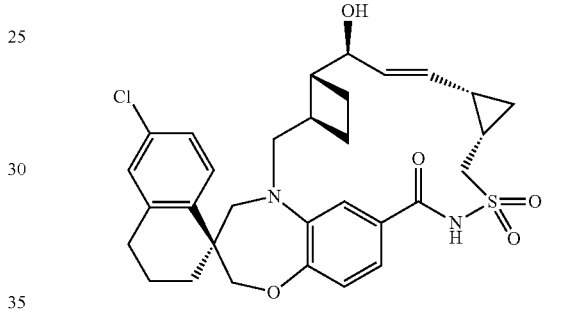

A 100 mL round bottom flask was charged with (S)-6'-chloro-5-(((1R,2R)-2-((S)-1-hydroxyallyl)cyclobutyl)methyl)-N-((((1R,2R)-2-((E)-prop-1-en-1-yl)cyclopropyl)methyl) sulfonyl)-3',4,4',5-tetrahydro-2H,2'H-spiro[benzo[b][1,4]oxazepine-3,1'-naphthalene]-7-carboxamide (Example 784, Step 10) (20.1 mg, 0.032 mmol) and Hoveyda-Grubbs II (16 mg, 0.026 mmol) and DCE (16.1 mL). The reaction mixture was subjected to three cycles of evacuation/back-filling with nitrogen and stirred at 60° C. for 6 h under nitrogen. SiliaMetS (0.2 g, 0.62 mmol/g) was added and stirred at r.t. for 30 min. The scavenger was filtrated off and the filtrate was concentrated. The residue was loaded on a 4 g ISCO Gold column and eluted with 0% to 60% EtOAc (containing 0.3% AcOH)/hexane (containing 0.3% AcOH) to provide the title compounds (5.5 mg, 9.4 μmol, 29% yield).

Step 2: (1S,3'R,6'R,7'S,10'S,12'R)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{10,12}$.0$^{20,25}$]hexacosa[17,19,25]trien]-16'-one 14',14'-dioxide and (1S,3'R,6'R,7'S,10'R,12'S)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{10,12}$.0$^{20,25}$]hexacosa[17,19,25]trien]-16'-one 14',14'-dioxide To a solution of (Example 787, Step 1) (20.2 mg, 0.034 mmol) in MeOH (17 mL) was added rhodium (3.6 mg, 1.7 μmol) (5 wt. % on carbon). The reaction mixture was subjected to three cycles of evacuation/back-filling with hydrogen and stirred at r.t. under hydrogen overnight. The catalyst was filtered off and the filtrate was concentrated. The residue was loaded on a 4 g ISCO Gold column and eluted with 0% to 60% EtOAc (containing 0.3% AcOH)/hexane (containing 0.3% AcOH) to provide the title compounds (0.98 mg, 1.7 µmol 10% yield). $^1$H NMR (500 MHz, CD$_3$CN) δ 7.72 (d, J=8.6 Hz, 1H), 7.20 (dd, J=2.4, 8.3 Hz, 1H), 7.15 (d, J=2.4 Hz, 1H), 7.05-7.02 (m, 1H), 6.92 (d, J=8.3 Hz, 2H), 4.17-4.07 (m, 2H), 3.84-3.78 (m, 1H), 3.66-3.51 (m, 2H), 3.40-3.35 (m, 1H), 2.99 (br s, 3H), 2.81-2.73 (m, 2H), 2.65-2.60 (m, 1H), 2.36-0.88 (m, 18H). m/z (ESI, +ve ion) 585.2 (M+H)$^+$.

Example 791. (3R,6R,7S,8E,12R,22S)-2'-chloro-7-hydroxy-12-methyl-7',8'-dihydro-6'H,15H-spiro[20-oxa-13-thia-1,14-diazatetracyclo [14.7.2.0$^{3,6}$.0$^{19,24}$]pentacosa-8,16,18,24-tetraene-22,5'-quinolin]-15-one 13,13-dioxide

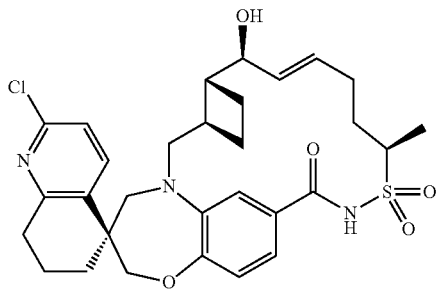 [SMILES: C[C@@H]1CC/C=C/[C@H](O)[C@@H]2CC[C@H]2CN2C[C@@]3(CCCc4nc(Cl)ccc43)COc3ccc(cc32)C(=O)NS1(=O)=O]

Step 1: (S)-5-(((1R,2R)-2-4S,E)-1-((tert-butyldimethylsilyl)oxy)hex-2-en-1-yl)cyclobutyl)methyl)-2'-chloro-N—((R)-HEX-5-en-2-ylsulfonyl)-4,5,7',8'-tetrahydro-2H,6'H-spiro[benzo[b][1,4]oxazepine-3,5'-quinolin]-7-carboxamide

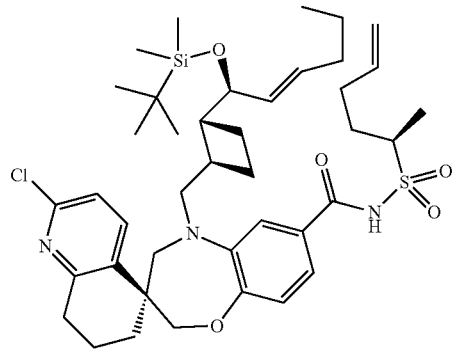 [SMILES: C=CCC[C@@H](C)S(=O)(=O)NC(=O)c1ccc2c(c1)N(C[C@@H]1CC[C@H]1[C@H](/C=C/CCC)O[Si](C)(C)C(C)(C)C)C[C@@]1(CCCc3nc(Cl)ccc31)CO2]

N,N-Dimethylpyridin-4-amine (DMAP) (23 mg, 0.19 mmol) was added to a solution of (S)-5-(((1R,2R)-2-((S,E)-1-((tert-butyldimethylsilyl)oxy)hex-2-en-1-yl)cyclobutyl)methyl)-2'-chloro-4,5,7',8'-tetrahydro-2H,6'H-spiro[benzo[b][1,4]oxazepine-3,5'-quinoline]-7-carboxylic acid (Example 798, Step 15) (60 mg, 0.096 mmol), (R)-hex-5-ene-2-sulfonamide (55 mg, 0.34 mmol) and DIEA (0.067 mL, 0.3844 mmol) in DCM (3.0 mL). Then N-(3-dimethylamino propyl)-N'-ethylcarbodiimide hydrochloride (147 mg, 0.768 mmol) was added and it was stirred at r.t.

overnight. After concentration the residue was loaded on a 4 g ISCO Gold column and eluted with 0% to 20% EtOAc (containing 0.3% AcOH)/hexane (containing 0.3% AcOH) to provide the title compound (67 mg, 0.087 mmol, 91% yield).

Step 2: (S)-2'-chloro-N—((R)-HEX-5-en-2-ylsulfonyl)-5-(((1R,2R)-2-((S,E)-1-hydroxyhex-2-en-1-yl)cyclobutyl)methyl)-4,5,7',8'-tetrahydro-2H,6'H-spiro[benzo[b][1,4]oxazepine-3,5'-quinoline]-7-carboxamide

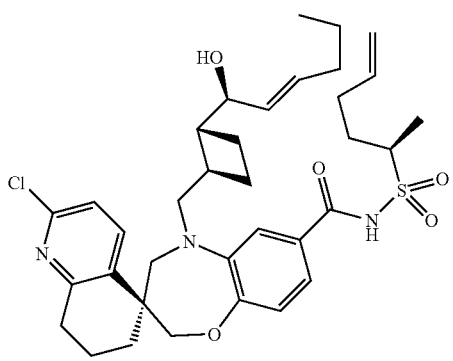 [SMILES: C=CCC[C@@H](C)S(=O)(=O)NC(=O)c1ccc2c(c1)N(C[C@@H]1CC[C@H]1[C@@H](O)/C=C/CCC)C[C@@]1(CCCc3nc(Cl)ccc31)CO2]

To a solution of (S)-5-(((1R,2R)-2-4S,E)-1-((tert-butyldimethylsilyl)oxy)hex-2-en-1-yl)cyclobutyl)methyl)-2'-chloro-N—((R)-hex-5-en-2-ylsulfonyl)-4,5,7',8'-tetrahydro-2H,6'H-spiro[benzo[b][1,4]oxazepine-3,5'-quinoline]-7-carboxamide (Example 791, Step 1) (67 mg, 0.087 mmol) in DCM (2.0 mL) was added tetrabutylammonium fluoride, 1.0 M solution in tetrahydrofuran (0.057 mL, 0.217 mmol) and small amount of moleculer sieve 4A. The mixture was stirred at 55° C. for 40 h. It was concentrated and the residue was purified by reverse phase preparatory HPLC (Gemini™ Prep C$_{18}$ 5 µm column; Phenomenex, Torrance, CA; MeCN in water with 0.1% TFA, gradient elution) to give the title compound (56 mg, 0.085 mmol, 98% yield).

Step 3: (3R,6R,7S,8E,12R,22S)-2'-chloro-7-hydroxy-12-methyl-7',8'-dihydro-6'H,15H-spiro[20-oxa-13-thia-1,14-diazatetracyclo[14.7.2.0$^{3,6}$.0$^{19,24}$]pentacosa-8,16,18,24-tetraene-22,5'-quinolin]-15-one 13,13-dioxide A 50 mL round bottom flask was charged with (S)-2'-chloro-N—((R)-hex-5-en-2-ylsulfonyl)-5-(((1R,2R)-2-((S,E)-1-hydroxyhex-2-en-1-yl)cyclobutyl)methyl)-4,5,7',8'-tetrahydro-2H,6'H-spiro[benzo[b][1,4]oxazepine-3,5'-quinoline]-7-carboxamide (Example 791, Step 2) (56 mg, 0.085 mmol) and Hoveyda-Grubbs II (21 mg, 0.034 mmol) and AcOH (43 mL). The mixture was stirred at r.t. for 36 h under vacuum. SiliaMet DMT (0.5 g, 0.62 mmol/g) was added to the reaction mixture and it was stirred at r.t. for 30 min. After concentration the residue was loaded on a 4 g ISCO Gold column and eluted with 0% to 60% EtOAc (containing 0.3% AcOH)/hexane (containing 0.3% AcOH) to provide the title compound (20 mg, 0.034 mmol, 40% yield). $^1$H NMR (500 MHz, CD$_3$CN) δ 8.09-8.05 (m, 1H), 7.26-7.20 (m, 1H), 7.02-6.97 (m, 1H), 6.92-6.88 (m, 1H), 6.87-6.84 (m, 1H), 5.74-5.66 (m, 1H), 5.50-5.46 (m, 1H), 4.48-4.43 (m, 1H), 4.10-4.02 (m, 3H), 3.80 (d, J=14.9 Hz, 1H), 3.66-3.61 (m, 1H), 3.31-3.25 (m, 3H), 3.05 (dd, J=10.1, 15.3 Hz, 1H), 2.96 (dd, 6.5 Hz, 1H), 2.90-2.76 (m, 2H), 2.38-1.61 (m, 10H), 1.55-1.48 (m, 2H), 1.46-1.42 (m, 3H). m/z (ESI, +ve ion) 586.2 (M+H)+.

Example 793. (1S,3'R,6'R,7'S,8'E,11R,13'R)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E,11'S,13'S)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E,11'S,13'R)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E,11'R,13'S)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide

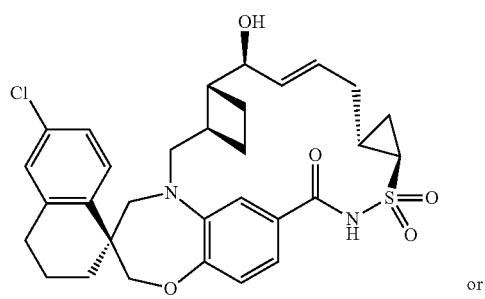

or

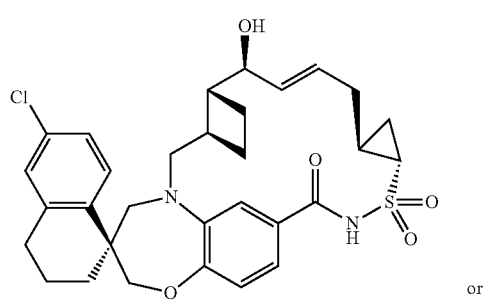

or

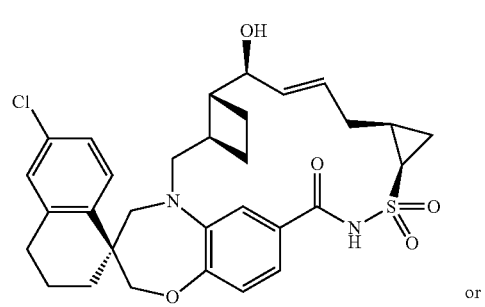

or

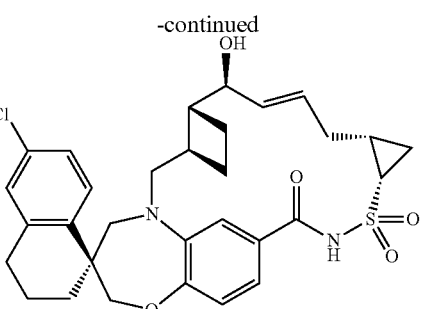

Step 1: 2-allyl-1,1-dibromocyclopropane

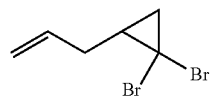

To a solution of 1,4-pentadiene (7.6 mL, 73 mmol), bromoform (7.1 mL, 81 mmol) and benzenemethanaminium N,N,N-triethyl chloride (1.67 g, 7.3 mmol) in DCM (60 mL) and pentane (60 mL) was slowly added sodium hydroxide (29.4 g, 734 mmol) solution in water (29.1 mL) at 0° C. The ice bath was removed after the addition. The reactiom mixture was stirred at r.t. overnight. The solid was filtered off and the filtrated was extracted with ether (80 ml). The organic phase was washed with brine, dried over anhydrous magnesium sulfate. The solvent was removed and disttilled under reduced prerssure to give the tittle compounds, 2-allyl-1,1-dibromocyclopropane (7.1 g, 29.6 mmol) as an oil (bp 50-55° C./3-5 mmHg).

Step 2: 1-allyl-2-bromocyclopropane

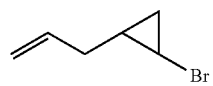

To 2-allyl-1,1-dibromocyclopropane (Example 793, Step 1) (2.6 g, 10.8 mmol) (containing 15% of bromoform) was added tributylstannane (2.96 mL, 10.8 mmol) at 0° C. during 40 min. The resulting mixture was stirred at r.t. over night. The reaction was monitored by NMR. Additional tributylstannane (1.0 mL) was added and it was stirred at r.t. until bromoform was completely consumed. The reaction mixture was directely disstilled under reduced pressure (b.p. 38-42° C./7-8 mmHg) to give the title product as an oil (0.5 g, 3.10 mmol).

Step 3: 1,2-di(pyrimidin-2-yl)disulfane

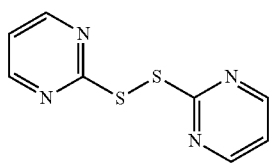 [SMILES: c1cnc(SSc2ncccn2)nc1]

To a solution of 2-mercapto-pyrimidine (2.0 g, 18 mmol) in acetonitril (80 mL) and water (16 mL) was added iodine (0.459 mL, 8.92 mmol). The resulting mixture was stirred at r.t. for 1 h. After concentration water was added and it was extracted with DCM (3×120 mL). The combined organic phase was washed with 30 mL of sodium thiosulfate (1 M), brine and dried over anhydrous MgSO$_4$. It was concentrated and the crude product was used for further reactions.

Step 4: 2-((2-allylcyclopropyl)thio)pyrimidine

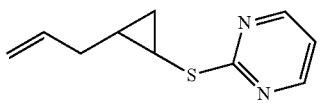

Magnesium (0.206 g, 8.47 mmol), which was washed with 0.1 N HCl (1 mL), MeOH (10×2 mL), ether (10 mL) and dried under vaccum, in THF (5.0 mL) was actived with a small amount of iodine and 1,2-dibromoethane (0.024 mL, 0.282 mmol) by sonication for 35 min. To this suspension was added one fifth amount of 1-allyl-2-bromocyclopropane (Example 793, Step 2) (1.0 g, 6.21 mmol) in THF (5.0 mL) at 50° C. during a period of 0.5 h. After the reaction occured, the rest of 1-allyl-2-bromocyclopropane was added dropwise at 20-30° C. and then it was stirred at r.t. for 1.5 h. The formed (2-allylcyclopropyl)magnesium bromide reagent was named Grignard A.

To a solution of 1,2-di(pyrimidin-2-yl)disulfane (Example 793, Step 3) (1.49 g, 6.71 mmol) in THF (10.0 mL) was slowly added (2-allylcyclopropyl)magnesium bromide (Grignard A) (1.13 g, 6.1 mmol) at 0° C. The resulting mixture was stirred at 0° C. for 12 min and then at r.t. for 1 h. The reaction was quenched by sat. NH$_4$Cl (10 mL). Water (20 mL) was added and it was extracted with ethyl acetate (3×40 mL), washed with brine, dried over anhydrous MgSO$_4$ and concentrated. The residue was loaded on a 4 g ISCO Gold column and eluted with 0% to 10% EtOAc/hexane to provide the title compound.

Step 5: 2-((2-allylcyclopropyl)sulfonyl)pyrimidine

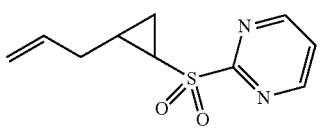

To a solution of 2-((2-allylcyclopropyl)thio)pyrimidine (Example 793, Step 4) (2.05 g, 10.7 mmol) in DCM (53 mL) was added 3-chloroperoxybenzoic acid, 77% max. (5.02 g, 22.39 mmol) in three portions at 0° C. during a period of about 15 min. The ice bath was then removed and the mixture was stirred at r.t. for 0.5 h. The reaction was then poured into ice and saturated sodium bicarbonate aqueous solution and extracted with DCM. The organic phase was washed with brine, dried over anhydrous MgSO$_4$ and concentrated. The residue was loaded on a 40 g ISCO Gold column and eluted with 0% to 70% EtOAc/hexane to provide the title compound (1.26 g, 52.7% yield).

Step 6: Sodium 2-allylcyclopropane-1-sulfinate

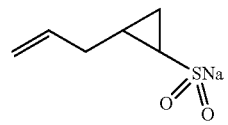

To a stirred solution of 2-((2-allylcyclopropyl)sulfonyl) pyrimidine (Example 793, Step 5) (0.8 g, 3.57 mmol) in MeOH (36 mL) was added sodium methoxide (0.82 ml, 3.6 mmol). The reaction was stirred at r.t. for 1.5 h. It was concentrated and then Et$_2$O was added. The precipitate was collected by filtration and the solid was washed with cold Et$_2$O and dried under vacuum to give the title product, which was used without futher purification in the next step.

Step 7: 2-allylcyclopropane-1-sulfonamide

A solution of sodium 2-allylcyclopropane-1-sulfinate (Example 793, Step 6) (0.59 g, 3.5 mmol) in water (23 mL) was treated with sodium acetate (0.432 g, 5.26 mmol) and hydroxylamine-o-sulfonic acid (0.529 g, 4.21 mmol). The mixture was stirred at 50° C. for 0.5 h and at r.t. for 1.5 h and then cooled to 0° C. It was basified with aqueous NaOH solution and extracted with EtOAc and then DCM. The organic phase was washed with brine, dried over anhydrous MgSO$_4$ and concentrated. The residue was loaded on a 12 g ISCO Gold column and eluted with 0% to 75% EtOAc/hexane to provide the title compound (0.56 g, 3.47 mmol, 99% yield).

Step 8: (S)—N-(((1R,2R)-2-allylcyclopropyl)sulfonyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide and (S)—N-(((1S,2S)-2-allylcyclopropyl)sulfonyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide and (S)—N-(((1S,2R)-2-allylcyclopropyl)sulfonyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide and (S)—N-(((1R,2S)-2-allylcyclopropyl)sulfonyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide

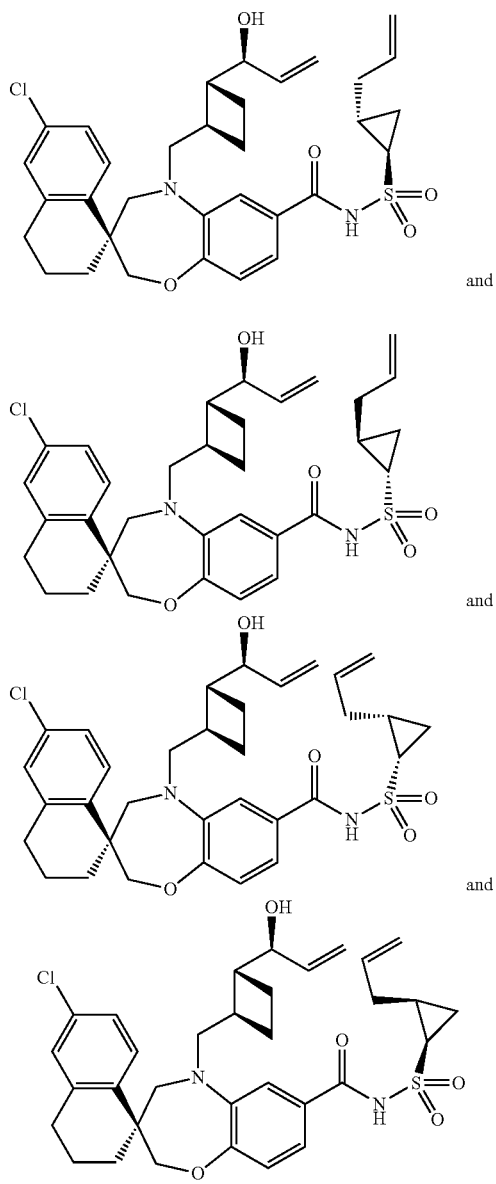

N,N-Dimethylpyridin-4-amine (DMAP) (52.2 mg, 0.427 mmol) was added to a solution of (S)-6'-chloro-5-(((1R,2R)-2-((S)-1-hydroxyallyl)cyclobutyl)methyl)-3',4,4',5-tetrahydro-2H,2'H-spiro [benzo[b][1,4]oxazepine-3,1'-naphthalene]-7-carboxylic acid (Intermediate AA11) (100 mg, 0.214 mmol), 2-allylcyclopropane-1-sulfonamide (Example 793, Step 7) and DIEA (0.149 ml, 0.855 mmol) in DCM (4.3 mL). Then N-(3-dimethylaminopropyl)-N'-ethylcarbodiimide hydrochloride (328 mg, 1.71 mmol) was added slowly. After the reaction mixture was stirred at r.t. overnight the reaction mixture was concentrated and the residue was loaded on a 12 g ISCO Gold column and eluted with 0% to 20% EtOAc (containing 0.3% HOAc)/hexane (containing 0.3% HOAc) to provide the title compound (112 mg, 0.183 mmol, 86% yield).

Step 9: (1S,3'R,6'R,7'S,8'E,11'R,13'R)-6-chloro-7'-hydroxy-3,4-dihydro-2H,16'H-spiro [naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E,11'S,13'S)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E,11'R,13'S)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E,11'S,13'R)-6-chloro-7'-hydroxy-3,4-dihydro-2H,16'H-spiro [naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide A 500 mL round bottom flask was charged with (S)—N—(((R)-2-allylcyclopropyl) sulfonyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide (Example 793, Step 8) (112 mg, 0.183 mmol), Hoveyda-Grubbs II (46 mg, 0.073 mmol) and AcOH (200 mL). The mixture was stirred at r.t. for about 36 h under house vacumm. Then SiliaMet DMT (1.0 g, 0.62 mmol/g) was added to the reaction mixture and stirred at r.t. for 30 min. The reaction mixture was concentrated and the residue was loaded on a 12 g ISCO Gold column and eluted with 0% to 40% EtOAc (containing 0.3% HOAc)/hexane (containing 0.3% HOAc) to provide a mixture of stereoisomers (59.1 mg, 0.101 mmol, 55% yield). The mixture of stereoisomers was purified by HPLC with chiral column (OJ) eluting with i-PrOH/hexane. The title compound (20.1 mg) was obtained as the first (faster) eluting isomer as a white solid $^1$H NMR (500 MHz, CD$_3$CN) δ 7.70 (d, J=8.6 Hz, 1H), 7.41 (br s, 1H), 7.21-7.09 (m, 3H), 6.82 (br s, 1H), 5.65-5.57 (m, 1H), 5.55-5.47 (m, 1H), 4.15-4.01 (m, 2H), 3.75-3.68 (m, 1H), 3.55 (br s, 1H), 3.44 (br s, 2H), 2.81-2.71 (m, 2H), 2.59 (d, J=11.2 Hz, 2H), 2.50-2.43 (m, 1H), 2.23-0.79 (m, 15H). m/z (ESI, +ve ion) 583.2 (M+H)$^+$.

Example 794. (1S,3'R,6'R,7'S,8'E,11'R,13'R)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E,11'S,13'S)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E,11'S,13'R)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E,11'R,13'S)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide

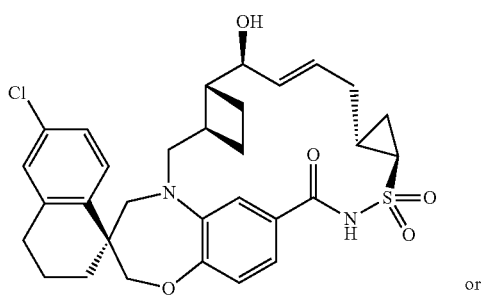

or

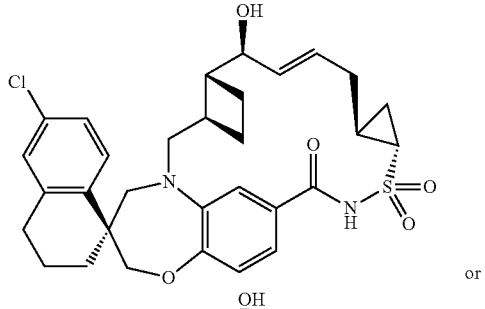

or

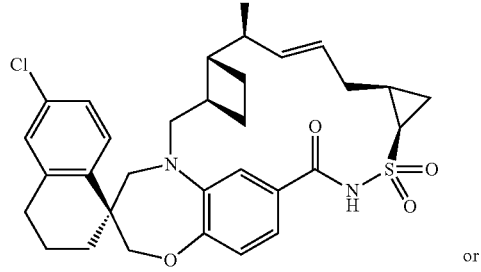

or

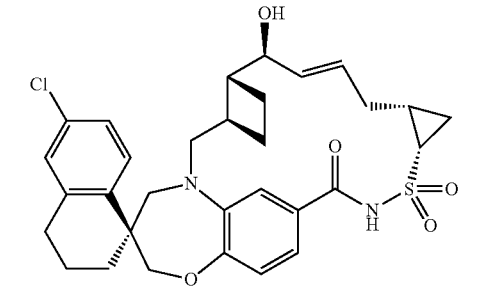

The title compound (3.7 mg) was obtained as the fourth (last) eluting isomer from Example 793 as a white solid. $^1$H NMR (500 MHz, CD$_3$OD) δ 7.74 (d, J=8.6 Hz, 1H), 7.45-7.35 (m, 2H), 7.18-7.15 (m, 1H), 7.13-7.12 (m, 1H), 6.87 (d, J=8.1 Hz, 1H), 5.80-5.73 (m, 1H), 5.57-5.49 (m, 1H), 4.27-4.22 (m, 1H), 4.14 (d, J=12.0 Hz, 1H), 3.74-3.67 (m, 1H), 3.63-3.56 (m, 2H), 3.55-3.50 (m, 1H), 3.23-3.10 (m, 2H), 2.90-2.76 (m, 3H), 2.70-2.54 (m, 3H), 2.15-2.08 (m, 1H), 1.99 (s, 1H), 1.94-1.87 (m, 2H), 1.86-1.70 (m, 3H), 1.59-1.50 (m, 1H), 1.31-1.23 (m, 3H). m/z (ESI, +ve ion) 583.2 (M+H)$^+$.

Example 795. (1S,3'R,6'R,7'S,8'E,11'R,13'R)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E,11'S,13'S)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E,11'S,13'R)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E,11'R,13'S)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide

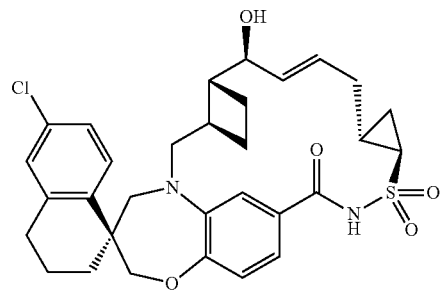

or

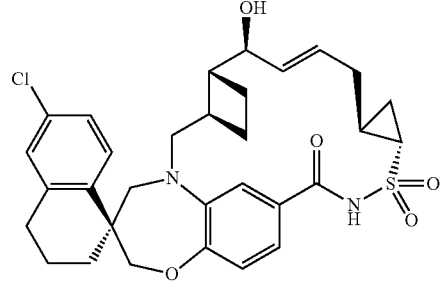

or

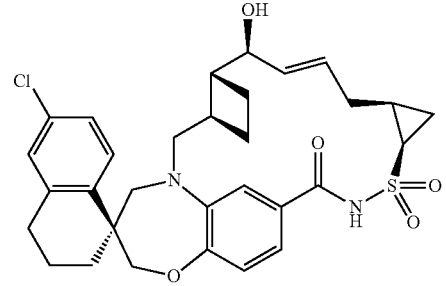

or

-continued

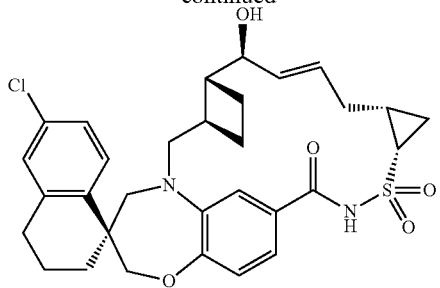

The title compound (3.5 mg) was obtained as the third eluting isomer from Example 793 as a white solid. $^1$H NMR (500 MHz, CD$_3$OD) δ 7.77-7.73 (m, 1H), 7.29-7.26 (m, 1H), 7.25-7.20 (m, 1H), 7.19-7.15 (m, 1H), 7.11-7.08 (m, 1H), 6.83-6.78 (m, 1H), 5.70-5.64 (m, 1H), 5.52-5.46 (m, 1H), 4.07-3.98 (m, 3H), 3.72-3.66 (m, 1H), 3.39 (d, J=14.4 Hz, 1H), 3.12 (dd, J=10.3, 15.2 Hz, 1H), 3.04 (d, J=5.4 Hz, 1H), 2.85-2.70 (m, 3H), 2.66-2.57 (m, 1H), 2.44-2.37 (m, 1H), 2.35-2.27 (m, 1H), 2.16-2.10 (m, 1H), 2.03-1.83 (m, 5H), 1.81-1.72 (m, 1H), 1.47-1.39 (m, 1H), 1.35-1.27 (m, 2H), 1.26-1.17 (m, 2H). m/z (ESI, +ve ion) 583.2 (M+H)$^+$.

Example 796. (1S,3'R,6'R,7'S,8'E,11'R,13'R)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E, 11'S,13'S)-6-chloro-7'-hydroxy-3,4-dihydro-2H, 16'H-spiro[naphthalene-1,23'-[21]oxa[14]thia[1,15] diazapentacyclo [15.7.2.0$^{3,6}$.0$^{11,13}$.0$^{20,25}$]hexacosa [8,17,19,25]tetraen]-16'-one 14',14'-dioxide or (1S, 3'R,6'R,7'S,8'E,11'S,13'R)-6-chloro-7'-hydroxy-3,4-dihydro-2H,16'H-spiro[naphthalene-1,23'-[21]oxa [14]thia[1,15]diazapentacyclo [15.7.2.0$^{3,6}$.0$^{11,13}$. 0$^{20,25}$]hexacosa[8,17,19,25]tetraen]-16'-one 14',14'-dioxide or (1S,3'R,6'R,7'S,8'E,11'R,13'S)-6-chloro-7'-hydroxy-3,4-dihydro-2H,16'H-spiro[naphthalene-1,23'-[21]oxa[14]thia[1,15]diazapentacyclo [15.7.2.0$^{3,6}$.0$^{11,13}$.0$^{20,25}$]hexacosa[8,17,19,25]tetraen]-16'-one 14',14'-dioxide

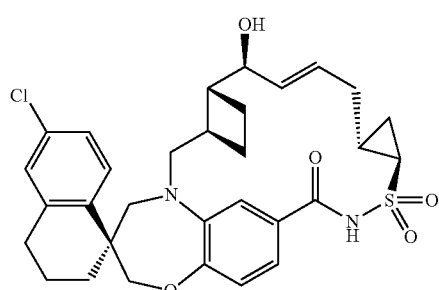

or

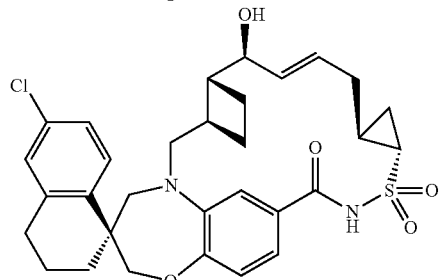

or

-continued

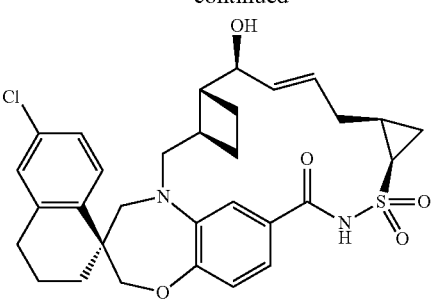

or

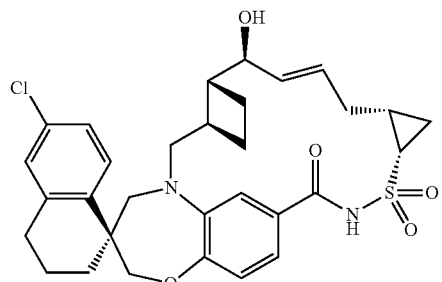

The title compound (12.1 mg) was obtained as the second eluting isomer from Example 793 as a white solid. $^1$H NMR (500 MHz, CD$_3$OD) δ 7.74 (d, J=8.6 Hz, 1H), 7.48 (br s, 1H), 7.40 (d, J=7.3 Hz, 1H), 7.16 (dd, J=2.4, 8.6 Hz, 1H), 7.13-7.10 (m, 1H), 6.84 (d, J=8.1 Hz, 1H), 5.70-5.62 (m, 1H), 5.56-5.48 (m, 1H), 4.23 (d, J=12.0 Hz, 1H), 4.08 (d, J=11.7 Hz, 1H), 3.60 (d, J=11.0 Hz, 3H), 3.46-3.39 (m, 1H), 3.26-3.17 (m, 1H), 2.90-2.74 (m, 4H), 2.68-2.60 (m, 2H), 2.18-2.09 (m, 1H), 2.04-1.98 (m, 1H), 1.91 (br s, 4H), 1.73-1.64 (m, 1H), 1.61-1.53 (m, 1H), 1.48-1.43 (m, 1H), 1.42-1.29 (m, 3H), 0.97-0.88 (m, 1H). m/z (ESI, +ve ion) 583.2 (M+H)$^+$.

Example 798. (3R,6R,7S,8E,12R,22S)-2'-chloro-12-ethyl-7-hydroxy-7',8'-dihydro-6'H,15H-spiro[20-oxa-13-thia-1,14-diazatetracyclo[14.7.2.0$^{3,6}$.0$^{19,24}$] pentacosa-8,16,18,24-tetraene-22,5'-quinolin]-15-one 13,13-dioxide

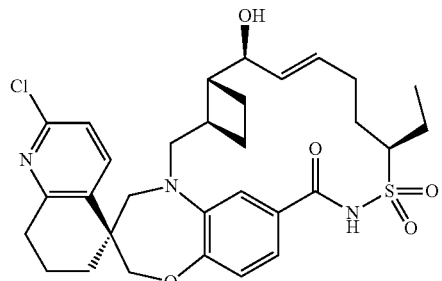

Step 1: 2-chloro-5,6,7,8-tetrahydroquinoline-5-carbaldehyde

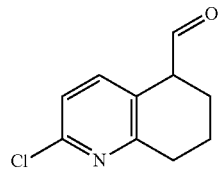 [SMILES: O=CC1CCCc2nc(Cl)ccc21]

To a stirred suspension of (methoxymethyl)triphenylphosphonium chloride (17.0 g, 49.6 mmol)) in THF (41 mL) was added slowly a solution of potassium 2-methylpropan-2-olate (41 mL, 41 mmol) at 0° C. via cannula under nitrogen. The resulting cherry-red solution was stirred at 0° C. for 1 h. A solution of 2-chloro-7,8-dihydroquinolin-5 (6H)-one (3.00 g, 16.5 mmol) in THF (10.0 mL) was added dropwaise. The reaction mixture was stirred at r.t. for 1 h. The reaction quenched with water (5 mL). It was concentrated at 35° C. to about 40 mL, then aqueous 30% $H_2SO_4$ (15 mL) was added at r.t. and it was stirred at 50° C. for 16 h. The reaction mixture was gradually poured into saturated sodium carbonate solution (70 mL) and ethyl acetate (100 mL). The aqueous layer was extracted with ethyl acetate (2×30 mL). The combined organic phases were washed with brine and dried over anhydrous $MgSO_4$. After concentration the residue was loaded on a 80 g ISCO Gold column and eluted with 0% to 90% EtOAc/hexane to provide the title compound (3.0 g, 15.3 mmol, 93% yield).

Step 2: 2'-chloro-7',8'-dihydro-6'H-spiro[[1,3]dioxane-5,5'-quinolin]-4-ol

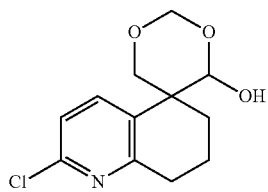 [SMILES: OC1OCOCC12CCCc1nc(Cl)ccc12]

To a reaction mixture of 2-chloro-5,6,7,8-tetrahydroquinoline-5-carbaldehyde (Example 798, Step 1) (3.0 g, 15.3 mmol) and formaldehyde (34.2 mL, 460 mmol) in DCM (77 mL) and MeOH (77 mL) was added sodium hydrogencarbonate (0.644 g, 7.67 mmol) in one portion. The resulting mixture was stirred at r.t. for 1 h. It was concentrated and extracted with ethyl acetate (100 mL). The organic phase was washed with brine and dried over anhydrous $MgSO_4$. It was concentrated to provide the title compound (3.90 g, 15.3 mmol, 99% yield) as a yellow oil which was used without further purification.

Step 3: 2'-chloro-7',8'-dihydro-6'H-spiro[[1,3]dioxane-5,5'-quinolin]-4-one

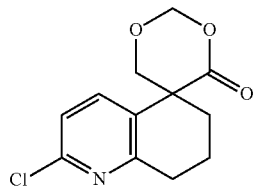 [SMILES: O=C1OCOCC12CCCc1nc(Cl)ccc12]

To a solution of 2'-chloro-7',8'-dihydro-6'H-spiro[[1,3]dioxane-5,5'-quinolin]-4-ol (Example 798, Step 2) (3.80 g, 14.8 mmol) in DCM (74 mL) was added Dess-Martin periodinane (9.45 g, 22.3 mmol) portionwise at 0° C. After it was stirred for 10 minutes, the cooling bath was removed. The mixture was stirred at r.t. for 1 h and then extracted with EtOAc. The organics were washed with 1 N sodium thiosulfate solution, saturated sodium bicarbonate solution, brine and dried over anhydrous $MgSO_4$. After concentration the residue was loaded on a 80 g ISCO Gold column and eluted with 0% to 30% EtOAc/hexane to provide the title compound (1.5 g, 5.91 mmol, 40% yield).

Step 4: 2-chloro-5-(hydroxymethyl)-5,6,7,8-tetrahydroquinoline-5-carboxylic Acid

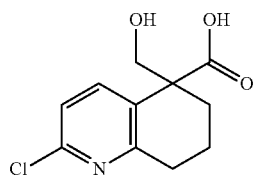 [SMILES: O=C(O)C1(CO)CCCc2nc(Cl)ccc21]

To a solution of 2'-chloro-7',8'-dihydro-6'H-spiro[[1,3]dioxane-5,5'-quinolin]-4-one (Example 798, Step 3) (1.50 g, 5.91 mmol) in THF (26 mL) and MeOH (13 mL) was added sodium hydroxide (23.6 mL, 47.3 mmol). The mixture was stirred at r.t. for 1 h. It was concentrated, acidified with 2N hydrochloric acid solution to pH=5 and extracted with EtOAc (80 mL). The combined organics were washed with brine, dried over anhydrous sodium sulfate. It was concentrated to afford the title compound (1.42 g, 5.88 mmol, 99% yield) as a pale yellow oil, which was used without further purification.

Step 5: methyl 2-chloro-5-(hydroxymethyl)-5,6,7,8-tetrahydroquinoline-5-carboxylate

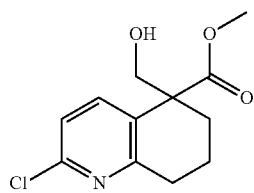 [SMILES: COC(=O)C1(CO)CCCc2nc(Cl)ccc21]

To a solution of 2-chloro-5-(hydroxymethyl)-5,6,7,8-tetrahydroquinoline-5-carboxylic acid (Example 798, Step 4) (1.4 g, 5.8 mmol) in MeOH (58 mL) and benzene (58 mL) was added slowly (trimethylsilyl)diazomethane, 2.0 M in diethyl ether (3.2 mL, 6.4 mmol). The reaction mixture was stirred at r.t. for 1 h. The reaction was quenched by addition of acetic acid (0.2 mL). After concentration the residue was loaded on a 40 g ISCO Gold column and eluted with 0% to 90% EtOAc/hexane to provide the title compound (1.48 g, 5.79 mmol, 100% yield).

Step 6: methyl 2-chloro-5-((4-(methoxycarbonyl)-2-nitrophenoxy) methyl)-5,6,7,8-tetrahydroquinoline-5-carboxylate

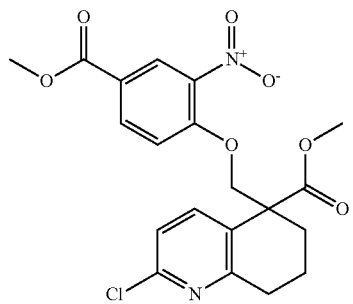

To a solution of methyl 2-chloro-5-(hydroxymethyl)-5,6,7,8-tetrahydroquinoline-5-carboxylate (Example 798, Step 5) (1.78 g, 7.0 mmol) in THF (26 mL) was added lithium bis(trimethylsilyl)amide (8.0 mL, 8.0 mmol). After the resulting mixture was stirred at r.t. for 20 min, methyl 4-fluoro-3-nitrobenzoate (1.66 g, 8.35 mmol) in THF (13 mL) was added. The resulting orange mixture was stirred at r.t. for 30 min. It was quenched with saturated ammonium chloride solution and extracted with EtOAc. The organics were washed with brine, dried (MgSO₄) and concentrated. The residue was loaded on a 40 g ISCO Gold column and eluted with 0% to 90% EtOAc/hexane to provide the title compound (3.05 g, 7.0 mmol, 100% yield).

Step 7: methyl 5-((2-amino-4-(methoxycarbonyl)phenoxy)methyl)-2-chloro-5,6,7,8-tetrahydroquinoline-5-carboxylate

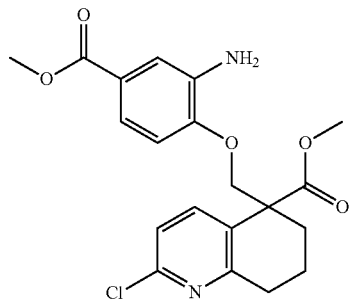

A 100 mL flask was charged with methyl 2-chloro-5-((4-(methoxycarbonyl)-2-nitrophenoxy)methyl)-5,6,7,8-tetrahydroquinoline-5-carboxylate (Example 798, Step 6) (3.2 g, 7.4 mmol), Acetic Acid (56 mL) and iron powder (4.11 g, 74 mmol). The mixture was stirred at 70° C. for 2.5 h. The reaction mixture was cooled to room temperature and filtered through celite and washed with EtOAc (100 mL). The filtrate was diluted with EtOAc (100 mL), washed with saturated aqueous sodium carbonate solution, brine and dried with over anhydrous sodium sulfate. It was concentrated to afford the title compound (3.0 g, 7.4 mmol, 100% yield), which was used without further purification.

Step 8: (Z)-methyl 2'-chloro-7',8'-dihydro-2H,6'H-spiro[benzo [b][1,4]oxazepine-3,5'-quinoline]-7-carboxylate

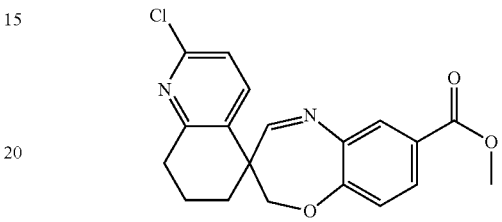

A 500 mL pear flask was charged with methyl 5-((2-amino-4-(methoxycarbonyl)phenoxy)methyl)-2-chloro-5,6,7,8-tetrahydroquinoline-5-carboxylate (Example 798, Step 7) (2.98 g, 7.36 mmol) and THF (74 mL) and it was cooled to −78° C. under nitrogen. To the cold solution was added dropwise lithium aluminum hydride, 2.0 M in THF (5.52 mL, 11.0 mmol). The resulting pale yellow solution was stirred for 10 minutes at −78° C. It was quenched carefully with MeOH (5.5 mL) (vigorous gas evolution) at the same temperature. The mixture was diluted with EtOAc (120 mL) and stirred over saturated aqueous Rochelle salt (50 mL) for 5 minutes. The organics were washed with brine and dried with over anhydrous sodium sulfate. It was concentrated to afford the title compound (2.63 g, 7.4 mmol, 100% yield) as a pale yellow oil, which was used without further purification.

Step 9: (S)-methyl 2'-chloro-4,5,7',8'-tetrahydro-2H,6'H-spiro[benzo[b][1,4]oxazepine-3,5'-quinoline]-7-carboxylate

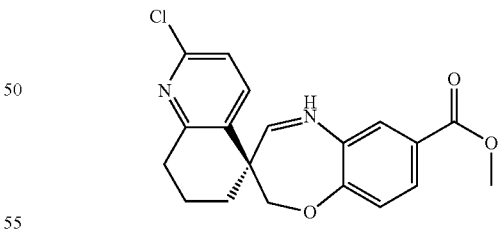

To a solution of (Z)-methyl 2'-chloro-7',8'-dihydro-2H,6'H-spiro[benzo[b][1,4]oxazepine-3,5'-quinoline]-7-carboxylate (Example 798, Step 8) (2.63 g, 7.37 mmol) and acetic acid (1.3 mL, 22 mmol) in DCE (61 mL) was added sodium triacetoxyborohydride (2.79 g, 14.7 mmol) at r.t. The resulting mixture was stirred at r.t overnight. Ethyl acetate (150 mL) was added and it was washed with sodium bicarbonate solution (2×40 mL), brine (40 mL), dried over Na₂SO₄ and concentrated. The residue was loaded on a 40 g ISCO Gold column and eluted with 0% to 85% EtOAc/hexane to give a racemic product, which was separated by Step 10: ((1R,2R)-2-((S,E)-1-hydroxyhex-2-en-1-yl)cyclobutyl)methyl benzoate

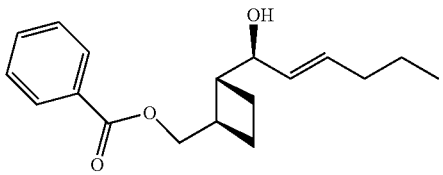 [SMILES: CCC/C=C/[C@H](O)[C@@H]1CC[C@H]1COC(=O)c1ccccc1]

A dry flask charged with dry hexane (14 mL) under nitrogen atmosphere was cooled to 0° C. (ice bath). Cyclohexene (2.8 mL, 27 mmol) was added and the mixture was stirred for 3 min. Then borane dimethyl sulfide complex (1.30 mL, 13.7 mmol) was added and it was stirred for 14 min. The reaction mixture was observed as a white suspension. To the white suspension was added n-propyl acetylene (1.36 mL, 13.7 mmol). The ice bath was removed and the reaction mixture was stirred at r.t. for 15 min. The mixture was cooled at −78° C. (dry ice bath) and diethylzinc, 1.0 M solution in heptane (13.7 mL, 13.7 mmol) was added. The cooling was switched to an ice bath (0° C.) and stirrd for 6 min (The solution became dark-grey). The solution was moved back to −78° C. bath. This solution was called solution A.
To a mixture of ((1R,2R)-2-formylcyclobutyl)methyl benzoate (Intermediate AA17, STEP 8) (1.00 g, 4.58 mmol), (2S)-3-exo-(morpholino)isobomeal (0.219 g, 0.916 mmol) in hexane (7.0 mL) and toluene (2.0 mL) at 0° C. was added 16 mL of solution A via syringe. After stirring at 0° C. for 3 min, the reaction was quenched with saturated NH$_4$Cl solution (15 mL), diluted with water (20 mL) and extracted with EtOAc. The organic phase was washed with brine, dried over Na$_2$SO$_4$ and concentrated. The residue was loaded on a 80 g ISCO Gold column and eluted with 0% to 20% EtOAc/hexane to give the title compound (0.56 g, 1.95 mmol, 43% yield).

Step 11: ((1R,2R)-2-((S,E)-1-((tert-butyldimethylsilyl)oxy)hex-2-en-1-yl)cyclobutyl)methyl benzoate

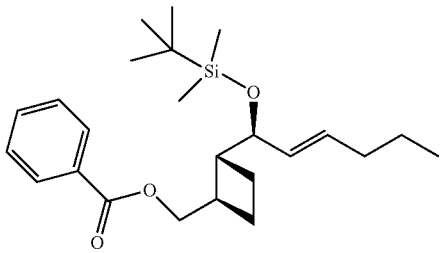 [SMILES: CCC/C=C/[C@H](O[Si](C)(C)C(C)(C)C)[C@@H]1CC[C@H]1COC(=O)c1ccccc1]

To a solution of ((1R,2R)-2-((S,E)-1-hydroxyhex-2-en-1-yl)cyclobutyl)methyl benzoate (Example 798, Step 10) (500 mg, 1.73 mmol) in DCM (12 mL) 0° C. (ice bath) under N$_2$ was added 2,6-dimethylpyridine (0.80 mL, 6.9 mmol) and followed by tert-butyldimethylsilyl trifluoromethanesulfonate (0.80 mL, 3.5 mmol). The mixture was stirred at 0° C. to r.t. overnight. The reaction was quenched with saturated NaHCO$_3$ solution, diluted with water and extracted with ethyl acetate. The organic phase was washed with citric acid (1.0 M, 2×20 mL), NaHCO$_3$ solution, brine and dried over MgSO$_4$ and concentrated. The residue was loaded on a 24 g ISCO Gold column and eluted with 0% to 20% EtOAc/hexane to give the title compound (0.56 g, 1.4 mmol, 80% yield).

Step 12: ((1R,2R)-2-((S,E)-1-((tert-butyldimethylsilyl)oxy)hex-2-en-1-yl)cyclobutyl)methanol

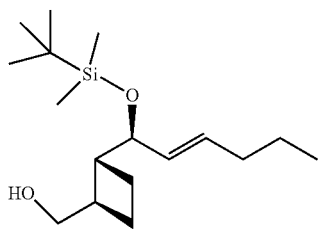

To a solution of ((1R,2R)-2-((S,E)-1-((tert-butyldimethylsilyl)oxy)hex-2-en-1-yl)cyclobutyl)methyl benzoate (Example 798, Step 11) (0.56 g, 1.4 mmol) in MeOH (5 mL) was added sodium methoxide (1.6 mL, 6.9 mmol). After stirring at r.t. for 2 h, the solution was treated with saturated NHCO$_3$ solution, diluted with water, and extracted with EtOAc (3×30 mL). The organic phase was washed with brine, dried over MgSO$_4$ and concentrated to give the title compound (0.40 g, 1.34 mmol, 96% yield).

Step 13: (1R,2R)-2-((S,E)-1-((tert-butyldimethylsilyl)oxy)hex-2-en-1-yl)cyclobutanecarbaldehyde

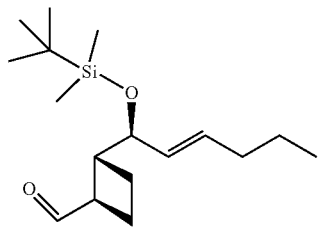 [SMILES: CCC/C=C/[C@H](O[Si](C)(C)C(C)(C)C)[C@@H]1CC[C@H]1C=O]

A solution of Dess Martin periodinane (0.852 g, 2.01 mmol) in DCM (2.5 mL) was added over 10 min to a solution of ((1R,2R)-2-((S,E)-1-((tert-butyldimethylsilyl)oxy)hex-2-en-1-yl)cyclobutyl)methanol (Example 798, Step 12) (0.4 g, 1.34 mmol) in DCM (2.5 mL). Water (0.024 mL, 1.34 mmol) in DCM (5 mL) was added dropwise over 5 min. The reaction was quenched with 20 mL of Dess-Martin Extractor (1:1 mixture of sat. NaHCO$_3$ solution/10% Na$_2$S$_2$O$_3$ solution). The mixture was stirred at r.t. for 15 min. The organic phase was washed with brine, dried over MgSO$_4$ and concentrated to afford the title compound (0.40 g, 1.34 mmol, 100% yield), which was used without futher purification.

Step 14: (S)-methyl 5-(((1R,2R)-2-((S,E)-1-((tert-butyldimethylsilyl)oxy) hex-2-en-1-yl)cyclobutyl)methyl)-2'-chloro-4,5,7',8'-tetrahydro-2H,6'H-spiro[benzo[b][1,4]oxazepine-3,5'-quinoline]-7-carboxylate

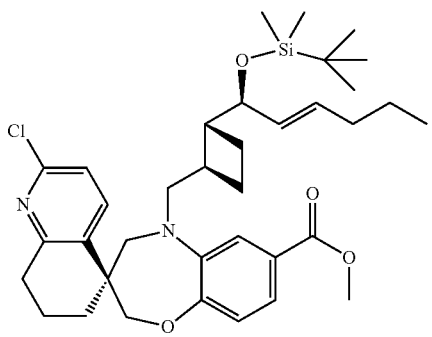 [SMILES: CCC/C=C/[C@H](O[Si](C)(C)C(C)(C)C)[C@@H]1CC[C@H]1CN1C[C@@]2(CCCc3nc(Cl)ccc32)COc2ccc(C(=O)OC)cc21]

A 10 mL of flask was charged with (S)-methyl 2'-chloro-4,5,7',8'-tetrahydro-2H,6'H-spiro[benzo[b][1,4]oxazepine-3,5'-quinoline]-7-carboxylate (Example 798, step 9) (101 mg, 0.281 mmol) and (1R,2R)-2-((S,E)-1-((tert-butyldimethylsilyl)oxy)hex-2-en-1-yl)cyclobutane carbaldehyde (Example 798, Step 13) (83 mg, 0.28 mmol) in DCM (2.8 mL). The reaction mixture was stirred at r.t. for 10 min and then sodium triacetoxyborohydride (179 mg, 0.844 mmol) was added. The mixture was stirred at r.t. for 20 min. Ethyl acetate (80 mL) was added. The mixture was washed with sodium bicarbonate solution (30 mL), brine (20 mL), dried over anhydrous MgSO$_4$ and concentrated. The residue was loaded on a 4 g ISCO Gold column and eluted with 0% to 80% EtOAc/hexane to give the title compound (150 mg, 0.235 mmol, 84% yield).

Step 15: (S)-5-(((1R,2R)-2-((S,E)-1-((tert-butyldimethylsilyl)oxy)hex-2-en-1-yl)cyclobutyl)methyl)-2'-chloro-4,5,7',8'-tetrahydro-2H,6'H-spiro[benzo[b][1,4]oxazepine-3,5'-quinoline]-7-carboxylic

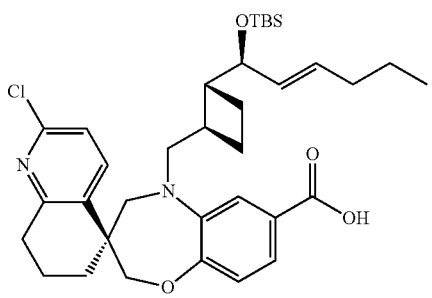 [SMILES: CCC/C=C/[C@H](O[Si](C)(C)C(C)(C)C)[C@@H]1CC[C@H]1CN1C[C@@]2(CCCc3nc(Cl)ccc32)COc2ccc(C(=O)O)cc21]

Lithium hydroxide solution (1.4 mL, 4.7 mmol) was added to a solution of (S)-methyl 5-(((1R,2R)-2-((S,E)-1-((tert-butyldimethylsilyl)oxy)hex-2-en-1-yl)cyclobutyl)methyl)-2'-chloro-4,5,7',8'-tetrahydro-2H,6'H-spiro[benzo[b][1,4]oxazepine-3,5'-quinoline]-7-carboxylate (Example 798, Step 14) (150 mg, 0.235 mmol) in MeOH (1.0 mL) and THF (2.0 mL). The resulting mixture was stirred at 40° C. for 24 h. The mixture was diluted with ethyl acetate (20 mL), washed with brine (pH-4, 10 mL), dried over anhydrous MgSO$_4$ and concentrated to provide the title compound (130 mg, 0.208 mmol, 89% yield).

Step 16: (S)-5-(((1R,2R)-2-((S,E)-1-((tert-butyldimethylsilyl)oxy)hex-2-en-1-yl)cyclobutyl)methyl)-2'-chloro-N—((R)-hept-6-en-3-ylsulfonyl)-4,5,7',8'-tetrahydro-2H,6'H-spiro[benzo[b][1,4]oxazepine-3,5'-quinoline]-7-carboxamide

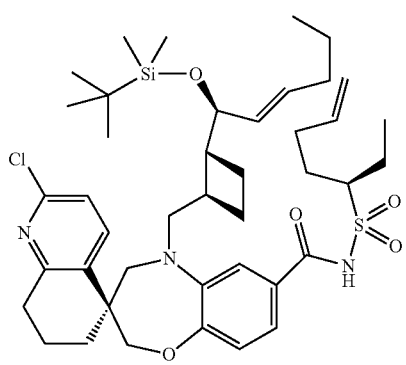 [SMILES: C=CCC[C@@H](CC)S(=O)(=O)NC(=O)c1ccc2c(c1)N(C[C@@H]1CC[C@H]1[C@H](/C=C/CCC)O[Si](C)(C)C(C)(C)C)C[C@@]1(CCCc3nc(Cl)ccc31)CO2]

N,N-Dimethylpyridin-4-amine (DMAP) (23 mg, 0.19 mmol) was added to a solution of Example 798, Step 15, (R)-hept-6-ene-3-sulfonamide (EE202) (59.5 mg, 0.336 mmol) and DIEA (0.067 mL, 0.384 mmol) in DCM (3 mL). Then N-(3-dimethylaminopropyl)-N'-ethylcarbodiimide hydrochloride (147 mg, 0.768 mmol) was added. After the reaction mixture was stirred at r.t. overnight it was concentrated. The residue was loaded on a 12 g ISCO Gold column and eluted with 0% to 20% EtOAc (containing 0.3% HOAc)/hexane (containing 0.3% HOAc) to provide the title compound (40 mg, 0.051 mmol, 53% yield).

Step 17: (S)-2'-chloro-N—((R)-hept-6-en-3-ylsulfonyl)-5-(((1R,2R)-2-((S,E)-1-hydroxyhex-2-en-1-yl)cyclobutyl)methyl)-4,5,7',8'-tetrahydro-2H,6'H-spiro[benzo[b][1,4]oxazepine-3,5'-quinoline]-7-carboxamide

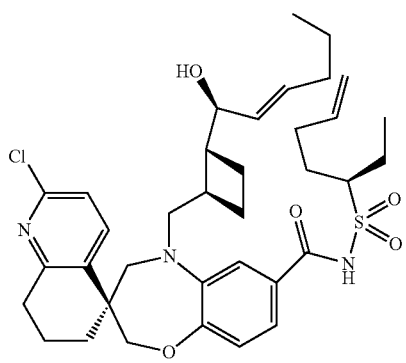 [SMILES: C=CCC[C@@H](CC)S(=O)(=O)NC(=O)c1ccc2c(c1)N(C[C@@H]1CC[C@H]1[C@@H](O)/C=C/CCC)C[C@@]1(CCCc3nc(Cl)ccc31)CO2]

To a solution of (S)-5-(((1R,2R)-2-((S,E)-1-((tert-butyldimethylsilyl)oxy)hex-2-en-1-yl)cyclobutyl)methyl)-2'-chloro-N—((R)-hept-6-en-3-ylsulfonyl)-4,5,7',8'-tetrahydro-2H,6'H-spiro[benzo[b][1,4]oxazepine-3,5'-quinoline]-7-carboxamide (Example 798, Step 16) (40 mg, 0.051 mmol) in DCM (2.0 mL) was added tetrabutylammonium fluoride, 1.0 M solution in THF (0.033 mL, 0.127 mmol) and small amount of 4A molecular sieve. The mixture was stirred at 55° C. for 36 h. It was concentrated and the residue was purified by reverse phase preparatory HPLC (Gemini™ Prep $C_{18}$ 5 µm column; Phenomenex, Torrance, CA; MeCN in water with 0.1% TFA, gradient elution) to give the title compound (34 mg, 0.051 mmol, 99% yield).

Step 18: (3R,6R,7S,8E,12R,22S)-2'-chloro-12-ethyl-7-hydroxy-7',8'-dihydro-6'H,15H-spiro[20-oxa-13-thia-1,14-diazatetracyclo[14.7.2.0$^{3,6}$.0$^{19,24}$]pentacosa-8,16,18,24-tetraene-22,5'-quinolin]-15-one 13,13-dioxide

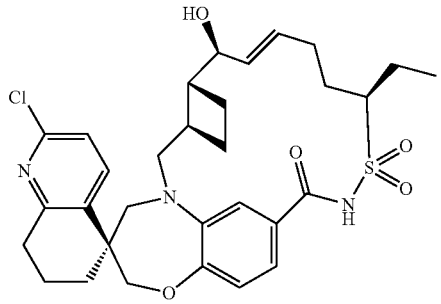 [SMILES: CC[C@@H]1CC/C=C/[C@H](O)[C@@H]2CC[C@H]2CN2C[C@@]3(CCCc4nc(Cl)ccc43)COc3ccc(cc32)C(=O)NS1(=O)=O]

A 50 mL round bottom flask was charged with (S)-2'-chloro-N—((R)-hept-6-en-3-ylsulfonyl)-5-(((1R,2R)-2-((S,E)-1-hydroxyhex-2-en-1-yl)cyclobutyl)methyl)-4,5,7',8'-tetrahydro-2H,6'H-spiro[benzo[b][1,4]oxazepine-3,5'-quinoline]-7-carboxamide (Example 798, Step 17) (34 mg, 0.051 mmol) and Hoveyda-Grubbs II (13 mg, 0.020 mmol) and AcOH (25 ml). The mixture was stirred at r.t for about 36 h under louse vacumm. SiliaMet DMT (0.25 g, 0.62 mmol/g) was added to the reaction mixture and it was stirred at r.t. for 30 min. It was concentrated and the residue was loaded on a 4 g ISCO Gold column and eluted with 0% to 60% EtOAc (containing 0.3% HOAc)/hexane (containing 0.3% HOAc) to provide the title compound (12 mg, 0.020 mmol, 39% yield). $^1$H NMR (500 MHz, CD$_3$CN) δ 8.07 (d, J=8.3 Hz, 1H), 7.22 (d, J=8.3 Hz, 1H), 7.01-6.97 (m, 1H), 6.91-6.88 (m, 1H), 6.87-6.84 (m, 1H), 5.75-5.69 (m, 1H), 5.68-5.63 (m, 1H), 4.11-4.01 (m, 3H), 3.96-3.89 (m, 1H), 3.80 (d, J=14.7 Hz, 1H), 3.63 (d, J=14.4 Hz, 1H), 3.28 (d, J=14.4 Hz, 1H), 3.05 (dd, J=10.0, 15.4 Hz, 1H), 2.91-2.84 (m, 1H), 2.84-2.75 (m, 1H), 2.60-2.54 (m, 1H), 2.42-1.87 (m, 10H), 1.84-1.67 (m, 5H), 1.47-1.39 (m, 1H), 1.13 (t, J=7.6 Hz, 3H). m/z (ESI, +ve ion) 600.2 (M+H)$^+$.

Example 801. (1S,3'R,6'R,7'S,8'E,10'R,12'S)-6-chloro-7'-hydroxy-3,4-dihydro-2H,16'H-spiro[naphthalene-1,23'-[21]oxa[14]thia[1,15]diazapentacyclo[15.7.2.0$^{3,6}$.0$^{10,12}$.0$^{20,25}$]hexacosa[8,17,19,25]tetraen]-16'-one 14',14'-dioxide or (1S,3'R,6'R,7'S,8'E,10'S,12'R)-6-chloro-7'-hydroxy-3,4-dihydro-2H,16'H-spiro[naphthalene-1,23'-[21]oxa[14]thia[1,15]diazapentacyclo[15.7.2.0$^{3,6}$.0$^{10,12}$.0$^{20,25}$]hexacosa[8,17,19,25]tetraen]-16'-one 14',14'-dioxide

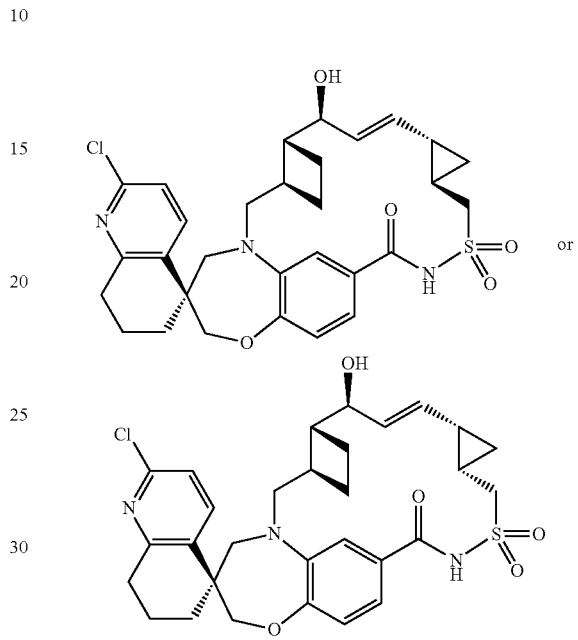

The title compound (1.3 mg) was obtained as a single isomer (second eluting peak) from the reverse phase preparative HPLC in Example 802 as a white solid. $^1$H NMR (500 MHz, CDCl$_3$) δ 7.76-7.67 (m, 1H), 7.57-7.45 (m, 1H), 7.23-7.16 (m, 2H), 7.12-7.07 (m, 1H), 7.02-6.94 (m, 1H), 5.83-5.65 (m, 1H), 5.63-5.39 (m, 1H), 4.15 (s, 2H), 3.88-3.72 (m, 1H), 3.68-3.53 (m, 1H), 3.48-3.32 (m, 1H), 3.27-3.06 (m, 1H), 2.82-2.69 (m, 2H), 2.35-2.21 (m, 2H), 2.16-0.65 (m, 16H). m/z (ESI, +ve ion) 583.2 (M+H)$^+$.

Example 802. (1S,3'R,6'R,7'S,8'E,10'R,12'S)-6-chloro-7'-hydroxy-3,4-dihydro-2H,16'H-spiro[naphthalene-1,23'-[21]oxa[14]thia[1,15]diazapentacyclo[15.7.2.0$^{3,6}$.0$^{10,12}$.0$^{20,25}$]hexacosa[8,17,19,25]tetraen]-16'-one 14',14'-dioxide or (1S,3'R,6'R,7'S,8'E,10'S,12'R)-6-chloro-7'-hydroxy-3,4-dihydro-2H,16'H-spiro[naphthalene-1,23'-[21]oxa[14]thia[1,15]diazapentacyclo[15.7.2.0$^{3,6}$.0$^{10,12}$.0$^{20,25}$]hexacosa[8,17,19,25]tetraen]-16'-one 14',14'-dioxide

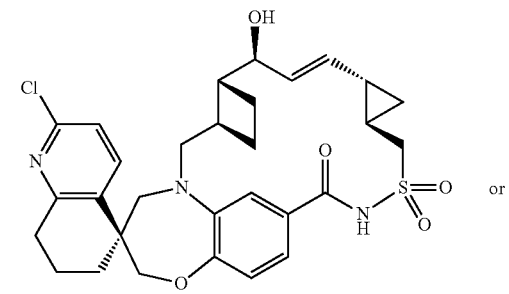

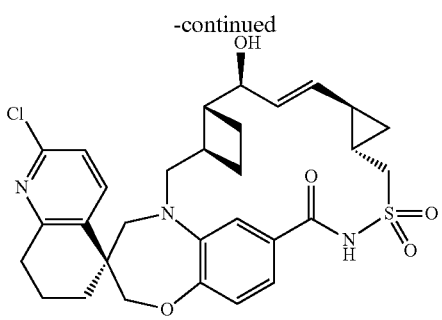

Step 1: ((1R,2S)-2-((E)-prop-1-en-1-yl)cyclopropyl)methanol and ((1S,2R)-2-((E)-prop-1-en-1-yl)cyclopropyl)methanol

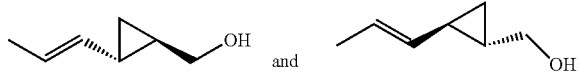

To a solution of diethylzine (1.0 M solution in hexane, 33.6 mL, 33.6 mmol) in DCM (61 mL) was added dropwise diiodomethane (5.4 mL, 67 mmol) at −10° C. After 15 min of stirring, a white precipitate was formed and a solution of (4R,5R)-(−)-2,2-dimethyl-α,α,α',α'-tetraphenyl-1,3-dioxolane-4,5-dimethaolato[1,2-bis(dimethoxy)ethane] titanium (IV)dichloride (1.09 g, 1.52 mmol) in DCM (8.0 mL) was added by cannula at −10° C. The solution was stirred at the same temperature for 5 min and a solution of (2E,4E)-hexa-2,4-dien-1-ol (3.0 g, 30.6 mmol) in DCM (61 mL) was added at −10° C. The resulting mixture was allowed to warm to 0° C. for 2 h with light exclusion. The reaction was quenched with 1.0 N HCl solution at −40° C. The mixture was extracted with DCM (2×30 mL) and the combined organic layers were washed with brine (20 mL), dried over anhydrous MgSO$_4$ and concentrated. The residue was loaded to a 40 g ISCO Gold column and eluted with 0% to 90% EtOAc/hexane to provide the title compound (2.2 g, 64% yield).

Step 2: 2-((((1R,2S)-2-((E)-prop-1-en-1-yl)cyclopropyl)methyl)thio)pyrimidine and 2-((((1S,2R)-2-((E)-prop-1-en-1-yl)cyclopropyl)methyl)thio)pyrimidine

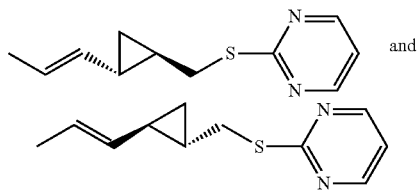

An oven-dried 25 mL flask was charged with triphenylphosphine (1.122 g, 4.28 mmol) in toluene (12 mL) under an atmosphere of nitrogen and then charged with (E)-diisopropyl diazene-1,2-dicarboxylate (0.84 ml, 4.3 mmol) in toluene (1 mL) at 0° C. It was added dropwise (E)-(2-(prop-1-en-1-yl)cyclopropyl)methanol (Example 802, Step 1; 0.4 g, 3.57 mmol) and stirred at 0° C. for 20 min. Then a solution of 2-mercapto-pyrimidine (0.480 g, 4.28 mmol) in THF (10 mL) was added slowly and it was stirred at rt for 5 h. It was concentrated and the residue was loaded to a 40 g ISCO Gold column and eluted with 0% to 90% EtOAc/hexane to provide the title compound (0.29 g, 1.41 mmol, 39% yield).

Step 3: 2-((((1R,2S)-2-((E)-prop-1-en-1-yl)cyclopropyl)methyl)sulfonyl)pyrimidine and 2-((((1S,2R)-2-((E)-prop-1-en-1-yl)cyclopropyl)methyl)sulfonyl)pyrimidine

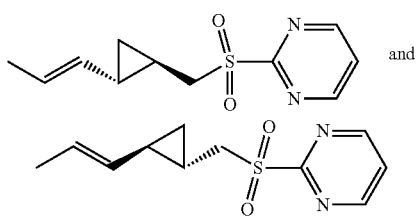

To a solution of (E)-2-(((2-(prop-1-en-1-yl)cyclopropyl)methyl)thio)pyrimidine (Example 802, Step 2; 0.63 g, 3.05 mmol) in DCM (15 mL) was added 3-chlorobenzoperoxoic acid (1.437 g, 6.41 mmol) in three portions at 0° C. during a period of 15 min. The ice bath was then removed and the mixture was stirred at rt for 3 h. The reaction was then poured into ice and saturated sodium bicarbonate solution. It was extracted with DCM (3×30 mL)) and the combined organic phases were washed with brine (10 mL), dried over anhydrous MgSO$_4$ and concentrated. The residue was loaded to a 80 g ISCO Gold column and eluted with 0% to 70% EtOAc/hexane to provide the title compound (0.043 g, 0.180 mmol, 6% yield).

Step 4: Sodium ((1R,2S)-2-((E)-prop-1-en-1-yl)cyclopropyl)methanesulfinate and SODIUM ((1S,2R)-2-((E)-prop-1-en-1-yl)cyclopropyl)methanesulfinate

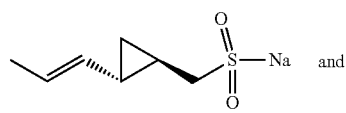

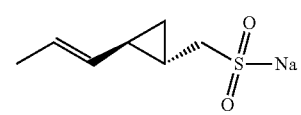

To a stirred solution of (E)-2-(((2-(prop-1-en-1-yl)cyclopropyl)methyl)sulfonyl)-pyrimidine (Example 802, Step 3; 43 mg, 0.18 mmol) in MeOH (1.8 mL) was added sodium methoxide (41.3 μl, 0.180 mmol). After the reaction was stirred at rt for 1.5 h it was concentrated evaporated and Et$_2$O was added. The solid was collected with filtration and purified by washing with cold Et$_2$O to give the title compound, which was used without further purification.

Step 5: ((1R,2S)-2-((E)-prop-1-en-1-yl)cyclopropyl)
methanesulfonamide and ((1S,2R)-2-((E)-prop-1-en-
1-yl)cyclopropyl)methanesulfonamide

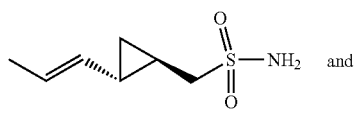

and

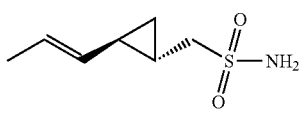

A solution of sodium (E)-(2-(prop-1-en-1-yl)cyclopropyl) methanesulfinate (Example 802, Step 4; 33 mg, 0.18 mmol) in water (1.2 mL) was treated with sodium acetate (22 mg, 0.27 mmol) and hydroxylamine-O-sulfonic acid (27 mg, 0.22 mmol). The reaction was stirred at 50° C. for 0.5 h and stirred at rt for 1.5 h. Then it was cooled to 0° C., basified with NaOH solution and extracted with DCM (2×40 mL). The combined organic phases were dried over anhydrous MgSO$_4$ and concentrated. The residue was loaded to a 12 g ISCO Gold column and eluted with 0% to 75% EtOAc/ hexane to provide the title compound (30 mg, 0.17 mmol, 95% yield).

Step 6: (S)-6'-chloro-5-(((1R,2R)-2-((S)-1-hydroxy-
allyl)cyclobutyl)methyl)-N-(((((1R,2S)-2-((E)-prop-
1-en-1-yl)cyclopropyl)methyl)sulfonyl)-3',4,4',5-
tetrahydro-2H,2'H-spiro[benzo[b][1,4]oxazepine-3,
1'-naphthalene]-7-carboxamide and (S)-6'-chloro-5-
(((1R,2R)-2-((S)-1-hydroxyallyl)cyclobutyl)methyl)-
N-((((1S,2R)-2-((E)-prop-1-en-1-yl)cyclopropyl)
methyl)sulfonyl)-3',4,4',5-tetrahydro-2H,2'H-spiro
[benzo[b][1,4]oxazepine-3,1'-naphthalene]-7-
carboxamide

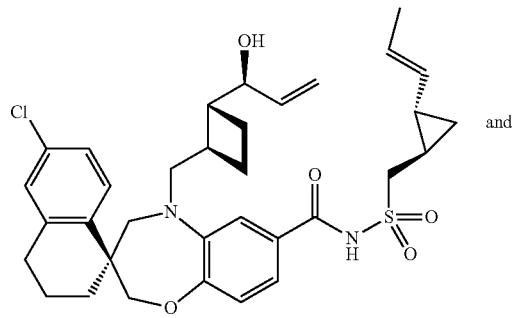

and

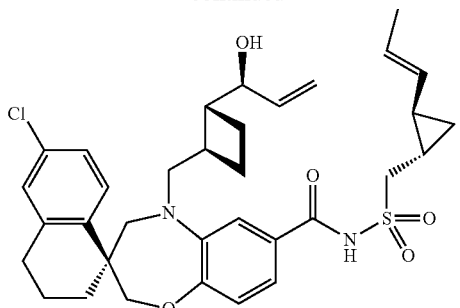

4-Pyrrolidinopyridine (22 mg, 0.15 mmol) was adde(S)-6'-chloro-5-(((1R,2R)-2-((S)-1-hydroxyallyl)cyclobutyl) methyl)-3',4,4',5-tetrahydro-2H,2'H-spiro[benzo[b][1,4] oxazepine-3,1'-naphthalene]-7-carboxylic acid (Intermediate AA11A; 70 mg, 0.15 mmol), Example 802, Step 5 (30 mg, 1.7 mmol) and DIEA (0.104 mL, 0.598 mmol) in DCM (1.3 ml). Then N-(3-dimethylaminopropyl)-N'-ethylcarbodiimide hydrochloride (143 mg, 0.748 mmol) was added slowly at 0° C. The reaction mixture was stirred at 0° C. overnight. After concentration the residue was loaded to a 12 g ISCO Gold column and eluted with 0% to 75% EtOAc (0.3% HOAc)/hexane (0.3% HOAc) to provide the title compound (35 mg, 0.056 mmol, 37% yield).

Step 7: (1S,3'R,6'R,7'S,8'E,10'R,12'S)-6-chloro-7'-
hydroxy-3,4-dihydro-2H,16'H-spiro[naphthalene-1,
23'-[21]oxa[14]thia[1,15]diazapentacyclo[15.7.2.
0$^{3,6}$.0$^{10,12}$.0$^{20,25}$]hexacosa[8,17,19,25]tetraen]-16'-
one 14',14'-dioxide or (1S,3'R,6'R,7'S,8'E,10'S,
12'R)-6-chloro-7'-hydroxy-3,4-dihydro-2H,16'H-
spiro[naphthalene-1,23'-[21]oxa[14]thia[1,15]
diazapentacyclo[15.7.2.0$^{3,6}$.0$^{10,12}$.0$^{20,25}$]hexacosa[8,
17,19,25]tetraen]-16'-one 14',14'-dioxide A 100 mL round bottom flask was charged with (1'S)-6'-chloro-5-(((1R,2R)-2-((S)-1-hydroxyallyl)cyclobutyl) methyl)-N-(((2-((E)-prop-1-en-1-yl)cyclopropyl)methyl) sulfonyl)-3',4,4',5-tetrahydro-2H,2'H-spiro[benzo[b][1,4] oxazepine-3,1'-naphthalene]-7-carboxamide (Example 802, Step 6; 35 mg, 0.056 mmol) and Hoveyda-Grubbs II (12 mg, 0.020 mmol) and DCE (28 mL). The reaction mixture was subjected to three cycles of evacuation/back-filling with nitrogen and heated at 60° C. for about 6 h under nitrogen. Then di(ethylene glycol) vinyl ether (3 mg, 0.022 mmol) was added and stirred at rt for 30 min. The reaction mixture was concentrated and the residue was loaded to a 12 g ISCO Gold column and eluted with 0% to 60% EtOAc (0.3% HOAc)/hexane (0.3% HOAc) to provide the title compound (3.9 mg, 6.7 μmol, 12% yield) as a single isomer (first eluting peak) as a white solid. $^1$H NMR (500 MHz, CD$_3$CN) δ 11.50 (s, 1H), 7.77-7.71 (m, 1H), 7.56-7.53 (m, 1H), 7.48-7.43 (m, 1H), 7.21-7.17 (m, 1H), 7.15-7.12 (m, 1H), 6.98-6.94 (m, 1H), 5.60-5.54 (m, 1H), 5.24-5.18 (m, 1H), 4.56-4.49 (m, 1H), 4.16-4.08 (m, 2H), 3.95-3.90 (m, 1H), 3.88-3.77 (m, 2H), 3.64-3.59 (m, 1H), 3.20-3.08 (m, 3H), 2.81-2.72 (m, 2H), 2.22-2.15 (m, 2H), 2.05-1.97 (m, 3H), 1.85 (br. s., 2H), 1.77-1.67 (m, 2H), 1.53-1.46 (m, 1H), 1.40-1.34 (m, 1H), 1.18-1.10 (m, 1H), 0.87-0.82 (m, 1H), 0.79-0.73 (m, 1H) m/z (ESI, +ve ion) 583.2 (M+H)$^+$.

Example 803. (1S,3'R,6'R,7'S,8'E,11'R,13'R)-6-chloro-7'-methoxy-3,4-dihydro-2H,16'H-spiro[naphthalene-1,23'-[21]oxa[14]thia[1,15]diazapentacyclo[15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E,11'S,13'S)-6-chloro-7'-methoxy-3,4-dihydro-2H,16'H-spiro[naphthalene-1,23'-[21]oxa[14]thia[1,15]diazapentacyclo[15.7.2.0$^{3,6}$.0$^{11,13}$.0$^{20,25}$]hexacosa[8,17,19,25]tetraen]-16'-one 14',14'-dioxide Example 804. (1S,3'R,6'R,7'S,8'E,11'S,13'S)-6-chloro-7'-methoxy-3,4-dihydro-2H,16'H-spiro[naphthalene-1,23'-[21]oxa[14]thia[1,15]diazapentacyclo[15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E,11'R,13'R)-6-chloro-7'-methoxy-3,4-dihydro-2H,16'H-spiro[naphthalene-1,23'-[21]oxa[14]thia[1,15]diazapentacyclo[15.7.2.0$^{3,6}$.0$^{11,13}$.0$^{20,25}$]hexacosa[8,17,19,25]tetraen]-16'-one 14',14'-dioxide

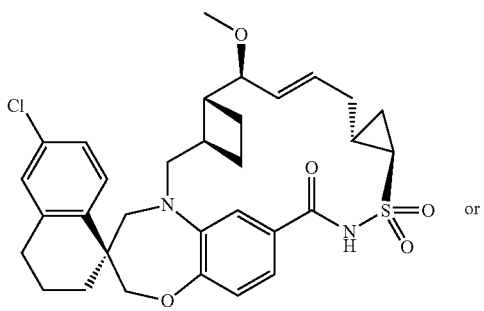 or

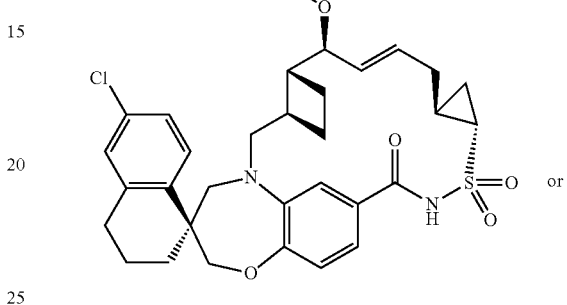 or

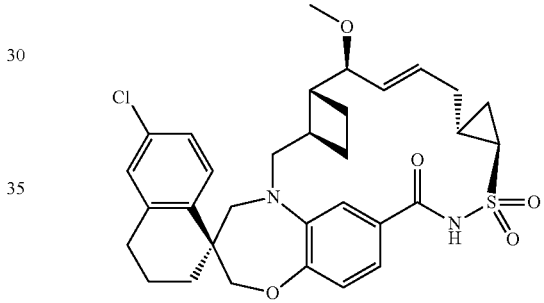

Sodium hydride (60% dispersion in mineral oil; 2.1 mg, 0.051 mmol) was added to a solution of Example 793 (6.0 mg, 10.3 μmol) in THF (1.0 mL) at 0° C. and it was stirred at the same temperature for 30 min. Then iodomethane (1.9 μL, 0.031 mmol) was added and then the reaction mixture was stirred at rt overnight. The reaction mixture was quenched with methanol (1 mL) and acidified with 1N HCl solution to pH 1-2. It was extracted with EtOAc (30 mL) and the organic phase was washed with brine, dried over anhydrous MgSO$_4$ and concentrated. The residue was purified by reverse phase preparatory HPLC (Gemini™ Prep C$_{18}$ 5 μm column; Phenomenex, Torrance, CA; MeCN in water with 0.1% TFA, gradient elution) to give the title compound (4.7 mg, 7.9 μmol, 77% yield) as a white solid. $^1$H NMR (500 MHz, CD$_3$CN) δ 9.37-9.31 (m, 1H), 7.71 (d, J=8.3 Hz, 1H), 7.21-7.18 (m, 1H), 7.17-7.13 (m, 2H), 7.08-7.04 (m, 1H), 6.92-6.88 (m, 1H), 5.68-5.60 (m, 1H), 5.44-5.37 (m, 1H), 4.17-4.05 (m, 2H), 3.64-3.59 (m, 1H), 3.54-3.47 (m, 1H), 3.42-3.34 (m, 2H), 3.28-3.23 (m, 1H), 3.04 (s, 3H), 2.80-2.74 (m, 3H), 2.73-2.69 (m, 2H), 2.59-2.55 (m, 1H), 2.52-2.48 (m, 1H), 2.07-2.01 (m, 1H), 1.88 (m, 8H), 1.42 (td, J=5.0, 9.7 Hz, 1H), 1.05-1.00 (m, 1H). m/z (ESI, +ve ion) 597.2 (M+H)$^+$.

Sodium hydride (60% dispersion in mineral oil; 2.3 mg, 0.057 mmol) was added to a solution of Example 796 (6.6 mg, 0.011 mmol) in THF (1.0 mL) at 0° C. and it was stirred at the same temperature for 30 min. Then iodomethane (2.1 μL, 0.034 mmol) was added and then the reaction mixture was stirred at rt overnight. The reaction mixture was quenched with methanol (1 mL) and acidified with 1N HCl solution to pH 1-2. It was extracted with EtOAc (30 mL) and the organic phase was washed with brine, dried over anhydrous MgSO$_4$ and concentrated. The residue was purified by reverse phase preparatory HPLC (Gemini™ Prep C$_{18}$ 5 μm column; Phenomenex, Torrance, CA; MeCN in water with 0.1% TFA, gradient elution) to give the title compound (6.3 mg, 10.6 μmol, 93% yield) as a white solid. $^1$H NMR (500 MHz, CD$_3$CN) δ 9.46-9.32 (m, 1H), 7.74-7.68 (m, 1H), 7.22-7.17 (m, 1H), 7.16-7.09 (m, 2H), 7.03-6.99 (m, 1H), 6.93-6.89 (m, 1H), 5.66-5.58 (m, 1H), 5.51-5.43 (m, 1H), 4.16-4.06 (m, 2H), 3.66-3.61 (m, 1H), 3.57-3.51 (m, 1H), 3.37-3.31 (m, 2H), 3.30-3.26 (m, 1H), 3.04 (s, 3H), 3.02-2.97 (m, 1H), 2.78-2.74 (m, 2H), 2.52-2.50 (m, 1H), 2.08-2.02 (m, 1H), 1.90-1.84 (m, 3H), 1.81-1.75 (m, 2H), 1.67-1.61 (m, 2H), 1.60-1.50 (m, 2H), 1.39-1.35 (m, 1H), 1.22 (d, J=3.7 Hz, 1H), 1.18-1.13 (m, 1H). m/z (ESI, +ve ion) 597.2 (M+H)$^+$.

Example 805. (1S,3'R,6'R,7'S,8'E,11'S,13'S)-6-chloro-7'-(2-methoxyethoxy)-3,4-dihydro-2H,16'H-spiro[naphthalene-1,23'-[21]oxa[14]thia[1,15]diazapentacyclo[15.7.2.0$^{3,6}$.0$^{11,13}$.0$^{20,25}$]hexacosa[8,17,19,25]tetraen]-16'-one 14',14'-dioxide or (1S,3'R,6'R,7'S,8'E,11'R,13'R)-6-chloro-7'-(2-methoxyethoxy)-3,4-dihydro-2H,16'H-spiro[naphthalene-1,23'-[21]oxa[14]thia[1,15]diazapentacyclo[15.7.2.0$^{3,6}$.0$^{11,13}$.0$^{20,25}$]hexacosa[8,17,19,25]tetraen]-16'-one 14',14'-dioxide

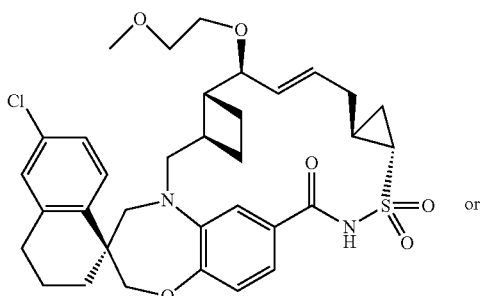

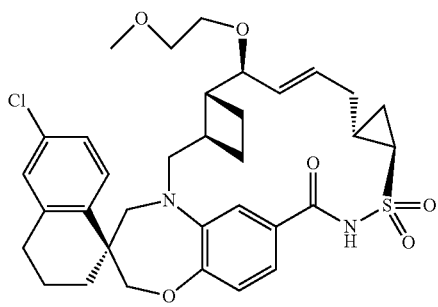

Sodium hydride (60% dispersion in mineral oil; 2.4 mg, 0.060 mmol) was added to a solution of Example 796 (7 mg, 0.012 mmol) in THF (1.0 mL) at 0° C. and it was stirred at this temperature for 30 min. Then 1-bromo-2-methoxyethane (3.38 μl, 0.036 mmol) was added slowly and it was stirred at rt overnight. The reaction mixture was quenched with water (15 mL) and acidified with 1N HCl solution to pH 1-2. It was extracted with EtOAc (30 mL) and the organic phase was washed with brine, dried over anhydrous MgSO$_4$ and concentrated. The residue was purified by reverse phase preparatory HPLC (Gemini™ Prep C$_{18}$ 5 μm column; Phenomenex, Torrance, CA; MeCN in water with 0.1% TFA, gradient elution) to give the title compound (1.2 mg, 1.8 μmol, 16% yield) as a white solid. $^1$H NMR (500 MHz, CD$_3$OD) δ 7.77-7.73 (m, 1H), 7.20-7.11 (m, 4H), 6.97-6.92 (m, 1H), 5.72-5.64 (m, 1H), 5.56-5.50 (m, 1H), 4.22-4.16 (m, 1H), 4.14-4.10 (m, 1H), 3.68 (d, J=14.7 Hz, 1H), 3.64-3.57 (m, 1H), 3.51 (dd, J=4.4, 8.1 Hz, 1H), 3.47-3.42 (m, 1H), 3.41-3.23 (m, 8H), 3.05 (td, J=4.3, 8.4 Hz, 1H), 2.87-2.75 (m, 3H), 2.65-2.53 (m, 2H), 2.14-2.08 (m, 1H), 2.03-1.97 (m, 1H), 1.94-1.88 (m, 2H), 1.86-1.79 (m, 1H), 1.72-1.65 (m, 2H), 1.64-1.54 (m, 2H), 1.51-1.43 (m, 2H), 1.22-1.18 (m, 1H). m/z (ESI, +ve ion) 641.2 (M+H)$^+$.

Example 807. (1S,3'R,6'R,7'S,9'Z)-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide

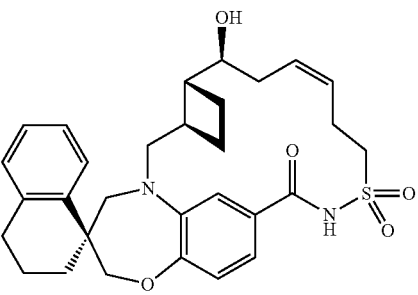

A mixture of (1S,3'R,6'R,7'S,9'Z)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (Example 834; 0.009 g, 0.016 mmol), 2-(di-tert-butylphosphino)biphenyl (0.94 mg, 3.15 μmol), palladium (II) acetate (0.3 mg, 1.5 μmol) and sodium formate (1.1 mg, 0.032 mmol) in MeOH (0.8 mL) was degassed by N$_2$. It was stirred at 72° C. for 16 h. The reaction mixture was filtered to get rid of the solid and the filtrate was concentrated. The residue was purified by reverse phase preparatory HPLC (Gemini™ Prep C$_{18}$ 5 μm column; Phenomenex, Torrance, CA; MeCN in water with 0.1% TFA, gradient elution) to give 3.6 mg of the title compound as a film. $^1$H NMR (400 MHz, CD$_2$Cl2) δ 10.88-10.21 (m, 1H), 7.73-7.61 (m, 1H), 7.45-7.27 (m, 2H), 7.23-7.05 (m, 3H), 6.99 (d, J=8.41 Hz, 1H), 5.63-5.51 (m, 1H), 5.48-5.37 (m, 1H), 4.36-4.27 (m, 1H), 4.23-4.15 (m, 1H), 3.91-3.81 (m, 1H), 3.73 (br. s., 1H), 3.64 (d, J=13.89 Hz, 1H), 3.50 (d, J=13.69 Hz, 1H), 3.32-3.12 (m, 2H), 2.78 (t, J=6.16 Hz, 2H), 2.62 (m, 2H), 2.37-2.15 (m, 3H), 1.91-1.50 (m, 11H). m/z (ESI, +ve ion) 537.2 (M+H)$^+$.

Example 808. (1S,3'R,6'R,7'S,10'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[10,16,18,24]tetraen]-15'-one 13',13'-dioxide

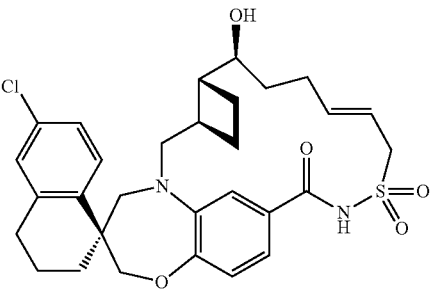

A 500 mL round bottom flask was charged with (1S,3'R,6'R,7'S,9'Z)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (Example 834; 0.142 g, 0.249 mmol) in toluene (210 mL). It was stirred at ambient temperature for 10 min to dissolve the solid starting material and then subjected to three cycles of evacuation/back-filling with nitrogen. To the homogeneous solution was added a solution of Hoveyda-Grubbs II (0.042 g, 0.050 mmol) in toluene (10 mL). After the mixture was stirred at 106° C. under nitrogen for 60 min it was concentrated. The residue was loaded to a 120 g ISCO Gold column and eluted with 0% to 20% EtOAc (containing 0.3% AcOH)/hexane (containing 0.3% AcOH). The third peak was collected and purified by SFC (Method: 250×21.2 mm IC—H column w/ 20 g/min MeOH (0.2% DEA)+60 g/min $CO_2$ on a Thar 80 SFC. Outlet pressure 100 bar; Temp. 20° C.; Wavelength 220 nm) to give the title compound (6.3 mg) as a white solid. $^1$H NMR (400 MHz, $CD_2Cl_2$) δ 7.72 (d, J=8.41 Hz, 1H), 7.42-7.36 (m, 1H), 7.22-7.14 (m, 2H), 7.11-7.07 (m, 1H), 6.98-6.93 (m, 1H), 6.16 (ddd, J=5.18, 10.03, 15.50 Hz, 1H), 5.65-5.53 (m, 1H), 4.16-4.04 (m, 2H), 3.95-3.87 (m, 1H), 3.87-3.79 (m, 1H), 3.67-3.60 (m, 1H), 3.52 (t, J=8.31 Hz, 1H), 3.15 (d, J=14.28 Hz, 1H), 3.06 (dd, J=8.51, 15.36 Hz, 1H), 2.80-2.72 (m, 2H), 2.44-2.52 (m, 1H), 2.25 (quin, J=8.85 Hz, 1H), 2.13-2.04 (m, 2H), 2.03-1.95 (m, 2H), 1.94-1.26 (m, 9H). m/z (ESI, +ve ion) 571.0 (M+H)$^+$.

Example 815. (3R,6S,22S)-6'-chloro-3',4'-dihydro-2'H,15H-spiro[10,20-dioxa-13-thia-1,14-diazatetracyclo[14.7.2.0$^{3,6}$.0$^{19,24}$]pentacosa-16,18,24-triene-22,1'-naphthalen]-15-one 13,13-dioxide

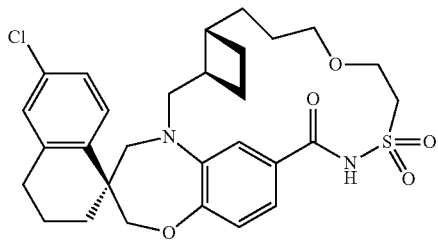

A 50 mL flask was charged with Example 826 (0.012 g, 0.022 mmol), EtOAc (21.5 mL) and platinum (IV) oxide (4.89 mg, 0.022 mmol) was added. The mixture was degassed by $N_2$ and was stirred at ambient temperature under hydrogen for 40 min. It was filtered through syringe filter to remove catalyst. The filtrate was concentrated and the residue was purified by SFC (Method: 250×21.2 mm IC—H column w/ 20 g/min MeOH (0.2% DEA)+60 g/min $CO_2$ on a Thar 80 SFC. Outlet pressure 100 bar; Temp. 20° C.; Wavelength 220 nm) to give the title compound (2.6 mg, second eluting peak) as a white solid. $^1$H NMR (400 MHz, $CD_2Cl_2$) δ 8.20-8.06 (m, 1H), 7.72 (m, 1H), 7.20-7.15 (m, 1H), 7.14-7.07 (m, 2H), 6.96 (s, 1H), 6.82 (m, 1H), 4.12-4.08 (m, 2H), 3.90-3.84 (m, 2H), 3.84-3.79 (m, 1H), 3.74-3.61 (m, 3H), 3.50-3.42 (m, 1H), 3.39-3.33 (m, 1H), 3.26 (d, J=14.28 Hz, 1H), 3.21-3.12 (m, 1H), 2.81-2.72 (m, 2H), 2.24-2.08 (m, 2H), 2.07-1.36 (m, 12H). m/z (ESI, +ve ion) 559.1 (M+H)$^+$.

Example 816. (3R,6S,22S)-5'-chloro-2',3'-dihydro-15H-spiro[10,20-dioxa-13-thia-1,14-diazatetracyclo[14.7.2.0$^{3,6}$.0$^{19,24}$]pentacosa-16,18,24-triene-22,1'-inden]-15-one 13,13-dioxide

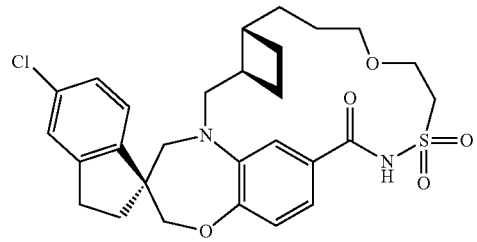

A 50 mL flask was charged with Example 817 (0.043 g, 0.079 mmol), EtOAc (26 mL). Platinum (IV) oxide (0.018 g, 0.079 mmol) was added and the mixture was degassed by $N_2$. It was stirred at ambient temperature under hydrogen for 65 min. It was filtered through syringe filter to remove catalyst. The filtrate was concentrated and the residue was purified by SFC (Method: 250×21.2 mm IC—H column w/ 20 g/min MeOH (0.2% DEA)+60 g/min $CO_2$ on a Thar 80 SFC. Outlet pressure 100 bar; Temp. 20° C.; Wavelength 220 nm). The title compound (17 mg) was obtained as a single isomer (second eluting peak) as a white solid. $^1$H NMR (400 MHz, $CD_2Cl_2$) δ 7.49-7.45 (m, 1H), 7.36-7.34 (m, 1H), 7.29-7.25 (m, 1H), 7.22-7.20 (m, 1H), 7.20-7.16 (m, 1H), 6.90-6.86 (m, 1H), 4.21-4.09 (m, 2H), 3.96 (td, J=6.53, 10.42 Hz, 1H), 3.89-3.82 (m, 1H), 3.71 (dd, J=2.93, 15.06 Hz, 1H), 3.61-3.51 (m, 2H), 3.48-3.32 (m, 4H), 3.21-3.15 (m, 2H), 3.01 (q, J=7.30 Hz, 4H), 2.96-2.87 (m, 1H), 2.35-2.25 (m, 1H), 2.23-2.15 (m, 1H), 2.05-1.94 (m, 1H), 1.93-1.80 (m, 3H), 1.68-1.55 (m, 1H), 1.53-1.26 (m, 2H). m/z (ESI, +ve ion) 545.0 (M+H)$^+$.

Example 817. (3R,6S,7E,22S)-5'-chloro-2',3'-dihydro-15H-spiro[10,20-dioxa-13-thia-1,14-diazatetracyclo[14.7.2.0$^{3,6}$.0$^{19,24}$]pentacosa-7,16,18,24-tetraene-22,1'-inden]-15-one 13,13-dioxide

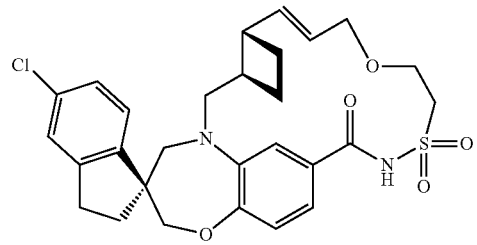

Step 1: 3-(2-bromoethoxy)prop-1-ene

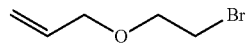

Perbromomethane (19.48 g, 58.7 mmol) was added to a solution of 2-(allyloxy)ethanol (5.0 g, 49.0 mmol) in DCM (190 mL). The resulting solution was cooled to 0° C. and triphenylphosphine (15.41 g, 58.7 mmol) was added. It was stirred at 0° C. to ambient temperature for 3 h. After concentration, the residue was loaded to a 80 g ISCO Gold column and eluted with 0% to 15% EtOAc/DCM to provide 4.14 g of the title compound as colorless oil. $^1$H NMR (400 MHz, DMSO-$d_6$) δ 5.89 (tdd, J=5.3, 10.5, 17.3 Hz, 1H), 5.29 (qd, J=1.8, 17.2 Hz, 1H), 5.21-5.11 (m, 1H), 4.01 (td, J=1.5, 5.3 Hz, 2H), 3.75-3.67 (m, 2H), 3.65-3.58 (m, 2H).

Step 2: Sodium 2-(allyloxy)ethanesulfonate

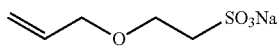

A mixture of 3-(2-bromoethoxy)prop-1-ene (Example 817, Step 1; 4.14 g, 25.09 mmol) and sodium sulfite (3.48 g, 27.6 mmol) in water (20 mL) was stirred at 110° C. for 4 h. After concentration, the residue was added acetone (10 mL) and stirred for a minute. The title compound (5.24 g) was collected as a white solid by filtration. $^1$H NMR (400 MHz, DMSO-$d_6$) δ 5.86 (tdd, J=5.4, 10.5, 17.2 Hz, 1H), 5.23 (qd, J=1.8, 17.2 Hz, 1H), 5.17-5.06 (m, 1H), 3.90 (td, J=1.6, 5.5 Hz, 2H), 3.67-3.51 (m, 2H), 2.75-2.63 (m, 2H).

Step 3: 2-(allyloxy)ethanesulfonamide

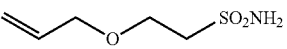

A mixture of sodium 2-(allyloxy)ethanesulfonate (Example 817, Step 2; 3.87 g, 20.57 mmol) and phosphorus oxychloride (54.6 mL, 596 mmol) was stirred at 130° C. for 4.6 h. It was concentrated by rotavapor. To the residue was added CH$_3$CN (32 mL) and stirred for 1 min. The mixture was filtered to remove the precipitate. NH$_3$ (30% aq.) (30 mL) was added slowly to the filtrate at 0° C. and it was stirred for 0.6 h. The reaction mixture was diluted with EtOAc (470 mL), washed with brine, dried over anhydrous sodium sulfate and concentrated. The residue was loaded to a 40 g ISCO Gold column and eluted with 0% to 15% EtOAc/hexane to provide 1.19 g of the title compound as a colorless oil. $^1$H NMR (400 MHz, DMSO-$d_6$) δ 6.72-6.91 (m, 2H), 5.81-5.95 (m, 1H), 5.27 (qd, J=1.74, 17.29 Hz, 1H), 5.22-5.34 (m, 1H), 5.10-5.21 (m, 1H), 3.97 (td, J=1.47, 5.48 Hz, 2H), 3.67-3.80 (m, 2H), 3.19-3.28 (m, 2H).

Step 4: ((1R,2R)-2-(((tetrahydro-2H-pyran-2-yl)oxy)methyl)cyclobutyl) methanol

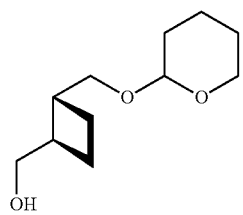

To a stirred solution of (1R,2R)-cyclobutane-1,2-diyldimethanol (1.5 g, 12.9 mmol) in dichloromethane (1.10 g, 12.9 mmol) at 23° C. was added 3,4-dihydro-2H-pyran (0.543 g, 6.46 mmol), followed by pyridine 4-methylbenzenesulfonate (0.325 g, 1.29 mmol). It was stirred at rt for 24 h. The mixture was concentrated to afford the title compound.

Step 5: (1R,2R)-2-(((tetrahydro-2H-pyran-2-yl)oxy)methyl)cyclobutanecarbaldehyde

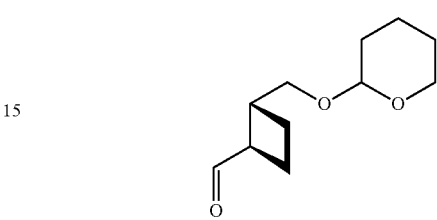

To a white slurry solution of iodobenzene diacetate (5.40 g, 16.8 mmol) and ((1S,2S)-2-(((tetrahydro-2H-pyran-2-yl)oxy)methyl)cyclobutyl)methanol (from Step 4, 2.80 g, 14.0 mmol) in DCM (7.0 ml) was added 2,2,6,6-Tetramethyl-1-piperidinyloxy, free radical, 2,2,6,6-Tetramethylpiperidine 1-oxyl (Tempo, 0.109 g, 0.699 mmol) in one portion at rt and then the mixture was vented to atmosphere and stirred at rt for 1.3 h. It was concentrated and the residue was loaded to a 80 g ISCO Gold column and eluted with 0% to 10% EtOAc/hexane to provide the title compound (0.806 g) as an oil.

Step 6: 2-(((1R,2S)-2-((E)-pent-1-en-1-yl)cyclobutyl)methoxy)tetrahydro-2H-pyran

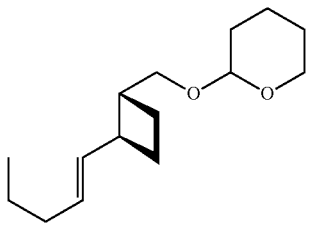

A solution of (butyl)triphenylphosphonium bromide (4.83 g, 12.1 mmol) in THF (50 ml) was cooled to 0° C. n-Butyllithium solution (2.5 M, in hexane, 5.33 ml, 13.3 mmol) was added dropwise and it was stirred at 0° C. for 22 min. (1S,2S)-2-(((tetrahydro-2H-pyran-2-yl)oxy)methyl)cyclobutanecarbaldehyde (Step 5, 0.800 g, 4.04 mmol) was added and it was stirred at 0° C. for 60 min. The reaction mixture was added to a stirred saturated NaHCO$_3$ solution (20 ml). The organic phase was separated and the aqueous was extracted with EtOAc (200 ml). The combined organics were dried (MgSO$_4$) and concentrated. It was concentrated and the residue was loaded to a 24 g ISCO Gold column and eluted with 0% to 5% EtOAc/hexane to provide the title compound (0.498 g) as a colorless oil.

Step 7: ((1R,2S)-2-((E)-pent-1-en-1-yl)cyclobutyl)methanol

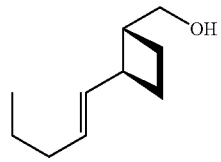

4-Methylbenzenesulfonic acid (0.071 g, 0.411 mmol) was added to a solution of 2-(((1S,2R)-2-((E)-pent-1-en-1-yl)cyclobutyl)methoxy)tetrahydro-2H-pyran (Step 6, 0.490 g, 2.056 mmol) in MeOH (29.4 ml). It was stirred at rt for 2 h. It was added saturated $Na_2CO_3$ solution (2 mL) and then concentrated. The residue was extracted with EtOAc (150 ml). The combined organics were dried over anhydrous sodium sulfate and filtered through a short plug of silica gel. The filtrate was concentrated to give the title compound, (0.268 g) as colorless oil.

Step 8: (1R,2S)-2-((E)-pent-1-en-1-yl)cyclobutanecarbaldehyde

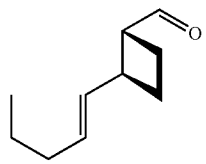

To a white slurry solution of iodobenzene diacetate (0.581 g, 1.80 mmol) and ((1S,2R)-2-((E)-pent-1-en-1-yl)cyclobutyl)methanol (Step 7, 0.265 g, 1.72 mmol) in DCM (0.86 ml) was added 2,2,6,6-Tetramethyl-1-piperidinyloxy, free radical, 2,2,6,6-Tetramethylpiperidine 1-oxyl (Tempo) (0.013 g, 0.086 mmol) in one portion. It was stirred at rt for 2 h. The mixture became a homogeneous, bright pale orange (1.6 M solution in DCM) and was used without work up.

Step 9: (S)-methyl 5'-chloro-5-(((1R,2S)-2-((E)-pent-1-en-1-yl)cyclobutyl)methyl)-2',3',4,5-tetrahydro-2H-spiro[benzo[b][1,4]oxazepine-3,1'-indene]-7-carboxylate

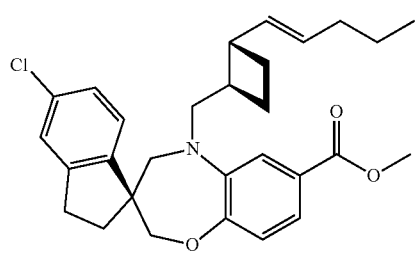

A screw-cap vial was charged with (S)-methyl 5'-chloro-2',3',4,5-tetrahydro-2H-spiro[benzo[b][1,4]oxazepine-3,1'-indene]-7-carboxylate (0.160 g, 0.465 mmol), (1S,2R)-2-((E)-pent-1-en-1-yl)cyclobutanecarbaldehyde (Step 8, 0.320 ml, 0.512 mmol) and acetic acid (0.53 ml, 9.3 mmol) in DCM (7.8 ml). The mixture was stirred at rt for 10 min. Sodium triacetoxyhydroborate (0.296 g, 1.39 mmol) was added in portions and the reaction was maintained at rt for 18 h. The reaction mixture was extracted with EtOAc (140 ml). The organic phase was washed with $Na_2CO_3$ solution and brine, dried over anhydrous sodium sulfate. It was concentrated and the residue was loaded to a 4 g ISCO Gold column and eluted with 0% to 10% EtOAc/hexane to provide the title compound (0.177 g) as a film.

Step 10: (S)—N-((2-(allyloxy)ethyl)sulfonyl)-5'-chloro-5-(((1R,2S)-2-((E)-pent-1-en-1-yl)cyclobutyl)methyl)-2',3',4,5-tetrahydro-2H-spiro[benzo[b][1,4]oxazepine-3,1'-indene]-7-carboxamide

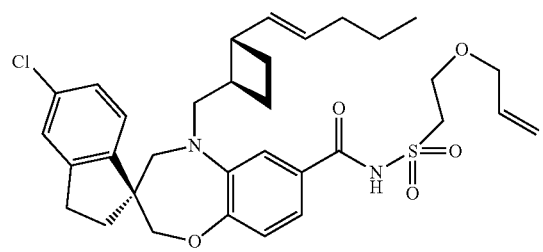

N-(3-Dimethylaminopropyl)-N'-ethylcarbodiimide hydrochloride (EDC; 0.097 g, 0.506 mmol) was added to a solution of (S)-5'-chloro-5-(((1S,2R)-2-((E)-pent-1-en-1-yl)cyclobutyl)methyl)-2',3',4,5-tetrahydro-2H-spiro[benzo[b][1,4]oxazepine-3,1'-indene]-7-carboxylic acid (Step 9; 0.118 g, 0.253 mmol) and 2-(allyloxy)ethanesulfonamide (Example 817, Step 3; 0.059 g, 0.354 mmol) in DCM (10 mL). Then N,N-dimethylpyridin-4-amine (DMAP) (0.062 g, 0.506 mmol) was added and it was stirred at ambient temperature for 15 h. The solution was concentrated and the residue was purified by reverse phase preparative HPLC (Gemini™ Prep $C_{18}$ 5 μm column; Phenomenex, Torrance, CA; MeCN in water with 0.1% TFA, gradient elution) to give 85 mg of the title compound as a film. m/z (ESI, +ve ion) 613.1 (M+H)⁺.

Step 11: (3R,6S,7E,22S)-5'-chloro-2',3'-dihydro-15H-spiro[10,20-dioxa-13-thia-1,14-diazatetracyclo[14.7.2.0³,⁶.0¹⁹,²⁴]pentacosa-7,16,18,24-tetraene-22,1'-inden]-15-one 13,13-dioxide

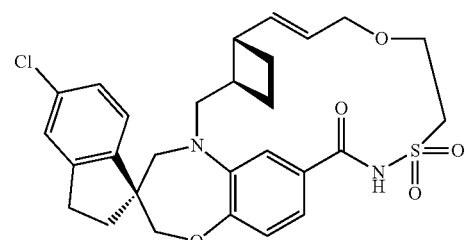

A 500 mL three-necked round bottom flask was charged with (S)—N-((2-(allyloxy)ethyl) sulfonyl)-5'-chloro-5-(((1S,2R)-2-((E)-pent-1-en-1-yl)cyclobutyl)methyl)-2',3',4,5-tetrahydro-2H-spiro[benzo[b][1,4]oxazepine-3,1'-indene]-7-carboxamide (Example 817, Step 10; 0.085 g, 0.139 mmol) in toluene (300 mL). It was stirred at ambient temperature for 10 min to dissolve the solid starting material and then subjected to three cycles of evacuation/back-filling with nitrogen. To the homogeneous solution was added a solution of Hoveyda-Grubbs II (0.017 g, 0.028 mmol) in toluene (5 mL). After the mixture was stirred at 107° C. under nitrogen for 1 h air was blown for 10 min to deactivate the catalyst, and then concentrated. The residue was purified by reverse phase preparative HPLC (Gemini™ Prep $C_8$ 5 μm column; Phenomenex, Torrance, CA; MeCN in water with 0.1% TFA, gradient elution) to give 57 mg of the title compound as a white solid. $^1$H NMR (400 MHz, $CD_2Cl_2$) δ 8.32-8.12 (m, 1H), 7.44-7.36 (m, 1H), 7.22 (s, 3H), 7.02-6.94 (m, 1H), 6.92-6.80 (m, 1H), 6.00-5.86 (m, 1H), 5.67-5.49 (m, 1H), 4.30-4.22 (m, 1H), 4.15 (m, 1H), 3.86-3.99 (m, 4H), 3.85-3.38 (m, 3H), 3.25 (dd, J=7.43, 15.45 Hz, 1H), 3.20-3.10 (m, 1H), 3.01-2.89 (m, 2H), 2.65-2.47 (m, 1H), 2.39-1.05 (m, 8H). m/z (ESI, +ve ion) 543.

Example 818. (1S,3'R,6'R)-6-chloro-3,4-dihydro-2H,14'H-spiro[naphthalene-1,21'-[19]oxa[12]thia[1,13]diazatetracyclo[13.7.2.0$^{3,6}$.0$^{18,23}$]tetracosa[15,17,23]trien]-14'-one 12',12'-dioxide

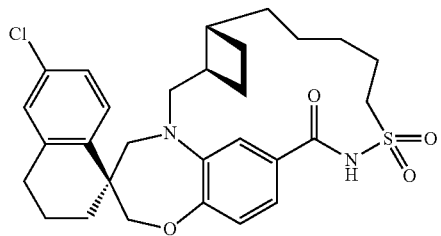

A 50 mL flask was charged with (1S,3'R,6'S, 7'E)-6-chloro-3,4-dihydro-2H,14'H-spiro [naphthalene-1,21'[19]oxa[12]thia[1,13]diazatetracyclo[13.7.2.0$^{3,6}$.0$^{18,23}$]tetracosa[7,15,17,23]tetraen]-14'-one 12',12'-dioxide (Example 829; 0.0046 g, 8.50 μmol), EtOAc (8.50 mL). It was added platinum (IV) oxide (1.93 mg, 8.5 μmol) and the mixture was degassed by $N_2$. After it was stirred at ambient temperature under hydrogen for 54 min it was filtered through syringe filter to remove catalyst. The filtrate was concentrated to give 4.4 mg of the title compound as a white solid. $^1$H NMR (400 MHz, $CD_2Cl_2$) δ 8.05 (br. s., 1H), 7.76-7.67 (m, 1H), 7.21-7.14 (m, 1H), 7.10 (dd, J=2.25, 4.99 Hz, 1H), 7.06-6.87 (m, 3H), 4.13-4.10 (m, 1H), 3.91-3.60 (m, 4H), 3.30-2.98 (m, 3H), 2.80-2.69 (m, 2H), 2.25-2.10 (m, 1H), 2.06-0.85 (m, 17H). m/z (ESI, +ve ion) 543.0 (M+H)$^+$.

Example 823. (1S,3'R,6'R)-3,4-dihydro-2H,14'H-spiro[naphthalene-1,21'-[19]oxa[12]thia[1,13]diazatetracyclo[13.7.2.0$^{3,6}$.0$^{18,23}$]tetracosa [15,17,23]trien]-14'-one 12',12'-dioxide

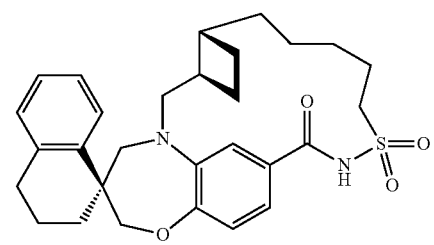

Under nitrogen atmosphere, 10% palladium on carbon (8 mg, 7.95 μmol) was added to a solution of Example 829 (0.0043 g, 8 μmol) in MeOH (8 mL). Then it was stirred at ambient temperature under $H_2$ for 90 min. The mixture was filtered through syringe filter to provide the title compound (3.6 mg) as a white solid. $^1$H NMR (400 MHz, $CD_2Cl_2$) δ 8.08-8.00 (m, 1H), 7.78-7.73 (m, 1H), 7.20-7.08 (m, 3H), 6.98 (s, 1H), 6.94-6.90 (m, 2H), 4.18-4.12 (m, 2H), 3.93-3.81 (m, 2H), 3.80-3.72 (m, 2H), 3.65 (br. s., 1H), 3.22 (d, J=14.48 Hz, 1H), 3.19-3.07 (m, 2H), 2.78 (dd, J=5.77, 9.49 Hz, 2H), 2.24-2.14 (m, 1H), 2.08-1.09 (m, 15H). m/z (ESI, +ve ion) 509.1 (M+H)$^+$.

Example 824. (3S,6R,22S)-3',4'-dihydro-2'H,15'H-spiro[10,20-dioxa-13-thia-1,14-diazatetracyclo[14.7.2.0$^{3,6}$.0$^{19,24}$]pentacosa-16,18,24-triene-22,1'-naphthalen]-15-one 13,13-dioxide

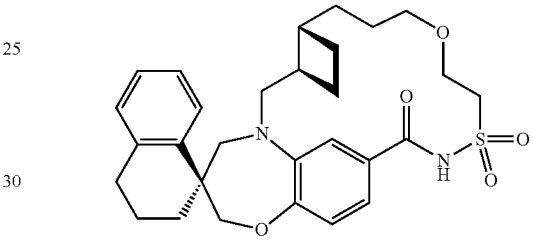

Under nitrogen atmosphere, 10% palladium on carbon (6 mg, 5.4 μmol) was added to a solution of (Example 826; 0.003 g, 5.4 μmol) in MeOH (5 mL). Then it was stirred at ambient temperature under $H_2$ for 3 h. It was filtered through syringe filter to afford the title compound (2.6 mg) as a white solid. $^1$H NMR (400 MHz, $CD_2Cl_2$) δ 8.14-8.10 (m, 1H), 7.76-7.72 (m, 1H), 7.22-7.15 (m, 2H), 7.12 (d, J=11.35 Hz, 2H), 6.97-6.94 (m, 1H), 6.84-6.79 (m, 1H), 4.14-4.10 (m, 3H), 3.90-3.84 (m, 3H), 3.79-3.75 (m, 1H), 3.68-3.63 (m, 3H), 3.48-3.45 (m, 1H), 3.38-3.34 (m, 1H), 3.29 (d, J=14.09 Hz, 2H), 3.23-3.17 (m, 1H), 2.79 (d, J=4.50 Hz, 2H), 2.21-1.25 (m, 11H). m/z (ESI, +ve ion) 525.2 (M+H)$^+$.

Example 825. (1S,3'R,6'S, 7'E)-6-chloro-3,4-dihydro-2H,13'H-spiro[naphthalene-1,20'-[18]oxa[11]thia[1,12]diazatetracyclo[12.7.2.0$^{3,6}$.0$^{17,22}$]tricosa[7,14,16,22]tetraen]-13'-one 11',11'-dioxide

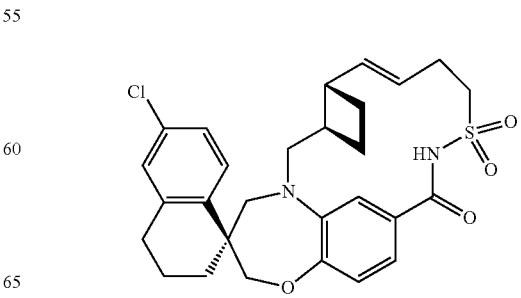

Step 1: (S)-methyl 6'-chloro-5-(((1R,2S)-2-((E)-pent-1-en-1-yl)cyclobutyl)methyl)-3',4,4',5-tetrahydro-2H,2'H-spiro[benzo[b][1,4]oxazepine-3,1'-naphthalene]-7-carboxylate

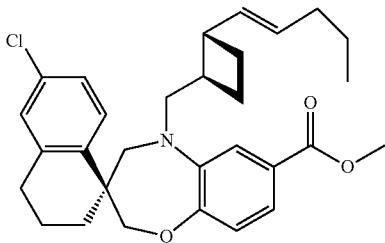

A screw-cap vial was charged with (S)-methyl 6'-chloro-3',4,4',5-tetrahydro-2H,2'H-spiro[benzo [b][1,4]oxazepine-3,1'-naphthalene]-7-carboxylate (Intermediate AA11A, Step 12A; 0.190 g, 0.53 mmol), (1S,2R)-2-((E)-pent-1-en-1-yl)cyclobutanecarbaldehyde (Example 817, Step 5; 0.43 ml, 0.69 mmol) and acetic acid (0.61 ml, 10.6 mmol) in DCM (8.8 ml). After the mixture was stirred at rt for 14 min, sodium triacetoxyhydroborate (0.563 g, 2.65 mmol) was added in portions and the reaction was maintained at rt for 15 h. The reaction mixture was extracted with EtOAc (140 mL). The organic phase was washed with $Na_2CO_3$ solution and brine, dried over anhydrous sodium sulfate. It was concentrated and the residue was loaded to a 4 g ISCO Gold column and eluted with 0% to 10% EtOAc/hexane to provide the title compound (0.12 g) as a film.

Step 2. (S)-6'-chloro-5-(((1R,2S)-2-((E)-pent-1-en-1-yl)cyclobutyl)methyl)-3',4,4',5-tetrahydro-2H,2'H-spiro[benzo[b][1,4]oxazepine-3,1'-naphthalene]-7-carboxylic Acid

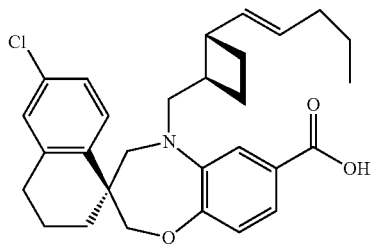

Lithium hydroxide solution (1.0 M aqueous solution, 2.4 ml, 2.4 mmol) was added to a solution of (S)-methyl 6'-chloro-5-(((1S,2R)-2-((E)-pent-1-en-1-yl)cyclobutyl)methyl)-3',4,4',5-tetrahydro-2H,2'H-spiro[benzo[b][1,4]oxazepine-3,1'-naphthalene]-7-carboxylate (Step 1, 0.118 g, 0.239 mmol) in THF (4.8 ml) and MeOH (2.4 ml). It was stirred at 50° C. for 12 h. It was concentrated, acidified with 1 N HCl and solid product was formed. It was filtered to collect the title compound (0.115 g) as a white solid.

Step 3: (S)—N-(but-3-en-1-ylsulfonyl)-6'-chloro-5-(((1R,2S)-2-((E)-pent-1-en-1-yl)cyclobutyl)methyl)-3',4,4',5-tetrahydro-2H,2'H-spiro[benzo[b][1,4]oxazepine-3,1'-naphthalene]-7-carboxamide

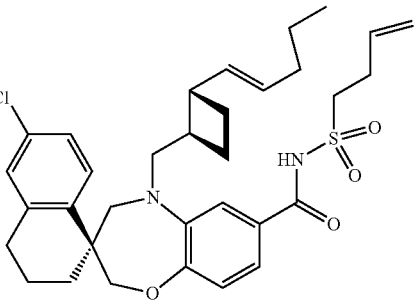

N-(3-Dimethylaminopropyl)-N'-ethylcarbodiimide hydrochloride (EDC; 0.016 g, 0.083 mmol) was added to a solution of (S)-6'-chloro-5-(((1S,2R)-2-((E)-pent-1-en-1-yl)cyclobutyl)methyl)-3',4,4',5-tetrahydro-2H,2'H-spiro[benzo[b][1,4]oxazepine-3,1'-naphthalene]-7-carboxylic acid (Step 2; 0.020 g, 0.042 mmol) and but-3-ene-1-sulfonamide (EE15; 0.011 g, 0.083 mmol) in DCM (1.7 mL). Then N,N-dimethylpyridin-4-amine (DMAP) (10 mg, 0.083 mmol) was added and it was stirred at ambient temperature overnight. The mixture was concentrated and the residue was purified by reverse phase preparative HPLC (Gemini™ Prep $C_{18}$ 5 μm column; Phenomenex, Torrance, CA; MeCN in water with 0.1% TFA, gradient elution) to give the title compound (24 mg) as a film. m/z (ESI, +ve ion) 597.2 $(M+H)^+$.

Step 4: (1S,3'R,6'S, 7'E)-6-chloro-3,4-dihydro-2H,13'H-spiro[naphthalene-1,20'-[18]oxa[11]thia[1,12]diazatetracyclo[12.7.2.0$^{3,6}$.0$^{17,22}$]tricosa[7,1 4,16,22]tetraen]-13'-one 11',11'-dioxide A 500 mL three-necked round bottom flask was charged with (S)—N-(but-3-en-1-ylsulfonyl)-6'-chloro-5-(((1S,2R)-2-((E)-pent-1-en-1-yl)cyclobutyl)methyl)-3',4,4',5-tetrahydro-2H,2'H-spiro[benzo[b][1,4]oxazepine-3,1'-naphthalene]-7-carboxamide (Step 3; 0.024 g, 0.040 mmol) in toluene (134 mL). It was stirred at ambient temperature for 10 min to dissolve the solid starting material and then subjected to three cycles of evacuation/back-filling with nitrogen. To the homogeneous solution was added a solution of Hoveyda-Grubbs II (5 mg, 8 μmol) in toluene (5 mL). After the mixture was stirred at 107° C. under nitrogen for 1 h, air was blown for 10 min to deactivate the catalyst and then concentrated. The residue was purified by reverse phase preparative HPLC (Gemini™ Prep $C_{15}$ 5 μm column; Phenomenex, Torrance, CA; MeCN in water with 0.1% TFA, gradient elution) to give the title compound (10.7 mg) as a white solid. $^1$H NMR (400 MHz, $CD_2Cl_2$) δ 8.16-8.04 (m, 1H), 7.79-7.63 (m, 1H), 7.29-7.14 (m, 2H), 7.13-7.07 (m, 1H), 7.02-6.94 (m, 1H), 6.76-6.68 (m, 1H), 5.89-5.78 (m, 1H), 5.45-5.35 (m, 1H), 4.24-4.14 (m, 2H), 4.03 (d, J=12.32 Hz, 1H), 3.54 (s, 4H), 3.36 (s, 1H), 2.81-2.39 (m, 6H), 2.02-1.16 (m, 8H). m/z (ESI, +ve ion) 527.2 $(M+H)^+$.

Example 826. (3S,6R,7E,22S)-6'-chloro-3',4'-dihydro-2'H,15H-spiro[10,20-dioxa-13-thia-1,14-diazatetracyclo[14.7.2.0³,⁶.0¹⁹,²⁴]pentacosa-7,16,18,24-tetraene-22,1'-naphthalen]-15-one 13,13-dioxide

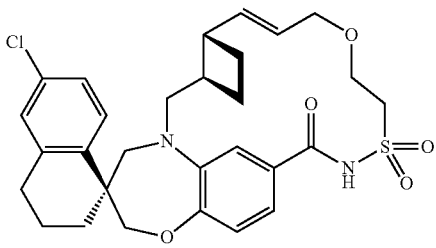

Step 1: (S)—N-((2-(allyloxy)ethyl)sulfonyl)-6'-chloro-5-(((1R,2S)-2-((E)-pent-1-en-1-yl)cyclobutyl)methyl)-3',4,4',5-tetrahydro-2H,2'H-spiro[benzo[b][1,4]oxazepine-3,1'-naphthalene]-7-carboxamide

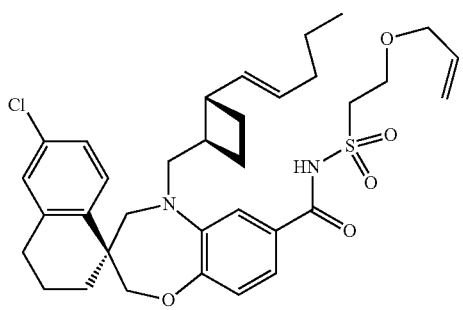

N-(3-Dimethylaminopropyl)-N'-ethylcarbodiimide hydrochloride (EDC; 0.056 g, 0.292 mmol) was added to a solution of (S)-6'-chloro-5-(((1S,2R)-2-((E)-pent-1-en-1-yl)cyclobutyl)methyl)-3',4,4',5-tetrahydro-2H,2'H-spiro[benzo[b][1,4]oxazepine-3,1'-naphthalene]-7-carboxylic acid (Example 825, Step 2; 0.070 g, 0.146 mmol) and 2-(allyloxy)ethanesulfonamide (Example 817, Step 3; 0.043 g, 0.262 mmol) in DCM (7 mL). Then N,N-dimethylpyridin-4-amine (DMAP) (0.036 g, 0.292 mmol) was added and it was stirred at rt overnight. The mixture was concentrated and the residue was purified by reverse phase preparative HPLC (Gemini™ Prep C$_{18}$ 5 μm column; Phenomenex, Torrance, CA; MeCN in water with 0.1% TFA, gradient elution) to give the title compound (34 mg) as a film. m/z (ESI, +ve ion) 627.2 (M+H)⁺.

Step 2: (3S,6R,7E,22S)-6'-chloro-3',4'-dihydro-2'H,15H-spiro[10,20-dioxa-13-thia-1,14-diazatetracyclo[14.7.2.0³,⁶.0¹⁹,²⁴]pentacosa-7,16,18,24-tetraene-22,1'-naphthalen]-15-one 13,13-dioxide A 500 mL three-necked round bottom flask was charged with (S)—N-((2-(allyloxy)ethyl)sulfonyl)-6'-chloro-5-(((1S,2R)-2-((E)-pent-1-en-1-yl)cyclobutyl)methyl)-3',4,4',5-tetrahydro-2H,2'H-spiro[benzo[b][1,4]oxazepine-3,1'-naphthalene]-7-carboxamide (Example 826, Step 1; 0.034 g, 0.054 mmol) in toluene (180 mL). It was stirred at rt for 10 min to dissolve the solid starting material and then subjected to three cycles of evacuation/back-filling with nitrogen. To the homogeneous solution was added a solution of Hoveyda-Grubbs II (7 mg, 11 μmol) in toluene (5 mL). After the mixture was stirred at 107° C. under nitrogen for 1 h, air was blown for 10 min to deactivate the catalyst. The mixture was concentrated and the residue was purified by reverse phase preparative HPLC (Gemini™ Prep C$_{18}$ 5 μm column; Phenomenex, Torrance, CA; MeCN in water with 0.1% TFA, gradient elution) to give the title compound (22 mg) as a white solid. ¹H NMR (400 MHz, CD$_2$Cl$_2$) δ 8.17-8.10 (m, 1H), 7.75-7.70 (m, 1H), 7.20-7.09 (m, 3H), 6.96 (s, 1H), 6.79-6.70 (m, 1H), 6.03-5.94 (m, 1H), 5.70-5.59 (m, 1H), 4.22-4.12 (m, 1H), 4.11-4.07 (m, 1H), 3.98-3.88 (m, 3H), 3.85-3.64 (m, 4H), 3.22 (d, J=14.28 Hz, 1H), 3.18-3.00 (m, 2H), 2.81-2.73 (m, 2H), 2.63-2.50 (m, 1H), 2.36-2.24 (m, 1H), 2.22-1.18 (m, 9H). m/z (ESI, +ve ion) 557.2 (M+H)⁺.

Example 827. (3S,6R,22S)-6'-chloro-3',4'-dihydro-2'H,15H-spiro[10,20-dioxa-13-thia-1,14-diazatetracyclo[14.7.2.0³,⁶.0¹⁹,²⁴]pentacosa-16,18,24-triene-22,1'-naphthalen]-15-one 13,13-dioxide

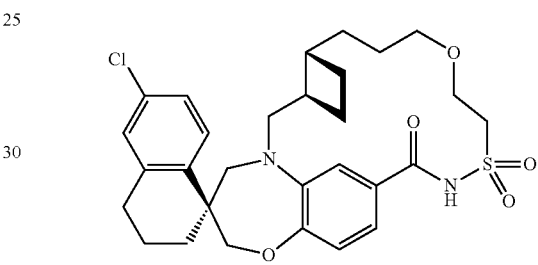

A 50 mL flask was charged with Example 826 (0.0038 g, 6.82 μmol), EtOAc (7 mL) and platinum (IV) oxide (1.6 mg, 6.82 μmol). After the mixture was degassed by N$_2$ it was stirred at rt under hydrogen for 44 min. It was filtered through syringe filter to remove catalyst. The filtrate was concentrated to give the title compound (3.8 mg) as a white solid. ¹H NMR (400 MHz, CD$_2$Cl$_2$) δ 8.16-8.10 (m, 1H), 7.75-7.68 (m, 1H), 7.19-7.07 (m, 3H), 6.97-6.92 (m, 1H), 6.87-6.80 (m, 1H), 4.13-4.08 (m, 2H), 3.88-3.84 (m, 2H), 3.72-3.65 (m, 2H), 3.50-3.43 (m, 1H), 3.39-3.32 (m, 1H), 3.26 (d, J=14.28 Hz, 1H), 3.17 (dd, J=7.04, 15.65 Hz, 1H), 2.80-2.73 (m, 2H), 2.24-1.76 (m, 6H), 1.71-1.40 (m, 8H). m/z (ESI, +ve ion) 559.1 (M+H)⁺.

Example 829. (1S,3'R,6'S, 7'E)-6-chloro-3,4-dihydro-2H,14'H-spiro[naphthalene-1,21'-[19]oxa[12]thia[1,13]diazatetracyclo[13.7.2.0³,⁶.0¹⁸,²³]tetracosa[7,15,17,23]tetraen]-14'-one 12',12'-dioxide

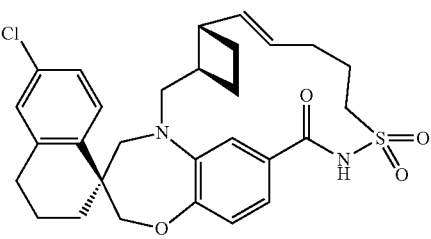

Step 1: (S)-6'-chloro-5-(((1R,2S)-2-((E)-pent-1-en-1-yl)cyclobutyl)methyl)-N-(pent-4-en-1-ylsulfonyl)-3',4',4',5-tetrahydro-2H,2'H-spiro[benzo[b][1,4]oxazepine-3,1'-naphthalene]-7-carboxamide

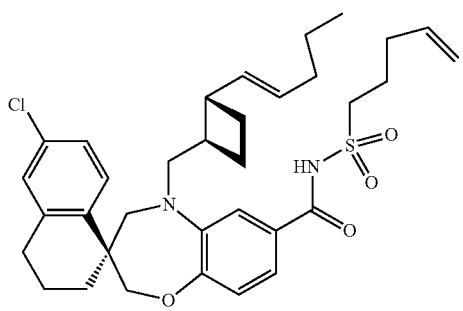

N-(3-Dimethylaminopropyl)-N'-ethylcarbodiimide hydrochloride (EDC; 0.016 g, 0.083 mmol) was added to a solution of (S)-6'-chloro-5-(((1S,2R)-2-((E)-pent-1-en-1-yl)cyclobutyl)methyl)-3',4',4',5-tetrahydro-2H,2'H-spiro[benzo[b][1,4]oxazepine-3,1'-naphthalene]-7-carboxylic acid (Example 825, Step 2; 0.020 g, 0.042 mmol) and pent-4-ene-1-sulfonamide (EE192; 0.012 g, 0.083 mmol) in DCM (1.7 mL). Then N,N-dimethylpyridin-4-amine (DMAP) (10 mg, 0.083 mmol) was added and it was stirred at rt for 22 h. It was concentrated and the residue was purified by reverse phase preparative HPLC (Gemini™ Prep C$_{18}$ 5 μm column; Phenomenex, Torrance, CA; MeCN in water with 0.1% TFA, gradient elution) to give the title compound (20 mg) as a film. m/z (ESI, +ve ion) 611.2 (M+H)$^+$.

Step 2: (1S,3'R,6'S, 7'E)-6-chloro-3,4-dihydro-2H,14'H-spiro[naphthalene-1,21'-[19]oxa[12]thia[1,13]diazatetracyclo[13.7.2.0$^{3,6}$.0$^{18,23}$]tetracosa [7,15,17,23]tetraen]-14'-one 12',12'-dioxide

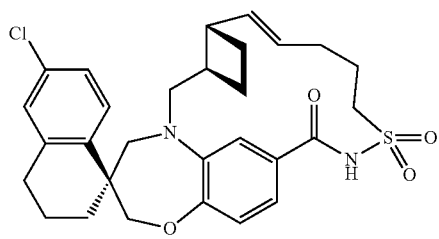

A 500 mL three-necked round bottom flask was charged with (S)-6'-chloro-5-(((1S,2R)-2-((E)-pent-1-en-1-yl)cyclobutyl)methyl)-N-(pent-4-en-1-ylsulfonyl)-3',4',4',5-tetra-hydro-2H,2'H-spiro[benzo[b][1,4]oxazepine-3,1'-naphthalene]-7-carboxamide (Example 829, Step 1; 0.020 g, 0.033 mmol) in toluene (110 mL). It was stirred at rt for 10 min to dissolve the solid starting material and then subjected to three cycles of evacuation/back-filling with nitrogen. To the homogeneous solution was added a solution of Hoveyda-Grubbs II (4.10 mg, 6.54 μmol) in toluene (5 mL). After the mixture was stirred at 107° C. under nitrogen for 56 min it was concentrated. The residue was purified by reverse phase preparative HPLC (Gemini™ Prep C$_{18}$ 5 μm column; Phenomenex, Torrance, CA; MeCN in water with 0.1% TFA, gradient elution) to give the title compound (10.7 mg) as a white solid. $^1$H NMR (400 MHz, CD$_2$Cl$_2$) δ 7.99 (br. s., 1H), 7.72 (d, J=8.61 Hz, 1H), 7.17 (td, J=2.27, 8.56 Hz, 1H), 7.12-7.08 (m, 1H), 7.04-6.96 (m, 1H), 6.95-6.90 (m, 1H), 6.75 (br. s., 1H), 5.61-5.51 (m, 2H), 4.12-4.07 (m, 2H), 3.81-3.66 (m, 3H), 3.49-3.31 (m, 2H), 3.23-3.03 (m, 2H), 2.81-2.67 (m, 3H), 2.24-2.12 (m, 3H), 2.09-1.98 (m, 4H), 1.23 (s, 5H). m/z (ESI, +ve ion) 541.1 (M+H)$^+$.

Example 830. (1S,3'S,6'S)-6-chloro-3,4-dihydro-2H,13'H-spiro[naphthalene-1,20'-[18]oxa[11]thia[1,12]diazatetracyclo[14.7.2.0$^{3,6}$.0$^{19,24}$]tricosa[14, 16,22]trien]-13'-one 11',11'-dioxide

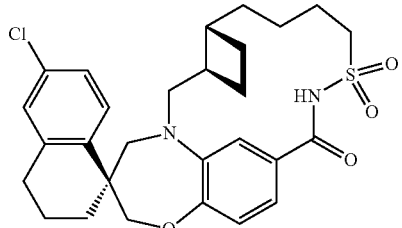

A 50 mL flask was charged with Example 825 (0.0031 g, 5.88 μmol), EtOAc (6 mL) and platinum (IV) oxide (1.3 mg, 5.88 μmol). The mixture was degassed by N$_2$ and it was stirred at rt under hydrogen for 1 h. The mixture was filtered through syringe filter to remove catalyst and the filtrate was concentrated to give the title compound (3.1 mg) as a white solid. $^1$H NMR (400 MHz, CD$_2$Cl$_2$) δ 7.76-7.69 (m, 1H), 7.21-7.06 (m, 3H), 7.02-6.84 (m, 2H), 4.08 (d, J=7.24 Hz, 2H), 3.73-3.60 (m, 3H), 3.50 (d, J=12.32 Hz, 1H), 3.39-3.32 (m, 1H), 3.27 (d, J=14.08 Hz, 1H), 2.76 (br. s., 2H), 2.33-2.21 (m, 1H), 2.14-1.22 (m, 15H). m/z (ESI, +ve ion) 529.1 (M+H)$^+$.

Example 831. (1S,3'R,6'R,7'R,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,10'R,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'R,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6R,7'S,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'R,11'R)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,10'S,11'R)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'S,11'R)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide

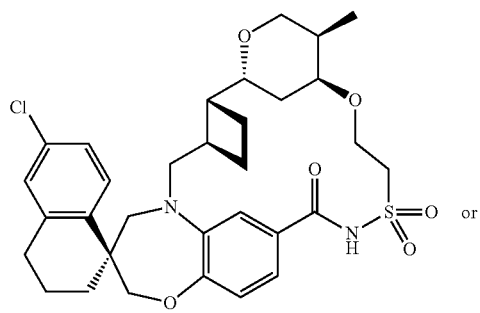 or

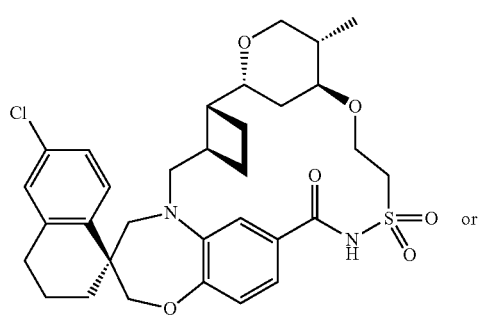 or

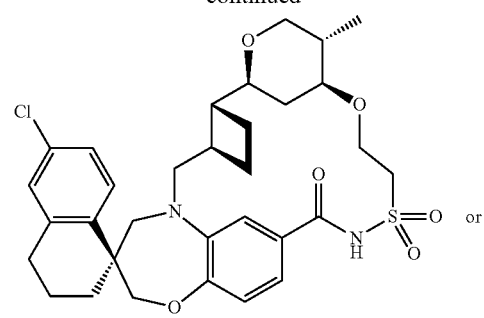 or

 or

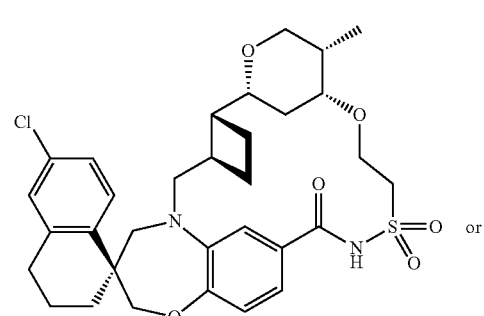 or

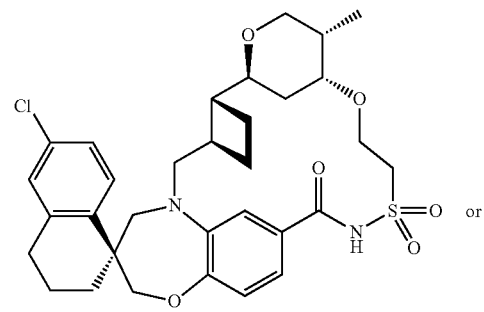 or

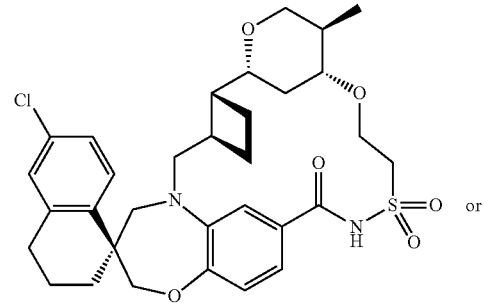 or

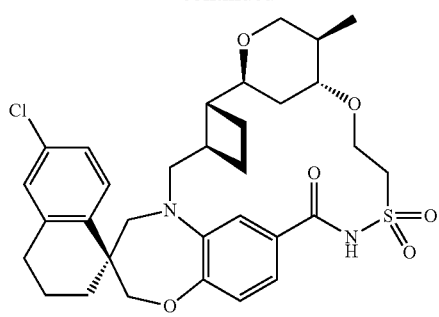

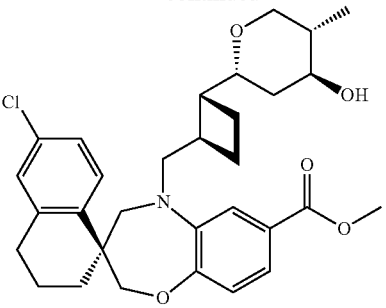

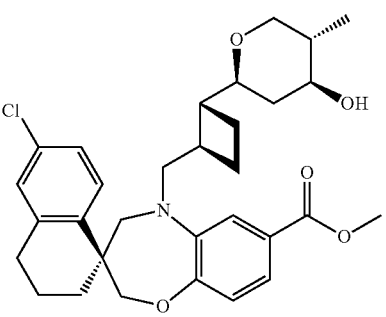

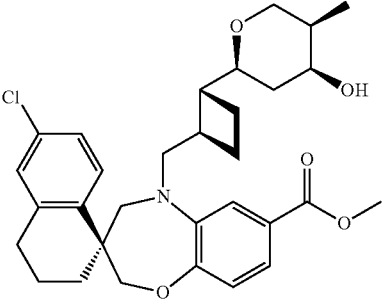

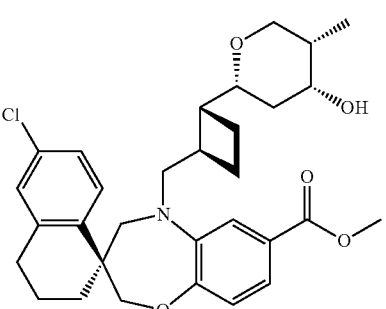

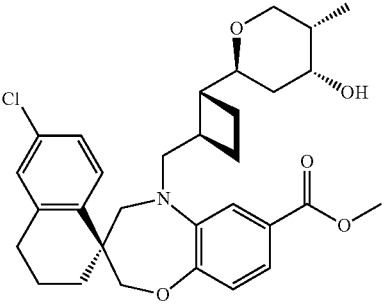

Step 1: (S)-Methyl 6'-chloro-5-(((1R,2R)-2-((2R,4S,5R)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S,5R)-4-hydroxy-5-methyl tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S,5S)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R,5S)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R,5S)-4-hydroxy-5-methyltetrahydro-2H-pyran-2-yl)cyclobutyl)methyl)-3',4,4',5-tetrahydro-2H,2'Hspiro[benzo[b][1,4]oxazepine-3,1'-naphthalene]-7-carboxylate or (S)-methyl 6'-chloro-5-(((1R,2R)-2-((2R,4R,5R)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R,5R)-4-hydroxy-5-methyltetrahydro-2H-pyran-2-yl)cyclobutyl) methyl)-3',4,4',5-tetrahydro-2H,2'H-spiro[benzo[b][1,4]oxazepine-3,1'-naphthalene]-7-carboxylate

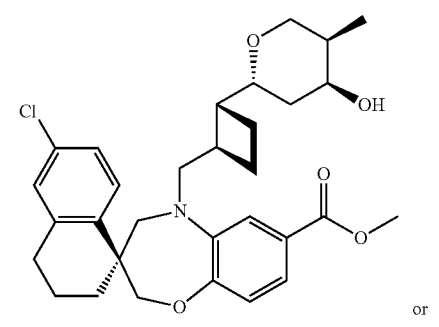

or

TFA (5.1 mL) was added slowly to a solution of (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, STEP 20A; 0.417 g, 0.919 mmol) and 2-methyl-3-buten-1-ol (0.123 mL, 1.19 mmol) in DCM (10 mL) which was degassed with N$_2$. It was stirred at rt for 22 min. The reaction mixture was added slowly to Na2CO3 (aq) solution (40 ml) and MeOH (20 mL). After it was stirred at rt for 15 min, the mixture was extracted with EtOAc (3×130 mL). The organic phase was dried over anhydrous sodium sulfate and concentrated. The residue was purified by reverse phase preparative HPLC (Gemini™ Prep C$_{18}$ 5 µm column; Phenomenex, Torrance, CA; MeCN in water with 0.1% TFA, gradient elution) to provide the title compound (32 mg, second eluting peak) as a white solid. m/z (ESI, +ve ion) 540.1 (M+H)$^+$.

Step 2:
N,N-bis(4-methoxybenzyl)ethenesulfonamide

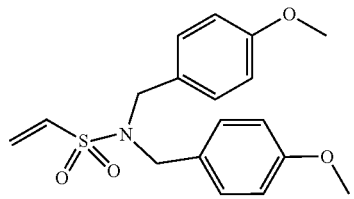 [SMILES: C=CS(=O)(=O)N(Cc1ccc(OC)cc1)Cc1ccc(OC)cc1]

2-Chloroethanesulfonyl chloride (0.645 mL, 6.13 mmol) was added dropwise to a solution of bis(4-methoxybenzyl) amine (EE11; 1.435 g, 5.58 mmol) and triethylamine (2.71 mL, 19.5 mmol) in DCM (20.7 mL) at 0° C. (ice bath). It was stirred at 0° C. for 28 min. EtOAc (200 mL) and water (10 mL) were added. The organic phase was washed with brine (3 mL), dried over anhydrous sodium sulfate and concentrated. The residue was loaded to a 80 g ISCO Gold column and eluted with 0% to 30% EtOAc/hexane to provide the title compound (1.68 grams) as a white solid. m/z (ESI, +ve ion) 370.0 (M+Na)$^+$.

Step 3: (S)-6'-chloro-5-((((1R,2R)-2-((2R,4S,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4S,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4S,5S)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4S,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R,5S)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,22R)-2-((2S,4R,5S)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4R,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid

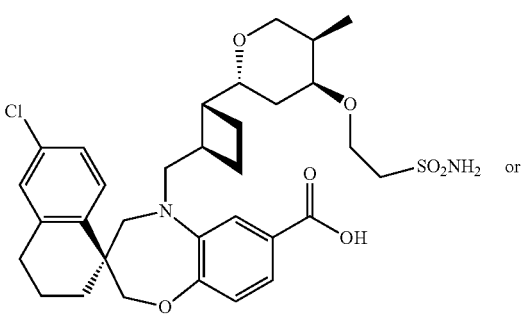

-continued

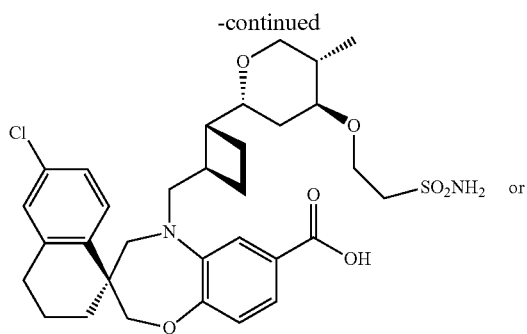

or

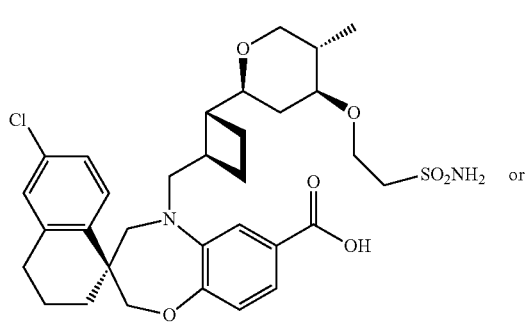

or

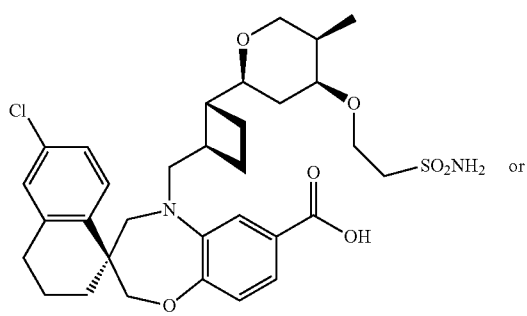

or

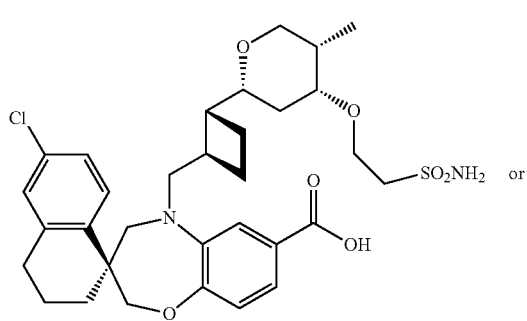

or

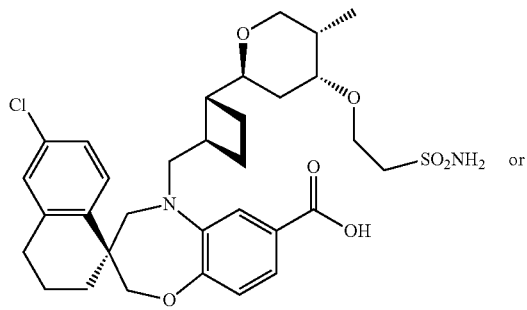

or

-continued

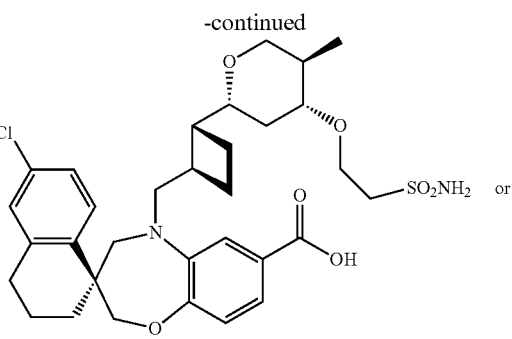

or

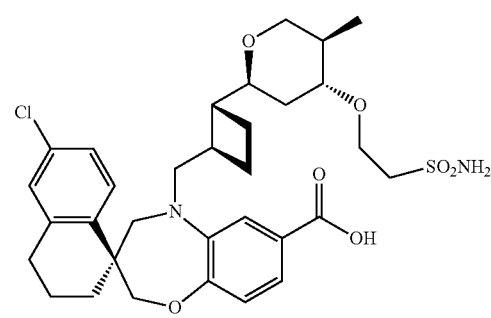

Sodium hydride (60% dispersion in mineral oil; 6.2 mg, 0.30 mmol) was added to a solution of (1'S)-methyl 6'-chloro-5-(((1R,2R)-2-((2R,4S)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 831, Step 1; 0.016 g, 0.030 mmol) in THF (0.8 mL), which was cooled by ice bath. After it was stirred at rt for 8 min N,N-bis(4-methoxybenzyl)ethenesulfonamide (Example 831, Step 2; 0.019 g, 0.053 mmol) in THF (1.5 mL) was added. It was stirred at rt for 60 min. Water (2 mL) and EtOAc (120 mL) were added. The organic phase was washed with brine, dried over anhydrous sodium sulfate and concentrated. The residue was purified by reverse phase preparative HPLC (Gemini™ Prep $C_{18}$ 5 μm column; Phenomenex, Torrance, CA; MeCN in water with 0.1% TFA, gradient elution) to provide the title compound (7.8 mg).

Hydrolysis I: The residue was dissolved in THF (3 mL), MeOH (6 mL) and 1M LiOH solution (6 mL) and the mixture was stirred at 50° C. for 3.5 h. It was concentrated, acidified with 1N HCl solution to pH 2-4, extracted with EtOAc (100 mL). The organic phase was washed with brine and dried over anhydrous sodium sulfate and concentrated.

Hydrolysis II: The residue was dissolved in 1:3 TFA/DCM (5 mL) and stirred at rt for 3 days. After it was concentrated the residue was purified by reverse phase preparative HPLC (Gemini™ Prep $C_{18}$ 5 μm column; Phenomenex, Torrance, CA; MeCN in water with 0.1% TFA, gradient elution) to provide the title compound (5 mg) as a white solid. m/z (ESI, +ve ion) 633.1 $(M+H)^+$.

Step 4: (1S,3'R,6'R,7'R,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,10'R,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'R,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6R,7'S,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'R,11'R)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,10'S,11'R)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'S,11'R)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide N,N-Dimethylpyridin-4-amine (DMAP) (0.012 g, 0.095 mmol) was added to a solution of (1'S)-6'-chloro-5-(((1R,2R)-2-((2R,4S)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid (Example 831, Step 3; 0.005 g, 7.90 μmol) in DCM (22 mL) at 0° C. Then N1-((ethylimino)methylene)-N3,N3-dimethylpropane-1,3-diamine hydrochloride (EDC; 0.014 g, 0.071 mmol) was added slowly in portions and it was stirred at 0° C. to rt for 19 h. It was concentrated and the residue was purified by reverse phase preparative HPLC (Gemini™ Prep C$_{18}$ 5 μm column; Phenomenex, Torrance, CA; MeCN in water with 0.1% TFA, gradient elution) to provide the title compound (3.4 mg) as a white solid. $^1$H NMR (400 MHz, CD$_2$Cl$_2$) δ 8.32-8.26 (m, 1H), 7.72 (d, J=8.61 Hz, 1H), 7.24-7.15 (m, 2H), 7.11-7.07 (m, 1H), 7.00 (s, 1H), 6.62-6.57 (m, 1H), 4.13-4.08 (m, 2H), 3.98-3.85 (m, 2H), 3.78-3.63 (m, 5H), 3.59 (d, J=2.74 Hz, 1H), 3.53-3.46 (m, 2H), 3.27 (d, J=14.48 Hz, 1H), 3.18 (dd, J=9.78, 15.45 Hz, 1H), 2.83-2.74 (m, 2H), 2.48-2.38 (m, 1H), 2.29-2.20 (m, 1H), 2.12-1.63 (m, 9H), 1.61-1.52 (m, 1H), 1.42 (t, J=12.62 Hz, 1H), 0.87 (d, J=7.04 Hz, 3H). m/z (ESI, +ve ion) 615.0 (M+H)$^+$.

Example 832. (1S,3'R,6'R)-6-chloro-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 13',13'-dioxide

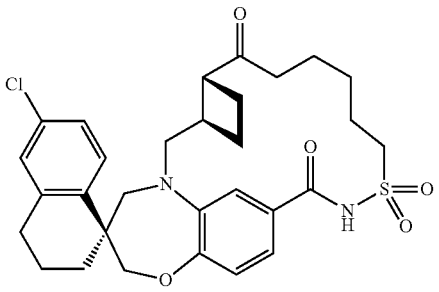

Step 1: (1S,3'R,6'R,7'S)-6-chloro-7'-hydroxy-3,4-dihydro-2H,15'Hspiro[naphthalene-1,22'[20]oxa[13]thia[1,14]diazatetracyclo[14.7.2.0$^{3,6}$.0$^{19,24}$]pentacosa[16,18,24]trien]-15'-one 13',13'-dioxide

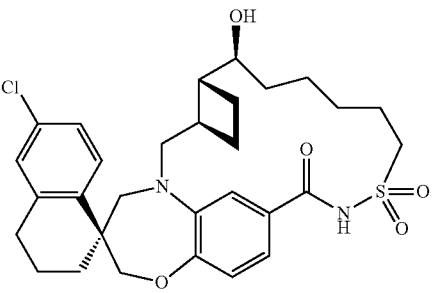

A mixture of (1S,3'R,6'R,7'S,9'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (Example 846; 0.112 g, 0.196 mmol) and platinum (IV) oxide (0.045 g, 0.196 mmol) in EtOAc (33 mL) was stirred under H$_2$ at rt for 3 h. It was filtered through syringe filter to remove solid catalyst and the solution was concentrated to provide title compound (112 mg) as a white solid. $^1$H NMR (400 MHz, CD$_2$Cl$_2$) δ 8.93 (m, 1H), 7.71 (m, 1H), 7.15 (m, 3H), 7.09 (d, J=2.35 Hz, 1H), 6.95 (m, 1H), 4.10 (m, 2H), 3.78-3.62 (m, 4H), 3.46-3.34 (m, 1H), 3.26 (d, J=14.28 Hz, 1H), 3.16 (dd, J=9.00, 15.26 Hz, 1H), 2.82-2.71 (m, 2H), 2.45-2.33 (m, 1H), 2.26-2.16 (m, 1H), 2.08-1.16 (m, 17H). m/z (ESI, +ve ion) 573.2 (M+H)$^+$.

Step 2: (1S,3'R,6'R)-6-chloro-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [16,18,24]triene]-7',15'-dione 13',13'-dioxide A flask charged dimethyl sulfoxide (0.019 mL, 0.27 mmol) and DCM (0.7 mL) was cooled to −78° C. Oxalyl chloride (2.0 M solution in DCM, 0.070 mL, 0.141 mmol) was added dropwise and the reaction was stirred for 16 min. A solution of the product (from Step 1; 0.031 g, 0.054 mmol) in DCM (0.5 mL) was added dropwise and the reaction was stirred at −78° C. for 25 min. Triethylamine (0.068 mL, 0.49 mmol) was added dropwise and it was stirred at rt for 1 h. The reaction mixture was quenched with water (2 mL), extracted with EtOAc (130 mL). The organic phase was washed with 1N HCl solution (2×3 mL), brine, dried over anhydrous sodium sulfate and concentrated. The residue was purified by reverse phase preparative HPLC (Gemini™ Prep $C_{18}$ 5 μm column; Phenomenex, Torrance, CA; MeCN in water with 0.1% TFA, gradient elution) to provide the title compound (9 mg) as a white solid. $^1$H NMR (400 MHz, $CD_2Cl_2$) δ 7.75-7.68 (m, 1H), 7.20-7.15 (m, 1H), 7.14-7.08 (m, 2H), 6.98-6.92 (m, 1H), 6.90-6.85 (m, 1H), 4.14-4.05 (m, 2H), 3.83-3.70 (m, 2H), 3.66-3.47 (m, 3H), 3.28 (d, J=14.28 Hz, 1H), 3.20 (dd, J=8.41, 15.45 Hz, 1H), 3.14-3.07 (m, 1H), 3.02-2.91 (m, 1H), 2.83-2.73 (m, 3H), 2.58-2.36 (m, 2H), 2.17-1.67 (m, 8H), 1.64-1.40 (m, 4H). m/z (ESI, +ve ion) 571.1 (M+H)$^+$.

Example 833. (1S,3'R,6'R,7'S,9'E)-6-chloro-7'-hydroxy-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide or (1S,3'R,6'R,7'S,9'Z)-6-chloro-7'-hydroxy-3,4-dihydro-2H,16'H-spiro[naphthalene-1,23'-[21]oxa[14]thia[1,15]diazatetracyclo[15.7.2.0$^{3,6}$.0$^{20,25}$]hexacosa [9,17,19,25]tetraen]-16'-one 14',14'-dioxide

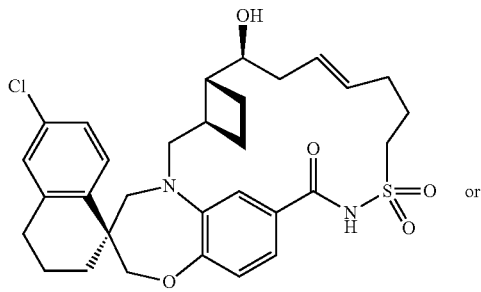

or

Step 1: (S)-6'-chloro-5-(((1R,2R)-2-((S)-1-hydroxybut-3-en-1-yl)cyclobutyl)methyl)-N-(pent-4-en-1-ylsulfonyl)-3',4,4',5-tetrahydro-2H,2'H-spiro[benzo[b][1,4]oxazepine-3,1'-naphthalene]-7-carboxamide

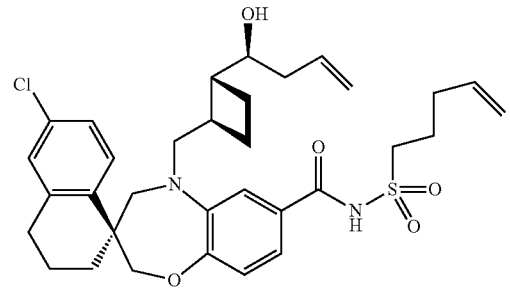

N-(3-Dimethylaminopropyl)-N'-ethylcarbodiimide hydrochloride (EDC; 0.036 g, 0.19 mmol) was added to a solution of (S)-6'-chloro-5-(((1R,2R)-2-((S)-1-hydroxybut-3-en-1-yl)cyclobutyl) methyl)-3',4,4',5-tetrahydro-2H,2'H-spiro[benzo[b][1,4]oxazepine-3,1'-naphthalene]-7-carboxylic acid (Intermediate AA13A; 0.045 g, 0.093 mmol) and pent-4-ene-1-sulfonamide (EE192; 0.098 g, 0.654 mmol) in DCM (6.2 mL). Then N,N-dimethylpyridin-4-amine (DMAP) (0.023 g, 0.19 mmol) was added and it was stirred at rt for 15 h. After it was concentrated, the residue was purified by reverse phase preparative HPLC (Gemini™ Prep $C_{18}$ 5 μm column; Phenomenex, Torrance, CA; MeCN in water with 0.1% TFA, gradient elution) to provide the title compound (22 mg) as a film. m/z (ESI, +ve ion) 613.0 (M+H)$^+$.

Step 2: (1S,3'R,6'R,7'S,9'E)-6-chloro-7'-hydroxy-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide or (1S,3'R,6'R,7'S,9'Z)-6-chloro-7'-hydroxy-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide

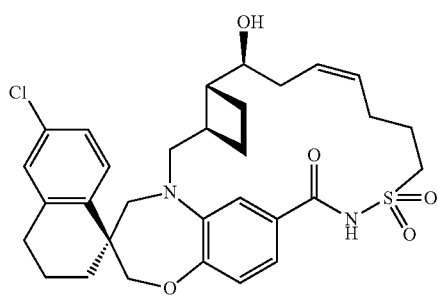

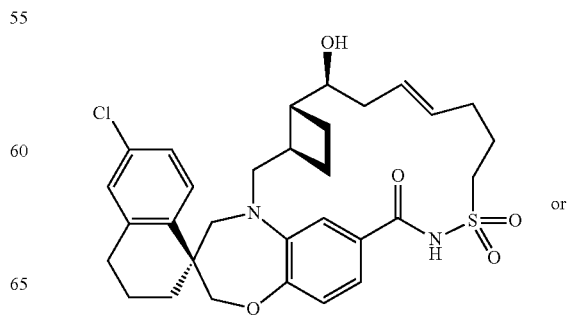

or

1707
-continued

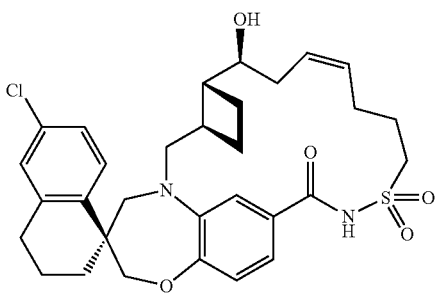

A 250 mL round bottom flask was charged with (1'S)-6'-chloro-5-(((1R,2R)-2-(1-hydroxybut-3-en-1-yl)cyclobutyl)methyl)-N-(pent-4-en-1-ylsulfonyl)-3',4,4',5-tetrahydro-2H,2'H-spiro[benzo [b][1,4]oxazepine-3,1'-naphthalene]-7-carboxamide (Example 833, Step 1; 0.022 g, 0.036 mmol) in toluene (90 mL). It was stirred at rt for 10 min to dissolve the solid starting material and then subjected to three cycles of evacuation/back-filling with nitrogen. To the homogeneous solution was added a solution of Hoveyda-Grubbs II (4.5 mg, 7.2 μmol) in toluene (5 mL). After the mixture was stirred at 106° C. under nitrogen for 73 min, air was blown for 10 min to deactivate the catalyst, and then concentrated. The residue was purified by reverse phase preparative HPLC (Gemini™ Prep $C_{18}$ 5 μm column; Phenomenex, Torrance, CA; MeCN in water with 0.1% TFA, gradient elution). The title compound (2.1 mg) was obtained as a single isomer (second eluting peak) as a white solid. $^1$H NMR (400 MHz, $CD_2Cl_2$) δ 9.54 (br. s., 1H), 7.73-7.67 (m, 1H), 7.32-7.28 (m, 1H), 7.27-7.23 (m, 1H), 7.20-7.15 (m, 1H), 7.12-7.07 (m, 1H), 6.98-6.93 (m, 1H), 5.64-5.55 (m, 1H), 5.53-5.44 (m, 1H), 4.21-4.09 (m, 2H), 3.72-3.53 (m, 4H), 3.35-3.29 (m, 1H), 2.80-2.74 (m, 2H), 2.71-2.64 (m, 1H), 2.55-1.42 (m, 18H). m/z (ESI, +ve ion) 585.0 (M+H)$^+$.

Example 834. (1S,3'R,6'R,7'S,9'Z)-6-chloro-7'-hydroxy-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide or (1S,3'R,6'R,7'S,9'E)-6-chloro-7'-hydroxy-3,4-dihydro-2H,16'H-spiro[naphthalene-1,23'-[21]oxa[14]thia[1,15]diazatetracyclo[15.7.2.0$^{3,6}$.0$^{20,25}$]hexacosa[9,17,19,25]tetraen]-16'-one 14',14'-dioxide

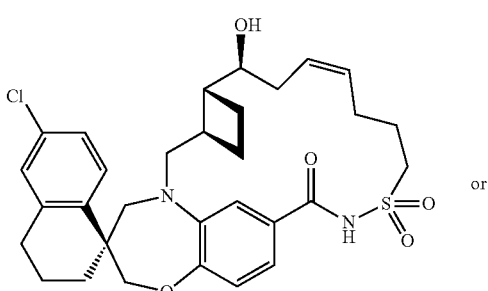

or

1708
-continued

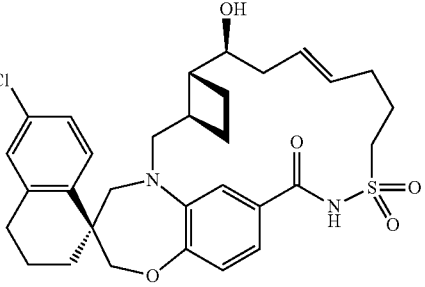

The title compound (5.0 mg) was obtained as a single isomer (first eluting peak) from the reverse phase preparative HPLC in Example 833 as a white solid. $^1$H NMR (400 MHz, $CD_2Cl_2$) δ 9.29-9.22 (m, 1H), 7.76-7.69 (m, 1H), 7.37-7.33 (m, 1H), 7.26-7.22 (m, 1H), 7.19-7.14 (m, 1H), 7.11-7.07 (m, 1H), 6.95 (d, J=8.22 Hz, 1H), 5.60-5.42 (m, 2H), 4.18-4.09 (m, 2H), 3.85-3.73 (m, 2H), 3.65 (d, J=14.48 Hz, 1H), 3.61-3.55 (m, 1H), 3.47 (td, J=7.19, 14.57 Hz, 1H), 3.28-3.16 (m, 2H), 2.80-2.72 (m, 2H), 2.41-2.34 (m, 1H), 2.15 (s, 16H). m/z (ESI, +ve ion) 585.0 (M+H)$^+$.

Example 835. (1S,3'R,6'R,7'S)-6-chloro-7'-hydroxy-3,4-dihydro-2H,16'H-spiro[naphthalene-1,23'[21]oxa[14]thia[1,15]diazatetracyclo[15.7.2.0$^{3,6}$.0$^{20,25}$]hexacosa[17,19,25]trien]-16'-one 14',14'-dioxide

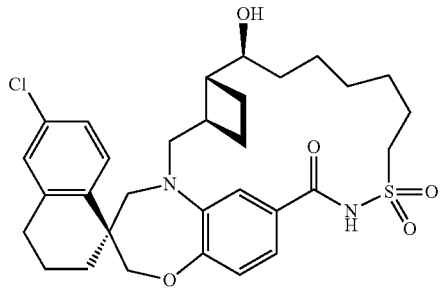

A mixture of (1S,3'R,6'R,7'S,9'E)-6-chloro-7'-hydroxy-3,4-dihydro-2H,16'H-spiro[naphthalene-1,23'-[21]oxa[14]thia[1,15]diazatetracyclo[15.7.2.0$^{3,6}$.0$^{0.25}$]hexacosa[9,17,19,25]tetraen]-16'-one 14',14'-dioxide (Example 833; 0.0021 g, 3.6 μmol) and platinum (IV) oxide (0.8 mg, 3.6 μmol) in EtOAc (1.4 mL) was stirred under $H_2$ at rt for 2 h. It was filtered through syringe filter to remove solid catalyst and the filtrate was concentrated to provide the title compound (1.8 mg) as a white solid. $^1$H NMR (400 MHz, $CD_2Cl_2$) δ 7.75-7.68 (m, 1H), 7.38-7.28 (m, 2H), 7.21-7.14 (m, 1H), 7.12-7.07 (m, 1H), 7.00-6.92 (m, 1H), 4.16-4.09 (m, 2H), 3.81-3.73 (m, 1H), 3.65 (d, J=13.50 Hz, 2H), 3.58-3.48 (m, 2H), 3.28 (d, J=14.48 Hz, 1H), 2.81-2.72 (m, 2H), 2.47-2.38 (m, 1H), 2.11-0.75 (m, 21H). m/z (ESI, +ve ion) 587.0 (M+H)$^+$.

1709

Example 836. (1S,3'R,6'R,7'S,11'S)-6-chloro-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{1,26}$]octacosa[18,20,26]trien]-17'-one 15',15'-dioxide or (1S,3'R,6'R,7'S,11'R)-6-chloro-3,4-dihydro-2H,17'H-spiro[naphthalene-1,24'-[8,12,22]trioxa[15]thia[1,1diazapentacyclo[16.7.2.1$^{7,11}$.0$^{3,6}$.0$^{1,26}$]octacosa[18,20,26]trien]-17'-one 15',15'-dioxide or (1S,3'R,6'S, 7'S,11'R)-6-chloro-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{1,26}$]octacosa[18,20,26]trien]-17'-one 15',15'-dioxide or (1S,3'R,6'S, 7'S,11'S)-6-chloro-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{1,26}$]octacosa[18,20,26]trien]-17'-one 15',15'-dioxide

1710

Step 1: (S)-methyl 6'-chloro-5-(((1R,2R)-2-((2R,4R)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

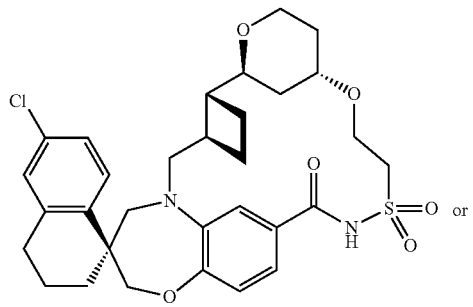 or

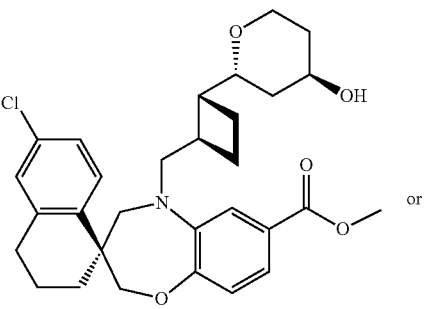 or

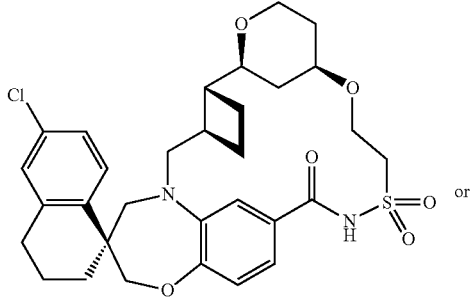 or

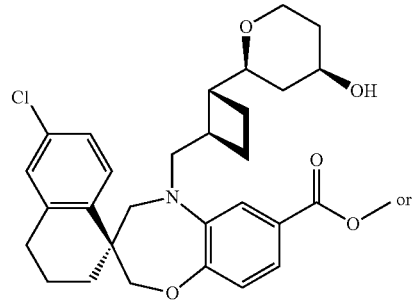 or

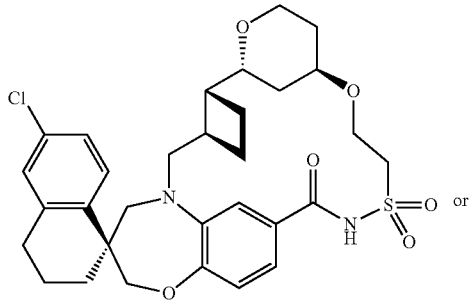 or

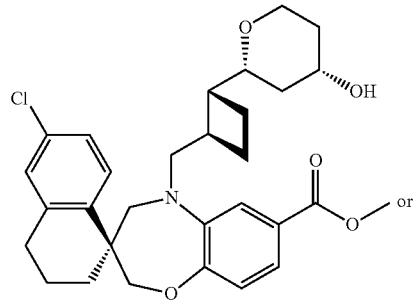 or

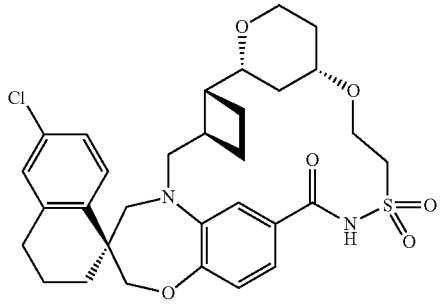

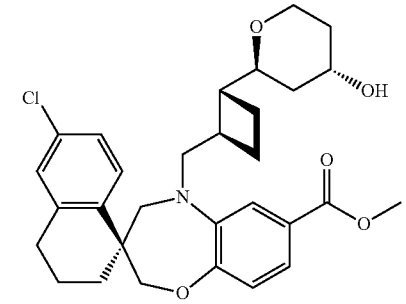

1711

A mixture of (S)-methyl 6'-chloro-5-(((1R,2R)-2-formyl-cyclobutyl)methyl)-3',4,4',5-tetrahydro-2H,2'H-spiro[benzo[b][1,4]oxazepine-3,1'-naphthalene]-7-carboxylate (Intermediate AA11A, STEP 20A; 0.243 g, 0.535 mmol), 3-buten-1-ol (0.541 ml, 0.696 mmol) in TFA (4.5 mL) and DCM (9 mL) was degassed with N$_2$ and stirred at rt for 30 min. It was quenched with NaHCO$_3$ solution to pH >7 and extracted with EtOAc (60 mL). The organic phase was dried over anhydrous sodium sulfate, concentrated. To the residue was added saturated Na$_2$CO$_3$ solution (1 mL), MeOH (2 mL) and THF (2 mL). After it was stirred at rt for 30 min it was neutralized with 1 N HCl solution to pH 7 and extracted with EtOAc (100 mL). The organic phase was washed with brine, dried over anhydrous sodium sulfate and concentrated. The residue was loaded to a 24 g ISCO Gold column and eluted with 0% to 50% EtOAc/hexane to provide the title compound (210 mg) as a white solid. m/z (ESI, +ve ion) 526.1 (M+H)$^+$.

Step 2: (S)-6'-chloro-5-(((1R,2R)-2-((2R,4R)-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4R)-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4S)-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4S)-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid

1712

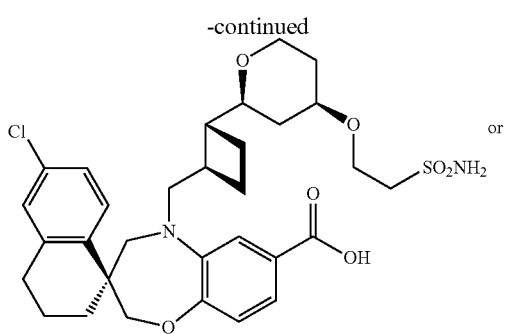

or

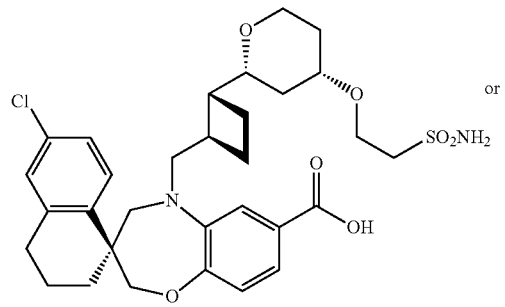

or

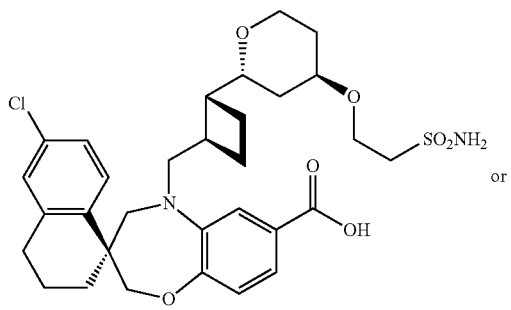

or

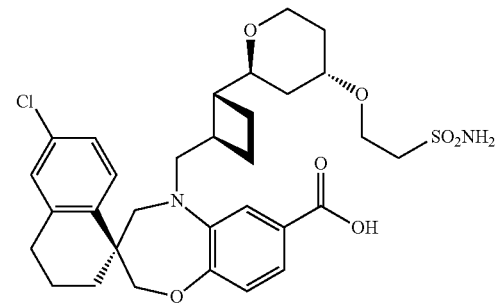

Sodium hydride (60% dispersion in mineral oil; 18 mg, 0.84 mmol) was added to a solution of (S)-methyl 6'-chloro-5-(((1R,2R)-2-((2S,4R)-4-hydroxytetrahydro-2H-pyran-2-yl)cyclobutyl) methyl)-3',4,4',5-tetrahydro-2H,2'H-spiro[benzo[b][1,4]oxazepine-3,1'-naphthalene]-7-carboxylate (Example 836, Step 1; 0.113 g, 0.215 mmol) in THF (9 mL), which was cooled to 0° C. After it was stirred at rt for 10 min, N,N-bis(4-methoxybenzyl) ethenesulfonamide (Example 831, Step 2; 0.112 g, 0.322 mmol) in THF (2.5 mL) was added and it was stirred at rt for 20 h. Water (2 mL) and EtOAc (130 mL) were added. The organic phase was washed with brine and dried over anhydrous sodium sulfate and concentrated to provide a residue.

Hydrolysis I: The residue was dissolved in THF (7 mL), MeOH (7 mL) and 1 M LiOH solution (5 mL) and stirred at 50° C. for 1.6 h. It was concentrated, acidified with 1 N HCl solution to pH 2-4, extracted with EtOAc (90 mL). The organic phase was washed with brine and dried over anhydrous sodium sulfate. It was concentrated to give a residue.

Hydrolysis II: The residue was dissolved in 1:3 TFA/DCM (4 mL) and stirred at rt for 20 h. After concentration, the residue was loaded to a 12 g ISCO Gold column and eluted with 0% to 15% EtOAc (containing 0.3% AcOH)/DCM (containing 0.3% AcOH) to provide the title compound (110 mg) as a film. m/z (ESI, +ve ion) 619.1 (M+H)$^+$.

Step 3: (1S,3'R,6'R,7'S,11'S)-6-chloro-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{1,26}$]octacosa[18,20,26]trien]-17'-one 15',15'-dioxide or (1S,3'R,6'R,7'S,11'R)-6-chloro-3,4-dihydro-2H,17'H-spiro[naphthalene-1,24'-[8,12,22]trioxa[15]thia[1,1diazapentacyclo[16.7.2.1$^{7,11}$.0$^{3,6}$.0$^{1,26}$]octacosa[18,20,26]trien]-17'-one 15',15'-dioxide or (1S,3'R, 6'S, 7'S,11'R)-6-chloro-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{1,26}$]octacosa[18,20,26]trien]-17'-one 15',15'-dioxide or (1S,3'R,6'S, 7'S,11'S)-6-chloro-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{1,26}$]octacosa[18,20,26]trien]-17'-one 15',15'-dioxide N,N-Dimethylpyridin-4-amine (DMAP) (0.150 g, 1.23 mmol) was added to a solution of (S)-6'-chloro-5-(((1R,2R)-2-((2S,4R)-4-(2-sulfamoylethoxy)tetrahydro-2H-pyran-2-yl)cyclobutyl) methyl)-3',4,4',5-tetrahydro-2H,2'H-spiro[benzo[b][1,4]oxazepine-3,1'-naphthalene]-7carboxylic acid (Example 836, Step 2; 0.095 g, 0.153 mmol) in DCM (200 mL) at 0° C. Then N1-((ethylimino)methylene)-N3,N3-dimethylpropane-1,3-diamine hydrochloride (EDC; 0.147 g, 0.767 mmol) was added slowly in portions and it was stirred at 0° C. to rt for 3 days. After it was concentrated, the residue was purified by reverse phase preparative HPLC (Gemini™ Prep C$_{18}$ 5 μm column; Phenomenex, Torrance, CA; MeCN in water with 0.1% TFA, gradient elution) to give the title compound (1.5 mg, third eluting peak) as a white solid. $^1$H NMR (400 MHz, CD$_2$Cl$_2$) δ 8.22-8.15 (m, 1H), 7.76-7.69 (m, 1H), 7.26-7.21 (m, 1H), 7.20-7.15 (m, 1H), 7.05-7.11 (m, 1H), 7.01-6.94 (m, 1H), 6.57-6.50 (m, 1H), 4.11-4.08 (m, 2H), 3.87 (br. s., 1H), 3.83-3.77 (m, 2H), 3.76-3.68 (m, 3H), 3.59-3.51 (m, 2H), 3.18 (d, J=14.28 Hz, 1H), 3.12 (dd, J=8.90, 15.55 Hz, 1H), 2.81-2.72 (m, 2H), 2.43-2.35 (m, 1H), 2.16-2.09 (m, 1H), 2.08-1.52 (m, 13H), 1.45-1.37 (m, 1H). m/z (ESI, +ve ion) 601.1 (M+H)$^+$.

Example 837. (1S,3'R,6'R,7'S,11'S)-6-chloro-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'R)-6-chloro-3,4-dihydro-2H,17'H-spiro[naphthalene-1,24'-[8,12,22]trioxa[15]thia[1,1diaza pentacyclo[16.7.2.1$^{7,11}$.0$^{3,6}$.0$^{21,26}$]octacosa[18,20,26]trien]-17'-one 15',15'-dioxide or (1S,3'R,6'S, 7'S,11'R)-6-chloro-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'S, 7'S,11'S)-6-chloro-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide

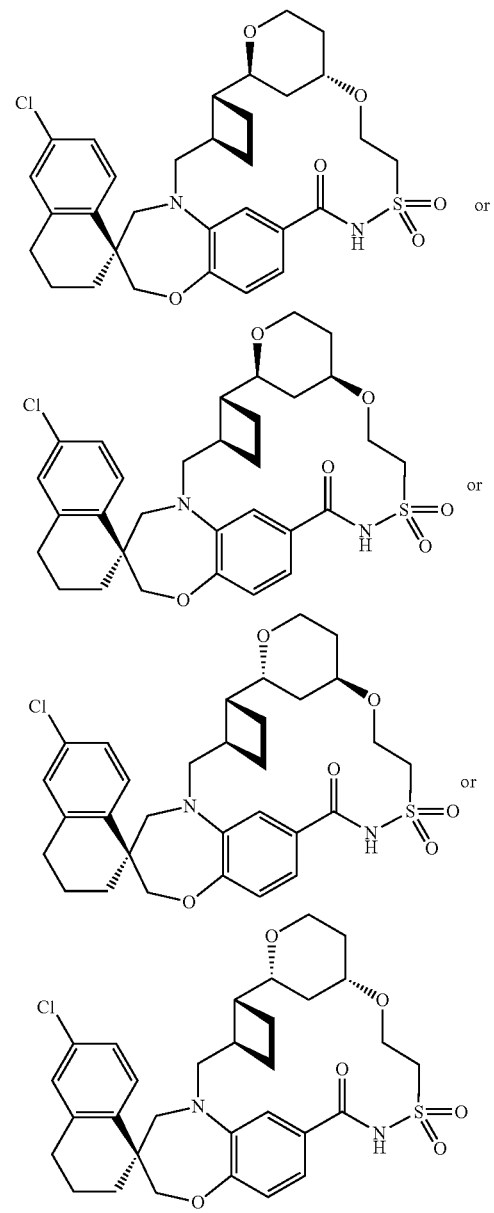

1715

The title compound (11.1 mg) was obtained as a single isomer (first eluting peak) from the reverse phase preparative HPLC in Example 836 as a white solid. ¹H NMR (400 MHz, CD₂Cl₂) δ 8.30-8.13 (m, 1H), 7.71 (m, 1H), 7.17 (m, 1H), 7.07 (m, 2H), 6.96 (m, 1H), 6.82 (m, 1H), 4.11 (m, 1H), 4.06-3.94 (m, 3H), 3.86 (ddd, J=3.42, 8.02, 11.44 Hz, 1H), 3.81-3.68 (m, 4H), 3.54-3.44 (m, 1H), 3.35-3.20 (m, 4H), 2.78 (d, J=5.09 Hz, 2H), 2.25-2.03 (m, 5H), 1.98-1.82 (m, 3H), 1.77-1.63 (m, 2H), 1.59-1.20 (m, 4H). m/z (ESI, +ve ion) 601.1 (M+H)⁺.

Example 838. (1S,3'R,6'R,7'S,11'S)-6-chloro-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'R)-6-chloro-3,4-dihydro-2H,17'H-spiro[naphthalene-1,24'-[8,12,22]trioxa[15]thia[1,1diazapentacyclo[16.7.2.1$^{7,11}$.0$^{3,6}$.0$^{21,26}$]octacosa[18,20,26]trien]-17'-one 15',15'-dioxide or (1S,3'R,6'S, 7'S,11'R)-6-chloro-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'S, 7'S,11'S)-6-chloro-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide

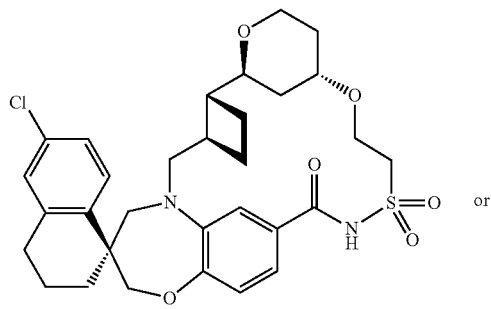 or

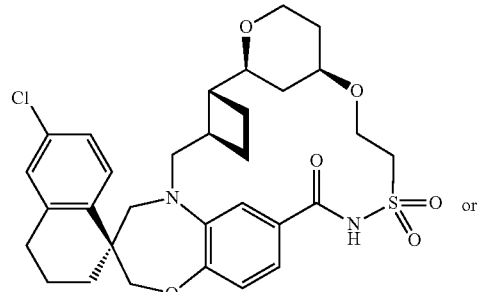 or

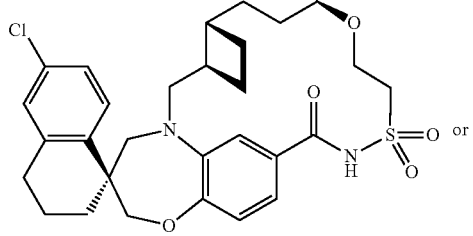 or

1716

-continued

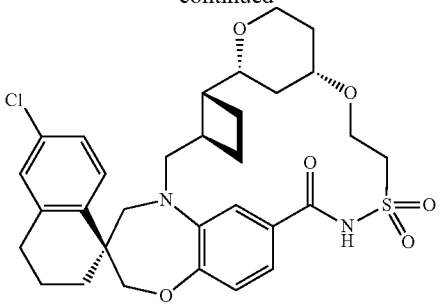

The title compound (12.1 mg) was obtained as a single isomer (second eluting peak) from the reverse phase preparative HPLC in Example 836 as a white solid. ¹H NMR (400 MHz, CD₂Cl₂) δ 8.25-8.18 (m, 1H), 7.71 (m, 1H), 7.19 (m, 1H), 7.09 (m, 1H), 7.02 (m, 1H), 6.95 (m, 1H), 6.82 (m, 1H), 4.20-4.03 (m, 3H), 4.03-3.94 (m, 3H), 3.84-3.62 (m, 3H), 3.57-3.36 (m, 3H), 3.34-3.20 (m, 1H), 3.19-2.87 (m, 3H), 2.81-2.70 (m, 2H), 2.42-1.71 (m, 9H), 1.69-1.58 (m, 1H), 1.47-1.37 (m, 1H), 1.33 (dd, J=5.09, 10.76 Hz, 1H). m/z (ESI, +ve ion) 601.1 (M+H)⁺.

Example 840. (1S,3'R,6'R,7'S,9'R,10'S)-6-chloro-7',9',10'-trihydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide and (1S,3'R,6'R,7'S,9'S,10'R)-6-chloro-7',9',10'-trihydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

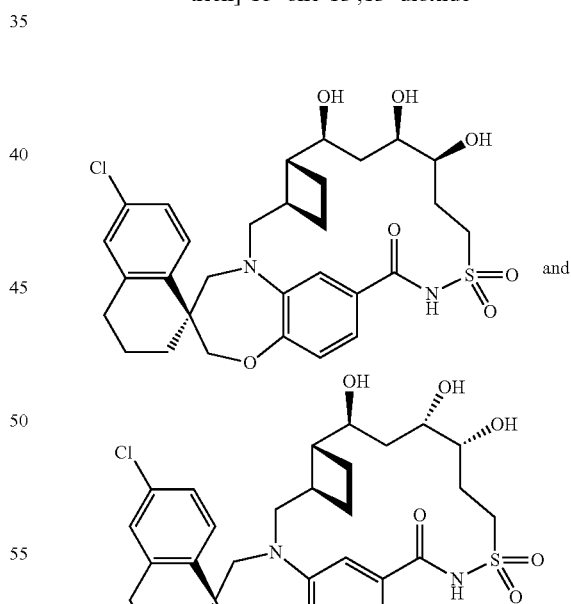

A solution of osmium (VIII) oxide (2.5% solution in tert-BuOH, 0.46 mL, 0.037 mmol) was added to a solution of (1S,3'R,6'R,7'S,9'Z)-6-chloro-7'-hydroxy-3,4-dihydro-2H,15'H-spiro [naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (Example 807; 0.105 g, 0.184 mmol) in acetone (8.4 mL) and THF (8.4 mL). Then 4-methylmorpholine N-oxide (0.058 g, 0.496 mmol) in water (0.08 mL) was added and the mixture was degassed with nitrogen and stirred at rt for 2 h. It was concentrated and the residue was purified by reverse phase preparative HPLC (Gemini™ Prep $C_{18}$ 5 μm column; Phenomenex, Torrance, CA; MeCN in water with 0.1% TFA, gradient elution) to give the title compound (5.2 mg) as a white solid. $^1$H NMR (400 MHz, $CD_2Cl_2$) δ 7.70 (t, J=7.43 Hz, 1H), 7.17 (br. s., 2H), 7.09 (br. s., 1H), 6.95 (d, J=8.22 Hz, 1H), 6.81-6.91 (m, 1H), 4.31 (br. s., 1H), 4.15-4.06 (m, 2H), 3.98-3.82 (m, 2H), 3.79-3.20 (m, 6H), 2.77 (br. s., 3H), 2.34-1.34 (m, 13H). m/z (ESI, +ve ion) 605.2 (M+H)$^+$.

Example 841. (1S,3'R,6'R,7'R,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,10'R,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'R,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6R,7'S,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'R,11'R)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,10'S,11'R)-6-chloro-10'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'S,11'R)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa [18,20,26]trien]-17'-one 15',15'-dioxide

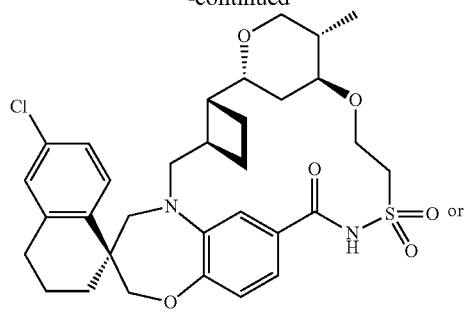

or

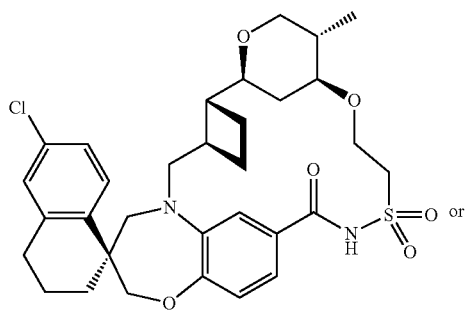

or

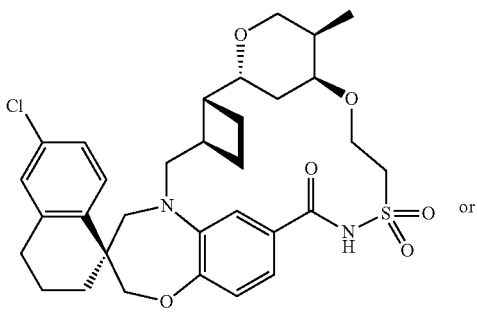

or

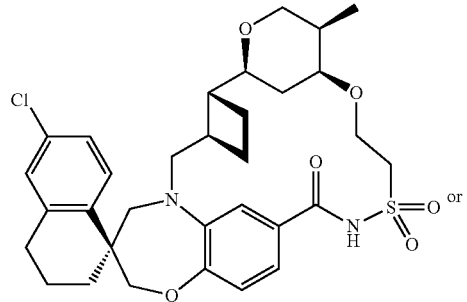

or

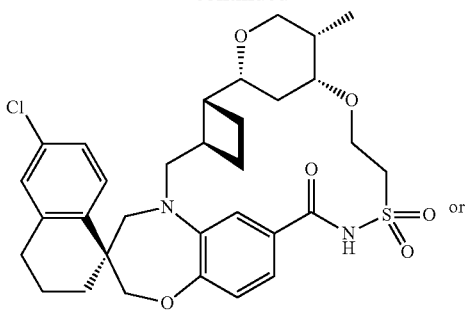

or


or

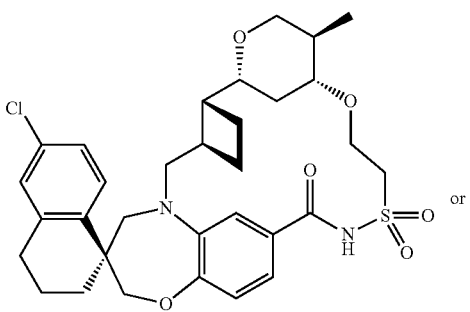

or

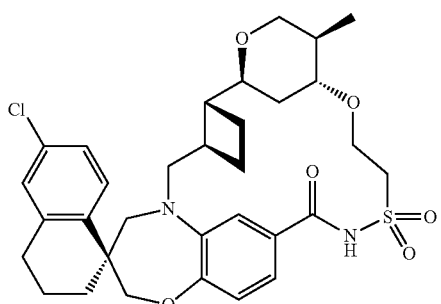

Step 1: (S)-methyl 6'-chloro-5-(((1R,2R)-2-((2R,4S,5R)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S,5R)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S,5S)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R,5S)-4-hydroxy-5-methyl tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R,5S)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R,5R)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R,5R)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

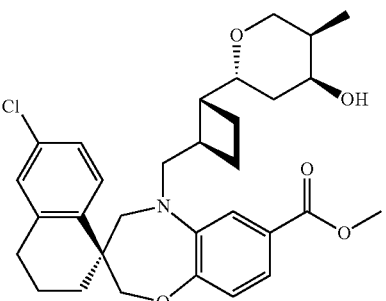

or

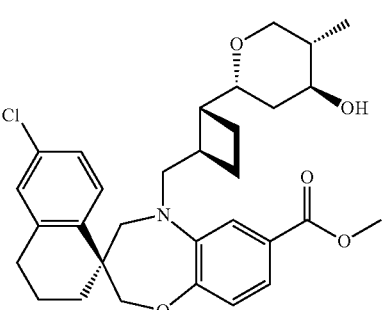

or

1721
-continued

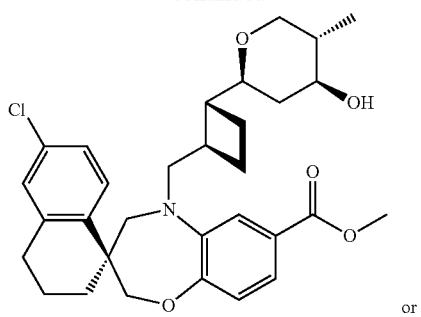

or

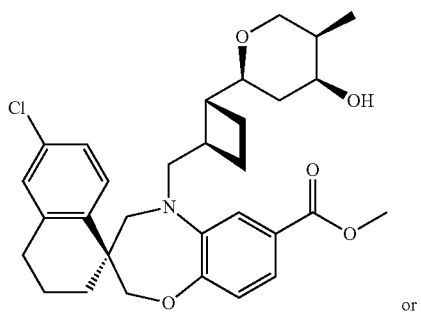

or

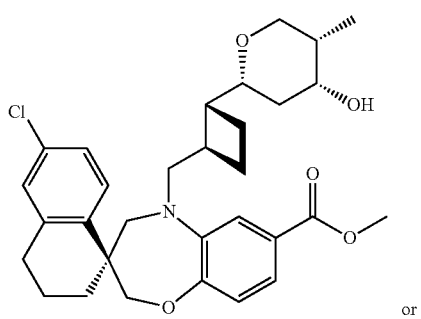

or

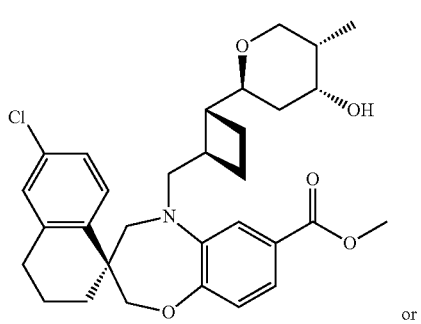

or

1722
-continued

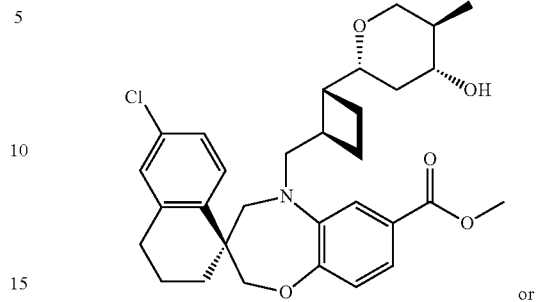

or

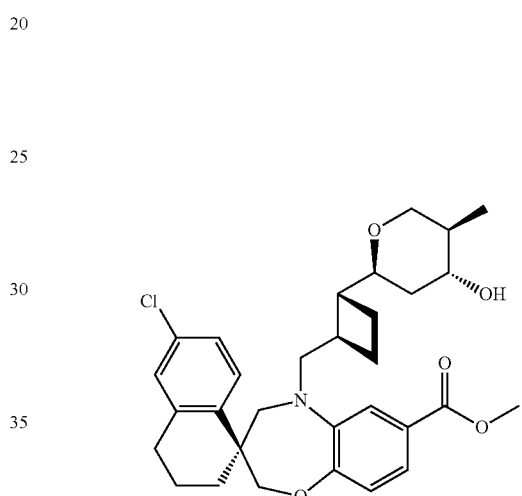

TFA (5.1 mL) was added slowly to a solution of (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, STEP 20A; 0.417 g, 0.919 mmol) and 2-methyl-3-buten-1-ol (0.123 mL, 1.19 mmol) in DCM (10 mL) which was degassed with $N_2$. It was stirred at rt for 22 min. The reaction mixture was added slowly to $Na_2CO_3$ (aq) solution (40 mL) and MeOH (20 mL). After it was stirred at rt for 15 min, the mixture was extracted with EtOAc (3×130 mL). The organic phase was dried over anhydrous sodium sulfate and concentrated. The residue was purified by reverse phase preparative HPLC (Gemini™ Prep $C_{18}$ 5 μm column; Phenomenex, Torrance, CA; MeCN in water with 0.1% TFA, gradient elution). The title compound (60 mg) was obtained as a single isomer (first eluting peak). m/z (ESI, +ve ion) 540.1 $(M+H)^+$.

Step 2: (S)-6'-chloro-5-(((1R,2R)-2-((2R,4S,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4S,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4S,5S)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4S,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R,5S)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4R,5S)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid

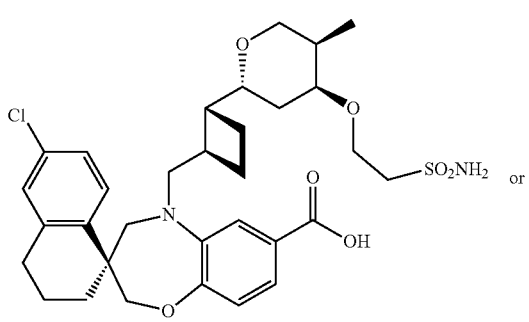 or

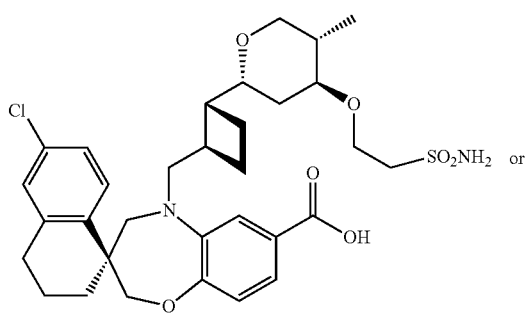 or

-continued

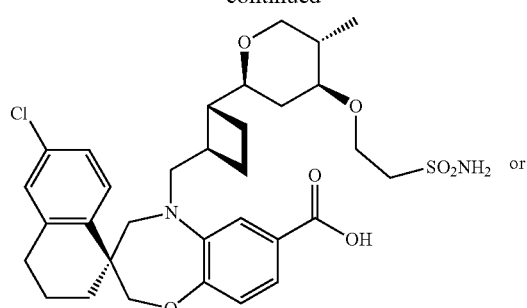 or

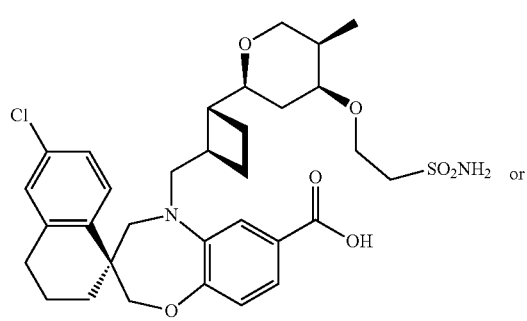 or

 or

 or

1725

-continued

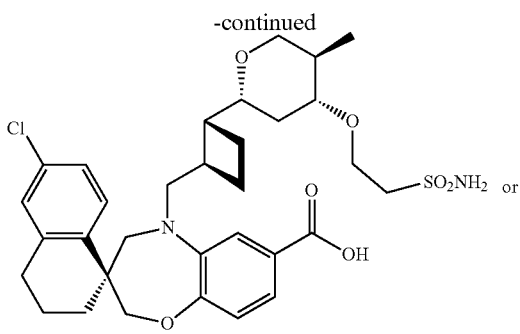

Sodium hydride (60% dispersion in mineral oil; 12 mg, 0.55 mmol) was added to a solution of (1'S)-methyl 6'-chloro-5-(((1R,2R)-2-((2R,4S)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 841, Step 1; 0.030 g, 0.030 mmol) in THF (1.6 mL), which was cooled by ice bath. After it was stirred at rt for 24 min N,N-bis(4-methoxybenzyl) ethenesulfonamide (Example 831, Step 2; 0.039 g, 0.111 mmol) in THF (2 mL) was added. It was stirred at rt for 60 min. Water (2 mL) and EtOAc (120 mL) were added. The organic phase was washed with brine, dried over anhydrous sodium sulfate and concentrated. The residue was purified by reverse phase preparative HPLC (Gemini™ Prep C$_{18}$ 5 µm column; Phenomenex, Torrance, CA; MeCN in water with 0.1% TFA, gradient elution) to provide the title compound (15 mg).

Hydrolysis I: The residue was dissolved in THF (3 mL), MeOH (6 mL) and 1M LiOH (6 mL) and the mixture was stirred at 50° C. for 3 h. It was concentrated, acidified with 1N HCl solution to pH 2-4, extracted with EtOAc (100 mL). The organic phase was washed with brine and dried over anhydrous sodium sulfate and concentrated.

Hydrolysis II: The residue was dissolved in 1:3 TFA/DCM (5 mL) and stirred at rt for 18 h. After it was concentrated the residue was purified by reverse phase preparative HPLC (Gemini™ Prep C$_{18}$ 5 µm column; Phenomenex, Torrance, CA; MeCN in water with 0.1% TFA, gradient elution) to provide the title compound (8 mg) as a white solid. m/z (ESI, +ve ion) 633.1 (M+H)$^+$.

Step 3: (1S,3'R,6'R,7'R,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,10'R,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'R,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6R,7'S,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'R,11'R)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,10'S,11'R)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'S,11'R)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide N,N-Dimethylpyridin-4-amine (DMAP) (0.026 g, 0.215 mmol) was added to a solution of (1'S)-6'-chloro-5-(((1R,2R)-2-((2R,4S)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid (Example 841, Step 2; 0.008 g, 13 µmol) in DCM (32 mL) at 0° C. Then N1-((ethylimino)methylene)-N3,N3-dimethylpropane-1,3-diamine hydrochloride (EDC) (0.027 g, 0.139 mmol) was added slowly in portions and it was stirred at 0° C. to rt for 17 h. It was concentrated and the residue was purified by reverse phase preparative HPLC (Gemini™ Prep C$_{18}$ 5 µm column; Phenomenex, Torrance, CA; MeCN in water with 0.1% TFA, gradient elution) to provide the title compound (5.5 mg) as a white solid. $^1$H NMR (400 MHz, CD$_2$Cl$_2$) δ 8.22 (s, 1H), 7.72 (d, J=8.61 Hz, 1H), 7.18 (dd, J=2.35, 8.41 Hz, 1H), 7.09 (d, J=2.35 Hz, 1H), 7.06-7.02 (m, 1H), 6.98-6.89 (m, 1H), 6.82 (d, J=1.96 Hz, 1H), 4.13-3.99 (m, 5H), 3.89-3.77 (m, 3H), 3.75-3.65 (m, 2H), 3.44 (d, J=11.54 Hz, 1H), 3.23-3.11 (m, 3H), 3.06 (t, J=11.44 Hz, 1H), 2.80-2.72 (m, 2H), 2.36-2.2 (m, 2H), 2.10-2.02 (m, 2H), 1.98-1.89 (m, 2H), 1.88-1.77 (m, 3H), 1.71-1.59 (m, 1H), 1.58-1.48 (m, 1H), 1.41 (t, J=12.81 Hz, 1H), 0.88-0.84 (m, 3H). m/z (ESI, +ve ion) 615.0 (M+H)$^+$.

Example 843. (1S,3'R,6'R,7'R)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

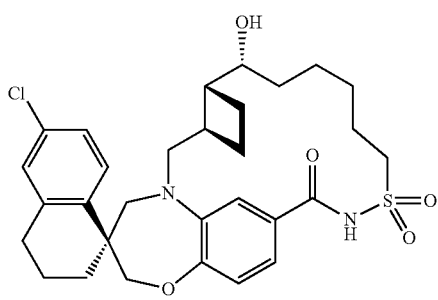

A mixture of (1S,3'R,6'R,7'R,9'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (Example 844; 0.248 g, 0.434 mmol) and platinum (IV) oxide (0.099 g, 0.434 mmol) in EtOAc (140 mL) was stirred under H$_2$ at rt for 1 h. The mixture was filtered through syringe filter to remove solid catalyst. The filtrate was concentrated to provide the title compound (5 mg) as a white solid. $^1$H NMR (400 MHz, CD$_2$Cl$_2$) δ 8.54 (m, 1H), 7.77-7.69 (m, 1H), 7.28 (m, 1H), 7.17 (m, 1H), 7.12-7.05 (m, 2H), 6.94 (m, 1H), 4.14-4.06 (m, 2H), 3.96-3.88 (m, 1H), 3.86-3.76 (m, 1H), 3.73-3.66 (m, 1H), 3.64-3.56 (m, 1H), 3.41-3.31 (m, 1H), 3.27-3.18 (m, 1H), 3.14-3.04 (m, 1H), 2.83-2.71 (m, 2H), 2.52-2.31 (m, 2H), 2.07-1.21 (m, 15H), 0.94-0.81 (m, 2H). m/z (ESI, +ve ion) 573.2 (M+H)$^+$.

Example 844. (1S,3'R,6'R,7'R,9'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide

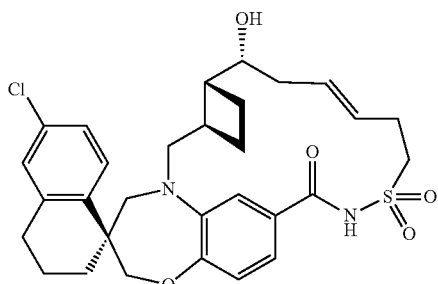

Step 1: (S)-methyl 6'-chloro-5-(((1R,2R)-2-((R)-1-hydroxybut-3-en-1-yl)cyclo butyl)methyl)-3',4,4',5-tetrahydro-2H,2'H-spiro[benzo[b][1,4]oxazepine-3,1'-naphthalene]-7-carboxylate

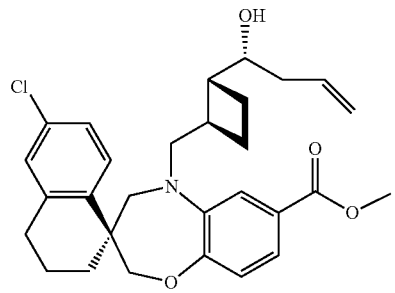

To a mixture of allyl iodide (0.81 mL, 8.8 mmol), indium powder (140 mg, 8.8 mmol) in DMF (41 mL) was added (1'S)-methyl 6'-chloro-5-((2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A; 1.00 g, 2.2 mmol) in DMF (15 mL). It was stirred at rt for 15 min. The reaction was diluted with water (30 mL) and EtOAc (300 mL). The organic phase was washed with water, brine, dried over anhydrous sodium sulfate and concentrated. The residue was loaded to a 40 g ISCO Gold column and eluted with 0% to 5% EtOAc/hexane to provide the title compound (304 mg) as a white solid. m/z (ESI, +ve ion) 496.0 (M+H)$^+$.

Step 2: (S)-6'-chloro-5-(((1R,2R)-2-((R)-1-hydroxy-but-3-en-1-yl)cyclobutyl)methyl)-3',4,4',5-tetra-hydro-2H,2'H-spiro[benzo[b][1,4]oxazepine-3,1'-naphthalene]-7-carboxylic Acid

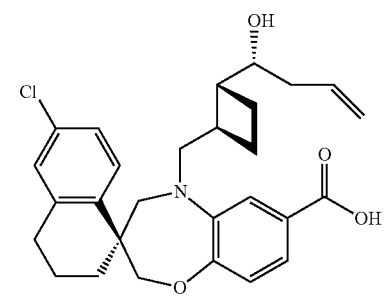

A mixture of lithium hydroxide (1.0 M aqueous solution, 6.45 mL, 6.45 mmol) and (1'S)-methyl 6'-chloro-5-((2-((R)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate (Example 844, Step 1; 0.32 g, 0.645 mmol) in MeOH (6.5 mL) and THF (6.5 mL) was stirred at 50° C. for 3 h. The reaction mixture was concentrated and the residue was acidified with 1N HCl solution to pH 2-3. It was extracted with EtOAc (200 mL), washed with brine (3 mL), dried over anhydrous sodium sulfate and concentrated to provide the title compound (311 mg) as a white solid. m/z (ESI, +ve ion) 482.1 (M+H)$^+$.

Step 3: (S)—N-(but-3-en-1-ylsulfonyl)-6'-chloro-5-(((1R,2R)-2-((R)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide

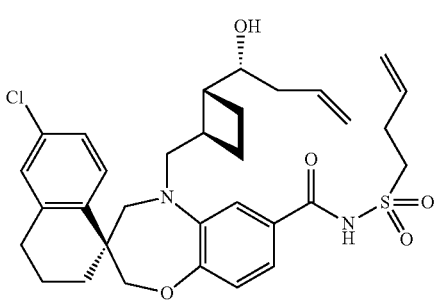

N-(3-Dimethylaminopropyl)-N'-ethylcarbodiimide hydrochloride (EDC; 0.247 g, 1.29 mmol) was added to a solution of (1'S)-6'-chloro-5-((2-((R)-1-hydroxybut-3-en-1-yl)cyclobutyl) methyl)-3',4,4',5-tetrahydro-2H,2'H-spiro [benzo[b][1,4]oxazepine-3,1'-naphthalene]-7-carboxylic acid (Example 844, Step 2; 0.311 g, 0.645 mmol) and but-3-ene-1-sulfonamide (EE15; 0.480 g, 3.55 mmol) in DCM (34 mL). Then N,N-dimethylpyridin-4-amine (DMAP) (0.150 g, 1.226 mmol) was added and it was stirred at rt overnight. After concentration the residue was loaded to a 24 g ISCO Gold column and eluted with 0% to 20% EtOAc (containing 0.3% AcOH)/hexane (containing 0.3% AcOH) to provide the title compound (303 mg) as a white solid. m/z (ESI, +ve ion) 599.2 (M+H)$^+$.

Step 4: (1S,3'R,6'R,7'R,9'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide

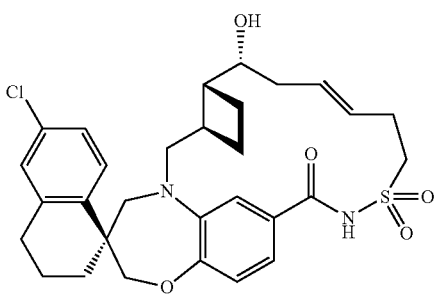

A 500 mL three-necked round bottom flask was charged with (S)—N-(but-3-en-1-ylsulfonyl)-6'-chloro-5-(((1R,2S)-2-((R)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide (Example 844, Step 3; 0.020 g, 0.033 mmol) in toluene (100 mL). It was stirred at rt for 10 min to dissolve the solid starting material and then subjected to three cycles of evacuation/back-filling with nitrogen. To the homogeneous solution was added a solution of Hoveyda-Grubbs II (4.18 mg, 6.68 μmol) in toluene (5 mL) at ambient temperature. The mixture was stirred at 106° C. under nitrogen for 1 h. Air was blown for 10 min to deactivate the catalyst and then it was concentrated. The residue was purified by reverse phase preparative HPLC (Gemini™ Prep C$_{18}$ 5 μm column; Phenomenex, Torrance, CA; MeCN in water with 0.1% TFA, gradient elution) to give the title compound (8.4 mg, second peak) as a white solid. $^1$H NMR (400 MHz, CD$_2$Cl$_2$) δ 9.96 (br. s., 1H), 7.75 (d, J=8.61 Hz, 1H), 7.52 (br. s., 1H), 7.15-7.38 (m, 2H), 7.09 (d, J=2.35 Hz, 1H), 6.98 (br. s., 1H), 5.73-5.63 (m, 1H), 5.54-5.45 (m, 1H), 4.10 (ddd, J=5.09, 13.01, 15.55 Hz, 3H), 3.92-3.61 (m, 2H), 3.42-3.28 (m, 1H), 3.25-2.98 (m, 2H), 2.80-2.63 (m, 4H), 2.61-2.51 (m, 2H), 2.33 (t, J=8.22 Hz, 1H), 2.24-1.23 (m, 11H). m/z (ESI, +ve ion) 571.1 (M+H)$^+$.

Example 845. (1S,3'R,6'R,7'R)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide

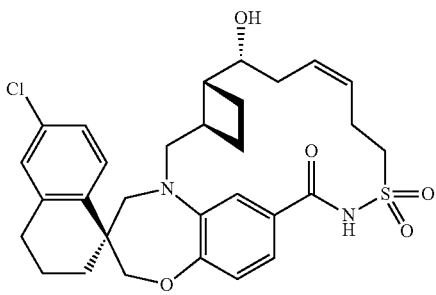

The title compound (4.5 mg) was obtained as a single isomer (first eluting peak) from the reverse phase preparative HPLC in Example 844 as a white solid. $^1$H NMR (400 MHz, CD$_2$Cl$_2$) δ 9.48-9.39 (m, 1H), 7.77-7.71 (m, 1H), 7.50-7.44 (m, 1H), 7.21-7.15 (m, 1H), 7.13-7.08 (m, 2H), 7.02-6.97 (m, 1H), 5.68-5.58 (m, 1H), 5.56-5.47 (m, 1H), 4.19-4.08 (m, 2H), 3.96 (ddd, J=2.15, 6.06, 15.06 Hz, 1H), 3.87 (d, J=15.45 Hz, 1H), 3.81 (dd, J=4.01, 8.71 Hz, 1H), 3.70 (d, J=14.28 Hz, 1H), 3.33-3.23 (m, 2H), 3.18 (dd, J=8.51, 15.55 Hz, 1H), 2.81-2.74 (m, 2H), 2.72-2.67 (m, 1H), 2.63-2.53 (m, 2H), 2.50-2.37 (m, 2H), 2.30 (m, 1H), 2.05 (m, 1H), 1.98-1.81 (m,), 4H 1.79-1.68 (m, 2H), 149-1.38 (m, 1H). m/z (ESI, +ve ion) 571.1 (M+H)$^+$.

Example 846. (1S,3'R,6'R,7'S,9'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide

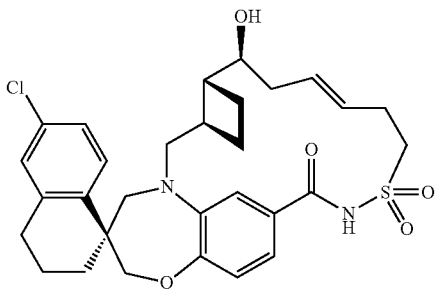

Step 1: (1'S)—N-(but-3-en-1-ylsulfonyl)-6'-chloro-5-(((1R,2R)-2-(1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide

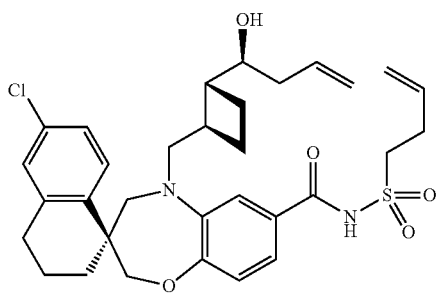

N,N-dimethylpyridin-4-amine (DMAP) (0.830 g, 6.80 mmol) was added to a solution of (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA13A; 1.82 g, 3.78 mmol) and but-3-ene-1-sulfonamide (1.873 g, 13.86 mmol) in DCM (140 mL) which was cooled to 0° C. Then EDC (1.303 g, 6.80 mmol) was added portion by portion and it was stirred at rt for 16 h. The reaction mixture was diluted with EtOAc (400 mL), washed with 1N HCl solution (2×5 mL), brine (3 mL), and dried over anhydrous sodium sulfate, concentrated. The residue was loaded to a 80 g ISCO Gold column and eluted with 0% to 15% EtOAc (containing 0.3% AcOH)/hexane (containing 0.3% AcOH) to provide the title compound (2.09 g) as a white solid. m/z (ESI, +ve ion) 599.0 (M+H)$^+$.

Step 2: (1S,3'R,6'R,7'S,9'E)-6-chloro-7'-hydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa[9,16,18,24]tetraen]-15'-one 13',13'-dioxide

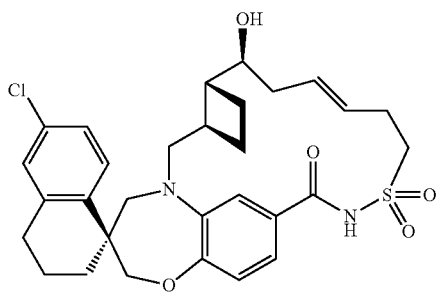

A 1 L round bottom flask was charged with (1'S)—N-(but-3-en-1-ylsulfonyl)-6'-chloro-5-(((1R,2R)-2-(1-hydroxybut-3-en-1-yl)cyclobutyl)methyl)-3',4,4',5-tetrahydro-2H,2'H-spiro [benzo[b][1,4]oxazepine-3,1'-naphthalene]-7-carboxamide (Example 846, Step 1; 1.02 g, 1.70 mmol) in toluene (587 mL). It was stirred at rt for 10 min to dissolve the solid starting material and then subjected to three cycles of evacuation/back-filling with nitrogen. To the homogeneous solution was added a solution of Hoveyda-Grubbs II (0.213 g, 0.340 mmol) in toluene (20 mL). After the mixture was stirred at 106° C. under nitrogen for 75 min air was blown for 10 min to deactivate the catalyst, and then concentrated. The residue was loaded to a 330 g ISCO Gold column and eluted with 0% to 25% EtOAc (containing 0.3% AcOH)/hexane (containing 0.3% AcOH) to give the title compound (0.27 g, second eluting peak) as a white solid. $^1$H NMR (400 MHz, CD$_2$Cl$_2$) δ 9.96 (br. s., 1H), 7.78-7.65 (m, 1H), 7.37 (dd, J=1.96, 8.22 Hz, 1H), 7.16 (dd, J=2.35, 8.61 Hz, 1H), 7.10 (d, J=2.15 Hz, 1H), 7.04 (br. s., 1H), 6.98 (m, 1H), 5.66-5.47 (m, 2H), 4.23-4.09 (m, 2H), 3.98 (ddd, J=5.18, 10.56, 15.55 Hz, 1H), 3.86 (dd, J=3.81, 9.49 Hz, 1H), 3.64-3.49 (m, 2H), 3.38 (td, J=4.74, 15.36 Hz, 2H), 2.92 (br. s., 1H), 2.81 (br. s., 1H), 2.79-2.73 (m, 2H), 2.73-2.63 (m, 1H), 2.52 (d, J=12.72 Hz, 1H), 2.40-2.25 (m, 2H), 2.18 (d, J=8.22 Hz, 1H), 2.01-1.52 (m, 8H). m/z (ESI, +ve ion) 571.0 (M+H)$^+$.

Example 850. (3R,6R,7S,11R,12Z,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide or (3R,6R,7R,11R,12Z,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide or (3R,6R,7S,11S,12Z,24S)-6'-chloro-11-hydroxy-3',4'-dihydro-2'H,17H-spiro[8,22-dioxa-15-thia-1,16-diazapentacyclo [16.7.2.1$^{7,11}$.0$^{3,6}$.0$^{21,26}$]octacosa-12,18,20,26-tetraene-24,1'-naphthalen]-17-one 15,15-dioxide or (3R,6R,7R,11S,12Z,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide

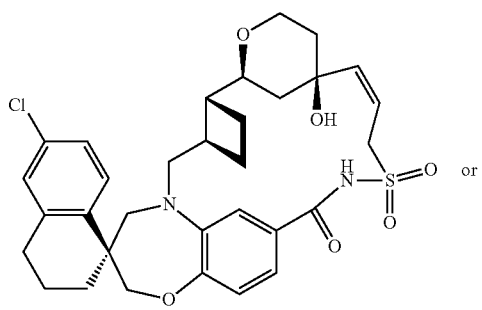

or

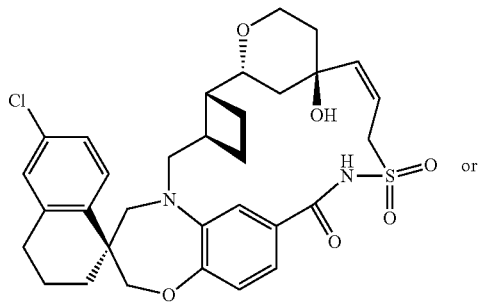

or

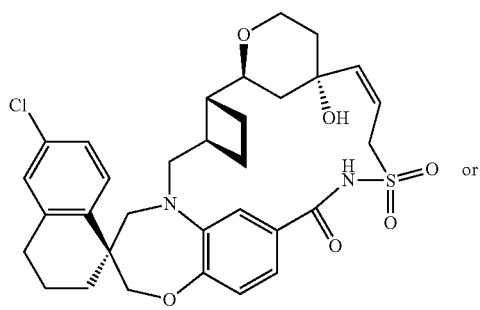

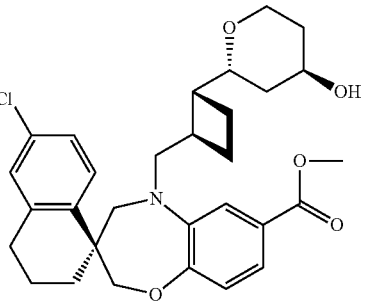

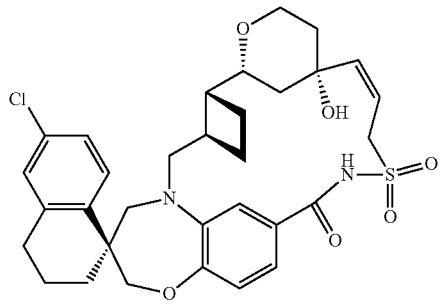

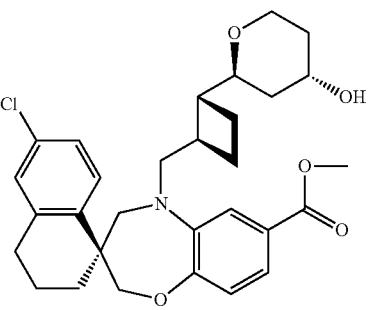

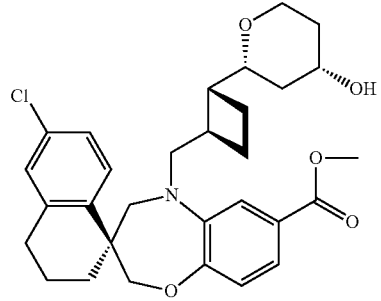

Step 1: (S)-methyl 6'-chloro-5-(((1R,2R)-2-((2S,4R)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-hydroxytetrahydro-2H-pyran-2-yl) cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

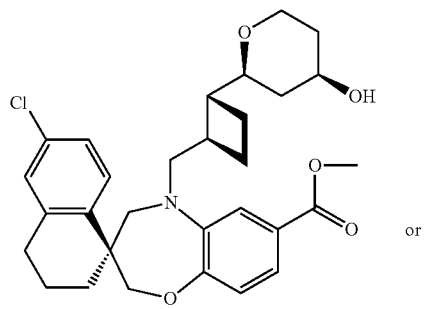

TFA (6 mL) was added slowly to a solution of (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A; 0.412 g, 0.91 mmol) and 3-buten-1-ol (0.10 mL, 1.18 mmol) in DCM (12 mL), which was degassed with N$_2$. After it was stirred at rt for 35 min, the reaction mixture was added slowly to Na$_2$CO$_3$ (aq) solution (50 mL) and MeOH (15 mL). It was stirred at rt for 1.5 h and then extracted with EtOAc (3×90 mL). The organic phase was washed with brine, dried over anhydrous sodium sulfate and concentrated. The residue was loaded to a 24 g ISCO Gold column and eluted with 0% to 30% EtOAc/hexane, to provide a mixture, which was purified by SFC (Method: 250×21.2 mm IC—H column w/ 20 g/min MeOH (0.2% DEA)+60 g/min CO$_2$ on a Thar 80 SFC. Outlet pressure 100 bar; Temp. 20° C.; Wavelength 220 nm). The title compound (102 mg) was obtained as a single isomer (second eluting peak). m/z (ESI, +ve ion) 526.1 (M+H)$^+$.

Step 2: (S)-methyl 6'-chloro-5-(((1R,2R)-2-((S)-4-oxotetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((R)-4-oxotetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate Step 3: (S)-methyl 6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-hydroxy-4-vinyltetrahydro-2H-pyran-2-yl)cyclobutyl)methyl)-3',4,4',5-tetrahydro-2H,2'Hspiro[benzo[b][1,4]oxazepine-3,1'-naphthalene]-7-carboxylate or (S)-methyl 6'-chloro-5-(((1R,2R)-2-((2S,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

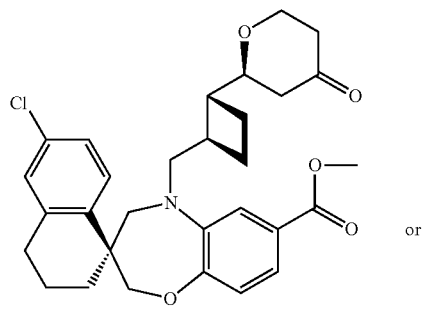

or

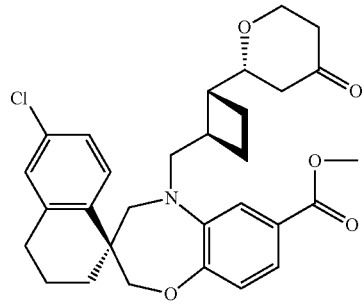

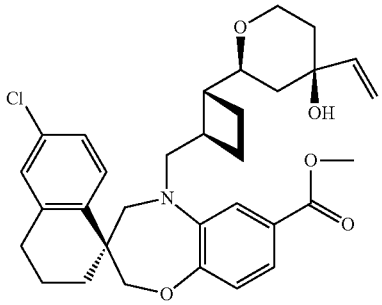

or

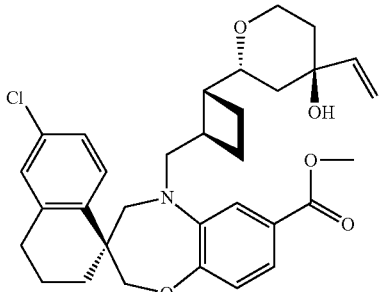

or

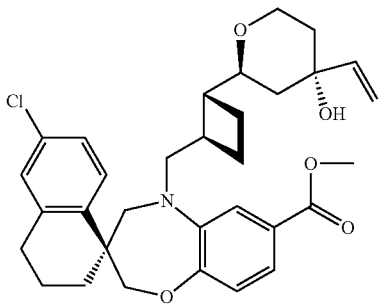

or

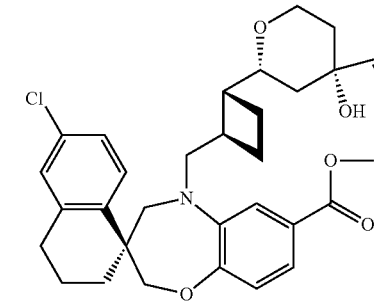

A 100 mL flask charged dimethyl sulfoxide (0.041 mL, 0.58 mmol) and DCM (2.8 mL) was cooled to −78° C. Oxalyl chloride (2.0 M solution in DCM, 0.15 mL, 0.29 mmol) was added dropwise and the reaction mixture was stirred for 10 min. (S)-Methyl 6'-chloro-5-(((1R,2R)-2-((2S,4R)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 850, Step 1; 0.102 g, 0.194 mmol) in DCM (2.8 mL) was added in one portion to above solution. After it was stirred at −78° C. for 17 min, triethylamine (0.135 mL, 0.97 mmol) was added and it was stirred at −78° C. to rt overnight. It was quenched with water (3 mL), extracted with (140 mL). The organic phase was washed with 1 N HCl solution, brine, dried over anhydrous sodium sulfate. It was filtered through silica gel and concentrated to provide the title compound (100 mg) as a white solid. m/z (ESI, +ve ion) 524.1 (M+H)⁺.

1737

Vinylmagnesium chloride (1.6 M solution in THF; 0.58 mL, 0.93 mmol) was added dropwise to a solution of (S)-methyl 6'-chloro-5-(((1R,2R)-2-((S)-4-oxotetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 850, Step 2; 0.097 g, 0.185 mmol) in THF (6 mL) at 0° C. It was stirred at 0° C. for 5 min. It was quenched with NH₄Cl solution and extracted with EtOAc (180 mL). The organic phase was washed with brine, dried over anhydrous sodium sulfate, filtered through short plug of silica gel. After concentration, the title compound was obtained (102 mg) as an oil. m/z (ESI, +ve ion) 552.1 (M+H)⁺.

Step 4: (S)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic

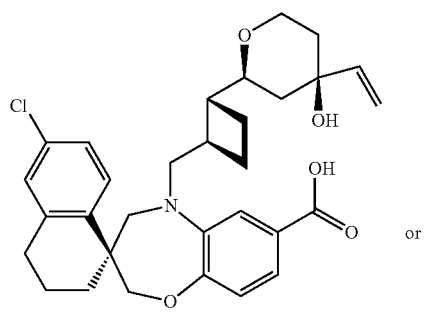

or

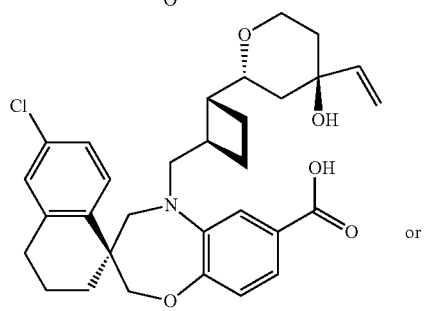

or

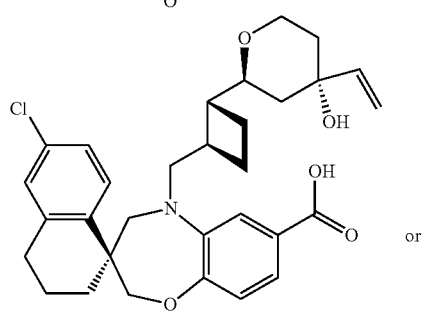

or

1738

-continued

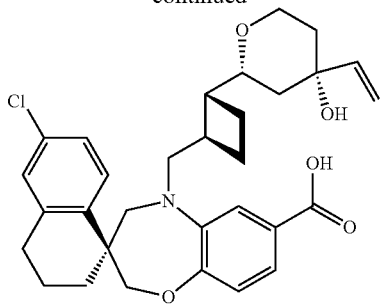

Lithium hydroxide (1.0 M aqueous solution, 5.43 mL, 5.43 mmol) was added to a solution of (1'S)-methyl 6'-chloro-5-(((1R,2R)-2-((2S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 850, Step 3; 0.100 g, 0.18 mmol) in THF (12 mL) and MeOH (6 mL). It was stirred at 50° C. for 60 min. It was concentrated, acidified with 1 N HCl solution to pH 2-4, extracted with EtOAc (160 mL). The organic phase was washed with brine, dried over anhydrous sodium sulfate and concentrated. The residue was purified by reverse phase preparative HPLC (Gemini™ Prep C₁₈ 5 μm column; Phenomenex, Torrance, CA; MeCN in water with 0.1% TFA, gradient elution). The title compound (33 mg) was obtained as a single isomer (first eluting peak) as a white solid. m/z (ESI, +ve ion) 538.1 (M+H)⁺.

Step 5: (S)—N-(allylsulfonyl)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2R)-2-((2R,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2R)-2-((2S,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide

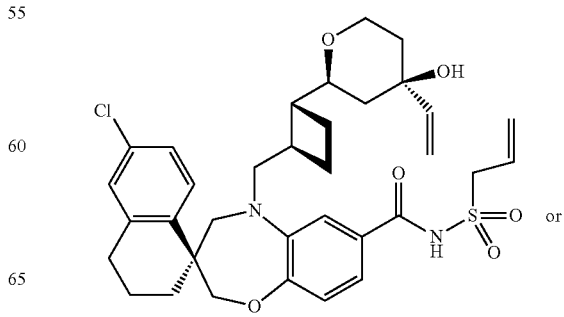

or

-continued

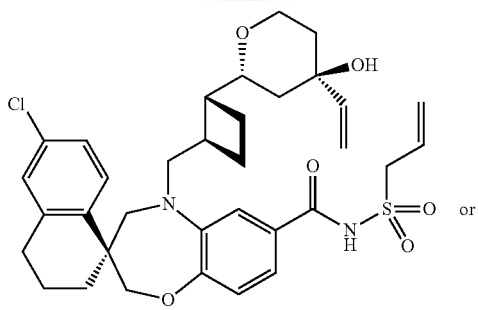

or

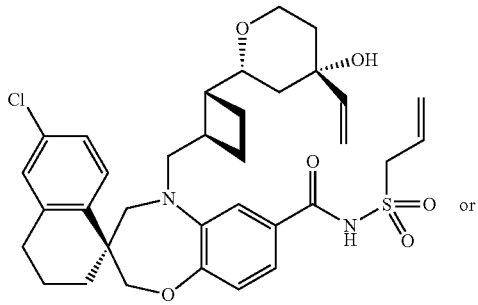

or

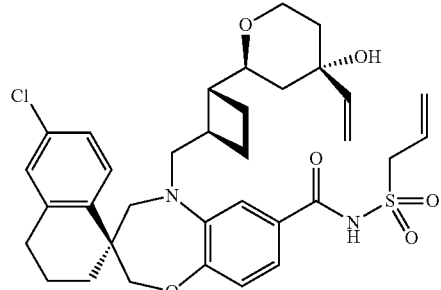

Step 6: (3R,6R,7S,11R,12Z,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide or (3R,6R,7R,11R,12Z,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide or (3R,6R,7S,11S,12Z,24S)-6'-chloro-11-hydroxy-3',4'-dihydro-2'H,17H-spiro[8,22-dioxa-15-thia-1,16-diazapentacyclo [16.7.2.1$^{7,11}$.0$^{3,6}$.0$^{21,26}$]octacosa-12,18,20,26-tetraene-24,1'-naphthalen]-17-one 15,15-dioxide or (3R,6R,7R,11S,12Z,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide

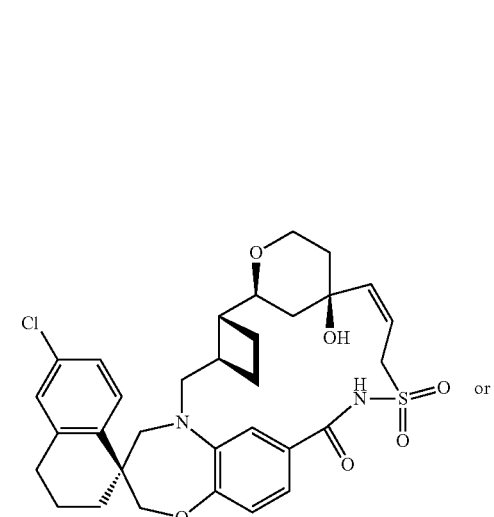

or

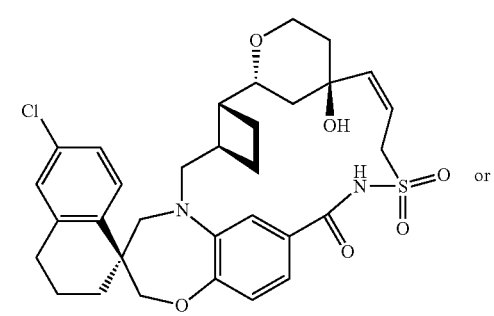

N,N-Dimethylpyridin-4-amine (DMAP) (9.54 mg, 0.078 mmol) was added to a solution of (S)-6'-chloro-5-(((1R,2R)-2-((2S,4R)-4-hydroxy-4-vinyltetrahydro-2H-pyran-2-yl)cyclobutyl) methyl)-3',4,4',5-tetrahydro-2H,2'H-spiro[benzo[b][1,4]oxazepine-3,1'-naphthalene]-7-carboxylic acid (Example 850, Step 4; 0.014 g, 0.026 mmol) in DCM (0.9 mL) at 0° C. Then N1-((ethylimino)methylene)-N3,N3-dimethylpropane-1,3-diamine hydrochloride (EDC) (10.5 mg, 0.055 mmol) was added slowly in portions and it was stirred at 0° C. to rt for 16 h. Then it was concentrated and the residue was purified by reverse phase preparative HPLC (Gemini™ Prep C$_{18}$ 5 µm column; Phenomenex, Torrance, CA; MeCN in water with 0.1% TFA, gradient elution) to give the title compound (11 mg) as a white solid. m/z (ESI, +ve ion) 641.1 (M+H)$^+$.

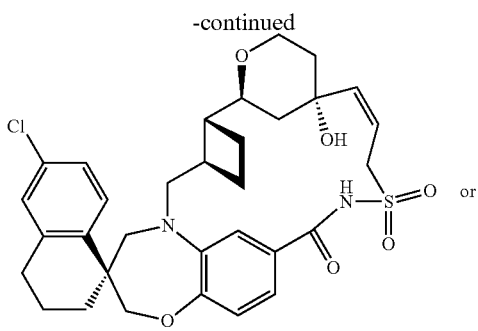

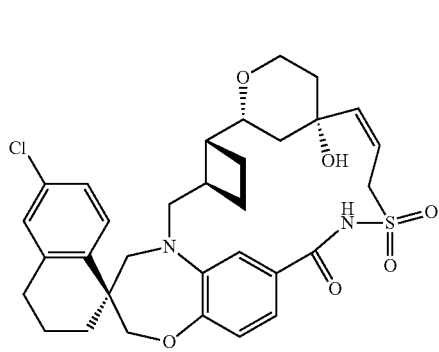

A 250 mL round bottom flask was charged with (S)—N-(allylsulfonyl)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide (Example 850, Step 5; 0.011 g, 0.017 mmol) in toluene (36 mL). It was stirred at rt for 10 min to dissolve the solid starting material and then subjected to three cycles of evacuation/back-filling with nitrogen. To the homogeneous solution was added a solution of Hoveyda-Grubbs II (2.2 mg, 3.4 μmol) in toluene (3 mL). The mixture was stirred at 106° C. under nitrogen for 1 h. Then it was concentrated and the residue was purified by reverse phase preparative HPLC (Gemini™ Prep C$_{18}$ 5 μm column; Phenomenex, Torrance, CA; MeCN in water with 0.1% TFA, gradient elution). The title compound (1.1 mg) was obtained as a single isomer (second eluting peak). $^1$H NMR (500 MHz, CD$_2$Cl$_2$) δ 8.11 (m, 1H), 7.69 (m, 1H), 7.17 (m, 1H), 7.09 (m, 2H), 6.92 (m, 2H), 6.10 (dd, J=1.96, 11.98 Hz, 1H), 5.84 (dd, J=12.59, 15.53 Hz, 1H), 5.53-5.45 (m, 2H), 4.13-4.01 (m, 2H), 3.94-3.80 (m, 3H), 3.73 (d, J=13.94 Hz, 1H), 3.46 (dt, J=3.91, 11.86 Hz, 1H), 3.20-3.05 (m, 3H), 2.82-2.72 (m, 2H), 2.17-1.99 (m, 6H), 1.96-1.34 (m, 9H). m/z (ESI, +ve ion) 613.0 (M+H)$^+$.

Example 851. (3R,6R,7S,11S,12E,24S)-6'-chloro-11-hydroxy-3',4'-dihydro-2'H,17H-spiro[8,22-dioxa-15-thia-1,16-diazapentacyclo [16.7.2.1$^{7,11}$.0$^{3,6}$.0$^{21,26}$]octacosa-12,18,20,26-tetraene-24,1'-naphthalen]-17-one 15,15-dioxide or (3R,6R,7R,11S,12E,24S)-6'-chloro-11-hydroxy-3',4'-dihydro-2'H,17H-spiro[8,22-dioxa-15-thia-1,16-diazapentacyclo [16.7.2.1$^{7,11}$.0$^{3,6}$.0$^{21,26}$]octacosa-12,18,20,26-tetraene-24,1'-naphthalen]-17-one 15,15-dioxide or (3R,6R,7R,11R,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide or (3R,6R,7S,11R,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide

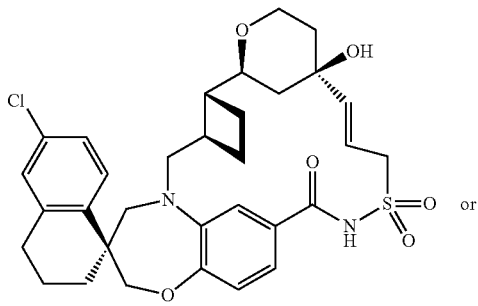

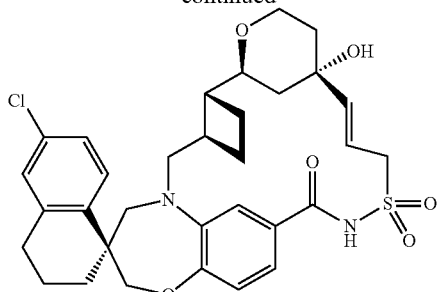

The title compound (4.6 mg) was obtained as a single isomer (first eluting peak) from the reverse phase preparative HPLC in Example 850. $^1$H NMR (500 MHz, CD$_2$Cl$_2$) δ 8.28 (br. s., 1H), 7.65 (d, J=8.56 Hz, 1H), 7.15 (dd, J=2.32, 8.44 Hz, 1H), 7.10 (d, J=2.20 Hz, 1H), 7.01 (dd, J=1.71, 8.07 Hz, 1H), 6.92-6.97 (m, 1H), 6.85 (s, 1H), 6.31 (d, J=15.41 Hz, 1H), 5.94 (ddd, J=6.11, 8.93, 15.28 Hz, 1H), 4.35-4.27 (m, 1H), 4.24-4.13 (m, 2H), 4.12-4.07 (m, 1H), 3.95-3.89 (m, 1H), 3.60 (d, J=14.18 Hz, 1H), 3.35-3.49 (m, 4H), 3.28 (dd, J=3.91, 10.76 Hz, 1H), 2.79-2.70 (m, 2H), 2.43 (d, J=3.91 Hz, 1H), 2.00-1.54 (m, 12H), 1.44 (br. s., 1H), 1.39-1.33 (m, 1H). m/z (ESI, +ve ion) 613.0 (M+H)$^+$.

Example 853. (1S,3'R,6'R,7'R,8'R)-6-chloro-7',8'-dihydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13', 13'-dioxide or (1S,3'R,6'R,7'S,8'S)-6-chloro-7',8'-dihydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13', 13'-dioxide

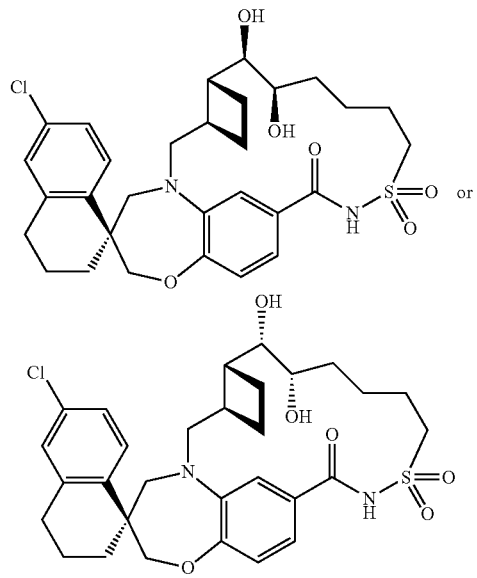

A solution of osmium(VIII) oxide (2.5% solution in tert-BuOH, 0.18 mL, 0.014 mmol) was added to a solution of (1S,3'R,6'S, 7'E)-6-chloro-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide (Example 858; 0.040 g, 0.072 mmol) in acetone (3.3 mL) and THF (3.3 mL). Then 4-methylmorpholine N-oxide (0.020 g, 0.173 mmol) was added and the mixture was degassed with nitrogen. It was stirred at rt for 2.5 h and concentrated. The residue was purified by reverse phase preparative HPLC (Gemini™ Prep C$_{18}$ 5 µm column; Phenomenex, Torrance, CA; MeCN in water with 0.1% TFA, gradient elution). The title compound (4.1 mg) was obtained as a single isomer (first eluting peak) as a white solid. $^1$H NMR (400 MHz, CD$_2$Cl$_2$) δ 8.53 (br. s., 1H), 7.69 (m, 1H), 7.18 (dd, J=2.25, 8.51 Hz, 1H), 7.09 (m, 2H), 7.02-6.89 (m, 2H), 4.16-4.04 (m, 2H), 3.85-3.69 (m, 2H), 3.67-3.48 (m, 2H), 3.44-3.30 (m, 2H), 3.22-3.09 (m, 2H), 2.84-2.73 (m, 2H), 2.59 (m, 1H), 2.39 (m, 1H), 2.18-1.28 (m, 16H). m/z (ESI, +ve ion) 589.1 (M+H)$^+$.

Example 857. (1S,3'R,6'R,7'R,8'R)-6-chloro-7',8'-dihydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13', 13'-dioxide or (1S,3'R,6'R,7'S,8'S)-6-chloro-7',8'-dihydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13', 13'-dioxide

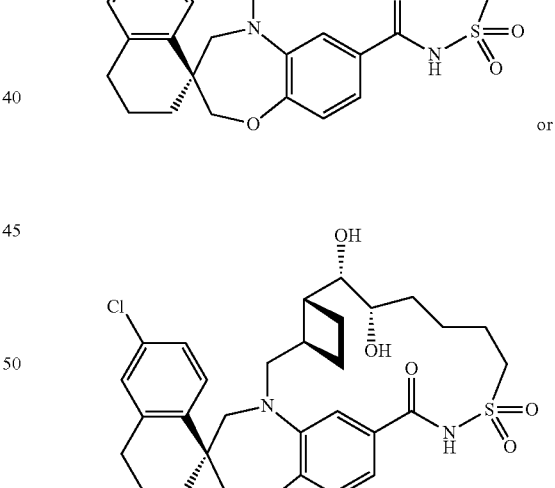

The title compound was obtained as a single isomer (second eluting peak) from the reverse phase perparative HPLC in Example 853. $^1$H NMR (400 MHz, CD$_2$Cl$_2$) δ 7.74 (m, 1H), 7.33-7.43 (m, 1H), 7.19 (m, 1H), 7.10 (d, J=4.50 Hz, 1H), 7.00-6.88 (m, 2H), 4.16-4.04 (m, 2H), 3.97-3.78 (m, 2H), 3.75-3.67 (m, 1H), 3.65-3.51 (m, 2H), 3.51-2.97 (m, 5H), 2.78 (br. s., 2H), 2.39-1.16 (m, 14H)). m/z (ESI, +ve ion) 589.1 (M+H)$^+$.

Example 858. (1S,3′R,6′S, 7′E)-6-chloro-3,4-di-hydro-2H,15′H-spiro[naphthalene-1,22′-[20]oxa[13]thia[1,14]diazatetracyclo[14.7.2.0³,⁶.0¹⁹,²⁴]pentacosa[7,16,18,24]tetraen]-15′-one 13′,13′-dioxide

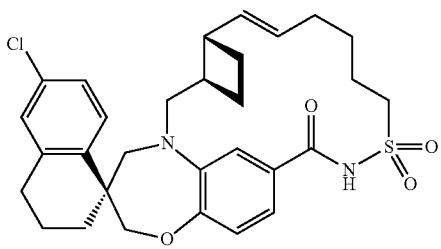

Step 1: (S)-methyl 6′-chloro-5-(((1R,2S)-2-vinylcyclobutyl)methyl)-3′,4,4′,5-tetrahydro-2H,2′H-spiro[benzo[b][1,4]oxazepine-3,1′-naphthalene]-7-carboxylate

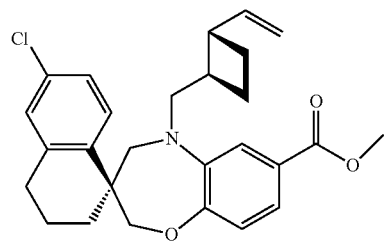

A solution of methyltriphenylphosphonium bromide (1.02 g, 2.86 mmol) in THF (5.7 mL) was cooled to 0° C. n-Butyl lithium solution (2.5 M in hexane, 1.03 mL, 2.58 mmol) was added dropwise and it was stirred at 0° C. for 9 min. The resulting Wittig reagent (yellow solution) was added to a solution of (S)-methyl 6′-chloro-5-(((1R,2R)-2-formylcyclobutyl)methyl)-3′,4,4′,5-tetrahydro-2H,2′H-spiro[benzo[b][1,4]oxazepine-3,1′-naphthalene]-7-carboxylate (Intermediate AA11A, Step 20A; 0.130 g, 0.286 mmol) in THF (1.2 mL) until the yellow color persisted. After it was stirred at 0° C. for 5 min, the reaction mixture was added to a stirred ice-water (3 mL). The organic phase was separated and the aqueous was extracted with EtOAc (120 mL). The combined organic phase was washed with brine, dried anhydrous sodium sulfate. After concentration the residue was loaded to a 4 g ISCO Gold column and eluted with 0% to 10% EtOAc/hexane to provide the title compound (92 mg) as a white solid. m/z (ESI, +ve ion) 452.1 (M+H)⁺.

Step 2: (S)-6′-chloro-5-(((1R,2S)-2-vinylcyclobutyl)methyl)-3′,4,4′,5-tetrahydro-2H,2′H-spiro[benzo[b][1,4]oxazepine-3,1′-naphthalene]-7-carboxylic Acid

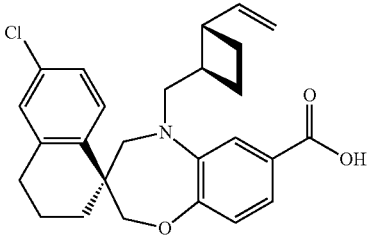

Lithium hydroxide (1M aqueous solution; 1.9 mL, 1.9 mmol) was added to a solution of (S)-methyl 6′-chloro-5-(((1R,2S)-2-vinylcyclobutyl)methyl)-3′,4,4′,5-tetrahydro-2H,2′H-spiro[benzo[b][1,4]oxazepine-3,1′-naphthalene]-7-carboxylate (Example 858, Step 1; 0.087 g, 0.192 mmol) in THF (4 mL) and MeOH (2 mL). It was stirred at 50° C. for 4 h. After concentration, it was acidified with 1 N HCl solution to pH 2-3, extracted with EtOAc (80 mL). The organic phase was washed with brine, dried over anhydrous sodium sulfate. The solution was concentrated to give the title compound (84 mg) as a white solid. m/z (ESI, +ve ion) 438.2 (M+H)⁺.

Step 3: (S)-6′-chloro-N—(HEX-5-en-1-ylsulfonyl)-5-(((1R,2S)-2-vinylcyclobutyl)methyl)-3′,4,4′,5-tetrahydro-2H,2′H-spiro[benzo[b][1,4]oxazepine-3,1′-naphthalene]-7-carboxamide

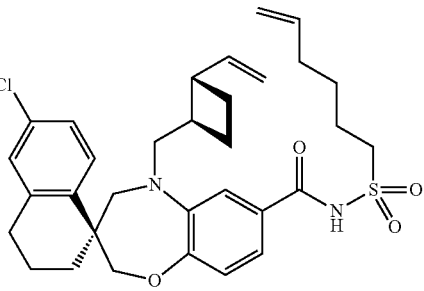

N,N-Dimethylpyridin-4-amine (DMAP) (0.030 g, 0.247 mmol) was added to a solution of (S)-6′-chloro-5-(((1R,2S)-2-vinylcyclobutyl)methyl)-3′,4,4′,5-tetrahydro-2H,2′H-spiro[benzo[b][1,4]oxazepine-3,1′-naphthalene]-7-carboxylic Acid (Example 858, Step 2; 0.060 g, 0.137 mmol) and hex-5-ene-1-sulfonamide (EE25; 0.112 g, 0.685 mmol) in DCM (5 mL) at 0° C. (ice bath). Then N-(3-dimethylaminopropyl)-N′-ethylcarbodiimide hydrochloride (EDC) (0.047 g, 0.25 mmol) was added portion by portion slowly and it was stirred at rt for 16 h. After it was concentrated the residue was purified by reverse phase preparative HPLC (Gemini™ Prep C₁₈ 5 μm column; Phenomenex, Torrance, CA; MeCN in water with 0.1% TFA, gradient elution) to give the title compound (72 mg) as a white solid. m/z (ESI, +ve ion) 583.3 (M+H)⁺.

Step 4: (1S,3'R,6'S, 7'E)-6-chloro-3,4-dihydro-2H, 15'H-spiro[naphthalene-1,22'-[20]oxa[13]thia[1,14] diazatetracyclo[14.7.2.0$^{3,6}$.0$^{19,24}$]pentacosa[7,16,18, 24]tetraen]-15'-one 13',13'-dioxide

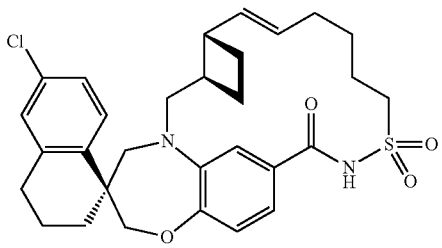

A 250 mL round bottom flask was charged with (S)-6'-chloro-N-(hex-5-en-1-ylsulfonyl)-5-(((1R,2S)-2-vinylcyclobutyl)methyl)-3',4,4',5-tetrahydro-2H,2'H-spiro[benzo[b][1,4]oxazepine-3,1'-naphthalene]-7-carboxamide (Example 858, Step 3; 0.072 g, 0.123 mmol) in toluene (137 mL). It was stirred at rt for 10 min to dissolve the solid starting material and then subjected to three cycles of evacuation/back-filling with nitrogen. To the homogeneous solution was added a solution of Hoveyda-Grubbs II (0.015 g, 0.025 mmol) in toluene (3 mL). The mixture was stirred at 106° C. under nitrogen for 1 h. After it was concentrated the residue was purified by reverse phase preparative HPLC (Gemini™ Prep C$_{18}$ 5 µm column; Phenomenex, Torrance, CA; MeCN in water with 0.1% TFA, gradient elution) to give the title compound (55 mg) as a white solid. $^1$H NMR (500 MHz, CD$_2$Cl$_2$) δ 8.05 (m, 1H), 7.72 (m, 1H), 7.17 (m, 1H), 7.09 (m, 1H), 6.99-6.91 (m, 2H), 6.79 (m, 1H), 5.71 (dd, J=6.24, 15.53 Hz, 1H), 5.48-5.39 (m, 1H), 4.13-4.04 (m, 2H), 3.83-3.69 (m, 2H), 3.64 (ddd, J=6.48, 9.23, 15.10 Hz, 1H), 3.47-3.36 (m, 1H), 3.24 (d, J=14.18 Hz, 1H), 3.08 (dd, J=9.54, 15.41 Hz, 1H), 2.83-2.70 (m, 3H), 2.57-2.49 (m, 1H), 2.29 (quin, J=8.93 Hz, 1H), 2.17-1.48 (m, 12H), 1.43 (t, J=12.35 Hz, 1H). m/z (ESI, +ve ion) 555.2 (M+H)$^+$.

Example 859. (1S,3'R,6'R,12'R)-6-chloro-12'-ethyl-7'-methylidene-3,4-dihydro-2H,15'H-spiro[naphthalene-1,22'-[20]oxa[13]thia[1,14]diazatetracyclo [14.7.2.0$^{3,6}$.0$^{19,24}$]pentacosa [16,18,24]trien]-15'-one 13',13'-dioxide

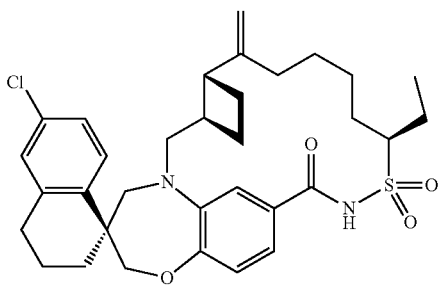

A solution of methyltriphenylphosphonium bromide (2.4 g, 6.8 mmol) in THF (20 mL) was cooled to 0° C. n-Butyl lithium solution (2.5 M in hexane; 2.5 mL, 6.16 mmol) was added dropwise and it was stirred at 0° C. for 10 min. The resulting Wittig reagent (yellow solution) was added dropwise to a solution of (1S,3'R,6'R,12'R)-6-chloro-12'-ethyl-3,4-dihydro-2H,7'H,15'H-spiro[naphthalene-1,22'-[20]oxa [13]thia[1,14]diazatetracyclo[14.7.2.0$^{3,6}$.0$^{19,24}$]pentacosa [16,18,24]triene]-7',15'-dione 13',13'-dioxide (Example 886; 0.410 g, 0.684 mmol) in THF (8 mL) at 0° C. until the yellow color persisted. After it was stirred at 0° C. for 12 min, the reaction mixture was added to a stirred ice-water (4 mL). It was acidified with 1N HCl solution to pH 2-4. The organic phase was separated and the aqueous phase was extracted with EtOAc (200 mL). The organic phase was washed with brine, dried anhydrous sodium sulfate. After concentration the residue was loaded to a 40 g ISCO Gold column and eluted with 0% to 10% EtOAc (containing 0.3% AcOH)/hexane (containing 0.3% AcOH) to provide the title compound (259 mg) as a white solid. $^1$H NMR (400 MHz, CD$_2$Cl$_2$) δ 8.09 (m, 1H), 7.73 (m, 1H), 7.19 (m, 1H), 7.09 (m, 1H), 6.97 (m, 1H), 6.88 (m, 2H), 4.75-4.64 (m, 2H), 4.14-4.04 (m, 2H), 3.87 (m, 1H), 3.82-3.69 (m, 2H), 3.27 (d, J=14.08 Hz, 1H), 3.05 (dd, J=7.04, 15.45 Hz, 1H), 2.88-2.71 (m, 3H), 2.61-2.51 (m, 1H), 2.14-1.25 (m, 18H), 1.19-1.11 (m, 3H). m/z (ESI, +ve ion) 597.1 (M+H)$^+$.

Example 861. (3R,6R,7S,12R,22S)-6'-chloro-7-hydroxy-12-methyl-3',4'-dihydro-2'H,15H-spiro[10,20-dioxa-13-thia-1,14-diazatetracyclo[14.7.2.0$^{3,6}$.0$^{19,24}$] pentacosa-16,18,24-triene-22,1'-naphthalen]-15-one 13,13-dioxide or (3R,6R,7S,12R,22R)-6'-chloro-7-hydroxy-12-methyl-3',4'-dihydro-2'H,15H-spiro[10, 20-dioxa-13-thia-1,14-diazatetracyclo[14.7.2. 0$^{3,6}$.0$^{19,24}$]pentacosa-16,18,24-triene-22,1'-naphthalen]-15-one 13,13-dioxide

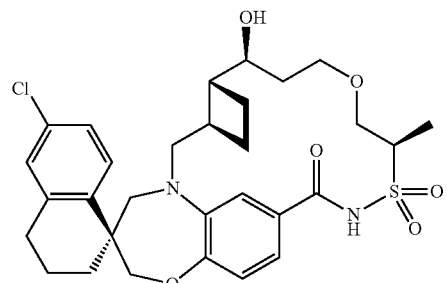

or

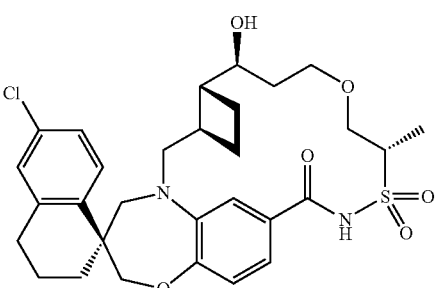

Step 1: bis(4-methoxybenzyl)amine

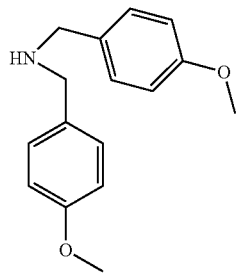 [SMILES: COc1ccc(CNCc2ccc(OC)cc2)cc1]

A solution of 4-methoxybenzaldehyde (10.7 mL, 88 mmol) and 4-methoxybenzylamine (4.5 g, 137 mmol) in DCM (105 mL) and AcOH (21 mL) was stirred at rt for 15 min. Then it was cooled to 0° C., and was added slowly sodium cyanoborohydride (2.8 g, 44 mmol). It was stirred at 0° C. to rt for 1 h. The reaction mixture was added slowly to NaOH solution, neutralized to pH=8-10 and extracted with EtOAc (2×200 mL). The organic phase was washed with brine and dried over anhydrous sodium sulfate and concentrated. The residue was loaded to a 330 g ISCO Gold column and eluted with 0% to 20% EtOAc/DCM to provide the title compound (6.0 g) as a white solid. m/z (ESI, +ve ion) 258.2 (M+H)$^+$.

Step 2: N,N-bis(4-methoxybenzyl)prop-1-ene-2-sulfonamide

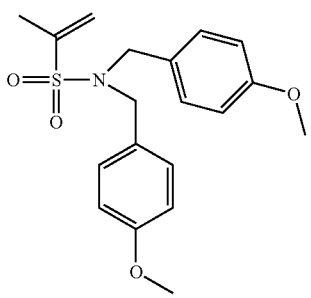 [SMILES: C=C(C)S(=O)(=O)N(Cc1ccc(OC)cc1)Cc1ccc(OC)cc1]

Prop-1-en-2-ylmagnesium bromide (0.5 M in THF; 20 mL, 10 mmol) was added dropwise to a solution of sulfuryl dichloride (1.2 mL, 15 mmol) in hexane (20 mL) at 0° C. It was allowed to rt and stirred for 1 h. To this mixture was added DCM (20 mL) and it was cooled in ice bath. Triethylamine (5.6 mL, 40 mmol) was added slowly, followed by addition dropwise of N,N-bis(4-methoxybenzyl)prop-1-ene-2-sulfonamide (Example 861, Step 1; 1.27 g, 3.51 mmol) in DCM (35 mL). It was stirred at 0° C. for 20 min. The reaction mixture was poured slowly into ice water (20 g), and extracted with EtOAc (340 mL). The organic phase was washed with 1 N HCl solution (20 mL), NaHCO$_3$ solution (10 mL), brine (4 mL), and dried over anhydrous sodium sulfate. After concentration the residue was loaded to a 120 g ISCO Gold column and eluted with 0% to 15% EtOAc/hexane to provide the title compound (1.27 g) as a pale yellow solid. m/z (ESI, +ve ion) 361.2 (M+H)$^+$.

Step 3: (S)-tert-butyl 6'-chloro-5-(((1R,2R)-2-((S)-1-((4-methoxybenzyl)oxy)but-3-en-1-yl)cyclobutyl)methyl)-3',4,4',5-tetrahydro-2H,2'H-spiro[benzo[b][1,4]oxazepine-3,1'-naphthalene]-7-carboxylate

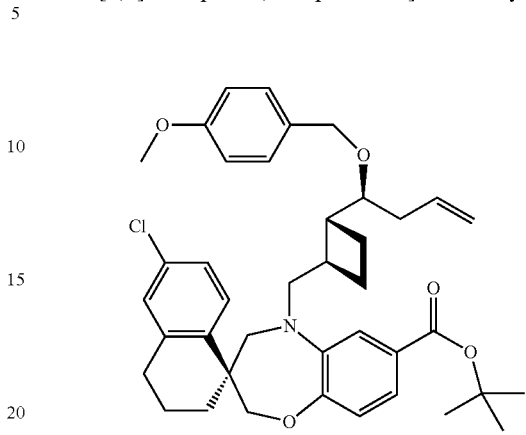

At 0° C., sodium hydride (60% dispersion in mineral oil; 43 mg, 2.1 mmol) was added to a solution of (S)-tert-butyl 6'-chloro-5-(((1R,2R)-2-((S)-1-hydroxybut-3-en-1-yl)cyclobutyl) methyl)-3',4,4',5-tetrahydro-2H,2'H-spiro[benzo[b][1,4]oxazepine-3,1'-naphthalene]-7-carboxylate (Intermediate AA13A, Step 1B; 0.82 g, 1.52 mmol) in DMF (6.6 mL). It was stirred at 0° C. for 26 min. Then 4-methoxybenzyl chloride (1.48 g, 9.45 mmol) and potassium iodide (0.142 g, 0.85 mmol) was added and it was stirred at 0° C. to rt for 3 days. The reaction mixture was poured into water (10 mL), and diluted with EtOAc (300 mL). After separation. The organic phase was washed with 1N HCl solution, NaHCO$_3$ solution, and brine, dried over anhydrous sodium sulfate and concentrated. The residue was loaded to a 80 g ISCO Gold column and eluted with 0% to 7% EtOAc/hexane to provide the title compound (241 mg) as a film. m/z (ESI, +ve ion) 658.3 (M+H)$^+$.

Step 4: (S)-tert-butyl 6'-chloro-5-(((1R,2R)-2-((S)-1-((4-methoxybenzyl)oxy)-3-oxopropyl)cyclobutyl)methyl)-3',4,4',5-tetrahydro-2H,2'H-spiro[benzo[b][1,4]oxazepine-3,1'-naphthalene]-7-carboxylate

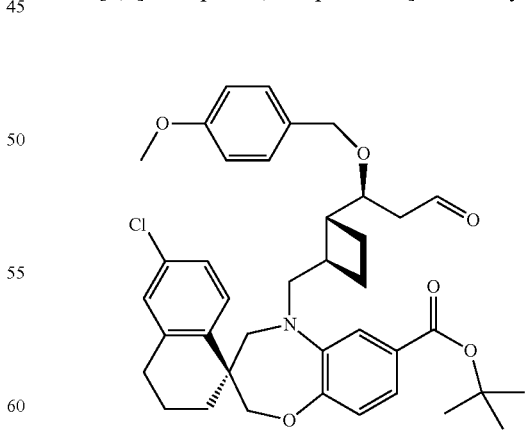

Sodium periodate (0.910 g, 4.25 mmol) was added to a solution of (S)-tert-butyl 6'-chloro-5-(((1R,2R)-2-((S)-1-((4-methoxybenzyl)oxy)but-3-en-1-yl)cyclobutyl)methyl)-3',4,4',5-tetrahydro-2H,2'H-spiro[benzo[b][1,4]oxazepine-3,1'-naphthalene]-7-carboxylate (Example 861, Step 3; 0.80 g, 1.2 mmol) in THF (8.7 mL), acetone (8.7 mL) and water (2.9 mL) at 0° C. It was added osmium tetroxide (2.5 wt % solution in 2-methyl-2-propanol; 0.71 mL, 0.073 mmol) and was stirred at 0° C. to rt for 21 h. The reaction mixture was diluted with EtOAc (300 mL) and the organic phase was washed with 1 N sodium thiosulfate solution (3 mL), brine (3 mL) and dried over anhydrous sodium sulfate. After concentration, the title compound was obtained, which was used for next reaction without purification. m/z (ESI, +ve ion) 660.3 (M+H)$^+$.

Step 5: (S)-tert-butyl 6'-chloro-5-(((1R,2R)-2-((S)-3-hydroxy-1-((4-methoxybenzyl)oxy)propyl)cyclobutyl)methyl)-3',4,4',5-tetrahydro-2H,2'H-spiro[benzo[b][1,4]oxazepine-3,1'-naphthalene]-7-carboxylate

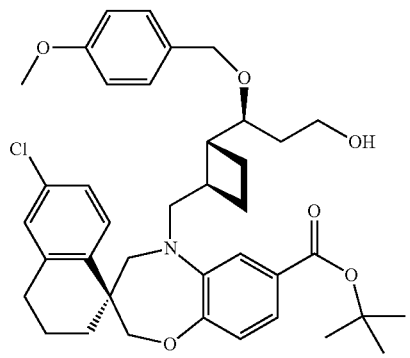

Sodium borohydride (10 mg, 2.9 mmol) was added portion by portion slowly to a solution of (S)-tert-butyl 6'-chloro-5-(((1R,2R)-2-((S)-1-((4-methoxybenzyl)oxy)-3-oxopropyl)cyclobutyl)methyl)-3',4,4',5-tetrahydro-2H,2'H-spiro[benzo[b][1,4]oxazepine-3,1'-naphthalene]-7-carboxylate (Example 861, Step 4; 0.480 g, 0.727 mmol) in MeOH (14 mL) at 0° C. and it was stirred at 0° C. for 10 min. Water (5 mL) was added and it was concentrated to remove the MeOH. Then it was extracted with EtOAc (220 mL), the organic phase was washed with Na$_2$CO$_3$ solution (1 mL), brine (1 mL), and dried over anhydrous sodium sulfate. After concentration the residue was loaded to a 80 g ISCO Gold column and eluted with 0% to 20% EtOAc/hexane to provide the title compound (290 mg) as a white solid. m/z (ESI, +ve ion) 662.2 (M+H)$^+$.

Step 6: (S)-tert-butyl 6'-chloro-5-(((1R,2R)-2-((S)-1-((4-methoxybenzyl)oxy)-N,N-bis(4-methoxybenzyl)-3-((R)-2-sulfamoylpropoxy)propyl)cyclobutyl)methyl)-3',4,4',5-tetrahydro-2H,2'H-spiro[benzo[b][1,4]oxazepine-3,1'-naphthalene]-7-carboxylate and (S)-tert-butyl 6'-chloro-5-(((1R,2R)-2-((S)-1-((4-methoxybenzyl)oxy)-N,N-bis(4-methoxybenzyl)-3-((S)-2-sulfamoylpropoxy)propyl)cyclobutyl)methyl)-3',4,4',5-tetrahydro-2H,2'H-spiro[benzo[b][1,4]oxazepine-3,1'-naphthalene]-7-carboxylate

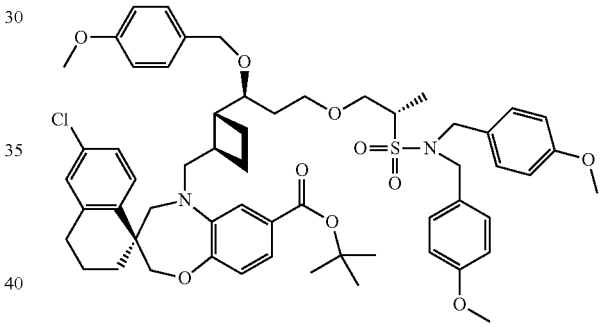

and

A solution of (S)-tert-butyl 6'-chloro-5-(((1R,2R)-2-((S)-3-hydroxy-1-((4-methoxybenzyl)oxy)propyl)cyclobutyl)methyl)-3',4,4',5-tetrahydro-2H,2'H-spiro[benzo[b][1,4]oxazepine-3,1'-naphthalene]-7-carboxylate (Example 861, Step 5; 0.287 g, 0.433 mmol) in THF (8.7 mL) was cooled with ice bath. Sodium hydride (57-63% oil dispersion, 16 mg, 0.74 mmol) was added and it was stirred at cooling for 19 min, to which a solution of N,N-bis(4-methoxybenzyl)prop-1-ene-2-sulfonamide (Example 861, Step 2; 0.28 g, 0.78 mmol) in THF (6 mL) was added. It was stirred at rt for 19 h. The reaction mixture was poured into water (2 mL) and extracted with EtOAc (170 mL). The organic phase was washed with brine, dried over anhydrous sodium sulfate and concentrated. The residue was purified by reverse phase preparative HPLC (Gemini™ Prep C$_{18}$ 5 μm column; Phenomenex, Torrance, CA; MeCN in water with 0.1% TFA, gradient elution). The HPLC fraction was concentrated at rt, then neutealized with NaHCO$_3$ solution to pH 7, extracted with EtOAc(150 mL). The organic phase was washed with brine and dried over anhydrous sodium sulfate and concentrated to provide the title compound (57 mg) as a mixture of two isomers.

Step 7: (S)-6'-chloro-5-(((1R,2R)-2-((S)-1-hydroxy-3-((R)-2-sulfamoylpropoxy)propyl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((S)-1-hydroxy-3-((S)-2-sulfamoylpropoxy)propyl)cyclobutyl)methyl)-3',4,4',5-tetrahydro-2H,2'H-spiro[benzo[b][1,4]oxazepine-3,1'-naphthalene]-7-carboxylic Acid Step 8: (3R,6R,7S,12R,22S)-6'-chloro-7-hydroxy-12-methyl-3',4'-dihydro-2'H,15H-spiro[10,20-dioxa-13-thia-1,14-diazatetracyclo[14.7.2.0$^{3,6}$.0$^{19,24}$]pentacosa-16,18,24-triene-22,1'-naphthalen]-15-one 13,13-dioxide or (3R,6R,7S,12R,22R)-6'-chloro-7-hydroxy-12-methyl-3',4'-dihydro-2'H,15H-spiro[10,20-dioxa-13-thia-1,14-diazatetracyclo[14.7.2.0$^{3,6}$.0$^{19,24}$]pentacosa-16,18,24-triene-22,1'-naphthalen]-15-one 13,13-dioxide

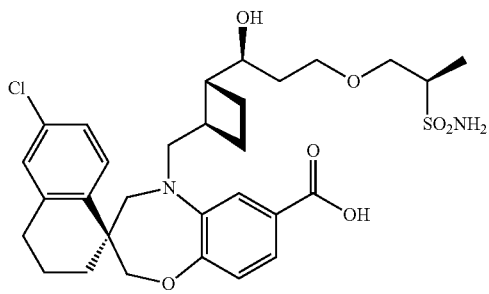

and

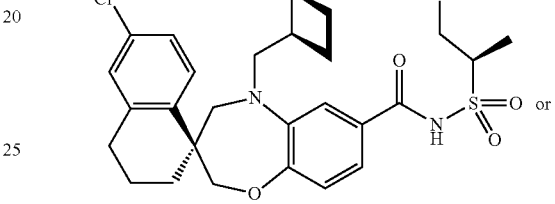

or

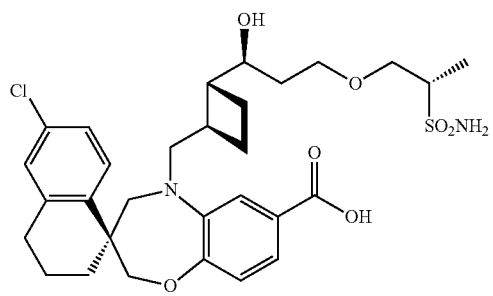

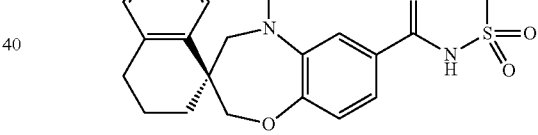

(S)-Tert-Butyl 6'-chloro-5-(((1R,2R)-2-((S)-1-((4-methoxybenzyl)oxy)-N,N-bis(4-methoxy-benzyl)-3-((R)-2-sulfamoylpropoxy)propyl)cyclobutyl)methyl)-3',4,4',5-tetrahydro-2H,2'H-spiro[benzo[b][1,4]oxazepine-3,1'-naphthalene]-7-carboxylate (Example 861, Step 6; 0.055 g, 0.054 mmol) was added to a mixed solvent TFA (4 mL) and DCM (12 mL). It was stirred at rt for 16 h. After concentration, the residue was purified by reverse phase preparative HPLC (Gemini™ Prep $C_{18}$ 5 μm column; Phenomenex, Torrance, CA; MeCN in water with 0.1% TFA, gradient elution) to provide the title compound (33 mg) as a white solid. m/z (ESI, +ve ion) 607.3 (M+H)$^+$.

4-Dimethylaminopyridine (DMAP) (0.073 g, 0.598 mmol) was added to a solution of (1'S)-6'-chloro-5-(((1R,2R)-2-((1S)-1-hydroxy-3-(2-sulfamoylpropoxy)propyl)cyclobutyl)methyl)-3',4,4',5-tetrahydro-2H,2'H-spiro[benzo[b][1,4]oxazepine-3,1'-naphthalene]-7-carboxylic acid (Example 861, Step 7; 0.033 g, 0.054 mmol) in DCM (100 mL). It was cooled by ice bath. EDC (0.063 g, 0.326 mmol) was added and it was stirred at 0° C. to rt for 3 days. It was concentrated and the residue was purified by SFC (Method: 250×21.2 mm IC—H column w/ 20 g/min MeOH (0.2% DEA)+60 g/min $CO_2$ on a Thar 80 SFC. Outlet pressure 100 bar; Temp. 20° C.; Wavelength 220 nm). The title compound was obtained as a single isomer (2.4 mg, first eluting peak) as a white solid. $^1$H NMR (500 MHz, $CD_2Cl_2$) δ 7.71 (m, 1H), 7.30 (m, 1H), 7.19-7.04 (m, 3H), 6.95 (m, 1H), 4.19 (m, 1H), 4.11 (m, 1H), 3.95 (br. s., 1H), 3.87-3.72 (m, 3H), 3.65-3.48 (m, 3H), 3.37 (d, J=16.87 Hz, 2H), 2.99-2.87 (m, 1H), 2.83-2.69 (m, 2H), 2.16-2.06 (m, 1H), 2.01-1.48 (m, 11H), 1.45-1.38 (m, 3H). m/z (ESI, +ve ion) 589.2 (M+H)$^+$.

Example 862. (3R,6R,7R,12S,22S)-6'-chloro-7-hydroxy-12-methyl-3',4'-dihydro-2'H,15H-spiro[10,20-dioxa-13-thia-1,14-diazatetracyclo[14.7.2.0³,⁶.0¹⁹,²⁴]pentacosa-16,18,24-triene-22,1'-naphthalen]-15-one 13,13-dioxide or (3R,6R,7S,12S,22S)-6'-chloro-7-hydroxy-12-methyl-3',4'-dihydro-2'H,15H-spiro[10,20-dioxa-13-thia-1,14-diazatetracyclo[14.7.2.0³,⁶.0¹⁹,²⁴]pentacosa-16,18,24-triene-22,1'-naphthalen]-15-one 13,13-dioxide

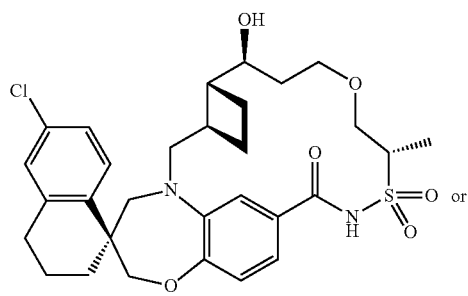 or

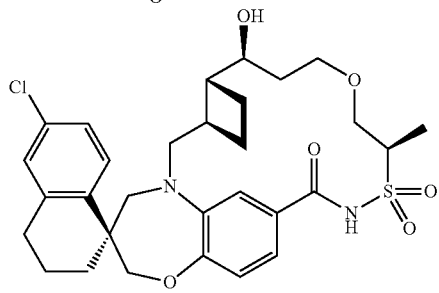

The title compound (4.2 mg) was obtained as a single isomer (second eluting peak) from the reverse phase preparative HPLC in Example 861. ¹H NMR (500 MHz, CD₂Cl₂) δ 7.72 (d, J=7.83 Hz, 1H), 7.43 (d, J=7.09 Hz, 1H), 7.17 (br. s., 2H), 7.09 (br. s., 1H), 6.92-6.99 (m, 1H), 4.07-4.14 (m, 3H), 3.89 (br. s., 2H), 3.83-3.75 (m, 3H), 3.70-3.58 (m, 3H), 3.26-3.07 (m, 2H), 2.76 (br. s., 3H), 2.41 (br. s., 1H), 2.11-1.08 (m, 13H). m/z (ESI, +ve ion) 589.2 (M+H)⁺.

Example 863. (3R,6R,7R,11E,22S)-6'-chloro-7-hydroxy-3',4'-dihydro-2'H,15H-spiro[9,20-dioxa-13-thia-1,14-diazatetracyclo[14.7.2.0³,⁶.0¹⁹,²⁴]pentacosa-11,16,18,24-tetraene-22,1'-naphthalen]-15-one 13,13-dioxide or (3R,6R,7S,11E,22S)-6'-chloro-7-hydroxy-3',4'-dihydro-2'H,15H-spiro[9,20-dioxa-13-thia-1,14-diazatetracyclo[14.7.2.0³,⁶.0¹⁹,²⁴]pentacosa-11,16,18,24-tetraene-22,1'-naphthalen]-15-one 13,13-dioxide

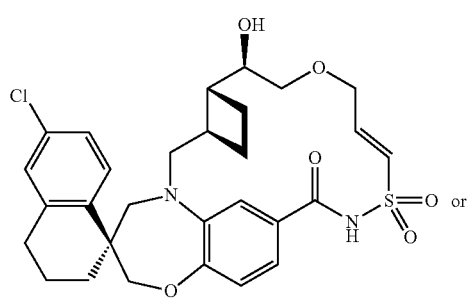 or

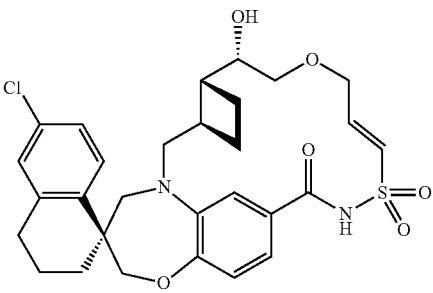

Step 1: (S)-tert-butyl 6'-chloro-5-(((1R,2S)-2-vinylcyclobutyl)methyl)-3',4,4',5-tetrahydro-2H,2'H-spiro[benzo[b][1,4]oxazepine-3,1'-naphthalene]-7-carboxylate

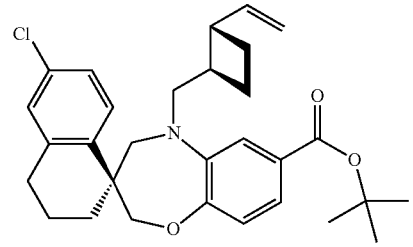

n-Butyl lithium (2.5 M solution in hexane; 2.0 mL, 4.94 mmol) was added to a solution of methyltriphenylphosphonium bromide (2.02 g, 5.64 mmol) in THF (25 mL) at 0° C., which was degassed by nitrogen. The reaction mixture was stirred at 0° C. for 10 min, becoming a yellow solution. The resulting solution (0.9 mL is enough) was added dropwise to a solution of (S)-tert-butyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20B; 0.700 g, 1.41 mmol) in THF (23.5 mL) at 0° C., which was degassed until the yellow color persisted. It was poured slowly to ice water (15 mL), extracted with EtOAc (200 mL). The organic phase was washed with brine (2 mL) and dried over anhydrous sodium sulfate and concentrated. The residue was loaded to a 80 g ISCO Gold column and eluted with 0% to 3% EtOAc/hexane to provide the title compound (617 mg) as a white solid. m/z (ESI, +ve ion) 494.2 (M+H)⁺.

1757

Step 2: (S)-tert-butyl 6'-chloro-5-(((1R,2R)-2-((R)-1,2-dihydroxyethyl)cyclobutyl)methyl)-3',4,4',5-tetrahydro-2H,2'H-spiro[benzo[b][1,4]oxazepine-3,1'-naphthalene]-7-carboxylate or (S)-tert-butyl 6'-chloro-5-(((1R,2R)-2-((S)-1,2-dihydroxyethyl)cyclobutyl)methyl)-3',4,4',5-tetrahydro-2H,2'H-spiro[benzo[b][1,4]oxazepine-3,1'-naphthalene]-7-carboxylate

1758

Step 3: (S)-tert-butyl 5-(((1R,2R)-2-((R)-2-(allyloxy)-1-hydroxyethyl)cyclobutyl)methyl)-6'-chloro-3',4,4',5-tetrahydro-2H,2'H-spiro[benzo[b][1,4]oxazepine-3,1'-naphthalene]-7-carboxylate or (S)-tert-butyl 5-(((1R,2R)-2-((S)-2-(allyloxy)-1hydroxyethyl)cyclobutyl)methyl)-6'-chloro-3',4,4',5-tetrahydro-2H,2'H-spiro[benzo[b][1,4]oxazepine-3,1'-naphthalene]-7-carboxylate

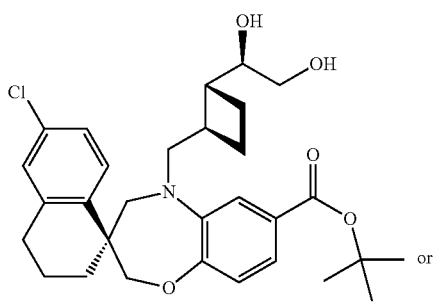

or

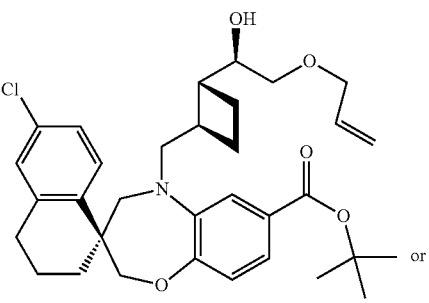

or

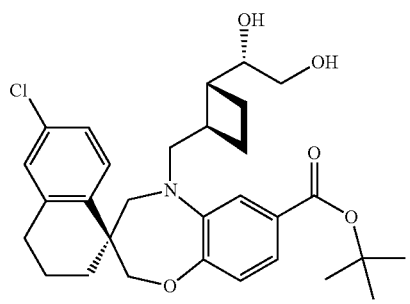

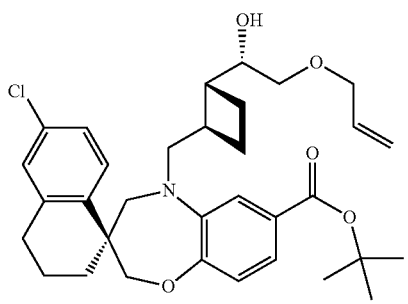

4-Methylmorpholine N-oxide (0.294 g, 2.51 mmol) was added to a solution of (S)-tert-butyl 6'-chloro-5-(((1R,2S)-2-vinylcyclobutyl)methyl)-3',4,4',5-tetrahydro-2H,2'H-spiro[benzo[b][1,4]oxazepine-3,1'-naphthalene]-7-carboxylate (Example 863, Step 1; 0.540 g, 1.09 mmol) in acetone (27 mL), THF (27 mL) and water (0.2 mL). After the reaction mixture was degassed with nitrogen, osmium tetroxide, (2.5 wt % solution in 2-methyl-2-propanol (1.1 mL, 0.11 mmol) was added dropwise and it was stirred at rt for 2.5 h. A solution of sodium thiosulfate (1.0 M aqueous solution, 3 mL) was added and stirred at rt for 20 min. It was concentrated extracted with EtOAc (200 mL). The organic phase was washed with brine, dried over anhydrous sodium sulfate and concentrated. The residue was loaded to a 220 g ISCO Gold column and eluted with 0% to 10% EtOAc/DCM. The title compound (288 mg) was obtained as a single isomer (first eluting peak). m/z (ESI, +ve ion) 528.1 (M+H)$^+$.

Sodium hydride (60% dispersion in mineral oil; 22 mg, 1.06 mmol) was added to a solution of (S)-tert-butyl 6'-chloro-5-(((1R,2R)-2-((R)-1,2-dihydroxyethyl)cyclobutyl)methyl)-3',4,4',5-tetrahydro-2H,2'H-spiro[benzo[b][1,4]oxazepine-3,1'-naphthalene]-7-carboxylate (Example 863, Step 2; 0.28 g, 0.53 mmol) in DMF (15.6 mL). It was stirred at 0° C. for 20 min. Allyl iodide (0.068 mL, 0.742 mmol) in DMF (0.8 mL) was added and it was stirred at 0° C. to rt for 19 h. It was quenched with water (2 mL) and extracted with EtOAc (200 mL). The organic phase was washed with brine, and dried over anhydrous sodium sulfate and concentrated. The residue was loaded to a 40 g ISCO Gold column and eluted with 0% to 20% EtOAc/hexane to provide the title compound (115 mg) as a film. m/z (ESI, +ve ion) 568.3 (M+H)$^+$.

1759

Step 4: (S)-6'-chloro-5-(((1R,2R)-2-((R)-1-hydroxy-2-(((E)-3-sulfamoylallyl)oxy)ethyl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((S)-1-hydroxy-2-(((E)-3-sulfamoylallyl)oxy)ethyl)cyclobutyl)methyl)-3',4,4',5-tetrahydro-2H,2'H-spiro[benzo[b][1,4]oxazepine-3,1'-naphthalene]-7-carboxylic Acid

1760

Step 5: (3R,6R,7R,11E,22S)-6'-chloro-7-hydroxy-3',4'-dihydro-2'H,15H-spiro[9,20-dioxa-13-thia-1,14-diazatetracyclo[14.7.2.0$^{3,6}$.0$^{19,24}$]pentacosa-11,16,18,24-tetraene-22,1'-naphthalen]-15-one 13,13-dioxide or (3R,6R,7S,11E,22S)-6'-chloro-7-hydroxy-3',4'-dihydro-2'H,15H-spiro[9,20-dioxa-13-thia-1,14-diazatetracyclo[14.7.2.0$^{3,6}$.0$^{19,24}$]pentacosa-11,16,18,24-tetraene-22,1'-naphthalen]-15-one 13,13-dioxide

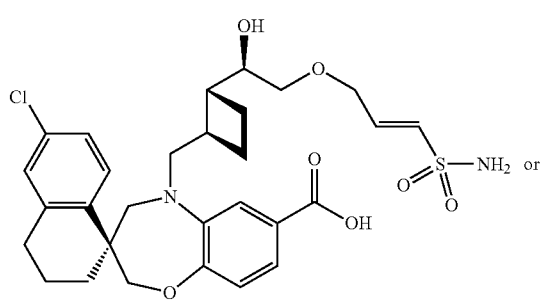

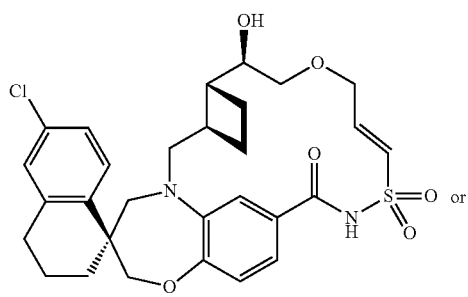

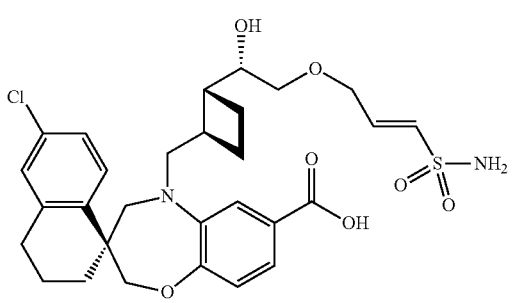

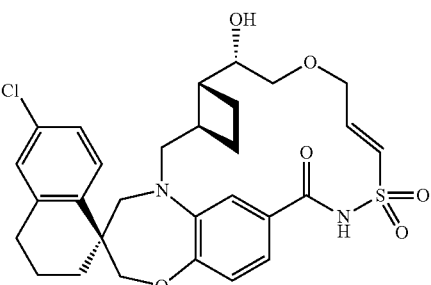

A flask was charged with (S)-tert-butyl 5-(((1R,2R)-2-((R)-2-(allyloxy)-1-hydroxyethyl) cyclobutyl)methyl)-6'-chloro-3',4,4',5-tetrahydro-2H,2'H-spiro[benzo[b][1,4]oxazepine-3,1'-naphthalene]-7-carboxylate (Example 863, Step 3; 0.025 g, 0.044 mmol) and N,N-bis(4-methoxybenzyl)ethenesulfonamide (Example 831, Step 2; 0.138 g, 0.396 mmol) in 1,2-Dichloroethane (1.5 mL). It was stirred at rt for 10 min to dissolve the solid starting material and then degassed with nitrogen. To the homogeneous solution was added a solution of Hoveyda-Grubbs II (7.5 mg, 8.8 μmol) in dichloroethane (0.5 mL) and it was stirred at 60° C. for 80 min. It was concentrated, dissolved in 1:3 TFA/DCM (0.4 mL) and stirred at rt for 19 h. It was concentrated and the residue was purified by reverse phase preparative HPLC (Gemini™ Prep C$_{18}$ 5 μm column; Phenomenex, Torrance, CA; MeCN in water with 0.1% TFA, gradient elution) to provide the title compound (35 mg) as a film. m/z (ESI, +ve ion) 591.1 (M+H)$^+$.

4-Dimethylaminopyridine (DMAP) (0.062 g, 0.51 mmol) was added to a solution of (S)-6'-chloro-5-(((1R,2R)-2-((R)-1-hydroxy-2-(((E)-3-sulfamoylallyl)oxy)ethyl)cyclobutyl)methyl)-3',4,4',5-tetrahydro-2H,2'H-spiro[benzo[b][1,4]oxazepine-3,1'-naphthalene]-7-carboxylic acid (Example 863, Step 4; 0.030 g, 0.051 mmol) in DCM (102 mL), which was cooled by ice bath. EDC (0.068 g, 0.355 mmol) was added slowly and it was stirred at 0° C. to rt for 22 h. It was concentrated and the residue was purified by reverse phase preparative HPLC (Gemini™ Prep C$_{18}$ 5 μm column; Phenomenex, Torrance, CA; MeCN in water with 0.1% TFA, gradient elution) to provide the title compound (13.5 mg) as a white solid. $^1$H NMR (400 MHz, CD$_2$Cl$_2$) δ 8.58-8.45 (m, 1H), 7.69 (m, 1H), 7.17 (m, 2H), 7.09 (d, J=2.35 Hz, 1H), 6.98 (m, 1H), 6.91 (m, 1H), 6.73 (d, J=15.06 Hz, 1H), 4.45 (d, J=18.39 Hz, 1H), 4.16-4.05 (m, 3H), 3.82-3.68 (m, 2H), 3.62 (d, J=13.89 Hz, 1H), 3.44 (m, 1H), 3.34 (m, 1H), 3.24 (m, 1H), 3.13 (dd, J=8.80, 14.67 Hz, 1H), 2.71-2.81 (m, 2H), 2.44-2.33 (m, 2H), 2.29-1.55 (m, 9H), 1.52-1.42 (m, 1H). m/z (ESI, +ve ion) 573.1 (M+H)$^+$.

Example 865. (S)-6'-chloro-5-(((1R,2S)-2-(2-hydroxyethyl)cyclobutyl)methyl)-N-(methylsulfonyl)-3',4,4',5-tetrahydro-2H,2'H-spiro[benzo[b][1,4]oxazepine-3,1'-naphthalene]-7-carboxamide

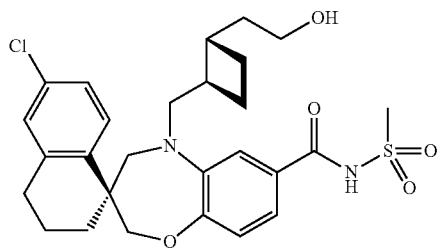

Step 1: (S)-methyl 6'-chloro-5-(((1R,2R)-2-((E)-2-methoxyvinyl)cyclobutyl)methyl)-3',4,4',5-tetrahydro-2H,2'H-spiro[benzo[b][1,4]oxazepine-3,1'-naphthalene]-7-carboxylate

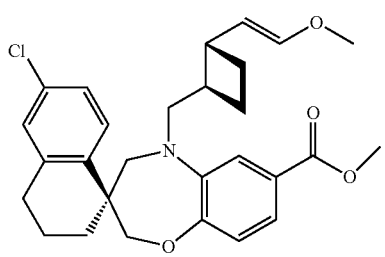

A solution of bromo(methoxymethyl)triphenylphosphorane (3.37 g, 8.70 mmol) in THF (22 mL) was cooled to 0° C. n-Butyl lithium (2.5 M solution in hexane; 2.78 mL, 6.96 mmol) was added dropwise and it was stirred at 0° C. for 17 min, which was yellow solution. This solution was added slowly to a solution of (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A; 0.395 g, 0.87 mmol) in THF (5 mL) until the yellow color persisted and it was stirred at 0° C. for 5 min. The reaction mixrure was poured slowly to ice-water (15 mL). It was extracted with EtOAc (200 mL) and the organic phase was dried over anhydrous sodium sulfate and concentrated. The residue was loaded to a 4 g ISCO Gold column and eluted with 0% to 10% EtOAc/hexane to provide the title compound (74 mg) as a white solid. m/z (ESI, +ve ion) 482.3 (M+H)$^+$.

Step 2: (S)-methyl 6'-chloro-5-(((1R,2S)-2-(2-oxoethyl)cyclobutyl)methyl)-3',4,4',5-tetrahydro-2H,2'H-spiro[benzo[b][1,4]oxazepine-3,1'-naphthalene]-7-carboxylate

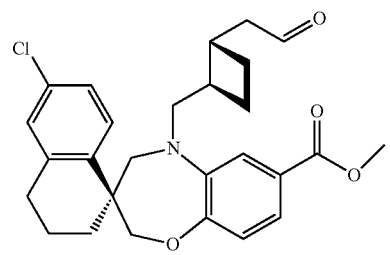

1 N HCl solution (0.5 mL) was added to a solution of a mixture of (S)-methyl 6'-chloro-5-(((1R,2R)-2-((E)-2-methoxyvinyl)cyclobutyl)methyl)-3',4,4',5-tetrahydro-2H,2'H-spiro[benzo[b][1,4]oxazepine-3,1'-naphthalene]-7-carboxylate (Example 865, Step 1; 0.034 g, 0.071 mmol) in acetone (1.8 mL). It was stirred at rt for 18 h. After it was concentrated, the residue was neutralized with NaHCO$_3$ solution and extracted with EtOAc (80 mL). The organic phase was washed with brine, dried over anhydrous sodium sulfate, concentrated to provide the title compound (33 mg) as a white solid. m/z (ESI, +ve ion) 468.2 (M+H)$^+$.

Step 3: (S)-methyl 6'-chloro-5-(((1R,2S)-2-(2-hydroxyethyl)cyclobutyl)methyl)-3',4,4',5-tetrahydro-2H,2'H-spiro[benzo[b][1,4]oxazepine-3,1'-naphthalene]-7-carboxylate

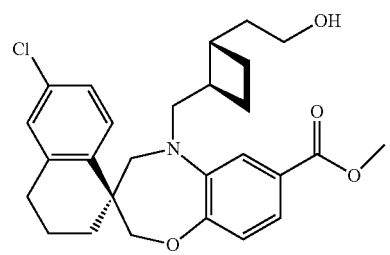

Sodium borohydrate (powder, reagent grade 98%; 6.8 mg, 0.194 mmol) was added to a solution of (S)-methyl 6'-chloro-5-(((1R,2S)-2-(2-oxoethyl)cyclobutyl)methyl)-3',4,4',5-tetrahydro-2H,2'H-spiro[benzo[b][1,4]oxazepine-3,1'-naphthalene]-7-carboxylate (Example 865, Step 2; 0.013 g, 0.028 mmol) in MeOH (0.9 mL). It was stirred at rt for 30 min. After concentration the residue was diluted with EtOAc (60 mL). The organic phase was washed with Na$_2$CO$_3$ solution and brine, dried over anhydrous sodium sulfate. It was concentrated and the residue was purified by reverse phase preparative HPLC (Gemini™ Prep C$_{18}$ 5 μm column; Phenomenex, Torrance, CA; MeCN in water with 0.1% TFA, gradient elution) to give the title product (23 mg) as a white solid. m/z (ESI, +ve ion) 470.1 (M+H)$^+$.

Step 4: (S)-6'-chloro-5-(((1R,2S)-2-(2-hydroxyethyl)cyclobutyl)methyl)-3',4,4',5-tetrahydro-2H,2'H-spiro[benzo[b][1,4]oxazepine-3,1'-naphthalene]-7-carboxylic Acid

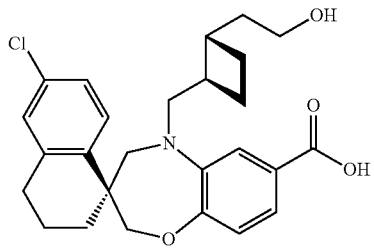

Lithium hydroxide (1 M aqueous solution, 0.5 mL, 0.5 mmol) was added to a solution of (S)-methyl 6'-chloro-5-(((1R,2S)-2-(2-hydroxyethyl)cyclobutyl)methyl)-3',4,4',5-tetrahydro-2H,2'H-spiro[benzo[b][1,4]oxazepine-3,1'-naphthalene]-7-carboxylate (Example 865, Step 3; 0.023 g, 0.049 mmol) in THF (1 mL) and MeOH (0.5 mL). After it was stirred at 50° C. for 2.6 h, it was concentrated, acidified with 1 N HCl solution to pH 2-3, diluted with EtOAc (80 mL), washed with brine, and dried over anhydrous sodium sulfate. The solution was concentrated to provide the title compound (22 mg) as a white solid. m/z (ESI, +ve ion) 456.3 (M+H)$^+$.

Step 5: (S)-6'-chloro-5-(((1R,2S)-2-(2-hydroxyethyl)cyclobutyl)methyl)-N-(methylsulfonyl)-3',4,4',5-tetrahydro-2H,2'H-spiro[benzo[b][1,4]oxazepine-3,1'-naphthalene]-7-carboxamide

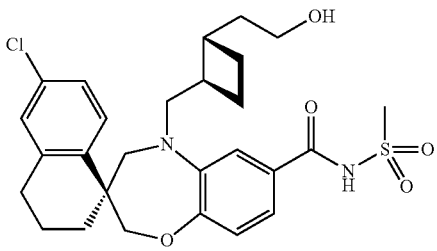

N,N-Dimethylpyridin-4-amine (DMAP) (5.8 mg, 0.047 mmol) was added to a solution of (S)-6'-chloro-5-(((1R,2S)-2-(2-hydroxyethyl)cyclobutyl)methyl)-3',4,4',5-tetrahydro-2H,2'Hspiro[benzo[b][1,4]oxazepine-3,1'-naphthalene]-7-carboxylic acid (Example 865, Step 4; 0.012 g, 0.026 mmol) and methanesulfonamide (0.013 g, 0.132 mmol) in DCM (1 mL) at 0° C. (ice bath). Then N-(3-dimethylaminopropyl)-N'-ethylcarbodiimide hydrochloride (EDC) (9 mg, 0.047 mmol) was added portion by portion slowly and it was stirred at rt for 20 h. It was concentrated and the residue was purified by reverse phase preparative HPLC (Gemini™ Prep C$_{18}$ 5 µm column; Phenomenex, Torrance, CA; MeCN in water with 0.1% TFA, gradient elution) to give the title product (55 mg) as a white solid. $^1$H NMR (400 MHz, CD$_2$Cl$_2$) δ 9.89-9.74 (m, 1H), 7.73 (m, 1H), 7.35-7.25 (m, 2H), 7.18 (m, 1H), 6.95 (m, 1H), 4.11 (m, 2H), 3.90 (d, J=14.87 Hz, 2H), 3.69 (d, J=14.09 Hz, 2H), 3.37 (m, 3H), 3.31 (d, J=14.28 Hz, 1H), 3.09 (dd, J=8.90, 14.97 Hz, 4H), 2.84-2.73 (m, 2H), 2.48-2.37 (m, 1H), 2.18-1.50 (m, 8H), 1.44 (t, J=11.93 Hz, 1H). m/z (ESI, +ve ion) 533.2 (M+H)$^+$.

Example 866. (3R,6R,7S,21S)-6'-chloro-7-hydroxy-3',4'-dihydro-2'H,14H-spiro[9,19-dioxa-12-thia-1,13-diazatetracyclo[13.7.2.0$^{3,6}$.0$^{18,23}$]tetracosa-15,17,23-triene-21,1'-naphthalen]-14-one 12,12-dioxide or (3R,6R,7R,21S)-6'-chloro-7-hydroxy-3',4'-dihydro-2'H,14H-spiro[9,19-dioxa-12-thia-1,13-diazatetracyclo[13.7.2.0$^{3,6}$.0$^{18,23}$]tetracosa-15,17,23-triene-21,1'-naphthalen]-14-one 12,12-dioxide

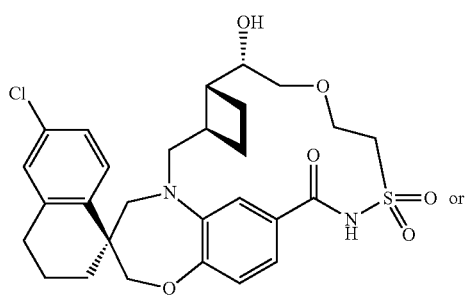 or

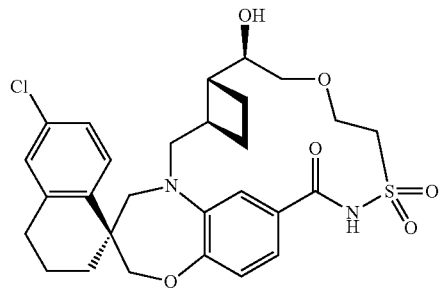

Step 1: (S)-tert-butyl 6'-chloro-5-(((1R,2R)-2-((R)-1,2-dihydroxyethyl)cyclo-butyl)methyl)-3',4,4',5-tetrahydro-2H,2'H-spiro[benzo[b][1,4]oxazepine-3,1'-NAPTHALENE]-7-carboxylate or (S)-tert-butyl 6'-chloro-5-(((1R,2R)-2-((S)-1,2-dihydroxyethyl)cyclobutyl)methyl)-3',4,4',5-tetrahydro-2H,2'H-spiro[benzo[b][1,4]oxazepine-3,1'-naphthalene]-7-carboxylate

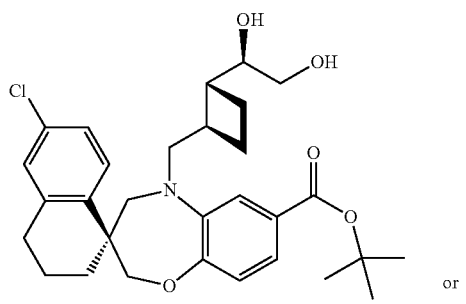 or

-continued

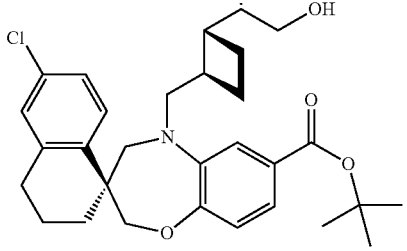

The title compound (289 mg) was obtained as a single isomer (second eluting peak) from the reverse phase preparative HPLC in Example 863, Step 2. m/z (ESI, +ve ion) 528.1 (M+H)+.

Step 2: (S)-6'-chloro-5-(((1R,2R)-2-((S)-1-hydroxy-2-(2-sulfamoylethoxy)ethyl)cyclobutyl) methyl)-3',4,4',5-tetrahydro-2H,2'H-spiro[benzo[b][1,4]oxazepine-3,1'-naphthalene]-7-carboxylic Acid or (S)-6'-chloro-5(((1R,2R)-2-((R)-1-hydroxy-2-(2-sulfamoylethoxy)ethyl) cyclobutyl)methyl)-3',4,4',5-tetrahydro-2H,2'H-spiro[benzo[b][1,4]oxazepine-3,1'-naphthalene]-7-carboxylic

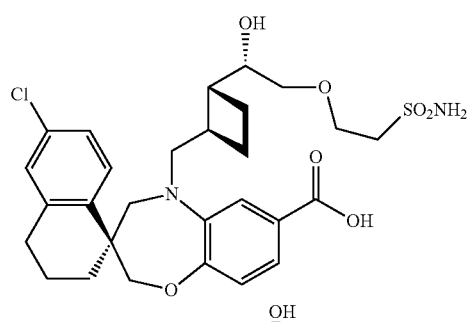

or

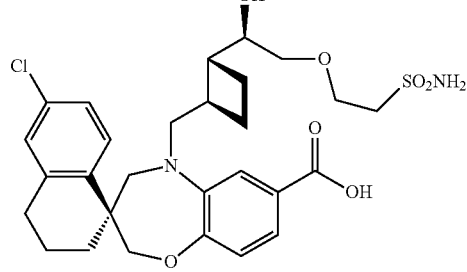

To a solution of (S)-tert-butyl 6'-chloro-5-(((1R,2R)-2-((S)-1,2-dihydroxyethyl)cyclobutyl)methyl)-3',4,4',5-tetrahydro-2H,2'H-spiro[benzo[b][1,4]oxazepine-3,1'-naphthalene]-7-carboxylate (Example 866, Step 1; 0.020 g, 0.038 mmol) in THF (0.95 mL) at 0° C. was added sodium hydride (57-63% oil dispersion; 2.8 mg, 0.133 mmol) and it was stirred at 0° C. for 19 min, and N,N-bis(4-methoxybenzyl) ethenesulfonamide (Example 831, Step 2; 0.020 g, 0.057 mmol) in THF (0.5 mL) was added. After it was stirred at 0° C. to rt for 2.7 h, the mixture was concentrated and added 4-methylanisole (100 mg) and cooled by ice bath. 1:3 TFA/DCM (3 mL) was added and it was stirred at 0° C. to rt for 19 h. It was concentrated and the residue was purified by reverse phase preparative HPLC (Gemini™ Prep C18 5 µm column; Phenomenex, Torrance, CA; MeCN in water with 0.1% TFA, gradient elution) to give the title product (9 mg) as a film. m/z (ESI, +ve ion) 579.1 (M+H)+.

Step 3: (3R,6R,7S,21S)-6'-chloro-7-hydroxy-3',4'-dihydro-2'H,14H-spiro[9,19-dioxa-12-thia-1,13-diazatetracyclo[13.7.2.0³,⁶.0¹⁸,²³]tetracosa-15,17,23-triene-21,1'-naphthalen]-14-one 12,12-dioxide or (3R,6R,7R,21S)-6'-chloro-7-hydroxy-3',4'-dihydro-2'H,14H-spiro[9,19-dioxa-12-thia-1,13-diazatetracyclo[13.7.2.0³,⁶.0¹⁸,²³]tetracosa-15,17,23-triene-21,1'-naphthalen]-14-one 12,12-dioxide

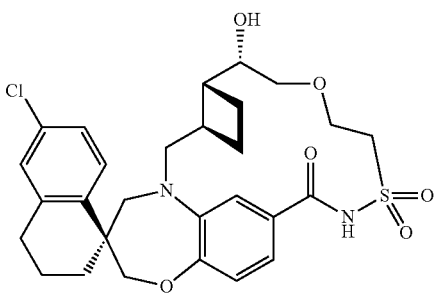

or

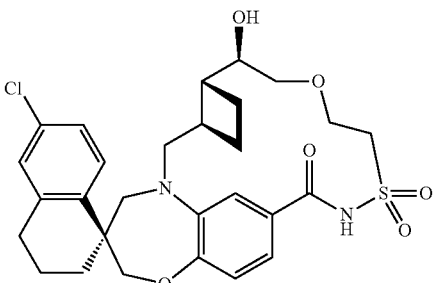

4-Dimethylaminopyridine (DMAP) (0.019 g, 0.155 mmol) was added to a solution of (S)-6'-chloro-5-(((1R,2R)-2-((S)-1-hydroxy-2-(2-sulfamoylethoxy)ethyl)cyclobutyl) methyl)-3',4,4',5-tetrahydro-2H,2'H-spiro[benzo[b][1,4]oxazepine-3,1'-naphthalene]-7-carboxylic acid (Example 866, Step 2; 0.009 g, 0.016 mmol) in DCM (31 mL) which was cooled by ice bath. EDC (0.021 g, 0.109 mmol) was added slowly and it was stirred at 0° C. to rt overnight. It was concentrated and the residue was purified by reverse phase preparative HPLC (Gemini™ Prep C18 5 µm column; Phenomenex, Torrance, CA; MeCN in water with 0.1% TFA, gradient elution) to give the title product (3.8 mg) as a film. ¹H NMR (400 MHz, CD₂Cl₂) δ 7.73 (m, 1H), 7.26 (m, 1H), 7.18 (m, 1H), 7.13 (m, 1H), 7.09 (m, 1H), 6.97 (m, 1H), 4.70 (m, 1H), 4.12 (m, 2H), 4.07 (m, 1H), 3.99-3.77 (m, 3H), 3.49-3.37 (m, 2H), 3.35-3.16 (m, 3H), 3.06 (dd, J=6.16, 15.55 Hz, 1H), 2.82-2.74 (m, 2H), 2.64 (dd, J=7.53, 16.73 Hz, 1H), 2.46 (br. s., 1H), 2.18-1.53 (m, 8H), 1.47-1.37 (m, 1H). m/z (ESI, +ve ion) 561.2 (M+H)+.

Example 867. (1S,3'R,6'S,8'S)-6-chloro-8'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'S,8'R)-6-chloro-8'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide Example 870. (3R,6R,7R,22S)-6'-chloro-7-hydroxy-3',4'-dihydro-2'H,15H-spiro[9,20-dioxa-13-thia-1,14-diazatetracyclo[14.7.2.0³,⁶.0¹⁹,²⁴]pentacosa-16,18,24-triene-22,1'-naphthalen]-15-one 13,13-dioxide or (3R,6R,7S,22S)-6'-chloro-7-hydroxy-3',4'-dihydro-2'H,15H-spiro[9,20-dioxa-13-thia-1,14-diazatetracyclo[14.7.2.0³,⁶.0¹⁹,²⁴]pentacosa-16,18,24-triene-22,1'-naphthalen]-15-one 13,13-dioxide

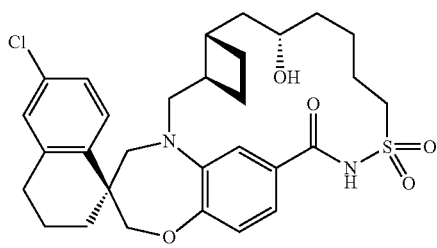

or

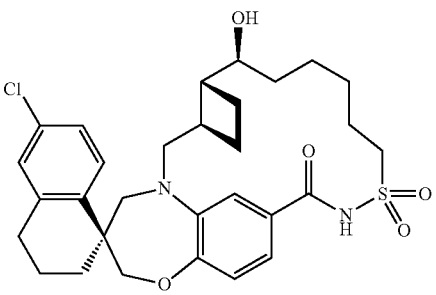

or

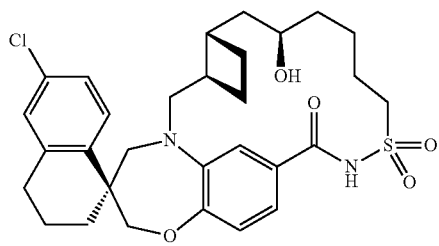

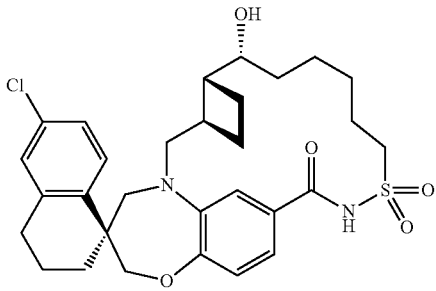

A mixture of (1S,3'R,6'S,8'R,9'E)-6-chloro-8'-hydroxy-3,4-dihydro-2H,15'H-spiro [naphthalene-1,22'[20]oxa[13]thia[1,14]diazatetracyclo[14.7.2.0³,⁶.0¹⁹,²⁴]pentacosa[9,16,18,24]tetraen]-15'-one 13',13'-dioxide (Example 884; 0.004 g, 7.00 μmol) and platinum (IV) oxide (1.6 mg, 7.0 μmol) in EtOAc (7 mL) was stirred under H₂ at rt for 46 min. It was filtered through syringe filter to remove solid catalyst. The filtrate was concentrated and the residue was purified by reverse phase preparative HPLC (Gemini™ Prep C₁₈ 5 μm column; Phenomenex, Torrance, CA; MeCN in water with 0.1% TFA, gradient elution) to give the title product (2 mg) as a white solid. ¹H NMR (500 MHz, CD₂Cl₂) δ 8.26 (br. s., 1H), 7.73 (m, 1H), 7.18 (dd, J=2.20, 8.56 Hz, 1H), 7.09 (d, J=2.45 Hz, 1H), 7.01 (m, 2H), 6.93 (m, 1H), 4.09 (m, 2H), 3.86-3.69 (m, 4H), 3.46-3.35 (m, 2H), 3.23 (d, J=14.18 Hz, 1H), 3.12-3.04 (m, 1H), 3.02-2.90 (m, 1H), 2.81-2.71 (m, 3H), 2.67-1.25 (m, 16H). m/z (ESI, +ve ion) 573.2 (M+H)⁺.

Platinum (IV) oxide (0.24 mg, 1.05 μmol) was added to a solution of Example 863 (0.003 g, 5.2 μmol) in EtOAc (1 mL). It was stirred under H₂ atmosphere for 2 h. It was concentrated and the residue was purified by reverse phase preparative HPLC (Gemini™ Prep C₁₈ 5 μm column; Phenomenex, Torrance, CA; MeCN in water with 0.1% TFA, gradient elution) to provide the title product (2.2 mg) as a film. ¹H NMR (500 MHz, CD₂Cl₂) δ 7.67 (m, 1H), 7.44 (br. s., 1H), 7.33 (br. s., 1H), 7.15 (dd, J=2.20, 8.56 Hz, 1H), 7.09 (d, J=2.20 Hz, 1H), 6.96 (d, J=8.07 Hz, 1H), 4.26-4.13 (m, 2H), 3.84 (m, 1H), 3.80-3.64-(m, 3H), 3.55 (br. s., 3H), 3.42-3.35 (m, 1H), 3.28 (dd, J=2.45, 9.54 Hz, 1H), 2.80-2.71 (m, 2H), 2.41-1.20 (m, 15H). m/z (ESI, +ve ion) 575.1 (M+H)⁺.

Example 872. (1S,3'R,6'R,8'E,12'R)-6-chloro-12'-ethyl-7'-methylidene-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

Example 876. (1S,3'R,6'R,7'R,9'R,11'R)-6-chloro-9'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,9'S,11'R)-6-chloro-9'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,9'R,11'R)-6-chloro-9'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,9'S,11'R)-6-chloro-9'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,9'R,11'S)-6-chloro-9'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,9'S,11'S)-6-chloro-9'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,9'R,11'S)-6-chloro-9'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,9'S,11'S)-6-chloro-9'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide

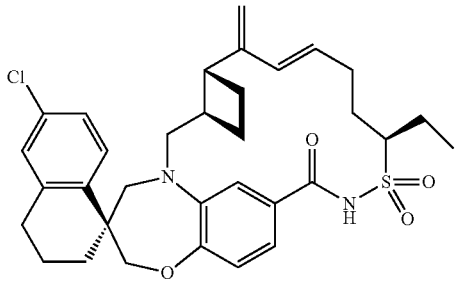

At 0° C., μ-chloro[di(cyclopenta-2,4-dien-1-yl)]dimethyl(μ-methylene)titaniumaluminum (Tebbe's reagent, 0.5 M solution in toluene; 1.9 mL, 0.97 mmol) was added to a solution of Example 915 (0.058 g, 0.097 mmol) in THF (2.4 mL). It was stirred at 0° C. for 10 min. It was poured into ice water (10 mL), acidified with 1 N HCl solution to pH 2-4, extracted with EtOAc (2×110 mL). The organic phase was washed with brine, dried over anhydrous sodium sulfate. After concentration the residue was purified by reverse phase preparative HPLC (Gemini™ Prep C$_{18}$ 5 μm column; Phenomenex, Torrance, CA; MeCN in water with 0.1% TFA, gradient elution) to provide the title product (19 mg) as a white solid. $^1$H NMR (500 MHz, CD$_2$Cl$_2$) δ 7.99-8.05 (m, 1H), 7.73 (m, 1H), 7.27 (m, 1H), 7.19 (m, 1H), 7.11 (m, 1H), 6.83 (m, 1H), 6.79 (m, 1H), 5.96 (m, 1H), 5.87-5.79 (m, 1H), 4.74 (s, 1H), 4.67 (s, 1H), 4.11-4.01 (m, 2H), 3.94-3.86 (m, 2H), 3.73 (d, J=14.18 Hz, 1H), 3.27 (d, J=14.18 Hz, 1H), 3.11 (m, 1H), 3.03 (dd, J=4.77, 15.53 Hz, 1H), 2.84-2.73 (m, 2H), 2.25-2.15 (m, 1H), 2.12-1.49 (m, 13H), 1.39 (t, J=12.96 Hz, 1H), 1.24-1.14 (m, 3H). m/z (ESI, +ve ion) 595.1 (M+H)$^+$.

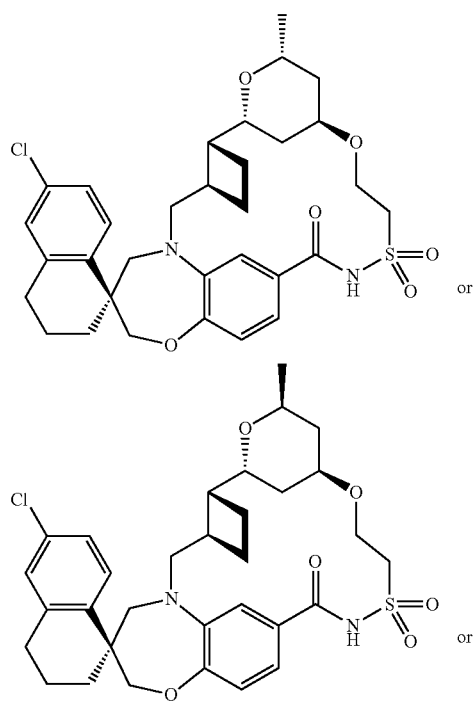

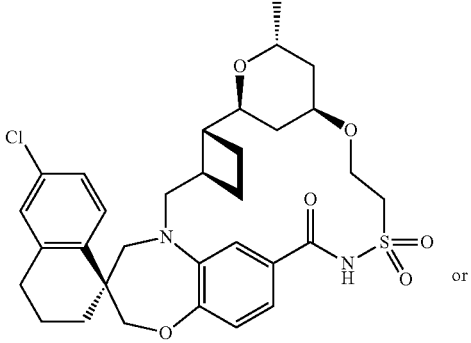

or

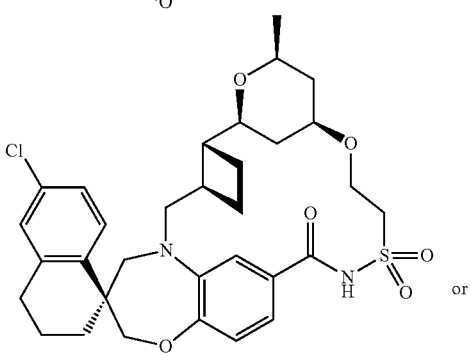

or

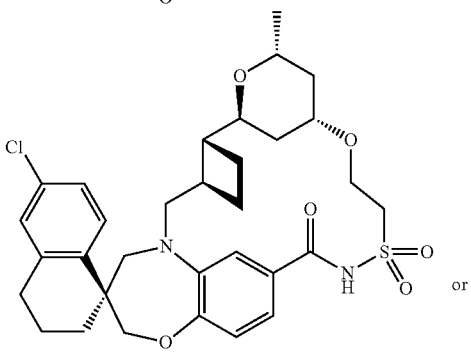

or

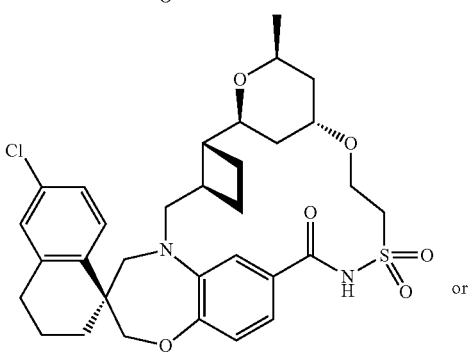

or

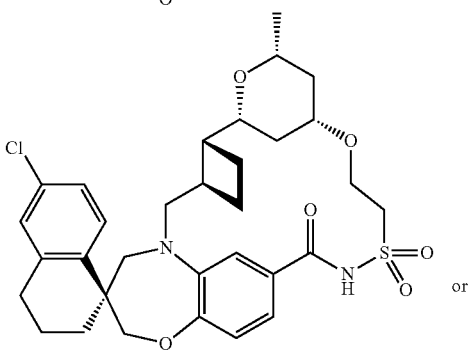

or

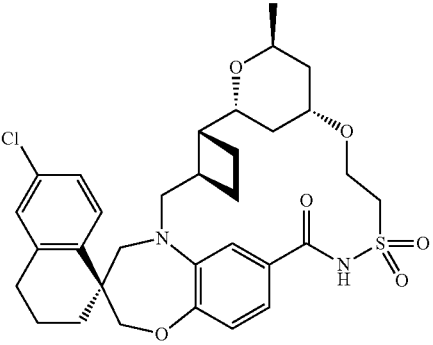

or

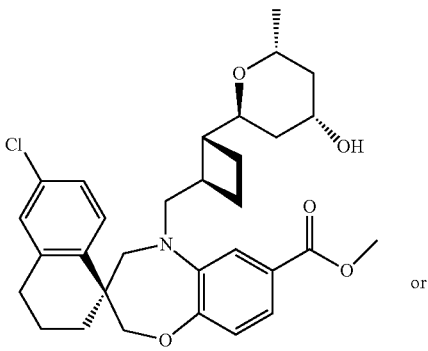

or

Step 1: (S)-methyl 6'-chloro-5-(((1R,2R)-2-((2S,4S,6R)-4-hydroxy-6-methyltetra-hydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S,6S)-4-hydroxy-6-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S,6R)-4-hydroxy-6-methyltetra-hydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S,6S)-4-hydroxy-6-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R,6R)-4-hydroxy-6-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R,6S)-4-hydroxy-6-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S,6R)-4-hydroxy-6-methyltetra-hydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R,6S)-4-hydroxy-6-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

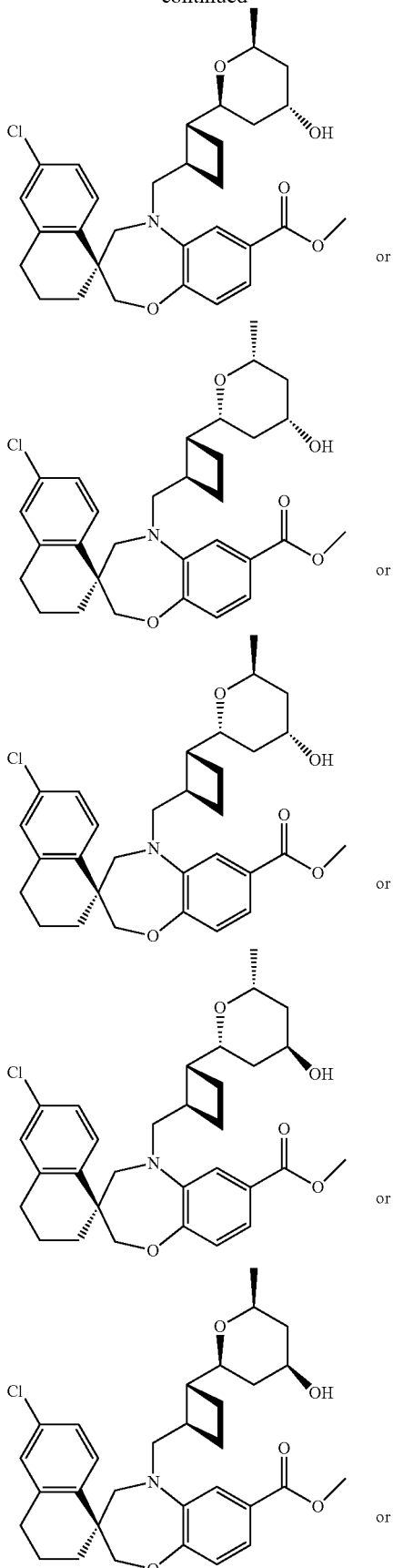

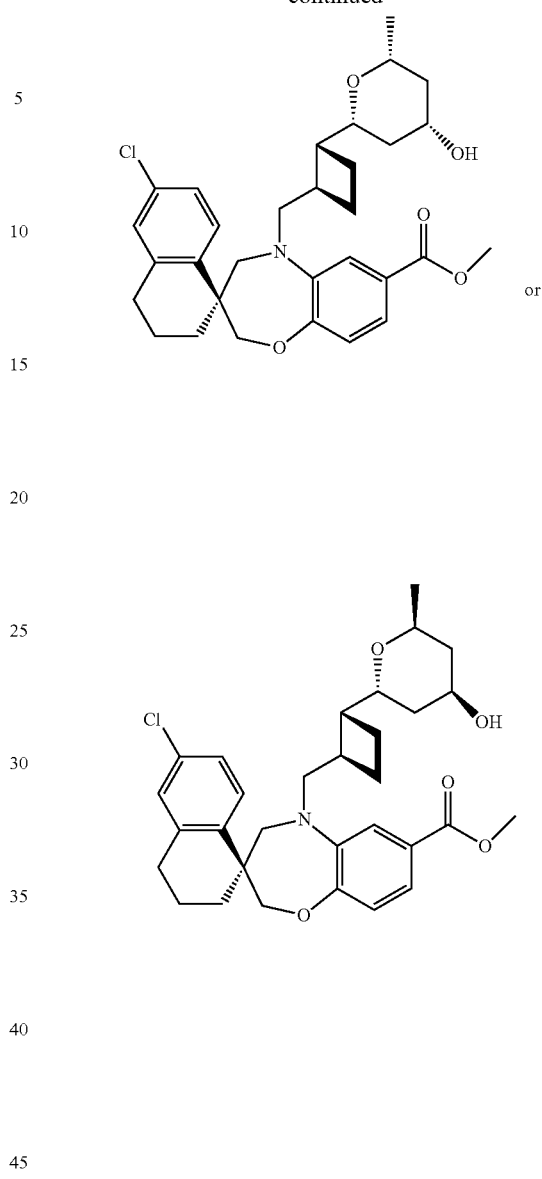

A mixture of (S)-methyl 6'-chloro-5-(((1R,2R)-2-formyl-cyclobutyl)methyl)-3',4,4',5-tetrahydro-2H,2'H-spiro[benzo [b][1,4]oxazepine-3,1'-naphthalene]-7-carboxylate (Intermediate AA11A, Step 20A; 0.190 g, 0.419 mmol) and 4-penten-2-ol (0.047 mL, 0.54 mmol) in TFA (1.7 mL) and DCM (3.5 mL) was degassed with $N_2$ and stirred at rt for 1 h. It was quenched with $NaHCO_3$ solution and extracted with EtOAc (60 mL). The organic phase was dried over anhydrous sodium sulfate and concentrated. The residue was loaded to a 12 g ISCO Gold column and eluted with 0% to 10% (EtOAc/hexane) to provide the title (124 mg) as a film. The film was stirred with saturated $Na_2CO_3$ solution (1 mL)/MeOH (2 mL) and THF (2 mL) at rt for 50 min. It was extracted with EtOAc (100 mL). The organic phase was washed with brine and dried over anhydrous sodium sulfate and concentrated. The residue was loaded to a 4 g ISCO Gold column and eluted with 0% to 40% (EtOAc/hexane) to provide the title compound (86 mg) as a white solid. m/z (ESI, +ve ion) 540.1 $(M+H)^+$.

1775

Step 2: (S)-6'-chloro-5-(((1R,2R)-2-((2S,4R,6R)-6-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4S,6S)-6-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R,6R)-6-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4S,6R)-6-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4R,6S)-6-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4S,6S)-6-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R,6S)-6-methyl-4-(2-sulfamoylethoxy) tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4S,6R)-6-methyl-4-(2-sulfamoylethoxy)tetrahydro-2H-pyran-2-yl)cyclobutyl)methyl)-3',4,4',5-tetrahydro-2H,2'H-spiro[benzo [b][1,4]oxazepine-3,1'-naphthalene]-7-carboxylic Acid

1776

-continued

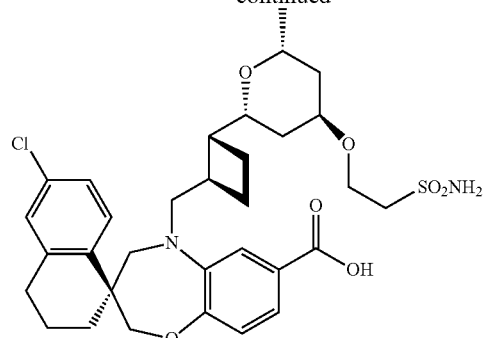

or

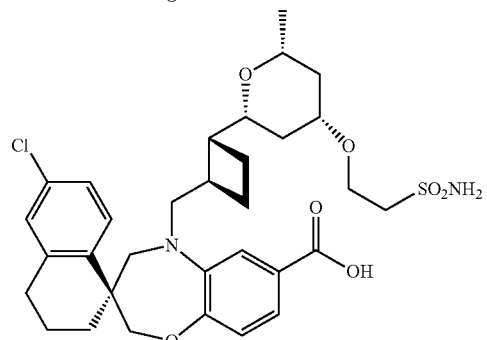

or

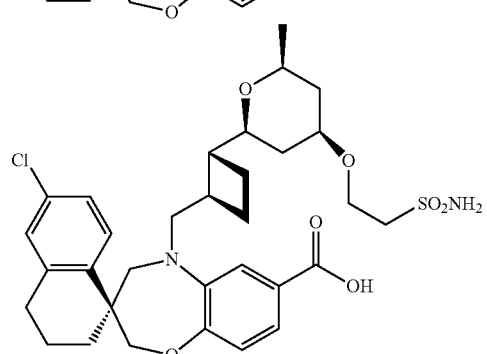

or

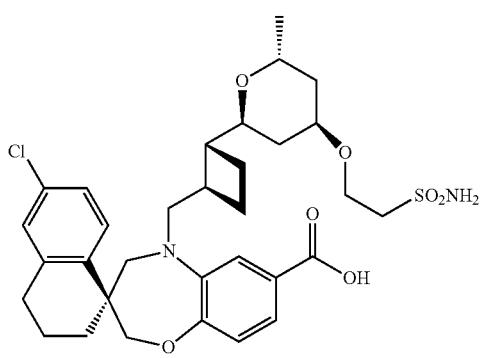

or

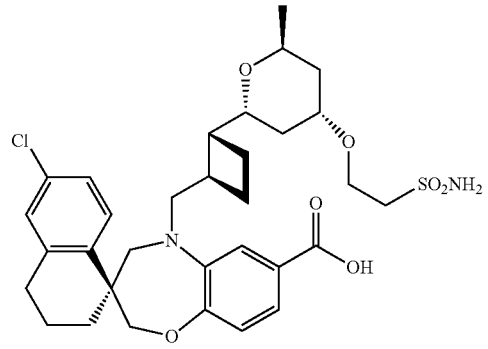

or

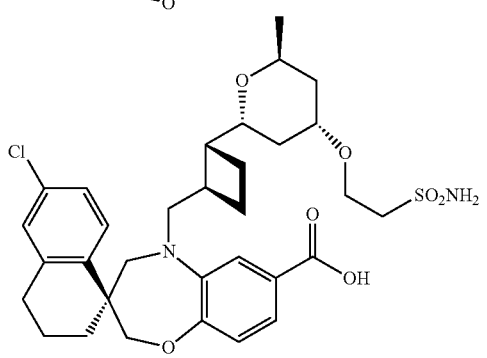

or

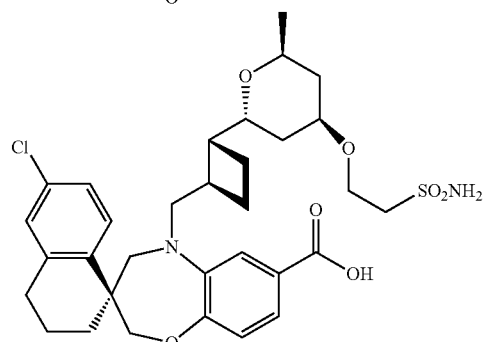

or

-continued

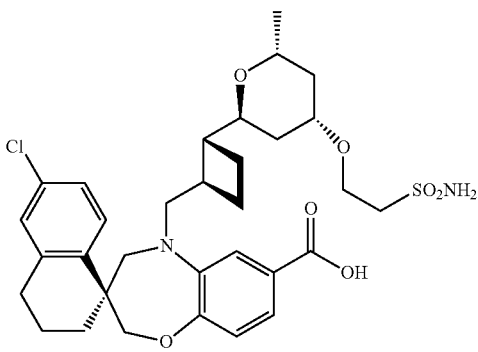

At 0° C., sodium hydride (60% dispersion in mineral oil; 14 mg, 0.650 mmol) was added to a solution of (1'S)-methyl 6'-chloro-5-(((1R,2R)-2-((2S,4R)-4-hydroxy-6-methyl-tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Step 1; 0.090 g, 0.167 mmol) in THF (6 mL). It was stirred at rt for 10 min. Then N,N-bis(4-methoxybenzyl)-ethenesulfonamide (Example 876, Step 1, 0.075 g, 0.217 mmol) in THF (2.5 mL) was added. It was stirred at rt for 19 h. The reaction was quenched with water (2 mL) and extracted with EtOAc (120 mL). The organic phase was washed with brine and dried over anhydrous sodium sulfate. After it was concentrated, the residue was purified by reverse phase preparative HPLC (Gemini™ Prep $C_{18}$ 5 μm column; Phenomenex, Torrance, CA; MeCN in water with 0.1% TFA, gradient elution) to provide an intermediate (120 mg) as a white solid.

Hydrolysis I. The white solid was dissolved in THF (4 mL), MeOH (4 mL) and 1 M LiOH solution (3 mL) and stirred at 43° C. for 16 h. It was concentrated, acidified with 1N HCl to pH 2-4, extracted with EtOAc (110 mL). The organic phase was washed with brine and dried over anhydrous sodium sulfate. It was concentrated to give a residue.

Hydrolysis II: The residue was dissolved in 1:2 TFA/DCM (5 mL) and stirred at rt overnight. It was concentrated and the residue was loaded on a 12 g ISCO Gold column and eluted with 0% to 50% (EtOAc(0.3% HOAc)/hexane), to provide the title compound (35 mg) as a film. m/z (ESI, +ve ion) 633.1 (M+H)⁺.

Step 3: (1S,3'R,6'R,7'R,9'R,11'R)-6-chloro-9'-methyl-3,4-dihydro-2H,17'H-spiro[naphthalene-1, 24'-[8,12,22]trioxa[15]thia[1,16]diazapentacyclo [16.7.2.1$^{7,11}$.0$^{3,6}$.0$^{21,26}$]octacosa[18,20,26]trien]-17'-one 15',15'-dioxide or (1S,3'R,6'R,7'R,9'S,11'R)-6-chloro-9'-methyl-3,4-dihydro-2H,17'H-spiro [naphthalene-1,24'-[8,12,22]trioxa[15]thia[1,16] diazapentacyclo[16.7.2.1$^{7,11}$.0$^{3,6}$.0$^{21,26}$]octacosa[18, 20,26]trien]-17'-one 15',15'-dioxide or (1S,3'R,6'R, 7'S,9R,11'R)-6-chloro-9'-methyl-3,4-dihydro-2H, 17'H-spiro[naphthalene-1,24'-[8,12,22]trioxa[15]thia [1,16]diazapentacyclo[16.7.2.1$^{7,11}$.0$^{3,6}$.0$^{21,26}$] octacosa[18,20,26]trien]-17'-one 15',15'-dioxide or (1S,3'R,6'R,7'S,9'S,11'R)-6-chloro-9'-methyl-3,4-dihydro-2H,17'H-spiro[naphthalene-1,24'-[8,12,22] trioxa[15]thia[1,16]diazapentacyclo[16.7.2.1$^{7,11}$.0$^{3,6}$. 0$^{21,26}$]octacosa[18,20,26]trien]-17'-one 15',15'-dioxide or (1S,3'R,6'R,7'S,9R,1']S)-6-chloro-9'-methyl-3,4-dihydro-2H,17'H-spiro[naphthalene-1,24'-[8,12, 22]trioxa[15]thia[1,16]diazapentacyclo[16.7.2.1$^{7,11}$. 0$^{3,6}$.0$^{21,26}$]octacosa[18,20,26]trien]-17'-one 15',15'-dioxide or (1S,3'R,6'R,7'S,9'S,11'S)-6-chloro-9'-methyl-3,4-dihydro-2H,17'H-spiro[naphthalene-1, 24'-[8,12,22]trioxa[15]thia[1,16]diazapentacyclo [16.7.2.1$^{7,11}$.0$^{3,6}$.0$^{21,26}$]octacosa[18,20,26]trien]-17'-one 15',15'-dioxide or (1S,3'R,6'R,7'S,9'R,11'S)-6-chloro-9'-methyl-3,4-dihydro-2H,17'H-spiro [naphthalene-1,24'-[8,12,22]trioxa[15]thia[1,16] diazapentacyclo[16.7.2.1$^{7,11}$.0$^{3,6}$.0$^{21,26}$]octacosa[18, 20,26]trien]-17'-one 15',15'-dioxide or (1S,3'R,6'R, 7'R,9'S,11'S)-6-chloro-9'-methyl-3,4-dihydro-2H, 17'H-spiro[naphthalene-1,24'-[8,12,22]trioxa[15]thia [1,16]diazapentacyclo[16.7.2.1$^{7,11}$.0$^{3,6}$.0$^{21,26}$] octacosa[18,20,26]trien]-17'-one 15',15'-dioxide N,N-dimethylpyridin-4-amine (DMAP) (0.061 g, 0.497 mmol) was added to a solution of (1'S)-6'-chloro-5-(((1R, 2R)-2-((2S,4R)-6-methyl-4-(2-sulfamoylethoxy)tetrahydro-2H-pyran-2-yl)cyclobutyl)methyl)-3',4,4',5-tetrahydro-2H, 2'H-spiro[benzo[b][1,4]oxazepine-3,1'-naphthalene]-7-carboxylic Acid (Example 876, Step 2; 0.035 g, 0.055 mmol) in DCM (50 mL) at 0° C. Then N1-((ethylimino) methyl)-N3,N3-dimethylpropane-1,3-diamine hydrochloride (EDC; 0.053 g, 0.276 mmol) was added slowly in portions and it was stirred at 0° C. to rt overnight. After it was concentrated, the residue was purified by reverse phase preparative HPLC (Gemini™ Prep $C_{18}$ 5 μm column; Phenomenex, Torrance, CA; MeCN in water with 0.1% TFA, gradient elution) to provide the title compound (4.5 mg) a white solid. ¹H NMR (500 MHz, CD$_2$Cl$_2$) δ 8.34-8.24 (m, 1H), 7.71 (s, 1H), 7.18 (m, 1H), 7.08 (m, 2H), 6.97 (s, 1H), 6.83 (m, 1H), 4.14-3.97 (m, 3H), 3.85 (ddd, J=3.30, 8.19, 11.49 Hz, 1H), 3.80-3.64 (m, 4H), 3.55-3.45 (m, 1H), 3.40-3.33 (m, 1H), 3.32-3.21 (m, 3H), 2.87-2.70 (m, 2H), 2.25-1.58 (m, 11H), 1.49-1.38 (m, 1H), 1.18 (d, J=6.11 Hz, 3H), 1.15-1.06 (m, 2H). m/z (ESI, +ve ion) 615.0 (M+H)⁺.

Example 877. (1S,3'R,6'R,8'R,9'R,12'R)-6-chloro-12'-ethyl-8',9'-dihydroxy-7'-methylidene-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,8'S,9'S,12'R)-6-chloro-12'-ethyl-8',9'-dihydroxy-7'-methylidene-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,8'R,9'R,12'R)-6-chloro-12'-ethyl-8',9'-dihydroxy-7'-methylidene-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,8'R,9'S,12'R)-6-chloro-12'-ethyl-8',9'-dihydroxy-7'-methylidene-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide

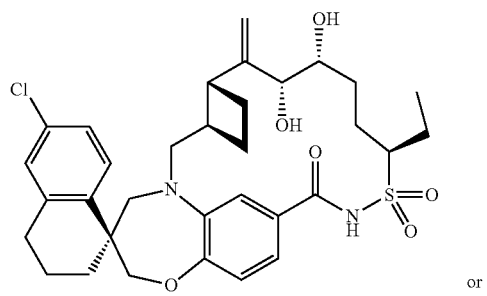

or

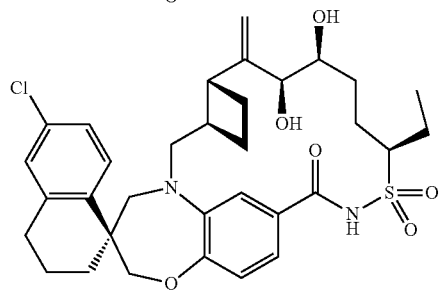

or

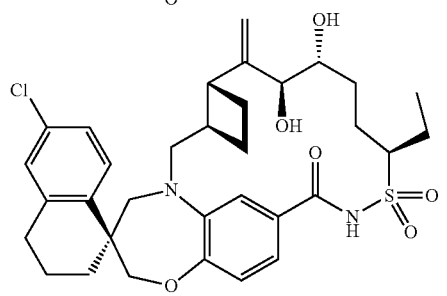

or

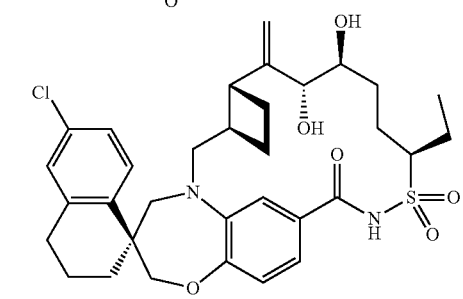

The title compound (1.8 mg) was obtained as a single isomer (second eluting peak) from the reverse phase preparative HPLC in Example 873 as a white solid. ¹H NMR (500 MHz, CD₃OD) δ 7.77 (m, 1H), 7.25 (m, 1H), 7.18 (m, 1H), 7.11 (m, 2H), 6.81 (m, 1H), 5.16 (s, 1H), 5.08 (s, 1H), 4.10-3.99 (m, 2H), 3.86 (d, J=7.58 Hz, 1H), 3.77 (dd, J=4.28, 15.28 Hz, 1H), 3.71-3.63 (m, 2H), 3.62-3.59 (m, 1H), 3.56-3.51 (m, 1H), 3.46 (m, 1H), 3.38 (m, 1H), 3.17 (m, 1H), 2.91-2.73 (m, 3H), 2.68 (br. s., 1H), 2.21-1.77 (m, 9H), 1.75-1.63 (m, 2H), 1.51-1.33 (m, 3H), 1.11 (t, J=6.85 Hz, 3H). m/z (ESI, +ve ion) 629.2 (M+H)⁺.

Example 878. (1S,3'R,6'R,7'S,11'S)-6-chloro-3,4-dihydro-2H,17'H-spiro[naphthalene-1,24'-[8,12,22]trioxa[15]thia[1,16]diazapentacyclo[16.7.2.1⁷,¹¹.0³,⁶.0²¹,²⁶]octacosa[18,20,26]trien]-17'-one 15',15'-dioxide or (1S,3'R,6'R,7'S,11'R)-6-chloro-3,4-dihydro-2H,17'H-spiro[naphthalene-1,24'-[8,12,22]trioxa[15]thia[1,1diazapentacyclo[16.7.2.1⁷,¹¹.0³,⁶.0²¹,²⁶]octacosa[18,20,26]trien]-17'-one 15',15'-dioxide or (1S,3'R,6'S, 7'S,11'R)-6-chloro-3,4-dihydro-2H,17'H-spiro[naphthalene-1,24'-[8,12,22]trioxa[15]thia[1,16]diazapentacyclo[16.7.2.1⁷,¹¹.0³,⁶.0²¹,²⁶]octacosa[18,20,26]trien]-17'-one 15',15'-dioxide or (1S,3'R,6'S, 7'S,11'S)-6-chloro-3,4-dihydro-2H,17'H-spiro[naphthalene-1,24'-[8,12,22]trioxa[15]thia[1,16]diazapentacyclo[16.7.2.1⁷,¹¹.0³,⁶.0²¹,²⁶]octacosa[18,20,26]trien]-17'-one 15',15'-dioxide

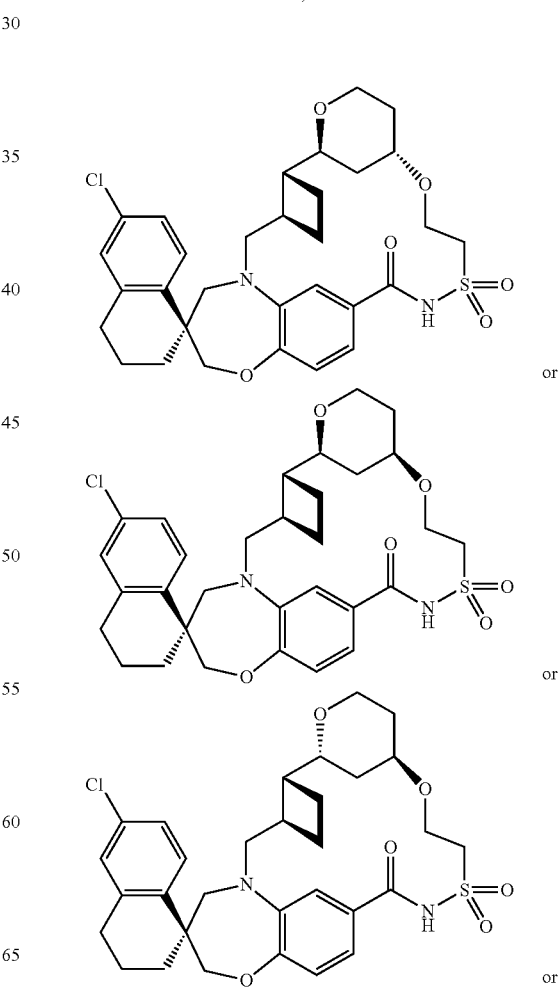

or

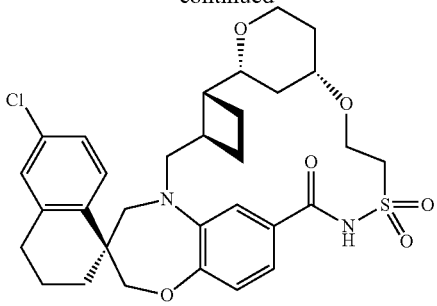

Step 1: (S)-methyl 6'-chloro-5-(((1R,2R)-2-((2R,4R)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

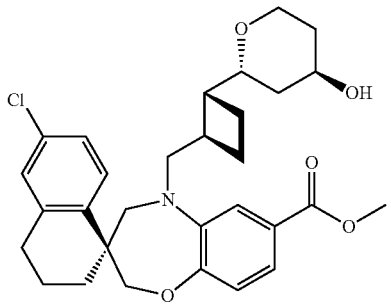

or

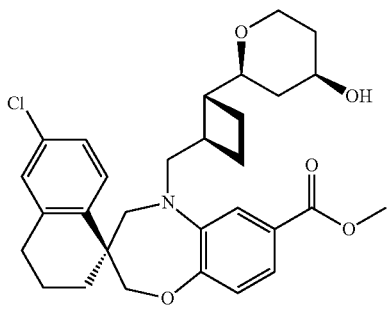

or

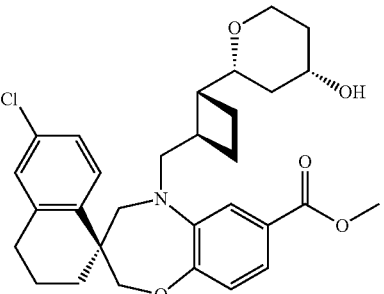

or

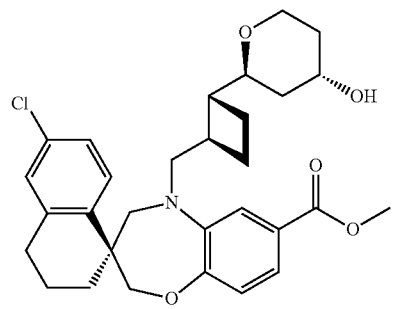

A mixture of (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A; 0.243 g, 0.535 mmol), 3-buten-1-ol (54 mg, 0.7 mmol) in TFA (4.5 mL) and DCM (9 mL) was degassed with N₂ and stirred at rt for 30 min. It was quenched with NaHCO₃ solution to pH >7 and extracted with EtOAc (60 mL). The organic phase was dried over anhydrous sodium sulfate, concentrated. To the residue was added saturated Na₂CO₃ solution (1 mL), MeOH (2 mL) and THF (2 mL). After it was stirred at rt for 30 min it was neutralized with 1N HCl solution to pH 7 and extracted with EtOAc (100 mL). The organic phase was washed with brine, dried over anhydrous sodium sulfate and concentrated. The residue was loaded to a 24 g ISCO Gold column and eluted with 0% to 50% EtOAc/hexane to provide the title compound (210 mg) as a white solid. m/z (ESI, +ve ion) 526.1 (M+H)⁺.

Step 2: (S)-6'-chloro-5-(((1R,2R)-2-((2R,4R)-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4R)-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4S)-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4S)-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid

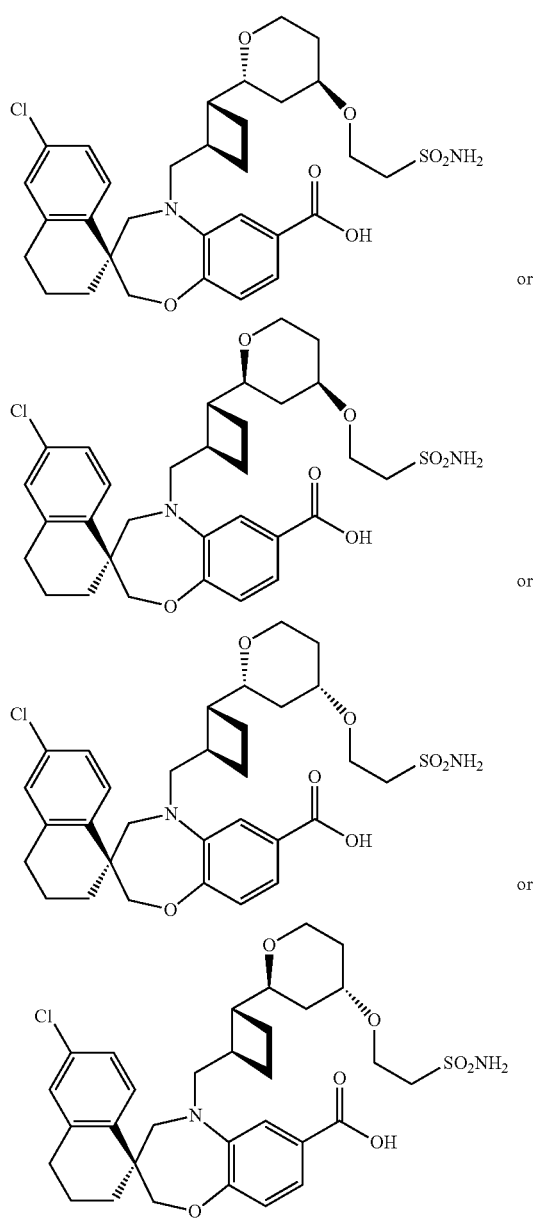

Sodium hydride (60% dispersion in mineral oil; 14 mg, 0.341 mmol) was added to a solution of (S)-methyl 6'-chloro-5-(((1R,2R)-2-((2R,4R)-4-hydroxytetrahydro-2H-pyran-2-yl)cyclobutyl) methyl)-3',4,4',5-tetrahydro-2H,2'H-spiro[benzo[b][1,4]oxazepine-3,1'-naphthalene]-7-carboxylate (Example 878, Step 1; 0.046 g, 0.087 mmol) in THF (2.5 mL), which was cooled to 0° C. After it was stirred at rt for 15 min, N,N-bis(4-methoxybenzyl)ethenesulfonamide (Example 831, Step 2; 0.052 g, 0.15 mmol) in THF (1.4 mL) was added. It was stirred at rt for 2 h. The reaction mixture was quenched with water (2 mL) and extracted with EtOAc (120 mL). The organic phase was washed with brine and dried over anhydrous sodium sulfate. It was concentrated and the residue was loaded to a 12 g ISCO Gold column and eluted with 0% to 10% (EtOAc/DCM) to provide the addition product (40 mg). The addition product was dissolved in THF (5 mL), MeOH (5 mL) and 1M LiOH solution (3 mL) and stirred at 50° C. for 2 h. It was concentrated, acidified with 1 N HCl solution to pH 2-4, extracted with EtOAc (110 mL). The organic phase was washed with brine and dried over anhydrous sodium sulfate. It was concentrated to give a residue. The residue was dissolved in 1:3 TFA/DCM (4 mL) and stirred at rt for 19 h. It was concentrated and the residue was loaded to a 4 g ISCO Gold column and eluted with 0% to 20% 30 min (EtOAc(0.2% HOAc)/DCM) to provide the title compound (11.5 mg) as a film. m/z (ESI, +ve ion) 619.1 (M+H)+.

Step 3: (1S,3'R,6'R,7'S,11'S)-6-chloro-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'R)-6-chloro-3,4-dihydro-2H,17'H-spiro[naphthalene-1,24'-[8,12,22]trioxa[15]thia[1,1diazapentacyclo[16.7.2.1$^{7,11}$.0$^{3,6}$.0$^{21,26}$]octacosa[18,20,2 6]trien]-17'-one 15',15'-dioxide or (1S,3'R,6'S,7'S,11'R)-6-chloro-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'S,7'S,11'S)-6-chloro-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide N,N-Dimethylpyridin-4-amine (DMAP) (0.018 g, 0.15 mmol) was added to a solution of (S)-6'-chloro-5-(((1R,2R)-2-((2R,4R)-4-(2-sulfamoylethoxy)tetrahydro-2H-pyran-2-yl)cyclobutyl) methyl)-3',4,4',5-tetrahydro-2H,2'H-spiro[benzo[b][1,4]oxazepine-3,1'-naphthalene]-7-carboxylic Acid (Example 878, Step 2; 0.0115 g, 0.019 mmol) in DCM (26 mL) at 0° C. Then N1-((ethylimino)methylene)-N3,N3-dimethylpropane-1,3-diamine hydrochloride (EDC) (0.019 g, 0.10 mmol) was added slowly in portions and it was stirred at 0° C. to rt for 22 h. It was diluted with EtOAc (100 mL), washed with 1 N HCl (2×1 mL), brine, dried over anhydrous sodium sulfate and concentrated. The residue was loaded to a 4 g ISCO Gold column and eluted with 0% to 7% (EtOAc(0.2% HOAc)/DCM) to provide the title compound (7.2 mg) as a white solid. $^1$H NMR (400 MHz, CD$_2$Cl$_2$) δ 8.13 (br. s., 1H), 7.70 (d, J=8.41 Hz, 1H), 7.17 (dd, J=2.35, 8.41 Hz, 1H), 7.10 (m, 2H), 6.96 (m, 1H), 6.71 (s, 1H), 4.09 (s, 2H), 4.04-3.95 (m, 2H), 3.85 (d, J=5.48 Hz, 1H), 3.81 (m, 1H), 3.73-3.66 (m, 2H), 3.64-3.59 (m, 1H), 3.58-3.49 (m, 3H), 3.32-3.17 (m, 2H), 2.81-2.73 (m, 2H), 2.42-2.31 (m, 1H), 2.04 (d, J=5.67 Hz, 1H), 1.99-1.24 (m, 12H). m/z (ESI, +ve ion) 601.1 (M+H)+.

Example 881. (1S,3'R,6'S,8'S)-6-chloro-8'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'S,8'R)-6-chloro-8'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide

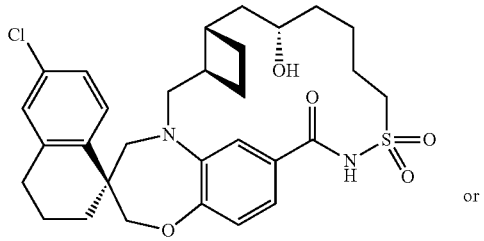

or

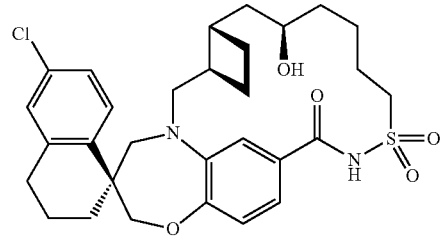

A mixture of (1S,3'R,6'S,8'R,9'E)-6-chloro-8'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (Example 883; 0.002 g, 3.5 µmol) and platinum (IV) oxide (0.79 mg, 3.5 µmol) in EtOAc (1.7 mL) was stirred under H$_2$ at rt for 1 h. It was filtered through syringe filter to remove solid catalyst and the filtrate was concentrated to provide the title compound (1.9 mg) as a white solid. $^1$H NMR (400 MHz, CD$_3$OD) δ 7.78 (d, J=8.41 Hz, 1H), 7.37 (br. s., 1H), 7.20 (dd, J=2.35, 8.41 Hz, 2H), 7.12 (d, J=2.15 Hz, 1H), 6.86 (m, 1H), 5.69 (br. s., 1H), 4.17-3.43 (m, 6H), 3.19-3.13 (m, 2H), 2.87-2.74 (m, 3H), 2.38 (br. s., 2H), 2.31-2.20 (m, 1H), 2.11 (d, J=13.11 Hz, 2H), 2.04-1.89 (m, 5H), 1.88-1.16 (m, 8H). m/z (ESI, +ve ion) 573.2 (M+H)+.

Example 882. (1S,3'R,6'R,7'R,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]]pentacosa[8,16,18,24]tetraen]-15'-one 13',13'-dioxide

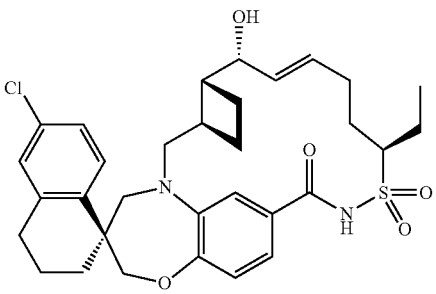

Step 1: (S)-tert-butyl 6'-chloro-5-(((1R,2R)-2-((R)-1-hydroxyallyl)cyclobutyl)methyl)-3',4,4',5-tetrahydro-2H,2'H-spiro[benzo[b][1,4]oxazepine-3,1'-naphthalene]-7-carboxylate

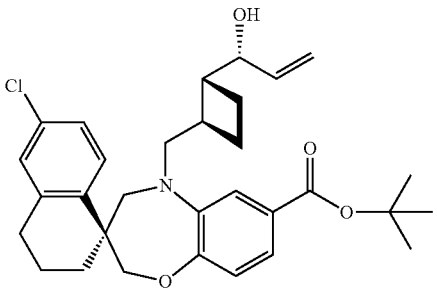

Vinylmagnesium chloride solution (1.4 mL, 2.23 mmol) was added dropwase to a solution of (S)-tert-butyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20B; 754 g, 1.52 mmol) in THF (19 mL) which was cooled with ice bath. It was stirred at 0° C. for 10 min. The reaction mixture was quenched with NH$_4$Cl solution and extracted with EtOAc (200 mL). The organic phase was washed with brine, dried over anhydrous sodium sulfate and concentrated. The residue was loaded to a 220 g ISCO Gold column and eluted with 0% to 10% (EtOAc/hexane). The second peak was the title compound (270 mg) as a white solid. m/z (ESI, +ve ion) 524.2 (M+H)+.

Step 2: (S)-6'-chloro-5-(((1R,2R)-2-((R)-1-hydroxy-allyl)cyclobutyl)methyl)-3',4,4',5-tetrahydro-2H,2'H-spiro[benzo[b][1,4]oxazepine-3,1'-naphthalene]-7-carboxylic Acid

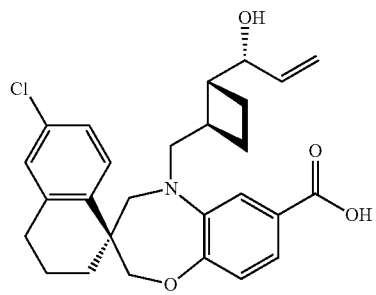

Lithium hydroxide (1.0 M aqueous solution; 6.4 mL, 6.4 mmol) was added to a solution of (S)-tert-butyl 6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylate (Example 882, Step 1; 0.306 g, 0.584 mmol) in THF (13 mL) and MeOH (6.5 mL). It was stirred at 77° C. for 4.5 h. The reaction mixture was concentrated, acidified with 1N HCl solution to pH 2-3 and extracted with EtOAc (200 mL). The organic phase was washed with brine, dried over anhydrous sodium sulfate and concentrated to give the title compound (273 mg) as a white solid. m/z (ESI, +ve ion) 468.2 (M+H)$^+$.

Step 3: (S)-6'-chloro-N—((R)-hept-6-en-3-ylsulfonyl)-5-(((1R,2R)-2-((R)-1-hydroxyallyl)cyclobutyl)methyl)-3',4,4',5-tetrahydro-2H,2'H-spiro[benzo[b][1,4]oxazepine-3,1'-naphthalene]-7-carboxamide

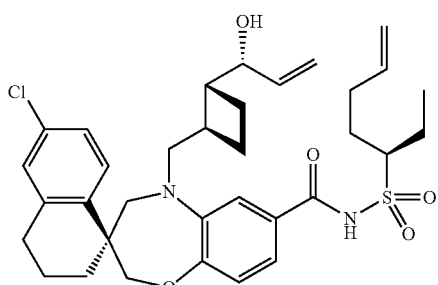

4-Dimethylaminopyridine (DMAP) (0.340 g, 2.78 mmol) was added to a solution of (S)-6'-chloro-5-(((1R,2R)-2-((R)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Example 882, Step 2; 0.186 g, 0.397 mmol) and (R)-hept-6-ene-3-sulfonamide (EE21; 0.137 g, 0.775 mmol) in DCM (8 mL). It was cooled with ice bath. Then EDC (0.229 g, 1.19 mmol) was added portion by portion and it was stirred at 0° C. to rt for 20 h. It was diluted with DCM (180 mL) and washed with 1N HCl (3 mL) and brine (1 mL). The organic phase was dried over anhydrous sodium sulfate and concentrated. The residue was loaded to a 40 g ISCO Gold column and eluted with 0% to 25% (EtOAc(0.2% HOAc)/hexane) to provide the title compound (107 mg) as a white solid. m/z (ESI, +ve ion) 627.1 (M+H)$^+$.

Step 4: (1S,3'R,6'R,7'R,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

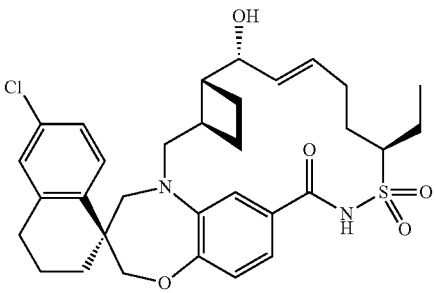

A solution of (S)-6'-chloro-N—((R)-hept-6-en-3-ylsulfonyl)-5-(((1R,2R)-2-((R)-1-hydroxyallyl) cyclobutyl) methyl)-3',4,4',5-tetrahydro-2H,2'H-spiro[benzo[b][1,4] oxazepine-3,1'-naphthalene]-7-carboxamide (Example 882, Step 3; 0.107 g, 0.171 mmol) in 1,2-dichloroethane (122 mL) was degassed with N$_2$. A solution of Hoveyda-Hoveyda-Grubbs II (0.021 g, 0.034 mmol) in 1,2-dichloroethane (5 mL) was added and the mixture was stirred at 45° C. for 4 h. After concentration, the residue was loaded to a 40 g ISCO Gold column and eluted with 0% to 30% (EtOAc (0.2% HOAc)/hexane) to provide the title compound (78 mg) as a white solid. $^1$H NMR (400 MHz, CD$_3$OD) δ 7.77 (m, 1H), 7.42 (m, 1H), 7.20 (m, 1H), 7.11 (m, 2H), 6.94 (m, 1H), 5.54-5.48 (m, 2H), 4.11 (m, 2H), 3.94 (dd, J=5.67, 15.45 Hz, 1H), 3.79 (m, 1H), 3.71 (m, 2H), 3.05 (dd, J=6.06, 15.26 Hz, 1H), 2.87-2.77 (m, 2H), 2.61-2.47 (m, 2H), 2.42-2.33 (m, 1H), 2.15-2.03 (m, 5H), 1.99-1.83 (m, 5H), 1.81-1.73 (m, 2H), 1.72-1.64 (m, 1H), 1.52-1.43 (m, 1H), 1.18 (t, J=7.53 Hz, 3H). m/z (ESI, +ve ion) 599.1 (M+H)$^+$.

Example 883. (1S,3'R,6'S,8'S,9'Z)-6-chloro-8'-hydroxy-3,4-dihydro-2H,15'H-spiro[naphthalene-1,22'[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'S,8'R,9'Z)-6-chloro-8'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide

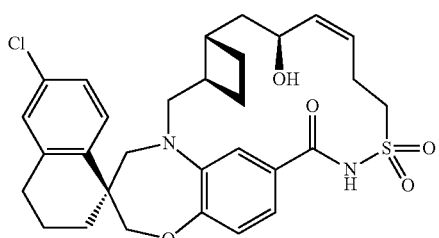

or

1789

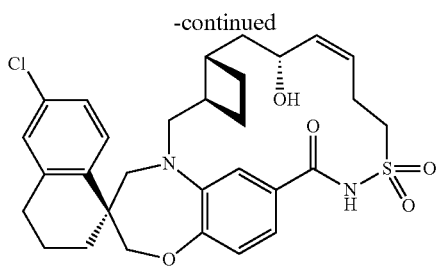

Step 1: (S)-6'-chloro-5-(((1R,2S)-2-((S)-2-hydroxy-but-3-en-1-yl)cyclobutyl)methyl)-3',4,4',5-tetra-hydro-2H,2'H-spiro[benzo[b][1,4]oxazepine-3,1'-naphthalene]-7-carboxylic Acid or (S)-6'-chloro-5-(((1R,2S)-2-((R)-2-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic Acid

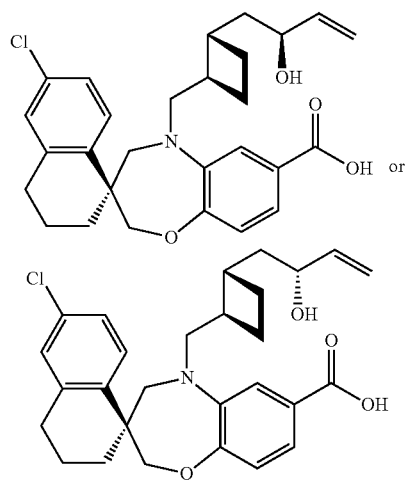

The title compound (16.7 mg) was obtained as a single isomer (first eluting peak) from the reverse phase preparative HPLC in Example 884, Step 3 as a white solid. m/z (ESI, +ve ion) 482.1 (M+H)+.

Step 2: (S)—N-(but-3-en-1-ylsulfonyl)-6'-chloro-5-(((1R,2S)-2-((S)-2-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(but-3-en-1-ylsulfonyl)-6'-chloro-5-(((1R,2S)-2-((R)-2-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide

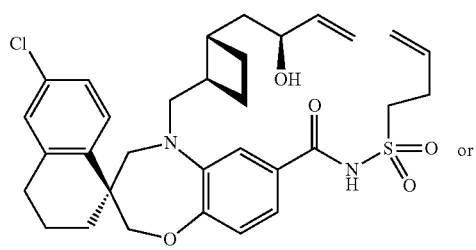

1790

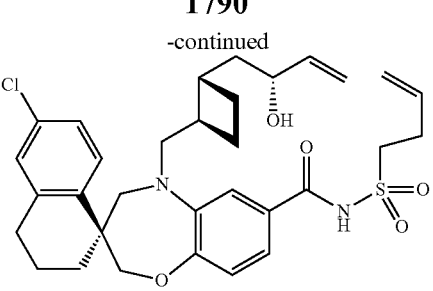

N,N-Dimethylpyridin-4-amine (DMAP) (10.7 mg, 0.087 mmol) was added to a solution of (S)-6'-chloro-5-(((1R,2S)-2-((S)-2-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Example 883, Step 1; 0.014 g, 0.029 mmol) and but-3-ene-1-sulfonamide (EE15; 0.018 g, 0.131 mmol) in DCM (1.1 mL) at 0° C. Then N-(3-dimethylaminopropyl)-N'-ethylcarbodiimide hydrochloride (EDC; 0.011 g, 0.058 mmol) was added portion by portion and it was stirred at rt for 18 h. It was concentrated and the residue was purified by reverse phase preparative HPLC (Gemini™ Prep $C_{18}$ 5 μm column; Phenomenex, Torrance, CA; MeCN in water with 0.1% TFA, gradient elution) to provide the title compound (6.5 mg) as a white solid. m/z (ESI, +ve ion) 599.2 (M+H)+.

Step 3: (1S,3'R,6'S,8'S,9'Z)-6-chloro-8'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'S,8'R,9'Z)-6-chloro-8'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide

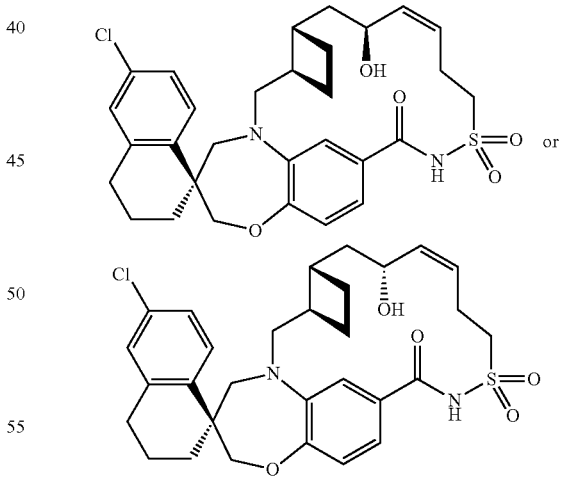

A 250 mL round bottom flask was charged with (S)—N-(but-3-en-1-ylsulfonyl)-6'-chloro-5-(((1R,2S)-2-((S)-2-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide (Example 883, Step 2; 8.0 mg, 0.013 mmol) in toluene (44 mL). It was stirred at rt for 10 min to dissolve the solid starting material and then subjected to three cycles of evacuation/back-filling with nitrogen. To the homogeneous solution was added a solution of Hoveyda-Grubbs II (1.7 mg, 2.6 μmol) in toluene. The mixture was stirred at 106° C. under nitrogen for 1 h and then concentrated. The residue was purified by reverse phase preparative HPLC (Gemini™ Prep C$_{18}$ 5 μm column; Phenomenex, Torrance, CA; MeCN in water with 0.1% TFA, gradient elution) to give the title compound (4.2 mg, second eluting peak) as a white solid. $^1$H NMR (500 MHz, CD$_2$Cl$_2$) δ 9.18 (br. s., 1H), 7.73 (m, 1H), 7.25 (d, J=7.34 Hz, 1H), 7.18 (dd, J=2.08, 8.44 Hz, 1H), 7.09 (d, J=2.20 Hz, 1H), 7.05 (br. s., 1H), 6.98 (m, 1H), 5.68-5.56 (m, 2H), 4.74-4.66 (m, 1H), 4.10 (s, 2H), 3.98 (d, J=15.41 Hz, 1H), 3.90-3.82 (m, 2H), 3.77 (d, J=13.94 Hz, 1H), 3.42-3.35 (m, 2H), 3.32-3.23 (m, 1H), 2.84-2.72 (m, 3H), 2.49-2.40 (m, 2H), 2.39-2.30 (m, 1H), 2.26-2.17 (m, 2H), 2.12-2.06 (m, 2H), 2.00-1.93 (m, 1H), 1.92-1.75 (m, 3H), 1.59-1.49 (m, 2H), 1.41 (t, J=13.33 Hz, 1H). m/z (ESI, +ve ion) 571.3 (M+H)$^+$.

Example 884. (1S,3'R,6'S,8'R,9'E)-6-chloro-8'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide or (1S,3'R,6'S,8'S,9'E)-6-chloro-8'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [9,16,18,24]tetraen]-15'-one 13',13'-dioxide

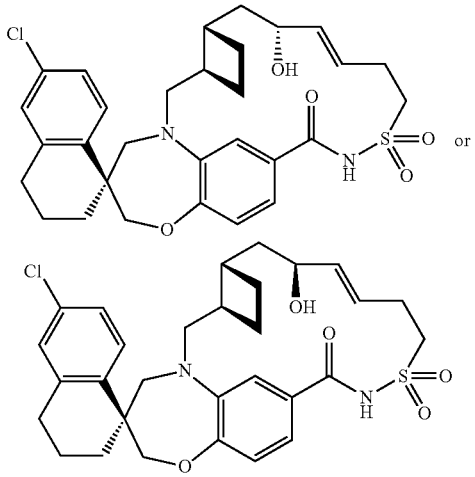

Step 1: (S)-methyl 6'-chloro-5-(((1R,2R)-2-((E)-2-methoxyvinyl)cyclobutyl)methyl)-3',4',5-tetrahydro-2H,2'H-spiro[benzo[b][1,4]oxazepine-3,1'-naphthalene]-7-carboxylate

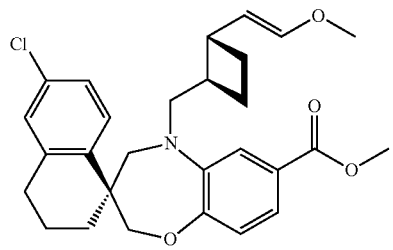

A solution of chloro(methoxymethyl)triphenylphosphorane (0.227 g, 0.661 mmol) in THF (5.5 mL) was cooled to 0° C. N-Butyl lithium solution (2.5 M in hexane; 0.25 mL, 0.63 mmol) was added dropwise and it was stirred at 0° C. for 7 min. (S)-methyl 6'-chloro-5-(((1R,2R)-2-formylcyclobutyl)methyl)-3',4',5-tetrahydro-2H,2'H-spiro[benzo[b][1,4]oxazepine-3,1'-naphthalene]-7-carboxylate (Intermediate AA11A, Step 20A; 0.075 g, 0.165 mmol) in THF (2 mL) was added in one portion and it was stirred at 0° C. for 8 min. The reaction mixture was poured slowly to ice-water (5 mL) and extracted with EtOAc (100 mL). The organic phase was dried over anhydrous sodium sulfate and concentrated. The residue was loaded to a 12 g ISCO Gold column and eluted with 0% to 10% (EtOAc/hexane) to provide the title compound (120 mg) as a white solid. m/z (ESI, +ve ion) 482.1 (M+H)$^+$.

Step 2: (S)-6'-chloro-5-(((1R,2S)-2-(2-oxoethyl)cyclobutyl)methyl)-3',4',5-tetrahydro-2H,2'H-spiro[benzo[b][1,4]oxazepine-3,1'-naphthalene]-7-carboxylic Acid

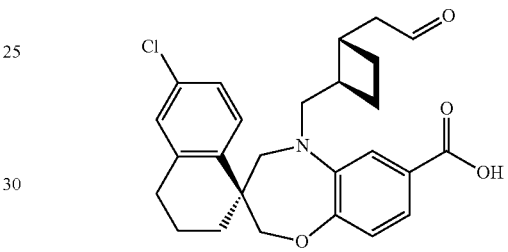

A mixture of (S)-methyl 6'-chloro-5-(((1R,2R)-2-((E)-2-methoxyvinyl)cyclobutyl)methyl)-3',4',5-tetrahydro-2H,2'H-spiro[benzo[b][1,4]oxazepine-3,1'-naphthalene]-7-carboxylate (Example 884, Step 1; 0.120 g, 0.249 mmol) and lithium hydroxide (1.0 M aqueous solution, 2 mL, 2 mmol) in MeOH (1 mL) and THF (1.5 mL) was stirred at rt for 3 days. It was concentrated and was added 1 N HCl solution (6 mL) and acetone (20 mL) and stirred at rt for 27 h. It was concentrated at rt and the residue was extracted with EtOAc (120 mL). The organic phase was washed with brine, dried over anhydrous sodium sulfate and concentrated to provide the title compound (109 mg) as a white solid. m/z (ESI, +ve ion) 454.1 (M+H)$^+$.

Step 3: (S)-6'-chloro-5-(((1R,2S)-2-((R)-2-hydroxybut-3-en-1-yl)cyclobutyl)methyl)-3',4',5-tetrahydro-2H,2'H-spiro[benzo[b][1,4]oxazepine-3,1'-naphthalene]-7-carboxylic Acid or (S)-6'-chloro-5-(((1R,2S)-2-((S)-2-hydroxybut-3-en-1-yl)cyclobutyl)methyl)-3',4',5-tetrahydro-2H,2'H-spiro[benzo[b][1,4]oxazepine-3,1'-naphthalene]-7-carboxylic Acid

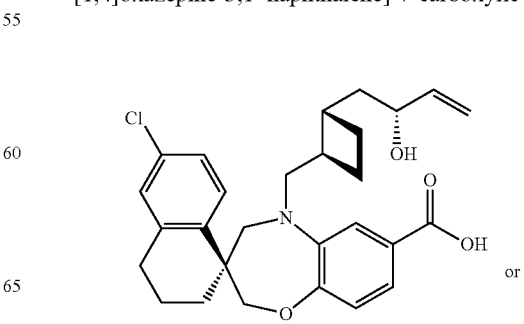

or

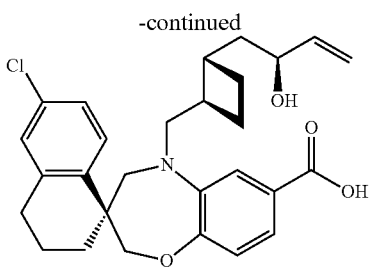

At 0° C., vinylmagnesium chloride (1.6 M solution in THF; 0.25 mL, 0.40 mmol) was added dropwise to a solution of (S)-6'-chloro-5-(((1R,2S)-2-(2-oxoethyl)cyclobutyl)methyl)-3',4,4',5-tetrahydro-2H,2'H-spiro[benzo[b][1,4]oxazepine-3,1'-naphthalene]-7-carboxylic acid (Example 884, Step 2; 0.060 g, 0.132 mmol) in THF (2.2 mL), which was cooled to 0° C. It was stirred at rt for 0.5 h. The reaction mixture was poured into ice-water, acidified with 1N HCl solution to pH 2-3, extracted with EtOAc (130 mL). The organic phase was washed with brine (1 mL), dried over anhydrous sodium sulfate, filtered through silica gel and concentrated. The residue was purified by reverse phase preparative HPLC (Gemini™ Prep C$_{18}$ 5 μm column; Phenomenex, Torrance, CA; MeCN in water with 0.1% TFA, gradient elution). The title compound (14 mg) was obtained as a single isomer (second eluting peak) as a white solid. m/z (ESI, +ve ion) 482.1 (M+H)$^+$.

Step 4: (S)—N-(but-3-en-1-ylsulfonyl)-6'-chloro-5-(((1R,2S)-2-((R)-2-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(but-3-en-1-ylsulfonyl)-6'-chloro-5-(((1R,2S)-2-((S)-2-hydroxybut-3-en-1-yl)cyclo-butyl)methyl)-3',4,4',5-tetrahydro-2H,2'H-spiro[benzo[b][1,4]oxazepine-3,1'-naphthalene]-7-carboxamide

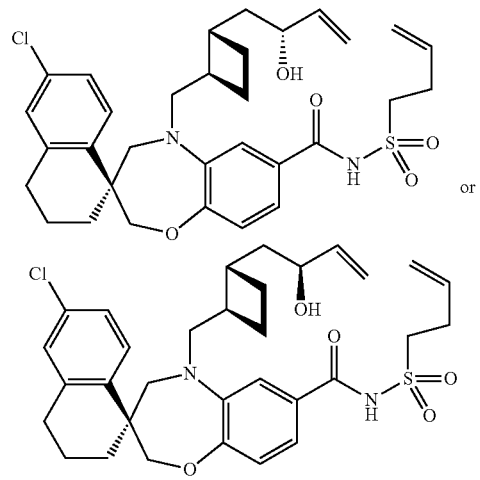

N,N-Dimethylpyridin-4-amine (DMAP) (9.12 mg, 0.075 mmol) was added to a solution of (S)-6'-chloro-5-(((1R,2S)-2-((R)-2-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Example 884, Step 3; 0.012 g, 0.025 mmol) and but-3-ene-1-sulfonamide (EE15; 0.015 g, 0.112 mmol) in DCM (0.9 mL) at 0° C. (ice bath). Then N-(3-dimethylaminopropyl)-N'-ethylcarbodiimide hydrochloride (EDC; 9 mg, 0.05 mmol) was added portion by portion slowly and it was stirred at rt for 18 h. It was concentrated and the residue was purified by reverse phase preparative HPLC (Gemini™ Prep C$_{18}$ 5 μm column; Phenomenex, Torrance, CA; MeCN in water with 0.1% TFA, gradient elution) to provide the title compound (8 mg) as a white solid. m/z (ESI, +ve ion) 599.2 (M+H)$^+$.

Step 5: (1S,3'R,6'S,8'R,9'E)-6-chloro-8'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide or (1S,3'R,6'S,8'S,9'E)-6-chloro-8'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide A 250 mL round bottom flask was charged with (S)—N-(but-3-en-1-ylsulfonyl)-6'-chloro-5-(((1R,2S)-2-((R)-2-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide (Example 884, Step 4; 0.008 g, 0.013 mmol) in toluene (33 mL). It was stirred at rt for 10 min to dissolve the solid starting material and then subjected to three cycles of evacuation/back-filling with nitrogen. To the homogeneous solution was added a solution of Hoveyda-Hoveyda-Grubbs II (1.7 mg, 2.7 μmol) in toluene (3 mL). The mixture was stirred at 106° C. under nitrogen for 53 min. It was concentrated and the residue was purified by reverse phase preparative HPLC (Gemini™ Prep C$_{18}$ 5 μm column; Phenomenex, Torrance, CA; MeCN in water with 0.1% TFA, gradient elution) to provide the title compound (2.1 mg) as a white solid. $^1$H NMR (500 MHz, CD$_2$Cl$_2$) δ 8.09 (m, 1H), 7.73 (m, 1H), 7.19 (m, 2H), 7.09 (m, 1H), 6.96 (m, 1H), 6.81 (m, 1H), 5.79 (dd, J=7.58, 15.41 Hz, 1H), 5.66-5.57 (m, 1H), 4.21-4.15 (m, 1H), 4.12-4.06 (m, 2H), 3.87 (ddd, J=3.30, 10.58, 15.47 Hz, 1H), 3.78 (dd, J=4.28, 15.53 Hz, 1H), 3.73 (d, J=14.18 Hz, 1H), 3.58 (ddd, J=2.93, 6.97, 15.53 Hz, 1H), 3.24 (d, J=14.43 Hz, 1H), 3.04 (dd, J=6.48, 15.53 Hz, 1H), 2.82-2.73 (m, 2H), 2.72-2.57 (m, 2H), 2.34-2.20 (m, 2H), 2.07-1.34 (m, 10H). m/z (ESI, +ve ion) 571.3 (M+H)$^+$.

Example 885. (1S,3'R,6'R,8'Z,12'R)-6-chloro-12'-ethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-7',15'-dione 13',13'-dioxide

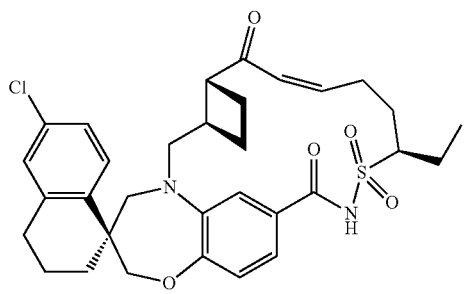

Step 1: (1S,3'R,6'R,7'S,8'Z,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

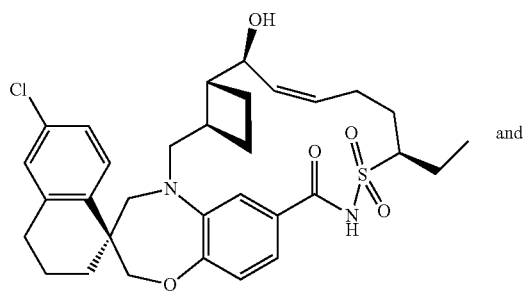

and

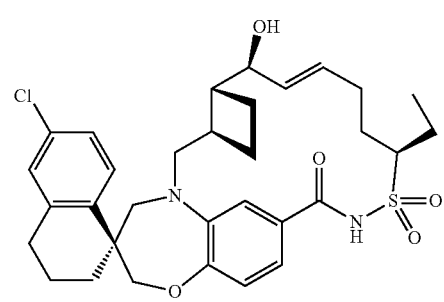

The title compounds were prepared by the same procedure described in Example 422, Step 1. The title compounds contained both trans- (1007) and cis-isomers. m/z (ESI, +ve ion) 599.1 (M+H)$^+$.

Step 2: (1S,3'R,6'R,8'Z,12'R)-6-chloro-12'-ethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [8,16,18,24]tetraene]-7',15'-dione 13',13'-dioxide

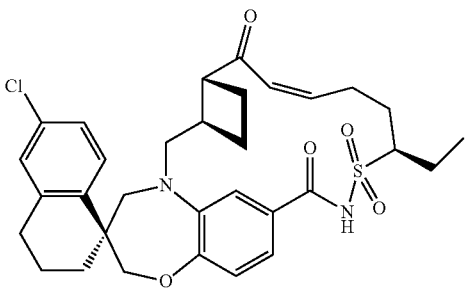

A 100 mL flask charged dimethyl sulfoxide (0.181 mL, 2.56 mmol) and DCM (5 mL) was cooled to −78° C. Oxalyl chloride (2.0 M solution in DCM, 0.68 mL, 1.36 mmol) was added dropwise and the reaction mixture was stirred for 17 min. The resulting solution was added to a mixture of Example 885, Step 1 (0.511 g, 0.853 mmol) in DCM (8.5 mL) (not homogenous solution), which was cooled to −78° C. After it was stirred at −78° C. for 56 min, triethylamine (0.5 mL, 3.4 mmol) was added dropwise and it was stirred at −78° C. for 1 h. It was quenched with water (30 mL) and extracted with EtOAc (200 mL). The organic phase was washed with 1 N HCl solution (6 mL), brine, dried over anhydrous sodium sulfate and concentrated. The residue was purified by reverse phase preparative HPLC (Gemini™ Prep C$_{18}$ 5 μm column; Phenomenex, Torrance, CA; MeCN in water with 0.1% TFA, gradient elution). The title compound (4.6 mg) was obtained as a single isomer (first eluting peak) as a white solid. $^1$H NMR (400 MHz, CD$_2$Cl$_2$) δ 9.45 (s, 1H), 7.72 (d, J=8.41 Hz, 1H), 7.32 (dd, J=2.15, 8.22 Hz, 1H), 7.22 (d, J=2.15 Hz, 1H), 7.17 (dd, J=2.35, 8.61 Hz, 1H), 7.10 (d, J=2.15 Hz, 1H), 6.95 (d, J=8.41 Hz, 1H), 6.46 (td, J=8.31, 11.15 Hz, 1H), 6.25 (d, J=11.15 Hz, 1H), 4.19-4.08 (m, 2H), 3.70 (dd, J=5.77, 14.77 Hz, 2H), 3.38-3.23 (m, 3H), 3.02 (q, J=9.59 Hz, 1H), 2.95-2.73 (m, 5H), 2.36-2.26 (m, 1H), 2.19 (d, J=9.39 Hz, 1H), 2.08-1.65 (m, 9H), 1.56-1.48 (m, 1H), 1.10 (t, J=7.43 Hz, 3H). m/z (ESI, +ve ion) 597.1 (M+H)$^+$.

Example 886. (1S,3'R,6'R,12'R)-6-chloro-12'-ethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [16,18,24]triene]-7',15'-dione 13',13'-dioxide

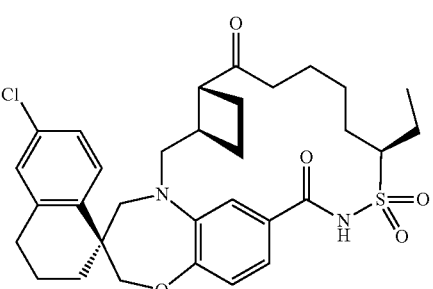

Step 1: (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

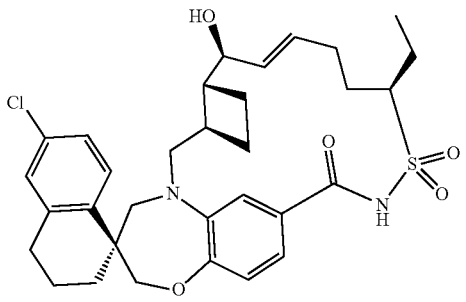 [SMILES: CC[C@@H]1CC/C=C/[C@H](O)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 719, Steps 1 and 2 using (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Intermediate AA11A) and (R)-hept-6-ene-3-sulfonamide (Intermediate EE21), and the desired product, (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was obtained (first eluting major peak) as a white solid from the reverse-phase preparative HPLC.

Step 2: (1S,3'R,6'R,7'S,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

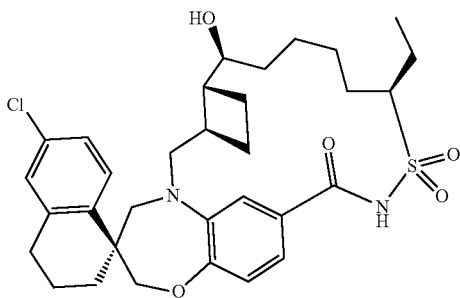 [SMILES: CC[C@@H]1CCCC[C@H](O)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example Example 925, Step 1, using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (from Step 2).

Step 3: (1S,3'R,6'R,12'R)-6-chloro-12'-ethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [16,18,24]triene]-7',15'-dione 13',13'-dioxide A 200 mL flask charged DMSO (1.7 mL, 25 mmol) and DCM (20 mL) was cooled to −78° C. Oxalyl chloride (2.0 M solution in DCM; 6.6 mL, 13 mmol) was added dropwise slowly and the resulting mixture was stirred at to −78° C. for 15 min. The mixture was called solution (I). (1S,3'R,6'R,7'S,12'R)-6-Chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (from Step 2, 0.79 g, 1.3 mmol) in DCM (20 mL) (not homogenous solution) was added dropwise to the above solution (I). After it was stirred at −78° C. for 1 h, triethylamine (5 mL, 35 mmol) was added dropwise and it was stirred at −78° C. for 1 h. The reaction was quenched with water (30 mL), extracted with EtOAc (400 mL). The organic phase was washed with 1 N HCl solution (2×13 mL), brine, dried over anhydrous sodium sulfate and concentrated. The residue was loaded to a 80 g ISCO Gold column and eluted with 0% to 15% EtOAc (containing 0.3% AcOH)/DCM (containing 0.3% AcOH) to provide the title compound (372 mg) as a white solid. $^1$H NMR (400 MHz, CD$_2$Cl$_2$) δ 8.27 (m, 1H), 7.73 (m, 1H), 7.18 (m, 1H), 7.10 (m, 1H), 6.99 (m, 2H), 6.92 (m, 1H), 4.16-4.05 (m, 2H), 3.86-3.66 (m, 3H), 3.29 (d, J=14.48 Hz, 1H), 3.22-3.11 (m, 2H), 2.85-2.72 (m, 3H), 2.41-2.31 (m, 1H), 2.31-2.19 (m, 1H), 2.16-2.06 (m, 2H), 2.05-1.71 (m, 9H), 1.64-1.56 (m, 1H), 1.50-1.34 (m, 4H), 1.14 (t, J=7.53 Hz, 3H). m/z (ESI, +ve ion) 599.1 (M+H)$^+$.

Example 891. (1S,3'R,6'R,7'S,10'S)-6-chloro-7',10'-dihydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa [16,18,24]trien]-15'-one 13',13'-dioxide or (1S,3'R,6'R,7'S,10'R)-6-chloro-7',10'-dihydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa [16,18,24]trien]-15'-one 13',13'-dioxide or (1S,3'R,6'R,7'S,9'S)-6-chloro-7',9'-dihydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa[16,18,24]trien]-15'-one 13',13'-dioxide or (1S,3'R,6'R,7'S,9'R)-6-chloro-7',9'-dihydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa [16,18,24]trien]-15'-one 13',13'-dioxide

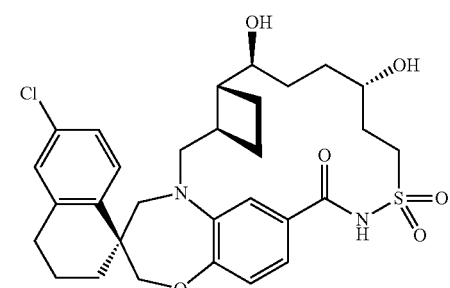

or

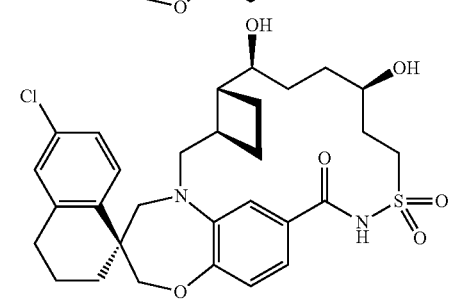

or

-continued

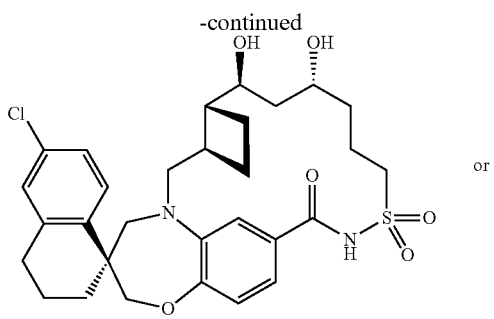

or

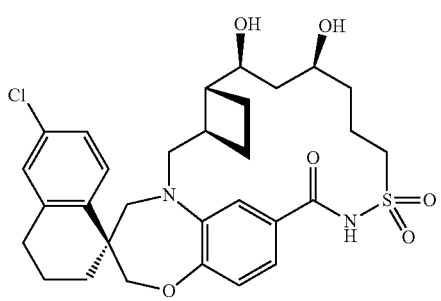

A solution of (1S,3'R,6'R,7'S,9'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (Example 846) in THF (4.3 mL) under $N_2$ was cooled to 0° C. and treated with borane THF complex (1.0 M solution in THF; 0.64 mL, 0.64 mmol). It was stirred at 0° C. for 2.5 h. Then N-methylmorpholine oxide (0.263 g, 2.243 mmol) was added in one portion and the mixture was stirred while allowing to reach rt for 30 min. After it was concentrated the residue was stirred in MeOH (35 mL) at 70° C. overnight. It was diluted with water, extracted with EtOAc, dried over anhydrous sodium sulfate and concentrated. The residue was purified by SFC (Method: 250×21.2 mm IC—H column w/ 20 g/min MeOH (0.2% DEA)+60 g/min $CO_2$ on a Thar 80 SFC. Outlet pressure 100 bar; Temp. 20° C.; Wavelength 220 nm) to give the titlt compound (7.8 mg, first eluting peak) as a white solid. $^1$H NMR (400 MHz, $CDCl_3$) δ 7.70 (m, 1H), 7.18 (m, 1H), 7.12-7.00 (m, 2H), 6.97-6.82 (m, 2H), 4.17-3.99 (m, 4H), 3.79-3.63 (m, 2H), 3.45-3.26 (m, 1H), 3.25-3.14 (m, 1H), 3.11-2.99 (m, 1H), 2.85-2.70 (m, 2H), 2.27 (br. s., 1H), 2.13-0.99 (m, 16H). m/z (ESI, +ve ion) 589.2 (M+H)$^+$.

Example 892. (1S,3'R,6'R,7'S,10'S)-6-chloro-7',10'-dihydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,10'R)-6-chloro-7',10'-dihydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'S)-6-chloro-7',9'-dihydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,9'R)-6-chloro-7',9'-dihydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

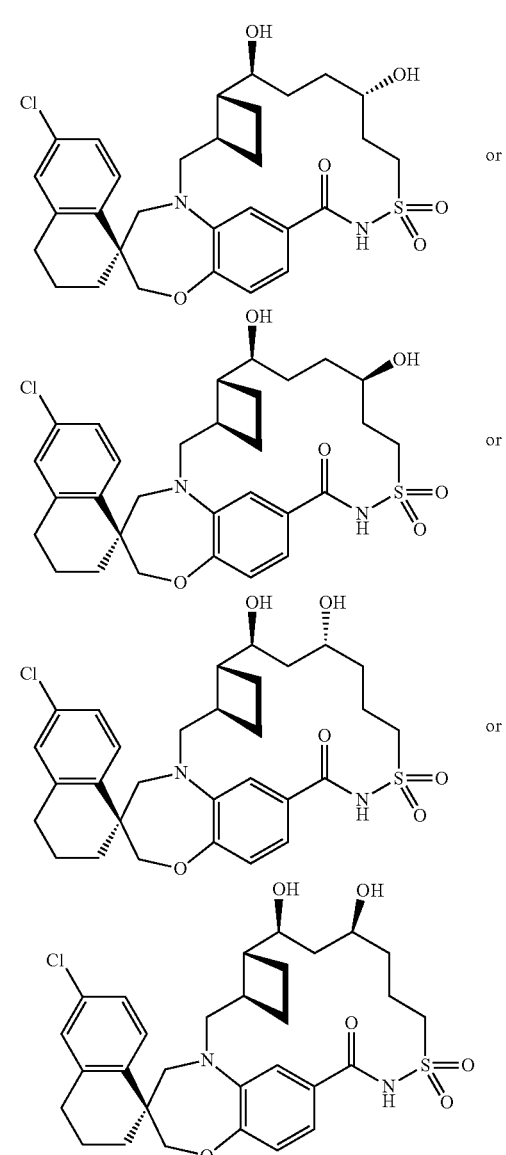

The title compound (7.4 mg) was obtained as a single isomer (second eluting peak) from the reverse phase preparative HPLC in Example 891 as a white solid. $^1$H NMR (400 MHz, CDCl$_3$) δ 9.06 (br. s., 1H), 7.70 (m, 1H), 7.17 (m, 2H), 7.13 (s, 1H), 7.09 (d, J=2.15 Hz, 1H), 6.94 (m, 1H), 4.13-4.02 (m, 2H), 3.96-3.87 (m, 2H), 3.80-3.65 (m, 3H), 3.63-3.56 (m, 1H), 3.25 (d, J=14.28 Hz, 1H), 3.18-3.09 (m, 1H), 2.83-2.74 (m, 2H), 2.44-2.32 (m, 2H), 2.07-0.99 (m, 16H). m/z (ESI, +ve ion) 589.1 (M+H)$^+$.

Example 893. (1S,3'R,6'R,7'S,10'S)-6-chloro-7',10'-dihydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa 10 [16,18,24]trien]-15'-one 13',13'-dioxide or (1S,3'R,6'R,7'S,1'R)-6-chloro-7',10'-dihydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa [16,18,24]trien]-15'-one 13',13'-dioxide or (1S,3'R,6'R,7'S,9'S)-6-chloro-7',9'-dihydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa [16,18,24]trien]-15'-one 13',13'-dioxide or (1S,3'R,6'R,7'S,9'R)-6-chloro-7',9'-dihydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa [16,18,24]trien]-15'-one 13',13'-dioxide

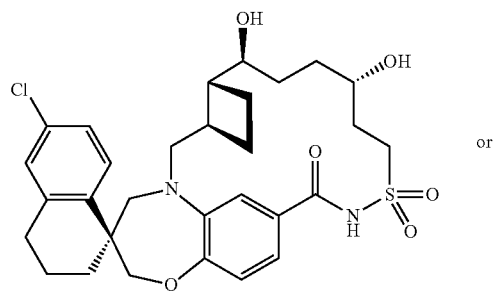

or

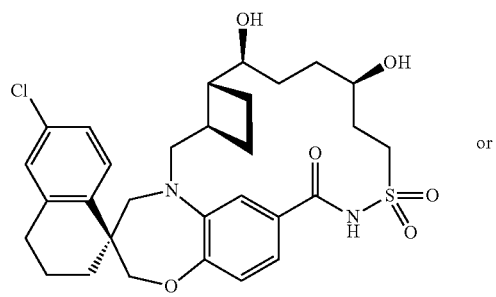

or


or

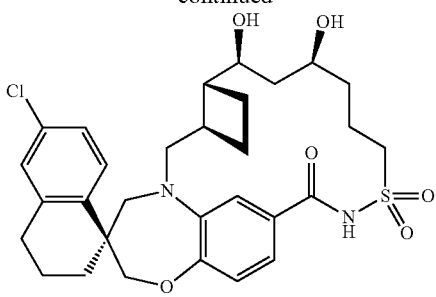

The title compound (7.5 mg) was obtained as a single isomer (third eluting peak) from the reverse phase preparative HPLC in Example 891. $^1$H NMR (400 MHz, CDCl$_3$) δ 7.70 (d, J=8.41 Hz, 1H), 7.18 (d, J=6.26 Hz, 2H), 7.12-7.04 (m, 2H), 6.96 (d, J=8.22 Hz, 1H), 4.35-4.26 (m, 1H), 4.16-4.07 (m, 2H), 3.84-3.60 (m, 5H), 3.30 (d, J=14.28 Hz, 1H), 3.21 (br. s., 1H), 2.83-2.73 (m, 2H), 2.54 (br. s., 1H), 2.24 (br. s., 2H), 2.04-1.02 (m, 13H). m/z (ESI, +ve ion) 589.1 (M+H)$^+$.

Example 894. (1S,3'R,6'R,7'S,10'S)-6-chloro-7',10'-dihydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa [16,18,24]trien]-15'-one 13',13'-dioxide or (1S,3'R,6'R,7'S,10'R)-6-chloro-7',10'-dihydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa [16,18,24]trien]-15'-one 13',13'-dioxide or (1S,3'R,6'R,7'S,9'S)-6-chloro-7',9'-dihydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa [16,18,24]trien]-15'-one 13',13'-dioxide or (1S,3'R,6'R,7'S,9'R)-6-chloro-7',9'-dihydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa [16,18,24]trien]-15'-one 13',13'-dioxide

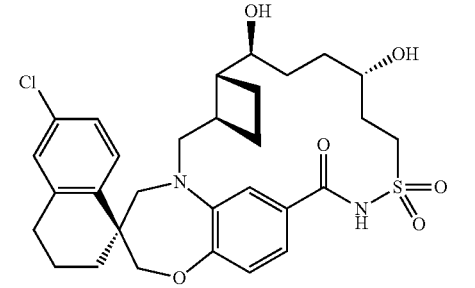

or

-continued

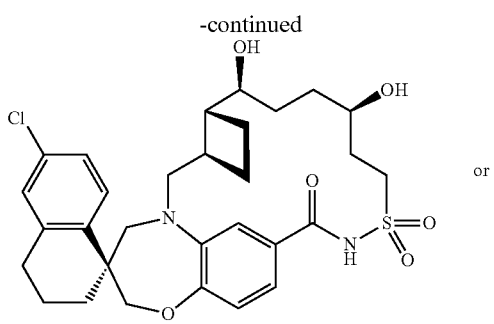

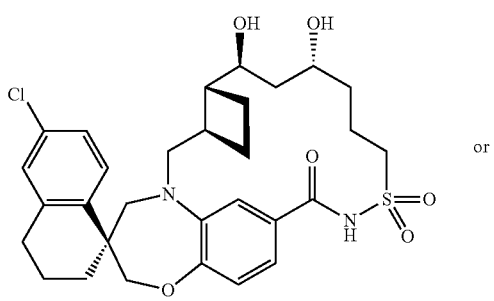

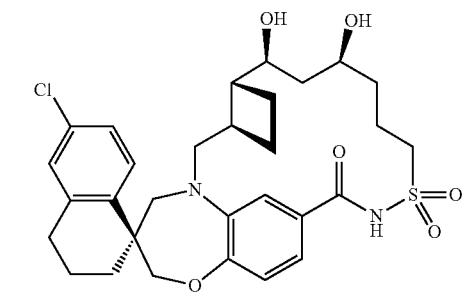

The title compound (7.7 mg) was obtained as a single isomer (fourth eluting peak) from the reverse phase preparative HPLC in Example 891. $^1$H NMR (400 MHz, CDCl$_3$) δ 7.68 (d, J=8.61 Hz, 1H), 7.35 (d, J=8.61 Hz, 1H), 7.25 (br. s., 1H), 7.17 (d, J=8.61 Hz, 1H), 7.09 (s, 1H), 6.94 (d, J=8.22 Hz, 1H), 4.25 (m, 1H), 4.18-3.98 (m, 3H), 3.85-3.51 (m, 6H), 3.30 (d, J=15.06 Hz, 1H), 3.20 (d, J=13.30 Hz, 2H), 2.77 (br. s., 3H), 2.39-2.18 (m, 3H), 2.10-1.13 (m, 9H). m/z (ESI, +ve ion) 589.1 (M+H)$^+$.

Example 895. (1S,3'R,6'R,7'R,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,10'R,1]'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'R,1]'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'S,11'S)-6-chloro-10'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6R,7'S,10'S,11'S)-6-chloro-10'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'R,11'R)-6-chloro-10'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,10'S,11'R)-6-chloro-10'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'S,11'R)-6-chloro-10'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide

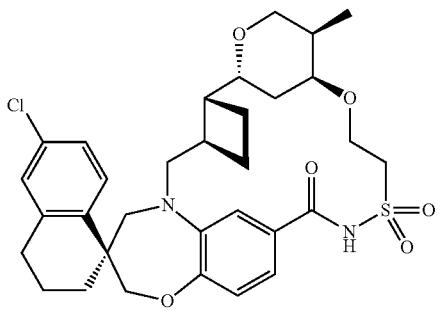

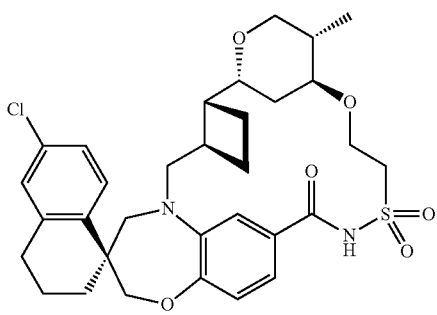

1805
-continued

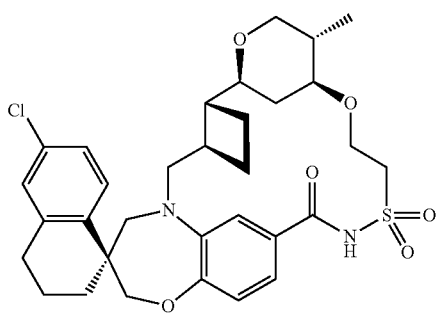

or

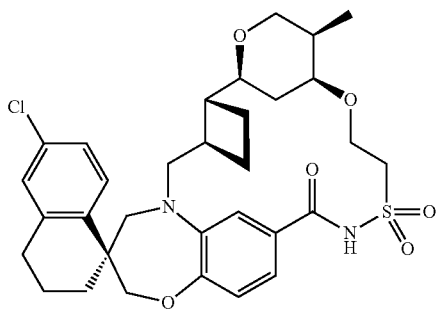

or

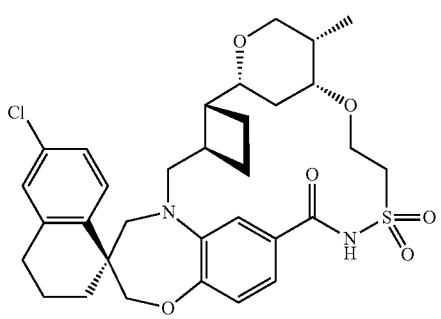

or

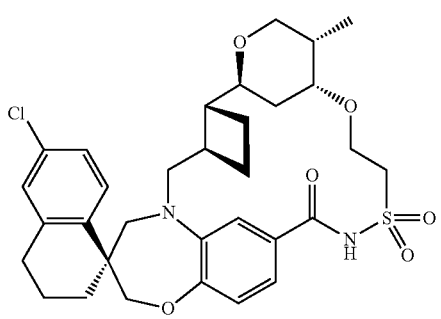

or

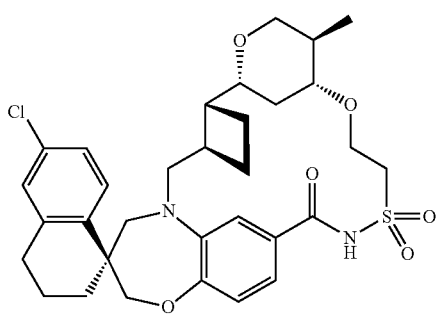

or

1806
-continued

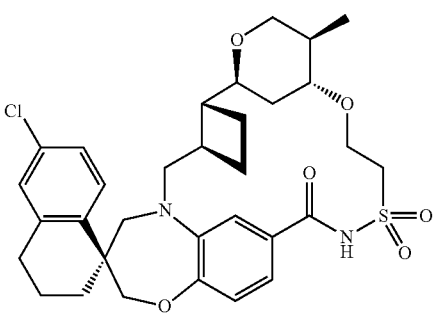

or

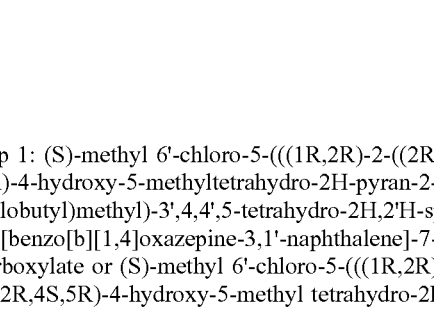

Step 1: (S)-methyl 6'-chloro-5-(((1R,2R)-2-((2R,4S,5R)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S,5R)-4-hydroxy-5-methyl tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S,5S)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R,5S)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R,5S)-4-hydroxy-5-methyl tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R,5R)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R,5R)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

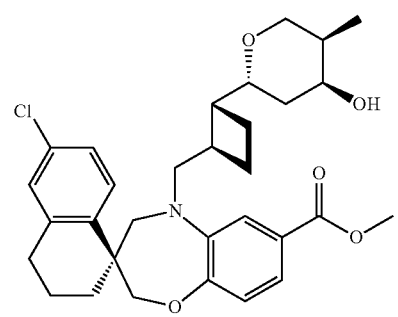

or

1807
-continued

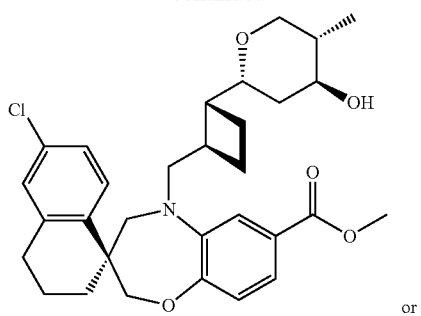

or


or


or

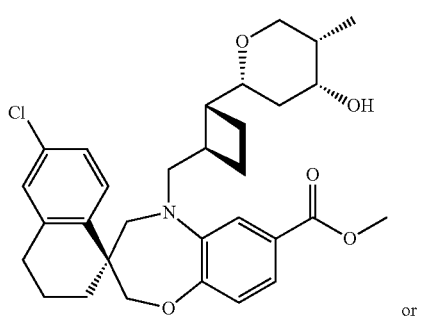

or

1808
-continued

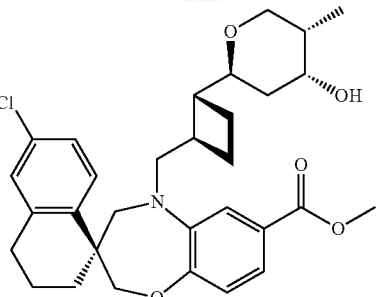

or

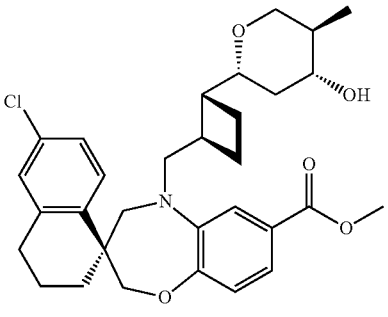

or

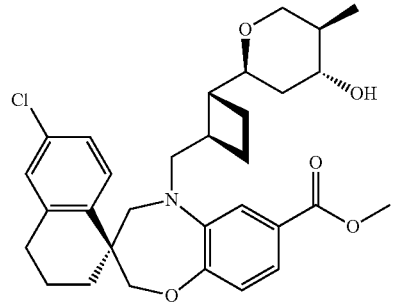

TFA (5.1 mL) was added slowly to a solution of (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A; 0.417 g, 0.919 mmol) and 2-methyl-3-buten-1-ol (0.123 ml, 1.19 mmol) in DCM (10 mL) which was degassed with $N_2$. It was stirred at rt for 22 min. The reaction mixture was added slowly to $Na_2CO_3$ solution (40 mL) and MeOH (20 mL). After it was stirred at rt for 15 min, the mixture was extracted with EtOAc (3×130 mL). The organic phase was dried over anhydrous sodium sulfate and concentrated. The residue was purified by reverse phase preparative HPLC (Gemini™ Prep $C_{18}$ 5 μm column; Phenomenex, Torrance, CA; MeCN in water with 0.1% TFA, gradient elution) to provide the title compound (24 mg, second eluting peak) as a white solid. m/z (ESI, +ve ion) 540.1 $(M+H)^+$.

Step 2: (S)-6'-chloro-5-(((1R,2R)-2-((2R,4S,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4S,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4S,5S)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4S,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R,5S)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4R,5S)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid

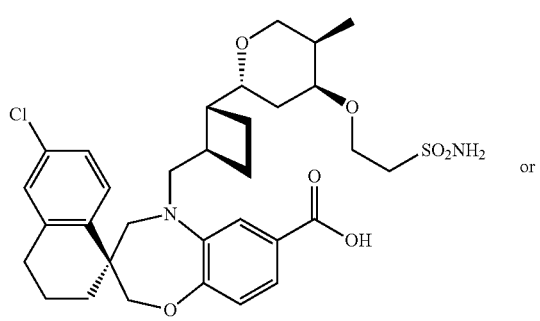 or

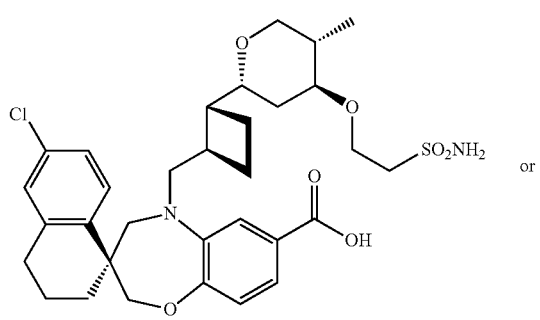 or

-continued

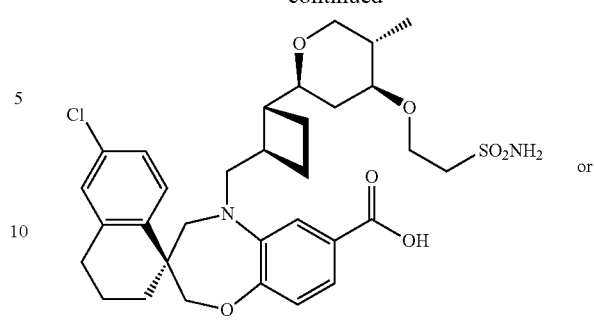 or

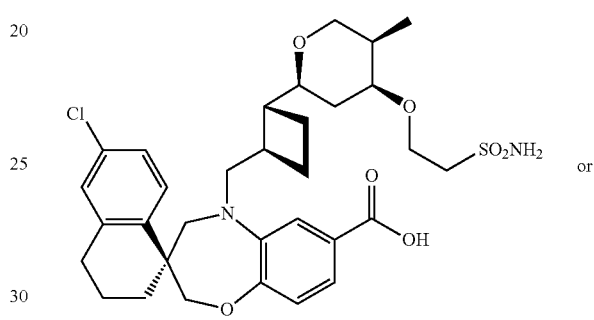 or

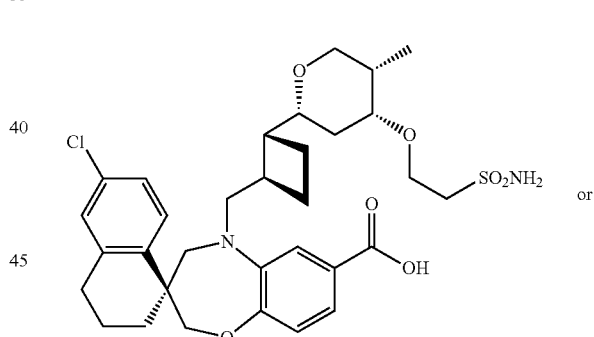 or

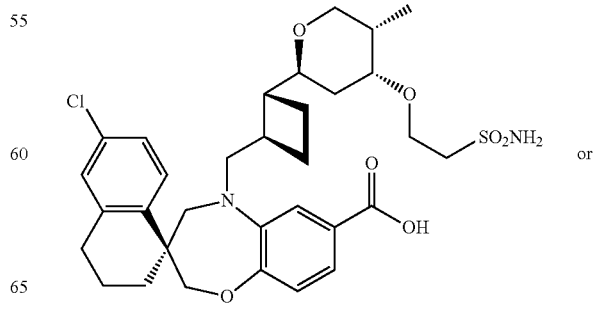 or

-continued

Sodium hydride (60% dispersion in mineral oil; 6.24 mg, 0.296 mmol) was added to a solution of (1'S)-methyl 6'-chloro-5-(((1R,2R)-2-((2R,4S)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 895, Step 1; 0.024 g, 0.044 mmol) in THF (1.3 mL), which was cooled by ice bath. After it was stirred at rt for 8 min N,N-bis(4-methoxybenzyl)ethenesulfonamide (Example 831, Step 2, 0.029 g, 0.084 mmol) in THF (1 mL) was added. It was stirred at rt for 2 h. Water (2 mL) and EtOAc (120 mL) were added. The organic phase was washed with brine, dried over anhydrous sodium sulfate and concentrated. The residue was purified by reverse phase preparative HPLC (Gemini™ Prep $C_{18}$ 5 μm column; Phenomenex, Torrance, CA; MeCN in water with 0.1% TFA, gradient elution) to provide the title compound (7 mg).
Hydrolysis I: The residue was dissolved in THF (4 mL), MeOH (4 mL) and 1M LiOH solution (3 mL) and the mixture was stirred at 50° C. for 2.5 h. It was concentrated, acidified with 1 N HCl solution to pH 2-4, extracted with EtOAc (80 mL). The organic phase was washed with brine and dried over anhydrous sodium sulfate and concentrated.
Hydrolysis II: The residue was dissolved in 1:3 TFA/DCM (4 mL) and stirred at rt for 20 h. After it was concentrated the residue was purified by reverse phase preparative HPLC (Gemini™ Prep $C_{18}$ 5 μm column; Phenomenex, Torrance, CA; MeCN in water with 0.1% TFA, gradient elution) to provide the title compound (5 mg) as a white solid. m/z (ESI, +ve ion) 633.1 (M+H)$^+$.

Step 3: (1S,3'R,6'R,7'R,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,10'R,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'R,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'S,11'S)-6-chloro-10'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6R,7'S,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'R,11'R)-6-chloro-10'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,10'S,11'R)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'S,11'R)-6-chloro-10'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide N,N-Dimethylpyridin-4-amine (DMAP) (0.014 g, 0.118 mmol) was added to a solution of (1'S)-6'-chloro-5-(((1R,2R)-2-((2S,4R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid (Example 895, Step 2; 0.005 g, 7.9 μmol) in DCM (32 mL) at 0° C. Then N1-((ethylimino)methylene)-N3,N3-dimethylpropane-1,3-diamine hydrochloride (EDC; 0.018 g, 0.095 mmol) was added slowly in portions and it was stirred at 0° C. to rt for 23 h. It was concentrated and the residue was purified by reverse phase preparative HPLC (Gemini™ Prep $C_{18}$ 5 μm column; Phenomenex, Torrance, CA; MeCN in water with 0.1% TFA, gradient elution) to provide the title compound (2.7 mg) as a white solid. $^1$H NMR (400 MHz, CD$_3$OD) δ 7.76 (d, J=8.61 Hz, 1H), 7.20 (dd, J=2.05, 8.31 Hz, 2H), 7.12 (d, J=2.15 Hz, 1H), 7.07 (d, J=1.96 Hz, 1H), 6.96 (d, J=8.22 Hz, 1H), 4.09-4.15 (m, 2H), 3.96-4.08 (m, 2H), 3.83 (dd, J=2.84, 7.92 Hz, 1H), 3.65-3.80 (m, 4H), 3.57 (br. s., 1H), 3.43 (dd, J=4.50, 11.15 Hz, 1H), 3.22-3.29 (m, 1H), 3.11-3.21 (m, 2H), 2.76-2.87 (m, 2H), 2.68 (s, 1H), 2.45-2.53 (m, 1H), 2.17-2.24 (m, 1H), 1.30-2.11 (m, 9H), 0.89-0.96 (m, 1H), 0.84 (d, J=6.85 Hz, 3H). m/z (ESI, +ve ion) 615.0 (M+H)$^+$.

1813

Example 898. (1S,3'R,6'R,7'R)-6-chloro-7'-(hydroxymethyl)-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'S)-6-chloro-7'-(hydroxymethyl)-3,4-dihydro-2H,15'H-spiro[naphthalene-1,22'[20]oxa[13]thia[1,14]diazatetracyclo[14.7.2.0³,⁶.0¹⁹,²⁴]pentacosa[16,18,24]trien]-15'-one 13',13'-dioxide

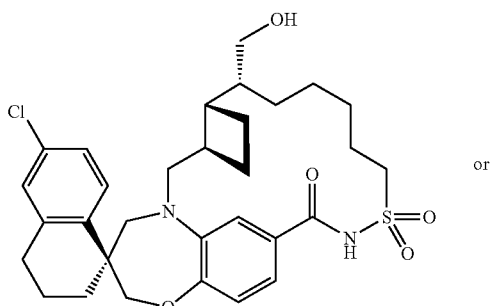

or

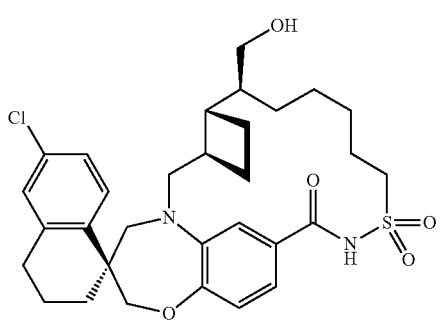

A solution of (1S,3'R,6'R)-6-chloro-7'-methylidene-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide (Example 904; 0.018 g, 0.031 mmol) in THF (1.5 mL) was cooled with ice bath. 9-BBN (0.5 M solution in tetrahydrofuran, 1.2 mL, 0.62 mmol) was added dropwise. After it was stirred at rt for 1 h, MeOH (10 mL) and trimethylamine N-oxide (0.208 g, 1.86 mmol) were added in one portion and the mixture was stirred at rt for 2 h. Then it was concentrated. The residue was stirred in MeOH (30 mL) at 68° C. for 20 h. It was diluted with water and extracted with EtOAc, dried over anhydrous sodium sulfate and concentrated. The residue was purified by reverse phase preparative HPLC (Gemini™ Prep $C_{18}$ 5 µm column; Phenomenex, Torrance, CA; MeCN in water with 0.1% TFA, gradient elution).) to provide the title compound (6.2 m, second eluting peak) as a white solid. $^1$H NMR (400 MHz, $CD_2Cl_2$) δ 7.77 (m, 1H), 7.19 (m, 2H), 7.13 (m, 1H), 7.04 (m, 1H), 6.97 (m, 1H), 4.44 (m, 1H), 4.17-4.04 (m, 2H), 4.00-3.82 (m, 2H), 3.81-3.69 (m, 2H), 3.63 (br. s., 1H), 3.19-3.05 (m, 1H), 2.90-2.74 (m, 2H), 2.65-2.48 (m, 1H), 2.39 (d, J=5.48 Hz, 1H), 2.25-2.18 (m, 1H), 2.12 (d, J=12.72 Hz, 1H), 2.06-1.26 (m, 17H). m/z (ESI, +ve ion) 587.1 (M+H)⁻

1814

Example 900. (3R,6R,7R,11S,24S)-6'-chloro-11-hydroxy-3',4'-dihydro-2'H,17H-spiro[8,22-dioxa-15-thia-1,16-diazapentacyclo[16.7.2.1⁷,¹¹.0³,⁶.0²¹,²⁶]octacosa-18,20,26-triene-24,1'-naphthalen]-17-one 15,15-dioxide or (3R,6R,7S,11R,24S)-6'-chloro-11-hydroxy-3',4'-dihydro-2'H,17H-spiro[8,22-dioxa-15-thia-1,16-diazapentacyclo[16.7.2.1⁷,¹¹.0³,⁶.0²¹,²⁶]octacosa-18,20,26-triene-24,1'-naphthalen]-17-one 15,15-dioxide or (3R,6R,7R,11R,24S)-6'-chloro-11-hydroxy-3',4'-dihydro-2'H,17H-spiro[8,22-dioxa-15-thia-1,16-diazapentacyclo[[16.7.2.1⁷,¹¹.0³,⁶.0²¹,²⁶]octacosa-18,20,26-triene-24,1'-naphthalen]-17-one 15,15-dioxide or (3R,6R,7S,11S,24S)-6'-chloro-11-hydroxy-3',4'-dihydro-2'H,17H-spiro[8,22-dioxa-15-thia-1,16-diazapentacyclo[16.7.2.1⁷,¹¹.0³,⁶.0²¹,²⁶]octacosa-18,20,26-triene-24,1'-naphthalen]-17-one 15,15-dioxide

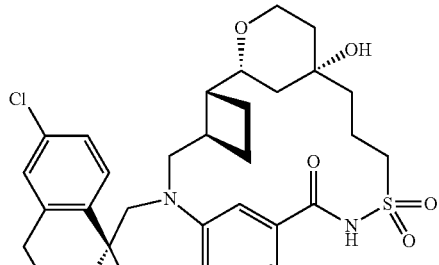

or

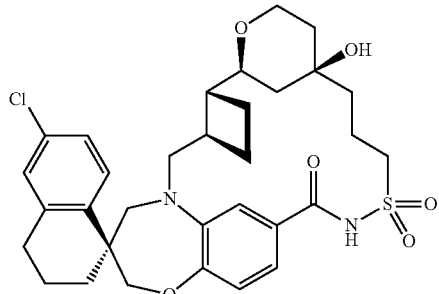

or

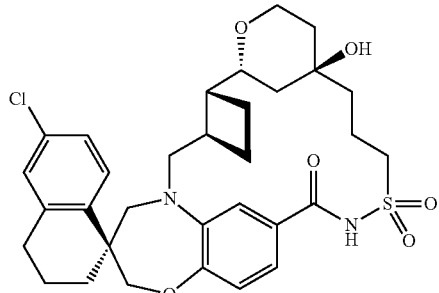

or

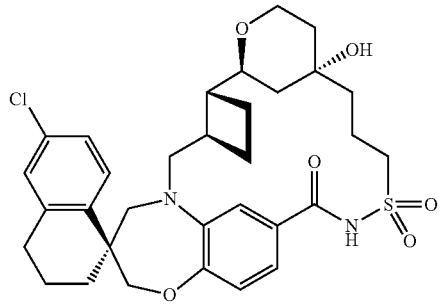

Step 1: (S)-methyl 6'-chloro-5-(((1R,2R)-2-((2S,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

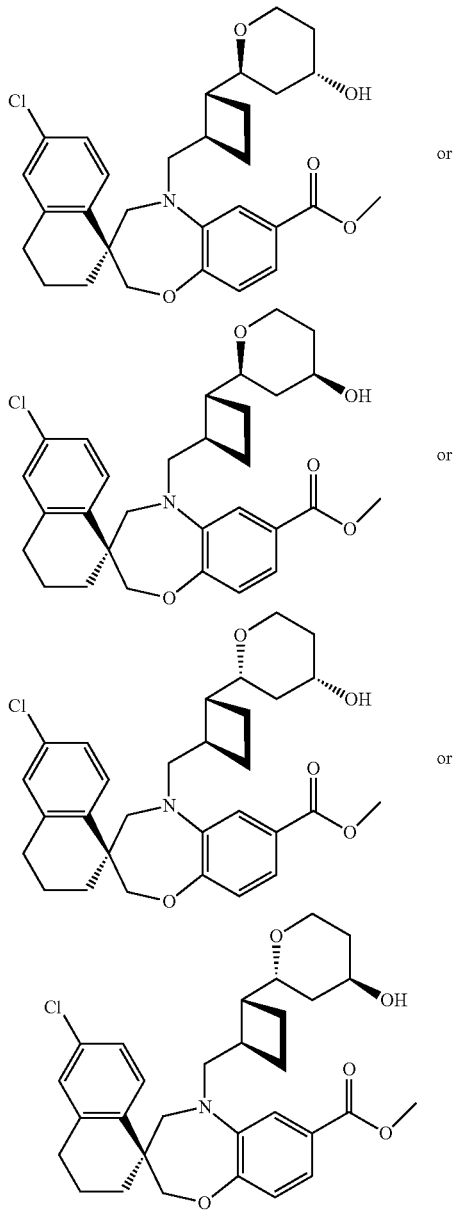

TFA (6 mL) was added slowly to a solution of (S)-methyl 6'-chloro-5-(((1R,2R)-2-formyl cyclobutyl)methyl)-3',4,4',5-tetrahydro-2H,2'H-spiro[benzo[b][1,4]oxazepine-3,1'-naphthalene]-7-carboxylate (Intermediate AA11A, Step 20A, 0.412 g, 0.908 mmol) and 3-buten-1-ol (0.10 ml, 1.18 mmol) in DCM (12 mL) which was degassed with N$_2$. It was stirred at rt for 35 min. The reaction mixture was added slowly to Na2CO3 (aq) solution (50 mL) and MeOH (15 mL). After the mixture was stirred at rt for 83 min, it was extracted with EtOAc (3×90 mL). The combined organic phases were dried over anhydrous sodium sulfate and concentrated. The residue was purified by SFC (Method: 250× 21.2 mm IC—H column w/ 20 g/min MeOH (0.2% DEA)+ 60 g/min CO$_2$ on a Thar 80 SFC. Outlet pressure 100 bar; Temp. 20° C.; Wavelength 220 nm) to provide the title compound (128 mg, first eluting isomer) as a white solid. m/z (ESI, +ve ion) 526.1 (M+H)$^+$.

Step 2: (S)-methyl 6'-chloro-5-(((1R,2R)-2-((S)-4-oxotetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((R)-4-oxotetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

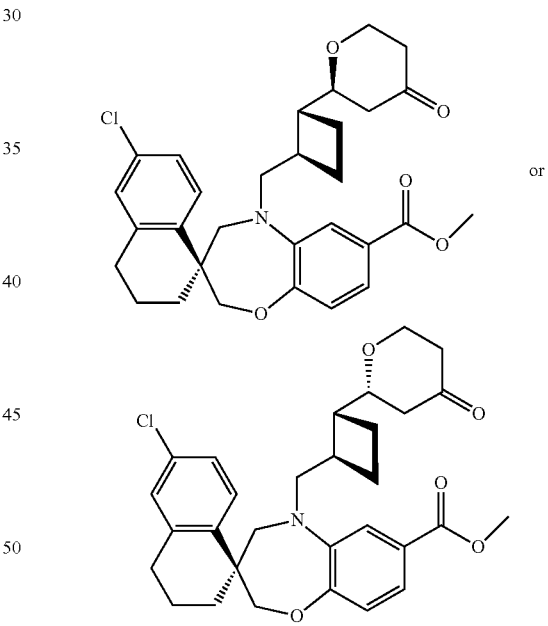

A 50 mL flask was charged with dimethyl sulfoxide (0.051 mL, 0.724 mmol) and DCM (3.5 mL) was cooled to −78° C. Oxalyl chloride (2.0 M solution in DCM, 0.18 mL, 0.36 mmol) was added dropwise slowly and the reaction stirred for 15 min. (S)-Methyl 6'-chloro-5-(((1R,2R)-2-((2R,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 900, Step 1, 0.127 g, 0.241 mmol) in DCM (3.5 mL) was added in one portion to above solution. It was stirred at −78° C. for 20 min. Then triethylamine (0.17 mL, 1.2 mmol) was added and it was stirred at −78° C. to rt for 2 h. It was quenched with water (3 mL) and extracted with EtOAc (130 mL). The organic phase was washed with 1 N HCl solution (2 mL), brine and dried over anhydrous sodium sulfate. It was filtered through silica gel to provide the title compound (126 mg) as a white solid. m/z (ESI, +ve ion) 524.1 (M+H)$^+$.

Step 3: (S)-methyl 6'-chloro-5-(((1R,2R)-2-((2S, 4S)-4-hydroxy-4-vinyltetrahydro-2H-pyran-2-yl) cyclobutyl)methyl)-3',4,4',5-tetrahydro-2H,2'H-spiro [benzo[b][1,4]oxazepine-3,1'-naphthalene]-7-carboxylate or (S)-methyl 6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

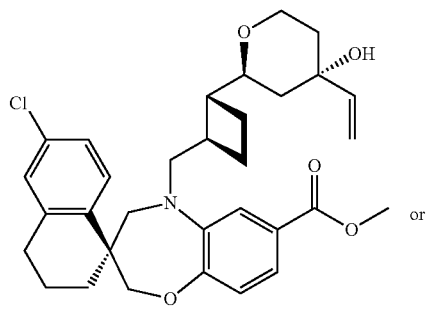

or

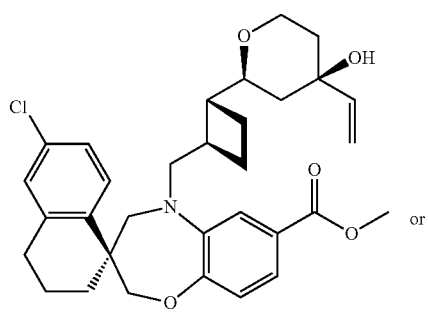

or

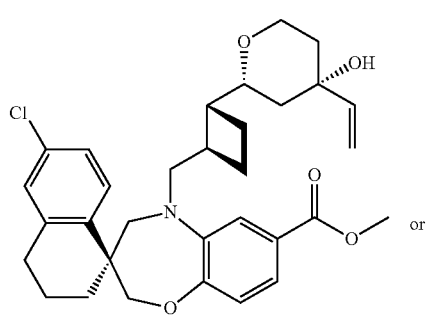

or

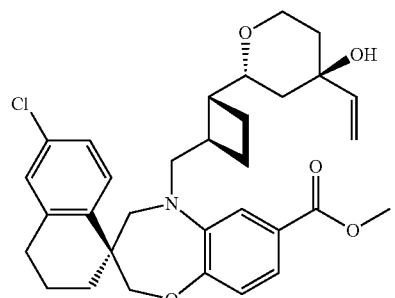

Vinylmagnesium chloride (1.6 M solution in tetrahydrofuran, 0.50 mL, 0.79 mmol) was added dropwise to a solution of (S)-methyl 6'-chloro-5-(((1R,2R)-2-((R)-4-oxotetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 900, Step 2, 0.126 g, 0.240 mmol) in THF (8 mL) at 0° C. It was stirred at 0° C. for 20 min. It was quenched with NH$_4$Cl solution and extracted with EtOAc (180 mL). The organic phase was washed with brine, dried over anhydrous sodium sulfate, filtered through short plug of silica gel and concentrated to give the title compound (133 mg) as an oil. m/z (ESI, +ve ion) 552.1 (M+H)$^+$.

Step 4: (S)-6'-chloro-5-(((1R,2R)-2-((2S,4S)-4-hydroxy-4-vinyltetrahydro-2H-pyran-2-yl)cyclobutyl) methyl)-3',4,4',5-tetrahydro-2H,2'H-spiro[benzo[b] [1,4]oxazepine-3,1'-naphthalene]-7-carboxylic Acid or (S)-6'-chloro-5-(((1R,2R)-2-((2S,4R)-4-hydroxy-4-vinyltetrahydro-2H-pyran-2-yl)cyclobutyl) methyl)-3',4,4',5-tetrahydro-2H,2'H-spiro[benzo[b] [1,4]oxazepine-3,1'-naphthalene]-7-carboxylic Acid or (S)-6'-chloro-5-(((1R,2R)-2-((2R,4S)-4-hydroxy-4-vinyltetrahydro-2H-pyran-2-yl)cyclobutyl) methyl)-3',4,4',5-tetrahydro-2H,2'H-spiro[benzo[b] [1,4]oxazepine-3,1'-naphthalene]-7-carboxylic Acid or (S)-6'-chloro-5-(((1R,2R)-2-((2R,4R)-4-hydroxy-4-vinyltetrahydro-2H-pyran-2-yl)cyclobutyl) methyl)-3',4,4',5-tetrahydro-2H,2'H-spiro[benzo[b] [1,4]oxazepine-3,1'-naphthalene]-7-carboxylic Acid

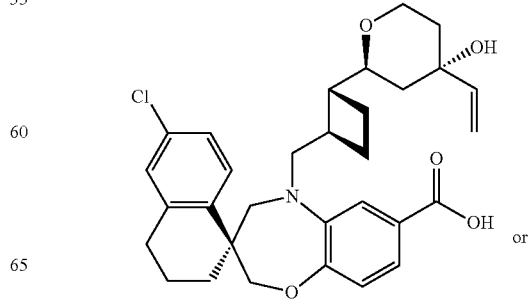

or

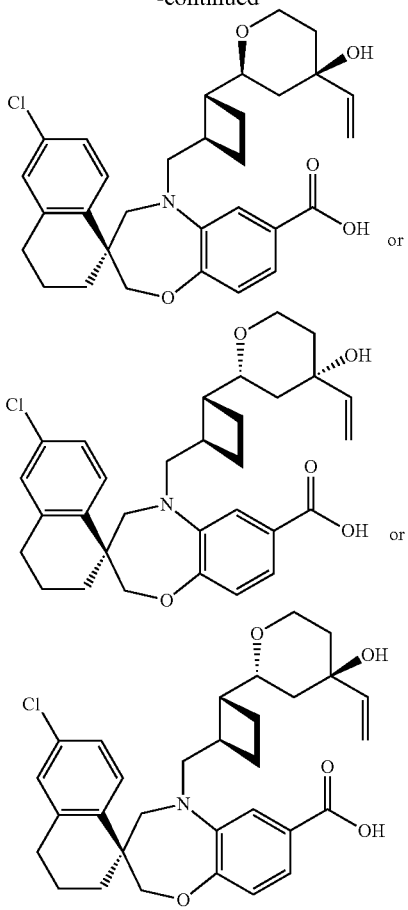

Lithium hydroxide (1.0 M aqueous solution, 7.2 mL, 7.2 mmol) was added to a solution of (1'S)-methyl 6'-chloro-5-(((1R,2R)-2-((2R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 900, Step 3, 0.133 g, 0.241 mmol) in THF (16 mL) and MeOH (8 mL). It was stirred at 50° C. for 3 h. The reaction mixture was concentrated, acidified with 1N HCl solution to pH 2-4, extracted with EtOAc (150 mL). The organic phase was washed with brine, dried over anhydrous sodium sulfate. After it was concentrated the residue was purified by reverse phase preparative HPLC (Gemini™ Prep $C_{18}$ 5 μm column; Phenomenex, Torrance, CA; MeCN in water with 0.1% TFA, gradient elution) to provide the title compound (50 mg, second eluting isomer) as a white solid. m/z (ESI, +ve ion) 538.1 (M+H)$^+$.

Step 5: prop-2-ene-1-sulfonamide

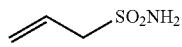

To a solution of ammonia (0.5 M solution in THF, 100 mL, 49.8 mmol) under $N_2$ was added 2-propene-1-sulfonyl chloride (2.0 mL, 14.2 mmol, Matrix Scientific). The mixture became cloudy upon addition, and was left stirring at rt for 4 h. To the mixture was added water, 1.0 N HCl and it was extracted with EtOAc. The organic phase was washed with water, brine, dried over anhydrous sodium sulfate and concentrated. The residue was loaded to a 40 g ISCO Gold column and eluted with 0% to 100% EtOAc/hexane to provide the title compound (669 mg) as a colorless solid. $^1$H NMR (400 MHz, CDCl$_3$) δ 6.05-5.89 (m, 1H), 5.57-5.41 (m, 2H), 4.99-4.78 (m, 2H), 3.89-3.79 (m, 2H).

Step 6: (S)—N-(allylsulfonyl)-6'-chloro-5-(((1R,2R)-2-((2S,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2R)-2-((2R,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide

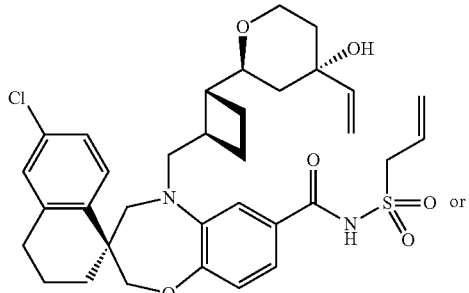

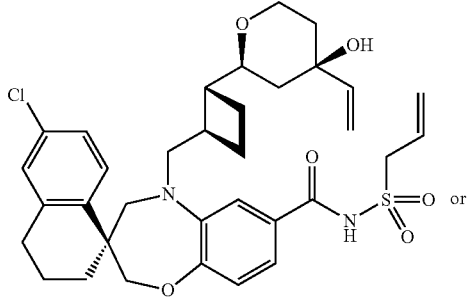

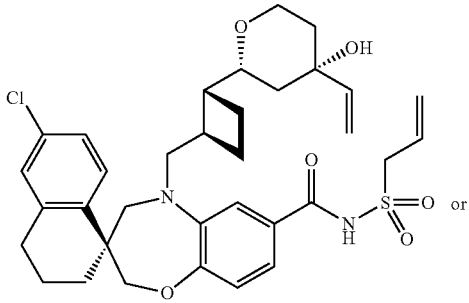

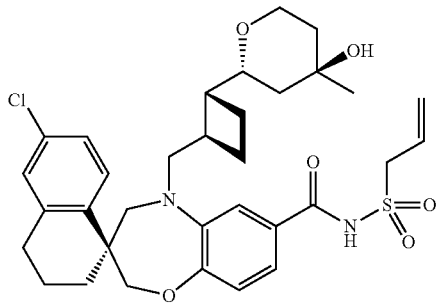

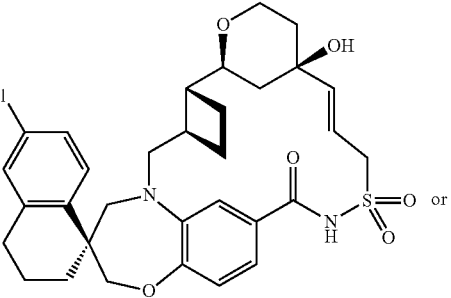

N,N-Dimethylpyridin-4-amine (DMAP) (0.016 g, 0.13 mmol) was added to a solution of (S)-6'-chloro-5-(((1R,2R)-2-((2R,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic acid (Example 900, Step 4; 0.023 g, 0.043 mmol) and prop-2-ene-1-sulfonamide (Example 900, Step 5; 0.020 g, 0.167 mmol) in DCM (1.4 mL) at 0° C. Then N1-((ethylimino)methylene)-N3,N3-dimethylpropane-1,3-diamine hydrochloride (EDC) (0.017 g, 0.090 mmol) was added in portions and it was stirred at 0° C. to rt for 3 days. Then it was concentrated. After it was concentrated the residue was purified by reverse phase preparative HPLC (Gemini™ Prep C$_{18}$ 5 μm column; Phenomenex, Torrance, CA; MeCN in water with 0.1% TFA, gradient elution) to provide the title compound (5.2 mg) as a white solid. m/z (ESI, +ve ion) 641.1 (M+H)$^+$.

Step 7: (3R,6R,7R,11S,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide or (3R,6R,7S,11R,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide or (3R,6R,7R,11R,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide or (3R,6R,7S,11S,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide

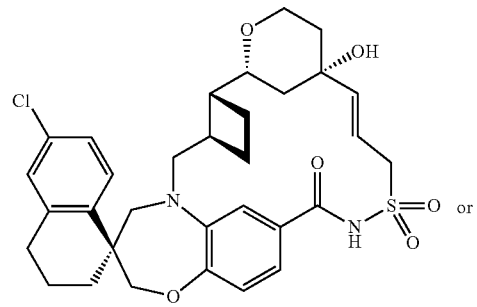

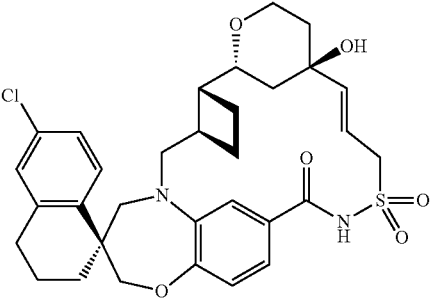

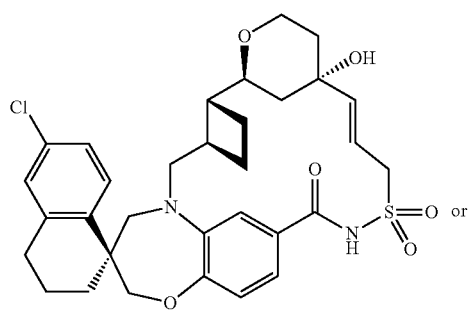

A 250 mL round bottom flask was charged with (S)—N-(allylsulfonyl)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide (Example 900, Step 6, 5.2 mg, 8.1 μmol) in toluene (17 mL). It was stirred at rt for 10 min to dissolve the solid starting material and then subjected to three cycles of evacuation/back-filling with nitrogen. To the homogeneous solution was added a solution of Hoveyda-Grubbs II (1 mg, 1.6 μmol) in toluene (3 mL). The mixture was stirred at 106° C. under nitrogen for 1 h. Then it was concentrated. After it was concentrated the residue was purified by reverse phase preparative HPLC (Gemini™ Prep C$_{18}$ 5 μm column; Phenomenex, Torrance, CA; MeCN in water with 0.1% TFA, gradient elution) to provide the title compound (3 mg) as a white solid. m/z (ESI, +ve ion) 613.0 (M+H)$^+$.

Step 8: (3R,6R,7R,11S,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide or (3R,6R,7S,11R,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide or (3R,6R,7R,11R,24S)-6'-chloro-11-hydroxy-3',4'-dihydro-2'H,17H-spiro[8,22-dioxa-15-thia-1,16-diazapentacyclo[[16.7.2.1$^{7,11}$.0$^{3,6}$.0$^{21,26}$]octacosa-18,20,26-triene-24,1'-naphthalen]-17-one 15,15-dioxide or (3R,6R,7S,11S,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide Platinum (IV) oxide (1.1 mg, 4.9 µmol) was added to a solution of (3R,6R,7R,11S,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide (Example 900, Step 7, 0.003 g, 5 µmol) in EtOAc (5 mL). It was stirred under H$_2$ for 1 h. After it was concentrated the residue was purified by reverse phase preparative HPLC (Gemini™ Prep C$_{18}$ 5 µm column; Phenomenex, Torrance, CA; MeCN in water with 0.1% TFA, gradient elution) to provide the title compound (1.2 mg) as a white solid. $^1$H NMR (400 MHz, CD$_2$Cl$_2$) δ 8.15 (m, 1H), 7.71 (d, J=8.61 Hz, 1H), 7.19 (m, 1H), 7.07-7.12 (m, 1H), 6.96 (m, 2H), 6.86 (m, 1H), 4.63-4.52 (m, 1H), 4.13-4.06 (m, 2H), 3.89-3.78 (m, 3H), 3.75-3.66 (m, 2H), 3.31 (ddd, J=6.26, 11.98, 14.82 Hz, 1H), 3.22 (d, J=14.28 Hz, 1H), 3.00 (dd, J=9.68, 14.97 Hz, 1H), 2.81-2.71 (m, 2H), 2.43 (br. s., 2H), 2.06 (d, J=13.50 Hz, 1H), 2.00-1.19 (m, 16H). m/z (ESI, +ve ion) 615.0 (M+H)$^+$.

Example 901. (3R,6R,7R,11S,24S)-6'-chloro-11-hydroxy-3',4'-dihydro-2'H,17H-spiro[8,22-dioxa-15-thia-1,16-diazapentacyclo [16.7.2.1$^{7,11}$.0$^{3,6}$.0$^{21,26}$] octacosa-18,20,26-triene-24,1'-naphthalen]-17-one 15,15-dioxide or (3R,6R,7S,11R,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$] octacosa-18,20,26-triene-24,1'-naphthalen]-17-one 15,15-dioxide or (3R,6R,7R,11R,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$] octacosa-18,20,26-triene-24,1'-naphthalen]-17-one 15,15-dioxide or (3R,6R,7S,11S,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$] octacosa-18,20,26-triene-24,1'-naphthalen]-17-one 15,15-dioxide

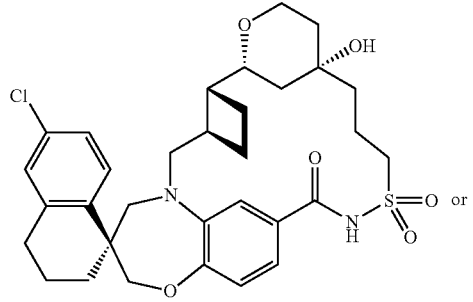 or

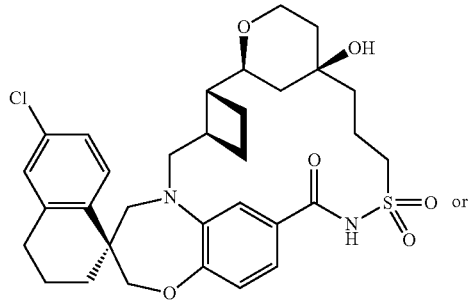 or

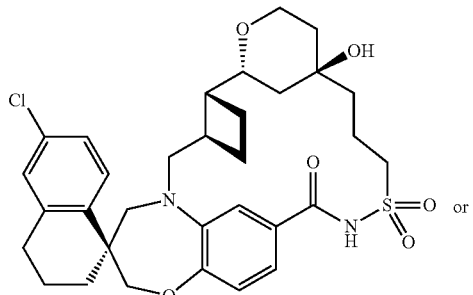 or

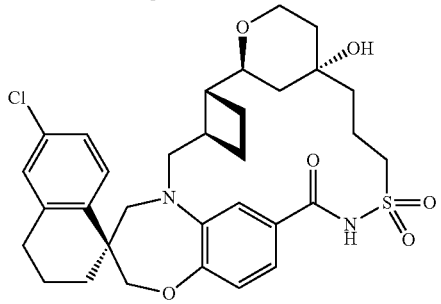

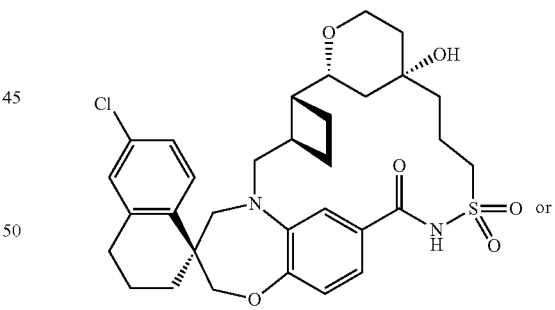 or

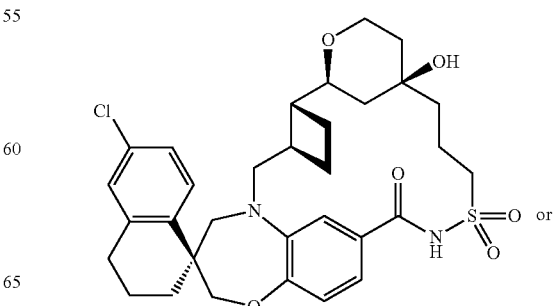 or

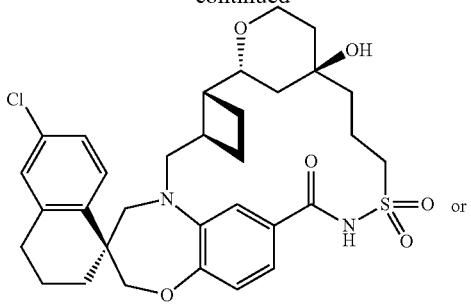

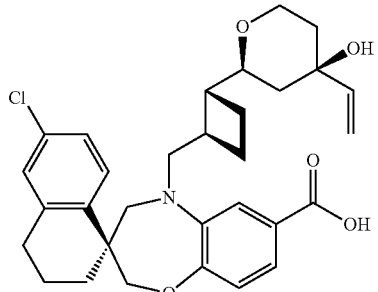

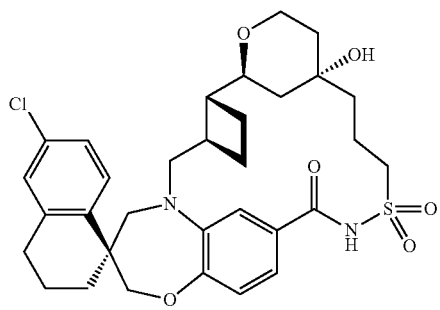

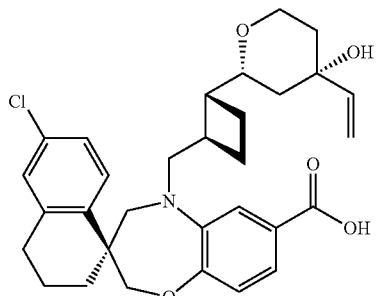

Step 1: (S)-6'-chloro-5-(((1R,2R)-2-((2S,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R)-4-hydroxy-4-vinyltetrahydro-2H-pyran-2-yl) cyclobutyl)methyl)-3',4,4',5-tetrahydro-2H,2'H-spiro[benzo[b][1,4]oxazepine-3,1'-naphthalene]-7-carboxylic Acid

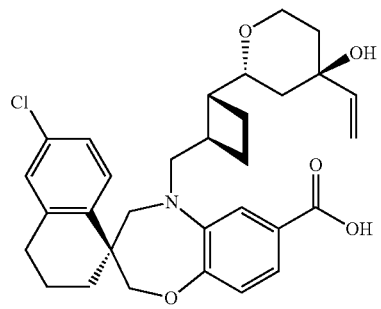

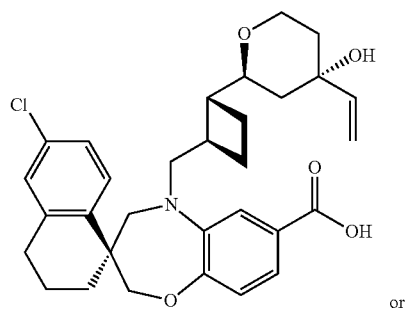

Lithium hydroxide (1.0 M aqueous solution, 7.2 mL, 7.2 mmol) was added to a solution of (1'S)-methyl 6'-chloro-5-(((1R,2R)-2-((2R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 900, Step 3; 0.133 g, 0.241 mmol) in THF (16 mL) and MeOH (8 mL). It was stirred at 50° C. for 3 h. The reaction mixture was concentrated, acidified with 1N HCl solution to pH 2-4, extracted with EtOAc (150 mL). The organic phase was washed with brine, dried over anhydrous sodium sulfate. After it was concentrated the residue was purified by reverse phase preparative HPLC (Gemini™ Prep $C_{18}$ 5 μm column; Phenomenex, Torrance, CA; MeCN in water with 0.1% TFA, gradient elution) to provide the title compound (29 mg, first eluting peak) as a white solid. m/z (ESI, +ve ion) 538.1 $(M+H)^+$.

Step 2: (S)—N-(allylsulfonyl)-6'-chloro-5-(((1R,2R)-2-((2S,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2R)-2-((2R,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide

 or

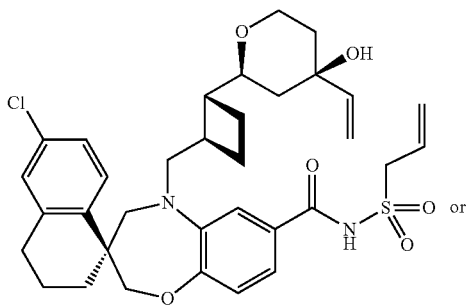 or

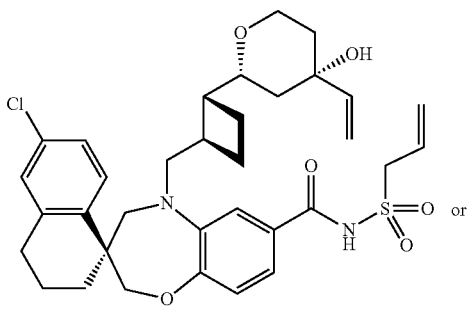 or

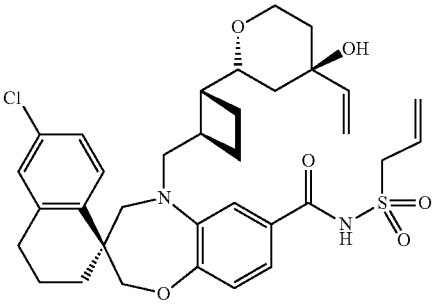

N,N-dimethylpyridin-4-amine (DMAP) (5.7 mg, 0.047 mmol) was added to a solution of (S)-6'-chloro-5-(((1R,2R)-2-((2R,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic acid (Example 901, Step 1; 0.023 g, 0.043 mmol) and prop-2-ene-1-sulfonamide (Example 900, Step 5; 0.013 g, 0.11 mmol) in DCM (0.6 mL) at 0° C. Then N1-((ethylimino)methylene)-N3,N3-dimethylpropane-1,3-diamine hydrochloride (EDC; 6.3 mg, 0.033 mmol) was added in portions and it was stirred at 0° C. to rt for 3 days. After it was concentrated the residue was purified by reverse phase preparative HPLC (Gemini™ Prep $C_{18}$ 5 μm column; Phenomenex, Torrance, CA; MeCN in water with 0.1% TFA, gradient elution) to provide the title compound (3.1 mg) as a white solid. m/z (ESI, +ve ion) 641.1 (M+H)$^+$.

Step 3: (3R,6R,7R,11S,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide or (3R,6R,7S,11R,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide or (3R,6R,7R,11R,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide or (3R,6R,7S,11S,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide

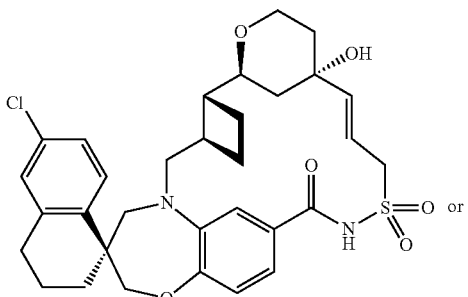 or

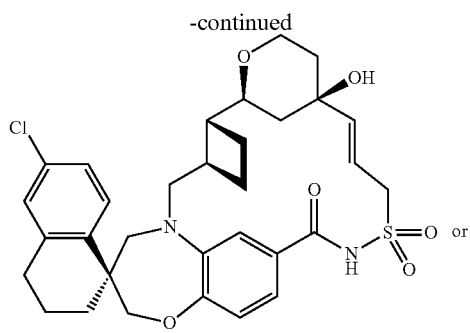

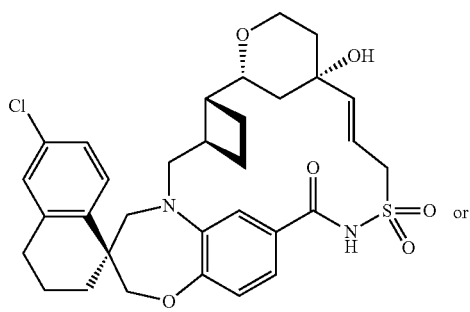

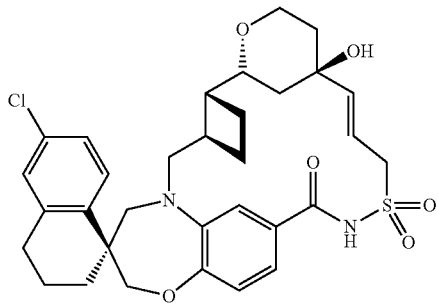

A 250 mL round bottom flask was charged with (S)—N-(allylsulfonyl)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide (Example 901, Step 2; 3.1 mg, 4.8 μmol) in toluene (17 mL). It was stirred at rt for 10 min to dissolve the solid starting material and then subjected to three cycles of evacuation/back-filling with nitrogen. To the homogeneous solution was added a solution of Hoveyda-Grubbs II (1 mg, 1.6 μmol) in toluene (3 mL). The mixture was stirred at 106° C. under nitrogen for 1 h. After it was concentrated the residue was purified by reverse phase preparative HPLC (Gemini™ Prep C$_{18}$ 5 μm column; Phenomenex, Torrance, CA; MeCN in water with 0.1% TFA, gradient elution) to provide the title compound (3 mg) as a white solid. m/z (ESI, +ve ion) 613.0 (M+H)$^+$.

Step 4: (3R,6R,7R,11S,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide
or (3R,6R,7S,11R,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide
or (3R,6R,7R,11R,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide
or (3R,6R,7S,11S,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide Platinum (IV) oxide (1.1 mg, 4.83 μmol) was added to a solution of (3R,6R,7R,11S,12E,24S)-6'-chloro-11-hydroxy-3',4'-dihydro-2'H,17H-spiro[8,22-dioxa-15-thia-1,16-diazapentacyclo-16.7.2.1$^{7,11}$.0$^{3,6}$.0$^{21,26}$]octacosa-18,20,26-triene-24,1'-naphthalen]-17-one 15,15-dioxide (Example 901, Step 3; 0.003 g, 5 μmol) in EtOAc (5 mL). It was stirred under H$_2$ for 1 h. After it was concentrated the residue was purified by reverse phase preparative HPLC (Gemini™ Prep C$_{18}$ 5 μm column; Phenomenex, Torrance, CA; MeCN in water with 0.1% TFA, gradient elution) to provide the title compound (1.3 mg) as a white solid. $^1$H NMR (400 MHz, CD$_2$Cl$_2$) δ 8.24 (s, 1H), 7.72 (d, J=8.41 Hz, 1H), 7.18 (dd, J=2.35, 8.41 Hz, 1H), 7.08 (m, 2H), 6.96 (m, 1H), 6.61 (d, J=1.96 Hz, 1H), 4.07 (m, 2H), 3.88 (m, 1H), 3.84-3.75 (m, 2H), 3.57-3.45 (m, 2H), 3.41 (d, J=12.13 Hz, 1H), 3.27 (d, J=14.08 Hz, 1H), 3.11 (dd, J=10.17, 15.65 Hz, 1H), 2.83-2.73 (m, 2H), 2.42 (m, 1H), 2.33-2.20 (m, 2H), 2.18-1.20 (m, 17H). m/z (ESI, +ve ion) 615.0 (M+H)$^+$.

Example 904. (1S,3'R,6'R)-6-chloro-7'-methylidene-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide

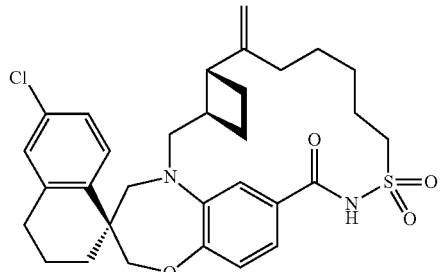

At 0° C., bis(cyclopentadienyl)-μ-chloro(dimethylaluminum)-μ-methylenetitanium, (Tebbe's reagent, 0.5 M solution in toluene, 10.5 mL, 5.25 mmol) was added to a solution of (S,3'R,6'R)-6-chloro-3,4-dihydro-2H,7'H,15'h-spiro[naphthalene-1,22'-[20]oxa[13]thia[1,14]diazatetracyclo[14.7.2.0$^{3,6}$.0$^{19,24}$]pentacosa[16,18,24]trien]-7',15'-dione 13',13'-dioxide (Example 832, 0.150 g, 0.263 mmol) in THF (10.5 mL). It was stirred at 0° C. for 5 min. The reaction mixture was poured into ice water (30 mL), acidified with 1 N HCl solution to pH 3-5, extracted with EtOAc (3×70 mL). The organic phase was washed with brine, dried over anhydrous sodium sulfate and concentrated. The residue was loaded to a 4 g ISCO Gold column and eluted with 0% to 15% EtOAc (containing 0.3% AcOH)/hexane (containing 0.3% AcOH) to provide the title compound (123 mg) as a white solid. $^1$H NMR (400 MHz, CD$_2$Cl$_2$) δ 8.05 (m, 1H), 7.72 (m, 1H), 7.17 (m, 1H), 7.09 (m, 1H), 6.93 (m, 2H), 6.83 (m, 1H), 4.79 (s, 1H), 4.73 (d, J=1.56 Hz, 1H), 4.15-4.06 (m, 2H), 3.97-3.87 (m, 1H), 3.78-3.69 (m, 2H), 3.35-3.23 (m, 2H), 3.06 (dd, J=8.02, 15.45 Hz, 1H), 2.84-2.74 (m, 3H), 2.60-2.50 (m, 1H), 2.08-1.38 (m, 14H). m/z (ESI, +ve ion) 569.0 (M+H)$^+$.

Example 905. (1S,3'R,6'R,9'E)-6-chloro-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [9,16,18,24]tetraene]-7',15'-dione 13',13'-dioxide

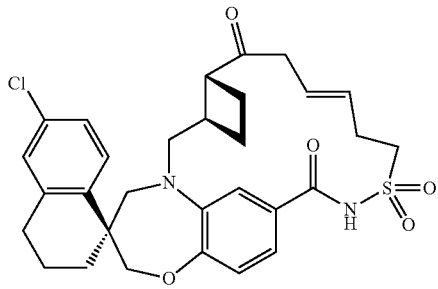

A flask charged dimethyl sulfoxide (0.10 mL, 1.42 mmol) and DCM (2 mL) was cooled to −78° C. Oxalyl chloride (2.0 M solution in DCM, 0.36 mL, 0.71 mmol) was added dropwise and the reaction was stirred for 30 min. A solution of (1S,3'R,6'R,7'S,9'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one-13',13'-dioxide (Example 846, 0.058 g, 0.102 mmol) in DCM (1.2 mL) was added dropwise and the reaction was stirred at −78° C. for 1 h. Triethylamine (0.35 mL, 2.5 mmol) was added dropwise and it was stirred at rt for 1 h. The reaction mixture was quenched with water (2 mL) and 1 N HCl solution (3 mL), extracted with EtOAc (130 mL). It was washed with brine, dried over anhydrous sodium sulfate and concentrated. The residue was loaded to a 4 g ISCO Gold column and eluted with 0% to 35% EtOAc (containing 0.3% AcOH)/hexane (containing 0.3% AcOH) to provide the title compound (16 mg) as a white solid. $^1$H NMR (400 MHz, CD$_2$Cl$_2$) δ 7.68 (d, J=8.61 Hz, 1H), 7.47 (dd, J=2.15, 8.41 Hz, 1H), 7.16 (dd, J=2.45, 8.51 Hz, 1H), 7.10 (d, J=2.35 Hz, 1H), 6.97 (m, 1H), 6.67 (d, J=2.15 Hz, 1H), 5.75 (td, J=7.43, 14.48 Hz, 1H), 5.35 (m, 1H), 4.18-4.10 (m, 2H), 3.87-3.79 (m, 1H), 3.77-3.63 (m, 2H), 3.54 (ddd, J=4.01, 6.55, 15.65 Hz, 1H), 3.36-3.22 (m, 3H), 3.10 (dd, J=6.06, 18.98 Hz, 1H), 2.98-2.90 (m, 1H), 2.80-2.75 (m, 2H), 2.73-2.66 (m, 1H), 2.63-2.54 (m, 1H), 2.15-1.40 (m, 8H). m/z (ESI, +ve ion) 571.1 (M+H)$^+$.

Example 906. (1S,3'R,6'R,7'R)-6-chloro-7'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7')-6-chloro-7'-(hydroxymethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

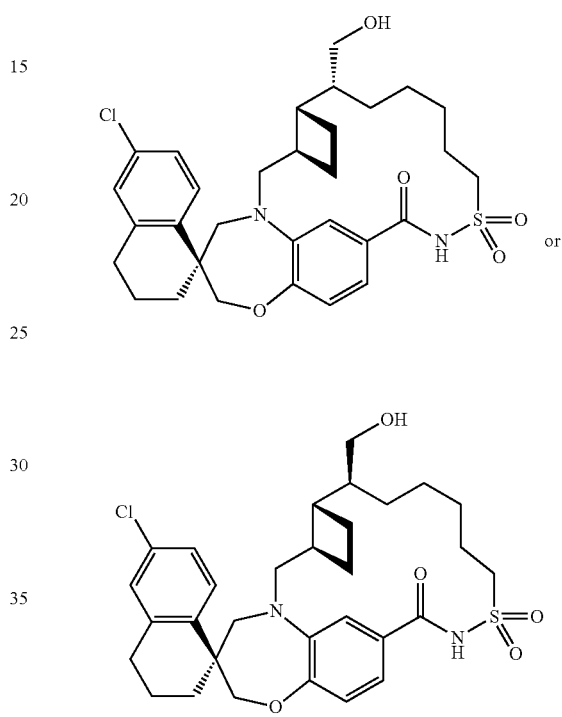

A solution of (1S,3'R,6'R)-6-chloro-7'-methylidene-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (Example 904, 0.018 g, 0.031 mmol) in THF (1.5 mL) was cooled with ice bath. 9-Borabicyclo[3.3.1]nonane (0.5 M solution in THF, 1.2 mL, 0.62 mmol) was added dropwise. After it was stirred at rt for 1 h, MeOH (10 mL) and trimethylamine N-oxide (0.208 g, 1.86 mmol) were added in one portion and the mixture was stirred at rt for 2 h. Then it was concentrated. The residue was stirred in MeOH (30 mL) at 68° C. for 20 h. It was diluted with water and extracted with EtOAc, dried over anhydrous sodium sulfate and concentrated. The residue was purified by reverse phase preparative HPLC (Gemini™ Prep C$_{18}$ 5 μm column; Phenomenex, Torrance, CA; MeCN in water with 0.1% TFA, gradient elution) to give the title compound (first eluting peak) as a white solid. $^1$H NMR (400 MHz, CD$_2$Cl$_2$) δ 7.58 (d, J=8.61 Hz, 1H), 7.01 (dd, J=2.74, 8.61 Hz, 1H), 6.93 (d, J=2.35 Hz, 1H), 6.87 (dd, J=1.76, 8.41 Hz, 1H), 6.76 (m, 2H), 3.91 (m, 2H), 3.73-3.66 (m, 1H), 3.55-3.48 (m, 2H), 3.40 (dd, J=3.81, 10.66 Hz, 1H), 3.25-3.19 (m, 1H), 3.05-2.95 (m, 2H), 2.87 (dd, J=8.61, 15.65 Hz, 1H), 2.65-2.56 (m, 2H), 2.30 (br. s., 2H), 1.93 (d, J=14.67 Hz, 1H), 1.83-0.98 (m, 17H). m/z (ESI, +ve ion) 587.1 (M+H)$^+$.

Example 907. (1S,3'R,6'S, 7'R)-6-chloro-7'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'S, 7'S)-6-chloro-7'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

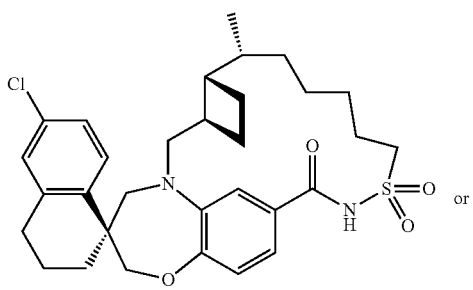

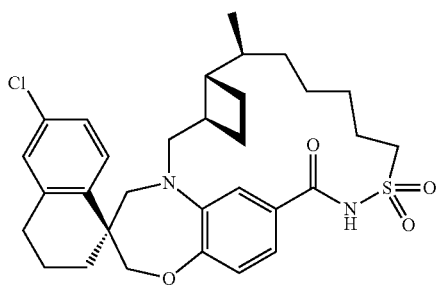

A mixture of (1S,3'R,6'R)-6-chloro-7'-methylidene-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (Example 904, 0.016 g, 0.028 mmol) and platinum (IV) oxide (6 mg, 0.028 mmol) in EtOAc (14 mL) were stirred under H$_2$ at rt for 20 min. The mixture was filtered through syringe filter to remove solid catalyst. The filtrate was concentrated and the residue was purified by SFC (Method: 250×21.2 mm IC—H column w/ 20 g/min MeOH (0.2% DEA)+60 g/min CO$_2$ on a Thar 80 SFC. Outlet pressure 100 bar; Temp. 20° C.; Wavelength 220 nm) to give the title compound (2.7 mg, second eluting peak) as a white solid. $^1$H NMR (400 MHz, CD$_2$Cl$_2$) δ 7.72 (m, 1H), 7.34 (br. s., 1H), 7.16 (d, J=5.48 Hz, 1H), 7.02-7.11 (m, 2H), 6.65 (br. s., 1H), 3.97 (br. s., 2H), 3.87-3.69 (m, 2H), 3.39 (br. s., 1H), 2.94 (br. s., 2H), 2.04 (br. s., 2H), 1.87 (br. s., 4H), 1.74-0.74 (m, 19H). m/z (ESI, +ve ion) 571.1 (M+H)$^+$.

Example 908. (1S,3'R,6'R,7R,10'S,11'S)-6-chloro-10'-methyl-3,4-dihydro-2H,17'H-spiro[naphthalene-1,24'-[8,12,22]trioxa[15]thia[1,16]diazapentacyclo [16.7.2.1$^{7,11}$.0$^{3,6}$.0$^{21,26}$]octacosa[18,20,26]trien]-17'-one 15',15'-dioxide or (1S,3'R,6'R,7'R,10'R,11'S)-6-chloro-10'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'R,11'S)-6-chloro-10'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'S,11'S)-6-chloro-10'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6R,7'S,10'S,11'S)-6-chloro-10'-methyl-3,4-dihydro-2H,17'H-spiro[naphthalene-1,24'-[8,12,22]trioxa[15]thia[1,16]diazapentacyclo [16.7.2.1$^{7,11}$.0$^{3,6}$.0$^{21,26}$]octacosa[18,20,26]trien]-17'-one 15',15'-dioxide or (1S,3'R,6'R,7'S,10'R,11'R)-6-chloro-10'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]18,20,26]trien]-17'-one 15',15'-dioxide or (1S,3'R,6'R,7'R,10'S,11'R)-6-chloro-10'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'S,11'R)-6-chloro-10'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide

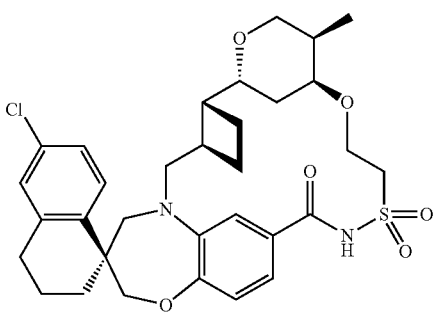

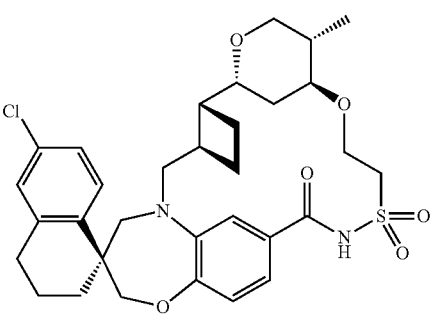

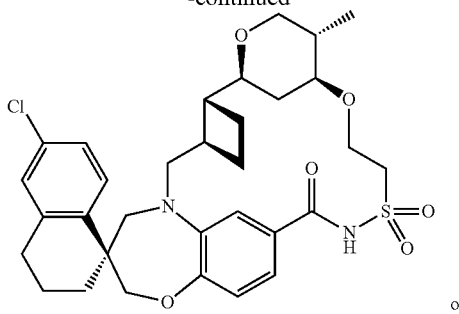

or

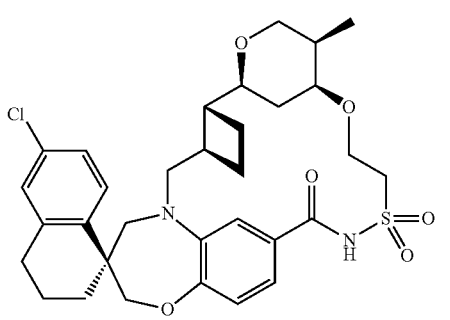

or

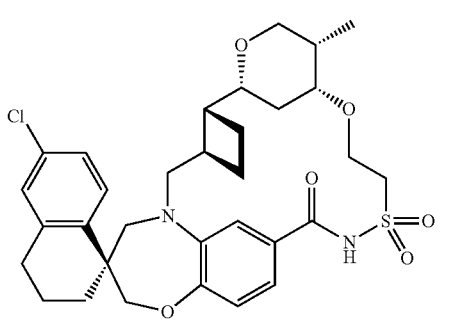

or

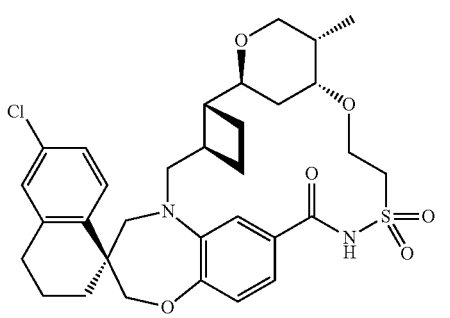

or

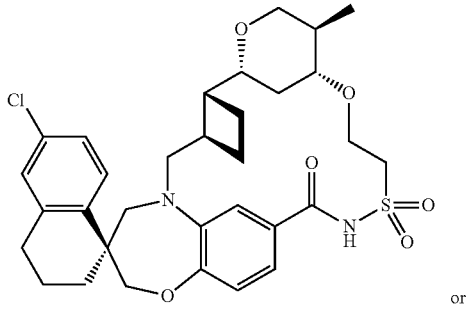

or

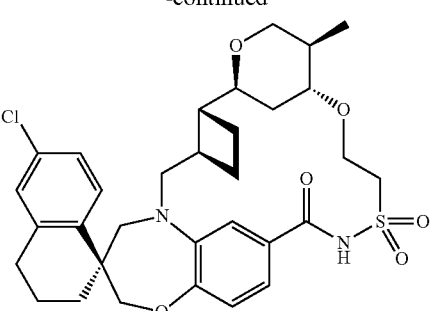

or

Step 1: (S)-methyl 6'-chloro-5-(((1R,2R)-2-((2R,4S,5R)-4-hydroxy-5-methyl tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S,5R)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S,5S)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R,5S)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R,5S)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R,5R)-4-hydroxy-5-methyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

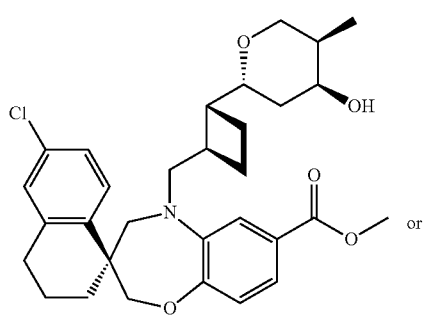

or

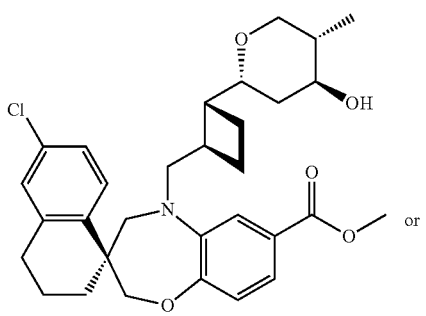 or

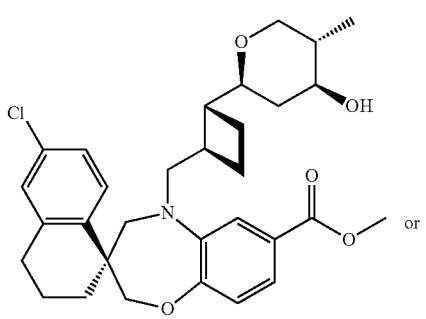 or

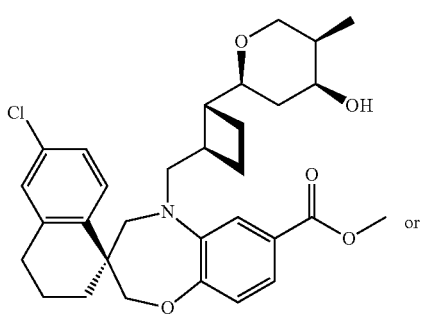 or

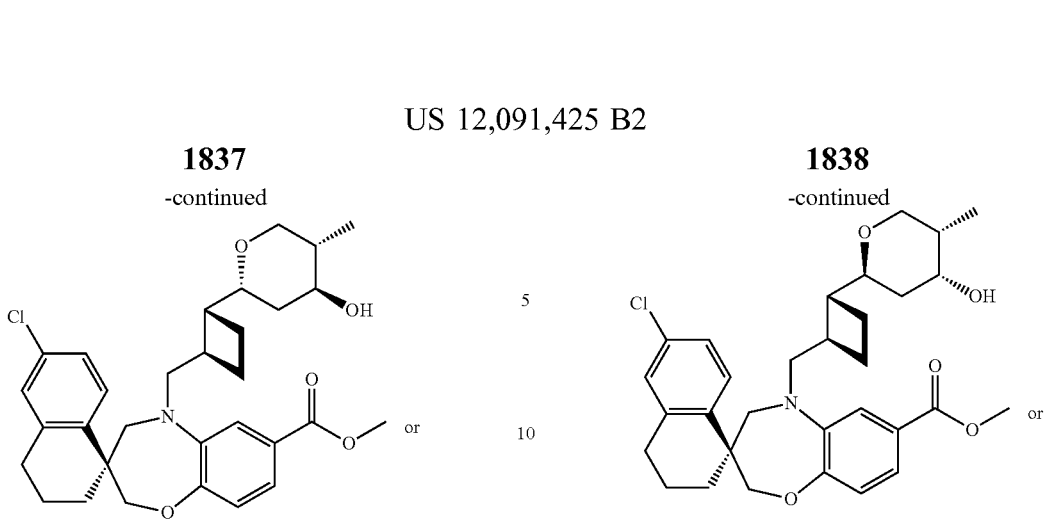 or

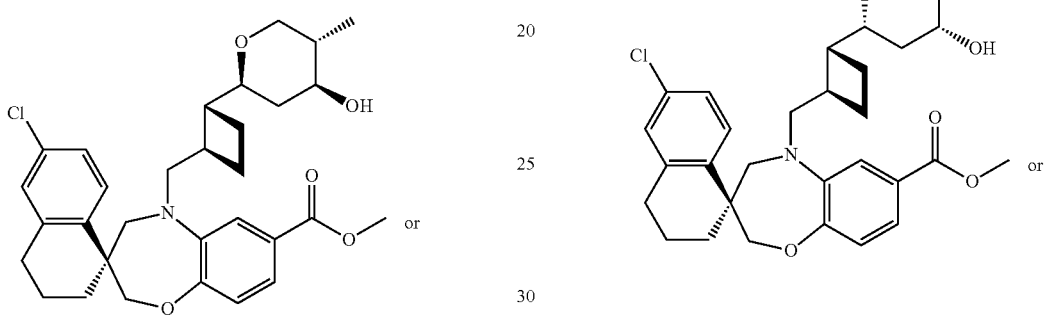 or

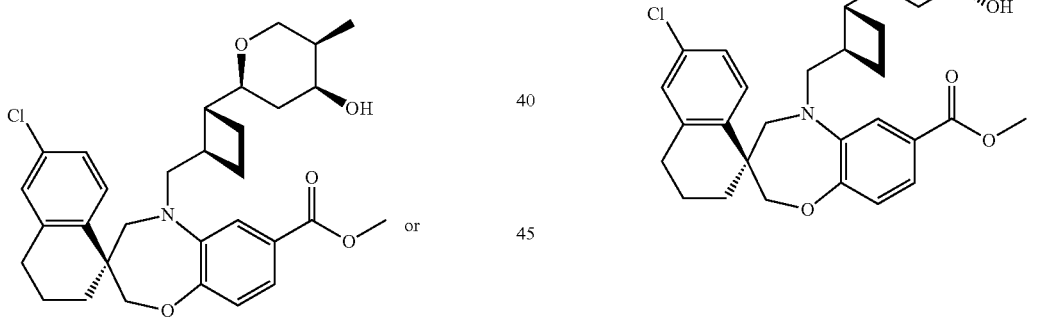 or

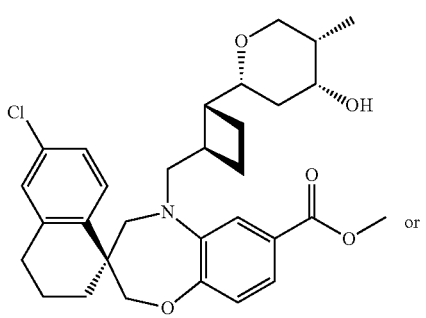 or

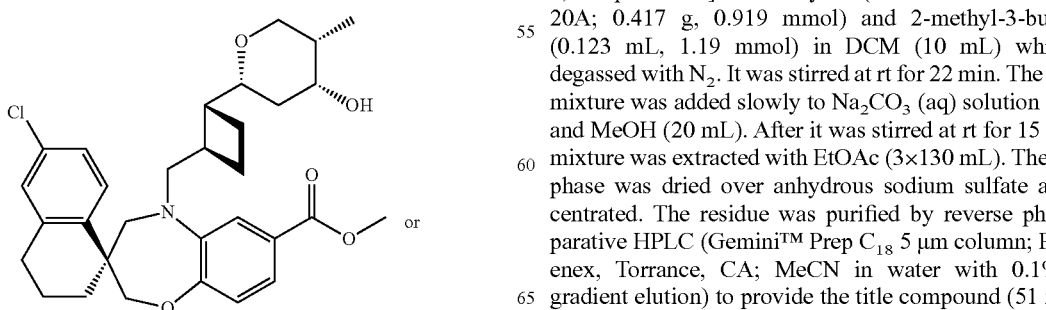

TFA (5.1 mL) was added slowly to a solution of (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A; 0.417 g, 0.919 mmol) and 2-methyl-3-buten-1-ol (0.123 mL, 1.19 mmol) in DCM (10 mL) which was degassed with $N_2$. It was stirred at rt for 22 min. The reaction mixture was added slowly to $Na_2CO_3$ (aq) solution (40 mL) and MeOH (20 mL). After it was stirred at rt for 15 min, the mixture was extracted with EtOAc (3×130 mL). The organic phase was dried over anhydrous sodium sulfate and concentrated. The residue was purified by reverse phase preparative HPLC (Gemini™ Prep $C_{18}$ 5 μm column; Phenomenex, Torrance, CA; MeCN in water with 0.1% TFA, gradient elution) to provide the title compound (51 mg, first eluting peak) as a white solid. m/z (ESI, +ve ion) 540.1 $(M+H)^+$.

Step 2: (S)-6'-chloro-5-(((1R,2R)-2-((2R,4S,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4S,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4S,5S)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4S,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R,5S)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4R,5S)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R,5R)-5-methyl-4-(2-sulfamoylethoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid

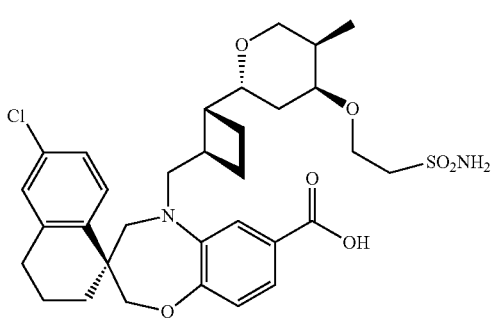 or

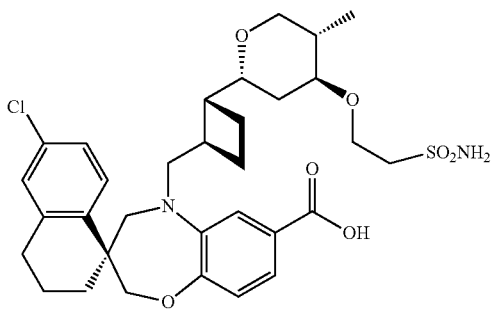 or

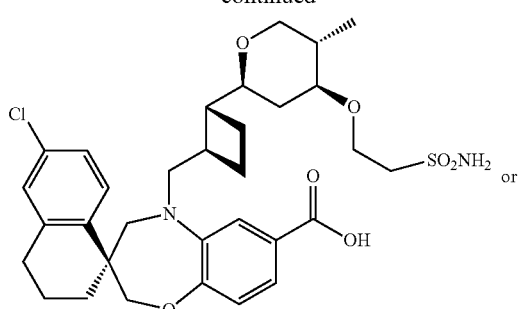 or

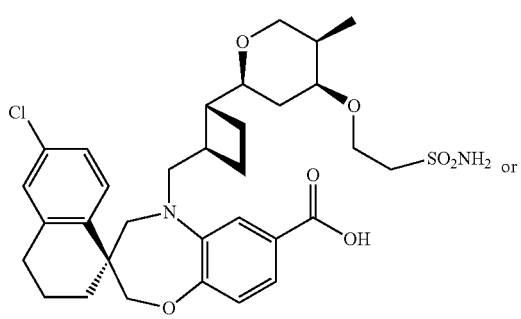 or

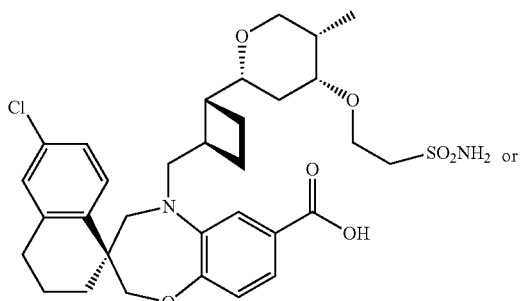 or

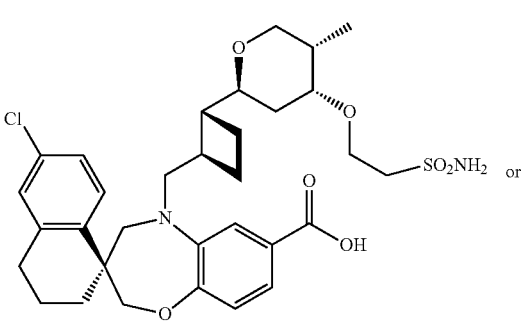 or

1841

-continued

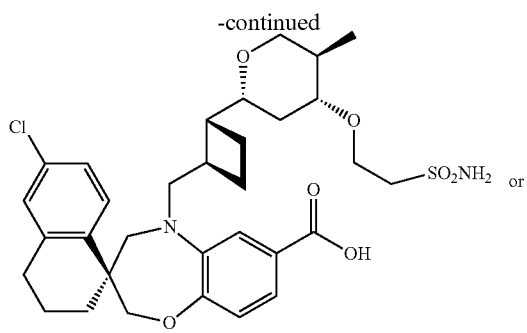

or

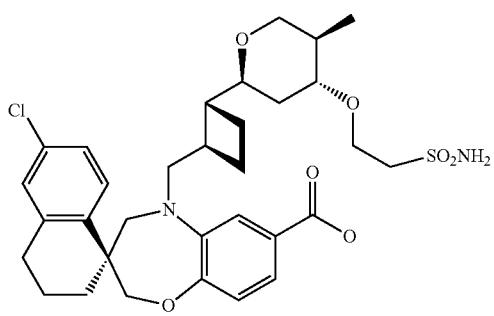

Sodium hydride (60% dispersion in mineral oil, 7.75 mg, 0.368 mmol) was added to a solution of (1'S)-methyl 6'-chloro-5-((((1R,2R)-2-((2R,4S)-4-hydroxy-5-methyltetrahydro-2H-pyran-2-yl) cyclobutyl)methyl)-3',4,4',5-tetrahydro-2H,2'H-spiro[benzo[b][1,4]oxazepine-3,1'-naphthalene]-7-carboxylate (Example 908, Step 1, 0.051 g, 0.094 mmol) in THF (2.7 mL), which was cooled by ice bath. After it was stirred at rt for 18 min N,N-bis(4-methoxybenzyl) ethenesulfonamide (Example 831, Step 2, 0.056 g, 0.161 mmol) in THF (1 mL) was added. It was stirred at rt for 2 h. Water (2 ml) and EtOAc (120 mL) were added. The organic phase was washed with brine, dried over anhydrous sodium sulfate and concentrated. The residue was purified by reverse phase preparative HPLC (Gemini™ Prep C$_{18}$ 5 µm column; Phenomenex, Torrance, CA; MeCN in water with 0.1% TFA, gradient elution) to provide the title compound (15 mg).

Hydrolysis I: The residue was dissolved in THF (3 mL), MeOH (6 mL) and 1M LiOH (6 mL) and the mixture was stirred at 50° C. for 2 h. It was concentrated, acidified with 1N HCl to pH 2-4, extracted with EtOAc 130 mL). The organic phase was washed with brine and dried over anhydrous sodium sulfate and concentrated.

Hydrolysis II: The residue was dissolved in 1:3 TFA/DCM (5 mL) and stirred at rt for 17 h. After it was concentrated the residue was purified by reverse phase preparative HPLC (Gemini™ Prep C$_{18}$ 5 µm column; Phenomenex, Torrance, CA; MeCN in water with 0.1% TFA, gradient elution) to provide the title compound (11 mg) as a white solid.

1842

Step 3. (1S,3'R,6'R,7'R,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,10'R,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'R,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6R,7'S,10'S,11'S)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'R,11'R)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]18,20,26]trien]-17'-one 15',15'-dioxide or (1S,3'R,6'R,7'R,10'S,11'R)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,10'S,11'R)-6-chloro-10'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide

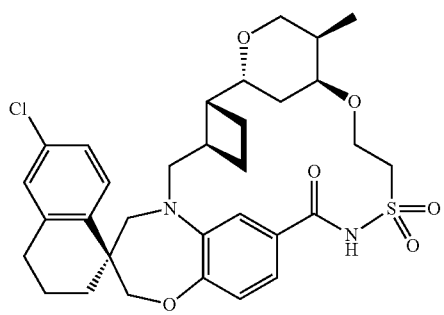

or

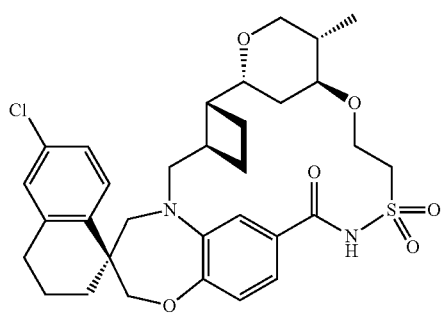

or

-continued

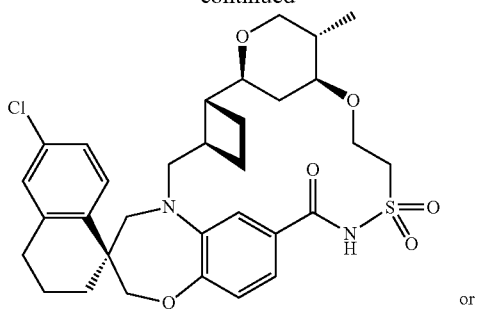

or

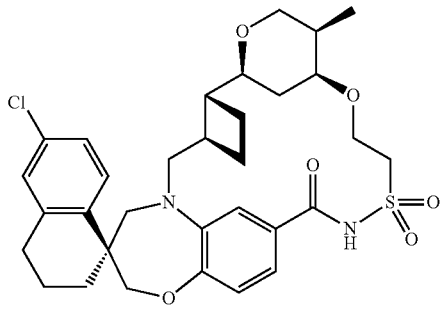

or


or

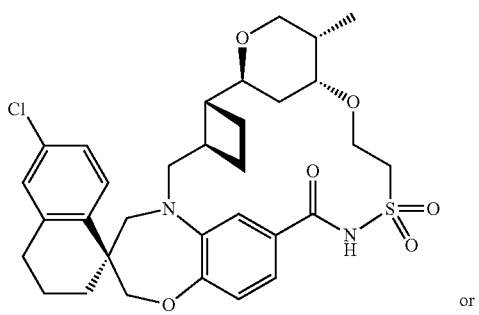

or

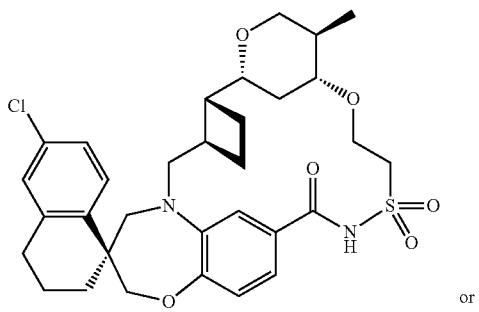

or

-continued

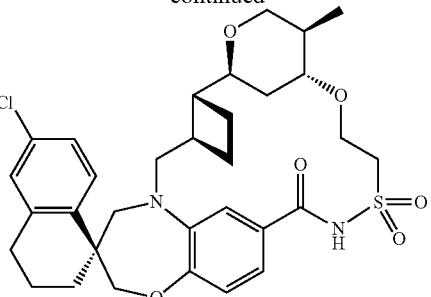

N,N-Dimethylpyridin-4-amine (DMAP) (0.032 g, 0.261 mmol) was added to a solution of (1'S)-6'-chloro-5-(((1R, 2R)-2-((2S,4R)-5-methyl-4-(2-sulfamoylethoxy)tetrahydro-2H-pyran-2-yl) cyclobutyl)methyl)-3',4,4',5-tetrahydro-2H, 2'H-spiro [benzo[b][1,4]oxazepine-3,1'-naphthalene]-7-carboxylic Acid (Example 908, Step 2, 0.011 g, 0.017 mmol) in DCM (50 mL) at 0° C. Then N1-((ethylimino)methylene)-N3,N3-dimethylpropane-1,3-diamine hydrochloride (EDC, 0.040 g, 0.208 mmol) was added slowly in portions and it was stirred at 0° C. to rt for 22 h. It was concentrated and the residue was purified by reverse phase preparative HPLC (Gemini™ Prep $C_{18}$ 5 μm column; Phenomenex, Torrance, CA; MeCN in water with 0.1% TFA, gradient elution) to provide the title compound (7.5 mg) as a white solid. $^1$H NMR (400 MHz, $CD_2Cl_2$) δ 8.24 (br. s., 1H), 7.72 (d, J=8.61 Hz, 1H), 7.16 (ddd, J=2.25, 8.36, 15.01 Hz, 2H), 7.10 (d, J=2.15 Hz, 1H), 6.98 (d, J=8.02 Hz, 1H), 6.74 (d, J=1.96 Hz, 1H), 4.14-4.03 (m, 2H), 3.91-3.70 (m, 5H), 3.46-3.35 (m, 2H), 3.29 (t, J=9.59 Hz, 1H), 3.04-2.93 (m, 3H), 2.86-2.73 (m, 3H), 2.37-2.16 (m, 4H), 2.13-1.72 (m, 5H), 1.69-1.60 (m, 1H), 1.44 (t, J=12.13 Hz, 1H), 1.14-1.29 (m, 2H), 0.89 (d, J=6.46 Hz, 3H). m/z (ESI, +ve ion) 615.0 (M+H)$^+$.

Example 910. (3R,6R,7R,11S,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$] octacosa-18,20,26-triene-24,1'-naphthalen]-17-one 15,15-dioxide or (3R,6R,7S,11R,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$] octacosa-18,20,26-triene-24,1'-naphthalen]-17-one 15,15-dioxide or (3R,6R,7R,11R,24S)-6'-chloro-11-hydroxy-3',4'-dihydro-2'H,17H-spiro[8,22-dioxa-15-thia-1,16-diazapenta cyclo[16.7.2.1$^{7,11}$.0$^{3,6}$.0$^{21,26}$] octacosa-18,20,26-triene-24,1'-naphthalen]-17-one 15,15-dioxide or (3R,6R,7S,11S,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$] octacosa-18,20,26-triene-24,1'-naphthalen]-17-one 15,15-dioxide

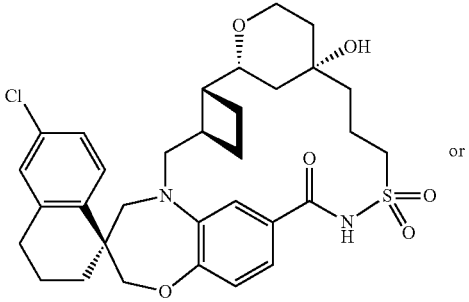

or

1845

-continued

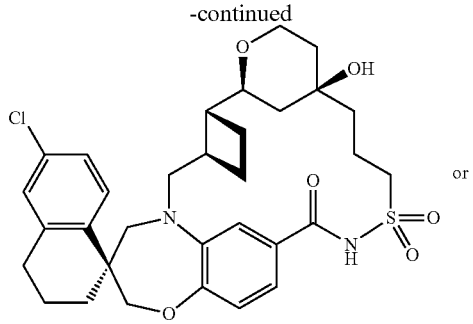

or

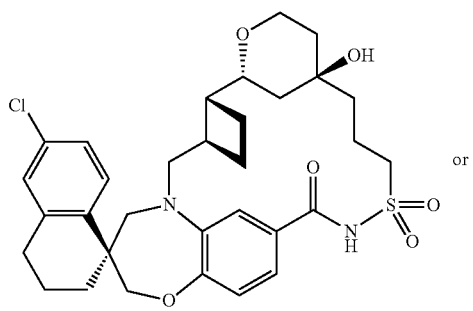

1846

Step 1: (S)-methyl 6'-chloro-5-(((1R,2R)-2-((2S,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

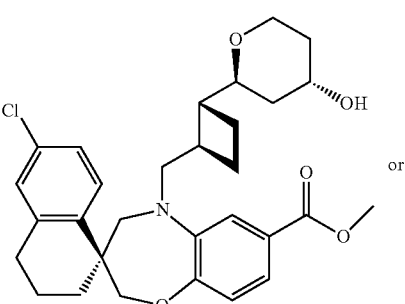

or

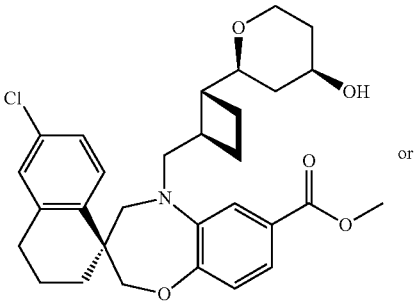

or

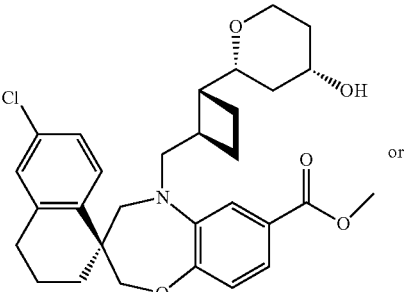

or

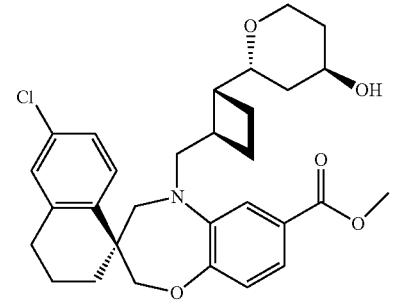

1847

TFA (6 mL) was added slowly to a solution of (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A; 0.412 g, 0.908 mmol) and 3-buten-1-ol (0.10 mL, 1.18 mmol) in DCM (12 mL) which was degassed with $N_2$. It was stirred at rt for 35 min. The reaction mixture was added slowly to $Na_2CO_3$ (aq) solution (50 mL) and MeOH (15 mL). After the mixture was stirred at rt for 83 min, it was extracted with EtOAc (3×90 mL). The combined organic phases were dried over anhydrous sodium sulfate and concentrated. The residue was purified by SFC (Method: 250× 21.2 mm IC—H column w/ 20 g/min MeOH (0.2% DEA)+ 60 g/min $CO_2$ on a Thar 80 SFC. Outlet pressure 100 bar; Temp. 20° C.; Wavelength 220 nm). The title compound was obtained a single isomer (102 mg, second eluting peak) as a white solid. m/z (ESI, +ve ion) 526.1 (M+H)$^+$.

Step 2: (S)-methyl 6'-chloro-5-(((1R,2R)-2-((S)-4-oxotetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((R)-4-oxotetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

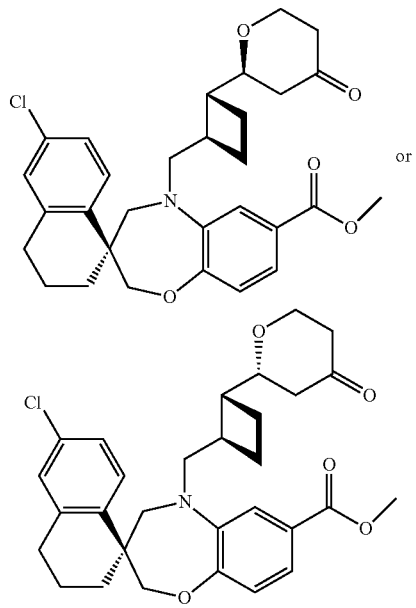

A 50 mL flask was charged with dimethyl sulfoxide (0.051 mL, 0.724 mmol) and DCM (3.5 mL) was cooled to −78° C. Oxalyl chloride (2.0 M solution in DCM, 0.18 ml, 0.36 mmol) was added dropwise slowly and the reaction stirred for 15 min. (S)-Methyl 6'-chloro-5-(((1R,2R)-2-((2R,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 910, Step 1, 0.127 g, 0.241 mmol) in DCM (3.5 mL) was added in one portion to above solution. It was stirred at −78° C. for 20 min. Then triethylamine (0.17 mL, 1.2 mmol) was added and it was stirred at −78° C. to rt for 2 h. It was quenched with water (3 mL) and extracted with EtOAc (130 mL). The organic phase was washed with 1 N HCl solution (2 mL),

1848 brine and dried over anhydrous sodium sulfate. It was filtered through silica gel to provide the title compound (126 mg) as a white solid. m/z (ESI, +ve ion) 524.1 (M+H)$^+$.

Step 3: (S)-methyl 6'-chloro-5-(((1R,2R)-2-((2S,4S)-4-hydroxy-4-vinyltetrahydro-2H-pyran-2-yl) cyclobutyl)methyl)-3',4,4',5-tetrahydro-2H,2'H-spiro [benzo[b][1,4]oxazepine-3,1'-naphthalene]-7-carboxylate or (S)-methyl 6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

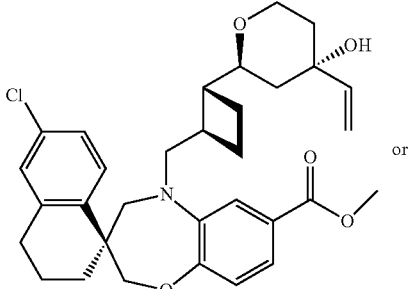

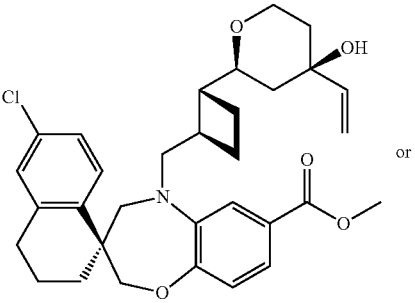

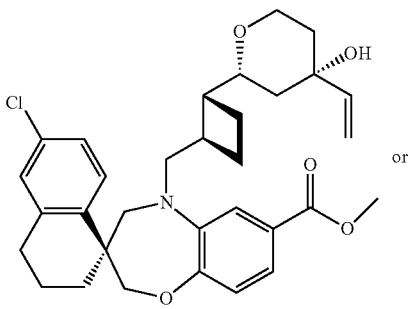

-continued

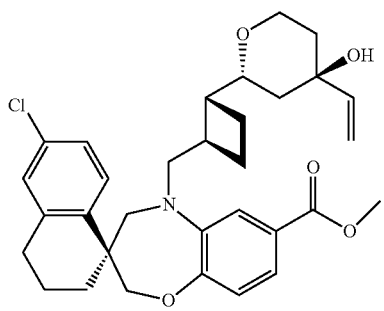

Vinylmagnesium chloride (1.6 M solution in tetrahydrofuran, 0.50 mL, 0.79 mmol) was added dropwise to a solution of (S)-methyl 6'-chloro-5-(((1R,2R)-2-((R)-4-oxo-tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 910, Step 2, 0.126 g, 0.240 mmol) in THF (8 mL) at 0° C. It was stirred at 0° C. for 20 min. It was quenched with NH$_4$Cl solution and extracted with EtOAc (180 mL). The organic phase was washed with brine, dried over anhydrous sodium sulfate, filtered through short plug of silica gel and concentrated to give the title compound (133 mg) as an oil. m/z (ESI, +ve ion) 552.1 (M+H)$^+$.

Step 4: (S)-6'-chloro-5-(((1R,2R)-2-((2S,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid

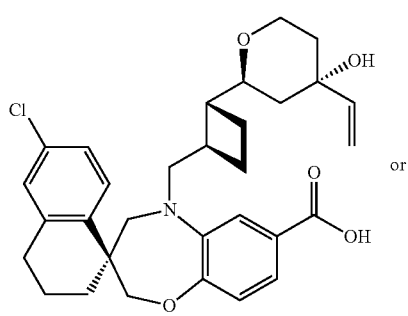

-continued

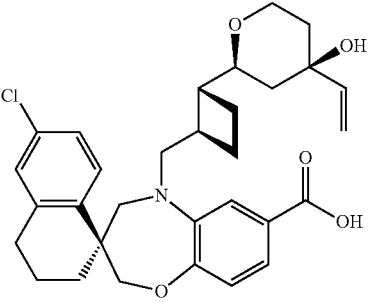

or

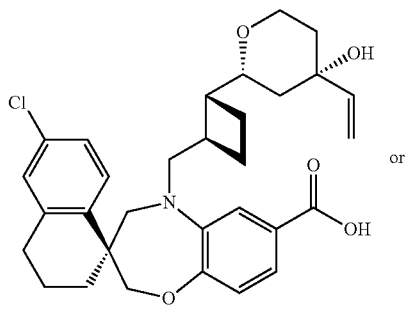

or

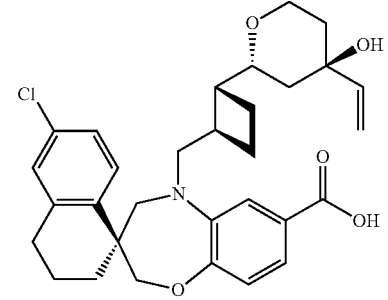

Lithium hydroxide (1.0 M aqueous solution, 7.2 mL, 7.2 mmol) was added to a solution of (1'S)-methyl 6'-chloro-5-(((1R,2R)-2-((2R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 910, Step 3; 0.133 g, 0.241 mmol) in THF (16 mL) and MeOH (8 mL). It was stirred at 50° C. for 3 h. The reaction mixture was concentrated, acidified with 1 N HCl solution to pH 2-4, extracted with EtOAc (150 mL). The organic phase was washed with brine, dried over anhydrous sodium sulfate. After it was concentrated the residue was purified by reverse phase preparative HPLC (Gemini™ Prep C$_{18}$ 5 μm column; Phenomenex, Torrance, CA; MeCN in water with 0.1% TFA, gradient elution) to provide the title compound (50 mg, second eluting peak) as a white solid. m/z (ESI, +ve ion) 538.1 (M+H)$^+$.

Step 5: (S)—N-(allylsulfonyl)-6'-chloro-5-(((1R,2R)-2-((2S,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2R)-2-((2R,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide

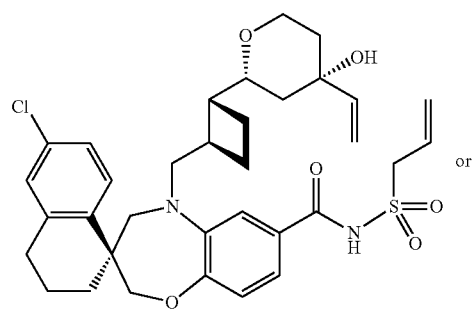

or


or


or

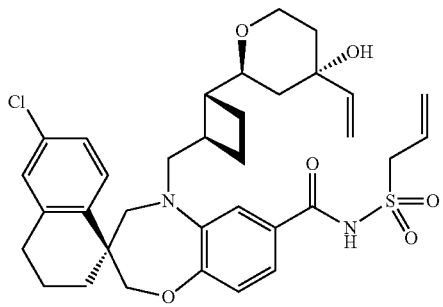

N,N-Dimethylpyridin-4-amine (DMAP) (0.016 g, 0.13 mmol) was added to a solution of (S)-6'-chloro-5-(((1R,2R)-2-((2R,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic acid (Example 910, Step 4; 0.023 g, 0.043 mmol)) and prop-2-ene-1-sulfonamide (Example 900, Step 5; 0.020 g, 0.167 mmol) in DCM (1.4 mL) at 0° C. Then N1-((ethylimino)methylene)-N3,N3-dimethyl propane-1,3-diamine hydrochloride (EDC; 0.017 g, 0.090 mmol) was added in portions and it was stirred at 0° C. to rt for 3 days. After it was concentrated the residue was purified by reverse phase preparative HPLC (Gemini™ Prep $C_{18}$ 5 μm column; Phenomenex, Torrance, CA; MeCN in water with 0.1% TFA, gradient elution) to provide the title compound (5.2 mg) as a white solid. m/z (ESI, +ve ion) 641.1 (M+H)⁺.

Step 6: (3R,6R,7R,11S,12E,24S)-6'-chloro-11-hydroxy-3',4'-dihydro-2'H,17H-spiro[8,22-dioxa-15-thia-1,16-diazapentacyclo[16.7.2.1⁷,¹¹.0³,⁶.0²¹,²⁶]octacosa-18,20,26-triene-24,1'-naphthalen]-17-one 15,15-dioxide or (3R,6R,7S,11R,12E,24S)-6'-chloro-11-hydroxy-3',4'-dihydro-2'H,17H-spiro[8,22-dioxa-15-thia-1,16-diazapentacyclo[16.7.2.1⁷,¹¹.0³,⁶.0²¹,²⁶]octacosa-18,20,26-triene-24,1'-naphthalen]-17-one 15,15-dioxide or (3R,6R,7R,11R,12E,24S)-6'-chloro-11-hydroxy-3',4'-dihydro-2'H,17H-spiro[8,22-dioxa-15-thia-1,16-diazapentacyclo[16.7.2.1⁷,¹¹.0³,⁶.0²¹,²⁶]octacosa-18,20,26-triene-24,1'-naphthalen]-17-one 15,15-dioxide or (3R,6R,7S,11S,12E,24S)-6'-chloro-11-hydroxy-3',4'-dihydro-2'H,17H-spiro[8,22-dioxa-15-thia-1,16-diazapentacyclo[16.7.2.1⁷,¹¹.0³,⁶.0²¹,²⁶]octacosa-18,20,26-triene-24,1'-naphthalen]-17-one 15,15-dioxide

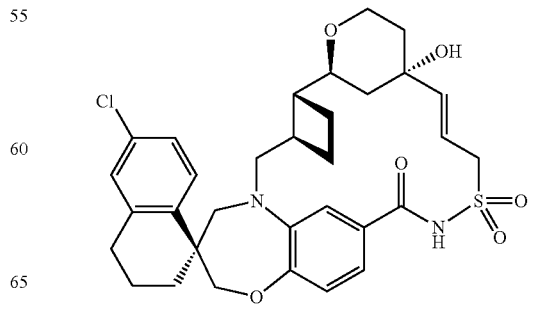

or


or

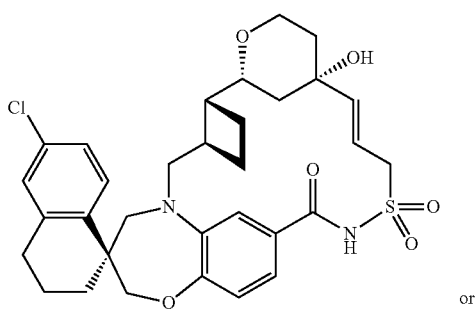

or

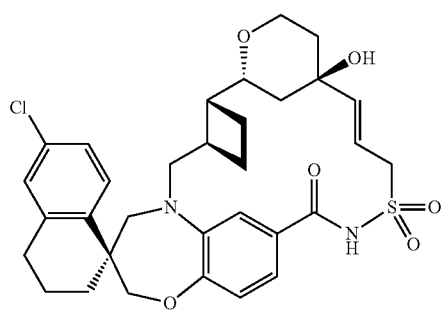

A 250 mL round bottom flask was charged with (S)—N-(allylsulfonyl)-6'-chloro-5-((((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide (Example 910, Step 5; 5.2 mg, 8.1 μmol) in toluene (17 mL). It was stirred at rt for 10 min to dissolve the solid starting material and then subjected to three cycles of evacuation/back-filling with nitrogen. To the homogeneous solution was added a solution of Hoveyda-Grubbs II (1 mg, 1.6 μmol) in toluene (3 mL). The mixture was stirred at 106° C. under nitrogen for 1 h. After it was concentrated the residue was purified by reverse phase preparative HPLC (Gemini™ Prep C$_{18}$ 5 μm column; Phenomenex, Torrance, CA; MeCN in water with 0.10% TFA, gradient elution) to provide the title compound (3 mg) as a white solid. m/z (ESI, +ve ion) 613.0 (M+H)$^+$.

Step 7: (3R,6R,7R,11S,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide or (3R,6R,7S,11R,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide or (3R,6R,7R,11R,24S)-6'-chloro-11-hydroxy-3',4'-dihydro-2'H,17H-spiro[8,22-dioxa-15-thia-1,16-diazapenta cyclo[16.7.2.1$^{7,11}$.0$^{3,6}$.0$^{21,26}$]octacosa-18,20,26-triene-24,1'-naphthalen]-17-one 15,15-dioxide or (3R,6R,7S,11S,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide Platinum (IV) oxide (1.1 mg, 4.9 μmol) was added to a solution of (3R,6R,7R,11S,12E,24S)-6'-chloro-11-hydroxy-3',4'-dihydro-2'H,17H-spiro[8,22-dioxa-15-thia-1,16-diazapentacyclo [16.7.2.1$^{7,11}$.0$^{3,6}$.0$^{21,26}$]octacosa-18,20,26-triene-24,1'-naphthalen]-17-one 15,15-dioxide (Example 910, Step 6; 0.003 g, 5 μmol) in EtOAc (5 mL). It was stirred under H$_2$ for 1 h. After it was concentrated the residue was purified by reverse phase preparative HPLC (Gemini™ Prep C$_{18}$ 5 μm column; Phenomenex, Torrance, CA; MeCN in water with 0.1% TFA, gradient elution) to provide the title compound (1.2 mg) as a white solid. $^1$H NMR (500 MHz, CD$_2$Cl$_2$) δ 8.06 (m, 1H), 7.71 (m, 1H), 7.18 (m, 1H), 7.09 (m, 1H), 6.93 (d, J=0.73 Hz, 2H), 6.83 (m, 1H), 4.11 (m, 2H), 3.84-3.75 (m, 3H), 3.70-3.62 (m, 3H), 3.35 (m, 1H), 3.23 (m, 1H), 2.82-2.73 (m, 2H), 2.33 (m, 1H), 2.13 (s, 1H), 2.08 (d, J=3.18 Hz, 1H), 2.05 (m, 2H), 2.01-1.04 (m, 15H). m/z (ESI, +ve ion) 615.0 (M+H)$^+$.

Example 911. (1S,3'R,6'S,8'S,10'Z)-6-chloro-8'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [10,16,18,24]tetraen]-15'-one 13',13'-dioxide or (1S,3'R,6'S,8'S,10'Z)-6-chloro-8'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [10,16,18,24]tetraen]-15'-one 13',13'-dioxide

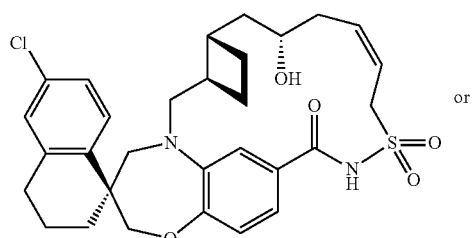

or

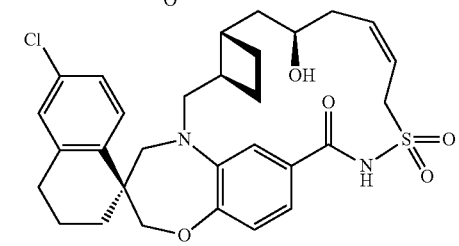

Step 1: (S)-6'-chloro-5-(((1R,2S)-2-(2-oxoethyl)cyclobutyl)methyl)-3',4,4',5-tetrahydro-2H,2'H-spiro[benzo[b][1,4]oxazepine-3,1'-naphthalene]-7-carboxylic Acid

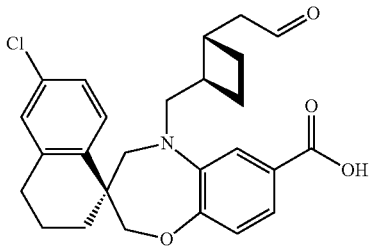

A mixture of (S)-methyl 6'-chloro-5-(((1R,2R)-2-((E)-2-methoxyvinyl)cyclobutyl)methyl)-3',4,4',5-tetrahydro-2H,2'H-spiro[benzo[b][1,4]oxazepine-3,1'-naphthalene]-7-carboxylate (Example 865, Step 1; 0.057 g, 0.118 mmol) and lithium hydroxide (1.0 M aqueous solution. 0.95 ml, 0.95 mmol) in MeOH (0.5 mL) and THF (0.8 mL) was stirred at 60° C. for 3 h. It was concentrated and was added 1 N HCl solution (2 mL) and acetone (6 mL) and stirred at rt for 18 h. It was concentrated and the residue was extracted with EtOAc (100 mL). The organic phase was washed with brine, dried over anhydrous sodium sulfate, concentrated to provide the title compound (51 mg) as a white solid. m/z (ESI, +ve ion) 454.1 (M+H)$^+$.

Step 2: (S)-6'-chloro-5-(((1R,2S)-2-((S)-2-hydroxypent-4-en-1-yl)cyclobutyl) methyl)-3',4,4',5-tetrahydro-2H,2'H-spiro[benzo[b][1,4]oxazepine-3,1'-naphthalene]-7-carboxylic Acid or (S)-6'-chloro-5-(((1R,2S)-2-((R)-2-hydroxypent-4-en-1-yl)cyclobutyl)methyl)-3',4,4',5-tetrahydro-2H,2'H-spiro[benzo[b][1,4]oxazepine-3,1'-naphthalene]-7-carboxylic Acid

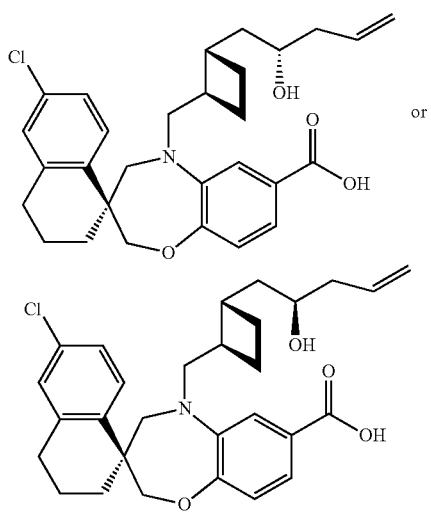

At 0° C., allylmagnesium bromide (1.0 M solution in diethyl ether, 0.67 mL, 0.67 mmol) was added dropwise to a solution of (S)-6'-chloro-5-(((1R,2S)-2-(2-oxoethyl)cyclobutyl)methyl)-3',4,4',5-tetrahydro-2H,2'H-spiro[benzo[b][1,4]oxazepine-3,1'-naphthalene]-7-carboxylic acid (Example 911, Step 1; 0.051 g, 0.112 mmol) in THF (1.9 mL). It was stirred at rt for 0.5 h. The reaction was quenched with NH$_4$Cl solution, acidified with 1 N HCl solution to pH 2-3 and extracted with EtOAc (130 mL). The organic phase was washed with brine (1 mL), dried over anhydrous sodium sulfate, filtered through silica gel, and concentrated. The residue was purified by SFC (Method: 250×21.2 mm IC—H column w/ 20 g/min MeOH (0.2% DEA)+60 g/min CO$_2$ on a Thar 80 SFC. Outlet pressure 100 bar; Temp. 20° C.; Wavelength 220 nm) to provide the title compound (14.5 mg, second eluting peak) as a white solid. m/z (ESI, +ve ion) 496.3 (M+H)$^+$.

Step 3: (S)—N-(allylsulfonyl)-6'-chloro-5-(((1R,2S)-2-((S)-2-hydroxypent-4-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2S)-2-((R)-2-hydroxypent-4-en-1-yl)cyclobutyl)methyl)-3',4,4',5-tetrahydro-2H,2'H-spiro[benzo[b][1,4]oxazepine-3,1'-naphthalene]-7-carboxamide

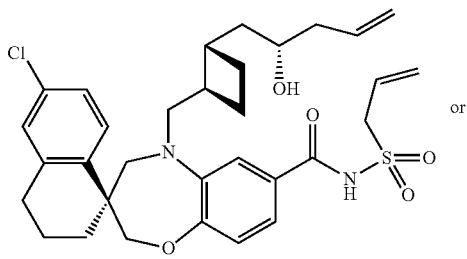

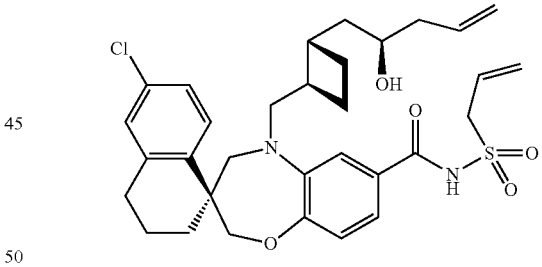

N,N-Dimethylpyridin-4-amine (DMAP) (9 mg, 0.07 mmol) was added to a solution of (S)-6'-chloro-5-(((1R,2S)-2-((S)-2-hydroxypent-4-en-1-yl)cyclobutyl)methyl)-3',4,4',5-tetrahydro-2H,2'H-spiro[benzo[b][1,4]oxazepine-3,1'-naphthalene]-7-carboxylic acid (Example 911, Step 2; 0.012 g, 0.024 mmol) and prop-2-ene-1-sulfonamide (Example 900, Step 5; 0.013 g, 0.109 mmol) in DCM (0.9 mL) at 0° C. Then N-(3-dimethylaminopropyl)-N'-ethylcarbodiimide hydrochloride (EDC, 9 mg, 0.047 mmol) was added portion by portion and it was stirred at rt for 16 h. After it was concentrated the residue was purified by reverse phase preparative HPLC (Gemini™ Prep C$_{18}$ 5 µm column; Phenomenex, Torrance, CA; MeCN in water with 0.1% TFA, gradient elution) to provide the title compound (5.7 mg) as a white solid. m/z (ESI, +ve ion) 599.3 (M+H)$^+$.

Step 4: (1S,3'R,6'S,8'S,10'Z)-6-chloro-8'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa [10,16,18,24]tetraen]-15'-one 13',13'-dioxide or (1S,3'R,6'S,8'S,10'Z)-6-chloro-8'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa [10,16,18,24]tetraen]-15'-one 13',13'-dioxide

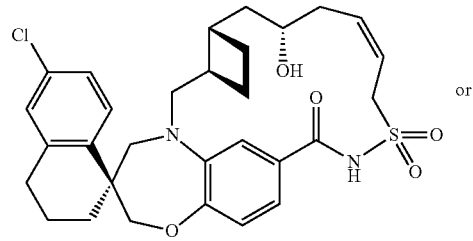

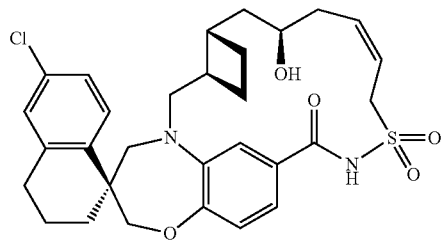

A 250 mL round bottom flask was charged with (S)—N-(allylsulfonyl)-6'-chloro-5-(((1R,2S)-2-((S)-2-hydroxypent-4-en-1-yl)cyclobutyl)methyl)-3',4,4',5-tetrahydro-2H,2'H-spiro[benzo[b][1,4]oxazepine-3,1'-naphthalene]-7-carboxamide (Example 911, Step 3; 5.7 mg, 9.5 µmol) in toluene (43 mL). It was stirred at rt for 10 min to dissolve the solid starting material and then subjected to three cycles of evacuation/back-filling with nitrogen. To the homogeneous solution was added a solution of Hoveyda-Grubbs II (1.2 mg, 1.9 µmol) in toluene (3 mL). The mixture was stirred at 106° C. under nitrogen for 1 h. After it was concentrated the residue was purified by reverse phase preparative HPLC (Gemini™ Prep C₁₈ 5 µm column; Phenomenex, Torrance, CA; MeCN in water with 0.1% TFA, gradient elution). The title compound (1.1 mg, first eluting peak) was obtained as a white solid. ¹H NMR (400 MHz, CD₂Cl₂) δ 8.11 (m, 1H), 7.68 (m, 1H), 7.19 (m, 1H), 7.15 (m, 1H), 7.08 (m, 1H), 6.89 (m, 1H), 5.94 (dd, J=8.02, 18.78 Hz, 1H), 5.58 (m, 1H), 4.56 (br. s., 1H), 4.11 (m, 2H), 3.61 (d, J=14.09 Hz, 2H), 3.51 (br. s., 1H), 3.31 (d, J=14.87 Hz, 1H), 3.24 (br. s., 1H), 2.79-2.70 (m, 2H), 2.27-2.15 (m, 3H), 2.09 (dd, J=7.04, 13.69 Hz, 1H), 2.02-1.95 (m, 2H), 1.89-1.77 (m, 2H), 1.73-1.04 (m, 8H). m/z (ESI, +ve ion) 571.1 (M+H)⁺.

Example 912. (1S,3'R,6'S,8'R,10'E)-6-chloro-8'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa [10,16,18,24]tetraen]-15'-one 13',13'-dioxide or (1S,3'R,6'S,8'S,10'E)-6-chloro-8'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa [10,16,18,24]tetraen]-15'-one 13',13'-dioxide

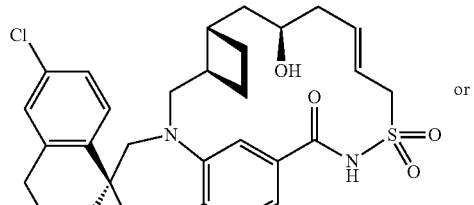

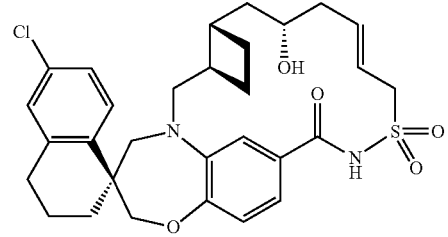

The title compound (2.5 mg) was obtained as a single isomer (second eluting peak) from the reverse phase preparative HPLC in Example 911 as a white solid. ¹H NMR (400 MHz, CD₂Cl₂) δ 8.37 (br. s., 1H), 7.71 (m, 1H), 7.18 (dd, J=2.35, 8.41 Hz, 1H), 7.06-7.13 (m, 2H), 6.95 (d, J=8.22 Hz, 1H), 6.89 (m, 1H), 5.79-5.89 (m, 1H), 5.66 (ddd, J=6.06, 8.80, 15.26 Hz, 1H), 4.22 (dd, J=8.61, 14.48 Hz, 1H), 4.13-4.01 (m, 3H), 3.84 (d, J=16.24 Hz, 1H), 3.73 (d, J=13.89 Hz, 1H), 3.62-3.69 (m, 1H), 3.26-3.15 (m, 2H), 2.81-2.71 (m, 2H), 2.30-2.18 (m, 3H), 2.15-1.18 (m, 12H). m/z (ESI, +ve ion) 571.1 (M+H)⁺.

Example 913. (1S,3'R,6'S,8'R,10'E)-6-chloro-8'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa [10,16,18,24]tetraen]-15'-one 13',13'-dioxide or (1S,3'R,6'S,8'S,10'E)-6-chloro-8'-hydroxy-3,4-dihydro-2H,15'Hspiro [naphthalene-1,22'-[20]oxa[13]thia[1,14]diazatetracyclo[14.7.2.0³,⁶.0¹⁹,²⁴]pentacosa [10,16,18, 24]tetraen]-15'-one 13',13'-dioxide

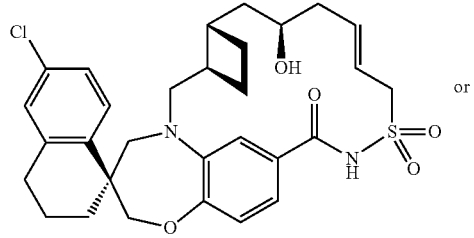

-continued

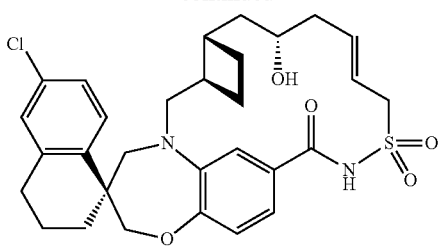

Step 1: (S)-6'-chloro-5-(((1R,2S)-2-((S)-2-hydroxy-pent-4-en-1-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2S)-2-((R)-2-hydroxypent-4-en-1-yl)cyclobutyl)methyl)-3',4,4',5-tetrahydro-2H,2'H-spiro[benzo[b][1,4]oxazepine-3,1'-naphthalene]-7-carboxylic Acid

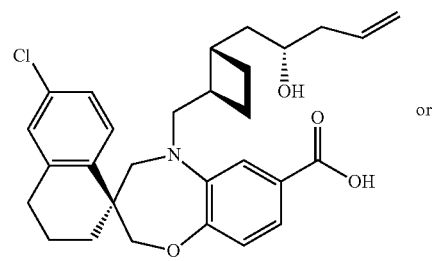

or

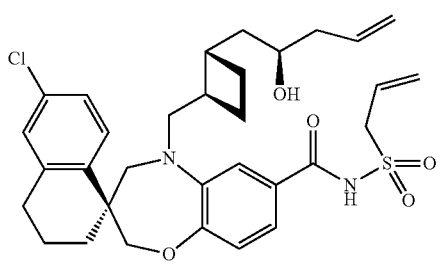

The title compound (11 mg) was obtained as a single isomer (first eluting peak) from the reverse phase preparative HPLC in Example 911, Step 2 as a white solid. m/z (ESI, +ve ion) 496.3 (M+H)+.

Step 2: (S)—N-(allylsulfonyl)-6'-chloro-5-(((1R,2S)-2-((S)-2-hydroxypent-4-en-1-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2S)-2-((R)-2-hydroxypent-4-en-1-yl)cyclobutyl)methyl)-3',4,4',5-tetrahydro-2H,2'H-spiro[benzo[b][1,4]oxazepine-3,1'-naphthalene]-7-carboxamide

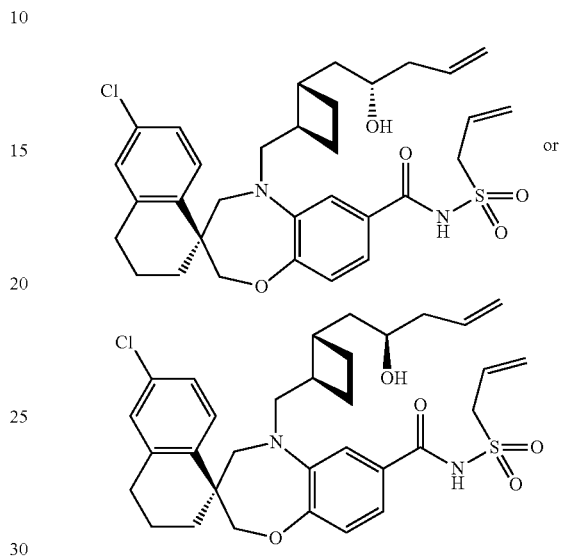

N,N-Dimethylpyridin-4-amine (DMAP) (9 mg, 0.07 mmol) was added to a solution of (S)-6'-chloro-5-(((1R,2S)-2-((S)-2-hydroxypent-4-en-1-yl)cyclobutyl)methyl)-3',4,4',5-tetrahydro-2H,2'H-spiro[benzo[b][1,4]oxazepine-3,1'-naphthalene]-7-carboxylic acid (Example 913, Step 1; 0.012 g, 0.024 mmol) and prop-2-ene-1-sulfonamide (Example 900, Step 5; 0.013 g, 0.109 mmol) in DCM (0.9 mL) at 0° C. Then N-(3-dimethylaminopropyl)-N'-ethylcarbodiimide hydrochloride (EDC, 9 mg, 0.047 mmol) was added portion by portion and it was stirred at rt for 16 h. After it was concentrated the residue was purified by reverse phase preparative HPLC (Gemini™ Prep C$_{18}$ 5 μm column; Phenomenex, Torrance, CA; MeCN in water with 0.1% TFA, gradient elution) to provide the title compound (5.7 mg) as a white solid. m/z (ESI, +ve ion) 599.3 (M+H)+.

Step 3: (1S,3'R,6'S,8'R,10'E)-6-chloro-8'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[10,16,18,24]tetraen]-15'-one 13',13'-dioxide or (1S,3'R,6'S,8'S,10'E)-6-chloro-8'-hydroxy-3,4-dihydro-2H,15'Hspiro[naphthalene-1,22'-[20]oxa[13]thia[1,14]diazatetracyclo[14.7.2.0$^{3,6}$.0$^{19,24}$]pentacosa[10,16,18,24]tetraen]-15'-one 13',13'-dioxide

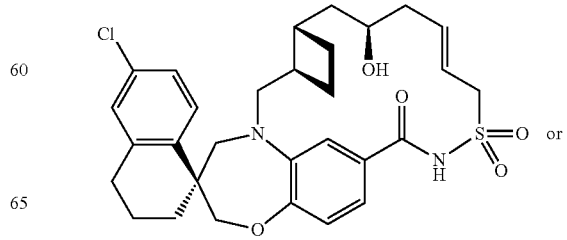 or

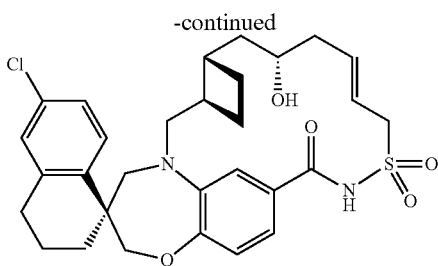

A 250 mL round bottom flask was charged with (S)—N-(allylsulfonyl)-6'-chloro-5-((((1R,2S)-2-((S)-2-hydroxypent-4-en-1-yl)cyclobutyl)methyl)-3',4,4',5-tetrahydro-2H,2'H-spiro[benzo[b][1,4]oxazepine-3,1'-naphthalene]-7-carboxamide (Example 913, Step 2; 5.7 mg, 9.5 μmol) in toluene (43 mL). It was stirred at rt for 10 min to dissolve the solid starting material and then subjected to three cycles of evacuation/back-filling with nitrogen. To the homogeneous solution was added a solution of Hoveyda-Grubbs II (1.2 mg, 1.9 μmol) in toluene (3 mL). The mixture was stirred at 106° C. under nitrogen for 1 h. After it was concentrated the residue was purified by reverse phase preparative HPLC (Gemini™ Prep $C_{18}$ 5 μm column; Phenomenex, Torrance, CA; MeCN in water with 0.1% TFA, gradient elution) to provide the title compound (1.1 mg, second eluting peak) as a white solid. $^1$H NMR (400 MHz, $CD_2Cl_2$) δ 8.46 (br. s., 1H), 7.69 (d, J=8.41 Hz, 1H), 7.16 (dd, J=2.45, 8.51 Hz, 1H), 7.13-7.06 (m, 2H), 6.98-6.90 (m, 2H), 5.95 (td, J=7.31, 15.50 Hz, 1H), 5.70-5.60 (m, 1H), 4.27 (dd, J=8.90, 14.77 Hz, 1H), 4.15-4.04 (m, 3H), 3.78 (d, J=10.96 Hz, 1H), 3.71-3.61 (m, 2H), 3.30-3.18 (m, 2H), 2.81-2.73 (m, 2H), 2.52-1.19 (m, 15H). m/z (ESI, +ve ion) 571.1 (M+H)$^+$.

Example 914. (1S,3'R,6'S,8'R,10'Z)-6-chloro-8'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [10,16,18,24]tetraen]-15'-one 13',13'-dioxide or (1S,3'R,6'S,8'S,10'Z)-6-chloro-8'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [10,16,18,24]tetraen]-15'-one 13',13'-dioxide

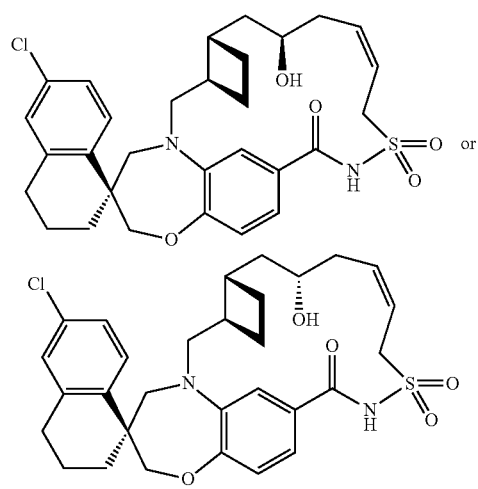

The title compound (1.8 mg) was obtained as a single isomer (first eluting peak) from the reverse phase preprartive HPLC in Example 913 as a white solid. $^1$H NMR (400 MHz, $CD_2Cl_2$) δ 8.24 (br. s., 1H), 7.71 (d, J=8.41 Hz, 1H), 7.17 (dd, J=2.45, 8.51 Hz, 1H), 7.09 (s, 2H), 6.95-7.01 (m, 1H), 6.90 (m, 1H), 5.84 (m, 1H), 5.67-5.58 (m, 1H), 4.87-4.77 (m, 1H), 4.14-4.06 (m, 2H), 3.87 (d, J=15.06 Hz, 1H), 3.82-3.65 (m, 3H), 3.21 (d, J=14.09 Hz, 1H), 3.09-3.02 (m, 1H), 2.82-2.73 (m, 2H), 2.40-1.03 (m, 16H). m/z (ESI, +ve ion) 571.1 (M+H)$^+$.

Example 915. (1S,3'R,6'R,8'E,12'R)-6-chloro-12'-ethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [8,16,18,24]tetraene]-7',15'-dione 13',13'-dioxide

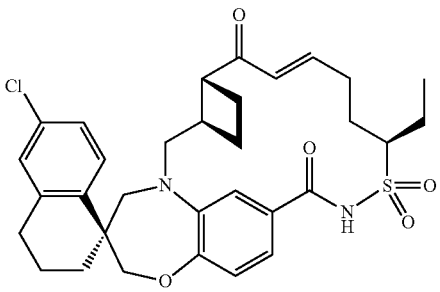

To a solution of Example 422, Step 1 (0.100 g, 0.167 mmol) in DCM (3.3 mL) was added slowly Dess-Martin periodinane (0.085 g, 0.200 mmol) in DCM (3.3 mL). It was stirred at rt for 10 min. The reaction was quenched with water (4 mL) and extracted with EtOAc (200 mL). The organic phase was washed with brine, dried over anhydrous sodium sulfate and concentrated. The residue was loaded to a 12 g ISCO Gold column and eluted with 0% to 25% EtOAc (containing 0.3% AcOH)/hexane (containing 0.3% AcOH) to provide the title compound (70 mg) as a white solid. $^1$H NMR (500 MHz, $CD_2Cl_2$) δ 8.14 (br. s., 1H), 7.76 (m, 1H), 7.25 (d, J=1.71 Hz, 1H), 7.20 (dd, J=2.32, 8.44 Hz, 1H), 7.10 (d, J=2.20 Hz, 1H), 6.88-6.77 (m, 2H), 6.63 (td, J=7.82, 15.65 Hz, 1H), 5.94 (d, J=15.89 Hz, 1H), 4.13-4.03 (m, 2H), 3.92-3.82 (m, 2H), 3.79-3.66 (m, 2H), 3.26 (d, J=14.43 Hz, 1H), 3.03-2.95 (m, 2H), 2.82-2.69 (m, 2H), 2.41-2.32 (m, 1H), 2.21-2.06 (m, 3H), 2.04-1.96 (m, 3H), 1.94-1.68 (m, 6H), 1.44-1.35 (m, 1H), 1.23-1.17 (m, 3H). m/z (ESI, +ve ion) 597.1 (M+H)$^+$.

Example 917. (3R,6R,7S,11E,22S)-6'-chloro-7-hydroxy-3',4'-dihydro-2'H,15H-spiro[9,20-dioxa-13-thia-1,14-diazatetracyclo[14.7.2.0³,⁶.0¹⁹,²⁴]pentacosa-11,16,18,24-tetraene-22,1'-naphthalen]-15-one 13,13-dioxide or (3R,6R,7R,11E, 22S)-6'-chloro-7-hydroxy-3',4'-dihydro-2'H,15H-spiro[9,20-dioxa-13-thia-1,14-diazatetracyclo[14.7.2.0³,⁶.0¹⁹,²⁴]pentacosa-11,16,18,24-tetraene-22,1'-naphthalen]-15-one 13,13-dioxide

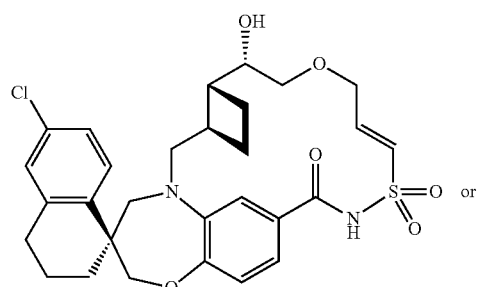

or

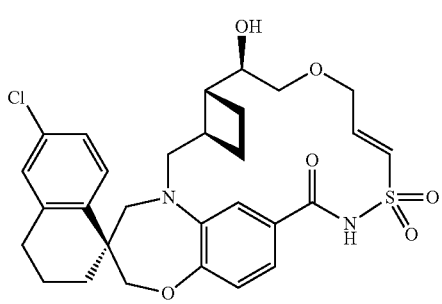

Step 1: (S)-tert-butyl 6'-chloro-5-(((1R,2R)-2-((R)-1,2-dihydroxyethyl)cyclo-butyl)methyl)-3',4,4',5-tetrahydro-2H,2'H-spiro[benzo[b][1,4]oxazepine-3,1'-NAPTHALENE]-7-carboxylate or (S)-tert-butyl 6'-chloro-5-(((1R,2R)-2-((S)-1,2-dihydroxyethyl) cyclobutyl)methyl)-3',4,4',5-tetrahydro-2H,2'H-spiro [benzo[b][1,4]oxazepine-3,1'-naphthalene]-7-carboxylate


or

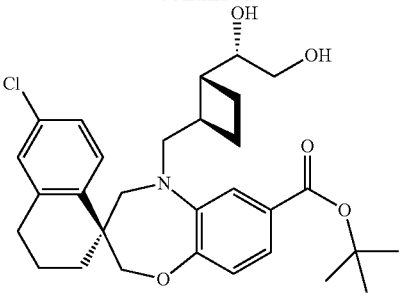

The title compound was obtained as the second eluting peak in Example 863, Step 2.

Step 2: (S)-tert-butyl 5-(((1R,2R)-2-((S)-2-(allyloxy)-1-hydroxyethyl)cyclobutyl)methyl)-6'-chloro-3',4,4',5-tetrahydro-2H,2'H-spiro[benzo[b][1,4] oxazepine-3,1'-naphthalene]-7-carboxylate or (S)-tert-butyl 5-(((1S,2R)-2-((S)-2-(allyloxy)-1-hydroxyethyl)cyclobutyl)methyl)-6'-chloro-3',4,4',5-tetrahydro-2H,2'H-spiro[benzo[b][1,4]oxazepine-3, 1'-naphthalene]-7-carboxylate

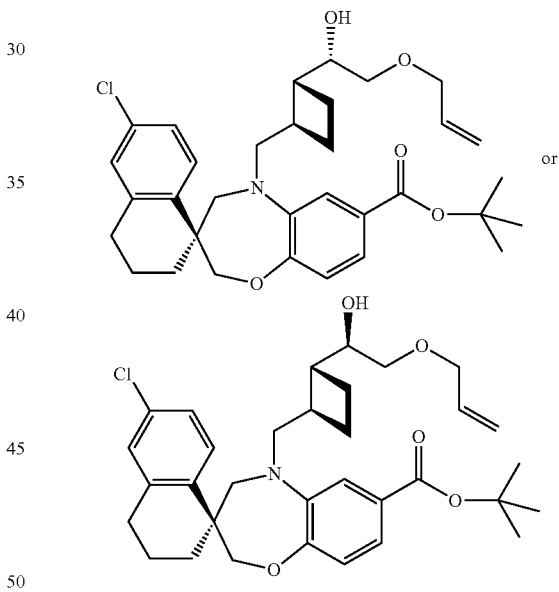

Sodium hydride (60% dispersion in mineral oil, 8.77 µl, 0.417 mmol) was added to a solution of (S)-tert-butyl 6'-chloro-5-(((1R,2R)-2-((S)-1,2-dihydroxyethyl)cyclobutyl)methyl)-3',4,4',5-tetrahydro-2H,2'H-spiro[benzo [b][1,4]oxazepine-3,1'-naphthalene]-7-carboxylate (Example 917, Step 1; 0.100 g, 0.189 mmol) in DMF (6 mL). After it was stirred at 0° C. for 20 min, allyl iodide (0.024 mL, 0.265 mmol) in DMF (0.7 mL) was added dropwise and it was stirred at 0° C. to rt for 2 h. The reaction mixture was quenched with water (2 mL) and extracted with EtOAc (200 mL). The organic phase was washed with brine, dried over anhydrous sodium sulfate and concentrated. The residue was loaded to a 40 g ISCO Gold column and eluted with 0% to 30% EtOAc (containing 0.3% AcOH)/hexane (containing 0.3% AcOH) to provide the title compound (47.6 mg) as an oil; m/z (ESI, +ve ion) 568.3 (M+H)⁺.

Step 3: (S)-6'-chloro-5-(((1R,2R)-2-((S)-1-hydroxy-2-(((E)-3-sulfamoylallyl)oxy)ethyl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((R)-1-hydroxy-2-(((E)-3-sulfamoylallyl)oxy)ethyl)cyclobutyl)methyl)-3',4,4',5-tetrahydro-2H,2'H-spiro[benzo[b][1,4]oxazepine-3,1'-naphthalene]-7-carboxylic Acid Step 4: (3R,6R,7S,11E,22S)-6'-chloro-7-hydroxy-3',4'-dihydro-2'H,15H-spiro[9,20-dioxa-13-thia-1,14-diazatetracyclo[14.7.2.0$^{3,6}$.0$^{19,24}$]pentacosa-11,16,18,24-tetraene-22,1'-naphthalen]-15-one 13,13-dioxide or (3R,6R,7R,11E,22S)-6'-chloro-7-hydroxy-3',4'-dihydro-2'H,15H-spiro[9,20-dioxa-13-thia-1,14-diazatetracyclo[14.7.2.0$^{3,6}$.0$^{19,24}$]pentacosa-11,16,18,24-tetraene-22,1'-naphthalen]-15-one 13,13-dioxide

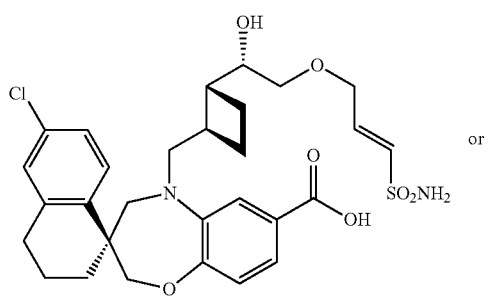

or

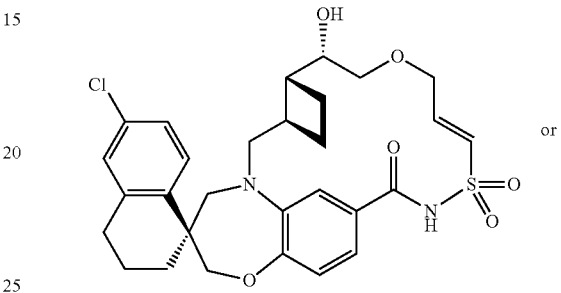

or

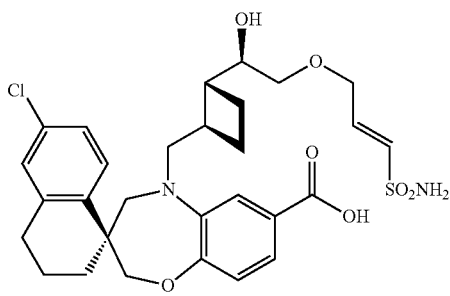

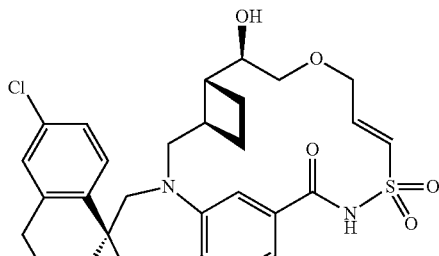

A flask was charged with (S)-tert-butyl 5-(((1R,2R)-2-((S)-2-(allyloxy)-1-hydroxyethyl)cyclobutyl)methyl)-6'-chloro-3',4,4',5-tetrahydro-2H,2'H-spiro[benzo[b][1,4]oxazepine-3,1'-naphthalene]-7-carboxylate (Example 917, Step 2; 0.020 g, 0.035 mmol) and N,N-bis(4-methoxybenzyl)ethenesulfonamide (Example 831, Step 2; 0.073 g, 0.211 mmol) in 1,2-dichloroethane (1.8 mL). It was stirred at rt for 10 min to dissolve the solid starting material and then degassed with nitrogen. To the homogeneous solution was added a solution of Hoveyda-Grubbs II (6 mg, 7 µmol) in DCM (1 mL) and it was stirred at 55° C. for 2 h. It was concentrated and the residue was dissolved in cold TFA and DCM (TFA/DCM:1:3, 2 mL) and stirred at rt for 19 h. After concentration, the residue was purified by reverse phase preparative HPLC (Gemini™ Prep C$_{18}$ 5 µm column; Phenomenex, Torrance, CA; MeCN in water with 0.1% TFA, gradient elution) to give the title compound (4.4 mg) as a film. m/z (ESI, +ve ion) 591.1 (M+H)$^{+}$.

4-Dimethylaminopyridine (DMAP) (9.1 mg, 0.074 mmol) was added to a solution of (S)-6'-chloro-5-(((1R,2R)-2-((S)-1-hydroxy-2-(((E)-3-sulfamoylallyl)oxy)ethyl)cyclobutyl)methyl)-3',4,4',5-tetrahydro-2H,2'H-spiro[benzo[b][1,4]oxazepine-3,1'-naphthalene]-7-carboxylic acid (Example 917, Step 3; 0.0044 g, 7.44 µmol) in DCM (20 mL), which was cooled by ice bath. Then N-(3-dimethylaminopropyl)-N'-ethylcarbodiimide hydrochloride (EDC, 10 mg, 0.052 mmol) was added and it was stirred at 0° C. to rt for 18 h. After concentration, the residue was purified by reverse phase preparative HPLC (Gemini™ Prep C$_{18}$ 5 µm column; Phenomenex, Torrance, CA; MeCN in water with 0.1% TFA, gradient elution) to give the title compound (1.6 mg) as a film. $^1$H NMR (500 MHz, CD$_2$Cl$_2$) δ 8.26 (br. s., 1H), 7.70 (d, J=8.31 Hz, 1H), 7.17 (dd, J=2.32, 8.44 Hz, 1H), 7.14-7.04 (m, 3H), 6.91 (m, 1H), 6.85 (m, 1H), 6.67 (d, J=15.41 Hz, 1H), 4.44 (ddd, J=1.71, 3.79, 15.28 Hz, 1H), 4.09 (s, 2H), 3.93 (d, J=15.41 Hz, 1H), 3.85-3.79 (m, 1H), 3.70-3.62 (m, 1H), 3.49 (dd, J=1.47, 9.05 Hz, 1H), 3.42 (s, 1H), 3.36-3.28 (m, 1H), 3.24-3.17 (m, 1H), 3.04 (dd, J=8.56, 15.41 Hz, 1H), 2.79-2.71 (m, 2H), 2.42-2.28 (m, 2H), 2.07-1.43 (m, 9H). m/z (ESI, +ve ion) 573.0 (M+H)$^{+}$.

Example 918. (3R,6R,7S,11S,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide or (3R,6R,7R,11S,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide or (3R,6R,7R,11R,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide or (3R,6R,7S,11R,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide

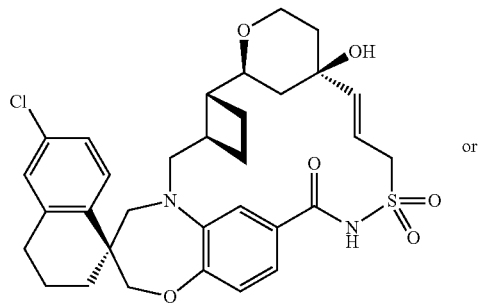

or

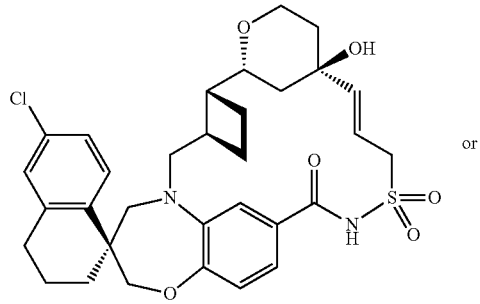

or

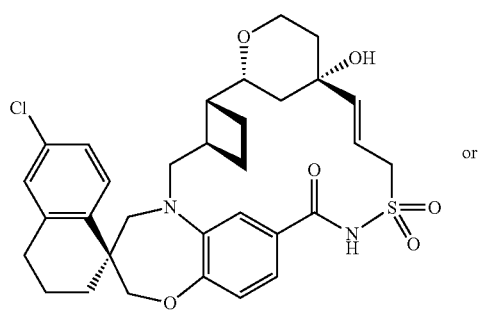

or

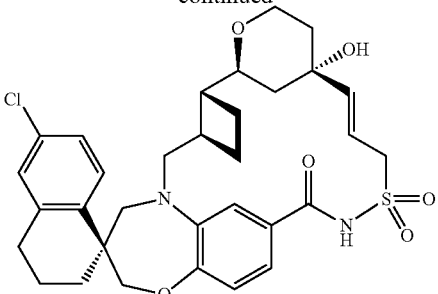

Step 1: (S)-methyl 6'-chloro-5-(((1R,2R)-2-((2S,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

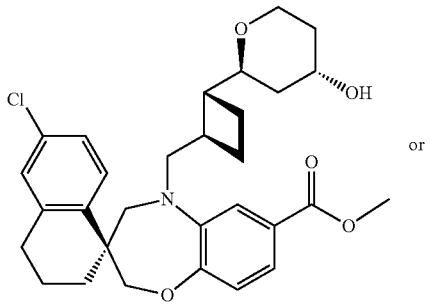

or

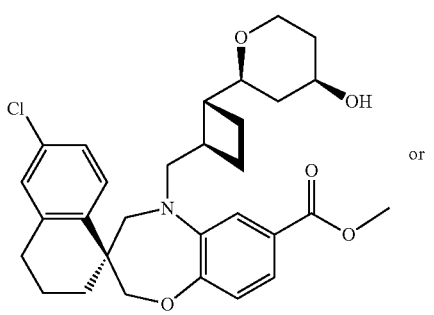

or

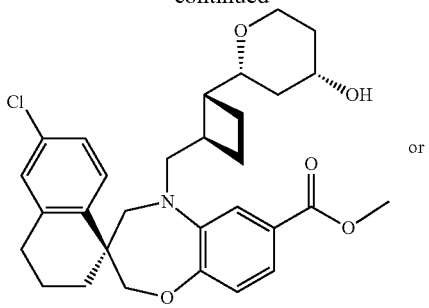

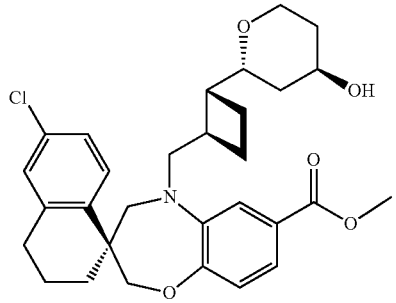

TFA (6 mL) was added slowly to a solution of (S)-methyl 6'-chloro-5-(((1R,2R)-2-formyl cyclobutyl)methyl)-3',4,4',5-tetrahydro-2H,2'H-spiro[benzo[b][1,4]oxazepine-3,1'-naphthalene]-7-carboxylate (Intermediate AA11A, Step 20A; 0.412 g, 0.908 mmol) and 3-buten-1-ol (0.10 mL, 1.18 mmol) in DCM (12 mL) which was degassed with N₂. It was stirred at rt for 35 min. The reaction mixture was added slowly to Na₂CO₃ (aq) solution (50 mL) and MeOH (15 mL). After the mixture was stirred at rt for 83 min, it was extracted with EtOAc (3×90 mL). The combined organic phases were dried over anhydrous sodium sulfate and concentrated. The residue was purified by SFC (Method: 250× 21.2 mm IC—H column w/ 20 g/min MeOH (0.2% DEA)+ 60 g/min CO₂ on a Thar 80 SFC. Outlet pressure 100 bar; Temp. 20° C.; Wavelength 220 nm). The title compound (102 mg, second eluting peak) was obtained as a white solid. m/z (ESI, +ve ion) 526.1 (M+H)⁺.

Step 2: (S)-methyl 6'-chloro-5-(((1R,2R)-2-((S)-4-oxotetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((R)-4-oxotetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

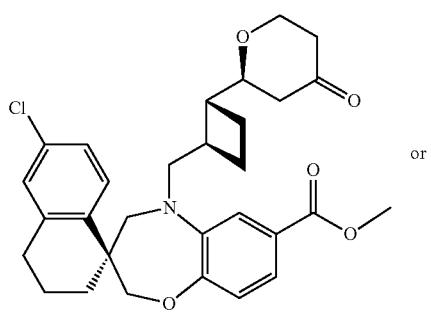

or

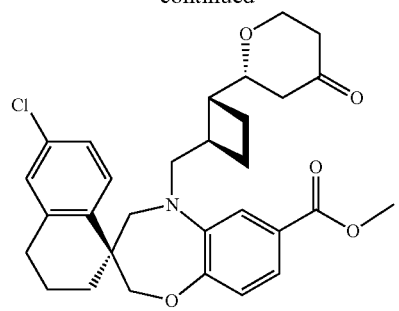

A 50 mL flask was charged with dimethyl sulfoxide (0.051 mL, 0.724 mmol) and DCM (3.5 mL) was cooled to −78° C. Oxalyl chloride (2.0 M solution in DCM, 0.18 mL, 0.36 mmol) was added dropwise slowly and the reaction stirred for 15 min. (S)-Methyl 6'-chloro-5-(((1R,2R)-2-((2R,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 918, Step 1; 0.127 g, 0.241 mmol) in DCM (3.5 mL) was added in one portion to above solution. It was stirred at −78° C. for 20 min. Then triethylamine (0.17 mL, 1.2 mmol) was added and it was stirred at −78° C. to rt for 2 h. The mixture was quenched with water (3 mL) and extracted with EtOAc (130 mL). The organic phase was washed with 1N HCl solution (2 mL), brine and dried over anhydrous sodium sulfate. It was filtered through silica gel to provide the title compound (126 mg) as a white solid. m/z (ESI, +ve ion) 524.1 (M+H)⁺.

Step 3: (S)-methyl 6'-chloro-5-(((1R,2R)-2-((2S,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

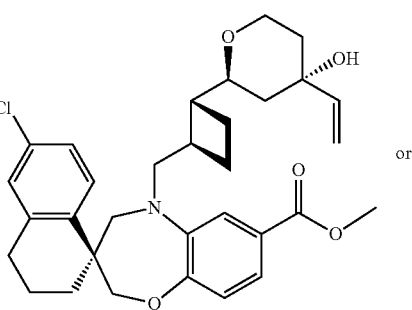

or

-continued

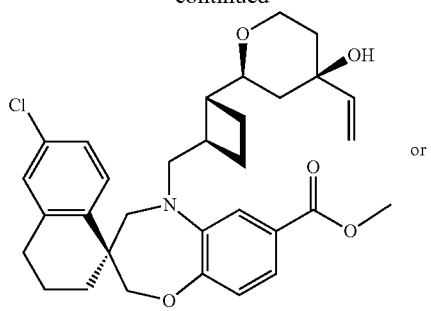

or

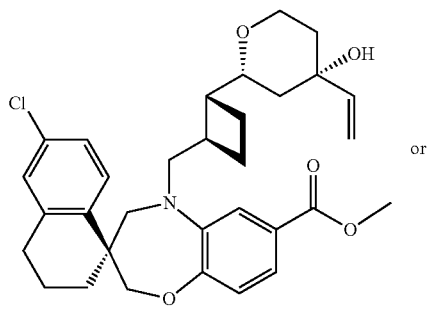

or

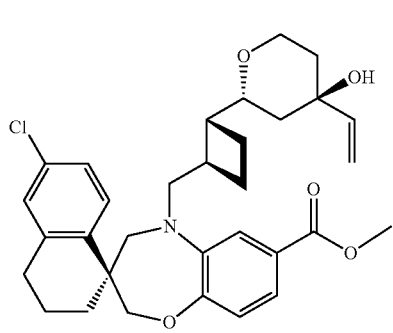

Step 4: (S)-6'-chloro-5-(((1R,2R)-2-((2S,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((2R,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid

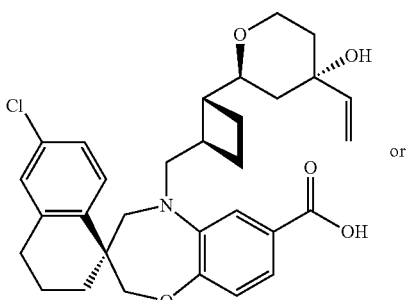

or

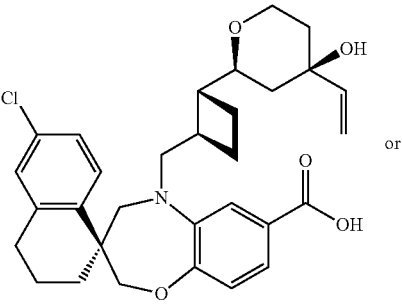

or

Vinylmagnesium chloride (1.6 M solution in tetrahydrofuran, 0.50 mL, 0.79 mmol) was added dropwise to a solution of (S)-methyl 6'-chloro-5-(((1R,2R)-2-((R)-4-oxotetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 918, Step 2; 0.126 g, 0.240 mmol) in THF (8 mL) at 0° C. After it was stirred at 0° C. for 20 min, it was quenched with NH$_4$Cl solution and extracted with EtOAc (180 mL). The organic phase was washed with brine, dried over anhydrous sodium sulfate, filtered through short plug of silica gel to provide the title compound (133 mg) as an oil. m/z (ESI, +ve ion) 552.1 (M+H)$^+$.

1873
-continued

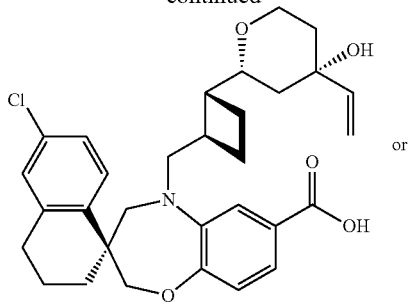

or

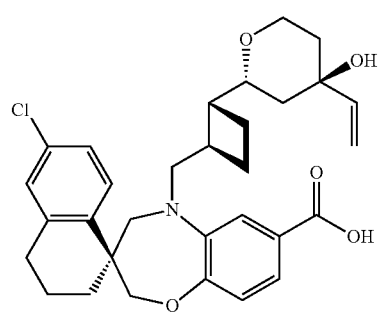

Lithium hydroxide (1.0 M solution, 7.2 mL, 7.2 mmol) was added to a solution of (1'S)-methyl 6'-chloro-5-(((1R,2R)-2-((2R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 918, Step 3; 0.133 g, 0.241 mmol) in THF (16 mL) and MeOH (8 mL). It was stirred at 50° C. for 3 h. The reaction mixture was concentrated, acidified with 1N HCl solution to pH 2-4, extracted with EtOAc (150 mL). The organic phase was washed with brine, dried over anhydrous sodium sulfate. After it was concentrated the residue was purified by reverse phase preparative HPLC (Gemini™ Prep C$_{18}$ 5 µm column; Phenomenex, Torrance, CA; MeCN in water with 0.1% TFA, gradient elution) to provide the title compound (50 mg, second eluting peak) as a white solid. m/z (ESI, +ve ion) 538.1 (M+H)$^+$.

1874

Step 5: (S)—N-(allylsulfonyl)-6'-chloro-5-(((1R,2R)-2-((2S,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide or (S)—N-(allylsulfonyl)-6'-chloro-5-(((1R,2R)-2-((2R,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide

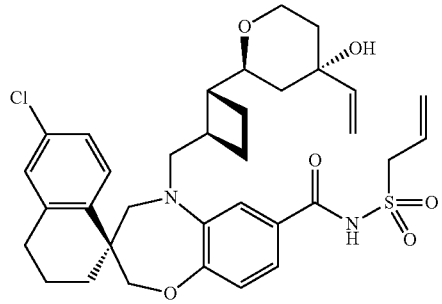

or

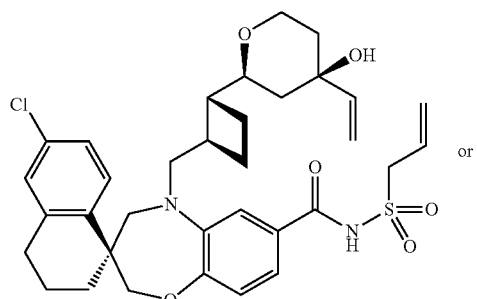

or

-continued

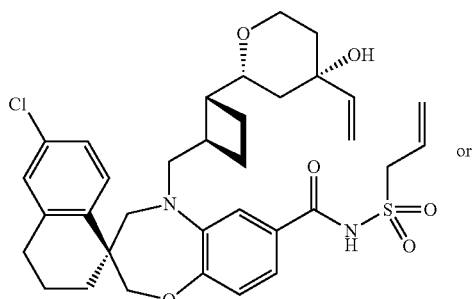

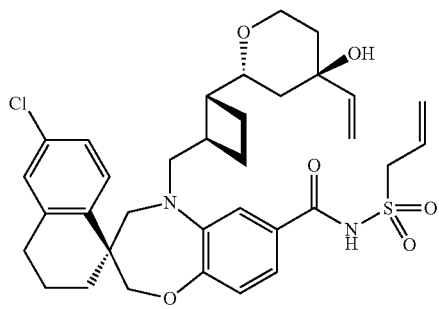

N,N-Dimethylpyridin-4-amine (DMAP) (0.016 g, 0.13 mmol) was added to a solution of (S)-6'-chloro-5-(((1R,2R)-2-((2R,4S)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic acid (Example 918, Step 4; 0.023 g, 0.043 mmol) and prop-2-ene-1-sulfonamide (Example 900, Step 5; 0.020 g, 0.17 mmol) in DCM (1.4 mL) at 0° C. Then N1-((ethylimino)methylene)-N3,N3-dimethylpropane-1,3-diamine hydrochloride (EDC) (0.017 g, 0.090 mmol) was added in portions and it was stirred at 0° C. to rt for 3 days. After it was concentrated the residue was purified by reverse phase preparative HPLC (Gemini™ Prep $C_{18}$ 5 µm column; Phenomenex, Torrance, CA; MeCN in water with 0.1% TFA, gradient elution) to provide the title compound (5.2 mg) as a white solid. m/z (ESI, +ve ion) 641.1 (M+H)⁺.

Step 6: (3R,6R,7S,11S,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide or (3R,6R,7R,11S,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide or (3R,6R,7R,11R,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide or (3R,6R,7S,11R,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide A 250 mL round bottom flask was charged with (S)—N-(allylsulfonyl)-6'-chloro-5-(((1R,2R)-2-((2S,4R)-4-hydroxy-4-vinyltetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxamide (Example 918, Step 5; 5.2 mg, 8.1 µmol) in toluene (17 mL). It was stirred at rt for 10 min to dissolve the solid starting material and then subjected to three cycles of evacuation/back-filling with nitrogen. To the homogeneous solution was added a solution of Hoveyda-Grubbs II (1 mg, 1.6 µmol) in toluene (3 mL). The mixture was stirred at 106° C. under nitrogen for 1 h. After it was concentrated the residue was purified by reverse phase preparative HPLC (Gemini™ Prep $C_{18}$ 5 µm column; Phenomenex, Torrance, CA; MeCN in water with 0.1% TFA, gradient elution) to provide the title compound (3 mg) as a white solid. $^1$H NMR (500 MHz, CD$_2$Cl$_2$) δ 8.10 (s, 1H), 7.69 (d, J=8.56 Hz, 1H), 7.17 (m, 1H), 7.08 (d, J=2.20 Hz, 1H), 6.92 (m, 2H), 6.81 (s, 1H), 6.00-5.92 (m, 1H), 5.83 (ddd, J=5.87, 8.93, 15.04 Hz, 1H), 4.30 (dd, J=8.68, 14.06 Hz, 1H), 4.26-4.16 (m, 1H), 4.12-4.05 (m, 2H), 3.97 (d, J=12.23 Hz, 1H), 3.86-3.70 (m, 4H), 3.62-3.54 (m, 1H), 3.22-3.14 (m, 2H), 2.83-2.71 (m, 2H), 2.24-1.55 (m, 11H), 1.47-1.41 (m, 1H), 1.41-1.33 (m, 2H). m/z (ESI, +ve ion) 613.0 (M+H)⁺.

Example 919. (1S,3'R,6'R,7'S,11'S,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,1]'S,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'R,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'R,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'S,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'S,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'R,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'S,13'S)-6-chloro-13'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'S,14'S)-6-chloro-14'-methyl-3,4-dihydro-2H,17'H-spiro[naphthalene-1,24'-[8,12,22]trioxa[15]thia[1,16]diazapentacyclo [16.7.2.1$^{7,11}$.0$^{3,6}$.0$^{21,26}$]octacosa[18,20,26]trien]-17'-one 15',15'-dioxide or (1S,3'R,6'R,7'S,11'S,14'R)-6-chloro-14'-methyl-3,4-dihydro-2H,17'H-spiro [naphthalene-1,24'-[8,12,22]trioxa[15]thia[1,16]diazapentacyclo[16.7.2.1$^{7,11}$~0$^{3,6}$.0$^{21,26}$]octacosa[18,20,26]trien]-17'-one 15',15'-dioxide or (1S,3'R,6'R,7'R,11'R,14'S)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'R,14'R)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$~0$^{3,6}$.0$^{21,26}$]octacosa[18,20,26]trien]-17'-one 15',15'-dioxide or (1S,3'R,6'R,7'R,11'S,14'S)-6-chloro-14'-methyl-3,4-dihydro-2H,17'H-spiro [naphthalene-1,24'-[8,12,22]trioxa[15]thia[1,16]diazapentacyclo [16.7.2.1$^{7,11}$.0$^{3,6}$.0$^{21,26}$]octacosa[18,20,26]trien]-17'-one 15',15'-dioxide or (1S,3'R,6'R,7'R,11'S,14'R)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'R,14'S)-6-chloro-14'-methyl-3,4-dihydro-2H,17'H-spiro[naphthalene-1,24'-[8,12,22]trioxa[15]thia[1,16]diazapentacyclo [16.7.2.1$^{7,11}$.0$^{3,6}$.0$^{21,26}$]octacosa[18,20,26]trien]-17'-one 15',15'-dioxide or (1S,3'R,6'R,7'S,11'R,14'R)-6-chloro-14'-methyl-3,4-dihydro-2H,17'H-spiro[naphthalene-1,24'-[8,12,22]trioxa[15]thia[1,16]diazapentacyclo

[16.7.2.1$^{7,11}$.0$^{3,6}$.0$^{21,26}$]octacosa[18,20,26]trien]-17'-one 15',15'-dioxide

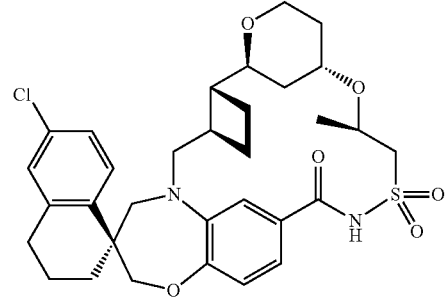

or

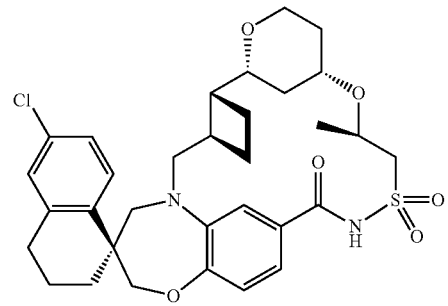

or

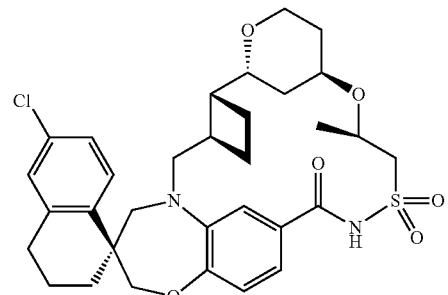

or

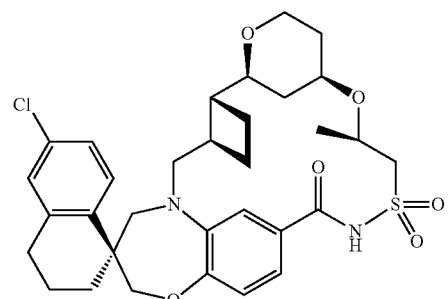

or

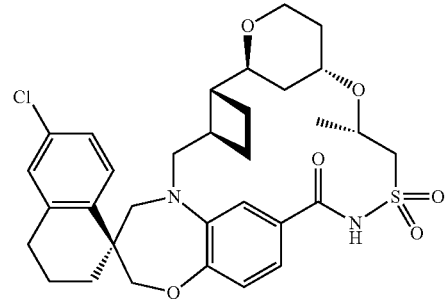

or

1879
-continued
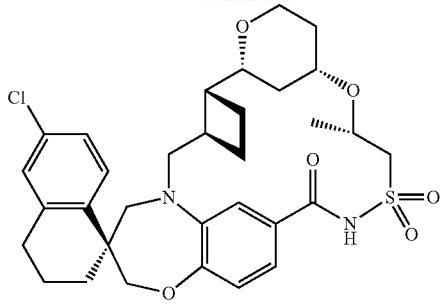
or
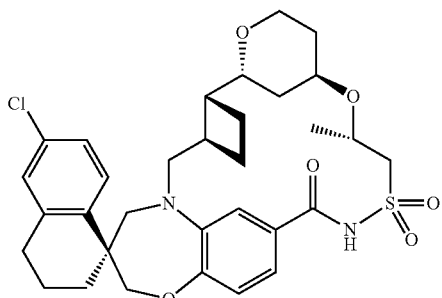
or
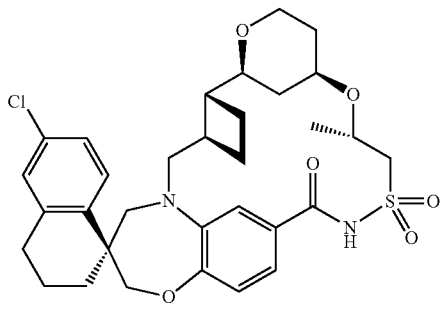
or
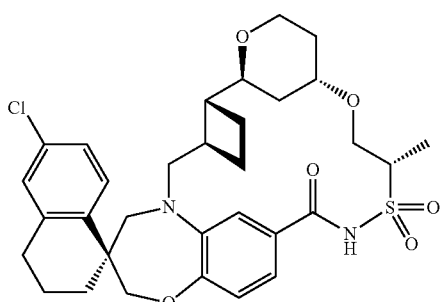
or
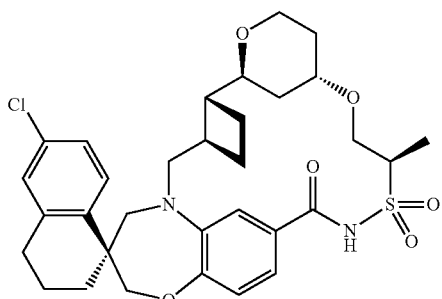
or
1880
-continued
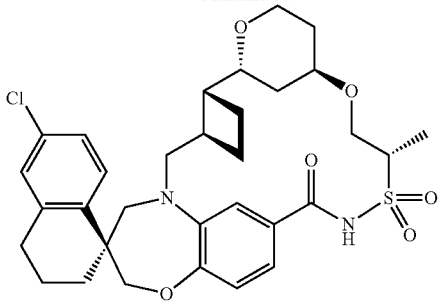
or
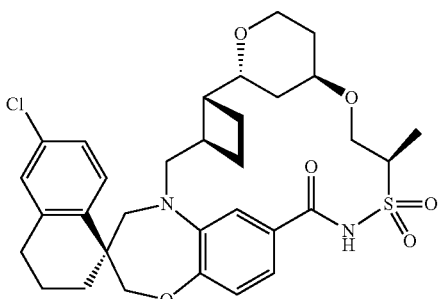
or
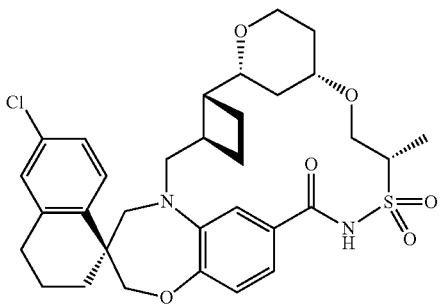
or
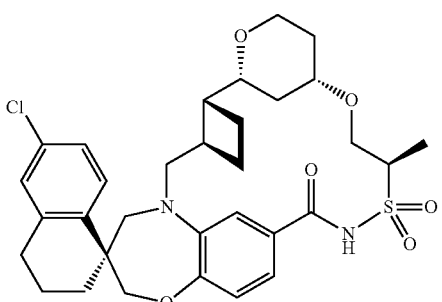
or
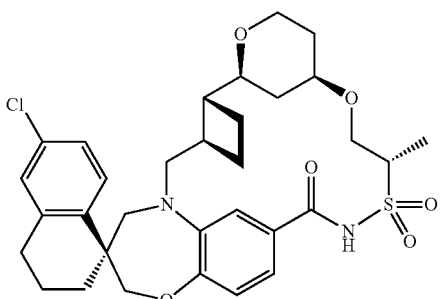
or -continued

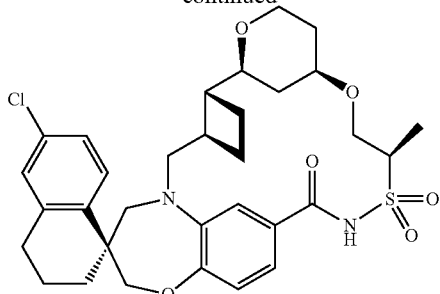

Step 1: (S)-methyl 6'-chloro-5-(((1R,2R)-2-((2R,4R)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate -continued

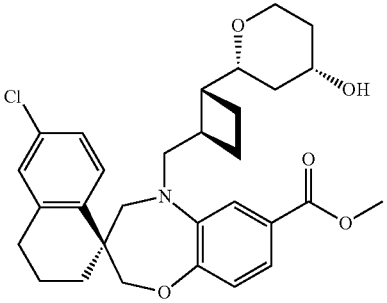

or

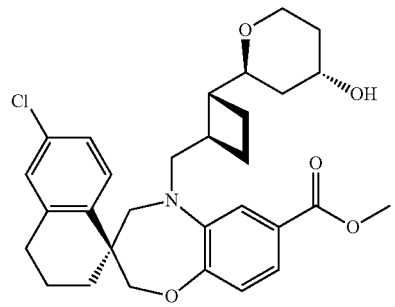

or

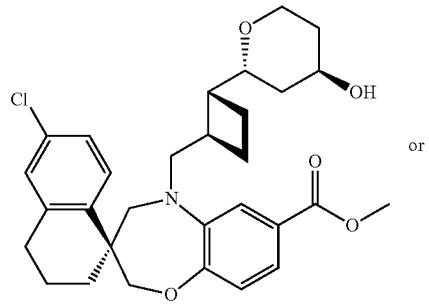

or

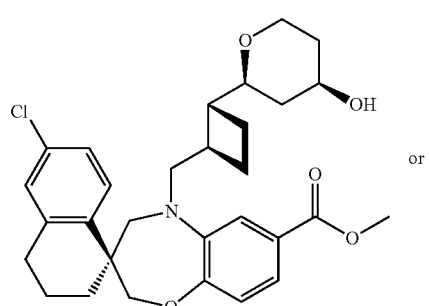

To a solution of (S)-methyl 6'-chloro-5-(((1R,2R)-2-((S)-4-oxotetrahydro-2H-pyran-2-yl) cyclobutyl)methyl)-3',4,4',5-tetrahydro-2H,2'H-spiro[benzo[b][1,4]oxazepine-3,1'-naphthalene]-7-carboxylate (Example 900, Step 2; 0.353 g, 0.674 mmol) in THF (10 mL), cooled to −78° C., was added dropwise lithium tri-sec-butyl(hydrido)borate (L-selectride®, 1.0 M solution in tetrahydrofuran, 1.0 mL, 1.0 mmol). After it was stirred at −78° C. for 24 min, it was quenched with potassium sodium tartrate (aq) (5 mL), diluted with Et₂O (10 mL) and stirred at rt for 1 h. The reaction mixture was extracted with EtOAc (150 mL). The organic phase was washed with brine, dried over anhydrous sodium sulfate and concentrated. The residue was loaded to a 24 g ISCO Gold column and eluted with 0% to 30% EtOAc/hexane to provide the title compound (308 mg) as a white solid. m/z (ESI, +ve ion) 526.1 (M+H)⁺.

Step 2: (S)-methyl 6'-chloro-5-(((1R,2R)-2-((2R,4R)-4-((R)-2-hydroxypropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-((R)-2-hydroxypropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-((S)-2-hydroxypropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-((S)-2-hydroxypropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-((R)-2-hydroxypropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-((R)-2-hydroxypropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-((S)-2-hydroxypropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-((S)-2-hydroxypropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-(((S)-1-hydroxypropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-(((S)-1-hydroxypropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-(((R)-1-hydroxypropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-(((R)-1-hydroxypropan-2-yl)oxy)tetrahydro-2H-pyran-2-yl)cyclobutyl)methyl)-3',4,4',5-tetrahydro-2H,2'H-spiro[benzo [b][1,4]oxazepine-3,1'-naphthalene]-7-carboxylate or (S)-methyl 6'-chloro-5-(((1R,2R)-2-((2R,4S)-4-(((S)-1-hydroxypropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-(((S)-1-hydroxypropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-(((R)-1-hydroxypropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-(((R)-1-hydroxypropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

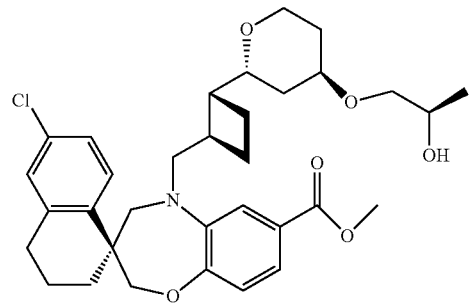

or

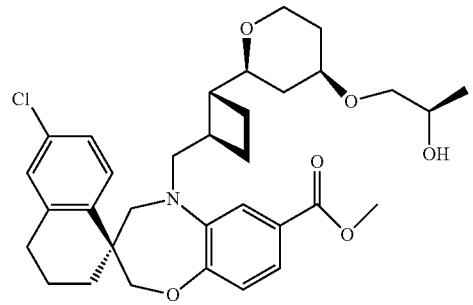

or

1885
-continued
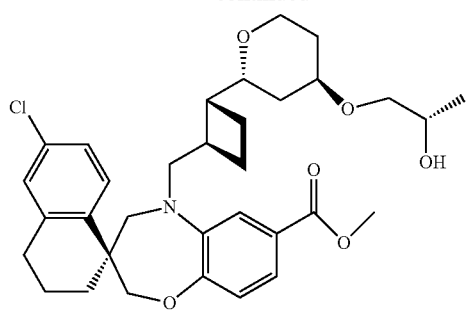
or
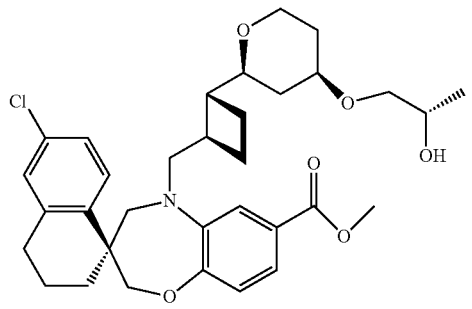
or
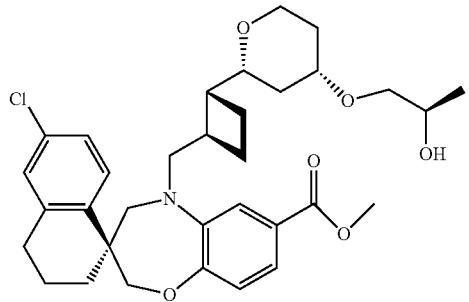
or
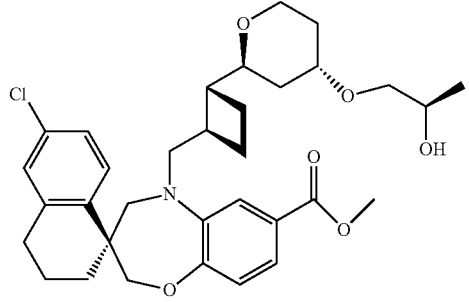
or
1886
-continued
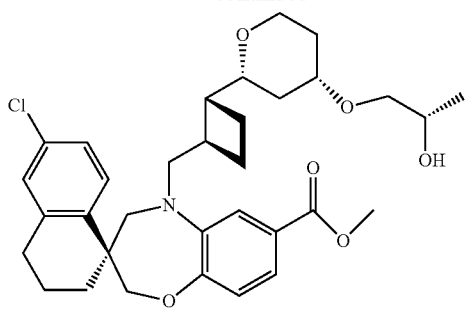
or
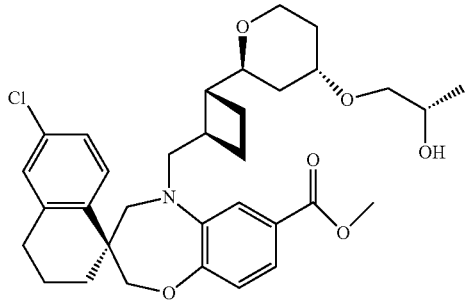
or
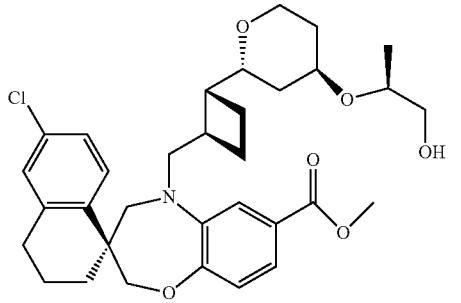
or

1887
-continued

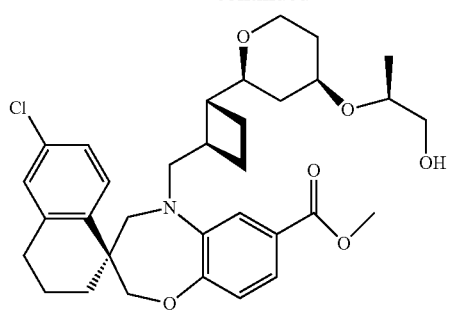

or

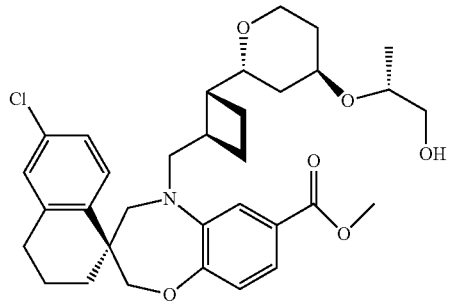

or

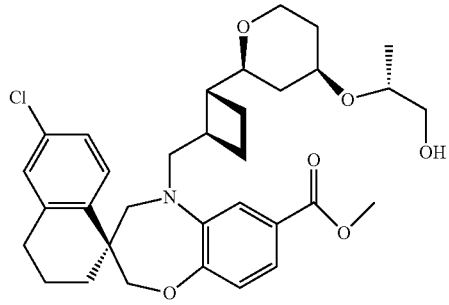

or

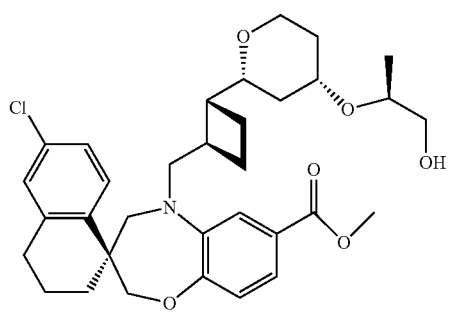

or

1888
-continued

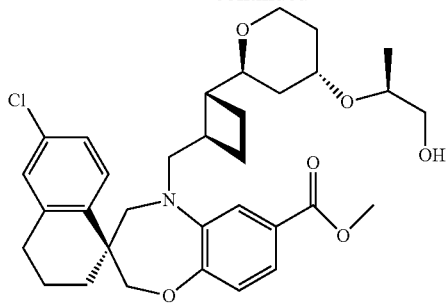

or

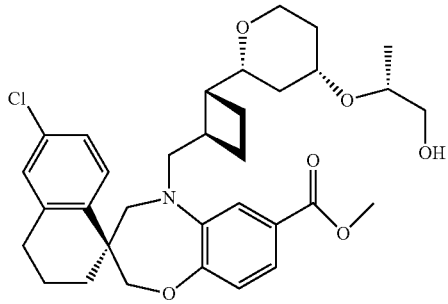

or

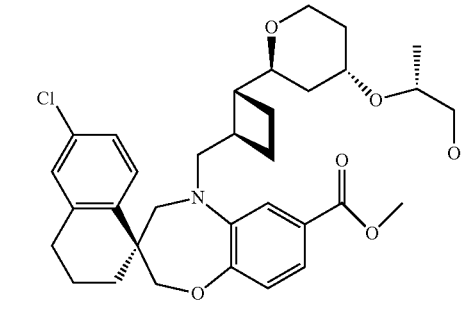

Boron trifluoride diethyl etherate (0.035 mL, 0.287 mmol) was added to a solution of(S)-methyl 6'-chloro-5-(((1R,2R)-2-((2S,4S)-4-hydroxytetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 919, Step 1; 0.302 g, 0.574 mmol) and (±)-propylene oxide (0.056 mL, 0.804 mmol) in DCM (5.7 mL). It was stirred at rt for 4 h. After concentration, the residue was purified by reverse phase preparative HPLC (Gemini™ Prep $C_{18}$ 5 μm column; Phenomenex, Torrance, CA; MeCN in water with 0.1% TFA, gradient elution) to give the title compound (32 mg) as a white solid. m/z (ESI, +ve ion) 584.2 $(M+H)^+$.

1889

Step 3: (S)-methyl 6'-chloro-5-(((1R,2R)-2-((2R,4R)-4-((R)-2-(pyrimidin-2-ylthio)propoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-((R)-2-(pyrimidin-2-ylthio)propoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-((S)-2-(pyrimidin-2-ylthio)propoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-((S)-2-(pyrimidin-2-ylthio)propoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-((R)-2-(pyrimidin-2-ylthio)propoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-((R)-2-(pyrimidin-2-ylthio)propoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-((S)-2-(pyrimidin-2-ylthio)propoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-((S)-2-(pyrimidin-2-ylthio)propoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-(((S)-1-(pyrimidin-2-ylthio)propan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-(((S)-1-(pyrimidin-2-ylthio)propan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-(((R)-1-(pyrimidin-2-ylthio)propan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-(((R)-1-(pyrimidin-2-ylthio)propan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-(((S)-1-

1890

(pyrimidin-2-ylthio)propan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-(((S)-1-(pyrimidin-2-ylthio)propan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-(((R)-1-(pyrimidin-2-ylthio)propan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-(((R)-1-(pyrimidin-2-ylthio)propan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate


or

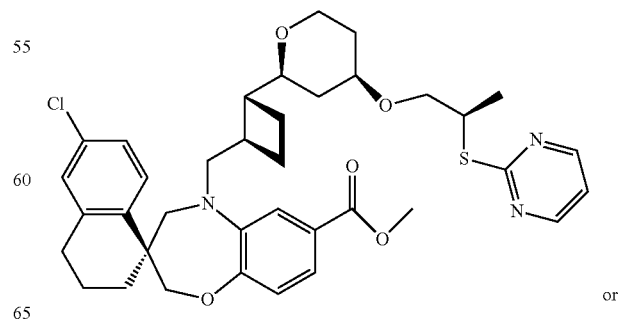

or

1891
-continued
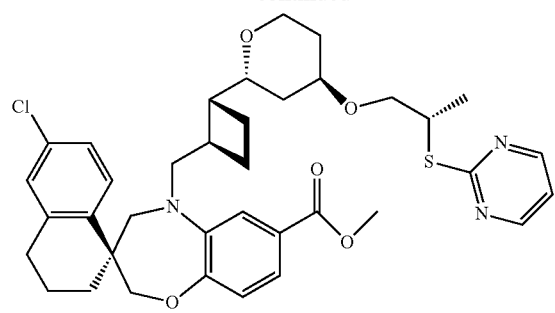
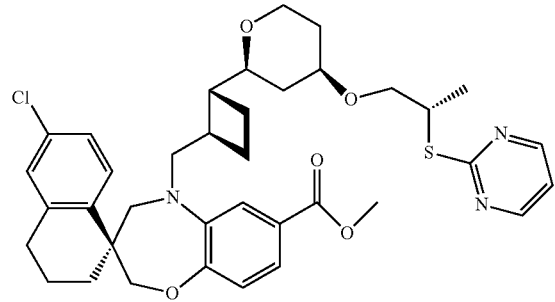
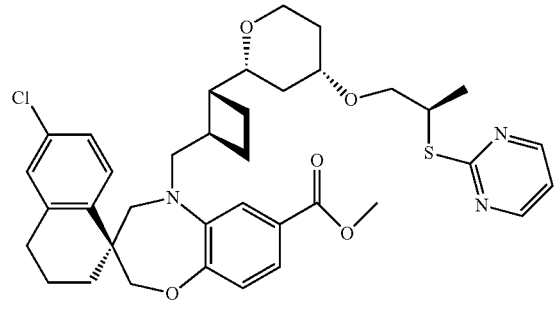
or
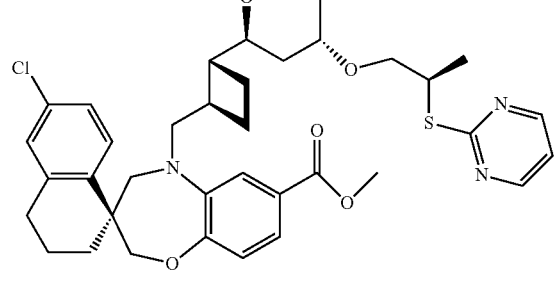
or
1892
-continued
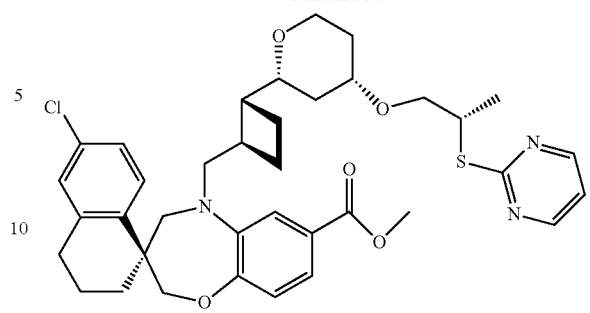
or
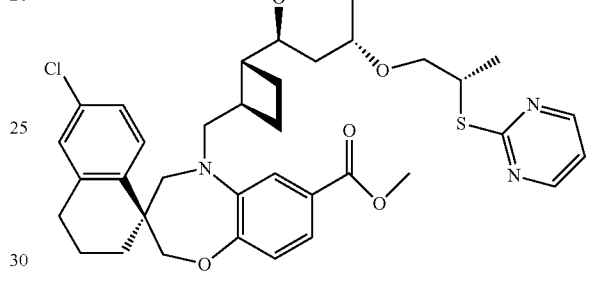
or
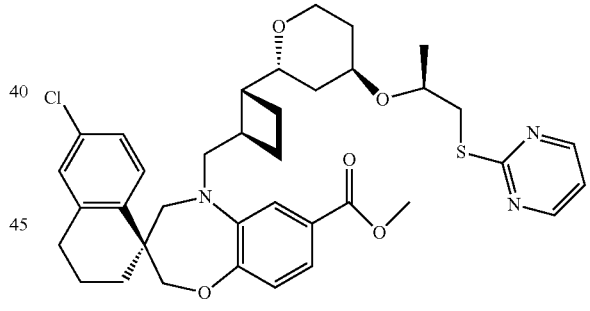
or
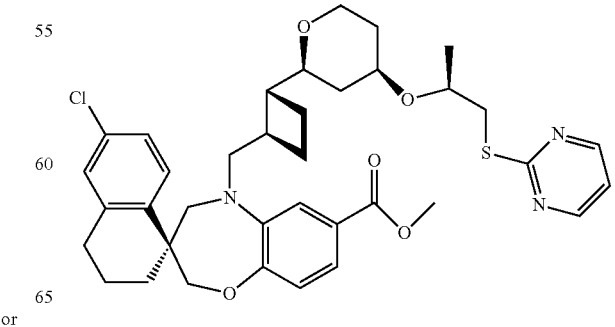
or

1893
-continued

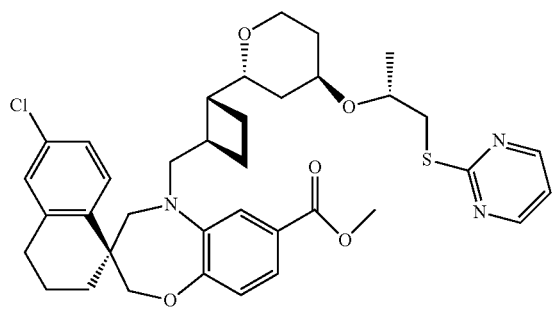

or

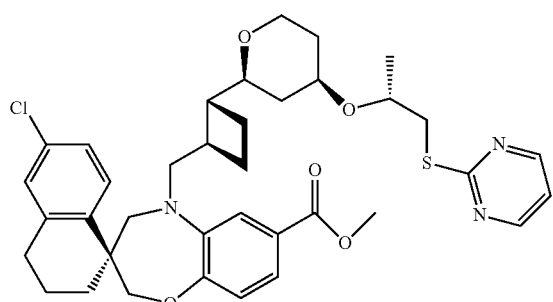

or

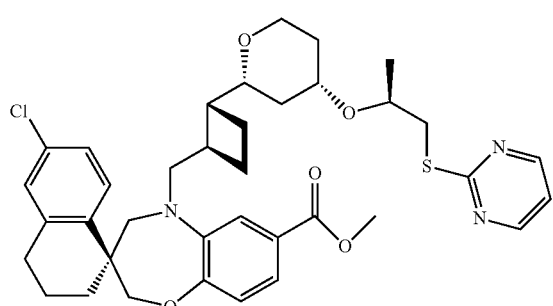

or

1894
-continued

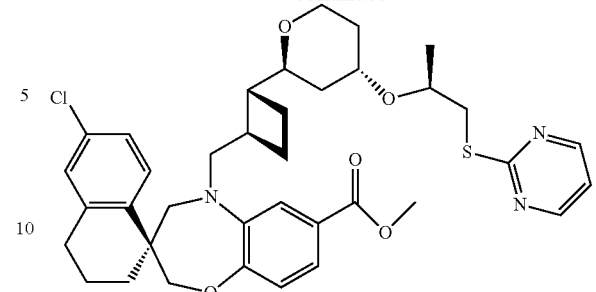

or

Triphenylphosphine (127 mg, 0.55 mmol) was added to a solution of (1'S)-methyl 6'-chloro-5-(((1R,2R)-2-((2S,4S)-4-((1-hydroxypropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 919, Step 2; 0.032 g, 0.055 mmol) and 2-mercapto-pyrimidine (0.061 g, 0.548 mmol) in THF (0.27 mL). It was degassed by argon and was added diethyl azodicarboxylate (40 wt % solution in toluene, 0.25 mL, 0.55 mmol). It was stirred at 60° C. for 1.6 h. After concentration, the residue was purified by reverse phase preparative HPLC (Gemini™ Prep C$_{18}$ 5 μm column; Phenomenex, Torrance, CA; MeCN in water with 0.1% TFA, gradient elution) to give the title compound (20 mg) as a film. m/z (ESI, +ve ion) 678.3 (M+H)$^+$.

Step 4: (S)-methyl 6'-chloro-5-(((1R,2R)-2-((2R,4R)-4-((R)-2-(pyrimidin-2-ylsulfonyl)propoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-((R)-2-(pyrimidin-2-ylsulfonyl)propoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-((S)-2-(pyrimidin-2-ylsulfonyl)propoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,44R)-4-((S)-2-(pyrimidin-2-ylsulfonyl)propoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-((R)-2-(pyrimidin-2-ylsulfonyl)propoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-((R)-2-(pyrimidin-2-ylsulfonyl)propoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-((S)-2-(pyrimidin-2-ylsulfonyl)propoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-((S)-2-(pyrimidin-2-ylsulfonyl)propoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-(((S)-1-(pyrimidin-2-ylsulfonyl)propan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-(((S)-1-(pyrimidin-2-ylsulfonyl)propan-2-yl)oxy)tetrahydro-2H-pyran-2-yl) cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-(((R)-1-(pyrimidin-2-ylsulfonyl)propan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-(((R)-1-(pyrimidin-2-ylsulfonyl)propan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-(((S)-1-(pyrimidin-2-ylsulfonyl)propan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-(((S)-1-(pyrimidin-2-ylsulfonyl)propan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-(((R)-1-(pyrimidin-2-ylsulfonyl)propan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-(((R)-1-(pyrimidin-2-ylsulfonyl)propan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

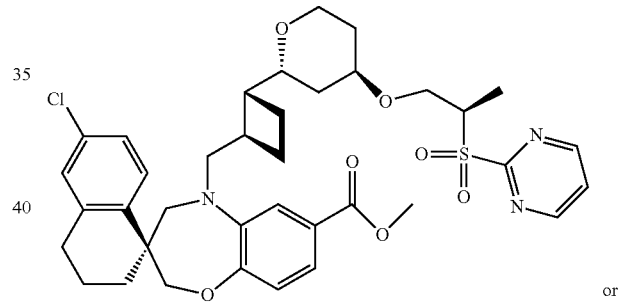

or

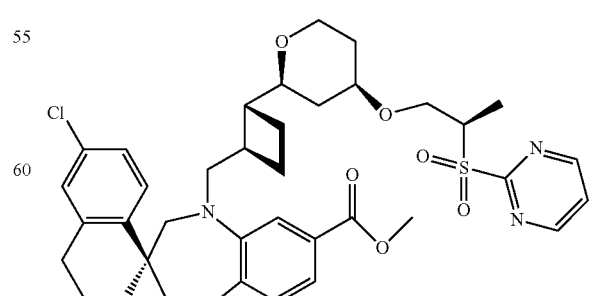

or

1897
-continued
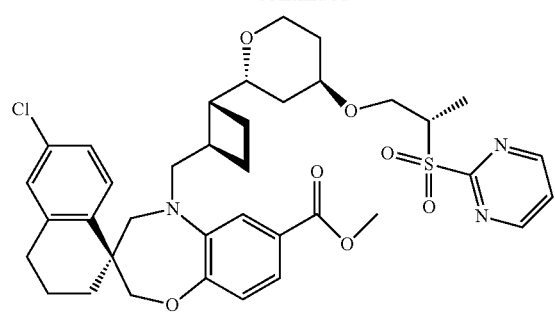
or
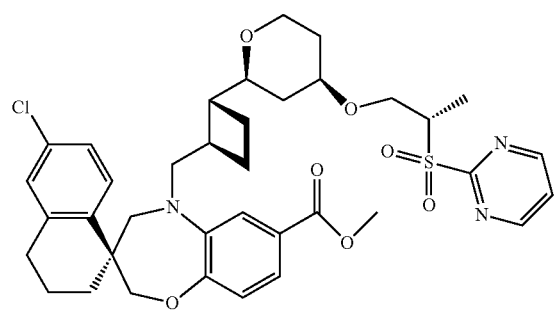
or
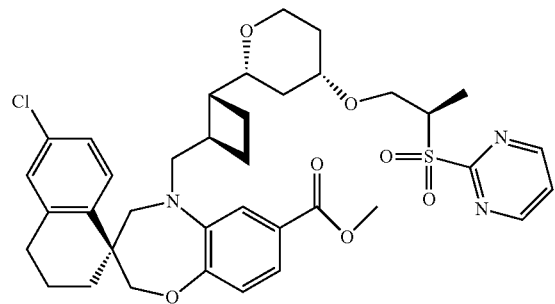
or
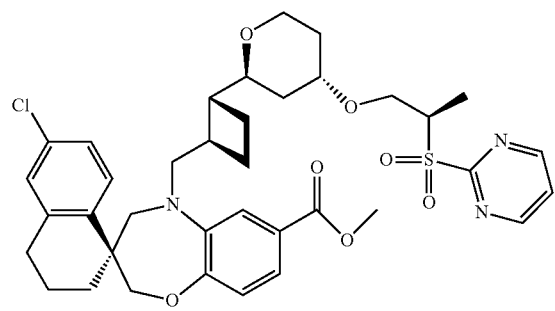
or
1898
-continued
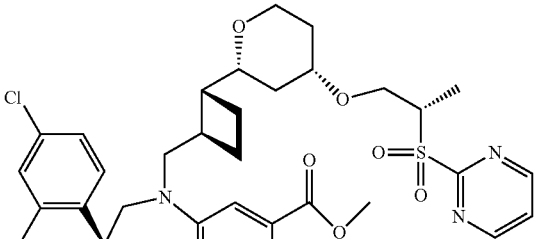
or
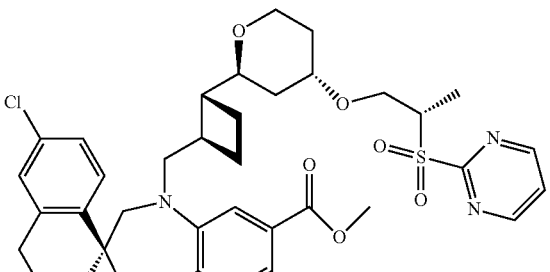
or
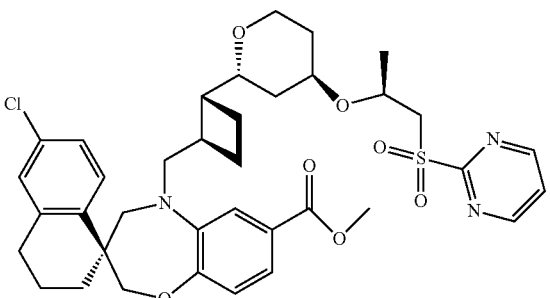
or
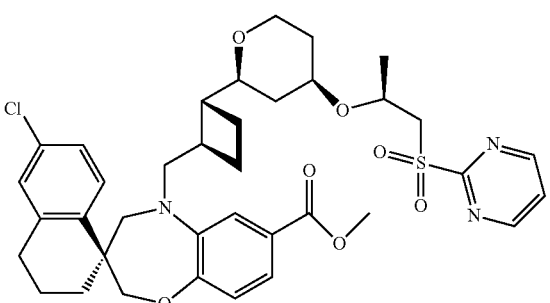
or

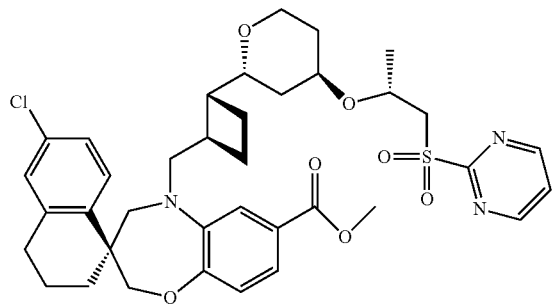

or

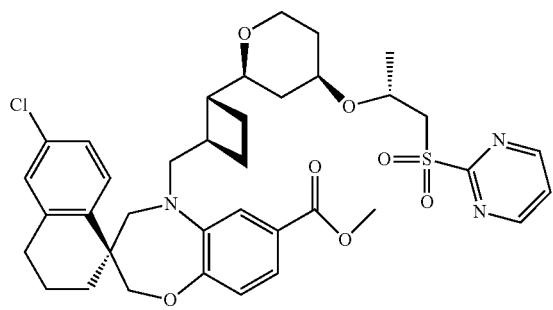

or

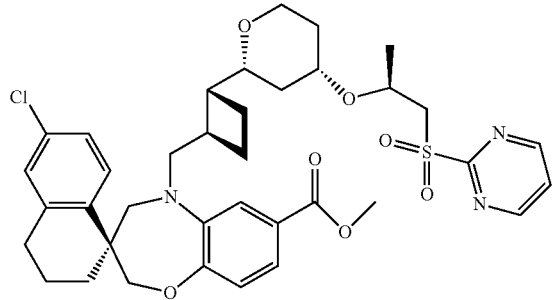

or

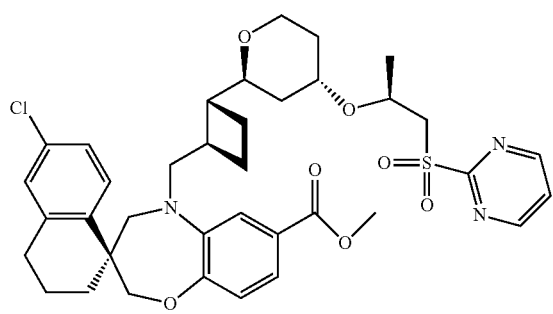

or

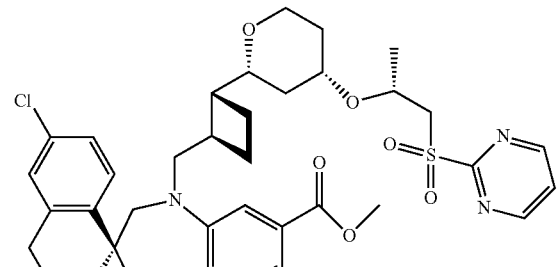

or

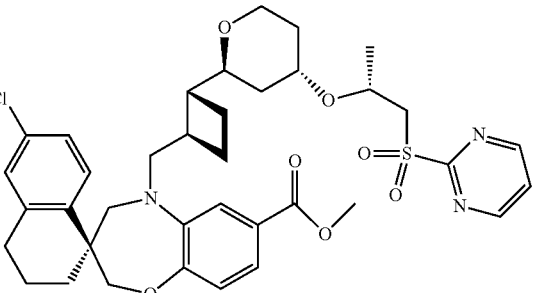

To a stirred solution of (1'S)-methyl 6'-chloro-5-(((1R,2R)-2-((2S,4S)-4-((1-(pyrimidin-2-ylthio)propan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 919, Step 3; 0.026 g, 0.038 mmol) in toluene (0.17 mL) and water (0.017 mL) was added sodium tungstate dihydrate (2.5 mg, 3.8 μmol), phenylphosphonic acid (0.4 mg, 4 μmol) and tetrabutyl-ammonium sulfate (50 wt. % solution in water, 2 μl, 4 μmol). After 2 min, hydrogen peroxide 30% in water (0.04 mL, 0.4 mmol) was added in one portion and it was stirred at 55° C. for 80 min. After concentration, the residue was purified by reverse phase preparative HPLC (Gemini™ Prep $C_{18}$ 5 μm column; Phenomenex, Torrance, CA; MeCN in water with 0.1% TFA, gradient elution) to give the title compound (14 mg) as a white solid. m/z (ESI, +ve ion) 710.1 (M+H)$^+$.

1901

Step 5: (S)-methyl 6'-chloro-5-(((1R,2R)-2-((2R,4R)-4-(((S)-1-sulfamoylpropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4—(((S)-1-sulfamoylpropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-(((R)-1-sulfamoylpropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-(((R)-1-sulfamoylpropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-(((S)-1-sulfamoylpropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-(((S)-1-sulfamoylpropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-(((R)-1-sulfa-moylpropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-(((R)-1-sulfa-moylpropan-2-yl)oxy)tetrahydro-2H-pyran-2-yl)cyclobutyl) methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-((R)-2-sulfamoylpropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-((R)-2-sulfamoylpropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4R)-4-((S)-2-sulfamoylpropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4R)-4-((S)-2-sulfamoylpropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-((R)-2-sulfamoylpropoxy)tetrahydro-2H-pyran-2-yl)cyclobutyl)methyl)-3',4,4',5-tetrahydro-

1902

2H,2'H-spiro[benzo[b][1,4]oxazepine-3,1'-naphthalene]-7-carboxylate or (S)-methyl 6'-chloro-5-(((1R,2R)-2-((2S,4S)-4-((R)-2-sulfamoylpropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2R,4S)-4-((S)-2-sulfamoylpropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate or (S)-methyl 6'-chloro-5-(((1R,2R)-2-((2S,4S)-4-((S)-2-sulfamoylpropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate

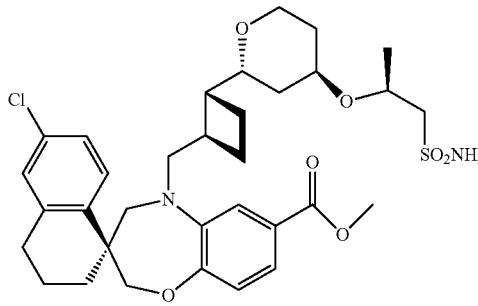

or

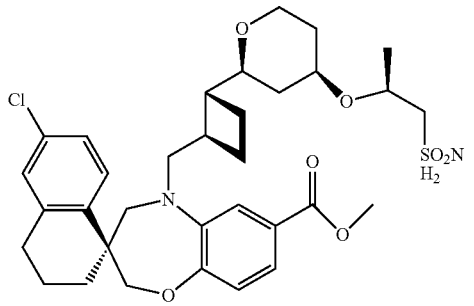

or

1903
-continued
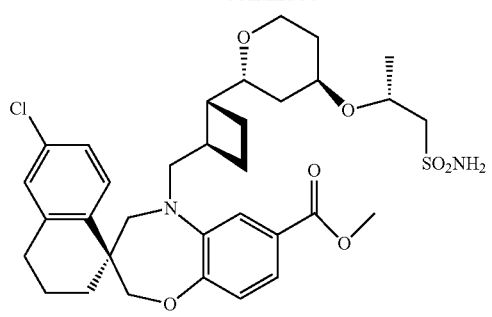
or
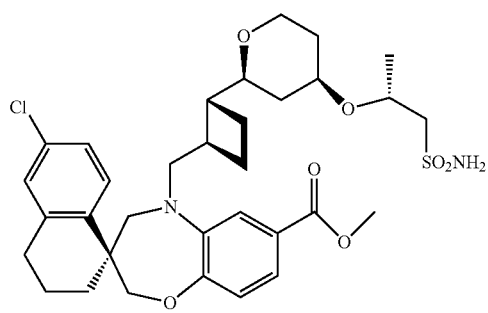
or
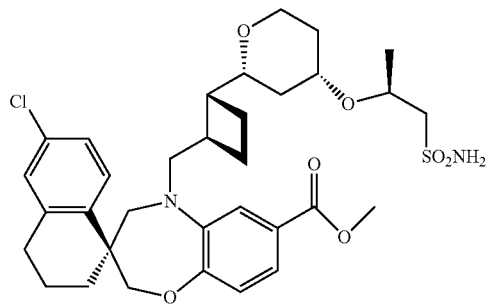
or
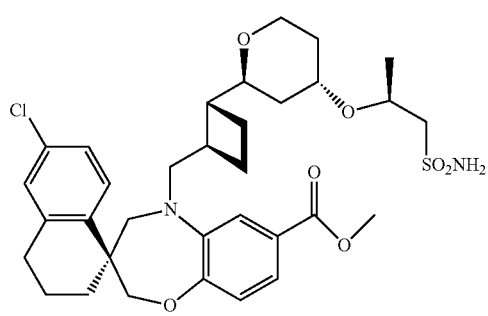
or
1904
-continued
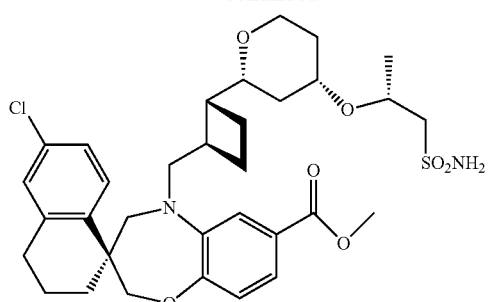
or
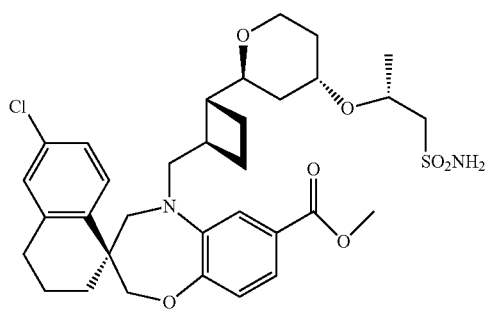
or
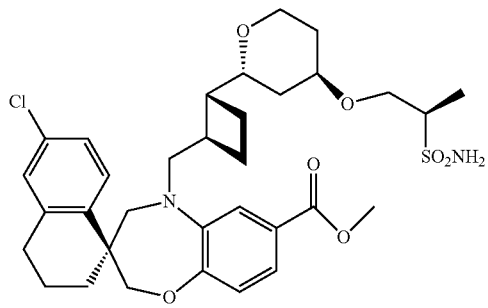
or
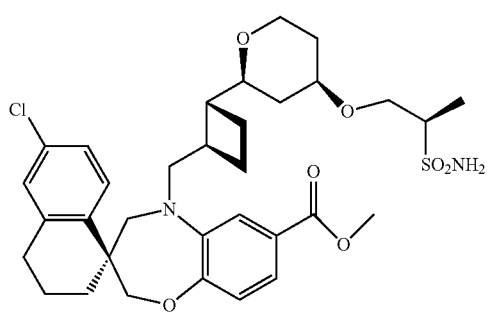
or 1905
-continued

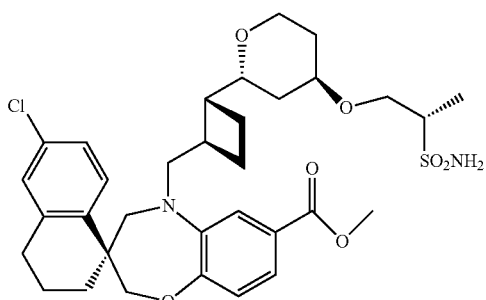

or

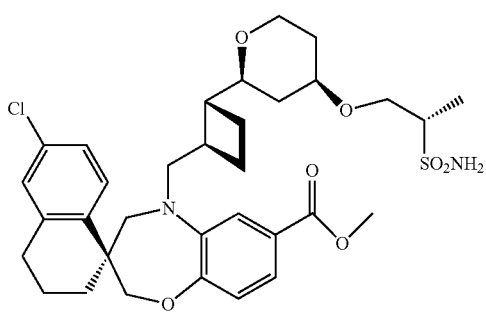

or

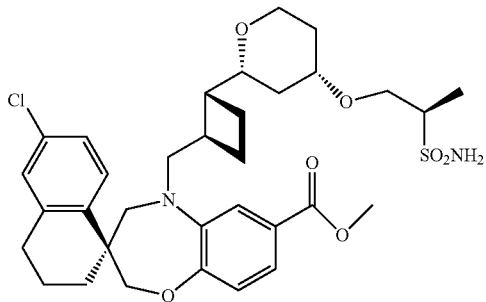

or

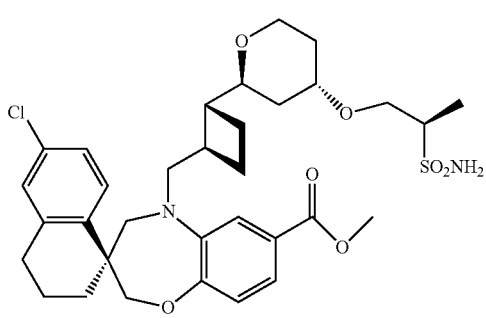

or

1906
-continued

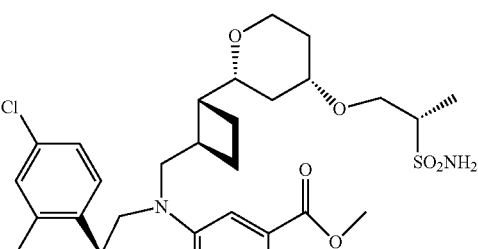

or

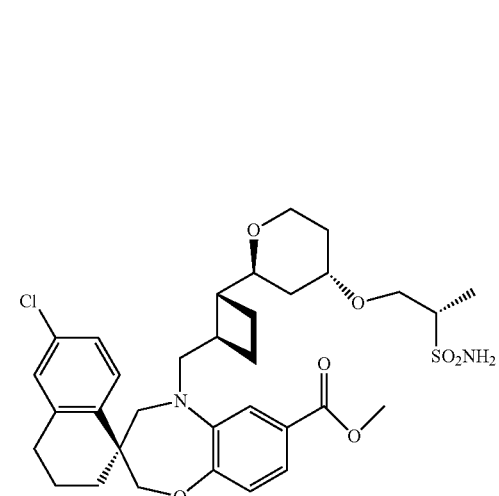

To a stirred solution of (1'S)-methyl 6'-chloro-5-(((1R, 2R)-2-((2S,4S)-4-((1-(pyrimidin-2-ylsulfonyl)propan-2-yl)oxy)tetrahydro-2H-pyran-2-yl)cyclobutyl)methyl)-3',4,4',5-tetrahydro-2H,2'H-spiro[benzo [b][1,4]oxazepine-3,1'-naphthalene]-7-carboxylate (Example 919, Step 4; 0.014 g, 0.020 mmol) in MeOH (0.7 mL) was added cesium carbonate (8 mg, 0.1 mmol). It was stirred at rt for 2 h. To this reaction mixture was added hydroxylamine-o-sulfonic acid (0.013 g, 0.118 mmol) in water (0.5 mL) and it was stirred at 50° C. for 30 min. After it was cooled to rt, EtOAc (70 mL) was added. The organic phase was washed with brine, dried over anhydrous sodium sulfate. The solution was filtered through a short plug of silica gel and concentrated to provide the title compound (9.5 mg) as a white solid. m/z (ESI, +ve ion) 647.3 (M+H)$^+$.

Step 6: (S)-6'-chloro-5-((((1R,2R)-2-((2R,4R)-4-((R)-2-sulfamoylpropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-((((1R,2R)-2-((2S,4R)-4-((R)-2-sulfamoylpropoxy)tetrahydro-2H-pyran-2-yl)cyclobutyl)methyl)-3',4,4',5-tetrahydro-2H,2'H-spiro [benzo[b][1,4]oxazepine-3,1'-naphthalene]-7-carboxylic Acid or (S)-6'-chloro-5-((((1R,2R)-2-((2R,4R)-4-((S)-2-sulfamoylpropoxy)tetrahydro-2H-pyran-2-yl)cyclobutyl)methyl)-3',4,4',5-tetrahydro-2H,2'H-spiro[benzo [b][1,4]oxazepine-3,1'-naphthalene]-7-carboxylic Acid or (S)-6'-chloro-5-((((1R,2R)-2-((2S,4R)-4-((S)-2-sulfamoylpropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-((((1R,2R)-2-((2R,4S)-4-((R)-2-sulfamoylpropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-((((1R,2R)-2-((2S,4S)-4-((R)-2-sulfamoylpropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-((((1R,2R)-2-((2R,4S)-4-((S)-2-sulfamoylpropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-((((1R,2R)-2-((2S,4S)-4-((S)-2-sulfamoylpropoxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-((((1R,2R)-2-((2R,4R)-4-(((S)-1-sulfamoylpropan-2-yl)oxy)tetrahydro-2H-pyran-2-yl)cyclobutyl)methyl)-3',4,4',5-tetrahydro-2H,2'H-spiro[benzo [b][1,4]oxazepine-3,1'-naphthalene]-7-carboxylic Acid or (S)-6'-chloro-5-((((1R,2R)-2-((2S,4R)-4-(((S)-1-sulfamoylpropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-((((1R,2R)-2-((2R,4R)-4-(((R)-1-sulfamoylpropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-((((1R,2R)-2-((2S,4R)-4-(((R)-1-sulfamoylpropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-((((1R,2R)-2-((2R,4S)-4-(((S)-1-sulfamoylpropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-((((1R,2R)-2-((2S,4S)-4-(((S)-1-sulfamoylpropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-((((1R,2R)-2-((2R,4S)-4-(((R)-1-sulfamoylpropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-((((1R,2R)-2-((2S,4S)-4-(((R)-1-sulfamoylpropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic Acid

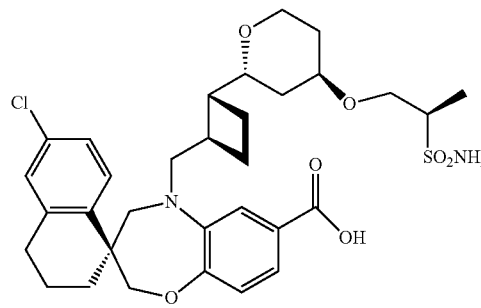

or

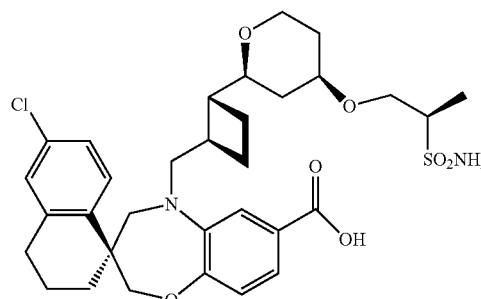

or

1909
-continued
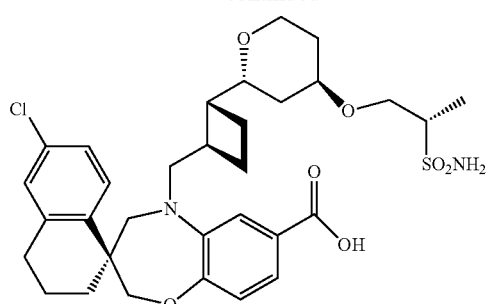
or
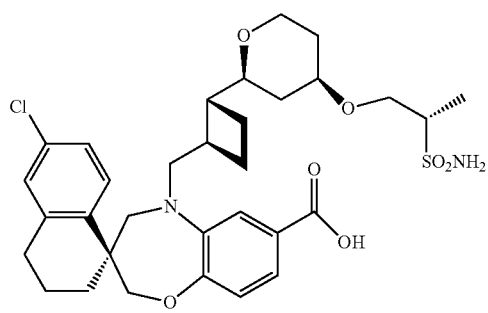
or
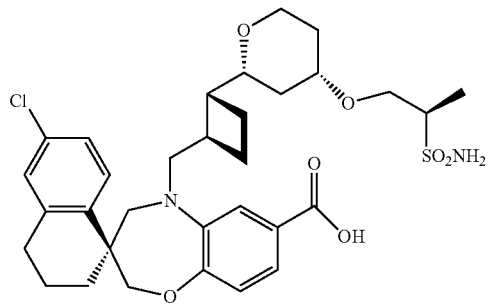
or
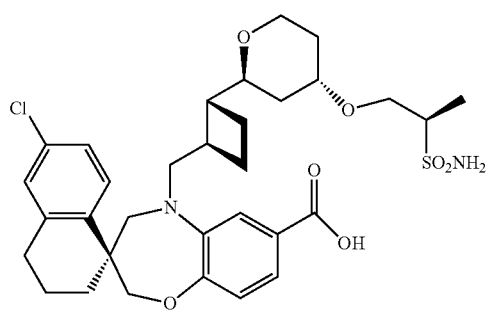
or
1910
-continued
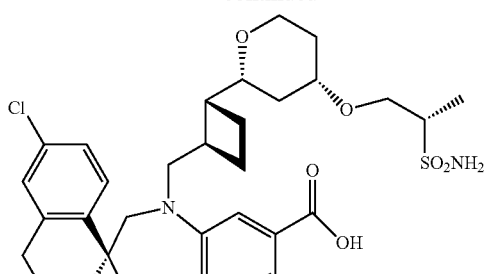
or
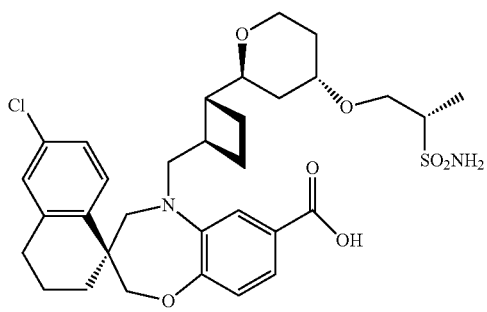
or
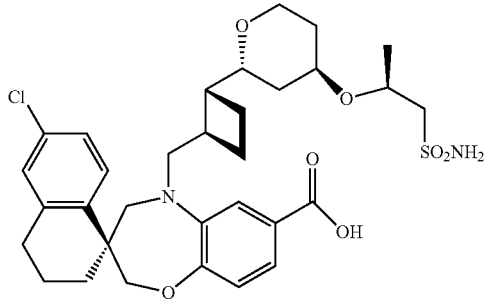
or
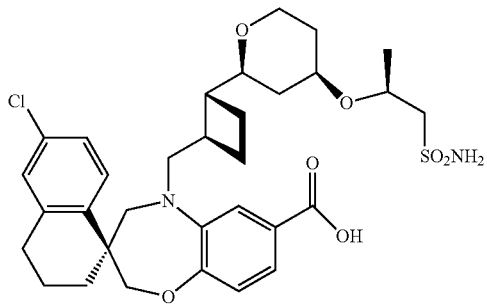
or -continued

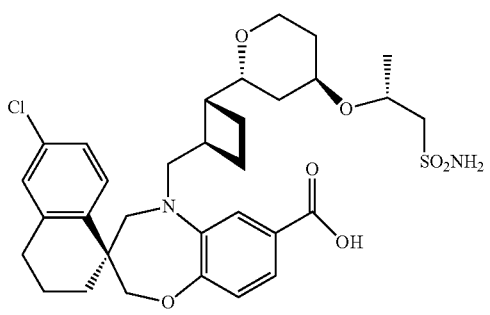

or

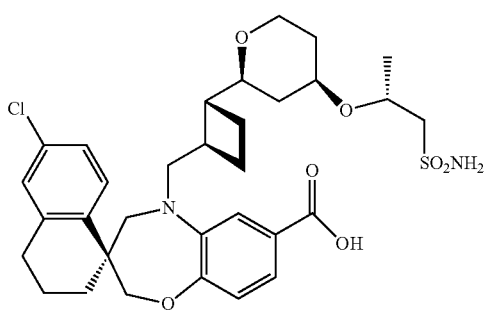

or

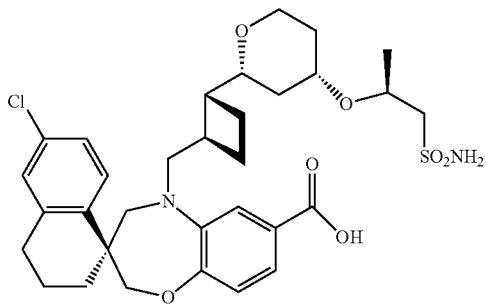

or

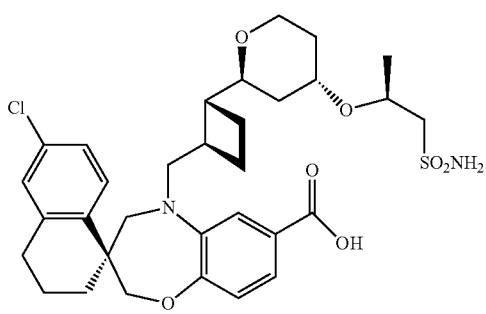

or

-continued

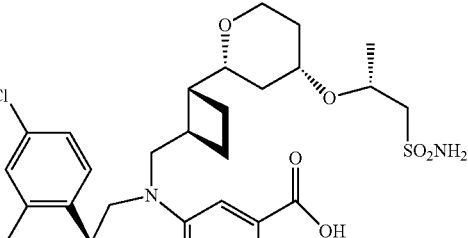

or

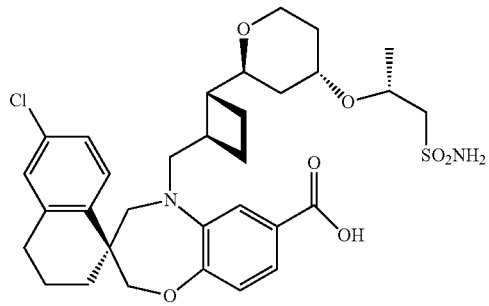

Lithium hydroxide (1M aqueous solution, 0.44 mL, 0.44 mmol) was added to a solution of (1'S)-methyl 6'-chloro-5-(((1R,2R)-2-((2S,4S)-4-((1-sulfamoylpropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylate (Example 919, Step 5; 0.0095 g, 0.015 mmol) in THF (0.5 mL) and MeOH (1 mL). It was stirred at 55° C. for 2 h. It was concentrated, acidified with 1 N HCl solution to pH 2-3 and extracted with EtOAc (60 mL). The organic phase was washed with brine, dried over anhydrous sodium sulfate. The filtrate was filtered through a short plug of silica gel and concentrated to get the title compound (8 mg) as a white solid. m/z (ESI, +ve ion) 633.0 (M+H)⁺.

Step 7: (1S,3'R,6'R,7'S,11'S,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'S,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'R,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'R,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'S,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,1]'S,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'R,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'S,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'S,14'S)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'S,14'R)-6-chloro-14'-methyl-3,4-dihydro-2H,17'H-spiro[naphthalene-1,24'-[8,12,22]trioxa[15]thia[1,16]diazapentacyclo [16.7.2.1$^{7,11}$~0$^{3,6}$.0$^{21,26}$]octacosa[18,20,26]trien]-17'-one 15',15'-dioxide or (1S,3'R,6'R,7'R,11'R,14'S)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'R,14'R)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$~0$^{3,6}$.0$^{21,26}$]octacosa[18,20,26]trien]-17'-one 15',15'-dioxide or (1S,3'R,6'R,7'R,11'S,14'S)-6-chloro-14'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'S,14'R)-6-chloro-14'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'R,14'S)-6-chloro-14'-methyl-3,4-dihydro-2H,17'H-spiro [naphthalene-1,24'-[8,12,22]trioxa[15]thia[1,16]diazapentacyclo [16.7.2.1$^{7,11}$.0$^{3,6}$.0$^{21,26}$]octacosa[18,20,26]trien]-17'-one 15',15'-dioxide or (1S,3'R,6'R,7'S,11'R,14'R)-6-chloro-14'-methyl-3,4-dihydro-2H,17'H-spiro [naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide N,N-Dimethylpyridin-4-amine (DMAP) (0.049 g, 0.40 mmol) was added to a solution of (1'S)-6'-chloro-5-(((1R,2R)-2-((2S,4S)-4-((1-sulfamoylpropan-2-yl)oxy)tetrahydro-2H-pyran-2-yl)cyclobutyl)methyl)-3',4,4',5-tetrahydro-2H,2'H-spiro[benzo[b][1,4]oxazepine-3,1'-naphthalene]-7-carboxylic acid (Example 919, Step 6; 0.009 g, 0.014 mmol) in DCM (20 mL) at 0° C. Then N1-((ethylimino)methylene)-N3,N3-dimethylpropane-1,3-diamine hydrochloride (EDC, 0.035 g, 0.185 mmol) was added slowly in portions and it was stirred at 0° C. to rt for 3 days. After it was concentrated the residue was purified by reverse phase preparative HPLC (Gemini™ Prep C$_{18}$ 5 μm column; Phenomenex, Torrance, CA; MeCN in water with 0.1% TFA, gradient elution). The title compound (1.5 mg) was obtained as a single isomer (fourth eluting peak). $^1$H NMR (400 MHz, CD$_2$Cl$_2$) δ 8.28 (m, 1H), 7.72 (m, 1H), 7.40 (m, 1H), 7.18 (m, 1H), 7.09 (m, 1H), 6.99 (d, J=8.22 Hz, 1H), 6.54 (d, J=1.96 Hz, 1H), 4.37-4.29 (m, 1H), 4.16-4.08 (m, 4H), 3.91-3.84 (m, 1H), 3.81-3.72 (m, 2H), 3.34 (br. s., 1H), 3.19 (m, 1H), 2.73-2.80 (m, 2H), 2.43 (d, J=6.46 Hz, 1H), 2.17-1.14 (m, 19H). m/z (ESI, +ve ion) 615.0 (M+H)$^+$.

Example 920. (1S,3'R,6'R,7'S,11'S,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'S,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'R,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'R,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'S,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'S,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'R,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'S,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'S,14'S)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'S,14'R)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'R,14'S)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'R,14'R)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'S,14'S)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'S,14'R)-6-chloro-14'-methyl-3,4-dihydro-2H,17'H-spiro[naphthalene-1,24'-[8,12,22]trioxa[15]thia[1,16]diazapentacyclo [16.7.2.1$^{7,11}$.0$^{3,6}$.0$^{21,26}$]octacosa[18,20,26]trien]-17'-one 15',15'-dioxide or (1S,3'R,6'R,7'S,11'R,14'S)-6-chloro-14'-methyl-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'R,14'R)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide

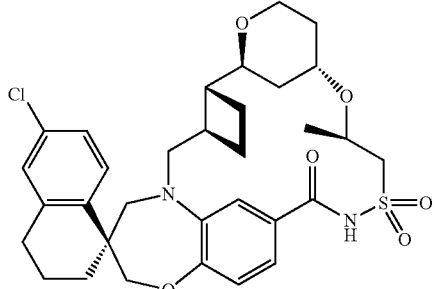

or

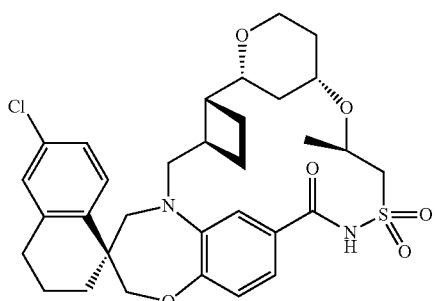

or

1917
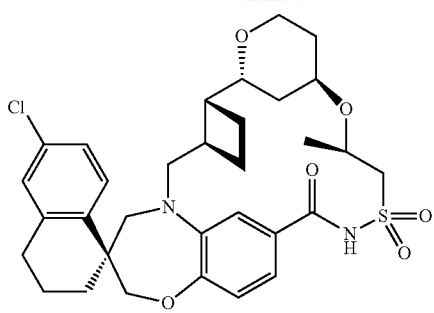
or
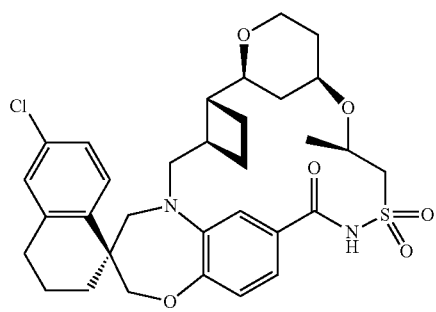
or
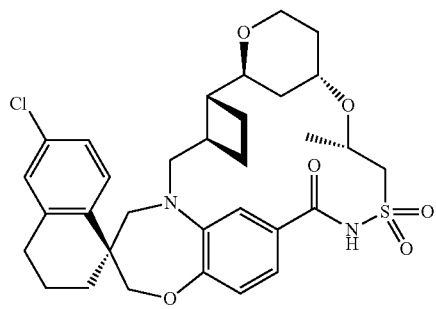
or
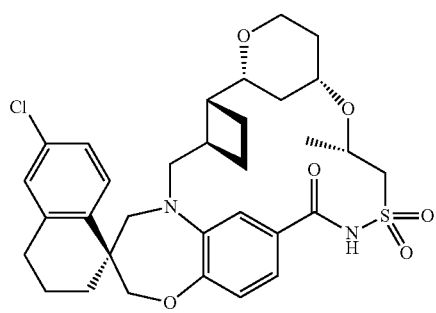
or
1918
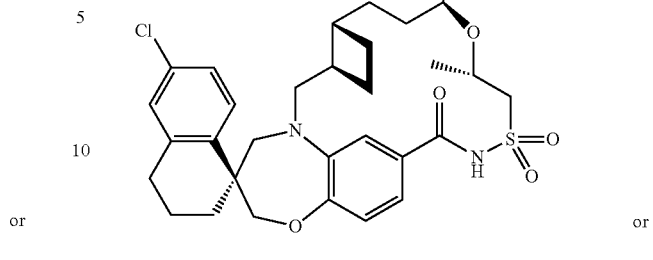
or
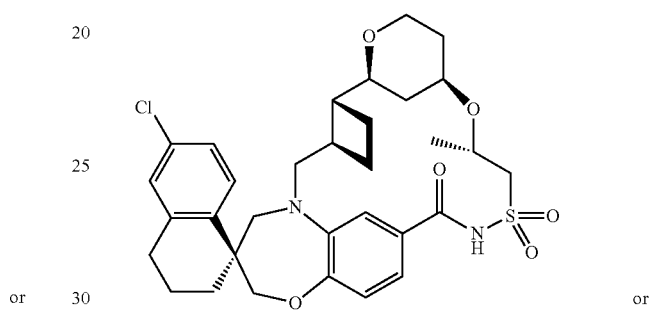
or
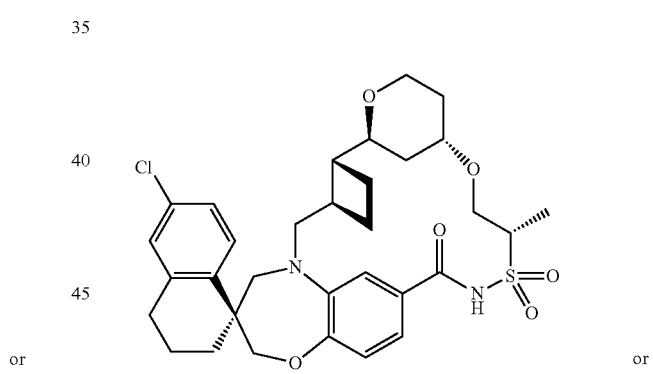
or
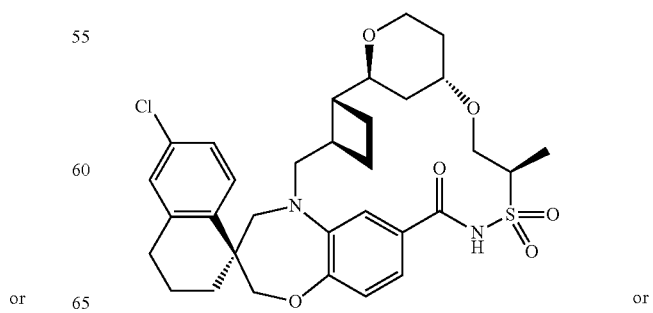
or

1919
-continued
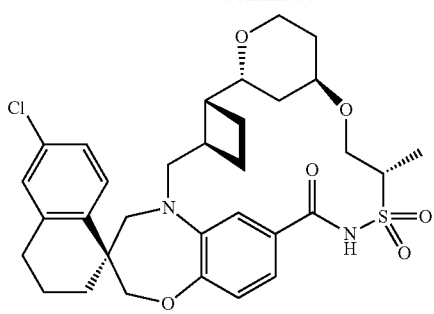
or
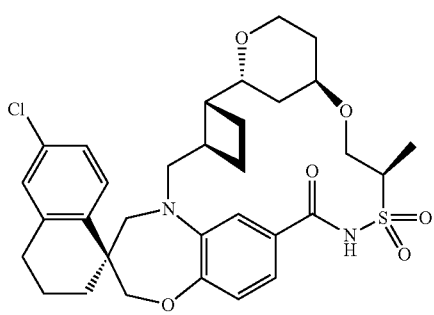
or
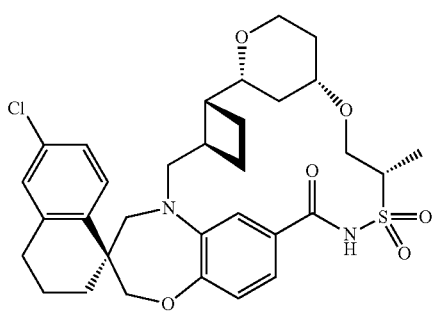
or
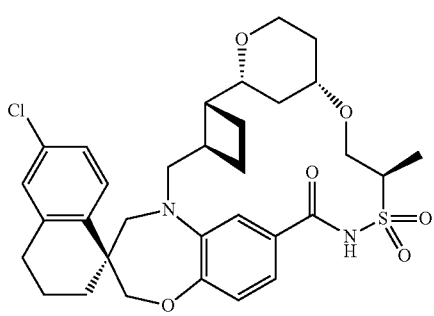
or
1920
-continued
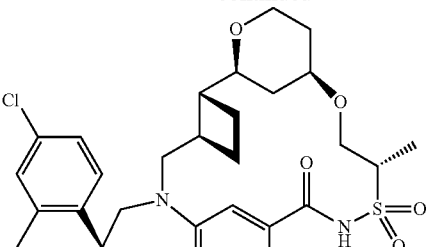
or
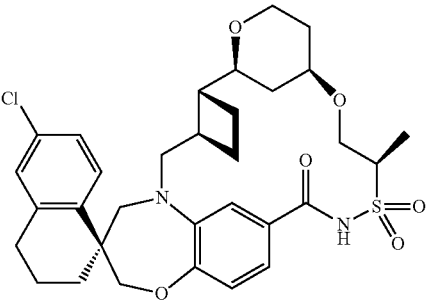
The title compound (1.4 mg) was obtained as a single isomer (third eluting peak) from the reverse phase preparative HPLC in Example 919. $^1$H NMR (400 MHz, CD$_2$Cl$_2$) δ 8.15 (s, 1H), 7.73 (d, J=8.61 Hz, 1H), 7.34 (dd, J=2.05, 8.31 Hz, 1H), 7.17 (dd, J=2.35, 8.41 Hz, 1H), 7.09 (d, J=2.15 Hz, 1H), 6.98 (d, J=8.41 Hz, 1H), 6.49 (d, J=2.15 Hz, 1H), 4.17-4.09 (m, 2H), 3.92-3.85 (m, 2H), 3.84-3.68 (m, 4H), 3.49-3.42 (m, 1H), 3.24-3.09 (m, 2H), 2.81-2.74 (m, 2H), 2.70 (s, 1H), 2.49-1.57 (m, 15H), 1.42 (d, J=7.04 Hz, 3H). m/z (ESI, +ve ion) 615.1 (M+H).

Example 921. (S,3'R,6'R,7'S,11'S,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'S,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'R,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'R,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'S,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'S,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'R,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]18,20,26]trien]-17'-one 15',15'-dioxide or (1S,3'R,6'R,7'R,11'S,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]18,20,26]trien]-17'-one 15',15'-dioxide or (1S,3'R,6'R,7'S,11'S,14'S)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'S,14'R)-6-chloro-14'-methyl-3,4-dihydro-2H,17'H-spiro[naphthalene-1,24'-[8,12,22]trioxa[15]thia[1,16]diazapentacyclo[16.7.2.1-7,11~.0~3,6~.0~21,26~]octacosa[18,20,26]trien]-17'-one 15',15'-dioxide or (1S,3'R,6'R,7'R,11'R,14'S)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'R,14'R)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'S,14'S)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'S,14'R)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$][18,20,26]trien]-17'-one 15',15'-dioxide or (1S,3'R,6'R,7'S,11'R,14'S)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'R,14'R)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide

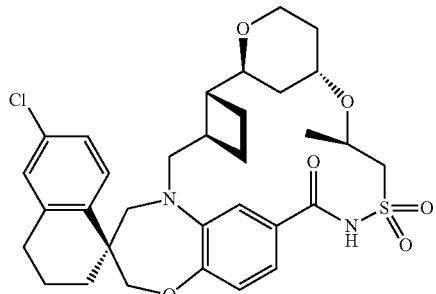

or

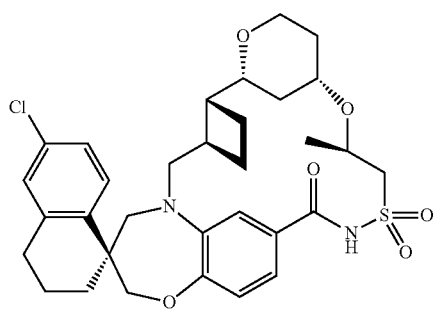

or

1923
-continued
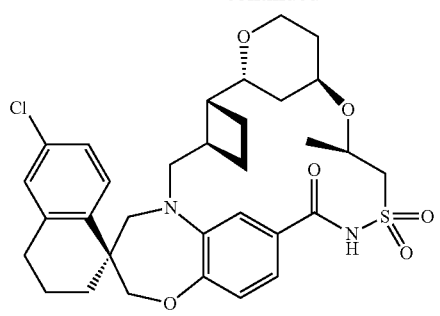
or
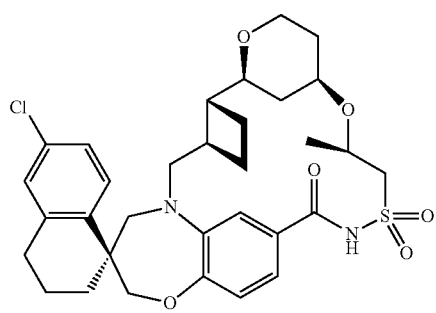
or
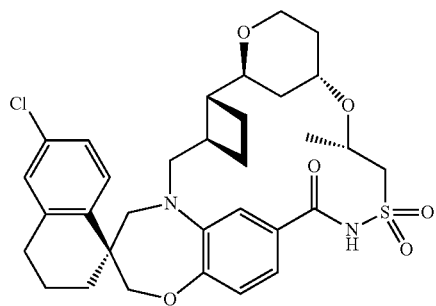
or
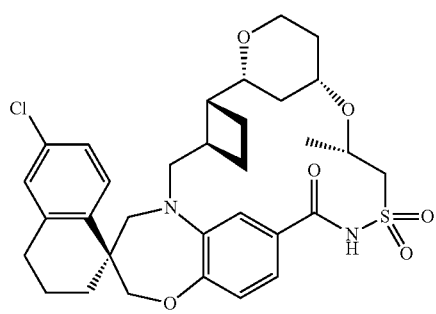
or
1924
-continued
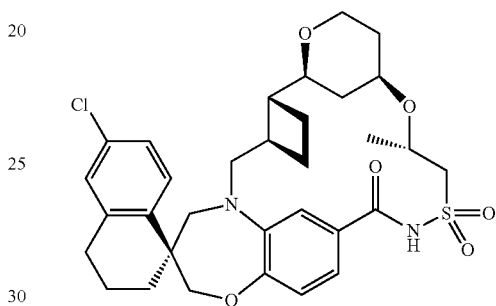
or
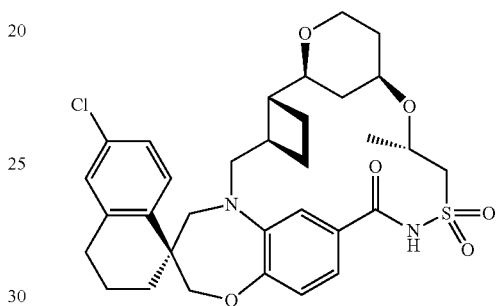
or
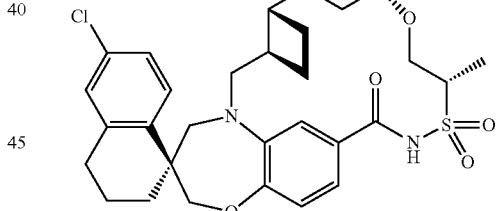
or
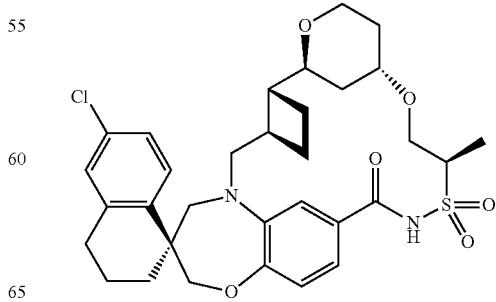
or 1925
-continued
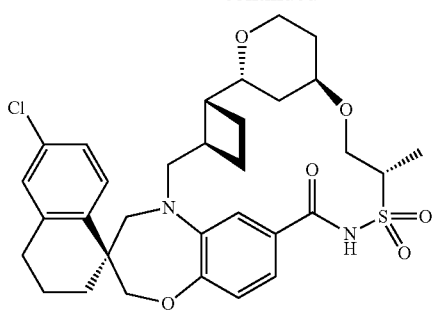
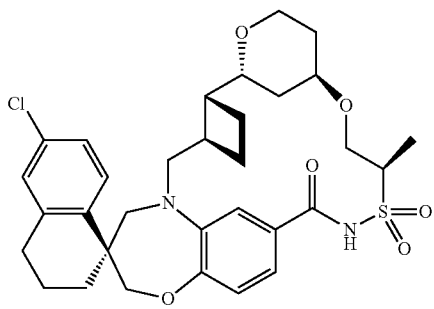
or
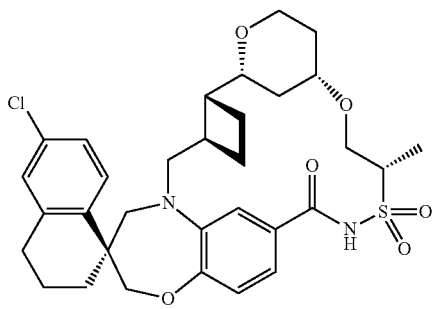
or
1926
-continued
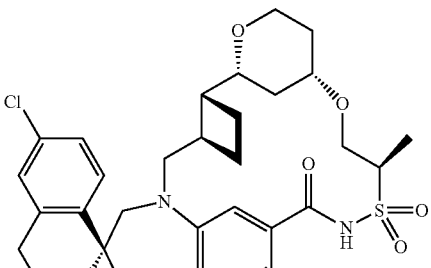
or
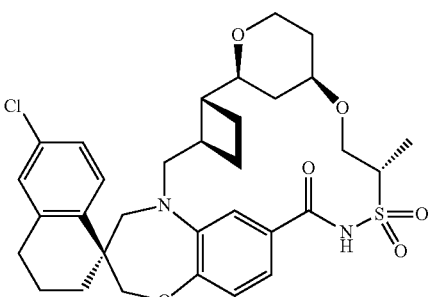
or
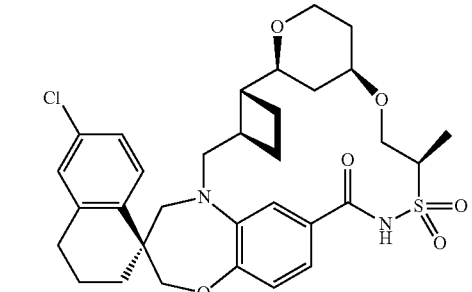
The title compound (2.1 mg) was obtained as a single isomer (first eluting peak) from the reverse phase preparative HPLC in Example 919. $^1$H NMR (400 MHz, CD$_2$Cl$_2$) δ 8.10 (br. s., 1H), 7.72 (d, J=8.61 Hz, 1H), 7.17 (dd, J=2.25, 8.51 Hz, 1H), 7.07 (m, 2H), 6.94 (d, J=8.02 Hz, 1H), 6.64 (s, 1H), 4.09 (d, J=7.04 Hz, 4H), 3.84 (d, J=6.46 Hz, 2H), 3.77 (d, J=2.54 Hz, 2H), 3.74-3.69 (m, 3H), 3.65-3.61 (m, 2H), 3.18-3.04 (m, 2H), 2.81-2.72 (m, 4H), 2.48-2.38 (m, 1H), 2.18-1.23 (m, 12H). m/z (ESI, +ve ion) 615.1 (M+H).

Example 922. (1S,3'R,6'R,7'S,11'S,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'S,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'R,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'R,13'R)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'S,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'S,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,1'R,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,1]'S,13'S)-6-chloro-13'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa [18,20,26]trien]-17'-one 15',15'-dioxide or (1S,3'R,6'R,7'S,11'S,14'S)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'S,14'R)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'R,14'S)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa [18,20,26]trien]-17'-one 15',15'-dioxide or (1S,3'R,6'R,7'R,11'R,14'R)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'S,14'S)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'R,11'S,14'R)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'R,14'S)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide or (1S,3'R,6'R,7'S,11'R,14'R)-6-chloro-14'-methyl-3,4-dihydro-2H,17'H-spiro[naphthalene-1,24'-[8,12,22]trioxa[15]thia[1,16]diazapentacyclo[16.7.2.1$^{7,11}$.0$^{3,6}$.0$^{21,26}$]octacosa[18,20,26]trien]-17'-one 15',15'-dioxide

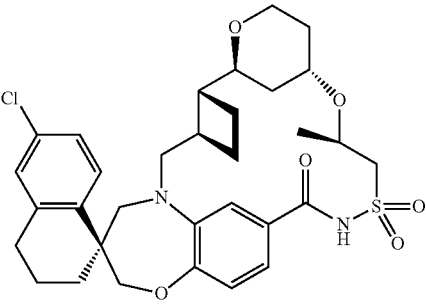

or

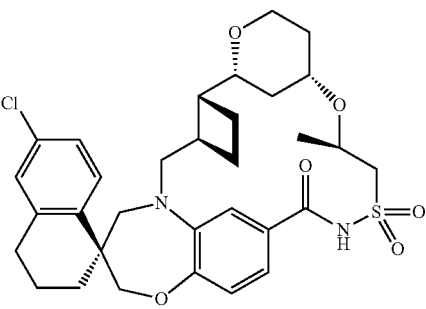

or

1929
-continued
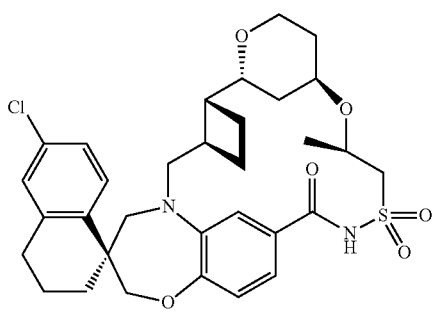
or
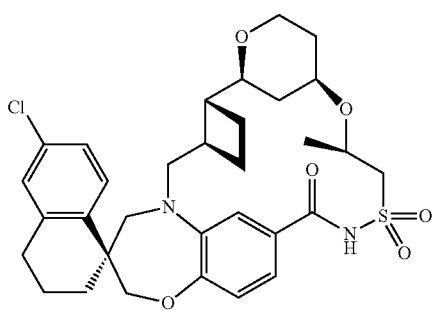
or
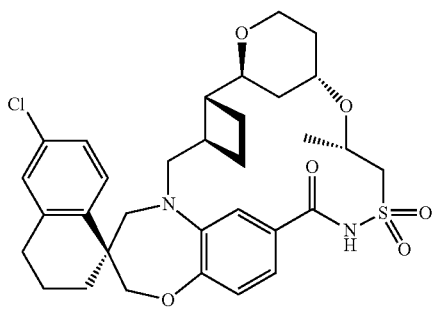
or
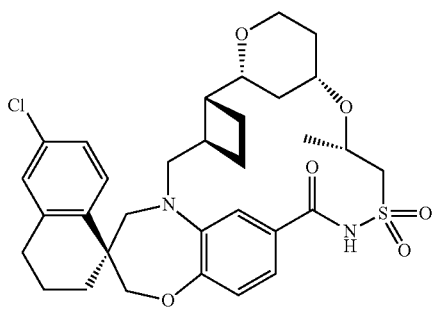
or
1930
-continued
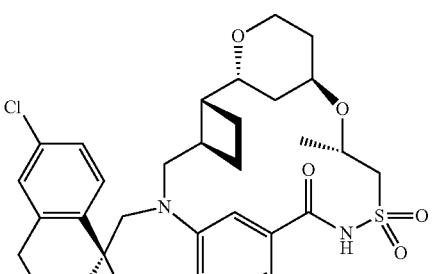
or
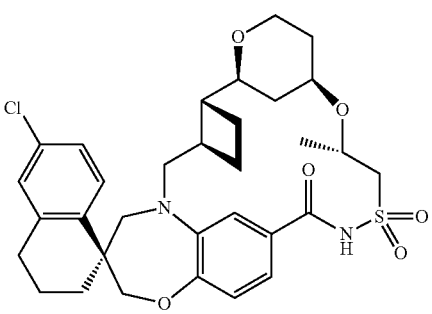
or
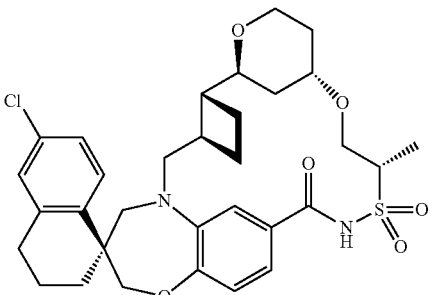
or
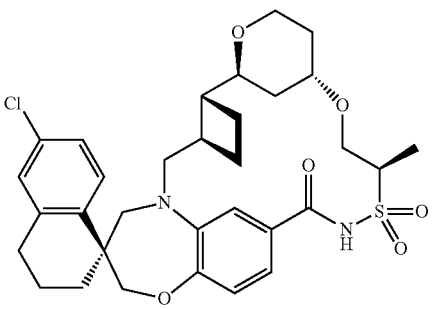
or -continued

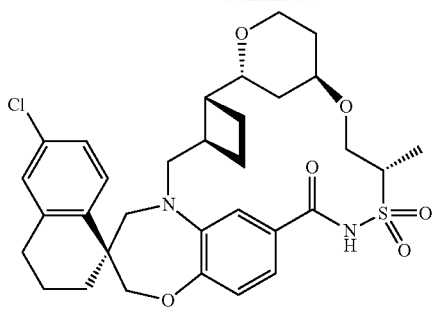

or

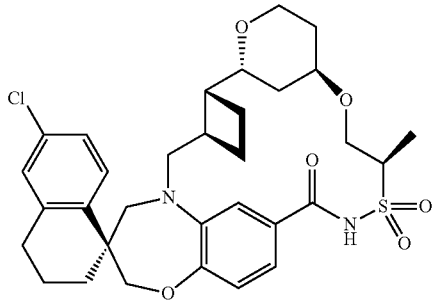

or

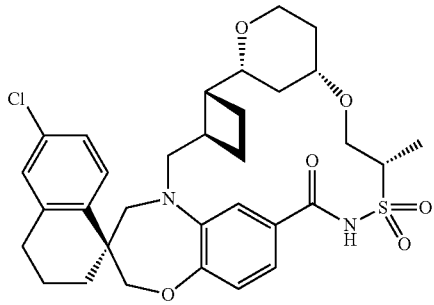

or

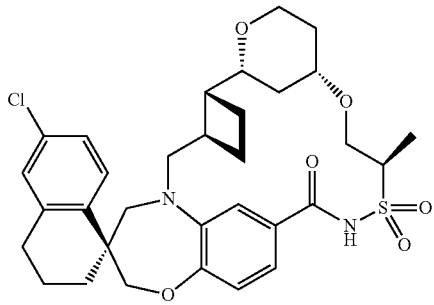

or

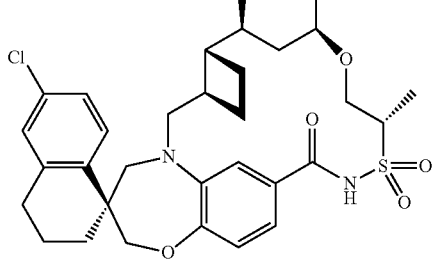

or

-continued

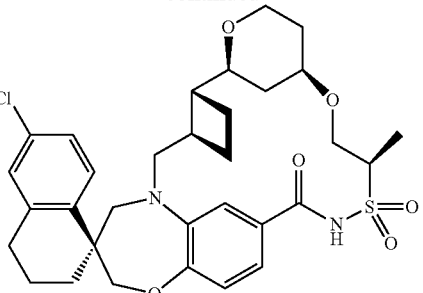

The title compound (3.5 mg) was obtained as a single isomer (second eluting peak) from the reverse phase preparative HPLC in Example 919. $^1$H NMR (400 MHz, CD$_2$Cl$_2$) δ 8.20 (m, 1H), 7.71 (m, 1H), 7.09 (s, 3H), 6.96 (m, 1H), 6.56 (m, 1H), 4.09 (d, J=7.24 Hz, 4H), 3.95-3.82 (m, 2H), 3.81-3.63 (m, 5H), 3.28 (br. s., 2H), 3.16 (d, J=6.46 Hz, 1H), 2.84-2.72 (m, 2H), 2.48-2.28 (m, 2H), 2.16-2.04 (m, 2H), 1.98-1.89 (m, 1H), 1.87-1.62 (m, 7H), 1.44 (t, J=12.23 Hz, 1H), 1.32 (d, J=6.06 Hz, 3H). m/z (ESI, +ve ion) 615.1 (M+H).

Example 923. (3R,6R,7S,22S)-6'-chloro-7-hydroxy-3',4'-dihydro-2'H,15H-spiro[9,20-dioxa-13-thia-1,14-diazatetracyclo[14.7.2.0$^{3,6}$.0$^{19,24}$]pentacosa-16,18,24-triene-22,1'-naphthalen]-15-one 13,13-dioxide or (3R,6R,7R,22S)-6'-chloro-7-hydroxy-3',4'-dihydro-2'H,15H-spiro[9,20-dioxa-13-thia-1,14-diazatetracyclo[14.7.2.0$^{3,6}$.0$^{19,24}$]pentacosa-16,18,24-triene-22,1'-naphthalen]-15-one 13,13-dioxide

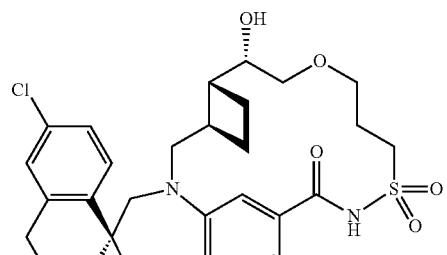

or

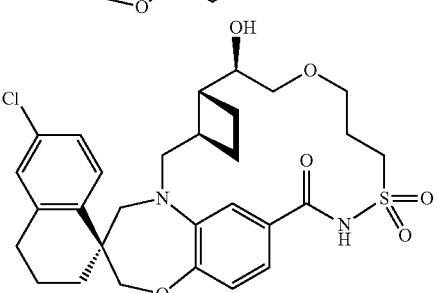

Platinum (IV) oxide (0.22 mg, 0.97 μmol) was added to a solution of Example 917 (0.003 g, 4.9 μmol) in EtOAc (1.6 mL). It was stirred under H$_2$ atmosphere for 36 min. It was concentrated and the residue was purified by reverse phase preparative HPLC (Gemini™ Prep C$_{18}$ 5 μm column; Phenomenex, Torrance, CA; MeCN in water with 0.1% TFA, gradient elution) to provide the title compound (1.3 mg) as a film. $^1$H NMR (400 MHz, CD$_2$Cl$_2$) δ 7.74 (m, 1H), 7.44

(m, 1H), 7.28 (m, 1H), 7.18 (m, 1H), 7.10 (m, 1H), 6.97 (m, 1H), 4.13 (d, J=4.11 Hz, 2H), 4.02 (m, 1H), 3.98-3.89 (m, 2H), 3.79 (dd, J=6.26, 9.00 Hz, 1H), 3.70-3.63 (m, 2H), 3.58-3.53 (m, 1H), 3.46 (d, J=6.65 Hz, 2H), 3.22-3.17 (m, 1H), 3.09-3.03 (m, 1H), 2.83-2.76 (m, 2H), 2.51 (d, J=7.43 Hz, 2H), 2.37-2.27 (m, 2H), 2.15-1.18 (m, 9H). m/z (ESI, +ve ion) 575.1 (M+H)+.

Example 924. (3R,6R,7R,11S,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide or (3R,6R,7S,11S,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide or (3R,6R,7R,11R,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide or (3R,6R,7S,11S,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-18,20,26-triene-24,1'-naphthalen]-17-one 15,15-dioxide

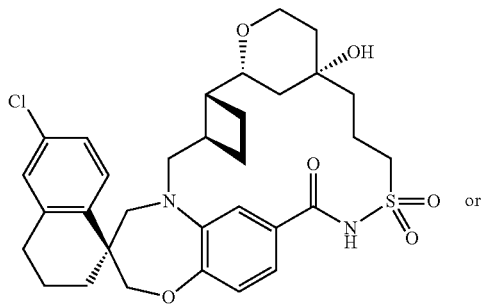

or

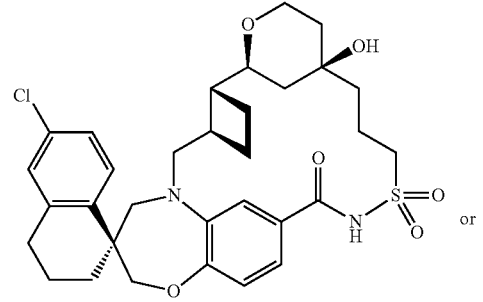

or

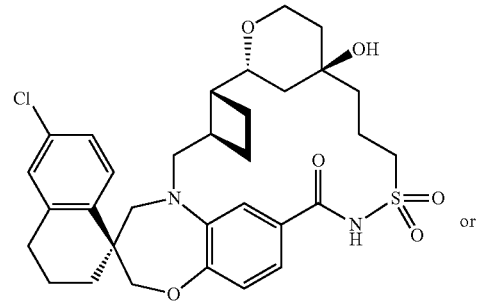

or

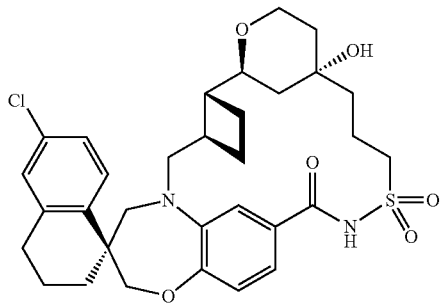

Platinum (IV) oxide (1.1 mg, 5 µmol) was added to a solution (3R,6R,7S,11S,12E,24S)-6'-chloro-11-hydroxy-3',4'-dihydro-2'H,17H-spiro[8,22-dioxa-15-thia-1,16-diazapentacyclo[16.7.2.1$^{7,11}$.0$^{3,6}$.0$^{21,26}$]octacosa-12,18,20,26-tetraene-24,1'-naphthalen]-17-one 15,15-dioxide (Example 851; 0.003 g, 5 µmol) in EtOAc (5 mL). It was stirred under H$_2$ for 1 h. After concentration the residue was purified by reverse phase preparative HPLC (Gemini™ Prep C$_{18}$ 5 µm column; Phenomenex, Torrance, CA; MeCN in water with 0.1% TFA, gradient elution) to provide the title compound (0.9 mg) as a white solid. $^1$H NMR (500 MHz, CD$_2$Cl$_2$) δ 8.00 (m, 1H), 7.70 (m, 1H), 7.17 (m, 1H), 7.10 (m, 1H), 6.96 (s, 2H), 6.79 (m, 1H), 4.16-4.04 (m, 2H), 3.91-3.80 (m, 2H), 3.78-3.62 (m, 2H), 3.48-3.31 (m, 3H), 3.28-3.15 (m, 2H), 2.83-2.71 (m, 2H), 2.56-2.47 (m, 1H), 2.38-2.29 (m, 1H), 2.14-2.06 (m, 1H), 2.03-1.35 (m, 16H). m/z (ESI, +ve ion) 615.0 (M+H)+.

Example 927. (1S,3'R,6'R,7'S)-6-chloro-7'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R)-6-chloro-7'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

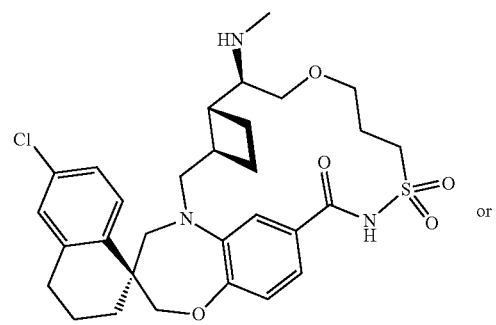

or

1935
-continued

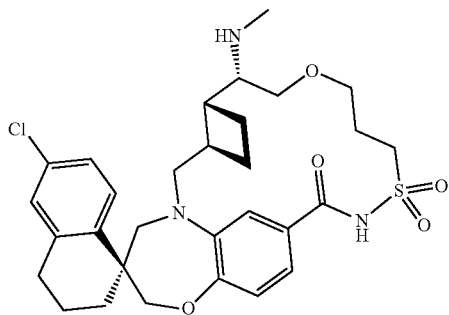

(1S,3'R,6'R)-6-Chloro-3,4-dihydro-2H,7'H,15'H-spiro [naphthalene-1,22'-[20]oxa[13]thia[1,14]diazatetracyclo [14.7.2.0$^{3,6}$.0$^{19,24}$pentacosa[16,18,24]triene]-7,15'-dione 13',13'-dioxide (Example 832; 12 mg, 0.021 mmol) was dissolved in 0.53 mL of THF and 0.53 mL of DCE. To this mixture was added methylamine (2.0 M solution in tetrahydrofuran, 42.0 µl, 0.084 mmol), acetic acid (4.81 µl, 0.084 mmol) and sodium triacetoxyborohydride (11.13 mg, 0.053 mmol). The reaction was stirred at rt for overnight. 3 mL of aq. Na$_2$CO$_3$ solution and 10 mL of EtOAc were added. The organic layer was concentrated and purified by reversed phase preparative HPLC (Gemini™ Prep C$_{18}$ 5 µm column; Phenomenex, Torrance, CA; gradient elution of 30% to 95% MeCN in water, where both solvents contain 0.1% TFA, 30 min method) to give (1S,3'R,6'R,7'S)-6-chloro-7'-(methylamino)-3,4-dihydro-2H,15'H-spiro[naphthalene-1,22'-[20] oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R, 7'R)-6-chloro-7'-(methylamino)-3,4-dihydro-2H,15'H-spiro [naphthalene-1,22'-[20]oxa[13]thia[1,14]diazatetracyclo [14.7.2.0$^{3,6}$.0$^{19,24}$]pentacosa[16,18,24]trien]-15'-one 13', 13'-dioxide (4.2 mg, 7.16 µmol, second eluting major peak) from the reverse phase preparative HPLC. $^1$H NMR (400 MHz, DMSO-d$_6$) δ 8.39 (br. s., 1H), 8.23 (br. s., 1H), 7.67 (d, J=8.4 Hz, 1H), 7.29 (dd, J=2.5, 8.8 Hz, 1H), 7.21 (d, J=2.0 Hz, 1H), 7.06 (d, J=8.6 Hz, 1H), 6.96 (d, J=8.2 Hz, 1H), 6.86 (s, 1H), 4.07 (dd, J=12.3, 37.8 Hz, 2H), 3.93 (d, J=15.5 Hz, 1H), 3.70 (d, J=15.1 Hz, 1H), 3.64 (d, J=14.1 Hz, 1H), 3.53 (br. s., 1H), 3.03 (dd, J=10.6, 14.3 Hz, 1H), 2.85-2.67 (m, 2H), 2.59-2.50 (m, 2H overlap with solvent) 2.34 (br. s., 2H), 1.99 (d, J=10.4 Hz, 1H), 1.95-1.18 (m, 17H). m/z (ESI, +ve ion) 586.2 (M+H)$^+$;

Example 928. (1S,3'R,6'R,7'R)-6-chloro-7'-((2-hydroxyethyl)amino)-3,4-dihydro-2H,15'H-spiro[naphthalene-1,22'-[20]oxa[13]thia[1,14]diazatetracyclo [14.7.2.0$^{3,6}$.0$^{19,24}$]pentacosa [16,18,24]trien]-15'-one 13',13'-dioxide or (1S,3'R,6'R,7'S)-6-chloro-7'-((2-hydroxyethyl)amino)-3,4-dihydro-2H,15'H-spiro [naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

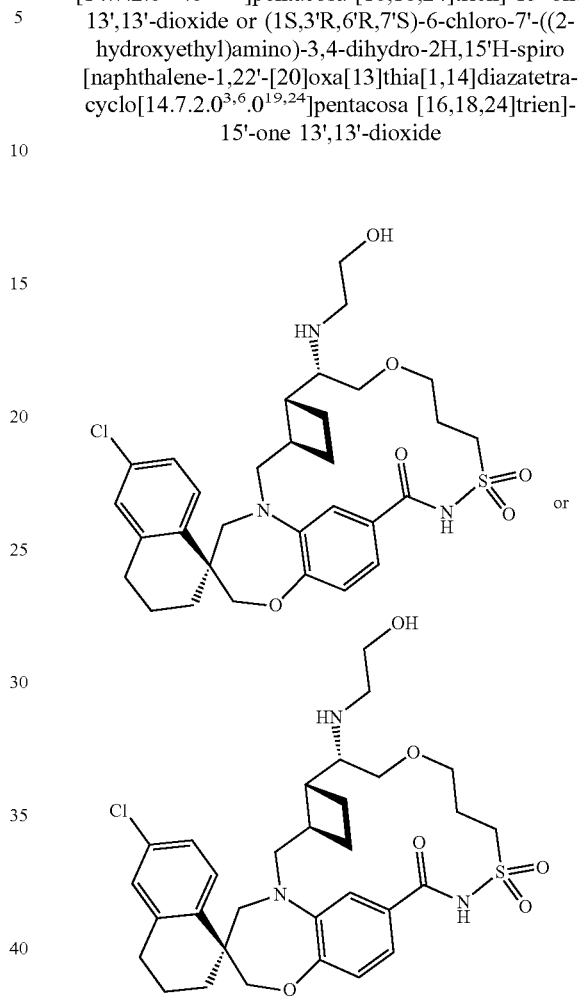

The title compound was prepared in an analogous manner to that described in Example 927, using (1S,3'R,6'R)-6-Chloro-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 13',13'-dioxide (Example 832) and ethanolamine (Aldrich), and the desired product, (1S,3'R,6'R,7'R)-6-chloro-7'-((2-hydroxyethyl) amino)-3,4-dihydro-2H,15'H-spiro[naphthalene-1,22'-[20] oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R, 7'S)-6-chloro-7'-((2-hydroxyethyl)amino)-3,4-dihydro-2H, 15'H-spiro[naphthalene-1,22'-[20]oxa[13]thia[1,14] diazatetracyclo[14.7.2.0$^{3,6}$.0$^{19,24}$]pentacosa[16,18,24] trien]-15'-one 13',13'-dioxide was isolated as a single isomer (first eluting major peak) from the reverse phase preparative HPLC. $^1$H NMR (400 MHz, CD$_3$OD) δ 7.76 (d, J=8.4 Hz, 1H), 7.21 (dd, J=2.2, 8.5 Hz, 1H), 7.14 (d, J=2.2 Hz, 1H), 7.07 (dd, J=2.0, 8.2 Hz, 1H), 7.01 (d, J=2.0 Hz, 1H), 6.99 (d, J=8.0 Hz, 1H), 4.20-4.14 (m, 1H), 4.04 (d, J=12.1 Hz, 1H), 3.93 (dd, J=3.5, 15.1 Hz, 1H), 3.86 (d, J=14.3 Hz, 1H), 3.81-3.73 (m, 2H), 3.69 (dd, J=8.2, 15.1 Hz, 1H), 3.53 (t, J=7.2 Hz, 1H), 3.25-3.18 (m, 2H), 3.14-3.04 (m, 1H), 2.88-2.77 (m, 2H), 2.77-2.65 (m, 1H), 2.57-2.36 (m, 1H), 2.10 (d, J=9.4 Hz, 3H), 2.01-1.77 (m, 6H), 1.75-1.61 (m, 4H), 1.61-1.45 (m, 3H). m/z (ESI, +ve ion) 616.1

Example 929. (1S,3'R,6'R,7'S)-6-chloro-7'-((2-hydroxyethyl)amino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R)-6-chloro-7'-((2-hydroxyethyl)amino)-3,4-dihydro-2H,15'H-spiro [naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide Example 930. (1S,3'R,6'R,7'R)-6-chloro-7'-((2,2,2-trifluoroethyl)amino)-3,4-dihydro-2H,15'H-spiro [naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S)-6-chloro-7'-((2,2,2-trifluoroethyl)amino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

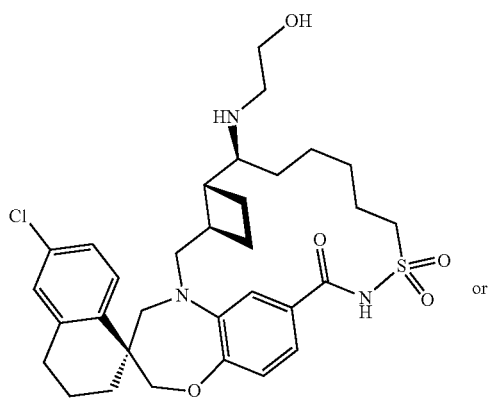

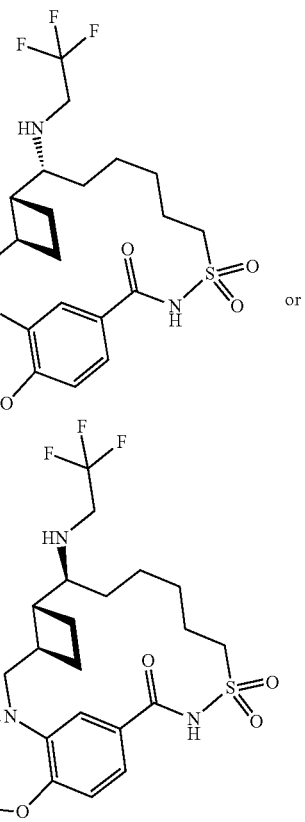

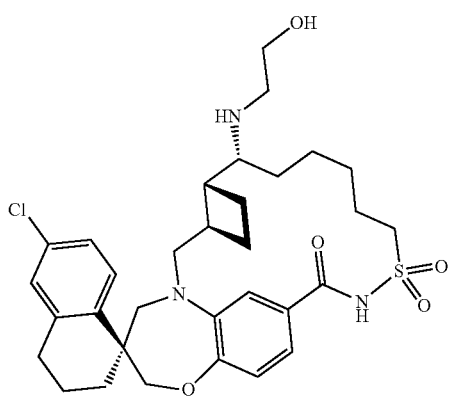

The title compound was obtained as a single isomer (second eluting peak) from the reverse preparative phase HPLC in Example 928. $^1$H NMR (500 MHz, CD$_3$OD) δ 7.76 (d, J=8.6 Hz, 1H), 7.20 (dd, J=2.3, 8.4 Hz, 1H), 7.14 (d, J=2.2 Hz, 1H), 7.10 (dd, J=2.0, 8.1 Hz, 1H), 6.99 (d, J=8.1 Hz, 1H), 6.87 (d, J=1.7 Hz, 1H), 6.88-6.86 (m, 1H), 4.12 (dd, J=11.5, 28.6 Hz, 2H), 4.01 (dd, J=7.1, 13.9 Hz, 1H), 3.93 (d, J=15.2 Hz, 1H), 3.87-3.81 (m, 2H), 3.75 (d, J=13.7 Hz, 1H), 3.49-3.40 (m, 2H), 3.22-3.03 (m, 3H), 2.87-2.74 (m, 2H), 2.63-2.50 (m, 2H), 2.14-2.02 (m, 2H), 2.00-1.67 (m, 8H), 1.67-1.54 (m, 3H), 1.54-1.44 (m, 2H). m/z (ESI, +ve ion) 616.1

The title compound was prepared in an analogous manner to that described in Example 927, using (1S,3'R,6'R)-6-Chloro-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 13',13'-dioxide (Example 832, 12 mg) and 2,2,2-trifluoroethylamine (Sigma), and the desired product, (1S,3'R,6'R,7'R)-6-chloro-7'-((2,2,2-trifluoroethyl)amino)-3,4-dihydro-2H,15'H-spiro [naphthalene-1,22'-[20]oxa[13]thia[1,14]diazatetracyclo [14.7.2.0$^{3,6}$.0$^{19,24}$]pentacosa[16,18,24]trien]-15'-one 13',13'-dioxide or (1S,3'R,6'R,7'S)-6-chloro-7'-((2,2,2-trifluoroethyl)amino)-3,4-dihydro-2H,15'H-spiro [naphthalene-1,22'-[20]oxa[13]thia[1,14]diazatetracyclo [14.7.2.0$^{3,6}$.0$^{19,24}$]pentacosa[16,18,24]trien]-15'-one 13',13'-dioxide was isolated as a single isomer (first eluting major peak) from the reverse phase preparative HPLC. $^1$H NMR (500 MHz, CD$_3$OD) δ 7.76 (d, J=8.6 Hz, 1H), 7.20 (dd, J=2.2, 8.3 Hz, 1H), 7.13 (d, J=2.2 Hz, 1H), 7.08 (dd, J=2.0, 8.3 Hz, 1H), 6.98 (d, J=8.1 Hz, 1H), 6.90 (d, J=2.0 Hz, 1H), 4.11 (dd, J=12.7, 24.7 Hz, 2H), 4.02-3.94 (m, 1H), 3.90 (d, J=15.4 Hz, 1H), 3.81-3.54 (m, 3H), 3.41-3.32 (m, 2H), 3.13 (dd, J=8.3, 15.4 Hz, 1H), 2.87-2.75 (m, 2H), 2.57-2.46 (m, 2H), 2.12 (d, J=13.7 Hz, 1H), 2.07-1.67 (m, 10H), 1.65-1.43 (m, 6H). m/z (ESI, +ve ion) 654.2 (M+H)+.

Example 931. (1S,3'R,6'R,7'S)-6-chloro-7'-((2,2,2-trifluoroethyl)amino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R)-6-chloro-7'-((2,2,2-trifluoroethyl)amino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

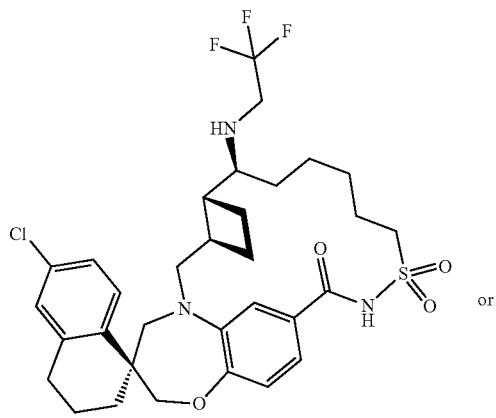

or

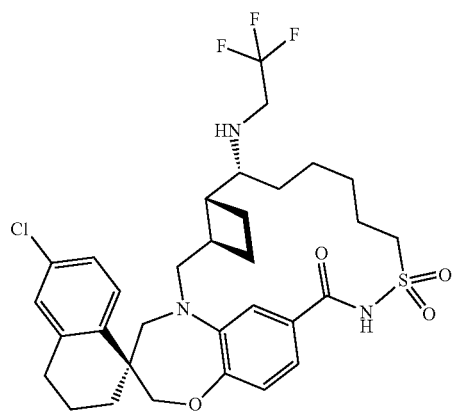

The title compound was obtained a as a single isomer (second eluting peak) from the reverse phase preparative HPLC in in Example 930. $^1$H NMR (500 MHz, CD$_3$OD) δ 7.72 (d, J=8.5 Hz, 1H), 7.23 (s, 1H), 7.18 (dd, J=2.2, 8.6 Hz, 1H), 7.11 (d, J=2.2 Hz, 1H), 7.04 (dd, J=2.0, 8.1 Hz, 1H), 6.94 (d, J=8.1 Hz, 1H), 4.08 (dd, J=12.2, 27.4 Hz, 2H), 3.99 (d, J=15.2 Hz, 1H), 3.85-3.78 (m, 1H), 3.72 (d, J=14.2 Hz, 1H), 3.63-3.48 (m, 2H), 3.11 (dd, J=8.7, 15.3 Hz, 1H), 2.84-2.73 (m, 3H), 2.61-2.54 (m, 1H), 2.46-2.40 (m, 1H), 2.08 (d, J=13.9 Hz, 1H), 2.02-1.84 (m, 5H), 1.75-1.64 (m, 4H), 1.61 (br. s., 2H), 1.57 (br. s., 1H), 1.54-1.39 (m, 5H). m/z (ESI, +ve ion) 654.2 (M+H)+.

Example 932. (1S,3'R,6'R,7'Z)-6-chloro-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa [16,18,24]triene]-7',15'-dione 7-OXIME 13',13'-dioxide and (1S,3'R,6'R,7'E)-6-chloro-3,4-dihydro-2H,7'H,15'H-spiro[naphthalene-1,22'-[20]oxa[13]thia[1,14]diazatetracyclo[14.7.2.0$^{3,6}$.0$^{19,24}$] pentacosa [16,18,24]triene]-7',15'-dione 7-OXIME 13',13'-dioxide

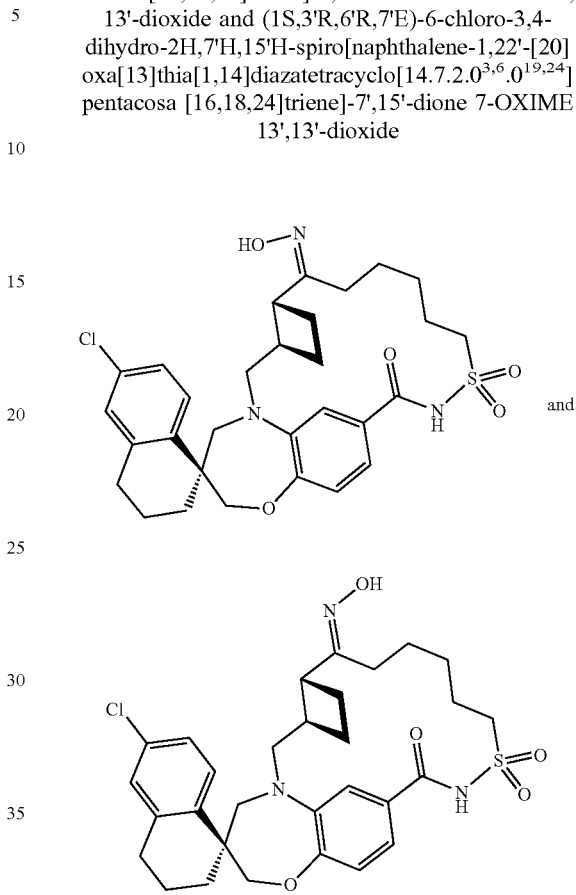

To a 25-mL round-bottomed flask was added (1S,3'R, 6'R)-6-chloro-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 13',13'-dioxide (Example 832; 205 mg, 0.36 mmol) and hydroxyammonium chloride (24.9 mg, 0.359 mmol, Alfa Aesar), ammonium acetate (25.8 μl, 0.36 mmol, Sigma), 0.3 mL of pyridine and 7.2 mL of EtOH. The reaction mixture was heated to reflux for 2 h. The reaction was concentrated and purified through a 4 g ISCO Gold column, eluting with 0-45% EtOAc(with 0.3% HOAc) in hexane to give (1S,3'R, 6'R,7'Z)-6-chloro-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 7'-oxime 13',13'-dioxide and (1S,3'R,6'R,7'Z)-6-chloro-3,4-dihydro-2H,7'H,15'H-spiro[naphthalene-1,22'-[20]oxa[13]thia[1,14] diazatetracyclo[14.7.2.0$^{3,6}$.0$^{19,24}$]pentacosa[16,18,24]triene]-7',15'-dione 7'-oxime 13',13'-dioxide (0.195 g, 0.33 mmol) as a mixture of trans and cis isomers. $^1$H NMR (400 MHz, CD$_3$OD) δ 7.75 (t, J=8.0 Hz, 1H), 7.17 (dd, J=2.2, 8.6 Hz, 1H), 7.10 (s, 1H), 7.07 (d, J=2.0 Hz, 0.5H), 7.03-6.99 (m, 1H), 6.94-6.86 (m, 1H), 6.85 (d, J=1.8 Hz, 0.5H), 4.10-3.96 (m, 3H), 3.87-3.69 (m, 3H), 3.43-3.34 (m, 2H), 3.43-3.34 (m, 2H), 3.43-3.34 (m, 2H), 3.17-3.07 (m, 1H), 3.05-2.94 (m, 1H), 2.90-2.63 (m, 3H), 2.36-2.27 (m, 1H), 2.20-1.66 (m, 7H), 1.58 (d, J=12.3 Hz, 1H), 1.54-1.37 (m, 2H). m/z (ESI, +ve ion) 586.2 (M+H)+.

Example 933. (1S,3'R,6'R,7'R)-6-chloro-7'-(hydroxyamino)-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide or (1S,3'R,6'R,7'S)-6-chloro-7'-(hydroxyamino)-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide

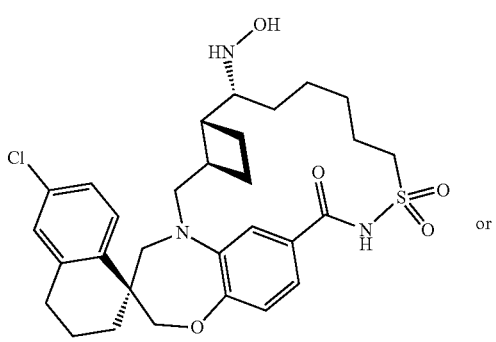 or

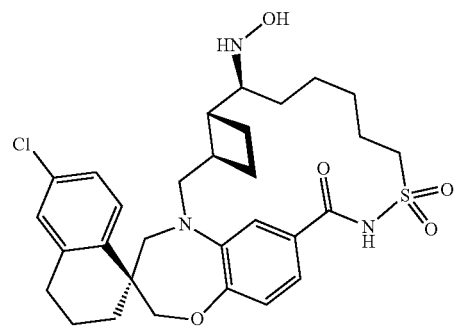

A mixture of (1S,3'R,6'R,7'Z)-6-chloro-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[16,18,24]triene]-7',15'-dione 7'-oxime 13',13'-dioxide and (1S,3'R,6'R,7'E)-6-chloro-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[16,18,24]triene]-7',15'-dione 7-oxime 13',13'-dioxide (Example 932; 32 mg, 0.054 mmol) was dissolved in 2 mL of MeOH, and then sodium cyanoborohydride (10.2 mg, 0.16 mmol, Aldrich), titanium chloride (63.4 µl, 0.11 mmol, Fisher Scientific) were added. The reaction mixture was stirred at rt overnight, and then conc, diluted with 30 mL of DCM and 1N aq. NaOH solution was added to adject pH to 10. The organic layer was concentrated and purified by reversed phase preparative HPLC (Gemini™ Prep C₁₈ 5 µm column; Phenomenex, Torrance, CA; gradient elution of 30% to 95% MeCN in water, where both solvents contain 0.1% TFA, 30 min method) to give (1S,3'R,6'R,7'R)-6-chloro-7'-(hydroxyamino)-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'S)-6-chloro-7'-(hydroxyamino)-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide (19 mg, 0.032 mmol; major isomer). ¹H NMR (400 MHz, CD₃OD) δ 7.76 (d, J=8.6 Hz, 1H), 7.25-7.19 (m, 2H), 7.14 (d, J=2.3 Hz, 1H), 7.04 (dd, J=2.2, 8.2 Hz, 1H), 6.97 (d, J=8.0 Hz, 1H), 4.16-4.03 (m, 3H), 3.94-3.83 (m, 1H), 3.77 (d, J=13.7 Hz, 1H), 3.30-3.20 (m, 2H), 3.11 (dd, J=9.9, 15.0 Hz, 1H), 2.89-2.69 (m, 3H), 2.49 (d, J=12.7 Hz, 1H), 2.17-1.39 (m, 17H). m/z (ESI, +ve ion) 588.2 (M+H)⁺.

Example 934. N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [16,18,24]trien]-7'-yl)acetamide or N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [16,18,24]trien]-7'-yl)acetamide

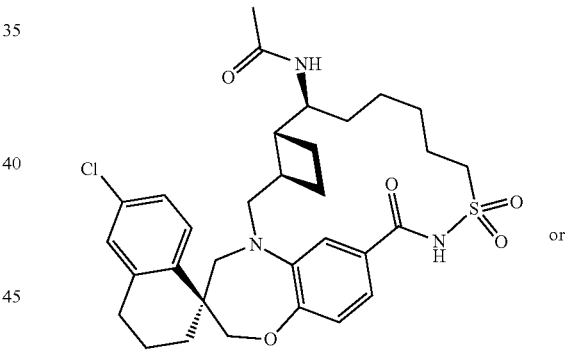 or

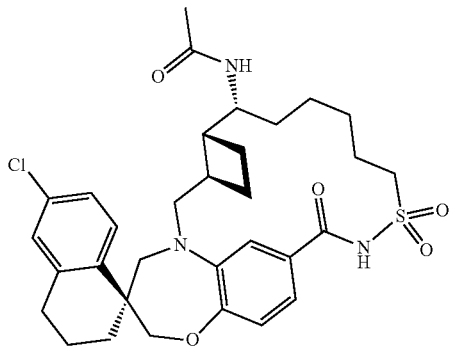

1943

Step 1: (1S,3'R,6'R,7'S)-6-chloro-7'-((4-methoxybenzyl)amino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'R)-6-chloro-7'-((4-methoxybenzyl)amino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

1944

Step 2: N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)-N-(4-methoxybenzyl)acetamide or N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)-N-(4-methoxybenzyl)acetamide

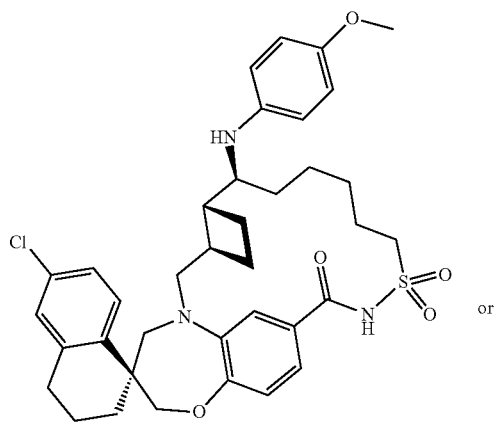

or

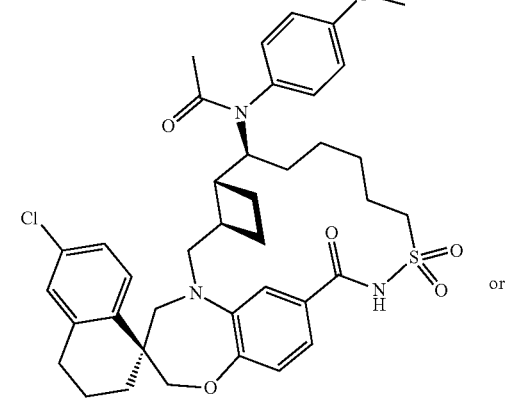

or

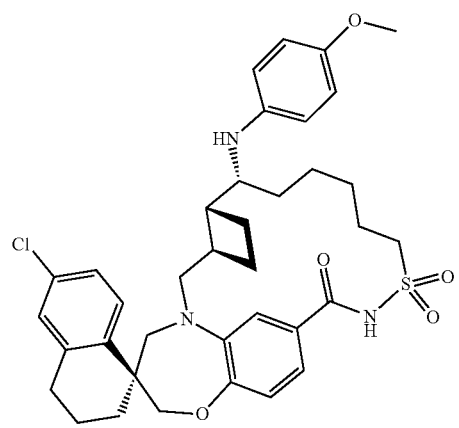

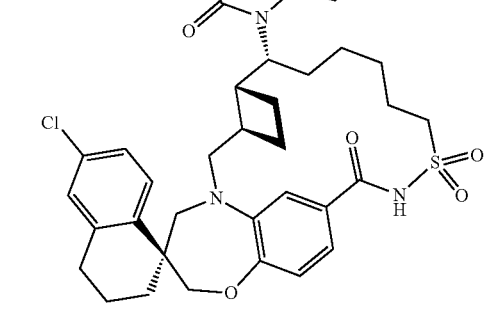

The title compound was prepared in an analogous manner to that described in Example 927, using (1S,3'R,6'R)-6-Chloro-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[16,18,24]triene]-7',15'-dione 13',13'-dioxide (Example 832, 12 mg) and 4-methoxybenzylamine (Alfa Aesar), and the desired product, (1S,3'R,6'R,7'S)-6-chloro-7'-((4-methoxybenzyl)amino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R)-6-chloro-7'-((4-methoxybenzyl)amino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (15.7 mg, 0.023 mmol) was isolated as a single isomer (first eluting major peak) from the reverse phase preparative HPLC.

To a 25-mL round-bottomed flask was added (1S,3'R,6'R,7'S)-6-chloro-7'-((4-methoxybenzyl)amino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R)-6-chloro-7'-((4-methoxybenzyl)amino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (first eluting major peak out of preparative reverse phase HPLC (from Step 1, 11.0 mg, 0.016 mmol), DMAP (1.94 mg, 0.016 mmol, Aldrich), DIEA (5.5 µl, 0.032 mmol, Aldrich) and 1.5 mL of DCM, and then acetyl chloride (1.5 mg, 0.019 mmol, Aldrich) was added. After 30 min, the reaction mixture was concentrated and purified by reversed phase preparative HPLC (Gemini™ Prep $C_{18}$ 5 µm column; Phenomenex, Torrance, CA; gradient elution of 60% to 95% MeCN in water, where both solvents contain 0.1% TFA, 30 min method) to give the title product (11.6 mg, 0.016 mmol).

Step 3: N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)acetamide or N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)acetamide The mixture of N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)-N-(4-methoxybenzyl)acetamide or N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)-N-(4-methoxybenzyl)acetamide (from Step 2; 11.6 mg, 0.016 mmol) in 4 mL of 100% TFA was heated to 80° C. for 24 h. The mixture was concentrated and purified by reversed phase preparative HPLC (Gemini™ Prep C$_{18}$ 5 μm column; Phenomenex, Torrance, CA; gradient elution of 40% to 95% MeCN in water, where both solvents contain 0.1% TFA, 30 min method) to give N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)acetamide or N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)acetamide (5.2 mg, 0.009 mmol). $^1$H NMR (400 MHz, CD$_3$OD) δ 7.73 (d, J=8.4 Hz, 1H), 7.17 (dd, J=2.3, 8.2 Hz, 1H), 7.10 (dd, J=2.1, 4.6 Hz, 2H), 7.07 (dd, J=2.0, 8.2 Hz, 1H), 6.95 (d, J=8.2 Hz, 1H), 4.09 (dd, J=11.9, 20.1 Hz, 2H), 3.80-3.65 (m, 4H), 3.38 (dd, J=7.6, 15.5 Hz, 1H), 3.19 (dd, J=7.9, 15.4 Hz, 1H), 2.84-2.70 (m, 2H), 2.50-2.39 (m, 1H), 2.39-2.27 (m, 1H), 2.05 (d, J=13.7 Hz, 1H), 1.97 (s, 3H), 1.95-1.32 (m, 14H). m/z (ESI, +ve ion) 614.2 (M+H)$^+$.

Example 935. N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)acetamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)acetamide

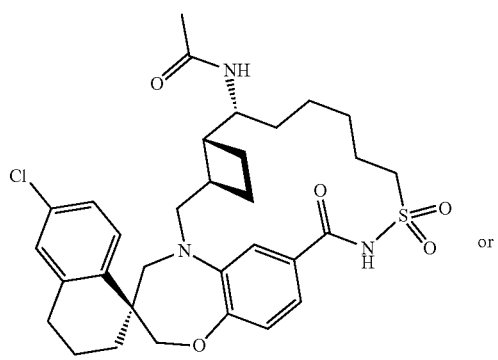

or

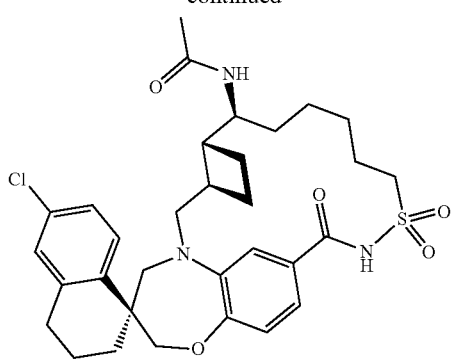

Step 1: (1S,3'R,6'R,7'R)-6-chloro-7'-((4-methoxybenzyl)amino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide and (1S,3'R,6'R,7'S)-6-chloro-7'-((4-methoxybenzyl)amino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

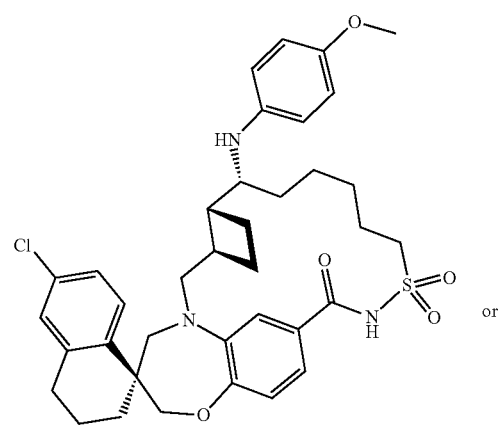

or

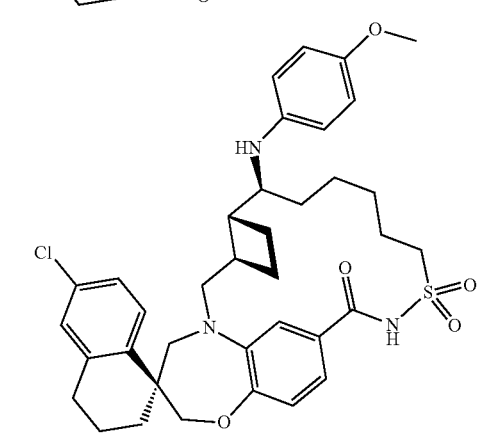

The title compound was obtained as a single isomer (second eluting major peak) from the reverse phase preparative HPLC in Example 934, Step 1.

Step 2: N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [16,18,24]trien]-7'-yl)-N-(4-methoxybenzyl)acetamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [16,18,24]trien]-7'-yl)-N-(4-methoxybenzyl)acetamide

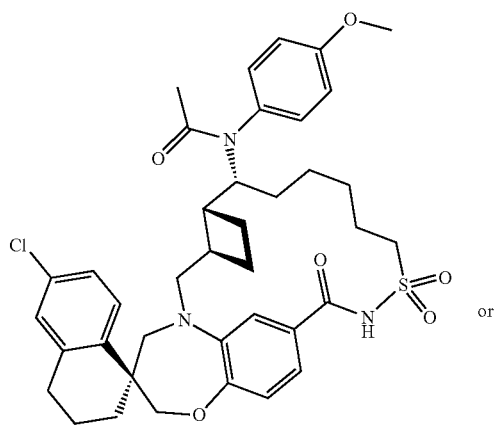

or

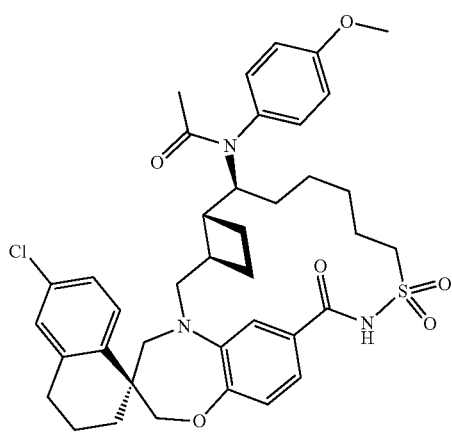

To a 25-mL round-bottomed flask was added (1S,3'R,6'R,7'R)-6-chloro-7'-((4-methoxybenzyl)amino)-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'S)-6-chloro-7'-((4-methoxybenzyl)amino)-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide (first eluting major isomer out of preparative reverse phase HPLC from Step 1, 17.2 mg, 0.025 mmol), DMAP (3.04 mg, 0.025 mmol, Aldrich), DIEA (8.68 μl, 0.05 mmol, Aldrich) and 2 mL of DCM, and then acetyl chloride (2.340 mg, 0.030 mmol, Aldrich) was added. After 30 min, the reaction mixture was concentrated and purified by reversed phase preparative HPLC (Gemini™ Prep C₁₈ 5 μm column; Phenomenex, Torrance, CA; gradient elution of 60% to 95% MeCN in water, where both solvents contain 0.1% TFA, 30 min method) to give the title product (18.2 mg, 0.025 mmol).

Step 3: N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [16,18,24]trien]-7'-yl)acetamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [16,18,24]trien]-7'-yl)acetamide The mixture of N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[16,18,24]trien]-7'-yl)-N-(4-methoxybenzyl)acetamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[16,18,24]trien]-7'-yl)-N-(4-methoxybenzyl)acetamide (from Step 2; 18 mg, 0.025 mmol) in 4 mL of 100% TFA was heated to 80° C. for 24 h. The mixture was concentrated and purified by reversed phase preparative HPLC (Gemini™ Prep C₁₈ 5 μm column; Phenomenex, Torrance, CA; gradient elution of 40% to 95% MeCN in water, where both solvents contain 0.1% TFA, 30 min method) to give N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[16,18,24]trien]-7'-yl)acetamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[16,18,24]trien]-7'-yl)acetamide (8.2 mg, 0.013 mmol). $^1$H NMR (400 MHz, CD$_3$OD) δ 7.76 (d, J=8.4 Hz, 1H), 7.20 (dd, J=2.2, 8.5 Hz, 1H), 7.13 (d, J=2.2 Hz, 1H), 7.09 (dd, J=2.0, 8.0 Hz, 1H), 7.01 (d, J=2.0 Hz, 1H), 6.98 (d, J=8.2 Hz, 1H), 4.11 (dd, J=12.1, 14.5 Hz, 2H), 3.99 (d, J=15.1 Hz, 2H), 3.83-3.75 (m, 1H), 3.72 (d, J=14.9 Hz, 1H), 3.46 (dd, J=8.0, 15.5 Hz, 1H), 3.10 (dd, J=9.4, 15.3 Hz, 1H), 2.87-2.73 (m, 2H), 2.44-2.30 (m, 2H), 2.14 (d, J=13.7 Hz, 1H), 2.00 (br. s., 1H), 1.97 (s, 3H), 1.94-1.63 (m, 7H), 1.60-1.36 (m, 6H). m/z (ESI, +ve ion) 614.2 (M+H)⁺.

Example 936. N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[[14.7.2.0³,⁶.0¹⁹,²⁴]pentacosa[16,18,24]trien]-7'-yl)-2-methylpropanamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [16,18,24]trien]-7'-yl)-2-methylpropanamide

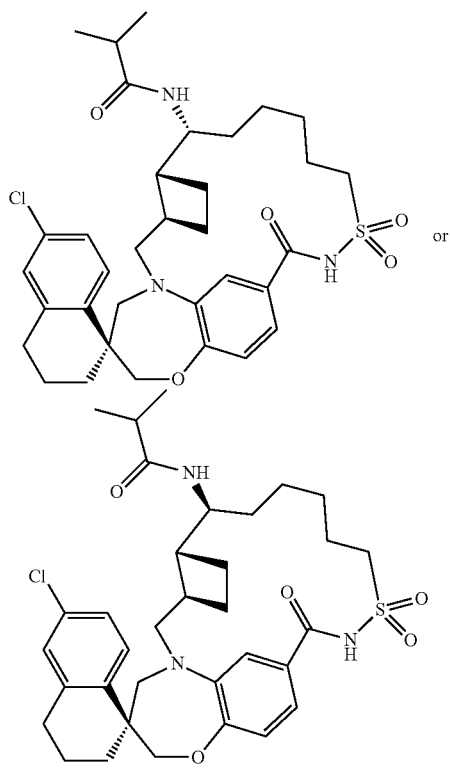

Step 1: (1S,3'R,6'R,7'R)-7'-amino-6-chloro-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'S)-7'-amino-6-chloro-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide

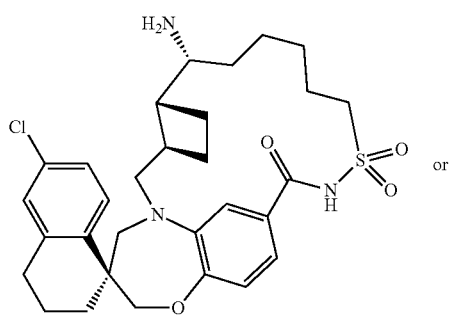

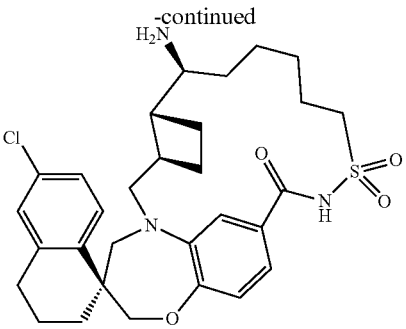

To a 25-mL round-bottomed flask was added (1S,3'R,6'R,7'R)-6-chloro-7'-(hydroxyamino)-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'S)-6-chloro-7'-(hydroxyamino)-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide (Example 933; 35 mg, 0.06 mmol), ammonium acetate (45.9 mg, 0.60 mmol) and zinc (38.9 mg, 0.60 mmol) in 4 mL of EtOH. The reaction mixture was heated to 90° C. for 30 min. The reaction mixture filtered and concentrated to give the crude desire product and directly go to next step.

Step 2: N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[[14.7.2.0³,⁶.0¹⁹,²⁴]pentacosa[16,18,24]trien]-7'-yl)-2-methylpropanamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa [16,18,24]trien]-7'-yl)-2-methylpropanamide The title compound was prepared in an analogous manner to that described in Example 935, Sep. 2, using (1S,3'R,6'R,7'R)-7'-amino-6-chloro-3,4-dihydro-2h,15'h-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'S)-7'-amino-6-chloro-3,4-dihydro-2h,15'h-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide (from Step 1), isobutyryl chloride (Fluka), and the desired product, N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[16,18,24]trien]-7'-yl)cyclopropanecarboxamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[16,18,24]trien]-7'-yl)cyclopropanecarboxamide was isolated as a white solid. $^1$H NMR (400 MHz, CD$_3$OD) δ 7.76 (d, J=8.4 Hz, 1H), 7.36 (d, J=7.5 Hz, 1H), 7.19 (dd, J=2.4, 8.5 Hz, 1H), 7.14 (d, J=2.0 Hz, 1H), 7.11 (dd, J=1.2, 7.8 Hz, 2H), 6.98 (d, J=8.0 Hz, 1H), 4.12 (dd, J=11.9, 17.4 Hz, 2H), 3.83-3.69 (m, 4H), 3.21 (dd, J=8.0, 15.3 Hz, 1H), 2.86-2.73 (m, 2H), 2.58-2.44 (m, 2H), 2.40-2.32 (m, 1H), 2.10-1.83 (m, 7H), 1.75-1.50 (m, 7H), 1.48-1.31 (m, 4H), 1.15 (d, J=6.8 Hz, 3H), 1.11 (d, J=6.8 Hz, 3H). m/z (ESI, +ve ion) 642.2 (M+H)⁺.

Example 937. N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)cyclopropanecarboxamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl) cyclopropanecarboxamide Example 938. N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)methanesulfonamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)methanesulfonamide

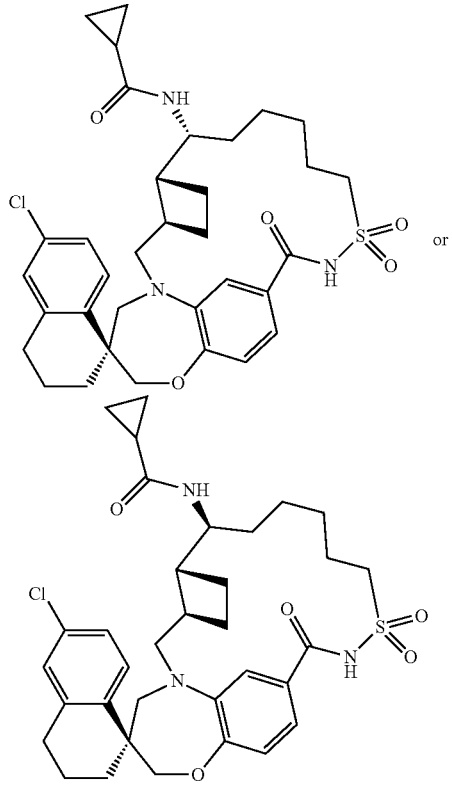

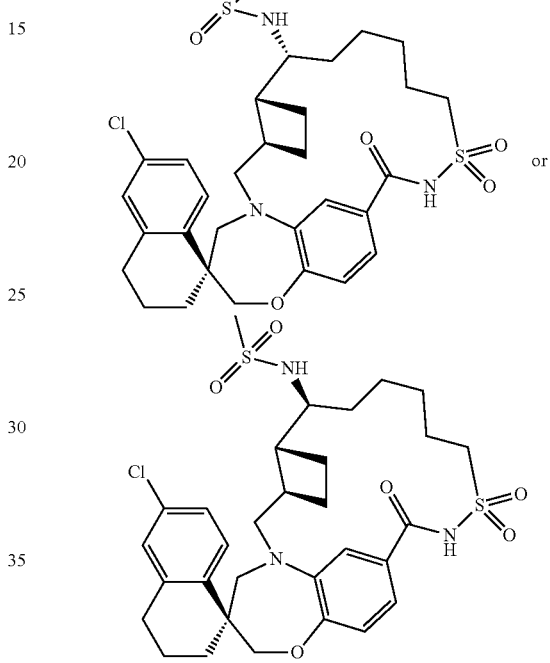

The title compound was prepared in an analogous manner to that described in Example 935, Step 2, using (1S,3'R,6'R,7'R)-7'-amino-6-chloro-3,4-dihydro-2h,15'h-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S)-7'-amino-6-chloro-3,4-dihydro-2h,15'h-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (from Example 936, Step 1) and cyclopropane carbonyl chloride (Sigma), and the desired product, N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)cyclopropanecarboxamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)cyclopropanecarboxamide was isolated as a white solid. $^1$H NMR (400 MHz, CD$_3$OD) δ 7.76 (d, J=8.6 Hz, 1H), 7.22-7.16 (m, 2H), 7.14-7.09 (m, 2H), 6.97 (d, J=8.0 Hz, 1H), 4.12 (dd, J=11.9, 18.0 Hz, 2H), 3.85-3.73 (m, 3H), 3.71 (d, J=14.3 Hz, 1H), 3.20 (dd, J=7.6, 14.1 Hz, 1H), 2.87-2.73 (m, 2H), 2.53-2.36 (m, 2H), 2.13-1.19 (m, 19H), 0.94-0.55 (m, 4H). m/z (ESI, +ve ion) 640.3 (M+H)$^+$.

The title compound was prepared in an analogous manner to that described in Example 935, Step 2, using (1S,3'R,6'R,7'R)-7'-amino-6-chloro-3,4-dihydro-2h,15'h-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S)-7'-amino-6-chloro-3,4-dihydro-2h,15'h-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (from Example 936, Step 1) and methanesulfonyl chloride (Sigma), and the desired product, N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)methanesulfonamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)methanesulfonamide was isolated as a white solid. $^1$H NMR (500 MHz, CD$_3$OD) δ 7.75 (d, J=9.0 Hz, 1H), 7.21 (d, J=2.0 Hz, 1H), 7.19 (dd, J=2.2, 8.6 Hz, 1H), 7.12 (d, J=2.0 Hz, 1H), 7.09 (dd, J=2.0, 8.1 Hz, 1H), 6.95 (d, J=8.1 Hz, 1H), 3.89 (d, J=13.4 Hz, 1H), 3.79 (d, J=14.2 Hz, 2H), 3.50-3.41 (m, 2H), 3.19 (dd, J=1.5, 3.2 Hz, 2H), 2.93 (s, 3H), 2.86-2.74 (m, 2H), 2.67-2.57 (m, 1H), 2.49 (br. s., 1H), 2.12-2.01 (m, 1H), 2.00-1.89 (m, 3H), 1.89-1.78 (m, 2H), 1.77-1.56 (m, 5H), 1.56-1.45 (m, 5H), 1.39-1.33 (m, 2H). m/z (ESI, +ve ion) 650.2 (M+H)$^+$.

Example 939. N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)-2-hydroxyacetamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)-2-hydroxyacetamide

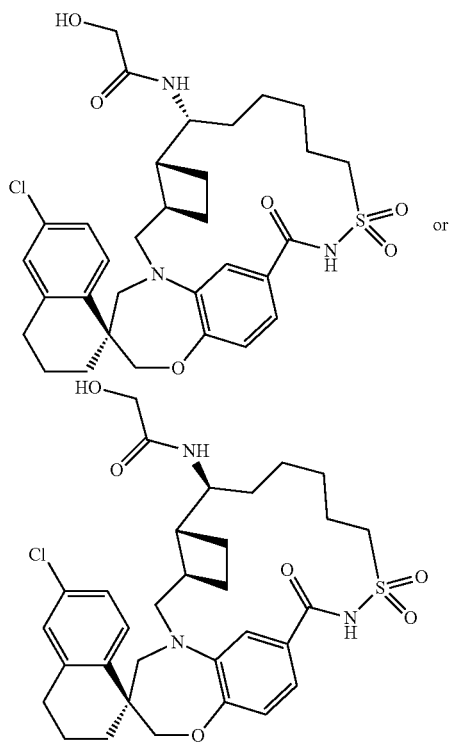

To a 25-mL round-bottomed flask was added (1S,3'R,6'R,7'R)-7'-amino-6-chloro-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S)-7'-amino-6-chloro-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (from Example 936, Step 1; 5.9 mg, 10.3 μmol), DIEA (3.60 μl, 0.02 mmol, Aldrich), HATU (3.92 mg, 10.3 μmol), glycolic acid (0.78 mg, 10.3 μmol) and 1 mL of DMF. After 1 h, the reaction mixture was filtered and purified by reverse phase preparative HPLC (Gemini™ Prep C$_{18}$ 5 μm column; Phenomenex, Torrance, CA; gradient elution of 30% to 95% MeCN in water, where both solvents contain 0.1% TFA, 30 min method) to give N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)-2-hydroxyacetamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)-2-hydroxyacetamide (4.2 mg, 6.66 μmol). $^1$H NMR (400 MHz, CDCl$_3$) δ 7.73 (d, J=8.4 Hz, 1H), 7.17 (dd, J=2.3, 8.4 Hz, 1H), 7.10 (d, J=4.3 Hz, 2H), 7.06 (dd, J=1.4, 7.6 Hz, 1H), 6.94 (d, J=8.2 Hz, 1H), 4.08 (dd, J=11.9, 25.6 Hz, 2H), 3.98 (dd, J=15.8, 19.4 Hz, 2H), 3.87-3.74 (m, 3H), 3.71 (d, J=14.1 Hz, 1H), 3.17 (dd, J=8.3, 15.4 Hz, 1H), 2.84-2.70 (m, 2H), 2.49 (d, J=9.0 Hz, 1H), 2.38-2.27 (m, 1H), 2.09-1.82 (m, 6H), 1.78-1.59 (m, 5H), 1.59-1.29 (m, 7H). m/z (ESI, +ve ion) 630.2 (M+H)$^+$.

Example 940. N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)-N-methylacetamide or N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)-N-methylacetamide

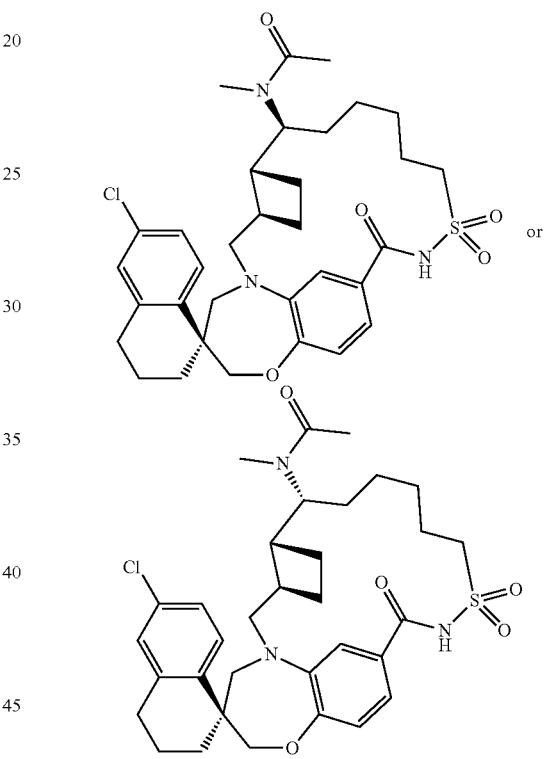

The title compound was prepared in an analogous manner to that described in Example 934, Step 2 using (1S,3'R,6'R,7'S)-6-chloro-7'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R)-6-chloro-7'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (Example 927, first eluting major peak out of preparative reverse phase HPLC) and acetyl chloride, and the corresponding desired product, N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)cyclopropanecarboxamide or N-((1S,3'R,6'R,R-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)cyclopropanecarboxamide was isolated. $^1$H NMR (400

MHz, CD₃OD) δ 7.75 (d, J=8.4 Hz, 1H), 7.19 (d, J=8.8 Hz, 1H), 7.12 (br. s., 1H), 6.97 (br. s., 3H), 4.13 (d, J=2448.3 Hz, 1H), 4.03 (t, J=11.6 Hz, 1H), 3.92-3.83 (m, 1H), 3.79 (d, J=14.5 Hz, 1H), 3.67-3.53 (m, 2H), 3.52-3.36 (m, 2H), 3.27-3.15 (m, 1H), 2.83 (br. s., 3H), 2.56 (br. s., 1H), 2.22-2.14 (m, 2H), 2.11 (s, 3H), 2.07-1.09 (m, 17H). m/z (ESI, +ve ion) 628.2 (M+H)⁺.

Example 941. N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)-N-methylacetamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)-N-methylacetamide

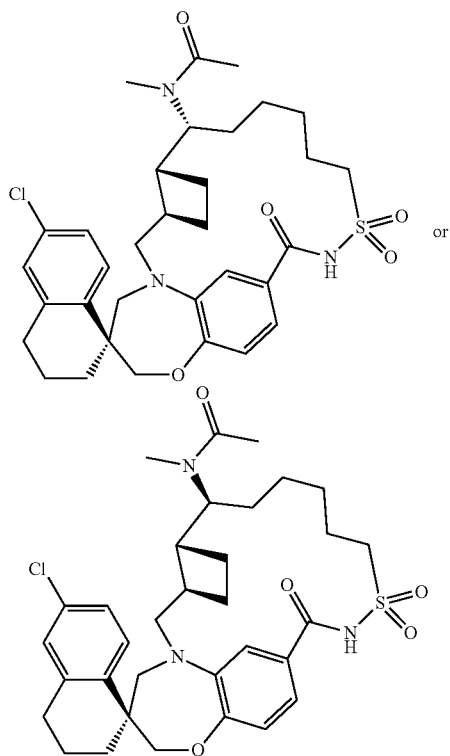

The title compound was prepared in an analogous manner to that described in 934, Step 2 using (1S,3'R,6'R,7'R)-6-chloro-7'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S)-6-chloro-7'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (Example 927, second eluting major isomer out of preparative reverse phase HPLC) and acetyl chloride, and the corresponding desired product, N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)cyclopropanecarboxamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)cyclopropanecarboxamide was isolated. ¹H NMR (400 MHz, CD₃OD) δ 7.76 (d, J=8.6 Hz, 1H), 7.19 (dd, J=2.2, 8.4 Hz, 1H), 7.14-7.10 (m, 1H), 7.07 (dd, J=1.9, 17.7 Hz, 1H), 7.00-6.93 (m, 2H), 4.13-3.93 (m, 3H), 3.89 (d, J=15.3 Hz, 1H), 3.78-3.69 (m, 2H), 3.53-3.45 (m, 1H), 3.17-3.01 (m, 1H), 2.86-2.70 (m, 4H), 2.69 (s, 1H), 2.36 (d, J=8.4 Hz, 1H), 2.30-2.16 (m, 2H), 2.13 (s, 3H), 2.01 (dd, J=6.8, 13.1 Hz, 2H), 1.97-1.82 (m, 5H), 1.80-1.73 (m, 3H), 1.71-1.62 (m, 1H), 1.53-1.43 (m, 2H), 1.38-1.23 (m, 3H). m/z (ESI, +ve ion) 628.2 (M+H)⁺.

Example 942. N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)-N-methylcyclopropanecarboxamide or N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)-N-methylcyclopropanecarboxamide

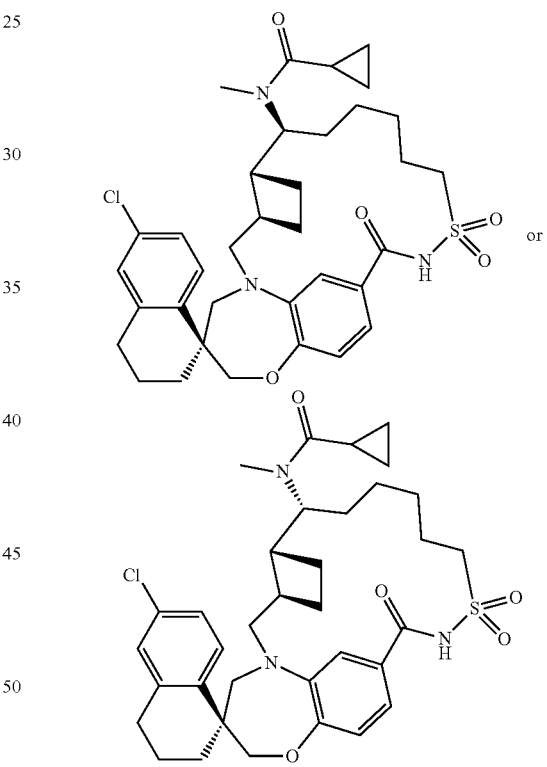

The title compound was prepared in an analogous manner to that described in 934, Step 2 using (1S,3'R,6'R,7'S)-6-chloro-7'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'R)-6-chloro-7'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (Example 927, first eluting major peak out of reverse phase preparative HPLC) and cyclopropane carbonyl chloride (Sigma), and the corresponding desired product, N-((1S,3'R,6'R,7'S)-6-chloro-13',13'-dioxido-15'-oxo-3,4-dihydro-2H-spiro[naphthalene- 1,22'-[20]oxa[13]thia[1,14]diazatetracyclo[14.7.2.0$^{3,6}$.0$^{19,}$ $^{24}$]pentacosa[16,18,24]trien]-7'-yl)-N-methylcyclopropanecarboxamide or N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)-N-methylcyclopropanecarboxamide was isolated. $^1$H NMR (400 MHz, CD$_3$OD) δ 7.76 (d, J=8.6 Hz, 1H), 7.20 (d, J=8.7 Hz, 1H), 7.13 (t, J=2.3 Hz, 1H), 7.01-6.94 (m, 3H), 4.16-4.00 (m, 2H), 3.89 (d, J=15.1 Hz, 1H), 3.80 (d, J=14.3 Hz, 1H), 3.65-3.42 (m, 3H), 3.30-3.19 (m, 1H), 2.99 (s, 2H), 2.87-2.74 (m, 2H), 2.73 (s, 1H), 2.59-2.49 (m, 1H), 2.33-2.21 (m, 1H), 2.20-2.00 (m, 3H), 2.00-1.15 (m, 15H), 0.96-0.81 (m, 4H). m/z (ESI, +ve ion) 654.2 (M+H)$^+$.

Example 943. N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)-N-methylcyclopropanecarboxamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)-N-methylcyclopropanecarboxamide

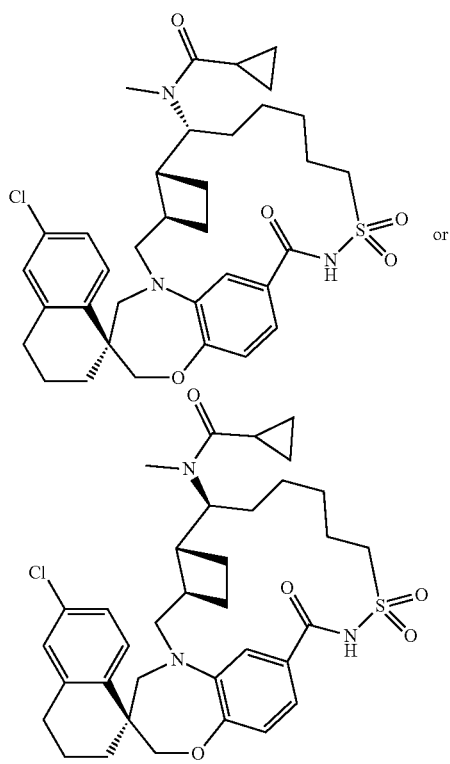

The title compound was prepared in an analogous manner to that described in 934, Step 2 using (1S,3'R,6'R,7'R)-6-chloro-7'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S)-6-chloro-7'-(methylamino)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (Example 927, second eluting major peak out of reverse phase preparative HPLC) and cyclopropane carbonyl chloride (Sigma), and the corresponding desired product, N-((1S,3'R,6'R,7'R)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)-N-methylcyclopropanecarboxamide or N-((1S,3'R,6'R,7'S)-6-chloro-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)-N-methylcyclopropanecarboxamide was isolated. $^1$H NMR (400 MHz, CD$_3$OD) δ 7.77 (d, J=8.0 Hz, 1H), 7.20 (dd, J=0.4, 8.8 Hz, 1H), 7.13 (br. s., 1H), 7.10 (td, J=2.3, 8.2 Hz, 1H), 7.05-6.94 (m, 2H), 4.16-3.88 (m, 4H), 3.80-3.70 (m, 2H), 3.37 (s, 3H), 3.22-3.11 (m, 1H), 3.07-2.96 (m, 2H), 2.85-2.68 (m, 3H), 2.38 (br. s., 1H), 2.23-1.14 (m, 20H), 1.01-0.83 (m, 4H). m/z (ESI, +ve ion) 654.2 (M+H)$^+$.

Example 945. (1S,3'R,6'S)-6-chloro-3,4-dihydro-2H,9'H,15'H-spiro[naphthalene-1,22'-[20]oxa[13]thia[1,10,14]triazatetracyclo[14.7.2.0$^{3,6}$.0$^{19,24}$]pentacosa [16,18,24]triene]-9',15'-dione 13',13'-dioxide

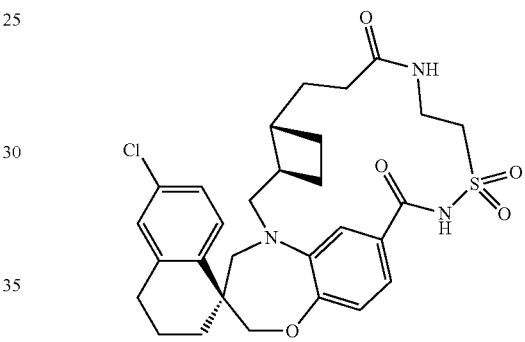

Step 1: (S)-tert-butyl 6'-chloro-5-(((1R,2S)-2-((E)-3-ethoxy-3-oxoprop-1-en-1-yl)cyclobutyl)methyl)-3',4,4',5-tetrahydro-2H,2'H-spiro[benzo[b][1,4]oxazepine-3,1'-naphthalene]-7-carboxylate

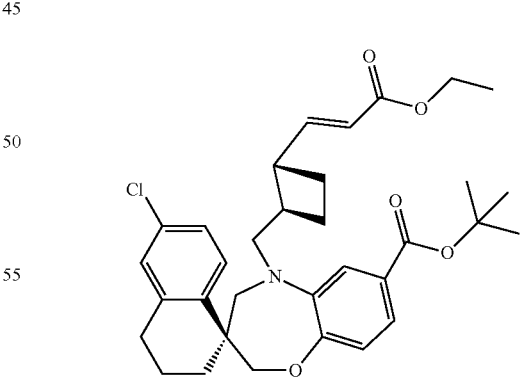

To a 100-mL round-bottomed flask was added sodium hydride (60% dispersion in mineral oil; 21.3 mg, 0.53 mmol, Aldrich) and 10 mL of THF. The reaction mixture was cooled to 0° C., and triethyl phosphonoacetate (81 μl, 0.363 mmol, Aldrich) was added dropwise. The reaction mixture was stirred at 0° C. for 30 min, (S)-tert-butyl 6'-chloro-5-(((1R,2R)-2-formylcyclobutyl)methyl)-3',4,4',5-tetrahydro- 2H,2'H-spiro[benzo[b][1,4]oxazepine-3,1'-naphthalene]-7-carboxylate (Intermediate AA11A, Step 20A; 120 mg, 0.242 mmol) was added in one portion. The reaction mixture was heated to 40° C. for 1 h. The reaction mixture was quenched with water. 40 mL of EtOAc and 20 mL of brine were added. The organic layer was concentrated, and go to next step directly.

Step 2: (S)-tert-butyl 6'-chloro-5-(((1R,2S)-2-(3-ethoxy-3-oxopropyl)cyclobutyl)methyl)-3',4,4',5-tetrahydro-2H,2'H-spiro[benzo[b][1,4]oxazepine-3,1'-naphthalene]-7-carboxylate

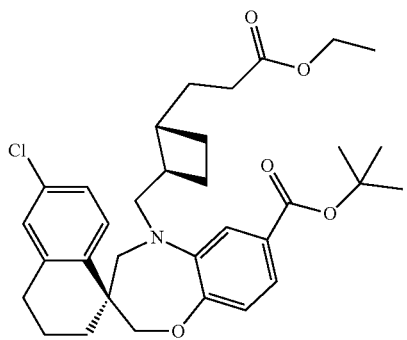 [SMILES: CCOC(=O)CC[C@@H]1CC[C@H]1CN1C[C@@]2(CCCc3cc(Cl)ccc32)COc2ccc(C(=O)OC(C)(C)C)cc21]

The crude product of (S)-tert-butyl 6'-chloro-5-(((1R,2S)-2-((E)-3-ethoxy-3-oxoprop-1-en-1-yl)cyclobutyl)methyl)-3',4,4',5-tetrahydro-2H,2'H-spiro[benzo[b][1,4]oxazepine-3,1'-naphthalene]-7-carboxylate from Step 1 above was dissolved with 20 mL of EtOAc, and then platinum(IV) oxide (54.9 mg, 0.24 mmol) was added. The reaction mixture was stirred under H$_2$ ballon at rt overnight, and then filtered through celite to remove solid catalyst. The filtrate was concentrated to give the crude desire product, and go to next step directly.

Step 3: 3-((1S,2R)-2-(((S)-7-(tert-butoxycarbonyl)-6'-chloro-3',4'-dihydro-2H,2'H-spiro[benzo[b][1,4]oxazepine-3,1'-naphthalen]-5 (4H)-yl)methyl)cyclobutyl)propanoic Acid

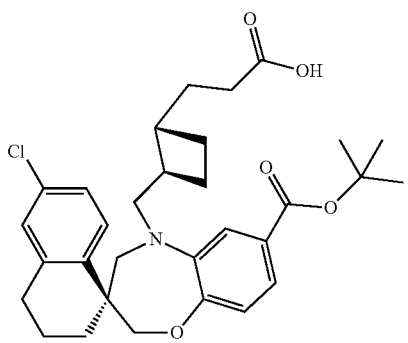 [SMILES: CC(C)(C)OC(=O)c1ccc2c(c1)N(C[C@@H]1CC[C@H]1CCC(=O)O)C[C@@]1(CCCc3cc(Cl)ccc31)CO2]

To a mixture of (S)-tert-butyl 6'-chloro-5-(((1R,2S)-2-(3-ethoxy-3-oxopropyl)cyclobutyl)methyl)-3',4,4',5-tetrahydro-2H,2'H-spiro[benzo[b][1,4]oxazepine-3,1'-naphthalene]-7-carboxylate from Step 2 above in 3 mL of THF, 3 mL of MeOH and 1 mL of water, lithium hydroxide (102 mg, 2.42 mmol, JT-Baker) was added. The reaction mixture was stirred at 50° C. overnight. The reaction mixture was acidified with 1 N aq. HCl solution, and then 50 mL of EtOAc was added. The organic layer was concentrated and purified through a 40 g ISCO Gold column, eluting with 0-35% EtOAc(with 0.3% HOAc) in hexane to give 3-((1S,2R)-2-(((S)-7-(tert-butoxycarbonyl)-6'-chloro-3',4'-dihydro-2H,2'H-spiro[benzo[b][1,4]oxazepine-3,1'-naphthalen]-5 (4H)-yl)methyl)cyclobutyl)propanoic acid (115 mg, 0.21 mmol).

Step 4: (S)-tert-butyl 6'-chloro-5-(((1R,2S)-2-(3-oxo-3-((2-sulfamoylethyl)amino)propyl)cyclobutyl)methyl)-3',4,4',5-tetrahydro-2H,2'H-spiro[benzo[b][1,4]oxazepine-3,1'-naphthalene]-7-carboxylate

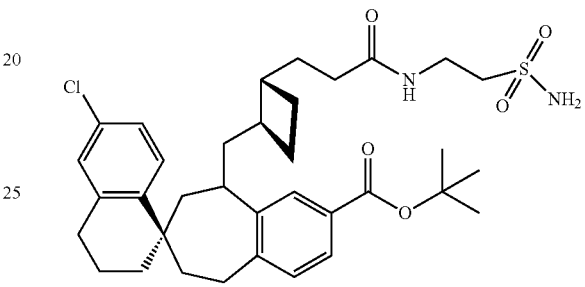

To a 100-mL round-bottomed flask was added 3-((1S,2R)-2-(((S)-7-(tert-butoxycarbonyl)-6'-chloro-3',4'-dihydro-2H,2'H-spiro[benzo[b][1,4]oxazepine-3,1'-naphthalen]-5 (4H)-yl)methyl)cyclobutyl)propanoic acid (from Step 3; 10 mg, 0.019 mmol), DIEA (9.70 µl, 0.056 mmol, Aldrich), 2-aminoethanesulfonamide (2.76 mg, 0.022 mmol, Biodfin) and 2 mL of DMF. The reaction stirred at rt overnight. The reaction mixture was diluted with 30 mL of EtOAc and 10 mL of water. The organic layer was concentrated and purified through a 12 g ISCO Gold column, eluting with 0-40% EtOAc(with 0.3% HOAc) in hexane to give the title compound.

Step 5: (S)-6'-chloro-5-(((1R,2S)-2-(3-oxo-3-((2-sulfamoylethyl)amino)propyl)cyclobutyl)methyl)-3',4,4',5-tetrahydro-2H,2'H-spiro[benzo[b][1,4]oxazepine-3,1'-naphthalene]-7-carboxylic Acid

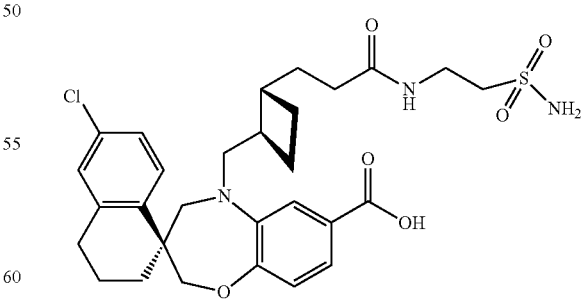

5 mL of 50% TFA in DCM was added to (S)-tert-butyl 6'-chloro-5-(((1R,2S)-2-(3-oxo-3-((2-sulfamoylethyl)amino)propyl)cyclobutyl)methyl)-3',4,4',5-tetrahydro-2H,2'H-spiro[benzo[b][1,4]oxazepine-3,1'-naphthalene]-7-carboxylate from Step 4 above. After 3 h, the deprotection was completed. The reaction mixture was concentrated and dried under Hi-Vac overnight to give the crude title compound (9.2 mg. 0.013 mmol).

Step 6: (1S,3'R,6'S)-6-chloro-3,4-dihydro-2H,9'H, 15'H-spiro[naphthalene-1,22'-[20]oxa[13]thia[1,10, 14]triazatetracyclo[14.7.2.0$^{3,6}$.0$^{19,24}$]pentacosa[16, 18,24]triene]-9',15'-dione 13',13'-dioxide N,N-Dimethylpyridin-4-amine (DMAP) (7.0 mg, 0.058 mmol) was added to a solution of (S)-6'-chloro-5-((((1R,2S)-2-(3-oxo-3-((2-sulfamoylethyl)amino)propyl)cyclobutyl) methyl)-3',4,4',5-tetrahydro-2H,2'H-spiro[benzo[b][1,4] oxazepine-3,1'-naphthalene]-7-carboxylic acid (from Step 5; 10 mg, 0.017 mmol) in DCM (1 mL) at 0° C., and then N-(3-dimethylaminopropyl)-N'-ethylcarbodiimide hydrochloride (13.0 mg, 0.068 mmol) was added slowly and it was stirred at rt overnight. The reaction mixture was diluted with Teac (30 ml), washed with 1 N HCl aq. solution (3 ml), brine (5 ml), dried over anhydrous sodium sulfate, concentrated and purified by reverse phase preparative HPLC (Gemini™ Prep C$_{18}$ 5 μm column; Phenomenex, Torrance, CA; gradient elution of 40% to 95% MeCN in water, where both solvents contain 0.1% TFA, 30 min method) to give (1S, 3'R,6'S)-6-chloro-3,4-dihydro-2H,9'H,15'H-spiro[naphthalene-1,22'-[20]oxa[13]thia[1,10,14]triazatetracyclo [14.7.2.0$^{3,6}$.0$^{19,24}$]pentacosa[16,18,24]triene]-9',15'-dione 13',13'-dioxide (5.9 mg, 10.31 μmol). $^1$H NMR (400 MHz, CD$_3$OD) δ 7.73 (d, J=8.6 Hz, 1H), 7.17 (dd, J=1.8, 8.2 Hz, 2H), 7.09 (dd, J=2.0, 14.1 Hz, 2H), 6.96 (d, J=8.2 Hz, 1H), 4.03 (dd, J=7.6, 15.7 Hz, 1H), 3.85 (dd, J=7.0, 15.1 Hz, 1H), 3.69 (dd, J=14.7, 34.2 Hz, 2H), 3.61 (s, 1H), 3.57 (dd, J=1.0, 8.0 Hz, 1H), 3.14 (dd, J=6.7, 15.6 Hz, 1H), 2.84-2.71 (m, 2H), 2.31 (d, J=8.0 Hz, 1H), 2.24-1.54 (m, 13H), 1.54-1.46 (m, 1H). m/z (ESI, +ve ion) 572.0 (M+H)$^+$.

Example 946. (1S,3'R,6'S,13'S)-6-chloro-3,4-dihydro-2H,9'H,16'H-spiro[naphthalene-1,23'-[21]oxa [14]thia[1,10,15]triazapentacyclo[15.7.2.1$^{10,13}$.
0$^{3,6}$.0$^{20,25}$]heptacosa[17,19,25]triene]-9',16'-dione 14',14'-dioxide or (1S,3'R,6'S,13'R)-6-chloro-3,4-dihydro-2H,9'H,16'H-spiro[naphthalene-1,23'-[21] oxa[14]thia[1,10,15]triazapentacyclo[15.7. 2.1$^{10,13}$.0$^{3,6}$.0$^{20,25}$]heptacosa[17,19,25]triene]-9',16'-dione 14',14'-dioxide

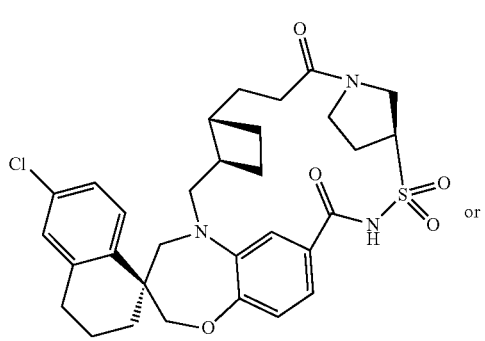

or

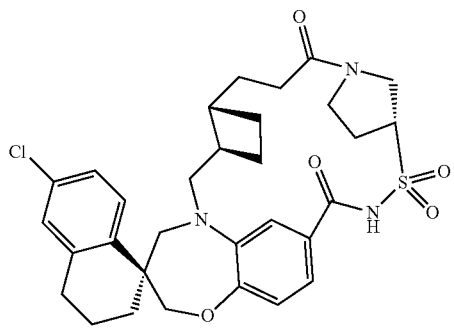

The title compound was prepared in an analogous manner to that described in Example 945, Steps 1-6, but replacing 2-aminoethanesulfonamide with pyrrolidine-3-sulfonamide in Step 4, and the desired product, (1S,3'R,6'S,13'S)-6-chloro-3,4-dihydro-2H,9'H,16'H-spiro[naphthalene-1,23'-[21]oxa[14]thia[1,10,15]triazapentacyclo[15.7.2.1$^{10,13}$.0$^{3,6}$.0$^{20,25}$]heptacosa[17,19,2 5]triene]-9',16'-dione 14',14'-dioxide or (1S,3'R,6'S,13'R)-6-chloro-3,4-dihydro-2H,9'H,16'H-spiro[naphthalene-1,23'-[21]oxa[14]thia[1,10,15]triazapentacyclo[15.7.2.1$^{10,13}$.0$^{3,6}$.0$^{20,25}$]heptacosa[17,19,2 5]triene]-9',16'-dione 14',14'-dioxide was isolated (first eluting major peak) out of reverse phase preparative HPLC. $^1$H NMR (400 MHz, CD$_3$OD) δ 7.76 (d, J=8.6 Hz, 1H), 7.21 (dd, J=2.2, 8.3 Hz, 1H), 7.14 (dd, J=2.3, 8.6 Hz, 2H), 7.07 (d, J=1.4 Hz, 1H), 6.99 (d, J=8.2 Hz, 1H), 4.21-3.97 (m, 5H), 3.85-3.74 (m, 2H), 3.58-3.47 (m, 2H), 2.89-2.72 (m, 3H), 2.69-2.40 (m, 5H), 2.30 (br. s., 1H), 2.14 (d, J=13.1 Hz, 1H), 2.08-2.03 (m, 1H), 2.02-1.74 (m, 8H), 1.53-1.43 (m, 1H). m/z (ESI, +ve ion) 598.2 (M+H)$^+$.

Example 947. (1S,3'R,6'S,13'R)-6-chloro-3,4-dihydro-2H,9'H,16'H-spiro[naphthalene-1,23'-[21]oxa [14]thia[1,10,15]triazapentacyclo[15.7.2.1$^{11,13}$.
0$^{3,6}$.0$^{20,25}$]heptacosa[17,19,25]triene]-9',16'-dione 14',14'-dioxide or (1S,3'R,6'S,13'S)-6-chloro-3,4-dihydro-2H,9'H,16'H-spiro[naphthalene-1,23'-[21] oxa[14]thia[1,10,15]triazapentacyclo[15.7. 2.1$^{10,13}$.0$^{3,6}$.0$^{20,25}$]heptacosa[17,19,25]triene]-9',16'-dione 14',14'-dioxide

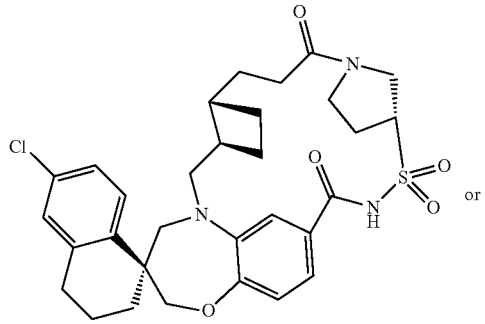

or

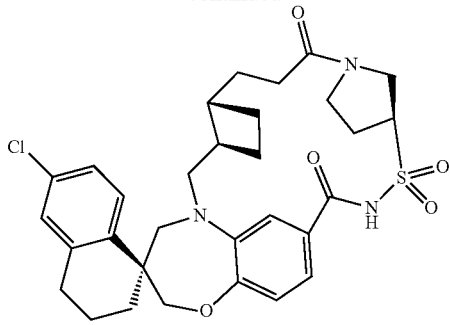

The title compound was obtain as a single isomer (second eluting major peak) from the reverse phase preparative HPLC in Example 946. $^1$H NMR (400 MHz, CDCl$_3$) δ 7.76 (d, J=8.6 Hz, 1H), 7.21 (dd, J=2.2, 8.3 Hz, 1H), 7.14 (dd, J=2.3, 8.6 Hz, 2H), 7.07 (d, J=1.4 Hz, 1H), 6.99 (d, J=8.2 Hz, 1H), 4.96-4.82 (m, 1H), 3.99-3.85 (m, 3H), 3.78 (d, J=9.6 Hz, 2H), 3.73-3.49 (m, 4H), 3.42-3.34 (m, 1H), 3.21 (d, J=14.3 Hz, 1H), 2.95-2.86 (m, 1H), 2.68 (br. s., 1H), 2.61 (br. s., 1H), 2.58-2.43 (m, 1H), 2.29 (br. s., 3H), 2.04 (br. s., 1H), 2.00-1.88 (m, 2H), 1.82 (br. s., 3H), 1.72 (br. s., 3H), 1.69-1.45 (m, 2H). m/z (ESI, +ve ion) 598.2 (M+H)$^+$.

Example 948. (1S,3'R,6'S,14'S,15'R)-6-chloro-3,4-dihydro-2H,9'H,17'H-spiro[naphthalene-1,24'-[22]oxa[15]thia[1,10,16]triazapentacyclo[16.7.2.1$^{10,14}$.0$^{3,6}$.0$^{21,26}$]octacosa[18,20,26]triene]-9',17'-dione 15'-oxide or (1S,3'R,6'S,14'S,15'S)-6-chloro-3,4-dihydro-2H,9'H,17'H-spiro[naphthalene-1,24'-[22]oxa[15]thia[1,10,16]triazapentacyclo[16.7.2.1$^{10,14}$.0$^{3,6}$.0$^{21,26}$]octacosa[18,20,26]triene]-9',17'-dione 15'-oxide

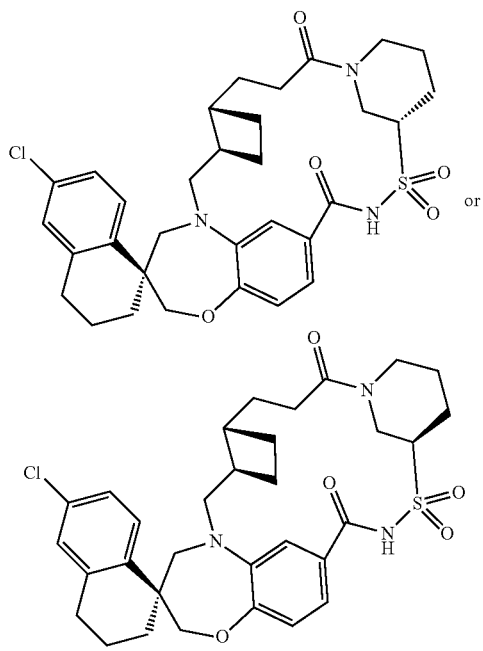

The title compound was prepared in an analogous manner to that described in Example 945, Steps 1-6, but replacing 2-aminoethanesulfonamide with piperidine-3-sulfonamide in Step 4, and the desired product, (1S,3'R,6'S,14'S,15'R)-6-chloro-3,4-dihydro-2H,9'H,17'H-spiro[naphthalene-1,24'-[22]oxa[15]thia[1,10,16]triazapentacyclo[16.7.2.1$^{10,14}$.0$^{3,6}$.0$^{21,26}$]octacosa[18,20,26]triene]-9',17'-dione 15'-oxide or (1S,3'R,6'S,14'S,15'S)-6-chloro-3,4-dihydro-2H,9'H,17'H-spiro[naphthalene-1,24'-[22]oxa[15]thia[1,10,16]triazapentacyclo[16.7.2.1$^{10,14}$.0$^{3,6}$.0$^{21,26}$]octacosa[18,20,26]triene]-9',17'-dione 15'-oxide was isolated (first eluting major peak) out of preparative reverse phase HPLC. $^1$H NMR (400 MHz, CD$_3$OD) δ 7.78 (d, J=8.4 Hz, 1H), 7.45 (br. s., 1H), 7.18 (dd, J=2.2, 8.4 Hz, 1H), 7.12 (t, J=6.9 Hz, 1H), 7.02 (dd, J=2.4, 8.3 Hz, 1H), 6.87 (br. s., 1H), 5.03-4.90 (m, 1H), 4.33-4.15 (m, 1H), 4.06 (dd, J=12.7, 21.3 Hz, 2H), 3.88 (d, J=14.9 Hz, 1H), 3.81-3.65 (m, 3H), 3.59-3.46 (m, 1H), 3.27-3.09 (m, 2H), 2.93 (d, J=4.9 Hz, 1H), 2.90-2.72 (m, 2H), 2.66-2.42 (m, 1H), 2.26 (d, J=5.7 Hz, 1H), 2.17-1.92 (m, 6H), 1.85-1.58 (m, 8H). m/z (ESI, +ve ion) 612.2 (M+H)$^+$.

Example 949. (1S,3'R,6'S,14'S,15'S)-6-chloro-3,4-dihydro-2H,9'H,17'H-spiro[naphthalene-1,24'-[22]oxa[15]thia[1,10,16]triazapentacyclo[16.7.2.1$^{10,14}$.0$^{3,6}$.0$^{21,26}$]octacosa[18,20,26]triene]-9',17'-dione 15'-oxide or (1S,3'R,6'S,14'S,15'R)-6-chloro-3,4-dihydro-2H,9'H,17'H-spiro[naphthalene-1,24'-[22]oxa[15]thia[1,10,16]triazapentacyclo[16.7.2.1$^{10,14}$.0$^{3,6}$.0$^{21,26}$]octacosa[18,20,26]triene]-9',17'-dione 15'-oxide

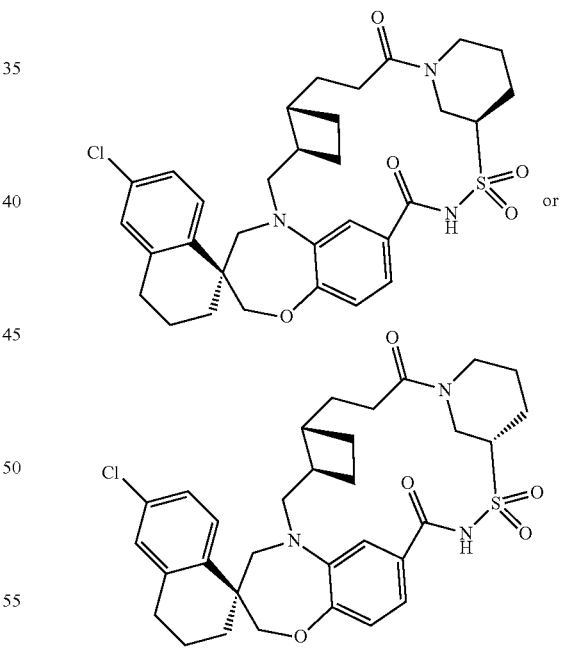

The title compound was obtain as a single isomer (second eluting major peak) from the reverse phase preparative HPLC in Example 948. $^1$H NMR (400 MHz, CD$_3$OD) δ 7.79 (d, J=8.6 Hz, 1H), 7.42 (br. s., 1H), 7.33-7.22 (m, 1H), 7.18 (dd, J=2.4, 8.1 Hz, 1H), 7.12 (d, J=1.8 Hz, 1H), 6.86 (br. s., 1H), 5.04-4.91 (m, 1H), 4.54 (br. s., 1H), 4.33 (d, J=11.2 Hz, 1H), 3.88 (d, J=13.3 Hz, 1H), 3.78-3.70 (m, 2H), 3.56 (d, J=10.8 Hz, 1H), 3.20-3.15 (m, 1H), 3.15-3.03 (m, 1H), 3.00-2.73 (m, 5H), 2.66 (d, J=8.4 Hz, 1H), 2.33 (d, J=6.8 Hz, 1H), 2.15-2.03 (m, 3H), 1.99-1.88 (m, 5H), 1.85-1.66 (m, 6H), 1.63-1.56 (m, 1H). m/z (ESI, +ve ion) 612.2 (M+H)+.

Example 950. (1S,3'R,6'R,7'S,8'R,10'R)-6-chloro-7'-hydroxy-3,4-dihydro-2H,16'H-spiro[naphthalene-1, 23'-[21]oxa[14]thia[1,15]diazapentacyclo[15.7.2. 0³,⁶.0⁸,¹⁰.0²⁰,²⁵]hexacosa[17,19,25]trien]-16'-one 14',14'-dioxide or (1S,3'R,6'R,7'S,8'S,10'S)-6-chloro-7'-hydroxy-3,4-dihydro-2H,16'H-spiro[naphthalene-1,23'-[21]oxa[14]thia[1,15]diazapentacyclo[15.7.2.0³,⁶.0⁸,¹⁰.0²⁰,²⁵]hexacosa[17,19,25]trien]-16'-one 14',14'-dioxide

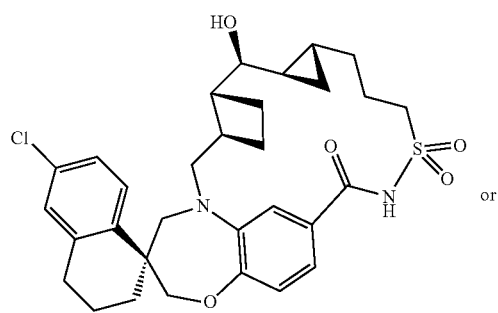

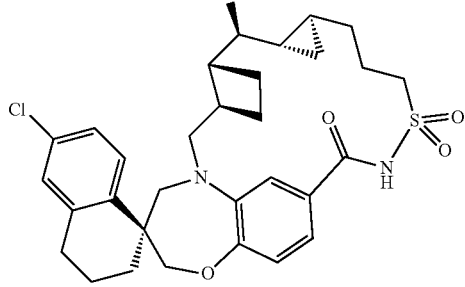

Step 1: (S)-tert-butyl 5-(((1R,2R)-2-((S,E)-6-(N,N-bis(4-methoxybenzyl)sulfamoyl)-1-hydroxyhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate

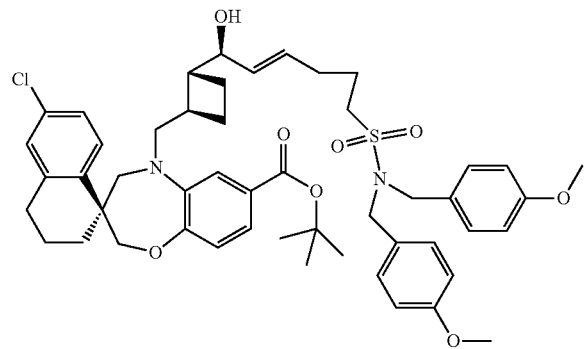 [SMILES: COc1ccc(CN(Cc2ccc(OC)cc2)S(=O)(=O)CCC/C=C/[C@H](O)[C@@H]2CC[C@H]2CN2C[C@@]3(CCCc4cc(Cl)ccc43)COc3ccc(C(=O)OC(C)(C)C)cc32)cc1]

A flask was charged with (S)-tert-butyl 6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylate (Intermediate AA13A, Step 1B;

0.065 g, 0.124 mmol) and N,N-bis(4-methoxybenzyl)pent-4-ene-1-sulfonamide (Intermediate EE19; 0.100 g, 0.25 mmol) in DCM (4.96 ml). It was stirred at rt for 10 min to dissolve the solid starting material and then subjected to three cycles of evacuation/back-filling with nitrogen. To the homogeneous solution was added a solution of Hoveyda-Grubbs II (7.77 mg, 0.012 mmol) and it was stirred at 30° C. overnight. The reaction mixture was concentrated and purified through a 40 g ISCO Gold column, eluting with 0-30% EtOAc in hexane to give (S)-tert-butyl 5-(((1R,2R)-2-((1S,6S,E)-6-(N,N-bis(4-methoxybenzyl)sulfamoyl)-1-hydroxyhept-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate (55.8 mg, 0.062 mmol).

Step 2: (S)-5-(((1R,2R)-2-((S)-((1S,2S)-2-(3-(N,N-bis(4-methoxybenzyl)sulfamoyl)propyl)cyclopropyl)(hydroxy) methyl)cyclobutyl)methyl)-6'-chloro-3',4,4',5-tetrahydro-2H,2'H-spiro[benzo[b][1,4]oxazepine-3,1'-naphthalene]-7-carboxylic Acid and (S)-5-(((1R,2R)-2-((S)-((1R,2R)-2-(3-(N,N-bis(4-methoxybenzyl)sulfamoyl)propyl)cyclopropyl)(hydroxy) methyl)cyclobutyl)methyl)-6'-chloro-3',4,4',5-tetrahydro-2H,2'H-spiro[benzo[b][1,4]oxazepine-3,1'-naphthalene]-7-carboxylic Acid

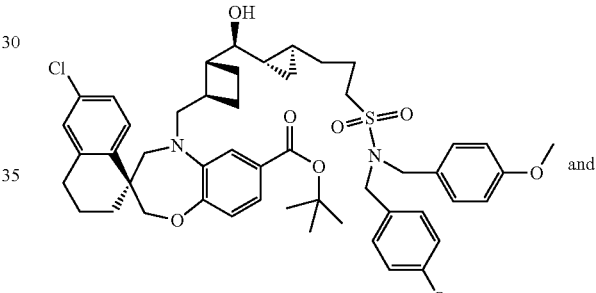

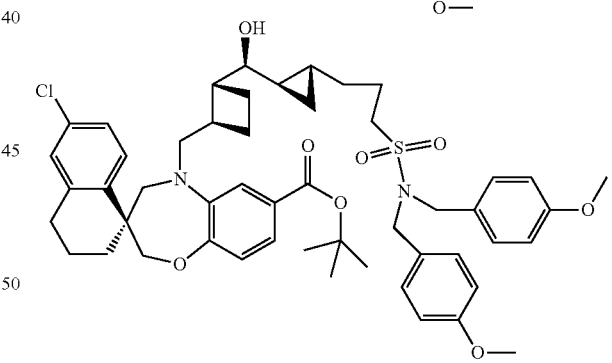

Diethylzinc (1.0 M solution in hexane, 171 μl, 0.17 mmol) was added to a stirred solution of (S)-tert-butyl 5-(((1R,2R)-2-((S,E)-6-(N,N-bis(4-methoxybenzyl)sulfamoyl)-1-hydroxyhex-2-en-1-yl)cyclobutyl)methyl)-6'-chloro-3',4,4',5-tetrahydro-2H,2'H-spiro[benzo[b][1,4]oxazepine-3,1'-naphthalene]-7-carboxylate (Step 1; 30.3 mg, 0.034 mmol) in 1 mL of DCM at −10° C., following by addition of diidomethane (13.76 μl, 0.171 mmol) under N₂ in absence of light. The reaction was warmed to rt and stirred overnight. Sat aq. NH4Cl solution was added to the reaction mixture, and more DCM was added. The organic layer was concentrated and purified through a 40 g ISCO Gold column, eluting with 0-30% EtOAc in hexane to give (S)-5-(((1R, 2R)-2-((S)-((1S,2S)-2-(3-(N,N-bis(4-methoxybenzyl)sulfamoyl)propyl)cyclopropyl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((S)-((1R,2S)-2-(3-(N,N-bis(4-methoxybenzyl)sulfamoyl)propyl)cyclopropyl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylic acid (2.5 mg, 2.96 μmol, first eluting peak), and S)-5-(((1R,2R)-2-((S)-((1S,2S)-2-(3-(N,N-bis(4-methoxybenzyl)sulfamoyl)propyl)cyclopropyl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((S)-((1R,2R)-2-(3-(N,N-bis(4-methoxybenzyl)sulfamoyl)propyl)cyclopropyl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylic acid (10.6 mg, 0.013 mmol, second eluting peak).

Step 3: (S)-6'-chloro-5-(((1R,2R)-2-((S)-hydroxy((1R,2R)-2-(3-sulfamoylpropyl)cyclopropyl)methyl)cyclobutyl)methyl)-3',4,4',5-tetrahydro-2H,2'H-spiro[benzo[b][1,4]oxazepine-3,1'-naphthalene]-7-carboxylic Acid or (S)-6'-chloro-5-(((1R,2R)-2-((S)-hydroxy((1S,2S)-2-(3-sulfamoylpropyl)cyclopropyl)methyl)cyclobutyl)methyl)-3',4,4',5-tetrahydro-2H,2'H-spiro[benzo[b][1,4]oxazepine-3,1'-naphthalene]-7-carboxylic Acid

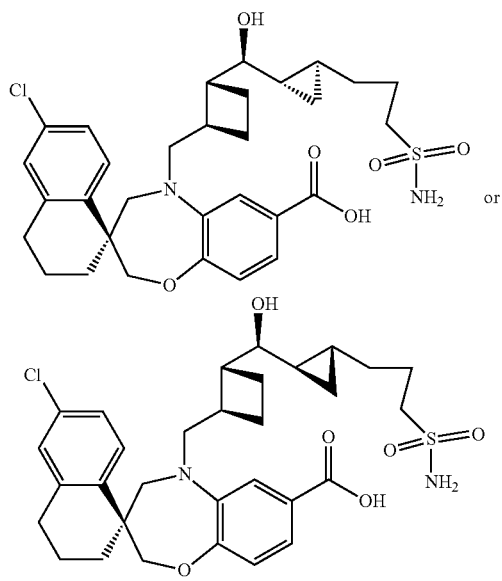

3 mL of 20% TFA/DCM was added to a mixture of (S)-5-(((1R,2R)-2-((S)-((1S,2S)-2-(3-(N,N-bis(4-methoxybenzyl)sulfamoyl)propyl)cyclopropyl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylic acid or (S)-5-(((1R,2R)-2-((S)-((1R,2R)-2-(3-(N,N-bis(4-methoxybenzyl)sulfamoyl)propyl)cyclopropyl)(hydroxy)methyl)cyclobutyl)methyl)-6'-chloro-3',4,4',5-tetrahydro-2H,2'H-spiro[benzo[b][1,4]oxazepine-3,1'-naphthalene]-7-carboxylic acid (Step 2, second eluting peak; 10.2 mg, 0.012 mmol) and thioanisole (14.20 μl, 0.121 mmol) at 0° C. After stirring for overnight, the reaction mixture was concentrated and purified reverse phase preparative HPLC (Gemini™ Prep $C_{18}$ 5 μm column; Phenomenex, Torrance, CA; gradient elution of 40% to 95% MeCN in water, where both solvents contain 0.1% TFA, 30 min method) to give (S)-6'-chloro-5-(((1R,2R)-2-((S)-hydroxy((1R,2R)-2-(3-sulfamoylpropyl)cyclopropyl)methyl)cyclobutyl)methyl)-3',4,4',5-tetrahydro-2H,2'H-spiro[benzo[b][1,4]oxazepine-3,1'-naphthalene]-7-carboxylic acid or (S)-6'-chloro-5-(((1R,2R)-2-((S)-hydroxy((1S,2S)-2-(3-sulfamoylpropyl)cyclopropyl)methyl)cyclobutyl)methyl)-3',4,4',5-tetrahydro-2H,2'H-spiro[benzo[b][1,4]oxazepine-3,1'-naphthalene]-7-carboxylic acid (1.7 mg, 2.82 μmol).

Step 4: (1S,3'R,6'R,7'S,8'R,10'R)-6-chloro-7'-hydroxy-3,4-dihydro-2H,16'H-spiro[naphthalene-1,23'-[21]oxa[14]thia[1,15]diazapentacyclo[15.7.2.0$^{3,6}$.0$^{8,10}$.0$^{20,25}$]hexacosa[17,19,25]trien]-16'-one 14',14'-dioxide or (1S,3'R,6'R,7'S,8'S,10'S)-6-chloro-7'-hydroxy-3,4-dihydro-2H,16'H-spiro[naphthalene-1,23'-[21]oxa[14]thia[1,15]diazapentacyclo[15.7.2.0$^{3,6}$.0$^{8,10}$.0$^{20,25}$]hexacosa[17,19,25]trien]-16'-one 14',14'-dioxide The title compound was prepared in an analogous manner to that described in Example 323, Step 7, and the desired product, (1S,3'R,6'R,7'S,8'R,10'R)-6-chloro-7'-hydroxy-3,4-dihydro-2H,16'H-spiro[naphthalene-1,23'-[21]oxa[14]thia[1,15]diazapentacyclo[15.7.2.0$^{3,6}$.0$^{8,10}$.0$^{20,25}$]hexacosa[17,19,25]trien]-16'-one 14',14'-dioxide or (1S,3'R,6'R,7'S,8'S,10'S)-6-chloro-7'-hydroxy-3,4-dihydro-2H,16'H-spiro[naphthalene-1,23'-[21]oxa[14]thia[1,15]diazapentacyclo[15.7.2.0$^{3,6}$.0$^{8,10}$.0$^{20,25}$]hexacosa[17,19,25]trien]-16'-one 14',14'-dioxide was isolated as a white solid. $^1$H NMR (500 MHz, CD$_3$OD) δ 7.77 (d, J=8.6 Hz, 1H), 7.20 (dd, J=2.0, 8.3 Hz, 1H), 7.13 (d, J=2.2 Hz, 1H), 7.10-7.03 (m, 2H), 6.96 (d, J=5.6 Hz, 1H), 4.15-4.00 (m, 3H), 3.88 (d, J=16.1 Hz, 1H), 3.71 (d, J=13.9 Hz, 1H), 3.61 (dd, J=3.7, 5.1 Hz, 1H), 3.47 (td, J=1.7, 3.2 Hz, 1H), 3.25-3.13 (m, 3H), 2.85-2.75 (m, 2H), 2.46-2.40 (m, 1H), 2.11 (d, J=13.9 Hz, 1H), 2.05-1.75 (m, 7H), 0.99-0.52 (m, 8H). m/z (ESI, +ve ion) 585.2 (M+H)$^+$.

Example 951. (1S,3'R,6'R,7'S,8'R,10'R,13'R)-6-chloro-7'-hydroxy-13'-methyl-3,4-dihydro-2H,16'H-spiro[naphthalene-1,23'-[21]oxa[14]thia[1,15]diazapentacyclo[15.7.2.0$^{3,6}$.0$^{8,10}$.0$^{20,25}$]hexacosa[17,19,25]trien]-16'-one 14',14'-dioxide or (1S,3'R,6'R,7'S,8'S,10'S,13'R)-6-chloro-7'-hydroxy-13'-methyl-3,4-dihydro-2H,16'H-spiro[naphthalene-1,23'-[21]oxa[14]thia[1,15]diazapentacyclo[15.7.2.0$^{3,6}$.0$^{8,10}$.0$^{20,25}$]hexacosa[17,19,25]trien]-16'-one 14',14'-dioxide

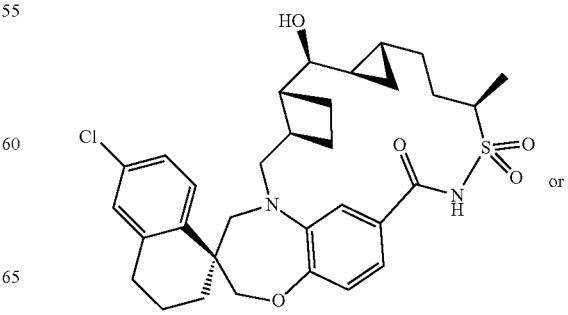

-continued

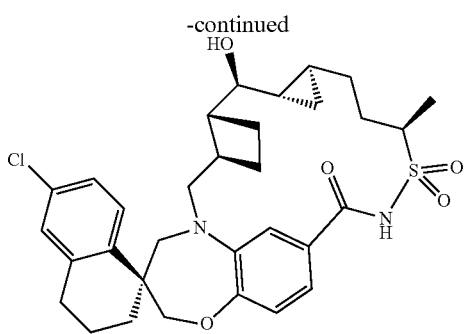

The title compound was prepared in an analogous manner to that described in Example 950, Steps 1 to 4, but replacing N,N-bis(4-methoxybenzyl)pent-4-ene-1-sulfonamide (Intermediate EE19) with (R)—N,N-bis(4-methoxybenzyl)hex-5-ene-2-sulfonamide (Intermediate EE20) in Step 1, and the desired product, (1S,3'R,6'R,7'S,8'R,10'R,13'R)-6-chloro-7'-hydroxy-13'-methyl-3,4-dihydro-2H,16'H-spiro[naphthalene-1,23'-[21]oxa[14]thia[1,15]diazapentacyclo[15.7.2.0$^{3,6}$.0$^{8,10}$.0$^{20,25}$]hexacosa[17,19,25]trien]-16'-one 14',14'-dioxide or (1S,3'R,6'R,7'S,8'S,10'S,13'R)-6-chloro-7'-hydroxy-13'-methyl-3,4-dihydro-2H,16'H-spiro[naphthalene-1,23'-[21]oxa[14]thia[1,15]diazapentacyclo[15.7.2.0$^{3,6}$.0$^{8,10}$.0$^{20,25}$]hexacosa[17,19,25]trien]-16'-one 14',14'-dioxide was isolated as a white solid. $^1$H NMR (400 MHz, CD$_3$OD) δ 7.77 (d, J=8.6 Hz, 1H), 7.21 (dd, J=2.2, 8.4 Hz, 1H), 7.13 (d, J=2.2 Hz, 1H), 6.96 (d, J=1.0 Hz, 2H), 6.89 (s, 1H), 4.15-4.01 (m, 2H), 3.88 (d, J=14.7 Hz, 1H), 3.79 (d, J=14.5 Hz, 1H), 3.53-3.45 (m, 1H), 3.31-3.22 (m, 2H), 2.93-2.77 (m, 3H), 2.74 (dd, J=2.1, 9.7 Hz, 1H), 2.37 (dd, J=7.2, 16.0 Hz, 1H), 2.25-1.92 (m, 7H), 1.90-1.75 (m, 3H), 1.54 (d, J=7.0 Hz, 3H), 0.85-0.74 (m, 2H), 0.73-0.70 (m, 1H), 0.65 (br. s., 1H), 0.51 (t, J=6.3 Hz, 2H). m/z (ESI, +ve ion) 599.2 (M+H)$^+$.

Example 952. (1S,3'R,6'R,7'R,8'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

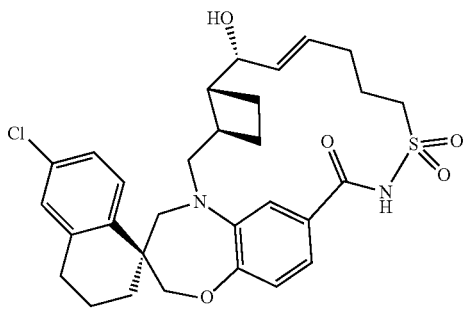 [SMILES: O=C1NS(=O)(=O)CCC/C=C/[C@@H](O)[C@@H]2CC[C@H]2CN2C[C@@]3(CCCc4cc(Cl)ccc43)COc3ccc1cc32]

The title compound was prepared in an analogous manner to that described in Example 719, Steps 1 and 2, using Intermediate AA11B and pent-4-ene-1-sulfonamide (Intermediate EE19, Step 2), and the desired product, (1S,3'R,6'R,7'R,8'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (400 MHz, CD$_3$OD) δ 7.76 (d, J=8.6 Hz, 1H), 7.28 (d, J=2.0 Hz, 1H), 7.19 (dd, J=2.3, 8.4 Hz, 1H), 7.12 (d, J=2.2 Hz, 1H), 7.03 (dd, J=2.0, 8.2 Hz, 1H), 6.94 (d, J=8.0 Hz, 1H), 5.76 (td, J=5.8, 15.4 Hz, 1H), 5.58 (dd, J=7.1, 15.6 Hz, 1H), 4.10 (s, 2H), 4.01-3.88 (m, 3H), 3.69 (d, J=14.1 Hz, 1H), 3.08 (dd, J=8.8, 15.3 Hz, 1H), 2.88-2.71 (m, 2H), 2.62-2.51 (m, 1H), 2.44-2.31 (m, 2H), 2.19-1.57 (m, 12H), 1.54-1.39 (m, 1H). m/z (ESI, +ve ion) 571.2 (M+H)$^+$.

Example 953. (1S,3'R,6'R,7'R,8'E,12'R)-6-chloro-7'-hydroxy-12'-methyl-3,4-dihydro-2H,15'H-spiro [naphthalene-1,22'-[20]oxa[13]thia[1,14]diazatetracyclo[14.7.2.0$^{3,6}$.0$^{19,24}$]pentacosa [8,16,18,24] tetraen]-15'-one 13',13'-dioxide and Example 954. (1S,3'R,6'R,7'R,8'E,12'S)-6-hloro-7'-hydroxy-12'-methyl-3,4-dihydro-2H,15'H-spiro[naphthalene-1, 22'-[20]oxa[13]thia[1,14]diazatetracyclo[14.7.2. 0$^{3,6}$.0$^{19,24}$]pentacosa [8,16,18,24]tetraen]-15'-one 13',13'-dioxide Example 953

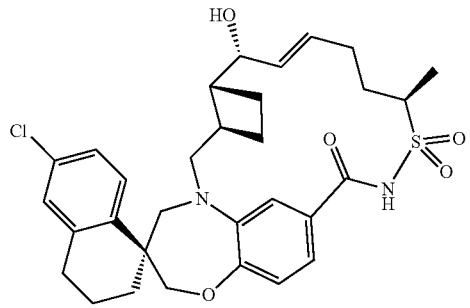

Example 954

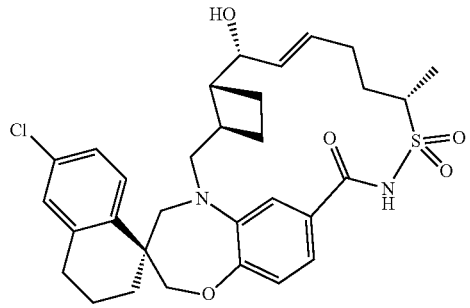

The title compounds were prepared in an analogous manner to that described in Example 719, Steps 1 and 2, using Intermediate AA11B and a racemic mixture of (R)-hex-5-ene-sulfonamide (Intermediate EE20) and (S)-hex-5-ene-sulfonamide (Intermediate EE202), and the desired products, (1S,3'R,6'R,7'R,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (second eluting peak out of reverse phase preparative HPLC) and (1S,3'R,6'R,7'R,8'E,12'S)-6-chloro-7'-hydroxy-12'-methyl- 3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (first eluting peak out of reverse phase preparative HPLC) were isolated. (1S,3'R,6'R,7'R,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 953). ¹H NMR (500 MHz, MeOH) δ 7.76 (d, J=8.6 Hz, 1H), 7.42 (d, J=1.5 Hz, 1H), 7.19 (dd, J=2.2, 8.6 Hz, 1H), 7.12 (d, J=2.0 Hz, 1H), 7.09 (dd, J=1.5, 8.1 Hz, 1H), 6.94 (d, J=8.0 Hz, 1H), 5.55 (d, J=3.4 Hz, 2H), 4.10 (s, 2H), 4.00-3.90 (m, 2H), 3.79 (d, J=2.4 Hz, 1H), 3.70 (d, J=14.2 Hz, 1H), 3.05 (dd, J=7.0, 15.3 Hz, 1H), 2.86-2.74 (m, 2H), 2.61-2.46 (m, 2H), 2.39-2.30 (m, 1H), 2.16-2.02 (m, 3H), 1.98-1.82 (m, 4H), 1.81-1.62 (m, 4H), 1.47 (d, J=7.1 Hz, 3H), 1.46-1.41 (m, 1H). m/z (ESI, +ve ion) 585.2 (M+H)⁺; (1S,3'R,6'R,7'R,8'E,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 954). ¹H NMR (400 MHz, CD₃OD) δ 7.74 (d, J=8.6 Hz, 1H), 7.19 (dd, J=2.2, 8.5 Hz, 1H), 7.13 (d, J=2.2 Hz, 1H), 6.99-6.87 (m, 3H), 5.90-5.81 (m, 1H), 5.54 (dd, J=7.9, 15.2 Hz, 1H), 4.15-3.96 (m, 4H), 3.69 (d, J=14.3 Hz, 1H), 3.59 (d, J=13.5 Hz, 1H), 3.49 (d, J=13.1 Hz, 1H), 3.27 (dd, J=9.4, 15.3 Hz, 1H), 2.88-2.73 (m, 2H), 2.56-2.37 (m, 2H), 2.24-2.15 (m, 1H), 2.13-1.89 (m, 7H), 1.88-1.69 (m, 3H), 1.58-1.50 (m, 1H), 1.51 (d, J=6.8 Hz, 3H). m/z (ESI, +ve ion) 585.2 (M+H)⁺.

Example 955. (1S,3'R,6'R,7'S,8'E,12'R)-6-chloro-7'-(((2R)-1-methoxy-2-propanyl)oxy)-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15',13'-dioxide and (1S,3'R,6'R,7'S,8'E,12'R)-6-chloro-7'-(((2S)-1-methoxy-2-propanyl)oxy)-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

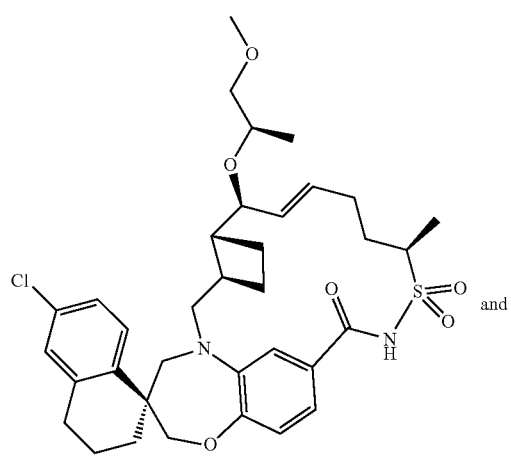

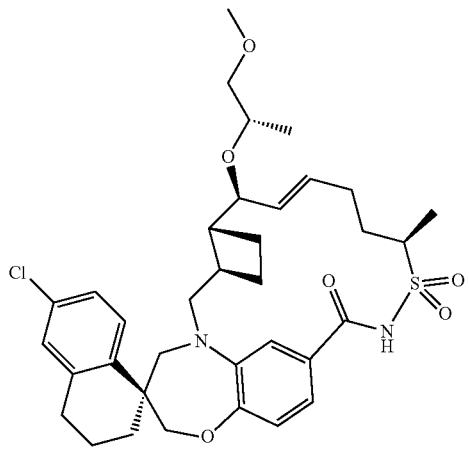

Sodium hydride (60% dispersion in mineral oil, 3.2 mg, 0.08 mmol) was added to a solution of (1S,3'R,6'R,7'S,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 404, Step 1; 9.4 mg, 0.016 mmol) in THF (535 μl) at 0° C. After 30 min, 2-bromo-1-methoxypropane (2.46 mg, 0.016 mmol, Bellen) was added. The reaction mixture was heated to 60° C. and stirred at for 48 h. The reaction mixture was quenched with water and 1 N HCl soluiton, 25 mL of EtOAc was added. The organic layer was concentrated and purified through a 4 g ISCO Gold column, eluting with 0-30% EtOAc(with 0.3% HOAc) in hexane to give a mixture of (1S,3'R,6'R,7'S,8'E,12'R)-6-chloro-7'-(((2R)-1-methoxy-2-propanyl)oxy)-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide and (1S,3'R,6'R,7'S,8'E,12'R)-6-chloro-7'-(((2S)-1-methoxy-2-propanyl)oxy)-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (1.7 mg, 2.59 μmol). ¹H NMR (500 MHz, CD₃OD) δ 7.75 (d, J=10.3 Hz, 1H), 7.19 (dd, J=1.7, 8.3 Hz, 1H), 7.13 (d, J=1.7 Hz, 1H), 7.02-6.98 (m, 1H), 6.95 (dd, J=1.0, 8.3 Hz, 1H), 6.88 (dd, J=1.7, 3.9 Hz, 1H), 5.86-5.79 (m, 1H), 5.64-5.57 (m, 1H), 4.21-4.14 (m, 1H), 4.09 (dd, J=12.0, 14.9 Hz, 2H), 4.01 (ddd, J=3.7, 8.6, 23.7 Hz, 1H), 3.85 (dd, J=4.4, 14.9 Hz, 1H), 3.74-3.65 (m, 2H), 3.33-3.29 (m, 3H overlap with solvent), 3.28-3.24 (m, 1H), 3.08 (dd, J=9.7, 14.8 Hz, 1H), 2.87-2.68 (m, 2H), 2.54-2.27 (m, 5H), 2.12 (d, J=13.7 Hz, 1H), 2.00-1.70 (m, 6H), 1.60 (dd, J=7.1, 11.2 Hz, 1H), 1.52 (d, J=6.8 Hz, 3H), 1.49-1.42 (m, 1H), 1.49-1.42 (m, 1H), 1.10 (dd, J=6.1, 35.0 Hz, 3H), 0.93 (t, J=7.1 Hz, 1H). m/z (ESI, +ve ion) 657.2 (M+H)⁺.

Example 956. (1S,3'R,6'R,7'S,8'E,12'R)-6-chloro-12'-methyl-7'-(2-pyrimidinylmethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

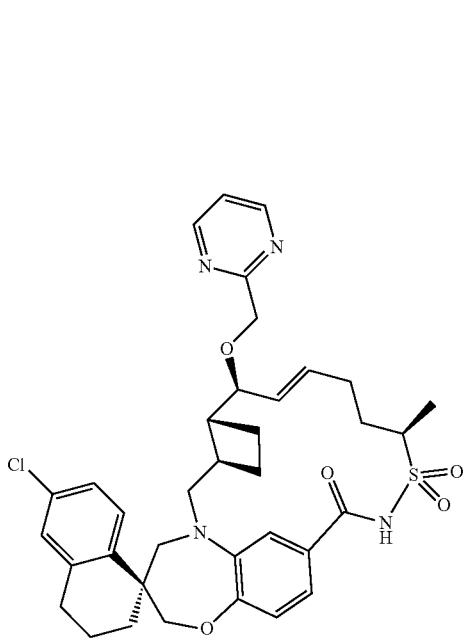 [SMILES: C[C@@H]1CC/C=C/[C@H](OCc2ncccn2)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 720 using (1S,3'R,6'R,7'S,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 404, Step 1) and 2-(chloromethyl)pyrimidine (TCI), and the desired product, (1S,3'R,6'R,7'S,8'E,12'R)-6-chloro-12'-methyl-7'-(2-pyrimidinylmethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide was isolated as a white solid. ¹H NMR (400 MHz, CD₃OD) δ 8.82 (d, J=4.9 Hz, 2H), 7.75 (d, J=8.6 Hz, 1H), 7.43 (t, J=5.1 Hz, 1H), 7.19 (t, J=6.0 Hz, 1H), 7.13 (s, J=5.1 Hz, 1H), 7.04 (d, J=6.5 Hz, 1H), 6.93-6.85 (m, 2H), 5.97-5.82 (m, 1H), 5.65 (dd, J=8.7, 15.2 Hz, 1H), 4.65 (dd, J=11.3, 24.6 Hz, 2H), 4.15-4.00 (m, 4H), 3.83 (d, J=14.7 Hz, 1H), 3.67 (d, J=14.5 Hz, 1H), 3.20-2.87 (m, 2H), 2.88-2.72 (m, 2H), 2.63 (d, J=5.1 Hz, 1H), 2.41 (br. s., 2H), 2.27 (br. s., 1H), 2.11 (d, J=14.3 Hz, 1H), 2.03-1.84 (m, 6H), 1.80-1.66 (m, 2H), 1.51 (d, J=6.5 Hz, 3H), 1.47-1.39 (m, 1H) m/z (ESI, +ve ion) 677.4 (M+H)⁺.

Example 957. (1S,3'R,6'R,7'S,8'E,12'R)-6-chloro-12'-methyl-7'-((2-methyl-2H-tetrazol-5-yl)methoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

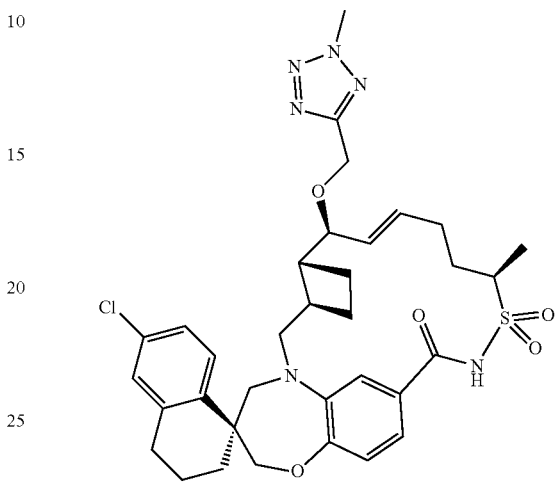

Step 1:5-(chloromethyl)-2-methyl-2H-tetrazole

To 5-(chloromethyl)-2H-tetrazole (516 ng, 4.4 mmol) in diethyl ether (8.7 mL), was slowly added trirethylsilydiazomethane (2.6 mL, 5.2 mmol, Aldrich) at 0° C. (this should be done slowly due to gas evolution). The yellow reaction was allowed to stir overnight at rt before being concentrated purified by chromatography using ISCO 40 G gold silica column, eluting with 5-50% EtOAc in hexanes. The product was collected and concentrated to afford the desired product as a colorless oil.

Step 2: (1S,3'R,6'R,7'S,8'E,12'R)-6-chloro-12'-methyl-7'-((2-methyl-2H-tetrazol-5-yl)methoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide The title compound was prepared in an analogous manner to that described in Example 720 using (1S,3'R,6'R,7'S,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 404, Step 1) and 5-(chloromethyl)-2-methyl-2H-tetrazole from Step 1, and the desired product, (1S,3'R,6'R,7'S,8'E,12'R)-6-chloro-12'- methyl-7'-((2-methyl-2H-tetrazol-5-yl)methoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (400 MHz, CD$_3$OD) δ 7.76 (d, J=8.6 Hz, 1H), 7.19 (d, J=8.7 Hz, 1H), 7.12 (d, J=2.2 Hz, 1H), 7.02 (d, J=7.2 Hz, 1H), 6.92-6.86 (m, 2H), 6.02-5.86 (m, 1H), 5.62 (dd, J=8.7, 15.2 Hz, 1H), 4.69 (dd, J=11.3, 28.2 Hz, 2H), 4.41 (s, 3H), 4.21-4.11 (m, 1H), 4.07 (dd, J=11.5, 15.3 Hz, 2H), 3.97 (dd, J=3.8, 8.7 Hz, 1H), 3.82 (d, J=14.7 Hz, 1H), 3.68 (d, J=14.1 Hz, 1H), 3.07 (dd, J=10.1, 15.0 Hz, 1H), 2.87-2.73 (m, 2H), 2.55-2.26 (m, 4H), 2.11 (d, J=13.3 Hz, 1H), 2.01 (s, 1H), 1.94 (br. s., 3H), 1.90-1.65 (m, 5H), 1.53 (d, J=6.8 Hz, 3H), 1.49-1.39 (m, 1H). m/z (ESI, +ve ion) 681.2 (M+H)$^+$.

Example 958. (1S,3'R,6'R,7'S,8'E,12'R)-6-chloro-12'-methyl-7'-(4H-1,2,4-triazol-3-ylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

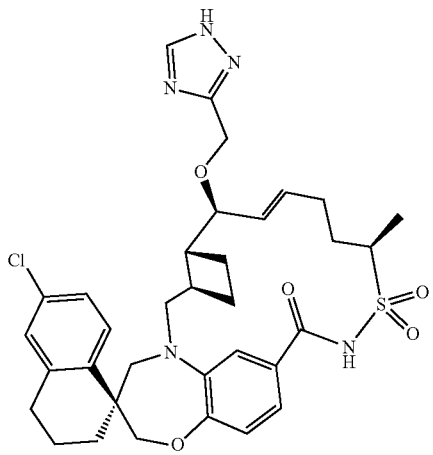 [SMILES: C[C@@H]1CC/C=C/[C@H](OCc2nc[nH]n2)[C@@H]2CC[C@H]2CN2C[C@@]3(CCCc4cc(Cl)ccc43)COc3ccc(cc32)C(=O)NS1(=O)=O]

Step 1:3-(chloromethyl)-1-((2-(trimethylsilyl)ethoxy)methyl)-1H-1,2,4-triazole and 3-(chloromethyl)-4-((2-(trimethylsilyl)ethoxy)methyl)-4H-1,2,4-triazole

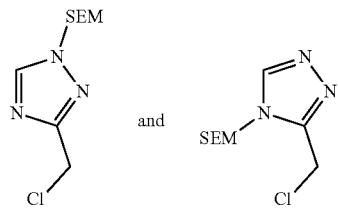 [SMILES: C[Si](C)(C)CCOCn1cnc(CCl)n1 ; C[Si](C)(C)CCOCn1cnnc1CCl]

Sodium hydride (60% dispersion in mineral oil, 292 mg, 7.31 mmol, Aldrich) was adde, 3-(chloromethyl)-1H-1,2,4-triazole (573 mg, 4.88 mmol, Anichem) in 20 mL of THF at 0° C. After 30 min, (2-(chloromethoxy)ethyl)trimethylsilane (975 mg, 5.85 mmol, Aldrich) was added slowly. The ice bath was removed and the reaction mixture was stirred at rt overnight. The reaction mixture was adjusted pH to 7 with 1 N aq. HCl solution, and then 15 mL of water and 30 mL of EtOAc was added. The organic layer was concentrated and purified by chromatography using ISCO 40 G gold silica column, eluting with 0-40% EtOAc/hexanes. The product was collected and concentrated to afford the desired product.

Step 2: (1S,3'R,6'R,7'S,8'E,12'R)-6-chloro-12'-methyl-7'-(4H-1,2,4-triazol-3-ylmethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide The title compound was prepared in an analogous manner to that described in Example 720 using (1S,3'R,6'R,7'S,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 404, Step 1) and 3-(chloromethyl)-1-((2-(trimethylsilyl)ethoxy)methyl)-1H-1,2,4-triazole with 3-(chloromethyl)-4-((2-(trimethylsilyl)ethoxy)methyl)-4H-1,2,4-triazole (1:1). Tetrabutylammonium fluoride (0.5 M solution in THF) was added to deprotect SEM goup to give the desired final product (1S,3'R,6'R,7'S,8'E,12'R)-6-chloro-12'-methyl-7'-(4H-1,2,4-triazol-3-ylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as a light-yellow solid. $^1$H NMR (500 MHz, CD$_3$OD) δ 8.59-7.82 (m, 1H), 7.71 (d, J=8.6 Hz, 1H), 7.14 (d, J=8.3 Hz, 1H), 7.08 (s, 1H), 7.01 (br. s., 1H), 6.85 (t, J=7.6 Hz, 2H), 5.94 (br. s., 1H), 5.59 (dd, J=8.8, 14.4 Hz, 1H), 4.57 (br. s., 2H), 4.13-3.96 (m, 3H), 3.94 (br. s., 1H), 3.80 (d, J=14.9 Hz, 1H), 3.62 (d, J=15.4 Hz, 1H), 3.67-3.60 (m, 1H), 3.33 (s, 2H), 3.06-2.98 (m, 1H), 2.85-2.70 (m, 2H), 2.50 (br. s., 1H), 2.39 (br. s., 2H), 2.25 (br. s., 1H), 2.07 (d, J=14.2 Hz, 1H), 1.93-1.86 (m, 3H), 1.86-1.77 (m, 2H), 1.76-1.65 (m, 2H), 1.47 (d, J=6.4 Hz, 3H), 1.44-1.36 (m, 1H). m/z (ESI, +ve ion) 666.2 (M+H)$^+$.

Example 964. 2-(((1S,3'R,6'R,7'S,8'Z,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-methylacetamide

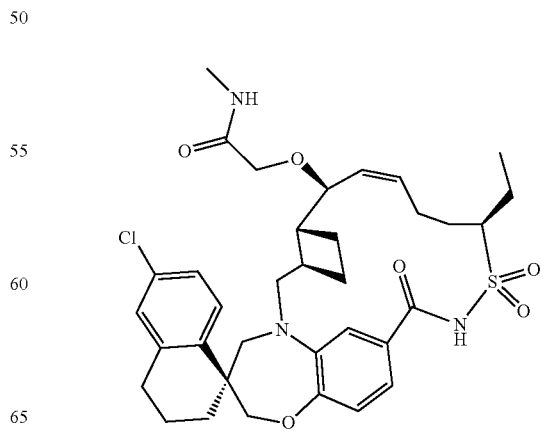

Step 1: (1S,3'R,6'R,7'S,8'Z,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

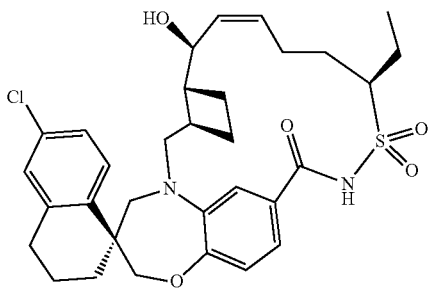 [SMILES: CC[C@@H]1CC/C=C\[C@H](O)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 719, Steps 1 and 2, using (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Intermediate AA11A) and a racemic mixture of (R)-hept-6-ene-3-sulfonamide (Intermediate EE21) and (S)-hept-6-ene-3-sulfonamide (Intermediate EE212), and the desired product, (1S,3'R,6'R,7'S,8'Z,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was obtained as a single isomer (second eluting peak) from the reverse phase preparative HPLC. $^1$H NMR (500 MHz, CD$_3$OD) δ 7.75 (d, J=8.6 Hz, 1H), 7.19 (dd, J=2.3, 8.4 Hz, 1H), 7.12 (d, J=2.2 Hz, 1H), 7.03 (dd, J=2.0, 8.1 Hz, 1H), 6.97-6.92 (m, 2H), 5.62-5.55 (m, 2H), 4.49 (dd, J=3.5, 7.9 Hz, 1H), 4.09 (dd, J=12.5, 21.8 Hz, 2H), 3.88 (d, J=15.7 Hz, 1H), 3.71 (d, J=14.4 Hz, 1H), 3.62 (br. s., 1H), 2.87-2.74 (m, 2H), 2.49-2.38 (m, 3H), 2.26-2.10 (m, 3H), 2.06-1.89 (m, 8H), 1.84-1.73 (m, 3H), 1.55-1.40 (m, 1H), 1.16 (t, J=7.5 Hz, 3H). m/z (ESI, +ve ion) 599.2 (M+H)$^+$.

Step 2: 2-(((1S,3'R,6'R,7'S,8'Z,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N-methylacetamide The title compound was prepared in an analogous manner to that described in Example 720 using (1S,3'R,6'R,7'S,8'Z,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 964, Step 1) and 2-chloro-N-methylacetamide (Aldrich), and the desired product, 2-(((1S,3'R,6'R,7'S,8'Z,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)-N-methylacetamide was isolated as a white solid. $^1$H NMR (400 MHz, CD$_3$OD) δ 7.74 (d, J=8.4 Hz, 1H), 7.19 (dd, J=2.2, 8.6 Hz, 1H), 7.12 (d, J=2.3 Hz, 1H), 7.00 (dd, J=2.0, 8.4 Hz, 1H), 6.95 (d, J=8.0 Hz, 1H), 6.90 (d, J=1.6 Hz, 1H), 5.77 (td, J=6.9, 11.1 Hz, 1H), 5.49 (t, J=10.6 Hz, 1H), 4.28 (dd, J=2.9, 9.4 Hz, 1H), 4.09 (ddd, J=12.1, 13.5, 25.8 Hz, 2H), 3.95-3.81 (m, 3H), 3.71 (d, J=14.1 Hz, 1H), 3.68-3.59 (m, 1H), 2.80 (s, 5H), 2.68-2.60 (m, 1H), 2.45-2.28 (m, 2H), 2.27-2.10 (m, 3H), 2.05-1.89 (m, 7H), 1.88-1.75 (m, 3H), 1.49 (t, J=10.9 Hz, 1H), 1.31 (s, 1H), 1.17 (t, J=7.5 Hz, 3H). m/z (ESI, +ve ion) 670.2 (M+H)$^+$.

Example 965. (1S,3'R,6'R,7'S,8'E,12'R)-6-chloro-12'-ethyl-7'-((1-methyl-1H-IMIDAZOL-2-yl)methoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

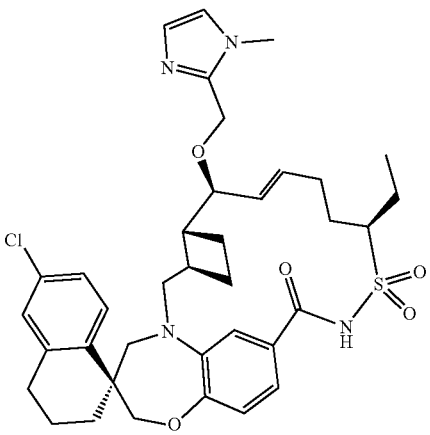 [SMILES: CC[C@@H]1CC/C=C/[C@H](OCc2nccn2C)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 2-(chloromethyl)-1-methyl-1H-imidazole (Matrix Scientific), and the desired product, (1S,3'R,6'R,7'S,8'E,12'R)-6-chloro-12'-ethyl-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (400 MHz, CD$_3$OD) δ 7.64 (d, J=8.6 Hz, 1H), 7.45 (dd, J=2.0, 18.4 Hz, 2H), 7.09 (dd, J=2.2, 8.5 Hz, 1H), 7.02 (d, J=2.2 Hz, 1H), 6.90 (dd, J=2.0, 8.4 Hz, 1H), 6.84 (d, J=8.0 Hz, 1H), 6.74 (d, J=1.8 Hz, 1H), 5.92-5.84 (m, 1H), 5.59 (dd, J=9.2, 15.3 Hz, 1H), 4.64 (dd, J=14.5, 28.6 Hz, 2H), 4.03-3.91 (m, 4H), 3.79 (s, 3H), 3.74 (d, J=16.0 Hz, 1H), 3.57 (d, J=14.9 Hz, 1H), 3.00 (dd, J=10.2, 15.3 Hz, 1H), 2.76-2.62 (m, 2H), 2.53-2.44 (m, 1H), 2.39-2.17 (m, 3H), 2.06-1.64 (m, 12H), 1.36 (t, J=11.5 Hz, 1H), 1.13 (t, J=7.4 Hz, 3H). m/z (ESI, +ve ion) 693.2 (M+H)$^+$.

Example 966. (1S,3'R,6'R,7'S,8'E,12'R)-6-chloro-12'-ethyl-7'-((5-methyl-1,3,4-oxadiazol-2-yl)methoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

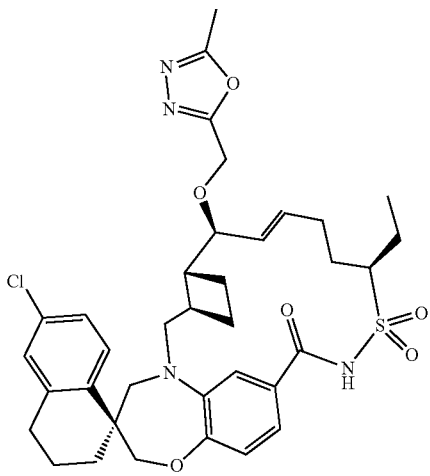 [SMILES: CC[C@@H]1CC/C=C/[C@H](OCc2nnc(C)o2)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 2-(chloromethyl)-5-methyl-1,3,4-oxadiazole (Frontier Scientific Services), and the desired product, (1S,3'R,6'R,7'S,8'E,12'R)-6-chloro-12'-ethyl-7'-((5-methyl-1,3,4-oxadiazol-2-yl)methoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (400 MHz, CD$_3$OD) δ 7.64 (d, J=8.6 Hz, 1H), 7.08 (dd, J=2.2, 8.5 Hz, 1H), 7.01 (d, J=2.2 Hz, 1H), 6.89 (dd, J=2.0, 8.2 Hz, 1H), 6.81 (d, J=7.8 Hz, 1H), 6.75 (d, J=2.2 Hz, 1H), 5.86-5.77 (m, 1H), 5.51 (dd, J=8.8, 15.3 Hz, 1H), 4.51 (dd, J=13.5, 18.8 Hz, 2H), 4.02-3.91 (m, 3H), 3.88 (dd, J=3.5, 8.6 Hz, 1H), 3.74 (d, J=14.9 Hz, 1H), 3.57 (d, J=14.1 Hz, 1H), 3.17 (d, J=14.5 Hz, 1H), 2.98 (dd, J=9.9, 15.4 Hz, 1H), 2.76-2.61 (m, 2H), 2.47 (s, 3H), 2.37-2.15 (m, 3H), 2.07-1.95 (m, 2H), 1.91-1.64 (m, 9H), 1.39-1.27 (m, 1H), 1.26-1.18 (m, 1H), 1.12 (t, J=7.5 Hz, 3H). m/z (ESI, +ve ion) 695.3 (M+H)$^+$.

Example 967. (1S,3'R,6'R,7'S,8'E,12'R)-6-chloro-7'-((1,3-dimethyl-1H-pyrazol-5-yl)methoxy)-12'-ethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

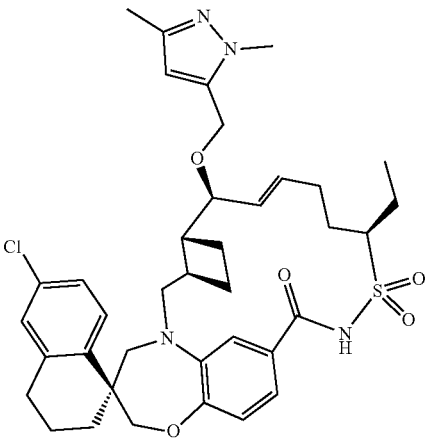 [SMILES: CC[C@@H]1CC/C=C/[C@H](OCc2cc(C)nn2C)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 5-(chloromethyl)-1,3-dimethyl-1H-pyrazole (Frontier Scientific Services), and the desired product, (1S,3'R,6'R,7'S,8'E,12'R)-6-chloro-7'-((1,3-dimethyl-1H-pyrazol-5-yl)methoxy)-12'-ethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (400 MHz, CD$_3$OD) δ 8.07-8.01 (m, 1H), 7.71 (d, J=8.6 Hz, 1H), 7.21 (dd, J=2.2, 8.5 Hz, 1H), 7.11 (d, J=2.2 Hz, 1H), 6.96-6.89 (m, 2H), 6.81 (d, J=1.6 Hz, 1H), 5.98 (s, 1H), 5.92-5.84 (m, 1H), 5.61 (dd, J=8.8, 15.3 Hz, 1H), 4.44 (d, J=12.1 Hz, 1H), 4.30 (d, J=12.3 Hz, 1H), 4.22-4.15 (m, 1H), 4.09 (dd, J=11.7, 21.1 Hz, 2H), 3.87 (dd, J=2.9, 8.6 Hz, 1H), 3.81 (d, J=14.9 Hz, 4H), 3.73 (d, J=13.9 Hz, 1H), 3.23 (d, J=14.3 Hz, 1H), 2.95 (d, J=29.1 Hz, 2H), 2.85-2.72 (m, 2H), 2.48-1.90 (m, 11H), 1.89-1.75 (m, 5H), 1.72-1.52 (m, 1H), 1.46-1.36 (m, 1H), 1.27 (d, J=7.4 Hz, 3H). m/z (ESI, +ve ion) 707.4 (M+H)$^+$.

Example 968. (1S,3'R,6'R,7'S,8'E,12'R)-6-chloro-7'-(2-(1,3-dioxolan-2-yl)ethoxy)-12'-ethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide Example 969. (1S,3'R,6'R,7'S,8'E,12'R)-6-chloro-12'-ethyl-7'-(2-((2S)-tetrahydro-2H-pyran-2-yloxy)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide and (1S,3'R,6'R,7'S,8'E,12'R)-6-chloro-12'-ethyl-7'-(2-((2R)-tetrahydro-2H-pyran-2-yloxy)ethoxy)-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

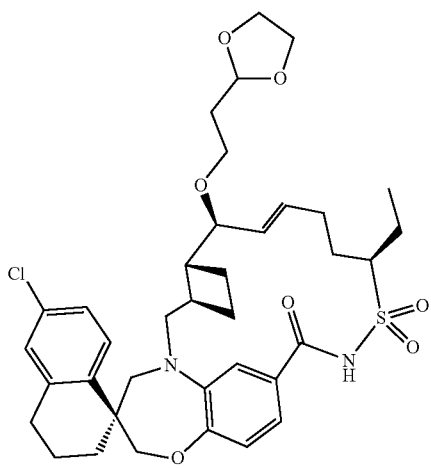 [SMILES: CC[C@@H]1CC/C=C/[C@H](OCCC2OCCO2)[C@@H]2CC[C@H]2CN2C[C@@]3(CCCc4cc(Cl)ccc43)COc3ccc(cc32)C(=O)NS1(=O)=O]

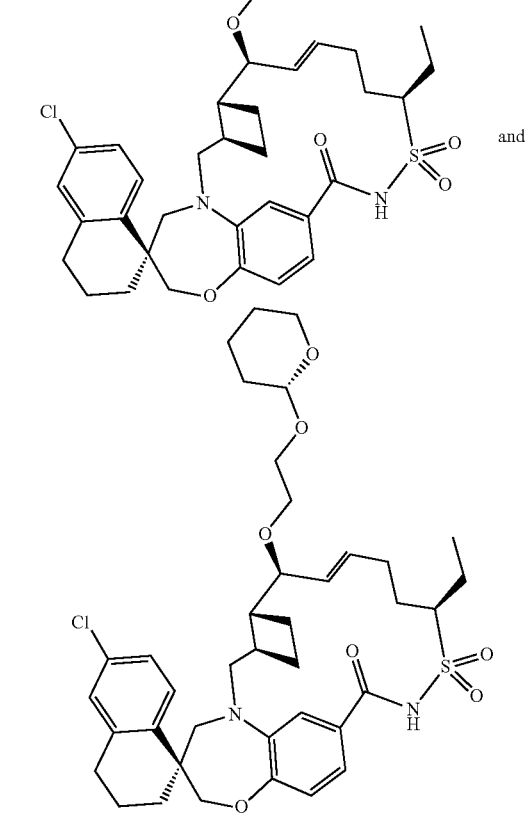

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 2-(2-bromoethyl)-1,3-dioxolane (Aldrich), and the desired product, (1S,3'R,6'R,7'S,8'E,12'R)-6-chloro-7'-(2-(1,3-dioxolan-2-yl)ethoxy)-12'-ethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (400 MHz, CD$_3$OD) δ 7.76 (d, J=8.4 Hz, 1H), 7.19 (dd, J=0.6, 8.2 Hz, 1H), 7.13 (d, J=1.8 Hz, 1H), 7.01 (dd, J=1.0, 8.0 Hz, 1H), 6.93 (d, J=8.2 Hz, 1H), 6.90-6.86 (m, 1H), 5.87 (ddd, J=6.3, 13.9, 21.3 Hz, 1H), 5.58 (dd, J=8.6, 15.3 Hz, 1H), 4.09 (d, J=2.7 Hz, 2H), 3.99-3.80 (m, 9H), 3.72-3.55 (m, 4H), 3.49-3.42 (m, 1H), 3.07 (dd, J=10.2, 16.6 Hz, 1H), 2.85-2.72 (m, 2H), 2.52-2.28 (m, 4H), 2.28-2.06 (m, 3H), 1.98-1.70 (m, 8H), 1.51-1.40 (m, 1H), 1.20 (t, J=7.5 Hz, 3H). m/z (ESI, +ve ion) 699.2 (M+H)$^+$.

The title compound was prepared in an analogous manner to that described in Example 720, using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 2-(2-bromoethoxy)tetrahydro-2H-pyran (Aldrich), and the desired products, a mixture of (1S,3'R,6'R,7'S,8'E,12'R)-6-chloro-12'-ethyl-7'-(2-((2S)-tetrahydro-2H-pyran-2-yloxy)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,12'R)-6-chloro-12'-ethyl-7'-(2-((2R)-tetrahydro-2H-pyran- 2-yloxy)ethoxy)-3,4-dihydro-2H,15'H-spiro[naphthalene-1, 22'-[20]oxa[13]thia[1,14]diazatetracyclo[14.7.2.0~3, 6~.0.0~19,24~]pentacosa[8,16,18,2 4]tetraen]-15'-one 13', 13'-dioxide was isolated as a white solid. $^1$H NMR (400 MHz, CD$_3$OD) δ 7.75 (d, J=8.4 Hz, 1H), 7.19 (dd, J=2.3, 8.4 Hz, 1H), 7.13 (d, J=2.2 Hz, 1H), 7.00 (dd, J=1.6, 8.0 Hz, 1H), 6.94 (d, J=8.0 Hz, 1H), 6.88 (d, J=1.8 Hz, 1H), 5.92-5.84 (m, 1H), 5.60 (dd, J=8.7, 15.2 Hz, 1H), 4.66 (ddd, J=2.3, 4.5, 6.8 Hz, 1H), 4.13-4.01 (m, 3H), 3.96-3.81 (m, 5H), 3.69 (d, J=15.8 Hz, 2H), 3.61 (d, J=9.6 Hz, 1H), 3.09 (dd, J=10.1, 15.4 Hz, 1H), 2.88-2.73 (m, 2H), 2.57-2.28 (m, 4H), 2.18-2.07 (m, 2H), 2.00-1.71 (m, 10H), 1.66-1.53 (m, 7H), 1.52-1.41 (m, 1H), 1.21 (t, J=7.5 Hz, 3H). m/z (ESI, +ve ion) 727.2 (M+H)$^+$.

Example 970. (1S,3'R,6'R,7'S,8'E,12'R)-6-chloro-12'-ethyl-7'-(2-hydroxyethoxy)-3,4-dihydro-2H, 15'H-spiro[naphthalene-1,22'-[20]oxa[13]thia[1,14]diazatetracyclo[14.7.2.0$^{3,6}$.0$^{19,24}$]pentacosa [8,16,18, 24]tetraen]-15'-one 13',13'-dioxide

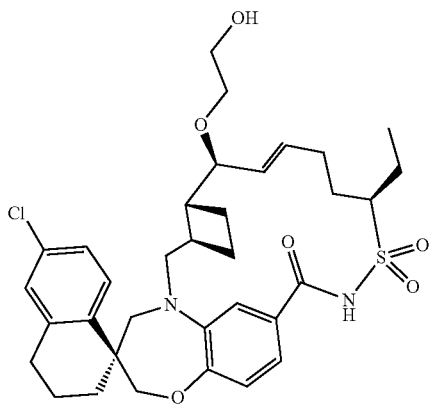 [SMILES: CC[C@@H]1CC/C=C/[C@H](OCCO)[C@@H]2CC[C@H]2CN2C[C@@]3(CCCc4cc(Cl)ccc43)COc3ccc(cc32)C(=O)NS1(=O)=O]

(1S,3'R,6'R,7'S,8'E,12'R)-6-chloro-12'-ethyl-7'-(2-((2S)-tetrahydro-2H-pyran-2-yloxy)ethoxy)-3,4-dihydro-2H, 15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (from Example 969; 4.1 mg, 5.6 μmol) was stirred at 55° C. in 2 N hydrochloric acid (2 mL, 4 mmol)/THF (2 mL) for 30 min, and then the reaction mixture was concentrated and purified by reverse phase preparative HPLC (Gemini™ Prep C$_{18}$ 5 μm column; Phenomenex, Torrance, CA; gradient elution of 40% to 95% MeCN in water, where both solvents contain 0.1% TFA, 30 min method) to give (1S,3'R,6'R,7'S,8'E,12'R)-6-chloro-12'-ethyl-7'-(2-hydroxyethoxy)-3,4-dihydro-2H,15'H-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (2.1 mg, 3.3 μmol). $^1$H NMR (400 MHz, CD$_3$OD) δ 7.74 (d, J=8.6 Hz, 1H), 7.19 (dd, J=2.3, 8.6 Hz, 1H), 7.13 (d, J=2.2 Hz, 1H), 6.99 (dd, J=2.0, 6.3 Hz, 1H), 6.95 (d, J=8.2 Hz, 1H), 6.87 (d, J=1.8 Hz, 1H), 5.91-5.82 (m, 1H), 5.65 (dd, J=8.6, 15.8 Hz, 1H), 4.15-4.01 (m, 3H), 3.91-3.82 (m, 2H), 3.72-3.62 (m, 3H), 3.58-3.49 (m, 1H), 3.45-3.38 (m, 1H), 3.08 (dd, J=10.6, 15.5 Hz, 1H), 2.84-2.73 (m, 2H), 2.61-2.48 (m, 1H), 2.46-2.27 (m, 3H), 2.18-2.05 (m, 2H), 2.00-1.80 (m, 8H), 1.54-1.37 (m, 1H), 1.32 (s, 2H), 1.21 (t, J=7.5 Hz, 3H). m/z (ESI, +ve ion) 643.2 (M+H)$^+$.

Example 971. tert-butyl (((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia [1,14]diazatetracyclo[14.7.2.0$^{3,6}$.0$^{19,24}$]pentacosa [8,16,18,24]tetraen]-7'-yl)oxy)acetate

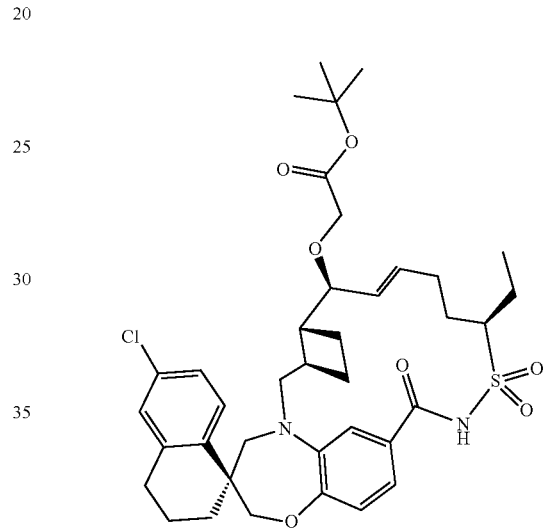

The title compound was prepared in an analogous manner to that described in Example 720 using (1S,3'R,6'R,7'S,8'E, 12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and bromoacetic acid tert-butyl ester (Alfa Aesar), and the desired product, tert-butyl (((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$] pentacosa[8,16,18,24]tetraen]-7'-yl)oxy)acetate was isolated as a white solid. $^1$H NMR (400 MHz, CDCl$_3$) δ 8.08 (br. s., 1H), 7.72 (d, J=8.6 Hz, 1H), 7.20 (dd, J=2.3, 8.4 Hz, 1H), 7.11 (d, J=2.3 Hz, 1H), 6.93 (d, J=8.0 Hz, 1H), 6.90 (dd, J=1.6, 8.2 Hz, 1H), 6.83 (d, J=1.6 Hz, 1H), 5.89-5.82 (m, 1H), 5.60 (dd, J=9.0, 15.3 Hz, 1H), 4.20-4.12 (m, 1H), 4.09 (dd, J=12.1, 19.8 Hz, 2H), 3.92-3.81 (m, 4H), 3.74 (d, J=14.3 Hz, 1H), 3.25 (d, J=14.1 Hz, 1H), 3.03 (dd, J=10.2, 15.3 Hz, 1H), 2.85-2.73 (m, 2H), 2.66-2.57 (m, 1H), 2.42-2.23 (m, 3H), 2.21-2.13 (m, 1H), 2.10-1.81 (m, 10H), 1.53 (s, 9H), 1.26 (m, 4H). m/z (ESI, +ve ion) 713.2 (M+H)$^+$.

Example 972. (1S,3'R,6'R,7'S,8'E,12'R)-6-chloro-12'-ethyl-7'-(2-hydroxy-2-methylpropoxy)-3,4-di-hydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide Example 973. 2-(((1S,3'R,6'R,7'S,8'E,12'R)-6-chloro-12'-ethyl-13',13'-dioxido-15'-oxo-3,4-di-hydro-2H-spiro[naphthalene-1,22'-[20]oxa[13]thia[1,14]diazatetracyclo[[14.7.2.0$^{3,6}$.0$^{19,24}$]pentacosa[8,16,18,24]tetraen]-7'-yl)oxy)-N,N-dimethylacetamide

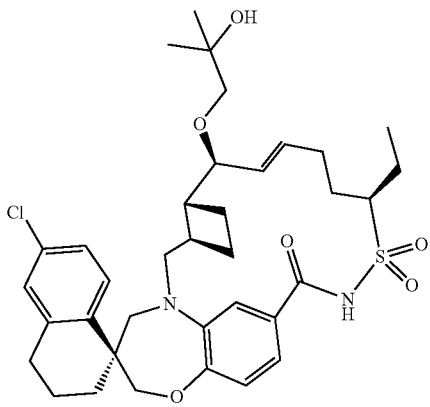 [SMILES: CC[C@@H]1CC/C=C/[C@H](OCC(C)(C)O)[C@@H]2CC[C@H]2CN2C[C@@]3(CCCc4cc(Cl)ccc43)COc3ccc(cc32)C(=O)NS1(=O)=O]

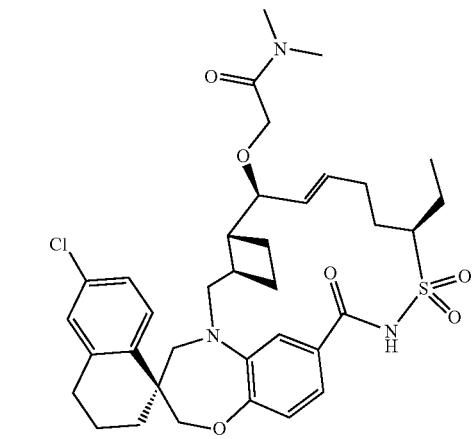 [SMILES: CC[C@@H]1CC/C=C/[C@H](OCC(=O)N(C)C)[C@@H]2CC[C@H]2CN2C[C@@]3(CCCc4cc(Cl)ccc43)COc3ccc(cc32)C(=O)NS1(=O)=O]

To a 25-mL round-bottomed flask was added tert-butyl (((1S,3'R,6'R,7'S,8'E,12'R)-6-chloro-12'-ethyl-13',13'-di-oxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetate (from Example 971; 15.4 mg, 0.022 mmol) in 1 mL of THF at 0° C., methylmagnesium bromide (3.0 M solution in diethyl ether, 12.87 μl, 0.11 mmol, Aldrich) was added. After 3 h, the reaction was quenched with aq NH$_4$Cl, and then 40 mL of EtOAc was added. The organic layer was concentrated and purified through a 24 g ISCO Gold column, eluting with 0-35% EtOAc(with 0.3% HOAc) in hexane to give (1S,3'R,6'R,7'S,8'E,12'R)-6-chloro-12'-ethyl-7'-(2-hydroxy-2-methylpropoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (9.5 mg, 0.014 mmol) as a white solid. $^1$H NMR (500 MHz, CD$_3$OD) δ 7.75 (d, J=8.6 Hz, 1H), 7.19 (d, J=7.8 Hz, 1H), 7.13 (s, 1H), 7.00 (d, J=7.8 Hz, 1H), 6.93 (d, J=8.1 Hz, 1H), 6.86 (s, 1H), 5.85 (ddd, J=6.6, 14.7, 21.3 Hz, 1H), 5.61 (dd, J=8.6, 14.9 Hz, 1H), 4.13-4.00 (m, 3H), 3.86 (dd, J=4.4, 7.6 Hz, 1H), 3.83 (br. s., 1H), 3.68 (d, J=13.9 Hz, 1H), 3.28 (dd, J=5.4, 9.0 Hz, 2H), 3.14 (d, J=9.5 Hz, 1H), 3.08 (dd, J=10.0, 15.4 Hz, 1H), 2.88-2.73 (m, 2H), 2.59-2.48 (m, 1H), 2.42 (br. s., 1H), 2.40-2.26 (m, 2H), 2.18-2.06 (m, 2H), 2.01-1.79 (m, 8H), 1.74 (dd, J=9.5, 18.8 Hz, 1H), 1.49-1.42 (m, 1H), 1.25-1.12 (m, 9H). m/z (ESI, +ve ion) 671.2 (M+H)$^+$.

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 2-chloro-N, N-dimethylacetamide (Aldrich), and the desired product, 2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N,N-dimethylacetamide was isolated as a white solid. $^1$H NMR (400 MHz, CD$_3$OD) δ 7.75 (d, J=8.4 Hz, 1H), 7.19 (dd, J=2.2, 8.5 Hz, 1H), 7.12 (d, J=2.2 Hz, 1H), 6.99 (dd, J=2.2, 8.2 Hz, 1H), 6.93 (d, J=8.2 Hz, 1H), 6.84 (d, J=1.8 Hz, 1H), 5.94-5.86 (m, 1H), 5.62 (dd, J=9.0, 15.3 Hz, 1H), 4.13 (d, J=5.1 Hz, 2H), 4.09 (d, J=3.1 Hz, 2H), 4.07-4.02 (m, 1H), 3.92 (dd, J=3.5, 9.0 Hz, 1H), 3.84 (d, J=14.1 Hz, 1H), 3.68 (d, J=14.3 Hz, 1H), 3.29 (d, J=14.1 Hz, 1H), 3.10 (dd, J=10.6, 15.7 Hz, 1H), 3.04 (s, 3H), 2.97 (s, 3H), 2.84-2.72 (m, 2H), 2.60 (dq, J=3.4, 9.1 Hz, 1H), 2.48-2.28 (m, 3H), 2.19-2.08 (m, 2H), 2.04-1.83 (m, 8H), 1.76 (dd, J=8.8, 18.0 Hz, 1H), 1.51-1.41 (m, 1H), 1.22 (d, J=7.4 Hz, 3H). m/z (ESI, +ve ion) 684.4 (M+H)$^+$.

1987

Example 974. 2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-methylacetamide

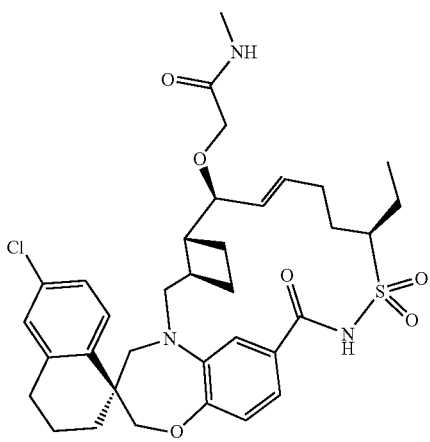 [SMILES: CC[C@@H]1CC/C=C/[C@H](OCC(=O)NC)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 2-chloro-N-methylacetamide (Aldrich), and the desired product, 2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-methylacetamide was isolated as a white solid. $^1$H NMR (400 MHz, CD$_3$OD) δ 7.75 (d, J=8.4 Hz, 1H), 7.19 (dd, J=2.9, 8.4 Hz, 1H), 7.13 (d, J=2.0 Hz, 1H), 6.99 (dd, J=1.8, 8.6 Hz, 1H), 6.95 (d, J=8.2 Hz, 1H), 6.85 (d, J=1.6 Hz, 1H), 5.95-5.86 (m, 1H), 5.64 (dd, J=9.2, 15.3 Hz, 1H), 4.09 (d, J=3.5 Hz, 2H), 4.07-4.02 (m, 1H), 3.94-3.89 (m, 2H), 3.88 (d, J=4.7 Hz, 2H), 3.69 (d, J=14.3 Hz, 1H), 3.10 (dd, J=10.0, 15.5 Hz, 1H), 2.81-2.80 (m, 3H), 2.67-2.56 (m, 1H), 2.48-2.27 (m, 4H), 2.12 (dd, J=7.2, 14.9 Hz, 2H), 2.04-1.83 (m, 10H), 1.80-1.73 (m, 1H), 1.51-1.37 (m, 1H), 1.22 (t, J=7.4 Hz, 3H). m/z (ESI, +ve ion) 670.2 (M+H)$^+$.

1988

Example 975. (1S,3'R,6'R,7'S,8'E,12'R)-6-chloro-7'-ethoxy-12'-ethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

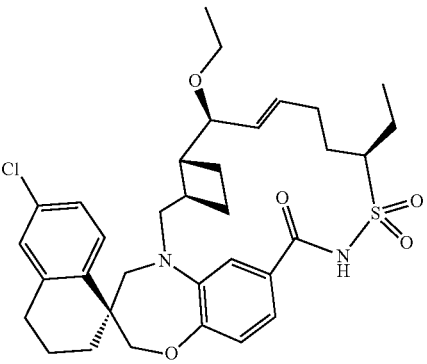 [SMILES: CCO[C@H]1/C=C/CC[C@@H](CC)S(=O)(=O)NC(=O)c2ccc3c(c2)N(C[C@@H]2CC[C@H]21)C[C@@]1(CCCc2cc(Cl)ccc21)CO3]

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and ethyl iodide (Fluka), and the desired product, (1S,3'R,6'R,7'S,8'E,12'R)-6-chloro-7'-ethoxy-12'-ethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (500 MHz, CD$_3$OD) δ 7.75 (d, J=8.6 Hz, 1H), 7.19 (dd, J=2.0, 8.3 Hz, 1H), 7.12 (dd, J=2.4, 6.8 Hz, 1H), 7.00 (dd, J=2.0, 6.4 Hz, 1H), 6.94 (dd, J=3.9, 8.3 Hz, 1H), 6.87 (d, J=1.5 Hz, 1H), 5.89-5.82 (m, 1H), 5.59 (dd, J=8.8, 15.4 Hz, 1H), 4.09 (dd, J=12.2, 16.6 Hz, 2H), 4.05-3.99 (m, 1H), 3.90-3.82 (m, 2H), 3.68 (d, J=14.2 Hz, 1H), 3.54 (dd, J=6.8, 9.8 Hz, 1H), 3.44-3.38 (m, 1H), 3.08 (dd, J=10.1, 15.3 Hz, 1H), 2.86-2.74 (m, 2H), 2.51-2.40 (m, 2H), 2.40-2.27 (m, 2H), 2.17-2.06 (m, 2H), 2.04-1.66 (m, 10H), 1.45 (t, J=12.0 Hz, 1H), 1.18 (td, J=7.3, 17.1 Hz, 6H). m/z (ESI, +ve ion) 627.2 (M+H)$^+$.

Example 976. (1S,3'R,6'R,7'S,8'E,12'R)-6-chloro-12'-ethyl-7'-(2-pyridinylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

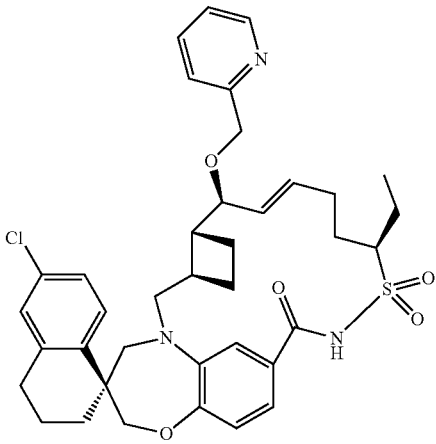 [SMILES: CC[C@@H]1CC/C=C/[C@H](OCc2ccccn2)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 2-(bromomethyl)pyridine, hydrobromide (Aldrich), and the desired product, (1S,3'R,6'R,7'S,8'E,12'R)-6-chloro-12'-ethyl-7'-(2-pyridinylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (400 MHz, CD$_3$OD) δ 8.48 (d, J=4.5 Hz, 1H), 7.86 (dt, J=1.6, 7.7 Hz, 1H), 7.74 (d, J=8.4 Hz, 1H), 7.49 (d, J=7.8 Hz, 1H), 7.34 (dd, J=5.1, 7.0 Hz, 1H), 7.18 (dd, J=2.2, 8.4 Hz, 1H), 7.11 (d, J=2.2 Hz, 1H), 7.07 (d, J=8.4 Hz, 1H), 6.95 (s, 1H), 6.84 (d, J=8.0 Hz, 1H), 6.09-6.00 (m, 1H), 5.63 (dd, J=8.8, 15.1 Hz, 1H), 4.62 (d, J=13.5 Hz, 1H), 4.51 (d, J=13.5 Hz, 1H), 4.04 (d, J=4.1 Hz, 2H), 4.02-3.99 (m, 1H), 3.85 (d, J=14.3 Hz, 1H), 3.64 (d, J=14.3 Hz, 1H), 3.07 (dd, J=10.0, 15.1 Hz, 1H), 2.84-2.75 (m, 2H), 2.72 (s, 2H), 2.65-2.40 (m, 3H), 2.29-2.07 (m, 3H), 2.01-1.72 (m, 9H), 1.49-1.38 (m, 1H), 1.19 (t, J=7.3 Hz, 3H). m/z (ESI, +ve ion) 690.2 (M+H)$^+$.

Example 977. (1S,3'R,6'R,7'S,8'E,12'R)-6-chloro-12'-ethyl-7'-(2-pyrimidinylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

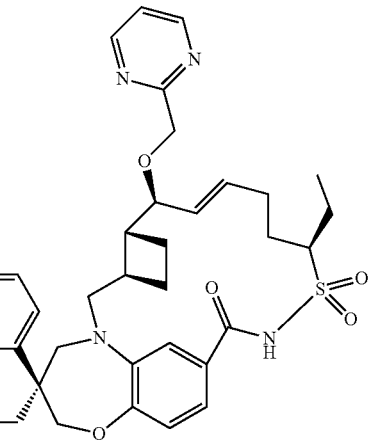

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 2-(chloromethyl)pyrimidine (TCI), and the desired product, (1S,3'R,6'R,7'S,8'E,12'R)-6-chloro-12'-ethyl-7'-(2-pyrimidinylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (500 MHz, CD$_3$OD) δ 8.84 (br. s., 2H), 7.74 (d, J=8.6 Hz, 1H), 7.46 (t, J=4.9 Hz, 1H), 7.19 (dd, J=2.2, 8.6 Hz, 1H), 7.12 (d, J=2.0 Hz, 1H), 6.98 (dd, J=2.0, 8.1 Hz, 1H), 6.92 (d, J=8.1 Hz, 1H), 6.82 (d, J=1.7 Hz, 1H), 5.90-5.84 (m, 1H), 5.65 (dd, J=8.8, 15.2 Hz, 1H), 4.64 (dd, J=14.2, 27.6 Hz, 2H), 4.08 (dd, J=12.5, 17.4 Hz, 2H), 4.04-3.98 (m, 2H), 3.82 (d, J=15.4 Hz, 1H), 3.67 (d, J=14.2 Hz, 1H), 3.09 (dd, J=10.0, 15.4 Hz, 1H), 2.86-2.74 (m, 2H), 2.68-2.61 (m, 1H), 2.45-2.26 (m, 3H), 2.15-2.07 (m, 2H), 2.00-1.84 (m, 9H), 1.76 (dd, J=10.5, 19.8 Hz, 1H), 1.48-1.41 (m, 1H), 1.22 (t, J=7.5 Hz, 3H). m/z (ESI, +ve ion) 691.2 (M+H)$^+$.

Example 978. (1S,3'R,6'R,7'S,8'E,12'R)-6-chloro-12'-ethyl-7'-((2R)-tetrahydro-2-furanylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide and (1S,3'R,6'R,7'S,8'E,12'R)-6-chloro-12'-ethyl-7'-((2S)-tetrahydro-2-furanylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

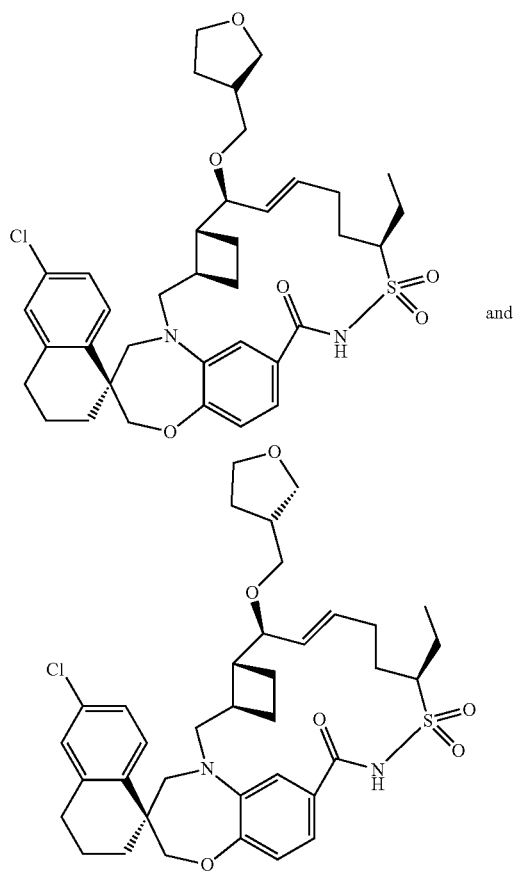

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide (Example 422, Step 1) and 3-(bromomethyl)tetrahydrofuran (ChemBridge), and the desired product, a mixture of (1S,3'R,6'R,7'S,8'E,12'R)-6-chloro-12'-ethyl-7'-((2R)-tetrahydro-2-furanylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide and (1S,3'R,6'R,7'S,8'E,12'R)-6-chloro-12'-ethyl-7'-((2S)-tetrahydro-2-furanylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (500 MHz, CD$_3$OD) δ 7.75 (d, J=8.6 Hz, 1H), 7.18 (dd, J=2.2, 8.8 Hz, 1H), 7.12 (d, J=2.2 Hz, 1H), 7.03 (d, J=7.3 Hz, 1H), 6.91 (d, J=7.6 Hz, 2H), 5.89 (br. s., 1H), 5.63-5.51 (m, 1H), 4.09 (dd, J=12.5, 17.9 Hz, 2H), 3.88-3.70 (m, 6H), 3.67 (d, J=13.9 Hz, 1H), 3.62-3.49 (m, 2H), 3.49-3.42 (m, 2H), 3.06 (dd, J=9.0, 15.4 Hz, 1H), 2.87-2.73 (m, 2H), 2.56-2.41 (m, 3H), 2.18-1.96 (m, 4H), 1.93 (d, J=8.1 Hz, 4H), 1.89-1.69 (m, 5H), 1.67-1.58 (m, 2H), 1.50-1.41 (m, 1H), 1.19 (t, J=7.5 Hz, 3H). m/z (ESI, +ve ion) 683.2 (M+H)$^+$.

Example 979. (1S,3'R,6'R,7'S,8'E,12'R)-6-chloro-12'-ethyl-7'-(2-(4-morpholinyl)-2-oxoethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

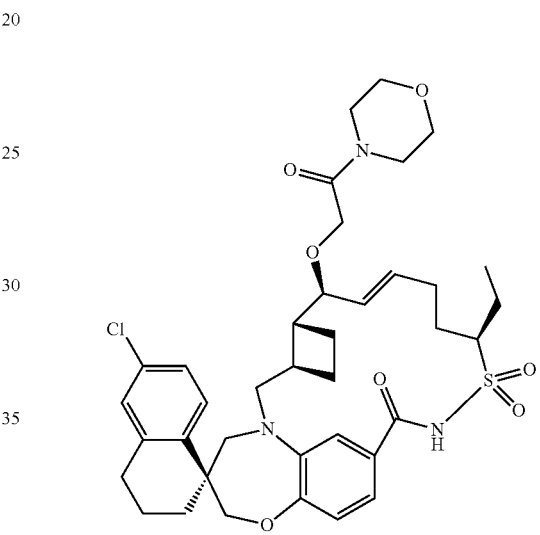

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 4-(bromoacetyl)morpholine (Aldrich), and the desired product, (1S,3'R,6'R,7'S,8'E,12'R)-6-chloro-12'-ethyl-7'-(2-(4-morpholinyl)-2-oxoethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (400 MHz, CD$_3$OD) δ 7.74 (d, J=8.8 Hz, 1H), 7.19 (dd, J=2.3, 8.4 Hz, 1H), 7.13 (d, J=2.0 Hz, 1H), 7.01 (dd, J=1.8, 8.2 Hz, 1H), 6.92 (d, J=8.0 Hz, 1H), 6.85 (d, J=1.8 Hz, 1H), 6.01-5.88 (m, 1H), 5.62 (dd, J=10.6, 15.7 Hz, 1H), 4.14 (d, J=2.5 Hz, 2H), 4.09 (d, J=3.3 Hz, 2H), 4.07-4.03 (m, 1H), 3.93 (dd, J=3.7, 9.0 Hz, 1H), 3.85 (d, J=14.9 Hz, 1H), 3.74-3.63 (m, 6H), 3.58 (dd, J=4.8, 12.4 Hz, 5H), 3.20-3.04 (m, 1H), 2.84-2.73 (m, 2H), 2.65-2.47 (m, 1H), 2.49-2.41 (m, 1H), 2.41-2.28 (m, 2H), 2.22-2.07 (m, 2H), 2.04-1.73 (m, 8H), 1.52-1.40 (m, 1H), 1.22 (t, J=7.5 Hz, 3H). m/z (ESI, +ve ion) 726.2 (M+H)$^+$.

Example 980. (1S,3'R,6'R,7'S,8'E,12'R)-6-chloro-12'-ethyl-7'-(2-methoxyethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

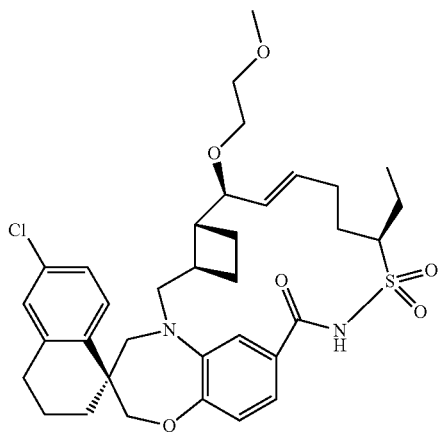 [SMILES: CC[C@@H]1CC/C=C/[C@H](OCCOC)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 1-bromo-2-methoxyethane (Aldrich), and the desired product, (1S,3'R,6'R,7'S,8'E,12'R)-6-chloro-12'-ethyl-7'-(2-methoxyethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (400 MHz, CD$_3$OD) δ 7.75 (d, J=8.6 Hz, 1H), 7.19 (dd, J=2.2, 8.8 Hz, 1H), 7.12 (d, J=2.2 Hz, 1H), 7.01 (dd, J=1.6, 8.2 Hz, 1H), 6.94 (d, J=8.2 Hz, 1H), 6.88 (d, J=1.6 Hz, 1H), 5.89 (ddd, J=6.1, 13.1, 21.5 Hz, 1H), 5.60 (dd, J=9.0, 15.1 Hz, 1H), 4.09 (dd, J=12.7, 15.3 Hz, 2H), 4.05-3.99 (m, 1H), 3.91-3.82 (m, 2H), 3.69 (d, J=14.5 Hz, 1H), 3.62-3.57 (m, 1H), 3.53 (dd, J=4.1, 8.0 Hz, 2H), 3.50-3.45 (m, 1H), 3.38 (s, 3H), 3.08 (dd, J=10.3, 15.2 Hz, 1H), 2.87-2.73 (m, 2H), 2.55-2.40 (m, 2H), 2.40-2.26 (m, 2H), 2.11 (dd, J=7.4, 15.1 Hz, 2H), 1.98-1.65 (m, 10H), 1.46 (t, J=10.9 Hz, 1H), 1.20 (t, J=7.4 Hz, 3H). m/z (ESI, +ve ion) 657.2 (M+H)$^+$.

Example 981. (1S,3'R,6'R,7'S,8'E,12'R)-6-chloro-12'-ethyl-7'-(2-(methylsulfonyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

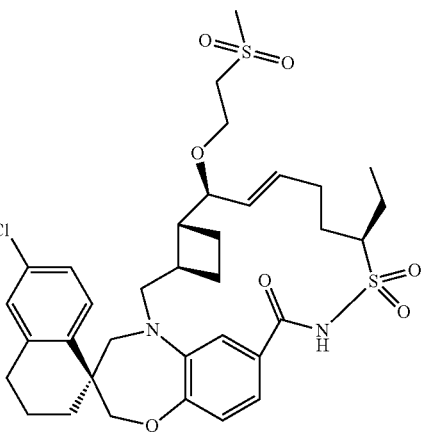

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 2-(bromoethyl)methylsulfone (Accela ChemBio), and the desired product, (1S,3'R,6'R,7'S,8'E,12'R)-6-chloro-12'-ethyl-7'-(2-(methylsulfonyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (500 MHz, CD$_3$OD) δ 7.75 (d, J=8.6 Hz, 1H), 7.19 (dd, J=1.7, 8.1 Hz, 1H), 7.12 (d, J=1.5 Hz, 1H), 7.00 (dd, J=1.7, 8.3 Hz, 1H), 6.93 (d, J=7.9 Hz, 1H), 6.86 (s, 1H), 5.98-5.90 (m, 1H), 5.63 (dd, J=9.0, 15.2 Hz, 1H), 4.09 (dd, J=12.7, 17.4 Hz, 2H), 4.06-4.02 (m, 1H), 3.93 (dd, J=3.4, 8.8 Hz, 1H), 3.90-3.80 (m, 2H), 3.76-3.70 (m, 1H), 3.68 (d, J=14.2 Hz, 1H), 3.29 (d, J=14.4 Hz, 2H), 3.09 (dd, J=10.0, 15.4 Hz, 1H), 3.01 (s, 3H), 2.87-2.74 (m, 2H), 2.56-2.41 (m, 2H), 2.41-2.28 (m, 2H), 2.19-2.07 (m, 2H), 2.01-1.92 (m, 4H), 1.92-1.71 (m, 6H), 1.46 (t, J=12.0 Hz, 1H), 1.21 (t, J=7.5 Hz, 3H). m/z (ESI, +ve ion) 705.2 (M+H)$^+$.

Example 982. (((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)acetonitrile Example 983. (1S,3'R,6'R,7'S,8'E,12'R)-6-chloro-12'-ethyl-7'-(tetrahydro-2H-pyran-4-ylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

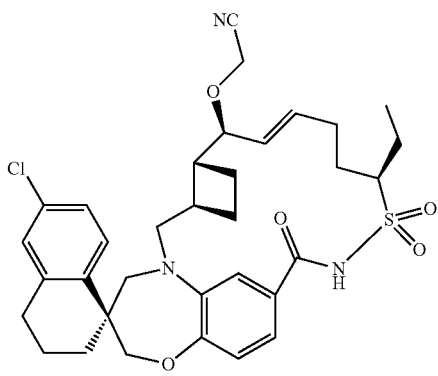 [SMILES: CC[C@@H]1CC/C=C/[C@H](OCC#N)[C@@H]2CC[C@H]2CN2C[C@@]3(CCCc4cc(Cl)ccc43)COc3ccc(cc32)C(=O)NS1(=O)=O]

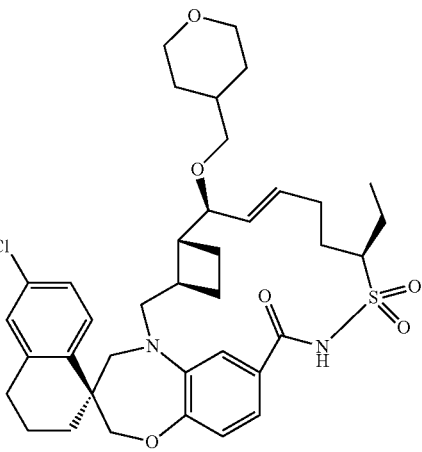

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and chloroacetonitrile (Aldrich), and the desired product, (((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetonitrile was isolated as a white solid. $^1$H NMR (500 MHz, CD$_3$OD) δ 7.74 (d, J=8.6 Hz, 1H), 7.19 (dd, J=2.0, 8.1 Hz, 1H), 7.12 (d, J=2.2 Hz, 1H), 7.00 (dd, J=2.0, 8.3 Hz, 1H), 6.94 (d, J=8.3 Hz, 1H), 6.85 (d, J=1.7 Hz, 1H), 6.06-5.98 (m, 1H), 5.64 (dd, J=8.8, 15.9 Hz, 1H), 4.27 (s, 2H), 4.08 (dd, J=11.7, 17.6 Hz, 3H), 4.02 (dd, J=3.2, 10.3 Hz, 1H), 3.87 (d, J=14.9 Hz, 1H), 3.69 (d, J=14.4 Hz, 1H), 3.10 (dd, J=10.5, 15.7 Hz, 1H), 2.87-2.74 (m, 2H), 2.60-2.41 (m, 2H), 2.40-2.30 (m, 2H), 2.18-2.08 (m, 2H), 2.02-1.80 (m, 9H), 1.77 (dd, J=7.8, 16.4 Hz, 1H), 1.48 (d, J=13.7 Hz, 1H), 1.22 (t, J=7.6 Hz, 3H). m/z (ESI, +ve ion) 638.2 (M+H)$^+$.

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 4-(bromomethyl)tetrahydropyran (Combi-Blocks), and the desired product, (1S,3'R,6'R,7'S,8'E,12'R)-6-chloro-12'-ethyl-7'-(tetrahydro-2H-pyran-4-ylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (500 MHz, CD$_3$OD) δ 7.75 (d, J=8.6 Hz, 1H), 7.19 (dd, J=2.2, 8.6 Hz, 1H), 7.12 (d, J=2.2 Hz, 1H), 7.00 (dd, J=1.7, 6.4 Hz, 1H), 6.94 (d, J=8.3 Hz, 1H), 6.89 (d, J=1.7 Hz, 1H), 5.84-5.78 (m, 1H), 5.58 (dd, J=8.6, 15.2 Hz, 1H), 4.09 (dd, J=12.2, 15.9 Hz, 2H), 4.04-3.98 (m, 1H), 3.97-3.91 (m, 2H), 3.85 (d, J=14.9 Hz, 1H), 3.79 (dd, J=3.9, 8.6 Hz, 1H), 3.69 (d, J=14.2 Hz, 1H), 3.46-3.39 (m, 2H), 3.31 (dd, J=6.6, 9.0 Hz, 4H), 3.19 (dd, J=6.2, 9.4 Hz, 1H), 3.09 (dd, J=9.9, 15.3 Hz, 1H), 2.86-2.74 (m, 2H), 2.50 (dq, J=3.5, 9.2 Hz, 1H), 2.45-2.26 (m, 3H), 2.11 (dd, J=6.6, 14.7 Hz, 2H), 1.99-1.84 (m, 6H), 1.84-1.78 (m, 3H), 1.74 (dd, J=9.0, 16.1 Hz, 1H), 1.62 (t, J=7.8 Hz, 2H), 1.46 (t, J=12.1 Hz, 1H), 1.20 (t, J=7.6 Hz, 3H). m/z (ESI, +ve ion) 697.2 (M+H)$^+$.

Example 984. (1S,3'R,6'R,7'S,8'E,12'R)-6-chloro-12'-ethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide Example 985. (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N,N-dimethylpropanamide and (2S)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N,N-dimethylpropanamide

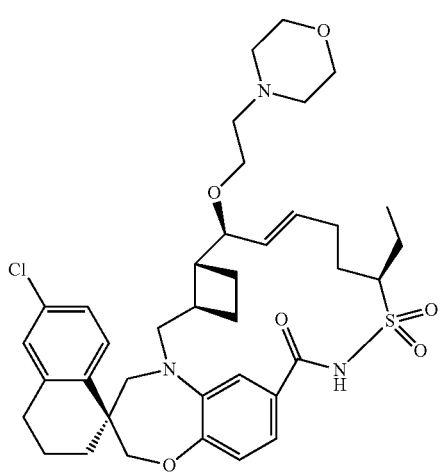 [SMILES: CC[C@@H]1CC/C=C/[C@H](OCCN2CCOCC2)[C@@H]2CC[C@H]2CN2C[C@@]3(CCCc4cc(Cl)ccc43)COc3ccc(cc32)C(=O)NS1(=O)=O]

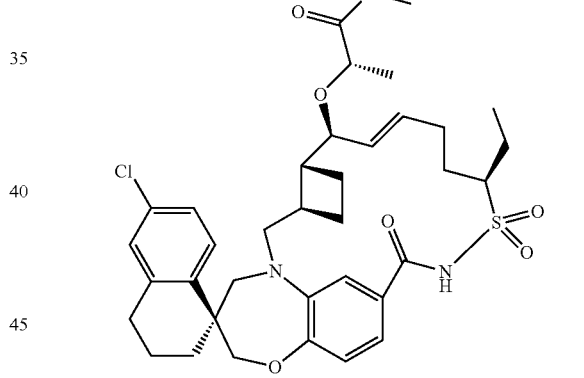

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 4-(2-bromoethyl)morpholine (Aldrich), and the desired product, (1S,3'R,6'R,7'S,8'E,12'R)-6-chloro-12'-ethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (500 MHz, CD$_3$OD) δ 7.75 (d, J=9.8 Hz, 1H), 7.20 (dd, J=2.4, 6.6 Hz, 1H), 7.12 (d, J=2.4 Hz, 1H), 7.01 (dd, J=1.7, 7.8 Hz, 1H), 6.95 (d, J=8.1 Hz, 1H), 6.84 (d, J=1.7 Hz, 1H), 5.98-5.91 (m, 1H), 5.66 (dd, J=8.8, 15.9 Hz, 1H), 4.15-4.00 (m, 5H), 3.94 (dd, J=3.7, 9.5 Hz, 1H), 3.86 (d, J=13.9 Hz, 1H), 3.83-3.77 (m, 2H), 3.72-3.64 (m, 2H), 3.47 (td, J=1.7, 3.2 Hz, 1H), 3.41-3.36 (m, 5H), 3.29-3.27 (m, 1H), 3.19 (td, J=1.6, 3.4 Hz, 1H), 3.09 (dd, J=9.8, 15.2 Hz, 1H), 2.87-2.74 (m, 1H), 2.59-2.49 (m, 1H), 2.49-2.29 (m, 3H), 2.16-2.06 (m, 2H), 2.02-1.73 (m, 9H), 1.47 (t, J=11.6 Hz, 1H), 1.21 (t, J=7.5 Hz, 3H). m/z (ESI, +ve ion) 712.1 (M+H)$^+$.

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 2-bromo-N,N-dimethylpropanamide (ChemBridge), and the desired product, a mixture of (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N,N-dimethylpropanamide and (2S)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N,N-dimethylpropanamide was isolated. $^1$H NMR (400 MHz, CD$_3$OD) δ 7.74 (d, J=8.6 Hz, 1H), 7.21-7.16 (m, 1H), 7.13 (dd, J=2.2, 5.1 Hz, 1H), 7.06 (dd, J=1.9, 8.1 Hz, 0.6H), 7.01-6.92 (m, 2H), 6.82 (dd, J=2.3, 6.5 Hz, 1H), 5.93-5.85 (m, 1H), 5.62 (dd, J=9.3, 15.2 Hz, 0.4H), 4.32 (q, J=6.7 Hz, 1H), 4.16 (s, 1H), 4.14-3.93 (m, 3H), 3.90-3.81 (m, 1H), 3.78-3.64 (m, 1H), 3.42 (d, J=5.7 Hz, 1H), 3.13 (s, 3H), 3.11-3.04 (m, 1H), 2.93 (s, 3H), 2.84-2.74 (m, 2H), 2.56-2.27 (m, 3H), 2.25-2.06 (m, 2H), 2.04-1.82 (m, 6H), 1.80-1.66 (m, 2H), 1.50-1.38 (m, 1H), 1.37-1.26 (m, 5H), 1.26-1.20 (m, 3H). m/z (ESI, +ve ion) 698.2 (M+H)$^+$.

Example 986. (1S,3'R,6'R,7'S,8'E,12'R)-6-chloro-12'-ethyl-7'-(1,3-oxazol-2-ylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide Example 987. (1S,3'R,6'R,7'S,8'E,12'R)-6-chloro-12'-ethyl-7'-((2-methyl-2H-tetrazol-5-yl)methoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

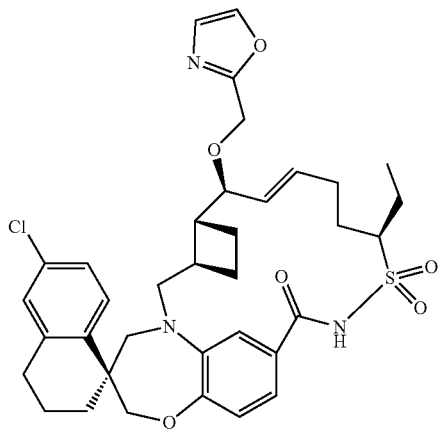 [SMILES: CC[C@@H]1CC/C=C/[C@H](OCc2ncco2)[C@@H]2CC[C@H]2CN2C[C@@]3(CCCc4cc(Cl)ccc43)COc3ccc(cc32)C(=O)NS1(=O)=O]

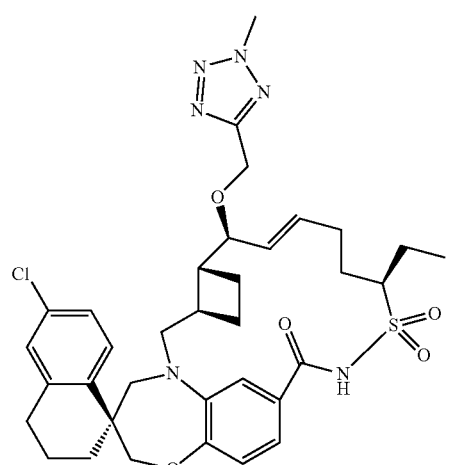

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 2-(chloromethyl)oxazole (Frontier Scientific Services), and the desired product, (1S,3'R,6'R,7'S,8'E,12'R)-6-chloro-12'-ethyl-7'-(1,3-oxazol-2-ylmethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (500 MHz, CDCl$_3$) δ 7.95 (s, 1H), 7.62 (d, J=8.8 Hz, 1H), 7.60 (s, 1H), 7.11 (dd, J=2.2, 8.3 Hz, 1H), 7.06-7.04 (m, 1H), 7.01 (d, J=2.2 Hz, 1H), 6.83 (d, J=8.1 Hz, 1H), 6.80 (dd, J=1.7, 8.3 Hz, 1H), 6.72 (d, J=1.5 Hz, 1H), 5.84-5.74 (m, 1H), 5.51 (dd, J=9.0, 15.4 Hz, 1H), 4.49 (d, J=13.2 Hz, 1H), 4.38 (d, J=13.4 Hz, 1H), 4.10-4.04 (m, 1H), 3.98 (dd, J=12.2, 24.9 Hz, 2H), 3.83 (dd, J=3.7, 9.0 Hz, 1H), 3.73 (d, J=15.4 Hz, 1H), 3.64 (d, J=14.2 Hz, 1H), 3.13 (d, J=14.2 Hz, 1H), 2.99-2.94 (m, 1H), 2.91 (dd, J=10.1, 15.3 Hz, 1H), 2.75-2.63 (m, 2H), 2.49-2.38 (m, 1H), 2.32-2.12 (m, 3H), 2.11-2.03 (m, 1H), 2.02-1.78 (m, 5H), 1.74 (dd, J=1.0, 10.0 Hz, 2H), 1.57 (dd, J=9.8, 19.3 Hz, 2H), 1.34-1.27 (m, 1H), 1.16 (t, J=7.5 Hz, 3H). m/z (ESI, +ve ion) 680.2 (M+H)$^+$.

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 5-(chloromethyl)-2-methyl-2H-tetrazole (Example 957, Step 1) and the desired product, (1S,3'R,6'R,7'S,8'E,12'R)-6-chloro-12'-methyl-7'-((2-methyl-2H-tetrazol-5-yl)methoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (500 MHz, CD$_3$OD) δ 7.75 (d, J=8.6 Hz, 1H), 7.19 (dd, J=2.4, 8.6 Hz, 1H), 7.12 (d, J=2.2 Hz, 1H), 6.98 (dd, J=2.0, 8.1 Hz, 1H), 6.90 (d, J=8.3 Hz, 1H), 6.83 (d, J=2.0 Hz, 1H), 5.92-5.86 (m, 1H), 5.62 (dd, J=8.7, 15.3 Hz, 1H), 4.67 (dd, J=9.8, 13.7 Hz, 2H), 4.42 (s, 3H), 4.10-4.02 (m, 3H), 3.93 (dd, J=4.0, 8.7 Hz, 1H), 3.79 (d, J=15.2 Hz, 1H), 3.68 (d, J=13.9 Hz, 1H), 3.26 (d, J=14.2 Hz, 1H), 3.07 (dd, J=9.8, 15.4 Hz, 1H), 2.86-2.73 (m, 2H), 2.55-2.41 (m, 2H), 2.32 (dd, J=8.8, 16.4 Hz, 2H), 2.19-2.07 (m, 2H), 2.01-1.80 (m, 8H), 1.74 (dd, J=10.8, 18.8 Hz, 1H), 1.45 (d, J=11.7 Hz, 1H), 1.23 (t, J=7.6 Hz, 3H). m/z (ESI, +ve ion) 695.2 (M+H)$^+$.

Example 988. (1S,3'R,6'R,7'S,8'E,12'R)-6-chloro-12'-ethyl-7'-((1-methyl-1H-tetrazol-5-yl)methoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

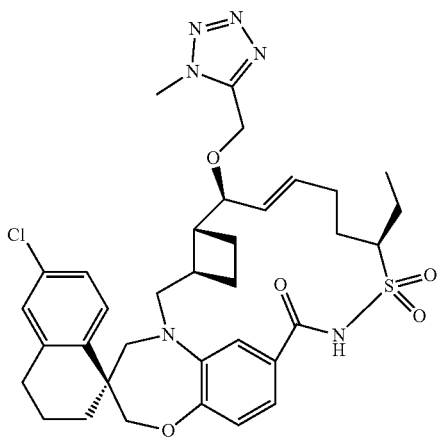 [SMILES: CC[C@@H]1CC/C=C/[C@H](OCc2nnnn2C)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 5-(chloromethyl)-1-methyl-1H-tetrazole (Princeston Bio), and the desired product, (1S,3'R,6'R,7'S,8'E,12'R)-6-chloro-12'-ethyl-7'-((1-methyl-1H-tetrazol-5-yl)methoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (500 MHz, CD$_3$OD) δ 7.74 (d, J=8.6 Hz, 1H), 7.19 (dd, J=2.2, 8.3 Hz, 1H), 7.12 (d, J=2.0 Hz, 1H), 7.00 (dd, J=1.7, 8.1 Hz, 1H), 6.92 (d, J=8.3 Hz, 1H), 6.84 (d, J=1.2 Hz, 1H), 5.98-5.91 (m, 1H), 5.62 (dd, J=9.2, 15.3 Hz, 1H), 4.81 (dd, J=13.2, 28.6 Hz, 2H), 4.11 (s, 3H), 4.07 (d, J=7.1 Hz, 2H), 4.06-4.03 (m, 1H), 4.01 (dd, J=3.9, 8.8 Hz, 1H), 3.85 (d, J=14.9 Hz, 1H), 3.67 (d, J=14.2 Hz, 1H), 3.28 (d, J=14.2 Hz, 1H), 3.08 (dd, J=10.1, 15.3 Hz, 1H), 2.86-2.73 (m, 1H), 2.60-2.53 (m, 1H), 2.45-2.25 (m, 3H), 2.19-2.06 (m, 2H), 2.03-1.93 (m, 3H), 1.91-1.71 (m, 6H), 1.50-1.41 (m, 1H), 1.24 (t, J=7.5 Hz, 3H). m/z (ESI, +ve ion) 695.2 (M+H)$^+$.

Example 989. 2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N,N-dimethylethanesulfonamide

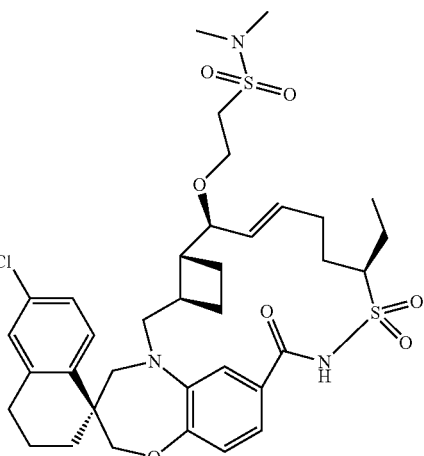

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and 2-chloro-N,N-dimethylethenesulfonamide (Chembridge), and the desired product, 2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N,N-dimethylethanesulfonamide was isolated as a white solid. $^1$H NMR (500 MHz, CD$_3$OD) δ 7.76 (d, J=8.3 Hz, 1H), 7.18 (dd, J=2.0, 8.6 Hz, 1H), 7.12 (d, J=2.2 Hz, 1H), 7.07 (br. s., 1H), 6.93 (br. s., 1H), 6.88 (d, J=8.0 Hz, 1H), 5.99 (br. s., 1H), 5.60 (dd, J=8.4, 15.0 Hz, 1H), 4.06 (dd, J=13.0, 20.1 Hz, 2H), 3.99-3.77 (m, 4H), 3.71-3.64 (m, 2H), 3.27 (t, J=5.9 Hz, 2H), 3.07 (dd, J=10.0, 15.2 Hz, 1H), 2.87 (s, 6H), 2.84-2.72 (m, 2H), 2.59-2.24 (m, 4H), 2.18-2.08 (m, 2H), 1.99-1.68 (m, 10H), 1.45 (t, J=11.6 Hz, 1H), 1.18 (t, J=7.5 Hz, 3H). m/z (ESI, +ve ion) 734.2 (M+H)$^+$.

Example 990. (1S,3'R,6'R,7'S,8'E,12'R)-6-chloro-12'-ethyl-7'-(1,3-thiazol-2-ylmethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

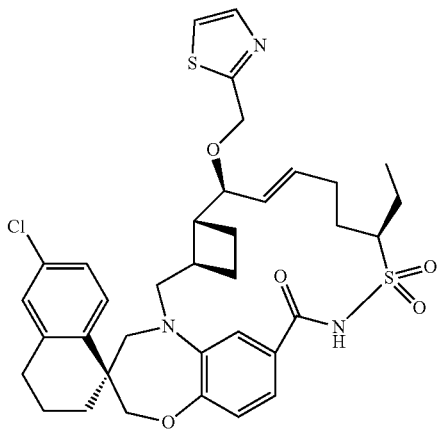 [SMILES: CC[C@@H]1CC/C=C/[C@H](OCc2nccs2)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 422, Step 1) and 2-(chloromethyl)thiazole (Chembridge), and the desired product, (1S,3'R,6'R,7'S,8'E,12'R)-6-chloro-12'-ethyl-7'-(1,3-thiazol-2-ylmethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide was isolated as a white solid. $^1$H NMR (500 MHz, CDCl$_3$) δ 7.73 (d, J=3.1 Hz, 1H), 7.54 (d, J=2.7 Hz, 1H), 7.16 (dd, J=2.7, 7.0 Hz, 1H), 7.10 (d, J=2.0 Hz, 1H), 6.97 (d, J=11.7 Hz, 1H), 6.88-6.74 (m, 1H), 6.20-6.03 (m, 1H), 5.61 (dd, J=9.0, 15.4 Hz, 1H), 4.49 (d, J=13.2 Hz, 1H), 4.38 (d, J=13.4 Hz, 1H), 4.10-4.04 (m, 1H), 3.98 (dd, J=12.2, 24.9 Hz, 2H), 3.83 (dd, J=3.7, 9.0 Hz, 1H), 3.73 (d, J=15.4 Hz, 1H), 3.64 (d, J=14.2 Hz, 1H), 3.13 (d, J=14.2 Hz, 1H), 2.99-2.94 (m, 1H), 2.91 (dd, J=10.1, 15.3 Hz, 1H), 2.75-2.63 (m, 2H), 2.49-2.38 (m, 1H), 2.32-2.12 (m, 3H), 2.11-2.03 (m, 1H), 2.02-1.78 (m, 5H), 1.74 (dd, J=1.0, 10.0 Hz, 2H), 1.57 (dd, J=9.8, 19.3 Hz, 2H), 1.34-1.27 (m, 1H), 1.16 (t, J=7.5 Hz, 3H). m/z (ESI, +ve ion) 696.2 (M+H)$^+$.

Example 991. methyl (((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl)oxy)acetate

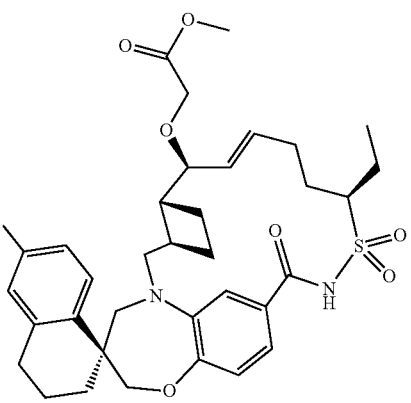

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 422, Step 1) and methyl bromoacetate (Alfa Aesar), and the desired product, methyl (((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl)oxy)acetate was isolated as a white solid. $^1$H NMR (400 MHz, CDCl$_3$) δ 8.01 (s, 1H), 7.62 (d, J=8.6 Hz, 1H), 7.10 (dd, J=2.2, 8.4 Hz, 1H), 7.01 (d, J=2.2 Hz, 1H), 6.87-6.78 (m, 2H), 6.72 (s, 1H), 5.81-5.72 (m, 1H), 5.49 (dd, J=9.0, 15.3 Hz, 1H), 4.10-3.74 (m, 7H), 3.70 (d, J=2.0 Hz, 3H), 3.64 (d, J=13.7 Hz, 1H), 3.15 (d, J=14.3 Hz, 1H), 2.93 (dd, J=10.3, 15.4 Hz, 1H), 2.77-2.62 (m, 2H), 2.57-2.38 (m, 1H), 2.32-2.13 (m, 3H), 2.06 (dd, J=7.5, 14.8 Hz, 1H), 1.99-1.70 (m, 9H), 1.58 (quin, J=9.6 Hz, 1H), 1.31 (t, J=12.5 Hz, 1H), 1.24-1.07 (m, 3H). m/z (ESI, +ve ion) 671.2 (M+H)$^+$.

Example 992. (((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)acetic Acid

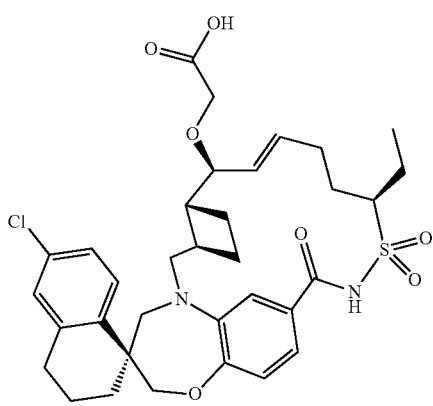 [SMILES: CC[C@@H]1CC/C=C/[C@H](OCC(=O)O)[C@@H]2CC[C@H]2CN2C[C@@]3(CCCc4cc(Cl)ccc43)COc3ccc(cc32)C(=O)NS1(=O)=O]

Lithium hydroxide monohydrate (14.0 mg, 0.334 mmol, JT-Baker) was added in a solution of methyl (((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetate (from Example 991; 5.9 mg, 0.008 mmol) in 1 mL THF and 1 mL of MeOH. The rection mixture was heated to 50° C. for 1 h, LC-MS showed the reaction went completely. 1 N HCl soluiton was added until the pH of the reaction mixture was about 1-2. 20 mL of EtOAc as added. The organic layer was concentrated and purified by reverse phase preparative HPLC (Gemini™ Prep C$_{18}$ 5 µm column; Phenomenex, Torrance, CA; gradient elution of 40% to 95% MeCN in water, where both solvents contain 0.1% TFA, 30 min method) to give (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic acid (9.5 mg, 0.014 mmol). $^1$H NMR (400 MHz, CD$_3$OD) δ 7.76 (d, J=8.4 Hz, 1H), 7.19 (dd, J=2.3, 8.4 Hz, 1H), 7.12 (d, J=2.2 Hz, 1H), 7.02 (dd, J=2.0, 8.0 Hz, 1H), 6.93-6.87 (m, 2H), 6.00-5.90 (m, 1H), 5.57 (dd, J=8.9, 15.2 Hz, 1H), 4.07 (d, J=2.0 Hz, 2H), 4.05-3.99 (m, 1H), 3.91-3.80 (m, 2H), 3.76-3.71 (m, 1H), 3.76-3.71 (m, 1H), 3.67 (d, J=13.9 Hz, 1H), 3.64-3.55 (m, 1H), 3.06 (dd, J=10.1, 15.0 Hz, 1H), 2.83-2.73 (m, 2H), 2.51 (t, J=6.5 Hz, 2H), 2.48-2.24 (m, 4H), 2.22-2.06 (m, 2H), 1.97-1.69 (m, 9H), 1.45 (t, J=11.9 Hz, 1H), 1.26-1.12 (m, 3H). m/z (ESI, +ve ion) 657.2 (M+H)$^+$.

Example 993. methyl (((1S,3'R,6'R,7'S,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)oxy)acetate

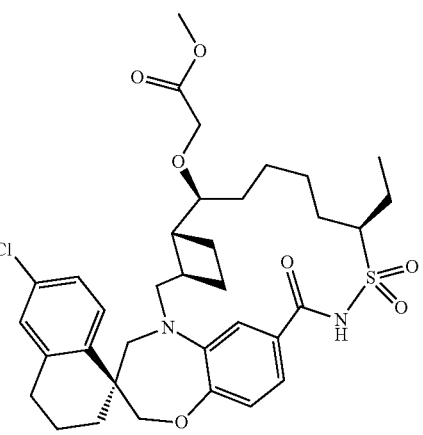

The title compound was prepared in an analogous manner to that described in Example 925, Step 1, using methyl (((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetate (Example 991), and the desired products, methyl (((1S,3'R,6'R,7'S,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)oxy)acetate was isolated. $^1$H NMR (400 MHz, CD$_3$OD) δ 7.64 (d, J=8.4 Hz, 1H), 7.08 (dd, J=2.2, 8.5 Hz, 1H), 7.02 (d, J=2.2 Hz, 1H), 6.98-6.93 (m, 2H), 6.83 (d, J=8.2 Hz, 1H), 4.03-3.91 (m, 4H), 3.76-3.67 (m, 2H), 3.60 (s, 3H), 3.57 (d, J=14.1 Hz, 1H), 3.43-3.37 (m, 1H), 3.05 (dd, J=7.3, 15.6 Hz, 1H), 2.76-2.62 (m, 2H), 2.58-2.49 (m, 1H), 2.32 (br. s., 1H), 2.06-1.94 (m, 2H), 1.89-1.74 (m, 6H), 1.71-1.55 (m, 4H), 1.49-1.23 (m, 7H), 1.08 (t, J=7.4 Hz, 3H). m/z (ESI, +ve ion) 673.2 (M+H)$^+$.

2007

Example 994. (((1S,3'R,6'R,7'S,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)oxy)acetic Acid

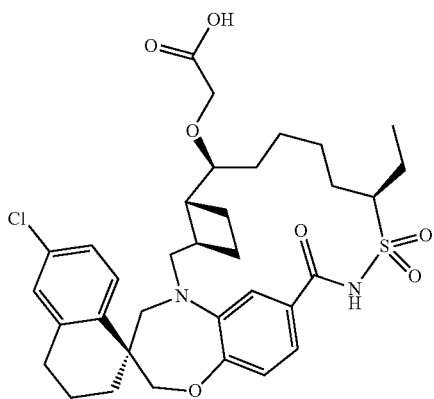 [SMILES: CC[C@@H]1CCCC[C@H](OCC(=O)O)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 925, Step 1 using (((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetic acid (Example 992), and the desired product, (((1S,3'R,6'R,7'S,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[16,18,24]trien]-7'-yl)oxy)acetic acid was isolated. $^1$H NMR (400 MHz, CD$_3$OD) δ 7.75 (d, J=8.6 Hz, 1H), 7.19 (dd, J=2.2, 8.6 Hz, 1H), 7.12 (d, J=2.2 Hz, 1H), 7.08-7.04 (m, 2H), 6.94 (d, J=7.4 Hz, 1H), 4.11 (s, 2H), 4.06 (d, J=6.1 Hz, 2H), 4.08-4.03 (m, 2H), 3.89-3.78 (m, 2H), 3.70 (d, J=13.9 Hz, 1H), 3.53 (br. s., 1H), 3.17 (dd, J=8.0, 15.1 Hz, 1H), 2.86-2.73 (m, 2H), 2.63 (d, J=5.3 Hz, 1H), 2.41 (br. s., 1H), 2.10 (dd, J=6.2, 14.0 Hz, 2H), 2.00-1.85 (m, 5H), 1.84-1.68 (m, 4H), 1.64-1.54 (m, 2H), 1.50 (d, J=8.6 Hz, 4H), 1.44-1.31 (m, 1H), 1.18 (t, J=7.4 Hz, 3H). m/z (ESI, +ve ion) 659.2 (M+H)$^+$.

2008

Example 995. 2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-(2-(dimethylamino)ethyl)acetamide

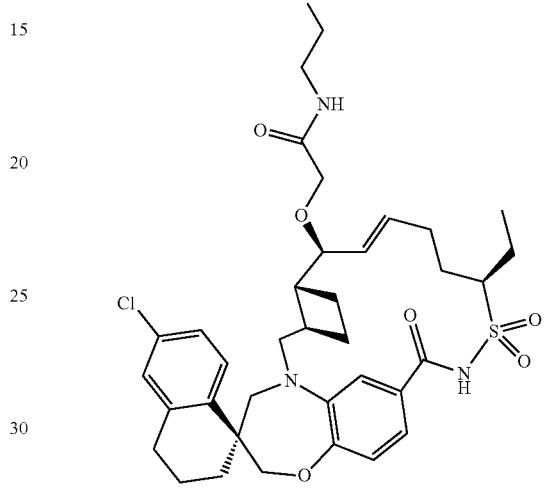

To a 25-mL round-bottomed flask was added (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic acid (from Example 992, 5.0 mg, 7.6 µmol) and HATU (7.0 mg, 18.2 µmol) in 1 mL of DMF, N1,N1-dimethylethane-1,2-diamine (2.0 mg, 22.8 µmol) was added. The reaction mixture was stirred at rt for 2 h, and then purified by reverse phase preparative HPLC (Gemini™ Prep C$_{18}$ 5 µm column; Phenomenex, Torrance, CA; gradient elution of 40% to 95% MeCN in water, where both solvents contain 0.1% TFA, 30 min method) to give 2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-(2-(dimethylamino)ethyl)acetamide (4.1 mg, 5.6 µmol) as a white solid. $^1$H NMR (400 MHz, CD$_3$OD) δ 7.75 (d, J=8.6 Hz, 1H), 7.20 (dd, J=2.2, 8.5 Hz, 1H), 7.13 (d, J=2.2 Hz, 1H), 7.01 (dd, J=2.0, 8.2 Hz, 1H), 6.95 (d, J=8.2 Hz, 1H), 6.84 (d, J=1.6 Hz, 1H), 5.93 (td, J=7.1, 13.6 Hz, 1H), 5.65 (dd, J=9.0, 15.1 Hz, 1H), 4.10 (dd, J=12.1, 17.8 Hz, 2H), 4.06-4.01 (m, 1H), 3.95 (dddd, J=13.1, 15.3, 19.2, 24.8 Hz, 3H), 3.85 (d, J=14.9 Hz, 1H), 3.71 (d, J=12.5 Hz, 1H), 3.65 (d, J=0.8 Hz, 2H), 3.3 (m, 2H overlap with solvent), 3.10 (dd, J=10.5, 15.4 Hz, 1H), 2.98 (s, 6H), 2.85-2.76 (m, 2H), 2.66-2.58 (m, 1H), 2.50-2.40 (m, 1H), 2.36 (dd, J=8.6, 16.0 Hz, 2H), 2.17-2.07 (m, 2H), 2.02-1.84 (m, 9H), 1.78 (dd, J=9.8, 17.6 Hz, 1H), 1.51-1.43 (m, 1H), 1.22 (t, J=7.4 Hz, 3H). m/z (ESI, +ve ion) 727.2 (M+H)$^+$.

2009

Example 996. 2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-(2-hydroxyethyl)acetamide

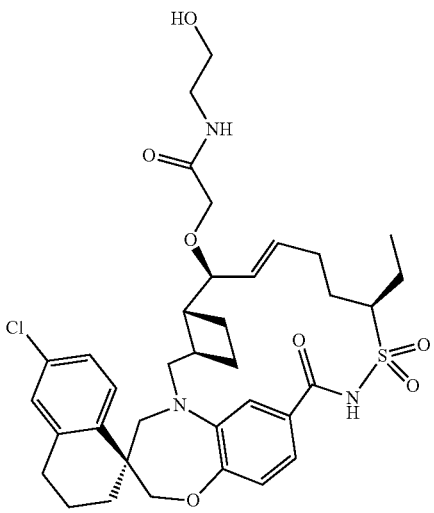 [SMILES: CC[C@@H]1CC/C=C/[C@H](OCC(=O)NCCO)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 995 using (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic acid (from Example 992) and 2-aminoethanol (Aldrich), and the desired product, 2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-(2-hydroxyethyl)acetamide was isolated as a white solid. $^1$H NMR (400 MHz, CD$_3$OD) δ 7.75 (d, J=8.4 Hz, 1H), 7.19 (dd, J=2.2, 8.5 Hz, 1H), 7.13 (d, J=2.2 Hz, 1H), 7.00 (dd, J=1.8, 8.0 Hz, 1H), 6.94 (d, J=8.4 Hz, 1H), 6.85 (d, J=1.8 Hz, 1H), 5.96-5.88 (m, 1H), 5.66 (dd, J=9.2, 15.5 Hz, 1H), 4.14-4.02 (m, 3H), 3.97-3.92 (m, 1H), 3.90 (d, J=3.5 Hz, 2H), 3.88-3.83 (m, 1H), 3.72-3.62 (m, 3H), 3.41-3.37 (m, 2H), 3.10 (dd, J=10.0, 15.3 Hz, 1H), 2.87-2.73 (m, 2H), 2.62 (dd, J=4.3, 10.0 Hz, 1H), 2.47-2.28 (m, 3H), 2.17-2.07 (m, 2H), 2.04-1.84 (m, 9H), 1.78 (dd, J=9.0, 18.0 Hz, 1H), 1.51-1.42 (m, 1H), 1.22 (t, J=7.5 Hz, 3H). m/z (ESI, +ve ion) 700.2 (M+H)$^+$.

2010

Example 997. (1S,3'R,6'R,7'S,8'E,12'R)-7'-(2-(1-azetidinyl)-2-oxoethoxy)-6-chloro-12'-ethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

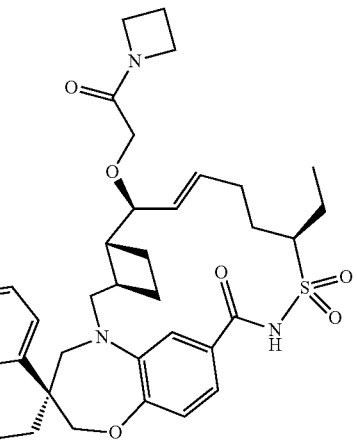

The title compound was prepared in an analogous manner to that described in Example 995 using (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic acid (from Example 992) and azetidine (Fluka), and the desired product, (1S,3'R,6'R,7'S,8'E,12'R)-7'-(2-(1-azetidinyl)-2-oxoethoxy)-6-chloro-12'-ethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (400 MHz, CD$_3$OD) δ 7.75 (d, J=8.4 Hz, 1H), 7.19 (dd, J=2.2, 8.6 Hz, 1H), 7.13 (d, J=2.2 Hz, 1H), 7.00 (dd, J=1.9, 8.1 Hz, 1H), 6.94 (d, J=8.0 Hz, 1H), 6.84 (d, J=1.8 Hz, 1H), 5.94-5.87 (m, 1H), 5.62 (dd, J=8.9, 15.0 Hz, 1H), 4.32 (t, J=7.8 Hz, 2H), 4.11-4.02 (m, 5H), 3.95 (d, J=6.5 Hz, 2H), 3.91-3.82 (m, 2H), 3.69 (d, J=14.3 Hz, 1H), 3.10 (dd, J=10.4, 15.3 Hz, 1H), 2.85-2.77 (m, 2H), 2.61-2.53 (m, 1H), 2.47-2.29 (m, 5H), 2.17-2.08 (m, 2H), 2.04-1.82 (m, 9H), 1.77 (dd, J=9.3, 17.9 Hz, 1H), 1.46 (t, J=14.0 Hz, 1H), 1.22 (t, J=7.5 Hz, 3H). m/z (ESI, +ve ion) 696.2 (M+H)$^+$.

Example 998. (1S,3'R,6'R,7'S,8'E,12'R)-6-chloro-7'-(2-(4,4-difluoro-1-piperidinyl)-2-oxoethoxy)-12'-ethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

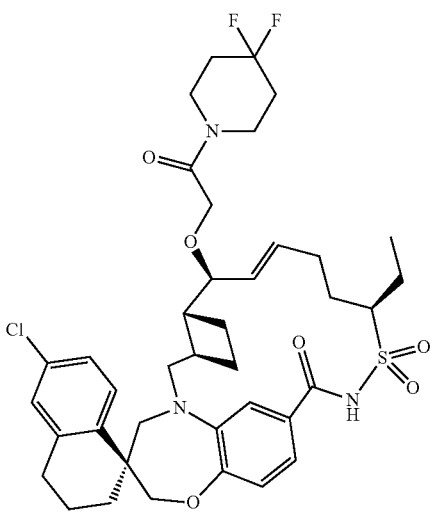 [SMILES: CC[C@@H]1CC/C=C/[C@H](OCC(=O)N2CCC(F)(F)CC2)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 995 using (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic acid (from Example 992) and 4,4-difluoropiperidine hydrochloride (Oakwood), and the desired product, (1S,3'R,6'R,7'S,8'E,12'R)-6-chloro-7'-(2-(4,4-difluoro-1-piperidinyl)-2-oxoethoxy)-12'-ethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (400 MHz, CD$_3$OD) δ 7.75 (d, J=8.4 Hz, 1H), 7.19 (dd, J=2.2, 8.6 Hz, 1H), 7.13 (d, J=2.0 Hz, 1H), 7.00 (dd, J=2.0, 8.4 Hz, 1H), 6.94 (d, J=7.8 Hz, 1H), 6.84 (d, J=1.6 Hz, 1H), 5.96-5.88 (m, 1H), 5.63 (dd, J=9.1, 15.4 Hz, 1H), 4.16 (dd, J=13.5, 17.8 Hz, 2H), 4.09 (d, J=3.1 Hz, 2H), 4.07-4.02 (m, 1H), 3.93 (dd, J=3.4, 9.1 Hz, 1H), 3.85 (d, J=15.1 Hz, 1H), 3.74-3.69 (m, 2H), 3.68-3.61 (m, 3H), 3.37 (s, 4H), 3.10 (dd, J=10.5, 15.4 Hz, 1H), 2.88-2.73 (m, 2H), 2.62-2.54 (m, 1H), 2.47-2.28 (m, 3H), 2.17-1.83 (m, 11H), 1.77 (dd, J=5.9, 14.9 Hz, 1H), 1.46 (t, J=11.6 Hz, 1H), 1.22 (t, J=7.4 Hz, 3H). m/z (ESI, +ve ion) 760.2 (M+H)$^+$.

Example 999. (1S,3'R,6'R,7'S,8'E,12'R)-6-chloro-7'-(2-(1,1-dioxido-4-thiomorpholinyl)-2-oxoethoxy)-12'-ethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

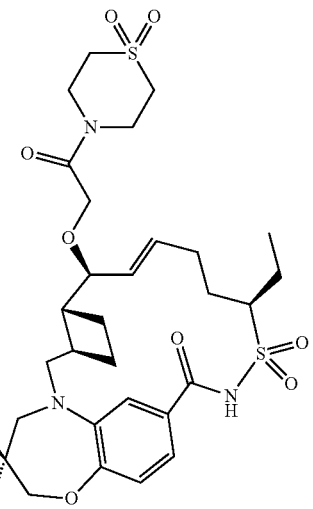

The title compound was prepared in an analogous manner to that described in Example 995 using (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic acid (from Example 992) and thiomorpholine 1,1-dioxide (from TCI), and the desired product, (1S,3'R,6'R,7'S,8'E,12'R)-6-chloro-7'-(2-(1,1-dioxido-4-thiomorpholinyl)-2-oxoethoxy)-12'-ethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (400 MHz, CD$_3$OD) δ 7.75 (d, J=8.4 Hz, 1H), 7.19 (dd, J=2.2, 8.5 Hz, 1H), 7.13 (d, J=2.2 Hz, 1H), 7.00 (dd, J=1.8, 7.2 Hz, 1H), 6.94 (d, J=8.2 Hz, 1H), 6.84 (d, J=1.8 Hz, 1H), 5.98-5.90 (m, 1H), 5.64 (dd, J=9.2, 15.3 Hz, 1H), 4.20 (dd, J=13.9, 20.9 Hz, 2H), 4.13-3.98 (m, 7H), 3.95 (dd, J=3.6, 9.1 Hz, 1H), 3.85 (d, J=15.1 Hz, 1H), 3.69 (d, J=14.1 Hz, 1H), 3.21 (br. s., 2H), 3.18-3.07 (m, 3H), 2.87-2.73 (m, 2H), 2.63-2.52 (m, 1H), 2.48-2.28 (m, 3H), 2.18-2.07 (m, 2H), 2.03-1.75 (m, 10H), 1.50-1.42 (m, 1H), 1.23 (t, J=7.5 Hz, 3H). m/z (ESI, +ve ion) 774.2 (M+H)$^+$.

Example 1000. 2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-4-pyridinylacetamide Example 1001. 2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-(2-methoxyethyl)acetamide

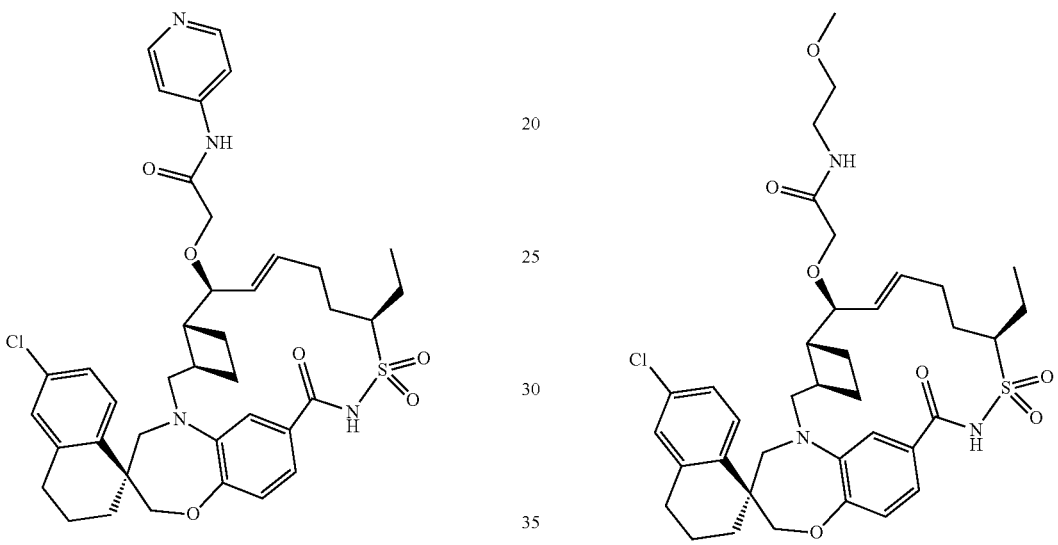

The title compound was prepared in an analogous manner to that described in Example 995 using (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic acid (from Example 992) and 4-aminopyridine (Acros), and the desired product, 2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-4-pyridinylacetamide was isolated as a white solid. $^1$H NMR (500 MHz, CD$_3$OD) δ 8.65 (br. s., 2H), 8.22 (br. s., 2H), 7.75 (d, J=8.6 Hz, 1H), 7.18 (dd, J=2.3, 8.4 Hz, 1H), 7.13 (d, J=2.0 Hz, 1H), 7.00 (dd, J=2.0, 7.8 Hz, 1H), 6.94 (d, J=7.8 Hz, 1H), 6.84 (d, J=1.7 Hz, 1H), 5.97-5.89 (m, 1H), 5.69 (dd, J=9.3, 15.2 Hz, 1H), 4.17 (s, 2H), 4.09 (dd, J=12.0, 18.3 Hz, 2H), 4.03 (dd, J=3.3, 8.9 Hz, 1H), 4.00 (dd, J=6.8, 13.0 Hz, 1H), 3.86 (d, J=15.4 Hz, 1H), 3.69 (d, J=14.4 Hz, 1H), 3.25-3.18 (m, 1H), 3.12 (dd, J=10.1, 15.3 Hz, 1H), 2.87-2.74 (m, 2H), 2.72-2.63 (m, 1H), 2.47-2.26 (m, 3H), 2.10 (td, J=7.2, 14.5 Hz, 2H), 2.02-1.89 (m, 6H), 1.85 (dd, J=6.1, 12.2 Hz, 2H), 1.79 (dd, J=0.5, 18.1 Hz, 1H), 1.51-1.43 (m, 1H), 1.20 (t, J=7.5 Hz, 3H). m/z (ESI, +ve ion) 733.2 (M+H)$^+$.

The title compound was prepared in an analogous manner to that described in Example 995 using (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic acid (from Example 992) and 2-methoxyethanamine (Aldrich), and the desired product, 2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-(2-methoxyethyl)acetamide was isolated as a white solid. $^1$H NMR (400 MHz, CD$_3$OD) δ 7.64 (d, J=8.4 Hz, 1H), 7.08 (dd, J=2.2, 8.5 Hz, 1H), 7.02 (d, J=2.0 Hz, 1H), 6.88 (dd, J=2.0, 8.4 Hz, 1H), 6.83 (d, J=8.2 Hz, 1H), 6.73 (d, J=1.8 Hz, 1H), 5.85-5.76 (m, 1H), 5.54 (dd, J=8.9, 15.0 Hz, 1H), 4.03-3.92 (m, 3H), 3.82 (dd, J=3.8, 9.1 Hz, 1H), 3.78 (d, J=2.3 Hz, 2H), 3.76-3.73 (m, 1H), 3.58 (d, J=13.9 Hz, 1H), 3.42-3.31 (m, 4H), 3.28 (s, 3H), 2.99 (dd, J=10.2, 15.3 Hz, 1H), 2.73-2.63 (m, 2H), 2.55-2.45 (m, 1H), 2.37-2.17 (m, 3H), 2.07-1.95 (m, 2H), 1.92-1.73 (m, 9H), 1.67 (dd, J=8.4, 16.8 Hz, 1H), 1.40-1.31 (m, 1H), 1.11 (t, J=7.5 Hz, 3H). m/z (ESI, +ve ion) 714.4 (M+H)$^+$.

2015

Example 1002. 2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-(2-(4-morpholinyl)ethyl)acetamide

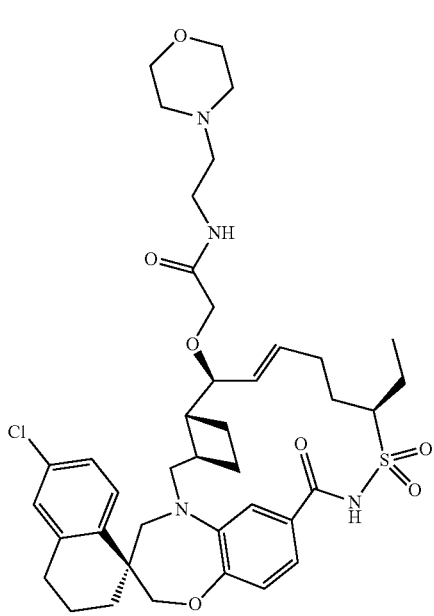 [SMILES: CC[C@@H]1CC/C=C/[C@H](OCC(=O)NCCN2CCOCC2)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 995 using (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic acid (from Example 992) and 4-(2-aminoethyl)morpholine (Avocado Research), and the desired product, 2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N-(2-(4-morpholinyl)ethyl)acetamide was isolated as a white solid. $^1$H NMR (400 MHz, CD$_3$OD) δ 7.75 (d, J=8.6 Hz, 1H), 7.20 (dd, J=2.3, 8.4 Hz, 1H), 7.13 (d, J=2.2 Hz, 1H), 7.02 (dd, J=1.9, 8.1 Hz, 1H), 6.95 (d, J=8.0 Hz, 1H), 6.84 (d, J=1.8 Hz, 1H), 5.96-5.89 (m, 1H), 5.65 (dd, J=9.1, 15.2 Hz, 1H), 4.10 (dd, J=12.1, 18.6 Hz, 3H), 4.05-3.99 (m, 2H), 3.99-3.89 (m, 4H), 3.85 (d, J=15.5 Hz, 2H), 3.73-3.64 (m, 4H), 3.38-3.32 (m, 4H overlap with solvent), 3.10 (dd, J=10.6, 15.5 Hz, 2H), 2.87-2.74 (m, 2H), 2.62 (d, J=9.0 Hz, 1H), 2.43 (br. s., 1H), 2.40-2.29 (m, 2H), 2.12 (dd, J=8.0, 15.3 Hz, 2H), 2.04-1.83 (m, 9H), 1.79 (dd, J=8.6, 17.4 Hz, 1H), 1.52-1.43 (m, 1H), 1.22 (t, J=7.5 Hz, 3H). m/z (ESI, +ve ion) 769.4 (M+H)$^+$.

2016

Example 1003. ethyl (((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetate

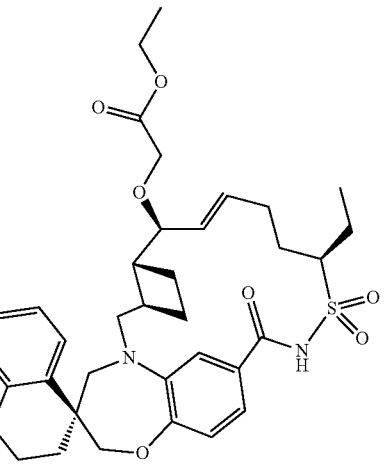

To a 25-mL round-bottomed flask was added (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1; 14 mg, 0.023 mmol) and ethyl diazoacetate (4.84 µl, 0.047 mmol, Aldrich) in DCM (779 µl) and then rhodium (II) acetate dimer (1.0 mg, 2.3 µmol, Aldrich) was added. The reaction mixture was stirred at rt overnight. The reaction mixture was concentrated and purified by reverse phase preparative HPLC (Gemini™ Prep C$_{18}$ 5 µm column; Phenomenex, Torrance, CA; gradient elution of 40% to 95% MeCN in water, where both solvents contain 0.1% TFA, 30 min method) to give ethyl (((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetate as a white solid (10.8 mg, 0.016 mmol). $^1$H NMR (400 MHz, CD$_3$OD) δ 7.75 (d, J=8.4 Hz, 1H), 7.19 (dd, J=2.2, 8.4 Hz, 1H), 7.13 (d, J=2.2 Hz, 1H), 7.00 (dd, J=2.2, 8.2 Hz, 1H), 6.94 (d, J=8.0 Hz, 1H), 6.84 (d, J=1.8 Hz, 1H), 5.92-5.84 (m, 1H), 5.61 (dd, J=9.0, 15.3 Hz, 1H), 4.23 (q, J=7.2 Hz, 2H), 4.09 (dd, J=12.3, 14.9 Hz, 2H), 4.03 (s, 3H), 3.95 (dd, J=3.6, 8.9 Hz, 1H), 3.84 (d, J=14.7 Hz, 1H), 3.68 (d, J=13.9 Hz, 1H), 3.10 (dd, J=10.2, 15.3 Hz, 1H), 2.84-2.73 (m, 2H), 2.64-2.55 (m, 1H), 2.47-2.26 (m, 3H), 2.19-2.06 (m, 2H), 2.00-1.73 (m, 10H), 1.46 (t, J=11.4 Hz, 1H), 1.31 (t, J=7.1 Hz, 3H), 1.22 (t, J=7.4 Hz, 3H). m/z (ESI, +ve ion) 685.2 (M+H)$^+$.

Example 1004. methyl (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoate and methyl (2S)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoate

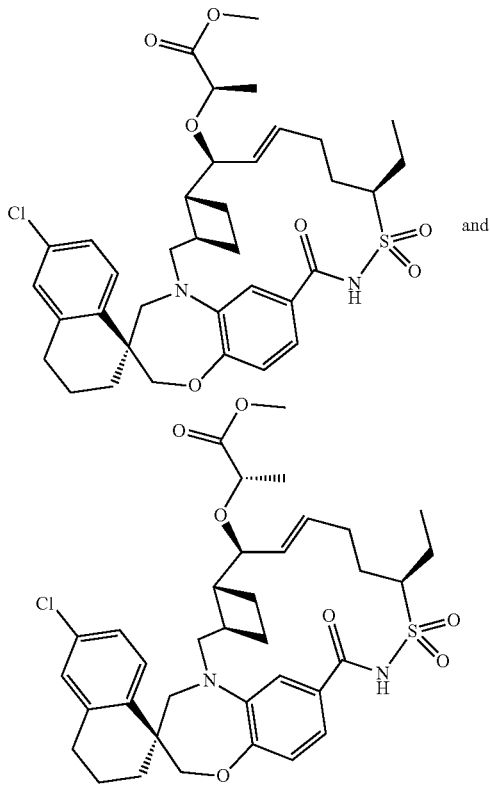

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and methyl 2-bromopropionate (Sigma), and the desired product, a mixture of methyl (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoate and methyl (2S)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoate was isolated as a white solid. $^1$H NMR (400 MHz, CD$_3$OD) δ 7.75 (d, J=8.6 Hz, 1H), 7.19 (dd, J=2.2, 8.5 Hz, 1H), 7.13 (d, J=2.2 Hz, 1H), 6.99 (dd, J=2.3, 8.0 Hz, 1H), 6.95-6.93 (m, 1H), 6.96-6.91 (m, 1H), 6.82 (d, J=1.8 Hz, 1H), 5.91-5.84 (m, 1H), 5.61 (dd, J=9.3, 15.4 Hz, 1H), 4.10 (dd, J=12.3, 15.5 Hz, 2H), 4.03 (dd, J=4.9, 11.9 Hz, 2H), 3.97 (dd, J=3.5, 9.2 Hz, 1H), 3.84 (d, J=14.9 Hz, 1H), 3.71 (s, 3H), 3.68 (d, J=14.7 Hz, 1H), 3.09 (dd, J=10.3, 15.4 Hz, 1H), 2.87-2.73 (m, 2H), 2.56-2.48 (m, 1H), 2.44-2.35 (m, 1H), 2.33-2.08 (m, 4H), 1.99-1.82 (m, 8H), 1.76 (dd, J=9.4, 18.2 Hz, 1H), 1.50-1.41 (m, 1H), 1.35 (d, J=6.7 Hz, 3H), 1.22 (t, J=7.5 Hz, 3H). m/z (ESI, +ve ion) 685.2 (M+H)$^+$.

Example 1005. (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic Acid and (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic Acid

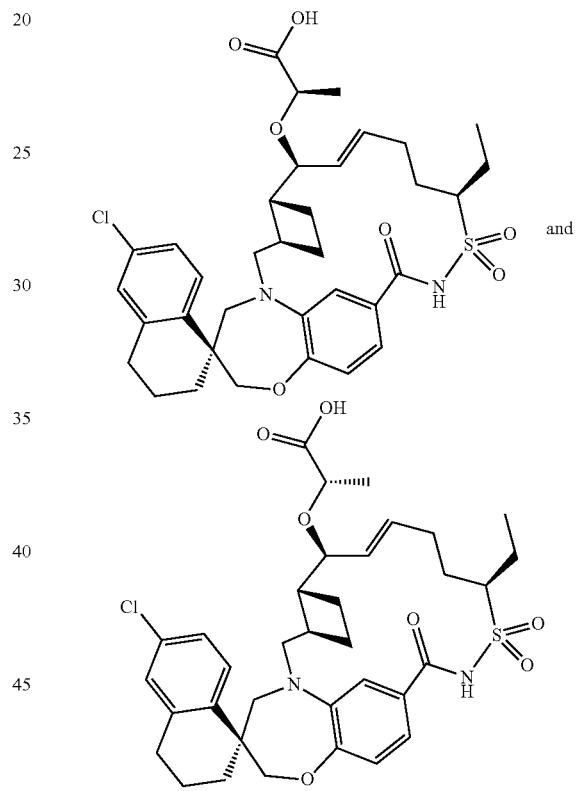

The title compound was prepared in an analogous manner to that described in Example 992 from a mixture of methyl (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoate and methyl (2S)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoate (Example 1004), and the desired product, a mixture of (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic acid and (2R)-2-(((1S,3'R,6'R,7'S,8'E,12'R)-6-chloro-12'-ethyl-13',13'-dioxido-15'-oxo-3,4-dihydro-2H- spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic acid was isolated as a white solid. $^1$H NMR (400 MHz, CD$_3$OD) δ 7.76 (d, J=8.7 Hz, 1H), 7.19 (dd, J=2.3, 8.4 Hz, 1H), 7.13 (d, J=2.2 Hz, 1H), 6.99 (dd, J=1.8, 8.2 Hz, 1H), 6.94 (d, J=8.2 Hz, 1H), 6.82 (d, J=1.8 Hz, 1H), 5.95-5.79 (m, 1H), 5.64 (dd, J=9.3, 15.2 Hz, 1H), 4.24 (q, J=6.6 Hz, 1H), 4.08 (d, J=2.9 Hz, 2H), 4.05 (t, J=6.3 Hz, 1H), 3.98 (ddd, J=3.3, 7.2, 13.9 Hz, 2H), 3.85 (d, J=15.3 Hz, 1H), 3.68 (d, J=14.1 Hz, 1H), 3.10 (dd, J=10.2, 15.3 Hz, 1H), 2.88-2.67 (m, 2H), 2.64-2.47 (m, 1H), 2.42-2.34 (m, 1H), 2.33-2.21 (m, 2H), 2.19-2.06 (m, 2H), 2.01-1.80 (m, 8H), 1.76 (dd, J=9.2, 18.4 Hz, 1H), 1.50-1.42 (m, 1H), 1.37 (d, J=6.8 Hz, 3H), 1.21 (t, J=7.5 Hz, 3H). m/z (ESI, +ve ion) 671.2 (M+H)$^+$.

Example 1006. (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanamide and (2S)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)propanamide

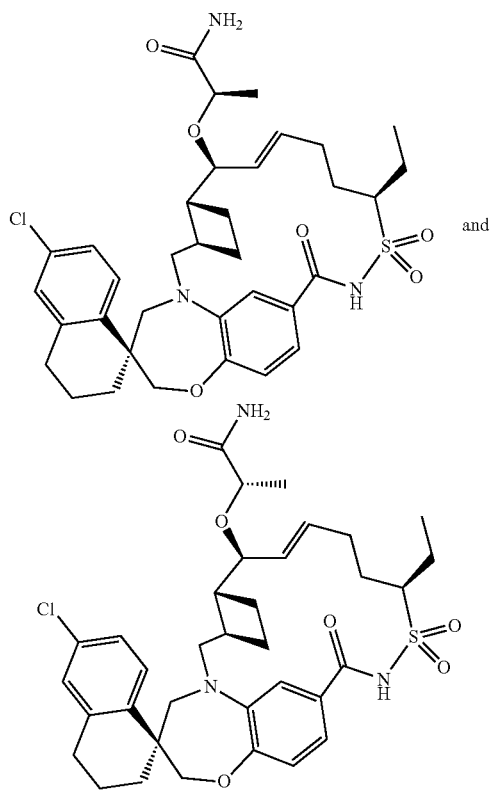

The title compound was prepared in an analogous manner to that described in Example 995 using a mixture of (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic acid and (2R)-2-(((1S,3'R,6'R,7'S,8'E,12'R)-6-chloro-12'-ethyl-13', 13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic acid (Example 1005) and ammonia (7 N solution in methanol, Aldrich), and the desired product, a mixture (2R)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanamide and (2S)-2-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanamide was isolated as a white solid. $^1$H NMR (400 MHz, CD$_3$OD) δ 7.65 (d, J=8.4 Hz, 1H), 7.10 (dd, J=2.2, 8.5 Hz, 1H), 7.03 (d, J=2.2 Hz, 1H), 6.90 (dd, J=1.9, 8.1 Hz, 1H), 6.84 (d, J=8.0 Hz, 1H), 6.78 (d, J=1.8 Hz, 1H), 5.82-5.74 (m, 1H), 5.57 (dd, J=9.1, 15.2 Hz, 1H), 4.00 (d, J=2.3 Hz, 2H), 3.97-3.87 (m, 2H), 3.77 (dd, J=5.9, 13.3 Hz, 2H), 3.60 (d, J=14.1 Hz, 1H), 3.00 (dd, J=10.2, 15.3 Hz, 1H), 2.79-2.64 (m, 2H), 2.49-2.41 (m, 1H), 2.34-2.13 (m, 3H), 2.07-1.98 (m, 2H), 1.92-1.73 (m, 9H), 1.68 (dd, J=10.6, 18.4 Hz, 1H), 1.41-1.30 (m, 1H), 1.25 (d, J=6.7 Hz, 3H), 1.11 (t, J=7.5 Hz, 3H). m/z (ESI, +ve ion) 670.2 (M+H)$^+$.

Example 1007. methyl 3-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoate

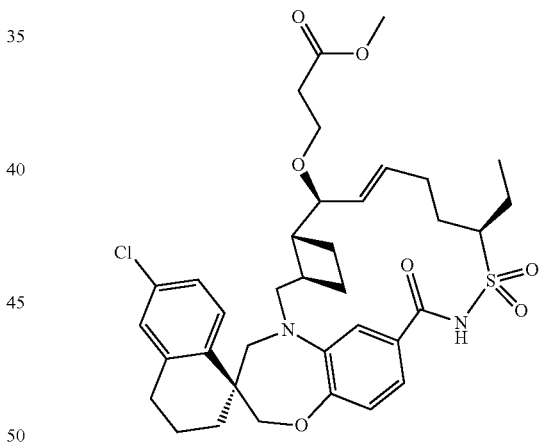

The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and methyl 3-bromopropanoate (Aldrich), and the desired product, methyl 3-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoate was isolated as a white solid. $^1$H NMR (400 MHz, CD$_3$OD) δ 7.75 (dd, J=1.8, 8.2 Hz, 1H), 7.23-7.16 (m, 1H), 7.15-7.08 (m, 1H), 7.00 (d, J=7.8 Hz, 1H), 6.94 (dd, J=2.2, 8.0 Hz, 1H), 6.87 (s, 1H), 5.91-5.80 (m, 1H), 5.60 (dd, J=7.0, 16.8 Hz, 1H), 4.19-3.98 (m, 3H), 3.87 (d, J=13.3 Hz, 2H), 3.74-3.68 (m, 4H), 3.11 (dd, J=9.4, 15.7 Hz, 1H), 2.82 (br. s., 2H), 2.55 (t, J=5.3 Hz, 2H), 2.46 (br. s., 2H), 2.38-2.27 (m, 2H), 2.12 (d, J=8.8 Hz, 2H), 2.08-2.03 (m, 6H), 1.96 (br. s., 3H), 1.84-1.66 (m, 3H), 1.50-1.42 (m, 1H), 1.21 (t, J=6.7 Hz, 3H). m/z (ESI, +ve ion) 685.2 (M+H)+.

Example 1008. 3-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic Acid

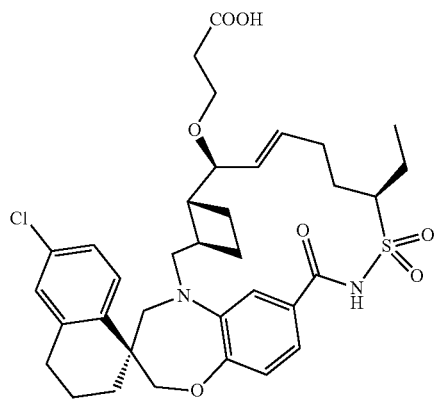 [SMILES: CC[C@@H]1CC/C=C/[C@H](OCCC(=O)O)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 992 using methyl 3-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoate (Example 1007), and the desired product, 3-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic acid was isolated as a white solid. $^1$H NMR (400 MHz, CD$_3$OD) δ 7.76 (d, J=8.4 Hz, 1H), 7.19 (dd, J=2.3, 8.4 Hz, 1H), 7.12 (d, J=2.2 Hz, 1H), 7.02 (dd, J=2.0, 8.0 Hz, 1H), 6.91-6.88 (m, 2H), 5.99-5.90 (m, 1H), 5.57 (dd, J=8.9, 15.2 Hz, 1H), 4.11-4.00 (m, 3H), 3.91-3.80 (m, 2H), 3.76-3.70 (m, 1H), 3.67 (d, J=13.9 Hz, 1H), 3.62-3.55 (m, 1H), 3.06 (dd, J=10.1, 15.0 Hz, 1H), 2.83-2.73 (m, 2H), 2.54-2.42 (m, 4H), 2.40-2.27 (m, 2H), 2.18-2.08 (m, 2H), 1.97-1.69 (m, 9H), 1.45 (t, J=11.9 Hz, 2H), 1.19 (t, J=7.5 Hz, 3H). m/z (ESI, +ve ion) 671.2 (M+H)+.

Example 1009. ethyl 3-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoate The title compound was prepared in an analogous manner to that described in Example 720 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 422, Step 1) and ethyl acrylate (Aldrich), and the desired product, ethyl 3-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoate was isolated as a white solid. $^1$H NMR (400 MHz, CD$_3$OD) δ 7.63 (d, J=7.7 Hz, 1H), 7.08 (dd, J=2.2, 8.4 Hz, 1H), 7.01 (d, J=2.0 Hz, 1H), 6.89 (dd, J=2.0, 8.2 Hz, 1H), 6.83 (d, J=7.6 Hz, 1H), 6.85-6.80 (m, 1H), 6.76 (d, J=1.8 Hz, 1H), 5.79-5.71 (m, 1H), 5.47 (dd, J=8.6, 15.3 Hz, 1H), 4.05 (q, J=7.0 Hz, 2H), 3.99 (d, J=3.1 Hz, 2H), 3.96-3.90 (m, 1H), 3.76 (d, J=2.9 Hz, 1H), 3.77-3.75 (m, 1H), 3.75-3.70 (m, 1H), 3.64-3.60 (m, 1H), 3.57 (d, J=12.7 Hz, 1H), 3.48 (td, J=6.2, 9.7 Hz, 1H), 2.97 (dd, J=10.0, 15.3 Hz, 1H), 2.77-2.61 (m, 2H), 2.43 (t, J=6.3 Hz, 2H), 2.40-2.17 (m, 4H), 2.01 (qd, J=7.1, 14.3 Hz, 2H), 1.90-1.75 (m, 6H), 1.75-1.56 (m, 3H), 1.35 (t, J=11.9 Hz, 1H), 1.17 (t, J=7.0 Hz, 3H), 1.10 (t, J=7.5 Hz, 3H). m/z (ESI, +ve ion) 699.2 (M+H)+.

Example 1010. 3-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N,N-dimethylpropanamide

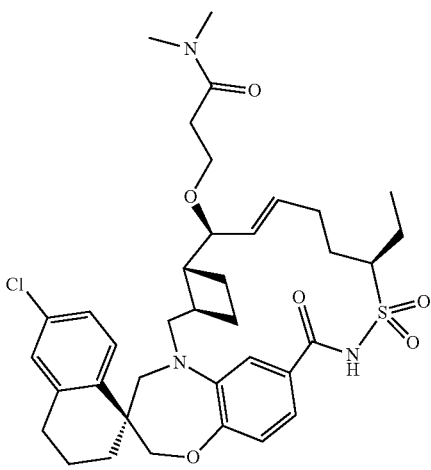 [SMILES: CC[C@@H]1CC/C=C/[C@H](OCCC(=O)N(C)C)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 995 using 3-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic acid (Example 1008) and dimethylamine (40 wt % solution in water, Acros), and the desired product, 3-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)-N,N-dimethylpropanamide was isolated as a white solid. $^1$H NMR (400 MHz, CD$_3$OD) δ 7.64 (d, J=8.6 Hz, 1H), 7.08 (dd, J=2.3, 8.4 Hz, 1H), 7.02 (d, J=2.3 Hz, 1H), 6.89 (dd, J=2.0, 8.2 Hz, 1H), 6.83 (d, J=8.2 Hz, 1H), 6.77 (d, J=1.8 Hz, 1H), 5.79-5.71 (m, 1H), 5.47 (dd, J=8.6, 15.3 Hz, 1H), 3.98 (d, J=2.9 Hz, 2H), 3.96-3.88 (m, 1H), 3.78-3.71 (m, 2H), 3.66-3.60 (m, 1H), 3.57 (d, J=14.3 Hz, 1H), 3.48 (td, J=6.5, 9.4 Hz, 1H), 2.99 (s, 3H), 2.96 (dd, J=9.6, 15.7 Hz, 1H), 2.85 (s, 3H), 2.73-2.60 (m, 2H), 2.50 (dt, J=2.2, 6.5 Hz, 2H), 2.41-2.17 (m, 4H), 2.05-1.95 (m, 2H), 1.90-1.62 (m, 10H), 1.35 (t, J=11.4 Hz, 1H), 1.10 (t, J=7.5 Hz, 3H). m/z (ESI, +ve ion) 698.2 (M+H)$^+$.

Example 1011. (1S,3'R,6'R,7'S,8'E,12'R)-6-chloro-12'-ethyl-7'-(3-(4-morpholinyl)-3-oxopropoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

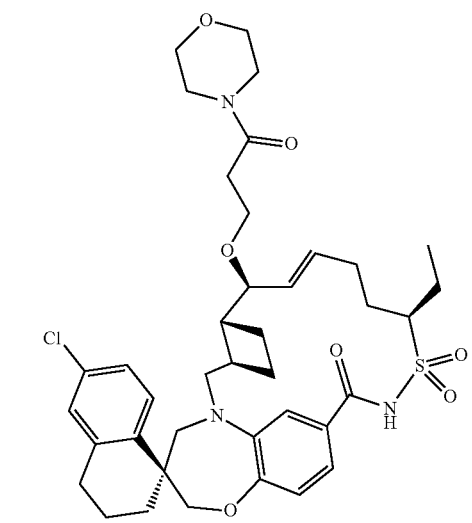 [SMILES: CC[C@@H]1CC/C=C/[C@H](OCCC(=O)N2CCOCC2)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 995 using 3-(((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)propanoic acid (Example 1008) and morpholine, and the desired product, (1S,3'R,6'R,7'S,8'E,12'R)-6-chloro-12'-ethyl-7'-(3-(4-morpholinyl)-3-oxopropoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (400 MHz, CD$_3$OD) δ 7.75 (d, J=8.4 Hz, 1H), 7.19 (dd, J=2.2, 8.4 Hz, 1H), 7.13 (d, J=2.2 Hz, 1H), 7.00 (dd, J=1.9, 8.1 Hz, 1H), 6.94 (d, J=8.0 Hz, 1H), 6.87 (d, J=1.6 Hz, 1H), 5.90-5.83 (m, 1H), 5.59 (dd, J=8.6, 15.1 Hz, 1H), 4.09 (d, J=2.7 Hz, 2H), 4.07-4.01 (m, 1H), 3.85 (dd, J=3.9, 8.6 Hz, 2H), 3.77-3.72 (m, 1H), 3.72-3.64 (m, 6H), 3.64-3.58 (m, 5H), 3.08 (dd, J=10.3, 15.4 Hz, 1H), 2.87-2.73 (m, 2H), 2.63 (t, J=6.3 Hz, 2H), 2.53-2.28 (m, 4H), 2.18-2.07 (m, 2H), 2.01-1.73 (m, 9H), 1.46 (t, J=12.2 Hz, 1H), 1.21 (t, J=7.4 Hz, 3H). m/z (ESI, +ve ion) 740.2 (M+H)$^+$.

Example 1012. (1S,3'R,6'R,7'S,8'E,12'S)-6-chloro-7'-hydroxy-12'-(2-(trifluoromethoxy)ethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-7'-hydroxy-12'-(2-(trifluoromethoxy)ethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

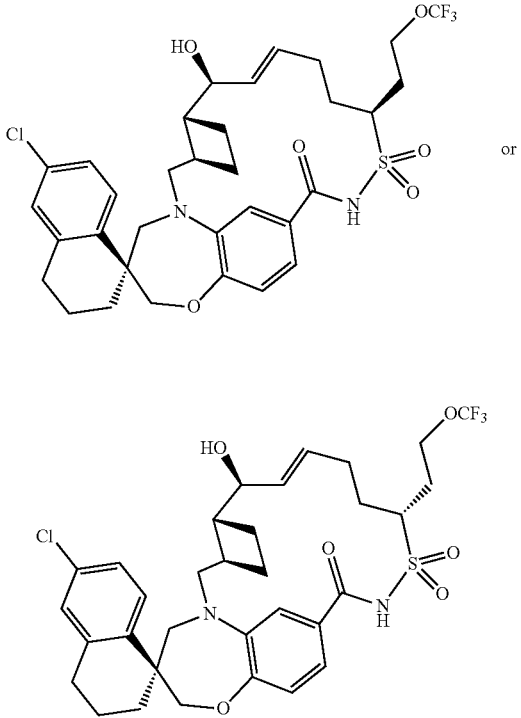 [SMILES: O=C1NS(=O)(=O)[C@H](CCOC(F)(F)F)CC/C=C/[C@H](O)[C@@H]2CC[C@H]2CN2C[C@@]3(CCCc4cc(Cl)ccc43)COc3ccc1cc32 ; O=C1NS(=O)(=O)[C@@H](CCOC(F)(F)F)CC/C=C/[C@H](O)[C@@H]2CC[C@H]2CN2C[C@@]3(CCCc4cc(Cl)ccc43)COc3ccc1cc32]

Step 1: (3S)-1-(trifluoromethoxy)-6-heptene-3-sulfonamide and (3R)-1-(trifluoromethoxy)-6-heptene-3-sulfonamide

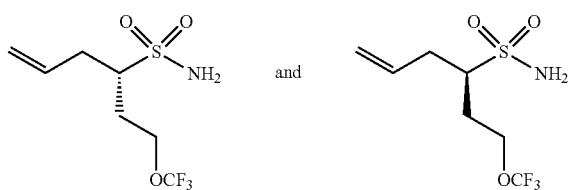

The title compound was prepared in an analogous manner to that described in Intermediates EE20 and EE202 using N,N-bis(4-methoxybenzyl)pent-4-ene-1-sulfonamide (Intermediate EE19) and 1-bromo-2-trifluoromethoxy-ethane (Oakwood), and the desired products (3S)-1-(trifluoromethoxy)-6-heptene-3-sulfonamide and (3R)-1-(trifluoromethoxy)-6-heptene-3-sulfonamide were isolated as a racemic mixture.

Step 2. (1S,3'R,6'R,7'S,8'E,12'S)-6-chloro-7'-hydroxy-12'-(2-(trifluoromethoxy)ethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-7'-hydroxy-12'-(2-(trifluoromethoxy)ethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide The title compound was prepared in an analogous manner to that described in Example 719, Steps 1 and 2, using (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Intermediate AA11A) and a mixture of (3S)-1-(trifluoromethoxy)-6-heptene-3-sulfonamide and (3R)-1-(trifluoromethoxy)-6-heptene-3-sulfonamide from Step 1, and the desired products, (1S,3'R,6'R,7'S,8'E,12'S)-6-chloro-7'-hydroxy-12'-(2-(trifluoromethoxy)ethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'R)-6-chloro-7'-hydroxy-12'-(2-(trifluoromethoxy)ethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (first eluting major peak out of preparative reverse phase HPLC) was isolated. $^{1}$H NMR (400 MHz, CD$_3$OD) δ 7.75 (d, J=8.4 Hz, 1H), 7.19 (dd, J=2.2, 8.5 Hz, 1H), 7.12 (d, J=2.3 Hz, 1H), 7.01 (dd, J=2.0, 8.2 Hz, 1H), 6.94 (d, J=8.6 Hz, 1H), 6.89 (d, J=1.8 Hz, 1H), 5.91-5.82 (m, 1H), 5.78-5.71 (m, 1H), 4.43-4.30 (m, 2H), 4.30-4.23 (m, 1H), 4.21 (dd, J=3.6, 8.1 Hz, 1H), 4.09 (dd, J=11.9, 14.7 Hz, 2H), 3.86 (d, J=14.9 Hz, 1H), 3.68 (d, J=14.1 Hz, 1H), 3.08 (dd, J=10.0, 15.3 Hz, 1H), 2.84-2.73 (m, 2H), 2.54-2.17 (m, 6H), 2.13 (d, J=14.3 Hz, 1H), 1.99-1.79 (m, 7H), 1.74 (dd, J=9.0, 18.2 Hz, 1H), 1.50-1.41 (m, 1H), 1.37-1.29 (m, 1H). m/z (ESI, +ve ion) 683.2 (M+H)$^+$.

Example 1013. (1S,3'R,6'R,7'S,8'E,12'R)-6-chloro-7'-hydroxy-12'-(2-(trifluoromethoxy)ethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,12'S)-6-chloro-7'-hydroxy-12'-(2-(trifluoromethoxy)ethyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

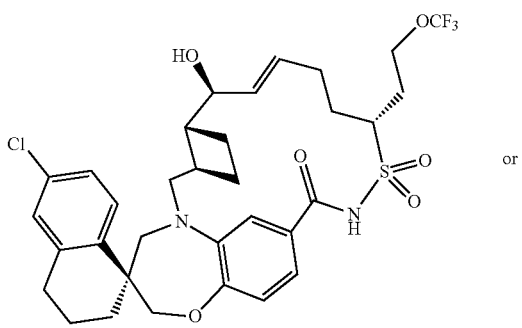

2027
-continued

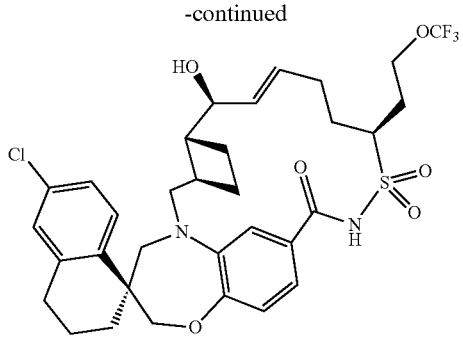

The title compound was obtained as a single isomer (second eluting peak) from the reverse phase preparative HPLC in Example 1012. $^1$H NMR (500 MHz, CD$_3$OD) δ 7.74 (d, J=8.6 Hz, 1H), 7.19 (dd, J=2.3, 8.4 Hz, 1H), 7.15 (br. s., 1H), 7.13 (d, J=2.2 Hz, 1H), 7.10 (dd, J=1.7, 7.8 Hz, 1H), 6.94 (d, J=8.1 Hz, 1H), 5.92-5.83 (m, 1H), 5.67 (dd, J=6.2, 15.3 Hz, 1H), 4.92 (s, 1H), 4.84 (s, 1H), 4.39-4.27 (m, 2H), 4.17-4.02 (m, 3H), 3.96-3.82 (m, 1H), 3.64 (d, J=13.9 Hz, 1H), 3.52-3.46 (m, 1H), 2.87-2.74 (m, 2H), 2.62-2.29 (m, 4H), 2.21-1.99 (m, 4H), 1.96-1.75 (m, 7H), 1.56 (t, J=9.0 Hz, 1H). m/z (ESI, +ve ion) 683.2 (M+H)$^+$.

Example 1014. (1S,3'R,6'R,7'S,8'E,10'R,12'R)-6-chloro-7'-hydroxy-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide and Example 1015. (1S,3'R,6'R,7'S,8'E,10'S,12'R)-6-chloro-7'-hydroxy-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide Example 1014

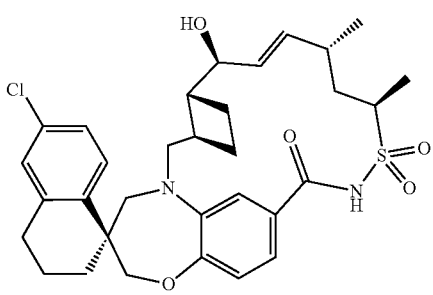

Example 1015

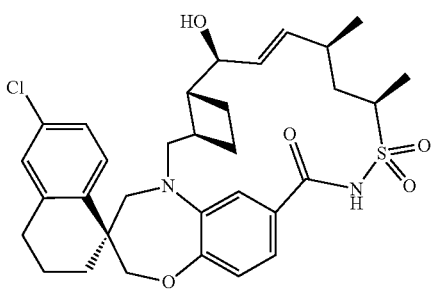

2028
Step 1: (2S,4R)-4-methylhex-5-en-2-ol and (2S,4S)-4-methylhex-5-en-2-ol

To 1-methyl-2-propenylmagnesium chloride (0.5 M solution in THF, 87 ml, 43.4 mmol) was added slowly to the solution of (S)-2-methyloxirane (1.2 g, 20.66 mmol) in Et$_2$O (21 ml) at −10 to −18° C. in a 500 mL single-necked round-bottomed flask at over. The resulting mixture was allowed to slowly warm up to rt and stirred at rt overnight. The reaction mixture was thoroughly cooled in an ice bath before slowly quenched with ice cold saturated ammonium chloride. This mixture was further diluted with more ether and ice cold water. The organic layer was concentrated and purified through a 120 g ISCO Gold column, eluting with 0-35% EtOAc in hexane to give a mixture of (2S,4R)-4-methylhex-5-en-2-ol and (2S,4S)-4-methylhex-5-en-2-ol (1.83 g, 16.03 mmol).

Step 2: (2R,4R)-4-methylhex-5-ene-2-sulfonamide and (2R,4S)-4-methylhex-5-ene-2-sulfonamide

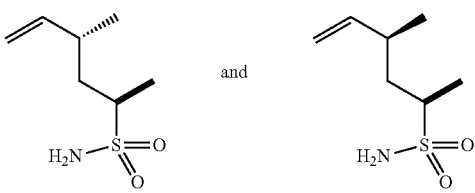

The title compound was prepared according to the general procedure described in Intermediate EE22, Steps 3-6 using a mixture of (2S,4R)-4-methylhex-5-en-2-ol and (2S,4S)-4-methylhex-5-en-2-ol in Step 3.

Step 3: (S)-6'-chloro-5-(((1R,2R)-2-((1S,4R,6R,E)-1-hydroxy-(4R)-methyl-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic Acid and (S)-6'-chloro-5-(((1R,2R)-2-((1S,4R,6R,E)-1-hydroxy-(4S)-methyl-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic Acid

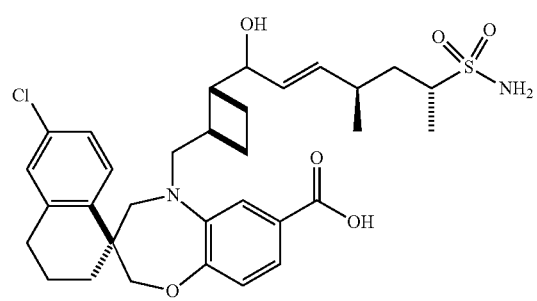

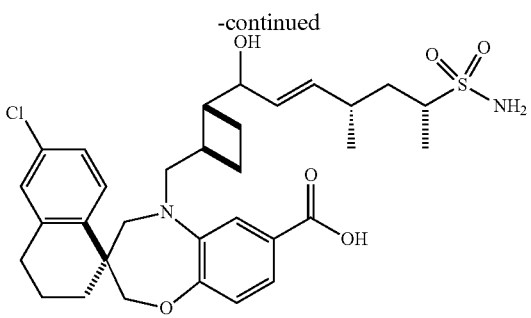

To a 50 mL single-necked round-bottomed flask were added (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic Acid (Intermediate AA12A; 92 mg, 0.18 mmol), a mixture of (2S,4R)-4-methylhex-5-en-2-ol and (2S,4S)-4-methylhex-5-en-2-ol (160 mg, 0.90 mmol) from Step 2 above, and AcOH (3.607 mL). The flask was stirred under nitrogen for 10 min before Hoveyda-Grubbs catalyst II (39.6 mg, 0.063 mmol) was added. The resulting mixture was stirred under Argon at rt for a period of 5 h. The mixture was concentrated and the crude mixture was loaded onto a 40 g ISCO Gold column and subjected to combi-flash column chromatography, eluting with 0-70% EtOAc EtOAc(with 0.3% HOAc) in hexane to give a mixture of the desired products, and then futher purified by reverse phase preparative HPLC (Gemini™ Prep $C_{18}$ 5 µm column; Phenomenex, Torrance, CA; gradient elution of 40% to 95% MeCN in water, where both solvents contain 0.1% TFA, 30 min method) to give (S)-6'-chloro-5-(((1R,2R)-2-((1S,4S,6R,E)-1-hydroxy-(4R)-methyl-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic acid (32.2 mg, 0.052 mmol, second eluting major peak and (S)-6'-chloro-5-(((1R,2R)-2-((1S,4S,6R,E)-1-hydroxy-(4S)-methyl-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic acid (15.7 mg, 0.025 mmol, first eluting major peak).

Step 4: (1S,3'R,6'R,7'S,8'E,10'R,12'R)-6-chloro-7'-hydroxy-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide (Example 1014)

N,N-Dimethylpyridin-4-amine (DMAP) (31.4 mg, 0.26 mmol, Aldrich) was added to a solution of (S)-6'-chloro-5-(((1R,2R)-2-((1S,4R,6R,E)-1-hydroxy-(4R)-methyl-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic acid (second eluting peak in Step 3; 31.7 mg, 0.051 mmol) in DCM (17.4 ml) at 0° C., and then N-(3-dimethylaminopropyl)-N'-ethylcarbodiimide hydrochloride (49.2 mg, 0.26 mmol, Aldrich) was added portion by portion slowly. The resulting solution was stirred at rt for 20 h. The mixture was washed with 1N HCl, the aqueous layer was extracted with EtOAc and the combined organic phase was dried over MgSO$_4$ filtered and concentrated. The crude material was purified by chromatography through a 12 g ISCO gold column, eluting with 0-40% EtOAc (containing 0.3% AcOH) in hexanes to give (1S,3'R,6'R,7'S,8'E,10'R,12'R)-6-chloro-7'-hydroxy-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (22.5 mg, 0.038 mmol) as a white solid. $^1$H NMR (500 MHz, CD$_3$OD) δ 7.75 (d, J=8.6 Hz, 1H), 7.19 (dd, J=2.3, 8.4 Hz, 1H), 7.12 (d, J=2.2 Hz, 1H), 7.00 (dd, J=2.2, 8.6 Hz, 1H), 6.94 (d, J=8.8 Hz, 1H), 6.83 (d, J=1.2 Hz, 1H), 6.00-5.92 (m, 1H), 5.63 (dd, J=7.5, 14.5 Hz, 1H), 4.29-4.21 (m, 2H), 4.09 (dd, J=12.5, 19.6 Hz, 2H), 3.85 (d, J=15.2 Hz, 1H), 3.66 (d, J=13.9 Hz, 1H), 3.22 (d, J=14.2 Hz, 1H), 3.06 (dd, J=9.5, 15.2 Hz, 1H), 2.86-2.73 (m, 2H), 2.58 (br. s., 1H), 2.49-2.39 (m, 1H), 2.24-2.15 (m, 2H), 2.11 (d, J=13.9 Hz, 1H), 1.98-1.66 (m, 6H), 1.48 (d, J=7.1 Hz, 3H), 1.44 (dd, J=1.0, 9.3 Hz, 2H), 1.08 (d, J=6.6 Hz, 3H). m/z (ESI, +ve ion) 599.2 (M+H)$^+$.

Step 5: (1S,3'R,6'R,7'S,8'E,10'S,12'R)-6-chloro-7'-hydroxy-10',12'-dimethyl-3,4-dihydro-2H,15'H-spiro [naphthalene-1,22'-[20]oxa[13]thia[1,14]diazatetracyclo[14.7.2.0$^{3,6}$.0$^{19,24}$]pentacosa [8,16,18,24] tetraen]-15'-one 13',13'-dioxide (Example 15)

The title compound was prepared in an analogous manner to that described in Example 1014, Step 4, using (S)-6'-chloro-5-(((1R,2R)-2-((1S,4S,6R,E)-1-hydroxy-(4S)-methyl-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic Acid (first eluting peak in Step 3), and the desired products, (1S,3'R,6'R,7'S,8'E,10'S,12'R)-6-chloro-7'-hydroxy-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (500 MHz, CD$_3$OD) δ=7.63 (d, J=8.6 Hz, 1H), 7.06 (dd, J=2.2, 8.3 Hz, 1H), 7.00 (d, J=2.2 Hz, 1H), 6.93 (dd, J=2.0, 8.1 Hz, 1H), 6.82 (d, J=8.1 Hz, 1H), 6.81 (d, J=1.7 Hz, 1H), 5.80 (dd, J=4.2, 15.7 Hz, 1H), 5.53 (ddd, J=1.6, 7.0, 15.8 Hz, 1H), 4.16 (dd, J=3.4, 6.8 Hz, 1H), 4.02-3.94 (m, 3H), 3.73 (d, J=15.2 Hz, 1H), 3.55 (d, J=14.2 Hz, 1H), 3.17 (d, J=14.2 Hz, 1H), 2.98 (dd, J=9.8, 15.4 Hz, 1H), 2.74-2.61 (m, 2H), 2.33-2.14 (m, 3H), 1.98 (d, J=13.4 Hz, 1H), 1.87-1.75 (m, 3H), 1.72-1.56 (m, 4H), 1.54-1.43 (m, 1H), 1.38 (d, J=6.8 Hz, 3H), 1.36-1.32 (m, 1H), 1.01 (d, J=6.8 Hz, 3H) m/z (ESI, +ve ion) 599.2 (M+H)$^+$.

Example 1016. (1S,3'R,6'R,7'S,8'E,10'R,12'R)-6-chloro-7'-methoxy-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

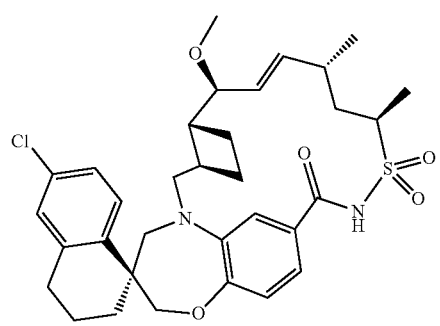 [SMILES: CO[C@H]1/C=C/[C@H](C)C[C@@H](C)S(=O)(=O)NC(=O)c2ccc3c(c2)N(C[C@@H]2CC[C@H]21)C[C@@]1(CCCc2cc(Cl)ccc21)CO3]

The title compound was prepared in an analogous manner to that described in Example 720 using (1S,3'R,6'R,7'S,8'E,10'R,12'R)-6-chloro-7'-hydroxy-10',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 1014) and methyl iodide, and the desired product, (1S,3'R,6'R,7'S,8'E,10'R,12'R)-6-chloro-7'-methoxy-10',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide was isolated as a white solid. $^1$H NMR (500 MHz, CD$_3$OD) δ 7.63 (d, J=8.6 Hz, 1H), 7.07 (dd, J=2.3, 8.4 Hz, 1H), 7.00 (d, J=2.2 Hz, 1H), 6.87 (dd, J=2.2, 8.1 Hz, 1H), 6.82 (d, J=8.1 Hz, 1H), 6.70 (d, J=2.0 Hz, 1H), 5.96 (dd, J=4.5, 15.5 Hz, 1H), 5.38 (ddd, J=1.7, 8.8, 15.7 Hz, 1H), 4.19 (dqd, 1H), 4.03-3.93 (m, 2H), 3.73 (d, J=15.2 Hz, 1H), 3.67 (dd, J=3.9, 8.8 Hz, 1H), 3.55 (d, J=14.2 Hz, 1H), 3.15 (s, 3H), 3.11 (d, J=13.9 Hz, 1H), 2.95 (dd, J=9.8, 15.4 Hz, 1H), 2.74-2.61 (m, 2H), 2.52-2.38 (m, 2H), 2.15-2.04 (m, 2H), 2.01 (d, J=14.2 Hz, 1H), 1.86-1.72 (m, 3H), 1.70-1.58 (m, 3H), 1.39 (d, J=6.8 Hz, 3H), 1.38-1.31 (m, 2H), 0.99 (d, J=6.8 Hz, 3H). m/z (ESI, +ve ion) 613.2 (M+H)$^+$.

Example 1017. (1S,3'R,6'R,7'S,8'E,10'R,12'R)-6-chloro-7'-(2-methoxyethoxy)-10',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

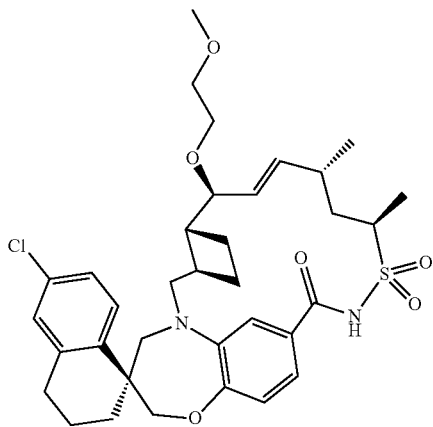 [SMILES: COCCO[C@H]1/C=C/[C@H](C)C[C@@H](C)S(=O)(=O)NC(=O)c2ccc3c(c2)N(C[C@@H]2CC[C@H]21)C[C@@]1(CCCc2cc(Cl)ccc21)CO3]

The title compound was prepared in an analogous manner to that described in Example 720 using (1S,3'R,6'R,7'S,8'E,10'R,12'R)-6-chloro-7'-hydroxy-10',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 1014) and 1-bromo-2-methoxyethane, and the desired product, (1S,3'R,6'R,7'S,8'E,10'R,12'R)-6-chloro-7'-(2-methoxyethoxy)-10',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide was isolated as a white solid. $^1$H NMR (400 MHz, CD$_3$OD) δ 7.75 (d, J=8.6 Hz, 1H), 7.19 (dd, J=2.2, 8.5 Hz, 1H), 7.12 (d, J=2.2 Hz, 1H), 6.99 (dd, J=2.3, 8.0 Hz, 1H), 6.94 (d, J=8.0 Hz, 1H), 6.83 (d, J=1.8 Hz, 1H), 6.06 (dd, J=4.5, 15.7 Hz, 1H), 5.52 (ddd, J=1.7, 8.6, 15.6 Hz, 1H), 4.29 (ddd, J=2.9, 7.0, 10.0 Hz, 1H), 4.09 (dd, J=12.1, 17.8 Hz, 2H), 3.92 (dd, J=3.8, 8.5 Hz, 1H), 3.85 (d, J=15.1 Hz, 1H), 3.67 (d, J=13.9 Hz, 1H), 3.64-3.46 (m, 4H), 3.38 (s, 3H), 3.27-3.20 (m, 1H), 3.07 (dd, J=9.7, 15.4 Hz, 1H), 2.86-2.72 (m, 2H), 2.64-2.51 (m, 2H), 2.26-2.16 (m, 2H), 2.11 (d, J=14.1 Hz, 1H), 1.98-1.71 (m, 6H), 1.51 (d, J=7.0 Hz, 3H), 1.49-1.42 (m, 2H), 1.10 (d, J=6.7 Hz, 3H). m/z (ESI, +ve ion) 657.2 (M+H)$^+$.

Example 1018. (1S,3'R,6'R,7'S,8'E,10'R,12'R)-6-chloro-10',12'-dimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

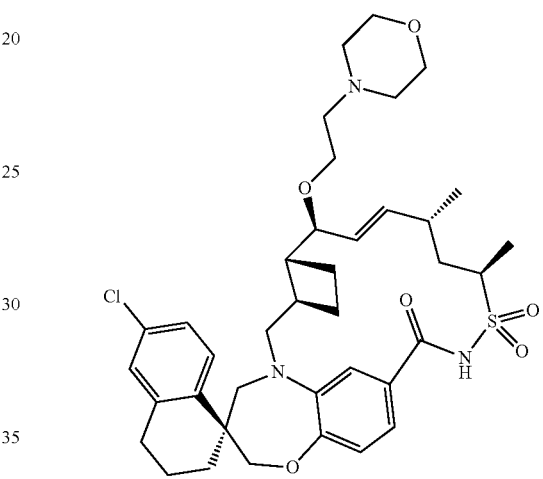

The title compound was prepared in an analogous manner to that described in Example 720 using (1S,3'R,6'R,7'S,8'E,10'R,12'R)-6-chloro-7'-hydroxy-10',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 1014) and 4-(2-bromoethyl)morpholine, and the desired product, (1S,3'R,6'R,7'S,8'E,10'R,12'R)-6-chloro-10',12'-dimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide was isolated as a white solid. $^1$H NMR (500 MHz, CD$_3$OD) δ 7.62 (d, J=8.3 Hz, 1H), 7.07 (dd, J=2.2, 8.6 Hz, 1H), 7.00 (d, J=2.2 Hz, 1H), 6.88 (dd, J=2.2, 8.1 Hz, 1H), 6.83 (d, J=8.6 Hz, 1H), 6.68 (d, J=1.5 Hz, 1H), 6.02 (dd, J=4.5, 15.5 Hz, 1H), 5.44 (ddd, J=1.5, 8.9, 15.5 Hz, 1H), 4.17 (ddd, J=3.3, 7.0, 10.0 Hz, 1H), 3.97 (q, J=12.2 Hz, 4H), 3.86 (dd, J=3.8, 8.9 Hz, 1H), 3.74 (d, J=14.9 Hz, 1H), 3.71-3.63 (m, 3H), 3.63-3.53 (m, 2H), 3.40 (br. s., 2H), 3.30-3.25 (m, 2H), 3.24-3.19 (m, 2H overlap with solvent), 3.11 (d, J=14.2 Hz, 2H), 2.96 (dd, J=9.9, 15.3 Hz, 1H), 2.76-2.61 (m, 2H), 2.53-2.43 (m, 2H), 2.15-2.05 (m, 2H), 1.98 (d, J=13.7 Hz, 1H), 1.87-1.81 (m, 3H), 1.81-1.68 (m, 3H), 1.63 (dd, J=8.1, 17.4 Hz, 1H), 1.39 (d, J=7.1 Hz, 3H), 1.38-1.31 (m, 2H), 1.00 (d, J=6.6 Hz, 3H). m/z (ESI, +ve ion) 712.1 (M+H)$^+$.

2033

Example 1019. (1S,3'R,6'R,7'S,8'E,10'S,12'R)-6-chloro-7'-methoxy-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

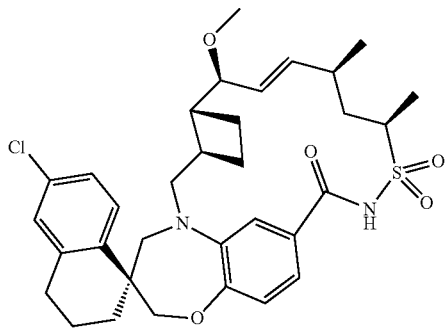 [SMILES: CO[C@H]1/C=C/[C@@H](C)C[C@@H](C)S(=O)(=O)NC(=O)c2ccc3c(c2)N(C[C@@H]2CC[C@H]21)C[C@@]1(CCCc2cc(Cl)ccc21)CO3]

The title compound was prepared in an analogous manner to that described in Example 720 using (1S,3'R,6'R,7'S,8'E,10'S,12'R)-6-chloro-7'-hydroxy-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 1015) and iodomethane, and the desired product, (1S,3'R,6'R,7'S,8'E,10'S,12'R)-6-chloro-7'-methoxy-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (500 MHz, CD$_3$OD) δ 7.75 (d, J=8.3 Hz, 1H), 7.18 (dd, J=2.0, 6.8 Hz, 1H), 7.13 (d, J=2.0 Hz, 1H), 7.03 (dd, J=1.7, 8.1 Hz, 1H), 6.95 (d, J=8.1 Hz, 1H), 6.91 (d, J=1.5 Hz, 1H), 5.93 (dd, J=3.4, 15.7 Hz, 1H), 5.51 (ddd, J=1.2, 8.6, 13.4 Hz, 1H), 4.16-4.11 (m, 1H), 4.10 (s, 2H), 3.85 (d, J=15.2 Hz, 1H), 3.76 (dd, J=3.2, 8.1 Hz, 1H), 3.68 (d, J=14.2 Hz, 1H), 3.26 (s, 3H), 3.11 (dd, J=10.0, 15.2 Hz, 1H), 2.88-2.74 (m, 2H), 2.53-2.44 (m, 1H), 2.42 (br. s., 1H), 2.32 (quin, J=9.0 Hz, 1H), 2.11 (d, J=14.4 Hz, 1H), 2.00-1.87 (m, 4H), 1.86-1.58 (m, 5H), 1.54 (d, J=6.8 Hz, 3H), 1.46 (t, J=12.0 Hz, 1H), 1.15 (d, J=6.8 Hz, 3H) m/z (ESI, +ve ion) 613.2 (M+H)$^+$.

2034

Example 1020. (1S,3'R,6'R,7'S,8'E,10'S,12'R)-6-chloro-7'-(2-methoxyethoxy)-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

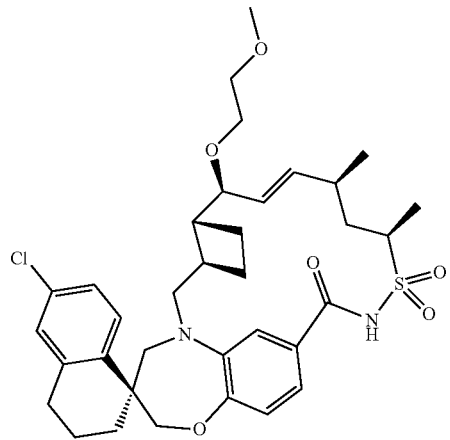 [SMILES: COCCO[C@H]1/C=C/[C@@H](C)C[C@@H](C)S(=O)(=O)NC(=O)c2ccc3c(c2)N(C[C@@H]2CC[C@H]21)C[C@@]1(CCCc2cc(Cl)ccc21)CO3]

The title compound was prepared in an analogous manner to that described in Example 720 using (1S,3'R,6'R,7'S,8'E,10'S,12'R)-6-chloro-7'-hydroxy-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 1015) and 1-bromo-2-methoxyethane, and the desired product, (1S,3'R,6'R,7'S,8'E,10'S,12'R)-6-chloro-7'-(2-methoxyethoxy)-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (500 MHz, CD$_3$OD) δ 7.75 (d, J=8.6 Hz, 1H), 7.19 (dd, J=2.2, 8.6 Hz, 1H), 7.12 (d, J=2.0 Hz, 1H), 7.04 (dd, J=1.7, 8.1 Hz, 1H), 6.95 (d, J=8.1 Hz, 1H), 6.93 (d, J=1.7 Hz, 1H), 5.91 (dd, J=3.8, 15.8 Hz, 1H), 5.53 (ddd, J=1.5, 8.1, 15.7 Hz, 1H), 4.17-4.04 (m, 3H), 3.90 (dd, J=3.2, 7.8 Hz, 1H), 3.86 (d, J=15.2 Hz, 1H), 3.68 (d, J=14.2 Hz, 1H), 3.61-3.44 (m, 4H), 3.38 (s, 3H), 3.11 (dd, J=9.9, 15.3 Hz, 1H), 2.87-2.74 (m, 2H), 2.52 (dd, J=9.3, 18.6 Hz, 1H), 2.43-2.35 (m, 1H), 2.34-2.29 (m, 1H), 2.11 (d, J=13.2 Hz, 1H), 2.01-1.87 (m, 4H), 1.83 (dd, J=9.5, 17.6 Hz, 2H), 1.78-1.71 (m, 1H), 1.71-1.64 (m, 1H), 1.63-1.56 (m, 1H), 1.53 (d, J=6.8 Hz, 3H), 1.50-1.43 (m, 1H), 1.14 (d, J=6.6 Hz, 3H). m/z (ESI, +ve ion) 657.2 (M+H)$^+$.

Example 1021. (1S,3'R,6'R,7'S,8'E,10'R,12'S)-6-chloro-7'-hydroxy-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'S)-6-chloro-7'-hydroxy-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide Example 1022. (1S,3'R,6'R,7'S,8'E,10'S,12'S)-6-chloro-7'-hydroxy-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'S)-6-chloro-7'-hydroxy-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

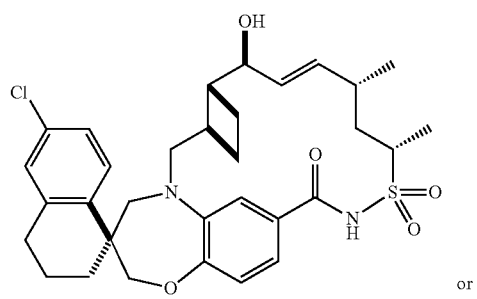

or

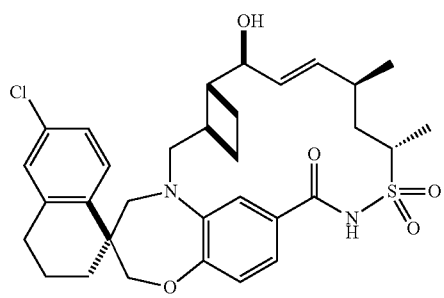

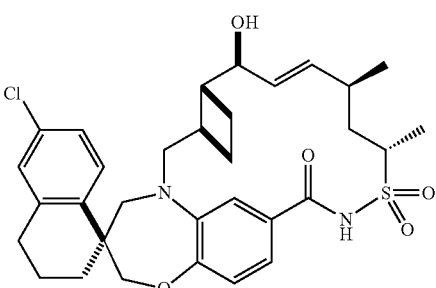

or

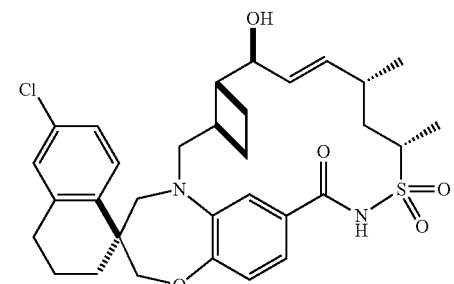

The title compounds were prepared in an analogous manner to that described in Example 1014, Steps 1 through 4, but replacing (S)-2-methyloxirane with (R)-2-methyloxirane in Step 1. The desired product, (1S,3'R,6'R,7'S,8'E,10'R,12'S)-6-chloro-7'-hydroxy-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'S)-6-chloro-7'-hydroxy-10',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated (first eluting major peak out of reverse phase preparative HPLC). $^1$H NMR (400 MHz, CD$_3$OD) δ 7.76 (d, J=9.0 Hz, 1H), 7.20 (dd, J=2.3, 8.6 Hz, 1H), 7.13 (d, J=2.3 Hz, 1H), 7.01 (s, 1H), 6.97 (dd, J=1.8, 8.2 Hz, 1H), 6.93 (d, J=8.0 Hz, 1H), 6.17 (dd, J=3.2, 15.6 Hz, 1H), 5.61 (ddd, J=1.7, 5.1, 15.7 Hz, 1H), 4.15-4.03 (m, 4H), 3.69-3.57 (m, 2H), 3.24 (dd, J=9.9, 15.0 Hz, 1H), 2.87-2.74 (m, 2H), 2.66 (d, J=8.2 Hz, 2H), 2.36-2.29 (m, 1H), 2.11-1.86 (m, 7H), 1.85-1.65 (m, 3H), 1.60-1.43 (m, 4H), 1.10 (d, J=6.8 Hz, 3H). m/z (ESI, +ve ion) 599.2 (M+H)$^+$.

The title was obtained as a single isomer (second eluting major peak) from the reverse phase preparative HPLC in Example 1021. $^1$H NMR (500 MHz, CD$_3$OD) δ 7.59 (d, J=8.6 Hz, 1H), 7.30 (br. s., 1H), 7.05 (d, J=8.3 Hz, 1H), 7.02-6.97 (m, 2H), 6.82 (d, J=8.3 Hz, 1H), 5.51 (dd, J=5.4, 16.6 Hz, 1H), 5.40 (br. s., 1H), 4.10 (t, J=12.7 Hz, 2H), 3.85 (br. s., 1H), 3.76-3.60 (m, 2H), 3.51 (d, J=14.2 Hz, 1H), 3.38 (d, J=16.9 Hz, 1H), 2.73-2.62 (m, 2H), 2.41 (br. s., 2H), 2.16-2.04 (m, 1H), 1.92-1.68 (m, 6H), 1.66-1.53 (m, 2H), 1.51-1.41 (m, 2H), 1.40 (d, J=7.1 Hz, 3H), 1.22-1.15 (m, 1H), 0.95 (d, J=6.6 Hz, 3H). m/z (ESI, +ve ion) 599.2 (M+H)$^+$.

Example 1023. (1S,3'R,6'R,7'S,8'E,10'R,12'R)-6-chloro-12'-ethyl-7'-hydroxy-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'R)-6-chloro-12'-ethyl-7'-hydroxy-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide Example 1024. (1S,3'R,6'R,7'S,8'E,10'S,12'R)-6-chloro-12'-ethyl-7'-hydroxy-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'R)-6-chloro-12'-ethyl-7'-hydroxy-10'-methyl-3,4-dihydro-2H,15'H-spiro [naphthalene-1,22'-[20]oxa[13]thia[1,14] diazatetracyclo[14.7.2.0$^{3,6}$.0$^{19,24}$]pentacosa [8,16,18,24]tetraen]-15'-one 13',13'-dioxide

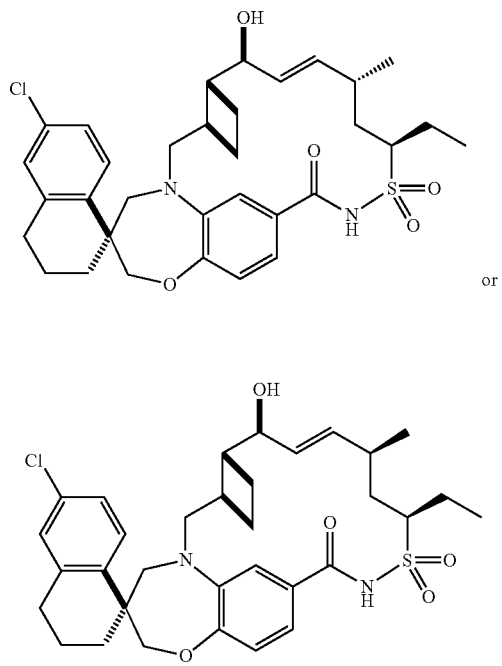

or

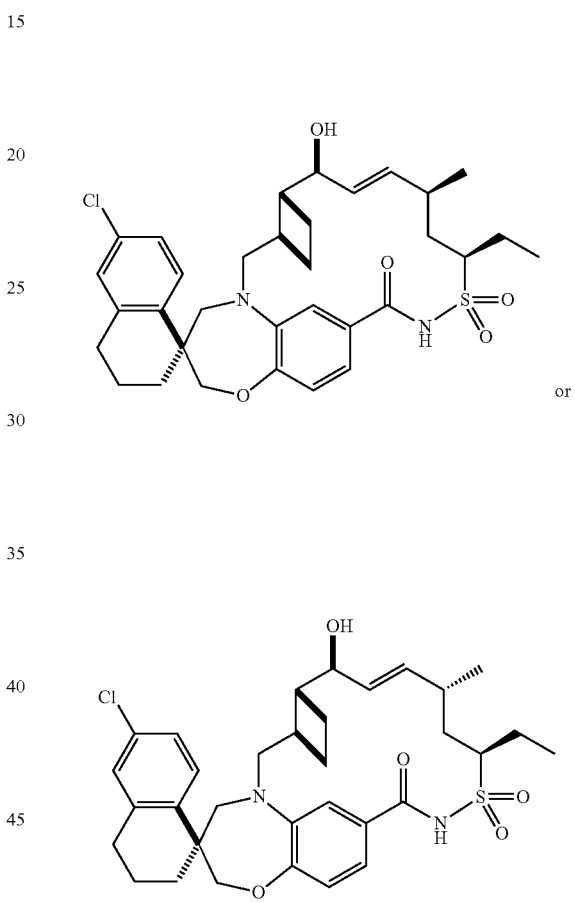

The title compounds were prepared in an analogous manner to that described in Example 1014, Steps 1 to 4, but replacing (S)-methyl oxirane with (S)-2-ethyloxirane, and the desired product, (1S,3'R,6'R,7'S,8'E,10'R,12'R)-6-chloro-12'-ethyl-7'-hydroxy-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-12'-ethyl-7'-hydroxy-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated (first eluting major peak out of reverse phase preparative HPLC). $^1$H NMR (500 MHz, CD$_3$OD) δ 7.75 (d, J=8.4 Hz, 1H), 7.19 (dd, J=2.0, 8.6 Hz, 1H), 7.12 (d, J=2.0 Hz, 1H), 6.99 (dd, J=1.7, 8.3 Hz, 1H), 6.95 (dd, J=1.2, 8.3 Hz, 1H), 6.81 (d, J=1.7 Hz, 1H), 5.89 (dd, J=5.4, 15.4 Hz, 1H), 5.64 (dd, J=7.1, 15.4 Hz, 1H), 4.28 (dd, J=4.4, 6.8 Hz, 1H), 4.10 (dd, J=12.2, 22.7 Hz, 3H), 3.85 (d, J=15.2 Hz, 1H), 3.66 (d, J=13.9 Hz, 1H), 3.22 (d, J=13.9 Hz, 1H), 3.06 (dd, J=9.7, 15.3 Hz, 1H), 2.86-2.73 (m, 2H), 2.56 (br. s., 1H), 2.46 (br. s., 1H), 2.25-2.08 (m, 4H), 1.95-1.65 (m, 7H), 1.60-1.43 (m, 2H), 1.12 (t, J=7.5 Hz, 3H), 1.10 (d, J=6.6 Hz, 3H). m/z (ESI, +ve ion) 613.2 (M+H)$^+$.

The title compounds was obtained as a simgle isomer (second eluting major peak) from the reverse phase preparative HPLC in Example 1023. $^1$H NMR (500 MHz, methanol-d$_4$) δ 7.76 (d, J=8.6 Hz, 1H), 7.19 (dd, J=2.1, 8.4 Hz, 1H), 7.12 (d, J=2.0 Hz, 1H), 7.06 (d, J=7.6 Hz, 1H), 6.95 (br. s., 1H), 6.93 (d, J=8.1 Hz, 1H), 5.92 (dd, J=4.2, 15.9 Hz, 1H), 5.66 (dd, J=6.0, 16.5 Hz, 1H), 4.28 (dd, J=3.2, 6.8 Hz, 1H), 4.10 (s, 2H), 3.96 (br. s., 1H), 3.85 (d, J=14.9 Hz, 1H), 3.67 (d, J=13.9 Hz, 1H), 3.11 (dd, J=9.5, 15.2 Hz, 1H), 2.87-2.74 (m, 2H), 2.45-2.28 (m, 3H), 2.13-1.93 (m, 6H), 1.93-1.63 (m, 7H), 1.47 (t, J=11.2 Hz, 1H), 1.21 (t, J=7.6 Hz, 3H), 1.12 (d, J=6.8 Hz, 3H). m/z (ESI, +ve ion) 613.2 (M+H)$^+$.

Example 1025. (1S,3'R,6'R,7'S,8'E,10'R,12'R)-6-chloro-12'-ethyl-7'-(2-methoxyethoxy)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,12'R)-6-chloro-12'-ethyl-7'-(2-methoxyethoxy)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

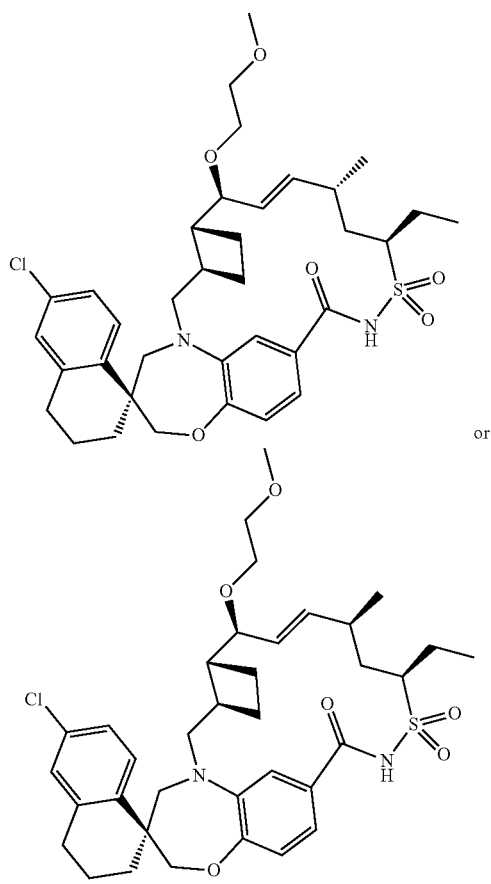

or

The title compound was prepared in an analogous manner to that described in Example 720 using (1S,3'R,6'R,7'S,8'E,10'R,12'R)-6-chloro-12'-ethyl-7'-hydroxy-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-12'-ethyl-7'-hydroxy-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (from Example 1023) and 1-bromo-2-methoxyethane (Aldrich), and the desired product, (1S,3'R,6'R,7'S,8'E,10'R,12'R)-6-chloro-12'-ethyl-7'-(2-methoxyethoxy)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-12'-ethyl-7'-(2-methoxyethoxy)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (500 MHz, CD$_3$OD) δ 7.75 (d, J=8.3 Hz, 1H), 7.19 (dd, J=2.3, 8.4 Hz, 1H), 7.12 (d, J=2.0 Hz, 1H), 6.99 (dd, J=1.7, 8.1 Hz, 1H), 6.93 (d, J=8.1 Hz, 1H), 6.82 (d, J=1.5 Hz, 1H), 6.04 (dd, J=3.7, 15.2 Hz, 1H), 5.54-5.47 (m, 1H), 4.14-4.03 (m, 3H), 3.95 (dd, J=3.8, 8.4 Hz, 1H), 3.85 (d, J=15.4 Hz, 1H), 3.67 (d, J=14.2 Hz, 1H), 3.62-3.46 (m, 4H), 3.38 (s, 3H), 3.22 (d, J=14.2 Hz, 1H), 3.06 (dd, J=9.7, 15.3 Hz, 1H), 2.85-2.73 (m, 2H), 2.62-2.52 (m, 2H), 2.24-2.09 (m, 4H), 1.98-1.85 (m, 3H), 1.84-1.68 (m, 4H), 1.55 (t, J=13.0 Hz, 1H), 1.45 (t, J=11.7 Hz, 1H), 1.14-1.08 (m, 6H). m/z (ESI, +ve ion) 671.2 (M+H)$^+$.

Example 1026. (1S,3'R,6'R,7'S,8'E,10'R,12'R)-6-chloro-12'-ethyl-10'-methyl-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

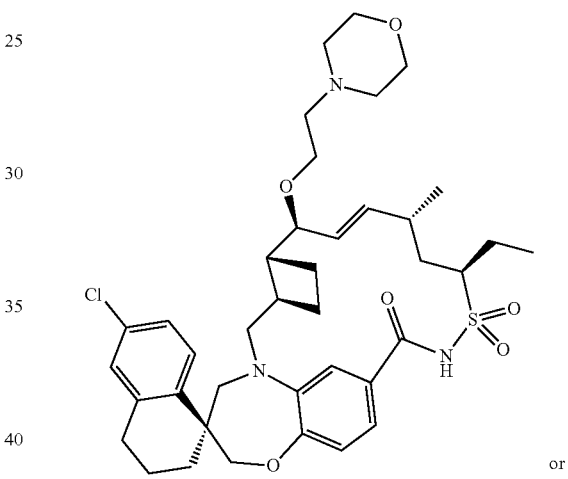

or

The title compound was prepared in an analogous manner to that described in Example 720 using (1S,3'R,6'R,7'S,8'E,10'R,12'R)-6-chloro-12'-ethyl-7'-hydroxy-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'R)-6-chloro-12'-ethyl-7'-hydroxy-10'-methyl-3,4- dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (from Example 1023) and 4-(2-bromoethyl)morpholine (Aldrich), and the desired product, (1S,3'R,6'R,7'S,8'E,10'R,12'R)-6-chloro-12'-ethyl-10'-methyl-7'-(2-(4-morpholinyl)ethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'S,12'R)-6-chloro-12'-ethyl-10'-methyl-7'-(2-(4-morpholinyl)ethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide was isolated as a white solid. ¹H NMR (500 MHz, CD₃OD) δ 7.75 (d, J=8.6 Hz, 1H), 7.19 (dd, J=2.7, 8.1 Hz, 1H), 7.13 (d, J=2.2 Hz, 1H), 6.99 (dd, J=1.5, 7.8 Hz, 1H), 6.79 (d, J=1.7 Hz, 1H), 6.11 (dd, J=4.4, 15.7 Hz, 1H), 5.57 (ddd, J=2.0, 9.0, 14.2 Hz, 1H), 5.61-5.52 (m, 1H), 4.11 (dd, J=11.7, 27.1 Hz, 4H), 4.00 (dd, J=3.9, 8.8 Hz, 1H), 3.99-3.98 (m, 1H), 3.87 (d, J=15.7 Hz, 1H), 3.82-3.75 (m, 2H), 3.73-3.65 (m, 2H), 3.43-3.38 (m, 2H), 3.37 (s, 2H), 3.30-3.27 (m, 2H), 3.23 (d, J=14.2 Hz, 2H), 3.08 (dd, J=9.7, 15.5 Hz, 1H), 2.87-2.73 (m, 2H), 2.65-2.54 (m, 2H), 2.27-2.03 (m, 6H), 1.99-1.89 (m, 2H), 1.89-1.69 (m, 5H), 1.61-1.39 (m, 2H), 1.16-1.09 (m, 6H). m/z (ESI, +ve ion) 726.4 (M+H)⁺.

Example 1027. (1S,3'R,6'R,7'S,8'E,10'S,12'R)-6-chloro-12'-ethyl-10'-methyl-7'-(2-(4-morpholinyl)ethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'R,12'R)-6-chloro-12'-ethyl-10'-methyl-7'-(2-(4-morpholinyl)ethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

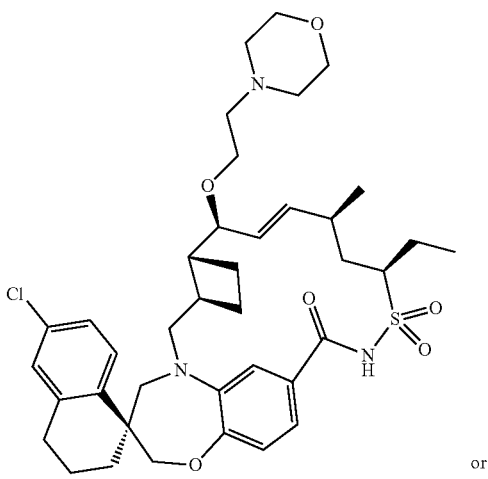

or

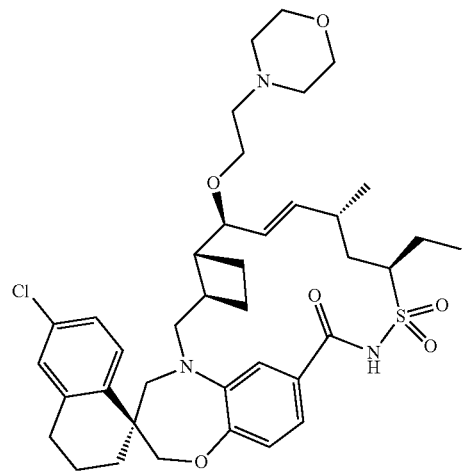

The title compound was prepared in an analogous manner to that described in Example 720 using (1S,3'R,6'R,7'S,8'E,10'S,12'R)-6-chloro-12'-ethyl-7'-hydroxy-10'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,12'R)-6-chloro-12'-ethyl-7'-hydroxy-10'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (from Example 1024) and 4-(2-bromoethyl)morpholine (Aldrich), and the desired product, (1S,3'R,6'R,7'S,8'E,10'R,12'R)-6-chloro-12'-ethyl-10'-methyl-7'-(2-(4-morpholinyl)ethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'S,12'R)-6-chloro-12'-ethyl-10'-methyl-7'-(2-(4-morpholinyl)ethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide was isolated as a white solid. ¹H NMR (500 MHz, CD₃OD) δ 7.75 (d, J=7.8 Hz, 1H), 7.19 (dd, J=2.7, 8.6 Hz, 1H), 7.14 (d, J=2.2 Hz, 1H), 7.05 (dd, J=2.7, 6.6 Hz, 1H), 6.96 (d, J=8.1 Hz, 1H), 6.91 (d, J=1.7 Hz, 1H), 5.99 (dd, J=3.2, 16.1 Hz, 1H), 5.59 (dd, J=8.7, 15.8 Hz, 1H), 5.63-5.54 (m, 1H), 4.15-4.03 (m, 3H), 3.99 (d, J=4.9 Hz, 2H), 3.91-3.77 (m, 4H), 3.68 (d, J=13.4 Hz, 1H), 3.52 (dd, J=6.6, 13.9 Hz, 2H), 3.41 (br. s., 2H), 3.28 (br. s., 2H), 3.22-3.03 (m, 3H), 2.86-2.74 (m, 3H), 2.60-2.51 (m, 1H), 2.43 (br. s., 1H), 2.37-2.29 (m, 1H), 2.15-1.71 (m, 10H), 1.61 (t, J=12.6 Hz, 1H), 1.49 (t, J=12.3 Hz, 1H), 1.23 (t, J=7.0 Hz, 3H), 1.16 (d, J=6.4 Hz, 3H). m/z (ESI, +ve ion) 726.4 (M+H)⁺.

Example 1028. (3R,6R,7S,8E,11S,15S,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7S,8E,11R,15R,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide Example 1029. (3R,6R,7S,8E,11R,15R,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7S,8E,11S,15S,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide

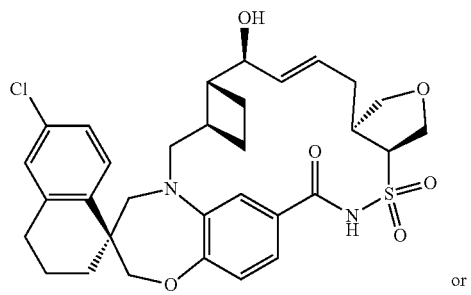

or

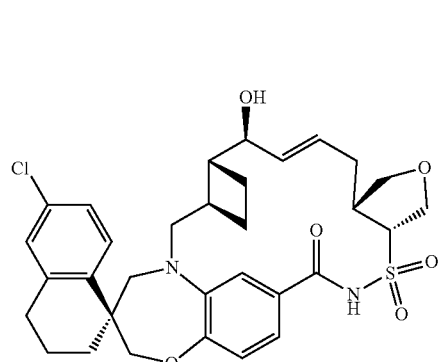

or

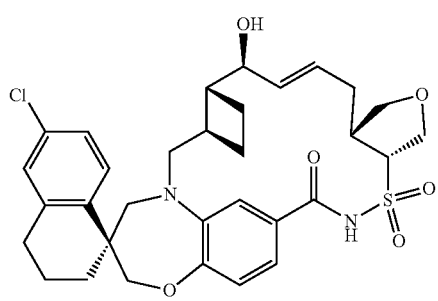

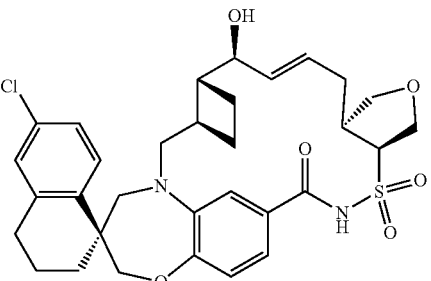

The title compounds were prepared in an analogous manner to that described in Examples 323 and 324, Steps 1 to 7, but replacing 1,2-epoxycyclopentane with 3,4-epoxytetrahydrofuran (TCI America) in Step 1, and the desired product, (3R,6R,7S,8E,11S,15S,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7S,8E,11R,15R,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide was isolated (first eluting major peak out of reverse phase preparative HPLC). $^1$H NMR (400 MHz, CD$_3$OD) δ 7.66 (d, J=8.6 Hz, 1H), 7.09 (d, J=8.0 Hz, 1H), 7.03 (d, J=2.5 Hz, 1H), 6.92-6.83 (m, 2H), 6.73-6.68 (m, 1H), 6.01-5.84 (m, 1H), 5.56 (dd, J=8.3, 14.2 Hz, 1H), 4.72 (br. s., 2H), 4.53 (d, J=9.8 Hz, 2H), 4.19 (dd, J=6.7, 8.2 Hz, 1H), 4.08-3.94 (m, 3H), 3.88 (d, J=7.6 Hz, 1H), 3.80 (d, J=10.4 Hz, 1H), 3.72 (d, J=15.3 Hz, 1H), 3.59 (d, J=13.7 Hz, 1H), 3.02 (dd, J=8.8, 14.9 Hz, 1H), 2.75-2.51 (m, 4H), 2.37-2.19 (m, 2H), 2.03 (d, J=14.9 Hz, 1H), 1.93-1.57 (m, 6H). 1.42-1.32 (m, 1H). m/z (ESI, +ve ion) 613.2 (M+H)$^+$.

The title compound was obtained as a single isomer (second eluting major peak) from the reverse phase preparative HPLC in Example 1028. $^1$H NMR (500 MHz, CD$_3$OD) δ 7.76 (d, J=8.6 Hz, 1H), 7.20 (d, J=6.1 Hz, 1H), 7.12 (d, J=2.2 Hz, 2H), 7.03-6.93 (m, 2H), 6.17 (br. s., 1H), 5.74 (dd, J=3.4, 16.4 Hz, 1H), 4.61-4.40 (m, 1H), 4.27-4.14 (m, 1H), 4.12 (d, J=11.0 Hz, 2H), 4.06-3.92 (m, 2H), 3.92-3.79 (m, 2H), 3.76 (d, J=13.9 Hz, 1H), 3.24-3.04 (m, 1H), 2.90-2.74 (m, 4H), 2.70-2.51 (m, 2H), 2.51-2.22 (m, 2H), 2.11 (d, J=13.2 Hz, 2H), 2.01-1.72 (m, 6H). 1.47 (t, J=9.8 Hz, 1H). m/z (ESI, +ve ion) 613.2 (M+H)$^+$.

Example 1030. (3R,6R,7S,8E,11R,15S,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7S,8E,11S,15R,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide Example 1031. (3R,6R,7S,8E,11S,15R,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7S,8E,11R,15S,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide

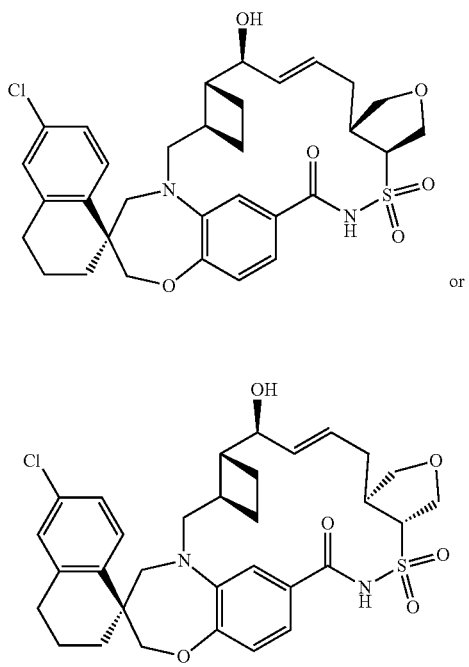

or

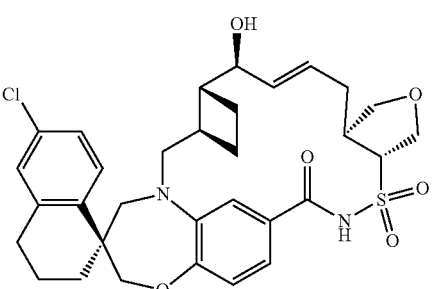

or

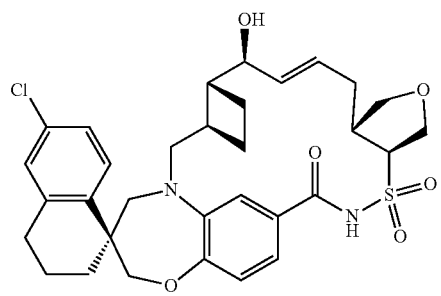

The title compounds were prepared in an analogous manner to that described in Examples 325 and 326, Steps 1 to 8, but replacing the mixture of (1R,2S)-2-allylcyclopentanol and (1S,2R)-2-allylcyclopentanol with a mixture of (3S,4S)-4-allyltetrahydrofuran-3-ol and (3R,4R)-4-allyltetrahydrofuran-3-ol (prepared from 3,4-epoxytetrahydrofuran (TCI America) using a similar procedure described in Example 323 in Step 1) in Step 1, and the desired product, (3R,6R,7S,8E,11R,15S,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7S,8E,11S,15R,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide was isolated (first eluting major peak out of reverse phase preparative HPLC). $^1$H NMR (400 MHz, CD$_3$OD) δ 7.75 (d, J=8.6 Hz, 1H), 7.19 (dd, J=2.2, 8.5 Hz, 1H), 7.13 (d, J=2.2 Hz, 1H), 7.07 (dd, J=2.0, 8.2 Hz, 1H), 6.99-6.94 (m, 2H), 5.85-5.71 (m, 2H), 4.64 (td, J=5.1, 8.1 Hz, 1H), 4.37-4.27 (m, 2H), 4.18 (dd, J=4.2, 7.5 Hz, 1H), 4.14-4.07 (m, 3H), 3.83 (d, J=15.1 Hz, 1H), 3.69 (d, J=14.7 Hz, 1H), 3.62 (dd, J=5.6, 8.3 Hz, 1H), 3.13 (dd, J=9.2, 15.3 Hz, 1H), 2.87-2.66 (m, 3H), 2.49-2.26 (m, 4H), 2.12 (d, J=13.5 Hz, 1H), 2.00-1.77 (m, 6H), 1.74 (dd, J=9.6, 19.2 Hz, 1H), 1.48 (t, J=11.6 Hz, 1H). m/z (ESI, +ve ion) 613.2 (M+H)$^+$.

The title compound was obtained as a single isomer (second eluting major peak) from the reverse phase preparative HPLC in Example 1030. $^1$H NMR (400 MHz, MeOH) δ 7.74 (d, J=8.6 Hz, 1H), 7.19 (d, J=6.5 Hz, 2H), 7.13 (d, J=2.2 Hz, 1H), 7.08 (dd, J=2.0, 8.2 Hz, 1H), 6.95 (d, J=8.2 Hz, 1H), 5.83-5.74 (m, 1H), 5.70 (dd, J=6.1, 15.5 Hz, 1H), 4.33-4.18 (m, 3H), 4.18-4.12 (m, 3H), 4.03 (t, J=5.0 Hz, 1H), 3.66-3.45 (m, 5H), 2.93-2.74 (m, 3H), 2.55-2.43 (m, 2H), 2.42-2.24 (m, 2H), 2.05 (d, J=11.2 Hz, 1H), 1.96-1.87 (m, 3H), 1.86-1.69 (m, 3H), 1.64-1.54 (m, 1H). m/z (ESI, +ve ion) 613.2 (M+H)$^+$.

Example 1032. (3R,6R,7S,8E,11R,15S,25S)-6'-chloro-7-methoxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7S,8E,11S,15R,25S)-6'-chloro-7-methoxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide

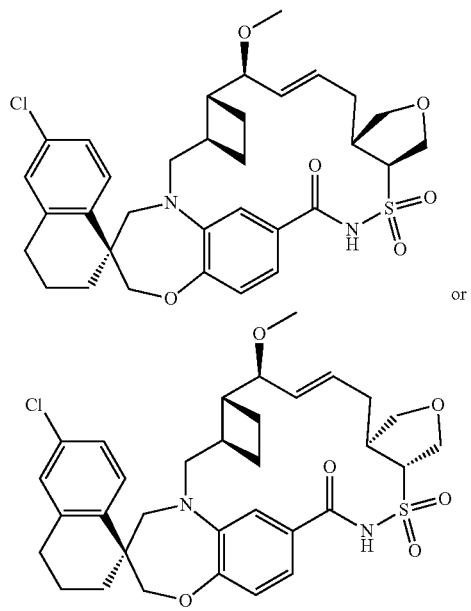

or

The title compound was prepared in an analogous manner to that described in Example 720 using (3R,6R,7S,8E,11R,15S,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7S,8E,11S,15R,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$ 0$^{22,27}$]octacosa-8,19,21,27-tetraene-25,1'-naphthalen]-18-one 16,16-dioxide (Example 1030) and methyl iodide, and the desired product, (3R,6R,7S,8E,11R,15S,25S)-6'-chloro-7-methoxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7S,8E,11S,15R,25S)-6'-chloro-7-methoxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide was isolated as a white solid. $^1$H NMR (400 MHz, CD$_3$OD) δ 7.74 (d, J=7.7 Hz, 1H), 7.18 (dd, J=2.3, 8.6 Hz, 1H), 7.12 (d, J=2.2 Hz, 1H), 7.06 (dd, J=1.8, 8.2 Hz, 1H), 6.97-6.91 (m, 2H), 5.93-5.83 (m, 1H), 5.59 (dd, J=8.8, 15.3 Hz, 1H), 4.67 (dd, J=0.6, 7.8 Hz, 1H), 4.36-4.28 (m, 2H), 4.16-4.10 (m, 1H), 4.09 (s, 2H), 3.81 (d, J=15.1 Hz, 1H), 3.72-3.69 (m, 1H), 3.66 (d, J=15.1 Hz, 1H), 3.62-3.54 (m, 1H), 3.22 (s, 3H), 3.13 (dd, J=10.0, 14.5 Hz, 1H), 2.86-2.62 (m, 3H), 2.55-2.29 (m, 4H), 2.11 (d, J=13.7 Hz, 1H), 1.99-1.67 (m, 7H), 1.52-1.41 (m, 1H). m/z (ESI, +ve ion) 627.2 (M+H)$^+$.

Example 1033. (3R,6R,7S,8E,11R,15S,25S)-6'-chloro-7-(2-methoxyethoxy)-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7S,8E,11S,15R,25S)-6'-chloro-7-(2-methoxyethoxy)-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide

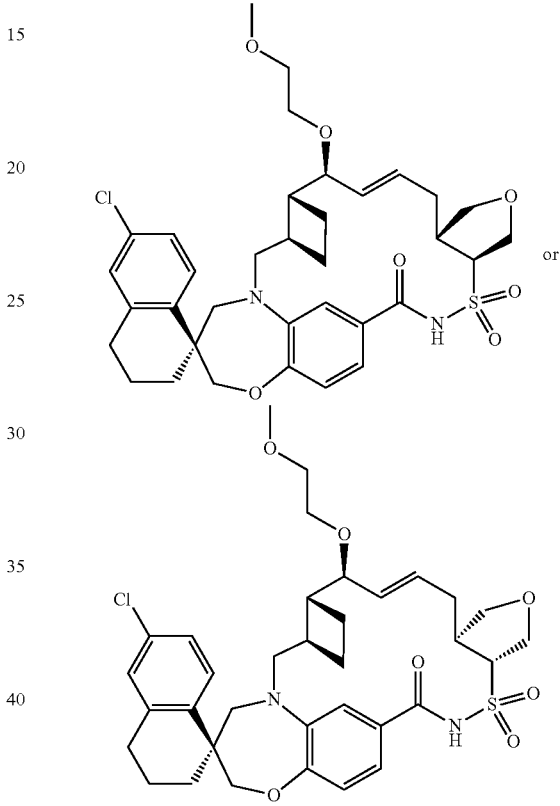

or

The title compound was prepared in an analogous manner to that described in Example 720 using (3R,6R,7S,8E,11R,15S,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7S,8E,11S,15R,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$ 0$^{22,27}$]octacosa-8,19,21,27-tetraene-25,1'-naphthalen]-18-one 16,16-dioxide (Example 1030) and 1-bromo-2-methoxyethane (Aldrich), and the desired product, (3R,6R,7S,8E,11R,15S,25S)-6'-chloro-7-(2-methoxyethoxy)-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7S,8E,11S,15R,25S)-6'-chloro-7-(2-methoxyethoxy)-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide was isolated as a white solid. $^1$H NMR (500 MHz, CD$_3$OD) δ 7.75 (d, J=8.6 Hz, 1H), 7.19 (dd, J=2.2, 8.6 Hz, 1H), 7.13 (d, J=2.0 Hz, 1H), 7.05 (dd, J=2.0, 8.1 Hz, 1H), 6.97 (d, J=1.7

Hz, 1H), 6.95 (d, J=8.1 Hz, 1H), 5.87-5.79 (m, 1H), 5.63 (dd, J=8.4, 15.3 Hz, 1H), 4.68-4.63 (m, 1H), 4.36-4.29 (m, 2H), 4.11 (t, J=8.6 Hz, 3H), 3.87-3.80 (m, 2H), 3.68 (d, J=14.2 Hz, 1H), 3.61-3.40 (m, 6H), 3.38-3.36 (m, 3H), 3.12 (dd, J=9.4, 15.0 Hz, 1H), 2.87-2.66 (m, 3H), 2.59-2.50 (m, 1H), 2.46-2.30 (m, 3H), 2.12 (d, J=14.2 Hz, 1H), 2.02-1.66 (m, 6H), 1.47 (t, J=11.9 Hz, 1H). m/z (ESI, +ve ion) 671.2 (M+H)$^+$.

Example 1034. (3R,6R,7S,8E,11S,15R,25S)-6'-chloro-7-(2-methoxyethoxy)-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7S,8E,11R,15S,25S)-6'-chloro-7-(2-methoxyethoxy)-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide

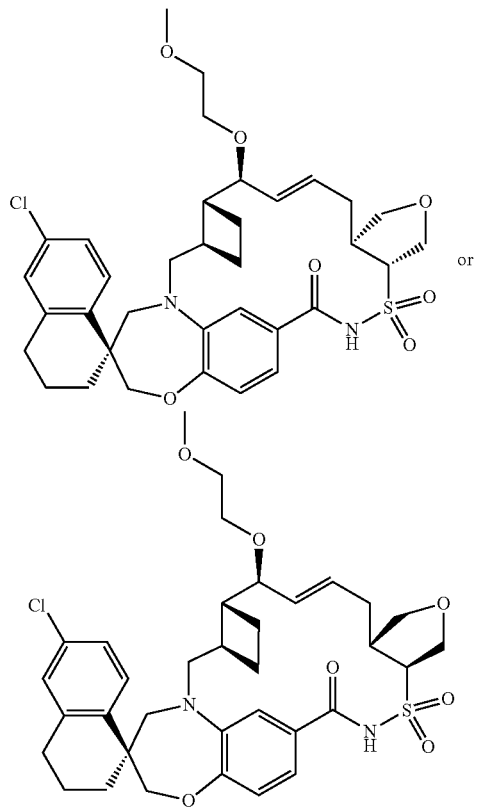

or

The title compound was prepared in an analogous manner to that described in Example 720 1 using (3R,6R,7S,8E,11S,15R,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7S,8E,11R,15S,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide (Example 1031) and 1-bromo-2-methoxyethane (Aldrich), and the desired product, (3R,6R,7S,8E,11S,15R,25S)-6'-chloro-7-(2-methoxyethoxy)-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7S,8E,11R,15S,25S)-6'-chloro-7-(2-methoxyethoxy)-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide was isolated as a white solid. $^1$H NMR (500 MHz, CD$_3$OD) δ 7.74 (d, J=8.6 Hz, 1H), 7.23-7.18 (m, 1H), 7.19 (dd, J=2.2, 8.6 Hz, 1H), 7.13 (d, J=2.2 Hz, 1H), 7.07 (dd, J=2.0, 8.1 Hz, 1H), 6.94 (d, J=8.0 Hz, 1H), 5.86-5.80 (m, 1H), 5.58 (dd, J=6.4, 15.7 Hz, 1H), 4.31 (dd, J=5.1, 9.3 Hz, 1H), 4.25-4.14 (m, 3H), 4.13 (s, 2H), 3.69 (t, J=5.7 Hz, 3H), 3.65-3.55 (m, 3H), 3.54-3.49 (m, 3H), 3.49-3.40 (m, 3H), 3.38 (s, 3H), 2.92-2.74 (m, 3H), 2.54-2.43 (m, 2H), 2.40-2.28 (m, 2H), 2.08-2.02 (m, 1H), 1.97-1.88 (m, 3H), 1.83-1.70 (m, 3H), 1.60-1.54 (m, 1H). m/z (ESI, +ve ion) 671.2 (M+H)$^+$.

Example 1035. (3R,6R,7R,8E,11R,15S,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7R,8E,11S,15R,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide

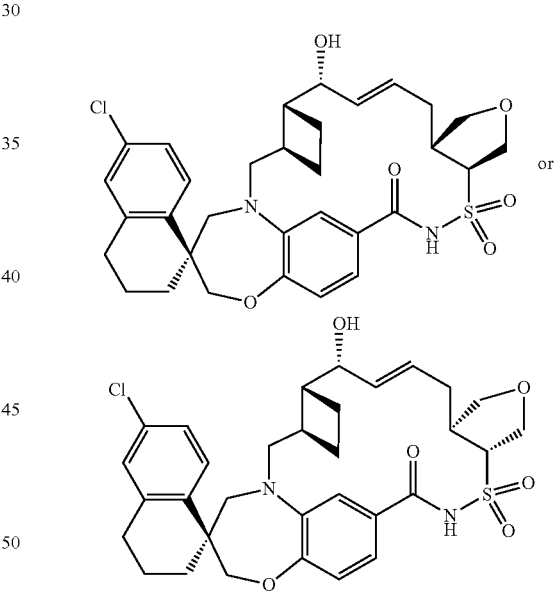

The title compounds were prepared in an analogous manner to that described in Examples 325 and 326, Step 1 to 8, but replacing Intermediate AA11A with Intermediate AA11B in Step 7, and the desired products, (3R,6R,7R,8E,11R,15S,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7R,8E,11S,15R,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide was isolated (first eluting major peak out of reverse phase preparative HPLC). $^1$H NMR (400 MHz, CD$_3$OD) δ 7.71 (d, J=8.61 Hz, 1H) 7.09-7.24 (m, 4H)

6.94-7.01 (m, 1H) 5.47-5.68 (m, 2H) 4.10-4.36 (m, 6H) 3.91-4.04 (m, 2H) 3.69 (d, J=13.69 Hz, 1H) 3.46-3.62 (m, 2H) 2.81 (d, J=4.89 Hz, 3H) 1.66-2.53 (m, 13H). m/z (ESI, +ve ion) 613.2 (M+H)⁺.

Example 1036. (3R,6R,7R,8E,11S,15R,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide or (3R,6R,7R,8E,11R,15S,25S)-6'-chloro-7-hydroxy-3',4'-dihydro-2'H,18H-spiro[13,23-dioxa-16-thia-1,17-diazapentacyclo[17.7.2.0$^{3,6}$.0$^{11,15}$.0$^{22,27}$]octacosa-8,19,21,27-tetraene-25,1'-naphthalen]-18-one 16,16-dioxide

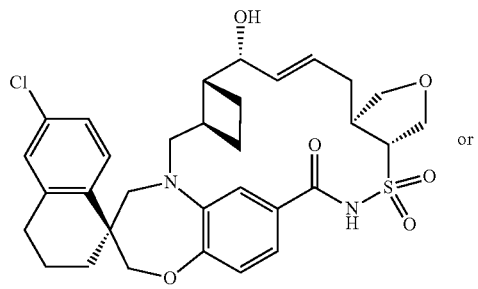

or

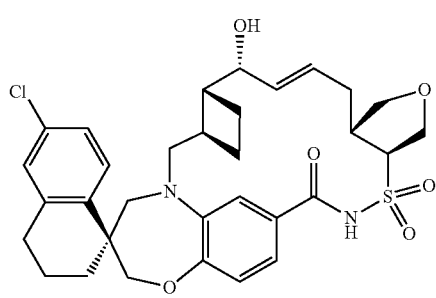

The title compound was obtained as a single isomer (second eluting major peak) from the reverse phase preparative HPLC in Example 1035. ¹H NMR (400 MHz, MeOH) δ 7.77 (d, J=8.6 Hz, 1H), 7.55 (d, J=2.0 Hz, 1H), 7.23-7.18 (m, 2H), 7.13 (d, J=2.3 Hz, 1H), 6.95 (d, J=8.2 Hz, 1H), 5.47 (dd, J=8.0, 15.3 Hz, 1H), 5.31-5.22 (m, 1H), 4.29-4.04 (m, 6H), 3.90 (dd, J=8.5, 15.6 Hz, 1H), 3.76 (d, J=14.3 Hz, 1H), 3.58 (dd, J=3.4, 8.7 Hz, 1H), 3.43 (d, J=8.2 Hz, 1H), 3.07-3.01 (m, 1H), 2.87-2.73 (m, 3H), 2.67-2.54 (m, 2H), 2.31 (d, J=14.9 Hz, 1H), 2.14-2.04 (m, 2H), 1.99-1.57 (m, 7H), 1.51-1.40 (m, 1H). m/z (ESI, +ve ion) 613.2 (M+H)⁺.

Example 1037. (1S,3'R,6'R,7'S,10'S,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,10'R,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

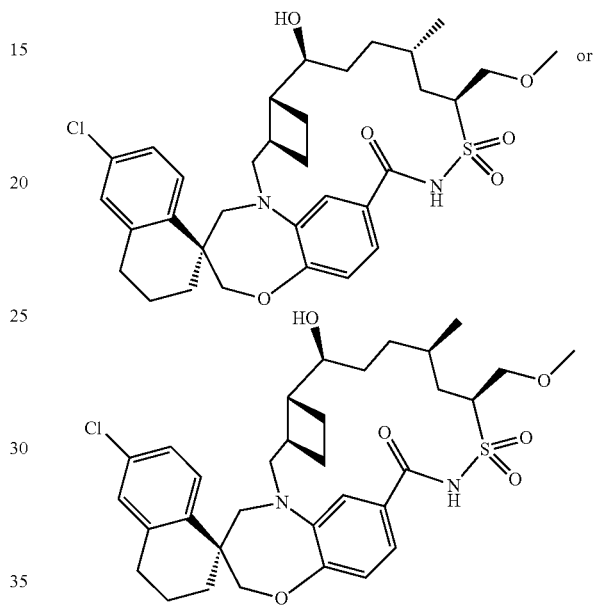

The title compound was prepared in an analogous manner to that described in Example 925, Step 1, using (1S,3'R,6'R,7'S,8'E,10'R,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 471), and the desired product, (1S,3'R,6'R,7'S,10'S,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S,10'R,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide was isolated. ¹H NMR (500 MHz, CD₃OD) δ 7.75 (d, J=8.4 Hz, 1H), 7.19 (dd, J=2.2, 8.6 Hz, 1H), 7.13 (d, J=2.2 Hz, 1H), 7.07 (dd, J=2.0, 8.1 Hz, 1H), 6.96 (d, J=8.3 Hz, 1H), 6.88 (d, J=1.7 Hz, 1H), 4.41-4.36 (m, 1H), 4.12 (dd, J=11.7, 20.3 Hz, 2H), 3.89 (dd, J=4.2, 9.8 Hz, 1H), 3.84-3.77 (m, 3H), 3.69 (d, J=13.9 Hz, 1H), 3.40 (s, 3H), 3.20 (d, J=14.2 Hz, 1H), 3.09 (dd, J=8.4, 15.5 Hz, 1H), 2.86-2.73 (m, 2H), 2.45-2.36 (m, 1H), 2.19-2.06 (m, 3H), 2.03-1.97 (m, 1H), 1.97-1.90 (m, 2H), 1.80-1.58 (m, 7H), 1.48 (t, J=11.7 Hz, 1H), 1.26-1.15 (m, 2H), 0.93 (d, J=5.6 Hz, 3H). m/z (ESI, +ve ion) 631.2 (M+H)⁺.

Example 1038. (1S,3'R,6'R,7'S,10'R,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide or (1S,3'R,6'R,7'S,10'S,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide Example 1039. (1S,3'R,6'R,7'S,8'E,10'S,12'S)-6-chloro-7'-(2-methoxyethoxy)-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,12'S)-6-chloro-7'-(2-methoxyethoxy)-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

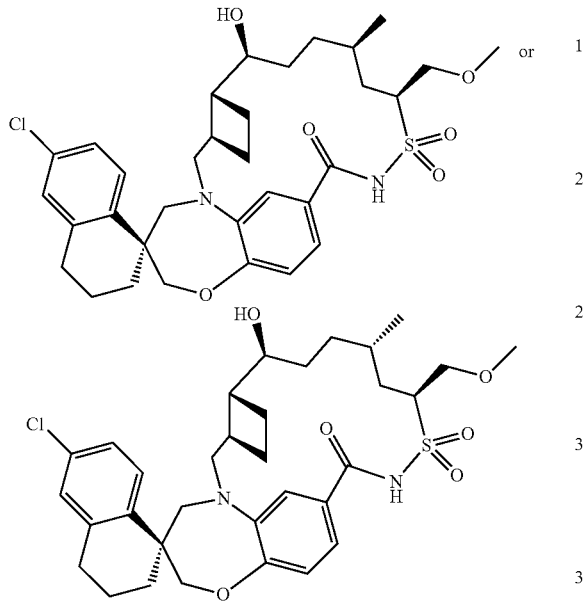

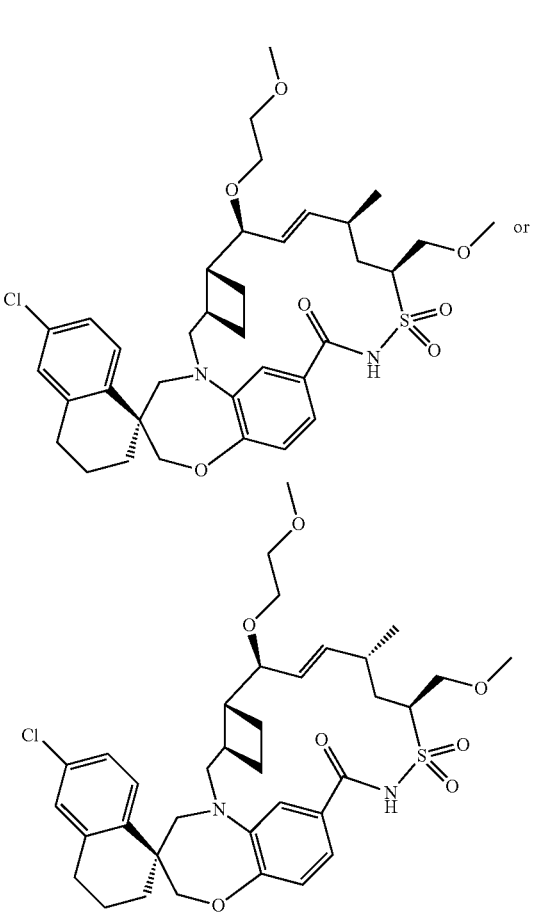

The title compound was prepared in an analogous manner to that described in Example 925, Step 1, using (1S,3'R,6'R,7'S,8'E,10'S,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 472), and the desired product, (1S,3'R,6'R,7'S,10'R,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S,10'S,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide was isolated. $^1$H NMR (500 MHz, CD$_3$OD) δ 7.77 (d, J=8.6 Hz, 1H), 7.21-7.17 (m, 2H), 7.13 (d, J=2.2 Hz, 1H), 7.05 (dd, J=2.0, 8.1 Hz, 1H), 6.92 (d, J=8.1 Hz, 1H), 4.11 (d, J=3.4 Hz, 2H), 4.09-4.05 (m, 1H), 3.96-3.85 (m, 3H), 3.74 (d, J=14.2 Hz, 1H), 3.53-3.43 (m, 2H), 3.42 (s, 2H), 3.41-3.39 (m, 1H), 3.38-3.35 (m, 2H), 3.31 (s, 3H), 3.11 (dd, J=7.2, 15.5 Hz, 1H), 2.86-2.74 (m, 2H), 2.70-2.63 (m, 1H), 2.50-2.43 (m, 1H), 2.09 (d, J=13.7 Hz, 1H), 1.99-1.85 (m, 5H), 1.80-1.63 (m, 5H), 1.72-1.62 (m, 3H), 1.59-1.50 (m, 2H), 1.50-1.42 (m, 1H), 0.94 (d, J=6.6 Hz, 3H). m/z (ESI, +ve ion) 631.2 (M+H)$^+$.

The title compound was prepared in an analogous manner to that described in Example 720 using (1S,3'R,6'R,7'S,8'E,10'S,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-7'-hydroxy-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 472) and 1-bromo-2-methoxyethane (Aldrich), and the desired product, (1S,3'R,6'R,7'S,8'E,10'S,12'S)-6-chloro-7'-(2-methoxyethoxy)-12'-(methoxymethyl)-10'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,12'S)-6-chloro-7'-(2-methoxyethoxy)-12'-(methoxymethyl)-10'-methyl-3, 4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide was isolated as a white solid. ¹H NMR (400 MHz, CD₃OD) δ 7.76 (d, J=8.6 Hz, 1H), 7.19 (dd, J=2.3, 8.6 Hz, 1H), 7.13 (d, J=2.2 Hz, 1H), 7.05 (dd, J=2.2, 8.2 Hz, 1H), 6.98 (d, J=2.0 Hz, 1H), 6.94 (d, J=8.2 Hz, 1H), 5.88 (dd, J=4.1, 15.8 Hz, 1H), 5.53 (ddd, J=1.8, 7.5, 15.8 Hz, 1H), 4.22 (dd, J=4.4, 10.1 Hz, 1H), 4.11 (s, 2H), 4.01 (dd, J=4.7, 11.2 Hz, 1H), 3.95 (dd, J=4.1, 11.3 Hz, 1H), 3.89 (dd, J=3.9, 8.4 Hz, 2H), 3.84 (s, 1H), 3.69 (d, J=14.5 Hz, 1H), 3.61-3.55 (m, 1H), 3.53-3.44 (m, 3H), 3.43 (s, 3H), 3.39-3.38 (m, 1H), 3.37 (s, 2H), 3.11 (dd, J=9.4, 15.5 Hz, 1H), 2.89-2.73 (m, 2H), 2.57-2.45 (m, 2H), 2.40-2.29 (m, 1H), 2.11 (d, J=13.9 Hz, 1H), 2.01-1.66 (m, 7H), 1.61 (t, J=12.9 Hz, 1H), 1.48 (t, J=12.7 Hz, 1H), 1.12 (d, J=6.7 Hz, 3H). m/z (ESI, +ve ion) 687.2 (M+H)⁺.

Example 1040. (1S,3'R,6'R,7'S,10'R,12'S)-6-chloro-7'-(2-methoxyethoxy)-12'-(methoxymethyl)-10'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'S,10'S,12'S)-6-chloro-7'-(2-methoxyethoxy)-12'-(methoxymethyl)-10'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide

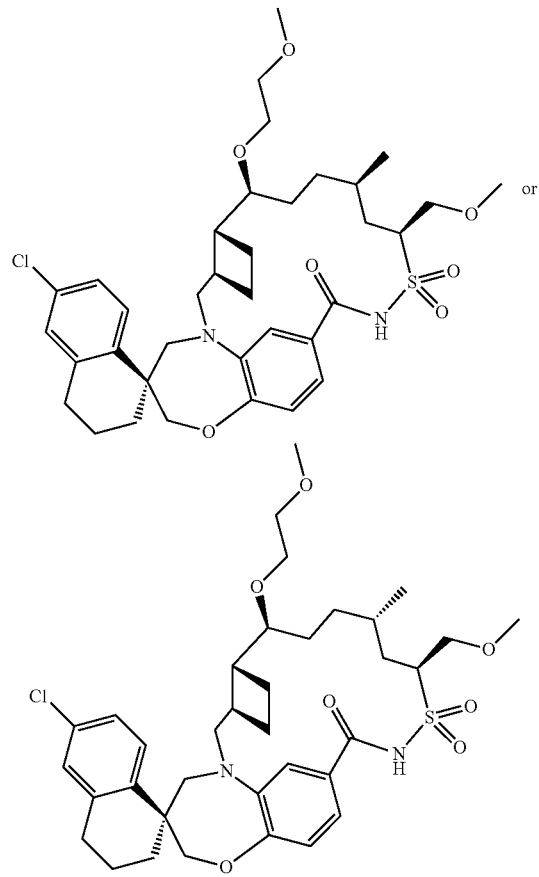

The title compound was prepared in an analogous manner to that described in Example 925, Step 1, using (1S,3'R,6'R, 7'S,8'E,10'S,12'S)-6-chloro-7'-(2-methoxyethoxy)-12'-(methoxymethyl)-10'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,12'S)-6-chloro-7'-(2-methoxyethoxy)-12'-(methoxymethyl)-10'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 1039), and the desired products, (1S,3'R,6'R,7'S,10'R,12'S)-6-chloro-7'-(2-methoxyethoxy)-12'-(methoxymethyl)-10'-methyl-3,4-dihydro-2H,15'H-spiro[naphthalene-1,22'-[20]oxa[13]thia[1,14]diazatetracyclo[[14.7.2.0³,⁶.0¹⁹,²⁴]pentacosa[16,18,24]trien]-15'-one 13',13'-dioxide or (1S,3'R,6'R,7'S,10'S,12'S)-6-chloro-7'-(2-methoxyethoxy)-12'-(methoxymethyl)-10'-methyl-3,4-dihydro-2H,15'H-spiro[naphthalene-1,22'-[20]oxa[13]thia[1,14]diazatetracyclo[[14.7.2.0³,⁶.0¹⁹,²⁴]pentacosa[16,18,24]trien]-15'-one 13',13'-dioxide was isolated. ¹H NMR (500 MHz, CD₃OD) δ 7.77 (d, J=8.6 Hz, 1H), 7.21-7.17 (m, 2H), 7.13 (d, J=2.2 Hz, 1H), 7.05 (dd, J=2.0, 8.1 Hz, 1H), 6.92 (d, J=8.1 Hz, 1H), 4.11 (d, J=3.4 Hz, 2H), 4.09-4.05 (m, 1H), 3.96-3.85 (m, 3H), 3.74 (d, J=14.2 Hz, 1H), 3.52-3.44 (m, 2H), 3.42 (s, 2H), 3.31 (s, 3H), 3.11 (dd, J=7.2, 15.5 Hz, 1H), 2.86-2.74 (m, 2H), 2.70-2.63 (m, 1H), 2.50-2.43 (m, 1H), 2.09 (d, J=13.7 Hz, 1H), 1.99-1.85 (m, 5H), 1.80-1.63 (m, 5H), 1.58-1.52 (m, 2H), 1.51-1.28 (m, 5H), 0.94 (d, J=6.6 Hz, 3H). m/z (ESI, +ve ion) 689.2 (M+H)⁺.

Example 1041. (1S,3'R,6'R,7'S,8'E,10'S,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide and Example 1042. (1S,3'R,6'R,7'S,8'E,10'R,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo14.7.2.0³,⁶.0¹⁹,²⁴]pentacosa[8,16,18,24]tetraen]-15'-one 13',13'-dioxide

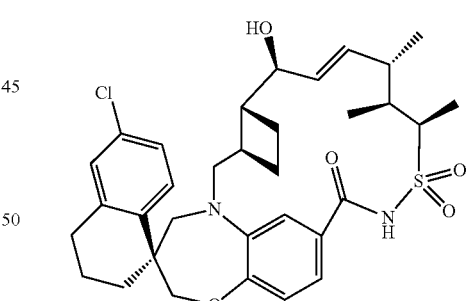

Example 1041

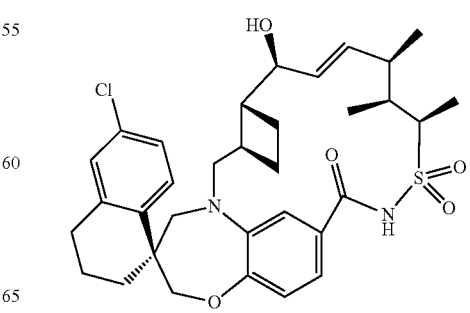

Example 1042

Step 1: (2S,3S,4S)-3,4-dimethylhex-5-en-2-ol, (2S,3S,4R)-3,4-dimethylhex-5-en-2-ol, (2R,3R,4S)-3,4-dimethylhex-5-en-2-ol and (2R,3R,4R)-3,4-dimethylhex-5-en-2-ol

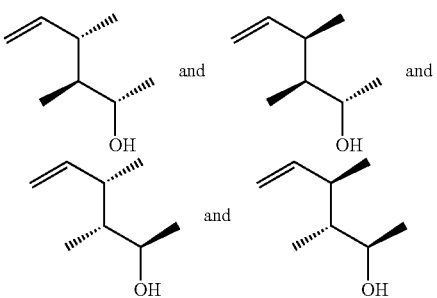

The title compounds were prepared in an analogous manner to that described in Example 1014, Step 1, but replacing (S)-2-methyloxirane with (2S, 3S)-2,3-dimethyl oxirane, and the desired products, a mixture of (2S,3S,4S)-3,4-dimethylhex-5-en-2-ol, (2S,3S,4R)-3,4-dimethylhex-5-en-2-ol, (2R,3R,4S)-3,4-dimethylhex-5-en-2-ol and (2R,3R,4R)-3,4-dimethylhex-5-en-2-ol were isolated and then submitted for DAS chiral speration to give a mixture of (2R,3R,4R)-3,4-dimethylhex-5-en-2-ol and (2R,3R,4S)-3,4-dimethylhex-5-en-2-ol as the first eluting major peak out of chiral chromagraphy, and another mixture of (2R,3S,4R)-3,4-dimethylhex-5-en-2-ol, (2R,3S,4S)-3,4-dimethylhex-5-en-2-ol as the second eluting major peak out of chiral chromagraphy.

Step 2: (1S,3'R,6'R,7'S,8'E,10'S,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo14.7.2.0$^{3,6}$.0$^{19,24}$]pentacosa[8,16,18,24]tetraen]-15'-one 13',13'-dioxide and (1S,3'R,6'R,7'S,8'E,10'R,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo14.7.2.0$^{3,6}$.0$^{19,24}$]pentacosa[8,16,18,24]tetraen]-15'-one 13',13'-dioxide The title compounds were prepared in an analogous manner to that described in Example 1014, Steps 2-4, using a mixture of (2R,3S,4R)-3,4-dimethylhex-5-en-2-ol, (2R,3S,4S)-3,4-dimethylhex-5-en-2-ol (Step 1, second eluting major peak) and the desired products, (1S,3'R,6'R,7'S,8'E,10'S,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (first eluting major peak out of reverse phase preparative HPLC) and (1S,3'R,6'R,7'S,8'E,10'R,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo14.7.2.0$^{3,6}$.0$^{19,24}$]pentacosa[8,16,18,24]tetraen]-15'-one 13',13'-dioxide (second eluting major peak out of reverse phase preparative HPLC) were isolated. (1S,3'R,6'R,7'S,8'E,10'S,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 1041). $^1$H NMR (500 MHz, CD$_3$OD) δ 7.75 (d, J=8.6 Hz, 1H), 7.18 (dd, J=2.0, 8.6 Hz, 1H), 7.12 (d, J=2.0 Hz, 1H), 7.07 (d, J=8.1 Hz, 1H), 6.94 (s, 1H), 6.92 (d, J=8.3 Hz, 1H), 5.95 (dd, J=6.5, 15.0 Hz, 1H), 5.64 (dd, J=8.3, 15.2 Hz, 1H), 4.20 (dd, J=3.3, 8.4 Hz, 1H), 4.11 (d, J=13.2 Hz, 3H), 3.83 (d, J=15.2 Hz, 1H), 3.64 (d, J=14.2 Hz, 1H), 3.10 (dd, J=9.8, 15.4 Hz, 1H), 2.87-2.71 (m, 2H), 2.55 (br. s., 1H), 2.47-2.34 (m, 1H), 2.33-2.17 (m, 2H), 2.11 (d, J=13.2 Hz, 1H), 2.00-1.77 (m, 6H), 1.72 (dd, J=10.0, 19.1 Hz, 1H), 1.51 (d, J=6.8 Hz, 3H), 1.49-1.43 (m, 1H), 1.09 (d, J=7.1 Hz, 3H), 1.07 (d, J=7.1 Hz, 3H). m/z (ESI, +ve ion) 613.2 (M+H); (1S,3'R,6'R,7'S,8'E,10'R,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 1042). $^1$H NMR (500 MHz, CD$_3$OD) δ 7.76 (d, J=8.6 Hz, 1H), 7.19 (dd, J=2.2, 8.3 Hz, 1H), 7.15-7.10 (m, 2H), 7.05 (d, J=1.2 Hz, 1H), 6.96 (d, J=8.1 Hz, 1H), 5.77 (dd, J=5.5, 15.8 Hz, 1H), 5.64 (dd, J=7.8, 15.7 Hz, 1H), 4.35 (dd, J=2.2, 6.6 Hz, 1H), 4.21-4.09 (m, 3H), 3.82 (d, J=15.4 Hz, 1H), 3.65 (d, J=13.9 Hz, 1H), 3.17 (dd, J=9.3, 16.1 Hz, 1H), 2.86-2.74 (m, 2H), 2.39 (dd, J=7.6, 17.6 Hz, 1H), 2.32-2.22 (m, 1H), 2.13-2.03 (m, 2H), 2.03-1.93 (m, 3H), 1.93-1.67 (m, 5H), 1.53-1.45 (m, 1H), 1.39 (d, J=7.1 Hz, 3H), 1.10 (d, J=6.8 Hz, 3H), 1.07 (d, J=6.8 Hz, 3H). m/z (ESI, +ve ion) 613.2 (M+H).

Example 1043. (1S,3'R,6'R,7'S,8'E,10'S,11'R,12'S)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or
Example 1044. (1S,3'R,6'R,7'S,8'E,10'R,11'R,12'S)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

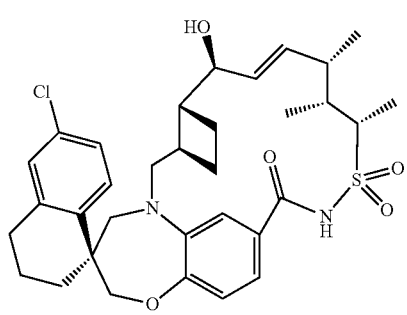

Example 1043

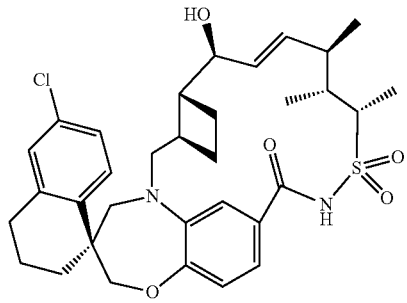

Example 1044

The title compounds were prepared in an analogous manner to that described in Example 1041 Step 2 using a mixture of (2R,3R,4R)-3,4-dimethylhex-5-en-2-ol and (2R, 3R,4S)-3,4-dimethylhex-5-en-2-ol (Example 1041, Step 1, the first eluting major peak out of chiral chromagraphy), and the desired product, (1S,3'R,6'R,7'S,8'E,10'S,11'R,12'S)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 1043, first eluting major isomer out of reverse phase preparative HPLC) was isolated. $^1$H NMR (500 MHz, CD$_3$OD) δ 7.73 (d, J=8.3 Hz, 1H), 7.42 (br. s., 1H), 7.19 (dd, J=2.2, 8.6 Hz, 1H), 7.13 (d, J=2.2 Hz, 1H), 7.07 (d, J=7.6 Hz, 1H), 6.93 (d, J=7.6 Hz, 1H), 5.92 (dd, J=6.1, 15.9 Hz, 1H), 5.65-5.59 (m, 1H), 4.17 (dd, J=12.2, 15.2 Hz, 2H), 4.01-3.89 (m, 2H), 3.80-3.66 (m, 1H), 3.51 (dd, J=14.2, 26.2 Hz, 2H), 2.84-2.74 (m, 2H), 2.55 (br. s., 2H), 2.50-2.37 (m, 1H), 2.23 (dd, J=3.3, 7.0 Hz, 1H), 2.01-1.59 (m, 9H), 1.50 (d, J=7.3 Hz, 3H), 1.09 (d, J=7.1 Hz, 3H), 1.06 (d, J=7.1 Hz, 3H). m/z (ESI, +ve ion) 613.2 (M+H). (1S,3'R,6'R,7'S,8'E,10'R,11'R,12'S)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 1044, second eluting peak out of reverse phase preparative HPLC) was isolated. $^1$H NMR (500 MHz, CD$_3$OD) δ 7.72 (d, J=8.3 Hz, 1H), 7.48 (br. s., 1H), 7.19 (dd, J=2.1, 8.4 Hz, 1H), 7.15-7.11 (m, 2H), 6.94 (d, J=8.0 Hz, 1H), 5.69 (dd, J=6.0, 15.8 Hz, 1H), 5.53-5.33 (m, 1H), 4.22 (dd, J=0.5, 10.8 Hz, 2H), 4.00-3.88 (m, 2H), 3.85-3.73 (m, 1H), 3.64-3.57 (m, 1H), 3.57-3.46 (m, 1H), 2.84-2.74 (m, 2H), 2.63-2.52 (m, 1H), 2.52-2.39 (m, 1H), 2.10-2.01 (m, 2H), 2.01-1.92 (m, 2H), 1.92-1.80 (m, 4H), 1.76-1.62 (m, 2H), 1.55 (d, J=10.0 Hz, 1H), 1.39 (d, J=7.3 Hz, 3H), 1.07 (d, J=6.6 Hz, 3H), 0.99 (d, J=5.9 Hz, 3H). m/z (ESI, +ve ion) 613.2 (M+H).

Example 1045. (1S,3'R,6'R,7'S,10'S,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

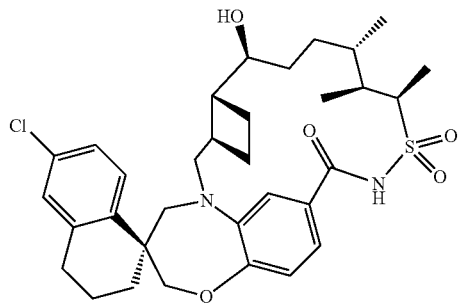 [SMILES: C[C@@H]1[C@@H](C)S(=O)(=O)NC(=O)c2ccc3c(c2)N(C[C@@H]2CC[C@H]2[C@@H](O)CC[C@@H]1C)C[C@@]1(CCCc2cc(Cl)ccc21)CO3]

The title compound was prepared in an analogous manner to that described in Example 925, Step 1, using (1S,3'R,6'R,7'S,8'E,10'S,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 1041), and the desired products, (1S,3'R,6'R,7'S,10'S,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide was isolated. $^1$H NMR (500 MHz, CD$_3$OD) δ 7.76 (d, J=8.6 Hz, 1H), 7.19 (dd, J=2.4, 7.1 Hz, 2H), 7.12 (d, J=2.0 Hz, 1H), 7.06 (dd, J=2.0, 8.1 Hz, 1H), 6.93 (d, J=8.1 Hz, 1H), 4.11 (dd, J=12.2, 18.1 Hz, 2H), 4.01 (dq, J=2.7, 7.2 Hz, 1H), 3.86 (dd, J=5.1, 15.4 Hz, 1H), 3.73 (d, J=14.2 Hz, 1H), 3.62-3.58 (m, 1H), 3.16 (dd, J=6.8, 15.7 Hz, 1H), 2.86-2.74 (m, 2H), 2.55-2.49 (m, 1H), 2.43-2.38 (m, 1H), 2.23-2.18 (m, 1H), 2.10 (d, J=13.7 Hz, 1H), 2.05-1.99 (m, 1H), 1.95-1.86 (m, 3H), 1.71-1.63 (m, 2H), 1.54 (dd, J=3.8, 7.2 Hz, 1H), 1.49 (br. s., 1H), 1.46 (d, J=7.1 Hz, 3H), 1.45-1.23 (m, 4H), 1.09 (d, J=7.1 Hz, 3H), 0.91 (d, J=6.8 Hz, 3H). m/z (ESI, +ve ion) 615.2 (M+H)$^+$.

Example 1046. (1S,3'R,6'R,7'S,10'R,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [16,18,24]trien]-15'-one 13',13'-dioxide

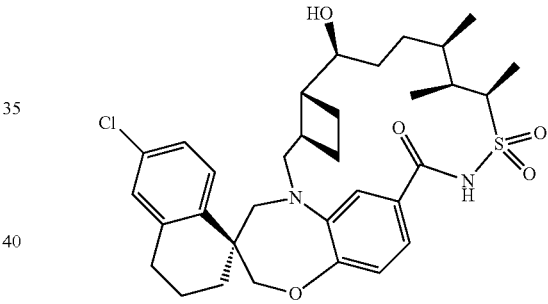

The title compound was prepared in an analogous manner to that described in Example 925, Step 1, using (1S,3'R,6'R,7'S,8'E,10'R,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 1042), and the desired products, (1S,3'R,6'R,7'S,10'R,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide was isolated. $^1$H NMR (400 MHz, CD$_3$OD) δ 7.64 (d, J=8.6 Hz, 1H), 7.07 (dd, J=2.2, 8.4 Hz, 1H), 7.00 (dt, J=2.1, 4.1 Hz, 2H), 6.89 (d, J=1.8 Hz, 1H), 6.84 (d, J=8.0 Hz, 1H), 4.04-3.97 (m, 3H), 3.71 (d, J=15.1 Hz, 1H), 3.64 (d, J=8.2 Hz, 1H), 3.54 (d, J=13.7 Hz, 1H), 3.08-2.92 (m, 1H), 2.74-2.61 (m, 2H), 2.27 (d, J=7.2 Hz, 2H), 2.00-1.87 (m, 2H), 1.83-1.76 (m, 2H), 1.76-1.48 (m, 6H), 1.42-1.33 (m, 2H), 1.31 (d, J=7.2 Hz, 3H), 1.29-1.23 (m, 3H), 0.92 (d, J=6.8 Hz, 3H), 0.82 (d, J=6.8 Hz, 3H). m/z (ESI, +ve ion) 615.2 (M+H)$^+$.

Example 1047. (1S,3'R,6'R,7'S,8'E,10'S,11'S,12'R)-6-chloro-7'-methoxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

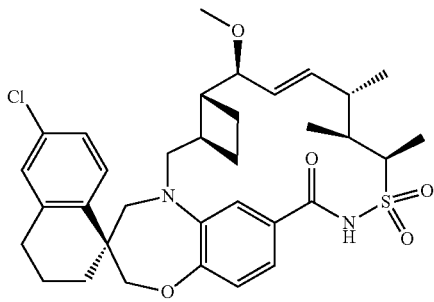 [SMILES: CO[C@H]1/C=C/[C@H](C)[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

The title compound was prepared in an analogous manner to that described in Example 720 using (1S,3'R,6'R,7'S,8'E,10'S,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[[14.7.2.0$^{3,6}$.0$^{19,24}$]pentacosa[8,16,18,24]tetra en]-15'-one 13',13'-dioxide (Example 1041) and iodomethane, and the desired product, (1S,3'R,6'R,7'S,8'E,10'S,11'S,12'R)-6-chloro-7'-methoxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (400 MHz, CD$_3$OD) δ 7.75 (d, J=8.4 Hz, 1H), 7.19 (dd, J=2.2, 8.5 Hz, 1H), 7.13 (d, J=2.3 Hz, 1H), 7.05 (dd, J=2.0, 8.0 Hz, 1H), 6.94 (d, J=8.2 Hz, 1H), 6.90 (d, J=2.0 Hz, 1H), 6.01 (dd, J=6.8, 15.5 Hz, 1H), 5.50 (dd, J=9.0, 15.5 Hz, 1H), 4.35-4.11 (m, 2H), 4.10 (s, 2H), 3.83 (d, J=15.5 Hz, 1H), 3.73 (dd, J=3.3, 9.0 Hz, 1H), 3.65 (d, J=14.1 Hz, 1H), 3.24 (s, 3H), 3.10 (dd, J=10.0, 15.3 Hz, 1H), 2.87-2.73 (m, 2H), 2.62 (br. s., 1H), 2.53-2.44 (m, 1H), 2.37-2.28 (m, 1H), 2.25 (dt, J=3.6, 6.9 Hz, 1H), 2.11 (d, J=13.7 Hz, 1H), 2.00-1.65 (m, 6H), 1.54 (d, J=7.0 Hz, 3H), 1.47 (t, J=12.5 Hz, 1H), 1.12 (d, J=2.0 Hz, 3H), 1.10 (d, J=1.8 Hz, 3H). m/z (ESI, +ve ion) 627.2 (M+H)$^+$.

Example 1048. (1S,3'R,6'R,7'S,8'E,10'S,11'S,12'R)-6-chloro-7'-(2-methoxyethoxy)-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

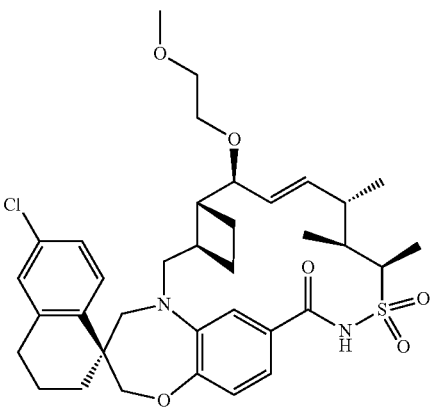 [SMILES: COCCO[C@H]1/C=C/[C@H](C)[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

The title compound was prepared in an analogous manner to that described in Example 720 using (1S,3'R,6'R,7'S,8'E,10'S,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 1041) and 1-bromo-2-methoxyethane (Aldrich), and the desired product, (1S,3'R,6'R,7'S,8'E,10'S,11'S,12'R)-6-chloro-7'-(2-methoxyethoxy)-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (500 MHz, CD$_3$OD) δ 7.63 (d, J=8.6 Hz, 1H), 7.06 (dd, J=2.2, 8.6 Hz, 1H), 7.00 (d, J=2.2 Hz, 1H), 6.93 (dd, J=1.6, 8.2 Hz, 1H), 6.80 (dd, J=4.6, 4463.4 Hz, 2H), 5.87 (dd, J=9.0, 15.4 Hz, 1H), 5.39 (dd, J=9.0, 15.6 Hz, 1H), 4.00 (dd, J=3.4, 7.1 Hz, 1H), 3.97 (s, 2H), 3.74 (dd, J=3.5, 9.2 Hz, 1H), 3.69 (d, J=14.7 Hz, 1H), 3.53 (d, J=14.4 Hz, 1H), 3.49-3.29 (m, 5H), 3.25 (s, 3H), 2.97 (dd, J=9.7, 15.3 Hz, 1H), 2.74-2.60 (m, 2H), 2.57-2.46 (m, 1H), 2.42-2.35 (m, 1H), 2.27-2.09 (m, 2H), 1.99 (d, J=13.4 Hz, 1H), 1.87-1.68 (m, 5H), 1.60 (dd, J=9.8, 19.1 Hz, 1H), 1.40 (d, J=7.1 Hz, 3H), 1.37-1.30 (m, 1H), 0.97 (d, J=7.1 Hz, 6H). m/z (ESI, +ve ion) 671.4 (M+H)$^+$.

2063

Example 1049. (1S,3'R,6'R,7'S,8'E,10'S,11'S,12'R)-6-chloro-10',11',12'-trimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

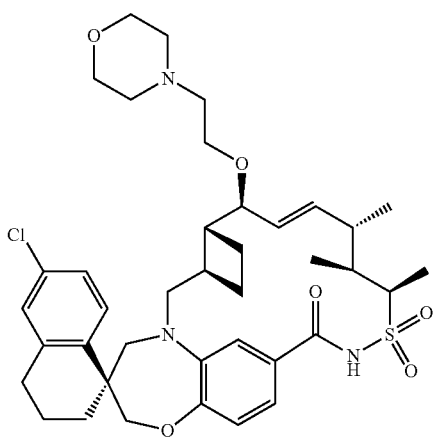 [SMILES: C[C@@H]1[C@@H](C)S(=O)(=O)NC(=O)c2ccc3c(c2)N(C[C@@H]2CC[C@H]2[C@@H](OCCN2CCOCC2)/C=C/[C@@H]1C)C[C@@]1(CCCc2cc(Cl)ccc21)CO3]

The title compound was prepared in an analogous manner to that described in Example 720 using (1S,3'R,6'R,7'S,8'E,10'S,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 1041) and 4-(2-bromoethyl)morpholine (Aldrich), and the desired product, (1S,3'R,6'R,7'S,8'E,10'S,11'S,12'R)-6-chloro-10',11',12'-trimethyl-7'-(2-(4-morpholinyl)ethoxy)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (400 MHz, CD$_3$OD) δ 7.77 (d, J=8.4 Hz, 1H), 7.19 (dd, J=2.2, 8.3 Hz, 1H), 7.15-7.11 (m, 1H), 7.09 (dd, J=1.8, 8.4 Hz, 1H), 6.94 (d, J=1.8 Hz, 1H), 6.88 (d, J=7.8 Hz, 1H), 6.14 (dd, J=6.5, 15.8 Hz, 1H), 5.50 (dd, J=9.2, 15.7 Hz, 1H), 4.16-4.09 (m, 1H), 4.07 (s, 2H), 3.89 (dd, J=3.0, 8.9 Hz, 1H), 3.84 (d, J=14.5 Hz, 1H), 3.79 (t, J=4.7 Hz, 4H), 3.69 (dd, J=5.1, 11.2 Hz, 1H), 3.64 (d, J=13.7 Hz, 1H), 3.55-3.48 (m, 1H), 3.40-3.33 (m, 2H overlap with solvent), 3.09 (dd, J=9.8, 15.7 Hz, 1H), 2.86-2.72 (m, 8H), 2.58-2.19 (m, 3H), 2.12 (d, J=12.7 Hz, 1H), 1.99-1.91 (m, 2H), 1.91-1.64 (m, 4H), 1.50 (d, J=7.0 Hz, 3H), 1.48-1.41 (m, 1H), 1.09 (d, J=7.2 Hz, 3H), 1.06 (d, J=7.0 Hz, 3H). m/z (ESI, +ve ion) 726.3 (M+H)$^+$.

2064

Example 1050. ethyl (((1S,3'R,6'R,7'S,8'E,10'S,11'S,12'R)-6-chloro-10',11',12'-trimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)oxy)acetate

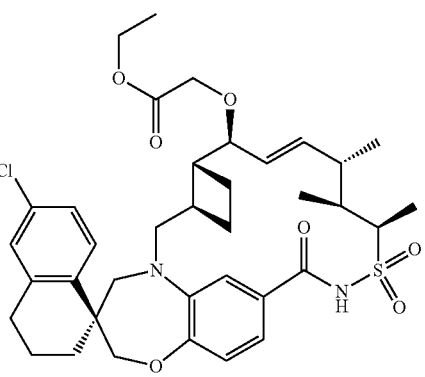

The title compound was prepared in an analogous manner to that described in Example 720 using (1S,3'R,6'R,7'S,8'E,10'S,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 1041) and ethyl acrylate, and the desired product, ethyl (((1S,3'R,6'R,7'S,8'E,10'S,11'S,12'R)-6-chloro-10',11',12'-trimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)oxy)acetate was isolated as a white solid. $^1$H NMR (400 MHz, CD$_3$OD) δ 7.75 (d, J=8.4 Hz, 1H), 7.19 (dd, J=2.2, 8.5 Hz, 1H), 7.13 (d, J=2.2 Hz, 1H), 7.04 (dd, J=2.0, 8.2 Hz, 1H), 6.94 (d, J=8.0 Hz, 1H), 6.89 (d, J=2.0 Hz, 1H), 5.97 (dd, J=6.8, 15.5 Hz, 1H), 5.54 (dd, J=8.1, 15.4 Hz, 1H), 4.26-4.18 (m, 2H), 4.13 (dd, J=3.1, 7.2 Hz, 1H), 4.11 (s, 2H), 4.02 (d, J=2.2 Hz, 2H), 3.95 (dd, J=3.5, 9.0 Hz, 1H), 3.82 (d, J=15.3 Hz, 1H), 3.65 (d, J=13.9 Hz, 1H), 3.12 (dd, J=9.6, 15.3 Hz, 1H), 2.87-2.73 (m, 2H), 2.63-2.55 (m, 2H), 2.32 (t, J=9.2 Hz, 1H), 2.27-2.20 (m, 1H), 2.11 (d, J=13.3 Hz, 1H), 2.01-1.83 (m, 5H), 1.76 (dd, J=9.4, 18.4 Hz, 1H), 1.54 (d, J=7.0 Hz, 3H), 1.52-1.44 (m, 1H), 1.31 (t, J=7.1 Hz, 4H), 1.10 (t, J=6.6 Hz, 6H). m/z (ESI, +ve ion) 699.2 (M+H)$^+$.

Example 1051. ((((1S,3'R,6'R,7'S,8'E,10'S,11'S, 12'R)-6-chloro-10',11',12'-trimethyl-13',13'-dioxido-15'-oxo-3,4-dihydro-2H-spiro[naphthalene-1,22'-[20]oxa[13]thia[1,14]diazatetracyclo[14.7.2.0^{3,6}.0^{19,24}]pentacosa [8,16,18,24]tetraen]-7'-yl)oxy)acetic Acid

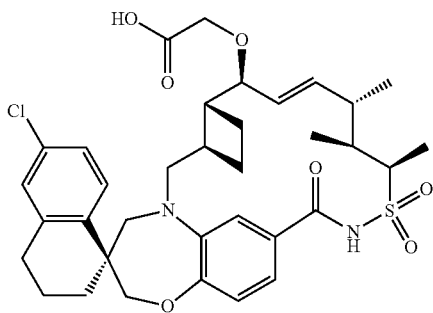 [SMILES: C[C@@H]1[C@@H](C)S(=O)(=O)NC(=O)c2ccc3c(c2)N(C[C@@H]2CC[C@H]2[C@@H](OCC(=O)O)/C=C/[C@@H]1C)C[C@@]1(CCCc2cc(Cl)ccc21)CO3]

The title compound was prepared in an analogous manner to that described in Example 992 using ethyl ((((1S,3'R,6'R, 7'S,8'E,10'S,11'S,12'R)-6-chloro-10',11',12'-trimethyl-13', 13'-dioxido-15'-oxo-3,4-dihydro-2H-spiro[naphthalene-1, 22'-[20]oxa[13]thia[1,14]diazatetracyclo[14.7.2.0^{3,6}.0^{19,24}] pentacosa[8,16,18,24]tetraen]-7'-yl)oxy)acetate (Example 1050), and the desired product, ((((1S,3'R,6'R,7'S,8'E,10'S, 11'S,12'R)-6-chloro-10',11',12'-trimethyl-13',13'-dioxido-15'-oxo-3,4-dihydro-2H-spiro[naphthalene-1,22'-[20]oxa [13]thia[1,14]diazatetracyclo[14.7.2.0^{3,6}.0^{19,24}]pentacosa [8,16,18,24]tetraen]-7'-yl)oxy)acetic acid was isolated as a white solid. $^1$H NMR (500 MHz, CD$_3$OD) δ 7.74 (d, J=8.6 Hz, 1H), 7.19 (dd, J=2.3, 8.4 Hz, 1H), 7.12 (d, J=2.2 Hz, 1H), 7.03 (dd, J=2.0, 8.1 Hz, 1H), 6.93 (d, J=8.1 Hz, 1H), 6.88 (d, J=1.7 Hz, 1H), 5.99 (dd, J=6.8, 15.4 Hz, 1H), 5.55 (dd, J=9.3, 15.4 Hz, 1H), 4.16-4.11 (m, 1H), 4.10 (s, 2H), 3.99 (d, J=4.2 Hz, 2H), 3.97-3.94 (m, 1H), 3.83 (d, J=15.2 Hz, 1H), 3.65 (d, J=14.2 Hz, 1H), 3.11 (dd, J=9.7, 15.3 Hz, 1H), 2.86-2.73 (m, 2H), 2.63-2.56 (m, 2H), 2.31 (t, J=9.2 Hz, 1H), 2.26-2.20 (m, 1H), 2.11 (d, J=13.4 Hz, 1H), 2.00-1.80 (m, 6H), 1.78-1.70 (m, 1H), 1.54 (d, J=7.1 Hz, 3H), 1.51-1.40 (m, 1H), 1.10 (d, J=7.1 Hz, 6H). m/z (ESI, +ve ion) 671.2 (M+H)$^+$.

Example 1052. 2-((((1S,3'R,6'R,7'S,8'E,10'S,11'S, 12'R)-6-chloro-10',11',12'-trimethyl-13',13'-dioxido-15'-oxo-3,4-dihydro-2H-spiro[naphthalene-1,22'-[20]oxa[13]thia[1,14]diazatetracyclo[14.7.2.0^{3,6}.0^{19,24}]pentacosa [8,16,18,24]tetraen]-7'-yl)oxy)-N, N-dimethylacetamide

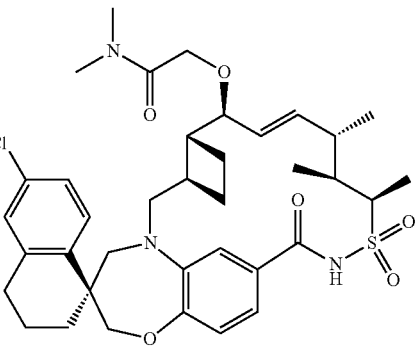

The title compound was prepared in an analogous manner to that described in Example 995 using ((((1S,3'R,6'R,7'S, 8'E,10'S,11'S,12'R)-6-chloro-10',11',12'-trimethyl-13',13'-dioxido-15'-oxo-3,4-dihydro-2H-spiro[naphthalene-1,22'-[20]oxa[13]thia[1,14]diazatetracyclo[14.7.2.0^{3,6}.0^{19,24}] pentacosa[8,16,18,24]tetraen]-7'-yl)oxy)acetic acid (Example 1051) and dimethylamine (40 wt % solution in water, Acros), and the desired product, 2-((((1S,3'R,6'R,7'S, 8'E,10'S,11'S,12'R)-6-chloro-10',11',12'-trimethyl-13',13'-dioxido-15'-oxo-3,4-dihydro-2H-spiro[naphthalene-1,22'-[20]oxa[13]thia[1,14]diazatetracyclo[14.7.2.0^{3,6}.0^{19,24}] pentacosa[8,16,18,24]tetraen]-7'-yl)oxy)-N,N-dimethylacetamide was isolated as a white solid. $^1$H NMR (400 MHz, CD$_3$OD) δ 7.75 (d, J=8.4 Hz, 1H), 7.19 (dd, J=2.2, 8.5 Hz, 1H), 7.13 (d, J=2.2 Hz, 1H), 7.04 (dd, J=2.0, 8.2 Hz, 1H), 6.94 (d, J=8.0 Hz, 1H), 6.89 (d, J=1.8 Hz, 1H), 6.01 (dd, J=6.7, 15.4 Hz, 1H), 5.56 (dd, J=8.7, 15.9 Hz, 1H), 4.22-4.03 (m, 6H), 3.92 (dd, J=3.3, 9.2 Hz, 1H), 3.84 (d, J=15.5 Hz, 1H), 3.65 (d, J=13.9 Hz, 1H), 3.18-3.08 (m, 1H), 3.04 (s, 3H), 2.97 (s, 3H), 2.88-2.71 (m, 3H), 2.64-2.56 (m, 2H), 2.36-2.20 (m, 2H), 2.11 (d, J=13.1 Hz, 1H), 2.01-1.88 (m, 4H), 1.75 (dd, J=9.2, 17.8 Hz, 1H), 1.54 (d, J=7.0 Hz, 3H), 1.47 (t, J=12.9 Hz, 1H), 1.11 (d, J=1.6 Hz, 3H), 1.10 (d, J=1.6 Hz, 3H). m/z (ESI, +ve ion) 698.3 (M+H)$^+$.

Example 1053. (1S,3'R,6'R,7'S,8'E,10'R,11'S,12'R)-6-chloro-7'-methoxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide Example 1054. (1S,3'R,6'R,7'S,8'E,10'S,11'S,12'R)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide or (1S,3'R,6'R,7'S,8'E,10'R,11'S,12'R)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide or (1S,3'R,6'R,7'S,8'E,10'S,11'R,12'S)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide or (1S,3'R,6'R,7'S,8'E,10'R,11'R,12'S)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$] pentacosa [8,16,18,24]tetraen]-15'-one 13',13'-dioxide

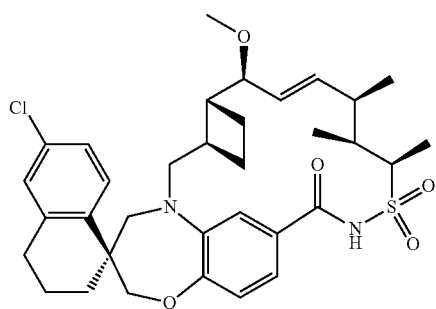 [SMILES: CO[C@H]1/C=C/[C@@H](C)[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

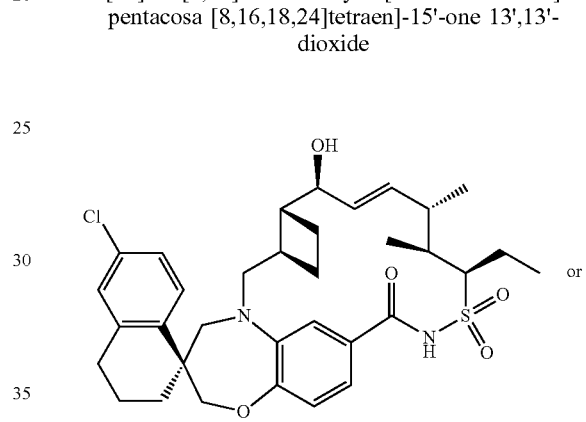

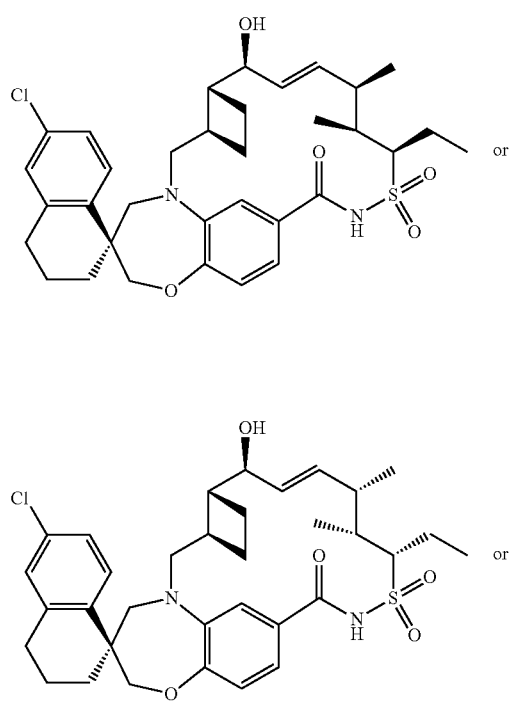

The title compound was prepared in an analogous manner to that described in Example 720 using (1S,3'R,6'R,7'S,8'E,10'R,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 1042) and methyl iodide, and the desired product, (1S,3'R,6'R,7'S,8'E,10'R,11'S,12'R)-6-chloro-7'-methoxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as a white solid. $^1$H NMR (500 MHz, CD$_3$OD) δ 7.76 (d, J=8.6 Hz, 1H), 7.19 (dd, J=2.2, 8.3 Hz, 1H), 7.15-7.10 (m, 2H), 7.05 (d, J=1.2 Hz, 1H), 6.96 (d, J=8.1 Hz, 1H), 6.10 (dd, J=4.1, 15.8 Hz, 1H), 5.46 (dd, J=9.0, 16.4 Hz, 1H), 4.35 (dd, J=2.2, 6.6 Hz, 1H), 4.21-4.09 (m, 3H), 3.82 (d, J=15.4 Hz, 1H), 3.65 (d, J=13.9 Hz, 1H), 3.24 (s, 3H), 3.17 (dd, J=9.3, 16.1 Hz, 1H), 2.86-2.74 (m, 2H), 2.39 (dd, J=7.6, 17.6 Hz, 1H), 2.32-2.22 (m, 1H), 2.13-2.03 (m, 2H), 2.03-1.93 (m, 3H), 1.93-1.67 (m, 5H), 1.53-1.45 (m, 1H), 1.39 (d, J=7.1 Hz, 3H), 1.10 (d, J=6.8 Hz, 3H), 1.07 (d, J=6.8 Hz, 3H). m/z (ESI, +ve ion) 627.2 (M+H)$^+$.

-continued

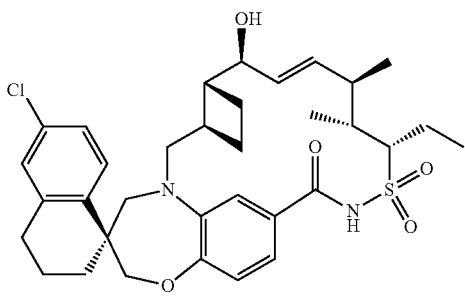

The title compounds were prepared in an analogous manner to that described in Example 1041, Steps 1 to 3, but replacing the mixture of (1S,2S)-1,2-dimethyloxirane and (1R,2R)-1,2-dimethyloxirane with a mixture of (2S,3S)-2-ethyl-3-methyloxirane and (1R,2R)-1-ethyl-2-methylcyclopropane (perpared according to the procedure by Hobson, Lindsay A. et al.; Organic and Biomolecular Chemistry, 2012, vol. 10, #37 p. 7510-7526) in Step 1, and the desired product, (1S,3'R,6'R,7'S,8'E,10'S,11'S,12'R)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,11'S,12'R)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,11'R,12'S)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,11'R,12'S)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide was isolated (first eluting major isomer out of preparative reverse phase HPLC). $^1$H NMR (400 MHz, CD$_3$OD) δ 7.75 (d, J=8.6 Hz, 1H), 7.19 (dd, J=2.2, 8.6 Hz, 1H), 7.12 (d, J=2.2 Hz, 1H), 7.04 (dd, J=1.7, 8.1 Hz, 1H), 6.92 (d, J=8.0 Hz, 2H), 5.95 (dd, J=6.5, 15.7 Hz, 1H), 5.63 (dd, J=8.1, 14.6 Hz, 1H), 4.21 (dd, J=3.5, 8.6 Hz, 1H), 4.09 (s, 2H), 3.96 (dd, J=4.9, 9.6 Hz, 1H), 3.83 (d, J=14.3 Hz, 1H), 3.65 (d, J=14.3 Hz, 1H), 3.10 (dd, J=9.8, 15.1 Hz, 1H), 2.89-2.69 (m, 2H), 2.63 (br. s., 1H), 2.46-2.36 (m, 1H), 2.35-2.23 (m, 2H), 2.17-2.04 (m, 3H), 1.99-1.65 (m, 7H), 1.51-1.42 (m, 1H), 1.26-1.21 (m, 3H), 1.09 (d, J=7.2 Hz, 3H), 1.06 (d, J=7.0 Hz, 3H). m/z (ESI, +ve ion) 627.2 (M+H)$^+$.

Example 1055. (1S,3'R,6'R,7'S,8'E,10'R,11'S,12'R)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,11'S,12'R)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'S,11'R,12'S)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,11'R,12'S)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

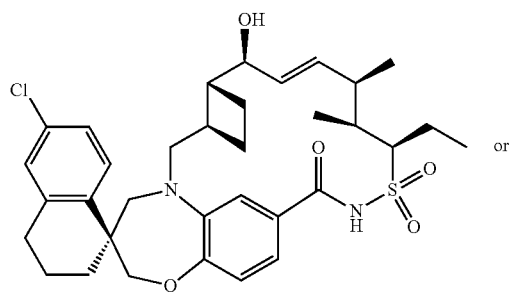

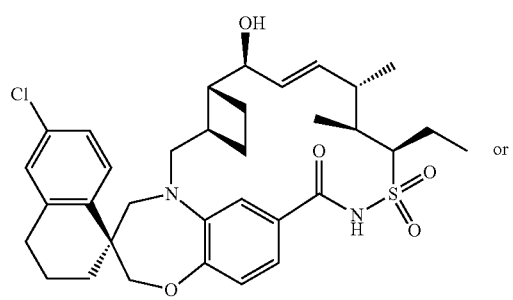

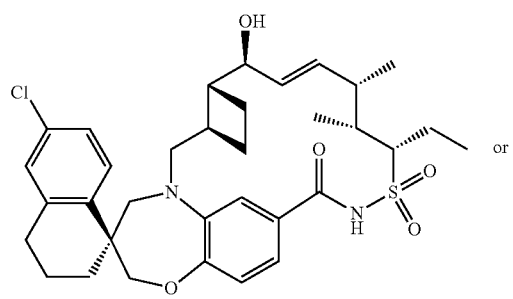

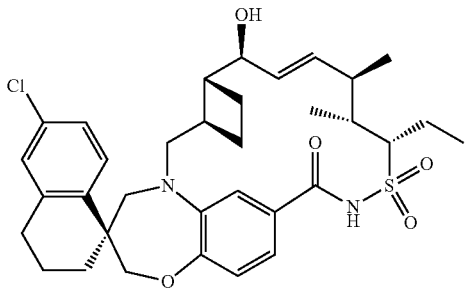

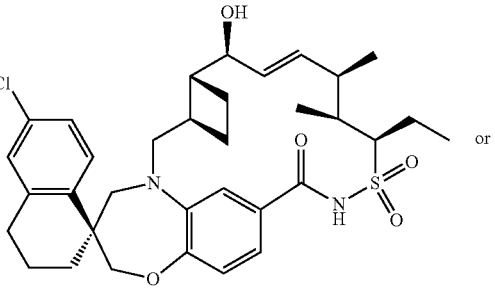

The title compound was obtained as a single isomer (second eluting major peak) from the reverse phase preparative HPLC in Example 1054. $^1$H NMR (400 MHz, CD$_3$OD) δ 7.76 (d, J=8.4 Hz, 1H), 7.19 (dd, J=2.2, 8.5 Hz, 1H), 7.11 (dd, J=2.0, 8.0 Hz, 2H), 7.05 (d, J=2.0 Hz, 1H), 6.96 (d, J=8.0 Hz, 1H), 5.77 (dd, J=6.1, 15.7 Hz, 1H), 5.61 (ddd, J=1.6, 6.7, 16.0 Hz, 1H), 4.35 (dd, J=2.9, 7.4 Hz, 1H), 4.14 (dd, J=12.3, 18.4 Hz, 2H), 3.99 (dd, J=4.8, 7.7 Hz, 1H), 3.84 (d, J=15.3 Hz, 1H), 3.66 (d, J=14.1 Hz, 1H), 3.20-3.10 (m, 1H), 2.88-2.73 (m, 2H), 2.47-2.33 (m, 1H), 2.33-2.19 (m, 1H), 2.19-1.92 (m, 6H), 1.92-1.69 (m, 6H), 1.53-1.44 (m, 1H), 1.25 (t, J=7.4 Hz, 3H), 1.11 (d, J=6.8 Hz, 3H), 1.06 (d, J=6.8 Hz, 3H). m/z (ESI, +ve ion) 627.2 (M+H)$^+$.

Example 1056. (1S,3'R,6'R,7'S,8'E,10'S,11'R,12'S)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,11'S,12'R)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'R,11'R,12'S)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,10'S,11'S,12'R)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

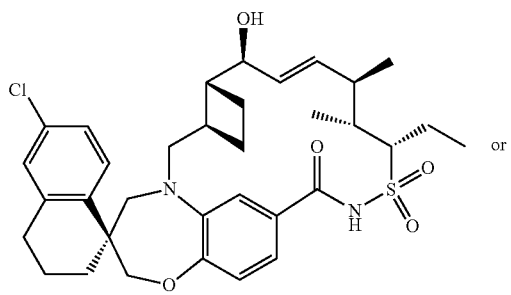

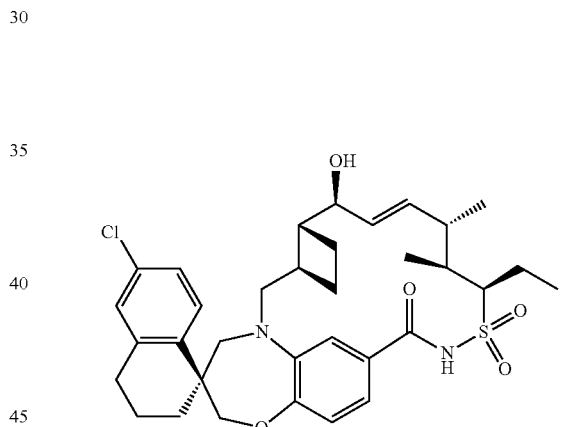

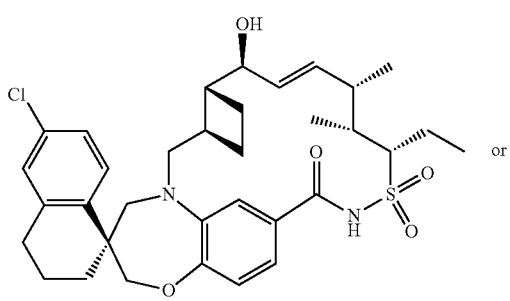

The title compound was obtained as a single isomer (third eluting peak) from the reverse phase preparative HPLC in Example 1054. $^1$H NMR (400 MHz, CD$_3$OD) δ 7.74 (d, J=3893.7 Hz, 1H), 7.19 (dd, J=2.2, 8.5 Hz, 2H), 7.13 (d, J=2.3 Hz, 1H), 7.10 (d, J=8.2 Hz, 1H), 6.94 (d, J=8.4 Hz, 1H), 6.01 (dd, J=5.2, 15.2 Hz, 1H), 5.63-5.58 (m, 1H), 4.19-4.11 (m, 1H), 4.07-4.01 (m, 1H), 3.80 (q, J=4.8 Hz, 1H), 3.64-3.43 (m, 4H), 2.86-2.73 (m, 2H), 2.69 (br. s., 1H), 2.60 (br. s., 1H), 2.50-2.34 (m, 1H), 2.30-2.17 (m, 1H), 2.13-1.94 (m, 3H), 1.94-1.86 (m, 3H), 1.86-1.55 (m, 5H), 1.21 (t, J=7.3 Hz, 3H), 1.11 (d, J=7.0 Hz, 3H), 1.06 (d, J=0.8 Hz, 3H). m/z (ESI, +ve ion) 627.2 (M+H)$^+$.

Example 1057. (1S,3'R,6'R,7'S,8'E,10'S,11'S,12'R)-6-chloro-12'-ethyl-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,11'S,12'R)-6-chloro-12'-ethyl-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'S,11'R,12'S)-6-chloro-12'-ethyl-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,11'R,12'S)-6-chloro-12'-ethyl-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide

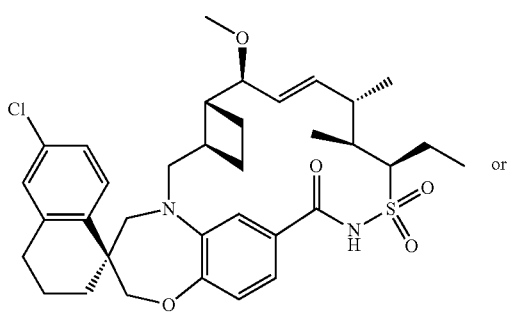

or

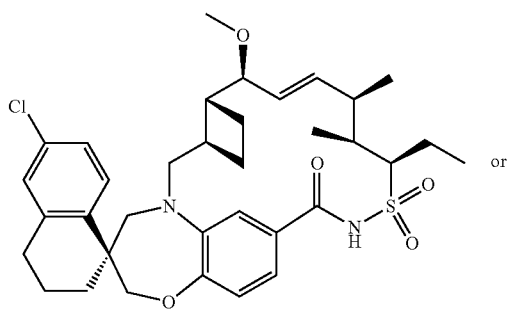

or

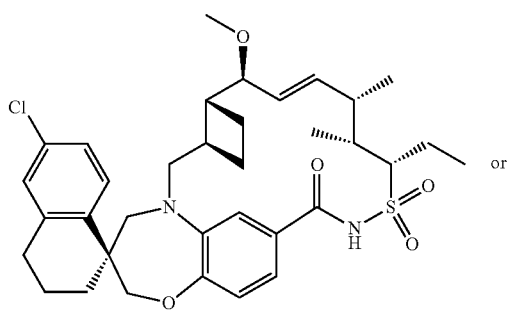

or

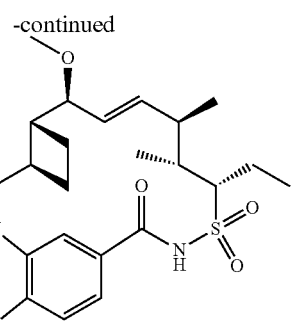

The title compound was prepared in an analogous manner to that described in Example 720 using (1S,3'R,6'R,7'S,8'E,10'S,11'S,12'R)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,11'S,12'R)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'S,11'R,12'S)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,11'R,12'S)-6-chloro-12'-ethyl-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 1056), and the desired product, (1S,3'R,6'R,7'S,8'E,10'S,11'S,12'R)-6-chloro-12'-ethyl-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,11'S,12'R)-6-chloro-12'-ethyl-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'S,11'R,12'S)-6-chloro-12'-ethyl-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,11'R,12'S)-6-chloro-12'-ethyl-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide was isolated as a white solid. $^1$H NMR (400 MHz, CDCl$_3$) δ 7.54 (d, J=8.6 Hz, 1H), 7.02 (dd, J=2.3, 8.6 Hz, 1H), 6.93 (d, J=2.2 Hz, 1H), 6.76 (s, 2H), 6.67 (s, 1H), 5.81 (dd, J=6.4, 15.6 Hz, 1H), 5.29 (dd, J=8.5, 15.9 Hz, 1H), 3.97 (q, J=7.0 Hz, 1H), 3.92 (s, 2H), 3.89 (br. s., 1H), 3.64 (d, J=15.5 Hz, 1H), 3.56-3.48 (m, 2H), 3.07 (s, 3H), 2.81 (dd, J=5.1, 15.3 Hz, 1H), 2.65-2.54 (m, 2H), 2.39 (br. s., 1H), 2.33-2.24 (m, 1H), 2.20-2.02 (m, 2H), 1.95-1.77 (m, 3H), 1.72-1.55 (m, 5H), 1.44 (dd, J=9.4, 18.6 Hz, 1H), 1.28-1.19 (m, 2H), 1.11 (t, J=7.1 Hz, 3H), 0.93 (d, J=7.2 Hz, 3H), 0.87 (d, J=7.0 Hz, 3H). m/z (ESI, +ve ion) 641.2 (M+H)$^+$.

Example 1058. (3R,6R,7S,8E,10S,11R,15S,25S)-6'-chloro-7-hydroxy-10-methyl-3',4'-dihydro-2'H,18H-spiro[13,23-dioxa-16-thia-1,17-diazapentacyclo[17.7.2.0³,⁶.0¹¹,¹⁵.0²²,²⁷]octacosa-8,19,21,27-tetraene-25,1'-naphthalen]-18-one 16,16-dioxide or (3R,6R,7S,8E,10R,11R,15S,25S)-6'-chloro-7-hydroxy-10-methyl-3',4'-dihydro-2'H,18H-spiro[13,23-dioxa-16-thia-1,17-diazapentacyclo[17.7.2.0³,⁶.0¹¹,¹⁵.0²²,²⁷]octacosa-8,19,21,27-tetraene-25,1'-naphthalen]-18-one 16,16-dioxide or (3R,6R,7S,8E,10S,11S,15R,25S)-6'-chloro-7-hydroxy-10-methyl-3',4'-dihydro-2'H,18H-spiro[13,23-dioxa-16-thia-1,17-diazapentacyclo[17.7.2.0³,⁶.0¹¹,¹⁵.0²²,²⁷]octacosa-8,19,21,27-tetraene-25,1'-naphthalen]-18-one 16,16-dioxide or (3R,6R,7S,8E,10R,11S,15R,25S)-6'-chloro-7-hydroxy-10-methyl-3',4'-dihydro-2'H,18H-spiro[13,23-dioxa-16-thia-1,17-diazapentacyclo[17.7.2.0³,⁶.0¹¹,¹⁵.0²²,²⁷]octacosa-8,19,21,27-tetraene-25,1'-naphthalen]-18-one 16,16-dioxide The title compounds were prepared in an analogous manner to that described in Example 1041 using 3,4-epoxytetrahydrofuran (TCI America) and 1-methyl-2-propenylmagnesium chloride in Step 1, and the desired product, (3R,6R,7S,8E,10S,11R,15S,25S)-6'-chloro-7-hydroxy-10-methyl-3',4'-dihydro-2'H,18H-spiro[13,23-dioxa-16-thia-1,17-diazapentacyclo[17.7.2.0³,⁶.0¹¹,¹⁵.0²²,²⁷]octacosa-8,19,21,27-tetraene-25,1'-naphthalen]-18-one 16,16-dioxide or (3R,6R,7S,8E,10R,11R,15S,25S)-6'-chloro-7-hydroxy-10-methyl-3',4'-dihydro-2'H,18H-spiro[13,23-dioxa-16-thia-1,17-diazapentacyclo[17.7.2.0³,⁶.0¹¹,¹⁵.0²²,²⁷]octacosa-8,19,21,27-tetraene-25,1'-naphthalen]-18-one 16,16-dioxide or (3R,6R,7S,8E,10S,11S,15R,25S)-6'-chloro-7-hydroxy-10-methyl-3',4'-dihydro-2'H,18H-spiro[13,23-dioxa-16-thia-1,17-diazapentacyclo[17.7.2.0³,⁶.0¹¹,¹⁵.0²²,²⁷]octacosa-8,19,21,27-tetraene-25,1'-naphthalen]-18-one 16,16-dioxide or (3R,6R,7S,8E,10R,11S,15R,25S)-6'-chloro-7-hydroxy-10-methyl-3',4'-dihydro-2'H,18H-spiro[13,23-dioxa-16-thia-1,17-diazapentacyclo[17.7.2.0³,⁶.0¹¹,¹⁵.0²²,²⁷]octacosa-8,19,21,27-tetraene-25,1'-naphthalen]-18-one 16,16-dioxide was isolated (fourth eluting major peakr out of preparative reverse phase HPLC). $^1$H NMR (500 MHz, CD$_3$OD) δ 7.75 (d, J=8.6 Hz, 1H), 7.19 (dd, J=2.3, 8.4 Hz, 1H), 7.13 (d, J=2.0 Hz, 1H), 7.05 (dd, J=2.0, 8.1 Hz, 1H), 6.96 (d, J=8.1 Hz, 1H), 6.91 (d, J=1.7 Hz, 1H), 5.86 (dd, J=6.0, 15.5 Hz, 1H), 5.70 (dd, J=6.1, 16.1 Hz, 1H), 4.29 (dd, J=4.6, 10.5 Hz, 1H), 4.26-4.20 (m, 2H), 4.15-4.13 (m, 1H), 4.11 (d, J=3.9 Hz, 2H), 3.84 (d, J=14.9 Hz, 1H), 3.73-3.58 (m, 3H), 3.10 (dd, J=9.5, 15.7 Hz, 1H), 2.92-2.73 (m, 3H), 2.64 (d, J=5.6 Hz, 1H), 2.56-2.39 (m, 1H), 2.28-2.15 (m, 1H), 2.13 (d, J=13.2 Hz, 1H), 2.02-1.61 (m, 7H), 1.57-1.43 (m, 1H), 1.10 (d, J=7.1 Hz, 3H). m/z (ESI, +ve ion) 627.2 (M+H)$^+$.

Example 1059. (1S,3'R,6'R,8'E,10'S,11'S)-6-chloro-10',11'-dimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa [8,16,18,24]tetraene]-7',15'-dione 13',13'-dioxide or (1S,3'R,6'R,8'E,10'R,11'R)-6-chloro-10',11'-dimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa [8,16,18,24]tetraene]-7',15'-dione 13',13'-dioxide

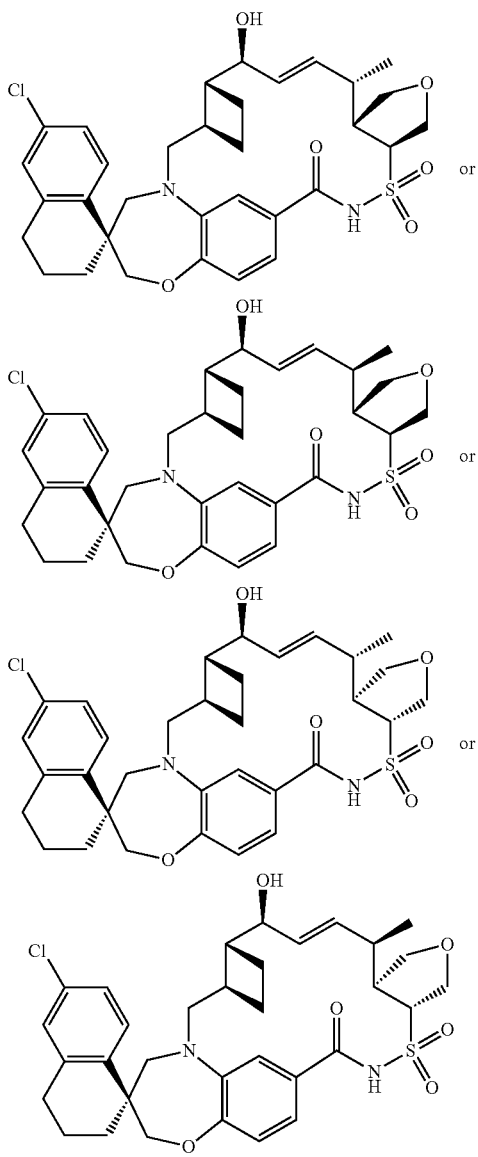

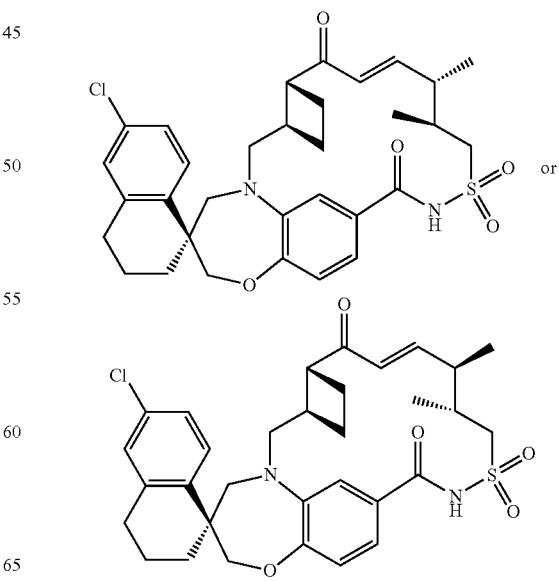

Step 1: (2R,3S)-2,3-dimethylbutane-1,4-diol

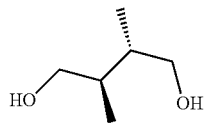

Meso-2,3-dimethylsuccinic acid (4.1 g, 28.1 mmol, Aldrich) in THF (28 ml) was transferred into a 3 neck round bottom flask fitted with an addition funnel, nitrogen inlet and thermometer and the flask was cooled to 0° C. Lithium aluminum hydride (2.0 M solution in tetrahydrafuran, 72.9 ml, 72.9 mmol, Aldrich) was then cannulated into the addition funnel, and then added into the stirred cooled mixture dropwise over 15 min. After the addition was completed the reaction was allowed to warm to rt overnight under a nitrogen atmosphere. The next day the reaction was quenched with MeOH dropwise at 0° C. and then 20% KOH aq solution was added slowly. The reaction mixture was stirred at 0° C. for 20 min, 50 mL of EtOAc was added and the organic phase was dried over MgSO₄ filtered and concentrated. The crude material was purified by chromatography through a 120 g ISCO gold column, eluting with 50-100% EtOAc in hexanes to give (2R,3S)-2,3-dimethylbutane-1,4-diol (2.7 g, 22.9 mmol).

Step 2: (2R,3S)-4-((tert-butyldimethylsilyl)oxy)-2,3-dimethylbutan-1-ol and (2S,3R)-4-((tert-butyldimethylsilyl)oxy)-2,3-dimethylbutan-1-ol

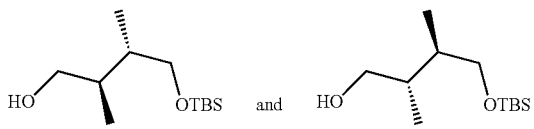

To a suspension of sodium hydride (60% dispersion in mineral oil, 1.35 g, 33.6 mmol, Aldrich) in THF (90 ml) at 0° C. under a N₂ atmosphere was added a solution of (2R,3S)-2,3-dimethylbutane-1,4-diol (2.65 g, 22.4 mmol) from Step 1 above in THF (15 mL) dropwise over 20 min. After addition the reaction was heated at 55° C. for 45 min and then it was cooled down to 0° C. and treated with a solution of tert-butyldimethylsilyl chloride (3.38 g, 22.4 mmol) in THF (15 mL). The reaction was stirred at rt overnight. The next day the reaction was quenched with saturated NH4Cl and diluted with EtOAc. The separated aqueous layer was extracted with EtOAc, and the combined organic extracts were washed with brine, dried over MgSO4, filtered and evaporated in vacuo. The crude material was purified by chromatography through a 120 g ISCO gold column, eluting with 0-20% EtOAc in hexanes to give a mixture of (2R,3S)-4-((tert-butyldimethylsilyl)oxy)-2,3-dimethylbutan-1-ol and (2S,3R)-4-((tert-butyldimethylsilyl)oxy)-2,3-dimethylbutan-1-ol (3.7 g, 15.9 mmol).

Step 3: (2R,3S)-4-((tert-butyldimethylsilyl)oxy)-2,3-dimethylbutanal and (2S,3R)-4-((tert-butyldimethylsilyl)oxy)-2,3-dimethylbutanal

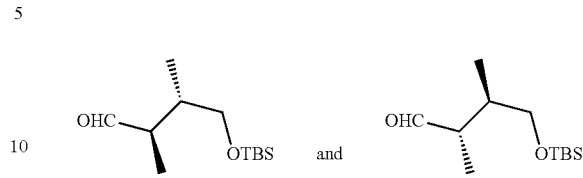

To a white slurry solution of (diacetoxyiodo)benzene (5.34 g, 16.6 mmol, Aldrich) and a mixture of (2R,3S)-4-((tert-butyldimethylsilyl)oxy)-2,3-dimethylbutan-1-ol and (2S,3R)-4-((tert-butyldimethylsilyl)oxy)-2,3-dimethylbutan-1-ol from Step 2 above in DCM (50 ml) was added 2,2,6,6-tetramethylpiperidinooxy (0.118 g, 0.75 mmol, Acros) in one portion at rt, and then the stirred for overnight. The reaction mixture was poured into 100 ml of DCM and washed with 30 mL of sodium bicarbonate saturated. aq solution and 30 mL of brine, dried over MgSO₄. The solvent was removed. The crude material was purified by chromatography through a 120 g ISCO gold column, eluting with 0-10% EtOAc in hexanes to give a mixture of (2R,3S)-4-((tert-butyldimethylsilyl)oxy)-2,3-dimethylbutanal and (2S,3R)-4-((tert-butyldimethylsilyl)oxy)-2,3-dimethylbutanal (1.8 g, 7.8 mmol, 51.9%).

Step 4: (2S,3S)-2,3-dimethylpent-4-en-1-ol and (2R,3R)-2,3-dimethylpent-4-en-1-ol

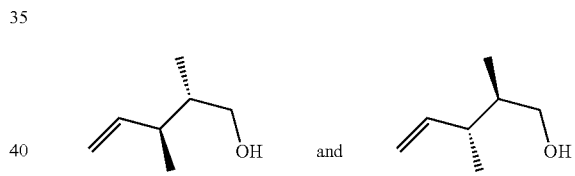

A solution of methyl phenylphosphonium bromide (8.06 g, 22.58 mmol, Aldrich) in THF (75 ml) was treated with butyllithium (2.5M solution in hexane, 7.53 ml, 18.8 mmol, Aldrich) at 0° C. After 10 min, the resulting yellow mixture was allowed to stir at rt for 20 min. After this time, a mixture of (2R,3S)-4-((tert-butyldimethylsilyl)oxy)-2,3-dimethylbutanal and (2S,3R)-4-((tert-butyldimethylsilyl)oxy)-2,3-dimethylbutanal (1.73 g, 7.5 mmol) from step 3 in THF (5 ml) was added to the reaction at −78° C. After 10 min, the reaction mixture was stirred at 0° C. for 2 h and then quenched with saturated aq. NH₄Cl solution and water (20 ml). The mixture was poured into a separatory funnel containing ether (50 ml). After separating the layers, the aqueous layer was extracted with ether (3×50 ml). The organic layers were combined, dried with MgSO₄, and evaporated in vacuo to give the crude desired product. 15 mL of 1 N HCl/ether (Aldrich) was added this crude product in 10 mL of DCM, the reaction mixture was stirred at rt for 30 min, TLC showed the deprotection was completely. The reaction mixture was concentrated and purified by chromatography through a 40 g ISCO gold column, eluting with 0-30% EtOAc in hexanes to give a mixture of (2S,3S)-2,3-dimethylpent-4-en-1-ol and (2R,3R)-2,3-dimethylpent-4-en-1-ol.

Step 5: (2S,3S)-2,3-dimethylpent-4-ene-1-sulfonamide and (2R,3R)-2,3-dimethylpent-4-ene-1-sulfonamide

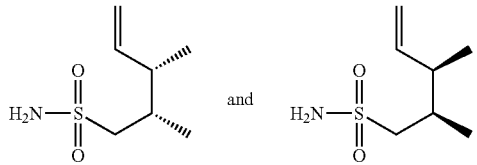

The title compound was prepared according to the general procedure described in Intermediate EE22, Steps 3-6 using a mixture of (2S,3S)-2,3-dimethylpent-4-en-1-ol and (2R,3R)-2,3-dimethylpent-4-en-1-ol in Step 4.

Step 6: (S)-6'-chloro-N-(((2S,3S)-2,3-dimethylpent-4-en-1-yl)sulfonyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide and (3S)-6'-chloro-N-(((2R,3R)-2,3-dimethyl-4-penten-1-yl)sulfonyl)-5-(((1R,2R)-2-((1S)-1-hydroxy-2-propen-1-yl)cyclobutyl)methyl)-3',4,4',5-tetrahydro-2'H-spiro[1,5-benzoxazepine-3,1'-naphthalene]-7-carboxamide

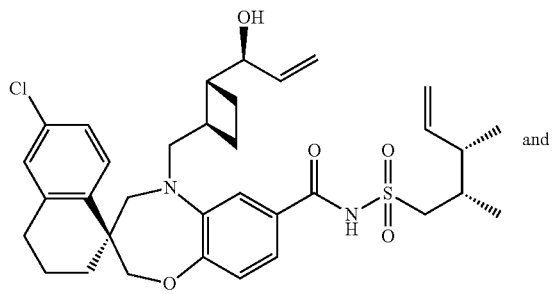

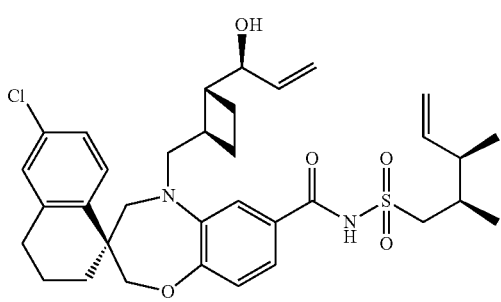

The title compound was prepared in an analogous manner to that described in Example 719, Step 1, using (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Intermediate AA11A) and (2S,3S)-2,3-dimethylpent-4-en-1-sulfonamide and (2R,3R)-2,3-dimethylpent-4-ene-1-sulfonamide from Step 5 above, and the desired product, a mixture of (S)-6'-chloro-N-(((2S,3S)-2,3-dimethylpent-4-en-1-yl)sulfonyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide and (3S)-6'-chloro-N-(((2R,3R)-2,3-dimethyl-4-penten-1-yl)sulfonyl)-5-(((1R,2R)-2-((1S)-1-hydroxy-2-propen-1-yl)cyclobutyl)methyl)-3',4,4',5-tetrahydro-2'H-spiro[1,5-benzoxazepine-3,1'-naphthalene]-7-carboxamide was isolated.

Step 7: (S)-5-(((1R,2R)-2-acryloylcyclobutyl)methyl)-6'-chloro-N-(((2S,3S)-2,3-dimethylpent-4-en-1-yl)sulfonyl)-3',4,4',5-tetrahydro-2H,2'H-spiro[benzo[b][1,4]oxazepine-3,1'-naphthalene]-7-carboxamide and (3S)-5-(((1R,2R)-2-acryloylcyclobutyl)methyl)-6'-chloro-N-(((2R,3R)-2,3-dimethyl-4-penten-1-yl)sulfonyl)-3',4,4',5-tetrahydro-2'H-spiro[1,5-benzoxazepine-3,1'-naphthalene]-7-carboxamide

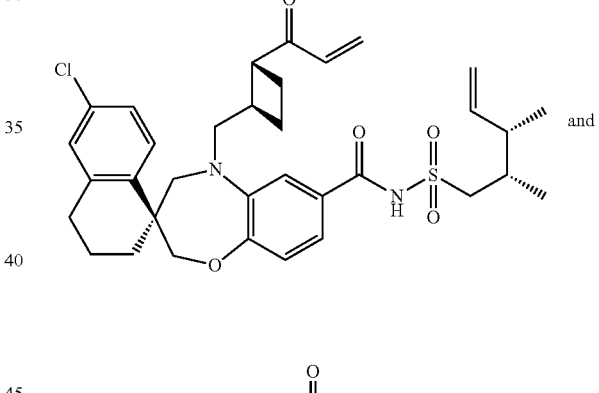

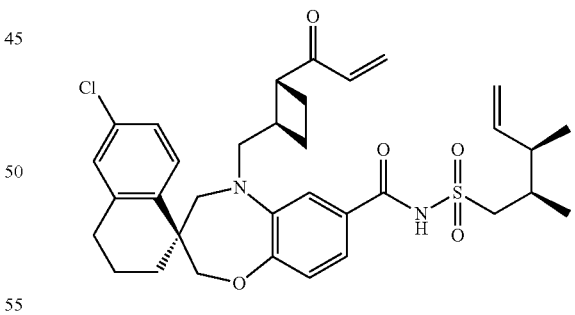

To a 250-mL round-bottomed flask, Dess-Martin periodinane (556 mg, 1.31 mmol, Aldrich) was added a mixture of (S)-6'-chloro-N-(((2S,3S)-2,3-dimethylpent-4-en-1-yl)sulfonyl)-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide and (3S)-6'-chloro-N-(((2R,3R)-2,3-dimethyl-4-penten-1-yl)sulfonyl)-5-(((1R,2R)-2-((1S)-1-hydroxy-2-propen-1-yl)cyclobutyl)methyl)-3',4,4',5-tetrahydro-2'H-spiro[1,5-benzoxazepine-3, 1'-naphthalene]-7-carboxamide (685 mg, 1.092 mmol) from Step 6 above in DCM (22 mL). The reaction mixture was stirred at rt for 1 h. The reaction mixture was was concentrated and purified by chromatography through a 80 g ISCO gold column, eluting with 0-20% EtOAc(containing 0.3% HOAc) in hexane to give (S)-5-(((1R,2R)-2-acryloylcyclobutyl)methyl)-6'-chloro-N-(((2S,3S)-2,3-dimethylpent-4-en-1-yl)sulfonyl)-3',4,4',5-tetrahydro-2H,2'H-spiro[benzo[b][1,4]oxazepine-3,1'-naphthalene]-7-carboxamide and (S)-5-(((1R,2R)-2-acryloylcyclobutyl)methyl)-6'-chloro-N-(((2R,3R)-2,3-dimethylpent-4-en-1-yl)sulfonyl)-3',4,4',5-tetrahydro-2H,2'H-spiro[benzo[b][1,4]oxazepine-3,1'-naphthalene]-7-carboxamide (520 mg, 0.83 mmol).

Step 8: (1S,3'R,6'R,8'E,10'S,11'S)-6-chloro-10',11'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dione 13',13'-dioxide A 500 mL of round bottom flask was charged with a mixture of (S)-5-(((1R,2R)-2-acryloylcyclobutyl)methyl)-6'-chloro-N-(((2S,3S)-2,3-dimethylpent-4-en-1-yl)sulfonyl)-3',4,4',5-tetrahydro-2H,2'H-spiro[benzo[b][1,4]oxazepine-3,1'-naphthalene]-7-carboxamide (from Step 6) and (S)-5-(((1R,2R)-2-acryloylcyclobutyl)methyl)-6'-chloro-N-(((2R,3R)-2,3-dimethylpent-4-en-1-yl)sulfonyl)-3',4,4',5-tetrahydro-2H,2'H-spiro[benzo[b][1,4]oxazepine-3,1'-naphthalene]-7-carboxamide (400 mg, 0.64 mmol) from Step 7 above in DCE (220 mL). It was stirred at rt under N$_2$ bubbling through the reaction mixture for 10 min. To the homogeneous solution was added Hoveyda-Grubbs II (120 mg, 0.19 mmol, Aldrich) at rt, and then the mixture was heated to at 80° C. for 5 h under a N$_2$ atmosphere. The reaction mixture was concentrated and purified by chromatography through a 220 g ISCO gold column, eluting with 0-40% EtOAc (containing 0.3% AcOH) in hexane to give (1S,3'R,6'R,8'E,10'S,11'S)-6-chloro-10',11'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dione 13',13'-dioxide or (1S,3'R,6'R,8'E,10'R,11'R)-6-Chloro-10',11'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dione 13',13'-dioxide (143 mg, 0.24 mmol, first eluting major peak) and (1S,3'R,6'R,8'E,10'R,11'R)-6-Chloro-10',11'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dione 13',13'-dioxide or (1S,3'R,6'R,8'E,10'S,11'S)-6-chloro-10',11'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dione 13',13'-dioxide (1S,3'R,6'R,8'E,10'S,11'S)-6-chloro-10',11'-dimethyl-3,4-dihydro-2H,7'H,15'H-spiro[naphthalene-1,22'-[20]oxa[13]thia[1,14]diazatetracyclo[14.7.2.0$^{3,6}$.0$^{19,24}$]pentacosa[8,16,18,24]tetraene]-7',15'-dione 13',13'-dioxide (145 mg, 0.024 mmol, second eluting major isomer). $^1$H NMR (400 MHz, CDCl$_3$) δ 8.18 (br. s., 1H), 7.66 (d, J=8.6 Hz, 1H), 7.19 (dd, J=2.2, 8.5 Hz, 1H), 7.11 (d, J=3651.5 Hz, 1H), 7.04 (s, 1H), 6.94-6.88 (m, 2H), 6.84 (dd, J=6.8, 16.2 Hz, 1H), 5.98 (d, J=14.9 Hz, 1H), 4.09 (s, 2H), 3.80 (d, J=15.3 Hz, 1H), 3.71-3.61 (m, 2H), 3.56-3.46 (m, 2H), 3.35 (d, J=18.4 Hz, 1H), 3.09-2.98 (m, 2H), 2.82-2.76 (m, 2H), 2.51 (br. s., 1H), 2.40 (br. s., 1H), 2.06-2.00 (m, 1H), 1.95-1.66 (m, 6H), 1.31 (d, J=6.7 Hz, 3H), 1.14 (d, J=14.5 Hz, 1H), 1.03 (d, J=6.8 Hz, 3H). m/z (ESI, +ve ion) 597.2 (M+H)$^+$.

Example 1060. (1S,3'R,6'R,7'S,8'E,10'S,11'S)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'R,8'E,10'S,11'S)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'S,8'E,10'R,11'R)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or AMG3101256. (1S,3'R,6'R,7'R,8'E,10'R,11'R)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

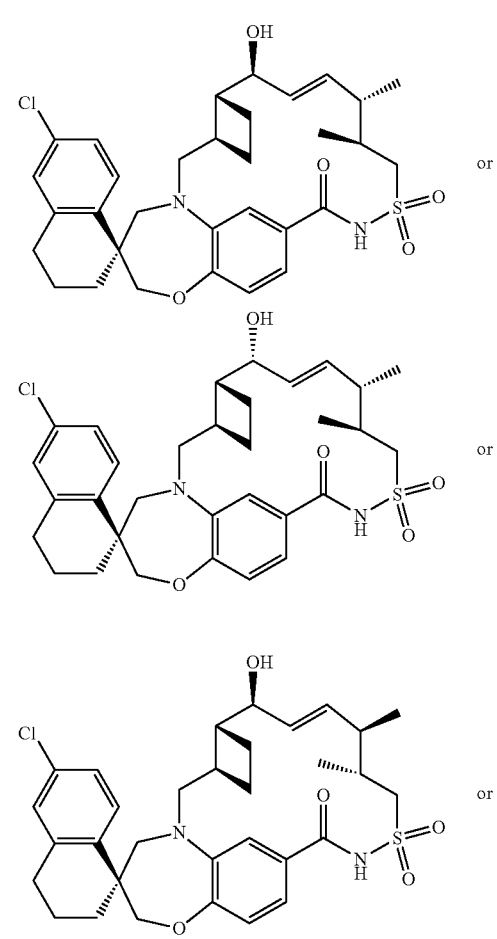

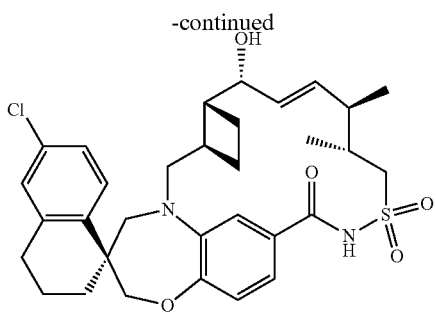

An 25 mL of round bottom flask was charged with (1S,3'R,6'R,8'E,10'S,11'S)-6-chloro-10',11'-dimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[8,16,18,24]tetraene]-7',15'-dione 13',13'-dioxide or (1S,3'R,6'R,8'E,10'R,11'R)-6-Chloro-10',11'-dimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[8,16,18,24]tetraene]-7',15'-dione 13',13'-dioxide (Example 1059; 140 mg, 0.234 mmol, first eluting major isomer) and 3 mL of THF, and then borane tetrahydrofuran complex (1.0 M soution in tetrahydrofuran, 350 μl, 0.35 mmol, Aldrich) was added at 0° C. The reaction mixture was stirred at 0° C. for 1 h. The reaction mixture was quenched with MeOH and added saturated aq. NH4Cl solution, and then 30 mL of EtOAc. The organic layer was concentrated and purified by chromatography through a 40 g ISCO gold column, eluting with 0-40% EtOAc (containing 0.3% AcOH) in hexane to give (1S,3'R,6'R,7'S,8'E,10'S,11'S)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'R,8'E,10'S,11'S)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,11'R)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'R,8'E,10'R,11'R)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (25.1 mg, 0.042 mmol, second eluting major peak). ¹H NMR (500 MHz, CD₃OD) δ 7.75 (d, J=8.6 Hz, 1H), 7.19 (dd, J=2.2, 8.6 Hz, 1H), 7.12 (d, J=2.2 Hz, 1H), 7.02 (dd, J=2.0, 8.1 Hz, 1H), 6.94 (d, J=8.1 Hz, 1H), 6.89 (d, J=1.7 Hz, 1H), 5.89 (dd, J=7.6, 15.2 Hz, 1H), 5.69 (dd, J=8.6, 15.2 Hz, 1H), 4.20 (dd, J=3.5, 8.7 Hz, 1H), 4.13 (dd, J=4.5, 15.0 Hz, 1H, 4.09 (s, 2H), 3.85 (d, J=15.2 Hz, 1H), 3.67 (d, J=14.2 Hz, 1H), 3.12-3.02 (m, 2H), 2.86-2.74 (m, 2H), 2.49-2.39 (m, 2H), 2.27 (quin, J=9.2 Hz, 1H), 2.11 (d, J=13.7 Hz, 1H), 2.05-1.80 (m, 7H), 1.74 (dd, J=9.5, 19.1 Hz, 1H), 1.50-1.42 (m, 1H), 1.16 (d, J=7.1 Hz, 3H), 1.02 (d, J=7.1 Hz, 3H). m/z (ESI, +ve ion) 599.2 (M+H)⁺.

Example 1061. (1S,3'R,6'R,7'R,8'E,10'S,11'S)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide or (1S,3'R,6'R,7'S,8'E,10'S,11'S)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,11'R)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or AMG3101256. (1S,3'R,6'R,7'R,8'E,10'R,11'R)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

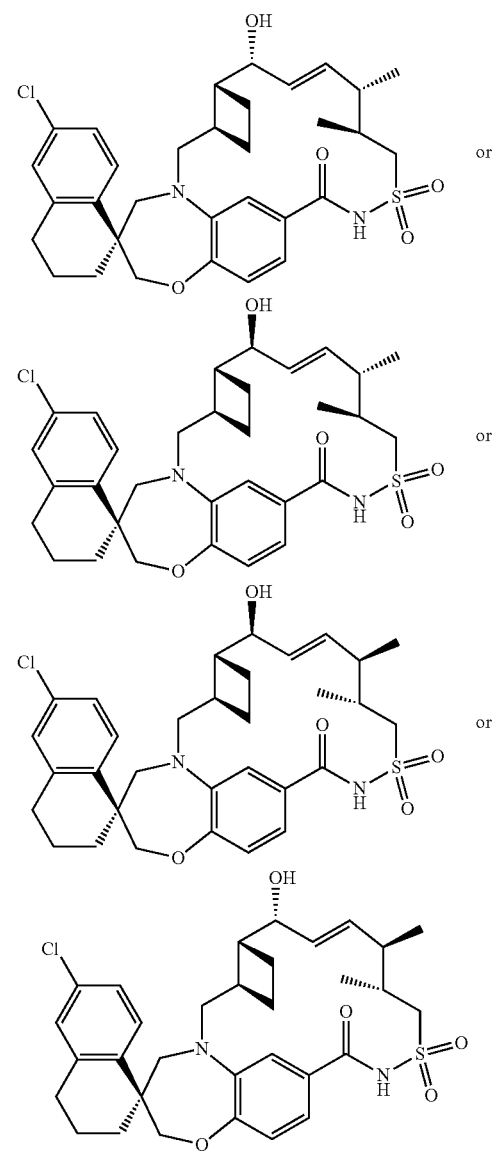

2085

The title compound was obtained as a single isomer (first eluting major peak) from the reverse phase preparative HPLC in Example 1060. ¹H NMR (400 MHz, CD₃OD) δ 7.77 (d, J=8.4 Hz, 1H), 7.50 (d, J=1.8 Hz, 1H), 7.20 (dd, J=2.2, 8.5 Hz, 1H), 7.16-7.11 (m, 2H), 6.94 (d, J=8.2 Hz, 1H), 5.53-5.44 (m, 2H), 4.11 (s, 2H), 3.98-3.86 (m, 2H), 3.73 (d, J=13.9 Hz, 1H), 3.64 (br. s., 1H), 3.04 (dd, J=4.4, 15.4 Hz, 1H), 2.89-2.73 (m, 3H), 2.59 (d, J=6.1 Hz, 2H), 2.36-2.29 (m, 1H), 2.20-2.03 (m, 2H), 1.97-1.81 (m, 5H), 1.77-1.63 (m, 2H), 1.50-1.41 (m, 1H), 1.23 (d, J=6.8 Hz, 3H), 0.94 (d, J=7.0 Hz, 3H). m/z (ESI, +ve ion) 599.2 (M+H)⁺.

Example 1062. (1S,3'R,6'R,7'R,8'E,10'R,11'R)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,11'R)-6-chloro-7'-hydroxy-10',11'-dimethyl-3,4-dihydro-2H,15'H-spiro[naphthalene-1,22'-[20]oxa[13]thia[1,14]diazatetracyclo[[14.7.2.0³,⁶.0¹⁹,²⁴]pentacosa[8,16,18,24]tetraen]-15'-one 13',13'-dioxide or (1S,3'R,6'R,7'S,8'E,10'S,11'S)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'R,8'E,10'S,11'S)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

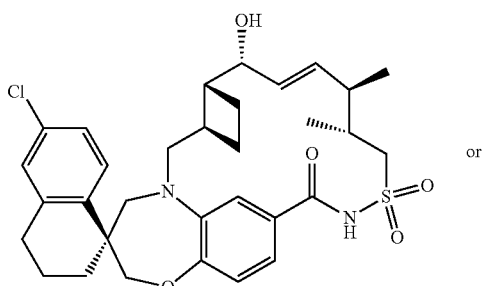

or

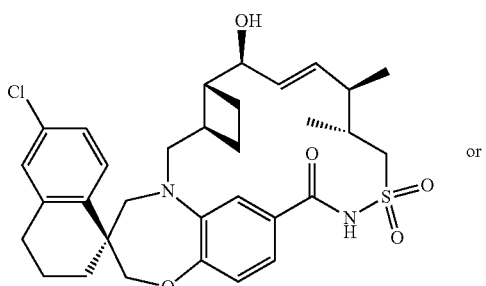

or

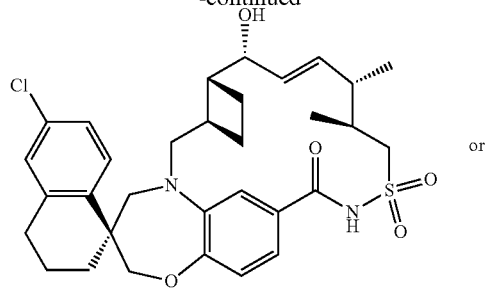

or

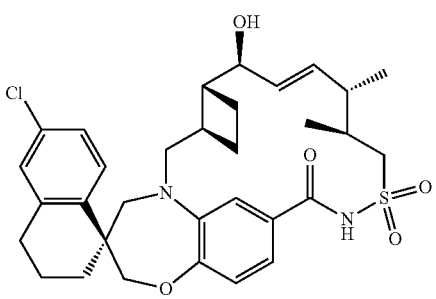

The title compound was prepared in an analogous manner to that described in Example 1060 using (1S,3'R,6'R,8'E,10'R,11'R)-6-chloro-10',11'-dimethyl-3,4-dihydro-2H,7'H,15'H-spiro[naphthalene-1,22'-[20]oxa[13]thia[1,14]diazatetracyclo[14.7.2.0³,⁶.0¹⁹,²⁴pentacosa[8,16,18,24]tetraene]-7',15'-dione 13',13'-dioxide or (1S,3'R,6'R,8'E,10'S,11'S)-6-chloro-10',11'-dimethyl-3,4-dihydro-2H,7'H,15'H-spiro [naphthalene-1,22'-[20]oxa[13]thia[1,14]diazatetracyclo [14.7.2.0³,⁶.0¹⁹,²⁴pentacosa[8,16,18,24]tetraene]-7',15'-dione 13',13'-dioxide (Example 1059, second eluting major peak), and the desired product, (1S,3'R,6'R,7'R,8'E,10'R,11'R)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴pentacosa[8,16,18,24] tetraen]-15'-one 13',13'-dioxide or (1S,3'R,6'R,7'S,8'E,10'R,11'R)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴pentacosa[8,16,18,24] tetraen]-15'-one 13',13'-dioxide or (1S,3'R,6'R,7'R,8'E,10'S,11'S)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴pentacosa[8,16,18,24] tetraen]-15'-one 13',13'-dioxide or (1S,3'R,6'R,7'S,8'E,10'S,11'S)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24] tetraen]-15'-one 13',13'-dioxide was isolated (first eluting major peak out of reverse phase preparative HPLC). ¹H NMR (500 MHz, CD₃OD) δ 7.73 (d, J=8.3 Hz, 1H), 7.19 (dd, J=2.3, 8.4 Hz, 1H), 7.12 (d, J=2.2 Hz, 1H), 6.99-6.87 (m, 3H), 5.87 (dd, J=6.8, 13.4 Hz, 1H), 5.46 (dd, J=8.6, 15.2 Hz, 1H), 4.11 (br. s., 2H), 4.04 (dd, J=4.9, 15.2 Hz, 1H), 3.98 (br. s., 1H), 3.64 (d, J=13.0 Hz, 1H), 3.52-3.37 (m, 4H), 3.07 (dd, J=7.6, 15.2 Hz, 1H), 2.86-2.74 (m, 2H), 2.59 (br. s., 1H), 2.44 (br. s., 1H), 2.21-1.73 (m, 10H), 1.61-1.46 (m, 1H), 1.13 (d, J=6.8 Hz, 3H), 1.01 (d, J=6.8 Hz, 3H). m/z (ESI, +ve ion) 599.2 (M+H)⁺.

Example 1063. (1S,3'R,6'R,7'S,8'E,10'R,11'R)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'R,8'E,10'R,11'R)-6-chloro-7'-hydroxy-10',11'-dimethyl-3,4-dihydro-2H,15'H-spiro[naphthalene-1,22'-[20]oxa[13]thia[1,14]diazatetracyclo[[14.7.2.0$^{3,6}$.0$^{19,24}$]pentacosa[8,16,18,24]tetraen]-15'-one 13',13'-dioxide or or (1S,3'R,6'R,7'S,8'E,10'S,11'S)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide or (1S,3'R,6'R,7'R,8'E,10'S,11'S)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0~3,6~.0~19,24~]pentacosa[8,16,18,24]tetraen]-15'-one 13',13'-dioxide

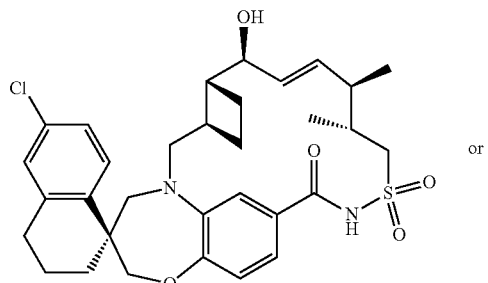

or

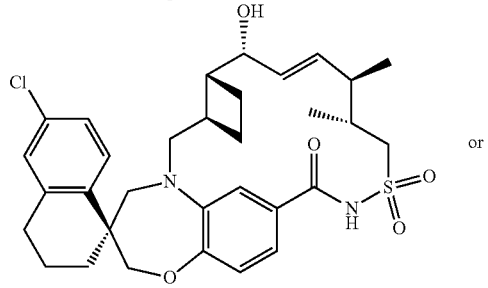

or

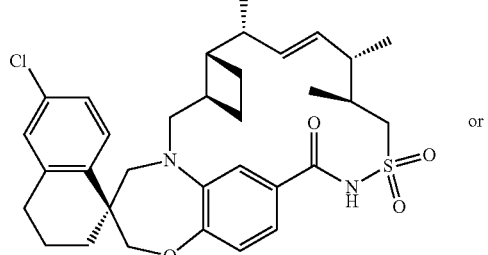

or

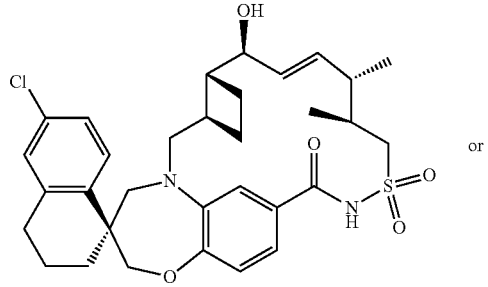

or

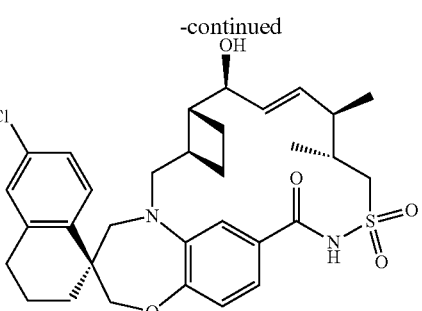

or

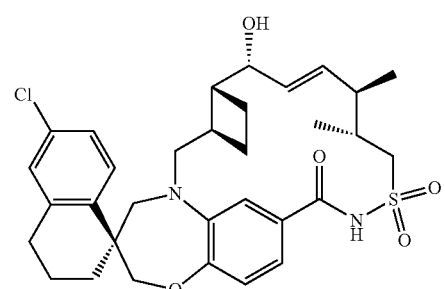

or

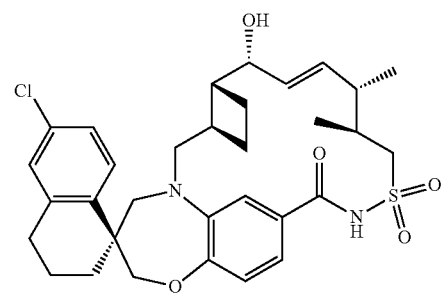

or

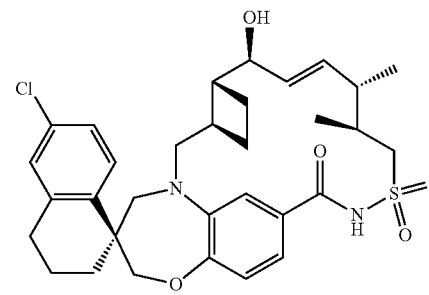

The title compound was obtained as a single isomer (second eluting major peak) from the reverse phase preparative HPLC in Example 1062. $^1$H NMR (400 MHz, CD$_3$OD) δ 7.73 (d, J=8.4 Hz, 1H), 7.19 (dd, J=2.5, 8.4 Hz, 2H), 7.13 (d, J=2.3 Hz, 1H), 7.00 (dd, J=2.2, 9.4 Hz, 1H), 6.93 (d, J=8.0 Hz, 1H), 6.05-5.93 (m, 1H), 5.62 (ddd, J=1.6, 4.3, 15.8 Hz, 1H), 4.14 (s, 2H), 4.06-4.02 (m, 1H), 4.00 (dd, J=5.3, 15.3 Hz, 1H), 3.68-3.47 (m, 3H), 3.22-3.09 (m, 1H), 2.86-2.73 (m, 2H), 2.67 (d, J=10.2 Hz, 1H), 2.45 (br. s., 1H), 2.39 (br. s., 1H), 2.15-1.94 (m, 4H), 1.91 (br. s., 2H), 1.79 (br. s., 3H), 1.71-1.50 (m, 1H), 1.13 (d, J=7.0 Hz, 3H), 1.01 (d, J=6.8 Hz, 3H). m/z (ESI, +ve ion) 599.2 (M+H)$^+$.

Example 1064. (1S,3'R,6'R,7'S,8'E,10'S,11'S)-6-chloro-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'R,8'E,10'S,11'S)-6-chloro-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'R,11'R)-6-chloro-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'R,8'E,10'R,11'R)-6-chloro-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

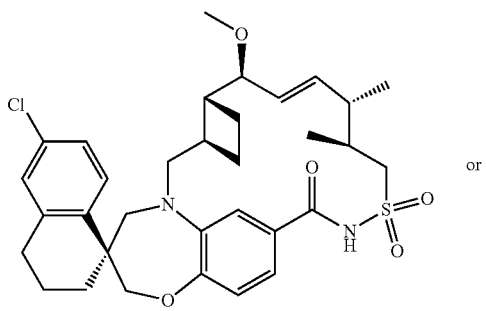

or

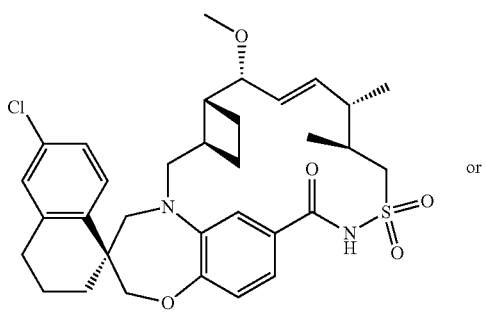

or

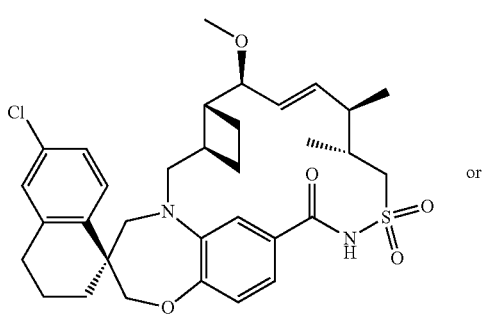

or

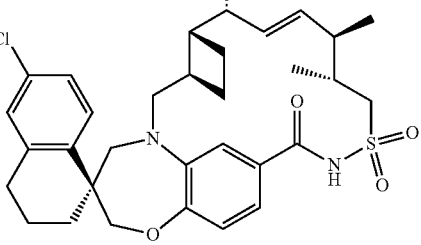

The title compound was prepared in an analogous manner to that described in Example 720 using (1S,3'R,6'R,7'S,8'E,10'S,11'S)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'R,8'E,10'S,11'S)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,11'R)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'R,8'E,10'R,11'R)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 1060) and methyl iodide, and the desired product, (1S,3'R,6'R,7'S,8'E,10'S,11'S)-6-chloro-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'R,8'E,10'S,11'S)-6-chloro-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,11'R)-6-chloro-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'R,8'E,10'R,11'R)-6-chloro-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide was isolated as a white solid. $^1$H NMR (500 MHz, CD$_3$OD) δ 7.75 (d, J=8.3 Hz, 1H), 7.18 (dd, J=2.2, 8.6 Hz, 1H), 7.12 (d, J=2.0 Hz, 1H), 7.02 (dd, J=1.7, 8.1 Hz, 1H), 6.93 (d, J=8.1 Hz, 1H), 6.87 (d, J=1.5 Hz, 1H), 5.99 (dd, J=7.3, 15.2 Hz, 1H), 5.52 (dd, J=9.3, 15.4 Hz, 1H), 4.18 (dd, J=4.9, 14.9 Hz, 1H), 4.08 (s, 2H), 3.85 (d, J=15.2 Hz, 1H), 3.73 (dd, J=3.4, 9.3 Hz, 1H), 3.67 (d, J=14.2 Hz, 1H), 3.24 (s, 3H), 3.12-3.04 (m, 2H), 2.86-2.73 (m, 2H), 2.58-2.46 (m, 2H), 2.39-2.27 (m, 1H), 2.11 (d, J=13.4 Hz, 1H), 2.08-1.99 (m, 2H), 1.98-1.79 (m, 5H), 1.75 (dd, J=10.5, 19.6 Hz, 1H), 1.49-1.39 (m, 1H), 1.15 (d, J=6.8 Hz, 3H), 1.05 (d, J=6.8 Hz, 3H). m/z (ESI, +ve ion) 613.2 (M+H)$^+$.

Example 1065. (1S,3'R,6'R,7'S,8'E,10'S,11'S)-6-chloro-7'-(2-methoxyethoxy)-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'R,8'E,10'S,11'S)-6-chloro-7'-(2-methoxyethoxy)-10',11'-dimethyl-3,4-dihydro-2H,15'H-spiro[naphthalene-1,22'-[20]oxa[13]thia[1,14]diazatetracyclo [14.7.2.0³,⁶.0¹⁹,²⁴]pentacosa[8,16,18,24]tetraen]-15'-one 13',13'-dioxide or (1S,3'R,6'R,7'S,8'E,10'R,11'R)-6-chloro-7'-(2-methoxyethoxy)-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'R,8'E,10'R,11'R)-6-chloro-7'-(2-methoxyethoxy)-10',11'-dimethyl-3,4-dihydro-2H,15'H-spiro [naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

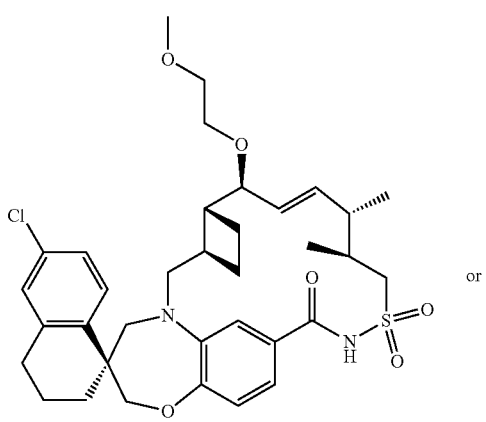

or

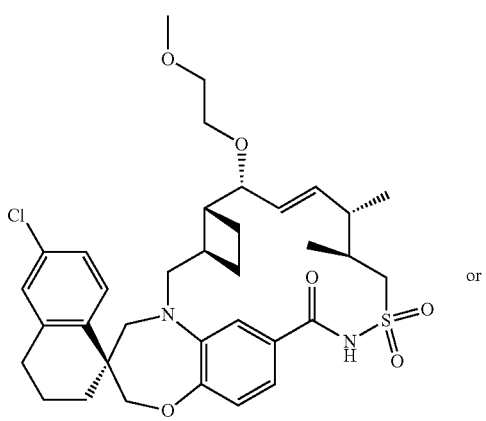

or

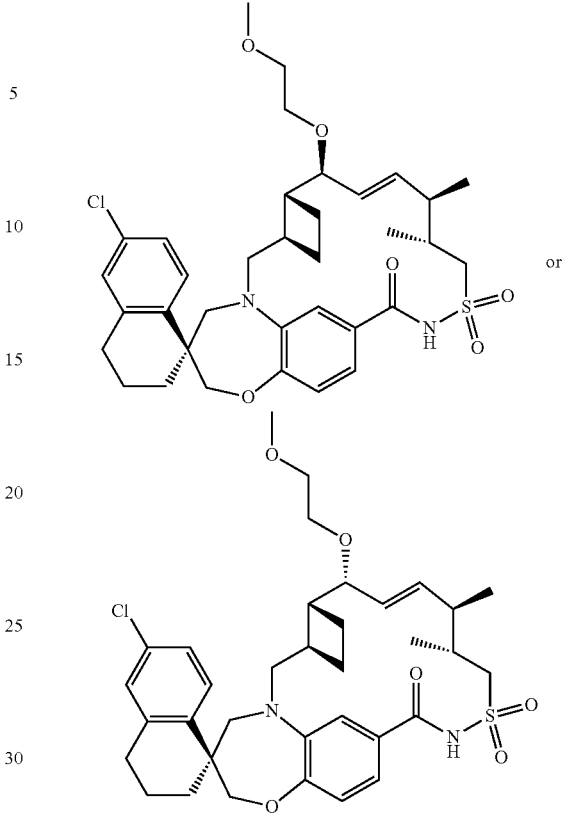

The title compound was prepared in an analogous manner to that described in Example 720 using (1S,3'R,6'R,7'S,8'E,10'S,11'S)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'R,8'E,10'S,11'S)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴pentacosa[8,16,18,24]tetraen]-15'-one 13',13'-dioxide or (1S,3'R,6'R,7'S,8'E,10'R,11'R)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'R,8'E,10'R,11'R)-6-chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴pentacosa[8,16,18,24]tetraen]-15'-one 13',13'-dioxide (Example 1060) and 1-bromo-2-methoxyethane (Aldrich), and the desired product, (1S,3'R,6'R,7'S,8'E,10'S,11'S)-6-chloro-7'-(2-methoxyethoxy)-10',11'-dimethyl-3,4-dihydro-2H,15'H-spiro[naphthalene-1,22'-[20]oxa[13]thia[1,14]diazatetracyclo [14.7.2.0³,⁶.0¹⁹,²⁴]pentacosa[8,16,18,24]tetraen]-15'-one 13',13'-dioxide or (1S,3'R,6'R,7'R,8'E,10'S,11'S)-6-chloro-7'-(2-methoxyethoxy)-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,11'R)-6-chloro-7'-(2-methoxyethoxy)-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'R,8'E,10'R,11'R)-6-chloro-7'-(2-methoxyethoxy)-10',11'-dimethyl-3,4- dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide was isolated as a white solid. ¹H NMR (400 MHz, CD₃OD) δ 7.64 (d, J=8.4 Hz, 1H), 7.06 (dd, J=1.8, 8.8 Hz, 1H), 6.99 (d, J=2.2 Hz, 1H), 6.94 (d, J=8.0 Hz, 1H), 6.79 (s, 1H), 6.75 (d, J=8.2 Hz, 1H), 5.95 (dd, J=10.8, 16.8 Hz, 1H), 5.38 (dd, J=9.1, 15.4 Hz, 1H), 4.04 (dd, J=5.7, 15.3 Hz, 1H), 3.94 (s, 2H), 3.82-3.70 (m, 2H), 3.54 (d, J=14.3 Hz, 1H), 3.51-3.29 (m, 5H), 3.25 (s, 2H), 2.93 (dd, J=10.4, 15.3 Hz, 1H), 2.78-2.60 (m, 2H), 2.51 (br. s., 1H), 2.43-2.31 (m, 1H), 2.22 (dd, J=7.9, 16.5 Hz, 1H), 1.99 (d, J=9.2 Hz, 2H), 1.95-1.44 (m, 8H), 1.36-1.27 (m, 1H), 0.97 (d, J=6.8 Hz, 3H), 0.92 (d, J=6.8 Hz, 3H). m/z (ESI, +ve ion) 657.2 (M+H)⁺.

Example 1066. (1S,3'R,6'R,7'R,8'E,10'R,11'R)-6-chloro-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'R,11'R)-6-chloro-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'R,8'E,10'S,11'S)-6-chloro-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'S,8'E,10'S,11'S)-6-chloro-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

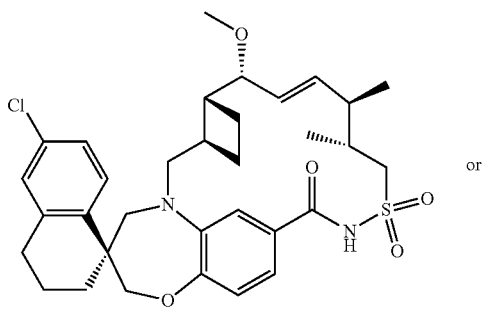

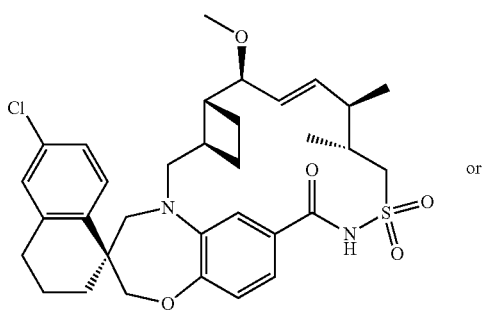

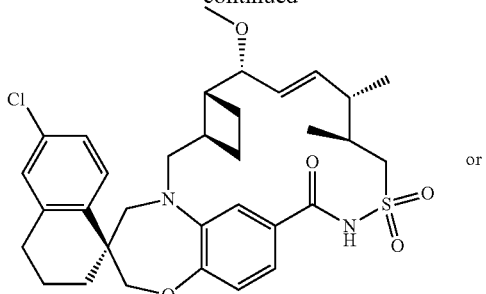

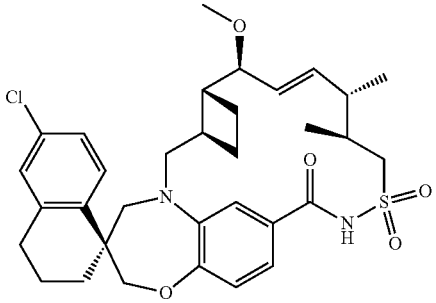

The title compound was prepared in an analogous manner to that described in Example 720 using (1S,3'R,6'R,7'R,8'E,10'R,11'R)-6-Chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,11'R)-6-Chloro-7'-hydroxy-10',11'-dimethyl-3,4-dihydro-2H,15'H-spiro[naphthalene-1,22'-[20]oxa[13]thia[1,14]diazatetracyclo[[14.7.2.0³,⁶.0¹⁹,²⁴]pentacosa[8,16,18,24]tetra en]-15'-one 13',13'-dioxide or (1S,3'R,6'R,7'R,8'E,10'S,11'S)-6-Chloro-7'-hydroxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'S,11'S)-6-Chloro-7'-hydroxy-10',11'-dimethyl-3,4-dihydro-2H,15'H-spiro[naphthalene-1,22'-[20]oxa[13]thia[1,14]diazatetracyclo[[14.7.2.0³,⁶.0¹⁹,²⁴]pentacosa[8,16,18,24]tetra en]-15'-one 13',13'-dioxide (Example 1062), and the desired product, (1S,3'R,6'R,7'R,8'E,10'R,11'R)-6-chloro-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'R,11'R)-6-chloro-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'R,8'E,10'S,11'S)-6-chloro-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,10'S,11'S)-6-chloro-7'-methoxy-10',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide was isolated as a white solid. ¹H NMR (500 MHz, CD₃OD) δ 7.74 (d, J=8.6 Hz, 1H), 7.18 (dd, J=2.4, 8.6 Hz, 1H), 7.12 (d, J=2.2 Hz, 1H), 7.01-6.83 (m, 3H), 6.07 (br. s., 1H), 5.27 (dd, J=9.4, 15.8 Hz, 1H), 4.07 (t, J=11.0 Hz, 3H), 3.67 (d, J=13.4 Hz, 1H), 3.56 (t, J=8.3 Hz, 2H), 3.48-3.38 (m, 2H), 3.23 (s, 3H), 2.86-2.71 (m, 2H), 2.68-

2.56 (m, 1H), 2.27-1.59 (m, 7H), 1.56-1.33 (m, 2H), 1.33-1.18 (s, 3H), 1.07 (d, J=6.6 Hz, 6H). m/z (ESI, +ve ion) 613.2 (M+H)+.

Example 1067. (1S,3'R,6'R,8'E,10'S,11'S,12'R)-6-chloro-10',11',12'-trimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa [8,16,18,24]tetraene]-7',15'-dione 13',13'-dioxide and (1S,3'R,6'R,8'E,10'R,11'S,12'R)-6-chloro-10',11',12'-trimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa [8,16,18,24]tetraene]-7',15'-dione 13',13'-dioxide

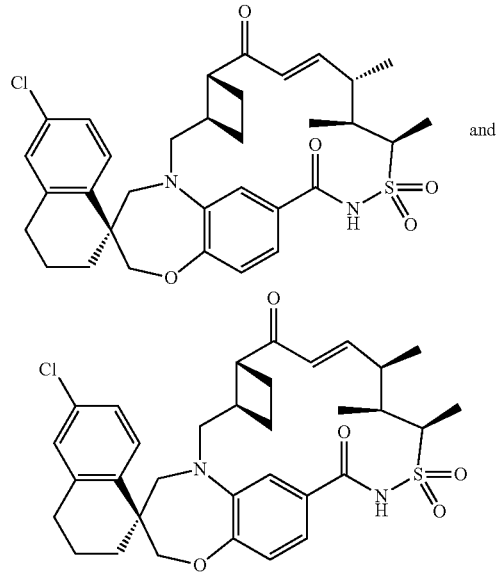

The title compound was prepared in an analogous manner to that described in Example 1059, Steps 1 to 7, but replacing the mixture of ((2R,3R)-2,3-dimethylpent-4-en-1-ol and (2S,3S)-2,3-dimethylpent-4-en-1-ol with a mixture of (2R,3S,4R)-3,4-dimethylhex-5-en-2-ol, (2R,3S,4S)-3,4-dimethylhex-5-en-2-ol in Step 5, and the desired product, a mixture of (1S,3'R,6'R,8'E,10'S,11'S,12'R)-6-chloro-10',11',12'-trimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[8,16,18,24]tetraene]-7',15'-dione 13',13'-dioxide and (1S,3'R,6'R,8'E,10'R,11'S,12'R)-6-chloro-10',11',12'-trimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[8,16,18,24]tetraene]-7',15'-dione 13',13'-dioxide was isolated. ¹H NMR (400 MHz, CDCl₃) δ 8.48-8.37 (m, 1H), 7.79 (d, J=8.4 Hz, 1H), 7.40 (s, 0.67H), 7.26 (d, J=1.6 Hz, 0.33H), 7.22 (dd, J=2.2, 8.6 Hz, 1H), 7.12-7.09 (m, 1H), 6.88-6.82 (m, 2H), 6.58-6.46 (m, 1H), 6.00 (d, J=15.8 Hz, 0.67H), 5.83 (dd, J=1.0, 15.8 Hz, 0.33H), 4.12-4.05 (m, 2H), 3.96-3.83 (m, 3H), 3.24 (d, J=14.5 Hz, 1H), 3.10-2.91 (m, 2H), 2.85-2.72 (m, 2H), 2.42-2.16 (m, 2H), 2.05-1.60 (m, 8H), 1.56 (d, J=7.2 Hz, 2H), 1.50 (d, J=7.4 Hz, 1H), 1.47-1.38 (m, 1H), 1.21 (d, J=7.0 Hz, 2H), 1.12 (d, J=6.8 Hz, 1H), 1.09-1.00 (m, 3H) m/z (ESI, +ve ion) 611.2 (M+H)+.

Example 1068. (1S,3'R,6'R,7'R,8'E,10'S,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'R,8'E,10'R,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

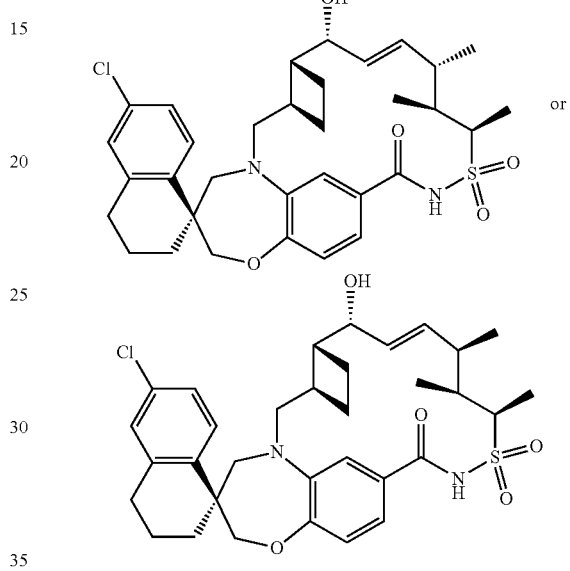

An 50 mL of round bottom flask was charged with a mixture of (1S,3'R,6'R,8'E,10'S,11'S,12'R)-6-chloro-10',11',12'-trimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[8,16,18,24]tetraene]-7',15'-dione 13',13'-dioxide and (1S,3'R,6'R,8'E,10'R,11'S,12'R)-6-chloro-10',11',12'-trimethyl-3,4-dihydro-2H,7'H,15'H-spiro[naphthalene-1,22'-[20]oxa[13]thia[1,14]diazatetracyclo[14.7.2.0³,⁶.0¹⁹,²⁴]pentacosa[8,16,18,24]tetraene]-7',15'-dione 13',13'-dioxide (Example 1067; 46 mg, 0.075 mmol) in 2 mL THF at −20° C., and then (R)-(+)-2-methyl-CBS-oxazaborolidine (1.0 M solution in toluene, 90 μl, 0.090 mmol) and borane tetrahydrofuran complex (1.0 M in tetrahydrofuran, 90 μl, 0.090 mmol) were added under N₂. The reaction mixture was stirred at −20° C. for 30 min, and LC-MS showed the reaction was completely. The reaction was quenched with MeOH, and concentrated and purified by reversed phase preparative HPLC (Gemini™ Prep C₁₈ 5 μm column; Phenomenex, Torrance, CA; gradient elution of 30% to 95% MeCN in water, where both solvents contain 0.1% TFA, 30 min method) to give (1S,3'R,6'R,7'R,8'E,10'S,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'R,8'E,10'R,11'S,12'R)-6-chloro-7'-hydroxy-10',11,12'-trimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (32.5 mg, 0.053 mmol) (first eluting major peak out of preparative reverse phase HPLC). ¹H NMR (400 MHz, CD₃OD) δ 7.77 (d, J=8.6 Hz, 1H), 7.58 (d, J=2.0 Hz, 1H), 7.23-7.17 (m, 2H), 7.13 (d, J=2.2 Hz, 1H), 6.94 (d, J=8.2 Hz, 1H), 5.40-5.31 (m, 2H), 4.12 (s, 2H), 3.90 (dd, J=8.9, 15.7 Hz, 1H), 3.76 (d, J=14.5 Hz, 1H), 3.70 (dd, J=6.5, 14.7 Hz, 1H), 3.39 (d, J=5.3 Hz, 1H), 3.04 (d, J=15.1 Hz, 1H), 2.87-2.73 (m, 2H), 2.68-2.57 (m, 2H), 2.44 (d, J=7.2 Hz, 1H), 2.27 (d, J=6.8 Hz, 1H), 2.08 (d, J=12.9 Hz, 1H), 1.98-1.82 (m, 5H), 1.74-1.59 (m, 2H), 1.49 (d, J=2.7 Hz, 1H), 1.42 (d, J=7.2 Hz, 3H), 1.18 (d, J=7.2 Hz, 3H), 0.97 (d, J=6.8 Hz, 3H). m/z (ESI, +ve ion) 613.2 (M+H)+.

Example 1069. (1S,3'R,6'R,7'R,8'E,10'R,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'R,8'E,10'S,11'S,12'R)-6-chloro-7'-hydroxy-10',11',12'-trimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

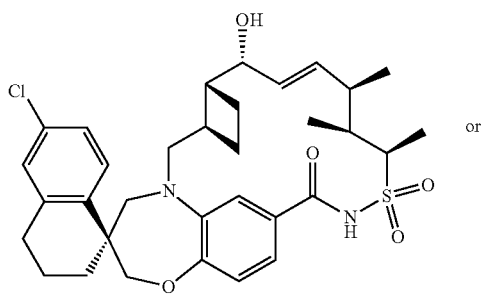

or

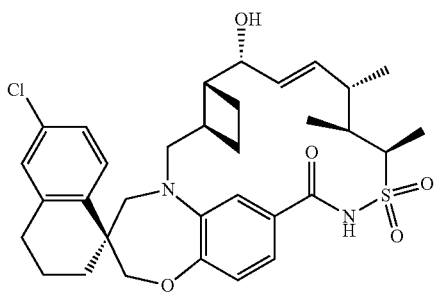

The title compound was obtained as a single isomer (second eluting major peak) from the reverse phase preparative HPLC in Example 1068. $^1$H NMR (400 MHz, CD$_3$OD) δ 7.77 (d, J=8.4 Hz, 1H), 7.65 (d, J=2.2 Hz, 1H), 7.21 (dd, J=2.0, 7.7 Hz, 2H), 7.13 (d, J=2.3 Hz, 1H), 6.95 (d, J=8.2 Hz, 1H), 5.41 (dd, J=9.0, 15.3 Hz, 1H), 5.15 (dd, J=8.3, 15.9 Hz, 1H), 4.13 (s, 2H), 3.96-3.81 (m, 2H), 3.73 (d, J=14.9 Hz, 1H), 3.42 (d, J=8.8 Hz, 1H), 3.06 (d, J=13.7 Hz, 1H), 2.87-2.73 (m, 2H), 2.61 (br. s., 2H), 2.11-1.84 (m, 8H), 1.76-1.61 (m, 2H), 1.52-1.40 (m, 1H), 1.36 (d, J=7.4 Hz, 3H), 1.08 (d, J=6.7 Hz, 3H), 0.98 (d, J=6.7 Hz, 3H). m/z (ESI, +ve ion) 613.2 (M+H)+.

Example 1070. (1S,3'R,6'R,7'R,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl acetate

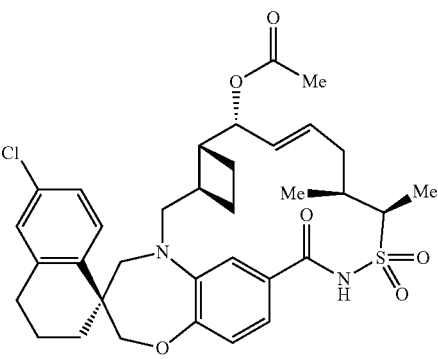 [SMILES: CC(=O)O[C@@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

To a mixture of (1S,3'R,6'R,7'R,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 208; 252 mg, 0.421 mmol), 4-dimethylaminopyridine (5.14 mg, 0.042 mmol, Aldrich) and triethylamine (21 µl, 1.47 mmol, Aldrich) in DCM (2.1 mL) at rt was added neat acetic anhydride (119 µl, 1.26 mmol) all at once. The reaction was stirred at rt for 2 h then partitioned between 20 ml of DCM and 20 mL of water. The aqueous separation was extracted again with 20 ml DCM. The combined organic extracts were stirred over anhydrous magnesium sulfate, filtered and the filtrate concentrated and purified by chromatography on 80 g RediSep Rf Gold column eluting with 20% EtOAc in hexane to give (1S,3'R,6'R,7'R,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl acetate (228 mg, 0.356 mmol). $^1$H NMR (400 MHz, CDCl$_3$) δ 8.06 (s, 1H), 7.74 (d, J=8.4 Hz, 1H), 7.22 (dd, J=2.3, 8.4 Hz, 1H), 7.12 (d, J=2.3 Hz, 1H), 6.98-6.93 (m, 2H), 5.77-5.66 (m, 1H), 5.65-5.55 (m, 1H), 5.30 (br. s., 1H), 4.24 (q, J=7.2 Hz, 1H), 3.91 (d, J=14.1 Hz, 1H), 3.74 (d, J=13.5 Hz, 1H), 3.22 (d, J=14.3 Hz, 1H), 3.01 (dd, J=8.7, 15.2 Hz, 1H), 2.81 (d, J=4.3 Hz, 2H), 2.60-2.45 (m, 2H), 2.34 (s, 3H), 2.10-1.68 (m, 13H), 1.48 (d, J=7.2 Hz, 3H), 1.46-1.36 (m, 1H), 1.08 (d, J=5.9 Hz, 3H). m/z (ESI, +ve ion) 641.2 (M+H)+.

Example 1071. ((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)acetic Acid

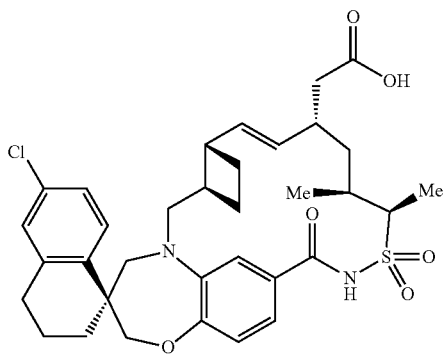 [SMILES: C[C@@H]1[C@@H](C)C[C@@H](CC(=O)O)/C=C/[C@@H]2CC[C@H]2CN2C[C@@]3(CCCc4cc(Cl)ccc43)COc3ccc(cc32)C(=O)NS1(=O)=O]

To a solution of (1S,3'R,6'R,7'R,8'E,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl acetate (Example 1070; 20 mg, 0.033 mmol) and chlorotrimethylsilane (18.13 mg, 0.17 mmol) dissolved in THF (1 mL) cooled by an acetone-dry ice bath was added lithium diisopropylamidesolution (2.0 M in THF/heptane/ethylbenzene, 0.05 mL, 0.10 mmol, Aldrich) all at once. The reaction was left stirring at −78° C. for 3 h then the cold bath was removed and the reaction equilibrated to rt over 30 min. The reaction was stirred at rt for 2 h then partitioned between 20 ml each saturated aqueous ammonium chloride and ethyl acetate. The aqueous separation was extracted again with 20 ml ethyl acetate. LC-MS showed the mixtue of the desired product and TMS ester were formed. The combined organic extracts were conc amd purified by reverse phase preparative HPLC (Gemini™ Prep C$_{18}$ 5 μm column; Phenomenex, Torrance, CA; gradient elution of 40% to 95% MeCN in water, where both solvents contain 0.1% TFA, 30 min method) to give ((1S,3'R,6'S,7'E,9'S,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)acetic acid (5.3 mg, 8.27 μmol). $^1$H NMR (500 MHz, CDCl$_3$) δ 7.88 (br. s., 1H), 7.61 (d, J=8.6 Hz, 1H), 7.11 (dd, J=1.8, 8.4 Hz, 1H), 7.02 (s, 1H), 6.93-6.83 (m, 2H), 6.75 (br. s., 1H), 5.55 (dd, J=7.2, 15.3 Hz, 1H), 5.07 (dd, J=8.8, 15.4 Hz, 1H), 4.04 (s, 2H), 3.80 (d, J=7.3 Hz, 1H), 3.71-3.56 (m, 2H), 3.26-3.14 (m, 2H), 2.72-1.91 (m, 11H), 1.84 (dd, J=3.9, 9.0 Hz, 1H), 1.74 (d, J=4.6 Hz, 1H), 1.67-1.48 (m, 2H), 1.44-1.39 (m, 1H), 1.37 (d, J=7.3 Hz, 3H), 1.32-1.13 (m, 3H), 0.94 (d, J=6.8 Hz, 3H). m/z (ESI, +ve ion) 641.2 (M+H)$^+$.

Example 1072. 2-((1S,3'R,6'S,7'E,9'R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)-N,N-dimethylacetamide

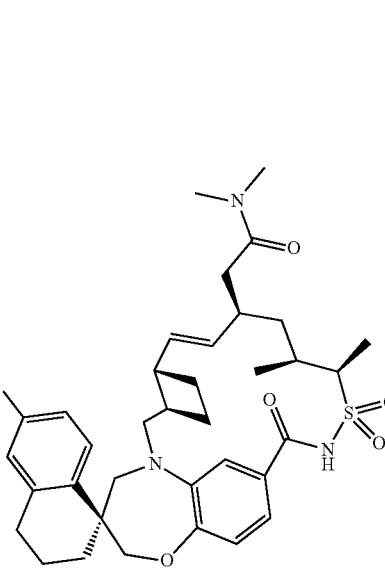

The title compound was prepared in an analogous manner to that described in Example 995 using ((1S,3'R,6'S,7'E,9'R,11'S,12'R)-6-chloro-11,12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)acetic acid (Example 206) and dimethylamine (40 wt % solution in water, Acros), and the desired product, 2-((1S,3'R,6'S,7'E,9'R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)-N,N-dimethylacetamide was isolated as a white solid. $^1$H NMR (500 MHz, CDCl$_3$) δ 7.92 (s, 1H), 7.73 (d, J=8.6 Hz, 1H), 7.20 (dd, J=2.2, 9.0 Hz, 1H), 7.11 (d, J=2.2 Hz, 1H), 7.04 (s, 1H), 7.00-6.93 (m, 2H), 5.89 (dd, J=4.8, 15.5 Hz, 1H), 5.32 (dd, J=7.8, 15.9 Hz, 1H), 4.29-4.23 (m, 1H), 4.17 (s, 1H), 4.15 (s, 2H), 3.85 (d, J=15.7 Hz, 1H), 3.66 (d, J=14.2 Hz, 1H), 3.20 (d, J=14.2 Hz, 1H), 3.08 (dd, J=8.3, 15.2 Hz, 1H), 3.04 (s, 3H), 2.96 (s, 3H), 2.82-2.74 (m, 2H), 2.64 (br. s., 1H), 2.56 (br. s., 1H), 2.36 (dd, J=4.0, 15.0 Hz, 1H), 2.30-2.18 (m, 2H), 2.03 (t, J=8.4 Hz, 3H), 1.98-1.89 (m, 2H), 1.87-1.71 (m, 4H), 1.50 (d, J=7.1 Hz, 5H), 1.01 (d, J=6.8 Hz, 3H). m/z (ESI, +ve ion) 668.2 (M+H)$^+$.

2101

Example 1073. 2-((1S,3'R,6'S,7'E,9'R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)-N-methylacetamide

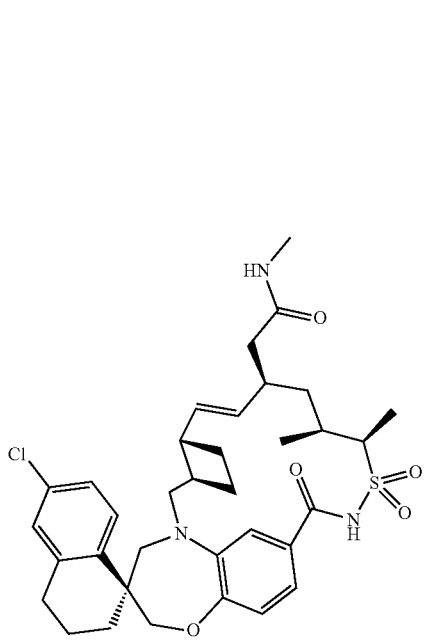 [SMILES: CNC(=O)C[C@@H]1/C=C/[C@@H]2CC[C@H]2CN2C[C@@]3(CCCc4cc(Cl)ccc43)COc3ccc(cc32)C(=O)NS(=O)(=O)[C@H](C)[C@@H](C)C1]

The title compound was prepared in an analogous manner to that described in Example 995 using ((1S,3'R,6'S,7'E,9'R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)acetic acid (Example 206) and methanamine (30 wt % solution in water, Aldrich), and the desired product, 2-((1S,3'R,6'S,7'E,9'R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)-N-methylacetamide was isolated as a white solid. $^1$H NMR (400 MHz, CD$_3$OD) δ 7.65 (d, J=8.6 Hz, 1H), 7.08 (dd, J=2.3, 8.4 Hz, 1H), 7.02 (d, J=2.3 Hz, 1H), 6.99 (t, J=3645.7 Hz, 1H), 6.95 (d, J=1.8 Hz, 1H), 6.85 (d, J=8.0 Hz, 1H), 5.76 (dd, J=5.1, 15.5 Hz, 1H), 5.21 (dd, J=6.7, 15.0 Hz, 1H), 4.07-4.00 (m, 3H), 3.71 (d, J=15.7 Hz, 1H), 3.52 (d, J=14.5 Hz, 1H), 3.15 (d, J=14.1 Hz, 1H), 3.05 (dd, J=8.6, 15.7 Hz, 1H), 2.72-2.65 (m, 2H), 2.62 (s, 3H), 2.54-2.43 (m, 2H), 2.16-2.06 (m, 2H), 2.00-1.77 (m, 8H), 1.76-1.57 (m, 2H), 1.46-1.32 (m, 2H), 1.27 (d, J=7.2 Hz, 3H), 0.92 (d, J=6.8 Hz, 3H). m/z (ESI, +ve ion) 654.2 (M+H)$^+$.

2102

Example 1074. (1S,3'R,6'S,7'E,9'R,11'S,12'R)-6-chloro-9'-(2-(3-hydroxy-1-azetidinyl)-2-oxoethyl)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide

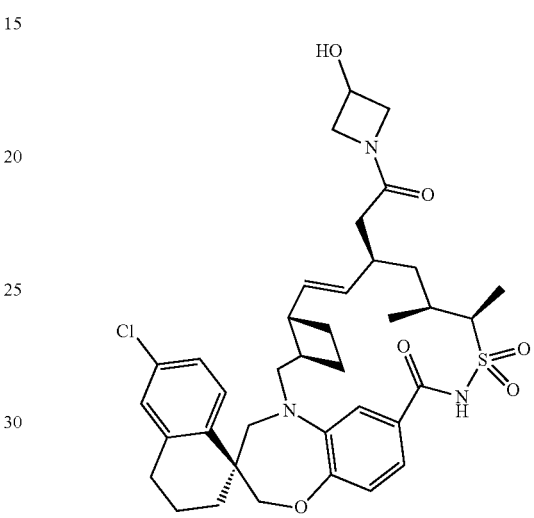

The title compound was prepared in an analogous manner to that described in Example 995 using ((1S,3'R,6'S,7'E,9'R,11'S,12'R)-6-chloro-11,12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)acetic acid (Example 206) and 3-(hydroxy)azetidine hydrochloride (Oakwood), and the desired product, (1S,3'R,6'S,7'E,9'R,11'S,12'R)-6-chloro-9'-(2-(3-hydroxy-1-azetidinyl)-2-oxoethyl)-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[7,16,18,24]tetraen]-15'-one 13',13'-dioxide was isolated as a white solid. $^1$H NMR (400 MHz, CD$_3$OD) δ 7.76 (d, J=8.4 Hz, 1H), 7.19 (dd, J=2.3, 8.4 Hz, 1H), 7.13 (d, J=2.2 Hz, 1H), 7.10 (dd, J=1.9, 8.1 Hz, 1H), 7.05 (d, J=1.8 Hz, 1H), 6.96 (d, J=8.0 Hz, 1H), 5.90 (dd, J=5.1, 15.7 Hz, 1H), 5.39-5.32 (m, 1H), 4.61-4.55 (m, 1H), 4.40 (t, J=9.5 Hz, 1H), 4.22-4.11 (m, 4H), 3.97 (dt, J=4.1, 9.5 Hz, 1H), 3.82 (d, J=15.3 Hz, 1H), 3.76 (td, J=5.3, 10.5 Hz, 1H), 3.63 (d, J=13.9 Hz, 1H), 3.17 (dd, J=8.7, 15.0 Hz, 1H), 2.85-2.73 (m, 2H), 2.61 (dd, J=7.2, 16.4 Hz, 2H), 2.23 (t, J=8.7 Hz, 1H), 2.19-2.12 (m, 1H), 2.11-1.78 (m, 9H), 1.73 (dd, J=10.0, 19.2 Hz, 1H), 1.57-1.44 (m, 2H), 1.41 (d, J=7.0 Hz, 3H), 1.37-1.29 (m, 1H), 1.03 (dd, J=1.3, 6.9 Hz, 3H). m/z (ESI, +ve ion) 696.2 (M+H)$^+$.

Example 1075. ((1S,3'R,6'S,7'E,9'R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)acetonitrile

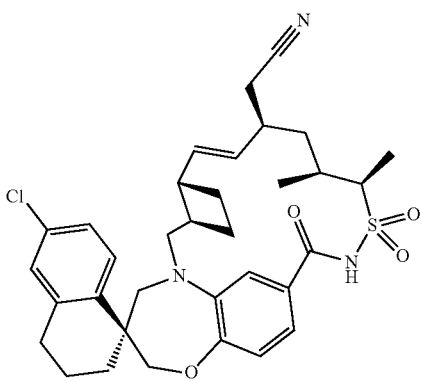 [SMILES: C[C@@H]1[C@@H](C)C[C@H](CC#N)/C=C/[C@@H]2CC[C@H]2CN2C[C@@]3(CCCc4cc(Cl)ccc43)COc3ccc(cc32)C(=O)NS1(=O)=O]

Step 1: 2-((1S,3'R,6'S,7'E,9'R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)acetamide

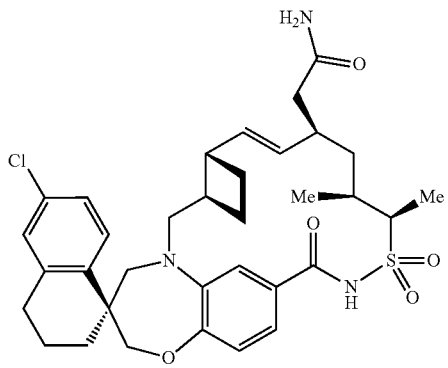

The title compound was prepared in an analogous manner to that described in Example 995 using ((1S,3'R,6'S,7'E,9'R,11'S,12'R)-6-chloro-11,12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)acetic acid (Example 206) and 28% ammonium hydroxide.

Step 2: ((1S,3'R,6'S,7'E,9'R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [7,16,18,24]tetraen]-9'-yl)acetonitrile A solution of 2-((1S,3'R,6'S,7'E,9'R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)acetamide (Step 1; 5.8 mg, 9.06 μmol) in phosphorus oxychloride (41.5 μl, 0.45 mmol) was heated at 60° C. from 2 h. The reaction was concentrated and purified by reverse phase preparative HPLC (Gemini™ Prep C$_{18}$ 5 μm column; Phenomenex, Torrance, CA; gradient elution of 40% to 95% MeCN in water, where both solvents contain 0.1% TFA, 30 min method) to give ((1S,3'R,6'S,7'E,9'R,11'S,12'R)-6-chloro-11',12'-dimethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[7,16,18,24]tetraen]-9'-yl)acetonitrile (4.5 mg, 7.23 μmol) as a white solid. $^1$H NMR (500 MHz, CD$_3$OD) δ 7.76 (d, J=8.6 Hz, 1H), 7.19 (dd, J=2.2, 8.6 Hz, 1H), 7.13 (d, J=2.0 Hz, 1H), 7.11 (dd, J=2.0, 8.1 Hz, 1H), 7.04 (d, J=1.7 Hz, 1H), 6.96 (d, J=8.1 Hz, 1H), 6.01 (dd, J=5.1, 15.7 Hz, 1H), 5.35 (dd, J=5.7, 15.5 Hz, 1H), 4.15 (s, 2H), 4.05 (dd, J=2.2, 7.8 Hz, 1H), 3.82 (d, J=15.2 Hz, 1H), 3.62 (d, J=13.9 Hz, 1H), 3.18 (dd, J=9.3, 15.9 Hz, 1H), 2.85-2.74 (m, 2H), 2.68-2.60 (m, 1H), 2.52-2.45 (m, 3H), 2.25 (quin, J=8.9 Hz, 1H), 2.11-1.99 (m, 4H), 1.95-1.70 (m, 5H), 1.65-1.47 (m, 3H), 1.46 (d, J=7.1 Hz, 3H), 1.07 (d, J=6.8 Hz, 3H). m/z (ESI, +ve ion) 622.2 (M+H)$^+$.

Example 1076. N-((1S,3'R,6'R,7'R,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)acetamide

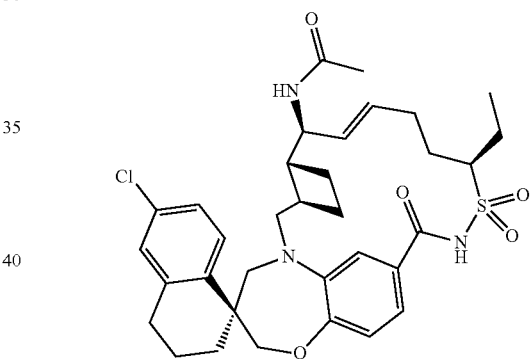

Step 1: (3S)-5-(((1R,2R)-2-((1S)-1-amino-2-propen-1-yl)cyclobutyl)methyl)-6'-chloro-N-((3R)-6-hepten-3-ylsulfonyl)-3',4',5-tetrahydro-2'H-spiro[1,5-benzoxazepine-3,1'-naphthalene]-7-carboxamide

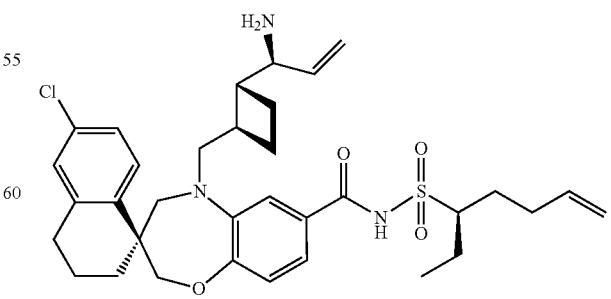

The title compound was prepared in an analogous manner to that described in Example 599, Steps 1 to 5, but replacing Intermediate EE20 with Intermediate EE21 in Step 4, and the desired product, (3S)-5-(((1R,2R)-2-((1S)-1-amino-2-propen-1-yl)cyclobutyl)methyl)-6'-chloro-N-((3R)-6-hepten-3-ylsulfonyl)-3',4',5-tetrahydro-2'H-spiro[1,5-benzoxazepine-3,1'-naphthalene]-7-carboxamide was isolated as a white solid.

Step 2: N-((1S,3'R,6'R,7'R,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24] tetraen]-7'-yl)acetamide The title compound was prepared in an analogous manner to that described in in Example 599, Steps 6 to 9 from (3S)-5-(((1R,2R)-2-((1S)-1-amino-2-propen-1-yl)cyclobutyl)methyl)-6'-chloro-N-((3R)-6-hepten-3-ylsulfonyl)-3',4',5-tetrahydro-2'H-spiro[1,5-benzoxazepine-3,1'-naphthalene]-7-carboxamide (Example 1076, Step 1), but replacing methyl bromoacetate with acetyl chloride (Aldrich) in Example 599, Step 9, and the desired product, N-((1S,3'R,6'R,7'R,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)acetamide was isolated as a white solid. $^1$H NMR (400 MHz, CD$_3$OD) δ 7.77 (d, J=8.4 Hz, 1H), 7.19 (dd, J=2.5, 8.6 Hz, 1H), 7.12 (d, J=2.3 Hz, 1H), 7.10-7.02 (m, 2H), 6.87 (d, J=8.0 Hz, 1H), 6.03 (dd, J=6.7, 14.7 Hz, 1H), 5.55 (dd, J=7.5, 15.2 Hz, 1H), 4.62-4.46 (m, 1H), 4.16-4.00 (m, 2H), 3.92-3.81 (m, 2H), 3.74-3.60 (m, 1H), 3.05 (dd, J=9.8, 15.1 Hz, 1H), 2.86-2.74 (m, 2H), 2.63-2.30 (m, 3H), 2.22-2.02 (m, 4H), 1.95 (s, 3H), 1.95-1.61 (m, 9H), 1.43 (d, J=8.6 Hz, 1H), 1.15 (t, J=7.5 Hz, 3H). m/z (ESI, +ve ion) 640.2 (M+H)$^+$.

Example 1077. N-((1S,3'R,6'R,7'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)-2-methylpropanamide

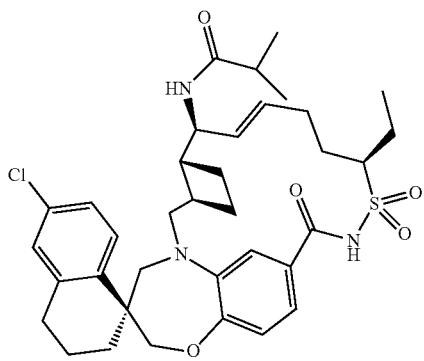 [SMILES: CC[C@@H]1CC/C=C/[C@H](NC(=O)C(C)C)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 1076, but replacing acetyl chloride with 2-methylpropanoyl chloride (Aldrich) in Step 9, and the desired product, N-((1S,3'R,6'R,7'S,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)-2-methylpropanamide was isolated. $^1$H NMR (400 MHz, CD$_3$OD) δ 7.75 (d, J=8.6 Hz, 1H), 7.19 (dd, J=2.3, 8.8 Hz, 1H), 7.13 (d, J=2.0 Hz, 1H), 7.02 (dd, J=2.0, 8.0 Hz, 1H), 6.97 (d, J=1.6 Hz, 1H), 6.95 (d, J=8.0 Hz, 1H), 5.88-5.73 (m, 1H), 5.66 (dd, J=0.6, 15.8 Hz, 1H), 4.48 (d, J=8.4 Hz, 1H), 4.15-4.04 (m, 2H), 4.01 (d, J=6.1 Hz, 1H), 3.93 (d, J=15.3 Hz, 1H), 3.69 (d, J=14.5 Hz, 1H), 3.07 (dd, J=9.2, 15.3 Hz, 1H), 2.87-2.73 (m, 2H), 2.46-2.33 (m, 4H), 2.15-2.03 (m, 3H), 2.00-1.84 (m, 7H), 1.84-1.66 (m, 3H), 1.46 (t, J=11.1 Hz, 1H), 1.19 (t, J=7.5 Hz, 3H), 1.10 (dd, J=5.0, 6.7 Hz, 6H). m/z (ESI, +ve ion) 668.2 (M+H)$^+$.

Example 1078. N-((1S,3'R,6'R,7'R,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24]tetraen]-7'-yl)acetamide and Example 1079. N-((1S,3'R,6'R,7'R,8'Z,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [8,16,18,24] tetraen]-7'-yl)acetamide Example 1078

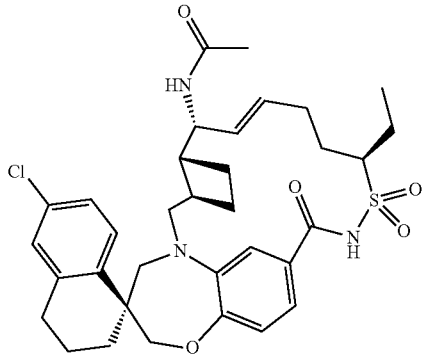

Example 1079

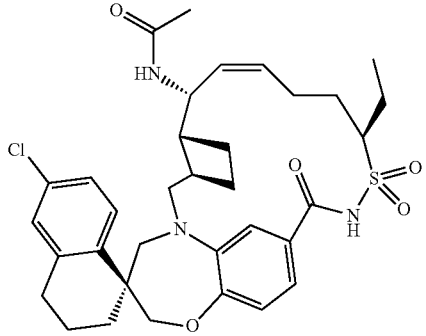

Step 1: (3S)-5-(((1R,2R)-2-((1R)-1-amino-2-propen-1-yl)cyclobutyl)methyl)-6'-chloro-N-((3R)-6-hepten-3-ylsulfonyl)-3',4,4',5-tetrahydro-2'H-spiro[1,5-benzoxazepine-3,1'-naphthalene]-7-carboxamide

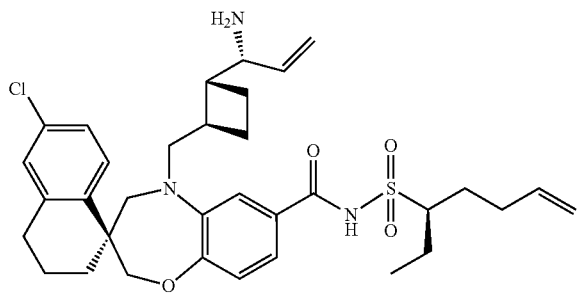 [SMILES: C=CCC[C@@H](CC)S(=O)(=O)NC(=O)c1ccc2c(c1)N(C[C@@H]1CC[C@H]1[C@H](N)C=C)C[C@@]1(CCCc3cc(Cl)ccc31)CO2]

The title compound was prepared in an analogous manner to that described in Example 599, Steps 1 to 5, but replacing (R)-(+)-2-methyl-2-propanesulfinamide with (S)-(−)-2-methyl-2-propane-sulfinamide in Step 1, and the desired product, (3S)-5-(((1R,2R)-2-((1R)-1-amino-2-propen-1-yl)cyclobutyl)methyl)-6'-chloro-N-((3R)-6-hepten-3-ylsulfonyl)-3',4,4',5-tetrahydro-2'H-spiro[1,5-benzoxazepine-3,1'-naphthalene]-7-carboxamide was isolated.

Step 2. N-((1S,3'R,6'R,7'R,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[[14.7.2.0$^{3,6}$.0$^{19,24}$]pentacosa[8,16,18,24]tetraen]-7'-yl)acetamide and N-((1S,3'R,6'R,7'R,8'Z,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)acetamide The title compound was prepared in an analogous manner to that described in Example 599, Steps 6 to 9, using (3S)-5-(((1R,2R)-2-((1R)-1-amino-2-propen-1-yl)cyclobutyl)methyl)-6'-chloro-N-((3R)-6-hepten-3-ylsulfonyl)-3',4,4',5-tetrahydro-2'H-spiro[1,5-benzoxazepine-3,1'-naphthalene]-7-carboxamide (Example 1078, Step 1), but replacing methyl bromoacetate with acetyl chloride (Aldrich) in Example 599, Step 9 and the desired products, N-((1S,3'R,6'R,7'R,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)acetamide (second eluting peak) and N-((1S,3'R,6'R,7'R,8'Z,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)acetamide (first eluting peak) were isolated as a white solid. N-((1S,3'R,6'R,7'R,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)acetamide (Example 1078). $^1$H NMR (500 MHz, CD$_3$OD) δ 7.80 (d, J=8.6 Hz, 1H), 7.41 (d, J=1.7 Hz, 1H), 7.18 (ddd, J=2.1, 8.4, 14.2 Hz, 2H), 7.11 (d, J=2.2 Hz, 1H), 6.93 (d, J=8.1 Hz, 1H), 5.49-5.37 (m, 2H), 4.15-4.05 (m, 3H), 3.87-3.77 (m, 2H), 3.73-3.63 (m, 1H), 3.21 (d, J=14.7 Hz, 1H), 3.06 (dd, J=5.1, 15.4 Hz, 1H), 2.85-2.73 (m, 2H), 2.69-2.62 (m, 1H), 2.46-2.27 (m, 2H), 2.10-1.98 (m, 4H), 1.98-1.93 (m, 1H), 1.93 (s, 3H), 1.92-1.78 (m, 5H), 1.77-1.62 (m, 2H), 1.50-1.42 (m, 1H), 1.18 (t, J=7.5 Hz, 3H). m/z (ESI, +ve ion) 640.2 (M+H)$^+$; and N-((1S,3'R,6'R,7'R,8'Z,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa[8,16,18,24]tetraen]-7'-yl)acetamide Example 1079]. $^1$H NMR (400 MHz, CD$_3$OD) δ 7.76 (d, J=8.4 Hz, 1H), 7.20 (dd, J=2.3, 8.6 Hz, 1H), 7.13 (d, J=2.2 Hz, 1H), 7.09 (s, 1H), 7.04 (dd, J=2.0, 8.0 Hz, 1H), 6.94 (d, J=8.0 Hz, 1H), 5.53-5.37 (m, 1H), 5.29 (t, J=10.1 Hz, 1H), 4.62 (t, J=8.5 Hz, 1H), 4.09 (dd, J=12.1, 22.3 Hz, 2H), 3.78-3.66 (m, 3H), 3.19-3.10 (m, 1H), 2.87-2.73 (m, 2H), 2.59 (br. s., 1H), 2.48-2.30 (m, 2H), 2.26-2.00 (m, 4H), 1.99-1.90 (m, 3H), 1.88 (s, 3H), 1.87-1.70 (m, 6H), 1.53-1.45 (m, 1H), 1.17 (t, J=7.4 Hz, 3H). m/z (ESI, +ve ion) 640.2 (M+H)$^+$.

Example 1080. N-((1S,3'R,6'R,7'R,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$]pentacosa [16,18,24]trien]-7'-yl)acetamide

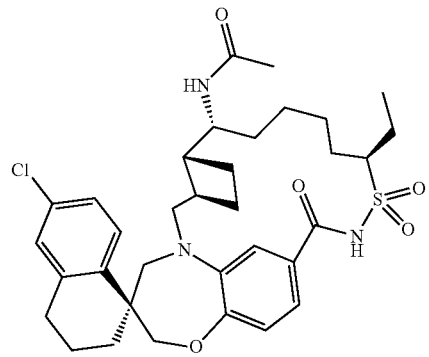 [SMILES: CC[C@@H]1CCCC[C@@H](NC(C)=O)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 925, Step 1, using N-((1S,3'R,6'R,7'R,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0~3,6~.0~19,24~]pentacosa[8,16,18,2 4]tetraen]-7'-yl)acetamide (Example 1078), and the desired products, N-((1S,3'R,6'R,7'R,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0$^{3,6}$.0$^{19,24}$pentacosa[16,18,24]trien]-7'-yl)acetamide was isolated. $^1$H NMR (400 MHz, CD$_3$OD) δ 7.76 (d, J=8.4 Hz, 1H), 7.22 (d, J=2.2 Hz, 1H), 7.19 (dd, J=2.3, 8.6 Hz, 1H), 7.12 (d, J=2.2 Hz, 1H), 7.10 (dd, J=2.0, 7.4 Hz, 1H), 6.96 (d, J=8.0 Hz, 1H), 4.11 (dd, J=11.9, 22.9 Hz, 2H), 3.83-3.71 (m, 3H), 3.66 (br. s., 1H), 3.16 (dd, J=7.0, 14.9 Hz, 1H), 2.86-2.73 (m, 2H), 2.54-2.39 (m, 2H), 2.14-2.03 (m, 2H), 2.02-1.62 (m, 10H), 1.97 (s, 3H), 1.61-1.35 (m, 5H), 1.17 (t, J=7.5 Hz, 3H). m/z (ESI, +ve ion) 642.2 (M+H)$^+$.

Example 1081. N-((1S,3'R,6'R,7'R,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl)-2-methylpropanamide and Example 1082. N-((1S,3'R,6'R,7'R,8'Z,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl)-2-methylpropanamide

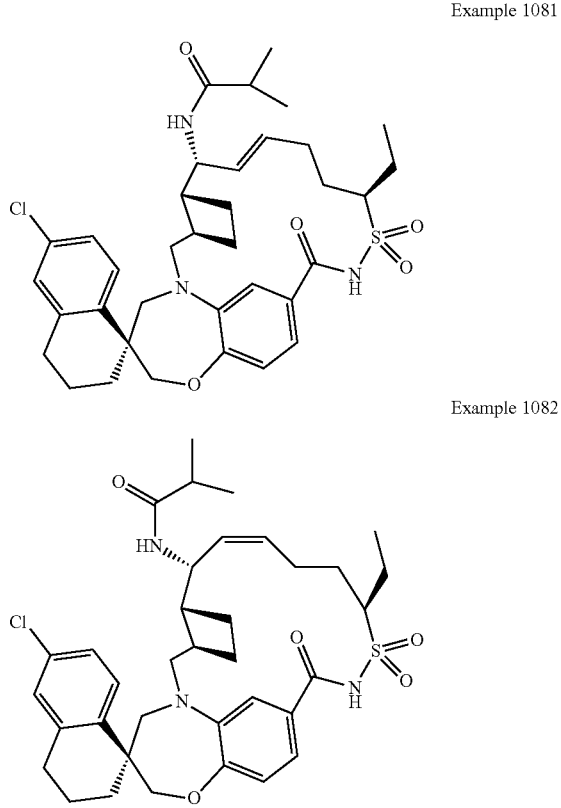

Example 1081

Example 1082

The title compounds were prepared in an analogous manner to that described in Examples 1078 and 1079, but replacing acetyl chloride with 2-methylpropanoyl chloride (Aldrich) in Step 9, and the desired products, N-((1S,3'R,6'R,7'R,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl)-2-methylpropanamide and N-((1S,3'R,6'R,7'R,8'Z,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl)-2-methylpropanamide were isolated. N-((1S,3'R,6'R,7'R,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl)-2-methylpropanamide (Example 1081). $^1$H NMR (400 MHz, CD$_3$OD) δ 7.80 (d, J=8.6 Hz, 1H), 7.41 (d, J=2.0 Hz, 1H), 7.21-7.12 (m, 2H), 7.11 (d, J=2.0 Hz, 1H), 6.95 (d, J=8.2 Hz, 1H), 5.43 (d, J=5.3 Hz, 2H), 4.13-4.06 (m, 3H), 3.95-3.76 (m, 3H), 3.69 (d, J=5.7 Hz, 2H), 3.19-3.01 (m, 1H), 2.84-2.74 (m, 2H), 2.67 (d, J=12.3 Hz, 1H), 2.53-2.26 (m, 3H), 2.11-1.88 (m, 7H), 1.88-1.79 (m, 2H), 1.76-1.59 (m, 2H), 1.54-1.42 (m, 1H), 1.18 (t, J=7.4 Hz, 3H), 1.06 (d, J=6.8 Hz, 3H), 1.00 (d, J=6.8 Hz, 3H). m/z (ESI, +ve ion) 668.2 (M+H)⁺; N-((1S,3'R,6'R,7'R,8'Z,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl)-2-methylpropanamide (Example 1082). $^1$H NMR (500 MHz, CD$_3$OD) δ 7.75 (d, J=8.6 Hz, 1H), 7.18 (dd, J=2.3, 8.4 Hz, 1H), 7.12 (d, J=2.2 Hz, 1H), 7.10 (br. s., 1H), 7.04 (d, J=8.1 Hz, 1H), 6.94 (d, J=8.1 Hz, 1H), 5.49 (td, J=6.7, 10.8 Hz, 1H), 5.30 (t, J=10.0 Hz, 1H), 4.62 (q, J=8.6 Hz, 1H), 4.08 (t, J=3061.3 Hz, 2H), 3.75 (d, J=14.7 Hz, 1H), 3.69 (br. s., 2H), 3.13 (dd, J=7.0, 15.3 Hz, 1H), 2.86-2.74 (m, 2H), 2.62-2.51 (m, 1H), 2.46-2.23 (m, 4H), 2.18-2.01 (m, 4H), 1.98-1.78 (m, 6H), 1.75-1.66 (m, 2H), 1.49 (t, J=11.4 Hz, 1H), 1.16 (t, J=7.5 Hz, 3H), 1.04 (t, J=6.7 Hz, 6H). m/z (ESI, +ve ion) 668.2 (M+H)⁺.

Example 1083. N-((1S,3'R,6'R,7'R,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[16,18,24]trien]-7'-yl)-2-methylpropanamide

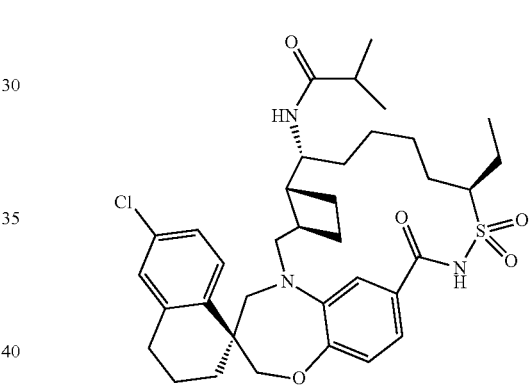

The title compound was prepared in an analogous manner to that described in Example 925, Step 1, using N-((1S,3'R,6'R,7'R,8'E,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[8,16,18,24]tetraen]-7'-yl)-2-methylpropanamide (Example 1081), and the desired product, N-((1S,3'R,6'R,7'R,12'R)-6-chloro-12'-ethyl-13',13'-dioxido-15'-oxo-3,4-dihydro-2H-spiro[naphthalene-1,22'-[20]oxa[13]thia[1,14]diazatetracyclo[14.7.2.0³,⁶.0¹⁹,²⁴]pentacosa[16,18,24]trien]-7'-yl)-2-methylpropanamide was isolated. $^1$H NMR (500 MHz, CD$_3$OD) δ 7.77 (d, J=8.2 Hz, 1H), 7.42 (d, J=5.9 Hz, 1H), 7.22 (d, J=1.5 Hz, 1H), 7.19 (dd, J=2.1, 8.4 Hz, 1H), 7.15-7.09 (m, 2H), 6.96 (dd, J=1.2, 8.0 Hz, 1H), 4.11 (dd, J=12.0, 18.8 Hz, 2H), 3.82-3.76 (m, 2H), 3.74 (d, J=14.7 Hz, 1H), 3.64 (ddd, J=4.6, 8.8, 13.2 Hz, 1H), 3.15 (dd, J=7.2, 15.3 Hz, 1H), 2.85-2.73 (m, 2H), 2.56-2.41 (m, 3H), 2.11-2.02 (m, 2H), 1.99 (d, J=6.8 Hz, 1H), 1.96-1.82 (m, 5H), 1.79-1.62 (m, 3H), 1.62-1.45 (m, 4H), 1.43-1.33 (m, 2H), 1.33-1.24 (m, 2H), 1.17 (t, J=7.5 Hz, 3H), 1.12 (d, J=6.8 Hz, 3H), 1.06 (d, J=6.6 Hz, 3H). m/z (ESI, +ve ion) 670.3 (M+H)⁺.

Example 1084. (1S,3'R,6'R)-6-chloro-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide

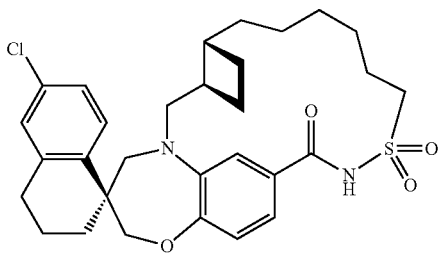

A mixture of Example 858 (0.004 g, 7 μmol) and platinum (IV) oxide (1.6 mg, 7 μmol) in EtOAc (1.2 mL) was stirred under H$_2$ at rt for 40 min. The reaction mixture was filtered through syringe filter to remove solid catalyst. The filtrate was concentrated to provide the title compound (3.4 mg) as a white solid. $^1$H NMR (400 MHz, CD$_2$Cl$_2$) δ 8.11 (m, 1H), 7.72 (m, 1H), 7.17 (m, 1H), 7.09 (m, 1H), 6.99 (m, 1H), 6.93 (s, 2H), 4.11 (m, 2H), 3.90 (ddd, J=4.70, 10.27, 14.97 Hz, 1H), 3.77-3.64 (m, 2H), 3.32-3.22 (m, 2H), 3.06 (dd, J=7.92, 15.36 Hz, 1H), 2.84-2.72 (m, 2H), 2.33-2.26 (m, 1H), 2.20 (d, J=4.70 Hz, 1H), 2.14-1.00 (m, 18H). m/z (ESI, +ve ion) 557.2 (M+H).

Example 1085. (1S,3'R,6'R,7'S,8'E,11'S)-6-chloro-7'-hydroxy-11'-(hydroxymethyl)-3,4-dihydro-2H,15'H-spiro [naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

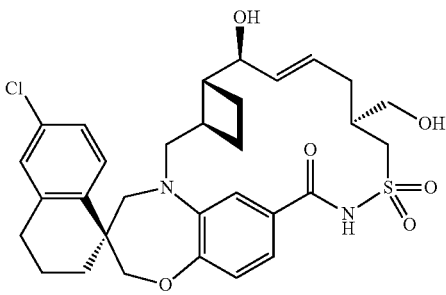

Step 1: 2-allylpropane-1, 3-diol

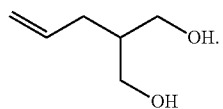

To a 2 litter three-neck Morton flask, equipped with an overhead stirrer, addition funnel and gas inlet was added lithium aluminum hydride (1.0 M solution in THF, 250 mL, 250 mmol). A solution of diethyl allylmalonate (29.7 mL, 150 mmol) in 100 mL of THF was then added using an addition funnel slowly enough allowing the reaction temperature was below 45° C. (the addition time is around 2.5 h). After addition of the starting material the reaction was heated to reflux using heating mantle for around 1 h. The reaction flask was submerged in a water-ice bath to cool to 5° C. and then quenched very slowly with 9.5 mL of water followed by 19 mL of 10% aqueous NaOH and 28 mL of water. The reaction mixture was stirred at rt for around 50 min and the resulting slurry was diluted with around 100 mL of ether and filtered with a Buchner funnel. The filtrate was dried with anhydrous Na$_2$SO$_4$, filtered and concentrated to yield the title compound (16.2 g, 140 mmol, crude yield 93.0%) as clear colorless oil.

Step 2: (R)-2-(((tert-butyldiphenylsilyl)oxy)methyl)pent-4-en-1-ol and (S)-2-(((tert-butyldiphenylsilyl)oxy)methyl)pent-4-en-1-ol

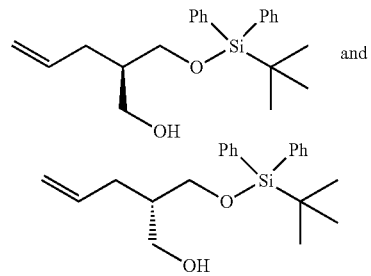

To a 2 litter three-neck Morton flask, equipped with a stir bar, N$_2$ inlet, thermocouple and addition funnel was added sodium hydride (60% dispersion in mineral oil, 3.73 g, 93.0 mmol) and 300 mL of THF and the flask was then submerged in an ice-bath. Once the temperature reached about 5° C., a solution of 2-allylpropane-1, 3-diol (10.8 g, 93.0 mmol) in 70 mL of THF was added dropwise by addition funnel in about 30 min. During the process of addition obvious gas evolution and slight temperature change were observed. A neat tert-butylchlorodiphenylsilane (24.2 mL, 93.0 mmol) was added and the reaction temperature rose from 6° C. to 10° C. during addition with an observation of gas evolution. The reaction was warmed to rt and sit in hood for overnight. The reaction was quenched with water and extracted with EtOAc. The EtOAc extract was washed with saturated NaCl and dried with anhydrous Na$_2$SO$_4$, filtered, and concentrated to give a residue. The residue was loaded onto a 330 g silica gel column and eluted with a gradient of 0-40% EtOAc in Hexane to give the title compound (28.3 g, 80.0 mmol, 86% yield) as clear colorless oil.

Step 3: (S)-2-(((tert-butyldiphenylsilyl)oxy)methyl)pent-4-en-1-yl methanesulfonate and (R)-2-(((tert-butyldiphenylsilyl)oxy)methyl)pent-4-en-1-yl methanesulfonate

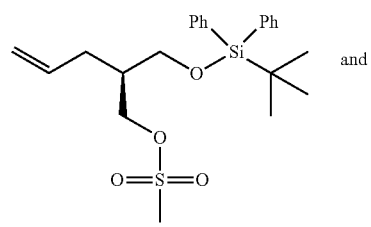

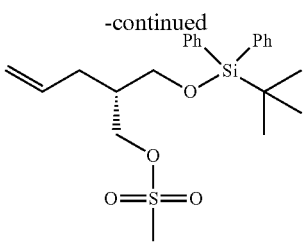

To a solution of (R)-2-(((tert-butyldiphenylsilyl)oxy)methyl)pent-4-en-1-ol and (S)-2-(((tert-butyldiphenylsilyl)oxy)methyl)pent-4-en-1-ol (Step 2; 5.00 g, 14.1 mmol) in 47 mL of DCM was added triethylamine (2.16 mL, 15.5 mmol) and DMAP (0.0520 g, 0.423 mmol) followed by an addition of methanesulfonyl chloride (1.09 mL, 14.1 mmol) via syringe in around 1 min and the resulting reaction was stirred at rt for 3.5 h. The reaction mixture was partitioned with saturated aq. NH$_4$Cl and DCM. The organic phase was dried with anhydrous Na$_2$SO$_4$, filtered and concentrated to yield the title compound (6.90 g, 15.9 mmol, crude yield 113%) as a clear oil with a tint of redness.

Step 4: (S)-2-((2-(((tert-butyldiphenylsilyl)oxy)methyl)pent-4-en-1-yl)thio)pyrimidine and (R)-2-((2-(((tert-butyldiphenylsilyl)oxy)methyl)pent-4-en-1-yl)thio)pyrimidine

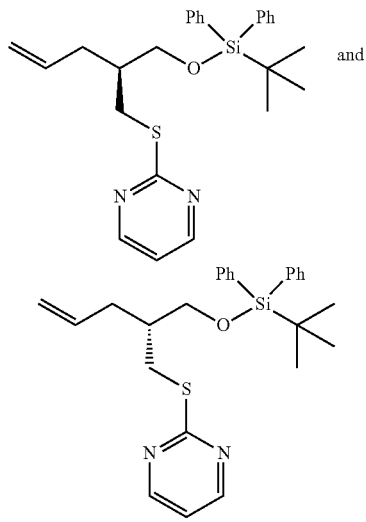

To a solution of (S)-2-(((tert-butyldiphenylsilyl)oxy)methyl)pent-4-en-1-yl methanesulfonate and (R)-2-(((tert-butyldiphenylsilyl)oxy)methyl)pent-4-en-1-yl methanesulfonate (Step 3; 6.90 g, 14.0 mmol) in 70 mL of DMF was added 2-mercaptopyrimidine (1.89 g, 16.8 mmol) and followed by an addition of K$_2$CO$_3$ (2.33 g, 16.8 mmol) in one portion. The resulting bright yellow slurry was stirred at rt for overnight and then more 2-mercaptopyrimidine (0.5 g, 4.44 mmol) and K$_2$CO$_3$ (1.0 g, 7.21 mmol) were added. The reaction was stirred at rt for 3 h and 45 min. The reaction was quenched with saturated aqueous NH$_4$Cl and extracted with ether. The organic extract was dried with anhydrous Na$_2$SO$_4$, filtered and concentrated to give a residue. This residue was dissolved in DCM and loaded onto a 120 g gold-capped ISCO Redisep silica gel column eluting with a gradient of 0-95% of EtOAc in hexane to afford 6.3 g of oil, NMR suggested that it is a mixture of desired product with around 50% of starting material. The isolated mixture was then re-dissolved 20 mL of EtOH and treated with a solution of 2-mercaptopyrimidine (0.9 g, 8.00 mmol) and NaOEt (21 w/w solution in ethanol, 3.14 ml, 8.42 mmol) in 15 mL of EtOH at rt for overnight and at at 65° C. for 7 h. The reaction was quenched with saturated aqueous NH$_4$Cl and extracted with ether. The organic extracts were combined, dried with anhydrous Na$_2$SO$_4$, filtered and concentrated to give a residue, which was purified by chromatograph on a 120 g gold-capped ISCO Redisep silica gel column eluting with a gradient of 0-50% of EtOAc in hexane to provide the title compound (4.76, 10.6 mmol, 76%) as a colorless oil.

Step 5: (S)-2-((2-(((tert-butyldiphenylsilyl)oxy)methyl)pent-4-en-1-yl)sulfonyl)pyrimidine and (R)-2-((2-(((tert-butyldiphenylsilyl)oxy)methyl)pent-4-en-1-yl)sulfonyl)pyrimidine

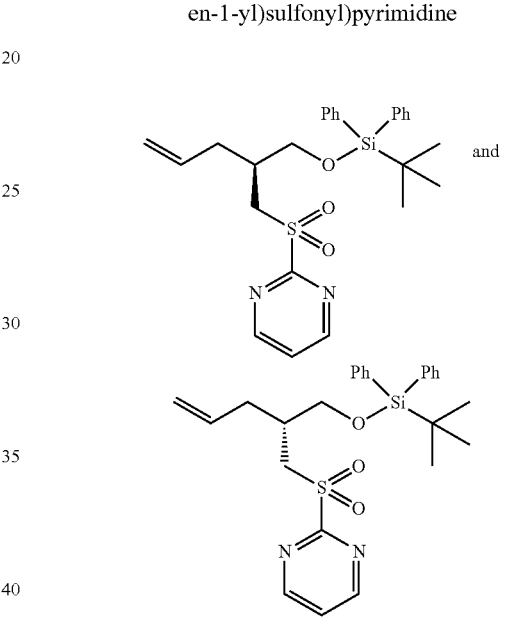

To a solution of (S)-2-((2-(((tert-butyldiphenylsilyl)oxy)methyl)pent-4-en-1-yl)thio)pyrimidine and (R)-2-((2-(((tert-butyldiphenylsilyl)oxy)methyl)pent-4-en-1-yl)thio)pyrimidine (Step 4; 4.76 g, 10.6 mmol) in 53 mL of DCM was added 3-chloroperoxybenzoic acid (77%, 5.23 g, 23.3 mmol) at ice-bath and the resulting reaction was then stirred at rt for 1 hour and 45 min, and LCMS indicated the formation of the desired product. Purification by column chromatography afforded the title compound (3.60 g, 7.49 mmol, 70.6%).

Step 6: (S)-2-(((tert-butyldiphenylsilyl)oxy)methyl)pent-4-ENE-1-sulfonamide and (R)-2-(((tert-butyldiphenylsilyl)oxy)methyl)pent-4-ene-1-sulfonamide

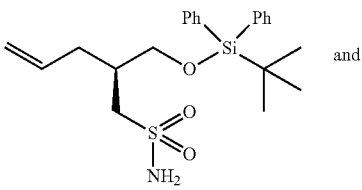

-continued

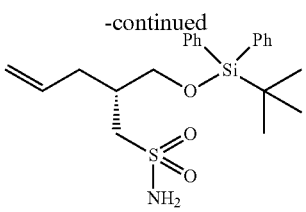

A solution of (S)-2-((2-(((tert-butyldiphenylsilyl)oxy)methyl)pent-4-en-1-yl)sulfonyl)pyrimidine and (R)-2-((2-(((tert-butyldiphenylsilyl)oxy)methyl)pent-4-en-1-yl)sulfonyl)pyrimidine (Step 5; 3.60 g, 7.49 mmol) in 74.9 mL of MeOH was treated with sodium methoxide (25 wt % solution in MeOH, 1.67 mL, 7.49 mmol) at rt for 1 h and the reaction was then concentrated to give a crude oil. To this oil was added 74.9 mL of water, sodium acetate (0.402 mL, 7.49 mmol), around 25 mL of MeOH and hydroxylamine-O-sulfonic acid (1.03 g, 8.24 mmol) in one portion and the resulting reaction was stirred at 50° C. for 1.5 h and then at 60° C. for overnight. The reaction was partitioned with water and ether. The ether extracts were combined, dried with anhydrous $Na_2SO_4$, filtered and concentrated to give crude, which was dissolved in DCM and loaded onto an 80 g ISCO Redisep silica gel column eluting with a gradient of 0-100% EtOAc in hexane to afford the title compound (1.65 g, 3.95 mmol, 52.8%).

Step 7: (S)—N—(((S)-2-(((tert-butyldiphenylsilyl)oxy)methyl)pent-4-en-1-yl)sulfonyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide and (S)—N—(((R)-2-(((tert-butyldiphenylsilyl)oxy)methyl)pent-4-en-1-yl)sulfonyl)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxamide

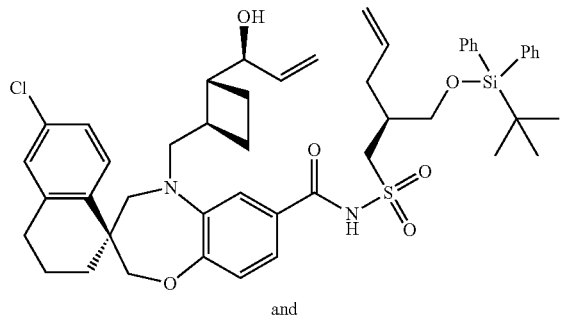

and

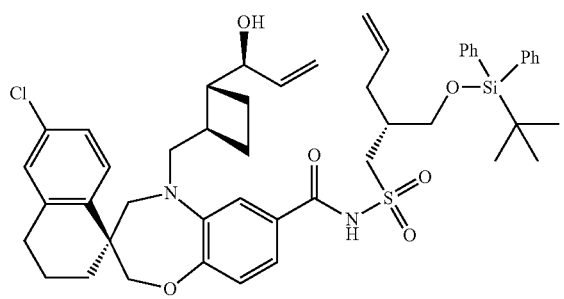

To a solution of Intermediate AA11A and (S)-2-(((tert-butyldiphenylsilyl)oxy)methyl)pent-4-ene-1-sulfonamide and (R)-2-(((tert-butyldiphenylsilyl)oxy)methyl)pent-4-ene-1-sulfonamide (Step 6; 241 mg, 0.577 mmol) in DCM (7.1 mL) was added DMAP (44.4 mg, 0.363 mmol) and triethylamine (89 µl, 0.641 mmol). The reaction mixture was cooled to 0° C. and EDC (82 mg, 0.427 mmol) was added in one portion. The reaction mixture was stirred for 25 h and 50 min and more EDC (60 mg, 0.313 mmol) was added. The reaction mixture was stirred for a further 2 h and 10 min and was then partitioned between DCM and an aqueous ammonium chloride solution. The organic layer was separated, dried over sodium sulfate, filtered and concentrated. The resulting residue was dissolved in a minimal amount of DCM and hexane, loaded onto a 24 g ISCO Gold column and eluted with a gradient of 0-30% EtOAc (containing 0.3% AcOH) in hexane. The title compound (158 mg, 0.182 mmol) was isolated in 85% yield.

Step 8: (1S,3'R,6'R,7'S,8'E,11'S)-11'-(((tert-butyl(diphenyl)silyl)oxy)methyl)-6-chloro-7'-hydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide

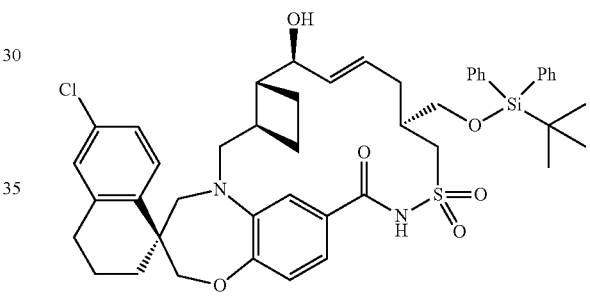

To a solution of the title compound (from Step 7; 158 mg, 0.182 mmol) in 1, 2-dichloroethane (130 mL) was bubbled with argon for 10 min and followed by an addition of (1,3-bis-(2,4,6-trimethylphenyl)-2-imidazolidinylidene)dichloro(o-isopropoxyphenylmethylene)ruthenium (22.8 mg, 0.036 mmol) and the resulting reaction mixture was stirred at 40° C. for 8 h and 15 min. Air was then blown through the mixture for 1 hour and the reaction mixture was concentrated under reduced pressure. The dark residue was taken-up in 3 mL of DCM, loaded onto a 4 g ISCO Gold column, and then eluted with a gradient of 0-70% EtOAc (containing 0.3% AcOH) in hexane to afford the title compound (45 mg, 0.054 mmol, 29.4%).

Step 9: (1S,3'R,6'R,7'S,8'E,11'S)-6-chloro-7'-hydroxy-11'-(hydroxymethyl)-3,4-dihydro-2H,15'H-spiro [naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compound (from Step 8; 45 mg, 0.054 mmol) was treated with tetrabutylammonium fluoride (1.0 M solution in tetrahydrofuran, 536 µL, 0.536 mmol) at rt for 22 h and 45 min. The reaction was diluted with acetonitrile and purified by preparative HPLC (system: Agilent 1100; column: Phenomenex Gemini C18 110 A, C18, 10 microns×30 mm I.D.×250 mm; mobile phase: A:$H_2O$ w/ 0.1% TFA, B:ACN w/ 0.1% TFA; method: 0:00-1:00 50% B, 50-95% B 1:00-20.99 min, 100% B 21.00-25.00 min, 50 ml/min) to give 6 mg of impurity containing sample. This sample was further purified by preparative TLC on a stock Analtech plate using 10% MeOH in DCM as a co-solvent to afford the title compound (3 mg, 9%) as a white solid. $^1$H NMR (400 MHz, CD$_3$OD) δ 7.72 (d, J=8.4 Hz, 1H), 7.17 (dd, J=2.3, 8.4 Hz, 1H), 7.10 (d, J=2.2 Hz, 1H), 7.07-6.99 (m, 2H), 6.90 (d, J=8.0 Hz, 1H), 6.06-5.89 (m, 1H), 5.66 (dd, J=7.0, 15.3 Hz, 1H), 4.13-4.00 (m, 3H), 3.77-3.50 (m, 6H), 3.38 (d, J=14.1 Hz, 1H), 3.26-3.10 (m, 1H), 2.88-2.69 (m, 2H), 2.52-2.27 (m, 3H), 2.23-2.10 (m, 2H), 2.09-2.01 (m, 1H), 1.98-1.83 (m, 3H), 1.81-1.66 (m, 3H), 1.56-1.41 (m, 1H). m/z (ESI, +ve ion) 601.2 (M+H)$^+$.

Example 1086. (1S,3'R,6'R,7'S,8'E,11'R)-6-chloro-7'-hydroxy-11'-(hydroxymethyl)-3,4-dihydro-2H, 15'H-spiro [naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

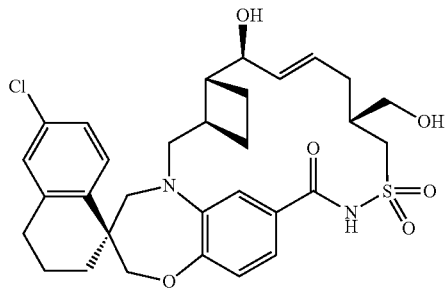 [SMILES: O=C1NS(=O)(=O)C[C@@H](CO)C/C=C/[C@H](O)[C@@H]2CC[C@H]2CN2C[C@@]3(CCCc4cc(Cl)ccc43)COc3ccc1cc32]

Step 1: (1S,3'R,6'R,7'S,8'E,11'R)-11'-(((tert-butyl(diphenyl)silyl)oxy)methyl)-6-chloro-7'-hydroxy-3,4-dihydro-2H,15'H-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide

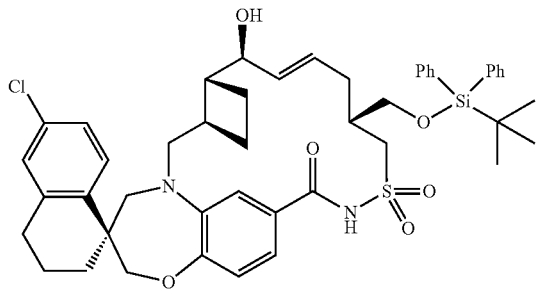 [SMILES: CC(C)(C)[Si](OC[C@H]1C/C=C/[C@H](O)[C@@H]2CC[C@H]2CN2C[C@@]3(CCCc4cc(Cl)ccc43)COc3ccc(cc32)C(=O)NS(=O)(=O)C1)(c1ccccc1)c1ccccc1]

The title compound was the other isomer isolated from the reaction described in Example 1085, Step 8 (43 mg, 0.051 mmol, 28.1%).

Step 2: (1S,3'R,6'R,7'S,8'E,11'R)-6-chloro-7'-hydroxy-11'-(hydroxymethyl)-3,4-dihydro-2H,15'H-spiro [naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compound was prepared from (1S,3'R,6'R,7'S,8'Z,11'R)-11'-(((tert-butyl (diphenyl)silyl)oxy)methyl)-6-chloro-7'-hydroxy-3,4-dihydro-2h,15'h-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (Example 1086, Step 1) by a procedure similar to the one described in Example 1085, Step 9 as a TFA salt. $^1$H NMR (400 MHz, CD$_2$Cl$_2$) δ 7.90-7.66 (m, 1H), 7.16 (dd, J=2.2, 8.5 Hz, 1H), 7.09 (d, J=2.2 Hz, 1H), 6.98-6.86 (m, 3H), 5.89-5.79 (m, 1H), 5.79-5.68 (m, 1H), 4.20 (dd, J=4.1, 7.6 Hz, 1H), 4.17-4.02 (m, 3H), 3.87-3.77 (m, 1H), 3.76-3.64 (m, 3H), 3.45-3.33 (m, 1H), 3.30-3.20 (m, 1H), 3.04 (dd, J=9.2, 15.3 Hz, 1H), 2.86-2.67 (m, 2H), 2.47-2.24 (m, 3H), 2.10-1.88 (m, 6H), 1.88-1.73 (m, 3H), 1.73-1.60 (m, 1H), 1.47-1.33 (m, 1H). m/z (ESI, +ve ion) 601.2 (M+H)$^+$.

Example 1087. (1S,3'R,6'R,7'S,8'E,11'R)-6-chloro-7'-hydroxy-11'-(methoxymethyl)-3,4-dihydro-2H, 15'H-spiro [naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

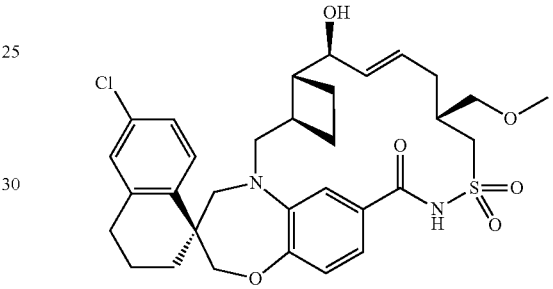

To a solution of (1S,3'R,6'R,7'S,8'E,11'R)-6-chloro-7'-hydroxy-11'-(hydroxymethyl)-3,4-dihydro-2h,15'h-spiro [naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide· TFA salt (Example 1086; 6.0 mg, 0.053 mmol) in THF (526 μL) at 0° C. was slowly added sodium hydride (60% dispersion in mineral oil, 10.5 mg, 0.263 mmol). The reaction mixture was stirred at 0° C. for 10 min and then at rt for 5 min. The mixture was cooled to 0° C. and 50 μL of a solution of iodomethane in THF (prepared by adding 3 mg of iodomethane in 100 μL of THF) was added. The reaction mixture was stirred at 0° C. for 40 min and the ice-bath was then removed. Another 50 μL of the previously prepared iodomethane solution in THF was added and the mixture was stirred at rt for 16 h. The reaction mixture was then diluted with THF (100 μL) and quenched by adding a drop of acetic acid. The reaction mixture was concentrated under reduced pressure to give a residue, which was purified by preparative TLC plate: the residue was dissolved in a minimal amount of DCM and loaded onto Analtech plate (Uniplate, 10×20×250 microns, silica gel HLF w/binder and uv254). The plate was eluded first with 50% EtOAc (containing 0.3% AcOH) in hexane. The plate was dried and 20 mL of EtOAc (containing 0.3% AcOH) was added to the previous eluent. This corresponded to approximately 60% EtOAc (containing 0.3% AcOH) in hexane. The plate was eluded and then dried again. The eluent was replaced with 80% EtOAc (containing 0.3% AcOH) in hexane and the plate was eluted one last time. Four bands were cut and collected, numbered from top to bottom, and extracted with 100% EtOAc (containing 0.3% AcOH). Each fraction was then concentrated and fraction 3 provided the title compound (1.25 mg, 2.03 μmoL, 3.86% yield). $^1$H NMR (400 MHz, CD$_2$Cl$_2$) δ 7.76-7.65 (m, 1H), 7.17 (dd, J=2.2, 8.5 Hz, 1H), 7.09 (d, J=2.3 Hz, 1H), 6.94-6.87 (m, 3H), 5.87-5.77 (m, 1H), 5.76-5.66 (m, 1H), 4.22-4.16 (m, 1H), 4.11-4.07 (m, 3H), 3.81 (d, J=15.3 Hz, 1H), 3.77-3.65 (m, 1H), 3.44-3.34 (m, 3H), 3.32 (s, 3H), 3.28-3.21 (m, 1H), 3.05 (dd, J=9.3, 15.4 Hz, 1H), 2.80-2.73 (m, 2H), 2.48-2.28 (m, 3H), 2.17-2.11 (m, 1H), 2.06-2.01 (m, 2H), 1.98-1.89 (m, 2H), 1.87-1.75 (m, 3H), 1.74-1.62 (m, 2H). m/z (ESI, +ve ion) 615.2 (M+H)$^+$.

Example 1088. (1S,3'R,6'R,7'R,8'E,11'S)-6-chloro-7'-hydroxy-11'-(methyl)-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide

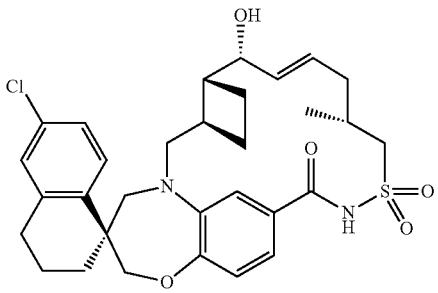 [SMILES: C[C@@H]1C/C=C/[C@@H](O)[C@@H]2CC[C@H]2CN2C[C@@]3(CCCc4cc(Cl)ccc43)COc3ccc(cc32)C(=O)NS(=O)(=O)C1]

Step 1: (R)-2-methylpent-4-en-1-ol

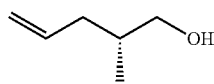

To a solution of (S)-(+)-3-bromo-2-methyl-1-propanol (4.56 mL, 44.1 mmol) in THF (110 mL) in a 250 mL round-bottomed flask equipped with an N$_2$ inlet and stir bar was added copper (I) iodide (0.420 g, 2.20 mmol) and followed by an addition of vinylmagnesium bromide (1.0 M solution in tetrahydrofuran, 44.1 mL, 44.1 mmol) via a syringe over about 20 min. The resulting dark black reaction mixture was stirred at rt for overnight. The reaction was submerged in an ice-bath and another 1.0 equivalent of vinyl magnesium bromide was added over 15 min. The reaction was stirred at rt for 8 h and 40 min and followed by an addition of another 4 mL of Grignard and the reaction was stirred at rt for overnight. The reaction was quenched with saturated aqueous NH$_4$Cl and extracted with DCM. The organic layer (it is a mixture of THF and DCM and is the top layer in the separation funnel) was collected, washed with saturated NaCl, dried with anhydrous sodium sulfate, filtered and concentrated to a afford the title compound as a light amber crude oil (5.1 g, crude yield 115%).

Step 2: (R)-2-methylpent-4-en-1-yl 4-methylbenzenesulfonate

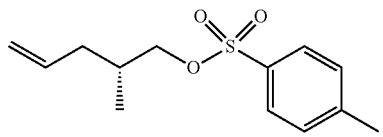 [SMILES: C=CC[C@@H](C)COS(=O)(=O)c1ccc(C)cc1]

To a solution of (R)-2-methylpent-4-en-1-ol (4.42 g, 44.1 mmol) in DCM (110 mL) was added pyridine (17.8 mL, 221 mmol) and followed by an addition of p-toluenesulfonyl chloride (8.83 g, 46.3 mmol) at ice-bath. The reaction was then stirred at rt over the weekend. The reaction was quenched with aqueous 1.2 M HCl and extracted with DCM. The organic layer was washed with aqueous 1.2 M HCl and brine, dried with sodium sulfate, filtered and concentrated. The residue was loaded onto a 330 g gold-capped ISCO Redisep silica gel column running with a gradient of 0-50% DCM in hexane to elute first peak and then eluting with a gradient of 50-100% of EtOAc to collect multiple fractions. These fractions were combined and concentrated to give an oil, which was loaded onto another 330 g gold capped silica gel column (ISCO Redisep) eluting with a gradient of 0-20% EtOAc in hexane to afford the title compound (total 3.67 g with about 30% impurity).

Step 3: (R)-2-((2-methylpent-4-en-1-yl) thio) pyrimidine

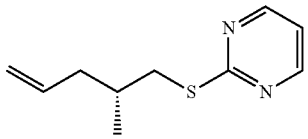

To a solution of 2-mercaptopyrimidine (1.73 g, 15.4 mmol) in 20 mL of EtOH was added sodium ethoxide (21 w/w solution in EtOH, 5.76 mL, 15.4 mmol) followed by an additon of a solution of (R)-2-methylpent-4-en-1-yl 4-methylbenzenesulfonate (Step 2, 3.57 g, 14.0 mmol) in EtOH. The reaction was stirred at rt for 24 h and then at 65° C. for overnight. The reaction was quenched with saturated NH$_4$Cl and extracted with DCM. The organic layer was dried with anhydrous sodium sulfate, filtered, concentrated and purified by a 120 g gold-capped Redisep silica gel column eluting with a gradient of 0-100% of EtOAc in hexane to afford the title compound (total 2.3 g with impurity) as an oil.

Step 4: (R)-2-((2-methylpent-4-en-1-yl) sulfonyl) pyrimidine

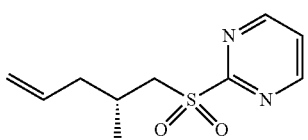

To a solution of (R)-2-((2-methylpent-4-en-1-yl) thio) pyrimidine (Step 3, 2.3 g, 11.8 mmol) in DCM (39.5 mL) was added 3-chloroperoxybenzoic acid (77%, 4.38 g, 19.5 mmol) at ice-bath and the resulting reaction mixture was stirred at rt for overnight. The reaction was concentrated and hexane was added and the mixture was then filtered to remove solid. The filtrate was concentrated and purified by a 80 g gold-capped Redsep column eluting with a gradient of 0-100% of EtOAc in hexane to afford the title compound (1.16 g, 5.13 mmol, 43.3%).

Step 5: (R)-2-methylpent-4-ene-1-sulfonamide

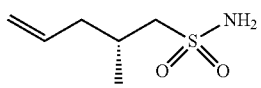

To a solution of (R)-2-((2-methylpent-4-en-1-yl)sulfonyl) pyrimidine (Step 4; 1.16 g, 5.13 mmol) in MeOH (51.3 mL) was added sodium methylate (1.17 mL, 5.13 mmol) and the reaction was stirred at rt for 4 h. To this reaction was added sodium acetate (0.421 g, 5.13 mmol) and sulfonic acid (0.709 g, 5.64 mmol) and the resulting reaction was stirred at 50° C. for 15 min followed by an addition of 35 mL of water. The reaction was stirred at 50° C. for overnight and the partitioned with ether and aqueous NH$_4$Cl. The organic extracts were combined, dried with anhydrous sodium sulfate, filtered and concentrated to give a residue. The residue was purified by a 40 g gold-capped Redsep column eluting with a gradient of 0-100% of EtOAc in hexane to afford the title compound (total 0.76 g with about 50% of one impurity).

Step 6: (S)-6'-chloro-5-(((1R,2R)-2-((R)-1-hydroxyallyl)cyclobutyl)methyl)-N—(((R)-2-methylpent-4-en-1-yl)sulfonyl)-3',4,4',5-tetrahydro-2H,2'H-spiro [benzo[b][1,4]oxazepine-3,1'-naphthalene]-7-carboxamide

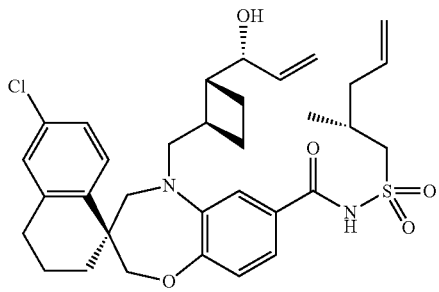 [SMILES: C=CC[C@@H](C)CS(=O)(=O)NC(=O)c1ccc2c(c1)N(C[C@@H]1CC[C@H]1[C@H](O)C=C)C[C@@]1(CCCc3cc(Cl)ccc31)CO2]

The title compound was prepared from Intermediate AA11B and (R)-2-methylpent-4-ene-1-sulfonamide (Step 5) by a procedure similar to the one described in Example 1085, Step 7. This compound was isolated by preparative HPLC (system: Agilent 1100; column: Phenomenex Gemini C18 110 A, C18, 10 microns×30 mm I.D.×250 mm; mobile phase: A:H$_2$O w/ 0.1% TFA, B:ACN w/ 0.1% TFA; method: 0:00-1:00 10% B, 50-100% B 1:00-18.00 min, 100% B 21.00-25.00 min, 50 ml/min) as a TFA salt.

Step 7: (1S,3'R,6'R,7'R,8'E,11'S)-6-chloro-7'-hydroxy-11'-(methyl)-3,4-dihydro-2H,15'H-spiro [naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide The title compound (42.2 mg, 0.072 mmol, 92%) was prepared from (S)-6'-chloro-5-(((1R,2R)-2-((R)-1-hydroxyallyl)cyclobutyl)methyl)-N—(((R)-2-methylpent-4-en-1-yl) sulfonyl)-3',4,4',5-tetrahydro-2h,2'h-spiro[benzo[b][1,4] oxazepine-3,1'-naphthalene]-7-carboxamide (Step 6) by a procedure similar to the one described in Example 1085, Step 8. $^1$H NMR (400 MHz, CD$_2$Cl$_2$) δ 7.72 (d, J=8.4 Hz, 1H), 7.29 (dd, J=2.0, 8.2 Hz, 1H), 7.17 (dd, J=2.2, 8.5 Hz, 1H), 7.09 (dd, J=2.2, 4.9 Hz, 2H), 6.95 (d, J=8.2 Hz, 1H), 5.99-5.89 (m, 1H), 5.78 (dd, J=8.2, 15.3 Hz, 1H), 4.26 (dd, J=5.5, 8.2 Hz, 1H), 4.11 (s, 2H), 3.89 (dd, J=8.7, 15.7 Hz, 1H), 3.80-3.71 (m, 1H), 3.64 (d, J=14.3 Hz, 1H), 3.35 (dd, J=3.9, 15.8 Hz, 1H), 3.31-3.24 (m, 1H), 3.11 (dd, J=8.9, 15.4 Hz, 1H), 2.84-2.69 (m, 2H), 2.62 (quin, J=9.0 Hz, 1H), 2.42-2.25 (m, 3H), 2.05-2.01 (m, 1H), 2.00-1.76 (m, 5H), 1.74-1.62 (m, 1H), 1.60-1.51 (m, 1H), 1.51-1.39 (m, 1H), 1.12 (d, J=6.8 Hz, 3H). m/z (ESI, +ve ion) 585.2 (M+H)$^+$.

Example 1089. (1S,3'R,6'R,7'R,8'E,11'R)-6-chloro-7'-hydroxy-11'-(hydroxymethyl)-3,4-dihydro-2H, 15'H-spiro [naphthalene-1,22'-[20]oxa[13]thia[1,14] diazatetracyclo[14.7.2.0$^{3,6}$.0$^{19,24}$]pentacosa [8,16,18, 24]tetraen]-15'-one 13',13'-dioxide or (1S,3'R,6'R, 7'R,8'E,11'S)-6-chloro-7'-hydroxy-11'-(hydroxymethyl)-3,4-dihydro-2H,15'H-spiro [naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

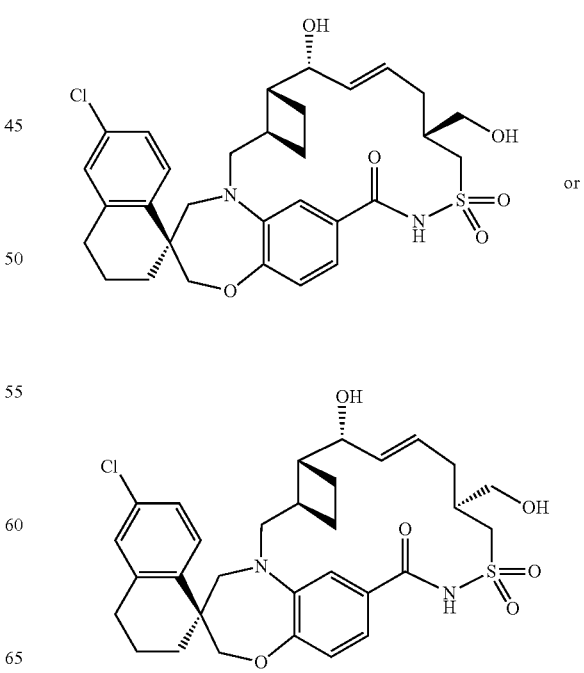

Step 1: (S)—N—(((S)-2-(((tert-butyldiphenylsilyl)oxy)methyl)pent-4-en-1-yl)sulfonyl)-6'-chloro-5-(((1R,2R)-2-((R)-1-hydroxyallyl)cyclobutyl)methyl)-3',4',5-tetrahydro-2H,2'H-spiro[benzo[b][1,4]oxazepine-3,1'-naphthalene]-7-carboxamide and (S)—N—(((R)-2-(((tert-butyldiphenylsilyl)oxy)methyl)pent-4-en-1-yl)sulfonyl)-6'-chloro-5-(((1R,2R)-2-((R)-1-hydroxyallyl)cyclobutyl)methyl)-3',4',5-tetrahydro-2H,2'H-spiro[benzo[b][1,4]oxazepine-3,1'-naphthalene]-7-carboxamide

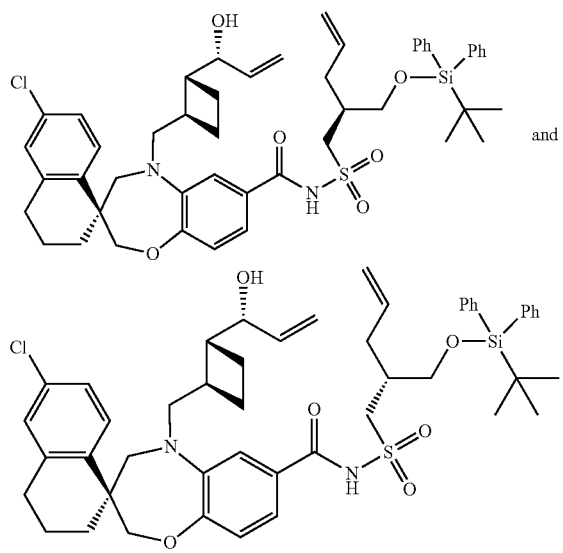

and

The title compound was prepared from Intermediate AA11B and (S)-2-(((tert-butyldiphenylsilyl)oxy)methyl)pent-4-ene-1-sulfonamide and (R)-2-(((tert-butyldiphenylsilyl)oxy)methyl)pent-4-ene-1-sulfonamide (Example 1085, Step 6) by a procedure similar to the one described in Example 1085, Step 7.

Step 2: (1S,3'R,6'R,7'R,8'E,11'R)-11'-(((tert-butyl(diphenyl)silyl)oxy)methyl)-6-chloro-7'-hydroxy-3,4-dihydro-2H,15'H-spiro[naphthalene-1,22'-[20]oxa[13]thia[1,14]diazatetracyclo [14.7.2.0³,⁶.0¹⁹,²⁴]pentacosa[8,16,18,24]tetraen]-15'-one 13',13'-dioxide and (1S,3'R,6'R,7'R,8'E,11'S)-11'-(((tert-butyl (diphenyl)silyl)oxy)methyl)-6-chloro-7'-hydroxy-3,4-dihydro-2H,15'H-spiro[naphthalene-1,22'-[20]oxa[13]thia[1,14]diazatetracyclo [14.7.2.0³,⁶.0¹⁹,²⁴]pentacosa[8,16,18,24]tetraen]-15'-one 13',13'-dioxide

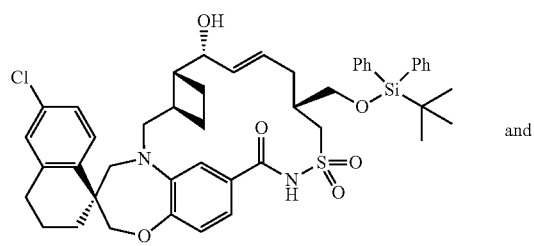

and

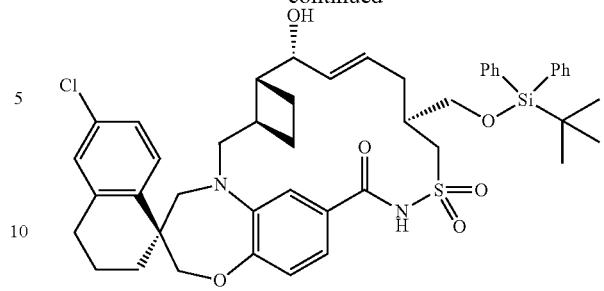

The title compound was prepared using the intermediate isolated from Example 1089, Step 1 by a procedure similar to the one described in Example 1085, Step 8.

Step 3: (1S,3'R,6'R,7'R,8'E,11'R)-6-chloro-7'-hydroxy-11'-(hydroxymethyl)-3,4-dihydro-2H,15'H-spiro [naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'R,8'E,11'S)-6-chloro-7'-hydroxy-11'-(hydroxymethyl)-3,4-dihydro-2H,15'H-spiro [naphthalene-1,22'-[20]oxa[13]thia[1,14]diazatetracyclo[14.7.2.0³,⁶.0¹⁹,²⁴] pentacosa [8,16,18,24]tetraen]-15'-one 13',13'-dioxide The title compound (20 mg, 0.033 mmol, 31.7%) was prepared from the intermediate in Example 1089, Step 2 by a procedure similar to the one described in Example 1085, Step 9. ¹H NMR (400 MHz, CD₂Cl₂) δ 7.70 (d, J=8.4 Hz, 1H), 7.39 (d, J=1.8 Hz, 1H), 7.16 (dd, J=2.2, 8.5 Hz, 1H), 7.08 (d, J=2.2 Hz, 1H), 7.04 (dd, J=1.9, 8.1 Hz, 1H), 6.91 (d, J=8.0 Hz, 1H), 5.78-5.62 (m, 2H), 4.11-4.05 (m, 2H), 4.05-3.99 (m, 1H), 3.93 (dd, J=4.2, 15.4 Hz, 2H), 3.74-3.61 (m, 3H), 3.35 (dd, J=7.4, 15.5 Hz, 1H), 3.20 (d, J=14.3 Hz, 1H), 2.97 (dd, J=7.0, 15.3 Hz, 1H), 2.84-2.66 (m, 2H), 2.49 (br. s., 2H), 2.37 (dd, J=4.4, 13.4 Hz, 1H), 2.14-2.07 (m, 1H), 2.04-1.84 (m, 5H), 1.83-1.73 (m, 2H), 1.69-1.51 (m, 2H), 1.35 (t, J=12.1 Hz, 1H). m/z (ESI, +ve ion) 601.2 (M+H)⁺.

Example 1090. (1S,3'R,6'R,7'R,8'E,11'S)-6-chloro-7'-hydroxy-11'-(hydroxymethyl)-3,4-dihydro-2H,15'H-spiro [naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide or (1S,3'R,6'R,7'R,8'E,11'R)-6-chloro-7'-hydroxy-11'-(hydroxymethyl)-3,4-dihydro-2H,15'H-spiro [naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

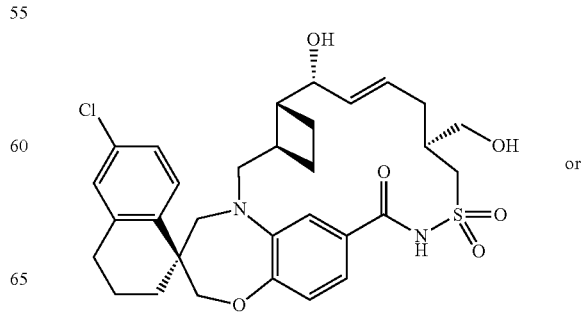

or

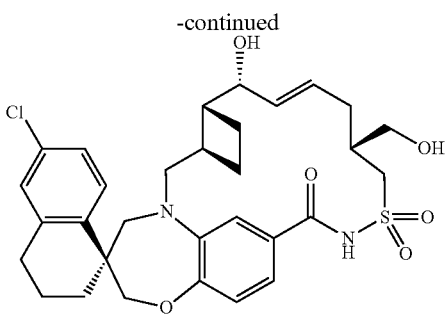

The title compound was isolated as the other isomer from the reaction of Example 1089, step 3. $^{19}$FNMR suggested that it is a TFA salt. $^1$H NMR (400 MHz, CD$_2$Cl$_2$) δ 7.71 (d, J=8.6 Hz, 1H), 7.26 (d, J=8.0 Hz, 1H), 7.16 (dd, J=2.1, 8.5 Hz, 1H), 7.11-7.03 (m, 2H), 7.01-6.86 (m, 1H), 5.98-5.87 (m, 1H), 5.85-5.76 (m, 1H), 4.31-4.21 (m, 1H), 4.14-4.04 (m, 2H), 3.90-3.60 (m, 5H), 3.59-3.49 (m, 1H), 3.34-3.21 (m, 1H), 3.10 (dd, J=9.0, 14.9 Hz, 1H), 2.83-2.68 (m, 2H), 2.65-2.53 (m, 1H), 2.43-2.24 (m, 3H), 2.10-1.75 (m, 7H), 1.68 (quin, J=9.4 Hz, 1H), 1.60-1.49 (m, 1H), 1.49-1.37 (m, 1H). m/z (ESI, +ve ion) 601.2 (M+H)$^+$.

Example 1091. (1S,3'R,6'R,7'R,8'E)-6-chloro-7'-methoxy-3,4-dihydro-2H,15'H-spiro [naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

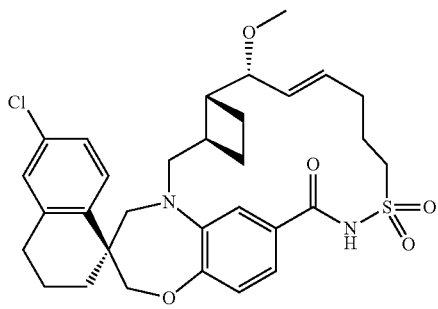 [SMILES: CO[C@@H]1/C=C/CCCS(=O)(=O)NC(=O)c2ccc3c(c2)N(C[C@@H]2CC[C@H]21)C[C@@]1(CCCc2cc(Cl)ccc21)CO3]

To a solution of (1S,3'R,6'R,7'R,8'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 952; 10 mg, 0.018 mmol) in THF (175 μL) in a vial with a septum cap was added sodium hydride (60% dispersion in mineral oil, 3.50 mg, 0.088 mmol) at ice-bath and the reaction was then stirred at rt for 20 min and followed by an addition of a solution of methyl iodide (1.64 μL, 0.026 mmol) in THF (100 μL). The resulting reaction was stirred at rt for about 2 h and quenched with saturated NH$_4$Cl and extracted with EtOAc three times. The combined extracts were dried with anhydrous sodium sulfate, filtered and concentrated. The residue was dissolved in DCM and purified by a 4 g gold-capped Redsep column eluting with a gradient of 0-100% EtOAc in hexane to afford the title compound (5.6 mg, 9.57 μmol, 54.7%) as a colorless resin. $^1$H NMR (400 MHz, CD$_2$Cl$_2$) δ 8.27 (br. s., 1H), 7.72 (d, J=8.6 Hz, 1H), 7.25 (d, J=1.6 Hz, 1H), 7.17 (dd, J=2.2, 8.5 Hz, 1H), 7.09 (d, J=2.2 Hz, 1H), 6.99-6.88 (m, 2H), 5.71 (td, J=5.2, 15.8 Hz, 1H), 5.38 (dd, J=8.3, 15.9 Hz, 1H), 4.04-3.89 (m, 2H), 3.70-3.63 (m, 1H), 3.51 (dd, J=4.1, 8.2 Hz, 1H), 3.33 (s, 3H), 3.26-3.16 (m, 2H), 2.97 (dd, J=9.3, 15.2 Hz, 1H), 2.83-2.68 (m, 2H), 2.57-2.29 (m, 3H), 2.20-2.02 (m, 3H), 1.97-1.76 (m, 4H), 1.75-1.67 (m, 1H), 1.65-1.35 (m, 5H). m/z (ESI, +ve ion) 585.2 (M+H)$^+$.

Example 1092. (1S,3'R,6'R,7'R,8'Z,12'R)-6-chloro-7'-hydroxy-12'-ethyl-3,4-dihydro-2H,15'H-spiro [naphthalene-1,22'-[20]oxa[13]thia[1,14]diazatetracyclo[14.7.2.0$^{3,6}$.0$^{19,24}$]pentacosa [8,16,18,24]tetraen]-15'-one 13',13'-dioxide

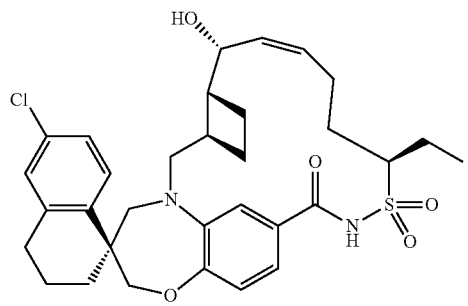 [SMILES: CC[C@@H]1CC/C=C\[C@@H](O)[C@@H]2CC[C@H]2CN2C[C@@]3(CCCc4cc(Cl)ccc43)COc3ccc(cc32)C(=O)NS1(=O)=O]

Step 1: (S)-6'-chloro-N—((R)-hept-6-en-3-ylsulfonyl)-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide

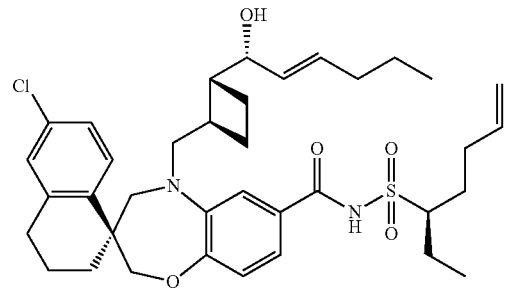 [SMILES: C=CCC[C@@H](CC)S(=O)(=O)NC(=O)c1ccc2c(c1)N(C[C@@H]1CC[C@H]1[C@H](O)/C=C/CCC)C[C@@]1(CCCc3cc(Cl)ccc31)CO2]

The title compound was prepared from intermediate AA12B and Intermediate EE21 by a procedure similar to the one described in Example 1085, Step 7 (121 mg, 0.181 mmol, 99%).

Step 2: (1S,3'R,6'R,7'R,8'Z,12'R)-6-chloro-7'-hydroxy-12'-ethyl-3,4-dihydro-2H,15'H-spiro [naphthalene-1,22'-[20]oxa[13]thia[1,14]diazatetracyclo [14.7.2.0$^{3,6}$.0$^{19,24}$]pentacosa [8,16,18,24]tetraen]-15'-one 13',13'-dioxide The title compound (5.0 mg, 8.34 μmol, 8.59%) was prepared from (S)-6'-chloro-N—((R)-hept-6-en-3-ylsulfonyl)-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxamide (Step 1) by a procedure similar to the one described in Example 1085, Step 8. $^1$H NMR (400 MHz, CD$_2$Cl$_2$) δ 8.29 (br. s., 1H), 7.72 (d, J=8.4 Hz, 1H), 7.18 (dd, J=2.3, 8.4 Hz, 1H), 7.09 (d, J=2.3 Hz, 1H), 6.99-6.90 (m, 3H), 5.53-5.44 (m, 1H), 5.44-5.37 (m, 1H), 4.18 (t, J=7.2 Hz, 1H), 4.14-4.08 (m, 1H), 4.08-4.01 (m, 1H), 3.81-3.68 (m, 3H), 3.29 (d, J=14.5 Hz, 1H), 2.80-2.69 (m, 2H), 2.56-2.43 (m, 1H), 2.40-2.10 (m, 4H), 2.07-1.88 (m, 5H), 1.88-1.74 (m, 4H), 1.73-1.61 (m, 1H), 1.48-1.34 (m, 2H), 1.14 (t, J=7.4 Hz, 3H). m/z (ESI, +ve ion) 599.2 (M+H)+.

Example 1093. (1S,3'R,6'R,7'R,8'E,12'R)-6-chloro-7'-methoxy-12'-ethyl-3,4-dihydro-2H,15'H-spiro [naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

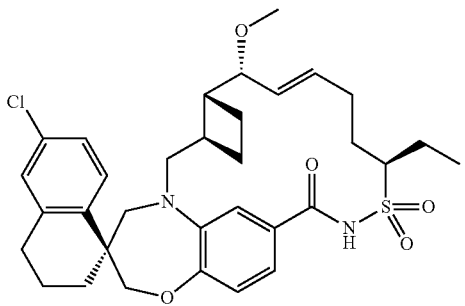 [SMILES: CC[C@@H]1CC/C=C/[C@@H](OC)[C@@H]2CC[C@H]2CN2C[C@@]3(CCCc4cc(Cl)ccc43)COc3ccc(cc32)C(=O)NS1(=O)=O]

Step 1: (1S,3'R,6'R,7'R,8'E,12'R)-6-chloro-7'-hydroxy-12'-ethyl-3,4-dihydro-2H,15'H-spiro [naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

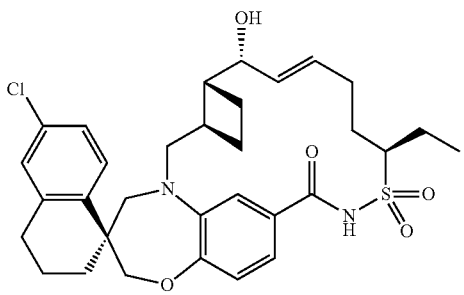 [SMILES: CC[C@@H]1CC/C=C/[C@@H](O)[C@@H]2CC[C@H]2CN2C[C@@]3(CCCc4cc(Cl)ccc43)COc3ccc(cc32)C(=O)NS1(=O)=O]

The title compound (15 mg, 0.025 mmol, 25.8%) was the other isomer isolated from the reaction described in Example 1092, Step 2.

Step 2: (1S,3'R,6'R,7'R,8'E,12'R)-6-chloro-7'-methoxy-12'-ethyl-3,4-dihydro-2H,15'H-spiro [naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide To a solution of (1S,3'R,6'R,7'R,8'E,12'R)-6-chloro-7'-hydroxy-12'-ethyl-3,4-dihydro-2h,15'h-spiro [naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide (Step 1; 9 mg, 0.015 mmol) in THF (150 µL) in a glass vial with a septum cap was added sodium hydride (60% dispersion in mineral oil, 1.80 mg, 0.075 mmol) at ice-bath and the reaction was stirred at this temperature for 10 min and at rt for another 10 min. The reaction was returned to the ice-bath, and to this reaction was added a solution of methyl iodide (4.26 mg, 0.030 mmol) in THF (400 µL). The reaction was stirred at rt for about 4 h and then quenched with saturated NH₄Cl and extracted with EtOAc. The organic extract was concentrated and purified by prearative TLC on a Analtech Uniplate Silica gel HLF (w/binder and 254) 10×20 cm×250 micron plate eluting with 30% EtOAc in hexane to afford the title compound (1.61 mg, 2.63 µmol, 17.5%) as a white solid. ¹H NMR (400 MHz, CD₂Cl₂) δ 8.08 (br. s., 1H), 7.72 (d, J=8.4 Hz, 1H), 7.31 (s, 1H), 7.17 (dd, J=2.3, 8.4 Hz, 1H), 7.09 (d, J=2.3 Hz, 1H), 6.95-6.86 (m, 2H), 5.55-5.45 (m, 1H), 5.35 (s, 1H), 4.09 (s, 2H), 3.99-3.80 (m, 2H), 3.66 (d, J=14.3 Hz, 1H), 3.31 (dd, J=3.1, 8.0 Hz, 1H), 3.23 (s, 3H), 3.20 (d, J=14.1 Hz, 1H), 2.96 (dd, J=7.6, 15.3 Hz, 1H), 2.81-2.70 (m, 2H), 2.55-2.42 (m, 2H), 2.42-2.28 (m, 1H), 2.21-2.01 (m, 3H), 1.99-1.76 (m, 5H), 1.71 (d, J=7.4 Hz, 1H), 1.65-1.53 (m, 2H), 1.45-1.31 (m, 1H), 1.13 (t, J=7.5 Hz, 3H). m/z (ESI, +ve ion) 613.3 (M+H)+.

Example 1094. (1S,3'R,6'R,7'R)-6-chloro-7'-methoxy-3,4-dihydro-2H,15'H-spiro [naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide

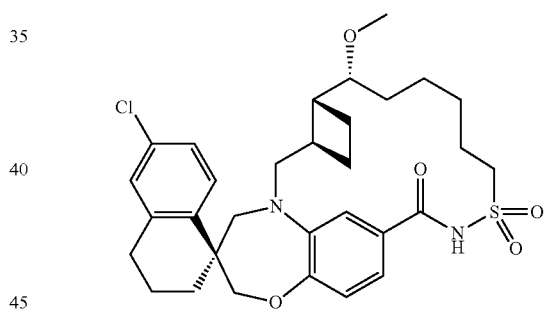

To a solution of Example 1091 (3.1 mg, 5.30 µmol) in EtOAc (883 µL) in a glass vial was added platinum (iv) oxide (0.241 mg, 1.06 µmol). The vial was capped with a septum and evacuated and back-filled with hydrogen, and the reaction was stirred at rt for 26 h. The reaction mixture was concentrated on Genevac, resuspended in DCM and eluted through a Pasteur Pipette silica gel column (1 cm height) with 50% EtOAc in hexane. The eluent was collected and concentrated on Genevac to afford the title compound (2.6 mg, 4.43 µmol, 84%). ¹H NMR (400 MHz, CD₂Cl₂) δ 8.79 (br. s., 1H), 7.73 (d, J=8.6 Hz, 1H), 7.24-7.14 (m, 3H), 7.09 (d, J=2.3 Hz, 1H), 6.94 (d, J=8.0 Hz, 1H), 4.10-4.08 (m, 2H), 3.81 (d, J=15.3 Hz, 1H), 3.70 (d, J=14.1 Hz, 1H), 3.63-3.48 (m, 2H), 3.45 (s, 3H), 3.21 (d, J=14.3 Hz, 1H), 3.12-3.03 (m, 2H), 2.83-2.70 (m, 2H), 2.68-2.57 (m, 1H), 2.48-2.37 (m, 1H), 2.08-2.01 (m, 2H), 1.96-1.89 (m, 1H), 1.89-1.77 (m, 4H), 1.74-1.58 (m, 4H), 1.51-1.36 (m, 5H). m/z (ESI, +ve ion) 587.2 (M+H)+.

2129

Example 1095. (1S,3'R,6'R,7'R,8'E)-6-chloro-7'-(2-(methylsulfonyl)ethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa [8,16,18,24]tetraen]-15'-one 13',13'-dioxide

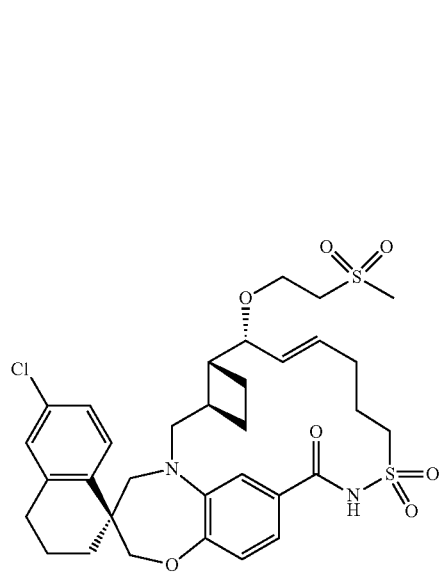 [SMILES: CS(=O)(=O)CCO[C@@H]1/C=C/CCCS(=O)(=O)NC(=O)c2ccc3c(c2)N(C[C@@H]2CC[C@H]21)C[C@@]1(CCCc2cc(Cl)ccc21)CO3]

To a solution of Example 991 (10 mg, 0.018 mmol) in THF (175 µL) in a vial with a septum cap was added sodium hydride (60% dispersion in mineral oil, 3.50 mg, 0.088 mmol) at ice-bath. The reaction was then stirred at rt for 20 min and followed by an addition of a solution of 2-(bromoethyl)methylsulfone (4.91 mg, 0.026 mmol) in THF (100 µL). The reaction was stirred at rt for about 2 h and at 50° C. to 60° C. for around 3 h. The reaction was quenched with saturated NH₄Cl and extracted with DCM. The DCM extracts were combined, dried with anhydrous sodium sulfate, filtered and concentrated. The residue was dissolved in DCM and loaded onto an Analtech preparative TLC plate (Uniplate silic gel HLF, w/binder, w/ 254; 10×20 cm×250 microns) and eluted with 3% MeOH in DCM to afford the title compound (7.6 mg, 0.011 mmol, 64.1%) as a white solid. ¹H NMR (400 MHz, CD₂Cl₂) δ 7.72 (d, J=8.6 Hz, 1H), 7.24 (s, 1H), 7.17 (dd, J=2.3, 8.6 Hz, 1H), 7.09 (d, J=2.3 Hz, 1H), 6.98-6.89 (m, 2H), 5.81-5.71 (m, 1H), 5.37 (dd, J=8.6, 16.0 Hz, 1H), 4.16-3.98 (m, 4H), 3.93 (d, J=15.3 Hz, 1H), 3.77-3.63 (m, 3H), 3.61-3.50 (m, 1H), 3.39-3.30 (m, 1H), 3.21-3.07 (m, 2H), 3.04 (s, 3H), 3.00-2.90 (m, 1H), 2.83-2.67 (m, 2H), 2.58-2.47 (m, 1H), 2.47-2.35 (m, 2H), 2.18-2.00 (m, 3H), 1.99-1.86 (m, 3H), 1.85-1.77 (m, 1H), 1.76-1.67 (m, 1H), 1.66-1.51 (m, 2H), 1.48-1.34 (m, 2H). m/z (ESI, +ve ion) 677.2 (M+H)⁺.

2130

Example 1096. (1S,3'R,6'R,7'R)-6-chloro-7'-(2-(methylsulfonyl)ethoxy)-3,4-dihydro-2H,15'H-spiro[naphthalene-1,22'-[20]oxa[13]thia[1,14]diazatetracyclo[14.7.2.0³,⁶.0¹⁹,²⁴]pentacosa [16,18,24]trien]-15'-one 13',13'-dioxide

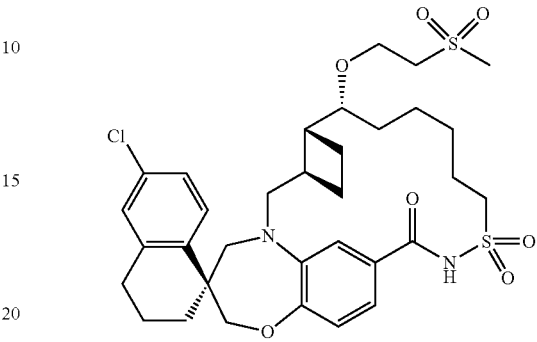

The title compound was prepared from Example 1095 by a procedure similar to the one described in Example 1094. ¹H NMR (400 MHz, CD₂Cl₂) δ 9.26 (br. s., 1H), 7.74 (d, J=8.6 Hz, 1H), 7.17 (dd, J=2.2, 8.5 Hz, 1H), 7.12-7.04 (m, 3H), 6.93 (d, J=8.0 Hz, 1H), 4.34 (dt, J=2.2, 10.0 Hz, 1H), 4.14-4.10 (m, 1H), 4.06-4.02 (m, 1H), 3.83-3.71 (m, 1H), 3.70-3.46 (m, 4H), 3.28-3.15 (m, 3H), 3.07-2.92 (m, 4H), 2.84-2.70 (m, 2H), 2.67-2.44 (m, 2H), 2.09 (d, J=12.3 Hz, 1H), 2.02 (br. s., 1H), 2.00-1.87 (m, 4H), 1.87-1.72 (m, 4H), 1.71-1.53 (m, 6H), 1.44-1.33 (m, 1H). m/z (ESI, +ve ion) 679.2 (M+H)⁺.

Biological Assays

Cell free Mcl-1: Bim Affinity Assay (Mcl-1 HTRF)

The inhibition of the Mcl-1/Bim interaction was measured using a time-resolved fluorescence resonance energy transfer (TR-FRET) assay. The recombinant human Mcl-1 (C-terminally 6×His tagged Mcl-1 containing residues 171-327) was generated at Amgen Inc (Thousand Oaks, CA). A biotinylated peptide derived from human Bim (residues 51-76) was purchased from CPC Scientific (San Jose, CA). The TR-FRET assay was conducted in a 384-well white OptiPlatem (PerkinElmer, Waltham, MA) in a total volume of 40 µL. The reaction mixture contained 0.1 nM Mcl-1 (171-327), 0.05 nM biotin-Bim (51-76), 0.05 nM LANCE® Eu-W1024 Anti-6×His (PerkinElmer), 0.072 nM Streptavidin-XLent (Cisbio, Bedford, MA), and serially diluted test compounds in the binding buffer of 20 mM Hepes, pH 7.5, 150 mM NaCl, 0.016 mM Brij®35, and 1 mM dithiothreitol. Test compounds were pre-incubated with Mcl-1 (171-327) and biotin-Bim (51-76) for 60 min before addition of the detection mixture (LANCE® Eu-W1024 Anti-6×His and Streptavidin-XLent). The reaction plates were further incubated overnight and then were read on an Envision® multimode reader (PerkinElmer). Fluorescence signals were measured at 620 nm (40-nm bandwidth) and 665 nm (7.5-nm bandwidth) with a 60 s delay after excitation at 320 nm (75-nm bandwidth). The signal ratio at 665/620 nm corresponded to the Mcl-1/Bim interaction and was used in all data analyses. The IC₅₀ values of test compounds were determined from duplicate data by analyzing competition curves using a four-parameter sigmoidal model in GraphPad Prism (GraphPad Software, San Diego, CA) or in Genedata Screener® (Genedata, Basel, Switzerland).

Cell Viability Assay (OPM-2 10 FBS)

The human multiple myeloma cell line, OPM-2, was cultured in complete growth medium containing RPMI 1640 and 10% fetal bovine serum (FBS). Cells were seeded into 384-well plates at 3000 cells/well density in complete growth medium containing 10% FBS, and incubated for 16 h with serially diluted test compounds in a 37° C. incubator with 5% $CO_2$. Cell viability was tested using CellTiter-Glo® assay (Promega, Madison, WI) according to the manufacturer recommendations. Luminescence was determined using an EnVision® Multilabel plate reader 25 min after the addition of detection reagent. $IC_{50}$ values were then calculated with Xlfit using a logistical 4-parameter fit model in GraphPad Prism (GraphPad Software, San Diego, CA) or in Genedata Screener® (Genedata, Basel, Switzerland).

Results for compounds tested in these biological assays are set forth below.

| Example # | Mcl-1 HTRF (µM) | OPM-2 10% FBS (µM) |
| --- | --- | --- |
| 1 | .00034 | .2544 |
| 2 | .00685 | NA |
| 3 | .0005185 | .4605 |
| 4 | .0010855 | .2985 |
| 5 | .0005395 | 0.329 |
| 8 | .0005635 | 1.455 |
| 9 | .00063 | .15529 |
| 10 | .00297 | .6295 |
| 11 | .005225 | 3.65 |
| 12 | .00337 | .404 |
| 13 | .0006855 | .3115 |
| 14 | .003925 | 1.1 |
| 15 | .0003925 | .8695 |
| 16 | .00221 | 3.58 |
| 17 | .00395 | 7.92 |
| 18 | .02015 | 15.2 |
| 19 | .0004945 | 1.2203 |
| 20 | .00085 | .8175 |
| 21 | .000806 | 1.0755 |
| 22 | .0003705 | .276 |
| 23 | .0003135 | 3.21 |
| 24 | .000465 | .683 |
| 25 | .0002465 | .1665 |
| 26 | .00020531 | .3118 |
| 27 | .000422 | .97 |
| 28 | .0008 | 1.7 |
| 29 | .00066 | 1.2767 |
| 30 | .001925 | NT |
| 31 | .000492 | .621 |
| 32 | .0006225 | .546 |
| 33 | .000168 | 8.16 |
| 34 | .0006205 | 3.6 |
| 35 | .00155 | 1.285 |
| 36 | .0005355 | 2.59 |
| 37 | .0006135 | 2.57 |
| 38 | .00054925 | .78 |
| 39 | .00065025 | .87267 |
| 40 | .0004615 | .971 |
| 41 | .0002005 | .0541 |
| 42 | .00057033 | .842 |
| 43 | .000995 | .53646 |
| 44 | .0001149 | NA |
| 45 | .0023 | NT |
| 46 | .0003675 | NT |
| 47 | .0006285 | 1.28 |
| 48 | .0005625 | .5245 |
| 49 | .000321 | .4445 |
| 50 | .00362 | 2.21 |
| 51 | .00559 | 1.83 |
| 52 | .00393 | 1.81 |
| 53 | .0007905 | .4865 |
| 54 | .000781 | .7745 |
| 55 | .006245 | 2.38 |
| 56 | .00304 | 1.79 |
| 57 | .0004905 | .555 |
| 58 | .0009935 | 1.18 |
| 59 | .00427 | 7.45 |
| 60 | .004075 | 2.69 |
| 61 | .000241 | .2775 |
| 62 | .000266 | .3618 |
| 63 | .000728 | .80967 |
| 64 | .0006785 | .39933 |
| 65 | .00238 | 1.1677 |
| 66 | .002315 | .492 |
| 67 | .00151 | .45 |
| 68 | .000359 | .2475 |
| 69 | .0005295 | .276 |
| 70 | .0011595 | .044167 |
| 71 | .00262 | 3.16 |
| 72 | .00032425 | .44475 |
| 73 | .000728 | 1.66 |
| 74 | .00113 | .381 |
| 75 | .001655 | .875 |
| 76 | .000405 | .14567 |
| 77 | .0005925 | .442 |
| 78 | .00145 | .587 |
| 79 | .00418 | 3.62 |
| 80 | .008985 | 6.53 |
| 81 | .03855 | 6.44 |
| 82 | .0078 | 2.92 |
| 83 | .000419 | .487 |
| 84 | .01315 | 5.9 |
| 85 | .00188 | 1.91 |
| 86 | .00404 | NT |
| 87 | .003315 | 3.54 |
| 88 | .00171 | 1.04 |
| 89 | .000666 | .798 |
| 90 | .00044025 | .3225 |
| 91 | .00306 | NT |
| 92 | .000781 | NT |
| 93 | .00049375 | .402 |
| 94 | .0004665 | .4315 |
| 95 | .0004595 | .572 |
| 96 | .03165 | NT |
| 97 | .0126 | NT |
| 98 | .015485 | NT |
| 99 | .02075 | NT |
| 100 | .002445 | NA |
| 101 | .002585 | 13 |
| 102 | .002725 | 18.6 |
| 103 | .00143 | N/A |
| 104 | .04 | 13 |
| 105 | .000589 | .33 |
| 106 | .0169 | N/A |
| 107 | .000597 | 17.3 |
| 108 | .001127 | 2.25 |
| 109 | .00134 | 12.2 |
| 110 | .00134 | 5.58 |
| 111 | .03075 | 17.8 |
| 112 | .00063 | .1724 |
| 113 | .000998 | 1.15 |
| 114 | .003595 | 3.4 |
| 115 | .002705 | N/A |
| 116 | .0008565 | NT |
| 117 | .002155 | NT |
| 118 | .0349 | NT |
| 119 | .02445 | NT |
| 120 | .000927 | NT |
| 121 | .0122 | NT |
| 122 | .007175 | NT |
| 123 | .004305 | NT |
| 124 | .0287 | NT |
| 125 | .00864 | NT |
| 126 | .0004475 | .496 |
| 127 | .000341 | 1.85 |
| 128 | .0006035 | 2.52 |
| 129 | .00579 | N/A |
| 130 | .000386 | .2285 |
| 131 | .00183 | 1.82 |
| 132 | .00707 | 5.73 |
| 133 | .0020025 | 2.75 |
| 134 | .0004945 | 1.041 |
| 135 | .000771 | 1.52 |

| Example # | Mcl-1 HTRF (μM) | OPM-2 10% FBS (μM) |
|---|---|---|
| 136 | .00025897 | .12978 |
| 137 | .00041625 | .419 |
| 138 | .000223 | .372 |
| 139 | .0001825 | .284 |
| 140 | .00024933 | .0962 |
| 141 | .03665 | N/A |
| 142 | .0004225 | NT |
| 143 | .002 | NT |
| 144 | .00147 | 3.43 |
| 145 | .000286 | 17 |
| 146 | .000276 | .556 |
| 147 | .00059 | .994 |
| 148 | .00028467 | .4585 |
| 149 | .00077 | 1.3275 |
| 150 | .005375 | N/A |
| 151 | .003565 | 9.17 |
| 152 | .0196 | 29.2 |
| 153 | .001225 | N/A |
| 154 | .0002585 | 7.58 |
| 155 | .0008455 | 11.6 |
| 156 | .000831 | .266 |
| 157 | .000558 | .48033 |
| 158 | .007595 | 9.36 |
| 159 | .00266 | 3.305 |
| 160 | .000397 | 5.295 |
| 161 | .001315 | .086 |
| 162 | .0009785 | 8.4 |
| 163 | .005075 | 18.9 |
| 164 | .00144 | 21.9 |
| 165 | .0038 | 25 |
| 166 | .000418 | 2.07 |
| 167 | .00025143 | .12162 |
| 168 | .000255 | .10724 |
| 169 | .0006105 | .405 |
| 170 | .002005 | .7035 |
| 176 | .000566 | .709 |
| 186 | .00791 | 4.66 |
| 187 | .000248 | .426 |
| 188 | .01135 | 3.9 |
| 189 | .003485 | 1.211 |
| 195 | .005725 | NT |
| 196 | .02225 | NT |
| 197 | .001125 | 2.6 |
| 198 | .00324 | N/A |
| 199 | .006045 | 10.2 |
| 200 | .003575 | 3.87 |
| 201 | .00269 | N/A |
| 202 | .0002175 | .5655 |
| 203 | .0003665 | 2.79 |
| 204 | .000732 | .6865 |
| 205 | .003165 | 3.29 |
| 206 | .0000514 | 3.34 |
| 207 | .0001033 | 2.285 |
| 209 | .005255 | 5.37 |
| 210 | .00159 | 1.53 |
| 211 | .00111 | 2.37 |
| 212 | .00296 | 18.2 |
| 213 | .0010835 | .835 |
| 214 | .0123 | 2.28 |
| 215 | .00132 | 8.74 |
| 216 | .00977 | 26.2 |
| 217 | .003815 | 2.66 |
| 218 | .000216 | 3.67 |
| 219 | .0024 | 1.83 |
| 220 | .001995 | 2.66 |
| 221 | .01085 | NT |
| 222 | .009085 | 30.8 |
| 225 | .02305 | N/A |
| 226 | .02565 | N/A |
| 227 | .03285 | 21.4 |
| 228 | .0131 | 23.1 |
| 229 | .001625 | 1.715 |
| 230 | .0323 | N/A |
| 231 | .0452 | 23.1 |
| 232 | .00164 | 3.47 |
| 233 | .00466 | 4.7 |
| 234 | .00167 | 1.925 |
| 235 | .00086975 | .4375 |
| 236 | .006425 | 13.7 |
| 237 | .00232 | 2.26 |
| 238 | .00157 | 17.6 |
| 239 | .00143 | 3.82 |
| 240 | .00254 | 3.73 |
| 241 | .004855 | 7.39 |
| 242 | .00305 | .46733 |
| 243 | .01092 | 12.1 |
| 244 | .00213 | .4095 |
| 245 | .01197 | 6.1 |
| 246 | .0358 | N/A |
| 247 | .0129 | 31.2 |
| 248 | .000701 | 2.165 |
| 249 | .0284 | N/A |
| 256 | .005585 | 27.8 |
| 257 | .00456 | 17.8 |
| 259 | .04435 | 23 |
| 260 | .001435 | 3.34 |
| 261 | .0339 | N/A |
| 262 | .01715 | 13.9 |
| 263 | .00842 | N/A |
| 264 | .00537 | 31.1 |
| 265 | .0002855 | .0815 |
| 266 | .000728 | 1.0715 |
| 267 | .004035 | 1.525 |
| 268 | .0046 | 3.62 |
| 269 | .0257 | 5.56 |
| 270 | .00103 | .1158 |
| 271 | .00489 | 20.9 |
| 272 | .000396 | 1.1915 |
| 276 | .01315 | 6.41 |
| 288 | .0002235 | .2795 |
| 292 | .000092875 | 1.109 |
| 293 | .00036 | 27.6 |
| 294 | .0002555 | .41 |
| 295 | .00018975 | .15125 |
| 296 | .0004965 | .5245 |
| 297 | .000654 | .4775 |
| 298 | .000425 | .86 |
| 299 | .0002755 | .2795 |
| 300 | .0002405 | .817 |
| 301 | .000245 | .8445 |
| 303 | .0002 | .567 |
| 304 | .0001513 | 2.28 |
| 305 | .000177 | .9975 |
| 306 | .0012 | 1.135 |
| 307 | .000127 | .3015 |
| 308 | .0003825 | .2135 |
| 309 | .0000805 | .4135 |
| 310 | .000109 | .7925 |
| 311 | .000138 | 1.4 |
| 312 | .000153 | 1.002 |
| 313 | .00018535 | .21975 |
| 314 | .00013585 | 2.125 |
| 315 | .000774 | .421 |
| 316 | .0000986 | .162 |
| 317 | .000223 | .1965 |
| 318 | .0002725 | .42967 |
| 320 | .0003285 | .342 |
| 321 | .002285 | 2.18 |
| 322 | .0004005 | .1228 |
| 323 | .002025 | 2.98 |
| 324 | .00168 | 1.94 |
| 325 | .000297 | .2075 |
| 326 | .005505 | 20 |
| 328 | .0004405 | .428 |
| 329 | .002585 | 3.48 |
| 330 | .000794 | 2.105 |
| 331 | .0002485 | .2835 |
| 332 | .00389 | 5.58 |
| 333 | .00096033 | 3.45 |
| 334 | .00692 | 2.66 |
| 335 | .000263 | 2.125 |
| 336 | .001505 | N/A |
| 337 | .000705 | .38333 |
| 338 | .000241 | 5.62 |

| Example # | Mcl-1 HTRF (μM) | OPM-2 10% FBS (μM) | Example # | Mcl-1 HTRF (μM) | OPM-2 10% FBS (μM) |
|---|---|---|---|---|---|
| 339 | .002705 | N/A | 436 | .0002425 | NT |
| 340 | .0001895 | .941 | 437 | .003765 | NT |
| 341 | .007075 | N/A | 438 | .000731 | NT |
| 342 | .005 | N/A | 439 | .00032125 | NT |
| 343 | .007275 | 6.49 | 440 | .00244 | NT |
| 344 | .00211 | .9115 | 441 | .0006315 | NT |
| 345 | .000877 | .488 | 442 | .0002924 | NT |
| 346 | .001895 | 2.27 | 443 | .001505 | NT |
| 347 | .00722 | 5.55 | 444 | .0007845 | NT |
| 348 | .00686 | 3.56 | 445 | .0004605 | NT |
| 349 | .0038267 | 1.0492 | 446 | .0004935 | .419 |
| 350 | .003735 | N/A | 447 | .000378 | NT |
| 353 | .009095 | N/A | 448 | .000951 | NT |
| 361 | .000519 | .509 | 449 | .000716 | .773 |
| 362 | .000639 | .476 | 450 | .00676 | NT |
| 363 | .000793 | .483 | 451 | .011485 | NT |
| 364 | .00312 | 30.9 | 452 | .000277 | .775 |
| 365 | .0007515 | 2.96 | 453 | .006735 | 21 |
| 367 | .0421 | N/A | 454 | .00021987 | .33765 |
| 368 | .00374 | NT | 455 | .00016602 | .071575 |
| 369 | .0039833 | NT | 456 | .0005405 | .701 |
| 370 | .0045 | NT | 457 | .00026333 | .2965 |
| 371 | .02075 | NT | 458 | .0002012 | .12187 |
| 372 | .009485 | 14.6 | 459 | .00337 | 3.3 |
| 373 | .000731 | .404 | 460 | .0003336 | .13154 |
| 374 | .00286 | 2.94 | 461 | .001795 | .775 |
| 375 | .007735 | 5.7 | 462 | .0005225 | .264 |
| 376 | .000403 | .2225 | 463 | .0004165 | .122 |
| 377 | .000303 | .1805 | 464 | .001485 | .65 |
| 378 | .0002405 | .14 | 465 | .00047 | .0564 |
| 379 | .0002115 | .1278 | 466 | .0003315 | .1275 |
| 385 | .001055 | .4845 | 467 | .00145 | 1.51 |
| 386 | .00062983 | .27267 | 468 | .0002985 | .2615 |
| 387 | .001645 | 1.252 | 469 | .0009735 | .334 |
| 393 | .00021325 | .13677 | 470 | .000726 | .355 |
| 394 | .0012635 | 1.25 | 471 | .000188 | .141 |
| 395 | .000403 | .7515 | 472 | .0002695 | .2065 |
| 396 | .0003841 | .18637 | 473 | .00036883 | .15983 |
| 397 | .000228 | .1431 | 474 | .0001945 | .426 |
| 398 | .000233 | .0883 | 475 | .0007185 | 1.535 |
| 399 | .000239 | .165 | 476 | .006695 | 8.35 |
| 400 | .0000856 | .0996 | 477 | .0003115 | .2865 |
| 401 | .000531 | .4525 | 478 | .0001965 | .4685 |
| 402 | .01865 | 13.6 | 479 | .00537 | 8.12 |
| 403 | .000495 | .10665 | 480 | .0003935 | 1.075 |
| 404 | .0004415 | NT | 481 | .000541 | 1.87 |
| 405 | .000543 | NT | 482 | .00752 | 7.64 |
| 406 | .0006015 | NT | 483 | .02015 | 12 |
| 407 | .00012697 | 14.4 | 484 | .0003305 | .4115 |
| 408 | .0003115 | .09885 | 485 | .000471 | .5575 |
| 409 | .00127 | .751 | 486 | .011715 | 15.3 |
| 410 | .000144 | .208 | 487 | .001046 | 5.8 |
| 411 | .00129 | 2.41 | 488 | .00521 | 12.9 |
| 412 | .0002665 | .325 | 489 | .0006665 | 1.225 |
| 413 | .0003575 | .3745 | 490 | .00209 | 7.96 |
| 414 | .000188 | .1605 | 491 | .000774 | 3.48 |
| 415 | .000276 | 2.64 | 492 | .000755 | 3.82 |
| 416 | .000377 | 1.059 | 493 | .000983 | .66 |
| 417 | .0002145 | .8335 | 494 | .00881 | 3.68 |
| 418 | .0002745 | .1108 | 495 | .002485 | NT |
| 419 | .0003335 | .3105 | 496 | .00633 | NT |
| 420 | .000349 | NT | 497 | .004 | NT |
| 421 | .000686 | .674 | 498 | .00903 | NT |
| 422 | .0008655 | NT | 499 | .024 | NT |
| 423 | .00024875 | .19832 | 500 | .00708 | NT |
| 424 | .0005015 | .2475 | 501 | .0014935 | NT |
| 425 | .0004 | .3045 | 502 | .002305 | NT |
| 426 | .002105 | .941 | 503 | .003965 | NT |
| 427 | .0004145 | .204 | 504 | .00255 | NT |
| 428 | .0003335 | .1765 | 505 | .010445 | NT |
| 429 | .00415 | 1.315 | 506 | .01555 | NT |
| 430 | .0007425 | .21633 | 507 | .0183 | NT |
| 431 | .000512 | .14033 | 508 | .006015 | 2.47 |
| 432 | .0009965 | NT | 509 | .0001875 | .235 |
| 433 | .0032267 | NT | 510 | .0012535 | .587 |
| 434 | .000273 | NT | 511 | .0015 | .311 |
| 435 | .002565 | NT | 512 | .000998 | .362 |

| Example # | Mcl-1 HTRF (μM) | OPM-2 10% FBS (μM) | Example # | Mcl-1 HTRF (μM) | OPM-2 10% FBS (μM) |
|---|---|---|---|---|---|
| 513 | .000395 | .18375 | 616 | .0001785 | .48218 |
| 514 | .0003905 | .165 | 617 | .0002205 | 11.5 |
| 515 | .00487 | 2.52 | 618 | .0001725 | .607 |
| 516 | .00027 | .0725 | 619 | .000187 | .40067 |
| 517 | .001865 | .467 | 620 | .00071 | 4.08 |
| 518 | .00049 | .257 | 621 | .000225 | 3.67 |
| 519 | .001435 | .33867 | 622 | .0002235 | .257 |
| 520 | .000279 | .1425 | 623 | .0006415 | .483 |
| 521 | .000291 | .166 | 624 | .000338 | .455 |
| 522 | .000284 | .15225 | 625 | .0383 | N/A |
| 523 | .00182 | .232 | 626 | .000305 | 2.2 |
| 524 | .0003645 | .11255 | 627 | .01007 | N/A |
| 525 | .0004155 | .186 | 628 | .0039 | N/A |
| 526 | .0010575 | .862 | 629 | .0023 | N/A |
| 527 | .0002175 | .0647 | 630 | .001615 | N/A |
| 528 | .0002525 | .0696 | 631 | .0002985 | 2.53 |
| 529 | .00097 | .7535 | 632 | .000187 | .8775 |
| 530 | .0007635 | .134 | 633 | .0231 | 17.8 |
| 531 | .0011535 | .811 | 634 | .0115 | 2.14 |
| 532 | .0004275 | .1555 | 635 | .0009845 | .0985 |
| 533 | .000583 | 14.2 | 636 | .0291 | 4.74 |
| 534 | .00078825 | .0993 | 637 | .00017073 | .10744 |
| 535 | .0003885 | .1625 | 638 | .000243 | .13086 |
| 536 | .00199 | 21.3 | 639 | .0008095 | .3485 |
| 539 | .00278 | N/A | 640 | .02085 | 5.4 |
| 540 | .0002355 | .094133 | 641 | .00053725 | .28225 |
| 543 | .0005355 | .699 | 642 | .00053875 | .35075 |
| 544 | .000193 | 1.52 | 643 | .0003365 | .151 |
| 546 | .00028 | .854 | 644 | .01135 | 4.26 |
| 547 | .0002395 | 2.22 | 645 | .0005885 | .125 |
| 548 | .0002745 | .4775 | 646 | .0453 | 23.7 |
| 549 | .0005545 | .285 | 647 | .00018785 | .13146 |
| 550 | .0005815 | 7.29 | 648 | .001445 | .154 |
| 551 | .00343 | N/A | 649 | .01385 | 6.63 |
| 552 | .0004815 | 2.51 | 650 | .003715 | 2.25 |
| 553 | .004 | NT | 651 | .000316 | .229 |
| 554 | .001835 | NT | 652 | .002395 | 4.46 |
| 555 | .00477 | 2.61 | 653 | .00072233 | .37067 |
| 556 | .00165 | .78133 | 654 | .0076033 | 3.51 |
| 557 | .0010755 | 1.0363 | 655 | .0008845 | .947 |
| 558 | .000284 | .891 | 656 | .00137 | .237 |
| 559 | .0005985 | 4.4233 | 657 | .01125 | 24.7 |
| 560 | .00483 | 12.2 | 658 | .000285 | .259 |
| 561 | .003575 | 8.47 | 659 | .00337 | 10.9 |
| 562 | .001115 | .9855 | 660 | .0003755 | .4165 |
| 563 | .00269 | 4.5 | 661 | .00251 | 2.76 |
| 564 | .000308 | 3.04 | 662 | .001115 | 1.3867 |
| 565 | .0006095 | 12.6 | 663 | .00031167 | 3.1085 |
| 566 | .0003835 | .282 | 665 | .00289 | 1.315 |
| 567 | .00369 | 4.51 | 666 | .00206 | 2.44 |
| 568 | .0011 | 1.31 | 667 | .0002445 | .378 |
| 569 | .0010195 | .759 | 668 | .017 | 11.6 |
| 570 | .00844 | 3.02 | 669 | .00137 | .272 |
| 571 | .0347 | 20.3 | 670 | .0024833 | 1.0003 |
| 572 | .0454 | 13.9 | 671 | .0198 | 5.65 |
| 573 | .0313 | 23.1 | 672 | .000193 | .2855 |
| 574 | .000393 | .188 | 673 | .0001835 | .445 |
| 575 | .00321 | 2.07 | 674 | .0082 | 1.09 |
| 576 | .0003815 | .2205 | 675 | .000437 | .48 |
| 581 | .00943 | N/A | 676 | .002035 | 3.91 |
| 597 | .00146 | NT | 677 | .009575 | 3.55 |
| 598 | .00149 | NT | 678 | .008025 | 7.29 |
| 599 | .00151 | .6515 | 679 | .0004295 | .205 |
| 600 | .0006465 | .104 | 680 | .0268 | NT |
| 601 | .001335 | N/A | 681 | .029 | NT |
| 602 | .00174 | .727 | 682 | .00178 | NT |
| 603 | .000667 | .4385 | 683 | .002315 | 2.09 |
| 604 | .0095775 | NT | 684 | .011 | N/A |
| 605 | .00094333 | NT | 685 | .00266 | 7.18 |
| 606 | .01354 | NT | 686 | .000597 | .993 |
| 609 | .00384 | N/A | 687 | .0002065 | .1485 |
| 610 | .000923 | 1.14 | 688 | .01415 | 13.6 |
| 611 | .0002755 | 8.49 | 689 | .0025325 | .8358 |
| 612 | .000362 | 15.2 | 690 | .01955 | 19 |
| 613 | .000329 | 1.5425 | 691 | .00181 | 2.33 |
| 614 | .00113 | 8.07 | 692 | .0006 | 1.52 |
| 615 | .000696 | .643 | 693 | .0002345 | .742 |

| Example # | Mcl-1 HTRF (μM) | OPM-2 10% FBS (μM) | Example # | Mcl-1 HTRF (μM) | OPM-2 10% FBS (μM) |
|---|---|---|---|---|---|
| 694 | .0007635 | .9685 | 772 | .005195 | NT |
| 695 | .00204 | NT | 773 | .002355 | NT |
| 696 | .000305 | NT | 774 | .00172 | NT |
| 697 | .0007465 | NT | 775 | .00294 | NT |
| 698 | .00067875 | NT | 776 | .00271 | NT |
| 699 | .00064886 | NT | 777 | .0138 | .912 |
| 700 | .02765 | NT | 778 | .00689 | NT |
| 701 | .00144 | 2.025 | 779 | .005546 | NT |
| 702 | .007665 | 13.4 | 780 | .0048433 | NT |
| 703 | .00509 | 2.06 | 781 | .011545 | N/A |
| 704 | .0405 | N/A | 783 | .001041 | NT |
| 705 | .02805 | 22.8 | 784 | .00269 | 14.2 |
| 706 | .00451 | NT | 785 | .003025 | 16 |
| 707 | .00225 | NT | 786 | .001035 | 1.48 |
| 708 | .00112 | NT | 787 | .02145 | N/A |
| 709 | .010495 | NT | 791 | .00621 | 23.3 |
| 710 | .0256 | NT | 793 | .00044 | .5365 |
| 711 | .008215 | NT | 794 | .00151 | 1.895 |
| 712 | .00099525 | NT | 795 | .00038 | .392 |
| 713 | .0017067 | NT | 796 | .00045 | .195 |
| 714 | .001815 | 1.365 | 798 | .00242 | 9.26 |
| 715 | .00726 | 13.7 | 801 | .00193 | 20.7 |
| 716 | .0173 | 23.5 | 802 | .00451 | 3.31 |
| 717 | .0286 | N/A | 803 | .00106 | .804 |
| 718 | .0014575 | 1.82 | 804 | .000658 | .377 |
| 719 | .00036609 | .11667 | 805 | .001063 | .7185 |
| 720 | .000327 | .0542 | 807 | .0423 | NT |
| 721 | .000539 | .073525 | 808 | .0015359 | NT |
| 722 | .01194 | .473 | 815 | .0012636 | NT |
| 723 | .0004855 | .1375 | 816 | .00472 | NT |
| 724 | .000485 | .4205 | 817 | .02935 | NT |
| 726 | .0122 | 2.145 | 818 | .013567 | NT |
| 727 | .0003645 | .147 | 823 | .0482 | NT |
| 728 | .000437 | .2685 | 824 | .0201 | NT |
| 729 | .000311 | .1185 | 825 | .026433 | NT |
| 730 | .0003075 | .157 | 826 | .01048 | NT |
| 731 | .0003015 | .117 | 827 | .00354 | NT |
| 732 | .000244 | .1695 | 829 | .0098667 | NT |
| 733 | .0002835 | .069667 | 830 | .021133 | NT |
| 734 | .001115 | .134 | 831 | .00135 | 4.46 |
| 735 | .0006815 | .20233 | 832 | .0082575 | NT |
| 736 | .0008905 | .19233 | 833 | .005125 | NT |
| 737 | .01515 | 3.39 | 834 | .0041 | NT |
| 738 | .003215 | 1.76 | 835 | .00344 | NT |
| 739 | .00014137 | 24.2 | 836 | .0006275 | .7055 |
| 740 | .000543 | .1702 | 837 | .001195 | 4.08 |
| 741 | .0135 | 3.11 | 838 | .00139 | 1.22 |
| 742 | .002 | NT | 840 | .00438 | NT |
| 743 | .0124 | NT | 841 | .001052 | 1.59 |
| 744 | .019345 | NT | 843 | .0068 | NT |
| 745 | .003345 | NT | 844 | .01105 | NT |
| 746 | .003265 | NT | 845 | .0043233 | NT |
| 747 | .0147 | NT | 846 | .0021779 | 2.7626 |
| 748 | .00501 | NT | 850 | .001995 | N/A |
| 749 | .002495 | NT | 851 | .001001 | 19.7 |
| 750 | .00541 | NT | 853 | .01173 | NT |
| 751 | .007725 | NT | 857 | .00846 | NT |
| 752 | .004395 | NT | 858 | .0278 | NT |
| 754 | .00893 | NT | 859 | .0158 | 11.5 |
| 755 | .000632 | NT | 861 | .0015903 | NT |
| 755 | .00349 | NT | 862 | .00275 | NT |
| 756 | .00112 | NT | 863 | .005375 | NT |
| 757 | .004105 | NT | 866 | .00953 | NT |
| 758 | .0004604 | 1.18 | 867 | .006815 | NT |
| 759 | .00398 | NT | 870 | .008255 | NT |
| 760 | .0158 | NT | 872 | .006355 | NT |
| 761 | .0017833 | NT | 876 | .0183 | N/A |
| 762 | .00057583 | NT | 877 | .02625 | NT |
| 763 | .002925 | NT | 878 | .009455 | 7 |
| 764 | .00011335 | 11.2 | 881 | .02225 | NT |
| 765 | .00389 | NT | 882 | .00114 | NT |
| 766 | .006495 | NT | 883 | .0485 | NT |
| 767 | .00655 | NT | 884 | .0012855 | NT |
| 768 | .00224 | NT | 885 | .018332 | .616 |
| 769 | .00097133 | NT | 886 | .00252 | 12.3 |
| 770 | .001335 | NT | 891 | .001335 | NT |
| 771 | .00409 | NT | 892 | .00817 | NT |

| Example # | Mcl-1 HTRF (μM) | OPM-2 10% FBS (μM) |
|---|---|---|
| 893 | .002515 | NT |
| 894 | .00534 | NT |
| 895 | .0405 | 25.8 |
| 898 | .00403 | NT |
| 900 | .00433 | N/A |
| 901 | .000568 | 5.5 |
| 904 | .0162 | NT |
| 905 | .0141 | NT |
| 906 | .00903 | NT |
| 907 | .0189 | NT |
| 908 | .002475 | 5.83 |
| 910 | .0058 | N/A |
| 911 | .00808 | NT |
| 912 | .00778 | NT |
| 913 | .0061 | NT |
| 914 | .00187 | NT |
| 915 | .016238 | NT |
| 917 | .004105 | NT |
| 918 | .00275 | 15.1 |
| 919 | .002315 | 6.11 |
| 920 | .001855 | 4.35 |
| 921 | .00209 | 9.16 |
| 922 | .0009745 | 2.4 |
| 923 | .01775 | NT |
| 924 | .00507 | N/A |
| 927 | .04625 | NT |
| 928 | NT | NT |
| 929 | .04 | NT |
| 930 | .0196 | NT |
| 931 | NT | NT |
| 932 | .003685 | NT |
| 933 | .015 | NT |
| 934 | .0020675 | NT |
| 935 | .00207 | NT |
| 936 | .00474 | NT |
| 937 | .004745 | NT |
| 938 | .00594 | NT |
| 939 | .006665 | NT |
| 940 | .01855 | NT |
| 941 | .008325 | NT |
| 942 | .03635 | NT |
| 943 | .0162 | NT |
| 945 | .01205 | NT |
| 946 | .00415 | NT |
| 947 | .0137 | NT |
| 948 | .01029 | NT |
| 949 | .008425 | NT |
| 950 | .00149 | NT |
| 951 | .013095 | NT |
| 952 | .0012825 | 6.38 |
| 953 | .0008 | 2.5 |
| 954 | .00354 | 21.5 |
| 955 | .0012333 | .567 |
| 956 | .0002755 | .211 |
| 957 | .0004415 | .3085 |
| 958 | .000253 | 3.89 |
| 964 | .001006 | NT |
| 965 | .000403 | .6932 |
| 966 | .0003485 | .754 |
| 967 | .001065 | .461 |
| 968 | .001895 | NT |
| 969 | .002905 | NT |
| 970 | .000859 | NT |
| 971 | .00844 | NT |
| 972 | .001595 | NT |
| 973 | .000378 | NT |
| 974 | .000716 | NT |
| 975 | .002155 | NT |
| 976 | .01044 | NT |
| 977 | .0003285 | .2655 |
| 978 | .00171 | NT |
| 979 | .000305 | NT |
| 979 | .0425 | 16.9 |
| 980 | .0007555 | NT |
| 981 | .0009425 | NT |
| 982 | .00314 | NT |
| 983 | .00123 | NT |
| 984 | .00109 | NT |
| 985 | .0014633 | NT |
| 986 | .0004755 | .2705 |
| 987 | .000616 | .3925 |
| 988 | .0005365 | 1.0015 |
| 989 | .000851 | .3305 |
| 990 | .003085 | 2.23 |
| 991 | .000644 | NT |
| 992 | .00010255 | 2.34 |
| 993 | .00201 | .373 |
| 994 | .0002205 | N/A |
| 995 | .000872 | 1.682 |
| 996 | .0004875 | 8.19 |
| 997 | .000336 | .96167 |
| 998 | .002135 | NT |
| 999 | .000373 | NT |
| 1000 | .00314 | NT |
| 1001 | .000573 | .861 |
| 1002 | .000448 | 1.225 |
| 1003 | .000844 | .273 |
| 1004 | .0006355 | .023628 |
| 1005 | .0001565 | 4.11 |
| 1006 | .00081 | 11.6 |
| 1007 | .0012 | .074 |
| 1008 | .0002315 | 5.59 |
| 1009 | .00123 | .70233 |
| 1010 | .000377 | .298 |
| 1011 | .0003475 | .5235 |
| 1012 | .0006975 | NT |
| 1013 | .01815 | NT |
| 1014 | .000267 | .329 |
| 1015 | .0002755 | .2348 |
| 1016 | .0004835 | .291 |
| 1017 | .000339 | .31 |
| 1018 | .000356 | .285 |
| 1019 | .0004975 | .475 |
| 1020 | .001055 | .759 |
| 1021 | .00909 | 27 |
| 1022 | .0235 | 22.7 |
| 1023 | .0003075 | .501 |
| 1024 | .0002965 | .414 |
| 1025 | .000411 | .14115 |
| 1026 | .001125 | .2885 |
| 1027 | .000945 | .218 |
| 1028 | .003485 | N/A |
| 1029 | .004425 | N/A |
| 1030 | .000195 | .27067 |
| 1031 | .006575 | N/A |
| 1032 | .000422 | .575 |
| 1033 | .0003665 | .20513 |
| 1034 | .00404 | 8.05 |
| 1035 | .01405 | 24.5 |
| 1036 | .00136 | 11.3 |
| 1037 | .0008305 | .7435 |
| 1038 | .00118 | 2.2 |
| 1039 | .0003885 | .198 |
| 1040 | .0010425 | 2.19 |
| 1041 | .00018325 | .0772 |
| 1042 | .00078 | .39333 |
| 1043 | .00609 | 6.74 |
| 1044 | .03585 | N/A |
| 1045 | .000294 | 1.137 |
| 1046 | .000785 | 2.52 |
| 1047 | .00042387 | .29963 |
| 1048 | .00029925 | .090833 |
| 1049 | .0002635 | .1265 |
| 1050 | .000589 | .288 |
| 1051 | .00001965 | 1.895 |
| 1052 | .0001099 | .09565 |
| 1053 | .0011945 | 1.48 |
| 1054 | .0002115 | .10105 |
| 1055 | .00039367 | .257 |
| 1056 | .004535 | 5.25 |
| 1057 | .000601 | .6275 |
| 1058 | .0002495 | .4555 |
| 1059 | .009695 | 4.91 |
| 1060 | .0001785 | .11583 |

-continued

| Example # | Mcl-1 HTRF (μM) | OPM-2 10% FBS (μM) |
|---|---|---|
| 1061 | .0007105 | 1.107 |
| 1062 | .007875 | 12.6 |
| 1063 | .011277 | 18.35 |
| 1064 | .0003635 | .15683 |
| 1065 | .000402 | .09485 |
| 1066 | .01785 | 15.2 |
| 1067 | .00555 | 5.71 |
| 1068 | .000442 | 1.955 |
| 1069 | .001675 | 1.505 |
| 1070 | .001066 | 1.2285 |
| 1071 | NT | NT |
| 1072 | .001356 | 1.5067 |
| 1073 | .0006175 | 1.115 |
| 1074 | .0009875 | 3.85 |
| 1075 | .00615 | 2.15 |
| 1076 | .001825 | NT |
| 1077 | .00345 | NT |
| 1078 | .000557 | NT |
| 1079 | .00548 | NT |
| 1080 | .00114 | NT |
| 1081 | .000947 | NT |
| 1082 | .018 | NT |
| 1083 | .00219 | NT |
| 1084 | .013578 | NT |
| 1085 | .00206 | N/A |
| 1086 | .000421 | 8.65 |
| 1087 | .0004935 | .6925 |
| 1088 | .004365 | 8.98 |
| 1089 | .000874 | N/A |
| 1090 | .002775 | N/A |
| 1091 | .003685 | NT |
| 1092 | .00653 | NT |
| 1093 | .002545 | NT |
| 1094 | .01785 | NT |
| 1095 | .001295 | NT |
| 1096 | .003485 | NT |
| 1104 | .0309 | NT |

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed:

1. A compound, wherein the compound has a formula selected from one of the following:

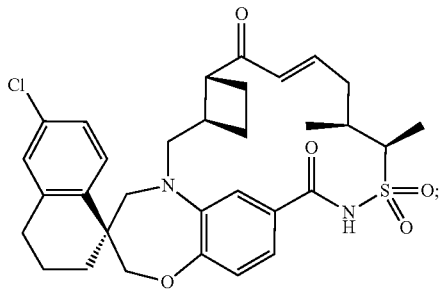

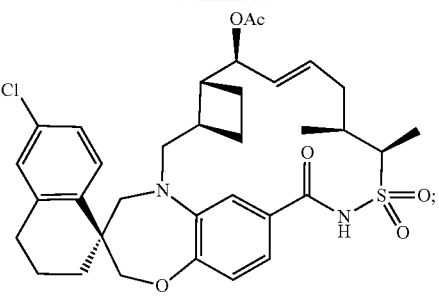

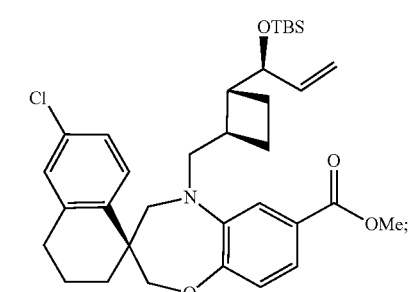

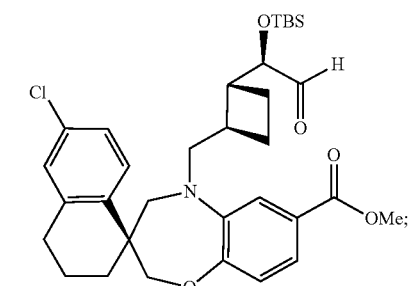

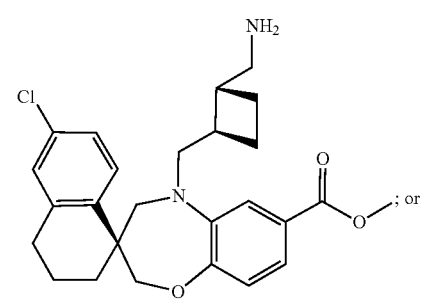

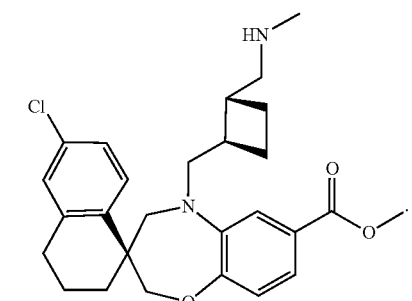

wherein TBS refers to the t-butyldimethylsilyl group.

2. The compound of claim 1, wherein the compound has the formula:
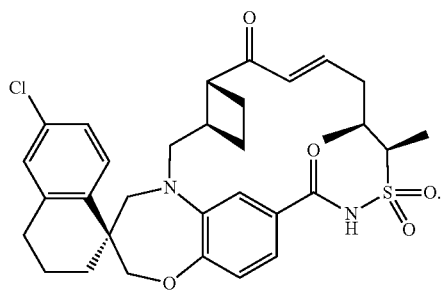 [SMILES: C[C@@H]1[C@@H](C)C/C=C/C(=O)[C@@H]2CC[C@H]2CN2C[C@@]3(CCCc4cc(Cl)ccc43)COc3ccc(cc32)C(=O)NS1(=O)=O]
3. The compound of claim 1, wherein the compound has the formula:
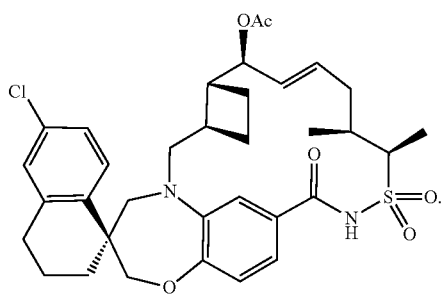 [SMILES: CC(=O)O[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]
4. The compound of claim 1, wherein the compound has the formula:
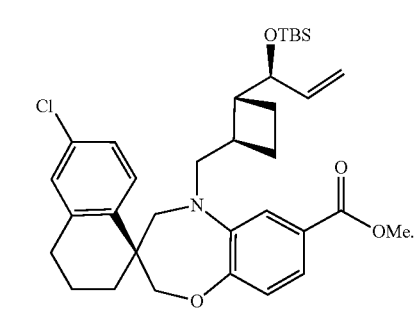 [SMILES: C=C[C@H](O[Si](C)(C)C(C)(C)C)[C@@H]1CC[C@H]1CN1C[C@@]2(CCCc3cc(Cl)ccc32)COc2ccc(C(=O)OC)cc21]
5. The compound of claim 1, wherein the compound has the formula:
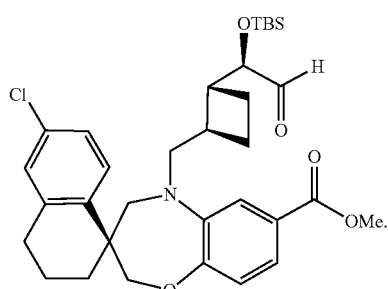
6. The compound of claim 1, wherein the compound has the formula:
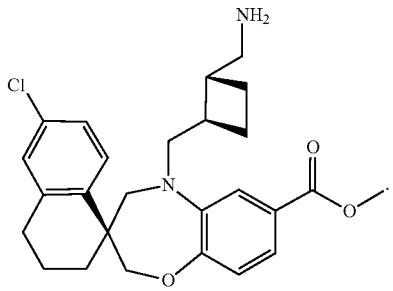
7. The compound of claim 1, wherein the compound has the formula:
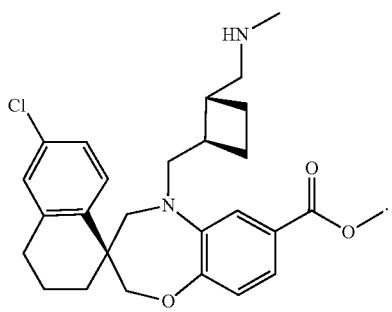
\* \* \* \* \*